US010717716B2

(12) United States Patent
Lee et al.

(10) Patent No.: US 10,717,716 B2
(45) Date of Patent: Jul. 21, 2020

(54) 1,3,4-OXADIAZOLE DERIVATIVE COMPOUNDS AS HISTONE DEACETYLASE 6 INHIBITOR, AND THE PHARMACEUTICAL COMPOSITION COMPRISING THE SAME

(71) Applicant: Chong Kun Dang Pharmaceutical Corp., Seoul (KR)

(72) Inventors: Jaekwang Lee, Gyeonggi-do (KR); Yuntae Kim, Gyeonggi-do (KR); Chang Sik Lee, Gyeonggi-do (KR); Hyeseung Song, Gyeonggi-do (KR); Dal-Yong Gwak, Gyeonggi-do (KR); Jaeyoung Lee, Gyeonggi-do (KR); Jung Taek Oh, Gyeonggi-do (KR); Chang Gon Lee, Gyeonggi-do (KR); Il Hyang Kim, Gyeonggi-do (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 15/750,067

(22) PCT Filed: Aug. 4, 2016

(86) PCT No.: PCT/KR2016/008622
§ 371 (c)(1),
(2) Date: Feb. 2, 2018

(87) PCT Pub. No.: WO2017/023133
PCT Pub. Date: Feb. 9, 2017

(65) Prior Publication Data
US 2018/0230114 A1    Aug. 16, 2018

(30) Foreign Application Priority Data
Aug. 4, 2015  (KR) .................. 10-2015-0110227

(51) Int. Cl.
| C07D 271/10 | (2006.01) |
| C07D 413/12 | (2006.01) |
| C07D 491/10 | (2006.01) |
| C07D 413/04 | (2006.01) |
| A61P 25/00  | (2006.01) |
| C07D 471/10 | (2006.01) |
| A61P 37/00  | (2006.01) |
| C07D 413/14 | (2006.01) |
| C07D 417/12 | (2006.01) |
| A61P 29/00  | (2006.01) |
| C07D 417/14 | (2006.01) |
| A61P 35/00  | (2006.01) |

(52) U.S. Cl.
CPC ............ *C07D 271/10* (2013.01); *A61P 25/00* (2018.01); *A61P 29/00* (2018.01); *A61P 35/00* (2018.01); *A61P 37/00* (2018.01); *C07D 413/04* (2013.01); *C07D 413/12* (2013.01); *C07D 413/14* (2013.01); *C07D 417/12* (2013.01); *C07D 417/14* (2013.01); *C07D 471/10* (2013.01); *C07D 491/10* (2013.01)

(58) Field of Classification Search
CPC .................................................... C07D 271/10
See application file for complete search history.

(56) References Cited

U.S. PATENT DOCUMENTS

| 4,871,753 A    | 10/1989 | Rorh          |
| 8,981,084 B2   | 3/2015  | Baloglu et al. |
| 9,670,193 B2   | 6/2017  | Hebach et al. |
| 2005/0288282 A1 | 12/2005 | Delorme et al. |
| 2006/0058298 A1 | 3/2006  | Delorme et al. |
| 2007/0293530 A1 | 12/2007 | Smil et al.   |
| 2012/0027874 A1 | 2/2012  | Charrier et al. |

(Continued)

FOREIGN PATENT DOCUMENTS

| CN | 104744446  | 7/2015 |
| JP | 2005513123 | 5/2005 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
CAS Registry No. 904548-10-3 (Aug. 25, 2006).
AU Examination Report No. 1 for App No. AU201603891, dated Nov. 16, 2018 (7 pages).
Bolden et al., Nat. Rev. Drug Discov. 5(9), 769-784 (2006).
Hassig et al., Curr. Opin. Chem. Biol. 1, 300-308 (1997).
Hu et al., J. Neurol. Sci. 304, 1-8 (2011).
Matthias et al., Mol. Cell. Biol. 28, 1688-1701 (2008).
Methot et al., Bioorg. Med. Chem. Lett. 18, 973-978 (2008).
Piekarz et al., Pharmaceuticals 3, 2751-2767 (2010).
Santo et al., Blood 119, 2579-2589 (2012).
Vishwakarma et al., International Immunopharmacology 16, 72-78 (2013).

(Continued)

Primary Examiner — Rebecca L Anderson
(74) Attorney, Agent, or Firm — Fish & Richardson P.C.

(57) ABSTRACT

The present invention relates to novel compounds having histone deacetylase 6 (HDAC6) in-hibitory activity, stereoisomers thereof or pharmaceutically acceptable salts thereof the use thereof for the preparation of therapeutic medicaments, pharmaceutical compositions containing the same, a method for treating diseases using the composition, and methods for preparing the novel compounds. The novel compounds stereoisomers thereof or pharmaceutically acceptable salts thereof according to the present invention have histone deacetylase (HDAC) inhibitory activity and are effective for the prevention or treatment of HDAC6-mediated diseases, including infectious diseases; neoplasms; endocrine, nutritional and metabolic diseases; mental and be-havioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities.

16 Claims, No Drawings

(56) References Cited

U.S. PATENT DOCUMENTS

| | | |
|---|---|---|
| 2012/0289495 A1 | 11/2012 | Baloglu et al. |
| 2013/0059883 A1 | 3/2013 | Baloglu et al. |
| 2014/0005133 A1 | 1/2014 | Trivedi et al. |
| 2014/0142105 A1 | 5/2014 | Hebach et al. |
| 2014/0329825 A1 | 11/2014 | Hebach et al. |
| 2017/0015809 A1 | 1/2017 | Hawkins et al. |
| 2018/0230114 A1 | 8/2018 | Lee et al. |
| 2018/0251437 A1 | 9/2018 | Lee et al. |

FOREIGN PATENT DOCUMENTS

| | | |
|---|---|---|
| JP | 2009542752 | 12/2009 |
| JP | 2011008205 | 1/2011 |
| JP | 2011502133 | 1/2011 |
| JP | 2012211149 | 11/2012 |
| JP | 2013517278 | 5/2013 |
| JP | 2013517281 | 5/2013 |
| JP | 2014520794 | 8/2014 |
| JP | 2014524922 | 9/2014 |
| JP | 2014533721 | 12/2014 |
| JP | 2014533734 | 12/2014 |
| KR | 100265385 | 11/2000 |
| KR | 100903743 | 6/2009 |
| KR | 20147017436 | 11/2012 |
| KR | 101262870 | 5/2013 |
| KR | 101320198 | 10/2013 |
| KR | 20130112911 | 10/2013 |
| KR | 20140097459 | 8/2014 |
| KR | 101561860 | 10/2015 |
| RU | 2515611 | 8/2012 |
| WO | 2003/028729 | 4/2003 |
| WO | WO 2007011626 | 1/2007 |
| WO | WO 2007/032445 | 3/2007 |
| WO | 2007/107758 | 9/2007 |
| WO | WO 2009/010479 | 1/2009 |
| WO | WO 2010/123933 | 10/2010 |
| WO | WO 2010/126002 | 11/2010 |
| WO | WO 2011/088181 | 7/2011 |
| WO | WO 2011/088192 | 7/2011 |
| WO | WO 2011/104680 | 9/2011 |
| WO | WO 2011/133888 | 10/2011 |
| WO | WO 2012/013716 | 2/2012 |
| WO | 2013/066835 | 5/2013 |
| WO | 2013/066839 | 5/2013 |
| WO | WO 2013/066833 | 5/2013 |
| WO | WO 2013/080120 | 6/2013 |
| WO | WO 2015/033301 | 3/2015 |
| WO | WO 2015/087151 | 6/2015 |
| WO | WO 2016082930 | 6/2016 |
| WO | WO 2017/018803 | 2/2017 |
| WO | WO 2017/018804 | 2/2017 |
| WO | WO 2017/018805 | 2/2017 |
| WO | WO 2017/023133 | 2/2017 |
| WO | WO 2017/065473 | 4/2017 |

OTHER PUBLICATIONS

Warrell et al., Natl. Cancer Inst. 90, 1621-1625 (1998).
Wiest et al., J. Org. Chem 78, 5051-5055 (2013).
Witt et al., Cancer Letters 277, 8-21 (2009).
Woster et al., Med. Chem. Commun., online publication (2015).
Yao et al., Mol. Cell 18,601-607 (2005).
International Search Report of ISA/KR for PCT/KR2016/008622 (dated Feb. 17, 2017).
Cancer [online], [retrieved on Jul. 6, 2007]. Retrieved from the internet, URL http://www.nlm.nih.gov/mededlineplus/cancer.html (10 pages).
Golub et al., Molecular Classification of Cancer: Class Discovery and Class Prediction by Gene Expression Monitoring, Science 286:531-537 (1999).
Lala et al., Role of nitric oxide in tumor progression: Lessons from experimental tumors, Cancer and Metastasis Reviews 17(1):91-106 (1998).
AU Examination Report No. 1 for App No. AU201603891, dated Nov. 16, 2019 (7 pages).
CA Office Action for App No. CA 2993929, dated Dec. 4, 2018 (4 pages).
CAS Registry No. 1384673-31-7 [Entered STN: Jul. 27, 2012] (Year: 2012).
CAS Registry No. 1436149-02-8 [Entered STN: Jun. 9, 2013] (Year: 2013).
CAS Registry No. 904635-69-4 (Aug. 25, 2006).
CAS Registry No. 904652-71-7 (Aug. 25, 2006).
CAS Registry No. 904653-13-0 (Aug. 25, 2006).
EP Suppl Search Report for App No. EP 16833369, dated Apr. 1, 2019 (6 pages).
IN Office Action for App No. 201817006324, dated Jun. 27, 2019 (6 pages).
Othman et al., *1,3,4-Oxadiazole, 1,3,4-thiadiazole and 1,2,4-triazole derivatives as potential antibacterial agents*, Arabian Journal of Chemistry (2014) https://doi.org/10.1016/j.arabjc.2014.09.003 (16 pages).
U.S. Appl. No. 15/747,952, filed Jan. 26, 2018, Lee et al.
U.S. Appl. No. 15/747,850, filed Jan. 26, 2018, Lee et al.
U.S. Appl. No. 15/748,081, filed Jan. 26, 2018, Lee et al.
U.S. Appl. No. 15/763,972, filed Mar. 28, 2018, Kim et al.
AU Office Action for AU App No. 2016299484, dated Aug. 28, 2018 (6 pages).
AU Office Action for AU App No. 2016299486, dated Jul. 31, 2018 (5 pages).
Chen, J.J. et al., *Discovery of 2-methylpyridine-based biaryl amides as y-secretase modulators for the treatment of Alzheimer's disease*, Bioorganic & Medicinal Chemistry letters, 2013, 23(23):6447-6454.
International Preliminary Report on Patentability and Written Opinion for Intl. App. No. PCT/KR2016/008214 dated Jan. 30, 2018 (8 pages).
International Preliminary Report on Patentability and Written Opinion for Intl. App. No. PCT/KR2016/008216 dated Jan. 30, 2018 (9 pages).
International Preliminary Report on Patentability and Written Opinion for Intl. App. No. PCT/KR2016/008218 dated Jan. 30, 2018 (8 pages).
International Preliminary Report on Patentability and Written Opinion for Intl. App. No. PCT/KR2016/008622 dated Feb. 6, 2018 (8 pages).
International Preliminary Report on Patentability and Written Opinion for Intl. App. No. PCT/KR2016/011355 dated Apr. 17, 2018 (6 pages).
International Search Report for Int. App. No. PCT /KR2016/ 011355, dated Jan. 26, 2017 (5 pages).
International Search Report of ISA/KR for PCT/KR2016/008214, dated Nov. 24, 2016 (5 pages).
International Search Report of ISA/KR for PCT/KR2016/008216, dated Nov. 21, 2016 (4 pages).
International Search Report of ISA/KR for PCT/KR2016/008218, dated Nov. 21, 2016 (5 pages).
Japan Office Action for JP App No. 2018-505725 dated Sep. 12, 2018 (3 pages).
Korea Office Action for KR Application No. 10-2016-0095332, dated Sep. 5, 2017 (15 pages).
Korea Office Action for KR Application No. 10-2016-0095334, dated Sep. 5, 2017 (17 pages).
Korea Office Action for KR Application No. 10-2016-0099508, dated Sep. 5, 2017 (20 pages).
Korea Office Action for KR Application No. 10-2016-0131245, dated Sep. 5, 2017 (7 pages).
Manku, et al., Synthesis and evaluation of lysine derived sulfamides as histone deacetylase inhibitors, Bioorganic & Medicinal Chemistry Letters 19, 1866-1870 (2009).
Pal et al., Hydroxamic acid—A novel molecule for anticancer therapy, Journal of Advanced Pharmaceutical Technology & Research, 3(2), 92-99 (Apr.-Jun. 2012).
Rajack et al., 2,5-Disubstituted-1,3,4-oxadiazoles/thiadiazole as surface recognition moiety: Design and synthesis of novel hydroxamic

(56) References Cited

OTHER PUBLICATIONS acid based histone deacetylase inhibitors, Bioorganic & Medical Chemistry Letters, 21:5735-5738 (2011).
STN Express; Chemical Abstract compound RN: 1355844-43-7 (Feb. 8, 2012).
STN Express; Chemical Abstract compound RN: 1708354-35-1 (May 20, 2015).
STN Express; Chemical Abstract compound RN: 1790675-44-3 (Jun. 29, 2015).
STN Express; Chemical Abstract compound RN: 1798074-73-3 (Jul. 9, 2015).
STN Express; Chemical Abstract compound RN: 904653-20-9 (Aug. 25, 2006).
Taiwan Office Action for TW App No. 105132939 dated Nov. 2, 2017 (with English translation) (8 pages).
CA Office Action for CA App No. 2993918, dated Dec. 4, 2018 (5 pages).
CAS Registry No. 904529-79-9 (Aug. 25, 2006).
CAS Registry No. 904541-56-6 (Aug. 25, 2006).
CAS Registry No. 904541-91-9 (Aug. 25, 2006).
CAS Registry No. 904548-90-9 (Aug. 25, 2006).
CAS Registry No. 904549-01-5 (Aug. 25, 2006).
CAS Registry No. 904549-10-3 (Aug. 25, 2006).
CAS Registry No. 904556-59-8 (Aug. 25, 2006).
CAS Registry No. 904568-68-9 (Aug. 25, 2006).
CS Registry No. 904568-84-9 (Aug. 25, 2006).
CAS Registry No. 904569-62-6 (Aug. 25, 2006).
CAS Registry No. 904635-15-0 (Aug. 25, 2006).
CAS Registry No. 904635-23-0 (Aug. 25, 2006).
CAS Registry No. 904635-49-0 (Aug. 25, 2006).
CAS Registry No. 904635-57-0 (Aug. 25, 2006).
CAS Registry No. 904635-61-6 (Aug. 25, 2006).
CAS Registry No. 904635-67-2 (Aug. 25, 2006).
CAS Registry No. 904644-90-2 (Aug. 25, 2006).
CAS Registry No. 904644-93-5 (Aug. 25, 2006).
CAS Registry No. 904645-01-8 (Aug. 25, 2006).
CAS Registry No. 904645-03-0 (Aug. 25, 2006).
CAS Registry No. 904645-27-8 (Aug. 25, 2006).
CAS Registry No. 904645-29-0 (Aug. 25, 2006).
CAS Registry No. 904645-35-2 (Aug. 25, 2006).
CAS Registry No. 904645-35-8 (Aug. 25, 2006).
CAS Registry No. 904645-37-0 (Aug. 25, 2006).
CAS Registry No. 904645-47-2 (Aug. 25, 2006).
CAS Registry No. 904652-55-1 (Aug. 25, 2006).
CAS Registry No. 904652-68-2 (Aug. 25, 2006).
CAS Registry No. 904653-05-0 (Aug. 25, 2006).
CAS Registry No. 904653-11-8 (Aug. 25, 2006).
CAS Registry No. 904653-15-2 (Aug. 25, 2006).
CAS Registry No. 904653-17-4 (Aug. 25, 2006).
CAS Registry No. 904653-21-0 (Aug. 25, 2006).
CAS Registry No. 904653-22-1 (Aug. 25, 2006).
JP Office Action for App No. JP 2018-504720, dated Jan. 8, 2019 (English Translation) (4 pages).
NZ Office Action for App No. NZ739211, dated Jun. 14, 2019 (3 pages).
RU Office Action for RU App. No. 2018106914, dated Nov. 15, 2018 (with English translation) (14 pages).
CAS Registry No. 904645-39-2 Database Registry [Online] retrieved from STN, searched on Nov. 14, 2018.
CAS Registry No. 904652-59-1 Database Registry [Online] retrieved from STN, searched on Nov. 14, 2018.
AU Office Action for AU App No. 2016299484, dated Dec. 18, 2018 (3 pages).
AU Office Action for AU App No. 2016299485, dated Sep. 13, 2018 (7 pages).
CA Office Action for CA App No. 2987570, dated Oct. 18, 2018 (5 pages).
EP Extended Search Report for EP App No. 16830836.9, dated Dec. 19, 2018 (7 pages).
EP Extended Search Report for EP App No. 16830837.7, dated Dec. 17, 2018 (9 pages).
EP Extended Search Report for EP App No. 16830838.5, dated Nov. 19, 2018 (7 pages).
JP Office Action for App No. JP 2018-503804, dated Dec. 18, 2018 (with English Translation) (4 pages).
JP Office Action for JP App No. 2018-504096, dated Dec. 18, 2018 (with English Translation) (5 pages).
Rossi et al., 4-N-Hydroxy-4-[1-(sulfonyl)piperidin-4-yl]-butyramides as HDAC inhibitors, Bioorganic & Medicinal Chemistry Letters, 21:6767-6769 (2011).
RU Office Action for App. No. RU2018106877, dated Oct. 18, 2018 (with English translation) (16 pages).
RU Office Action for RU App. No. 2018106904, dated Sep. 20, 2018 (with English translation) (14 pages).
Gamal El-Din. et, al, *Synthesis and in vitro antiproliferative activity of new 1,3,4-oxadiazole derivatives possessing sulfonamide moiety*, European Journal of Medicinal Chemistry, 90:45-52, (Jan. 27, 2015).
IN Office Action for App No. 201727037873, dated May 21, 2019 (7 pages).

\* cited by examiner

1,3,4-OXADIAZOLE DERIVATIVE COMPOUNDS AS HISTONE DEACETYLASE 6 INHIBITOR, AND THE PHARMACEUTICAL COMPOSITION COMPRISING THE SAME

TECHNICAL FIELD

The present invention relates to 1,3,4-oxadiazole derivative compounds having histone deacetylase 6 (HDAC6) inhibitory activity, stereoisomers thereof, or pharmaceutically acceptable salts thereof; uses thereof for the preparation of therapeutic medicaments; methods of treating diseases using the same; pharmaceutical compositions comprising the same; and methods for preparing the same.

BACKGROUND ART

Post-translational modifications such as acetylation are very crucial regulatory modules at the heart of biological processes in the cells and are tightly regulated by a multitude of enzymes. Histones are the chief protein components of chromatin and act as spools around which DNA strands. Also, the balance of histone acetylation and deacetylation is a critical role in the regulation of gene expression.

Histone deacetylases (HDACs) are enzymes that remove acetyl groups from lysine residues on histone proteins of chromatin, and are known to be associated with gene silencing and induce cell cycle arrest, angiogenic inhibition, immune regulation, cell death, etc. (Hassig et al., Curr. Opin. Chem. Biol. 1997, 1, 300-308). In addition, it was reported that the inhibition of enzymatic function of HDACs induces the apoptosis of cancer cells in vivo by reducing the activity of cancer cell survival-associated factors and activating cancer cell apoptosis-associated factors (Warrell et al, J. Natl. Cancer Inst. 1998, 90, 1621-1625).

In humans, 18 HDACs have been identified and are subdivided into four classes based on their homology to yeast HDACs. Among them, 11 HDACs use zinc as a cofactor and can be divided into three groups: Class I (HDAC1, 2, 3 and 8). Class II (IIa: HDAC4, 5, 7 and 9; IIb: HDAC6 and 10). Class IV (HDAC 11). Additionally, 7 HDACs of Class III (SIRT 1-7) require NAD+ instead of zinc as a cofactor (Bolden et al., Nat. Rev. Drug Discov. 2006, 5(9), 769-784).

Various HDAC inhibitors are in preclinical or clinical development, but to date, only non-selective HDAC inhibitors have been identified as anticancer agents, and only vorinostat (SAHA) and romidepsin (FK228) have been approved for the treatment of cutaneous T-cell lymphoma. However, non-selective HDAC inhibitors are known to cause side effects such as fatigue and nausea, generally at high doses (Piekarz et al., Pharmaceuticals 2010, 3, 2751-2767). Such side effects have been reported to be due to the inhibition of class I HDACs. Due to such side effects, the use of non-selective HDAC inhibitors in the development of drugs other than anticancer drugs has been limited (Witt et al., Cancer Letters, 2009, 277, 8-21).

Meanwhile, it was reported that the selective inhibition of class II HDACs would not show toxicity shown in the inhibition of class I HDACs. Also, when selective HDAC inhibitors are developed, side effects such as toxicity, which are caused by the non-selective HDAC inhibition, can be overcome. Thus, selective HDAC inhibitors have potential to be developed as therapeutic agents effective for the treatment of various diseases (Matthias et al., Mol. Cell. Biol. 2008, 28, 1688-1701).

It is known that HDAC6, a member of Class IIb HDACs, is present mainly in the cytoplasm and is involved in the deacetylation of a number of non-histone substrates (HSP90, cortactin, etc.), including tubulin, (Yao et al., Mol. Cell 2005, 18, 601-607). HDAC6 has two catalytic domains, and the zinc finger domain of C-terminal can bind to ubiquitinated proteins. It is known that HDAC6 has a number of non-histone proteins as substrates, and thus plays an important role in various diseases, including cancer, inflammatory diseases, autoimmune diseases, neurological diseases and neurodegenerative disorders (Santo et al., Blood 2012 119: 2579-259; Vishwakarma et al., International Immunopharmacology 2013, 16, 72-78; Hu et al., J. Neurol. Sci. 2011, 304, 1-8).

The common structural characteristic of various HDAC inhibitors is a structure consisting of a cap group, a linker and a zinc-binding group (ZBG), as shown in the following Vorinostat structure. Many researchers have conducted studies on enzyme inhibitory activity and selectivity by structurally modifying the cap group and the linker. Among these groups, the zinc-binding group is known to play a more important role in enzyme inhibitory activity and selectivity (Wiest et al., J. Org. Chem. 2013 78: 5051-5055; Methot et al., Bioorg. Med. Chem. Lett. 2008, 18, 973-978).

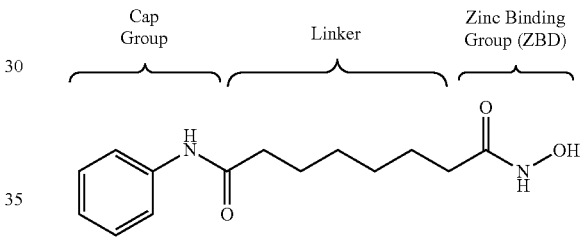

The zinc-binding group is generally a hydroxamic acid or benzamide derivative. Herein, the hydroxamic acid derivative exhibits a potent HDAC inhibitory effect, but has problems of low bioavailability and severe off-target activity. In addition, the benzamide derivative has a problem in that it can produce toxic metabolites in vivo, because it contains aniline (Woster et al., Med. Chem. Commun. 2015, online publication).

Accordingly, there is a need for the development of selective HDAC 6 inhibitors for treatment of diseases such as cancer, inflammatory diseases, autoimmune diseases, neurological diseases and neurodegenerative disorders, which have a zinc-binding group with improved bioavailability and, at the same time, cause no side effects, unlike non-selective inhibitors that cause side effects.

DISCLOSURE OF INVENTION

Technical Problem

It is an object of the present invention to provide 1,3,4-oxadiazole derivative compounds having selective HDAC6 inhibitory activity, stereoisomers thereof, or pharmaceutically acceptable salts thereof.

Another object of the present invention is to provide pharmaceutical compositions containing 1,3,4-oxadiazole derivative compounds having selective HDAC6 inhibitory activity, stereoisomers thereof, or pharmaceutically acceptable salts thereof.

Still another object of the present invention is to provide methods for preparing the novel compounds.

Still another object of the present invention is to provide pharmaceutical compositions for prevention or treatment of HDAC6 activity-associated diseases, including infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities, which contain the above compound.

Still another object of the present invention is to provide the use of the compounds for the preparation of therapeutic medicaments against HDAC6 activity-associated diseases.

Yet another object of the present invention is to provide methods for treating HDAC6 activity-associated diseases, which comprise administering a therapeutically effective amount of the pharmaceutical compositions containing the compounds.

Solution to Problem

The present inventors have discovered 1,3,4-oxadiazole derivative compounds, which have histone deacetylase 6 (HDAC6) inhibitory activity, and have found that these compounds can be used for the inhibition or treatment of histone deacetylase 6 (HDAC6) activity-associated diseases, thereby completing the present invention.

1,3,4-Oxadiazole Derivative Compounds

To achieve the above objects, the present invention provides an 1,3,4-oxadiazole derivative compound represented by the following formula I, a stereoisomer thereof, or a pharmaceutically acceptable salt thereof:

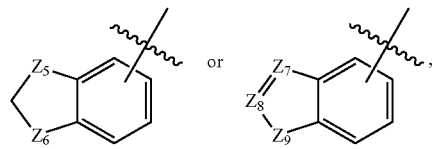

[Formula I]

wherein $L_1$, $L_2$ or $L_3$ are each independently —$(C_0$-$C_2$ alkyl)-:
$R_1$ is —$CX_2H$ or —$CX_3$;
$R_2$ is —$NR^AR^B$, —$OR^C$,

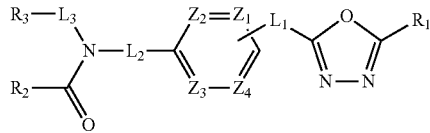

wherein at least one H of or

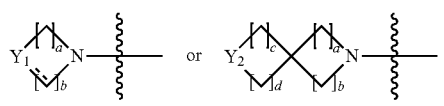

may be substituted with —X, —OH, —$O(C_1$-$C_4$ alkyl), —$NR^DR^E$, —$(C_1$-$C_4$ alkyl), —$CF_3$, —$CF_2H$, —CN, -aryl, -heteroaryl, —$(C_1$-$C_4$ alkyl)-aryl or —$(C_1$-$C_4$ alkyl)-heteroaryl, wherein at least one H of the -aryl, -heteroaryl, —$(C_1$-$C_4$ alkyl)-aryl or —$(C_1$-$C_4$ alkyl)-heteroaryl may be substituted with —X, —OH, —$CF_3$ or —$CF_2H$;

$R_3$ is —H, —$(C_1$-$C_4$ alkyl), —$(C_1$-$C_4$ alkyl)-$O(C_1$-$C_4$ alkyl), —$(C_1$-$C_4$ alkyl)-C(=O)—$O(C_1$-$C_4$ alkyl), —$(C_3$-$C_7$ cycloalkyl), —$(C_2$-$C_6$ heterocycloalkyl), -aryl, -heteroaryl, -adamantyl,

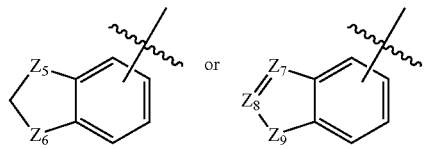

wherein at least one H of the —$(C_1$-$C_4$ alkyl) may be substituted with —X or —OH, at least one H of the -aryl or -heteroaryl may be substituted with —X, —OH, —$O(C_1$-$C_4$ alkyl), —$OCF_3$, —O-aryl, —$NR^DR^E$, —$(C_1$-$C_4$ alkyl), —$CF_3$, —$CF_2H$, —C(=O)—$(C_1$-$C_4$ alkyl), —C(=O)—$O(C_1$-$C_4$ alkyl), —C(=O)—$NR^DR^E$, —$S(=O)_2$—$(C_1$-$C_4$ alkyl), -aryl, -heteroaryl,

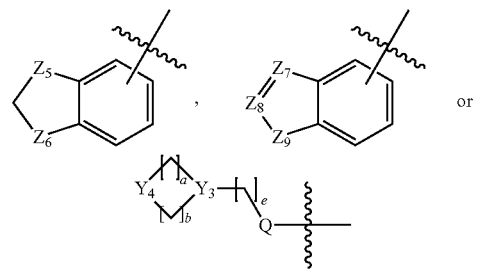

wherein at least one H of

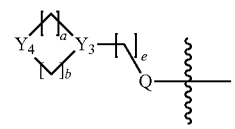

may be substituted with —X, —$(C_1$-$C_4$ alkyl), —$CF_3$ or —$CF_2H$, and at least one H of the —$(C_3$-$C_7$ cycloalkyl), —$(C_{2-6}$ heterocycloalkyl), -adamantyl,


may be substituted with —X, —OH or —$(C_1$-$C_4$ alkyl);

$Y_1$, $Y_2$ and $Y_4$ are each independently —$CH_2$—, —$NR^F$—, —O—, —C(=O)— or —$S(=O)_2$—;
$Y_3$ is —$CH_2$— or —N—;
$Z_1$ to $Z_4$ are each independently N or $CR^Z$, wherein at least three of $Z_1$ to $Z_4$ may not be simultaneously N, and $R^Z$ is —H, —X or —$O(C_1$-$C_4$ alkyl);
$Z_5$ and $Z_6$ are each independently —$CH_2$— or —O—;

$Z_7$ and $Z_8$ are each independently =CH— or =N—;
$Z_9$ is —$NR^G$— or —S—;
$R^A$ and $R^B$ are each independently —H, —($C_1$-$C_4$ alkyl), —($C_1$-$C_4$ alkyl)-OH, —($C_1$-$C_4$ alkyl)-$NR^DR^E$, -aryl, —($C_1$-$C_4$ alkyl)-aryl, -heteroaryl, —($C_1$-$C_4$ alkyl)-heteroaryl, —($C_1$-$C_7$ cycloalkyl), —($C_2$-$C_6$ heterocycloalkyl) or

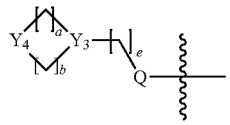

wherein at least one H of the —($C_1$-$C_4$ alkyl), —($C_1$-$C_4$ alkyl)-OH or —($C_1$-$C_4$ alkyl)-$NR^DR^E$ may be substituted with —X, at least one H of the -aryl, —($C_1$-$C_4$ alkyl)-aryl, -heteroaryl, —($C_1$-$C_4$ alkyl)-heteroaryl, —($C_3$-$C_7$ cycloalkyl) or —($C_2$-$C_6$ heterocycloalkyl) may be substituted with —X, —OH, —O($C_1$-$C_4$ alkyl), —($C_1$-$C_4$ alkyl), —$CF_3$, —$CF_2H$ or —CN, and at least one H of

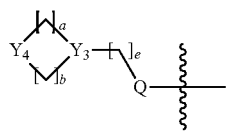

may be substituted with —X, —OH, —O($C_1$-$C_4$ alkyl), —($C_1$-$C_4$ alkyl), —CF, —$CF_2H$, —CN, —($C_2$-$C_6$ heterocycloalkyl), -aryl, —($C_1$-$C_4$ alkyl)-aryl or -heteroaryl;

$R^C$ is —($C_1$-$C_4$ alkyl), -aryl, —($C_1$-$C_4$ alkyl)-aryl, -heteroaryl or —($C_1$-$C_4$ alkyl)-heteroaryl,
wherein at least one H of the —($C_1$-$C_4$ alkyl) may be substituted with —X or —OH, and
at least one H of the -aryl, —($C_1$-$C_4$ alkyl)-aryl, -heteroaryl or —($C_1$-$C_4$ alkyl)-heteroaryl may be substituted with —X, —OH, —CF, or —$CF_2H$;

$R^D$ and $R^E$ are each independently —H, —($C_1$-$C_4$ alkyl), -aryl or —($C_1$-$C_4$ alkyl)-aryl,
wherein at least one H of the —($C_1$-$C_4$ alkyl) may be substituted with —X or —OH, and
at least one H of the -aryl or —($C_1$-$C_4$ alkyl)-aryl may be substituted with —X, —OH, —$CF_3$ or —$CF_2H$;

$R^F$ is —H, —($C_1$-$C_6$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —($C_1$-$C_4$ alkyl)-C(=O)—O($C_1$-$C_4$ alkyl), —($C_1$-$C_4$ alkyl)-$NR^DR^E$, —S(=O)$_2$—($C_1$-$C_4$ alkyl), -aryl, —($C_1$-$C_4$ alkyl)-aryl, —($C_2$-$C_4$ alkenyl)-aryl, -heteroaryl, —($C_1$-$C_4$ alkyl)-heteroaryl, —C(=O)—($C_3$-$C_7$ cycloalkyl), —($C_2$-$C_6$ heterocycloalkyl) or —($C_1$-$C_4$ alkyl)-C(=O)—($C_2$-$C_6$ heterocycloalkyl),
wherein at least one H of the —($C_1$-$C_4$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —($C_1$-$C_4$ alkyl)-C(=O)—O($C_1$-$C_4$ alkyl), —($C_1$-$C_4$ alkyl)-$NR^DR^E$ or —S(=O)$_2$—($C_1$-$C_4$ alkyl) may be substituted with —X, and
wherein at least one H of the -aryl, —($C_1$-$C_4$ alkyl)-aryl, —($C_2$-$C_4$ alkenylaryl, -heteroaryl, —($C_1$-$C_4$ alkyl)-heteroaryl, —C(=O)—($C_3$-$C_7$ cycloalkyl), —($C_2$-$C_6$ heterocycloalkyl) or —($C_1$-$C_4$ alkyl)-C(=O)—($C_2$-$C_6$ heterocycloalkyl) may be substituted with —X, —OH, —CF, or —$CF_2H$;

$R^C$ is —H or —($C_1$-$C_4$ alkyl);
Q is —O— or null.
==== is a single bond or a double bond, provided that ==== is a double bond, $Y_1$ is =CH—;
a to e are each independently an integer of 0, 1, 2, 3 or 4, provided that a and b may not be simultaneously 0, and c and d may not be simultaneously 0; and
X is F, Cl, Br or I.

According to preferable embodiment of the present invention,
$L_1$, $L_2$ or $L_3$ are each independently —($C_0$-$C_2$ alkyl)-;
$R_1$ is —$CX_2H$ or —$CX_3$;
$R^2$ is —$NR^AR^B$, —$OR^C$,
wherein at least one H of

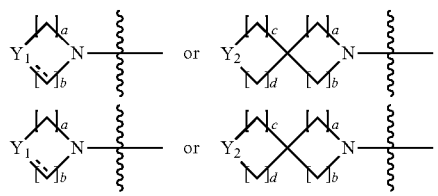

may be substituted with —X, —OH, —$NR^DR^E$, —($C_1$-$C_4$ alkyl) or -aryl, wherein at least one H of the -aryl may be substituted with —X, —OH, —$CF_3$ or —$CF_2H$;

$R_3$ is —H, —($C_1$-$C_4$ alkyl), —($C_3$-$C_7$ cycloalkyl), -aryl, -heteroaryl, -adamantyl,

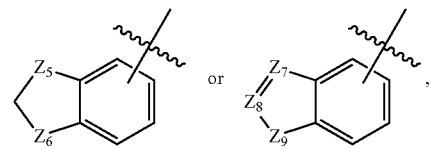

wherein at least one H of the —($C_1$-$C_4$ alkyl) may be substituted with —X or —OH,
at least one H of the -aryl or -heteroaryl may be substituted with —X, —O($C_1$-$C_4$ alkyl), —$OCF_3$, —O-aryl, —($C_1$-$C_4$ alkyl), —$CF_3$, —S(=O)$_2$—($C_1$-$C_4$ alkyl), -aryl, -heteroaryl,

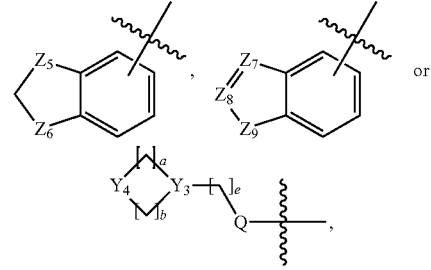

wherein at least one H of

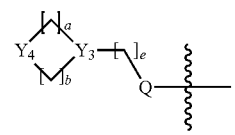

may be substituted with —X or —($C_1$-$C_4$ alkyl), and
at least one H of the —($C_7$-$C_7$ cycloalkyl), -adamantyl,

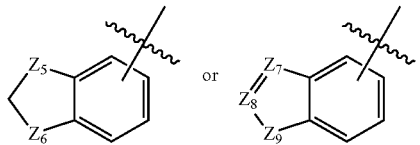

may be substituted with —X, —OH or —($C_1$-$C_4$ alkyl);

$Y_1$, $Y_2$ and $Y_4$ are each independently —$CH_2$—, —$NR^F$—, —O—, —C(=O)— or —S(=O)$_2$—;

$Y_3$ is —$CH_2$— or —N—;

$Z_1$ to $Z_4$ are each independently N or $CR^Z$, wherein at least three of $Z_1$ to $Z_4$ may not be simultaneously N, and $R^Z$ is —H, —X or —O($C_1$-$C_4$ alkyl);

$Z_5$ and $Z_6$ are each independently —$CH_2$— or —O—;

$Z_7$ and $Z_8$ are each independently =CH— or =N—;

$Z_9$ is —$NR^G$— or —S—;

$R^A$ and $R^B$ are each independently —H, —($C_1$-$C_4$ alkyl), —($C_1$-$C_4$ alkyl)-OH, —($C_1$-$C_4$ alkyl)-$NR^DR^E$, -aryl, —($C_1$-$C_4$ alkyl)-aryl, —($C_3$-$C_7$ cycloalkyl) or

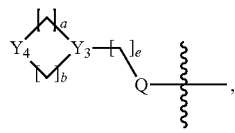

wherein at least one H of the —($C_1$-$C_4$ alkyl), —($C_1$-$C_4$ alkyl)-OH or —($C_1$-$C_4$ alkyl)-$NR^DR^E$ may be substituted with —X, at least one H of the -aryl, —($C_1$-$C_4$ alkyl)-aryl or —($C_3$-$C_7$ cycloalkyl) may be substituted with —X, —OH, —O($C_1$-$C_4$ alkyl), —($C_1$-$C_4$ alkyl), —$CF_3$, —$CF_2H$ or —CN, and at least one H of

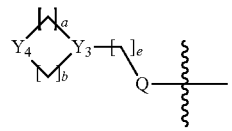

may be substituted with —X, —($C_1$-$C_4$ alkyl), —$CF_3$, —($C_2$-$C_6$ heterocycloalkyl), —($C_1$-$C_4$ alkyl)-aryl or -heteroaryl;

$R^C$ is —($C_1$-$C_4$ alkyl) or -aryl, wherein at least one H of the —($C_1$-$C_4$ alkyl) may be substituted with —X or —OH, and at least one H of the -aryl may be substituted with —X, —OH, —$CF_3$ or —$CF_2H$;

$R^D$ and $R^E$ are each independently —($C_1$-$C_4$ alkyl) or —($C_1$-$C_4$ alkyl)-aryl, wherein at least one H of the —($C_1$-$C_4$ alkyl) may be substituted with —X or —OH, and at least one H of the —($C_1$-$C_4$ alkyl)-aryl may be substituted with —X, —OH, —$CF_3$ or —$CF_2H$;

$R^F$ is —H, —($C_1$-$C_6$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —($C_1$-$C_4$ alkyl)-C(=O)—O($C_1$-$C_4$ alkyl), —($C_1$-$C_4$ alkyl)-$NR^DR^E$, —S(=O)$_2$—($C_1$-$C_4$ alkyl), -aryl, —($C_1$-$C_4$ alkyl)-aryl, —($C_2$-$C_4$ alkenyl)-aryl, -heteroaryl, —($C_1$-$C_4$ alkyl)-heteroaryl, —C(=O)—($C_3$-$C_7$ cycloalkyl), —($C_2$-$C_6$ heterocycloalkyl) or —($C_1$-$C_4$ alkyl)-C(=O)—($C_2$-$C_6$ heterocycloalkyl), wherein at least one H of the —($C_1$-$C_4$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —($C_1$-$C_4$ alkyl)-C(=O)—O($C_1$-$C_4$ alkyl), —($C_1$-$C_4$ alkyl)-$NR^DR^E$ or —S(=O)$_2$—($C_1$-$C_4$ alkyl) may be substituted with —X, and wherein at least one H of the -aryl, —($C_1$-$C_4$ alkyl)-aryl, —($C_2$-$C_4$ alkenylaryl, -heteroaryl, —($C_1$-$C_4$ alkyl)-heteroaryl, —C(=O)—($C_3$-$C_7$ cycloalkyl), —($C_2$-$C_6$ heterocycloalkyl) or —($C_1$-$C_4$ alkyl)-C(=O)—($C_2$-$C_6$ heterocycloalkyl) may be substituted with —X, —OH, —$CF_3$ or —$CF_2H$;

$R^G$ is —H or —($C_1$-$C_4$ alkyl);

Q is —O— or null,

---- is a single bond or a double bond, provided that ---- is a double bond, $Y_1$ is =CH—;

a to e are each independently an integer of 0, 1, 2, 3 or 4, provided that a and b may not be simultaneously 0, and c and d may not be simultaneously 0; and X is F, Cl, Br or I.

According to more preferable embodiment of the present invention, $L_1$ or $L_2$ are each independently —($C_0$ alkyl)-;

$L_2$ is —($C_1$ alkyl)-;

$R_1$ is —$CF_2H$ or —$CF_3$;

$R_2$ is —$NR^AR^B$,

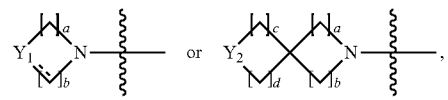

wherein at least one H of

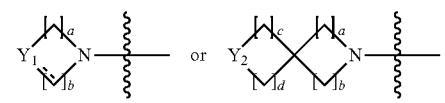

may be substituted with —X, —$NR^DR^E$ or —($C_1$-$C_4$ alkyl);

$R_3$ is -aryl, -heteroaryl,

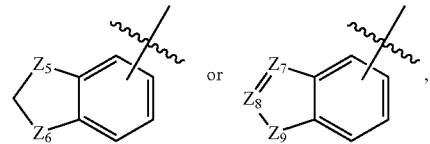

wherein at least one H of the -aryl or -heteroaryl may be substituted with —X, —O($C_1$-$C_4$ alkyl), —$OCF_3$, —($C_1$-$C_4$ alkyl), -heteroaryl or

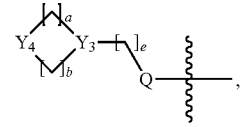

wherein at least one H of

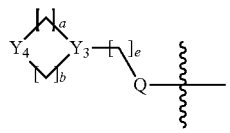

may be substituted with —X or —($C_1$-$C_4$ alkyl), and
at least one H of the

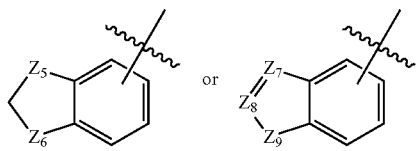

may be substituted with —X, —OH or —($C_1$-$C_4$ alkyl);
$Y_1$ is —$CH_2$—, —$NR^F$—, —O— or —$S(=O)_2$—;
$Y_2$ is —$NR^F$— or —O—;
$Y_3$ is —N—;
$Y_4$ is —$NR^F$—, —O— or —$S(=O)_2$—;
$Z_1$ to $Z_4$ are each independently N or $CR^Z$, wherein at least two of $Z_1$ to $Z_4$ may not be simultaneously N, and $R^Z$ is —H or —X;
$Z_5$ and $Z_6$ are each independently —$CH_2$— or —O—;
$Z_7$ and $Z_8$ are each independently =CH— or =N—;
$Z_9$ is —$NR^G$—;
$R^A$ and $R^B$ are each independently —($C_1$-$C_4$ alkyl), —($C_1$-$C_4$ alkyl)-OH, —($C_1$-$C_4$ alkyl)-$NR^D R^E$ or

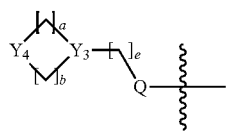

wherein at least one H of the —($C_1$-$C_4$ alkyl), —($C_1$-$C_4$ alkyl)-OH or —($C_1$-$C_4$ alkyl)-$NR^D R^E$ may be substituted with —X, and
at least one H of

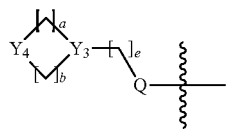

may be substituted with —X or —($C_1$-$C_4$ alkyl);
$R^D$ and $R^E$ are each independently —($C_1$-$C_4$ alkyl), wherein at least one H of the —($C_1$-$C_4$ alkyl) may be substituted with —X or —OH;
$R^E$ is —H, —($C_1$-$C_6$ alkyl), —($C_1$-$C_4$ alkyl)-OH, —C(=O)—($C_1$-$C_4$ alkyl), —$S(=O)_2$—($C_1$-$C_4$ alkyl) or —($C_2$-$C_6$ heterocycloalkyl),
wherein at least one H of the —($C_1$-$C_4$ alkyl), —($C_1$-$C_4$ alkyl)-OH, —C(=O)—($C_1$-$C_4$ alkyl) or —$S(=O)_2$—($C_1$-$C_4$ alkyl) may be substituted with —X, and
wherein at least one H of the —($C_2$-$C_6$ heterocycloalkyl) may be substituted with —X, —OH, —$CF_3$ or —$CF_2$H;
$R^G$ is —H or —($C_1$-$C_4$ alkyl);
==== is a single bond;
a to d are each independently an integer of 1 or 2;

e is an integer of 0, 1, 2, 3 or 4; and
X is F, Cl or Br.
According to particularly preferable embodiment of the present invention,
$L_1$ or $L_3$ are each independently —($C_0$ alkyl)-;
$L_2$ is —($C_1$ alkyl)-;
$R_1$ is —$CF_2$H;
$R_2$ is —$NR^A R^B$.
wherein at least one H of

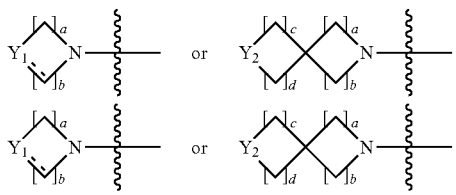

may be substituted with —X or —$NR^D R^E$;
$R_3$ is -aryl, -heteroaryl or

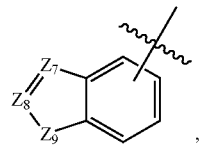

wherein at least one H of the -aryl or -heteroaryl may be substituted with —X, —($C_1$-$C_4$ alkyl) or -heteroaryl, and
at least one H of the

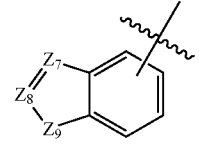

may be substituted with —X, —OH or —($C_1$-$C_4$ alkyl);
$Y_1$ is —$CH_2$—, —$NR^F$—, —O— or —$S(=O)_2$—;
$Y_2$ is —$NR^F$— or —O—;
$Z_1$ to $Z_4$ are each independently N or $CR^Z$, wherein at least two of $Z_1$ to $Z_4$ may not be simultaneously N, and $R^Z$ is —H or —X;
$Z_7$ and $Z_8$ are each independently =CH— or =N—;
$Z_9$ is —$NR^G$—;
$R^A$ and $R^B$ are each independently —($C_1$-$C_4$ alkyl) or —($C_1$-$C_4$ alkyl)-OH,
wherein at least one H of the —($C_1$-$C_4$ alkyl) or —($C_1$-$C_4$ alkyl)-OH may be substituted with —X;
$R^D$ and $R^E$ are each independently —($C_1$-$C_4$ alkyl), wherein at least one H of the —($C_1$-$C_4$ alkyl) may be substituted with —X or —OH;
$R^F$ is —H, —($C_1$-$C_6$ alkyl), —($C_1$-$C_4$ alkyl)-OH, —C(=O)—($C_1$-$C_4$ alkyl), —$S(=O)_2$—($C_1$-$C_4$ alkyl) or —($C_2$-$C_6$ heterocycloalkyl),
wherein at least one H of the —($C_1$-$C_4$ alkyl), —($C_1$-$C_4$ alkyl)-OH, —C(=O)—($C_1$-$C_4$ alkyl) or —$S(=O)_2$—($C_1$-$C_4$ alkyl) may be substituted with —X, and
wherein at least one H of the —($C_2$-$C_6$ heterocycloalkyl) may be substituted with —X, —OH, —$CF_3$ or —$CF_2$H;
$R^G$ is —H or —($C_1$-$C_4$ alkyl);
==== is a single bond;
a to d are each independently an integer of 1 or 2; and
X is F, Cl or Br.

The specific compounds represented by formula I are shown in Table 1 below:
TABLE 1
| Ex. | Comp. | Structure |
|---|---|---|
| 1 | 21249 | 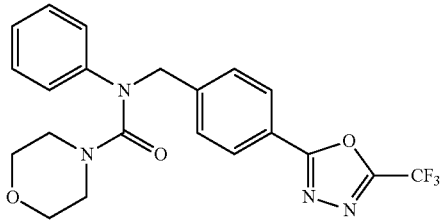 [SMILES: O=C(N1CCOCC1)N(Cc1ccc(-c2nnc(C(F)(F)F)o2)cc1)c1ccccc1] |
| 2 | 21285 | 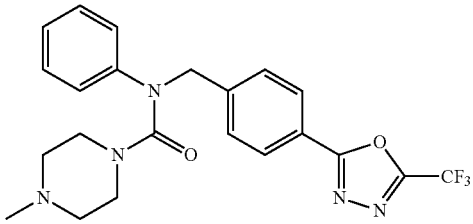 [SMILES: CN1CCN(C(=O)N(Cc2ccc(-c3nnc(C(F)(F)F)o3)cc2)c2ccccc2)CC1] |
| 3 | 21318 | 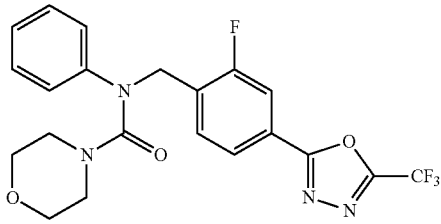 [SMILES: O=C(N1CCOCC1)N(Cc1ccc(-c2nnc(C(F)(F)F)o2)cc1F)c1ccccc1] |
| 4 | 21319 | 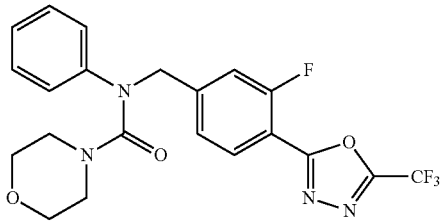 [SMILES: O=C(N1CCOCC1)N(Cc1ccc(-c2nnc(C(F)(F)F)o2)c(F)c1)c1ccccc1] |
| 5 | 21325 | 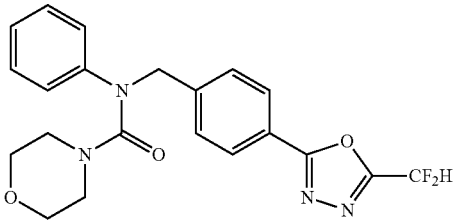 [SMILES: O=C(N1CCOCC1)N(Cc1ccc(-c2nnc(C(F)F)o2)cc1)c1ccccc1] |
| 6 | 21327 | 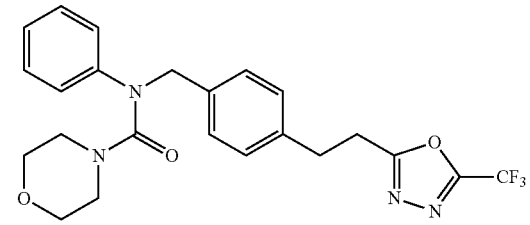 [SMILES: O=C(N1CCOCC1)N(Cc1ccc(CCc2nnc(C(F)(F)F)o2)cc1)c1ccccc1] |

TABLE 1-continued

| Ex. | Comp. | Structure |
|---|---|---|
| 7 | 21329 | 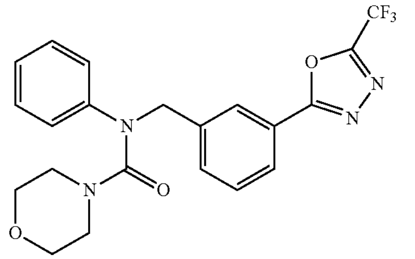 [SMILES: O=C(N1CCOCC1)N(Cc1cccc(-c2nnc(C(F)(F)F)o2)c1)c1ccccc1] |
| 8 | 21333 | 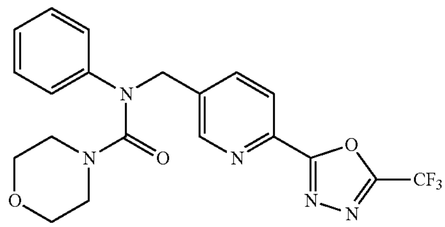 [SMILES: O=C(N1CCOCC1)N(Cc1ccc(-c2nnc(C(F)(F)F)o2)nc1)c1ccccc1] |
| 9 | 21336 | 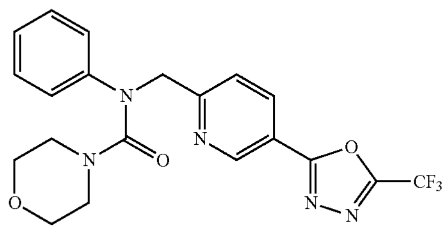 [SMILES: O=C(N1CCOCC1)N(Cc1ccc(-c2nnc(C(F)(F)F)o2)cn1)c1ccccc1] |
| 10 | 21337 | 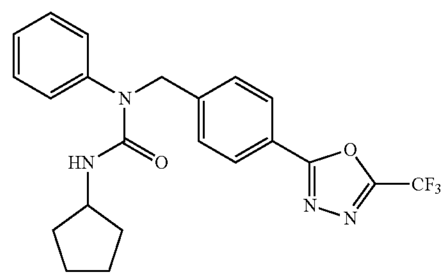 [SMILES: O=C(NC1CCCC1)N(Cc1ccc(-c2nnc(C(F)(F)F)o2)cc1)c1ccccc1] |
| 11 | 21340 | 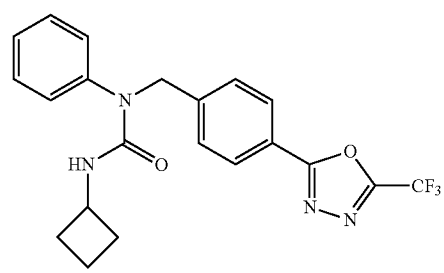 [SMILES: O=C(NC1CCC1)N(Cc1ccc(-c2nnc(C(F)(F)F)o2)cc1)c1ccccc1] |
| 12 | 21341 | 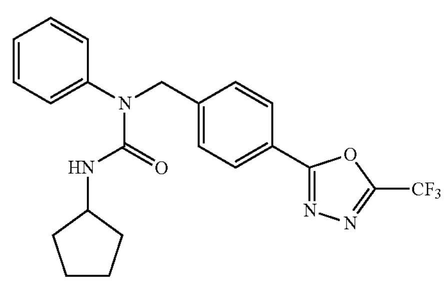 [SMILES: O=C(NC1CCCC1)N(Cc1ccc(-c2nnc(C(F)(F)F)o2)cc1)c1ccccc1] |

TABLE 1-continued

| Ex. | Comp. | Structure |
|---|---|---|
| 13 | 21342 | 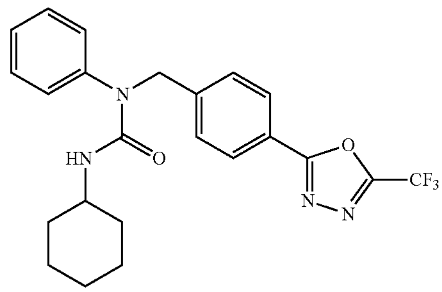 [SMILES: O=C(NC1CCCCC1)N(Cc1ccc(-c2nnc(C(F)(F)F)o2)cc1)c1ccccc1] |
| 14 | 21343 | 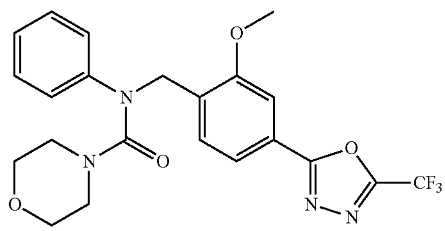 [SMILES: COc1cc(-c2nnc(C(F)(F)F)o2)ccc1CN(C(=O)N1CCOCC1)c1ccccc1] |
| 15 | 21344 | 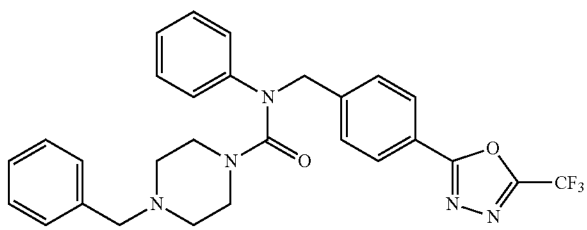 [SMILES: O=C(N1CCN(Cc2ccccc2)CC1)N(Cc1ccc(-c2nnc(C(F)(F)F)o2)cc1)c1ccccc1] |
| 16 | 21345 | 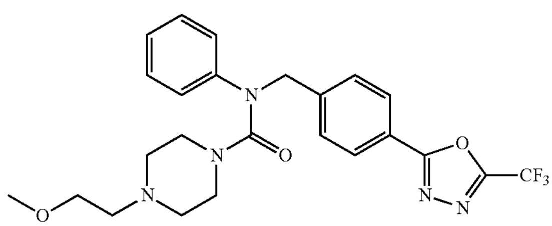 [SMILES: COCCN1CCN(C(=O)N(Cc2ccc(-c3nnc(C(F)(F)F)o3)cc2)c2ccccc2)CC1] |
| 17 | 21346 | 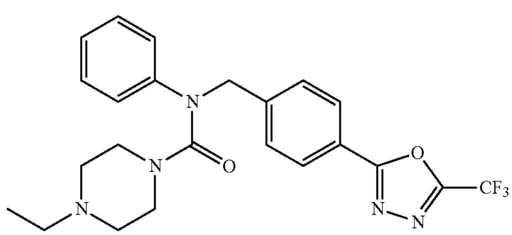 [SMILES: CCN1CCN(C(=O)N(Cc2ccc(-c3nnc(C(F)(F)F)o3)cc2)c2ccccc2)CC1] |
| 18 | 21347 | 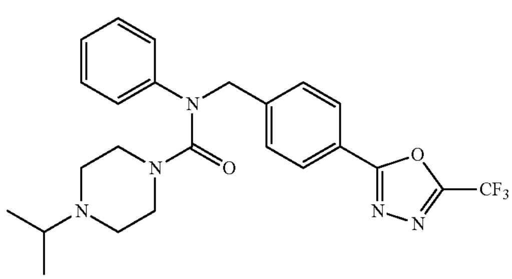 [SMILES: CC(C)N1CCN(C(=O)N(Cc2ccc(-c3nnc(C(F)(F)F)o3)cc2)c2ccccc2)CC1] |

TABLE 1-continued
| Ex. | Comp. | Structure |
|---|---|---|
| 19 | 21348 | 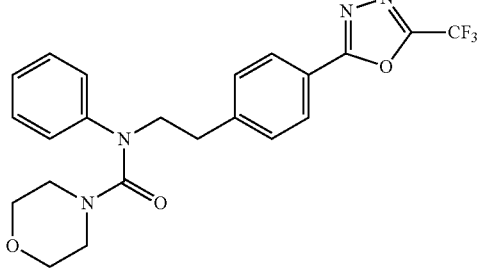 |
| 20 | 21349 | 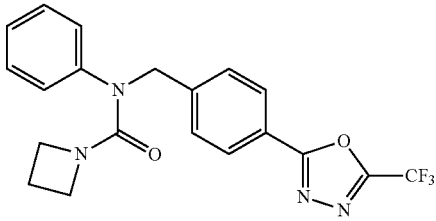 [SMILES: O=C(N1CCC1)N(Cc1ccc(-c2nnc(C(F)(F)F)o2)cc1)c1ccccc1] |
| 21 | 21350 | 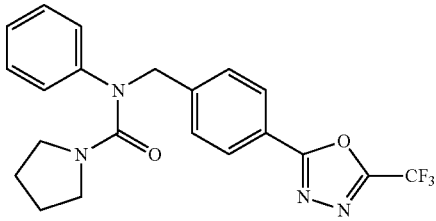 [SMILES: O=C(N1CCCC1)N(Cc1ccc(-c2nnc(C(F)(F)F)o2)cc1)c1ccccc1] |
| 22 | 21351 | 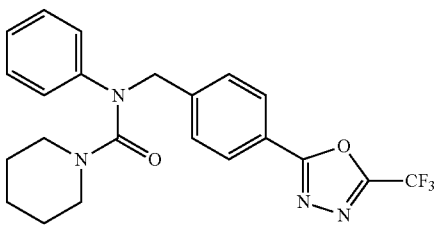 [SMILES: O=C(N1CCCCC1)N(Cc1ccc(-c2nnc(C(F)(F)F)o2)cc1)c1ccccc1] |
| 23 | 21352 | 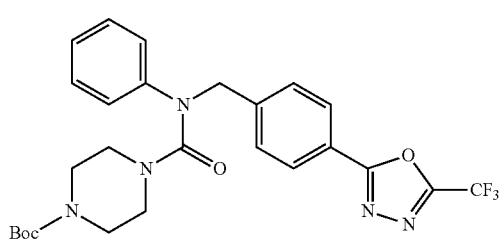 [SMILES: CC(C)(C)OC(=O)N1CCN(C(=O)N(Cc2ccc(-c3nnc(C(F)(F)F)o3)cc2)c2ccccc2)CC1] |
| 24 | 21353 | 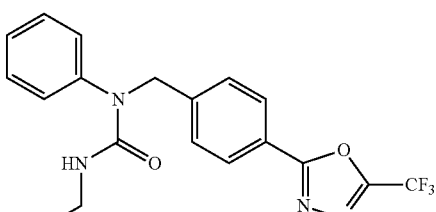 |

TABLE 1-continued

| Ex. | Comp. | Structure |
|---|---|---|
| 25 | 21354 | 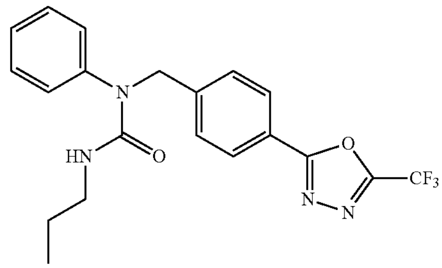 [SMILES: CCCNC(=O)N(Cc1ccc(-c2nnc(C(F)(F)F)o2)cc1)c1ccccc1] |
| 26 | 21355 | 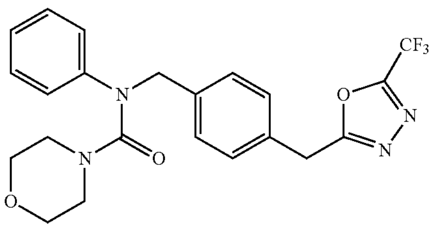 [SMILES: O=C(N1CCOCC1)N(Cc1ccc(Cc2nnc(C(F)(F)F)o2)cc1)c1ccccc1] |
| 27 | 21357 | 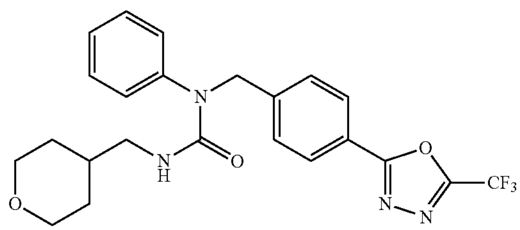 [SMILES: O=C(NCC1CCOCC1)N(Cc1ccc(-c2nnc(C(F)(F)F)o2)cc1)c1ccccc1] |
| 28 | 21358 | 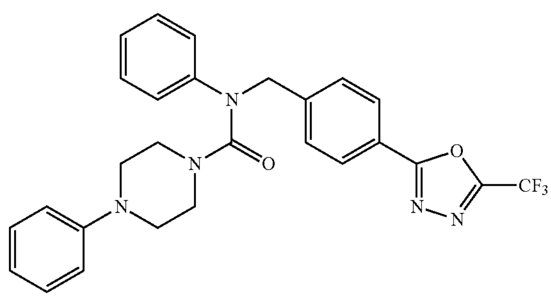 [SMILES: O=C(N1CCN(c2ccccc2)CC1)N(Cc1ccc(-c2nnc(C(F)(F)F)o2)cc1)c1ccccc1] |
| 29 | 21359 | 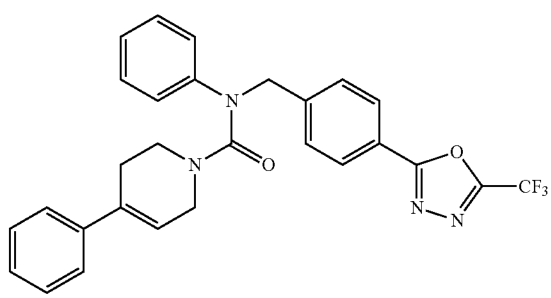 [SMILES: O=C(N1CC=C(c2ccccc2)CC1)N(Cc1ccc(-c2nnc(C(F)(F)F)o2)cc1)c1ccccc1] |
| 30 | 21360 | 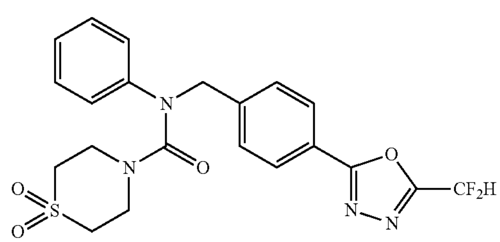 [SMILES: O=C(N1CCS(=O)(=O)CC1)N(Cc1ccc(-c2nnc(C(F)F)o2)cc1)c1ccccc1] |

TABLE 1-continued

| Ex. | Comp. | Structure |
|---|---|---|
| 31 | 21361 | 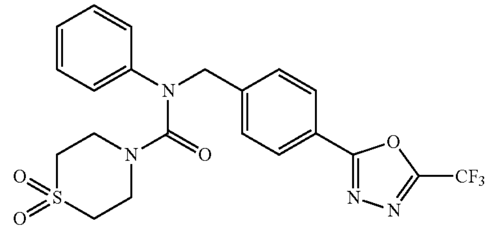 [SMILES: O=C(N1CCS(=O)(=O)CC1)N(Cc1ccc(-c2nnc(C(F)(F)F)o2)cc1)c1ccccc1] |
| 32 | 21362 | 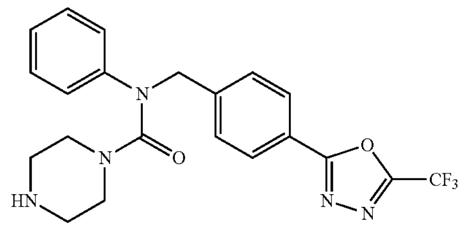 [SMILES: O=C(N1CCNCC1)N(Cc1ccc(-c2nnc(C(F)(F)F)o2)cc1)c1ccccc1] |
| 33 | 21363 | 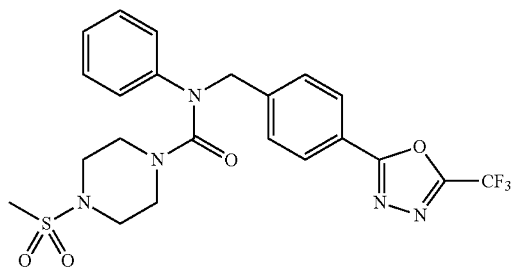 [SMILES: CS(=O)(=O)N1CCN(C(=O)N(Cc2ccc(-c3nnc(C(F)(F)F)o3)cc2)c2ccccc2)CC1] |
| 34 | 21364 | 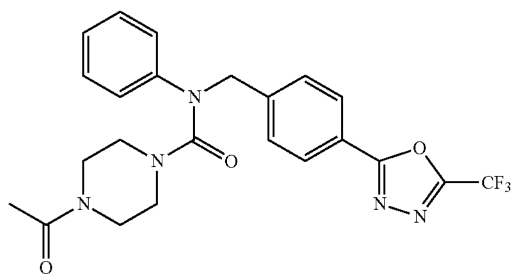 [SMILES: CC(=O)N1CCN(C(=O)N(Cc2ccc(-c3nnc(C(F)(F)F)o3)cc2)c2ccccc2)CC1] |
| 35 | 21365 | 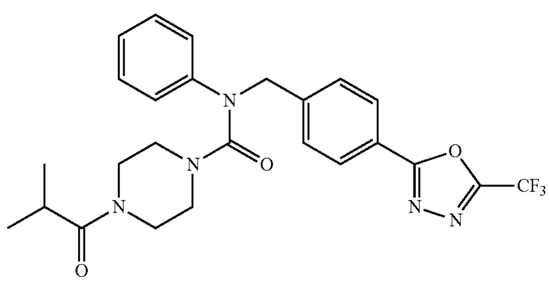 [SMILES: CC(C)C(=O)N1CCN(C(=O)N(Cc2ccc(-c3nnc(C(F)(F)F)o3)cc2)c2ccccc2)CC1] |
| 36 | 21366 | 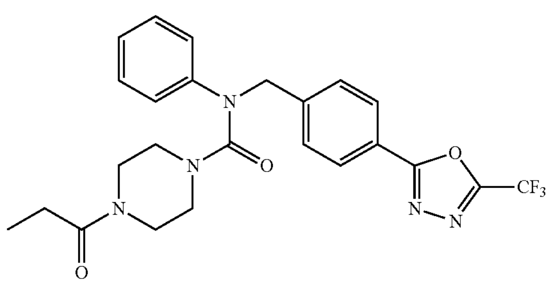 [SMILES: CCC(=O)N1CCN(C(=O)N(Cc2ccc(-c3nnc(C(F)(F)F)o3)cc2)c2ccccc2)CC1] |

TABLE 1-continued
| Ex. | Comp. | Structure |
|---|---|---|
| 37 | 21367 | 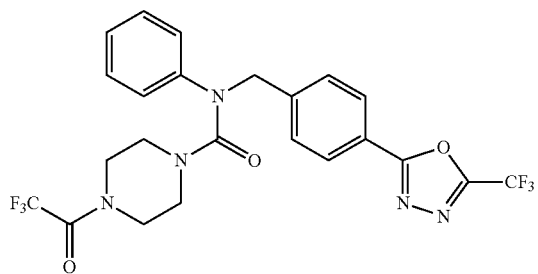 [SMILES: O=C(N1CCN(C(=O)C(F)(F)F)CC1)N(Cc1ccc(-c2nnc(C(F)(F)F)o2)cc1)c1ccccc1] |
| 38 | 21368 | 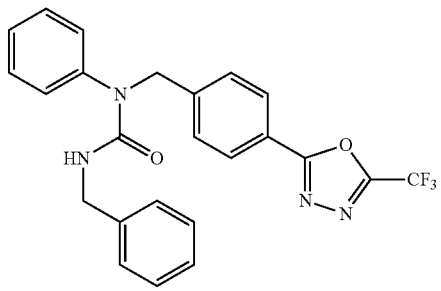 [SMILES: O=C(NCc1ccccc1)N(Cc1ccc(-c2nnc(C(F)(F)F)o2)cc1)c1ccccc1] |
| 39 | 21369 | 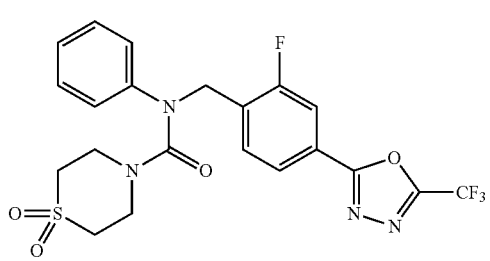 [SMILES: O=C(N1CCS(=O)(=O)CC1)N(Cc1ccc(-c2nnc(C(F)(F)F)o2)cc1F)c1ccccc1] |
| 40 | 21370 | 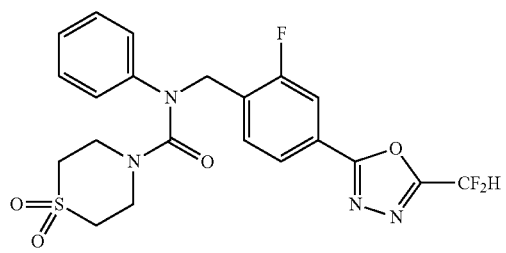 [SMILES: O=C(N1CCS(=O)(=O)CC1)N(Cc1ccc(-c2nnc(C(F)F)o2)cc1F)c1ccccc1] |
| 41 | 21371 | 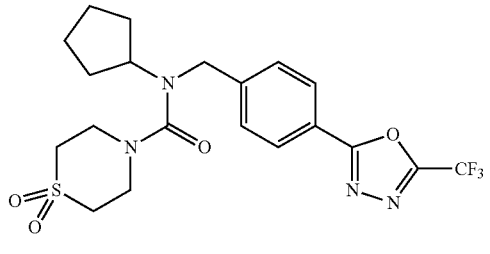 [SMILES: O=C(N1CCS(=O)(=O)CC1)N(Cc1ccc(-c2nnc(C(F)(F)F)o2)cc1)C1CCCC1] |
| 42 | 21372 | 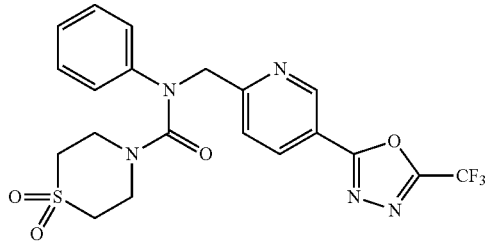 [SMILES: O=C(N1CCS(=O)(=O)CC1)N(Cc1ccc(-c2nnc(C(F)(F)F)o2)cn1)c1ccccc1] |

TABLE 1-continued

| Ex. | Comp. | Structure |
|---|---|---|
| 43 | 21373 | 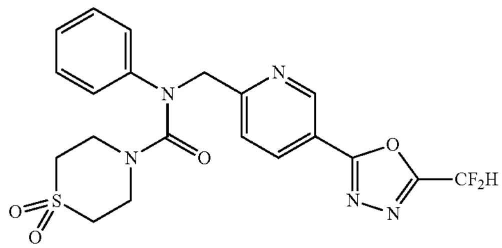 [SMILES: O=C(N1CCS(=O)(=O)CC1)N(Cc1ccc(-c2nnc(C(F)F)o2)cn1)c1ccccc1] |
| 44 | 21374 | 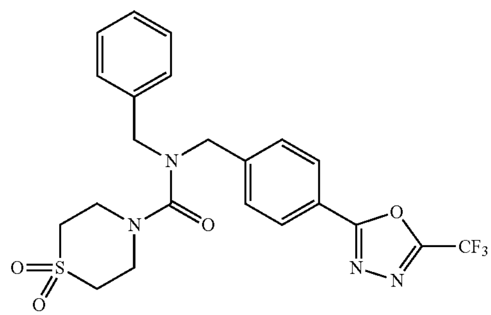 [SMILES: O=C(N1CCS(=O)(=O)CC1)N(Cc1ccccc1)Cc1ccc(-c2nnc(C(F)(F)F)o2)cc1] |
| 45 | 21375 | 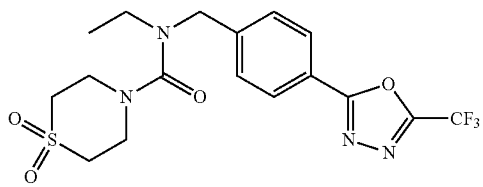 [SMILES: CCN(Cc1ccc(-c2nnc(C(F)(F)F)o2)cc1)C(=O)N1CCS(=O)(=O)CC1] |
| 46 | 21376 | 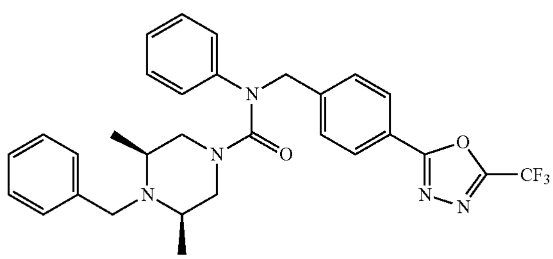 [SMILES: C[C@@H]1CN(C(=O)N(Cc2ccc(-c3nnc(C(F)(F)F)o3)cc2)c2ccccc2)C[C@H](C)N1Cc1ccccc1] |
| 47 | 21377 | 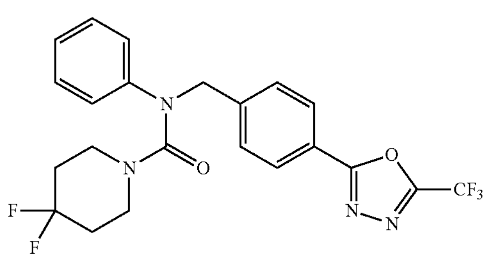 [SMILES: O=C(N1CCC(F)(F)CC1)N(Cc1ccc(-c2nnc(C(F)(F)F)o2)cc1)c1ccccc1] |
| 48 | 21378 | 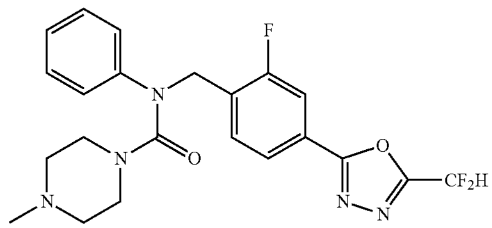 [SMILES: CN1CCN(C(=O)N(Cc2ccc(-c3nnc(C(F)F)o3)cc2F)c2ccccc2)CC1] |

TABLE 1-continued

| Ex. | Comp. | Structure |
|---|---|---|
| 49 | 21379 | 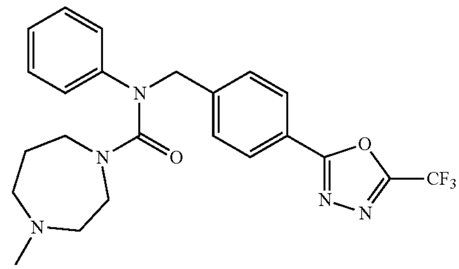 [SMILES: CN1CCCN(C(=O)N(Cc2ccc(-c3nnc(C(F)(F)F)o3)cc2)c2ccccc2)CC1] |
| 50 | 21380 | 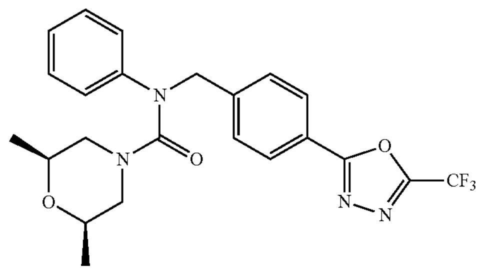 [SMILES: C[C@@H]1CN(C(=O)N(Cc2ccc(-c3nnc(C(F)(F)F)o3)cc2)c2ccccc2)C[C@H](C)O1] |
| 51 | 21381 | 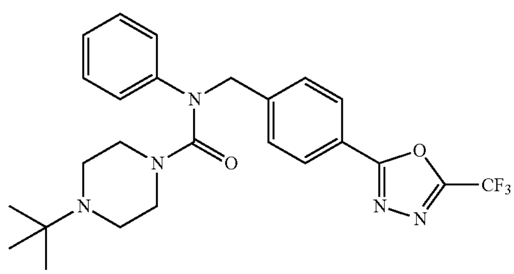 [SMILES: CC(C)(C)N1CCN(C(=O)N(Cc2ccc(-c3nnc(C(F)(F)F)o3)cc2)c2ccccc2)CC1] |
| 52 | 21382 | 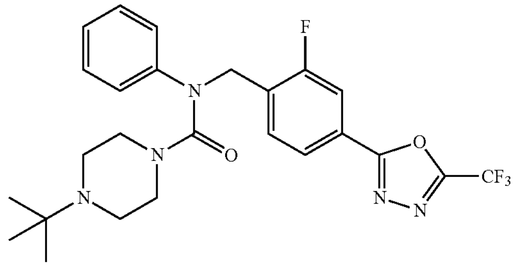 [SMILES: CC(C)(C)N1CCN(C(=O)N(Cc2ccc(-c3nnc(C(F)(F)F)o3)cc2F)c2ccccc2)CC1] |
| 53 | 21383 | 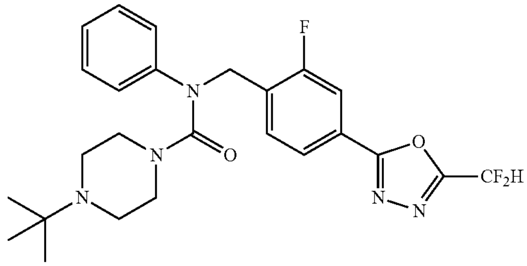 [SMILES: CC(C)(C)N1CCN(C(=O)N(Cc2ccc(-c3nnc(C(F)F)o3)cc2F)c2ccccc2)CC1] |

TABLE 1-continued

| Ex. | Comp. | Structure |
|---|---|---|
| 54 | 21384 | 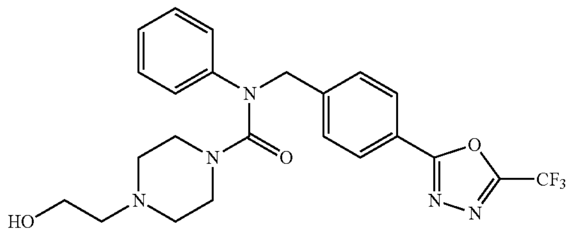 [SMILES: O=C(N1CCN(CCO)CC1)N(Cc1ccc(-c2nnc(C(F)(F)F)o2)cc1)c1ccccc1] |
| 55 | 21385 | 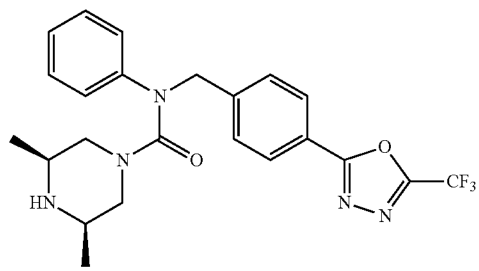 [SMILES: C[C@@H]1CN(C(=O)N(Cc2ccc(-c3nnc(C(F)(F)F)o3)cc2)c2ccccc2)C[C@H](C)N1] |
| 56 | 21386 | 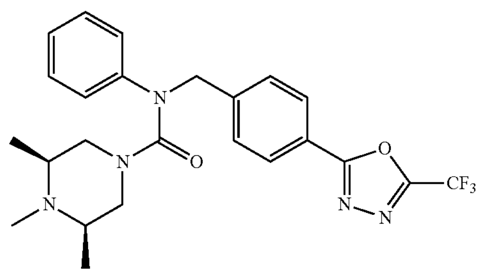 [SMILES: C[C@@H]1CN(C(=O)N(Cc2ccc(-c3nnc(C(F)(F)F)o3)cc2)c2ccccc2)C[C@H](C)N1C] |
| 57 | 21387 | 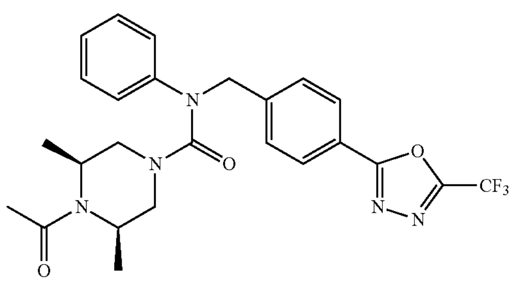 [SMILES: CC(=O)N1[C@H](C)CN(C(=O)N(Cc2ccc(-c3nnc(C(F)(F)F)o3)cc2)c2ccccc2)C[C@@H]1C] |
| 58 | 21388 | 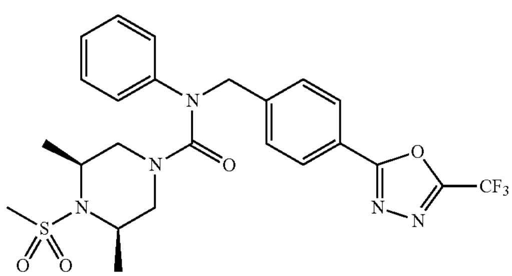 [SMILES: C[C@@H]1CN(C(=O)N(Cc2ccc(-c3nnc(C(F)(F)F)o3)cc2)c2ccccc2)C[C@H](C)N1S(C)(=O)=O] |
| 59 | 21389 | 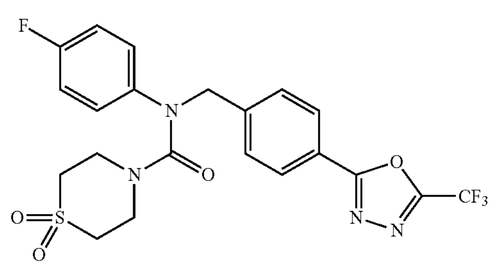 [SMILES: O=C(N1CCS(=O)(=O)CC1)N(Cc1ccc(-c2nnc(C(F)(F)F)o2)cc1)c1ccc(F)cc1] |

TABLE 1-continued

| Ex. | Comp. | Structure |
|-----|-------|-----------|
| 60 | 21390 | 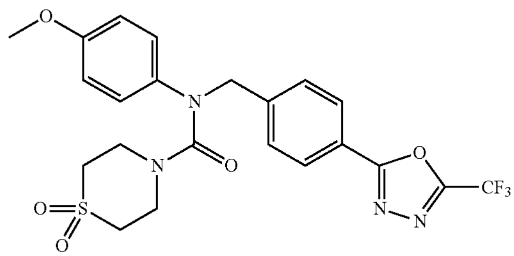 [SMILES: COc1ccc(N(Cc2ccc(-c3nnc(C(F)(F)F)o3)cc2)C(=O)N2CCS(=O)(=O)CC2)cc1] |
| 61 | 21391 | 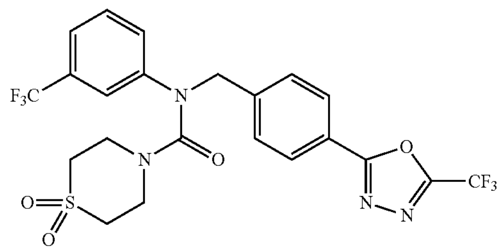 [SMILES: O=C(N1CCS(=O)(=O)CC1)N(Cc1ccc(-c2nnc(C(F)(F)F)o2)cc1)c1cccc(C(F)(F)F)c1] |
| 62 | 21392 | 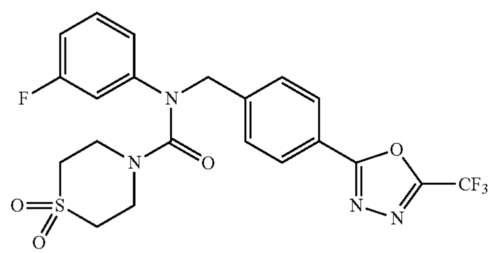 [SMILES: O=C(N1CCS(=O)(=O)CC1)N(Cc1ccc(-c2nnc(C(F)(F)F)o2)cc1)c1cccc(F)c1] |
| 63 | 21393 | 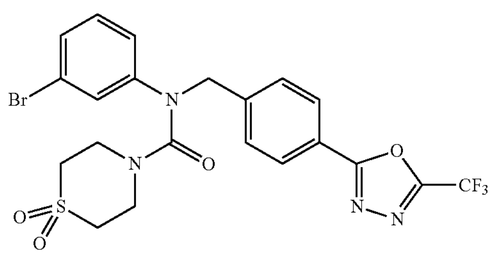 [SMILES: O=C(N1CCS(=O)(=O)CC1)N(Cc1ccc(-c2nnc(C(F)(F)F)o2)cc1)c1cccc(Br)c1] |
| 64 | 21394 | 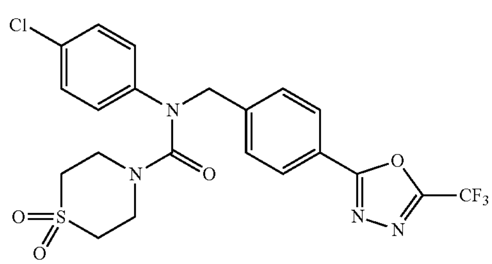 [SMILES: O=C(N1CCS(=O)(=O)CC1)N(Cc1ccc(-c2nnc(C(F)(F)F)o2)cc1)c1ccc(Cl)cc1] |
| 65 | 21395 | 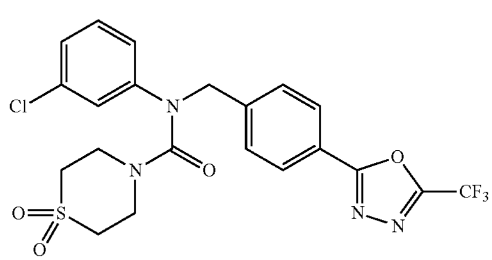 [SMILES: O=C(N1CCS(=O)(=O)CC1)N(Cc1ccc(-c2nnc(C(F)(F)F)o2)cc1)c1cccc(Cl)c1] |

TABLE 1-continued

| Ex. | Comp. | Structure |
|---|---|---|
| 66 | 21396 | 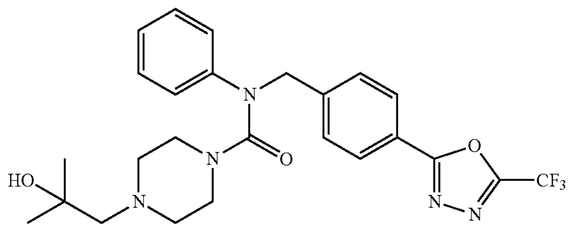 [SMILES: CC(C)(O)CN1CCN(C(=O)N(Cc2ccc(-c3nnc(C(F)(F)F)o3)cc2)c2ccccc2)CC1] |
| 67 | 21397 | 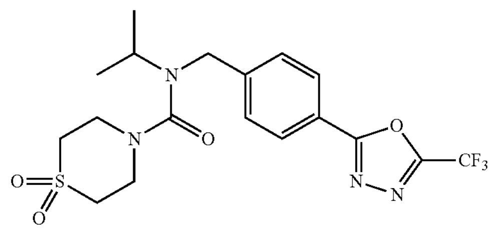 [SMILES: CC(C)N(Cc1ccc(-c2nnc(C(F)(F)F)o2)cc1)C(=O)N1CCS(=O)(=O)CC1] |
| 68 | 21398 | 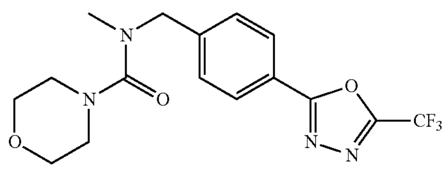 [SMILES: CN(Cc1ccc(-c2nnc(C(F)(F)F)o2)cc1)C(=O)N1CCOCC1] |
| 69 | 21399 | 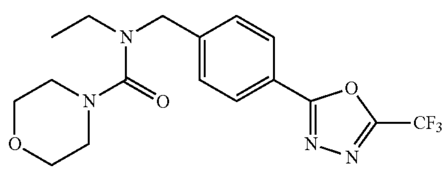 [SMILES: CCN(Cc1ccc(-c2nnc(C(F)(F)F)o2)cc1)C(=O)N1CCOCC1] |
| 70 | 21400 | 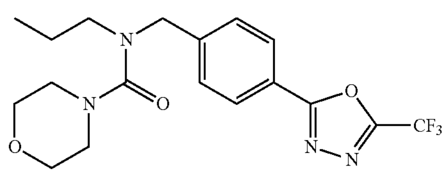 [SMILES: CCCN(Cc1ccc(-c2nnc(C(F)(F)F)o2)cc1)C(=O)N1CCOCC1] |
| 71 | 21401 | 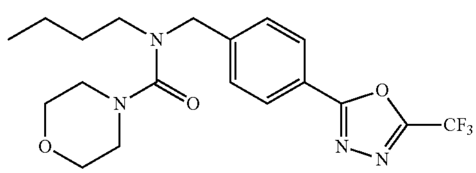 [SMILES: CCCCN(Cc1ccc(-c2nnc(C(F)(F)F)o2)cc1)C(=O)N1CCOCC1] |
| 72 | 21402 | 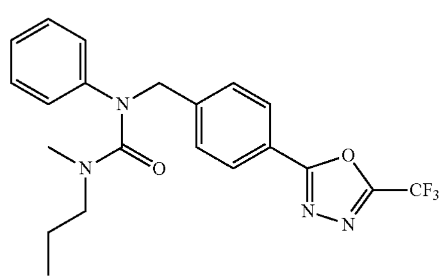 [SMILES: CCCN(C)C(=O)N(Cc1ccc(-c2nnc(C(F)(F)F)o2)cc1)c1ccccc1] |

TABLE 1-continued

| Ex. | Comp. | Structure |
|---|---|---|
| 73 | 21403 | 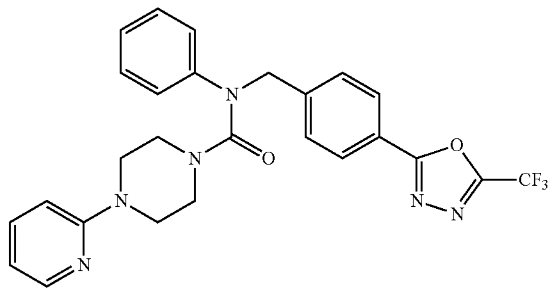 [SMILES: O=C(N1CCN(c2ccccn2)CC1)N(Cc1ccc(-c2nnc(C(F)(F)F)o2)cc1)c1ccccc1] |
| 74 | 21404 | 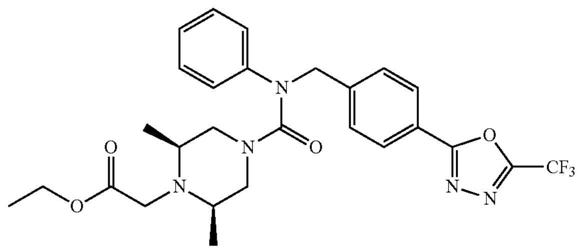 [SMILES: CCOC(=O)CN1[C@H](C)CN(C(=O)N(Cc2ccc(-c3nnc(C(F)(F)F)o3)cc2)c2ccccc2)C[C@@H]1C] |
| 75 | 21405 | 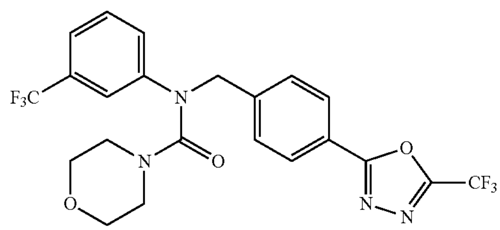 [SMILES: O=C(N1CCOCC1)N(Cc1ccc(-c2nnc(C(F)(F)F)o2)cc1)c1cccc(C(F)(F)F)c1] |
| 76 | 21406 | 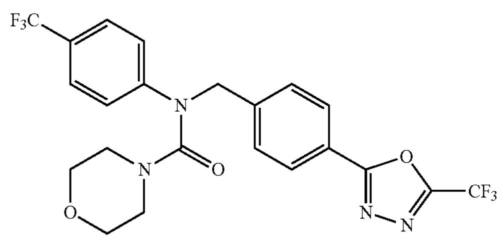 [SMILES: O=C(N1CCOCC1)N(Cc1ccc(-c2nnc(C(F)(F)F)o2)cc1)c1ccc(C(F)(F)F)cc1] |
| 77 | 21407 | 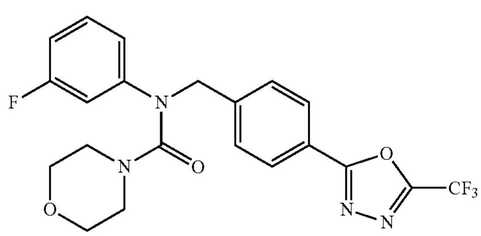 [SMILES: O=C(N1CCOCC1)N(Cc1ccc(-c2nnc(C(F)(F)F)o2)cc1)c1cccc(F)c1] |
| 78 | 21408 | 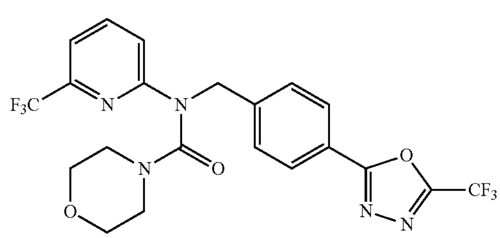 [SMILES: O=C(N1CCOCC1)N(Cc1ccc(-c2nnc(C(F)(F)F)o2)cc1)c1cccc(C(F)(F)F)n1] |

TABLE 1-continued
| Ex. | Comp. | Structure |
|---|---|---|
| 79 | 21409 | 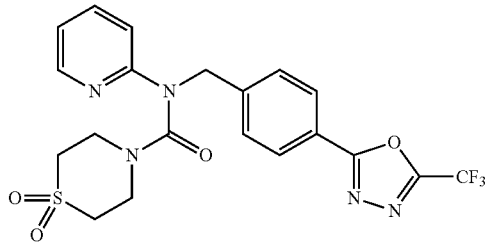 [SMILES: O=C(N1CCS(=O)(=O)CC1)N(Cc1ccc(-c2nnc(C(F)(F)F)o2)cc1)c1ccccn1] |
| 80 | 21410 | 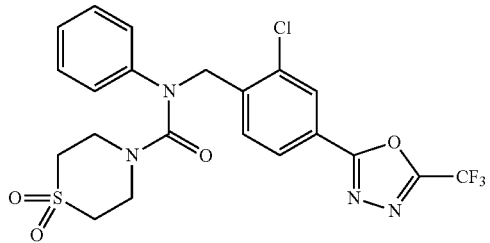 [SMILES: O=C(N1CCS(=O)(=O)CC1)N(Cc1ccc(-c2nnc(C(F)(F)F)o2)cc1Cl)c1ccccc1] |
| 81 | 21411 | 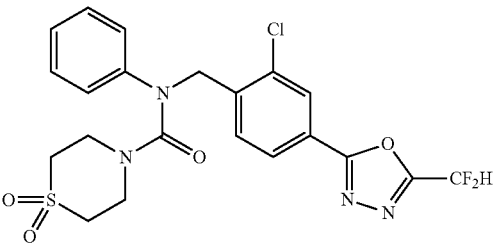 [SMILES: O=C(N1CCS(=O)(=O)CC1)N(Cc1ccc(-c2nnc(C(F)F)o2)cc1Cl)c1ccccc1] |
| 82 | 21412 | 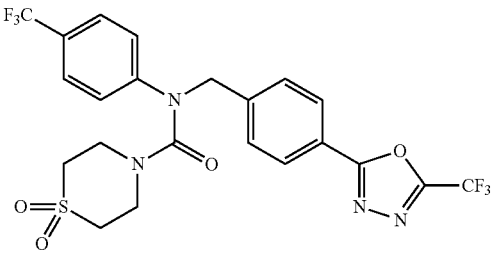 [SMILES: O=C(N1CCS(=O)(=O)CC1)N(Cc1ccc(-c2nnc(C(F)(F)F)o2)cc1)c1ccc(C(F)(F)F)cc1] |
| 83 | 21413 | 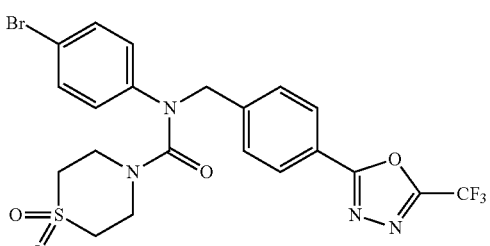 |
| 84 | 21414 | 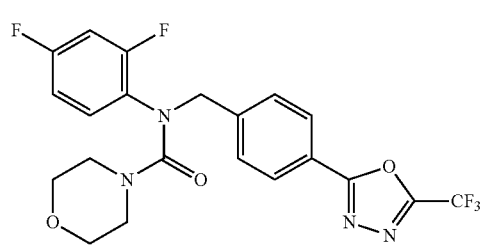 [SMILES: O=C(N1CCOCC1)N(Cc1ccc(-c2nnc(C(F)(F)F)o2)cc1)c1ccc(F)cc1F] |

TABLE 1-continued

| Ex. | Comp. | Structure |
|---|---|---|
| 85 | 21415 | 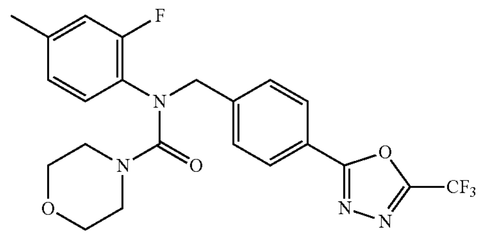 [SMILES: Cc1ccc(N(Cc2ccc(-c3nnc(C(F)(F)F)o3)cc2)C(=O)N2CCOCC2)c(F)c1] |
| 86 | 21416 | 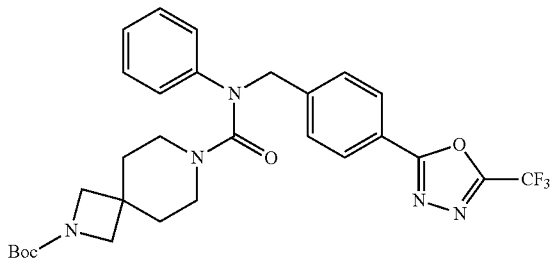 [SMILES: CC(C)(C)OC(=O)N1CC2(CCN(C(=O)N(Cc3ccc(-c4nnc(C(F)(F)F)o4)cc3)c3ccccc3)CC2)C1] |
| 87 | 21417 | 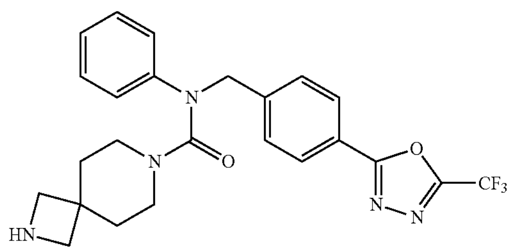 [SMILES: O=C(N1CCC2(CC1)CNC2)N(Cc1ccc(-c2nnc(C(F)(F)F)o2)cc1)c1ccccc1] |
| 88 | 21418 | 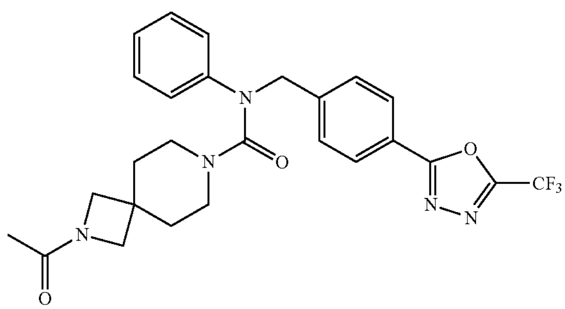 [SMILES: CC(=O)N1CC2(CCN(C(=O)N(Cc3ccc(-c4nnc(C(F)(F)F)o4)cc3)c3ccccc3)CC2)C1] |
| 89 | 21419 | 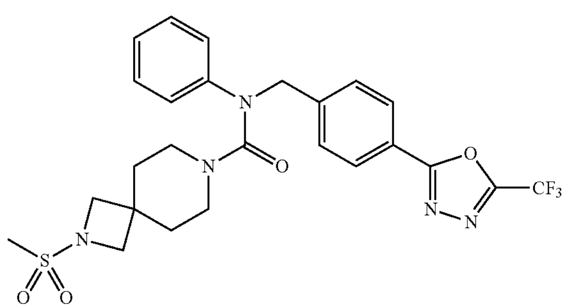 [SMILES: CS(=O)(=O)N1CC2(CCN(C(=O)N(Cc3ccc(-c4nnc(C(F)(F)F)o4)cc3)c3ccccc3)CC2)C1] |

TABLE 1-continued

| Ex. | Comp. | Structure |
|---|---|---|
| 90 | 21420 | 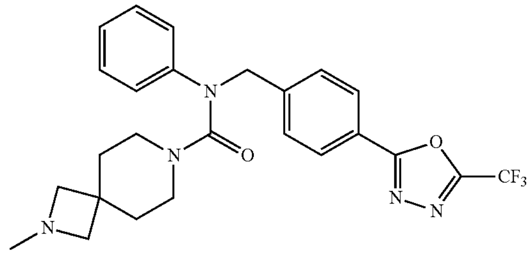 [SMILES: CN1CC2(CCN(C(=O)N(Cc3ccc(-c4nnc(C(F)(F)F)o4)cc3)c3ccccc3)CC2)C1] |
| 91 | 21421 | 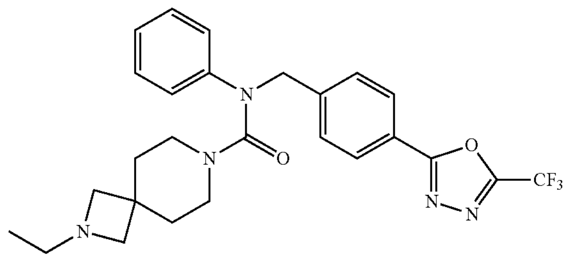 [SMILES: CCN1CC2(CCN(C(=O)N(Cc3ccc(-c4nnc(C(F)(F)F)o4)cc3)c3ccccc3)CC2)C1] |
| 92 | 21422 | 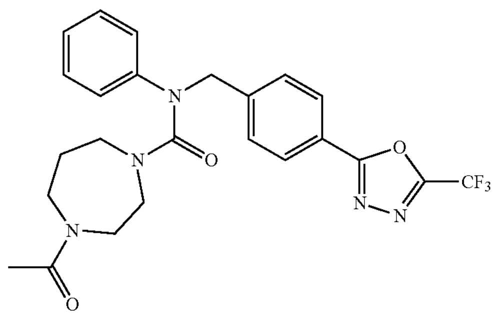 [SMILES: CC(=O)N1CCCN(C(=O)N(Cc2ccc(-c3nnc(C(F)(F)F)o3)cc2)c2ccccc2)CC1] |
| 93 | 21423 | 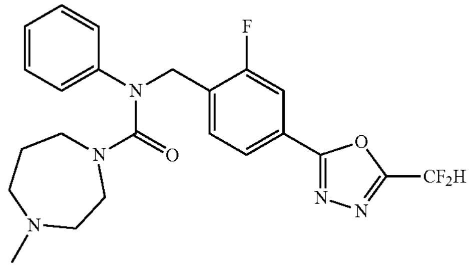 [SMILES: CN1CCCN(C(=O)N(Cc2ccc(-c3nnc(C(F)F)o3)cc2F)c2ccccc2)CC1] |
| 94 | 21424 | 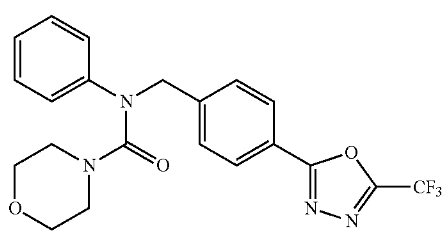 [SMILES: O=C(N1CCOCC1)N(Cc1ccc(-c2nnc(C(F)(F)F)o2)cc1)c1ccccc1] |
| 95 | 21425 | 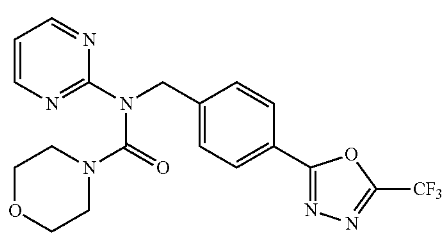 [SMILES: O=C(N1CCOCC1)N(Cc1ccc(-c2nnc(C(F)(F)F)o2)cc1)c1ncccn1] |

TABLE 1-continued

| Ex. | Comp. | Structure |
|---|---|---|
| 96 | 21426 | 4-fluorophenyl-N-benzyl-morpholine-4-carboxamide with 5-(trifluoromethyl)-1,3,4-oxadiazole |
| 97 | 21427 | pyridin-3-yl-N-benzyl-morpholine-4-carboxamide with 5-(trifluoromethyl)-1,3,4-oxadiazole |
| 98 | 21428 | 2-fluorophenyl-N-benzyl-morpholine-4-carboxamide with 5-(trifluoromethyl)-1,3,4-oxadiazole |
| 99 | 21429 | phenyl-N-(2-chlorobenzyl)-morpholine-4-carboxamide with 5-(trifluoromethyl)-1,3,4-oxadiazole |
| 100 | 21431 | phenyl-N-(2,6-difluorobenzyl)-morpholine-4-carboxamide with 5-(trifluoromethyl)-1,3,4-oxadiazole |
| 101 | 21432 | phenyl-N-(2,6-difluorobenzyl)-morpholine-4-carboxamide with 5-(difluoromethyl)-1,3,4-oxadiazole |

TABLE 1-continued

| Ex. | Comp. | Structure |
|---|---|---|
| 102 | 21433 | 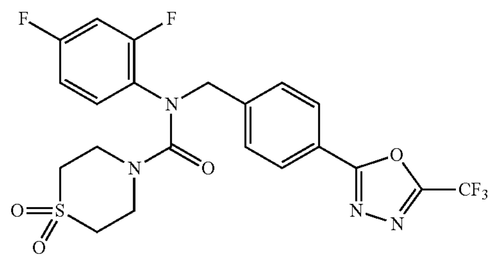 [SMILES: O=C(N1CCS(=O)(=O)CC1)N(Cc1ccc(-c2nnc(C(F)(F)F)o2)cc1)c1ccc(F)cc1F] |
| 103 | 21434 | 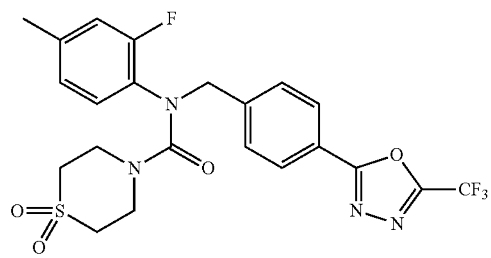 [SMILES: Cc1ccc(N(Cc2ccc(-c3nnc(C(F)(F)F)o3)cc2)C(=O)N2CCS(=O)(=O)CC2)c(F)c1] |
| 104 | 21435 | 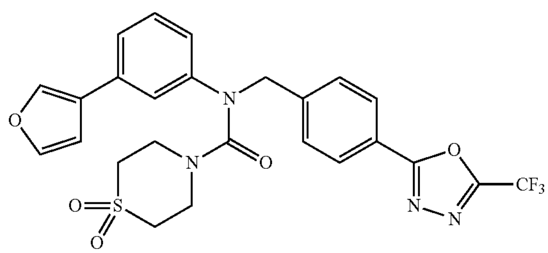 [SMILES: O=C(N1CCS(=O)(=O)CC1)N(Cc1ccc(-c2nnc(C(F)(F)F)o2)cc1)c1cccc(-c2ccoc2)c1] |
| 105 | 21436 | 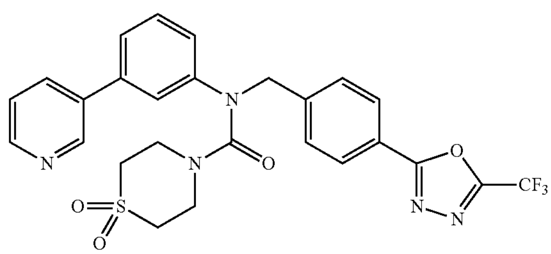 [SMILES: O=C(N1CCS(=O)(=O)CC1)N(Cc1ccc(-c2nnc(C(F)(F)F)o2)cc1)c1cccc(-c2cccnc2)c1] |
| 106 | 21437 | 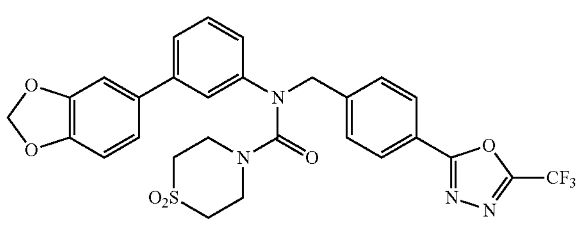 [SMILES: O=C(N1CCS(=O)(=O)CC1)N(Cc1ccc(-c2nnc(C(F)(F)F)o2)cc1)c1cccc(-c2ccc3c(c2)OCO3)c1] |
| 107 | 21438 | 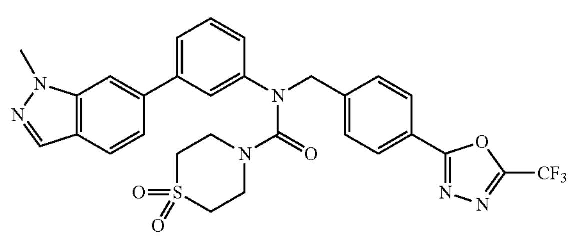 [SMILES: Cn1ncc2ccc(-c3cccc(N(Cc4ccc(-c5nnc(C(F)(F)F)o5)cc4)C(=O)N4CCS(=O)(=O)CC4)c3)cc21] |

TABLE 1-continued

| Ex. | Comp. | Structure |
|-----|-------|-----------|
| 108 | 21439 | 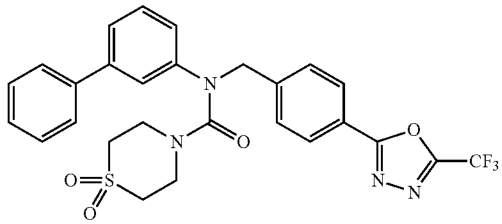 [SMILES: O=C(N1CCS(=O)(=O)CC1)N(Cc1ccc(-c2nnc(C(F)(F)F)o2)cc1)c1cccc(-c2ccccc2)c1] |
| 109 | 21440 | 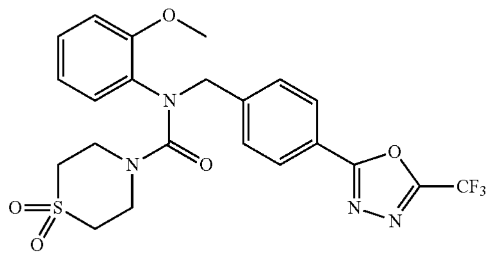 [SMILES: COc1ccccc1N(Cc1ccc(-c2nnc(C(F)(F)F)o2)cc1)C(=O)N1CCS(=O)(=O)CC1] |
| 110 | 21441 | 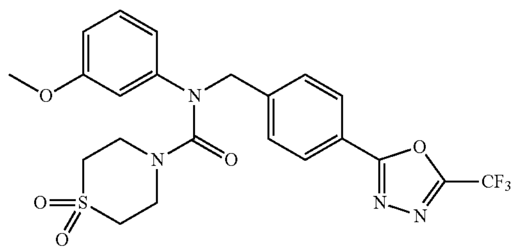 [SMILES: COc1cccc(N(Cc2ccc(-c3nnc(C(F)(F)F)o3)cc2)C(=O)N2CCS(=O)(=O)CC2)c1] |
| 111 | 21442 | 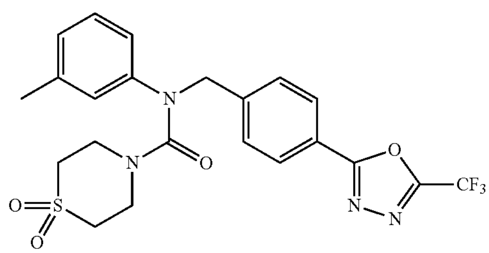 [SMILES: Cc1cccc(N(Cc2ccc(-c3nnc(C(F)(F)F)o3)cc2)C(=O)N2CCS(=O)(=O)CC2)c1] |
| 112 | 21443 | 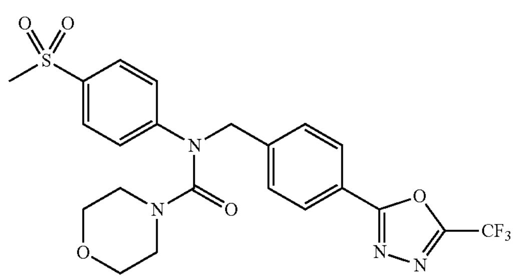 [SMILES: CS(=O)(=O)c1ccc(N(Cc2ccc(-c3nnc(C(F)(F)F)o3)cc2)C(=O)N2CCOCC2)cc1] |
| 113 | 21444 | 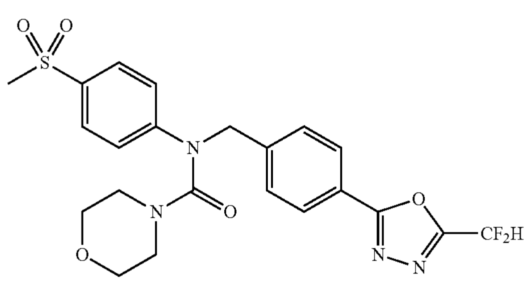 [SMILES: CS(=O)(=O)c1ccc(N(Cc2ccc(-c3nnc(C(F)F)o3)cc2)C(=O)N2CCOCC2)cc1] |

TABLE 1-continued

| Ex. | Comp. | Structure |
|-----|-------|-----------|
| 114 | 21445 | 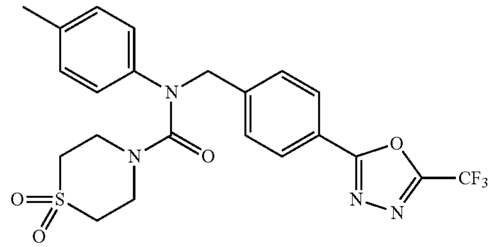 [SMILES: Cc1ccc(N(Cc2ccc(-c3nnc(C(F)(F)F)o3)cc2)C(=O)N2CCS(=O)(=O)CC2)cc1] |
| 115 | 21446 | 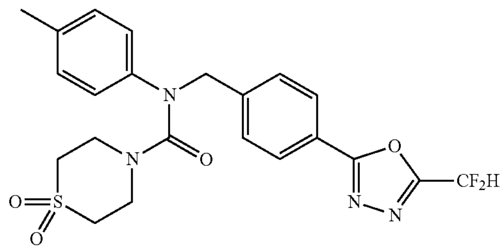 [SMILES: Cc1ccc(N(Cc2ccc(-c3nnc(C(F)F)o3)cc2)C(=O)N2CCS(=O)(=O)CC2)cc1] |
| 116 | 21447 | 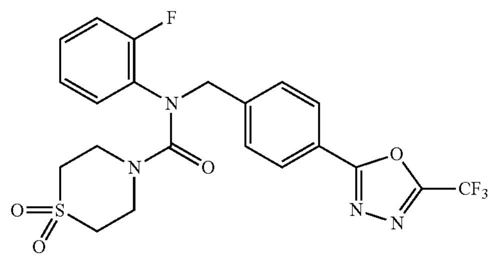 [SMILES: O=C(N1CCS(=O)(=O)CC1)N(Cc1ccc(-c2nnc(C(F)(F)F)o2)cc1)c1ccccc1F] |
| 117 | 21448 | 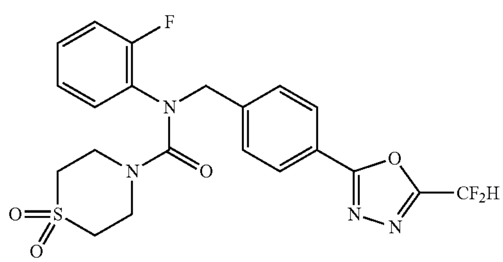 [SMILES: O=C(N1CCS(=O)(=O)CC1)N(Cc1ccc(-c2nnc(C(F)F)o2)cc1)c1ccccc1F] |
| 118 | 21449 | 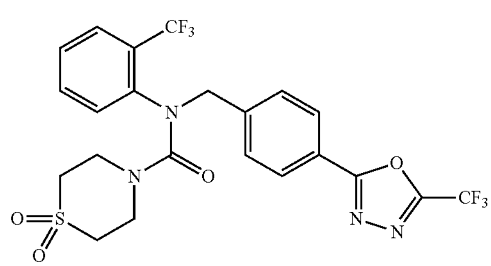 [SMILES: O=C(N1CCS(=O)(=O)CC1)N(Cc1ccc(-c2nnc(C(F)(F)F)o2)cc1)c1ccccc1C(F)(F)F] |
| 119 | 21450 | 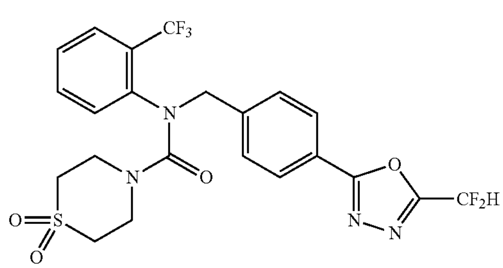 [SMILES: O=C(N1CCS(=O)(=O)CC1)N(Cc1ccc(-c2nnc(C(F)F)o2)cc1)c1ccccc1C(F)(F)F] |

TABLE 1-continued
| Ex. | Comp. | Structure |
|---|---|---|
| 120 | 21451 | 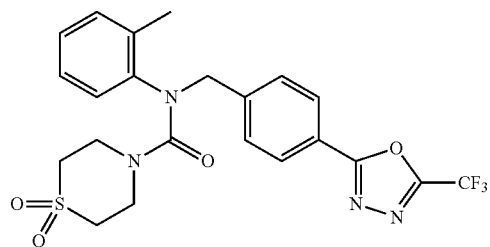 [SMILES: Cc1ccccc1N(Cc1ccc(-c2nnc(C(F)(F)F)o2)cc1)C(=O)N1CCS(=O)(=O)CC1] |
| 121 | 21452 | 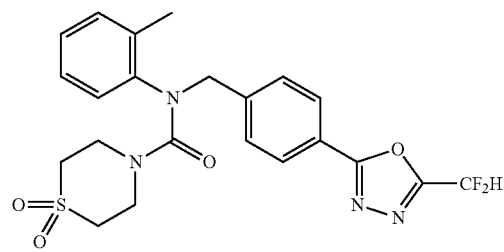 [SMILES: Cc1ccccc1N(Cc1ccc(-c2nnc(C(F)F)o2)cc1)C(=O)N1CCS(=O)(=O)CC1] |
| 122 | 21453 | 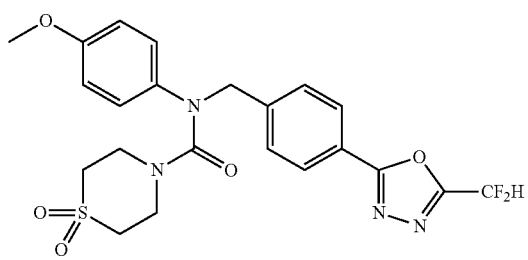 [SMILES: COc1ccc(N(Cc2ccc(-c3nnc(C(F)F)o3)cc2)C(=O)N2CCS(=O)(=O)CC2)cc1] |
| 123 | 21454 | 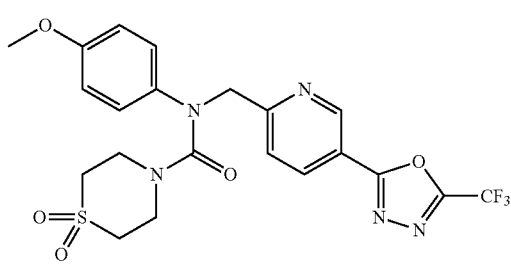 |
| 124 | 21455 | 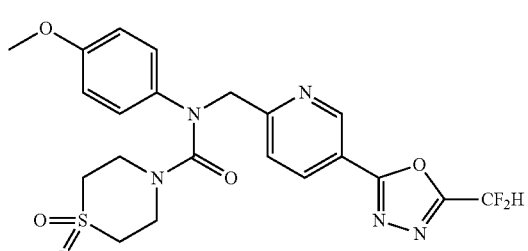 |
| 125 | 21456 | 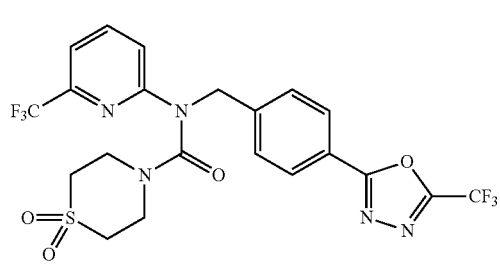 [SMILES: O=C(N1CCS(=O)(=O)CC1)N(Cc1ccc(-c2nnc(C(F)(F)F)o2)cc1)c1cccc(C(F)(F)F)n1] |

TABLE 1-continued

| Ex. | Comp. | Structure |
|---|---|---|
| 126 | 21457 | 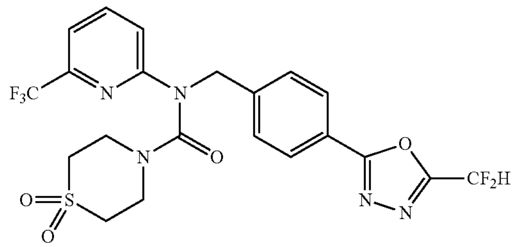 [SMILES: O=C(N1CCS(=O)(=O)CC1)N(Cc1ccc(-c2nnc(C(F)F)o2)cc1)c1cccc(C(F)(F)F)n1] |
| 127 | 21458 | 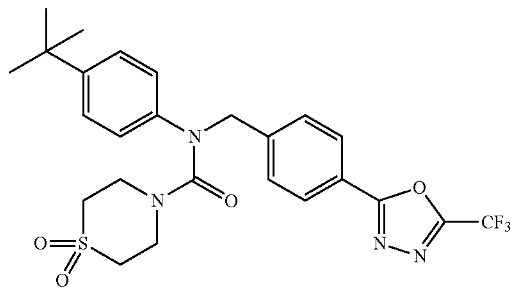 [SMILES: CC(C)(C)c1ccc(N(Cc2ccc(-c3nnc(C(F)(F)F)o3)cc2)C(=O)N2CCS(=O)(=O)CC2)cc1] |
| 128 | 21459 | 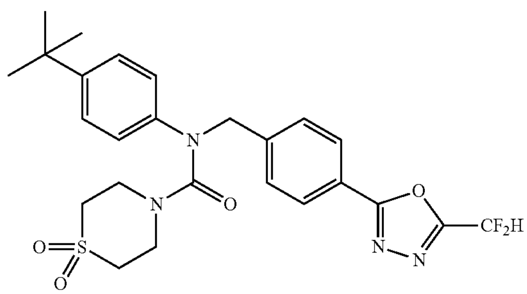 [SMILES: CC(C)(C)c1ccc(N(Cc2ccc(-c3nnc(C(F)F)o3)cc2)C(=O)N2CCS(=O)(=O)CC2)cc1] |
| 129 | 21460 | 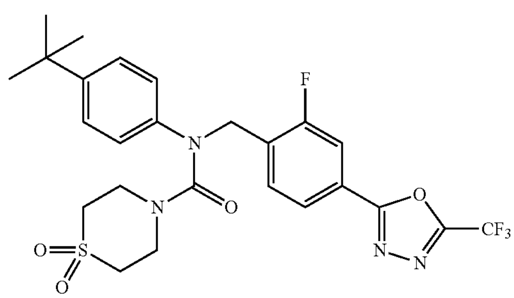 [SMILES: CC(C)(C)c1ccc(N(Cc2ccc(-c3nnc(C(F)(F)F)o3)cc2F)C(=O)N2CCS(=O)(=O)CC2)cc1] |
| 130 | 21461 | 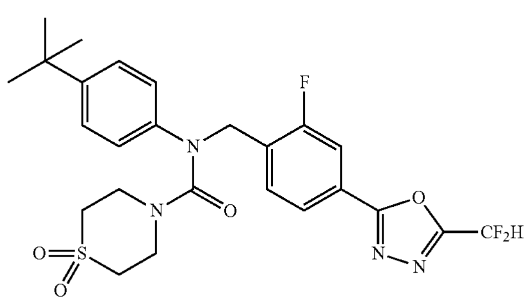 [SMILES: CC(C)(C)c1ccc(N(Cc2ccc(-c3nnc(C(F)F)o3)cc2F)C(=O)N2CCS(=O)(=O)CC2)cc1] |

TABLE 1-continued
| Ex. | Comp. | Structure |
|---|---|---|
| 131 | 21462 | 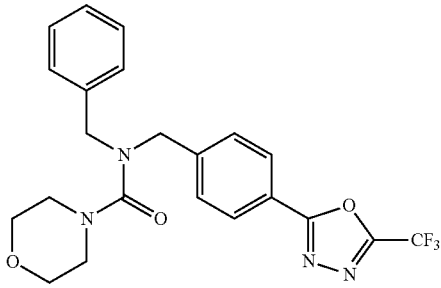 [SMILES: O=C(N1CCOCC1)N(Cc1ccccc1)Cc1ccc(-c2nnc(C(F)(F)F)o2)cc1] |
| 132 | 21463 | 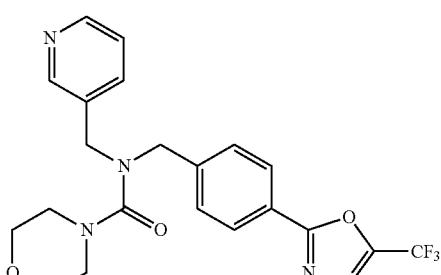 |
| 133 | 21464 | 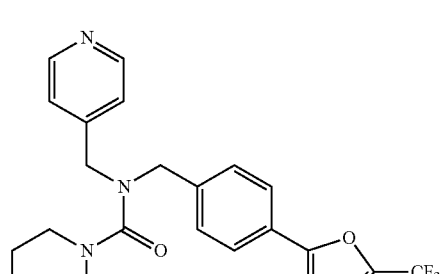 |
| 134 | 21465 | 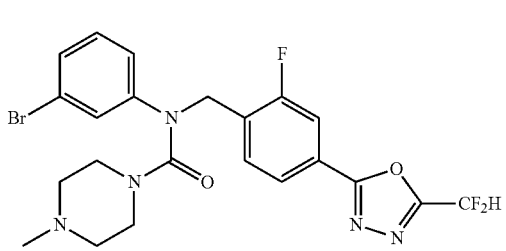 [SMILES: CN1CCN(C(=O)N(Cc2ccc(-c3nnc(C(F)F)o3)cc2F)c2cccc(Cl)c2)CC1] |
| 135 | 21466 | 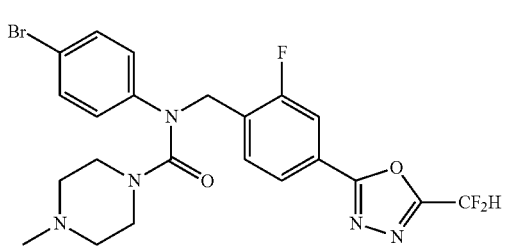 [SMILES: CN1CCN(C(=O)N(Cc2ccc(-c3nnc(C(F)F)o3)cc2F)c2ccc(Cl)cc2)CC1] |
| 136 | 21467 | 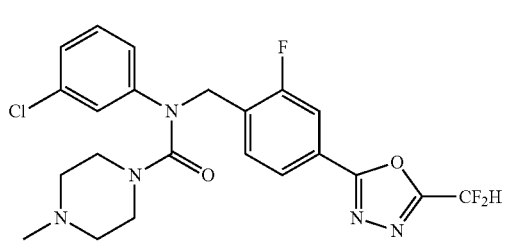 |

TABLE 1-continued

| Ex. | Comp. | Structure |
|---|---|---|
| 137 | 21468 | 4-Cl-C6H4-N(CH2-Ar)-C(O)-N(piperazine-N-Me); Ar = 2-F-4-(5-CF2H-1,3,4-oxadiazol-2-yl)phenyl |
| 138 | 21469 | 2-Me-C6H4-N(CH2-Ar)-C(O)-N(piperazine-N-Me); Ar = 2-F-4-(5-CF2H-1,3,4-oxadiazol-2-yl)phenyl |
| 139 | 21470 | 3-Me-C6H4-N(CH2-Ar)-C(O)-N(piperazine-N-Me); Ar = 2-F-4-(5-CF2H-1,3,4-oxadiazol-2-yl)phenyl |
| 140 | 21471 | 4-Me-C6H4-N(CH2-Ar)-C(O)-N(piperazine-N-Me); Ar = 2-F-4-(5-CF2H-1,3,4-oxadiazol-2-yl)phenyl |
| 141 | 21472 | 2-MeO-C6H4-N(CH2-Ar)-C(O)-N(piperazine-N-Me); Ar = 2-F-4-(5-CF2H-1,3,4-oxadiazol-2-yl)phenyl |
| 142 | 21473 | 3-MeO-C6H4-N(CH2-Ar)-C(O)-N(piperazine-N-Me); Ar = 2-F-4-(5-CF2H-1,3,4-oxadiazol-2-yl)phenyl |

TABLE 1-continued

| Ex. | Comp. | Structure |
|-----|-------|-----------|
| 143 | 21474 | 2-methoxyphenyl-N-(4-(5-(difluoromethyl)-1,3,4-oxadiazol-2-yl)benzyl)-1,1-dioxo-thiomorpholine-4-carboxamide |
| 144 | 21475 | 3-methoxyphenyl-N-(4-(5-(difluoromethyl)-1,3,4-oxadiazol-2-yl)benzyl)-1,1-dioxo-thiomorpholine-4-carboxamide |
| 145 | 21476 | 3-methylphenyl-N-(4-(5-(difluoromethyl)-1,3,4-oxadiazol-2-yl)benzyl)-1,1-dioxo-thiomorpholine-4-carboxamide |
| 146 | 21477 | 4-methoxyphenyl-N-(2-fluoro-4-(5-(trifluoromethyl)-1,3,4-oxadiazol-2-yl)benzyl)-1,1-dioxo-thiomorpholine-4-carboxamide |
| 147 | 21478 | 4-methoxyphenyl-N-(2-fluoro-4-(5-(difluoromethyl)-1,3,4-oxadiazol-2-yl)benzyl)-1,1-dioxo-thiomorpholine-4-carboxamide |
| 148 | 21479 | 2-methoxyphenyl-N-(2-fluoro-4-(5-(trifluoromethyl)-1,3,4-oxadiazol-2-yl)benzyl)-1,1-dioxo-thiomorpholine-4-carboxamide |

TABLE 1-continued

| Ex. | Comp. | Structure |
|---|---|---|
| 149 | 21480 | 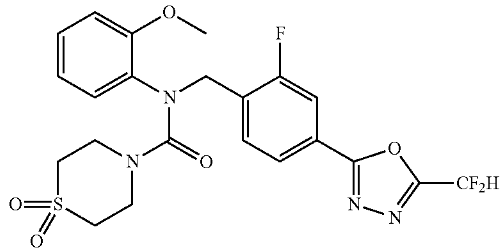 [SMILES: COc1ccccc1N(Cc1ccc(-c2nnc(C(F)F)o2)cc1F)C(=O)N1CCS(=O)(=O)CC1] |
| 150 | 21481 | 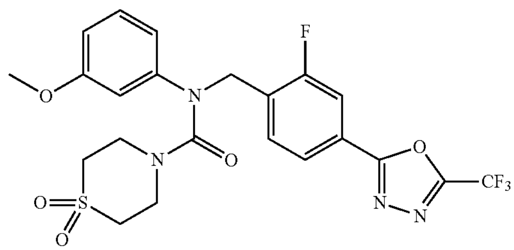 [SMILES: COc1cccc(N(Cc2ccc(-c3nnc(C(F)(F)F)o3)cc2F)C(=O)N2CCS(=O)(=O)CC2)c1] |
| 151 | 21482 | 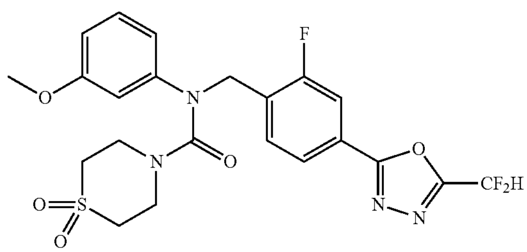 [SMILES: COc1cccc(N(Cc2ccc(-c3nnc(C(F)F)o3)cc2F)C(=O)N2CCS(=O)(=O)CC2)c1] |
| 152 | 21483 | 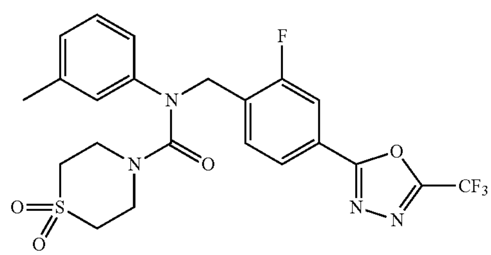 [SMILES: Cc1cccc(N(Cc2ccc(-c3nnc(C(F)(F)F)o3)cc2F)C(=O)N2CCS(=O)(=O)CC2)c1] |
| 153 | 21484 | 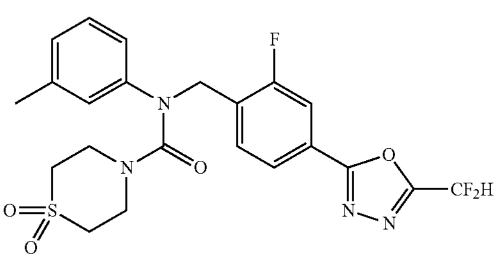 |
| 154 | 21485 | 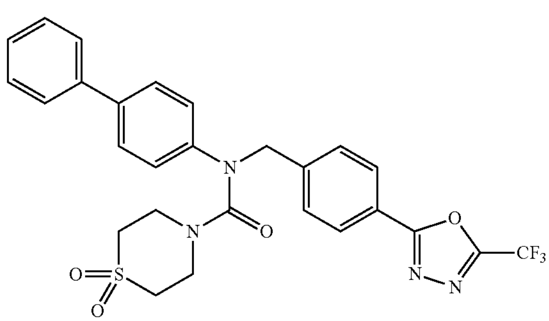 [SMILES: O=C(N1CCS(=O)(=O)CC1)N(Cc1ccc(-c2nnc(C(F)(F)F)o2)cc1)c1ccc(-c2ccccc2)cc1] |

TABLE 1-continued
| Ex. | Comp. | Structure |
|---|---|---|
| 155 | 21486 | 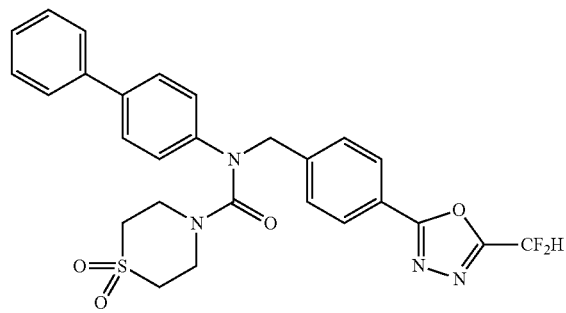 [SMILES: O=C(N1CCS(=O)(=O)CC1)N(Cc1ccc(-c2nnc(C(F)F)o2)cc1)c1ccc(-c2ccccc2)cc1] |
| 156 | 21487 | 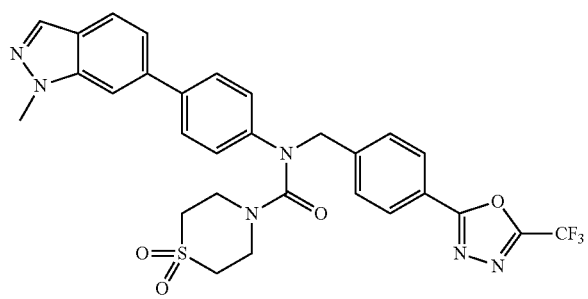 [SMILES: Cn1ncc2ccc(-c3ccc(N(Cc4ccc(-c5nnc(C(F)(F)F)o5)cc4)C(=O)N4CCS(=O)(=O)CC4)cc3)cc21] |
| 157 | 21488 | 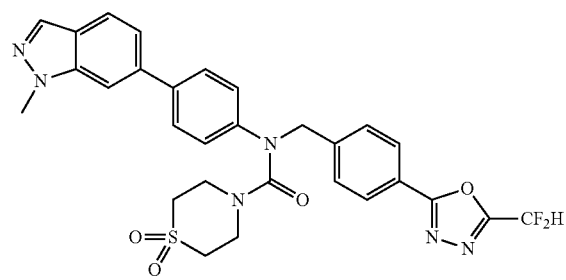 [SMILES: Cn1ncc2ccc(-c3ccc(N(Cc4ccc(-c5nnc(C(F)F)o5)cc4)C(=O)N4CCS(=O)(=O)CC4)cc3)cc21] |
| 158 | 21489 | 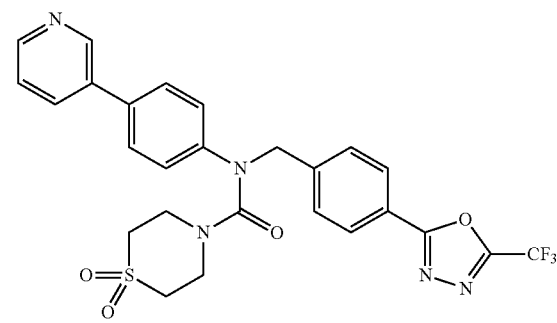 [SMILES: O=C(N1CCS(=O)(=O)CC1)N(Cc1ccc(-c2nnc(C(F)(F)F)o2)cc1)c1ccc(-c2cccnc2)cc1] |
| 159 | 21490 | 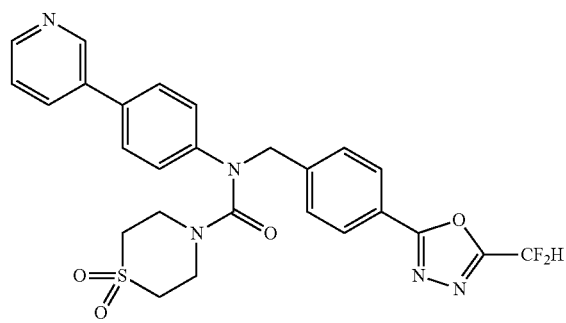 [SMILES: O=C(N1CCS(=O)(=O)CC1)N(Cc1ccc(-c2nnc(C(F)F)o2)cc1)c1ccc(-c2cccnc2)cc1] |

TABLE 1-continued
| Ex. | Comp. | Structure |
|---|---|---|
| 160 | 21491 | 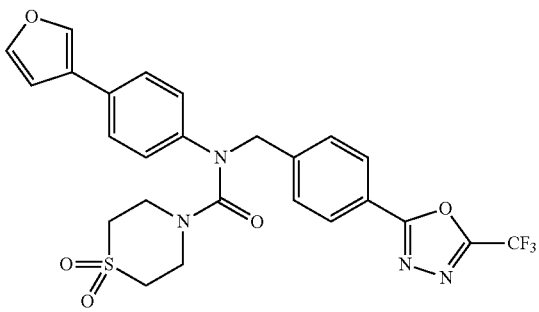 [SMILES: O=C(N1CCS(=O)(=O)CC1)N(Cc1ccc(-c2nnc(C(F)(F)F)o2)cc1)c1ccc(-c2ccoc2)cc1] |
| 161 | 21492 | 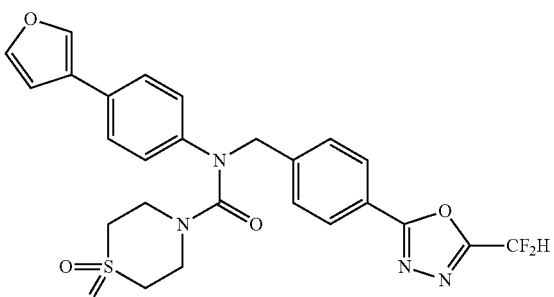 |
| 162 | 21493 | 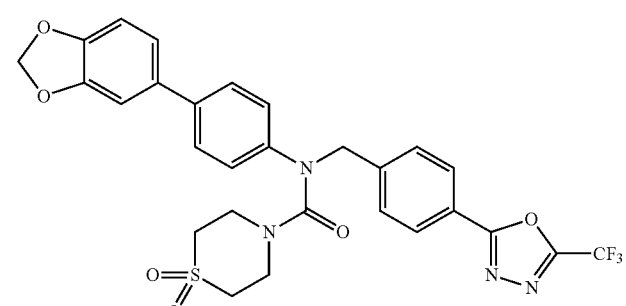 |
| 163 | 21494 | 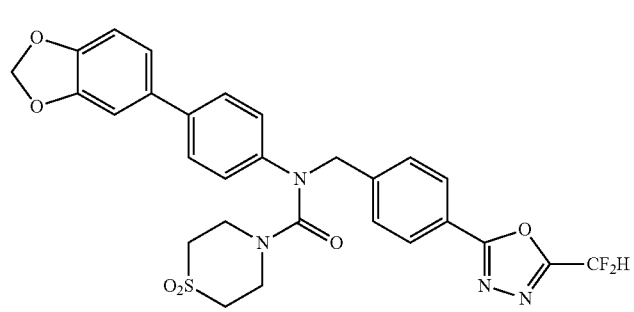 [SMILES: O=C(N1CCS(=O)(=O)CC1)N(Cc1ccc(-c2nnc(C(F)F)o2)cc1)c1ccc(-c2ccc3c(c2)OCO3)cc1] |
| 164 | 21495 | 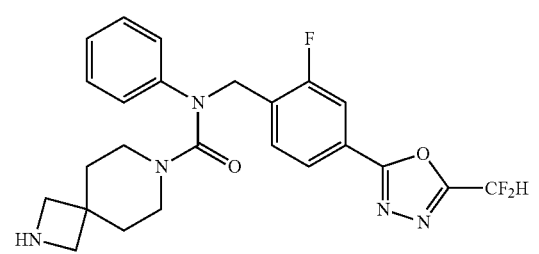 [SMILES: O=C(N1CCC2(CC1)CNC2)N(Cc1ccc(-c2nnc(C(F)F)o2)cc1F)c1ccccc1] |

TABLE 1-continued
| Ex. | Comp. | Structure |
|---|---|---|
| 165 | 21496 | 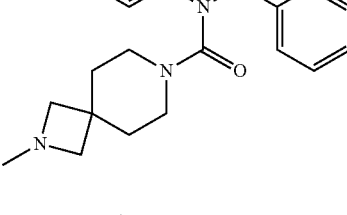 |
| 166 | 21497 | 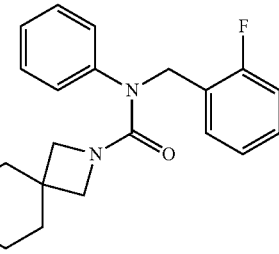 |
| 167 | 21498 | 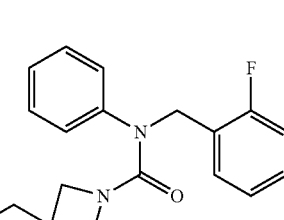 |
| 168 | 21499 | 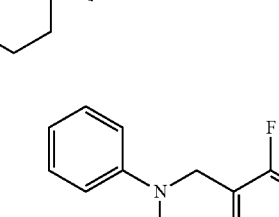 |
| 169 | 21500 | 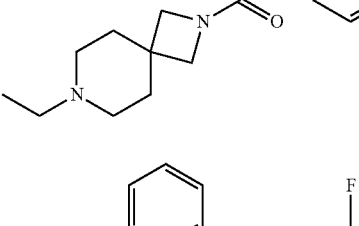 |

TABLE 1-continued
| Ex. | Comp. | Structure |
|---|---|---|
| 170 | 21501 | 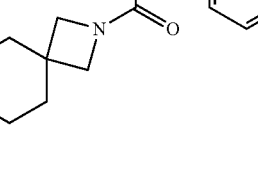 |
| 171 | 21502 | 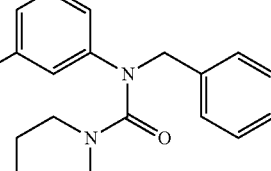 |
| 172 | 21511 | 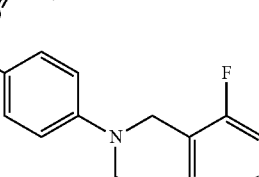 |
| 173 | 21512 | 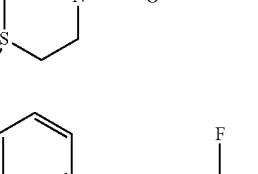 |
| 174 | 21513 | 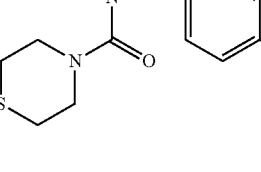 |
| 175 | 21514 | 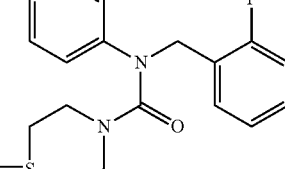 |

TABLE 1-continued
| Ex. | Comp. | Structure |
|---|---|---|
| 176 | 21515 | 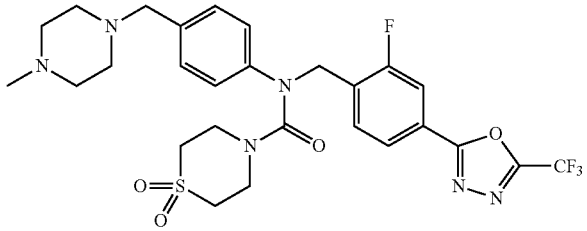 [SMILES: CN1CCN(Cc2ccc(N(Cc3ccc(-c4nnc(C(F)(F)F)o4)cc3F)C(=O)N3CCS(=O)(=O)CC3)cc2)CC1] |
| 177 | 21516 | 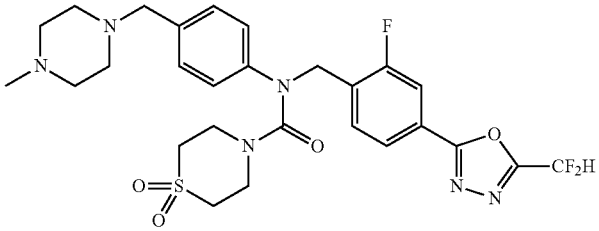 [SMILES: CN1CCN(Cc2ccc(N(Cc3ccc(-c4nnc(C(F)F)o4)cc3F)C(=O)N3CCS(=O)(=O)CC3)cc2)CC1] |
| 178 | 21517 | 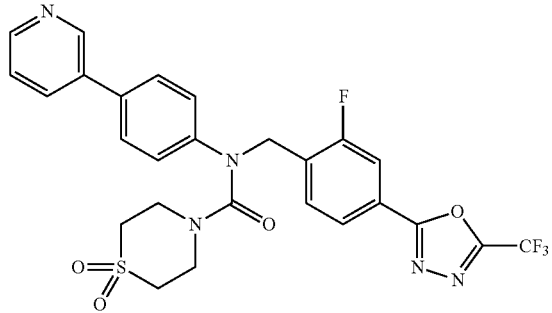 [SMILES: O=C(N1CCS(=O)(=O)CC1)N(Cc1ccc(-c2nnc(C(F)(F)F)o2)cc1F)c1ccc(-c2cccnc2)cc1] |
| 179 | 21518 | 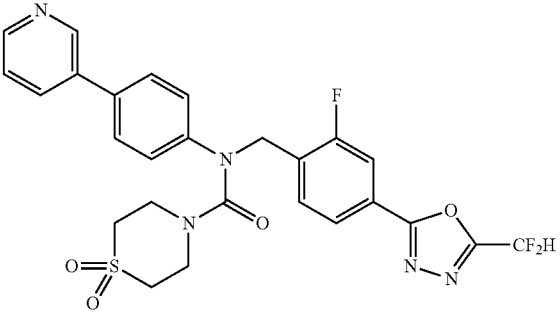 [SMILES: O=C(N1CCS(=O)(=O)CC1)N(Cc1ccc(-c2nnc(C(F)F)o2)cc1F)c1ccc(-c2cccnc2)cc1] |
| 180 | 21519 | 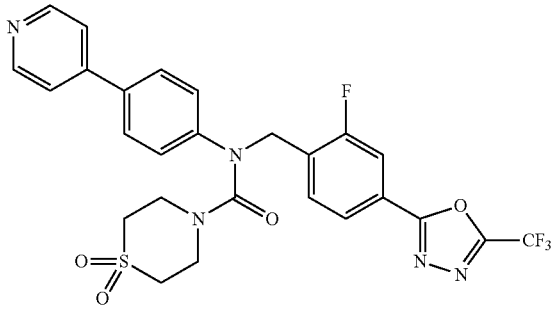 [SMILES: O=C(N1CCS(=O)(=O)CC1)N(Cc1ccc(-c2nnc(C(F)(F)F)o2)cc1F)c1ccc(-c2ccncc2)cc1] |

TABLE 1-continued

| Ex. | Comp. | Structure |
|---|---|---|
| 181 | 21520 | 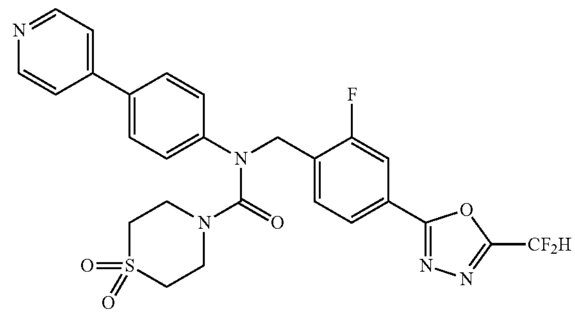 [SMILES: O=C(N1CCS(=O)(=O)CC1)N(Cc1ccc(-c2nnc(C(F)F)o2)cc1F)c1ccc(-c2ccncc2)cc1] |
| 182 | 21521 | 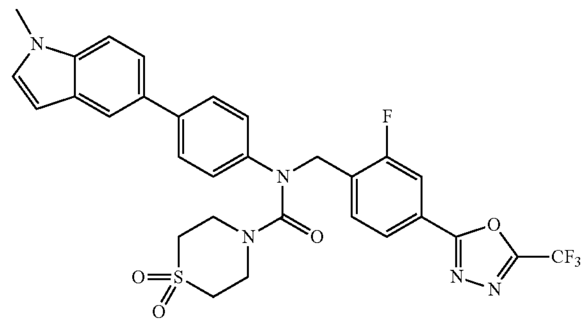 [SMILES: Cn1ccc2cc(-c3ccc(N(Cc4ccc(-c5nnc(C(F)(F)F)o5)cc4F)C(=O)N4CCS(=O)(=O)CC4)cc3)ccc21] |
| 183 | 21522 | 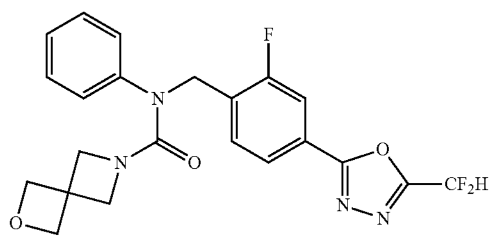 [SMILES: O=C(N1CC2(COC2)C1)N(Cc1ccc(-c2nnc(C(F)F)o2)cc1F)c1ccccc1] |
| 184 | 21527 | 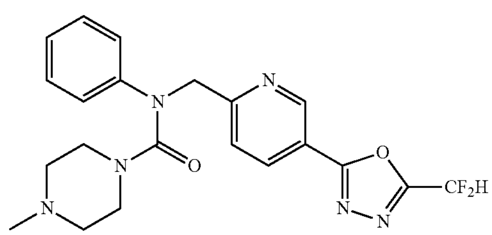 |
| 185 | 21528 | 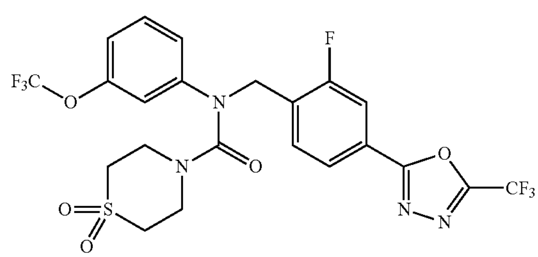 [SMILES: O=C(N1CCS(=O)(=O)CC1)N(Cc1ccc(-c2nnc(C(F)(F)F)o2)cc1F)c1cccc(OC(F)(F)F)c1] |

TABLE 1-continued

| Ex. | Comp. | Structure |
|---|---|---|
| 186 | 21529 | 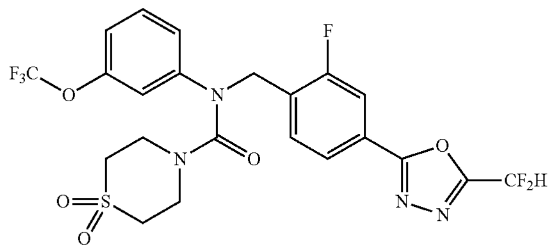 [SMILES: O=C(N1CCS(=O)(=O)CC1)N(Cc1ccc(-c2nnc(C(F)F)o2)cc1F)c1cccc(OC(F)(F)F)c1] |
| 187 | 21530 | 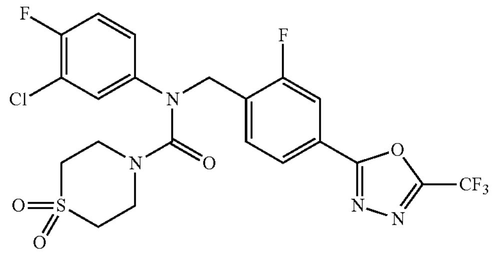 [SMILES: O=C(N1CCS(=O)(=O)CC1)N(Cc1ccc(-c2nnc(C(F)(F)F)o2)cc1F)c1ccc(F)c(Cl)c1] |
| 188 | 21531 | 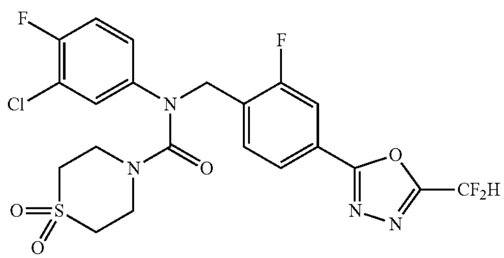 [SMILES: O=C(N1CCS(=O)(=O)CC1)N(Cc1ccc(-c2nnc(C(F)F)o2)cc1F)c1ccc(F)c(Cl)c1] |
| 189 | 21532 | 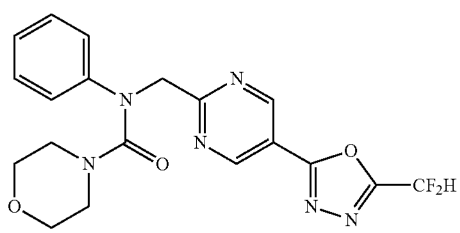 [SMILES: O=C(N1CCOCC1)N(Cc1ncc(-c2nnc(C(F)F)o2)cn1)c1ccccc1] |
| 190 | 21533 | 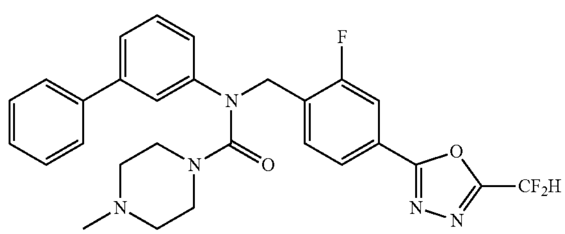 [SMILES: CN1CCN(C(=O)N(Cc2ccc(-c3nnc(C(F)F)o3)cc2F)c2cccc(-c3ccccc3)c2)CC1] |
| 191 | 21534 | 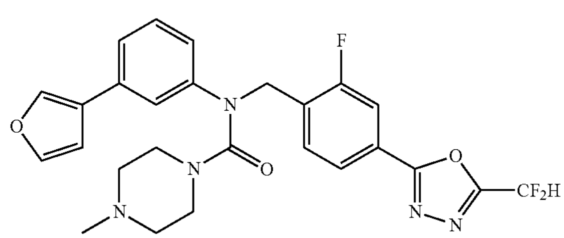 [SMILES: CN1CCN(C(=O)N(Cc2ccc(-c3nnc(C(F)F)o3)cc2F)c2cccc(-c3ccoc3)c2)CC1] |

TABLE 1-continued

| Ex. | Comp. | Structure |
|---|---|---|
| 192 | 21535 | 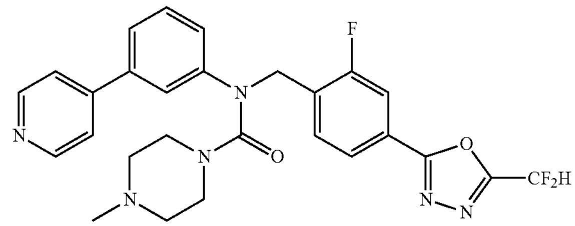 [SMILES: CN1CCN(C(=O)N(Cc2ccc(-c3nnc(C(F)F)o3)cc2F)c2cccc(-c3ccncc3)c2)CC1] |
| 193 | 21536 | 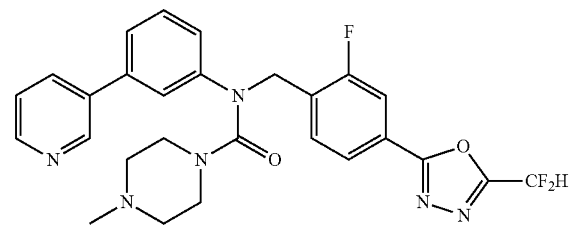 [SMILES: CN1CCN(C(=O)N(Cc2ccc(-c3nnc(C(F)F)o3)cc2F)c2cccc(-c3cccnc3)c2)CC1] |
| 194 | 21537 | 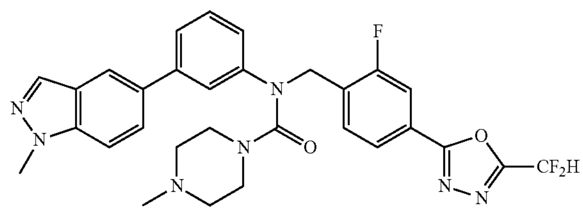 [SMILES: CN1CCN(C(=O)N(Cc2ccc(-c3nnc(C(F)F)o3)cc2F)c2cccc(-c3ccc4c(cnn4C)c3)c2)CC1] |
| 195 | 21540 | 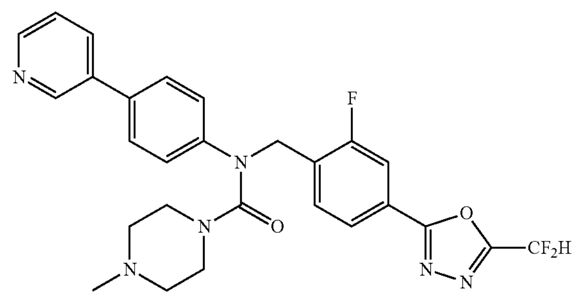 [SMILES: CN1CCN(C(=O)N(Cc2ccc(-c3nnc(C(F)F)o3)cc2F)c2ccc(-c3cccnc3)cc2)CC1] |
| 196 | 21541 | 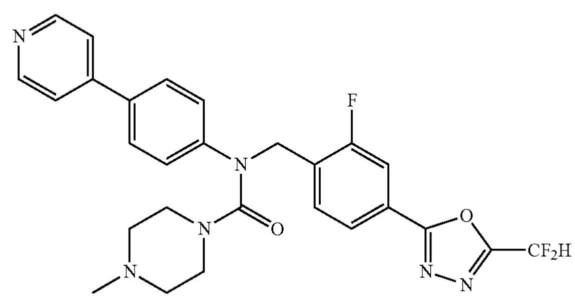 [SMILES: CN1CCN(C(=O)N(Cc2ccc(-c3nnc(C(F)F)o3)cc2F)c2ccc(-c3ccncc3)cc2)CC1] |
| 197 | 21542 | 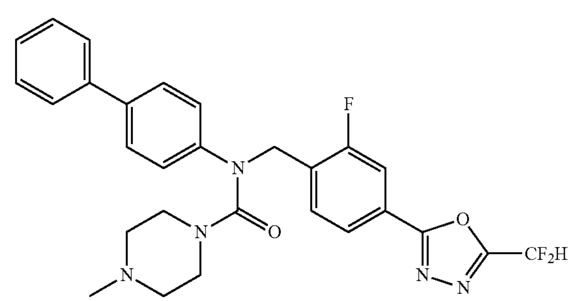 [SMILES: CN1CCN(C(=O)N(Cc2ccc(-c3nnc(C(F)F)o3)cc2F)c2ccc(-c3ccccc3)cc2)CC1] |

TABLE 1-continued

| Ex. | Comp. | Structure |
|---|---|---|
| 198 | 21543 | 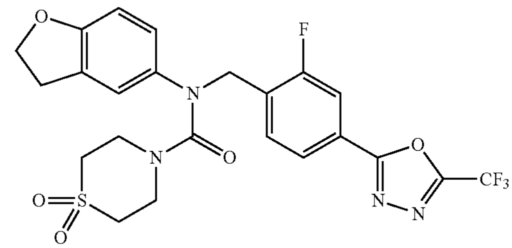 [SMILES: O=C(N1CCS(=O)(=O)CC1)N(Cc1ccc(-c2nnc(C(F)(F)F)o2)cc1F)c1ccc2c(c1)CCO2] |
| 199 | 21544 | 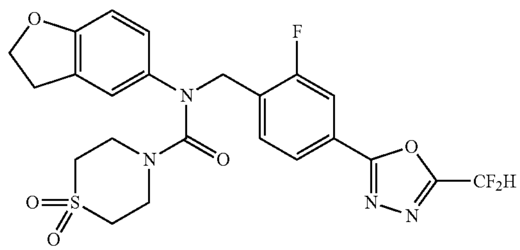 |
| 200 | 21545 | 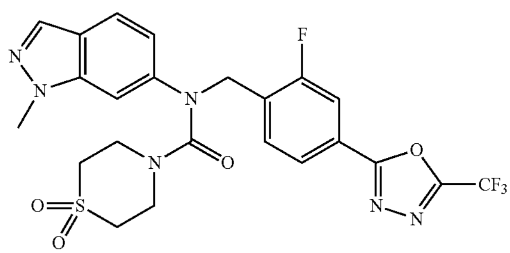 [SMILES: Cn1ncc2ccc(N(Cc3ccc(-c4nnc(C(F)(F)F)o4)cc3F)C(=O)N3CCS(=O)(=O)CC3)cc21] |
| 201 | 21546 | 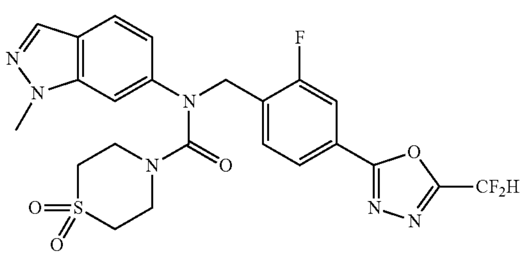 [SMILES: Cn1ncc2ccc(N(Cc3ccc(-c4nnc(C(F)F)o4)cc3F)C(=O)N3CCS(=O)(=O)CC3)cc21] |
| 202 | 21552 | 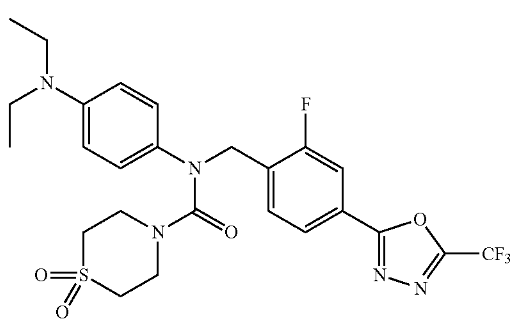 [SMILES: CCN(CC)c1ccc(N(Cc2ccc(-c3nnc(C(F)(F)F)o3)cc2F)C(=O)N2CCS(=O)(=O)CC2)cc1] |

TABLE 1-continued

| Ex. | Comp. | Structure |
|---|---|---|
| 203 | 21553 | 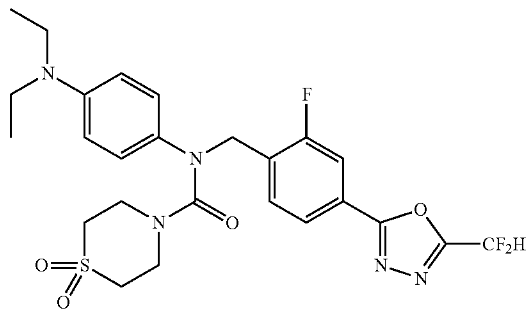 [SMILES: CCN(CC)c1ccc(N(Cc2ccc(-c3nnc(C(F)F)o3)cc2F)C(=O)N2CCS(=O)(=O)CC2)cc1] |
| 204 | 21554 | 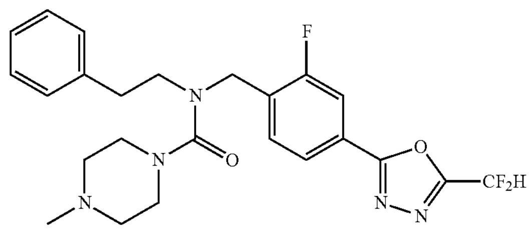 [SMILES: CN1CCN(C(=O)N(CCc2ccccc2)Cc2ccc(-c3nnc(C(F)F)o3)cc2F)CC1] |
| 205 | 21555 | 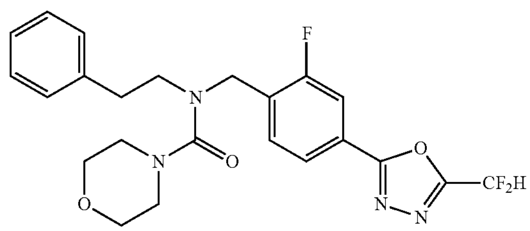 [SMILES: O=C(N1CCOCC1)N(CCc1ccccc1)Cc1ccc(-c2nnc(C(F)F)o2)cc1F] |
| 206 | 21556 | 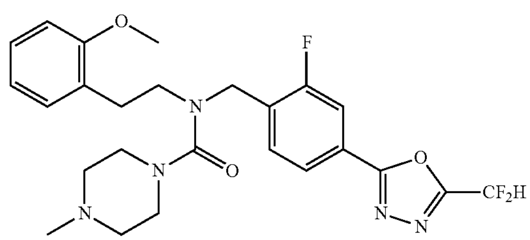 [SMILES: COc1ccccc1CCN(Cc1ccc(-c2nnc(C(F)F)o2)cc1F)C(=O)N1CCN(C)CC1] |
| 207 | 21557 | 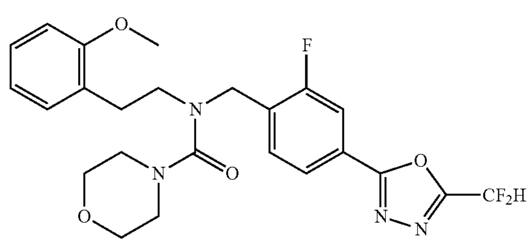 [SMILES: COc1ccccc1CCN(Cc1ccc(-c2nnc(C(F)F)o2)cc1F)C(=O)N1CCOCC1] |
| 208 | 21564 | 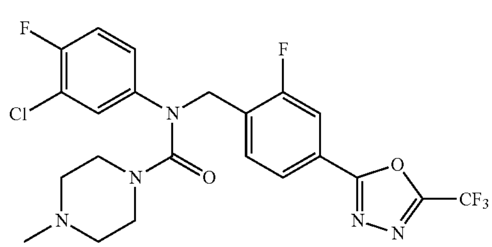 [SMILES: CN1CCN(C(=O)N(Cc2ccc(-c3nnc(C(F)(F)F)o3)cc2F)c2ccc(F)c(Cl)c2)CC1] |

TABLE 1-continued

| Ex. | Comp. | Structure |
|---|---|---|
| 209 | 21565 | 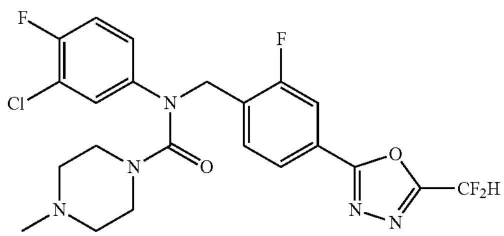 [SMILES: CN1CCN(C(=O)N(Cc2ccc(-c3nnc(C(F)F)o3)cc2F)c2ccc(F)c(Cl)c2)CC1] |
| 210 | 21566 | 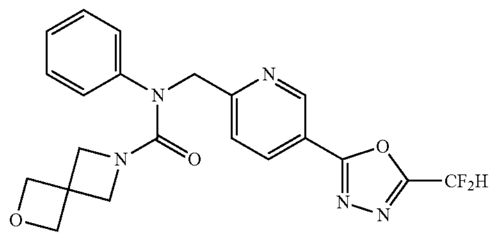 [SMILES: O=C(N1CC2(COC2)C1)N(Cc1ccc(-c2nnc(C(F)F)o2)cn1)c1ccccc1] |
| 211 | 21568 | 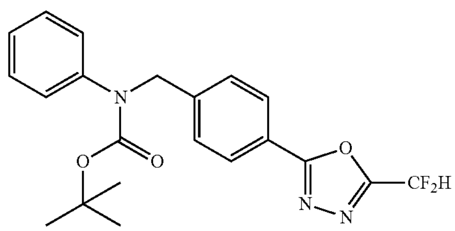 [SMILES: CC(C)(C)OC(=O)N(Cc1ccc(-c2nnc(C(F)F)o2)cc1)c1ccccc1] |
| 212 | 21569 | 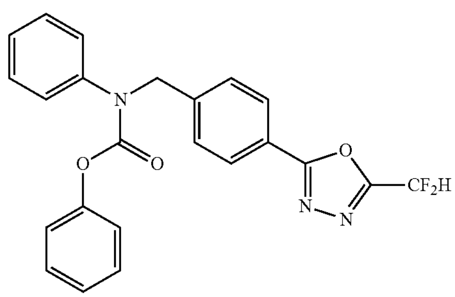 [SMILES: O=C(Oc1ccccc1)N(Cc1ccc(-c2nnc(C(F)F)o2)cc1)c1ccccc1] |
| 213 | 21570 | 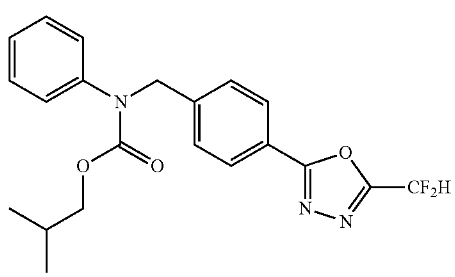 [SMILES: CC(C)COC(=O)N(Cc1ccc(-c2nnc(C(F)F)o2)cc1)c1ccccc1] |
| 214 | 21576 | 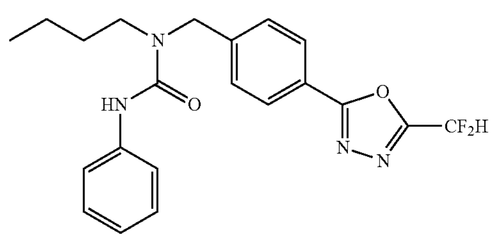 [SMILES: CCCCN(Cc1ccc(-c2nnc(C(F)F)o2)cc1)C(=O)Nc1ccccc1] |

TABLE 1-continued

| Ex. | Comp. | Structure |
|---|---|---|
| 215 | 21577 | 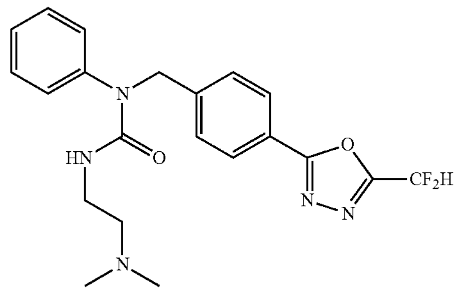 [SMILES: CN(C)CCNC(=O)N(Cc1ccc(-c2nnc(C(F)F)o2)cc1)c1ccccc1] |
| 216 | 21578 | 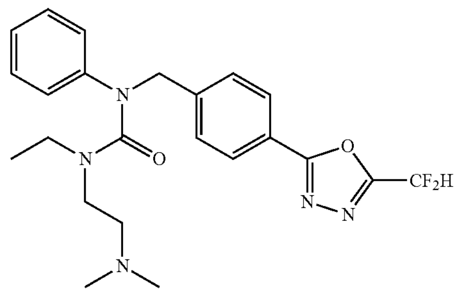 [SMILES: CCN(CCN(C)C)C(=O)N(Cc1ccc(-c2nnc(C(F)F)o2)cc1)c1ccccc1] |
| 217 | 21583 | 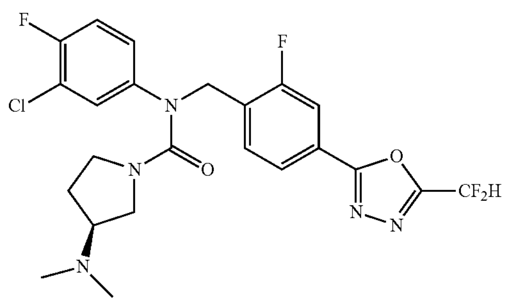 [SMILES: CN(C)[C@H]1CCN(C(=O)N(Cc2ccc(-c3nnc(C(F)F)o3)cc2F)c2ccc(F)c(Cl)c2)C1] |
| 218 | 21584 | 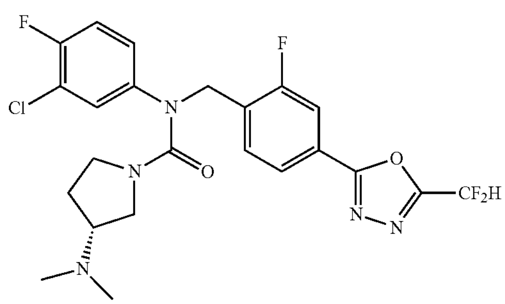 [SMILES: CN(C)[C@@H]1CCN(C(=O)N(Cc2ccc(-c3nnc(C(F)F)o3)cc2F)c2ccc(F)c(Cl)c2)C1] |
| 219 | 21585 | 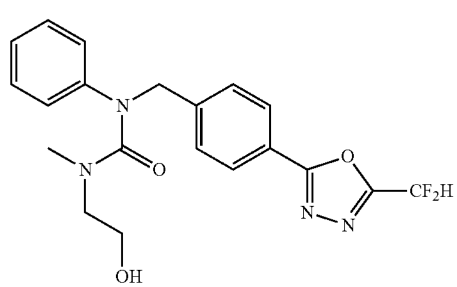 [SMILES: CN(CCO)C(=O)N(Cc1ccc(-c2nnc(C(F)F)o2)cc1)c1ccccc1] |

TABLE 1-continued

| Ex. | Comp. | Structure |
|---|---|---|
| 220 | 21586 | 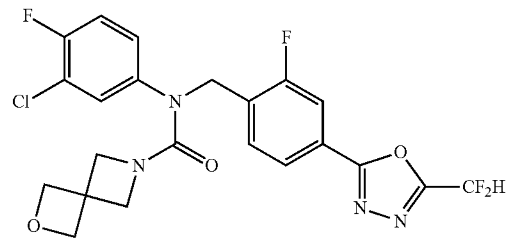 [SMILES: O=C(N1CC2(COC2)C1)N(Cc1ccc(-c2nnc(C(F)F)o2)cc1F)c1ccc(F)c(Cl)c1] |
| 221 | 21587 | 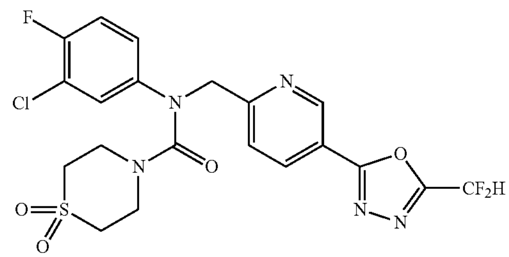 [SMILES: O=C(N1CCS(=O)(=O)CC1)N(Cc1ccc(-c2nnc(C(F)F)o2)cn1)c1ccc(F)c(Cl)c1] |
| 222 | 21591 | 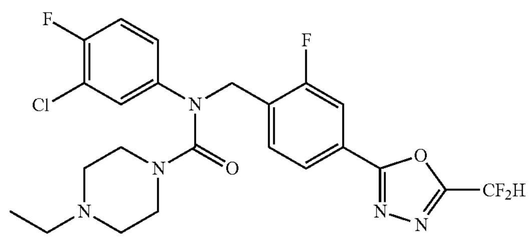 [SMILES: CCN1CCN(C(=O)N(Cc2ccc(-c3nnc(C(F)F)o3)cc2F)c2ccc(F)c(Cl)c2)CC1] |
| 223 | 21592 | 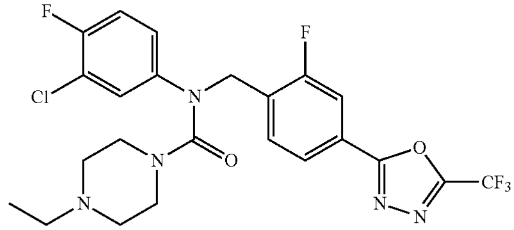 [SMILES: CCN1CCN(C(=O)N(Cc2ccc(-c3nnc(C(F)(F)F)o3)cc2F)c2ccc(F)c(Cl)c2)CC1] |
| 224 | 21593 | 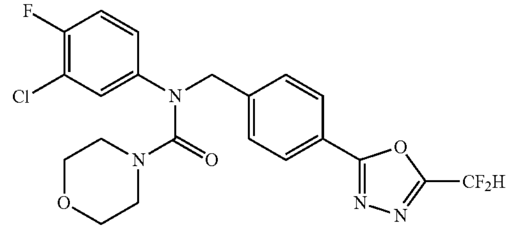 [SMILES: O=C(N1CCOCC1)N(Cc1ccc(-c2nnc(C(F)F)o2)cc1)c1ccc(F)c(Cl)c1] |
| 225 | 21594 | 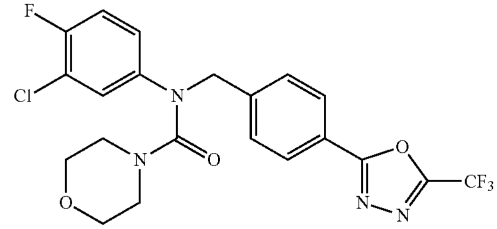 [SMILES: O=C(N1CCOCC1)N(Cc1ccc(-c2nnc(C(F)(F)F)o2)cc1)c1ccc(F)c(Cl)c1] |

TABLE 1-continued

| Ex. | Comp. | Structure |
|---|---|---|
| 226 | 21597 | 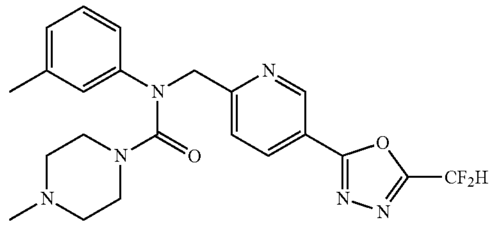 [SMILES: Cc1cccc(N(Cc2ccc(-c3nnc(C(F)F)o3)cn2)C(=O)N2CCN(C)CC2)c1] |
| 227 | 21598 | 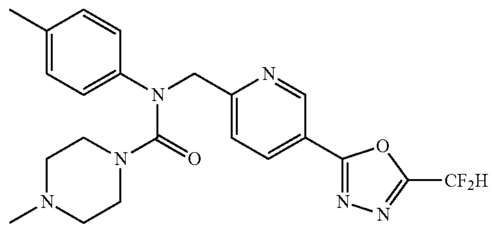 [SMILES: Cc1ccc(N(Cc2ccc(-c3nnc(C(F)F)o3)cn2)C(=O)N2CCN(C)CC2)cc1] |
| 228 | 21599 | 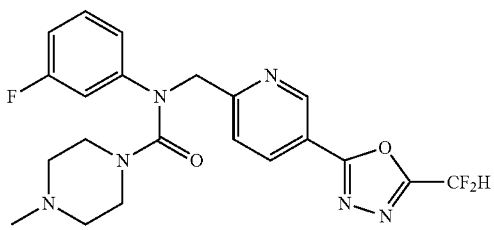 [SMILES: CN1CCN(C(=O)N(Cc2ccc(-c3nnc(C(F)F)o3)cn2)c2cccc(F)c2)CC1] |
| 229 | 21600 | 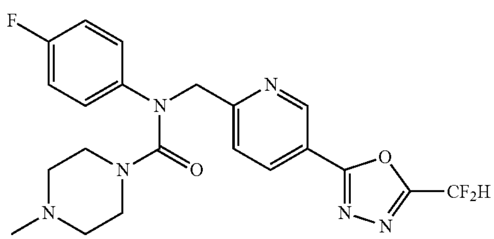 [SMILES: CN1CCN(C(=O)N(Cc2ccc(-c3nnc(C(F)F)o3)cn2)c2ccc(F)cc2)CC1] |
| 230 | 21601 | 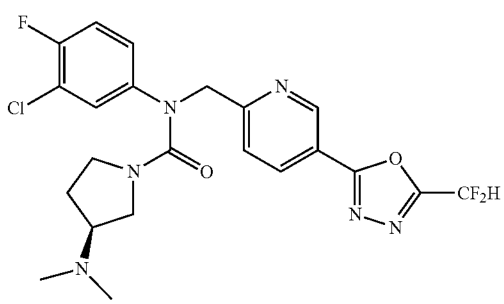 [SMILES: CN(C)[C@H]1CCN(C(=O)N(Cc2ccc(-c3nnc(C(F)F)o3)cn2)c2ccc(F)c(Cl)c2)C1] |
| 231 | 21602 | 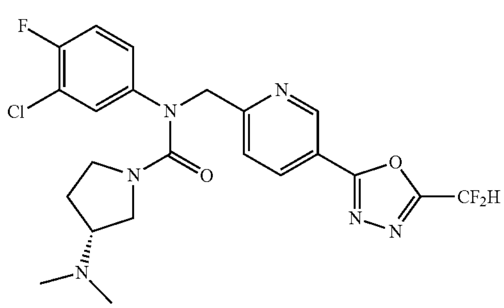 [SMILES: CN(C)[C@@H]1CCN(C(=O)N(Cc2ccc(-c3nnc(C(F)F)o3)cn2)c2ccc(F)c(Cl)c2)C1] |

TABLE 1-continued

| Ex. | Comp. | Structure |
|---|---|---|
| 232 | 21619 | 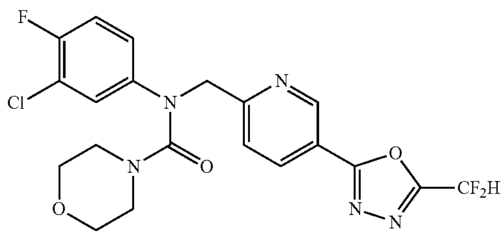 [SMILES: O=C(N1CCOCC1)N(Cc1ccc(-c2nnc(C(F)F)o2)cn1)c1ccc(F)c(Cl)c1] |
| 233 | 21620 | 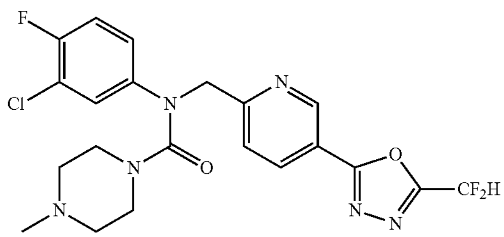 [SMILES: CN1CCN(C(=O)N(Cc2ccc(-c3nnc(C(F)F)o3)cn2)c2ccc(F)c(Cl)c2)CC1] |
| 234 | 21621 | 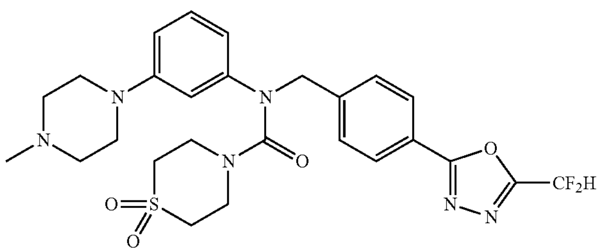 [SMILES: CN1CCN(c2cccc(N(Cc3ccc(-c4nnc(C(F)F)o4)cc3)C(=O)N3CCS(=O)(=O)CC3)c2)CC1] |
| 235 | 21622 | 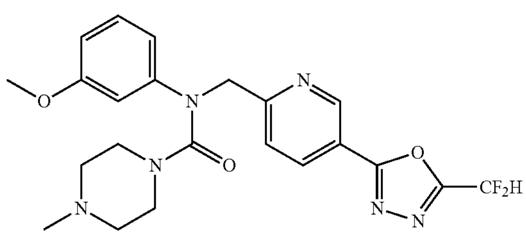 [SMILES: COc1cccc(N(Cc2ccc(-c3nnc(C(F)F)o3)cn2)C(=O)N2CCN(C)CC2)c1] |
| 236 | 21623 | 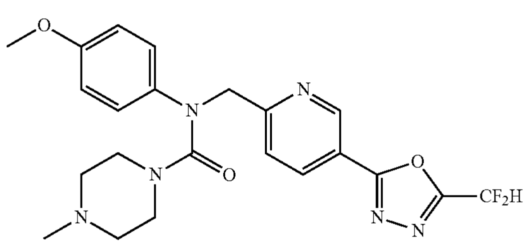 [SMILES: COc1ccc(N(Cc2ccc(-c3nnc(C(F)F)o3)cn2)C(=O)N2CCN(C)CC2)cc1] |
| 237 | 21624 | 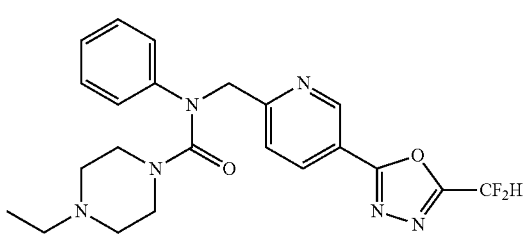 [SMILES: CCN1CCN(C(=O)N(Cc2ccc(-c3nnc(C(F)F)o3)cn2)c2ccccc2)CC1] |

TABLE 1-continued

| Ex. | Comp. | Structure |
|-----|-------|-----------|
| 238 | 21625 | 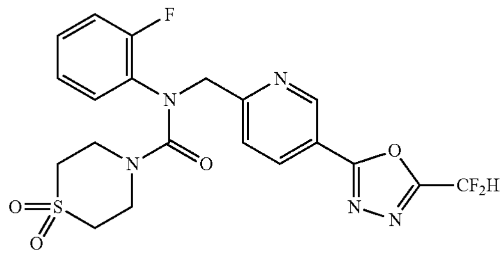 |
| 239 | 21626 | 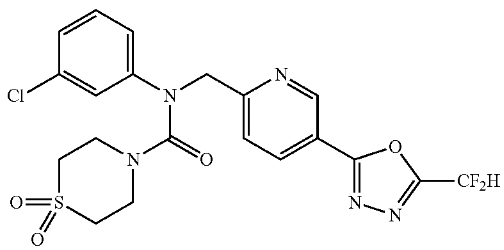 [SMILES: O=C(N1CCS(=O)(=O)CC1)N(Cc1ccc(-c2nnc(C(F)F)o2)cn1)c1cccc(Cl)c1] |
| 240 | 21627 | 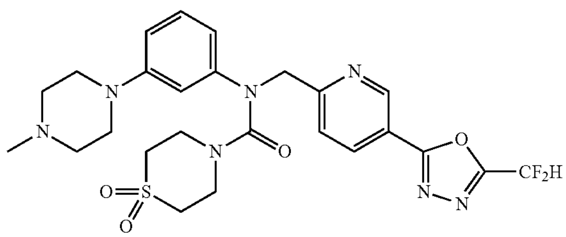 [SMILES: CN1CCN(c2cccc(N(Cc3ccc(-c4nnc(C(F)F)o4)cn3)C(=O)N3CCS(=O)(=O)CC3)c2)CC1] |
| 241 | 21628 | 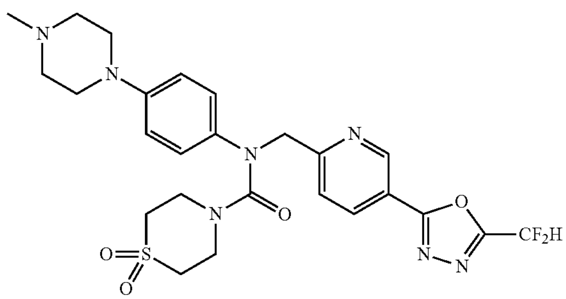 [SMILES: CN1CCN(c2ccc(N(Cc3ccc(-c4nnc(C(F)F)o4)cn3)C(=O)N3CCS(=O)(=O)CC3)cc2)CC1] |
| 242 | 21629 | 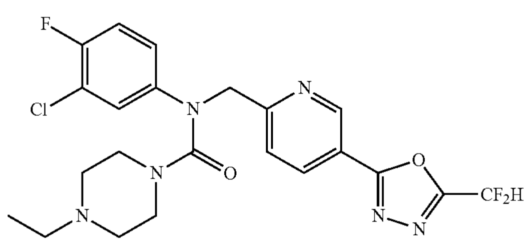 [SMILES: CCN1CCN(C(=O)N(Cc2ccc(-c3nnc(C(F)F)o3)cn2)c2ccc(F)c(Cl)c2)CC1] |
| 243 | 21630 | 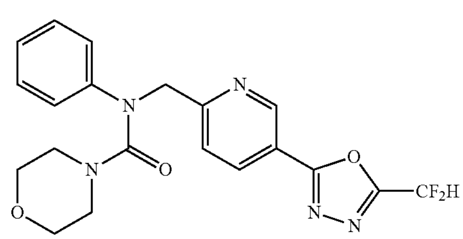 |

TABLE 1-continued

| Ex. | Comp. | Structure |
|-----|-------|-----------|
| 244 | 21631 | 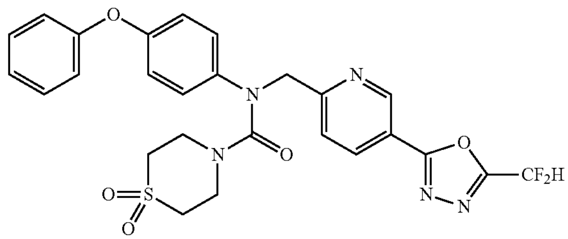 [SMILES: O=C(N1CCS(=O)(=O)CC1)N(Cc1ccc(-c2nnc(C(F)F)o2)cn1)c1ccc(Oc2ccccc2)cc1] |
| 245 | 21632 | 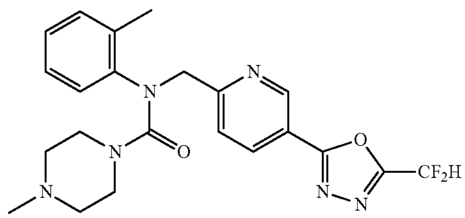 [SMILES: Cc1ccccc1N(Cc1ccc(-c2nnc(C(F)F)o2)cn1)C(=O)N1CCN(C)CC1] |
| 246 | 21633 | 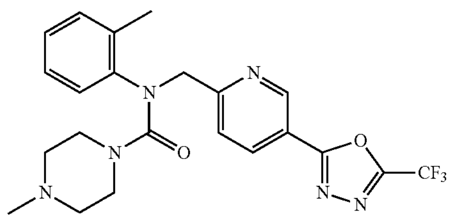 [SMILES: Cc1ccccc1N(Cc1ccc(-c2nnc(C(F)(F)F)o2)cn1)C(=O)N1CCN(C)CC1] |
| 247 | 21634 | 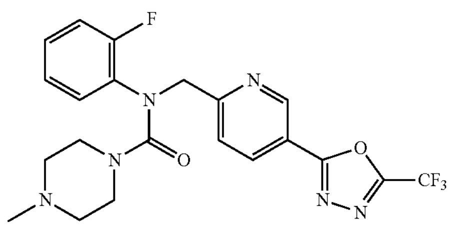 [SMILES: CN1CCN(C(=O)N(Cc2ccc(-c3nnc(C(F)(F)F)o3)cn2)c2ccccc2F)CC1] |
| 248 | 21643 | 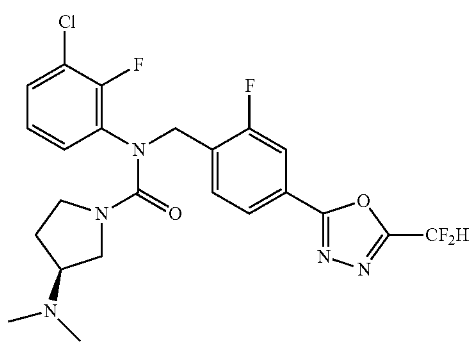 [SMILES: CN(C)[C@H]1CCN(C(=O)N(Cc2ccc(-c3nnc(C(F)F)o3)cc2F)c2cccc(Cl)c2F)C1] |
| 249 | 21644 | 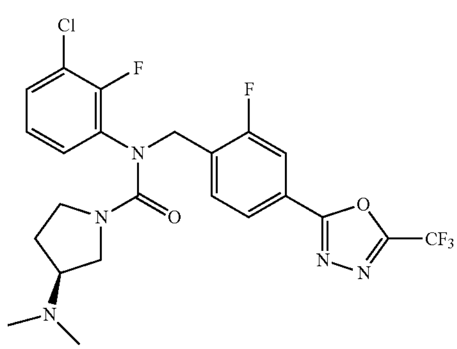 [SMILES: CN(C)[C@H]1CCN(C(=O)N(Cc2ccc(-c3nnc(C(F)(F)F)o3)cc2F)c2cccc(Cl)c2F)C1] |

TABLE 1-continued

| Ex. | Comp. | Structure |
|---|---|---|
| 250 | 21645 | 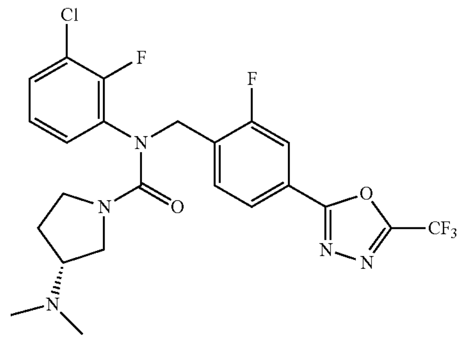 [SMILES: CN(C)[C@@H]1CCN(C(=O)N(Cc2ccc(-c3nnc(C(F)(F)F)o3)cc2F)c2cccc(Cl)c2F)C1] |
| 251 | 21646 | 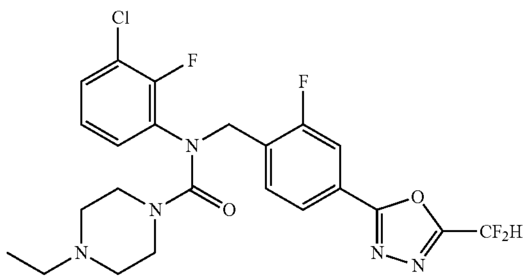 [SMILES: CCN1CCN(C(=O)N(Cc2ccc(-c3nnc(C(F)F)o3)cc2F)c2cccc(Cl)c2F)CC1] |
| 252 | 21650 | 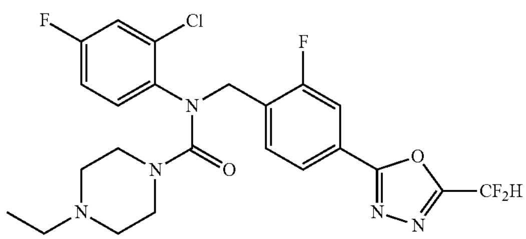 [SMILES: CCN1CCN(C(=O)N(Cc2ccc(-c3nnc(C(F)F)o3)cc2F)c2ccc(F)cc2Cl)CC1] |
| 253 | 21651 | 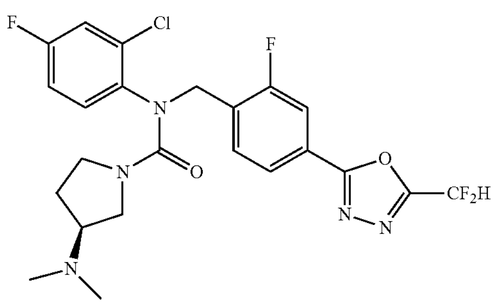 [SMILES: CN(C)[C@H]1CCN(C(=O)N(Cc2ccc(-c3nnc(C(F)F)o3)cc2F)c2ccc(F)cc2Cl)C1] |
| 254 | 21652 | 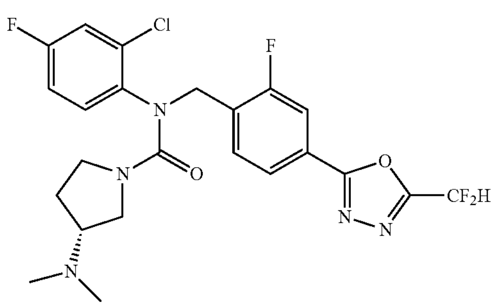 [SMILES: CN(C)[C@@H]1CCN(C(=O)N(Cc2ccc(-c3nnc(C(F)F)o3)cc2F)c2ccc(F)cc2Cl)C1] |

TABLE 1-continued

| Ex. | Comp. | Structure |
|---|---|---|
| 255 | 21653 | 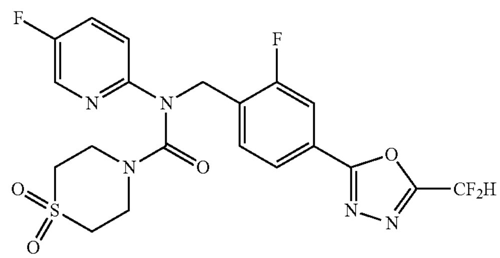 [SMILES: O=C(N1CCS(=O)(=O)CC1)N(Cc1ccc(-c2nnc(C(F)F)o2)cc1F)c1ccc(F)cn1] |
| 256 | 21654 | 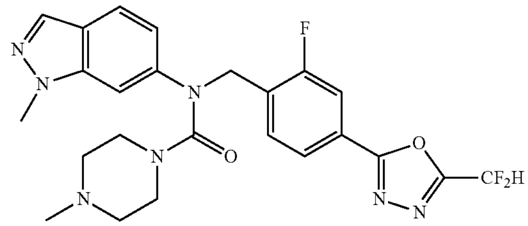 [SMILES: CN1CCN(C(=O)N(Cc2ccc(-c3nnc(C(F)F)o3)cc2F)c2ccc3cnn(C)c3c2)CC1] |
| 257 | 21655 | 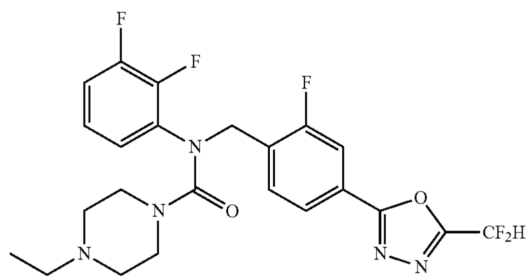 [SMILES: CCN1CCN(C(=O)N(Cc2ccc(-c3nnc(C(F)F)o3)cc2F)c2cccc(F)c2F)CC1] |
| 258 | 21656 | 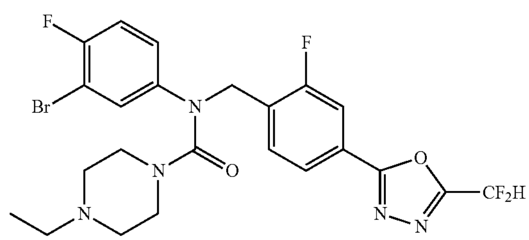 [SMILES: CCN1CCN(C(=O)N(Cc2ccc(-c3nnc(C(F)F)o3)cc2F)c2ccc(F)c(Br)c2)CC1] |
| 259 | 21657 | 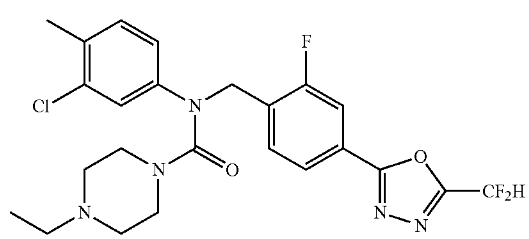 [SMILES: CCN1CCN(C(=O)N(Cc2ccc(-c3nnc(C(F)F)o3)cc2F)c2ccc(C)c(Cl)c2)CC1] |
| 260 | 21658 | 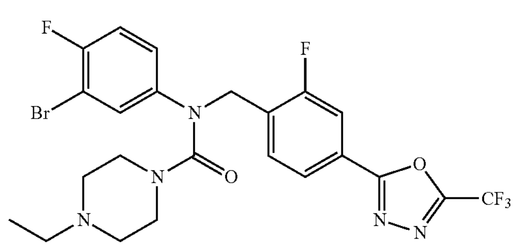 [SMILES: CCN1CCN(C(=O)N(Cc2ccc(-c3nnc(C(F)(F)F)o3)cc2F)c2ccc(F)c(Br)c2)CC1] |

TABLE 1-continued

| Ex. | Comp. | Structure |
|---|---|---|
| 261 | 21659 | 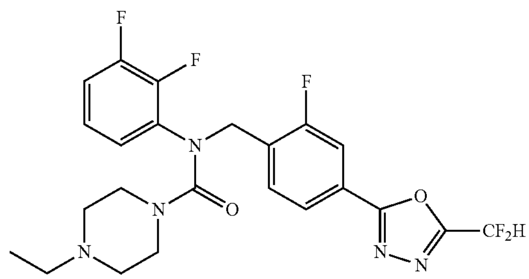 [SMILES: CCN1CCN(C(=O)N(Cc2ccc(-c3nnc(C(F)F)o3)cc2F)c2cccc(F)c2F)CC1] |
| 262 | 21660 | 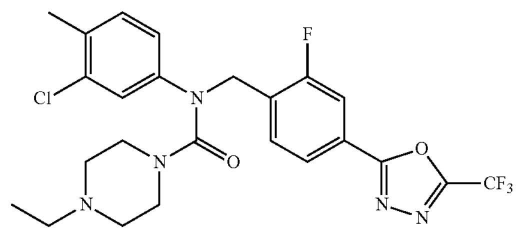 [SMILES: CCN1CCN(C(=O)N(Cc2ccc(-c3nnc(C(F)(F)F)o3)cc2F)c2ccc(C)c(Cl)c2)CC1] |
| 263 | 21664 | 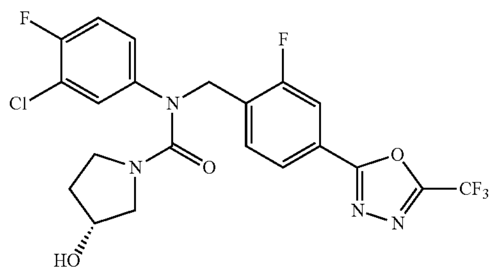 [SMILES: O=C(N1CC[C@@H](O)C1)N(Cc1ccc(-c2nnc(C(F)(F)F)o2)cc1F)c1ccc(F)c(Cl)c1] |
| 264 | 21665 | 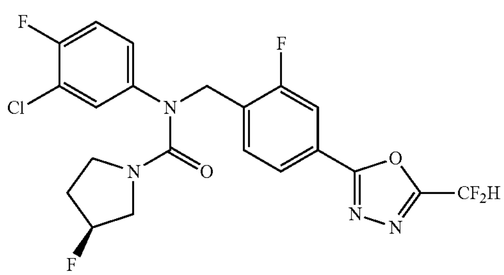 [SMILES: O=C(N1CC[C@H](F)C1)N(Cc1ccc(-c2nnc(C(F)F)o2)cc1F)c1ccc(F)c(Cl)c1] |
| 265 | 21666 | 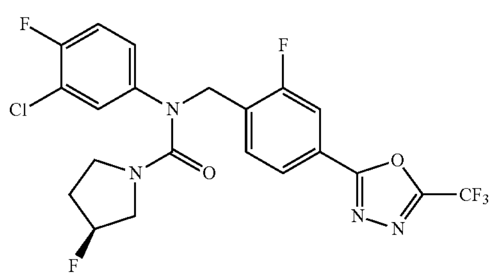 [SMILES: O=C(N1CC[C@H](F)C1)N(Cc1ccc(-c2nnc(C(F)(F)F)o2)cc1F)c1ccc(F)c(Cl)c1] |
| 266 | 21667 | 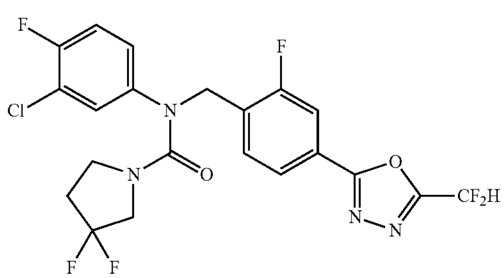 [SMILES: O=C(N1CCC(F)(F)C1)N(Cc1ccc(-c2nnc(C(F)F)o2)cc1F)c1ccc(F)c(Cl)c1] |

TABLE 1-continued

| Ex. | Comp. | Structure |
|---|---|---|
| 267 | 21668 | 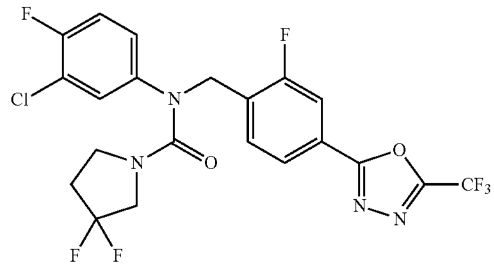 [SMILES: O=C(N1CCC(F)(F)C1)N(Cc1ccc(-c2nnc(C(F)(F)F)o2)cc1F)c1ccc(F)c(Cl)c1] |
| 268 | 21669 | 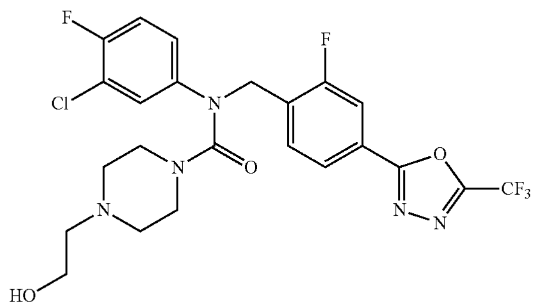 [SMILES: O=C(N1CCN(CCO)CC1)N(Cc1ccc(-c2nnc(C(F)(F)F)o2)cc1F)c1ccc(F)c(Cl)c1] |
| 269 | 21679 | 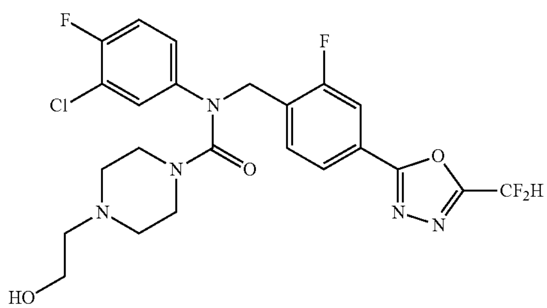 [SMILES: O=C(N1CCN(CCO)CC1)N(Cc1ccc(-c2nnc(C(F)F)o2)cc1F)c1ccc(F)c(Cl)c1] |
| 270 | 21707 | 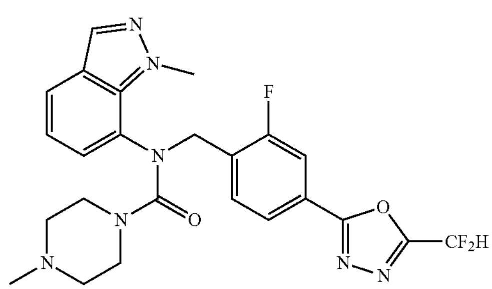 |
| 271 | 21708 | 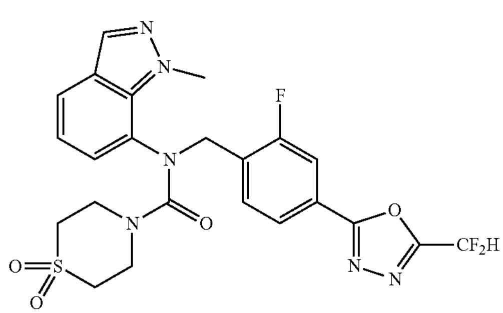 |

TABLE 1-continued

| Ex. | Comp. | Structure |
|---|---|---|
| 272 | 21709 | 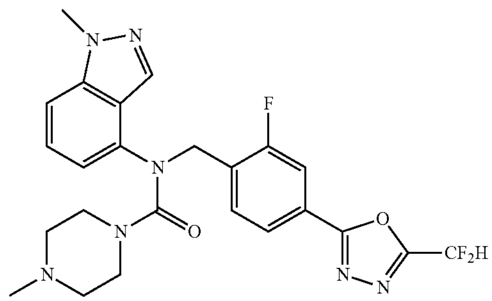 [SMILES: CN1CCN(C(=O)N(Cc2ccc(-c3nnc(C(F)F)o3)cc2F)c2cccc3c2cnn3C)CC1] |
| 273 | 21710 | 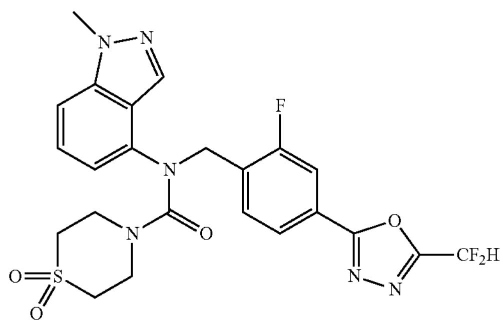 [SMILES: Cn1ncc2c(N(Cc3ccc(-c4nnc(C(F)F)o4)cc3F)C(=O)N3CCS(=O)(=O)CC3)cccc21] |
| 274 | 21724 | 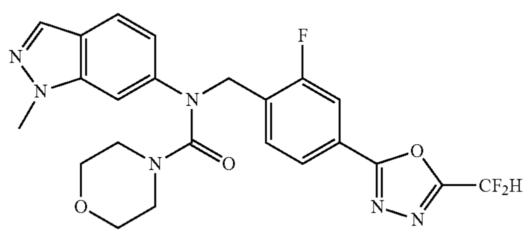 [SMILES: Cn1ncc2ccc(N(Cc3ccc(-c4nnc(C(F)F)o4)cc3F)C(=O)N3CCOCC3)cc21] |
| 275 | 21735 | 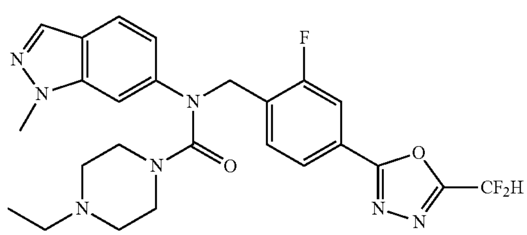 [SMILES: CCN1CCN(C(=O)N(Cc2ccc(-c3nnc(C(F)F)o3)cc2F)c2ccc3cnn(C)c3c2)CC1] |
| 276 | 21746 | 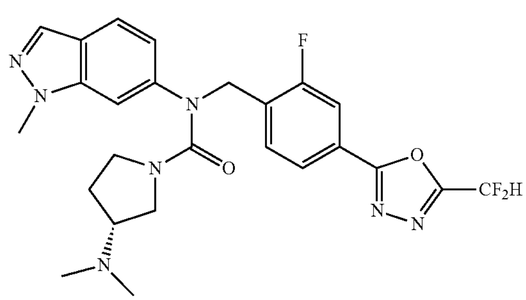 [SMILES: CN(C)[C@@H]1CCN(C(=O)N(Cc2ccc(-c3nnc(C(F)F)o3)cc2F)c2ccc3cnn(C)c3c2)C1] |

TABLE 1-continued

| Ex. | Comp. | Structure |
|---|---|---|
| 277 | 21759 | 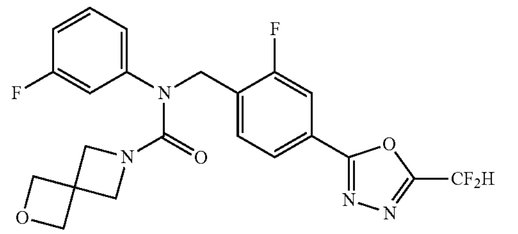 [SMILES: O=C(N1CC2(COC2)C1)N(Cc1ccc(-c2nnc(C(F)F)o2)cc1F)c1cccc(F)c1] |
| 278 | 21760 | 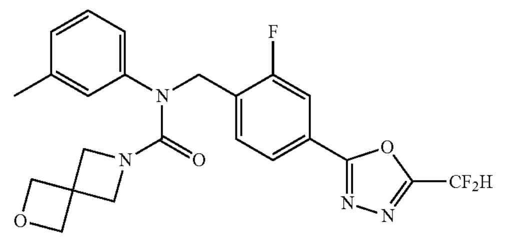 [SMILES: Cc1cccc(N(Cc2ccc(-c3nnc(C(F)F)o3)cc2F)C(=O)N2CC3(COC3)C2)c1] |
| 279 | 21765 | 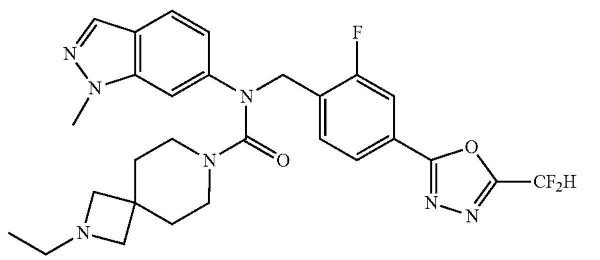 [SMILES: CCN1CC2(CCN(C(=O)N(Cc3ccc(-c4nnc(C(F)F)o4)cc3F)c3ccc4cnn(C)c4c3)CC2)C1] |
| 280 | 21766 | 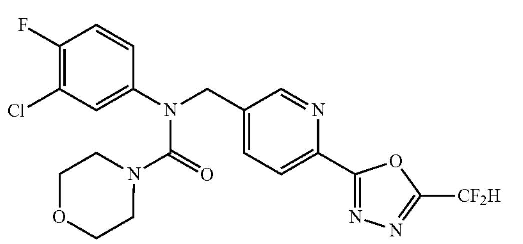 |
| 281 | 21767 | 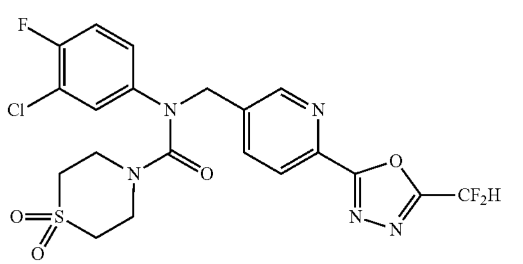 [SMILES: O=C(N1CCS(=O)(=O)CC1)N(Cc1ccc(-c2nnc(C(F)F)o2)nc1)c1ccc(F)c(Cl)c1] |
| 282 | 21797 | 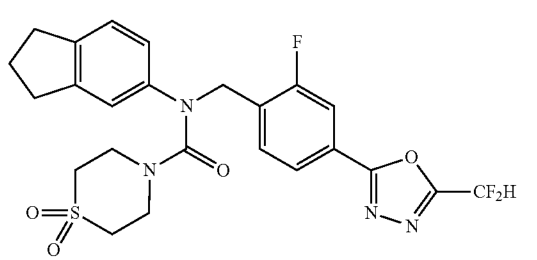 |

TABLE 1-continued

| Ex. | Comp. | Structure |
|---|---|---|
| 283 | 21798 | 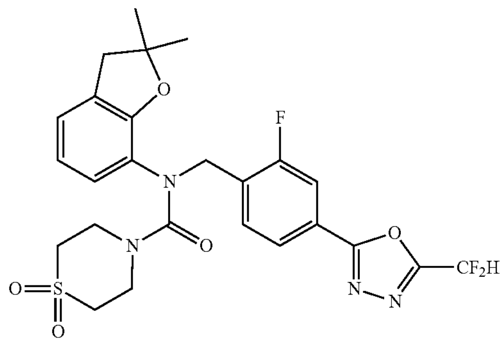 [SMILES: CC1(C)Cc2cccc(N(Cc3ccc(-c4nnc(C(F)F)o4)cc3F)C(=O)N3CCS(=O)(=O)CC3)c2O1] |
| 284 | 21799 | 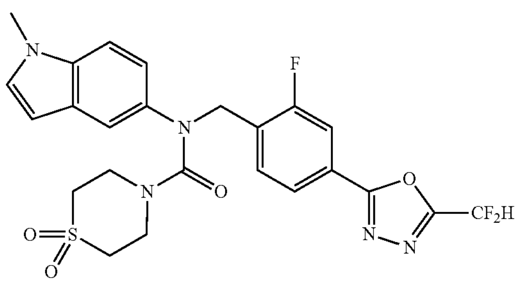 [SMILES: Cn1ccc2cc(N(Cc3ccc(-c4nnc(C(F)F)o4)cc3F)C(=O)N3CCS(=O)(=O)CC3)ccc21] |
| 285 | 21806 | 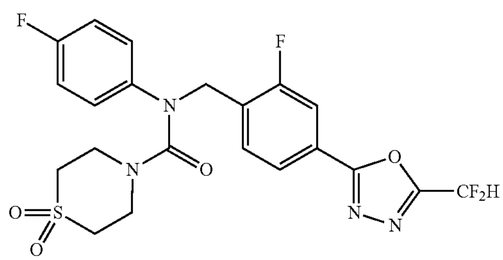 [SMILES: O=C(N1CCS(=O)(=O)CC1)N(Cc1ccc(-c2nnc(C(F)F)o2)cc1F)c1ccc(F)cc1] |
| 286 | 21807 | 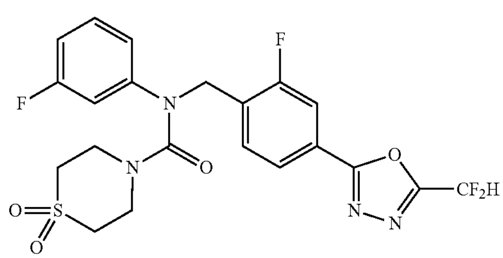 |
| 287 | 21808 | 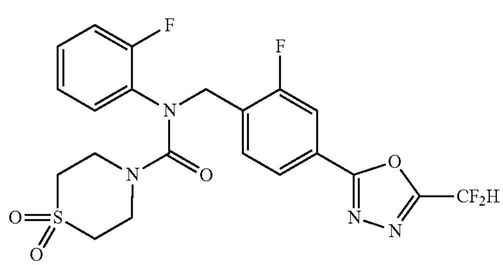 [SMILES: O=C(N1CCS(=O)(=O)CC1)N(Cc1ccc(-c2nnc(C(F)F)o2)cc1F)c1ccccc1F] |

TABLE 1-continued

| Ex. | Comp. | Structure |
|---|---|---|
| 288 | 21809 | 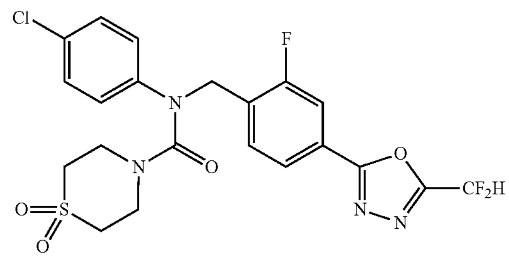 [SMILES: O=C(N1CCS(=O)(=O)CC1)N(Cc1ccc(-c2nnc(C(F)F)o2)cc1F)c1ccc(Cl)cc1] |
| 289 | 21810 | 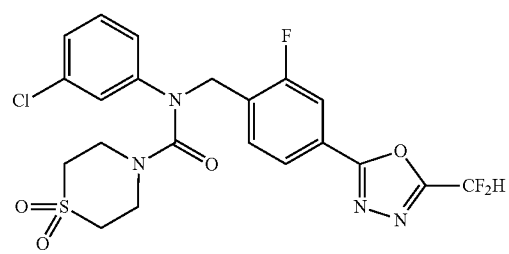 [SMILES: O=C(N1CCS(=O)(=O)CC1)N(Cc1ccc(-c2nnc(C(F)F)o2)cc1F)c1cccc(Cl)c1] |
| 290 | 21811 | 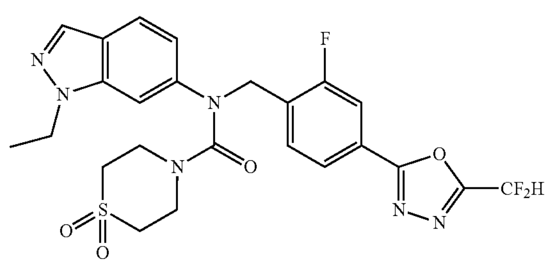 [SMILES: CCn1ncc2ccc(N(Cc3ccc(-c4nnc(C(F)F)o4)cc3F)C(=O)N3CCS(=O)(=O)CC3)cc21] |
| 291 | 21812 | 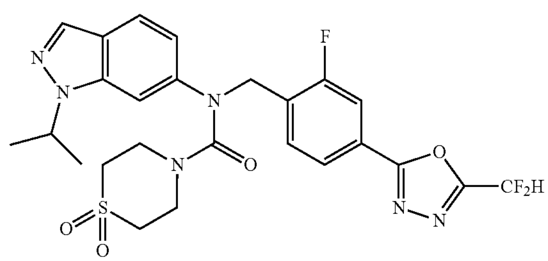 [SMILES: CC(C)n1ncc2ccc(N(Cc3ccc(-c4nnc(C(F)F)o4)cc3F)C(=O)N3CCS(=O)(=O)CC3)cc21] |
| 292 | 21813 | 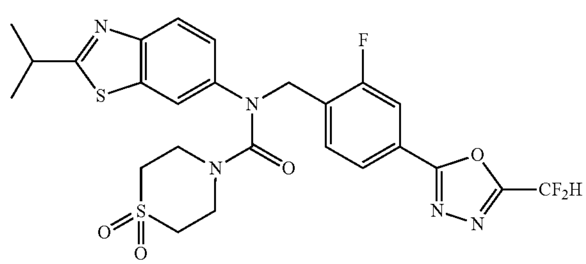 [SMILES: CC(C)c1nc2ccc(N(Cc3ccc(-c4nnc(C(F)F)o4)cc3F)C(=O)N3CCS(=O)(=O)CC3)cc2s1] |
| 293 | 21823 | 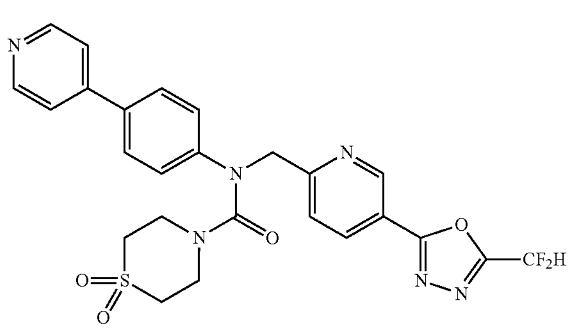 [SMILES: O=C(N1CCS(=O)(=O)CC1)N(Cc1ccc(-c2nnc(C(F)F)o2)cn1)c1ccc(-c2ccncc2)cc1] |

TABLE 1-continued

| Ex. | Comp. | Structure |
|---|---|---|
| 294 | 21824 | 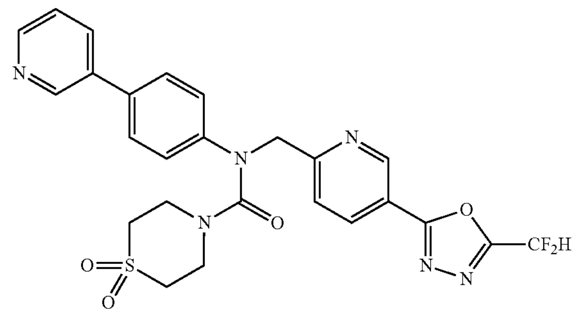 [SMILES: O=C(N1CCS(=O)(=O)CC1)N(Cc1ccc(-c2nnc(C(F)F)o2)cn1)c1ccc(-c2cccnc2)cc1] |
| 295 | 21829 | 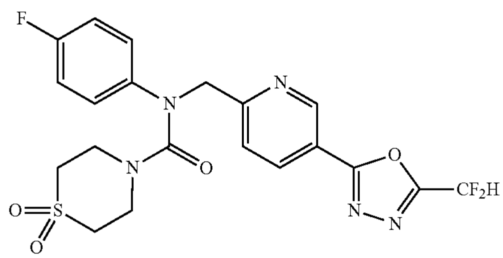 [SMILES: O=C(N1CCS(=O)(=O)CC1)N(Cc1ccc(-c2nnc(C(F)F)o2)cn1)c1ccc(F)cc1] |
| 296 | 21830 | 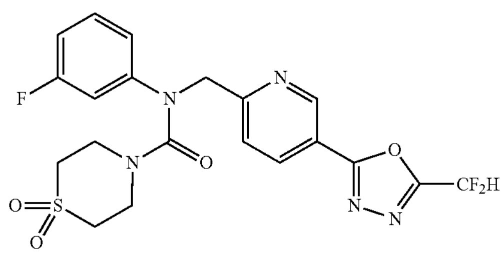 |
| 297 | 21831 | 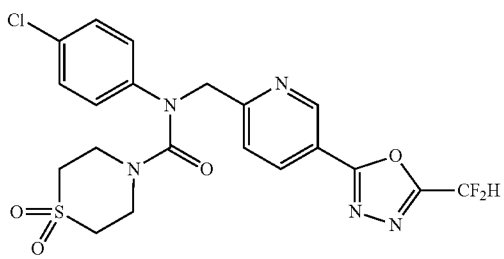 [SMILES: O=C(N1CCS(=O)(=O)CC1)N(Cc1ccc(-c2nnc(C(F)F)o2)cn1)c1ccc(Cl)cc1] |
| 298 | 21839 | 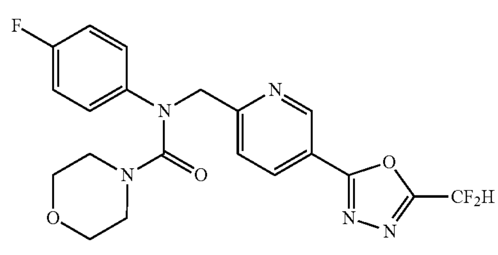 [SMILES: O=C(N1CCOCC1)N(Cc1ccc(-c2nnc(C(F)F)o2)cn1)c1ccc(F)cc1] |
| 299 | 21840 | 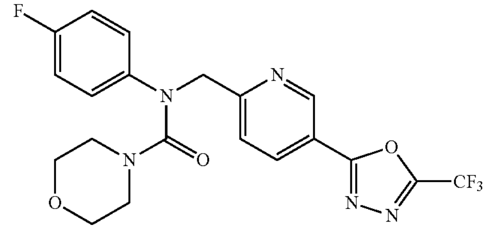 [SMILES: O=C(N1CCOCC1)N(Cc1ccc(-c2nnc(C(F)(F)F)o2)cn1)c1ccc(F)cc1] |

TABLE 1-continued

| Ex. | Comp. | Structure |
|---|---|---|
| 300 | 21841 | 4-fluorophenyl, morpholine carbonyl, CH2, 2-fluoro-4-(5-(difluoromethyl)-1,3,4-oxadiazol-2-yl)phenyl |
| 301 | 21842 | 4-fluorophenyl, morpholine carbonyl, CH2, 2-fluoro-4-(5-(trifluoromethyl)-1,3,4-oxadiazol-2-yl)phenyl |
| 302 | 21843 | 3-fluorophenyl, morpholine carbonyl, CH2, 5-(5-(difluoromethyl)-1,3,4-oxadiazol-2-yl)pyridin-2-yl |
| 303 | 21844 | 3-fluorophenyl, morpholine carbonyl, CH2, 5-(5-(trifluoromethyl)-1,3,4-oxadiazol-2-yl)pyridin-2-yl |
| 304 | 21845 | 3-fluorophenyl, morpholine carbonyl, CH2, 2-fluoro-4-(5-(difluoromethyl)-1,3,4-oxadiazol-2-yl)phenyl |
| 305 | 21846 | 3-fluorophenyl, morpholine carbonyl, CH2, 2-fluoro-4-(5-(trifluoromethyl)-1,3,4-oxadiazol-2-yl)phenyl |

TABLE 1-continued

| Ex. | Comp. | Structure |
|---|---|---|
| 306 | 21847 | 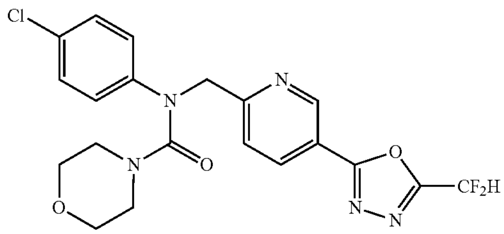 [SMILES: O=C(N1CCOCC1)N(Cc1ccc(-c2nnc(C(F)F)o2)cn1)c1ccc(Cl)cc1] |
| 307 | 21848 | 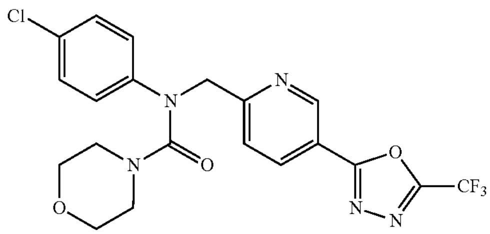 [SMILES: O=C(N1CCOCC1)N(Cc1ccc(-c2nnc(C(F)(F)F)o2)cn1)c1ccc(Cl)cc1] |
| 308 | 21849 | 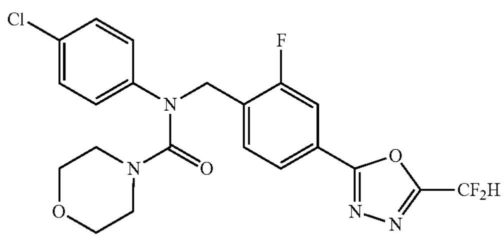 [SMILES: O=C(N1CCOCC1)N(Cc1ccc(-c2nnc(C(F)F)o2)cc1F)c1ccc(Cl)cc1] |
| 309 | 21850 | 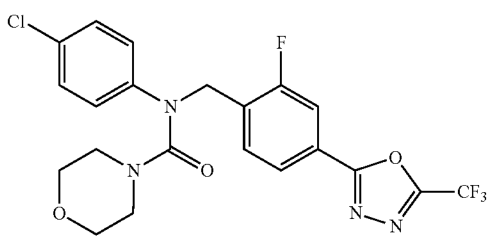 [SMILES: O=C(N1CCOCC1)N(Cc1ccc(-c2nnc(C(F)(F)F)o2)cc1F)c1ccc(Cl)cc1] |
| 310 | 21851 | 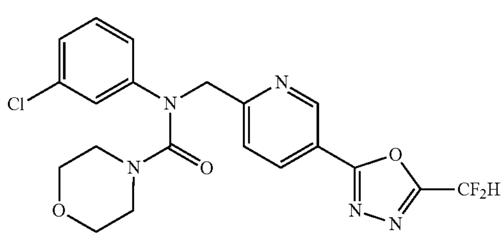 [SMILES: O=C(N1CCOCC1)N(Cc1ccc(-c2nnc(C(F)F)o2)cn1)c1cccc(Cl)c1] |
| 311 | 21852 | 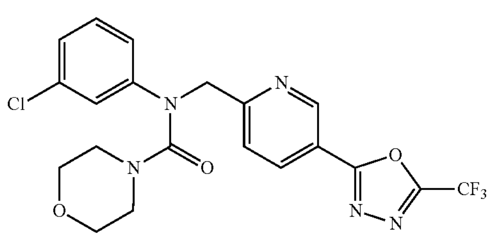 [SMILES: O=C(N1CCOCC1)N(Cc1ccc(-c2nnc(C(F)(F)F)o2)cn1)c1cccc(Cl)c1] |

TABLE 1-continued

| Ex. | Comp. | Structure |
|---|---|---|
| 312 | 21853 | 3-Cl-C6H4-N(C(O)-morpholine)-CH2-(2-F-C6H3)-[1,3,4-oxadiazole-5-CF2H] |
| 313 | 21854 | 3-Cl-C6H4-N(C(O)-morpholine)-CH2-(2-F-C6H3)-[1,3,4-oxadiazole-5-CF3] |
| 314 | 21855 | 4-Me-2-F-C6H3-N(C(O)-morpholine)-CH2-(pyridin-2-yl)-[1,3,4-oxadiazole-5-CF2H] |
| 315 | 21856 | 4-Me-2-F-C6H3-N(C(O)-morpholine)-CH2-(2-F-C6H3)-[1,3,4-oxadiazole-5-CF2H] |
| 316 | 21857 | 2,4-diF-C6H3-N(C(O)-morpholine)-CH2-(pyridin-2-yl)-[1,3,4-oxadiazole-5-CF3] |
| 317 | 21858 | 2,4-diF-C6H3-N(C(O)-morpholine)-CH2-(2-F-C6H3)-[1,3,4-oxadiazole-5-CF2H] |

TABLE 1-continued

| Ex. | Comp. | Structure |
|---|---|---|
| 318 | 21859 | 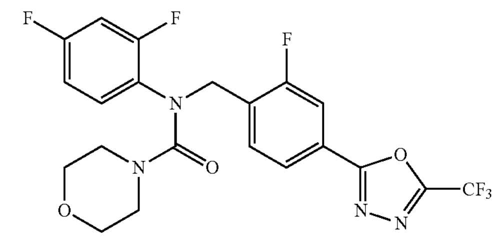 [SMILES: O=C(N1CCOCC1)N(Cc1ccc(-c2nnc(C(F)(F)F)o2)cc1F)c1ccc(F)cc1F] |
| 319 | 21860 | 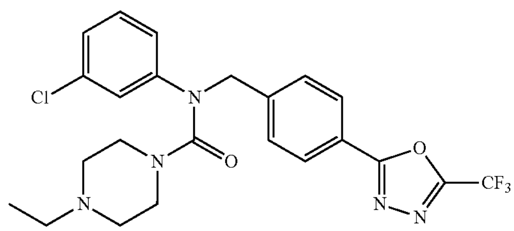 [SMILES: CCN1CCN(C(=O)N(Cc2ccc(-c3nnc(C(F)(F)F)o3)cc2)c2cccc(Cl)c2)CC1] |
| 320 | 21861 | 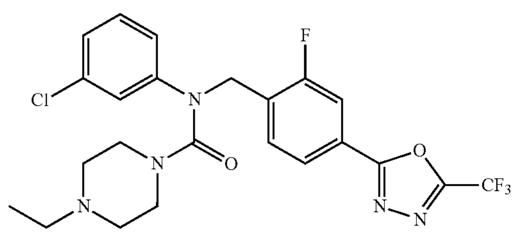 [SMILES: CCN1CCN(C(=O)N(Cc2ccc(-c3nnc(C(F)(F)F)o3)cc2F)c2cccc(Cl)c2)CC1] |
| 321 | 21862 | 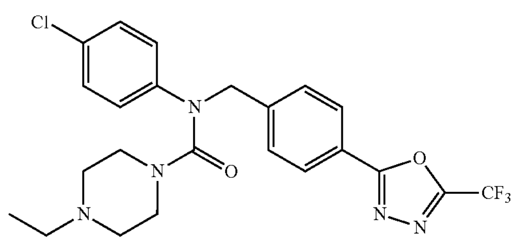 [SMILES: CCN1CCN(C(=O)N(Cc2ccc(-c3nnc(C(F)(F)F)o3)cc2)c2ccc(Cl)cc2)CC1] |
| 322 | 21863 | 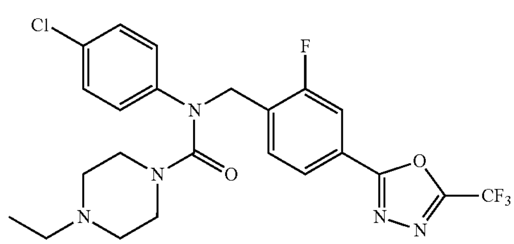 [SMILES: CCN1CCN(C(=O)N(Cc2ccc(-c3nnc(C(F)(F)F)o3)cc2F)c2ccc(Cl)cc2)CC1] |
| 323 | 21864 | 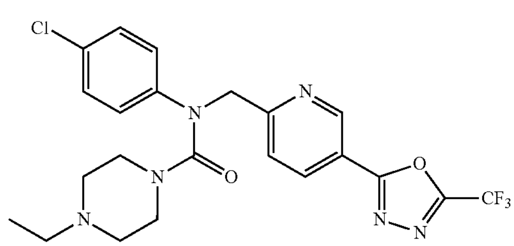 [SMILES: CCN1CCN(C(=O)N(Cc2ccc(-c3nnc(C(F)(F)F)o3)cn2)c2ccc(Cl)cc2)CC1] |

TABLE 1-continued

| Ex. | Comp. | Structure |
|---|---|---|
| 324 | 21865 | 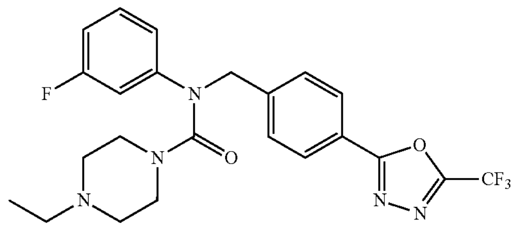 [SMILES: CCN1CCN(C(=O)N(Cc2ccc(-c3nnc(C(F)(F)F)o3)cc2)c2cccc(F)c2)CC1] |
| 325 | 21866 | 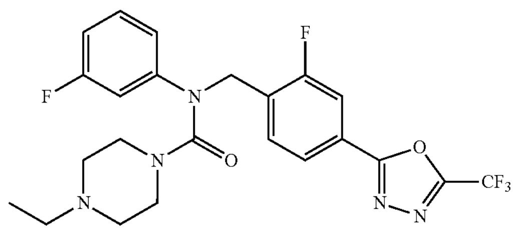 [SMILES: CCN1CCN(C(=O)N(Cc2ccc(-c3nnc(C(F)(F)F)o3)cc2F)c2cccc(F)c2)CC1] |
| 326 | 21867 | 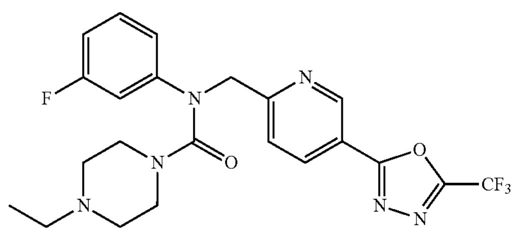 [SMILES: CCN1CCN(C(=O)N(Cc2ccc(-c3nnc(C(F)(F)F)o3)cn2)c2cccc(F)c2)CC1] |
| 327 | 21868 | 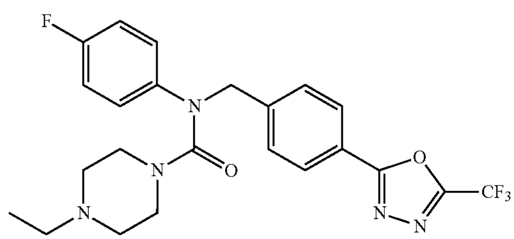 |
| 328 | 21869 | 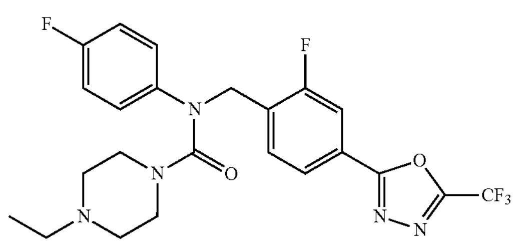 [SMILES: CCN1CCN(C(=O)N(Cc2ccc(-c3nnc(C(F)(F)F)o3)cc2F)c2ccc(F)cc2)CC1] |
| 329 | 21870 | 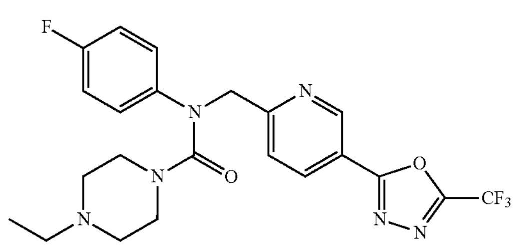 [SMILES: CCN1CCN(C(=O)N(Cc2ccc(-c3nnc(C(F)(F)F)o3)cn2)c2ccc(F)cc2)CC1] |

| Ex. | Comp. | Structure |
|---|---|---|
| 330 | 21871 | 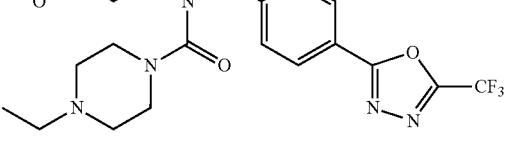 |
| 331 | 21872 | 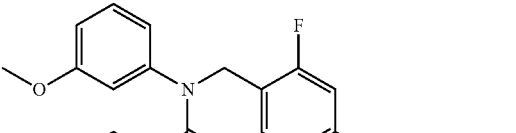 |
| 332 | 21873 | 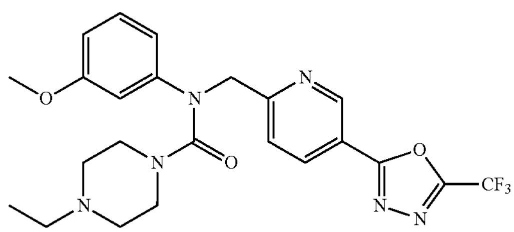 [SMILES: CCN1CCN(C(=O)N(Cc2ccc(-c3nnc(C(F)(F)F)o3)cn2)c2cccc(OC)c2)CC1] |
| 333 | 21874 | 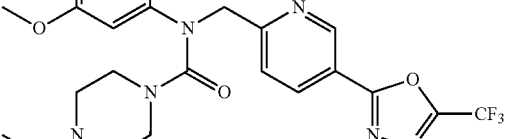 |
| 334 | 21875 | 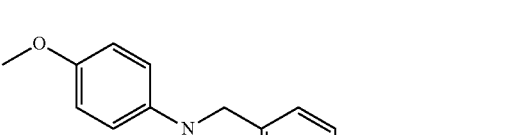 |
| 335 | 21876 | 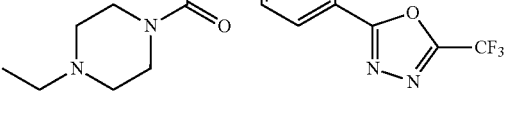 |

TABLE 1-continued

| Ex. | Comp. | Structure |
|---|---|---|
| 336 | 21877 | 3-Cl-C6H4-N(C(O)-4-ethylpiperazin-1-yl)-CH2-(4-(5-(CF2H)-1,3,4-oxadiazol-2-yl)phenyl) |
| 337 | 21878 | 3-Cl-C6H4-N(C(O)-4-ethylpiperazin-1-yl)-CH2-(2-F-4-(5-(CF2H)-1,3,4-oxadiazol-2-yl)phenyl) |
| 338 | 21879 | 3-Cl-C6H4-N(C(O)-4-ethylpiperazin-1-yl)-CH2-(5-(5-(CF2H)-1,3,4-oxadiazol-2-yl)pyridin-2-yl) |
| 339 | 21880 | 4-Cl-C6H4-N(C(O)-4-ethylpiperazin-1-yl)-CH2-(4-(5-(CF2H)-1,3,4-oxadiazol-2-yl)phenyl) |
| 340 | 21881 | 4-Cl-C6H4-N(C(O)-4-ethylpiperazin-1-yl)-CH2-(2-F-4-(5-(CF2H)-1,3,4-oxadiazol-2-yl)phenyl) |
| 341 | 21882 | 4-Cl-C6H4-N(C(O)-4-ethylpiperazin-1-yl)-CH2-(5-(5-(CF2H)-1,3,4-oxadiazol-2-yl)pyridin-2-yl) |

TABLE 1-continued

| Ex. | Comp. | Structure |
|---|---|---|
| 342 | 21883 | 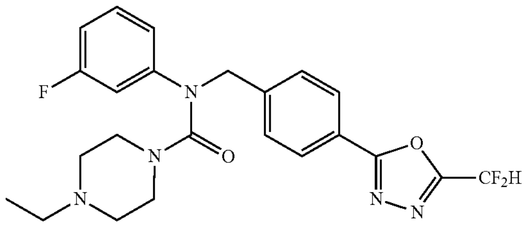 [SMILES: CCN1CCN(C(=O)N(Cc2ccc(-c3nnc(C(F)F)o3)cc2)c2cccc(Cl)c2)CC1] |
| 343 | 21884 | 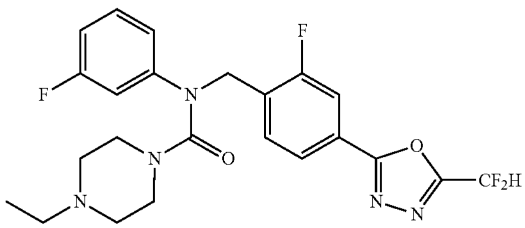 |
| 344 | 21885 | 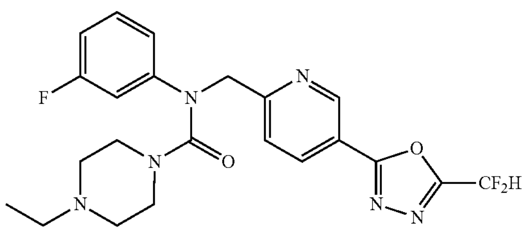 [SMILES: CCN1CCN(C(=O)N(Cc2ccc(-c3nnc(C(F)F)o3)cn2)c2cccc(Cl)c2)CC1] |
| 345 | 21886 | 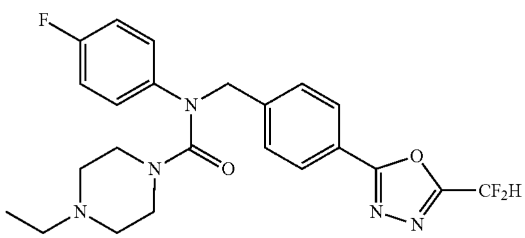 [SMILES: CCN1CCN(C(=O)N(Cc2ccc(-c3nnc(C(F)F)o3)cc2)c2ccc(F)cc2)CC1] |
| 346 | 21887 | 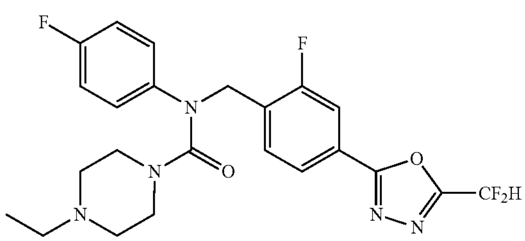 [SMILES: CCN1CCN(C(=O)N(Cc2ccc(-c3nnc(C(F)F)o3)cc2F)c2ccc(F)cc2)CC1] |
| 347 | 21888 | 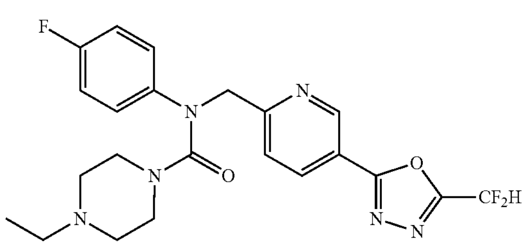 [SMILES: CCN1CCN(C(=O)N(Cc2ccc(-c3nnc(C(F)F)o3)cn2)c2ccc(F)cc2)CC1] |

TABLE 1-continued

| Ex. | Comp. | Structure |
|---|---|---|
| 348 | 21889 | 3-methoxyphenyl-N-(4-(5-(difluoromethyl)-1,3,4-oxadiazol-2-yl)benzyl)-4-ethylpiperazine-1-carboxamide |
| 349 | 21890 | 3-methoxyphenyl-N-(2-fluoro-4-(5-(difluoromethyl)-1,3,4-oxadiazol-2-yl)benzyl)-4-ethylpiperazine-1-carboxamide |
| 350 | 21891 | 3-methoxyphenyl-N-((5-(5-(difluoromethyl)-1,3,4-oxadiazol-2-yl)pyridin-2-yl)methyl)-4-ethylpiperazine-1-carboxamide |
| 351 | 21892 | 4-methoxyphenyl-N-(4-(5-(difluoromethyl)-1,3,4-oxadiazol-2-yl)benzyl)-4-ethylpiperazine-1-carboxamide |
| 352 | 21893 | 4-methoxyphenyl-N-(2-fluoro-4-(5-(difluoromethyl)-1,3,4-oxadiazol-2-yl)benzyl)-4-ethylpiperazine-1-carboxamide |
| 353 | 21894 | 4-methoxyphenyl-N-((5-(5-(difluoromethyl)-1,3,4-oxadiazol-2-yl)pyridin-2-yl)methyl)-4-ethylpiperazine-1-carboxamide |

TABLE 1-continued

| Ex. | Comp. | Structure |
|---|---|---|
| 354 | 21895 | 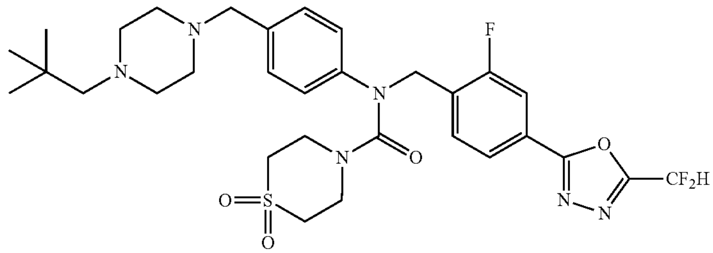 [SMILES: CC(C)(C)CN1CCN(Cc2ccc(N(Cc3ccc(-c4nnc(C(F)F)o4)cc3F)C(=O)N3CCS(=O)(=O)CC3)cc2)CC1] |
| 355 | 21896 | 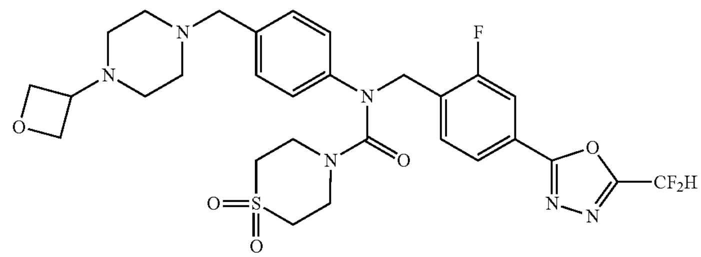 [SMILES: O=C(N1CCS(=O)(=O)CC1)N(Cc1ccc(-c2nnc(C(F)F)o2)cc1F)c1ccc(CN2CCN(C3COC3)CC2)cc1] |
| 356 | 21897 | 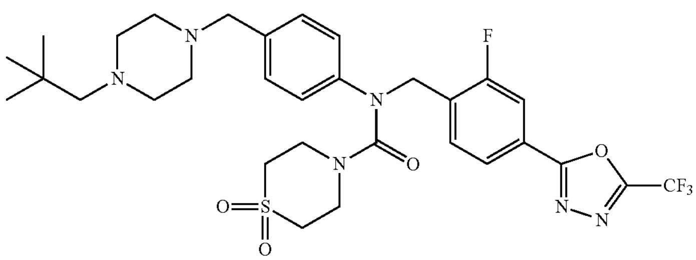 [SMILES: CC(C)(C)CN1CCN(Cc2ccc(N(Cc3ccc(-c4nnc(C(F)(F)F)o4)cc3F)C(=O)N3CCS(=O)(=O)CC3)cc2)CC1] |
| 357 | 21898 | 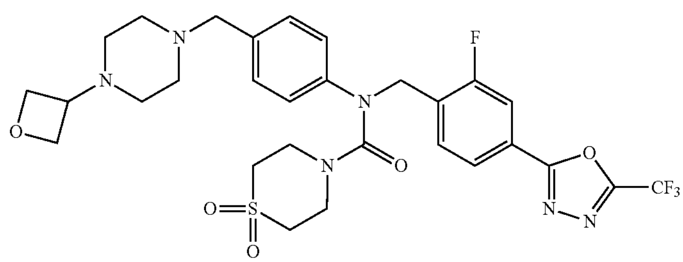 [SMILES: O=C(N1CCS(=O)(=O)CC1)N(Cc1ccc(-c2nnc(C(F)(F)F)o2)cc1F)c1ccc(CN2CCN(C3COC3)CC2)cc1] |
| 358 | 21899 | 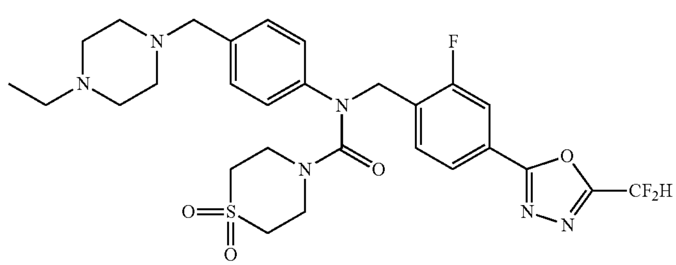 [SMILES: CCN1CCN(Cc2ccc(N(Cc3ccc(-c4nnc(C(F)F)o4)cc3F)C(=O)N3CCS(=O)(=O)CC3)cc2)CC1] |
| 359 | 21900 | 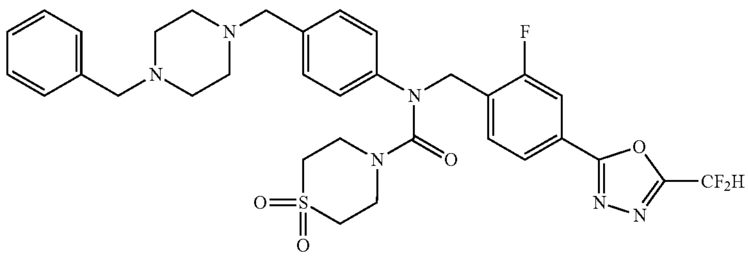 [SMILES: O=C(N1CCS(=O)(=O)CC1)N(Cc1ccc(-c2nnc(C(F)F)o2)cc1F)c1ccc(CN2CCN(Cc3ccccc3)CC2)cc1] |

TABLE 1-continued

| Ex. | Comp. | Structure |
|---|---|---|
| 360 | 21901 | 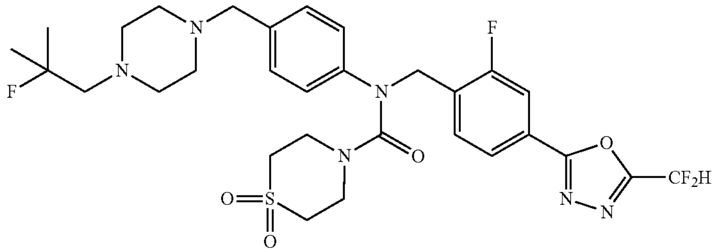 [SMILES: CC(C)(F)CN1CCN(Cc2ccc(N(Cc3ccc(-c4nnc(C(F)F)o4)cc3F)C(=O)N3CCS(=O)(=O)CC3)cc2)CC1] |
| 361 | 21902 | 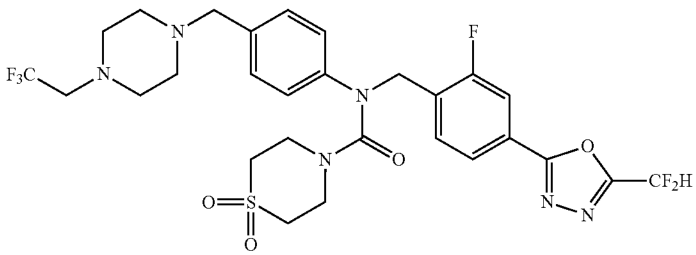 [SMILES: O=C(N1CCS(=O)(=O)CC1)N(Cc1ccc(-c2nnc(C(F)F)o2)cc1F)c1ccc(CN2CCN(CC(F)(F)F)CC2)cc1] |
| 362 | 21905 | 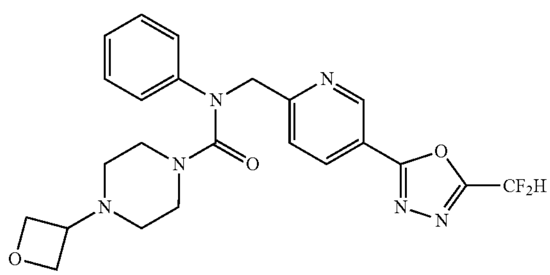 [SMILES: O=C(N1CCN(C2COC2)CC1)N(Cc1ccc(-c2nnc(C(F)F)o2)cn1)c1ccccc1] |
| 363 | 21910 | 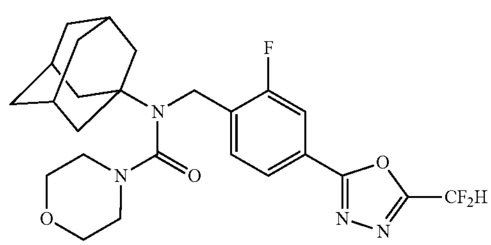 [SMILES: O=C(N1CCOCC1)N(Cc1ccc(-c2nnc(C(F)F)o2)cc1F)C12CC3CC(CC(C3)C1)C2] |
| 364 | 21914 | 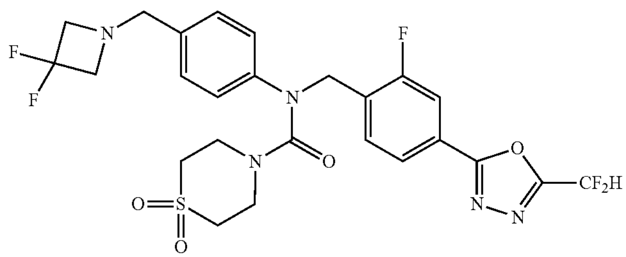 [SMILES: O=C(N1CCS(=O)(=O)CC1)N(Cc1ccc(-c2nnc(C(F)F)o2)cc1F)c1ccc(CN2CC(F)(F)C2)cc1] |
| 365 | 21915 | 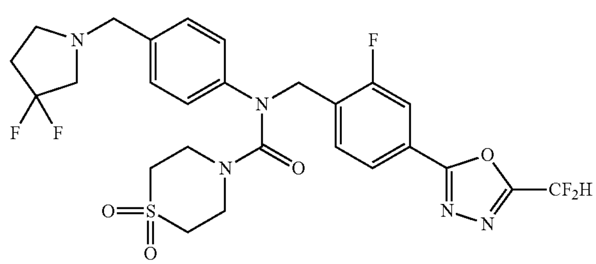 [SMILES: O=C(N1CCS(=O)(=O)CC1)N(Cc1ccc(-c2nnc(C(F)F)o2)cc1F)c1ccc(CN2CCC(F)(F)C2)cc1] |

TABLE 1-continued

| Ex. | Comp. | Structure |
|---|---|---|
| 366 | 21916 | 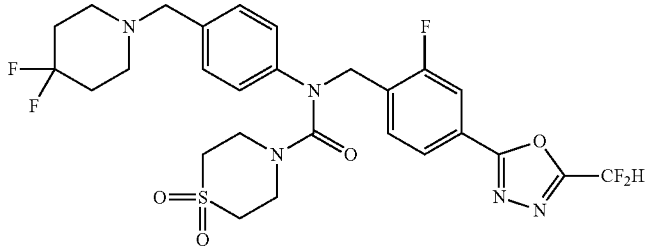 [SMILES: O=C(N1CCS(=O)(=O)CC1)N(Cc1ccc(-c2nnc(C(F)F)o2)cc1F)c1ccc(CN2CCC(F)(F)CC2)cc1] |
| 367 | 21917 | 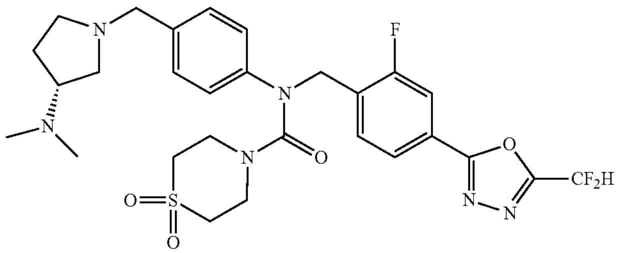 [SMILES: CN(C)[C@@H]1CCN(Cc2ccc(N(Cc3ccc(-c4nnc(C(F)F)o4)cc3F)C(=O)N3CCS(=O)(=O)CC3)cc2)C1] |
| 368 | 21918 | 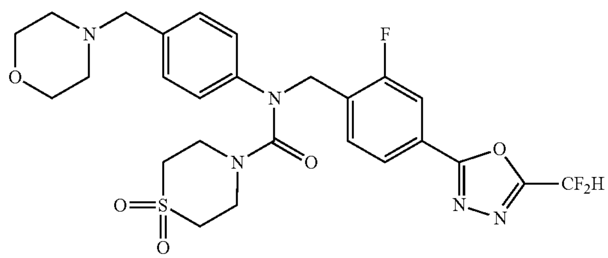 [SMILES: O=C(N1CCS(=O)(=O)CC1)N(Cc1ccc(-c2nnc(C(F)F)o2)cc1F)c1ccc(CN2CCOCC2)cc1] |
| 369 | 21919 | 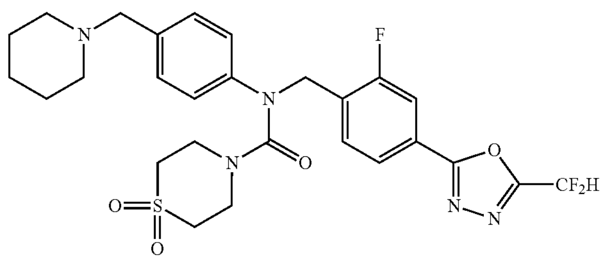 [SMILES: O=C(N1CCS(=O)(=O)CC1)N(Cc1ccc(-c2nnc(C(F)F)o2)cc1F)c1ccc(CN2CCCCC2)cc1] |
| 370 | 21924 | 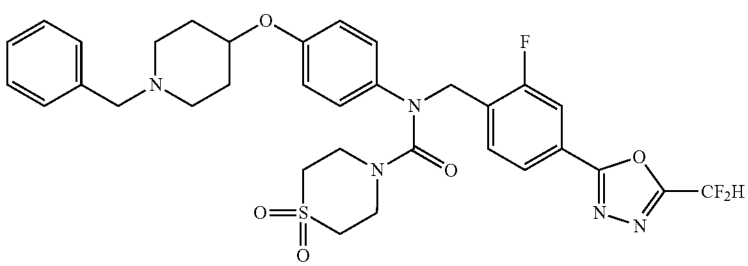 [SMILES: O=C(N1CCS(=O)(=O)CC1)N(Cc1ccc(-c2nnc(C(F)F)o2)cc1F)c1ccc(OC2CCN(Cc3ccccc3)CC2)cc1] |
| 371 | 21925 | 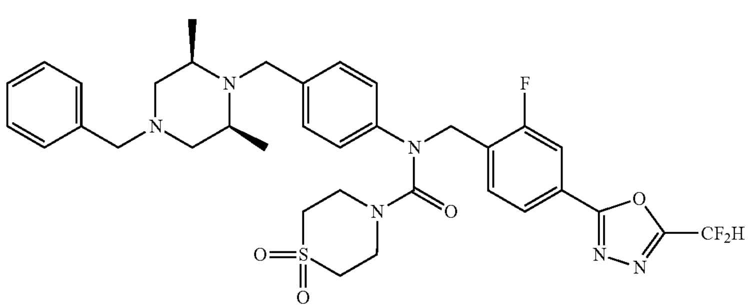 [SMILES: C[C@@H]1CN(Cc2ccccc2)C[C@H](C)N1Cc1ccc(N(Cc2ccc(-c3nnc(C(F)F)o3)cc2F)C(=O)N2CCS(=O)(=O)CC2)cc1] |

TABLE 1-continued
| Ex. | Comp. | Structure |
|---|---|---|
| 372 | 21926 | 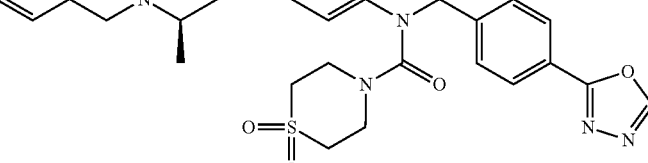 |
| 373 | 21929 | 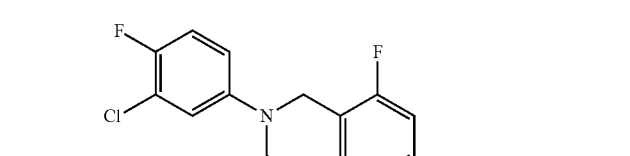 |
| 374 | 21930 | 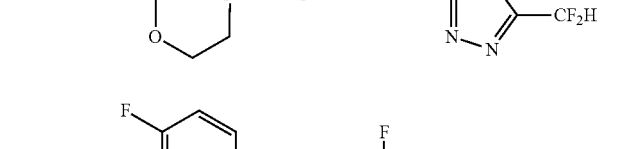 |
| 375 | 21931 | 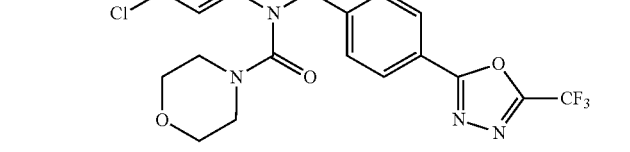 |
| 376 | 21932 | 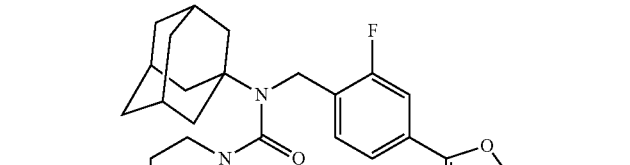 |
| 377 | 21933 | 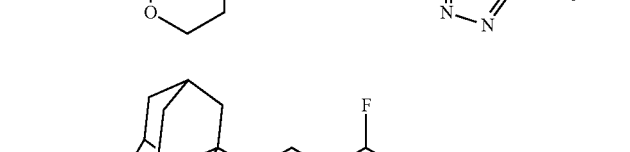 |

TABLE 1-continued

| Ex. | Comp. | Structure |
|---|---|---|
| 378 | 21934 | 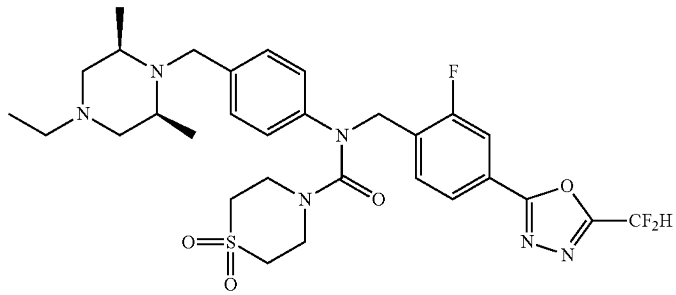 [SMILES: CCN1C[C@@H](C)N(Cc2ccc(N(Cc3ccc(-c4nnc(C(F)F)o4)cc3F)C(=O)N3CCS(=O)(=O)CC3)cc2)[C@@H](C)C1] |
| 379 | 21935 | 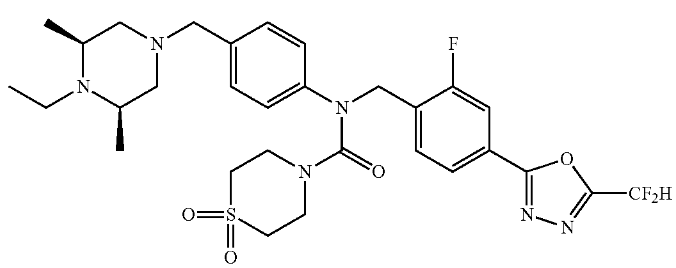 [SMILES: CCN1[C@H](C)CN(Cc2ccc(N(Cc3ccc(-c4nnc(C(F)F)o4)cc3F)C(=O)N3CCS(=O)(=O)CC3)cc2)C[C@@H]1C] |
| 380 | 21936 | 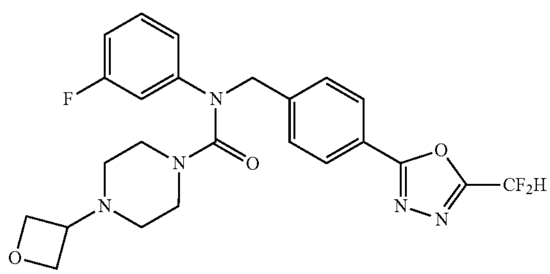 [SMILES: O=C(N1CCN(C2COC2)CC1)N(Cc1ccc(-c2nnc(C(F)F)o2)cc1)c1cccc(F)c1] |
| 381 | 21937 | 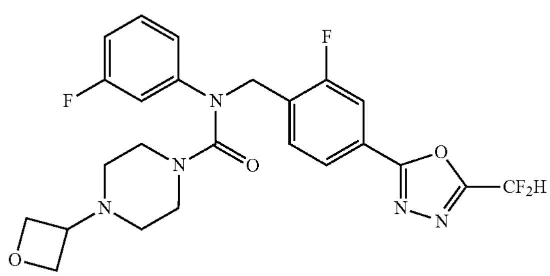 [SMILES: O=C(N1CCN(C2COC2)CC1)N(Cc1ccc(-c2nnc(C(F)F)o2)cc1F)c1cccc(F)c1] |
| 382 | 21938 | 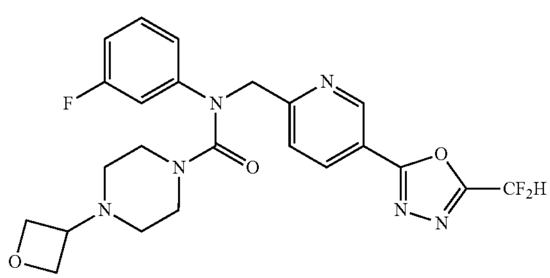 [SMILES: O=C(N1CCN(C2COC2)CC1)N(Cc1ccc(-c2nnc(C(F)F)o2)cn1)c1cccc(F)c1] |

TABLE 1-continued
| Ex. | Comp. | Structure |
|---|---|---|
| 383 | 21939 | 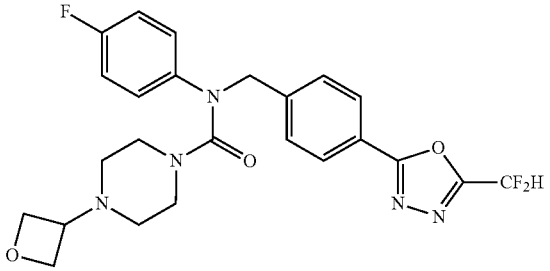 [SMILES: O=C(N1CCN(C2COC2)CC1)N(Cc1ccc(-c2nnc(C(F)F)o2)cc1)c1ccc(F)cc1] |
| 384 | 21940 | 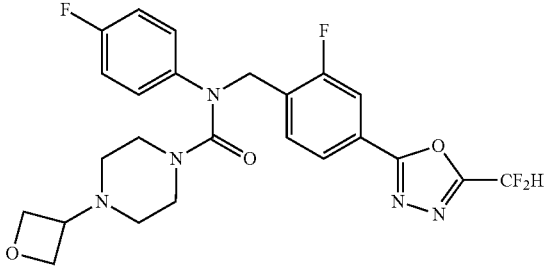 [SMILES: O=C(N1CCN(C2COC2)CC1)N(Cc1ccc(-c2nnc(C(F)F)o2)cc1F)c1ccc(F)cc1] |
| 385 | 21941 | 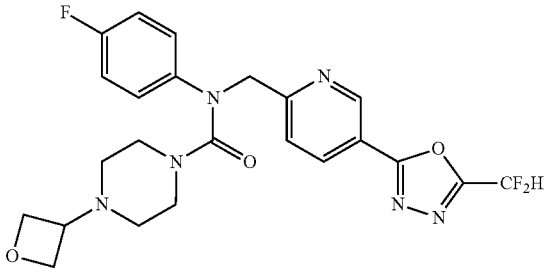 |
| 386 | 21942 | 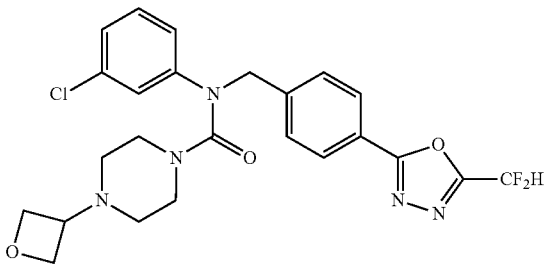 |
| 387 | 21943 | 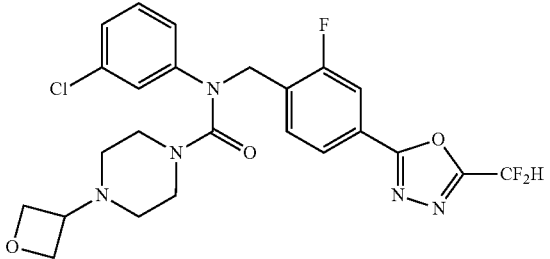 [SMILES: O=C(N1CCN(C2COC2)CC1)N(Cc1ccc(-c2nnc(C(F)F)o2)cc1F)c1cccc(Cl)c1] |

TABLE 1-continued

| Ex. | Comp. | Structure |
|-----|-------|-----------|
| 388 | 21944 | 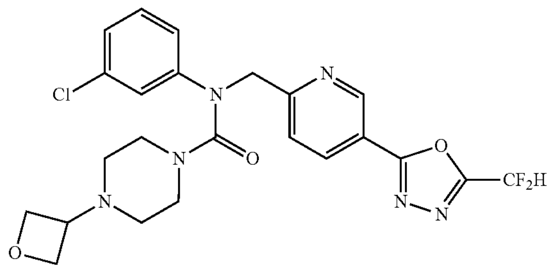 |
| 389 | 21945 | 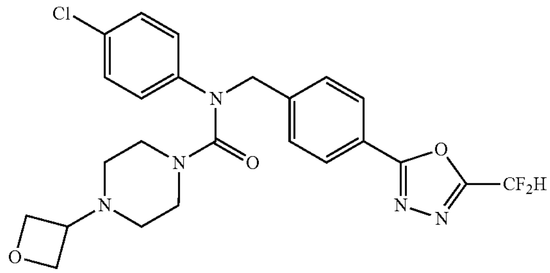 [SMILES: O=C(N1CCN(C2COC2)CC1)N(Cc1ccc(-c2nnc(C(F)F)o2)cc1)c1ccc(Cl)cc1] |
| 390 | 21946 | 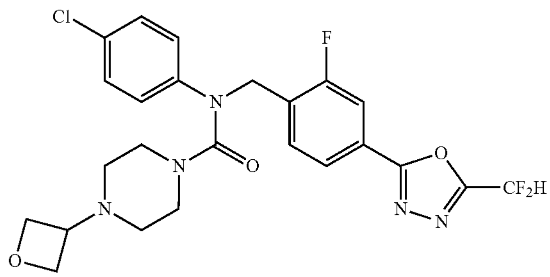 |
| 391 | 21947 | 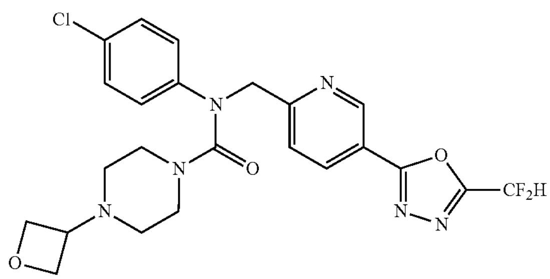 [SMILES: O=C(N1CCN(C2COC2)CC1)N(Cc1ccc(-c2nnc(C(F)F)o2)cn1)c1ccc(Cl)cc1] |
| 392 | 21948 | 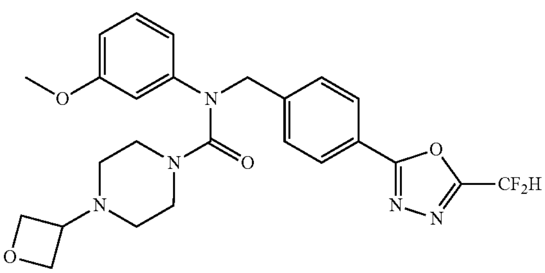 [SMILES: COc1cccc(N(Cc2ccc(-c3nnc(C(F)F)o3)cc2)C(=O)N2CCN(C3COC3)CC2)c1] |

TABLE 1-continued
| Ex. | Comp. | Structure |
|---|---|---|
| 393 | 21949 | 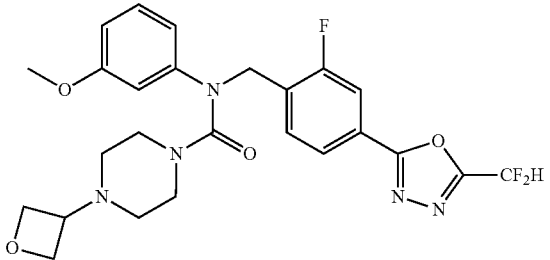 [SMILES: COc1cccc(N(Cc2ccc(-c3nnc(C(F)F)o3)cc2F)C(=O)N2CCN(C3COC3)CC2)c1] |
| 394 | 21950 | 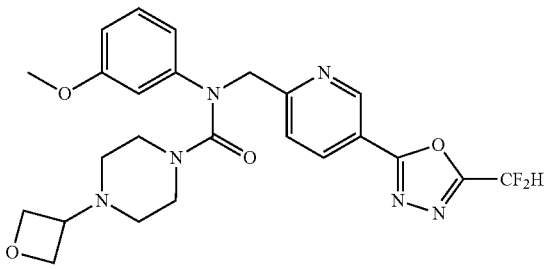 |
| 395 | 21951 | 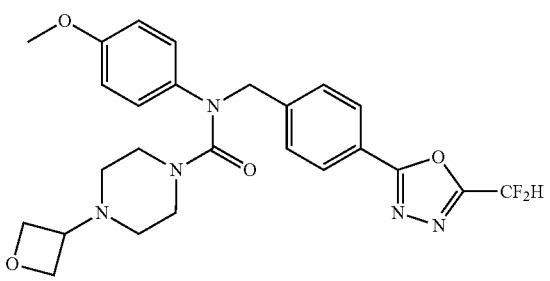 [SMILES: COc1ccc(N(Cc2ccc(-c3nnc(C(F)F)o3)cc2)C(=O)N2CCN(C3COC3)CC2)cc1] |
| 396 | 21952 | 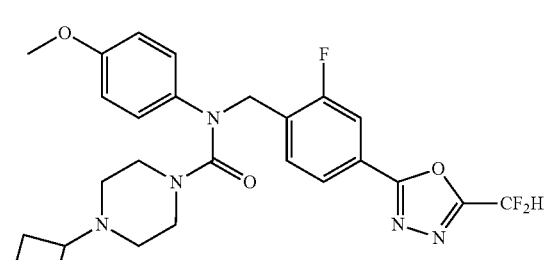 |
| 397 | 21953 | 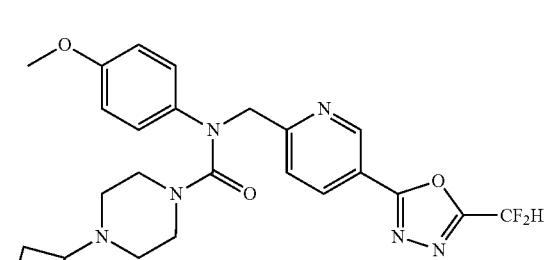 |

TABLE 1-continued

| Ex. | Comp. | Structure |
|---|---|---|
| 398 | 21954 | 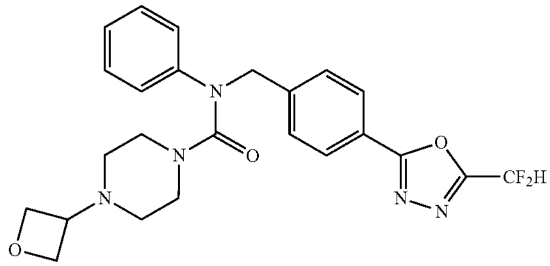 [SMILES: O=C(N1CCN(C2COC2)CC1)N(Cc1ccc(-c2nnc(C(F)F)o2)cc1)c1ccccc1] |
| 399 | 21955 | 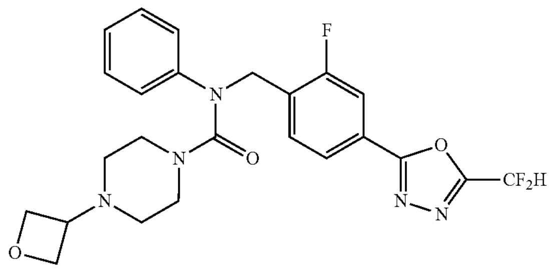 [SMILES: O=C(N1CCN(C2COC2)CC1)N(Cc1ccc(-c2nnc(C(F)F)o2)cc1F)c1ccccc1] |
| 400 | 21956 | 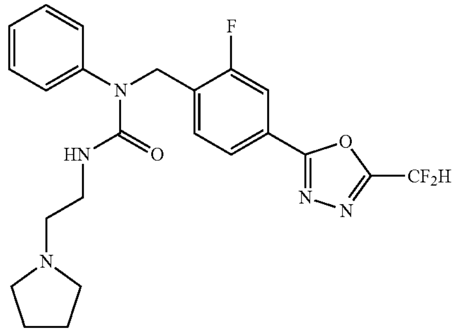 [SMILES: O=C(NCCN1CCCC1)N(Cc1ccc(-c2nnc(C(F)F)o2)cc1F)c1ccccc1] |
| 401 | 21957 | 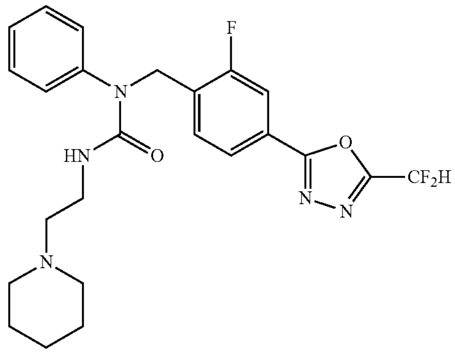 [SMILES: O=C(NCCN1CCCCC1)N(Cc1ccc(-c2nnc(C(F)F)o2)cc1F)c1ccccc1] |

TABLE 1-continued

| Ex. | Comp. | Structure |
|---|---|---|
| 402 | 21958 | 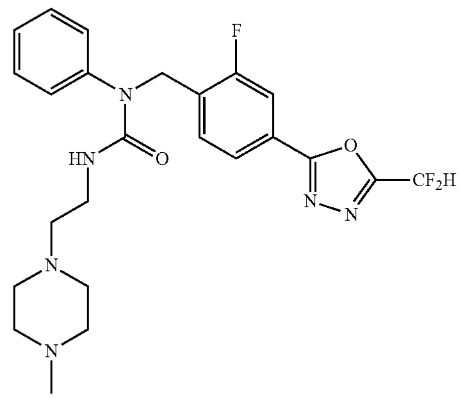 [SMILES: CN1CCN(CCNC(=O)N(Cc2ccc(-c3nnc(C(F)F)o3)cc2F)c2ccccc2)CC1] |
| 403 | 21970 | 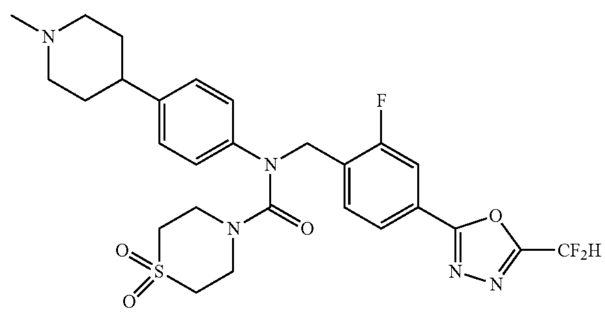 [SMILES: CN1CCC(c2ccc(N(Cc3ccc(-c4nnc(C(F)F)o4)cc3F)C(=O)N3CCS(=O)(=O)CC3)cc2)CC1] |
| 404 | 21971 | 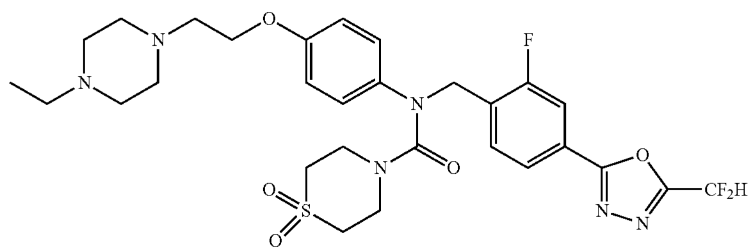 [SMILES: CCN1CCN(CCOc2ccc(N(Cc3ccc(-c4nnc(C(F)F)o4)cc3F)C(=O)N3CCS(=O)(=O)CC3)cc2)CC1] |
| 405 | 21972 | 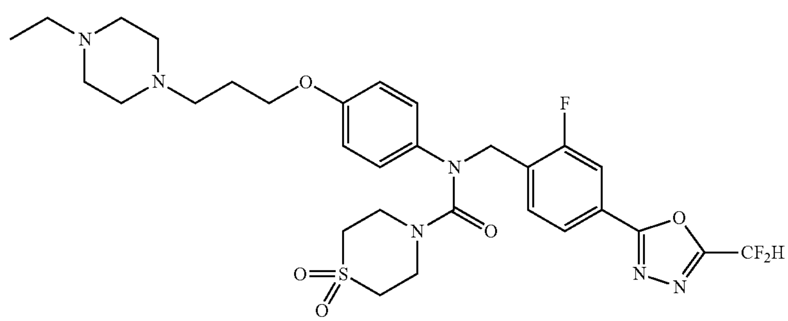 [SMILES: CCN1CCN(CCCOc2ccc(N(Cc3ccc(-c4nnc(C(F)F)o4)cc3F)C(=O)N3CCS(=O)(=O)CC3)cc2)CC1] |
| 406 | 21973 | 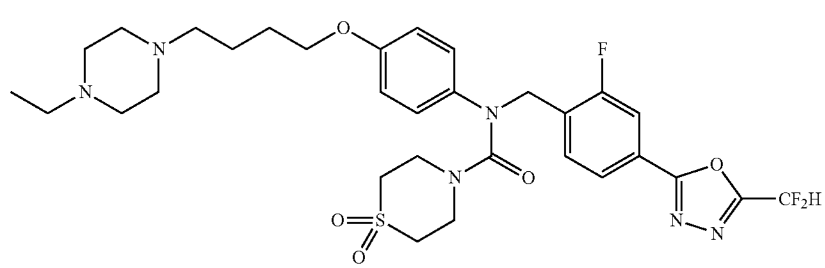 [SMILES: CCN1CCN(CCCCOc2ccc(N(Cc3ccc(-c4nnc(C(F)F)o4)cc3F)C(=O)N3CCS(=O)(=O)CC3)cc2)CC1] |

TABLE 1-continued

| Ex. | Comp. | Structure |
|---|---|---|
| 407 | 21979 | 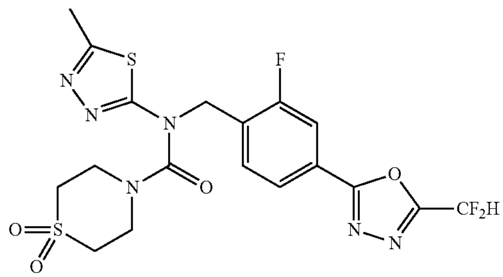 [SMILES: Cc1nnc(N(Cc2ccc(-c3nnc(C(F)F)o3)cc2F)C(=O)N2CCS(=O)(=O)CC2)s1] |
| 408 | 21980 | 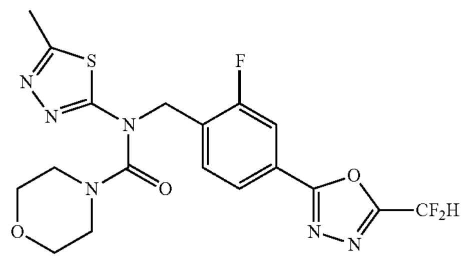 [SMILES: Cc1nnc(N(Cc2ccc(-c3nnc(C(F)F)o3)cc2F)C(=O)N2CCOCC2)s1] |
| 409 | 21981 | 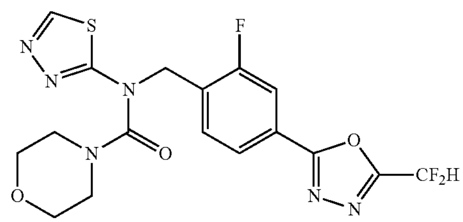 |
| 410 | 21982 | 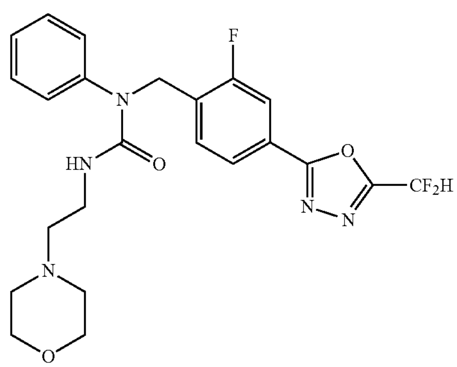 [SMILES: O=C(NCCN1CCOCC1)N(Cc1ccc(-c2nnc(C(F)F)o2)cc1F)c1ccccc1] |
| 411 | 21983 | 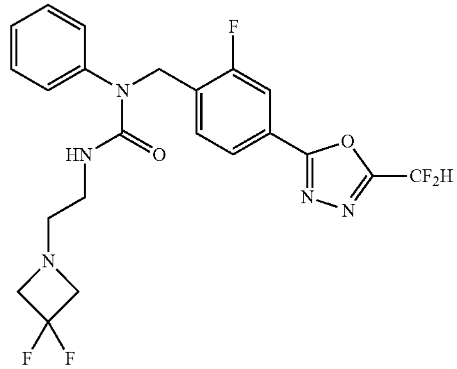 [SMILES: O=C(NCCN1CC(F)(F)C1)N(Cc1ccc(-c2nnc(C(F)F)o2)cc1F)c1ccccc1] |

TABLE 1-continued

| Ex. | Comp. | Structure |
|---|---|---|
| 412 | 21984 | 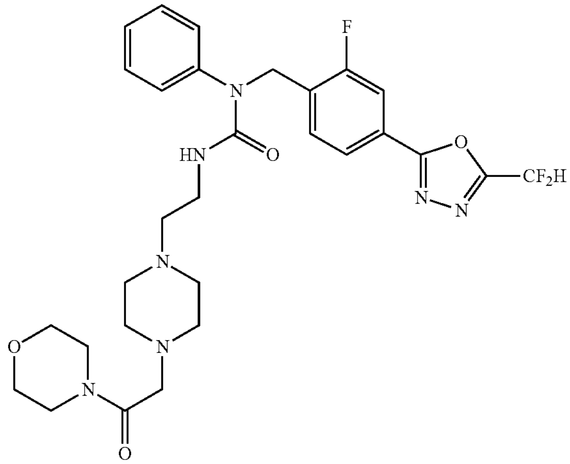 [SMILES: O=C(CN1CCN(CCNC(=O)N(Cc2ccc(-c3nnc(C(F)F)o3)cc2F)c2ccccc2)CC1)N1CCOCC1] |
| 413 | 21985 | 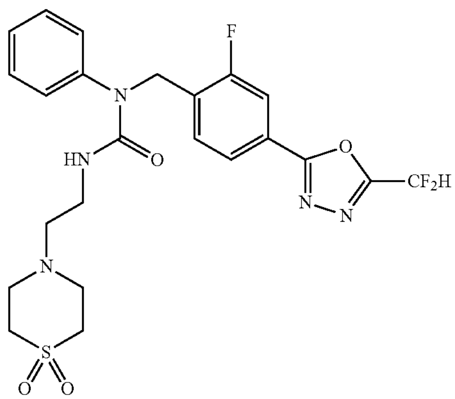 [SMILES: O=C(NCCN1CCS(=O)(=O)CC1)N(Cc1ccc(-c2nnc(C(F)F)o2)cc1F)c1ccccc1] |
| 414 | 21986 | 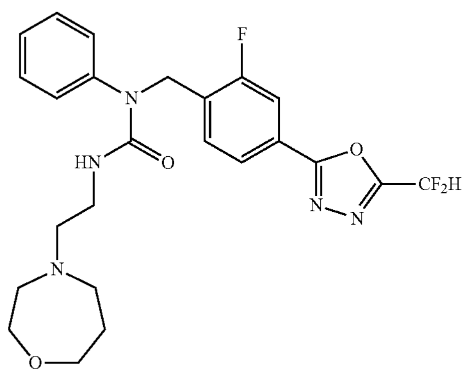 [SMILES: O=C(NCCN1CCCOCC1)N(Cc1ccc(-c2nnc(C(F)F)o2)cc1F)c1ccccc1] |
| 415 | 21987 | 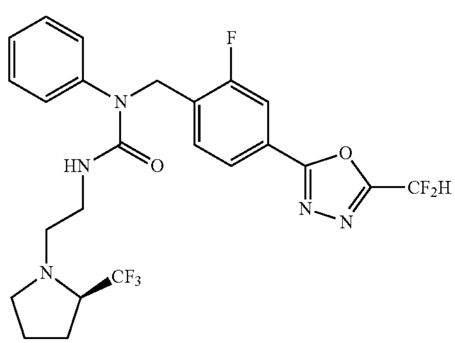 [SMILES: O=C(NCCN1CCC[C@@H]1C(F)(F)F)N(Cc1ccc(-c2nnc(C(F)F)o2)cc1F)c1ccccc1] |

US 10,717,716 B2
157                                                                                                                  158
TABLE 1-continued
| Ex. | Comp. | Structure |
|---|---|---|
| 416 | 21988 | 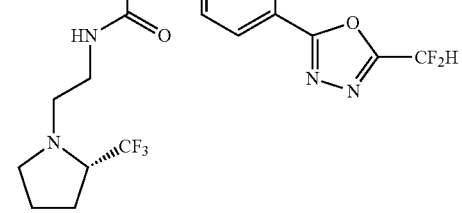 |
| 417 | 21989 | 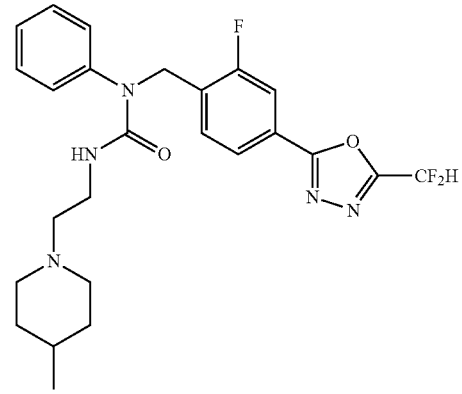 [SMILES: CC1CCN(CCNC(=O)N(Cc2ccc(-c3nnc(C(F)F)o3)cc2F)c2ccccc2)CC1] |
| 418 | 21990 | 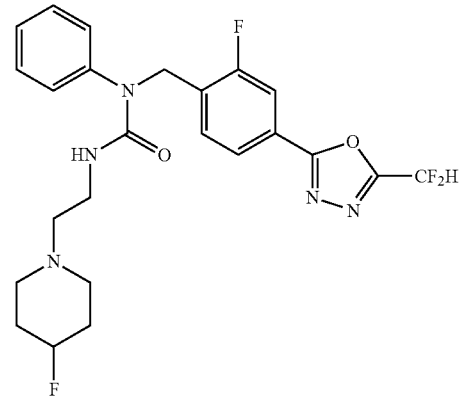 [SMILES: O=C(NCCN1CCC(F)CC1)N(Cc1ccc(-c2nnc(C(F)F)o2)cc1F)c1ccccc1] |
| 419 | 21991 | 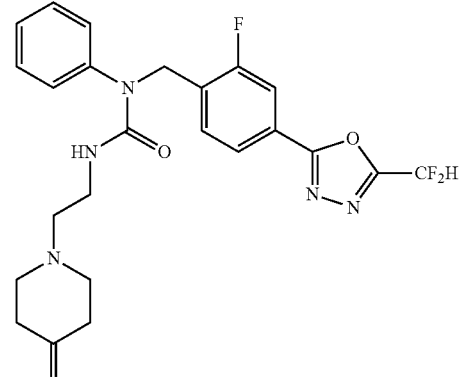 |

TABLE 1-continued

| Ex. | Comp. | Structure |
|---|---|---|
| 420 | 21992 | 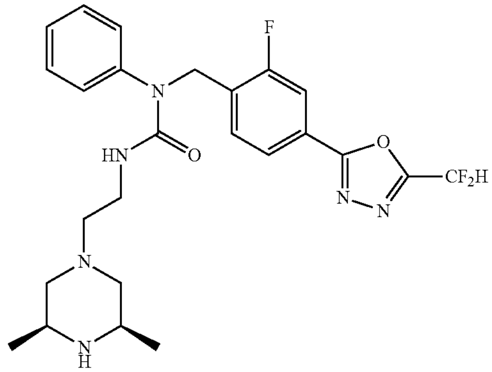 [SMILES: C[C@@H]1CN(CCNC(=O)N(Cc2ccc(-c3nnc(C(F)F)o3)cc2F)c2ccccc2)C[C@H](C)N1] |
| 421 | 21993 | 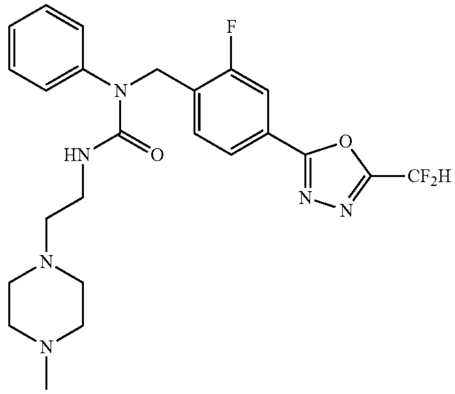 [SMILES: CN1CCN(CCNC(=O)N(Cc2ccc(-c3nnc(C(F)F)o3)cc2F)c2ccccc2)CC1] |
| 422 | 21994 | 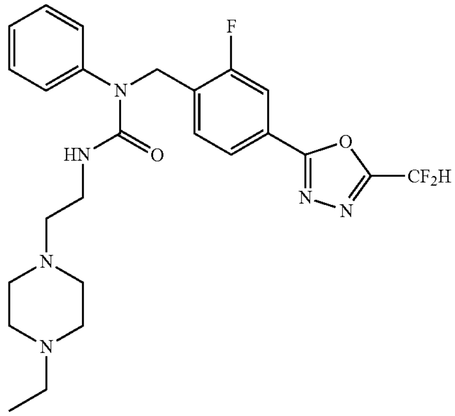 [SMILES: CCN1CCN(CCNC(=O)N(Cc2ccc(-c3nnc(C(F)F)o3)cc2F)c2ccccc2)CC1] |
| 423 | 21995 | 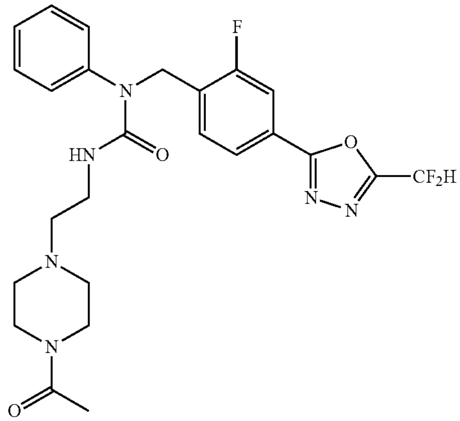 [SMILES: CC(=O)N1CCN(CCNC(=O)N(Cc2ccc(-c3nnc(C(F)F)o3)cc2F)c2ccccc2)CC1] |

| Ex. | Comp. | Structure |
|---|---|---|
| 424 | 21996 | 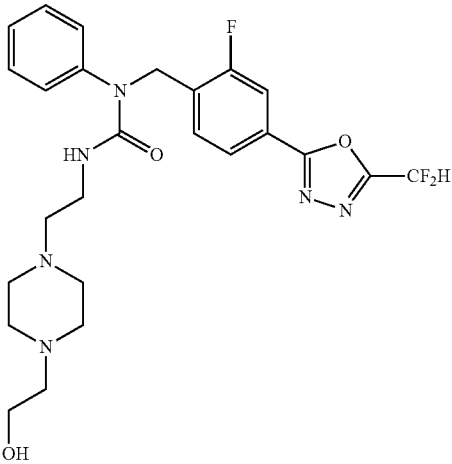 [SMILES: O=C(NCCN1CCN(CCO)CC1)N(Cc1ccc(-c2nnc(C(F)F)o2)cc1F)c1ccccc1] |
| 425 | 21997 | 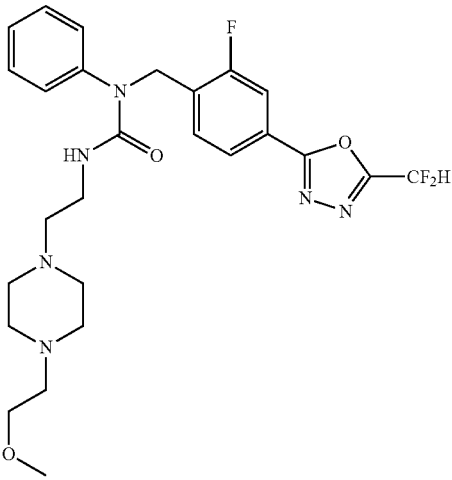 [SMILES: COCCN1CCN(CCNC(=O)N(Cc2ccc(-c3nnc(C(F)F)o3)cc2F)c2ccccc2)CC1] |
| 426 | 21998 | 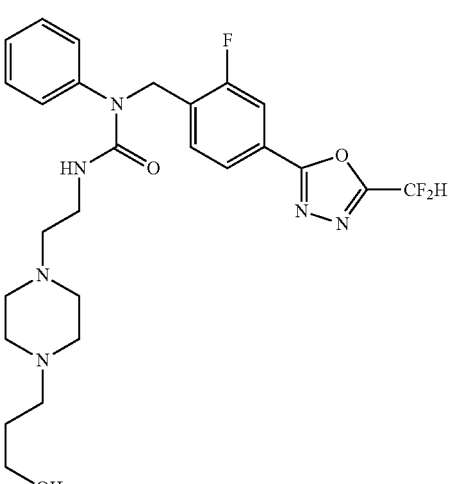 |

TABLE 1-continued
| Ex. | Comp. | Structure |
|---|---|---|
| 427 | 21999 | 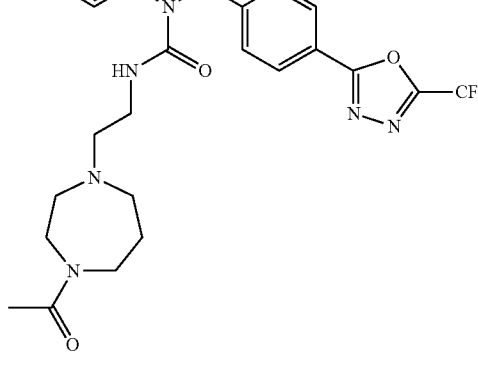 |
| 428 | 22000 | 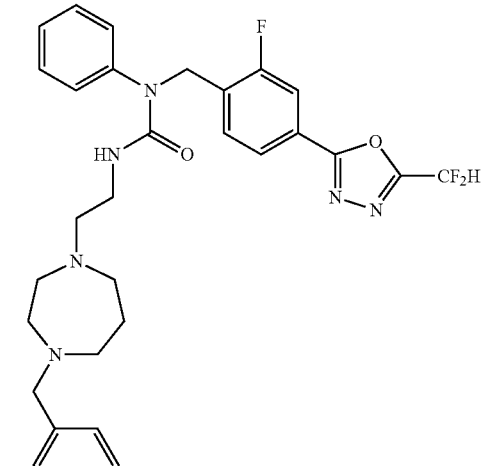 |
| 429 | 22001 | 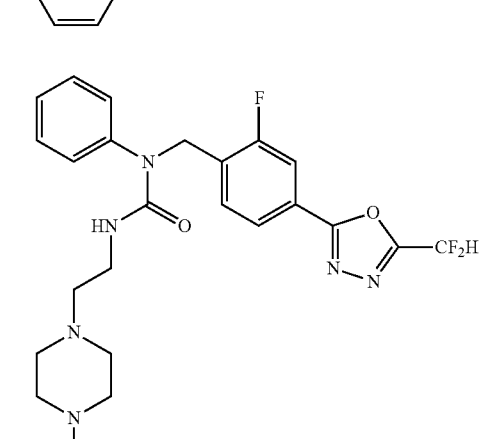 |

TABLE 1-continued
| Ex. | Comp. | Structure |
|---|---|---|
| 430 | 22002 | 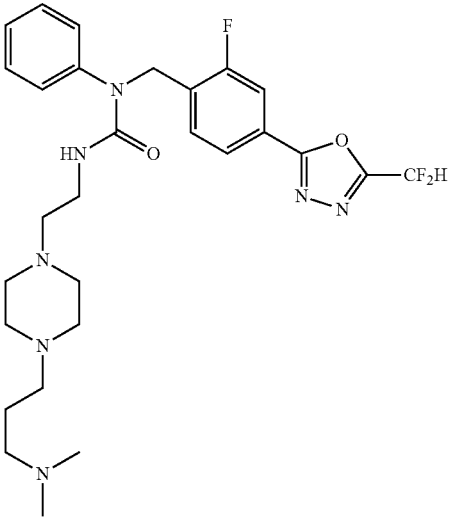 [SMILES: CN(C)CCCN1CCN(CCNC(=O)N(Cc2ccc(-c3nnc(C(F)F)o3)cc2F)c2ccccc2)CC1] |
| 431 | 22003 | 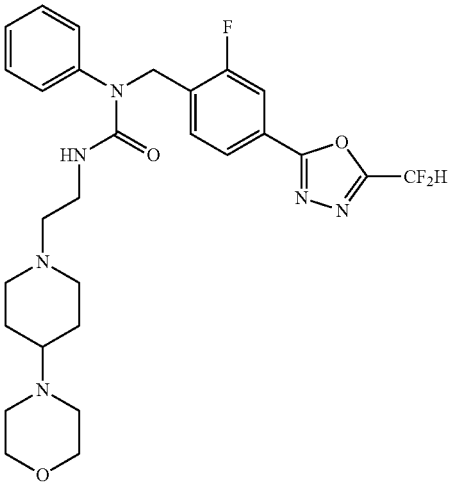 [SMILES: O=C(NCCN1CCC(N2CCOCC2)CC1)N(Cc1ccc(-c2nnc(C(F)F)o2)cc1F)c1ccccc1] |
| 432 | 22004 | 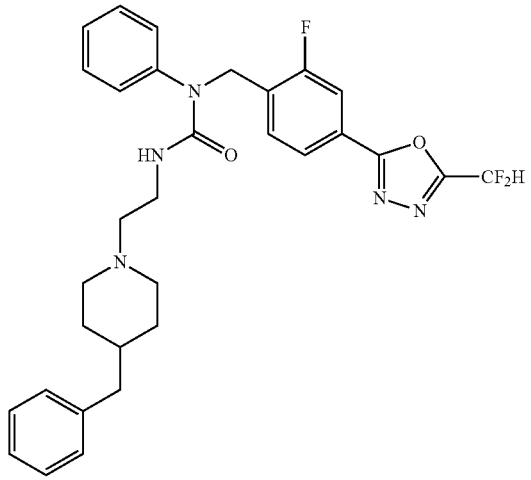 [SMILES: O=C(NCCN1CCC(Cc2ccccc2)CC1)N(Cc1ccc(-c2nnc(C(F)F)o2)cc1F)c1ccccc1] |

TABLE 1-continued

| Ex. | Comp. | Structure |
|---|---|---|
| 433 | 22005 | 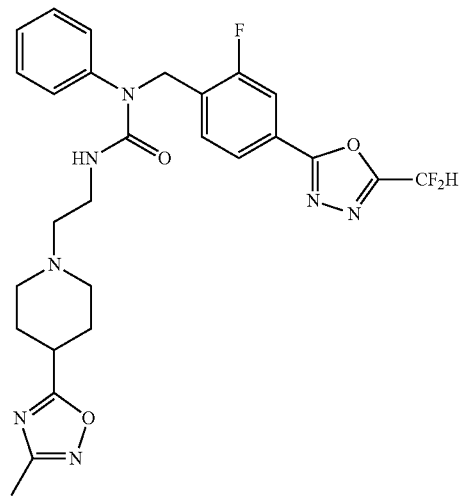 [SMILES: Cc1noc(C2CCN(CCNC(=O)N(Cc3ccc(-c4nnc(C(F)F)o4)cc3F)c3ccccc3)CC2)n1] |
| 434 | 22006 | 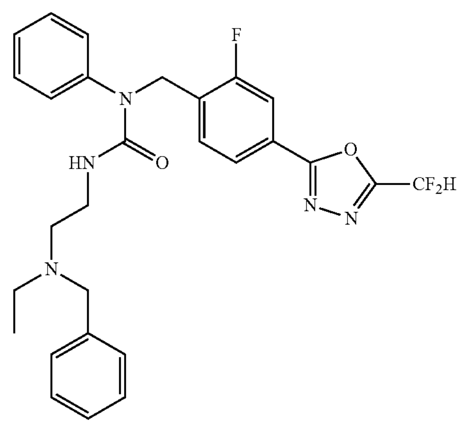 [SMILES: CCN(CCNC(=O)N(Cc1ccc(-c2nnc(C(F)F)o2)cc1F)c1ccccc1)Cc1ccccc1] |
| 435 | 22007 | 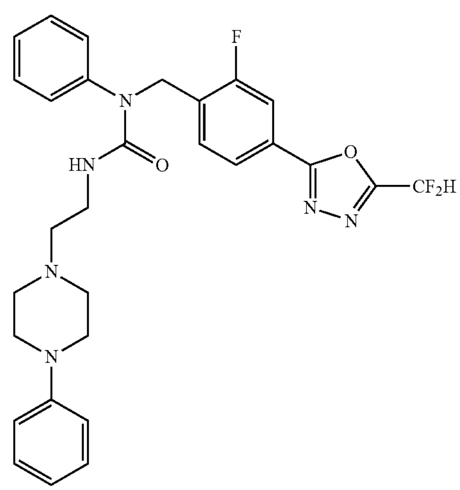 [SMILES: O=C(NCCN1CCN(c2ccccc2)CC1)N(Cc1ccc(-c2nnc(C(F)F)o2)cc1F)c1ccccc1] |

TABLE 1-continued

| Ex. | Comp. | Structure |
|---|---|---|
| 436 | 22008 | 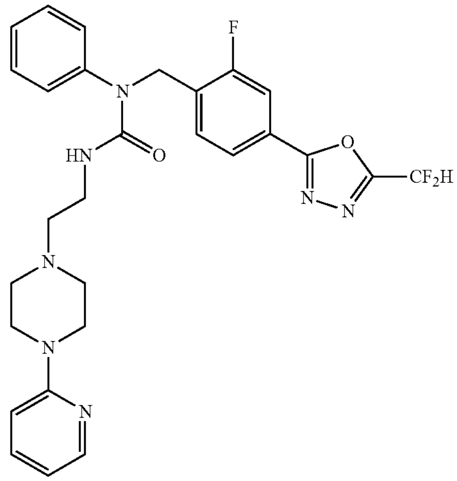 |
| 437 | 22009 | 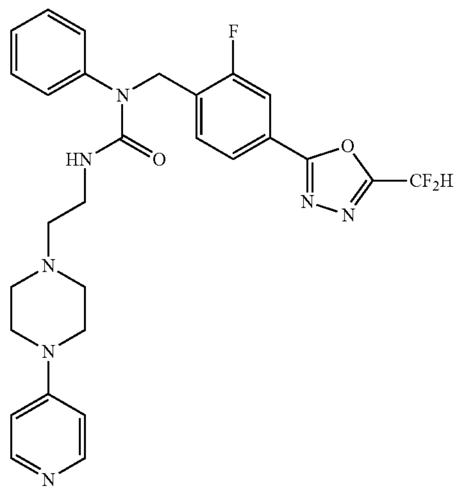 [SMILES: O=C(NCCN1CCN(c2ccncc2)CC1)N(Cc1ccc(-c2nnc(C(F)F)o2)cc1F)c1ccccc1] |
| 438 | 22010 | 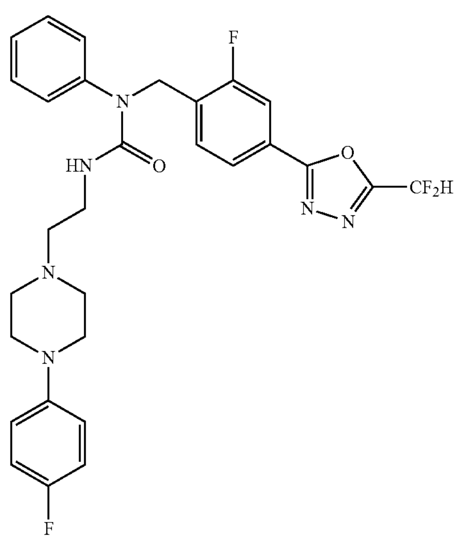 [SMILES: O=C(NCCN1CCN(c2ccc(F)cc2)CC1)N(Cc1ccc(-c2nnc(C(F)F)o2)cc1F)c1ccccc1] |

TABLE 1-continued
| Ex. | Comp. | Structure |
|---|---|---|
| 439 | 22011 | 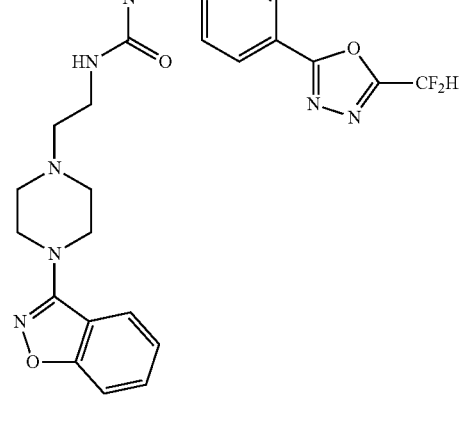 |
| 440 | 22012 | 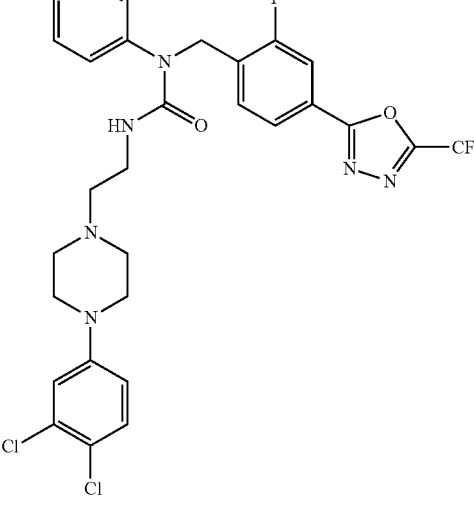 |
| 441 | 22013 | 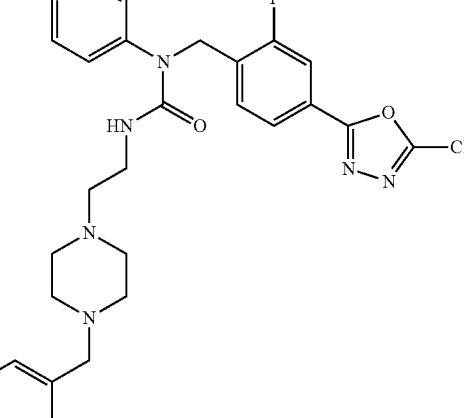 |

US 10,717,716 B2
173 174
TABLE 1-continued
| Ex. | Comp. | Structure |
|---|---|---|
| 442 | 22014 | 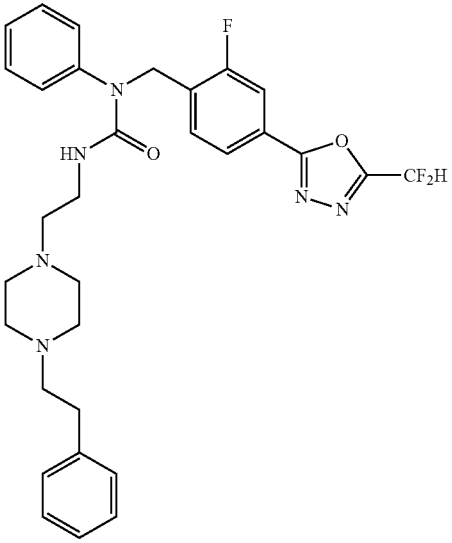 [SMILES: O=C(NCCN1CCN(CCc2ccccc2)CC1)N(Cc1ccc(-c2nnc(C(F)F)o2)cc1F)c1ccccc1] |
| 443 | 22015 | 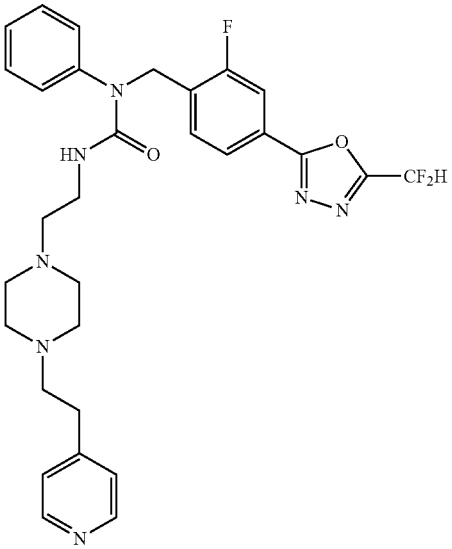 [SMILES: O=C(NCCN1CCN(CCc2ccncc2)CC1)N(Cc1ccc(-c2nnc(C(F)F)o2)cc1F)c1ccccc1] |

TABLE 1-continued
| Ex. | Comp. | Structure |
|-----|-------|-----------|
| 444 | 22016 | 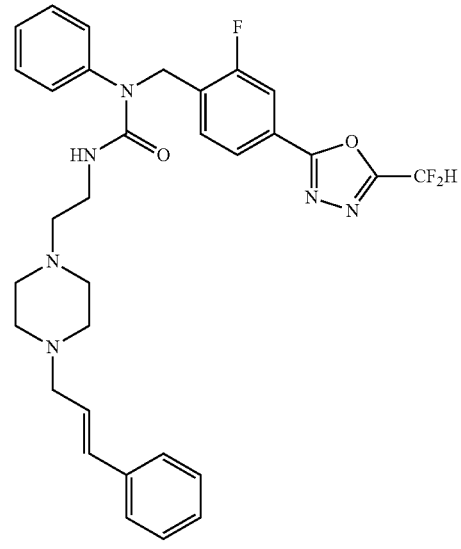 [SMILES: O=C(NCCN1CCN(C/C=C/c2ccccc2)CC1)N(Cc1ccc(-c2nnc(C(F)F)o2)cc1F)c1ccccc1] |
| 445 | 22017 | 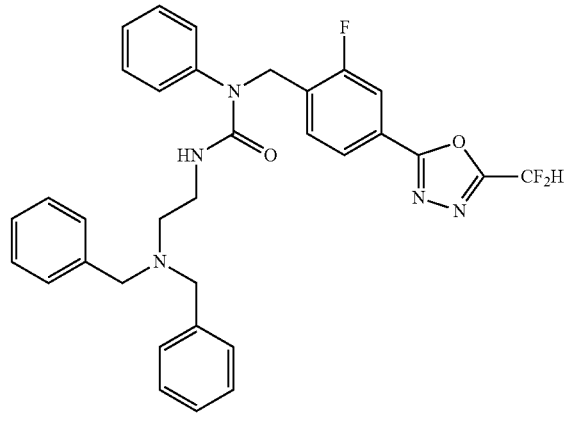 [SMILES: O=C(NCCN(Cc1ccccc1)Cc1ccccc1)N(Cc1ccc(-c2nnc(C(F)F)o2)cc1F)c1ccccc1] |
| 446 | 22018 | 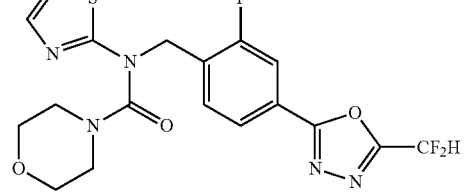 |
| 447 | 22019 | 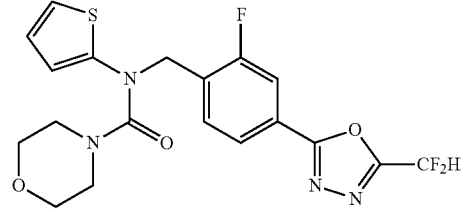 [SMILES: O=C(N1CCOCC1)N(Cc1ccc(-c2nnc(C(F)F)o2)cc1F)c1cccs1] |

TABLE 1-continued

| Ex. | Comp. | Structure |
|---|---|---|
| 448 | 22020 | 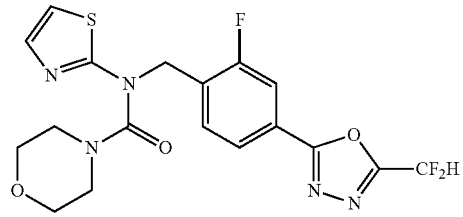 |
| 449 | 22021 | 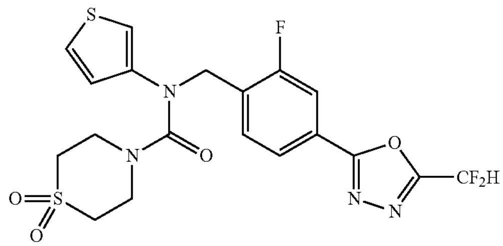 [SMILES: O=C(N1CCS(=O)(=O)CC1)N(Cc1ccc(-c2nnc(C(F)F)o2)cc1F)c1ccsc1] |
| 450 | 22024 | 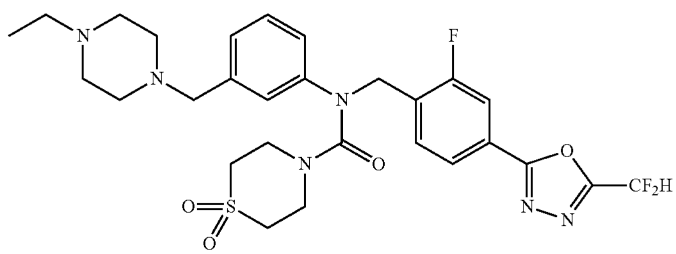 [SMILES: CCN1CCN(Cc2cccc(N(Cc3ccc(-c4nnc(C(F)F)o4)cc3F)C(=O)N3CCS(=O)(=O)CC3)c2)CC1] |

Preferably, the compounds represented by formula I, stereoisomers thereof or pharmaceutically acceptable salts thereof may be selected from the group consisting of compounds 21325, 21337, 21360, 21370, 21373, 21378, 21383, 21386, 21423, 21432, 21448, 21455, 21465, 21467, 21469, 21470, 21471, 21472, 21473, 21478, 21480, 21482, 21484, 21490, 21492, 21495, 21496, 21497, 21498, 21499, 21500, 21501, 21514, 21516, 21518, 21522, 80721527, 21529, 21531, 21532, 21535, 2158316, 21540, 21544, 21546, 21565, 21566, 21578, 21583, 21584, 21585, 21586, 21587, 21591, 21593, 21597, 21598, 21599, 21600, 21602, 21619, 21620, 21622, 21623, 21624, 21625, 21626, 21629, 21630, 21632, 21643, 21646, 21652, 21653, 21654, 21655, 21656, 21657, 21665, 21667, 21679, 20707, 21709, 21710, 21724, 21735, 21736, 21759, 21760, 21806, 21807, 21808, 21810, 21824, 21829, 21830, 21831, 21839, 21841, 21843, 21845, 21847619, 21851, 21855, 21858, 21877, 21878, 62921879, 21881, 21882, 21883, 21884, 21885, 21886, 21887, 21888, 21894, 21905, 21943, 21944, 21985 and 21986. More preferably, the compounds represented by formula I, stereoisomers thereof or pharmaceutically acceptable salts thereof may be selected from the group consisting of compounds 21337, 21370, 21373, 21378, 21423, 21465, 21484, 21496, 21498, 21499, 21500, 21501, 21518, 21522, 21527, 21531, 21536, 21540, 21546, 21565, 21566, 21583, 21584, 21585, 21586, 21587, 21591, 21593, 21599, 21600, 21602, 21619, 21620.21624, 21625, 21626, 21629, 21630.21643, 21654, 21655, 21665, 21709, 21710, 21724.21735, 21759, 21808, 21810, 21841, 21843, 21851, 21879, 21885 and 21888.

As used herein, the term "pharmaceutically acceptable salt" means any salt that is generally used in the pharmaceutical field. Examples of the pharmaceutically acceptable salt include, but are not limited to, salts with inorganic ions such as calcium, potassium, sodium or magnesium ions, salts with inorganic acids such as hydrochloric acid, nitric acid, phosphoric acid, bromic acid, iodic acid, perchloric acid or sulfuric acid, salts with organic acids such as acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid or the like, salts with sulfonic acids such as methanesulfonic acid, ethanesulfonic acid, benzenesulfonic acid, p-toluenesulfonic acid or naphthalenesulfonic acid, salts with amino acids such as glycine, arginine or lysine, and salts with amines such as trimethylamine, triethylamine, ammonia, pyridine or picoline.

In the present invention, preferred salts include salts with hydrochloric acid, phosphoric acid, sulfuric acid, trifluoroacetic acid, citric acid, bromic acid, maleic acid, tartaric acid or the like, and preferred examples of such compounds include compounds 21378 as disclosed herein.

The compounds represented by formula I may contain one or more asymmetrical carbon atoms, and thus may exist in the form of racemates, racemic mixtures, single enantiomers, diastereomeric mixtures, and individual diastereomers. The compounds of formula I can be separated into such isomers by methods known in the art, for example, column chromatography or HPLC. Alternatively, stereoisomers of the compounds of formula I may be synthesized by stereospecific synthesis using optically pure starting materials and/or reagents of known configuration.

Methods for Preparation of 1,3,4-Oxadiazole Derivative Compounds

The present invention provides methods for the preparation of the 1,3,4-oxadiazole derivative compounds presented by formula I, stereoisomers thereof, or pharmaceutically acceptable salts thereof.

Preferred methods for the preparation of the 1,3,4-oxadiazole derivative compounds presented by formula I, stereoisomers thereof, or pharmaceutically acceptable salts thereof are as shown in reaction schemes 1 to 19 below, and also include modifications obvious to those skilled in the art.

is also prepared by reacting a compound of formula 4-1-5 or formula 4-1-6 with an amine compound to yield a compound of formula 4-1-7, followed by a substitution reaction with a compound of formula 4-1-1. The ester moiety of the compound of formula 4-1-8 is substituted with hydrazine, and then reacted with trifluoroacetic anhydride or difluoroacetic anhydride, thereby preparing a compound of formula 4-1-11. Meanwhile, a compound of formula 4-1-10, which has no oxadiazole ring, is reacted with 1-methoxy-N-triethyl-ammoniosulfonyl-methaneimidate (Burgess reagent), thereby preparing a compound of formula 4-1-11.

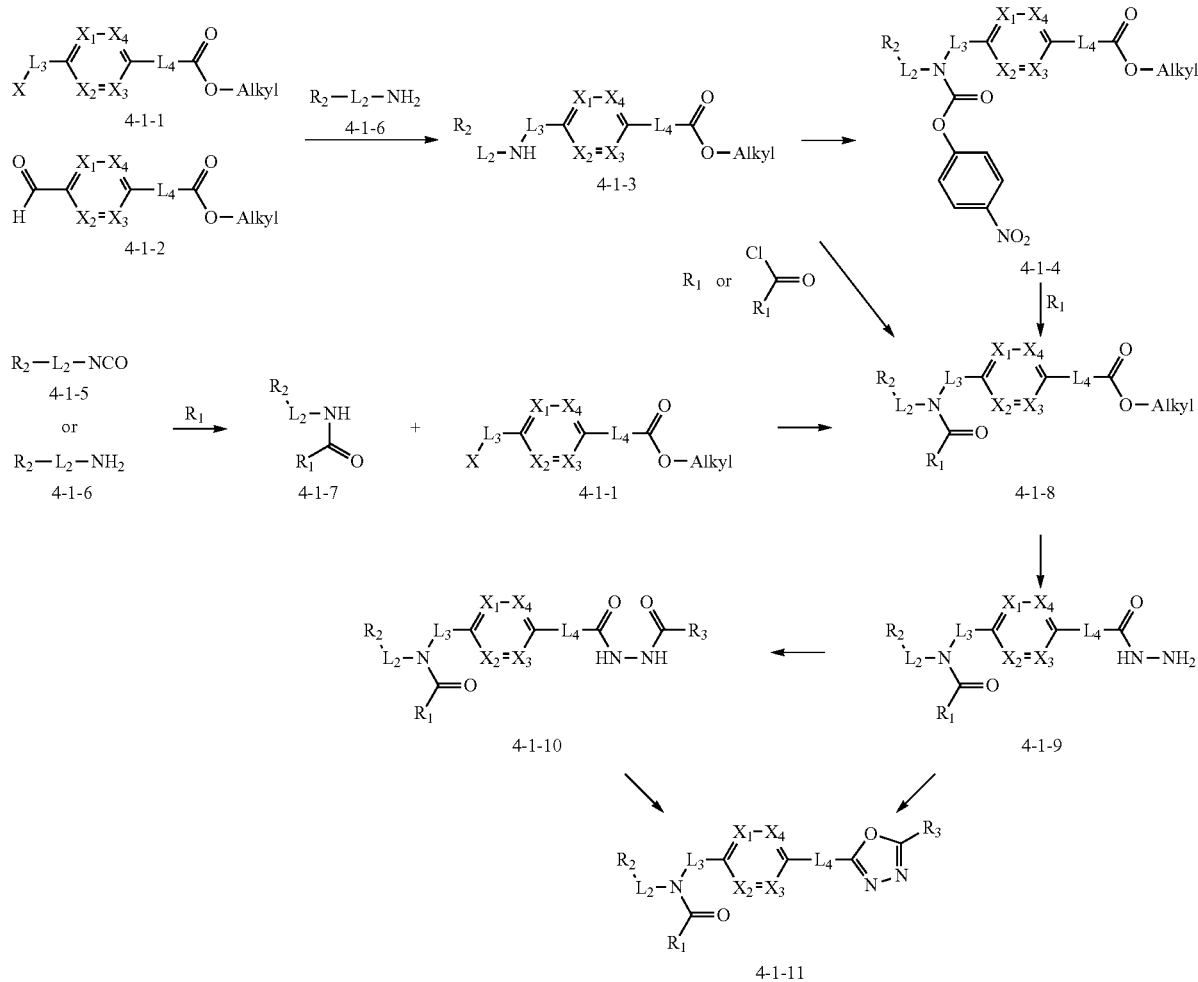

[Reaction Scheme 1]

Reaction scheme 1 above shows a method for preparing compounds having a urea structure. As shown therein, a compound of formula 4-1-1 is subjected to a substitution reaction with an amine compound, or a compound of formula 4-1-2 is subjected to a reductive amination reaction with an amine compound, thereby preparing a compound of formula 4-1-3. The compound of formula 4-1-3 is reacted with acyl chloride or an amine compound to yield a compound of formula 4-1-8 which has a urea structure. Alternatively, the compound of formula 4-1-8 is prepared by reacting a compound of formula 4-1-3 with p-nitrophenyl chloroformate to yield a compound of formula 4-1-4, followed by reaction with an amine compound. Alternatively, the compound of formula 4-1-8, which has a urea structure, Compounds that are prepared according to reaction scheme 1 above are compounds 21249, 21285, 21318, 21319, 21325, 21327, 21329, 21333, 21336, 21337, 21340, 21341, 21342, 21343, 21344, 21345, 21346, 21347, 21348, 21349, 21350, 21351, 21352, 21353, 21354, 21355, 21357, 21358, 21359, 21360, 21361, 21368, 21369, 21370, 21371, 21372, 21373, 21374, 21375, 21376, 21377, 21378, 21379, 21380, 21381, 21382, 21383, 21389, 21390, 21391.21392, 21393, 21394, 21395, 21397, 21398, 21399, 21400, 21401, 21402, 21403, 21405, 21406, 21407, 21408, 21409, 21410, 21411, 21412, 21413, 21414, 21415, 21416, 21422, 21423, 21424, 21425, 21426, 21427, 21428, 21429, 21433, 21434, 21440, 21441, 21442, 21445, 21446, 21447, 21448, 21449, 21450, 21451, 21452, 21453, 21454, 21455, 21456, 21457, 21458, 21459, 21460, 21461, 21462, 21463, 21464, 21465, 21466, 21467, 21468, 21469, 21470, 21471, 21472, 21473, 21474, 21475, 21476, 21477, 21478, 21479, 21480, 21481, 21482, 21483, 21484, 21511, 21512, 21513, 21514, 21522, 21527, 21528, 21529, 21530, 21531, 21532, 21543, 21544, 21545, 21546, 21552, 21553, 21554, 21555, 21556, 21557, 21564, 21565, 21566, 21583, 21584, 21586, 21587, 21591, 21592, 21593, 21594, 21597, 21598, 21599, 21600, 21601, 21602, 21619, 21620, 21622, 21623, 21624, 21625, 21626, 21629, 21630, 21631, 21632, 21633, 21634, 21643, 21644, 21645, 21646, 21650, 21651, 21652, 21653, 21654, 21655, 21656, 21657, 21658, 21659, 21660, 21664, 21665, 21666, 21667, 21668, 21669, 21679, 21707, 21708, 21709, 21710, 21724, 21735, 21736, 21759, 21760, 21766, 21767, 21797, 21798, 21799, 21806, 21807, 21808, 21809, 21810, 21811, 21812, 21813, 21829, 21830, 21831, 21839, 21840, 21841, 21842, 21843, 21844, 21845, 21846, 21847, 21848, 21849, 21850, 21851, 21852, 21853, 21854, 21855, 21856, 21857, 21858, 21859, 21860, 21861, 21862, 21863, 21864, 21865, 21866, 21867, 21868, 21869, 21870, 21871, 21872, 21873, 21874, 21875, 21876, 21877, 21878, 21879, 21880, 21881, 21882, 21883, 21884, 21885, 21886, 21887, 21888, 21889, 21890, 21891, 21892, 21893, 21894, 21910, 21929, 21930, 21931, 21932 and 21933.

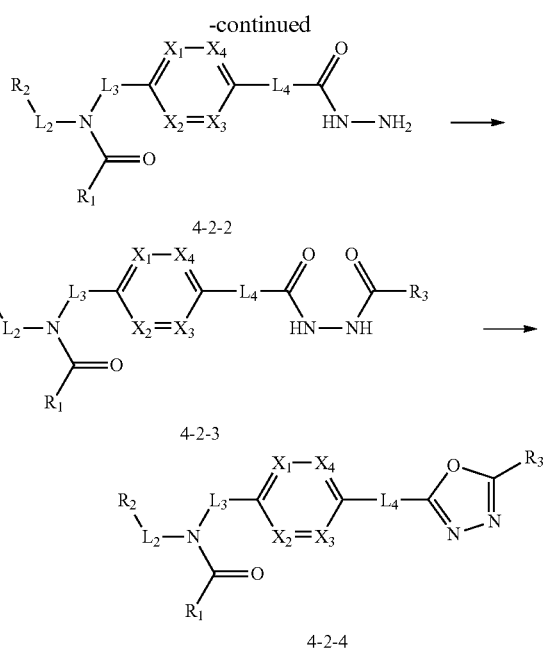

[Reaction Scheme 2]

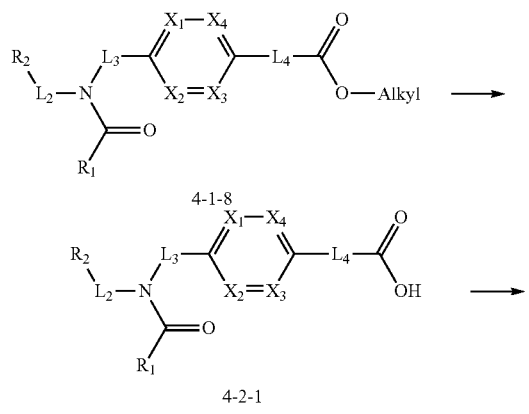

Reaction scheme 2 above shows another method for preparing compounds having a urea structure. As shown therein, the compound of formula 4-1-8, synthesized according to reaction scheme 1, is hydrolyzed with lithium hydroxide to yield a compound of formula 4-2-1, which is then subjected to an amide coupling reaction with hydrazine, thereby preparing a compound of formula 4-2-2. The compound of formula 4-2-2 is reacted with trifluoroacetic anhydride or difluoroacetic anhydride to yield a compound of formula 4-2-3, which is then reacted with 1-methoxy-N-triethylammoniosulfonyl-methaneimidate (Burgess reagent), thereby preparing a compound of formula 4-2-4.

Compounds that are prepared according to reaction scheme 2 above are compounds 21431 and 21432.

[Reaction Scheme 3]

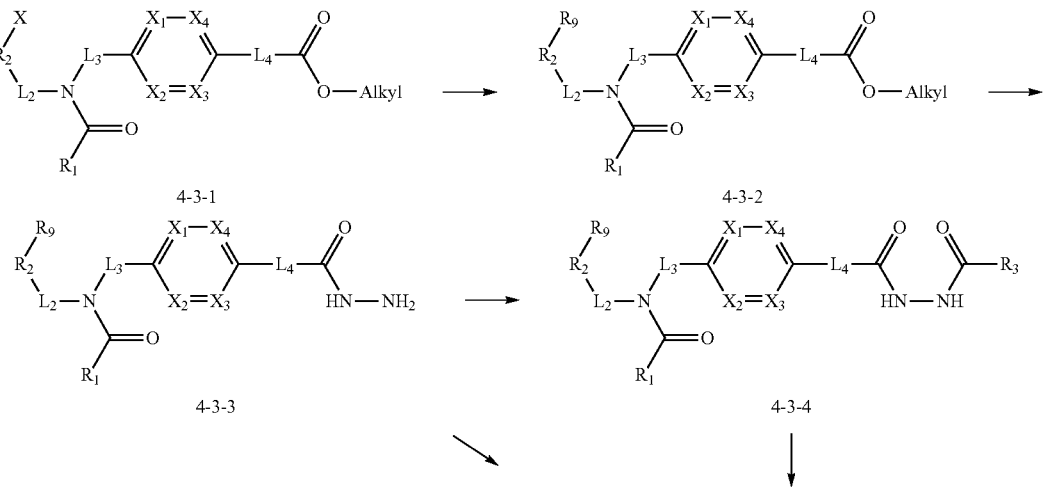

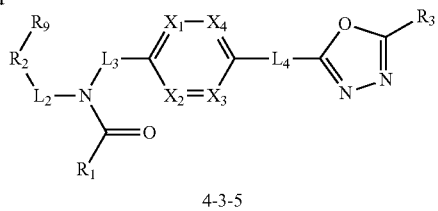

4-3-5

Reaction scheme 3 above shows a method for preparing a urea compound having a biaryl structure. As shown therein, a compound of formula 4-3-1 is subjected to a Suzuki reaction with boronic acid or boronic ester or a Buckwald reaction with an amine compound, thereby preparing a compound of formula 4-3-2. Then, the prepared compound of formula 4-3-2 is reacted with hydrazine to yield a compound of formula 4-3-3, which is then reacted with trifluoroacetic anhydride or difluoroacetic anhydride, thereby preparing a compound of formula 4-3-5. Alternatively, a compound of formula 4-3-4, which has no oxadiazole ring, is reacted with 1-methoxy-N-tiethylammoniosulfonyl-methaneimidate (Burgess reagent), thereby preparing the compound of formula 4-3-5.

Compounds that are prepared according to reaction scheme 3 above are compounds 21435, 21436, 21437, 21438, 21439, 21485, 21486, 21487, 21488, 21489, 21490, 21491, 21492, 21493, 21494, 21502, 21517, 21518, 21519, 21520, 21521, 21533, 21534, 21535, 21536, 21537, 21540, 21541, 21542, 21621, 21627, 21628, 21823 and 21824.

[Reaction Scheme 4]

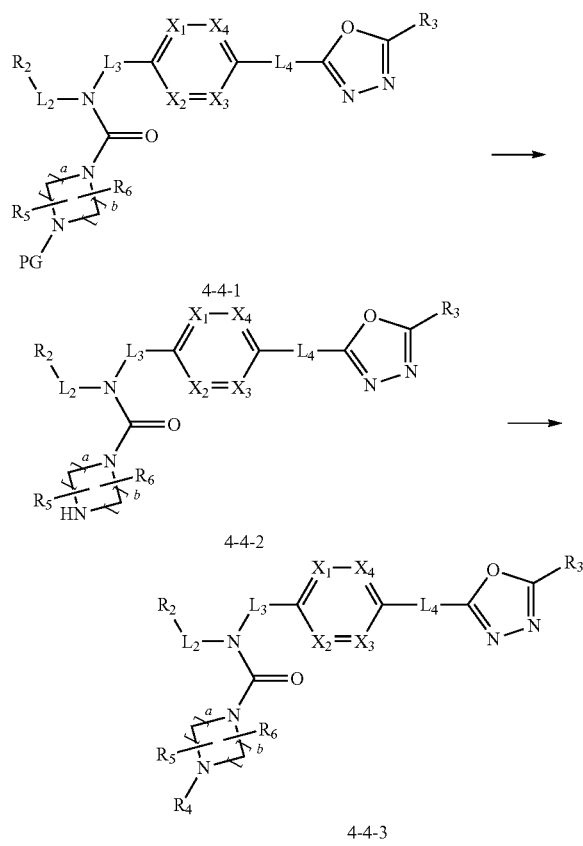

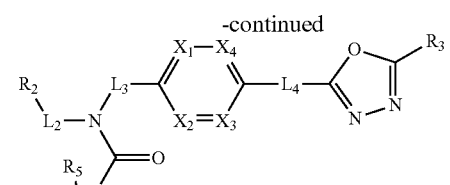

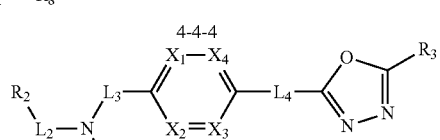

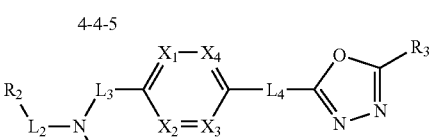

Reaction scheme 4 above shows a method of introducing a substituent into secondary amine. As shown therein, compounds of formula 4-4-1 and formula 4-4-4 are deprotected to yield compounds of formula 4-4-2 and formula 4-4-5, respectively. The compounds of formula 4-4-2 and formula 4-4-5 are reacted with acyl chloride or sulfonyl chloride to introduce a substituent therein or are subjected to a reductive amination reaction and a substitution reaction, thereby preparing compounds of formula 4-4-3 and formula 4-4-6, respectively.

Compounds that are prepared according to reaction scheme 4 above are compounds 21362, 21363, 21364, 21365, 21366, 21367, 21384, 21385, 21386, 21387, 21388, 21394, 21404, 21417, 21418, 21419, 21420, 21421, 21495, 21496, 21497, 21498, 21499, 21500 and 21501.

[Reaction Scheme 5]

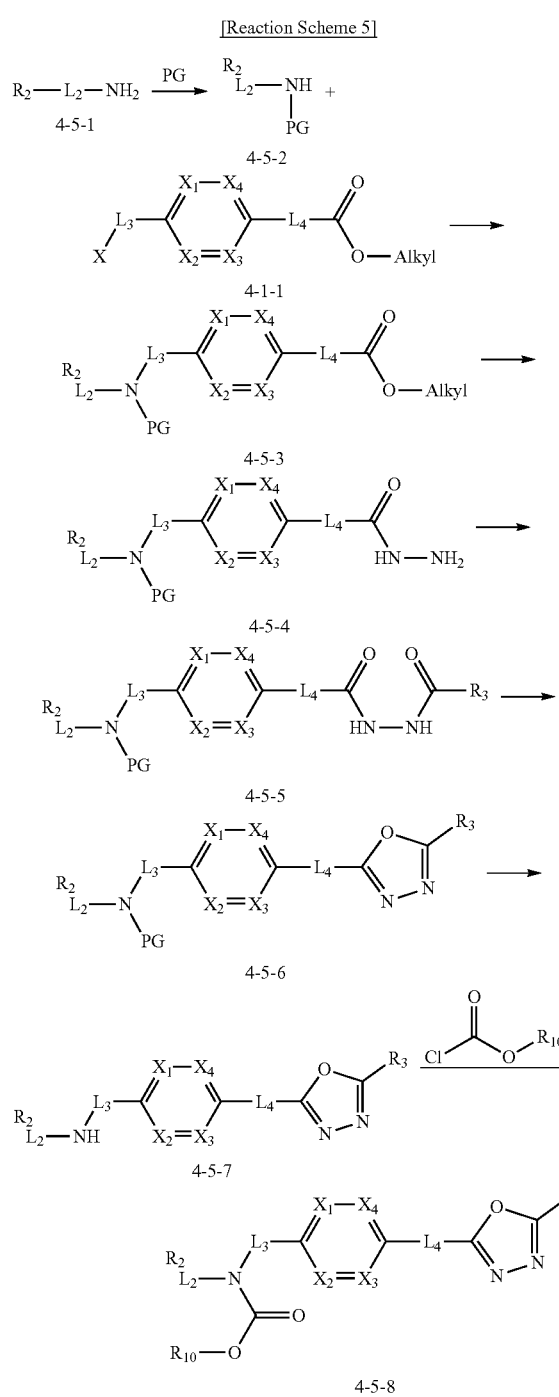

4-5-6, which is then deprotected, thereby preparing a compound of formula 4-5-7. Then, the compound of formula 4-5-7 is reacted with a chloroformate compound to yield a compound of formula 4-5-8.

Compounds that are prepared according to reaction scheme 5 above are compounds 21568, 21569 and 21570.

[Reaction Scheme 6]

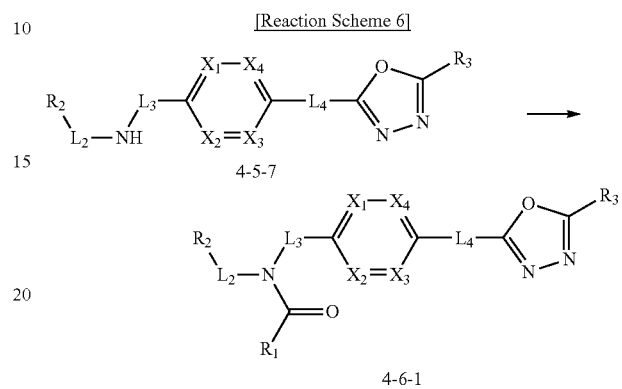

Reaction scheme 6 above shows a method for preparing compounds having a urea structure. As shown therein, the compound of formula 4-5-7, synthesized according to reaction scheme 5, is reacted with an amine and triphosgene or reacted with isocyanate, thereby preparing a compound of formula 4-6-1.

Compounds that are prepared according to reaction scheme 6 above are compounds 21576, 21577, 21578 and 21585.

[Reaction Scheme 7]

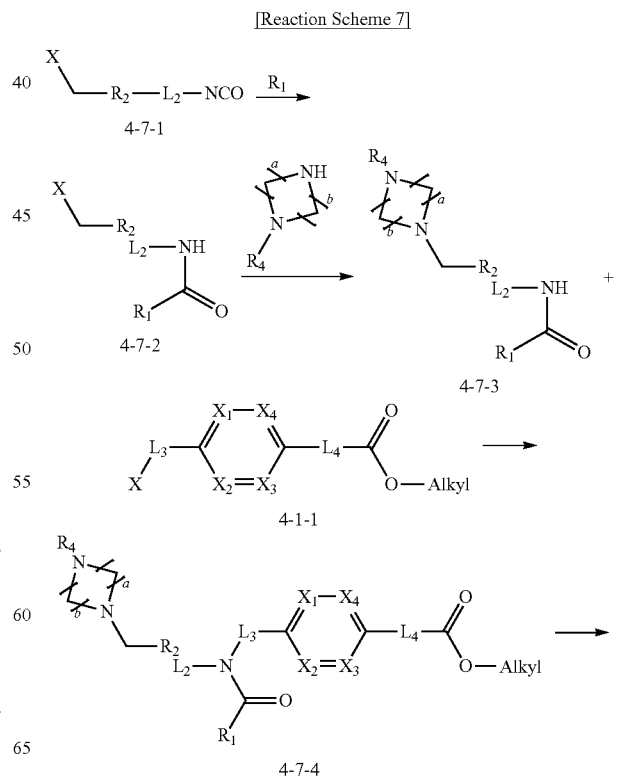

Reaction scheme 5 above shows a method for synthesizing compounds having a carbamate structure. As shown therein, a protecting group is introduced into an amine of formula 4-5-1 to yield a compound of formula 4-5-2, which is then subjected to a substitution reaction with a compound of formula 4-1-1 to yield a compound of formula 4-5-3. Then, the compound of formula 4-5-3 is reacted with hydrazine, and then reacted with trifluoroacetic anhydride or difluoroacetic anhydride, thereby preparing a compound of formula 4-5-5. Then, the compound of formula 4-5-5 is reacted with 1-methoxy-N-triethylammoniosulfonyl-methaneimidate (Burgess reagent) to yield a compound of formula

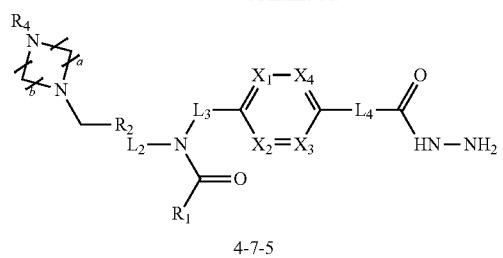

4-7-5

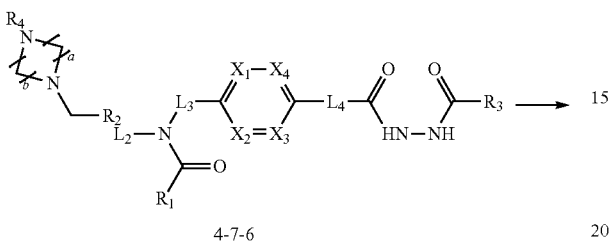

4-7-6

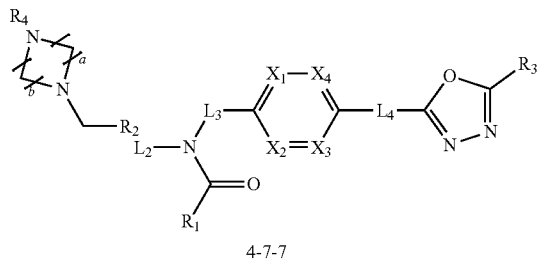

4-7-7

Reaction scheme 7 above shows a method for preparing urea compounds having a heterocycloalkyl structure introduced therein. As shown in reaction scheme 7, a compound of formula 4-7-1 is reacted with an amine compound to yield a compound of formula 4-7-2, which is then subjected to a substitution reaction with an amine compound to yield a compound of formula 4-7-3. Then, an alkyl group is introduced into the compound of formula 4-7-3 in the presence of sodium hydride to yield a compound of formula 4-7-4. Then, the compound of formula 4-7-4 is reacted with hydrazine to yield a compound of formula 4-7-5, which is then reacted with trifluoroacetic anhydride or difluoroacetic anhydride to yield a compound of formula 4-7-6. The compound of formula 4-7-6 is reacted with 1-methoxy-N-triethylammoniosulfonyl-methaneimidate (Burgess reagent), thereby preparing a compound of formula 4-7-7.

Compounds that are prepared according to reaction scheme 7 above are compounds 21515 and 21516.

[Reaction Scheme 8]

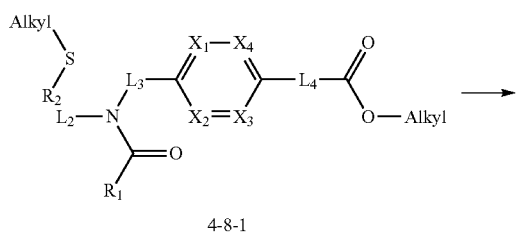

4-8-1

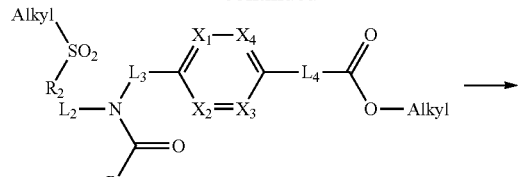

4-8-2

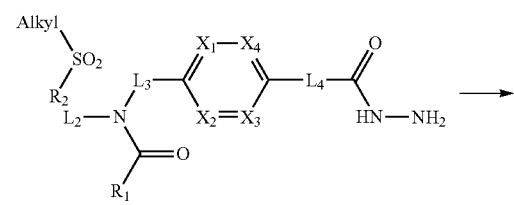

4-8-3

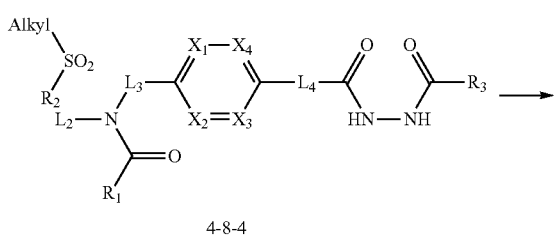

4-8-4

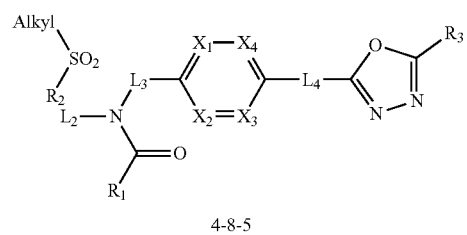

4-8-5

Reaction scheme 8 above shows a method for preparing compounds having an alkyl sulfonyl substituent introduced therein. As shown in reaction scheme 8, a compound of formula 4-8-1 is subjected to an oxidation reaction to yield a compound of formula 4-8-2, which is then reacted with hydrazine to yield a compound of formula 4-8-3. Then, the prepared compound of formula 4-8-3 is reacted with trifluoroacetic anhydride or difluoroacetic anhydride to yield a compound of formula 4-8-4, which is then reacted with 1-methoxy-N-triethylammoniosulfonyl-methaneimidate (Burgess reagent), thereby preparing a compound of formula 4-8-5.

Compounds that are prepared according to reaction scheme 8 above are compounds 21443 and 21444.

[Reaction Scheme 9]
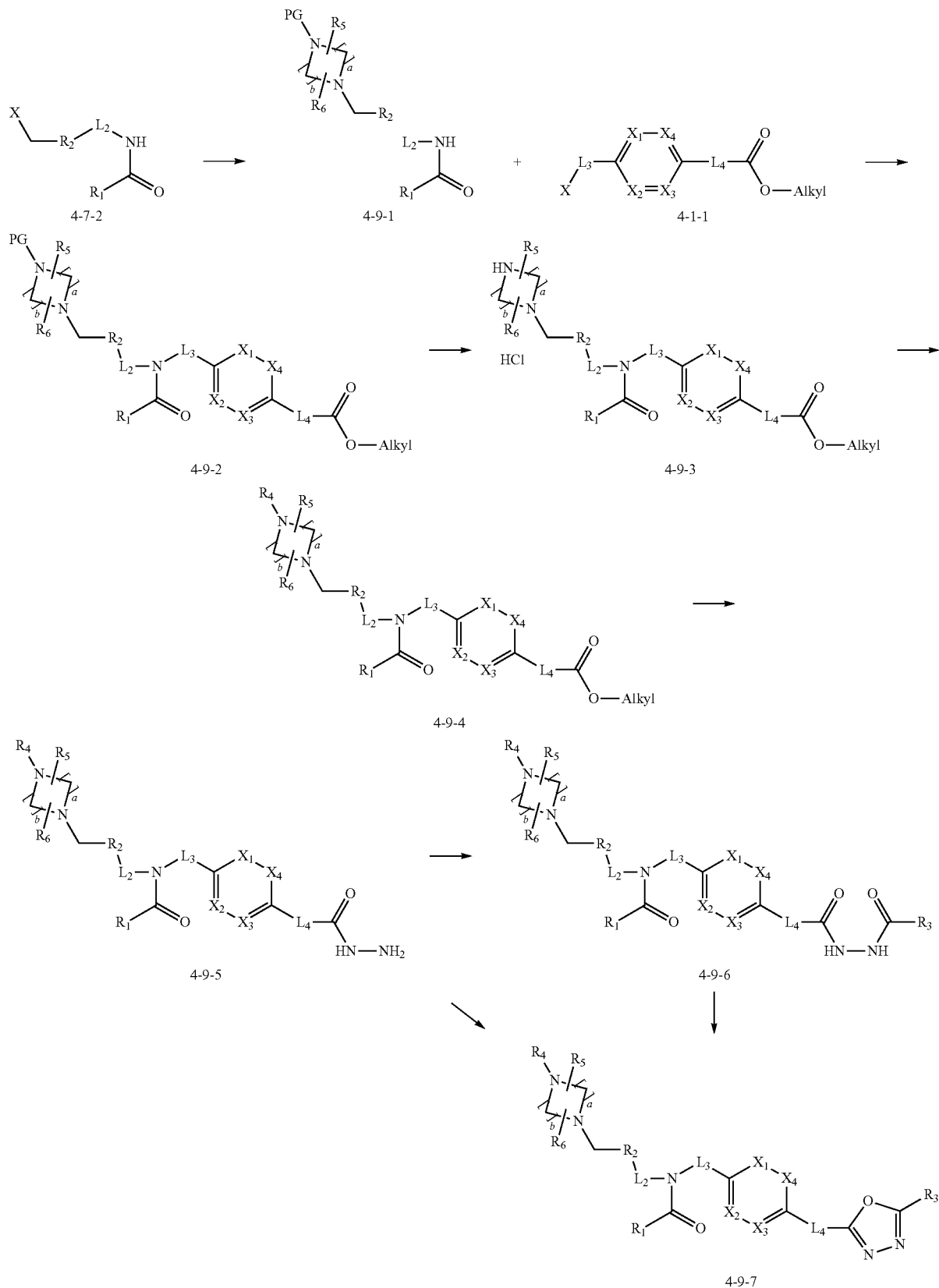

Reaction scheme 9 above shows a method for preparing urea compounds having a heterocycloalkyl structure introduced therein. As shown in reaction scheme 9, the compound of formula 4-7-2, synthesized according to reaction scheme 7, is subjected to a substitution reaction with an amine compound to yield a compound of formula 4-9-1. Then, an alkyl group is introduced into the compound of formula 4-9-1 in the presence of sodium hydride to yield a compound of formula 4-9-2. The compound of formula 4-9-2 is deprotected under an acidic condition to yield a compound of formula 4-9-3, which is then subjected to an alkylation reaction or a reductive amination reaction to introduce various substituents therein, thereby preparing a compound of formula 4-9-4. The compound of formula 4-9-4 is reacted with hydrazine to yield a compound of formula 4-9-5, which is then reacted with trifluoroacetic anhydride or difluoroacetic anhydride to yield a compound of formula 4-9-7. Alternatively, a compound of formula 4-9-6, which has no oxadiazole ring, is reacted with 1-methoxy-N-triethylammoniosulfonyl-methaneimidate (Burgess reagent) to yield the compound of formula 4-9-7.

Compounds that are prepared according to reaction scheme 9 above are compounds 21895, 21896, 21897, 21898, 21901, 21902, 21925, 21926, 21934 and 21935.

[Reaction Scheme 10]

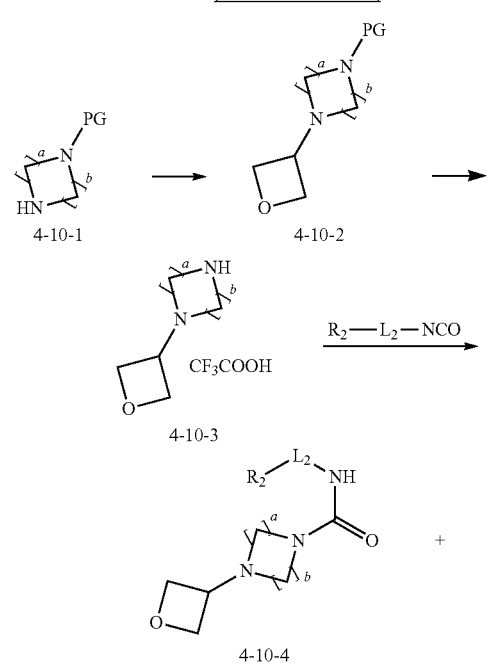

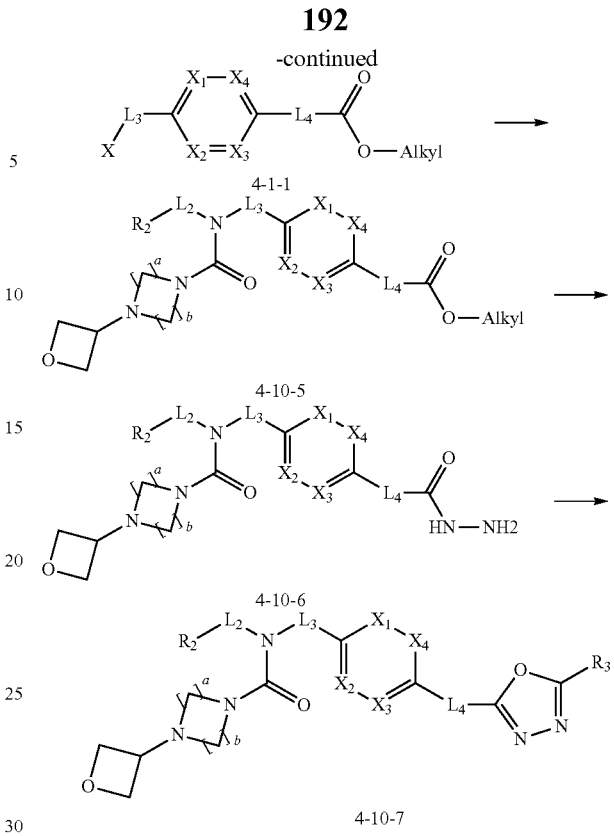

Reaction scheme 10 above shows a method for preparing urea compounds having an oxetane structure introduced therein. As shown in reaction scheme 10, a compound of formula 4-10-1 is reacted with an oxetanone compound to yield a compound of formula 4-10-2, which is then deprotected to yield a compound of formula 4-10-3. The compound of formula 4-10-3 is reacted with isocyanate (formula 4-1-5) to yield a compound of formula 4-10-4, which has a urea structure, after which the compound of formula 4-10-4 is subjected to a substitution reaction with a compound of formula 4-1-1 to yield a compound of formula 4-10-5. The compound of formula 4-10-5 is reacted with hydrazine to yield a compound of formula 4-10-6, which is then reacted with trifluoroacetic anhydride or difluoroacetic anhydride, thereby preparing a compound of formula 4-10-7.

Compound that is prepared according to reaction scheme 10 above is compound 21905.

[Reaction Scheme 11]

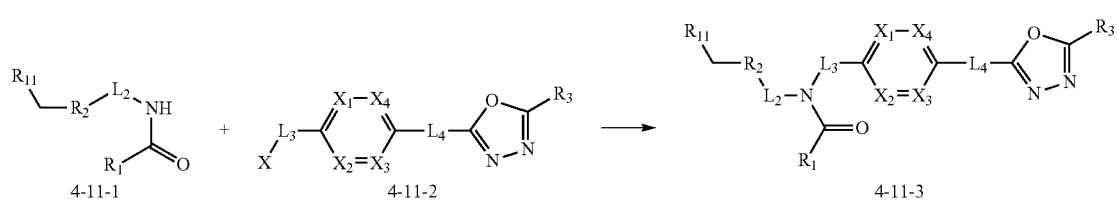

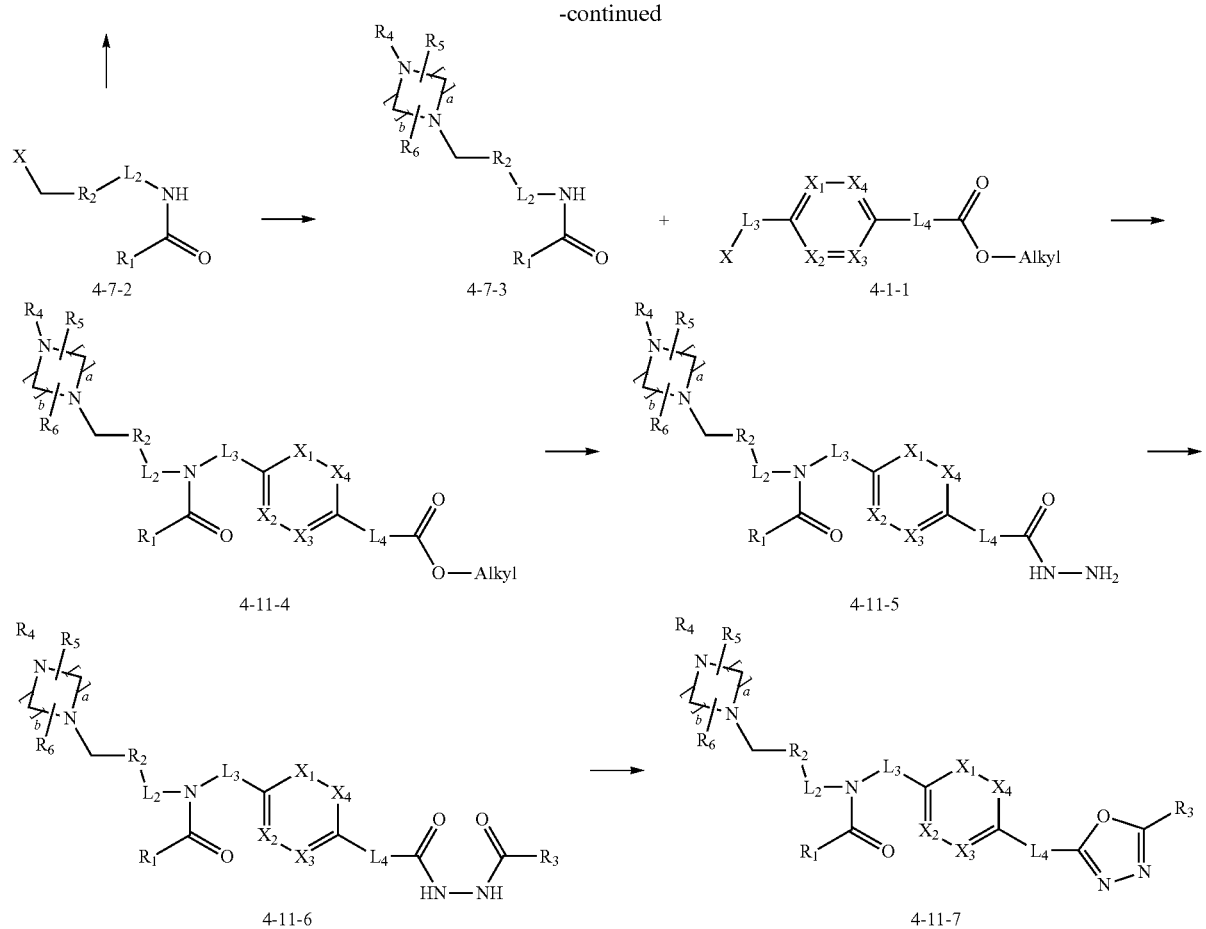

Reaction scheme 11 above shows a method for preparing urea compounds having a heterocycloalkyl structure introduced therein. As shown in reaction scheme 11, the compound of formula 4-7-2, synthesized according to reaction scheme 7, is subjected to a substitution reaction with an amine compound to yield a compound of formula 4-11-1. The compound of formula 4-11-1 is subjected to an alkylation reaction in the presence of sodium hydride, thereby preparing a compound of formula 4-11-3.

In addition, the compound of formula 4-7-3, synthesized according to reaction scheme 7, is subjected to an alkylation reaction in the presence of sodium hydride to yield a compound of formula 4-11-4, which is then reacted with hydrazine to yield a compound of formula 4-11-5. The compound of formula 4-11-5 is reacted with trifluoroacetic anhydride or difluoroacetic anhydride to yield a compound of formula 4-11-6. Then, the compound of 4-11-6 is reacted with 1-methoxy-N-triethylammoniosulfonyl-methaneimidate (Burgess reagent), thereby preparing a compound of formula 4-11-7.

Compounds that are prepared according to reaction scheme 11 above are compounds 21899, 21900, 21914, 21915, 21916, 21917, 21918 and 21919.

[Reaction Scheme 12]

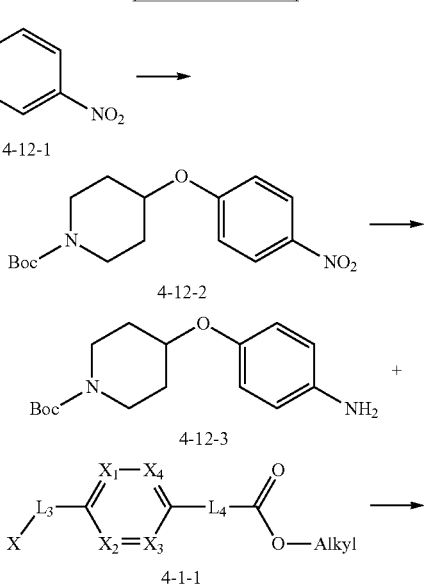

195
-continued

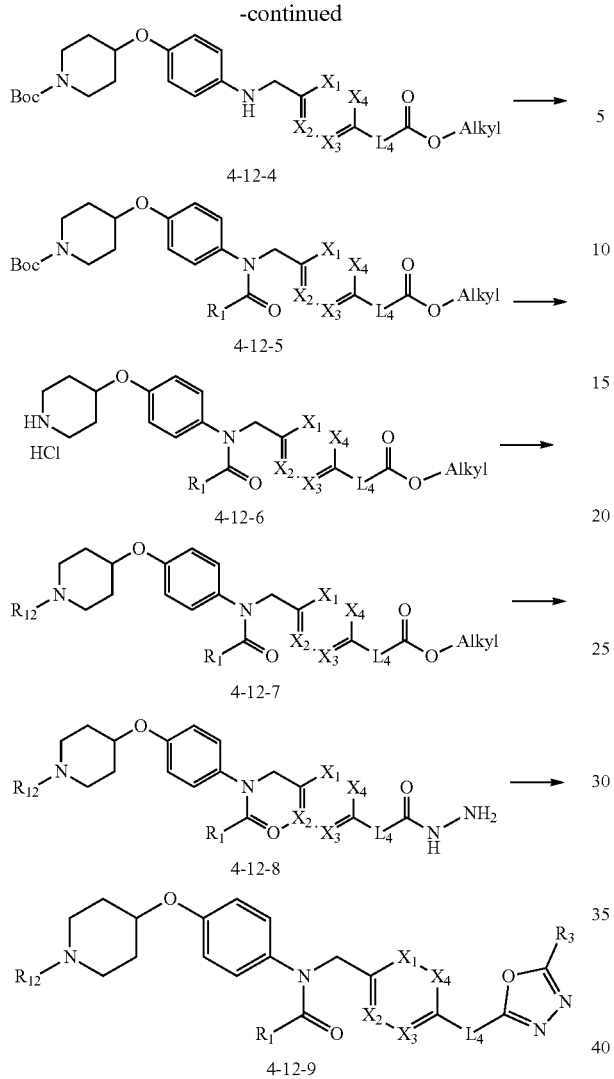

Reaction scheme 12 above shows a method for preparing urea compounds having a heterocycloalkyl structure introduced therein. As shown in reaction scheme 12, a compound of formula 4-12-1 is subjected to a Mitsunobu reaction with an alkoxy compound to yield a compound of formula 4-12-2. The compound of formula 4-12-2 is hydrogenated to yield a compound of formula 4-12-3, which is then subjected to an alkylation reaction in the presence of sodium hydride to yield a compound of formula 4-12-4. The resulting compound is reacted with an amine compound to yield a compound of formula 4-12-5, which has a urea structure. Then, the compound of formula 4-12-5 is deprotected under an acidic condition to yield a compound of formula 4-12-6. The compound of formula 4-12-6 is subjected to an alkylation reaction to introduce a substituent therein, and then reacted with hydrazine to yield a compound of formula 4-12-8. The compound of formula 4-12-8 is reacted with difluoroacetic anhydride to yield a compound of formula 4-12-9.

Compound that is prepared according to reaction scheme 12 above is compound 21924.

196

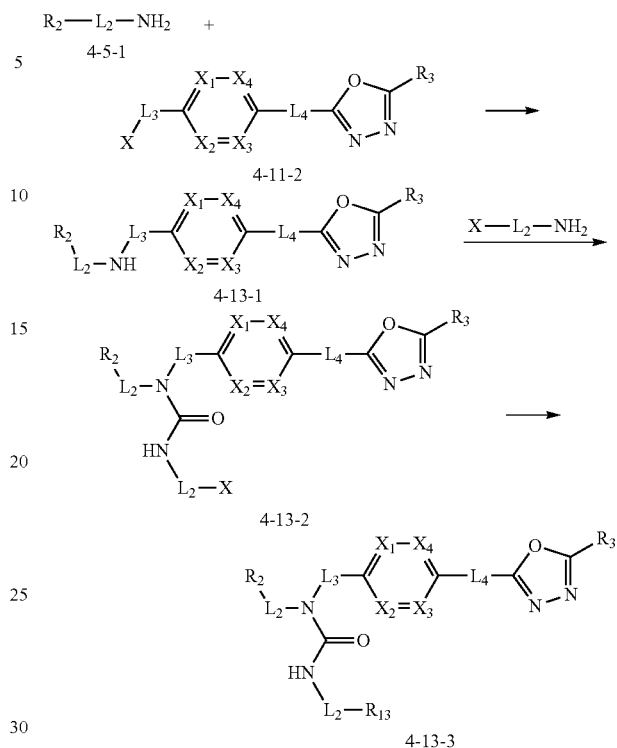

Reaction scheme 13 above shows a method for preparing urea compounds having an aminoalkyl chain structure introduced therein. As shown in reaction scheme 13, an amine compound (formula 4-5-1) is subjected to an alkylation reaction in the presence of sodium hydride to yield a compound of formula 4-13-1. The compound of formula 4-13-1 is reacted with an amine compound and triphosgene to yield a compound of formula 4-13-2, which has a urea structure, after which the compound of formula 4-13-2 is subjected to a substitution reaction with an amine compound, thereby preparing a compound of formula 4-13-3.

Compounds that are prepared according to reaction scheme 13 above are compounds 21956, 21957, 21958, 21982, 21983, 21984, 21985, 21986, 21987, 21988, 21989, 21990, 21991, 21992, 21993, 21994, 21995, 21996, 21997, 21998, 21999, 22000, 22001, 22002, 22003, 22004, 22005, 22006, 22007, 22008, 22009, 22010, 22011, 22012, 22013, 22014, 22015, 22016 and 22017.

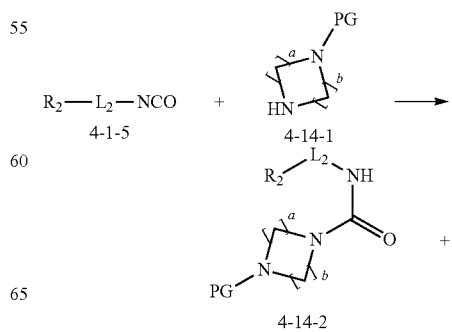

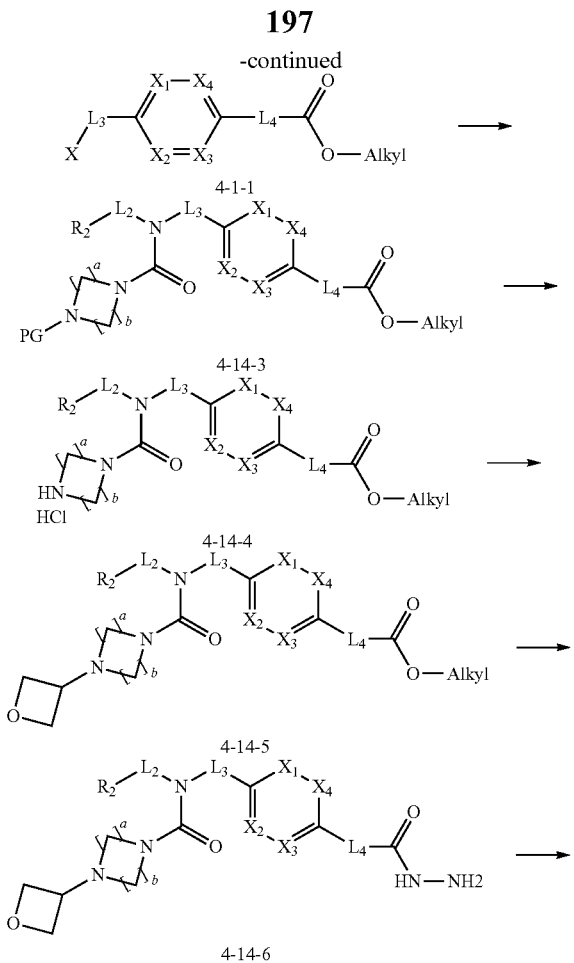

Reaction scheme 14 above shows a method for preparing compounds having an oxetane structure introduced therein. As shown in reaction scheme 14, a compound of formula 4-1-5 is reacted with a compound of formula 4-14-1 to yield a compound of formula 4-14-2, which has a urea structure. The compound of formula 4-14-2 is subjected to a substitution reaction with a compound of formula 4-1-1 to yield a compound of formula 4-14-3. The compound of formula 4-14-3 is deprotected to yield a compound of formula 4-14-4, which is then reacted with oxetanone to yield a compound of formula 4-14-5. The compound of formula 4-14-5 is reacted with hydrazine to yield a compound of formula 4-14-6, which is then trifluoroacetic anhydride or difluoroacetic anhydride, thereby preparing a compound of formula 4-14-7.

Compounds that are prepared according to reaction scheme 14 above are compounds 21936, 21937, 21938, 21939, 21940, 21941, 21942, 21943, 21944, 21945, 21946, 21947, 21948, 21949, 21950, 21951, 21952, 21953, 21954 and 21955.

[Reaction Scheme 15]

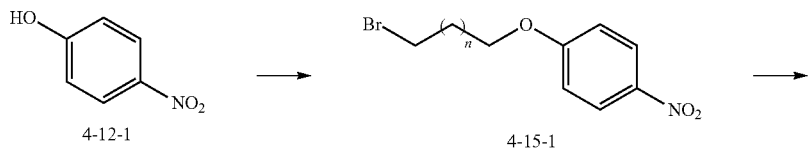

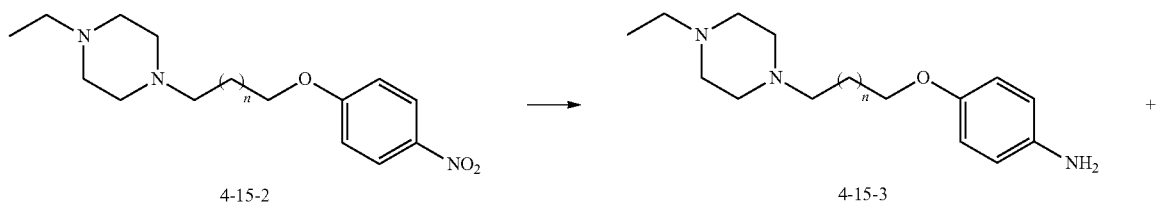

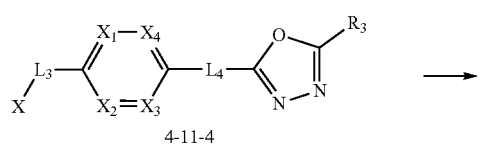

-continued

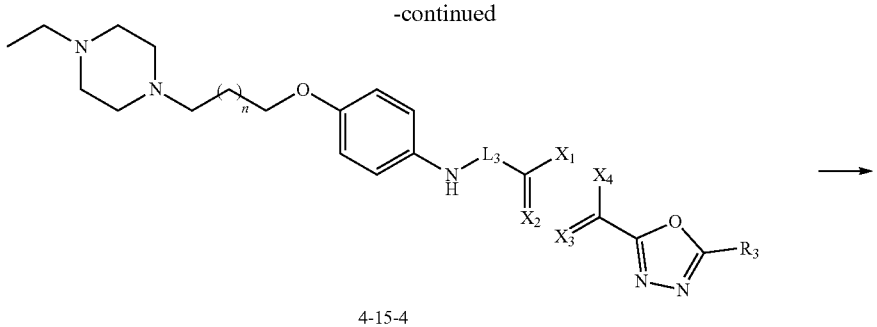

4-15-4

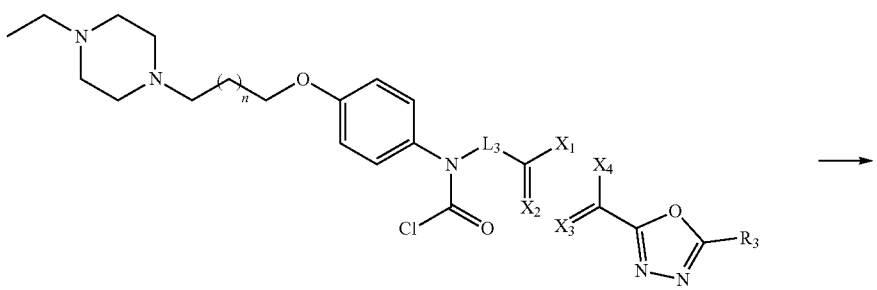

4-15-5

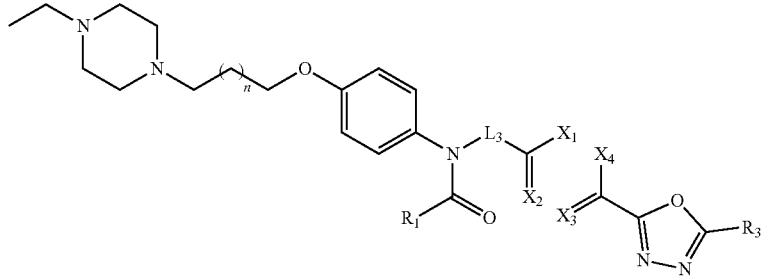

4-15-6

Reaction scheme 15 above shows a method for preparing a urea compound having a heterocycloalkyl structure introduced therein. As shown in reaction scheme 15, a compound of formula 4-12-1 is subjected to a substitution reaction with dibromoalkane to yield a compound of formula 4-15-1. Then, the compound of formula 4-15-1 is subjected to a substitution reaction with ethylpiperazine to yield a compound of formula 4-15-2, which is then hydrogenated to yield a compound of formula 4-15-3. The compound of formula 4-15-3 is subjected to an alkylation reaction in the presence of sodium hydride to yield a compound of formula 4-15-4, which is then reacted with triphosgene to yield a compound of formula 4-15-5. The compound of formula 4-15-5 is subjected to a substitution reaction with an amine compound, thereby preparing a compound of formula 4-15-6.

Compounds that are prepared according to reaction scheme 15 above are compounds 21971, 21972 and 21973.

[Reaction Scheme 16]

R$_2$—L$_2$—NH$_2$   +

4-5-1

-continued

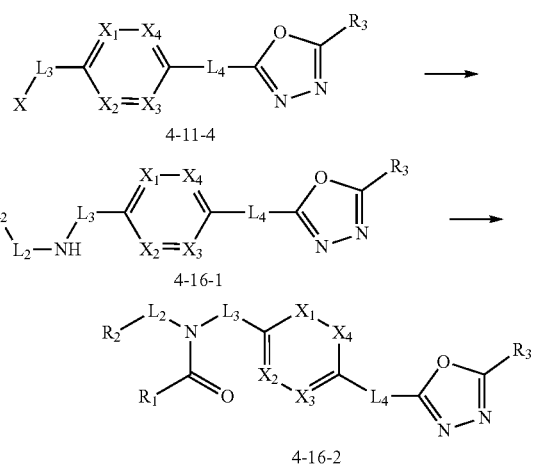

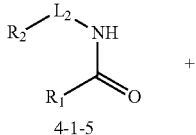

4-1-5

-continued

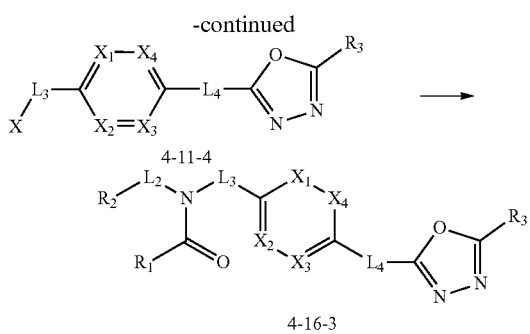

4-11-4

4-16-3

Reaction scheme 16 above shows a method for preparing compounds having a urea structure. As shown in reaction scheme 16, an amine compound (formula 4-5-1) is subjected to an alkylation reaction in the presence of sodium hydride to yield a compound of formula 4-16-1, which is then reacted with amine and triphosgene to yield a compound of formula 4-16-2. Then, the compound of formula 4-11-4 is subjected to an alkylation reaction with a compound of formula 4-1-5 in the presence of sodium hydride, thereby preparing a compound of formula 4-16-3.

Compounds that are prepared according to reaction scheme 16 above are compounds 21979, 21980, 21981, 22018, 22019, 22020 and 22021.

[Reaction Scheme 17]

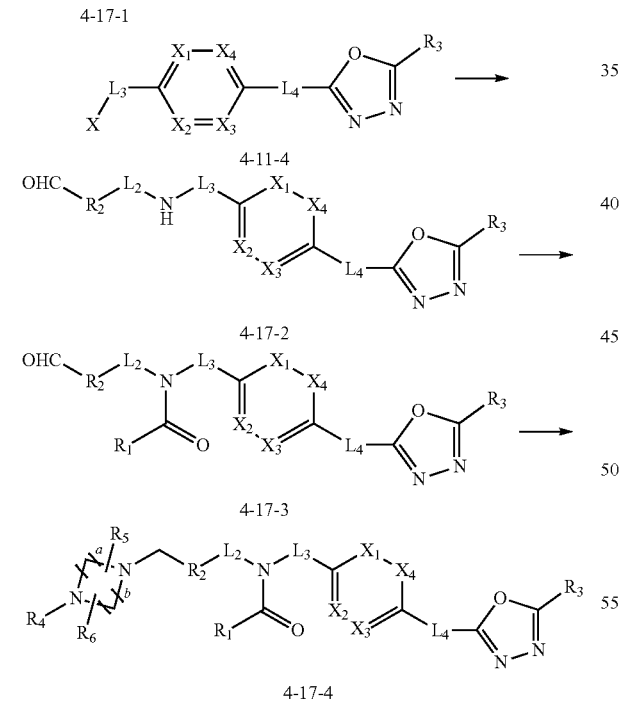

Reaction scheme 17 above shows a method for preparing urea compounds having a heterocycloalkyl structure introduced therein. As shown in reaction scheme 17, a compound of formula 4-17-1 having an aldehyde introduced therein is reacted with a compound of formula 4-11-4 to yield a compound of formula 4-17-2. The compound of formula 4-17-2 is reacted with amine and triphosgene to yield a compound of formula 4-17-3 having a urea structure, after which the compound of formula 4-17-3 is subjected to a reductive amination reaction with an amine compound, thereby preparing a compound of formula 4-17-4.

Compound that is prepared according to reaction scheme 17 above is compound 22024.

[Reaction Scheme 18]

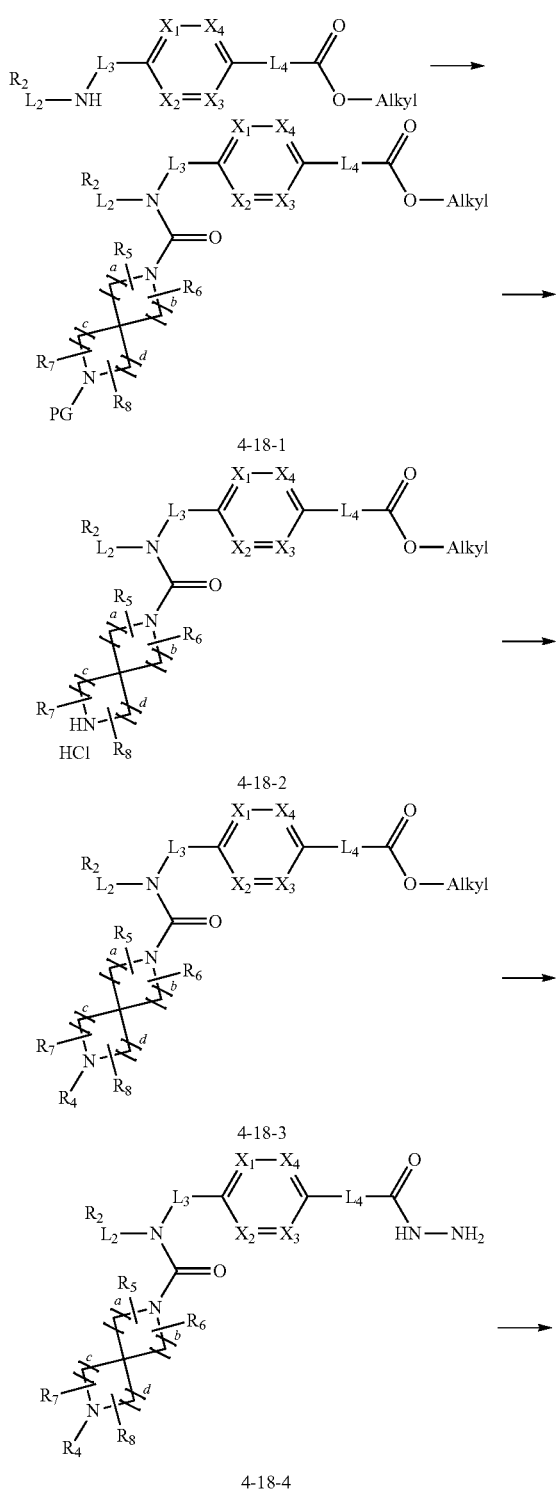

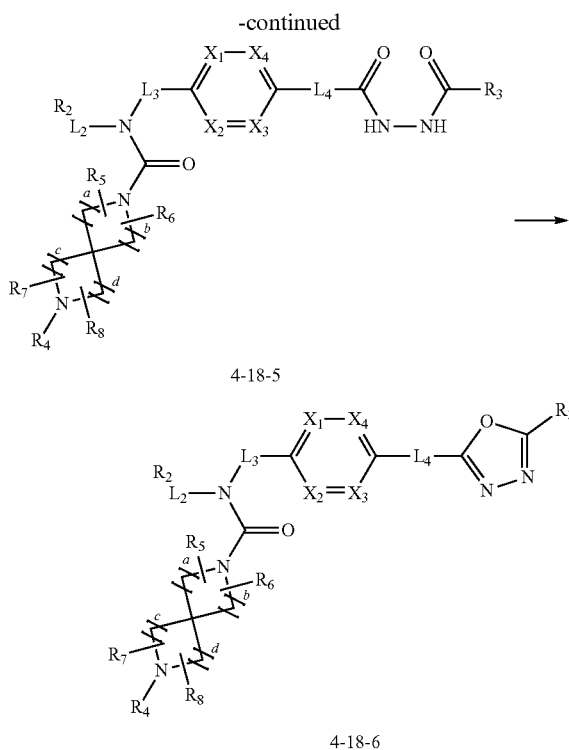

4-18-5

4-18-6

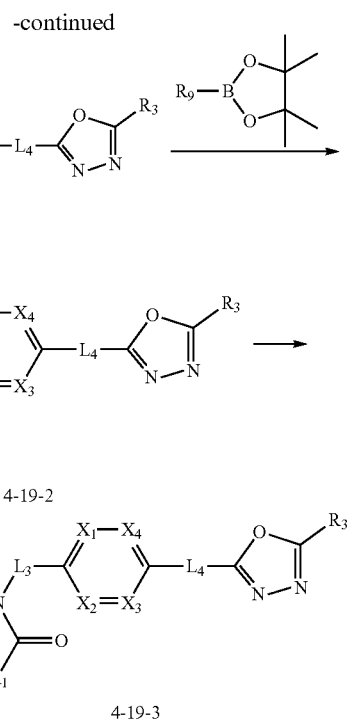

4-19-1

4-19-2

4-19-3

Reaction scheme 18 above shows a method of introducing a substituent into secondary amine. As shown in reaction scheme 18, the compound of formula 4-1-3, synthesized according to reaction scheme 1, is reacted with triphosgene to yield a compound of formula 4-18-1. The compound of formula 4-18-1 is deprotected to yield a compound of formula 4-18-2, which is then subjected to a reductive amination reaction with aldehyde to yield a compound of formula 4-18-3. The compound of formula 4-18-4 is reacted with hydrazine to yield a compound of formula 4-18-4, which is then reacted with trifluoroacetic anhydride or difluoroacetic anhydride to yield a compound of formula 4-18-5. The compound of formula 4-18-5 is reacted with 1-methoxy-N-triethylammoniosulfonyl-methaneimidate (Burgess reagent), thereby preparing a compound of formula 4-18-6.

Compound that is prepared according to reaction scheme 18 above is compound 21765.

[Reaction Scheme 19]

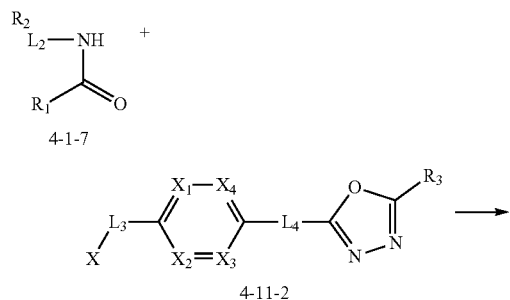

Reaction scheme 19 above shows a method for synthesizing urea compounds having a heterocycloalkyl structure. As shown in reaction scheme 19, the compound of formula 4-1-7, synthesized according to reaction scheme 1, is subjected to an alkylation reaction in the presence of sodium hydride to yield a compound of formula 4-19-1, which is then subjected to a Suzuki reaction with boronic ester to yield a compound of formula 4-19-2. Then, the compound of formula 4-19-2 is subjected to a reduction reaction in the presence of palladium, thereby preparing a compound of formula 4-19-3.

Compound that is prepared according to reaction scheme 18 above is compound 21970.

Compositions Comprising 1,3,4-Oxadiazole Derivative Compounds, the Use Thereof and the Method of Treating Diseases The present invention provides a pharmaceutical composition for preventing or treating histone deacetylase 6 (HDAC6) activity-associated diseases, which contains, as an active ingredient, a compound represented by the following formula I, a stereoisomer thereof or a pharmaceutically acceptable salt thereof:

[Formula I]

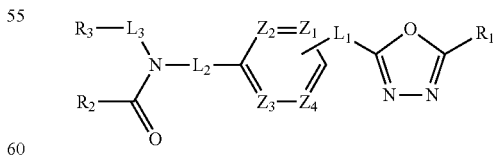

wherein formula I is as defined above.

The pharmaceutical composition according to the present invention exhibits a remarkable effect on the prevention or treatment of histone deacetylase 6 (HDAC6) activity-associated diseases by selectively inhibiting histone deacetylase 6 (HDAC6).

The histone deacetylase 6 (HDAC6) activity-associated diseases include infectious diseases such as prion disease; neoplasms such as benign tumor (e.g. myelodysplastic syndrome) or malignant tumor (e.g. multiple myeloma, lymphoma, leukemia, lung cancer, rectal cancer, colon cancer, prostate cancer, urothelial carcinoma, breast cancer, melanoma, skin cancer, liver cancer, brain cancer, gastric cancer, ovarian Cancer, pancreatic cancer, head and neck cancer, oral cancer, or glioma); endocrine, nutritional and metabolic diseases such as Wilson's disease, amyloidosis or diabetes; mental and behavioral disorders such as depression or Rett's syndrome, and the like; neurological diseases such as atrophy of central nervous system (e.g. Huntington's disease, spinal muscular atrophy (SMA), spinocerebellar ataxia (SCA)), neurodegenerative disease (e.g. Alzheimer's disease), movement disorder (e.g. Parkinson's disease), neuropathy (e.g. hereditary neuropathy (Charcot-Marie-Tooth disease), sporadic neuropathy, inflammatory neuropathy, drug-induced neuropathy), motor neuron diseases (amyotrophic lateral sclerosis (ALS)), or demyelinating diseases of the central nervous system (e.g. multiple sclerosis (MS)), and the like; diseases of the eye and adnexa, such as uveitis; cardiovascular diseases such as atrial fibrillation or stroke and the like; respiratory diseases such as asthma; digestive diseases such as alcoholic liver disease, inflammatory bowel disease, Crohn's disease or ulcerative bowel disease, and the like; diseases of the skin and subcutaneous tissue, such as psoriasis; diseases of the musculoskeletal system and connective tissue, such as rheumatoid arthritis, osteoarthritis or systemic lupus erythematosus (SLE), and the like; or congenital malformations, deformations and chromosomal abnormalities, such as autosomal dominant polycystic kidney disease, as well as disorders or diseases associated with the abnormal function of histone deacetylase.

The pharmaceutically acceptable salt is as described above with respect to a pharmaceutically acceptable salt of the compound represented by formula I according to the present invention.

For administration, the pharmaceutical composition according to the present invention may further contain at least one pharmaceutically acceptable carrier in addition to the compound of formula I, an isomer thereof or a pharmaceutically acceptable salt thereof. The pharmaceutically acceptable carrier that is used in the present invention may be at least one of physiological saline, sterile water, Ringer solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, the composition can be formulated into injectable formulations such as solutions, suspensions, turbid fluid, etc, pills, capsules, granules or tablets using a diluent, a dispersing agent, a surfactant, a binder and a lubricant. Thus, the composition of the present invention may be in the form of patches, liquids, pills, capsules, granules, tablets, suppositories, etc. These formulations can be prepared either by conventional methods that are used for formulation in the art or by the method disclosed in Remington's Pharmaceutical Science (the latest edition), Mack Publishing Company, Easton Pa.

The pharmaceutical composition of the present invention may be administered orally or parenterally (e.g., intravenously, subcutaneously, intraperitoneally or topically) depending on the intended use. The dose of the pharmaceutical composition varies depending on the patient's weight, age, sex, health conditions and diet, the time of administration, the mode of administration, excretion rate, the severity of the disease, and the like. The daily dose of the compound of formula I according to the present invention may be about 1 to 500 mg/kg, preferably 5 to 100 mg/kg, and may be administered once to several times a day.

The pharmaceutical composition of the present invention may further contain, in addition to the compound represented by formula I, a stereoisomer thereof or a pharmaceutically acceptable salt thereof, one or more active ingredients that exhibit medicinal efficacy identical or similar thereto.

The present invention also provides a method for preventing or treating a histone deacetylase-mediated disease, which comprises administering a therapeutically effective amount of the compound represented by formula I, a stereoisomer thereof or a pharmaceutically acceptable salt thereof.

As used herein, the term "therapeutically effective amount" refers to the amount of the compound represented by formula I, which is effective for the prevention or treatment of histone deacetylase 6 activity-associated diseases.

The present invention also provides a method of selectively inhibiting HDAC6, which comprises administering the compound of formula I, a stereoisomer thereof or a pharmaceutically acceptable salt thereof to mammals including humans.

The method of preventing or treating histone deacetylase 6 activity-associated disease according to the present invention includes inhibiting or averting the disease as well as addressing the disease itself, prior to the onset of symptoms by administering the compound represented by formula I. In the management of diseases, the magnitude of a prophylactic or therapeutic dose of a particular active ingredient will vary with the nature and severity of the disease or condition, and may also vary according to the route by which the active ingredient is administered. The dose and the dose frequency will also vary according to the age, body weight, and response of the individual patient. Suitable dosing regimens can be readily selected by those skilled in the art with due consideration of such factors. In addition, the method of preventing or treating histone deacetylase 6 activity-associated disease according to the present invention may further comprise administering a therapeutically effective amount of an additional active agent helpful for the treatment of the disease together with the compound represented by formula I, in which the additional active agent Can exhibit a synergistic effect with the compound of formula I or an assistant effect.

The present invention is also intended to provide the use of the compound represented by formula I, a stereoisomer thereof or a pharmaceutically acceptable salt thereof, for the preparation of a medicament for treating histone deacetylase 6 activity-associated disease. For the preparation of the medicament, the compound represented by formula I may be mixed with a pharmaceutically acceptable adjuvant, diluent, carrier or the like, and combined with other active agents such that the active ingredients can have synergistic effects.

The particulars mentioned in the use, composition and treatment method of the present invention may be appropriately combined unless contradictory to one another.

Advantageous Effects of Invention

The compounds represented by formula I, stereoisomers thereof or pharmaceutically acceptable salts thereof can selectively inhibit HDAC6, and thus exhibit excellent effects on the prevention or treatment of histone deacetylase 6 activity-associated diseases.

MODE FOR THE INVENTION

Hereinafter, preferred examples will be presented to assist in the understanding of the present invention. However, these examples are provided only for a better understanding of the present invention and are not intended to limit the scope of the present invention.

Preparation of 1,3,4-oxadiazole Derivative Compounds

Specific methods for preparing the compounds of formula I are as follows.

Example 1. Compound 21249: N-phenyl-N-(4-(5-(trifluoromethyl)-1,3,4-oxadiazol-2-yl)benzyl)morpholine-4-carboxamide

[Step 1] Methyl 4-((N-phenylmorpholine-4-carboxamido)methyl)benzoate

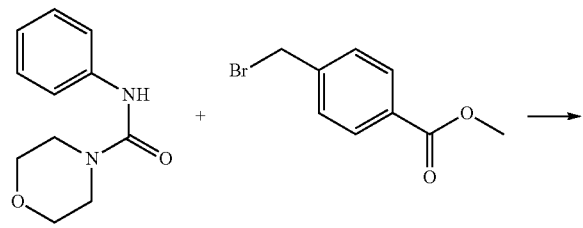

To a stirred solution of N-phenylmorpholine-4-carboxamide (1.000 g, 4.848 mmol) in N,N-dimethylformamide (20 mL) was added at 0° C. methyl 4-(bromomethyl)benzoate (1.222 g, 5.333 mmol). The reaction mixture was stirred at the same temperature for 1 hr, treated at the room temperature with sodium hydride (60.00%, 0.291 g, 7.273 mmol), and stirred for additional 8 hr. Then, water was added to the reaction mixture, followed by extraction with ethyl acetate. The organic layer was washed with brine (saturated aqueous sodium chloride solution), dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound methyl 4-((N-phenylmorpholine-4-carboxamido)methyl)benzoate as Colorless oil (1.400 g, 81.5%).

[Step 2] N-(4-(hydrazinecarbonyl)benzyl)-N-phenylmorpholine-4-carboxamide

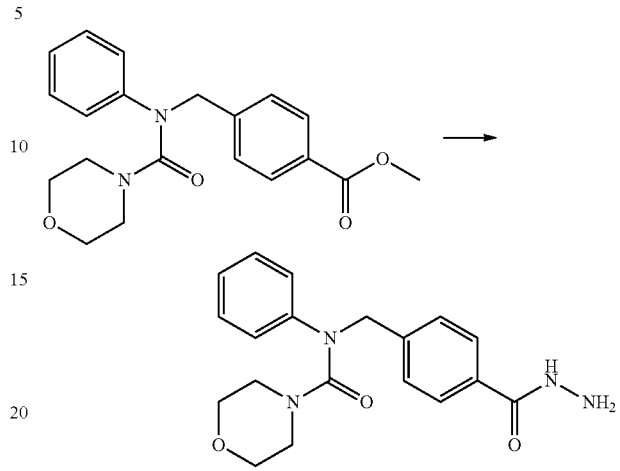

A mixture of methyl 4-((N-phenylmorpholine-4-carboxamido)methyl)benzoate (1.000 g, 2.822 mmol) prepared in Step 1 and hydrazine monohydrate (2.737 mL, 56.432 mmol) in ethanol (5 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-(4-(hydrazinecarbonyl)benzyl)-N-phenylmorpholine-4-carboxamide as Colorless oil (0.700 g, 70.0%).

[Step 3] N-phenyl-N-(4-(2-(2,2,2-trifluoroacetyl)hydrazine-1-carbonyl)benzyl)morpholine-4-carboxamide

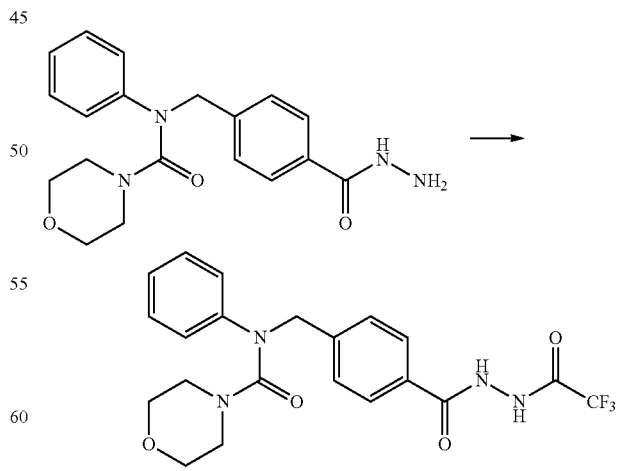

A solution of N-(4-(hydrazinecarbonyl)benzyl)-N-phenylmorpholine-4-carboxamide (0.670 g, 1.890 mmol) prepared in Step 2, trifluoroacetic anhydride (0.236 mL, 1.701 mmol) and triethylamine (0.427 mL, 2.836 mmol) in dichloromethane (10 mL) was stirred at the room temperature for 3 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-phenyl-N-(4-(2-(2,2,2-trifluoroacetyl)hydrazine-1-carbonyl)benzyl)morpholine-4-carboxamide as White solid (0.650 g, 76.3%).

[Step 4] Compound 21249

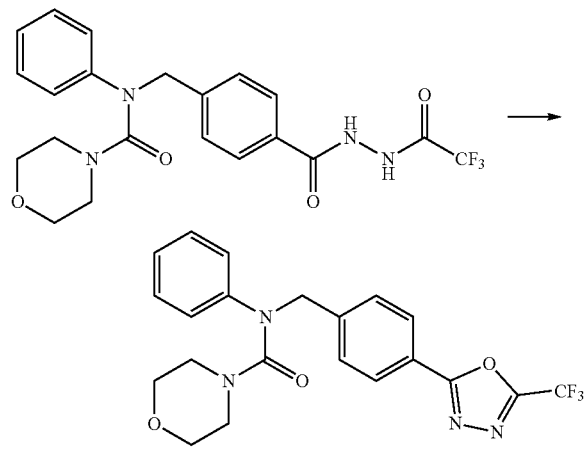

A mixture of N-phenyl-N-(4-(2-(2,2,2-trifluoroacetyl)hydrazine-1-carbonyl)benzyl)morpholine-4-carboxamide (0.440 g, 0.977 mmol) prepared in Step 3 and 1-methoxy-N-triethylammoniosulfonyl-methanimidate (Burgess reagent, 0.303 g, 1.270 mmol) in tetrahydrofuran (10 mL) was heated at 150° C. for 30 min under the microwaves, and cooled to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-phenyl-N-(4-(5-(trifluoromethyl)-1,3,4-oxadiazol-2-yl)benzyl)morpholine-4-carboxamide as Colorless oil (0.280 g, 66.3%).

$^1$H NMR (400 MHz, CDCl$_3$) δ 8.04-8.02 (m, 2H), 7.51-7.48 (m, 2H), 7.35-7.30 (m, 2H), 7.16-7.07 (m, 3H), 4.96 (s, 2H), 3.50 (t, 4H, J=4.8 Hz), 3.26 (t, 4H, J=4.8 Hz) LRMS (E S) m/z 433.35 (M$^+$+1).

Example 2. Compound 21285: 4-methyl-N-phenyl-N-(4-(5-(trifluoromethyl)-1,3,4-oxadiazol-2-yl)benzyl)piperazine-1-carboxamide

[Step 1] Methyl 4-((4-methyl-N-phenylpiperazine-1-carboxamido)methyl)benzoate

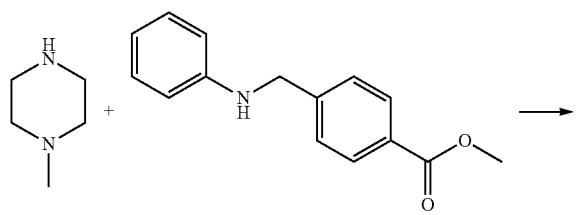

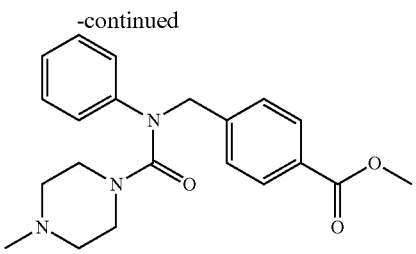

To a stirred solution of methyl 4-((phenylamino)methyl)benzoate (0.472 g, 1.957 mmol) in dichloromethane (10 mL) were added at 0° C. triphosgene (0.464 g, 1.565 mmol) and N,N-diisopropylethylamine (1.704 mL, 9.783 mmol). The reaction mixture was stirred at the same temperature for 30 min, treated at the room temperature with 1-methylpiperazine (0.237 g, 2.348 mmol), and stirred for additional 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound methyl 4-((4-methyl-N-phenylpiperazine-1-carboxamido)methyl)benzoate as Yellow oil (0.496 g, 69.0%).

[Step 2] N-(4-(hydrazinecarbonyl)benzyl)-4-methyl-N-phenylpiperazine-1-carboxamide

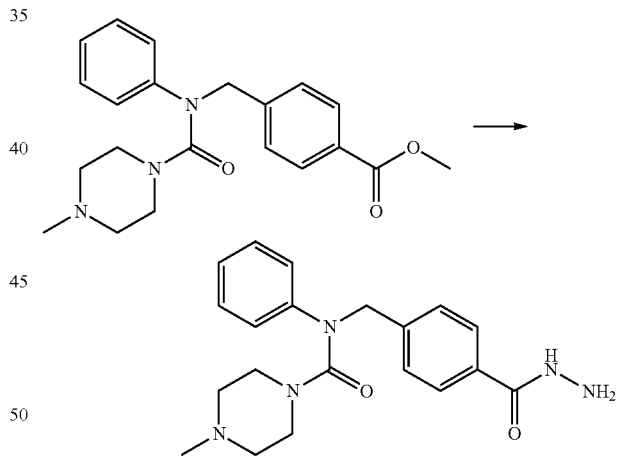

A mixture of methyl 4-((4-methyl-N-phenylpiperazine-1-carboxamido)methyl)benzoate (0.496 g, 1.350 mmol) prepared in Step 1 and hydrazine monohydrate (1.275 mL, 26.998 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-(hydrazinecarbonyl)benzyl)-4-methyl-N-phenylpiperazine-1-carboxamide as Yellow oil (0.323 g, 65.1%).

[Step 3] 4-Methyl-N-phenyl-N-(4-(2-(2,2,2-trifluoroacetyl)hydrazine-1-carbonyl)benzyl)piperazine-1-carboxamide


A solution of N-(4-(hydrazinecarbonyl)benzyl)-4-methyl-N-phenylpiperazine-1-carboxamide (0.323 g, 0.879 mmol) prepared in Step 2, triethylamine (0.184 mL, 1.319 mmol) and trifluoroacetic anhydride (0.110 mL, 0.791 mmol) in dichloromethane (10 mL) was stirred at the room temperature for 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 15%) to give the title compound 4-methyl-N-phenyl-N-(4-(2-(2,2,2-trifluoroacetyl)hydrazine-1-carbonyl)benzyl)piperazine-1-carboxamide as Colorless oil (0.139 g, 34.1%).

[Step 4] Compound 21285


A mixture of 4-methyl-N-phenyl-N-(4-(2-(2,2,2-trifluoroacetyl)hydrazine-1-carbonyl)benzyl)piperazine-1-carboxamide (0.139 g, 0.300 mmol) prepared in Step 3 and 1-methoxy-N-triethylammoniosulfonyl-methanimidate (Burgess reagent, 0.107 g, 0.450 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound 4-methyl-N-phenyl-N-(4-(5-(trifluoromethyl)-1,3,4-oxadiazol-2-yl)benzyl)piperazine-1-carboxamide as brown oil (0.100 g, 74.8%).

$^1$H NMR (400 MHz, CDCl$_3$) δ 8.05-5.03 (m, 2H), 7.50 (d, 2H, J=8.3 Hz), 7.34-7.30 (m, 2H), 7.14 (t, 1H, J=7.4 Hz), 7.08-7.05 (m, 2H), 4.97 (s, 2H), 3.42-3.39 (m, 4H), 2.38-2.34 (m, 7H) LRMS (ES) m/z 446.1 (M$^+$+1).

Example 3. Compound 21318: N-(2-fluoro-4-(5-(trifluoromethyl)-1,3,4-oxadiazol-2-yl)benzyl)-N-phenylmorpholine-4-carboxamide

[Step 1] Methyl 3-fluoro-4-((N-phenylmorpholine-4-carboxamido)methyl)benzoate

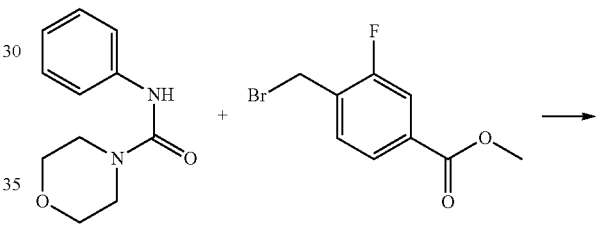

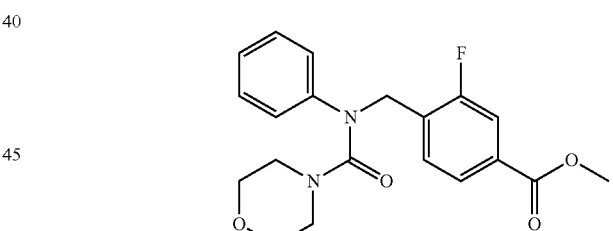

A solution of N-phenylmorpholine-4-carboxamide (0.300 g, 1.455 mmol) and sodium hydride (60.00%, 0.058 g, 1.455 mmol) in N,N-dimethylformamide (10 mL) was mixed at the room temperature with methyl 4-(bromomethyl)-3-fluorobenzoate (0.359 g, 1.455 mmol). The reaction mixture was stirred at the same temperature for 16, hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=10% to 30%) to give the title compound methyl 3-fluoro-4-((N-phenylmorpholine-4-carboxamido)methyl)benzoate as yellow solid (0.347 g, 64.1%).

[Step 2] N-(2-fluoro-4-(hydrazinecarbonyl)benzyl)-N-phenylmorpholine-4-carboxamide

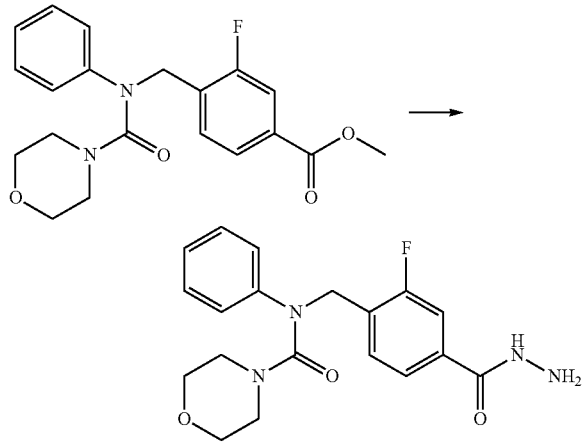

A mixture of methyl 3-fluoro-4-((N-phenylmorpholine-4-carboxamido)methyl)benzoate (0.347 g, 0.932 mmol) prepared in Step 1 and hydrazine monohydrate (0.880 mL, 18.636 mmol) in ethanol (10 mL) was heated at 100° C. for 1 hr under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(hydrazinecarbonyl)benzyl)-N-phenylmorpholine-4-carboxamide as white solid (0.353 g, 101.7%).

[Step 3] N-(2-fluoro-4-(2-(2,2,2-trifluoroacetyl)hydrazine-1-carbonyl)benzyl)-N-phenylmorpholine-4-carboxamide

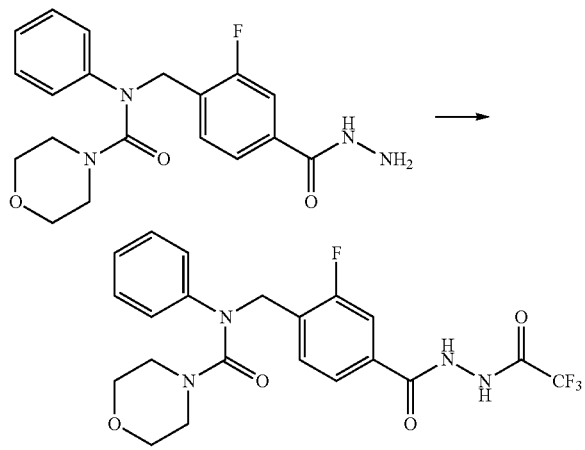

A solution of N-(2-fluoro-4-(hydrazinecarbonyl)benzyl)-N-phenylmorpholine-4-carboxamide (0.353 g, 0.948 mmol) and triethylamine (0.262 mL, 1.896 mmol) in dichloromethane (4 mL) was mixed at the room temperature with trifluoroacetic anhydride (0.148 mL, 0.853 mmol). The reaction mixture was stirred at the same temperature for 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(2-(2,2,2-trifluoroacetyl)hydrazine-1-carbonyl)benzyl)-N-phenylmorpholine-4-carboxamide as white solid (0.446 g, 100.4%).

[Step 4] Compound 21318

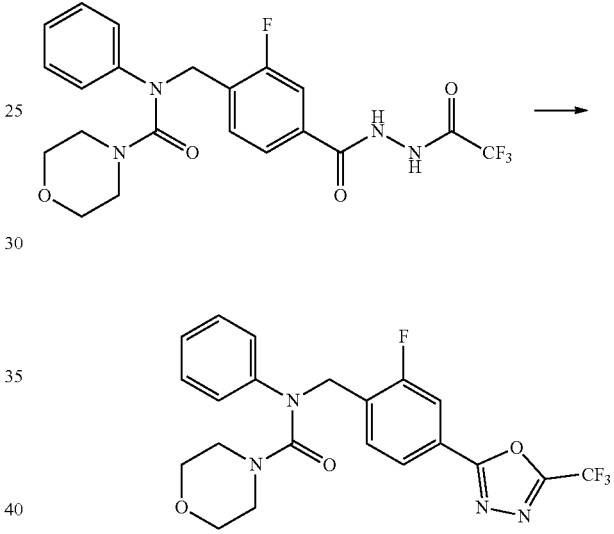

A mixture of N-(2-fluoro-4-(2-(2,2,2-trifluoroacetyl)hydrazine-1-carbonyl)benzyl)-N-phenylmorpholine-4-carboxamide (0.100 g, 0.213 mmol) prepared in Step 3 and 1-methoxy-N-triethylammoniosulfonyl-methanimidate (Burgess reagent, 0.076 g, 0.320 mmol) in tetrahydrofuran (2 mL) was heated at 150° C. for 30 min under the microwaves, and cooled down to the room temperature to terminate the reaction. Then, water was added to the reaction mixture, followed by extraction with dichloromethan. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-(2-fluoro-4-(5-(trifluoromethyl)-1,3,4-oxadiazol-2-yl)benzyl)-N-phenylmorpholine-4-carboxamide as colorless oil (0.053 g, 54.7%).

$^1$H NMR (400 MHz, CDCl$_3$) δ 7.85 (dd, 1H, J=8.0, 1.7 Hz), 7.77-7.66 (m, 2H), 7.37-7.26 (m, 2H), 7.18-7.07 (m, 3H), 4.98 (s, 2H), 3.52-3.44 (m, 4H), 3.24 (dd, 4H, J=5.5, 4.0 Hz); LRMS (ES) m/z 451.33 (M$^+$+1).

215

Example 4. Compound 21319: N-(3-fluoro-4-(5-(trifluoromethyl)-1,3,4-oxadiazol-2-yl)benzyl)-N-phenylmorpholine-4-carboxamide

[Step 1] Methyl 2-fluoro-4-((phenylamino)methyl)benzoate

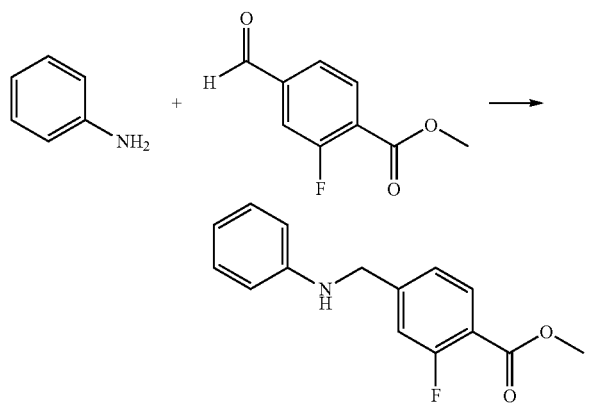

A solution of aniline (0.200 g, 2.148 mmol), methyl 2-fluoro-4-formylbenzoate (0.411 g, 2.255 mmol) and sodium triacetoxyborohydride (0.683 g, 3.221 mmol) in dichloromethane (10 mL) was stirred at the room temperature for 16 hr. Then, water was added to the reaction mixture, followed by extraction with dichloromethan. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=10% to 30%) to give the title compound methyl 2-fluoro-4-((phenylamino) methyl)benzoate as brown solid (0.162 g, 29.1%).

[Step 2] Methyl 2-fluoro-4-((N-phenylmorpholine-4-carboxamido)methyl)benzoate

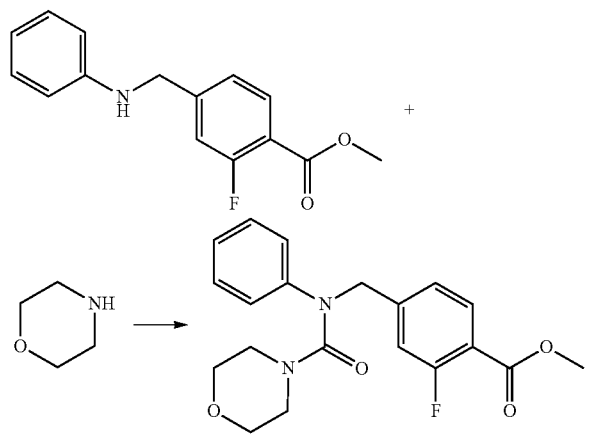

To a stirred solution of methyl 2-fluoro-4-((phenylamino) methyl)benzoate (0.362 g, 1.396 mmol) prepared in Step 1 in dichloromethane (4 mL) were added at the room temperature triphosgene (0.207 g, 0.698 mmol) and N,N-diisopropylethylamine (1.449 mL, 8.377 mmol), and stirred at the same temperature for 2 hr. The reaction mixture was treated with morpholine (0.134 mL, 1.536 mmol), and stirred at the same temperature for 2 hr. Then, water was added to the reaction mixture, followed by extraction with dichloromethan. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; ethyl acetate/hexane=20% to 50%) to give the title compound methyl 2-fluoro-4-((N-phenylmorpholine-4-carboxamido)methyl)benzoate as white solid (0.435 g, 83.7%).

[Step 3] N-(3-fluoro-4-(hydrazinecarbonyl)benzyl)-N-phenylmorpholine-4-carboxamide

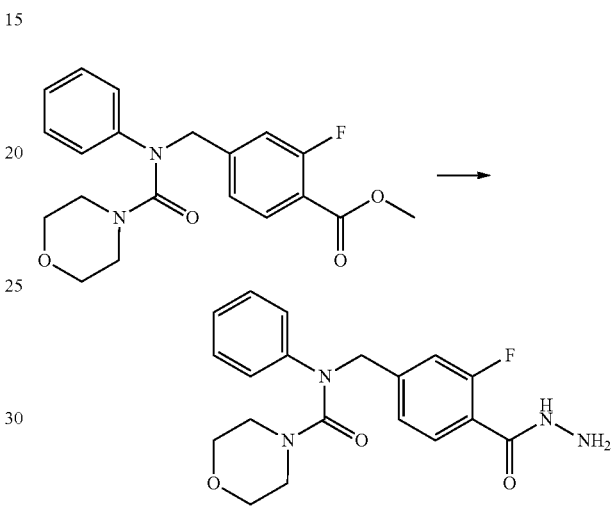

A mixture of methyl 2-fluoro-4-((N-phenylmorpholine-4-carboxamido)methyl)benzoate (0.435 g, 1.169 mmol) prepared in Step 2 and hydrazine monohydrate (1.104 mL, 23.373 mmol) in ethanol (10 mL) was heated at 100° C. for 1 hr under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-(3-fluoro-4-(hydrazinecarbonyl)benzyl)-N-phenylmorpholine-4-carboxamide as white solid (0.301 g, 69.1%).

[Step 4] N-(3-fluoro-4-(2-(2,2,2-trifluoroacetyl)hydrazine-1-carbonyl)benzyl)-N-phenylmorpholine-4-carboxamide

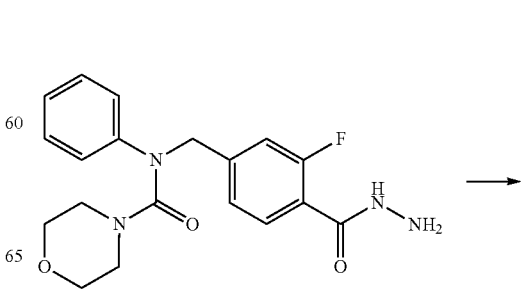

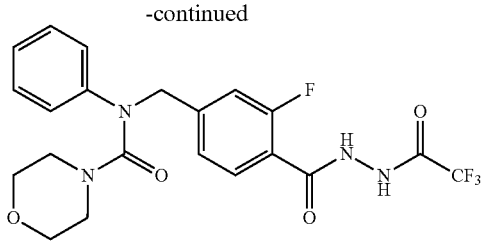

A solution of N-(3-fluoro-4-(hydrazinecarbonyl)benzyl)-N-phenylmorpholine-4-carboxamide (0.301 g, 0.808 mmol) prepared in Step 3 and triethylamine (0.223 mL, 1.616 mmol) in dichloromethane (4 mL) was mixed at the room temperature with trifluoroacetic anhydride (0.126 mL, 0.727 mmol). The reaction mixture was stirred at the same temperature for 4 hr. Then, water was added to the reaction mixture, followed by extraction with dichloromethan. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(3-fluoro-4-(2-(2,2,2-trifluoroacetyl) hydrazine-1-carbonyl)benzyl)-N-phenylmorpholine-4-carboxamide as colorless oil (0.346 g, 91.5%).

[Step 5] Compound 21319

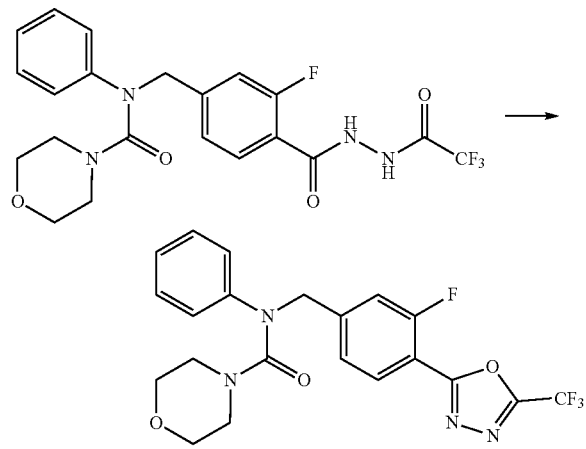

A mixture of N-(3-fluoro-4-(2-(2,2,2-trifluoroacetyl)hydrazine-1-carbonyl)benzyl)-N-phenylmorpholine-4-carboxamide (0.100 g, 0.213 mmol) prepared in Step 4 and 1-methoxy-N-triethylammoniosulfonyl-methanimidate (Burgess reagent, 0.076 g, 0.320 mmol) in tetrahydrofuran (2 mL) was heated at 150° C. for 30 min under the microwaves, and cooled down to the room temperature to terminate the reaction. Then, water was added to the reaction mixture, followed by extraction with dichloromethan. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-(3-fluoro-4-(5-(trifluoromethyl)-1,3,4-oxadiazol-2-yl)benzyl)-N-phenylmorpholine-4-carboxamide as colorless oil (0.070 g, 72.4%).

$^1$H NMR (400 MHz, CDCl$_3$) δ 8.00 (dd, 1H, J=8.3, 7.2 Hz), 7.37-7.28 (m, 3H), 7.25 (m, 1H), 7.14 (m, 1H), 7.11-7.03 (m, 2H), 4.92 (s, 2H), 3.49 (dd, 4H, J=5.7, 3.8 Hz), 3.25 (dd, 4H, J=5.5, 4.1 Hz); LRMS (ES) m/z 451.4 (M$^+$+1).

Example 5. Compound 21325: N-(4-(5-(difluoromethyl)-1,3,4-oxadiazol-2-yl)benzyl)-N-phenylmorpholine-4-carboxamide

[Step 1] N-(4-(2-(2,2-difluoroacetyl)hydrazine-1-carbonyl)benzyl)-N-phenylmorpholine-4-carboxamide

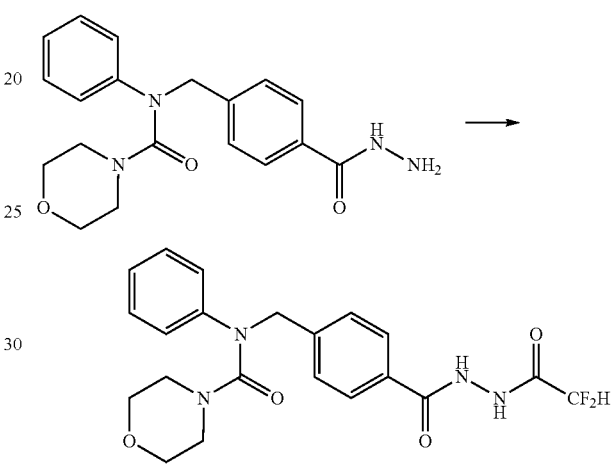

A solution of N-(4-(hydrazinecarbonyl)benzyl)-N-phenylmorpholine-4-carboxamide (0.169 g, 0.477 mmol) prepared in Step 2 of Example 1, difluoroacetic anhydride (0.056 mL, 0.429 mmol) and triethylamine (0.099 mL, 0.715 mmol) in dichloromethane (10 mL) was stirred at the room temperature for 3 hr. Then, water was added to the reaction mixture, followed by extraction with dichloromethan. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-(2-(2,2-difluoroacetyl)hydrazine-1-carbonyl)benzyl)-N-phenylmorpholine-4-carboxamide as Colorless oil (0.140 g, 67.9%).

[Step 2] Compound 21325

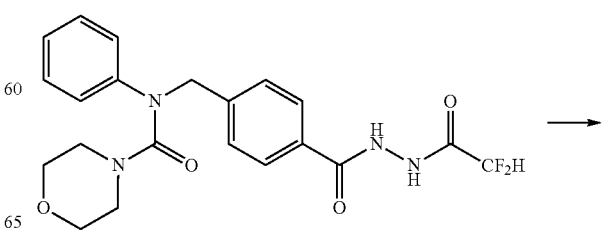

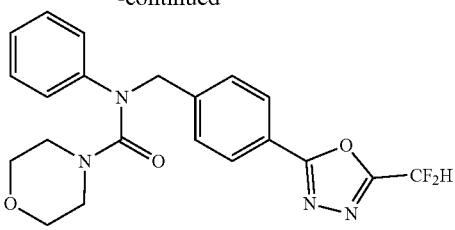

A mixture of N-(4-(2-(2,2-difluoroacetyl)hydrazine-1-carbonyl)benzyl)-N-phenylmorpholine-4-carboxamide (0.140 g, 0.324 mmol) prepared in Step 1 and 1-methoxy-N-triethylammoniosulfonyl-methanimidate (Burgess reagent, 0.116 g, 0.486 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-(5-(difluoromethyl)-1,3,4-oxadiazol-2-yl)benzyl)-N-phenylmorpholine-4-carboxamide as Colorless oil (0.110 g, 82.0%).

$^1$H NMR (400 MHz, CDCl$_3$) δ 8.04 (d, 2H, J=8.4 Hz), 7.49 (d, 2H, J=8.5 Hz), 7.33 (t, 2H, J=7.9 Hz), 7.14 (t, 1H, J=7.5 Hz), 7.09 (d, 2H, J=7.5 Hz), 7.05-7.67 (m, 1H), 4.98 (s, 2H), 3.51 (t, 4H, J=4.6 Hz), 3.27 (t, 4H, J=4.6 Hz); LRMS (ES) m/z 415.1 (M$^+$+1).

Example 6. Compound 21327: N-phenyl-N-(4-(2-(5-(trifluoromethyl)-1,3,4-oxadiazol-2-yl)ethyl)benzyl)morpholine-4-carboxamide

[Step 1] Methyl (E)-3-(4-((N-phenylmorpholine-4-carboxamido)methyl)phenyl)acrylate

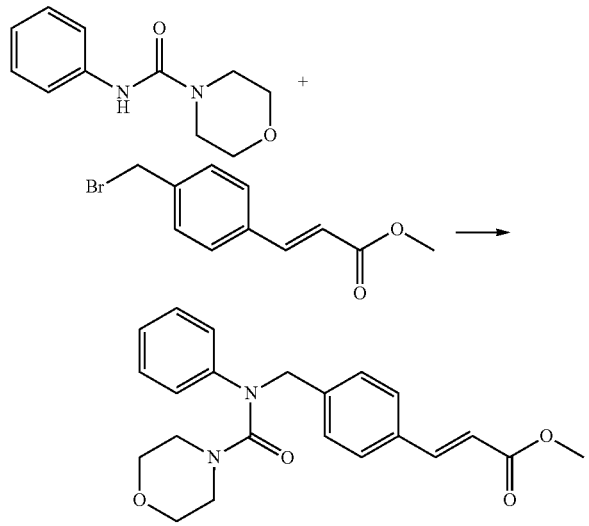

A solution of N-phenylmorpholine-4-carboxamide (1.000 g, 4.848 mmol) and sodium hydride (60.00%, 0.291 g, 7.273 mmol) in N,N-dimethylformamide (20 mL) was stirred at 0° C. for 20 min, and mixed with methyl (E)-3-(4-(bromomethyl)phenyl)acrylate (1.299 g, 5.091 mmol). The reaction mixture was stirred at the room temperature for additional 3 hr. Then, aqueous 1N-sodium bicarbonate solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 40 g cartridge; ethyl acetate/hexane=0% to 40%) to give the title compound methyl (E)-3-(4-((N-phenylmorpholine-4-carboxamido)methyl)phenyl)acrylate as yellow solid (0.855 g, 46.4%).

[Step 2] Methyl 3-(4-((N-phenylmorpholine-4-carboxamido)methyl)phenyl)propanoate

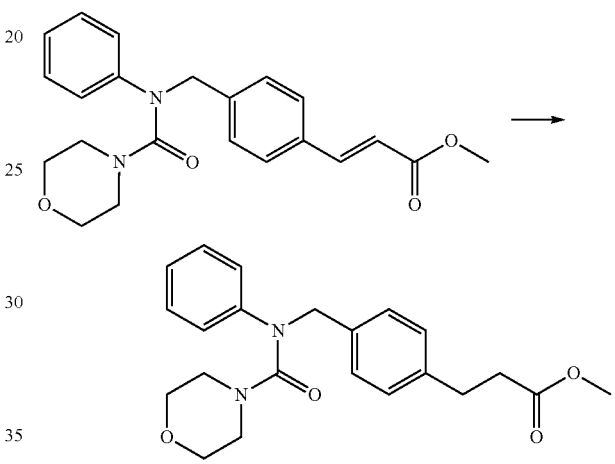

Methyl (E)-3-(4-((N-phenylmorpholine-4-carboxamido)methyl)phenyl)acrylate (0.423 g, 1.112 mmol) prepared in Step 1 and Pd/C (0.043 g) were dissolved in methanol (5 mL) at the room temperature and stirred at the same temperature under the hydrogen atmosphere (H2 balloon) for 16 hr. The reaction mixture was filtered through a celite pad to remove, solids, and the filtrate was concentrated under the reduced pressure to remove the solvent. The concentrate was purified and concentrated by column chromatography (SiO$_2$, 12 g cartridge; ethyl acetate/hexane=0% to 40%) to give the title compound methyl 3-(4-((N-phenylmorpholine-4-carboxamido)methyl)phenyl)propanoate as white solid (0.365 g, 85.8%).

[Step 3] N-(4-(3-hydrazinyl-3-oxopropyl)benzyl)-N-phenylmorpholine-4-carboxamide

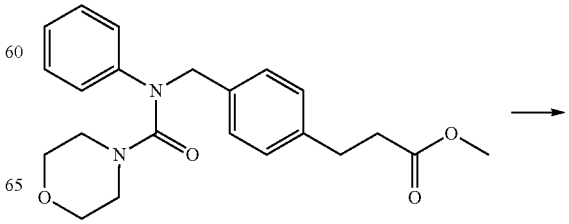

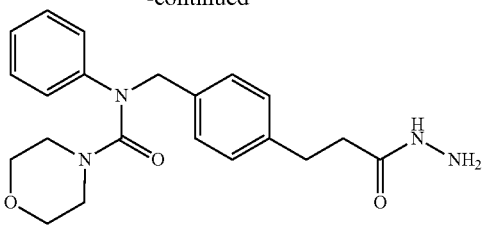

A mixture of methyl 3-(4-((N-phenylmorpholine-4-carboxamido)methyl)phenyl)propanoate (0.365 g, 0.954 mmol) prepared in Step 2 and hydrazine monohydrate (0.901 mL, 19.087 mmol) in ethanol (10 mL) was heated at 120° C. for 1 hr under the microwaves, and cooled down to the room temperature to terminate the reaction. Then, aqueous 1N-sodium bicarbonate solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 5%) to give the title compound N-(4-(3-hydrazinyl-3-oxopropyl)benzyl)-N-phenylmorpholine-4-carboxamide as colorless oil (0.250 g, 68.5%).

[Step 4] N-(4-(3-oxo-3-(2-(2,2,2-trifluoroacetyl)hydrazinyl)propyl)benzyl)-N-phenylmorpholine-4-carboxamide

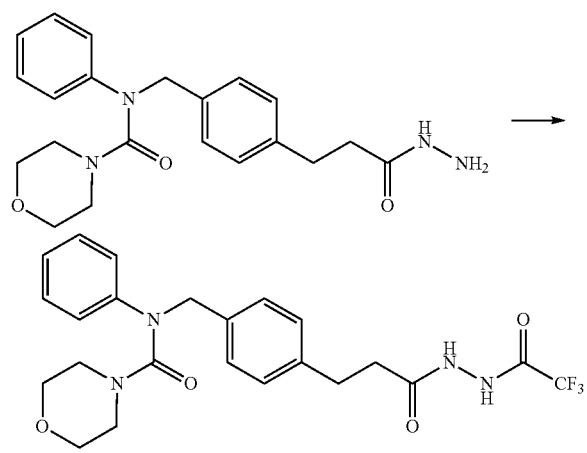

A solution of N-(4-(3-hydrazinyl-3-oxopropyl)benzyl)-N-phenylmorpholine-4-carboxamide (0.250 g, 0.654 mmol) prepared in Step 3, triethylamine (0.136 mL, 0.980 mmol) and trifluoroacetic anhydride (0.082 mL, 0.588 mmol) in dichloromethane (3 mL) was stirred at the room temperature for 16 hr. Then, aqueous 1N-sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 5%) to give the title compound N-(4-(3-oxo-3-(2-(2,2,2-trifluoroacetyl)hydrazinyl)propyl)benzyl)-N-phenylmorpholine-4-carboxamide as white solid (0.179 g, 57.2%).

[Step 5] Compound 21327

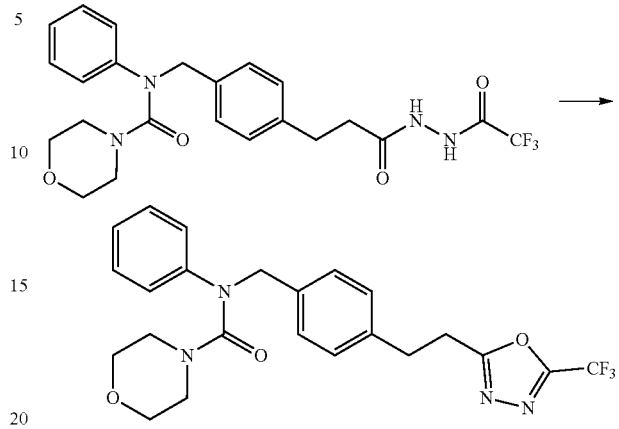

A mixture of N-(4-(3-oxo-3-(2-(2,2,2-trifluoroacetyl)hydrazinyl)propyl)benzyl)-N-phenylmorpholine-4-carboxamide (0.167 g, 0.349 mmol) prepared in Step 4 and 1-methoxy-N-triethylammoniosulfonyl-methanimidate (Burgess reagent, 0.125 g, 0.524 mmol) in tetrahydrofuran (3 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 4 g cartridge; ethyl acetate/hexane=0% to 40%) to give the title compound N-phenyl-N-(4-(2-(5-(trifluoromethyl)-1,3,4-oxadiazol-2-yl)ethyl)benzyl)morpholine-4-carboxamide as colorless oil (0.136 g, 84.6%).

$^1$H NMR (400 MHz, CDCl$_3$) δ 7.30-7.26 (m, 2H), 7.22 (d, 2H, J=8.0 Hz), 7.12-7.03 (m, 5H), 4.82 (s, 2H), 3.47-3.45 (m, 4H), 3.25-3.11 (m, 8H); LRMS (ES) m/z 461.0 (M$^+$+1):

Example 7. Compound 21329: N-phenyl-N-(3-(5-(trifluoromethyl)-1,3,4-oxadiazol-2-yl)benzyl)morpholine-4-carboxamide

[Step 1] Methyl 3-((N-phenylmorpholine-4-carboxamido)methyl)benzoate

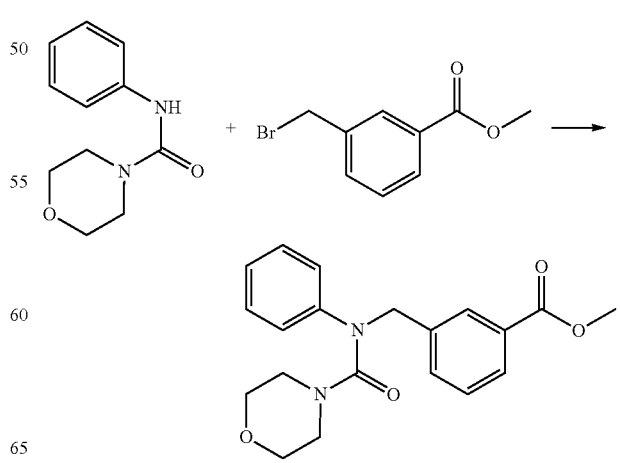

A solution of N-phenylmorpholine-4-carboxamide (0.500 g, 2.424 mmol) and sodium hydride (60.00%, 0.107 g, 2.667 mmol) in N,N-dimethylformamide (30 mL) was mixed at 0° C. with methyl 3-(bromomethyl)benzoate (0.666 g, 2.909 mmol), and stirred at the same temperature for 30 min. The reaction mixture was stirred at the same temperature for additional 2 hr, quenched at 0° C. by the addition of saturated aqueous sodium bicarbonate solution (5 mL, 10 min stirring), and concentrated under the reduced pressure to remove the solvent. The concentrate was purified and concentrated by column chromatography (SiO₂, 12 g cartridge; ethyl acetate/hexane=10% to 70%) to give the title compound methyl 3-((N-phenylmorpholine-4-carboxamido)methyl)benzoate as pale yellow oil (0.794 g, 92.4%).

[Step 2] N-(3-(hydrazinecarbonyl)benzyl)-N-phenylmorpholine-4-carboxamide

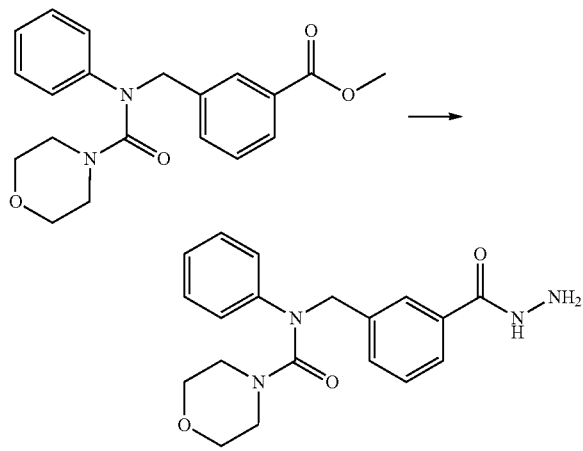

Methyl 3-((N-phenylmorpholine-4-carboxamido)methyl)benzoate (0.600 g, 1.693 mmol) prepared, in Step 1 and hydrazine monohydrate (1.646 mL, 33.859 mmol) in ethanol (10 mL) was mixed at the room temperature and then heated at 120° C. under the microwaves for 1 hr, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-(3-(hydrazinecarbonyl)benzyl)-N-phenylmorpholine-4-carboxamide as pale yellow oil (0.389 g, 64.8%).

[Step 3] N-phenyl-N-(3-(2-(2,2,2-trifluoroacetyl)hydrazine-1-carbonyl)benzyl)morpholine-4-carboxamide

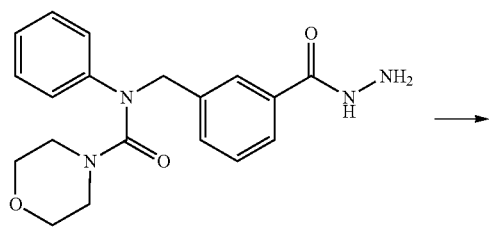

-continued

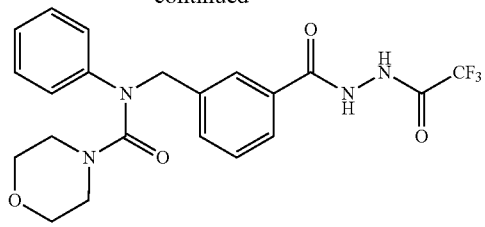

A solution of N-(3-(hydrazinecarbonyl)benzyl)-N-phenylmorpholine-4-carboxamide (0.400 g, 1.129 mmol) prepared in Step 2 and triethylamine (0.235 mL, 1.693 mmol) in dichloromethane (10 mL) was mixed at the room temperature with trifluoroacetic anhydride (0.141 mL, 1.016 mmol). The reaction mixture was stirred at the same temperature for 5 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 10%) to give the title compound N-phenyl-N-(3-(2-(2,2,2-trifluoroacetyl)hydrazine-1-carbonyl)benzyl)morpholine-4-carboxamide as white solid (0.412 g, 81.0%).

[Step 4] Compound 21329

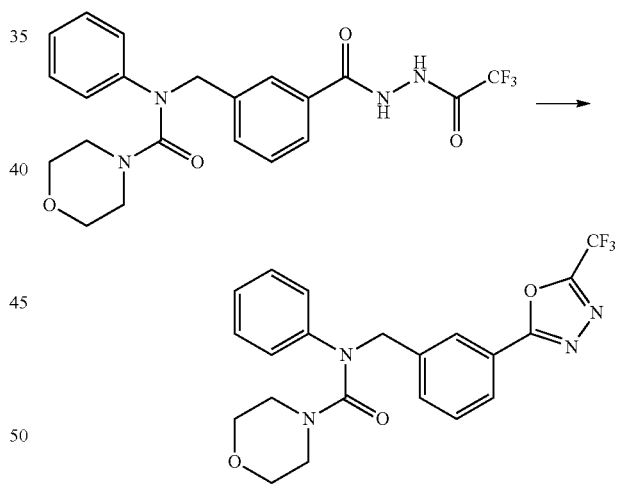

N-phenyl-N-(3-(2-(2,2,2-trifluoroacetyl)hydrazine-1-carbonyl)benzyl)morpholine-4-carboxamide (0.500 g, 1.110 mmol) prepared in Step 3 and 1-methoxy-N-triethylammoniosulfonyl-methanimidate (Burgess reagent, 0.397 g, 1.665 mmol) in tetrahydrofuran (10 mL) was mixed at the room temperature and then heated at 150° C. under the microwaves for 30 min, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound N-phenyl- N-(3-(5-(trifluoromethyl)-1,3,4-oxadiazol-2-yl)benzyl)morpholine-4-carboxamide as colorless oil (0.098 g, 20.4%).

¹H NMR (400 MHz, CDCl₃) δ 8.03 (s, 1H), 7.99 (d, 1H, s=8.1 Hz), 7.61 (d, 1H, J=7.8 Hz), 7.50 (t, 1H, J=7.7 Hz), 7.34 (t, 2H, J=7.7 Hz), 7.15 (t, 1H, J=7.4 Hz), 7.10 (d, 2H, J=8.5 Hz), 4.97 (s, 2H), 3.52 (t, 4H, J=4.7 Hz), 3.28 (t, 4H, J=4.7 Hz): LRMS (ESI) m/z 433.2 (M⁺+H).

Example 8. Compound 21333: N-phenyl-N-((6-(5-(trifluoromethyl)-1,3,4-oxadiazol-2-yl)pyridin-3-yl)methyl)morpholine-4-carboxamide

[Step 1] N-phenyl-N-((6-(2-(2,2,2-trifluoroacetyl)hydrazine-1-carbonyl)pyridin-3-yl)methyl)morpholine-4-carboxamide

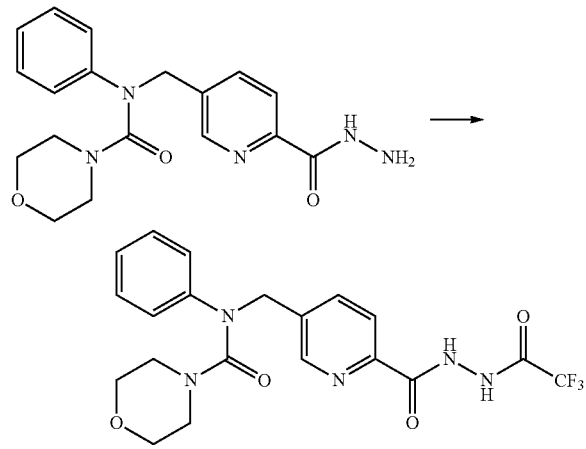

A solution of N-((6-(hydrazinecarbonyl)pyridin-3-yl)methyl)-N-phenylmorpholine-4-carboxamide (0.467 g, 1.314 mmol), trifluoroacetic anhydride (0.164 mL, 1.183 mmol) and triethylamine (0.273 mL, 1.971 mmol) in dichloromethane (10 mL) was stirred at the room temperature for 4 hr. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-phenyl-N-((6-(2-(2,2,2-trifluoroacetyl)hydrazine-1-carbonyl)pyridin-3-yl)methyl)morpholine-4-carboxamide as Colorless oil (0.449 g, 75.7%).

[Step 2] Compound 21333

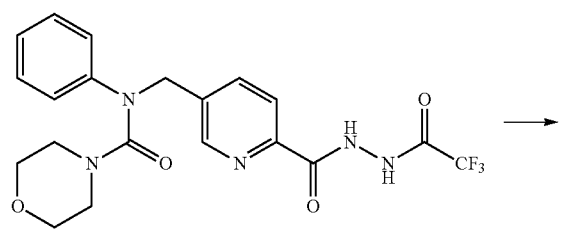

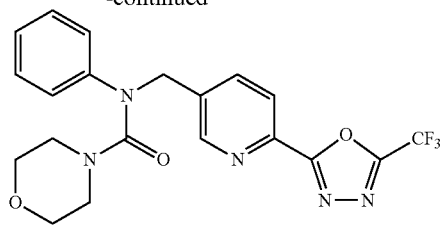

A mixture of N-phenyl-N-((6-(2-(2,2,2-trifluoroacetyl)hydrazine-1-carbonyl)pyridin-3-yl)methyl)morpholine-4-carboxamide (0.449 g, 0.995 mmol) prepared in Step 1 and 1-methoxy-N-triethylammoniosulfonyl-methanimidate (Burgess reagent, 0.308 g, 1.293 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 60%) to give the title compound N-phenyl-N-46-(5-(trifluoromethyl)-1,3,4-oxadiazol-2-yl)pyridin-3-yl)methyl)morpholine-4-carboxamide as Colorless oil (0.230 g, 53.4%).

¹H NMR (400 MHz, CDCl₃) δ 8.65 (s, 1H), 8.25-8.22 (m, 1H), 8.00-8.98 (m, 1H), 7.37-7.28 (m, 2H), 7.19-7.15 (m, 1H), 7.09-7.06 (m, 2H), 5.32 (s, 2H), 3.50 (t, 4H, J=4.6 Hz), 3.25 (t, 4H, J=4.6 Hz); LRMS (ES) m/z 434.05 (M⁺+1).

Example 9. Compound 21336: N-phenyl-N-((5-(5-(trifluoromethyl)-1,3,4-oxadiazol-2-yl)pyridin-2-yl)methyl)morpholine-4-carboxamide

[Step 1] Methyl 6-((N-phenylmorpholine-4-carboxamido)methyl)nicotinate

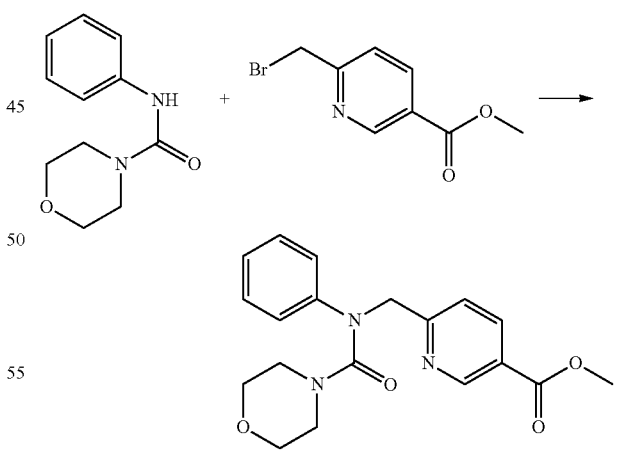

To a stirred solution of N-phenylmorpholine-4-carboxamide (1.000 g, 4.849 mmol) in N,N-dimethylformamide (30 mL) was added at 0° C. sodium hydride (60.00%, 0.291 g, 7.273 mmol). The reaction mixture was stirred at the same temperature for 30 min, treated at the room temperature with methyl 6-(bromomethyl)nicotinate (1.450 g, 6.303 mmol), and stirred for additional 5 hr. Then, aqueous 1N-hydrochloric acid solution was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound methyl 6-((N-phenylmorpholine-4-carboxamido)methyl)nicotinate as Brown oil (0.600 g, 34.8%).

[Step 2] N-((5-(hydrazinecarbonyl)pyridin-2-yl)methyl)-N-phenylmorpholine-4-carboxamide

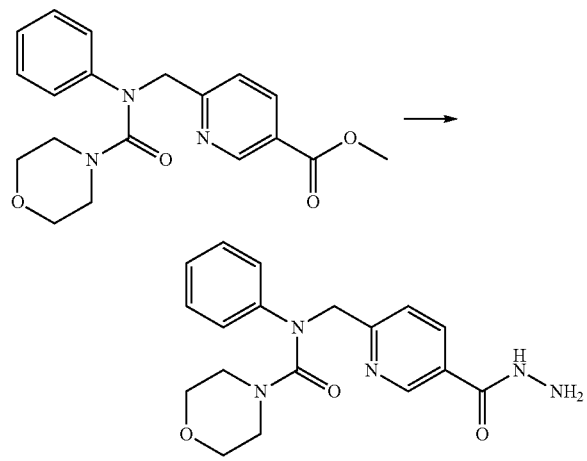

A mixture of methyl 6-((N-phenylmorpholine-4-carboxamido)methyl)nicotinate (0.420 g, 1.182 mmol) prepared in Step 1 and hydrazine monohydrate (1.116 mL, 23.636 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 10%) to give the title compound N-((5-(hydrazinecarbonyl)pyridin-2-yl)methyl)-N-phenylmorpholine-4-carboxamide as colorless oil (0.286 g, 68.1%).

[Step 3] N-phenyl-N-((5-(2-(2,2,2-trifluoroacetyl)hydrazine-1-carbonyl)pyridin-2-yl)methyl)morpholine-4-carboxamide

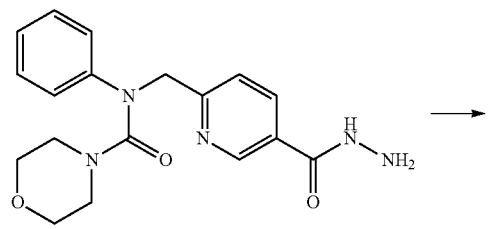

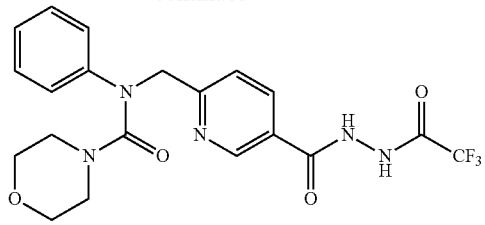

A solution of N-((5-(hydrazinecarbonyl)pyridin-2-yl)methyl)-N-phenylmorpholine-4-carboxamide (0.286 g, 0.805 mmol) prepared in Step 2, trifluoroacetic anhydride (0.101 mL, 0.724 mmol) and triethylamine (0.167 mL, 1.207 mmol) in dichloromethane (10 mL) was stirred at the room temperature for 4 hr. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-phenyl-N-((5-(2-(2,2,2-trifluoroacetyl)hydrazine-1-carbonyl)pyridin-2-yl)methyl)morpholine-4-carboxamide as Colorless oil (0.224 g, 61.7%).

[Step 4] Compound 21336

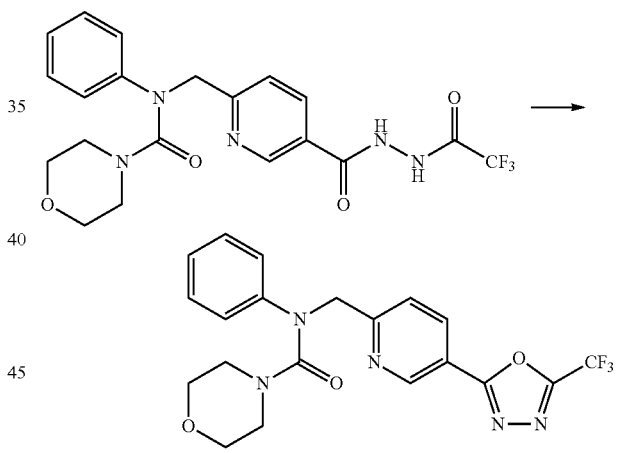

A mixture of N-phenyl-N-((5-(2-(2,2,2-trifluoroacetyl)hydrazine-1-carbonyl)pyridin-2-yl)methyl)morpholine-4-carboxamide (0.224 g, 0.496 mmol) prepared in Step 3 and 1-methoxy-N-triethylammoniosulfonyl-methanimidate (Burgess reagent, 0.154 g, 0.645 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound N-phenyl-N-45-(5-(trifluoromethyl)-1,3,4-oxadiazol-2-yl)pyridin-2-yl)methyl)morpholine-4-carboxamide as Colorless oil (0.150 g, 69.7%).
¹H NMR (400 MHz, CDCl₃) δ 9.25 (d, 1H, J=2.2 Hz), 8.40 (dd, 1H, J=8.3, 2.3 Hz), 7.71 (d, 1H, J=8.4 Hz), 7.35 (t, 2H, J=7.9 Hz), 7.21-7.20 (m, 2H), 7.17-7.12 (m, 1H), 5.17 (s, 2H), 3.54 (t, 4H, J=4.8 Hz), 3.29 (t, 4H, J=4.7 Hz); LRMS (ES) m/z 434.1 (M⁺+1).

Example 10, Compound 21337: N-(4-(5-(difluoromethyl)-1,3,4-oxadiazol-2-yl)-2-fluorobenzyl)-N-phenylmorpholine-4-carboxamide

[Step 1] N-(4-(2-(2,2-difluoroacetyl)hydrazine-1-carbonyl)-2-fluorobenzyl)-N-phenylmorpholine-4-carboxamide

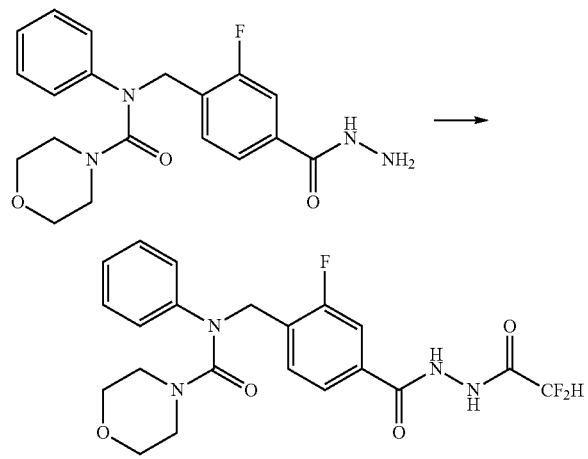

A solution of N-(2-fluoro-4-(hydrazinecarbonyl)benzyl)-N-phenylmorpholine-4-carboxamide (0.205 g, 0.550 mmol) prepared in Step 2 of Example 3, 2,2-difluoroacetic anhydride (0.062 mL, 0.495 mmol) and triethylamine (0.115 mL, 0.826 mmol) in dichloromethane (5 mL) was stirred at the room temperature for 1 hr. Then, water was added to the reaction mixture, followed by extraction with dichloromethane. The bi-phasic mixture was passed through a plastic frit to remove solid residues and aqueous layer; and the organic layer collected was concentrated in vacuo. The concentrate was purified and concentrated by column chromatography (SiO₂, 4 g cartridge; methanol/dichloromethane=0% to 5%) to give the title compound N-(4-(2-(2,2-difluoroacetyl)hydrazine-1-carbonyl)-2-fluorobenzyl)-N-phenylmorpholine-4-carboxamide as colorless oil (0.220 g, 88.7%).

[Step 2] Compound 21337

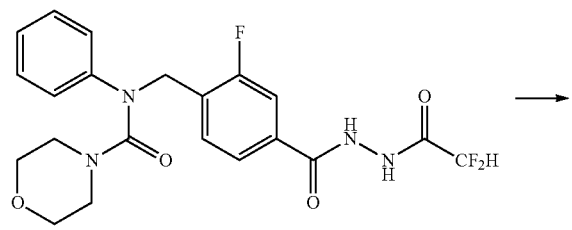

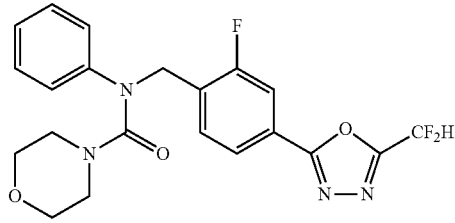

N-(4-(2-(2,2-difluoroacetyl)hydrazine-1-carbonyl)-2-fluorobenzyl)-N-phenylmorpholine-4-carboxamide (0.220 g, 0488 mmol) prepared in Step 1 and 1-methoxy-N-triethylammoniosulfonyl-methanimidate (Burgess reagent, 0.175 g, 0.733 mmol) in tetrahydrofuran (5 mL) was mixed at the room temperature and then heated at 150° C. under the microwaves for 30 min, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 4 g cartridge; ethyl acetate/hexane=30% to 100%) to give the title compound N-(4-(5-(difluoromethyl)-1,3,4-oxadiazol-2-yl)-2-fluorobenzyl)-N-phenylmorpholine-4-carboxamide as colorless oil (0.125 g, 59.2%).

¹H NMR (400 MHz, CDCl₃) δ 7.88 (dd, 1H, J=8.0, 1.6 Hz), 7.76 (dd, 1H, J=10.1, 1.6 Hz), 7.71 (t, 1H, J=7.6 Hz), 7.34 (t, 2H, J=7.9 Hz), 7.18-7.12 (m, 3H), 6.93 (t, 1H, J=51.7 Hz), 5.00 (s, 2H), 3.50 (t, 4H, J=4.8 Hz), 3.26 (t, 4H, J=4.8 Hz); LRMS (ESI) m/z 433.4 (M⁺+H).

Example 11. Compound 21340: 3-Cyclobutyl-1-phenyl-1-(4-(5-(trifluoromethyl)-1,3,4-oxadiazol-2-yl)benzyl)urea

[Step 1] Methyl 4-((phenylamino)methyl)benzoate

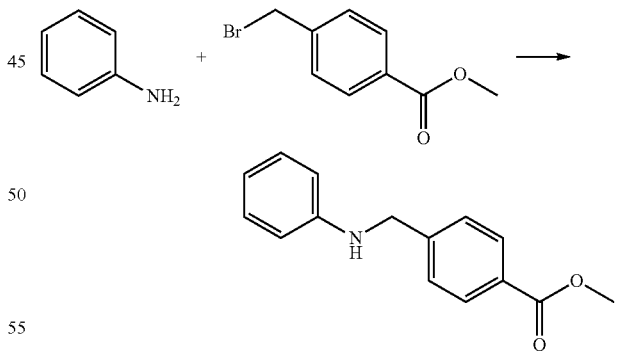

A solution of aniline (9.804 mL, 107.377 mmol) and methyl 4-(bromomethyl)benzoate (25.827 g, 112.746 mmol) in N,N-dimethylformamide (200 mL) was mixed at 0° C. with sodium hydride (60.00%, 5.154 g, 128.852 mmol), and stirred at the room temperature for 1 hr. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 120 g cartridge; ethyl acetate/hexane=0% to 5%) to give the title compound methyl 4-((phenylamino)methyl)benzoate as colorless oil (17.530 g, 67.7%).

[Step 2] Methyl 4-((3-cyclobutyl-1-phenylureido)methyl)benzoate

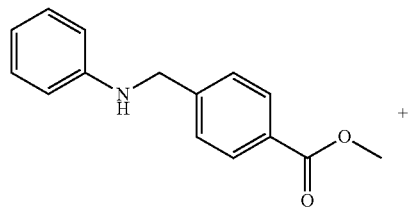

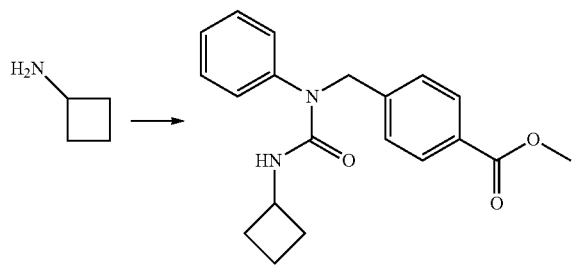

A solution of methyl 4-((phenylamino)methyl)benzoate (0.500 g, 2.072 mmol) prepared in Step 1, triphosgene (0.676 g, 2.279 mmol) and N,N-diisopropylethylamine (3.619 mL, 20.722 mmol) in dichloromethane (10 mL) was mixed at 0° C. with cyclobutylamine hydrochloride (0.245 g, 2.279 mmol), and stirred at the room temperature for 16 hr. Then, water was added to the reaction mixture, followed by extraction with ethyl acetate. The organic layer was washed with brine, dried (anhydrous $MgSO_4$), filtered, and concentrated in vacuo. The concentrate was purified and concentrated by column chromatography ($SiO_2$, 12 g cartridge; dichloromethane/hexane=0% to 30%) to give the title compound methyl 4-((3-cyclobutyl-1-phenylureido)methyl)benzoate as white solid (0.586 g, 83.6%).

[Step 3] 3-Cyclobutyl-1-(4-(hydrazinecarbonyl)benzyl)-1-phenylurea

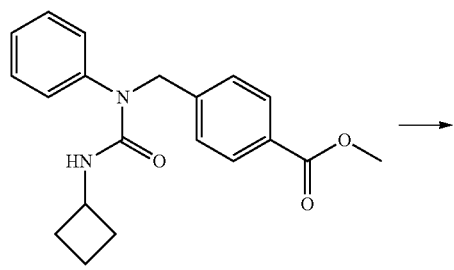

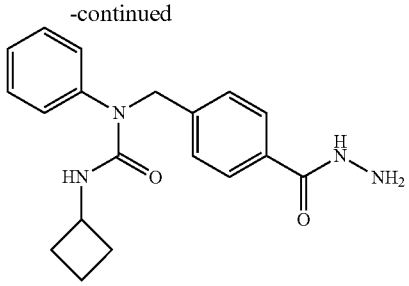

A mixture of methyl 4-((3-cyclobutyl-1-phenylureido)methyl)benzoate (0.300 g, 0.886 mmol) prepared in Step 2 and hydrazine monohydrate (0.837 mL, 17.730 mmol) in ethanol (5 mL) was heated at 120° C. for 1 hr under the microwaves, and cooled down to the room temperature to terminate the reaction. The reaction mixture was concentrated under the reduced pressure to remove the solvent and saturated aqueous sodium bicarbonate solution was added to the concentrate, followed by extraction with ethyl acetate. The organic layer was washed with brine, dried (anhydrous $MgSO_4$), filtered, and concentrated in vacuo. The concentrate was purified and concentrated by column chromatography ($SiO_2$, 12 g cartridge; methanol/dichloromethane=0% to 5%) to give the title compound 3-cyclobutyl-1-(4-(hydrazinecarbonyl)benzyl)-1-phenylurea as white solid (0.159 g, 53.0%).

[Step 4] Compound 21340

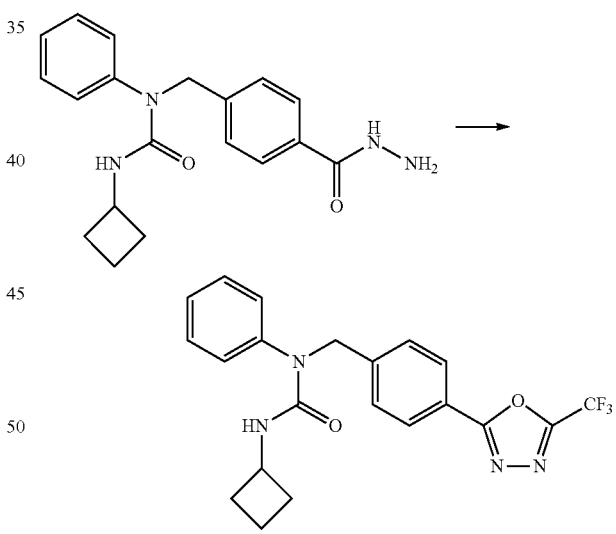

A solution of 3-cyclobutyl-1-(4-(hydrazinecarbonyl)benzyl)-1-phenylurea (0.149 g, 0.440 mmol) prepared in Step 3 and triethylamine (0.092 mL, 0.660 mmol) in dichloromethane (3 mL) was mixed at 0° C. with trifluoroacetic anhydride (0.055 mL, 0.396 mmol), and stirred at the room temperature for 60 hr. Then, saturated aqueous sodium bicarbonate solution was added to the reaction mixture, followed by extraction with dichloromethane. The organic layer was washed with brine, dried (anhydrous $MgSO_4$), filtered, and concentrated in vacuo. The concentrate was purified and concentrated by column chromatography ($SiO_2$, 4 g cartridge; methanol/dichloromethane=0% to 3%) to give the title compound 3-cyclobutyl-1-phenyl-1-(4-(5-(trifluoromethyl)-1,3,4-oxadiazol-2-yl)benzyl)urea as white solid (0.053 g, 28.9%).

$^1$H NMR (400 MHz, CDCl$_3$) δ 8.01 (d, 2H, J=8.3 Hz), 7.43-7.28 (m, 5H), 7.10-7.05 (m, 2H), 4.92 (s, 2H), 4.41-4.39 (m, 1H), 4.32-4.28 (m, 1H), 2.30-2.27 (m, 2H), 1.66-1.56 (m, 4H); LRMS (ES) m/z 416.9 (M$^+$+1).

Example 12. Compound 21341: 3-Cyclopentyl-1-phenyl-1-(4-(5-(trifluoromethyl)-1,3,4-oxadiazol-2-yl)benzyl)urea

[Step 1] Methyl 4-((3-cyclopentyl-1-phenylureido)methyl)benzoate

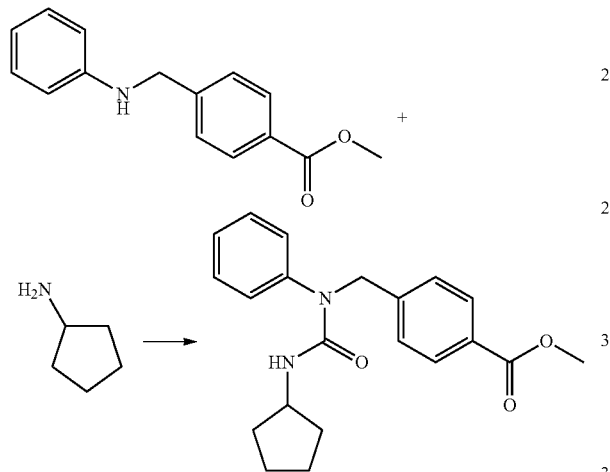

A solution of methyl 4-((phenylamino)methyl)benzoate (0.500 g, 2.072 mmol) prepared in Step 1 of Example 11, triphosgene (0.676 g, 2.279 mmol) and N,N-diisopropylethylamine (3.619 mL, 20.722 mmol) in dichloromethane (10 mL) was mixed at 0° C. with cyclopentylamine (0.225 mL, 2.279 mmol), and stirred at the room temperature for 16 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-((3-cyclopentyl-1-phenylureido)methyl)benzoate as white solid (0.475 g, 65.0%).

[Step 2] 3-Cyclopentyl-1-(4-(hydrazinecarbonyl)benzyl)-1-phenylurea

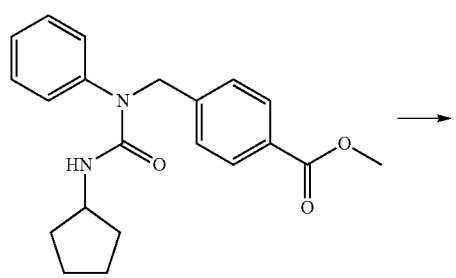

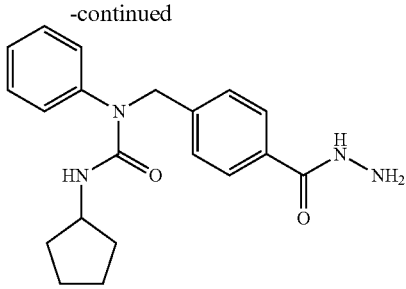

A mixture of methyl 4-((3-cyclopentyl-1-phenylureido)methyl)benzoate (0.300 g, 0.851 mmol) prepared in Step 1 and hydrazine monohydrate (0.804 mL, 17.025 mmol) in ethanol (5 mL) was heated at 120° C. for 1 hr under the microwaves, and cooled down to the room temperature to terminate the reaction. The reaction mixture was concentrated under the reduced pressure to remove the solvent, and saturated aqueous sodium bicarbonate solution was added to the concentrate, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 5%) to give the title compound 3-cyclopentyl-1-(4-(hydrazinecarbonyl)benzyl)-1-phenylurea as white solid (0.213 g, 71.0%).

[Step 3] Compound 21341

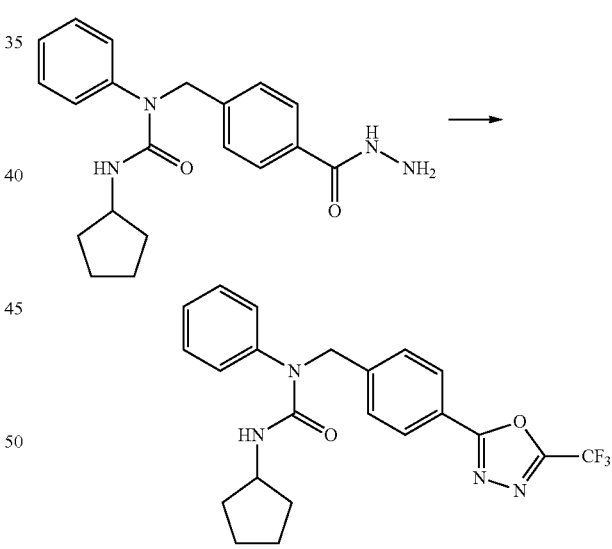

A solution of 3-cyclopentyl-1-(4-(hydrazinecarbonyl)benzyl)-1-phenylurea (0.208 g, 0.590 mmol) prepared in Step 2 and triethylamine (0.123 mL, 0.885 mmol) in dichloromethane (3 mL) was mixed at 0° C. with trifluoroacetic anhydride (0.074 mL, 0.531 mmol), and stirred at the room temperature for 60 hr. Then, saturated aqueous sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 4 g cartridge; methanol/dichloromethane=0% to 3%) to give the title compound 3-cyclopentyl-1-phenyl-1-(4-(5-(trifluoromethyl)-1,3,4-oxadiazol-2-yl)benzyl)urea as white solid (0.142 g, 55.9%).

$^1$H NMR (400 MHz, CDCl$_3$) δ 8.01 (d, 2H, J=8.2 Hz), 7.44 (d, 2H, J=8.1 Hz), 7.35-7.28 (m, 3H), 7.09-7.04 (m, 2H), 4.94 (s, 2H), 4.23-4.18 (m, 1H), 4.14-4.10 (m, 1H), 1.96-1.91 (m, 2H), 1.53-1.51 (m, 4H), 1.23-1.18 (m, 2H); LRMS (ES) m/z 430.85 (M$^+$+1).

Example 13. Compound 21342: 3-Cyclohexyl-1-phenyl-1-(4-(5-(trifluoromethyl)-1,3,4-oxadiazol-2-yl)benzyl)urea

[Step 1] Methyl 4-((3-cyclohexyl-1-phenylureido)methyl)benzoate

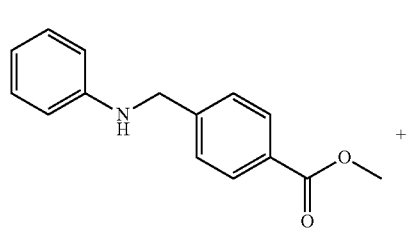

+

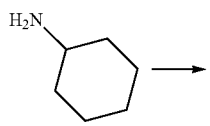

→

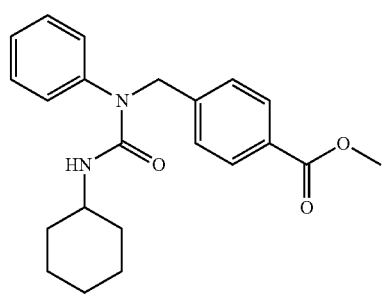

A solution of methyl 4-((phenylamino)methyl)benzoate (0.500 g, 2.072 mmol) prepared in Step 1 of Example 11, triphosgene (0.676 g, 2.279 mmol) and N,N-diisopropylethylamine (3.619 mL, 20.722 mmol) in dichloromethane (10 mL) was mixed at 0° C. with cyclohexylamine (0.261 mL, 2.279 mmol), and stirred at the room temperature for 16 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-((3-cyclohexyl-1-phenylureido)methyl)benzoate as white solid (0.474 g, 62.4%).

[Step 2] 3-Cyclohexyl-1-(4-(hydrazinecarbonyl)benzyl)-1-phenylurea

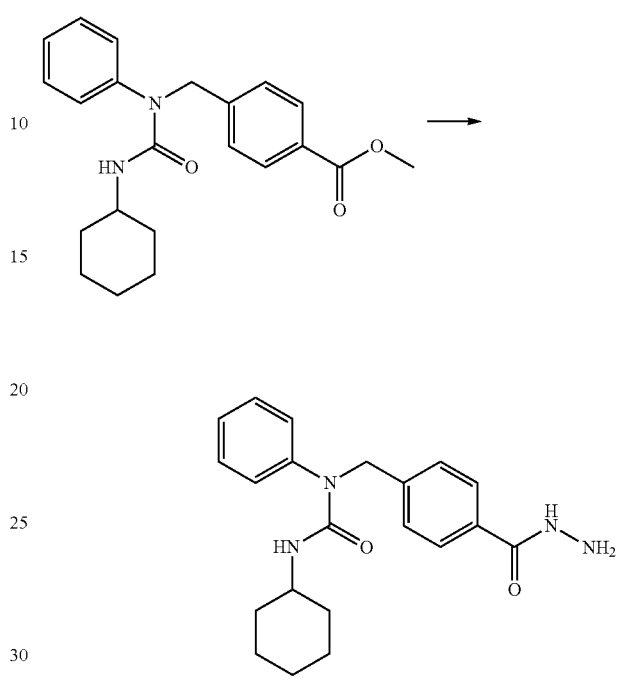

A mixture of methyl 4-((3-cyclohexyl-1-phenylureido)methyl)benzoate (0.300 g, 0.819 mmol) prepared in Step 1 and hydrazine monohydrate (0.773 mL, 16.373 mmol) in ethanol (5 mL) was heated at 120° C. for 1 hr under the microwaves, and cooled down to the room temperature to terminate the reaction. The reaction mixture was concentrated under the reduced pressure to remove the solvent, and saturated aqueous sodium bicarbonate solution was added to the concentrate, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 5%) to give the title compound 3-cyclohexyl-1-(4-(hydrazinecarbonyl)benzyl)-1-phenylurea as white solid (0.206 g, 68.7%).

[Step 3] Compound 21342

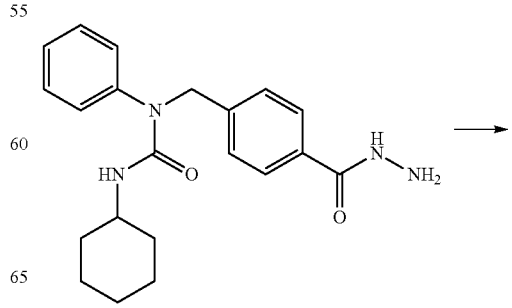

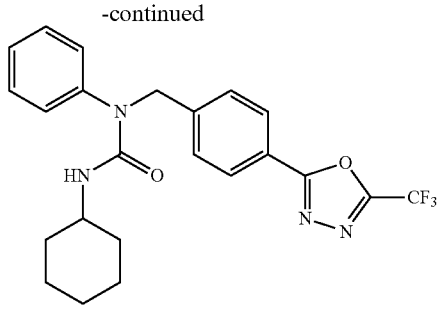

A solution of 3-cyclohexyl-1-(4-(hydrazinecarbonyl)benzyl)-1-phenylurea (0.197 g, 0.538 mmol) prepared in Step 2 and triethylamine (0.112 mL, 0.806 mmol) in dichloromethane (3 mL) was mixed at 0° C. with trifluoroacetic anhydride (0.067 mL, 0.484 mmol), and stirred at the room temperature for 60 hr. Then, saturated aqueous sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 4 g cartridge; methanol/dichloromethane=0% to 3%) to give the title compound 3-cyclohexyl-1-phenyl-1-(4-(5-(trifluoromethyl)-1,3,4-oxadiazol-2-yl)benzyl)urea as bright yellow solid (0.117 g, 48.9%).

$^1$H NMR (400 MHz, CDCl$_3$) δ 8.00 (d, 2H, J=8.0 Hz), 7.43-7.27 (m, 5H), 7.08-7.05 (m, 2H), 4.92 (s, 2H), 4.17-4.15 (m, 1H), 3.68-3.64 (m, 1H), 1.87-1.84 (m, 2H), 1.59-1.51 (m, 3H), 1.35-1.23 (m, 2H), 1.06-0.93 (m, 3H); LRMS (ES) m/z 445.1 (M$^+$+1).

Example 14. Compound 21343: N-(2-methoxy-4-(5-(trifluoromethyl)-1,3,4-oxadiazol-2-yl)benzyl)-N-phenylmorpholine-4-carboxamide

[Step 1] Methyl 3-methoxy-4-((N-phenylmorpholine-4-carboxamido)methyl)benzoate

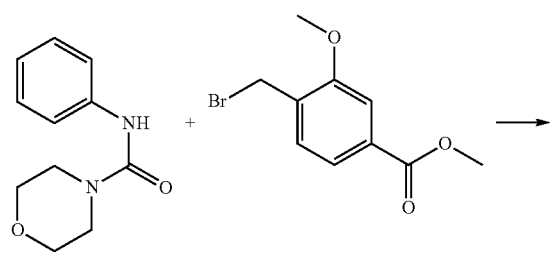

To a stirred solution of N-phenylmorpholine-4-carboxamide (0.500 g, 2.424 mmol) in N,N-dimethylformamide (10 mL) was added at 0° C. methyl 4-(bromomethyl)-3-methoxybenzoate (0.817 g, 3.152 mmol). The reaction mixture was stirred at the same temperature for 30 min, treated at the room temperature with sodium hydride (60.00%, 0.194 g, 4.849 mmol), and stirred for additional 4 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 40%) to give the title compound methyl 3-methoxy-4-((N-phenylmorpholine-4-carboxamido)methyl)benzoate as Colorless oil (0.690 g, 74.0%).

[Step 2] N-(4-(hydrazinecarbonyl)-2-methoxybenzyl)-N-phenylmorpholine-4-carboxamide

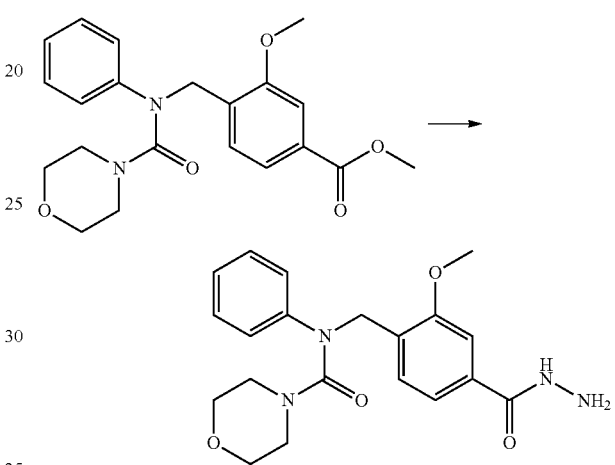

A mixture of methyl 3-methoxy-4-((N-phenylmorpholine-4-carboxamido)methyl)benzoate (0.600 g, 1.561 mmol) prepared in Step 1 and hydrazine monohydrate (0.737 mL, 15.608 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo to give the title compound N-(4-(hydrazinecarbonyl)-2-methoxybenzyl)-N-phenylmorpholine-4-carboxamide (0.600 g, 100.0%, Colorless oil).

[Step 3] N-(2-methoxy-4-(2-(2,2,2-trifluoroacetyl)hydrazine-1-carbonyl)benzyl)-N-phenylmorpholine-4-carboxamide

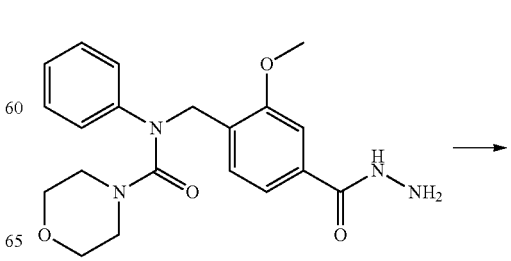

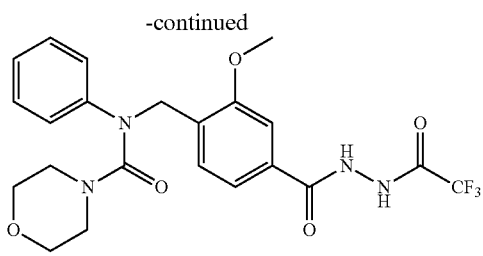

A solution of N-(4-(hydrazinecarbonyl)-2-methoxybenzyl)-N-phenylmorpholine-4-carboxamide (0.762 g, 1.982 mmol) prepared in Step 2, trifluoroacetic anhydride (0.248 mL, 1.784 mmol) and triethylamine (0.412 mL, 2.973 mmol) in dichloromethane (10 mL) was stirred at the room temperature for 2 hr. Then, water was added to the reaction mixture, followed by extraction with dichloromethane. The organic layer was washed with brine, dried (anhydrous $MgSO_4$), filtered, and concentrated in vacuo. The concentrate was purified and concentrated by column chromatography ($SiO_2$, 12 g cartridge; ethyl acetate/hexane=0% to 10%) to give the title compound N-(2-methoxy-4-(2-(2,2,2-trifluoroacetyl)hydrazine-1-carbonyl)benzyl)-N-phenylmorpholine-4-carboxamide as White solid (0.600 g, 63.0 (7c).

[Step 4] Compound 21343

A mixture of N-(2-methoxy-4-(2-(2,2,2-trifluoroacetyl) hydrazine-1-carbonyl)benzyl)-N-phenylmorpholine-4-carboxamide (0.364 g, 0.758 mmol) prepared in Step 3 and 1-methoxy-N-triethylammoniosulfonyl-methanimidate (Burgess reagent, 0.235 g, 0.985 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous $MgSO_4$), filtered, and concentrated in vacuo. The concentrate was purified and concentrated by column chromatography ($SiO_2$, 12 g cartridge; ethyl acetate/hexane=0% to 50%) to give the title compound N-(2-methoxy-4-(5-(trifluoromethyl)-1,3,4-oxadiazol-2-yl)benzyl)-N-phenylmorpholine-4-carboxamide as Colorless oil (0.250 g, 71.4%).

$^1$H NMR (400 MHz, $CDCl_3$) δ 7.66 (d, 1H, J=1.5 Hz), 7.64-7.54 (m, 2H), 7.32-7.28 (m, 2H), 7.13-7.08 (m, 3H), 4.96 (s, 2H), 3.88 (s, 3H), 3.50 (t, 4H, J=4.8 Hz), 3.26 (t, 4H, J=4.8 Hz); LRMS (ES) m/z 463.2 ($M^+$+1).

Example 15. Compound 21344: 4-Benzyl-N-phenyl-N-(4-(5-(trifluoromethyl)-1,3,4-oxadiazol-2-yl)benzyl)piperazine-1-carboxamide

[Step 1] Methyl 4-((4-benzyl-N-phenylpiperazine-1-carboxamido)methyl)benzoate

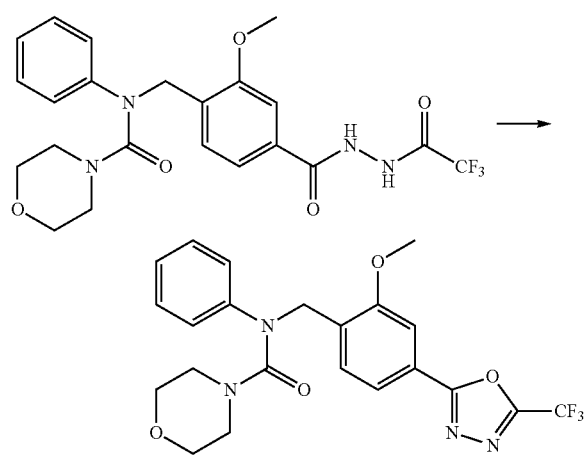

To a stirred solution of methyl 4-((phenylamino)methyl) benzoate (2.000 g, 8.290 mmol) in dichloromethane (30 mL) were added at 0° C. N,N-diisopropylethylamine (7.220 mL, 41.452 mmol) and triphosgene (1.968 g, 6.632 mmol). The reaction mixture was stirred at the same temperature for 1 hr, treated at the room temperature with 1-benzylpiperazine (1.607 g, 9.120 mmol), and stirred for additional 4 hr. Then, water was added to the reaction mixture, followed by extraction with dichloromethane. The organic layer was washed with brine, dried (anhydrous $MgSO_4$), filtered, and concentrated in vacuo. The concentrate was purified and concentrated by column chromatography ($SiO_2$, 12 g cartridge; ethyl acetate/hexane=0% to 50%) to give the title compound methyl 4-((4-benzyl-N-phenylpiperazine-1-carboxamido)methyl)benzoate as Yellow oil (3.600 g, 97.9%).

[Step 2] 4-Benzyl-N-(4-(hydrazinecarbonyl)benzyl)-N-phenylpiperazine-1-carboxamide

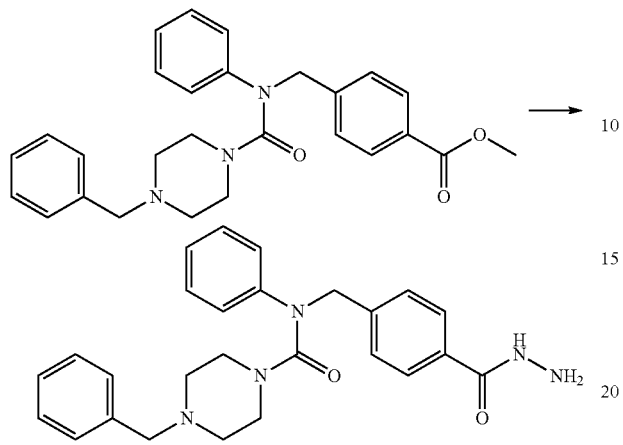

A mixture of methyl 4-((4-benzyl-N-phenylpiperazine-1-carboxamido)methyl)benzoate (3.600 g, 8.116 mmol) prepared in Step 1 and hydrazine monohydrate (3.833 mL, 81.163 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO₄), filtered, and concentrated in vacuo to give the title compound 4-benzyl-N-(4-(hydrazinecarbonyl)benzyl)-N-phenylpiperazine-1-carboxamide (1.820 g, 50.6%, White solid).

[Step 3] 4-Benzyl-N-phenyl-N-(4-(2-(2,2,2-trifluoroacetyl)hydrazine-1-carbonyl)benzyl)piperazine-1-carboxamide

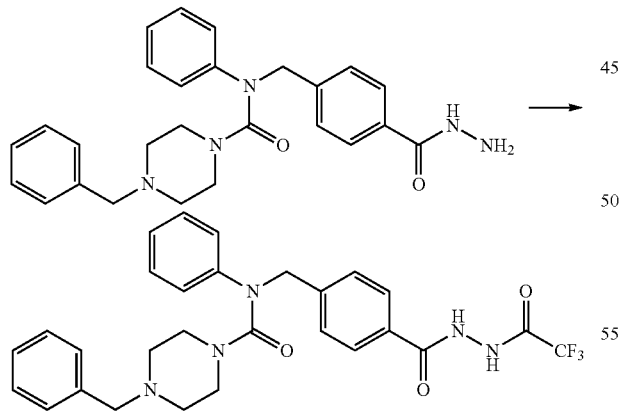

A solution of 4-benzyl-N-(4-(hydrazinecarbonyl)benzyl)-N-phenylpiperazine-1-carboxamide (1.820 g, 4.103 mmol) prepared in Step 2, trifluoroacetic anhydride (0.514 mL, 3.693 mmol) and triethylamine (0.853 mL, 6.155 mmol) in dichloromethane (20 mL) was stirred at the room temperature for 3 hr. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound 4-benzyl-N-phenyl-N-(4-(2-(2,2,2-trifluoroacetyl)hydrazine-1-carbonyl)benzyl)piperazine-1-carboxamide as Colorless oil (1.400 g, 63.2%).

[Step 4] Compound 21344

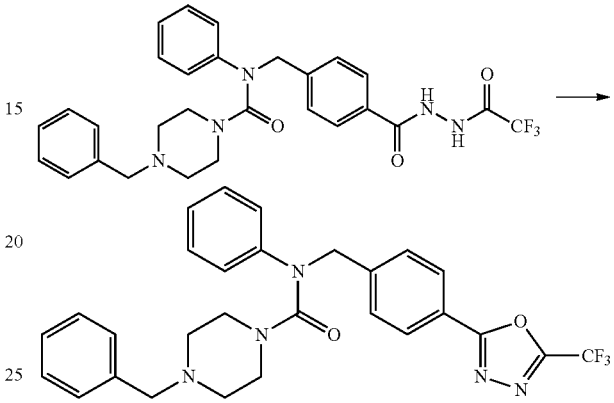

A mixture of 4-benzyl-N-phenyl-N-(4-(2-(2,2,2-trifluoroacetyl)hydrazine-1-carbonyl)benzyl)piperazine-1-carboxamide (1.000 g, 1.853 mmol) prepared in Step 3 and 1-methoxy-N-triethylammoniosulfonyl-methanimidate (Burgess reagent, 0.574 g, 2.409 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound 4-benzyl-N-phenyl-N-(4-(5-(trifluoromethyl)-1,3,4-oxadiazol-2-yl)benzyl)piperazine-1-carboxamide as Colorless oil (0.700 g, 72.4%).
¹H NMR (400 MHz, CDCl₃) δ 7.99 (d, 2H, J=8.4 Hz), 7.46 (d, 2H, J=8.4 Hz), 7.27-7.23 (m, 7H), 7.07 (t, 1H, J=7.4 Hz), 7.00 (d, 2H, J=7.6 Hz), 4.91 (s, 2H), 3.42 (s, 2H), 3.26 (s, 4H), 2.25 (s, 4H); LRMS (ES) m/z 522.3 (M⁺+1).

Example 16. Compound 21345: 4-(2-Methoxyethyl)-N-phenyl-N-(4-(5-(trifluoromethyl)-1,3,4-oxadiazol-2-yl)benzyl)piperazine-1-carboxamide

[Step 1] Methyl 4-((4-(2-methoxyethyl)-N-phenylpiperazine-1-carboxamido)methyl)benzoate

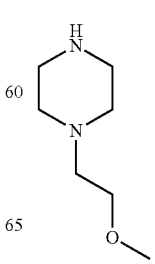

+

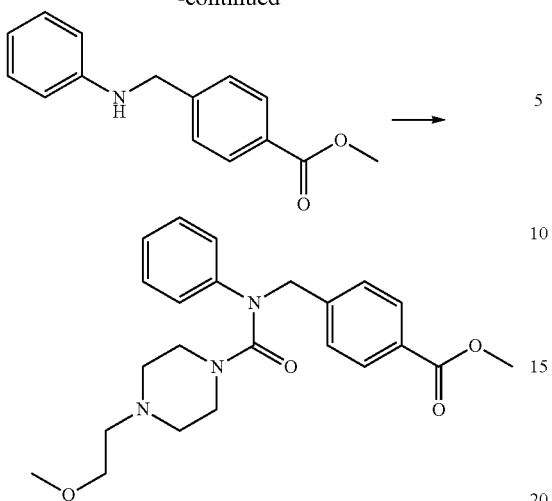

To a stirred solution of methyl 4-((phenylamino)methyl)benzoate (0.500 g, 2.073 mmol) in dichloromethane (10 mL) were added at 0° C. N,N-diisopropylethylamine (1.805 mL, 10.363 mmol) and triphosgene (0.490 g, 1.658 mmol), and stirred for 30 min. The reaction mixture was treated with 1-(2-methoxyethyl)piperazine (0.339 mL, 2.280 mmol), stirred at the same temperature for 30 min, and cooled down to the room temperature to terminate the reaction. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound methyl 4-((4-(2-methoxyethyl)-N-phenylpiperazine-1-carboxamido)methyl)benzoate as Yellow oil (0.700 g, 82.1%).

[Step 2] N-(4-(hydrazinecarbonyl)benzyl)-4-(2-methoxyethyl)-N-phenylpiperazine-1-carboxamide

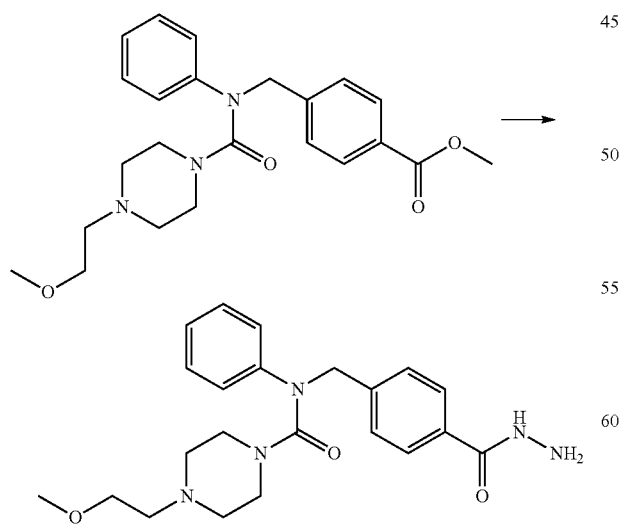

A mixture of methyl 4-((4-(2-methoxyethyl)-N-phenylpiperazine-1-carboxamido)methyl)benzoate (0.800 g, 1.944 mmol) prepared in Step 1 and hydrazine monohydrate (0.918 mL, 19.441 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO₄), filtered, and concentrated in vacuo to give the title compound N-(4-(hydrazinecarbonyl)benzyl)-4-(2-methoxyethyl)-N-phenylpiperazine-1-carboxamide (0.800 g, 100.0%, Yellow oil).

[Step 3] 4-(2-Methoxyethyl)-N-phenyl-N-(4-(2-(2,2,2-trifluoroacetyl)hydrazine-1-carbonyl)benzyl)piperazine-1-carboxamide

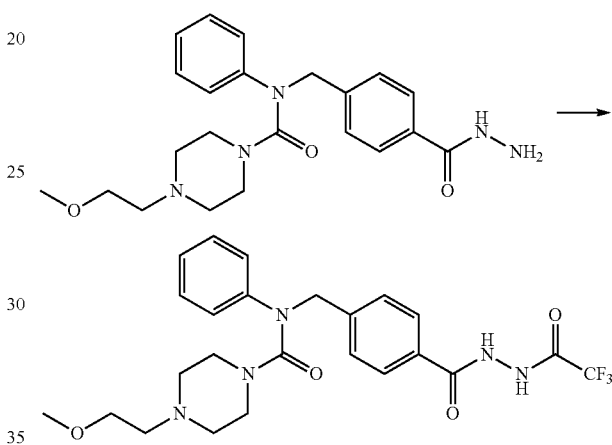

A solution of N-(4-(hydrazinecarbonyl)benzyl)-4-(2-methoxyethyl)-N-phenylpiperazine-1-carboxamide (0.744 g, 1.808 mmol) prepared in Step 2, trifluoroacetic anhydride (0.226 mL, 1.627 mmol) and triethylamine (0.376 mL, 2.712 mmol) in dichloromethane (10 mL) was stirred at the room temperature for 3 hr. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound 4-(2-methoxyethyl)-N-phenyl-N-(4-(2-(2,2,2-trifluoroacetyl)hydrazine-1-carbonyl)benzyl)piperazine-1-carboxamide as Colorless oil (0.368 g, 40.1%).

[Step 4] Compound 21345

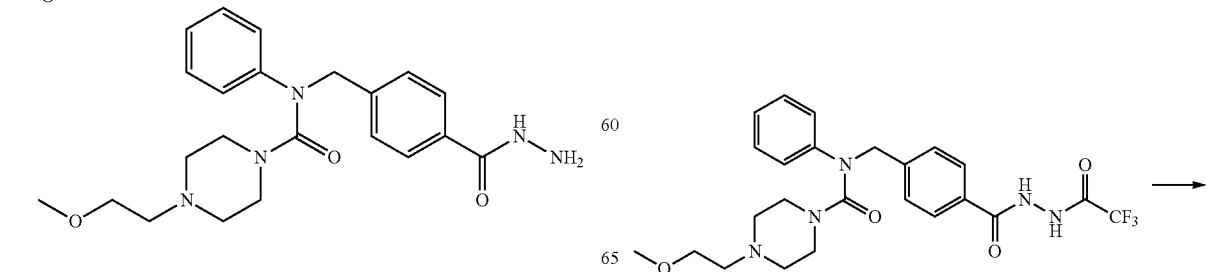

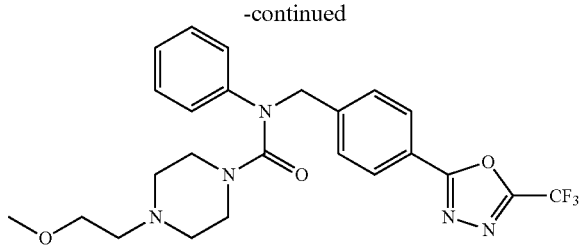

A mixture of 4-(2-methoxyethyl)-N-phenyl-N-(4-(2-(2,2,2-trifluoroacetyl)hydrazine-1-carbonyl)benzyl)piperazine-1-carboxamide (0.060 g, 0.118 mmol) prepared in Step 3 and 1-methoxy-N-triethylammoniosulfonyl-methanimidate (Burgess reagent, 0.037 g, 0.154 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound 4-(2-methoxyethyl)-N-phenyl-N-(4-(5-(trifluoromethyl)-1,3,4-oxadiazol-2-yl)benzyl)piperazine-1-carboxamide as Colorless oil (0.020 g, 34.6%).

$^1$H NMR (400 MHz, CDCl$_3$) δ 8.04-8.01 (m, 2H), 7.50 (d, 2H, J=8:3 Hz), 7.32-7.28 (m, 2H), 7.13-7.04 (m, 3H), 4.92 (s, 2H), 3.46 (t, 2H, J=5.4 Hz), 3.33-3.30 (m, 7H), 2.52 (t, 2H, J=5.4 Hz), 2.33 (t, 4H, J=4.7 Hz); LRMS (ES) m/z 490.2 (M$^+$+1).

Example 17. Compound 21346: 4-Ethyl-N-phenyl-N-(4-(5-(trifluoromethyl)-1,3,4-oxadiazol-2-yl)benzyl)piperazine-1-carboxamide

[Step 1] Methyl 4-((4-ethyl-N-phenylpiperazine-1-carboxamido)methyl)benzoate

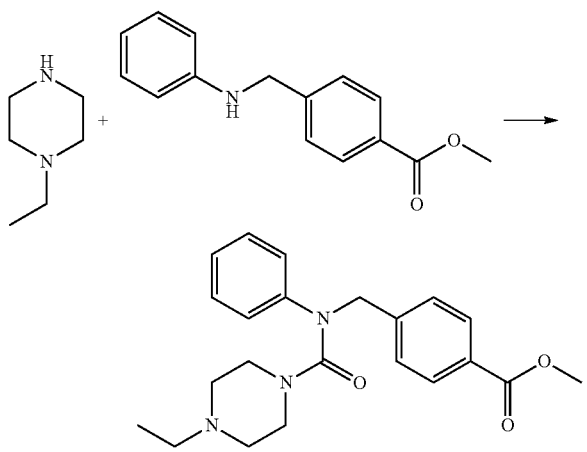

To a stirred solution of methyl 4-((phenylamino)methyl)benzoate (0.400 g, 1.658 mmol) in dichloromethane (20 mL) were added at 0° C. N,N-diisopropylethylamine (1.071 g, 8.290 mmol) and triphosgene (0.394 g, 1.326 mmol). The reaction mixture was stirred at the same temperature for 30 min, treated at the room temperature with 1-ethylpiperazine (0.232 mL, 1.824 mmol), and stirred for additional 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((4-ethyl-N-phenylpiperazine-1-carboxamido)methyl)benzoate as Yellow oil (0.569 g, 90.0%).

[Step 2] 4-Ethyl-N-(4-(hydrazinecarbonyl)benzyl)-N-phenylpiperazine-1-carboxamide

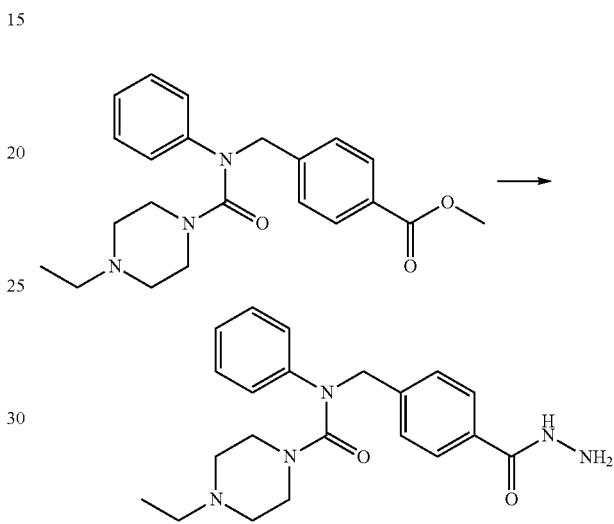

A mixture of methyl 4-((4-ethyl-N-phenylpiperazine-1-carboxamido)methyl)benzoate (0.569 g, 1.492 mmol) prepared in Step 1 and hydrazine monohydrate (0.704 mL, 14.916 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO$_4$), filtered, and concentrated in vacuo to give the title compound 4-ethyl-N-(4-(hydrazinecarbonyl)benzyl)-N-phenylpiperazine-1-carboxamide (0.550 g, 96.7%, Colorless oil).

[Step 3] 4-Ethyl-N-phenyl-N-(4-(2-(2,2,2-trifluoroacetyl)hydrazine-1-carbonyl)benzyl)piperazine-1-carboxamide

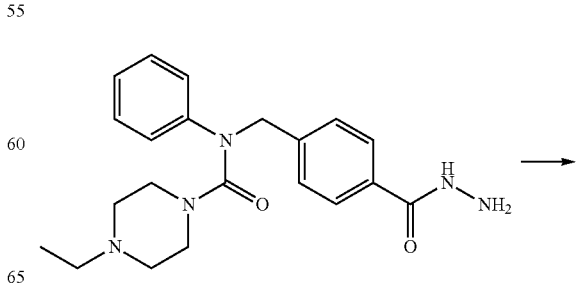

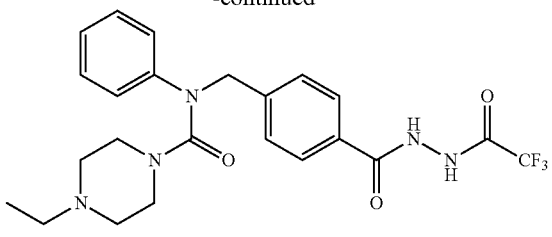

A solution of 4-ethyl-N-(4-(hydrazinecarbonyl)benzyl)-N-phenylpiperazine-1-carboxamide (0.569 g, 1.492 mmol) prepared in Step 2, trifluoroacetic anhydride (0.187 mL, 1.342 mmol) and triethylamine (0.310 mL, 2.237 mmol) in dichloromethane (10 mL) was stirred at the room temperature for 3 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound 4-ethyl-N-phenyl-N-(4-(2-(2,2,2-trifluoroacetyl)hydrazine-1-carbonyl)benzyl)piperazine-1-carboxamide as Colorless oil (0.442 g, 62.1%).

[Step 4] Compound 21346

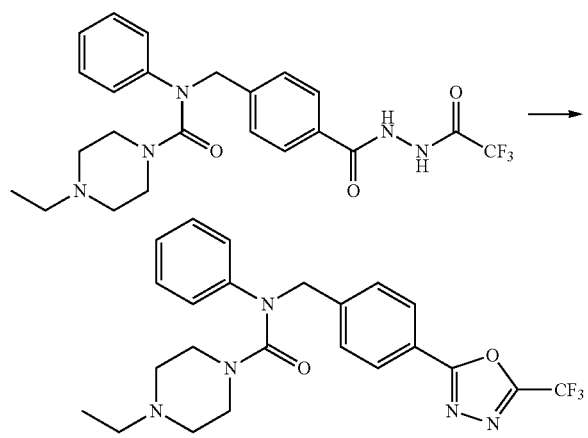

A mixture of 4-ethyl-N-phenyl-N-(4-(2-(2,2,2-trifluoroacetyl)hydrazine-1-carbonyl)benzyl)piperazine-1-carboxamide (0.442 g, 0.988 mmol) prepared in Step 3 and 1-methoxy-N-triethylammoniosulfonyl-methanimidate (Burgess reagent, 0.306 g, 1.284 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound 4-ethyl-N-phenyl-N-(4-(5-(trifluoromethyl)-1,3,4-oxadiazol-2-yl)benzyl)piperazine-1-carboxamide as Colorless oil (0.380 g, 83.7%).

$^1$H NMR (400 MHz, CDCl$_3$) δ 8.01 (d, 2H, J=8.2 Hz), 7.49 (d, 2H, J=8.2 Hz), 7.30-7.26 (m, 2H), 7.09 (t, 1H, J=7.4 Hz), 7.04 (d, 2H, J=7.5 Hz), 4.94 (s, 2H), 3.30-3.28 (m, 4H), 2.34 (q, 2H, J=7.2 Hz), 2.27-2.04 (m, 4H), 1.02 (t, 3H, J=7.2 Hz); LRMS (ES) m/z 474.27 (M$^+$+1).

Example 18. Compound 21347: 4-Isopropyl-N-phenyl-N-(4-(5-(trifluoromethyl)-1,3,4-oxadiazol-2-yl)benzyl)piperazine-1-carboxamide

[Step 1] Methyl 4-((4-isopropyl-N-phenylpiperazine-1-carboxamido)methyl)benzoate

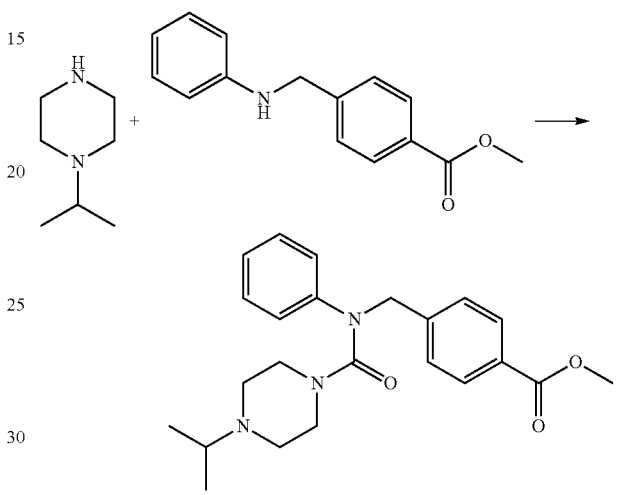

To a stirred solution of methyl 4-((phenylamino)methyl)benzoate (0.400 g, 1.658 mmol) in dichloromethane (20 mL) were added at 0° C. N,N-diisopropylethylamine (1.071 g, 8.290 mmol) and triphosgene (0.394 g, 1.326 mmol). The reaction mixture was stirred at the same temperature for 30 min, treated at the room temperature with 1-isopropylpiperazine (0.260 mL, 1.824 mmol), and stirred for additional 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((4-isopropyl-N-phenylpiperazine-1-carboxamido)methyl)benzoate as Yellow oil (0.600 g, 91.5%).

[Step 2] N-(4-(hydrazinecarbonyl)benzyl)-4-isopropyl-N-phenylpiperazine-1-carboxamide

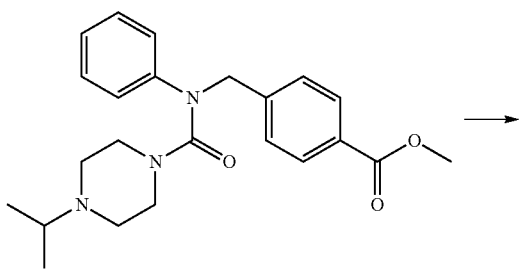

249

-continued

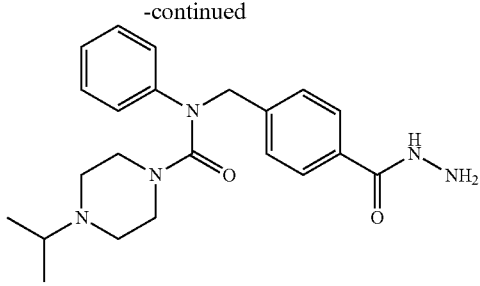

A mixture of methyl 4-((4-isopropyl-N-phenylpiperazine-1-carboxamido)methyl)benzoate (0.714 g, 1.805 mmol) prepared in Step 1 and hydrazine monohydrate (0.853 mL, 18.053 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO$_4$), filtered, and concentrated in vacuo to give the title compound N-(4-(hydrazinecarbonyl)benzyl)-4-isopropyl-N-phenylpiperazine-1-carboxamide (0.695 g, 97.3%, Colorless oil).

[Step 3] 4-Isopropyl-N-phenyl-N-(4-(2-(2,2,2-trifluoroacetyl)hydrazine-1-carbonyl)benzyl)piperazine-1-carboxamide

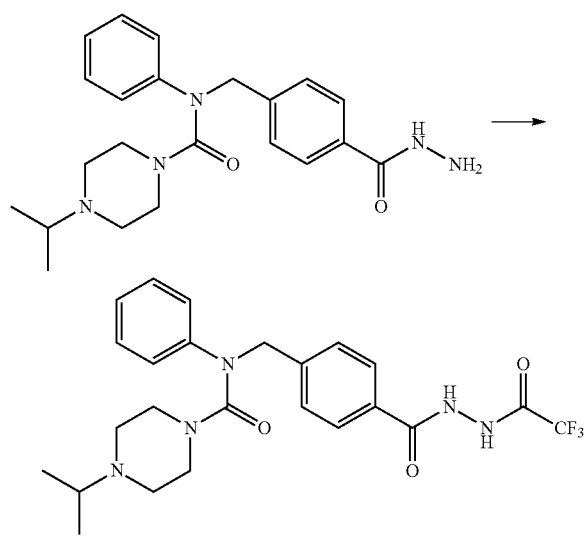

A solution of N-(4-(hydrazinecarbonyl)benzyl)-4-isopropyl-N-phenylpiperazine-1-carboxamide (0.659 g, 1.666 mmol) prepared in Step 2, trifluoroacetic anhydride (0.209 mL, 1.500 mmol) and triethylamine (0.346 mL, 2.499 mmol) in dichloromethane (10 mL) was stirred at the room temperature for 3 hr. Then, water was added to the reaction mixture, followed by extraction with dichloromethane. The organic layer was washed with brine, dried (anhydrous MgSO$_4$), and concentrated in vacuo. The concentrate was purified and concentrated by column chromatography (SiO$_2$, 12 g cartridge; methanol/dichloromethane=0% to 10%) to give the title compound 4-isopropyl-N-phenyl-

250

N-(4-(2-(2,2,2-trifluoroacetyl)hydrazine-1-carbonyl)benzyl)piperazine-1-carboxamide as Colorless oil (0.507 g, 61.9%).

[Step 4] Compound 21347

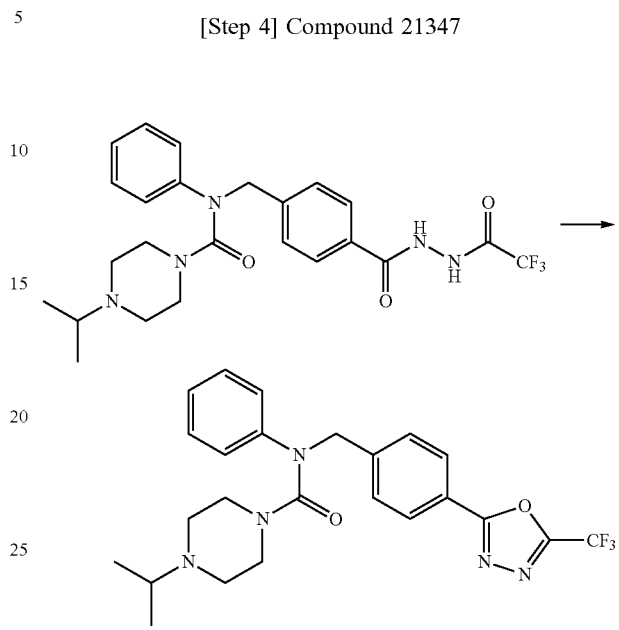

A mixture of 4-isopropyl-N-phenyl-N-(4-(2-(2,2,2-trifluoroacetyl)hydrazine-1-carbonyl)benzyl)piperazine-1-carboxamide (0.507 g, 1.031 mmol) prepared in Step 3 and 1-methoxy-N-triethylammoniosulfonyl-methanimidate (Burgess reagent, 0.320 g, 1.341 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound 4-isopropyl-N-phenyl-N-(4-(5-(trifluoromethyl)-1,3,4-oxadiazol-2-yl)benzyl)piperazine-1-carboxamide as Colorless oil (0.400 g, 81.9%).

$^1$H NMR (400 MHz, CDCl$_3$) δ 8.05-8.04 (m, 2H), 7.52-7.50 (m, 2H), 7.32-7.27 (m, 2H), 7.13-7.09 (m, 1H), 7.06-7.04 (m, 2H), 4.96 (s, 2H), 3.30 (t, 4H, J=4.9 Hz), 2.64-2.59 (m, 1H), 2.35 (t, 4H, J=4.9 Hz), 0.99 (d, 6H, J=6.5 Hz); LRMS (ES) m/z 460.40 (M$^+$+1).

Example 19. Compound 21348: N-phenyl-N-(4-(5-(trifluoromethyl)-1,3,4-oxadiazol-2-yl)phenethyl)morpholine-4-carboxamide

[Step 1] Methyl 4-(2-(phenylamino)ethyl)benzoate

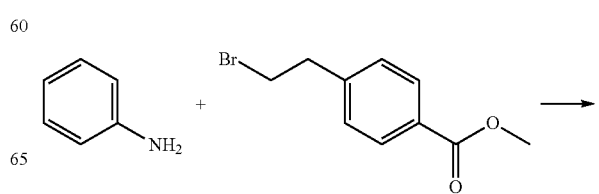

-continued

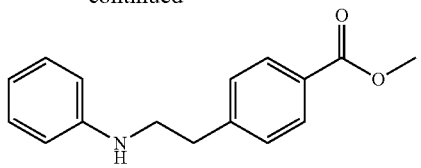

A mixture of aniline (0.500 g, 5.369 mmol), methyl 4-(2-bromoethyl)benzoate (1.305 g, 5.369 mmol) and KI (potassium iodide) (0.089 g, 0.537 mmol) in acetonitrile (10 mL) was stirred at 120° C. for 1 min, then heated at 100° C. under the microwaves for 16 hr, and cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=0% to 5%) to give the title compound methyl 4-(2-(phenylamino)ethyl)benzoate as brown oil (0.675 g, 49.2%).

[Step 2] Methyl 4-(2-(N-phenylmorpholine-4-carboxamido)ethyl)benzoate

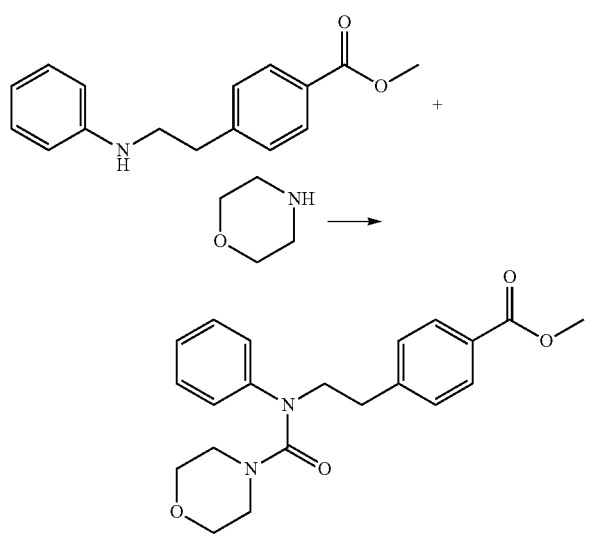

To a stirred solution of methyl 4-(2-(phenylamino)ethyl)benzoate (0.675 g, 2.643 mmol) prepared in Step 1 and N,N-diisopropylethylamine (2.743 mL, 15.855 mmol) in dichloromethane (10 mL) was added at 0° C. triphosgene (0.392 g, 1.321 mmol). The reaction mixture was stirred at the same temperature for 30 min, treated at the room temperature with morpholine (0.254 mL, 2.907 mmol), and stirred for additional 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound methyl 4-(2-(N-phenylmorpholine-4-carboxamido)ethyl)benzoate as colorless oil (0.971 g, 99.8%).

[Step 3] N-(4-(hydrazinecarbonyl)phenethyl)-N-phenylmorpholine-4-carboxamide

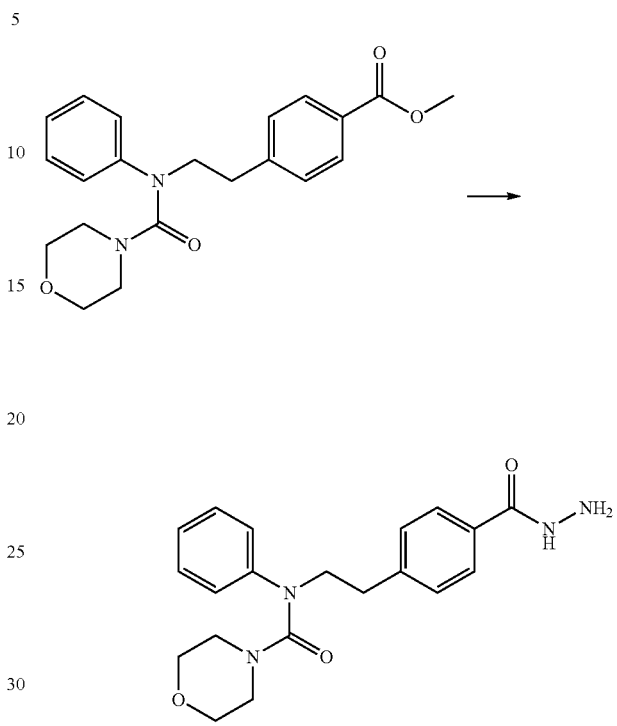

A mixture of methyl 4-(2-(N-phenylmorpholine-4-carboxamido)ethyl)benzoate (0.971 g, 2.636 mmol) prepared in Step 2 and hydrazine monohydrate (2.490 mL, 52.726 mmol) in ethanol (10 mL) was heated at the room temperature for 1 hr under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 5%) to give the title compound N-(4-(hydrazinecarbonyl)phenethyl)-N-phenylmorpholine-4-carboxamide as colorless oil (0.746 g, 76.8%).

[Step 4] N-phenyl-N-(4-(2-(2,2,2-trifluoroacetyl) hydrazine-1-carbonyl)phenethyl)morpholine-4-carboxamide

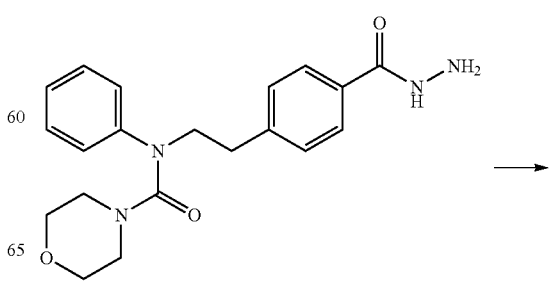

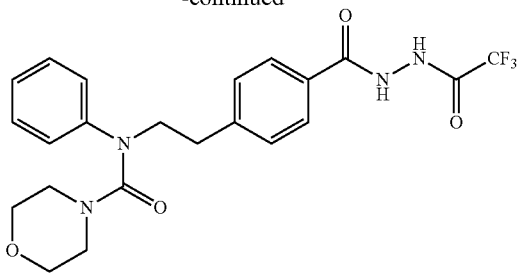

A solution of N-(4-(hydrazinecarbonyl)phenethyl)-N-phenylmorpholine-4-carboxamide (0.746 g, 2.024 mmol) prepared in Step 3 and triethylamine (0.560 mL, 4.048 mmol) in dichloromethane (10 mL) was mixed at the room temperature with trifluoroacetic anhydride (0.316 mL, 1.822 mmol), and stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-phenyl-N-(4-(2-(2,2,2-trifluoroacetyl)hydrazine-1-carbonyl)phenethyl)morpholine-4-carboxamide as colorless oil (0.817 g, 86.9%).

[Step 5] Compound 21348

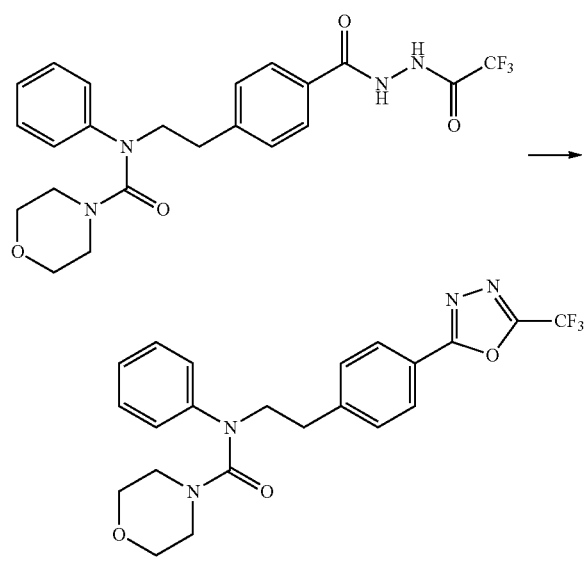

A mixture of N-phenyl-N-(4-(2-(2,2,2-trifluoroacetyl)hydrazine-1-carbonyl)phenethyl)morpholine-4-carboxamide (0.200 g, 0.431 mmol) prepared in Step 4 and 1-methoxy-N-triethylammoniosulfonyl-methanimidate (Burgess reagent, 0.154 g, 0.646 mmol) in tetrahydrofuran (2 mL) was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-phenyl-N-(4-(5-(trifluoromethyl)-1,3,4-oxadiazol-2-yl)phenethyl)morpholine-4-carboxamide as yellow oil (0.178 g, 92.6%).

$^1$H NMR (400 MHz, CDCl$_3$) δ 8.04-7.97 (m, 2H), 7.40-7.34 (m, 2H), 7.34-7.27 (m, 2H), 7.18-7.08 (m, 1H), 7.02-6.94 (m, 2H), 3.89-3.81 (m, 2H), 3.50-3.41 (m, 4H), 3.19-3.11 (m, 4H), 3.03-2.94 (m, 2H); LRMS (ES) m/z 447.21 (M$^+$+1).

Example 20. Compound 21349: N-phenyl-N-(4-(5-(trifluoromethyl)-1,3,4-oxadiazol-2-yl)benzyl)azetidine-1-carboxamide

[Step 1] Methyl 4-((N-phenylazetidine-1-carboxamido)methyl)benzoate

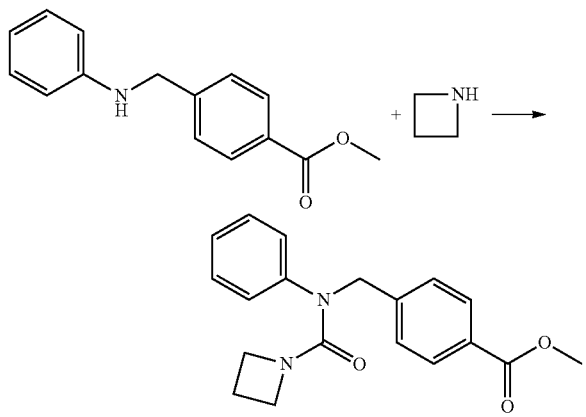

To a stirred solution of methyl 4-((phenylamino)methyl)benzoate (0.500 g, 2.072 mmol) and N,N-diisopropylethylamine (2.151 mL, 12.433 mmol) in dichloromethane (10 mL) was added at 0° C. triphosgene (0.307 g, 1.036 mmol). The reaction mixture was stirred at the same temperature for 30 min, treated at the room temperature with azetidine hydrochloride (0.213 g, 2.279 mmol), and stirred for additional 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=10% to 30%) to give the title compound methyl 4-((N-phenylazetidine-1-carboxamido)methyl)benzoate as yellow oil (0.242 g, 36.0%).

[Step 2] N-(4-(hydrazinecarbonyl)benzyl)-N-phenylazetidine-1-carboxamide

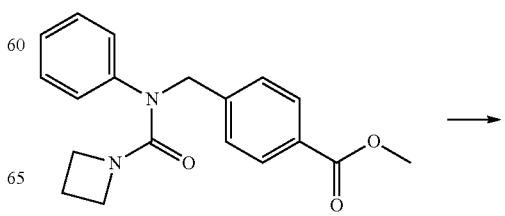

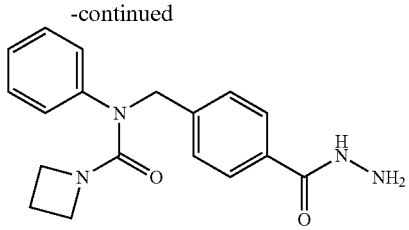

Methyl 4-((N-phenylazetidine-1-carboxamido)methyl)benzoate (0.242 g, 0.746 mmol) prepared in Step 1 and hydrazine monohydrate (0.705 mL, 14.921 mmol) in ethanol (10 mL) was mixed at the room temperature and then heated at 100° C. under the microwaves for 1 hr, and cooled down to the room temperature to terminate the reaction. The reaction mixture was concentrated under the reduced pressure to remove the solvent. The crude product was crystallized at the room temperature using methanol (5 mL). The resulting precipitates were filtered, washed by methanol, and dried to give the title compound N-(4-(hydrazinecarbonyl)benzyl)-N-phenylazetidine-1-carboxamide as white solid (0.175 g, 72.5%).

[Step 3] N-phenyl-N-(4-(2-(2,2,2-trifluoroacetyl)hydrazine-1-carbonyl)benzyl)azetidine-1-carboxamide

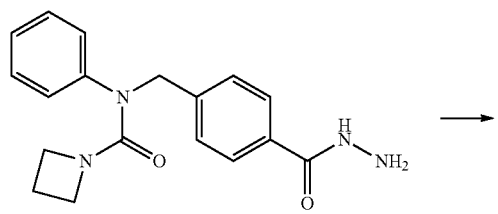

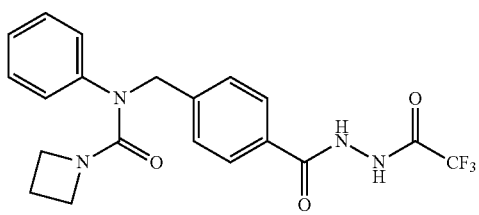

A solution of N-(4-(hydrazinecarbonyl)benzyl)-N-phenylazetidine-1-carboxamide (0.175 g, 0.541 mmol) prepared in Step 2 and triethylamine (0.149 mL, 1.081 mmol) in dichloromethane (2 mL) was mixed at the room temperature with trifluoroacetic anhydride (0.084 mL, 0.487 mmol), and stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-phenyl-N-(4-(2-(2,2,2-trifluoroacetyl)hydrazine-1-carbonyl)benzyl)azetidine-1-carboxamide as colorless oil (0.210 g, 92.4%).

[Step 4] Compound 21349

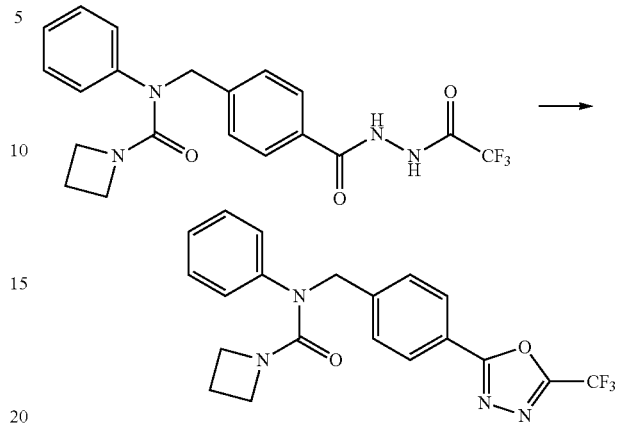

A mixture of N-phenyl-N-(4-(2-(2,2,2-trifluoroacetyl)hydrazine-1-carbonyl)benzyl)azetidine-1-carboxamide (0.210 g, 0.500 mmol) prepared in Step 3 and 1-methoxy-N-triethylammoniosulfonyl-methanimidate (Burgess reagent, 0.179 g, 0.749 mmol) in tetrahydrofuran (2 mL) was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=3%) to give the title compound N-phenyl-N-(4-(5-(trifluoromethyl)-1,3,4-oxadiazol-2-yl)benzyl)azetidine-1-carboxamide as yellow oil (0.140 g, 69.8%).

$^1$H NMR (400 MHz, CDCl₃) δ 8.03-7.96 (m, 2H), 7.44 (d, 2H, J=8.3 Hz), 7.33-7.24 (m, 2H), 7.22-7.13 (m, 1H), 7.12-7.04 (m, 2H), 4.92 (s, 2H), 3.59 (t, 4H, J=7.6 Hz), 1.99 (dq, 2H, J=8.5, 7.6 Hz); LRMS (ES) m/z 403.23 (M⁺+1).

Example 21. Compound 21350: N-phenyl-N-(4-(5-(trifluoromethyl)-1,3,4-oxadiazol-2-yl)benzyl)pyrrolidine-1-carboxamide

[Step 1] Methyl 4-((N-phenylpyrrolidine-1-carboxamido)methyl)benzoate

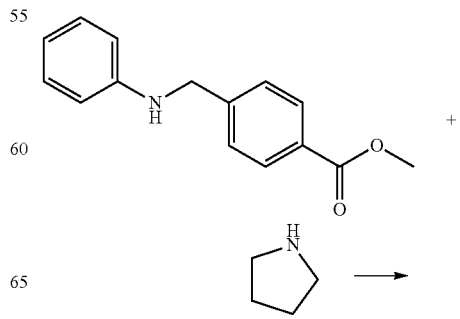

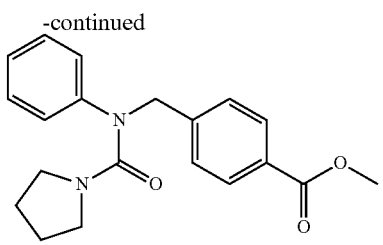

To a stirred solution of methyl 4-((phenylamino)methyl)benzoate (0.500 g, 2.072 mmol) and N,N-diisopropylethylamine (2.151 mL, 12.433 mmol) in dichloromethane (10 mL) was added at 0° C. triphosgene (0.307 g, 1.036 mmol). The reaction mixture was stirred at the same temperature for 30 min, treated at the room temperature with pyrrolidine (0.190 mL, 2.279 mmol), and stirred for additional 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=10% to 30%) to give the title compound methyl 4-((N-phenylpyrrolidine-1-carboxamido)methyl)benzoate as yellow solid (0.713 g, 101.7%).

[Step 2] N-(4-(hydrazinecarbonyl)benzyl)-N-phenylpyrrolidine-1-carboxamide

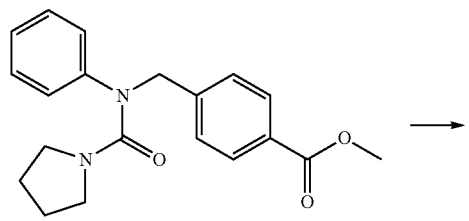

Methyl 4-((N-phenylpyrrolidine-1-carboxamido)methyl)benzoate (0.713 g, 2.107 mmol) prepared in Step 1 and hydrazine monohydrate (1.990 mL, 42.138 mmol) in ethanol (10 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated, in vacuo. The concentrate was purified and concentrated by column chromatography (SiO$_2$, 4 g cartridge; methanol/dichloromethane=0% to 3%) to give the title compound N-(4-(hydrazinecarbonyl)benzyl)-N-phenylpyrrolidine-1-carboxamide as colorless oil (0.282 g, 39.6%).

[Step 3] N-phenyl-N-(4-(2-(2,2,2-trifluoroacetyl)hydrazine-1-carbonyl)benzyl)pyrrolidine-1-carboxamide

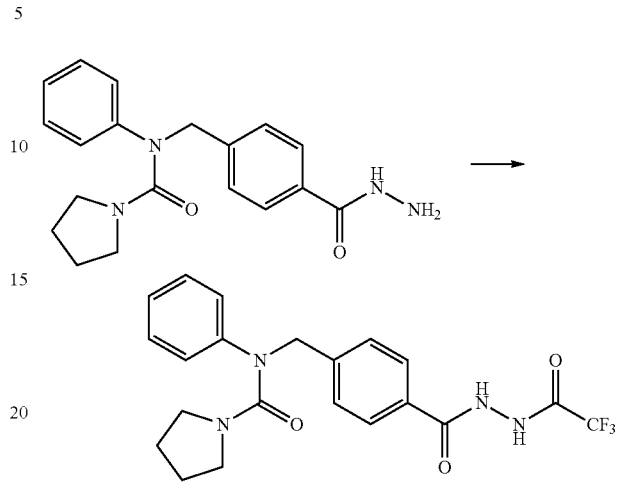

A solution of N-(4-(hydrazinecarbonyl)benzyl)-N-phenylpyrrolidine-1-carboxamide (0.282 g, 0.834 mmol) prepared in Step 2 and triethylamine (0.230 mL, 1.667 mmol) in dichloromethane (2 mL) was mixed at the room temperature with trifluoroacetic anhydride (0.130 mL, 0.750 mmol), and stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-phenyl-N-(4-(2-(2,2,2-trifluoroacetyl)hydrazine-1-carbonyl)benzyl)pyrrolidine-1-carboxamide as colorless oil (0.335 g, 92.5%).

[Step 4] Compound 21350

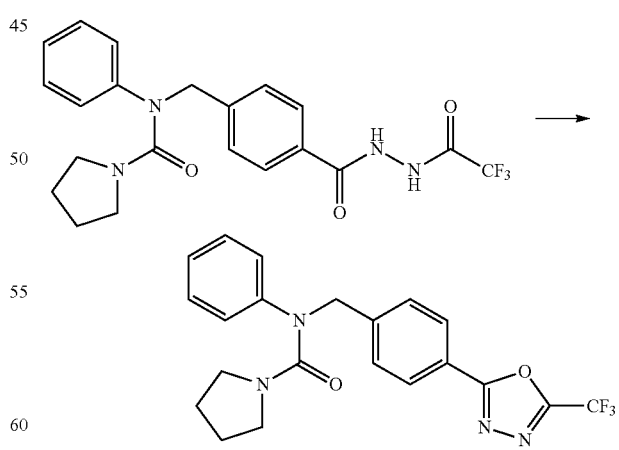

A mixture of N-phenyl-N-(4-(2-(2,2,2-trifluoroacetyl)hydrazine-1-carbonyl)benzyl)pyrrolidine-1-carboxamide (0.335 g, 0.771 mmol) prepared in Step 3 and 1-methoxy-N-triethylammoniosulfonyl-methanimidate (Burgess reagent, 0.276 g, 1.157 mmol) in tetrahydrofuran (2 mL)

was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=3%) to give the title compound N-phenyl-N-(4-(5-(trifluoromethyl)-1,3,4-oxadiazol-2-yl)benzyl)pyrrolidine-1-carboxamide as yellow oil (0.235 g, 73.3%).

¹H NMR (400 MHz, CDCl₃) δ 8.03-7.96 (m, 2H), 7.49 (d, 2H, J=8.3 Hz), 7.27 (dd, 2H, J=8.4, 7.4 Hz), 7.15-7.08 (m, 1H), 7.08-6.99 (m, 2H), 4.94 (s, 2H), 3.15-3.04 (m, 4H), 1.78-1.65 (m, 4H); LRMS (ES) m/z 417.31 (M⁺+1).

Example 22. Compound 21351: N-phenyl-N-(4-(5-(trifluoromethyl)-1,3,4-oxadiazol-2-yl)benzyl)piperidine-1-carboxamide

[Step 1] Methyl 4-((N-phenylpiperidine-1-carboxamido)methyl)benzoate

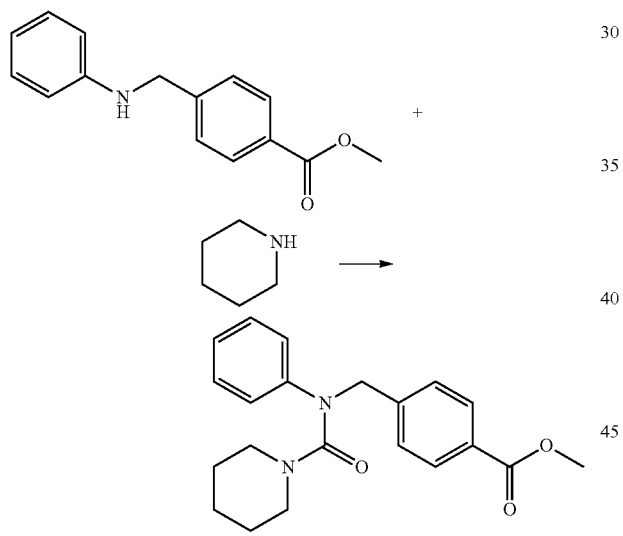

To a stirred solution of methyl 4-((phenylamino)methyl)benzoate (0.500 g, 2.072 mmol) and N,N-diisopropylethylamine (2.151 mL, 12.433 mmol) in dichloromethane (10 mL) was added at 0° C. triphosgene (0.307 g, 1.036 mmol). The reaction mixture was stirred at the same temperature for 30 min, treated at the room temperature with piperidine (0.225 mL, 2.279 mmol), and stirred for additional 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; ethyl acetate/hexane=10% to 30%) to give the title compound methyl 4-((N-phenylpiperidine-1-carboxamido)methyl)benzoate as yellow solid (0.739 g, 101.1%).

[Step 2] N-(4-(hydrazinecarbonyl)benzyl)-N-phenylpiperidine-1-carboxamide

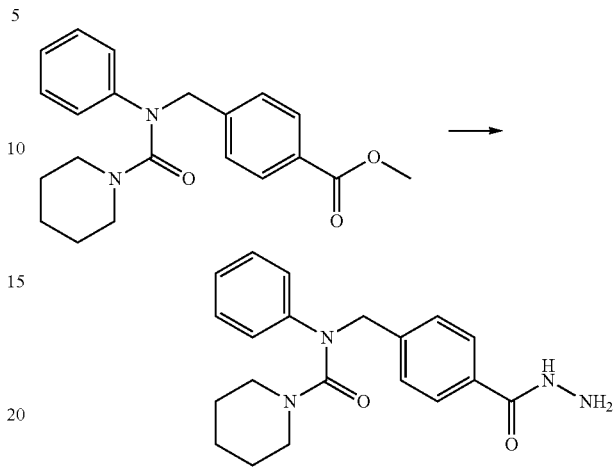

Methyl 4-((N-phenylpiperidine-1-carboxamido)methyl)benzoate (0.739 g, 2.096 mmol) prepared in Step 1 and hydrazine monohydrate (1.979 mL, 41.915 mmol) in ethanol (10 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 3%) to give the title compound N-(4-(hydrazinecarbonyl)benzyl)-N-phenylpiperidine-1-carboxamide as colorless oil (0.379 g, 51.3%).

[Step 3] N-phenyl-N-(4-(2-(2,2,2-trifluoroacetyl)hydrazine-1-carbonyl)benzyl)piperidine-1-carboxamide

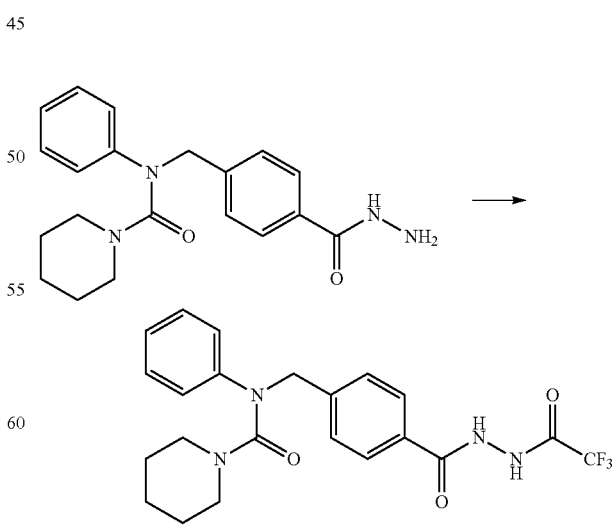

A solution of N-(4-(hydrazinecarbonyl)benzyl)-N-phenylpiperidine-1-carboxamide (0.379 g, 1.076 mmol) prepared in Step 2 and triethylamine (0297 mL, 2.151 mmol) in dichloromethane (5 mL) was mixed at the room temperature with trifluoroacetic anhydride (0.168 mL, 0.968 mmol), and stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-phenyl-N-(4-(2-(2,2,2-trifluoroacetyl)hydrazine-1-carbonyl)benzyl)piperidine-1-carboxamide as colorless oil (0.435 g, 90.2%).

[Step 4] Compound 21351

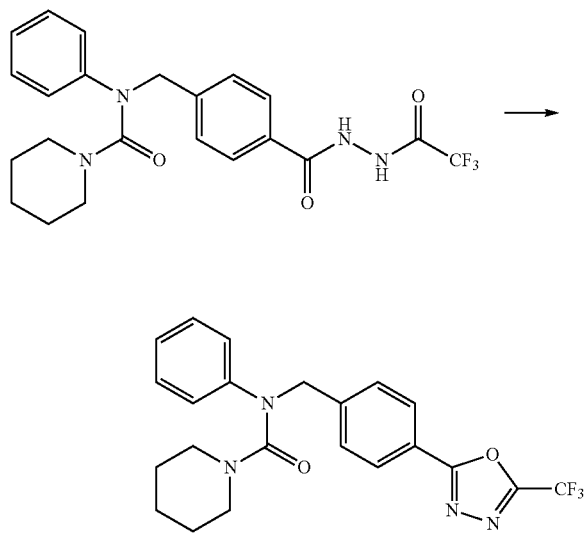 [SMILES: O=C(NNC(=O)C(F)(F)F)c1ccc(CN(C(=O)N2CCCC2)c2ccccc2)cc1 ; O=C(N1CCCC1)N(Cc1ccc(-c2nnc(C(F)(F)F)o2)cc1)c1ccccc1]

A mixture of N-phenyl-N-(4-(2-(2,2,2-trifluoroacetyl)hydrazine-1-carbonyl)benzyl)piperidine-1-carboxamide (0.435 g, 0.970 mmol) prepared in Step 3 and 1-methoxy-N-triethylammoniosulfonyl-methanimidate (Burgess reagent, 0.347 g, 1.455 mmol) in tetrahydrofuran (2 mL) was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-phenyl-N-(4-(5-(trifluoromethyl)-1,3,4-oxadiazol-2-yl)benzyl)piperidine-1-carboxamide as yellow oil (0.324 g, 77.6%).

$^1$H NMR (400 MHz, CDCl$_3$) δ 8.02 (d, 2H, J=8.3 Hz), 7.50 (d, 2H, J=8.3 Hz), 7.33-7.24 (m, 2H), 7.13-7.00 (m, 3H), 4.93 (s, 2H), 3.26-3.18 (m, 4H), 1.48 (m, 2H), 1.36 (m, 4H); LRMS (ES) m/z 431.04 (M$^+$+1).

Example 23. Compound 21352: Tert-butyl 4-(phenyl(4-(5-(trifluoromethyl)-1,3,4-oxadiazol-2-yl)benzyl)carbamoyl)piperazine-1-carboxylate

[Step 1] Tert-butyl 4-((4-(methoxycarbonyl)benzyl)(phenyl)carbamoyl)piperazine-1-carboxylate

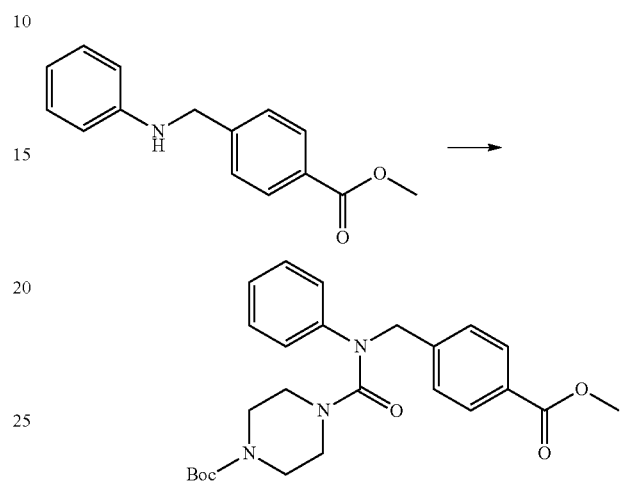

To a stirred solution of methyl 4-((phenylamino)methyl)benzoate (2.000 g, 8.289 mmol) in dichloromethane (100 mL) were added at 0° C. triphosgene (1.968 g, 6.631 mmol) and N,N-diisopropylethylamine (7.238 mL, 41.444 mmol). The reaction mixture was stirred at the same temperature for 1 hr, treated at the same temperature with tert-butyl piperazine-1-carboxylate (1.853 g, 9.947 mmol), stirred for additional 2 hr, and quenched at 0° C. by the addition of saturated aqueous sodium bicarbonate solution (150 mL, 10 min stirring). Then, saturated aqueous sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 40 g cartridge; ethyl acetate/hexane=10% to 70%) to give the title compound tert-butyl 4-((4-(methoxycarbonyl)benzyl)(phenyl)carbamoyl)piperazine-1-carboxylate as white solid (3.700 g, 98.4%).

[Step 2] Tert-butyl 4-((4-(hydrazinecarbonyl)benzyl)(phenyl)carbamoyl)piperazine-1-carboxylate

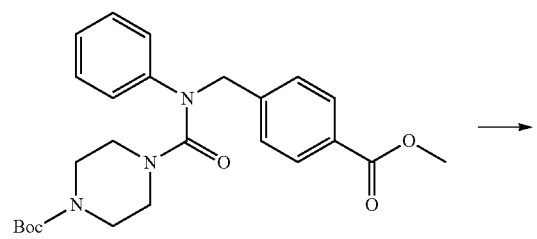

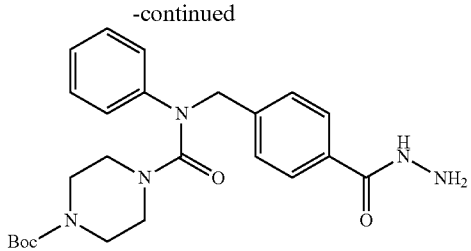

Tert-butyl 4-((4-(methoxycarbonyl)benzyl)(phenyl)carbamoyl)piperazine-1-carboxylate (2.500 g, 5.512 mmol) prepared in Step 1 and hydrazine monohydrate (5.358 mL, 110.244 mmol) in ethanol (30 mL) was mixed at the room temperature and then heated at 120° C. under the microwaves for 2 hr, and cooled down to the room temperature to terminate the reaction. Then, the reaction mixture was concentrated under the reduced pressure to remove the solvent. The concentrate was purified and concentrated by column chromatography (SiO$_2$, 40 g cartridge; methanol/dichloromethane=0% to 10%) to give the title compound tert-butyl 4-((4-(hydrazinecarbonyl)benzyl)(phenyl)carbamoyl)piperazine-1-carboxylate as colorless oil (1.220 g, 48.8%).

[Step 3] Tert-butyl 4-(phenyl(4-(2-(2,2,2-trifluoroacetyl)hydrazine-1-carbonyl)benzyl)carbamoyl)piperazine-1-carboxylate

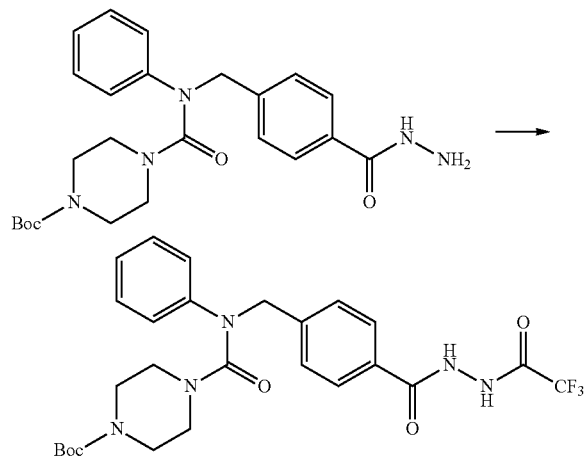

A solution of tert-butyl 4-((4-(hydrazinecarbonyl)benzyl)(phenyl)carbamoyl)piperazine-1-carboxylate (2.250 g, 4.961 mmol) prepared in Step 2, trifluoroacetic anhydride (0.555 mL, 4.465 mmol) and triethylamine (1.032 mL, 7.441 mmol) in dichloromethane (100 mL) was stirred at the room temperature for 17 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 40 g cartridge; ethyl acetate/hexane=50% to 100%) to give the title compound tert-butyl 4-(phenyl(4-(2-(2,2,2-trifluoroacetyl)hydrazine-1-carbonyl)benzyl)carbamoyl)piperazine-1-carboxylate as colorless oil (1.440 g, 52.8%).

[Step 4] Compound 21352

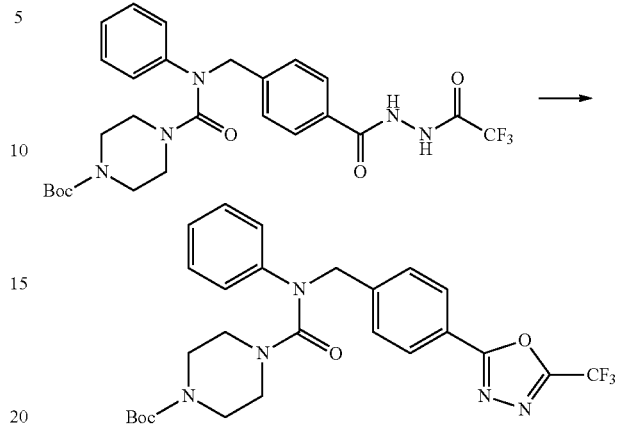

Tert-butyl 4-(phenyl(4-(2-(2,2,2-trifluoroacetyl)hydrazine-1-carbonyl)benzyl)carbamoyl)piperazine-1-carboxylate (1.100 g, 2.002 mmol) prepared in Step 3 and 1-methoxy-N-triethylammoniosulfonyl-methanimidate (Burgess reagent, 0.715 g, 3.002 mmol) in tetrahydrofuran (15 mL) was mixed at the room temperature and then heated at 100° C. under the microwaves for 30 min, and cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=20% to 30%) to give the title compound tert-butyl 4-(phenyl(4-(5-(trifluoromethyl)-1,3,4-oxadiazol-2-yl)benzyl)carbamoyl)piperazine-1-carboxylate as white solid (0.776 g, 72.9%).
$^1$H NMR (400 MHz, CDCl$_3$) δ 8.04 (d, 2H, J=8.3 Hz), 7.50 (d, 2H, J=8.3 Hz), 7.33 (t, 2H, J=7.9 Hz), 7.15 (t, 1H, J=7.4 Hz), 7.08 (d, 2H, J=8.6 Hz), 4.95 (s, 2H), 3.24 (s, 8H), 1.44 (s, 9H); LRMS (ES) m/z 530.7 (M−1).

Example 24. Compound 21353: 3-Ethyl-1-phenyl-1-(4-(5-(trifluoromethyl)-1,3,4-oxadiazol-2-yl)benzyl)urea

[Step 1] Methyl 4-((3-ethyl-1-phenylureido)methyl)benzoate

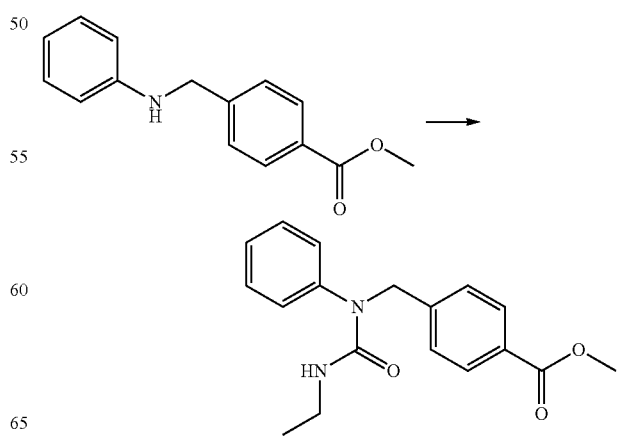

A solution of methyl 4-((phenylamino)methyl)benzoate (0.500 g, 2.072 mmol) in dichloromethane (10 mL) was mixed at 0° C. with triphosgene (0.492 g, 1.658 mmol) and N,N-diisopropylethylamine (1.339 g, 10.361 mmol), and stirred at the same temperature for 1 hr. The reaction mixture was stirred at the room temperature for additional 17 hr. Then, saturated aqueous sodium bicarbonate solution was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound methyl 4-((3-ethyl-1-phenylureido)methyl)benzoate as pale yellow oil (0.413 g, 63.8%).

[Step 2] 3-Ethyl-1-phenyl-1-(4-(2-(2,2,2-trifluoroacetyl)hydrazine-1-carbonyl)benzyl)urea

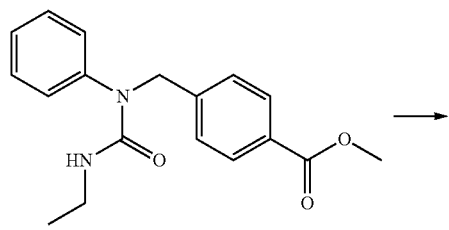

Methyl 4-((3-ethyl-1-phenylureido)methyl)benzoate (0.413 g, 1.322 mmol) prepared in Step 1 and hydrazine monohydrate (1.285 mL, 26.443 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent. The concentrate was purified and concentrated by column chromatography (SiO₂, 12 g cartridge; ethyl acetate/hexane=60% to 100%) to give the title compound 3-ethyl-1-phenyl-1-(4-(2-(2,2,2-trifluoroacetyl)hydrazine-1-carbonyl)benzyl)urea as white solid (0.232 g, 56.2%).

[Step 3] 3-Ethyl-1-phenyl-1-(4-(2-(2,2,2-trifluoroacetyl)hydrazine-1-carbonyl)benzyl)urea

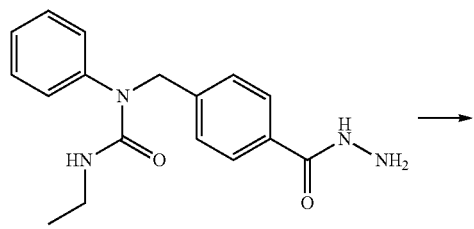

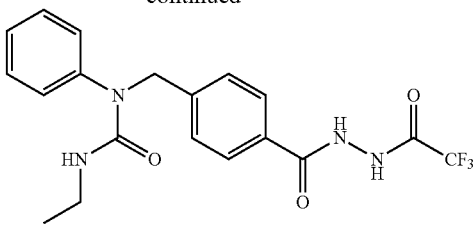

A solution of 3-ethyl-1-(4-(hydrazinecarbonyl)benzyl)-1-phenylurea (0.232 g, 0.743 mmol) prepared in Step 2 and triethylamine (0.154 mL, 1.114 mmol) in dichloromethane (10 mL) was mixed at the room temperature with trifluoroacetic anhydride (0.083 mL, 0.668 mmol). The reaction mixture was stirred at the same temperature for 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; ethyl acetate/hexane=0% to 5%) to give the title compound 3-ethyl-1-phenyl-1-(4-(2-(2,2,2-trifluoroacetyl)hydrazine-1-carbonyl)benzyl)urea as white solid (0.119 g, 39.2%).

[Step 4] Compound 21353

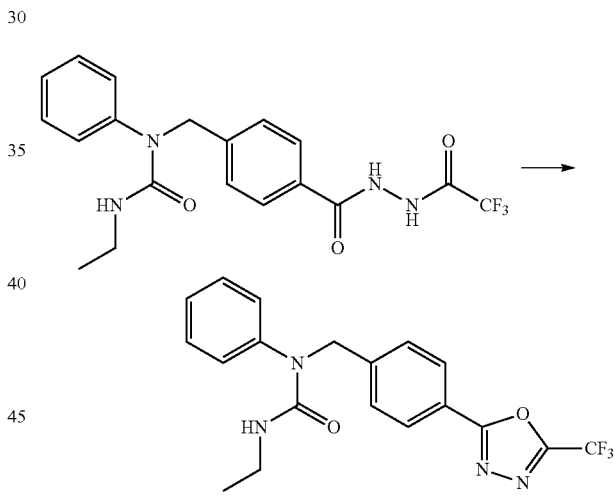

3-Ethyl-1-phenyl-1-(4-(2-(2,2,2-trifluoroacetyl)hydrazine-1-carbonyl)benzyl)urea (0.119 g, 0.291 mmol) and 1-methoxy-N-triethylammoniosulfonyl-methanimidate (Burgess reagent, 0.104 g, 0.437 mmol) in tetrahydrofuran (4 mL) was mixed at the room temperature and then heated at 150° C. under the microwaves for 30 min, and cooled down to the room temperature to terminate the reaction. The reaction mixture was concentrated under the reduced pressure to remove the solvent. The concentrate was purified and concentrated by column chromatography (SiO₂, 4 g cartridge; ethyl acetate/hexane=10% to 30%) to give the title compound 3-ethyl-1-phenyl-1-(4-(5-(trifluoromethyl)-1,3,4-oxadiazol-2-yl)benzyl)urea as pale yellow oil (0.026 g, 22.9%).

$^1$H NMR (400 MHz, CDCl₃) δ 8.04 (d, 2H, J=8.3 Hz), 7.47 (d, 2H, J=8.3 Hz), 7.41-7.37 (m, 2H), 7.32-7.30 (m, 1H), 7.13-7.11 (m, 2H), 4.98 (s, 2H), 4.31 (brs, 1H), 3.28 (q, 2H, J=7.1 Hz), 1.08 (t, 3H, J=7.2 Hz).

267

Example 25. Compound 21354: 1-Phenyl-3-propyl-1-(4-(5-(trifluoromethyl)-1,3,4-oxadiazol-2-yl)benzyl)urea

[Step 1] Methyl 4-((1-phenyl-3-propylureido)methyl)benzoate

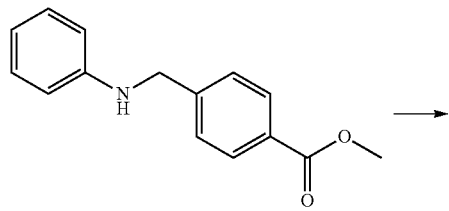

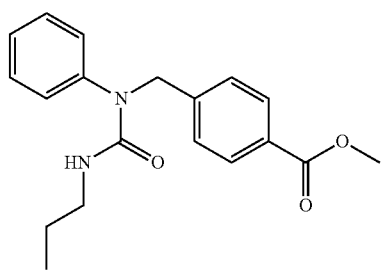

To a stirred solution of methyl 4-((phenylamino)methyl)benzoate (0.500 g, 2.072 mmol) in dichloromethane (10 mL) were added at 0° C. triphosgene (0.492 g, 1.658 mmol) and N,N-diisopropylethylamine (1.339 g, 10.361 mmol). The reaction mixture was stirred at the same temperature for 1 hr, treated at the room temperature with propylamine (0.204 mL, 2.487 mmol), and stirred for additional 17 hr. Then, saturated aqueous sodium bicarbonate solution was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 20%) to give the title compound methyl 4-((1-phenyl-3-propylureido)methyl)benzoate as white solid (0.622 g, 92.0%).

[Step 2] 1-(4-(Hydrazinecarbonyl)benzyl)-1-phenyl-3-propylurea

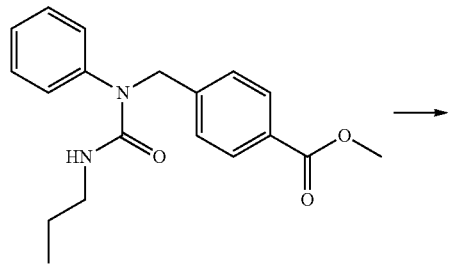

268

-continued

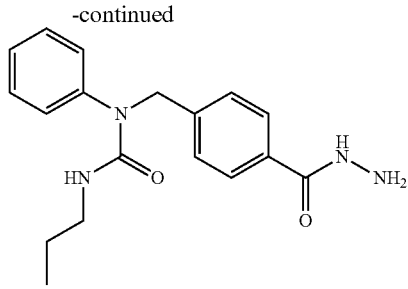

Methyl 4-((1-phenyl-3-propylureido)methyl)benzoate (0.622 g, 1.906 mmol) prepared in Step 1 and hydrazine monohydrate (1.852 mL, 38.113 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent. The concentrate was purified and concentrated by column chromatography (SiO₂, 12 g cartridge; ethyl acetate/hexane=40% to 100%) to give the title compound 1-(4-(hydrazinecarbonyl)benzyl)-1-phenyl-3-propylurea as white solid (0.570 g, 91.6%).

[Step 3] 1-Phenyl-3-propyl-1-(4-(2-(2,2,2-trifluoroacetyl)hydrazine-1-carbonyl)benzyl)urea

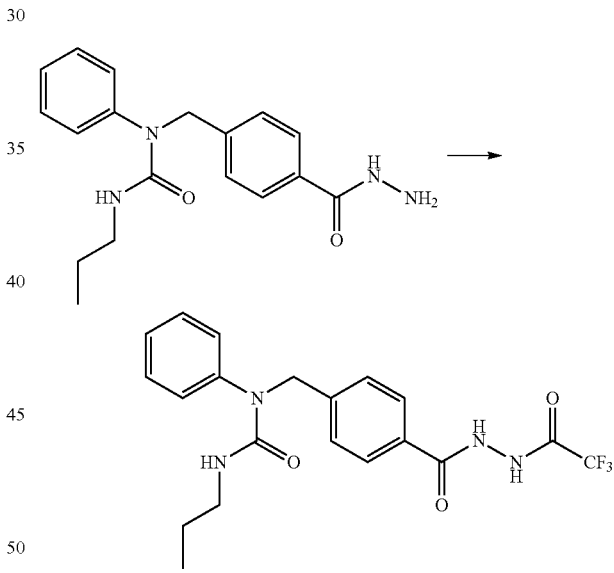

A solution of 1-(4-(hydrazinecarbonyl)benzyl)-1-phenyl-3-propylurea (0.570 g, 1.746 mmol) prepared in Step 2 and triethylamine (0.363 mL, 2.619 mmol) in dichloromethane (10 mL) was mixed at the room temperature with trifluoroacetic anhydride (0.195 mL, 1.572 mmol). The reaction mixture was stirred at the same temperature for 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; ethyl acetate/hexane=0% to 5%) to give the title compound 1-phenyl-3-propyl-1-(4-(2-(2,2,2-trifluoroacetyl)hydrazine-1-carbonyl)benzyl)urea as white solid (0.215 g, 29.1%).

[Step 4] Compound 21354

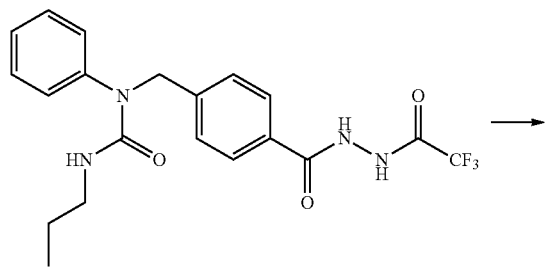

1-Phenyl-3-propyl-1-(4-(2-(2,2,2-trifluoroacetyl)hydrazine-1-carbonyl)benzyl)urea (0.215 g, 0.509 mmol) prepared in Step 3 and 1-methoxy-N-triethylammoniosulfonylmethanimidate (Burgess reagent, 0.182 g, 0.763 mmol) in tetrahydrofuran (4 mL) was mixed at the room temperature and then heated at 150° C. under the microwaves for 30 min, and cooled down to the room temperature to terminate the reaction. The reaction mixture was concentrated under the reduced pressure to remove the solvent. The concentrate was purified and concentrated by column chromatography (SiO$_2$, 4 g cartridge; ethyl acetate/hexane=0% to 20%) to give the title compound 1-phenyl-3-propyl-1-(4-(5-(trifluoromethyl)-1,3,4-oxadiazol-2-yl)benzyl)urea as pale yellow oil (0.007 g, 3.4%).

$^1$H NMR (400 MHz, CDCl$_3$) δ 8.04 (d, 2H, J=8.3 Hz), 7.47 (d, 2H, J=8.3 Hz), 7.41-7.36 (m, 2H), 7.34-7.28 (m, 1H), 7.13-7.11 (m, 2H), 4.97 (s, 2H), 4.35 (brs, 1H), 3.20 (q, 2H, J=6.5 Hz), 1.49-1.42 (m, 2H), 0.86 (t, 3H, J=7.4 Hz).

Example 26. Compound 21355: N-phenyl-N-(4-((5-(trifluoromethyl)-1,3,4-oxadiazol-2-yl)methyl)benzyl)morpholine-4-carboxamide

[Step 1] Methyl 2-(4-((phenylamino)methyl)phenyl)acetate

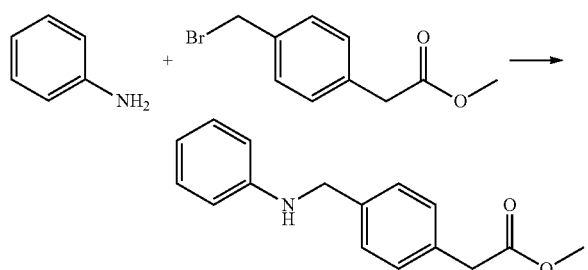

A solution of aniline (1.471 mL, 16.107 mmol) and sodium hydride (60.00%, 0.966 g, 24.160 mmol) in N,N-dimethylformamide (100 mL) was stirred at the room temperature for 30 min, and mixed with methyl 2-(4-(bromomethyl)phenyl)acetate (4.307 g, 17.717 mmol). The reaction mixture was stirred at the same temperature for additional 17 hr, and quenched at the room temperature by the addition of saturated aqueous sodium bicarbonate solution (50 mL, 30 min stirring). Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 40 g cartridge; ethyl acetate/hexane=0% to 10%) to give the title compound methyl 2-(4-((phenylamino)methyl)phenyl)acetate as pale yellow oil (1.710 g, 41.6%).

[Step 2] Methyl 2-(4-((N-phenylmorpholine-4-carboxamido)methyl)phenyl)acetate

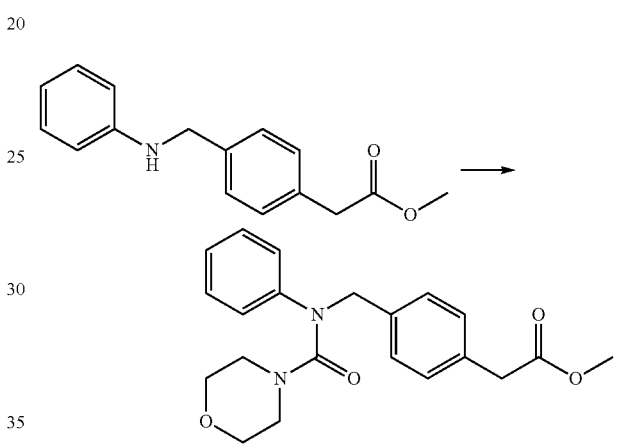

Methyl 2-(4-((phenylamino)methyl)phenyl)acetate (1.710 g, 6.697 mmol) prepared in Step 1, morpholine-4-carbonyl chloride (1.172 mL, 10.046 mmol), N,N-diisopropylethylamine (2.339 mL, 13.395 mmol) and N,N-dimethylaminopyridine (DMAP) (0.082 g, 0.670 mmol) were mixed at the room temperature in toluene (50 mL) and then stirred at 100° C. for 48 hr, and cooled down to the room temperature to terminate the reaction. The reaction mixture was concentrated under the reduced pressure to remove the solvent. The concentrate was purified and concentrated by column chromatography (SiO$_2$, 40 g cartridge; ethyl acetate/hexane=30% to 50%) to give the title compound methyl 2-(4-((N-phenylmorpholine-4-carboxamido)methyl)phenyl)acetate as brown oil (2.110 g, 85.5%).

[Step 3] N-(4-(2-hydrazinyl-2-oxoethyl)benzyl)-N-phenylmorpholine-4-carboxamide

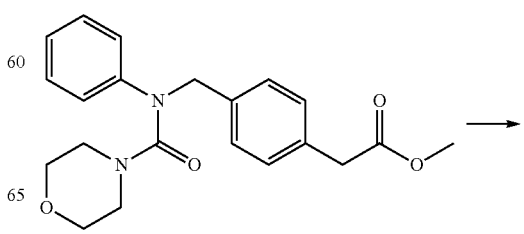

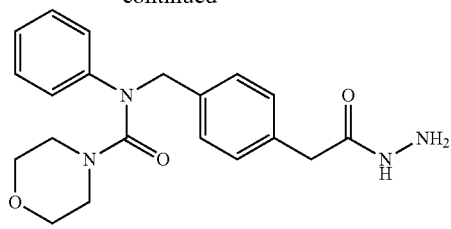

Methyl 2-(4-((N-phenylmorpholine-4-carboxamido)methyl)phenyl)acetate (1.000 g, 2.714 mmol) prepared in Step 2 and hydrazine monohydrate (2.638 mL, 54.284 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=30% to 100%) to give the title compound N-(4-(2-hydrazinyl-2-oxoethyl)benzyl)-N-phenylmorpholine-4-carboxamide as pale yellow oil (0.693 g, 69.3%).

[Step 4] N-(4-(2-oxo-2-(2-(2,2,2-trifluoroacetyl)hydrazinyl)ethyl)benzyl)-N-phenylmorpholine-4-carboxamide

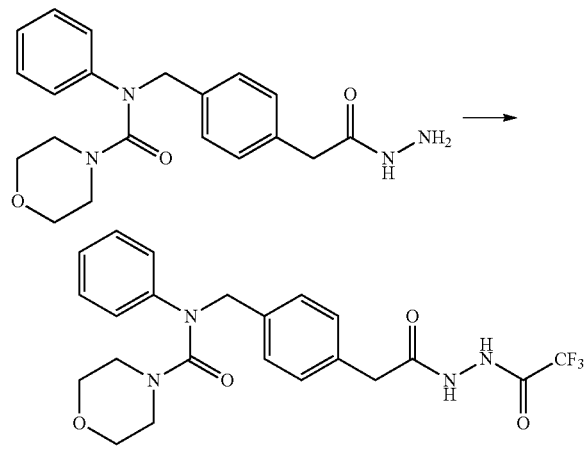

A solution of N-(4-(2-hydrazinyl-2-oxoethyl)benzyl)-N-phenylmorpholine-4-carboxamide (0.693 g, 1.881 mmol) prepared in Step 3 and triethylamine (0.391 mL, 2.821 mmol) in dichloromethane (10 mL) was mixed at the room temperature with trifluoroacetic anhydride (0.210 mL, 1.693 mmol). The reaction mixture was stirred at the same temperature for 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 5%) to give the title compound N-(4-(2-oxo-2-(2-(2,2,2-trifluoroacetyl)hydrazinyl)ethyl)benzyl)-N-phenylmorpholine-4-carboxamide as pale yellow oil (0.404 g, 46.2%).

[Step 5] Compound 21355

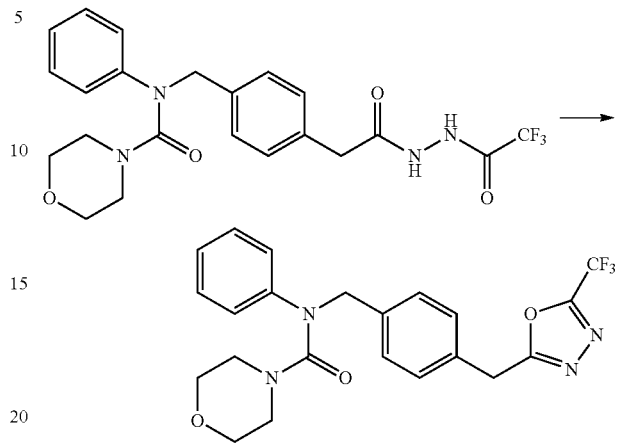

N-(4-(2-oxo-2-(2-(2,2,2-trifluoroacetyl)hydrazinyl)ethyl)benzyl)-N-phenylmorpholine-4-carboxamide (0.200 g, 0.431 mmol) prepared in Step 4 and 1-methoxy-N-triethylammoniosulfonyl-methanimidate (Burgess reagent, 0.154 g, 0.646 mmol) in tetrahydrofuran (4 mL) was mixed at the room temperature and then heated at 150° C. under the microwaves for 30 min, and cooled down to the room temperature to terminate the reaction. The reaction mixture was concentrated under the reduced pressure to remove the solvent. The concentrate was purified and concentrated by column chromatography (SiO$_2$, 4 g cartridge; ethyl acetate/hexane=10% to 50%) to give the title compound N-phenyl-N-(4-((5-(trifluoromethyl)-1,3,4-oxadiazol-2-yl)methyl)benzyl)morpholine-4-carboxamide as pale yellow oil (0.043 g, 22.4%).

$^1$H NMR (400 MHz, CDCl$_3$) δ 7.30-7.28 (m, 4H), 7.26-7.24 (m, 2H), 7.13 (t, 1H, J=7.4 Hz), 7.08 (dd, 2H, J=8.5, 1.0 Hz), 4.87 (s, 2H), 4.27 (s, 2H), 3.49 (t, 4H, J=4.8 Hz), 3.25 (t, 4H, J=4.8 Hz); LRMS (ES) m/z 447.5 (M$^+$+1).

Example 27. Compound 21357: 1-Phenyl-3-((tetrahydro-2H-pyran-4-yl)methyl)-1-(4-(5-(trifluoromethyl)-1,3,4-oxadiazol-2-yl)benzyl)urea

[Step 1] Methyl 4-((1-phenyl-3-((tetrahydro-2H-pyran-4-yl)methyl)ureido)methyl)benzoate

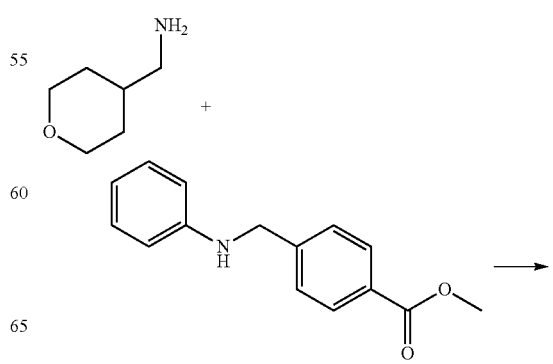

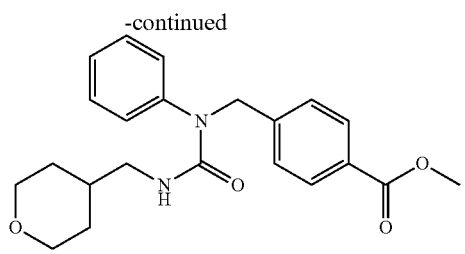

To a stirred solution of methyl 4-((phenylamino)methyl)benzoate (0.300 g, 1.244 mmol) in dichloromethane (10 mL) were added at 0° C. N,N-diisopropylethylamine (1.101 mL, 6.218 mmol) and triphosgene (0.295 g, 0.995 mmol). The reaction mixture was stirred at the same temperature for 30 min, treated at the room temperature with (tetrahydro-2H-pyran-4-yl)methanamine (0.162 mL, 1.368 mmol), and stirred for additional 4 hr. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound methyl 4-((1-phenyl-3-((tetrahydro-2H-pyran-4-yl)methyl)ureido)methyl)benzoate as Colorless oil (0.447 g, 94.0%).

[Step 2] 1-(4-(Hydrazinecarbonyl)benzyl)-1-phenyl-3-((tetrahydro-2H-pyran-4-yl)methyl)urea

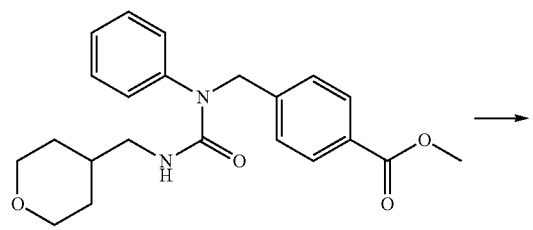

A mixture of methyl 4-((1-phenyl-3-((tetrahydro-2H-pyran-4-yl)methyl)ureido)methyl)benzoate (0.447 g, 1.169 mmol) prepared in Step 1 and hydrazine monohydrate (0.552 mL, 11.687 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo to give the title compound 1-(4-(hydrazinecarbonyl)benzyl)-1-phenyl-3-((tetrahydro-2H-pyran-4-yl)methyl)urea (0.440 g, 98.4%, Colorless oil).

[Step 3] 1-Phenyl-3-((tetrahydro-2H-pyran-4-yl)methyl)-1-(4-(2-(2,2,2-trifluoroacetyl)hydrazine-1-carbonyl)benzyl)urea

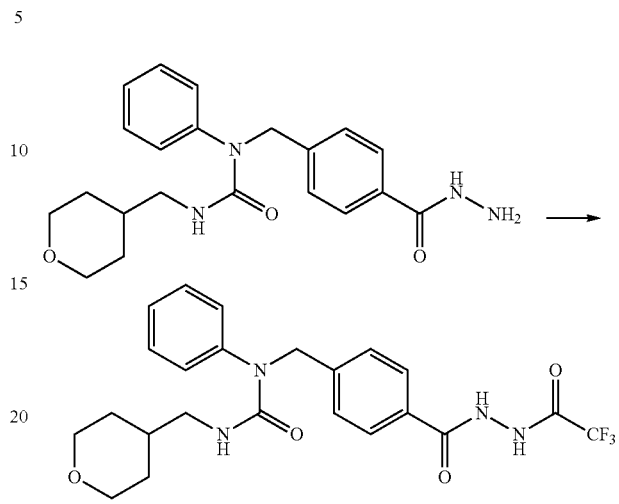

A solution of 1-(4-(hydrazinecarbonyl)benzyl)-1-phenyl-3-((tetrahydro-2H-pyran-4-yl)methyl)urea (0.436 g, 1.140 mmol) prepared in Step 2, trifluoroacetic anhydride (0.143 mL, 1.026 mmol) and triethylamine (0.237 mL, 1.710 mmol) in dichloromethane (10 mL) was stirred at the room temperature for 4 hr. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound 1-phenyl-3-((tetrahydro-2H-pyran-4-yl)methyl)-1-(4-(2-(2,2,2-trifluoroacetyl)hydrazine-1-carbonyl)benzyl)urea as Colorless oil (0.349 g, 64.0%).

[Step 4] Compound 21357

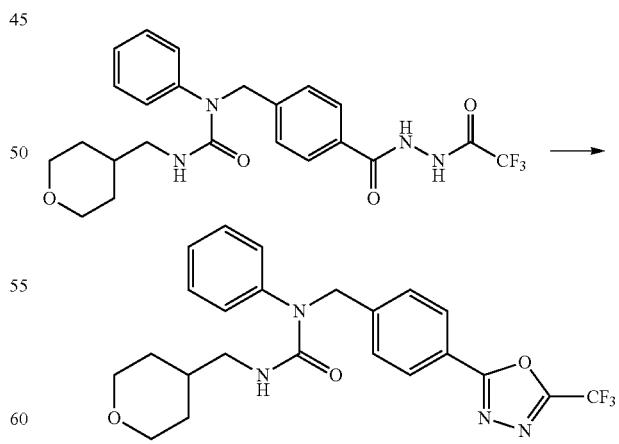

A mixture of 1-phenyl-3-((tetrahydro-2H-pyran-4-yl)methyl)-1-(4-(2-(2,2,2-trifluoroacetyl)hydrazine-1-carbonyl)benzyl)urea (0.349 g, 0.729 mmol) prepared in Step 3 and 1-methoxy-N-triethylammoniosulfonyl-methanimidate (Burgess reagent, 0.226 g, 0.948 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound 1-phenyl-3-((tetrahydro-2H-pyran-4-yl)methyl)-1-(4-(5-(trifluoromethyl)-1,3,4-oxadiazol-2-yl)benzyl)urea as Colorless oil (0.200 g, 59.5%).

$^1$H NMR (400 MHz, CDCl₃) δ 8.06-8.03 (m, 2H), 7.46 (d, 2H, J=8.4 Hz), 7.42-7.32 (m, 3H), 7.13-7:10 (m, 2H), 4.97 (s, 2H), 4.42 (t, 1H, J=6.0 Hz), 3.97 (dd, 2H, J=11.0, 3.3 Hz), 3.40-3.33 (m, 2H), 3.13 (t, 2H, J=6.4 Hz), 1.76-1.70 (m, 1H), 1.54-1.51 (m, 2H), 1.29-1.18 (m, 2H), 1.29-1.18 (m, 2H) LRMS (ES) m/z 461.2 (M$^+$+1).

Example 28. Compound 21358: N,4-diphenyl-N-(4-(5-(trifluoromethyl)-1,3,4-oxadiazol-2-yl)benzyl)piperazine-1-carboxamide

[Step 1] Methyl 4-((N,4-diphenylpiperazine-1-carboxamido)methyl)benzoate

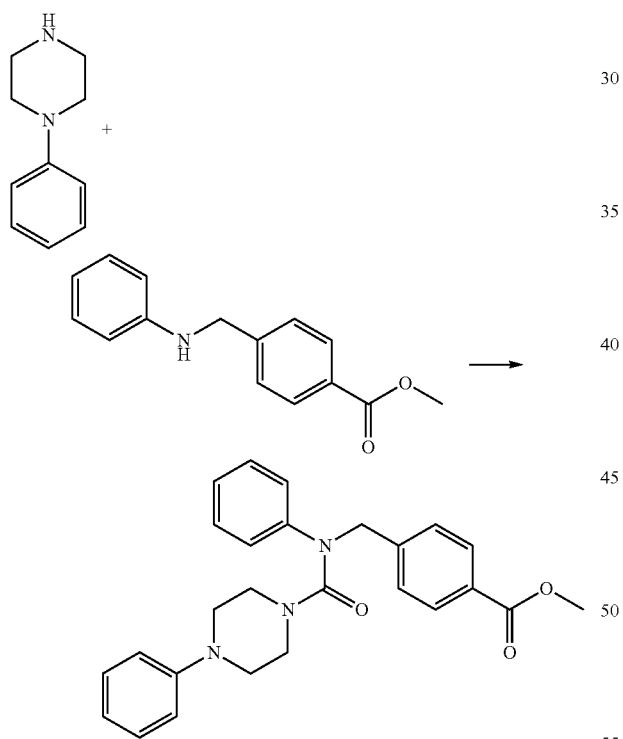

To a stirred solution of methyl 4-((phenylamino)methyl)benzoate (0.300 g, 1.244 mmol) in dichloromethane (10 mL) were added at 0° C. N,N-diisopropylethylamine (1.101 mL, 6.218 mmol) and triphosgene (0.295 g, 0.995 mmol). The reaction mixture was stirred at the same temperature for 30 min, treated at the room temperature with 1-phenylpiperazine (0.215 mL, 1.368 mmol), and stirred for additional 4 hrr. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound methyl 4-((N,4-diphenylpiperazine-1-carboxamido)methyl)benzoate as Colorless oil (0.450 g, 84.2%).

[Step 2] N-(4-(hydrazinecarbonyl)benzyl)-N,4-diphenylpiperazine-1-carboxamide

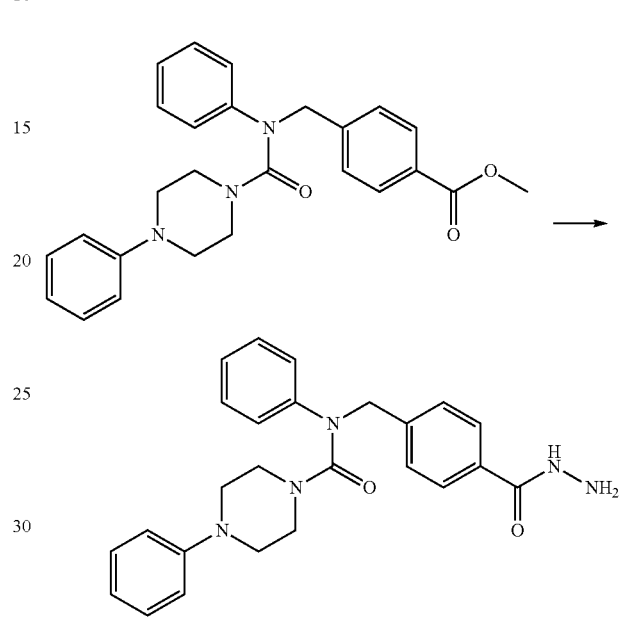

A mixture of methyl 4-((N,4-diphenylpiperazine-1-carboxamido)methyl)benzoate (0.450 g, 1.048 mmol) prepared in Step 1 and hydrazine monohydrate (0.495 mL, 10.477 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO₄), filtered, and concentrated in vacuo to give the title compound N-(4-(hydrazinecarbonyl)benzyl)-N,4-diphenylpiperazine-1-carboxamide (0.450 g, 100.0%, Colorless oil)

[Step 3] N,4-diphenyl-N-(4-(2-(2,2,2-trifluoroacetyl)hydrazine-1-carbonyl)benzyl)piperazine-1-carboxamide

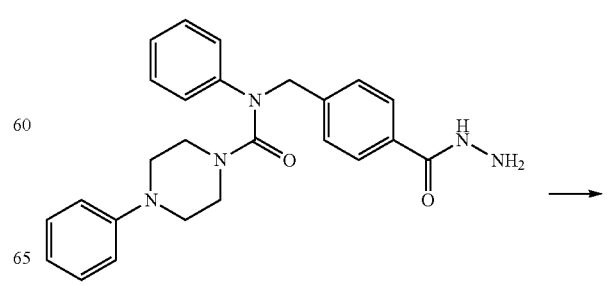

-continued

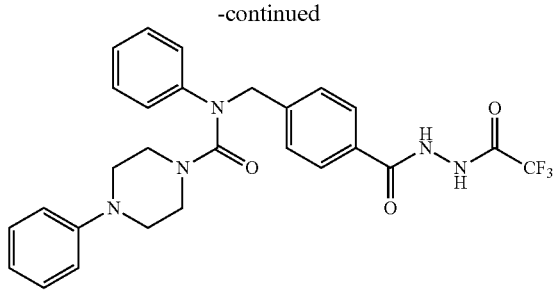

A solution of N-(4-(hydrazinecarbonyl)benzyl)-N,4-diphenylpiperazine-1-carboxamide (0.450 g, 1.048 mmol) prepared in Step 2, trifluoroacetic anhydride (0.131 mL, 0.943 mmol) and triethylamine (0.218 mL, 1,572 mmol) in dichloromethane (10 mL) was stirred at the room temperature for 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N,4-diphenyl-N-(4-(2-(2,2,2-trifluoroacetyl)hydrazine-1-carbonyl)benzyl)piperazine-1-carboxamide as Colorless oil (0.195 g, 35.4%).

[Step 4] Compound 21358

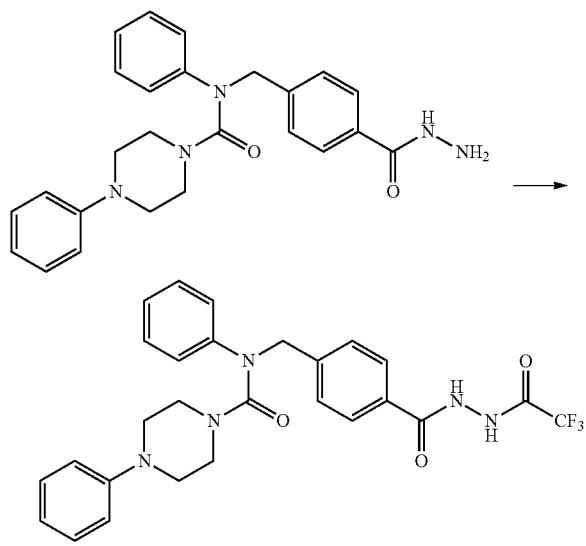

A mixture of N,4-diphenyl-N-(4-(2-(2,2,2-trifluoroacetyl) hydrazine-1-carbonyl)benzyl)piperazine-1-carboxamide (0.195 Si, 0.371 mmol) prepared in Step 3 and 1-methoxy-N-triethylammoniosulfonyl-methanimidate (Burgess reagent, 0.115 g, 0.482 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N,4-diphenyl-N-(4-(5-(trifluoromethyl)-1,3,4-oxadiazol-2-yl)benzyl)piperazine-1-carboxamide as Colorless oil (0.100 g, 53.1%).

$^1$H NMR (400 MHz, CDCl$_3$) δ 8.04 (d, 2H, J=8.4 Hz), 7.52 (d, 2H, J=8.5 Hz), 7.35-7.23 (m, 4H), 7.16-7.10 (m, 3H), 6.91-6.85 (m, 3H), 4.98 (s, 2H), 3.45-3.34 (m, 4H), 3.00 (t, 4H, J=4.7 Hz); LRMS (ES) m/z 508.2 (M$^+$+1).

Example 29. Compound 21359: N,4-diphenyl-N-(4-(5-(trifluoromethyl)-1,3,4-oxadiazol-2-yl)benzyl)-3,6-dihydropyridine-1(2H)-carboxamide

[Step 1] Methyl 4-((N,4-diphenyl-1,2,3,6-tetrahydropyridine-1-carboxamido)methyl)benzoate

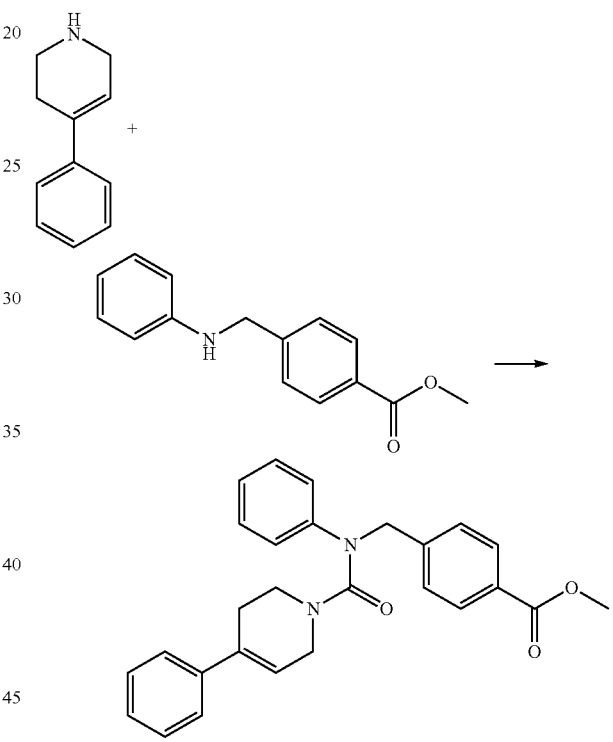

To a stirred solution of methyl 4-((phenylamino)methyl) benzoate (0.300 g, 1.244 mmol) in dichloromethane (20 mL) were added at 0° C. N,N-diisopropylethylamine (1.083 mL, 6.218 mmol) and triphosgene (0.295 g, 0.995 mmol). The reaction mixture was stirred at the same temperature for 30 min, treated at the room temperature with 4-phenyl-1,2,3,6-tetrahydropyridine (0.268 g, 1.368 mmol), and stirred for additional 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-((N,4-diphenyl-1,2,3,6-tetrahydropyridine-1-carboxamido)methyl)benzoate as Colorless oil (0.237 g, 44.7%).

[Step 2] N-(4-(hydrazinecarbonyl)benzyl)-N,4-diphenyl-3,6-dihydropyridine-1(2H)-carboxamide

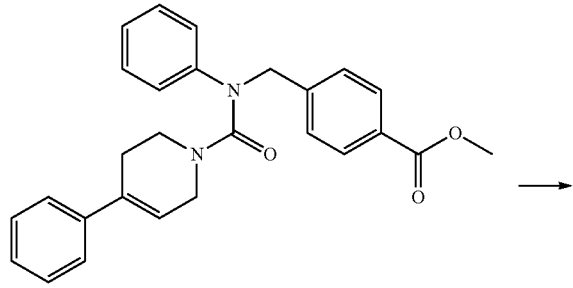

A mixture of methyl 4-((N,4-diphenyl-1,2,3,6-tetrahydropyridine-1-carboxamido)methyl)benzoate (0.237 g, 0.556 mmol) prepared in Step 1 and hydrazine monohydrate (0.262 mL, 5.557 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with brine, dried (anhydrous MgSO$_4$), filtered, and concentrated in vacuo to give the title compound N-(4-(hydrazinecarbonyl)benzyl)-N,4-diphenyl-3,6-dihydropyridine-1(2H)-carboxamide (0.230 g, 97.0%, Colorless oil).

[Step 3] N,4-diphenyl-N-(4-(2-(2,2,2-trifluoroacetyl)hydrazine-1-carbonyl)benzyl)-3,6-dihydropyridine-1(2H)-carboxamide

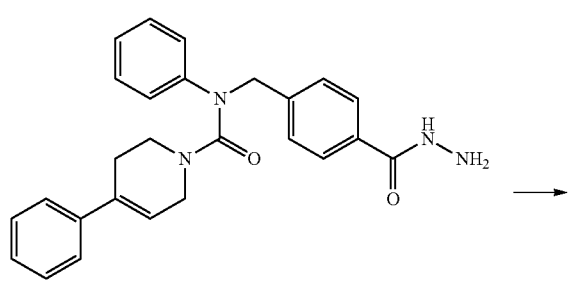

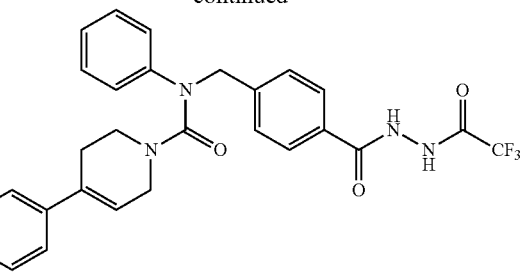

A solution of N-(4-(hydrazinecarbonyl)benzyl)-N,4-diphenyl-3,6-dihydropyridine-1(2H)-carboxamide (0.230 g, 0.539 mmol) prepared in Step 2, trifluoroacetic anhydride (0.068 mL, 0.485 mmol) and triethylamine (0.112 mL, 0.809 mmol) in dichloromethane (10 mL) was stirred at the room temperature for 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N,4-diphenyl-N-(4-(2-(2,2,2-trifluoroacetyl)hydrazine-1-carbonyl)benzyl)-3,6-dihydropyridine-1(2H)-carboxamide as Colorless oil (0.222 g, 78.8%).

[Step 4] Compound 21359

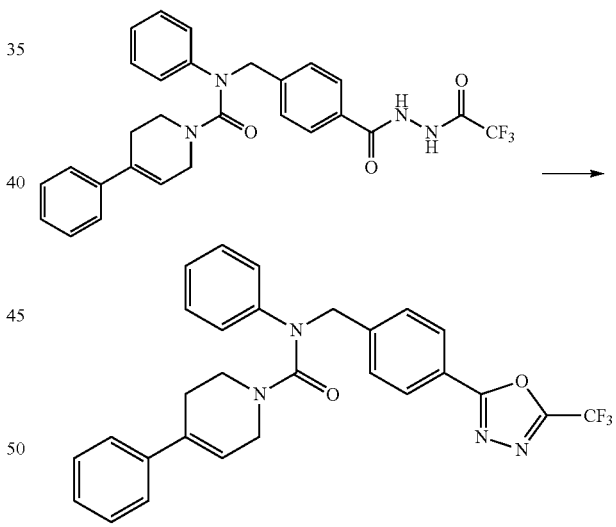

A mixture of N,4-diphenyl-N-(4-(2-(2,2,2-trifluoroacetyl)hydrazine-1-carbonyl)benzyl)-3,6-dihydropyridine-1(2H)-carboxamide (0.222 g, 0.425 mmol) prepared in Step 3 and 1-methoxy-N-triethylammoniosulfonyl-methanimidate (Burgess reagent, 0.132 g, 0.552 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N,4-diphenyl-N-(4-(5-(trifluoromethyl)-1,3,4-oxadiazol-2-yl)benzyl)-3,6-dihydropyridine-1(2H)-carboxamide as Colorless oil (0.120 g, 56.0%).

$^1$H NMR (400 MHz, CDCl$_3$) δ 8.03 (d, 2H, J=8.2 Hz), 7.52 (d, 2H, J=8.1 Hz), 7.35-7.23 (m, 7.16-7.08 (m, 3H), 5.96 (s, 1H), 4.99 (s, 2H), 3.86 (d, 2H, J=2.7 Hz), 3.54 (t, 2H, J=5.5 Hz), 2.33 (s, 2H); LRMS (ES) m/z 505.2 (M$^+$+1).

Example 30. Compound 21360: N-(4-(5-(difluoromethyl)-1,3,4-oxadiazol-2-yl)benzyl)-N-phenylthiomorpholine-4-carboxamide 1,1-dioxide

[Step 1] N-phenylthiomorpholine-4-carboxamide 1,1-dioxide

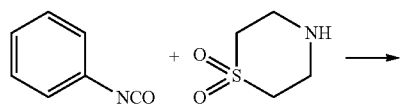

A solution of thiomorpholine dioxide (5.592 g, 41.370 mmol) in diethylether (100 mL) was mixed at the room temperature with phenylisocyanate (4.480 g, 37.609 mmol). The reaction mixture was stirred at the same temperature for 1 hr. The precipitates were collected by filtration, washed by hexane, and dried to give the title compound N-phenylthiomorpholine-4-carboxamide 1,1-dioxide as white solid (9.200 g, 96.2%).

[Step 2] Methyl 4-((1,1-dioxido-N-phenylthiomorpholine-4-carboxamido)methyl)benzoate

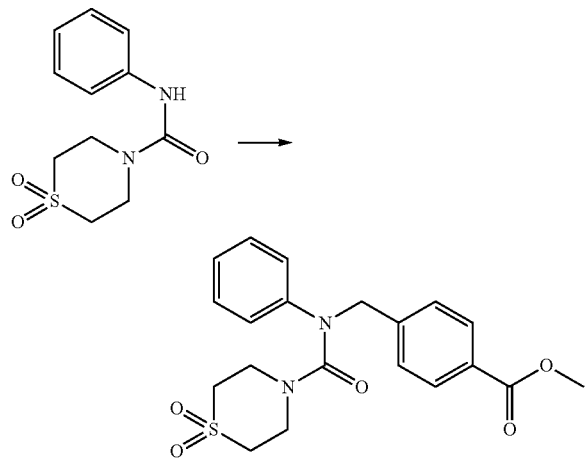

To a stirred solution of N-phenylthiomorpholine-4-carboxamide 1,1-dioxide (1.000 g, 3.932 mmol) prepared in Step 1 in N,N-dimethylformamide (20 mL) was added at 0° C. sodium hydride (60.00%, 0.220 g, 5.505 mmol). The reaction mixture was stirred at the same temperature for 20 min, treated at the room temperature with methyl 4-(bromomethyl)benzoate (1.171 g, 5.112 mmol), and stirred for additional 12 hr. Then, saturated aqueous ammonium chloride solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 24 g cartridge; methanol/dichloromethane=0% to 10%) to give the title compound methyl 4-1,1-dioxido-N-phenylthiomorpholine-4-carboxamido)methyl)benzoate as white solid (0.830 g, 52.4%).

[Step 3] N-(4-(hydrazinecarbonyl)benzyl)-N-phenylthiomorpholine-4-carboxamide 1,1-dioxide

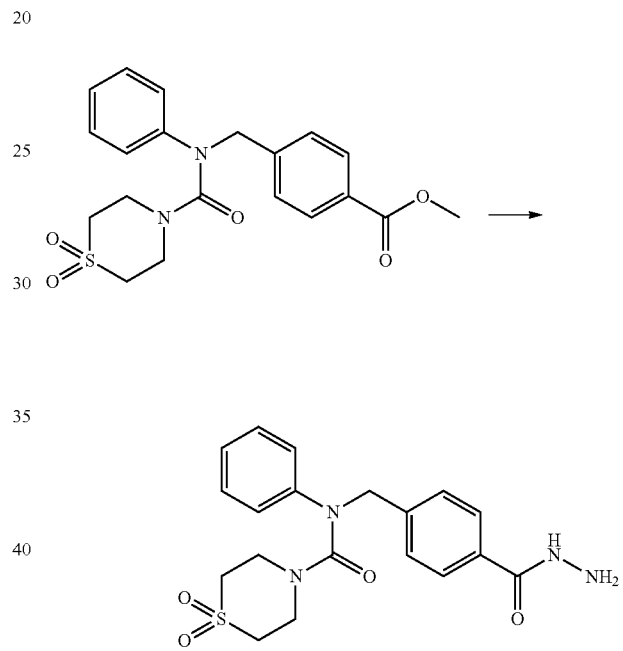

A mixture of methyl 4-((1,1-dioxido-N-phenylthiomorpholine-4-carboxamido)methyl)benzoate (0.830 g, 2.062 mmol) prepared in Step 2 and hydrazine monohydrate (2.005 mL, 41.246 mmol) in ethanol (10 mL) was heated at 120° C. for 1 hr under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 40 g cartridge; methanol/dichloromethane=0% to 30%) to give the title compound N-(4-(hydrazinecarbonyl)benzyl)-N-phenylthiomorpholine-4-carboxamide 1,1-dioxide as white foam solid (0.693 g, 83.5%).

[Step 4] N-(4-(2-(2,2-difluoroacetyl)hydrazine-1-carbonyl)benzyl)-N-phenylthiomorpholine-4-carboxamide 1,1-dioxide

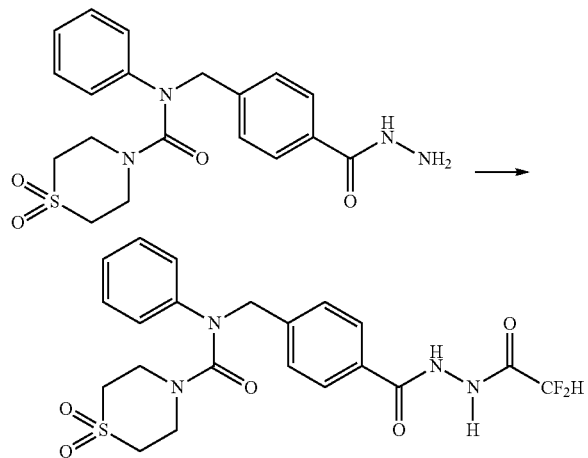

A solution of N-(4-(hydrazinecarbonyl)benzyl)-N-phenylthiomorpholine-4-carboxamide 1,1-dioxide (0.127 g, 0.316 mmol) prepared in Step 3, 2,2-difluoroacetic anhydride (0.037 mL, 0.284 mmol) and Triethylamine (0.066 mL, 0.473 mmol) in dichloromethane (10 mL) was stirred at the room temperature for 1 hr. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 24 g cartridge; methanol/dichloromethane=0% to 10%) to give the title compound N-(4-(2-(2,2-difluoroacetyl)hydrazine-1-carbonyl)benzyl)-N-phenylthiomorpholine-4-carboxamide 1,1-dioxide as white foam solid (0.107 g, 70.6%).

[Step 5] Compound 21360

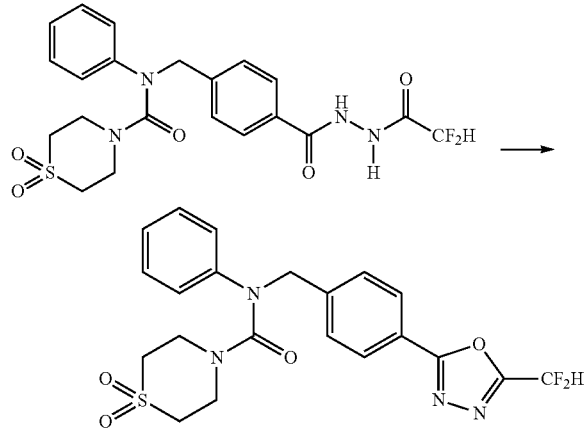

A mixture of N-(4-(2-(2,2-difluoroacetyl)hydrazine-1-carbonyl)benzyl)-N-phenylthiomorpholine-4-carboxamide 1,1-dioxide (0.107 g, 0.223 mmol) prepared in Step 4 and 1-methoxy-N-triethylammoniosulfonyl-methanimidate (Burgess reagent, 0.069 g, 0.289 mmol) in tetrahydrofuran (5 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound N-(4-(5-(difluoromethyl)-1,3,4-oxadiazol-2-yl)benzyl)-N-phenylthiomorpholine-4-carboxamide 1,1-dioxide as white solid (0.068 g, 66.0%).

¹H NMR (400 MHz, DMSO-d₆) δ 7.95 (d, 2H, J=8.3 Hz), 7.53 (d, 1H, J=102.6 Hz), 7.54 (d, 2H, J=8.7 Hz), 7.34 (t, 3H, J=8.3 Hz), 7.27 (m, 2H), 7.13 (t, 1H, J=7.3 Hz), 4.94 (s, 2H), 3.57 (s, 4H), 2.93 (s, 4H); LRMS (ES) m/z 463.0 (M⁺+H).

Example 31. Compound 21361: N-phenyl-N-(4-(5-(trifluoromethyl)-1,3,4-oxadiazol-2-yl)benzyl)thiomorpholine-4-carboxamide 1,1-dioxide

[Step 1] N-phenyl-N-(4-(2-(2,2,2-trifluoroacetyl)hydrazine-1-carbonyl)benzyl)thiomorpholine-4-carboxamide 1,1-dioxide

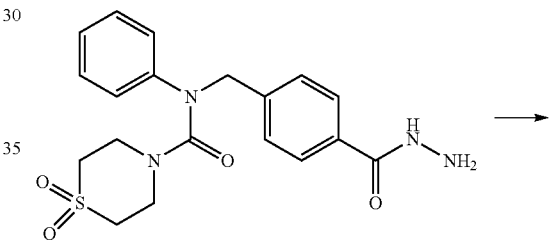

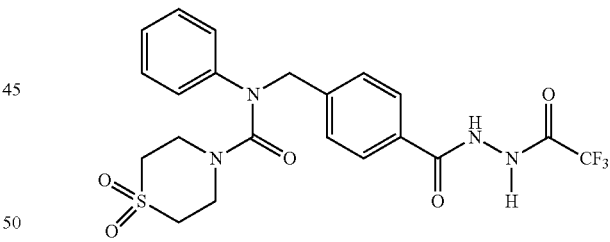

A solution of N-(4-(hydrazinecarbonyl)benzyl)-N-phenylthiomorpholine-4-carboxamide 1,1-dioxide (0.690 g, 1.714 mmol) prepared in Step 3 of Example 30 and Triethylamine (0.356 mL, 2.572 mmol) in dichloromethane (10 mL) was mixed at 0° C. with trifluoroacetic anhydride (0.215 mL, 1.543 mmol), and stirred at the room temperature for 12 hr. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 20%) to give the title compound N-(4-(hydrazinecarbonyl)benzyl)-N-phenylthiomorpholine-4-carboxamide 1,1-dioxide as white foam solid (0.783 g, 91.6%).

[Step 2] Compound 21361

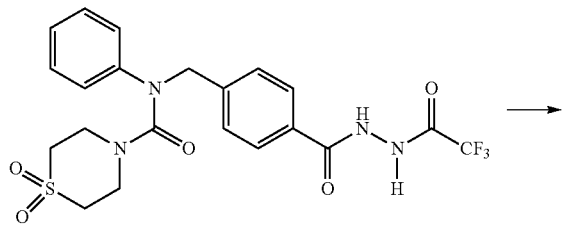

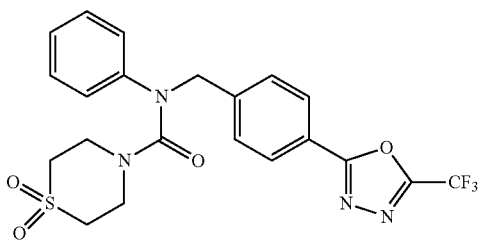

A mixture of N-phenyl-N-(4-(2-(2,2,2-trifluoroacetyl)hydrazine-1-carbonyl)benzyl)thiomorpholine-4-carboxamide 1,1-dioxide (0.440 g, 0.883 mmol) prepared in Step 1 and 1-methoxy-N-triethylammoniosulfonyl-methanimidate (Burgess reagent, 0.273 g, 1.147 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous $MgSO_4$), filtered, and concentrated in vacuo. The concentrate was purified and concentrated by column chromatography ($SiO_2$, 24 g cartridge; methanol/dichloromethane=0% to 20%) to give the title compound N-phenyl-N-(4-(5-(trifluoromethyl)-1,3,4-oxadiazol-2-yl)benzyl)thiomorpholine-4-carboxamide 1,1-dioxide as white foam solid (0.350 g, 82.5%).

$^1$H NMR (400 MHz, DMSO-$d_6$) δ 7.97 (d, 2H, J=8.4 Hz), 7.55 (d, 2H, J=8.4 Hz), 7.33 (t, 3H, J=8.4 Hz), 7.25 (dd, 2H, J=8.6, 1.2 Hz), 7.12 (t, 1H, J=7.3 Hz), 4.95 (s, 2H), 3.59 (s, 4H), 2.93 (s, 4H); LRMS (ES) m/z 481.2 (M$^+$+1).

Example 32. Compound 21362: N-phenyl-N-(4-(5-(trifluoromethyl)-1,3,4-oxadiazol-2-yl)benzyl)piperazine-1-carboxamide

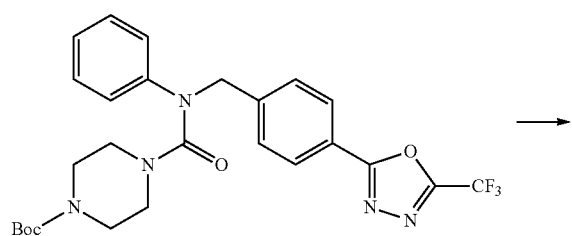

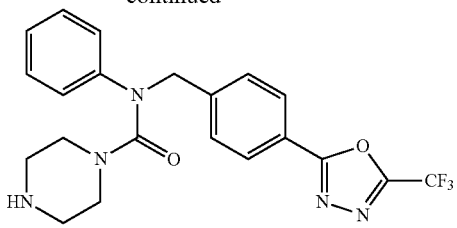

A solution of tert-butyl 4-(phenyl(4-(5-(trifluoromethyl)-1,3,4-oxadiazol-2-yl)benzyl)carbamoyl)piperazine-1-carboxylate (0.776 g, 1.460 mmol) prepared in Example 23 and TFA (2.234 mL, 29.198 mmol) in dichloromethane (8 mL) was stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo to give the title compound N-phenyl-N-(4-(5-(trifluoromethyl)-1,3,4-oxadiazol-2-yl)benzyl)piperazine-1-carboxamide without further purification (0.600 g, 95.3%, pale yellow oil).

$^1$H NMR (400 MHz, CDCl$_3$) δ 8.03 (d, 2H, J=8.2 Hz), 7.51 (d, 2H, J=8.2 Hz), 7.31 (t, 2H, J=7.9 Hz), 7.12 (t, 1H, J=7.4 Hz), 7.08-7.06 (m, 2H), 4.95 (s, 2H), 3.26 (t, 4H, J=4.5 Hz), 2.69 (t, 4H, J=5.0 Hz), 2.08 (brs, 1H).

Example 33. Compound 21363: 4-(Methylsulfonyl)-N-phenyl-N-(4-(5-(trifluoromethyl)-1,3,4-oxadiazol-2-yl)benzyl)piperazine-1-carboxamide

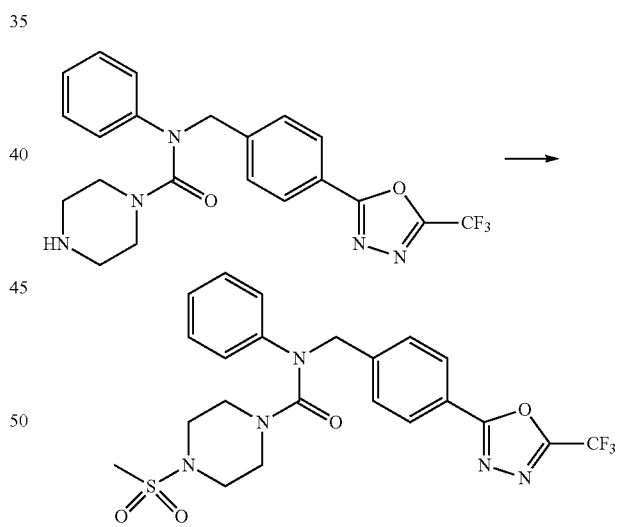

A solution of N-phenyl-N-(4-(5-(trifluoromethyl)-1,3,4-oxadiazol-2-yl)benzyl)piperazine-1-carboxamide (0.100 g, 0.232 mmol) prepared in Example 32 and triethylamine (0.048 mL, 0.348 mmol) in dichloromethane (4 mL) was mixed at the room temperature with methanesulfonyl chloride (0.020 mL, 0.255 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=30% to 80%) to give the title compound 4-(methylsulfonyl)-N-phenyl-N-(4-(5-(trifluoromethyl)-1,3,4-oxadiazol-2-yl)benzyl)piperazine-1-carboxamide as colorless oil (0.112 g, 94.8%).

$^1$H NMR (400 MHz, CDCl$_3$) δ 8.01 (d, 2H, J=8.2 Hz), 7.46 (d, 2H, J=8.2 Hz), 7.32 (t, 2H, J=7.8 Hz), 7.16 (t, 1H, J=7.4 Hz), 7.05 (d, 2H, J=7.6 Hz), 4.92 (s, 2H), 3.35 (t, 4H, J=4.9 Hz), 3.02 (t, 4H, J=4.9 Hz), 2.72 (s, 3H); LRMS (ESI) m/z 510.2 (M$^+$+H).

Example 34. Compound 21364: 4-Acetyl-N-phenyl-N-(4-(5-(trifluoromethyl)-1,3,4-oxadiazol-2-yl)benzyl)piperazine-1-carboxamide

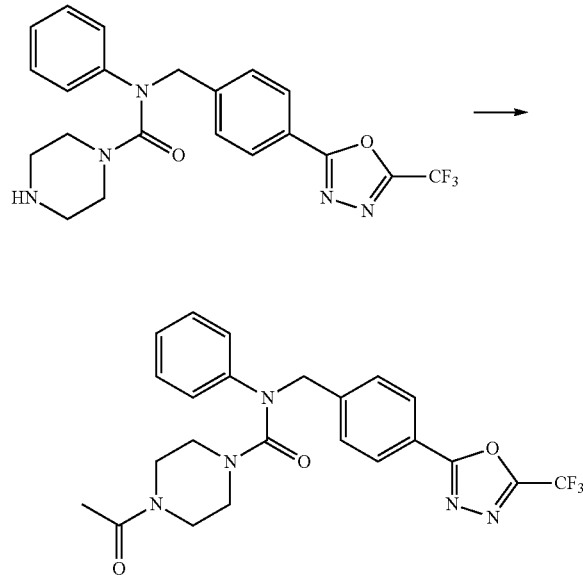

A solution of N-phenyl-N-(4-(5-(trifluoromethyl)-1,3,4-oxadiazol-2-yl)benzyl)piperazine-1-carboxamide (0.050 g, 0.116 mmol) prepared in Example 32 and triethylamine (0.032 mL, 0.232 mmol) in dichloromethane (3 mL) was mixed at the room temperature with acetylchloride (0.010 mL, 0.139 mmol). The reaction mixture was stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=70% to 100%) to give the title compound 4-acetyl-N-phenyl-N-(4-(5-(trifluoromethyl)-1,3,4-oxadiazol-2-yl)benzyl)piperazine-1-carboxamide as pale yellow oil (0.043 g, 78.4%).

$^1$H NMR (400 MHz, CDCl$_3$) δ 8.01 (d, 2H, J=8.3 Hz), 7.47 (d, 2H J=8.3 Hz), 7.31 (t, 2H, J=7.9 Hz), 7.14 (t, 1H, J=7.4 Hz), 7.07-7.05 (m, 2H), 4.93 (s, 2H), 3.31-3.26 (m, 8H), 2.04 (s, 3H); LRMS (ESI) m/z 474.2 (M$^+$+H).

Example 35. Compound 21365: 4-Isobutyryl-N-phenyl-N-(4-(5-(trifluoromethyl)-1,3,4-oxadiazol-2-yl)benzyl)piperazine-1-carboxamide

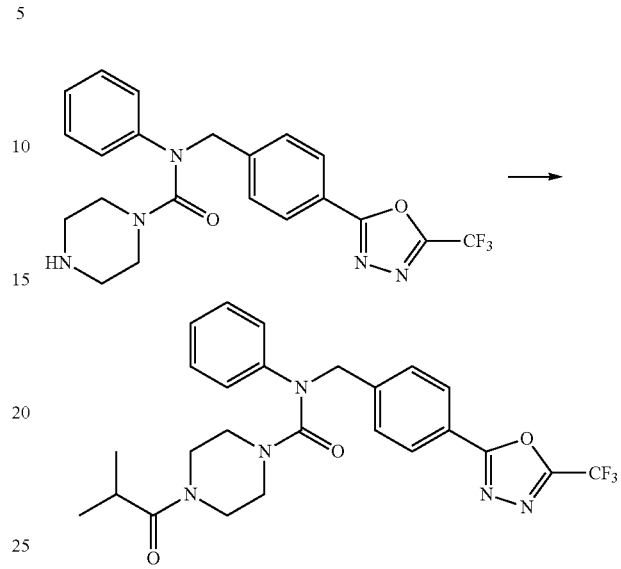

A solution of N-phenyl-N-(4-(5-(trifluoromethyl)-1,3,4-oxadiazol-2-yl)benzyl)piperazine-1-carboxamide (0.050 g, 0.116 mmol) prepared in Example 32 and triethylamine (0.032 mL, 0.232 mmol) in dichloromethane (4 mL) was mixed at the room temperature with propionyl chloride (0.014 mL, 0.139 mmol). The reaction mixture was stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=10% to 50%) to give the title compound 4-isobutyryl-N-phenyl-N-(4-(5-(trifluoromethyl)-1,3,4-oxadiazol-2-yl)benzyl)piperazine-1-carboxamide as pale yellow oil (0.045 g, 77.4%).

$^1$H NMR (400 MHz, CDCl$_3$) δ 8.01 (d, 2H, J=8.4 Hz), 7.47 (d, 2H, J=8.4 Hz), 7.31 (t, 2H, J=7.9 Hz), 7.14 (t, 1H, J=7.5 Hz), 7.08-7.05 (m, 2H), 4.93 (s, 2H), 3.38-3.36 (m, 4H), 3.25 (brs, 4H), 2.71- 2.68 (m, 1H), 1.07 (d, 6H, J=6.8 Hz); LRMS (ESI) m/z 502.2 (M$^+$+H).

Example 36. Compound 21366: N-phenyl-4-propionyl-N-(4-(5-(trifluoromethyl)-1,3,4-oxadiazol-2-yl)benzyl)piperazine-1-carboxamide

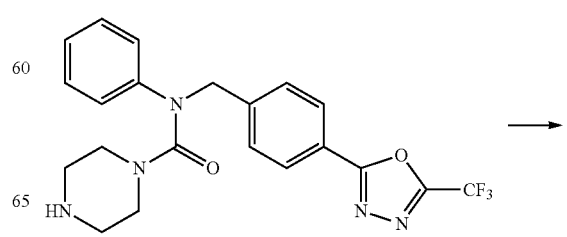

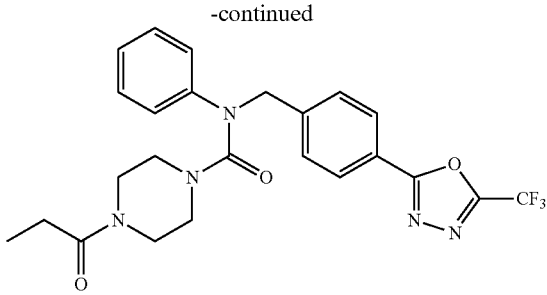

A solution of N-phenyl-N-(4-(5-(trifluoromethyl)-1,3,4-oxadiazol-2-yl)benzyl)piperazine-1-carboxamide (0.050 g, 0.116 mmol) prepared in Example 32 and triethylamine (0.032 mL, 0.232 mmol) in dichloromethane (4 mL) was mixed at the room temperature with isobutyryl chloride (0.013 mL, 0.139 mmol). The reaction mixture was stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=40% to 100%) to give the title compound N-phenyl-4-propionyl-N-(4-(5-(trifluoromethyl)-1,3,4-oxadiazol-2-yl)benzyl)piperazine-1-carboxamide as colorless oil (0.044 g, 77.9%).

$^1$H NMR (400 MHz, CDCl$_3$) δ 8.01 (d, 2H, J=8.3 Hz), 7.47 (d, 2H, J=8.2 Hz), 7.31 (t, 2H, J=7.1 Hz), 7.14 (t, 1H, J=7.5 Hz), 7.07-7.05 (m, 2H), 4.93 (s, 2H), 3.35 (brs, 4H), 3.25 (brs, 4H), 2.29 (q, 2H, J=7.5 Hz), 1.10 (t, 3H, J=7.4 Hz); LRMS (ESI) m/z 488.2 (M$^+$+H).

Example 37. Compound 21367: N-phenyl-4-(2,2,2-trifluoroacetyl)-N-(4-(5-(trifluoromethyl)-1,3,4-oxadiazol-2-yl)benzyl)piperazine-1-carboxamide

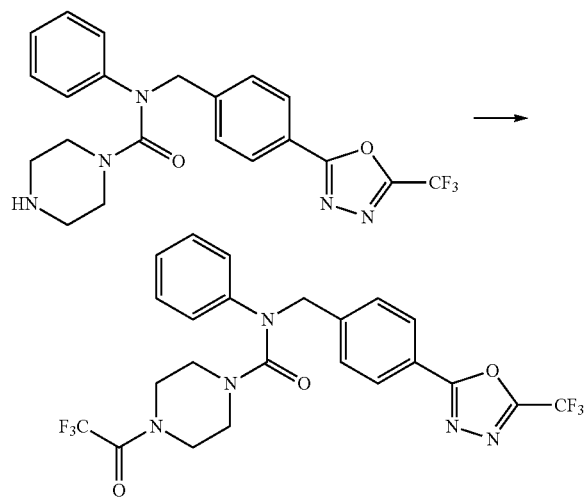

A solution of N-phenyl-N-(4-(5-(trifluoromethyl)-1,3,4-oxadiazol-2-yl)benzyl)piperazine-1-carboxamide (0.050 g, 0.116 mmol) prepared in Example 32 and triethylamine (0.032 mL, 0.232 mmol) in dichloromethane (4 mL) was mixed at the room temperature with trifluoroacetic anhydride (0.019 mL, 0.139 mmol). The reaction mixture was stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 40%) to give the title compound N-phenyl-4-(2,2,2-trifluoroacetyl)-N-(4-(5-(trifluoromethyl)-1,3,4-oxadiazol-2-yl)benzyl)piperazine-1-carboxamide as colorless oil (0.049 g, 80.2%).

$^1$H NMR (400 MHz, CDCl$_3$) δ 8.01 (d, 2H, J=8.5 Hz), 7.46 (d, 2H, J=8.5 Hz), 7.33 (t, 2H, J=7.9 Hz), 7.17 (t, 1H, J=7.4 Hz), 7.09-7.06 (m, 2H), 4.93 (s, 2H), 3.48-3.46 (m, 2H), 3.41-3.40 (m, 2H), 3.33-3.27 (m, 4H); LRMS (ESI) m/z 528.2 (M$^+$+H).

Example 38. Compound 21368: 3-Benzyl-1-phenyl-1-(4-(5-(trifluoromethyl)-1,3,4-oxadiazol-2-yl)benzyl)urea

[Step 1] Methyl 4-((3-benzyl-1-phenylureido)methyl)benzoate

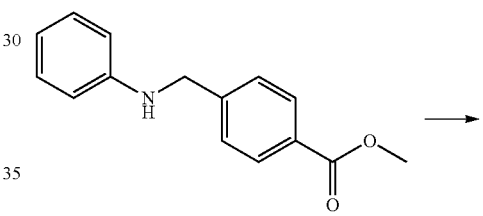

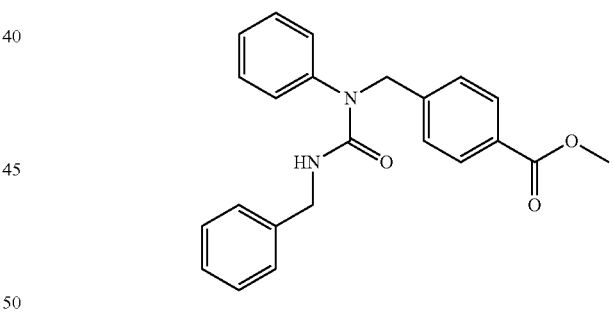

To a stirred solution of methyl 4-((phenylamino)methyl)benzoate (0.500 g, 2.072 mmol) in dichloromethane (10 mL) were added at 0° C. triphosgene (0.492 g, 1.658 mmol) and N,N-diisopropylethylamine (1.810 mL, 10.361 mmol). The reaction mixture was stirred at the same temperature for 1 hr, treated at the room temperature with benzylamine (0.266 g, 2.487 mmol), and stirred for additional 5 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=10% to 50%) to give the title compound methyl 4-((3-benzyl-1-phenylureido)methyl)benzoate as pale yellow oil (0.760 g, 97.9%).

[Step 2] 3-Benzyl-1-(4-(hydrazinecarbonyl)benzyl)-1-phenylurea

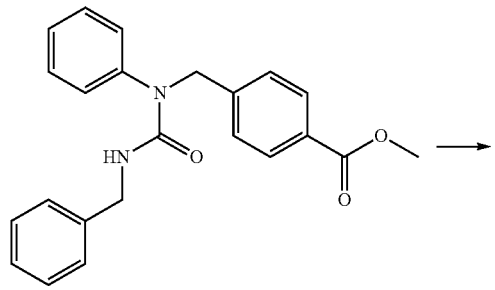

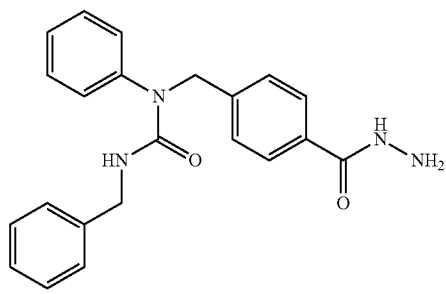

Methyl 4-((3-benzyl-1-phenylureido)methyl)benzoate (0.500 g, 1.335 mmol) prepared in Step 1 and hydrazine monohydrate (1.298 mL, 26.707 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=70% to 100%) to give the title compound 3-benzyl-1-(4-(hydrazinecarbonyl)benzyl)-1-phenylurea as pale yellow oil (0.144 g, 28.8%).

[Step 3] 3-Benzyl-1-phenyl-1-(4-(2-(2,2,2-trifluoroacetyl)hydrazine-1-carbonyl)benzyl)urea

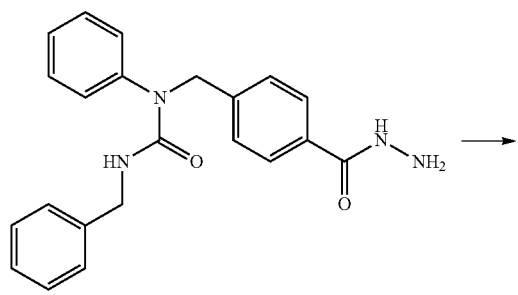

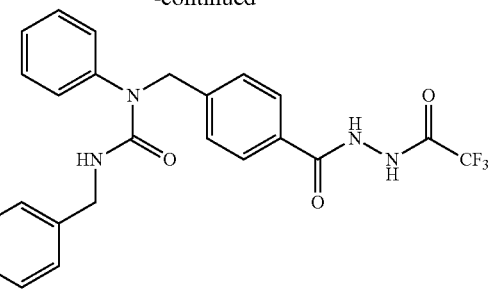

A solution of 3-benzyl-1-(4-(hydrazinecarbonyl)benzyl)-1-phenylurea (0.144 g, 0.385 mmol) prepared in Step 2 and triethylamine (0.080 mL, 0.577 mmol) in dichloromethane (5 mL) was mixed at the room temperature with trifluoroacetic anhydride (0.043 mL, 0.346 mmol). The reaction mixture was stirred at the same temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 70%) to give the title compound 3-benzyl-1-phenyl-1-(4-(2-(2,2,2-trifluoroacetyl)hydrazine-1-carbonyl)benzyl)urea as pale yellow oil (0.135 g, 74.6%).

[Step 4] Compound 21368

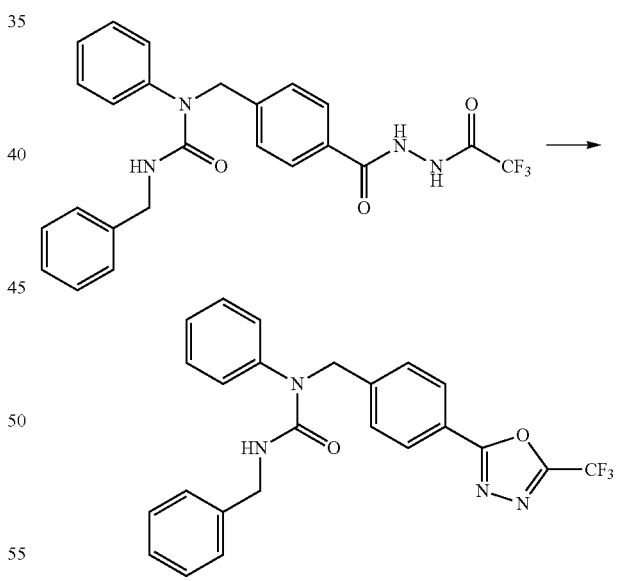

3-Benzyl-1-phenyl-1-(4-(2-(2,2,2-trifluoroacetyl)hydrazine-1-carbonyl)benzyl)urea (0.135 g, 0.287 mmol) prepared in Step 3 and 1-methoxy-N-triethylammoniosulfonyl-methanimidate (Burgess reagent, 0.103 g, 0.430 mmol) were mixed at the room temperature in tetrahydrofuran (4 mL) and then stirred at 150° C. for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=10% to 50%) to give the title compound 3-benzyl-1-phenyl-1-(4-(5-(trifluoromethyl)-1,3,4-oxadiazol-2-yl)benzyl)urea as colorless oil (0.059 g, 45.4%).

$^1$H NMR (400 MHz, CDCl$_3$) δ 8.04 (d, 2H, J=1.8 Hz), 7.46 (d, 2H, J=8.2 Hz), 7.37-7.28 (m, 5H), 7.25-7.21 (m, 3H), 7.12- 7.10 (m, 2H), 4.99 (s, 2H), 4.68 (t, 1H, J=5.8 Hz), 4.43 (d, 2H, J=5.7 Hz); LRMS (ESI) m/z 453.2 (M$^+$+H).

Example 39. Compound 21369: N-(2-fluoro-4-(5-(trifluoromethyl)-1,3,4-oxadiazol-2-yl)benzyl)-N-phenylthiomorpholine-4-carboxamide 1,1-dioxide

[Step 1] Methyl 4-((1,1-dioxido-N-phenylthiomorpholine-4-carboxamido)methyl)-3-fluorobenzoate

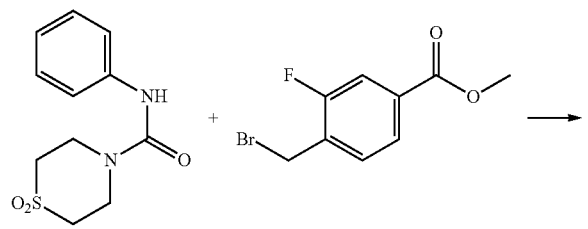

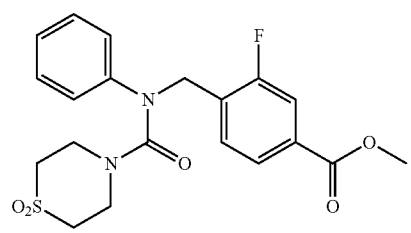

A solution of N-phenylthiomorpholine-4-carboxamide 1,1-dioxide (1.000 g, 3.932 mmol) and sodium hydride (60.00%, 0.189 g, 4.719 mmol) in N,N-dimethylformamide (30 mL) was mixed at 0° C. with methyl 4-(bromomethyl)-3-fluorobenzoate (1.020 g, 4.129 mmol), and stirred at the room temperature for 18 hr. Then, saturated aqueous sodium bicarbonate solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 40 g cartridge; ethyl acetate/hexane=0% to 50%) to give the title compound methyl 4-((1,1-dioxido-N-phenylthiomorpholine-4-carboxamido)methyl)-3-fluorobenzoate as white solid (1.240 g, 75.0%).

[Step 2] N-(2-fluoro-4-(hydrazinecarbonyl)benzyl)-N-phenylthiomorpholine-4-carboxamide 1,1-dioxide

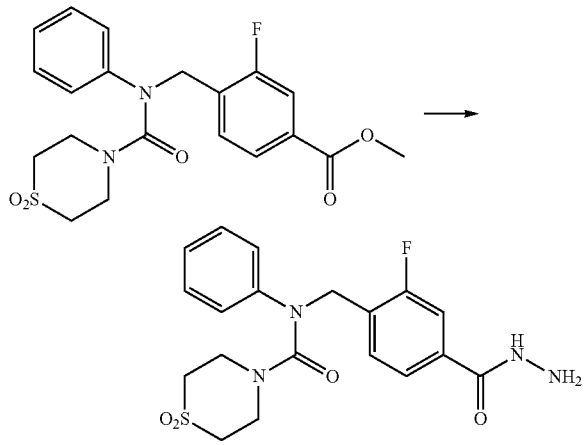

A solution of methyl 4-((1,1-dioxido-N-phenylthiomorpholine-4-carboxamido)methyl)-3-fluorobenzoate (1.240 g, 2.949 mmol) prepared in Step 1 and hydrazine monohydrate (2.786 mL, 58.983 mmol) in ethanol (15 mL) was stirred at 120° C. for 1 hr, and cooled down to the room temperature to terminate the reaction. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The crude title compound N-(2-fluoro-4-(hydrazinecarbonyl)benzyl)-N-phenylthiomorpholine-4-carboxamide 1,1-dioxide was used without further purification (1.240 g, 100.0%, white solid).

[Step 3] N-(2-fluoro-4-(2-(2,2,2-trifluoroacetyl)hydrazine-1-carbonyl)benzyl)-N-phenylthiomorpholine-4-carboxamide 1,1-dioxide

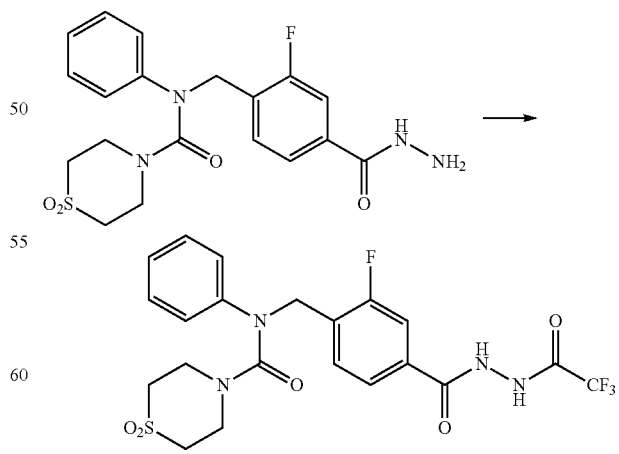

A solution of N-(2-fluoro-4-(hydrazinecarbonyl)benzyl)-N-phenylthiomorpholine-4-carboxamide 1,1-dioxide (0.615 g, 1.463 mmol) prepared in Step 2, triethylamine (0.304 mL, 2.194 mmol) and trifluoroacetic anhydride (0.183 mL, 1.316 mmol) in dichloromethane (10 mL) was stirred at the room temperature for 16 hr. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound N-(2-fluoro-4-(2-(2,2,2-trifluoroacetyl)hydrazine-1-carbonyl)benzyl)-N-phenylthiomorpholine-4-carboxamide 1,1-dioxide as white solid (0.606 g, 80.2%).

[Step 4] Compound 21369

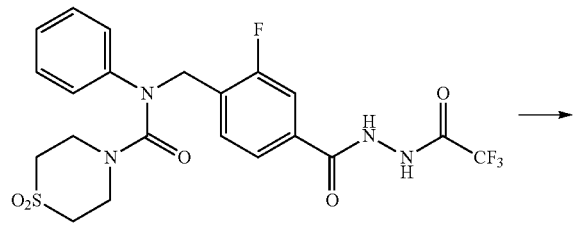

A mixture of N-(2-fluoro-4-(2-(2,2,2-trifluoroacetyl)hydrazine-1-carbonyl)benzyl)-N-phenylthiomorpholine-4-carboxamide 1,1-dioxide (0.606 g, 1.173 mmol) prepared in Step 3 and 1-methoxy-N-triethylammoniosulfonyl-methanimidate (Burgess reagent, 0.419 g, 1.760 mmol) in tetrahydrofuran (10 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; ethyl acetate/hexane=0% to 50%) to give the title compound N-(2-fluoro-4-(5-(trifluoromethyl)-1,3,4-oxadiazol-2-yl)benzyl)-N-phenylthiomorpholine-4-carboxamide 1,1-dioxide as white solid (0.462 g, 79.0%).

$^1$H NMR (400 MHz, CDCl₃) δ 7.87-7.85 (m, 1H), 7.75-7.72 (m, 1H), 7.70-7.66 (m, 1H), 7.38-7.35 (m, 2H), 7.25-7.21 (m, 1H), 7.13-7.11 (m, 2H), 4.92 (s, 1H), 3.72-3.70 (m, 4H), 2.77-2.75 (m, 4H); LRMS (ES) m/z 499.1 (M⁺+1).

Example 40. Compound 21370: N-(4-(5-(difluoromethyl)-1,3,4-oxadiazol-2-yl)-2-fluorobenzyl)-N-phenylthiomorpholine-4-carboxamide 1,1-dioxide

[Step 1] N-(4-(2-(2,2-difluoroacetyl)hydrazine-1-carbonyl)-2-fluorobenzyl)-N-phenylthiomorpholine-4-carboxamide 1,1-dioxide

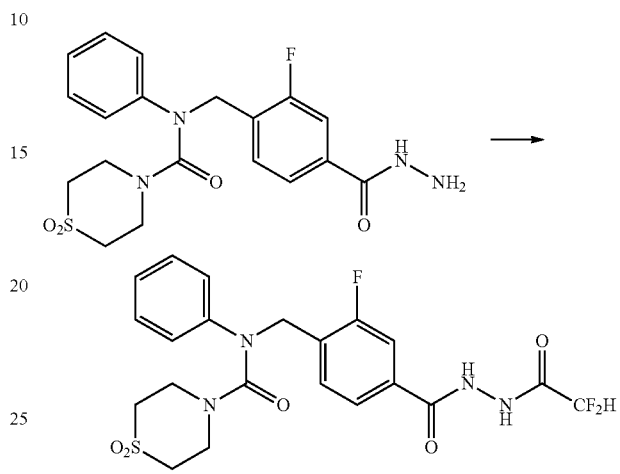

A solution of N-(2-fluoro-4-(hydrazinecarbonyl)benzyl)-N-phenylthiomorpholine-4-carboxamide 1,1-dioxide (0.615 g, 1.463 mmol) prepared in Step 2 of Example 39, triethylamine (0.304 mL, 2.194 mmol) and difluoroacetic anhydride (0.164 mL, 1.316 mmol) in dichloromethane (10 mL) was stirred at the room temperature for 18 hr. Then, saturated aqueous sodium bicarbonate solution was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 24 g cartridge; methanol/dichloromethane=0% to 3%) to give the title compound N-(4-(2-(2,2-difluoroacetyl)hydrazine-1-carbonyl)-2-fluorobenzyl)-N-phenylthiomorpholine-4-carboxamide 1,1-dioxide as white solid (0.462 g, 63.4%).

[Step 2] Compound 21370

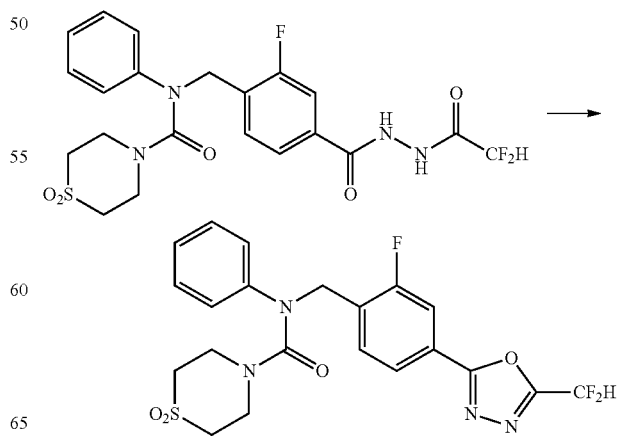

A mixture of N-(4-(2-(2,2-difluoroacetyl)hydrazine-1-carbonyl)-2-fluorobenzyl)-N-phenylthiomorpholine-4-carboxamide 1,1-dioxide (0.462 g, 0.927 mmol) prepared in Step 1 and 1-methoxy-N-triethylammoniosulfonyl-methanimidate (burgess reagent, 0.331 g, 1.390 mmol) in tetrahydrofuran (10 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 50%) to give the title compound N-(4-(5-(difluoromethyl)-1,3,4-oxadiazol-2-yl)-2-fluorobenzyl)-N-phenylthiomorpholine-4-carboxamide 1,1-dioxide as white solid (0.337 g, 75.7%).

$^1$H NMR (400 MHz, CDCl$_3$) δ 7.87-7.85 (m, 1H), 7.75-7.72 (m, 1H), 7.67-7.64 (m, 1H), 7.38-7.34 (m, 2H), 7.25-7.20 (m, 1H), 7.13-7.10 (m, 2H), 7.03-6.77 (m, 1H), 4.92 (s, 2H), 3.71-3.67 (m, 4H), 2.77-2.74 (m, 4H); LRMS (ES) m/z 481.1 (M++1).

Example 41. Compound 21371: N-cyclopentyl-N-(4-(5-(trifluoromethyl)-1,3,4-oxadiazol-2-yl)benzyl)thiomorpholine-4-carboxamide 1,1-dioxide

[Step 1]
N-cyclopentylthiomorpholine-4-carboxamide 1,1-dioxide

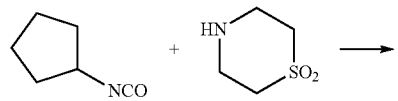

A solution of isocyanatocyclopentane (2.028 mL, 17.995 mmol) and thiomorpholine 1,1-dioxide (2.554 g, 18.895 mmol) in diethylether (50 mL) was stirred at the room temperature for 16 hr. The precipitates were collected by filtration, washed by diethylether, and dried to give the title compound N-cyclopentylthiomorpholine-4-carboxamide 1,1-dioxide as white solid (2.500 g, 56.4%).

[Step 2] Methyl 4-((N-cyclopentyl-1,1-dioxidothiomorpholine-4-carboxamido)methyl)benzoate

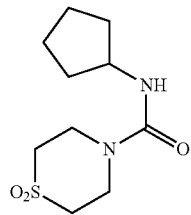

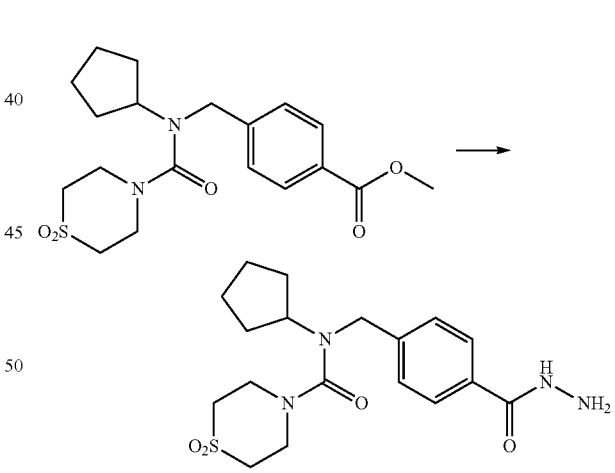

A solution of N-cyclopentylthiomorpholine-4-carboxamide 1,1-dioxide (0.300 g, 1.218 mmol) prepared in Step 1 and sodium hydride (60.00%, 0.058 g, 1.461 mmol) in N,N-dimethylformamide (5 mL) was mixed at 0° C. with methyl 4-(bromomethyl)benzoate (0.307 g, 1.340 mmol), and stirred at the room temperature for 16 hr. Then, saturated aqueous sodium bicarbonate solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((N-cyclopentyl-1,1-dioxidothiomorpholine-4-carboxamido)methyl)benzoate as white solid (0.154 g, 32.1%).

[Step 3] N-cyclopentyl-N-(4-(hydrazinecarbonyl)benzyl)thiomorpholine-4-carboxamide 1,1-dioxide

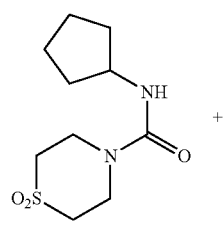

A mixture of methyl 4-((N-cyclopentyl-1,1-dioxidothiomorpholine-4-carboxamido)methyl)benzoate (0.146 g, 0.370 mmol) prepared in Step 2 and hydrazine monohydrate (0.350 mL, 7.402 mmol) in ethanol (3 mL) was heated at 120° C. for 1 hr under the microwaves, and cooled down to the room temperature to terminate the reaction. The reaction mixture was concentrated under the reduced pressure to remove the solvent, and saturated aqueous sodium bicarbonate solution was added to the concentrate, followed by extraction with ethyl acetate. The organic layer was washed with brine, dried (anhydrous MgSO$_4$), filtered, and concentrated in vacuo. The crude title compound N-cyclopentyl- N-(4-(hydrazinecarbonyl)benzyl)thiomorpholine-4-carboxamide 1,1-dioxide was used without further purification (0.148 g, 101.4%, white solid).

[Step 4] N-cyclopentyl-N-(4-(2-(2,2,2-trifluoroacetyl)hydrazine-1-carbonyl)benzyl)thiomorpholine-4-carboxamide 1,1-dioxide

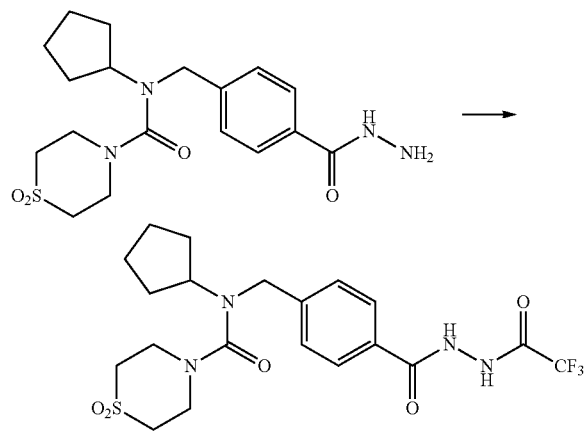

A solution of N-cyclopentyl-N-(4-(hydrazinecarbonyl)benzyl)thiomorpholine-4-carboxamide 1,1-dioxide (0.148 g, 0.375 mmol) prepared in Step 3, triethylamine (0.078 mL, 0.563 mmol) and trifluoroacetic anhydride (0.047 mL, 0.338 mmol) in dichloromethane (2 mL) was stirred at the room temperature for 18 hr. Then, saturated aqueous sodium bicarbonate solution was added to the reaction mixture, followed by extraction with dichloromethane. The organic layer was washed with brine, dried (anhydrous CaCl2), filtered, and concentrated in vacuo. The concentrate was purified and concentrated by column chromatography (SiO$_2$, 4 g cartridge; methanol/dichloromethane=0% to 5%) to give the title compound N-cyclopentyl-N-(4-(2-(2,2,2-trifluoroacetyl)hydrazine-1-carbonyl)benzyl)thiomorpholine-4-carboxamide 1,1-dioxide as white solid (0.035 g, 19.0%).

[Step 5] Compound 21371

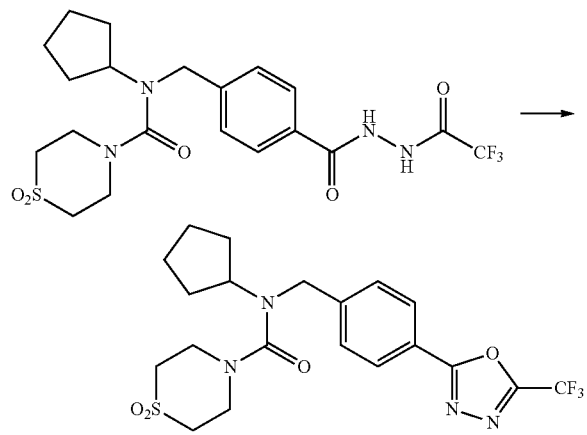

A solution of N-cyclopentyl-N-(4-(2-(2,2,2-trifluoroacetyl)hydrazine-1-carbonyl)benzyl)thiomorpholine-4-carboxamide 1,1-dioxide (0.033 g, 0.067 mmol) prepared in Step 4 and burgess reagent (0.024 g, 0.101 mmol) in tetrahydrofuran (0.5 mL) was stirred at the room temperature for 30 min. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-cyclopentyl-N-(4-(5-(trifluoromethyl)-1,3,4-oxadiazol-2-yl)benzyl)thiomorpholine-4-carboxamide 1,1-dioxide as white solid (0.027 g, 84.9%).

$^1$H NMR (400 MHz, CDCl$_3$) δ 8.07 (d, 2H, J=8.4 Hz), 7.41 (d, 2H, J=8.1 Hz), 4.33 (s, 2H), 4.06-4.02 (m, 1H), 3.79-3.75 (m, 4H), 2.98-2.95 (m, 4H), 1.95-1.92 (m, 2H), 1.75-1.76 (m, 2H), 1.61-1.57 (m, 4H); LRMS (ES) m/z 473.2 (M$^+$+1).

Example 42. Compound 21372: N-phenyl-N-((5-(5-(trifluoromethyl)-1,3,4-oxadiazol-2-yl)pyridin-2-yl)methyl)thiomorpholine-4-carboxamide 1,1-dioxide

[Step 1] N-phenylthiomorpholine-4-carboxamide 1,1-dioxide

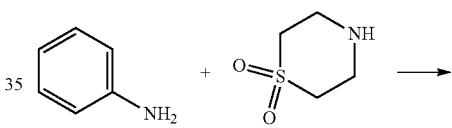

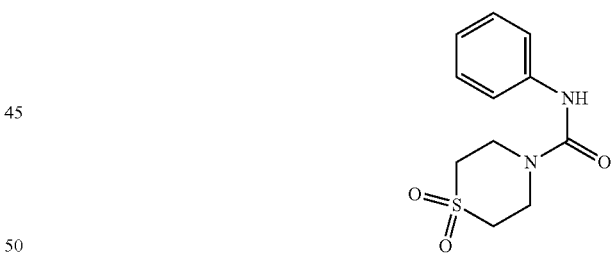

To a stirred solution of aniline (3.000 g, 32.213 mmol) and N,N-diisopropylethylamine (33.439 mL, 193.278 mmol) in dichloromethane (100 mL) was added at 0° C. triphosgene (4.780 g, 16.107 mmol). The reaction mixture was stirred at the same temperature, treated at the room temperature with thiomorpholine 1,1-dioxide (4.790 g, 35.434 mmol), and stirred for additional 16 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 40 g cartridge; methanol/dichloromethane=2%) to give the title compound N-phenylthiomorpholine-4-carboxamide 1,1-dioxide as yellow solid (1.325 g, 16.2%).

[Step 2] Methyl 6-((1,1-dioxido-N-phenylthiomorpholine-4-carboxamido)methyl)nicotinate

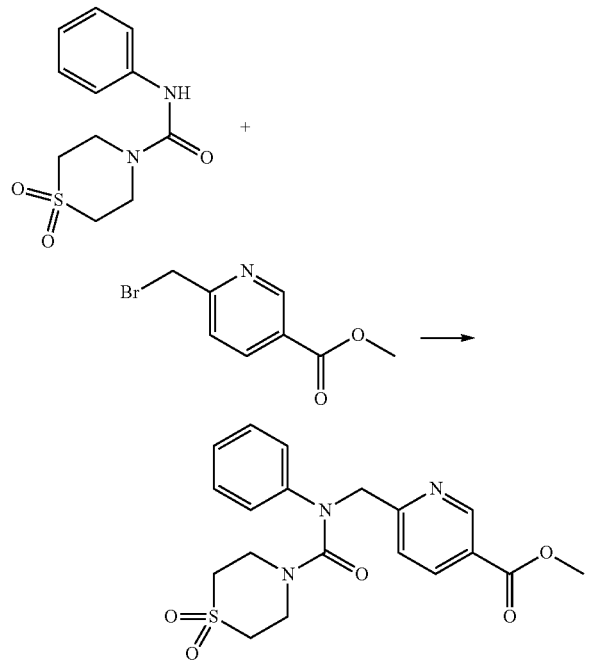 [SMILES: O=C(Nc1ccccc1)N1CCS(=O)(=O)CC1 ; COC(=O)c1ccc(CBr)nc1 ; COC(=O)c1ccc(CN(C(=O)N2CCS(=O)(=O)CC2)c2ccccc2)nc1]

A solution of N-phenylthiomorpholine-4-carboxamide 1,1-dioxide (1.000 g, 3.932 mmol) prepared in Step 1 and sodium hydride (60.00%, 0.157 g, 3.932 mmol) in N,N-dimethylformamide (10 mL) was stirred at 0° C. for 1 hr, and mixed with methyl 4-(bromomethyl)-3-fluorobenzoate (0.905 g, 3.932 mmol). The reaction mixture was stirred at the room temperature for additional 2 hr. The reaction mixture was concentrated under the reduced pressure to remove the solvent, and water was added to the concentrate, followed by extraction with ethyl acetate. The organic layer was washed with brine, dried (anhydrous MgSO$_4$), filtered, and concentrated in vacuo. The crude product was crystallized at the room temperature using methanol (20 mL). The resulting precipitates were filtered, washed by methanol, and dried to give the title compound methyl 6-((1,1-dioxido-N-phenylthiomorpholine-4-carboxamido)methyl)nicotinate as brown solid (0.816 g, 51.4%).

[Step 3] N-((5-(hydrazinecarbonyl)pyridin-2-yl)methyl)-N-phenylthiomorpholine-4-carboxamide 1,1-dioxide

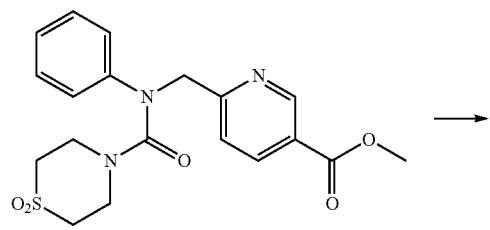

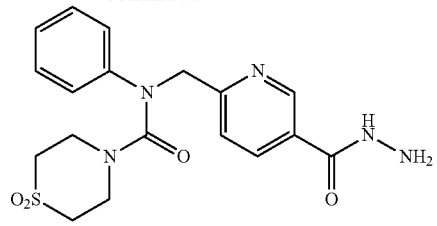

Methyl 6-((1,1-dioxido-N-phenylthiomorpholine-4-carboxamido)methyl)nicotinate (0.816 g, 2.023 mmol) prepared in Step 2 and hydrazine monohydrate (1.910 mL, 40.451 mmol) in ethanol (10 mL) was mixed at the room temperature and then heated at 100° C. under the microwaves for 1 hr, and cooled down to the room temperature to terminate the reaction. The reaction mixture was concentrated under the reduced pressure to remove the solvent. The crude product was crystallized at the room temperature using dichloromethane (20 mL). The resulting precipitates were filtered, washed by dichloromethane, and dried to give the title compound N-((5-(hydrazinecarbonyl)pyridin-2-yl)methyl)-N-phenylthiomorpholine-4-carboxamide 1,1-dioxide as light brown solid (0.560 g, 68.6%).

[Step 4] N-phenyl-N-((5-(2-(2,2,2-trifluoroacetyl)hydrazine-1-carbonyl)pyridin-2-yl)methyl)thiomorpholine-4-carboxamide 1,1-dioxide

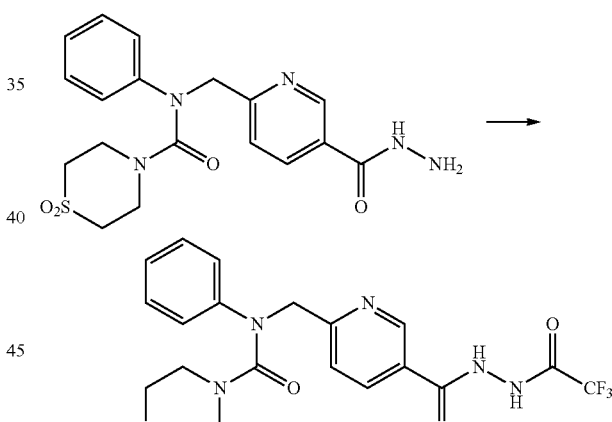

A solution of N-((5-(hydrazinecarbonyl)pyridin-2-yl)methyl)-N-phenylthiomorpholine-4-carboxamide 1,1-dioxide (0.260 g, 0.644 mmol) prepared in Step 3 and triethylamine (0.178 mL, 1.289 mmol) in dichloromethane (2 mL) was mixed at the room temperature with trifluoroacetic anhydride (0.101 mL, 0.580 mmol). The reaction mixture was stirred at the same temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-phenyl-N-((5-(2-(2,2,2-trifluoroacetyl)hydrazine-1-carbonyl)pyridin-2-yl)methyl)thiomorpholine-4-carboxamide 1,1-dioxide as white foam (0.268 g, 83.3%).

[Step 5] Compound 21372

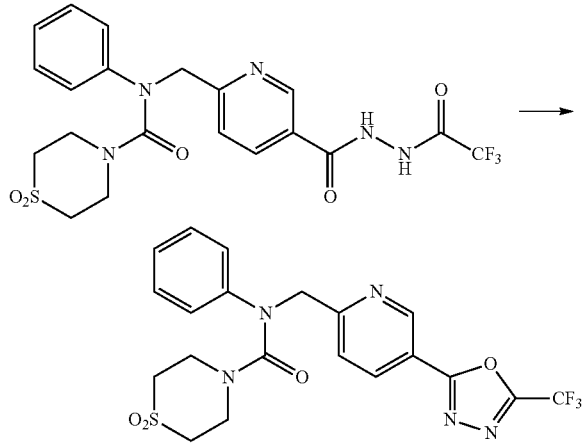

A mixture of N-phenyl-N-((5-(2-(2,2,2-trifluoroacetyl)hydrazine-1-carbonyl)pyridin-2-yl)methyl)thiomorpholine-4-carboxamide 1,1-dioxide (0.268 g, 0.537 mmol) prepared in Step 4 and 1-methoxy-N-triethylammoniosulfonyl-methanimidate (Burgess reagent, 0.192 g, 0.805 mmol) in tetrahydrofuran (2 mL) was heated at 150° C. for 30 min under the microwaves, and cooled down to the room temperature to terminate the reaction. Then, water was added to the reaction mixture, followed extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-phenyl-N-((5-(5-(trifluoromethyl)-1,3,4-oxadiazol-2-yl)pyridin-2-yl)methyl)thiomorpholine-4-carboxamide 1,1-dioxide as colorless oil (0.028 g, 10.9%).

$^1$H NMR (400 MHz, CDCl$_3$) δ 9.23 (d, 1H, J=2.2 Hz), 8.38 (dd, 1H, J=8.2, 2.3 Hz), 7.56 (d, 1H, J=8.2 Hz), 7.36 (t, 2H, J=7.9 Hz), 7.29-7.16 (m, 3H), 5.10 (s, 2H), 3.72 (t, 4H, J=5.2 Hz), 2.94 (t, 4H, J=5.3 Hz); LRMS (ES) m/z 482.37 (M$^+$+1).

Example 43. Compound 21373: N-((5-(5-(difluoromethyl)-1,3,4-oxadiazol-2-yl)pyridin-2-yl)methyl)-N-phenylthiomorpholine-4-carboxamide 1,1-dioxide

[Step 1] N-((5-(2-(2,2-difluoroacetyl)hydrazine-1-carbonyl)pyridin-2-yl)methyl)-N-phenylthiomorpholine-4-carboxamide 1,1-dioxide

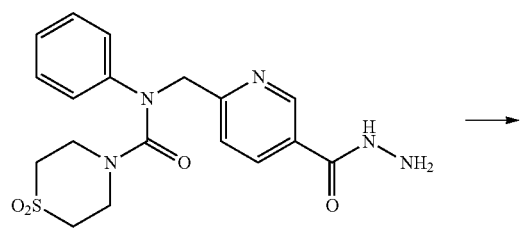

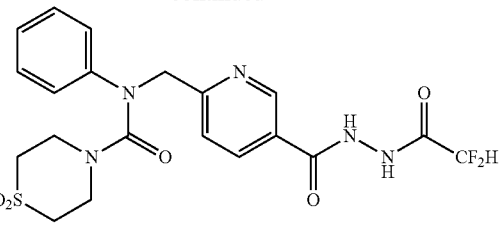

A solution of N-((5-(hydrazinecarbonyl)pyridin-2-yl)methyl)-N-phenylthiomorpholine-4-carboxamide 1,1-dioxide (0.260 g, 0.644 mmol) prepared in Step 3 of Example 42 and triethylamine (0.178 mL, 1.289 mmol) in dichloromethane (2 mL) was mixed at the room temperature with Difluoroacetic Anhydride (0.087 mL, 0.580 mmol). The reaction mixture was stirred at the same temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-((5-(2-(2,2-difluoroacetyl)hydrazine-1-carbonyl)pyridin-2-yl)methyl)-N-phenylthiomorpholine-4-carboxamide 1,1-dioxide as white foam (0.156 g, 50.3%).

[Step 2] Compound 21373

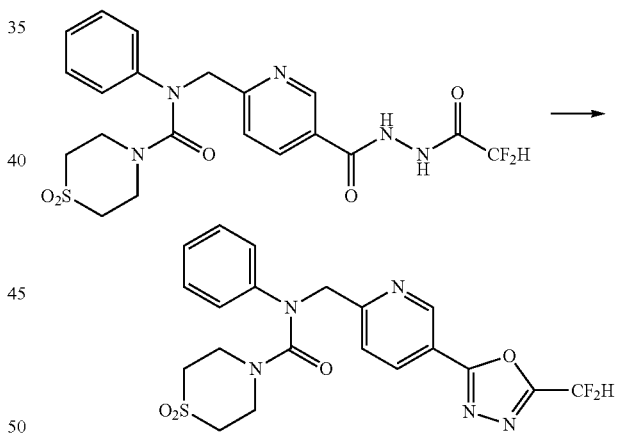

A mixture of N-((5-(2-(2,2-difluoroacetyl)hydrazine-1-carbonyl)pyridin-2-yl)methyl)-N-phenylthiomorpholine-4-carboxamide 1,1-dioxide (0.156 g, 0.324 mmol) prepared in Step 1 and 1-methoxy-N-triethylammoniosulfonyl-methanimidate (Burgess reagent, 0.116 g, 0.486 mmol) in tetrahydrofuran (2 mL) was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-((5-(5-(difluoromethyl)-1,3,4-oxadiazol- 2-yl)pyridin-2-yl)methyl)-N-phenylthiomorpholine-4-carboxamide 1,1-dioxide as colorless oil (0.078 g, 51.9%).

$^1$H NMR (400 MHz, CDCl$_3$) δ 9.23 (d, 1H, J=2.2 Hz), 8.38 (dd, 1H, J=8.2, 2.2 Hz), 7.54 (d, 1H, J=8.2 Hz), 7.41-7.31 (m, 2H), 7.19 (ddd, 3H, J=6.4, 3.0, 1.6 Hz), 6.94 (m, 1H), 5.10 (s, 2H), 3.72 (dd, 4H, J=6.9, 3.7 Hz), 2.97-2.90 (m, 4H); LRMS (ES) m/z 464.2 (M$^+$+1).

Example 44. Compound 21374: N-benzyl-N-(4-(5-(trifluoromethyl)-1,3,4-oxadiazol-2-yl)benzyl)thiomorpholine-4-carboxamide 1,1-dioxide

[Step 1] N-benzylthiomorpholine-4-carboxamide 1,1-dioxide

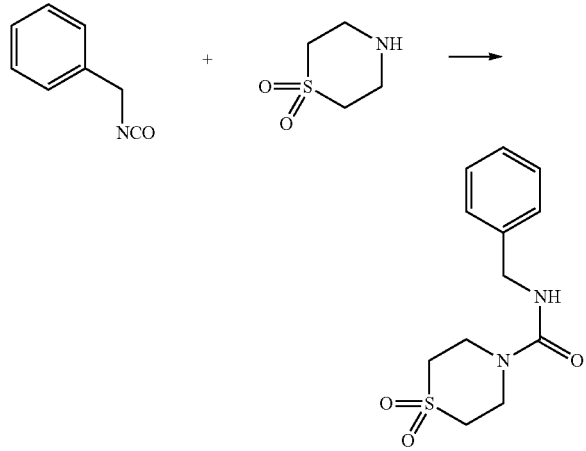

A solution of (isocyanatomethyl)benzene (1.000 g, 7.510 mmol) and thiomorpholine 1,1-dioxide (1.015 g, 7.510 mmol) in diethylether (10 mL) was stirred at the room temperature for 3 hr. The precipitates were collected by filtration, washed by diethylether, and dried to give the title compound N-benzylthiomorpholine-4-carboxamide 1,1-dioxide as white solid (1.769 g, 87.8%).

[Step 2] Methyl 4-((N-benzyl-1,1-dioxidothiomorpholine-4-carboxamido)methyl)benzoate

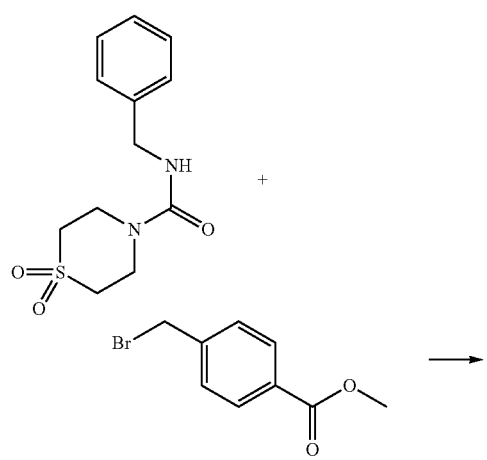

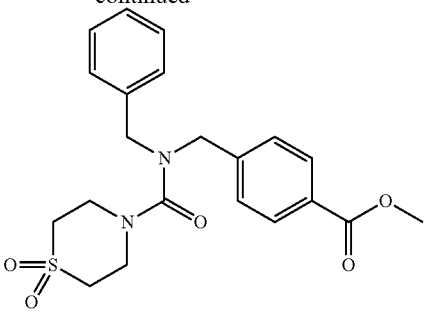

To a stirred solution of N-benzylthiomorpholine-4-carboxamide 1,1-dioxide (1.000 g, 3.727 mmol) prepared in Step 1 in N,N-dimethylformamide (10 mL) was added at 0° C. sodium hydride (60.00%, 0.149 g, 3.727 mmol). The reaction mixture was stirred at the same temperature for 30 min, treated at the room temperature with methyl 4-(bromomethyl)benzoate (0.854 g, 3.727 mmol), and stirred for additional 16 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 24 g cartridge; ethyl acetate/hexane=50% to 70%) to give the title compound methyl 4-((N-benzyl-1,1-dioxidothiomorpholine-4-carboxamido)methyl)benzoate as white solid (1.595 g, 102.8%).

[Step 3] N-benzyl-N-(4-(hydrazinecarbonyl)benzyl)thiomorpholine-4-carboxamide 1,1-dioxide

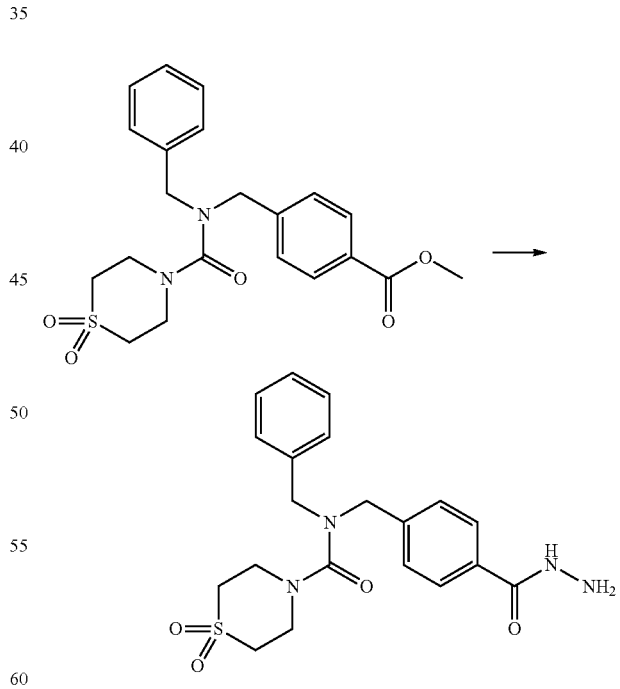

Methyl 4-((N-benzyl-1,1-dioxidothiomorpholine-4-carboxamido)methyl)benzoate (0.750 g, 1.801 mmol) prepared in Step 2 and hydrazine monohydrate (1.701 mL, 36.015 mmol) in ethanol (10 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude title compound N-benzyl-N-(4-(hydrazinecarbonyl)benzyl)thiomorpholine-4-carboxamide 1,1-dioxide was used without further purification (0.385 g, 51.3%, colorless oil).

[Step 4] N-benzyl-N-(4-(2-(2,2,2-trifluoroacetyl)hydrazine-1-carbonyl)benzyl)thiomorpholine-4-carboxamide 1,1-dioxide

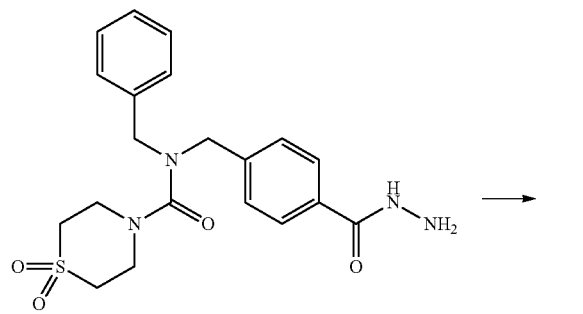

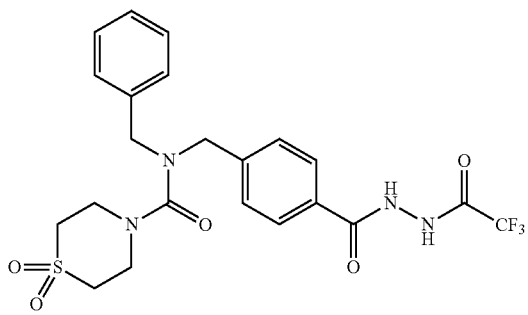

A solution of N-benzyl-N-(4-(hydrazinecarbonyl)benzyl)thiomorpholine-4-carboxamide 1,1-dioxide (0.385 g, 0,924 mmol) prepared in Step 3 and triethylamine (0.256 mL, 1.849 mmol) in dichloromethane (2 mL) was mixed at the room temperature with trifluoroacetic anhydride (0.144 mL, 0.832 mmol). The reaction mixture was stirred at the same temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-benzyl-N-(4-(2-(2,2,2-trifluoroacetyl)hydrazine-1-carbonyl)benzyl)thiomorpholine-4-carboxamide 1,1-dioxide as white foam (0.259 g, 54.6%).

[Step 5] Compound 21374

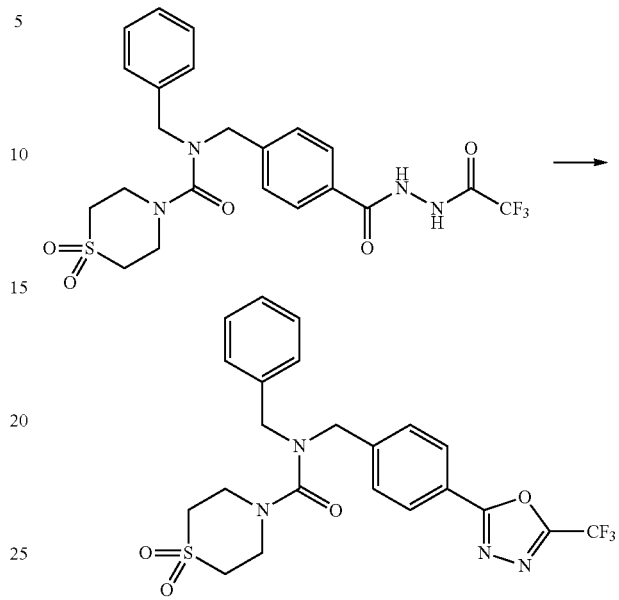

A mixture of N-benzyl-N-(4-(2-(2,2,2-trifluoroacetyl)hydrazine-1-carbonyl)benzyl)thiomorpholine-4-carboxamide 1,1-dioxide (0.259 g, 0.505 mmol) prepared in Step 4 and 1-methoxy-N-triethylammoniosulfonyl-methanimidate (Burgess reagent, 0.180 g, 0.757 mmol) in tetrahydrofuran (2 mL) was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-benzyl-N-(4-(5-(trifluoromethyl)-1,3,4-oxadiazol-2-yl)benzyl)thiomorpholine-4-carboxamide 1,1-dioxide as white foam (0.197 g, 79.0%).
$^1$H NMR (400 MHz, CDCl$_3$) δ 8.15-7.97 (m, 2H), 7.43-7.29 (m, 5H), 7.18-7.10 (m, 2H), 4.43 (s, 2H), 4.38 (s, 2H), 3.82 (t, 4H, J=5.4 Hz), 3.11 (t, 4H, J=5.3 Hz); LRMS (ES) m/z 495.51 (M$^+$+1).

Example 45. Compound 21375: N-ethyl-N-(4-(5-(trifluoromethyl)-1,3,4-oxadiazol-2-yl)benzyl)thiomorpholine-4-carboxamide 1,1-dioxide

[Step 1] N-ethylthiomorpholine-4-carboxamide 1,1-dioxide

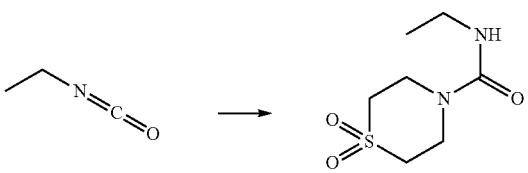

A solution of Ethyl isocyanate (0.690 g, 9.707 mmol) in diethylether (20 mL) was mixed at the room temperature with Thiomorpholine 1,1-Dioxide (1.575 g, 11.649 mmol). The reaction mixture was stirred at the same temperature for 1 hr. Then, water was added to the reaction mixture, followed by extraction with ethyl acetate. The organic layer was washed with brine, dried (anhydrous $MgSO_4$), filtered, and concentrated in vacuo. The precipitates were collected by filtration, washed by hexane, and dried to give the title compound N-ethylthiomorpholine-4-carboxamide 1,1-dioxide as white solid (1.790 g, 89.4%).

[Step 2] Methyl 4-((N-ethyl-1,1-dioxidothiomorpholine-4-carboxamido)methyl)benzoate

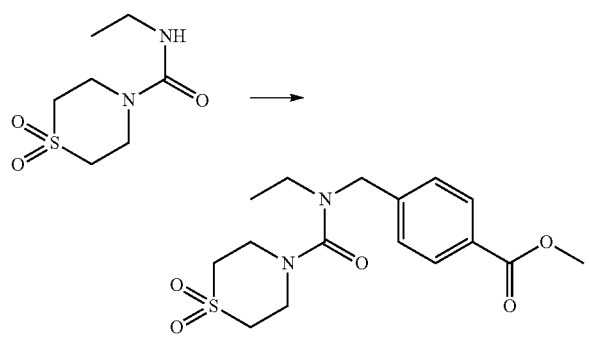

To a stirred solution of N-ethylthiomorpholine-4-carboxamide 1,1-dioxide (0.5 g, 2.42 mmol) prepared in Step 1 in N,N-dimethylformamide (10 mL) were added at 0° C. sodium hydride (60.0%, 0.136 g, 3.39 mmol). The reaction mixture was stirred at the same temperature for 20 min, treated at the room temperature with methyl 4-(bromomethyl)benzoate (0.72 g, 3.15 mmol), and stirred for additional 5 hr. Then, water was added to the reaction mixture, followed by extraction with ethyl acetate. The organic layer was washed with brine, dried (anhydrous $MgSO_4$), filtered, and concentrated in vacuo. The concentrate was purified and concentrated by column chromatography ($SiO_2$, 24 g cartridge; methanol/hexane=0% to 10%) to give the title compound methyl 4-((N-ethyl-1,1-dioxidothiomorpholine-4-carboxamido)methyl)benzoate as colorless oil (0.527 g, 61.3%).

[Step 3] N-ethyl-N-(4-(hydrazinecarbonyl)benzyl)thiomorpholine-4-carboxamide 1,1-dioxide

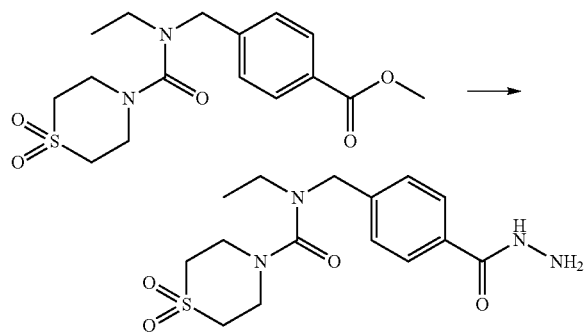

A mixture of methyl 4-((N-ethyl-1,1-dioxidothiomorpholine-4-carboxamido)methyl)benzoate (0.527 g, 1.487 mmol) prepared in Step 2 and hydrazine hydrate (1.445 mL, 29.739 mmol) in ethanol (10 mL) was heated at the room temperature for 1 hr under the microwaves. Then, water was added to the reaction mixture, followed by extraction with dichloromethane. The organic layer was washed with brine, dried (anhydrous $MgSO_4$), filtered, and concentrated in vacuo. The concentrate was purified and concentrated by column chromatography ($SiO_2$, 12 g cartridge; methanol/dichloromethane=0% to 30%) to give the title compound N-ethyl-N-(4-(hydrazinecarbonyl)benzyl)thiomorpholine-4-carboxamide 1,1-dioxide as white form (0.219 g, 41.6%).

[Step 4] N-ethyl-N-(4-(2-(2,2,2-trifluoroacetyl)hydrazine-1-carbonyl)benzyl)thiomorpholine-4 carboxamide 1,1-dioxide


N-ethyl-N-(4-(hydrazinecarbonyl)benzyl)thiomorpholine-4-carboxamide 1,1-dioxide (0.210 g, 0.593 mmol) prepared in Step 3, trifluoroacetic anhydride (0.074 mL, 0.533 mmol) and Triethylamine (0.123 mL, 0.889 mmol) were mixed at 0° C. in dichloromethane (10 mL) and then stirred at the room temperature for 12 hr. Then, water was added to the reaction mixture, followed by extraction with ethyl acetate. The organic layer was washed with brine, dried (anhydrous $MgSO_4$), filtered, and concentrated in vacuo. The concentrate was purified and concentrated by column chromatography ($SiO_2$, 24 g cartridge; methanol/dichloromethane=0% to 30%) to give the title compound N-ethyl-N-(4-(2-(2,2,2-trifluoroacetyl)hydrazine-1-carbonyl)benzyl)thiomorpholine-4 carboxamide 1,1-dioxide as white foam solid (0.165 g, 61.8%).

[Step 5] Compound 21375

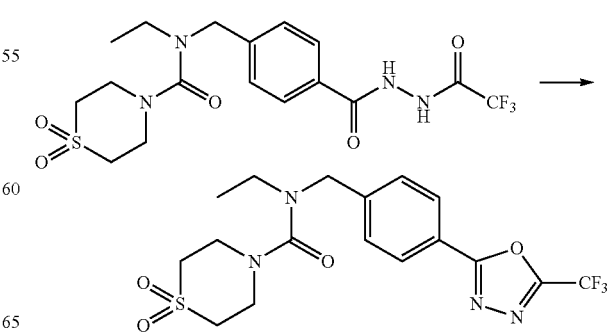

A mixture of N-ethyl-N-(4-(2-(2,2,2-trifluoroacetyl)hydrazine-1-carbonyl)benzyl)thiomorpholine-4-carboxamide 1,1-dioxide (0.165 g, 0.366 mmol) prepared in Step 4 and 1-methoxy-N-triethylammoniosulfonyl-methanimidate (Burgess reagent, 0.113 g, 0.476 mmol) in tetrahydrofuran (10 mL) was heated at the room temperature for 1 hr under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 20%) to give the title compound N-ethyl-N-(4-(5-(trifluoromethyl)-1,3,4-oxadiazol-2-yl)benzyl)thiomorpholine-4-carboxamide 1,1-dioxide as colorless oil (0.097 g, 61.2%).

$^1$H NMR (400 MHz, DMSO-d$_6$) δ 8.06 (d, 2H, J=8.5 Hz), 7.55 (d, 2H, J=8.5 Hz), 4.49 (s, 2H), 3.58 (m, 4H), 3.19-3.13 (m, 6H), 1.09 (t, 3H, J=7.0 Hz); LRMS (ES) m/z 433.1 (M$^+$+1).

Example 46. Compound 21376: (3S,5R)-4-Benzyl-3,5-dimethyl-N-phenyl-N-(4-(5-(trifluoromethyl)-1,3,4-oxadiazol-2-yl)benzyl)piperazine-1-carboxamide

[Step 1] Methyl 4-(((3S,5R)-4-benzyl-3,5-dimethyl-N-phenylpiperazine-1-carboxamido)methyl)benzoate

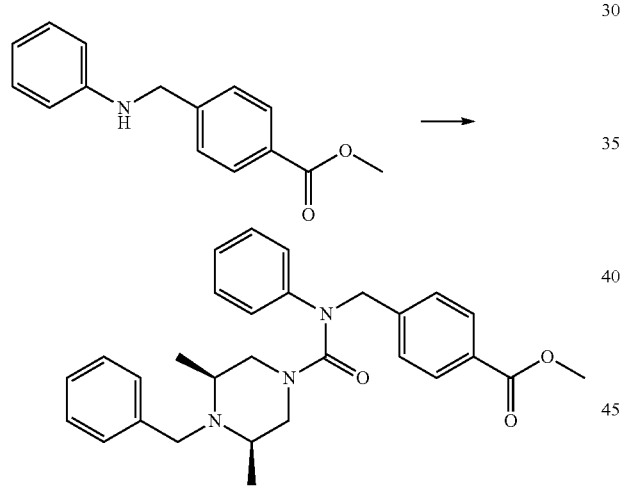

To a stirred solution of methyl 4-((phenylamino)methyl)benzoate (5.000 g, 20.722 mmol) in dichloromethane (10 mL) were added at 0° C. triphosgene (4.919 g, 16.578 mmol) and N,N-diisopropylethylamine (18.095 mL, 103.610 mmol). The reaction mixture was stirred at the same temperature for 1 hr, treated at the room temperature with (2S,6R)-1-benzyl-2,6-dimethylpiperazine (5.081 g, 24.866 mmol), and stirred for additional 17 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=30% to 80%) to give the title compound methyl 4-(((3S,5R)-4-benzyl-3,5-dimethyl-N-phenylpiperazine-1-carboxamido)methyl)benzoate as pale yellow oil (4.300 g, 44.0%).

[Step 2] (3S,5R)-4-Benzyl-N-(4-(hydrazinecarbonyl)benzyl)-3,5-dimethyl-N-phenylpiperazine-1-carboxamide

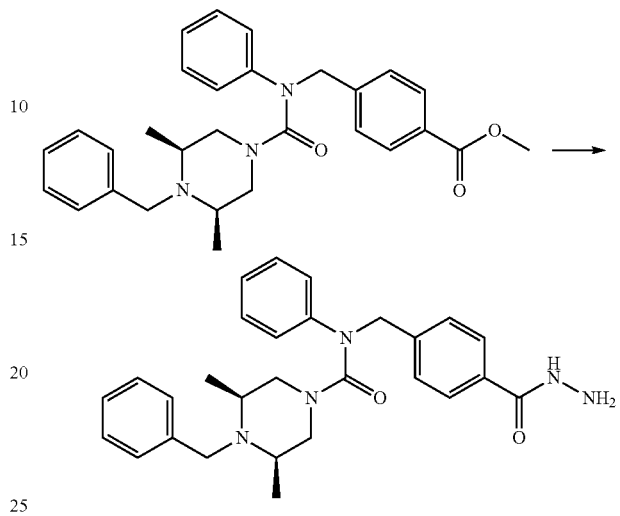

Methyl 4-(((3S,5R)-4-benzyl-3,5-dimethyl-N-phenylpiperazine-1-carboxamido)methyl)benzoate (4.500 g, 9.542 mmol) prepared in Step 1 and hydrazine monohydrate (9.275 mL, 190.840 mmol) in ethanol (15 mL) was mixed at the room temperature and then heated at 120° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The organic layer was washed with brine, dried (anhydrous MgSO$_4$), filtered, and concentrated in vacuo. The title compound (3S,5R)-4-benzyl-N-(4-(hydrazinecarbonyl)benzyl)-3,5-dimethyl-N-phenylpiperazine-1-carboxamide was used without further purification (4.230 g, 94.0%, white solid).

[Step 3] (3S,5R)-4-Benzyl-3,5-dimethyl-N-phenyl-N-(4-(2-(2,2,2-trifluoroacetyl)hydrazine-1-carbonyl)benzyl)piperazine-1-carboxamide

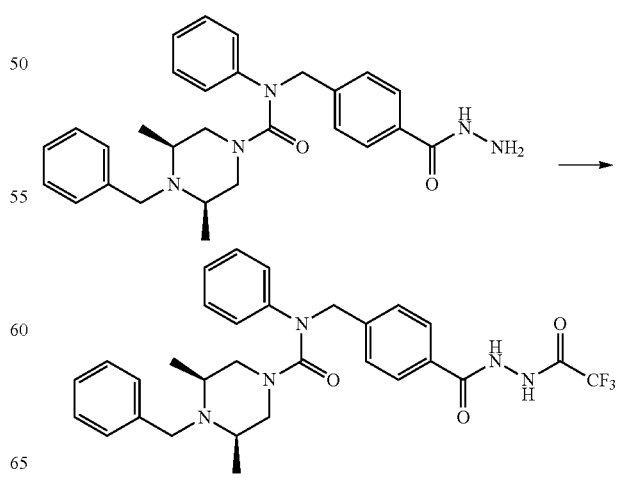

A solution of (3S,5R)-4-benzyl-N-(4-(hydrazinecarbonyl)benzyl)-3,5-dimethyl-N-phenylpiperazine-1-carboxamide (4.230 g, 8.969 mmol) prepared in Step 2 and triethylamine (1.865 mL, 13.454 mmol) in dichloromethane (200 mL) was mixed at the room temperature with trifluoroacetic anhydride (1.004 mL, 8.072 mmol). The reaction mixture was stirred at the same temperature for 2 hr. Then, saturated aqueous sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 40 g cartridge; ethyl acetate/hexane=40% to 100%) to give the title compound (3S,5R)-4-benzyl-3,5-dimethyl-N-phenyl-N-(4-(2-(2,2,2-trifluoroacetyl)hydrazine-1-carbonyl)benzyl)piperazine-1-carboxamide as pale yellow oil (1.830 g, 35.9%).

[Step 4] Compound 21376

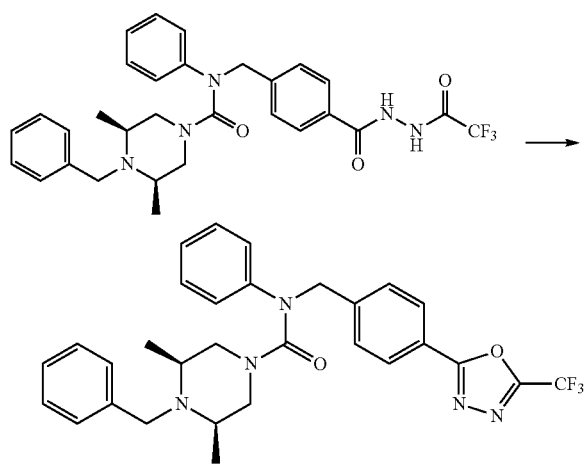

(3S,5R)-4-benzyl-3,5-dimethyl-N-phenyl-N-(4-(2-(2,2,2-trifluoroacetyl)hydrazine-1-carbonyl)benzyl)piperazine-1-carboxamide (1.830 g, 3.224 mmol) prepared in Step 3 and 1-methoxy-N-triethylammoniosulfonyl-methanimidate (Burgess reagent, 1.152 g, 4.836 mmol) in tetrahydrofuran (30 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=30% to 50%) to give the title compound (3S,5R)-4-benzyl-3,5-dimethyl-N-phenyl-N-(4-(5-(trifluoromethyl)-1,3,4-oxadiazol-2-yl)benzyl)piperazine-1-carboxamide as yellow solid (1.180 g, 66.6%).

$^1$H NMR (400 MHz, CDCl$_3$) δ 8.02 (d, 2H, J=8.2 Hz), 7.49 (d, 2H, J=8.1 Hz), 7.31-7.26 (m, 7H), 7.12 (t, 1H, J=7.3 Hz), 7.04 (d, 2H, J=7.9 Hz), 4.93 (s, 2H), 3.75 (s, 2H), 3.65 (d, 2H, J=11.2 Hz), 2.58-2.52 (m, 2H), 2.41 (brs, 1H), 0.91 (s, 6H); LRMS (ESI) m/z 550.4 (M$^+$+H).

Example 47. Compound 21377: 4,4-Difluoro-N-phenyl-N-(4-(5-(trifluoromethyl)-1,3,4-oxadiazol-2-yl)benzyl)piperidine-1-carboxamide

[Step 1] Methyl 4-((4,4-difluoro-N-phenylpiperidine-1-carboxamido)methyl)benzoate

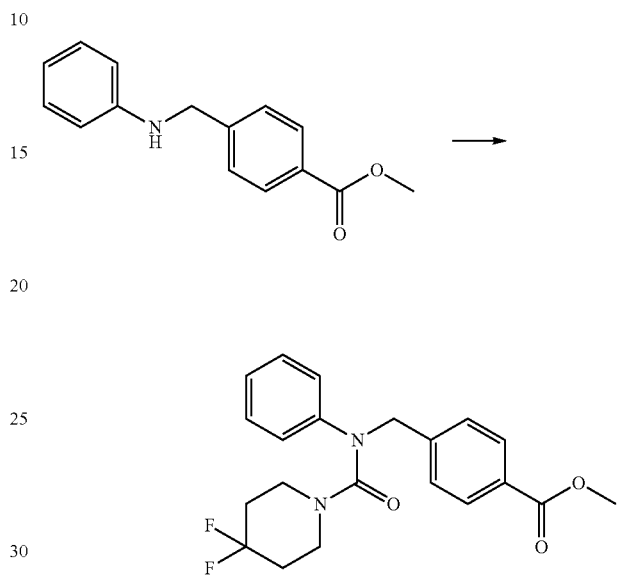

To a stirred solution of methyl 4-((phenylamino)methyl)benzoate (0.280 g, 1.160 mmol) in dichloromethane (5 mL) were added at 0° C. triphosgene (0.275 g, 0.928 mmol) and N,N-diisopropylethylamine (1.013 mL, 5.802 mmol). The reaction mixture was stirred at the same temperature for 30 min, treated at the room temperature with 4,4-difluoropiperidine hydrochloride (0:219 g, 1.393 mmol), and stirred for additional 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 10%) to give the title compound methyl 4-((4,4-difluoro-N-phenylpiperidine-1-carboxamido)methyl)benzoate as pale yellow oil (0.443 g, 98.3%).

[Step 2] 4,4-Difluoro-N-(4-(hydrazinecarbonyl)benzyl)-N-phenylpiperidine-1-carboxamide

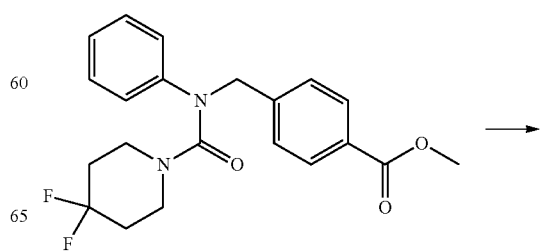

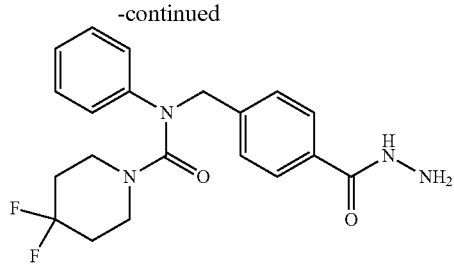

Methyl 4-((4,4-difluoro-N-phenylpiperidine-1-carboxamido)methyl)benzoate (0.443 g, 1.141 mmol) prepared in Step 1 and hydrazine monohydrate (1.109 mL, 22.811 mmol) in ethanol (10 mL) was mixed at the room temperature and then heated at 120° C. under the microwaves for 2 hr, and cooled down to the room temperature to terminate the reaction. The reaction mixture was concentrated under the reduced pressure to remove the solvent, and water was added to the concentrate, followed by extraction with ethyl acetate. The organic layer was washed with brine, dried (anhydrous MgSO$_4$), filtered, and concentrated in vacuo. The title compound 4,4-difluoro-N-(4-(hydrazinecarbonyl)benzyl)-N-phenylpiperidine-1-carboxamide was used without further purification (0.400 g, 90.3%, white solid (foam)).

[Step 3] 4,4-Difluoro-N-phenyl-N-(4-(2-(2,2,2-trifluoroacetyl)hydrazine-1-carbonyl)benzyl)piperidine-1-carboxamide

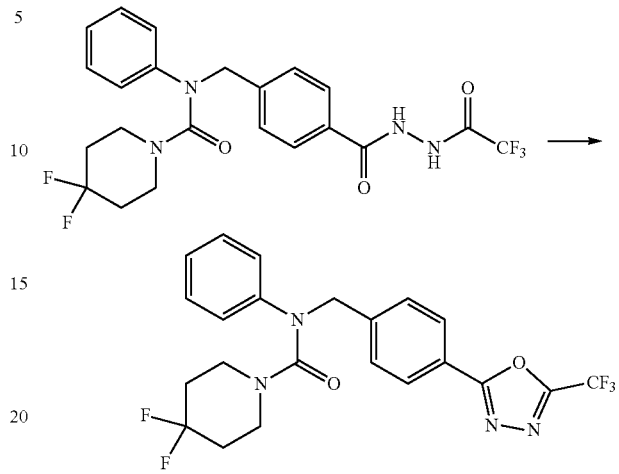

A solution of 4,4-difluoro-N-(4-(hydrazinecarbonyl)benzyl)-N-phenylpiperidine-1-carboxamide (0.400 g, 1.030 mmol) prepared in Step 2 and triethylamine (0.214 mL, 1.545 mmol) in dichloromethane (10 mL) was mixed at the room temperature with trifluoroacetic anhydride (0.115 mL, 0.927 mmol). The reaction mixture was stirred at the same temperature for 1 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=10% to 100%) to give the title compound 4,4-difluoro-N-phenyl-N-(4-(2-(2,2,2-trifluoroacetyl)hydrazine-1-carbonyl)benzyl)piperidine-1-carboxamide as white solid (0.211 g, 42.3%).

[Step 4] Compound 21377

4,4-Difluoro-N-phenyl-N-(4-(2-(2,2,2-trifluoroacetyl)hydrazine-1-carbonyl)benzyl)piperidine-1-carboxamide (0.211 g, 0.436 mmol) prepared in Step 3 and 1-methoxy-N-triethylammoniosulfonyl-methanimidate (Burgess reagent, 0.156 g, 0.653 mmol) in tetrahydrofuran (10 mL) was mixed at the room temperature and then heated at 150° C. under the microwaves for 30 min, and cooled down to the room temperature to terminate the reaction The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 30%) to give the title compound 4,4-difluoro-N-phenyl-N-(4-(5-(trifluoromethyl)-1,3,4-oxadiazol-2-yl)benzyl)piperidine-1-carboxamide as colorless oil (0.144 g, 70.9%).

$^1$H NMR (400 MHz, CDCl$_3$) δ 8.01 (d, 2H, J=8.2 Hz), 7.47 (d, 2H, J=8.2 Hz), 7.32 (t, 2H, J=7.8 Hz), 7.15 (t, 1H, J=7.4 Hz), 7.07 (d, 2H, J=7.6 Hz), 4.92 (s, 2H), 3.35 (t, 4H, J=5.7 Hz), 1.81-1.62 (m, 4H); LRMS (ESI) m/z 467.2 (M$^+$+H).

Example 48. Compound 21378 Hydrochloride: N-(4-(5-(difluoromethyl)-1,3,4-oxadiazol-2-yl)-2-fluorobenzyl)-4-methyl-N-phenylpiperazine-1-carboxamide

[Step 1] Methyl 3-fluoro-4-((4-methyl-N-phenylpiperazine-1-carboxamido)methyl)benzoate

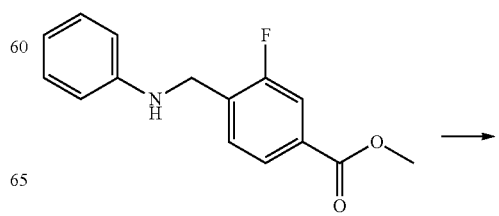

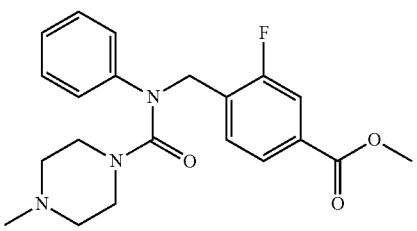

To a stirred solution of methyl 3-fluoro-4-((phenylamino)methyl)benzoate (3.000 g, 11.571 mmol) in dichloromethane (100 mL) were added at 0° C. triphosgene (2.747 g, 9.256 mmol) and N,N-diisopropylethylamine (10.104 mL, 57.853 mmol). The reaction mixture was stirred at the same temperature for 1 hr, treated at the room temperature with 1-methylpiperazine (1.391 g, 13.885 mmol), and stirred for additional 5 hr. Then, saturated aqueous sodium bicarbonate solution was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 40 g cartridge; methanol/dichloromethane=0% to 10%) to give the title compound methyl 3-fluoro-4-((4-methyl-N-phenylpiperazine-1-carboxamido)methyl)benzoate as brown oil (2.750 g, 61.7%).

[Step 2] N-(2-fluoro-4-(hydrazinecarbonyl)benzyl)-4-methyl-N-phenylpiperazine-1-carboxamide

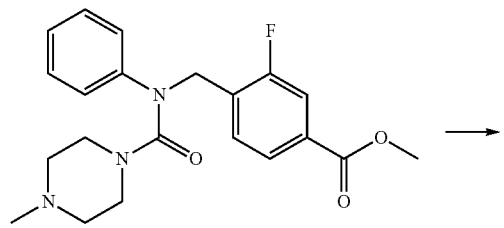

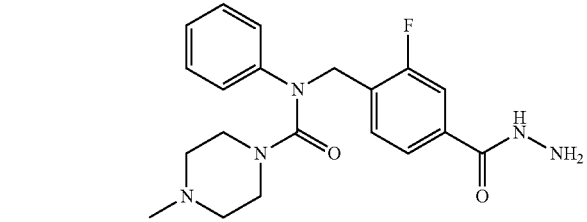

Methyl 3-fluoro-4-((4-methyl-N-phenylpiperazine-1-carboxamido)methyl)benzoate (2.740 g, 7.109 mmol) prepared in Step 1 and hydrazine monohydrate (6.910 mL, 142.175 mmol) in ethanol (30 mL) was mixed at the room temperature and then heated at 120° C. under the microwaves for 1 hr, and cooled down to the room temperature to terminate the reaction. The reaction mixture was concentrated under the reduced pressure to remove the solvent. The title compound N-(2-fluoro-4-(hydrazinecarbonyl)benzyl)-4-methyl-N-phenylpiperazine-1-carboxamide was used without further purification (2.410 g, 88.0%, white solid).

[Step 3] N-(4-(2-(2,2-difluoroacetyl)hydrazine-1-carbonyl)-2-fluorobenzyl)-4-methyl-N-phenylpiperazine-1-carboxamide

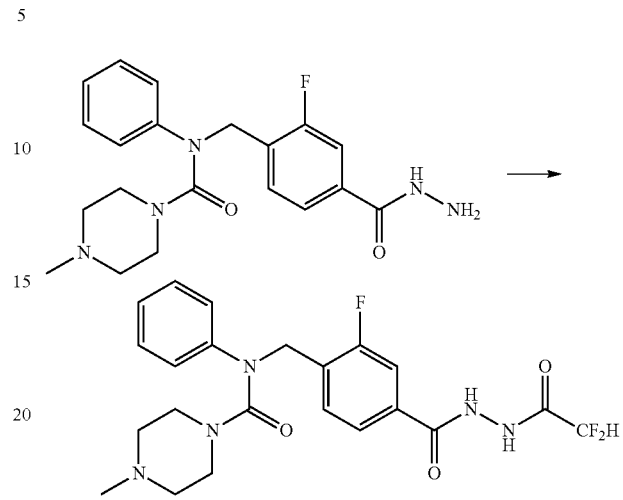

A solution of (2-fluoro-4-(hydrazinecarbonyl)benzyl)-4-methyl-N-phenylpiperazine-1-carboxamide (1.400 g, 3.632 mmol) prepared in Step 2 and triethylamine (0.755 mL, 5.448 mmol) in dichloromethane (30 mL) was mixed at the room temperature with 2,2-difluoroacetic anhydride (0.406 mL, 3.269 mmol). The reaction mixture was stirred at the same temperature for 1 hr. Then, saturated aqueous sodium bicarbonate solution was added to the reaction mixture, followed by extraction with dichloremethane. The organic layer was washed with brine, dried (anhydrous MgSO₄), filtered, and concentrated in vacuo. The concentrate was purified and concentrated by column chromatography (SiO₂, 40 g cartridge; methanol/dichloromethane=0% to 10%) to give the title compound N-(4-(2-(2,2-difluoroacetyl)hydrazine-1-carbonyl)-2-fluorobenzyl)-4-methyl-N-phenylpiperazine-1-carboxamide as pale yellow oil (0.300 g, 17.8%).

[Step 4] Compound 21378

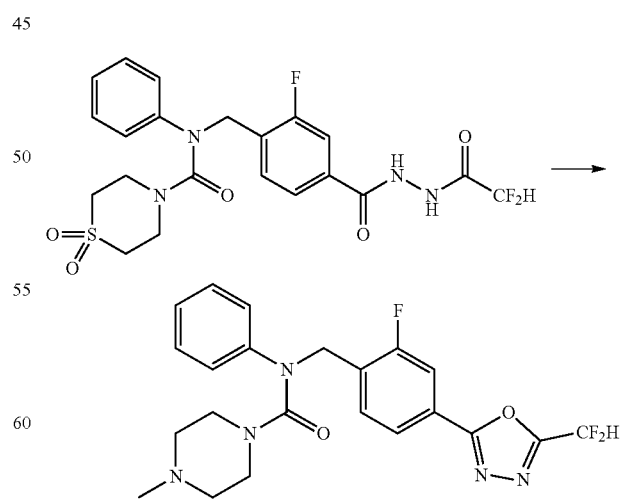

N-(4-(2-(2,2-difluoroacetyl)hydrazine-1-carbonyl)-2-fluorobenzyl)-4-methyl-N-phenylpiperazine-1-carboxamide (0.300 g, 0.647 mmol) prepared in Step 3 and 1-methoxy- N-triethylammoniosulfonyl-methanimidate (Burgess reagent, 0.231 g, 0.971 mmol) in tetrahydrofuran (10 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(5-(difluoromethyl)-1,3,4-oxadiazol-2-yl)-2-fluorobenzyl)-4-methyl-N-phenylpiperazine-1-carboxamide as colorless oil (0.098 g, 34.0%).

$^1$H NMR (400 MHz, CDCl$_3$) δ 7.85 (dd, 1H, J=7.9, 1.5 Hz), 7.73 (dd, 1H, J=10.1, 1.5 Hz), 7.31 (t, 2H, J=7.9 Hz), 7.13 (t, 1H, J=7.5 Hz), 7.10-7.08 (m, 2H), 6.90 (t, 1H, J=51.7 Hz), 4.96 (s, 2H), 3.36 (brs, 4H), 2.32 (brs, 7H); LRMS (ESI) m/z 446.2 (M$^+$+H).

[Step 5] Compound 21378 Hydrochloride: N-(4-(5-(difluoromethyl)-1,3,4-oxadiazol-2-yl)-2-fluorobenzyl)-4-methyl-N-phenylpiperazine-1-carboxamide hydrochloride

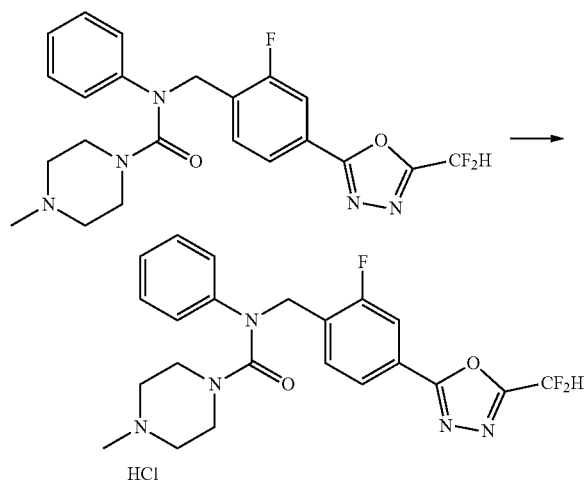

To a solution of N-(4-(5-(difluoromethyl)-1,3,4-oxadiazol-2-yl)-2-fluorobenzyl)-4-methyl-N-phenylpiperazine-1-carboxamide (0.100 g, 0.224 mmol) prepared in Step 4 in ethyl acetate (3 mL) was added at the room temperature HCl (1.00 M solution in EtOAc, 0.236 mL, 0.236 mmol), and stirred at the same temperature for 1 hr. The precipitates were collected by filtration, washed by ethyl acetate, and dried to give the title compound N-(4-(5-(difluoromethyl)-1,3,4-oxadiazol-2-yl)-2-fluorobenzyl)-4-methyl-N-phenylpiperazine-1-carboxamide hydrochloride as white solid (0.076 g, 70.3%).

$^1$H NMR (400 MHz, DMSO-d$_6$) δ 10.60 (brs, 1H), 7.86 (dd, 1H, J=8.0, 1.6 Hz), 7.78 (dd, 1H, J=10.3, 1.6 Hz), 7.72 (t, 1H, J=7.8 Hz), 7.55 (t, 1H, J=51.3 Hz), 7.38 (t, 2H, J=7.9 Hz), 7.25 (d, 2H, J=7.6 Hz), 7.16 (t, 1H, J=7.3 Hz), 4.97 (s, 2H), 3.76 (d, 2H, J=13.8 Hz), 3.25 (d, 2H, J=10.2 Hz), 3.01-3.00 (m, 2H), 2.80 (brs, 2H); LRMS (ES) m/z 446.50 (M$^+$+1).

Example 49. Compound 21379: 4-Methyl-N-phenyl-N-(4-(5-(trifluoromethyl)-1,3,4-oxadiazol-2-yl)benzyl)-1,4-diazepane-1-carboxamide

[Step 1] Methyl 4-((4-methyl-N-phenyl-1,4-diazepane-1-carboxamido)methyl)benzoate

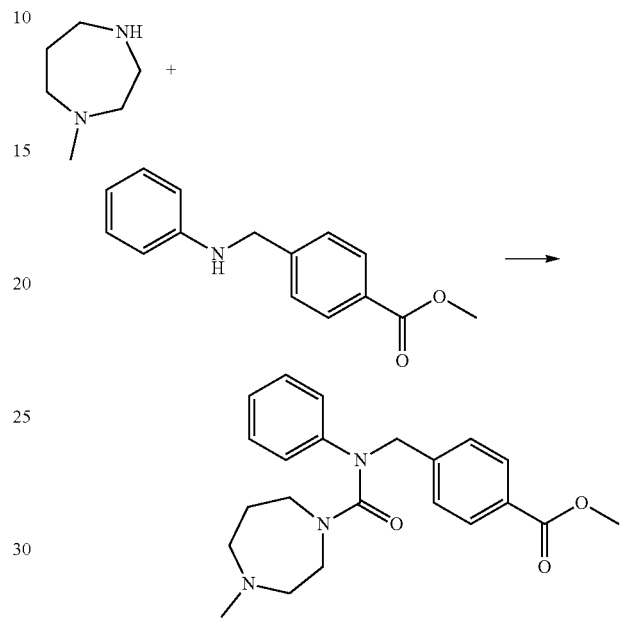

To a stirred solution of methyl 4-((phenylamino)methyl)benzoate (0.300 g, 1.244 mmol) in dichloromethane (10 mL) were added at 0° C. N,N-diisopropylethylamine (1.083 mL, 6.218 mmol) and triphosgene (0.295 g, 0.995 mmol). The reaction mixture was stirred at the same temperature for 30 min, treated at the room temperature with 1-methyl-1,4-diazepane (0.170 mL, 1.368 mmol), and stirred for additional 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((4-methyl-N-phenyl-1,4-diazepane-1-carboxamido)methyl)benzoate as Colorless oil (0.450 g, 94.9%).

[Step 2] N-(4-(hydrazinecarbonyl)benzyl)-4-methyl-N-phenyl-1,4-diazepane-1-carboxamide

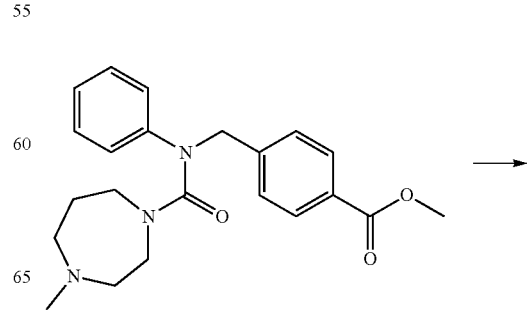

-continued

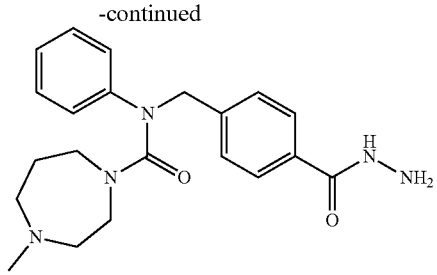

A mixture of methyl 4-((4-methyl-N-phenyl-1,4-diazepane-1-carboxamido)methyl)benzoate (0.420 g, 1.101 mmol) prepared in Step 1 and hydrazine hydrate (1.040 mL, 22.020 mmol) in ethanol (10 mL) was heated at 120° C. for 1 hr under the microwaves, and cooled down to the room temperature to terminate the reaction. Then, water was added to the reaction mixture, followed by extraction with dichloremethane. The organic layer was washed with brine, dried (anhydrous MgSO₄), filtered, and concentrated in vacuo to give the title compound N-(4-(hydrazinecarbonyl)benzyl)-4-methyl-N-phenyl-1,4-diazepane-1-carboxamide (0.420 g, 100.0%. Colorless oil).

[Step 3] 4-Methyl-N-phenyl-N-(4-(2-(2,2,2-trifluoroacetyl)hydrazine-1-carbonyl)benzyl)-1,4-diazepane-1-carboxamide

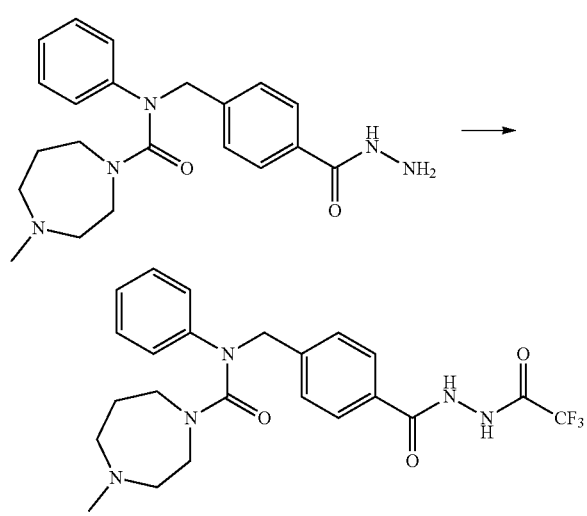

A solution of N-(4-(hydrazinecarbonyl)benzyl)-4-methyl-N-phenyl-1,4-diazepane-1-carboxamide (0.444 g, 1.164 mmol) prepared in Step 2, trifluoroacetic anhydride (0.146 mL, 1.047 mmol) and triethylamine (0.242 mL, 1.746 mmol) in dichloromethane (10 mL) was stirred at the room temperature for 4 hr. Then, water was added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound 4-methyl-N-phenyl-N-(4-(2-(2,2,2-trifluoroacetyl)hydrazine-1-carbonyl)benzyl)-1,4-diazepane-1-carboxamide as Colorless oil (0.348 g, 62.6%).

[Step 4] Compound 21379

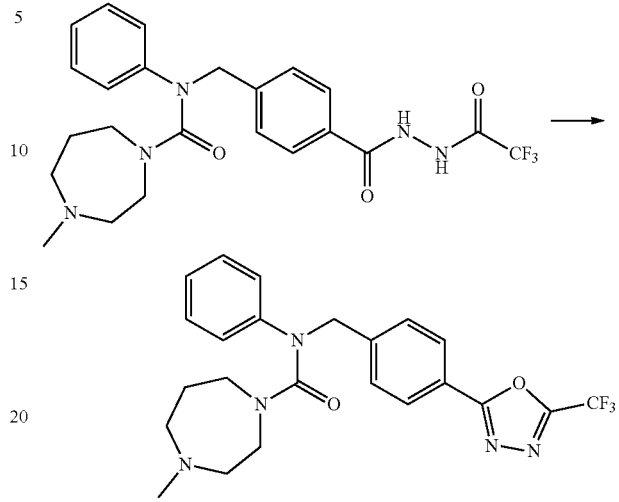

A mixture of 4-methyl-N-phenyl-N-(4-(2-(2,2,2-trifluoroacetyl)hydrazine-1-carbonyl)benzyl)-1,4-diazepane-1-carboxamide (0.348 g, 0.729 mmol) prepared in Step 3 and 1-methoxy-N-triethylammoniosulfonyl-methanimidate (Burgess reagent, 0.261 g, 1.093 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound 4-methyl-N-phenyl-N-(4-(5-(trifluoromethyl)-1,3,4-oxadiazol-2-yl)benzyl)-1,4-diazepane-1-carboxamide as Colorless oil (0.143 g, 42.7%).
$^1$H NMR (400 MHz, CDCl₃) δ 8.01 (d, 2H, J=8.5 Hz), 7.51 (d, 2H, J=8.6 Hz), 7.12-7.07 (m, 1H), 7.02-6.99 (m, 2H), 4.91 (s, 2H), 3.41-3.39 (m, 2H), 2.55 (t, 2H, J=4.7 Hz), 2.48 (t, 2H, J=5.3 Hz), 2.31 (s, 3H), 1.78-1.74 (m, 2H); LRMS (ES) m/z 460.2 (M⁺+1).

Example 50. Compound 21380: (2S,6R)-2,6-Dimethyl-N-phenyl-N-(4-(5-(trifluoromethyl)-1,3,4-oxadiazol-2-yl)benzyl) morpholine-4-carboxamide

[Step 1] Methyl 4-(((2S,6R)-2,6-dimethyl-N-phenylmorpholine-4-carboxamido)methyl)benzoate

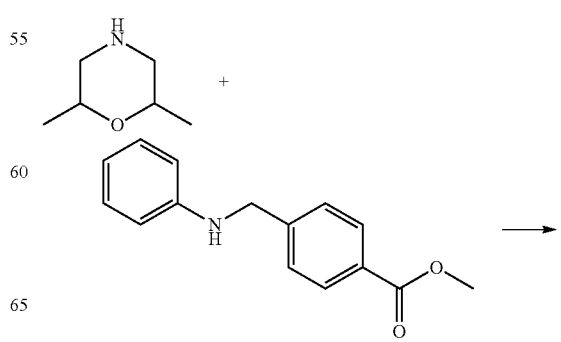

-continued

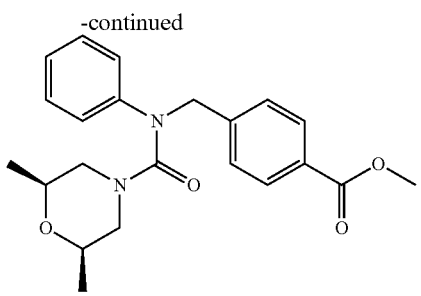

To a stirred solution of methyl 4-((phenylamino)methyl)benzoate (0.300 g, 1.244 mmol) in dichloromethane (10 mL) were added at 0° C. N,N-diisopropylethylamine (1.083 mL, 6.218 mmol) and triphosgene (0.295 g, 0.995 mmol). The reaction mixture was stirred at the same temperature for 1 hr, treated at the room temperature with 2,6-dimethylmorpholine (0.168 mL, 1.368 mmol), and stirred for additional 4 hr. Then, water was added to the reaction mixture, followed by extraction with dichloremethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-(((2S,6R)-2,6-dimethyl-N-phenylmorpholine-4-carboxamido)methyl)benzoate as Colorless oil (0.392 g, 82.4%).

[Step 2] (2S,6R)—N-(4-(hydrazinecarbonyl)benzyl)-2,6-dimethyl-N-phenylmorpholine-4-carboxamide

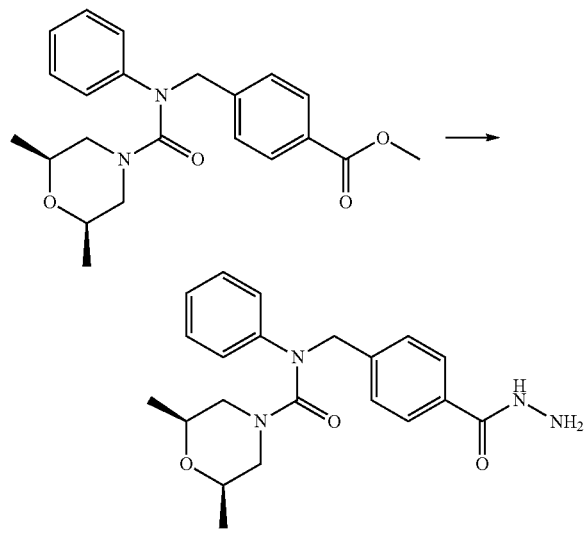

A mixture of methyl 4-(((2S,6R)-2,6-dimethyl-N-phenylmorpholine-4-carboxamido)methyl)benzoate (0.392 g, 1.025 mmol) prepared in Step 1 and hydrazine hydrate (0.968 mL, 20.499 mmol) in ethanol (10 mL) was heated at 120° C. for 1 hr under the microwaves, and cooled down to the room temperature to terminate the reaction. Then, water was added to the reaction mixture, followed by extraction with dichloremethane. The organic layer was washed with brine, dried (anhydrous MgSO$_4$), filtered, and concentrated in vacuo to give the title compound (2S,6R)—N-(4-(hydrazinecarbonyl)benzyl)-2,6-dimethyl-N-phenylmorpholine-4-carboxamide (0.380 g, 96.9%, Colorless oil).

[Step 3] (2S,6R)-2,6-Dimethyl-N-phenyl-N-(4-(2-(2,2,2-trifluoroacetyl)hydrazine-1-carbonyl)benzyl)morpholine-4-carboxamide

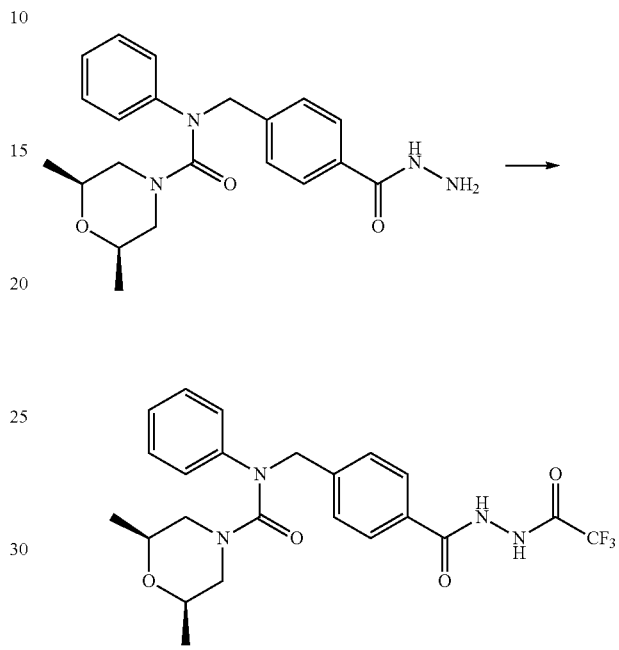

A solution of (2S,6R)—N-(4-(hydrazinecarbonyl)benzyl)-2,6-dimethyl-N-phenylmorpholine-4-carboxamide (0.337 g, 0.881 mmol) prepared in Step 2, trifluoroacetic anhydride (0.110 mL, 0.793 mmol) and triethylamine (0.183 mL, 1.322 mmol) in dichloromethane (10 mL) was stirred at the room temperature for 3 hr. Then, water was added to the reaction mixture, followed by extraction with dichloremethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 30%) to give the title compound (2S,6R)-2,6-dimethyl-N-phenyl-N-(4-(2-(2,2,2-trifluoroacetyl)hydrazine-1-carbonyl)benzyl)morpholine-4-carboxamide as Colorless oil (0.316 g, 75.0%).

[Step 4] Compound 21380

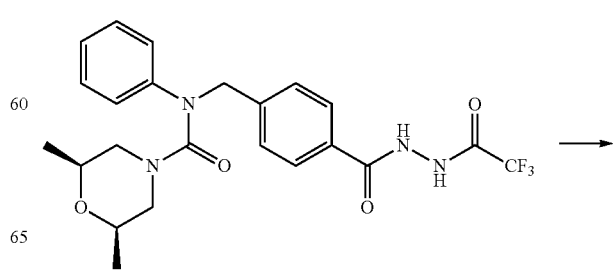

-continued

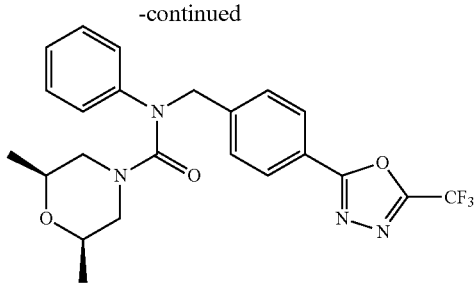

A mixture of (2S,6R)-2,6-dimethyl-N-phenyl-N-(4-(2-(2,2,2-trifluoroacetyl)hydrazine-1-carbonyl)benzyl)morpholine-4-carboxamide (0.316 g, 0.660 mmol) prepared in Step 3 and 1-methoxy-N-triethylammoniosulfonyl-methanimidate (Burgess reagent, 0.236 g, 0.991 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound (2S,6R)-2,6-dimethyl-N-phenyl-N-(4-(5-(trifluoromethyl)-1,3,4-oxadiazol-2-yl)benzyl) morpholine-4-carboxamide as Colorless oil (0.110 g, 36.2%).

$^1$H NMR (400 MHz, CDCl$_3$) δ 8.03 (d, 2H, J=8.4 Hz), 7.50 (d, 2H, J=8.4 Hz), 7.32-7.28 (m, 2H), 7.15-7.11 (m, 1H), 7.07-7.05 (m, 2H), 4.94 (s, 2H), 3.67 (d, 2H, J=12.9 Hz), 3.42-3.37 (m, 2H), 2.39-2.33 (m, 2H), 1.04 (d, 6H, J=6.3 Hz); LRMS (ES) m/z 461.2 (M$^+$+1).

Example 51. Compound 21381: 4-(Tert-butyl)-N-phenyl-N-(4-(5-(trifluoromethyl)-1,3,4-oxadiazol-2-yl)benzyl)piperazine-1-carboxamide

[Step 1] Methyl 4-((4-(tert-butyl)-N-phenylpiperazine-1-carboxamido)methyl)benzoate

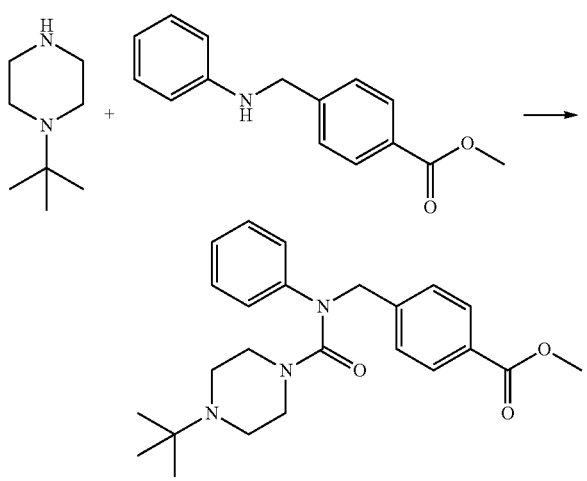

To a stirred solution of methyl 4-((phenylamino)methyl)benzoate (0.300 g, 1.244 mmol) in dichloromethane (20 mL) were added at 0° C. N,N-diisopropylethylamine (1.083 mL, 6.218 mmol) and triphosgene (0.295 g, 0.995 mmol). The reaction mixture was stirred at the same temperature for 1 hr, treated at the room temperature with 1-(tert-butyl)piperazine (0.265 g, 1.865 mmol), and stirred for additional 8 hr. Then, water was added to the reaction mixture, followed by extraction with dichloremethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((4-(tert-butyl)-N-phenylpiperazine-1-carboxamido)methyl)benzoate as Red oil (0.440 g, 86.4%).

[Step 2] 4-(Tert-butyl)-N-(4-(hydrazinecarbonyl)benzyl)-N-phenylpiperazine-1-carboxamide

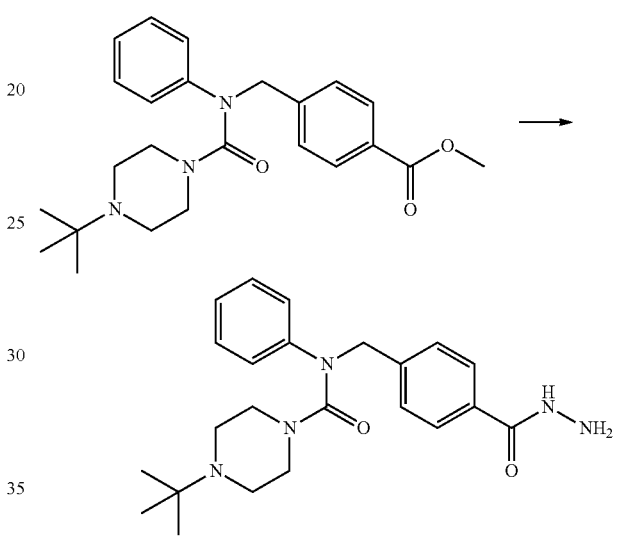

A mixture of methyl 4-((4-(tert-butyl)-N-phenylpiperazine-1-carboxamido)methyl)benzoate (0.300 g, 0.733 mmol) prepared in Step 1 and hydrazine monohydrate (0.692 mL, 14.651 mmol) in ethanol (10 mL) was heated at 120° C. for 1 hr under the microwaves, and cooled down to the room temperature to terminate the reaction. Then, water was added to the reaction mixture, followed by extraction with dichloremethane. The organic layer was washed with brine, dried (anhydrous MgSO$_4$), filtered, and concentrated in vacuo to give the title compound 4-(tert-butyl)-N-(4-(hydrazinecarbonyl)benzyl)-N-phenylpiperazine-1-carboxamide (0.300 g, 100.0%, Colorless oil).

[Step 3] 4-(Tert-butyl)-N-phenyl-N-(4-(2-(2,2,2-trifluoroacetyl)hydrazine-1-carbonyl)benzyl)piperazine-1-carboxamide

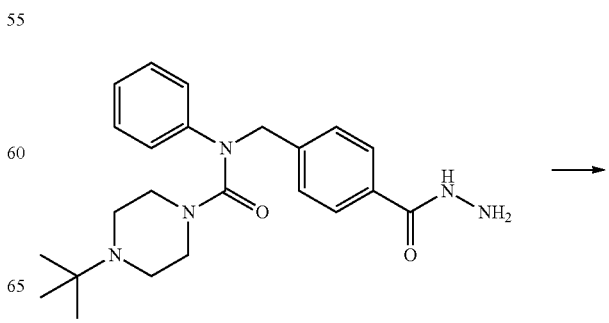

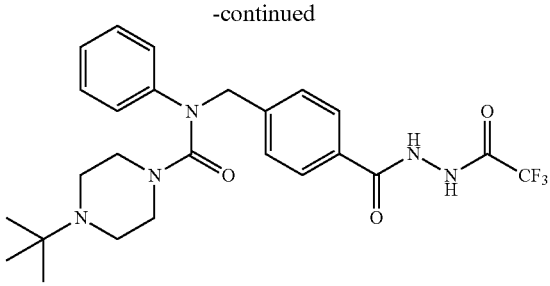

A solution of 4-(tert-butyl)-N-(4-(hydrazinecarbonyl)benzyl)-N-phenylpiperazine-1-carboxamide (0.400 g, 0.977 mmol) prepared in Step 2, trifluoroacetic anhydride (0.122 mL, 0.879 mmol) and triethylamine (0.203 mL, 1.465 mmol) in dichloromethane (10 mL) was stirred at the room temperature for 4 hr. Then, water was added to the reaction mixture, followed by extraction with dichloremethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound 4-(tert-butyl)-N-phenyl-N-(4-(2-(2,2,2-trifluoroacetyl)hydrazine-1-carbonyl)benzyl)piperazine-1-carboxamide as Colorless oil (0.300 g, 60.8%).

[Step 4] Compound 21381

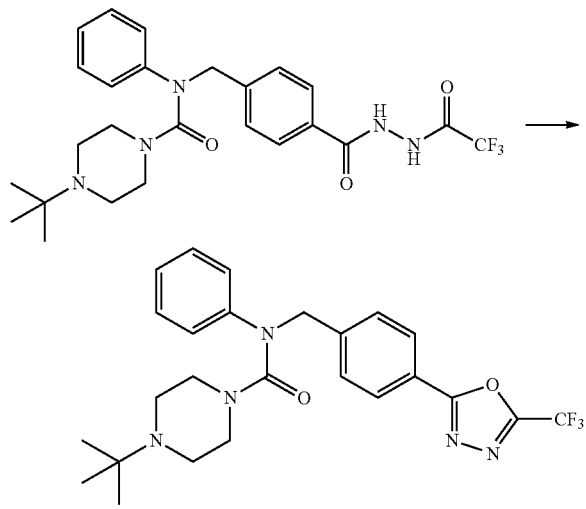

A mixture of 4-(tert-butyl)-N-phenyl-N-(4-(2-(2,2,2-trifluoroacetyl)hydrazine-1-carbonyl)benzyl)piperazine-1-carboxamide (0.300 g, 0.593 mmol) prepared in Step 3 and 1-methoxy-N-triethylammoniosulfonyl-methanimidate (Burgess reagent, 0.212 g, 0.890 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound 4-(tert-butyl)-N-phenyl-N-(4-(5-(trifluoromethyl)-1,3,4-oxadiazol-2-yl)benzyl)piperazine-1-carboxamide as Colorless oil (0.120 g, 41.5%).
$^1$H NMR (400 MHz, CDCl$_3$) δ 8.04 (dd, 2H, J=6.6, 1.8 Hz), 7.51 (d, 2H, J=8.4 Hz), 7.32-7.28 (m, 2H), 7.11 (t, 1H, J=7.4 Hz), 7.05 (dd, 2H, J=8.5, 1.1 Hz), 4.96 (s, 2H), 3.29 (s, 4H), 2.20 (s, 4H), 1.11 (s, 9H); LRMS (ES) m/z 488.2 (M$^+$+1).

Example 52. Compound 21382: 4-(Tert-butyl)-N-(2-fluoro-4-(5-(trifluoromethyl)-1,3,4-oxadiazol-2-yl)benzyl)-N-phenylpiperazine-1-carboxamide

[Step 1] Methyl 4-((4-(tert-butyl)-N-phenylpiperazine-1-carboxamido)methyl)-3-fluorobenzoate

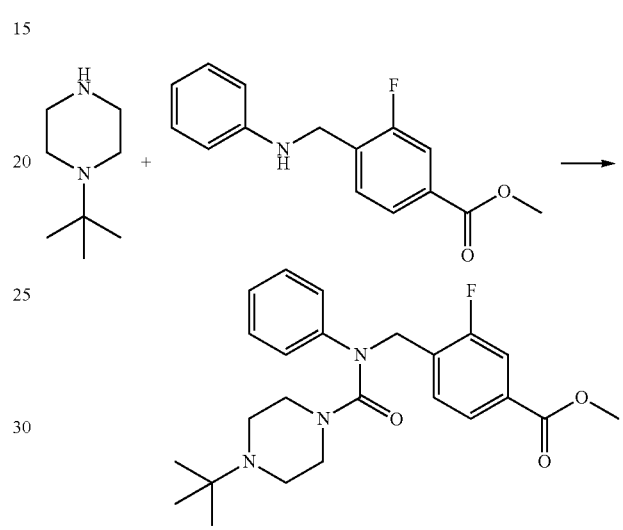

To a stirred solution of methyl 3-fluoro-4-((phenylamino)methyl)benzoate (0.300 g, 1.157 mmol) in dichloromethane (20 mL) were added at 0° C. N,N-diisopropylethylamine (1.010 mL, 5.785 mmol) and triphosgene (0.275 g, 0.926 mmol). The reaction mixture was stirred at the same temperature for 1 hr, treated at the room temperature with 1-(tert-butyl)piperazine (0.247 g, 1.736 mmol), and stirred for additional 4 hr. Then, water was added to the reaction mixture, followed by extraction with dichloremethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((4-(tert-butyl)-N-phenylpiperazine-1-carboxamido)methyl)-3-fluorobenzoate as Red oil (0.450 g, 91.0%).

[Step 2] 4-(Tert-butyl)-N-(2-fluoro-4-(hydrazinecarbonyl)benzyl)-N-phenylpiperazine-1-carboxamide

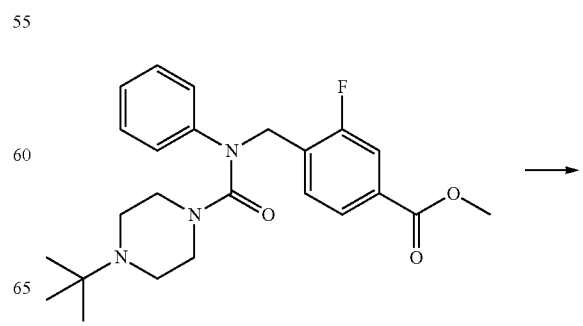

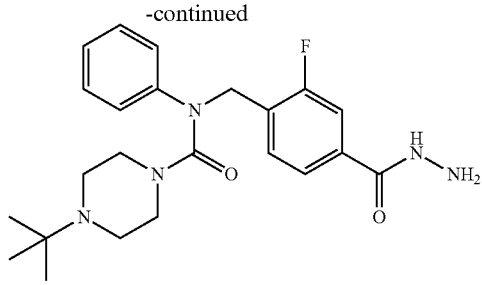

A mixture of methyl 4-((4-(tert-butyl)-N-phenylpiperazine-1-carboxamido)methyl)-3-fluorobenzoate (0.400 g, 0.936 mmol) prepared in Step 1 and hydrazine hydrate (0.884 mL, 18.713 mmol) in ethanol (10 mL) was heated at 120° C. for 1 hr under the microwaves, and cooled down to the room temperature to terminate the reaction. Then, water was added to the reaction mixture, followed by extraction with dichloremethane. The organic layer was washed with brine, dried (anhydrous MgSO$_4$), filtered, and concentrated in vacuo to give the title compound 4-(tert-butyl)-N-(2-fluoro-4-(hydrazinecarbonyl)benzyl)-N-phenylpiperazine-1-carboxamide (0.400 g, 100.0%, Colorless oil).

[Step 3] 4-(Tert-butyl)-N-(2-fluoro-4-(2-(2,2,2-trifluoroacetyl)hydrazine-1-carbonyl)benzyl)-N-phenylpiperazine-1-carboxamide

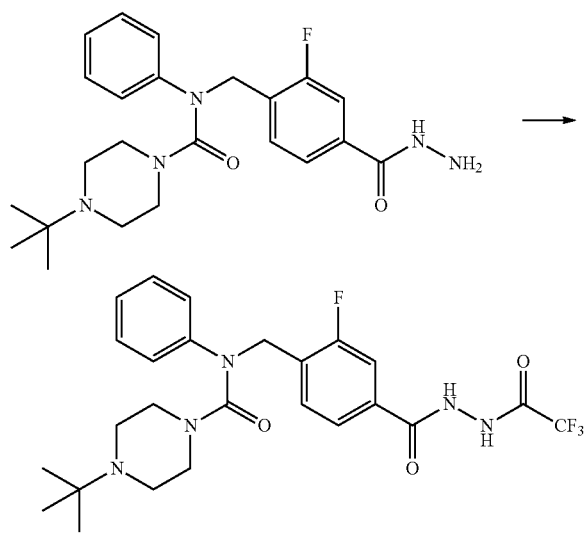 [SMILES: CC(C)(C)N1CCN(C(=O)N(Cc2ccc(C(=O)NN)cc2F)c2ccccc2)CC1 ; CC(C)(C)N1CCN(C(=O)N(Cc2ccc(C(=O)NNC(=O)C(F)(F)F)cc2F)c2ccccc2)CC1]

A solution of 4-(tert-butyl)-N-(2-fluoro-4-(hydrazinecarbonyl)benzyl)-N-phenylpiperazine-1-carboxamide (0.400 g, 0.936 mmol) prepared in Step 2, trifluoroacetic anhydride (0.117 mL, 0.842 mmol) and triethylamine (0.195 mL, 1.403 mmol) in dichloromethane (10 mL) was stirred at the room temperature for 4 hr. Then, water was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound 4-(tert-butyl)-N-(2-fluoro-4-(2-(2,2,2-trifluoroacetyl)hydrazine-1-carbonyl)benzyl)-N-phenylpiperazine-1-carboxamide as Colorless oil (0.330 g, 67.4%).

[Step 4] Compound 21382

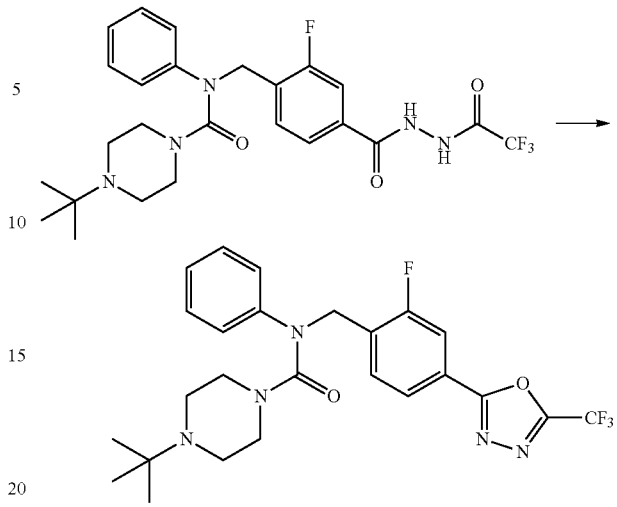

A mixture of 4-(tert-butyl)-N-(2-fluoro-4-(2-(2,2,2-trifluoroacetyl)hydrazine-1-carbonyl)benzyl)-N-phenylpiperazine-1-carboxamide (0.336 g, 0.642 mmol) prepared in Step 3 and 1-methoxy-N-triethylammoniosulfonyl-methanimidate (Burgess reagent, 0.229 g, 0.963 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound 4-(tert-butyl)-N-(2-fluoro-4-(5-(trifluoromethyl)-1,3,4-oxadiazol-2-yl)benzyl)-N-phenylpiperazine-1-carboxamide as Colorless oil (0.130 g, 40.1%).

$^1$H NMR (400 MHz, CDCl$_3$) δ 7.87 (dd, 1H, J=8.0, 1.6 Hz), 7.77-7.71 (m, 2H), 7.33-7.28 (m, 2H), 7.14-7.08 (m, 3H), 5.00 (s, 2H), 3.28 (s, 4H), 2.41 (s, 4H), 0.90 (s, 9H); LRMS (ES) m/z 506.2 (M$^+$+1).

Example 53. Compound 21383: 4-(Tert-butyl)-N-(4-(5-(difluoromethyl)-1,3,4-oxadiazol-2-yl)-2-fluorobenzyl)-N-phenylpiperazine-1-carboxamide

[Step 1] 4-(Tert-butyl)-N-(4-(2-(2,2-difluoroacetyl)hydrazine-1-carbonyl)-2-fluorobenzyl)-N-phenylpiperazine-1-carboxamide

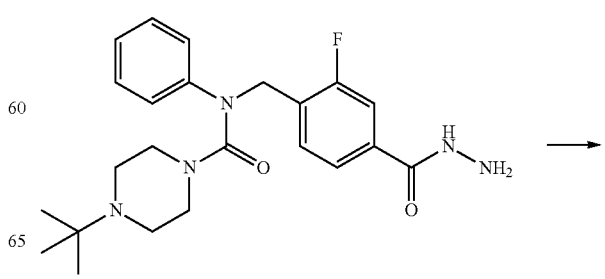

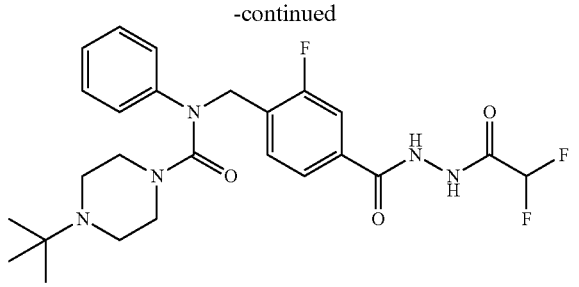

A solution of 4-(tert-butyl)-N-(2-fluoro-4-(hydrazinecarbonyl)benzyl)-N-phenylpiperazine-1-carboxamide (0.472 g, 1.104 mmol) prepared in Step 2 of Example 52, 2,2-difluoroacetic anhydride (0.108 mL, 0.994 mmol) and triethylamine (0.112 mL, 0.806 mmol) in dichloromethane (20 mL) was stirred at the room temperature for 4 hr. Then, water was added to the reaction mixture, followed by extraction with dichloremethane. The organic layer was washed with brine, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound 4-(tert-butyl)-N-(4-(2-(2,2-difluoroacetyl)hydrazine-1-carbonyl)-2-fluorobenzyl)-N-phenylpiperazine-1-carboxamide as Colorless oil (0.419 g, 75.1%).

[Step 2] Compound 21383

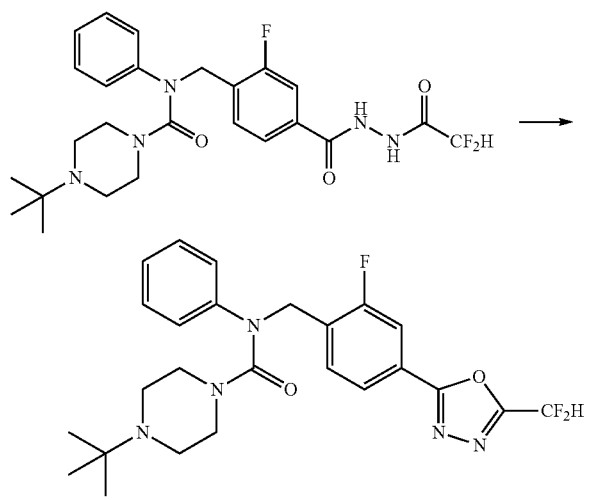

A mixture of 4-(tert-butyl)-N-(4-(2-(2,2-difluoroacetyl)hydrazine-1-carbonyl)-2-fluorobenzyl)-N-phenylpiperazine-1-carboxamide (0.419 g, 0.829 mmol) prepared in Step 1 and 1-methoxy-N-triethylammoniosulfonyl-methanimidate (Burgess reagent, 0.296 g, 1.243 mmol) in tetrahydrofuran (10 mL) was heated at 150° C. for 30 hr under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound 4-(tert-butyl)-N-(4-(5-(difluoromethyl)-1,3,4-oxadiazol-2-yl)-2-fluorobenzyl)-N-phenylpiperazine-1-carboxamide as Colorless oil (0.210 g, 52.0%).

$^1$H NMR (400 MHz, CDCl₃) δ 7.87 (dd, 1H, J=8.0, 1.6 Hz), 7.77-7.71 (m, 2H), 7.33-7.28 (m, 2H), 7.14-7.08 (m, 3H), 7.05-6.80 (m, 1H), 5.00 (s, 2H), 3.28-3.27 (m, 4H), 2.41-2.40 (m, 4H), 1.01 (s, 9H); LRMS (ES) m/z 488.2 (M⁺+1).

Example 54. Compound 21384: 4-(2-Hydroxyethyl)-N-phenyl-N-(4-(5-(trifluoromethyl)-1,3,4-oxadiazol-2-yl)benzyl)piperazine-1-carboxamide

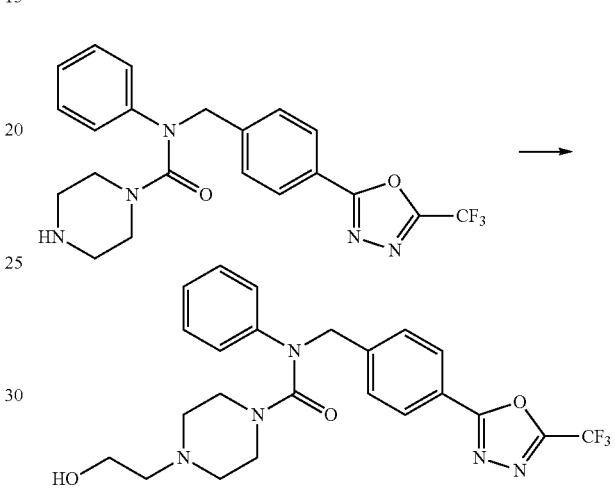

N-phenyl-N-(4-(5-(trifluoromethyl)-1,3,4-oxadiazol-2-yl)benzyl)piperazine-1-carboxamide (0.100 g, 0.232 mmol) prepared in Example 32, 2-iodoethan-1-ol (0.048 g, 0.278 mmol) and cesium carbonate (0.113 g, 0.348 mmol) were dissolved in acetonitrile (4 mL) at the room temperature and then the solution was heated at reflux for 17 hr, and cooled down to the room temperature to terminate the reaction. The reaction mixture was concentrated under the reduced pressure to remove the solvent, and water was added to the concentrate, followed by extraction with dichloremethane. The bi-phasic mixture was passed through a plastic frit to remove solid residues and aqueous layer, and the organic layer collected was concentrated in vacuo. The concentrate was purified by column chromatography (Waters, C18; aqueous 0.1%-acetonitrile solution/aqueous 0.1%-formic acid solution=5% to 75%), and the fraction containing the product was passed through an SPE cartridge (PL-HCO3 MPresin) to give the crude product which was subsequently chromatographed (SiO₂, 4 g cartridge; methanol/dichloromethane=0% to 10%) to give the title compound 4-(2-hydroxyethyl)-N-phenyl-N-(4-(5-(trifluoromethyl)-1,3,4-oxadiazol-2-yl)benzyl)piperazine-1-carboxamide as pale yellow oil (0.014 g, 12.7%).

$^1$H NMR (400 MHz, CDCl₃) δ 8.03 (d, 2H, J=8.2 Hz), 7.50 (d, 2H, J=8.2 Hz), 7.32 (t, 2H, J=7.8 Hz), 7.14 (t, 1H, J=7.4 Hz), 7.07 (d, 2H, J=7.7 Hz), 4.95 (s, 2H), 3.61 (t, 2H, J=5.2 Hz), 3.33 (t, 4H, J=4.7 Hz), 2.74 (brs, 1H), 2.54 (t, 2H, J=5.2 Hz), 2.40 (t, 4H, J=4.6 Hz); LRMS (ES) m/z 476.3 (M⁺+1).

Example 55. Compound 21385: (3S,5R)-3,5-Dimethyl-N-phenyl-N-(4-(5-(trifluoromethyl)-1,3,4-oxadiazol-2-yl)benzyl)piperazine-1-carboxamide

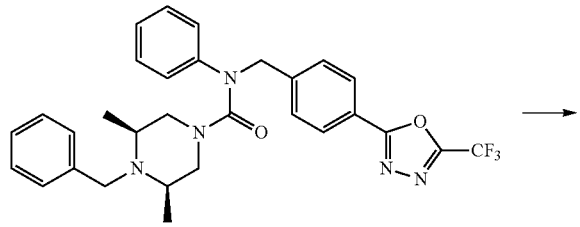

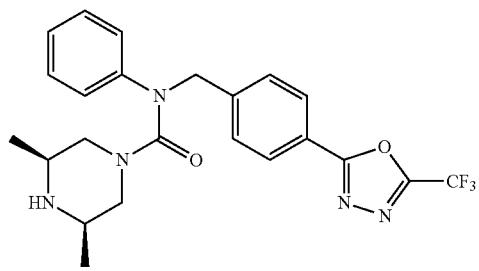

A solution of (3S,5R)-4-benzyl-3,5-dimethyl-N-phenyl-N-(4-(5-(trifluoromethyl)-1,3,4-oxadiazol-2-yl)benzyl)piperazine-1-carboxamide (1.160 g, 2.111 mmol) in ethanol (20 mL) was slowly treated at the room temperature with 10% Pd/C (200 mg), and stirred at the same temperature under the hydrogen atmosphere (H2 balloon) for 5 hr. The reaction mixture was filtered through a celite pad to remove solids, and concentrated under the reduced pressure to remove the solvent. The title compound (3S,5R)-3,5-dimethyl-N-phenyl-N-(4-(5-(trifluoromethyl)-1,3,4-oxadiazol-2-yl)benzyl) piperazine-1-carboxamide was obtained without further purification (1.000 g, 103.1%, yellow oil).

$^1$H NMR (400 MHz, CDCl$_3$) δ 8.01 (d, 2H, J=8.4 Hz), 7.48 (d, 2H), J=8.4 Hz, 7.28 (t, 2H, J=8.2 Hz), 7.10 (t, 1H, J=7.4 Hz), 7.04-7.02 (m, 2H), 4.91 (s, 2H), 3.74-3.68 (m, 2H), 2.66-2.61 (m, 2H), 2.22 (t, 2H, J=11.7 Hz), 0.92 (d, 6H, J=6.3 Hz).

Example 56. Compound 21386: (3R,5S)-3,4,5-Trimethyl-N-phenyl-N-(4-(5-(trifluoromethyl)-1,3,4-oxadiazol-2-yl)benzyl)piperazine-1-carboxamide

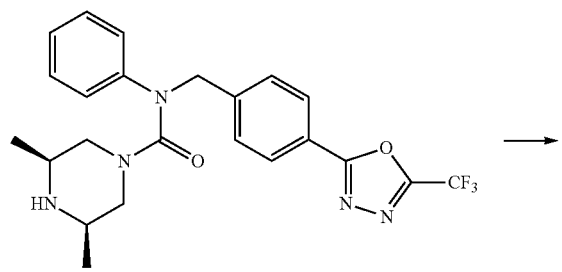

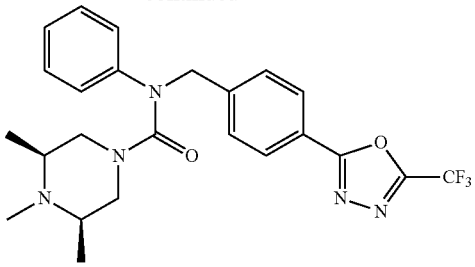

A solution of (3S,5R)-3,5-dimethyl-N-phenyl-N-(4-(5-(trifluoromethyl)-1,3,4-oxadiazol-2-yl)benzyl)piperazine-1-carboxamide (0.200 g, 0.435 mmol) prepared in Example 55, CH3I (0.041 mL, 0.653 mmol) and cesium carbonate (0.284 g, 0.871 mmol) in acetonitrile (3 mL) was stirred at the room temperature for 17 hr. The reaction mixture was concentrated under the reduced pressure to remove the solvent, and water was added to the concentrate, followed by extraction with dichloremethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound (3R,5S)-3,4,5-trimethyl-N-phenyl-N-(4-(5-(trifluoromethyl)-1,3,4-oxadiazol-2-yl)benz yl)piperazine-1-carboxamide as yellow oil (0.017 g, 8.2%).

$^1$H NMR (400 MHz, CDCl$_3$) δ 8.01 (d, 2H, J=8.3 Hz), 7.47 (d, 2H, J=8.2 Hz), 7.30 (t, 2H, J=7.8 Hz), 7.13 (t, 1H, J=7.2 Hz), 7.05-7.02 (m, 2H), 4.92 (s, 2H), 3.66 (d, 2H, J=12.8 Hz), 2.50 (brs, 2H), 2.23 (brs, 3H), 2.04 (brs, 2H), 0.98 (brs, 6H); LRMS (ESI) m/z 474.1 (M$^+$+H).

Example 57. Compound 21387: (3R,5S)-4-Acetyl-3,5-dimethyl-N-phenyl-N-(4-(5-(trifluoromethyl)-1,3,4-oxadiazol-2-yl)benzyl)piperazine-1-carboxamide

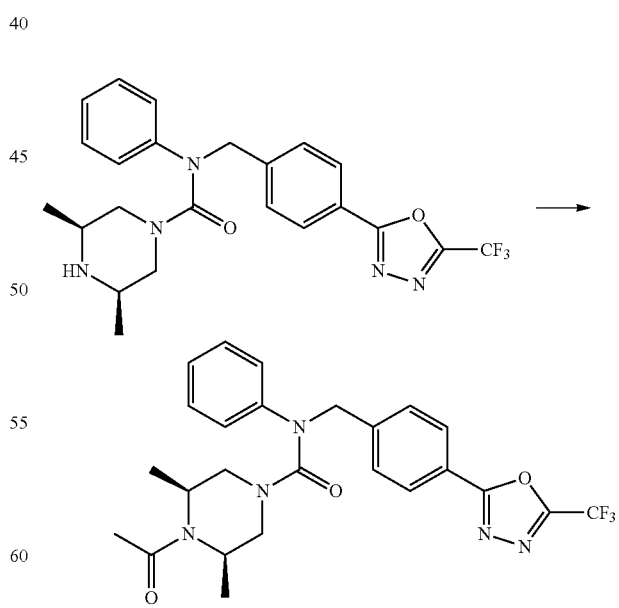

A solution of (3S,5R)-3,5-dimethyl-N-phenyl-N-(4-(5-(trifluoromethyl)-1,3,4-oxadiazol-2-yl)benzyl)piperazine-1-carboxamide (0.200 g, 0.435 mmol) prepared in Example 55 and triethylamine (0.121 mL, 0.871 mmol) in dichloromethane (4 mL) was mixed at 0° C. with acetyl chloride (0.046 mL, 0.653 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=30% to 80%) to give the title compound (3R,5S)-4-acetyl-3,5-dimethyl-N-phenyl-N-(4-(5-(trifluoromethyl)-1,3,4-oxadiazol-2-yl)benzyl)piperazine-1-carboxamide as pale yellow oil (0.083 g, 38.0%).

$^1$H NMR (400 MHz, CDCl$_3$) δ 8.04 (d, 2H, J=8.0 Hz), 7.52 (d, 2H, J=8.0 Hz), 7.35 (t, 2H, J=7.7 Hz), 7.19 (t, 1H, J=7.4 Hz), 7.07 (d, 2H, J=8.3 Hz), 4.93 (s, 2H), 3.67 (brs, 2H), 2.83-2.81 (m, 2H), 2.09 (s, 3H), 1.75 (s, 2H), 1.07 (brs, 6H); MS (ESI) m/z 502.4 (M$^+$+H).

Example 58. Compound 21388: (3R,5S)-3,5-Dimethyl-4-(methylsulfonyl)-N-phenyl-N-(4-(5-(trifluoromethyl)-1,3,4-oxadiazol-2-yl)benzyl)piperazine-1-carboxamide

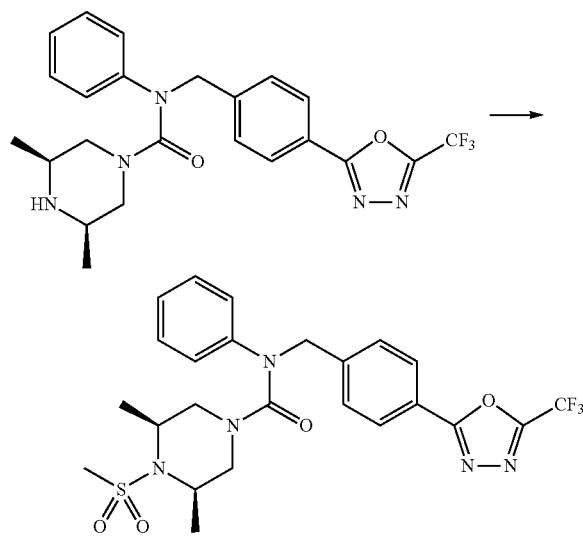

A solution of (3S,5R)-3,5-dimethyl-N-phenyl-N-(4-(5-(trifluoromethyl)-1,3,4-oxadiazol-2-yl)benzyl)piperazine-1-carboxamide (0.100 g, 0.221 mmol) prepared in Example 55 and triethylamine (0.045 g, 0.441 mmol) in dichloromethane (4 mL) was mixed at 0° C. with methanesulfonyl chloride (0.030 g, 0.265 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=40% to 100%) to give the title compound (3R,5S)-3,5-dimethyl-4-(methylsulfonyl)-N-phenyl-N-(4-(5-(trifluoromethyl)-1,3,4-oxadiazol-2-yl)benzyl)piperazine-1-carboxamide as pale yellow oil (0.063 g, 53.1%).

$^1$H NMR (400 MHz, CDCl$_3$) δ 8.02 (d, 2H, J=8.4 Hz), 7.49 (d, 2H, J=8.4 Hz), 7.33 (t, 2H, J=7.9 Hz), 7.17 (t, 1H, J=6.4 Hz), 7.04-7.02 (m, 2H), 4.90 (s, 2H), 3.96-3.93 (m, 2H), 3.61 (d, 2H, J=13.3 Hz), 2.84 (dd, 2H, J=13.1, 4.6 Hz), 2.80 (s, 3H), 1.16 (d, 6H, J=7.0 Hz); LRMS (ESI) m/z 538.0 (M$^+$+H).

Example 59. Compound 21389: N-(4-Fluorophenyl)-N-(4-(5-(trifluoromethyl)-1,3,4-oxadiazol-2-yl)benzyl)thiomorpholine-4-carboxamide 1,1-dioxide

[Step 1] Methyl 4-(((4-fluorophenyl)amino)methyl)benzoate

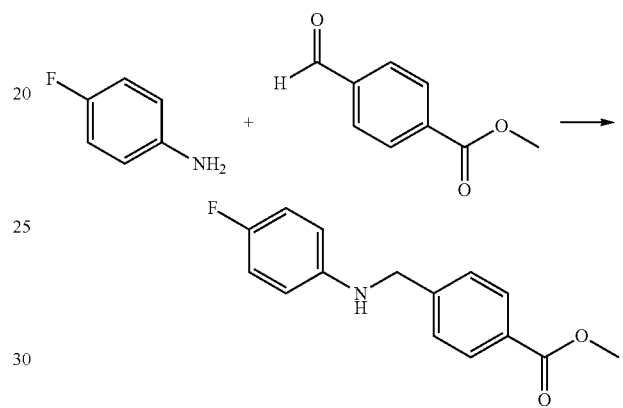

A solution of 4-fluoroaniline (0.500 g, 4.500 mmol) and methyl 4-formylbenzoate (0.776 g, 4.725 mmol) in dichloromethane (20 mL) was mixed at the room temperature with sodium triacetoxyborohydride (3.815 g, 17.999 mmol). The reaction mixture was stirred at the same temperature for 16 hr. Then, saturated aqueous sodium bicarbonate solution was added to the reaction mixture, followed by extraction with dichloromethane. The organic layer was washed with saturated aqueous ammonium chloride solution, dried (anhydrous MgSO$_4$), filtered, and concentrated in vacuo. The concentrate was purified and concentrated by column chromatography (SiO$_2$, 12 g cartridge; ethyl acetate/hexane=10% to 30%) to give the title compound methyl 4-(((4-fluorophenyl)amino)methyl)benzoate as orange solid (1.119 g, 95.9%).

[Step 2] Methyl 4-((N-(4-fluorophenyl)-1,1-dioxidothiomorpholine-4-carboxamido)methyl)benzoate

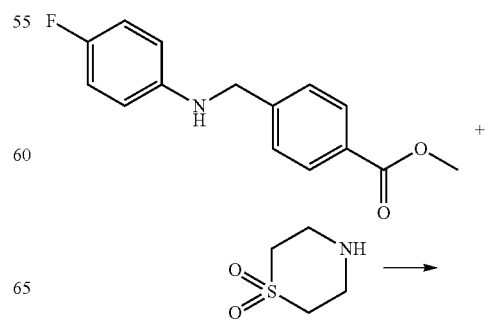

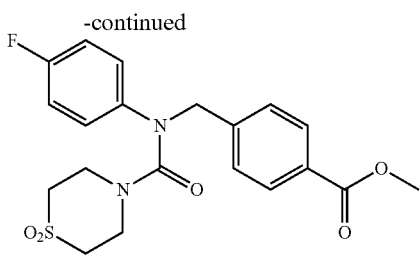

A solution of methyl 4-(((4-fluorophenyl)amino)methyl)benzoate (0.500 g, 1.928 mmol) prepared in Step 1, thiomorpholine 1,1-dioxide (0.287 g, 2.121 mmol), triphosgene (0.286 g, 0.964 mmol) and N,N-diisopropylethylamine (2.002 mL, 11.571 mmol) in dichloromethane (10 mL) was stirred at the room temperature for 2 hr. Then, water was added to the reaction mixture, followed by extraction with dichloremethane. The organic layer was washed with brine, dried (anhydrous $MgSO_4$), filtered, and concentrated in vacuo. The crude product was crystallized at the room temperature using diethylether (20 mL). The resulting precipitates were filtered, washed by diethylether, and dried to give the title compound methyl 4-((N-(4-fluorophenyl)-1,1-dioxidothiomorpholine-4-carboxamido)methyl)benzoate as white solid (0.817 g, 100.8%).

[Step 3] N-(4-fluorophenyl)-N-(4-(hydrazinecarbonyl)benzyl)thiomorpholine-4-carboxamide 1,1-dioxide

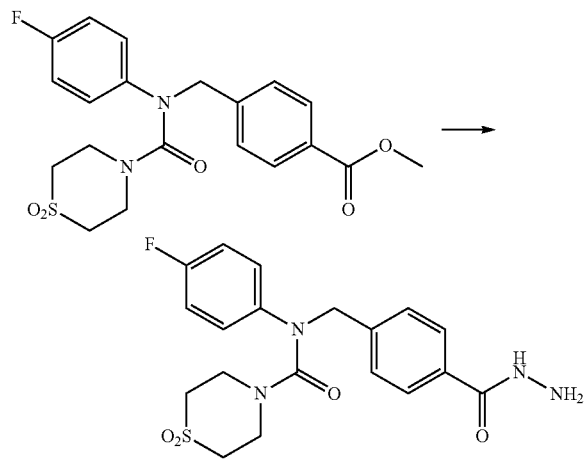

Methyl 4-((N-(4-fluorophenyl)-1,1-dioxidothiomorpholine-4-carboxamido)methyl)benzoate (0.817 g, 1.943 mmol) prepared in Step 2 and hydrazine monohydrate (1.835 mL, 38.862 mmol) in ethanol (3 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 3%) to give the title compound N-(4-fluorophenyl)-N-(4-(hydrazinecarbonyl)benzyl)thiomorpholine-4-carboxamide 1,1-dioxide as pink solid (0.417 g, 51.0%).

[Step 4] N-(4-fluorophenyl)-N-(4-(2-(2,2,2-trifluoroacetyl)hydrazine-1-carbonyl)benzyl)thiomorpholine-4-carboxamide 1,1-dioxide

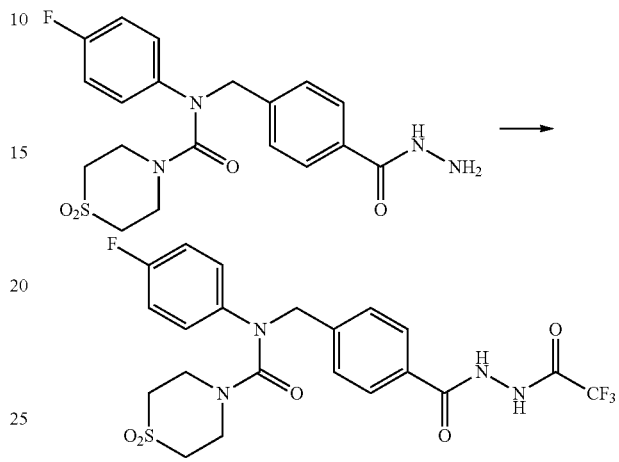

A solution of N-(4-fluorophenyl)-N-(4-(hydrazinecarbonyl)benzyl)thiomorpholine-4-carboxamide 1,1-dioxide (0.417 g, 0.991 mmol) prepared in Step 3 and triethylamine (0.274 mL, 1.983 mmol) in dichloromethane (2 mL) was mixed at the room temperature with trifluoroacetic anhydride (0.155 mL, 0.892 mmol). The reaction mixture was stirred at the same temperature for 2 hr. Then, water was added to the reaction mixture, followed by extraction with dichloremethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 5%) to give the title compound N-(4-fluorophenyl)-N-(4-(2-(2,2,2-trifluoroacetyl)hydrazine-1-carbonyl)benzyl)thiomorpholine-4-carboxamide 1,1-dioxide as colorless oil (0.464 g, 90.7%).

[Step 5] Compound 21389

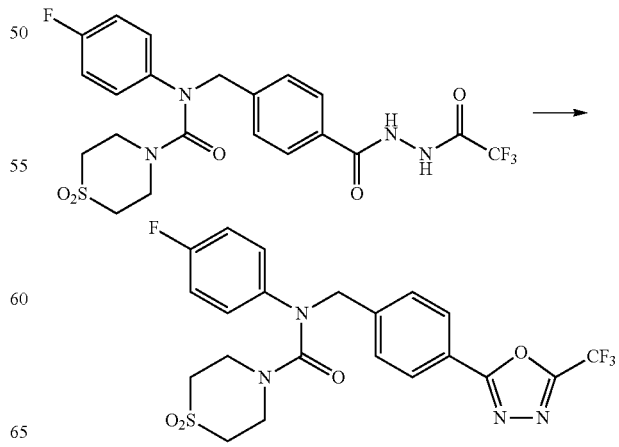

A mixture of N-(4-fluorophenyl)-N-(4-(2-(2,2,2-trifluoroacetyl)hydrazine-1-carbonyl)benzyl)thiomorpholine-4-carboxamide 1,1-dioxide (0.464 g, 0.899 mmol) prepared in Step 4 and 1-methoxy-N-triethylammoniosulfonyl-methanimidate (Burgess reagent, 0.321 g, 1.348 mmol) in tetrahydrofuran (2 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloremethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-(4-fluorophenyl)-N-(4-(5-(trifluoromethyl)-1,3,4-oxadiazol-2-yl)benzyl)thiomorpholine-4-carboxamide 1,1-dioxide as white foam (0.326 g, 72.8%).

$^1$H NMR (400 MHz, CDCl$_3$) δ 8.06-7.98 (m, 2H), 7.47-7.39 (m, 2H), 7.10-6.98 (m, 4H), 4.86 (s, 2H), 3.79-3.67 (m, 4H), 2.87-2.80 (m, 4H); LRMS (ES) m/z 499.03 (M$^+$+1).

Example 60. Compound 21390: N-(4-Methoxyphenyl)-N-(4-(5-(trifluoromethyl)-1,3,4-oxadiazol-2-yl)benzyl)thiomorpholine-4-carboxamide 1,1-dioxide

[Step 1] N-(4-methoxyphenyl)thiomorpholine-4-carboxamide 1,1-dioxide

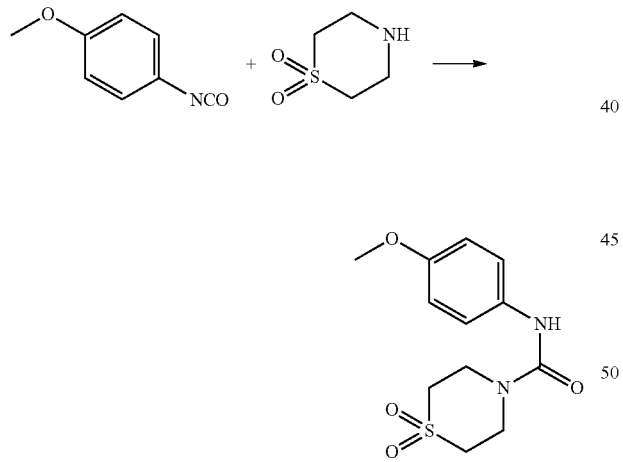

A solution of 1-isocyanato-4-methoxybenzene (0.500 g, 3.352 mmol) and thiomorpholine 1,1-dioxide (0.449 g, 3.319 mmol) in diethylether (10 mL) was stirred at the room temperature for 3 hr. The precipitates were collected by filtration, washed by diethylether, and dried to give the title compound N-(4-methoxyphenyl)thiomorpholine-4-carboxamide 1,1-dioxide as white solid (0.541 g, 56.8%).

[Step 2] Methyl 4-((N-(4-methoxyphenyl)-1,1-dioxidothiomorpholine-4-carboxamido)methyl)benzoate

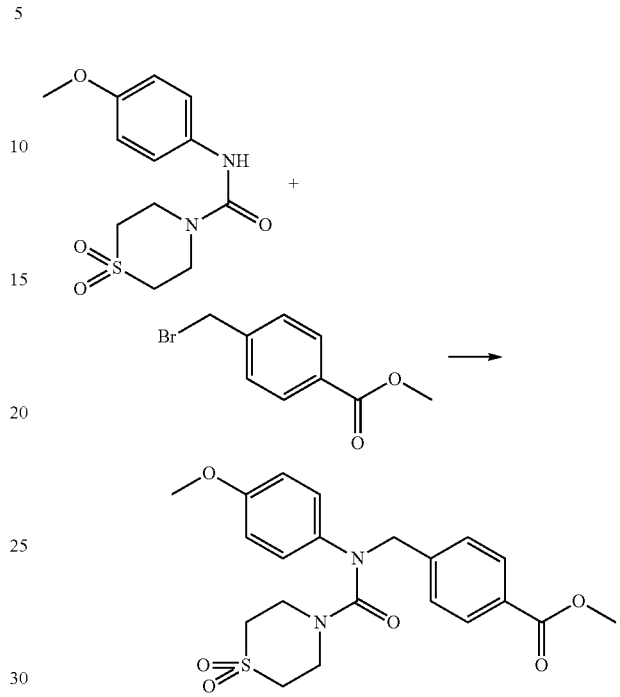

N-(4-methoxyphenyl)thiomorpholine-4-carboxamide 1,1-dioxide (0.541 g, 1.903 mmol) prepared in Step 1, methyl 4-(bromomethyl)benzoate (0.436 g, 1.903 mmol) and sodium hydride (60.00%, 0.076 g, 1.903 mmol) were mixed at 0° C. in N,N-dimethylformamide (10 mL) and then stirred at the room temperature for 2 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=30% to 50%) to give the title compound methyl 4-((N-(4-methoxyphenyl)-1,1-dioxidothiomorpholine-4-carboxamido)methyl)benzoate as yellow foam (0.670 g, 81.4%).

[Step 3] N-(4-(hydrazinecarbonyl)benzyl)-N-(4-methoxyphenyl)thiomorpholine-4-carboxamide 1,1-dioxide

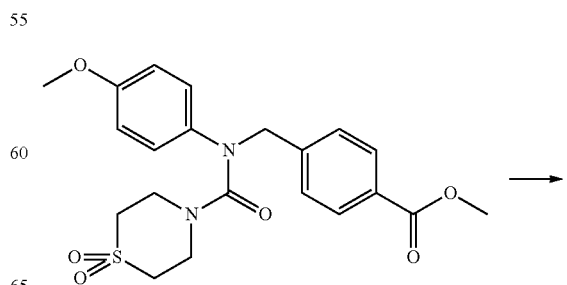

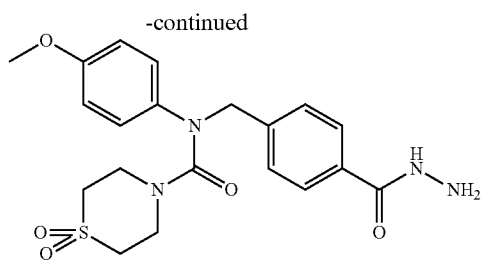

Methyl 4-((N-(4-methoxyphenyl)-1,1-dioxidothiomorpholine-4-carboxamido)methyl)benzoate (0.670 g, 1.550 mmol) prepared in Step 2 and hydrazine monohydrate (1.551 g, 30.993 mmol) in ethanol (5 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloremethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 3%) to give the title compound N-(4-(hydrazinecarbonyl)benzyl)-N-(4-methoxyphenyl)thiomorpholine-4-carboxamide 1,1-dioxide as yellow foam (0.670 g, 100.0%).

[Step 4] N-(4-methoxyphenyl)-N-(4-(2-(2,2,2-trifluoroacetyl)hydrazine-1-carbonyl)benzyl)thiomorpholine-4-carboxamide 1,1-dioxide

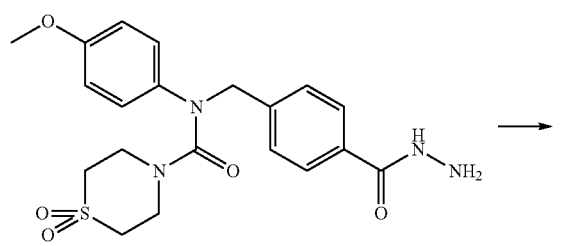

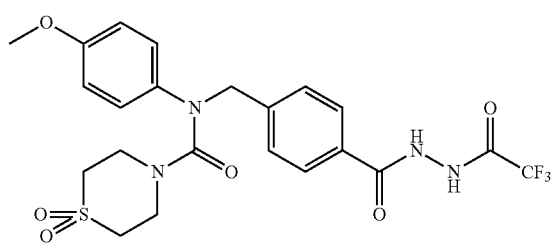

A solution of N-(4-(hydrazinecarbonyl)benzyl)-N-(4-methoxyphenyl)thiomorpholine-4-carboxamide 1,1-dioxide (0.670 g, 1.549 mmol) prepared in Step 3 and triethylamine (0.428 mL, 3.098 mmol) in dichloromethane (10 mL) was mixed at the room temperature with trifluoroacetic anhydride (0.242 mL, 1.394 mmol). The reaction mixture was stirred at the same temperature for 2 hr. Then, water was added to the reaction mixture, followed by extraction with dichloremethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 3%) to give the title compound N-(4-methoxyphenyl)-N-(4-(2-(2,2,2-trifluoroacetyl)hydrazine-1-carbonyl)benzyl)thiomorpholine-4-carboxamide 1,1-dioxide as colorless oil (0.510 g, 62.3%).

[Step 5] Compound 21390

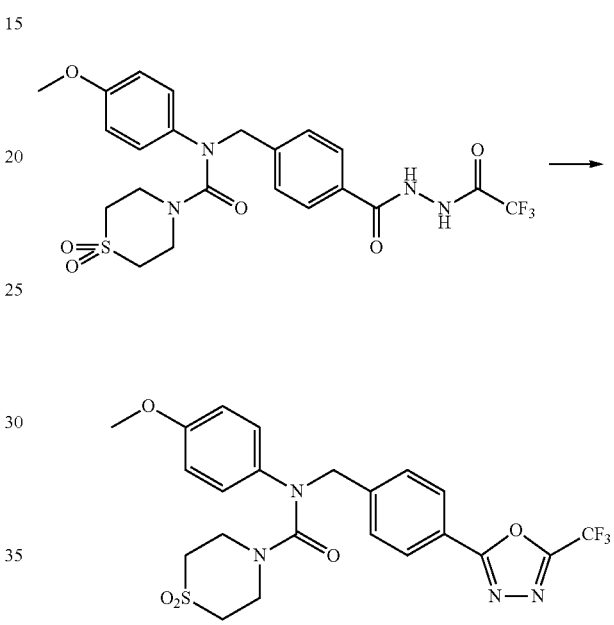

A mixture of N-(4-methoxyphenyl)-N-(4-(2-(2,2,2-trifluoroacetyl)hydrazine-1-carbonyl)benzyl)thiomorpholine-4-carboxamide 1,1-dioxide (0.242 g, 0.458 mmol) prepared in Step 4 and 1-methoxy-N-triethylammoniosulfonylmethanimidate (Burgess reagent, 0.164 g, 0.687 mmol) in tetrahydrofuran (2 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloremethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=3%) to give the title compound N-(4-methoxyphenyl)-N-(4-(5-(trifluoromethyl)-1,3,4-oxadiazol-2-yl)benzyl)thiomorpholine-4-carboxamide 1,1-dioxide as light brown foam (0.170 g, 72.7%).

$^1$H NMR (400 MHz, $CDCl_3$) δ 8.04-7.97 (m, 2H), 7.45-7.38 (m, 2H), 7.00-6.91 (m, 2H), 6.88-6.80 (m, 2H), 4.82 (s, 2H), 3.78 (s, 3H), 3.71 (m, 4H), 3.48 (s, 5H), 2.82-2.74 (m, 4H); LRMS (ES) m/z 511.36 ($M^+$+1).

343

Example 61. Compound 21391: N-(4-(5-(trifluoromethyl)-1,3,4-oxadiazol-2-yl)benzyl)-N-(3-(trifluoromethyl)phenyl)thiomorpholine-4-carboxamide 1,1-dioxide

[Step 1] Methyl 4-((1,1-dioxido-N-(3-(trifluoromethyl)phenyl)thiomorpholine-4-carboxamido)methyl) benzoate

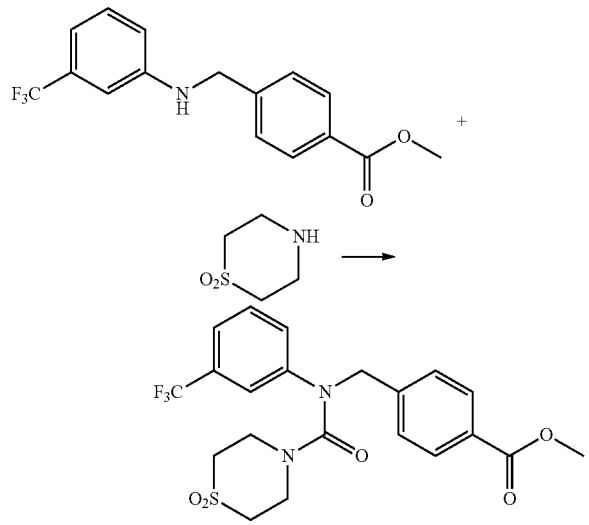

A solution of methyl 4-(((3-(trifluoromethyl)phenyl)amino)methyl)benzoate (0.300 g, 0.970 mmol), triphosgene (0.317 g, 1.067 mmol) and N,N-diisopropylethylamine (1.694 mL, 9.700 mmol) in dichloromethane (5 mL) was mixed at 0° C. with thiomorpholine 1,1-dioxide (0.138 g, 1.018 mmol), and stirred at the room temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound methyl 4-((1,1-dioxido-N-(3-(trifluoromethyl)phenyl)thiomorpholine-4-carboxamido)methyl) benzoate as bright yellow solid (0.456 g, 100.0%).

[Step 2] N-(4-(hydrazinecarbonyl)benzyl)-N-(3-(trifluoromethyl)phenyl)thiomorpholine-4-carboxamide 1,1-dioxide

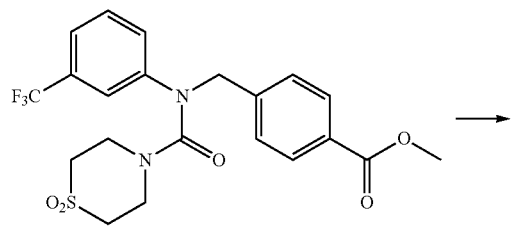

344

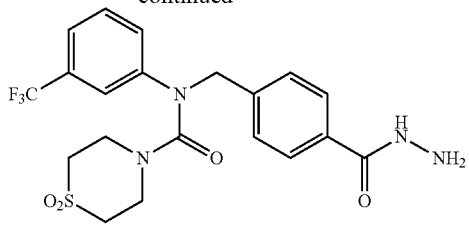

A mixture of methyl 4-((1,1-dioxido-N-(3-(trifluoromethyl)phenyl)thiomorpholine-4-carboxamido)methyl) benzoate (0.460 g, 0.978 mmol) prepared in Step 1 and hydrazine monohydrate (0.924 mL, 19.555 mmol) in ethanol (10 mL) was heated at 120° C. for 1 hr under the microwaves, and cooled down to the room temperature to terminate the reaction. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-(4-(hydrazinecarbonyl)benzyl)-N-(3-(trifluoromethyl)phenyl)thiomorpholine-4-carboxamide 1,1-dioxide as white solid (0.460 g, 100.0%).

[Step 3] N-(4-(2-(2,2,2-trifluoroacetyl)hydrazine-1-carbonyl)benzyl)-N-(3-(trifluoromethyl)phenyl)thiomorpholine-4-carboxamide 1,1-dioxide

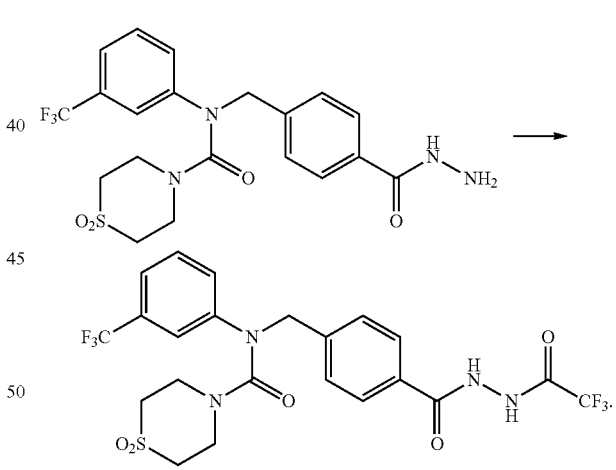

A solution of N-(4-(hydrazinecarbonyl)benzyl)-N-(3-(trifluoromethyl)phenyl)thiomorpholine-4-carboxamide 1,1-dioxide (0.460 g, 0.978 mmol) prepared in Step 2 and triethylamine (0.203 mL, 1.467 mmol) in dichloromethane (10 mL) was mixed at 0° C. with trifluoroacetic anhydride (0.122 mL, 0.880 mmol), and stirred at the room temperature for 16 hr. Then, saturated aqueous sodium bicarbonate solution was added to the reaction mixture, followed by extraction with ethyl acetate. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge;

methanol/dichloromethane=0% to 5%) to give the title compound N-(4-(2-(2,2,2-trifluoroacetyl)hydrazine-1-carbonyl)benzyl)-N-(3-(trifluoromethyl)phenyl)thiomorpholine-4-carboxamide 1,1-dioxide as white solid (0.249 g, 45.0%).

[Step 4] Compound 21391

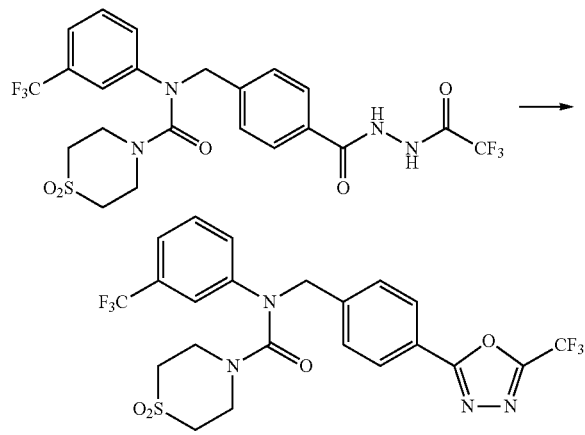

A mixture of N-(4-(2-(2,2,2-trifluoroacetyl)hydrazine-1-carbonyl)benzyl)-N-(3-(trifluoromethyl)phenyl)thiomorpholine-4-carboxamide 1,1-dioxide (0.239 g, 0.422 mmol) prepared in Step 3 and burgess reagent (0.151 g, 0.633 mmol) in tetrahydrofuran (5 mL) was heated at 150° C. for 30 min under the microwaves, and cooled down to the room temperature to terminate the reaction. Then, saturated aqueous sodium bicarbonate solution added to the reaction mixture, followed by extraction with dichloromethane. The organic layer was washed with brine, dried (anhydrous MgSO₄), filtered, and concentrated in vacuo. The concentrate was purified and concentrated by column chromatography (SiO₂, 4 g cartridge; methanol/dichloromethane=0 to 3%) to give the title compound N-(4-(5-(trifluoromethyl)-1,3,4-oxadiazol-2-yl)benzyl)-N-(3-(trifluoromethyl)phenyl)thiomorpholine-4-carboxamide 1,1-dioxide as white solid (0.162 g, 70.0%).

¹H NMR (400 MHz, CDCl₃) δ 8.04 (d, 2H, J=8.2 Hz), 7.48-7.43 (m, 4H), 7.35-7.34 (m, 1H), 7.25-7.23 (m, 1H), 4.93 (s, 2H), 3.72-3.69 (m, 4H), 0.87-2.84 (m, 4H); LRMS (ES) m/z 549.4 (M⁺+1).

Example 62. Compound 21392: N-(3-fluorophenyl)-N-(4-(5-(trifluoromethyl)-1,3,4-oxadiazol-2-yl)benzyl)thiomorpholine-4-carboxamide 1,1-dioxide

[Step 1] Methyl 4-((N-(3-fluorophenyl)-1,1-dioxidothiomorpholine-4-carboxamido)methyl)benzoate

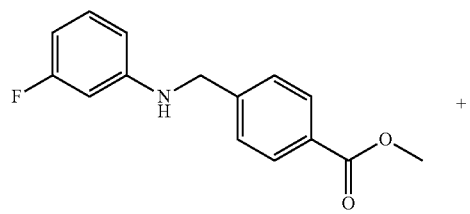

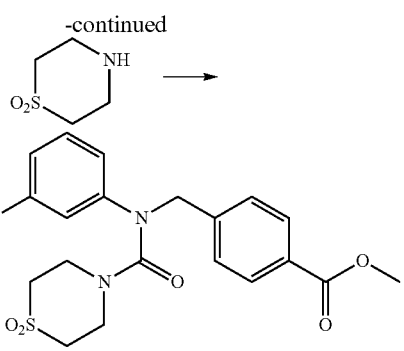

A solution of methyl 4-(((3-fluorophenyl)amino)methyl)benzoate (0.300 g, 1.157 mmol), triphosgene (0.378 g, 1.273 mmol) and N,N-diisopropylethylamine (2.021 mL, 11.571 mmol) in dichloromethane (5 mL) was mixed at 0° C. with thiomorpholine 1,1-dioxide (0.164 g, 1.215 mmol), and stirred at the room temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 3%) to give the title compound methyl 4-((N-(3-fluorophenyl)-1,1-dioxidothiomorpholine-4-carboxamido)methyl)benzoate as bright yellow solid (0.461 g, 94.8%).

[Step 2] N-(3-fluorophenyl)-N-(4-(hydrazinecarbonyl)benzyl)thiomorpholine-4-carboxamide 1,1-dioxide

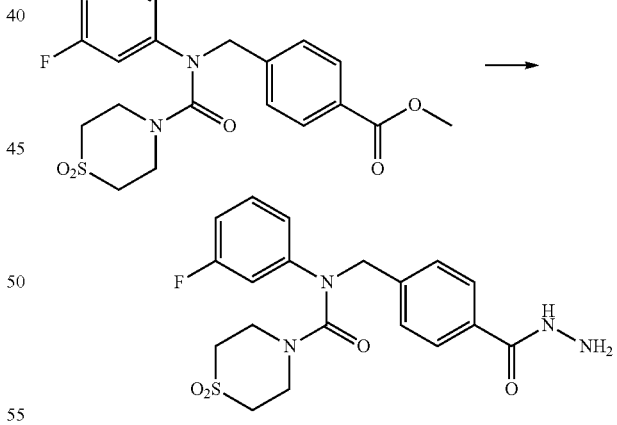

A mixture of methyl 4-((N-(3-fluorophenyl)-1,1-dioxidothiomorpholine-4-carboxamido)methyl)benzoate (0.450 g, 1.070 mmol) prepared in Step 1 and hydrazine monohydrate (1.011 mL, 21.405 mmol) in ethanol (10 mL) was heated at 120° C. for 1 hr under the microwaves, and cooled down to the room temperature to terminate the reaction. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(3-fluorophenyl)-N-(4-(hydrazinecarbonyl)benzyl)thiomorpholine-4-carboxamide 1,1-dioxide as white solid (0.450 g, 100.0%).

[Step 3] N-(3-fluorophenyl)-N-(4-(2-(2,2,2-trifluoroacetyl)hydrazine-1-carbonyl)benzyl)thiomorpholine-4-carboxamide 1,1-dioxide

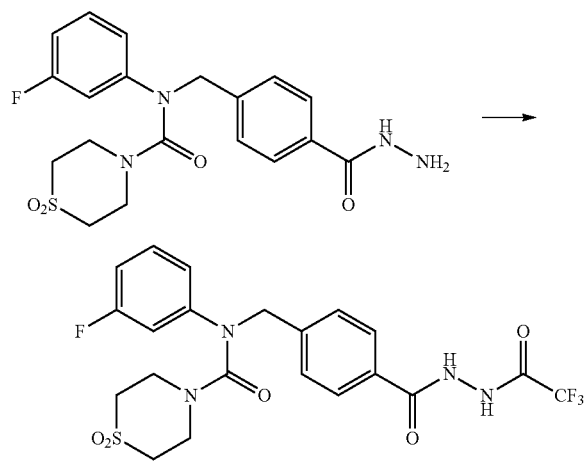

A solution of N-(3-fluorophenyl)-N-(4-(hydrazinecarbonyl)benzyl)thiomorpholine-4-carboxamide 1,1-dioxide (0.450 g, 1.070 mmol) prepared in Step 2 and triethylamine (0.223 mL, 1.605 mmol) in dichloromethane (10 mL) was mixed at 0° C. with trifluoroacetic anhydride (0.134 mL, 0.963 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(3-fluorophenyl)-N-(4-(2-(2,2,2-trifluoroacetyl)hydrazine-1-carbonyl)benzyl)thiomorpholine-4-carboxamide 1,1-dioxide as white solid (0.064 g, 11.5%).

[Step 4] Compound 21392

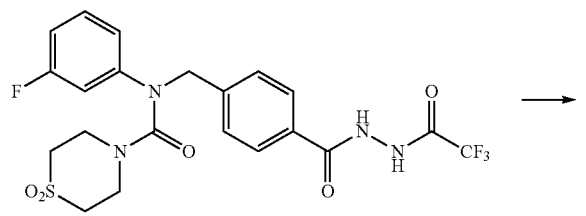

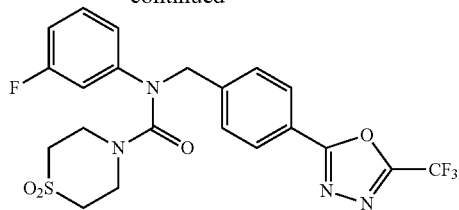

A mixture of N-(3-fluorophenyl)-N-(4-(2-(2,2,2-trifluoroacetyl)hydrazine-1-carbonyl)benzyl)thiomorpholine-4-carboxamide 1,1-dioxide (0.054 g, 0.104 mmol) prepared in Step 3 and burgess reagent (0.037 g, 0.156 mmol) in tetrahydrofuran (10 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(3-fluorophenyl)-N-(4-(5-(trifluoromethyl)-1,3,4-oxadiazol-2-yl)benzyl)thiomorpholine-4-carboxamide 1,1-dioxide as colorless oil (0.040 g, 77.0%).

$^1$H NMR (400 MHz, CDCl$_3$) δ 8.03 (d, 2H, J=8.4 Hz), 7.45 (d, 2H, J=8.2 Hz); 7.34-7.32 (m, 1H), 6.93-6.89 (m, 1H), 6.87-6.84 (m, 1H), 6.83-6.79 (m, 1H), 4.90 (s, 2H), 3.74-3.71 (m, 4H), 2.88-2.86 (m, 4H); LRMS (ES) m/z 499.1 (M$^+$+1).

Example 63. Compound 21393: N-(3-bromophenyl)-N-(4-(5-(trifluoromethyl)-1,3,4-oxadiazol-2-yl)benzyl)thiomorpholine-4-carboxamide 1,1-dioxide

[Step 1] Methyl 4-((N-(3-bromophenyl)-1,1-dioxidothiomorpholine-4-carboxamido)methyl)benzoate

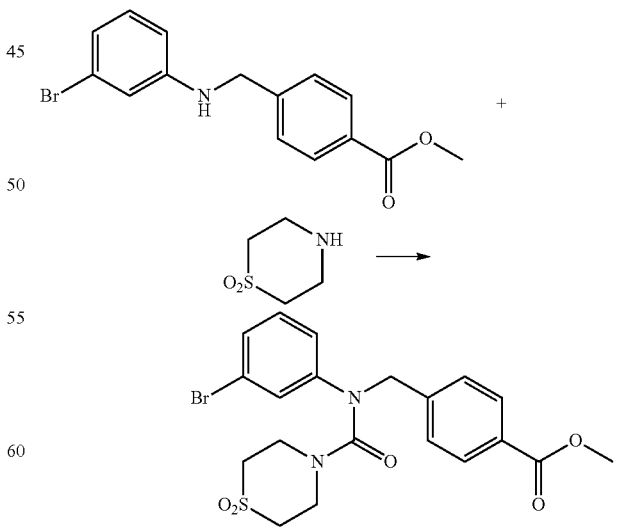

A solution of methyl 4-(((3-bromophenyl)amino)methyl)benzoate (0.300 g, 0.937 mmol), triphosgene (0.306 g, 1.031 mmol) and N,N-diisopropylethylamine (1.636 mL, 9.369 mmol) in dichloromethane (10 mL) was mixed at 0° C. with thiomorpholine 1,1-dioxide (0.133 g, 0.984 mmol), and stirred at the room temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound methyl 4-((N-(3-bromophenyl)-1,1-dioxidothiomorpholine-4-carboxamido)methyl)benzoate as bright yellow solid (0.451 g, 100.0%).

[Step 2] N-(3-bromophenyl)-N-(4-(hydrazinecarbonyl)benzyl)thiomorpholine-4-carboxamide 1,1-dioxide

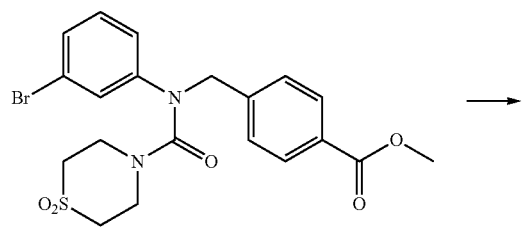

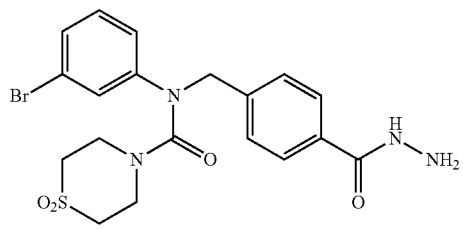

A mixture of methyl 4-((N-(3-bromophenyl)-1,1-dioxidothiomorpholine-4-carboxamido)methyl)benzoate (0.460 g, 0.956 mmol) prepared in Step 1 and hydrazine monohydrate (0.903 mL, 19.113 mmol) in ethanol (10 mL) was heated at 120° C. for 1 hr under the microwaves, cooled down to the room temperature to terminate the reaction. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(3-bromophenyl)-N-(4-(hydrazinecarbonyl)benzyl)thiomorpholine-4-carboxamide 1,1-dioxide as white solid (0.460 g, 100.0%).

[Step 3] N-(3-bromophenyl)-N-(4-(2-(2,2,2-trifluoroacetyl)hydrazine-1-carbonyl)benzyl)thiomorpholine-4-carboxamide 1,1-dioxide

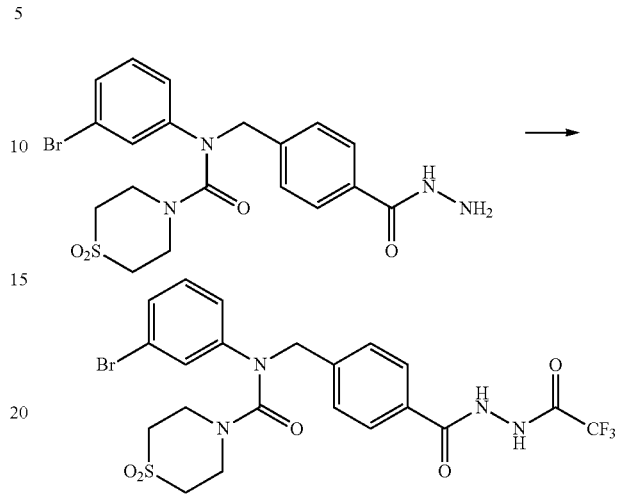

A solution of N-(3-bromophenyl)-N-(4-(hydrazinecarbonyl)benzyl)thiomorpholine-4-carboxamide 1,1-dioxide (0.460 g, 0.956 mmol) prepared in Step 2 and triethylamine (0.199 mL, 1.433 mmol) in dichloromethane (10 mL) was mixed at 0° C. with trifluoroacetic anhydride (0.120 mL, 0.860 mmol), and stirred at the room temperature for 16 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 24 g cartridge; methanol/dichloromethane=0% to 5%) to give the title compound N-(3-bromophenyl)-N-(4-(2-(2,2,2-trifluoroacetyl)hydrazine-1-carbonyl)benzyl)thiomorpholine-4-carboxamide 1,1-dioxide as white solid (0.083 g, 15.1%).

[Step 4] Compound 21393

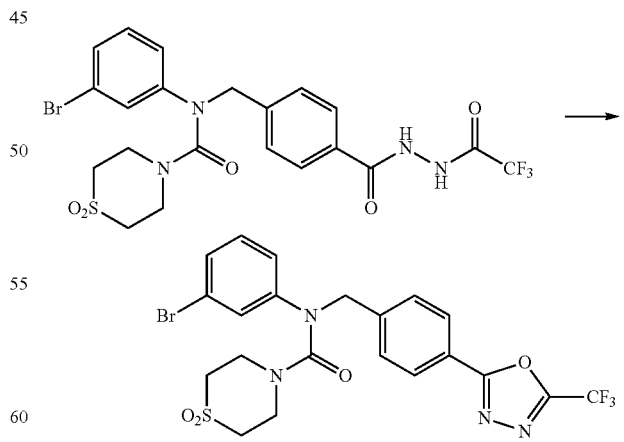

A mixture of N-(3-bromophenyl)-N-(4-(2-(2,2,2-trifluoroacetyl)hydrazine-1-carbonyl)benzyl)thiomorpholine-4-carboxamide 1,1-dioxide (0.073 g, 0.127 mmol) prepared in Step 3 and burgess reagent (0.045 g, 0.190 mmol) in tetrahydrofuran (1 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(3-bromophenyl)-N-(4-(5-(trifluoromethyl)-1,3,4-oxadiazol-2-yl)benzyl)thiomorpholine-4-carboxamide 1,1-dioxide as colorless oil (0.064 g, 90.5%).

$^1$H NMR (400 MHz, CDCl$_3$) δ 8.03 (d, 2H, J=8.2 Hz), 7.44 (d, 2H, J=8.1 Hz), 7.35-7.32 (m, 1H), 7.27-7.26 (m, 1H), 7.23-7.19 (m, 1H), 7.00-6.98 (m, 1H), 4.89 (s, 2H), 3.73-3.70 (m, 4H), 2.87-2.85 (m, 4H); LRMS (ES) m/z 559.2, 561.3 (M$^+$+1).

Example 64. Compound 21394: N-(4-chlorophenyl)-N-(4-(5-(trifluoromethyl)-1,3,4-oxadiazol-2-yl)benzyl)thiomorpholine-4-carboxamide 1,1-dioxide

[Step 1]
N-(4-chlorophenyl)thiomorpholine-4-carboxamide 1,1-dioxide

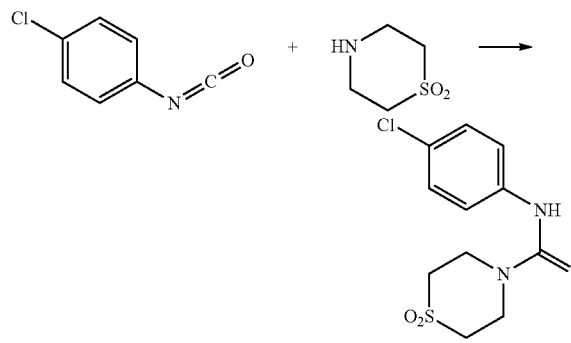

A solution of 1-chloro-4-isocyanatobenzene (0.300 g, 2.219 mmol) and thiomorpholine 1,1-dioxide (0.358 g, 2.330 mmol) in diethylether (10 mL) was stirred at the room temperature for 16 hr. The precipitates were collected by filtration, washed by diethylether, and dried to give the title compound N-(4-chlorophenyl)thiomorpholine-4-carboxamide 1,1-dioxide as white solid (0.626 g, 94.1%).

[Step 2] Methyl 4-((N-(4-chlorophenyl)-1,1-dioxidothiomorpholine-4-carboxamido)methyl)benzoate

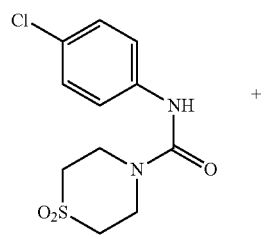

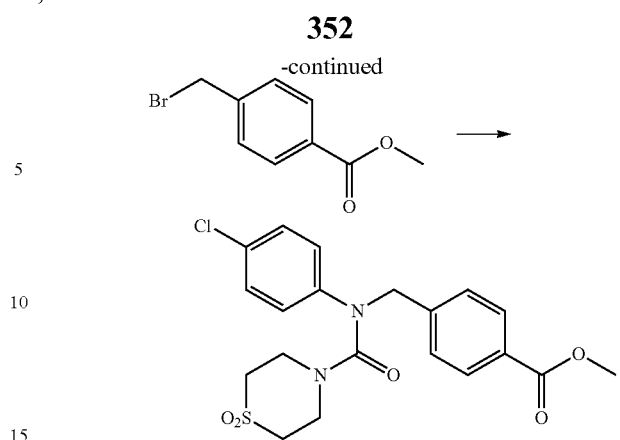

A solution of N-(4-chlorophenyl)thiomorpholine-4-carboxamide 1,1-dioxide (0.500 g, 1.732 mmol) prepared in Step 1 and sodium hydride (60.00%, 0.083 g, 2.078 mmol) in N,N-dimethylformamide (10 mL) was mixed at 0° C. with methyl 4-(bromomethyl)benzoate (0.416 g, 1.818 mmol), and stirred at the room temperature for 3 hr. Then, aqueous 1N-sodium bicarbonate solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 24 g cartridge; ethyl acetate/hexane=0% to 50%) to give the title compound methyl 4-((N-(4-chlorophenyl)-1,1-dioxidothiomorpholine-4-carboxamido)methyl)benzoate as white solid (0.583 g, 77.1%).

[Step 3] N-(4-chlorophenyl)-N-(4-(hydrazinecarbonyl)benzyl)thiomorpholine-4-carboxamide 1,1-dioxide

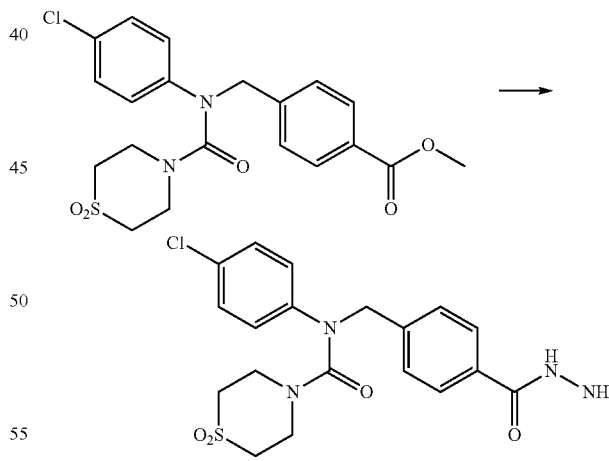

A mixture of methyl 4-((N-(4-chlorophenyl)-1,1-dioxidothiomorpholine-4-carboxamido)methyl)benzoate (0.560 g, 1.282 mmol) prepared in Step 2 and hydrazine monohydrate (1.211 mL, 25.635 mmol) in ethanol (10 mL) was heated at 120° C. for 1 hr under the microwaves, and cooled down to the room temperature to terminate the reaction. The precipitates were collected by filtration, washed by hexane, and dried to give the title compound N-(4-chlorophenyl)-N-(4-(hydrazinecarbonyl)benzyl)thiomorpholine-4-carboxamide 1,1-dioxide as white solid (0.397 g, 70.9%).

[Step 4] N-(4-chlorophenyl)-N-(4-(2-(2,2,2-trifluoroacetyl)hydrazine-1-carbonyl)benzyl)thiomorpholine-4-carboxamide 1,1-dioxide

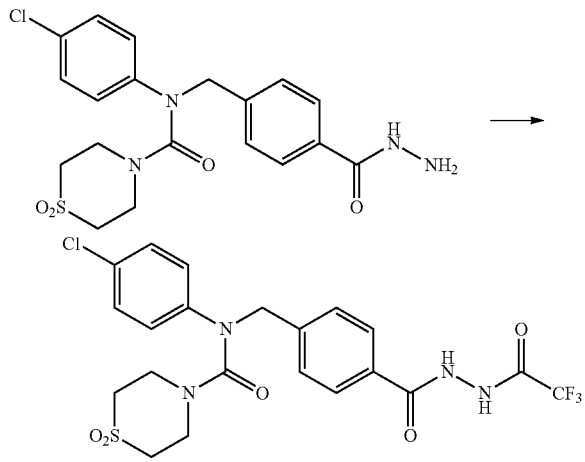

A solution of N-(4-chlorophenyl)-N-(4-(hydrazinecarbonyl)benzyl)thiomorpholine-4-carboxamide 1,1-dioxide (0.397 g, 0.909 mmol) prepared in Step 3 and triethylamine (0.189 mL, 1.363 mmol) in dichloromethane (10 mL) was mixed at 0° C. with trifluoroacetic anhydride (0.114 mL, 0.818 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(4-chlorophenyl)-N-(4-(2-(2,2,2-trifluoroacetyl)hydrazine-1-carbonyl)benzyl)thiomorpholine-4-carboxamide 1,1-dioxide as white solid (0.079 g, 16.2%).

[Step 5] Compound 21394

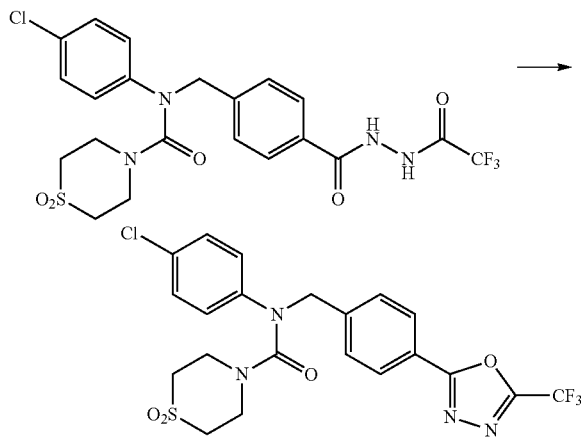

A mixture of N-(4-chlorophenyl)-N-(4-(2-(2,2,2-trifluoroacetyl)hydrazine-1-carbonyl)benzyl)thiomorpholine-4-carboxamide 1,1-dioxide (0.069 g, 0.129 mmol) prepared in Step 4 and burgess reagent (0.046 g, 0.193 mmol) in tetrahydrofuran (1 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-chlorophenyl)-N-(4-(5-(trifluoromethyl)-1,3,4-oxadiazol-2-yl)benzyl)thiomorpholine-4-carboxamide 1,1-dioxide as colorless oil (0.053 g, 80.1%).

$^1$H NMR (400 MHz, CDCl$_3$) δ 8.02 (d, 2H, J=8.2 Hz), 7.43 (d, 2H, J=8.2 Hz), 7.33-7.32 (m, 2H), 7.01-6.99 (m, 2H), 4.87 (s, 2H), 3.71-3.68 (m, 4H), 2.87-2.84 (m, 4H); LRMS (ES) m/z 515.3 (M$^+$+1).

Example 65. Compound 21395: N-(3-chlorophenyl)-N-(4-(5-(trifluoromethyl)-1,3,4-oxadiazol-2-yl)benzyl)thiomorpholine-4-carboxamide 1,1-dioxide

[Step 1] N-(3-chlorophenyl)thiomorpholine-4-carboxamide 1,1-dioxide

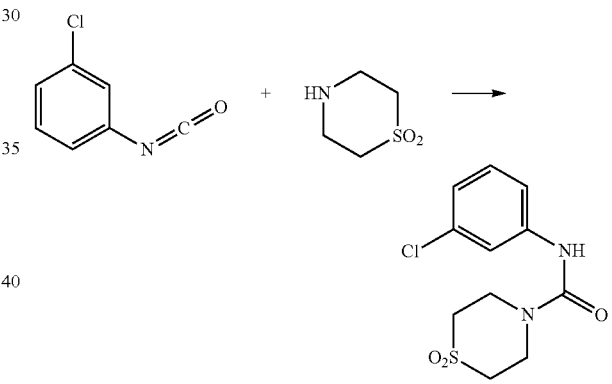

A solution of 1-chloro-3-isocyanatobenzene (0.305 g, 2.256 mmol) and thiomorpholine 1,1-dioxide (0.287 mL, 2.369 mmol) in diethylether (10 mL) was stirred at the room temperature for 16 hr. The precipitates were collected by filtration, washed by diethylether, and dried to give the title compound N-(3-chlorophenyl)thiomorpholine-4-carboxamide 1,1-dioxide as white solid (0.651 g, 99.9%).

[Step 2] Methyl 4-((N-(3-chlorophenyl)-1,1-dioxidothiomorpholine-4-carboxamido)methyl)benzoate

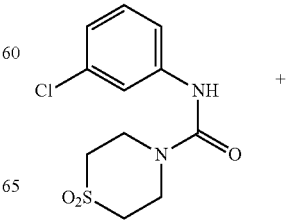 +

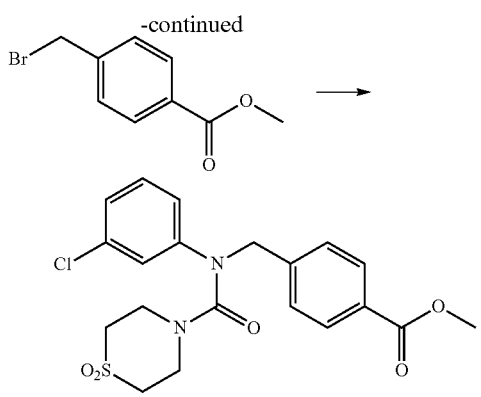

A mixture of N-(3-chlorophenyl)thiomorpholine-4-carboxamide 1,1-dioxide (0.500 g, 1.732 mmol) prepared in Step 1, methyl 4-(bromomethyl)benzoate (0.416 g, 1.818 mmol) and sodium hydride (60.00%, 0.083 g, 2.078 mmol) in ethanol (10 mL) was heated at 120° C. for 1 hr under the microwaves, and cooled down to the room temperature to terminate the reaction. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=0% to 50%) to give the title compound methyl 4-((N-(3-chlorophenyl)-1,1-dioxidothiomorpholine-4-carboxamido)methyl)benzoate as white solid (0.750 g, 99.1%).

[Step 3] N-(3-chlorophenyl)-N-(4-(hydrazinecarbonyl)benzyl)thiomorpholine-4-carboxamide 1,1-dioxide

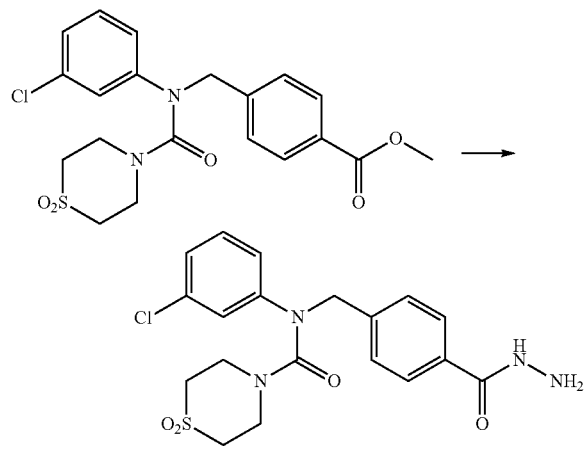

A mixture of methyl 4-((N-(3-chlorophenyl)-1,1-dioxidothiomorpholine-4-carboxamido)methyl)benzoate (0.750 g, 1.717 mmol) prepared in Step 2 and hydrazine monohydrate (1.621 mL, 34.332 mmol) in ethanol (10 mL) was heated at 120° C. for 1 hr under the microwaves, and cooled down to the room temperature to terminate the reaction. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(3-chlorophenyl)-N-(4-(hydrazinecarbonyl)benzyl)thiomorpholine-4-carboxamide 1,1-dioxide as white solid (0.750 g, 100.0%).

[Step 4] N-(3-chlorophenyl)-N-(4-(2-(2,2,2-trifluoroacetyl)hydrazine-1-carbonyl)benzyl)thiomorpholine-4-carboxamide 1,1-dioxide

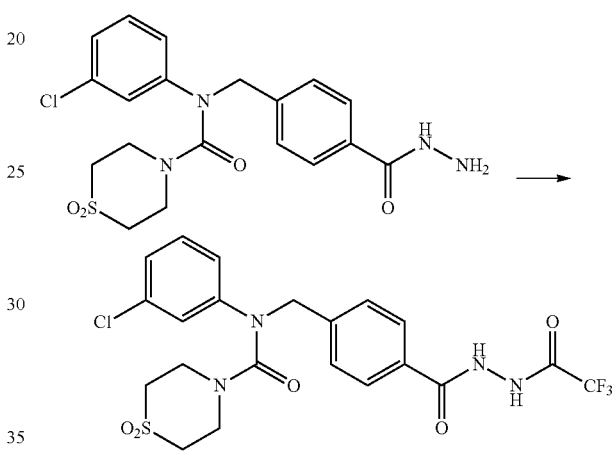

A solution of N-(3-chlorophenyl)-N-(4-(hydrazinecarbonyl)benzyl)thiomorpholine-4-carboxamide 1,1-dioxide (0.750 g, 1.717 mmol) prepared in Step 3 and triethylamine (0.357 mL, 2.575 mmol) in dichloromethane (10 mL) was mixed at 0° C. with trifluoroacetic anhydride (0.215 mL, 1.545 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(3-chlorophenyl)-N-(4-(2-(2,2,2-trifluoroacetyl)hydrazine-1-carbonyl)benzyl)thiomorpholine-4-carboxamide 1,1-dioxide as white solid (0.254 g, 27.8%).

[Step 5] Compound 21395

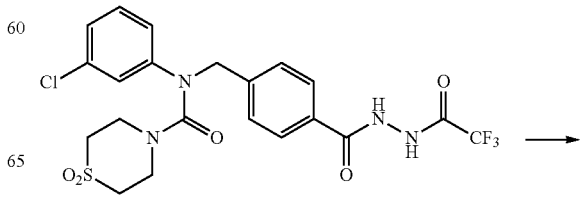

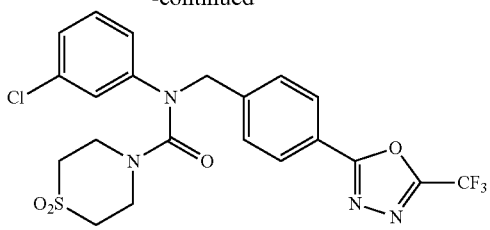

A mixture of N-(3-chlorophenyl)-N-(4-(2-(2,2,2-trifluoroacetyl)hydrazine-1-carbonyl)benzyl)thiomorpholine-4-carboxamide 1,1-dioxide (0.254 g, 0.477 mmol) prepared in Step 4 and burgess reagent (0.170 g, 0.715 mmol) in tetrahydrofuran (5 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(3-chlorophenyl)-N-(4-(5-(trifluoromethyl)-1,3,4-oxadiazol-2-yl)benzyl)thiomorpholine-4-carboxamide 1,1-dioxide as white solid (0.185 g, 75.4%).

$^1$H NMR (400 MHz, CDCl$_3$) δ 8.03 (d, 2H, J=8.3 Hz), 7.45 (d, 2H, J=8.3 Hz), 7.30-7.28 (m, 1H), 7.19-7.17 (m, 1H), 7.11-7.10 (m, 1H), 6.96-6.94 (m, 1H), 4.89 (s, 2H), 3.73-3.71 (m, 4H), 2.88-2.85 (m, 4H); LRMS (ES) m/z 515.3 (M$^+$+1).

Example 66. Compound 21396: 4-(2-hydroxy-2-methylpropyl)-N-phenyl-N-(4-(5-(trifluoromethyl)-1,3,4-oxadiazol-2-yl)benzyl)piperazine-1-carboxamide

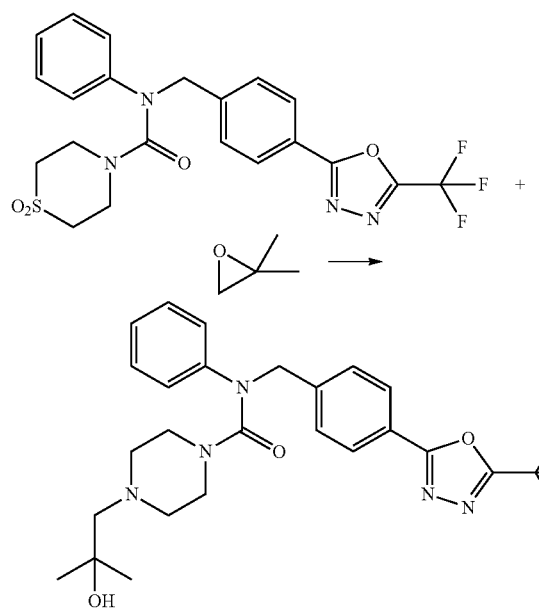

A mixture of N-phenyl-N-(4-(5-(trifluoromethyl)-1,3,4-oxadiazol-2-yl)benzyl)piperazine-1-carboxamide (0.100 g, 0.232 mmol) prepared in Example 32, 2,2-dimethyloxirane (0.022 g, 0.301 mmol) and N,N-diisopropylethylamine (0.101 mL, 0.579 mmol) in ethanol (10 mL) was heated at 120° C. for 30 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound 4-(2-hydroxy-2-methylpropyl)-N-phenyl-N-(4-(5-(trifluoromethyl)-1,3,4-oxadiazol-2-yl)benzyl)piperazine-1-carboxamide as colorless oil (0.040 g, 34.3%).

$^1$H NMR (400 MHz, CDCl$_3$) δ 8.04 (d, J=8.3 Hz, 2H), 7.51 (d, J=8.3 Hz, 2H), 7.32 (t, J=7.9 Hz, 2H), 7.13 (t, J=7.4 Hz, 1H), 7.06 (d, J=7.5 Hz, 2H), 4.97-4.92 (m, 2H), 3.29-3.28 (m, 4H), 2.48-2.46 (m, 4H), 2.06 (s, 2H), 1.14 (s, 6H)); LRMS (ES) m/z 504.2 (M$^+$+1).

Example 67. Compound 21397: N-isopropyl-N-(4-(5-(trifluoromethyl)-1,3,4-oxadiazol-2-yl)benzyl)thiomorpholine-4-carboxamide 1,1-dioxide

[Step 1] N-isopropylthiomorpholine-4-carboxamide 1,1-dioxide

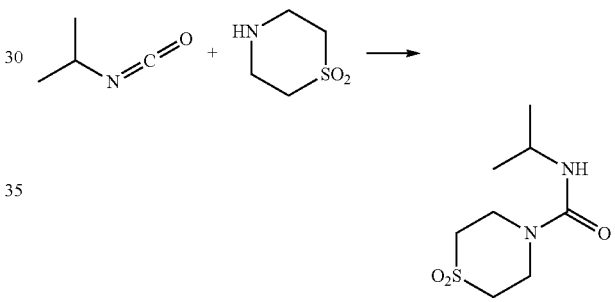

A solution of 2-isocyanatopropane (2.000 g, 23.499 mmol) and thiomorpholine 1,1-dioxide (3.335 g, 24.674 mmol) in diethylether (50 mL) was stirred at the room temperature for 16 hr. The precipitates were collected by filtration, washed by diethylether, and dried to give the title compound N-isopropylthiomorpholine-4-carboxamide 1,1-dioxide as white solid (3.830 g, 74.0%).

[Step 2] Methyl 4-((N-isopropyl-1,1-dioxidothiomorpholine-4-carboxamido)methyl)benzoate

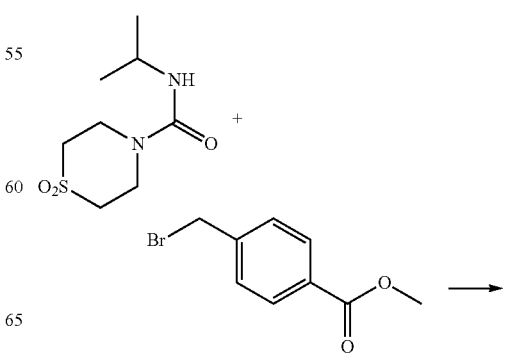

-continued

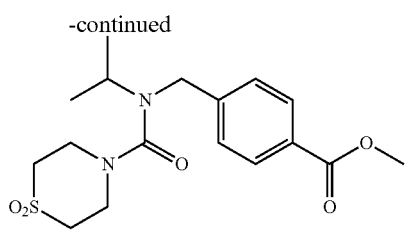

To a stirred solution of N-isopropylthiomorpholine-4-carboxamide 1,1-dioxide (1.730 g, 7.853 mmol) prepared in Step 1 and sodium hydride (60.00%, 0.346 g, 8.639 mmol) in N,N-dimethylformamide (10 mL) was added at 0° C. methyl 4-(bromomethyl)benzoate (1.979 g, 8.639 mmol). The reaction mixture was stirred at the same temperature for 16 hr. Then, saturated aqueous sodium bicarbonate solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 40 g cartridge; methanol/dichloromethane=0% to 50%) to give the title compound methyl 4-((N-isopropyl-1,1-dioxidothiomorpholine-4-carboxamido)methyl)benzoate as white solid (0.599 g, 19.3%).

[Step 3] N-(4-(hydrazinecarbonyl)benzyl)-N-isopropylthiomorpholine-4-carboxamide 1,1-dioxide

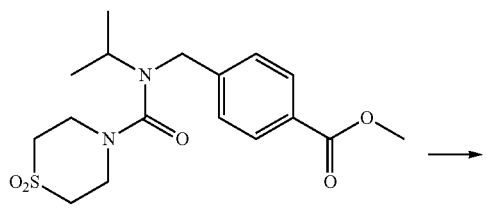

A solution of methyl 4-((N-isopropyl-1,1-dioxidothiomorpholine-4-carboxamido)methyl)benzoate (0.550 g, 1.493 mmol) prepared in Step 2 and hydrazine monohydrate (1.410 mL, 29.855 mmol) in ethanol (10 mL) was stirred at 120° C. for 1 hr, and cooled down to the room temperature to terminate the reaction. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give the title compound N-(4-(hydrazinecarbonyl)benzyl)-N-isopropylthiomorpholine-4-carboxamide 1,1-dioxide as white solid (0.224 g, 40.7%).

[Step 4] N-isopropyl-N-(4-(2-(2,2,2-trifluoroacetyl)hydrazine-1-carbonyl)benzyl)thiomorpholine-4-carboxamide 1,1-dioxide

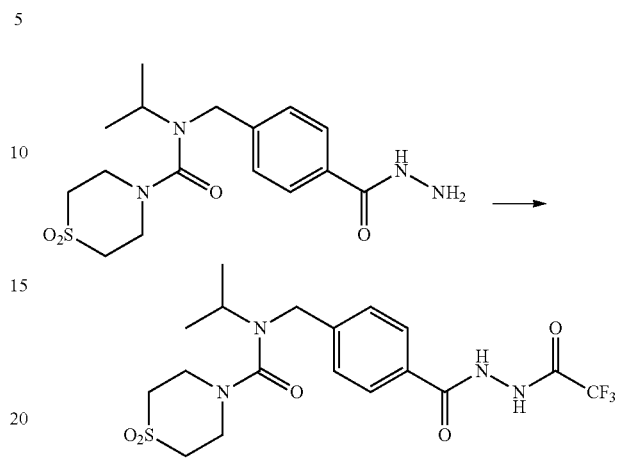

A solution of N-(4-(hydrazinecarbonyl)benzyl)-N-isopropylthiomorpholine-4-carboxamide 1,1-dioxide (0.214 g, 0.581 mmol) prepared in Step 3, triethylamine (0.121 mL, 0.871 mmol) and trifluoroacetic anhydride (0.073 mL, 0.523 mmol) in dichloromethane (5 mL) was stirred at the room temperature for 16 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound N-isopropyl-N-(4-(2-(2,2,2-trifluoroacetyl)hydrazine-1-carbonyl)benzyl)thiomorpholine-4-carboxamide 1,1-dioxide as white solid (0.088 g, 32.6%).

[Step 5] Compound 21397

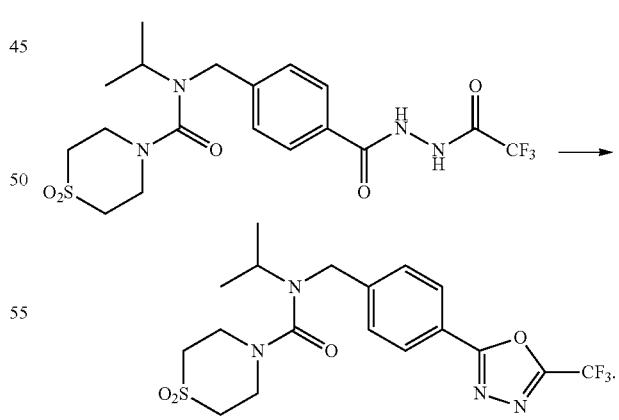

A mixture of N-isopropyl-N-(4-(2-(2,2,2-trifluoroacetyl)hydrazine-1-carbonyl)benzyl)thiomorpholine-4-carboxamide 1,1-dioxide (0.088 g, 0.189 mmol) prepared in Step 4 and burgess reagent (0.067 g, 0.284 mmol) in tetrahydrofuran (3 mL) was heated at 150° C. for 30 min under the microwaves, and cooled down to the room temperature to terminate the reaction. Then, saturated aqueous sodium bicarbonate solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 4 g cartridge; methanol/dichloromethane=0% to 3%) to give the title compound N-isopropyl-N-(4-(5-(trifluoromethyl)-1,3,4-oxadiazol-2-yl)benzyl)thiomorpholine-4-carboxamide 1,1-dioxide as brown oil (0.460 g, 543.8%).

$^1$H NMR (400 MHz, CDCl$_3$) δ 8.06 (d, 2H, J=8.3 Hz), 7.43 (d, 2H, J=8.4 Hz), 4.30 (s, 2H), 3.94-3.87 (m, 1H), 3.74-3.73 (m, 4H), 2.96-2.93 (m, 4H), 1.29 (d, 6H, J=6.7 Hz); LRMS (ES) m/z 447.1 (M$^+$+1).

Example 68. Compound 21398: N-methyl-N-(4-(5-(trifluoromethyl)-1,3,4-oxadiazol-2-yl)benzyl)morpholine-4-carboxamide

[Step 1] Methyl 4-((morpholine-4-carboxamido)methyl)benzoate

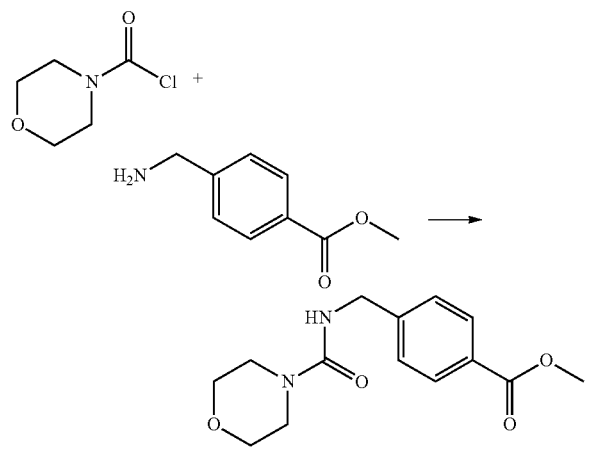

A solution of methyl 4-(aminomethyl)benzoate (2.000 g, 9.918 mmol), morpholine-4-carbonyl chloride (1.635 g, 10.910 mmol) and N,N-diisopropylethylamine (5.183 mL, 29.755 mmol) in dichloromethane (20 mL) was stirred at the room temperature for 12 hr. The reaction mixture was concentrated under the reduced pressure to remove the solvent, and water was added to the concentrate, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((morpholine-4-carboxamido)methyl)benzoate as White solid (2.200 g, 79.7%).

[Step 2] Methyl 4-((N-methylmorpholine-4-carboxamido)methyl)benzoate

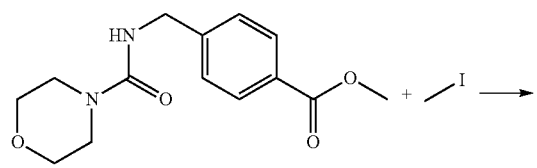

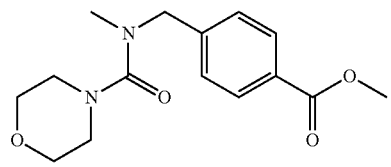

To a stirred solution of methyl 4-((morpholine-4-carboxamido)methyl)benzoate (0.300 g, 1.078 mmol) prepared in Step 1 in N,N-dimethylformamide (10 mL) was added at 0° C. sodium hydride (60.00%, 0.065 g, 1.617 mmol). The reaction mixture was stirred at the same temperature for 30 min, treated at the room temperature with Methyl iodide (0.074 mL, 1.186 mmol), and stirred for additional 12 hr. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-((N-methylmorpholine-4-carboxamido)methyl)benzoate as Colorless oil (0.210 g, 67.1%).

[Step 3] N-(4-(hydrazinecarbonyl)benzyl)-N-methylmorpholine-4-carboxamide

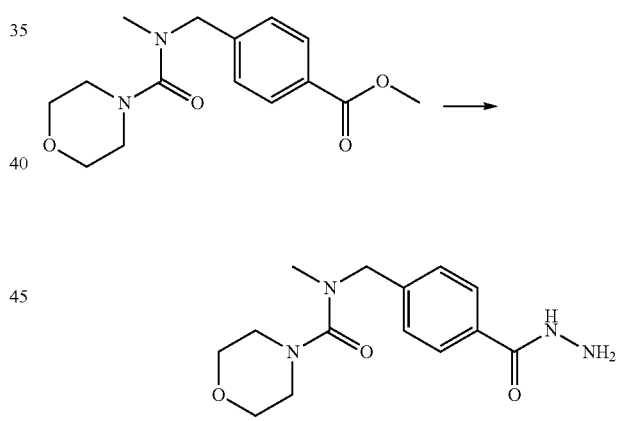

A mixture of methyl 4-((N-methylmorpholine-4-carboxamido)methyl)benzoate (0.210 g, 0.723 mmol) prepared in Step 2 and hydrazine hydrate (0.683 mL, 14.465 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(4-(hydrazinecarbonyl)benzyl)-N-methylmorpholine-4-carboxamide, 0.210 g, 100.0%, Colorless oil).

[Step 4] N-methyl-N-(4-(2-(2,2,2-trifluoroacetyl)hydrazine-1-carbonyl)benzyl)morpholine-4-carboxamide

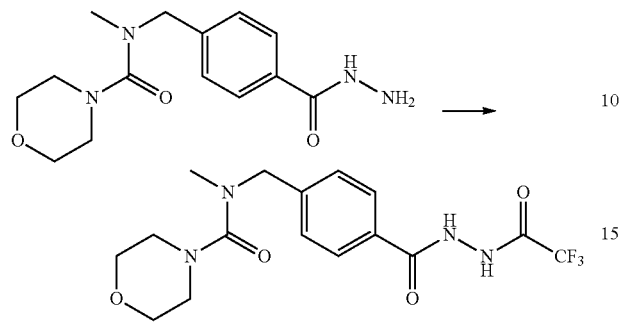

A solution of N-(4-(hydrazinecarbonyl)benzyl)-N-methylmorpholine-4-carboxamide (0.196 g, 0.670 mmol) prepared in Step 3, trifluoroacetic anhydride (0.084 mL, 0.603 mmol) and triethylamine (0.139 mL, 1.006 mmol) in dichloromethane (10 mL) was stirred at the room temperature for 2 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-methyl-N-(4-(2-(2,2,2-trifluoroacetyl)hydrazine-1-carbonyl)benzyl)morpholine-4-carboxamide as Colorless oil (0.115 g, 44.4%).

[Step 5] Compound 21398

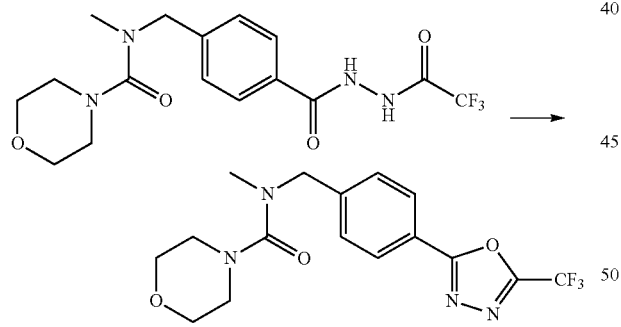

A mixture of N-methyl-N-(4-(2-(2,2,2-trifluoroacetyl)hydrazine-1-carbonyl)benzyl)morpholine-4-carboxamide (0.115 g, 0.296 mmol) prepared in Step 4 and 1-methoxy-N-triethylammoniosulfonyl-methanimidate (Burgess reagent, 0.106 g, 0.444 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound N-methyl-N-(4-(5-(trifluoromethyl)-1,3,4-oxadiazol-2-yl)benzyl)morpholine-4-carboxamide as Colorless oil0 (0.080 g, 73.3%).

$^1$H NMR (400 MHz, CDCl$_3$) δ 8.10 (d, 2H, J=8.0 Hz), 7.47 (d, 2H, J=8.0 Hz), 4.50 (s, 2H), 3.73 (t, 4H, J=4.6 Hz), 3.31 (t, 4H, J=4.7 Hz), 2.84 (s, 3H); LRMS (ES) m/z 371.2 (M$^+$+1).

Example 69. Compound 21399: N-ethyl-N-(4-(5-(trifluoromethyl)-1,3,4-oxadiazol-2-yl)benzyl)morpholine-4-carboxamide

[Step 1] Methyl 4-((N-ethylmorpholine-4-carboxamido)methyl)benzoate

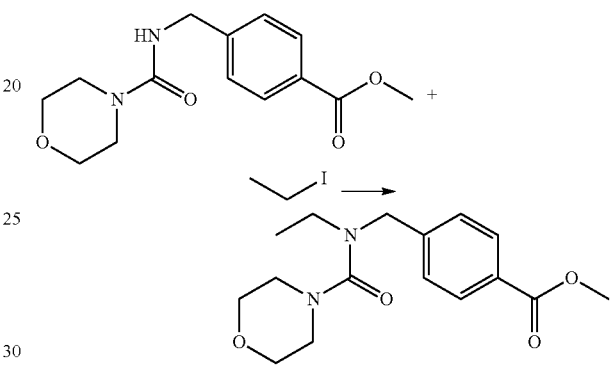

To a stirred solution of methyl 4-((morpholine-4-carboxamido)methyl)benzoate (0.300 g, 1.078 mmol) in N,N-dimethylformamide (10 mL) was added at 0° C. sodium hydride (60.00%, 0.065 g, 1.617 mmol). The reaction mixture was stirred at the same temperature for 30 min, treated at the room temperature with Ethyl iodide (0.095 mL, 1.186 mmol), and stirred for additional 12 hr. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-((N-ethylmorpholine-4-carboxamido)methyl)benzoate as Colorless oil (0.135 g, 41.1%).

[Step 2] N-ethyl-N-(4-(hydrazinecarbonyl)benzyl)morpholine-4-carboxamide

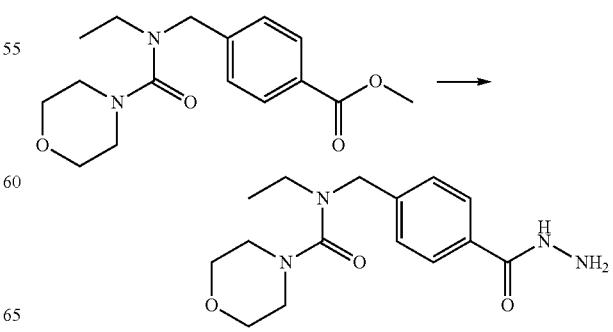

A mixture of methyl 4-((N-ethylmorpholine-4-carboxamido)methyl)benzoate (0.135 g, 0.444 mmol) prepared in Step 1 and hydrazine hydrate (0.419 mL, 8.870 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-ethyl-N-(4-(hydrazinecarbonyl)benzyl)morpholine-4-carboxamide, 0.135 g, 100.0%, Colorless oil).

[Step 3] N-ethyl-N-(4-(2-(2,2,2-trifluoroacetyl)hydrazine-1-carbonyl)benzyl)morpholine-4-carboxamide

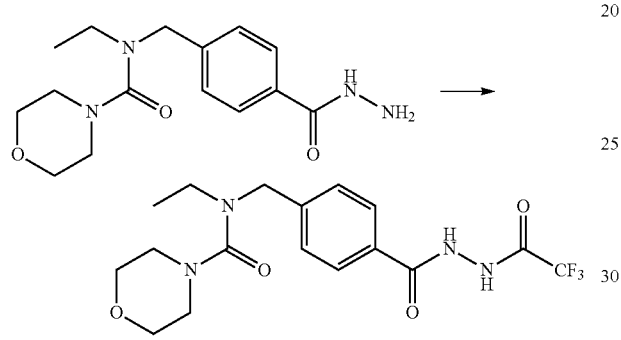

A solution of N-ethyl-N-(4-(hydrazinecarbonyl)benzyl)morpholine-4-carboxamide (0.190 g, 0.620 mmol) prepared in Step 2, trifluoroacetic anhydride (0.117 g, 0.558 mmol) and triethylamine (0.094 g, 0.930 mmol) in dichloromethane (10 mL) was stirred at the room temperature for 3 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-ethyl-N-(4-(2-(2,2,2-trifluoroacetyl)hydrazine-1-carbonyl)benzyl)morpholine-4-carboxamide as Colorless oil (0.120 g, 48.3%).

[Step 4] Compound 21399

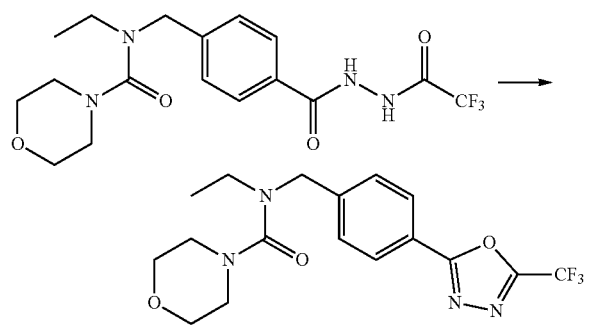

A mixture of N-ethyl-N-(4-(2-(2,2,2-trifluoroacetyl)hydrazine-1-carbonyl)benzyl)morpholine-4-carboxamide (0.120 g, 0.300 mmol) prepared in Step 3 and 1-methoxy-N-triethylammoniosulfonyl-methanimidate (Burgess reagent, 0.107 g, 0.450 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound N-ethyl-N-(4-(5-(trifluoromethyl)-1,3,4-oxadiazol-2-yl)benzyl)morpholine-4-carboxamide as Colorless oil (0.080 g, 69.8%).

$^1$H NMR (400 MHz, CDCl$_3$) δ 8.11-8.09 (m, 2H), 7.48 (dd, 2H, J=8.0, 0.6 Hz), 4.50 (s, 2H), 3.71 (t, 4H, J=4.7 Hz), 3.31 (t, 4H, J=4.7 Hz), 3.22 (q, 2H, J=7.1 Hz), 1.18-1.15 (m, 3H)); LRMS (ES) m/z 385.2 (M$^+$+1).

Example 70. Compound 21400: N-propyl-N-(4-(5-(trifluoromethyl)-1,3,4-oxadiazol-2-yl)benzyl)morpholine-4-carboxamide

[Step 1] Methyl 4-((N-propylmorpholine-4-carboxamido)methyl)benzoate

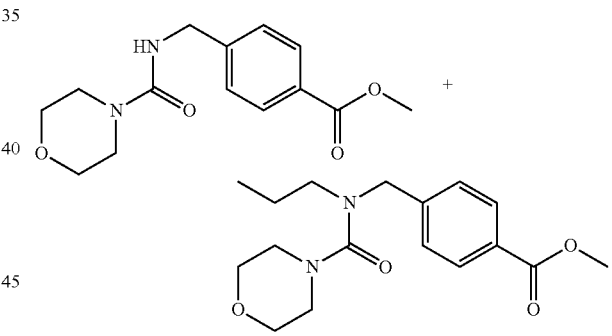

To a stirred solution of methyl 4-((morpholine-4-carboxamido)methyl)benzoate (0.300 g, 1.078 mmol) in N,N-dimethylformamide (20 mL) was added at 0° C. sodium hydride (60.00%, 0.065 g, 1.617 mmol). The reaction mixture was stirred at the same temperature for 30 min, treated at the room temperature with 1-bromopropane (0.108 mL, 1.186 mmol), and stirred for additional 12 hr. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-((N-propylmorpholine-4-carboxamido)methyl)benzoate as Colorless oil (0.097 g, 28.3%).

[Step 2] N-(4-(hydrazinecarbonyl)benzyl)-N-propyl-morpholine-4-carboxamide

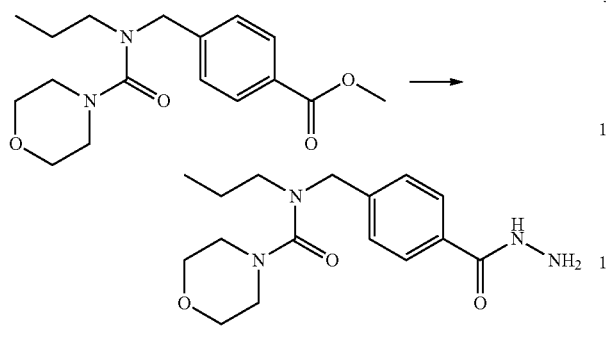

A mixture of methyl 4-((N-propylmorpholine-4-carboxamido)methyl)benzoate (0.097 g, 0.305 mmol) prepared in Step 1 and hydrazine hydrate (0.288 mL, 6.093 mmol) in ethanol (10 mL) was heated at 120° C. for 1 hr under the microwaves, and cooled down to the room temperature to terminate the reaction. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The crude product was used without further purification (N-(4-(hydrazinecarbonyl)benzyl)-N-propylmorpholine-4-carboxamide, 0.090 g, 92.8%, Colorless oil).

[Step 3] N-propyl-N-(4-(2-(2,2,2-trifluoroacetyl)hydrazine-1-carbonyl)benzyl)morpholine-4-carboxamide

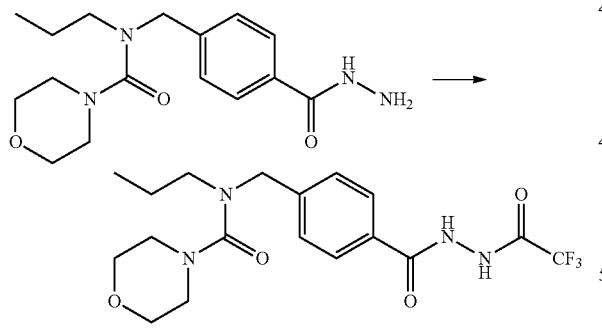

A solution of N-(4-(hydrazinecarbonyl)benzyl)-N-propylmorpholine-4-carboxamide (0.087 g, 0.272 mmol) prepared in Step 2, trifluoroacetic anhydride (0.051 g, 0.244 mmol) and triethylamine (0.041 g, 0.407 mmol) in dichloromethane (10 mL) was stirred at the room temperature for 3 hr. The reaction mixture was concentrated under the reduced pressure to remove the solvent, and water was added to the concentrate, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-propyl-N-(4-(2-(2,2,2-trifluoroacetyl)hydrazine-1-carbonyl)benzyl)morpholine-4-carboxamide as Colorless oil (0.081 g, 72.0%).

[Step 4] Compound 21400

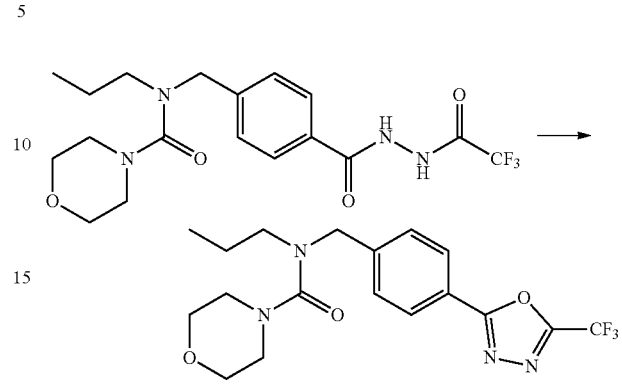

A mixture of N-propyl-N-(4-(2-(2,2,2-trifluoroacetyl)hydrazine-1-carbonyl)benzyl)morpholine-4-carboxamide (0.081 g, 0.195 mmol) prepared in Step 3 and 1-methoxy-N-triethylammoniosulfonyl-methanimidate (Burgess reagent, 0.070 g, 0.292 mmol) in tetrahydrofuran (10 mL) was heated at 120° C. for 30 min under the microwaves, and cooled down to the room temperature to terminate the reaction. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound N-propyl-N-(4-(5-(trifluoromethyl)-1,3,4-oxadiazol-2-yl)benzyl)morpholine-4-carboxamide as Colorless oil (0.050 g, 64.8%).

$^1$H NMR (400 MHz, CDCl$_3$) δ 8.10 (d, 2H, J=8.2 Hz), 7.46 (d, 2H, J=8.1 Hz), 4.51 (s, 2H), 3.73-3.70 (m, 4H), 3.31 (t, 4H, J=4.7 Hz), 3.10 (t, 2H, J=7.6 Hz), 1.63-1.58 (m, 2H), 0.89 (t, 3H, J=7.4 Hz); LRMS (ES) m/z 399.2 (M$^+$+1).

Example 71. Compound 21401: N-butyl-N-(4-(5-(trifluoromethyl)-1,3,4-oxadiazol-2-yl)benzyl)morpholine-4-carboxamide

[Step 1] Methyl 4-((N-butylmorpholine-4-carboxamido)methyl)benzoate

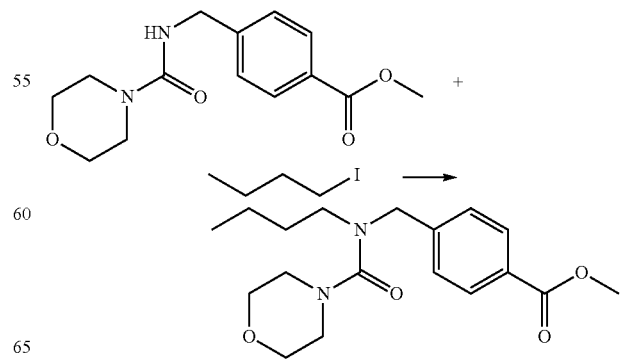

To a stirred solution of methyl 4-((morpholine-4-carboxamido)methyl)benzoate (0.300 g, 1.078 mmol) in N,N-dimethylformamide (10 mL) was added at 0° C. sodium hydride (60.00%, 0.065 g, 1.617 mmol). The reaction mixture was stirred at the same temperature for 30 min, treated at the room temperature with 1-iodobutane (0.135 mL, 1.186 mmol), and stirred for additional 12 hr. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-((N-butylmorpholine-4-carboxamido)methyl)benzoate as Colorless oil (0.195 g, 54.4%).

[Step 2] N-butyl-N-(4-(hydrazinecarbonyl)benzyl)morpholine-4-carboxamide

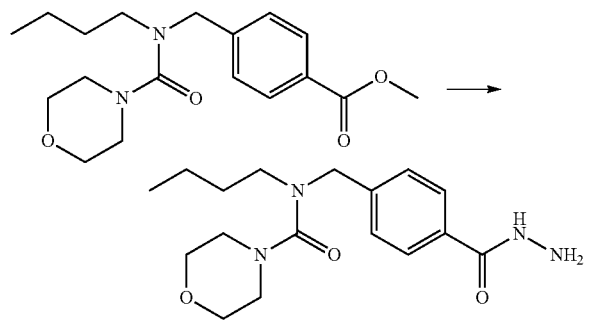

A mixture of methyl 4-((N-butylmorpholine-4-carboxamido)methyl)benzoate (0.195 g, 0.583 mmol) prepared in Step 1 and hydrazine hydrate (0.551 mL, 11.661 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-butyl-N-(4-(hydrazinecarbonyl)benzyl)morpholine-4-carboxamide, 0.190 g, 97.4%, Colorless oil).

[Step 3] N-butyl-N-(4-(2-(2,2,2-trifluoroacetyl)hydrazine-1-carbonyl)benzyl)morpholine-4-carboxamide

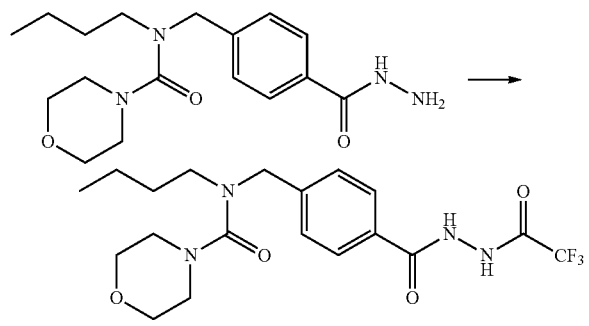

A solution of N-butyl-N-(4-(hydrazinecarbonyl)benzyl)morpholine-4-carboxamide (0.188 g, 0.562 mmol) prepared in Step 2, trifluoroacetic anhydride (0.106 g, 0.506 mmol) and triethylamine (0.085 g, 0.843 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-butyl-N-(4-(2-(2,2,2-trifluoroacetyl)hydrazine-1-carbonyl)benzyl)morpholine-4-carboxamide as Colorless oil (0.132 g, 54.8%).

[Step 4] Compound 21401

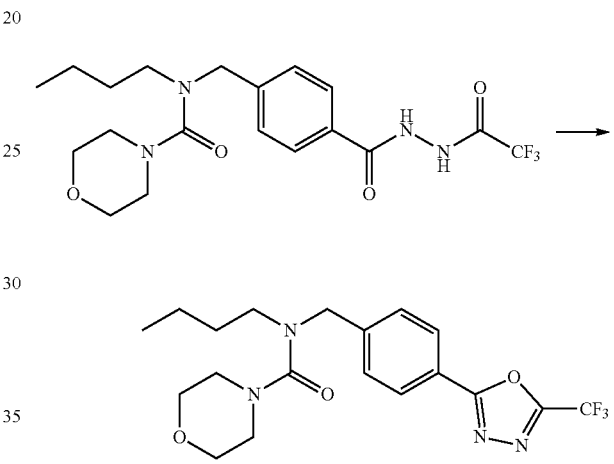

A mixture of N-butyl-N-(4-(2-(2,2,2-trifluoroacetyl)hydrazine-1-carbonyl)benzyl)morpholine-4-carboxamide (0.132 g, 0.307 mmol) prepared in Step 3 and 1-methoxy-N-triethylammoniosulfonyl-methanimidate (Burgess reagent, 0.110 g, 0.460 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound N-butyl-N-(4-(5-(trifluoromethyl)-1,3,4-oxadiazol-2-yl)benzyl)morpholine-4-carboxamide as Colorless oil (0.100 g, 79.1%).

$^1$H NMR (400 MHz, CDCl$_3$) δ 8.10 (dd, 2H, J=8.4, 1.7 Hz), 7.46 (d, 2H, J=8.5 Hz), 4.50 (s, 2H), 3.73-3.69 (m, 4H), 3.31 (t, 4H, J=4.7 Hz), 3.14 (t, 2H, J=7.6 Hz), 1.58-1.53 (m, 2H), 1.32-1.27 (m, 2H), 0.94-0.92 (m, 3H)); LRMS (ES) m/z 413.2 (M$^+$+1):

Example 72. Compound 21402: 1-Methyl-3-phenyl-1-propyl-3-(4-(5-(trifluoromethyl)-1,3,4-oxadiazol-2-yl)benzyl)urea

[Step 1] Methyl 4-((3-methyl-1-phenylureido)methyl)benzoate

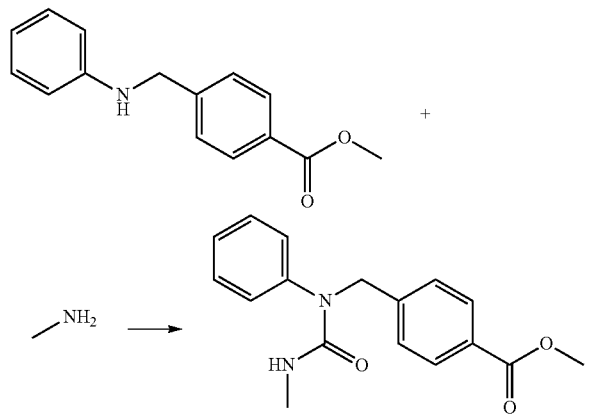

A solution of methyl 4-((phenylamino)methyl)benzoate (2.000 g, 8.290 mmol), methyl amine (2.00 M solution, 6.218 mL, 12.436 mmol), N,N-diisopropylethylamine (7.220 mL, 41.452 mmol) and triphosgene (1.968 g, 6.632 mmol) in dichloromethane (10 mL) was stirred at the room temperature for 12 hr. The reaction mixture was concentrated under the reduced pressure to remove the solvent, and water was added to the concentrate, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound methyl 4-((3-methyl-1-phenylureido)methyl)benzoate as Colorless oil (1.500 g, 60.6%).

[Step 2] Methyl 4-((3-methyl-1-phenyl-3-propylureido)methyl)benzoate

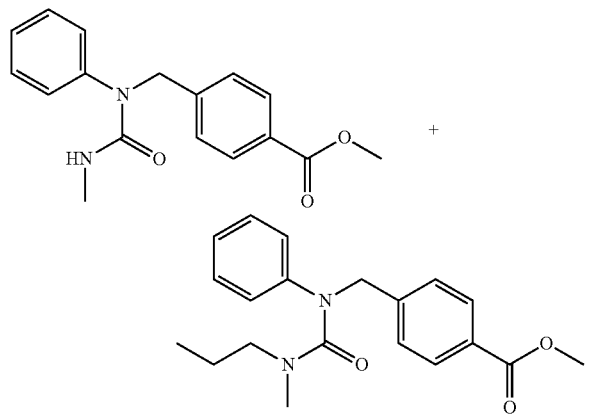

To a stirred solution of methyl 4-((3-methyl-1-phenylureido)methyl)benzoate (0.400 g, 1.341 mmol) prepared in Step 1 in N,N-dimethylformamide (10 mL) was added at 0° C. sodium hydride (60.00%, 0.080 g, 2.011 mmol). The reaction mixture was stirred at the same temperature for 30 min, treated at the room temperature with 1-bromopropane (0.134 mL, 1.475 mmol), and stirred for additional 12 hr. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound methyl 4-((3-methyl-1-phenyl-3-propylureido) methyl)benzoate as Yellow oil (0.220 g, 48.2%).

[Step 3] 1-(4-(hydrazinecarbonyl)benzyl)-3-methyl-1-phenyl-3-propylurea

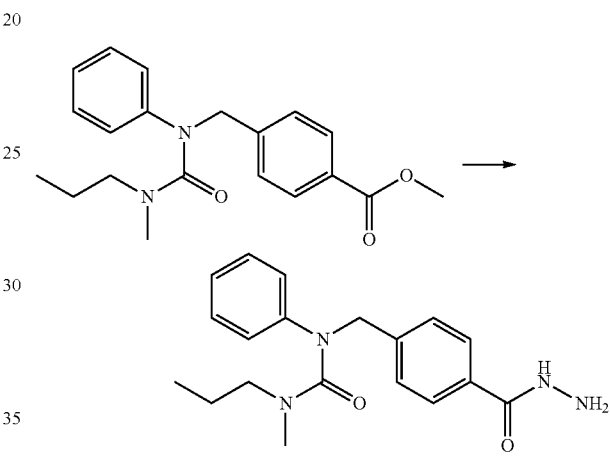

A solution of methyl 4-((3-methyl-1-phenyl-3-propylureido)methyl)benzoate (0.220 g, 0.646 mmol) prepared in Step 2 and hydrazine hydrate (0.610 mL, 12.925 mmol) in dichloromethane (10 mL) was stirred at the room temperature for 1 hr. The reaction mixture was concentrated under the reduced pressure to remove the solvent, and water was added to the concentrate, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound 1-(4-(hydrazinecarbonyl)benzyl)-3-methyl-1-phenyl-3-propylurea as Colorless oil (0.210 g, 95.5%).

[Step 4] 1-methyl-3-phenyl-1-propyl-3-(4-(2-(2,2,2-trifluoroacetyl)hydrazine-1-carbonyl)benzyl)urea

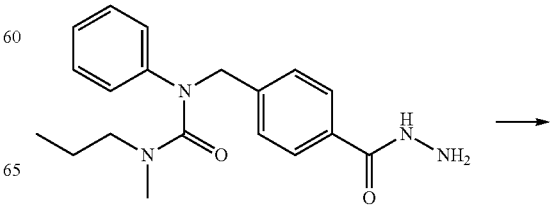

-continued

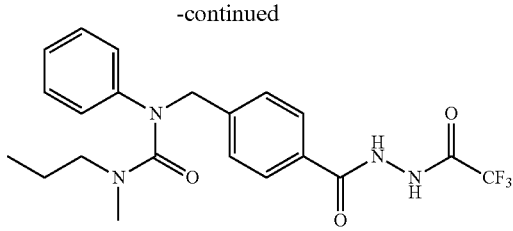

A solution of 1-(4-(hydrazinecarbonyl)benzyl)-3-methyl-1-phenyl-3-propylurea (0.210 g, 0.617 mmol) prepared in Step 3, trifluoroacetic anhydride (0.117 g, 0.555 mmol) and triethylamine (0.094 g, 0.925 mmol) in dichloromethane (10 mL) was stirred at the room temperature for 3 hr. The reaction mixture was concentrated under the reduced pressure to remove the solvent, and water was added to the concentrate, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound 1-methyl-3-phenyl-1-propyl-3-(4-(2-(2,2,2-trifluoroacetyl)hydrazine-1-carbonyl)benzyl)urea as Colorless oil (0.230 g, 85.4%).

[Step 5] Compound 21402

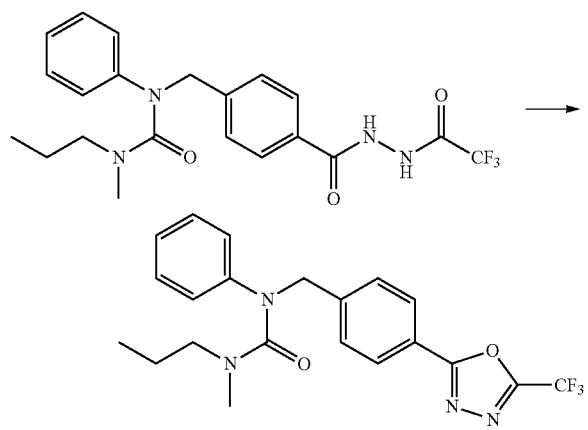

A mixture of 1-methyl-3-phenyl-1-propyl-3-(4-(2-(2,2,2-trifluoroacetyl)hydrazine-1-carbonyl)benzyl)urea (0.231 g, 0.529 mmol) prepared in Step 4 and 1-methoxy-N-triethylammoniosulfonyl-methanimidate (Burgess reagent, 0.189 g, 0.794 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound 1-methyl-3-phenyl-1-propyl-3-(4-(5-(trifluoromethyl)-1,3,4-oxadiazol-2-yl)benzyl)urea as colorless oil (0.050 g, 22.6%).

$^1$H NMR (400 MHz, CDCl$_3$) δ 8.03 (d, 2H, J=8.4 Hz), 7.53 (d, 2H, J=8.4 Hz), 7.32-7.28 (m, 2H), 7.15-7.09 (m, 1H), 7.05-7.03 (m, 2H), 4.92 (s, 2H), 3.16 (t, 2H, J=7.6 Hz), 2.65 (s, 3H), 1.47-1.46 (m, 2H), 0.83 (t, 3H, J=7.4 Hz); LRMS (ES) m/z 419.2 (M$^+$+1).

Example 73. Compound 21403: N-phenyl-4-(pyridin-2-yl)-N-(4-(5-(trifluoromethyl)-1,3,4-oxadiazol-2-yl)benzyl)piperazine-1-carboxamide

[Step 1] Methyl 4-((N-phenyl-4-(pyridin-2-yl)piperazine-1-carboxamido)methyl)benzoate

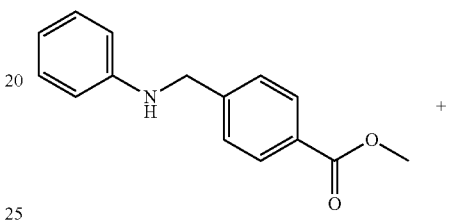

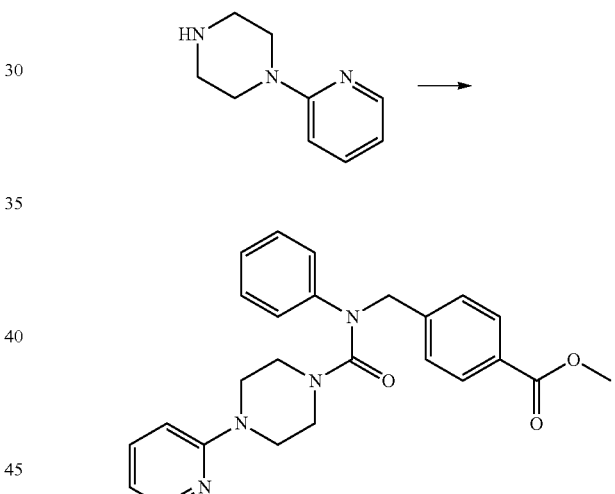

To a stirred solution of methyl 4-((phenylamino)methyl)benzoate (0.300 g, 1.244 mmol) in dichloromethane (10 mL) were added at 0° C. N,N-diisopropylethylamine (1.083 mL, 6.218 mmol) and triphosgene (0.295 g, 0.995 mmol). The reaction mixture was stirred at the same temperature for 30 min, treated at the room temperature with 1-(pyridin-2-yl)piperazine (0.199 mL, 1.368 mmol), and stirred for additional 4 hr. The reaction mixture was concentrated under the reduced pressure to remove the solvent, and water was added to the concentrate, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((N-phenyl-4-(pyridin-2-yl)piperazine-1-carboxamido)methyl)benzoate as Colorless oil (0.391 g, 73.0%).

[Step 2] N-(4-(hydrazinecarbonyl)benzyl)-N-phenyl-4-(pyridin-2-yl)piperazine-1-carboxamide

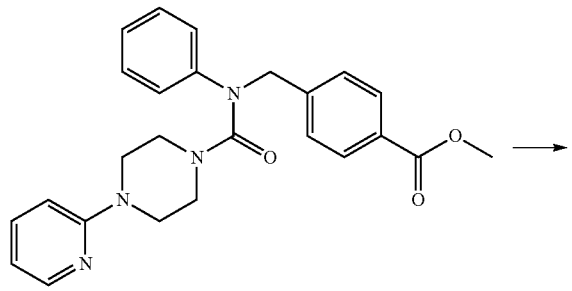

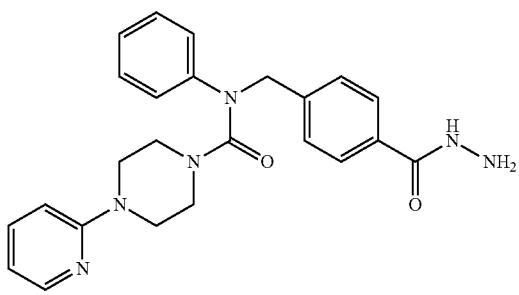

A mixture of methyl 4-((N-phenyl-4-(pyridin-2-yl)piperazine-1-carboxamido)methyl)benzoate (0.391 g, 0.908 mmol) prepared in Step 1 and hydrazine hydrate (0.858 mL, 18.169 mmol) in ethanol (20 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous $MgSO_4$), filtered, and concentrated in vacuo. The concentrate was purified and concentrated by column chromatography ($SiO_2$, 12 g cartridge; ethyl acetate/hexane=0% to 30%) to give the title compound N-(4-(hydrazinecarbonyl)benzyl)-N-phenyl-4-(pyridin-2-yl)piperazine-1-carboxamide as Colorless oil (0.390 g, 99.7%).

[Step 3] N-phenyl-4-(pyridin-2-yl)-N-(4-(2-(2,2,2-trifluoroacetyl)hydrazine-1-carbonyl)benzyl)piperazine-1-carboxamide

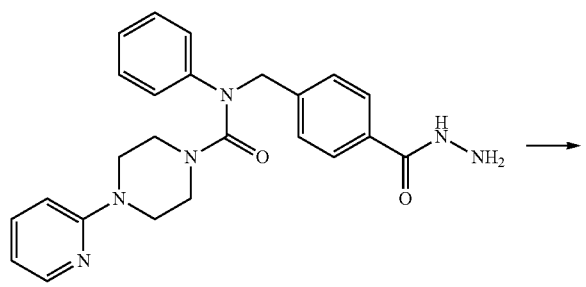

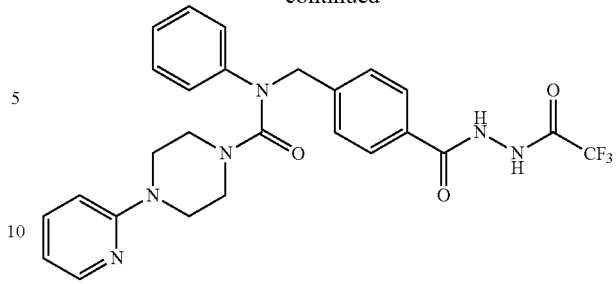

A solution of N-(4-(hydrazinecarbonyl)benzyl)-N-phenyl-4-(pyridin-2-yl)piperazine-1-carboxamide (0.391 g, 0.908 mmol) prepared in Step 2, trifluoroacetic anhydride (0.172 g, 0.817 mmol) and triethylamine (0.138 g, 1.362 mmol) in dichloromethane (10 mL) was stirred at the room temperature for 3 hr. The reaction mixture was concentrated under the reduced pressure to remove the solvent, and water was added to the concentrate, followed by extraction with dichloromethane. The organic layer was washed with aqueous saturated sodium chloride solution, dried (anhydrous $MgSO_4$), filtered, and concentrated in vacuo. The concentrate was purified and concentrated by column chromatography ($SiO_2$, 12 g cartridge; methanol/dichloromethane=0% to 10%) to give the title compound N-phenyl-4-(pyridin-2-yl)-N-(4-(2-(2,2,2-trifluoroacetyl)hydrazine-1-carbonyl)benzyl)piperazine-1-carboxamide as Colorless oil (0.435 g, 91.0%).

[Step 4] Compound 21403

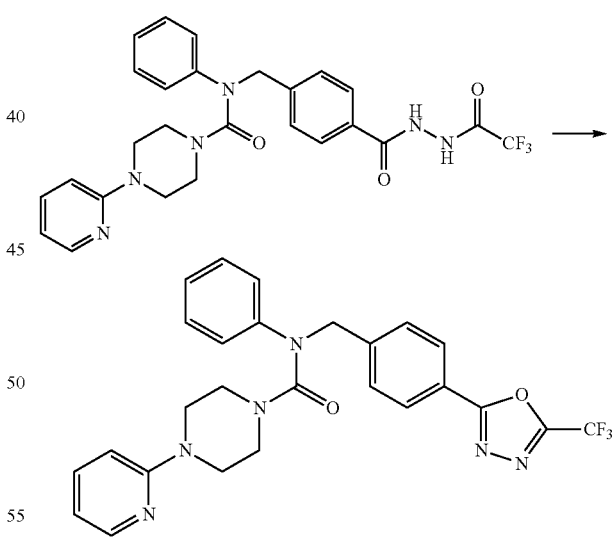

A mixture of N-phenyl-4-(pyridin-2-yl)-N-(4-(2-(2,2,2-trifluoroacetyl)hydrazine-1-carbonyl)benzyl)piperazine-1-carboxamide (0.435 g, 0.826 mmol) prepared in Step 3 and 1-methoxy-N-triethylammoniosulfonyl-methanimidate (Burgess reagent, 0.295 g, 1.239 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound N-phenyl-4-(pyridin-2-yl)-N-(4-(5-(trifluoromethyl)-1,3,4-oxadiazol-2-yl)benzyl)piperazine-1-carboxamide as Colorless oil (0.320 g, 76.2%).

¹H NMR (400 MHz, CDCl₃) δ 8.17-8.15 (m, 1H), 8.05-8.02 (m, 2H), 7.53-7.48 (m, 3H), 7.34-7.28 (m, 2H), 7.16-7.10 (m, 3H), 6.67-6.60 (m, 1H), 4.98 (s, 2H), 3.41 (s, 8H); LRMS (ES) m/z 433.35 (M⁺+1).

Example 74. Compound 21404: Ethyl 2-((2S,6R)-2,6-dimethyl-4-(phenyl(4-(5-(trifluoromethyl)-1,3,4-oxadiazol-2-yl)benzyl) carbamoyl)piperazin-1-yl)acetate

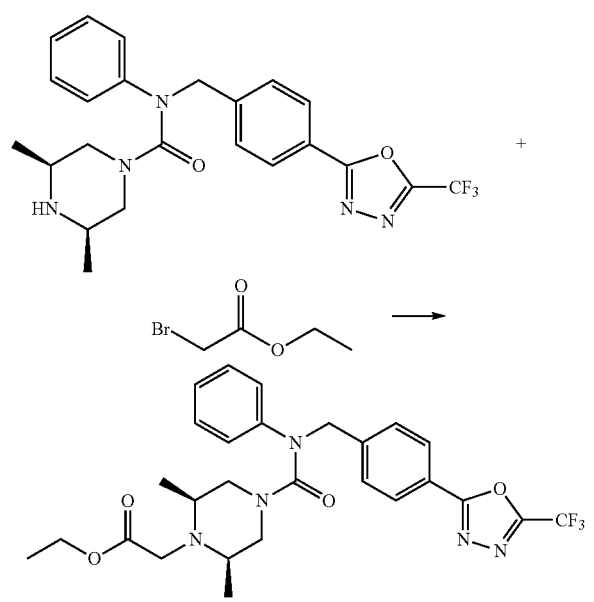

A solution of (3S,5R)-3,5-dimethyl-N-phenyl-N-(4-(5-(trifluoromethyl)-1,3,4-oxadiazol-2-yl)benzyl)piperazine-1-carboxamide (0.300 g, 0.653 mmol) prepared in Example 55, ethyl 2-bromoacetate (0.164 g, 0.979 mmol) and cesium carbonate (0.425 g, 1.306 mmol) in acetonitrile (10 mL) was stirred at the room temperature for 12 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound ethyl 2-((2S,6R)-2,6-dimethyl-4-(phenyl(4-(5-(trifluoromethyl)-1,3,4-oxadiazol-2-yl)benzyl) carbamoyl)piperazin-1-yl)acetate as Colorless oil (0.100 g, 28.1%).

¹H NMR (400 MHz, CDCl₃) δ 8.04-8.01 (m, 2H), 7.51-7.49 (m, 2H), 7.32-7.28 (m, 2H), 7.11 (t, 1H, J=7.4 Hz), 7.06-7.04 (m, 2H), 4.93 (s, 2H), 4.17-4.10 (m, 2H), 3.67 (d, 2H, J=12.8 Hz), 3.48 (s, 2H), 2.76 (s, 2H), 2.43 (t, 2H, J=11.7 Hz), 1.29-1.24 (m, 3H), 0.94 (d, 6H, J=6.2 Hz); LRMS (ES) m/z 546.2 (M⁺+1).

Example 75. Compound 21405: N-(4-(5-(trifluoromethyl)-1,3,4-oxadiazol-2-yl)benzyl)-N-(3-(trifluoromethyl)phenyl)morpholine-4-carboxamide

[Step 1] Methyl 4-((N-(3-(trifluoromethyl)phenyl)morpholine-4-carboxamido)methyl)benzoate

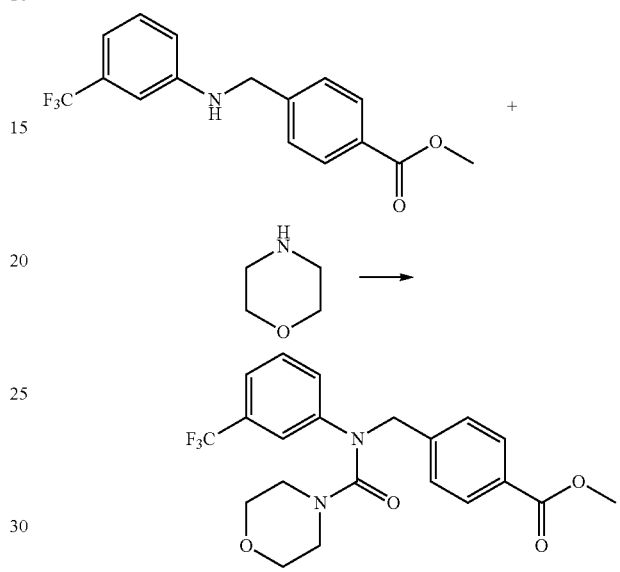

To a stirred solution of methyl 4-(((3-(trifluoromethyl)phenyl)amino)methyl)benzoate (0.810 g, 2.619 mmol) in dichloromethane (10 mL) were added at 0° C. N,N-diisopropylethylamine (2.281 mL, 13.095 mmol) and triphosgene (0.622 g, 2.095 mmol). The reaction mixture was stirred at the same temperature for 30 min, treated at the room temperature with morpholine (0.249 mL, 2.881 mmol), and stirred for additional 2 hr. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound methyl 4-((N-(3-(trifluoromethyl)phenyl)morpholine-4-carboxamido)methyl)benzoate as Colorless oil (1.080 g, 97.6%).

[Step 2] N-(4-(hydrazinecarbonyl)benzyl)-N-(3-(trifluoromethyl)phenyl)morpholine-4-carboxamide

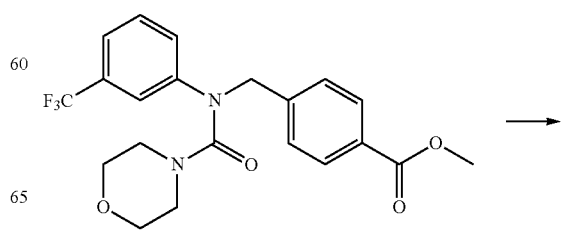

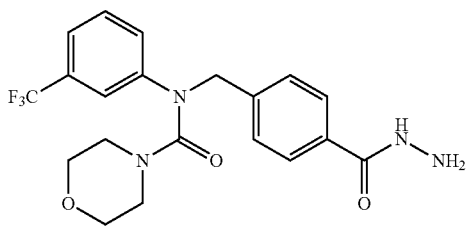

A mixture of methyl 4-((N-(3-(trifluoromethyl)phenyl)morpholine-4-carboxamido)methyl)benzoate (1.080 g, 2.557 mmol) prepared in Step 1 and hydrazine monohydrate (2.415 mL, 51.136 mmol) in ethanol (10 mL) was heated at the room temperature for 1 hr under the microwaves. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(4-(hydrazinecarbonyl)benzyl)-N-(3-(trifluoromethyl)phenyl)morpholine-4-carboxamide, 1.000 g, 92.6%, Colorless oil).

[Step 3] N-(4-(2-(2,2,2-trifluoroacetyl)hydrazine-1-carbonyl)benzyl)-N-(3-(trifluoromethyl)phenyl)morpholine-4-carboxamide

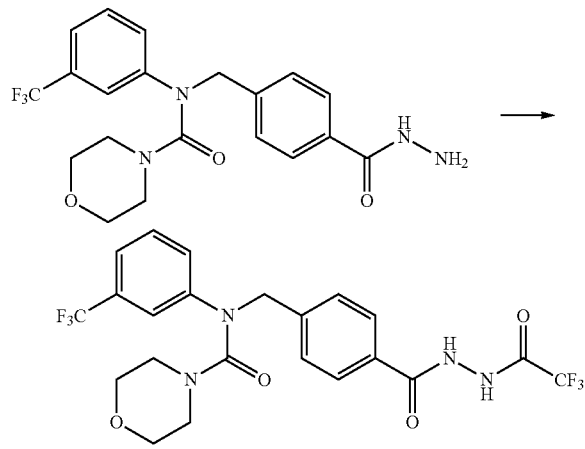

A solution of N-(4-(hydrazinecarbonyl)benzyl)-N-(3-(trifluoromethyl)phenyl)morpholine-4-carboxamide (0.895 g, 2.119 mmol) prepared in Step 2, trifluoroacetic anhydride (0.401 g, 1.907 mmol) and triethylamine (0.322 g, 3.178 mmol) in dichloromethane (10 mL) was stirred at the room temperature for 2 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-(2-(2,2,2-trifluoroacetyl)hydrazine-1-carbonyl)benzyl)-N-(3-(trifluoromethyl)phenyl)morpholine-4-carboxamide as Colorless oil (0.930 g, 84.7%).

[Step 4] Compound 21405

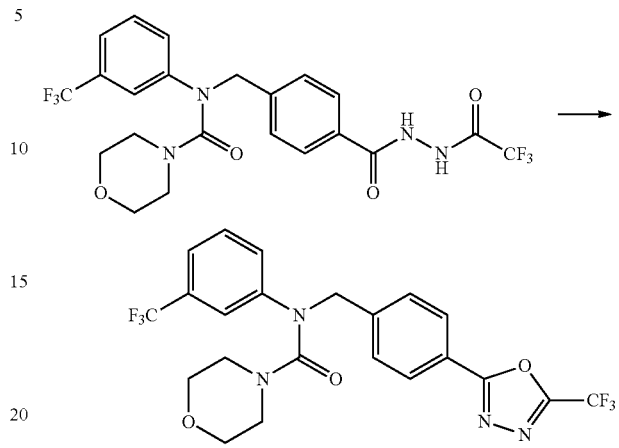

A mixture of N-(4-(2-(2,2,2-trifluoroacetyl)hydrazine-1-carbonyl)benzyl)-N-(3-(trifluoromethyl)phenyl)morpholine-4-carboxamide (0.930 g, 1.794 mmol) prepared in Step 3 and 1-methoxy-N-triethylammoniosulfonyl-methanimidate (Burgess reagent, 0.641 g, 2.691 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-(4-(5-(trifluoromethyl)-1,3,4-oxadiazol-2-yl)benzyl)-N-(3-(trifluoromethyl)phenyl)morpholine-4-carboxamide as Colorless oil (0.600 g, 66.9%).

$^1$H NMR (400 MHz, CDCl$_3$) δ 8.08-8.06 (m, 2H), 7.54-7.36 (m, 5H), 7.28-7.25 (m, 1H), 5.00 (s, 2H), 3.55-3.51 (m, 4H), 3.30-3.27 (m, 4H); LRMS (ES) m/z 501.0 (M$^+$+1).

Example 76. Compound 21406: N-(4-(5-(trifluoromethyl)-1,3,4-oxadiazol-2-yl)benzyl)-N-(4-(trifluoromethyl)phenyl)morpholine-4-carboxamide

[Step 1] Methyl 4-(((4-(trifluoromethyl)phenyl)amino)methyl)benzoate

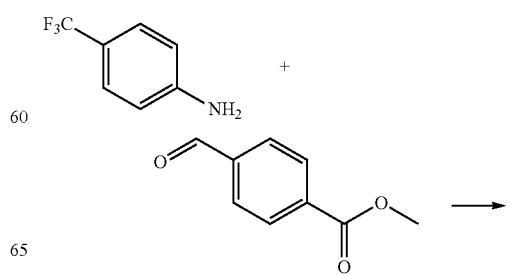

-continued

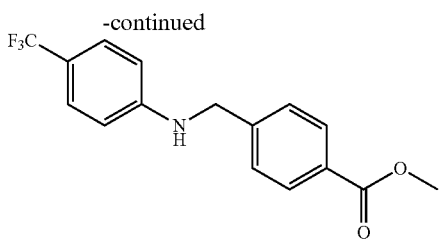

A solution of 4-(trifluoromethyl)aniline (1.000 g, 6.207 mmol), methyl 4-formylbenzoate (1.121 g, 6.827 mmol) and sodium triacetoxyborohydride (1.973 g, 9.310 mmol) in dichloromethane (10 mL) was stirred at the room temperature for 4 hr. Then, water was added to the reaction mixture, followed by extraction with dichloromethane. The organic layer was washed with aqueous saturated sodium chloride solution, dried (anhydrous $MgSO_4$), filtered, and concentrated in vacuo. The concentrate was purified and concentrated by column chromatography ($SiO_2$, 12 g cartridge; ethyl acetate/hexane=0% to 30%) to give the title compound methyl 4-(((4-(trifluoromethyl)phenyl)amino)methyl)benzoate as Colorless oil (0.670 g, 34.9%).

[Step 2] Methyl 4-((N-(4-(trifluoromethyl)phenyl)morpholine-4-carboxamido)methyl)benzoate

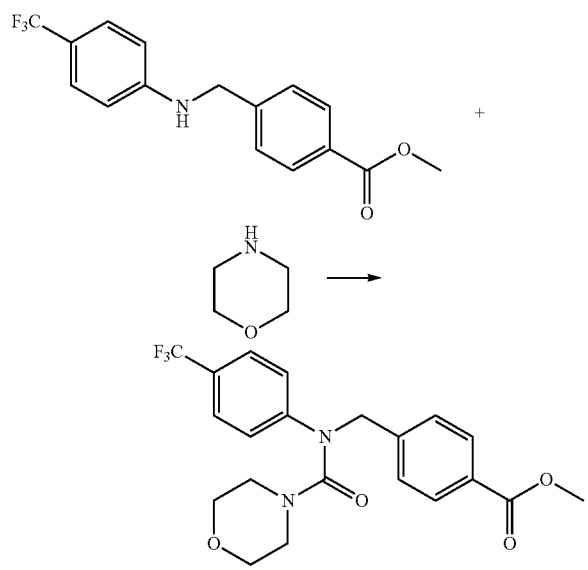

To a stirred solution of methyl 4-(((4-(trifluoromethyl)phenyl)amino)methyl)benzoate (0.670 g, 2.166 mmol) prepared in Step 1 in dichloromethane (10 mL) were added at 0° C. N,N-diisopropylethylamine (1.400 g, 10.831 mmol) and triphosgene (0.514 g, 1.733 mmol). The reaction mixture was stirred at the same temperature for 30 min, treated at the room temperature with morpholine (0.208 g, 2.383 mmol), and stirred for additional 4 hr. Then, water was added to the reaction mixture, followed by extraction with dichloromethane. The organic layer was washed with aqueous saturated sodium chloride solution, dried (anhydrous $MgSO_4$), filtered, and concentrated in vacuo. The concentrate was purified and concentrated by column chromatography ($SiO_2$, 12 g cartridge; ethyl acetate/hexane=0% to 30%) to give the title compound methyl 4-((N-(4-(trifluoromethyl)phenyl)morpholine-4-carboxamido)methyl)benzoate as Colorless oil (0.850 g, 92.9%).

[Step 3] N-(4-(hydrazinecarbonyl)benzyl)-N-(4-(trifluoromethyl)phenyl)morpholine-4-carboxamide

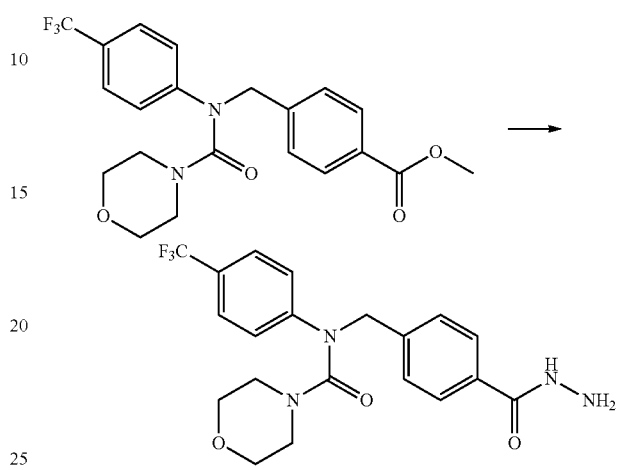

A mixture of methyl 4-((N-(4-(trifluoromethyl)phenyl)morpholine-4-carboxamido)methyl)benzoate (0.859 g, 2.034 mmol) prepared in Step 2 and hydrazine monohydrate (1.921 mL, 40.672 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous $MgSO_4$), filtered, and concentrated in vacuo. The crude product was used without further purification (N-(4-(hydrazinecarbonyl)benzyl)-N-(4-(trifluoromethyl)phenyl)morpholine-4-carboxamide, 0.800 g, 93.1%, Colorless oil).

[Step 4] N-(4-(2-(2,2,2-trifluoroacetyl)hydrazine-1-carbonyl)benzyl)-N-(4-(trifluoromethyl)phenyl)morpholine-4-carboxamide

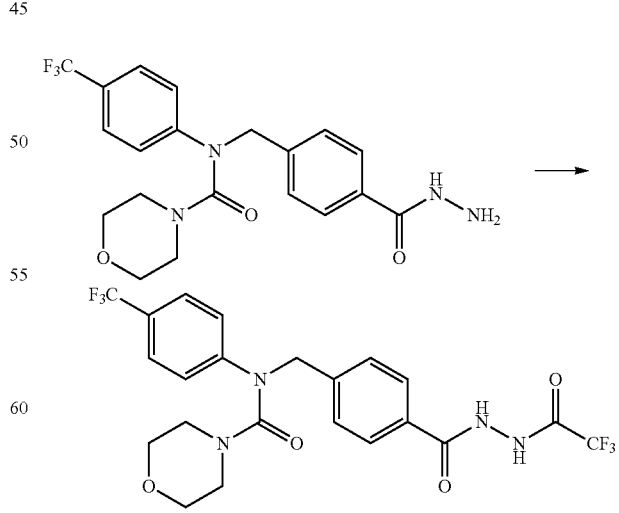

A solution of N-(4-(hydrazinecarbonyl)benzyl)-N-(4-(trifluoromethyl)phenyl)morpholine-4-carboxamide (0.795 g, 1.882 mmol) prepared in Step 3, trifluoroacetic anhydride (0.356 g, 1.694 mmol) and triethylamine (0.286 g, 2.823 mmol) in dichloromethane (10 mL) was stirred at the room temperature for 2 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-(2-(2,2,2-trifluoroacetyl)hydrazine-1-carbonyl)benzyl)-N-(4-(trifluoromethyl)phenyl)morpholine-4-carboxamide as Colorless oil (0.481 g, 49.3%).

[Step 5] Compound 21406

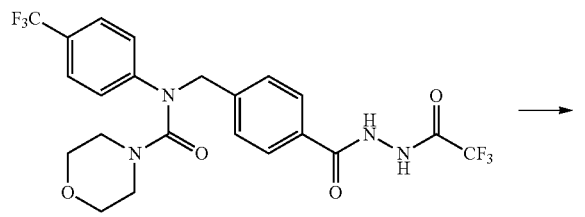

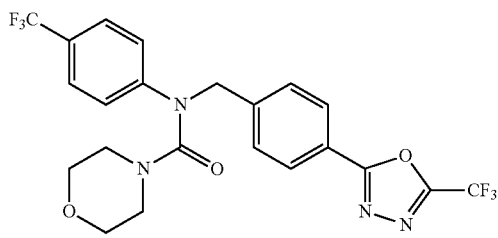

A mixture of N-(4-(2-(2,2,2-trifluoroacetyl)hydrazine-1-carbonyl)benzyl)-N-(4-(trifluoromethyl)phenyl)morpholine-4-carboxamide (0.481 g, 0.928 mmol) prepared in Step 4 and 1-methoxy-N-triethylammoniosulfonyl-methanimidate (Burgess reagent, 0.265 g, 1.113 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-(4-(5-(trifluoromethyl)-1,3,4-oxadiazol-2-yl)benzyl)-N-(4-(trifluoromethyl)phenyl)morpholine-4-carboxamide as Colorless oil (0.210 g, 45.2%).

$^1$H NMR (400 MHz, CDCl$_3$) δ 8.05 (d, 2H, J=8.3 Hz), 7.57 (d, 2H, J=8.8 Hz), 7.50 (d, 2H, J=8.1 Hz), 7.17 (d, 2H, J=8.7 Hz), 5.00 (s, 2H), 3.56-3.54 (m, 4H), 3.31-3.28 (m, 4H); LRMS (ES) m/z 501.0 (M$^+$+1).

Example 77. Compound 21407: N-(3-fluorophenyl)-N-(4-(5-(trifluoromethyl)-1,3,4-oxadiazol-2-yl)benzyl)morpholine-4-carboxamide

[Step 1] N-(3-fluorophenyl)-N-(4-(hydrazinecarbonyl)benzyl)morpholine-4-carboxamide

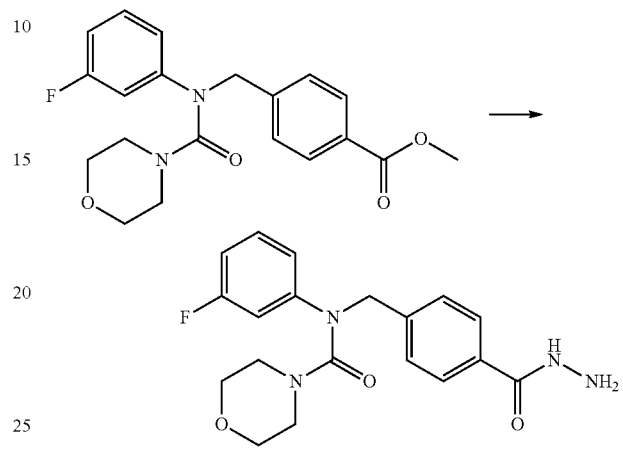

A mixture of methyl 4-((N-(3-fluorophenyl)morpholine-4-carboxamido)methyl)benzoate (0.349 g, 0.937 mmol) and hydrazine monohydrate (0.885 mL, 18.743 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(3-fluorophenyl)-N-(4-(hydrazinecarbonyl)benzyl)morpholine-4-carboxamide, 0.340 g, 97.4%, Colorless oil).

[Step 2] N-(3-fluorophenyl)-N-(4-(2-(2,2,2-trifluoroacetyl)hydrazine-1-carbonyl)benzyl)morpholine-4-carboxamide

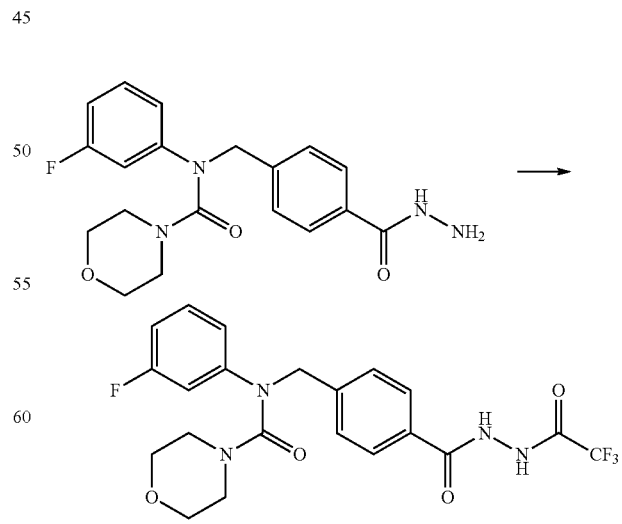

A solution of N-(3-fluorophenyl)-N-(4-(hydrazinecarbonyl)benzyl)morpholine-4-carboxamide (0.306 g, 0.822 mmol) prepared in Step 1, trifluoroacetic anhydride (0.155 g, 0.740 mmol) and triethylamine (0.125 g, 1.233 mmol) in dichloromethane (10 mL) was stirred at the room temperature for 2 hr. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; methanol/dichloromethane=0% to 30%) to give the title compound N-(3-fluorophenyl)-N-(4-(2-(2,2,2-trifluoroacetyl)hydrazine-1-carbonyl)benzyl)morpholine-4-carboxamide as Colorless oil (0.316 g, 82.1%).

[Step 3] Compound 21407

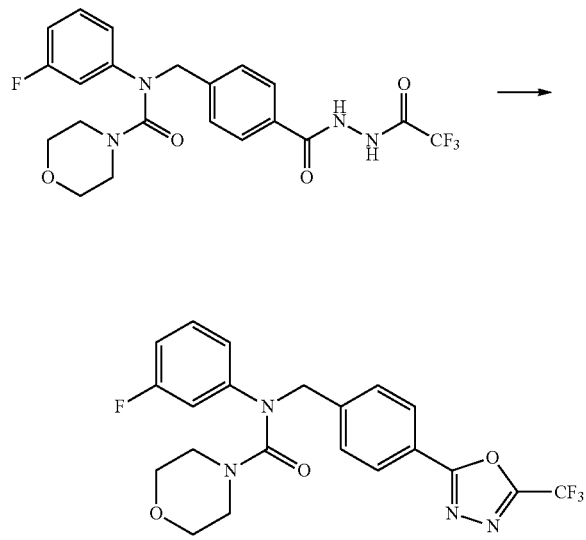

A mixture of N-(3-fluorophenyl)-N-(4-(2-(2,2,2-trifluoroacetyl)hydrazine-1-carbonyl)benzyl)morpholine-4-carboxamide (0.316 g, 0.675 mmol) prepared in Step 2 and 1-methoxy-N-triethylammoniosulfonyl-methanimidate (Burgess reagent, 0.193 g, 0.810 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound N-(3-fluorophenyl)-N-(4-(5-(trifluoromethyl)-1,3,4-oxadiazol-2-yl)benzyl)morpholine-4-carboxamide as Colorless oil (0.200 g, 65.8%).

¹H NMR (400 MHz, CDCl₃) δ 8.05 (d, 2H, J=10.3 Hz), 7.50 (d, 2H, J=8.2 Hz), 7.31-7.25 (m, 1H), 6.88-6.79 (m, 3H), 4.96 (s, 2H), 3.55 (t, 4H, J=4.8 Hz), 3.29 (t, 4H, J=4.8 Hz); LRMS (ES) m/z 451.1 (M⁺+1).

Example 78. Compound 21408: N-(4-(5-(trifluoromethyl)-1,3,4-oxadiazol-2-yl)benzyl)-N-(6-(trifluoromethyl)pyridin-2-yl)morpholine-4-carboxamide

[Step 1] Methyl 4-((N-(6-(trifluoromethyl)pyridin-2-yl)morpholine-4-carboxamido)methyl)benzoate

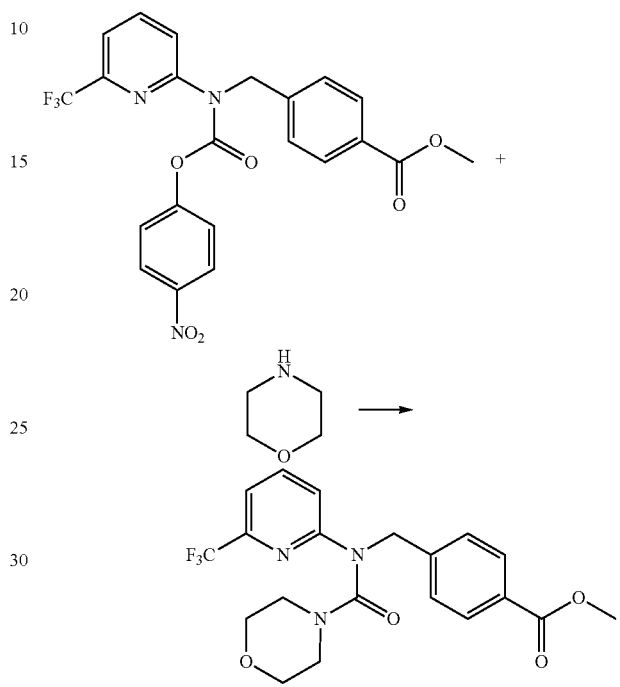

A solution of methyl 4-((((4-nitrophenoxy)carbonyl)(6-(trifluoromethyl)pyridin-2-yl)amino)methyl)benzoate (0.600 g, 1.262 mmol), morpholine (0.546 mL, 6.311 mmol) and potassium carbonate (0.349 g, 2.524 mmol) in N,N-dimethylformamide (10 mL) was stirred at the room temperature for 12 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound methyl 4-((N-(6-(trifluoromethyl)pyridin-2-yl)morpholine-4-carboxamido)methyl)benzoate as Colorless oil (0.450 g, 84.2%).

[Step 2] N-(4-(hydrazinecarbonyl)benzyl)-N-(6-(trifluoromethyl)pyridin-2-yl)morpholine-4-carboxamide

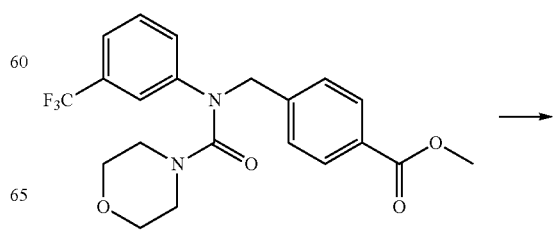

-continued

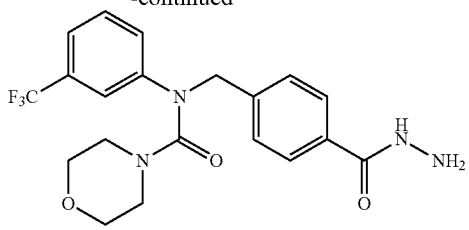

A mixture of methyl 4-((N-(6-(trifluoromethyl)pyridin-2-yl)morpholine-4-carboxamido)methyl)benzoate (0.470 g, 1.110 mmol) prepared in Step 1 and hydrazine monohydrate (1.049 mL, 22.202 mmol) in ethanol (10 mL) was heated at 120° C. for 1 hr under the microwaves, cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(4-(hydrazinecarbonyl)benzyl)-N-(6-(trifluoromethyl)pyridin-2-yl)morpholine-4-carboxamide, 0.462 g, 98.3%, Colorless oil).

[Step 3] N-(4-(2-(2,2,2-trifluoroacetyl)hydrazine-1-carbonyl)benzyl)-N-(6-(trifluoromethyl)pyridin-2-yl)morpholine-4-carboxamide

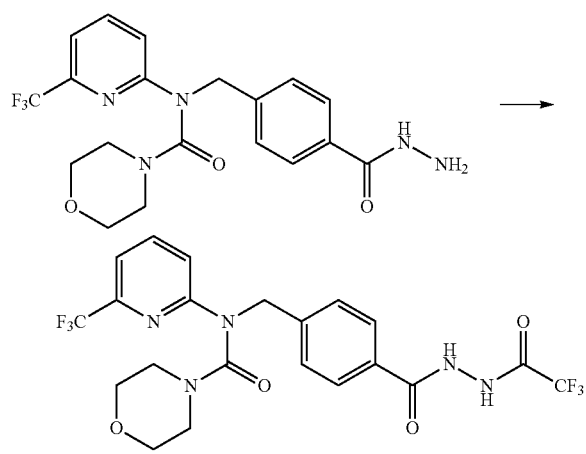

A solution of N-(4-(hydrazinecarbonyl)benzyl)-N-(6-(trifluoromethyl)pyridin-2-yl)morpholine-4-carboxamide (0.462 g, 1.091 mmol) prepared in Step 2, trifluoroacetic anhydride (0.137 mL, 0.982 mmol) and triethylamine (0.227 mL, 1.637 mmol) in dichloromethane (10 mL) was stirred at the room temperature for 3 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-(2-(2,2,2-trifluoroacetyl)hydrazine-1-carbonyl)benzyl)-N-(6-(trifluoromethyl)pyridin-2-yl)morpholine-4-carboxamide as Colorless oil (0.380 g, 98.3%).

[Step 4] Compound 21408

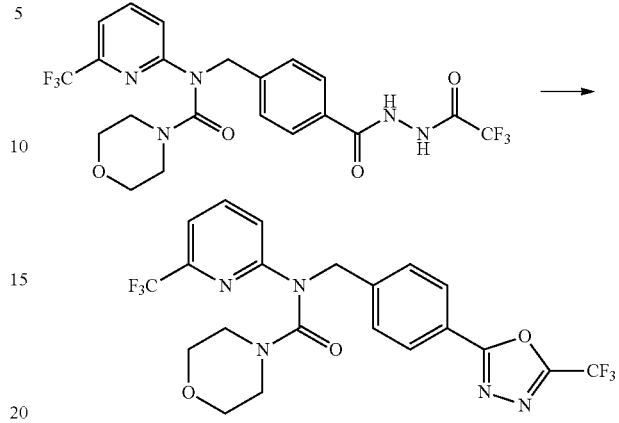

A mixture of N-(4-(2-(2,2,2-trifluoroacetyl)hydrazine-1-carbonyl)benzyl)-N-(6-(trifluoromethyl)pyridin-2-yl)morpholine-4-carboxamide (0.380 g, 0.732 mmol) prepared in Step 3 and 1-methoxy-N-triethylammoniosulfonyl-methanimidate (Burgess reagent, 0.209 g, 0.878 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-(4-(5-(trifluoromethyl)-1,3,4-oxadiazol-2-yl)benzyl)-N-(6-(trifluoromethyl)pyridin-2-yl)morpholine-4-carboxamide as Colorless oil (0.180 g, 49.1%).

$^1$H NMR (400 MHz, CDCl$_3$) δ 8.05-8.02 (m, 2H), 7.73 (t, 1H, J=7.9 Hz), 7.66 (d, 2H, J=8.2 Hz), 7.25 (d, 2H, J=7.4 Hz), 7.06 (d, 2H, J=8.4 Hz), 5.15 (s, 2H), 3.57 (t, 4H, J=4.8 Hz), 3.36 (t, 4H, J=4.8 Hz); LRMS (ES) m/z 502.1 (M$^+$+1).

Example 79. Compound 21409: N-(pyridin-2-yl)-N-(4-(5-(trifluoromethyl)-1,3,4-oxadiazol-2-yl)benzyl)thiomorpholine-4-carboxamide 1,1-dioxide

[Step 1] Methyl 4-((1,1-dioxido-N-(pyridin-2-yl)thiomorpholine-4-carboxamido)methyl)benzoate

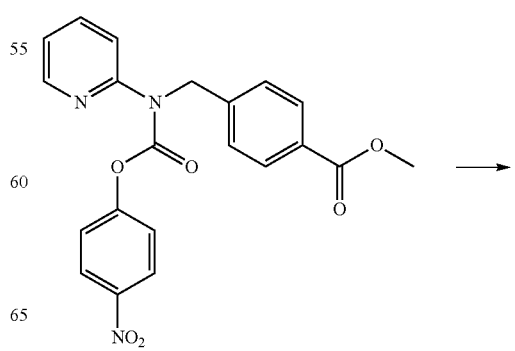

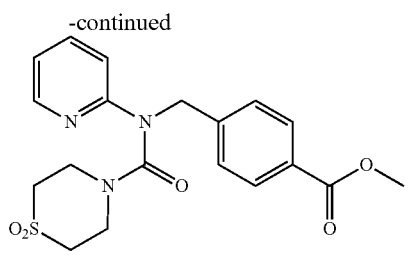

A solution of methyl 4-((((4-nitrophenoxy)carbonyl)(pyridin-2-yl)amino)methyl)benzoate (1.000 g, 2.455 mmol), thiomorpholine 1,1-dioxide (1.659 g, 12.274 mmol) and potassium carbonate (0.679 g, 4.909 mmol) in N,N-dimethylformamide (10 mL) was stirred at 40° C. for 12 hr, and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 24 g cartridge; methanol/dichloromethane=0% to 30%) to give the title compound methyl 4-((1,1-dioxido-N-(pyridin-2-yl)thiomorpholine-4-carboxamido)methyl)benzoate as white foam solid (0.690 g, 69.7%)

[Step 2] N-(4-(hydrazinecarbonyl)benzyl)-N-(pyridin-2-yl)thiomorpholine-4-carboxamide 1,1-dioxide

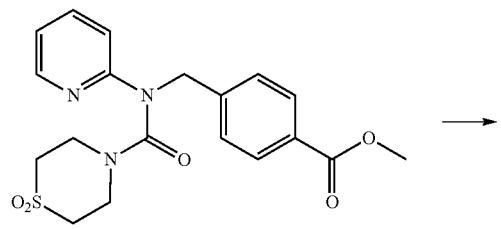

A mixture of methyl 4-((1,1-dioxido-N-(pyridin-2-yl)thiomorpholine-4-carboxamido)methyl)benzoate (0.690 g, 1.710 mmol) prepared in Step 1 and hydrazine monohydrate (1.659 mL, 34.205 mmol) in ethanol (10 mL) was heated at the room temperature for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound N-(4-(hydrazinecarbonyl)benzyl)-N-(pyridin-2-yl)thiomorpholine-4-carboxamide 1,1-dioxide as colorless oil (0.138 g, 20.0%).

[Step 3] N-(pyridin-2-yl)-N-(4-(2-(2,2,2-trifluoroacetyl)hydrazine-1-carbonyl)benzyl)thiomorpholine-4-carboxamide 1,1-dioxide

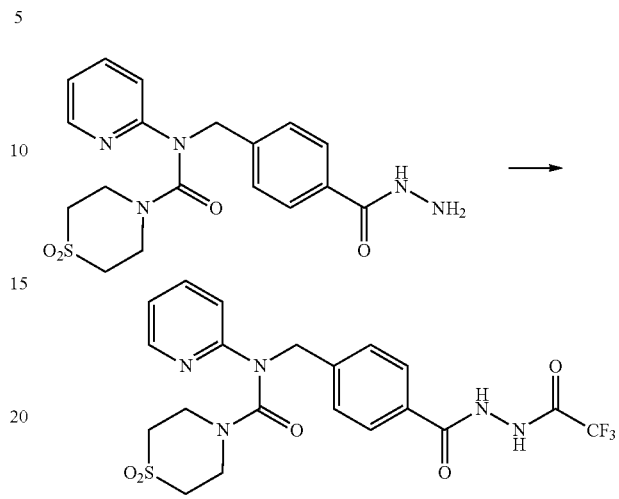

To a stirred solution of N-(4-(hydrazinecarbonyl)benzyl)-N-(pyridin-2-yl)thiomorpholine-4-carboxamide 1,1-dioxide (0.138 g, 0.342 mmol) prepared in Step 2 in dichloromethane (3 mL) was added at 0° C. triethylamine (0.071 mL, 0.513 mmol). The reaction mixture was stirred at the same temperature, treated at the room temperature with trifluoroacetic anhydride (0.043 mL, 0.308 mmol), and stirred for additional 5 hr. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-(pyridin-2-yl)-N-(4-(2-(2,2,2-trifluoroacetyl)hydrazine-1-carbonyl)benzyl)thiomorpholine-4-carboxamide 1,1-dioxide as white foam solid (0.062 g, 36.3%).

[Step 4] Compound 21409

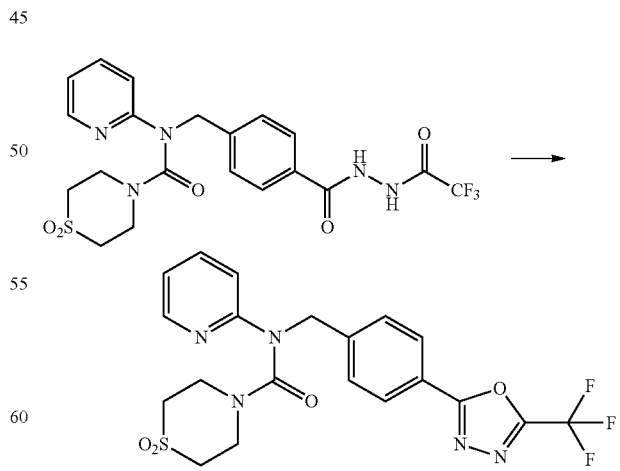

A mixture of N-(pyridin-2-yl)-N-(4-(2-(2,2,2-trifluoroacetyl)hydrazine-1-carbonyl)benzyl)thiomorpholine-4-carboxamide 1,1-dioxide (0.062 g, 0.124 mmol) prepared in Step 3 and 1-methoxy-N-triethylammoniosulfonyl-methanimidate (Burgess reagent, 0.038 g, 0.161 mmol) in tetrahydrofuran (3 mL) was heated at 150° C. for 30 min under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; methanol/dichloromethane=0% to 20%) to give the title compound N-(pyridin-2-yl)-N-(4-(5-(trifluoromethyl)-1,3,4-oxadiazol-2-yl)benzyl)thiomorpholine-4-carboxamide 1,1-dioxide as colorless oil (0.008 g, 13.1%).

¹H NMR (400 MHz, CDCl₃) δ 8.45 (m, 1H), 8.05 (dd, 2H, J=8.2, 1.4 Hz), 7.68 (m, 1H), 7.60 (dd, 2H, J=8.1, 1.2 hz), 7.08 (m, 1H), 7.00 (m, 1H), 3.77 (m, 4H), 2.93 (m, 4H); LRMS (ES) m/z 482.1 (M⁺+H).

Example 80. Compound 21410: N-(2-chloro-4-(5-(trifluoromethyl)-1,3,4-oxadiazol-2-yl)benzyl)-N-phenylthiomorpholine-4-carboxamide 1,1-dioxide

[Step 1] Methyl 3-chloro-4-((1,1-dioxido-N-phenylthiomorpholine-4-carboxamido)methyl)benzoate

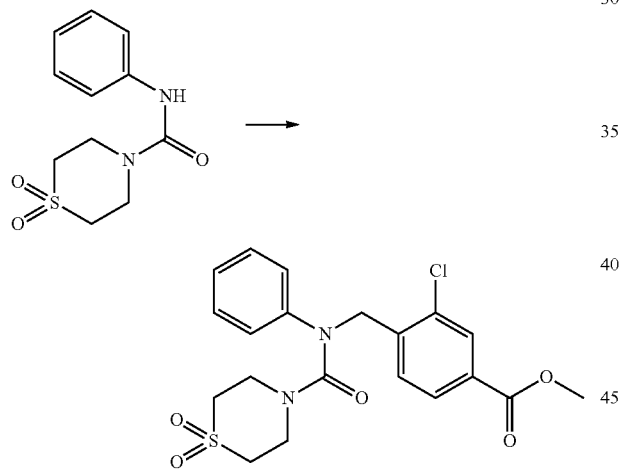

To a stirred solution of N-phenylthiomorpholine-4-carboxamide 1,1-dioxide (1.000 g, 3.932 mmol) in N,N-dimethylformamide (10 mL) was added at 0° C. sodium hydride (60.00%, 0.236 g, 5.899 mmol). The reaction mixture was stirred at the same temperature for 10 min, treated at the room temperature with methyl 4-(bromomethyl)-3-chlorobenzoate (1.347 g, 5.112 mmol), and stirred for additional 12 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 24 g cartridge; ethyl acetate/hexane=10% to 60%) to give the title compound methyl 3-chloro-4-((1,1-dioxido-N-phenylthiomorpholine-4-carboxamido)methyl)benzoate as colorless oil (1.300 g, 75.7%).

[Step 2] N-(2-chloro-4-(hydrazinecarbonyl)benzyl)-N-phenylthiomorpholine-4-carboxamide 1,1-dioxide

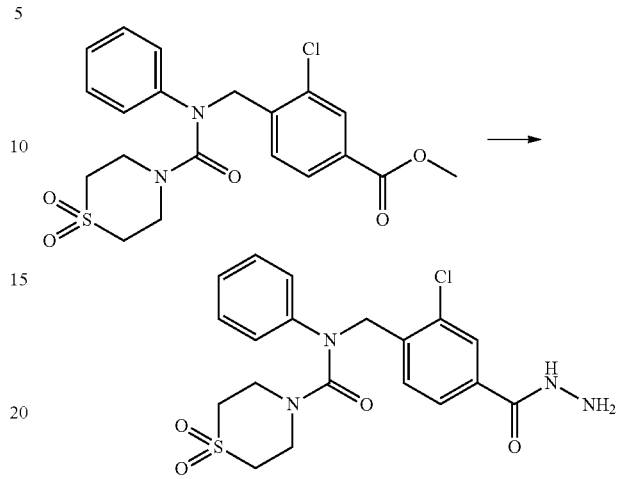

A mixture of methyl 3-chloro-4-((1,1-dioxido-N-phenylthiomorpholine-4-carboxamido)methyl)benzoate (1.300 g, 2.975 mmol) prepared in Step 1 and hydrazine monohydrate (2.892 mL, 59.509 mmol) in ethanol (10 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 40 g cartridge; methanol/dichloromethane=0% to 30%) to give the title compound N-(2-chloro-4-(hydrazinecarbonyl)benzyl)-N-phenylthiomorpholine-4-carboxamide 1,1-dioxide as white foam solid (0.917 g, 70.5%).

[Step 3] N-(2-chloro-4-(2-(2,2,2-trifluoroacetyl)hydrazine-1-carbonyl)benzyl)-N-phenylthiomorpholine-4-carboxamide 1,1-dioxide

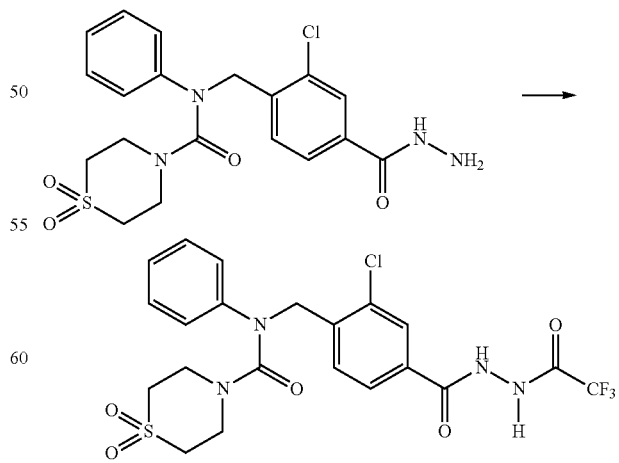

To a stirred solution of N-(2-chloro-4-(hydrazinecarbonyl)benzyl)-N-phenylthiomorpholine-4-carboxamide 1,1- dioxide (0.300 g, 0.687 mmol) prepared in Step 2 in dichloromethane (10 mL) was added at 0° C. triethylamine (0.143 mL, 1.030 mmol). The reaction mixture was stirred at the same temperature, treated at the room temperature with trifluoroacetic anhydride (0.086 mL, 0.618 mmol), and stirred for additional 12 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; methanol/dichloromethane=0% to 10%) to give the title compound N-(2-chloro-4-(2-(2,2,2-trifluoroacetyl)hydrazine-1-carbonyl)benzyl)-N-phenylthiomorpholine-4-carboxamide 1,1-dioxide as white foam solid (0.244 g, 66.7%).

[Step 4] Compound 21410

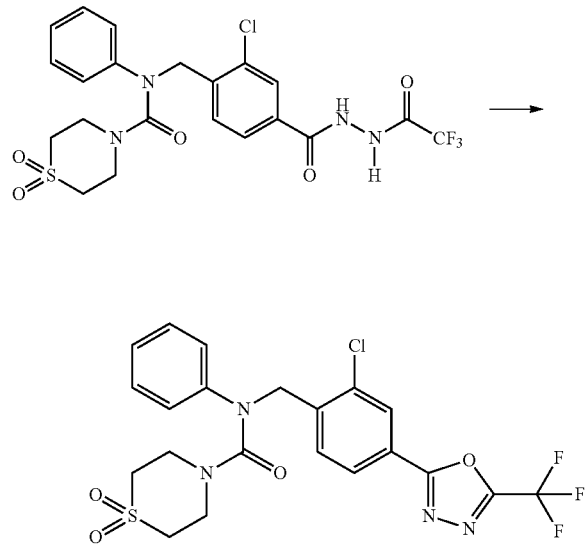 [SMILES: O=C(NNC(=O)C(F)(F)F)c1ccc(CN(C(=O)N2CCS(=O)(=O)CC2)c2ccccc2)c(Cl)c1 ; O=C(N1CCS(=O)(=O)CC1)N(Cc1ccc(-c2nnc(C(F)(F)F)o2)cc1Cl)c1ccccc1]

A mixture of N-(2-chloro-4-(2-(2,2,2-trifluoroacetyl)hydrazine-1-carbonyl)benzyl)-N-phenylthiomorpholine-4-carboxamide 1,1-dioxide (0.244 g, 0.458 mmol) prepared in Step 3 and 1-methoxy-N-triethylammoniosulfonyl-methanimidate (Burgess reagent, 0.142 g, 0.595 mmol) in tetrahydrofuran (5 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; methanol/dichloromethane=0% to 10%) to give the title compound N-(2-chloro-4-(5-(trifluoromethyl)-1,3,4-oxadiazol-2-yl)benzyl)-N-phenylthiomorpholine-4-carboxamide 1,1-dioxide as colorless oil (0.167 g, 70.8%).

$^1$H NMR (400 MHz, DMSO-d$_6$) δ 8.05 (d, 1H, J=1.7 Hz), 8.01 (dd, 1H, J=9.8, 1.7 Hz), 7.72 (d, 1H, J=8.2 Hz), 7.37 (m, 2H), 7.30 (dd, 2H, J=8.6, 1.2 Hz), 7.18 (m, 1H), 4.99 (s, 2H), 3.59 (m, 4H), 2.95 (m, 4H); LRMS (ES) m/z 513.23 (M$^+$+H).

Example 81. Compound 21411: N-(2-chloro-4-(5-(difluoromethyl)-1,3,4-oxadiazol-2-yl)benzyl)-N-phenylthiomorpholine-4-carboxamide 1,1-dioxide

[Step 1] N-(2-chloro-4-(2-(2,2-difluoroacetyl)hydrazine-1-carbonyl)benzyl)-N-phenylthiomorpholine-4-carboxamide 1,1-dioxide

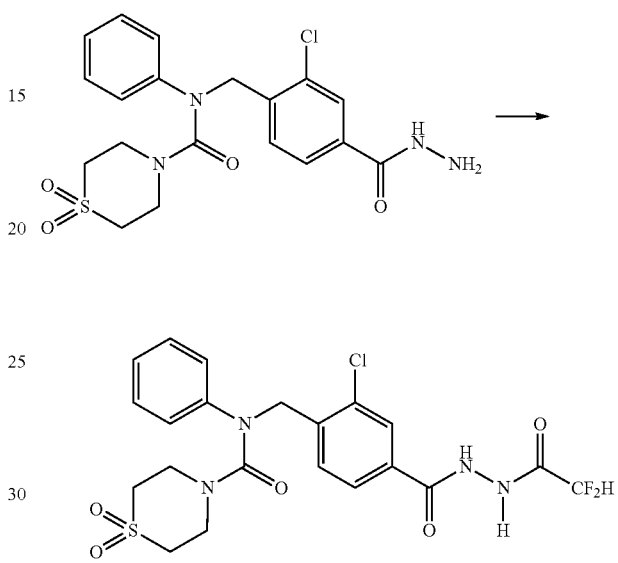

To a stirred solution of N-(2-chloro-4-(hydrazinecarbonyl)benzyl)-N-phenylthiomorpholine-4-carboxamide 1,1-dioxide (0.300 g, 0.687 mmol) prepared in Step 2 of Example 80 in dichloromethane (10 mL) was added at 0° C. triethylamine (0.143 mL, 1.030 mmol). The reaction mixture was stirred at the same temperature, treated at the room temperature with 2,2-difluoroacetic anhydride (0.067 mL, 0.618 mmol), and stirred for additional 12 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; methanol/dichloromethane=0% to 10%) to give the title compound N-(2-chloro-4-(2-(2,2-difluoroacetyl)hydrazine-1-carbonyl)benzyl)-N-phenylthiomorpholine-4-carboxamide 1,1-dioxide as white foam solid (0.171 g, 48.4%).

[Step 2] Compound 21411

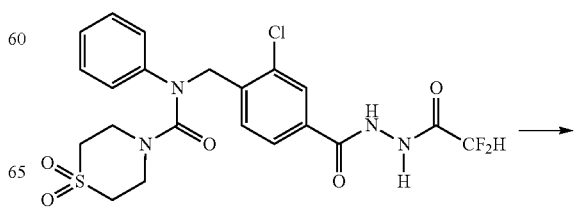

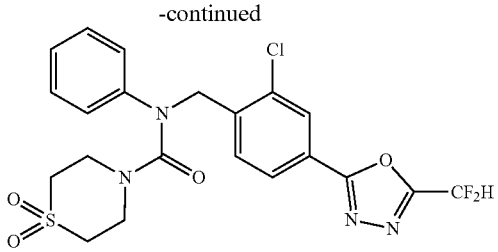

A mixture of N-(2-chloro-4-(2-(2,2-difluoroacetyl)hydrazine-1-carbonyl)benzyl)-N-phenylthiomorpholine-4-carboxamide 1,1-dioxide (0.171 g, 0.332 mmol) prepared in Step 1 and 1-methoxy-N-triethylammoniosulfonyl-methanimidate (Burgess reagent, 0.103 g, 0.432 mmol) in tetrahydrofuran (5 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; methanol/dichloromethane=0% to 10%) to give the title compound N-(2-chloro-4-(5-(difluoromethyl)-1,3,4-oxadiazol-2-yl)benzyl)-N-phenylthiomorpholine-4-carboxamide 1,1-dioxide as colorless oil (0.110 g, 66.7%).

$^1$H NMR (400 MHz, DMSO-d$_6$) δ 8.02 (d, 1H, J=1.7 Hz), 7.99 (dd, 1H, J=8.1, 1.7 Hz), 7.71 (d, 1H, J=8.2 Hz), 7.55 (t, 1H, J=51.3 Hz), 7.38 (m, 2H), 7.30 (dd, 2H, J=8.6, 1.2 Hz), 7.18 (m, 1H); LRMS (ES) m/z 497.37 (M$^+$+H).

Example 82. Compound 21412: N-(4-(5-(trifluoromethyl)-1,3,4-oxadiazol-2-yl)benzyl)-N-(4-(trifluoromethyl)phenyl)thiomorpholine-4-carboxamide 1,1-dioxide

[Step 1] N-(4-(trifluoromethyl)phenyl)thiomorpholine-4-carboxamide 1,1-dioxide

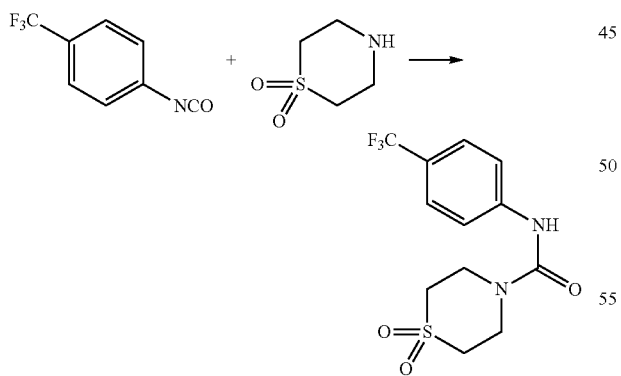

A solution of 1-isocyanato-4-(trifluoromethyl)benzene (0.500 g, 2.672 mmol) and thiomorpholine 1,1-dioxide (0.361 g, 2.672 mmol) in diethylether (10 mL) was stirred at the room temperature for 3 hr. The precipitates were collected by filtration, washed by diethylether, and dried to give the title compound N-(4-(trifluoromethyl)phenyl)thiomorpholine-4-carboxamide 1,1-dioxide as white solid (0.714 g, 82.9%).

[Step 2] Methyl 4-((1,1-dioxido-N-(4-(trifluoromethyl)phenyl)thiomorpholine-4-carboxamido)methyl) benzoate

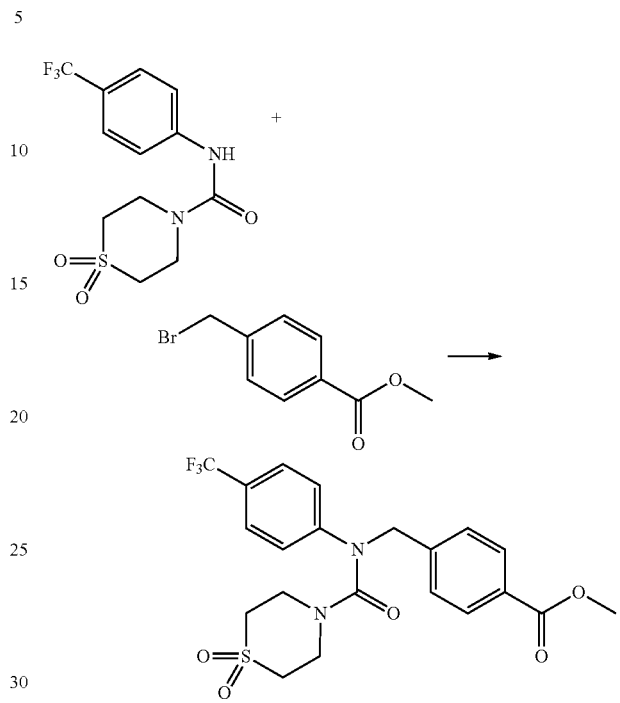

To a stirred solution of N-(4-(trifluoromethyl)phenyl)thiomorpholine-4-carboxamide 1,1-dioxide (0.714 g, 2.215 mmol) prepared in Step 1 in N,N-dimethylformamide (10 mL) was added at 0° C. sodium hydride (60.00%, 0.089 g, 2.215 mmol). The reaction mixture was stirred at the same temperature for 30 min, treated at the room temperature with methyl 4-(bromomethyl)benzoate (0.507 g, 2.215 mmol), and stirred for additional 16 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=30% to 50%) to give the title compound methyl 4-((1,1-dioxido-N-(4-(trifluoromethyl)phenyl)thiomorpholine-4-carboxamido)methyl) benzoate as white foam (0.925 g, 88.8%).

[Step 3] N-(4-(hydrazinecarbonyl)benzyl)-N-(4-(trifluoromethyl)phenyl)thiomorpholine-4-carboxamide 1,1-dioxide

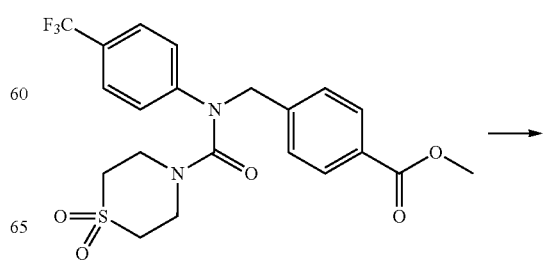

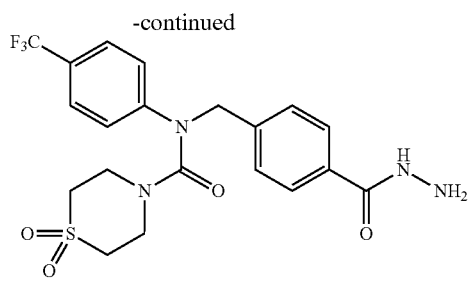

Methyl 4-((1,1-dioxido-N-(4-(trifluoromethyl)phenyl)thiomorpholine-4-carboxamido)methyl) benzoate (0.300 g, 0.638 mmol) prepared in Step 2 and hydrazine monohydrate (0.602 mL, 12.753 mmol) in ethanol (5 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(hydrazinecarbonyl)benzyl)-N-(4-(trifluoromethyl)phenyl)thiomorpholine-4-carboxamide 1,1-dioxide as white solid (0.222 g, 74.0%).

[Step 4] N-(4-(2-(2,2,2-trifluoroacetyl)hydrazine-1-carbonyl)benzyl)-N-(4-(trifluoromethyl)phenyl)thiomorpholine-4-carboxamide 1,1-dioxide

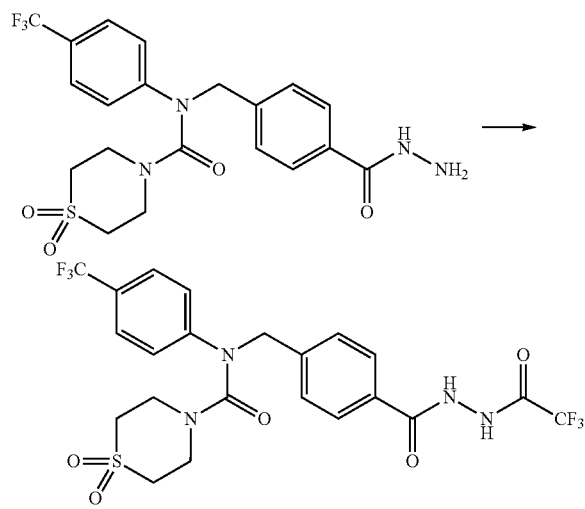

A solution of N-(4-(hydrazinecarbonyl)benzyl)-N-(4-(trifluoromethyl)phenyl)thiomorpholine-4-carboxamide 1,1-dioxide (0.222 g, 0.472 mmol) prepared in Step 3 and triethylamine (0.130 mL, 0.943 mmol) in dichloromethane (2 mL) was mixed at the room temperature with trifluoroacetic anhydride (0.074 mL, 0.424 mmol). The reaction mixture was stirred at the same temperature for 2 hr. Then, water was added to the reaction mixture, followed by extraction with dichloromethane. The bi-phasic mixture was passed through plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(2-(2,2,2-trifluoroacetyl)hydrazine-1-carbonyl)benzyl)-N-(4-(trifluoromethyl)phenyl)thiomorpholine-4-carboxamide 1,1-dioxide as white foam (0.233 g, 87.2%).

[Step 5] Compound 21412

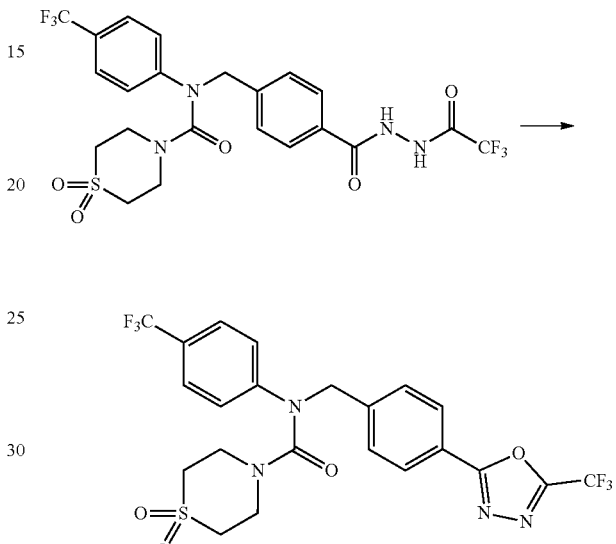

A mixture of N-(4-(2-(2,2,2-trifluoroacetyl)hydrazine-1-carbonyl)benzyl)-N-(4-(trifluoromethyl)phenyl)thiomorpholine-4-carboxamide 1,1-dioxide (0.233 g, 0.411 mmol) prepared in Step 4 and 1-methoxy-N-triethylammoniosulfonyl-methanimidate (Burgess reagent, 0.147 g, 0.617 mmol) in tetrahydrofuran (2 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-(4-(5-(trifluoromethyl)-1,3,4-oxadiazol-2-yl)benzyl)-N-(4-(trifluoromethyl)phenyl)thiomorpholine-4-carboxamide 1,1-dioxide as white solid (0.141 g, 62.5%).

$^1$H NMR (400 MHz, CDCl$_3$) δ 8.07-8.00 (m, 2H), 7.61 (d, 2H, J=8.5 Hz), 7.49-7.42 (m, 2H), 7.20 (d, 2H, J=8.4 Hz), 4.96 (s, 2H), 3.75-3.68 (m, 4H), 2.91 (dd, 4H, J=6.6, 4.0 Hz); LRMS (ESI) m/z 549.45 (M$^+$+H).

Example 83. Compound 21413: N-(4-bromophenyl)-N-(4-(5-(trifluoromethyl)-1,3,4-oxadiazol-2-yl)benzyl)thiomorpholine-4-carboxamide 1,1-dioxide

[Step 1] N-(4-bromophenyl)thiomorpholine-4-carboxamide 1,1-dioxide

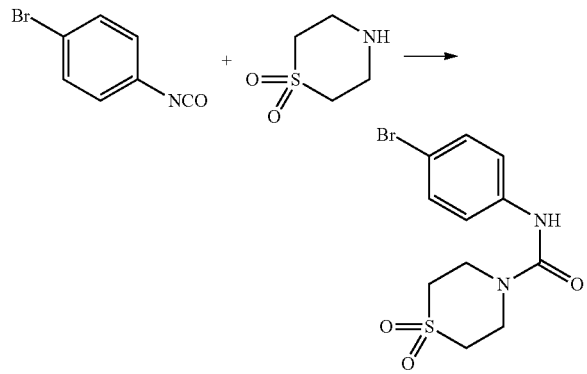

A solution of 1-bromo-4-isocyanatobenzene (2.000 g, 10.100 mmol) and thiomorpholine 1,1-dioxide (1.365 g, 10.100 mmol) in diethylether (10 mL) was stirred at the room temperature for 3 hr. The precipitates were collected by filtration, washed by diethylether, and dried to give the title compound N-(4-bromophenyl)thiomorpholine-4-carboxamide 1,1-dioxide as white solid (3.168 g, 94.1%).

[Step 2] Methyl 4-((N-(4-bromophenyl)-1,1-dioxidothiomorpholine-4-carboxamido)methyl)benzoate

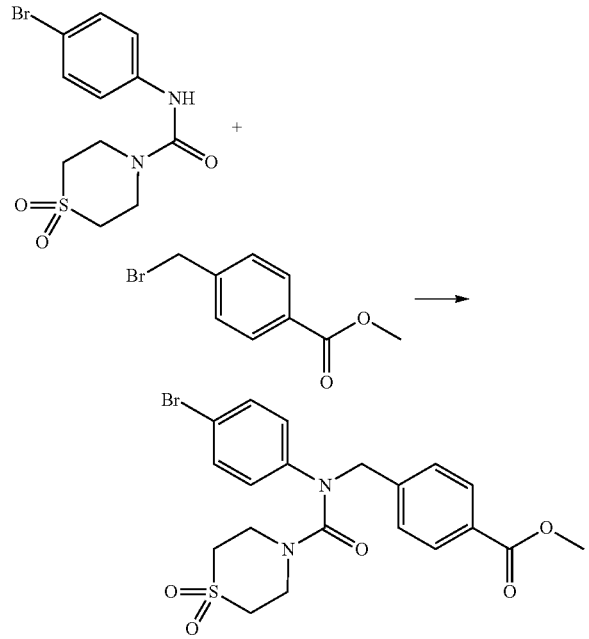

To a stirred solution of N-(4-bromophenyl)thiomorpholine-4-carboxamide 1,1-dioxide (1.000 g, 3.001 mmol) prepared in Step 1 in N,N-dimethylformamide (10 mL) was added at 0° C. sodium hydride (60.00%, 0.120 g, 3.001 mmol). The reaction mixture was stirred at the same temperature for 30 min, treated at the room temperature with methyl 4-(bromomethyl)benzoate (0.687 g, 3.001 mmol), and stirred for additional 16 hr. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=30% to 50%) to give the title compound methyl 4-((N-(4-bromophenyl)-1,1-dioxidothiomorpholine-4-carboxamido)methyl)benzoate as white foam (1.216 g, 84.2%).

[Step 3] N-(4-bromophenyl)-N-(4-(hydrazinecarbonyl)benzyl)thiomorpholine-4-carboxamide 1,1-dioxide

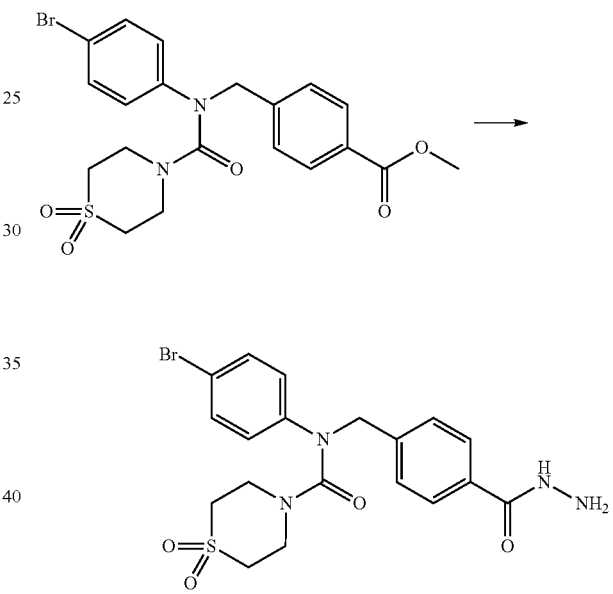

Methyl 4-((N-(4-bromophenyl)-1,1-dioxidothiomorpholine-4-carboxamido)methyl)benzoate (0.300 g, 0.623 mmol) prepared in Step 2 and hydrazine monohydrate (0.589 mL, 12.465 mmol) in ethanol (5 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 3%) to give the title compound N-(4-bromophenyl)-N-(4-(hydrazinecarbonyl)benzyl)thiomorpholine-4-carboxamide 1,1-dioxide as white solid (0.204 g, 67.8%).

401

[Step 4] N-(4-bromophenyl)-N-(4-(2-(2,2,2-trifluoroacetyl)hydrazine-1-carbonyl)benzyl)thiomorpholine-4-carboxamide 1,1-dioxide

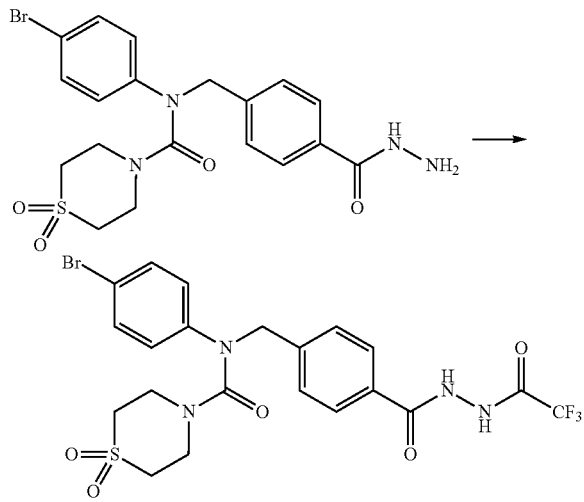

A solution of N-(4-bromophenyl)-N-(4-(hydrazinecarbonyl)benzyl)thiomorpholine-4-carboxamide 1,1-dioxide (0.204 g, 0.423 mmol) prepared in Step 3 and triethylamine (0.117 mL, 0.846 mmol) in dichloromethane (2 mL) was mixed at the room temperature with trifluoroacetic anhydride (0.066 mL, 0.380 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-bromophenyl)-N-(4-(2-(2,2,2-trifluoroacetyl)hydrazine-1-carbonyl)benzyl)thiomorpholine-4-carboxamide 1,1-dioxide as white foam (0.214 g, 87.7%).

[Step 5] Compound 21413

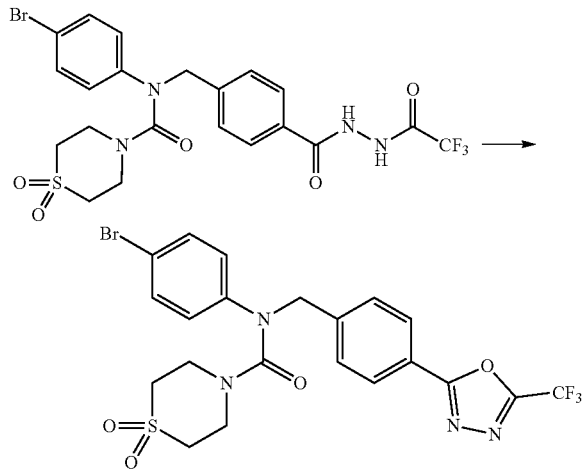

402

A mixture of N-(4-bromophenyl)-N-(4-(2-(2,2,2-trifluoroacetyl)hydrazine-1-carbonyl)benzyl)thiomorpholine-4-carboxamide 1,1-dioxide (0.214 g, 0.371 mmol) prepared in Step 4 and 1-methoxy-N-triethylammoniosulfonyl-methanimidate (Burgess reagent, 0.132 g, 0.556 mmol) in tetrahydrofuran (2 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-bromophenyl)-N-(4-(5-(trifluoromethyl)-1,3,4-oxadiazol-2-yl)benzyl)thiomorpholine-4-carboxamide 1,1-dioxide as white solid (0.178 g, 86.0%).

$^1$H NMR (400 MHz, CDCl$_3$) δ 8.06-7.99 (m, 2H), 7.51-7.40 (m, 4H), 7.00-6.91 (m, 2H), 4.88 (s, 2H), 3.71 (dd, 4H, J=6.8, 3.8 Hz), 2.91-2.83 (m, 4H); LRMS (ESI) m/z 559.16 (M$^+$+H).

Example 84. Compound 21414: N-(2,4-difluorophenyl)-N-(4-(5-(trifluoromethyl)-1,3,4-oxadiazol-2-yl)benzyl)morpholine-4-carboxamide

[Step 1] Methyl 4-(((2,4-difluorophenyl)amino)methyl)benzoate

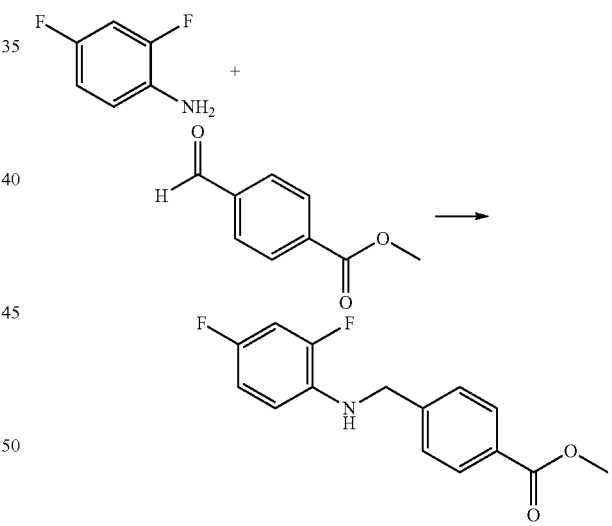

A solution of 2,4-difluoroaniline (0.500 g, 3.873 mmol), methyl 4-formylbenzoate (0.668 g, 4.066 mmol) and sodium triacetoxyborohydride (0.903 g, 4.260 mmol) in dichloromethane (20 mL) was stirred at the room temperature for 6 hr. Then, saturated aqueous sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=5% to 20%) to give the title compound methyl 4-(((2,4-difluorophenyl)amino)methyl)benzoate as light yellow solid (0.496 g, 46.1%).

[Step 2] Methyl 4-((N-(2,4-difluorophenyl)morpholine-4-carboxamido)methyl)benzoate

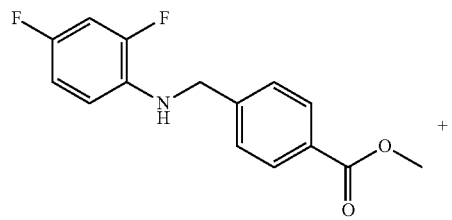

+

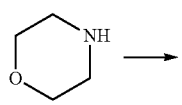

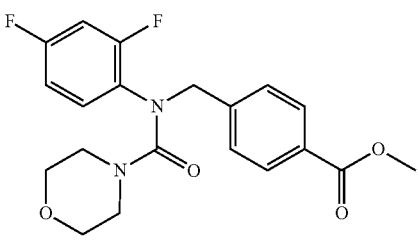

To a stirred solution of methyl 4-(((2,4-difluorophenyl)amino)methyl)benzoate (0.496 g, 1.787 mmol) prepared in Step 1 and N,N-diisopropylethylamine (1.855 mL, 10.722 mmol) in dichloromethane (5 mL) was added at 0° C. triphosgene (0.265 g, 0.894 mmol). The reaction mixture was stirred at the same temperature for 30 min, treated at the room temperature with Morpholine (0.172 mL, 1.966 mmol), and stirred for additional 16 hr. The reaction mixture was concentrated under the reduced pressure to remove the solvent, and saturated aqueous ammonium chloride solution was added to the concentrate, followed by extraction with dichloromethane. The organic layer was washed with brine, dried (anhydrous $MgSO_4$), filtered, and concentrated in vacuo. The concentrate was purified and concentrated by column chromatography ($SiO_2$, 12 g cartridge; ethyl acetate/hexane=20% to 50%) to give the title compound methyl 4-((N-(2,4-difluorophenyl)morpholine-4-carboxamido)methyl)benzoate as yellow solid (0.618 g, 88.6%).

[Step 3] N-(2,4-difluorophenyl)-N-(4-(hydrazinecarbonyl)benzyl)morpholine-4-carboxamide

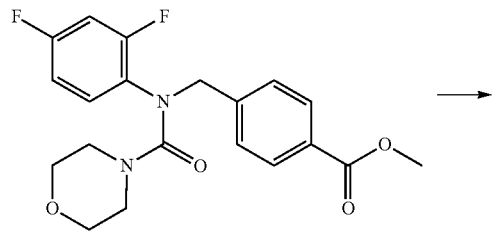

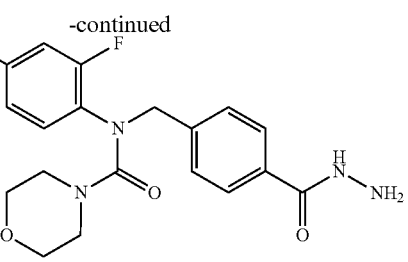

Methyl 4-((N-(2,4-difluorophenyl)morpholine-4-carboxamido)methyl)benzoate (0.300 g, 0.768 mmol) prepared in Step 2 and hydrazine monohydrate (0.726 mL, 15.369 mmol) in ethanol (5 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 3%) to give the title compound N-(2,4-difluorophenyl)-N-(4-(hydrazinecarbonyl)benzyl)morpholine-4-carboxamide as colorless oil (0.253 g, 84.3%).

[Step 4] N-(2,4-difluorophenyl)-N-(4-(2-(2,2,2-trifluoroacetyl)hydrazine-1-carbonyl)benzyl)morpholine-4-carboxamide

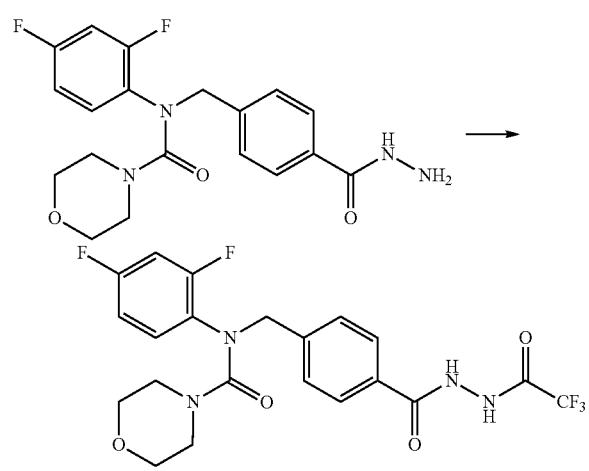

A solution of N-(2,4-difluorophenyl)-N-(4-(hydrazinecarbonyl)benzyl)morpholine-4-carboxamide (0.253 g, 0.648 mmol) prepared in Step 3 and triethylamine (0.179 mL, 1.296 mmol) in dichloromethane (2 mL) was mixed at the room temperature with trifluoroacetic anhydride (0.101 mL, 0.583 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 5%) to give the title compound N-(2,4-difluorophenyl)-N-(4-(2-(2,2,2-trifluoroacetyl)hydrazine-1-carbonyl)benzyl)morpholine-4-carboxamide as white foam (0.228 g, 72.2%).

[Step 5] Compound 21414

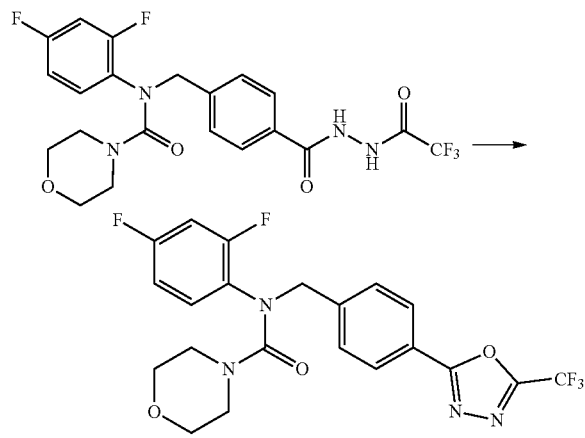

A mixture of N-(2,4-difluorophenyl)-N-(4-(2-(2,2,2-trifluoroacetyl)hydrazine-1-carbonyl)benzyl)morpholine-4-carboxamide (0.228 g, 0.468 mmol) prepared in Step 4 and 1-methoxy-N-triethylammoniosulfonyl-methanimidate (Burgess reagent, 0.167 g, 0.702 mmol) in tetrahydrofuran (2 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=3%) to give the title compound N-(2,4-difluorophenyl)-N-(4-(5-(trifluoromethyl)-1,3,4-oxadiazol-2-yl)benzyl)morpholine-4-carboxamide as white foam (0.182 g, 82.9%).

$^1$H NMR (400 MHz, CDCl$_3$) δ 8.05 (d, 2H, J=8.3 Hz), 7.48 (d, 2H, J=8.1 Hz), 6.65-6.50 (m, 3H), 4.94 (s, 2H), 3.61-3.54 (m, 4H), 3.35-3.28 (m, 4H); LRMS (ESI) m/z 469.11 (M$^+$+H).

Example 85. Compound 21415: N-(2-fluoro-4-methylphenyl)-N-(4-(5-(trifluoromethyl)-1,3,4-oxadiazol-2-yl)benzyl)morpholine-4-carboxamide

[Step 1] Methyl 4-4-(2-fluoro-4-methylphenyl)amino)methyl)benzoate

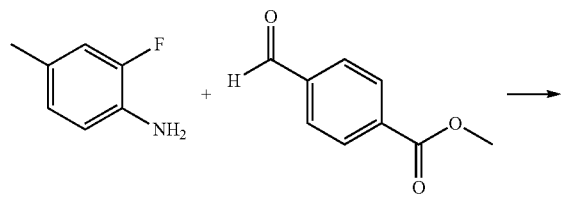

-continued

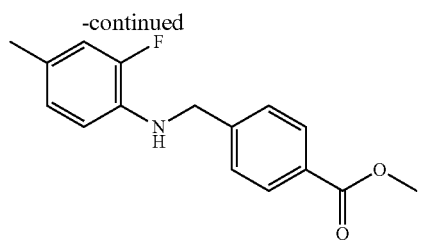

A solution of 2-fluoro-4-methylaniline (0.500 g, 3.995 mmol), methyl 4-formylbenzoate (0.689 g, 4.195 mmol) and sodium triacetoxyborohydride (0.931 g, 4.395 mmol) in dichloromethane (20 mL) was stirred at the room temperature for 6 hr. Then, saturated aqueous sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=5% to 20%) to give the title compound methyl 4-(((2-fluoro-4-methylphenyl)amino)methyl)benzoate as light yellow solid (0.748 g, 68.5%).

[Step 2] Methyl 4-((N-(2-fluoro-4-methylphenyl)morpholine-4-carboxamido)methyl)benzoate

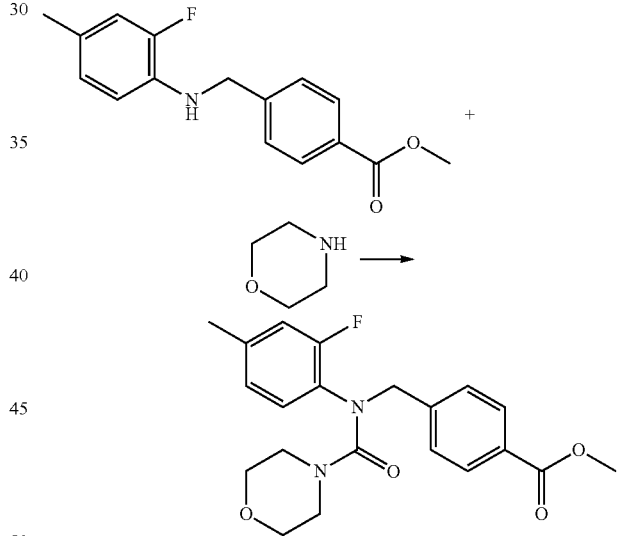

To a stirred solution of methyl 4-(((2-fluoro-4-methylphenyl)amino)methyl)benzoate (0.748 g, 2.738 mmol) prepared in Step 1 and N,N-diisopropylethylamine (2.843 mL, 16.430 mmol) in dichloromethane (5 mL) was added at 0° C. triphosgene (0.406 g, 1.369 mmol). The reaction mixture was stirred at the same temperature for 30 min, treated at the room temperature with Morpholine (0.263 mL, 3.012 mmol), and stirred for additional 16 hr. The reaction mixture was concentrated under the reduced pressure to remove the solvent, and saturated aqueous ammonium chloride solution was added to the concentrate, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=20% to 50%) to give the title compound methyl 4-((N-(2-fluoro-4-methylphenyl)morpholine-4-carboxamido)methyl)benzoate as yellow solid (0.618 g, 58.4%).

[Step 3] N-(2-fluoro-4-methylphenyl)-N-(4-(hydrazinecarbonyl)benzyl)morpholine-4-carboxamide

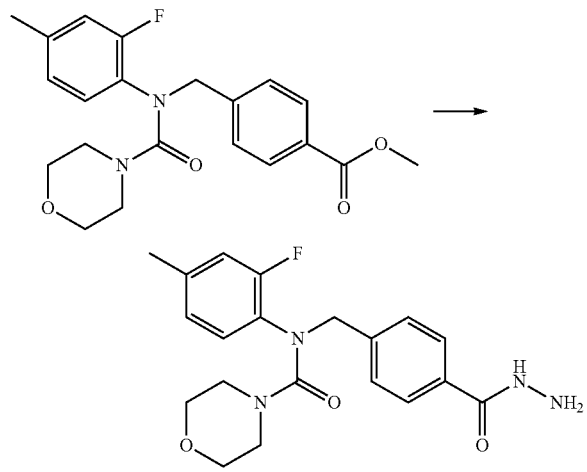

Methyl 4-((N-(4-fluoro-2-methylphenyl)morpholine-4-carboxamido)methyl)benzoate (0.300 g, 0.776 mmol) prepared in Step 2 and hydrazine monohydrate (0.733 mL, 15.527 mmol) in ethanol (5 mL) was mixed at the room temperature and then heated at 100° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(2-fluoro-4-methylphenyl)-N-(4-(hydrazinecarbonyl)benzyl)morpholine-4-carboxamide as white foam (0.257 g, 85.8%).

[Step 4] N-(2-fluoro-4-methylphenyl)-N-(4-(2-(2,2,2-trifluoroacetyl)hydrazine-1-carbonyl)benzyl) morpholine-4-carboxamide

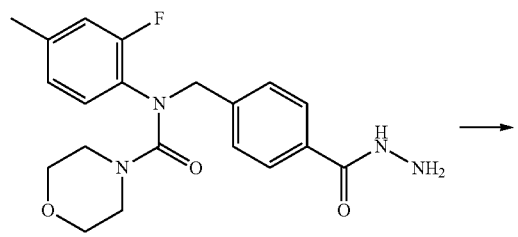

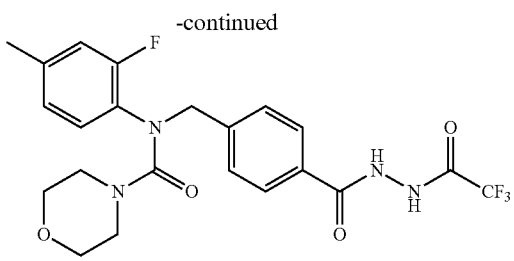

A solution of N-(4-fluoro-2-methylphenyl)-N-(4-(hydrazinecarbonyl)benzyl)morpholine-4-carboxamide (0.257 g, 0.666 mmol) prepared in Step 4 and triethylamine (0.184 mL, 1.332 mmol) in dichloromethane (2 mL) was mixed at the room temperature with trifluoroacetic anhydride (0.104 mL, 0.599 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-methylphenyl)-N-(4-(2-(2,2,2-trifluoroacetyl)hydrazine-1-carbonyl)benzyl)morpholine-4-carboxamide as white foam (0.323 g, 100.6%).

[Step 5] Compound 21415

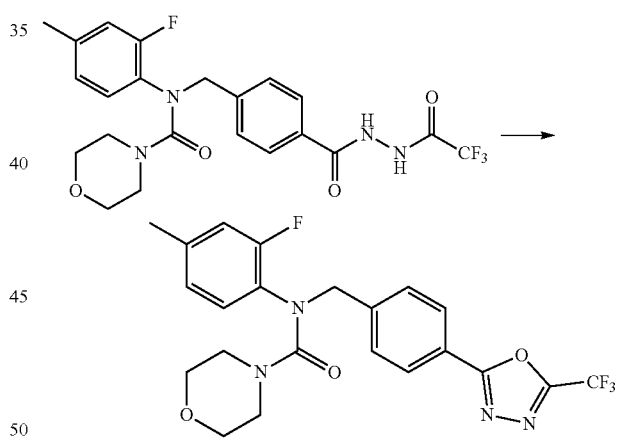

A solution of N-(4-fluoro-2-methylphenyl)-N-(4-(2-(2,2,2-trifluoroacetyl)hydrazine-1-carbonyl)benzyl) morpholine-4-carboxamide (0.323 g, 0.670 mmol) prepared in Step 4 and 1-methoxy-N-triethylammoniosulfonyl-methanimidate (Burgess reagent, 0.239 g, 1.004 mmol) in dichloromethane (10 mL) was stirred at the room temperature for 1 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound N-(2-fluoro-4-methylphenyl)-N-(4-(5-(trifluoromethyl)-1,3,4-oxadiazol-2-yl)benzyl)morpholine-4-carboxamide as white foam (0.219 g, 70.4%).

$^1$H NMR (400 MHz, CDCl$_3$) δ 8.03-7.95 (m, 2H), 7.55-7.47 (m, 2H), 6.95-6.82 (m, 3H), 4.79 (s, 2H), 3.49-3.41 (m, 4H), 3.24-3.17 (m, 4H), 2.31 (s, 3H); LRMS (ESI) m/z 465.03 (M$^+$+H).

Example 86. Compound 21416: Ten-butyl 7-(phenyl(4-(5-(trifluoromethyl)-1,3,4-oxadiazol-2-yl)benzyl)carbamoyl)-2,7-diazaspiro[3.5]nonane-2-carboxylate

[Step 1] Tert-butyl 7-((4-(methoxycarbonyl)benzyl)(phenyl)carbamoyl)-2,7-diazaspiro[3.5]nonane-2-carboxylate

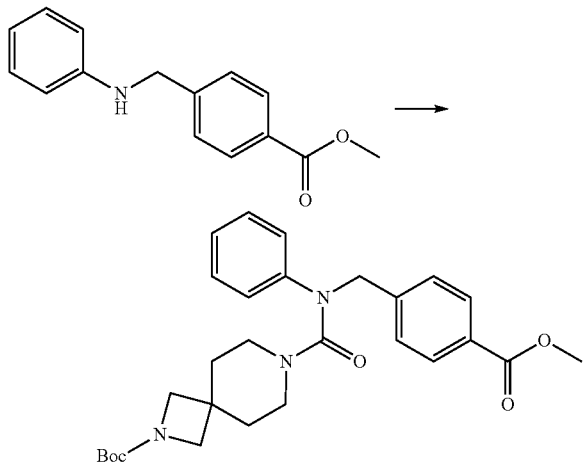

A solution of methyl 4-((phenylamino)methyl)benzoate (2.000 g, 8.289 mmol), tert-butyl 2,7-diazaspiro[3.5]nonane-2-carboxylate (1.876 g, 8.289 mmol), triphosgene (1.968 g, 6.631 mmol) and N,N-diisopropylethylamine (7.238 mL, 41.444 mmol) in dichloromethane (50 mL) was stirred at 0° C. for 30 min and then for additional 3 hr at the room temperature. Then, saturated aqueous sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 40 g cartridge; ethyl acetate/hexane=0% to 30%) to give the title compound tert-butyl 7-((4-(methoxycarbonyl)benzyl)(phenyl)carbamoyl)-2,7-diazaspiro[3.5]nonane-2-carboxylate as orange solid (3.600 g, 88.0%).

[Step 2] Tert-butyl 7-((4-(hydrazinecarbonyl)benzyl)(phenyl)carbamoyl)-2,7-diazaspiro[3.5]nonane-2-carboxylate

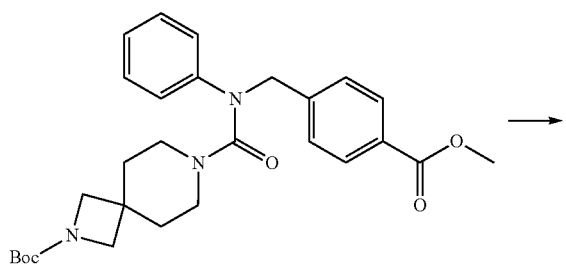

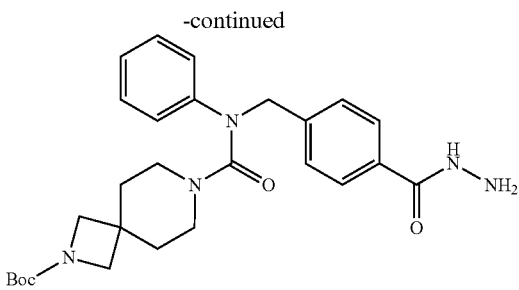

Tert-butyl 7-((4-(methoxycarbonyl)benzyl)(phenyl)carbamoyl)-2,7-diazaspiro[3.5]nonane-2-carboxylate (3.600 g, 7.293 mmol) prepared in Step 1 and hydrazine monohydrate (7.085 mL, 145.867 mmol) in ethanol (40 mL) was mixed at the room temperature and then heated at 120° C. under the microwaves for 2 hr, and cooled down to the room temperature to terminate the reaction. The reaction mixture was concentrated under the reduced pressure to remove the solvent, and water was added to the concentrate, followed by extraction with ethyl acetate. The organic layer was washed with brine, dried (anhydrous MgSO$_4$), filtered, and concentrated in vacuo. The title compound tert-butyl 7-((4-(hydrazinecarbonyl)benzyl)(phenyl)carbamoyl)-2,7-diazaspiro[3.5]nonane-2-carboxylate was used without further purification (3.600 g, 100.0%, white solid).

[Step 3] Tert-butyl 7-(phenyl(4-(2-(2,2,2-trifluoroacetyl)hydrazine-1-carbonyl)benzyl)carbamoyl)-2,7-diazaspiro[3.5]nonane-2-carboxylate

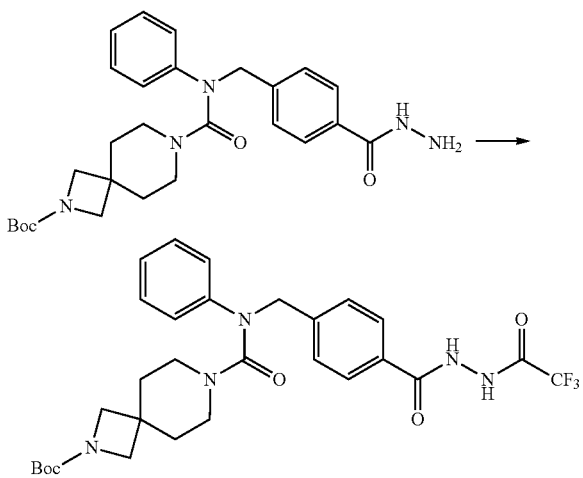

A solution of tert-butyl 7-((4-(hydrazinecarbonyl)benzyl)(phenyl)carbamoyl)-2,7-diazaspiro[3.5]nonane-2-carboxylate (3.600 g, 7.293 mmol) prepared in Step 2 and triethylamine (1.516 mL, 10.940 mmol) in dichloromethane (100 mL) was mixed at the room temperature with trifluoroacetic anhydride (0.816 mL, 6.564 mmol). The reaction mixture was stirred at the same temperature for 3 hr. Then, saturated aqueous sodium bicarbonate solution was added to the reaction mixture, followed by extraction with dichloromethane. The organic layer was washed with brine, dried (anhydrous MgSO$_4$), filtered, and concentrated in vacuo. The concentrate was purified and concentrated by column chromatography (SiO$_2$, 40 g cartridge; methanol/dichloromethane=0% to 10%) to give the title compound tert-butyl 7-(phenyl(4-(2-(2,2,2-trifluoroacetyl)hydrazine-1-carbonyl)benzyl)carbamoyl)-2,7-diazaspiro[3.5]nonane-2-carboxylate as white solid (1.710 g, 39.8%).

[Step 4] Compound 21416

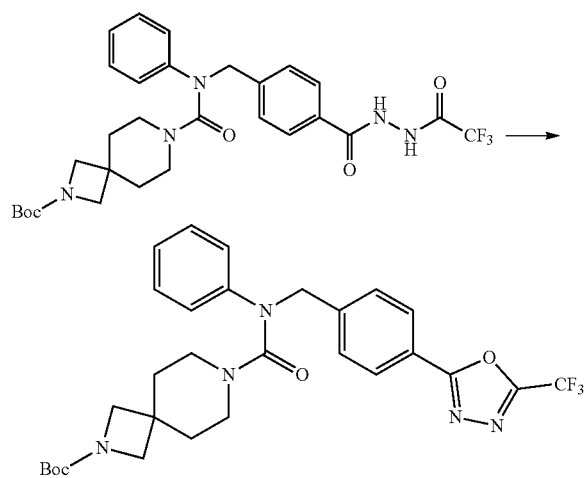

Tert-butyl 7-(phenyl(4-(2-(2,2,2-trifluoroacetyl)hydrazine-1-carbonyl)benzyl)carbamoyl)-2,7-diazaspiro[3.5]nonane-2-carboxylate (1.710 g, 2.900 mmol) prepared in Step 3 and 1-methoxy-N-triethylammoniosulfonyl-methanimidate (Burgess reagent, 1.037 g, 4.350 mmol) in tetrahydrofuran (40 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=10% to 60%) to give the title compound tert-butyl 7-(phenyl(4-(5-(trifluoromethyl)-1,3,4-oxadiazol-2-yl)benzyl)carbamoyl)-2,7-diazaspiro[3.5]nonane-2-carboxylate as white solid (1.230 g, 74.2%).

$^1$H NMR (400 MHz, CDCl$_3$) δ 8.03 (d, 2H, J=8.4 Hz), 7.50 (d, 2H, J=8.5 Hz), 7.31 (t, 2H, J=7.9 Hz), 7.13 (t, 1H, J=7.4 Hz), 7.07-7.05 (m, 2H), 4.93 (s, 2H), 3.58 (s, 4H), 3.20 (t, 4H, J=5.5 Hz), 1.55 (t, 4H, J=5.5 Hz), 1.43 (s, 9H), 7.13 (t, 1H, J=7.4 Hz).

Example 87. Compound 21417: N-phenyl-N-(4-(5-(trifluoromethyl)-1,3,4-oxadiazol-2-yl)benzyl)-2,7-diazaspiro[3.5]nonane-7-carboxamide

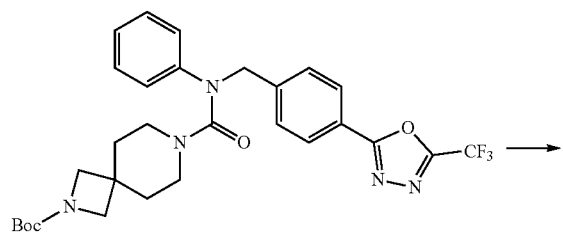

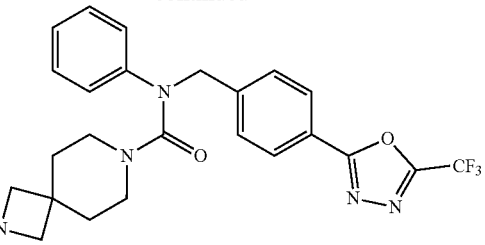

A solution of tert-butyl 7-(phenyl(4-(5-(trifluoromethyl)-1,3,4-oxadiazol-2-yl)benzyl)carbamoyl)-2,7-diazaspiro[3.5]nonane-2-carboxylate (1.230 g, 2.152 mmol) prepared in Example 86 and TFA (4.943 mL, 64.556 mmol) in dichloromethane (40 mL) was stirred at the room temperature for 17 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 20%) to give the title compound N-phenyl-N-(4-(5-(trifluoromethyl)-1,3,4-oxadiazol-2-yl)benzyl)-2,7-diazaspiro[3.5]nonane-7-carboxamide as pale yellow oil (0.600 g, 59.1%).

$^1$H NMR (400 MHz, CDCl$_3$) δ 9.64 (brs, 1H), 8.00 (d, 2H, J=8.3 Hz), 7.45 (d, 2H, J=8.3 Hz), 7.29 (t, 2H, J=7.8 Hz), 7.13 (t, 1H, J=7.4 Hz), 7.02 (d, 2H, J=7.6 Hz), 4.89 (s, 2H), 3.71-3.66 (m, 4H), 3.15-3.13 (m, 4H), 1.65-1.62 (m, 4H); LRMS (ES) m/z 472.2 (M$^+$+1).

Example 88. Compound 21418: 2-Acetyl-N-phenyl-N-(4-(5-(trifluoromethyl)-1,3,4-oxadiazol-2-yl)benzyl)-2,7-diazaspiro[3.5]nonane-7-carboxamide

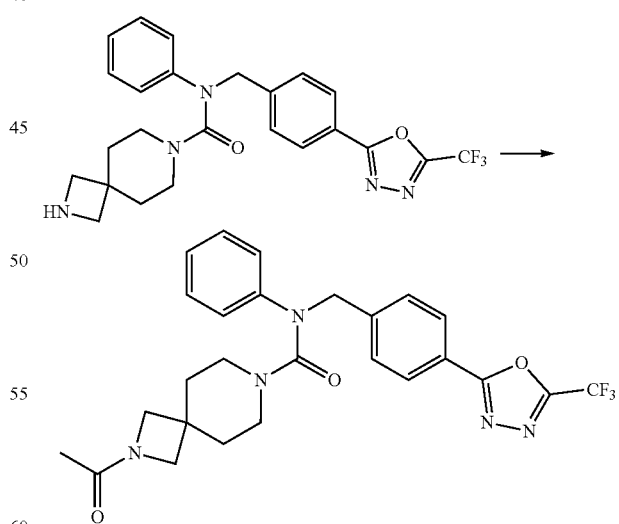

A solution of N-phenyl-N-(4-(5-(trifluoromethyl)-1,3,4-oxadiazol-2-yl)benzyl)-2,7-diazaspiro[3.5]nonane-7-carboxamide (0.150 g, 0.318 mmol) prepared in Example 87 and triethylamine (0.089 mL, 0.636 mmol) in dichloromethane (4 mL) was mixed at 0° C. with acetyl chloride (0.034 mL, 0.477 mmol). The reaction mixture was stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound 2-acetyl-N-phenyl-N-(4-(5-(trifluoromethyl)-1,3,4-oxadiazol-2-yl)benzyl)-2,7-diazaspiro[3.5]nonane-7-carboxamide as yellow solid (0.114 g, 69.8%).

$^1$H NMR (400 MHz, CDCl$_3$.) δ 8.01 (d, 2H, J=8.3 Hz), 7.47 (d, 2H, J=8.3 Hz), 7.30 (t, 2H, J=7.9 Hz), 7.12 (t, 1H, J=7.4 Hz), 7.05 (d, 2H, J=8.6 Hz), 4.91 (s, 2H), 3.68 (s, 4H), 3.19-3.18 (m, 4H), 1.85 (s, 3H), 1.55 (t, 4H, J=5.5 Hz); LRMS (ES) m/z 514.1 (M$^+$+1).

Example 89. Compound 21419: 2-(Methylsulfonyl)-N-phenyl-N-(4-(5-(trifluoromethyl)-1,3,4-oxadiazol-2-yl)benzyl)-2,7-diazaspiro[3.5]nonane-7-carboxamide

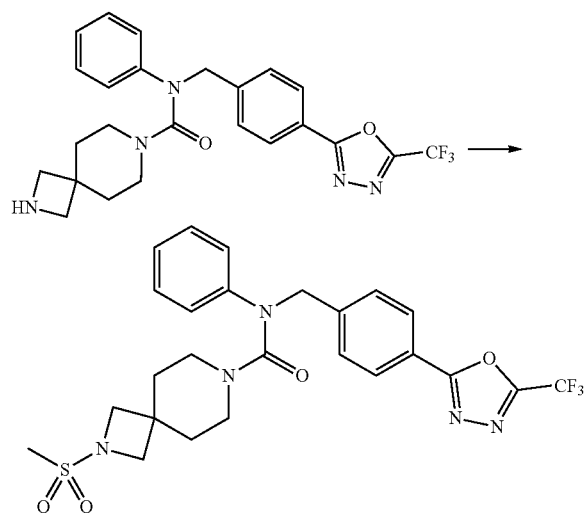

A solution of N-phenyl-N-(4-(5-(trifluoromethyl)-1,3,4-oxadiazol-2-yl)benzyl)-2,7-diazaspiro[3.5]nonane-7-carboxamide (0.150 g, 0.318 mmol) prepared in Example 87 and triethylamine (0.088 mL, 0.636 mmol) in dichloromethane (4 mL) was mixed at 0° C. with methanesulfonyl chloride (0.037 mL, 0.477 mmol). The reaction mixture was stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 60%) to give the title compound 2-(methylsulfonyl)-N-phenyl-N-(4-(5-(trifluoromethyl)-1,3,4-oxadiazol-2-yl)benzyl)-2,7-diazaspiro[3.5]nonane-7-carboxamide as white solid (0.097 g, 55.5%).

$^1$H NMR (400 MHz, CDCl$_3$) δ 8.01 (d, 2H, J=8.3 Hz), 7.47 (d, 2H, J=8.2 Hz), 7.30 (t, 2H, J=7.9 Hz), 7.12 (t, 1H, J=7.4 Hz), 7.04 (d, 2H, J=7.6 Hz), 4.91 (s, 2H), 3.59 (s, 4H), 3.18 (t, 4H, J=5.5 Hz), 2.82 (s, 3H), 1.58 (t, 4H, J=5.5 Hz); LRMS (ES) m/z 550.4 (M$^+$+1).

Example 90. Compound 21420: 2-Methyl-N-phenyl-N-(4-(5-(trifluoromethyl)-1,3,4-oxadiazol-2-yl)benzyl)-2,7-diazaspiro[3.5]nonane-7-carboxamide

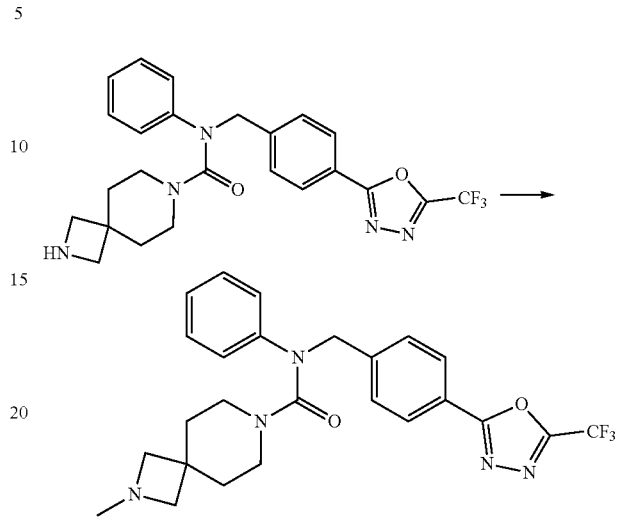

A solution of N-phenyl-N-(4-(5-(trifluoromethyl)-1,3,4-oxadiazol-2-yl)benzyl)-2,7-diazaspiro[3.5]nonane-7-carboxamide (0.150 g, 0.318 mmol) prepared in Example 87 and formaldehyde (37.00% solution in water, 0.036 mL, 0.477 mmol) in dichloromethane (4 mL) was stirred at the room temperature for 30 min, and mixed with sodium triacetoxyborohydride (0.135 g, 0.636 mmol). The reaction mixture was stirred at the same temperature for additional 1 hr and saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 20%) to give the title compound 2-methyl-N-phenyl-N-(4-(5-(trifluoromethyl)-1,3,4-oxadiazol-2-yl)benzyl)-2,7-diazaspiro[3.5]nonane-7-carboxamide as white solid (0.100 g, 64.7%).

$^1$H NMR (400 MHz, CDCl$_3$) δ 8.00 (d, 2H, J=8.3 Hz), 7.45 (d, 2H, J=8.3 Hz), 7.29 (t, 2H, J=7.9 Hz), 7.13 (t, 1H, J=7.4 Hz), 7.02 (d, 2H, J=7.5 Hz), 4.89 (s, 2H), 3.65 (brs, 4H), 3.16 (t, 4H, J=5.2 Hz), 2.74 (s, 3H), 1.67 (t, 4H, J=5.4 Hz); LRMS (ES) m/z 486.3 (M$^+$+1).

Example 91. Compound 21421: 2-Ethyl-N-phenyl-N-(4-(5-(trifluoromethyl)-1,3,4-oxadiazol-2-yl)benzyl)-2,7-diazaspiro[3.5]nonane-7-carboxamide

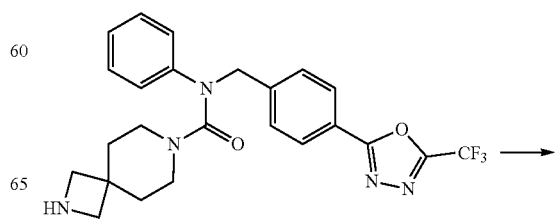

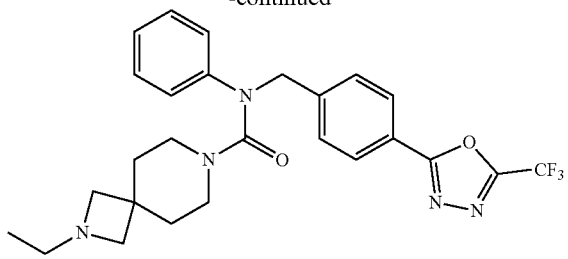

A solution of N-phenyl-N-(4-(5-(trifluoromethyl)-1,3,4-oxadiazol-2-yl)benzyl)-2,7-diazaspiro[3.5]nonane-7-carboxamide (0.150 g, 0.318 mmol) prepared in Example 87 and acetaldehyde (0.027 mL, 0.477 mmol) in dichloromethane (4 mL) was stirred at the room temperature for 30 min, and mixed with sodium triacetoxyborohydride (0.135 g, 0.636 mmol). The reaction mixture was stirred at the same temperature for additional 1 hr, and saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 20%) to give the title compound 2-ethyl-N-phenyl-N-(4-(5-(trifluoromethyl)-1,3,4-oxadiazol-2-yl)benzyl)-2,7-diazaspiro[3.5]nonane-7-carboxamide as white solid (0.014 g, 44.2%).

$^1$H NMR (400 MHz, CDCl$_3$) δ 8.00 (d, 2H, J=8.2 Hz), 7.45 (d, 2H, J=8.3 Hz), 7.29 (t, 2H, J=7.8 Hz), 7.14 (t, 1H, J=7.4 Hz), 7.02 (d, 2H, J=7.6 Hz), 4.89 (s, 2H), 4.14-4.10 (m, 2H), 3.34-3.30 (m, 2H), 3.23 (t, 2H, J=5.2 Hz), 3.10-3.06 (m, 4H), 1.76 (t, 2H, J=5.1 Hz), 1.64 (t, 2H, J=5.4 Hz), 1.25 (t, 3H, J=7.2 Hz); LRMS (ES) m/z 500.4 (M$^+$+1).

Example 92. Compound 21422: 4-Acetyl-N-phenyl-N-(4-(5-(trifluoromethyl)-1,3,4-oxadiazol-2-yl)benzyl)-1,4-diazepane-1-carboxamide

[Step 1] Methyl 4-((4-acetyl-N-phenyl-1,4-diazepane-1-carboxamido)methyl)benzoate

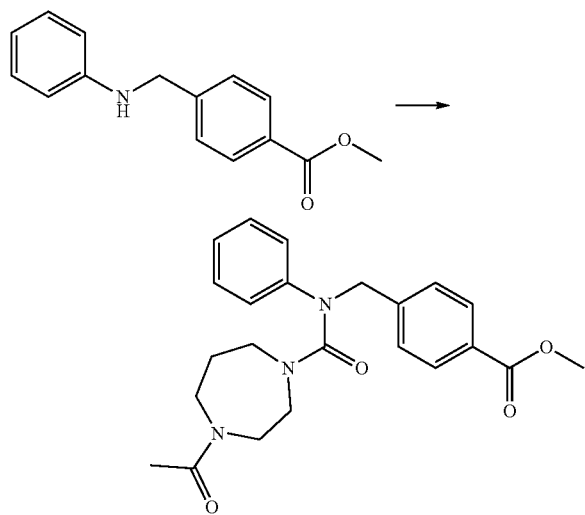

To a stirred solution of methyl 4-((phenylamino)methyl)benzoate (0.500 g, 2.072 mmol) in dichloromethane (20 mL) were added at 0° C. triphosgene (0.492 g, 1.658 mmol) and N,N-diisopropylethylamine (1.810 mL, 10.361 mmol). The reaction mixture was stirred at the same temperature for 1 hr, treated at the room temperature with 1-(1,4-diazepan-1-yl)ethan-1-one (0.354 g, 2.487 mmol), and stirred for additional 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound methyl 4-((4-acetyl-N-phenyl-1,4-diazepane-1-carboxamido)methyl)benzoate as pale yellow oil (0.844 g, 99.5%).

[Step 2] 4-Acetyl-N-(4-(hydrazinecarbonyl)benzyl)-N-phenyl-1,4-diazepane-1-carboxamide

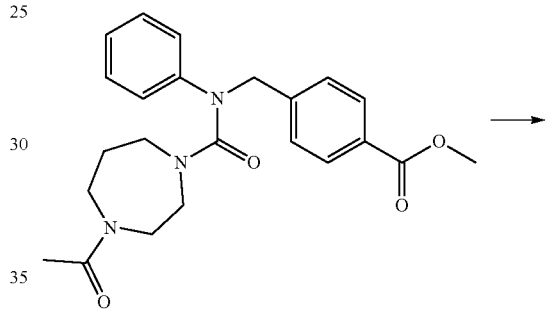

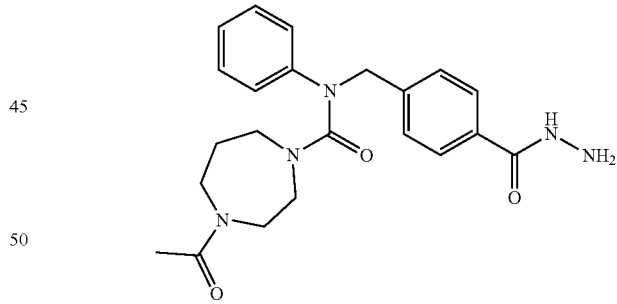

Methyl 4-((4-acetyl-N-phenyl-1,4-diazepane-1-carboxamido)methyl)benzoate (0.844 g, 2,061 mmol) prepared in Step 1 and hydrazine monohydrate (2.002 mL, 41.222 mmol) in ethanol (15 mL) was mixed at the room temperature and then heated at 120° C. under the microwaves for 1 hr, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The title compound 4-acetyl-N-(4-(hydrazinecarbonyl)benzyl)-N-phenyl-1,4-diazepane-1-carboxamide was used without further purification (0.807 g, 95.6%, white solid).

[Step 3] 4-Acetyl-N-phenyl-N-(4-(2-(2,2,2-trifluoro-acetyl)hydrazine-1-carbonyl)benzyl)-1,4-diazepane-1-carboxamide

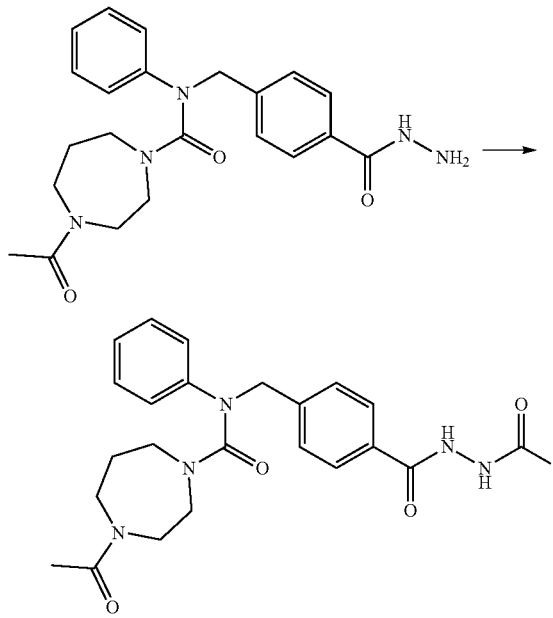

A solution of 4-acetyl-N-(4-(hydrazinecarbonyl)benzyl)-N-phenyl-1,4-diazepane-1-carboxamide (0.807 g, 1.971 mmol) prepared in Step 2 and triethylamine (0.410 mL, 2.956 mmol) in dichloromethane (10 mL) was mixed at the room temperature with trifluoroacetic anhydride (0.247 mL, 1.774 mmol). The reaction mixture was stirred at the same temperature for 3 hr, and saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 20%) to give the title compound 4-acetyl-N-phenyl-N-(4-(2-(2,2,2-trifluoro-acetyl)hydrazine-1-carbonyl)benzyl)-1,4-diazepane-1-carboxamide as white solid (0.517 g, 51.9%).

[Step 4] Compound 21422

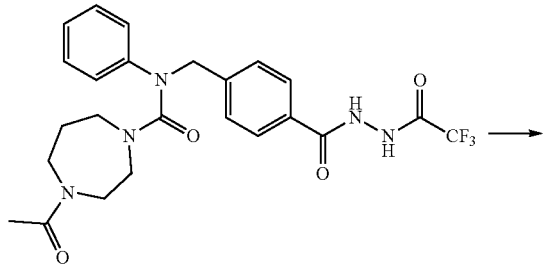

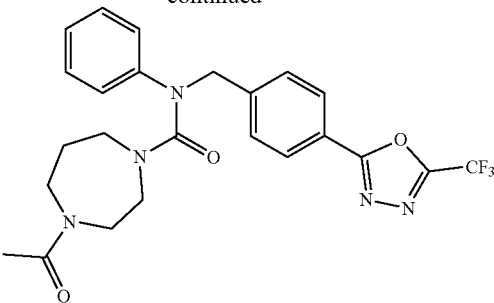

4-Acetyl-N-phenyl-N-(4-(2-(2,2,2-trifluoroacetyl)hydrazine-1-carbonyl)benzyl)-1,4-diazepane-1-carboxamide (0.517 g, 1.023 mmol) prepared in Step 3 and 1-methoxy-N-triethylammoniosulfonyl-methanimidate (Burgess reagent, 0.366 g, 1.534 mmol) in tetrahydrofuran (20 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=0% to 40%) to give the title compound 4-acetyl-N-phenyl-N-(4-(5-(trifluoromethyl)-1,3,4-oxadiazol-2-yl)benzyl)-1,4-diazepane-1-carboxamide as white solid (0.211 g, 42.3%).

$^1$H NMR (400 MHz, CDCl$_3$) δ 8.04-8.01 (m, 2H), 7.50-7.46 (m, 2H), 7.31-7.27 (m, 2H), 7.16-7.11 (m, 1H), 7.03 (d, 2H, J=7.7 Hz), 4.86-4.85 (m, 2H), 3.47-3.34 (m, 6H), 3.22 (t, 1H, J=5.6 Hz), 3.12 (t, 1H, J=6.0 Hz), 2.03 (s, 3H), 1.71-1.69 (m, 1H), 1.55-1.52 (m, 1H); LRMS (ES) m/z 488.5 (M$^+$+1).

Example 93. Compound 21423: N-(4-(5-(difluoromethyl)-1,3,4-oxadiazol-2-yl)-2-fluorobenzyl)-4-methyl-N-phenyl-1,4-diazepane-1-carboxamide

[Step 1] Methyl 3-fluoro-4-((4-methyl-N-phenyl-1,4-diazepane-1-carboxamido)methyl)benzoate

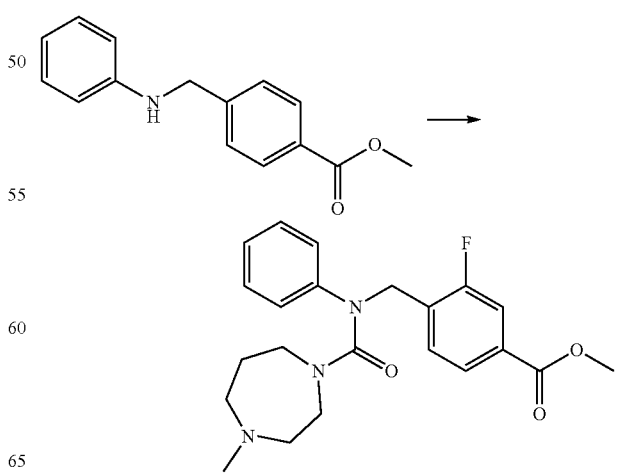

To a stirred solution of methyl 3-fluoro-4-((phenylamino)methyl)benzoate (0.500 g, 1.928 mmol) in dichloromethane (20 mL) were added at 0° C. triphosgene (0.458 g, 1.543 mmol) and N,N-diisopropylethylamine (1.684 mL, 9.642 mmol). The reaction mixture was stirred at the same temperature for 1 hr, treated at the room temperature with 1-methyl-1,4-diazepane (0.264 g, 2.314 mmol), and stirred for additional 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 10%) to give the title compound methyl 3-fluoro-4-((4-methyl-N-phenyl-1,4-diazepane-1-carboxamido)methyl)benzoate as yellow oil (0.684 g, 88.8%).

[Step 2] N-(2-fluoro-4-(hydrazinecarbonyl)benzyl)-4-methyl-N-phenyl-1,4-diazepane-1-carboxamide

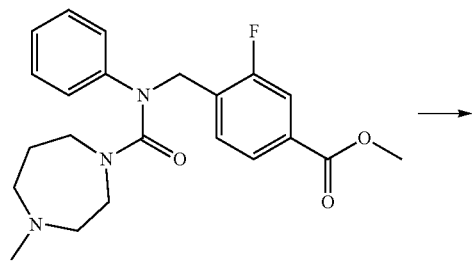

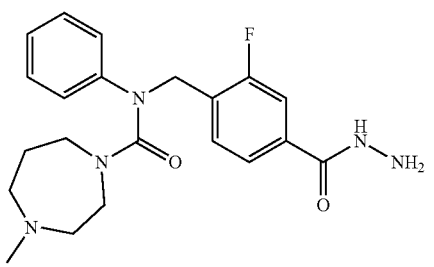

Methyl 3-fluoro-4-((4-methyl-N-phenyl-1,4-diazepane-1-carboxamido)methyl)benzoate (0.684 g, 1.712 mmol) prepared in Step 1 and hydrazine monohydrate (1.663 mL, 34.245 mmol) in ethanol (10 mL) was mixed at the room temperature and then heated at 120° C. under the microwaves for 1 hr, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The title compound N-(2-fluoro-4-(hydrazinecarbonyl)benzyl)-4-methyl-N-phenyl-1,4-diazepane-1-carboxamide was used without further purification (0.674 g, 98.5%, white solid).

[Step 3] N-(4-(2-(2,2-difluoroacetyl)hydrazine-1-carbonyl)-2-fluorobenzyl)-4-methyl-N-phenyl-1,4-diazepane-1-carboxamide

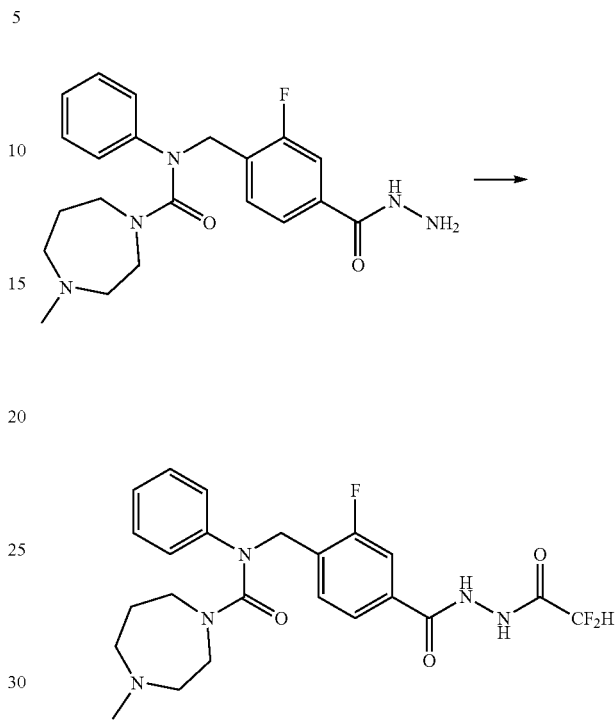

A solution of N-(2-fluoro-4-(hydrazinecarbonyl)benzyl)-4-methyl-N-phenyl-1,4-diazepane-1-carboxamide (0.674 g, 1.687 mmol) prepared in Step 2 and triethylamine (0.351 mL, 2.531 mmol) in dichloromethane (10 mL) was mixed at the room temperature with 2,2-difluoroacetic anhydride (0.165 mL, 1.519 mmol). The reaction mixture was stirred at the same temperature for 3 hr, and saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 20%) to give the title compound N-(4-(2-(2,2-difluoroacetyl)hydrazine-1-carbonyl)-2-fluorobenzyl)-4-methyl-N-phenyl-1,4-diazepane-1-carboxamide as white solid (0.598 g, 74.2%).

[Step 4] Compound 21423

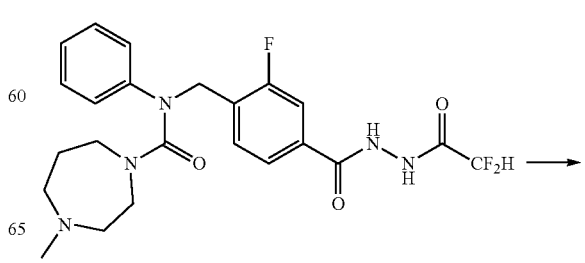

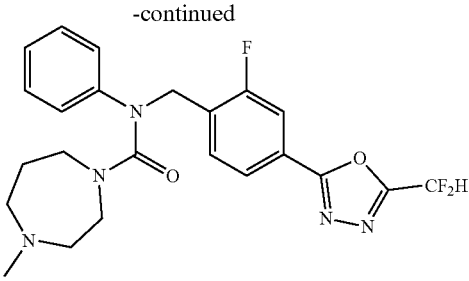

N-(4-(2-(2,2-difluoroacetyl)hydrazine-1-carbonyl)-2-fluorobenzyl)-4-methyl-N-phen yl-1,4-diazepane-1-carboxamide (0.587 g, 1.229 mmol) prepared in Step 3 and 1-methoxy-N-triethylammoniosulfonyl-methanimidate (Burgess reagent, 0.439 g, 1.844 mmol) in tetrahydrofuran (15 mL) was mixed at the room temperature and then heated at 150° C. under the microwaves for 30 min, and cooled down to the room temperature to terminate the reaction. The reaction mixture was concentrated under the reduced pressure to remove the solvent. The concentrate was purified and concentrated by column chromatography ($SiO_2$, 12 g cartridge; methanol/dichloromethane=0% to 10%) to give the title compound N-(4-(5-(difluoromethyl)-1,3,4-oxadiazol-2-yl)-2-fluorobenzyl)-4-methyl-N-phenyl-1,4-diazepane-1-carboxamide as pale yellow solid (0.215 g, 38.1%).

$^1$H NMR (400 MHz, $CDCl_3$) δ 7.86-7.84 (m, 1H), 7.75-7.70 (m, 2H), 7.30 (t, 2H, J=7.9 Hz), 7.12 (t, 1H, J=7.4 Hz), 7.06-6.77 (m, 3H), 4.93 (s, 2H), 3.47 (brs, 2H), 3.15 (brs, 2H), 2.64-2.57 (m, 4H), 2.39 (s, 3H), 1.84 (brs, 2H); LRMS (ES) m/z 460.3 ($M^+$+1).

Example 94. Compound 21424: N-(pyridin-2-yl)-N-(4-(5-(trifluoromethyl)-1,3,4-oxadiazol-2-yl)benzyl)morpholine-4-carboxamide

[Step 1] N-(4-(hydrazinecarbonyl)benzyl)-N-(pyridin-2-yl)morpholine-4-carboxamide

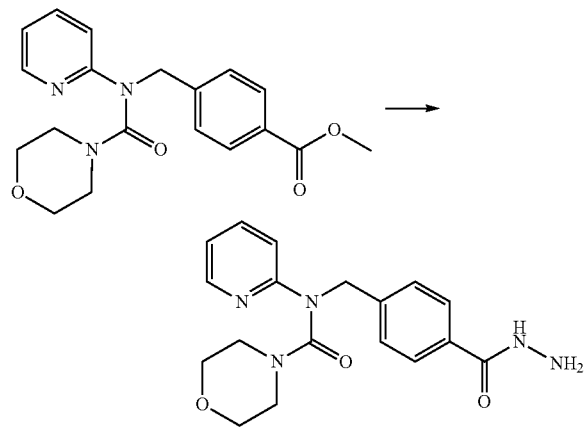

Methyl 4-((N-(pyridin-2-yl)morpholine-4-carboxamido)methyl)benzoate (0.300 g, 0.844 mmol) and hydrazine monohydrate (0.820 mL, 16.883 mmol) in ethanol (15 mL) was mixed at the room temperature and then heated at 120° C. under the microwaves for 1 hr, and cooled down to the room temperature to terminate the reaction. The reaction mixture was concentrated under the reduced pressure to remove the solvent. The title compound N-(4-(hydrazinecarbonyl)benzyl)-N-(pyridin-2-yl)morpholine-4-carboxamide was used without further purification (0.300 g, 100.0%, pale yellow solid).

[Step 2] N-(pyridin-2-yl)-N-(4-(2-(2,2,2-trifluoroacetyl)hydrazine-1-carbonyl)benzyl)morpholine-4-carboxamide

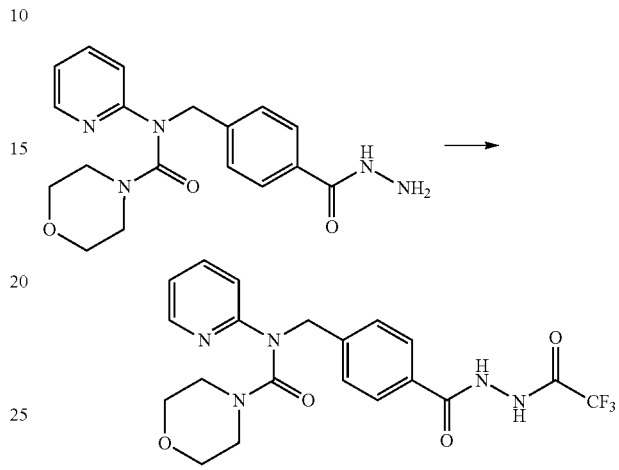

A solution of N-(4-(hydrazinecarbonyl)benzyl)-N-(pyridin-2-yl)morpholine-4-carboxamide (0.300 g, 0.844 mmol) prepared in Step 1 and triethylamine (0.176 mL, 1.266 mmol) in dichloromethane (10 mL) was mixed at the room temperature with trifluoroacetic anhydride (0.114 mL, 0.760 mmol), and stirred at the same temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 12 g cartridge; methanol/dichloromethane=0% to 10%) to give the title compound N-(pyridin-2-yl)-N-(4-(2-(2,2,2-trifluoroacetyl)hydrazine-1-carbonyl)benzyl)morpholine-4-carboxamide as pale yellow oil (0.069 g, 18.1%).

[Step 3] Compound 21424

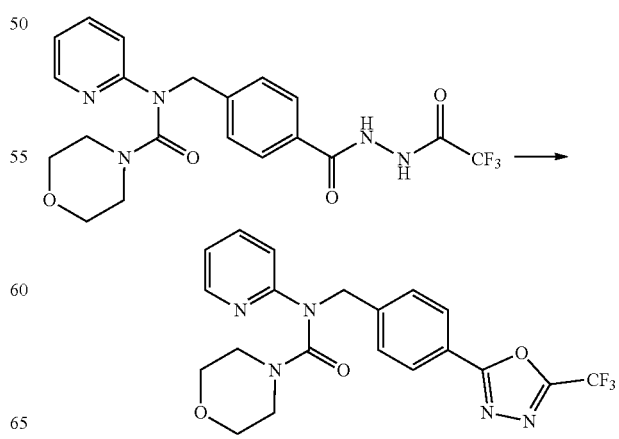

N-(pyridin-2-yl)-N-(4-(2-(2,2,2-trifluoroacetyl)hydrazine-1-carbonyl)benzyl)morpholine-4-carboxamide (0.069 g, 0.153 mmol) prepared in Step 2 and 1-methoxy-N-triethylammoniosulfonyl-methanimidate (Burgess reagent, 0.055 g, 0.229 mmol) in tetrahydrofuran (3 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit (with anhydrous $Na_2SO_4$ cartridge attached) to remove solid residues and aqueous layer, and the organic layer collected was concentrated in vacuo. The concentrate was purified and concentrated by column chromatography ($SiO_2$, 4 g cartridge; methanol/dichloromethane=0% to 2.5%) to give the title compound N-(pyridin-2-yl)-N-(4-(5-(trifluoromethyl)-1,3,4-oxadiazol-2-yl)benzyl)morpholine-4-carboxamide as colorless oil (0.003 g, 4.5%).

$^1$H NMR (400 MHz, $CDCl_3$) δ 8.40-8.39 (m, 1H), 8.04 (d, 2H, J=8.4 Hz), 7.64-7.60 (m, 3H), 6.98-6.94 (m, 2H), 5.19 (s, 2H), 3.56 (t, 4H, J=4.8 Hz), 3.32 (t, 4H, J=4.8 Hz); LRMS (ES) m/z 434.4 ($M^+$+1).

Example 95. Compound 21425: N-(pyrimidin-2-yl)-N-(4-(5-(trifluoromethyl)-1,3,4-oxadiazol-2-yl)benzyl)morpholine-4-carboxamide

[Step 1] N-(4-(hydrazinecarbonyl)benzyl)-N-(pyrimidin-2-yl)morpholine-4-carboxamide

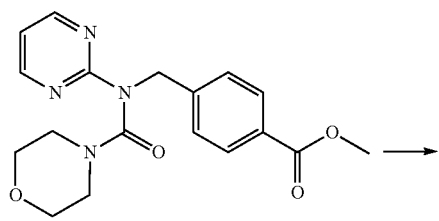

Methyl 4-((N-(pyrimidin-2-yl)morpholine-4-carboxamido)methyl)benzoate (0.300 g, 0.842 mmol) and hydrazine monohydrate (0.818 mL, 16.836 mmol) in ethanol (15 mL) was mixed at the room temperature and then heated at 120° C. under the microwaves for 1 hr, and cooled down to the room temperature to terminate the reaction. The reaction mixture was concentrated under the reduced pressure to remove the solvent. The title compound N-(4-(hydrazinecarbonyl)benzyl)-N-(pyrimidin-2-yl)morpholine-4-carboxamide was used without further purification (0.300 g, 100.0%, yellow solid).

[Step 2] N-(pyrimidin-2-yl)-N-(4-(2-(2,2,2-trifluoroacetyl)hydrazine-1-carbonyl)benzyl)morpholine-4-carboxamide

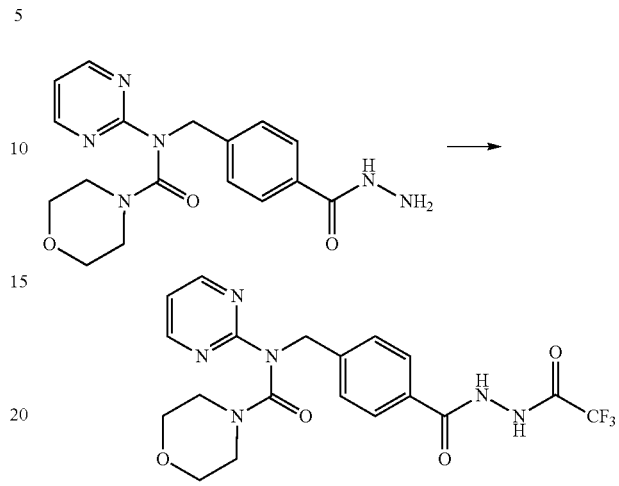

A solution of N-(4-(hydrazinecarbonyl)benzyl)-N-(pyrimidin-2-yl)morpholine-4-carboxamide (0.300 g, 0.842 mmol) prepared in Step 1 and triethylamine (0.175 mL, 1.263 mmol) in dichloromethane (10 mL) was mixed at the room temperature with trifluoroacetic anhydride (0.105 mL, 0.758 mmol), and stirred at the same temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 12 g cartridge; methanol/dichloromethane=0% to 10%) to give the title compound N-(pyrimidin-2-yl)-N-(4-(2-(2,2,2-trifluoroacetyl)hydrazine-1-carbonyl)benzyl)morpholine-4-carboxamide as pale yellow oil (0.034 g, 8.9%).

[Step 3] Compound 21425

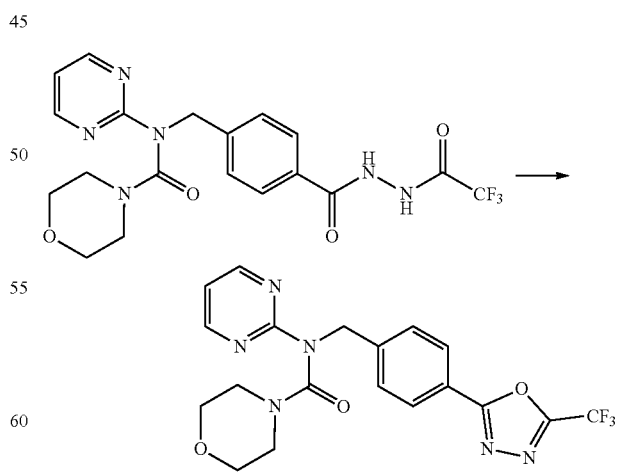

N-(pyrimidin-2-yl)-N-(4-(2-(2,2,2-trifluoroacetyl)hydrazine-1-carbonyl)benzyl)morpholine-4-carboxamide (0.034 g, 0.075 mmol) prepared in Step 2 and 1-methoxy-N-triethylammoniosulfonyl-methanimidate (Burgess reagent, 0.027 g, 0.113 mmol) in tetrahydrofuran (3 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit (with anhydrous Na$_2$SO$_4$ cartridge attached) to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(pyrimidin-2-yl)-N-(4-(5-(trifluoromethyl)-1,3,4-oxadiazol-2-yl)benzyl)morpholine-4-carboxamide as pale yellow oil (0.006 g, 18.4%).

$^1$H NMR (400 MHz, CDCl$_3$) δ 8.48 (d, 2H, J=4.8 Hz), 8.08 (d, 2H, J=8.3 Hz), 7.65 (d, 2H, J=8.3 Hz), 6.83 (t, 1H, J=4.8 Hz), 5.20 (s, 2H), 3.56 (t, 4H, J=4.7 Hz), 3.47-3.46 (m, 4H); LRMS (ES) m/z 435.3 (M$^+$+1).

Example 96. Compound 21426: N-(4-fluorophenyl)-N-(4-(5-(trifluoromethyl)-1,3,4-oxadiazol-2-yl)benzyl)morpholine-4-carboxamide

[Step 1] Methyl 4-((N-(4-fluorophenyl)morpholine-4-carboxamido)methyl)benzoate

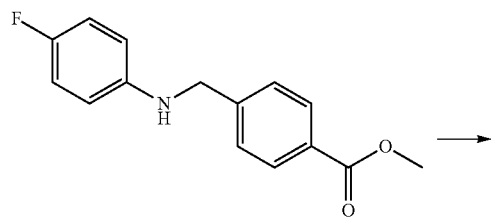

Methyl 4-(((4-fluorophenyl)amino)methyl)benzoate (0.500 g, 1.928 mmol), morpholine-4-carbonyl chloride (0.248 mL, 2.121 mmol), DMAP (0.016 mL, 0.096 mmol) and N,N-diisopropylethylamine (1.246 g, 9.642 mmol) were mixed at the room temperature in toluene (10 mL) and then stirred at 100° C. for 17 hr, and cooled down to the room temperature to terminate the reaction. The reaction mixture was concentrated under the reduced pressure to remove the solvent. The concentrate was purified and concentrated by column chromatography (SiO$_2$, 12 g cartridge; ethyl acetate/hexane=10% to 60%) to give the title compound methyl 4-((N-(4-fluorophenyl)morpholine-4-carboxamido)methyl)benzoate as pale yellow solid (0.277 g, 38.6%).

[Step 2] N-(4-fluorophenyl)-N-(4-(hydrazinecarbonyl)benzyl)morpholine-4-carboxamide

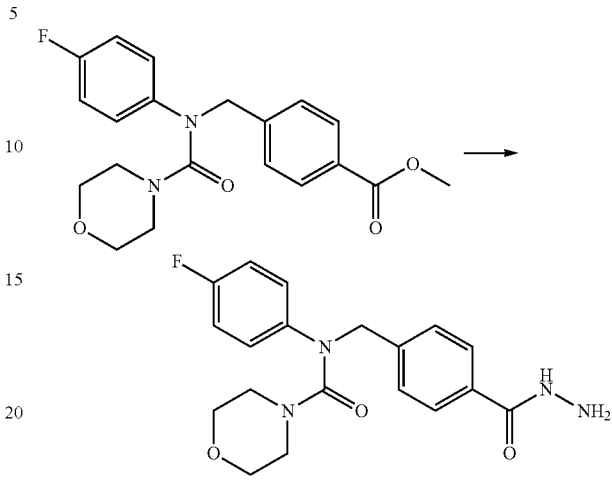

Methyl 4-((N-(4-fluorophenyl)morpholine-4-carboxamido)methyl)benzoate (0.277 g, 0.744 mmol) prepared in Step 1 and hydrazine monohydrate (0.723 mL, 14.876 mmol) in ethanol (15 mL) was mixed at the room temperature and then heated at 120° C. under the microwaves for 1 hr, and cooled down to the room temperature to terminate the reaction. The reaction mixture was concentrated under the reduced pressure to remove the solvent. The title compound N-(4-fluorophenyl)-N-(4-(hydrazinecarbonyl)benzyl)morpholine-4-carboxamide was used without further purification (0.277 g, 100.0%, white solid).

[Step 3] N-(4-fluorophenyl)-N-(4-(2-(2,2,2-trifluoroacetyl)hydrazine-1-carbonyl)benzyl)morpholine-4-carboxamide

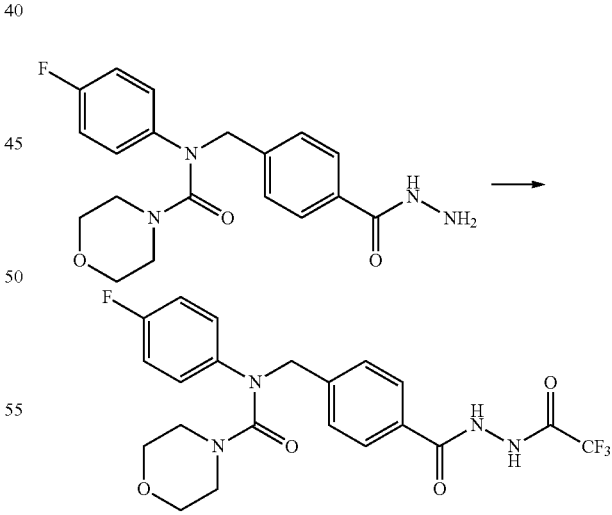

A solution of N-(4-fluorophenyl)-N-(4-(hydrazinecarbonyl)benzyl)morpholine-4-carboxamide (0.277 g, 0.744 mmol) prepared in Step 2 and triethylamine (0.155 mL, 1.116 mmol) in dichloromethane (10 mL) was mixed at the room temperature with trifluoroacetic anhydride (0.100 mL, 0.669 mmol), stirred at the same temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 10%) to give the title compound N-(4-fluorophenyl)-N-(4-(2-(2,2,2-trifluoroacetyl)hydrazine-1-carbonyl)benzyl)morpholine-4-carboxamide as pale yellow oil (0.050 g, 14.4%).

[Step 4] Compound 21426

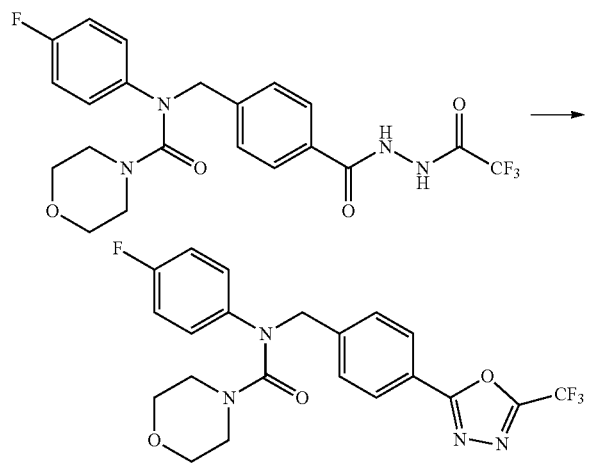

A solution of N-(4-fluorophenyl)-N-(4-(2-(2,2,2-trifluoroacetyl)hydrazine-1-carbonyl)benzyl)morpholine-4-carboxamide (0.050 g, 0.107 mmol) prepared in Step 3 and 1-methoxy-N-triethylammoniosulfonyl-methanimidate (Burgess reagent, 0.038 g, 0.160 mmol) in dichloromethane (10 mL) was stirred at the room temperature for 1 hr. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=10% to 60%) to give the title compound N-(4-fluorophenyl)-N-(4-(5-(trifluoromethyl)-1,3,4-oxadiazol-2-yl)benzyl)morpholine-4-carboxamide as colorless oil (0.025 g, 52.0%).
$^1$H NMR (400 MHz, CDCl$_3$) δ 8.04 (d, 2H, J=8.3 Hz), 7.48 (d, 2H, J=8.4 Hz), 7.05-6.99 (m, 4H), 4.91 (s, 2H), 3.51 (t, 4H, J=4.7 Hz), 3.25 (t, 4H, J=4.7 Hz); LRMS (ES) m/z 451.2 (M$^+$+1).

Example 97: Compound 21427: N-(pyridin-3-yl)-N-(4-(5-(trifluoromethyl)-1,3,4-oxadiazol-2-yl)benzyl)morpholine-4-carboxamide

[Step 1] Methyl 4-((pyridin-3-ylamino)methyl)benzoate

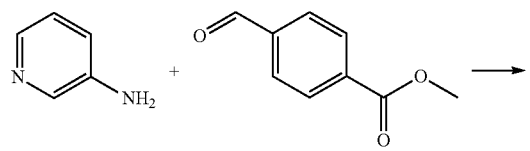

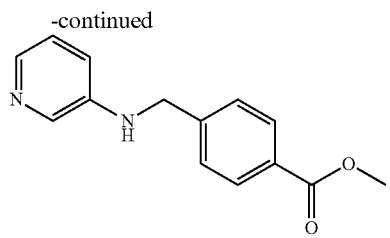

A solution of pyridin-3-amine (0.500 g, 5.312 mmol) and methyl 4-formylbenzoate (1.308 g, 7.969 mmol) in dichloromethane (10 mL) was stirred at the room temperature for 10 min, and mixed with sodium triacetoxyborohydride (2.252 g, 10.625 mmol). The reaction mixture was stirred at the same temperature for additional 17 hr, and saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 60%) to give the title compound methyl 4-((pyridin-3-ylamino)methyl)benzoate as white solid (0.458 g, 35.6%).

[Step 2] Methyl 4-((N-(pyridin-3-yl)morpholine-4-carboxamido)methyl)benzoate

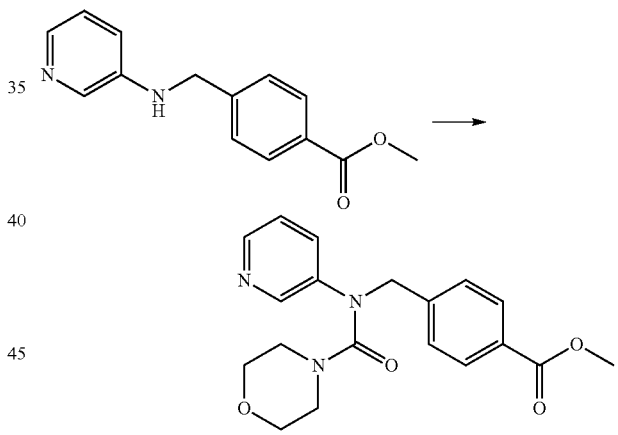

To a stirred solution of methyl 4-((pyridin-3-ylamino)methyl)benzoate (0.450 g, 1.857 mmol) prepared in Step 1 in dichloromethane (10 mL) were added at 0° C. triphosgene (0.441 g, 1.486 mmol) and N,N-diisopropylethylamine (1.622 mL, 9.287 mmol). The reaction mixture was stirred at the same temperature for 10 min, treated at the room temperature with morpholine (0.195 mL, 2.229 mmol), and stirred for additional 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=10% to 70%) to give the title compound methyl 4-((N-(pyridin-3-yl)morpholine-4-carboxamido)methyl)benzoate as pale yellow oil (0.517 g, 78.3%).

[Step 3] N-(4-(hydrazinecarbonyl)benzyl)-N-(pyridin-3-yl)morpholine-4-carboxamide

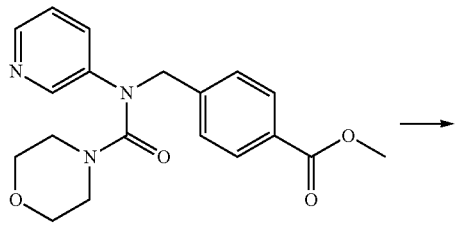

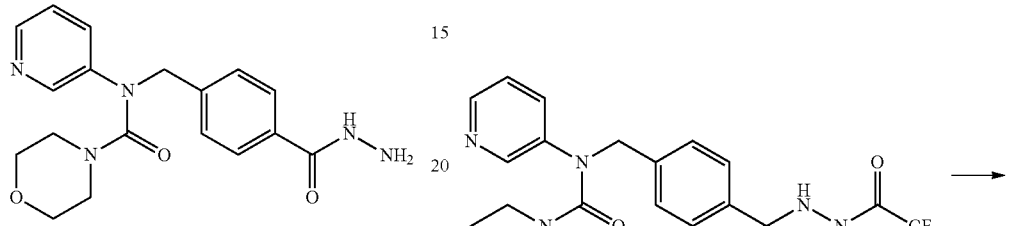

Methyl 4-((N-(pyridin-3-yl)morpholine-4-carboxamido)methyl)benzoate (0.160 g, 0.450 mmol) prepared in Step 2 and hydrazine monohydrate (0.438 mL, 9.004 mmol) in ethanol (3 mL) were mixed at the room temperature and then heated at 120° C. under the microwaves for 1 hr, and cooled down to the room temperature to terminate the reaction. The reaction mixture was concentrated under the reduced pressure to remove the solvent. The title compound N-(4-(hydrazinecarbonyl)benzyl)-N-(pyridin-3-yl)morpholine-4-carboxamide was used without further purification (0.160 g, 100.0%, white solid).

[Step 4] N-(pyridin-3-yl)-N-(4-(2-(2,2,2-trifluoroacetyl)hydrazine-1-carbonyl)benzyl)morpholine-4-carboxamide

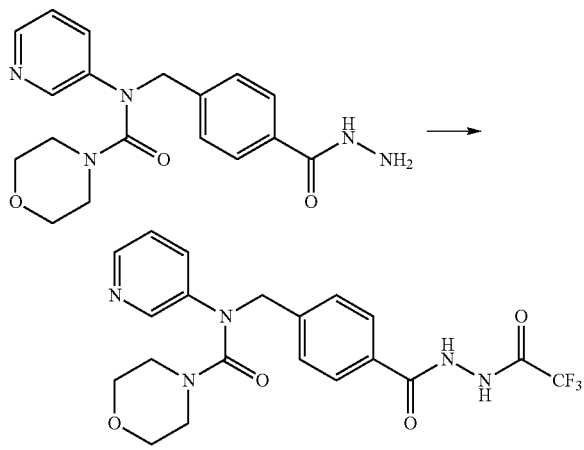

A solution of N-(4-(hydrazinecarbonyl)benzyl)-N-(pyridin-3-yl)morpholine-4-carboxamide (0.322 g, 0.906 mmol) prepared in Step 3 and triethylamine (0.189 mL, 1.359 mmol) in dichloromethane (10 mL) was mixed at the room temperature with trifluoroacetic anhydride (0.113 mL, 0.815 mmol), and stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 10%) to give the title compound N-(pyridin-3-yl)-N-(4-(2-(2,2,2-trifluoroacetyl)hydrazine-1-carbonyl)benzyl)morpholine-4-carboxamide as pale yellow solid (0.107 g, 26.2%).

[Step 5] Compound 21427

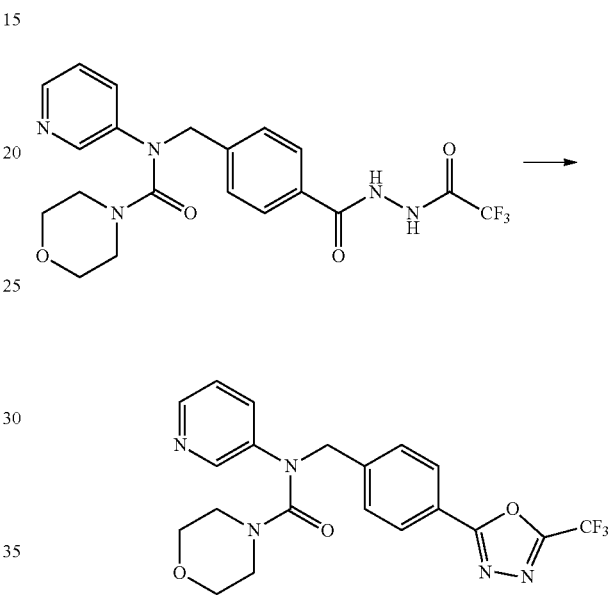

N-(pyridin-3-yl)-N-(4-(2-(2,2,2-trifluoroacetyl)hydrazine-1-carbonyl)benzyl)morpholine-4-carboxamide (0.107 g, 0.237 mmol) prepared in Step 4 and 1-methoxy-N-triethylammoniosulfonyl-methanimidate (Burgess reagent, 0.085 g, 0.356 mmol) in tetrahydrofuran (15 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(pyridin-3-yl)-N-(4-(5-(trifluoromethyl)-1,3,4-oxadiazol-2-yl)benzyl)morpholine-4-carboxamide as white solid (0.003 g, 2.9%).

$^1$H NMR (400 MHz, CDCl$_3$) δ 8.42 (d, 1H, J=2.3 Hz), 8.36 (d, 1H, J=3.8 Hz), 8.04 (d, 2H, J=8.3 Hz), 7.49 (d, 2H, J=8.2 Hz), 7.41-7.39 (m, 1H), 7.29-7.27 (m, 1H), 8.36 (d, 1H, J=3.8 Hz), 4.96 (s, 2H), 3.52 (t, 4H, J=4.7 Hz), 3.26 (t, 4H, J=4.7 Hz); LRMS (ES) m/z 434.1 (M$^+$+1).

Example 98. Compound 21428: N-(2-fluorophenyl)-N-(4-(5-(trifluoromethyl)-1,3,4-oxadiazol-2-yl)benzyl)morpholine-4-carboxamide

[Step 1] Methyl 4-4-(2-fluorophenyl)amino)methyl)benzoate

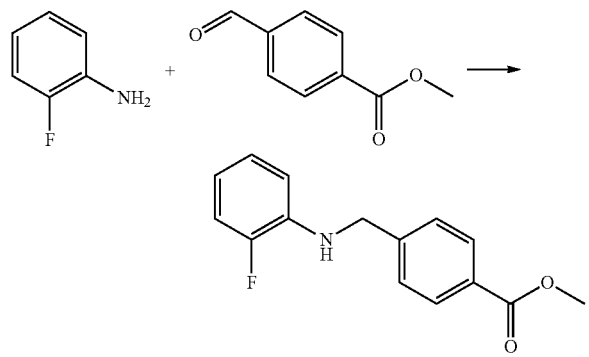

A solution of 2-fluoroaniline (0.500 g, 4.500 mmol) and methyl 4-formylbenzoate (1.108 g, 6.749 mmol) in dichloromethane (10 mL) was stirred at the room temperature for 10 min, and mixed with sodium triacetoxyborohydride (1.907 g, 8.999 mmol). The reaction mixture was stirred at the same temperature for additional 17 hr, and saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; ethyl acetate/hexane=0% to 20%) to give the title compound methyl 4-(((2-fluorophenyl)amino)methyl)benzoate as pale yellow solid (0.582 g, 49.9%).

[Step 2] Methyl 4-((N-(2-fluorophenyl)morpholine-4-carboxamido)methyl)benzoate

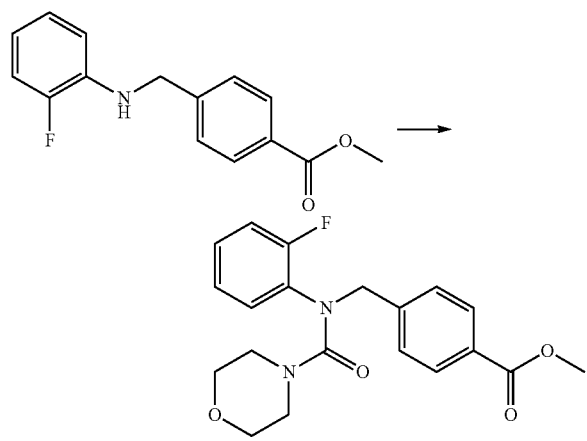

To a stirred solution of methyl 4-(((2-fluorophenyl)amino)methyl)benzoate (0.500 g, 1.928 mmol) prepared in Step 1 in dichloromethane (10 mL) were added at 0° C. triphosgene (0.458 g, 1.543 mmol) and N,N-diisopropylethylamine (1.684 mL, 9.642 mmol). The reaction mixture was stirred at the same temperature for 10 min, treated at the room temperature with morpholine (0.202 mL, 2.314 mmol), and stirred for additional 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; ethyl acetate/hexane=10% to 70%) to give the title compound methyl 4-((N-(2-fluorophenyl)morpholine-4-carboxamido)methyl)benzoate as pale yellow oil (0.693 g, 96.5%).

[Step 3] N-(2-fluorophenyl)-N-(4-(hydrazinecarbonyl)benzyl)morpholine-4-carboxamide

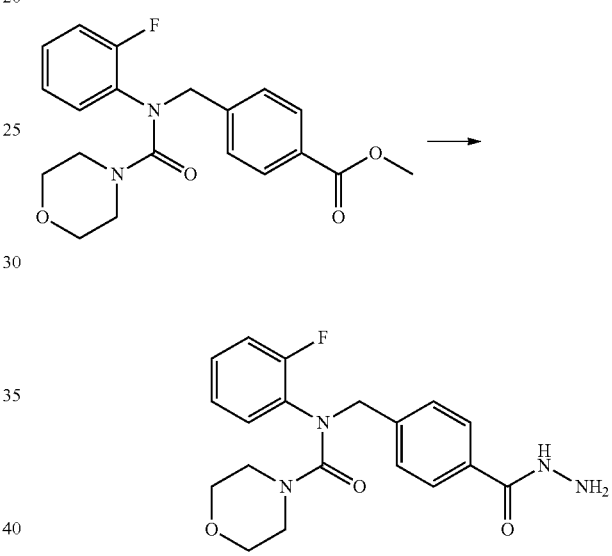

Methyl 4-((N-(2-fluorophenyl)morpholine-4-carboxamido)methyl)benzoate (0.693 g, 1.861 mmol) prepared in Step 2 and hydrazine monohydrate (1.808 mL, 37.218 mmol) in ethanol (20 mL) was mixed at the room temperature and then heated at 120° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using dichloromethane (5 mL). The resulting precipitates were filtered, washed by hexane, and dried to give the title compound N-(2-fluorophenyl)-N-(4-(hydrazinecarbonyl)benzyl)morpholine-4-carboxamide as white solid (0.422 g, 60.9%).

433

[Step 4] N-(2-fluorophenyl)-N-(4-(2-(2,2,2-trifluoroacetyl)hydrazine-1-carbonyl)benzyl)morpholine-4-carboxamide

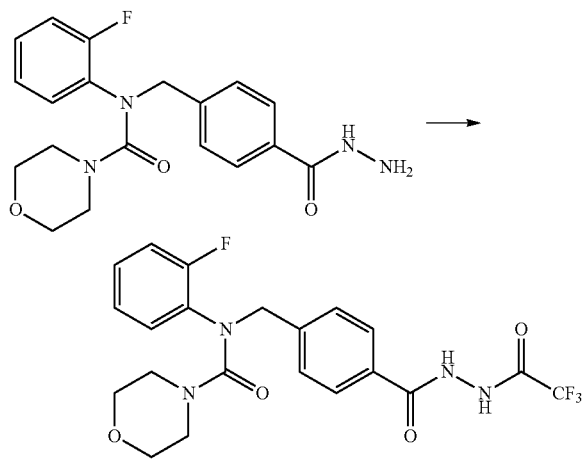

A solution of N-(2-fluorophenyl)-N-(4-(hydrazinecarbonyl)benzyl)morpholine-4-carboxamide (0.422 g, 1.133 mmol) prepared in Step 3 and triethylamine (0.237 mL, 1.700 mmol) in dichloromethane (10 mL) was mixed at the room temperature with trifluoroacetic anhydride (0.142 mL, 1.020 mmol), stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-(2-fluorophenyl)-N-(4-(2-(2,2,2-trifluoroacetyl)hydrazine-1-carbonyl)benzyl)morpholine-4-carboxamide as colorless oil (0.303 g, 57.1%).

[Step 5] Compound 21428

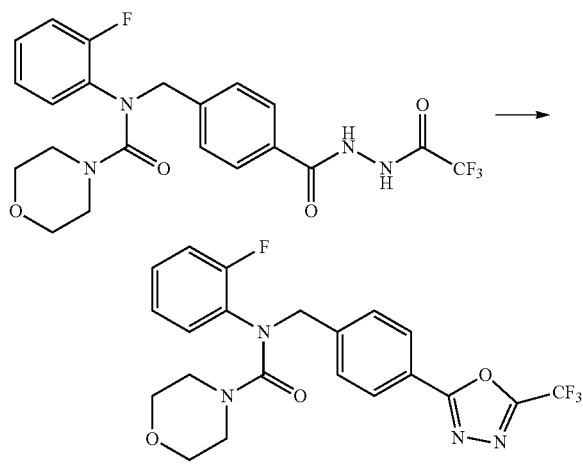

N-(2-fluorophenyl)-N-(4-(2-(2,2,2-trifluoroacetyl)hydrazine-1-carbonyl)benzyl)morpholine-4-carboxamide (0.303

434 g, 0.647 mmol) prepared in Step 4 and 1-methoxy-N-triethylammoniosulfonyl-methanimidate (Burgess reagent, 0.231 g, 0.970 mmol) in tetrahydrofuran (15 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=10% to 50%) to give the title compound N-(2-fluorophenyl)-N-(4-(5-(trifluoromethyl)-1,3,4-oxadiazol-2-yl)benzyl)morpholine-4-carboxamide as pale yellow oil (0.202 g, 69.3%).

$^1$H NMR (400 MHz, CDCl$_3$) δ 7.99 (d, 2H, J=8.3 Hz), 7.51 (d, 2H, J=8.2 Hz), 7.19-7.18 (m, 1H), 7.17-7.03 (m, 3H), 4.83 (s, 2H), 3.45 (t, 4H, J=4.7 Hz), 3.21 (t, 4H, J=4.7 Hz); LRMS (ES) m/z 451.0 (M$^+$+1).

Example 99. Compound 21429: N-(2-chloro-4-(5-(trifluoromethyl)-1,3,4-oxadiazol-2-yl)benzyl)-N-phenylmorpholine-4-carboxamide

[Step 1] Methyl 3-chloro-4-((phenylamino)methyl)benzoate

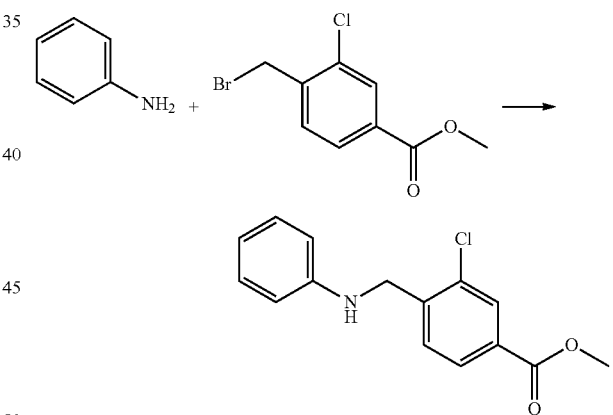

A solution of aniline (0.500 g, 5.369 mmol) and sodium hydride (60.00%, 0.215 g, 5.369 mmol) in N,N-dimethylformamide (15 mL) was stirred at the room temperature for 10 min, and mixed with methyl 4-(bromomethyl)-3-chlorobenzoate (1.556 g, 5.906 mmol). The reaction mixture was stirred at the same temperature for additional 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 3-chloro-4-((phenylamino)methyl)benzoate as pale yellow solid (1.490 g, 100.8%).

[Step 2] Methyl 3-chloro-4-((N-phenylmorpholine-4-carboxamido)methyl)benzoate

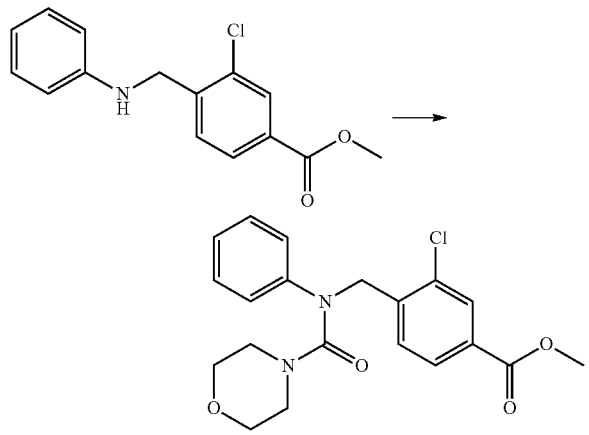

A solution of methyl 3-chloro-4-((phenylamino)methyl)benzoate (1.490 g, 5.404 mmol) prepared in Step 1, triphosgene (1.283 g, 4.323 mmol) and N,N-diisopropylethylamine (4.719 mL, 27.019 mmol) in dichloromethane (60 mL) was stirred at 0° C. for 10 min, and mixed with morpholine (0.567 mL, 6.485 mmol). The reaction mixture was stirred at the same temperature for additional 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=40% to 80%) to give the title compound methyl 3-chloro-4-((N-phenylmorpholine-4-carboxamido)methyl)benzoate as white solid (1.950 g, 92.8%).

[Step 3] N-(2-chloro-4-(hydrazinecarbonyl)benzyl)-N-phenylmorpholine-4-carboxamide

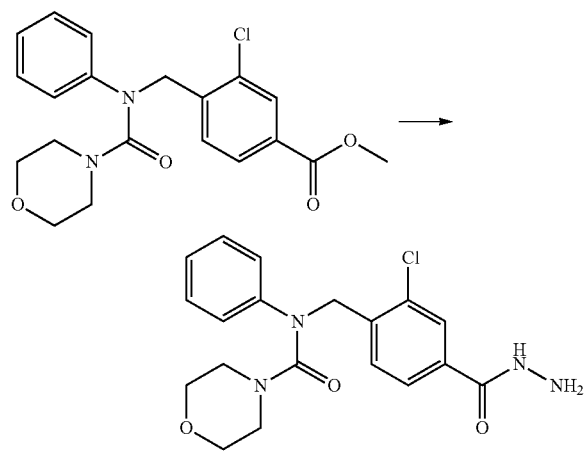

Methyl 3-chloro-4-((N-phenylmorpholine-4-carboxamido)methyl)benzoate (1.950 g, 5.015 mmol) prepared in Step 2 and hydrazine monohydrate (4.875 mL, 100.296 mmol) in ethanol (20 mL) was mixed at the room temperature and then heated at 120° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The obtained title compound N-(2-chloro-4-(hydrazinecarbonyl)benzyl)-N-phenylmorpholine-4-carboxamide was used without further purification (1.950 g, 100.0%, white solid).

[Step 4] N-(2-chloro-4-(2-(2,2,2-trifluoroacetyl)hydrazine-1-carbonyl)benzyl)-N-phenylmorpholine-4-carboxamide

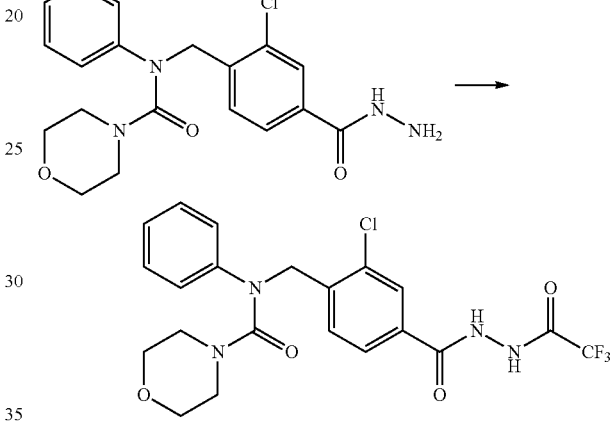

A solution of N-(2-chloro-4-(hydrazinecarbonyl)benzyl)-N-phenylmorpholine-4-carboxamide (0.300 g, 0.772 mmol) prepared in Step 3 and triethylamine (0.161 mL, 1.157 mmol) in dichloromethane (10 mL) was mixed at the room temperature with trifluoroacetic anhydride (0.097 mL, 0.694 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer; and the organic layer collected was concentrated in vacuo. The concentrate was purified and concentrated by column chromatography (SiO$_2$, 4 g cartridge; methanol/dichloromethane=0% to 10%) to give the title compound N-(2-chloro-4-(2-(2,2,2-trifluoroacetyl)hydrazine-1-carbonyl)benzyl)-N-phenylmorpholine-4-carboxamide as pale yellow oil (0.334 g, 89.4%).

[Step 5] Compound 21429

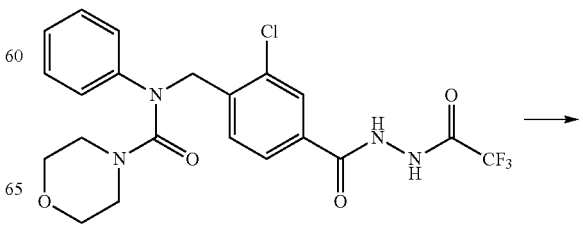

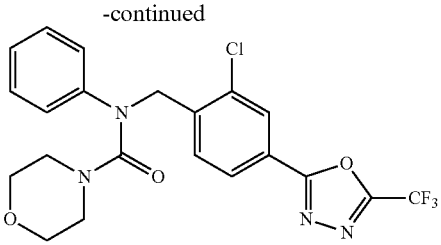

N-(2-chloro-4-(2-(2,2,2-trifluoroacetyl)hydrazine-1-carbonyl)benzyl)-N-phenylmorpholine-4-carboxamide (0.434 g, 0.895 mmol) prepared in Step 4 and 1-methoxy-N-triethylammoniosulfonyl-methanimidate (Burgess reagent, 0.320 g, 1.343 mmol) in tetrahydrofuran (10 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 12 g cartridge; ethyl acetate/hexane=20% to 70%) to give the title compound N-(2-chloro-4-(5-(trifluoromethyl)-1,3,4-oxadiazol-2-yl)benzyl)-N-phenylmorpholine-4-carboxamide as white solid (0.110 g, 26.3%).

$^1$H NMR (400 MHz, $CDCl_3$) δ 8.08 (d, 1H, J=1.6 Hz), 7.97 (dd, 1H, J=8.1, 1.6 Hz), 7.65 (d, 2H, J=8.2 Hz), 7.32 (t, 2H, J=7.9 Hz), 7.15-7.10 (m, 3H), 5.05 (s, 2H), 3.51 (t, 4H, J=4.7 Hz), 3.28 (t, 4H, J=4.7 Hz).

Example 100. Compound 21431: N-(2,6-difluoro-4-(5-(trifluoromethyl)-1,3,4-oxadiazol-2-yl)benzyl)-N-phenylmorpholine-4-carboxamide

[Step 1] Tert-butyl 3,5-difluoro-4-((phenylamino)methyl)benzoate

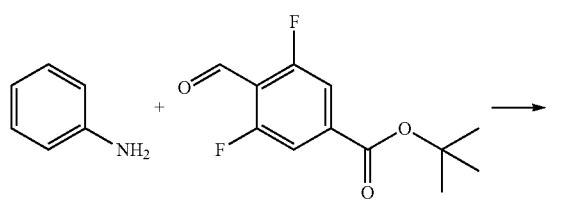

A solution of aniline (0.350 g, 3.758 mmol) and tert-butyl 3,5-difluoro-4-formylbenzoate (1.001 g, 4.134 mmol) in dichloromethane (10 mL) was stirred at the room temperature for 10 min, and mixed with sodium triacetoxyborohydride (1.593 g, 7.516 mmol). The reaction mixture was stirred at the same temperature for additional 17 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The title compound tert-butyl 3,5-difluoro-4-((phenylamino)methyl)benzoate was used without further purification (1.290 g, 107.5%, pale yellow oil).

[Step 2] Tert-butyl 3,5-difluoro-4-((N-phenylmorpholine-4-carboxamido)methyl)benzoate

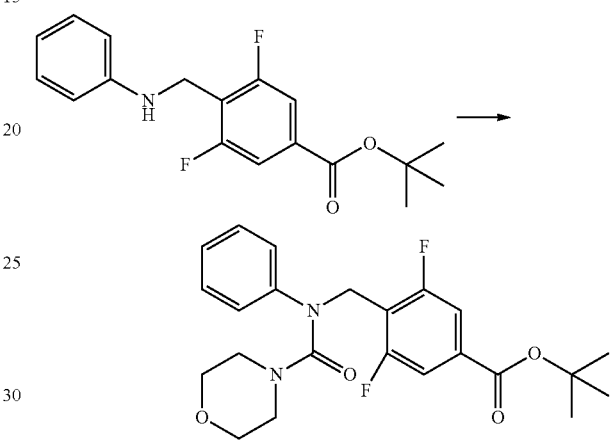

To a stirred solution of tert-butyl 3,5-difluoro-4-((phenylamino)methyl)benzoate (1.000 g, 3.131 mmol) prepared in Step 1 in dichloromethane (40 mL) were added at 0° C. triphosgene (0.743 g, 2.505 mmol) and N,N-diisopropylethylamine (2.734 mL, 15.657 mmol). The reaction mixture was stirred at the same temperature for 1 hr, treated at the room temperature with morpholine (0.327 mL, 3.758 mmol), and stirred for additional 2 hr. Then, saturated aqueous sodium bicarbonate solution was added to the reaction mixture, followed by extraction with dichloromethane. The organic layer was washed with brine, dried (anhydrous $MgSO_4$), filtered, and concentrated in vacuo. The concentrate was purified and concentrated by column chromatography ($SiO_2$, 24 g cartridge; ethyl acetate/hexane=0% to 30%) to give the title compound tert-butyl 3,5-difluoro-4-((N-phenylmorpholine-4-carboxamido)methyl)benzoate as pale yellow oil (0.737 g, 54.4%).

[Step 3] 3,5-Difluoro-4-((N-phenylmorpholine-4-carboxamido)methyl)benzoic acid

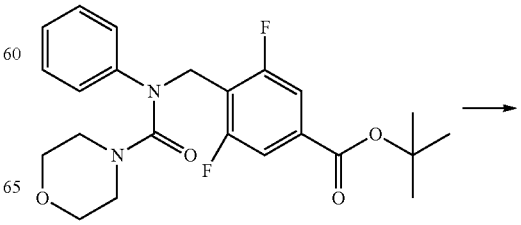

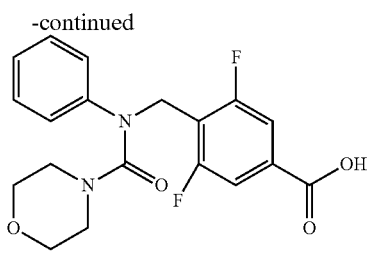

Tert-butyl 3,5-difluoro-4-((N-phenylmorpholine-4-carboxamido)methyl)benzoate (0.637 g, 1.473 mmol) prepared in Step 2 and lithium hydroxide (0.071 g, 2.946 mmol) were mixed at the room temperature in methanol (10 mL)/water (5 mL) and then stirred at 50° C. for 17 hr, and cooled down to the room temperature to terminate the reaction. The reaction mixture was concentrated under the reduced pressure to remove the solvent. The residue was diluted with aqueous 1N-hydrochloric acid solution (50 mL) and stirred at the ambient temperature. The resulting precipitates were collected by filtration, washed by water, and dried to give the title compound 3,5-difluoro-4-((N-phenylmorpholine-4-carboxamido)methyl)benzoic acid as white solid (0.491 g, 88.6%).

[Step 4] N-(2,6-difluoro-4-(hydrazinecarbonyl)benzyl)-N-phenylmorpholine-4-carboxamide

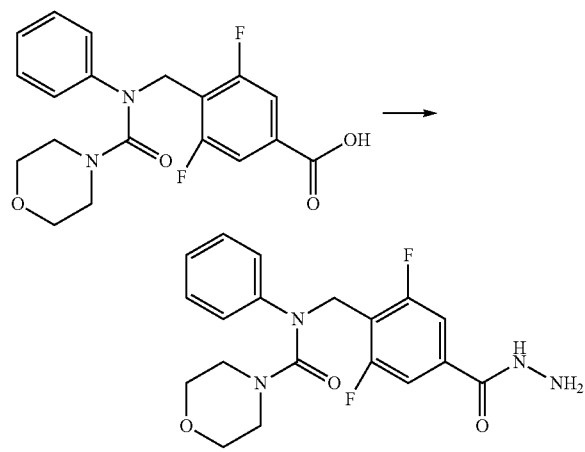

A solution of 3,5-difluoro-4-((N-phenylmorpholine-4-carboxamido)methyl)benzoic acid (0.390 g, 1.036 mmol) prepared in Step 3, hydrazine monohydrate (2.521 mL, 51.874 mmol), 1-Ethyl-3-(3-dimethylaminopropyl)carbodiimide (EDC, 0.397 g, 2.072 mmol), 1H-benzo[d][1,2,3]triazol-1-ol (HOBt, 0.280 g, 2.072 mmol) and N,N-diisopropylethylamine (0.905 mL, 5.181 mmol) in dichloromethane (10 mL) was stirred at the room temperature for 17 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 10%) to give the title compound N-(2,6-difluoro-4-(hydrazinecarbonyl)benzyl)-N-phenylmorpholine-4-carboxamide as pale yellow solid (0.347 g, 85.8%).

[Step 5] N-(2,6-difluoro-4-(2-(2,2,2-trifluoroacetyl)hydrazine-1-carbonyl)benzyl)-N-phenylmorpholine-4-carboxamide

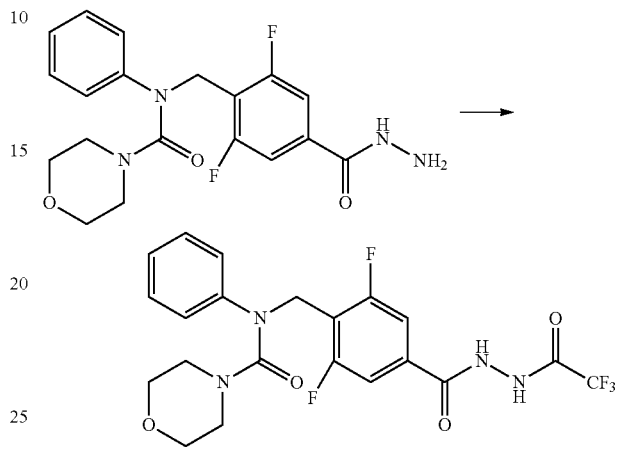

A solution of N-(2,6-difluoro-4-(hydrazinecarbonyl)benzyl)-N-phenyl morpholine-4-carboxamide (0.170 g, 0.435 mmol) prepared in Step 4 and triethylamine (0.091 mL, 0.653 mmol) in dichloromethane (10 mL) was mixed at the room temperature with trifluoroacetic anhydride (0.049 mL, 0.392 mmol). The reaction mixture was stirred at the same temperature for 1 hr, and saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(2,6-difluoro-4-(2-(2,2,2-trifluoroacetyl)hydrazine-1-carbonyl)benzyl)-N-phenylmorpholine-4-carboxamide as pale yellow oil (0.116 g, 56.9%).

[Step 6] Compound 21431

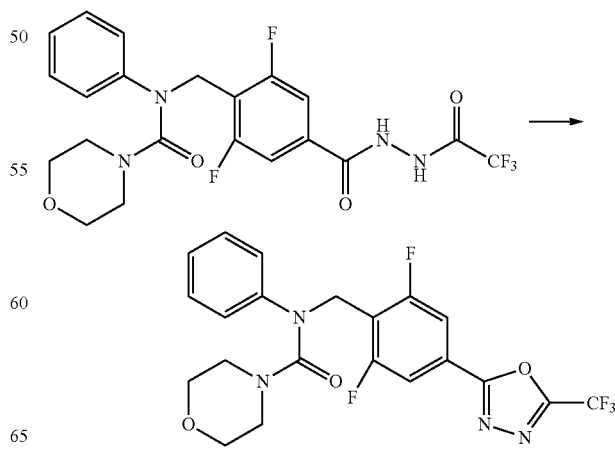

N-(2,6-difluoro-4-(2-(2,2,2-trifluoroacetyl)hydrazine-1-carbonyl)benzyl)-N-phenylmorpholine-4-carboxamide (0.227 g, 0.467 mmol) prepared in Step 5 and 1-methoxy-N-triethylammoniosulfonyl-methanimidate (Burgess reagent, 0.167 g, 0.700 mmol) in tetrahydrofuran (10 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=20% to 70%) to give the title compound N-(2,6-difluoro-4-(5-(trifluoromethyl)-1,3,4-oxadiazol-2-yl)benzyl)-N-phenylmorpholine-4-carboxamide as white solid (0.074 g, 33.9%).

$^1$H NMR (400 MHz, CDCl$_3$) δ 7.65 (d, 2H, J=7.1 Hz), 7.34 (t, 2H, J=7.9 Hz), 7.18 (t, 1H, J=7.4 Hz), 7.12 (d, 2H, J=8.3 Hz), 4.93 (s, 2H), 3.41 (t, 4H, J=4.8 Hz), 3.19 (t, 4H, J=4.8 Hz); LRMS (ES) m/z 469.4 (M$^+$+1).

Example 101. Compound 21432: N-(4-(5-(difluoromethyl)-1,3,4-oxadiazol-2-yl)-2,6-difluorobenzyl)-N-phenylmorpholine-4-carboxamide

[Step 1] N-(4-(2-(2,2-difluoroacetyl)hydrazine-1-carbonyl)-2,6-difluorobenzyl)-N-phenylmorpholine-4-carboxamide

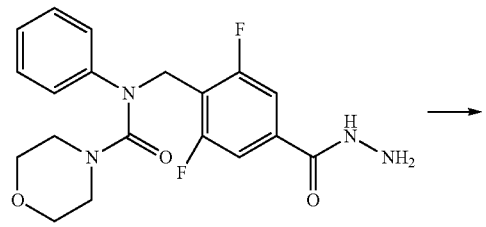

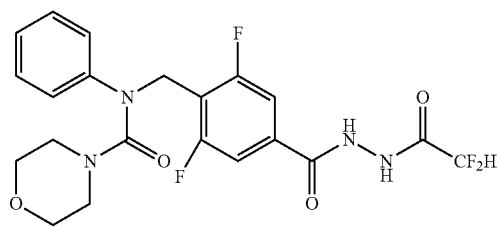

A solution of N-(2,6-difluoro-4-(hydrazinecarbonyl)benzyl)-N-phenylmorpholine-4-carboxamide (0.170 g, 0.435 mmol) prepared in Step 4 of Example 100 and triethylamine (0.091 mL, 0.653 mmol) in dichloromethane (10 mL) was mixed at the room temperature with 2,2-difluoroacetic anhydride (0.049 mL, 0.392 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(2-(2,2-difluoroacetyl)hydrazine-1-carbonyl)-2,6-difluorobenzyl)-N-phenylmorpholine-4-carboxamide as pale yellow oil (0.116 g, 56.9%).

[Step 2] Compound 21432

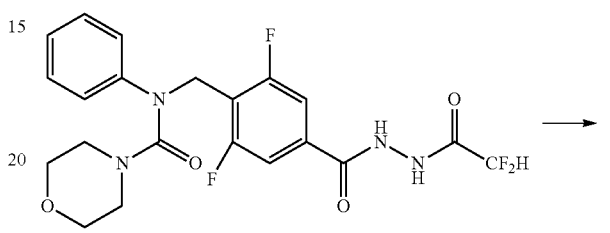

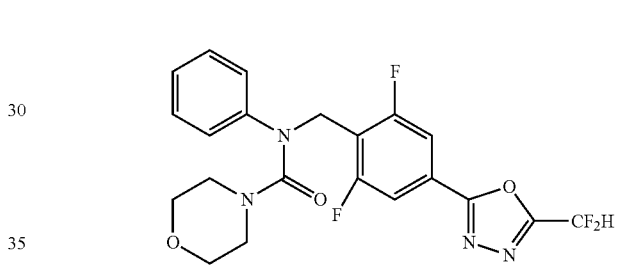

N-(4-(2-(2,2-difluoroacetyl)hydrazine-1-carbonyl)-2,6-difluorobenzyl)-N-phenylmorpholine-4-carboxamide (0.200 g, 0.427 mmol) prepared in Step 1 and 1-methoxy-N-triethylammoniosulfonyl-methanimidate (Burgess reagent, 0.153 g, 0.640 mmol) in tetrahydrofuran (10 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=20% to 70%) to give the title compound N-(4-(5-(difluoromethyl)-1,3,4-oxadiazol-2-yl)-2,6-difluorobenzyl)-N-phenylmorpholine-4-carboxamide as white solid (0.027 g, 14:0%).

$^1$H NMR (400 MHz, CDCl$_3$) δ 7.65 (d, 2H, J=7.3 Hz), 7.34 (t, 2H, J=7.8 Hz), 7.17 (t, 1H, J=7.4 Hz), 7.12 (d, 2H, J=7.6 Hz), 6.92 (t, 1H, J=51.6 Hz); LRMS (ES) m/z 451.5 (M$^+$+1).

Example 102. Compound 21433: N-(2,4-difluorophenyl)-N-(4-(5-(trifluoromethyl)-1,3,4-oxadiazol-2-yl)benzyl)thiomorpholine-4-carboxamide 1,1-dioxide

[Step 1] Methyl 4-((N-(2,4-difluorophenyl)-1,1-dioxidothiomorpholine-4-carboxamido)methyl)benzoate

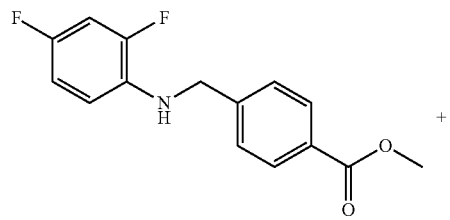

+

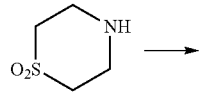

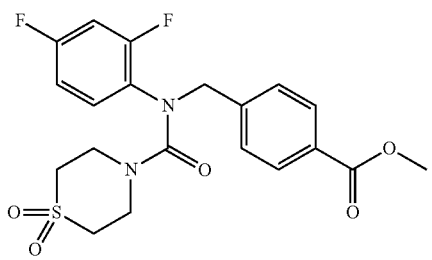

To a stirred solution of methyl 4-(((2,4-difluorophenyl)amino)methyl)benzoate (0.200 g, 0.721 mmol) and N,N-diisopropylethylamine (0.749 mL, 4.328 mmol) in dichloromethane (5 mL) was added at 0° C. triphosgene (0.107 g, 0.361 mmol). The reaction mixture was stirred at the same temperature for 30 min, treated at the room temperature with thiomorpholine 1,1-dioxide (0.107 g, 0.793 mmol), and stirred for additional 16 hr. The reaction mixture was concentrated under the reduced pressure to remove the solvent, and saturated aqueous ammonium chloride solution was added to the concentrate, followed by extraction with dichloromethane. The organic layer was washed with brine, dried (anhydrous MgSO₄), filtered, and concentrated in vacuo. The concentrate was purified and concentrated by column chromatography (SiO₂, 12 g cartridge; ethyl acetate/hexane=20% to 50%) to give the title compound methyl 4-((N-(2,4-difluorophenyl)-1,1-dioxidothiomorpholine-4-carboxamido)methyl)benzoat e as white solid (0.256 g, 80.9%).

[Step 2] N-(2,4-difluorophenyl)-N-(4-(hydrazinecarbonyl)benzyl)thiomorpholine-4-carboxamide 1,1-dioxide

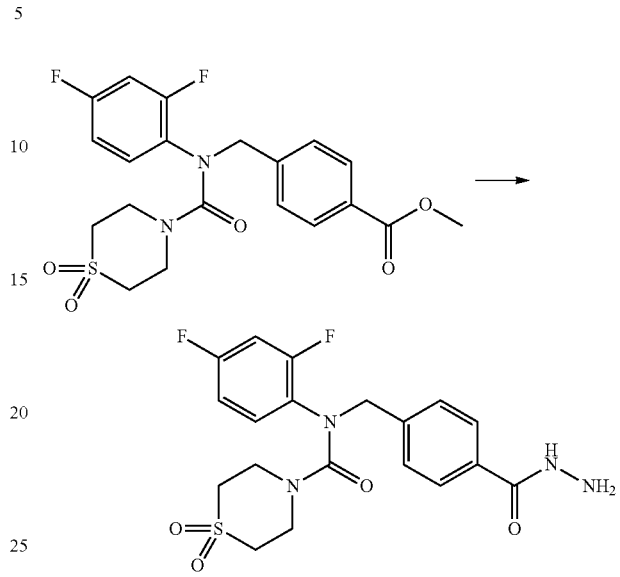

Methyl 4-((N-(2,4-difluorophenyl)-1,1-dioxidothiomorpholine-4-carboxamido)methyl)benzoat e (0.256 g, 0.584 mmol) prepared in Step 1 and hydrazine monohydrate (0.585 g, 11.678 mmol) in dichloromethane (3 mL) was mixed at the room temperature and then heated at 120° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-(2,4-difluorophenyl)-N-(4-(hydrazinecarbonyl)benzyl)thiomorpholine-4-carboxamide 1,1-dioxide as white foam (0.150 g, 58.6%).

[Step 3] N-(2,4-difluorophenyl)-N-(4-(2-(2,2,2-trifluoroacetyl)hydrazine-1-carbonyl)benzyl)thiomorpholine-4-carboxamide 1,1-dioxide

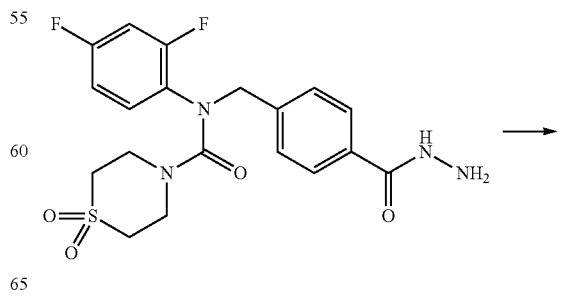

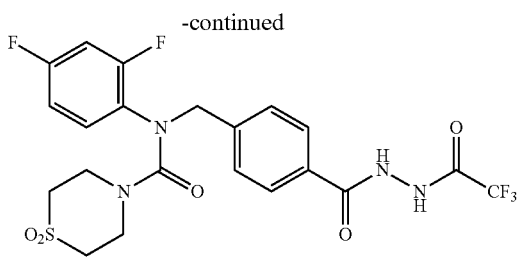

A solution of N-(2,4-difluorophenyl)-N-(4-(hydrazinecarbonyl)benzyl)thiomorpholine-4-carboxamide 1,1-dioxide (0.150 g, 0.342 mmol) prepared in Step 2 and triethylamine (0.095 mL, 0.684 mmol) in dichloromethane (10 mL) was mixed at the room temperature with trifluoroacetic anhydride (0.053 mL, 0.308 mmol). The reaction mixture was stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-(2,4-difluorophenyl)-N-(4-(2-(2,2,2-trifluoroacetyl)hydrazine-1-carbonyl)benzyl)thiomorpholine-4-carboxamide 1,1-dioxide as white foam (0.110 g, 60.2%).

[Step 4] Compound 21433

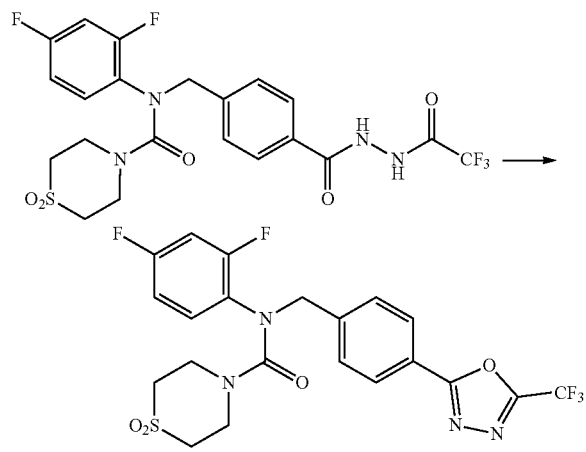

N-(2,4-difluorophenyl)-N-(4-(2-(2,2,2-trifluoroacetyl)hydrazine-1-carbonyl)benzyl)thiomorpholine-4-carboxamide 1,1-dioxide (0.110 g, 0.206 mmol) prepared in Step 3 and 1-methoxy-N-triethylammoniosulfonyl-methanimidate 1-methoxy-N-triethylammoniosulfonyl-methanimidate (Burgess reagent, 0.074 g, 0.309 mmol) in tetrahydrofuran (2 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(2,4-difluorophenyl)-N-(4-(5-(trifluoromethyl)-1,3,4-oxadiazol-2-yl)benzyl)thiomorpholine-4-carboxamide 1,1-dioxide as white solid (0.058 g, 54.1%).

$^1$H NMR (400 MHz, CDCl$_3$) δ 8.05 (d, 2H, J=8.3 Hz), 7.46 (d, 2H, J=8.3 Hz), 6.70-6.58 (m, 3H), 4.92 (s, 2H), 3.79-3.71 (m, 4H), 2.99-2.91 (m, 4H); LRMS (ESI) m/z 517.06 (M$^+$+H).

Example 103. Compound 21434: N-(2-fluoro-4-methylphenyl)-N-(4-(5-(trifluoromethyl)-1,3,4-oxadiazol-2-yl)benzyl)thiomorpholine-4-carboxamide 1,1-dioxide

[Step 1] Methyl 4-((N-(2-fluoro-4-methylphenyl)-1,1-dioxidothiomorpholine-4-carboxamido)methyl)benzoate

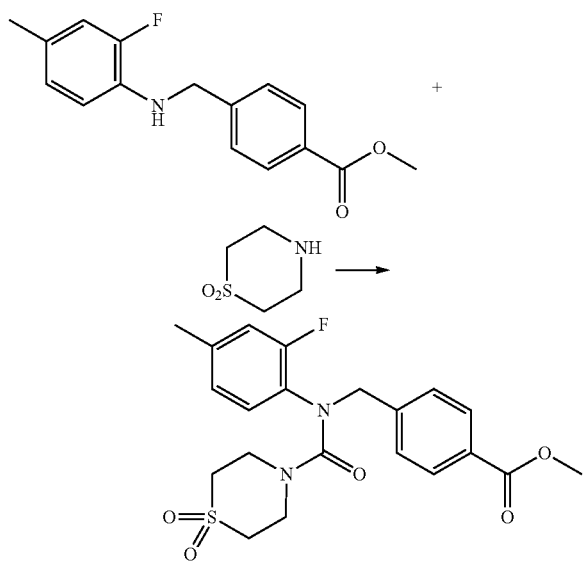

To a stirred solution of methyl 4-(((2-fluoro-4-methylphenyl)amino)methyl)benzoate (0.200 g, 0.732 mmol) and N,N-diisopropylethylamine (0.760 mL, 4.391 mmol) in dichloromethane (5 mL) was added at 0° C. triphosgene (0.109 g, 0.366 mmol). The reaction mixture was stirred at the same temperature for 30 min, treated at the room temperature with thiomorpholine 1,1-dioxide (0.109 g, 0.805 mmol), and stirred for additional 16 hr. The reaction mixture was concentrated under the reduced pressure to remove the solvent, and saturated aqueous ammonium chloride solution was added to the concentrate, followed by extraction with dichloromethane. The organic layer was washed with brine, dried (anhydrous MgSO$_4$), filtered, and concentrated in vacuo. The concentrate was purified and concentrated by column chromatography (SiO$_2$, 12 g cartridge; ethyl acetate/hexane=20% to 50%) to give the title compound methyl 4-((N-(2-fluoro-4-methylphenyl)-1,1-dioxidothiomorpholine-4-carboxamido)methyl)benzoate as yellow solid (0.231 g, 72.7%).

447

[Step 2] N-(2-fluoro-4-methylphenyl)-N-(4-(hydrazinecarbonyl)benzyl)thiomorpholine-4-carboxamide 1,1-dioxide

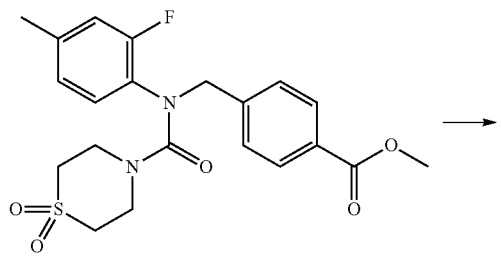

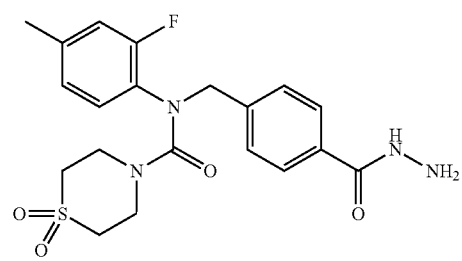

Methyl 4-((N-(2-fluoro-4-methylphenyl)-1,1-dioxidothiomorpholine-4-carboxamido)methyl)benzoate (0.231 g, 0.532 mmol) prepared in Step 1 and hydrazine monohydrate (0.532 g, 10.633 mmol) in dichloromethane (3 mL) was mixed at the room temperature and then heated at 120° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-(2-fluoro-4-methylphenyl)-N-(4-(hydrazinecarbonyl)benzyl)thiomorpholine-4-carboxamide 1,1-dioxide as white foam (0.149 g, 64.6%).

[Step 3] N-(2-fluoro-4-methylphenyl)-N-(4-(2-(2,2,2-trifluoroacetyl)hydrazine-1-carbonyl)benzyl) thiomorpholine-4-carboxamide 1,1-dioxide

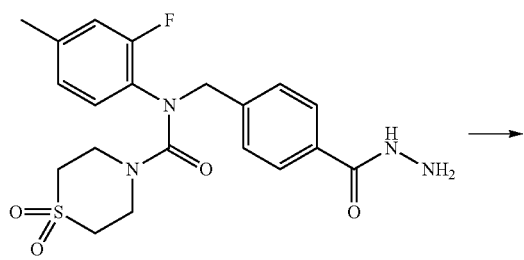

448

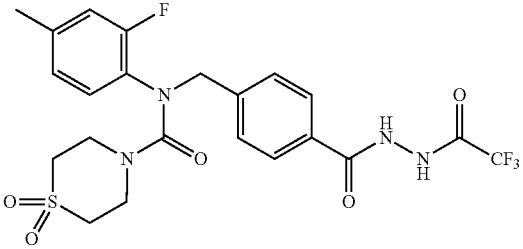

A solution of N-(2-fluoro-4-methylphenyl)-N-(4-(hydrazinecarbonyl)benzyl)thiomorpholine-4-carboxamide 1,1-dioxide (0.150 g, 0.345 mmol) prepared in Step 2 and triethylamine (0.095 mL, 0.690 mmol) in dichloromethane (10 mL) was mixed at the room temperature with trifluoroacetic anhydride (0.054 mL, 0.311 mmol). The reaction mixture was stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 5%) to give the title compound N-(2-fluoro-4-methylphenyl)-N-(4-(2-(2,2,2-trifluoroacetyl)hydrazine-1-carbonyl)benzyl)thiomorpholine-4-carboxamide 1,1-dioxide as white foam (0.139 g, 75.6%).

[Step 4] Compound 21434

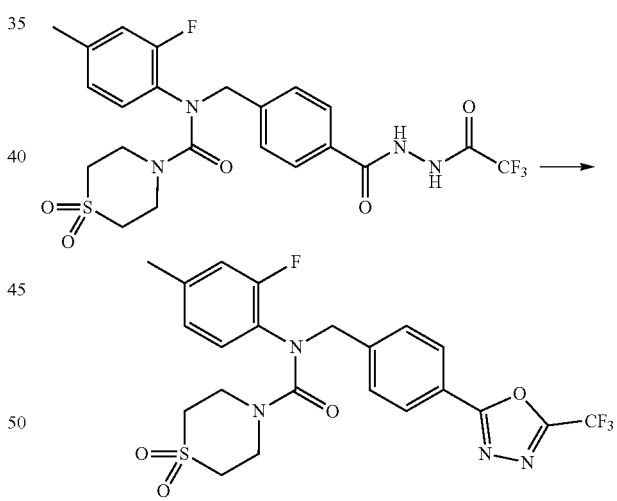

N-(2-fluoro-4-methylphenyl)-N-(4-(2-(2,2,2-trifluoroacetyl)hydrazine-1-carbonyl)benzyl)thiomorpholine-4-carboxamide 1,1-dioxide (0.139 g, 0.261 mmol) prepared in Step 3 and 1-methoxy-N-triethylammoniosulfonyl-methanimidate (Burgess reagent, 0.093 g, 0.392 mmol) in tetrahydrofuran (2 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(2-fluoro-4-methylphenyl)-N-(4-(5-(trifluoromethyl)-1,3,4-oxadiazol-2-yl)benzyl)thiomorpholine-4-carboxamide 1,1-dioxide as light brown foam (0.084 g, 62.6%).

$^1$H NMR (400 MHz, CDCl$_3$) δ 8.03-7.96 (m, 2H), 7.50-7.43 (m, 2H), 6.98-6.88 (m, 3H), 4.78 (s, 2H), 3.74-3.66 (m, 4H), 2.78-2.71 (m, 4H), 2.33 (s, 3H); LRMS (ESI) m/z 513.05 (M$^+$+H).

Example 104. Compound 21435: N-(3-(furan-3-yl)phenyl)-N-(4-(5-(trifluoromethyl)-1,3,4-oxadiazol-2-yl)benzyl)thiomorpholine-4-carboxamide 1,1-dioxide

[Step 1] N-(3-bromophenyl)thiomorpholine-4-carboxamide 1,1-dioxide

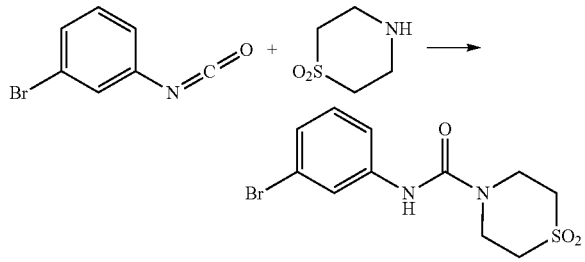

A solution of 1-bromo-3-isocyanatobenzene (3.145 mL, 25.250 mmol) and thiomorpholine 1,1-dioxide (3.447 g, 25.502 mmol) in diethylether (100 mL) was stirred at the room temperature for 18 hr. The precipitates were collected by filtration, washed by diethylether, and dried to give the title compound N-(3-bromophenyl)thiomorpholine-4-carboxamide 1,1-dioxide as white solid (8.240 g, 97.9%).

[Step 2] Methyl 4-((N-(3-bromophenyl)-1,1-dioxidothiomorpholine-4-carboxamido)methyl)benzoate

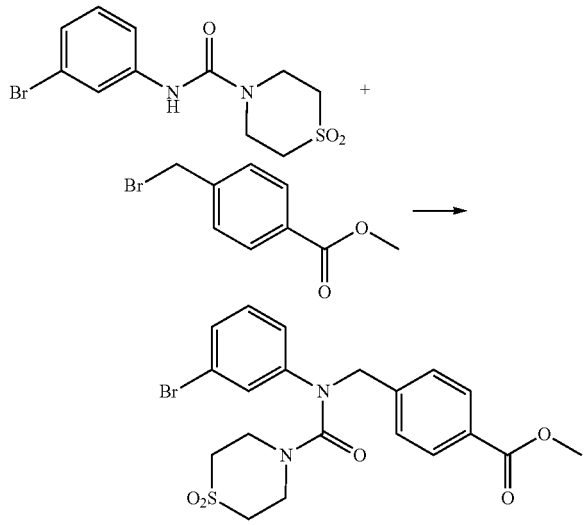

To a stirred solution of N-(3-bromophenyl)thiomorpholine-4-carboxamide 1,1-dioxide (8.240 g, 24.730 mmol) prepared in Step 1 in N,N-dimethylformamide (100 mL) was added at 0° C. sodium hydride (60.00%, 1.088 g, 27.203 mmol). The reaction mixture was stirred at the same temperature, treated at the room temperature with methyl 4-(bromomethyl)benzoate (6.231 g, 27.203 mmol), and stirred for additional 2 hr. Then, saturated aqueous sodium bicarbonate solution was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 80 g cartridge; methanol/dichloromethane=0% to 3%) to give the title compound methyl 4-((N-(3-bromophenyl)-1,1-dioxidothiomorpholine-4-carboxamido)methyl)benzoate as white solid (11.900 g, 100.0%).

[Step 3] Methyl 4-((N-(3-(furan-3-yl)phenyl)-1,1-dioxidothiomorpholine-4-carboxamido)methyl)benzoate

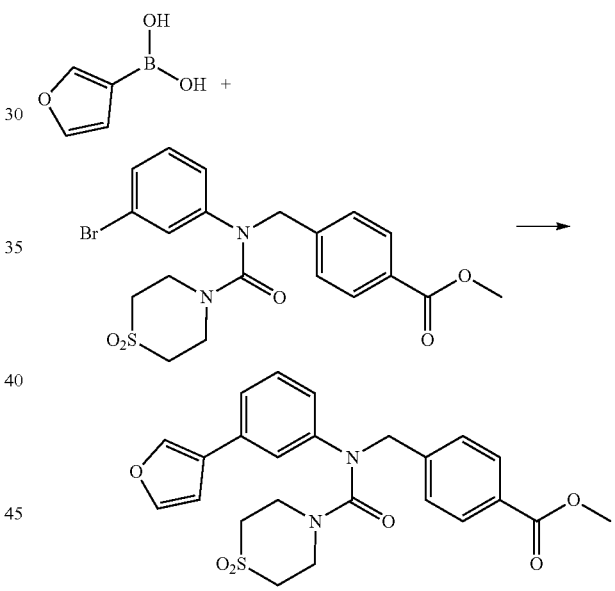

A mixture of methyl 4-((N-(3-bromophenyl)-1,1-dioxidothiomorpholine-4-carboxamido)methyl)benzoate (0.500 g, 1.039 mmol) prepared in Step 2, 3-furanylboronic acid (0.139 g, 1.246 mmol), [1,1'-bis(di-tert-butylphosphino)ferrocene]palladium(II) dichloride (0.034 g, 0.052 mmol) and Cs2CO3 (1.009 g, 3.116 mmol) in water (3 mL)/1,4-dioxane (12 mL) was heated at 140° C. for 20 min under the microwaves, and cooled down to the room temperature to terminate the reaction. Then, water was added to the reaction mixture, followed by extraction with ethyl acetate. The organic layer was washed with brine, dried (anhydrous MgSO$_4$), filtered, and concentrated in vacuo. The concentrate was purified and concentrated by column chromatography (SiO$_2$, 24 g cartridge; ethyl acetate/hexane=0% to 50%) to give the title compound methyl 4-((N-(3-(furan-3-yl)phenyl)-1,1-dioxidothiomorpholine-4-carboxamido)methyl)benzoate as brown solid (0.403 g, 82.8%).

[Step 4] N-(3-(furan-3-yl)phenyl)-N-(4-(hydrazinecarbonyl)benzyl)thiomorpholine-4-carboxamide 1,1-dioxide

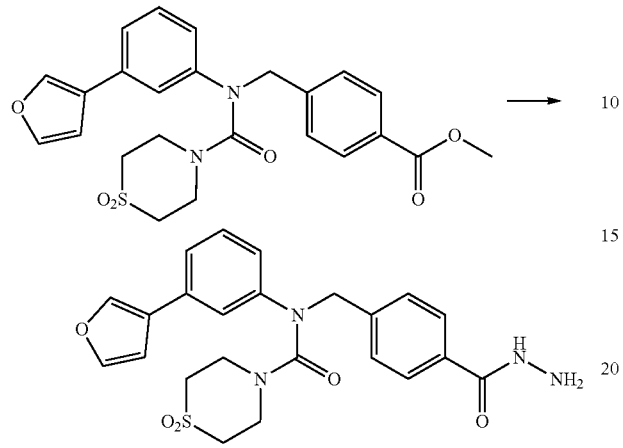

A mixture of methyl 4-((N-(3-(furan-3-yl)phenyl)-1,1-dioxidothiomorpholine-4-carboxamido)methyl)benzoate (0.403 g, 0.860 mmol) prepared in Step 3 and hydrazine monohydrate (0.812 mL, 17.203 mmol) in ethanol (10 mL) was heated at reflux for 16 hr, and cooled down to the ambient temperature. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(3-(furan-3-yl)phenyl)-N-(4-(hydrazinecarbonyl)benzyl)thiomorpholine-4-carboxamide 1,1-dioxide as white solid (0.229 g, 56.8%).

[Step 5] N-(3-(furan-3-yl)phenyl)-N-(4-(2-(2,2,2-trifluoroacetyl)hydrazine-1-carbonyl)benzyl)thiomorpholine-4-carboxamide 1,1-dioxide

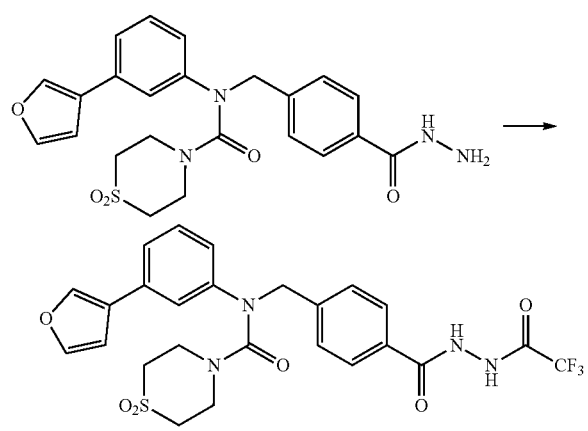

A solution of N-(3-(furan-3-yl)phenyl)-N-(4-(hydrazinecarbonyl)benzyl)thiomorpholine-4-carboxamide 1,1-dioxide (0.229 g, 0.489 mmol) prepared in Step 4 and triethylamine (0.102 mL, 0.733 mmol) in dichloromethane (5 mL) was mixed at 0° C. with trifluoroacetic anhydride (0.061 mL, 0.440 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-(3-(furan-3-yl)phenyl)-N-(4-(2-(2,2,2-trifluoroacetyl)hydrazine-1-carbonyl)benzyl)thiomorpholine-4-carboxamide 1,1-dioxide as white solid (0.076 g, 27.5%).

[Step 6] Compound 21435

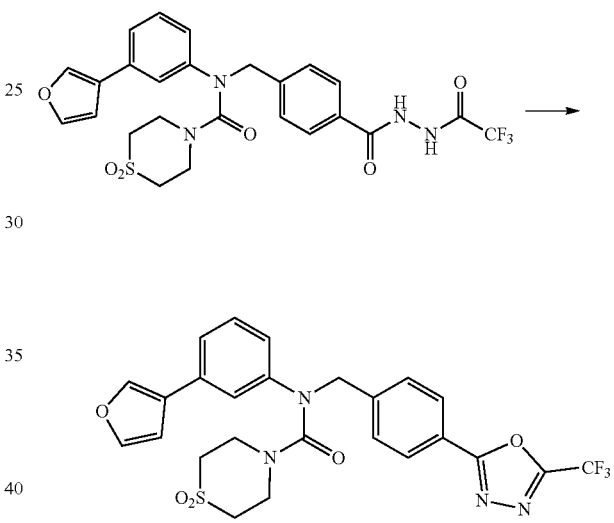

A mixture of N-(3-(furan-3-yl)phenyl)-N-(4-(2-(2,2,2-trifluoroacetyl)hydrazine-1-carbonyl)benzyl)thiomorpholine-4-carboxamide 1,1-dioxide (0.076 g, 0.135 mmol) prepared in Step 5 and 1-methoxy-N-triethylammoniosulfonyl-methanimidate (Burgess reagent, 0.048 g, 0.202 mmol) in tetrahydrofuran (1 mL) was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(3-(furan-3-yl)phenyl)-N-(4-(5-(trifluoromethyl)-1,3,4-oxadiazol-2-yl)benzyl)thiomorpholine-4-carboxamide 1,1-dioxide as bright yellow solid (0.044 g, 60.2%).

$^1$H NMR (400 MHz, CDCl$_3$) δ 8.03 (d, 2H, J=8.1 Hz), 7.70-7.69 (m, 1H), 7.49-7.48 (m, 1H), 7.47 (d, 2H, J=8.2 Hz), 7.35-7.33 (m, 2H), 7.18-7.17 (m, 1H), 6.94-6.92 (m, 1H), 6.61-6.60 (m, 1H), 4.92 (s, 2H), 3.74-3.73 (m, 4H), 2.83-2.81 (m, 4H); LRMS (ES) m/z 547.41 (M$^+$+1).

453

Example 105. Compound 21436: N-(3-(pyridin-3-yl)phenyl)-N-(4-(5-(trifluoromethyl)-1,3,4-oxadiazol-2-yl)benzyl)thiomorpholine-4-carboxamide 1,1-dioxide

[Step 1] Methyl 4-((1,1-dioxido-N-(3-(pyridin-3-yl)phenyl)thiomorpholine-4-carboxamido)methyl)benzoate

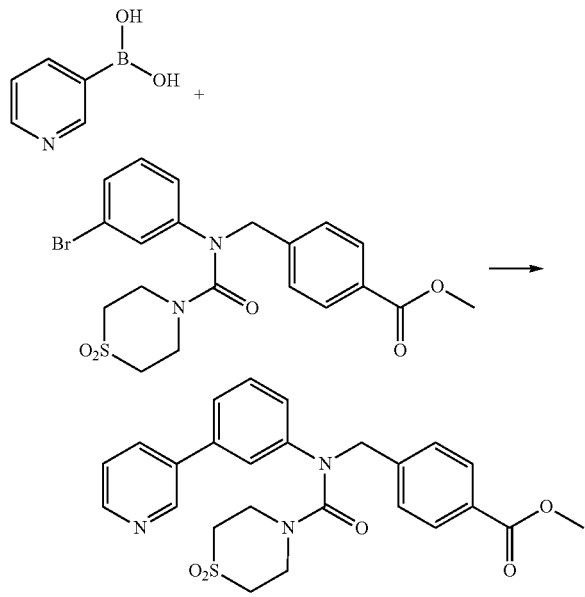

A mixture of methyl 4-((N-(3-bromophenyl)-1,1-dioxido-thiomorpholine-4-carboxamido)methyl)benzoate (0.500 g, 1.039 mmol) prepared in Step 2 of Example 104, 3-pyridineboronic acid (0.153 g, 1.246 mmol), Pd(dtbpf)Cl2 (0.034 g, 0.052 mmol) and Cs2CO3 (1.009 g, 3.116 mmol) in water (2 mL)/1,4-dioxane (8 mL) was heated at 140° C. for 20 min under the microwaves, and cooled down to the room temperature to terminate the reaction. Then, water was added to the reaction mixture, followed by extraction with ethyl acetate. The organic layer was washed with brine, dried (anhydrous MgSO4), filtered, and concentrated in vacuo. The concentrate was purified and concentrated by column chromatography (SiO2, 24 g cartridge; methanol/dichloromethane=0% to 5%) to give the title compound methyl 4-((1,1-dioxido-N-(3-(pyridin-3-yl)phenyl)thiomorpholine-4-carboxamido)methyl)benzoate as brown solid (0.402 g, 80.7%).

[Step 2] N-(4-(hydrazinecarbonyl)benzyl)-N-(3-(pyridin-3-yl)phenyl)thiomorpholine-4-carboxamide 1,1-dioxide

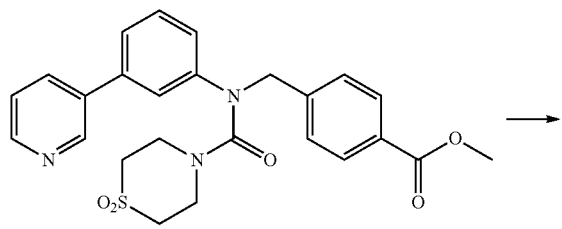

454

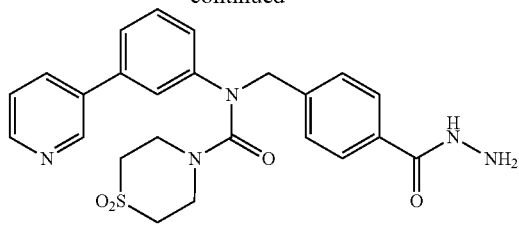

A mixture of methyl 4-((1,1-dioxido-N-(3-(pyridin-3-yl)phenyl)thiomorpholine-4-carboxamido)methyl)benzoate (0.402 g, 0.858 mmol) prepared in Step 1 and hydrazine monohydrate (0.810 mL, 17.160 mmol) in ethanol (10 mL) was heated at reflux for 16 hr, and cooled down to the ambient temperature. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO2, 24 g cartridge; methanol/dichloromethane=0% to 5%) to give the title compound N-(4-(hydrazinecarbonyl)benzyl)-N-(3-(pyridin-3-yl)phenyl)thiomorpholine-4-carboxamide 1,1-dioxide as white solid (0.403 g, 97.9%).

[Step 3] N-(3-(pyridin-3-yl)phenyl)-N-(4-(2-(2,2,2-trifluoroacetyl)hydrazine-1-carbonyl)benzyl)thiomorpholine-4-carboxamide 1,1-dioxide

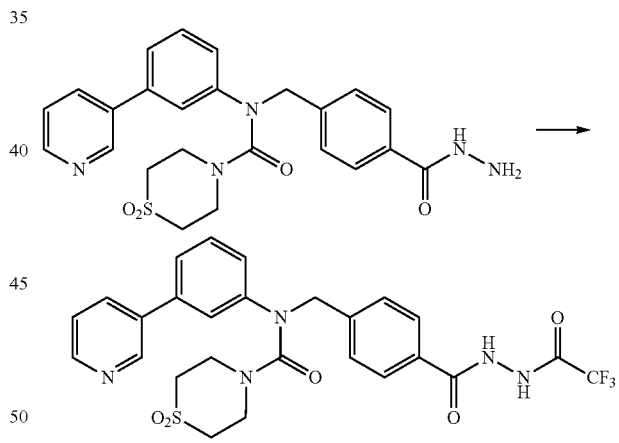

A solution of N-(4-(hydrazinecarbonyl)benzyl)-N-(3-(pyridin-3-yl)phenyl)thiomorpholine-4-carboxamide 1,1-dioxide (0.403 g, 0.840 mmol) prepared in Step 2 and triethylamine (0.175 mL, 1.261 mmol) in dichloromethane (10 mL) was mixed at 0° C. with trifluoroacetic anhydride (0.105 mL, 0.756 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO2, 24 g cartridge; methanol/dichloromethane=0% to 5%) to give the title compound N-(3-(pyridin-3-yl)phenyl)-N-(4-(2-(2,2,2-trifluoroacetyl)hydrazine-1-carbonyl)benzyl)thiomorpholine-4-carboxamide 1,1-dioxide as white solid (0.333 g, 68.8%).

[Step 4] Compound 21436

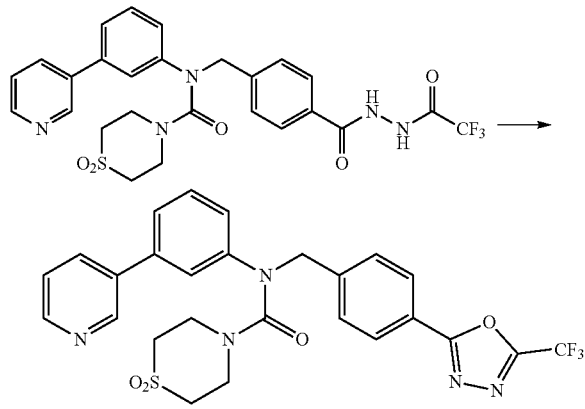

A mixture of N-(3-(pyridin-3-yl)phenyl)-N-(4-(2-(2,2,2-trifluoroacetyl)hydrazine-1-carbonyl)benzyl)thiomorpholine-4-carboxamide 1,1-dioxide (0.333 g, 0.579 mmol) prepared in Step 3 and 1-methoxy-N-triethylammoniosulfonyl-methanimidate (Burgess reagent, 0.207 g, 0.868 mmol) in tetrahydrofuran (2 mL) was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; ethyl acetate/hexane=0% to 50%) to give the title compound N-(3-(pyridin-3-yl)phenyl)-N-(4-(5-(trifluoromethyl)-1,3,4-oxadiazol-2-yl)benzyl)thiomorpholine-4-carboxamide 1,1-dioxide as white solid (0.178 g, 55.2%).

$^1$H NMR (400 MHz, CDCl₃) δ 8.83-8.82 (m, 1H), 8.66-8.65 (m, 1H), 8.04 (d, 2H, J=8.2 Hz), 7.92-7.89 (m, 1H), 7.52-7.42 (m, 5H), 7.33-7.32 (m, 1H), 7.15-7.13 (m, 1H), 4.97 (s, 2H), 3.75-3.74 (m, 4H), 2.89-2.86 (m, 4H); LRMS (ES) m/z 558.25 (M⁺+1).

Example 106. Compound 21437: N-(3-(benzo[d][1,3]dioxol-5-yl)phenyl)-N-(4-(5-(trifluoromethyl)-1,3,4-oxadiazol-2-yl)benzyl)thiomorpholine-4-carboxamide 1,1-dioxide

[Step 1] Methyl 4-((N-(3-(benzo[d][1,3]dioxol-5-yl)phenyl)-1,1-dioxidothiomorpholine-4-carboxamido)methyl)benzoate

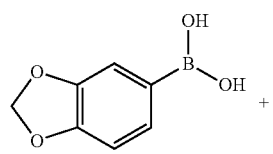

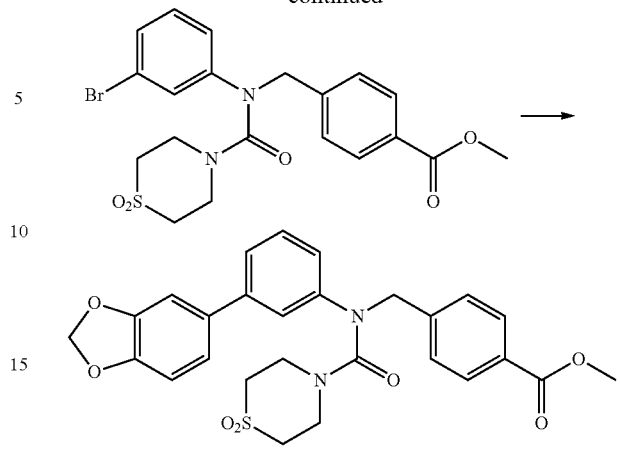

A mixture of methyl 4-((N-(3-bromophenyl)-1,1-dioxidothiomorpholine-4-carboxamido)methyl)benzoate (0.500 g, 1.039 mmol) prepared in Step 2 of Example 104, 3,4-methylenedioxyphenylboronic acid (0.207 g, 1.246 mmol), Pd(dtbpf)Cl2 (0.034 g, 0.052 mmol) and Cs2CO3 (1.009 g, 3.116 mmol) in water (3 mL)/1,4-dioxane (12 mL) was heated at 140° C. for 20 min under the microwaves, and cooled down to the room temperature to terminate the reaction. Then, water was added to the reaction mixture, followed by extraction with ethyl acetate. The organic layer was washed with brine, dried (anhydrous MgSO₄), filtered, and concentrated in vacuo. The concentrate was purified and concentrated by column chromatography (SiO₂, 24 g cartridge; ethyl acetate/hexane=0% to 50%) to give the title compound methyl 4-((N-(3-(benzo[d][1,3]dioxol-5-yl)phenyl)-1,1-dioxidothiomorpholine-4-carboxamido)methyl)benzoate as brown solid (0.486 g, 89.5%).

[Step 2] N-(3-(benzo[d][1,3]dioxol-5-yl)phenyl)-N-(4-(hydrazinecarbonyl)benzyl)thiomorpholine-4-carboxamide 1,1-dioxide

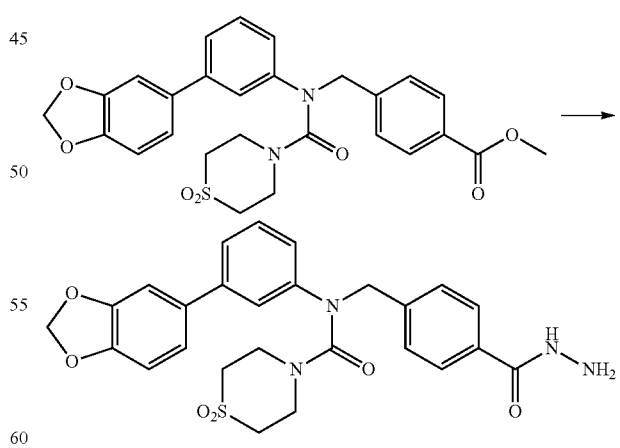

A mixture of methyl 4-((N-(3-(benzo[d][1,3]dioxol-5-yl)phenyl)-1,1-dioxidothiomorpholine-4-carboxamido)methyl)benzoate (0.486 g, 0.930 mmol) prepared in Step 1 and hydrazine monohydrate (0.878 mL, 18.600 mmol) in ethanol (10 mL) was heated at reflux for 16 hr, and cooled down to the ambient temperature. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(3-(benzo[d][1,3]dioxol-5-yl)phenyl)-N-(4-(hydrazinecarbonyl)benzyl) thiomorpholine-4-carboxamide 1,1-dioxide as brown solid (0.144 g, 29.6%).

[Step 3] N-(3-(benzo[d][1,3]dioxol-5-yl)phenyl)-N-(4-(2-(2,2,2-trifluoroacetyl)hydrazine-1-carbonyl) benzyl)thiomorpholine-4-carboxamide 1,1-dioxide

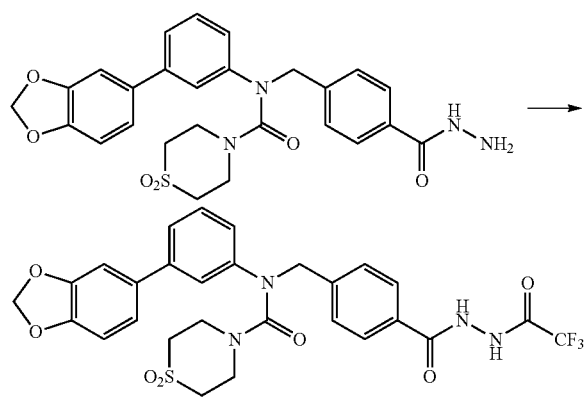

A solution of N-(3-(benzo[d][1,3]dioxol-5-yl)phenyl)-N-(4-(hydrazinecarbonyl)benzyl)thiomorpholine-4-carboxamide 1,1-dioxide (0.144 g, 0.276 mmol) prepared in Step 2 and triethylamine (0.057 mL, 0.413 mmol) in dichloromethane (3 mL) was mixed at 0° C. with trifluoroacetic anhydride (0.034 mL, 0.248 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-(3-(benzo[d][1,3]dioxol-5-yl)phenyl)-N-(4-(2-(2,2,2-trifluoroacetyl)hydrazine-1-carbonyl)benzyl)thiomorpholine-4-carboxamide 1,1-dioxide as white solid (0.019 g, 11.1%).

[Step 4] Compound 21437

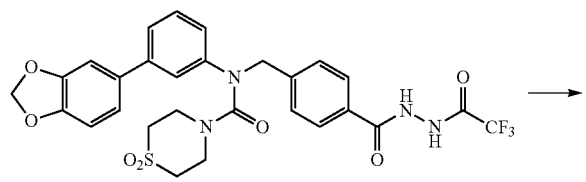

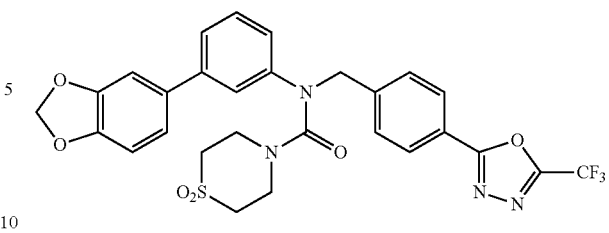

A mixture of N-(3-(benzo[d][1,3]dioxol-5-yl)phenyl)-N-(4-(2-(2,2,2-trifluoroacetyl)hydrazine-1-carbonyl)benzyl) thiomorpholine-4-carboxamide 1,1-dioxide (0.019 g, 0.031 mmol) prepared in Step 3 and 1-methoxy-N-triethylammoniosulfonyl-methanimidate (Burgess reagent, 0.011 g, 0.046 mmol) in tetrahydrofuran (1 mL) was heated at 150° C. for 30 min under the microwaves, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(3-(benzo[d][1,3]dioxol-5-yl)phenyl)-N-(4-(5-(trifluoromethyl)-1,3,4-oxadiazol-2-yl)benzyl)thiomorpholine-4-carboxamide 1,1-dioxide as white solid (0.011 g, 59.4%).

$^1$H NMR (400 MHz, CDCl$_3$) δ 8.03 (d, 2H, J=8.4 Hz), 7.47 (d, 2H, J=8.2 Hz), 7.38-7.33 (m, 2H), 7.18-7.17 (m, 1H), 7.01-6.98 (m, 1H), 6.94-6.85 (m, 3H), 4.93 (s, 2H), 3.74-3.73 (m, 4H), 2.83-2.81 (m, 4H); LRMS (ES) m/z 601.34 (M$^+$+1).

Example 107. Compound 21438: N-(3-(1-methyl-1H-indazol-6-yl)phenyl)-N-(4-(5-(trifluoromethyl)-1,3,4-oxadiazol-2-yl) benzyl)thiomorpholine-4-carboxamide 1,1-dioxide

[Step 1] Methyl 4-((N-(3-(1-methyl-1H-indazol-6-yl)phenyl)-1,1-dioxidothiomorpholine-4-carboxamido)methyl)benzoate

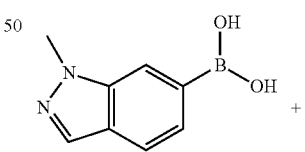
+

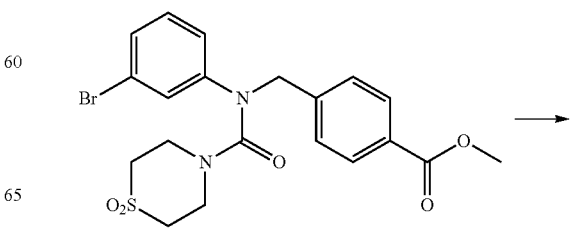

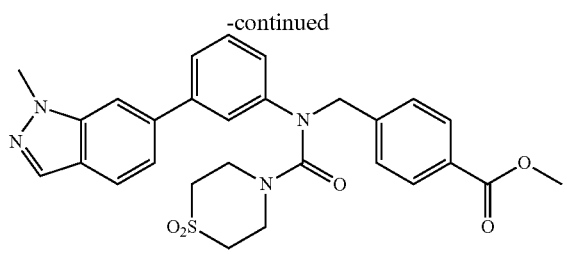

A mixture of methyl 4-((N-(3-bromophenyl)-1,1-dioxido-thiomorpholine-4-carboxamido)methyl)benzoate (0.500 g, 1.039 mmol) prepared in Step 2 of Example 104, 1-methyl-1H-indazole-6-boronic acid (0.219 g, 1.246 mmol), Pd(dt-bpf)Cl2 (0.034 g, 0.052 mmol) and Cs2CO3 (1.009 g, 3.116 mmol) in water (3 mL)/1,4-dioxane (12 mL) was heated at 140° C. for 20 min under the microwaves, and cooled down to the room temperature to terminate the reaction. Then, water was added to the reaction mixture, followed by extraction with ethyl acetate. The organic layer was washed with brine, dried (anhydrous MgSO4), filtered, and concentrated in vacuo. The concentrate was purified and concentrated by column chromatography (SiO2, 24 g cartridge; methanol/dichloromethane=0% to 5%) to give the title compound methyl 4-((N-(3-(1-methyl-1H-indazol-6-yl)phenyl)-1,1-dioxidothiomorpholine-4-carboxamido)methyl)benzoate as brown solid (0.484 g, 87.5%).

[Step 2] N-(4-(hydrazinecarbonyl)benzyl)-N-(3-(1-methyl-1H-indazol-6-yl)phenyl)thiomorpholine-4-carboxamide 1,1-dioxide

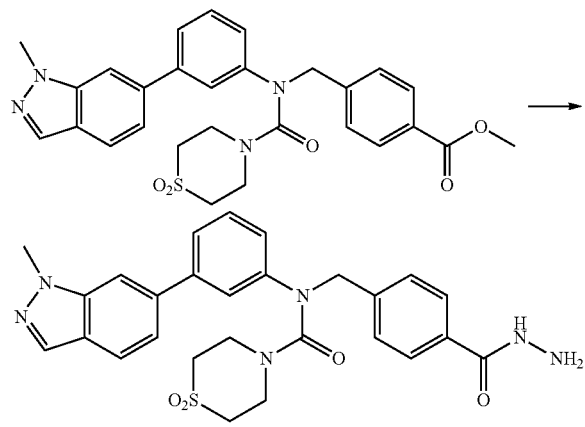

A mixture of methyl 4-((N-(3-(1-methyl-1H-indazol-6-yl)phenyl)-1,1-dioxidothiomorpholine-4-carboxamido)methyl)benzoate (0.484 g, 0.909 mmol) prepared in Step 1 and hydrazine monohydrate (0.858 mL, 18.174 mmol) in ethanol (10 mL) was heated at reflux for 16 hr, and cooled down to the ambient temperature. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO2, 24 g cartridge; methanol/dichloromethane=0% to 5%) to give the title compound N-(4-(hydrazinecarbonyl)benzyl)-N-(3-(1-methyl-1H-indazol-6-yl)phenyl)thiomorpholine-4-carboxamide 1,1-dioxide as brown solid (0.131 g, 27.1%).

[Step 3] N-(3-(1-methyl-11-1-indazol-6-yl)phenyl)-N-(4-(2-(2,2,2-trifluoroacetyl)hydrazine-1-carbonyl)benzyl)thiomorpholine-4-carboxamide 1,1-dioxide

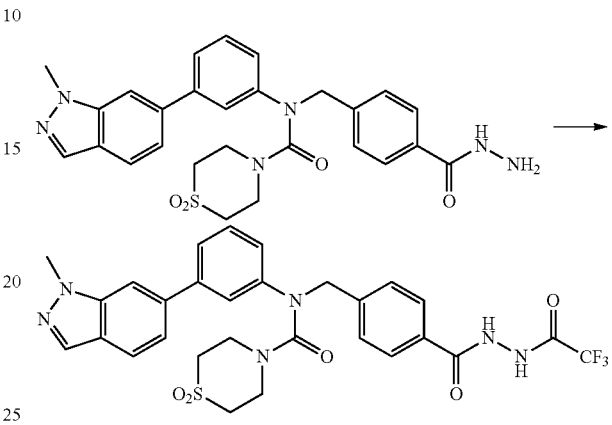

A solution of N-(4-(hydrazinecarbonyl)benzyl)-N-(3-(1-methyl-1H-indazol-6-yl)phenylthiomorpholine-4-carboxamide 1,1-dioxide (0.131 g, 0.246 mmol) prepared in Step 2 and triethylamine (0.051 mL, 0.369 mmol) in dichloromethane (3 mL) was mixed at 0° C. with trifluoroacetic anhydride (0.031 mL, 0.221 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO2, 12 g cartridge; methanol/dichloromethane=0% to 5%) to give the title compound N-(3-(1-methyl-1H-indazol-6-yl)phenyl)-N-(4-(2-(2,2,2-trifluoroacetyl)hydrazine-1-carbonyl)benzyl)thiomorpholine-4-carboxamide 1,1-dioxide as white solid (0.095 g, 61.4%).

[Step 4] Compound 21438

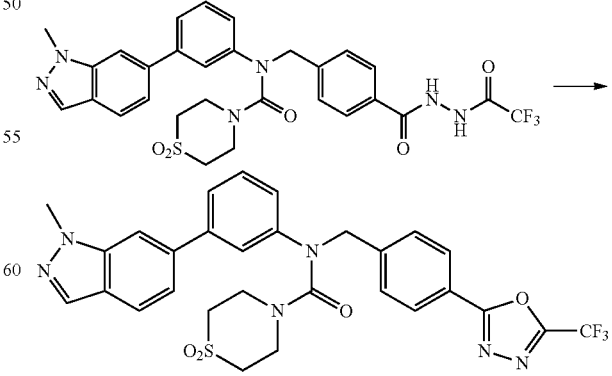

A mixture of N-(3-(1-methyl-1H-indazol-6-yl)phenyl)-N-(4-(2-(2,2,2-trifluoroacetyl)hydrazine-1-carbonyl)benzyl)

thiomorpholine-4-carboxamide 1,1-dioxide (0.095 g, 0.151 mmol) prepared in Step 3 and 1-methoxy-N-triethylammoniosulfonyl-methanimidate (Burgess reagent, 0.054 g, 0.227 mmol) in tetrahydrofuran (2 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(3-(1-methyl-1H-indazol-6-yl)phenyl)-N-(4-(5-(trifluoromethyl)-1,3,4-oxadiazol-2-yl)benzyl)thiomorpholine-4-carboxamide 1,1-dioxide as bright yellow solid (0.059 g, 63.5%).

$^1$H NMR (400 MHz, CDCl$_3$) δ 8.06-8.04 (m, 3H), 7.80-7.78 (m, 1H), 7.53-7.43 (m, 5H), 7.35-7.34 (m, 1H), 7.26-7.23 (m, 1H), 7.09-7.08 (m, 1H), 4.98 (s, 2H), 4.12 (s, 3H), 3.78-3.77 (m, 4H), 2.85-2.84 (m, 4H); LRMS (ES) m/z 611.2 (M$^+$+1).

Example 108. Compound 21439: N-([1,1'-biphenyl]-3-yl)-N-(4-(5-(trifluoromethyl)-1,3,4-oxadiazol-2-yl)benzyl)thiomorpholine-4-carboxamide 1,1-dioxide

[Step 1] Methyl 4-((N-([1,1'-biphenyl]-3-yl)-1,1-dioxidothiomorpholine-4-carboxamido)methyl)benzoate

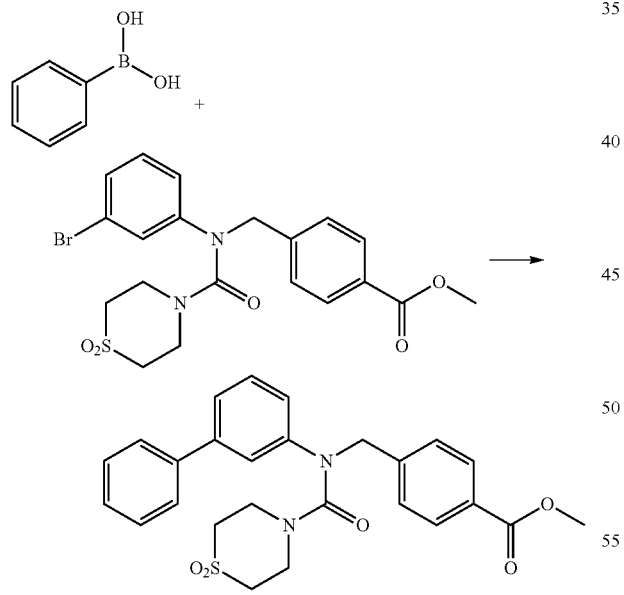

A mixture of methyl 4-((N-(3-bromophenyl)-1,1-dioxidothiomorpholine-4-carboxamido)methyl)benzoate (0.500 g, 1.000 mmol) prepared in Step 2 of Example 104, phenylboronic acid (0.146 g, 1.200 mmol), [1,1'-bis(di-tert-butylphosphino)ferrocene]palladium(II) dichloride (Pd(dtbpf)Cl2, 0.033 g, 0.050 mmol) and cesium carbonate (0.971 g, 3.000 mmol) in water (3 mL)/1,4-dioxane (12 mL) was heated at 140° C. for 20 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; ethyl acetate/hexane=0% to 50%) to give the title compound methyl 4-((N-([1,1'-biphenyl]-3-yl)-1,1-dioxidothiomorpholine-4-carboxamido)methyl)benzoate as white solid (0.411 g, 85.9%).

[Step 2] N-([1,1'-biphenyl]-3-yl)-N-(4-(hydrazinecarbonyl)benzyl)thiomorpholine-4-carboxamide 1,1-dioxide

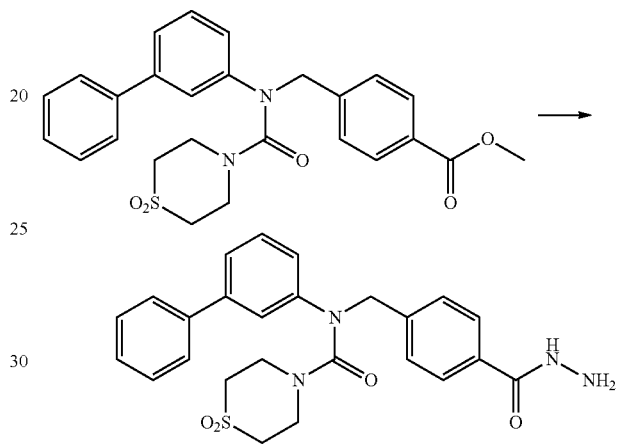

A mixture of methyl 4-((N-([1,1'-biphenyl]-3-yl)-1,1-dioxidothiomorpholine-4-carboxamido)methyl)benzoate (0.411 g, 0.859 mmol) prepared in Step 1 and hydrazine monohydrate (0.811 mL, 17.177 mmol) in ethanol (10 mL) was heated at reflux for 16 hr, and cooled down to the ambient temperature. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-([1,1'-biphenyl]-3-yl)-N-(4-(hydrazinecarbonyl)benzyl)thiomorpholine-4-carboxamide 1,1-dioxide as white solid (0.320 g, 77.9%).

[Step 3] N-([1,1'-biphenyl]-3-yl)-N-(4-(2-(2,2,2-trifluoroacetyl)hydrazine-1-carbonyl)benzyl)thiomorpholine-4-carboxamide 1,1-dioxide

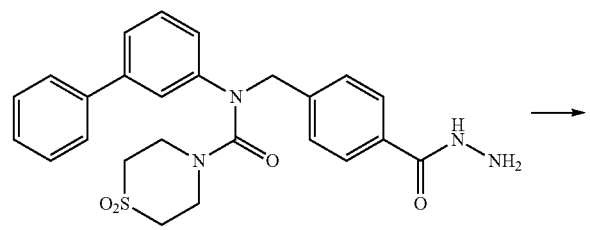

-continued

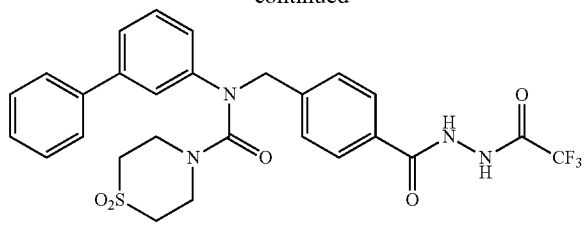

A solution of N-([1,1'-biphenyl]-3-yl)-N-(4-(hydrazinecarbonyl)benzyl)thiomorpholine-4-carboxamide 1,1-dioxide (0.320 g, 0.669 mmol) prepared in Step 2 and triethylamine (0.139 mL, 1.003 mmol) in dichloromethane (10 mL) was mixed at 0° C. with trifluoroacetic anhydride (0.084 mL, 0.602 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 24 g cartridge; methanol/dichloromethane=0% to 5%) to give the title compound N-([1,1'-biphenyl]-3-yl)-N-(4-(2-(2,2,2-trifluoroacetyl)hydrazine-1-carbonyl)benzyl)thiomorpholine-4-carboxamide 1,1-dioxide as white solid (0.326 g, 84.9%).

[Step 4] Compound 21439

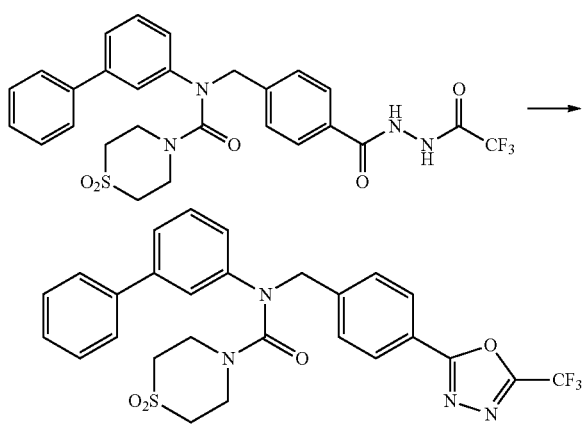

A mixture of N-([1,1'-biphenyl]-3-yl)-N-(4-(2-(2,2,2-trifluoroacetyl)hydrazine-1-carbonyl)benzyl)thiomorpholine-4-carboxamide 1,1-dioxide (0.326 g, 0.567 mmol) prepared in Step 3 and 1-methoxy-N-triethylammoniosulfonylmethanimidate (Burgess reagent, 0.203 g, 0.851 mmol) in tetrahydrofuran (2 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 3%) to give the title compound N-([1,1'-biphenyl]-3-yl)-N-(4-(5-(trifluoromethyl)-1,3,4-oxadiazol-2-yl)benzyl)thiomorpholine-4-carboxamide 1,1-dioxide as white solid (0.192 g, 60.7%).
$^1$H NMR (400 MHz, $CDCl_3$) δ 8.03 (d, 1H, J=8.4 Hz), 7.50-7.39 (m, 1H), 7.29-7.29 (m, 1H), 7.29-7.28 (m, 1H), 7.05-7.03 (m, 1H), 4.95 (s, 1H), 3.77-3.74 (m, 1H), 2.85-2.82 (m, 1H); LRMS (ES) m/z 557.3 ($M^+$+1).

Example 109. Compound 21440: N-(2-methoxyphenyl)-N-(4-(5-(trifluoromethyl)-1,3,4-oxadiazol-2-yl)benzyl)thiomorpholine-4-carboxamide 1,1-dioxide

[Step 1] N-(2-methoxyphenyl)thiomorpholine-4-carboxamide 1,1-dioxide

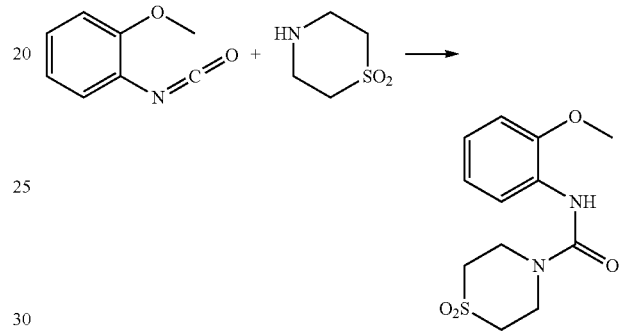

A solution of 1-isocyanato-2-methoxybenzene (0.891 mL, 6.705 mmol) and thiomorpholine 1,1-dioxide (0.915 g, 6.772 mmol) in diethylether (100 mL) was stirred at the room temperature for 16 min. The precipitates were collected by filtration, washed by 1N-diethylether solution, and dried to give the title compound N-(2-methoxyphenyl)thiomorpholine-4-carboxamide 1,1-dioxide as white solid (1.810 g, 94.9%).

[Step 2] Methyl 4-((N-(2-methoxyphenyl)-1,1-dioxidothiomorpholine-4-carboxamido)methyl)benzoate

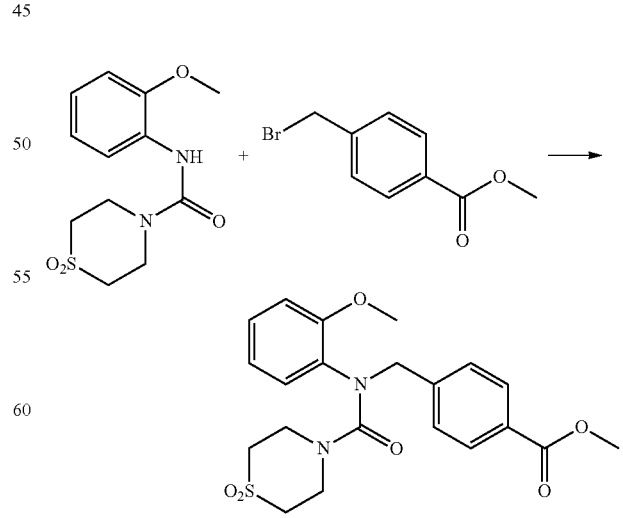

To a stirred solution of N-(2-methoxyphenyl)thiomorpholine-4-carboxamide 1,1-dioxide (0.500 g, 1.759 mmol) prepared in Step 1 in N,N-dimethylformamide (10 mL) was added at 0° C. sodium hydride (60.00%, 0.077 g, 1.934 mmol). The reaction mixture was stirred at the same temperature, treated at the room temperature with methyl 4-(bromomethyl)benzoate (0.443 g, 1.934 mmol), and stirred for additional 1 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The crude title compound methyl 4-((N-(2-methoxyphenyl)-1,1-dioxidothiomorpholine-4-carboxamido)methyl)benzoate was used without further purification (0.530 g, 69.7%, white solid).

[Step 3] N-(4-(hydrazinecarbonyl)benzyl)-N-(2-methoxyphenyl)thiomorpholine-4-carboxamide 1,1-dioxide

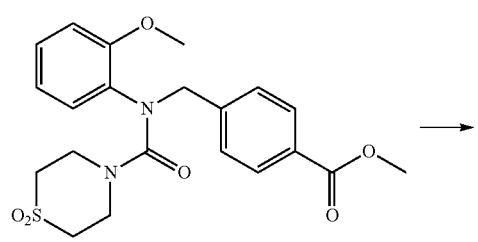

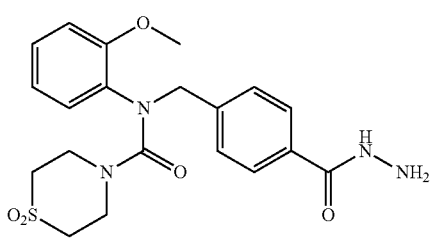

A mixture of methyl 4-((N-(2-methoxyphenyl)-1,1-dioxidothiomorpholine-4-carboxamido)methyl)benzoate (0.510 g, 1.179 mmol) prepared in Step 2 and hydrazine monohydrate (1.114 mL, 23.584 mmol) in ethanol (10 mL) was heated at reflux for 16 hr, and cooled down to the ambient temperature. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 24 g cartridge; methanol/dichloromethane=0% to 5%) to give the title compound N-(4-(hydrazinecarbonyl) benzyl)-N-(2-methoxyphenyl)thiomorpholine-4-carboxamide 1,1-dioxide as white solid (0.095 g, 18.6%).

[Step 4] N-(2-methoxyphenyl)-N-(4-(2-(2,2,2-trifluoroacetyl)hydrazine-1-carbonyl)benzyl)thiomorpholine-4-carboxamide 1,1-dioxide

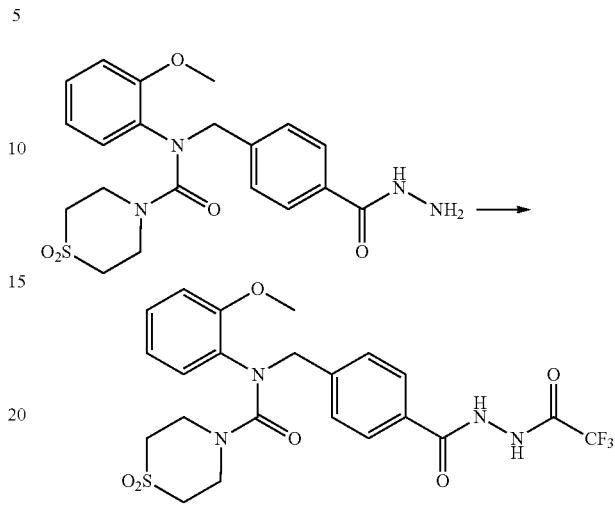

A solution of N-(4-(hydrazinecarbonyl)benzyl)-N-(2-methoxyphenyl)thiomorpholine-4-carboxamide 1,1-dioxide (0.095 g, 0.220 mmol) prepared in Step 3 and triethylamine (0.046 mL, 0.329 mmol) in dichloromethane (3 mL) was mixed at 0° C. with trifluoroacetic anhydride (0.027 mL, 0.198 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-(2-methoxyphenyl)-N-(4-(2-(2,2,2-trifluoroacetyl)hydrazine-1-carbonyl)benzyl)thiomorpholine-4-carboxamide 1,1-dioxide as white solid (0.020 g, 17.2%).

[Step 5] Compound 21440

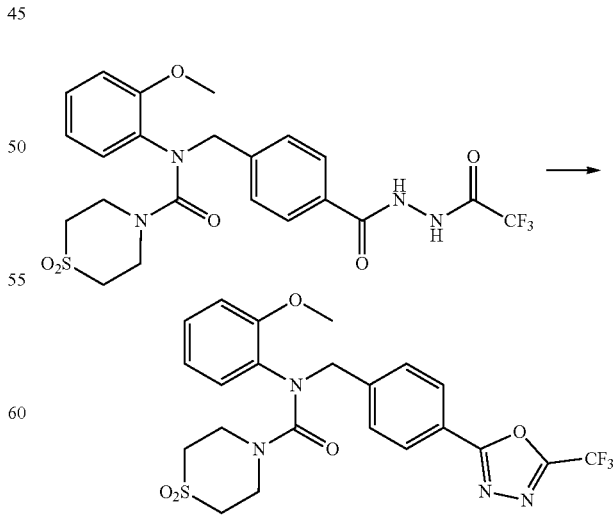

A mixture of N-(2-methoxyphenyl)-N-(4-(2-(2,2,2-trifluoroacetyl)hydrazine-1-carbonyl)benzyl)thiomorpholine- 4-carboxamide 1,1-dioxide (0.020 g, 0.038 mmol) prepared in Step 4 and 1-methoxy-N-triethylammoniosulfonyl-methanimidate (Burgess reagent, 0.014 g, 0.057 mmol) in tetrahydrofuran (1 mL) was heated at 150° C. for 30 min under the microwaves, and cooled down to the room temperature to terminate the reaction. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated ill vacuo. The concentrate was purified and concentrated by column chromatography (SiO$_2$, 4 g cartridge; methanol/dichloromethane=0% to 3%) to give the title compound N-(2-methoxyphenyl)-N-(4-(5-(trifluoromethyl)-1,3,4-oxadiazol-2-yl)benzyl)thiomorpholine-4-carboxamide 1,1-dioxide as white solid (0.008 g, 43.0%).

$^1$H NMR (400 MHz, CDCl$_3$) δ 7.98 (d, 2H, J=8.4 Hz), 7.47 (d, 2H, J=8.5 Hz), 7.28-7.24 (m, 1H), 6.97-6.91 (m, 3H), 4.73 (s, 2H), 3.82 (s, 3H), 3.69-3.66 (m, 4H), 2.66-2.63 (m, 4H); LRMS (ES) m/z 511.3 (M$^+$+1).

Example 110. Compound 21441: N-(3-methoxyphenyl)-N-(4-(5-(trifluoromethyl)-1,3,4-oxadiazol-2-yl) benzyl)thiomorpholine-4-carboxamide 1,1-dioxide

[Step 1] N-(3-methoxyphenyl)thiomorpholine-4-carboxamide 1,1-dioxide

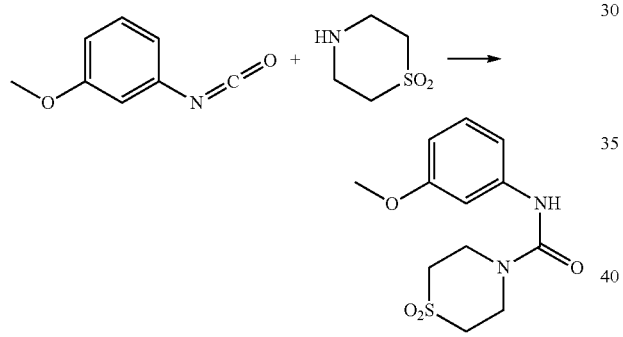

A solution of 1-isocyanato-3-methoxybenzene (0.879 mL, 6.705 mmol) and thiomorpholine 1,1-dioxide (0.915 g, 6.772 mmol) in diethylether (100 mL) was stirred at the room temperature for 16 hr. The precipitates were collected by filtration, washed by 1N-diethylether solution, and dried to give the title compound N-(3-methoxyphenyl)thiomorpholine-4-carboxamide 1,1-dioxide as white solid (1.920 g, 100.7%).

[Step 2] Methyl 4-((N-(3-methoxyphenyl)-1,1-dioxidothiomorpholine-4-carboxamido)methyl)benzoate

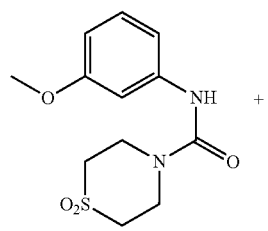

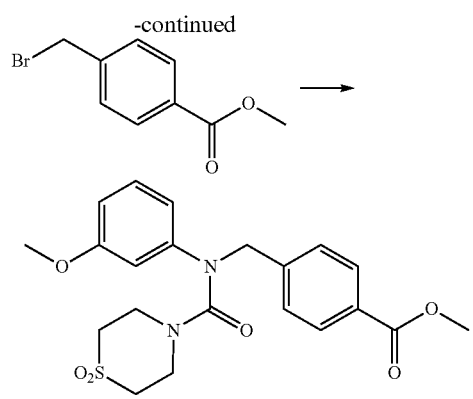

To a stirred solution of N-(3-methoxyphenyl)thiomorpholine-4-carboxamide 1,1-dioxide (0.500 g, 1.759 mmol) prepared in Step 1 in N,N-dimethylformamide (10 mL) was added at 0° C. sodium hydride (60.00 To, 0.077 g, 1.934 mmol). The reaction mixture was stirred at the same temperature, treated at the room temperature with methyl 4-(bromomethyl)benzoate (0.443 g, 1.934 mmol), and stirred for additional 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; ethyl acetate/hexane=0% to 50%) to give the title compound methyl 4-((N-(3-methoxyphenyl)-1,1-dioxidothiomorpholine-4-carboxamido)methyl)benzoate as white solid (0.378 g, 49.7%).

[Step 3] N-(4-(hydrazinecarbonyl)benzyl)-N-(3-methoxyphenyl)thiomorpholine-4-carboxamide 1,1-dioxide

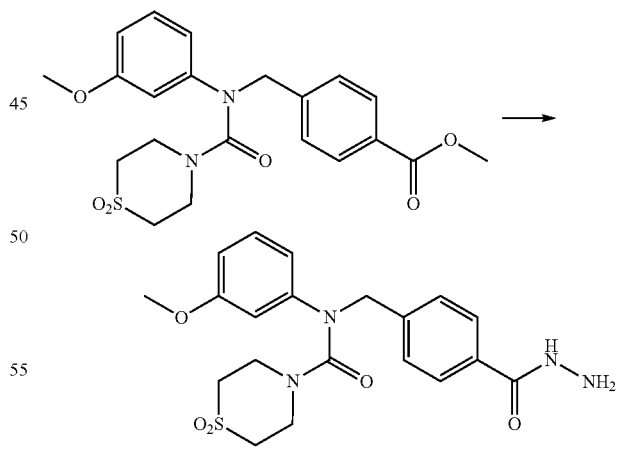

A mixture of methyl 4-((N-(3-methoxyphenyl)-1,1-dioxidothiomorpholine-4-carboxamido)methyl)benzoate (0.360 g, 0.832 mmol) prepared in Step 2 and hydrazine monohydrate (0.786 mL, 16.648 mmol) in ethanol (10 mL) was heated at reflux for 16 hr, and cooled down to the ambient temperature. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 24 g cartridge; methanol/dichloromethane=0% to 5%) to give the title compound N-(4-(hydrazinecarbonyl)benzyl)-N-(3-methoxyphenyl)thiomorpholine-4-carboxamide 1,1-dioxide as white solid (0.342 g, 95.1%).

[Step 4] N-(3-methoxyphenyl)-N-(4-(2-(2,2,2-trifluoroacetyl)hydrazine-1-carbonyl)benzyl)thiomorpholine-4-carboxamide 1,1-dioxide

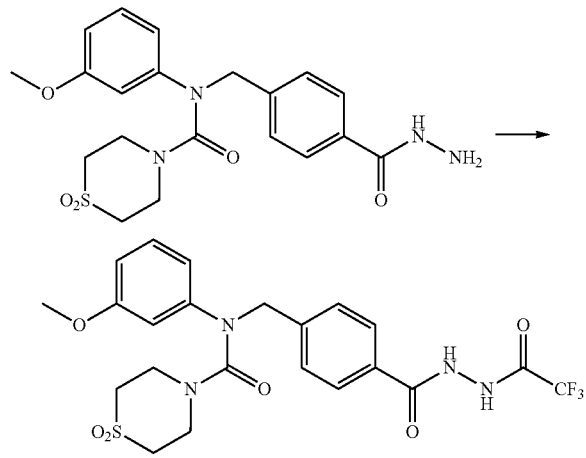

A solution of N-(4-(hydrazinecarbonyl)benzyl)-N-(3-methoxyphenyl)thiomorpholine-4-carboxamide 1,1-dioxide (0.332 g, 0.718 mmol) prepared in Step 3 and triethylamine (0.149 mL, 1.077 mmol) in dichloromethane (10 mL) was mixed at 0° C. with trifluoroacetic anhydride (0.090 mL, 0.646 mmol), and stirred at the room temperature for 3 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 5%) to give the title compound N-(3-methoxyphenyl)-N-(4-(2-(2,2,2-trifluoroacetyl)hydrazine-1-carbonyl)benzyl)thiomorpholine-4-carboxamide 1,1-dioxide as white solid (0.335 g, 88.3%).

[Step 5] Compound 21441

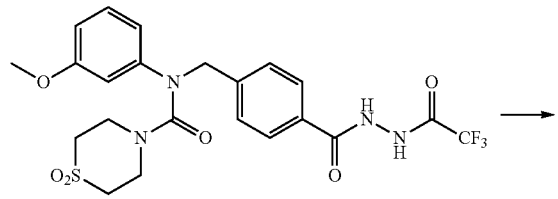

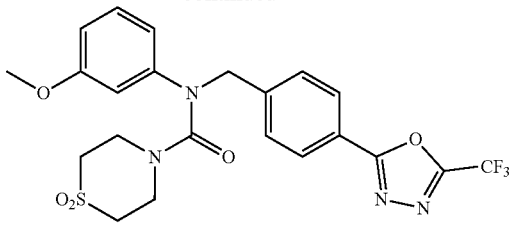

A mixture of N-(3-methoxyphenyl)-N-(4-(2-(2,2,2-trifluoroacetyl)hydrazine-1-carbonyl)benzyl)thiomorpholine-4-carboxamide 1,1-dioxide (0.335 g, 0.634 mmol) prepared in Step 4 and 1-methoxy-N-triethylammoniosulfonylmethanimidate (Burgess reagent, 0.227 g, 0.951 mmol) in tetrahydrofuran (5 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 3%) to give the title compound N-(3-methoxyphenyl)-N-(4-(5-(trifluoromethyl)-1,3,4-oxadiazol-2-yl)benzyl)thiomorpholine-4-carboxamide 1,1-dioxide as white solid (0.232 g, 71.5%).

$^1$H NMR (400 MHz, CDCl₃) δ 8.02 (d, 1H, J=8.4 Hz), 7.45 (d, 1H, J=8.4 Hz), 7.27-7.23 (m, 1H), 6.74-6.72 (m, 1H), 6.56-6.63 (m, 1H), 6.62-6.61 (m, 1H), 4.88 (s, 1H), 3.75-3.72 (m, 1H), 2.84-2.81 (m, 1H); LRMS (ES) m/z 511.3 (M⁺+1).

Example 111. Compound 21442: N-(m-tolyl)-N-(4-(5-(trifluoromethyl)-1,3,4-oxadiazol-2-yl)benzyl)thiomorpholine-4-carboxamide 1,1-dioxide

[Step 1] N-(m-tolyl)thiomorpholine-4-carboxamide 1,1-dioxide

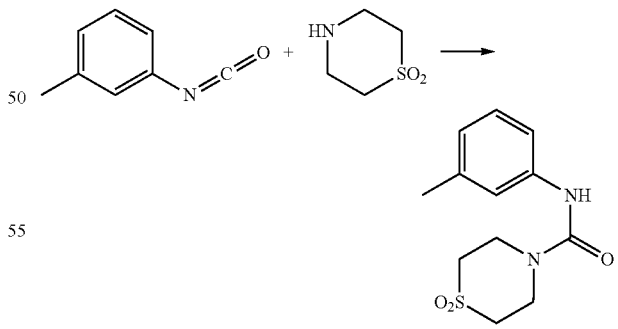

A solution of 1-isocyanato-3-methylbenzene (0.968 mL, 7.510 mmol) and thiomorpholine 1,1-dioxide (1.025 g, 7.585 mmol) in diethylether (100 mL) was stirred at the room temperature for 16 hr. The precipitates were collected by filtration, washed by 1N-diethylether solution, and dried to give the title compound N-(m-tolyl)thiomorpholine-4-carboxamide 1,1-dioxide as white solid (2.010 g, 99.7%).

[Step 2] Methyl 4-((1,1-dioxido-N-(m-tolyl)thiomorpholine-4-carboxamido)methyl)benzoate

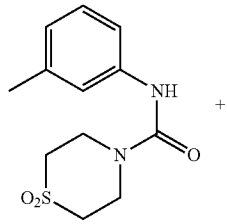

+

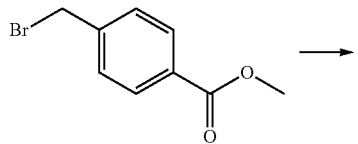

→

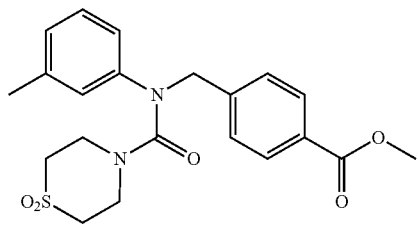

To a stirred solution of N-(m-tolyl)thiomorpholine-4-carboxamide 1,1-dioxide (0.500 g, 1.863 mmol) prepared in Step 1 in N,N-dimethylformamide (10 mL) was added at 0° C. sodium hydride (60.00%, 0.082 g, 2.050 mmol). The reaction mixture was stirred at the same temperature, treated at the room temperature with methyl 4-(bromomethyl)benzoate (0.470 g, 2.050 mmol), and stirred for additional 1 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 24 g cartridge; ethyl acetate/hexane=0% to 50%) to give the title compound methyl 4-((1,1-dioxido-N-(m-tolyl)thiomorpholine-4-carboxamido)methyl)benzoate as white solid (0.321 g, 41.4%).

[Step 3] N-(4-(hydrazinecarbonyl)benzyl)-N-(m-tolyl)thiomorpholine-4-carboxamide 1,1-dioxide

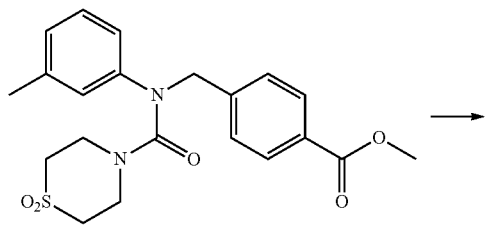

→

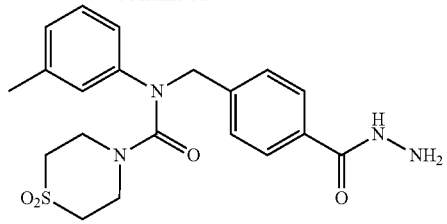

A mixture of methyl 4-((1,1-dioxido-N-(m-tolyl)thiomorpholine-4-carboxamido)methyl)benzoate (0.310 g, 0.744 mmol) prepared in Step 2 and hydrazine monohydrate (0.703 mL, 14.886 mmol) in ethanol (10 mL) was heated at reflux for 16 hr, and cooled down to the ambient temperature. The reaction mixture was concentrated under the reduced pressure to remove the solvent, and saturated aqueous sodium bicarbonate solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 24 g cartridge; methanol/dichloromethane=0% to 5%) to give the title compound N-(4-(hydrazinecarbonyl)benzyl)-N-(m-tolyl)thiomorpholine-4-carboxamide 1,1-dioxide as white solid (0.230 g, 74.2%).

[Step 4] N-(m-tolyl)-N-(4-(2-(2,2,2-trifluoroacetyl)hydrazine-1-carbonyl)benzyl)thiomorpholine-4-carboxamide 1,1-dioxide

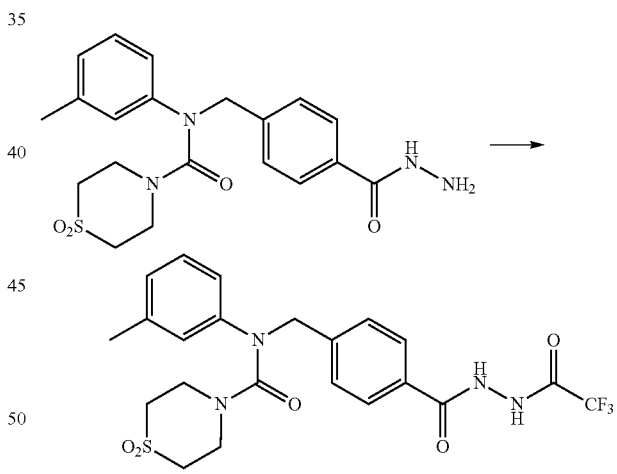

A solution of N-(4-(hydrazinecarbonyl)benzyl)-N-(m-tolyl)thiomorpholine-4-carboxamide 1,1-dioxide (0.219 g, 0.526 mmol) prepared in Step 3 and triethylamine (0.109 mL, 0.789 mmol) in dichloromethane (5 mL) was mixed at 0° C. with trifluoroacetic anhydride (0.066 mL, 0.473 mmol), and stirred at the room temperature for 3 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified by column chromatography (SiO₂, 12 g cartridge; methanol/dichloromethane=0% to 5%) to give the title compound N-(m-tolyl)-N-(4-(2-(2,2,2-trifluoroacetyl)hydrazine-1-carbonyl)benzyl)thiomorpholine-4-carboxamide 1,1-dioxide as white solid (0.213 g, 79.0%).

[Step 5] Compound 21442

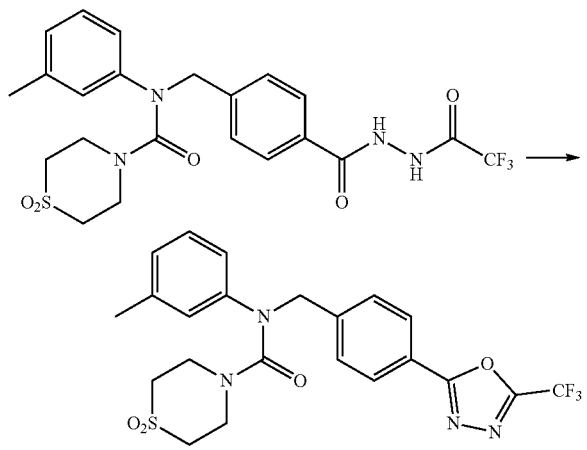

A mixture of N-(m-tolyl)-N-(4-(2-(2,2,2-trifluoroacetyl)hydrazine-1-carbonyl)benzyl)thiomorpholine-4-carboxamide 1,1-dioxide (0.213 g, 0.416 mmol) prepared in Step 4 and 1-methoxy-N-triethylammoniosulfonyl-methanimidate (Burgess reagent, 0.149 g, 0.623 mmol) in tetrahydrofuran (5 mL) was heated at 150° C. for 30 min under the microwaves, and cooled down to the room temperature to terminate the reaction. Then, saturated aqueous sodium bicarbonate solution was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 3%) to give the title compound N-(m-tolyl)-N-(4-(5-(trifluoromethyl)-1,3,4-oxadiazol-2-yl)benzyl)thiomorpholine-4-carboxamide 1,1-dioxide as bright yellow solid (0.135 g, 65.4%).

$^1$H NMR (400 MHz, CDCl$_3$) δ 8.02 (d, 2H, J=8.4 Hz), 7.44 (d, 2H, J=8.3 Hz), 7.22 (t, 1H, J=7.8 Hz), 7.03-7.01 (m, 1H), 6.89-6.84 (m, 2H), 4.87 (s, 2H), 3.73-3.71 (m, 4H), 2.80-2.78 (m, 4H), 2.32 (s, 3H); LRMS (ES) m/z 495.2 (M$^+$+1).

Example 112. Compound 21443: N-(4-(methylsulfonyl)phenyl)-N-(4-(5-(trifluoromethyl)-1,3,4-oxadiazol-2-yl)benzyl)morpholine-4-carboxamide

[Step 1]
N-(4-(methylthio)phenyl)morpholine-4-carboxamide

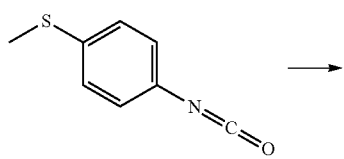

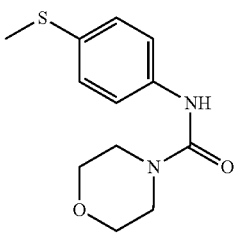

A solution of (4-isocyanatophenyl)(methyl)sulfane (2.000 g, 12.106 mmol) in diethylether (50 mL) was mixed at the room temperature with morpholine (1.262 mL, 14.527 mmol). The reaction mixture was stirred at the same temperature for 1 hr. The precipitates were collected by filtration, washed by aqueous 1N-acetic acid solution, and dried to give the title compound N-(4-(methylthio)phenyl)morpholine-4-carboxamide as white solid (2.700 g, 88.4%).

[Step 2] Methyl 4-((N-(4-(methylthio)phenyl)morpholine-4-carboxamido)methyl)benzoate

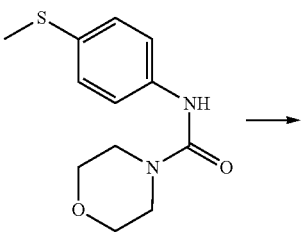

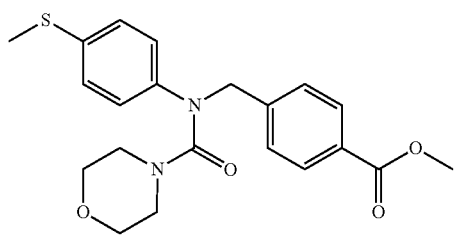

To a stirred solution of N-(4-(methylthio)phenyl)morpholine-4-carboxamide (1.010 g, 4.003 mmol) prepared in Step 1 in N,N-dimethylformamide (10 mL) was added at 0° C. sodium hydride (60.00%, 0.240 g, 6.004 mmol). The reaction mixture was stirred for 10 min, treated with methyl 4-(bromomethyl)benzoate (1.192 g, 5.204 mmol), and stirred at the same temperature for 10 min. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; ethyl acetate/hexane=10% to 70%) to give the title compound methyl 4-((N-(4-(methylthio)phenyl)morpholine-4-carboxamido)methyl)benzoate as yellow oil (1.270 g, 79.2%).

[Step 3] Methyl 4-((N-(4-(methylsulfonyl)phenyl)morpholine-4-carboxamido)methyl)benzoate

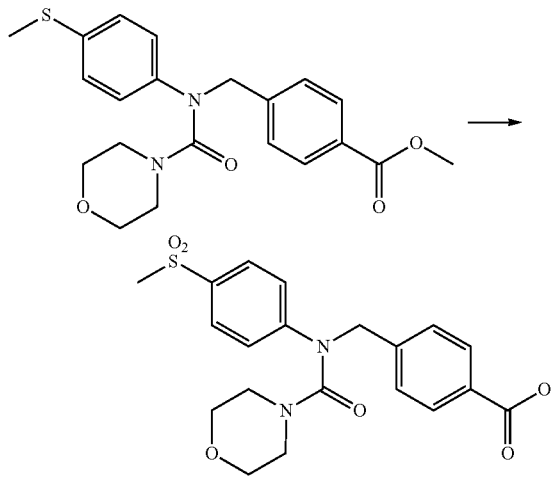

A solution of methyl 4-((N-(4-(methylthio)phenyl)morpholine-4-carboxamido)methyl)benzoate (1.200 g, 2.996 mmol) prepared in Step 2 in dichloromethane (20 mL) was mixed at the room temperature with meta-Chloroperoxybenzoic acid (70.00%, 1.551 g, 6.292 mmol). The reaction mixture was stirred at the same temperature for 1 hr. Then, saturated aqueous sodium bicarbonate solution was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; ethyl acetate/hexane=5% to 60%) to give the title compound methyl 4-((N-(4-(methylsulfonyl)phenyl)morpholine-4-carboxamido)methyl)benzoate as yellow solid (1.230 g, 94.9%).

[Step 4] N-(4-(hydrazinecarbonyl)benzyl)-N-(4-(methylsulfonyl)phenyl)morpholine-4-carboxamide

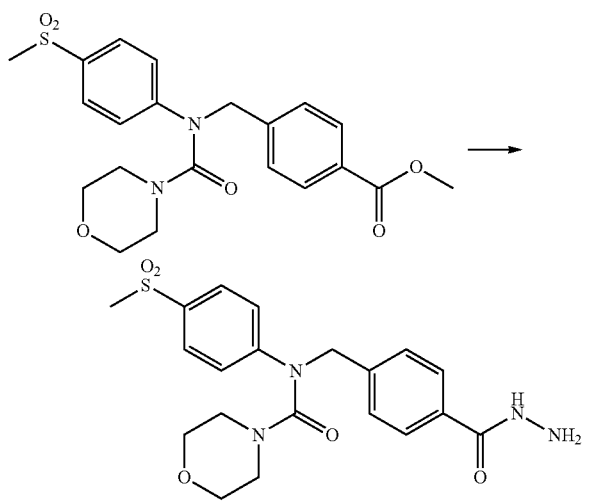

A mixture of methyl 4-((N-(4-(methylsulfonyl)phenyl)morpholine-4-carboxamido)methyl)benzoate (0.911 g, 2.106 mmol) prepared in Step 3 and hydrazine monohydrate (2.044 mL, 42.128 mmol) in ethanol (10 mL) was heated at the room temperature for 1 hr under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; methanol/dichloromethane=0% to 20%) to give the title compound N-(4-(hydrazinecarbonyl)benzyl)-N-(4-(methylsulfonyl)phenyl)morpholine-4-carboxamide as colorless oil (0.600 g, 65.9%).

[Step 5] N-(4-(methylsulfonyl)phenyl)-N-(4-(2-(2,2,2-trifluoroacetyl)hydrazine-1-carbonyl)benzyl) morpholine-4-carboxamide

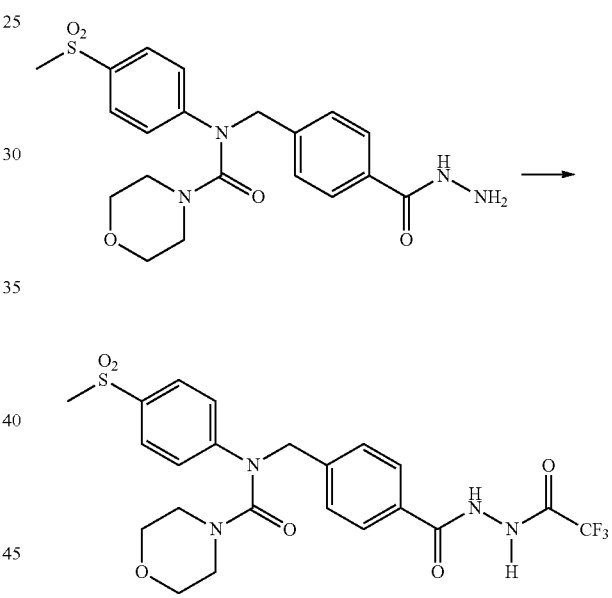

A solution of N-(4-(hydrazinecarbonyl)benzyl)-N-(4-(methylsulfonyl)phenyl)morpholine-4-carboxamide (0.340 g, 0.786 mmol) prepared in Step 4, trifluoroacetic anhydride (0.098 mL, 0.708 mmol) and triethylamine (0.163 mL, 1.179 mmol) in dichloromethane (10 mL) was stirred at the room temperature for 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound N-(4-(methylsulfonyl)phenyl)-N-(4-(2-(2,2,2-trifluoroacetyl)hydrazinecarbonyl)benzyl)morpholine-4-carboxamide as white solid (0.102 g, 24.6%).

[Step 6] Compound 21443

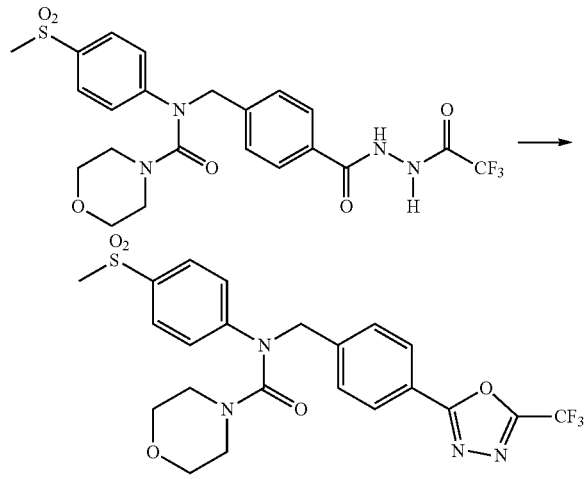

A mixture of N-(4-(methylsulfonyl)phenyl)-N-(4-(2-(2,2,2-trifluoroacetyl)hydrazine-1-carbonyl)benzyl) morpholine-4-carboxamide (0.065 g, 0.122 mmol) prepared in Step 5 and 1-methoxy-N-triethylammoniosulfonyl-methanimidate (Burgess reagent, 0.038 g, 0.159 mmol) in tetrahydrofuran (3 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 4 g cartridge; methanol/dichloromethane=0% to 20%) to give the title compound N-(4-(methylsulfonyl)phenyl)-N-(4-(5-(trifluoromethyl)-1,3,4-oxadiazol-2-yl)benzyl)morpholine-4-carboxamide as white solid (0.023 g, 36.9%).

$^1$H NMR (400 MHz, DMSO-d$_6$) δ 8.02 (d, 2H, J=8.4 Hz), 7.80 (d, 2H, J=8.8 Hz), 7.61 (d, 2H, J=8.4 Hz), 7.33 (d, 2H, J=8.8 Hz), 5.05 (s, 2H), 3.49 (m, 4H), 3.25 (m, 4H), 3.16 (s, 3H); LRMS (ES) m/z 511.22 (M$^+$+H).

Example 113. Compound 21444: N-(4-(5-(difluoromethyl)-1,3,4-oxadiazol-2-yl)benzyl)-N-(4-(methylsulfonyl)phenyl)morpholine-4-carboxamide

[Step 1] N-(4-(2-(2,2-difluoroacetyl)hydrazine-1-carbonyl)benzyl)-N-(4-(methylsulfonyl)phenyl)morpholine-4-carboxamide

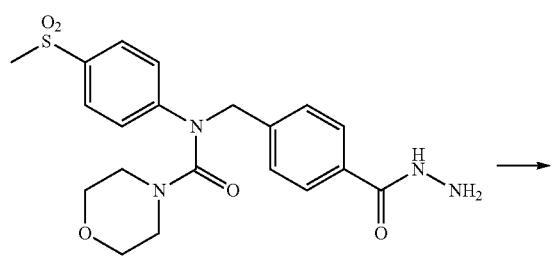

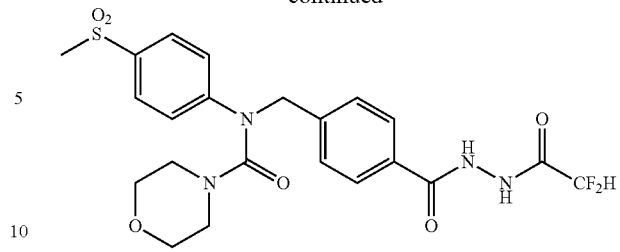

A solution of N-(4-(hydrazinecarbonyl)benzyl)-N-(4-(methylsulfonyl)phenyl)morpholine-4-carboxamide (0.300 g, 0.694 mmol) prepared in Step 4 of Example 112, 2,2-difluoroacetic anhydride (0.068 mL, 0.624 mmol) and triethylamine (0.144 mL, 1.040 mmol) in dichloromethane (10 mL) was stirred at the room temperature for 1 hr. Then, water was added to the reaction mixture, followed by extraction with ethyl acetate. The organic layer was washed with aqueous saturated sodium solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound N-(4-(2-(2,2-difluoroacetyl)hydrazinecarbonyl)benzyl)-N-(4-(methylsulfonyl)phenyl)morpholine-4-carboxamide as white solid (0.145 g, 40.9%).

[Step 2] Compound 21444

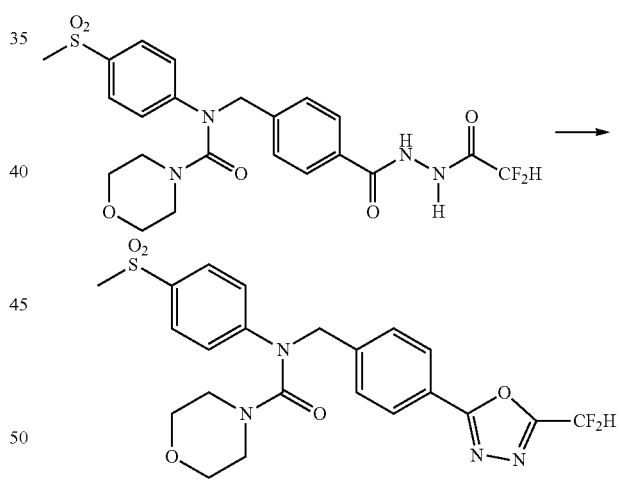

A mixture of N-(4-(2-(2,2-difluoroacetyl)hydrazine-1-carbonyl)benzyl)-N-(4-(methylsulfonyl)phenyl) morpholine-4-carboxamide (0.135 g, 0.264 mmol) prepared in Step 1 and 1-methoxy-N-triethylammoniosulfonyl-methanimidate (Burgess reagent, 0.082 g, 0.344 mmol) in tetrahydrofuran (3 mL) was heated at 150° C. for 30 min under the microwaves, and cooled down to the room temperature. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 20%) to give the title compound N-(4-

(5-(difluoromethyl)-1,3,4-oxadiazol-2-yl)benzyl)-N-(4-(methylsulfonyl)phenyl)morpholine-4-carboxamide as white solid (0.067 g, 51.4%).

$^1$H NMR (400 MHz, DMSO-d$_6$) δ 8.00 (d, 2H, J=8.4 Hz), 7.81 (d, 2H, J=8.8 Hz), 7.60 (d, 2H, J=8.3 Hz), 7.54 (t, 1H, J=51.4 Hz), 7.33 (d, 2H, J=8.8 Hz), 3.49 (m, 4H), 3.25 (m, 4H), 3.16 (s, 3H); LRMS (ES) m/z 493.30 (M$^+$+H).

Example 114. Compound 21445: N-(p-tolyl)-N-(4-(5-(trifluoromethyl)-1,3,4-oxadiazol-2-yl)benzyl)thiomorpholine-4-carboxamide 1,1-dioxide

[Step 1] N-(p-tolyl)thiomorpholine-4-carboxamide 1,1-dioxide

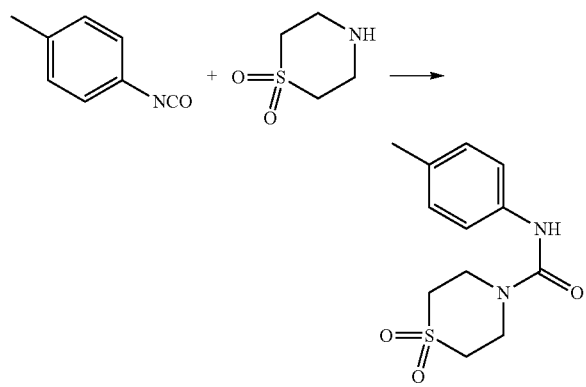

A solution of 1-isocyanato-4-methylbenzene (1.000 g, 7.510 mmol) and thiomorpholine 1,1-dioxide (1.015 g, 7.510 mmol) in diethylether (20 mL) was stirred at the room temperature for 16 hr. The precipitates were collected by filtration, washed by diethylether, and dried to give the title compound N-(p-tolyl)thiomorpholine-4-carboxamide 1,1-dioxide as white solid (1.931 g, 95.8%).

[Step 2] Methyl 4-((1,1-dioxido-N-(p-tolyl)thiomorpholine-4-carboxamido)methyl)benzoate

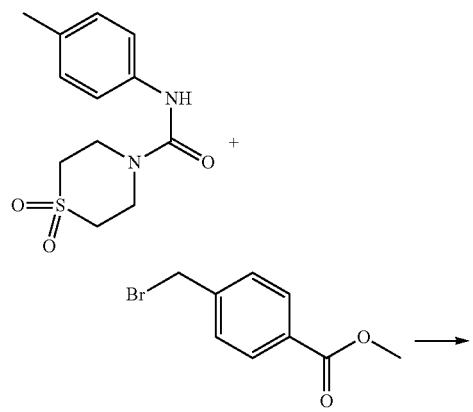

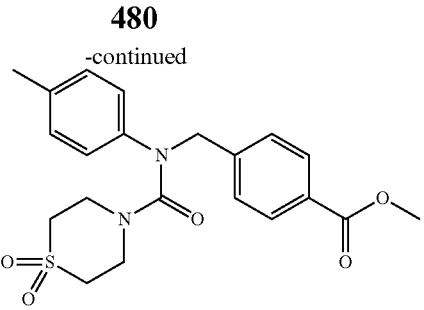

To a stirred solution of N-(p-tolyl)thiomorpholine-4-carboxamide 1,1-dioxide (0.300 g, 1.118 mmol) prepared in Step 1 in N,N-dimethylformamide (2 mL) was added at 0° C. sodium hydride (60.00%, 0.045 g, 1.118 mmol). The reaction mixture was stirred at the same temperature for 30 min, treated at the room temperature with methyl 4-(bromomethyl)benzoate (0.256 g, 1.118 mmol), and stirred for additional 2 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using ethyl acetate (1 mL) and hexane (10 mL). The resulting precipitates were filtered, washed by hexane, and dried to give the title compound methyl 4-((1,1-dioxido-N-(p-tolyl)thiomorpholine-4-carboxamido)methyl)benzoate as white solid (0.207 g, 44.5%).

[Step 3] N-(4-(hydrazinecarbonyl)benzyl)-N-(p-tolyl)thiomorpholine-4-carboxamide 1,1-dioxide

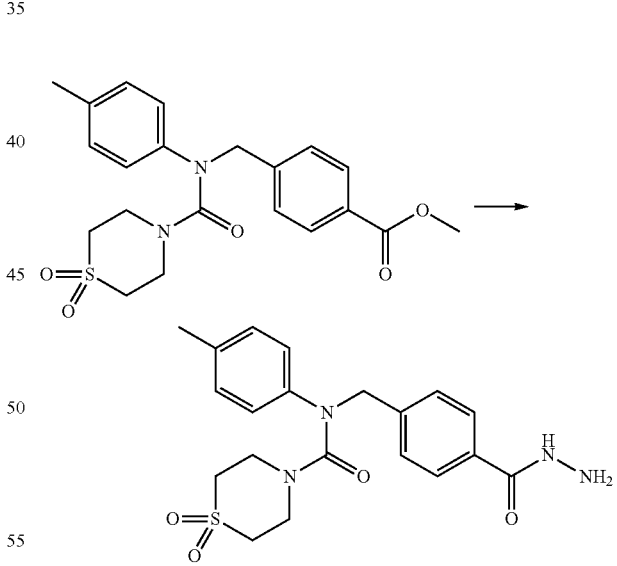

Methyl 4-((1,1-dioxido-N-(p-tolyl)thiomorpholine-4-carboxamido)methyl)benzoate (0.207 g, 0.497 mmol) prepared in Step 2 and hydrazine monohydrate (0.470 mL, 9.950 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to

481 remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-(4-(hydrazinecarbonyl)benzyl)-N-(p-tolyl)thiomorpholine-4-carboxamide 1,1-dioxide as white foam (0.185 g, 89.4%).

[Step 4] (N-(p-tolyl)-N-(4-(2-(2,2,2-trifluoroacetyl) hydrazine-1-carbonyl)benzyl)thiomorpholine-4-carboxamide 1,1-dioxide

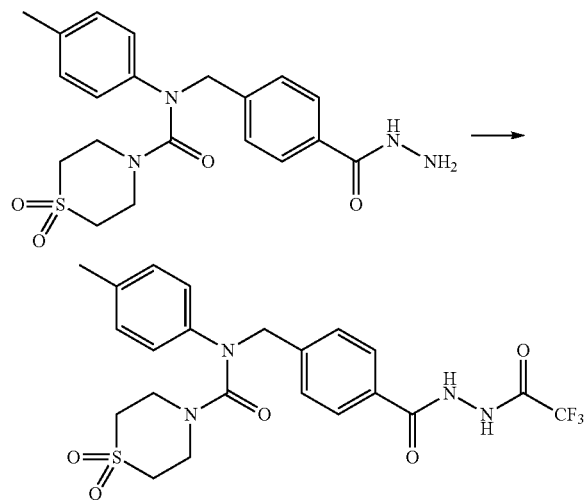

A solution of N-(4-(hydrazinecarbonyl)benzyl)-N-(p-tolyl)thiomorpholine-4-carboxamide 1,1-dioxide (0.093 g, 0.222 mmol) prepared in Step 3 and triethylamine (0.061 mL, 0.445 mmol) in tetrahydrofuran (2 mL) was mixed at the room temperature with trifluoroacetic anhydride (0.035 mL, 0.200 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(p-tolyl)-N-(4-(2-(2,2,2-trifluoroacetyl)hydrazine-1-carbonyl)benzyl)thiomorpholine-4-carboxamide 1,1-dioxide, 0.110 g, 96.5%, brown foam).

[Step 5] Compound 21445

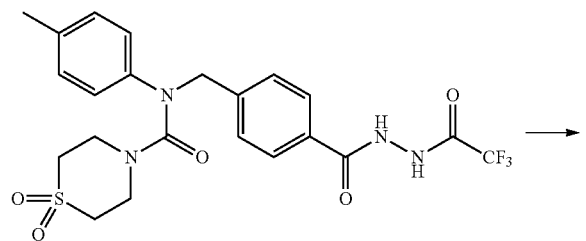

482

-continued

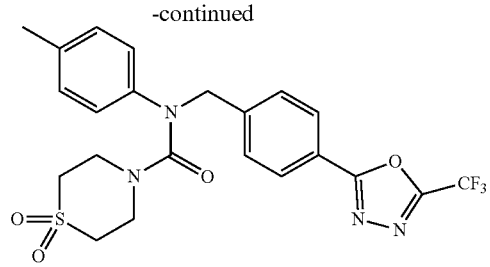

N-(p-tolyl)-N-(4-(2-(2,2,2-trifluoroacetyl)hydrazine-1-carbonyl)benzyl)thiomorpholine-4-carboxamide 1,1-dioxide (0.110 g, 0.215 mmol) prepared in Step 4 and 1-methoxy-N-triethylammoniosulfonyl-methanimidate (Burgess reagent, 0.077 g, 0.322 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; ethyl acetate/hexane=20% to 50%) to give the title compound N-(p-tolyl)-N-(4-(5-(trifluoromethyl)-1,3,4-oxadiazol-2-yl)benzyl)thiomorpholine-4-carboxamide 1,1-dioxide as white solid (0.056 g, 52.7%).
$^1$H NMR (400 MHz, CDCl₃) δ 8.01 (d, 2H, J=8.4 Hz), 7.43 (d, 2H, J=8.4 Hz), 7.14 (d, 2H, J=8.1 Hz), 6.98-6.90 (m, 2H), 4.86 (s, 2H), 3.72 (t, 4H, J=5.3 Hz), 2.78 (t, 4H, J=5.3 Hz), 2.32 (s, 3H); LRMS (ESI) m/z 495.02 (M⁺+H).

Example 115. Compound 21446: N-(4-(5-(difluoromethyl)-1,3,4-oxadiazol-2-yl)benzyl)-N-(p-tolyl) thiomorpholine-4-carboxamide 1,1-dioxide

[Step 1] (N-(4-(2-(2,2-difluoroacetyl)hydrazine-1-carbonyl)benzyl)-N-(p-tolyl)thiomorpholine-4-carboxamide 1,1-dioxide

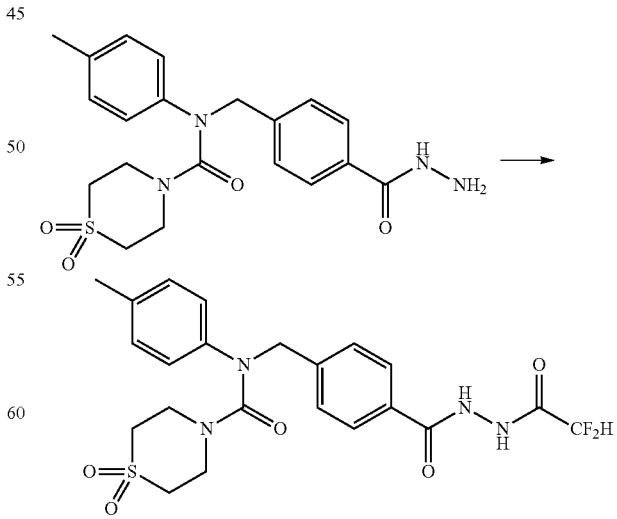

A solution of N-(4-(hydrazinecarbonyl)benzyl)-N-(p-tolyl)thiomorpholine-4-carboxamide 1,1-dioxide (0.093 g, 0.222 mmol) prepared in Step 3 of Example 114 and triethylamine (0.061 mL, 0.445 mmol) in tetrahydrofuran (2 mL) was mixed at the room temperature with Difluoroacetic Anhydride (0.030 mL, 0.200 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2-difluoroacetyl)hydrazine-1-carbonyl)benzyl)-N-(p-tolyl)thiomorpholine-4-carboxamide 1,1-dioxide, 0.106 g, 96.4%, brown foam).

[Step 2] Compound 21446

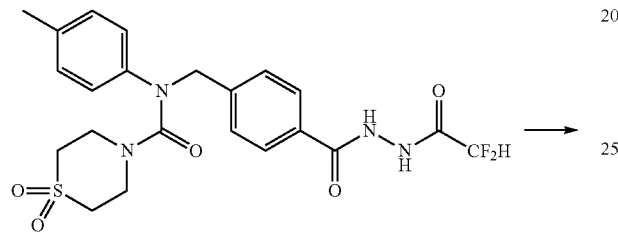

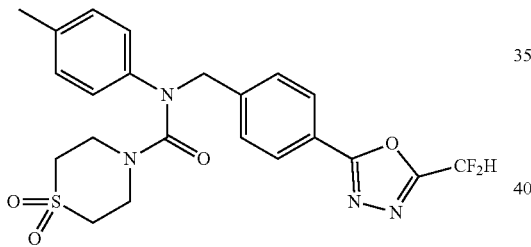

N-(4-(2-(2,2-difluoroacetyl)hydrazine-1-carbonyl)benzyl)-N-(p-tolyl)thiomorpholine-4-carboxamide 1,1-dioxide (0.106 g, 0.214 mmol) prepared in Step 1 and 1-methoxy-N-triethylammoniosulfonyl-methanimidate (Burgess reagent, 0.077 g, 0.322 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-(4-(5-(difluoromethyl)-1,3,4-oxadiazol-2-yl)benzyl)-N-(p-tolyl)thiomorpholine-4-carboxamide 1,1-dioxide as white solid (0.040 g, 39.4%).

$^1$H NMR (400 MHz, CDCl$_3$) δ 8.01 (d, 2H, J=8.3 Hz), 7.42 (d, 2H, J=8.3 Hz), 7.14 (d, 2H, J=8.2 Hz), 7.06-6.75 (m, 3H), 4.85 (s, 2H), 3.72 (t, 4H, J=5.3 Hz), 2.78 (t, 4H, J=5.3 Hz), 2.32 (s, 3H); LRMS (ESI) m/z 477.00 (M$^+$+H).

Example 116. Compound 21447: N-(2-fluorophenyl)-N-(4-(5-(trifluoromethyl)-1,3,4-oxadiazol-2-yl)benzyl)thiomorpholine-4-carboxamide 1,1-dioxide

[Step 1] N-(2-fluorophenyl)thiomorpholine-4-carboxamide 1,1-dioxide

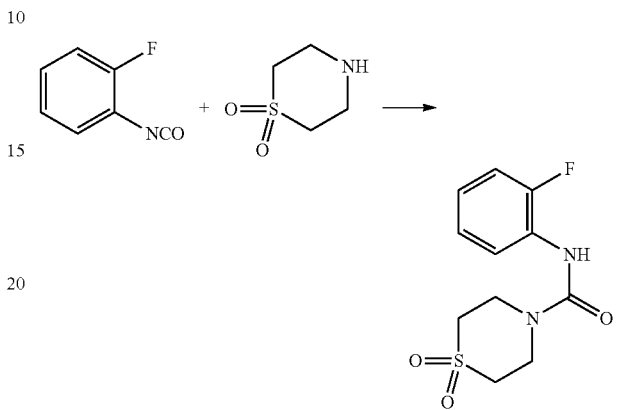

A solution of 1-fluoro-2-isocyanatobenzene (1.000 g, 7.293 mmol) and thiomorpholine 1,1-dioxide (0.986 g, 7.293 mmol) in diethylether (20 mL) was stirred at the room temperature for 16 hr. The precipitates were collected by filtration, washed by diethylether, and dried to give the title compound N-(2-fluorophenyl)thiomorpholine-4-carboxamide 1,1-dioxide as white solid (1.931 g, 97.2%).

[Step 2] Methyl 4-((N-(2-fluorophenyl)-1,1-dioxidothiomorpholine-4-carboxamido)methyl)benzoate

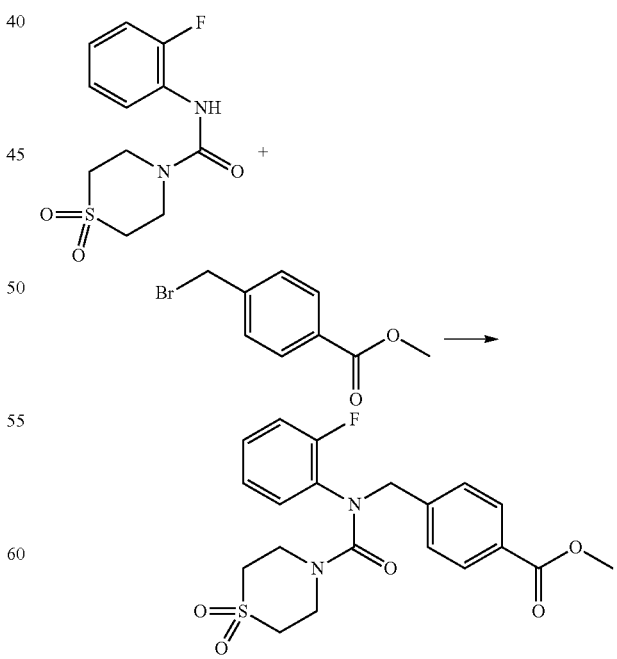

To a stirred solution of N-(2-fluorophenyl)thiomorpholine-4-carboxamide 1,1-dioxide (0.300 g, 1.102 mmol) prepared in Step 1 in N,N-dimethylformamide (2 mL) was added at 0° C. sodium hydride (60.00%, 0.044 g, 1.102 mmol). The reaction mixture was stirred at the same temperature for 30 min, treated at the room temperature with methyl 4-(bromomethyl)benzoate (0.252 g, 1.102 mmol), and stirred for additional 2 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using ethyl acetate (1 mL) and hexane (10 mL). The resulting precipitates were filtered, washed by hexane, and dried to give the title compound methyl 4-((N-(2-fluorophenyl)-1,1-dioxidothiomorpholine-4-carboxamido)methyl)benzoate as white solid (0.278 g, 60.1%).

[Step 3] N-(2-fluorophenyl)-N-(4-(hydrazinecarbonyl)benzyl)thiomorpholine-4-carboxamide 1,1-dioxide

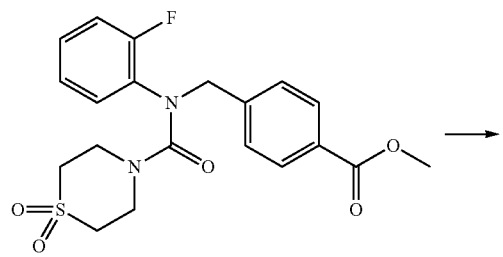

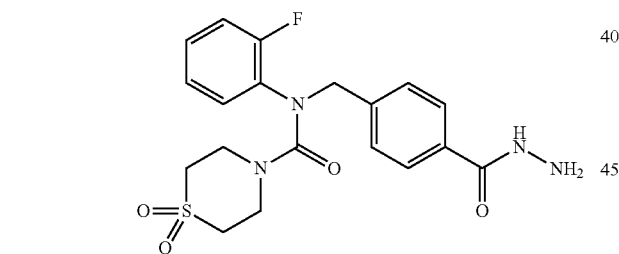

Methyl 4-((N-(2-fluorophenyl)-1,1-dioxidothiomorpholine-4-carboxamido)methyl)benzoate (0.278 g, 0.662 mmol) prepared in Step 2 and hydrazine monohydrate (0.625 mL, 13.243 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluorophenyl)-N-(4-(hydrazinecarbonyl)benzyl)thiomorpholine-4-carboxamide 1,1-dioxide as white foam (0.248 g, 89.1%).

[Step 4] (N-(2-fluorophenyl)-N-(4-(2-(2,2,2-trifluoroacetyl)hydrazine-1-carbonyl)benzyl)thiomorpholine-4-carboxamide 1,1-dioxide

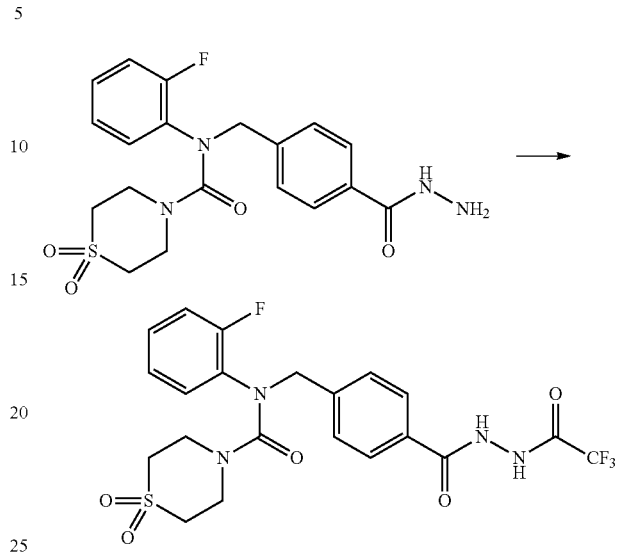

A solution of N-(2-fluorophenyl)-N-(4-(hydrazinecarbonyl)benzyl)thiomorpholine-4-carboxamide 1,1-dioxide (0.124 g, 0.295 mmol) prepared in Step 3 and triethylamine (0.082 mL, 0.590 mmol) in tetrahydrofuran (2 mL) was mixed at the room temperature with trifluoroacetic anhydride (0.046 mL, 0.265 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(2-fluorophenyl)-N-(4-(2-(2,2,2-trifluoroacetyl)hydrazine-1-carbonyl)benzyl)thiomorpholine-4-carboxamide 1,1-dioxide, 0.144 g, 94.5%, light brown foam).

[Step 5] Compound 21447

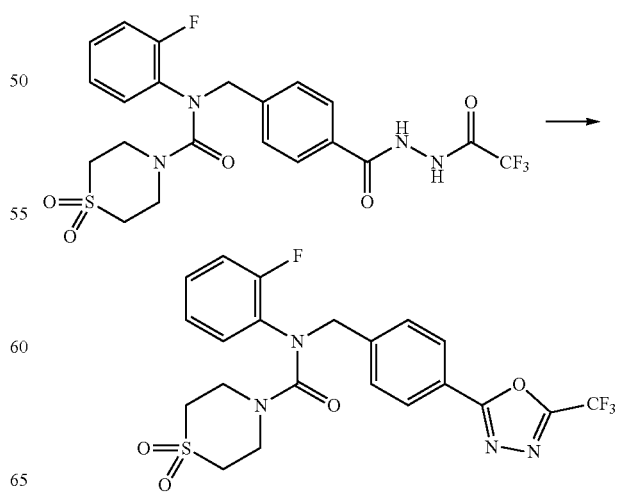

N-(2-fluorophenyl)-N-(4-(2-(2,2,2-trifluoroacetyl)hydrazine-1-carbonyl)benzyl)thiomorpholine-4-carboxamide 1,1-dioxide (0.141 g, 0.273 mmol) prepared in Step 4 and 1-methoxy-N-triethylammoniosulfonyl-methanimidate (Burgess reagent, 0.098 g, 0.410 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-(2-fluorophenyl)-N-(4-(5-(trifluoromethyl)-1,3,4-oxadiazol-2-yl)benzyl)thiomorpholine-4-carboxamide 1,1-dioxide as white solid (0.085 g, 62.8%).

$^1$H NMR (400 MHz, CDCl$_3$) δ 8.00 (d, 2H, J=8.3 Hz), 7.47 (d, 2H, J=8.2 Hz), 7.20-7.03 (m, 3H), 4.82 (s, 2H), 3.75-3.67 (m, 4H), 2.75 (t, 4H, J=5.4 Hz); LRMS (ESI) m/z 499.17 (M$^+$+H).

Example 117. Compound 21448: N-(4-(5-(difluoromethyl)-1,3,4-oxadiazol-2-yl)benzyl)-N-(2-fluorophenyl)thiomorpholine-4-carboxamide 1,1-dioxide

[Step 1] (N-(4-(2-(2,2-difluoroacetyl)hydrazine-1-carbonyl)benzyl)-N-(2-fluorophenyl)thiomorpholine-4-carboxamide 1,1-dioxide

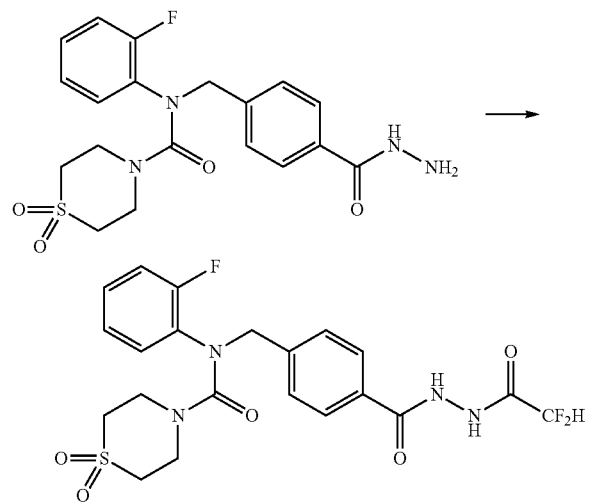

A solution of N-(2-fluorophenyl)-N-(4-(hydrazinecarbonyl)benzyl)thiomorpholine-4-carboxamide 1,1-dioxide (0.124 g, 0.295 mmol) prepared in Step 3 of Example 116 and triethylamine (0.082 mL, 0.590 mmol) in tetrahydrofuran (2 mL) was mixed at the room temperature with Difluoroacetic Anhydride (0.040 mL, 0.265 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2-difluoroacetyl)hydrazine-1-carbonyl)benzyl)-N-(2-fluorophenyl)thiomorpholine-4-carboxamide 1,1-dioxide, 0.141 g, 95.9%, light brown foam).

[Step 2] Compound 21448

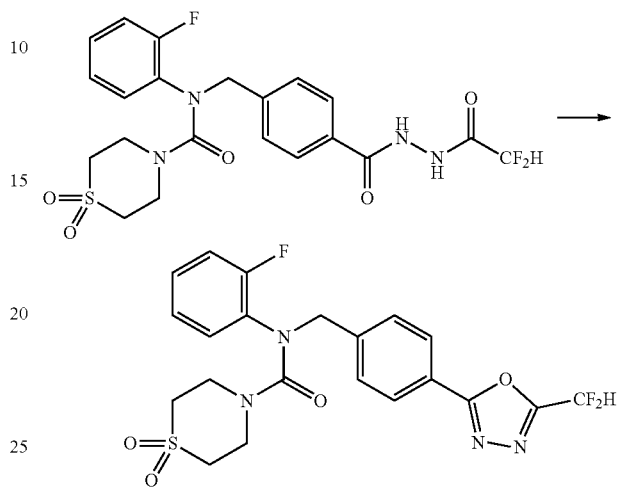

N-(4-(2-(2,2-difluoroacetyl)hydrazine-1-carbonyl)benzyl)-N-(2-fluorophenyl)thiomorpholine-4-carboxamide 1,1-dioxide (0.141 g, 0.283 mmol) prepared in Step 1 and 1-methoxy-N-triethylammoniosulfonyl-methanimidate (Burgess reagent, 0.101 g, 0.424 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-(4-(5-(difluoromethyl)-1,3,4-oxadiazol-2-yl)benzyl)-N-(2-fluorophenyl)thiomorpholine-4-carboxamide 1,1-dioxide as white solid (0.063 g, 46.2%).

$^1$H NMR (400 MHz, CDCl$_3$) δ 8.04-7.97 (m, 2H), 7.49-7.42 (m, 2H), 7.31-7.20 (m, 1H), 7.18-7.03 (m, 3H), 4.82 (s, 2H), 3.71 (t, 4H, J=5.3 Hz), 2.75 (t, 4H, J=5.3 Hz); LRMS (ESI) m/z 481.01 (M$^+$+H).

Example 118. Compound 21449: N-(4-(5-(trifluoromethyl)-1,3,4-oxadiazol-2-yl)benzyl)-N-(2-(trifluoromethyl)phenyl)thiomorpholine-4-carboxamide 1,1-dioxide

[Step 1] N-(2-(trifluoromethyl)phenyl)thiomorpholine-4-carboxamide 1,1-dioxide

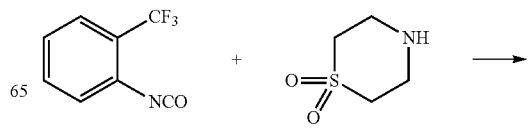

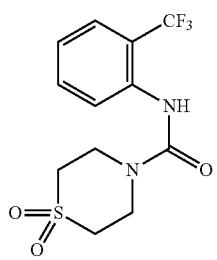

A solution of 1-isocyanato-2-(trifluoromethyl)benzene (1.000 g, 5.344 mmol) and thiomorpholine 1,1-dioxide (0.722 g, 5.344 mmol) in diethylether (20 mL) was stirred at the room temperature for 16 hr. The precipitates were collected by filtration, washed by diethylether, and dried to give the title compound N-(2-(trifluoromethyl)phenyl)thiomorpholine-4-carboxamide 1,1-dioxide as white solid (1.674 g, 97.2%).

[Step 2] Methyl 4-((1,1-dioxido-N-(2-(trifluoromethyl)phenyl)thiomorpholine-4-carboxamido)methyl) benzoate

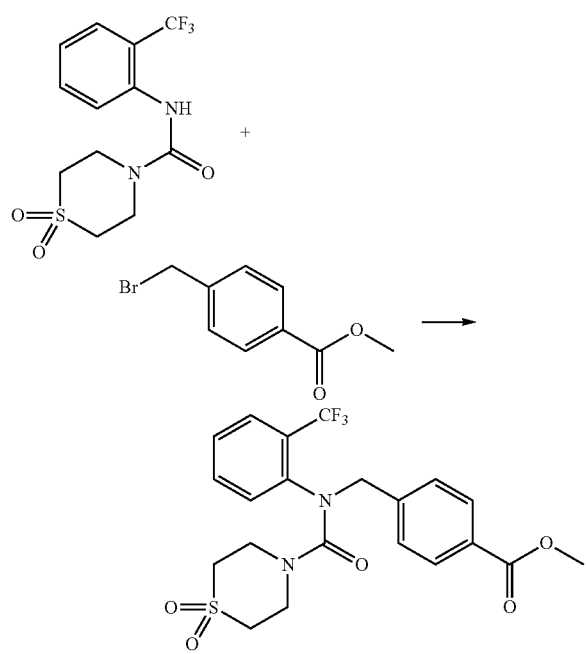

To a stirred solution of N-(2-(trifluoromethyl)phenyl)thiomorpholine-4-carboxamide 1,1-dioxide (0.300 g, 0.931 mmol) prepared in Step 1 in N,N-dimethylformamide (2 mL) was added at 0° C. sodium hydride (60.00%, 0.037 g, 0.931 mmol). The reaction mixture was stirred at the same temperature for 30 min, treated at the room temperature with methyl 4-(bromomethyl)benzoate (0.213 g, 0.931 mmol), and stirred for additional 2 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using ethyl acetate (1 mL) and hexane (10 mL). The resulting precipitates were filtered, washed by hexane, and dried to give the title compound methyl 4-((1,1-dioxido-N-(2-(trifluoromethyl)phenyl)thiomorpholine-4-carboxamido)methyl) benzoate as white solid (0.380 g, 86.7%).

[Step 3] N-(4-(hydrazinecarbonyl)benzyl)-N-(2-(trifluoromethyl)phenyl)thiomorpholine-4-carboxamide 1,1-dioxide

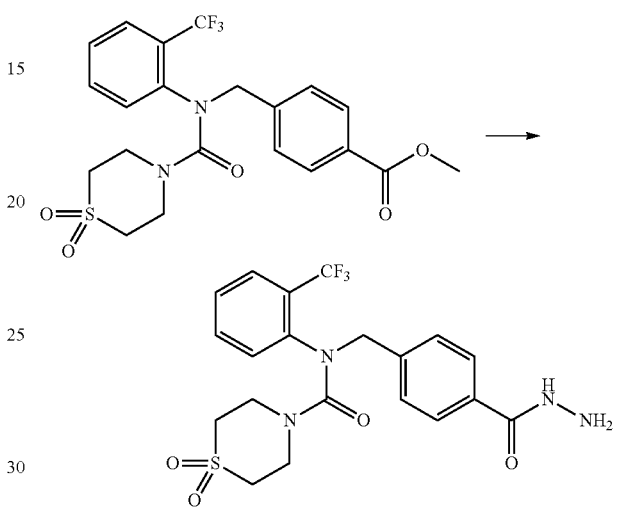

Methyl 4-((1,1-dioxido-N-(2-(trifluoromethyl)phenyl)thiomorpholine-4-carboxamido)methyl) benzoate (0.380 g, 0.807 mmol) prepared in Step 2 and hydrazine monohydrate (0.762 mL, 16.142 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(hydrazinecarbonyl)benzyl)-N-(2-(trifluoromethyl)phenyl)thiomorpholine-4-carboxamide 1,1-dioxide as white foam (0.317 g, 83.5%).

[Step 4] (N-(4-(2-(2,2,2-trifluoroacetyl)hydrazine-1-carbonyl)benzyl)-N-(2-(trifluoromethyl)phenyl)thiomorpholine-4-carboxamide 1,1-dioxide

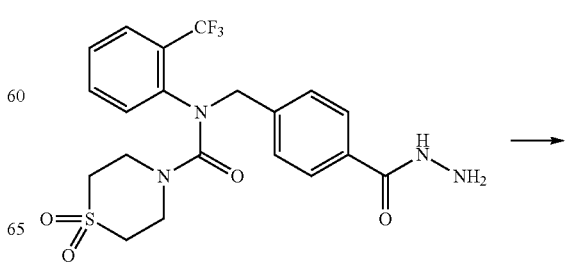

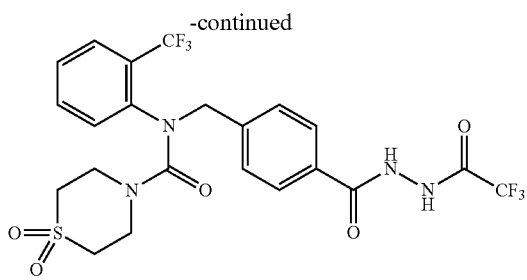

A solution of N-(4-(hydrazinecarbonyl)benzyl)-N-(2-(trifluoromethyl)phenyl)thiomorpholine-4-carboxamide 1,1-dioxide (0.159 g, 0.337 mmol) prepared in Step 3 and triethylamine (0.093 mL, 0.674 mmol) in tetrahydrofuran (2 mL) was mixed at the room temperature with trifluoroacetic anhydride (0.053 mL, 0.303 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2,2-trifluoroacetyl)hydrazine-1-carbonyl)benzyl)-N-(2-(trifluoromethyl)phenyl)thiomorpholine-4-carboxamide 1,1-dioxide, 0.181 g, 94.8%, light brown foam).

[Step 5] Compound 21449

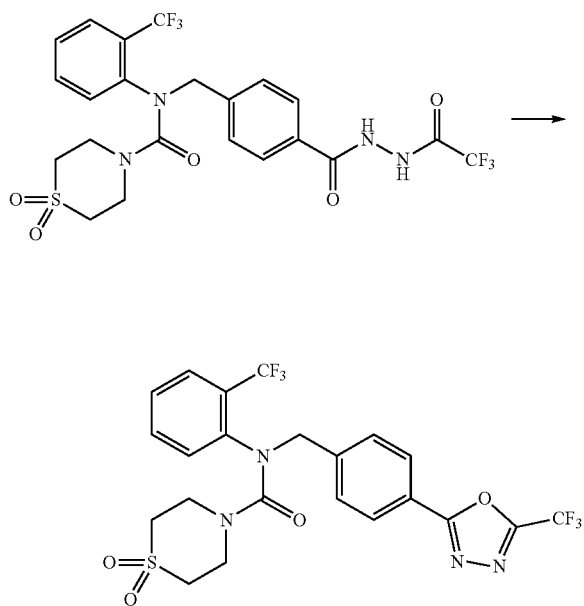 [SMILES: Cc1ccc(N(Cc2ccc(C(=O)NNC(=O)C(F)(F)F)cc2)C(=O)N2CCS(=O)(=O)CC2)c(F)c1 ; Cc1ccc(N(Cc2ccc(-c3nnc(C(F)(F)F)o3)cc2)C(=O)N2CCS(=O)(=O)CC2)c(F)c1]

N-(4-(2-(2,2,2-trifluoroacetyl)hydrazine-1-carbonyl)benzyl)-N-(2-(trifluoromethyl)phenyl)thiomorpholine-4-carboxamide 1,1-dioxide (0.181 g, 0.320 mmol) prepared in Step 4 and 1-methoxy-N-triethylammoniosulfonyl-methanimidate (Burgess reagent, 0.114 g, 0.479 mmol) in tetrahydrofuran (2 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-(4-(5-(trifluoromethyl)-1,3,4-oxadiazol-2-yl)benzyl)-N-(2-(trifluoromethyl)phenyl)thiomorpholine-4-carboxamide 1,1-dioxide as white solid (0.100 g, 57.2%).

$^1$H NMR (400 MHz, CDCl$_3$) δ 8.03 (d, 2H, J=8.3 Hz), 7.80 (dd, 1H, J=7.6, 1.9 Hz), 7.55-7.39 (m, 4H), 7.00-6.93 (m, 1H), 5.20 (s, 1H), 4.47 (s, 1H), 3.67 (d, 4H, J=7.0 Hz), 2.82 (t, 4H, J=5.3 Hz); LRMS (ESI) m/z 549.24 (M$^+$+H).

Example 119. Compound 21450: N-(4-(5-(difluoromethyl)-1,3,4-oxadiazol-2-yl)benzyl)-N-(2-(trifluoromethyl)phenyl)thiomorpholine-4-carboxamide 1,1-dioxide

[Step 1] (N-(4-(2-(2,2-difluoroacetyl)hydrazine-1-carbonyl)benzyl)-N-(2-(trifluoromethyl)phenyl)thiomorpholine-4-carboxamide 1,1-dioxide

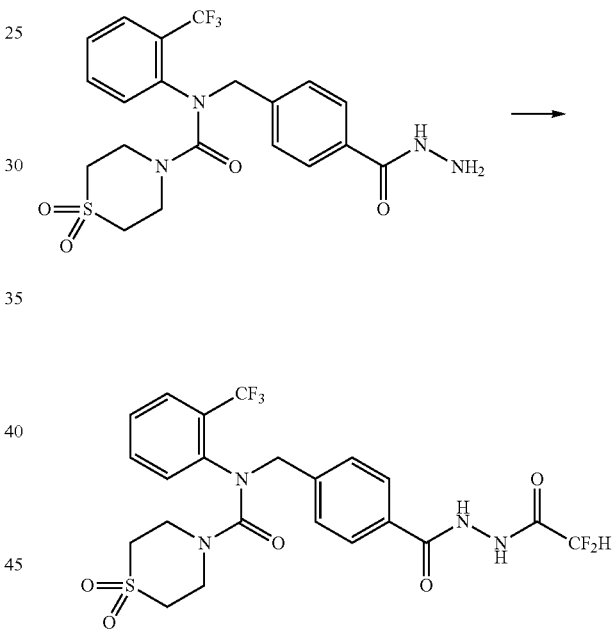

A solution of N-(4-(hydrazinecarbonyl)benzyl)-N-(2-(trifluoromethyl)phenyl)thiomorpholine-4-carboxamide 1,1-dioxide (0.159 g, 0.337 mmol) prepared in Step 3 of Example 118 and triethylamine (0.093 mL, 0.674 mmol) in tetrahydrofuran (2 mL) was mixed at the room temperature with Difluoroacetic Anhydride (0.045 mL, 0.303 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2-difluoroacetyl)hydrazine-1-carbonyl)benzyl)-N-(2-(trifluoromethyl)phenyl)thiomorpholine-4-carboxamide 1,1-dioxide, 0.178 g, 96.3%, light brown foam).

493

[Step 2] Compound 21450

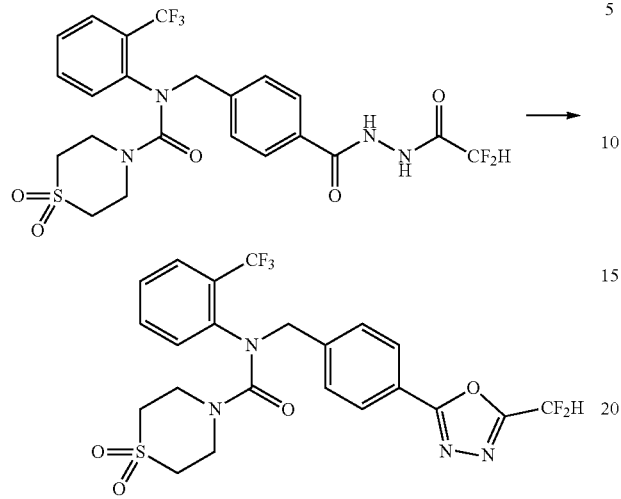

N-(4-(2-(2,2-difluoroacetyl)hydrazine-1-carbonyl)benzyl)-N-(2-(trifluoromethyl)phenyl)thiomorpholine-4-carboxamide 1,1-dioxide (0.178 g, 0.325 mmol) prepared in Step 1 and 1-methoxy-N-triethylammoniosulfonyl-methanimidate (Burgess reagent, 0.116 g, 0.487 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-(4-(5-(difluoromethyl)-1,3,4-oxadiazol-2-yl)benzyl)-N-(2-(trifluoromethyl)phenyl)thiomorpholine-4-carboxamide 1,1-dioxide as white solid (0.103 g, 59.5%).

$^1$H NMR (400 MHz, CDCl$_3$) δ 8.07-7.99 (m, 2H), 7.80 (dd, 1H, J=7.7, 2.0 Hz), 7.55-7.37 (m, 4H), 7.08-6.72 (m, 2H), 5.22 (s, 1H), 4.46 (s, 1H), 3.67 (s, 4H), (t, 4H, J=5.3 Hz); LRMS (ESI) m/z 531.00 (M$^+$+H).

Example 120. Compound 21451: N-(o-tolyl)-N-(4-(5-(trifluoromethyl)-1,3,4-oxadiazol-2-yl)benzyl)thiomorpholine-4-carboxamide 1,1-dioxide

[Step 1] N-(o-tolyl)thiomorpholine-4-carboxamide 1,1-dioxide

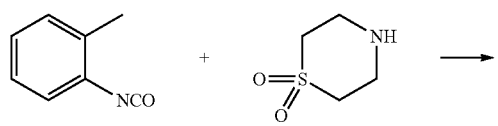

494

-continued

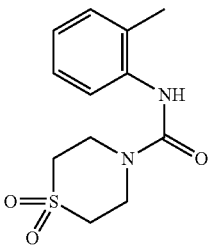

A solution of 1-isocyanato-2-methylbenzene (1.000 g, 7.510 mmol) and thiomorpholine 1,1-dioxide (1.015 g, 7.510 mmol) in diethylether (20 mL) was stirred at the room temperature for 16 hr. The precipitates were collected by filtration, washed by diethylether, and dried to give the title compound N-(o-tolyl)thiomorpholine-4-carboxamide 1,1-dioxide as white solid (1.941 g, 96.3%).

[Step 2] Methyl 4-((1,1-dioxido-N-(o-tolyl)thiomorpholine-4-carboxamido)methyl)benzoate

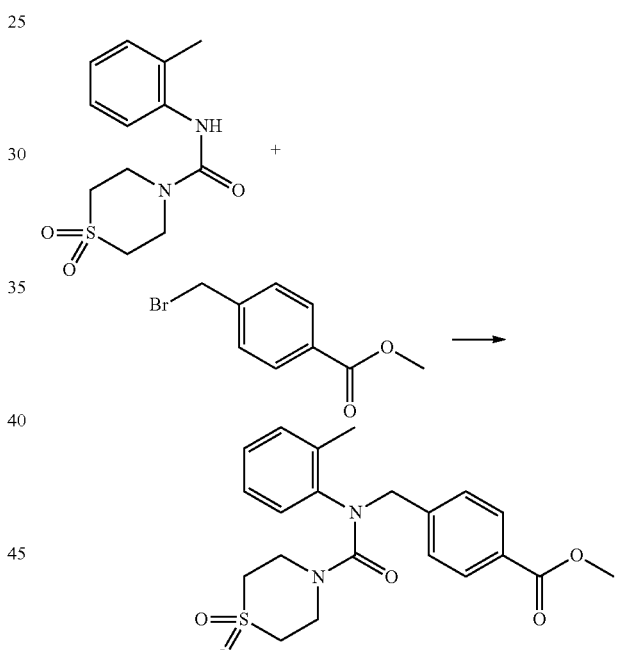

To a stirred solution of N-(o-tolyl)thiomorpholine-4-carboxamide 1,1-dioxide (0.300 g, 1.118 mmol) prepared in Step 1 in N,N-dimethylformamide (2 mL) was added at 0° C. sodium hydride (60.00%, 0.045 g, 1.118 mmol). The reaction mixture was stirred at the same temperature for 30 min, treated at the room temperature with methyl 4-(bromomethyl)benzoate (0.256 g, 1.118 mmol), and stirred for additional 2 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using ethyl acetate (1 mL) and hexane (10 mL). The resulting precipitates were filtered, washed by hexane, and dried to give the title compound methyl 4-((1,1-dioxido-N-(o-tolyl)thiomorpholine-4-carboxamido)methyl)benzoate as white solid (0.367 g, 78.7%).

[Step 3] N-(4-(hydrazinecarbonyl)benzyl)-N-(o-tolyl)thiomorpholine-4-carboxamide 1,1-dioxide

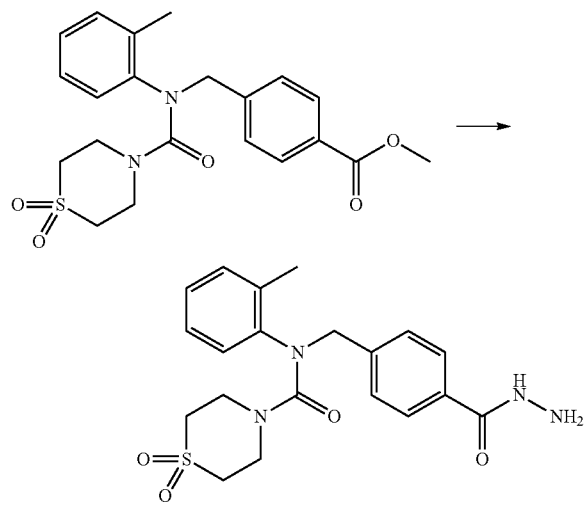

Methyl 4-((1,1-dioxido-N-(o-tolyl)thiomorpholine-4-carboxamido)methyl)benzoate (0.367 g, 0.880 mmol) prepared in Step 2 and hydrazine monohydrate (0.831 mL, 17.604 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(hydrazinecarbonyl)benzyl)-N-(o-tolyl)thiomorpholine-4-carboxamide 1,1-dioxide as white foam (0.241 g, 65.6%).

[Step 4] (N-(o-tolyl)-N-(4-(2-(2,2,2-trifluoroacetyl) hydrazine-1-carbonyl)benzyl)thiomorpholine-4-carboxamide 1,1-dioxide

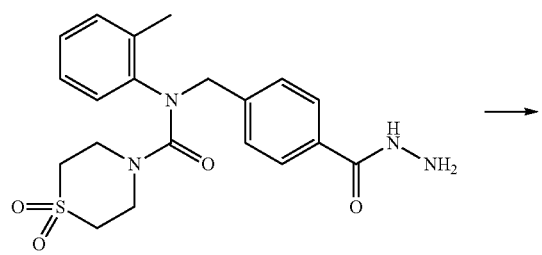

-continued

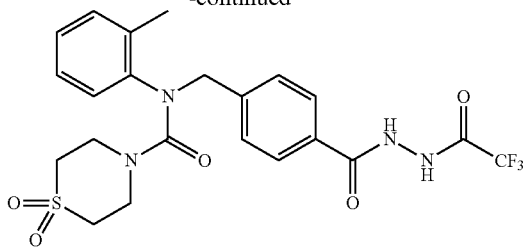

A solution of N-(4-(hydrazinecarbonyl)benzyl)-N-(o-tolyl)thiomorpholine-4-carboxamide 1,1-dioxide (0.120 g, 0.289 mmol) prepared in Step 3 and triethylamine (0.080 mL, 0.577 mmol) in tetrahydrofuran (2 mL) was mixed at the room temperature with trifluoroacetic anhydride (0.045 mL, 0.260 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(o-tolyl)-N-(4-(2-(2,2,2-trifluoroacetyl)hydrazine-1-carbonyl)benzyl)thiomorpholine-4-carboxamide 1,1-dioxide, 0.141 g, 95.3%, light brown foam).

[Step 5] Compound 21451

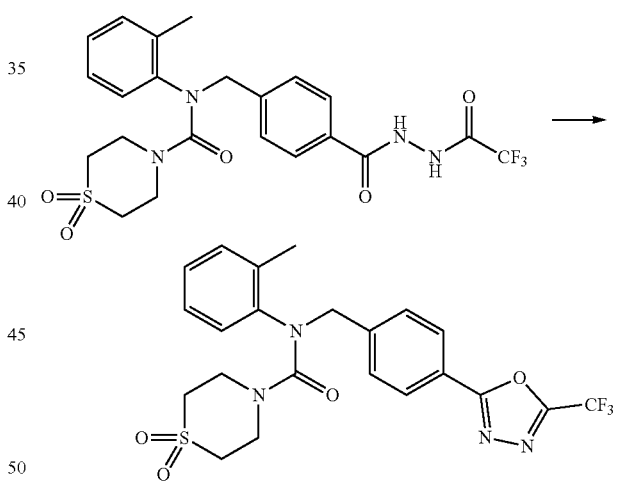

N-(o-tolyl)-N-(4-(2-(2,2,2-trifluoroacetyl)hydrazine-1-carbonyl)benzyl)thiomorpholine-4-carboxamide 1,1-dioxide (0.141 g, 0.275 mmol) prepared in Step 4 and 1-methoxy-N-triethylammoniosulfonyl-methanimidate (Burgess reagent, 0.098 g, 0.413 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50. %) to give the title compound N-(o-tolyl)-N-(4-(5-(trifluoromethyl)-1,3,4-oxadiazol-2-yl)benzyl)thiomorpholine-4-carboxamide 1,1-dioxide as white solid (0.077 g, 56.6%).

$^1$H NMR (400 MHz, CDCl$_3$) δ 7.99 (d, 2H, J=8.1 Hz), 7.40 (d, 2H, J=8.1 Hz), 7.22 (dddd, 3H, J=14.3, 11.0, 8.1, 4.5 Hz), 6.94 (dd, 1H, J=6.8, 2.2 Hz), 4.76 (s, 2H), 3.66 (t, 4H, J=5.2 Hz), 2.70 (t, 4H, J=5.3 Hz), 2.08 (s, 3H); LRMS (ESI) 495.0 (M$^+$+H).

Example 121. Compound 21452: N-(4-(5-(difluoromethyl)-1,3,4-oxadiazol-2-yl)benzyl)-N-(o-tolyl)thiomorpholine-4-carboxamide 1,1-dioxide

[Step 1] (N-(4-(2-(2,2-difluoroacetyl)hydrazine-1-carbonyl)benzyl)-N-(o-tolyl)thiomorpholine-4-carboxamide 1,1-dioxide

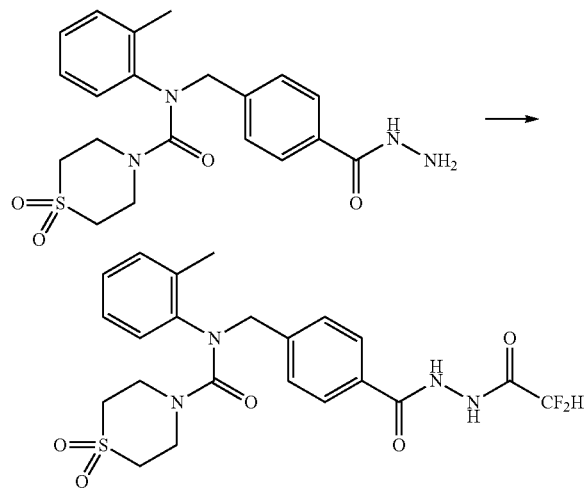

A solution of N-(4-(hydrazinecarbonyl)benzyl)-N-(o-tolyl)thiomorpholine-4-carboxamide 1,1-dioxide (0.120 g, 0.289 mmol) prepared in Step 3 of Example 120 and triethylamine (0.080 mL, 0.577 mmol) in tetrahydrofuran (2 mL) was mixed at the room temperature with Difluoroacetic Anhydride (0.039 mL, 0.260 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2-difluoroacetyl)hydrazine-1-carbonyl)benzyl)-N-(o-tolyl)thiomorpholine-4-carboxamide 1,1-dioxide, 0.137 g, 96.0%, light brown foam).

[Step 2] Compound 21451

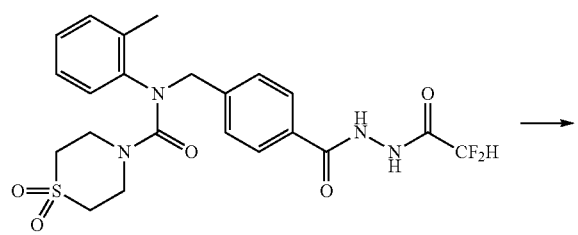

-continued

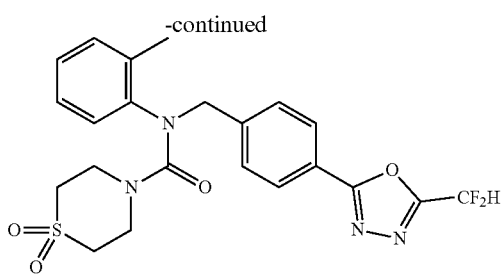

N-(4-(2-(2,2-difluoroacetyl)hydrazine-1-carbonyl)benzyl)-N-(o-tolyl)thiomorpholine-4-carboxamide 1,1-dioxide (0.137 g, 0.277 mmol) prepared in Step 1 and 1-methoxy-N-triethylammoniosulfonyl-methanimidate (Burgess reagent, 0.099 g, 0.416 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-(4-(5-(difluoromethyl)-1,3,4-oxadiazol-2-yl)benzyl)-N-(o-tolyl)thiomorpholine-4-carboxamide 1,1-dioxide as white solid (0.051 g, 38.6%).

$^1$H NMR (400 MHz, CDCl$_3$) δ 8.03-7.96 (m, 2H), 7.39 (d, 2H, J=8.1 Hz), 7.28-7.15 (m, 4H), 7.08-6.68 (m, 3H), 4.76 (s, 2H), 3.67 (s, 4H), 2.70 (t, 4H, J=5.3 Hz), 2.08 (s, 3H); LRMS (ESI) m/z 477.1 (M$^+$+H).

Example 122. Compound 21453: N-(4-(5-(difluoromethyl)-1,3,4-oxadiazol-2-yl)benzyl)-N-(4-methoxyphenyl)thiomorpholine-4-carboxamide 1,1-dioxide

[Step 1] N-(4-methoxyphenyl)thiomorpholine-4-carboxamide 1,1-dioxide

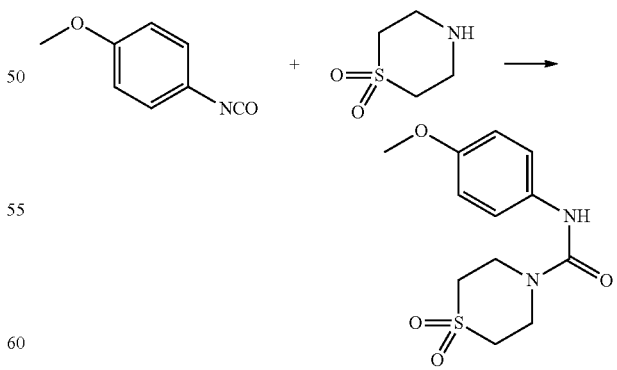

A solution of 1-isocyanato-4-methoxybenzene (3.800 g, 25.478 mmol) and thiomorpholine 1,1-dioxide (3.444 g, 25.478 mmol) in diethylether (20 mL) was stirred at the room temperature for 16 hr. The precipitates were collected by filtration, washed by diethylether, and dried to give the title compound N-(4-methoxyphenyl)thiomorpholine-4-carboxamide 1,1-dioxide as white solid (6.875 g, 94.9%).

[Step 2] Methyl 4-((N-(4-methoxyphenyl)-1,1-dioxidothiomorpholine-4-carboxamido)methyl)benzoate

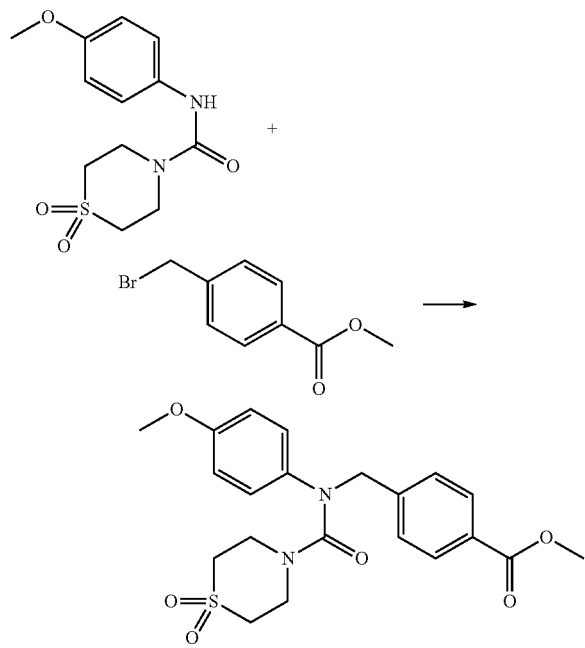

To a stirred solution of N-(4-methoxyphenyl)thiomorpholine-4-carboxamide 1,1-dioxide (0.300 g, 1.055 mmol) prepared in Step 1 in N,N-dimethylformamide (2 mL) was added at 0° C. sodium hydride (60.00%, 0.042 g, 1.055 mmol). The reaction mixture was stirred at the same temperature for 30 min, treated at the room temperature with methyl 4-(bromomethyl)benzoate (0.242 g, 1.055 mmol), and stirred for additional 2 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using ethyl acetate (1 mL) and hexane (10 mL). The resulting precipitates were filtered, washed by hexane, and dried to give the title compound methyl 4-((N-(4-methoxyphenyl)-1,1-dioxidothiomorpholine-4-carboxamido)methyl)benzoate as white solid (0.355 g, 77.8%).

[Step 3] N-(4-(hydrazinecarbonyl)benzyl)-N-(4-methoxyphenyl)thiomorpholine-4-carboxamide 1,1-dioxide

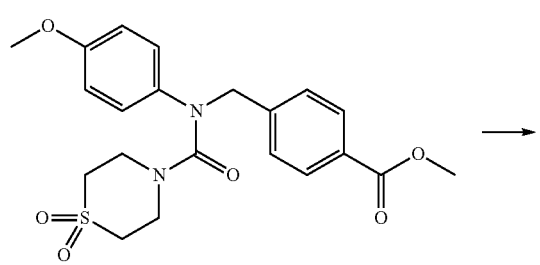

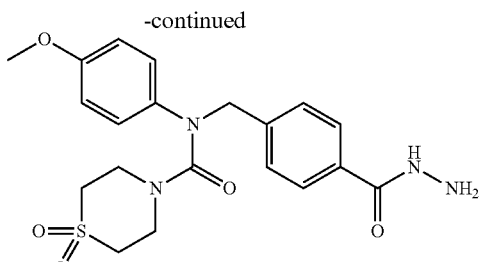

Methyl 4-((N-(4-methoxyphenyl)-1,1-dioxidothiomorpholine-4-carboxamido)methyl)benzoate (0.355 g, 0.820 mmol) prepared in Step 2 and hydrazine monohydrate (0.775 mL, 16.407 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(hydrazinecarbonyl)benzyl)-N-(4-methoxyphenyl)thiomorpholine-4-carboxamide 1,1-dioxide as white foam (0.350 g, 98.5%).

[Step 4] (N-(4-(2-(2,2-difluoroacetyl)hydrazine-1-carbonyl)benzyl)-N-(4-methoxyphenyl)thiomorpholine-4-carboxamide 1,1-dioxide

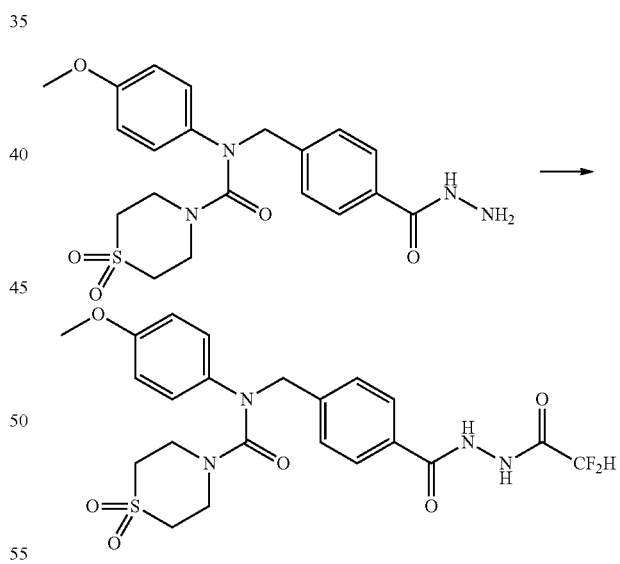

A solution of N-(4-(hydrazinecarbonyl)benzyl)-N-(4-methoxyphenyl)thiomorpholine-4-carboxamide 1,1-dioxide (0.175 g, 0.405 mmol) prepared in Step 3 and triethylamine (0.112 mL, 0.809 mmol) in tetrahydrofuran (2 mL) was mixed at the room temperature with Difluoroacetic Anhydride (0.055 mL, 0.364 mmol) stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2-difluoroacetyl)hydrazine-1-carbonyl)benzyl)-N-(4-methoxyphenyl)thiomorpholine-4-carboxamide 1,1-dioxide, 0.199 g, 96.3%, light brown foam).

[Step 5] Compound 21453

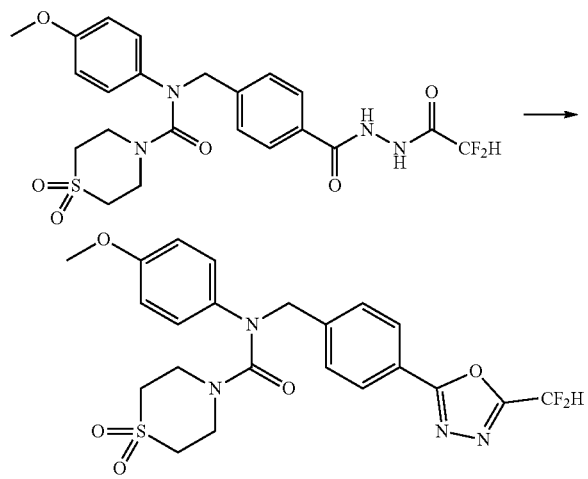

N-(4-(2-(2,2-difluoroacetyl)hydrazine-1-carbonyl)benzyl)-N-(4-methoxyphenyl)thiomorpholine-4-carboxamide 1,1-dioxide (0.199 g, 0.390 mmol) prepared in Step 4 and 1-methoxy-N-triethylammoniosulfonyl-methanimidate (Burgess reagent, 0.139 g, 0.585 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic fit to remove solid residues and aqueous layer, and the organic layer collected was concentrated in vacuo. The concentrate was purified and concentrated by column chromatography (SiO₂, 4 g cartridge; ethyl acetate/hexane=20% to 50%) to give the title compound N-(4-(5-(difluoromethyl)-1,3,4-oxadiazol-2-yl)benzyl)-N-(4-methoxyphenyl)thiomorpholine-4-carboxamide 1,1-dioxide as white solid (0.094 g, 49.0%).

¹H NMR (400 MHz, CDCl₃) δ 8.05-7.98 (m, 2H), 7.45-7.38 (m, 2H), 7.06-6.74 (m, 3H), 4.82 (s, 2H), 3.79 (d, 3H, J=0.8 Hz), 3.72 (t, 4H, J=5.6 Hz), 1.78 (t, 4H, J=5.3 Hz); LRMS (ESI) m/z 493.12 (M⁺+H).

Example 123. Compound 21454: N-(4-methoxyphenyl)-N-((5-(5-(trifluoromethyl)-1,3,4-oxadiazol-2-yl)pyridin-2-yl)methyl)thiomorpholine-4-carboxamide 1,1-dioxide

[Step 1] Methyl 6-((N-(4-methoxyphenyl)-1,1-dioxidothiomorpholine-4-carboxamido)methyl)nicotinate

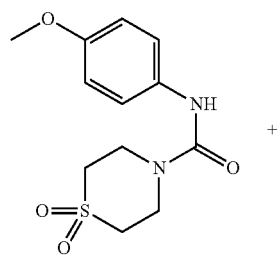

+

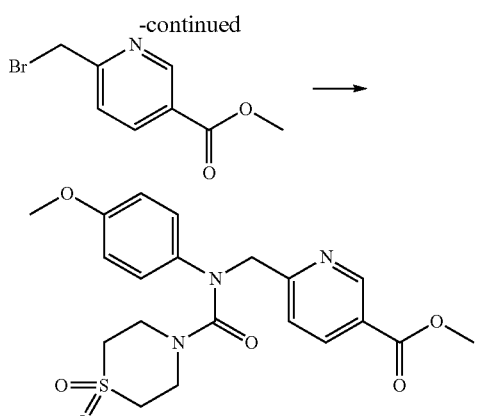

To a stirred solution of N-(4-methoxyphenyl)thiomorpholine-4-carboxamide 1,1-dioxide (0.300 g, 1.055 mmol) in N,N-dimethylformamide (2 mL) was added at 0° C. sodium hydride (60.00%, 0.042 g, 1.055 mmol). The reaction mixture was stirred at the same temperature for 30 min, treated at the room temperature with methyl 6-(bromomethyl)nicotinate (0.243 g, 1.055 mmol), and stirred for additional 2 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using ethyl acetate (1 mL) and hexane (10 mL). The resulting precipitates were filtered, washed by hexane, and dried to give the title compound methyl 6-((N-(4-methoxyphenyl)-1,1-dioxidothiomorpholine-4-carboxamido)methyl)nicotinat e as white solid (0.283 g, 61.8%).

[Step 2] N-((5-(hydrazinecarbonyl)pyridin-2-yl)methyl)-N-(4-methoxyphenyl)thiomorpholine-4-carboxamide 1,1-dioxide

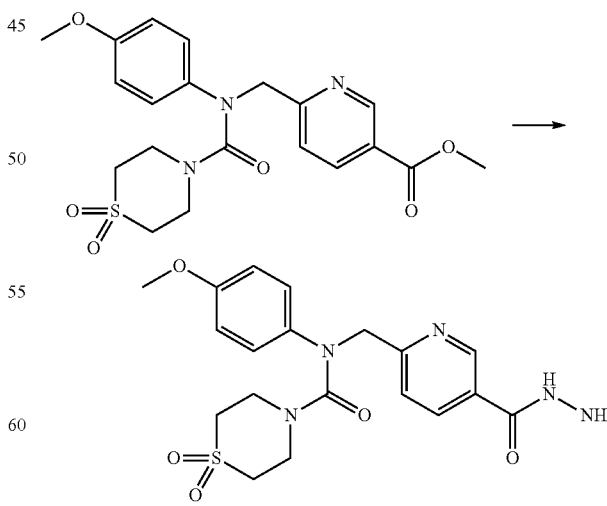

Methyl 6-((N-(4-methoxyphenyl)-1,1-dioxidothiomorpholine-4-carboxamido)methyl)nicotinat e (0.283 g, 0.652 mmol) prepared in Step 1 and hydrazine monohydrate (0.616 mL, 13.039 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-((5-(hydrazinecarbonyl)pyridin-2-yl)methyl)-N-(4-methoxyphenyl)thiomorpholine-4-carboxamide 1,1-dioxide as white foam (0.130 g, 45.9%).

[Step 3] (N-(4-methoxyphenyl)-N-((5-(2-(2,2,2-trifluoroacetyl)hydrazine-1-carbonyl)pyridin-2-yl)methyl)thiomorpholine-4-carboxamide 1,1-dioxide

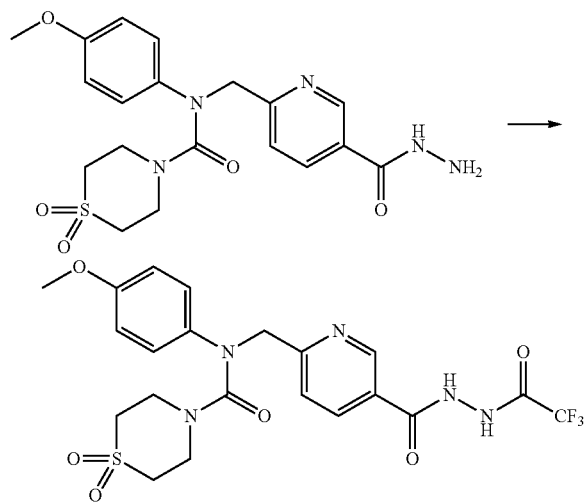

A solution of N-((5-(hydrazinecarbonyl)pyridin-2-yl)methyl)-N-(4-methoxyphenyl)thiomorpholine-4-carboxamide 1,1-dioxide (0.065 g, 0.150 mmol) prepared in Step 2 and triethylamine (0.041 mL, 0.299 mmol) in tetrahydrofuran (2 mL) was mixed at the room temperature with trifluoroacetic anhydride (0.023 mL, 0.135 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-methoxyphenyl)-N-((5-(2-(2,2,2-trifluoroacetyl)hydrazine-1-carbonyl)pyridin-2-yl)methyl)thiomorpholine-4-carboxamide 1,1-dioxide, 0.076 g, 95.9%, light brown foam).

[Step 4] Compound 21454

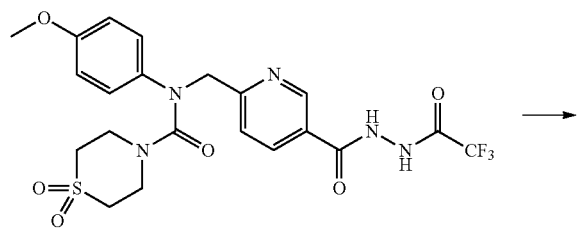

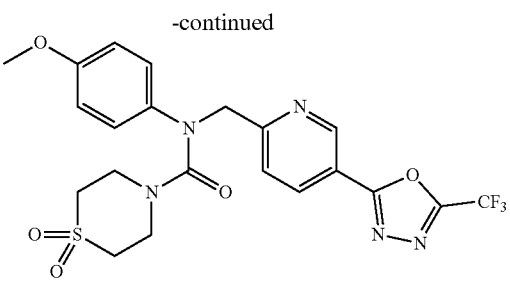

N-(4-methoxyphenyl)-N-((5-(2-(2,2,2-trifluoroacetyl)hydrazine-1-carbonyl)pyridin-2-yl)methyl)thiomorpholine-4-carboxamide 1,1-dioxide (0.076 g, 0.144 mmol) prepared in Step 3 and 1-methoxy-N-triethylammoniosulfonyl-methanimidate (Burgess reagent, 0.051 g, 0.215 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-(4-methoxyphenyl)-N-((5-(5-(trifluoromethyl)-1,3,4-oxadiazol-2-yl)pyridin-2-yl)methyl)thiomorpholine-4-carboxamide 1,1-dioxide as white solid (0.020 g, 27.0%).

$^1$H NMR (400 MHz, CDCl$_3$) δ 9.23 (dd, 1H, J=2.2, 0.9 Hz), 8.37 (ddd, 1H, J=8.2, 2.2, 0.9 Hz), 7.56 (d, 1H, J=8.2 Hz), 7.17-7.07 (m, 2H), 6.91-6.82 (m, 2H), 5.03 (s, 2H), 3.80 (d, 3H, J=0.9 Hz), 3.71 (d, 4H, J=5.6 Hz), 2.91 (t, 4H, J=5.3 Hz); LRMS (ESI) m/z 512.06 (M$^+$+H).

Example 124. Compound 21455: N-((5-(5-(difluoromethyl)-1,3,4-oxadiazol-2-yl)pyridin-2-yl)methyl)-N-(4-methoxyphenyl)thiomorpholine-4-carboxamide 1,1-dioxide

[Step 1] N-((5-(2-(2,2-difluoroacetyl)hydrazine-1-carbonyl)pyridin-2-yl)methyl)-N-(4-methoxyphenyl)thiomorpholine-4-carboxamide 1,1-dioxide

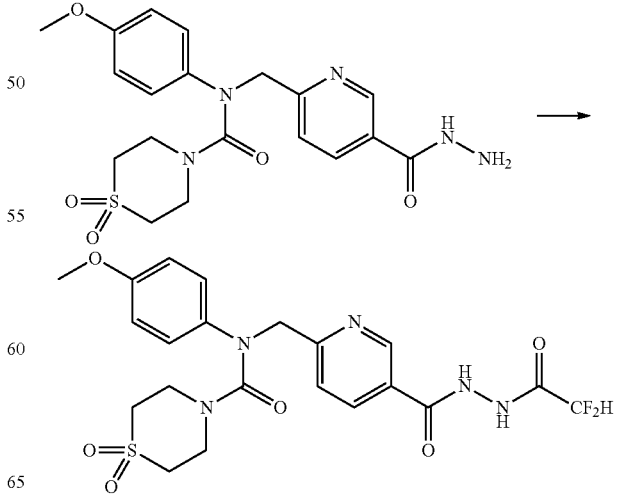

A solution of N-((5-(hydrazinecarbonyl)pyridin-2-yl)methyl)-N-(4-methoxyphenyl)thiomorpholine-4-carboxamide 1,1-dioxide (0.065 g, 0.150 mmol) prepared in Step 3 of Example 123 and triethylamine (0.041 mL, 0.299 mmol) in tetrahydrofuran (2 mL) was mixed at the room temperature with Difluoroacetic Anhydride (0.020 mL, 0.135 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product N-((5-(2-(2,2-difluoroacetyl)hydrazine-1-carbonyl)pyridin-2-yl)methyl)-N-(4-methoxyphenyl)thiomorpholine-4-carboxamide 1,1-dioxide was used without further purification (0.073 g, 95.3%, light brown foam).

[Step 2] Compound 21455

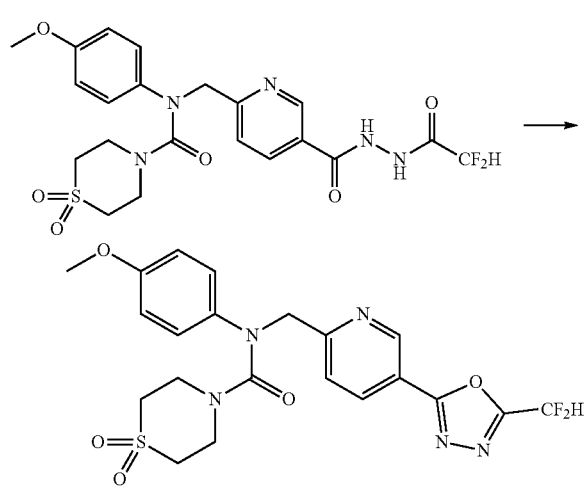

N-((5-(2-(2,2-difluoroacetyl)hydrazine-1-carbonyl)pyridin-2-yl)methyl)-N-(4-methoxyphenyl)thiomorpholine-4-carboxamide 1,1-dioxide (0.073 g, 0.143 mmol) prepared in Step 1 and 1-methoxy-N-triethylammoniosulfonyl-methanimidate (Burgess reagent, 0.051 g, 0.214 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-((5-(5-(difluoromethyl)-1,3,4-oxadiazol-2-yl)pyridin-2-yl)methyl)-N-(4-methoxyphenyl)thiomorpholine-4-carboxamide 1,1-dioxide as light yellow solid (0.028 g, 40.3%).

$^1$H NMR (400 MHz, CDCl$_3$) δ 9.23 (dd, 1H, J=2.3, 0.8 Hz), 8.36 (dd, 1H, J=8.2, 2.2 Hz), 7.54 (d, 1H, J=8.2 Hz), 7.17-7.09 (m, 2H), 7.08-6.78 (m, 3H), 5.03 (s, 2H), 3.79 (s, 3H), 3.71 (t, 4H, J=5.5 Hz), 2.91 (t, 4H, J=5.3 Hz); LRMS (ESI) m/z 494.1 (M$^+$+H).

Example 125. Compound 21456: N-(4-(5-(trifluoromethyl)-1,3,4-oxadiazol-2-yl)benzyl)-N-(6-(trifluoromethyl)pyridin-2-yl)thiomorpholine-4-carboxamide 1,1-dioxide

[Step 1] Methyl 4-(((6-(trifluoromethyl)pyridin-2-yl)amino)methyl)benzoate

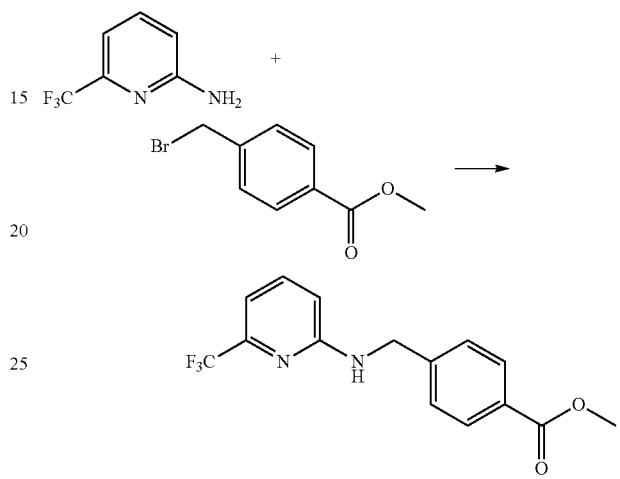

A solution of 6-(trifluoromethyl)pyridin-2-amine (10.000 g, 61.687 mmol), methyl 4-(bromomethyl)benzoate (16.957 g, 74.024 mmol) and N,N-diisopropylethylamine (16.010 mL, 92.530 mmol) in acetonitrile (150 mL) was stirred at 70° C. for 16 hr, and cooled down to the room temperature to terminate the reaction. Then, water was added to the reaction mixture, followed by extraction with dichloromethane. The organic layer was washed with aqueous saturated ammonium chloride solution, dried (anhydrous MgSO$_4$), filtered, and concentrated in vacuo. The concentrate was purified and concentrated by column chromatography (SiO$_2$, 120 g cartridge; ethyl acetate/hexane=0% to 15%) to give the title compound methyl 4-(((6-(trifluoromethyl)pyridin-2-yl)amino)methyl)benzoate as white solid (9.000 g, 47.0%).

[Step 2] Methyl 4-((((4-nitrophenoxy)carbonyl)(6-(trifluoromethyl)pyridin-2-yl)amino)methyl)benzoate

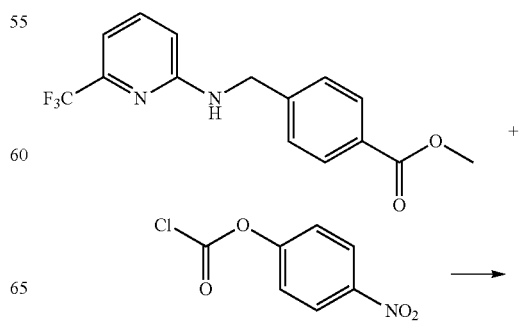

-continued

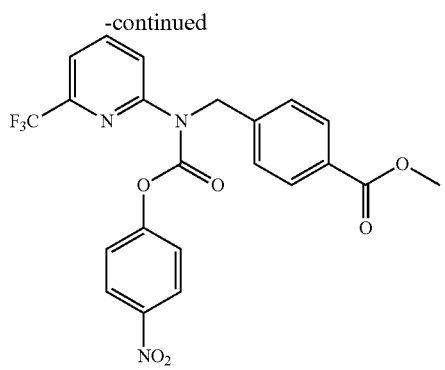

A solution of methyl 4-(((6-(trifluoromethyl)pyridin-2-yl)amino)methyl)benzoate (6.000 g, 19.338 mmol) prepared in Step 1, 4-Nitrophenyl chloroformate (7.796 g, 38.676 mmol) and K2CO3 (5.345 g, 38.676 mmol) in acetonitrile (100 mL) was stirred at the room temperature for 16 hr. The reaction mixture was filtered through a paper filter to remove solids, and the filtrate was concentrated under the reduced pressure to remove the solvent. The concentrate was purified and concentrated by column chromatography (SiO₂, 80 g cartridge; ethyl acetate/hexane=5% to 15%) to give the title compound methyl 4-(((((4-nitrophenoxy)carbonyl)(6-(trifluoromethyl)pyridin-2-yl)amino)methyl)benzoat e as yellow solid (5.074 g, 55.2%).

[Step 3] Methyl 4-((1,1-dioxido-N-(6-(trifluoromethyl)pyridin-2-yl)thiomorpholine-4-carboxamido)methyl)benzoate

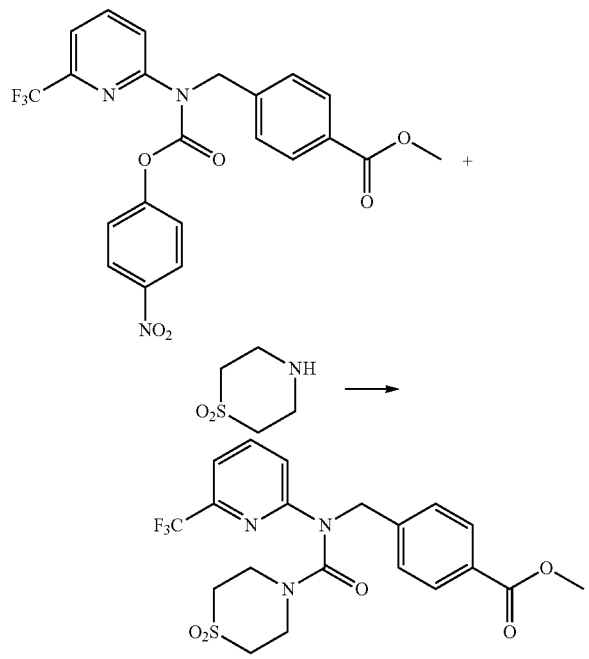

Methyl 4-(((((4-nitrophenoxy)carbonyl)(6-(trifluoromethyl)pyridin-2-yl)amino)methyl)benzoat e (0.500 g, 1.054 mmol) prepared in Step 2, thiomorpholine 1,1-dioxide (0.157 g, 1.159 mmol) and potassium carbonate (0.291 g, 2.108 mmol) were mixed at the room temperature in N,N-dimethylformamide (2 mL) and then stirred at 40° C. for 18 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using ethyl acetate (1 mL) and hexane (10 mL). The resulting precipitates were filtered, washed by hexane, and dried to give the title compound methyl 4-((1,1-dioxido-N-(6-(trifluoromethyl)pyridin-2-yl)thiomorpholine-4-carboxamido)methyl)benzoate as white solid (0.225 g, 45.2%).

[Step 4] N-(4-(hydrazinecarbonyl)benzyl)-N-(6-(trifluoromethyl)pyridin-2-yl)thiomorpholine-4-carboxamide 1,1-dioxide

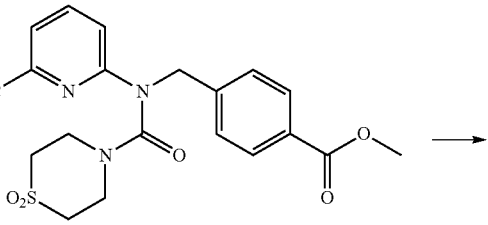

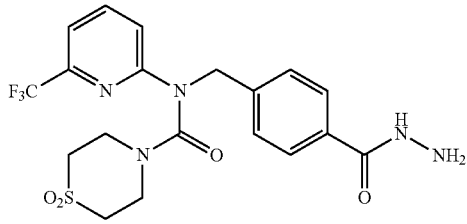

Methyl 4-((1,1-dioxido-N-(6-(trifluoromethyl)pyridin-2-yl)thiomorpholine-4-carboxamido)methyl)benzoate (0.225 g, 0.477 mmol) prepared in Step 3 and hydrazine monohydrate (0.450 mL, 9.532 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane-. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-(4-(hydrazinecarbonyl)benzyl)-N-(6-(trifluoromethyl)pyridin-2-yl)thiomorpholine-4-carboxamide 1,1-dioxide as white foam (0.154 g, 68.6%).

509

[Step 5] N-(4-(2-(2,2,2-trifluoroacetyl)hydrazine-1-carbonyl)benzyl)-N-(6-(trifluoromethyl)pyridin-2-yl)thiomorpholine-4-carboxamide 1,1-dioxide

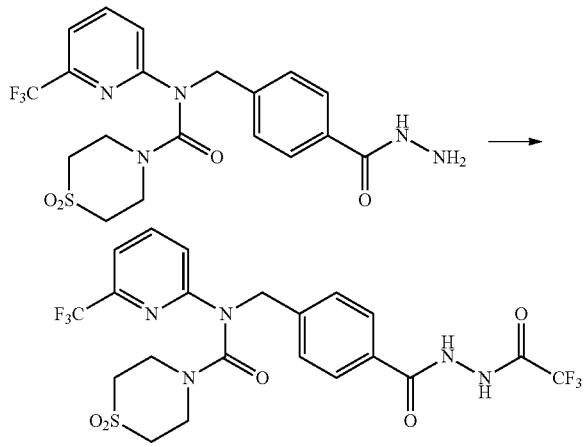

A solution of N-(4-(hydrazinecarbonyl)benzyl)-N-(6-(trifluoromethyl)pyridin-2-yl)thiomorpholine-4-carboxamide 1,1-dioxide (0.077 g, 0.164 mmol) prepared in Step 4 and triethylamine (0.045 mL, 0.327 mmol) in tetrahydrofuran (2 mL) was mixed at the room temperature with trifluoroacetic anhydride (0.026 mL, 0.147 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2,2-trifluoroacetyl)hydrazine-1-carbonyl)benzyl)-N-(6-(trifluoromethyl)pyridin-2-yl)thiomorpholine-4-carboxamide 1,1-dioxide, 0.084 g, 90.5%, light brown foam).

[Step 6] Compound 21456

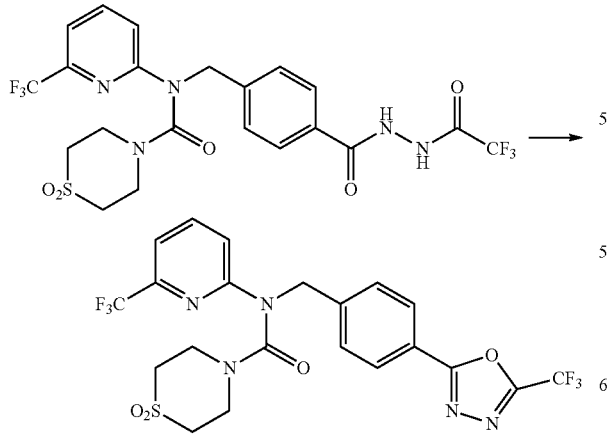

N-(4-(2-(2,2,2-trifluoroacetyl)hydrazine-1-carbonyl)benzyl)-N-(6-(trifluoromethyl)pyridin-2-yl)thiomorpholine-4-carboxamide 1,1-dioxide (0.084 g, 0.148 mmol) prepared in Step 5 and 1-methoxy-N-triethylammoniosulfonyl-methan-

510 imidate (Burgess reagent, 0.053 g, 0.222 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=20% to 50%) to give the title compound N-(4-(5-(trifluoromethyl)-1,3,4-oxadiazol-2-yl)benzyl)-N-(6-(trifluoromethyl)pyridin-2-yl)thiomorpholine-4-carboxamide 1,1-dioxide as light yellow solid (0.015 g, 18.3%).

$^1$H NMR (400 MHz, CDCl$_3$) δ 8.09-8.02 (m, 2H), 7.79 (t, 1H, J=8.0 Hz), 7.66-7.52 (m, 2H), 7.35 (d, 1H, J=7.5 Hz), 7.12 (d, 1H, J=8.4 Hz), 5.17 (s, 2H), 3.80 (t, 4H, J=5.3 Hz), 2.97-2.90 (m, 4H); LRMS (ESI) m/z 550.22 (M$^+$+H).

Example 126. Compound 21457: N-(4-(5-(difluoromethyl)-1,3,4-oxadiazol-2-yl)benzyl)-N-(6-(trifluoromethyl)pyridin-2-yl)thiomorpholine-4-carboxamide 1,1-dioxide

[Step 1] N-(4-(2-(2,2-difluoroacetyl)hydrazine-1-carbonyl)benzyl)-N-(6-(trifluoromethyl)pyridin-2-yl)thiomorpholine-4-carboxamide 1,1-dioxide

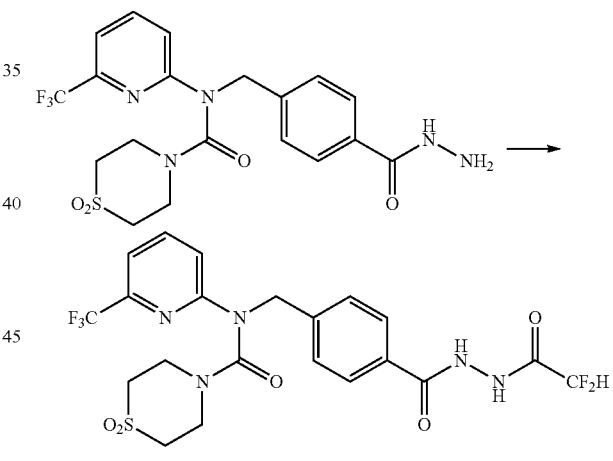

A solution of N-(4-(hydrazinecarbonyl)benzyl)-N-(6-(trifluoromethyl)pyridin-2-yl)thiomorpholine-4-carboxamide 1,1-dioxide (0.077 g, 0.164 mmol) prepared in Step 4 of Example 125 and triethylamine (0.045 mL, 0.327 mmol) in tetrahydrofuran (2 mL) was mixed at the room temperature with Difluoroacetic Anhydride (0.022 mL, 0.147 mmol), stirred at 70° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2-difluoroacetyl)hydrazine-1-carbonyl)benzyl)-N-(6-(trifluoromethyl)pyridin-2-yl)thiomorpholine-4-carboxamide 1,1-dioxide, 0.086 g, 95.7%, light brown foam).

[Step 2] Compound 21457

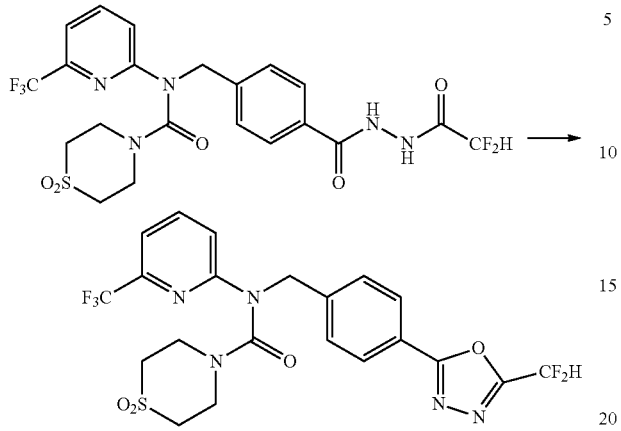

N-(4-(2-(2,2-difluoroacetyl)hydrazine-1-carbonyl)benzyl)-N-(6-(trifluoromethyl)pyridin-2-yl)thiomorpholine-4-carboxamide 1,1-dioxide (0.086 g, 0.157 mmol) prepared in Step 1 and 1-methoxy-N-triethylammoniosulfonyl-methanimidate (Burgess reagent, 0.056 g, 0.235 mmol) in tetrahydrofuran (3 mL) was mixed at the room temperature and then heated at 150° C. under the microwaves for 30 min, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; acetonitrile/formic acid=5% to 70%) to give the title compound N-(4-(5-(difluoromethyl)-1,3,4-oxadiazol-2-yl)benzyl)-N-(6-(trifluoromethyl)pyridin-2-yl)thiomorpholine-4-carboxamide 1,1-dioxide as white solid (0.004 g, 4.7%).
$^1$H NMR (400 MHz, CDCl$_3$) δ 8.05 (d, 2H, J=8.1 Hz), 7.84-7.74 (m, 1H), 7.61 (d, 2H, J=8.0 Hz), 7.35 (d, 1H, J=7.5 Hz), 7.11 (d, 1H, J=8.3 Hz), 7.06-6.73 (m, 1H), 5.17 (s, 2H), 3.80 (s, 4H), 2.93 (t, 4H, J=5.3 Hz); LRMS (ESI) m/z 532.20 (M$^+$+H).

Example 127. Compound 21458: N-(4-(tert-butyl)phenyl)-N-(4-(5-(trifluoromethyl)-1,3,4-oxadiazol-2-yl)benzyl)thiomorpholine-4-carboxamide 1,1-dioxide

[Step 1] N-(4-(tert-butyl)phenyl)-N-(4-(hydrazinecarbonyl)benzyl)thiomorpholine-4-carboxamide 1,1-dioxide

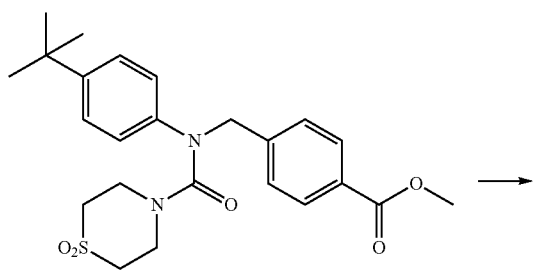

A mixture of methyl 4-((N-(4-(tert-butyl)phenyl)-1,1-dioxidothiomorpholine-4-carboxamido)methyl)benzoate (0.368 g, 0.802 mmol) and hydrazine monohydrate (0.758 mL, 16.050 mmol) in ethanol (10 mL) was heated at reflux for 16 hr, and cooled down to the ambient temperature. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 5%) to give the title compound N-(4-(tert-butyl)phenyl)-N-(4-(hydrazinecarbonyl)benzyl)thiomorpholine-4-carboxamide 1,1-dioxide as white solid (0.257 g, 69.8%).

[Step 2] N-(4-(tert-butyl)phenyl)-N-(4-(2-(2,2,2-trifluoroacetyl)hydrazine-1-carbonyl)benzyl)thiomorpholine-4-carboxamide 1,1-dioxide

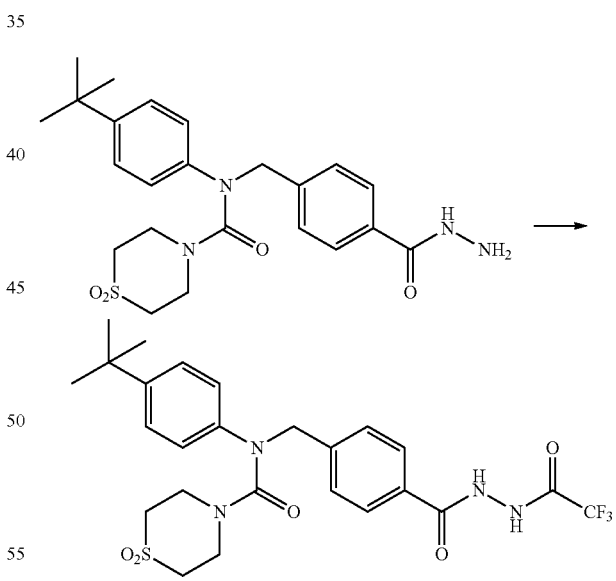

A solution of N-(4-(tert-butyl)phenyl)-N-(4-(hydrazinecarbonyl)benzyl)thiomorpholine-4-carboxamide 1,1-dioxide (0.128 g, 0.279 mmol) prepared in Step 1 and triethylamine (0.058 mL, 0.419 mmol) in dichloromethane (5 mL) was mixed at 0° C. with trifluoroacetic anhydride (0.035 mL, 0.251 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-(4-(tert-butyl)phenyl)-N-(4-(2-(2,2,2-trifluoroacetyl)hydrazine-1-carbonyl)benzyl)thiomorpholine-4-carboxamide 1,1-dioxide as white solid (0.097 g, 62.8%).

[Step 3] Compound 21458

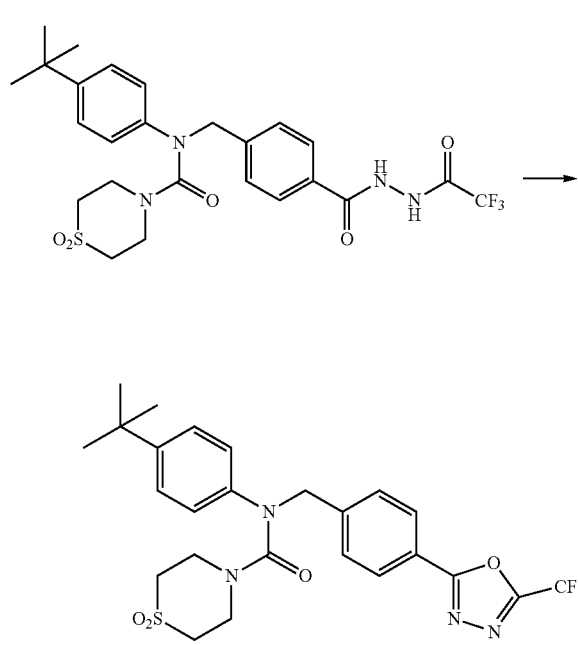

A mixture of N-(4-(tert-butyl)phenyl)-N-(4-(2-(2,2,2-trifluoroacetyl)hydrazine-1-carbonyl)benzyl)thiomorpholine-4-carboxamide 1,1-dioxide (0.097 g, 0.175 mmol) prepared in Step 2 and 1-methoxy-N-triethylammoniosulfonylmethanimidate (Burgess reagent, 0.063 g, 0.263 mmol) in tetrahydrofuran (2 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(tert-butyl)phenyl)-N-(4-(5-(trifluoromethyl)-1,3,4-oxadiazol-2-yl)benzyl)thiomorpholine-4-carboxamide 1,1-dioxide as white solid (0.071 g, 75.5%).

$^1$H NMR (400 MHz, CDCl$_3$) δ 8.02 (d, 2H, J=8.4 Hz), 7.45 (d, 2H, J=8.4 Hz), 7.35 (d, 2H, J=8.6 Hz), 6.99 (d, 2H, J=8.6 Hz), 4.87 (s, 2H), 3.71-3.68 (m, 4H), 2.79-2.77 (m, 4H), 1.29 (s, 9H); LRMS (ES) m/z 537.2 (M$^+$+1).

Example 128. Compound 21459: N-(4-(tert-butyl)phenyl)-N-(4-(5-(difluoromethyl)-1,3,4-oxadiazol-2-yl)benzyl)thiomorpholine-4-carboxamide 1,1-dioxide

[Step 1] N-(4-(tert-butyl)phenyl)-N-(4-(2-(2,2-difluoroacetyl)hydrazine-1-carbonyl)benzyl)thiomorpholine-4-carboxamide 1,1-dioxide

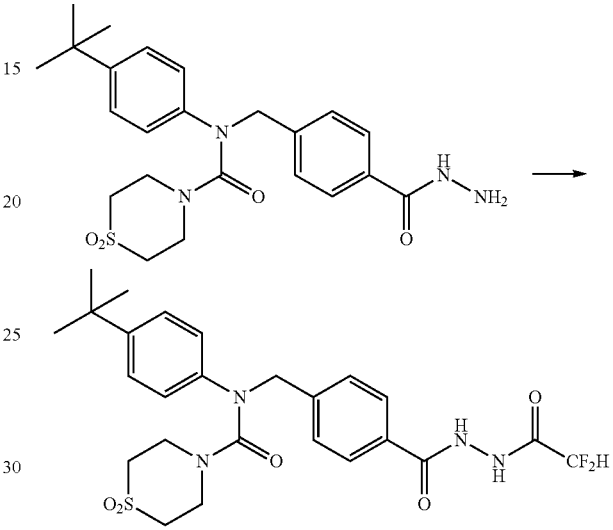

A solution of N-(4-(tert-butyl)phenyl)-N-(4-(hydrazinecarbonyl)benzyl)thiomorpholine-4-carboxamide 1,1-dioxide (0.128 g, 0.279 mmol) prepared in Step 1 of Example 127 and triethylamine (0.058 mL, 0.419 mmol) in dichloromethane (5 mL) was mixed at 0° C. with difluoroacetic anhydride (0.035 mL, 0.251 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to N-(4-(tert-butyl)phenyl)-N-(4-(2-(2,2-difluoroacetyl)hydrazine-1-carbonyl)benzyl)thiomorpholine-4-carboxamide 1,1-dioxide as white solid (0.119 g, 79.7%).

[Step 2] Compound 21459

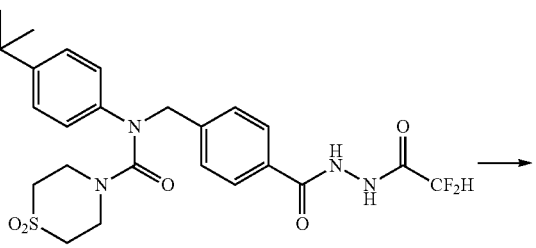

515
-continued

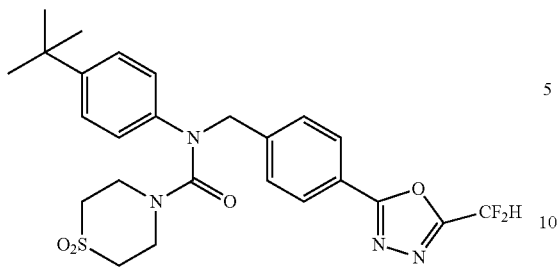

A mixture of N-(4-(tert-butyl)phenyl)-N-(4-(2-(2,2-difluoroacetyl)hydrazine-1-carbonyl)benzyl)thiomorpholine-4-carboxamide 1,1-dioxide (0.119 g, 0.223 mmol) prepared in Step 1 and 1-methoxy-N-triethylammoniosulfonyl-methanimidate (Burgess reagent, 0.080 g, 0.334 mmol) in tetrahydrofuran (3 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(tert-butyl)phenyl)-N-(4-(5-(difluoromethyl)-1,3,4-oxadiazol-2-yl)benzyl)thiomorpholine-4-carboxamide 1,1-dioxide as white solid (0.067 g, 58.1%).

$^1$H NMR (400 MHz, CDCl$_3$) δ 8.06-7.97 (m, 2H), 7.49-7.40 (m, 2H), 7.39-7.30 (m, 2H), 7.06-6.75 (m, 3H), 4.87 (s, 2H), 3.73-3.69 (m, 4H), 2.82-2.74 (m, 4H), 1.29 (S, 9H); LRMS (ES) m/z 519.2 (M$^+$+1).

Example 129. Compound 21460: N-(4-(tert-butyl)phenyl)-N-(2-fluoro-4-(2-(2,2,2-trifluoroacetyl)hydrazine-1-carbonyl)benzyl)thiomorpholine-4-carboxamide 1,1-dioxide

[Step 1] N-(4-(tert-butyl)phenyl)-N-(2-fluoro-4-(2-(2,2,2-trifluoroacetyl)hydrazine-1-carbonyl)benzyl)thiomorpholine-4-carboxamide 1,1-dioxide

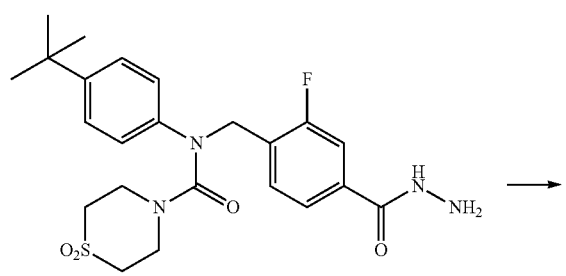

516
-continued

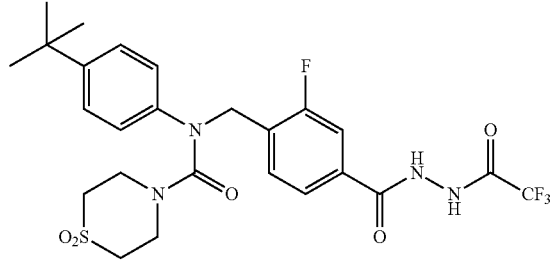

A solution of N-(4-(tert-butyl)phenyl)-N-(2-fluoro-4-(hydrazinecarbonyl)benzyl)thiomorpholine-4-carboxamide 1,1-dioxide (0.162 g, 0.340 mmol) and triethylamine (0.071 mL, 0.510 mmol) in dichloromethane (5 mL) was mixed at 0° C. with trifluoroacetic anhydride (0.043 mL, 0.306 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 5%) to give the title compound N-(4-(tert-butyl)phenyl)-N-(2-fluoro-4-(2-(2,2,2-trifluoroacetyl)hydrazine-1-carbonyl)benzyl)thiomorpholine-4-carboxamide 1,1-dioxide as white solid (0.190 g, 97.6%).

[Step 2] Compound 21460

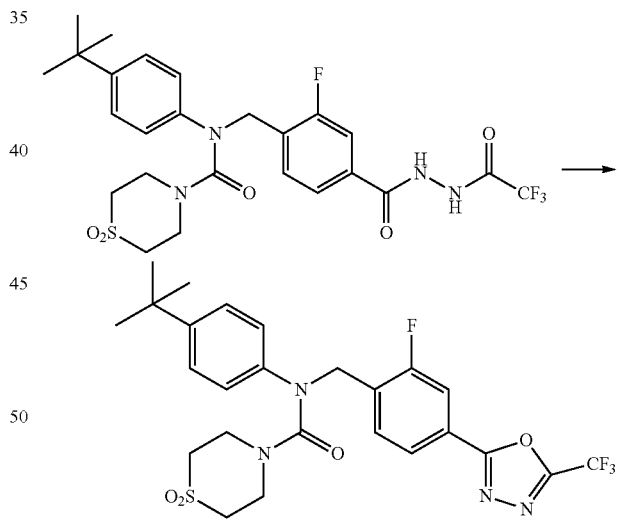

A mixture of N-(4-(tert-butyl)phenyl)-N-(2-fluoro-4-(2-(2,2,2-trifluoroacetyl)hydrazine-1-carbonyl)benzyl)thiomorpholine-4-carboxamide 1,1-dioxide (0.190 g, 0.332 mmol) prepared in Step 1 and 1-methoxy-N-triethylammoniosulfonyl-methanimidate (Burgess reagent, 0.119 g, 0:498 mmol) in tetrahydrofuran (3 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 3%) to give the title compound N-(4-(tert-butyl)phenyl)-N-(2-fluoro-4-(5-(trifluoromethyl)-1,3,4-oxadiazol-2-yl)benzyl)thiomorpholine-4-carboxamide 1,1-dioxide as white solid (0.104 g, 56.5%).

$^{1}$H NMR (400 MHz, CDCl₃) δ 7.87 (dd, 1H, J=8.0, 1.7 Hz), 7.76 (dd, 1H, J=10.0, 1.7 Hz), 7.66 (t, 1H, J=7.6 Hz), 7.41-7.33 (m, 2H), 7.08-7.00 (m, 2H), 4.90 (s, 2H), 3.74-3.67 (m, 4H), 2.79-2.73 (m, 4H), 1.30 (s, 9H); LRMS (ES) m/z 555.2 (M⁺+1).

Example 130. Compound 21461: N-(4-(tert-butyl)phenyl)-N-(4-(5-(difluoromethyl)-1,3,4-oxadiazol-2-yl)-2-fluorobenzyl)thiomorpholine-4-carboxamide 1,1-dioxide

[Step 1] N-(4-(tert-butyl)phenyl)-N-(4-(2-(2,2-difluoroacetyl)hydrazine-1-carbonyl)-2-fluorobenzyl)thiomorpholine-4-carboxamide 1,1-dioxide

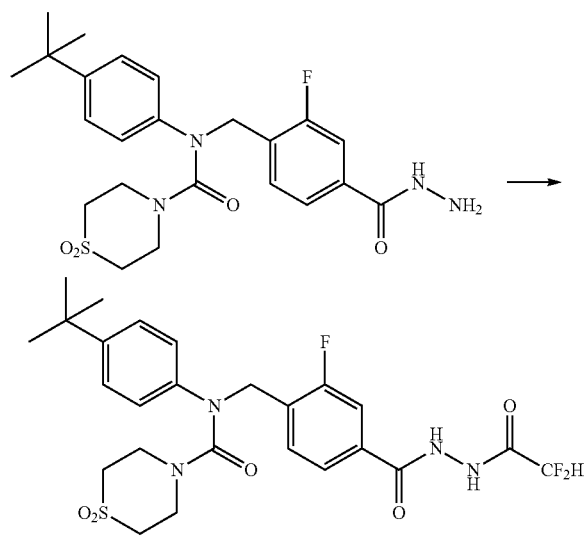

A solution of N-(4-(tert-butyl)phenyl)-N-(2-fluoro-4-(hydrazinecarbonyl)benzyl)thiomorpholine-4-carboxamide 1,1-dioxide (0.162 g, 0.340 mmol) and triethylamine (0.071 mL, 0.510 mmol) in dichloromethane (5 mL) was mixed at 0° C. with difluoroacetic anhydride (0.033 mL, 0.306 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 5%) to give the title compound N-(4-(tert-butyl)phenyl)-N-(4-(2-(2,2-difluoroacetyl)hydrazine-1-carbonyl)-2-fluorobenzyl)thiomorpholine-4-carboxamide 1,1-dioxide as white solid (0.181 g, 96.0%).

[Step 2] Compound 21461

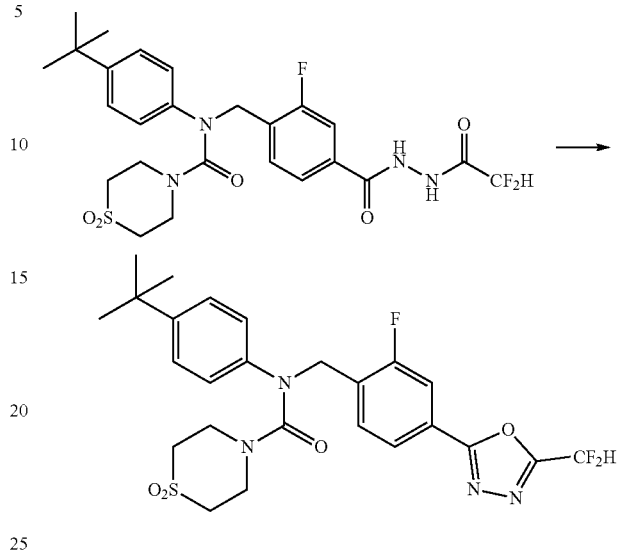

A mixture of N-(4-(tert-butyl)phenyl)-N-(4-(2-(2,2-difluoroacetyl)hydrazine-1-carbonyl)-2-fluorobenzyl)thiomorpholine-4-carboxamide 1,1-dioxide (0.181 g, 0.326 mmol) prepared in Step 1 and 1-methoxy-N-triethylammoniosulfonyl-methanimidate (Burgess reagent, 0.117 g, 0.490 mmol) in tetrahydrofuran (3 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 3%) to give the title compound N-(4-(tert-butyl)phenyl)-N-(4-(5-(difluoromethyl)-1,3,4-oxadiazol-2-yl)-2-fluorobenzyl)thiomorpholine-4-carboxamide 1,1-dioxide as white solid (0.097 g, 55.4%).

$^{1}$H NMR (400 MHz, CDCl₃) δ 7.87 (m, 1H), 7.75 (m, 1H), 7.64 (t, 1H, J=7.6 Hz), 7.40-7.32 (m, 2H), 7.06-7.02 (m, 3H), 4.90 (s, 2H), 3.74-3.67 (m, 4H), 2.76 (m, 4H), 1.29 (s, 9H); LRMS (ES) m/z 537.2 (M⁺+1).

Example 131. Compound 21462: N-benzyl-N-(4-(5-(trifluoromethyl)-1,3,4-oxadiazol-2-yl)benzyl)morpholine-4-carboxamide

[Step 1] Methyl 4-((benzylamino)methyl)benzoate

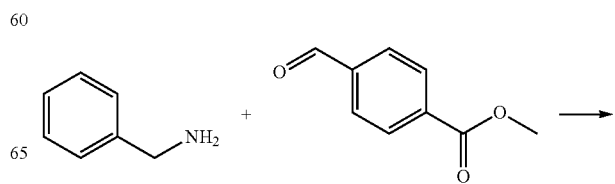

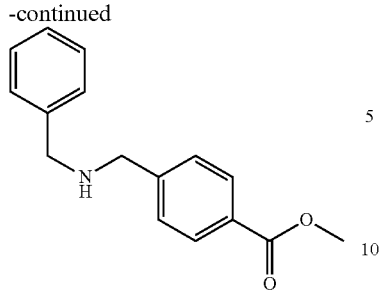

A solution of phenylmethanamine (1.000 g, 9.332 mmol), methyl 4-formylbenzoate (1.532 g, 9.332 mmol) and sodium triacetoxyborohydride (3.956 g, 18.664 mmol) in dichloromethane (30 mL) was stirred at the room temperature for 8 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((benzylamino)methyl)benzoate as Colorless oil (1.200 g, 50.4%).

[Step 2] Methyl 4-((N-benzylmorpholine-4-carboxamido)methyl)benzoate

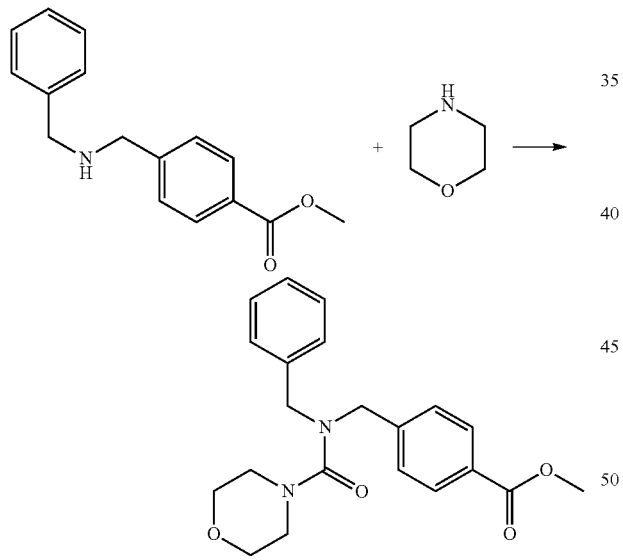

To a stirred solution of methyl 4-((benzylamino)methyl) benzoate (1.200 g, 4.700 mmol) prepared in Step 1 in dichloromethane (20 mL) were added at 0° C. N,N-diisopropylethylamine (4.093 mL, 23.500 mmol) and triphosgene (1.116 g, 3.760 mmol). The reaction mixture was stirred at the same temperature for 30 min, treated at the room temperature with morpholine (0.446 mL, 5.170 mmol), and stirred for additional 2 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 4-((N-benzylmorpholine-4-carboxamido)methyl)benzoate as Colorless oil (1.200 g, 69.3%).

[Step 3] N-benzyl-N-(4-(hydrazinecarbonyl)benzyl)morpholine-4-carboxamide

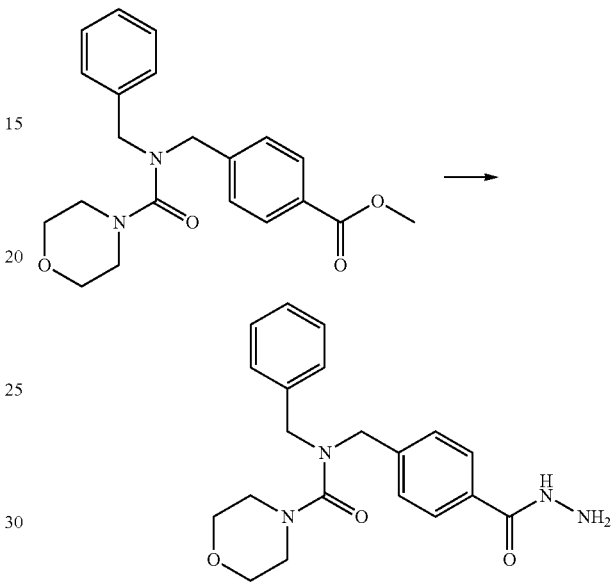

A mixture of methyl 4-((N-benzylmorpholine-4-carboxamido)methyl)benzoate (1.200 g, 3.257 mmol) prepared in Step 2 and hydrazine monohydrate (3.076 mL, 65.141 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-benzyl-N-(4-(hydrazinecarbonyl)benzyl)morpholine-4-carboxamide, 1.200 g, 100.0%, Colorless oil).

[Step 4] N-benzyl-N-(4-(2-(2,2,2-trifluoroacetyl)hydrazine-1-carbonyl)benzyl)morpholine-4-carboxamide

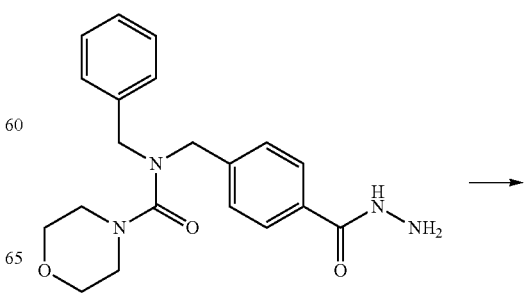

-continued

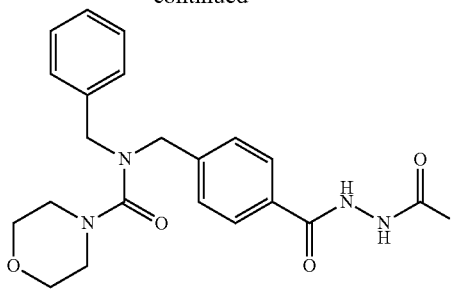

solution of N-benzyl-N-(4-(hydrazinecarbonyl)benzyl)morpholine-4-carboxamide (0.679 g, 1.843 mmol) prepared in Step 3, trifluoroacetic anhydride (0.350 g, 1.659 mmol) and triethylamine (0.383 mL, 2.764 mmol) in dichloromethane (10 mL) was stirred at the room temperature for 2 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-benzyl-N-(4-(2-(2,2,2-trifluoroacetyl)hydrazine-1-carbonyl)benzyl)morpholine-4-carboxamide as Colorless oil (0.700 g, 81.8%).

[Step 5] Compound 21462

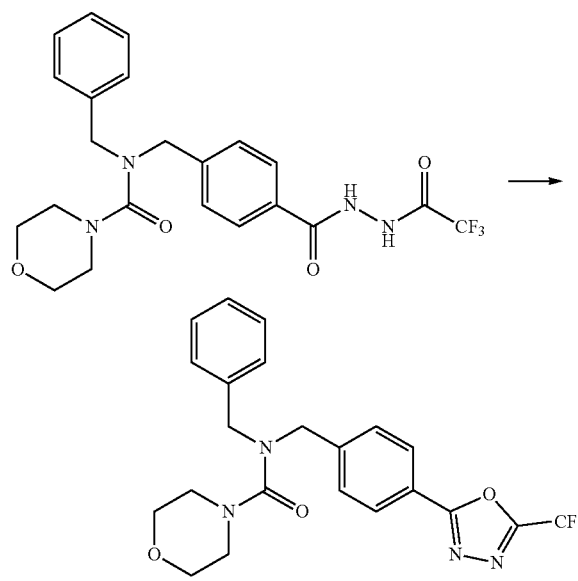

A mixture of N-benzyl-N-(4-(2-(2,2,2-trifluoroacetyl)hydrazine-1-carbonyl)benzyl)morpholine-4-carboxamide (0.421 g, 0.906 mmol) prepared in Step 4 and 1-methoxy-N-triethylammoniosulfonyl-methanimidate (Burgess reagent, 0.324 g, 1.360 mmol) in tetrahydrofuran (10 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-benzyl-N-(4-(5-(trifluoromethyl)-1,3,4-oxadiazol-2-yl)benzyl)morpholine-4-carboxamide as Colorless oil (0.200 g, 49.4%).

$^1$H NMR (400 MHz, CDCl$_3$) δ 8.10 (d, 2H, J=8.4 Hz), 7.40-7.31 (m, 5H), 7.19-7.17 (m, 2H), 4.41 (s, 2H), 4.37 (s, 2H), 3.74 (t, 4H, J=4.7 Hz), 3.38 (t, 4H, J=4.7 Hz); LRMS (ES) m/z 448.2 (M$^+$+1).

Example 132. Compound 21463: N-(pyridin-3-ylmethyl)-N-(4-(5-(trifluoromethyl)-1,3,4-oxadiazol-2-yl)benzyl)morpholine-4-carboxamide

[Step 1] Methyl 4-(((pyridin-3-ylmethyl)amino)methyl)benzoate

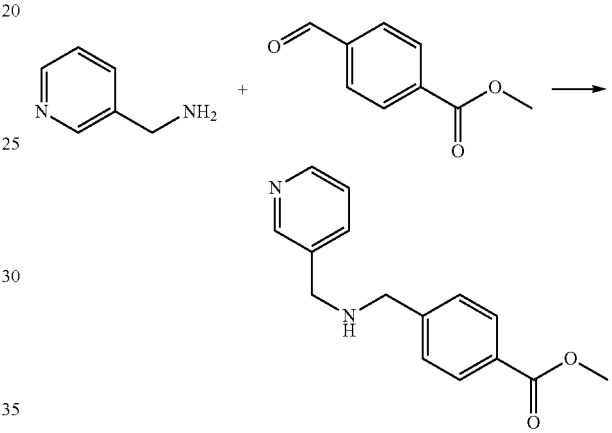

A solution of pyridin-3-ylmethanamine (0.700 g, 6.473 mmol), methyl 4-formylbenzoate (1.063 g, 6.473 mmol) and sodium triacetoxyborohydride (2.744 g, 12.946 mmol) in dichloromethane (30 mL) was stirred at the room temperature for 8 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 20%) to give the title compound methyl 4-(((pyridin-3-ylmethyl)amino)methyl)benzoate as Colorless oil (0.839 g, 50.6%).

[Step 2] Methyl 4-((N-(pyridin-3-ylmethyl)morpholine-4-carboxamido)methyl)benzoate

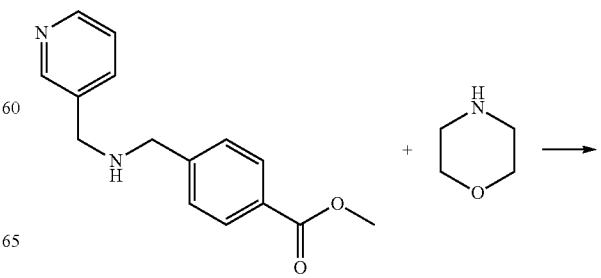

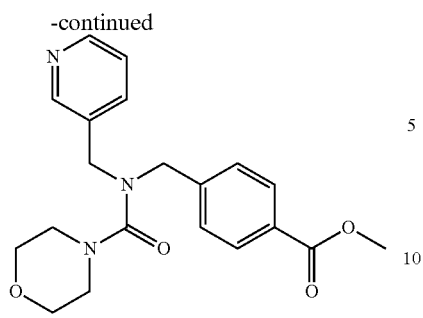

To a stirred solution of methyl 4-(((pyridin-3-ylmethyl)amino)methyl)benzoate (0.839 g, 3.273 mmol) prepared in Step 1 in dichloromethane (20 mL) were added at 0° C. N,N-diisopropylethylamine (2.858 mL, 16.367 mmol) and triphosgene (0.777 g, 2.619 mmol). The reaction mixture was stirred at the same temperature for 30 min, treated at the room temperature with morpholine (0.311 mL, 3.601 mmol), and stirred for additional 2 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound methyl 4-((N-(pyridin-3-ylmethyl)morpholine-4-carboxamido)methyl)benzoate as Black oil (0.850 g, 70.3%).

[Step 3] N-(4-(hydrazinecarbonyl)benzyl)-N-(pyridin-3-ylmethyl)morpholine-4-carboxamide

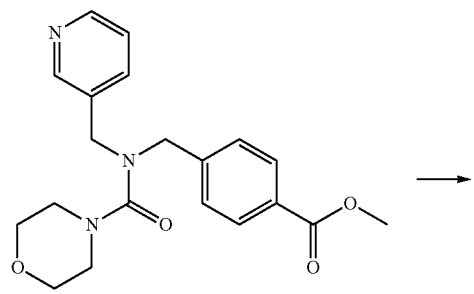

A mixture of methyl 4-((N-(pyridin-3-ylmethyl)morpholine-4-carboxamido)methyl)benzoate (0.850 g, 2.144 mmol) prepared in Step 2 and hydrazine monohydrate (2.025 mL, 42.884 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(4-(hydrazinecarbonyl)benzyl)-N-(pyridin-3-ylmethyl)morpholine-4-carboxamide, 0.850 g, 100.0%, Black oil).

[Step 4] N-(pyridin-3-ylmethyl)-N-(4-(2-(2,2,2-trifluoroacetyl)hydrazine-1-carbonyl)benzyl)morpholine-4-carboxamide

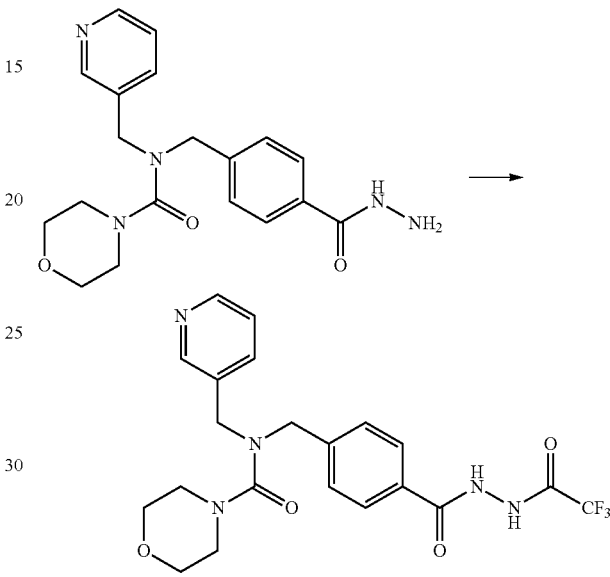

A solution of N-(4-(hydrazinecarbonyl)benzyl)-N-(pyridin-3-ylmethyl)morpholine-4-carboxamide (0.899 g, 2.433 mmol) prepared in Step 3, trifluoroacetic anhydride (0.462 g, 2.190 mmol) and triethylamine (0.369 g, 3.650 mmol) in dichloromethane (10 mL) was stirred at the room temperature for 3 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(pyridin-3-ylmethyl)-N-(4-(2-(2,2,2-trifluoroacetyl)hydrazine-1-carbonyl)benzyl)morpholine-4-carboxamide as Brown oil (0.700 g, 61.8%).

[Step 5] Compound 21463

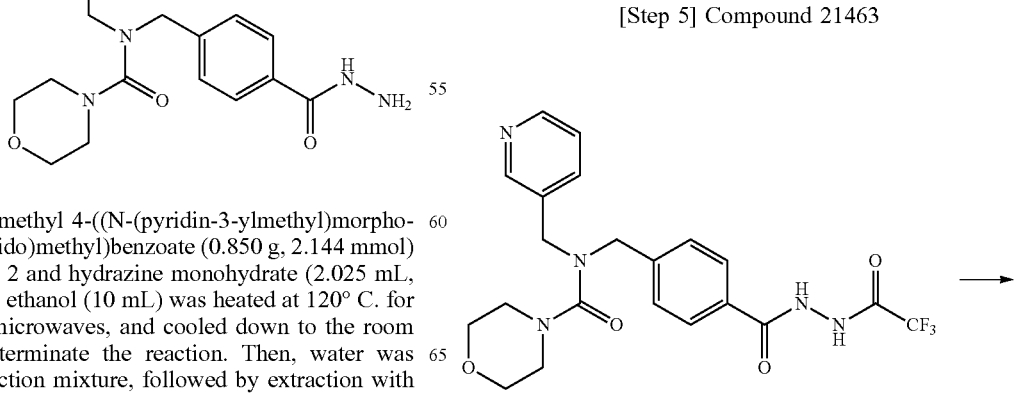

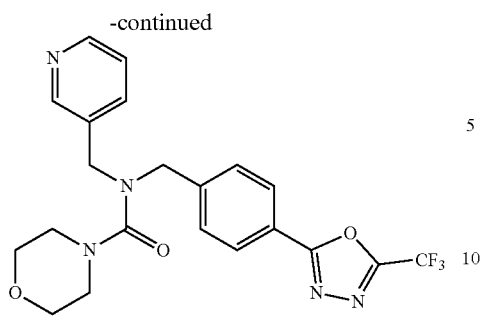

A mixture of N-(pyridin-3-ylmethyl)-N-(4-(2-(2,2,2-trifluoroacetyl)hydrazine-1-carbonyl)benzyl)morpholine-4-carboxamide (0.388 g, 0.834 mmol) prepared in Step 4 and 1-methoxy-N-triethylammoniosulfonyl-methanimidate (Burgess reagent, 0.298 g, 1.250 mmol) in tetrahydrofuran (10 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(pyridin-3-ylmethyl)-N-(4-(5-(trifluoromethyl)-1,3,4-oxadiazol-2-yl)benzyl)morpholine-4-carboxamide as Colorless oil (0.050 g, 13.4%).

$^1$H NMR (400 MHz, CDCl$_3$) δ 8.58 (dd, 1H, J=4.8, 1.4 Hz), 8.44 (d, 1H, J=1.4 Hz), 8.13-8.11 (m, 2H), 7.62-7.59 (m, 1H), 7.40 (d, 2H, J=8.5 Hz), 7.34-7.31 (m, 1H), 4.41 (s, 2H), 4.37 (s, 2H), 3.73 (t, 4H, J=4.7 Hz), 3.38 (t, 4H, J=4.7 Hz); LRMS (ES) m/z 449.11 (M$^+$+1).

Example 133. Compound 21464: N-(pyridin-4-ylmethyl)-N-(4-(5-(trifluoromethyl)-1,3,4-oxadiazol-2-yl)benzyl)morpholine-4-carboxamide

[Step 1] Methyl 4-(((pyridin-4-ylmethyl)amino)methyl)benzoate

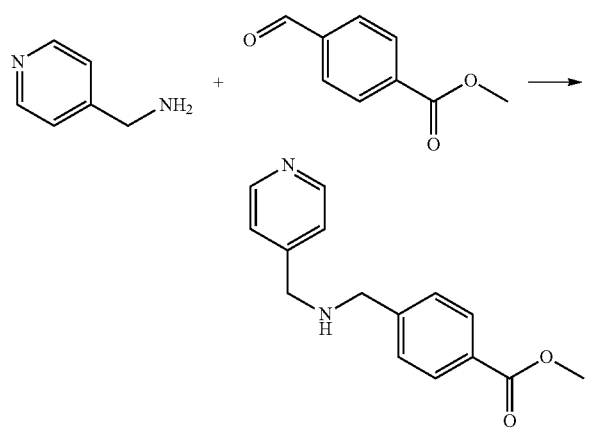

A solution of pyridin-4-ylmethanamine (0.700 g, 6.473 mmol), methyl 4-formylbenzoate (1.063 g, 6.473 mmol) and sodium cyanoborohydride (2.744 g, 12.946 mmol) in dichloromethane (30 mL) was stirred at the room temperature for 8 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 20%) to give the title compound methyl 4-(((pyridin-4-ylmethyl)amino)methyl)benzoate as Black oil (0.896 g, 54.0%).

[Step 2] Methyl 4-((N-(pyridin-4-ylmethyl)morpholine-4-carboxamido)methyl)benzoate

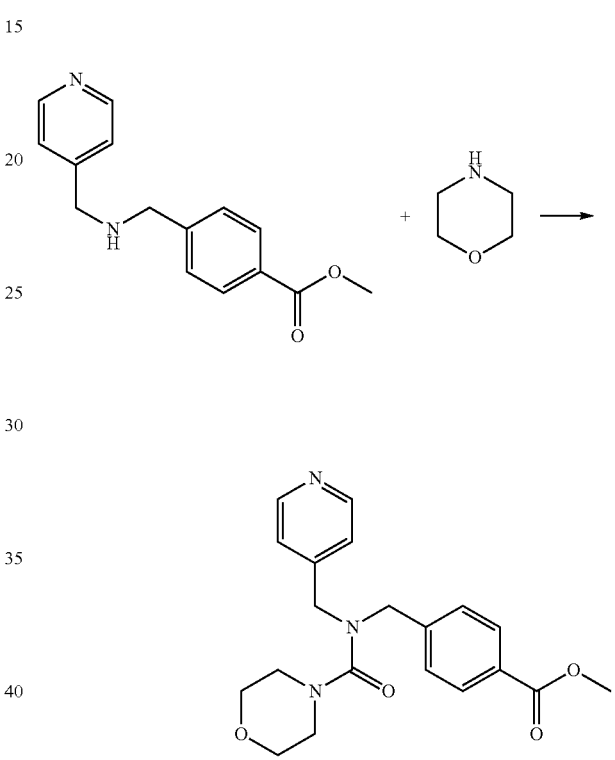

To a stirred solution of methyl 4-(((pyridin-4-ylmethyl)amino)methyl)benzoate (0.896 g, 3.496 mmol) prepared in Step 1 in dichloromethane (20 mL) were added at 0° C. N,N-diisopropylethylamine (2.259 g, 17.479 mmol) and triphosgene (0.830 g, 2.797 mmol). The reaction mixture was stirred at the same temperature for 30 min, treated at the room temperature with morpholine (0.335 g, 3.845 mmol), and stirred for additional 2 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 20%) to give the title compound methyl 4-((N-(pyridin-4-ylmethyl)morpholine-4-carboxamido)methyl)benzoate as Black oil (0.850 g, 65.8%).

527

[Step 3] N-(4-(hydrazinecarbonyl)benzyl)-N-(pyridin-4-ylmethyl)morpholine-4-carboxamide

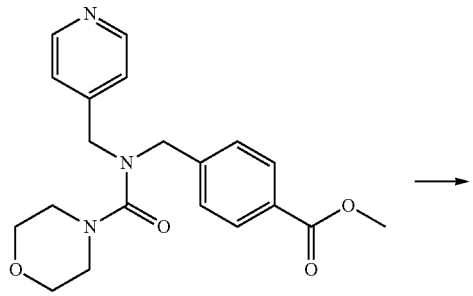

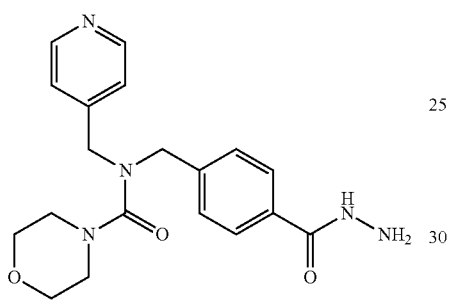

A mixture of methyl 4-((N-(pyridin-4-ylmethyl)morpholine-4-carboxamido)methyl)benzoate (0.724 g, 1.826 mmol) prepared in Step 2 and hydrazine monohydrate (1.829 g, 36.527 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(4-(hydrazinecarbonyl)benzyl)-N-(pyridin-4-ylmethyl)morpholine-4-carboxamide, 0.720 g, 99.5%, Black oil).

[Step 4] N-(pyridin-4-ylmethyl)-N-(4-(2-(2,2,2-trifluoroacetyl)hydrazine-1-carbonyl)benzyl)morpholine-4-carboxamide

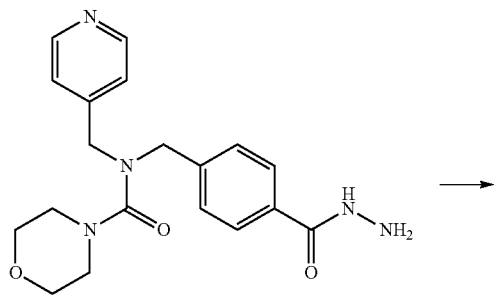

528

-continued

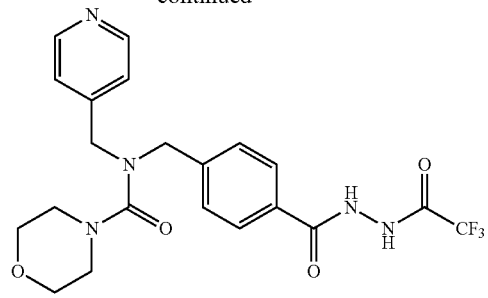

A solution of N-(4-(hydrazinecarbonyl)benzyl)-N-(pyridin-4-ylmethyl)morpholine-4-carboxamide (0.724 g, 1.960 mmol) prepared in Step 3, trifluoroacetic anhydride (0.372 g, 1.764 mmol) and triethylamine (0.297 g, 2.940 mmol) in dichloromethane (10 mL) was stirred at the room temperature for 3 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 30%) to give the title compound N-(pyridin-4-ylmethyl)-N-(4-(2-(2,2,2-trifluoroacetyl)hydrazine-1-carbonyl)benzyl)morpholine-4-carboxamide as Brown oil (0.200 g, 21.9%).

[Step 5] Compound 21464

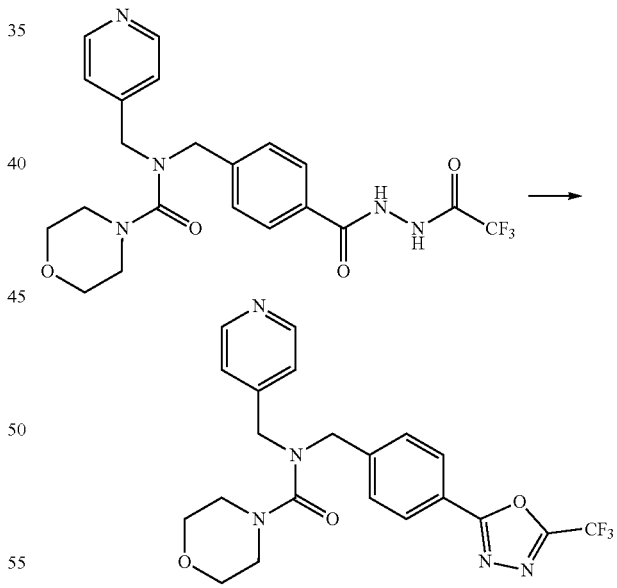

mixture of N-(pyridin-4-ylmethyl)-N-(4-(2-(2,2,2-trifluoroacetyl)hydrazine-1-carbonyl)benzyl)morpholine-4-carboxamide (0.148 g, 0.318 mmol) prepared in Step 4 and 1-methoxy-N-triethylammoniosulfonyl-methanimidate (Burgess reagent, 0.114 g, 0.477 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-(pyridin-4-ylmethyl)-N-(4-(5-(trifluoromethyl)-1,3,4-oxadiazol-2-yl)benzyl)morpholine-4-carboxamide as Colorless oil (0.040 g, 28.1%).

¹H NMR (400 MHz, CDCl₃) δ 8.61 (d, 2H, J=4.4 Hz), 8.12 (d, 2H, J=8.2 Hz), 7.40 (d, 2H, J=8.1 Hz), 7.16 (d, 2H, J=5.4 Hz), 4.45 (s, 2H), 4.36 (s, 2H), 3.38 (t, 4H, J=4.7 Hz); LRMS (ES) m/z 449.18 (M⁺+1).

Example 134. Compound 21465: N-(3-bromophenyl)-N-(4-(5-(difluoromethyl)-1,3,4-oxadiazol-2-yl)-2-fluorobenzyl)-4-methylpiperazine-1-carboxamide

[Step 1] N-(3-bromophenyl)-4-methylpiperazine-1-carboxamide

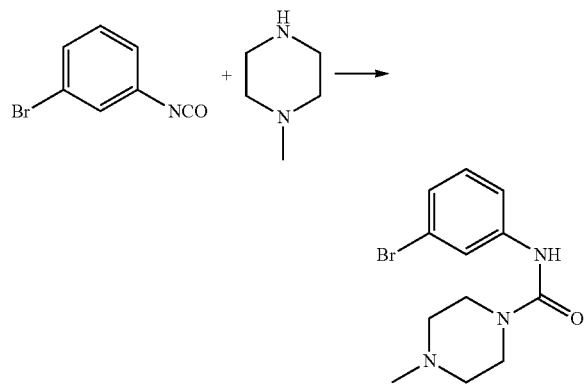

A solution of 1-bromo-3-isocyanatobenzene (4.000 g, 20.200 mmol) and 1-methylpiperazine (2.023 g, 20.200 mmol) in diethylether (20 mL) was stirred at the room temperature for 1 hr. The precipitates were collected by filtration, washed by diethylether, and dried to give the title compound N-(3-bromophenyl)-4-methylpiperazine-1-carboxamide as White solid (5.250 g, 87.2%).

[Step 2] Methyl 4-((N-(3-bromophenyl)-4-methylpiperazine-1-carboxamido)methyl)-3-fluorobenzoate

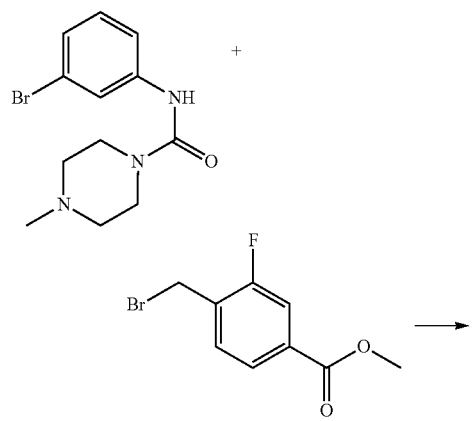

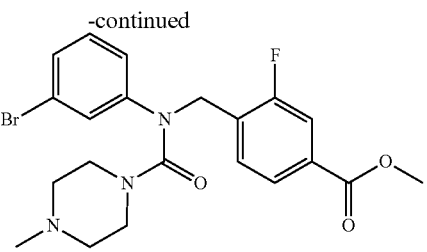

To a stirred solution of N-(3-bromophenyl)-4-methylpiperazine-1-carboxamide (5.280 g, 17.707 mmol) prepared in Step 1 in N,N-dimethylformamide (50 mL) was added at 0° C. sodium hydride (60.00%, 1.062 g, 26.561 mmol). The reaction mixture was stirred at the same temperature for 30 min, treated at the room temperature with methyl 4-(bromomethyl)-3-fluorobenzoate (4.812 g, 19.478 mmol), and stirred for additional 12 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound methyl 4-((N-(3-bromophenyl)-4-methylpiperazine-1-carboxamido)methyl)-3-fluorobenzoate as Yellow oil (6.200 g, 75.4%).

[Step 3] N-(3-bromophenyl)-N-(2-fluoro-4-(hydrazinecarbonyl)benzyl)-4-methylpiperazine-1-carboxamide

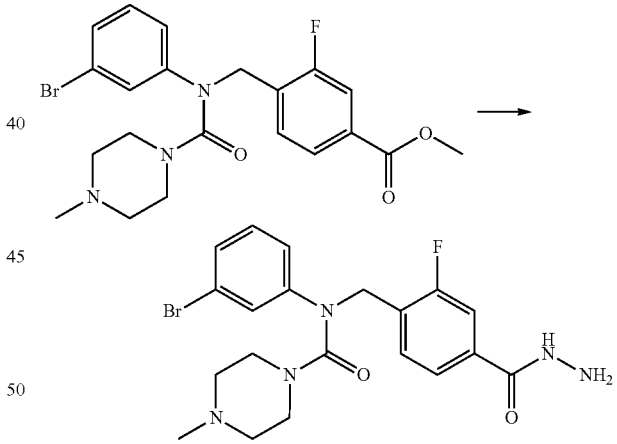

A mixture of methyl 4-((N-(3-bromophenyl)-4-methylpiperazine-1-carboxamido)methyl)-3-fluorobenzoate (1.000 g, 2.154 mmol) prepared in Step 2 and hydrazine monohydrate (2.034 mL, 43.072 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO₄), filtered, and concentrated in vacuo. The crude product was used without further purification (N-(3-bromophenyl)-N-(2-fluoro-4-(hydrazinecarbonyl)benzyl)-4-methylpiperazine-1-carboxamide, 0.900 g, 90.0%, Colorless oil).

[Step 4] N-(3-bromophenyl)-N-(4-(2-(2,2-difluoroacetyl)hydrazine-1-carbonyl)-2-fluorobenzyl)-4-methylpiperazine-1-carboxamide

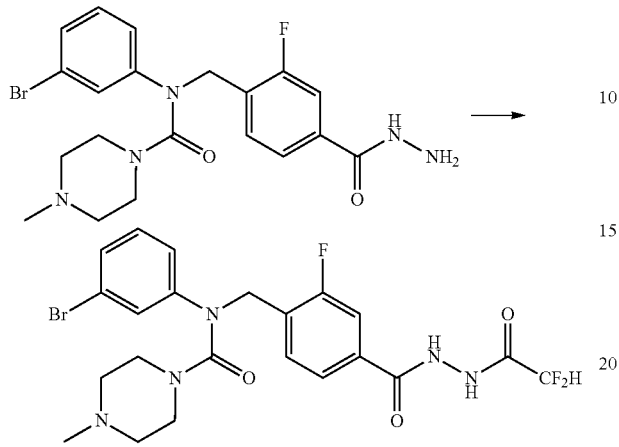

A solution of N-(3-bromophenyl)-N-(2-fluoro-4-(hydrazinecarbonyl)benzyl)-4-methylpiperazine-1-carboxamide (0.956 g, 2.059 mmol) prepared in Step 3. Difluoroacetic anhydride (0.202 mL, 1.853 mmol) and triethylamine (0.428 mL, 3.088 mmol) in dichloromethane (10 mL) was stirred at the room temperature for 3 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(3-bromophenyl)-N-(4-(2-(2,2-difluoroacetyl)hydrazine-1-carbonyl)-2-fluorobenzyl)-4-methylpiperazine-1-carboxamide as Colorless oil (0.242 g, 21.7%).

[Step 5] Compound 21465

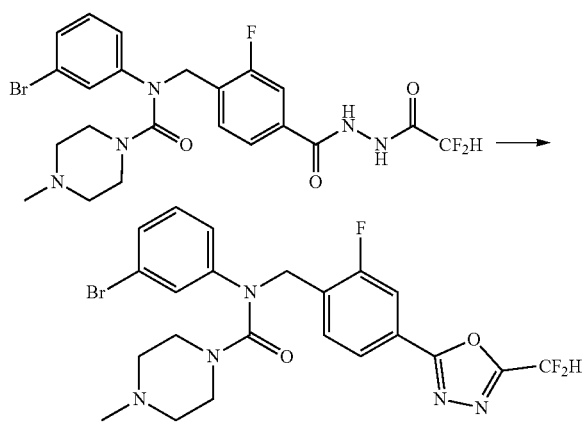

A mixture of N-(3-bromophenyl)-N-(4-(2-(2,2-difluoroacetyl)hydrazine-1-carbonyl)-2-fluorobenzyl)-4-methylpiperazine-1-carboxamide (0.242 g, 0.446 mmol) prepared in Step 4 and 1-methoxy-N-triethylammoniosulfonyl-methanimidate (Burgess reagent, 0.159 g, 0.669 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-(3-bromophenyl)-N-(4-(5-(difluoromethyl)-1,3,4-oxadiazol-2-yl)-2-fluorobenzyl)-4-methylpiperazine-1-carboxamide as Colorless oil (0.152 g, 65.0%).

$^1$H NMR (400 MHz, CDCl$_3$) δ 7.90-7.88 (m, 1H), 7.78 (dd, 1H), 7.68 (t, 1H, J=7.6 Hz), 7.29-7.28 (m, 2H), 7.26 (s, 1H), 7.20 (t, 1H, J=7.9 Hz), 7.02-6.80 (m, 1H), 4.97 (s, 2H), 3.38-3.33 (m, 4H), 2.27-2.21 (m, 7H); LRMS (ES) m/z 524.19 (M$^+$+1).

Example 135. Compound 21466: N-(4-bromophenyl)-N-(4-(5-(difluoromethyl)-1,3,4-oxadiazol-2-yl)-2-fluorobenzyl)-4-methylpiperazine-1-carboxamide

[Step 1]
N-(4-bromophenyl)-4-methylpiperazine-1-carboxamide

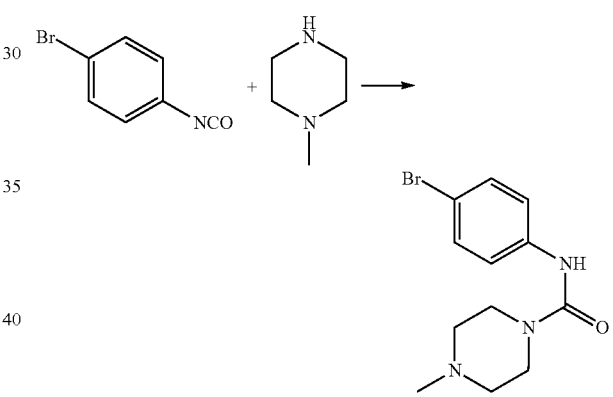

A solution of 1-bromo-4-isocyanatobenzene (0.629 mL, 5.050 mmol) and 1-methylpiperazine (0.556 mL, 5.050 mmol) in diethylether (10 mL) was stirred at the room temperature for 1 hr. The precipitates were collected by filtration, washed by 1N-diethylether solution, and dried to give the title compound N-(4-bromophenyl)-4-methylpiperazine-1-carboxamide as White solid (1.480 g, 98.3%).

[Step 2] Methyl 4-((N-(4-bromophenyl)-4-methylpiperazine-1-carboxamido)methyl)-3-fluorobenzoate

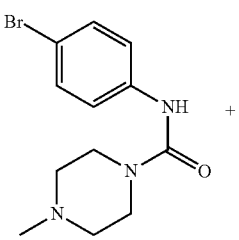

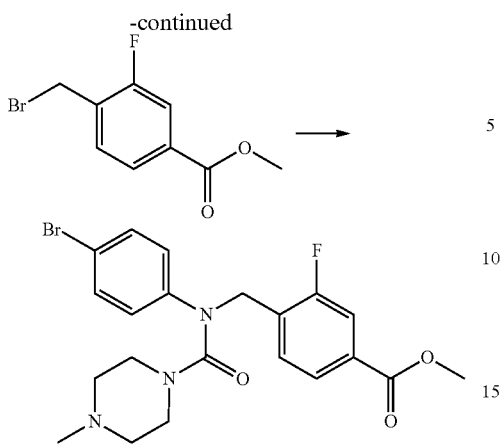

To a stirred solution of N-(4-bromophenyl)-4-methylpiperazine-1-carboxamide (0.500 g, 1.677 mmol) prepared in Step 1 in N,N-dimethylformamide (10 mL) was added at 0° C. sodium hydride (60.00%, 0.101 g, 2.515 mmol). The reaction mixture was stirred at the same temperature for 30 min, treated at the room temperature with methyl 4-(bromomethyl)-3-fluorobenzoate (0.456 g, 1.845 mmol), and stirred for additional 8 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 4-((N-(4-bromophenyl)-4-methylpiperazine-1-carboxamido)methyl)-3-fluorobenzoate as Colorless oil (0.588 g, 75.5%).

[Step 3] N-(4-bromophenyl)-N-(2-fluoro-4-(hydrazinecarbonyl)benzyl)-4-methylpiperazine-1-carboxamide

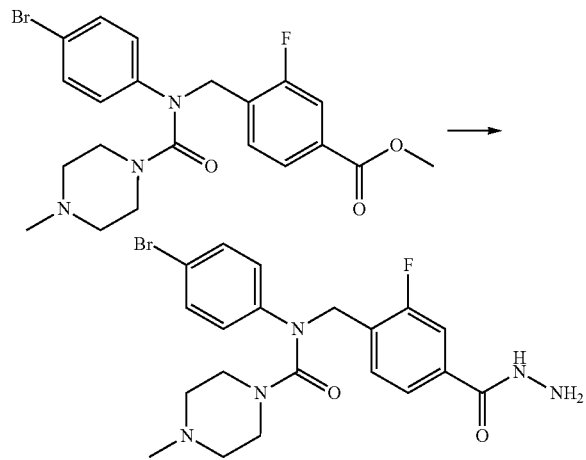

A mixture of methyl 4-((N-(4-bromophenyl)-4-methylpiperazine-1-carboxamido)methyl)-3-fluorobenzoate (0.588 g, 1.266 mmol) prepared in Step 2 and hydrazine monohydrate (1.196 mL, 25.326 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(4-bromophenyl)-N-(2-fluoro-4-(hydrazinecarbonyl)benzyl)-4-methylpiperazine-1-carboxamide, 0.580 g, 98.6%, Colorless oil).

[Step 4] N-(4-bromophenyl)-N-(4-(2-(2,2-difluoroacetyl)hydrazine-1-carbonyl)-2-fluorobenzyl)-4-methylpiperazine-1-carboxamide

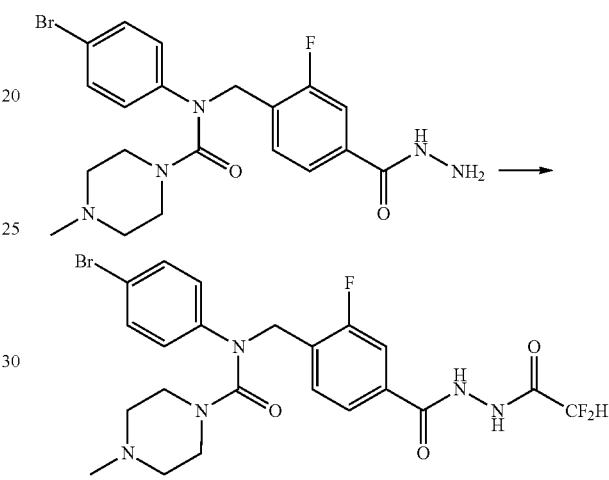

A solution of N-(4-bromophenyl)-N-(2-fluoro-4-(hydrazinecarbonyl)benzyl)-4-methylpiperazine-1-carboxamide (0.515 g, 1.109 mmol) prepared in Step 3, Difluoroacetic anhydride (0.174 g, 0.998 mmol) and triethylamine (0.168 g, 1.664 mmol) in dichloromethane (10 mL) was stirred at the room temperature for 3 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-bromophenyl)-N-(4-(2-(2,2-difluoroacetyl)hydrazine-1-carbonyl)-2-fluorobenzyl)-4-methylpiperazine-1-carboxamide as Colorless oil (0.234 g, 38.9%).

[Step 5] Compound 21466

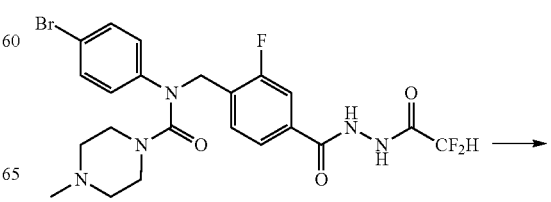

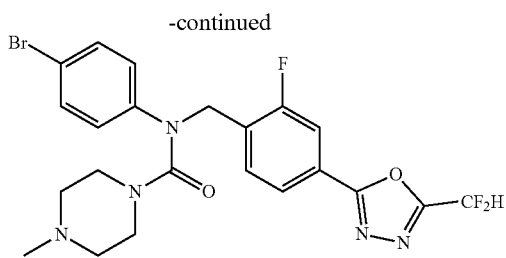

A mixture of N-(4-bromophenyl)-N-(4-(2-(2,2-difluoroacetyl)hydrazine-1-carbonyl)-2-fluorobenzyl)-4-methylpiperazine-1-carboxamide (0.234 g, 0.431 mmol) prepared in Step 4 and 1-methoxy-N-triethylammoniosulfonyl-methanimidate (Burgess reagent, 0.154 g, 0.647 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-(4-bromophenyl)-N-(4-(5-(difluoromethyl)-1,3,4-oxadiazol-2-yl)-2-fluorobenzyl)-4-methylpiperazine-1-carboxamide as Colorless oil (0.134 g, 59.2%).

$^1$H NMR (400 MHz, CDCl$_3$) δ 7.87 (dd, 1H, J=8.0, 1.3 Hz), 7.77-7.75 (m, 1H), 7.69 (t, 1H, J=7.7 Hz), 7.45-7.41 (m, 2H), 7.06 (s, 0.25H), 7.01-7.68 (m, 2H), 6.93 (s, 0.5H), 6.80 (s, 0.25H), 4.96 (s, 2H), 3.29 (t, 4H, J=4.8 Hz), 2.27-2.25 (m, 7H); LRMS (ES) m/z 525.88 (M$^+$+1).

Example 136. Compound 21467: N-(3-chlorophenyl)-N-(4-(5-(difluoromethyl)-1,3,4-oxadiazol-2-yl)-2-fluorobenzyl)-4-methylpiperazine-1-carboxamide

[Step 1] Methyl 4-(((3-chlorophenyl)amino)methyl)-3-fluorobenzoate

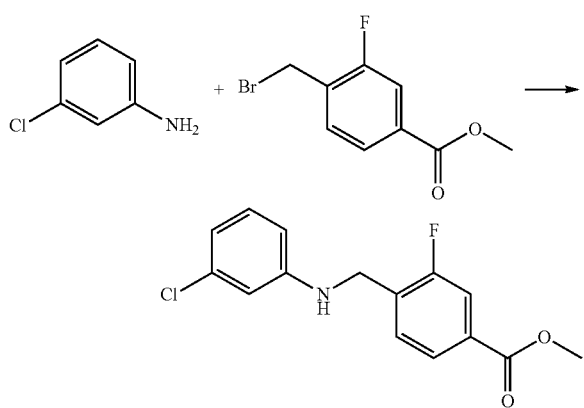

A solution of 3-chloroaniline (0.498 mL, 4.703 mmol) and sodium hydride (60.00%, 0.198 g, 4.938 mmol) in N,N-dimethylformamide (10 mL) was stirred at 0° C. for 10 min, and mixed with methyl 4-(bromomethyl)-3-fluorobenzoate (1.278 g, 5.174 mmol). The reaction mixture was stirred at the same temperature for additional 1 hr, and quenched at the room temperature by the addition of saturated aqueous sodium bicarbonate solution (10 mL, 10 min stirring). Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 20%) to give the title compound methyl 4-(((3-chlorophenyl)amino)methyl)-3-fluorobenzoate as orange oil (1.110 g, 80.4%).

[Step 2] Methyl 4-((N-(3-chlorophenyl)-4-methylpiperazine-1-carboxamido)methyl)-3-fluorobenzoate

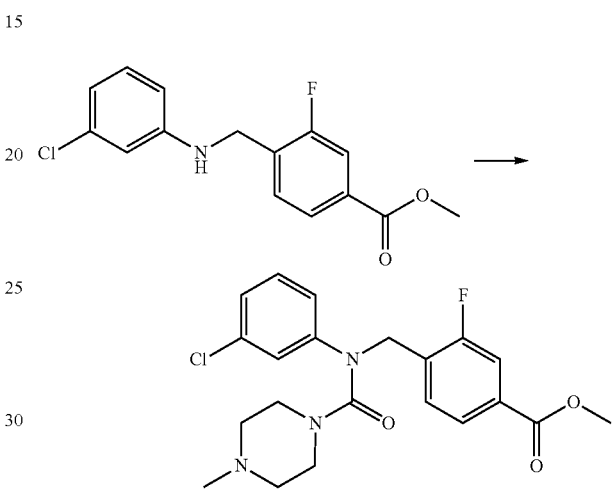

A solution of methyl 4-(((3-chlorophenyl)amino)methyl)-3-fluorobenzoate (1.110 g, 3.779 mmol) prepared in Step 1, triphosgene (0.897 g, 3.023 mmol) and N,N-diisopropylethylamine (3.300 mL, 18.896 mmol) in dichloromethane (10 mL) was stirred at 0° C. for 10 min, and mixed with 4-methyl piperazine (0.454 g, 4.535 mmol). The reaction mixture was stirred at the same temperature for additional 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 10%) to give the title compound methyl 4-((N-(3-chlorophenyl)-4-methylpiperazine-1-carboxamido)methyl)-3-fluorobenzoate as yellow oil (1.440 g, 90.8%).

[Step 3] N-(3-chlorophenyl)-N-(2-fluoro-4-(hydrazinecarbonyl)benzyl)-4-methylpiperazine-1-carboxamide

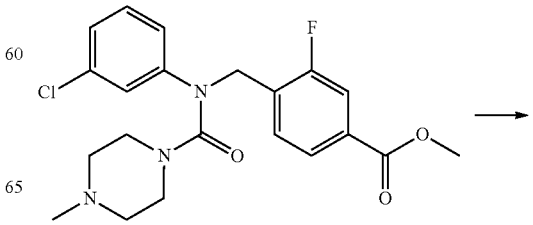

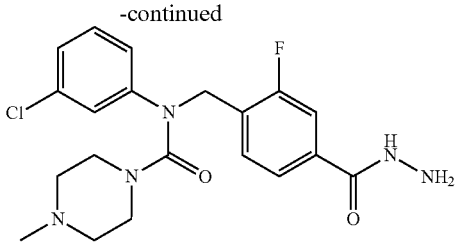

Methyl 4-((N-(3-chlorophenyl)-4-methylpiperazine-1-carboxamido)methyl)-3-fluorobenzoate (1.440 g, 3.430 mmol) prepared in Step 2 and hydrazine monohydrate (3.334 mL, 68.591 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound N-(3-chlorophenyl)-N-(2-fluoro-4-(hydrazinecarbonyl)benzyl)-4-methylpiperazine-1-carboxamide was used without further purification (1.350 g, 93.7%, white solid).

[Step 4] N-(3-chlorophenyl)-N-(4-(2-(2,2-difluoroacetyl)hydrazine-1-carbonyl)-2-fluorobenzyl)-4-methylpiperazine-1-carboxamide

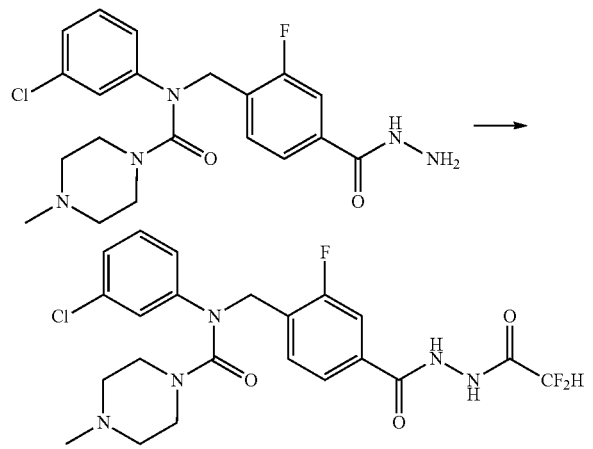

A solution of N-(3-chlorophenyl)-N-(2-fluoro-4-(hydrazinecarbonyl)benzyl)-4-methylpiperazine-1-carboxamide (1.000 g, 2.382 mmol) prepared in Step 3 and triethylamine (0.500 mL, 3.572 mmol) in dichloromethane (10 mL) was mixed at the room temperature with 2,2-difluoroacetic anhydride (0.266 mL, 2.143 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The title compound N-(3-chlorophenyl)-N-(4-(2-(2,2-difluoroacetyl)hydrazine-1-carbonyl)-2-fluorobenzyl)-4-methylpiperazine-1-carboxamide was used without further purification (1.330 g, 112.2%, pale yellow solid).

[Step 5] Compound 21467

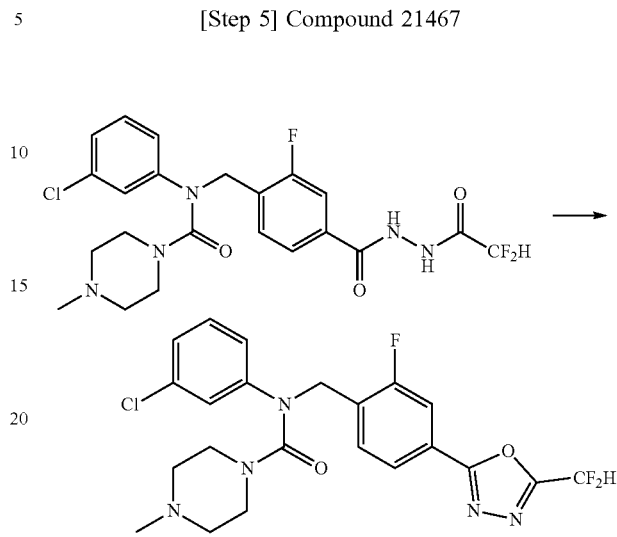

N-(3-chlorophenyl)-N-(4-(2-(2,2-difluoroacetyl)hydrazine-1-carbonyl)-2-fluorobenzyl)-4-methylpiperazine-1-carboxamide (0.300 g, 0.603 mmol) prepared in Step 4 and 1-methoxy-N-triethylammoniosulfonyl-methanimidate (Burgess reagent, 0.216 g, 0.905 mmol) in tetrahydrofuran (10 mL) was mixed at the room temperature and then heated at 150° C. under the microwaves for 30 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; ethyl acetate/hexane=10% to 60%) to give the title compound N-(3-chlorophenyl)-N-(4-(5-(difluoromethyl)-1,3,4-oxadiazol-2-yl)-2-fluorobenzyl)-4-methylpiperazine-1-carboxamide as colorless oil (0.168 g, 58.0%).

$^1$H NMR (400 MHz, $CDCl_3$) δ 7.89 (dd, 1H, J=8.0, 1.4 Hz), 7.78 (dd, 1H, J=10.1, 1.4 Hz), 7.68 (t, 1H, J=7.7 Hz), 7.28-7.24 (m, 1H), 7.14-7.12 (m, 2H), 7.06-6.80 (m, 2H), 4.97 (s, 2H), 3.38 (brs, 4H), 2.34 (brs, 7H); LRMS (ES) m/z 480.5 ($M^+$+1).

Example 137. Compound 21468: N-(4-chlorophenyl)-N-(4-(5-(difluoromethyl)-1,3,4-oxadiazol-2-yl)-2-fluorobenzyl)-4-methylpiperazine-1-carboxamide

[Step 1] Methyl 4-(((4-chlorophenyl)amino)methyl)-3-fluorobenzoate

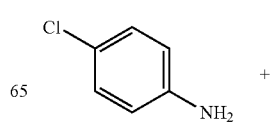

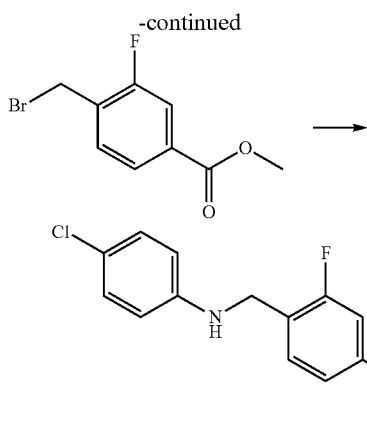

A solution of 4-chloroaniline hydrochloride (0.600 g, 3.658 mmol) and sodium hydride (60.00%, 0.154 g, 3.841 mmol) in N,N-dimethylformamide (10 mL) was stirred at 0° C. for 10 min, and mixed with methyl 4-(bromomethyl)-3-fluorobenzoate (0.994 g, 4.024 mmol). The reaction mixture was stirred at the same temperature for additional 1 hr, and quenched at the room temperature by the addition of saturated aqueous sodium bicarbonate Solution (10 mL, 10 min stirring). Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 20%) to give the title compound methyl 4-(((4-chlorophenyl)amino)methyl)-3-fluorobenzoate as pale yellow solid (0.623 g, 58.0%).

[Step 2] Methyl 4-((N-(4-chlorophenyl)-4-methyl-piperazine-1-carboxamido)methyl)-3-fluorobenzoate

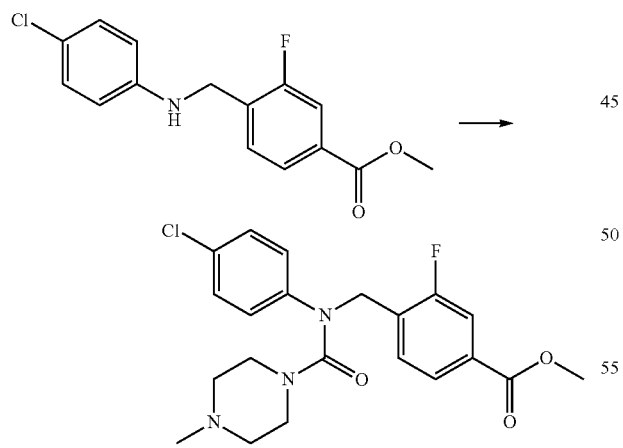

A solution of methyl 4-(((4-chlorophenyl)amino)methyl)-3-fluorobenzoate (0.623 g, 2.121 mmol) prepared in Step 1, triphosgene (0.504 g, 1.697 mmol) and N,N-diisopropylethylamine (1.852 mL, 10.605 mmol) in dichloromethane (10 mL) was stirred at 0° C. for 10 min, and mixed with 4-methyl piperazine (0.255 g, 2.545 mmol). The reaction mixture was stirred at the same temperature for additional 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 10%) to give the title compound methyl 4-((N-(4-chlorophenyl)-4-methylpiperazine-1-carboxamido)methyl)-3-fluorobenzoate as yellow oil (0.811 g, 91.1%).

[Step 3] N-(4-chlorophenyl)-N-(2-fluoro-4-(hydrazinecarbonyl)benzyl)-4-methylpiperazine-1-carboxamide

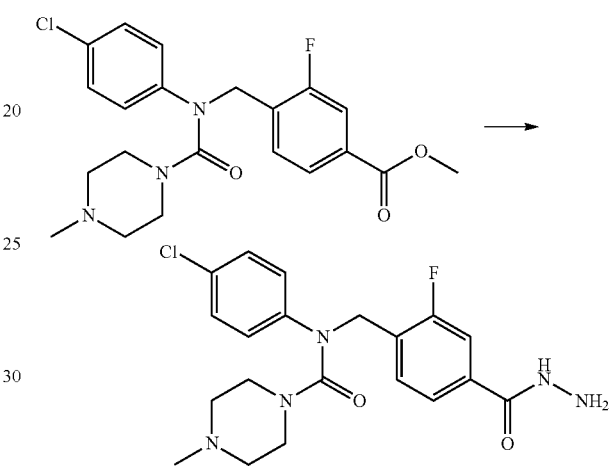

Methyl 4-((N-(4-chlorophenyl)-4-methylpiperazine-1-carboxamido)methyl)-3-fluorobenzoate (0.811 g, 1.932 mmol) prepared in Step 2 and hydrazine monohydrate (1.877 mL, 38.630 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound N-(4-chlorophenyl)-N-(2-fluoro-4-(hydrazinecarbonyl)benzyl)-4-methylpiperazine-1-carboxamide was used without further purification (0.791 g, 97.5%, white solid).

[Step 4] N-(4-chlorophenyl)-N-(4-(2-(2,2-difluoroacetyl)hydrazine-1-carbonyl)-2-fluorobenzyl)-4-methylpiperazine-1-carboxamide

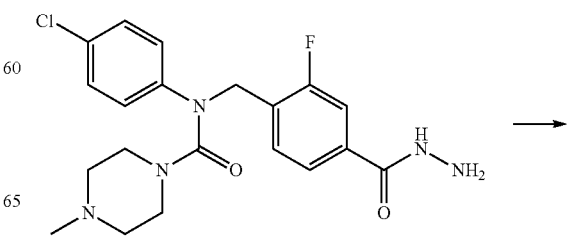

-continued

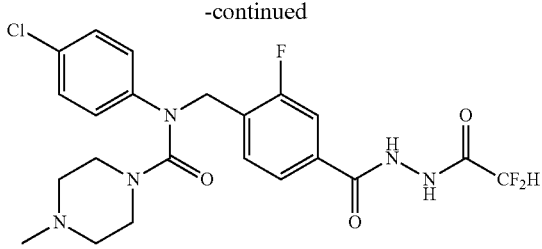

A solution of N-(4-chlorophenyl)-N-(2-fluoro-4-(hydrazinecarbonyl)benzyl)-4-methylpiperazine-1-carboxamide (0.791 g, 1.884 mmol) prepared in Step 3 and triethylamine (0.395 mL, 2.826 mmol) in dichloromethane (10 mL) was mixed at the room temperature with 2,2-difluoroacetic anhydride (0.211 mL, 1.695 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The title compound N-(4-chlorophenyl)-N-(4-(2-(2,2-difluoroacetyl)hydrazine-1-carbonyl)-2-fluorobenzyl)-4-methylpiperazine-1-carboxamide was used without further purification (1.020 g, 108.7%, pale yellow solid).

[Step 5] Compound 21468

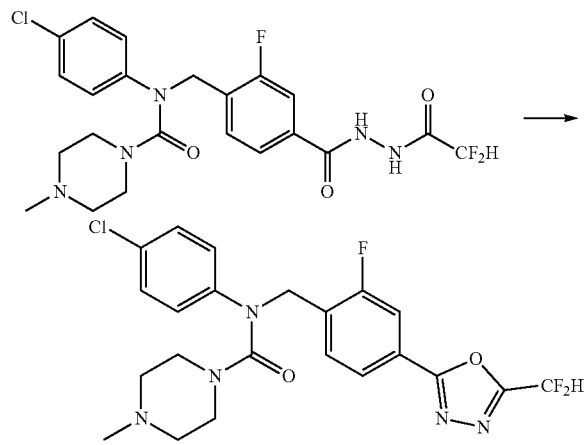

N-(4-chlorophenyl)-N-(4-(2-(2,2-difluoroacetyl)hydrazine-1-carbonyl)-2-fluorobenzyl)-4-methylpiperazine-1-carboxamide (0.300 g, 0.603 mmol) prepared in Step 4 and 1-methoxy-N-triethylammoniosulfonyl-methanimidate (Burgess reagent, 0.216 g, 0.905 mmol) in tetrahydrofuran (10 mL) was mixed at the room temperature and then heated at 150° C. under the microwaves for 30 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; ethyl acetate/hexane=10% to 60%) to give the title compound N-(4-chlorophenyl)-N-(4-(5-(difluoromethyl)-1,3,4-oxadiazol-2-yl)-2-fluorobenzyl)-4-methylpiperazine-1-carboxamide as white solid (0.137 g, 47.3%).

$^1$H NMR (400 MHz, $CDCl_3$) δ 7.88 (dd, 1H, J=8.0, 1.6 Hz), 7.77 (dd, 1H, J=10.0, 1.6 Hz), 7.69 (t, 1H, J=7.6 Hz), 7.31-7.28 (m, 2H), 7.07-7.02 (m, 2H), 6.93 (t, 1H, J=51.0 Hz), 4.96 (s, 2H), 3.39 (brs, 4H), 2.39 (brs, 7H); LRMS (ES) m/z 480.5 ($M^+$+1).

Example 138. Compound 21469: N-(4-(5-(difluoromethyl)-1,3,4-oxadiazol-2-yl)-2-fluorobenzyl)-4-methyl-N-(m-tolyl)piperazine-1-carboxamide

[Step 1]
4-Methyl-N-(o-tolyl)piperazine-1-carboxamide

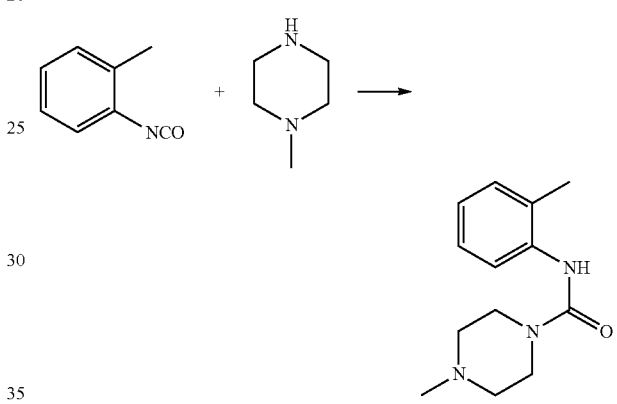

A solution of 1-isocyanato-2-methylbenzene (0.943 mL, 7.510 mmol) and 1-methylpiperazine (0.827 mL, 7.510 mmol) in diethylether (10 mL) was stirred at the room temperature for 1 hr. The precipitates were collected by filtration, washed by hexane, and dried to give the title compound 4-methyl-N-(o-tolyl)piperazine-1-carboxamide as White solid (1.500 g, 85.6%).

[Step 2] Methyl 3-fluoro-4-((4-methyl-N-(o-tolyl)piperazine-1-carboxamido)methyl)benzoate

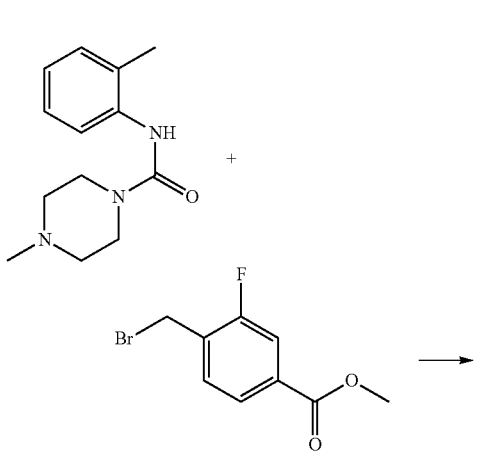

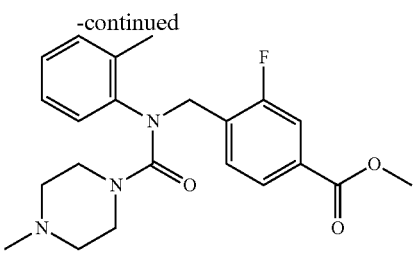

To a stirred solution of 4-methyl-N-(o-tolyl)piperazine-1-carboxamide (0.700 g, 3.000 mmol) prepared in Step 1 in N,N-dimethylformamide (10 mL) was added at 0° C. sodium hydride (60.00%, 0.180 g, 4.500 mmol). The reaction mixture was stirred at the same temperature for 30 min, treated at the room temperature with methyl 4-(bromomethyl)-3-fluorobenzoate (0.889 g, 3.600 mmol), and stirred for additional 12 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 3-fluoro-4-((4-methyl-N-(o-tolyl)piperazine-1-carboxamido)methyl)benzoate as Colorless oil (0.500 g, 41.7%).

[Step 3] N-(2-fluoro-4-(hydrazinecarbonyl)benzyl)-4-methyl-N-(o-tolyl)piperazine-1-carboxamide

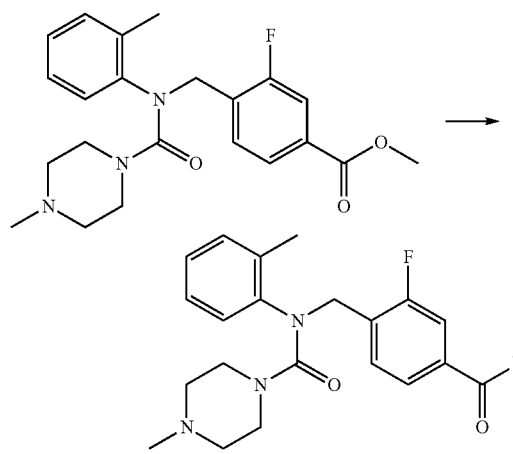

A mixture of methyl 3-fluoro-4-((4-methyl-N-(o-tolyl)piperazine-1-carboxamido)methyl)benzoate (0.500 g, 1.252 mmol) prepared in Step 2 and hydrazine monohydrate (1.182 mL, 25.033 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(2-fluoro-4-(hydrazinecarbonyl)benzyl)-4-methyl-N-(o-tolyl)piperazine-1-carboxamide, 0.289 g, 57.8%, Colorless oil).

[Step 4] N-(4-(2-(2,2-difluoroacetyl)hydrazine-1-carbonyl)-2-fluorobenzyl)-4-methyl-N-(o-tolyl)piperazine-1-carboxamide

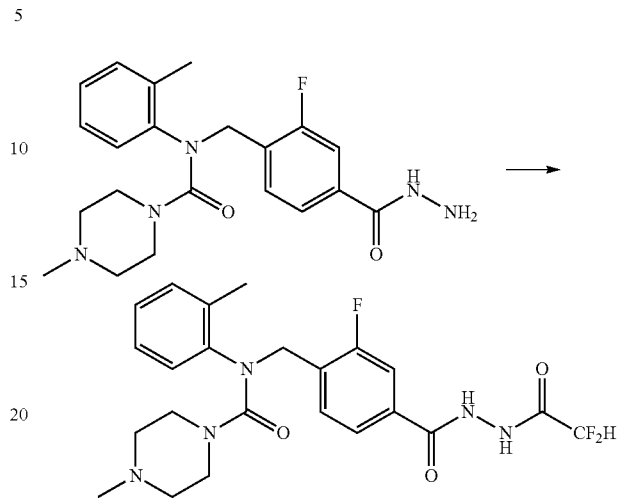

A solution of N-(2-fluoro-4-(hydrazinecarbonyl)benzyl)-4-methyl-N-(o-tolyl)piperazine-1-carboxamide (0.289 g, 0.723 mmol) prepared in Step 3, Difluoroacetic anhydride (0.126 mL, 1.158 mmol) and triethylamine (0.150 mL, 1.085 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-(2-(2,2-difluoroacetyl)hydrazine-1-carbonyl)-2-fluorobenzyl)-4-methyl-N-(o-tolyl)piperazine-1-carboxamide as Colorless oil (0.183 g, 56.5%)

[Step 5] Compound 21469

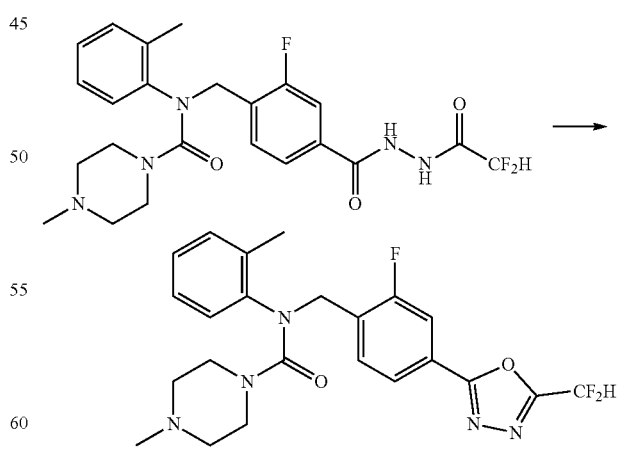

A mixture of N-(4-(2-(2,2-difluoroacetyl)hydrazine-1-carbonyl)-2-fluorobenzyl)-4-methyl-N-(o-tolyl)piperazine-1-carboxamide (0.183 g, 0.383 mmol) prepared in Step 4 and 1-methoxy-N-triethylammoniosulfonyl-methanimidate (Burgess reagent, 0.137 g, 0.575 mmol) in tetrahydrofuran (10 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound N-(4-(5-(difluoromethyl)-1,3,4-oxadiazol-2-yl)-2-fluorobenzyl)-4-methyl-N-(o-tolyl)piperazine-1-carboxamide as Colorless oil (0.090 g, 51.1%).

$^1$H NMR (400 MHz, CDCl$_3$) δ 7.89 (dd, 1H, J=8.1, 1.6 Hz), 7.83 (t, 1H, J=7.5 Hz), 7.69 (dd, 1H, J=9.9, 1.5 Hz), 7.24-7.22 (m, 1H), 7.18-7.14 (m, 1H), 7.18-7.14 (m, 2H), 7.05 (s, 0.25H), 6.99-6.96 (m, 1H), 6.92 (s, 0.5H), 6.79 (s, 0.25H), 4.84 (s, 2H), 3.23 (t, 4H, J=4.9 Hz), 2.20-2.19 (m, 6H), 2.14 (t, 4H, J=4.9 Hz); LRMS (ES) m/z 460.09 (M$^+$+1).

Example 139. Compound 21470: N-(4-(5-(difluoromethyl)-1,3,4-oxadiazol-2-yl)-2-fluorobenzyl)-4-methyl-N-(m-tolyl)piperazine-1-carboxamide

[Step 1]
4-Methyl-N-(m-tolyl)piperazine-1-carboxamide

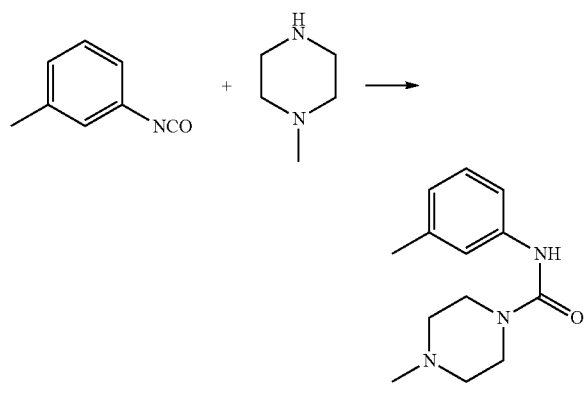

A solution of 1-isocyanato-3-methylbenzene (1.000 g, 7.510 mmol) and 1-methylpiperazine (0.752 g, 7.510 mmol) in diethylether (10 mL) was stirred at the room temperature for 1 hr. The precipitates were collected by filtration, washed by hexane, and dried to give 4-methyl-N-(m-tolyl)piperazine-1-carboxamide as White solid (1.510 g, 86.2%).

[Step 2] Methyl 3-fluoro-4-((4-methyl-N-(m-tolyl)piperazine-1-carboxamido)methyl)benzoate

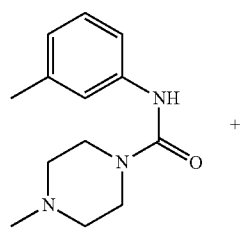

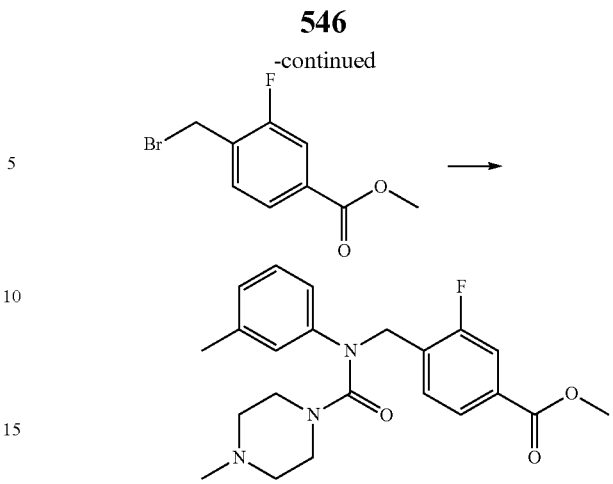

To a stirred solution of 4-methyl-N-(m-tolyl)piperazine-1-carboxamide (0.700 g, 3.000 mmol) prepared in Step 1 in N,N-dimethylformamide (10 mL) was added at 0° C. sodium hydride (60.00%, 0.180 g, 4.500 mmol). The reaction mixture was stirred at the same temperature for 30 min, treated at the room temperature with methyl 4-(bromomethyl)-3-fluorobenzoate (0.889 g, 3.600 mmol), and stirred for additional 10 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 30%) to give the title compound methyl 3-fluoro-4-((4-methyl-N-(m-tolyl)piperazine-1-carboxamido)methyl)benzoate as Colorless oil (0.590 g, 49.2%).

[Step 3] N-(2-fluoro-4-(hydrazinecarbonyl)benzyl)-4-methyl-N-(m-tolyl)piperazine-1-carboxamide

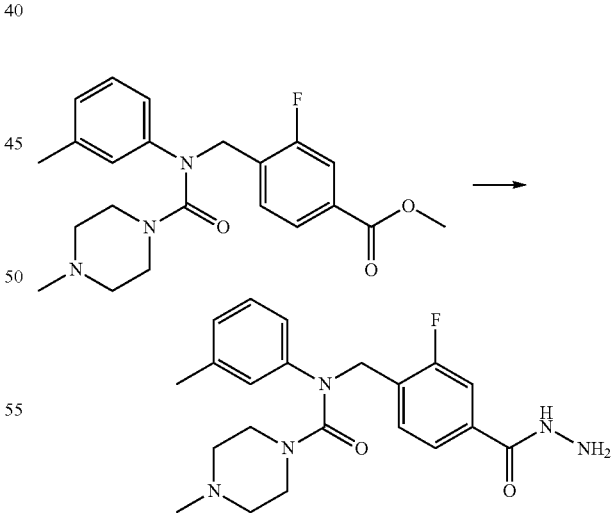

A mixture of methyl 3-fluoro-4-((4-methyl-N-(m-tolyl)piperazine-1-carboxamido)methyl)benzoate (0.590 g, 1.477 mmol) prepared in Step 2 and hydrazine monohydrate (1.395 mL, 29.539 mmol) in N,N-dimethylformamide (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO₄), filtered, and concentrated in vacuo. The crude product was used without further purification (N-(2-fluoro-4-(hydrazinecarbonyl)benzyl)-4-methyl-N-(m-tolyl)piperazine-1-carboxamide, 0.581 g, 98.5%. Colorless oil).

[Step 4] N-(4-(2-(2,2-difluoroacetyl)hydrazine-1-carbonyl)-2-fluorobenzyl)-4-methyl-N-(m-tolyl)piperazine-1-carboxamide

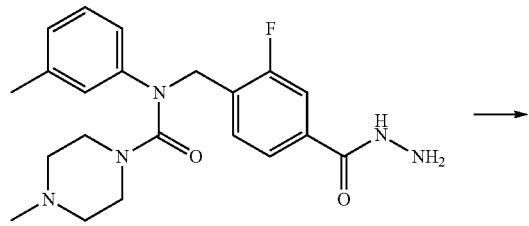

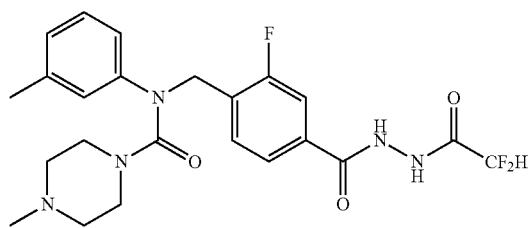

A solution of N-(2-fluoro-4-(hydrazinecarbonyl)benzyl)-4-methyl-N-(m-tolyl)piperazine-1-carboxamide (0.580 g, 1.452 mmol) prepared in Step 3, Difluoroacetic anhydride (0.253 mL, 2.323 mmol) and triethylamine (0.302 mL, 2.178 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-(4-(2-(2,2-difluoroacetyl)hydrazine-1-carbonyl)-2-fluorobenzyl)-4-methyl-N-(m-tolyl)piperazine-1-carboxamide as Colorless oil (0.540 g, 83.1%).

[Step 5] Compound 21470

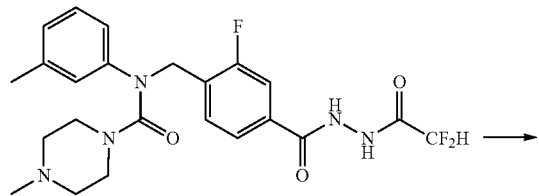

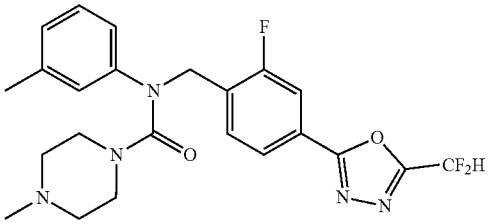

A mixture of N-(4-(2-(2,2-difluoroacetyl)hydrazine-1-carbonyl)-2-fluorobenzyl)-4-methyl-N-(m-tolyl)piperazine-1-carboxamide (0.540 g, 1.131 mmol) prepared in Step 4 and 1-methoxy-N-triethylammoniosulfonyl-methanimidate (Burgess reagent, 0.404 g, 1.696 mmol) in tetrahydrofuran (10 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound N-(4-(5-(difluoromethyl)-1,3,4-oxadiazol-2-yl)-2-fluorobenzyl)-4-methyl-N-(m-tolyl)piperazine-1-carboxamide as Colorless oil (0.340 g, 65.4%).

$^1$H NMR (400 MHz, CDCl₃) δ 7.86 (dd, 1H, J=8.0, 1.7 Hz), 7.75 (dd, 1H, J=10.0, 1.6 Hz), 7.68 (t, 1H, J=7.7 Hz), 7.19 (t, 1H, =7.7 Hz), 7.05 (s, 0.25H), 6.94-6.89 (m, 3.5H), 6.79 (s, 0.5H), 4.96 (s, 2H), 3.31-3.27 (m, 4H), 2.32 (s, 3H), 2.24-2.22 (m, 7H); LRMS (ES) m/z 460.41 (M⁺+1).

Example 140. Compound 21471: N-(4-(5-(difluoromethyl)-1,3,4-oxadiazol-2-yl)-2-fluorobenzyl)-4-methyl-N-(p-tolyl)piperazine-1-carboxamide

[Step 1] 4-Methyl-N-(p-tolyl)piperazine-1-carboxamide

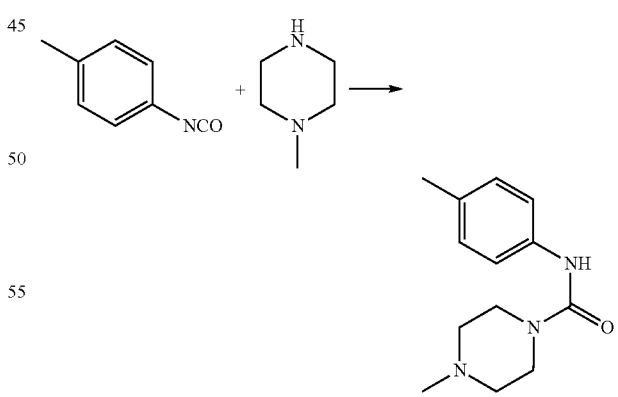

A solution of 1-isocyanate-4-methylbenzene (1.000 g, 7.510 mmol) and 1-methylpiperazine (0.752 g, 7.510 mmol) in diethylether (10 mL) was stirred at the room temperature for 1 hr. The precipitates were collected by filtration, washed by hexane, and dried to give the title compound 4-methyl-N-(p-tolyl)piperazine-1-carboxamide as White solid (1.400 g, 79.9%).

549

[Step 2] Methyl 3-fluoro-4-((4-methyl-N-(p-tolyl)piperazine-1-carboxamido)methyl)benzoate

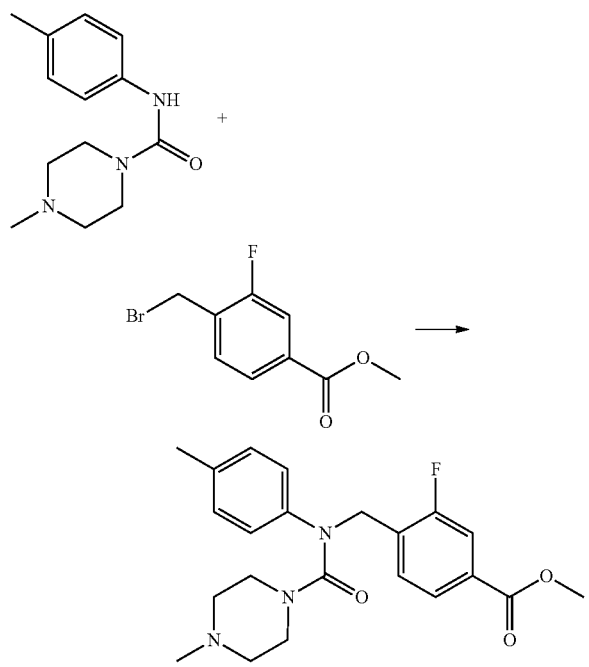

To a stirred solution of 4-methyl-N-(p-tolyl)piperazine-1-carboxamide (0.700 g, 3.000 mmol) prepared in Step 1 in N,N-dimethylformamide (10 mL) was added at 0° C. sodium hydride (60.00%, 0.180 g, 4.500 mmol). The reaction mixture was stirred at the same temperature for 30 min, treated at the room temperature with methyl 4-(bromomethyl)-3-fluorobenzoate (0.889 g, 3.600 mmol), and stirred for additional 10 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound methyl 3-fluoro-4-((4-methyl-N-(p-tolyl)piperazine-1-carboxamido)methyl)benzoate as Colorless oil (0.630 g, 52.6%).

[Step 3] N-(2-fluoro-4-(hydrazinecarbonyl)benzyl)-4-methyl-N-(p-tolyl)piperazine-1-carboxamide

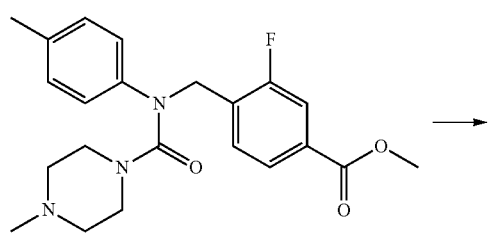

550

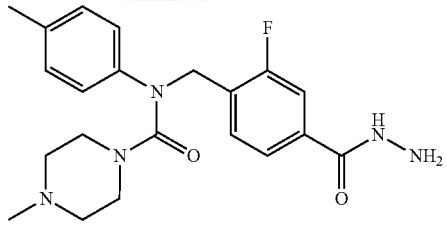

A mixture of methyl 3-fluoro-4-((4-methyl-N-(p-tolyl)piperazine-1-carboxamido)methyl)benzoate (0.630 g, 1.577 mmol) prepared in Step 2 and hydrazine monohydrate (1.490 mL, 31.542 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 30%) to give the title compound N-(2-fluoro-4-(hydrazinecarbonyl)benzyl)-4-methyl-N-(p-tolyl)piperazine-1-carboxamide as Colorless oil (0.622 g, 98.7%).

[Step 4] N-(4-(2-(2,2-difluoroacetyl)hydrazine-1-carbonyl)-2-fluorobenzyl)-4-methyl-N-(p-tolyl)piperazine-1-carboxamide

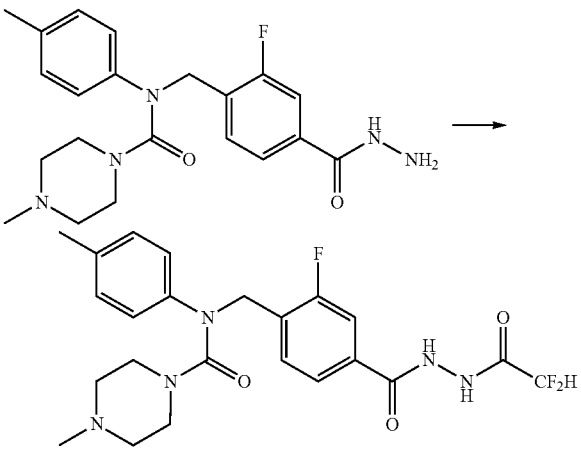

A solution of N-(2-fluoro-4-(hydrazinecarbonyl)benzyl)-4-methyl-N-(p-tolyl)piperazine-1-carboxamide (0.424 g, 1.061 mmol) prepared in Step 3, Difluoroacetic anhydride (0.104 mL, 0.955 mmol) and triethylamine (0.221 mL, 1.592 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-(4-(2-(2,2-difluoroacetyl)hydrazine-1-carbonyl)-2-fluorobenzyl)-4-methyl-N-(p-tolyl)piperazine-1-carboxamide as Colorless oil (0.400 g, 78.9%).

[Step 5] Compound 21471

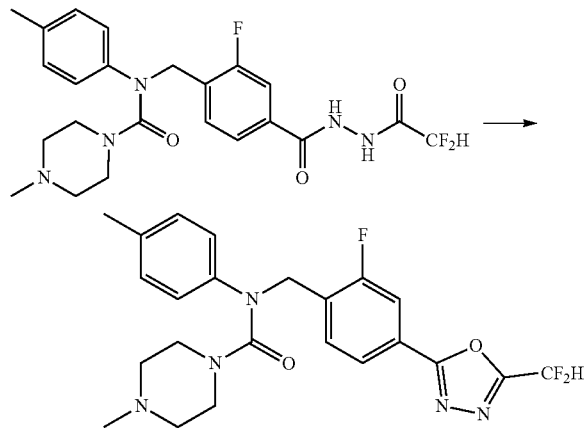

A mixture of N-(4-(2-(2,2-difluoroacetyl)hydrazine-1-carbonyl)-2-fluorobenzyl)-4-methyl-N-(p-tolyl)piperazine-1-carboxamide (0.362 g, 0.758 mmol) prepared in Step 4 and 1-methoxy-N-triethylammoniosulfonyl-methanimidate (Burgess reagent, 0.271 g, 1.137 mmol) in tetrahydrofuran (10 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-(4-(5-(difluoromethyl)-1,3,4-oxadiazol-2-yl)-2-fluorobenzyl)-4-methyl-N-(p-tolyl)piperazine-1-carboxamide as Colorless oil (0.180 g, 51.7%).

$^1$H NMR (400 MHz, CDCl$_3$) δ 7.86 (dd, 1H, J=8.0, 1.6 Hz), 7.74 (dd, 1H, J=10.0, 1.7 Hz), 7.70 (t, 1H, J=7.7 Hz), 7.11-7.09 (m, 2H), 7.05 (s, 0.25H), 7.00-6.97 (m, 2H), 6.92 (s, 0.5H), 6.79 (s, 0.25H), 4.95 (s, 2H), 3.28 (t, 4H, J=5.0 Hz), 2.31 (s, 3H), 2.23-2.18 (m, 7H); LRMS (ES) m/z 460.34 (M$^+$+1).

Example 141. Compound 21472: N-(4-(5-(difluoromethyl)-1,3,4-oxadiazol-2-yl)-2-fluorobenzyl)-N-(2-methoxyphenyl)-4-methylpiperazine-1-carboxamide

[Step 1] N-(2-methoxyphenyl)-4-methylpiperazine-1-carboxamide

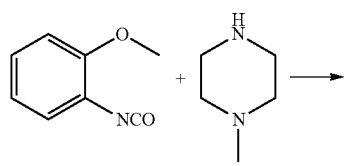

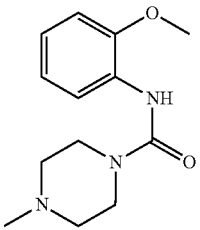

A solution of 1-isocyanato-2-methoxybenzene (1.000 g, 6.705 mmol) and 1-methylpiperazine (0.672 g, 6.705 mmol) in diethylether (10 mL) was stirred at the room temperature for 1 hr. The precipitates were collected by filtration, washed by hexane, and dried to give the title compound N-(2-methoxyphenyl)-4-methylpiperazine-1-carboxamide as White solid (1.500 g, 89.7%).

[Step 2] Methyl 3-fluoro-4-((N-(2-methoxyphenyl)-4-methylpiperazine-1-carboxamido)methyl)benzoate To a stirred solution of N-(2-methoxyphenyl)-4-methylpiperazine-1-carboxamide (0.700 g, 2.808 mmol) prepared in Step 1 in N,N-dimethylformamide (10 mL) was added at 0° C. sodium hydride (60.00%, 0.168 g, 4.212 mmol). The reaction mixture was stirred at the same temperature for 30 min, treated at the room temperature with methyl 4-(bromomethyl)-3-fluorobenzoate (0.832 g, 3.369 mmol), and stirred for additional 10 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 3-fluoro-4-((N-(2-methoxyphenyl)-4-methylpiperazine-1-carboxamido)methyl)benzoat e as Colorless oil (0.450 g, 38.6%).

[Step 3] N-(2-fluoro-4-(hydrazinecarbonyl)benzyl)-N-(2-methoxyphenyl)-4-methylpiperazine-1-carboxamide

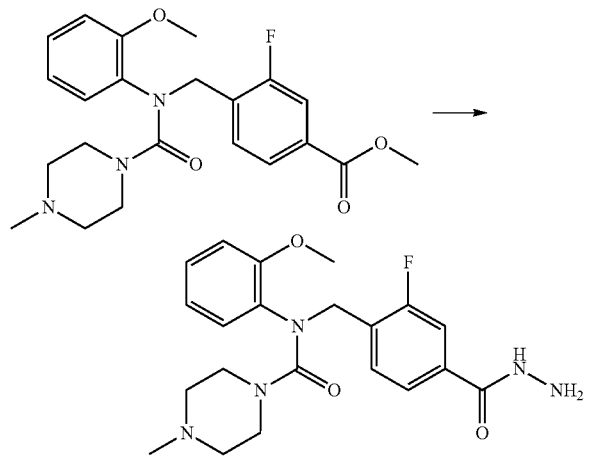

A mixture of methyl 3-fluoro-4-((N-(2-methoxyphenyl)-4-methylpiperazine-1-carboxamido)methyl)benzoat e (0.450 g, 1.083 mmol) prepared in Step 2 and hydrazine monohydrate (1.023 mL, 21.662 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO₄), filtered, and concentrated in vacuo. The title compound N-(2-fluoro-4-(hydrazinecarbonyl)benzyl)-N-(2-methoxyphenyl)-4-methylpiperazine-1-carboxamide was used without further purification (0.424 g, 94.2%, colorless oil).

[Step 4] N-(4-(2-(2,2-difluoroacetyl)hydrazine-1-carbonyl)-2-fluorobenzyl)-N-(2-methoxyphenyl)-4-methylpiperazine-1-carboxamide

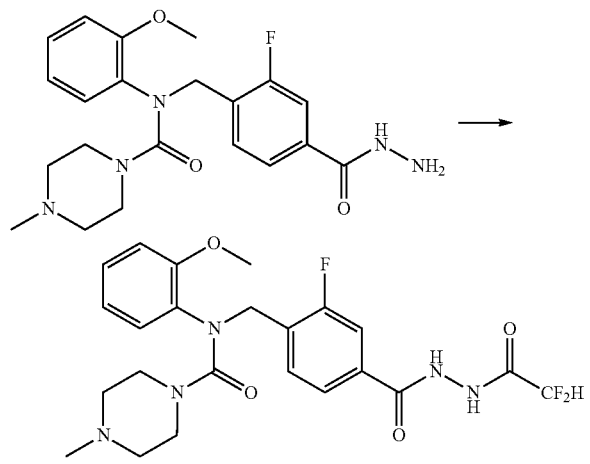

solution of N-(2-fluoro-4-(hydrazinecarbonyl)benzyl)-N-(2-methoxyphenyl)-4-methylpiperazine-1-carboxamide (0.424 g, 1.021 mmol) prepared in Step 3, Difluoroacetic anhydride (0.100 mL, 0.918 mmol) and triethylamine (0.212 mL, 1.531 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; methanol/dichloromethane=0% to 10%) to give the title compound N-(4-(2-(2,2-difluoroacetyl)hydrazine-1-carbonyl)-2-fluorobenzyl)-N-(2-methoxyphenyl)-4-methylpiperazine-1-carboxamide as Colorless oil (0.362 g, 71.9%).

[Step 5] Compound 21472

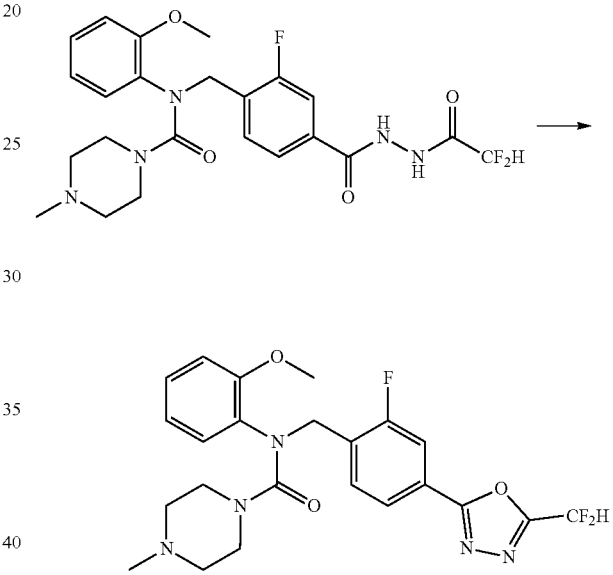

A mixture of N-(4-(2-(2,2-difluoroacetyl)hydrazine-1-carbonyl)-2-fluorobenzyl)-N-(2-methoxyphenyl)-4-methylpiperazine-1-carboxamide (0.361 g, 0.732 mmol) prepared in Step 4 and 1-methoxy-N-triethylammoniosulfonylmethanimidate (Burgess reagent, 0.261 g, 1.097 mmol) in tetrahydrofuran (10 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 12 g cartridge; ethyl acetate/hexane=0% to 50%) to give the title compound N-(4-(5-(difluoromethyl)-1,3,4-oxadiazol-2-yl)-2-fluorobenzyl)-N-(2-methoxyphenyl)-4-methylpiperazine-1-carboxamide as colorless oil (0.160 g, 47.6%).

$^1$H NMR (400 MHz, CDCl₃) δ 7.85 (dd, 1H, J=8.0, 1.5 Hz), 7.74 (dd, 1H, J=10.1, 1.6 Hz), 7.68 (t, 1H, J=7.7 Hz), 7.22-7.18 (m, 7.04 (s, 025H), 6.92 (s, 0.5H), 6.79 (s, 0.25H), 6.70-6.64 (m, 3H), 4.97 (s, 2H), 3.77 (s, 3H), 3.30 (t, 4H, J=4.9 Hz), 2.25-2.23 (m, 7H); LRMS (ES) m/z 477.26 (M⁺+1).

Example 142. Compound 21473: N-(4-(5-(difluoromethyl)-1,3,4-oxadiazol-2-yl)-2-fluorobenzyl)-N-(3-methoxyphenyl)-4-methylpiperazine-1-carboxamide

[Step 1] N-(3-methoxyphenyl)-4-methylpiperazine-1-carboxamide

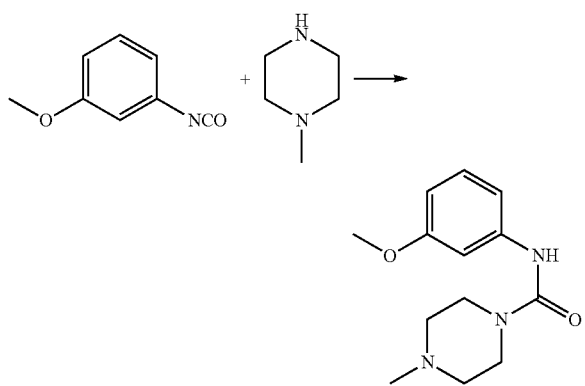

A solution of 1-isocyanato-3-methoxybenzene (1.000 g, 6.705 mmol) and 1-methylpiperazine (0.672 g, 6.705 mmol) in diethylether (10 mL) was stirred at the room temperature for 1 hr. The precipitates were collected by filtration, washed by hexane, and dried to give the title compound N-(3-methoxyphenyl)-4-methylpiperazine-1-carboxamide as White solid (1.450 g, 86.7%).

[Step 2] Methyl 3-fluoro-4-((N-(3-methoxyphenyl)-4-methylpiperazine-1-carboxamido)methyl)benzoat

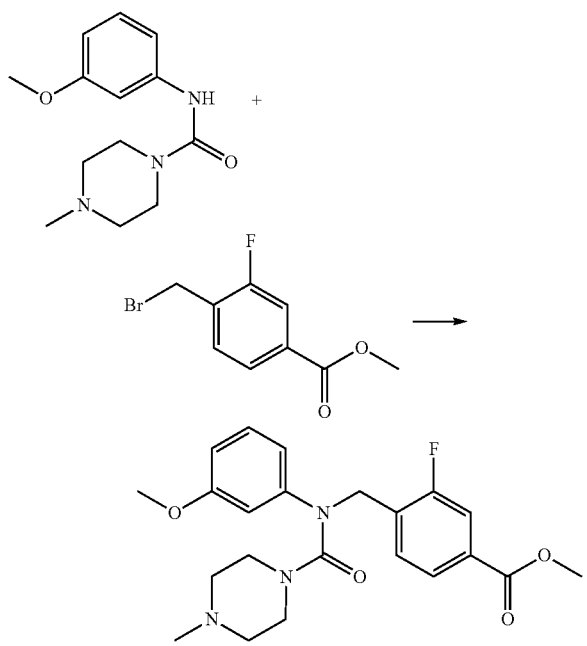

To a stirred solution of N-(3-methoxyphenyl)-4-methylpiperazine-1-carboxamide (0.700 g, 2.808 mmol) prepared in Step 1 in N,N-dimethylformamide (10 mL) was added at 0° C. sodium hydride (60.00%, 0.168 g, 4.212 mmol). The reaction mixture was stirred at the same temperature for 30 min, treated at the room temperature with methyl 4-(bromomethyl)-3-fluorobenzoate (0.832 g, 3.369 mmol), and stirred for additional 10 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound methyl 3-fluoro-4-((N-(3-methoxyphenyl)-4-methylpiperazine-1-carboxamido)methyl)benzoat e as Colorless oil (0.460 g, 39.4%).

[Step 3] N-(2-fluoro-4-(hydrazinecarbonyl)benzyl)-N-(3-methoxyphenyl)-4-methylpiperazine-1-carboxamide

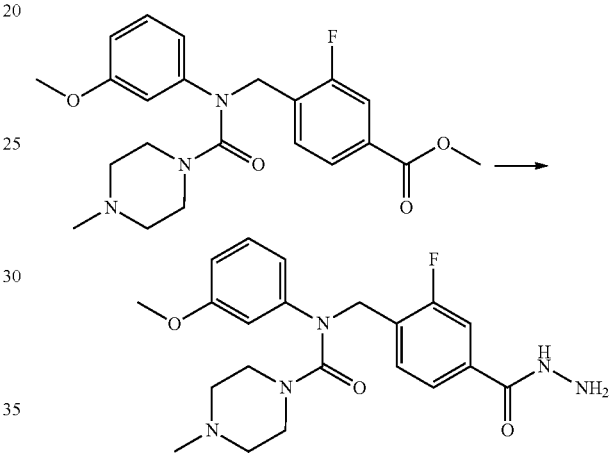

A mixture of methyl 3-fluoro-4-((N-(3-methoxyphenyl)-4-methylpiperazine-1-carboxamido)methyl)benzoat e (0.460 g, 1.107 mmol) prepared in Step 2 and hydrazine monohydrate (1.046 mL, 22.144 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The crude product was used without further purification (N-(2-fluoro-4-(hydrazinecarbonyl)benzyl)-N-(3-methoxyphenyl)-4-methylpiperazine-1-carboxamide, 0.456 g, 99.1%, Colorless oil).

[Step 4] N-(4-(2-(2,2-difluoroacetyl)hydrazine-1-carbonyl)-2-fluorobenzyl)-N-(3-methoxyphenyl)-4-methylpiperazine-1-carboxamide

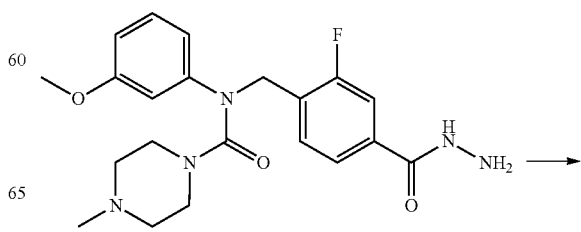

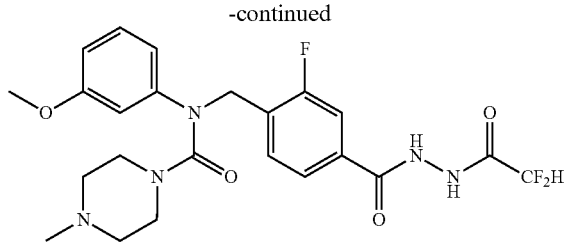

A solution of N-(2-fluoro-4-(hydrazinecarbonyl)benzyl)-N-(3-methoxyphenyl)-4-methylpiperazine-1-carboxamide (0.456 g, 1.098 mmol) prepared in Step 3, Difluoroacetic anhydride (0.107 mL, 0.988 mmol) and triethylamine (0.185 mL, 1.646 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 10%) to give the title compound N-(4-(2-(2,2-difluoroacetyl)hydrazine-1-carbonyl)-2-fluorobenzyl)-N-(3-methoxyphenyl)-4-methylpiperazine-1-carboxamide as Colorless oil (0.361 g, 66.7%).

[Step 5] Compound 21473

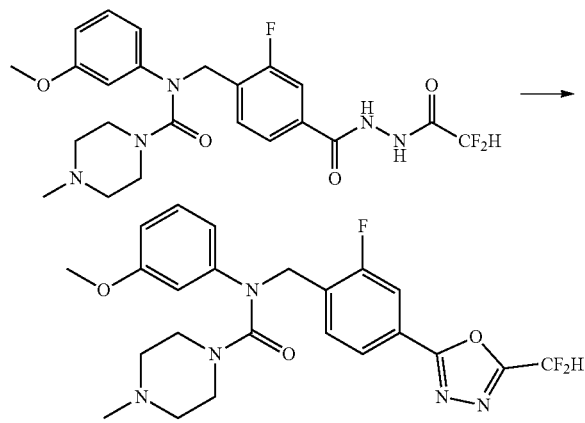

A mixture of N-(4-(2-(2,2-difluoroacetyl)hydrazine-1-carbonyl)-2-fluorobenzyl)-N-(3-methoxyphenyl)-4-methylpiperazine-1-carboxamide (0.361 g, 0.732 mmol) prepared in Step 4 and 1-methoxy-N-triethylammoniosulfonylmethanimidate (Burgess reagent, 0.261 g, 1.097 mmol) in tetrahydrofuran (10 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; ethyl acetate/hexane=0% to 50%) to give the title compound N-(4-(5-(difluoromethyl)-1,3,4-oxadiazol-2-yl)-2-fluorobenzyl)-N-(3-methoxyphenyl)-4-methylpiperazine-1-carboxamide as Colorless oil (0.150 g, 44.6%).

$^1$H NMR (400 MHz, CDCl$_3$) δ 7.86-7.85 (m, 2H), 7.68-7.65 (m, 1H), 7.21-7.17 (m, 1H), 7.04-6.78 (m, 4H), 4.85 (s, 2H), 3.84 (s, 3H), 3.22 (t, 4H, J=5.0 Hz), 2.20 (s, 3H), 2.15 (t, 4H, J=5.0 Hz)); LRMS (ES) m/z 477.13 (M$^+$+1).

Example 143. Compound 21474: N-(4-(5-(difluoromethyl)-1,3,4-oxadiazol-2-yl)benzyl)-N-(2-methoxyphenyl)thiomorpholine-4-carboxamide 1,1-dioxide

[Step 1] Methyl 4-((N-(2-methoxyphenyl)-1,1-dioxidothiomorpholine-4-carboxamido)methyl)benzoate

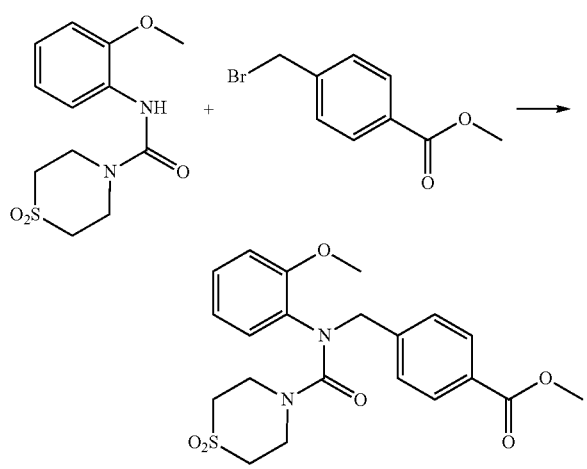

To a stirred solution of N-(2-methoxyphenyl)thiomorpholine-4-carboxamide 1,1-dioxide (0.500 g, 1.759 mmol) in N,N-dimethylformamide (20 mL) was added at 0° C. sodium hydride (60.00%, 0.084 g, 2.110 mmol). The reaction mixture was stirred at the same temperature, treated at the room temperature with methyl 4-(bromomethyl)benzoate (0.443 g, 1.934 mmol), and stirred for additional 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; methanol/dichloromethane=0% to 5%) to give the title compound methyl 4-((N-(2-methoxyphenyl)-1,1-dioxidothiomorpholine-4-carboxamido)methyl)benzoate as bright yellow solid (0.278 g, 36.5%).

[Step 2] N-(4-(hydrazinecarbonyl)benzyl)-N-(2-methoxyphenyl)thiomorpholine-4-carboxamide 1,1-dioxide

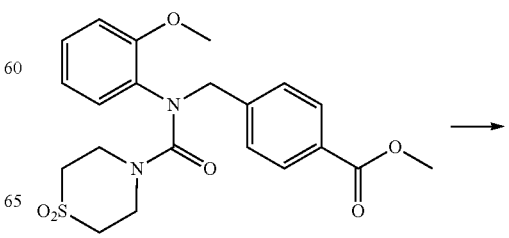

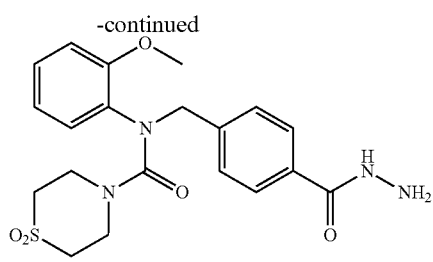

A mixture of methyl 4-((N-(2-methoxyphenyl)-1,1-dioxidothiomorpholine-4-carboxamido)methyl)benzoate (0.278 g, 0.642 mmol) prepared in Step 1 and hydrazine monohydrate (0.606 mL, 12.842 mmol) in ethanol (10 mL) was heated at reflux for 16 hr, and cooled down to the ambient temperature. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 5%) to give the title compound N-(4-(hydrazinecarbonyl)benzyl)-N-(2-methoxyphenyl)thiomorpholine-4-carboxamide 1,1-dioxide as white solid (0.161 g, 58.0%)

[Step 3] Compound 21474

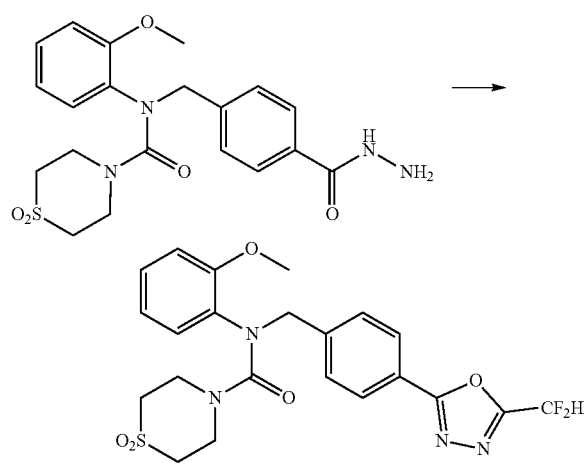

A solution of N-(4-(hydrazinecarbonyl)benzyl)-N-(2-methoxyphenyl)thiomorpholine-4-carboxamide 1,1-dioxide (0.161 g, 0.372 mmol) prepared in Step 2 and triethylamine (0.077 mL, 0.558 mmol) in dichloromethane (3 mL) was mixed at 0° C. with difluoroacetic anhydride (0.036 mL, 0.335 mmol), and stirred at the room temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound N-(4-(5-(difluoromethyl)-1,3,4-oxadiazol-2-yl)benzyl)-N-(2-methoxyphenyl)thiomorpholine-4-carboxamide 1,1-dioxide as bright yellow solid (0.124 g, 67.6%).

$^1$H NMR (400 MHz, CDCl$_3$) δ 8.03-7.94 (m, 2H), 7.49-7.42 (m, 2H), 7.30-7.21 (m, 1H), 7.05-6.75 (m, 4H), 4.73 (s, 2H), 3.81 (s, 3H), 3.68 (m, 4H), 2.64 (m, 4H); LRMS (ES) m/z 493.2 (M$^+$+1).

Example 144. Compound 21475: N-(4-(5-(difluoromethyl)-1,3,4-oxadiazol-2-yl)benzyl)-N-(3-methoxyphenyl)thiomorpholine-4-carboxamide 1,1-dioxide

[Step 1] Methyl 4-((N-(3-methoxyphenyl)-1,1-dioxidothiomorpholine-4-carboxamido)methyl)benzoate

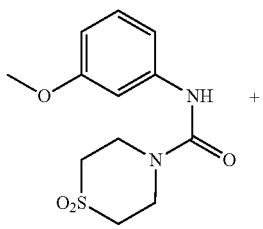

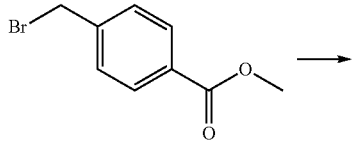

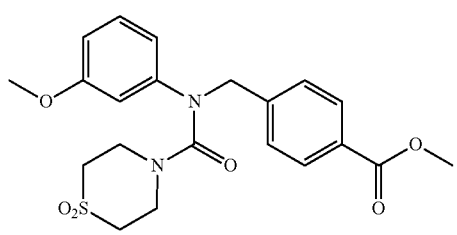

To a stirred solution of N-(3-methoxyphenyl)thiomorpholine-4-carboxamide 1,1-dioxide (0.500 g, 1.759 mmol) in N,N-dimethylformamide (20 mL) was added at 0° C. sodium hydride (60.00%, 0.084 g, 2.110 mmol). The reaction mixture was stirred at the same temperature, treated at the room temperature with methyl 4-(bromomethyl)benzoate (0.443 g, 1.934 mmol), and stirred for additional 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; methanol/dichloromethane=0% to 5%) to give the title compound methyl 4-((N-(3-methoxyphenyl)-1,1-dioxidothiomorpholine-4-carboxamido)methyl)benzoate as white solid (0.238 g, 31.3%).

[Step 2] N-(4-(hydrazinecarbonyl)benzyl)-N-(3-methoxyphenyl)thiomorpholine-4-carboxamide 1,1-dioxide

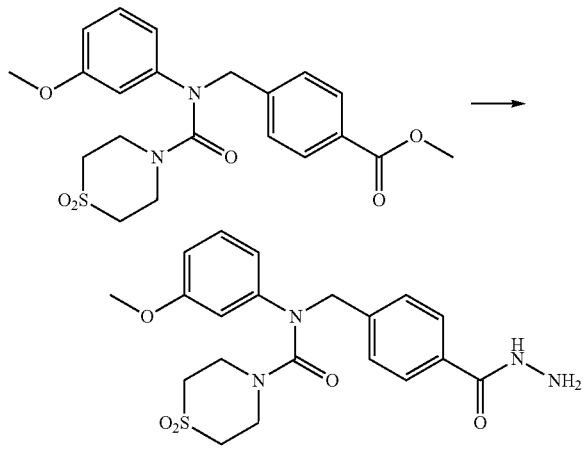

A mixture of methyl 4-((N-(3-methoxyphenyl)-1,1-dioxidothiomorpholine-4-carboxamido)methyl)benzoate (0.238 g, 0.551 mmol) prepared in Step 1 and hydrazine monohydrate (0.521 mL, 11.025 mmol) in ethanol (10 mL) was heated at reflux for 16 hr, and and cooled down to the ambient temperature. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 12 g cartridge; methanol/dichloromethane=0% to 5%) to give the title compound N-(4-(hydrazinecarbonyl)benzyl)-N-(3-methoxyphenyl)thiomorpholine-4-carboxamide 1,1-dioxide as white solid (0.135 g, 56.6%).

[Step 3] Compound 21475

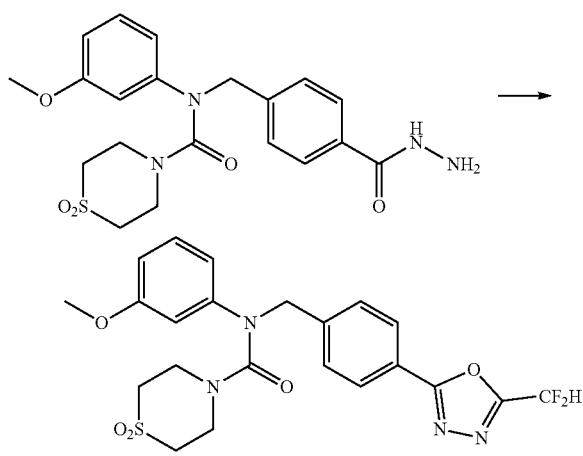

A solution of N-(4-(hydrazinecarbonyl)benzyl)-N-(3-methoxyphenyl)thiomorpholine-4-carboxamide 1,1-dioxide (0.135 g, 0.312 mmol) prepared in Step 2 and triethylamine (0.065 mL, 0.468 mmol) in dichloromethane (3 mL) was mixed at 0° C. with difluoroacetic anhydride (0.031 mL, 0.281 mmol), and stirred at the room temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give N-(4-(5-(difluoromethyl)-1,3,4-oxadiazol-2-yl)benzyl)-N-(3-methoxyphenyl)thiomorpholine-4-carboxamide 1,1-dioxide as yellow solid (0.119 g, 77.4%).

$^1$H NMR (400 MHz, CDCl$_3$) δ 8.05-7.98 (m, 2H), 7.43 (d, 2H, J=8.3, 1.8 Hz), 7.27-7.22 (m, 1H), 7.05-6.76 (m, 1H), 6.75-6.70 (m, 1H), 6.67-6.58 (m, 2H), 4.88 (s, 2H), 3.78-3.69 (m, 4H), 2.86-2.78 (m, 4H); LRMS (ES) m/z 493.2 (M$^+$+1).

Example 145. Compound 21476: N-(4-(5-(difluoromethyl)-1,3,4-oxadiazol-2-yl)benzyl)-N-(m-tolyl)thiomorpholine-4-carboxamide 1,1-dioxide

[Step 1] Methyl 4-((1,1-dioxido-N-(m-tolyl)thiomorpholine-4-carboxamido)methyl)benzoate

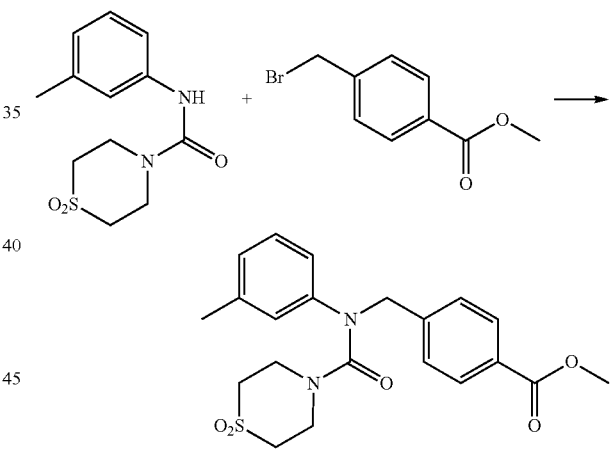

To a stirred solution of N-(m-tolyl)thiomorpholine-4-carboxamide 1,1-dioxide (0.500 g, 1.863 mmol) in N,N-dimethylformamide (20 mL) was added at 0° C. sodium hydride (60.00%, 0.089 g, 2.236 mmol). The reaction mixture was stirred at the same temperature, treated at the room temperature with methyl 4-(bromomethyl)benzoate (0.470 g, 2.050 mmol), and stirred for additional 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 24 g cartridge; methanol/dichloromethane=0% to 5%) to give the title compound methyl 4-((1,1-dioxido-N-(m-tolyl)thiomorpholine-4-carboxamido)methyl)benzoate as white solid (0.427 g, 55.0%).

[Step 2] N-(4-(hydrazinecarbonyl)benzyl)-N-(m-tolyl)thiomorpholine-4-carboxamide 1,1-dioxide

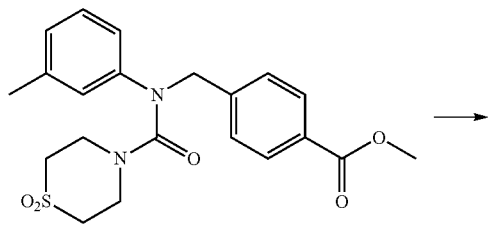

A mixture of methyl 4-((1,1-dioxido-N-(m-tolyl)thiomorpholine-4-carboxamido)methyl)benzoate (0.427 g, 1.025 mmol) prepared in Step 1 and hydrazine monohydrate (0.968 mL, 20.505 mmol) in ethanol (10 mL) was heated at reflux for 16 hr, and cooled down to the ambient temperature. The reaction mixture was concentrated under the reduced pressure to remove the solvent, and water was added to the concentrate, followed by extraction with ethyl acetate. The organic layer was washed with aqueous saturated sodium chloride solution, dried (anhydrous $MgSO_4$), filtered, and concentrated in vacuo. The concentrate was purified and concentrated by column chromatography ($SiO_2$, 24 g cartridge; methanol/dichloromethane=0% to 5%) to give the title compound N-(4-(hydrazinecarbonyl)benzyl)-N-(m-tolyl)thiomorpholine-4-carboxamide 1,1-dioxide as white solid (0.419 g, 98.1%).

[Step 3] N-(4-(2-(2,2-difluoroacetyl)hydrazine-1-carbonyl)benzyl)-N-(m-tolyl)thiomorpholine-4-carboxamide 1,1-dioxide

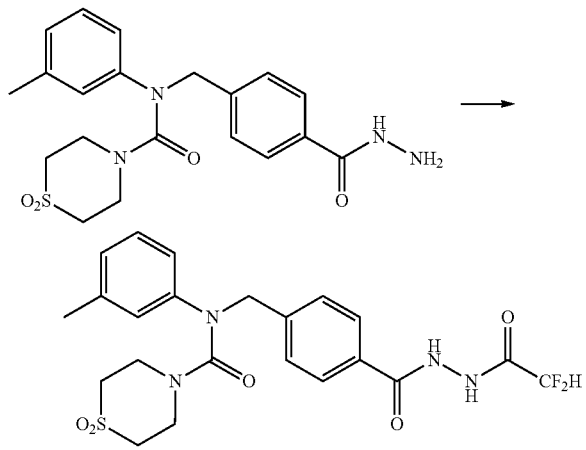

A solution of N-(4-(hydrazinecarbonyl)benzyl)-N-(m-tolyl)thiomorpholine-4-carboxamide 1,1-dioxide (0.419 g, 1.006 mmol) prepared in Step 2 and triethylamine (0.209 mL, 1.509 mmol) in dichloromethane (10 mL) was mixed at 0° C. with difluoroacetic anhydride (0.098 mL, 0.905 mmol), and stirred at the room temperature for 3 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromotography ($SiO_2$, 24 g cartridge; methanol/dichloromethane=0% to 5%) to give the title compound N-(4-(2-(2,2-difluoroacetyl)hydrazine-1-carbonyl)benzyl)-N-(m-tolyl)thiomorpholine-4-carboxamide 1,1-dioxide as white solid (0.415 g, 83.4%).

[Step 4] Compound 21476

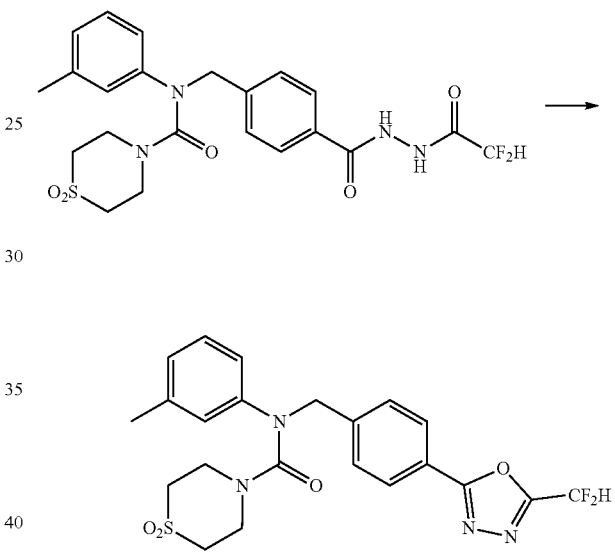

A mixture of N-(4-(2-(2,2-difluoroacetyl)hydrazine-1-carbonyl)benzyl)-N-(m-tolyl)thiomorpholine-4-carboxamide 1,1-dioxide (0.415 g, 0.839 mmol) prepared in Step 3 and 1-methoxy-N-triethylammoniosulfonyl-methanimidate (Burgess reagent, 0.300 g, 1.259 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 12 g cartridge; methanol/dichloromethane=0% to 3%) to give the title compound N-(4-(5-(difluoromethyl)-1,3,4-oxadiazol-2-yl)benzyl)-N-(m-tolyl)thiomorpholine-4-carboxamide 1,1-dioxide as white solid (0.300 g, 75.0%).

$^1$H NMR (400 MHz, $CDCl_3$) δ 8.06-7.98 (m, 2H), 7.47-7.40 (m, 2H), 7.23-7.20 (m, 1H), 7.06-6.74 (m, 4H), 4.87 (s, 2H), 3.76-3.66 (m, 4H), 2.79 (m, 4H), 2.32 (s, 3H); LRMS (ES) m/z 477.1 ($M^+$+1).

Example 146. Compound 21477: N-(2-fluoro-4-(5-(trifluoromethyl)-1,3,4-oxadiazol-2-yl)benzyl)-N-(4-methoxyphenyl)thiomorpholine-4-carboxamide 1,1-dioxide

[Step 1] Methyl 3-fluoro-4-((N-(4-methoxyphenyl)-1,1-dioxidothiomorpholine-4-carboxamido)methyl) benzoate

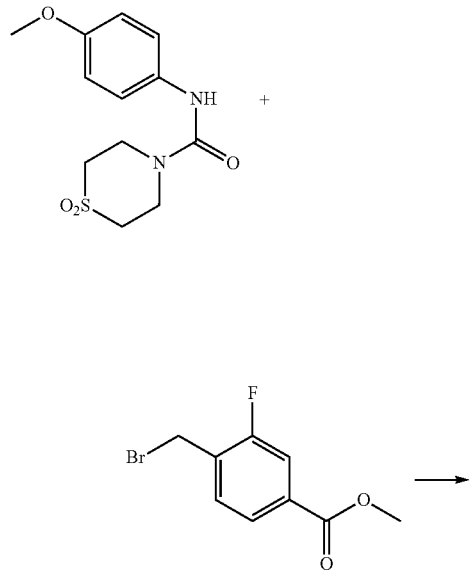

To a stirred solution of N-(4-methoxyphenyl)thiomorpholine-4-carboxamide 1,1-dioxide (1.000 g, 3.517 mmol) in N,N-dimethylformamide (20 mL) was added at 0° C. sodium hydride (60.00%, 0.169 g, 4.220 mmol). The reaction mixture was stirred at the same temperature, treated at the room temperature with methyl 4-(bromomethyl)-3-fluorobenzoate (0.956 g, 3.869 mmol), and stirred for additional 1 hr. Then, aqueous 1N-sodium bicarbonate solution was added to the reaction mixture, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 40 g cartridge; methanol/dichloromethane=0% to 5%) to give the title compound methyl 3-fluoro-4-((N-(4-methoxyphenyl)-1,1-dioxidothiomorpholine-4-carboxamido)methyl) benzoate as bright yellow solid (1.130 g, 71.3%).

[Step 2] N-(2-fluoro-4-(hydrazinecarbonyl)benzyl)-N-(4-methoxyphenyl)thiomorpholine-4-carboxamide 1,1-dioxide

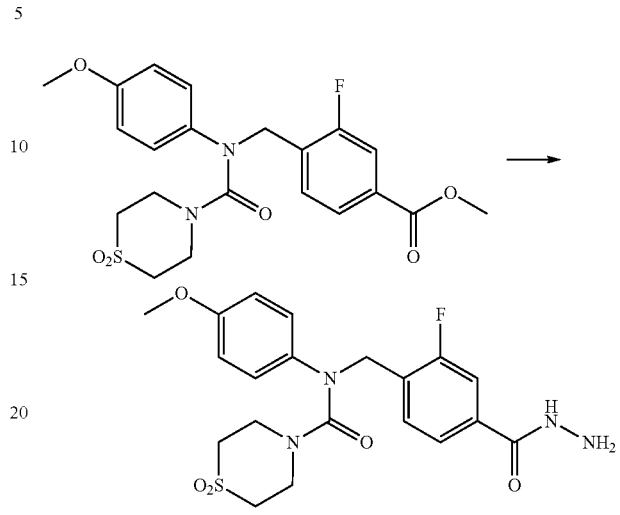

A mixture of methyl 3-fluoro-4-((N-(4-methoxyphenyl)-1,1-dioxidothiomorpholine-4-carboxamido)methyl) benzoate (1.130 g, 2.508 mmol) prepared in Step 1 and hydrazine monohydrate (2.369 mL, 50.169 mmol) in ethanol (10 mL) was heated at reflux for 16 hr, and cooled down to the ambient temperature. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 40 g cartridge; methanol/dichloromethane=0% to 5%) to give the title compound N-(2-fluoro-4-(hydrazinecarbonyl)benzyl)-N-(4-methoxyphenyl)thiomorpholine-4-carboxamide 1,1-dioxide as white solid (0.928 g, 82.1%).

[Step 3] N-(2-fluoro-4-(2-(2,2,2-trifluoroacetyl)hydrazine-1-carbonyl)benzyl)-N-(4-methoxyphenyl)thiomorpholine-4-carboxamide 1,1-dioxide

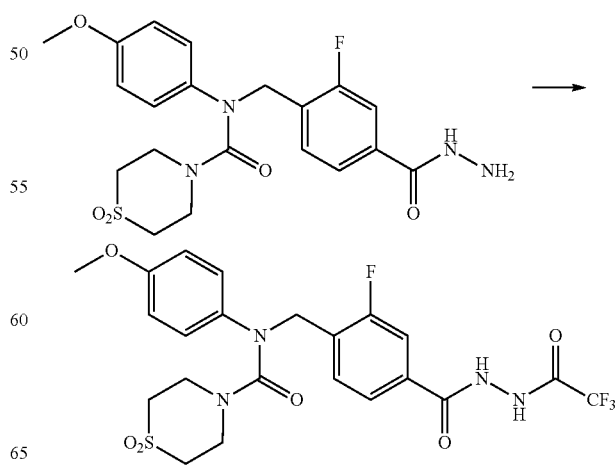

A solution of N-(2-fluoro-4-(hydrazinecarbonyl)benzyl)-N-(4-methoxyphenyl)thiomorpholine-4-carboxamide 1,1-dioxide (0.414 g, 0.919 mmol) prepared in Step 2 and triethylamine (0.191 mL, 1.378 mmol) in dichloromethane (10 mL) was mixed at 0° C. with trifluoroacetic anhydride (0.115 mL, 0.827 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(2-fluoro-4-(2-(2,2,2-trifluoroacetyl)hydrazine-1-carbonyl)benzyl)-N-(4-methoxyphenyl)thiomorpholine-4-carboxamide 1,1-dioxide as white solid (0.502 g, 100.0%).

[Step 4] Compound 21477

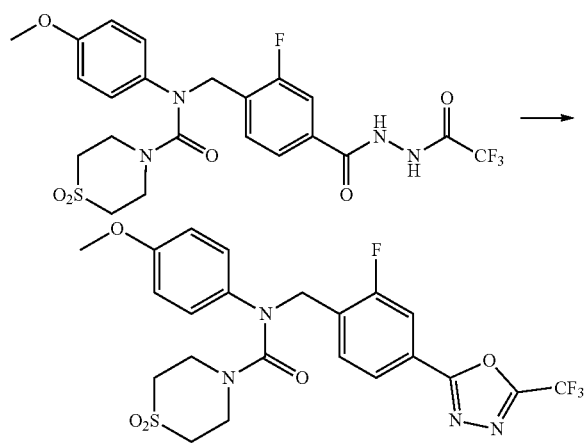

A mixture of N-(2-fluoro-4-(2-(2,2,2-trifluoroacetyl)hydrazine-1-carbonyl)benzyl)-N-(4-methoxyphenyl)thiomorpholine-4-carboxamide 1,1-dioxide (0.543 g, 0.994 mmol) prepared in Step 3 and 1-methoxy-N-triethylammoniosulfonyl-methanimidate (Burgess reagent, 0.355 g, 1.490 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give the title compound N-(2-fluoro-4-(5-(trifluoromethyl)-1,3,4-oxadiazol-2-yl)benzyl)-N-(4-methoxyphenyl)thiomorpholine-4-carboxamide 1,1-dioxide as white solid (0.355 g, 67.6%).

$^1$H NMR (400 MHz, CDCl$_3$) δ 7.88-7.83 (m, 1H), 7.75-7.70 (m, 1H), 7.70-7.64 (m, 1H), 7.05-6.97 (m, 2H), 6.89-6.81 (m, 2H), 4.86 (s, 2H), 3.79 (s, 3H), 3.73-3.68 (m, 4H), 2.80-2.73 (m, 4H); LRMS (ES) m/z 529.1 (M$^+$+1).

Example 147. Compound 21478: N-(4-(5-(difluoromethyl)-1,3,4-oxadiazol-2-yl)-2-fluorobenzyl)-N-(4-methoxyphenyl)thiomorpholine-4-carboxamide 1,1-dioxide

[Step 1] N-(4-(2-(2,2-difluoroacetyl)hydrazine-1-carbonyl)-2-fluorobenzyl)-N-(4-methoxyphenyl) thiomorpholine-4-carboxamide 1,1-dioxide

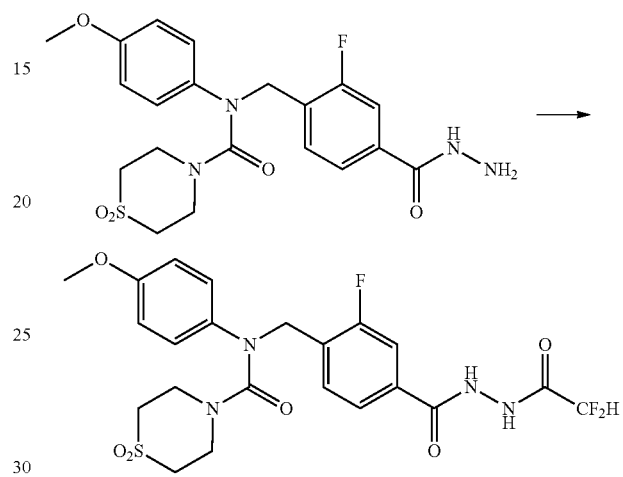

A solution of N-(2-fluoro-4-(hydrazinecarbonyl)benzyl)-N-(4-methoxyphenyl)thiomorpholine-4-carboxamide 1,1-dioxide (0.414 g, 0.919 mmol) prepared in Step 2 of Example 146 and triethylamine (0.191 mL, 1.378 mmol) in dichloromethane (10 mL) was mixed at 0° C. with difluoroacetic anhydride (0.090 mL, 0.827 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(4-(2-(2,2-difluoroacetyl)hydrazine-1-carbonyl)-2-fluorobenzyl)-N-(4-methoxyphenyl) thiomorpholine-4-carboxamide 1,1-dioxide as white solid (0.475 g, 97.8%).

[Step 2] Compound 21478

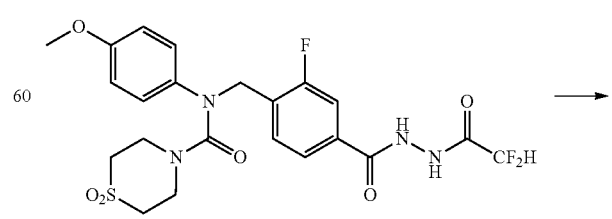

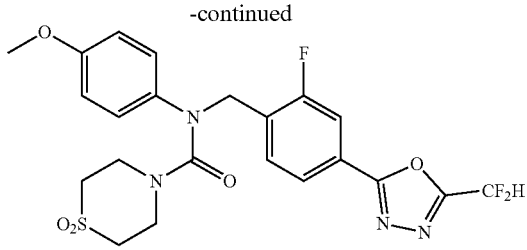

A mixture of N-(4-(2-(2,2-difluoroacetyl)hydrazine-1-carbonyl)-2-fluorobenzyl)-N-(4-methoxyphenyl) thiomorpholine-4-carboxamide 1,1-dioxide (0.475 g, 0.899 mmol) prepared in Step 1 and 1-methoxy-N-triethylammoniosulfonyl-methanimidate (Burgess reagent, 0.321 g, 1.348 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give the title compound N-(4-(5-(difluoromethyl)-1,3,4-oxadiazol-2-yl)-2-fluorobenzyl)-N-(4-methoxyphenyl)thiomorpholine-4-carboxamide 1,1-dioxide as white solid (0.321 g, 70.0%).

$^1$H NMR (400 MHz, CDCl$_3$) δ 7.87-7.83 (m, 1H), 7.73 (dd, 1H, J=10.0, 1.6 Hz), 7.66-7.63 (m, 1H), 7.06-6.75 (m, 5H), 4.86 (s, 2H), 3.79 (s, 3H), 3.71-3.67 (m, 4H), 2.77-2.74 (m, 4H); LRMS (ES) m/z 511 (M$^+$+1).

Example 148. Compound 21479: N-(2-fluoro-4-(5-(trifluoromethyl)-1,3,4-oxadiazol-2-yl)benzyl)-N-(2-methoxyphenyl)thiomorpholine-4-carboxamide 1,1-dioxide

[Step 1] Methyl 3-fluoro-4-((N-(2-methoxyphenyl)-1,1-dioxidothiomorpholine-4-carboxamido)methyl) benzoate

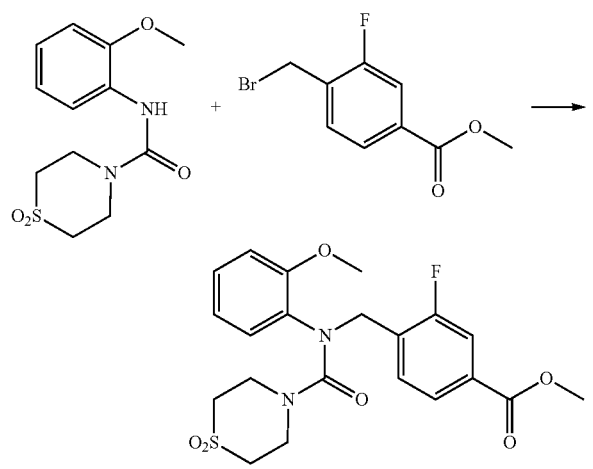

To a stirred solution of N-(2-methoxyphenyl)thiomorpholine-4-carboxamide 1,1-dioxide (1.000 g, 3.517 mmol) in N,N-dimethylformamide (10 mL) was added at 0° C. sodium hydride (60.00%, 0.169 g, 4.220 mmol). The reaction mixture was stirred at the same temperature, treated at the room temperature with methyl 4-(bromomethyl)-3-fluorobenzoate (0.956 g, 3.869 mmol), and stirred for additional 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 40 g cartridge; methanol/dichloromethane=0% to 5%) to give the title compound methyl 3-fluoro-4-((N-(2-methoxyphenyl)-1,1-dioxidothiomorpholine-4-carboxamido)methyl) benzoate as white solid (1.582 g, 99.9%).

[Step 2] N-(2-fluoro-4-(hydrazinecarbonyl)benzyl)-N-(2-methoxyphenyl)thiomorpholine-4-carboxamide 1,1-dioxide

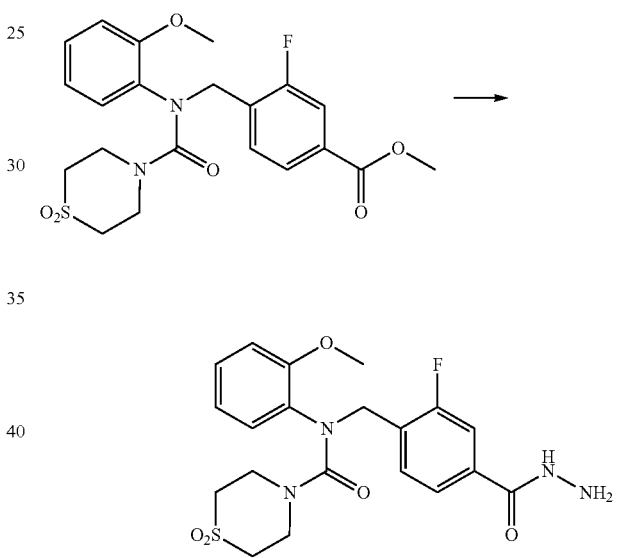

A mixture of methyl 3-fluoro-4-((N-(2-methoxyphenyl)-1,1-dioxidothiomorpholine-4-carboxamido)methyl) benzoate (1.580 g, 3.507 mmol) prepared in Step 1 and hydrazine monohydrate (3.313 mL, 70.147 mmol) in ethanol (10 mL) was heated at reflux for 16 hr, and cooled down to the ambient temperature. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 40 g cartridge; methanol/dichloromethane=0% to 5%) to give the title compound N-(2-fluoro-4-(hydrazinecarbonyl)benzyl)-N-(2-methoxyphenyl)thiomorpholine-4-carboxamide 1,1-dioxide as white solid (1.580 g, 100.0%).

[Step 3] N-(2-fluoro-4-(2-(2,2,2-trifluoroacetyl)hydrazine-1-carbonyl)benzyl)-N-(2-methoxyphenyl)thiomorpholine-4-carboxamide 1,1-dioxide

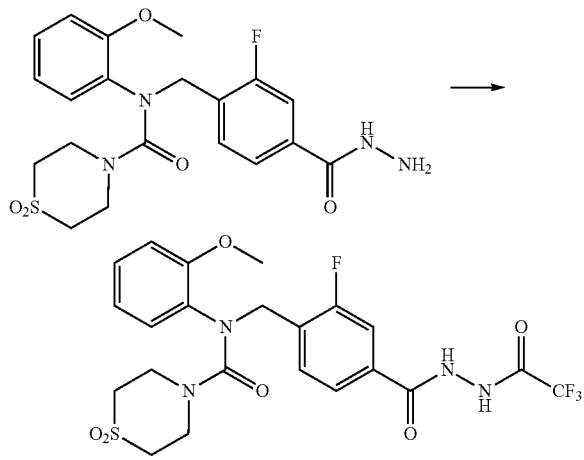

A solution of N-(2-fluoro-4-(hydrazinecarbonyl)benzyl)-N-(2-methoxyphenyl)thiomorpholine-4-carboxamide 1,1-dioxide (0.500 g, 1.110 mmol) prepared in Step 2 and triethylamine (0.231 mL, 1.665 mmol) in dichloromethane (10 mL) was mixed at 0° C. with trifluoroacetic anhydride (0.139 mL, 0.999 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(2-fluoro-4-(2-(2,2,2-trifluoroacetyl)hydrazine-1-carbonyl)benzyl)-N-(2-methoxyphenyl)thiomorpholine-4-carboxamide 1,1-dioxide as white solid (0.268 g, 44.2%).

[Step 4] Compound 21479

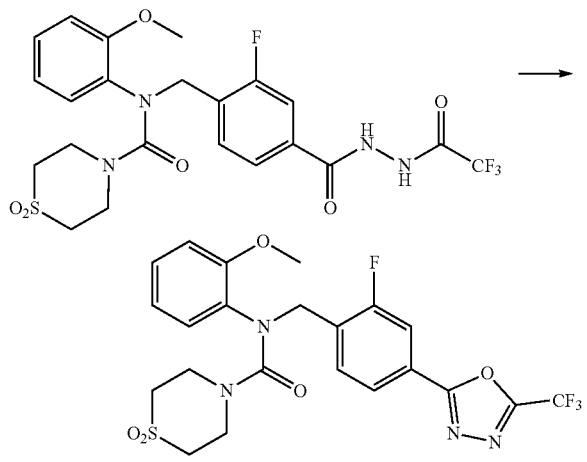

A mixture of N-(2-fluoro-4-(2-(2,2,2-trifluoroacetyl)hydrazine-1-carbonyl)benzyl)-N-(2-methoxyphenyl)thiomorpholine-4-carboxamide 1,1-dioxide (0.268 g, 0.490 mmol) prepared in Step 3 and 1-methoxy-N-triethylammoniosulfonyl-methanimidate (Burgess reagent, 0.175 g, 0.736 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound N-(2-fluoro-4-(5-(trifluoromethyl)-1,3,4-oxadiazol-2-yl)benzyl)-N-(2-methoxyphenyl)thiomorpholine-4-carboxamide 1,1-dioxide as white solid (0.175 g, 67.5%).
$^1$H NMR (400 MHz, CDCl$_3$) δ 7.86-7.76 (m, 2H), 7.66 (dd, 1H, J=9.8, 1.6 Hz), 7.29-7.23 (m, 1H), 6.98-6.87 (m, 4H), 4.82 (s, 2H), 3.82 (s, 3H), 3.71-3.64 (m, 4H), 2.68-2.61 (m, 4H); LRMS (ES) m/z 529 (M$^+$+1).

Example 149. Compound 21480: N-(4-(5-(difluoromethyl)-1,3,4-Oxadiazol-2-yl)-2-fluorobenzyl)-N-(2-methoxyphenyl)thiomorpholine-4-carboxamide 1,1-dioxide

[Step 1] N-(4-(2-(2,2-difluoroacetyl)hydrazine-1-carbonyl)-2-fluorobenzyl)-N-(2-methoxyphenyl)thiomorpholine-4-carboxamide 1,1-dioxide

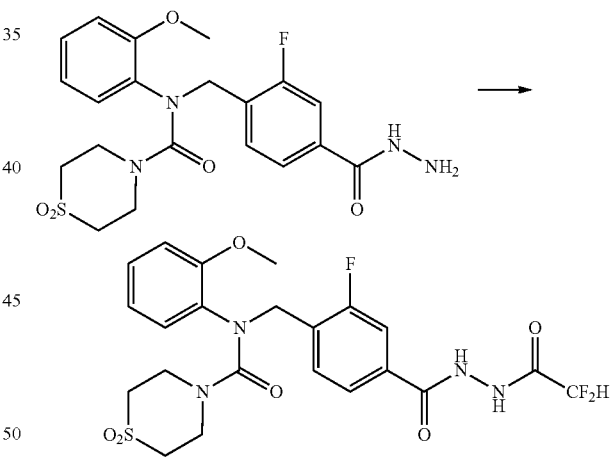

A solution of N-(2-fluoro-4-(hydrazinecarbonyl)benzyl)-N-(2-methoxyphenyl)thiomorpholine-4-carboxamide 1,1-dioxide (0.500 g, 1.110 mmol) prepared in Step 2 of Example 148 and triethylamine (0.231 mL, 1.665 mmol) in dichloromethane (10 mL) was mixed at 0° C. with difluoroacetic anhydride (0.109 mL, 0.999 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(4-(2-(2,2-difluoroacetyl)hydrazine-1- carbonyl)-2-fluorobenzyl)-N-(2-methoxyphenyl) thiomorpholine-4-carboxamide 1,1-dioxide as white solid (0.304 g, 51.8%).

[Step 2] Compound 21480

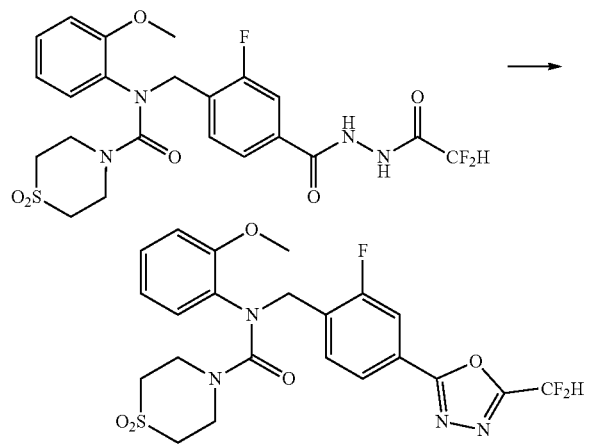

A mixture of N-(4-(2-(2,2-difluoroacetyl)hydrazine-1-carbonyl)-2-fluorobenzyl)-N-(2-methoxyphenyl) thiomorpholine-4-carboxamide 1,1-dioxide (0.304 g, 0.575 mmol) prepared in Step 1 and 1-methoxy-N-triethylammoniosulfonyl-methanimidate (Burgess reagent, 0.206 g, 0.863 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added, to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound N-(4-(5-(difluoromethyl)-1,3,4-oxadiazol-2-yl)-2-fluorobenzyl)-N-(2-methoxyphenyl)thiomorpholine-4-carboxamide 1,1-dioxide as white solid (0.206 g, 70.2%).

$^1$H NMR (400 MHz, CDCl$_3$) δ 7.84 (dd, 1H, J=7.9, 1.5 Hz), 7.80-7.73 (m, 1H), 7.66 (dd, 1H, J=9.9, 1.7 Hz), 7.30-7.19 (m, 1H), 7.04-6.75 (m, 4H), 4.82 (s, 2H), 3.83 (s, 3H), 3.72-3.64 (m, 4H), 2.68-2.61 (m, 4H); LRMS (ES) m/z 511.1 (M$^+$+1).

Example 150. Compound 21481: N-(2-fluoro-4-(5-(trifluoromethyl)-1,3,4-oxadiazol-2-yl)benzyl)-N-(3-methoxyphenyl)thiomorpholine-4-carboxamide 1,1-dioxide

[Step 1] Methyl 3-fluoro-4-((N-(3-methoxyphenyl)-1,1-dioxidothiomorpholine-4-carboxamido)methyl) benzoate

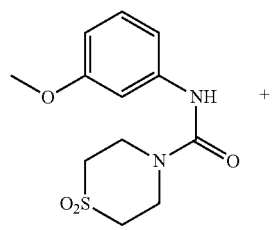

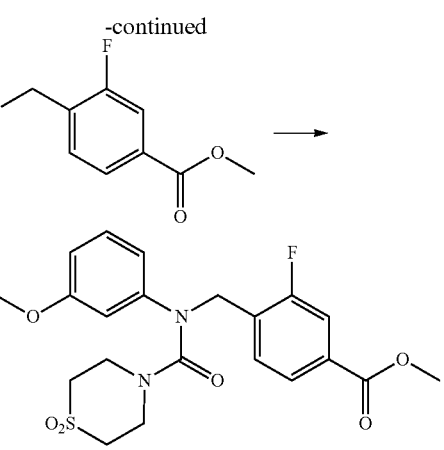

To a stirred solution of N-(3-methoxyphenyl)thiomorpholine-4-carboxamide 1,1-dioxide (1.000 g, 3.517 mmol) in N,N-dimethylformamide (10 mL) was added at 0° C. sodium hydride (60.00%, 0.169 g, 4.220 mmol). The reaction mixture was stirred at the same temperature, treated at the room temperature with methyl 4-(bromomethyl)-3-fluorobenzoate (0.956 g, 3.869 mmol), and stirred for additional 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 40 g cartridge; methanol/dichloromethane=0% to 5%) to give the title compound methyl 3-fluoro-4-((N-(3-methoxyphenyl)-1,1-dioxidothiomorpholine-4-carboxamido)methyl) benzoate as white solid (1.110 g, 70.1%).

[Step 2] N-(2-fluoro-4-(hydrazinecarbonyl)benzyl)-N-(3-methoxyphenyl)thiomorpholine-4-carboxamide 1,1-dioxide

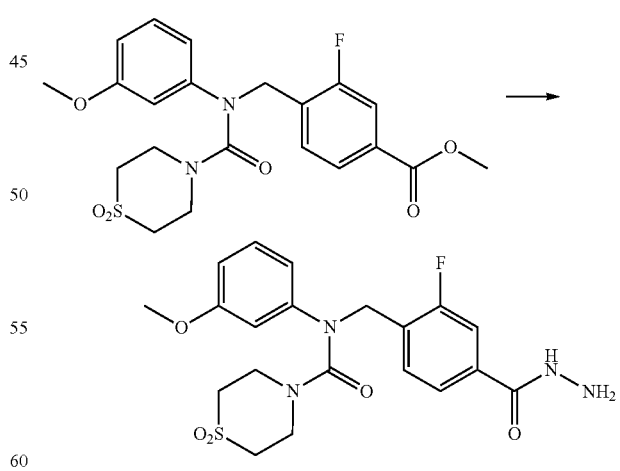

A mixture of methyl 3-fluoro-4-((N-(3-methoxyphenyl)-1,1-dioxidothiomorpholine-4-carboxamido)methyl) benzoate (1.110 g, 2.464 mmol) prepared in Step 1 and hydrazine monohydrate (2.327 mL, 49.281 mmol) in ethanol (10 mL) was heated at reflux for 16 hr, and cooled down to the ambient temperature. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 40 g cartridge; methanol/dichloromethane=0% to 5%) to give the title compound N-(2-fluoro-4-(hydrazinecarbonyl)benzyl)-N-(3-methoxyphenyl)thiomorpholine-4-carboxamide 1,1-dioxide as white solid (0.897 g, 80.8%).

[Step 3] N-(2-fluoro-4-(2-(2,2,2-trifluoroacetyl)hydrazine-1-carbonyl)benzyl)-N-(3-methoxyphenyl)thiomorpholine-4-carboxamide 1,1-dioxide

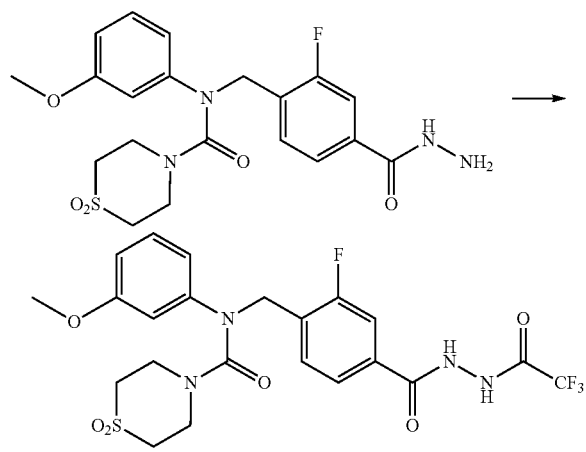

A solution of N-(2-fluoro-4-(hydrazinecarbonyl)benzyl)-N-(3-methoxyphenyl)thiomorpholine-4-carboxamide 1,1-dioxide (0.448 g, 0.994 mmol) prepared in Step 2 and triethylamine (0.207 mL, 1.492 mmol) in dichloromethane (10 mL) was mixed at 0° C. with trifluoroacetic anhydride (0.124 mL, 0.895 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(2-fluoro-4-(2-(2,2,2-trifluoroacetyl)hydrazine-1-carbonyl)benzyl)-N-(3-methoxyphenyl)thiomorpholine-4-carboxamide 1,1-dioxide as white solid (0.416 g, 76.5%).

[Step 4] Compound 21481

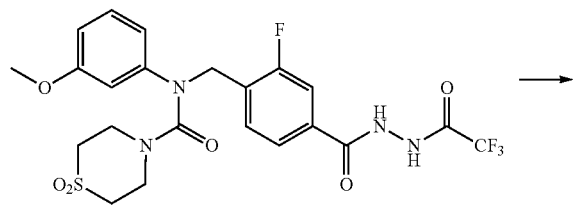

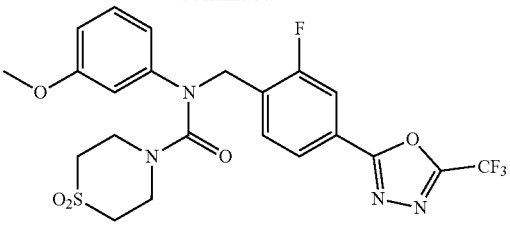

A mixture of N-(2-fluoro-4-(2-(2,2,2-trifluoroacetyl)hydrazine-1-carbonyl)benzyl)-N-(3-methoxyphenyl)thiomorpholine-4-carboxamide 1,1-dioxide (0.416 g, 0.761 mmol) prepared in Step 3 and 1-methoxy-N-triethylammoniosulfonyl-methanimidate (Burgess reagent, 0.272 g, 1.142 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound N-(2-fluoro-4-(5-(trifluoromethyl)-1,3,4-oxadiazol-2-yl)benzyl)-N-(3-methoxyphenyl)thiomorpholine-4-carboxamide 1,1-dioxide as white solid (0.272 g, 67.6%).

$^1$H NMR (400 MHz, CDCl$_3$) δ 7.90-7.82 (m, 1H), 7.79-7.71 (m, 1H), 7.71-7.62 (m, 1H), 7.29-7.21 (m, 1H), 6.75-6.69 (m, 3H), 4.92 (s, 2H), 3.78 (s, 3H), 3.73-3.41 (m, 4H), 2.80-2.79 (m, 4H); LRMS (ES) m/z 529 (M$^+$+1).

Example 151. Compound 21482: N-(4-(5-(difluoromethyl)-1,3,4-oxadiazol-2-yl)-2-fluorobenzyl)-N-(3-methoxyphenyl)thiomorpholine-4-carboxamide 1,1-dioxide

[Step 1] N-(4-(2-(2,2-difluoroacetyl)hydrazine-1-carbonyl)-2-fluorobenzyl)-N-(3-methoxyphenyl)thiomorpholine-4-carboxamide 1,1-dioxide

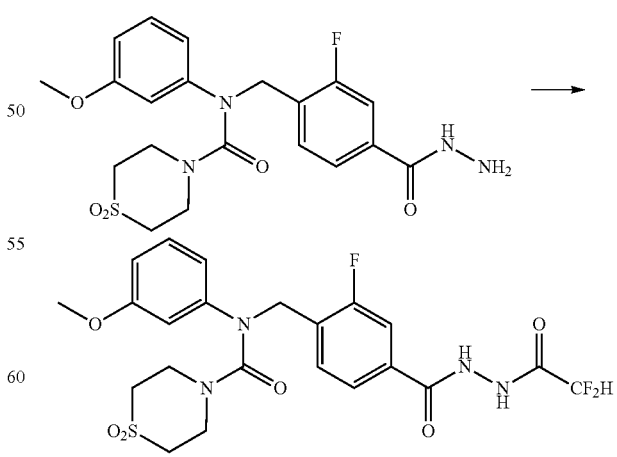

A solution of N-(2-fluoro-4-(hydrazinecarbonyl)benzyl)-N-(3-methoxyphenyl)thiomorpholine-4-carboxamide 1,1-dioxide (0.448 g, 0.994 mmol) prepared in Step 2 of Example 150 and triethylamine (0.207 mL, 1.492 mmol) in dichloromethane (10 mL) was mixed at 0° C. with difluoroacetic anhydride (0.097 mL, 0.895 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(4-(2-(2,2-difluoroacetyl)hydrazine-1-carbonyl)-2-fluorobenzyl)-N-(3-methoxyphenyl) thiomorpholine-4-carboxamide 1,1-dioxide as white solid (0.525 g, 99.9%).

[Step 2] Compound 21482

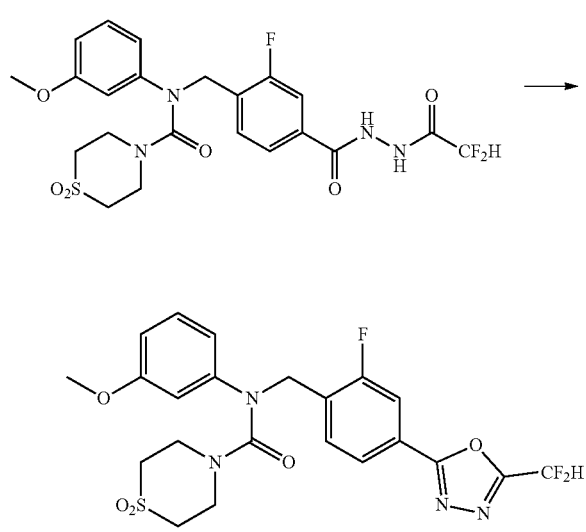 [SMILES: COc1cccc(N(Cc2ccc(C(=O)NNC(=O)C(F)F)cc2F)C(=O)N2CCS(=O)(=O)CC2)c1 ; COc1cccc(N(Cc2ccc(-c3nnc(C(F)F)o3)cc2F)C(=O)N2CCS(=O)(=O)CC2)c1]

A mixture of N-(4-(2-(2,2-difluoroacetyl)hydrazine-1-carbonyl)-2-fluorobenzyl)-N-(3-methoxyphenyl) thiomorpholine-4-carboxamide 1,1-dioxide (0.544 g, 1.029 mmol) prepared in Step 1 and 1-methoxy-N-triethylammoniosulfonyl-methanimidate (Burgess reagent, 0.368 g, 1.544 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give the title compound N-(4-(5-(difluoromethyl)-1,3,4-oxadiazol-2-yl)-2-fluorobenzyl)-N-(3-methoxyphenyl)thiomorpholine-4-carboxamide 1,1-dioxide as white solid (0.368 g, 70.0%).

$^1$H NMR (400 MHz, CDCl$_3$) δ 7.86 (dd, 1H, J=8.0, 1.7 Hz), 7.75 (dd, 1H, J=10.1, 1.6 Hz), 7.64 (t, 1H, J=7.6 Hz), 7.30-7.23 (m, 1H), 7.30-6.77 (m, 1H), 6.75-6.73 (m, 1H), 6.70-6.66 (m, 2H), 4.92 (s, 2H), 3.77 (s, 3H), 3.74-3.72 (m, 4H), 2.84-2.77 (m, 4H); LRMS (ES) m/z 511.1 (M$^+$+1).

Example 152. Compound 21483: N-(2-fluoro-4-(5-(trifluoromethyl)-1,3,4-oxadiazol-2-yl)benzyl)-N-(m-tolyl)thiomorpholine-4-carboxamide 1,1-dioxide

[Step 1] Methyl 4-((1,1-dioxido-N-(m-tolyl)thiomorpholine-4-carboxamido)methyl)-3-fluorobenzoate

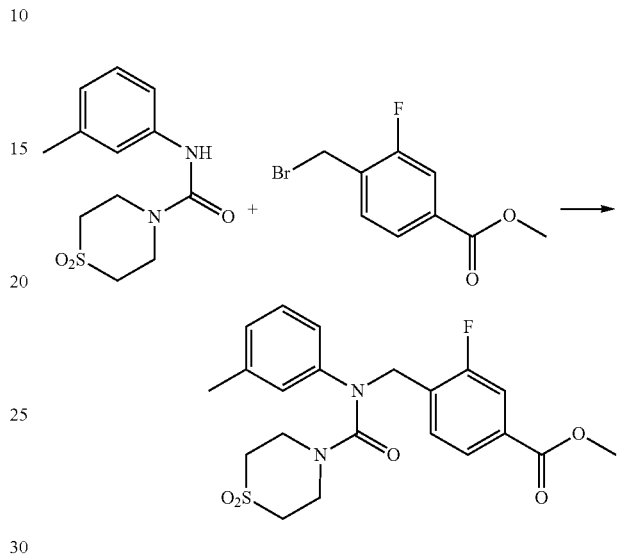

To a stirred solution of N-(m-tolyl)thiomorpholine-4-carboxamide 1,1-dioxide (1.000 g, 3.727 mmol) in N,N-dimethylformamide (10 mL) was added at 0° C. sodium hydride (60.00%, 0.179 g, 4.472 mmol). The reaction mixture was stirred at the same temperature, treated at the room temperature with methyl 4-(bromomethyl)-3-fluorobenzoate (1.013 g, 4.099 mmol), and stirred for additional 1 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The concentrate was purified and concentrated by column chromatography (SiO$_2$, 40 g cartridge; methanol/dichloromethane=0% to 5%) to give the title compound methyl 4-((1,1-dioxido-N-(m-tolyl)thiomorpholine-4-carboxamido)methyl)-3-fluorobenzoate as white solid (0.690 g, 42.6%).

[Step 2] N-(2-fluoro-4-(hydrazinecarbonyl)benzyl)-N-(m-tolyl)thiomorpholine-4-carboxamide 1,1-dioxide

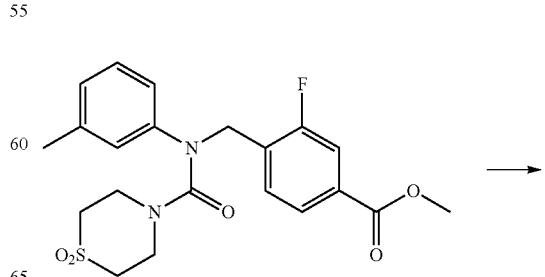

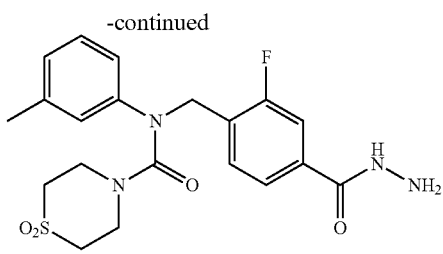

A mixture of methyl 4-((1,1-dioxido-N-(m-tolyl)thiomorpholine-4-carboxamido)methyl)-3-fluorobenzoate (0.690 g, 1.588 mmol) prepared in Step 1 and hydrazine monohydrate (1.500 mL, 31.762 mmol) in ethanol (10 mL) was heated at reflux for 16 hr, and cooled down to the ambient temperature. The reaction mixture was concentrated under the reduced pressure to remove the solvent, and water was added to the concentrate, followed by extraction with ethyl acetate. The organic layer was washed with aqueous saturated sodium chloride solution, dried (anhydrous MgSO₄), filtered, and concentrated in vacuo. The concentrate was purified and concentrated by column chromatography (SiO₂, 24 g cartridge; methanol/dichloromethane=0% to 5%) to give the title compound N-(2-fluoro-4-(hydrazinecarbonyl)benzyl)-N-(m-tolyl)thiomorpholine-4-carboxamide 1,1-dioxide as white solid (0.519 g, 75.2%).

[Step 3] N-(2-fluoro-4-(2-(2,2,2-trifluoroacetyl)hydrazine-1-carbonyl)benzyl)-N-(m-tolyl)thiomorpholine-4-carboxamide 1,1-dioxide

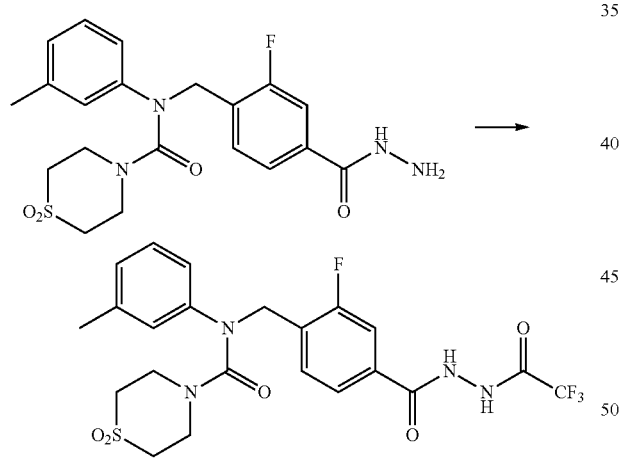

A solution of N-(2-fluoro-4-(hydrazinecarbonyl)benzyl)-N-(m-tolyl)thiomorpholine-4-carboxamide 1,1-dioxide (0.259 g, 0.596 mmol) prepared in Step 2 and triethylamine (0.124 mL, 0.894 mmol) in dichloromethane (5 mL) was mixed at 0° C. with trifluoroacetic anhydride (0.075 mL, 0.536 mmol), and stirred at the room temperature for 3 hr. Then, aqueous 1N-sodium bicarbonate solution was added to the reaction mixture, followed by extraction with ethyl acetate. The bi-phasic mixture was passed through a plastic frit to remove solid residues and aqueous layer, and the organic layer collected was concentrated in vacuo. The concentrate was purified and concentrated by column chromatography (SiO₂, 24 g cartridge; methanol/dichloromethane=0% to 5%) to give the title compound N-(2-fluoro-4-(2-(2,2,2-trifluoroacetyl)hydrazine-1-carbonyl)benzyl)-N-(m-tolyl)thiomorpholine-4-carboxamide 1,1-dioxide as white solid (0.172 g, 54.4%).

[Step 4] Compound 21483

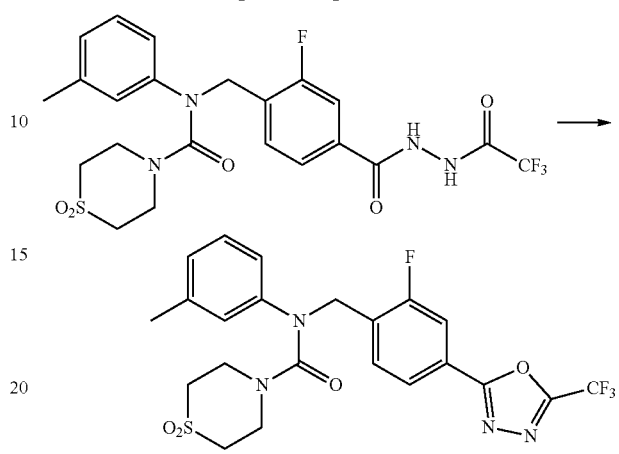

A mixture of N-(2-fluoro-4-(2-(2,2,2-trifluoroacetyl)hydrazine-1-carbonyl)benzyl)-N-(m-tolyl)thiomorpholine-4-carboxamide 1,1-dioxide (0.172 g, 0.324 mmol) prepared in Step 3 and 1-methoxy-N-triethylammoniosulfonyl-methanimidate (Burgess reagent, 0.116 g, 0.486 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 3%) to give the title compound N-(2-fluoro-4-(5-(trifluoromethyl)-1,3,4-oxadiazol-2-yl)benzyl)-N-(m-tolyl)thiomorpholine-4-carboxamide 1,1-dioxide as white solid (0.116 g, 69.8%).

$^1$H NMR (400 MHz, CDCl$_3$) δ 7.90-7.82 (m, 1H), 7.75 (dd, 1H, J=10.0, 1.6 Hz), 7.66 (t, 1H, J=7.6 Hz), 7.26-7.20 (m, 2H), 7.06-7.01 (m, 1H), 6.96-6.87 (m, 2H), 4.91 (s, 2H), 3.72-3.67 (m, 4H), 2.80-2.74 (m, 4H), 2.33 (s, 3H); LRMS (ES) m/z 513 (M$^+$+1).

Example 153. Compound 21484: N-(4-(5-(difluoromethyl)-1,3,4-oxadiazol-2-yl)-2-fluorobenzyl)-N-(m-tolyl)thiomorpholine-4-carboxamide 1,1-dioxide

[Step 1] N-(4-(2-(2,2-difluoroacetyl)hydrazine-1-carbonyl)-2-fluorobenzyl)-N-(m-tolyl)thiomorpholine-4-carboxamide 1,1-dioxide

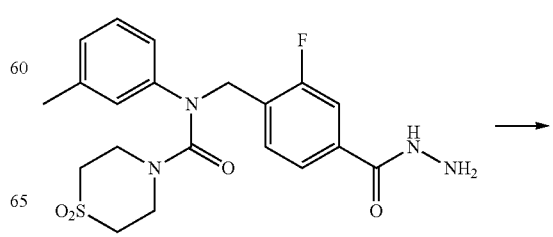

-continued

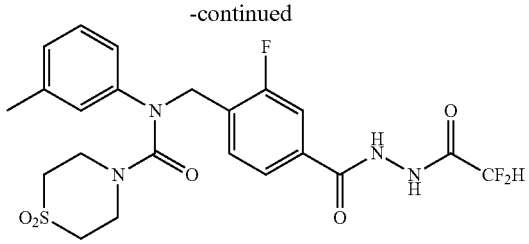

A solution of N-(2-fluoro-4-(hydrazinecarbonyl)benzyl)-N-(m-tolyl)thiomorpholine-4-carboxamide 1,1-dioxide (0.259 g, 0.596 mmol) prepared in Step 2 of Example 152 and triethylamine (0.124 mL, 0.894 mmol) in dichloromethane (5 mL) was mixed at 0° C. with difluoroacetic anhydride (0.058 mL, 0.536 mmol), and stirred at the room temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 5%) to give the title compound N-(4-(2-(2,2-difluoroacetyl)hydrazine-1-carbonyl)-2-fluorobenzyl)-N-(m-tolyl)thiomorpholine-4-carboxamide 1,1-dioxide as white solid (0.215 g, 70.4%).

[Step 2] Compound 21484

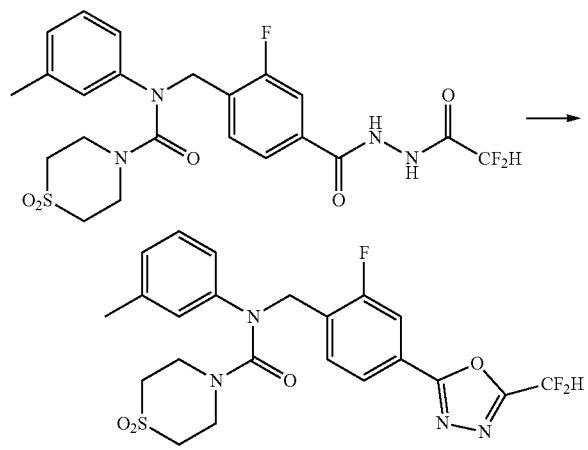

A mixture of N-(4-(2-(2,2-difluoroacetyl)hydrazine-1-carbonyl)-2-fluorobenzyl)-N-(m-tolyl)thiomorpholine-4-carboxamide 1,1-dioxide (0.215 g, 0.420 mmol) prepared in Step 1 and 1-methoxy-N-triethylammoniosulfonyl-methanimidate (Burgess reagent, 0.150 g, 0.629 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound N-(4-(5-(difluoromethyl)-1,3,4-oxadiazol-2-yl)-2-fluorobenzyl)-N-(m-tolyl)thiomorpholine-4-carboxamide 1,1-dioxide as white solid (0.150 g, 72.3%).

$^1$H NMR (400 MHz, CDCl$_3$) δ 7.86 (dd, 1H, J=8.0, 1.7 Hz), 7.75 (dd, 1H, J=10.1, 1.7 Hz), 7.65 (t, 1H, J=7.6 Hz), 7.25-7.21 (m, 1H), 7.07-6.77 (m, 4H), 4.90 (s, 2H), 3.76-3.68 (m, 4H), 2.81-2.73 (m, 4H), 2.33 (s, 3H); LRMS (ES) m/z 495.1 (M$^+$+1).

Example 154. Compound 21485: N-([1,1'-biphenyl]-4-yl)-N-(4-(5-(trifluoromethyl)-1,3,4-oxadiazol-2-yl)benzyl)thiomorpholine-4-carboxamide 1,1-dioxide

[Step 1] Methyl 4-((N-(4-bromophenyl)-1,1-dioxidothiomorpholine-4-carboxamido)methyl)benzoate

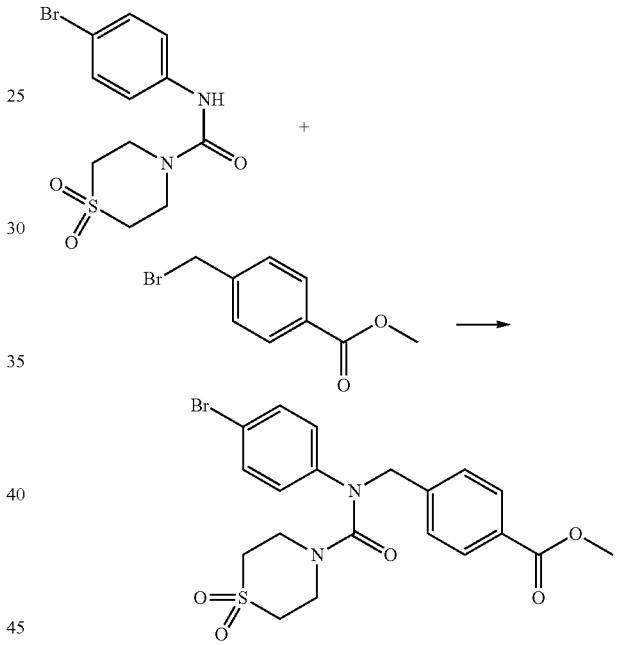

To a stirred solution of N-(4-bromophenyl)thiomorpholine-4-carboxamide 1,1-dioxide (2.098 g, 6.297 mmol) in N,N-dimethylformamide (2 mL) was added at 0° C. sodium hydride (60.00%, 0.252 g, 6.297 mmol). The reaction mixture was stirred at the same temperature for 30 min, treated at the room temperature with methyl 4-(bromomethyl)benzoate (1.442 g, 6.297 mmol), and stirred for additional 2 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The crude product was crystallized at the room temperature using ethyl acetate (1 mL) and hexane (10 mL). The resulting precipitates were filtered, washed by hexane, and dried to give the title compound methyl 4-((N-(4-bromophenyl)-1,1-dioxidothiomorpholine-4-carboxamido)methyl)benzoate as white solid (2.847 g, 93.9%).

583

[Step 2] Methyl 4-((N-([1,1'-biphenyl]-4-yl)-1,1-dioxidothiomorpholine-4-carboxamido)methyl)benzoate

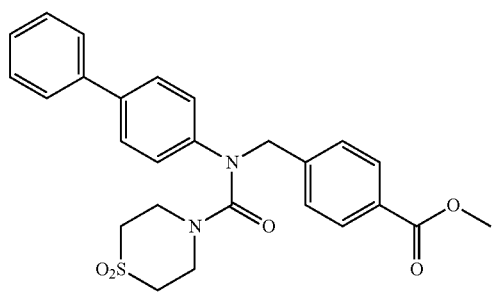

Methyl 4-((N-(4-bromophenyl)-1,1-dioxidothiomorpholine-4-carboxamido)methyl)benzoate (0.300 g, 0.623 mmol) prepared in Step 1, phenylboronic acid (0.091 g, 0.748 mmol), [1,1'-bis(di-tert-butylphosphino)ferrocene]palladium(II) dichloride (Pd(dtbpf)Cl2, 0.020 g, 0.031 mmol) and cesium carbonate (0.605 g, 1.870 mmol) in water (1 mL)/1,4-dioxane (3 mL) was mixed at the room temperature and then heated at 120° C. under the microwaves for 20 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO2, 4 g cartridge; methanol/dichloromethane=0% to 5%) to give the title compound methyl 4-((N-([1,1'-biphenyl]-4-yl)-1,1-dioxidothiomorpholine-4-carboxamido)methyl)benzoate as brown foam (0.283 g, 94.9%).

584

[Step 3] N-([1,1'-biphenyl]-4-yl)-N-(4-(hydrazinecarbonyl)benzyl)thiomorpholine-4-carboxamide 1,1-dioxide

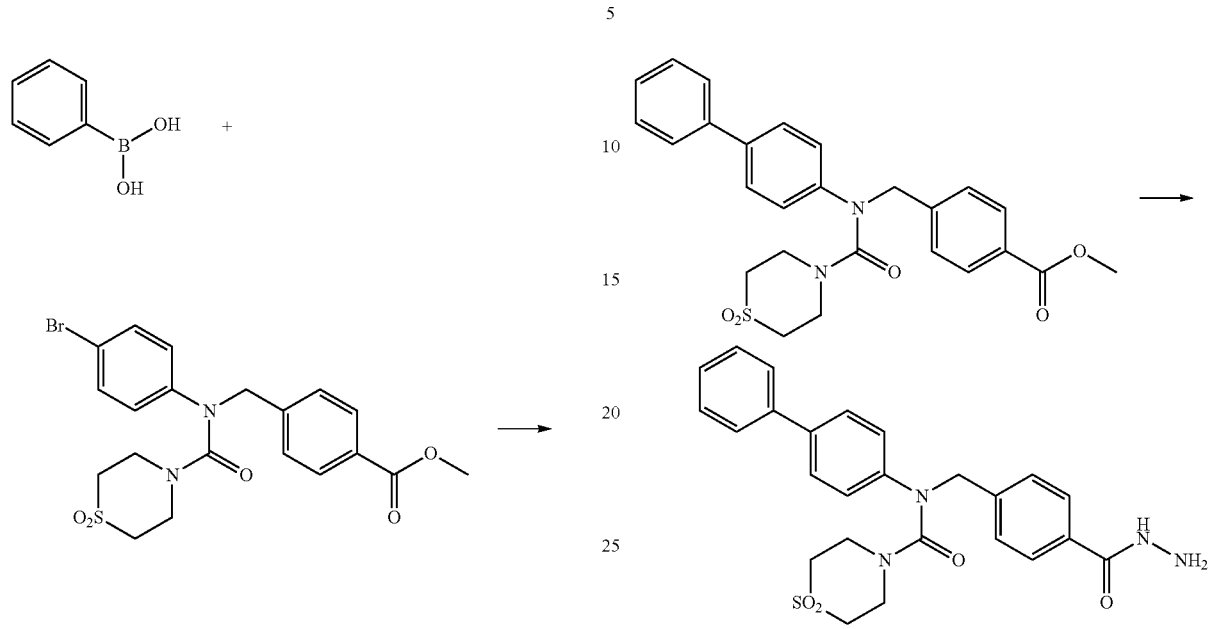

Methyl 4-((N-([1,1'-biphenyl]-4-yl)-1,1-dioxidothiomorpholine-4-carboxamido)methyl)benzoate (0.283 g, 0.591 mmol) prepared in Step 2 and hydrazine monohydrate (0.559 mL, 11.827 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO2, 4 g cartridge; methanol/dichloromethane=0% to 5%) to give the title compound, N-([1,1'-biphenyl]-4-yl)-N-(4-(hydrazinecarbonyl)benzyl)thiomorpholine-4-carboxamide 1,1-dioxide as yellow foam (0.238 g, 84.1%).

[Step 4] (N-([1,1'-biphenyl]-4-yl)-N-(4-(2-(2,2,2-trifluoroacetyl)hydrazine-1-carbonyl)benzyl)thiomorpholine-4-carboxamide 1,1-dioxide

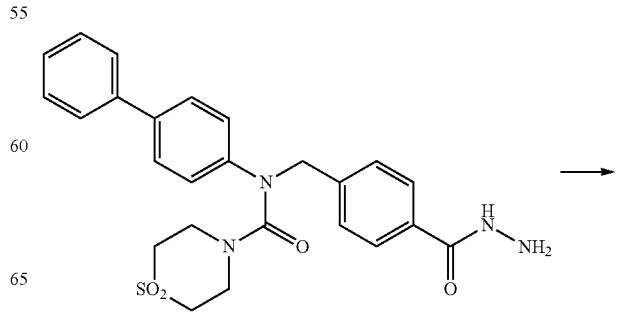

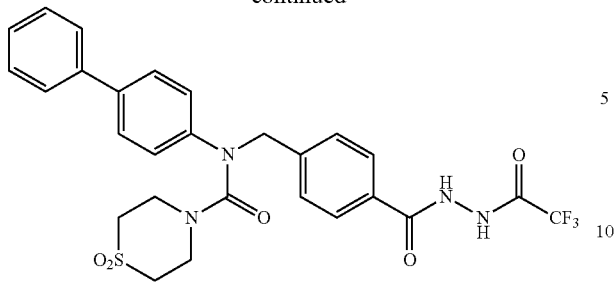

A solution of N-([1,1'-biphenyl]-4-yl)-N-(4-(hydrazinecarbonyl)benzyl)thiomorpholine-4-carboxamide 1,1-dioxide (0.119 g, 0.250 mmol) prepared in Step 3 and triethylamine (0.069 mL, 0.500 mmol) in dichloromethane (1 mL) was mixed at the room temperature with trifluoroacetic anhydride (0.039 mL, 0.225 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-([1,1'-biphenyl]-4-yl)-N-(4-(2-(2,2,2-trifluoroacetyl)hydrazine-1-carbonyl)benzyl)thiomorpholine-4-carboxamide 1,1-dioxide, 0.120 g, 83.5%, brown oil).

[Step 5] Compound 21485

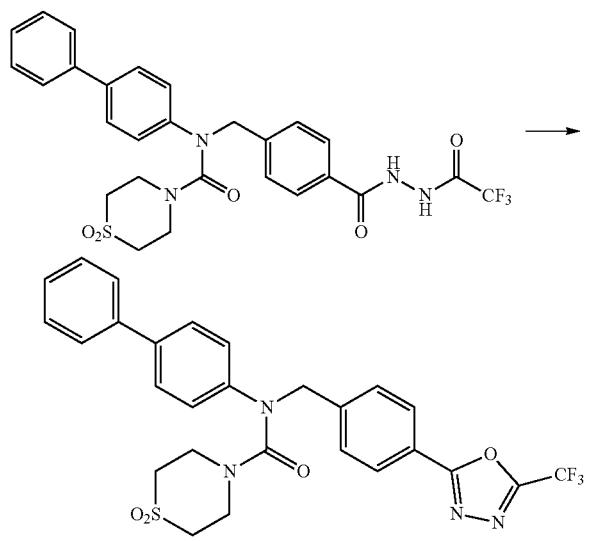

N-([1,1'-biphenyl]-4-yl)-N-(4-(2-(2,2,2-trifluoroacetyl)hydrazine-1-carbonyl)benzyl)thiomorpholine-4-carboxamide 1,1-dioxide (0.120 g, 0.209 mmol) prepared in Step 4 and 1-methoxy-N-triethylammoniosulfonyl-methanimidate (Burgess reagent, 0.075 g, 0.313 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-([1,1'-biphenyl]-4-yl)-N-(4-(5-(trifluoromethyl)-1,3,4-oxadiazol-2-yl)benzyl)thiomorpholine-4-carboxamide 1,1-dioxide as yellow solid (0.096 g, 82.3%).

$^1$H NMR (400 MHz, CDCl$_3$) δ 8.03 (d, 2H, J=8.3 Hz), 7.65-7.28 (m, 9H), 7.14 (dd, 2H, J=8.9, 2.4 Hz), 3.75 (m, 4H), 2.85 (m, 4H); LRMS (ESI) m/z 557.27 (M$^+$+H).

Example 155. Compound 21486: N-([1,1'-biphenyl]-4-yl)-N-(4-(5-(difluoromethyl)-1,3,4-oxadiazol-2-yl)benzyl)thiomorpholine-4-carboxamide 1,1-dioxide

[Step 1] (N-([1,1'-biphenyl]-4-yl)-N-(4-(2-(2,2-difluoroacetyl)hydrazine-1-carbonyl)benzyl)thiomorpholine-4-carboxamide 1,1-dioxide

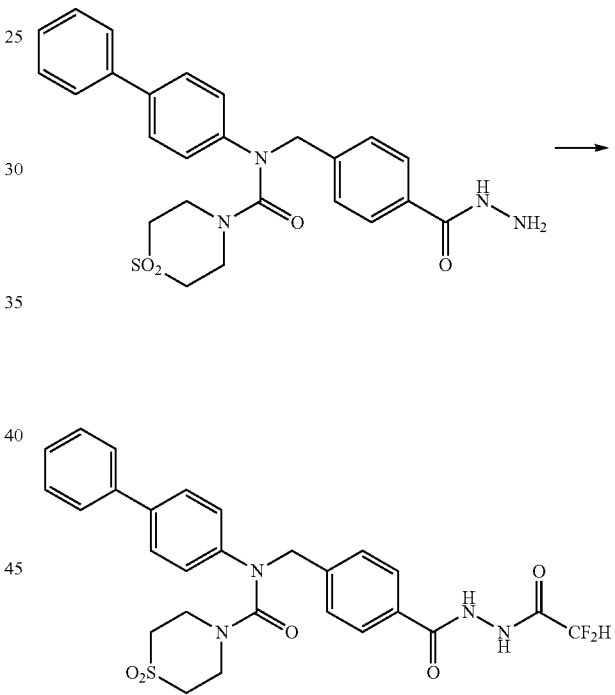

A solution of N-([1,1'-biphenyl]-4-yl)-N-(4-(hydrazinecarbonyl)benzyl)thiomorpholine-4-carboxamide 1,1-dioxide (0.119 g, 0.250 mmol) prepared in Step 3 of Example 154 and triethylamine (0.069 mL, 0.500 mmol) in dichloromethane (1 mL) was mixed at the room temperature with Difluoroacetic Anhydride (0.028 mL, 0.225 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-([1,1'-biphenyl]-4-yl)-N-(4-(2-(2,2-difluoroacetyl)hydrazine-1-carbonyl)benzyl)thiomorpholine-4-carboxamide 1,1-dioxide, 0.120 g, 86.2%, brown oil).

[Step 2] Compound 21486

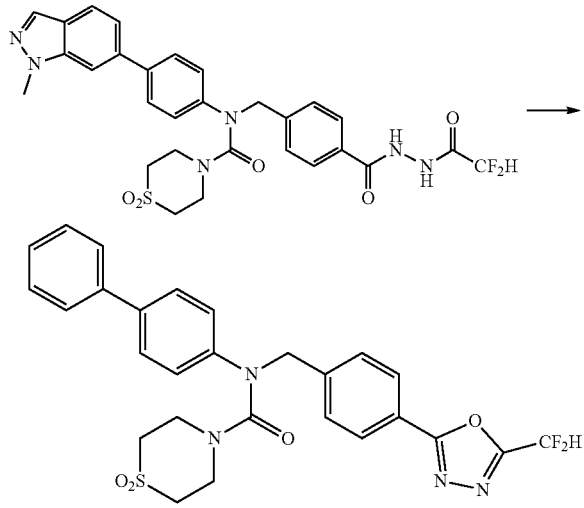

N-([1,1'-biphenyl]-4-yl)-N-(4-(2-(2,2-difluoroacetyl)hydrazine-1-carbonyl)benzyl)thiomorpholine-4-carboxamide 1,1-dioxide (0.120 g, 0.216 mmol) prepared in Step 1 and 1-methoxy-N-triethylammoniosulfonyl-methanimidate (Burgess reagent, 0.077 g, 0.323 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-([1,1'-biphenyl]-4-yl)-N-(4-(5-(difluoromethyl)-1,3,4-oxadiazol-2-yl)benzyl)thiomorpholine-4-carboxamide 1,1-dioxide as yellow solid (0.091 g, 78.4%).

$^1$H NMR (400 MHz, CDCl$_3$) δ 8.09-7.98 (m, 2H), 7.64-7.33 (m, 7H), 7.15 (t, 6H, J=12.0 Hz), 4.96 (s, 2H), 3.79 (m, 4H), 2.87 (m, 4H); LRMS (ESI) m/z 539.23 (M$^+$+H).

Example 156. Compound 21487: N-(4-(1-methyl-1H-indazol-6-yl)phenyl)-N-(4-(5-(trifluoromethyl)-1,3,4-oxadiazol-2-yl) benzyl)thiomorpholine-4-carboxamide 1,1-dioxide

[Step 1] Methyl 4-((N-(4-(1-methyl-1H-indazol-6-yl)phenyl)-1,1-dioxidothiomorpholine-4-carboxamido)methyl)benzoate

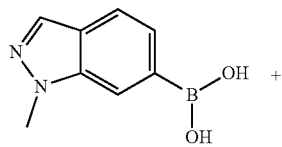

-continued

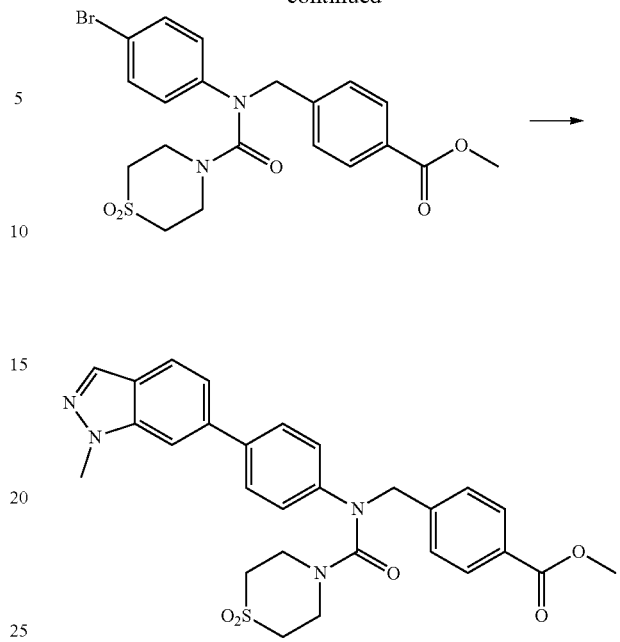

Methyl 4-((N-(4-bromophenyl)-1,1-dioxidothiomorpholine-4-carboxamido)methyl)benzoate (0.300 g, 0.623 mmol), (1-methyl-1H-indazol-6-yl)boronic acid (0.132 g, 0.748 mmol), [1,1'-bis(di-tert-butylphosphino)ferrocene] palladium(II) dichloride (Pd(dtbpf)Cl2, 0.020 g, 0.031 mmol) and cesium carbonate (0.605 g, 1.870 mmol) in water (1 mL)/1,4-dioxane (3 mL) was mixed at the room temperature and then heated at 120° C. under the microwaves for 20 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound methyl 4-((N-(4-(1-methyl-1H-indazol-6-yl)phenyl)-1,1-dioxidothiomorpholine-4-carboxamido)methyl)benzoate as brown foam (0.139 g, 41.9%).

[Step 2] N-(4-(hydrazinecarbonyl)benzyl)-N-(4-(1-methyl-1H-indazol-6-yl)phenyl)thiomorpholine-4-carboxamide 1,1-dioxide

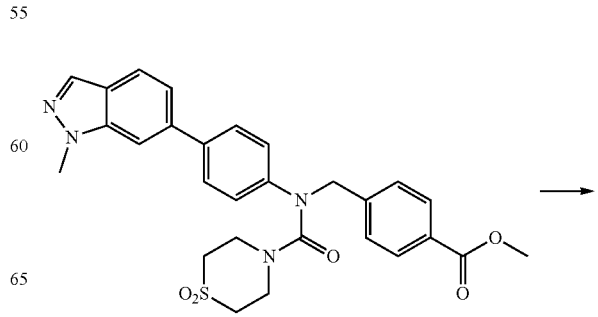

-continued

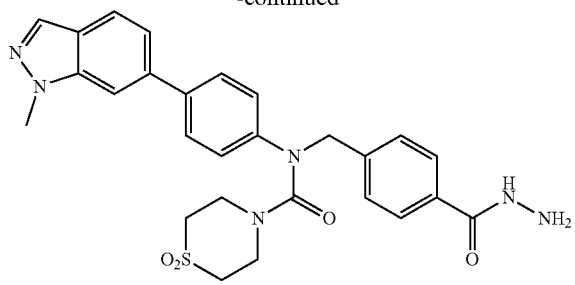

Methyl 4-((N-(4-(1-methyl-1H-indazol-6-yl)phenyl)-1,1-dioxidothiomorpholine-4-carboxamido)methyl)benzoate (0.139 g, 0.261 mmol) prepared in Step 1 and hydrazine monohydrate (0.246 mL, 5.219 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(hydrazinecarbonyl)benzyl)-N-(4-(1-methyl-1H-indazol-6-yl)phenyl)thiomorpholine-4-carboxamide 1,1-dioxide as white foam (0.117 g, 84.2%).

[Step 3] (N-(4-(1-methyl-1H-indazol-6-yl)phenyl)-N-(4-(2-(2,2,2-trifluoroacetyl)hydrazine-1-carbonyl)benzyl)thiomorpholine-4-carboxamide 1,1-dioxide

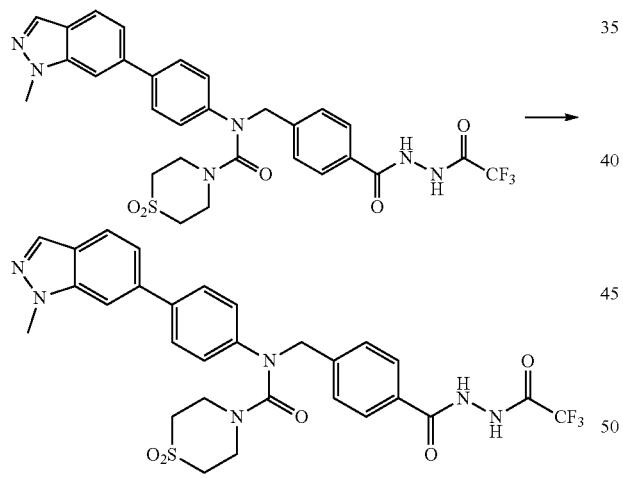

A solution of N-(4-(hydrazinecarbonyl)benzyl)-N-(4-(1-methyl-1H-indazol-6-yl)phenyl)thiomorpholine-4-carboxamide 1,1-dioxide (0.059 g, 0.110 mmol) prepared in Step 2 and triethylamine (0.030 mL, 0.220 mmol) in dichloromethane (1 mL) was mixed at the room temperature with trifluoroacetic anhydride (0.017 mL, 0.099 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(1-methyl-11-1-indazol-6-yl)phenyl)-N-(4-(2-(2,2,2-trifluoroacetyl)hydrazine-1-carbonyl)benzyl)thiomorpholine-4-carboxamide 1,1-dioxide, 0.060 g, 86.9%, brown oil).

[Step 4] Compound 21487

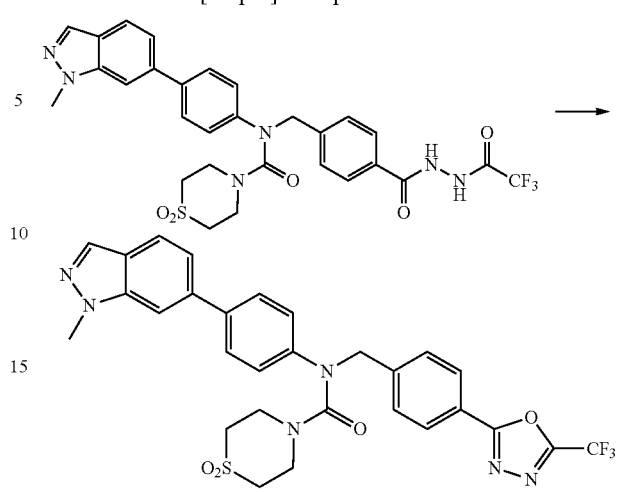

N-(4-(1-methyl-1H-indazol-6-yl)phenyl)-N-(4-(2-(2,2,2-trifluoroacetyl)hydrazine-1-carbonyl)benzyl)thiomorpholine-4-carboxamide 1,1-dioxide (0.060 g, 0.095 mmol) prepared in Step 3 and 1-methoxy-N-triethylammoniosulfonylmethanimidate (Burgess reagent, 0.034 g, 0.143 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(1-methyl-1H-indazol-6-yl)phenyl)-N-(4-(5-(trifluoromethyl)-1,3,4-oxadiazol-2-yl) benzyl)thiomorpholine-4-carboxamide 1,1-dioxide as white solid (0.031 g, 53.9%).

$^1$H NMR (400 MHz, CDCl$_3$) δ 8.10-8.00 (m, 3H), 7.81 (d, 1H, J=8.4 Hz), 7.72-7.65 (m, 2H), 7.52 (m, 3H), 7.36 (m, 1H), 7.20 (d, 2H, J=8.5 Hz), 4.99 (s, 2H), 4.15 (s, 3H), 3.80 (s, 4H), 2.90 (s, 4H); LRMS (ESI) m/z 611.2 (M$^+$+H).

Example 157. Compound 21488: N-(4-(5-(difluoromethyl)-1,3,4-oxadiazol-2-yl)benzyl)-N-(4-(1-methyl-1H-indazol-6-yl)phenyl)thiomorpholine-4-carboxamide 1,1-dioxide

[Step 1] N-(4-(2-(2,2-difluoroacetyl)hydrazine-1-carbonyl)benzyl)-N-(4-(1-methyl-1H-indazol-6-yl)phenyl)thiomorpholine-4-carboxamide 1,1-dioxide

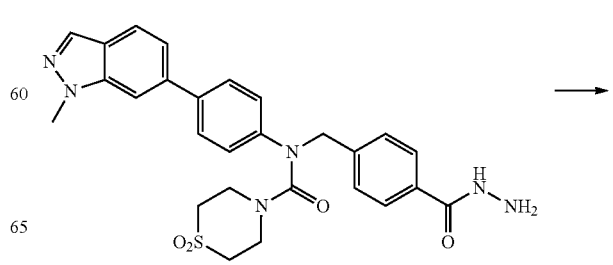

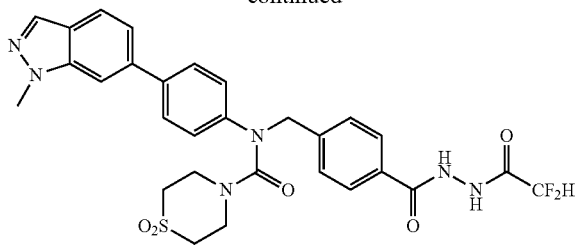

A solution of N-(4-(hydrazinecarbonyl)benzyl)-N-(4-(1-methyl-1H-indazol-6-yl)phenyl)thiomorpholine-4-carboxamide 1,1-dioxide (0.059 g, 0.110 mmol) prepared in Step 2 of Example 156 and triethylamine (0.030 mL, 0.220 mmol) in dichloromethane (1 mL) was mixed at the room temperature with Difluoroacetic Anhydride (0.012 mL, 0.099 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2-difluoroacetyl)hydrazine-1-carbonyl)benzyl)-N-(4-(1-methyl-1H-indazol-6-yl)phenyl)thiomorpholine-4-carboxamide 1,1-dioxide, 0.060 g, 89.5%, brown oil).

[Step 2] Compound 21488

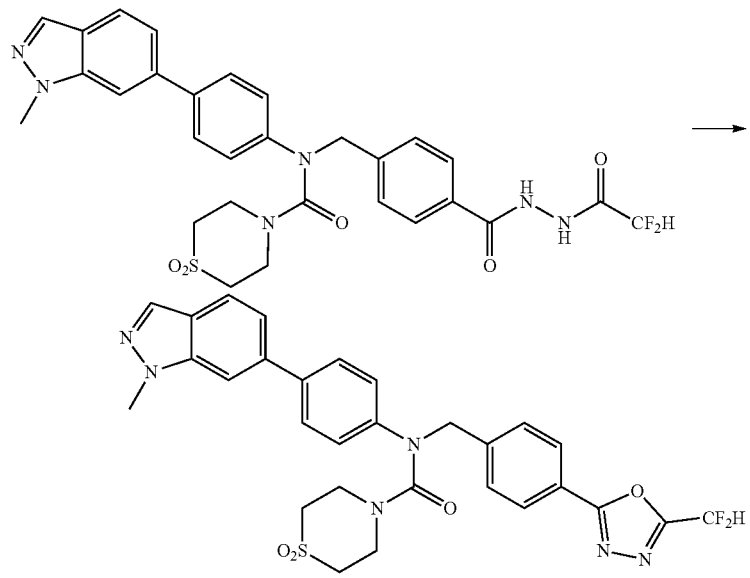

N-(4-(1-methyl-1H-indazol-6-yl)phenyl)-N-(4-(2-(2,2,2-trifluoroacetyl)hydrazine-1-carbonyl)benzyl)thiomorpholine-4-carboxamide 1,1-dioxide (0.060 g, 0.095 mmol) prepared in Step 1 and 1-methoxy-N-triethylammoniosulfonylmethanimidate (Burgess reagent, 0.034 g, 0.143 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(5-(difluoromethyl)-1,3,4-oxadiazol-2-yl)benzyl)-N-(4-(1-methyl-1H-indazol-6-yl)phenyl)thiomorpholine-4-carboxamide 1,1-dioxide as yellow solid (0.021 g, 36.6%).
$^1$H NMR (400 MHz, CDCl$_3$) δ 8.10-8.00 (m, 3H), 7.81 (d, 1H, J=8.3 Hz), 7.71-7.32 (m, 6H), 7.28 (d, 2H, J=0.8 Hz), 6.92 (t, 1H, J=51.7 Hz), 4.97 (d, 2H, J=8.2 Hz), 4.15 (s, 3H), 3.79 (s, 4H), 2.91 (d, 4H, J=7.4 Hz); LRMS (ESI) m/z 593.36 (M$^+$+H).

Example 158. Compound 21489: N-(4-(pyridin-3-yl)phenyl)-N-(4-(5-(trifluoromethyl)-1,3,4-oxadiazol-2-yl)benzyl)thiomorpholine-4-carboxamide 1,1-dioxide

[Step 1] Methyl 4-((1,1-dioxido-N-(4-(pyridin-3-yl)phenyl)thiomorpholine-4-carboxamido)methyl)benzoate

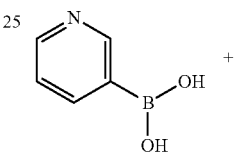

+

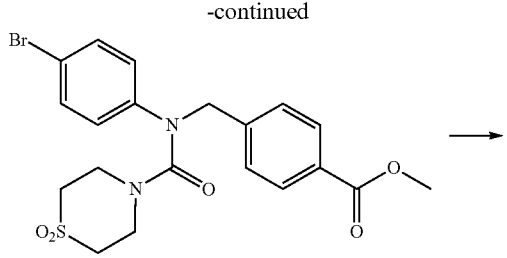

-continued

-continued

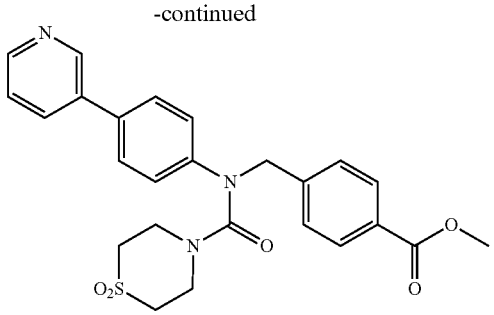

Methyl 4-((N-(4-bromophenyl)-1,1-dioxidothiomorpholine-4-carboxamido)methyl)benzoate (0.300 g, 0.623 mmol), pyridin-3-ylboronic acid (0.092 g, 0.748 mmol), [1,1'-bis(di-tert-butylphosphino)ferrocene]palladium(II) dichloride (Pd(dtbpf)Cl2, 0.020 g, 0.031 mmol) and cesium carbonate (0.605 g, 1.870 mmol) in water (1 mL)/1,4-dioxane (3 mL) was mixed at the room temperature and then heated at 120° C. under the microwaves for 20 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound methyl 4-((1,1-dioxido-N-(4-(pyridin-3-yl)phenyl)thiomorpholine-4-carboxamido)methyl)benzoate as brown foam (0.311 g, 104.1%).

[Step 2] N-(4-(hydrazinecarbonyl)benzyl)-N-(4-(pyridin-3-yl)phenyl)thiomorpholine-4-carboxamide 1,1-dioxide

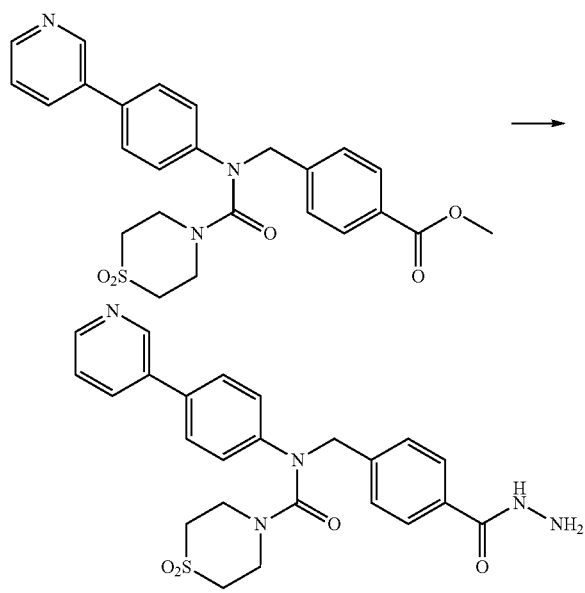

Methyl 4-((1,1-dioxido-N-(4-(pyridin-3-yl)phenyl)thiomorpholine-4-carboxamido)methyl)benzoate (0.311 g, 0.649 mmol) prepared in Step 1 and hydrazine monohydrate (0.613 mL, 12.970 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(hydrazinecarbonyl)benzyl)-N-(4-(pyridin-3-yl)phenyl) thiomorpholine-4-carboxamide 1,1-dioxide as white foam (0.230 g, 73.8%).

[Step 3] N-(4-(pyridin-3-yl)phenyl)-N-(4-(2-(2,2,2-trifluoroacetyl)hydrazine-1-carbonyl)benzyl)thiomorpholine-4-carboxamide 1,1-dioxide


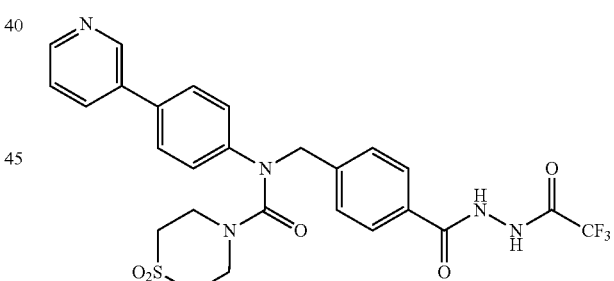

A solution of N-(4-(hydrazinecarbonyl)benzyl)-N-(4-(pyridin-3-yl)phenyl)thiomorpholine-4-carboxamide 1,1-dioxide (0.115 g, 0.239 mmol) prepared in Step 2 and triethylamine (0.066 mL, 0.479 mmol) in dichloromethane (1 mL) was mixed at the room temperature with trifluoroacetic anhydride (0.037 mL, 0.215 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(pyridin-3-yl)phenyl)-N-(4-(2-(2,2,2-trifluoroacetyl)hydrazine-1-carbonyl)benzyl)thiomorpholine-4-carboxamide 1,1-dioxide, 0.120 g, 87.1%, brown oil).

[Step 4] Compound 21489

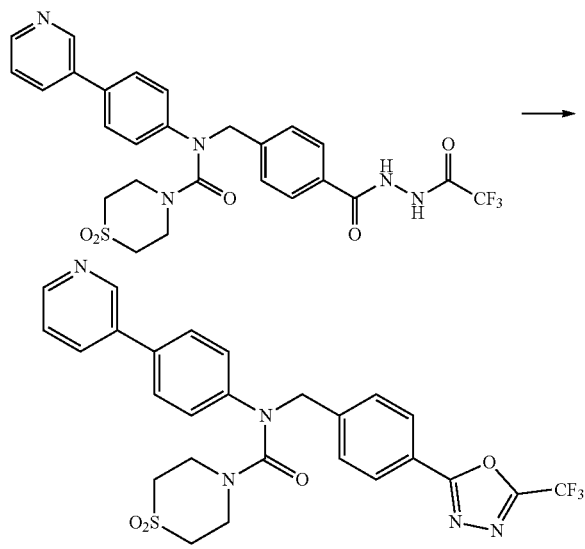

N-(4-(pyridin-3-yl)phenyl)-N-(4-(2-(2,2,2-trifluoroacetyl)hydrazine-1-carbonyl)benzyl)thiomorpholine-4-carboxamide 1,1-dioxide (0.120 g, 0.208 mmol) prepared in Step 3 and 1-methoxy-N-triethylammoniosulfonyl-methanimidate (Burgess reagent, 0.074 g, 0.312 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(pyridin-3-yl)phenyl)-N-(4-(5-(trifluoromethyl)-1,3,4-oxadiazol-2-yl)benzyl)thiomorpholine-4-carboxamide 1,1-dioxide as yellow solid (0.057 g, 49.5%).

$^1$H NMR (400 MHz, CDCl$_3$) δ 8.84 (m, 1H, J=2.4 Hz), 8.64 (dd, 1H, J=4.8, 1.6 Hz), 8.10-7.93 (m, 2H), 7.86 (dt, 1H, J=8.0, 2.0 Hz), 7.65-7.56 (m, 2H), 7.51 (d, 2H, J=8.3 Hz), 7.40 (dd, 1H, J=7.9, 4.8 Hz), 7.24-7.06 (m, 2H), 4.98 (s, 2H), 3.78 (m, 4H), 2.90 (m, 4H); LRMS (ESI) m/z 558.03 (M$^+$+H).

Example 159. Compound 21490: N-(4-(5-(difluoromethyl)-1,3,4-oxadiazol-2-yl)benzyl)-N-(4-(pyridin-3-yl)phenyl)thiomorpholine-4-carboxamide 1,1-dioxide

[Step 1] N-(4-(2-(2,2-difluoroacetyl)hydrazine-1-carbonyl)benzyl)-N-(4-(pyridin-3-yl)phenyl)thiomorpholine-4-carboxamide 1,1-dioxide

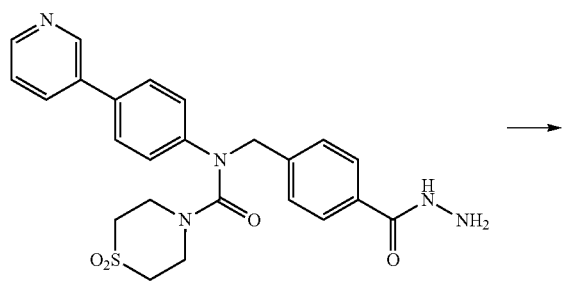

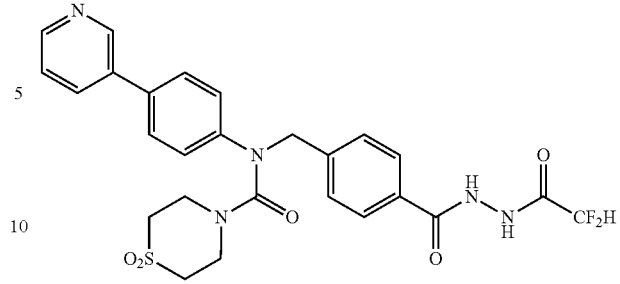

A solution of N-(4-(hydrazinecarbonyl)benzyl)-N-(4-(pyridin-3-yl)phenyl)thiomorpholine-4-carboxamide 1,1-dioxide (0.115 g, 0.239 mmol) prepared in Step 2 of Example 158 and triethylamine (0.066 mL, 0.479 mmol) in dichloromethane (1 mL) was mixed at the room temperature with Difluoroacetic Anhydride (0.027 mL, 0.215 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(2-(2,2-difluoroacetyl)hydrazine-1-carbonyl)benzyl)-N-(4-(pyridin-3-yl)phenyl)thiomorpholine-4-carboxamide 1,1-dioxide, 0.120 g, 89.9%, brown oil).

[Step 2] Compound 21490

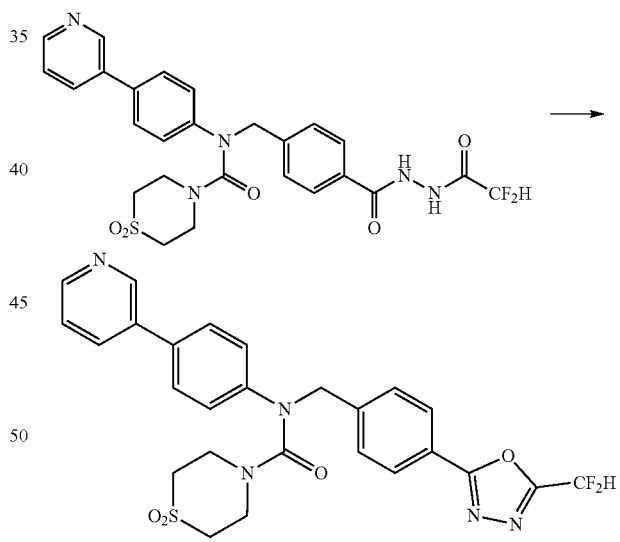

N-(4-(2-(2,2-difluoroacetyl)hydrazine-1-carbonyl)benzyl)-N-(4-(pyridin-3-yl)phenyl) thiomorpholine-4-carboxamide 1,1-dioxide (0.120 g, 0.208 mmol) prepared in Step 1 and 1-methoxy-N-triethylammoniosulfonyl-methanimidate (Burgess reagent, 0.074 g, 0.312 mmol) were mixed at the room temperature in tetrahydrofuran (2 mL) and then stirred at 80° C. for 16 hr. and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(5-(difluoromethyl)-1,3,4-oxadiazol-2-yl)benzyl)-N-(4-(pyridin-3-yl)phenyl)thiomorpholine-4-carboxamide 1,1-dioxide as yellow solid (0.052 g, 46.5%).

$^1$H NMR (400 MHz, CDCl$_3$) δ 8.84 (d, 1H, J=2.5 Hz), 8.63 (dt, 1H, J=4.8, 1.3 Hz), 8.06 (d, 2H, J=8.0 Hz), 7.90-7.70 (m, 1H), 7.60 (d, 2H, J=8.4 Hz), 7.53-7.31 (m, 3H), 7.22 (d, 2H, J=8.4 Hz), 6.92 (m, 1H), 4.98 (s, 2H), 3.77 (s, 4H), 2.91 (s, 4H); LRMS (ESI) m/z 540.0 (M$^+$+H).

Example 160. Compound 21491: N-(4-(furan-3-yl)phenyl)-N-(4-(5-(trifluoromethyl)-1,3,4-oxadiazol-2-yl)benzyl)thiomorpholine-4-carboxamide 1,1-dioxide

[Step 1] Methyl 4-((N-(4-(furan-3-yl)phenyl)-1,1-dioxidothiomorpholine-4-carboxamido)methyl)benzoate

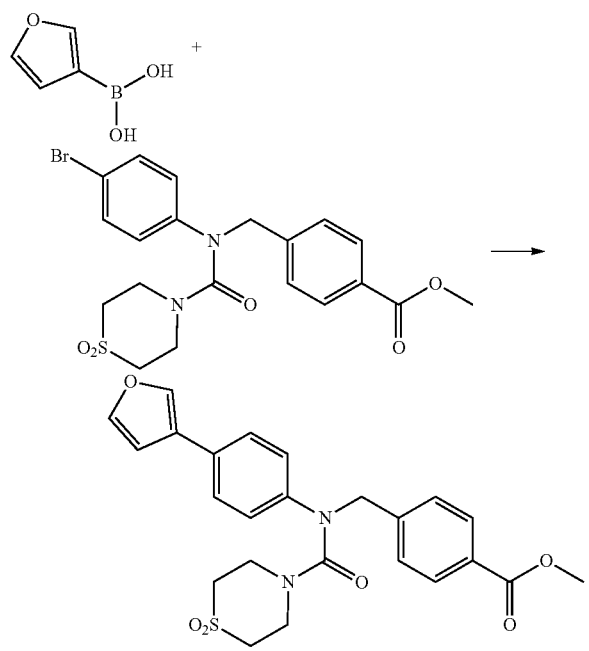

Methyl 4-((N-(4-bromophenyl)-1,1-dioxidothiomorpholine-4-carboxamido)methyl)benzoate (0.300 g, 0.623 mmol), furan-3-ylboronic acid (0.084 g, 0.748 mmol), [1,1'-bis(di-tert-butylphosphino)ferrocene]palladium(II) dichloride (Pd(dtbpf)Cl2, 0.020 g, 0.031 mmol) and cesium carbonate (0.605 g, 1.870 mmol) in water (1 mL)/1,4-dioxane (3 mL) was mixed at the room temperature and then heated at 120° C. under the microwaves for 20 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound methyl 4-((N-(4-(furan-3-yl)phenyl)-1,1-dioxidothiomorpholine-4-carboxamido)methyl)benzoate as brown foam (0.330 g, 113.0%).

[Step 2] N-(4-(furan-3-yl)phenyl)-N-(4-(hydrazinecarbonyl)benzyl)thiomorpholine-4-carboxamide 1,1-dioxide

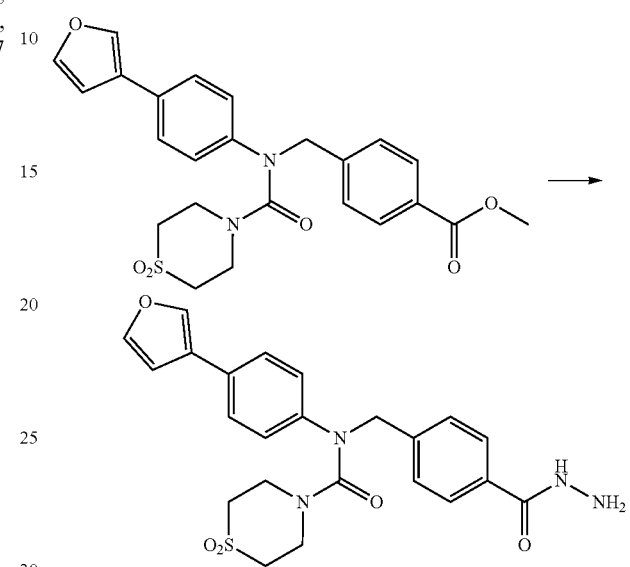

Methyl 4-((N-(4-(furan-3-yl)phenyl)-1,1-dioxidothiomorpholine-4-carboxamido)methyl)benzoate (0.330 g, 0.704 mmol) prepared in Step 1 and hydrazine monohydrate (0.665 mL, 14.087 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(furan-3-yl)phenyl)-N-(4-(hydrazinecarbonyl)benzyl)thiomorpholine-4-carboxamide 1,1-dioxide as white foam (0.249 g, 75.4%).

[Step 3] (N-(4-(furan-3-yl)phenyl)-N-(4-(2-(2,2,2-trifluoroacetyl)hydrazine-1-carbonyl)benzyl)thiomorpholine-4-carboxamide 1,1-dioxide

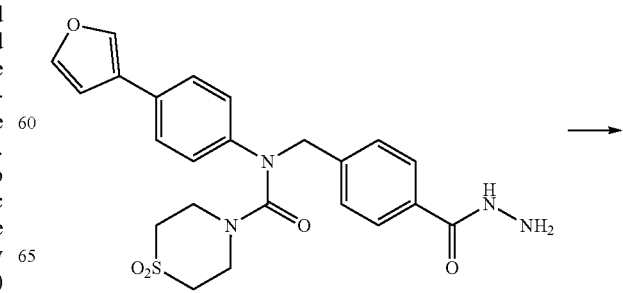

-continued

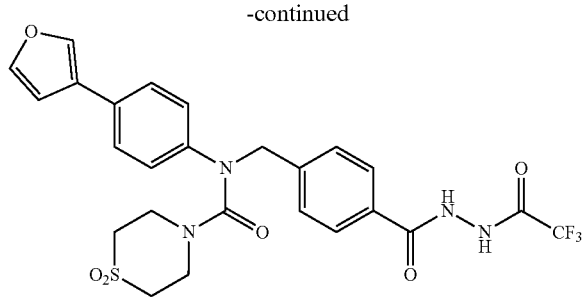

A solution of N-(4-(furan-3-yl)phenyl)-N-(4-(hydrazinecarbonyl)benzyl)thiomorpholine-4-carboxamide 1,1-dioxide (0.124 g, 0.265 mmol) prepared in Step 2 and triethylamine (0.073 mL, 0.531 mmol) in dichloromethane (1 mL) was mixed at the room temperature with trifluoroacetic anhydride (0.041 mL, 0.239 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The crude product was used without further purification (N-(4-(furan-3-yl)phenyl)-N-(4-(2-(2,2,2-trifluoroacetyl)hydrazine-1-carbonyl)benzyl)thiomorpholine-4-carboxamide 1,1-dioxide, 0.131 g, 87.5%, brown oil).

[Step 4] Compound 21491

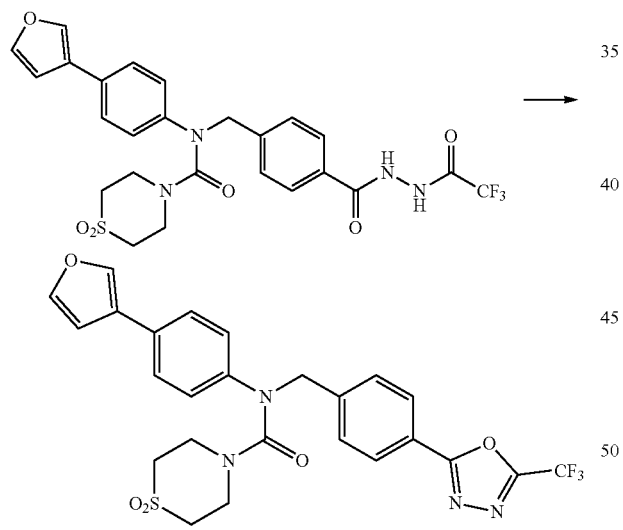

N-(4-(furan-3-yl)phenyl)-N-(4-(2-(2,2,2-trifluoroacetyl)hydrazine-1-carbonyl)benzyl)thiomorpholine-4-carboxamide 1,1-dioxide (0.131 g, 0.232 mmol) prepared in Step 3 and 1-methoxy-N-triethylammoniosulfonyl-methanimidate (Burgess reagent, 0.083 g, 0.348 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(furan-3-yl)phenyl)-N-(4-(5-(trifluoromethyl)-1,3,4-oxadiazol-2-yl)benzyl)thiomorpholine-4-carboxamide 1,1-dioxide as brown solid (0.108 g, 85.2%).

$^1$H NMR (400 MHz, CDCl$_3$) δ 8.04 (d, 2H, J=8.2 Hz), 7.74 (d, 1H, J=1.3 Hz), 7.54-7.43 (m, 5H), 7.13-7.03 (m, 2H), 6.68 (d, 1H, J=1.8 Hz), 4.93 (s, 2H), 3.84-3.68 (m, 4H), 2.86 (m, 4H); LRMS (ESI) m/z 547.1 (M$^+$+H).

Example 161. Compound 21492: N-(4-(5-(difluoromethyl)-1,3,4-oxadiazol-2-yl)benzyl)-N-(4-(furan-3-yl)phenyl)thiomorpholine-4-carboxamide 1,1-dioxide

[Step 1] N-(4-(2-(2,2-difluoroacetyl)hydrazine-1-carbonyl)benzyl)-N-(4-(furan-3-yl)phenyl)thiomorpholine-4-carboxamide 1,1-dioxide

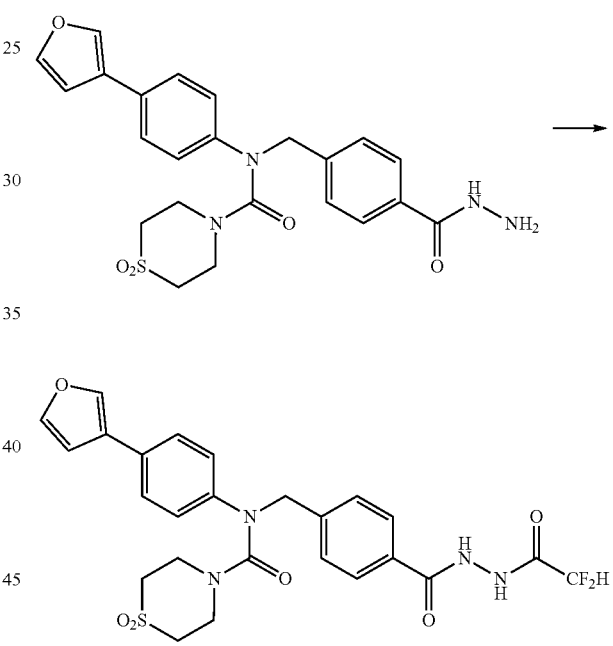

A solution of N-(4-(furan-3-yl)phenyl)-N-(4-(hydrazinecarbonyl)benzyl)thiomorpholine-4-carboxamide 1,1-dioxide (0.124 g, 0.265 mmol) prepared in Step 2 of Example 160 and triethylamine (0.073 mL, 0.531 mmol) in dichloromethane (1 mL) was mixed at the room temperature with difluoroacetic anhydride (0.030 mL, 0.239 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The crude title compound was used without further purification (0.126 g, 86.9%, brown oil).

601

[Step 2] Compound 21492

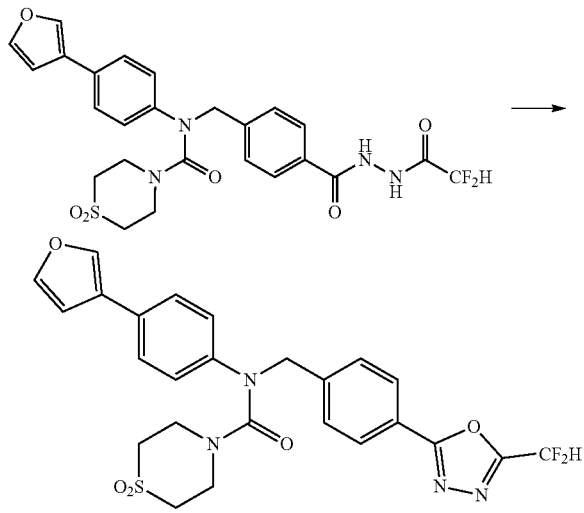

N-(4-(2-(2,2-difluoroacetyl)hydrazine-1-carbonyl)benzyl)-N-(4-(furan-3-yl)phenyl)thiomorpholine-4-carboxamide 1,1-dioxide (0.126 g, 0.223 mmol) prepared in Step 1 and 1-methoxy-N-triethylammoniosulfonyl-methanimidate (Burgess reagent, 0.080 g, 0.335 mmol) were mixed at the room temperature in tetrahydrofuran (2 mL) and then stirred at 80° C. for 16 hr, cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 3%) to give the title compound N-(4-(5-(difluoromethyl)-1,3,4-oxadiazol-2-yl)benzyl)-N-(4-(furan-3-yl)phenyl)thiomorpholine-4-carboxamide 1,1-dioxide as brown foam (0.095 g, 80.1%).

$^1$H NMR (400 MHz, CDCl₃) δ 8.04 (dd, 2H, J=9.5, 3.1 Hz), 7.74 (d, 1H, J=1.2 Hz), 7.54-7.35 (m, 5H), 7.13-6.54 (m, 4H), 4.91 (s, 2H), 3.76 (m, 4H), 2.85 (m, 4H); LRMS (ESI) m/z 529.2 (M⁺+

Example 162. Compound 21493: N-(4-(benzo[d][1,3]dioxol-5-yl)phenyl)-N-(4-(5-(trifluoromethyl)-1,3,4-oxadiazol-2-yl)benzyl)thiomorpholine-4-carboxamide 1,1-dioxide

[Step 1] Methyl 4-((N-(4-(benzo[d][1,3]dioxol-5-yl)phenyl)-1,1-dioxidothiomorpholine-4-carboxamido)methyl)benzoate

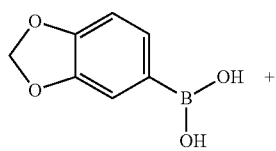

602

-continued

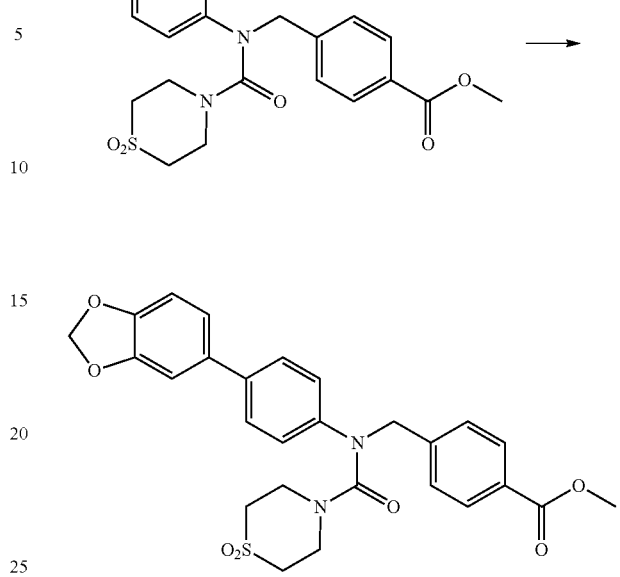

Methyl 4-((N-(4-bromophenyl)-1,1-dioxidothiomorpholine-4-carboxamido)methyl)benzoate (0.300 g, 0.623 mmol), 3,4-methylenedioxyphenylboronic acid (0.124 g, 0.748 mmol), [1,1'-bis(di-tert-butylphosphino)ferrocene] palladium(II) dichloride (Pd(dtbpf)Cl₂, 0.020 g, 0.031 mmol) and cesium carbonate (0.605 g, 1.870 mmol) in water (1 mL)/1,4-dioxane (3 mL) was mixed at the room temperature and then heated at 120° C. under the microwaves for 20 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound methyl 4-((N-(4-(benzo[d][1,3]dioxol-5-yl)phenyl)-1,1-dioxidothiomorpholine-4-carboxamido)methyl)benzoate as brown foam (0.277 g, 85.1%).

[Step 2] N-(4-(benzo[d][1,3]dioxol-5-yl)phenyl)-N-(4-(hydrazinecarbonyl)benzyl)thiomorpholine-4-carboxamide 1,1-dioxide

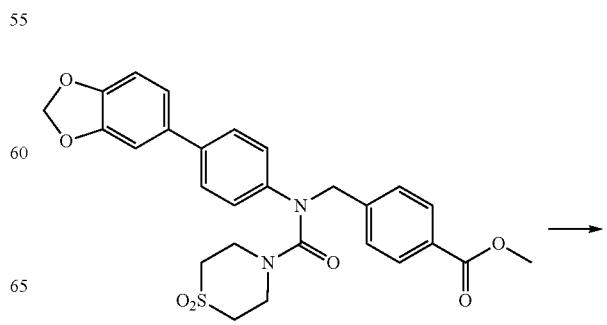

-continued

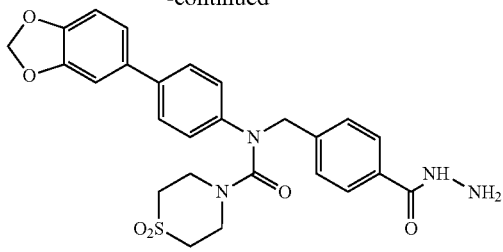

Methyl 4-((N-(4-(benzo[d] [1,3]dioxol-5-yl)phenyl)-1,1-dioxidothiomorpholine-4-carboxamido)methyl)benzoate (0.277 g, 0.531 mmol) prepared in Step 1 and hydrazine monohydrate (0.501 mL, 10.613 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(benzo[d][1,3]dioxol-5-yl)phenyl)-N-(4-(hydrazinecarbonyl)benzyl)thiomorpholine-4-carboxamide 1,1-dioxide as white foam (0.253 g, 91.1%).

[Step 3] N-(4-(benzo[d][1,3]dioxol-5-yl)phenyl)-N-(4-(2-(2,22-trifluoroacetyl)hydrazine-1-carbonyl)benzyl)thiomorpholine-4-carboxamide 1,1-dioxide

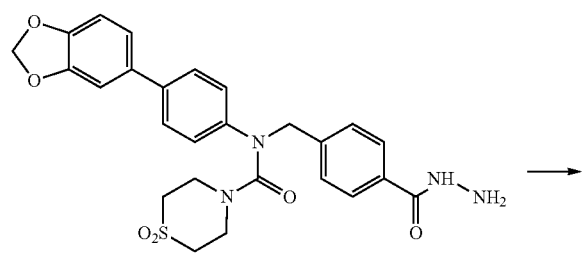

A solution of N-(4-(benzo[d][1,3]dioxol-5-yl)phenyl)-N-(4-(hydrazinecarbonyl)benzyl)thiomorpholine-4-carboxamide 1,1-dioxide (0.126 g, 0.242 mmol) prepared in Step 2 and triethylamine (0.067 mL, 0.483 mmol) in dichloromethane (1 mL) was mixed at the room temperature with trifluoroacetic anhydride (0.038 mL, 0.218 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.118 g, 78.9%, brown oil).

[Step 4] Compound 21493

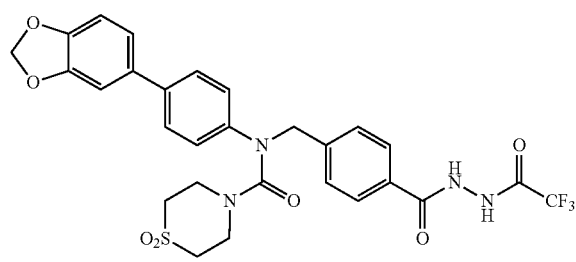

N-(4-(benzo[d][1,3]dioxol-5-yl)phenyl)-N-(4-(2-(2,2,2-trifluoroacetyl)hydrazine-1-carbonyl)benzyl)thiomorpholine-4-carboxamide 1,1-dioxide (0.118 g, 0.191 mmol) prepared in Step 3 and 1-methoxy-N-triethylammoniosulfonylmethanimidate (Burgess reagent, 0.068 g, 0.286 mmol) were mixed at the room temperature in tetrahydrofuran (2 mL) and then stirred at 80° C. for 16 hr, and cooled down to the room temperature to terminate the reaction. Then, water was added to reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(benzo[d][1,3]dioxol-5-yl)phenyl)-N-(4-(5-(trifluoromethyl)-1,3,4-oxadiazol-2-yl)benzyl)thiomorpholine-4-carboxamide 1,1-dioxide as yellow solid (0.117 g, 102.5%).

$^1$H NMR (400 MHz, CDCl$_3$) δ 8.05 (dd, 2H, J=9.4, 2.9 Hz), 7.55-7.44 (m, 4H), 7.17-7.08 (m, 2H), 7.07-6.93 (m, 2H), 6.90 (d, 1H, J=8.5 Hz), 6.03 (s, 2H), 4.95 (s, 2H), 3.77 (s, 4H), 2.87 (m, 4H); LRMS (ESI) m/z 601.2 (M$^+$+H)

Example 163. Compound 21494: N-(4-(benzo[d][1,3]dioxol-5-yl)phenyl)-N-(4-(5-(difluoromethyl)-1,3,4-oxadiazol-2-yl)benzyl)thiomorpholine-4-carboxamide 1,1-dioxide

[Step 1] N-(4-(benzo[d][1,3]dioxol-5-yl)phenyl)-N-(4-(2-(2,2-difluoroacetyl)hydrazine-1-carbonyl)benzyl)thiomorpholine-4-carboxamide 1,1-dioxide

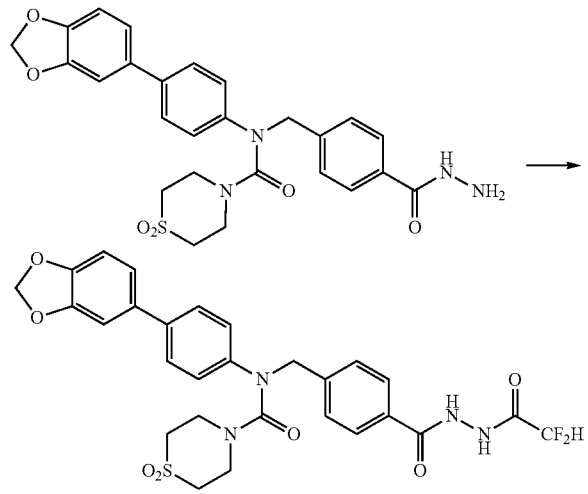

A solution of N-(4-(benzo[d][1,3]dioxol-5-yl)phenyl)-N-(4-(hydrazinecarbonyl)benzyl)thiomorpholine-4-carboxamide 1,1-dioxide (0.126 g, 0.242 mmol) prepared in Step 2 of Example 162 and triethylamine (0.067 mL, 0.483 mmol) in dichloromethane (1 mL) was mixed at the room temperature with difluoroacetic anhydride (0.027 mL, 0.218 mmol). The reaction mixture was stirred at the same temperature for 2 hr Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.121 g, 83.4%, brown oil).

[Step 2] Compound 21494

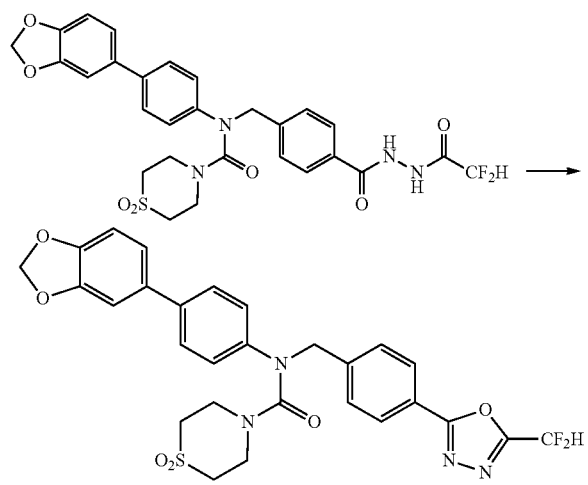

N-(4-(benzo[d][1,3]dioxol-5-yl)phenyl)-N-(4-(2-(2,2-difluoroacetyl)hydrazine-1-carbonyl)benzyl)thiomorpholine-4-carboxamide 1,1-dioxide (0.121 g, 0.196 mmol) prepared in Step 1 and 1-methoxy-N-triethylammoniosulfonyl-methanimidate (Burgess reagent, 0.070 g, 0.293 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(benzo[d][1,3]dioxol-5-yl)phenyl)-N-(4-(5-(difluoromethyl)-1,3,4-oxadiazol-2-yl)benzyl)thiomorpholine-4-carboxamide 1,1-dioxide as yellow foam (0.095 g, 83.1%).

$^1$H NMR (400 MHz, CDCl$_3$) δ 8.05 (d, 2H, J=8.1 Hz), 7.50 (dd, 4H, J=11.2, 8.1 Hz), 7.16-7.09 (m, 2H), 7.04 (ddd, 2H, J=5.3, 3.8, 1.9 Hz), 6.95-6.74 (m, 1H), 6.03 (s, 2H), 4.93 (d, 2H, J=11.5 Hz), 3.76 (s, 4H), 2.87 (s, 4H); LRMS (ESI) m/z 583.3 (M$^+$+H).

Example 164. Compound 21495: N-(4-(5-(difluoromethyl)-1,3,4-oxadiazol-2-yl)-2-fluorobenzyl)-N-phenyl-2,7-diazaspiro[3.5]nonane-7-carboxamide

[Step 1] Tert-butyl 7-((2-fluoro-4-(methoxycarbonyl)benzyl)(phenyl)carbamoyl)-2,7-diazaspiro[3.5]nonane-2-carboxylate

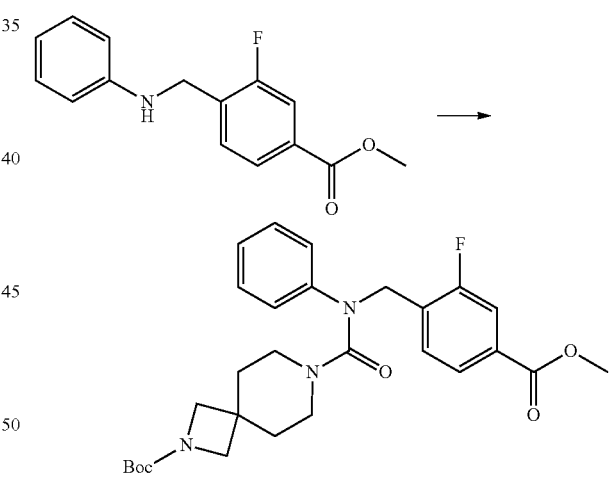

A solution of methyl 3-fluoro-4-((phenylamino)methyl)benzoate (1.000 g, 3.857 mmol), triphosgene (0.916 g, 3.085 mmol) and N,N-diisopropylethylamine (3.368 mL, 19.284 mmol) in dichloromethane (10 mL) was stirred at 0° C. for 10 min, and mixed with tert-butyl 2,7-diazaspiro[3.5]nonane-2-carboxylate (1.047 g, 4.628 mmol). The reaction mixture was stirred at the same temperature for additional 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/ hexane=10% to 60%) to give the title compound tert-butyl 7-((2-fluoro-4-(methoxycarbonyl)benzyl)(phenyl)carbamoyl)-2,7-diazaspiro[3.5]nonane-2-carboxylate as pale yellow oil (1.970 g, 99.8%).

[Step 2] Tert-butyl 7-((2-fluoro-4-(hydrazinecarbonyl)benzyl)(phenyl)carbamoyl)-2,7-diazaspiro[3.5]nonane-2-carboxylate

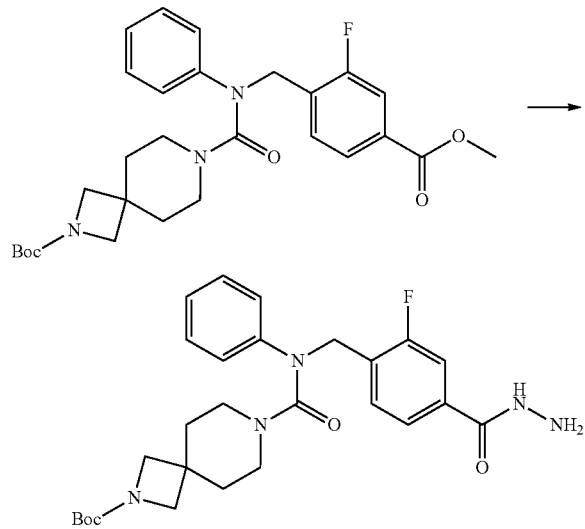

Tert-butyl 7-((2-fluoro-4-(methoxycarbonyl)benzyl)(phenyl)carbamoyl)-2,7-diazaspiro[3.5]nonane-2-carboxylate (1.980 g, 3.870 mmol) prepared in Step 1 and hydrazine monohydrate (3.762 mL, 77.406 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (1.910 g, 96.5%, white solid).

[Step 3] Tert-butyl 7-((4-(2-(2,2-difluoroacetyl)hydrazine-1-carbonyl)-2-fluorobenzyl)(phenyl)carbamoyl)-2,7-diazaspiro[3.5]nonane-2-carboxylate

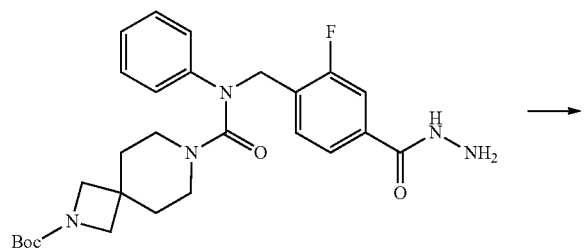

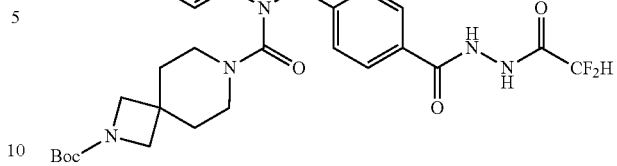

A solution of tert-butyl 7-((2-fluoro-4-(hydrazinecarbonyl)benzyl)(phenyl)carbamoyl)-2,7-diazaspiro[3.5]nonane-2-carboxylate (1.910 g, 3.733 mmol) prepared in Step 2 and triethylamine (0.776 mL, 5.600 mmol) in dichloromethane (10 mL) was mixed at the room temperature with 2,2-difluoroacetic anhydride (0.418 mL, 3.360 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (2.250 g, 102.2%, pale yellow solid).

[Step 4] Tert-butyl 7-((4-(5-(difluoromethyl)-1,3,4-oxadiazol-2-yl)-2-fluorobenzyl)(phenyl)carbamoyl)-2,7-diazaspiro[3.5]nonane-2-carboxylate

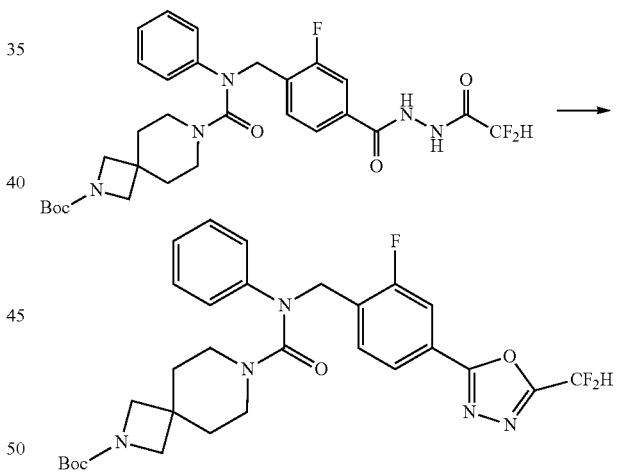

Tert-butyl 7-((4-(2-(2,2-difluoroacetyl)hydrazine-1-carbonyl)-2-fluorobenzyl)(phenyl)carbamoyl)-2,7-diazaspiro[3.5]nonane-2-carboxylate (1.910 g, 3.239 mmol) prepared in Step 3 and 1-methoxy-N-triethylammoniosulfonyl-methanimidate (Burgess reagent, 1.158 g, 4.859 mmol) in tetrahydrofuran (10 mL) was mixed at the room temperature and then heated at 150° C. under the microwaves for 30 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=10% to 60%) to give the title compound tert-butyl 7-((4-(5-(difluoromethyl)-1,3,4-oxadiazol-2-yl)-2-fluorobenzyl)(phenyl)carbamoyl)-2,7-diazaspiro[3.5]nonane-2-carboxylate as pale yellow solid (1.330 g, 71.8%).

[Step 5] Compound 21495

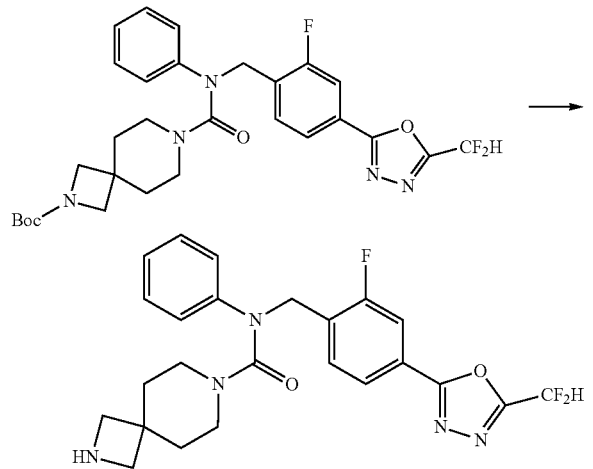

A solution of tert-butyl 7-((4-(5-(difluoromethyl)-1,3,4-oxadiazol-2-yl)-2-fluorobenzyl)(phenyl)carbamoyl)-2,7-diazaspiro[3.5]nonane-2-carboxylate (1.330 g, 2.327 mmol) prepared in Step 4 and trifluoroacetic acid (1.782 mL, 23.268 mmol) in dichloromethane (10 mL) was stirred at the room temperature for 17 hr, and saturated aqueous sodium bicarbonate solution added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 20%) to give the title compound N-(4-(5-(difluoromethyl)-1,3,4-oxadiazol-2-yl)-2-fluorobenzyl)-N-phenyl-2,7-diazaspiro[3.5]nonane-7-carboxamide as white solid (0.686 g, 62.5%).

$^1$H NMR (400 MHz, CDCl$_3$) δ 7.85 (dd, 1H, J=8.1, 1.2 Hz), 7.73 (dd, 1H, J=10.0, 1.3 Hz), 7.65 (t, 1H, J=7.6 Hz), 7.32 (t, 2H, J=7.8 Hz), 7.15 (t, 1H, J=7.4 Hz), 7.08 (d, 2H, J=7.6 Hz), 6.92 (t, 1H, J=51.7 Hz), 4.93 (s, 2H), 3.68 (s, 4H), 3.15-3.14 (m, 4H), 1.63 (t, 4H, J=5.0 Hz); LRMS (ES) m/z 472.4 (M$^+$+1).

Example 165. Compound 21496: N-(4-(5-(difluoromethyl)-1,3,4-oxadiazol-2-yl)-2-fluorobenzyl)-2-methyl-N-phenyl-2,7-diazaspiro[3.5]nonane-7-carboxamide

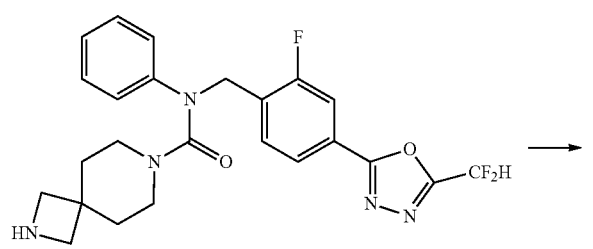

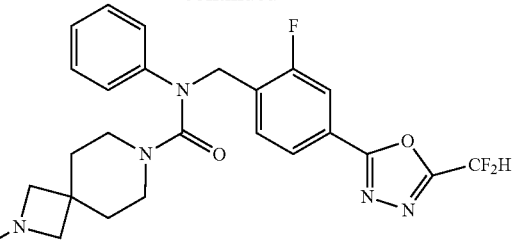

A solution of N-(4-(5-(difluoromethyl)-1,3,4-oxadiazol-2-yl)-2-fluorobenzyl)-N-phenyl-2,7-diazaspiro[3.5]nonane-7-carboxamide (0.100 g, 0.212 mmol) prepared in Example 164 and formaldehyde (37.00% solution in water, 0.024 mL, 0.318 mmol) in dichloromethane (4 mL) was mixed at the room temperature with sodium triacetoxyborohydride (0.090 g, 0.424 mmol), stirred at the same temperature for 17 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified by column chromatography (Waters, C18; acetonitrile/aqueous 0.1%-formic acid solution=5% to 75%), and the fraction containing the product was passed through an SPE cartridge (MP-HCO3 resin) to give the title compound N-(4-(5-(difluoromethyl)-1,3,4-oxadiazol-2-yl)-2-fluorobenzyl)-2-methyl-N-phenyl-2,7-diazaspiro[3.5]nonane-7-carboxamide as white solid (0.005 g, 4.9%).

$^1$H NMR (400 MHz, MeOD) δ 7.95 (d, 1H, J=7.0 Hz), 7.90-7.72 (m, 2H), 7.41-7.35 (m, 2H), 7.23-7.10 (m, 3H), 4.97 (s, 2H), 3.43 (s, 4H), 3.23-3.20 (m, 4H), 2.58 (s, 3H), 1.62-1.59 (m, 4H); LRMS (ES) m/z 486.0 (M$^+$+1).

Example 166. Compound 21497: N-(4-(5-(difluoromethyl)-1,3,4-oxadiazol-2-yl)-2-fluorobenzyl)-N-phenyl-2,7-diazaspiro[3.5]nonane-2-carboxamide

[Step 1] Tert-butyl 2-((2-fluoro-4-(methoxycarbonyl)benzyl)(phenyl)carbamoyl)-2,7-diazaspiro[3.5]nonane-7-carboxylate

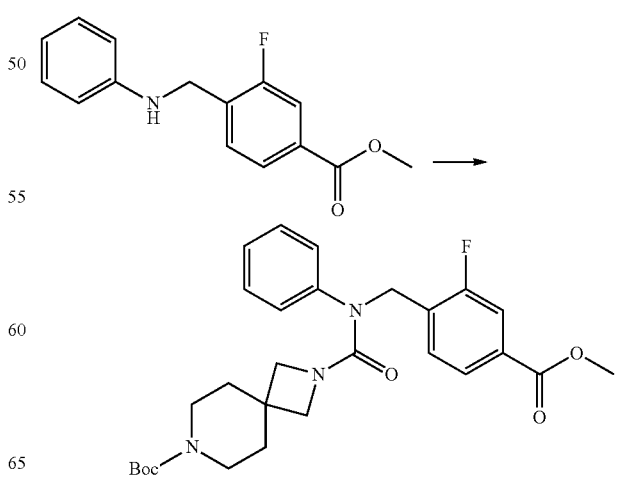

A solution of methyl 3-fluoro-4-((phenylamino)methyl)benzoate (1.000 g, 3.857 mmol), triphosgene (0.916 g, 3.085 mmol) and N,N-diisopropylethylamine (3.368 mL, 19.284 mmol) in dichloromethane (10 mL) was stirred at 0° C. for 10 min, and mixed with tert-butyl 2,7-diazaspiro[3.5]nonane-7-carboxylate (1.047 g, 4.628 mmol). The reaction mixture was stirred at the same temperature for additional 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=10% to 70%) to give the title compound tert-butyl 2-((2-fluoro-4-(methoxycarbonyl)benzyl)(phenyl)carbamoyl)-2,7-diazaspiro[3.5]nonane-7-carboxylate as pale yellow oil (1.890 g, 95.8%).

[Step 2] Tert-butyl 2-((2-fluoro-4-(hydrazinecarbonyl)benzyl)(phenyl)carbamoyl)-2,7-diazaspiro[3.5]nonane-7-carboxylate

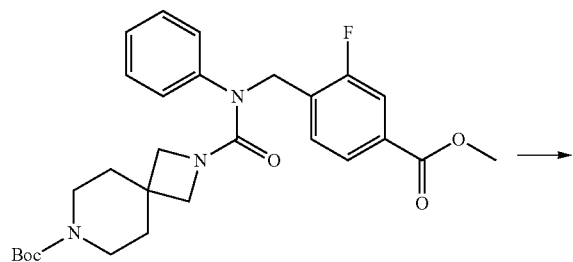

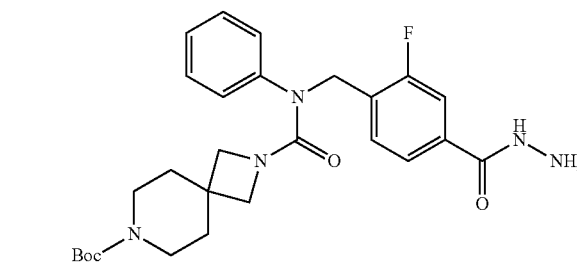

Tert-butyl 2-((2-fluoro-4-(methoxycarbonyl)benzyl)(phenyl)carbamoyl)-2,7-diazaspiro[3.5]nonane-7-carboxylate (1.890 g, 3.694 mmol) prepared in Step 1 and hydrazine monohydrate (3.591 mL, 73.887 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (1.740 g, 92.1%, white solid).

[Step 3] Tert-butyl 2-((4-(2-(2,2-difluoroacetyl)hydrazine-1-carbonyl)-2-fluorobenzyl)(phenyl)carbamoyl)-2,7-diazaspiro[3.5]nonane-7-carboxylate

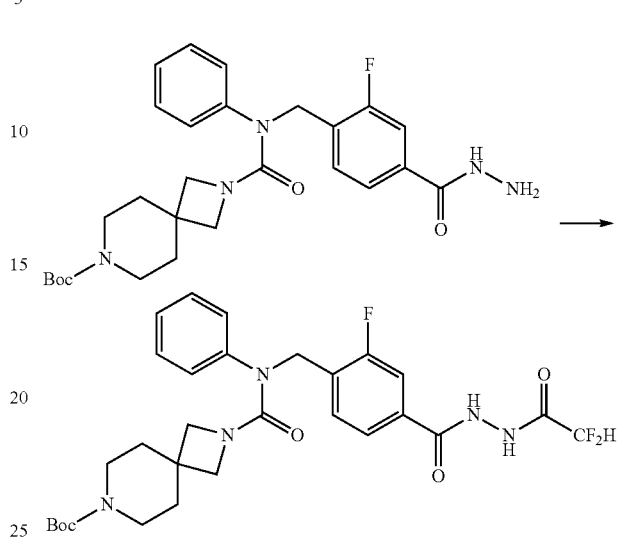

A solution of tert-butyl 2-((2-fluoro-4-(hydrazinecarbonyl)benzyl)(phenyl)carbamoyl)-2,7-diazaspiro[3.5]nonane-7-carboxylate (1.740 g, 3.401 mmol) prepared in Step 2 and triethylamine (0.707 mL, 5.102 mmol) in dichloromethane (10 mL) was mixed at the room temperature with 2,2-difluoroacetic anhydride (0.381 mL, 3.061 mmol). The reaction mixture was stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (2.160 g, 107.7%, pale yellow solid).

[Step 4] Tert-butyl 2-((4-(5-(difluoromethyl)-1,3,4-oxadiazol-2-yl)-2-fluorobenzyl)(phenyl)carbamoyl)-2,7-diazaspiro[3.5]nonane-7-carboxylate

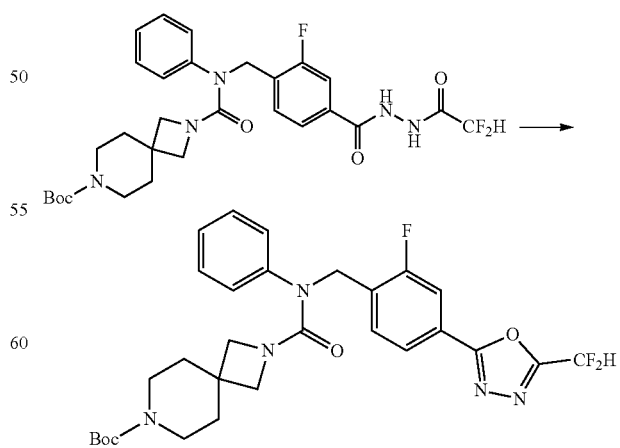

Tert-butyl 2-((4-(2-(2,2-difluoroacetyl)hydrazine-1-carbonyl)-2-fluorobenzyl)(phenyl)carbamoyl)-2,7-diazaspiro

[3.5]nonane-7-carboxylate (2.160 g, 3.663 mmol) prepared in Step 3 and 1-methoxy-N-triethylammoniosulfonyl-methanimidate (Burgess reagent, 1.309 g, 5.495 mmol) in tetrahydrofuran (10 mL) was mixed at the room temperature and then heated at 150° C. under the microwaves for 30 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=10% to 60%) to give the title compound tert-butyl 2-((4-(5-(difluoromethyl)-1,3,4-oxadiazol-2-yl)-2-fluorobenzyl)(phenyl)carbamoyl)-2,7-diazaspiro[3.5]nonane-7-carboxylate as pale yellow solid (1.200 g, 57.3%).

[Step 5] Compound 21497

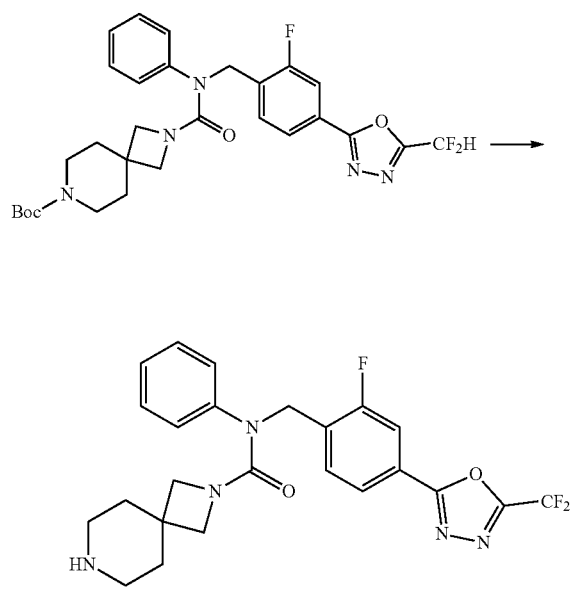

A solution of tert-butyl 2-((4-(5-(difluoromethyl)-1,3,4-oxadiazol-2-yl)-2-fluorobenzyl)(phenyl)carbamoyl)-2,7-diazaspiro[3.5]nonane-7-carboxylate (1.200 g, 2.099 mmol) prepared in Step 4 and trifluoroacetic acid (1.607 mL, 20.994 mmol) in dichloromethane (10 mL) was stirred at the room temperature for 17 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 20%) to give the title compound N-(4-(5-(difluoromethyl)-1,3,4-oxadiazol-2-yl)-2-fluorobenzyl)-N-phenyl-2,7-diazaspiro[3.5]nonane-2-carboxamide as white solid (0.264 g, 26.7%).

$^1$H NMR (400 MHz, CDCl$_3$) δ 7.87 (dd, 1H, J=8.0, 1.5 Hz), 7.75-7.68 (m, 2H), 7.32 (t, 2H, J=7.6 Hz), 7.24-7.20 (m, 1H), 7.16-7.14 (m, 2H), 6.92 (t, 1H, J=51.7 Hz), 5.02 (s, 2H), 3.29 (s, 4H), 2.69 (s, 4H), 1.58 (t, 4H, J=5.3 Hz).

Example 167. Compound 21498: N-(4-(5-(difluoromethyl)-1,3,4-oxadiazol-2-yl)-2-fluorobenzyl)-7-methyl-N-phenyl-2,7-diazaspiro[3.5]nonane-2-carboxamide

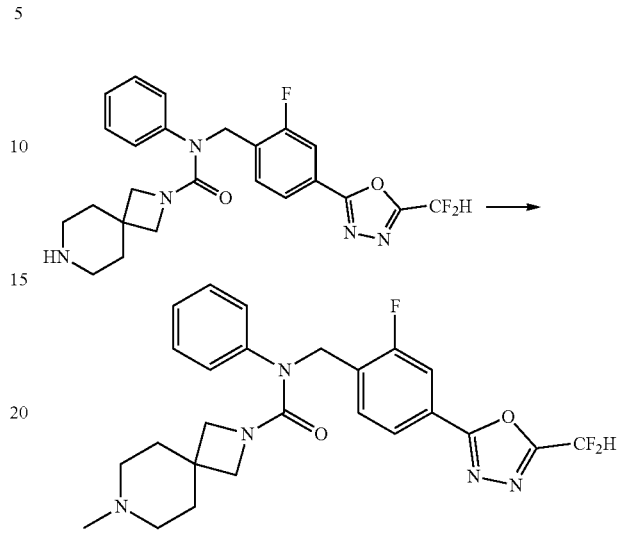

A solution of N-(4-(5-(difluoromethyl)-1,3,4-oxadiazol-2-yl)-2-fluorobenzyl)-N-phenyl-2,7-diazaspiro[3.5]nonane-2-carboxamide (0.100 g, 0.212 mmol) prepared in Example 166 and formaldehyde (37.00% solution in water, 0.024 mL, 0.318 mmol) in dichloromethane (4 mL) was mixed at the room temperature with sodium triacetoxyborohydride (0.090 g, 0.424 mmol), and stirred at the same temperature for 17 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified by column chromatography (Waters, C18; acetonitrile/aqueous 0.1%-formic acid solution=5% to 75%), and the fraction containing the product was passed through an SPE cartridge (MP-HCO$_3$ resin) to give the title compound N-(4-(5-(difluoromethyl)-1,3,4-oxadiazol-2-yl)-2-fluorobenzyl)-7-methyl-N-phenyl-2,7-diazaspiro[3.5]nonane-2-carboxamide as white solid (0.005 g, 4.9%).

$^1$H NMR (400 MHz, MeOD) δ 7.87 (dd, 1H, J=20.0, 12.0 Hz), 7.75-7.69 (m, 2H), 7.33 (t, 2H, J=7.7 Hz), 7.24 (t, 1H, J=7.4 Hz), 7.16 (d, 2H, J=7.2 Hz), 6.92 (t, 1H, J=51.7 Hz), 5.02 (s, 2H), 3.34-3.33 (m, 8H), 1.69 (s, 3H), 1.60 (s, 4H); LRMS (ES) m/z 486.0 (M$^+$+1).

Example 168. Compound 21499: N-(4-(5-(difluoromethyl)-1,3,4-oxadiazol-2-yl)-2-fluorobenzyl)-7-ethyl-N-phenyl-2,7-diazaspiro[3.5]nonane-2-carboxamide

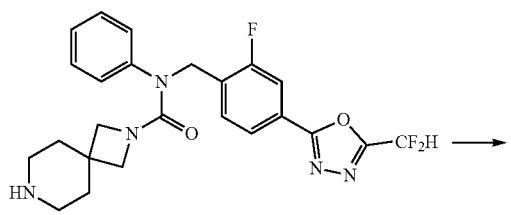

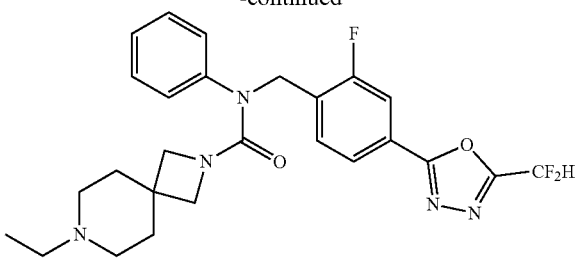

A solution of N-(4-(5-(difluoromethyl)-1,3,4-oxadiazol-2-yl)-2-fluorobenzyl)-N-phenyl-2,7-diazaspiro[3.5]nonane-2-carboxamide (0.100 g, 0.212 mmol) prepared in Example 166 and acetaldehyde (0.018 mL, 0.318 mmol) in dichloromethane (4 mL) was mixed at the room temperature with sodium triacetoxyborohydride (0.090 g, 0.424 mmol), and stirred at the same temperature for 17 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified by column chromatography (Waters, C18; acetonitrile/aqueous 0.1%-formic acid solution=5% to 75%), and the fraction containing the product was passed through an SPE cartridge (MP-HCO3 resin) to give the title compound N-(4-(5-(difluoromethyl)-1,3,4-oxadiazol-2-yl)-2-fluorobenzyl)-7-ethyl-N-phenyl-2,7-diazaspiro[3.5]nonane-2-carboxamide as white solid (0.009 g, 8.5%).

$^1$H NMR (400 MHz, MeOD) δ 7.90 (dd, 1H, J=8.0, 1.6 Hz), 7.76-7.71 (m, 2H), 7.40-7.36 (m, 2H), 7.29-7.10 (m, 4H), 5.03 (s, 2H), 3.26 (s, 4H), 2.48-2.45 (m, 6H), 1.69-1.68 (m, 4H), 1.10 (t, 3H, J=7.2 Hz); LRMS (ES) m/z 500.4 ($M^+$+1).

Example 169. Compound 21500: 7-Acetyl-N-(4-(5-(difluoromethyl)-1,3,4-oxadiazol-2-yl)-2-fluorobenzyl)-N-phenyl-2,7-diazaspiro[3.5]nonane-2-carboxamide

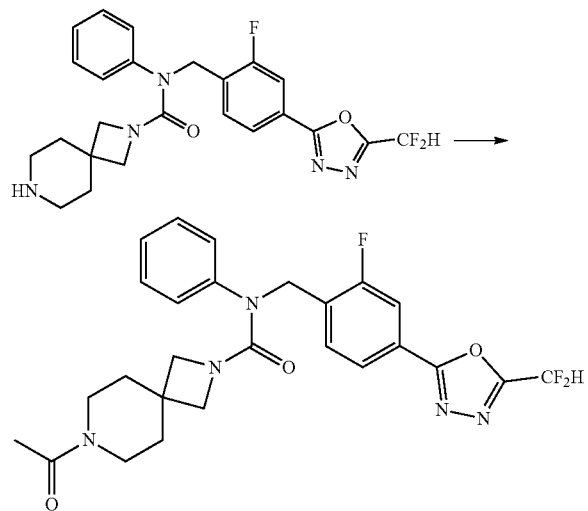

A solution of N-(4-(5-(difluoromethyl)-1,3,4-oxadiazol-2-yl)-2-fluorobenzyl)-N-phenyl-2,7-diazaspiro[3.5]nonane-2-carboxamide (0.100 g, 0.212 mmol) prepared in Example 166 and triethylamine (0.059 mL, 0.424 mmol) in dichloromethane (4 mL) was mixed at the room temperature with acetyl chloride (0.023 mL, 0.318 mmol), and stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound 7-acetyl-N-(4-(5-(difluoromethyl)-1,3,4-oxadiazol-2-yl)-2-fluorobenzyl)-N-phenyl-2,7-diazaspiro[3.5]nonane-2-carboxamide as colorless oil (0.101 g, 92.7%).

$^1$H NMR (400 MHz, CDCl$_3$) δ 7.88 (dd, 1H, J=8.0, 1.6 Hz), 7.74-7.69 (m, 2H), 7.33 (t, 2H, J=7.6 Hz), 7.23 (t, 1H, J=7.4 Hz), 7.16-7.14 (m, 2H), 6.92 (t, 1H, J=51.7 Hz), 5.02 (s, 2H), 3.33 (s, 8H), 2.06 (s, 3H), 1.61 (s, 4H); LRMS (ES) m/z 514.5 ($M^+$+1).

Example 170. Compound 21501: N-(4-(5-(difluoromethyl)-1,3,4-oxadiazol-2-yl)-2-fluorobenzyl)-7-(methylsulfonyl)-N-phenyl-2,7-diazaspiro[3.5]nonane-2-carboxamide

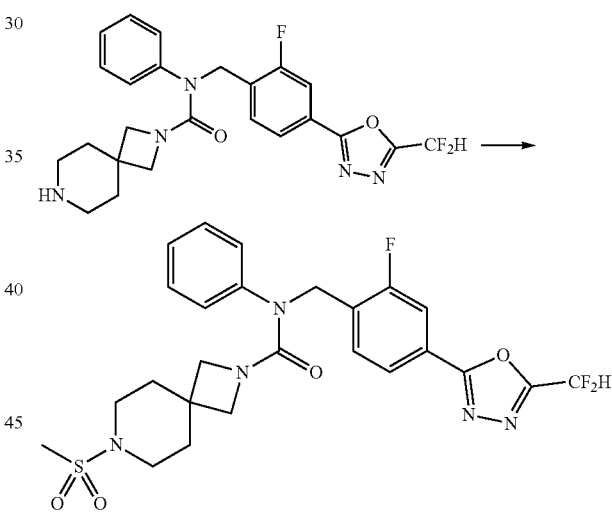

A solution of N-(4-(5-(difluoromethyl)-1,3,4-oxadiazol-2-yl)-2-fluorobenzyl)-N-phenyl-2,7-diazaspiro[3.5]nonane-2-carboxamide (0.100 g, 0.212 mmol) prepared in Example 166 and triethylamine (0.059 mL, 0.424 mmol) in dichloromethane (4 mL) was mixed at the room temperature with methanesulfonyl chloride (0.025 mL, 0.318 mmol), and stirred at the same temperature for 1 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(5-(difluoromethyl)-1,3,4-oxadiazol-2-yl)-2-fluorobenzyl)-7-(methylsulfonyl)-N-phenyl-2,7-diazaspiro[3.5]nonane-2-carboxamide as colorless oil (0.114 g, 97.8%).

$^1$H NMR (400 MHz, CDCl$_3$) δ 7.88 (dd, 1H, J=0.8.0, 1.5 Hz), 7.74-7.69 (m, 2H), 7.34 (t, 2H, J=7.6 Hz), 7.24 (t, 1H, J=7.4 Hz), 7.16-7.14 (m, 2H), 5.02 (s, 2H), 3.32 (s, 4H), 3.09 (t, 4H, J=5.4 Hz), 2.75 (s, 3H), 1.73 (t, 4H, J=5.5 Hz); LRMS (ES) m/z 550.4 (M$^+$+1).

Example 171. Compound 21502: N-([1,1'-biphenyl]-3-yl)-N-(4-(5-(difluoromethyl)-1,3,4-oxadiazol-2-yl)benzyl)thiomorpholine-4-carboxamide 1,1-dioxide

[Step 1] N-([1,1'-biphenyl]-3-yl)-N-(4-(2-(2,2-difluoroacetyl)hydrazine-1-carbonyl)benzyl)thiomorpholine-4-carboxamide 1,1-dioxide

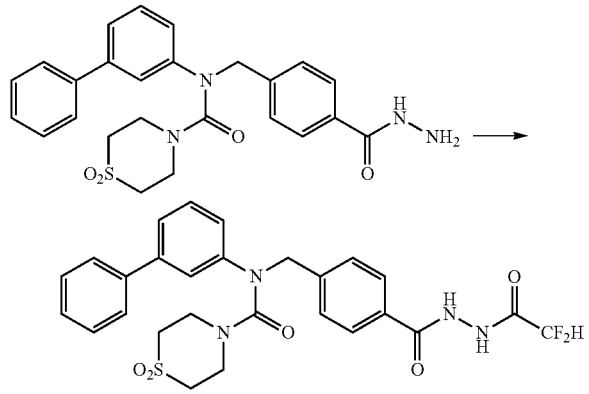

A solution of N-([1,1'-biphenyl]-3-yl)-N-(4-(hydrazinecarbonyl)benzyl)thiomorpholine-4-carboxamide 1,1-dioxide (0.466 g, 0.974 mmol) prepared in Step 2 of Example 108 and triethylamine (0.202 mL, 1.461 mmol) in dichloromethane (10 mL) was mixed at the room temperature with difluoroacetic anhydride (0.101 mL, 0.876 mmol). The reaction mixture was stirred at the same temperature for 3 hr. Then, aqueous 1N-sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; dichloromethane/methanol=0% to 5%) to give the title compound N-([1,1'-biphenyl]-3-yl)-N-(4-(2-(2,2-difluoroacetyl)hydrazine-1-carbonyl)benzyl)thiomorpholine-4-carboxamide 1,1-dioxide as white solid (0.338 g, 62.7%).

[Step 2] Compound 21502

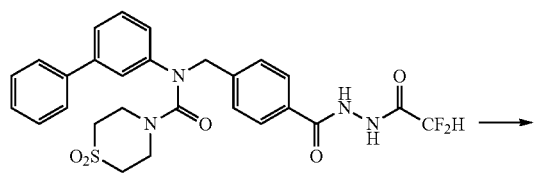

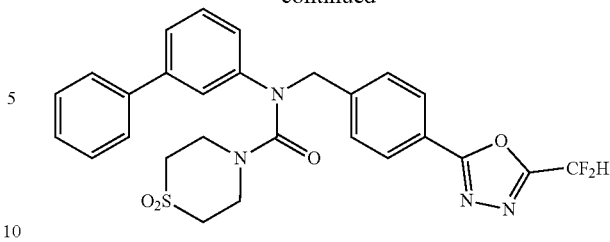

A mixture of N-([1,1'-biphenyl]-3-yl)-N-(4-(2-(2,2-difluoroacetyl)hydrazine-1-carbonyl)benzyl)thiomorpholine-4-carboxamide 1,1-dioxide (0.338 g, 0.611 mmol) prepared in Step 1 and 1-methoxy-N-triethylammoniosulfonylmethanimidate (Burgess reagent, 0.218 g, 0.916 mmol) in tetrahydrofuran (3 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=0% to 3%) to give the title compound N-([1,1'-biphenyl]-3-yl)-N-(4-(5-(difluoromethyl)-1,3,4-oxadiazol-2-yl)benzyl)thiomorpholine-4-carboxamide 1,1-dioxide as white solid (0.223 g, 67.8%).

$^1$H NMR (400 MHz, CDCl$_3$) δ 8.07-8.00 (m, 2H), 7.51-7.33 (m, 9H), 7.32-7.25 (m, 1H), 7.08-6.74 (m, 2H), 4.95 (s, 2H), 3.82-3.72 (m, 4H), 2.87-2.79 (m, 4H); LRMS (ES) m/z 539.2 (M$^+$+1).

Example 172. Compound 21511: N-(4-ethylphenyl)-N-(2-fluoro-4-(5-(trifluoromethyl)-1,3,4-oxadiazol-2-yl)benzyl)thiomorpholine-4-carboxamide 1,1-dioxide

[Step 1] N-(4-ethylphenyl)thiomorpholine-4-carboxamide 1,1-dioxide

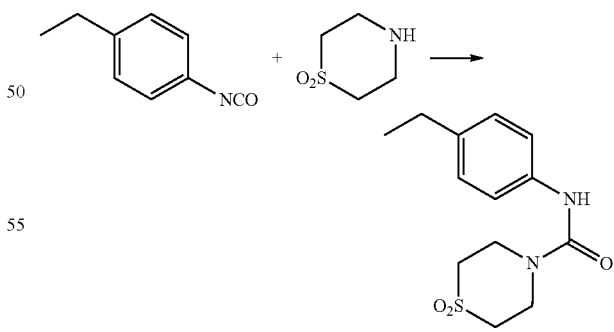

A solution of 1-ethyl-4-isocyanatobenzene (0.962 mL, 6.794 mmol) and thiomorpholine 1,1-dioxide (0.964 g, 7.134 mmol) in diethylether (100 mL) was stirred at the room temperature for 16 hr. The precipitates were collected by filtration, washed by diethylether, and dried to give the title compound N-(4-ethylphenyl)thiomorpholine-4-carboxamide 1,1-dioxide as white solid (1.910 g, 99.6%).

[Step 2] Methyl 4-((N-(4-ethylphenyl)-1,1-dioxido-thiomorpholine-4-carboxamido)methyl)-3-fluorobenzoate

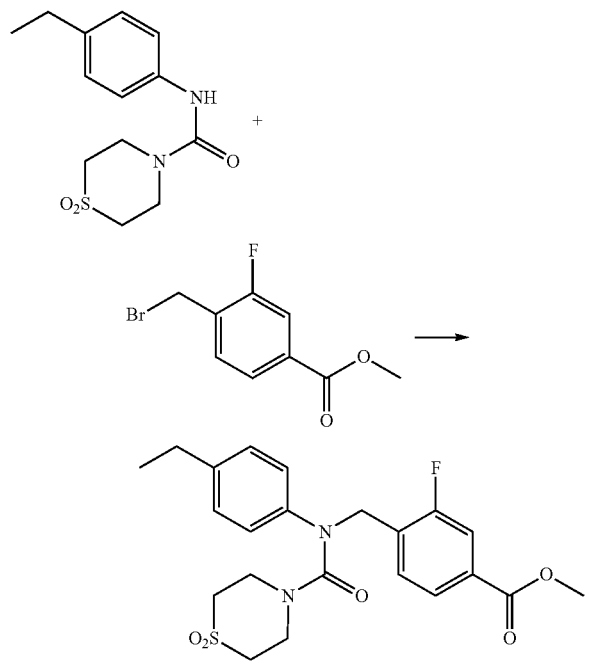

To a stirred solution of N-(4-ethylphenyl)thiomorpholine-4-carboxamide 1,1-dioxide (1.000 g, 3.542 mmol) prepared in Step 1 in N,N-dimethylformide (30 mL) was added at 0° C. sodium hydride (60.00%, 0.170 g, 4.250 mmol). The reaction mixture was stirred at the same temperature. Methyl 4-(bromomethyl)benzoate (0.884 g, 3.577 mmol) was added to the reaction mixture, and stirred for additional 3 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 40 g cartridge; ethyl acetate/hexane=0% to 50%) to give the title compound methyl 4-((N-(4-ethylphenyl)-1,1-dioxidothiomorpholine-4-carboxamido)methyl)-3-fluorobenzoate as white solid (1.300 g, 81.8%).

[Step 3] N-(4-ethylphenyl)-N-(2-fluoro-4-(hydrazinecarbonyl)benzyl)thiomorpholine-4-carboxamide 1,1-dioxide

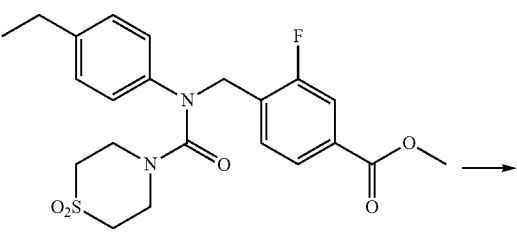

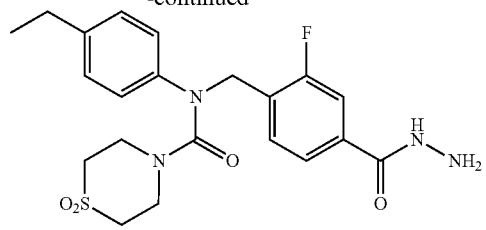

A mixture of methyl 4-((N-(4-ethylphenyl)-1,1-dioxido-thiomorpholine-4-carboxamido)methyl)-3-fluorobenzoate (1.000 g, 2.230 mmol) prepared in Step 2 and hydrazine monohydrate (2.106 mL, 44.592 mmol) in ethanol (10 mL) was heated at reflux for 16 hr, and cooled down to the room temperature. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (1.000 g, 100.0%, light yellow solid).

[Step 4] N-(4-ethylphenyl)-N-(2-fluoro-4-(2-(2,2,2-trifluoroacetyl)hydrazine-1-carbonyl)benzyl)thiomorpholine-4-carboxamide 1,1-dioxide

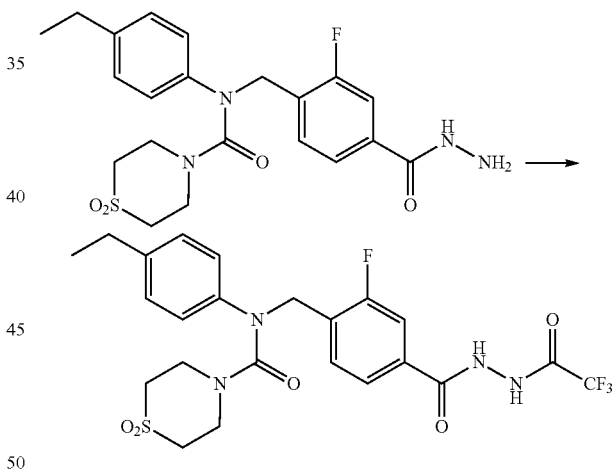

A solution of N-(4-ethylphenyl)-N-(2-fluoro-4-(hydrazinecarbonyl)benzyl)thiomorpholine-4-carboxamide 1,1-dioxide (0.500 g, 1.115 mmol) prepared in Step 3 and triethylamine (0.232 mL, 1.672 mmol) in dichloromethane (10 mL) was mixed at 0° C. with trifluoroacetic anhydride (0.140 mL, 1.003 mmol), and stirred at the room temperature for 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 24 g cartridge; methanol/dichloromethane=0% to 3%) to give the title compound N-(4-ethylphenyl)-N-(2-fluoro-4-(2-(2,2,2-trifluoroacetyl)hydrazine-1-carbonyl)benzyl)thiomorpholine-4-carboxamide 1,1-dioxide as white solid (0.597 g, 98.3%).

[Step 5] Compound 21511

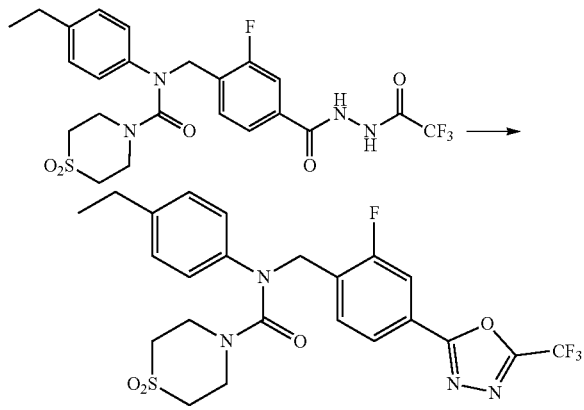

A mixture of N-(4-ethylphenyl)-N-(2-fluoro-4-(2-(2,2,2-trifluoroacetyl)hydrazine-1-carbonyl)benzyl)thiomorpholine-4-carboxamide 1,1-dioxide (0.597 g, 1.096 mmol) prepared in Step 4 and 1-methoxy-N-triethylammoniosulfonyl-methanimidate (Burgess reagent, 0.392 g, 1.645 mmol) in trifluoroacetic acid (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=0% to 50%) to give the title compound N-(4-ethylphenyl)-N-(2-fluoro-4-(5-(trifluoromethyl)-1,3,4-oxadiazol-2-yl)benzyl)thiomorpholine-4-carboxamide 1,1-dioxide as white solid (0.411 g, 71.2%).

$^1$H NMR (400 MHz, CDCl$_3$) δ 7.86 (dd, 1H, J=8.0, 1.6 Hz), 7.74 (dd, 1H, J=10.0, 1.7 Hz), 7.67 (t, 1H, J=7.6 Hz), 7.21-7.14 (m, 2H), 7.06-6.99 (m, 2H), 4.90 (s, 2H), 3.75-3.65 (m, 5H), 2.80-2.72 (m, 4H), 2.63 (q, 2H, J=7.6 Hz), 1.22 (t, 3H, J=7.6 Hz); LRMS (ES) m/z 527.07 (M$^+$+1).

Example 173. Compound 21512: N-(4-(5-(difluoromethyl)-1,3,4-oxadiazol-2-yl)-2-fluorobenzyl)-N-(4-ethylphenyl)thiomorpholine-4-carboxamide 1,1-dioxide

[Step 1] N-(4-(2-(2,2-difluoroacetyl)hydrazine-1-carbonyl)-2-fluorobenzyl)-N-(4-ethylphenyl)thiomorpholine-4-carboxamide 1,1-dioxide

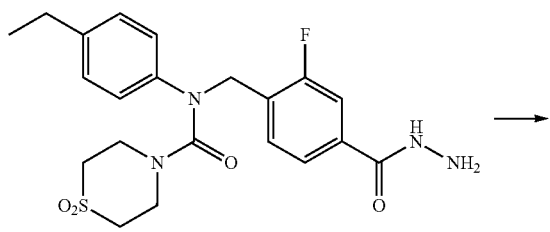

-continued

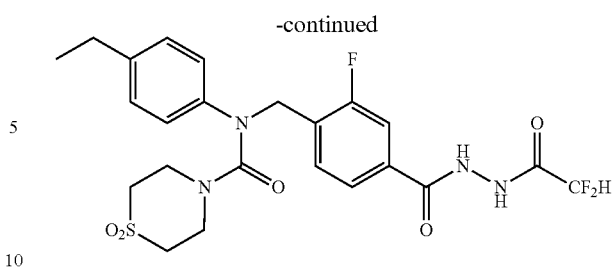

A solution of N-(4-ethylphenyl)-N-(2-fluoro-4-(hydrazinecarbonyl)benzyl)thiomorpholine-4-carboxamide 1,1-dioxide (0.500 g, 1.115 mmol) prepared in Step 3 of Example 172 and triethylamine (0.232 mL, 1.672 mmol) in dichloromethane (10 mL) was mixed at 0° C. with difluoroacetic anhydride (0.109 mL, 1.003 mmol), and stirred at the room temperature for 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give the title compound N-(4-(2-(2,2-difluoroacetyl)hydrazine-1-carbonyl)-2-fluorobenzyl)-N-(4-ethylphenyl)thiomorpholine-4-carboxamide 1,1-dioxide as white solid (0.574 g, 97.8%).

[Step 2] Compound 21512

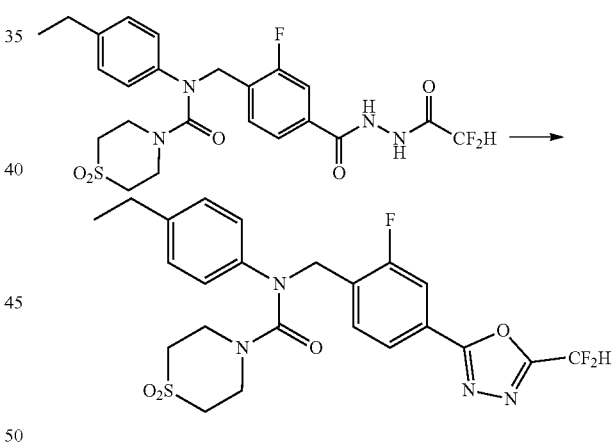

A mixture of N-(4-(2-(2,2-difluoroacetyl)hydrazine-1-carbonyl)-2-fluorobenzyl)-N-(4-ethylphenyl)thiomorpholine-4-carboxamide 1,1-dioxide (0.574 g, 1.090 mmol) prepared in Step 1 and 1-methoxy-N-triethylammoniosulfonyl-methanimidate (Burgess reagent, 0.390 g, 1.635 mmol) in tetrahydrofuran (10 mL) was heated at 150° C. for 30 min under the microwaves, and cooled down to the room temperature. The reaction mixture was concentrated under the reduced pressure to remove the solvent, and and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=0% to 50%) to give the title compound N-(4-(5-(difluoromethyl)-1,3,4-oxadiazol-2-yl)-2-fluorobenzyl)-N-(4-ethyl-phenyl)thiomorpholine-4-carboxamide 1,1-dioxide as white solid (0.323 g, 58.3%).

$^1$H NMR (400 MHz, CDCl$_3$) δ 7.86 (dd, 1H, J=8.0, 1.7 Hz), 7.74 (dd, 1H, J=10.1, 1.6 Hz), 7.65 (t, 1H, J=7.7 Hz), 7.21-7.14 (m, 2H), 7.06-6.98 (m, 3H), 4.89 (s, 2H), 3.75-3.65 (m, 4H), 2.76-2.74 (m, 4H), 2.62 (q, 2H), 1.22 (t, 3H, J=7.6 Hz); LRMS (ES) m/z 509.34 (M$^+$+1).

Example 174. Compound 21513: N-(2-fluoro-4-(5-(trifluoromethyl)-1,3,4-oxadiazol-2-yl)benzyl)-N-(4-(trifluoromethoxy) phenyl)thiomorpholine-4-carboxamide 1,1-dioxide

[Step 1] N-(4-(trifluoromethoxy)phenyl)thiomorpholine-4-carboxamide 1,1-dioxide

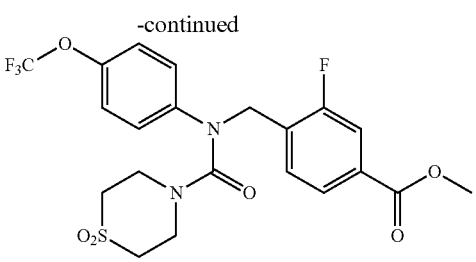

A solution of 1-isocyanato-4-(trifluoromethoxy)benzene (0.735 mL, 4.923 mmol) and thiomorpholine 1,1-dioxide (0.699 g, 5.169 mmol) in diethylether (100 mL) was stirred at the room temperature for 16 hr. The precipitates were collected by filtration, washed by diethylether, and dried to give the title compound N-(4-(trifluoromethoxy)phenyl)thiomorpholine-4-carboxamide 1,1-dioxide as white solid (1.660 g, 99.7%).

[Step 2] Methyl 4-((1,1-dioxido-N-(4-(trifluoromethoxy)phenyl)thiomorpholine-4-carboxamido)methyl)-3-fluorobenzoate

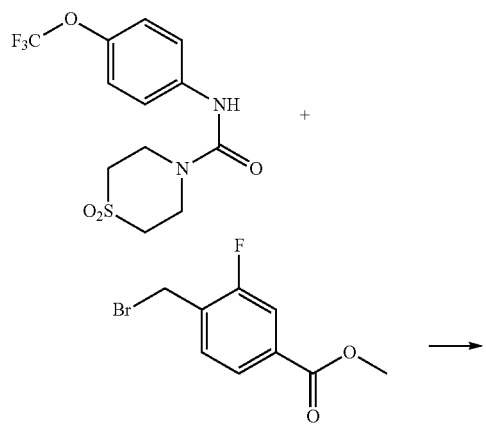

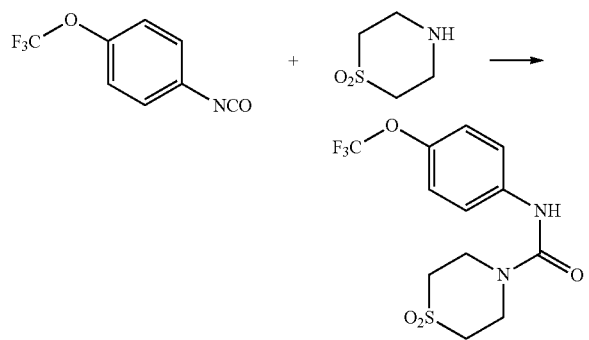

To a stirred solution of N-(4-(trifluoromethoxy)phenyl)thiomorpholine-4-carboxamide 1,1-dioxide (1.000 g, 2.956 mmol) prepared in Step 1 in N,N-dimethylformide (30 mL) was added at 0° C. sodium hydride (60.00%, 0.142 g, 3.547 mmol). The reaction mixture was stirred at the same temperature. Methyl 4-(bromomethyl)-3-fluorobenzoate (0.738 g, 2.986 mmol) was added to the reaction mixture, and stirred at the room temperature for additional 3 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 50%) to give the title compound methyl 4-((1,1-dioxido-N-(4-(trifluoromethoxy)phenyl)thiomorpholine-4-carboxamido)methyl)-3-fluorobenzoate as colorless oil (1.480 g, 99.3%).

[Step 3] N-(2-fluoro-4-(hydrazinecarbonyl)benzyl)-N-(4-(trifluoromethoxy)phenyl)thiomorpholine-4-carboxamide 1,1-dioxide

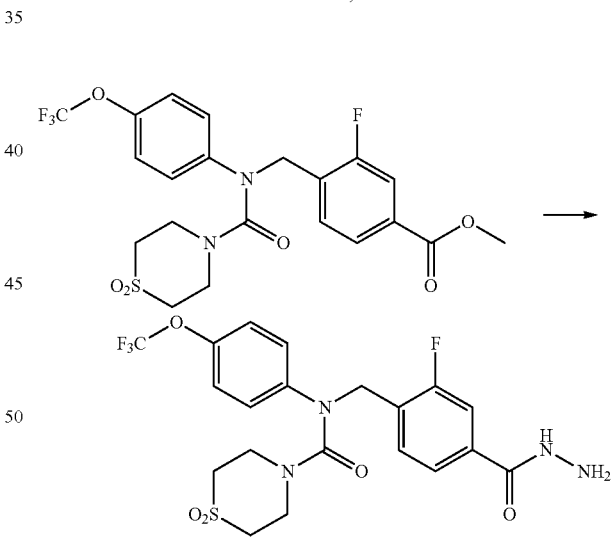

A mixture of methyl 4-((1,1-dioxido-N-(4-(trifluoromethoxy)phenyl)thiomorpholine-4-carboxamido)methyl)-3-fluorobenzoate (1.000 g, 1.982 mmol) prepared in Step 2 and hydrazine monohydrate (1.872 mL, 39.647 mmol) in ethanol (10 mL) was heated at reflux for 16 hr, and cooled down to the room temperature. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concen-

[Step 4] N-(2-fluoro-4-(2-(2,2,2-trifluoroacetyl)hydrazine-1-carbonyl)benzyl)-N-(4-(trifluoromethoxy)phenyl)thiomorpholine-4-carboxamide 1,1-dioxide

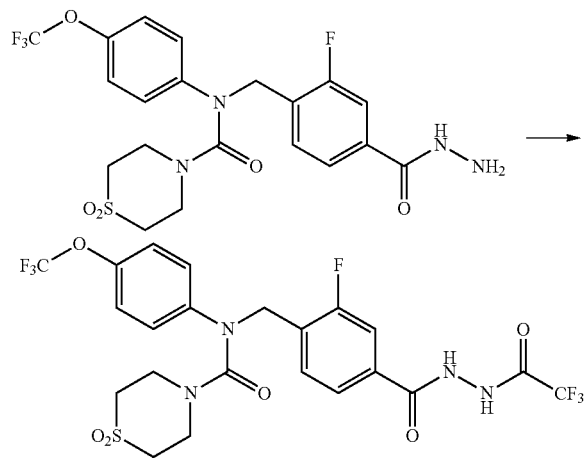

A solution of N-(2-fluoro-4-(hydrazinecarbonyl)benzyl)-N-(4-(trifluoromethoxy)phenyl)thiomorpholine-4-carboxamide 1,1-dioxide (0.400 g, 0.793 mmol) prepared in Step 3 and triethylamine (0.165 mL, 1.189 mmol) in dichloromethane (10 mL) was mixed at 0° C. with trifluoroacetic anhydride (0.099 mL, 0.714 mmol), and stirred at the room temperature for 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give the title compound N-(2-fluoro-4-(2-(2,2,2-trifluoroacetyl)hydrazine-1-carbonyl)benzyl)-N-(4-(trifluoromethoxy)phenyl)thiomorpholine-4-carboxamide 1,1-dioxide as white solid (0.457 g, 96.0%).

[Step 5] Compound 21513

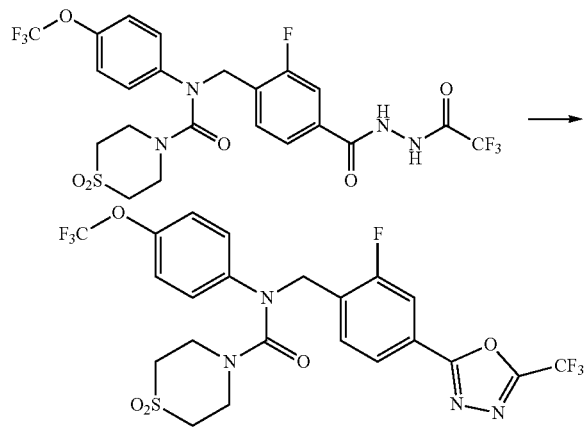

A mixture of N-(2-fluoro-4-(2-(2,2,2-trifluoroacetyl)hydrazine-1-carbonyl)benzyl)-N-(4-(trifluoromethoxy)phenyl)thiomorpholine-4-carboxamide 1,1-dioxide (0.457 g, 0.761 mmol) prepared in Step 4 and 1-methoxy-N-triethylammoniosulfonyl-methanimidate (Burgess reagent, 0.272 g, 1.142 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=0% to 50%) to give the title compound N-(2-fluoro-4-(5-(trifluoromethyl)-1,3,4-oxadiazol-2-yl)benzyl)-N-(4-(trifluoromethoxy) phenyl)thiomorpholine-4-carboxamide 1,1-dioxide as white solid (0.259 g, 58.4%).

$^1$H NMR (400 MHz, CDCl$_3$) δ 7.88 (dd, 1H, J=8.0, 1.7 Hz), 7.76 (dd, 1H, J=10.0, 1.7 Hz), 7.73-7.64 (m, 1H), 7.26-7.19 (m, 2H), 7.19-7.12 (m, 2H), 4.92 (s, 2H), 3.73-3.65 (m, 4H), 2.88-2.80 (m, 4H); LRMS (ES) m/z 583.28 (M$^+$+1).

Example 175. Compound 21514: N-(4-(5-(difluoromethyl)-1,3,4-oxadiazol-2-yl)-2-fluorobenzyl)-N-(4-(trifluoromethoxy)phenyl)thiomorpholine-4-carboxamide 1,1-dioxide

[Step 1] N-(4-(2-(2,2-difluoroacetyl)hydrazine-1-carbonyl)-2-fluorobenzyl)-N-(4-(trifluoromethoxy)phenyl)thiomorpholine-4-carboxamide 1,1-dioxide

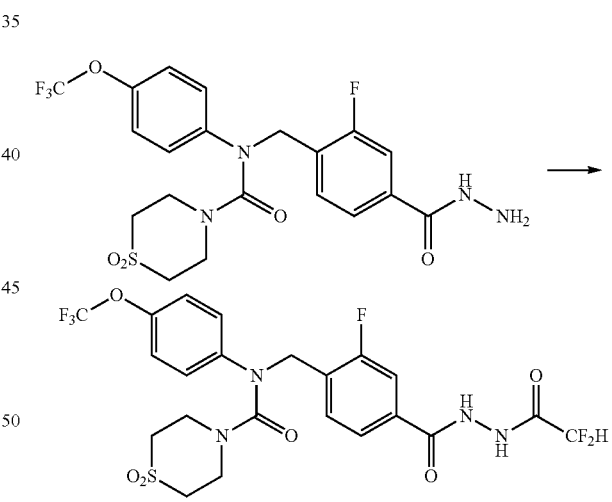

A solution of N-(2-fluoro-4-(hydrazinecarbonyl)benzyl)-N-(4-(trifluoromethoxy)phenyl)thiomorpholine-4-carboxamide 1,1-dioxide (0.400 g, 0.793 mmol) prepared in Step 3 of Example 174 and triethylamine (0.165 mL, 1.189 mmol) in dichloromethane (10 mL) was mixed at 0° C. with difluoroacetic anhydride (0.078 mL, 0.714 mmol), and stirred at the room temperature for 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give N-(4-(2-(2,2-difluoroacetyl)hydrazine-1-carbonyl)-2-fluorobenzyl)-N-(4-(trifluoromethoxy)phenyl)thiomorpholine-4-carboxamide 1,1-dioxide as white solid (0.450 g, 97.4%).

[Step 2] Compound 21514

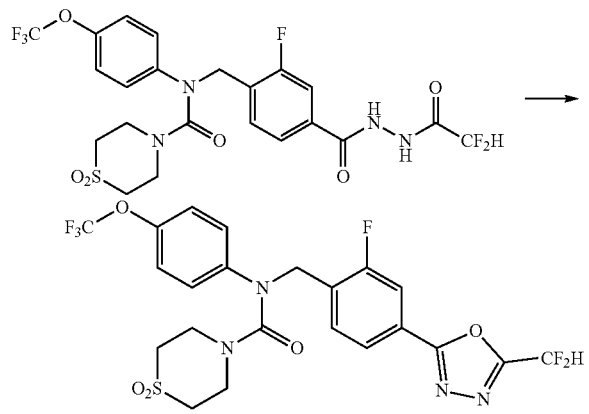

A mixture of N-(4-(2-(2,2-difluoroacetyl)hydrazine-1-carbonyl)-2-fluorobenzyl)-N-(4-(trifluoromethoxy)phenyl)thiomorpholine-4-carboxamide 1,1-dioxide (0.450 g, 0.773 mmol) prepared in Step 1 and 1-methoxy-N-triethylammoniosulfonyl-methanimidate (Burgess reagent, 0.276 g, 1.159 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 24 g cartridge; ethyl acetate/hexane=0% to 50%) to give the title compound N-(4-(5-(difluoromethyl)-1,3,4-oxadiazol-2-yl)-2-fluorobenzyl)-N-(4-(trifluoromethoxy)phenyl)thiomorpholine-4-carboxamide 1,1-dioxide as white solid (0.210 g, 48.2%).

$^1$H NMR (400 MHz, $CDCl_3$) δ 7.92-7.84 (m, 1H), 7.80-7.72 (m, 1H), 7.66 (t, 1H, J=7.6 Hz), 7.25-7.18 (m, 2H), 7.18-7.11 (m, 2H), 6.91 (t, 1H, J=51.6 Hz), 4.91 (s, 2H), 3.73-3.65 (m, 4H), 2.88-2.80 (m, 4H); LRMS (ES) m/z 565.29 ($M^+$+1).

Example 176. Compound 21515: N-(2-fluoro-4-(5-(trifluoromethyl)-1,3,4-oxadiazol-2-yl)benzyl)-N-(4-((4-methylpiperazin-1-yl)methyl)phenyl)thiomorpholine-4-carboxamide 1,1-dioxide

[Step 1] N-(4-(chloromethyl)phenyl)thiomorpholine-4-carboxamide 1,1-dioxide

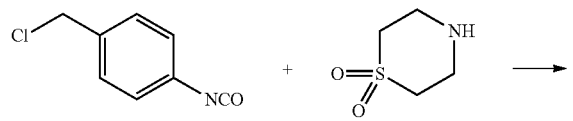

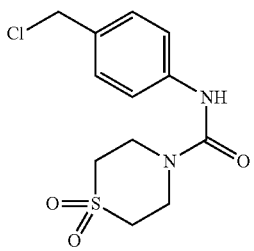

A solution of 1-(chloromethyl)-4-isocyanatobenzene (0.500 g, 2.983 mmol) and thiomorpholine 1,1-dioxide (0.403 g, 2.983 mmol) in diethylether (20 mL) was stirred at the room temperature for 16 hr. The precipitates were collected by filtration, washed by diethylether, and dried to give the title compound N-(4-(chloromethyl)phenyl)thiomorpholine-4-carboxamide 1,1-dioxide as yellow solid (0.832 g, 92.1%).

[Step 2] N-(4-((4-methylpiperazin-1-yl)methyl)phenyl)thiomorpholine-4-carboxamide 1,1-dioxide

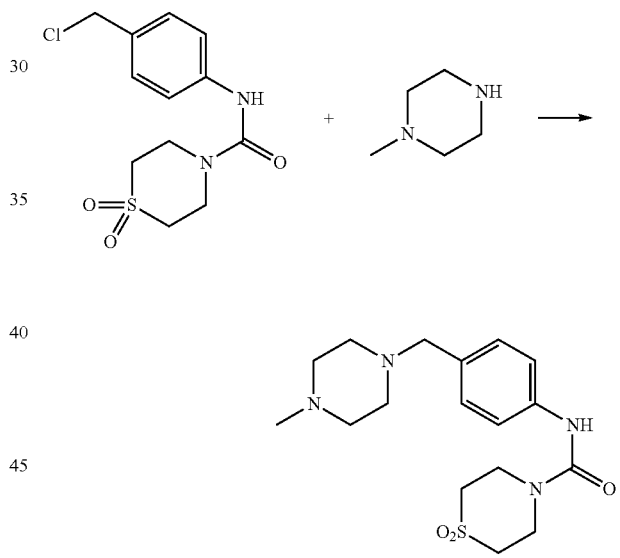

A solution of N-(4-(chloromethyl)phenyl)thiomorpholine-4-carboxamide 1,1-dioxide (0.300 g, 0.991 mmol) prepared in Step 1,1-methylpiperazine (0.330 mL, 2.973 mmol) and potassium carbonate (0.151 g, 1.090 mmol) in acetonitrile (2 mL) was stirred at the room temperature for 1 hr. The reaction mixture was filtered through a plastic frit to remove solids, and the filtrate was concentrated under the reduced pressure to remove the solvent. The concentrate was diluted with diethylether (10 mL) and stirred. The resulting precipitates were collected by filtration, washed by diethylether, and dried to give the title compound N-(4-((4-methylpiperazin-1-yl)methyl)phenyl)thiomorpholine-4-carboxamide 1,1-dioxide as white solid (0.249 g, 68.6%).

629

[Step 3] Methyl 3-fluoro-4-((N-(4-((4-methylpiperazin-1-yl)methyl)phenyl)-1,1-dioxidothiomorpholine-4-carboxamido)methyl)benzoate

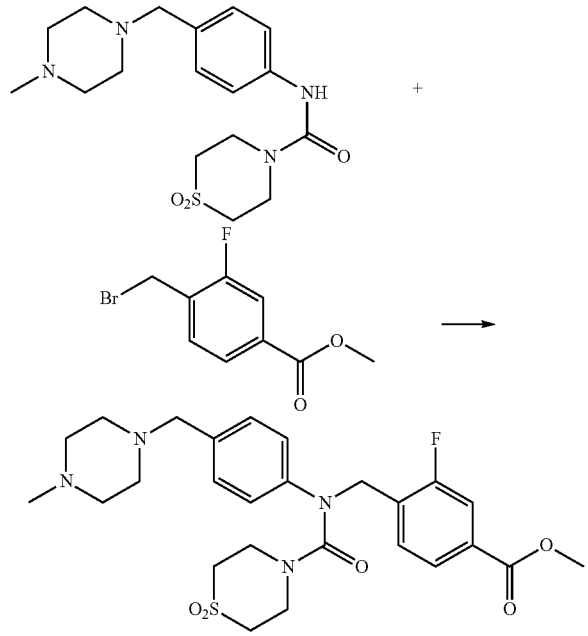

To a stirred solution of N-(4-((4-methylpiperazin-1-yl)methyl)phenyl)thiomorpholine-4-carboxamide 1,1-dioxide (0.249 g, 0.679 mmol) prepared in Step 2 in N,N-dimethylformamide (3 mL) was added at 0° C. sodium hydride (60.00%, 0.027 g, 0.679 mmol). The reaction mixture was stirred at the same temperature for 30 min. Methyl 4-(bromomethyl)-3-fluorobenzoate (0.168 g, 0.679 mmol) was added to the reaction mixture, and stirred at the room temperature for additional 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; methanol/dichloromethane=5% to 15%) to give the title compound methyl 3-fluoro-4-((N-(4-((4-methylpiperazin-1-yl)methyl)phenyl)-1,1-dioxidothiomorpholine-4-carboxamido)methyl)benzoate as colorless oil (0.182 g, 50.2%).

[Step 4] N-(2-fluoro-4-(hydrazinecarbonyl)benzyl)-N-(4-((4-methylpiperazin-1-yl)methyl)phenyl) thiomorpholine-4-carboxamide 1,1-dioxide

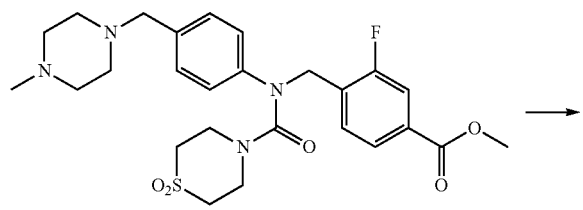

630

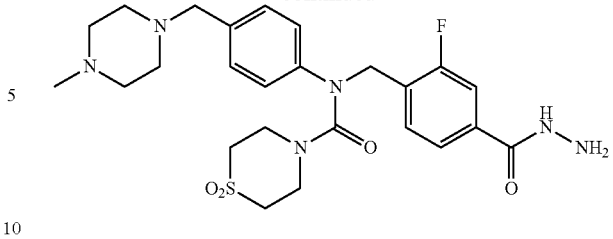

Methyl 3-fluoro-4-((N-(4-((4-methylpiperazin-1-yl)methyl)phenyl)-1,1-dioxidothiomorpholine-4-carboxamido)methyl)benzoate (0.171 g, 0.321 mmol) prepared in Step 1 and hydrazine monohydrate (0.152 mL, 3.210 mmol) were mixed at the room temperature in water (1 mL)/1,4-dioxane (4 mL) and then stirred at 100° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(hydrazinecarbonyl)benzyl)-N-(4-((4-methylpiperazin-1-yl)methyl)phenyl) thiomorpholine-4-carboxamide 1,1-dioxide as pale brown foam (0.116 g, 68.0%).

[Step 5] N-(2-fluoro-4-(2-(2,2,2-trifluoroacetyl)hydrazine-1-carbonyl)benzyl)-N-(4-((4-methylpiperazin-1-yl)methyl)phenyl)thiomorpholine-4-carboxamide 1,1-dioxide

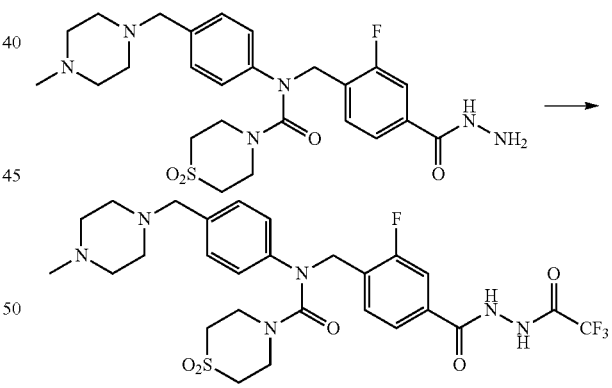

A solution of N-(2-fluoro-4-(hydrazinecarbonyl)benzyl)-N-(4-((4-methylpiperazin-1-yl)methyl)phenyl) thiomorpholine-4-carboxamide 1,1-dioxide (0.058 g, 0.109 mmol) prepared in Step 4 and triethylamine (0.030 mL, 0.218 mmol) in dichloromethane (1 mL) was mixed at the room temperature with trifluoroacetic anhydride (0.017 mL, 0.098 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.058 g, 84.6%, brown foam).

631

[Step 6] Compound 21515

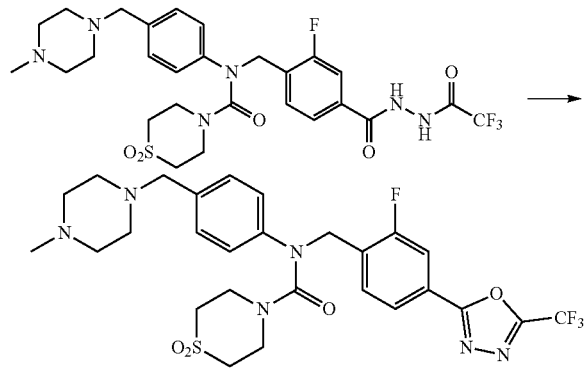

N-(2-fluoro-4-(2-(2,2,2-trifluoroacetyl)hydrazine-1-carbonyl)benzyl)-N-(4-((4-methylpiperazin-1-yl)methyl)phenyl)thiomorpholine-4-carboxamide 1,1-dioxide (0.058 g, 0.092 mmol) prepared in Step 1 and 1-methoxy-N-triethylammoniosulfonyl-methanimidate (Burgess reagent, 0.033 g, 0.138 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(2-fluoro-4-(5-(trifluoromethyl)-1,3,4-oxadiazol-2-yl)benzyl)-N-(4-((4-methylpiperazin-1-yl)methyl)phenyl)thiomorpholine-4-carboxamide 1,1-dioxide as pale yellow foam (0.016 g, 28.8%).

$^1$H NMR (400 MHz, CDCl$_3$) δ 7.87 (dd, 1H, J=8.0, 1.7 Hz), 7.74 (dd, 1H, J=10.0, 1.7 Hz), 7.68 (t, 1H, J=7.6 Hz), 7.31 (d, 2H, J=8.2 Hz), 7.07 (d, 2H, J=8.3 Hz), 4.91 (s, 2H), 3.70 (d, 4H, J=5.8 Hz), 3.51 (s, 2H), 2.85-2.38 (m, 15H); LRMS (ESI) m/z 611.4 (M$^+$+H).

Example 177. Compound 21516: N-(4-(5-(difluoromethyl)-1,3,4-oxadiazol-2-yl)-2-fluorobenzyl)-N-(4-((4-methylpiperazin-1-yl)methyl)phenyl)thiomorpholine-4-carboxamide 1,1-dioxide

[Step 1] (N-(4-(2-(2,2-difluoroacetyl)hydrazine-1-carbonyl)-2-fluorobenzyl)-N-(4-((4-methylpiperazin-1-yl)methyl)phenyl)thiomorpholine-4-carboxamide 1,1-dioxide

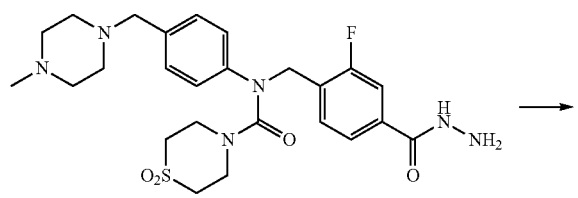

632

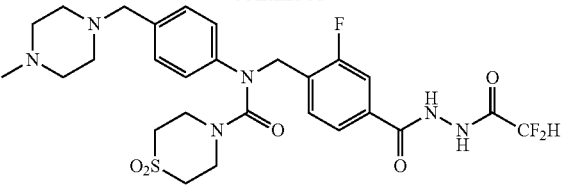

A solution of N-(2-fluoro-4-(hydrazinecarbonyl)benzyl)-N-(4-((4-methylpiperazin-1-yl)methyl)phenyl) thiomorpholine-4-carboxamide 1,1-dioxide (0.058 g, 0.109 mmol) prepared in Step 4 of Example 176 and triethylamine (0.030 mL, 0.218 mmol) in dichloromethane (1 mL) was mixed at the room temperature with difluoroacetic anhydride (0.012 mL, 0.098 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The the title compound was used without further purification (0.054 g, 81.1%, brown foam).

[Step 2] Compound 21516

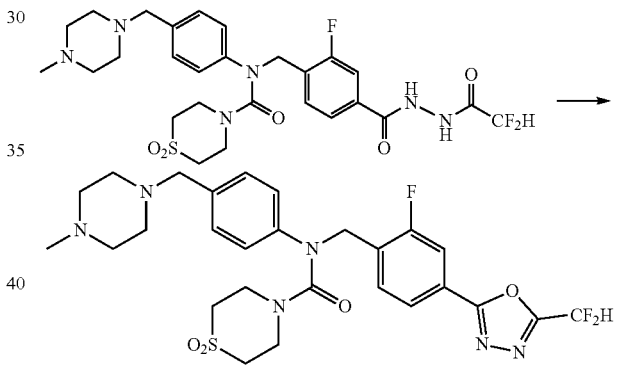

N-(4-(2-(2,2-difluoroacetyl)hydrazine-1-carbonyl)-2-fluorobenzyl)-N-(4-((4-methylpiperazin-1-yl)methyl)phenyl)thiomorpholine-4-carboxamide 1,1-dioxide (0.054 g, 0.088 mmol) prepared in Step 1 and 1-methoxy-N-triethylammoniosulfonyl-methanimidate (Burgess reagent, 0.032 g, 0.133 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(5-(difluoromethyl)-1,3,4-oxadiazol-2-yl)-2-fluorobenzyl)-N-(4-((4-methylpiperazin-1-yl)methyl)phenyl)thiomorpholine-4-carboxamide 1,1-dioxide as pale yellow foam (0.023 g, 42.9%).

$^1$H NMR (400 MHz, CDCl$_3$) δ 7.87 (dd, 1H, J=8.0, 1.7 Hz), 7.74 (dd, 1H, J=10.1, 1.6 Hz), 7.66 (t, 1H, J=7.6 Hz), 7.30 (d, 2H, J=8.2 Hz), 7.11-7.06 (m, 2H), 6.92 (t, 1H,

J=51.7 Hz), 4.90 (s, 2H), 3.71 (s, 4H), 3.55 (s, 2H), 3.12-2.50 (m, 15H); LRMS (ESI) m/z 593.1 (M⁺+H).

Example 178. Compound 21517: N-(2-fluoro-4-(5-(trifluoromethyl)-1,3,4-oxadiazol-2-yl)benzyl)-N-(4-(pyridin-3-yl)phenyl)thiomorpholine-4-carboxamide 1,1-dioxide

[Step 1] N-(4-bromophenyl)thiomorpholine-4-carboxamide 1,1-dioxide

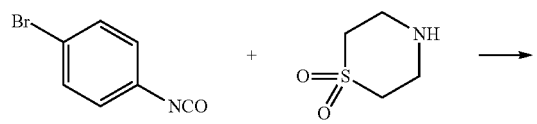

A solution of 1-bromo-4-isocyanatobenzene (2.000 g, 10.100 mmol) and thiomorpholine 1,1-dioxide (1.365 g, 10.100 mmol) in diethylether (50 mL) was stirred at the room temperature for 16 hr. The precipitates were collected by filtration, washed by diethylether, and dried to give the title compound N-(4-bromophenyl)thiomorpholine-4-carboxamide 1,1-dioxide as white solid (3.268 g, 97.1%).

[Step 2] Methyl 4-((N-(4-bromophenyl)-1,1-dioxidothiomorpholine-4-carboxamido)methyl)-3-fluorobenzoate

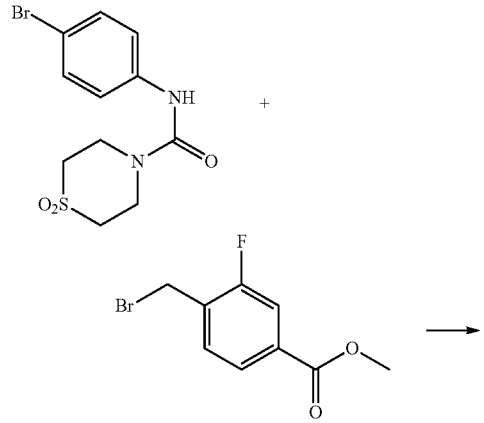

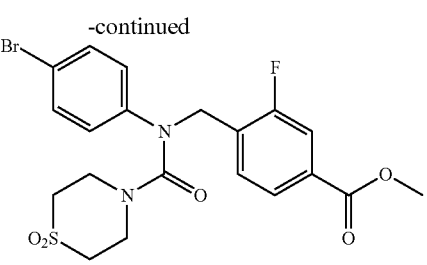

To a stirred solution of N-(4-bromophenyl)thiomorpholine-4-carboxamide 1,1-dioxide (1.500 g, 4.502 mmol) prepared in Step 1 in N,N-dimethylformamide (15 mL) was added at 0.0° C. sodium hydride (60.00%, 0.180 g, 4.502 mmol). The reaction mixture was stirred at the same temperature for 30 min. Methyl 4-(bromomethyl)-3-fluorobenzoate (1.112 g, 4.502 mmol) was added to the reaction mixture, and stirred at the room temperature for additional 4 hr. The precipitates were collected by filtration, washed by diethylether, and dried to give the title compound methyl 4-((N-(4-bromophenyl)-1,1-dioxidothiomorpholine-4-carboxamido)methyl)-3-fluorobenzoate as white solid (1.314 g, 58.5%).

[Step 3] Methyl 4-((1,1-dioxido-N-(4-(pyridin-3-yl)phenyl)thiomorpholine-4-carboxamido)methyl)-3-fluorobenzoate

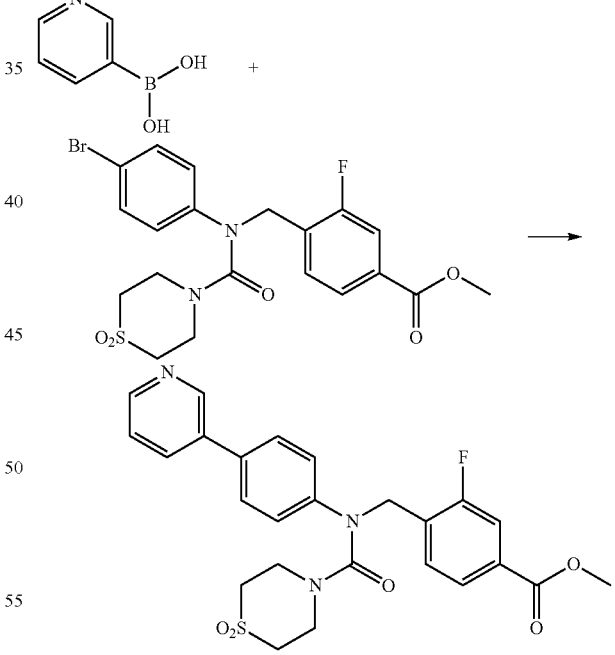

Methyl 4-((N-(4-bromophenyl)-1,1-dioxidothiomorpholine-4-carboxamido)methyl)-3-fluorobenzoate (0.300 g, 0.601 mmol) prepared in Step 2, pyridin-3-ylboronic acid (0.089 g, 0.721 mmol), [1,1'-bis(di-tert-butylphosphino)ferrocene]palladium(II) dichloride (Pd(dtbpf)Cl₂, 0.020 g, 0.030 mmol) and cesium carbonate (0.584 g, 1.802 mmol) in water (1 mL)/1,4-dioxane (3 mL) was mixed at the room temperature and then heated at 100° C. under the microwaves for 20 min, and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound methyl 4-((1,1-dioxido-N-(4-(pyridin-3-yl)phenyl)thiomorpholine-4-carboxamido)methyl)-3-fluorobenzoate as brown foam (0.262 g, 87.7%).

[Step 4] N-(2-fluoro-4-(hydrazinecarbonyl)benzyl)-N-(4-(pyridin-3-yl)phenyl)thiomorpholine-4-carboxamide 1,1-dioxide

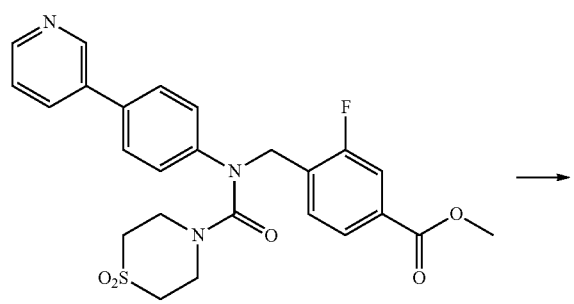

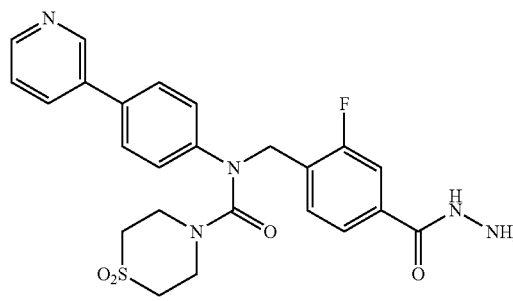

Methyl 4-((1,1-dioxido-N-(4-(pyridin-3-yl)phenyl)thiomorpholine-4-carboxamido)methyl)-3-fluorobenzoate (0.262 g, 0.527 mmol) prepared in Step 3 and hydrazine monohydrate (0.249 mL, 5.266 mmol) were mixed at the room temperature in water (1 mL)/1,4-dioxane (4 mL) and then stirred at 100° C. for 16 hr, and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(hydrazinecarbonyl)benzyl)-N-(4-(pyridin-3-yl)phenyl)thiomorpholine-4-carboxamide 1,1-dioxide as pale brown foam (0.244 g, 93.2%).

[Step 5] N-(2-fluoro-4-(2-(2,2,2-trifluoroacetyl)hydrazine-1-carbonyl)benzyl)-N-(4-(pyridin-3-yl) phenyl)thiomorpholine-4-carboxamide 1,1-dioxide


A solution of N-(2-fluoro-4-(hydrazinecarbonyl)benzyl)-N-(4-(pyridin-3-yl)phenyl)thiomorpholine-4-carboxamide 1,1-dioxide (0.122 g, 0.245 mmol) prepared in Step 4 and triethylamine (0.068 mL, 0.491 mmol) in dichloromethane (1 mL) was mixed at the room temperature with trifluoroacetic anhydride (0.038 mL, 0.221 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.122 g, 83.8%, brown foam).

[Step 6] Compound 21517


N-(2-fluoro-4-(2-(2,2,2-trifluoroacetyl)hydrazine-1-carbonyl)benzyl)-N-(4-(pyridin-3-yl)phenyl)thiomorpholine-4-carboxamide 1,1-dioxide (0.122 g, 0.206 mmol) prepared in Step 5 and 1-methoxy-N-triethylammoniosulfonyl-methanimidate (Burgess reagent, 0.073 g, 0.308 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(2-fluoro-4-(5-(trifluoromethyl)-1,3,4-oxadiazol-2-yl)benzyl)-N-(4-(pyridin-3-yl)phenyl)thiomorpholine-4-carboxamide 1,1-dioxide as pale yellow foam (0.028 g, 23.8%).

$^1$H NMR (400 MHz, CDCl$_3$) δ 8.83 (d, 1H, J=2.3 Hz), 8.65-8.59 (m, 1H), 7.89 (dd, 1H, J=8.0, 1.7 Hz), 7.85 (ddd, 1H, J=8.0, 2.5, 1.7 Hz), 7.77 (dd, 1H, J=10.0, 1.7 Hz), 7.72 (t, 1H, J=7.6 Hz), 7.63-7.56 (m, 2H), 7.43-7.34 (m, 1H), 7.24 (d, 1H, J=2.1 Hz), 4.99 (s, 2H), 3.76 (d, 4H, J=5.4 Hz), 2.87 (t, 4H, J=5.3 Hz); LRMS (ESI) m/z 576.13 (M$^+$+H).

Example 179. Compound 21518: N-(4-(5-(difluoromethyl)-1,3,4-oxadiazol-2-yl)-2-fluorobenzyl)-N-(4-(pyridin-3-yl)phenyl)thiomorpholine-4-carboxamide 1,1-dioxide

[Step 1] (N-(4-(2-(2,2-difluoroacetyl)hydrazine-1-carbonyl)-2-fluorobenzyl)-N-(4-(pyridin-3-yl)phenyl)thiomorpholine-4-carboxamide 1,1-dioxide

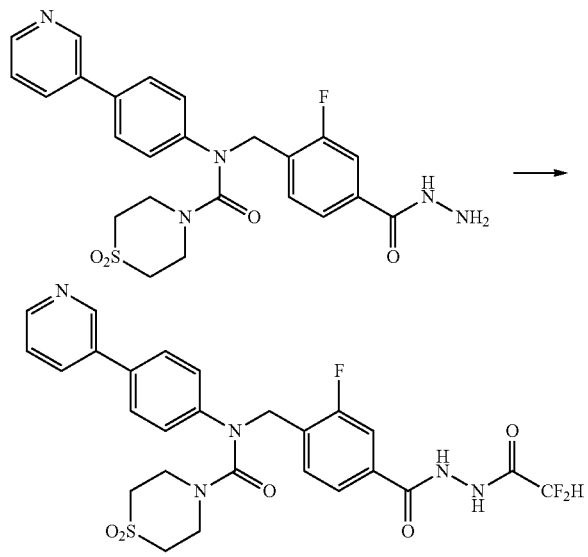

A solution of N-(2-fluoro-4-(hydrazinecarbonyl)benzyl)-N-(4-(pyridin-3-yl)phenyl)thiomorpholine-4-carboxamide 1,1-dioxide (0.122 g, 0.245 mmol) prepared in Step 4 of Example 178 and triethylamine (0.068 mL, 0.491 mmol) in dichloromethane (1 mL) was mixed at the room temperature with difluoroacetic anhydride (0.027 mL, 0.221 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.106 g, 75.0%, brown foam).

[Step 2] Compound 21518

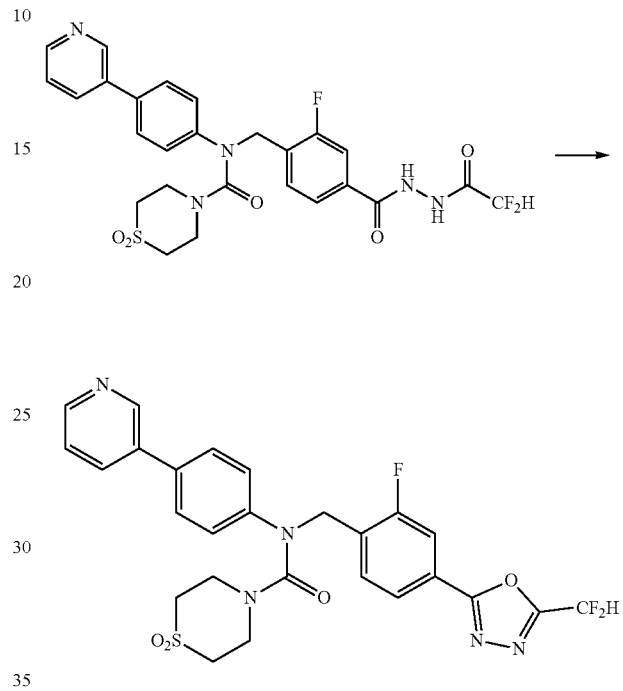

N-(4-(2-(2,2-difluoroacetyl)hydrazine-1-carbonyl)-2-fluorobenzyl)-N-(4-(pyridin-3-yl)phenyl)thiomorpholine-4-carboxamide 1,1-dioxide (0.106 g, 0.184 mmol) prepared in Step 1 and 1-methoxy-N-triethylammoniosulfonyl-methanimidate (Burgess reagent, 0.066 g, 0.276 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(5-(difluoromethyl)-1,3,4-oxadiazol-2-yl)-2-fluorobenzyl)-N-(4-(pyridin-3-yl)phenyl)thiomorpholine-4-carboxamide 1,1-dioxide as pale yellow foam (0.024 g, 23.6%).

$^1$H NMR (400 MHz, CDCl$_3$) δ 8.83 (s, 1H), 8.62 (d, 1H, J=4.8 Hz), 7.89 (dd, 1H, J=8.0, 1.7 Hz), 7.85 (dt, 1H, J=7.9, 2.1 Hz), 7.77 (dd, 1H, J=10.0, 1.6 Hz), 7.70 (t, 1H, J=7.7 Hz), 7.63-7.56 (m, 2H), 7.38 (dd, 1H, J=7.9, 4.8 Hz), 7.24 (d, 2H, J=8.6 Hz), 6.91 (s, 1H), 4.99 (s, 2H), 3.75 (d, 4H, J=5.9 Hz), 2.87 (t, 4H, J=5.3 Hz); LRMS (ESI) m/z 558.3 (M$^+$+H).

Example 180. Compound 21519: N-(2-fluoro-4-(5-(trifluoromethyl)-1,3,4-oxadiazol-2-yl)benzyl)-N-(4-(pyridin-4-yl)phenyl)thiomorpholine-4-carboxamide 1,1-dioxide

[Step 1] Methyl 4-((1,1-dioxido-N-(4-(pyridin-4-yl)phenyl)thiomorpholine-4-carboxamido)methyl)-3-fluorobenzoate

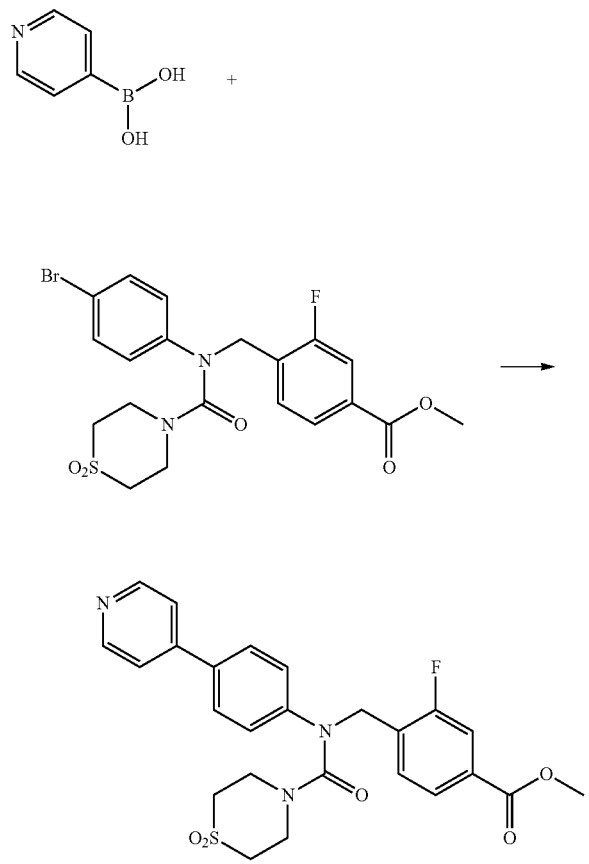

Methyl 4-((N-(4-bromophenyl)-1,1-dioxidothiomorpholine-4-carboxamido)methyl)-3-fluorobenzoate (0.300 g, 0.601 mmol) prepared in Step 2 of Example 178, pyridin-4-ylboronic acid (0.089 g, 0.721 mmol), [1,1'-bis(di-tert-butylphosphino)ferrocene]palladium(II) dichloride (Pd(dtb-pf)Cl$_2$, 0.020 g, 0.030 mmol) and cesium carbonate (0.584 g, 1.802 mmol) in water (1 mL)/1,4-dioxane (3 mL) was mixed at the room temperature and then heated at 100° C. under the microwaves for 20 min, and cooled down to the room temperature to terminate the reaction. The reaction mixture was concentrated under the reduced pressure and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound methyl 4-((1,1-dioxido-N-(4-(pyridin-4-yl)phenyl)thiomorpholine-4-carboxamido)methyl)-3-fluorobenzoate as brown foam (0.175 g, 58.4%).

[Step 2] N-(2-fluoro-4-(hydrazinecarbonyl)benzyl)-N-(4-(pyridin-4-yl)phenyl)thiomorpholine-4-carboxamide 1,1-dioxide

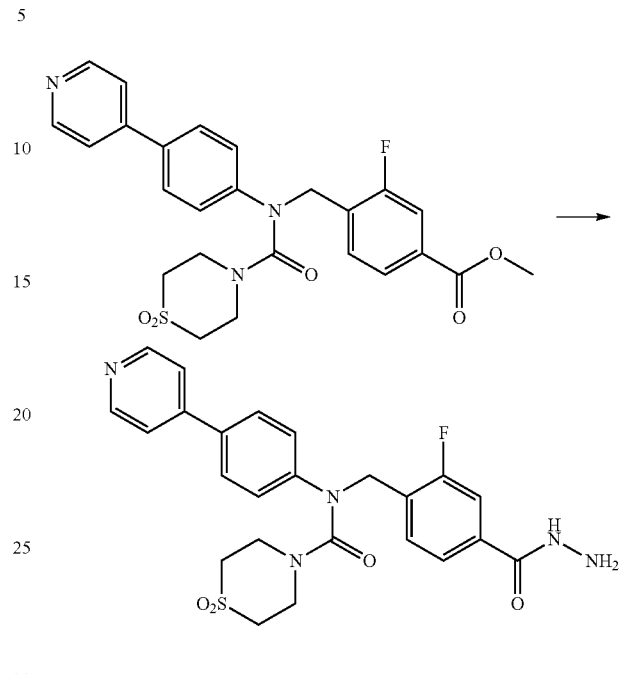

Methyl 4-((1,1-dioxido-N-(4-(pyridin-4-yl)phenyl)thiomorpholine-4-carboxamido)methyl)-3-fluorobenzoate (0.175 g, 0.351 mmol) prepared in Step 1 and hydrazine monohydrate (0.166 mL, 3.513 mmol) were mixed at the room temperature in water (1 mL)/1,4-dioxane (4 mL) and then stirred at 100° C. for 16 hr, and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(hydrazinecarbonyl)benzyl)-N-(4-(pyridin-4-yl)phenyl)thiomorpholine-4-carboxamide 1,1-dioxide as pale brown foam (0.160 g, 91.4%).

[Step 3] N-(2-fluoro-4-(2-(2,2,2-trifluoroacetyl)hydrazine-1-carbonyl)benzyl)-N-(4-(pyridin-4-yl)phenyl)thiomorpholine-4-carboxamide 1,1-dioxide

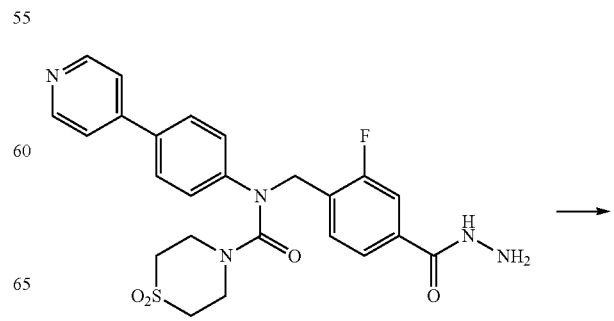

-continued

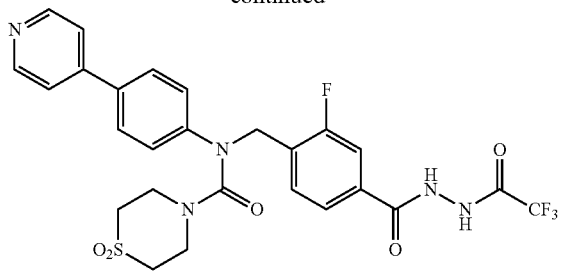

A solution of N-(2-fluoro-4-(hydrazinecarbonyl)benzyl)-N-(4-(pyridin-4-yl)phenyl)thiomorpholine-4-carboxamide 1,1-dioxide (0.075 g, 0.151 mmol) prepared in Step 2 and triethylamine (0.042 mL, 0.301 mmol) in dichloromethane (1 mL) was mixed at the room temperature with trifluoroacetic anhydride (0.024 mL, 0.135 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.073 g, 81.7%, brown foam).

[Step 4] Compound 21519

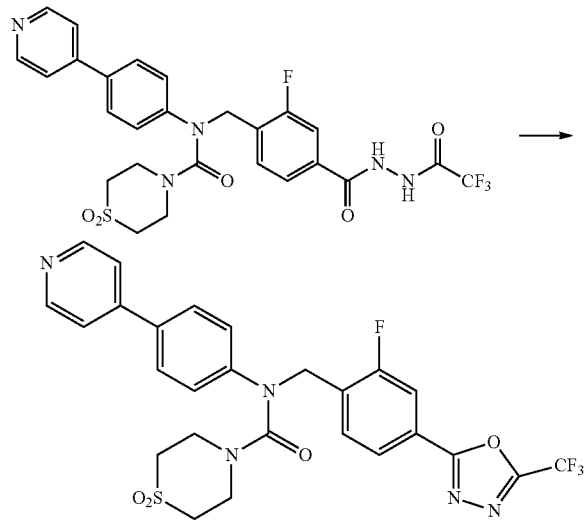

N-(2-fluoro-4-(2-(2,2,2-trifluoroacetyl)hydrazine-1-carbonyl)benzyl)-N-(4-(pyridin-4-yl)phenyl)thiomorpholine-4-carboxamide 1,1-dioxide (0.073 g, 0.123 mmol) prepared in Step 3 and 1-methoxy-N-triethylammoniosulfonyl-methanimidate (Burgess reagent, 0.044 g, 0.184 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(2-fluoro-4-(5-(trifluoromethyl)-1,3,4-oxadiazol-2-yl)benzyl)-N-(4-(pyridin-4-yl)phenyl)thiomorpholine-4-carboxamide 1,1-dioxide as pale yellow foam (0.027 g, 38.3%).

$^1$H NMR (400 MHz, CDCl$_3$) δ 8.71-8.65 (m, 2H), 7.89 (dd, 1H, J=8.0, 1.7 Hz), 7.77 (dd, 1H, J=10.1, 1.7 Hz), 7.71 (t, 1H, J=7.6 Hz), 7.68-7.62 (m, 2H), 7.50-7.44 (m, 2H), 7.25 (d, 1H, J=2.0 Hz), 5.00 (s, 2H), 3.75 (s, 4H), 2.87 (t, 4H, J=5.3 Hz); LRMS (ESI) m/z 576.0 (M$^+$+H).

Example 181. Compound 21520: N-(4-(5-(difluoromethyl)-1,3,4-oxadiazol-2-yl)-2-fluorobenzyl)-N-(4-(pyridin-4-yl)phenyl)thiomorpholine-4-carboxamide 1,1-dioxide

[Step 1] N-(4-(2-(2,2-difluoroacetyl)hydrazine-1-carbonyl)-2-fluorobenzyl)-N-(4-(pyridin-4-yl)phenyl)thiomorpholine-4-carboxamide 1,1-dioxide

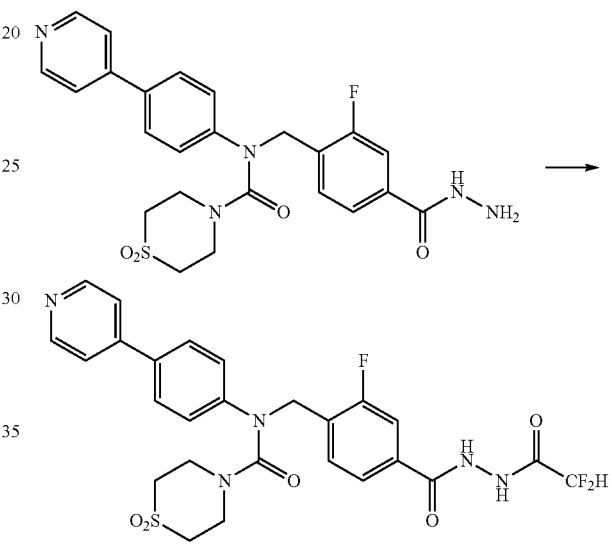

A solution of N-(2-fluoro-4-(hydrazinecarbonyl)benzyl)-N-(4-(pyridin-4-yl)phenyl)thiomorpholine-4-carboxamide 1,1-dioxide (0.075 g, 0.151 mmol) prepared in Step 2 of Example 180 and triethylamine (0.042 mL, 0.301 mmol) in dichloromethane (1 mL) was mixed at the room temperature with difluoroacetic anhydride (0.017 mL, 0.135 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.065 g, 75.0%, brown foam).

[Step 2] Compound 21520

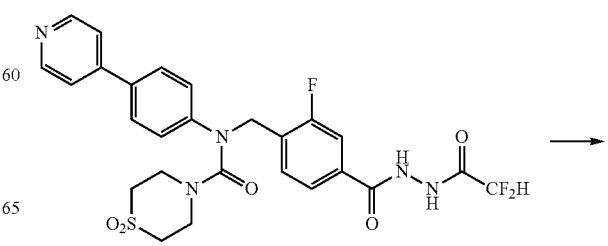

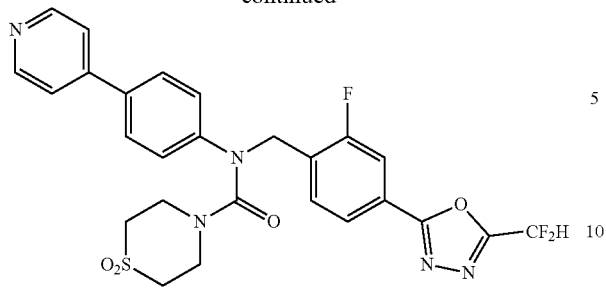

N-(4-(2-(2,2-difluoroacetyl)hydrazine-1-carbonyl)-2-fluorobenzyl)-N-(4-(pyridin-4-yl)phenyl)thiomorpholine-4-carboxamide 1,1-dioxide (0.065 g, 0.113 mmol) prepared in Step 1 and 1-methoxy-N-triethylammoniosulfonyl-methanimidate (Burgess reagent, 0.040 g, 0.169 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 3%) to give the title compound N-(4-(5-(difluoromethyl)-1,3,4-oxadiazol-2-yl)-2-fluorobenzyl)-N-(4-(pyridin-4-yl)phenyl)thiomorpholine-4-carboxamide 1,1-dioxide as pale yellow foam (0.029 g, 46.4%).

$^1$H NMR (400 MHz, $CDCl_3$) δ 8.71-8.65 (m, 2H), 7.89 (dd, 1H, J=8.0, 1.7 Hz), 7.77 (dd, 1H, J=10.2, 1.6 Hz), 7.69 (t, 1H, J=7.7 Hz), 7.67-7.62 (m, 2H), 7.50-7.44 (m, 2H), 7.24 (s, 1H), 6.91 (s, 1H), 4.99 (s, 2H), 3.74 (d, 4H, J=5.5 Hz), 2.87 (t, 4H, J=5.3 Hz); LRMS (ESI) m/z 558.3 (M$^+$+H).

Example 182. Compound 21521: N-(2-fluoro-4-(5-(trifluoromethyl)-1,3,4-oxadiazol-2-yl)benzyl)-N-(4-(1-methyl-1H-indol-5-yl)phenyl)thiomorpholine-4-carboxamide 1,1-dioxide

[Step 1] Methyl 3-fluoro-4-((N-(4-(1-methyl-1H-indol-5-yl)phenyl)-1,1-dioxidothiomorpholine-4-carboxamido)methyl)benzoate

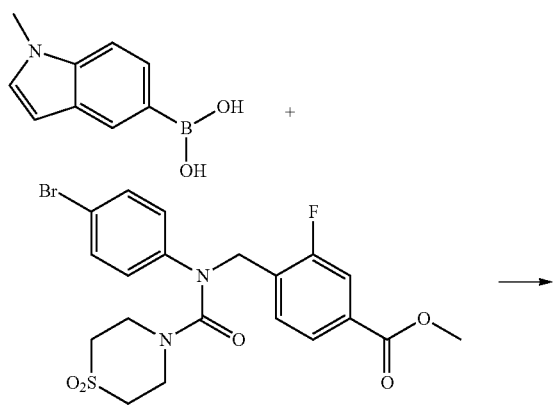

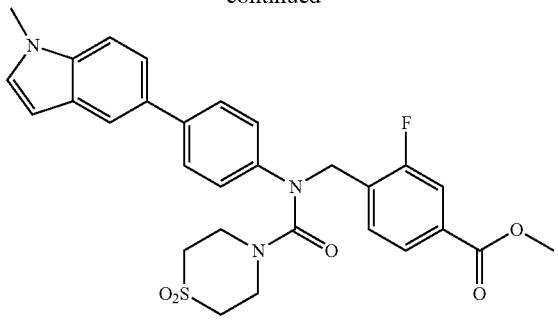

Methyl 4-((N-(4-bromophenyl)-1,1-dioxidothiomorpholine-4-carboxamido)methyl)-3-fluorobenzoate (0.300 g, 0.601 mmol) prepared in Step 2 of Example 178, (1-methyl-1H-indol-5-yl)boronic acid (0.126 g, 0.721 mmol), [1,1'-bis(di-tert-butylphosphino)ferrocene]palladium(II) dichloride (Pd(dtbpf)Cl$_2$, 0.020 g, 0.030 mmol) and cesium carbonate (0.584 g, 1.802 mmol) in water (1 mL)/1,4-dioxane (3 mL) was mixed at the room temperature and then heated at 100° C. under the microwaves for 20 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 5%) to give the title compound methyl 3-fluoro-4-((N-(4-(1-methyl-1H-indol-5-yl)phenyl)-1,1-dioxidothiomorpholine-4-carboxamido)methyl)benzoate as brown foam (0.352 g, 106.5%).

[Step 2] N-(2-fluoro-4-(hydrazinecarbonyl)benzyl)-N-(4-(1-methyl-1H-indol-5-yl)phenyl)thiomorpholine-4-carboxamide 1,1-dioxide

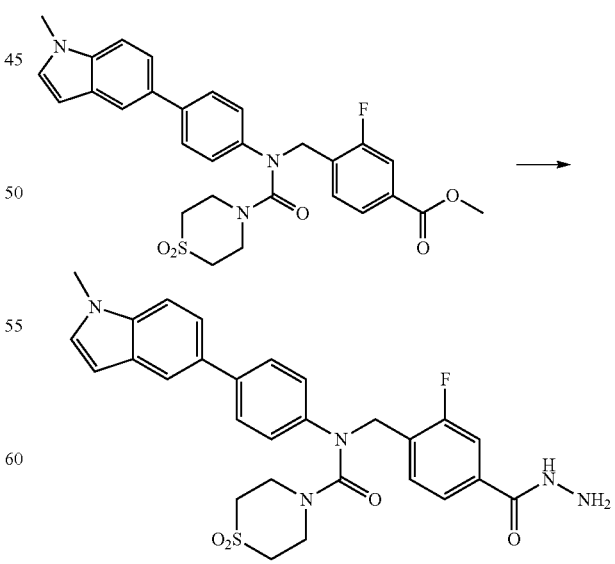

Methyl 3-fluoro-4-((N-(4-(1-methyl-1H-indol-5-yl)phenyl)-1,1-dioxidothiomorpholine-4-carboxamido)methyl)

benzoate (0.352 g, 0.640 mmol) prepared in Step 1 and hydrazine monohydrate (0.302 mL, 6.401 mmol) were mixed at the room temperature in water (1 mL)/1,4-dioxane (4 mL) and then stirred at 100° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(hydrazinecarbonyl)benzyl)-N-(4-(1-methyl-1H-indol-5-yl)phenyl)thiomorpholine-4-carboxamide 1,1-dioxide as pale brown foam (0.297 g, 84.3%).

[Step 3] N-(2-fluoro-4-(2-(2,2,2-trifluoroacetyl)hydrazine-1-carbonyl)benzyl)-N-(4-(1-methyl-1H-indol-5-yl)phenyl)thiomorpholine-4-carboxamide 1,1-dioxide

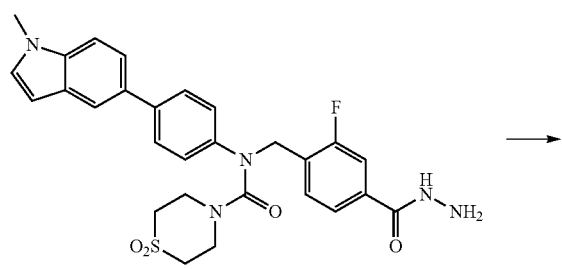

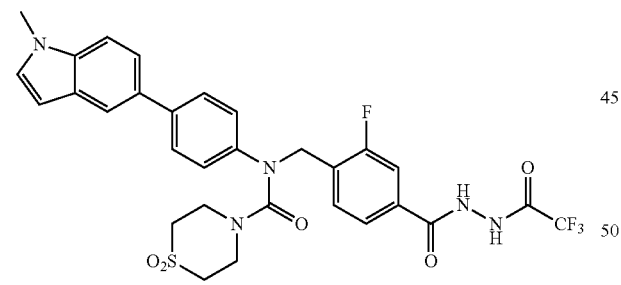

A solution of N-(2-fluoro-4-(hydrazinecarbonyl)benzyl)-N-(4-(1-methyl-1H-indol-5-yl)phenyl)thiomorpholine-4-carboxamide 1,1-dioxide (0.148 g, 0.230 mmol) prepared in Step 2 and triethylamine (0.063 mL, 0.459 mmol) in dichloromethane (1 mL) was mixed at the room temperature with trifluoroacetic anhydride (0.036 mL; 0.207 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.102 g, 68.8%, brown foam).

[Step 4] Compound 21521

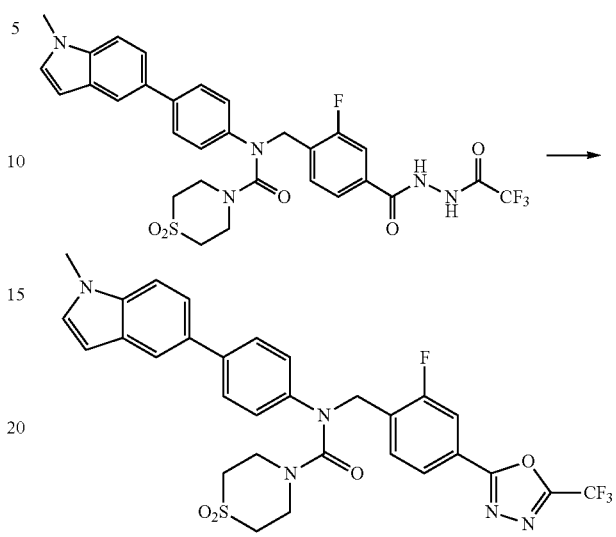

N-(2-fluoro-4-(2-(2,2,2-trifluoroacetyl)hydrazine-1-carbonyl)benzyl)-N-(4-(1-methyl-1H-indol-5-yl)phenyl)thiomorpholine-4-carboxamide 1,1-dioxide (0.102 g, 0.158 mmol) prepared in Step 3 and 1-methoxy-N-triethylammoniosulfonyl-methanimidate (Burgess reagent, 0.056 g, 0.237 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (Waters, C18; acetonitrile/aqueous 5%-formic acid solution=5% to 75%) to give the title compound N-(2-fluoro-4-(5-(trifluoromethyl)-1,3,4-oxadiazol-2-yl)benzyl)-N-(4-(1-methyl-1H-indol-5-yl)phenyl)thiomorpholine-4-carboxamide 1,1-dioxide as white solid (0.003 g, 3.0%).

$^1$H NMR (400 MHz, CDCl$_3$) δ 7.88 (s, 1H), 7.83-7.60 (m, 4H), 7.52-7.32 (m, 2H), 7.22-7.07 (m, 2H), 6.53 (m, 3H), 4.98 (s, 2H), 3.86 (s, 3H), 3.70 (s, 4H), 2.84 (s, 4H); LRMS (ESI) m/z 628.3 (M$^+$+H).

Example 183. Compound 21522: N-(4-(5-(difluoromethyl)-1,3,4-oxadiazol-2-yl)-2-fluorobenzyl)-N-phenyl-2-oxa-6-azaspiro[3.3]heptane-6-carboxamide

[Step 1] Methyl 3-fluoro-4-((N-phenyl-2-oxa-6-azaspiro[3.3]heptane-6-carboxamido)methyl)benzoate

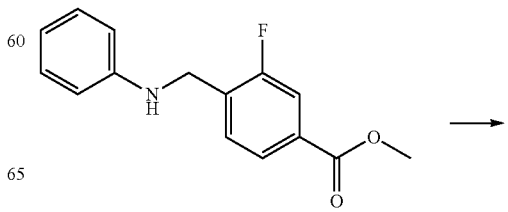

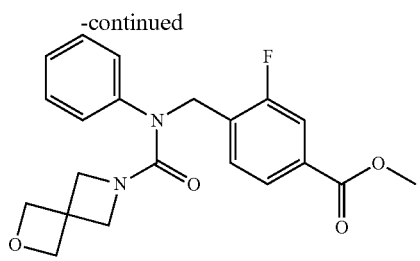

A solution of methyl 3-fluoro-4-((phenylamino)methyl) benzoate (0.500 g, 1.928 mmol), triphosgene (0.458 g, 1.543 mmol) and N,N-diisopropylethylamine (1.684 mL, 9.642 mmol) in dichloromethane (10 mL) was mixed at 0° C. with 2-oxa-6-azaspiro[3.3]heptane (0.229 g, 2.314 mmol), and stirred at the same temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 12 g cartridge; ethyl acetate/hexane=40% to 70%) to give the title compound methyl 3-fluoro-4-((N-phenyl-2-oxa-6-azaspiro[3.3]heptane-6-carboxamido)methyl)benzoate as pale yellow oil (0.558 g, 75.3%).

[Step 2] N-(2-fluoro-4-(hydrazinecarbonyl)benzyl)-N-phenyl-2-oxa-6-azaspiro[3.3]heptane-6-carboxamide

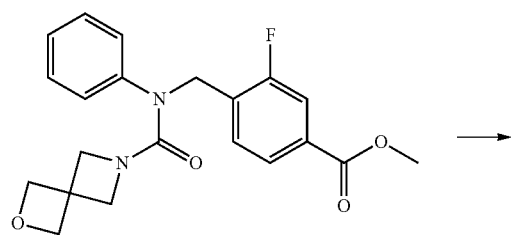

Methyl 3-fluoro-4-((N-phenyl-2-oxa-6-azaspiro[3.3]heptane-6-carboxamido)methyl)benzoate (0.558 g, 1.452 mmol) prepared in Step 1 and hydrazine monohydrate (1.411 mL, 29.032 mmol) in ethanol (10 mL) was mixed at the room temperature and then heated at 120° C. under the microwaves for 1 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (0.504 g, 90.3%, white solid).

[Step 3] N-(4-(2-(2,2-difluoroacetyl)hydrazine-1-carbonyl)-2-fluorobenzyl)-N-phenyl-2-oxa-6-azaspiro[3.3]heptane-6-carboxamide

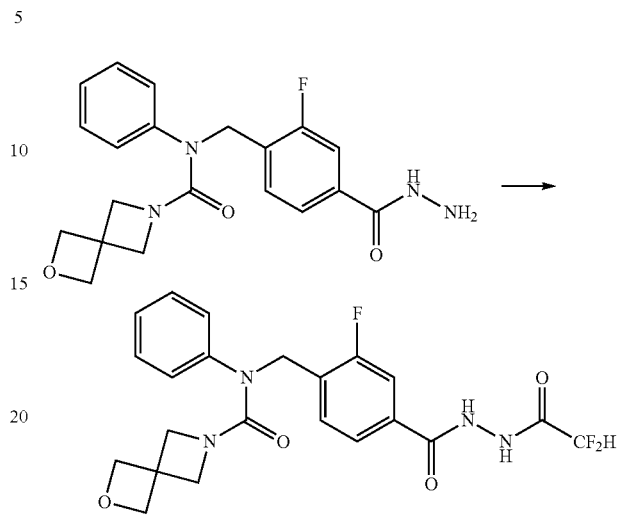

A solution of N-(2-fluoro-4-(hydrazinecarbonyl)benzyl)-N-phenyl-2-oxa-6-azaspiro[3.3]heptane-6-carboxamide (0.504 g, 1.311 mmol) prepared in Step 2 and triethylamine (0.273 mL, 1.967 mmol) in dichloromethane (10 mL) was mixed at the room temperature with 2,2-difluoroacetic anhydride (0.147 mL, 1.180 mmol), and stirred at the same temperature for 1 hr. The reaction mixture was concentrated under the reduced pressure to remove the solvent. The concentrate was purified and concentrated by column chromatography ($SiO_2$, 12 g cartridge; methanol/dichloromethane=0% to 10%) to give the title compound N-(4-(2-(2,2-difluoroacetyl)hydrazine-1-carbonyl)-2-fluorobenzyl)-N-phenyl-2-oxa-6-azaspiro[3.3]heptane-6-carboxamide as white solid (0.471 g, 77.7%).

[Step 4] Compound 21522

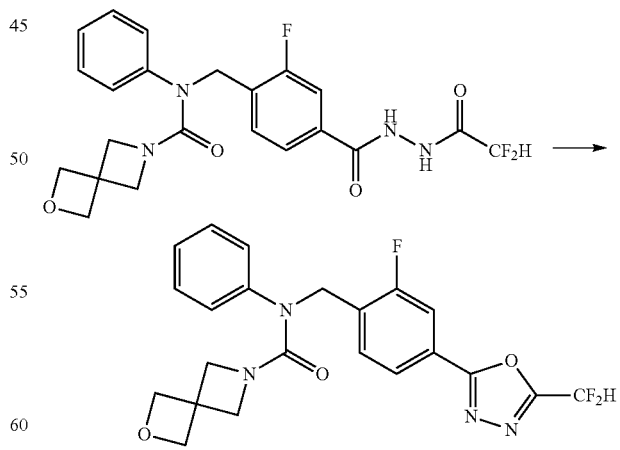

N-(4-(2-(2,2-difluoroacetyl)hydrazine-1-carbonyl)-2-fluorobenzyl)-N-phenyl-2-oxa-6-azaspiro[3.3]heptane-6-carboxamide (0.471 g, 1.019 mmol) prepared in Step 3 and 1-methoxy-N-triethylammoniosulfonyl-methanimidate (Burgess reagent, 0.364 g, 1.528 mmol) in tetrahydrofuran (10 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=30% to 80%) to give the title compound N-(4-(5-(difluoromethyl)-1.3.4-oxadiazol-2-yl)-2-fluorobenzyl)-N-phenyl-2-oxa-6-azaspiro[3.3]heptane-6-carboxamide as white solid (0.079 g, 17.5%).

$^1$H NMR (400 MHz, CDCl$_3$) δ 7.87 (dd, 1H. J=8.0, 1.5 Hz), 7.73-7.69 (m, 2H), 7.35 (t, 2H, J=7.5 Hz), 7.27-7.25 (m, 1H), 7.15-7.13 (m, 2H), 6.92 (t, 1H, J=51.7 Hz), 5.00 (s, 2H), 4.63 (s, 4H), 3.73 (s, 4H); LRMS (ES) m/z 445.4 (M$^+$+1).

Example 184. Compound 21527: N-((5-(5-(difluoromethyl)-1,3,4-oxadiazol-2-yl)pyridin-2-yl)methyl)-4-methyl-N-phenylpiperazine-1-carboxamide

[Step 1] 4-Methyl-N-phenylpiperazine-1-carboxamide

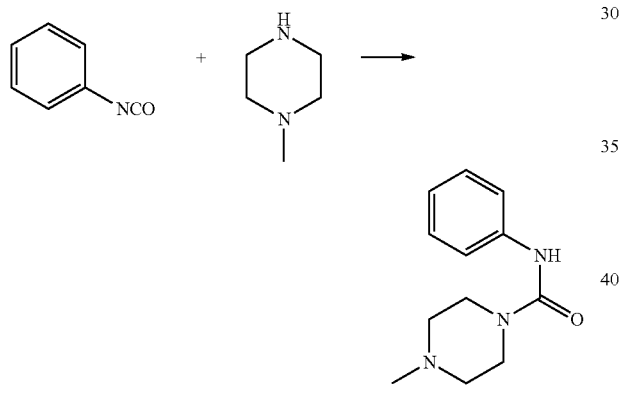

A solution of isocyanatobenzene (1.372 mL, 12.592 mmol) and 1-methylpiperazine (1.314 mL, 12.592 mmol) in diethylether (20 mL) was stirred at the room temperature for 2 hr. The precipitates were collected by filtration, washed by aqueous 1N-acetic acid solution, and dried to give the title compound 4-methyl-N-phenylpiperazine-1-carboxamide as white solid (1.870 g. 67.7%).

[Step 2] Methyl 6-((4-methyl-N-phenylpiperazine-1-carboxamido)methyl)nicotinate

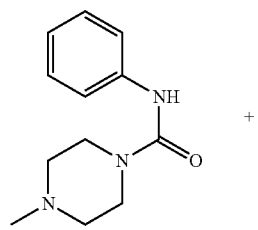

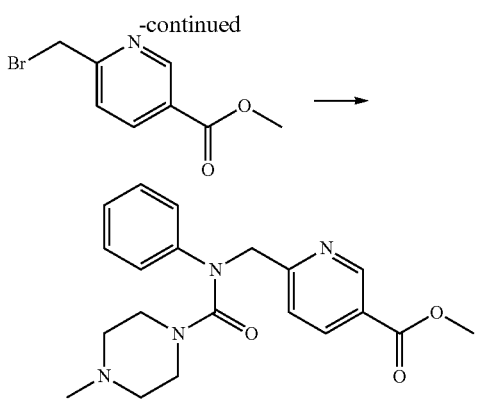

To a stirred solution of 4-methyl-N-phenylpiperazine-1-carboxamide (0.480 g, 2.189 mmol) in N,N-dimethylformamide (20 mL) was added at the room temperature sodium hydride (60.00%, 0.140 g, 3.502 mmol). The reaction mixture was stirred at the same temperature for 30 min. Methyl 6-(bromomethyl)nicotinate (0.504 g, 2.189 mmol) was added to the reaction mixture. and stirred at the same temperature for additional 8 hr. Then, water was added to the reaction mixture. followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give the title compound methyl 6-((4-methyl-N-phenylpiperazine-1-carboxamido)methyl)nicotinate as colorless oil (0.250 g, 31.0%).

[Step 3] N-((5-(hydrazinecarbonyl)pyridin-2-yl)methyl)-4-methyl-N-phenylpiperazine-1-carboxamide

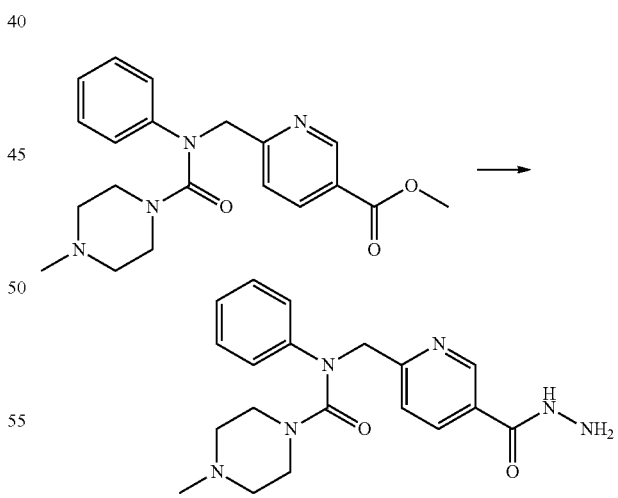

A mixture of methyl 6-((4-methyl-N-phenylpiperazine-1-carboxamido)methyl)nicotinate (0.250 g, 0.679 mmol) prepared in Step 2 and hydrazine hydrate (0.641 mL, 13.571 mmol) in ethanol (10 mL) was heated at 120° C. for 1 hr under the microwaves, and cooled down to the room temperature to terminate the reaction. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (0.192 g, 76.8%, colorless oil).

[Step 4] N-((5-(2-(2,2-difluoroacetyl)hydrazine-1-carbonyl)pyridin-2-yl)methyl)-4-methyl-N-phenylpiperazine-1-carboxamide

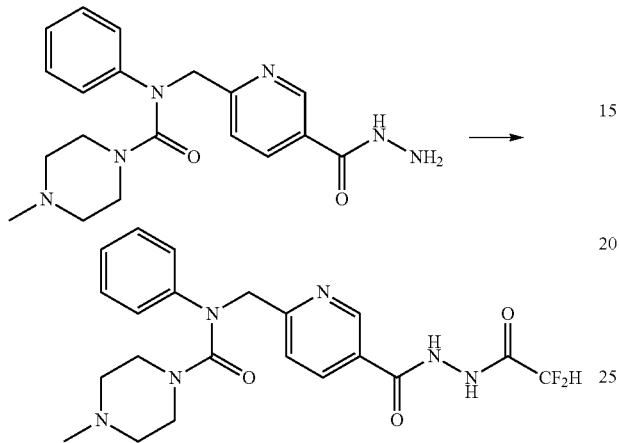

A solution of N-((5-(hydrazinecarbonyl)pyridin-2-yl) methyl)-4-methyl-N-phenylpiperazine-1-carboxamide (0.192 g, 0.521 mmol) prepared in Step 3, triethylamine (0.108 mL, 0.782 mmol) and difluoroacetic anhydride (0.051 mL, 0.469 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give the title compound N-((5-(2-(2,2-difluoroacetyl)hydrazine-1-carbonyl)pyridin-2-yl)methyl)-4-methyl-N-phenylpiperazine-1-carboxamide as colorless oil (0.230 g, 98.9%).

[Step 5] Compound 21527

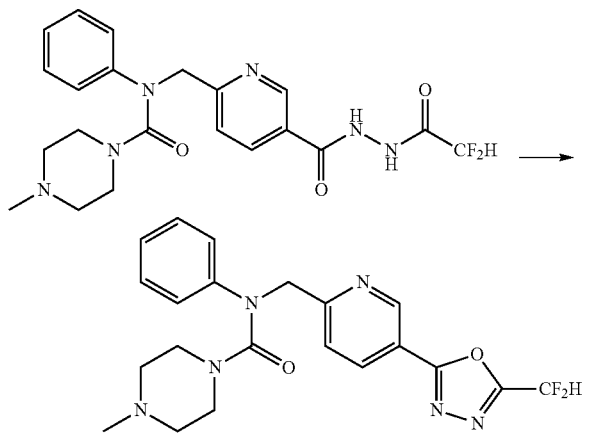

A mixture of N-((5-(2-(2,2-difluoroacetyl)hydrazine-1-carbonyl)pyridin-2-yl)methyl)-4-methyl-N-phenylpiperazine-1-carboxamide (0.260 g, 0.582 mmol) prepared in Step 4 and 1-methoxy-N-triethylammoniosulfonyl-methanimidate (Burgess reagent, 0.208 g, 0.874 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 50%) to give the title compound N-((5-(5-(difluoromethyl)-1,3,4-oxadiazol-2-yl) pyridin-2-yl)methyl)-4-methyl-N-phenylpiperazine-1-carboxamide as colorless oil (0.100 g, 40.1%).

$^1$H NMR (400 MHz, CDCl₃) δ 9.22 (dd, 1H, J=5.0, 3.6 Hz), 8.33 (dd, 1H, J=8.2, 2.2 Hz), 7.62 (d, 1H, J=8.2 Hz), 7.33-7.28 (m, 2H), 7.17-7.14 (m, 2H), 7.17-7.12 (m, 1H), 7.07 (s, 0.25H), 6.94 (s, 0.5H), 6.81 (s, 0.25H), 3.31 (t, 4H, J=4.9 Hz), 2.29-2.25 (m, 7H); LRMS (ES) m/z 429.1 (M⁺+1).

Example 185. Compound 21528: N-(2-fluoro-4-(5-(trifluoromethyl)-1,3,4-oxadiazol-2-yl)benzyl)-N-(3-(trifluoromethoxy) phenyl)thiomorpholine-4-carboxamide 1,1-dioxide

[Step 1] Methyl 3-fluoro-4-(((3-(trifluoromethoxy) phenyl)amino)methyl)benzoate

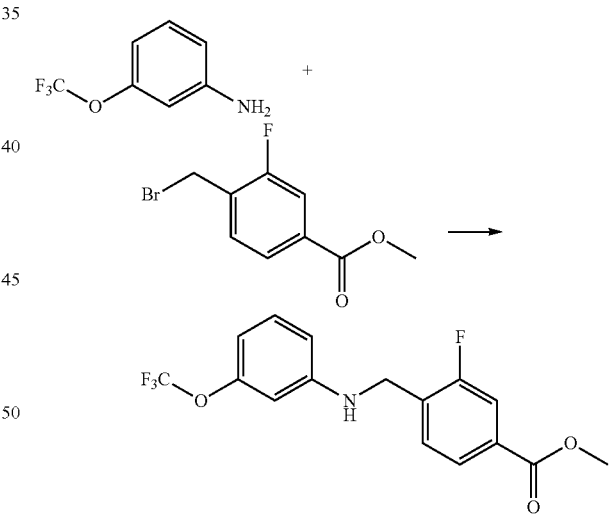

A solution of 3-(trifluoromethoxy)aniline (0.500 g, 2.823 mmol) and N,N-diisopropylethylamine (0.739 mL, 4.234 mmol) in acetonitrile (10 mL) was mixed at the room temperature with methyl 4-(bromomethyl)-3-fluorobenzoate (0.704 g, 2.851 mmol). The reaction mixture was stirred at the same temperature for 16 hr, concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; ethyl acetate/hexane=0% to 10%) to give the title compound methyl 3-fluoro-4-(((3-(trifluoromethoxy)phenyl)amino)methyl)benzoate as white solid (0.638 g, 65.8%).

[Step 2] Methyl 4-((1,1-dioxido-N-(3-(trifluoromethoxy)phenyl)thiomorpholine-4-carboxamido)methyl)-3-fluorobenzoate

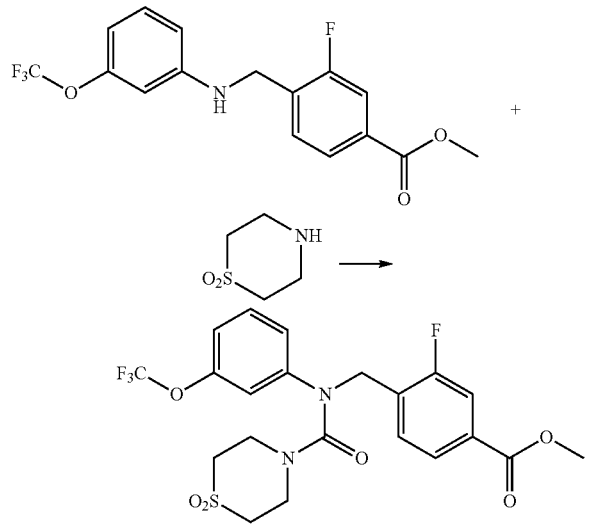

A solution of methyl 3-fluoro-4-(((3-(trifluoromethoxy)phenyl)amino)methyl)benzoate (0.766 g, 2.231 mmol) prepared in Step 1, triphosgene (0.728 g, 2.455 mmol) and N,N-diisopropylethylamine (3.897 mL, 22.314 mmol) in dichloromethane (10 mL) was mixed at 0° C. with thiomorpholine 1,1-dioxide (0.317 g, 2.343 mmol), and stirred at the room temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 40 g cartridge; ethyl acetate/hexane=0% to 50%) to give the title compound methyl 4-((1,1-dioxido-N-(3-(trifluoromethoxy)phenyl)thiomorpholine-4-carboxamido)methyl)-3-fluorobenzoate as yellow solid (0.930 g, 82.6%).

[Step 3] N-(2-fluoro-4-(hydrazinecarbonyl)benzyl)-N-(3-(trifluoromethoxy)phenyl)thiomorpholine-4-carboxamide 1,1-dioxide

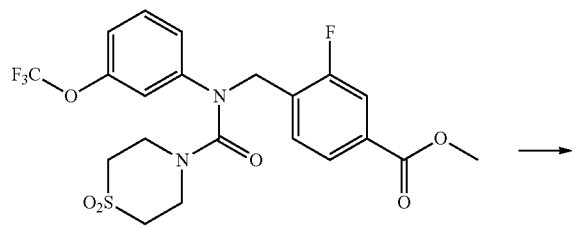

-continued

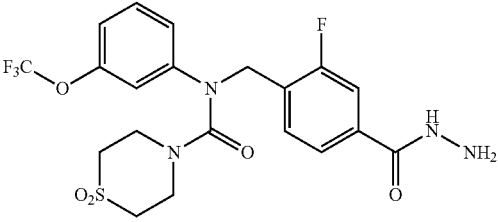

A mixture of methyl 4-((1,1-dioxido-N-(3-(trifluoromethoxy)phenyl)thiomorpholine-4-carboxamido)methyl)-3-fluorobenzoate (0.900 g, 1.784 mmol) prepared in Step 2 and hydrazine monohydrate (1.685 mL, 35.682 mmol) in ethanol (10 mL) was heated at reflux for 16 hr, and cooled down to the room temperature. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (0.838 g, 93.1%, white solid).

[Step 4] N-(2-fluoro-4-(2-(2,2,2-trifluoroacetyl)hydrazine-1-carbonyl)benzyl)-N-(3-(trifluoromethoxy)phenyl)thiomorpholine-4-carboxamide 1,1-dioxide

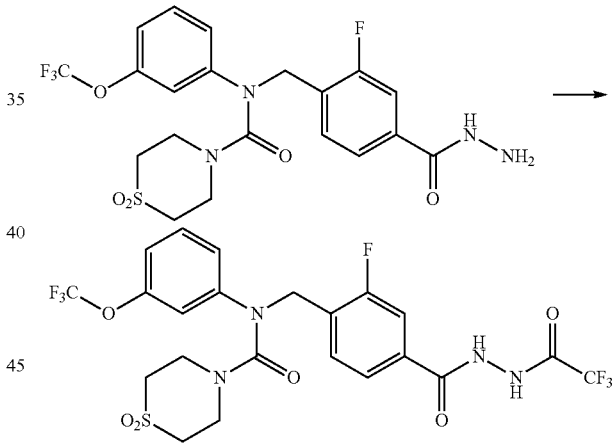

A solution of N-(2-fluoro-4-(hydrazinecarbonyl)benzyl)-N-(3-(trifluoromethoxy)phenyl)thiomorpholine-4-carboxamide 1,1-dioxide (0.419 g, 0.831 mmol) prepared in Step 3 and triethylamine (0.173 mL, 1.246 mmol) in dichloromethane (10 mL) was mixed at the room temperature with trifluoroacetic anhydride (0.104 mL, 0.748 mmol). The reaction mixture was stirred at the same temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give the title compound N-(2-fluoro-4-(2-(2,2,2-trifluoroacetyl)hydrazine-1-carbonyl)benzyl)-N-(3-(trifluoromethoxy)phenyl)thiomorpholine-4-carboxamide 1,1-dioxide as white solid (0.348 g, 69.8%).

655
[Step 5] Compound 21528

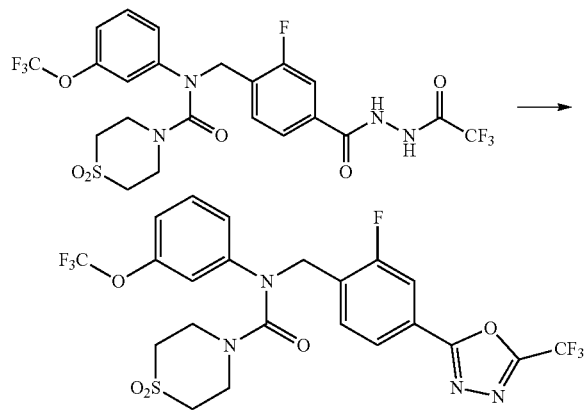

A mixture of N-(2-fluoro-4-(2-(2,2,2-trifluoroacetyl)hydrazine-1-carbonyl)benzyl)-N-(3-(trifluoromethoxy)phenyl)thiomorpholine-4-carboxamide 1,1-dioxide (0.330 g, 0.550 mmol) prepared in Step 4 and 1-methoxy-N-triethylammoniosulfonyl-methanimidate (Burgess reagent, 0.196 g, 0.824 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(2-fluoro-4-(5-(trifluoromethyl)-1,3,4-oxadiazol-2-yl)benzyl)-N-(3-(trifluoromethoxy)phenyl)thiomorpholine-4-carboxamide 1,1-dioxide as white solid (0.126 g, 39.4%).

$^1$H NMR (400 MHz, CDCl$_3$) δ 7.88 (dd, 1H, J=8.0, 1.7 Hz), 7.76 (dd, 1H, J=10.0, 1.7 Hz), 7.68 (t, 1H), 7.41 (t, 1H, J=8.2 Hz), 7.13-7.04 (m, 2H), 7.03-6.97 (m, 1H), 4.94 (s, 2H), 3.75-3.65 (m, 4H), 2.87-2.79 (m, 4H); LRMS (ES) m/z 583 (M$^+$+1).

Example 186. Compound 21529: N-(4-(5-(difluoromethyl)-1,3,4-oxadiazol-2-yl)-2-fluorobenzyl)-N-(3-(trifluoromethoxy)phenyl)thiomorpholine-4-carboxamide 1,1-dioxide

[Step 1] N-(4-(2-(2,2-difluoroacetyl)hydrazine-1-carbonyl)-2-fluorobenzyl)-N-(3-(trifluoromethoxy)phenyl)thiomorpholine-4-carboxamide 1,1-dioxide

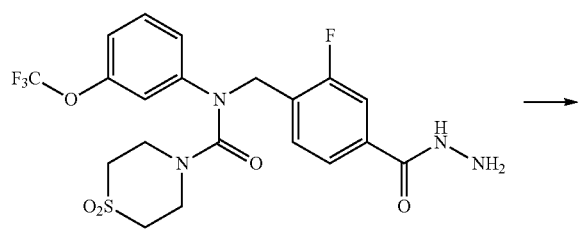

656
-continued

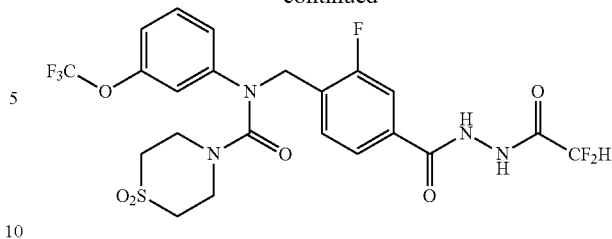

A solution of N-(2-fluoro-4-(hydrazinecarbonyl)benzyl)-N-(3-(trifluoromethoxy)phenyl)thiomorpholine-4-carboxamide 1,1-dioxide (0.419 g, 0.831 mmol) prepared in Step 3 of Example 185 and triethylamine (0.173 mL, 1.246 mmol) in dichloromethane (10 mL) was mixed at the room temperature with difluoroacetic anhydride (0.081 mL, 0.748 mmol). The reaction mixture was stirred at the same temperature for 16 hr. Then, aqueous 1N-water solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 24 g cartridge; methanol/dichloromethane=0% to 3%) to give the title compound N-(4-(2-(2,2-difluoroacetyl)hydrazine-1-carbonyl)-2-fluorobenzyl)-N-(3-(trifluoromethoxy)phenyl)thiomorpholine-4-carboxamide 1,1-dioxide as white solid (0.312 g, 64.5%).

[Step 2] Compound 21529

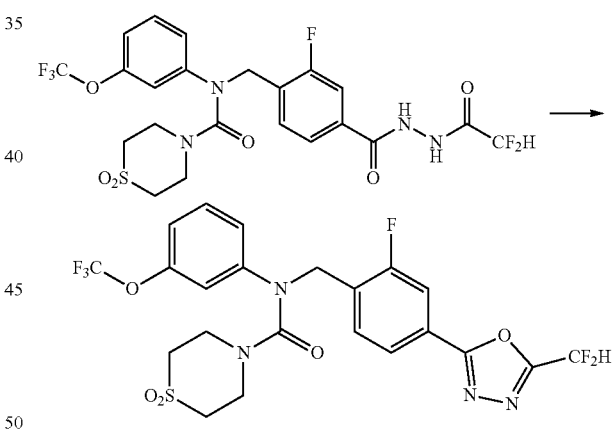

A mixture of N-(4-(2-(2,2-difluoroacetyl)hydrazine-1-carbonyl)-2-fluorobenzyl)-N-(3-(trifluoromethoxy)phenyl)thiomorpholine-4-carboxamide 1,1-dioxide (0.300 g, 0.515 mmol) prepared in Step 1 and 1-methoxy-N-triethylammoniosulfonyl-methanimidate (Burgess reagent, 0.184 g, 0.773 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(4-(5-(difluoromethyl)-1,3,4-oxadiazol-2-yl)-2-fluorobenzyl)-N-(3-(trifluoromethoxy)phenyl)thiomorpholine-4-carboxamide 1,1-dioxide as white solid (0.100 g, 34.4%).

¹H NMR (400 MHz, CDCl₃) δ 7.88 (dd, 1H, J=8.0, 1.7 Hz), 7.76 (dd, 1H, J=10.1, 1.6 Hz), 7.70-7.62 (m, 1H), 7.45-7.35 (m, 1H), 7.12-7.05 (m, 2H), 7.05-6.76 (m, 2H), 4.93 (s, 2H), 3.75-3.66 (m, 4H), 2.87-2.79 (m, 4H); LRMS (ES) m/z 565 (M⁺+1).

Example 187. Compound 21530: N-(3-chloro-4-fluorophenyl)-N-(2-fluoro-4-(5-(trifluoromethyl)-1,3,4-oxadiazol-2-yl)benzyl)thiomorpholine-4-carboxamide 1,1-dioxide

[Step 1] Methyl 4-(((3-chloro-4-fluorophenyl)amino)methyl)-3-fluorobenzoate

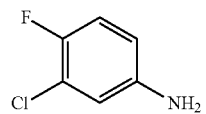

A solution of 3-chloro-4-fluoroaniline (0.600 g, 4.122 mmol) and N,N-diisopropylethylamine (1.080 mL, 6.183 mmol) in acetonitrile (10 mL) was mixed at the room temperature with methyl 4-(bromomethyl)-3-fluorobenzoate (1.029 g, 4.163 mmol). The reaction mixture was stirred at the same temperature for 16 hr. concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 24 g cartridge; ethyl acetate/hexane=0% to 10%) to give the title compound methyl 4-4-(3-chloro-4-fluorophenyl)amino)methyl)-3-fluorobenzoate as ivory solid (1.080 g, 84.1%).

[Step 2] Methyl 4-((N-(3-chloro-4-fluorophenyl)-1,1-dioxidothiomorpholine-4-carboxamido)methyl)-3-fluorobenzoate

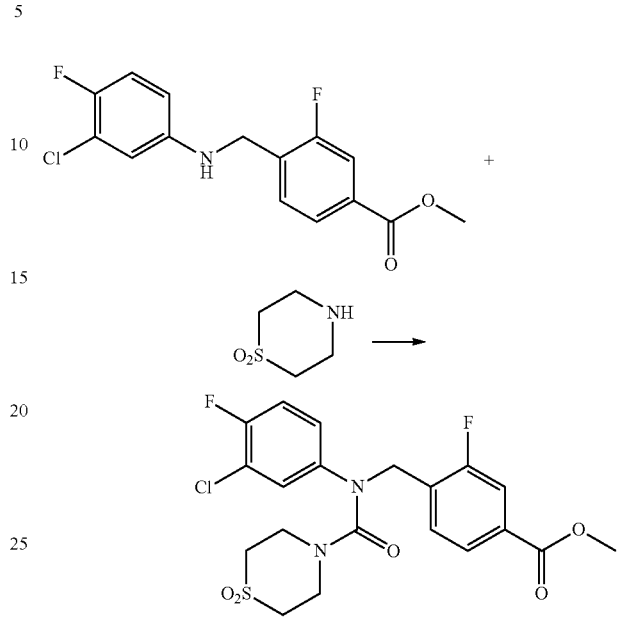

A solution of methyl 4-(((3-chloro-4-fluorophenyl)amino)methyl)-3-fluorobenzoate (1.080 g, 3.465 mmol) prepared in Step 1, triphosgene (1.131 g, 3.811 mmol) and N,N-diisopropylethylamine (6.051 mL, 34.648 mmol) in dichloromethane (10 mL) was mixed at 0° C. with thiomorpholine 1,1-dioxide (0.492 g, 3.638 mmol), and stirred at the room temperature for 16 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 24 g cartridge; ethyl acetate/hexane=0% to 50%) to give the title compound methyl 4-((N-(3-chloro-4-fluorophenyl)-1,1-dioxidothiomorpholine-4-carboxamido)methyl)-3-fluorobenzoate as purple solid (1.560 g, 95.2%).

[Step 3] N-(3-chloro-4-fluorophenyl)-N-(2-fluoro-4-(hydrazinecarbonyl)benzyl)thiomorpholine-4-carboxamide 1,1-dioxide

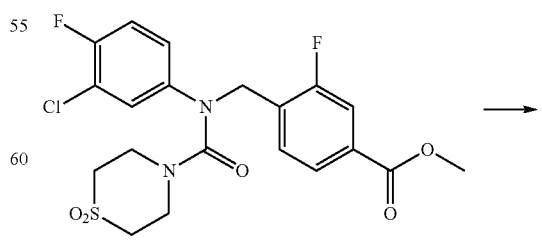

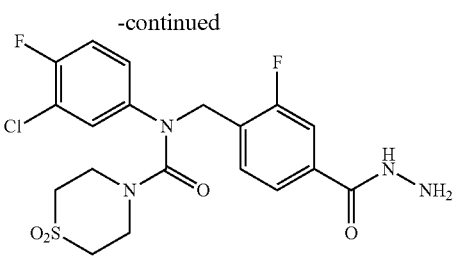

A solution of methyl 4-((N-(3-chloro-4-fluorophenyl)-1,1-dioxidothiomorpholine-4-carboxamido)methyl)-3-fluorobenzoate (1.500 g, 3.172 mmol) prepared in Step 2 and hydrazine monohydrate (2.996 mL, 63.440 mmol) in ethanol (15 mL) was stirred at the room temperature, heated at reflux for 16 hr, and cooled down to the room temperature. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (1.480 g, 98.7%, white solid).

[Step 4] N-(3-chloro-4-fluorophenyl)-N-(2-fluoro-4-(2-(2,2,2-trifluoroacetyl)hydrazine-1-carbonyl)benzyl)thiomorpholine-4-carboxamide 1,1-dioxide

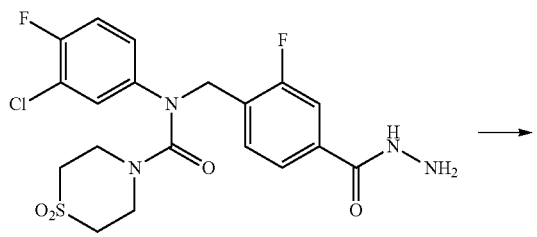

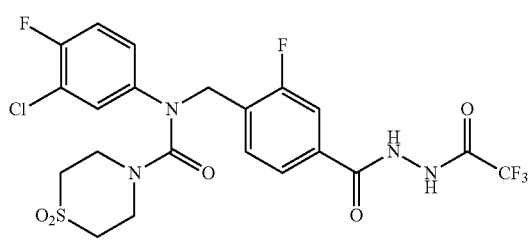

A solution of N-(3-chloro-4-fluorophenyl)-N-(2-fluoro-4-(hydrazinecarbonyl)benzyl)thiomorpholine-4-carboxamide 1,1-dioxide (0.740 g, 1.565 mmol) prepared in Step 3 and triethylamine (0.325 mL, 2.347 mmol) in dichloromethane (10 mL) was mixed at the room temperature with trifluoroacetic anhydride (0.196 mL, 1.408 mmol). The reaction mixture was stirred at the same temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 40 g cartridge; methanol/dichloromethane=0% to 3%) to give the title compound N-(3-chloro-4-fluorophenyl)-N-(2-fluoro-4-(2-(2,2,2-trifluoroacetyl)hydrazine-1-carbonyl)benzyl)thiomorpholine-4-carboxamide 1,1-dioxide as light yellow solid (0.494 g, 55.5%).

[Step 5] Compound 21530

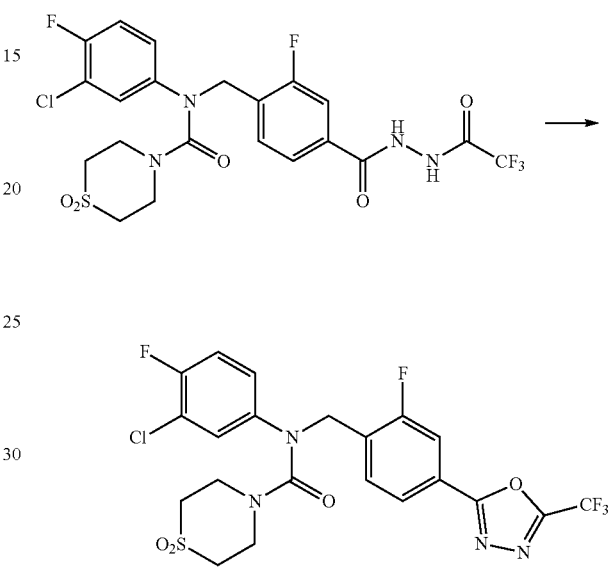

A mixture of N-(3-chloro-4-fluorophenyl)-N-(2-fluoro-4-(2-(2,2,2-trifluoroacetyl)hydrazine-1-carbonyl)benzyl)thiomorpholine-4-carboxamide 1,1-dioxide (0.480 g, 0.844 mmol) prepared in Step 4 and 1-methoxy-N-triethylammoniosulfonyl-methanimidate (Burgess reagent, 0.302 g, 1.266 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 50%) to give the title compound N-(3-chloro-4-fluorophenyl)-N-(2-fluoro-4-(5-(trifluoromethyl)-1,3,4-oxadiazol-2-yl)benzyl)thiomorpholine-4-carboxamide 1,1-dioxide as white solid (0.131 g, 28.2%).

$^1$H NMR (400 MHz, CDCl$_3$) δ 7.89 (dd, 1H, J=8.0, 1.7 Hz), 7.77 (dd, 1H, J=10.0, 1.7 Hz), 7.68 (t, 1H, J=7.6 Hz), 7.21 (d, 1H, J=2.7 Hz), 7.14 (t, 1H, J=8.5 Hz), 7.00-6.97 (m, 1H), 4.88 (s, 2H), 3.74-3.65 (m, 4H), 2.91-2.83 (m, 4H); LRMS (ES) m/z 551 (M$^+$+1).

661

Example 188. Compound 21531: N-(3-chloro-4-fluorophenyl)-N-(4-(5-(difluoromethyl)-1,3,4-oxadiazol-2-yl)-2-fluorobenzyl)thiomorpholine-4-carboxamide 1,1-dioxide

[Step 1] N-(3-chloro-4-fluorophenyl)-N-(4-(2-(2,2-difluoroacetyl)hydrazine-1-carbonyl)-2-fluorobenzyl)thiomorpholine-4-carboxamide 1,1-dioxide

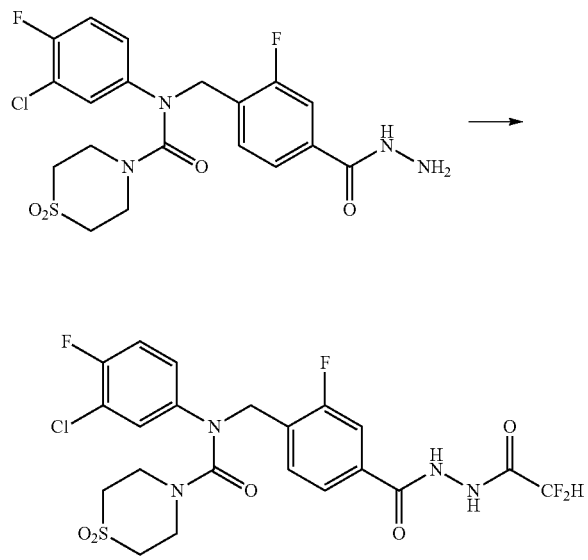

A solution of N-(3-chloro-4-fluorophenyl)-N-(2-fluoro-4-(hydrazinecarbonyl)benzyl)thiomorpholine-4-carboxamide 1,1-dioxide (0.740 g, 1.565 mmol) and triethylamine (0.325 mL, 2.347 mmol) in dichloromethane (10 mL) was mixed at the room temperature with trifluoroacetic anhydride (0.153 mL, 1.408 mmol). The reaction mixture was stirred at the same temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 40 g cartridge; methanol/dichloromethane=0% to 3%) to give the title compound N-(3-chloro-4-fluorophenyl)-N-(4-(2-(2,2-difluoroacetyl)hydrazine-1-carbonyl)-2-fluorobenzyl)thiomorpholine-4-carboxamide 1,1-dioxide as white solid (0.542 g, 62.9%).

[Step 2] Compound 21531

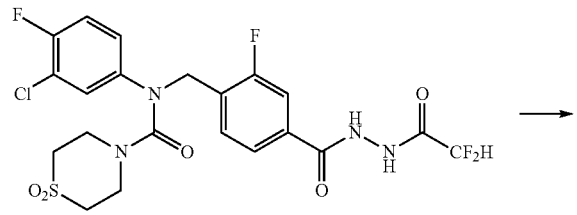

662

-continued

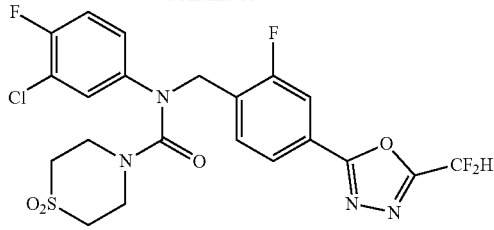

A mixture of N-(3-chloro-4-fluorophenyl)-N-(4-(2-(2,2-difluoroacetyl)hydrazine-1-carbonyl)-2-fluorobenzyl)thiomorpholine-4-carboxamide 1,1-dioxide (0.530 g, 0.962 mmol) prepared in Step 1 and 1-methoxy-N-triethylammoniosulfonyl-methanimidate (Burgess reagent, 0.344 g, 1.443 mmol) in tetrahydrofuran (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 50%) to give the title compound N-(3-chloro-4-fluorophenyl)-N-(4-(5-(difluoromethyl)-1,3,4-oxadiazol-2-yl)-2-fluorobenzyl)thiomorpholine-4-carboxamide 1,1-dioxide as white solid (0.301 g, 58.7%).

$^1$H NMR (400 MHz, CDCl$_3$) δ 7.89 (dd, 1H, J=8.0, 1.7 Hz), 7.77 (dd, 1H, J=10.2, 1.7 Hz), 7.66 (t, 1H, J=7.6 Hz), 7.21 (dd, 1H, J=6:3, 2.7 Hz), 7.18-7.10 (m, 1H), 7.06-6.75 (m, 2H), 4.87 (s, 2H), 3.74-3.66 (m, 4H), 2.91-2.83 (m, 4H); LRMS (ES) m/z 533 (M$^+$+1).

Example 189. Compound 21532: N-((5-(5-(difluoromethyl)-1,3,4-oxadiazol-2-yl)pyrimidin-2-yl)methyl)-N-phenylmorpholine-4-carboxamide

[Step 1] Methyl 2-((phenylamino)methyl)pyrimidine-5-carboxylate

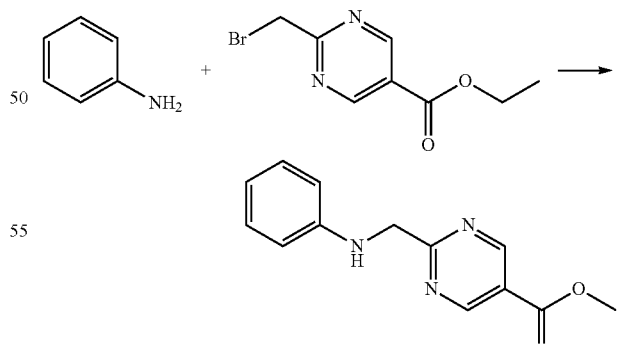

A solution of aniline (0.300 g, 3.221 mmol), methyl 2-(bromomethyl)pyrimidine-5-carboxylate (0.744 g, 3.221 mmol) and potassium carbonate (0.890 g, 6.443 mmol) in N,N-dimethylformamide (10 mL) was stirred at the room temperature for 12 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give methyl 2-((phenylamino)methyl)pyrimidine-5-carboxylate as colorless oil (0.150 g, 19.1%).

[Step 2] Methyl 2-((N-phenylmorpholine-4-carboxamido)methyl)pyrimidine-5-carboxylate

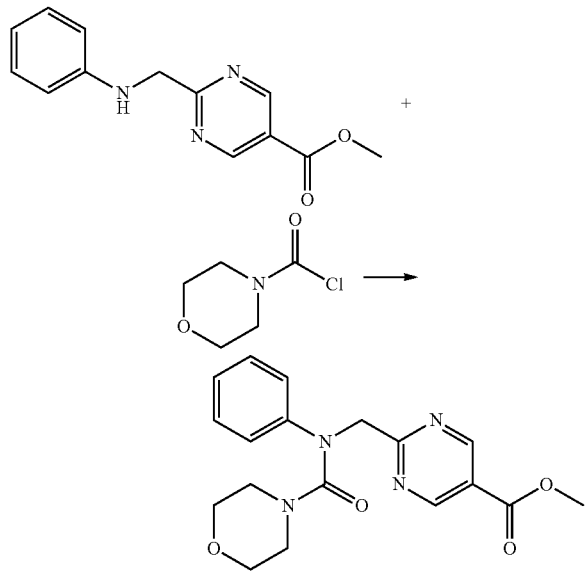

A solution of methyl 2-((phenylamino)methyl)pyrimidine-5-carboxylate (0.200 g, 0.822 mmol) prepared in Step 1, morpholine-4-carbonyl chloride (0.246 g, 1.644 mmol), N,N-diisopropylethylamine (0.443 mL, 2.466 mmol) and N,N-dimethylpyridin-4-amine (DMAP, 0.010 g, 0.082 mmol) in toluene (10 mL) was stirred at 90° C. for 48 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 50%) to give the title compound methyl 2-((N-phenylmorpholine-4-carboxamido)methyl)pyrimidine-5-carboxylate as colorless oil (0.150 g, 51.2%).

[Step 3] N-((5-(hydrazinecarbonyl)pyrimidin-2-yl)methyl)-N-phenylmorpholine-4-carboxamide

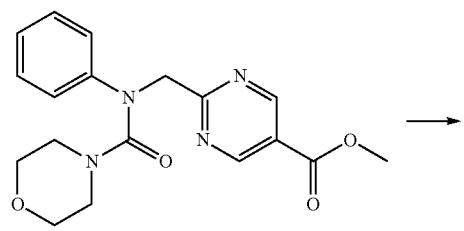

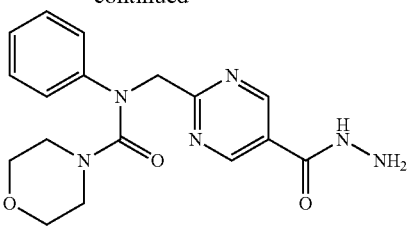

A mixture of methyl 2-((N-phenylmorpholine-4-carboxamido)methyl)pyrimidine-5-carboxylate (0.150 g, 0.421 mmol) prepared in Step 2 and hydrazine monohydrate (0.398 mL, 8.418 mmol) in ethanol (10 mL) was heated at 120° C. for 1 hr under the microwaves, and cooled down to the room temperature to terminate the reaction. The reaction mixture was concentrated under the reduced pressure to remove the solvent. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (0.067 g, 44.7%, colorless oil).

[Step 4] N-((5-(2-(2,2-difluoroacetyl)hydrazine-1-carbonyl)pyrimidin-2-yl)methyl)-N-phenylmorpholine-4-carboxamide

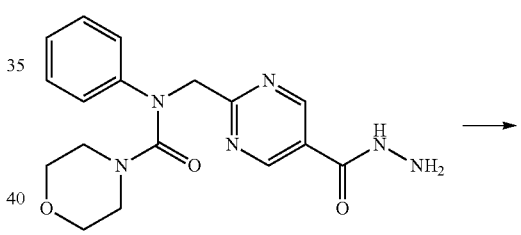

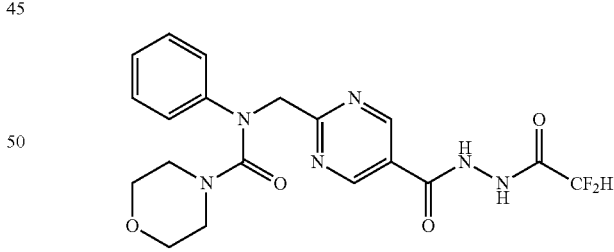

A solution of N-((5-(hydrazinecarbonyl)pyrimidin-2-yl)methyl)-N-phenylmorpholine-4-carboxamide, (0.067 g, 0.188 mmol) prepared in Step 3, difluoroacetic anhydride (0.029 g, 0.169 mmol) and triethylamine (0:029 g, 0.282 mmol) in dichloromethane (3 mL) was stirred at the room temperature for 1 hr. Then, water was added to the reaction mixture, followed by extraction with dichloromethane. The organic layer was washed with aqueous saturated sodium chloride solution, dried with anhydrous MgSO₄, filtered, and concentrated in vacuo. The title compound was used without further purification (0.087 g, 106.5%, colorless oil).

665

[Step 5] Compound 21532

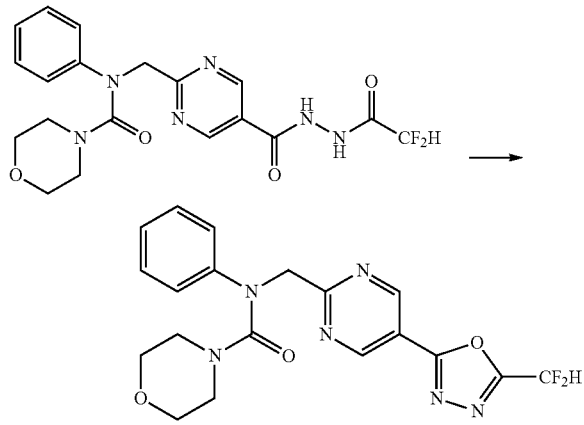

A mixture of N-((5-(2-(2,2-difluoroacetyl)hydrazine-1-carbonyl)pyrimidin-2-yl)methyl)-N-phenylmorpholine-4-carboxamide (0.080 g, 0.184 mmol) prepared in Step 4 and 1-methoxy-N-triethylammoniosulfonyl-methanimidate (Burgess reagent, 0.066 g, 0.276 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 50%) to give the title compound N-((5-(5-(difluoromethyl)-1,3,4-oxadiazol-2-yl)pyrimidin-2-yl)methyl)-N-phenylmorpholine-4-carboxamide as brown oil (0.021 g, 27.4%).

$^1$H NMR (400 MHz, CDCl$_3$) δ 9.38 (5, 2H), 7.36-7.32 (m, 2H), 7.22 (dd, 2H, J=8.4, 1.2 Hz), 7.16-7.12 (m, 1H), 7.10-7.68 (m, 1H), 5.26 (s, 2H), 3.56 (t, 4H, J=4.8 Hz), 3.29 (t, 4H, J=4.8 Hz); LRMS (ES) m/z 417.11 (M$^+$+1).

Example 190. Compound 21533: N-([1,1'-biphenyl]-3-yl)-N-(4-(5-(difluoromethyl)-1,3,4-oxadiazol-2-yl)-2-fluorobenzyl)-4-methylpiperazine-1-carboxamide

[Step 1] Methyl 4-((N-([1,1'-biphenyl]-3-yl)-4-methylpiperazine-1-carboxamido)methyl)-3-fluorobenz oate

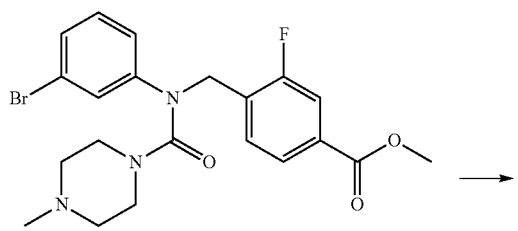

666

-continued

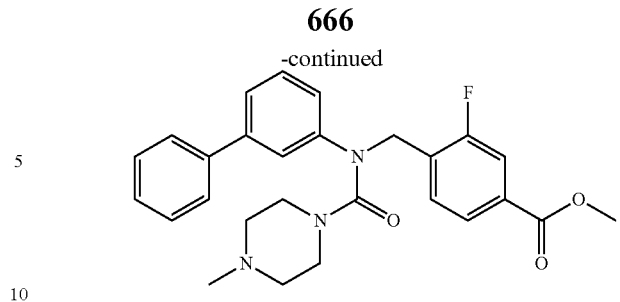

Methyl 4-((N-(3-bromophenyl)-4-methylpiperazine-1-carboxamido)methyl)-3-fluorobenzoate (0.300 g, 0.646 mmol), phenylboronic acid (0.095 g, 0.775 mmol), [1,1'-bis(di-tert-butylphosphino)ferrocene]palladium(II) dichloride (Pd(dtbpf)Cl₂ (0.021 g, 0.032 mmol) and cesium carbonate (0.632 g, 1.938 mmol) in 1,4-dioxane (4 mL)/water (1 mL) was mixed at the room temperature and then heated at 120° C. under the microwaves for 20 min, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 10%) to give the title compound methyl 4-((N-([1,1'-biphenyl]-3-yl)-4-methylpiperazine-1-carboxamido)methyl)-3-fluorobenz oate as brown oil (0.089 g, 29.8 (7c).

[Step 2] N-([1,1'-biphenyl]-3-yl)-N-(2-fluoro-4-(hydrazinecarbonyl)benzyl)-4-methylpiperazine-1-carboxamide

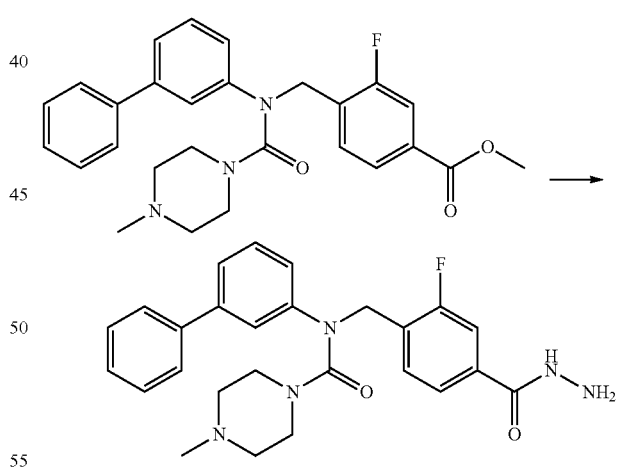

Methyl 4-((N-([1,1'-biphenyl]-3-yl)-4-methylpiperazine-1-carboxamido)methyl)-3-fluorobenz oate (0.089 g, 0.193 mmol) prepared in Step 1 and hydrazine monohydrate (0.187 mL, 3.857 mmol) were mixed at the room temperature in ethanol (4 mL) and then stirred at 120° C. for 17 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (0.095 g, 106.7%, brown oil).

[Step 3] N-([1,1'-biphenyl]-3-yl)-N-(4-(2-(2,2-difluoroacetyl)hydrazine-1-carbonyl)-2-fluorobenzyl)-4-methylpiperazine-1-carboxamide

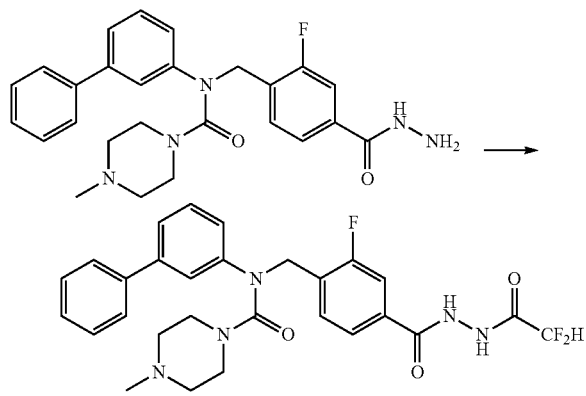

A solution of N-([1,1'-biphenyl]-3-yl)-N-(2-fluoro-4-(hydrazinecarbonyl)benzyl)-4-methylpiperazine-1-carboxamide (0.095 g, 0.206 mmol) prepared in Step 2 and triethylamine (0.043 mL, 0.309 mmol) in dichloromethane (10 mL) was mixed at the room temperature with 2,2-difluoroacetic anhydride (0.023 mL, 0.185 mmol), and stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-([1,1'-biphenyl]-3-yl)-N-(4-(2-(2,2-difluoroacetyl)hydrazine-1-carbonyl)-2-fluorobenzyl)-4-methylpiperazine-1-carboxamide as brown oil (0.092 g, 82.8%).

[Step 4] Compound 21533

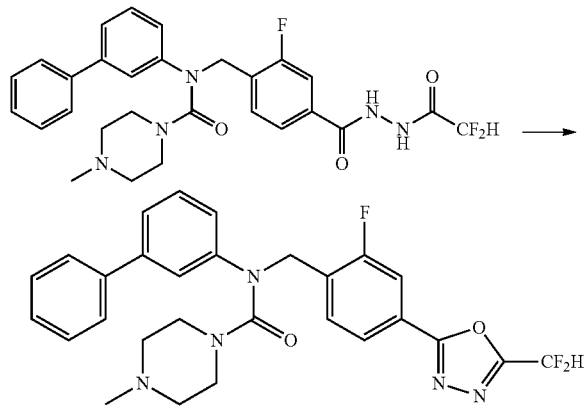

N-([1,1'-biphenyl]-3-yl)-N-(4-(2-(2,2-difluoroacetyl)hydrazine-1-carbonyl)-2-fluorobenzyl)-4-methylpiperazine-1-carboxamide (0.092 g, 0.171 mmol) prepared in Step 3 and 1-methoxy-N-triethylammoniosulfonyl-methanimidate (Burgess reagent, 0.061 g, 0.256 mmol) in tetrahydrofuran (4 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-([1,1'-biphenyl]-3-yl)-N-(4-(5-(difluoromethyl)-1,3,4-oxadiazol-2-yl)-2-fluorobenzyl)-4-methylpiperazine-1-carboxamide as pale orange solid (0.008 g, 9.0%).

$^1$H NMR (400 MHz, CDCl$_3$) δ 7.89 (d, 1H, J=8.2 Hz), 7.78 (d, 1H, J=10.1 Hz), 7.73 (t, 1H, J=7.7 Hz), 7.53 (d, 2H, J=7.4 Hz), 7.47 (t, 2H, J=7.6 Hz), 7.41-7.38 (m, 3H), 7.34 (s, 1H); LRMS (ES) m/z 522.2 (M$^+$+1).

Example 191. Compound 21534: N-(4-(5-(difluoromethyl)-1,3,4-oxadiazol-2-yl)-2-fluorobenzyl)-N-(3-(furan-3-yl)phenyl)-4-methylpiperazine-1-carboxamide

[Step 1] Methyl 3-fluoro-4-((N-(3-(furan-3-yl)phenyl)-4-methylpiperazine-1-carboxamido)methyl) benzoate

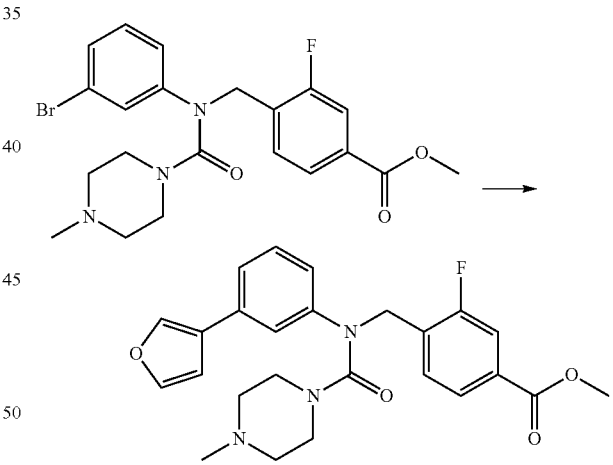

Methyl 4-((N-(3-bromophenyl)-4-methylpiperazine-1-carboxamido)methyl)-3-fluorobenzoate (0.300 g, 0.646 mmol), furan-3-ylboronic acid (0.087 g, 0.775 mmol), [1,1'-bis(di-tert-butylphosphino)ferrocene]palladium(II) dichloride (Pd(dtbpf)Cl$_2$ (0.021 g, 0.032 mmol) and cesium carbonate (0.632 g, 1.938 mmol) in 1,4-dioxane (4 mL)/water (1 mL) was mixed at the room temperature and then heated at 120° C. under the microwaves for 20 min, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound methyl 3-fluoro-4-((N-(3-(furan-3-yl)phenyl)-4-methylpiperazine-1-carboxamido)methyl)benzoate as brown oil (0.126 g, 43.2%).

[Step 2] N-(2-fluoro-4-(hydrazinecarbonyl)benzyl)-N-(3-(furan-3-yl)phenyl)-4-methylpiperazine-1-carboxamide

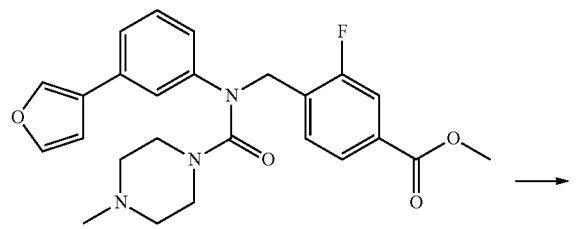

Methyl 3-fluoro-4-((N-(3-(furan-3-yl)phenyl)-4-methylpiperazine-1-carboxamido)methyl)benzoate (0.126 g, 0.279 mmol) prepared in Step 1 and hydrazine monohydrate (0.271 mL, 5.581 mmol) were mixed at the room temperature in ethanol (4 mL) and then stirred at 120° C. for 17 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (0.123 g, 97.6%, brown oil).

[Step 3] N-(4-(2-(2,2-difluoroacetyl)hydrazine-1-carbonyl)-2-fluorobenzyl)-N-(3-(furan-3-yl)phenyl)-4-methylpiperazine-1-carboxamide

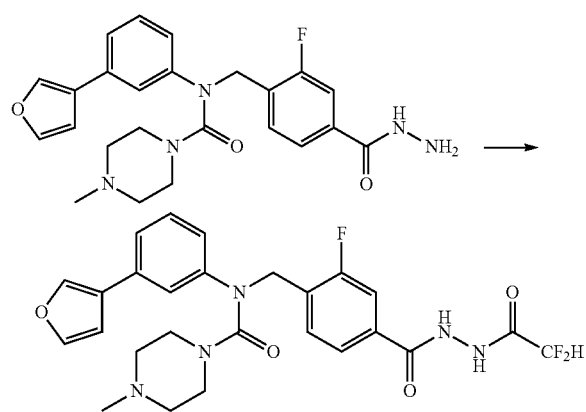

A solution of N-(2-fluoro-4-(hydrazinecarbonyl)benzyl)-N-(3-(furan-3-yl)phenyl)-4-methylpiperazine-1-carboxamide (0.123 g, 0.272 mmol) prepared in Step 2 and triethylamine (0.057 mL, 0.409 mmol) in dichloromethane (10 mL) was mixed at the room temperature with 2,2-difluoroacetic anhydride (0.030 mL, 0.245 mmol), and stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(2-(2,2-difluoroacetyl)hydrazine-1-carbonyl)-2-fluorobenzyl)-N-(3-(furan-3-yl)phenyl)-4-methylpiperazine-1-carboxamide as brown oil (0.143 g, 99.1%).

[Step 4] Compound 21534

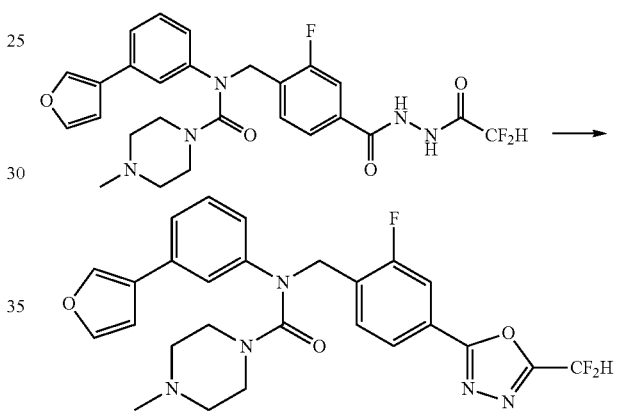

N-(4-(2-(2,2-difluoroacetyl)hydrazine-1-carbonyl)-2-fluorobenzyl)-N-(3-(furan-3-yl) phenyl)-4-methylpiperazine-1-carboxamide (0.163 g, 0.308 mmol) prepared in Step 3 and 1-methoxy-N-triethylammoniosulfonyl-methanimidate (Burgess reagent, 0.110 g, 0.462 mmol) in tetrahydrofuran (4 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(5-(difluoromethyl)-1,3,4-oxadiazol-2-yl)-2-fluorobenzyl)-N-(3-(furan-3-yl)phenyl)-4-methylpiperazine-1-carboxamide as yellow solid (0.018 g, 11.4%).

$^1$H NMR (400 MHz, CDCl$_3$) δ 7.89 (dd, 1H, J=8.0, 1.6 Hz), 7.78 (dd, 1H, J=10.1, 1.5 Hz), 7.73-7.70 (m, 2H), 7.51 (t, 1H, J=1.7 Hz), 7.34 (t, 1H, J=7.8 Hz), 7.27 (s, 1H), 7.23 (t, 1H, J=1.8 Hz), 7.06-6.93 (m, 2H), 6.66-6.65 (m, 1H), 5.02 (s, 2H), 3.46 (brs, 4H), 2.38 (brs, 7H); LRMS (ES) m/z 512.4 (M$^+$+1).

Example 192. Compound 21535: N-(4-(5-(difluoromethyl)-1,3,4-oxadiazol-2-yl)-2-fluorobenzyl)-4-methyl-N-(3-(pyridin-4-yl)phenyl)piperazine-1-carboxamide

[Step 1] Methyl 3-fluoro-4-((4-methyl-N-(3-(pyridin-4-yl)phenyl)piperazine-1-carboxamido)methyl)benzoate

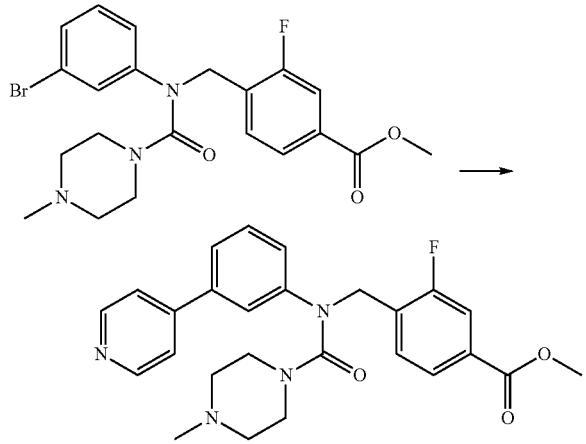

Methyl 4-((N-(3-bromophenyl)-4-methylpiperazine-1-carboxamido)methyl)-3-fluorobenzoate (0.300 g, 0.646 mmol), pyridin-4-ylboronic acid (0.095 g, 0.775 mmol), [1,1'-bis(di-tert-butylphosphino)ferrocene]palladium(II) dichloride (Pd(dtbpf)Cl$_2$, 0.021 g, 0.032 mmol) and cesium carbonate (0.632 g, 1.938 mmol) in 1,4-dioxane (4 mL)/water (I mL) was mixed at the room temperature and then heated at 120° C. under the microwaves for 20 min, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified by column chromatography (SiO$_2$, 4 g cartridge; methanol/dichloromethane=0% to 10%) to give the title compound methyl 3-fluoro-4-((4-methyl-N-(3-(pyridin-4-yl)phenyl)piperazine-1-carboxamido)methyl)benzoate as brown oil (0.136 g, 45.5%).

[Step 2] N-(2-fluoro-4-(hydrazinecarbonyl)benzyl)-4-methyl-N-(3-(pyridin-4-yl)phenyl)piperazine-1-carboxamide

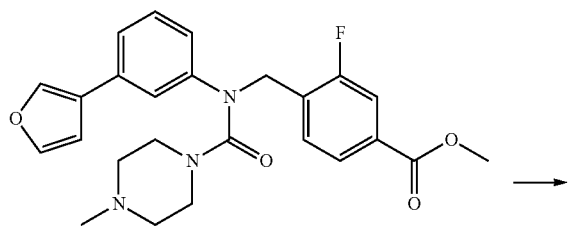

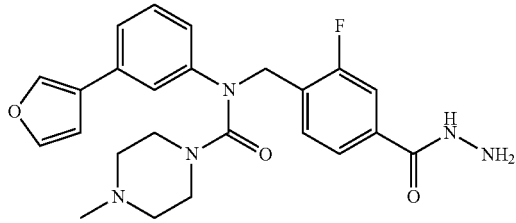

Methyl 3-fluoro-4-((4-methyl-N-(3-(pyridin-4-yl)phenyl)piperazine-1-carboxamido)methyl)benzoate (0.136 g, 0.294 mmol) prepared in Step 1 and hydrazine monohydrate (0.286 mL, 5.881 mmol) were mixed at the room temperature in ethanol (4 mL) and then stirred at 120° C. for 17 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (0.128 g, 94.1%, brown oil).

[Step 3] N-(4-(2-(2,2-difluoroacetyl)hydrazine-1-carbonyl)-2-fluorobenzyl)-4-methyl-N-(3-(pyridin-4-yl)phenyl)piperazine-1-carboxamide

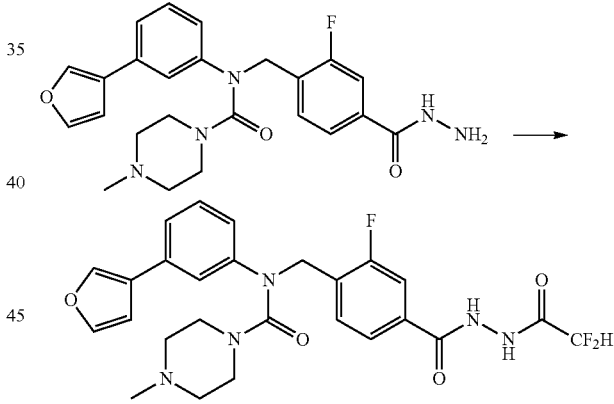

A solution of N-(2-fluoro-4-(hydrazinecarbonyl)benzyl)-4-methyl-N-(3-(pyridin-4-yl)phenyl)piperazine-1-carboxamide (0.128 g, 0.277 mmol) prepared in Step 2 and triethylamine (0.058 mL, 0.415 mmol) in dichloromethane (10 mL) was mixed at the room temperature with 2,2-difluoroacetic anhydride (0.031 mL, 0.249 mmol), and stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(2-(2,2-difluoroacetyl)hydrazine-1-carbonyl)-2-fluorobenzyl)-4-methyl-N-(3-(pyridin-3-yl)phenyl)piperazine-1-carboxamide as brown oil (0.120 g, 80.2%).

[Step 4] Compound 21535

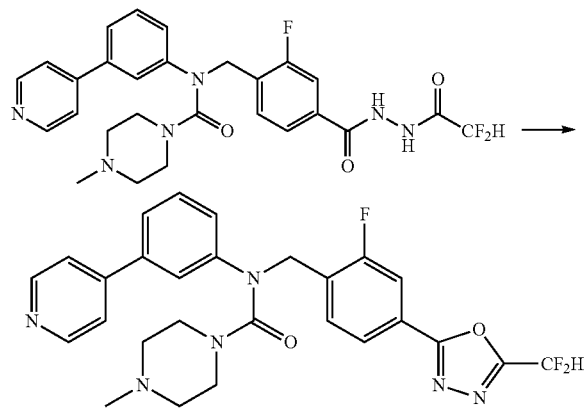

N-(4-(2-(2,2-difluoroacetyl)hydrazine-1-carbonyl)-2-fluorobenzyl)-4-methyl-N-(3-(pyridin-4-yl)phenyl)piperazine-1-carboxamide (0.120 g, 0.222 mmol) and 1-methoxy-N-triethylammoniosulfonyl-methanimidate (Burgess reagent, 0.079 g, 0.333 mmol) in tetrahydrofuran (4 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(5-(difluoromethyl)-1,3,4-oxadiazol-2-yl)-2-fluorobenzyl)-4-methyl-N-(3-(pyridin-4-yl)phenyl) piperazine-1-carboxamide as yellow solid (0.025 g, 21.6%).

$^1$H NMR (400 MHz, CDCl$_3$) δ 8.70 (d, 2H, J=6.1 Hz), 7.90 (dd, 1H, J=8.0, 1.5 Hz), 7.80-7.73 (m, 2H), 7.48-7.42 (m, 4H), 7.39-7.38 (m, 1H), 7.17 (dt, 1H, J=7.3, 1.9 Hz), 6.93 (t, 1H, J=51.7 Hz), 5.05 (s, 2H), 3.46 (brs, 4H), 2.46-2.39 (m, 7H); LRMS (ES) m/z 523.3 (M$^+$+1).

Example 193. Compound 21536: N-(4-(5-(difluoromethyl)-1,3,4-oxadiazol-2-yl)-2-fluorobenzyl)-4-methyl-N-(3-(pyridin-3-yl)phenyl)piperazine-1-carboxamide

[Step 1] Methyl 3-fluoro-4-((4-methyl-N-(3-(pyridin-3-yl)phenyl)piperazine-1-carboxamido)methyl)benzoate

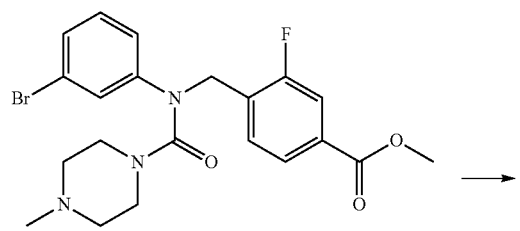

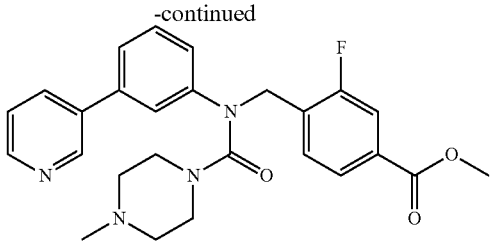

Methyl 4-((N-(3-bromophenyl)-4-methylpiperazine-1-carboxamido)methyl)-3-fluorobenzoate (0.300 g, 0.646 mmol), pyridin-3-ylboronic acid (0.095 g, 0.775 mmol), [1,1'-bis(di-tert-butylphosphino)ferrocene]palladium(II) dichloride (Pd(dtbpf)Cl$_2$, 0.021 g, 0.032 mmol) and cesium carbonate (0.632 g, 1.938 mmol) in 1,4-dioxane (4 mL)/water (1 mL) was mixed at the room temperature and then heated at 120° C. under the microwaves for 20 min, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound methyl 3-fluoro-4-((4-methyl-N-(3-(pyridin-3-yl)phenyl)piperazine-1-carboxamido)methyl)benzoate as brown oil (0.134 g, 44.8%).

[Step 2] N-(2-fluoro-4-(hydrazinecarbonyl)benzyl)-4-methyl-N-(3-(pyridin-3-yl)phenyl)piperazine-1-carboxamide

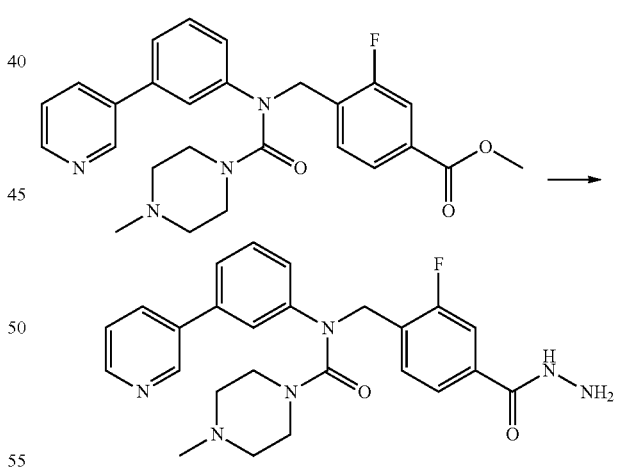

Methyl 3-fluoro-4-((4-methyl-N-(3-(pyridin-3-yl)phenyl)piperazine-1-carboxamido)methyl)benzoate (0.134 g, 0.290 mmol) prepared in Step 1 and hydrazine monohydrate (0.282 mL, 5.794 mmol) were mixed at the room temperature in ethanol (4 mL) and then stirred at 120° C. for 17 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (0.117 g, 87.3%, brown oil).

[Step 3] N-(4-(2-(2,2-difluoroacetyl)hydrazine-1-carbonyl)-2-fluorobenzyl)-4-methyl-N-(3-(pyridin-3-yl)phenyl)piperazine-1-carboxamide

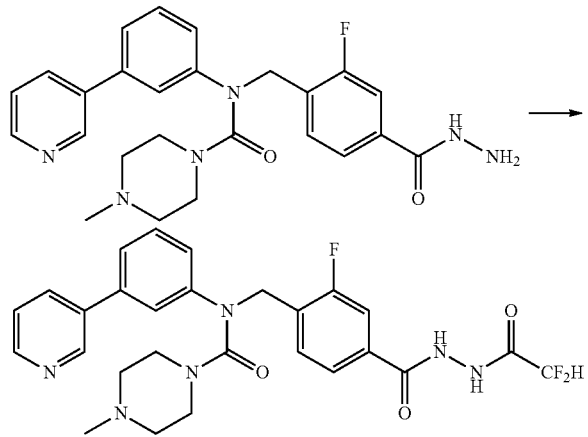

A solution of N-(2-fluoro-4-(hydrazinecarbonyl)benzyl)-4-methyl-N-(3-(pyridin-3-yl)phenyl)piperazine-1-carboxamide (0.117 g, 0.253 mmol) prepared in Step 2 and triethylamine (0.053 mL, 0.379 mmol) in dichloromethane (10 mL) was mixed at the room temperature with 2,2-difluoroacetic anhydride (0.028 mL, 0.228 mmol), and stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(2-(2,2-difluoroacetyl)hydrazine-1-carbonyl)-2-fluorobenzyl)-4-methyl-N-(3-(pyridin-3-yl)phenyl)piperazine-1-carboxamide as brown oil (0.126 g, 92.1%).

[Step 4] Compound 21536

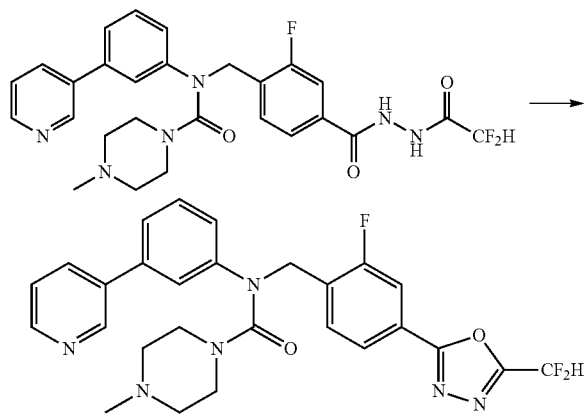

N-(4-(2-(2,2-difluoroacetyl)hydrazine-1-carbonyl)-2-fluorobenzyl)-4-methyl-N-(3-(pyridin-3-yl)phenyl)piperazine-1-carboxamide (0.126 g, 0.233 mmol) prepared in Step 3 and 1-methoxy-N-triethylammoniosulfonyl-methanimidate (Burgess reagent, 0.083 g, 0.350 mmol) in tetrahydrofuran (4 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(4-(5-(difluoromethyl)-1,3,4-oxadiazol-2-yl)-2-fluorobenzyl)-4-methyl-N-(3-(pyridin-3-yl)phenyl)piperazine-1-carboxamide as yellow solid (0.032 g, 26.3%).

$^1$H NMR (400 MHz, CDCl$_3$) δ 8.79 (d, 1H, J=1.7 Hz), 8.65 (dd, 1H, J=4.8, 1.4 Hz), 7.90 (dd, 1H, J=8.0, 1.6 Hz), 7.83 (dt, 1H, J=8.0, 2.0 Hz), 7.78 (dd, 1H, J=10.1, 1.5 Hz), 7.73 (t, 1H, J=7.7 Hz), 7.46 (t, 1H, J=7.8 Hz), 7.43-7.40 (m, 2H), 7.33 (t, 1H, J=1.8 Hz), 7.13 (d, 1H, J=7.9 Hz), 6.93 (t, 11-1. J=51.7 Hz), 5.05 (s, 2H), 3.58 (brs, 4H), 2.54 (brs, 7H); LRMS (ES) m/z 523.3 (M$^+$+1).

Example 194. Compound 21537: N-(4-(5-(difluoromethyl)-1,3,4-oxadiazol-2-yl)-2-fluorobenzyl)-4-methyl-N-(3-(1-methyl-1H-indazol-5-yl)phenyl)piperazine-1-carboxamide

[Step 1] Methyl 3-fluoro-4-((4-methyl-N-(3-(1-methyl-1H-indazol-5-yl)phenyl)piperazine-1-carboxamido)methyl)benzoate

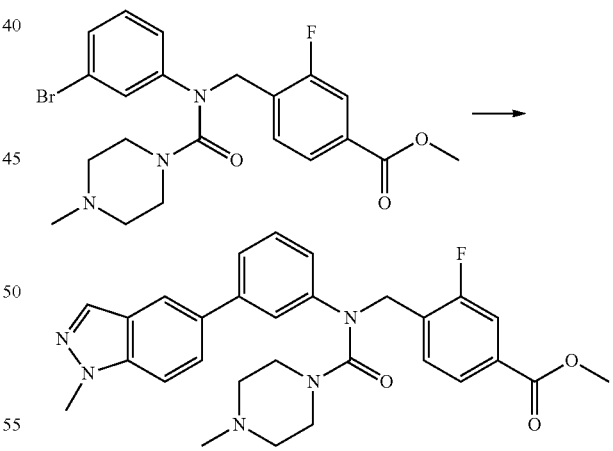

Methyl 4-((N-(3-bromophenyl)-4-methylpiperazine-1-carboxamido)methyl)-3-fluorobenzoate (0.300 g, 0.646 mmol), (1-methyl-1H-indazol-6-yl)boronic acid (0.136 g, 0.775 mmol), [1,1'-bis(di-tert-butylphosphino)ferrocene] palladium(II) dichloride (Pd(dtbpf)Cl$_2$, 0.021 g, 0.032 mmol) and cesium carbonate (0.632 g, 1.938 mmol) in 1,4-dioxane (4 mL)/water (1 mL) was mixed at the room temperature and then heated at 120° C. under the microwaves for 20 min, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 10%) to give the title compound methyl 3-fluoro-4-((4-methyl-N-(3-(1-methyl-1H-indazol-5-yl)phenyl)piperazine-1-carboxamido)methyl)benzoate as brown oil (0.060 g, 18.0%).

[Step 2] N-(2-fluoro-4-(hydrazinecarbonyl)benzyl)-4-methyl-N-(3-(1-methyl-1H-indazol-5-yl)phenyl)piperazine-1-carboxamide

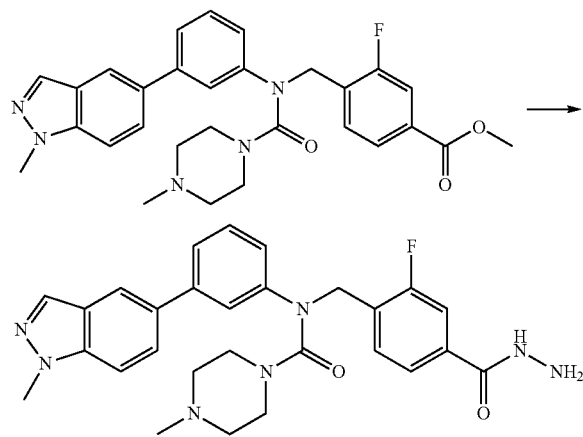

Methyl 3-fluoro-4-((4-methyl-N-(3-(1-methyl-1H-indazol-5-yl)phenyl)piperazine-1-carboxamido)methyl)benzoate (0.060 g, 0.116 mmol) prepared in Step 1 and hydrazine monohydrate (0.113 mL, 2.327 mmol) were mixed at the room temperature in ethanol (4 mL) and then stirred at 120° C. for 17 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (0.057 g, 95.0%, brown oil).

[Step 3] N-(4-(2-(2,2-difluoroacetyl)hydrazine-1-carbonyl)-2-fluorobenzyl)-4-methyl-N-(3-(1-methyl-1H-indazol-5-yl)phenyl)piperazine-1-carboxamide

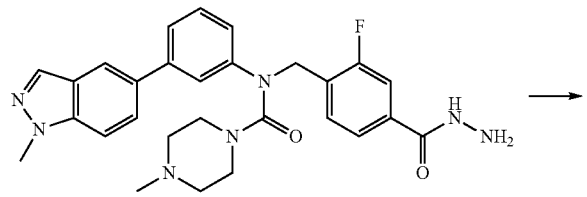

-continued

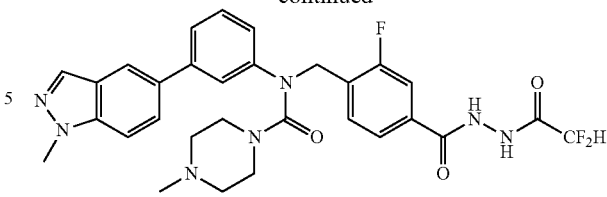

A solution of N-(2-fluoro-4-(hydrazinecarbonyl)benzyl)-4-methyl-N-(3-(1-methyl-1H-indazol-5-yl)phenyl)piperazine-1-carboxamide (0.057 g, 0.111 mmol) prepared in Step 2 and triethylamine (0.023 mL, 0.166 mmol) in dichloromethane (10 mL) was mixed at the room temperature with 2,2-difluoroacetic anhydride (0.012 mL, 0.099 mmol), and stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 10%) to give the title compound N-(4-(2-(2,2-difluoroacetyl)hydrazine-1-carbonyl)-2-fluorobenzyl)-4-methyl-N-(3-(1-methyl-1H-indazol-5-yl)phenyl)piperazine-1-carboxamide as brown oil (0.049 g, 74.7%).

[Step 4] Compound 21537

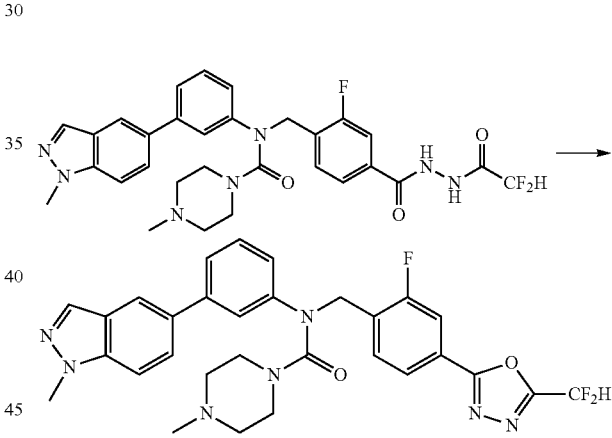

N-(4-(2-(2,2-difluoroacetyl)hydrazine-1-carbonyl)-2-fluorobenzyl)-4-methyl-N-(3-(1-methyl-1H-indazol-5-yl)phenyl)piperazine-1-carboxamide (0.049 g, 0.083 mmol) prepared in Step 1 and 1-methoxy-N-triethylammoniosulfonyl-methanimidate (Burgess reagent, 0.030 g, 0.124 mmol) in tetrahydrofuran (4 mL) was mixed at the room temperature and then heated at 150° C. under the microwaves for 30 min, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 10%) to give the title compound N-(4-(5-(difluoromethyl)-1,3,4-oxadiazol-2-yl)-2-fluorobenzyl)-4-methyl-N-(3-(1-methyl-1H-indazol-5-yl)phenyl)piperazine-1-carboxamide as white solid (0.010 g, 21.0%).

¹H NMR (400 MHz, CDCl₃) δ 8.02 (s, 1H), 7.90 (dd, J=8.0, 1.1 Hz, 1H), 7.81-7.75 (m, 3H), 7.50-7.40 (m, 4H), 7.33 (d, J=8.3 Hz, 1H), 7.12 (d, J=7.3 Hz, 1H), 6.92 (t, J=51.7 Hz, 1H), 5.07 (s, 2H), 4.14 (s, 3H), 3.42 (s, 4H), 2.37 (s, 4H), 2.30 (s, 3H); LRMS (ES) m/z 576.4 (M⁺+1).

Example 195. Compound 21540: N-(4-(5-(difluoromethyl)-1,3,4-oxadiazol-2-yl)-2-fluorobenzyl)-4-methyl-N-(4-(pyridin-3-yl)phenyl)piperazine-1-carboxamide

[Step 1] Methyl 4-((N-(4-bromophenyl)-4-methylpiperazine-1-carboxamido)methyl)-3-fluorobenzoate

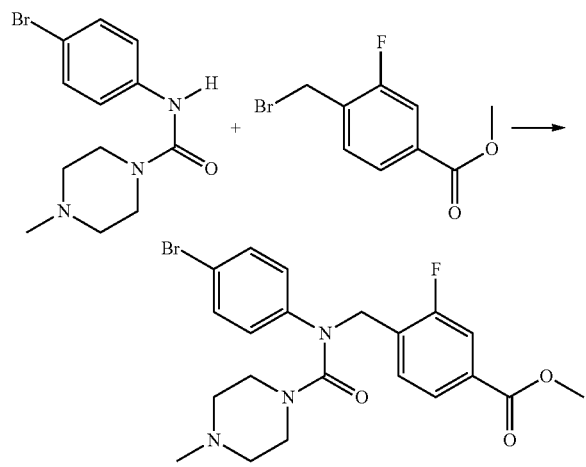

To a stirred solution of N-(4-bromophenyl)-4-methylpiperazine-1-carboxamide (2.000 g, 6.707 mmol) in N,N-dimethylformamide (30 mL) was added at 0° C. sodium hydride (60.00%, 0.402 g, 10.061 mmol). The reaction mixture was stirred at the same temperature for 30 min. Methyl 4-(bromomethyl)-3-fluorobenzoate (1.823 g, 7.378 mmol) was added to the reaction mixture, and stirred at the room temperature for additional 5 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give the title compound methyl 4-((N-(4-bromophenyl)-4-methylpiperazine-1-carboxamido)methyl)-3-fluorobenzoate as white solid (2.800 g, 89.9%).

[Step 2] Methyl 3-fluoro-4-((4-methyl-N-(4-(pyridin-3-yl)phenyl)piperazine-1-carboxamido)methyl)benzoate

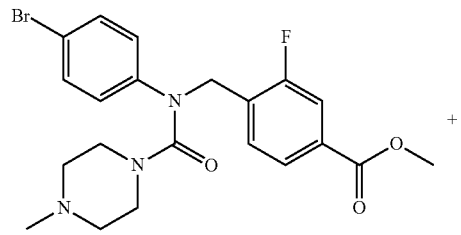

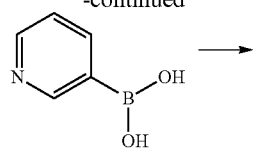

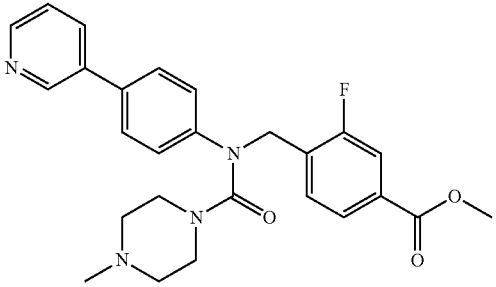

A mixture of methyl 4-((N-(4-bromophenyl)-4-methylpiperazine-1-carboxamido)methyl)-3-fluorobenzoate (0.428 g, 0.922 mmol), pyridin-3-ylboronic acid (0.113 g, 0.922 mmol), [1,1'-bis(di-tert-butylphosphino)ferrocene]palladium(II) dichloride (Pd(dtbpf)Cl₂, 0.060 g, 0.092 mmol) and sodium carbonate (0.293 g, 2.765 mmol) in 1,2-dimethoxyethane (10 mL)/water (3 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 50%) to give the title compound methyl 3-fluoro-4-((4-methyl-N-(4-(pyridin-3-yl)phenyl)piperazine-1-carboxamido)methyl)benzoate as brown oil (0.255 g, 59.8%).

[Step 3] N-(2-fluoro-4-(hydrazinecarbonyl)benzyl)-4-methyl-N-(4-(pyridin-3-yl)phenyl)piperazine-1-carboxamide

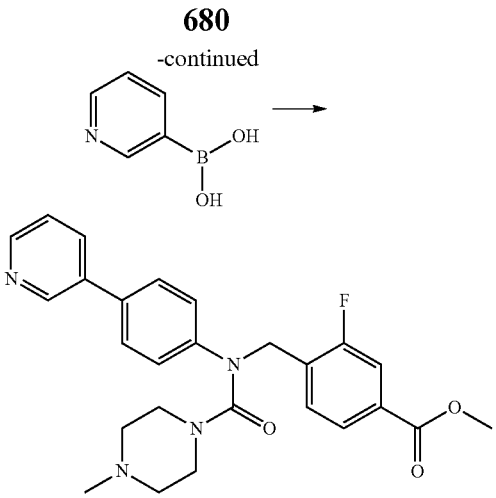

A mixture of methyl 3-fluoro-4-((4-methyl-N-(4-(pyridin-3-yl)phenyl)piperazine-1-carboxamido)methyl)benzoate (0.255 g, 0.551 mmol) prepared in Step 2 and hydrazine monohydrate (0.521 mL, 11.026 mmol) in ethanol (10 mL) was heated at 120° C. for 1 hr under the microwaves, and cooled down to the room temperature to terminate the reaction. The reaction mixture was concentrated under the reduced pressure to remove the solvent, and water was added to the concentrate, followed by extraction with dichloromethane. The organic layer was washed with aqueous saturated sodium chloride solution, dried with anhydrous MgSO₄, filtered, and concentrated in vacuo. The title compound was used without further purification (0.251 g, 98.4%, colorless oil).

[Step 4] N-(4-(2-(2,2-difluoroacetyl)hydrazine-1-carbonyl)-2-fluorobenzyl)-4-methyl-N-(4-(pyridin-3-yl)phenyl)piperazine-1-carboxamide

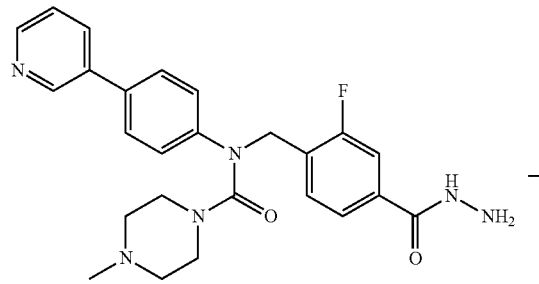

A solution of N-(2-fluoro-4-(hydrazinecarbonyl)benzyl)-4-methyl-N-(4-(pyridin-3-yl)phenyl)piperazine-1-carboxamide (0.251 g, 0.543 mmol) prepared in Step 3, difluoroacetic anhydride (0.053 mL, 0.488 mmol) and triethylamine (0.113 mL, 0.814 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give the title compound N-(4-(2-(2,2-difluoroacetyl)hydrazine-1-carbonyl)-2-fluorobenzyl)-4-methyl-N-(4-(pyridin-3-yl)phenyl)piperazine-1-carboxamide as colorless oil (0.276 g, 94.1%).

[Step 5] Compound 21540

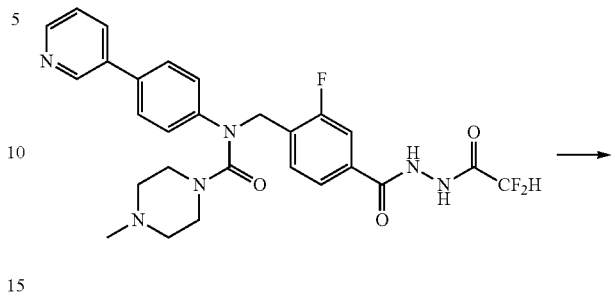

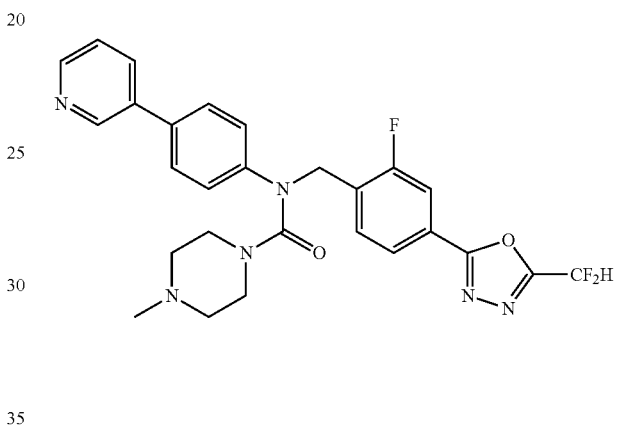

A mixture of N-(4-(2-(2,2-difluoroacetyl)hydrazine-1-carbonyl)-2-fluorobenzyl)-4-methyl-N-(4-(pyridin-3-yl)phenyl)piperazine-1-carboxamide (0.276 g, 0.511 mmol) prepared in Step 4 and 1-methoxy-N-triethylammoniosulfonyl-methanimidate (Burgess reagent, 0.183 g, 0.766 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 50%) to give the title compound N-(4-(5-(difluoromethyl)-1,3,4-oxadiazol-2-yl)-2-fluorobenzyl)-4-methyl-N-(4-(pyridin-3-yl)phenyl)piperazine-1-carboxamide as colorless oil (0.160 g, 60.0%).

$^1$H NMR (400 MHz, CDCl₃) δ 8.80 (d, 1H, J=2.3 Hz), 8.56 (dd, 1H, J=4.8, 1.6 Hz), 7.87-7.82 (m, 2H), 7.75-7.68 (m, 2H), 7.55-7.51 (m, 2H), 7.36-7.33 (m, 1H), 7.21-7.18 (m, 2H), 7.04 (s, 0.25H), 6.91 (s, 0.5H), 6.78 (s, 0.25H), 5.01 (s, 2H), 3.32 (t, 4H, J=4.8 Hz), 2.26-2.20 (m, 7H)); LRMS (ES) m/z 523.1 (M⁺+1).

Example 196. Compound 21541: N-(4-(5-(difluoromethyl)-1,3,4-oxadiazol-2-yl)-2-fluorobenzyl)-4-methyl-N-(4-(pyridin-4-yl)phenyl)piperazine-1-carboxamide

[Step 1] Methyl 3-fluoro-4-((4-methyl-N-(4-(pyridin-4-yl)phenyl)piperazine-1-carboxamido)methyl)benzoate

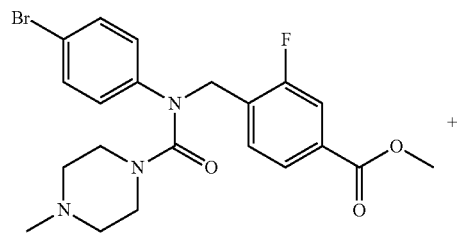

+

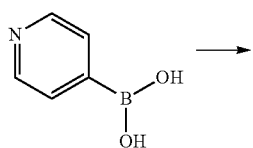

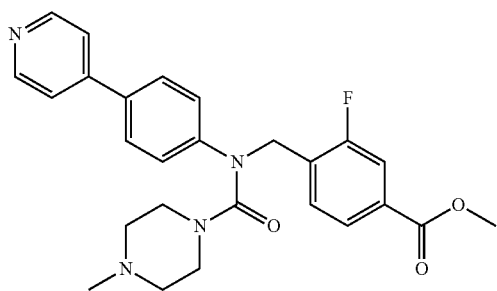

A mixture of methyl 4-((N-(4-bromophenyl)-4-methyl-piperazine-1-carboxamido)methyl)-3-fluorobenzoate (0.495 g, 1.066 mmol), pyridin-4-ylboronic acid (0.131 g, 1.066 mmol), [1,1'-bis(di-tert-butylphosphino)ferrocene]palladium(II) dichloride (Pd(dtbpf)Cl$_2$, 0.069 g, 0:107 mmol) and sodium carbonate (0.339 g, 3.198 mmol) in 1,2-dimethoxyethane (10 mL)/water (3 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give the title compound methyl 3-fluoro-4-((4-methyl-N-(4-(pyridin-4-yl)phenyl)piperazine-1-carboxamido)methyl)benzoate as brown oil (0.371 g, 75.2%).

[Step 2] N-(2-fluoro-4-(hydrazinecarbonyl)benzyl)-4-methyl-N-(4-(pyridin-4-yl)phenyl)piperazine-1-carboxamide

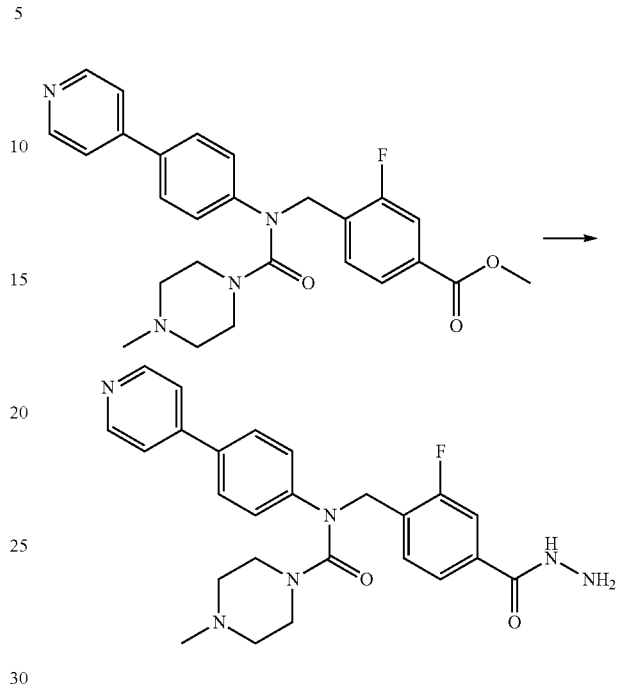

A mixture of methyl 3-fluoro-4-((4-methyl-N-(4-(pyridin-4-yl)phenyl)piperazine-1-carboxamido)methyl)benzoate (0.371 g, 0.802 mmol) prepared in Step 1 and hydrazine monohydrate (0.758 mL, 16.042 mmol) in ethanol (10 mL) was heated at 120° C. for 1 hr under the microwaves, and cooled down to the room temperature to terminate the reaction. The reaction mixture was concentrated under the reduced pressure to remove the solvent, and water was added to the concentrate, followed by extraction with dichloromethane. The organic layer was washed with aqueous saturated sodium chloride solution, dried with anhydrous MgSO$_4$, filtered, and concentrated in vacuo. The title compound was used without further purification (0.275 g, 74.1%, colorless oil).

[Step 3] N-(4-(2-(2,2-difluoroacetyl)hydrazine-1-carbonyl)-2-fluorobenzyl)-4-methyl-N-(4-(pyridin-4-yl)phenyl)piperazine-1-carboxamide

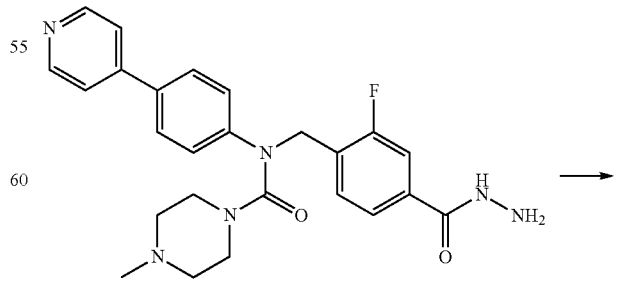

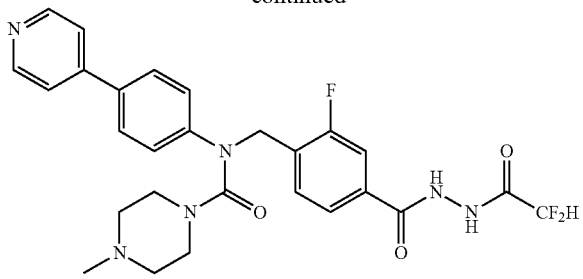

A solution of N-(2-fluoro-4-(hydrazinecarbonyl)benzyl)-4-methyl-N-(4-(pyridin-4-yl)phenyl)piperazine-1-carboxamide (0.275 g, 0.595 mmol) prepared in Step 2, difluoroacetic anhydride (0.093 g, 0.535 mmol) and triethylamine (0.090 g, 0.892 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (0.310 g, 96.5%, colorless oil).

[Step 4] Compound 21541

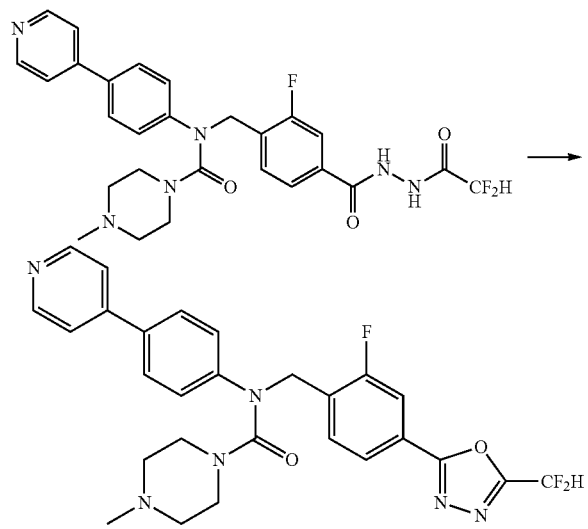

A mixture of N-(4-(2-(2,2-difluoroacetyl)hydrazine-1-carbonyl)-2-fluorobenzyl)-4-methyl-N-(4-(pyridin-4-yl)phenyl)piperazine-1-carboxamide (0.310 g, 0.573 mmol) prepared in Step 3 and 1-methoxy-N-triethylammoniosulfonyl-methanimidate (Burgess reagent, 0.205 g, 0.860 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give the title compound N-(4-(5-(difluoromethyl)-1,3,4-oxadiazol-2-yl)-2-fluorobenzyl)-4-methyl-N-(4-(pyridin-4-yl)phenyl)piperazine-1-carboxamide as colorless oil (0.220 g, 73.4%).

$^1$H NMR (400 MHz, CDCl$_3$) δ 8.65-8.63 (m, 2H), 7.87 (dd, 1H, J=8.0, 1.6 Hz), 7.71 (t, 1H, J=7.6 Hz), 7.62-7.59 (m, 2H), 7.48-7.46 (m, 2H), 7.23-7.19 (m, 2H), 7.04 (s, 0.25H), 6.92 (s, 0.5H), 6.79 (s, 0.25H), 5.03 (s, 2H), 3.33 (t, 4H, J=4.8 Hz), 2.28-2.24 (m, 7H); LRMS (ES) m/z 523.1 (M$^+$+1).

Example 197. Compound 21542: N-([1,1'-biphenyl]-4-yl)-N-(4-(5-(difluoromethyl)-1,3,4-oxadiazol-2-yl)-2-fluorobenzyl)-4-methylpiperazine-1-carboxamide

[Step 1] Methyl 4-((N-([1,1'-biphenyl]-4-yl)-4-methylpiperazine-1-carboxamido)methyl)-3-fluorobenzoate

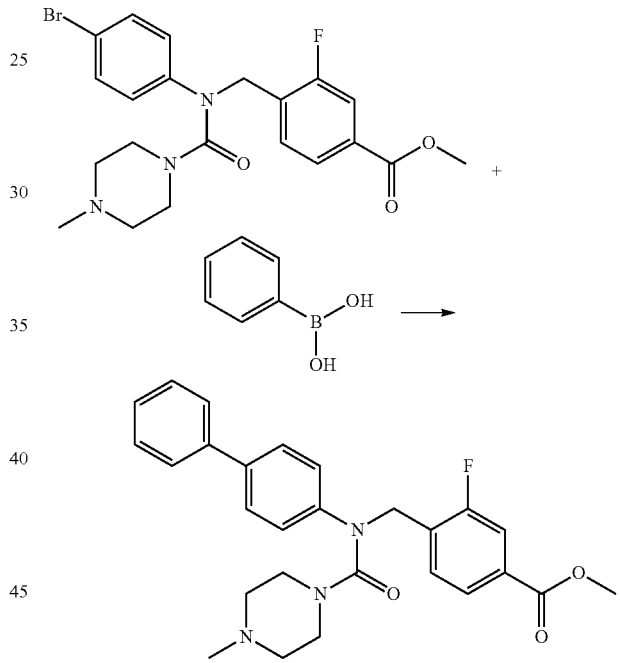

A mixture of methyl 4-((N-(4-bromophenyl)-4-methylpiperazine-1-carboxamido)methyl)-3-fluorobenzoate (0.330 g, 0.711 mmol), phenylboronic acid (0.087 g, 0.711 mmol), [1,1'-bis(di-tert-butylphosphino)ferrocene]palladium(II) dichloride (Pd(dtbpf)Cl$_2$, 0.046 g, 0.071 mmol) and sodium carbonate (0.226 g, 2.132 mmol) in 1,2-dimethoxyethane (10 mL)/water (3 mL) was heated at 120° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 cartridge; ethyl acetate/hexane=0% to 50%) to give the title compound methyl 4-((N-([1,1'-biphenyl]-4-yl)-4-methylpiperazine-1-carboxamido)methyl)-3-fluorobenz oate as brown oil (0.240 g, 73.2%).

687

[Step 2] N-([1,1'-biphenyl]-4-yl)-N-(2-fluoro-4-(hydrazinecarbonyl)benzyl)-4-methylpiperazine-1-carboxamide

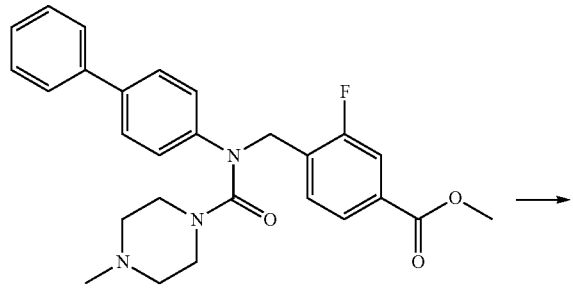

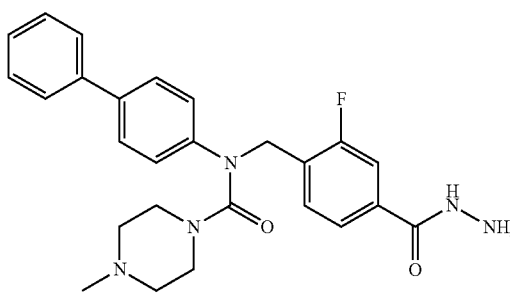

A mixture of methyl 4-((N-([1,1'-biphenyl]-4-yl)-4-methylpiperazine-1-carboxamido)methyl)-3-fluorobenzoate (0.249 g, 0.539 mmol) prepared in Step 1 and hydrazine monohydrate (0.510 mL, 10.790 mmol) in ethanol (10 mL) was heated at 120° C. for 1 hr under the microwaves, and cooled down to the room temperature to terminate the reaction. The reaction mixture was concentrated under the reduced pressure to remove the solvent, and water was added to the concentrate, followed by extraction with dichloromethane. The organic layer was washed with aqueous saturated sodium chloride solution, dried with anhydrous MgSO$_4$, filtered, and concentrated in vacuo. The title compound was used without further purification (0.218 g, 87.6%, colorless oil).

[Step 3] N-([1,1'-biphenyl]-4-yl)-N-(4-(2-(2,2-difluoroacetyl)hydrazine-1-carbonyl)-2-fluorobenzyl)-4-methylpiperazine-1-carboxamide

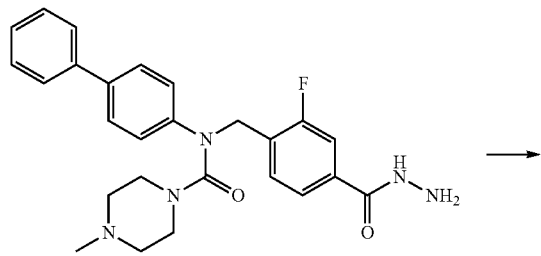

688

-continued

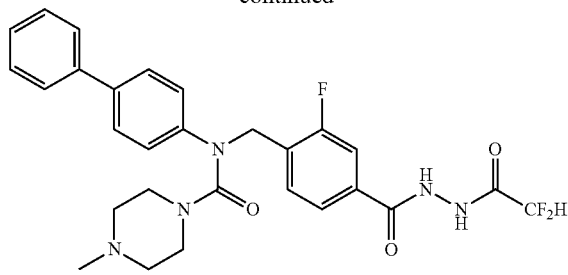

A solution of N-([1,1'-biphenyl]-4-yl)-N-(2-fluoro-4-(hydrazinecarbonyl)benzyl)-4-methylpiperazine-1-carboxamide (0.218 g, 0.472 mmol) prepared in Step 2, difluoroacetic anhydride (0.074 g, 0.425 mmol) and triethylamine (0.072 g, 0.708 mmol) in dichloromethane (10 mL) was stirred at the room temperature for 1 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The title compound was used without further purification (0.220 g, 86.3%, colorless oil).

[Step 4] Compound 21542

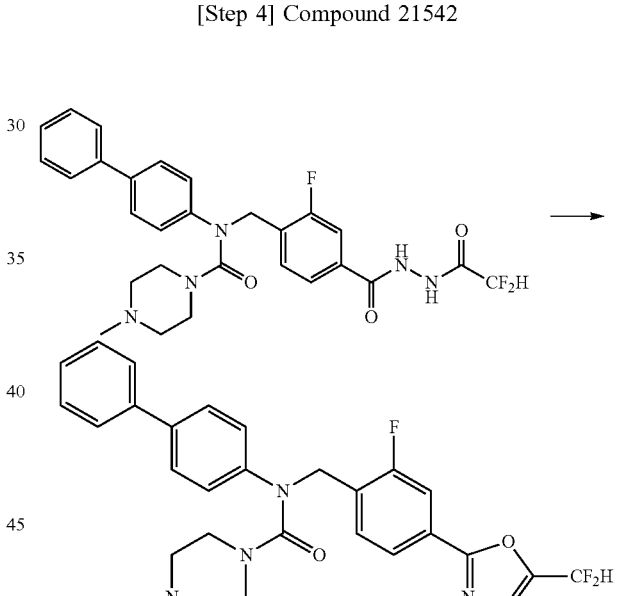

A mixture of N-([1,1'-biphenyl]-4-yl)-N-(4-(2-(2,2-difluoroacetyl)hydrazine-1-carbonyl)-2-fluorobenzyl)-4-methylpiperazine-1-carboxamide (0.220 g, 0.408 mmol) prepared in Step 3 and 1-methoxy-N-triethylammoniosulfonylmethanimidate (Burgess reagent, 0.146 g, 0.612 mmol) in tetrahydrofuran (10 mL) was heated at 150° C. for 30 min under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give the title compound N-([1,1'-biphenyl]-4-yl)-N-(4-(5-(difluoromethyl)-1,3,4-oxadiazol-2-yl)-2-fluorobenzyl)-4-methylpiperazine-1-carboxamide as colorless oil (0.160 g, 75.2%).

$^1$H NMR (400 MHz, CDCl$_3$) δ 7.88 (d, 1H, J=8.2 Hz), 7.77-7.70 (m, 2H), 7.58-7.54 (m, 4H), 7.46-7.42 (m, 2H), 7.37-7.33 (m, 1H), 7.19-7.16 (m, 2H), 7.05-6.79 (m, 1H), 5.03 (s, 2H), 3.34 (t, 4H, J=4.6 Hz), 2.28-2.24 (m, 7H); LRMS (ES) m/z 523.1 (M$^+$+1).

Example 198. Compound 21543: N-(2,3-dihydrobenzofuran-5-yl)-N-(2-fluoro-4-(5-(trifluoromethyl)-1,3,4-oxadiazol-2-yl) benzyl)thiomorpholine-4-carboxamide 1,1-dioxide

[Step 1] N-(2,3-dihydrobenzofuran-5-yl)thiomorpholine-4-carboxamide 1,1-dioxide

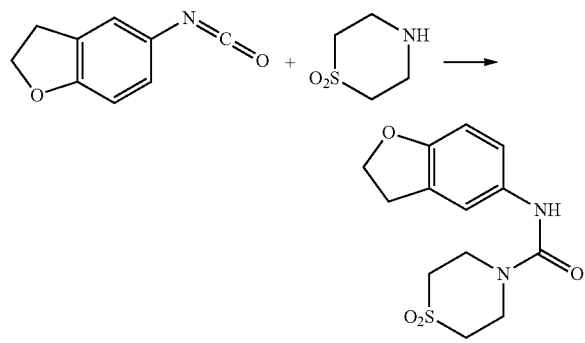

A solution of 5-isocyanato-2,3-dihydrobenzofuran (1.000 g, 6.205 mmol) and thiomorpholine 1,1-dioxide (0.847 g, 6.267 mmol) in diethylether (100 mL) was stirred at the room temperature for 16 hr. The precipitates were collected by filtration, washed by diethylether, and dried to give the title compound N-(2,3-dihydrobenzofuran-5-yl)thiomorpholine-4-carboxamide 1,1-dioxide as white solid (1.780 g, 96.8%).

[Step 2] Methyl 4-((N-(2,3-dihydrobenzofuran-5-yl)-1,1-dioxidothiomorpholine-4-carboxamido)methyl)-3-fluorobenzoate

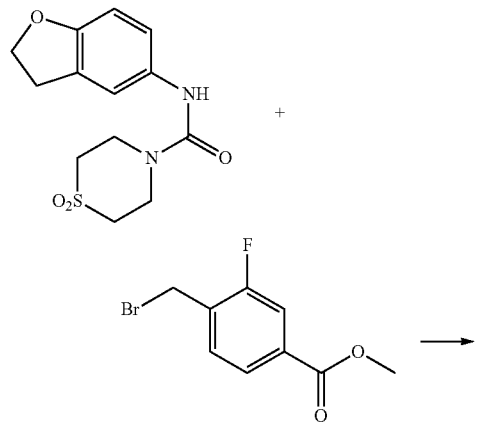

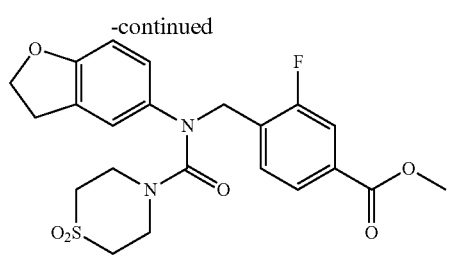

To a stirred solution of N-(2,3-dihydrobenzofuran-5-yl) thiomorpholine-4-carboxamide 1,1-dioxide (0.250 g, 0.844 mmol) in N,N-dimethylformide (3 mL) was added at 0° C. sodium hydride (60.00%, 0.051 g, 1.265 mmol). The reaction mixture was stirred at the same temperature. Methyl 4-(bromomethyl)-3-fluorobenzoate (0.211 g, 0.852 mmol) was added to the reaction mixture, and stirred at the room temperature for additional 3 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give the title compound methyl 4-((N-(2,3-dihydrobenzofuran-5-yl)-1,1-dioxidothiomorpholine-4-carboxamido)methyl)-3-fluorobenzoate as light yellow solid (0.124 g, 31.8%).

[Step 3] N-(2,3-dihydrobenzofuran-5-yl)-N-(2-fluoro-4-(hydrazinecarbonyl)benzyl)thiomorpholine-4-carboxamide 1,1-dioxide

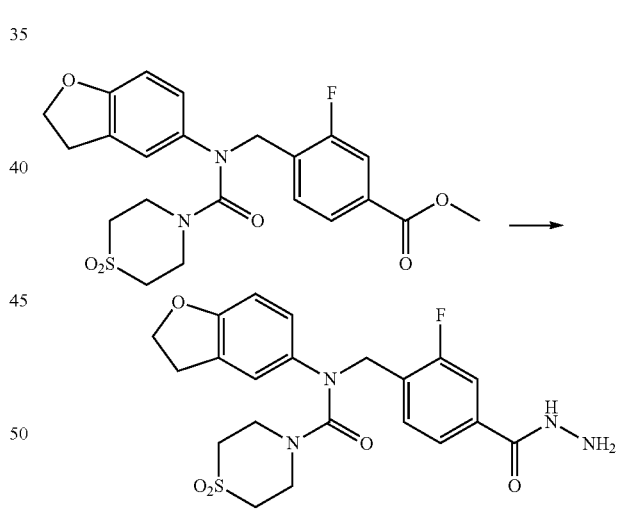

A mixture of methyl 4-((N-(2,3-dihydrobenzofuran-5-yl)-1,1-dioxidothiomorpholine-4-carboxamido)methyl)-3-fluorobenzoate (0.124 g, 0.268 mmol) prepared in Step 2 and hydrazine monohydrate (0.253 mL, 5.362 mmol) in ethanol (5 mL) was heated at reflux for 16 hr, and cooled down to the room temperature. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The title compound was used without further purification (0.119 g, 96.0%, white solid).

[Step 4] N-(2,3-dihydrobenzofuran-5-yl)-N-(2-fluoro-4-(2-(2,2,2-trifluoroacetyl)hydrazine-1-carbonyl)benzyl)thiomorpholine-4-carboxamide 1,1-dioxide

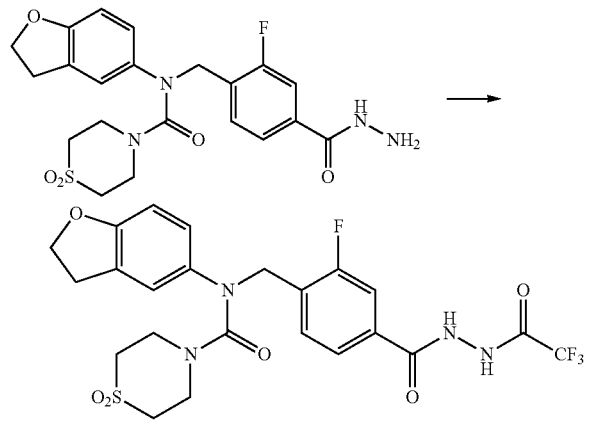

A solution of N-(2,3-dihydrobenzofuran-5-yl)-N-(2-fluoro-4-(hydrazinecarbonyl)benzyl)thiomorpholine-4-carboxamide 1,1-dioxide (0.059 g, 0.128 mmol) prepared in Step 3 and N,N-diisopropylethylamine (0.027 mL, 0.191 mmol) in dichloromethane (1 mL) was mixed at 0° C. with trifluoroacetic anhydride (0.016 mL, 0.115 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(2,3-dihydrobenzofuran-5-yl)-N-(2-fluoro-4-(2-(2,2,2-trifluoroacetyl)hydrazine-1-carbonyl)benzyl)thiomorpholine-4-carboxamide 1,1-dioxide as light yellow solid (0.071 g, 99.7%).

[Step 5] Compound 21543

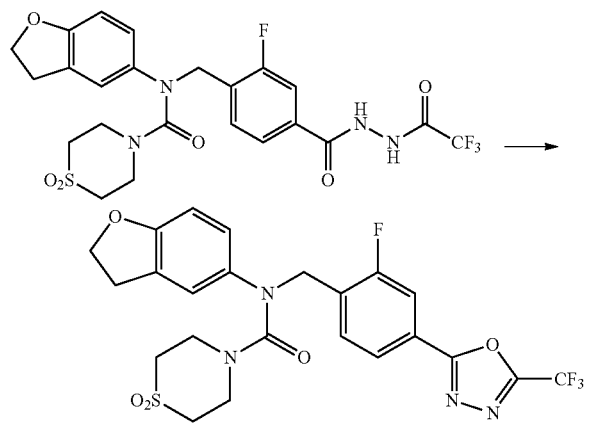

A mixture of N-(2,3-dihydrobenzofuran-5-yl)-N-(2-fluoro-4-(2-(2,2,2-trifluoroacetyl)hydrazine-1-carbonyl)benzyl)thiomorpholine-4-carboxamide 1,1-dioxide (0.075 g, 0.134 mmol) prepared in Step 4 and 1-methoxy-N-triethylammoniosulfonyl-methanimidate (Burgess reagent, 0.048 g, 0.201 mmol) in tetrahydrofuran (1 mL) was heated at 150° C. for 30 min under the microwaves, and cooled down to the room temperature to terminate the reaction. The reaction mixture was concentrated under the reduced pressure to remove the solvent, and aqueous 1N-water solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(2,3-dihydrobenzofuran-5-yl)-N-(2-fluoro-4-(5-(trifluoromethyl)-1,3,4-oxadiazol-2-yl) benzyl)thiomorpholine-4-carboxamide 1,1-dioxide as white solid (0.022 g, 29.8%).

$^1$H NMR (400 MHz, CDCl$_3$) δ 7.87 (dd, 1H, J=7.9, 1.6 Hz), 7.74 (dd, 1H, J=10.1, 1.6 Hz), 7.67 (t, 1H, J=7.6 Hz), 6.98-6.92 (m, 1H), 6.81 (dd, 1H, J=8.4, 2.3 Hz), 6.71 (d, 1H, J=8.5 Hz), 4.85 (s, 2H), 4.61 (t, 2H, J=8.7 Hz), 3.76-3.68 (m, 4H), 3.20 (t, 2H, J=8.7 Hz), 2.83-2.75 (m, 4H); LRMS (ES) m/z 541.3 (M$^+$+1).

Example 199. Compound 21544: N-(4-(5-(difluoromethyl)-1,3,4-oxadiazol-2-yl)-2-fluorobenzyl)-N-(2,3-dihydrobenzofuran-5-yl)thiomorpholine-4-carboxamide 1,1-dioxide

[Step 1] N-(4-(2-(2,2-difluoroacetyl)hydrazine-1-carbonyl)-2-fluorobenzyl)-N-(2,3-dihydrobenzofuran-5-yl)thiomorpholine-4-carboxamide 1,1-dioxide

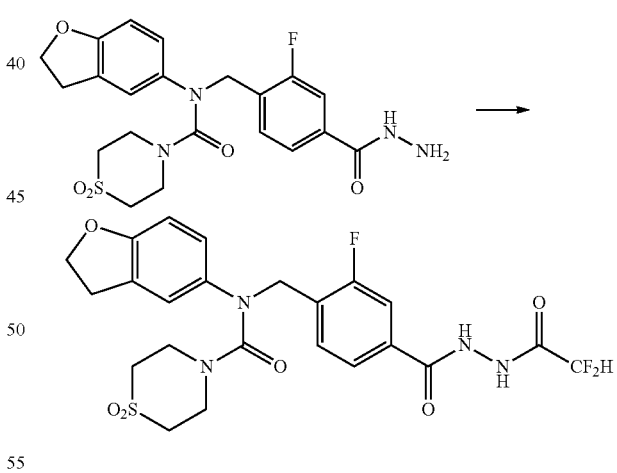

A solution of N-(2,3-dihydrobenzofuran-5-yl)-N-(2-fluoro-4-(hydrazinecarbonyl)benzyl)thiomorpholine-4-carboxamide 1,1-dioxide (0.059 g, 0.128 mmol) prepared in Step 3 of Example 198 and N,N-diisopropylethylamine (0.027 mL, 0.191 mmol) in dichloromethane (1 mL) was mixed at 0° C. with difluoroacetic anhydride (0.012 mL, 0.115 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(4-(2-(2,2-difluoroacetyl)hydrazine-1-carbonyl)-2-fluorobenzyl)-N-(2,3-dihydrobenzofuran-5-yl)thiomorpholine-4-carboxamide 1,1-dioxide as light yellow solid (0.058 g, 84.1%).

[Step 2] Compound 21544

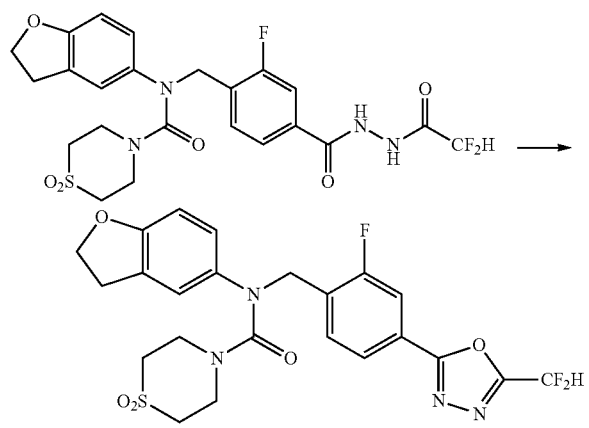

A mixture of N-(4-(2-(2,2-difluoroacetyl)hydrazine-1-carbonyl)-2-fluorobenzyl)-N-(2,3-dihydrobenzofuran-5-yl)thiomorpholine-4-carboxamide 1,1-dioxide (0.058 g, 0.107 mmol) prepared in Step 1 and 1-methoxy-N-triethylammoniosulfonyl-methanimidate (Burgess reagent, 0.038 g, 0.161 mmol) in tetrahydrofuran (1 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(4-(5-(difluoromethyl)-1,3,4-oxadiazol-2-yl)-2-fluorobenzyl)-N-(2,3-dihydrobenzofuran-5-yl)thiomorpholine-4-carboxamide 1,1-dioxide as white solid (0.021 g, 36.6%).
$^1$H NMR (400 MHz, CDCl$_3$) δ 7.86 (dd, 1H, J=8.1, 1.7 Hz), 7.74 (dd, 1H, J=10.0, 1.6 Hz), 7.65 (t, 1H, J=7.7 Hz), 7.05-6.77 (m, 3H), 6.71 (d, 1H, J=8.4 Hz), 4.84 (s, 2H), 4.61 (t, 2H, J=8.7 Hz), 3.76-3.68 (m, 4H), 3.19 (t, 2H, J=8.7 Hz), 2.83-2.75 (m, 4H); LRMS (ES) m/z 523.19 (M$^+$+1).

Example 200. Compound 21545: N-(2-fluoro-4-(5-(trifluoromethyl)-1,3,4-oxadiazol-2-yl)benzyl)-N-(1-methyl-1H-indazol-6-yl)thiomorpholine-4-carboxamide 1,1-dioxide

[Step 1] Methyl 3-fluoro-4-(((1-methyl-1H-indazol-6-yl)amino)methyl)benzoate

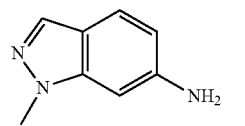 +

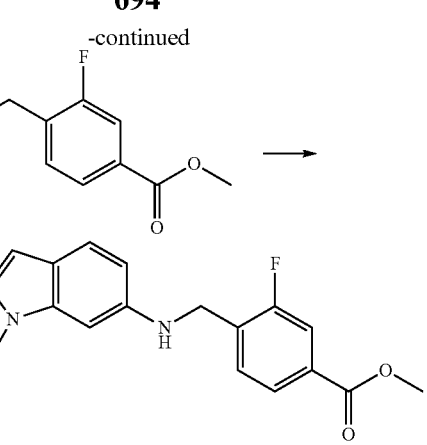

A solution of 1-methyl-1H-indol-6-amine (0.300 g, 1.214 mmol) and N,N-diisopropylethylamine (0.254 mL, 1.457 mmol) in N,N-dimethylformide (3 mL) was mixed at the room temperature with methyl 4-(bromomethyl)-3-fluorobenzoate (0.303 g, 1.226 mmol). The reaction mixture was stirred at the same temperature for 16 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give the title compound methyl 3-fluoro-4-(((1-methyl-1H-indazol-6-yl)amino)methyl)benzoate as white solid (0.381 g, 100.0%).

[Step 2] Methyl 3-fluoro-4-((N-(1-methyl-1H-indazol-6-yl)-1,1-dioxidothiomorpholine-4-carboxamido)methyl)benzoate

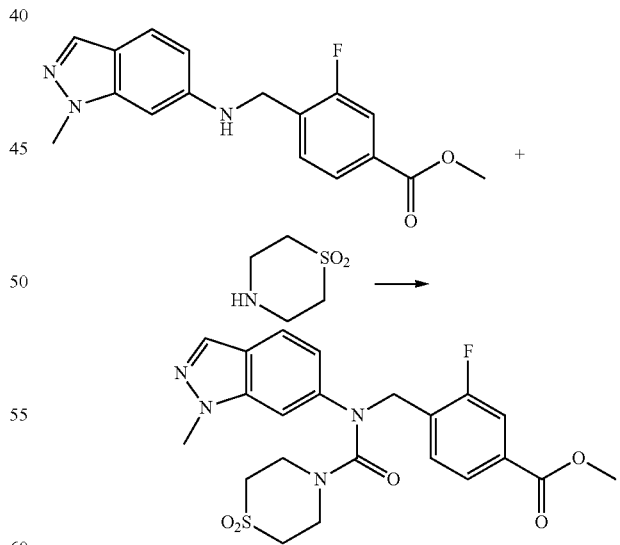

A solution of methyl 3-fluoro-4-(((1-methyl-1H-indazol-6-yl)amino)methyl)benzoate (0.380 g, 1.213 mmol) prepared in Step 1, triphosgene (0.396 g, 1.334 mmol) and N,N-diisopropylethylamine (2.118 mL, 12.128 mmol) in dichloromethane (10 mL) was mixed at 0° C. with thiomorpholine 1,1-dioxide (0.172 g, 1.273 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 12 g cartridge; methanol/dichloromethane=0% to 3%) to give the title compound methyl 3-fluoro-4-((N-(1-methyl-1H-indazol-6-yl)-1,1-dioxidothiomorpholine-4-carboxamido)methyl)benzoate as light yellow solid (0.400 g, 69.5%).

[Step 3] N-(2-fluoro-4-(hydrazinecarbonyl)benzyl)-N-(1-methyl-1H-indazol-6-yl)thiomorpholine-4-carboxamide 1,1-dioxide

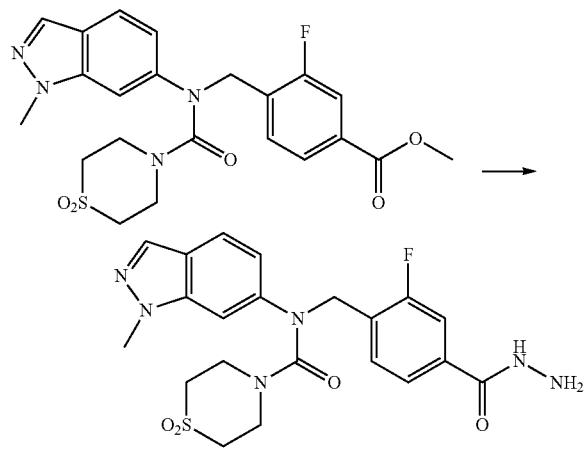

A mixture of methyl 3-fluoro-4-((N-(1-methyl-1H-indazol-6-yl)-1,1-dioxidothiomorpholine-4-carboxamido)methyl)benzoate (0.400 g, 0.843 mmol) and hydrazine monohydrate (0.796 mL, 16.859 mmol) in ethanol (10 mL) was heated at reflux for 16 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 5%) to give the title compound N-(2-fluoro-4-(hydrazinecarbonyl)benzyl)-N-(1-methyl-1H-indazol-6-yl)thiomorpholine-4-carboxamide 1,1-dioxide as light yellow solid (0.358 g, 89.5%).

[Step 4] N-(2-fluoro-4-(2-(2,2,2-trifluoroacetyl)hydrazine-1-carbonyl)benzyl)-N-(1-methyl-1H-indazol-6-yl)thiomorpholine-4-carboxamide 1,1-dioxide

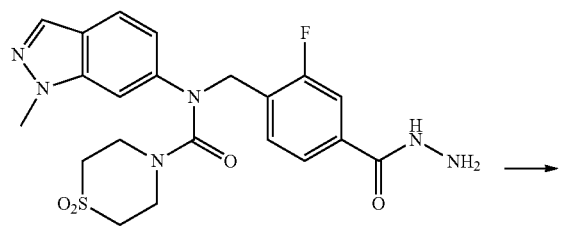

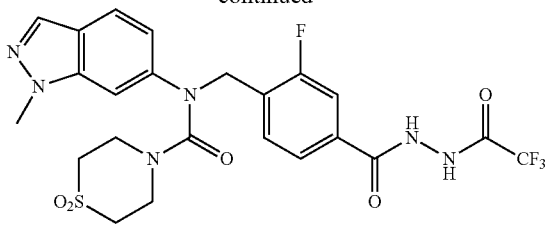

A solution of N-(2-fluoro-4-(hydrazinecarbonyl)benzyl)-N-(1-methyl-1H-indazol-6-yl)thiomorpholine-4-carboxamide 1,1-dioxide (0.179 g, 0.377 mmol) prepared in Step 3 and N,N-diisopropylethylamine (0.078 mL, 0.566 mmol) in dichloromethane (3 mL) was mixed at 0° C. with trifluoroacetic anhydride (0.047 mL, 0.340 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-(2-fluoro-4-(2-(2,2,2-trifluoroacetyl)hydrazine-1-carbonyl)benzyl)-N-(1-methyl-1H-indazol-6-yl)thiomorpholine-4-carboxamide 1,1-dioxide as light yellow solid (0.214 g, 99.4%).

[Step 5] Compound 21545

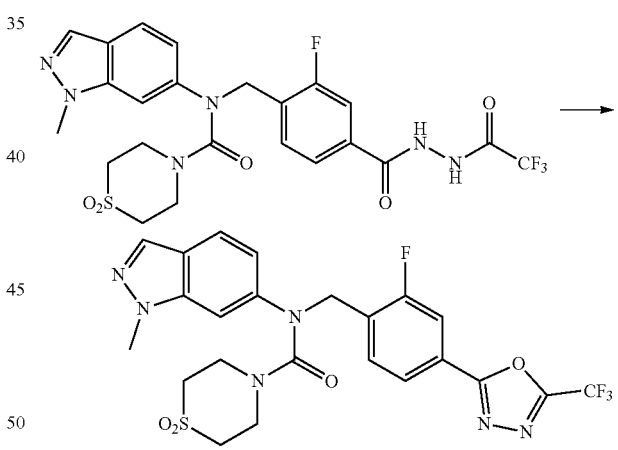

A mixture of N-(2-fluoro-4-(2-(2,2,2-trifluoroacetyl)hydrazine-1-carbonyl)benzyl)-N-(1-methyl-1H-indazol-6-yl)thiomorpholine-4-carboxamide 1,1-dioxide (0.214 g, 0.375 mmol) prepared in Step 4 and 1-methoxy-N-triethylammoniosulfonyl-methanimidate (Burgess reagent, 0.134 g, 0.563 mmol) in tetrahydrofuran (3 mL) was heated at 150° C. for 30 min under the microwaves, and cooled down to the room temperature to terminate the reaction. The reaction mixture was concentrated under the reduced pressure to remove the solvent, and 1N-water solution was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(2-fluoro-4-(5-(trifluoromethyl)-1,3,4-oxadiazol-2-yl)benzyl)-N-(1-methyl-1H-indazol-6-yl)thiomorpholine-4-carboxamide 1,1-dioxide as white solid (0.065 g, 31.1%).

$^1$H NMR (400 MHz, CDCl$_3$) δ 7.99-7.94 (m, 1H), 7.88 (dd, 1H, J=8.1, 1.7 Hz), 7.78-7.66 (m, 3H), 7.17-7.11 (m, 1H), 6.92 (dd, 1H, J=8.6, 1.8 Hz), 5.01 (s, 2H), 4.04 (s, 3H), 3.77-3.69 (m, 4H), 2.85-2.77 (m, 4H); LRMS (ES) m/z 553.33 (M$^+$+1).

Example 201. Compound 21546: N-(4-(5-(difluoromethyl)-1,3,4-oxadiazol-2-yl)-2-fluorobenzyl)-N-(1-methyl-1H-indazol-6-yl)thiomorpholine-4-carboxamide 1,1-dioxide

[Step 1] N-(4-(2-(2,2-difluoroacetyl)hydrazine-1-carbonyl)-2-fluorobenzyl)-N-(1-methyl-1H-indazol-6-yl)thiomorpholine-4-carboxamide 1,1-dioxide

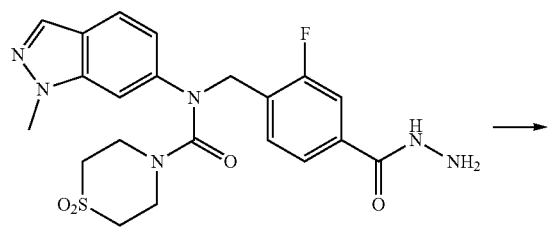

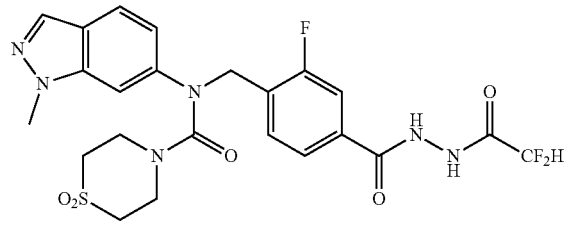

A solution of N-(2-fluoro-4-(hydrazinecarbonyl)benzyl)-N-(1-methyl-1H-indazol-6-yl)thiomorpholine-4-carboxamide 1,1-dioxide (0.179 g, 0.377 mmol) prepared in Step 3 of Example 200 and N,N-diisopropylethylamine (0.078 mL, 0.566 mmol) in dichloromethane (3 mL) was mixed at 0° C. with difluoroacetic anhydride (0.037 mL, 0.340 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; diisoprpylether/dichloromethane=0% to 5%) to give the title compound N-(4-(2-(2,2-difluoroacetyl)hydrazine-1-carbonyl)-2-fluorobenzyl)-N-(1-methyl-1H-indazol-6-yl)thiomorpholine-4-carboxamide 1,1-dioxide as light yellow solid (0.209 g, 100.0%).

[Step 2] Compound 21546

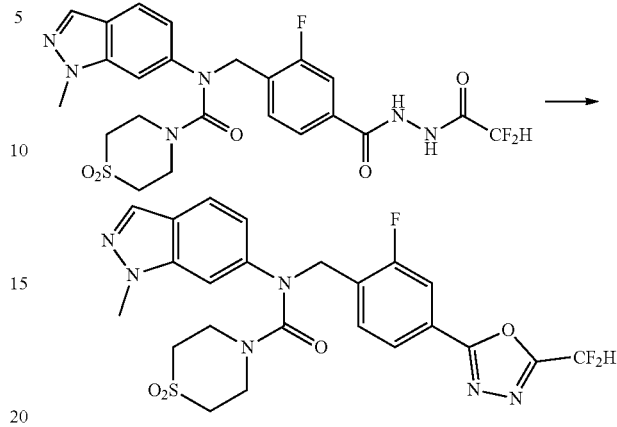

A mixture of N-(4-(2-(2,2-difluoroacetyl)hydrazine-1-carbonyl)-2-fluorobenzyl)-N-(1-methyl-1H-indazol-6-yl)thiomorpholine-4-carboxamide 1,1-dioxide (0.230 g, 0.416 mmol) prepared in Step 1 and 1-methoxy-N-triethylammoniosulfonyl-methanimidate (Burgess reagent, 0.149 g, 0.624 mmol) in tetrahydrofuran (3 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(4-(5-(difluoromethyl)-1,3,4-oxadiazol-2-yl)-2-fluorobenzyl)-N-(1-methyl-1H-indazol-6-yl)thiomorpholine-4-carboxamide 1,1-dioxide as white solid (0.079 g, 35.3%).

$^1$H NMR (400 MHz, CDCl$_3$) δ 7.99-7.94 (m, 1H), 7.88 (dd, 1H, J=8.0, 1.7 Hz), 7.75 (dd, 1H, J=10.1, 1.7 Hz), 7.72-7.66 (m, 2H), 7.16-7.10 (m, 1H), 7.05-6.76 (m, 2H), 5.01 (s, 2H), 4.04 (s, 3H), 3.77-3.69 (m, 4H), 2.85-2.77 (m, 4H); LRMS (ES) m/z 535.28 (M$^+$+1).

Example 202. Compound 21552: N-(4-(diethylamino)phenyl)-N-(2-fluoro-4-(5-(trifluoromethyl)-1,3,4-oxadiazol-2-yl)benzyl)thiomorpholine-4-carboxamide 1,1-dioxide

[Step 1] Methyl 4-((N-(4-(diethylamino)phenyl)-1,1-dioxidothiomorpholine-4-carboxamido)methyl)-3-fluorobenzoate

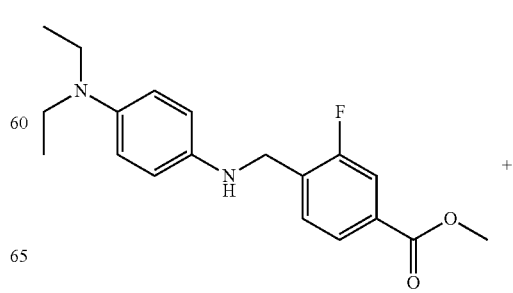

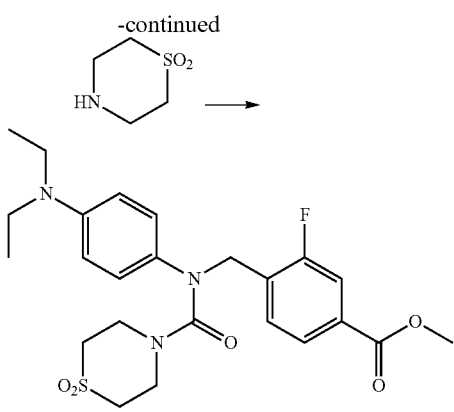

To a stirred solution of methyl 4-(((4-(diethylamino)phenyl)amino)methyl)-3-fluorobenzoate (0.330 g, 0.999 mmol) and N,N-diisopropylethylamine (1.744 mL, 9.988 mmol) in dichloromethane (10 mL) was added at 0° C. triphosgene (0.326 g, 1.099 mmol). The reaction mixture was stirred at the same temperature. Thiomorpholine 1,1-dioxide (0.142 g, 1.049 mmol) was added to the reaction mixture, and stirred at the room temperature for additional 3 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 12 g cartridge; methanol/dichloromethane=0% to 3%) to give the title compound methyl 4-((N-(4-(diethylamino)phenyl)-1,1-dioxidothiomorpholine-4-carboxamido)methyl)-3-fluorobenzoate as light yellow solid (0.288 g, 58.7%).

[Step 2] N-(4-(diethylamino)phenyl)-N-(2-fluoro-4-(hydrazinecarbonyl)benzyl)thiomorpholine-4-carboxamide 1,1-dioxide

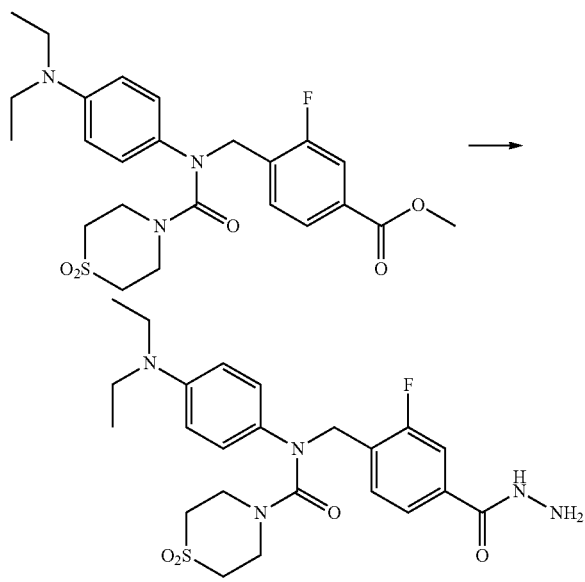

A mixture of methyl 4-((N-(4-(diethylamino)phenyl)-1,1-dioxidothiomorpholine-4-carboxamido)methyl)-3-fluorobenzoate (0.288 g, 0.586 mmol) prepared in Step 1 and hydrazine monohydrate (0.553 mL, 11.717 mmol) in ethanol (3 mL) was heated at reflux for 16 hr, and cooled down to the room temperature. The reaction mixture was concentrated under the reduced pressure to remove the solvent, and water was added to the concentrate, followed by extraction with ethyl acetate. The organic layer was washed with aqueous saturated sodium chloride solution, dried with anhydrous $MgSO_4$, filtered, and concentrated in vacuo. The title compound was used without further purification (0.225 g, 78.1%, light yellow solid).

[Step 3] N-(4-(diethylamino)phenyl)-N-(2-fluoro-4-(2-(2,2,2-trifluoroacetyl)hydrazine-1-carbonyl)benzyl)thiomorpholine-4-carboxamide 1,1-dioxide

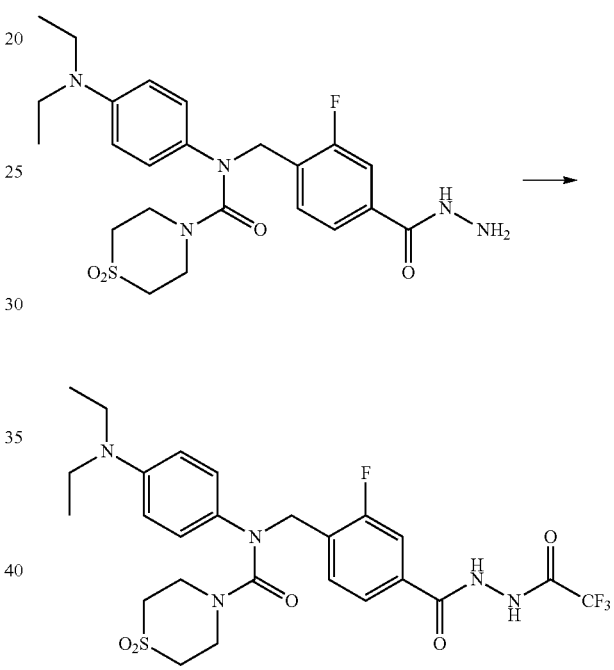

A solution of N-(4-(diethylamino)phenyl)-N-(2-fluoro-4-(hydrazinecarbonyl)benzyl)thiomorpholine-4-carboxamide 1,1-dioxide (0.112 g, 0.228 mmol) prepared in Step 2 and N,N-diisopropylethylamine (0.060 mL, 0.342 mmol) in dichloromethane (3 mL) was mixed at 0° C. with trifluoroacetic anhydride (0.029 mL, 0.205 mmol), and stirred at the room temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 5%) to give the title compound N-(4-(diethylamino)phenyl)-N-(2-fluoro-4-(2-(2,2,2-trifluoroacetyl)hydrazine-1-carbonyl)benzyl)thiomorpholine-4-carboxamide 1,1-dioxide as white solid (0.103 g, 76.9%).

[Step 4] Compound 21552

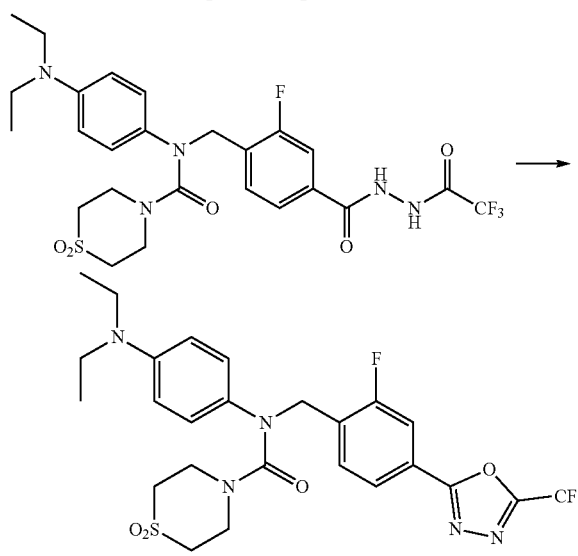

A mixture of N-(4-(diethylamino)phenyl)-N-(2-fluoro-4-(2-(2,2,2-trifluoroacetyl)hydrazine-1-carbonyl)benzyl)thiomorpholine-4-carboxamide 1,1-dioxide (0.110 g, 0.187 mmol) prepared in Step 1 and 1-methoxy-N-triethylammoniosulfonyl-methanimidate (Burgess reagent, 0.067 g, 0.281 mmol) in tetrahydrofuran (1 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 3%) to give the title compound N-(4-(diethylaminophenyl)-N-(2-fluoro-4-(5-(trifluoromethyl)-1,3,4-oxadiazol-2-yl)benzyl)thiomorpholine-4-carboxamide 1,1-dioxide as white solid (0.061 g, 57.0%).

$^1$H NMR (400 MHz, $CDCl_3$) δ 7.86 (d, 1H, J=8.0 Hz), 7.74 (dd, 1H, J=10.0, 1.6 Hz), 7.66 (t, 1H, J=7.6 Hz), 6.93-6.86 (m, 2H), 6.60-6.53 (m, 2H), 4.84 (s, 2H), 3.77-3.70 (m, 4H), 3.36-3.29 (m, 4H), 2.78-2.73 (m, 4H), 1.19-1.11 (m, 6H); LRMS (ES) m/z 570.24 ($M^+$+1).

Example 203. Compound 21553: N-(4-(diethylaminophenyl)-N-(4-(5-(difluoromethyl)-1,3,4-oxadiazol-2-yl)-2-fluorobenzyl)thiomorpholine-4-carboxamide 1,1-dioxide

[Step 1] N-(4-(diethylamino)phenyl)-N-(4-(2-(2,2-difluoroacetyl)hydrazine-1-carbonyl)-2-fluorobenzyl)thiomorpholine-4-carboxamide 1,1-dioxide

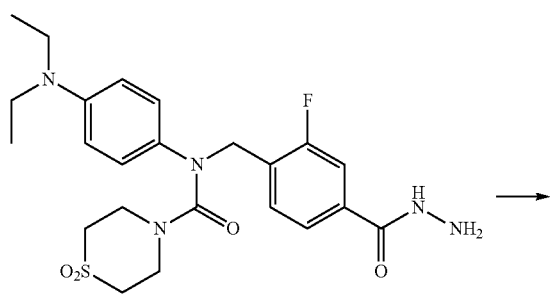

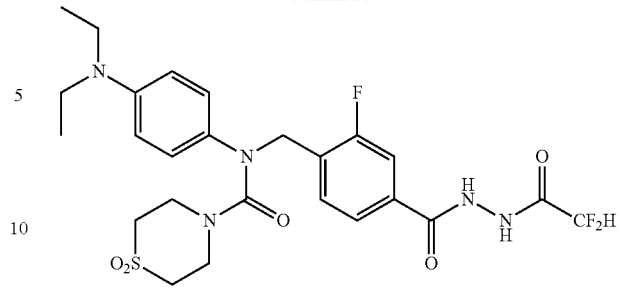

A solution of N-(4-(diethylamino)phenyl)-N-(2-fluoro-4-(hydrazinecarbonyl)benzyl)thiomorpholine-4-carboxamide 1,1-dioxide (0.112 g, 0.228 mmol) prepared in Step 2 of Example 202 and N,N-diisopropylethylamine (0.060 mL, 0.342 mmol) in dichloromethane (3 mL) was mixed at 0° C. with difluoroacetic anhydride (0.022 mL, 0.205 mmol), and stirred at the room temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography ($SiO_2$, 4 g cartridge; methanol/dichloromethane=0% to 5%) to give the title compound N-(4-(diethylamino)phenyl)-N-(4-(2-(2,2-difluoroacetyl)hydrazine-1-carbonyl)-2-fluorobenzyl)thiomorpholine-4-carboxamide 1,1-dioxide as white solid (0.106 g, 81.7%).

[Step 2] Compound 21553

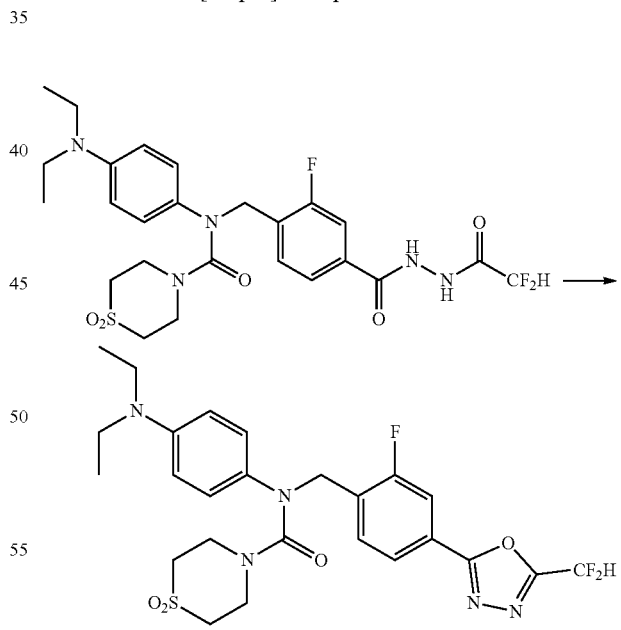

A mixture of N-(4-(diethylamino)phenyl)-N-(4-(2-(2,2-difluoroacetyl)hydrazine-1-carbonyl)-2-fluorobenzyl)thiomorpholine-4-carboxamide 1,1-dioxide (0.106 g, 0.186 mmol) prepared in Step 1 and 1-methoxy-N-triethylammoniosulfonyl-methanimidate (Burgess reagent, 0.067 g, 0.279 mmol) in tetrahydrofuran (1 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(diethylamino)phenyl)-N-(4-(5-(difluoromethyl)-1,3,4-oxadiazol-2-yl)-2-fluorobenzyl)thiomorpholine-4-carboxamide 1,1-dioxide as white solid (0.048 g, 46.8%).

$^1$H NMR (400 MHz; CDCl$_3$) δ 7.86 (dd, 1H, J=8.0, 1.7 Hz), 7.74 (dd, 1H, J=10.0, 1.7 Hz), 7.64 (t, 1H, J=7.6 Hz), 7.06-6.76 (m, 3H), 6.60-6.53 (m, 1H), 4.83 (s, 2H), 3.77-3.72 (m, 4H), 3.37-3.27 (m, 4H), 2.77-2.72 (m, 4H), 1.15 (t, 6H, J=7.0 Hz); LRMS (ES) m/z 552.07 (M$^+$+1).

Example 204. Compound 21554: N-(4-(5-(difluoromethyl)-1,3,4-oxadiazol-2-yl)-2-fluorobenzyl)-4-methyl-N-phenethylpiperazine-1-carboxamide

[Step 1] N-(2-fluoro-4-(hydrazinecarbonyl)benzyl)-4-methyl-N-phenethylpiperazine-1-carboxamide

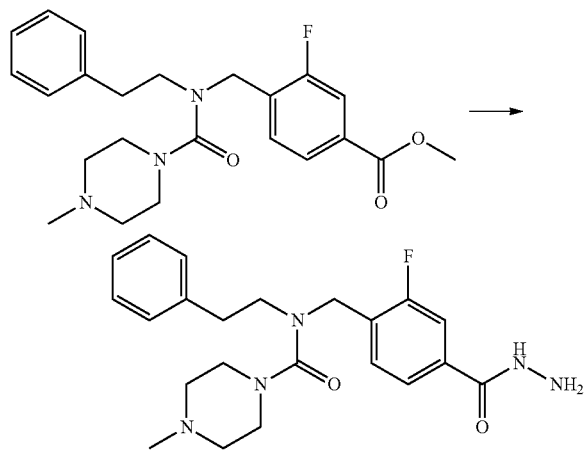

Methyl 3-fluoro-4-((4-methyl-N-propylpiperazine-1-carboxamido)methyl)benzoate (0.178 g, 0.430 mmol) and hydrazine monohydrate (0.203 mL, 4.300 mmol) were mixed at the room temperature in ethanol (3 mL) and then stirred at 120° C. for 16 hr, and cooled down to the room temperature, concentrated under the reduced pressure to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(hydrazinecarbonyl)benzyl)-4-methyl-N-phenethylpiperazine-1-carboxamide as white foam (0.104 g, 58.3%).

[Step 2] (N-(4-(2-(2,2-difluoroacetyl)hydrazine-1-carbonyl)-2-fluorobenzyl)-4-methyl-N-phenethylpiperazine-1-carboxamide

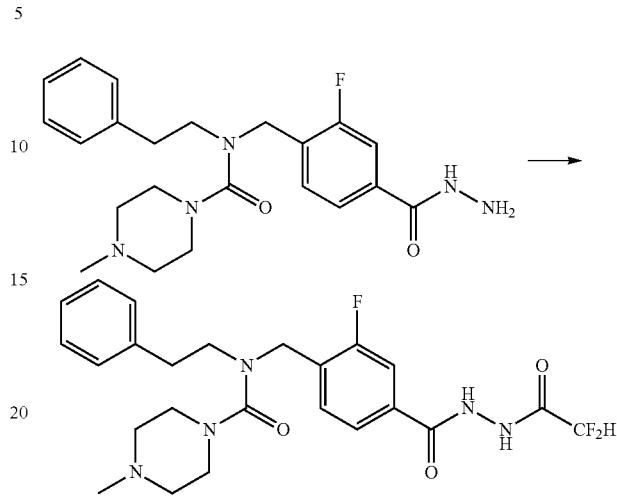

A solution of N-(2-fluoro-4-(hydrazinecarbonyl)benzyl)-4-methyl-N-phenethylpiperazine-1-carboxamide (0.104 g, 0.251 mmol) prepared in Step 1 and triethylamine (0.069 mL, 0.502 mmol) in dichloromethane (1 mL) was mixed at the room temperature with difluoroacetic anhydride (0.031 mL, 0.251 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.120 g, 97.4%, yellow foam).

[Step 3] Compound 21554

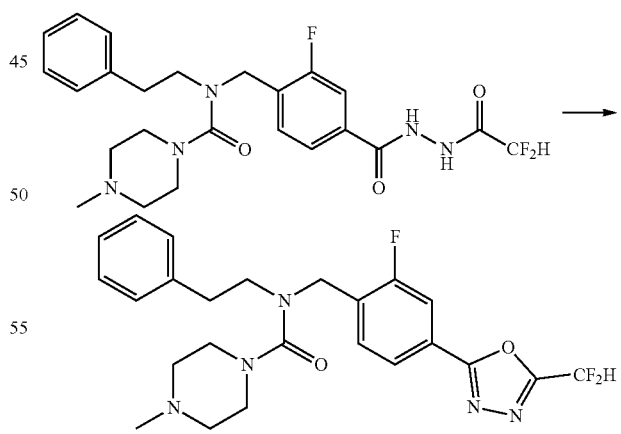

N-(4-(2-(2,2-difluoroacetyl)hydrazine-1-carbonyl)-2-fluorobenzyl)-4-methyl-N-phenethylpiperazine-1-carboxamide (0.120 g, 0.244 mmol) prepared in Step 2 and 1-methoxy-N-triethylammoniosulfonyl-methanimidate (Burgess reagent, 0.087 g, 0.366 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(5-(difluoromethyl)-1,3,4-oxadiazol-2-yl)-2-fluorobenzyl)-4-methyl-N-phenethylpiperazine-1-carboxamide as yellow oil (0.038 g, 32.4%).

$^1$H NMR (400 MHz, CDCl$_3$) δ 7.90-7.77 (m, 2H), 7.43 (t, 1H, J=7.6 Hz), 7.34-7.18 (m, 3H), 7.20-7.12 (m, 2H), 6.92 (t, 1H, J=51.7 Hz), 4.51 (s, 2H), 3.37 (dd, 2H, J=8.4, 6.5 Hz), 3.30 (t, 4H, J=4.9 Hz), 2.89 (dd, 2H, J=8.3, 6.5 Hz), 2.46 (s, 4H), 2.36 (s, 3H); LRMS (ESI) m/z 474.4 (M$^+$+H).

Example 205. Compound 21555: N-(4-(5-(difluoromethyl)-1,3,4-oxadiazol-2-yl)-2-fluorobenzyl)-N-phenethylmorpholine-4-carboxamide

[Step 1] N-(2-fluoro-4-(hydrazinecarbonyl)benzyl)-N-phenethylmorpholine-4-carboxamide

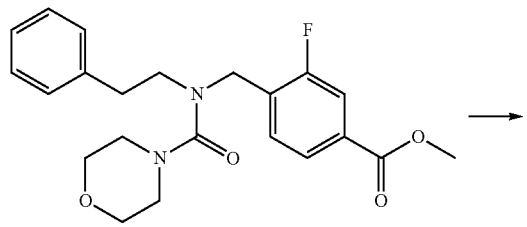

Methyl 3-fluoro-4-((N-phenethylmorpholine-4-carboxamido)methyl)benzoate (0.149 g, 0.373 mmol) and hydrazine monohydrate (0.176 mL, 3.728 mmol) were mixed at the room temperature in ethanol (3 mL) and then stirred at 100° C. for 16 hr, and cooled down to the room temperature, concentrated under the reduced pressure to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(hydrazinecarbonyl)benzyl)-N-phenethylmorpholine-4-carboxamide as white foam (0.099 g, 66.0%).

[Step 2] N-(4-(2-(2,2-difluoroacetyl)hydrazine-1-carbonyl)-2-fluorobenzyl)-N-phenethylmorpholine-4-carboxamide

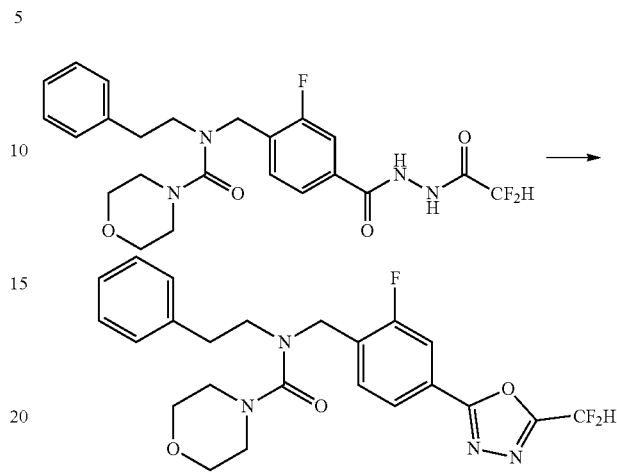

A solution of N-(2-fluoro-4-(hydrazinecarbonyl)benzyl)-N-phenethylmorpholine-4-carboxamide (0.099 g, 0.246 mmol) prepared in Step 1 and triethylamine (0.068 mL, 0.492 mmol) in dichloromethane (1 mL) was mixed at the room temperature with difluoroacetic anhydride (0.031 mL, 0.246 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.110 g, 93.5%, yellow foam).

[Step 3] Compound 21555

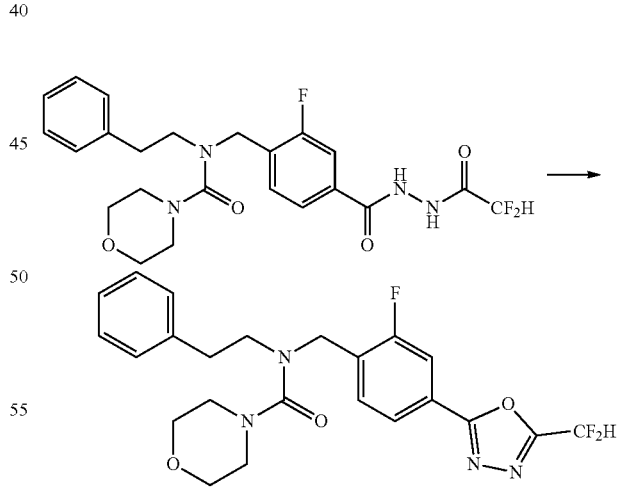

N-(4-(2-(2,2-difluoroacetyl)hydrazine-1-carbonyl)-2-fluorobenzyl)-N-phenethylmorpholine-4-carboxamide (0.110 g, 0.230 mmol) prepared in Step 2 and 1-methoxy-N-triethylammoniosulfonyl-methanimidate (Burgess reagent, 0.082 g, 0.345 mmol) were mixed at the room temperature in tetrahydrofuran (2 mL) and then stirred at 80° C. for 16 hr, and cooled down to the room temperature. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 3%) to give the title compound N-(4-(5-(difluoromethyl)-1,3,4-oxadiazol-2-yl)-2-fluorobenzyl)-N-phenethylmorpholine-4-carboxamide as yellow oil (0.041 g, 38.9%).

¹H NMR (400 MHz, CDCl₃) δ 7.89-7.77 (m, 2H), 7.43 (t, 1H, J=7.6 Hz), 7.36-7.27 (m, 2H), 7.25-7.12 (m, 3H), 6.92 (t, 1H, J=51.7 Hz), 4.51 (s, 2H), 3.62 (m, 5H), 3.38 (dd, 2H, J=8.4, 6.5 Hz), 3.22-3.13 (m, 4H), 2.89 (dd, 2H, J=8.3, 6.4 Hz); LRMS (ESI) m/z 461.0 (M⁺+H).

Example 206. Compound 21556: N-(4-(5-(difluoromethyl)-1,3,4-oxadiazol-2-yl)-2-fluorobenzyl)-N-(2-methoxyphenethyl)-4-methylpiperazine-1-carboxamide

[Step 1] N-(2-fluoro-4-(hydrazinecarbonyl)benzyl)-N-(2-methoxyphenethyl)-4-methylpiperazine-1-carboxamide

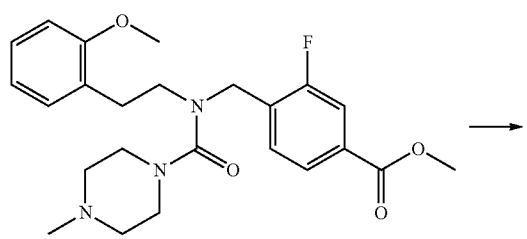

Methyl 4-((N-(2-methoxyphenethyl)-4-methylpiperazine-1-carboxamido)methyl)benzoate (0.073 g, 0.164 mmol) and hydrazine monohydrate (0.078 mL, 1.641 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound N-(4-(hydrazinecarbonyl)benzyl)-N-(2-methoxyphenethyl)-4-methylpiperazine-1-carboxamide as brown foam (0.024 g, 32.4%).

[Step 2] N-(4-(2-(2,2-difluoroacetyl)hydrazine-1-carbonyl)-2-fluorobenzyl)-N-(2-methoxyphenethyl)-4-methylpiperazine-1-carboxamide

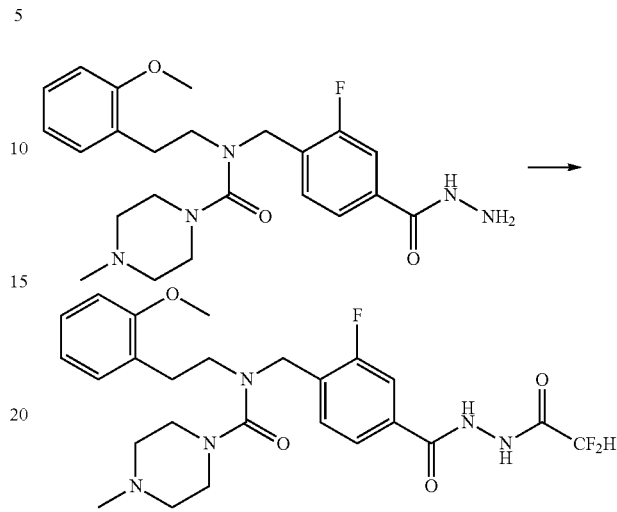

A solution of N-(2-fluoro-4-(hydrazinecarbonyl)benzyl)-N-(2-methoxyphenethyl)-4-methylpiperazine-1-carboxamide (0.024 g, 0.053 mmol) prepared in Step 1 and triethylamine (0.015 mL, 0.106 mmol) in dichloromethane (1 mL) was mixed at the room temperature with difluoroacetic anhydride (0.007 mL, 0.053 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.025 g, 90.1%, brown foam).

[Step 3] Compound 21556

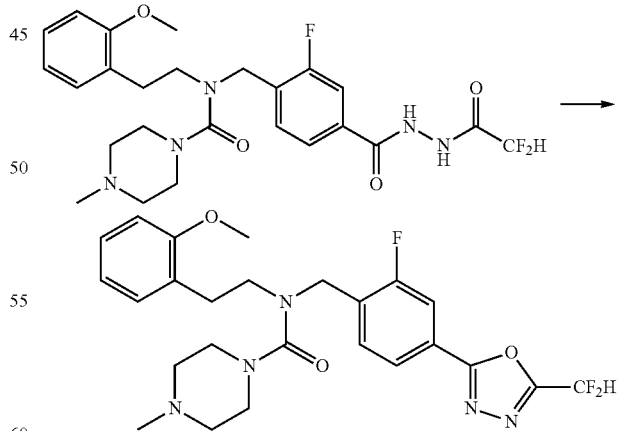

N-(4-(2-(2,2-difluoroacetyl)hydrazine-1-carbonyl)-2-fluorobenzyl)-N-(2-methoxyphenethyl)-4-methylpiperazine-1-carboxamide (0.025 g, 0.048 mmol) prepared in Step 2 and 1-methoxy-N-triethylammoniosulfonyl-methanimidate (Burgess reagent, 0.017 g, 0.072 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(4-(5-(difluoromethyl)-1,3,4-oxadiazol-2-yl)-2-fluorobenzyl)-N-(2-methoxyphenethyl)-4-methylpiperazine-1-carboxamide as colorless oil (0.004 g, 15.7%).

$^1$H NMR (400 MHz, CDCl$_3$) δ 7.90-7.77 (m, 2H), 7.47 (t, 1H, J=7.7 Hz), 7.21 (td, 1H, J=7.8, 1.8 Hz), 7.09 (dd, 1H, J=7.4, 1.7 Hz), 7.06-6.76 (m, 3H), 4.56 (s, 2H), 3.80 (s, 3H), 3.34 (m, 4H), 2.90 (t, 2H, J=7.4 Hz), 2.52 (s, 4H), 2.41 (s, LRMS (ESI) m/z 504.08 (M$^+$+H).

Example 207. Compound 21557: N-(4-(5-(difluoromethyl)-1,3,4-oxadiazol-2-yl)-2-fluorobenzyl)-N-(2-methoxyphenethyl) morpholine-4-carboxamide

[Step 1] N-(2-fluoro-4-(hydrazinecarbonyl)benzyl)-N-(2-methoxyphenethyl)morpholine-4-carboxamide

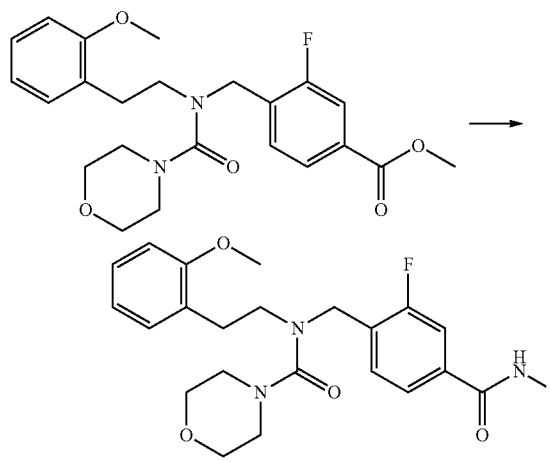

Methyl 3-fluoro-4-((N-(2-methoxyphenethyl)morpholine-4-carboxamido)methyl)benzoate (0.073 g, 0.168 mmol) and hydrazine monohydrate (0.080 mL, 1.684 mmol) were mixed at the room temperature in ethanol (3 mL) and then stirred at 120° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(2-fluoro-4-(hydrazinecarbonyl)benzyl)-N-(2-methoxyphenethyl)morpholine-4-carboxamide as white foam (0.031 g, 43.0%).

[Step 2] N-(4-(2-(2,2-difluoroacetyl)hydrazine-1-carbonyl)-2-fluorobenzyl)-N-(2-methoxyphenethyl) morpholine-4-carboxamide

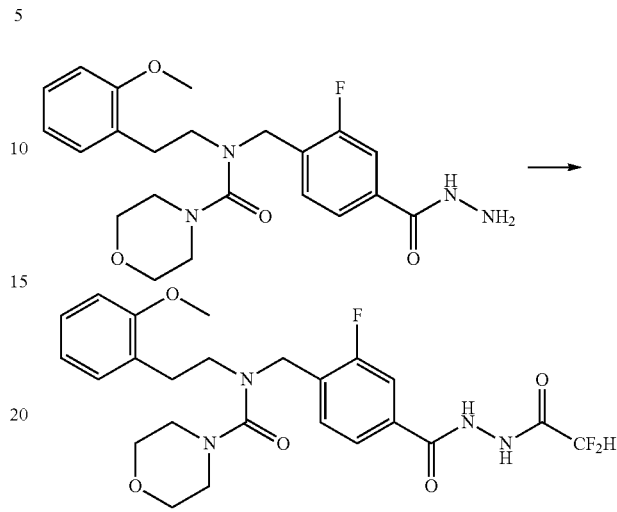

A solution of N-(2-fluoro-4-(hydrazinecarbonyl)benzyl)-N-(2-methoxyphenethyl)morpholine-4-carboxamide (0.031 g, 0.072 mmol) prepared in Step 1 and triethylamine (0.020 mL, 0.145 mmol) in dichloromethane (1 mL) was mixed at the room temperature with difluoroacetic anhydride (0.009 mL, 0.072 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.035 g, 95.0%, brown foam).

[Step 3] Compound 21557

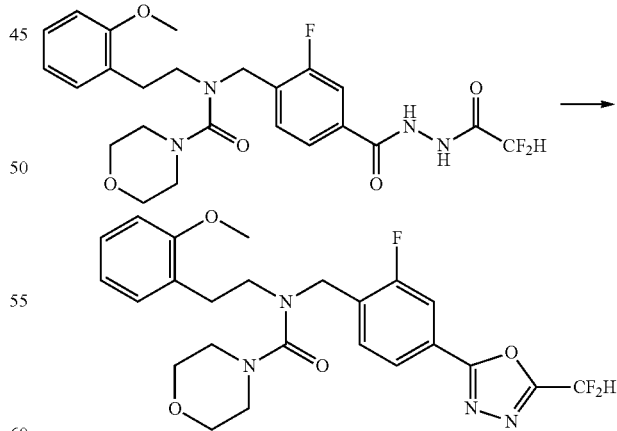

N-(4-(2-(2,2-difluoroacetyl)hydrazine-1-carbonyl)-2-fluorobenzyl)-N-(2-methoxyphenethyl)morpholine-4-carboxamide (0.035 g, 0.069 mmol) prepared in Step 2 and 1-methoxy-N-triethylammoniosulfonyl-methanimidate (Burgess reagent, 0.025 g, 0.103 mmol) were mixed at the room temperature in tetrahydrofuran (2 mL) and then stirred at 80° C. for 16 hr, and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 3%) to give the title compound N-(4-(5-(difluoromethyl)-1,3,4-oxadiazol-2-yl)-2-fluorobenzyl)-N-(2-methoxyphenethyl) morpholine-4-carboxamide as yellow oil (0.029 g, 86.5%).

¹H NMR (400 MHz, CDCl₃) δ 7.89-7.77 (m, 2H), 7.48 (t, 1H, J=7.6 Hz), 7.24-7.17 (m, 1H), 7.10 (dd, 1H, J=7.4, 1.8 Hz), 7.05-6.76 (m, 3H), 4.57 (s, 2H), 3.80 (s, 3H), 3.67-3.60 (m, 4H), 3.39-3.30 (m, 2H), 3.24-3.16 (m, 4H), 2.96-2.87 (m, 2H); LRMS (ESI) m/z 491.0 (M⁺+H).

Example 208. Compound 21564: N-(3-chloro-4-fluorophenyl)-N-(2-fluoro-4-(5-(trifluoromethyl)-1,3,4-oxadiazol-2-yl)benzyl)-4-methylpiperazine-1-carboxamide

[Step 1] Methyl 44N-(3-chloro-4-fluorophenyl)-4-methylpiperazine-1-carboxamido)methyl)-3-fluorobenzoate

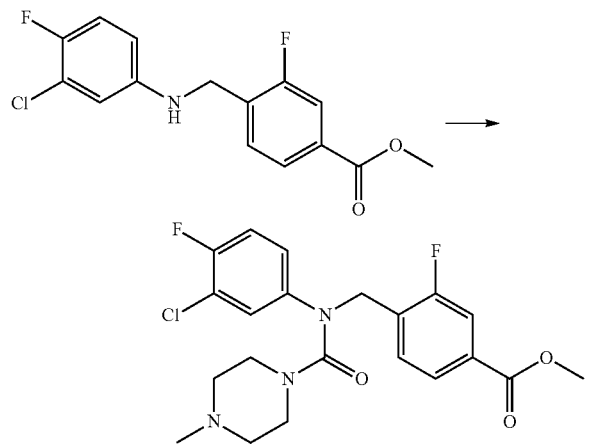

A solution of methyl 4-(((3-chloro-4-fluorophenyl)amino)methyl)-3-fluorobenzoate (0.200 g, 0.642 mmol), 1-methylpiperazine (0.072 mL, 0.648 mmol), triphosgene (0.209 g, 0.706 mmol) and N,N-diisopropylethylamine (1.118 mL, 6.416 mmol) in dichloromethane (10 mL) was stirred at the room temperature for 1 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound methyl 4-((N-(3-chloro-4-fluorophenyl)-4-methylpiperazine-1-carboxamido)methyl)-3-fluorobenzoate as yellow oil (0.244 g, 86.8%).

[Step 2] N-(3-chloro-4-fluorophenyl)-N-(2-fluoro-4-(hydrazinecarbonyl)benzyl)-4-methylpiperazine-1-carboxamide

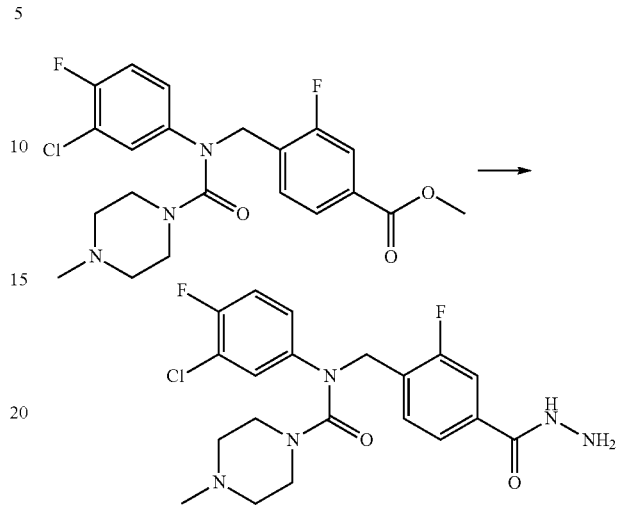

A mixture of methyl 4-((N-(3-chloro-4-fluorophenyl)-4-methylpiperazine-1-carboxamido)methyl)-3-fluorobenzoate (0.244 g, 0.557 mmol) prepared in Step 1 and hydrazine monohydrate (0.526 mL, 11.145 mmol) in ethanol (2 mL) was heated at reflux for 16 hr, and cooled down to the room temperature. The reaction mixture was concentrated under the reduced pressure to remove, the solvent, and water was added to the concentrate, followed by extraction with ethyl acetate. The organic layer was washed with aqueous saturated sodium chloride solution, dried with anhydrous MgSO₄, filtered, and concentrated in vacuo. The title compound was used without further purification (0.240 g, 98.4%, white solid).

[Step 3] N-(3-chloro-4-fluorophenyl)-N-(2-fluoro-4-(2-(2,2,2-trifluoroacetyl)hydrazine-1-carbonyl)benzyl)-4-methylpiperazine-1-carboxamide

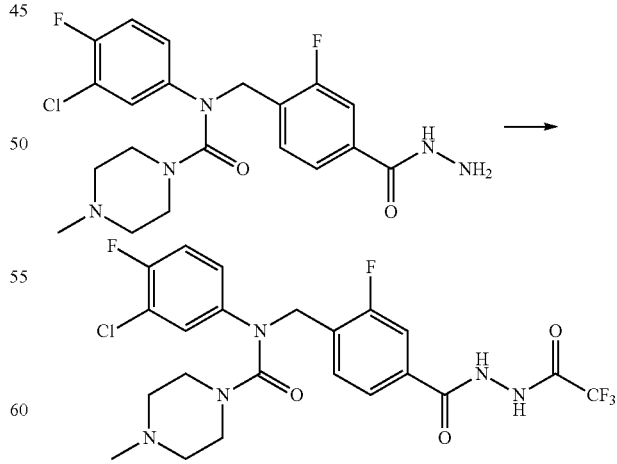

A solution of N-(3-chloro-4-fluorophenyl)-N-(2-fluoro-4-(hydrazinecarbonyl)benzyl)-4-methylpiperazine-1-carboxamide (0.120 g, 0.274 mmol) prepared in Step 2 and N,N-diisopropylethylamine (0.072 mL, 0.411 mmol) in dichloromethane (2 mL) was mixed at 0° C. with trifluoroacetic anhydride (0.035 mL, 0.247 mmol), and stirred at the room temperature for 3 hr. Then; saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(3-chloro-4-fluorophenyl)-N-(2-fluoro-4-(2-(2,2,2-trifluoroacetyl)hydrazine-1-carbonyl)benzyl)-4-methylpiperazine-1-carboxamide as white solid (0.146 g, 99.8%).

[Step 4] Compound 21564

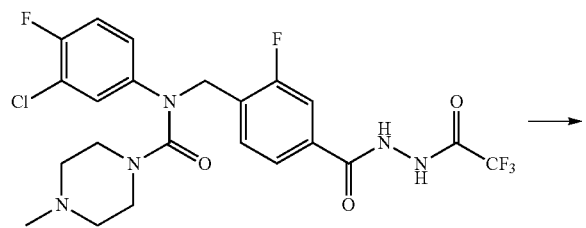

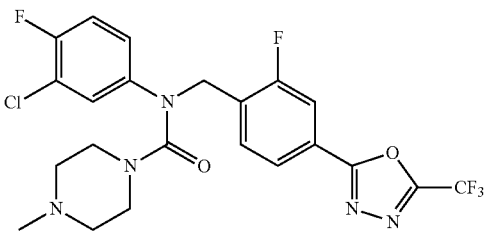

A mixture of N-(3-chloro-4-fluorophenyl)-N-(2-fluoro-4-(2-(2,2,2-trifluoroacetyl)hydrazine-1-carbonyl)benzyl)-4-methylpiperazine-1-carboxamide (0.146 g, 0.273 mmol) prepared in Step 3 and 1-methoxy-N-triethylammoniosulfonyl-methanimidate (Burgess reagent, 0.098 g, 0.410 mmol) in dichloromethane (10 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound N-(3-chloro-4-fluorophenyl)-N-(2-fluoro-4-(5-(trifluoromethyl)-1,3,4-oxadiazol-2-yl)benzyl)-4-methylpiperazine-1-carboxamide as yellow oil (0.058 g, 41.1%).

$^1$H NMR (400 MHz, CDCl$_3$) δ 7.91-7.83 (m, 1H), 7.79-7.72 (m, 1H), 7.72-7.65 (m, 1H), 7.20-7.12 (m, 1H), 7.13-7.04 (m, 1H), 7.01-6.92 (m, 1H), 4.90 (s, 2H), 3.41-3.27 (m, 4H), 2.33-2.30 (d, 4H); LRMS (ES) m/z 516.3 (M$^+$+1).

Example 209. Compound 21565: N-(3-chloro-4-fluorophenyl)-N-(4-(5-(difluoromethyl)-1,3,4-oxadiazol-2-yl)-2-fluorobenzyl)-4-methylpiperazine-1-carboxamide

[Step 1] N-(3-chloro-4-fluorophenyl)-N-(4-(2-(2,2-difluoroacetyl)hydrazine-1-carbonyl)-2-fluorobenzyl)-4-methylpiperazine-1-carboxamide

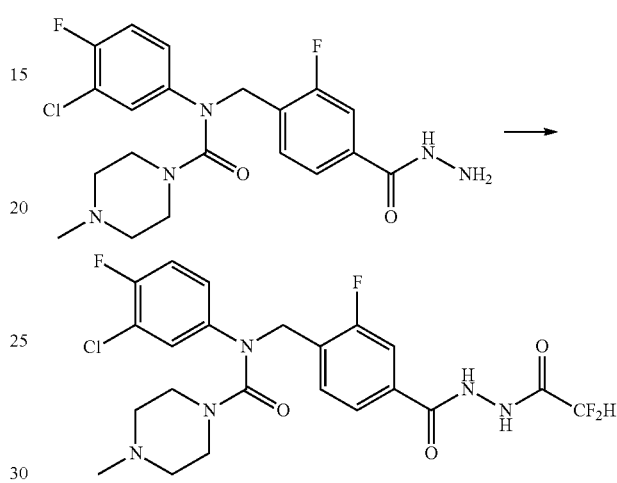

A solution of N-(3-chloro-4-fluorophenyl)-N-(2-fluoro-4-(hydrazinecarbonyl)benzyl)-4-methylpiperazine-1-carboxamide (0.120 g, 0.274 mmol) prepared in Step 2 of Example 208 and N,N-diisopropylethylamine (0.072 mL, 0.411 mmol) in dichloromethane (2 mL) was mixed at 0° C. with difluoroacetic anhydride (0.027 mL, 0.247 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-(3-chloro-4-fluorophenyl)-N-(4-(2-(2,2-difluoroacetyl)hydrazine-1-carbonyl)-2-fluorobenzyl)-4-methylpiperazine-1-carboxamide as yellow oil (0.029 g, 20.5%).

[Step 2] Compound 21565

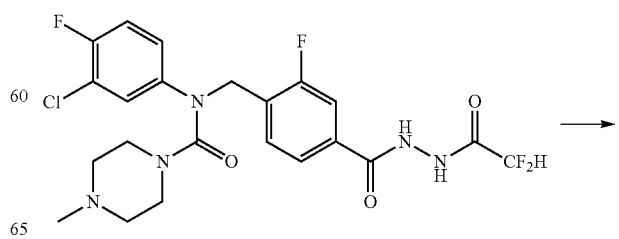

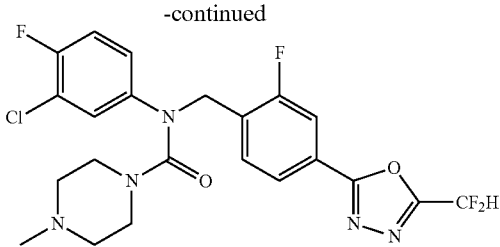

A mixture of N-(3-chloro-4-fluorophenyl)-N-(4-(2-(2,2-difluoroacetyl)hydrazine-1-carbonyl)-2-fluorobenzyl)-4-methylpiperazine-1-carboxamide (0.300 g, 0.582 mmol) prepared in Step 1 and 1-methoxy-N-triethylammoniosulfonyl-methanimidate (Burgess reagent, 0.208 g, 0.872 mmol) in tetrahydrofuran (3 mL) was heated at 150° C. for 30 min under the microwaves, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 12 g cartridge; ethyl acetate/hexane=0% to 50%) to give the title compound N-(3-chloro-4-fluorophenyl)-N-(4-(5-(difluoromethyl)-1,3,4-oxadiazol-2-yl)-2-fluorobenzyl)-4-methylpiperazine-1-carboxamide as white solid (0.073 g, 25.2%).

$^1$H NMR (400 MHz, CDCl$_3$) δ 7.87 (dd, 1H, J=7.9, 1.7 Hz), 7.76 (dd, 1H, J=10.2, 1.7 Hz), 7.67 (t, 1H, J=7.6 Hz), 7.17 (dd, 1H, J=6.3, 2.7 Hz), 7.09 (t, 1H, J=8.6 Hz), 7.05-6.76 (m, 2H), 4.90 (s, 2H), 3.43-3.38 (m, 4H), 2.41-2.36 (m, 4H); LRMS (ES) m/z 498.12 (M$^+$+1).

Example 210. Compound 21566: N-((5-(5-(difluoromethyl)-1,3,4-oxadiazol-2-yl)pyridin-2-yl)methyl)-N-phenyl-2-oxa-6-azaspiro[3.3]heptane-6-carboxamide

[Step 1] N-phenyl-2-oxa-6-azaspiro[3.3]heptane-6-carboxamide

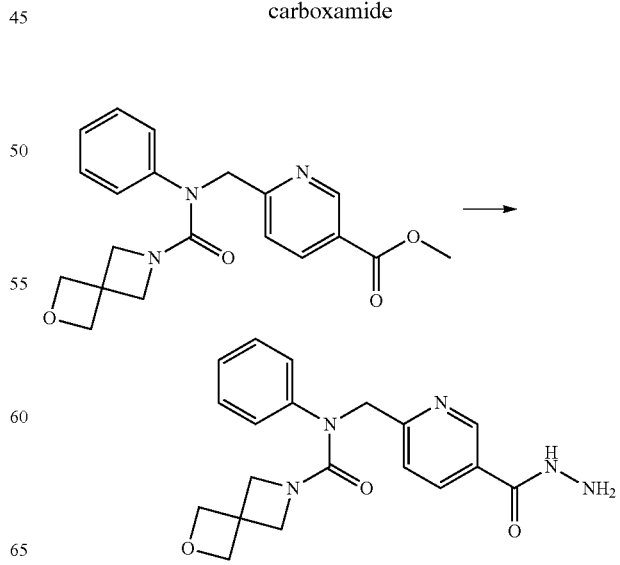

A solution of isocyanatobenzene (0.300 g, 2.518 mmol) and 2-oxa-6-azaspiro[3.3]heptane (0.250 g, 2.518 mmol) in diethylether (10 mL) was stirred at the room temperature for 16 hr. The precipitates were collected by filtration, washed by diethylether, and dried to give the title compound N-phenyl-2-oxa-6-azaspiro[3.3]heptane-6-carboxamide as white solid (0.400 g, 72.8%).

[Step 2] Methyl 6-((N-phenyl-2-oxa-6-azaspiro[3.3]heptane-6-carboxamido)methyl)nicotinate

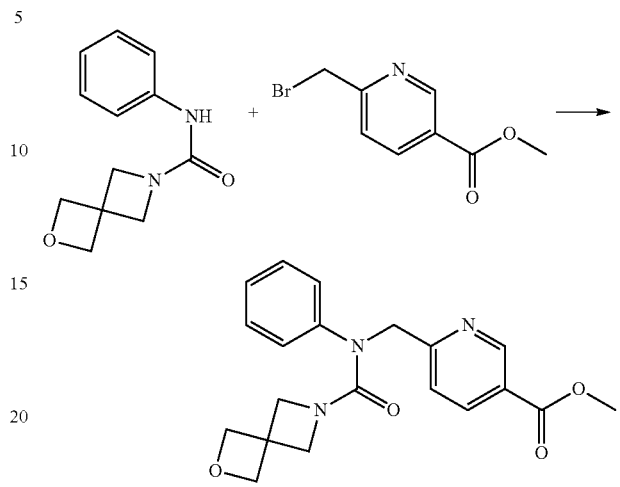

To a stirred solution of N-phenyl-2-oxa-6-azaspiro[3.3]heptane-6-carboxamide (0.300 g, 1.375 mmol) prepared in Step 1 in N,N-dimethylformamide (2 mL) was added at 0° C. sodium hydride (60.00%, 0.055 g, 1.375 mmol). The reaction mixture was stirred at the same temperature for 30 min. Methyl 6-(bromomethyl)nicotinate (0.316 g, 1.375 mmol) was added to the reaction mixture, and stirred at the room temperature for additional 2 hr. The reaction mixture was concentrated under the reduced pressure to remove the solvent, and water was added to the concentrate, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 4 g cartridge; methanol/dichloromethane=0% to 5%) to give the title compound methyl 6-((N-phenyl-2-oxa-6-azaspiro[3.3]heptane-6-carboxamido)methyl)nicotinate as brown oil (0.426 g, 84.4%).

[Step 3] N-((5-(hydrazinecarbonyl)pyridin-2-yl)methyl)-N-phenyl-2-oxa-6-azaspiro[3.3]heptane-6-carboxamide Methyl 6-((N-phenyl-2-oxa-6-azaspiro[3.3]heptane-6-carboxamido)methyl)nicotinate (0.326 g, 0.887 mmol) prepared in Step 2 and hydrazine monohydrate (0.419 mL, 8.873 mmol) were mixed at the room temperature in ethanol (3 mL) and then stirred at 100° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound N-((5-(hydrazinecarbonyl)pyridin-2-yl)methyl)-N-phenyl-2-oxa-6-azaspiro[3.3]heptane-6-carboxamide as white foam (0.036 g, 11.0%).

[Step 4] N-((5-(2-(2,2-difluoroacetyl)hydrazine-1-carbonyl)pyridin-2-yl)methyl)-N-phenyl-2-oxa-6-azaspiro[3.3]heptane-6-carboxamide

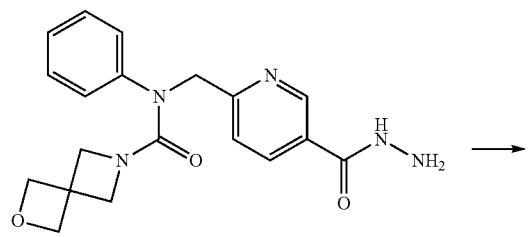

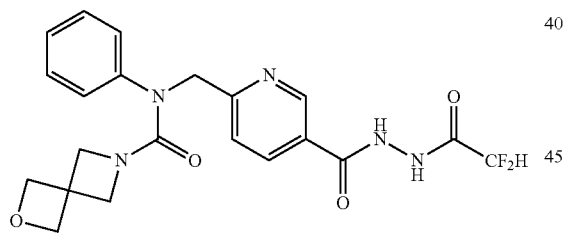

A solution of N-((5-(hydrazinecarbonyl)pyridin-2-yl)methyl)-N-phenyl-2-oxa-6-azaspiro[3.3]heptane-6-carboxamide (0.036 g, 0.098 mmol) prepared in Step 3 and triethylamine (0.027 mL, 0.196 mmol) in dichloromethane (1 mL) was mixed at the room temperature with difluoroacetic anhydride (0.012 mL, 0.098 mmol). The reaction mixture was stirred at the same temperature for 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The title compound was used without further purification (0.042 g, 96.2%, brown oil).

[Step 5] Compound 21566

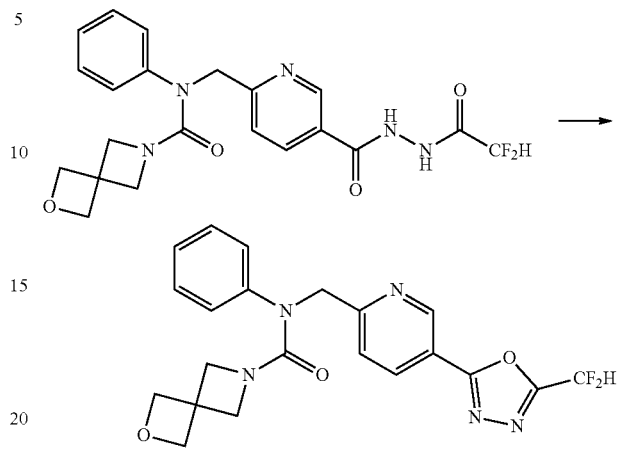

N-((5-(2-(2,2-difluoroacetyl)hydrazine-1-carbonyl)pyridin-2-yl)methyl)-N-phenyl-2-oxa-6-azaspiro[3.3]heptane-6-carboxamide (0.042 g, 0.094 mmol) prepared in Step 4 and 1-methoxy-N-triethylammoniosulfonyl-methanimidate (Burgess reagent, 0.034 g, 0.141 mmol) were mixed at the room temperature in tetrahydrofuran (2 mL) and then stirred at 80° C. for 16 hr, and cooled down to the room temperature. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-((5-(5-(difluoromethyl)-1,3,4-oxadiazol-2-yl)pyridin-2-yl)methyl)-N-phenyl-2-oxa-6-azaspiro[3.3]heptane-6-carboxamide as white solid (0.039 g, 96.3%).

$^1$H NMR (400 MHz, CDCl$_3$) δ 9.20 (dd, 1H, J=2.2, 0.8 Hz), 8.36 (dd, 1H, J=8.2, 2.2 Hz), 7.65 (dd, 1H, J=8.2, 0.8 Hz), 7.39-7.29 (m, 2H), 7.25-7.19 (m, 2H), 6.92 (t, 1H, J=51.7 Hz), 5.08 (s, 2H), 4.62 (s, 4H), 3.74 (s, 4H); LRMS (ESI) m/z 428.07 (M$^+$+H).

Example 211. Compound 21568: Tert-butyl (4-(5-(difluoromethyl)-1,3,4-oxadiazol-2-yl)benzyl)(phenyl)carbamate

[Step 1] Tert-butyl phenylcarbamate

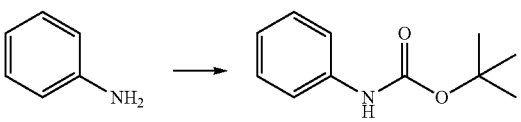

A solution of aniline (2.941 mL, 32.213 mmol), di-tert-butyl dicarbonate (8.437 g, 38.656 mmol) and potassium carbonate (5.342 g, 38.656 mmol) in tetrahydrofuran (100 mL) was stirred at the room temperature for 16 hr. The reaction mixture was concentrated under the reduced pressure to remove the solvent, and water was added to the concentrate, followed by extraction with ethyl acetate. The organic layer was washed with aqueous saturated sodium chloride solution, dried with anhydrous MgSO$_4$, filtered, and concentrated in vacuo. The concentrate was diluted with ethyl acetate (50 mL) and hexane (50 mL) and stirred. The resulting precipitates were collected by filtration, washed by hexane, and dried to give the title compound tert-butyl phenylcarbamate product as white solid (3.560 g, 57.2%).

[Step 2] Methyl 4-(((tert-butoxycarbonyl)(phenyl)amino)methyl)benzoate

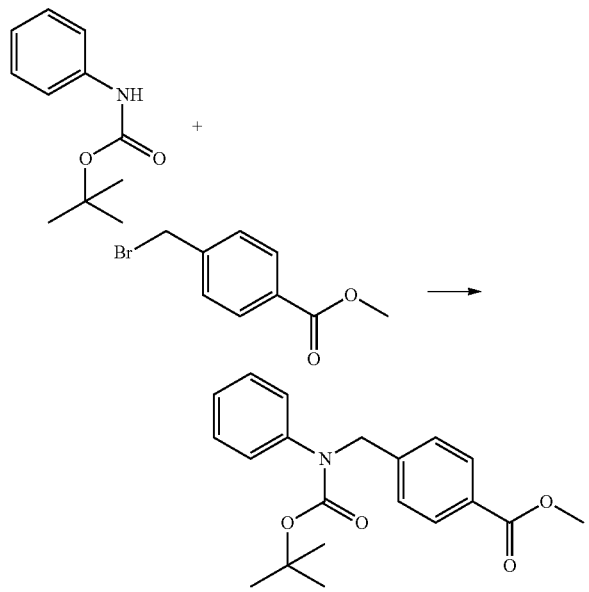

To a stirred solution of tert-butyl phenylcarbamate (1.700 g, 8.797 mmol) in N,N-dimethylformide (80 mL) was added at 0° C. sodium hydride (60.00%, 0.422 g, 10.556 mmol). The reaction mixture was stirred at the same temperature. Methyl 4-(bromomethyl)benzoate (2.418 g, 10.556 mmol) was added to the reaction mixture, and stirred at the room temperature for additional 1 hr. to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 10%) to give the title compound methyl 4-(((tert-butoxycarbonyl)(phenyl)amino)methyl)benzoate as colorless oil (3.003 g, 100.0%).

[Step 3] Tert-butyl (4-(hydrazinecarbonyl)benzyl)(phenyl)carbamate

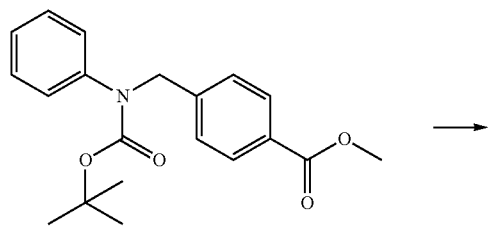

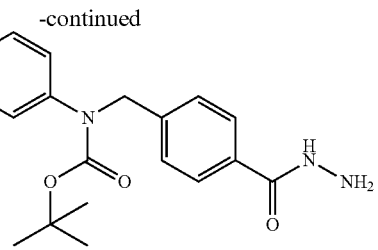

A mixture of methyl 4-(((tert-butoxycarbonyl)(phenyl)amino)methyl)benzoate (3.000 g, 8.787 mmol) prepared in Step 2 and hydrazine monohydrate (8.300 mL, 175.742 mmol) in ethanol (10 mL) was heated at reflux for 16 hr, and cooled down to the room temperature to terminate the reaction. The reaction mixture was concentrated under the reduced pressure to remove the solvent, and water was added to the concentrate, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; methanol/dichloromethane=0% to 5%) to give the title compound tert-butyl (4-(hydrazinecarbonyl)benzyl)(phenyl)carbamate as white solid (3.000 g, 100.0%).

[Step 4] Tert-butyl (4-(2-(2,2-difluoroacetyl)hydrazine-1-carbonyl)benzyl)(phenyl)carbamate

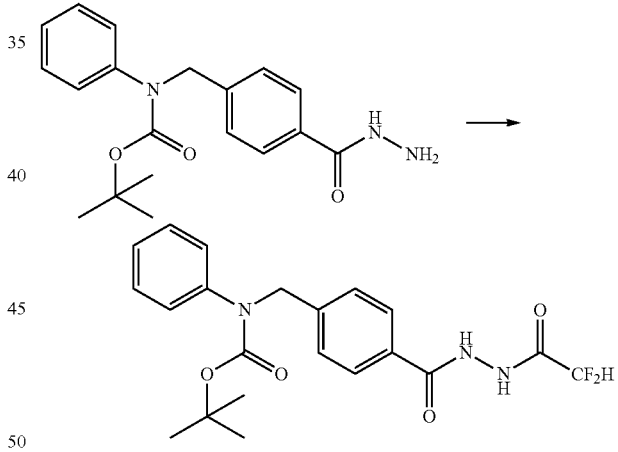

A solution of tert-butyl (4-(hydrazinecarbonyl)benzyl)(phenyl)carbamate (3.000 g, 8.787 mmol) prepared in Step 3 and N,N-diisopropylethylamine (2.296 mL, 13.181 mmol) in dichloromethane (50 mL) was mixed at 0° C. with difluoroacetic anhydride (1.147 mL, 10.545 mmol), and stirred at the room temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; methanol/dichloromethane=0% to 5%) to give the title compound tert-butyl (4-(2-(2,2-difluoroacetyl)hydrazine-1-carbonyl)benzyl)(phenyl)carbamate as white solid (3.687 g, 100.0%).

[Step 5] Compound 21568

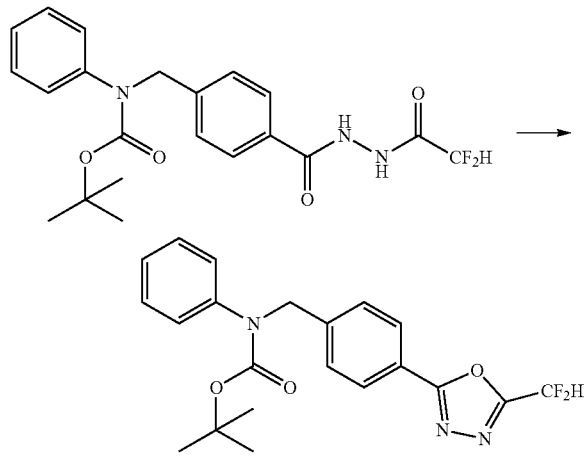

A mixture of tert-butyl (4-(2-(2,2-difluoroacetyl)hydrazine-1-carbonyl)benzyl)(phenyl)carbamate (3.680 g, 8.774 mmol) prepared in Step 4 and 1-methoxy-N-triethylammoniosulfonyl-methanimidate (Burgess reagent, 3.136 g, 13.161 mmol) in tetrahydrofuran (100 mL) was heated at reflux for 16 hr, and cooled down to the room temperature. The reaction mixture was concentrated under the reduced pressure to remove the solvent, and water was added to the concentrate, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 20%) to give the title compound tert-butyl (4-(5-(difluoromethyl)-1,3,4-oxadiazol-2-yl)benzyl)(phenyl)carbamate as white solid (2.070 g, 58.8%).

$^1$H NMR (400 MHz, CDCl$_3$) δ 8.10-8.02 (m, 2H), 7.45-7.40 (m, 2H), 7.28-7.26 (m, 2H), 7.21-7.11 (m, 3H), 6.91 (t, 1H, J=51.7 Hz), 4.91 (s, 2H), 1.42 (s, 9H).

Example 212. Compound 21569: Phenyl (4-(5-(difluoromethyl)-1,3,4-oxadiazol-2-yl)benzyl)(phenyl)carbamate

[Step 1] N-(4-(5-(difluoromethyl)-1,3,4-oxadiazol-2-yl)benzyl)aniline

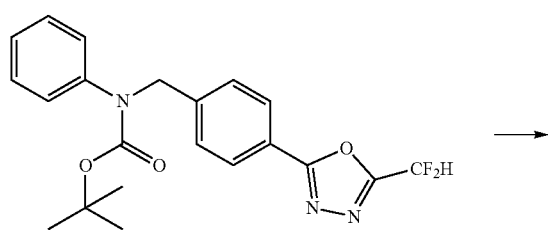

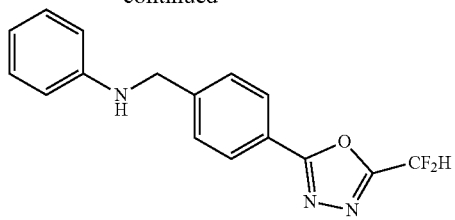

A mixture of tert-butyl (4-(5-(difluoromethyl)-1,3,4-oxadiazol-2-yl)benzyl)(phenyl)carbamate (2.000 g, 4.982 mmol) prepared in Example 210 and trifluoroacetic acid (3.815 mL, 49.824 mmol) in tetrahydrofuran (30 mL) was stirred at the room temperature, heated at reflux for 16 hr, and cooled down to the room temperature. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; ethyl acetate/hexane=0% to 20%) to give the title compound N-(4-(5-(difluoromethyl)-1,3,4-oxadiazol-2-yl)benzyl)aniline as colorless oil (0.254 g, 16.9%).

[Step 2] Compound 21569

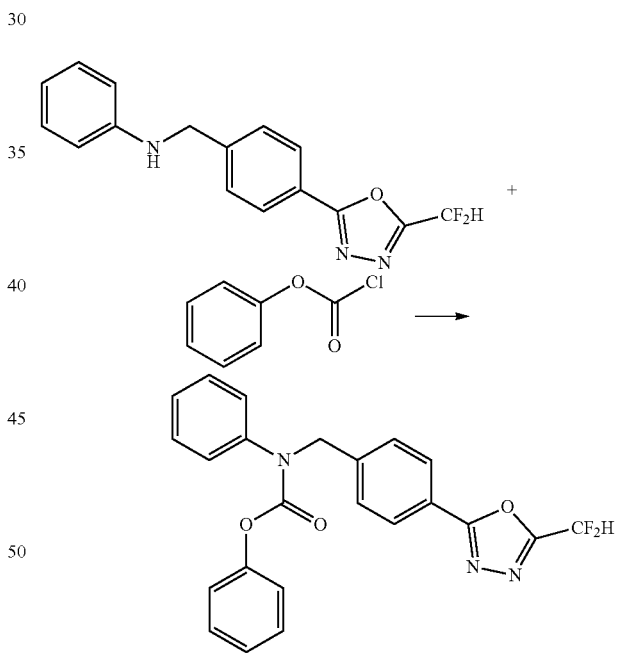

A solution of N-(4-(5-(difluoromethyl)-1,3,4-oxadiazol-2-yl)benzyl)aniline (0.050 g, 0.166 mmol) prepared in Step 1 and potassium carbonate (0.034 g, 0.249 mmol) in acetonitrile (1 mL) was mixed at the room temperature with phenyl carbonochloridate (0.025 mL, 0.199 mmol). The reaction mixture was stirred at the same temperature for 16 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 20%) to give the title compound phenyl (4-(5-(difluoromethyl)-1,3,4-oxadiazol-2-yl)benzyl)(phenyl)carbamate as white solid (0.042 g, 60.1%).

$^1$H NMR (400 MHz, CDCl$_3$) δ 8.10 (d, 2H, J=7.9 Hz), 7.52 (d, 2H, J=8.1 Hz), 7.43-7.33 (m, 4H), 7.33-7.19 (m, 4H), 7.14-7.09 (m, 2H), 6.94 (t, 1H, J=51.7 Hz), 5.05 (s, 2H); LRMS (ES) m/z 422.1 (M$^+$+1).

Example 213. Compound 21570: Isobutyl (4-(5-(difluoromethyl)-1,3,4-oxadiazol-2-yl)benzyl)(phenyl)carbamate

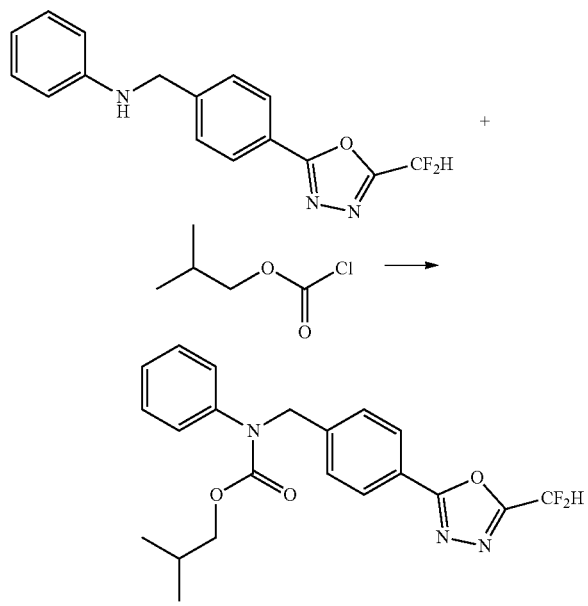

A solution of N-(4-(5-(difluoromethyl)-1,3,4-oxadiazol-2-yl)benzyl)aniline (0.050 g, 0.166 mmol) prepared in Step 1 of Example 212 and potassium carbonate (0.034 g, 0.249 mmol) in acetonitrile (1 mL) was mixed at the room temperature with isobutyl carbonochloridate (0.027 g, 0.199 mmol). The reaction mixture was stirred at the same temperature for 16 hr. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 20%) to give the title compound isobutyl (4-(5-(difluoromethyl)-1,3,4-oxadiazol-2-yl)benzyl)(phenyl)carbamate as white solid (0.041 g, 61.5%).

$^1$H NMR (400 MHz, CDCl$_3$) δ 8.09-8.01 (m, 2H), 7.47-7.40 (m, 2H), 7.34-7.28 (m, 2H), 7.25-7.18 (m, 3H), 6.90 (t, 1H, J=51.7 Hz), 4.94 (s, 2H), 3.92 (d, 2H, J=6.6 Hz), 1.90-1.79 (m, 1H), 0.81 (d, 6H, J=6.7 Hz); LRMS (ES) m/z 402.3 (M$^+$+1).

Example 214. Compound 21576: 1-Butyl-1-(4-(5-(difluoromethyl)-1,3,4-oxadiazol-2-yl)benzyl)-3-phenylurea

[Step 1] Methyl 4-((butylamino)methyl)benzoate

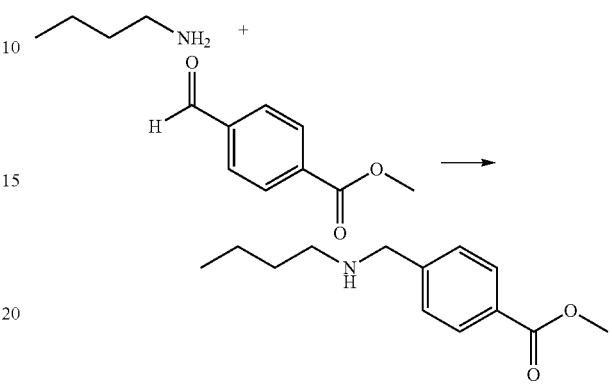

A solution of butan-1-amine (0.500 g, 6.836 mmol) and methyl 4-formylbenzoate (1.122 g, 6.836 mmol) in dichloromethane (50 mL) was mixed at the room temperature with sodium triacetoxyborohydride (1.594 g, 7.520 mmol). The reaction mixture was stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 30%) to give the title compound methyl 4-((butylamino)methyl)benzoate as colorless oil (0.826 g, 54.6%).

[Step 2] Methyl 4-(((tert-butoxycarbonyl)(butyl)amino)methyl)benzoate

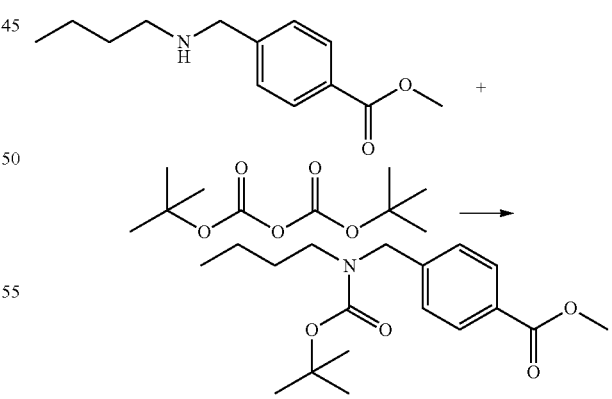

A solution of methyl 4-((butylamino)methyl)benzoate (0.483 g, 2.183 mmol) prepared in Step 1, di-tert-butyl dicarbonate (0.476 g, 2.183 mmol) and triethylamine (0.453 mL, 3.274 mmol) in dichloromethane (10 mL) was stirred at the room temperature for 4 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 10%) to give the title compound methyl 4-(((tert-butoxycarbonyl)(butyl) amino)methyl)benzoate as colorless oil (0.531 g, 75.7%).

[Step 3] Tert-butyl butyl(4-(hydrazinecarbonyl)benzyl)carbamate

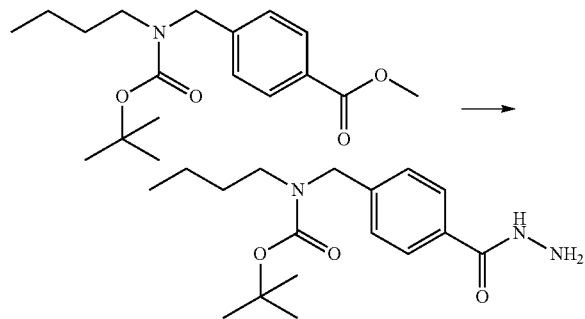

Methyl 4-(((tert-butoxycarbonyl)(butyl)amino)methyl) benzoate (0.180 g, 0.560 mmol) prepared in Step 2 and hydrazine monohydrate (0.264 mL, 5.600 mmol) were mixed at the room temperature in ethanol (3 mL) and then stirred at 100° C. for 16 hr, and cooled down to the room temperature to terminate the reaction. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 5%) to give the title compound tert-butyl butyl(4-(hydrazinecarbonyl)benzyl)carbamate as white solid (0.179 g, 99.2%).

[Step 4] Tert-butyl butyl(4-(2-(2,2-difluoroacetyl) hydrazine-1-carbonyl)benzyl)carbamate

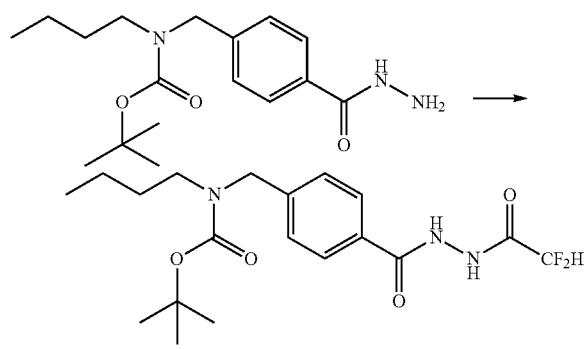

A solution of tert-butyl butyl(4-(hydrazinecarbonyl)benzyl)carbamate (0.178 g, 0.554 mmol) prepared in Step 3 and triethylamine (0.153 mL, 1.108 mmol) in dichloromethane (2 mL) was mixed at the room temperature with difluoroacetic anhydride (0.080 mL, 0.554 mmol). The reaction mixture was stirred at the same temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The obtained product was used without further purification (0.198 g, 89.5%, yellow oil).

[Step 5] Tert-butyl butyl(4-(5-(difluoromethyl)-1,3, 4-oxadiazol-2-yl)benzyl)carbamate

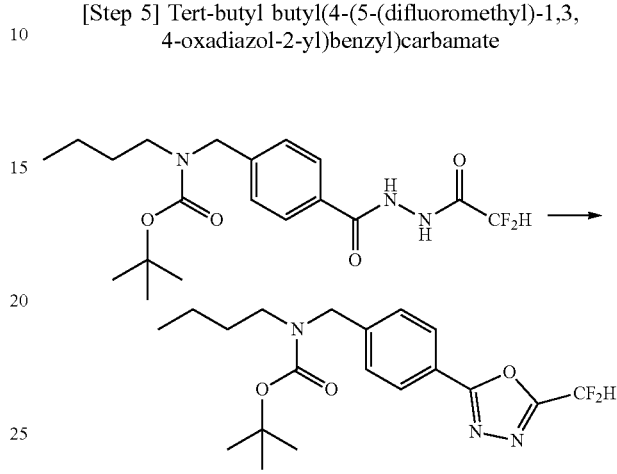

Tert-butyl butyl(4-(2-(2,2-difluoroacetyl)hydrazine-1-carbonyl)benzyl)carbamate (0.198 g, 0.496 mmol) prepared in Step 4 and 1-methoxy-N-triethylammoniosulfonylmethanimidate (Burgess reagent, 0.177 g, 0.744 mmol) were mixed at the room temperature in tetrahydrofuran (2 mL) and then stirred at 80° C. for 16 hr. and cooled down to the room temperature to terminate the reaction. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO₂, 4 g cartridge; methanol/dichloromethane=0% to 3%) to give the title compound tert-butyl butyl (4-(5-(difluoromethyl)-1,3,4-oxadiazol-2-yl)benzyl) carbamate as colorless oil (0.150 g, 79.3%).

[Step 6] N-(4-(5-(difluoromethyl)-1,3,4-oxadiazol-2-yl)benzyl)butan-1-amine

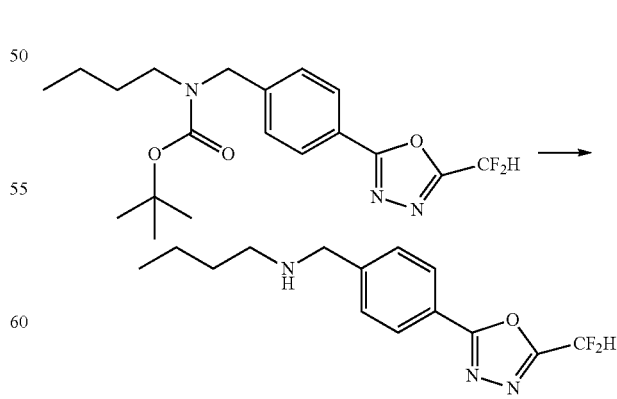

A solution of tert-butyl butyl(4-(5-(difluoromethyl)-1,3, 4-oxadiazol-2-yl)benzyl)carbamate (0.150 g, 0.393 mmol) prepared in Step 5 and trifluoroacetic acid (0.301 mL, 3.933 mmol) in tetrahydrofuran (2 mL) was stirred at the room temperature for 16 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 5%) to give the title compound N-(4-(5-(difluoromethyl)-1,3,4-oxadiazol-2-yl)benzyl)butan-1-amine as white foam (0.107 g, 96.9%).

[Step 7] Compound 21576

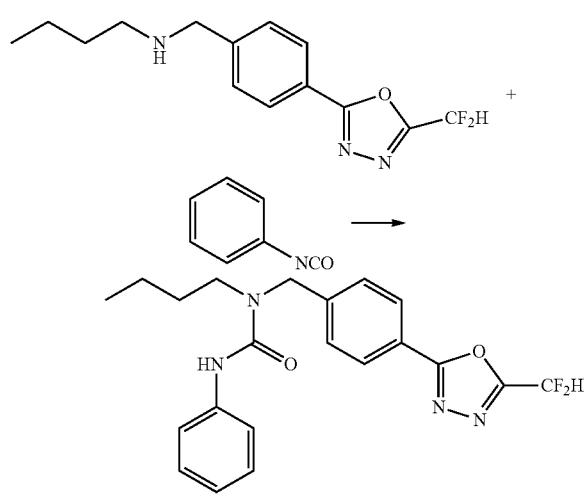

A solution of N-(4-(5-(difluoromethyl)-1,3,4-oxadiazol-2-yl)benzyl)butan-1-amine (0.108 g, 0.383 mmol) prepared in Step 1 and isocyanatobenzene (0.046 g, 0.383 mmol) in diethylether (2 mL) was stirred at the room temperature for 18 hr. The reaction mixture was concentrated under the reduced pressure to remove the solvent. The concentrate was purified and concentrated by column chromatography (SiO$_2$, 4 g cartridge; methanol/dichloromethane=0% to 3%) to give the title compound 1-butyl-1-(4-(5-(difluoromethyl)-1,3,4-oxadiazol-2-yl)benzyl)-3-phenylurea as colorless oil (0.034 g, 22.2%).

$^1$H NMR (400 MHz, CDCl$_3$) δ 8.15-8.07 (m, 2H), 7.54-7.47 (m, 2H), 7.39-7.27 (m, 4H), 7.07-6.74 (m, 2H), 6.35 (s, 1H), 4.68 (s, 2H), 3.39-3.31 (m, 2H), 1.65 (m, 3H), 1.46-1.32 (m, 2H), 0.96 (t, 3H, J=7.3 Hz); LRMS (ESI) m/z 401.2 (M$^+$+H).

Example 215. Compound 21577: 1-(4-(5-(Difluoromethyl)-1,3,4-oxadiazol-2-yl)benzyl)-3-(2-(dimethylamino)ethyl)-1-phenylurea

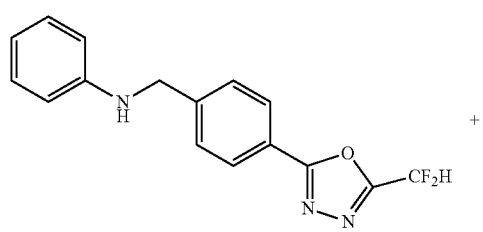

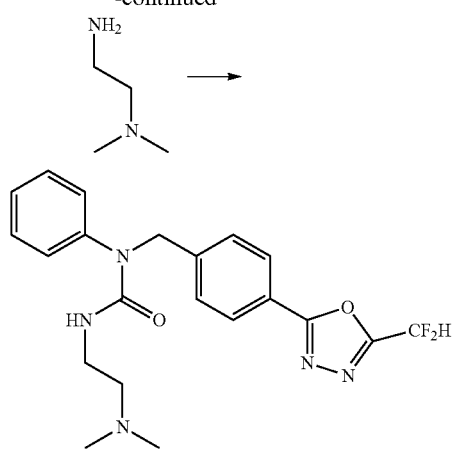

To a stirred solution of N-(4-(5-(difluoromethyl)-1,3,4-oxadiazol-2-yl)benzyl)aniline (0.030 g, 0.100 mmol) prepared in Step 1 of Example 212 and N,N-diisopropylethylamine (0.104 mL, 0.597 mmol) in dichloromethane (1 mL) was added at 0° C. triphosgene (0.015 g, 0.050 mmol). The reaction mixture was stirred at the same temperature for 1 hr. N1,N1-dimethylethane-1,2-diamine (0.010 g, 0.110 mmol) was added to the reaction mixture, and stirred at the room temperature for additional 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to the title compound give 1-(4-(5-(difluoromethyl)-1,3,4-oxadiazol-2-yl)benzyl)-3-(2-(dimethylamino)ethyl)-1-phenylurea as yellow oil (0.030 g, 73.0%).

$^1$H NMR (400 MHz, CDCl$_3$) δ 8.06-7.98 (m, 2H), 7.47-7.27 (m, 5H), 7.12 (dt, 2H, J=7.0, 1.4 Hz), 6.84 (dd, 1H, J=51.8, 1.2 Hz), 4.95 (s, 2H), 3.40 (q, 2H, J=5.6 Hz), 2.56 (s, 2H), 2.30 (d, 6H, J=15.2 Hz); LRMS (ESI) m/z 416.1 (M$^+$+H).

Example 216. Compound 21578: 1-(4-(5-(Difluoromethyl)-1,3,4-oxadiazol-2-yl)benzyl)-3-(2-(dimethylamino)ethyl)-3-ethyl-1-phenylurea

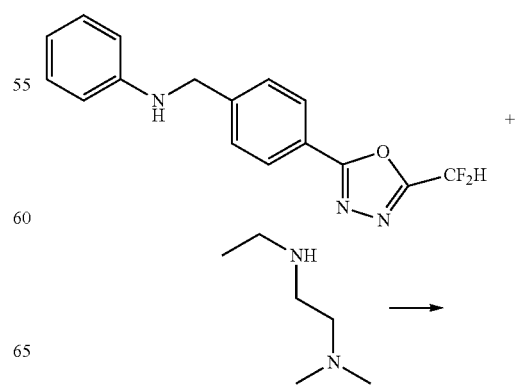

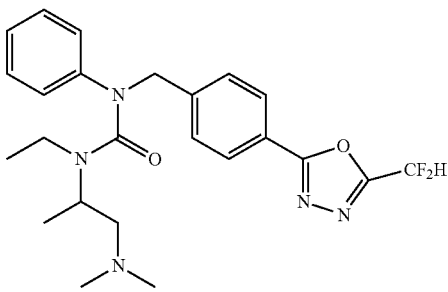

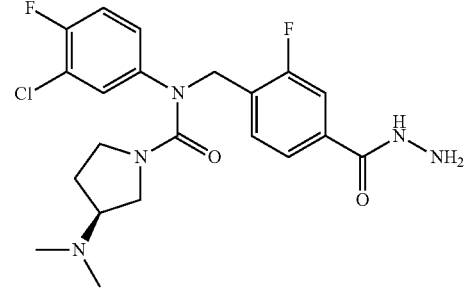

To a stirred solution of N-(4-(5-(difluoromethyl)-1,3,4-oxadiazol-2-yl)benzyl)aniline (0.030 g, 0.100 mmol) prepared in Step 1 of Example 212 and N,N-diisopropylethylamine (0.104 mL, 0.597 mmol) in dichloromethane (1 mL) was added at 0° C. triphosgene (0.015 g, 0.050 mmol). The reaction mixture was stirred at the same temperature for 1 hr. N1-ethyl-N2,N2-dimethylethane-1,2-diamine (0.013 g, 0.110 mmol) was added to the reaction mixture, and stirred at the room temperature for additional 2 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound 1-(4-(5-(difluoromethyl)-1,3,4-oxadiazol-2-yl)benzyl)-3-(2-(dimethylamino)ethyl)-3-ethyl-1-phenylurea as yellow oil (0.021 g, 47.6%).

$^1$H NMR (400 MHz, CDCl$_3$) δ 8.06-7.98 (m, 2H), 7.52-7.45 (m, 2H), 7.35-7.23 (m, 2H), 7.18-7.11 (m, 1H), 7.11-7.03 (m, 2H), 6.96 (d, 1H, J=51.8 Hz), 4.84 (s, 2H), 3.38 (d, 2H, J=7.9 Hz), 3.12 (q, 2H, J=7.1 Hz), 2.49 (s, 2H), 2.35 (s, 6H), 0.87 (t, 3H, J=7.1 Hz); LRMS (ESI) m/z 444.1 (M$^+$+H).

Example 217. Compound 21583: (S)—N-(3-chloro-4-fluorophenyl)-N-(4-(5-(difluoromethyl)-1,3,4-oxadiazol-2-yl)-2-fluorobenzyl)-3-(dimethylamino)pyrrolidine-1-carboxamide

[Step 1] (S)—N-(3-chloro-4-fluorophenyl)-3-(dimethylamino)-N-(2-fluoro-4-(hydrazinecarbonyl)benzyl)pyrrolidine-1-carboxamide

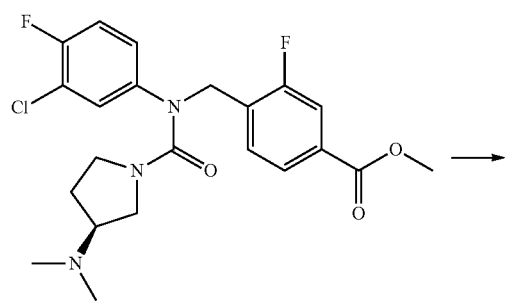

A mixture of methyl (S)-4-((N-(3-chloro-4-fluorophenyl)-3-(dimethylamino)pyrrolidine-1-carboxamido)methyl)-3-fluorobenzoate (0.322 g, 0.713 mmol) and hydrazine monohydrate (0.673 mL, 14.251 mmol) in ethanol (5 mL) was stirred at the room temperature, heated at reflux for 16 hr, and cooled down to the room temperature. The reaction mixture was concentrated under the reduced pressure to remove the solvent, and water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (0.222 g, 68.9%, yellow solid).

[Step 2] Compound 21583

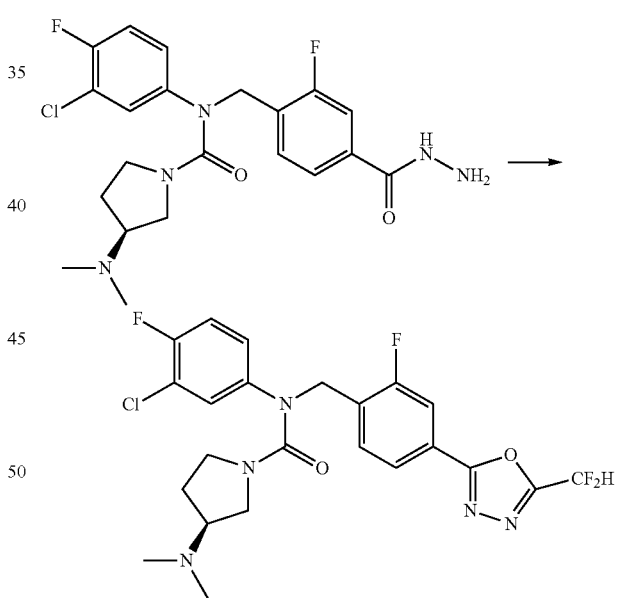

A solution of (S)—N-(3-chloro-4-fluorophenyl)-3-(dimethylamino)-N-(2-fluoro-4-(hydrazinecarbonyl)benzyl)pyrrolidine-1-carboxamide (0.222 g, 0.491 mmol) prepared in Step 1 and N,N-diisopropylethylamine (0.128 mL, 0.737 mmol) in dichloromethane (3 mL) was mixed at 0° C. with 2,2-difluoroacetic anhydride (0.064 mL, 0.590 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound (S)—N-(3-chloro-4-fluorophenyl)-N-(4-(5-(difluoromethyl)-1,3,4-oxadiazol-2-yl)-2-fluorobenzyl)-3-(dimethylamino)pyrrolidine-1-carboxamide as brown solid (0.134 g, 51.5%).

$^1$H NMR (400 MHz, CDCl$_3$) δ 7.86 (dd, 1H, J=8.1, 1.7 Hz), 7.78-7.68 (m, 2H), 7.16 (dd, 1H, J=6.3, 2.7 Hz), 7.11-7.01 (m, 1H), 7.01-6.75 (m, 2H), 4.94 (d, 1H, J=15.3 Hz), 4.83 (d, 1H, J=15.4 Hz), 3.52-3.42 (m, 1H), 3.35-3.25 (m, 1H), 3.11-2.93 (m, 2H), 2.81-2.68 (m, 1H), 2.27 (s, 6H), 2.06-1.95 (m, 1H), 1.85-1.71 (m, 1H); LRMS (ES) m/z 512.4 (M$^+$+1).

Example 218. Compound 21584: (R)—N-(3-chloro-4-fluorophenyl)-N-(4-(5-(difluoromethyl)-1,3,4-oxadiazol-2-yl)-2-fluorobenzyl)-3-(dimethylamino)pyrrolidine-1-carboxamide

[Step 1] (R)—N-(3-chloro-4-fluorophenyl)-3-(dimethylamino)-N-(2-fluoro-4-(hydrazinecarbonyl)benzyl)pyrrolidine-1-carboxamide

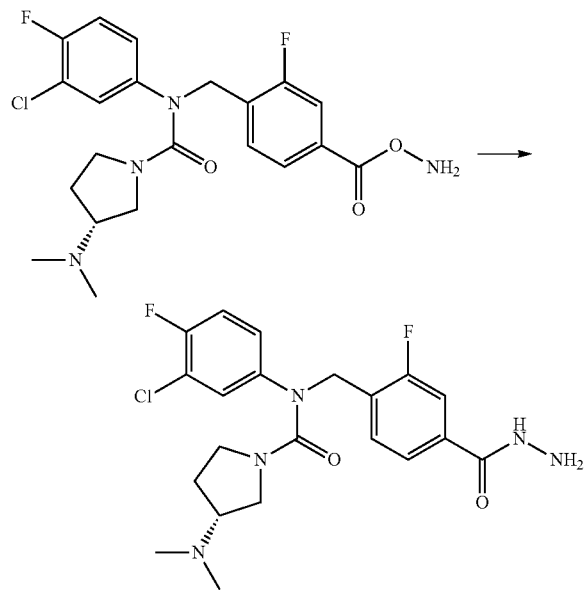

A mixture of methyl (R)-4-((N-(3-chloro-4-fluorophenyl)-3-(dimethylamino)pyrrolidine-1-carboxamido)methyl)-3-fluorobenzoate (0.279 g, 0.617 mmol) and hydrazine monohydrate (0.583 mL, 12.348 mmol) in ethanol (5 mL) was stirred at the room temperature, heated at reflux for 16 hr, and cooled down to the room temperature. The reaction mixture was concentrated under the reduced pressure to remove the solvent, and water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (0.208 g, 74.6%, yellow solid).

[Step 2] Compound 21584

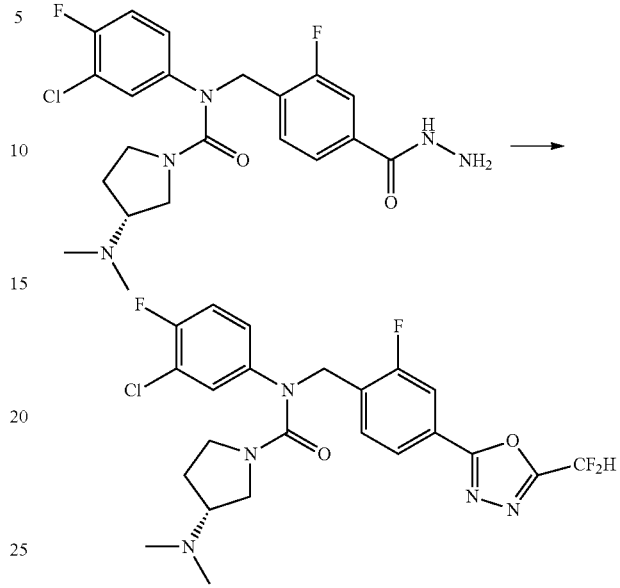

A solution of (R)—N-(3-chloro-4-fluorophenyl)-3-(dimethylamino)-N-(2-fluoro-4-(hydrazinecarbonyl)benzyl)pyrrolidine-1-carboxamide (0.208 g, 0.460 mmol) prepared in Step 1 and N,N-diisopropylethylamine (0.120 mL, 0.690 mmol) in dichloromethane (3 mL) was mixed at 0° C. with 2,2-difluoroacetic anhydride (0.060 mL, 0.552 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound (R)—N-(3-chloro-4-fluorophenyl)-N-(4-(5-(difluoromethyl)-1,3,4-oxadiazol-2-yl)-2-fluorobenzyl)-3-(dimethylamino)pyrrolidine-1-carboxamide as brown solid (0.066 g, 26.9%).

$^1$H NMR (400 MHz, CDCl$_3$) δ 7.87 (dd, 1H, J=8.1, 1.7 Hz), 7.78-7.69 (m, 2H), 7.17 (dd, 1H, J=6.4, 2.7 Hz), 7.08 (t, 1H, J=8.6 Hz), 7.05-6.76 (m, 2H), 4.93 (d, 1H, J=15.3 Hz), 4.84 (d, 1H, J=15.4 Hz), 3.53-3.48 (m, 1H), 3.34-3.25 (m, 1H), 3.09-2.98 (m, 2H), 2.82-2.77 (m, 1H), 2.32 (s, 6H), 2.05-2.00 (m, 1H), 1.95-1.73 (m, 1H); LRMS (ES) m/z 512.41 (M$^+$+1).

Example 219. Compound 21585: 1-(4-(5-(Difluoromethyl)-1,3,4-oxadiazol-2-yl)benzyl)-3-(2-hydroxyethyl)-3-methyl-1-phenylurea

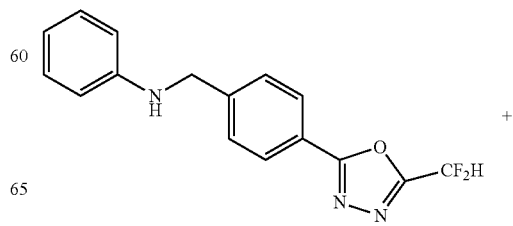

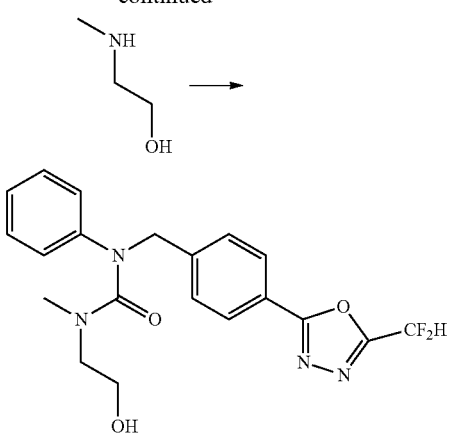

To a stirred solution of N-(4-(5-(difluoromethyl)-1,3,4-oxadiazol-2-yl)benzyl)aniline (0.047 g, 0.157 mmol) prepared in Step 1 of Example 212 and N,N-diisopropylethylamine (0.164 mL, 0.940 mmol) in dichloromethane (2 mL) was added at 0° C. triphosgene (0.023 g, 0.078 mmol). The reaction mixture was stirred at the same temperature for 1 hr. 2-(Methylamino)ethan-1-ol (0.013 g, 0.172 mmol) was added to the reaction mixture, and stirred at the room temperature for additional 4 hr. Then, water was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 5%) to give the title compound 1-(4-(5-(difluoromethyl)-1,3,4-oxadiazol-2-yl)benzyl)-3-(2-hydroxyethyl)-3-methyl-1-phenylurea as yellow oil (0.024 g, 37.4%).

$^1$H NMR (400 MHz, CDCl$_3$) δ 8.05-7.98 (m, 2H), 7.50-7.42 (m, 2H), 7.35-7.27 (m, 2H), 7.16-7.08 (m, 1H), 7.06-6.73 (m, 3H), 4.94 (s, 2H), 3.80-3.73 (m, 2H), 3.47-3.40 (m, 2H), 2.55 (s, 3H); LRMS (ESI) m/z 403.3 (M$^+$+H).

Example 220. Compound 21586: N-(3-chloro-4-fluorophenyl)-N-(4-(5-(difluoromethyl)-1,3,4-oxadiazol-2-yl)-2-fluorobenzyl)-2-oxa-6-azaspiro[3.3]heptane-6-carboxamide

[Step 1] N-(3-chloro-4-fluorophenyl)-N-(2-fluoro-4-(hydrazinecarbonyl)benzyl)-2-oxa-6-azaspiro [3.3]heptane-6-carboxamide

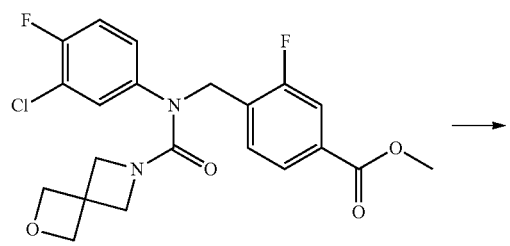

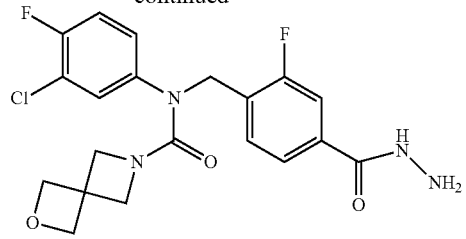

A mixture of methyl 4-((N-(3-chloro-4-fluorophenyl)-2-oxa-6-azaspiro[3.3]heptane-6-carboxamido)methyl)-3-fluorobenzoate (0.274 g, 0.627 mmol) and hydrazine monohydrate (0.592 mL, 12.545 mmol) in methanol (5 mL) was stirred at the room temperature, heated at reflux for 16 hr, and cooled down to the room temperature. The reaction mixture was concentrated under the reduced pressure to remove the solvent, and water was added to the concentrate, followed by extraction with ethyl acetate. The organic layer was washed with aqueous saturated sodium chloride solution, dried with anhydrous MgSO$_4$, filtered, and concentrated in vacuo. The the title compound was used without further purification (0.226 g, 82.5%, yellow solid).

[Step 2] N-(3-chloro-4-fluorophenyl)-N-(4-(2-(2,2-difluoroacetyl)hydrazine-1-carbonyl)-2-fluorobenzyl)-2-oxa-6-azaspiro[3.3]heptane-6-carboxamide

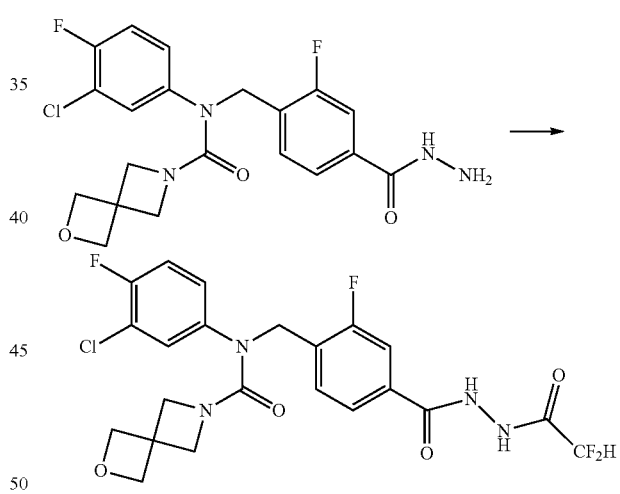

A solution of N-(3-chloro-4-fluorophenyl)-N-(2-fluoro-4-(hydrazinecarbonyl)benzyl)-2-oxa-6-azaspiro [3.3]heptane-6-carboxamide (0.226 g, 0:517 mmol) prepared in Step 1 and N,N-diisopropylethylamine (0.135 mL, 0.776 mmol) in dichloromethane (3 mL) was mixed at 0° C. with 2,2-difluoroacetic anhydride (0.068 mL, 0.621 mmol), and stirred at the room temperature for 3 hr. Then, 1N-aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(3-chloro-4-fluorophenyl)-N-(4-(2-(2, 2-difluoroacetyl)hydrazine-1-carbonyl)-2-fluorobenzyl)-2-oxa-6-azaspiro[3.3]heptane-6-carboxamide as white solid (0.160 g, 60.1%).

[Step 3] Compound 21586

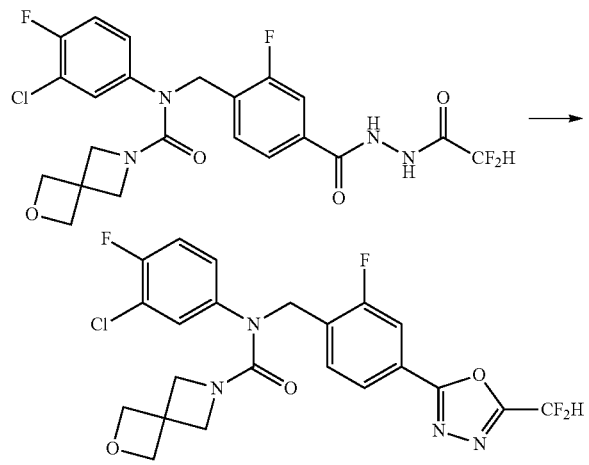

A mixture of N-(3-chloro-4-fluorophenyl)-N-(4-(2-(2,2-difluoroacetyl)hydrazine-1-carbonyl)-2-fluorobenzyl)-2-oxa-6-azaspiro[3.3]heptane-6-carboxamide (0.150 g, 0.291 mmol) prepared in Step 2 and 1-methoxy-N-triethylammoniosulfonyl-methanimidate (Burgess reagent, 0.083 g, 0.350 mmol) in tetrahydrofuran (1 mL) was heated at 120° C. for 30 min under the microwaves. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(3-chloro-4-fluorophenyl)-N-(4-(5-(difluoromethyl)-1,3,4-oxadiazol-2-yl)-2-fluorobenzyl)-2-oxa-6-azaspiro[3.3]heptane-6-carboxamide as white solid (0.023 g, 15.9%).

$^1$H NMR (400 MHz, CDCl$_3$) δ 7.87 (dd, 1H, J=8.0, 1.7 Hz), 7.75-7.63 (m, 2H), 7.20 (dd, 1H, J=6.4, 2.6 Hz), 7.10 (t, 1H, J=8.6 Hz), 7.04-6.76 (m, 2H), 4.91 (s, 2H), 4.64 (s, 4H), 3.76 (s, 4H); LRMS (ES) m/z 497.31 (M$^+$+1).

Example 221. Compound 21587: N-(3-chloro-4-fluorophenyl)-N-((5-(5-(difluoromethyl)-1,3,4-oxadiazol-2-yl)pyridin-2-yl)methyl)thiomorpholine-4-carboxamide 1,1-dioxide

[Step 1] N-(3-chloro-4-fluorophenyl)thiomorpholine-4-carboxamide 1,1-dioxide

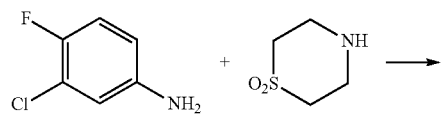

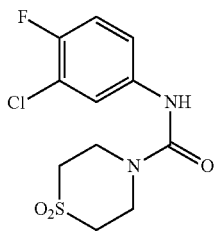

To a stirred solution of 3-chloro-4-fluoroaniline (0.500 g, 3.435 mmol) in dichloromethane (10 mL) were added at 0° C. triphosgene (0.917 g, 3.092 mmol) and N,N-diisopropylethylamine (1.795 mL, 10.305 mmol). The reaction mixture was treated with thiomorpholine 1,1-dioxide (0.557 g, 4.122 mmol), and stirred at the same temperature. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=0% to 50%) to give the title compound N-(3-chloro-4-fluorophenyl)thiomorpholine-4-carboxamide 1,1-dioxide as purple solid (0.346 g, 32.8%).

[Step 2] Methyl 6-((N-(3-chloro-4-fluorophenyl)-1,1-dioxidothiomorpholine-4-carboxamido)methyl)nicotinate

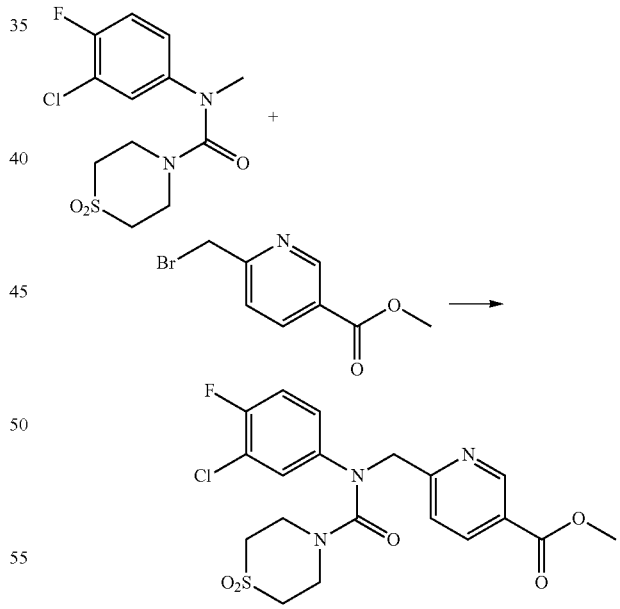

To a stirred solution of N-(3-chloro-4-fluorophenyl)thiomorpholine-4-carboxamide 1,1-dioxide (0.261 g, 0.851 mmol) prepared in Step 1 in N,N-dimethylformide (5 mL) was added at 0° C. sodium hydride (60.00%, 0.041 g, 1.021 mmol). The reaction mixture was stirred at the same temperature. Methyl 6-(bromomethyl)nicotinate (0.215 g, 0.936 mmol) was added to the reaction mixture, and stirred at the room temperature for additional 16 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$; 4 g cartridge; methanol/dichloromethane=0% to 3%) to give the title compound methyl 6-((N-(3-chloro-4-fluorophenyl)-1,1-dioxidothiomorpholine-4-carboxamido)methyl)nicotinate as white solid (0.251 g, 64.7%).

[Step 3] N-(3-chloro-4-fluorophenyl)-N-((5-(hydrazinecarbonyl)pyridin-2-yl)methyl)thiomorpholine-4-carboxamide 1,1-dioxide

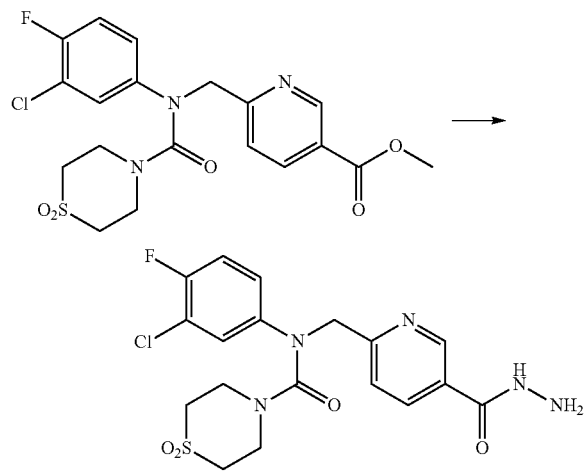

A mixture of methyl 6-((N-(3-chloro-4-fluorophenyl)-1,1-dioxidothiomorpholine-4-carboxamido)methyl)nicotinate (0.251 g, 0.551 mmol) prepared in Step 2 and hydrazine monohydrate (0.520 mL, 11.011 mmol) in methanol (7 mL) was stirred at the room temperature, heated at reflux for 16 hr, and cooled down to the room temperature The reaction mixture was concentrated under the reduced pressure to remove the solvent, and water was added to the concentrate, followed by extraction with ethyl acetate. The organic layer was washed with aqueous saturated sodium chloride solution, dried with anhydrous MgSO$_4$, filtered, and concentrated in vacuo. The title compound was used without further purification (0.146 g, 58.2%, ivory solid).

[Step 4] N-(3-chloro-4-fluorophenyl)-N-((5-(2-(2,2-difluoroacetyl)hydrazine-1-carbonyl)pyridin-2-yl)methyl)thiomorpholine-4-carboxamide 1,1-dioxide

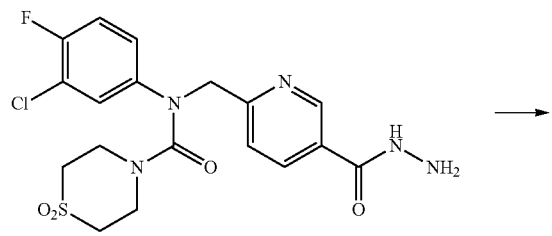

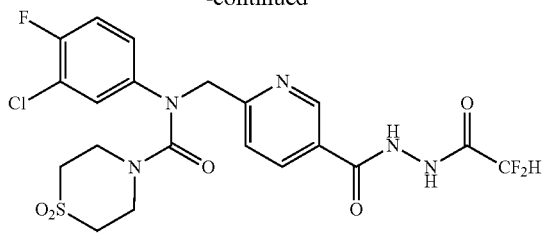

A solution of N-(3-chloro-4-fluorophenyl)-N-((5-(hydrazinecarbonyl)pyridin-2-yl)methyl)thiomorpholine-4-carboxamide 1,1-dioxide (0.146 g, 0.320 mmol) prepared in Step 3 and N,N-diisopropylethylamine (0.084 mL, 0.480 mmol) in dichloromethane (3 mL) was mixed at 0° C. with 2,2-difluoroacetic anhydride (0.042 mL, 0.384 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; methanol/dichloromethane=0% to 3%) to give the title compound N-(3-chloro-4-fluorophenyl)-N-((5-(2-(2,2-difluoroacetyl)hydrazine-1-carbonyl)pyridin-2-yl)methyl)thiomorpholine-4-carboxamide 1,1-dioxide as white solid (0.049 g, 28.4%).

[Step 5] Compound 21587

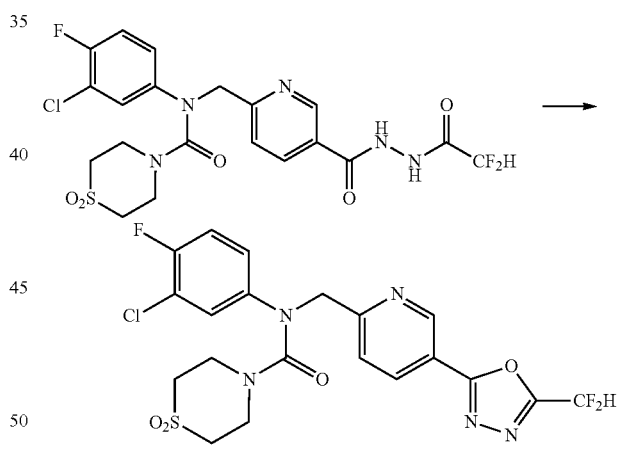

A mixture of N-(3-chloro-4-fluorophenyl)-N-((5-(2-(2,2-difluoroacetyl)hydrazine-1-carbonyl)pyridin-2-yl)methyl)thiomorpholine-4-carboxamide 1,1-dioxide (0.045 g, 0.084 mmol) prepared in Step 4 and 1-methoxy-N-triethylammoniosulfonyl-methanimidate (Burgess reagent, 0.024 g, 0.101 mmol) in tetrahydrofuran (1 mL) was heated at 120° C. for 30 min under the microwaves. The reaction mixture was concentrated under the reduced pressure to remove the solvent, and water was added to the concentrate, followed by extraction with dichloromethane. The bi-phasic mixture was passed through a plastic frit to remove solid residues and aqueous layer, and the organic layer collected was concentrated in vacuo. The concentrate was purified and concentrated by column chromatography (SiO$_2$, 4 g cartridge; ethyl acetate/hexane=0% to 50%) to give the title compound N-(3-chloro-4-fluorophenyl)-N-((5-(5-(difluoromethyl)-1,3,4-oxadiazol-2-yl)pyridin-2-yl)methyl)thiomorpholine-4-carboxamide 1,1-dioxide as white solid (0.010 g, 23.0%).

$^{1}$H NMR (400 MHz, CDCl$_{3}$) δ 9.28-9.27 (m, 1H), 8.49 (dd, 1H, J=8.2, 2.2 Hz), 7.34 (dd, 1H, J=6.0, 2.4 Hz), 7.20-7.12 (m, 2H), 6.95 (t, 1H, J=51.6 Hz), 5.05 (s, 2H), 3.73-3.70 (m, 4H), 3.01-2.98 (m, 4H); LRMS (ES) m/z 516.3 (M$^{+}$+1).

Example 222. Compound 21591: N-(3-chloro-4-fluorophenyl)-N-(4-(5-(difluoromethyl)-1,3,4-oxadiazol-2-yl)-2-fluorobenzyl)-4-ethylpiperazine-1-carboxamide

[Step 1] Methyl 4-4-(3-chloro-4-fluorophenyl)amino)methyl)-3-fluorobenzoate

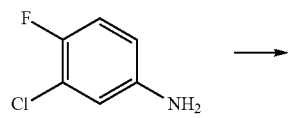

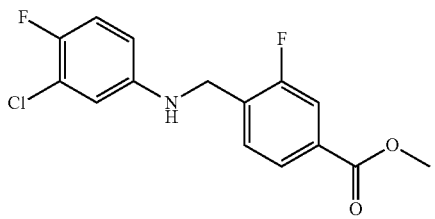

A solution of 3-chloro-4-fluoroaniline (3.000 g, 20.610 mmol), methyl 4-(bromomethyl)-3-fluorobenzoate (6.110 g, 24.732 mmol) and potassium carbonate (5.697 g, 41.220 mmol) in acetonitrile (30 mL) was stirred at the room temperature for 14 hr, filtered to remove solids, and concentrated under the reduced pressure. The residue was chromatographed (SiO$_{2}$, 80 g cartridge; ethyl acetate/hexane=0% to 10%) to give methyl 4-(((3-chloro-4-fluorophenyl)amino)methyl)-3-fluorobenzoate as yellow oil (4.030 g, 62.7%).

[Step 2] Methyl 4-(((3-chloro-4-fluorophenyl)((4-nitrophenoxy)carbonyl)amino)methyl)-3-fluorobenzoate

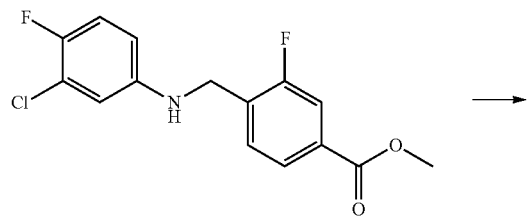

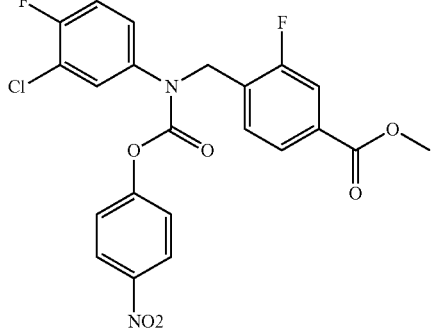

A solution of methyl 4-(((3-chloro-4-fluorophenyl)amino)methyl)-3-fluorobenzoate (2.000 g, 6.416 mmol), 4-nitrophenyl carbonochloridate (1.940 g, 9.624 mmol) and potassium carbonate (2.660 g, 19.249 mmol) in dichloromethane (20 mL) was stirred at the room temperature for 7 hr. Then, water was added to the reaction mixture, followed by extraction with dichloromethane. The organic layer was washed with aqueous saturated sodium chloride solution, dried (anhydrous MgSO$_{4}$), filtered, and concentrated in vacuo. The residue was chromatographed (SiO$_{2}$, 40 g cartridge; ethyl acetate/hexane=0% to 20%) to give methyl 4-(((3-chloro-4-fluorophenyl)((4-nitrophenoxy)carbonyl)amino)methyl)-3-fluorobenzoate as white solid (2.150 g, 70.3%).

[Step 3] Methyl 4-((N-(3-chloro-4-fluorophenyl)-4-ethylpiperazine-1-carboxamido)methyl)-3-fluorobenzoate

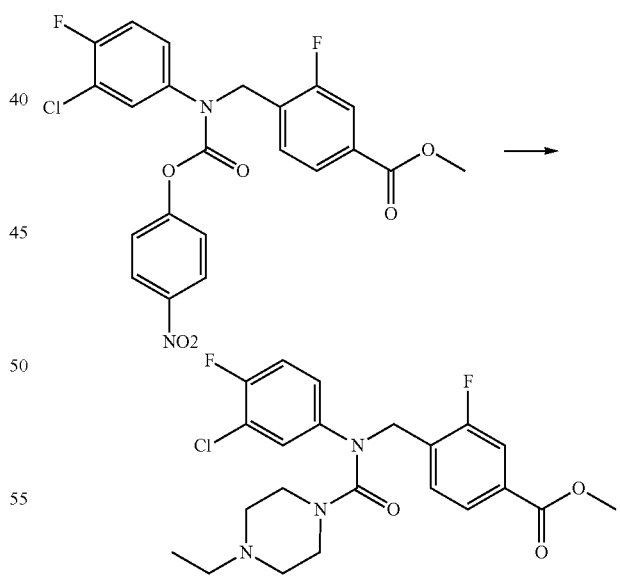

A solution of methyl 4-(((3-chloro-4-fluorophenyl)((4-nitrophenoxy)carbonyl)amino)methyl)-3-fluorobenzoate (0.200 g, 0.419 mmol), 1-ethylpiperazine (0.239 g, 2.097 mmol) and potassium carbonate (0.580 g, 4.194 mmol) in N,N-dimethylformamide (3 mL) was stirred at 100° C. for 3 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The methyl 4-((N-(3-chloro-4-fluorophenyl)-4-ethylpiperazine-1-carboxamido)methyl)-3-fluorobenzoate was used without further purification (0.168 g, 88.6%, pale yellow oil).

[Step 4] N-(3-chloro-4-fluorophenyl)-4-ethyl-N-(2-fluoro-4-(hydrazinecarbonyl)benzyl)piperazine-1-carboxamide

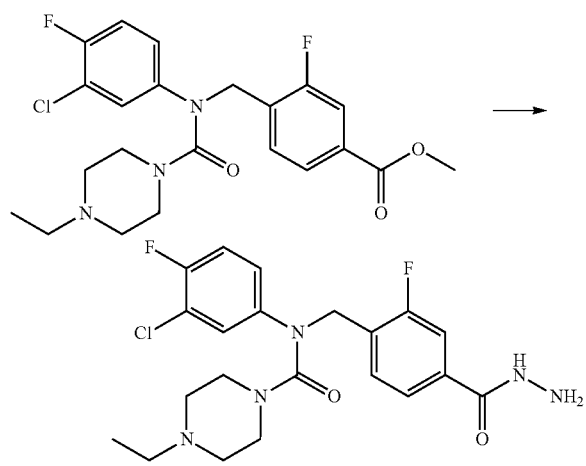

Methyl 4-((N-(3-chloro-4-fluorophenyl)-4-ethylpiperazine-1-carboxamido)methyl)-3-fluorobenzoate (0.230 g, 0.509 mmol) and hydrazine monohydrate (0.247 mL, 5.090 mmol) were mixed at the room temperature in ethanol (10 mL) and then stirred at 100° C. for 18 hr and cooled down to the room temperature to terminate the reaction. The reaction mixture was concentrated under the reduced pressure to remove the solvent and then, water was added to the resultant concentrate, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(3-chloro-4-fluorophenyl)-4-ethyl-N-(2-fluoro-4-(hydrazinecarbonyl)benzyl)piperazine-1-carboxamide as white solid (0.230 g, 100.0%).

[Step 5] N-(3-chloro-4-fluorophenyl)-N-(4-(2-(2,2-difluoroacetyl)hydrazine-1-carbonyl)-2-fluorobenzyl)-4-ethylpiperazine-1-carboxamide

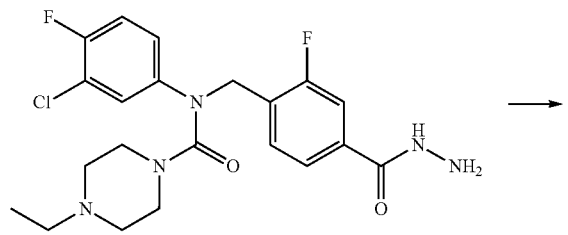

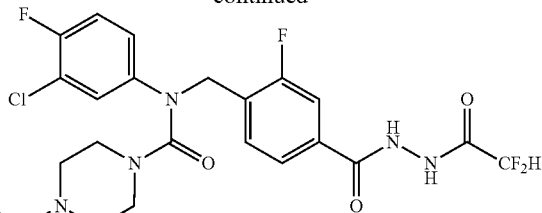

A solution of N-(3-chloro-4-fluorophenyl)-4-ethyl-N-(2-fluoro-4-(hydrazinecarbonyl)benzyl)piperazine-1-carboxamide (0.115 g, 0.254 mmol), triethylamine (0.071 mL, 0.509 mmol) and 2,2-difluoroacetic anhydride (0.028 mL, 0.254 mmol) in dichloromethane (2 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(3-chloro-4-fluorophenyl)-N-(4-(2-(2,2-difluoroacetyl)hydrazine-1-carbonyl)-2-fluorobenzyl)-4-ethylpiperazine-1-carboxamide as yellow oil (0.110 g, 81.6%).

[Step 6] Compound 21591

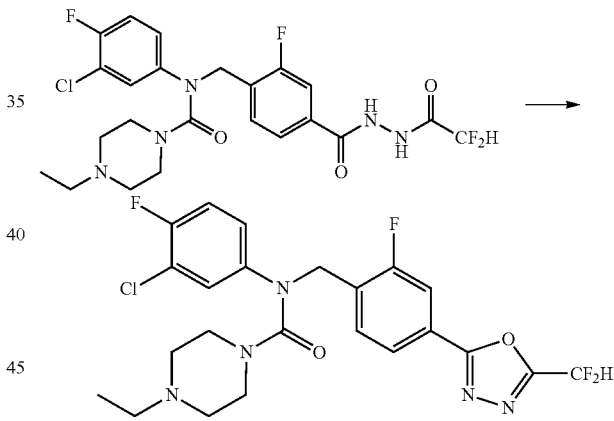

N-(3-chloro-4-fluorophenyl)-N-(4-(2-(2,2-difluoroacetyl)hydrazine-1-carbonyl)-2-fluorobenzyl)-4-ethylpiperazine-1-carboxamide (0.110 g, 0.208 mmol) and 1-methoxy-N-triethylammoniosulfonyl-methanimidate (Burgess reagent, 0.059 g, 0.249 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 3%) to give N-(3-chloro-4-fluorophenyl)-N-(4-(5-(difluoromethyl)-1,3,4-oxadiazol-2-yl)-2-fluorobenzyl)-4-ethylpiperazine-1-carboxamide as yellow oil (0.090 g, 84.7%).

¹H NMR (400 MHz, CDCl₃) δ 7.87 (dd, 1H, J=8.0, 1.7 Hz), 7.75 (dd, 1H, J=10.1, 1.7 Hz), 7.68 (t, 1H, J=7.7 Hz), 7.16 (dd, 1H, J=6.3, 2.7 Hz), 7.07 (t, 1H, J=8.6 Hz), 7.04-6.73 (m, 2H), 4.90 (s, 2H), 3.31 (t, 4H, J=5.1 Hz), 2.47-2.35 (m, 2H), 2.31 (s, 4H), 1.06 (t, 3H, J=7.2 Hz); LRMS (ES) m/z 512.9 (M$^+$+1).

Example 223. Compound 21592: N-(3-chloro-4-fluorophenyl)-4-ethyl-N-(2-fluoro-4-(5-(trifluoromethyl)-1,3,4-oxadiazol-2-yl)benzyl)piperazine-1-carboxamide

[Step 1] N-(3-chloro-4-fluorophenyl)-4-ethyl-N-(2-fluoro-4-(2-(2,2,2-trifluoroacetyl)hydrazine-1-carbonyl)benzyl)piperazine-1-carboxamide

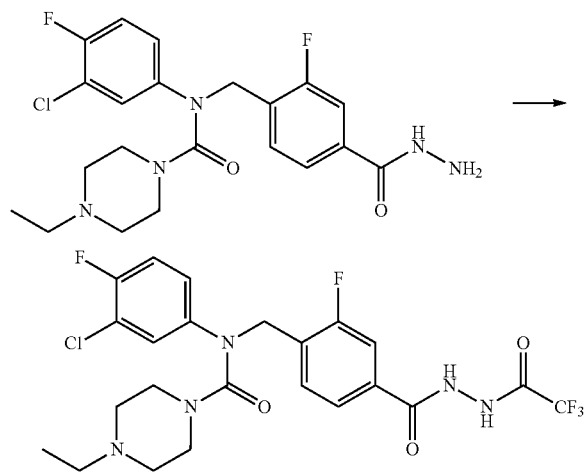

A solution of N-(3-chloro-4-fluorophenyl)-4-ethyl-N-(2-fluoro-4-(hydrazinecarbonyl)benzyl)piperazine-1-carboxamide (0.115 g, 0.254 mmol), triethylamine (0.071 mL, 0.509 mmol) and trifluoroacetic anhydride (0.036 mL, 0.254 mmol) in dichloromethane (2 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-4-ethyl-N-(2-fluoro-4-(2-(2,2,2-trifluoroacetyl)hydrazine-1-carbonyl)benzyl)piperazine-1-carboxamide as yellow oil (0.108 g, 77.5%).

[Step 2] Compound 21592

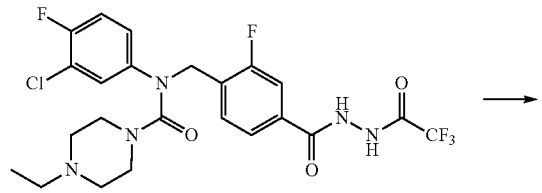

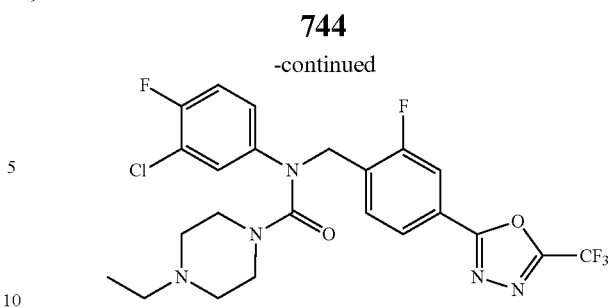

N-(3-chloro-4-fluorophenyl)-4-ethyl-N-(2-fluoro-4-(2-(2,2,2-trifluoroacetyl)hydrazine-1-carbonyl)benzyl)piperazine-1-carboxamide (0.108 g, 0.197 mmol) and 1-methoxy-N-triethylammoniosulfonyl-methanimidate (Burgess reagent, 0.056 g, 0.237 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(3-chloro-4-fluorophenyl)-4-ethyl-N-(2-fluoro-4-(5-(trifluoromethyl)-1,3,4-oxadiazol-2-yl)benzyl)piperazine-1-carboxamide as yellow oil (0.034 g, 32.6%).

$^1$H NMR (400 MHz, CDCl$_3$) δ 7.87 (dd, 1H, J=8.0, 1.7 Hz), 7.75 (dd, 1H, J=9.9, 1.7 Hz), 7.70 (t, 1H, J=7.6 Hz), 7.16 (dd, 1H, J=6.3, 2.7 Hz), 7.08 (t, 1H, J=8.6 Hz), 7.01-6.92 (m, 1H), 4.91 (s, 2H), 3.37-3.28 (m, 4H), 2.45-2.38 (m, 2H), 2.33 (s, 4H), 1.07 (t, 3H, J=7.2 Hz); LRMS (ES) m/z 530.2 (M$^+$+1).

Example 224. Compound 21593: N-(3-chloro-4-fluorophenyl)-N-(4-(5-(difluoromethyl)-1,3,4-oxadiazol-2-yl)benzyl)morpholine-4-carboxamide

[Step 1] N-(3-chloro-4-fluorophenyl)-N-(4-(hydrazinecarbonyl)benzyl)morpholine-4-carboxamide

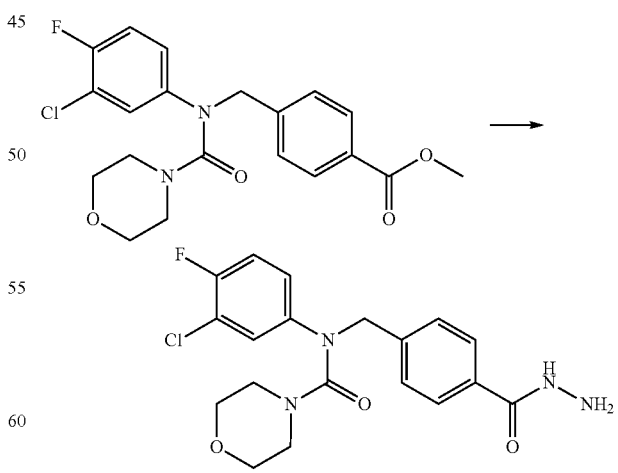

Methyl 4-((N-(3-chloro-4-fluorophenyl)morpholine-4-carboxamido)methyl)benzoate (0.300 g, 0.737 mmol) and hydrazine monohydrate (0.358 mL, 7.374 mmol) were mixed at the room temperature in ethanol (10 mL) and then stirred at 100° C. for 18 hr and cooled down to the room temperature to terminate the reaction. The reaction mixture was concentrated under the reduced pressure to remove the solvent. Then, water was added to the resultant concentrate, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-N-(4-(hydrazinecarbonyl)benzyl)morpholine-4-carboxamide as white solid (0.290 g, 96.7%).

[Step 2] N-(3-chloro-4-fluorophenyl)-N-(4-(2-(2,2-difluoroacetyl)hydrazine-1-carbonyl)benzyl)morpholine-4-carboxamide

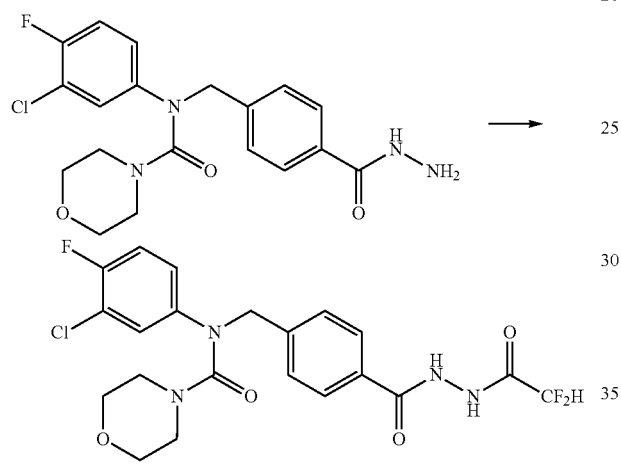

A solution of N-(3-chloro-4-fluorophenyl)-N-(4-(hydrazinecarbonyl)benzyl)morpholine-4-carboxamide (0.145 g, 0.356 mmol), triethylamine (0.099 mL, 0.713 mmol) and 2,2-difluoroacetic anhydride (0.039 mL, 0.356 mmol) in dichloromethane (2 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-N-(4-(2-(2,2-difluoroacetyl)hydrazine-1-carbonyl)benzyl)morpholine-4-carboxamide as yellow oil (0.127 g, 73.5%).

[Step 3] Compound 21593

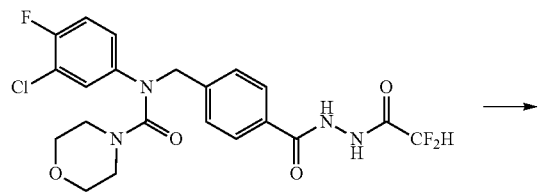

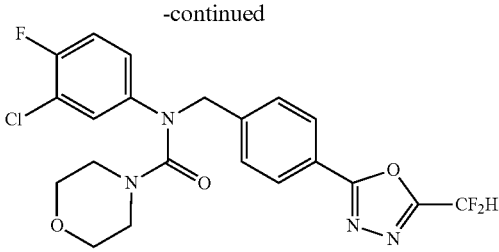

N-(3-chloro-4-fluorophenyl)-N-(4-(2-(2,2-difluoroacetyl)hydrazine-1-carbonyl)benzyl)morpholine-4-carboxamide (0.127 g, 0.262 mmol) and 1-methoxy-N-triethylammoniosulfonyl-methanimidate (Burgess reagent, 0.075 g, 0.314 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(3-chloro-4-fluorophenyl)-N-(4-(5-(difluoromethyl)-1,3,4-oxadiazol-2-yl)benzyl)morpholine-4-carboxamide as yellow oil (0.052 g, 42.6%).
$^1$H NMR (400 MHz, CDCl$_3$) δ 8.08-8.01 (m, 2H), 7.49-7.41 (m, 2H), 7.14 (dd, 1H, J=6.3, 2.7 Hz), 7.07 (t, 1H, J=8.6 Hz), 7.04-6.75 (m, 2H), 4.89 (s, 4H), 3.55-3.50 (m, 4H), 3.29-3.21 (m, 4H); LRMS (ES) m/z 467.3 (M$^+$+1).

Example 225. Compound 21594: N-(3-chloro-4-fluorophenyl)-N-(4-(5-(trifluoromethyl)-1,3,4-oxadiazol-2-yl)benzyl)morpholine-4-carboxamide

[Step 1] N-(3-chloro-4-fluorophenyl)-N-(4-(2-(2,2,2-trifluoroacetyl)hydrazine-1-carbonyl)benzyl) morpholine-4-carboxamide

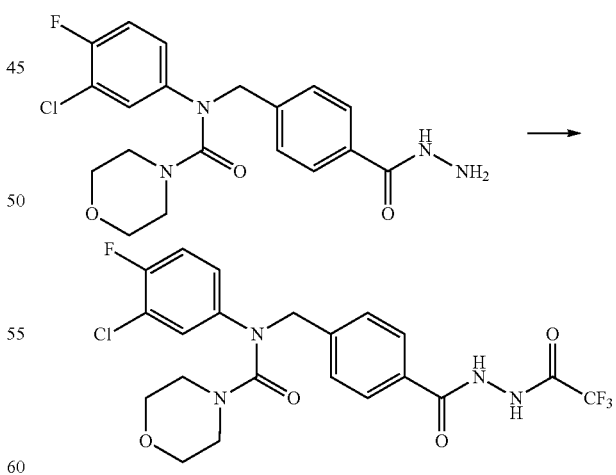

A solution of N-(3-chloro-4-fluorophenyl)-N-(4-(hydrazinecarbonyl)benzyl)morpholine-4-carboxamide (0.145 g, 0.356 mmol), triethylamine (0.099 mL, 0.713 mmol) and trifluoroacetic anhydride (0.050 mL, 0.356 mmol) in dichloromethane (2 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(3-chloro-4-fluorophenyl)-N-(4-(2-(2,2,2-trifluoroacetyl)hydrazine-1-carbonyl)benzyl) morpholine-4-carboxamide as yellow oil (0.126 g, 70.3%).

[Step 2] Compound 21594

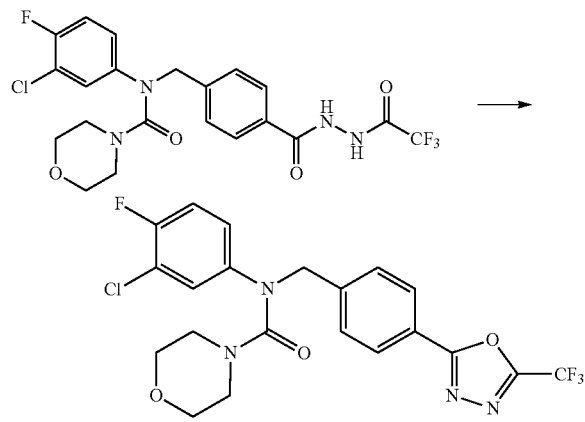

N-(3-chloro-4-fluorophenyl)-N-(4-(2-(2,2,2-trifluoroacetyl)hydrazine-1-carbonyl)benzyl)morpholine-4-carboxamide (0.126 g, 0.251 mmol) and 1-methoxy-N-triethylammoniosulfonyl-methanimidate (Burgess reagent, 0.072 g, 0.301 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 3%) to give N-(3-chloro-4-fluorophenyl)-N-(4-(5-(trifluoromethyl)-1,3,4-oxadiazol-2-yl)benzyl) morpholine-4-carboxamide as yellow oil (0.032 g, 26.3%).

¹H NMR (400 MHz, CDCl₃) δ 8.06 (d, 2H, J=8.3 Hz), 7.49 (d, 2H, J=8.3 Hz), 7.16 (dd, 1H, J=6.3, 2.7 Hz), 7.10 (t, 1H, J=8.6 Hz), 6.95 (ddd, 1H, J=8.9, 4.1, 2.8 Hz), 4.92 (s, 2H), 3.58-3.52 (m, 4H), 3.32-3.24 (m, 4H); LRMS (ES) m/z 485.3 (M⁺+1).

Example 226. Compound 21597: N-((5-(5-(difluoromethyl)-1,3,4-oxadiazol-2-yl)pyridin-2-yl)methyl)-4-methyl-N-(m-tolyl)piperazine-1-carboxamide

[Step 1]
4-Methyl-N-(m-tolyl)piperazine-1-carboxamide

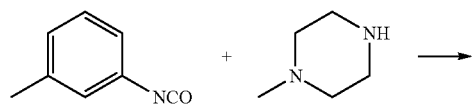

-continued

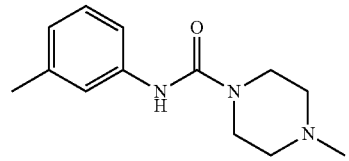

A solution of 1-isocyanato-3-methylbenzene (0.467 mL, 3.755 mmol) and 1-methylpiperazine (0.437 mL, 3.943 mmol) in diethylether (10 mL) was stirred at the room temperature for 18 hr. The precipitates were collected by filtration, washed by hexane, and dried to give 4-methyl-N-(m-tolyl)piperazine-1-carboxamide as white solid (0.565 g, 64.5%).

[Step 2] Ethyl 6-((4-methyl-N-(m-tolyl)piperazine-1-carboxamido)methyl)nicotinate

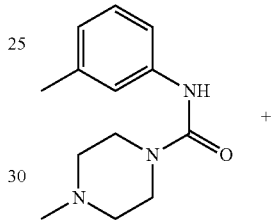

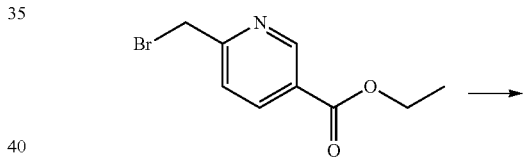

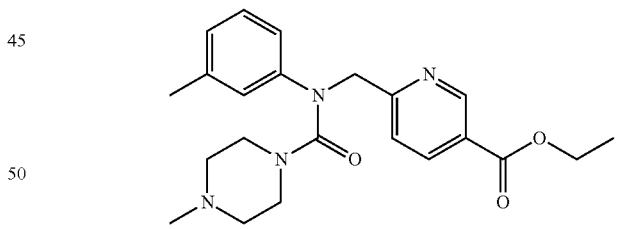

A solution of 4-methyl-N-(m-tolyl)piperazine-1-carboxamide (0.200 g, 0.857 mmol) and sodium hydride (60.00%, 0.041 g, 1.029 mmol) in N,N-dimethylformide (3 mL) was mixed at 0° C. with ethyl 6-(bromomethyl)nicotinate (0.211 g, 0.866 mmol), and stirred at the room temperature for 2 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 4 g cartridge; methanol/dichloromethane=0% to 5%) to give ethyl 6-((4-methyl-N-(m-tolyl)piperazine-1-carboxamido)methyl)nicotinate as brown oil (0.082 g, 24.1%).

[Step 3] N-((5-(hydrazinecarbonyl)pyridin-2-yl)methyl)-4-methyl-N-(m-tolyl)piperazine-1-carboxamide

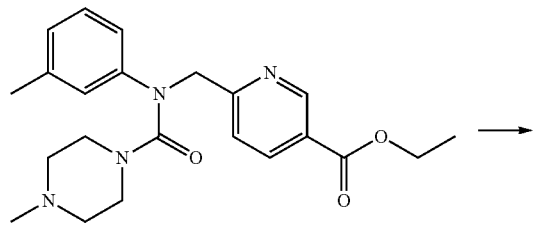

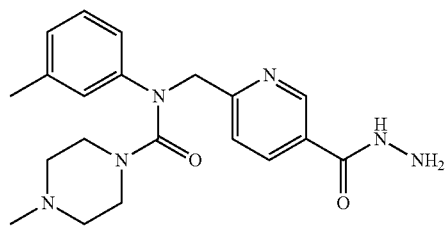

A mixture of ethyl 6-((4-methyl-N-(m-tolyl)piperazine-1-carboxamido)methyl)nicotinate (0.081 g, 0.204 mmol) and hydrazine monohydrate (0.199 mL, 4.086 mmol) in ethanol (1 mL) was heated at reflux for 16 hr, and cooled down to the ambient temperature, concentrated under the reduced pressure. Then, water was added to the reaction mixture, followed by extraction with ethyl acetate. The organic layer was washed with aqueous saturated sodium chloride solution, dried (anhydrous MgSO₄), filtered, and concentrated in vacuo. The crude N-((5-(hydrazinecarbonyl)pyridin-2-yl)methyl)-4-methyl-N-(m-tolyl)piperazine-1-carboxamide was used without further purification (0.066 g, 84.1%, light yellow solid).

[Step 4] N-((5-(2-(2,2-difluoroacetyl)hydrazine-1-carbonyl)pyridin-2-yl)methyl)-4-methyl-N-(m-tolyl)piperazine-1-carboxamide

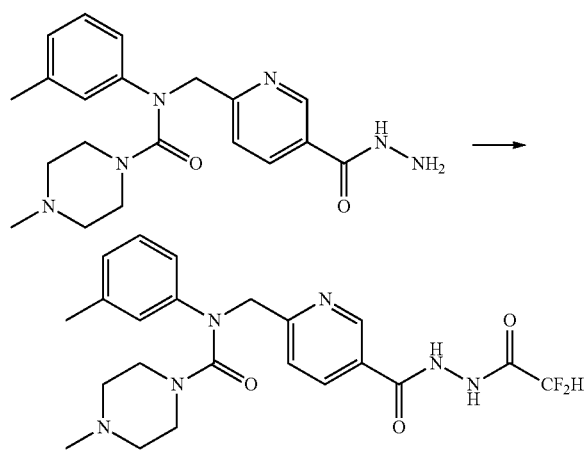

A solution of N-((5-(hydrazinecarbonyl)pyridin-2-yl)methyl)-4-methyl-N-(m-tolyl)piperazine-1-carboxamide (0.066 g, 0.172 mmol) and N,N-diisopropylethylamine (0.045 mL, 0.258 mmol) in dichloromethane (1 mL) was mixed at 0° C. with 2,2-difluoroacetic anhydride (0.037 mL, 0.344 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 10%) to give N-((5-(2-(2,2-difluoroacetyl)hydrazine-1-carbonyl)pyridin-2-yl)methyl)-4-methyl-N-(m-tolyl)piperazine-1-carboxamide as yellow solid (0.079 g, 99.9%).

[Step 5] Compound 21597

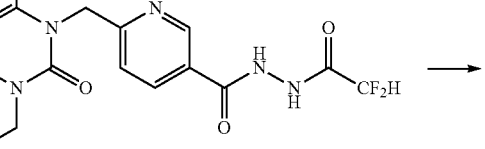

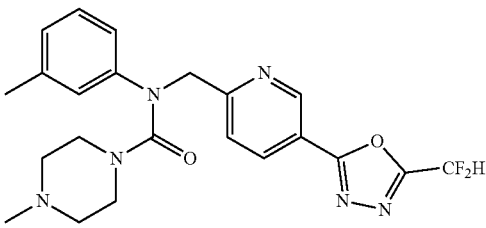

A mixture of N-((5-(2-(2,2-difluoroacetyl)hydrazine-1-carbonyl)pyridin-2-yl)methyl)-4-methyl-N-(m-tolyl)piperazine-1-carboxamide (0.079 g, 0.172 mmol) and 1-methoxy-N-triethylammoniosulfonyl-methanimidate (Burgess reagent, 0.061 g, 0.257 mmol) in tetrahydrofuran (1 mL) was heated at reflux for 18 hr, and cooled down to the ambient temperature, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 10%) to give N-((5-(5-(difluoromethyl)-1,3,4-oxadiazol-2-yl)pyridin-2-yl)methyl)-4-methyl-N-(m-tolyl)piperazine-1-carboxamide as yellow oil (0.019 g, 25.0%).

¹H NMR (400 MHz, CDCl₃) δ 9.21-9.21 (m, 1H), 8.31 (dd, J=8.2, 2.2 Hz, 1H), 7.60 (d, J=8.3 Hz, 1H), 7.18-7.15 (m, 1H), 7.05-6.79 (m, 4H), 5.08 (s, 2H), 3.32-3.30 (m, 4H), 2.29-2.25 (m, 10H); LRMS (ES) m/z 443.5 (M⁺+1).

Example 227. Compound 21598: N-((5-(5-(difluoromethyl)-1,3,4-oxadiazol-2-yl)pyridin-2-yl)methyl)-4-methyl-N-(p-tolyl)piperazine-1-carboxamide

[Step 1]
4-Methyl-N-(p-tolyl)piperazine-1-carboxamide

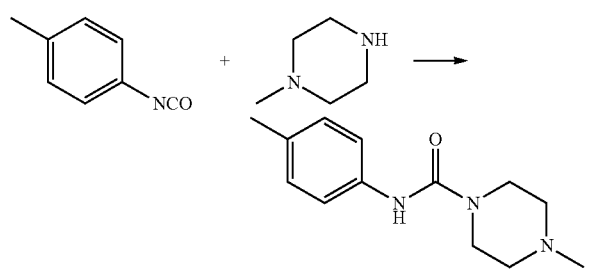

A solution of 1-isocyanato-4-methylbenzene (0.472 mL, 3.755 mmol) and 1-methylpiperazine (0.437 mL, 3.943 mmol) in diethylether (10 mL) was stirred at the room temperature for 18 hr. The precipitates were collected by filtration, washed by hexane, and dried to give 4-methyl-N-(p-tolyl)piperazine-1-carboxamide as white solid (0.546 g, 62.3%).

[Step 2] Ethyl 6-((4-methyl-N-(p-tolyl)piperazine-1-carboxamido)methyl)nicotinate

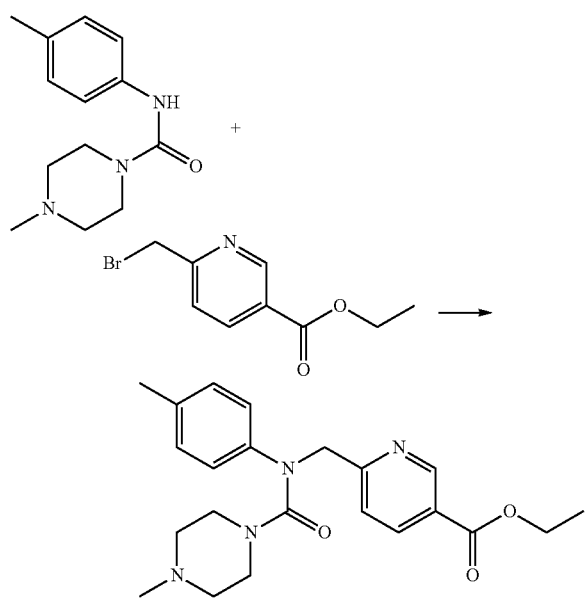

A solution of 4-methyl-N-(p-tolyl)piperazine-1-carboxamide (0.200 g, 0.857 mmol) and sodium hydride (60.00%, 0.041 g, 1.029 mmol) in N,N-dimethylformide (3 mL) was mixed at 0° C. with ethyl 6-(bromomethyl)nicotinate (0.211 g, 0.866 mmol), and stirred at the room temperature for 2 hr. Then, water was added to the reaction mixture, followed by extraction with ethyl acetate. The organic layer was washed with aqueous saturated sodium chloride solution, dried (anhydrous MgSO₄), filtered, and concentrated in vacuo.

The residue was chromatographed (SiO₂, 4 g cartridge; methanol/dichloromethane=0% to 5%) to give ethyl 6-((4-methyl-N-(p-tolyl)piperazine-1-carboxamido)methyl)nicotinate as brown oil (0.107 g, 31.4%).

[Step 3] N-((5-(hydrazinecarbonyl)pyridin-2-yl)methyl)-4-methyl-N-(p-tolyl)piperazine-1-carboxamide

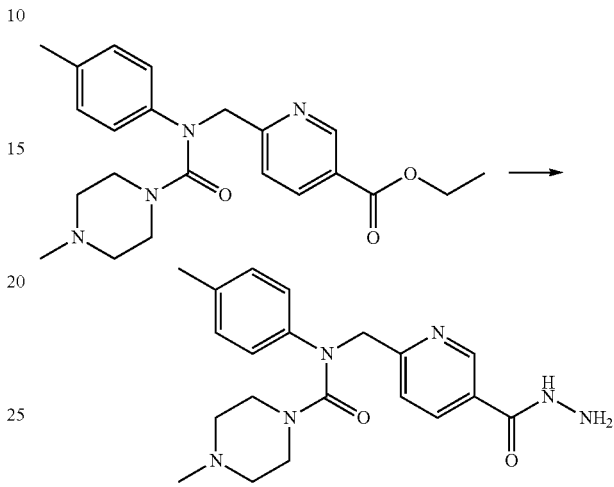

A mixture of ethyl 6-((4-methyl-N-(p-tolyl)piperazine-1-carboxamido)methyl)nicotinate (0.106 g, 0.267 mmol) and hydrazine monohydrate (0.260 mL, 5.347 mmol) in ethanol (1 mL) was heated at reflux for 16 hr, and cooled down to the ambient temperature, concentrated under the reduced pressure. Then, water was added to the reaction mixture, followed by extraction with ethyl acetate. The organic layer was washed with aqueous saturated sodium chloride solution, dried (anhydrous MgSO₄), filtered, and concentrated in vacuo. The crude N-((5-(hydrazinecarbonyl)pyridin-2-yl)methyl)-4-methyl-N-(p-tolyl)piperazine-1-carboxamide was used without further purification (0.095 g, 93.3%, white solid).

[Step 4] N-((5-(2-(2,2-difluoroacetyl)hydrazine-1-carbonyl)pyridin-2-yl)methyl)-4-methyl-N-(p-tolyl)piperazine-1-carboxamide

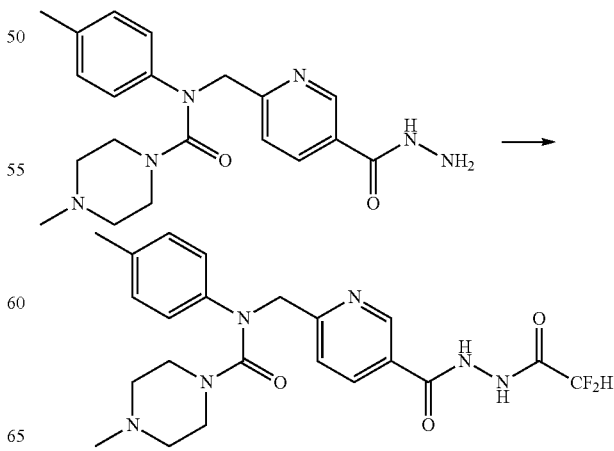

A solution of N-((5-(hydrazinecarbonyl)pyridin-2-yl)methyl)-4-methyl-N-(p-tolyl)piperazine-1-carboxamide (0.095 g, 0.249 mmol) and N,N-diisopropylethylamine (0.065 mL, 0.374 mmol) in dichloromethane (1 mL) was mixed at 0° C. with 2,2-difluoroacetic anhydride (0.054 mL, 0.499 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-((5-(2-(2,2-difluoroacetyl)hydrazine-1-carbonyl)pyridin-2-yl)methyl)-4-methyl-N-(p-tolyl)piperazine-1-carboxamide as yellow solid (0.114 g, 99.3%).

[Step 5] Compound 21598

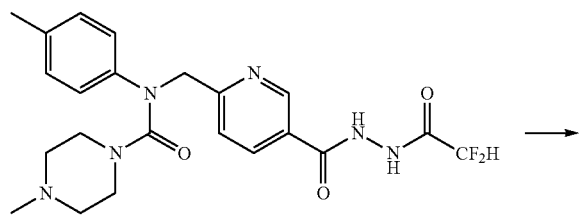

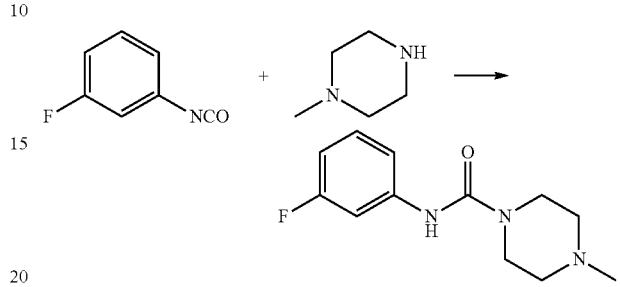

A mixture of N-((5-(2-(2,2-difluoroacetyl)hydrazine-1-carbonyl)pyridin-2-yl)methyl)-4-methyl-N-(p-tolyl)piperazine-1-carboxamide (0.114 g, 0.248 mmol) and 1-methoxy-N-triethylammoniosulfonyl-methanimidate (Burgess reagent, 0.088 g, 0.371 mmol) in tetrahydrofuran (1 mL) was heated at reflux for 18 hr, and cooled down to the ambient temperature, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-((5-(5-(difluoromethyl)-1,3,4-oxadiazol-2-yl)pyridin-2-yl)methyl)-4-methyl-N-(p-tolyl)piperazine-1-carboxamide as yellow oil (0.017 g, 15.8%).

$^1$H NMR (400 MHz, CDCl$_3$) δ 9.19 (dd, J=2.2, 0.8 Hz, 1H), 8.30 (dd, J=8.3, 2.3 Hz, 1H), 7.60 (dd, J=8.2, 0.8 Hz, 1H), 7.09-7.07 (m, 2H), 7.05-6.79 (m, 3H), 5.07 (s, 2H), 3.32-3.29 (m, 4H), 2.30-2.28 (m, 7H), 2.26 (s, 3H); LRMS (ES) m/z 443.43 (M$^+$+1).

Example 228. Compound 21599: N-((5-(5-(difluoromethyl)-1,3,4-oxadiazol-2-yl)pyridin-2-yl)methyl)-N-(3-fluorophenyl)-4-methylpiperazine-1-carboxamide

[Step 1] N-(3-fluorophenyl)-4-methylpiperazine-1-carboxamide

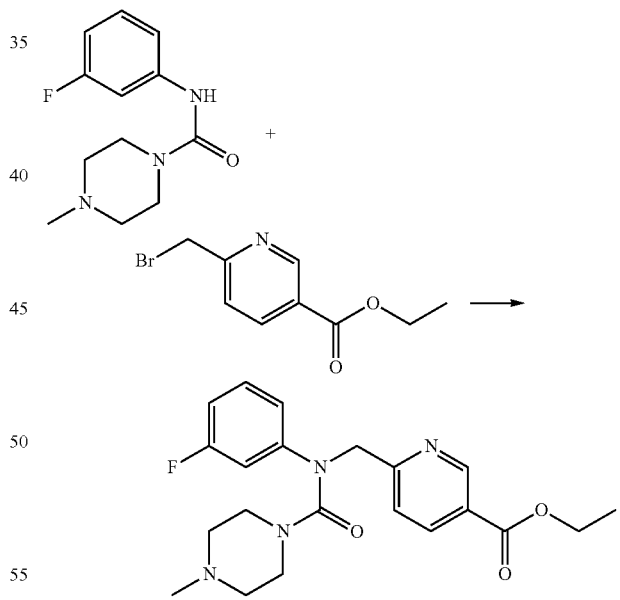

A solution of 1-fluoro-3-isocyanatobenzene (0.413 mL, 3.647 mmol) and 1-methylpiperazine (0.425 mL, 3.829 mmol) in diethylether (10 mL) was stirred at the room temperature for 18 hr. The crude N-(3-fluorophenyl)-4-methylpiperazine-1-carboxamide was used without further purification (0.703 g, 81.2%, white solid).

[Step 2] Ethyl 6-((N-(3-fluorophenyl)-4-methylpiperazine-1-carboxamido)methyl)nicotinate A solution of N-(3-fluorophenyl)-4-methylpiperazine-1-carboxamide (0.200 g, 0.843 mmol) and sodium hydride (60.00%, 0.040 g, 1.011 mmol) in N,N-dimethylformide (3 mL) was mixed at 0° C. with ethyl 6-(bromomethyl)nicotinate (0.208 g, 0.851 mmol), and stirred at the room temperature for 2 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 4 g cartridge; methanol/dichloromethane=0% to 5%) to give ethyl 6-((N-(3-fluorophenyl)-4-methylpiperazine-1-carboxamido)methyl)nicotinate as brown oil (0.135 g, 40.0%).

[Step 3] N-(3-fluorophenyl)-N-((5-(hydrazinecarbonyl)pyridin-2-yl)methyl)-4-methylpiperazine-1-carboxamide

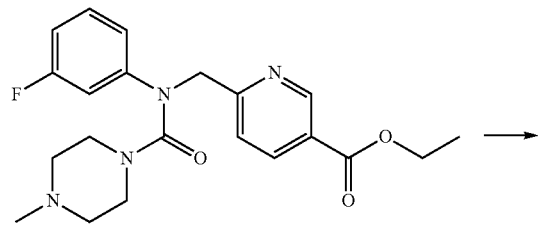

A mixture of ethyl 6-((N-(3-fluorophenyl)-4-methylpiperazine-1-carboxamido)methyl)nicotinate (0.134 g, 0.335 mmol) and hydrazine monohydrate (0.325 mL, 6.692 mmol) in ethanol (1 mL) was heated at reflux for 16 hr, and cooled down to the ambient temperature, concentrated under the reduced pressure. Then, water was added to the reaction mixture, followed by extraction with ethyl acetate. The organic layer was washed with aqueous saturated sodium chloride solution, dried (anhydrous MgSO$_4$), filtered, and concentrated in vacuo. The crude N-(3-fluorophenyl)-N-((5-(hydrazinecarbonyl)pyridin-2-yl)methyl)-4-methylpiperazine-1-carboxamide was used without further purification (0.108 g, 83.3%, white solid).

[Step 4] N-((5-(2-(2,2-difluoroacetyl)hydrazine-1-carbonyl)pyridin-2-yl)methyl)-N-(3-fluorophenyl)-4-methylpiperazine-1-carboxamide

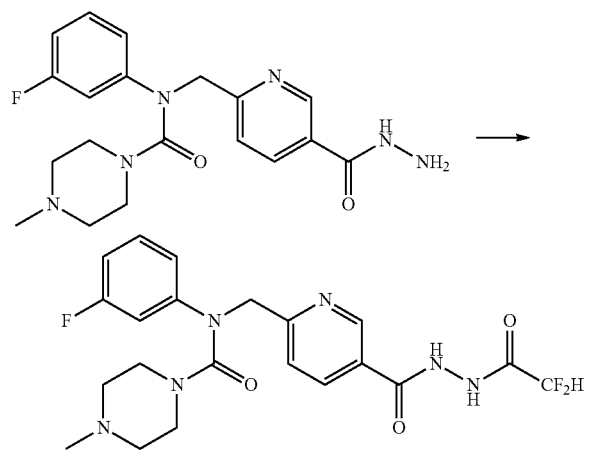

A solution of N-(3-fluorophenyl)-N-((5-(hydrazinecarbonyl)pyridin-2-yl)methyl)-4-methylpiperazine-1-carboxamide (0.108 g, 0.279 mmol) and N,N-diisopropylethylamine (0.073 mL, 0.418 mmol) in dichloromethane (1 mL) was mixed at 0° C. with 2,2-difluoroacetic anhydride (0.061 mL, 0.557 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-((5-(2-(2,2-difluoroacetyl)hydrazine-1-carbonyl)pyridin-2-yl)methyl)-N-(3-fluorophenyl)-4-methylpiperazine-1-carboxamide as yellow solid (0.129 g, 99.7%).

[Step 5] Compound 21599

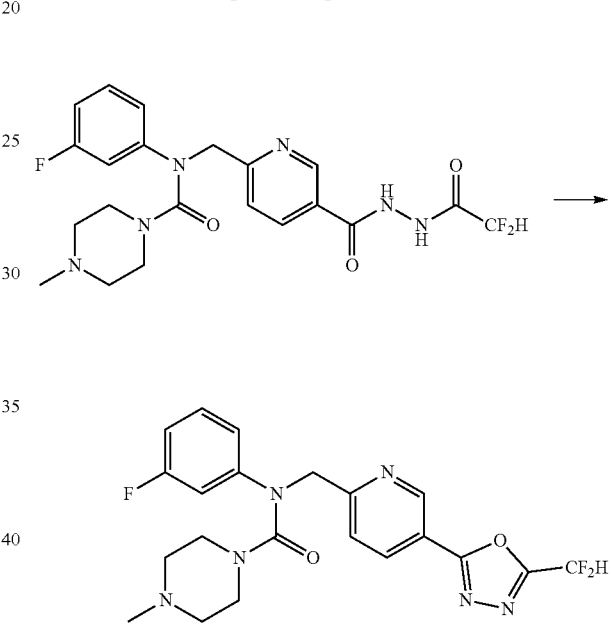

A mixture of N-((5-(2-(2,2-difluoroacetyl)hydrazine-1-carbonyl)pyridin-2-yl)methyl)-N-(3-fluorophenyl)-4-methylpiperazine-1-carboxamide (0.129 g, 0.278 mmol) and 1-methoxy-N-triethylammoniosulfonyl-methanimidate (Burgess reagent, 0.099 g, 0.417 mmol) in tetrahydrofuran (1 mL) was heated at reflux for 18 hr, and cooled down to the ambient temperature, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-((5-(5-(difluoromethyl)-1,3,4-oxadiazol-2-yl)pyridin-2-yl)methyl)-N-(3-fluorophenyl)-4-methylpiperazine-1-carboxamide as yellow oil (0.023 g, 18.2%).

$^1$H NMR (400 MHz, CDCl$_3$) δ 9.22-9.22 (m, 1H), 8.32 (dd, J=8.2, 2.2 Hz, 1H), 7.57 (d, J=8.2 Hz, 1H), 7.27-7.23 (m, 1H), 7.05-6.78 (m, 1H), 5.09 (s, 1H), 3.35-3.33 (m, 1H), 2.33-2.31 (m, 1H), 2.27 (s, 1H); LRMS (ES) m/z 447.3 (M$^+$+1).

Example 229. Compound 21600: N-((5-(5-(difluoromethyl)-1,3,4-oxadiazol-2-yl)pyridin-2-yl)methyl)-N-(4-fluorophenyl)-4-methylpiperazine-1-carboxamide

[Step 1] N-(4-fluorophenyl)-4-methylpiperazine-1-carboxamide

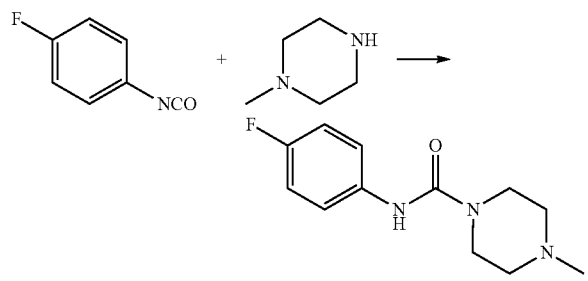

A solution of 1-fluoro-4-isocyanatobenzene (0.410 mL, 3.647 mmol) and 1-methylpiperazine (0.425 mL, 3.829 mmol) in diethylether (10 mL) was stirred at the room temperature for 18 hr. The crude N-(4-fluorophenyl)-4-methylpiperazine-1-carboxamide was used without further purification (0.582 g, 67.3%, white solid).

[Step 2] Ethyl 6-((N-(4-fluorophenyl)-4-methylpiperazine-1-carboxamido)methyl)nicotinate

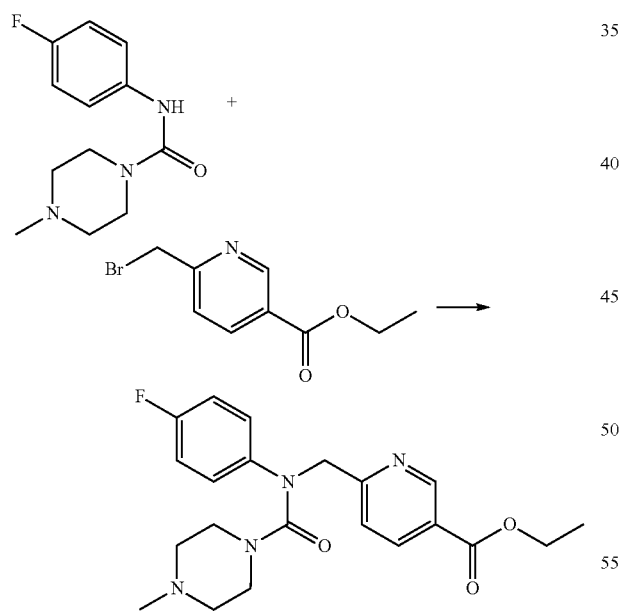

A solution of N-(4-fluorophenyl)-4-methylpiperazine-1-carboxamide (0.200 g, 0.843 mmol) and sodium hydride (60.00%, 0.040 g, 1.011 mmol) in N,N-dimethylformide (3 mL) was mixed at 0° C. with ethyl 6-(bromomethyl)nicotinate (0.208 g, 0.851 mmol), and stirred at the room temperature for 2 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 4 g cartridge; methanol/dichloromethane=0% to 5%) to give ethyl 6-((N-(4-fluorophenyl)-4-methylpiperazine-1-carboxamido)methyl)nicotinate as brown oil (0.054 g, 15.9%).

[Step 3] N-(4-fluorophenyl)-N-((5-(hydrazinecarbonyl)pyridin-2-yl)methyl)-4-methylpiperazine-1-carboxamide

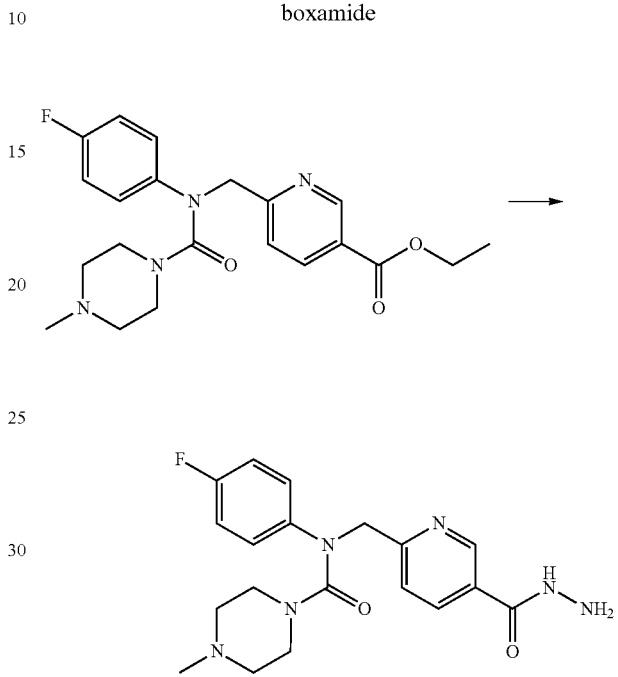

A mixture of ethyl 6-((N-(4-fluorophenyl)-4-methylpiperazine-1-carboxamido)methyl)nicotinate (0.053 g, 0.132 mmol) and hydrazine monohydrate (0.129 mL, 2.647 mmol) in ethanol (1 mL) was heated at reflux for 16 hr, and cooled down to the ambient temperature, concentrated under the reduced pressure. Then, water was added to the reaction mixture, followed by extraction with ethyl acetate. The organic layer was washed with aqueous saturated sodium chloride solution, dried (anhydrous MgSO$_4$), filtered, and concentrated in vacuo. The crude N-(4-fluorophenyl)-N-((5-(hydrazinecarbonyl)pyridin-2-yl)methyl)-4-methylpiperazine-1-carboxamide was used without further purification (0.047 g, 91.5%, light yellow solid).

[Step 4] N-((5-(2-(2,2-difluoroacetyl)hydrazine-1-carbonyl)pyridin-2-yl)methyl)-N-(4-fluorophenyl)-4-methylpiperazine-1-carboxamide

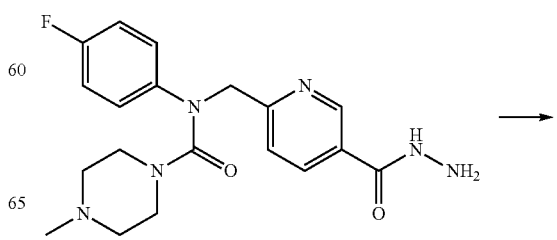

759
-continued

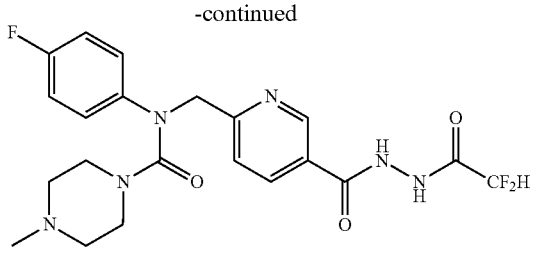

A solution of N-(4-fluorophenyl)-N-((5-(hydrazinecarbonyl)pyridin-2-yl)methyl)-4-methylpiperazine-1-carboxamide (0.047 g, 0.121 mmol) and N,N-diisopropylethylamine (0.032 mL, 0.182 mmol) in dichloromethane (1 mL) was mixed at 0° C. with 2,2-difluoroacetic anhydride (0.026 mL, 0.242 mmol), and stirred at the room temperature for 3 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-((5-(2-(2,2-difluoroacetyl)hydrazine-1-carbonyl)pyridin-2-yl)methyl)-N-(4-fluorophenyl)-4-methylpiperazine-1-carboxamide as yellow solid (0.054 g, 96.0%).

[Step 5] Compound 21600

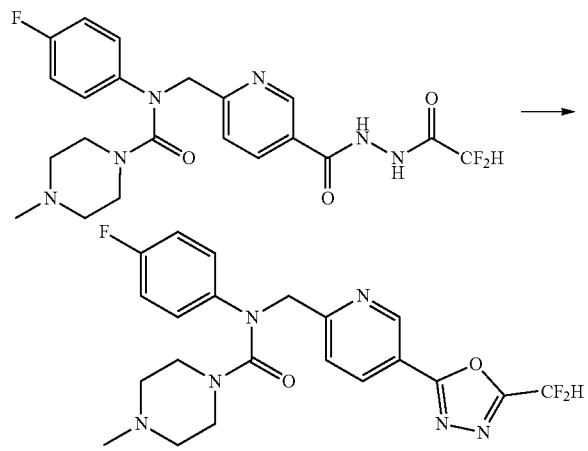

A mixture of N-((5-(2-(2,2-difluoroacetyl)hydrazine-1-carbonyl)pyridin-2-yl)methyl)-N-(4-fluorophenyl)-4-methylpiperazine-1-carboxamide (0.054 g, 0.116 mmol) and 1-methoxy-N-triethylammoniosulfonyl-methanimidate (Burgess reagent, 0.042 g, 0.174 mmol) in tetrahydrofuran (1 mL) was heated at reflux for 18 hr, and cooled down to the ambient temperature, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-((5-(5-(difluoromethyl)-1,3,4-oxadiazol-2-yl)pyridin-2-yl)methyl)-N-(4-fluorophenyl)-4-methylpiperazine-1-carboxamide as yellow oil (0.006 g, 11.0%).

760

$^1$H NMR (400 MHz, CDCl$_3$) δ 9.21 (dd, J=2.2, 0.7 Hz, 1H), 8.33 (dd, J=8.2, 2.2 Hz, 1H), 7.60 (d, J=8.2 Hz, 1H), 7.16-7.12 (m, 2H), 7.05-6.80 (m, 3H), 5.05 (s, 2H), 3.34-3.32 (m, 4H), 2.35-2.34 (m, 4H), 2.30 (s, 3H); LRMS (ES) m/z 447.4 (M++1).

Example 230. Compound 21601: (S)—N-(3-chloro-4-fluorophenyl)-N-((5-(5-(difluoromethyl)-1,3,4-oxadiazol-2-yl)pyridin-2-yl)methyl)-3-(dimethylamino)pyrrolidine-1-carboxamide

[Step 1] (S)—N-(3-chloro-4-fluorophenyl)-3-(dimethylamino)pyrrolidine-1-carboxamide

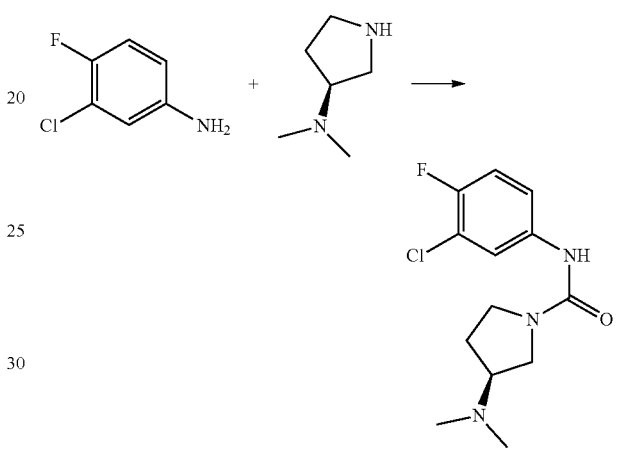

3-Chloro-4-fluoroaniline (0.500 g, 3.435 mmol) and N,N-diisopropylethylamine (1.795 mL, 10.305 mmol) in dichloromethane (10 mL) was mixed at 0° C. with triphosgene (0.917 g, 3.092 mmol). The reaction mixture was added with (S)—N,N-dimethylpyrrolidin-3-amine (0.431 g, 3.779 mmol), and stirred at the room temperature for additional 3 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 12 g cartridge; methanol/dichloromethane=0% to 10%) to give (S)—N-(3-chloro-4-fluorophenyl)-3-(dimethylamino)pyrrolidine-1-carboxamide as brown solid (0.449 g, 45.7%).

[Step 2] Ethyl (S)-6-((N-(3-chloro-4-fluorophenyl)-3-(dimethylamino)pyrrolidine-1-carboxamido)methyl)nicotinate

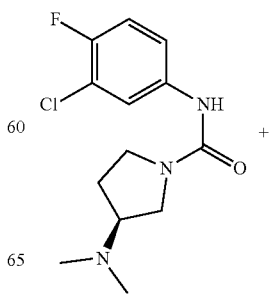

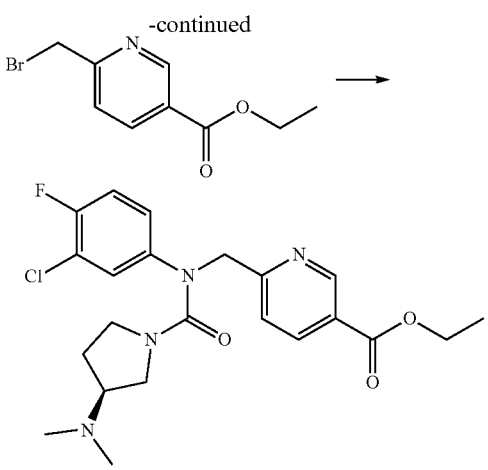

A solution of (S)—N-(3-chloro-4-fluorophenyl)-3-(dimethylamino)pyrrolidine-1-carboxamide (0.449 g, 1.571 mmol) in N,N-dimethylformide (10 mL) was stirred at 0° C. for 1 hr, and mixed with sodium hydride (60.00%, 0.094 g, 2.357 mmol). The reaction mixture was stirred at the room temperature for additional 2 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; methanol/dichloromethane=0% to 5%) to give ethyl (S)-6-((N-(3-chloro-4-fluorophenyl)-3-(dimethylamino)pyrrolidine-1-carboxamido)methyl)nicotinate as brown oil (0.135 g, 19.1%).

[Step 3] (S)—N-(3-chloro-4-fluorophenyl)-3-(dimethylamino)-N-((5-(hydrazinecarbonyl)pyridin-2-yl)methyl)pyrrolidine-1-carboxamide

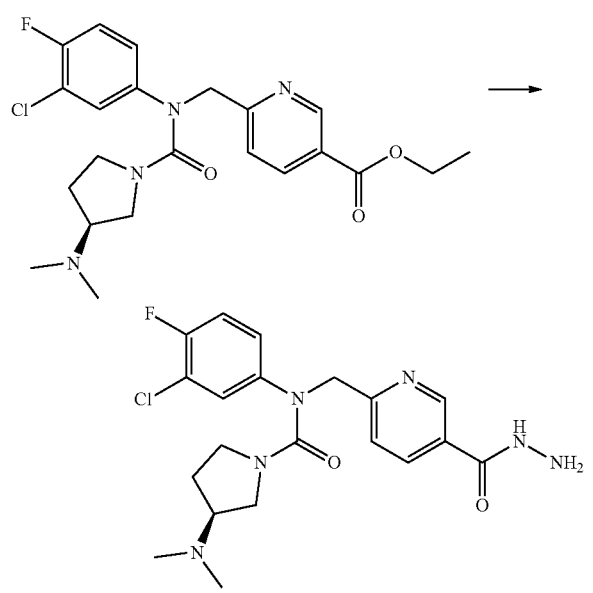

A mixture of ethyl (S)-6-((N-(3-chloro-4-fluorophenyl)-3-(dimethylamino)pyrrolidine-1-carboxamido)methyl)nicotinate (0.135 g, 0.301 mmol) and hydrazine monohydrate (0.292 mL, 6.014 mmol) in ethanol (2 mL) was heated at reflux for 18 hr, cooled down to the ambient temperature, and concentrated under the reduced pressure. Then, water was added to the reaction mixture, followed by extraction with ethyl acetate. The bi-phasic mixture was passed through a plastic frit to remove the solid residues and aqueous layer, and the organic layer collected was concentrated in vacuo. The crude (S)—N-(3-chloro-4-fluorophenyl)-3-(dimethylamino)-N-((5-(hydrazinecarbonyl)pyridin-2-yl)methyl)pyrrolidine-1-carboxamide was used without further purification (0.108 g, 82.5%, yellow oil).

[Step 4] Compound 21601

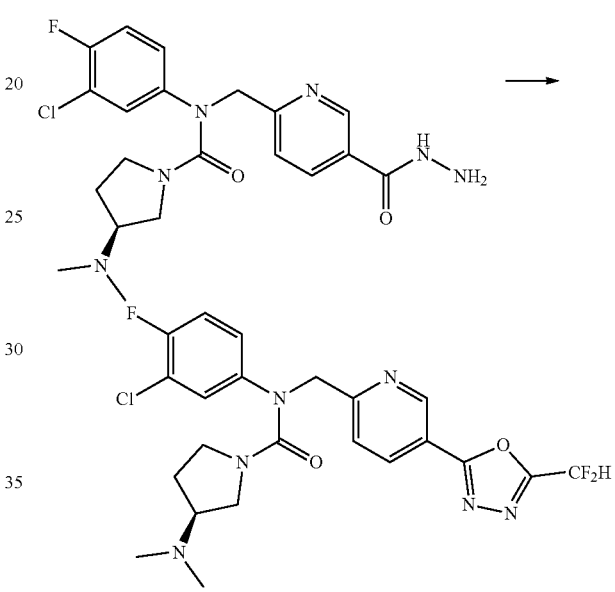

A solution of (S)—N-(3-chloro-4-fluorophenyl)-3-(dimethylamino)-N-((5-(hydrazinecarbonyl)pyridin-2-yl)methyl)pyrrolidine-1-carboxamide (0.107 g, 0.246 mmol) and N,N-diisopropylethylamine (0.064 mL, 0.369 mmol) in dichloromethane (3 mL) was mixed with 2,2-difluoroacetic anhydride (0.054 mL, 0.492 mmol) at 0° C., and stirred at the room temperature for 16 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; hexane/dichloromethane=0% to 5%) to give (S)—N-(3-chloro-4-fluorophenyl)-N-((5-(5-(difluoromethyl)-1,3,4-oxadiazol-2-yl)pyridin-2-yl)methyl)-3-(dimethylamino)pyrrolidine-1-carboxamide as brown solid (0.034 g, 27.9%).

$^1$H NMR (400 MHz, CDCl$_3$) δ 9.22 (dd, 1H, J=2.2, 0.8 Hz), 8.34 (dd, 1H, J=8.2, 2.2 Hz), 7.63-7.61 (m, 1H), 7.29-7.27 (m, 1H), 7.09-7.07 (m, 2H), 6.93 (t, 1H, J=51.6 Hz), 5.08 (d, 1H, J=16.1 Hz), 4.96 (d, 1H, J=16.2 Hz), 3.52-3.47 (m, 1H), 3.36-3.30 (m, 1H), 3.13-3.06 (m, 2H), 2.76-2.75 (m, 1H), 2.29 (s, 6H), 2.04-1.98 (m, 1H), 1.84-1.79 (m, 1H); LRMS (ES) m/z 495.4 (M$^+$+1).

Example 231. Compound 21602: (R)—N-(3-chloro-4-fluorophenyl)-N-((5-(5-(difluoromethyl)-1,3,4-oxadiazol-2-yl)pyridin-2-yl)methyl)-3-(dimethylamino)pyrrolidine-1-carboxamide

[Step 1] (R)—N-(3-chloro-4-fluorophenyl)-3-(dimethylamino)pyrrolidine-1-carboxamide

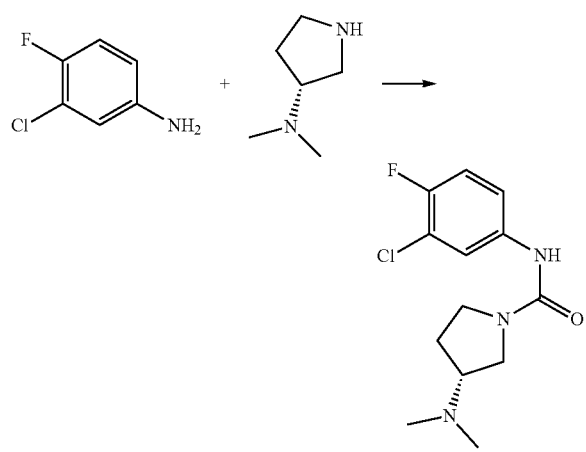

3-Chloro-4-fluoroaniline (0.500 g, 3.435 mmol) and N,N-diisopropylethylamine (1.795 mL, 10.305 mmol) in dichloromethane (10 mL) was mixed with triphosgene (0.917 g, 3.092 mmol) at 0° C. The reaction mixture was added with (R)—N,N-dimethylpyrrolidin-3-amine (0.479 mL, 3.779 mmol), and stirred at the room temperature for additional 3 hr. Then, water was added to the reaction mixture, followed by extraction with dichloromethane. The organic layer was washed with aqueous saturated sodium chloride solution, dried (anhydrous MgSO₄), filtered, and concentrated in vacuo. The residue was chromatographed (SiO₂, 12 g cartridge; hexane/dichloromethane=0% to 10%) to give (R)—N-(3-chloro-4-fluorophenyl)-3-(dimethylamino)pyrrolidine-1-carboxamide as brown solid (0.470 g, 47.9%).

[Step 2] Ethyl (R)-6-((N-(3-Chloro-4-fluorophenyl)-3-(dimethylamino)pyrrolidine-1-carboxamido)methyl)nicotinate

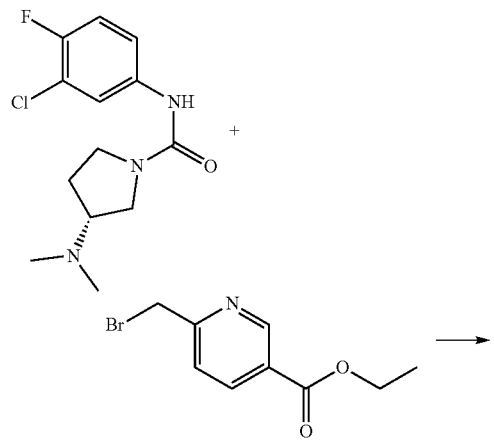

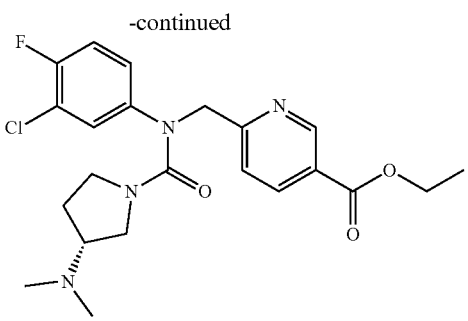

To a stirred solution of (R)—N-(3-chloro-4-fluorophenyl)-3-(dimethylamino)pyrrolidine-1-carboxamide (0.470 g, 1.645 mmol) in N,N-dimethylformide (10 mL) was added at 0° C. sodium hydride (60.00%, 0.099 g, 2.467 mmol). The reaction mixture was stirred at the same temperature for 1 hr, added with ethyl 6-(bromomethyl)nicotinate (0.442 g, 1.809 mmol) at the room temperature and stirred for additional 2 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 12 g cartridge; methanol/dichloromethane=0% to 5%) to give ethyl (R)-6-((N-(3-chloro-4-fluorophenyl)-3-(dimethylamino)pyrrolidine-1-carboxamido)methyl)nicotinate as brown oil (0.289 g, 39.1%).

[Step 3] (R)—N-(3-chloro-4-fluorophenyl)-3-(dimethylamino)-N-((5-(hydrazinecarbonyl)pyridin-2-yl)methyl)pyrrolidine-1-carboxamide

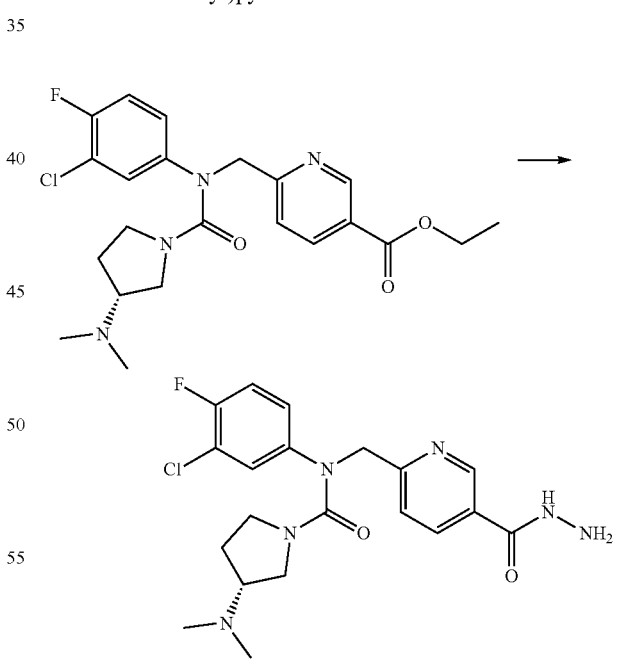

A mixture of ethyl (R)-6-((N-(3-chloro-4-fluorophenyl)-3-(dimethylamino)pyrrolidine-1-carboxamido)methyl)nicotinate (0.289 g, 0.644 mmol) and hydrazine monohydrate (0.626 mL, 12.875 mmol) in ethanol (3 mL) was heated at reflux for 18 hr, and cooled down to the ambient temperature, concentrated under the reduced pressure, and Then, water was added to the reaction mixture, followed by extraction with ethyl acetate. The organic layer was washed with aqueous saturated sodium chloride solution, dried (anhydrous MgSO₄), filtered, and concentrated in vacuo. The crude (R)—N-(3-chloro-4-fluorophenyl)-3-(dimethylamino)-N-((5-(hydrazinecarbonyl)pyridin-2-yl)methyl)pyrrolidine-1-carboxamide was used without further purification (0.277 g, 98.9%, yellow oil).

[Step 4] Compound 21602

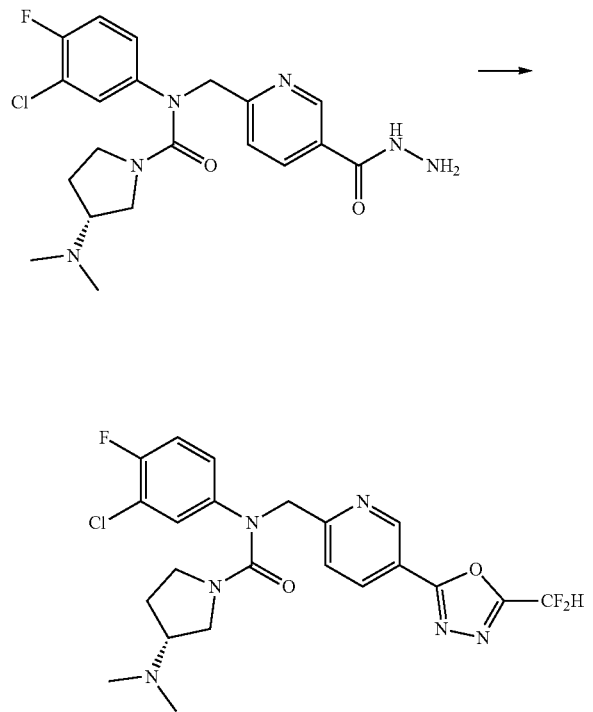

A solution of (R)—N-(3-chloro-4-fluorophenyl)-3-(dimethylamino)-N-((5-(hydrazinecarbonyl)pyridin-2-yl)methyl)pyrrolidine-1-carboxamide (0.277 g, 0.637 mmol) and N,N-diisopropylethylamine (0.166 mL, 0.955 mmol) in dichloromethane (5 mL) was mixed at 0° C. with 2,2-difluoroacetic anhydride (0.139 mL, 1.274 mmol), and stirred at the room temperature for 16 hr. Then, saturated aqueous sodium bicarbonate solution was added to the reaction mixture, followed by extraction with dichloromethane. The organic layer was washed with aqueous saturated sodium chloride solution, dried (anhydrous MgSO₄), filtered, and concentrated in vacuo. The residue was chromatographed (SiO₂, 4 g cartridge; methanol/dichloromethane=0% to 5%) to give (R)—N-(3-chloro-4-fluorophenyl)-N-((5-(5-(difluoromethyl)-1,3,4-oxadiazol-2-yl)pyridin-2-yl)methyl)-3-(dimethylamino)pyrrolidine-1-carboxamide as brown solid (0.067 g, 21.1%).

¹H NMR (400 MHz, CDCl₃) δ 9.22 (dd, 1H, J=2.2, 0.8 Hz), 8.34 (dd, 1H, J=8.2, 2.2 Hz), 7.64-7.61 (m, 1H), 7.29-7.26 (m, 1H), 7.09-7.07 (m, 2H), 6.93 (t, 1H, J=51.7 Hz), 5.08 (d, 1H, J=16.1 Hz), 4.96 (d, 1H, J=16.1 Hz), 3.50-3.46 (m, 1H), 3.36-3.30 (m, 1H), 3.13-3.01 (m, 2H), 2.71-2.70 (m, 1H), 2.25 (s, 6H), 2.03-1.96 (m, 1H), 1.80-1.75 (m, 1H); LRMS (ES) m/z 495.4 (M⁺+1).

Example 232. Compound 21619: N-(3-chloro-4-fluorophenyl)-N-((5-(5-(difluoromethyl)-1,3,4-oxadiazol-2-yl)pyridin-2-yl)methyl)morpholine-4-carboxamide

[Step 1] N-(3-chloro-4-fluorophenyl)morpholine-4-carboxamide

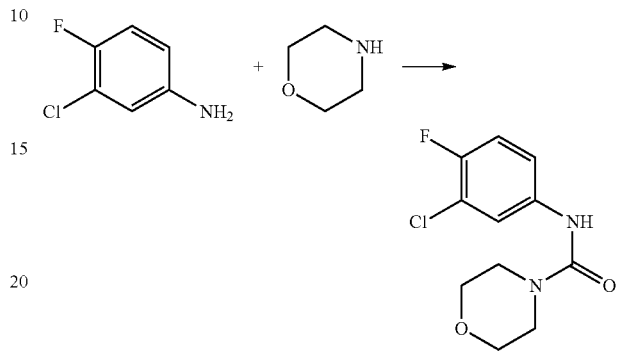

A solution of 3-chloro-4-fluoroaniline (0.500 g, 3.435 mmol), 1,1'-carbonyldiimidazole (0.613 g, 3.779 mmol) and triethylamine (0.575 mL, 4.122 mmol) in acetonitrile (10 mL) was mixed at the room temperature with morpholine (0.311 mL, 3.607 mmol). The reaction mixture was stirred at the same temperature for 18 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 12 g cartridge; methanol/dichloromethane=0% to 5%) to give N-(3-chloro-4-fluorophenyl)morpholine-4-carboxamide as purple solid (0.200 g 22.5%).

[Step 2] Methyl 6-((N-(3-chloro-4-fluorophenyl)morpholine-4-carboxamido)methyl)nicotinate

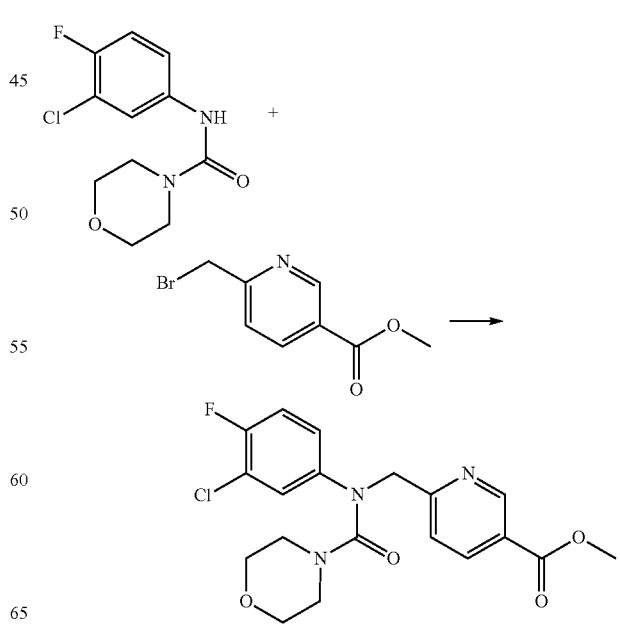

To a stirred solution of N-(3-chloro-4-fluorophenyl)morpholine-4-carboxamide (0.200 g, 0.773 mmol) in N,N-dimethylformide (5 mL) was added at 0° C. sodium hydride (60.00%, 0.037 g, 0.928 mmol). The reaction mixture was stirred at the same temperature, treated at the room temperature with methyl 6-(bromomethyl)nicotinate (0.196 g, 0.850 mmol), and stirred for additional 3 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 4 g cartridge; ethyl acetate/hexane=0% to 70%) to give methyl 6-((N-(3-chloro-4-fluorophenyl)morpholine-4-carboxamido)methyl)nicotinate as brown oil (0.110 g, 34.9%).

[Step 3] N-(3-chloro-4-fluorophenyl)-N-((5-(hydrazinecarbonyl)pyridin-2-yl)methyl)morpholine-4-carboxamide

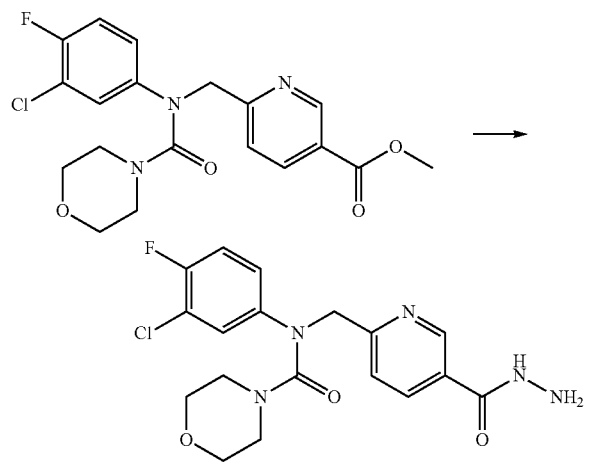

A mixture of methyl 6-((N-(3-chloro-4-fluorophenyl)morpholine-4-carboxamido)methyl)nicotinate (0.110 g, 0.270 mmol) and hydrazine monohydrate (0.262 mL, 5.394 mmol) in ethanol (5 mL) was heated at reflux for 18 hr, and cooled down to the ambient temperature. Then, water was added to the reaction mixture, followed by extraction with ethyl acetate. The organic layer was washed with aqueous saturated sodium chloride solution, dried (anhydrous MgSO$_4$), filtered, and concentrated in vacuo. The crude N-(3-chloro-4-fluorophenyl)-N-((5-(hydrazinecarbonyl)pyridin-2-yl)methyl)morpholine-4-carboxamide was used without further purification (0.110 g, 100.0%, light yellow solid).

[Step 4] Compound 21619

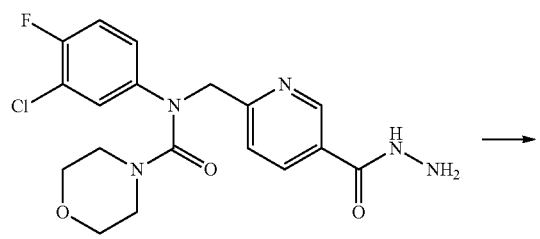

-continued

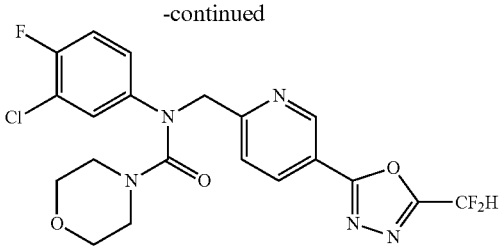

A solution of N-(3-chloro-4-fluorophenyl)-N-((5-(hydrazinecarbonyl)pyridin-2-yl)methyl)morpholine-4-carboxamide (0.110 g, 0.270 mmol) and N,N-diisopropylethylamine (0.070 mL, 0.405 mmol) in dichloromethane (3 mL) was mixed at 0° C. with 2,2-difluoroacetic anhydride (0.059 mL, 0.539 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-N-((5-(5-(difluoromethyl)-1,3,4-oxadiazol-2-yl)pyridin-2-yl)methyl)morpholine-4-carboxamide as yellow solid (0.057 g, 45.2%).

$^1$H NMR (400 MHz, CDCl$_3$) δ 9.24-9.24 (m, 1H), 8.36 (dd, 1H, J=8.2, 2.2 Hz), 7.59 (dd, 1H, J=8.2, 0.8 Hz), 7.30-7.28 (m, 1H), 7.10-7.08 (m, 2H), 6.93 (t, 1H, J=51.6 Hz), 5.05 (s, 2H), 3.54-3.52 (m, 4H), 3.27-3.26 (m, 4H); LRMS (ES) m/z 468.2 (M$^+$+1).

Example 233. Compound 21620: N-(3-chloro-4-fluorophenyl)-N-((5-(5-(difluoromethyl)-1,3,4-oxadiazol-2-yl)pyridin-2-yl)methyl)-4-methylpiperazine-1-carboxamide

[Step 1] N-(3-chloro-4-fluorophenyl)-4-methylpiperazine-1-carboxamide

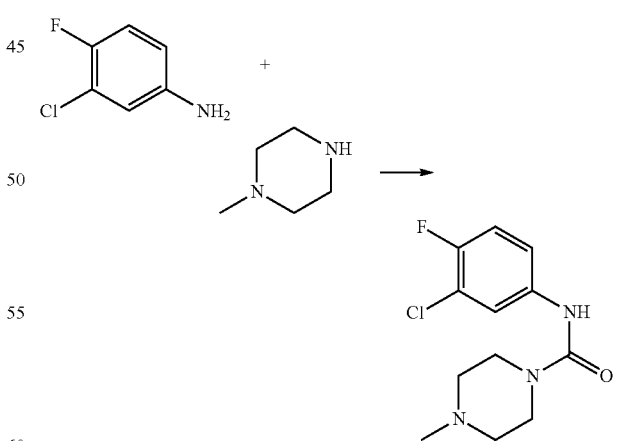

To a stirred solution of 3-chloro-4-fluoroaniline (0.500 g, 3.435 mmol) and N,N-diisopropylethylamine (1.795 mL, 10.305 mmol) in dichloromethane (10 mL) was added at 0° C. triphosgene (0.917 g, 3.092 mmol). The reaction mixture was stirred at the same temperature, added at the room temperature with 1-methylpiperazine (0.401 mL, 3.607 mmol), and stirred for additional 3 hr. Then, saturated aqueous sodium bicarbonate solution was added to the reaction mixture, followed by extraction with dichloromethane. The organic layer was washed with aqueous saturated sodium chloride solution, dried (anhydrous MgSO₄), filtered, and concentrated in vacuo. The residue was chromatographed (SiO₂, 12 g cartridge; methanol/dichloromethane=0% to 5%) to give N-(3-chloro-4-fluorophenyl)-4-methylpiperazine-1-carboxamide as white solid (0.933 g, 100.0%).

[Step 2] Methyl 6-((N-(3-chloro-4-fluorophenyl)-4-methylpiperazine-1-carboxamido)methyl)nicotinate

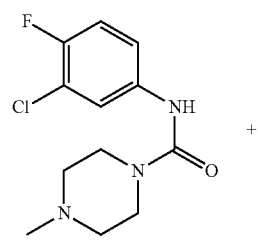

+

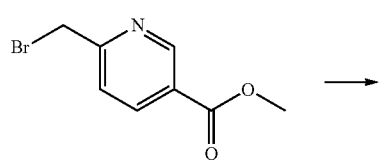

A solution of N-(3-chloro-4-fluorophenyl)-4-methylpiperazine-1-carboxamide (0.500 g, 1.840 mmol), potassium tert-butoxide (0.413 g, 3.680 mmol) and methyl 6-(bromomethyl)nicotinate (0.466 g, 2.024 mmol) in tetrahydrofuran (10 mL) was stirred at the room temperature for 16 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 12 g cartridge; methanol/dichloromethane=0% to 5%) to give methyl 6-((N-(3-chloro-4-fluorophenyl)-4-methylpiperazine-1-carboxamido)methyl)nicotinate as brown oil (0.056 g, 7.2%).

[Step 3] N-(3-chloro-4-fluorophenyl)-N-((5-(hydrazinecarbonyl)pyridin-2-yl)methyl)-4-methylpiperazine-1-carboxamide

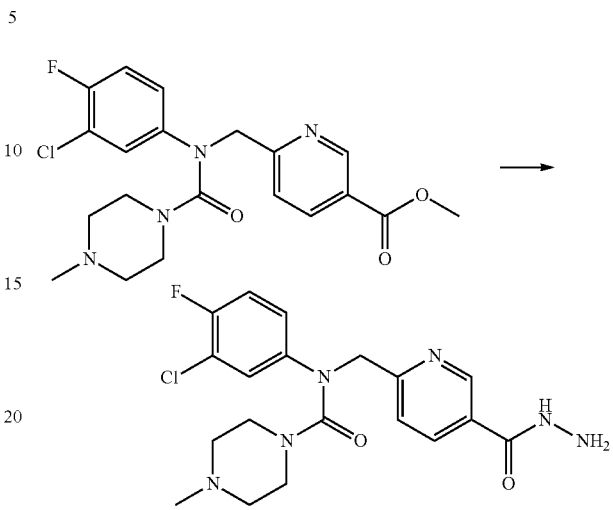

A mixture of methyl 6-((N-(3-chloro-4-fluorophenyl)-4-methylpiperazine-1-carboxamido)methyl)nicotinate (0.056 g, 0.133 mmol) and hydrazine monohydrate (0.129 mL, 2.661 mmol) in ethanol (1 mL) was heated at reflux for 16 hr, cooled down to the ambient temperature, and concentrated under the reduced pressure. Then, water was added to the reaction mixture, followed by extraction with ethyl acetate. The organic layer was washed with aqueous saturated sodium chloride solution, dried (anhydrous MgSO₄), filtered, and concentrated in vacuo. The crude N-(3-chloro-4-fluorophenyl)-N-((5-(hydrazinecarbonyl)pyridin-2-yl)methyl)-4-methylpiperazine-1-carboxamide was used without further purification (0.052 g, 92.9%, yellow solid).

[Step 4] Compound 21620

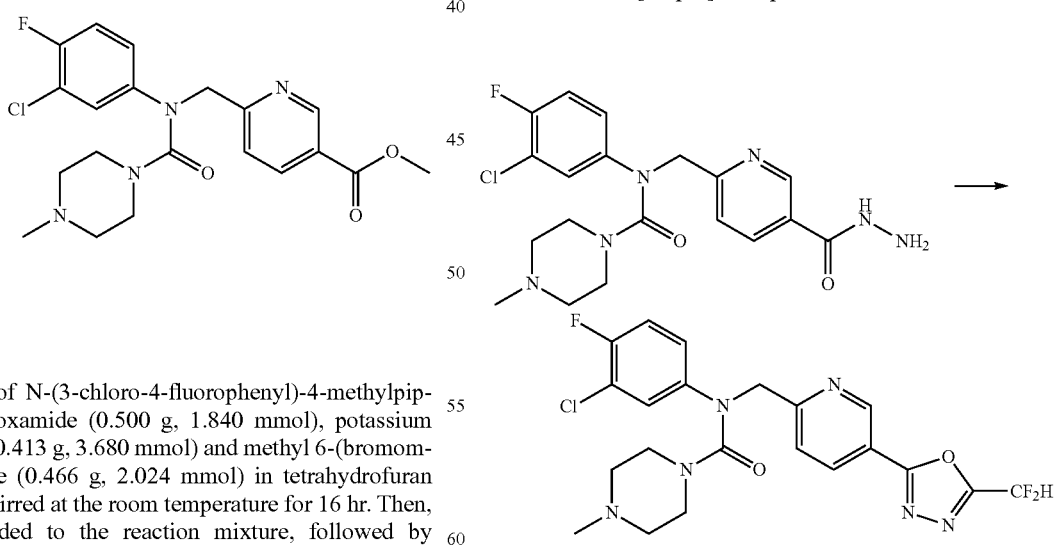

A solution of N-(3-chloro-4-fluorophenyl)-N-((5-(hydrazinecarbonyl)pyridin-2-yl)methyl)-4-methylpiperazine-1-carboxamide (0.052 g, 0.124 mmol) and N,N-diisopropylethylamine (0.032 mL, 0.185 mmol) in dichloromethane (1 mL) was mixed at 0° C. with 2,2-difluoroacetic anhydride (0.027 mL, 0.247 mmol), and stirred at the room temperature for 16 hr. Then, saturated aqueous sodium bicarbonate solution was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 4 g cartridge; methanol/dichloromethane=0% to 5%) to give N-(3-chloro-4-fluorophenyl)-N-((5-(5-(difluoromethyl)-1,3,4-oxadiazol-2-yl)pyridin-2-yl)methyl)-4-methylpiperazine-1-carboxamide as yellow oil (0.022 g, 37.0%).

$^1$H NMR (400 MHz, CDCl$_3$) δ 9.24-9.23 (m, 1H), 8.35 (dd, 1H, J=8.2, 2.2 Hz), 7.58-7.56 (m, 1H), 7.27-7.24 (m, 1H), 7.09-6.80 (m, 3H), 5.04 (s, 2H), 3.38-3.39 (m, 4H), 2.42-2.43 (m, 4H), 2.35 (s, 3H); LRMS (ES) m/z 481.5 (M$^+$+1).

Example 234. Compound 21621: N-(4-(5-(difluoromethyl)-1,3,4-oxadiazol-2-yl)benzyl)-N-(3-(4-methylpiperazin-1-yl)phenyl)thiomorpholine-4-carboxamide 1,1-dioxide

[Step 1] Methyl 4-((N-(3-(4-methylpiperazin-1-yl)phenyl)-1,1-dioxidothiomorpholine-4-carboxamido)methyl)benzoate

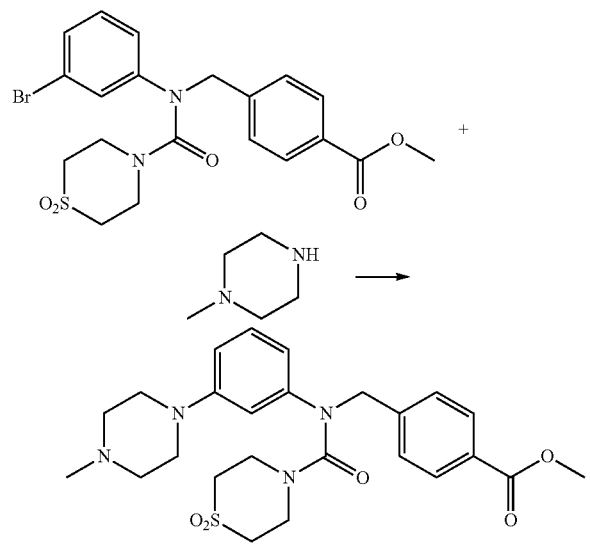

Methyl 4-((N-(3-bromophenyl)-1,1-dioxidothiomorpholine-4-carboxamido)methyl)benzoate (0.400 g, 0.831 mmol), 1-methylpiperazine (0.111 mL, 0.997 mmol), sodium tert-butoxide (0.096 g, 0.997 mmol) and Bis(tri-tert-butylphosphine)Pd (0.042 g, 0.083 mmol) were mixed at the room temperature in toluene (2 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=3%) to give methyl 4-((N-(3-(4-methylpiperazin-1-yl)phenyl)-1,1-dioxidothiomorpholine-4-carboxamido)methyl)benzoate as yellow oil (0.122 g, 29.3%).

[Step 2] N-(4-(hydrazinecarbonyl)benzyl)-N-(3-(4-methylpiperazin-1-yl)phenyl)thiomorpholine-4-carboxamide 1,1-dioxide

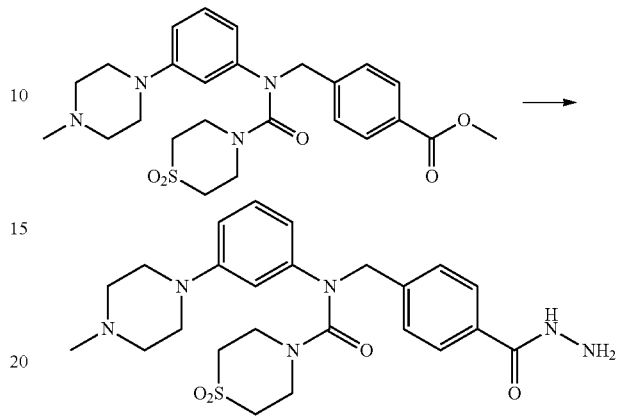

Methyl 4-((N-(3-(4-methylpiperazin-1-yl)phenyl)-1,1-dioxidothiomorpholine-4-carboxamido)methyl)benzoate (0.122 g, 0.244 mmol) and hydrazine monohydrate (0.012 mL, 0.244 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=5% to 15%) to give N-(4-(hydrazinecarbonyl)benzyl)-N-(3-(4-methylpiperazin-1-yl)phenyl)thiomorpholine-4-carboxamide 1,1-dioxide as brown oil (0.099 g, 81.3%).

[Step 3] Compound 21621

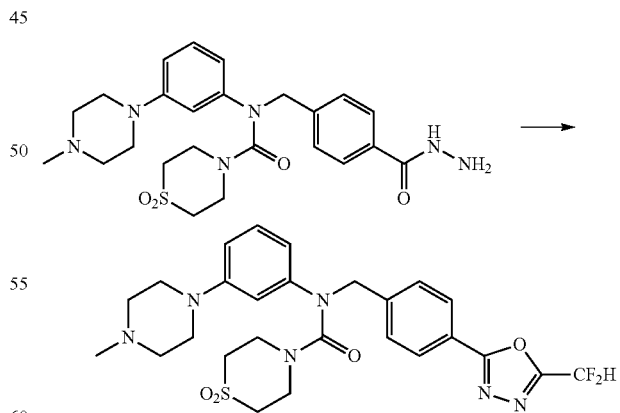

N-(4-(hydrazinecarbonyl)benzyl)-N-(3-(4-methylpiperazin-1-yl)phenyl)thiomorpholine-4-carboxamide 1,1-dioxide (0.062 g, 0.124 mmol), triethylamine (0.086 mL, 0.619 mmol) and 2,2-difluoroacetic anhydride (0.040 mL, 0.372 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(4-(5-(difluoromethyl)-1,3,4-oxadiazol-2-yl)benzyl)-N-(3-(4-methylpiperazin-1-yl)phenyl)thiomorpholine-4-carboxamide 1,1-dioxide as brown foam (0.033 g, 46.8%).

$^1$H NMR (400 MHz, CDCl$_3$) δ 8.03 (d, 2H, J=8.2 Hz), 7.42 (d, 2H, J=8.2 Hz), 6.92 (t, 2H), 6.71 (dd, 2H, J=34.2, 8.2 Hz), 6.55 (s, 1H), 4.87 (s, 2H), 3.75-3.70 (m, 4H), 3.68-3.47 (m, 6H), 3.14-2.89 (m, 4H), 2.88-2.83 (m, 6H); LRMS (ES) m/z 561.3 (M$^+$+1).

Example 235. Compound 21622: N-((5-(5-(difluoromethyl)-1,3,4-oxadiazol-2-yl)pyridin-2-yl) methyl)-N-(3-methoxyphenyl)-4-methylpiperazine-1-carboxamide

[Step 1] N-(3-methoxyphenyl)-4-methylpiperazine-1-carboxamide

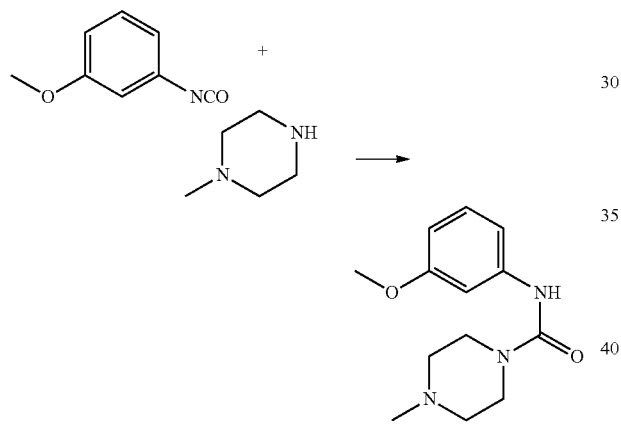

A solution of 1-isocyanato-3-methoxybenzene (0.500 g, 3.352 mmol) and 1-methylpiperazine (0.372 mL, 3.352 mmol) in diethylether (10 mL) was stirred at the room temperature for 18 hr, and concentrated under the reduced pressure. The precipitates were collected by filtration, washed by diethylether, and dried to give N-(3-methoxyphenyl)-4-methylpiperazine-1-carboxamide as white solid (0.581 g, 69.5%).

[Step 2] Methyl 6-((N-(3-methoxyphenyl)-4-methylpiperazine-1-carboxamido)methyl)nicotinate

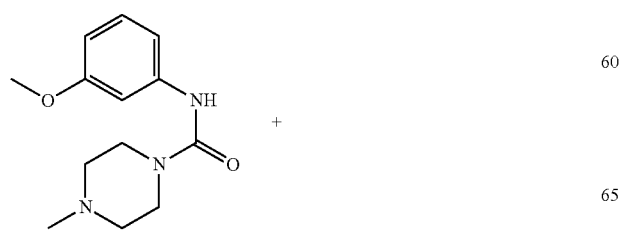

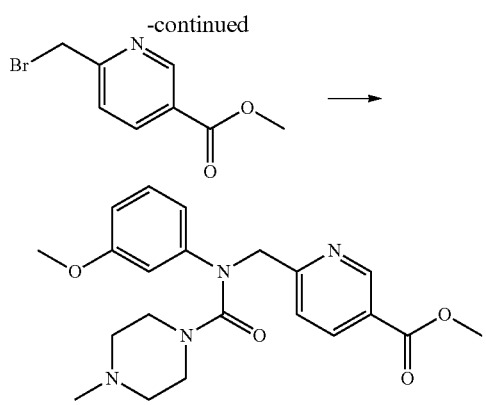

To a stirred solution of N-(3-methoxyphenyl)-4-methylpiperazine-1-carboxamide (0.300 g, 1.203 mmol) in N,N-dimethylformamide (5 mL) was added at 0° C. sodium hydride (60.00%, 0.048 g, 1.203 mmol). The reaction mixture was stirred at the same temperature for 1 hr, added at the same temperature with methyl 6-(bromomethyl)nicotinate (0.277 g, 1.203 mmol), and stirred for additional 2 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 4 g cartridge; methanol/dichloromethane=0% to 5%) to give methyl 6-((N-(3-methoxyphenyl)-4-methylpiperazine-1-carboxamido)methyl)nicotinate as brown oil (0.125 g, 26.1%).

[Step 3] N-((5-(hydrazinecarbonyl)pyridin-2-yl) methyl)-N-(3-methoxyphenyl)-4-methylpiperazine-1-carboxamide

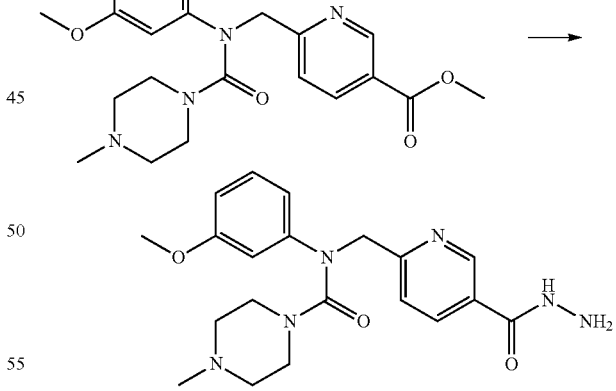

Methyl 6-((N-(3-methoxyphenyl)-4-methylpiperazine-1-carboxamido)methyl)nicotinate (0.125 g, 0.314 mmol) and hydrazine monohydrate (0.153 mL, 3.145 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=5% to 15%) to give N-((5-(hydrazinecarbonyl)pyridin-2-yl)methyl)-N-(3-methoxyphenyl)-4-methylpiperazine-1-carboxamide as brown oil (0.125 g, 100.0%).

[Step 4] Compound 21622

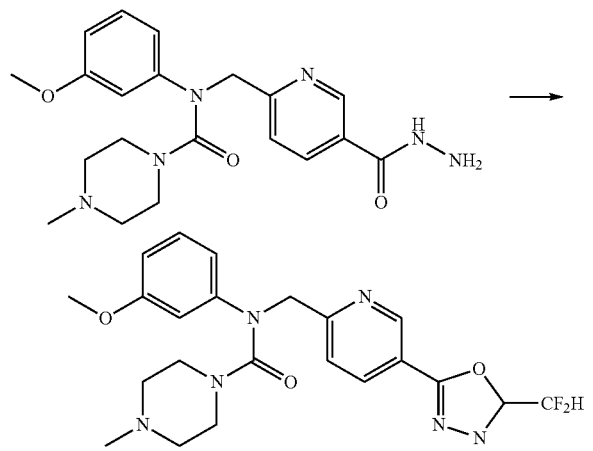

N-((5-(hydrazinecarbonyl)pyridin-2-yl)methyl)-N-(3-methoxyphenyl)-4-methylpiperazine-1-carboxamide (0.125 g, 0.314 mmol), triethylamine (0.219 mL, 1.568 mmol) and 2,2-difluoroacetic anhydride (0.102 mL, 0.941 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-((5-(5-(difluoromethyl)-1,3,4-oxadiazol-2-yl)pyridin-2-yl)methyl)-N-(3-methoxyphenyl)-4-methylpiperazine-1-carboxamide as brown foam (0.069 g, 48.1%).

$^1$H NMR (400 MHz, CDCl$_3$) δ 9.25 (dd, 1H, J=2.3, 0.9 Hz), 8.37 (dd, 1H, J=8.2, 2.2 Hz), 7.57 (dd, 1H, J=8.2, 0.9 Hz), 7.25 (td, 1H, J=8.1, 0.6 Hz), 6.96 (t, 1H, J 51.7 Hz), 6.79-6.66 (m, 3H), 5.12 (s, 2H), 3.80 (s, 3H), 3.56 (s, 4H), 2.80 (s, 4H), 2.59 (s, 3H); LRMS (ES) m/z 459.4 (M$^+$+1).

Example 236. Compound 21623: N-((5-(5-(difluoromethyl)-1,3,4-oxadiazol-2-yl)pyridin-2-yl)methyl)-N-(4-methoxyphenyl)-4-methylpiperazine-1-carboxamide

[Step 1] N-(4-methoxyphenyl)-4-methylpiperazine-1-carboxamide

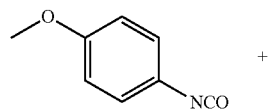

+

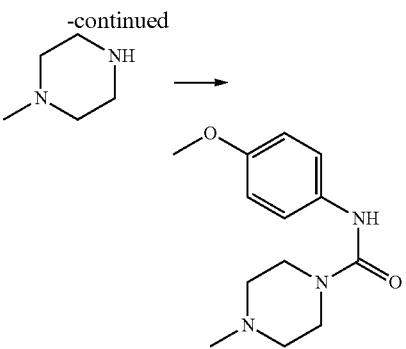

-continued

A solution of 1-isocyanato-4-methoxybenzene (0.500 g, 3.352 mmol) in diethylether (20 mL) was mixed at the room temperature with 1-methylpiperazine (0.373 mL, 3.352 mmol). The reaction mixture was stirred at the same temperature for 18 hr. The precipitates were collected by filtration, washed by diethylether, and dried to give N-(4-methoxyphenyl)-4-methylpiperazine-1-carboxamide as white solid (0.782 g, 93.6%).

[Step 2] Methyl 6-((N-(4-methoxyphenyl)-4-methylpiperazine-1-carboxamido)methyl)nicotinate

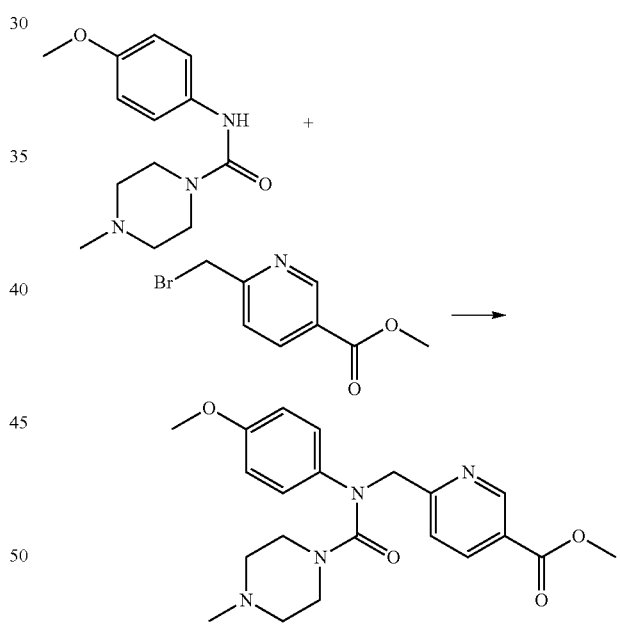

To a stirred solution of N-(4-methoxyphenyl)-4-methylpiperazine-1-carboxamide (0.300 g, 1.203 mmol) in N,N-dimethylformamide (5 mL) was added at 0° C. sodium hydride (60.00%, 0.048 g, 1.203 mmol). The reaction mixture was stirred at the same temperature for 1 hr, added at the same temperature with methyl 6-(bromomethyl)nicotinate (0.277 g, 1.203 mmol), and stirred for additional 2 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 4 g cartridge; methanol/dichloromethane=0% to 5%) to give methyl 6-((N-(4-methoxyphenyl)-4-methylpiperazine-1-carboxamido)methyl)nicotinate as brown oil (0.079 g, 16.5%).

[Step 3] N-((5-(hydrazinecarbonyl)pyridin-2-yl)methyl)-N-(4-methoxyphenyl)-4-methylpiperazine-1-carboxamide

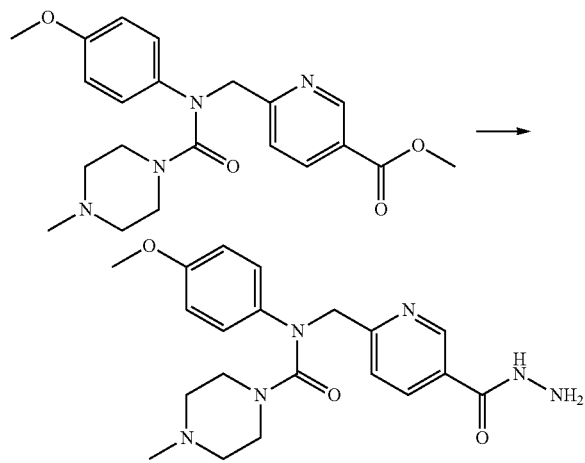

Methyl 6-((N-(4-methoxyphenyl)-4-methylpiperazine-1-carboxamido)methyl)nicotinate (0.079 g, 0.199 mmol) and hydrazine monohydrate (0.097 mL, 1.988 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=5% to 15%) to give N-((5-(hydrazinecarbonyl)pyridin-2-yl)methyl)-N-(4-methoxyphenyl)-4-methylpiperazine-1-carboxamide as brown oil (0.080 g, 100.9%).

[Step 4] Compound 21623

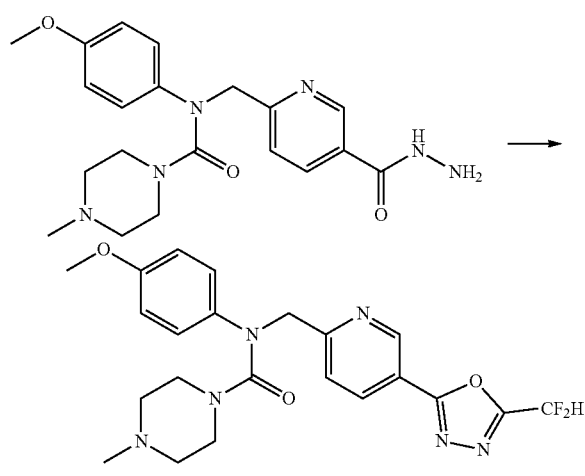

N-((5-(hydrazinecarbonyl)pyridin-2-yl)methyl)-N-(4-methoxyphenyl)-4-methylpiperazine-1-carboxamide (0.080 g, 0.201 mmol), triethylamine (0.140 mL, 1.003 mmol) and 2,2-difluoroacetic anhydride (0.065 mL, 0.602 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-((5-(5-(difluoromethyl)-1,3,4-oxadiazol-2-yl)pyridin-2-yl)methyl)-N-(4-methoxyphenyl)-4-methylpiperazine-1-carboxamide as brown foam (0.024 g, 26.0%).

$^1$H NMR (400 MHz, CDCl$_3$) δ 9.23 (dd, 1H, J=2.2, 0.9 Hz), 8:35 (dd, 1H, J=8.2, 2.2 Hz), 7.63 (dd, 1H, J=8.3, 0.9 Hz), 7.15-7.05 (m, 2H), 6.98-6.79 (m, 3H), 5.07 (s, 2H), 3.80 (s, 3H), 3.39 (s, 4H), 2.44 (s, 4H), 2.37 (s, 3H); LRMS (ES) m/z 459.2 (M$^+$+1).

Example 237. Compound 21624: N-((5-(5-(difluoromethyl)-1,3,4-oxadiazol-2-yl)pyridin-2-yl)methyl)-4-ethyl-N-phenylpiperazine-1-carboxamide

[Step 1] 4-Ethyl-N-phenylpiperazine-1-carboxamide

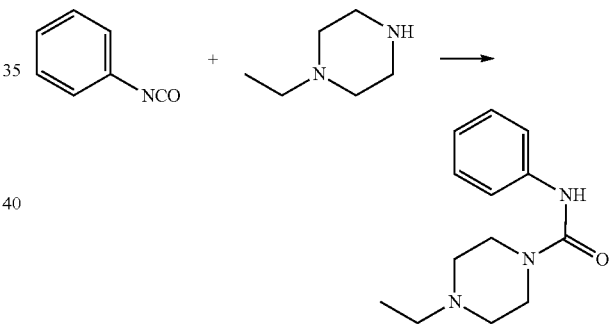

A solution of isocyanatobenzene (1.000 g, 8.395 mmol) and 1-ethylpiperazine (1.066 mL, 8.395 mmol) in diethylether (20 mL) was stirred at the room temperature for 18 hr. The precipitates were collected by filtration, washed by diethylether, and dried to give 4-ethyl-N-phenylpiperazine-1-carboxamide as white solid (1.362 g, 69.5%).

[Step 2] Methyl 6-((4-ethyl-N-phenylpiperazine-1-carboxamido)methyl)nicotinate

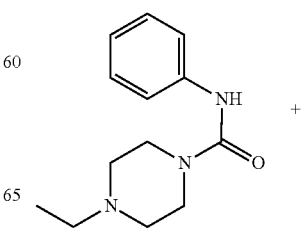

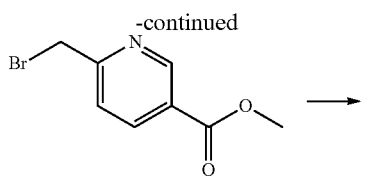

To a stirred solution of 4-ethyl-N-phenylpiperazine-1-carboxamide (0.200 g, 0.857 mmol) in N,N-dimethylformamide (5 mL) was added at 0° C. sodium hydride (60.00%, 0.034 g, 0.857 mmol). The reaction mixture was stirred at the same temperature for 1 hr, added at the same temperature with methyl 6-(bromomethyl)nicotinate (0.197 g, 0.857 mmol), and stirred for additional 2 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; methanol/dichloromethane=0% to 5%) to give methyl 6-((4-ethyl-N-phenylpiperazine-1-carboxamido)methyl)nicotinate as brown oil (0.073 g, 22.3%).

[Step 3] 4-Ethyl-N-((5-(hydrazinecarbonyl)pyridin-2-yl)methyl)-N-phenylpiperazine-1-carboxamide

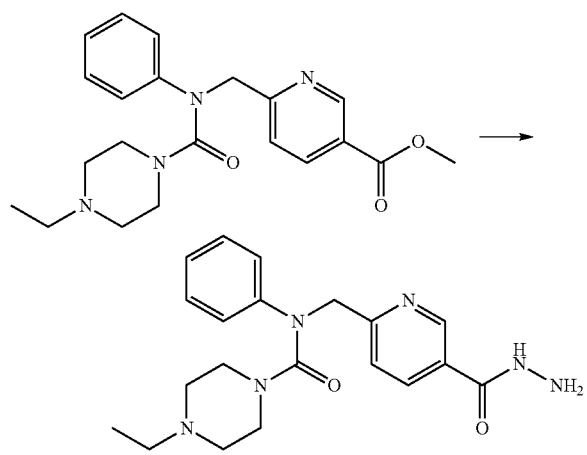

Methyl 6-((4-ethyl-N-phenylpiperazine-1-carboxamido)methyl)nicotinate (0.073 g, 0.191 mmol) and hydrazine monohydrate (0.093 mL, 1.909 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=5% to 15%) to give 4-ethyl-N-((5-(hydrazinecarbonyl)pyridin-2-yl)methyl)-N-phenylpiperazine-1-carboxamide as brown oil (0.073 g, 100.0%).

[Step 4] Compound 21624

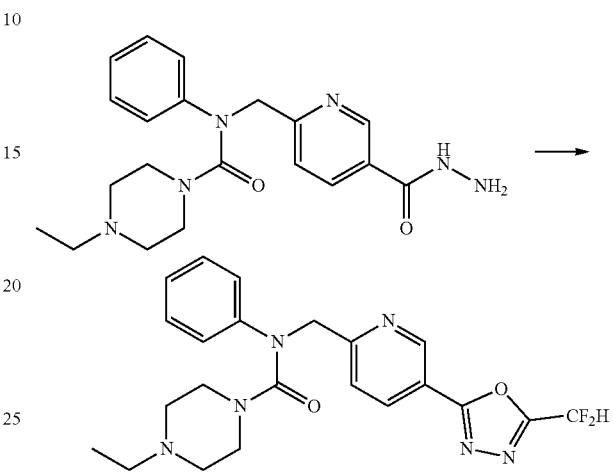

4-ethyl-N-((5-(hydrazinecarbonyl)pyridin-2-yl)methyl)-N-phenylpiperazine-1-carboxamide (0.073 g, 0.191 mmol), triethylamine (0.133 mL, 0.954 mmol) and 2,2-difluoroacetic anhydride (0.062 mL, 0.573 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-((5-(5-(difluoromethyl)-1,3,4-oxadiazol-2-yl)pyridin-2-yl)methyl)-4-ethyl-N-phenylpiperazine-1-carboxamide as brown foam (0.017 g, 20.4%).

$^1$H NMR (400 MHz, CDCl$_3$) δ 9.24 (dd, 1H, J=2.2, 0.8 Hz), 8.35 (dd, 1H, J=8.2, 2.2 Hz), 7.62 (dd, 1H, J=8.3, 0.8 Hz), 7.36-7.29 (m, 2H), 7.20-7.09 (m, 3H), 7.01 (t, 1H, J=51.7 Hz), 5.13 (s, 2H), 3.43 (s, 4H), 2.67-2.38 (m, 7H); LRMS (ES) m/z 443.3 (M$^+$+1).

Example 238. Compound 21625: N-((5-(5-(difluoromethyl)-1,3,4-oxadiazol-2-yl)pyridin-2-yl)methyl)-N-(2-fluorophenyl)thiomorpholine-4-carboxamide 1,1-dioxide

[Step 1]
N-(2-fluorophenyl)thiomorpholine-4-carboxamide 1,1-dioxide

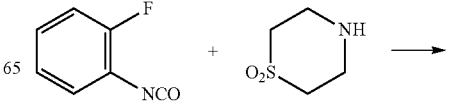

-continued

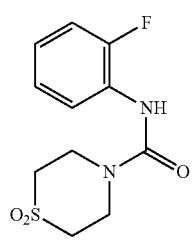

A solution of 1-fluoro-2-isocyanatobenzene (1.000 g, 7.293 mmol) and thiomorpholine 1,1-dioxide (0.976 g, 7.220 mmol) diethylether (20 mL) was stirred at the room temperature for 18 hr. The precipitates were collected by filtration, washed by diethylether, and dried to give N-(2-fluorophenyl)thiomorpholine-4-carboxamide 1,1-dioxide as white solid (1.920 g, 96.7%).

[Step 2] Methyl 6-((N-(2-fluorophenyl)-1,1-dioxidothiomorpholine-4-carboxamido)methyl)nicotinate

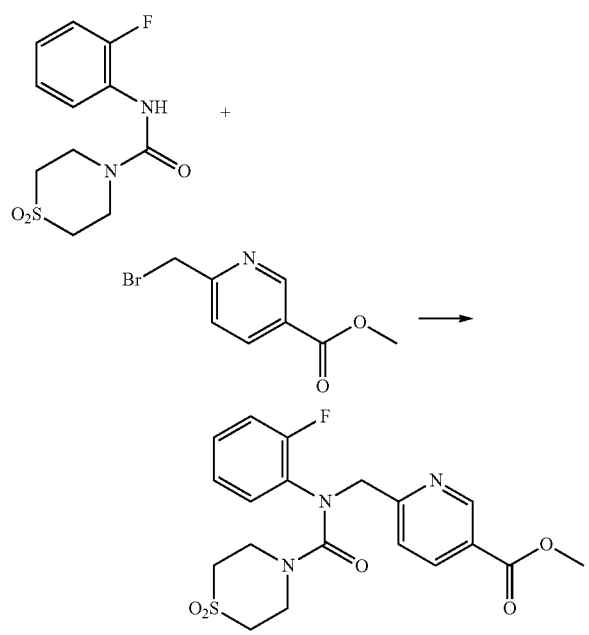

To a stirred solution of N-(2-fluorophenyl)thiomorpholine-4-carboxamide 1,1-dioxide (0.200 g, 0.735 mmol) in N,N-dimethylformamide (5 mL) was added at 0° C. sodium hydride (60.00%, 0.029 g, 0.735 mmol). The reaction mixture was stirred at the same temperature for 1 hr, added at the same temperature with methyl 6-(bromomethyl)nicotinate (0.169 g, 0.735 mmol), and stirred for additional 2 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 12 g cartridge; methanol/dichloromethane=0% to 5%) to give methyl 6-((N-(2-fluorophenyl)-1,1-dioxidothiomorpholine-4-carboxamido)methyl)nicotinate as brown oil (0.229 g, 73.9%).

[Step 3] N-(2-fluorophenyl)-N-((5-(hydrazinecarbonyl)pyridin-2-yl)methyl)thiomorpholine-4-carboxamide 1,1-dioxide

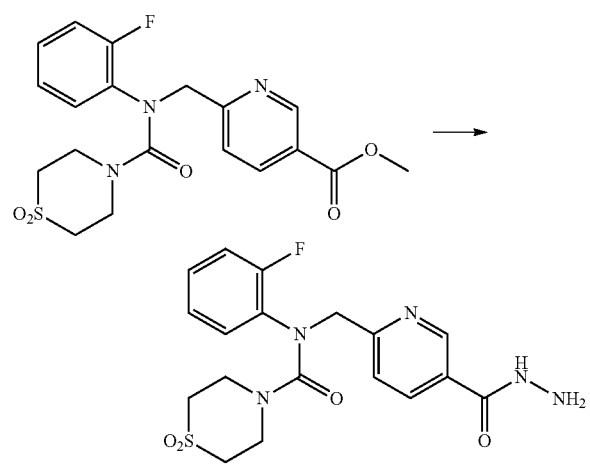

Methyl 6-((N-(2-fluorophenyl)-1,1-dioxidothiomorpholine-4-carboxamido)methyl)nicotinate (0.229 g, 0.543 mmol) and hydrazine monohydrate (0.264 mL, 5.429 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=5% to 15%) to give N-(2-fluorophenyl)-N-((5-(hydrazinecarbonyl)pyridin-2-yl)methyl)thiomorpholine-4-carboxamide 1,1-dioxide as brown oil (0.229 g, 100.0%).

[Step 4] Compound 21625

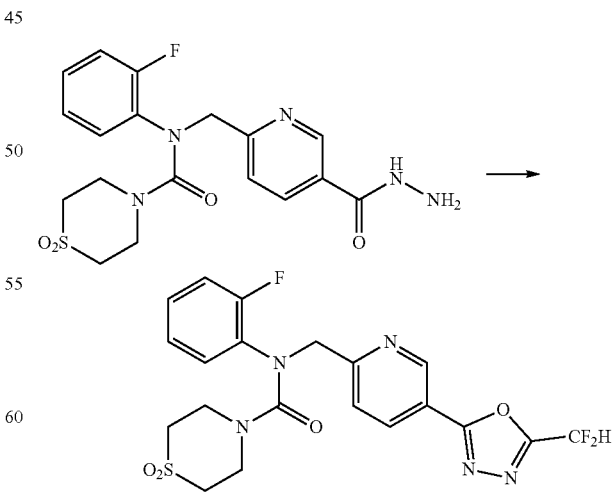

N-(2-fluorophenyl)-N-((5-(hydrazinecarbonyl)pyridin-2-yl)methyl)thiomorpholine-4-carboxamide 1,1-dioxide (0.228 g, 0.541 mmol), triethylamine (0.377 mL, 2.705 mmol) and 2,2-difluoroacetic anhydride (0.177 mL, 1.623 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-((5-(5-(difluoromethyl)-1,3,4-oxadiazol-2-yl)pyridin-2-yl)methyl)-N-(2-fluorophenyl)thiomorpholine-4-carboxamide 1,1-dioxide as orange foam (0.073 g, 28.0%).

$^1$H NMR (400 MHz, CDCl$_3$) δ 9.23 (d, 1H, J=2.0 Hz), 8.40 (dd, 1H, J=8.2, 2.2 Hz), 7.66 (d, 1H, J=8.2 Hz), 7.40-7.31 (m, 1H), 7.30-7.12 (m, 3H), 6.95 (t, 1H, J=51.6 Hz), 5.04 (s, 2H), 3.79-3.71 (m, 4H), 2.88 (t, 4H, J=5.3 Hz); LRMS (ES) m/z 482.2 (M$^+$+1).

Example 239. Compound 21626: N-(3-chlorophenyl)-N-((5-(5-(difluoromethyl)-1,3,4-oxadiazol-2-yl)pyridin-2-yl)methyl)thiomorpholine-4-carboxamide 1,1-dioxide

[Step 1]
N-(3-chlorophenyl)thiomorpholine-4-carboxamide 1,1-dioxide

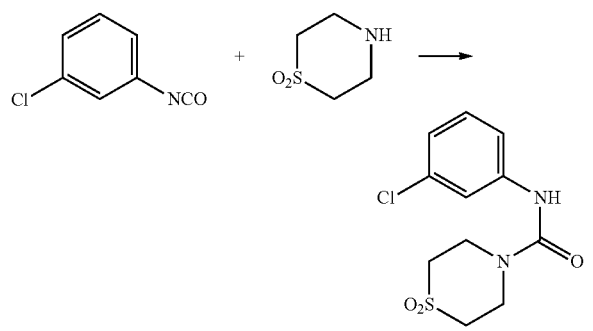

A solution of 1-chloro-3-isocyanatobenzene (1.000 g, 6.512 mmol) and thiomorpholine 1,1-dioxide (0.871 g, 6.447 mmol) in diethylether (20 mL) was stirred at the room temperature for 18 hr. The precipitates were collected by filtration, washed by diethylether, and dried to give N-(3-chlorophenyl)thiomorpholine-4-carboxamide 1,1-dioxide as white solid (1.811 g, 96.3%).

[Step 2] Methyl 6-((N-(3-chlorophenyl)-1,1-dioxidothiomorpholine-4-carboxamido)methyl)nicotinate

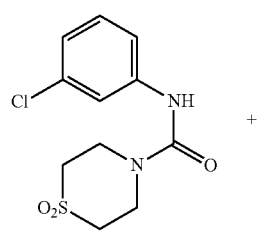

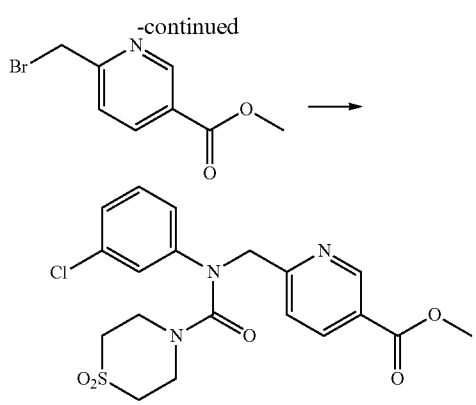

To a stirred solution of N-(3-chlorophenyl)thiomorpholine-4-carboxamide 1,1-dioxide (0.200 g, 0.693 mmol) in N,N-dimethylformamide (5 mL) was added at 0° C. sodium hydride (60.00%, 0.028 g, 0.693 mmol). The reaction mixture was stirred at the same temperature for 1 hr, added at the same temperature with methyl 6-(bromomethyl)nicotinate (0.159 g, 0.693 mmol), and stirred for additional 2 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; methanol/dichloromethane=0% to 5%) to give methyl 6-((N-(3-chlorophenyl)-1,1-dioxidothiomorpholine-4-carboxamido)methyl)nicotinate as brown oil (0.261 g, 86.0%).

[Step 3] N-(3-chlorophenyl)-N-((5-(hydrazinecarbonyl)pyridin-2-yl)methyl)thiomorpholine-4-carboxamide 1,1-dioxide

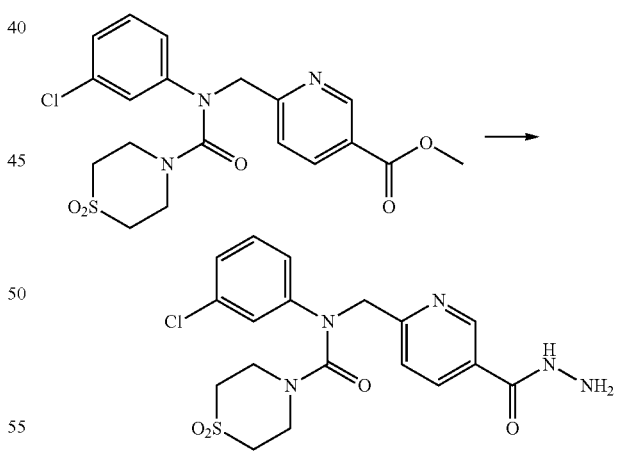

Methyl 6-((N-(3-chlorophenyl)-1,1-dioxidothiomorpholine-4-carboxamido)methyl)nicotinate (0.261 g, 0.596 mmol) and hydrazine monohydrate (0.290 mL, 5.958 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=5% to 15%) to give N-(3-chlorophenyl)-N-((5-(hydrazinecarbonyl)pyridin-2-yl)methyl)thiomorpholine-4-carboxamide 1,1-dioxide as brown oil (0.261 g, 100.0%).

[Step 4] Compound 21626

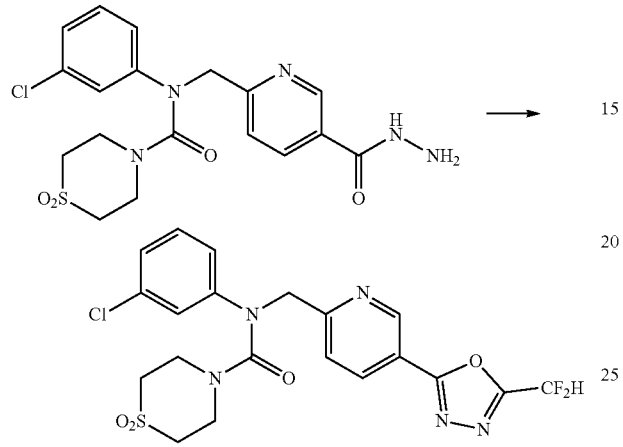

N-(3-chlorophenyl)-N-((5-(hydrazinecarbonyl)pyridin-2-yl)methyl)thiomorpholine-4-carboxamide 1,1-dioxide (0.261 g, 0.596 mmol), triethylamine (0.415 mL, 2.980 mmol) and 2,2-difluoroacetic anhydride (0.195 mL, 1.788 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 3%) to give N-(3-chlorophenyl)-N-((5-(5-(difluoromethyl)-1,3,4-oxadiazol-2-yl)pyridin-2-yl)methyl)thiomorpholine-4-carboxamide 1,1-dioxide as yellow foam (0.087 g, 29.3%).

$^1$H NMR (400 MHz, CDCl₃) δ 9.27 (dd, 1H, J=2.2, 0.8 Hz), 8.43 (dd, 1H, J=8.2, 2.2 Hz), 7.55 (dd, 1H, J=8.2, 0.9 Hz), 7.31 (t, 1H, J=8.0 Hz), 7.23 (t, 1H, J=2.1 Hz), 7.21-7.10 (m, 2H), 7.10 (t, 1H), 5.12 (s, 2H), 3.75 (t, 4H, J=5.3 Hz), 3.06-2.99 (m, 4H); LRMS (ES) m/z 498.3 (M⁺+1).

Example 240. Compound 21627: N-((5-(5-(difluoromethyl)-1,3,4-oxadiazol-2-yl)pyridin-2-yl)methyl)-N-(3-(4-methylpiperazin-1-yl)phenyl)thiomorpholine-4-carboxamide 1,1-dioxide

[Step 1] N-(3-bromophenyl)thiomorpholine-4-carboxamide 1,1-dioxide

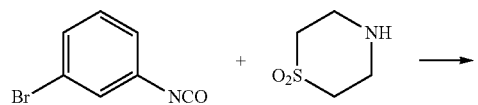

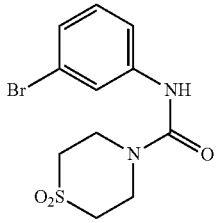

A solution of 1-bromo-3-isocyanatobenzene (1.000 g, 5.050 mmol) in diethylether (20 mL) was mixed at the room temperature with thiomorpholine 1,1-dioxide (0.683 g, 5.050 mmol). The reaction mixture was stirred at the same temperature for 18 hr. The precipitates were collected by filtration, washed by diethylether, and dried to give N-(3-bromophenyl)thiomorpholine-4-carboxamide 1,1-dioxide as white solid (1.660 g, 98.7%).

[Step 2] Methyl 6-((N-(3-bromophenyl)-1,1-dioxidothiomorpholine-4-carboxamido)methyl)nicotinate

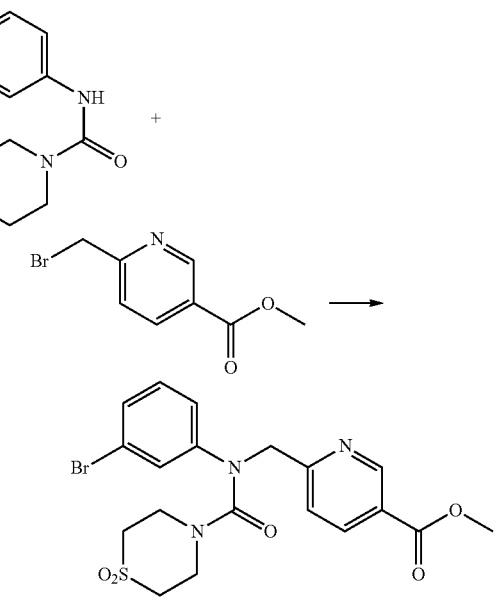

To a stirred solution of N-(3-bromophenyl)thiomorpholine-4-carboxamide 1,1-dioxide (0.830 g, 2.491 mmol) in N,N-dimethylformamide (5 mL) was added at 0° C. sodium hydride (60.00%, 0.100 g, 2.491 mmol). The reaction mixture was stirred at the same temperature for 1 hr, added at the same temperature with methyl 6-(bromomethyl)nicotinate (0.573 g, 2.491 mmol), and stirred for additional 2 hr.

Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 4 g cartridge; methanol/dichloromethane=0% to 5%) to give methyl 6-((N-(3-bromophenyl)-1,1-dioxidothiomorpholine-4-carboxamido)methyl)nicotinate as brown oil (0.850 g, 70.7%).

787

[Step 3] Methyl 6-((N-(3-(4-methylpiperazin-1-yl)phenyl)-1,1-dioxidothiomorpholine-4-carboxamido)methyl)nicotinate

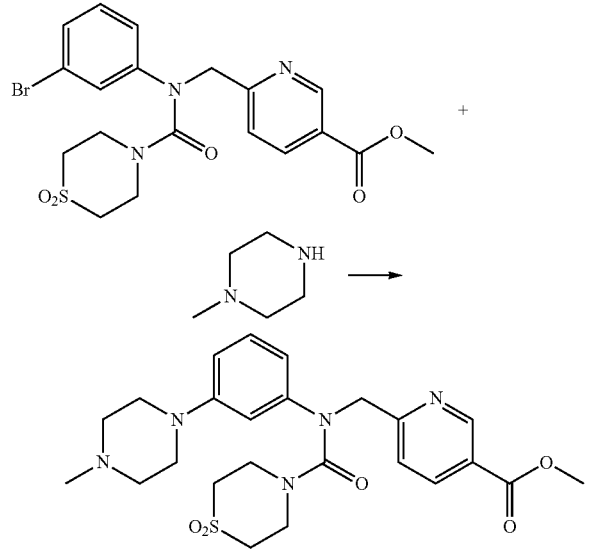

Methyl 6-((N-(3-bromophenyl)-1,1-dioxidothiomorpholine-4-carboxamido)methyl)nicotinate (0.297 g, 0.616 mmol), 1-methylpiperazine (0.082 mL, 0.739 mmol), sodium tert-butoxide (0.071 g, 0.739 mmol) and Bis(tri-tert-butylphosphine)Pd (0.031 g, 0.062 mmol) were mixed at the room temperature in toluene (2 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 100%) to give methyl 6-((N-(3-(4-methylpiperazin-1-yl)phenyl)-1,1-dioxidothiomorpholine-4-carboxamido) methyl)nicotinate as yellow oil (0.118 g, 38.2%).

[Step 4] N-((5-(hydrazinecarbonyl)pyridin-2-yl)methyl)-N-(3-(4-methylpiperazin-1-yl)phenyl)thiomorpholine-4-carboxamide 1,1-dioxide

788

-continued

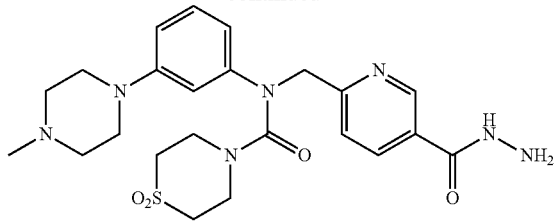

Methyl 6-((N-(3-(4-methylpiperazin-1-yl)phenyl)-1,1-dioxidothiomorpholine-4-carboxamido) methyl)nicotinate (0.118 g, 0.235 mmol) and hydrazine monohydrate (0.114 mL, 2.352 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=5% to 15%) to give N-((5-(hydrazinecarbonyl)pyridin-2-yl)methyl)-N-(3-(4-methylpiperazin-1-yl)phenyl)thiomorpholine-4-carboxamide 1,1-dioxide as brown oil (0.053 g, 45.0%).

[Step 5] Compound 21627

N-((5-(hydrazinecarbonyl)pyridin-2-yl)methyl)-N-(3-(4-methylpiperazin-1-yl)phenyl)thiomorpholine-4-carboxamide 1,1-dioxide (0.053 g, 0.106 mmol), triethylamine (0.074 mL, 0.528 mmol) and 2,2-difluoroacetic anhydride (0.034 mL, 0.317 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-((5-(5-(difluoromethyl)-1,3,4-oxadiazol-2-yl)pyridin-2-yl)

methyl)-N-(3-(4-methylpiperazin-1-yl)phenyl)thiomorpholine-4-carboxamide 1,1-dioxide as brown foam (0.005 g, 8.6%).

¹H NMR (400 MHz, CDCl₃) δ 9.25 (dd, 1H, J=2.2, 0.9 Hz), 8.39 (dd, 1H, J=8.2, 2.2 Hz), 7.60-7.53 (m, 1H), 7.15 (d, 2H, J=8.9 Hz), 7.10-6.81 (m, 3H), 5.06 (s, 2H), 3.81-3.67 (m, 4H), 3.63-3.58 (m, 4H), 2.95 (t, 4H, J=5.3 Hz), 2.88 (s, 3H); LRMS (ES) m/z 562.4 (M⁺+1).

Example 241. Compound 21628: N-((5-(5-(difluoromethyl)-1,3,4-oxadiazol-2-yl)pyridin-2-yl)methyl)-N-(4-(4-methylpiperazin-1-yl)phenyl)thiomorpholine-4-carboxamide 1,1-dioxide

[Step 1] N-(4-bromophenyl)thiomorpholine-4-carboxamide 1,1-dioxide

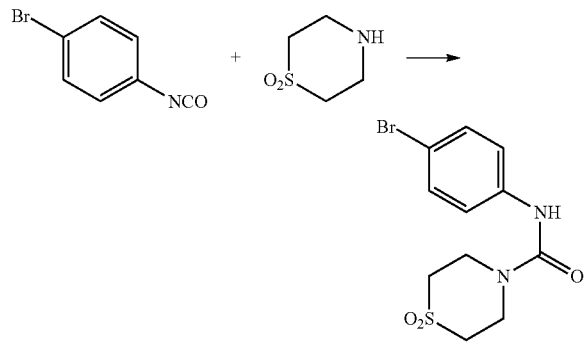

A solution of 1-bromo-4-isocyanatobenzene (1.000 g, 5.050 mmol) in diethylether (20 mL) was mixed at the room temperature with thiomorpholine 1,1-dioxide (0.683 g, 5.050 mmol). The reaction mixture was stirred at the same temperature for 18 hr. The precipitates were collected by filtration, washed by diethylether, and dried to give N-(4-bromophenyl)thiomorpholine-4-carboxamide 1,1-dioxide as white solid (1.622 g, 96.4%).

[Step 2] Methyl 6-((N-(4-bromophenyl)-1,1-dioxidothiomorpholine-4-carboxamido)methyl)nicotinate

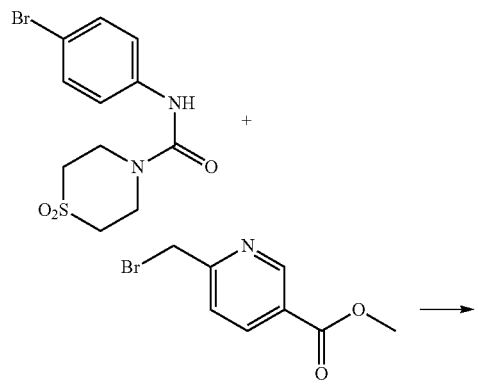

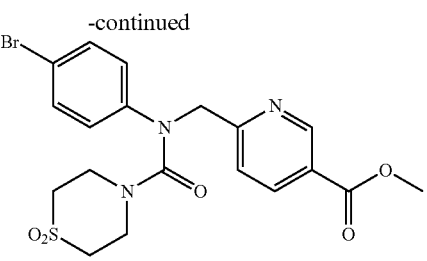

To a stirred solution of N-(4-bromophenyl)thiomorpholine-4-carboxamide 1,1-dioxide (0.810 g, 2.431 mmol) in N,N-dimethylformamide (5 mL) was added at 0° C. sodium hydride (60.00%, 0.097 g, 2.431 mmol). The reaction mixture was stirred at the same temperature for 1 hr, added at the same temperature with methyl 6-(bromomethyl)nicotinate (0.559 g, 2.431 mmol), and stirred for additional 2 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 4 g cartridge; methanol/dichloromethane=0% to 5%) to give methyl 6-((N-(4-bromophenyl)-1,1-dioxidothiomorpholine-4-carboxamido)methyl)nicotinate as brown oil (0.298 g, 25.4%).

[Step 3] Methyl 6-((N-(4-(4-methylpiperazin-1-yl)phenyl)-1,1-dioxidothiomorpholine-4-carboxamido)methyl)nicotinate

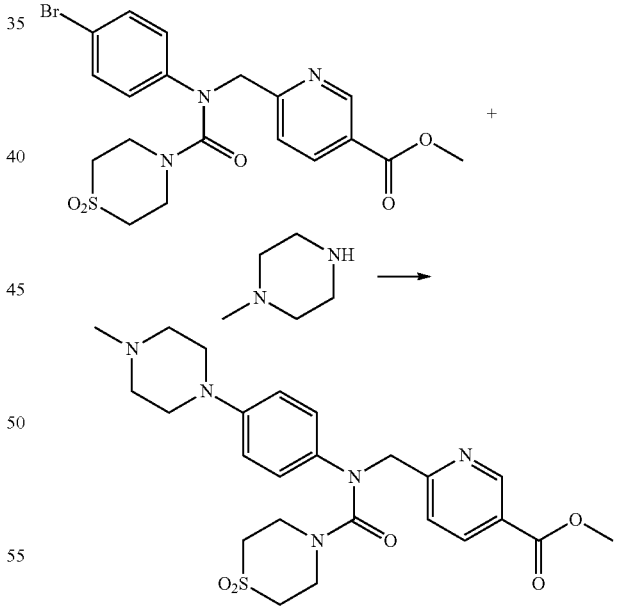

Methyl 6-((N-(4-bromophenyl)-1,1-dioxidothiomorpholine-4-carboxamido)methyl)nicotinate (0.400 g, 0.829 mmol), 1-methylpiperazine (0.111 mL, 0.995 mmol), sodium tert-butoxide (0.096 g, 0.995 mmol) and Bis(tri-tert-butylphosphine)Pd (0.042 g, 0.083 mmol) were mixed at the room temperature in toluene (2 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 100%) to give methyl 6-((N-(4-(4-methylpiperazin-1-yl)phenyl)-1,1-dioxidothiomorpholine-4-carboxamido) methyl)nicotinate as yellow oil (0.128 g, 30.8%).

[Step 4] N-((5-(hydrazinecarbonyl)pyridin-2-yl)methyl)-N-(4-(4-methylpiperazin-1-yl)phenyl)thiomorpholine-4-carboxamide 1,1-dioxide

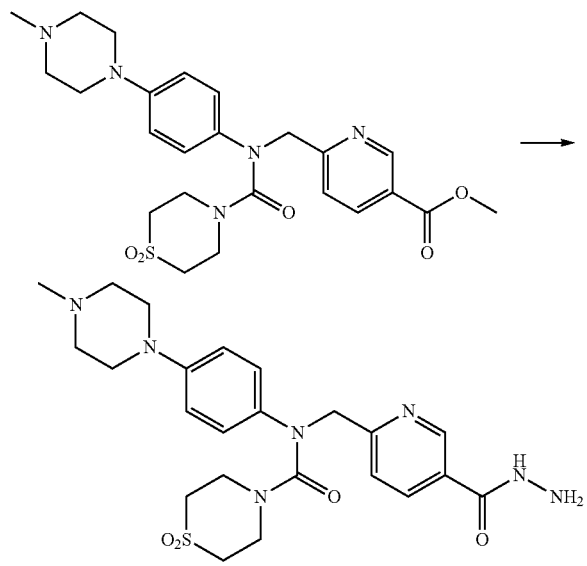

Methyl 6-((N-(4-(4-methylpiperazin-1-yl)phenyl)-1,1-dioxidothiomorpholine-4-carboxamido) methyl)nicotinate (0.128 g, 0,255 mmol) and hydrazine monohydrate (0.124 mL, 2.552 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=5% to 15%) to give N-((5-(hydrazinecarbonyl)pyridin-2-yl)methyl)-N-(4-(4-methylpiperazin-1-yl)phenyl)thiomorpholine-4-carboxamide 1,1-dioxide as brown oil (0.072 g, 56.3%).

[Step 5] Compound 21628

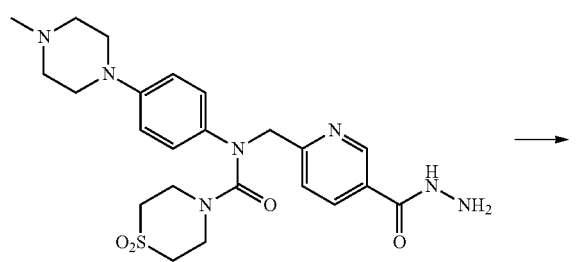

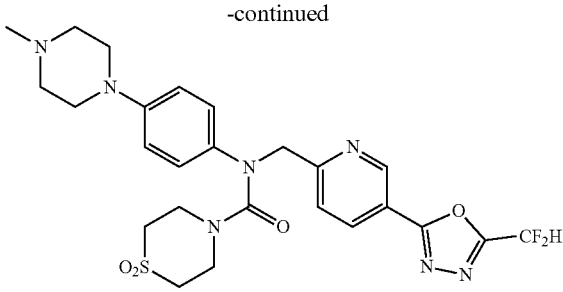

N-((5-(hydrazinecarbonyl)pyridin-2-yl)methyl)-N-(4-(4-methylpiperazin-1-yl)phenyl)thiomorpholine-4-carboxamide 1,1-dioxide (0.072 g, 0.144 mmol), triethylamine (0.100 mL, 0.719 mmol) and 2,2-difluoroacetic anhydride (0.047 mL, 0.431 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove, the solid residues and aqueous layer, and the organic layer collected was concentrated in vacuo. The residue was chromatographed (SiO$_2$, 4 g cartridge; methanol/dichloromethane=0% to 3%) to give N-((5-(5-(difluoromethyl)-1,3,4-oxadiazol-2-yl)pyridin-2-yl)methyl)-N-(4-(4-methylpiperazin-1-yl)phenyl)thiomorpholine-4-carboxamide 1,1-dioxide as brown foam (0.006 g, 7.7%).

$^1$H NMR (400 MHz, CDCl$_3$) δ 9.26 (dd, 1H, J=2.3, 0.9 Hz), 8.39 (dd, 1H, J=8.2, 2.2 Hz), 7.55 (dd, 1H, J=8.2, 0.9 Hz), 7.24 (t, 1H, J=8.1 Hz), 6.90 (d, 1H, J=51.7 Hz), 6.81-6.63 (m, 3H), 5.09 (s, 2H), 3.82-3.68 (m, 4H), 3.29 (t, 4H, J=5.0 Hz), 2.96 (t, 4H, J=5.3 Hz), 2.77 (s, 4H), 2.50 (s, 3H); LRMS (ES) m/z 562.3 (M$^+$+1).

Example 242. Compound 21629: N-(3-chloro-4-fluorophenyl)-N-((5-(5-(difluoromethyl)-1,3,4-oxadiazol-2-yl)pyridin-2-yl)methyl)-4-ethylpiperazine-1-carboxamide

[Step 1] N-(3-chloro-4-fluorophenyl)-4-ethylpiperazine-1-carboxamide

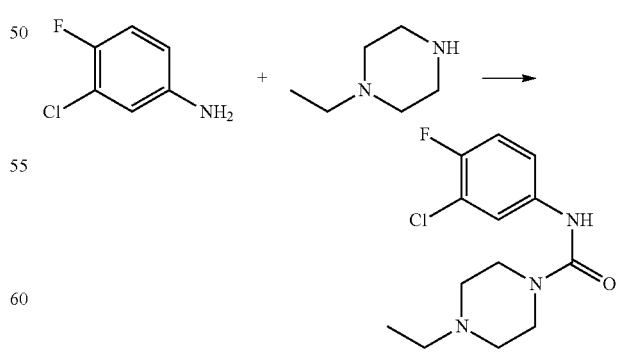

A solution of 3-chloro-4-fluoroaniline (0.500 g, 3.435 mmol), 1,1'-carbonyldiimidazole (0.613 g, 3.779 mmol) and triethylamine (0.575 mL, 4.122 mmol) in acetonitrile (10 mL) was mixed at the room temperature with 1-ethylpiperazine (0.458 mL, 3.607 mmol). The reaction mixture was stirred at the same temperature for 18 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; methanol/dichloromethane=0% to 5%) to give N-(3-chloro-4-fluorophenyl)-4-ethylpiperazine-1-carboxamide as purple solid (0.410 g, 41.8%).

[Step 2] Methyl 6-((N-(3-chloro-4-fluorophenyl)-4-ethylpiperazine-1-carboxamido)methyl)nicotinate

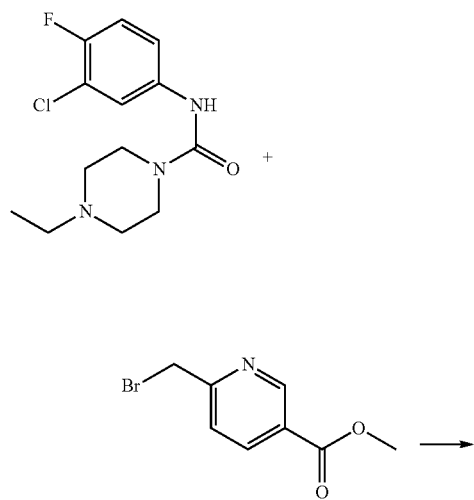

To a stirred solution of N-(3-chloro-4-fluorophenyl)-4-ethylpiperazine-1-carboxamide (0.410 g, 1.435 mmol) in N,N-dimethylformide (10 mL) was added at 0° C. sodium hydride (60.00%, 0.069 g, 1.722 mmol). The reaction mixture was stirred at the same temperature, added at the room temperature with methyl 6-(bromomethyl)nicotinate (0.363 g, 1.578 mmol), and stirred at the room temperature for additional 3 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; methanol/dichloromethane=0% to 5%) to give methyl 6-((N-(3-chloro-4-fluorophenyl)-4-ethylpiperazine-1-carboxamido)methyl)nicotinate as brown oil (0.190 g, 30.4%).

[Step 3] N-(3-chloro-4-fluorophenyl)-4-ethyl-N-((5-(hydrazinecarbonyl)pyridin-2-yl)methyl)piperazine-1-carboxamide

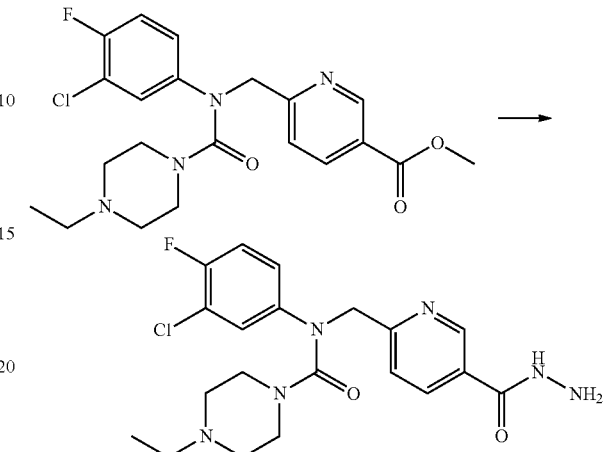

A mixture of methyl 6-((N-(3-chloro-4-fluorophenyl)-4-ethylpiperazine-1-carboxamido)methyl)nicotinate (0.190 g, 0.437 mmol) and hydrazine monohydrate (0.425 mL, 8.738 mmol) in ethanol (5 mL) was heated at reflux for 16 hr, and cooled down to the ambient temperature, concentrated under the reduced pressure. Then, water was added to the reaction mixture, followed by extraction with ethyl acetate. The organic layer was washed with aqueous saturated sodium chloride solution, dried (anhydrous MgSO$_4$), filtered, and concentrated in vacuo. The crude N-(3-chloro-4-fluorophenyl)-4-ethyl-N-((5-(hydrazinecarbonyl)pyridin-2-yl)methyl)piperazine-1-carboxamide was used without further purification (0.039 g, 20.5%, yellow solid).

[Step 4] N-(3-chloro-4-fluorophenyl)-N-((5-(2-(2,2-difluoroacetyl)hydrazine-1-carbonyl)pyridin-2-yl)methyl)-4-ethylpiperazine-1-carboxamide

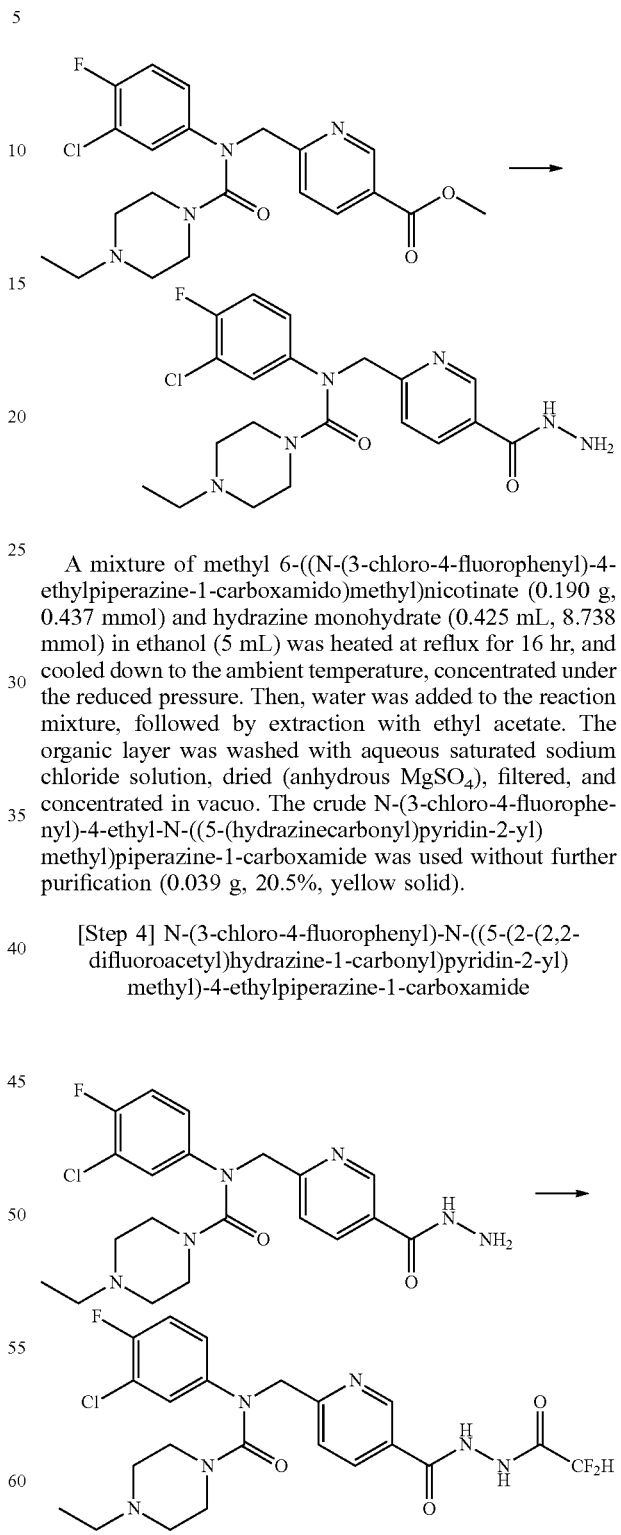

A solution of N-(3-chloro-4-fluorophenyl)-4-ethyl-N-((5-(hydrazinecarbonyl)pyridin-2-yl)methyl)piper azine-1-carboxamide (0.039 g, 0.090 mmol) and N,N-diisopropylethylamine (0.023 mL, 0.135 mmol) in dichloromethane (1 mL) was mixed at 0° C. with 2,2-difluoroacetic anhydride (0.020 mL, 0.179 mmol), and stirred at the room temperature for 16 hr. Then, water was added to the reaction mixture, followed by extraction with dichloromethane. The organic layer was washed with aqueous saturated sodium chloride solution, dried (anhydrous MgSO₄), filtered, and concentrated in vacuo. The crude N-(3-chloro-4-fluorophenyl)-N-((5-(2-(2,2-difluoroacetyl)hydrazine-1-carbonyl)pyridin-2-yl)methyl)-4-ethylpiperazine-1-carboxamide was used without further purification (0.021 g, 45.7%, yellow oil).

[Step 5] Compound 21629

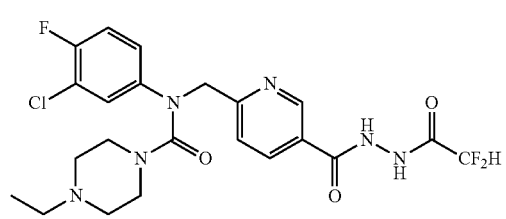

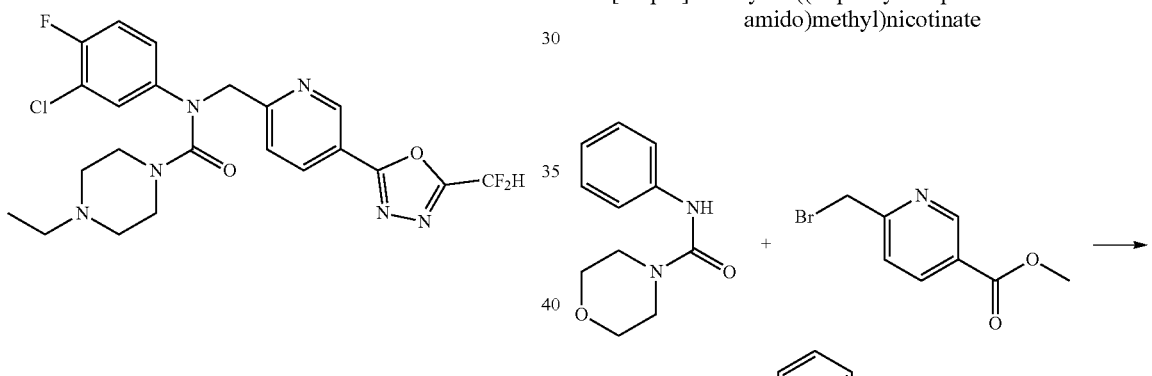

A mixture of N-(3-chloro-4-fluorophenyl)-N-((5-(2-(2,2-difluoroacetyl)hydrazine-1-carbonyl)pyridin-2-yl)methyl)-4-ethylpiperazine-1-carboxamide (0.021 g, 0.041 mmol) and 1-methoxy-N-triethylammoniosulfonyl-methanimidate (Burgess reagent, 0.047 g, 0.363 mmol) in tetrahydrofuran (1 mL) was heated at reflux for 16 hr, and cooled down to the ambient temperature and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(3-chloro-4-fluorophenyl)-N-((5-(5-(difluoromethyl)-1,3,4-oxadiazol-2-yl)pyridin-2-yl)methyl)-4-ethylpiperazine-1-carboxamide as white solid (0.007 g, 32.1%).

¹H NMR (400 MHz, CDCl₃) δ 9.23-9.22 (m, 1H), 8.34 (dd, J=8.2, 2.2 Hz, 1H), 7.59-7.56 (m, 1H), 7.26-7.23 (m, 1H), 7.08-6.80 (m, 3H), 5.04 (s, 2H), 3.36-3.35 (m, 4H), 2.45-2.39 (m, 6H), 1.10 (t, J=7.1 Hz, 3H); LRMS (ES) m/z 495.2 (M⁺+1).

Example 243. Compound 21630: N-((5-(5-(difluoromethyl)-1,3,4-oxadiazol-2-yl)pyridin-2-yl)methyl)-N-phenylmorpholine-4-carboxamide

[Step 1] N-phenylmorpholine-4-carboxamide

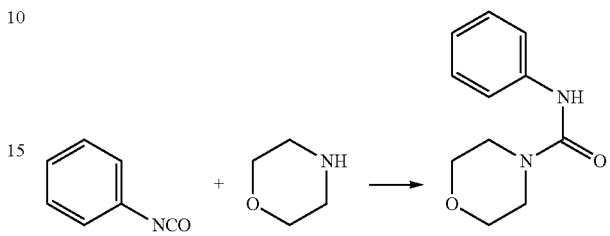

A solution of isocyanatobenzene (1.000 g, 8.395 mmol) and morpholine (0.726 mL, 8.395 mmol) in diethylether (20 mL) was stirred at the room temperature for 18 hr. The precipitates were collected by filtration, washed by diethylether, and dried to give N-phenylmorpholine-4-carboxamide as white solid (1.717 g, 99.2%).

[Step 2] Methyl 6-((N-phenylmorpholine-4-carboxamido)methyl)nicotinate

To a stirred solution of N-phenylmorpholine-4-carboxamide (0.200 g, 0.970 mmol) in N,N-dimethylformamide (5 mL) was added at 0° C. sodium hydride (60.00%, 0.039 g, 0.970 mmol). The reaction mixture was stirred at the same temperature for 1 hr, added at the same temperature with methyl 6-(bromomethyl)nicotinate (0.223 g, 0.970 mmol), and stirred for additional 2 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 4 g cartridge; methanol/dichloromethane=0% to 5%) to give methyl 6-((N-phenylmorpholine-4-carboxamido)methyl)nicotinate as brown oil (0.294 g, 85.4%).

[Step 3] N-((5-(hydrazinecarbonyl)pyridin-2-yl)methyl)-N-phenylmorpholine-4-carboxamide

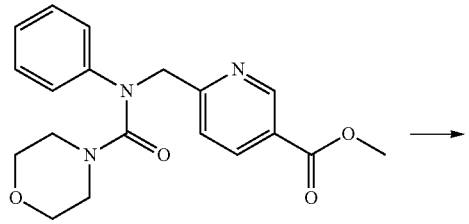

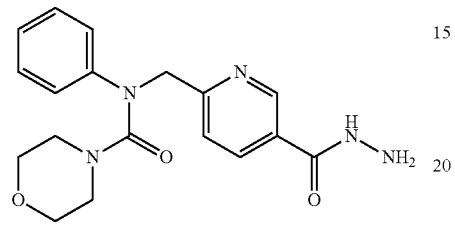

Methyl 6-((N-phenylmorpholine-4-carboxamido)methyl)nicotinate (0.294 g, 0.828 mmol) and hydrazine monohydrate (0.403 mL, 8.284 mmol) were mixed at the room temperature in ethanol (2 mL) and then stirred at 110° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=5% to 15%) to give N-((5-(hydrazinecarbonyl)pyridin-2-yl)methyl)-N-phenylmorpholine-4-carboxamide as brown oil (0.294 g, 100.0%).

[Step 4] N-((5-(2-(2,2-difluoroacetyl)hydrazine-1-carbonyl)pyridin-2-yl)methyl)-N-phenylmorpholine-4-carboxamide

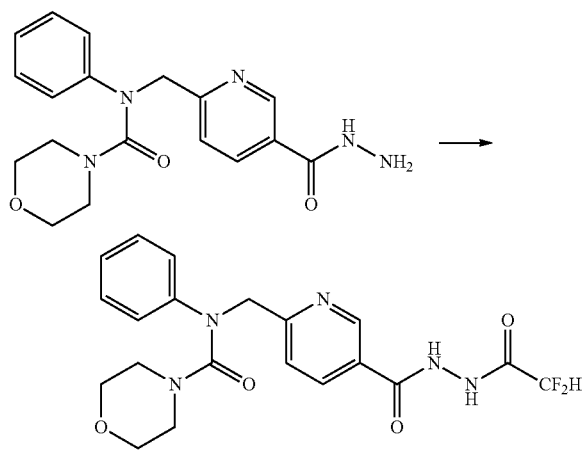

N-((5-(hydrazinecarbonyl)pyridin-2-yl)methyl)-N-phenylmorpholine-4-carboxamide (0.294 g, 0.828 mmol), triethylamine (0.577 mL, 4.142 mmol) and 2,2-difluoroacetic anhydride (0.270 mL, 2.485 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-((5-(2-(2,2-difluoroacetyl)hydrazine-1-carbonyl)pyridin-2-yl)methyl)-N-phenylmorpholine-4-carboxamide as yellow solid (0.130 g, 44.2%).

[Step 5] Compound 21630

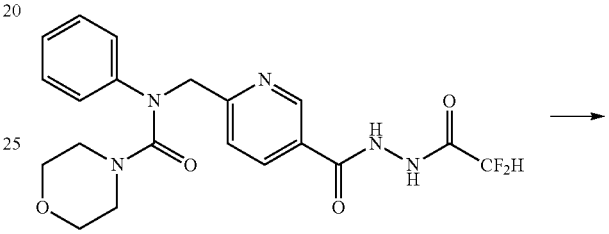

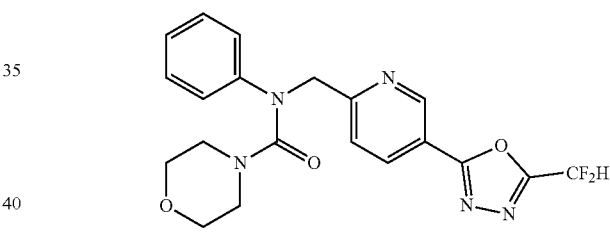

N-((5-(2-(2,2-difluoroacetyl)hydrazine-1-carbonyl)pyridin-2-yl)methyl)-N-phenylmorpholine-4-carboxamide (0.130 g, 0.300 mmol) and 1-methoxy-N-triethylammoniosulfonyl-methanimidate (Burgess reagent, 0.107 g, 0.450 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-((5-(5-(difluoromethyl)-1,3,4-oxadiazol-2-yl)pyridin-2-yl)methyl)-N-phenylmorpholine-4-carboxamide as yellow oil (0.089 g, 71.0%).

$^1$H NMR (400 MHz, CDCl$_3$) δ 9.24 (dd, 1H, J=2.2, 0.8 Hz), 8.37 (dd, 1H, J=8.2, 2.2 Hz), 7.66 (dd, 1H, J=8.2, 0.8 Hz), 7.39-7.30 (m, 2H), 7.24-7.17 (m, 2H), 7.15-7.09 (m, 1H), 7.01 (t, 1H, J=51.7 Hz), 5.15 (s, 2H), 3.53 (dd, 4H, J=5.6, 4.0 Hz), 3.28 (dd, 4H, J=5.6, 4.0 Hz); LRMS (ES) m/z 416.1 (M$^+$+1).

Example 244: Compound 21631: N-((5-(5-(difluoromethyl)-1,3,4-oxadiazol-2-yl)pyridin-2-yl)methyl)-N-(4-phenoxyphenyl)thiomorpholine-4-carboxamide 1,1-dioxide

[Step 1] N-(4-phenoxyphenyl)thiomorpholine-4-carboxamide 1,1-dioxide

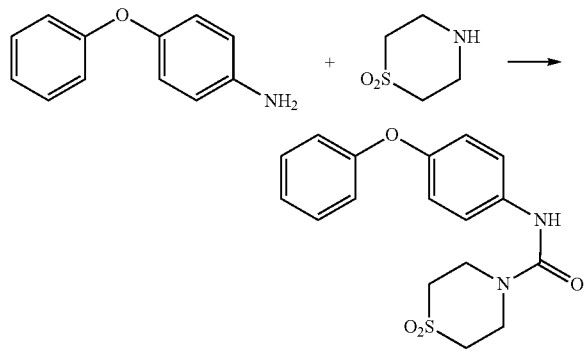

To a stirred solution of 4-phenoxyaniline (0.300 g, 1.620 mmol) and N,N-diisopropylethylamine (1.693 mL, 9.718 mmol) in dichloromethane (20 mL) was added at 0° C. triphosgene (0.240 g, 0.810 mmol). The reaction mixture was stirred at the same temperature, added at the room temperature with thiomorpholine 1,1-dioxide (0.219 g, 1.620 mmol), and stirred for additional 2 hr. Then, water was added to the reaction mixture, followed by extraction with dichloromethane. The organic layer was washed with aqueous saturated sodium chloride solution, dried (anhydrous MgSO₄), filtered, and concentrated in vacuo. The residue was diluted with diethylether (20 mL) and stirred at the ambient temperature. The resulting precipitates were collected by filtration, washed by diethylether, and dried to give N-(4-phenoxyphenyl)thiomorpholine-4-carboxamide 1,1-dioxide as brown solid (0.319 g, 56.9%).

[Step 2] Methyl 6-((1,1-dioxido-N-(4-phenoxyphenyl)thiomorpholine-4-carboxamido)methyl)nicotinate

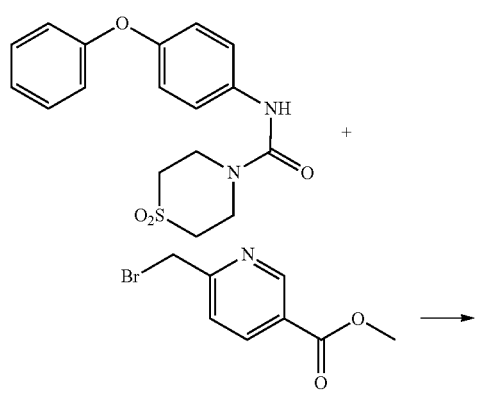

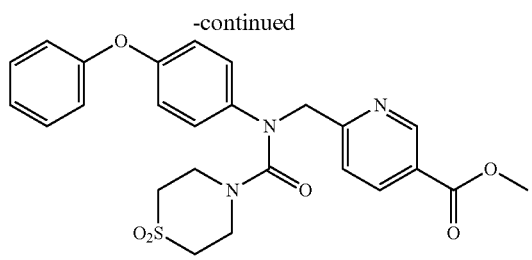

To a stirred solution of N-(4-phenoxyphenyl)thiomorpholine-4-carboxamide 1,1-dioxide (0.319 g, 0.921 mmol) in N,N-dimethylformamide (2 mL) was added at 0° C. sodium hydride (60.00%, 0.037 g, 0.921 mmol). The reaction mixture was stirred at the same temperature for 1 hr, added at the same temperature with methyl 6-(bromomethyl)nicotinate (0.212 g, 0.921 mmol), and stirred for additional 3 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 4 g cartridge; methanol/dichloromethane=0% to 5%) to give methyl 6-((1,1-dioxido-N-(4-phenoxyphenyl)thiomorpholine-4-carboxamido)methyl)nicotinat e as brown oil (0.372 g, 81.5%).

[Step 3] N-((5-(hydrazinecarbonyl)pyridin-2-yl)methyl)-N-(4-phenoxyphenyl)thiomorpholine-4-carboxamide 1,1-dioxide

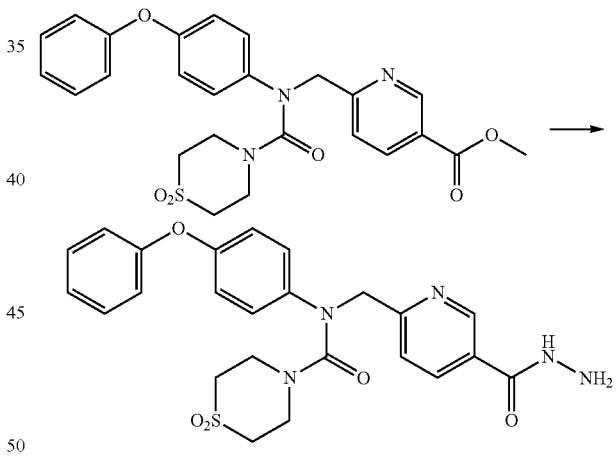

Methyl 6-((1,1-dioxido-N-(4-phenoxyphenyl)thiomorpholine-4-carboxamido)methyl)nicotinat e (0.372 g, 0.750 mmol) and hydrazine monohydrate (0.365 mL, 7.503 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=5% to 10%) to give N-((5-(hydrazinecarbonyl)pyridin-2-yl)methyl)-N-(4-phenoxyphenyl)thiomorpholine-4-carboxamide 1,1-dioxide as brown foam (0.203 g, 54.6%).

801

[Step 4] Compound 21631

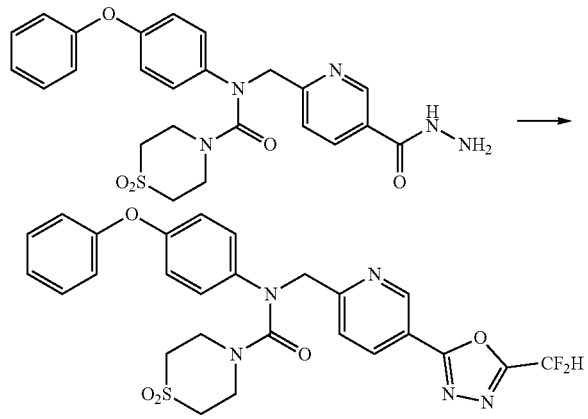

N-((5-(hydrazinecarbonyl)pyridin-2-yl)methyl)-N-(4-phenoxyphenyl)thiomorpholine-4-carboxamide 1,1-dioxide (0.203 g, 0.410 mmol), triethylamine (0.285 mL, 2.048 mmol) and 2,2-difluoroacetic anhydride (0.134 mL, 1.229 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water Was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=10% to 30%) to give ((5-(5-(difluoromethyl)-1,3,4-oxadiazol-2-yl)pyridin-2-yl)methyl)-N-(4-phenoxyphenyl)thiomorpholine-4-carboxamide 1,1-dioxide as brown foam (0.196 g, 86.3%).

$^1$H NMR (400 MHz, CDCl$_3$) δ 9.25 (dd, 1H, J=2.2, 0.8 Hz), 8.40 (dd, 1H, J=8.2, 2.2 Hz), 7.56 (dd, 1H; J=8.2, 0.8 Hz), 7.44-7.30 (m, 2H), 7.20-7.12 (m, 3H), 7.08-6.79 (m, 5H), 5.07 (s, 2H), 3.77-3.69 (m, 4H), 3.00-2.92 (m, 4H); LRMS (ES) m/z 556.2 (M$^+$+1).

Example 245. Compound 21632: N-((5-(5-(difluoromethyl)-1,3,4-oxadiazol-2-yl)pyridin-2-yl)methyl)-4-methyl-N-(o-tolyl)piperazine-1-carboxamide

[Step 1] Methyl 6-((4-methyl-N-(o-tolyl)piperazine-1-carboxamido)methyl)nicotinate

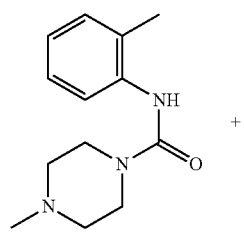

802

-continued

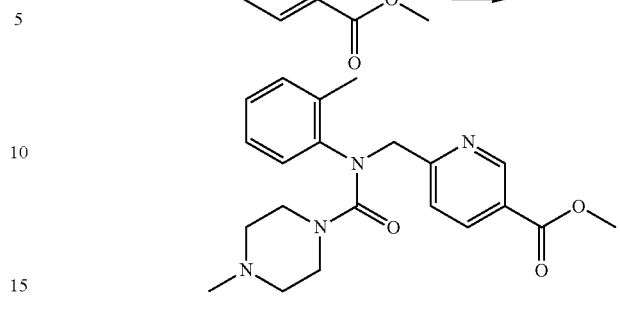

To a stirred solution of 4-methyl-N-(o-tolyl)piperazine-1-carboxamide (0.480 g, 2.057 mmol) in N,N-dimethylformamide (5 mL) was added at 0° C. sodium hydride (60.00%, 0.082 g, 2.057 mmol). The reaction mixture was stirred at the same temperature for 1 hr, added at the same temperature with methyl 6-(bromomethyl)nicotinate (0.473 g, 2.057 mmol), and stirred for additional 3 hr. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 4 g cartridge; methanol/dichloromethane=0% to 5%) to give methyl 6-((4-methyl-N-(o-tolyl)piperazine-1-carboxamido)methyl)nicotinate as white foam (0.335 g, 42.6%).

[Step 2] N-((5-(hydrazinecarbonyl)pyridin-2-yl)methyl)-4-methyl-N-(o-tolyl)piperazine-1-carboxamide

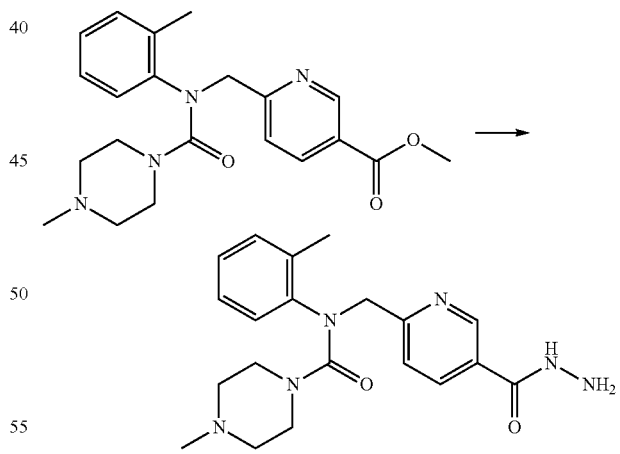

Methyl 6-((4-methyl-N-(o-tolyl)piperazine-1-carboxamido)methyl)nicotinate (0.335 g, 0.876 mmol) and hydrazine monohydrate (0.426 mL, 8.759 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-((5-(hydrazinecarbonyl)pyridin-2-yl)methyl)-4-methyl-N-(o-tolyl)piperazine-1-carboxamide as yellow foam (0.284 g, 84.8%).

[Step 3] Compound 21632

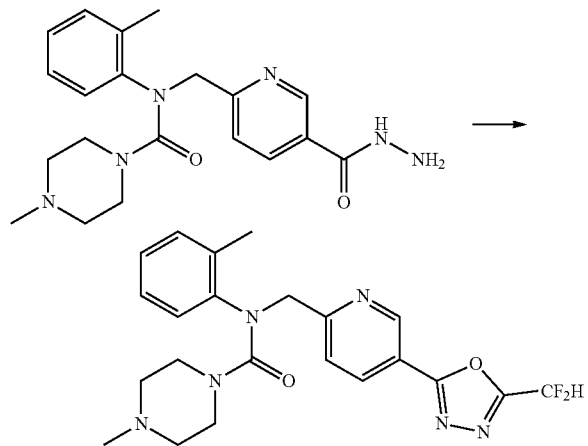

N-((5-(hydrazinecarbonyl)pyridin-2-yl)methyl)-4-methyl-N-(o-tolyl)piperazine-1-carboxamide (0.142 g, 0.371 mmol), triethylamine (0.259 mL, 1.856 mmol) and 2,2-difluoroacetic anhydride (0.121 mL, 1.114 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 3%) to give N-((5-(5-(difluoromethyl)-1,3,4-oxadiazol-2-yl)pyridin-2-yl)methyl)-4-methyl-N-(o-tolyl) piperazine-1-carboxamide as orange foam (0.057 g, 34.5%).

¹H NMR (400 MHz, CDCl₃) δ 9.22 (dd, 1H, J=2.2, 0.8 Hz), 8.37 (dd, 1H, J=8.2, 2.2 Hz), 7.70 (dd, 1H, J=8.2, 0.8 Hz), 7.28-7.10 (m, 4H), 7.08 (t, 1H), 4.93 (s, 2H), 3.30 (t, 4H, J=5.1 Hz), 2.33-2.28 (m, 6H), 2.26 (s, 4H); LRMS (ES) m/z 443.4 (M++1).

Example 246. Compound 21633: 4-Methyl-N-(o-tolyl)-N-((5-(5-(trifluoromethyl)-1,3,4-oxadiazol-2-yl)pyridin-2-yl)methyl)piperazine-1-carboxamide

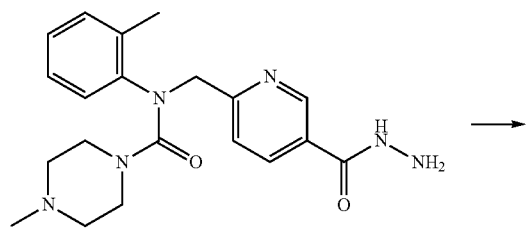

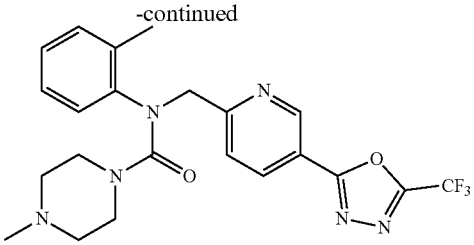

N-((5-(hydrazinecarbonyl)pyridin-2-yl)methyl)-4-methyl-N-(o-tolyl)piperazine-1-carboxamide (0.142 g, 0.371 mmol), triethylamine (0.259 mL, 1.856 mmol) and trifluoroacetic anhydride (0.157 mL, 1.114 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 3%) to give 4-methyl-N-(o-tolyl)-N-((5-(5-(trifluoromethyl)-1,3,4-oxadiazol-2-yl)pyridin-2-yl)methyl) piperazine-1-carboxamide as yellow foam (0.129 g, 75.2 To).

¹H NMR (400 MHz, CDCl₃) δ 9.22-9.21 (m, 1H), 8.37 (dd, 1H, J=8.2, 2.3 Hz), 7.71 (d, 1H, J=8.2 Hz), 7.26-7.23 (m, 1H), 7.19-7.11 (m, 3H), 4.92 (s, 2H), 3.27 (t, 4H, J=4.8 Hz), 2.27-2.26 (m, 10H); LRMS (ES) m/z 461.4 (M⁺+1).

Example 247. Compound 21634: N-(2-fluorophenyl)-4-methyl-N-((5-(5-(trifluoromethyl)-1,3,4-oxadiazol-2-yl)pyridin-2-yl)methyl)piperazine-1-carboxamide

[Step 1] Methyl 6-((N-(2-fluorophenyl)-4-methylpiperazine-1-carboxamido)methyl)nicotinate

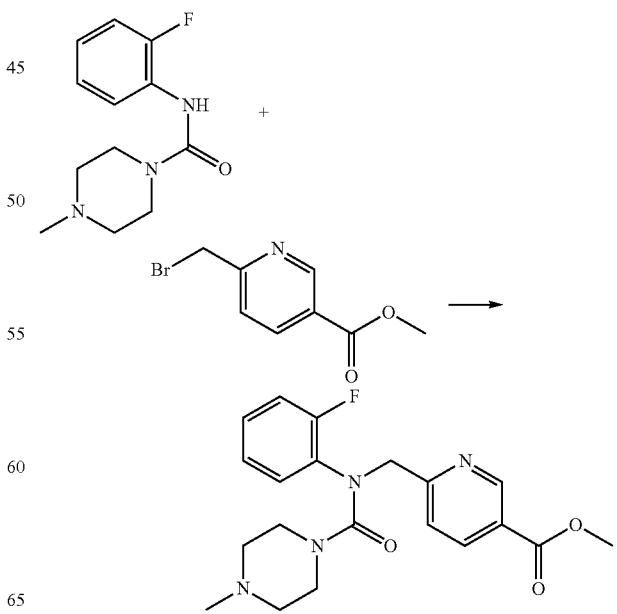

To a stirred solution of N-(2-fluorophenyl)-4-methylpiperazine-1-carboxamide (0.380 g, 1.601 mmol) in N,N-dimethylformamide (5 mL) was added at 0° C. sodium hydride (60.00%, 0.064 g, 1.601 mmol). The reaction mixture was stirred at the same temperature for 1 hr, added at the same temperature with methyl 6-(bromomethyl)nicotinate (0.368 g, 1.601 mmol), and stirred for additional 3 hr, and Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 4 g cartridge; methanol/dichloromethane=0% to 5%) to give methyl 6-((N-(2-fluorophenyl)-4-methylpiperazine-1-carboxamido)methyl)nicotinate as white foam (0.405 g, 65.4%).

[Step 2] N-(2-fluorophenyl)-N-((5-(hydrazinecarbonyl)pyridin-2-yl)methyl)-4-methylpiperazine-1-carboxamide

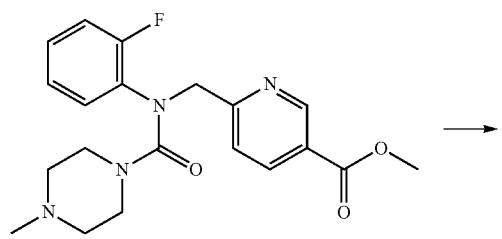

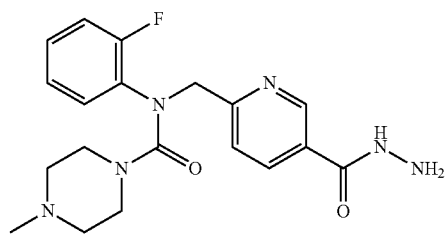

Methyl 6-((N-(2-fluorophenyl)-4-methylpiperazine-1-carboxamido)methyl)nicotinate (0.405 g, 1.048 mmol) and hydrazine monohydrate (0.509 mL, 10.481 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(2-fluorophenyl)-N-((5-(hydrazinecarbonyl)pyridin-2-yl)methyl)-4-methylpiperazine-1-carboxamide as yellow oil (0.223 g, 55.0%).

[Step 3] N-(2-fluorophenyl)-4-methyl-N-((5-(2-(2,2,2-trifluoroacetyl)hydrazine-1-carbonyl)pyridin-2-yl)methyl)piperazine-1-carboxamide

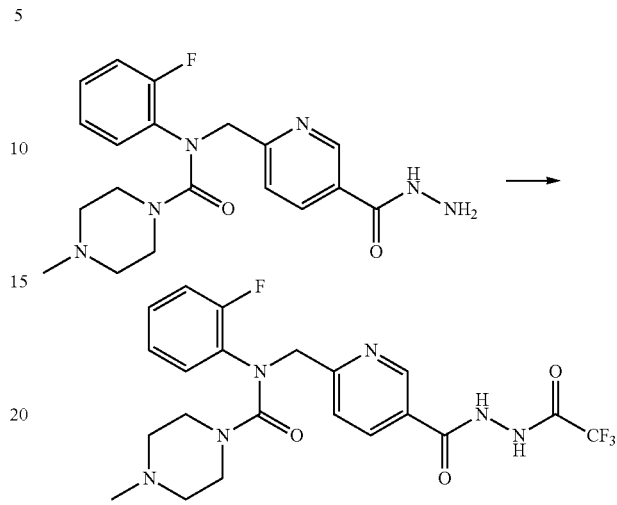

N-(2-fluorophenyl)-N-((5-(hydrazinecarbonyl)pyridin-2-yl)methyl)-4-methylpiperazine-1-carboxamide (0.111 g, 0.287 mmol), triethylamine (0.200 mL, 1.436 mmol) and trifluoroacetic anhydride (0.122 mL, 0.862 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(2-fluorophenyl)-4-methyl-N-((5-(2-(2,2,2-trifluoroacetyl)hydrazine-1-carbonyl)pyridin-2-yl)methyl)piperazine-1-carboxamide as yellow oil (0.076 g, 54.8%).

[Step 4] Compound 21634

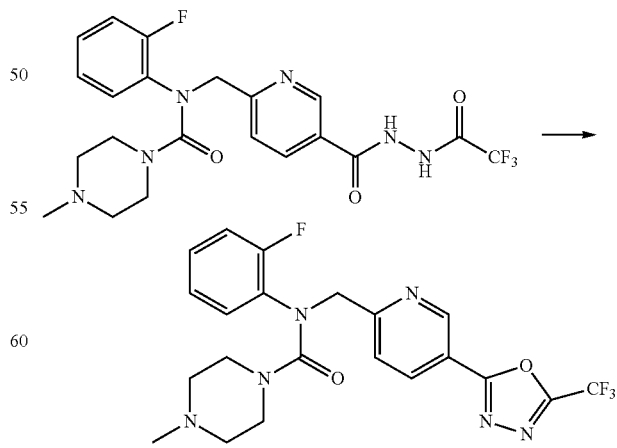

N-(2-fluorophenyl)-4-methyl-N-((5-(2-(2,2,2-trifluoroacetyl)hydrazine-1-carbonyl)pyridin-2-yl)methyl)piperazine-1-carboxamide (0.076 g, 0.158 mmol) and 1-methoxy-N-triethylammoniosulfonyl-methanimidate (Burgess reagent, 0.056 g, 0.236 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(2-fluorophenyl)-4-methyl-N-((5-(5-(trifluoromethyl)-1,3,4-oxadiazol-2-yl)pyridin-2-yl)methyl)piperazine-1-carboxamide as orange foam (0.052 g, 71.3%).

$^1$H NMR (400 MHz, CDCl$_3$) δ 9.21 (dd, 1H, J=2.3, 0.8 Hz), 8.37 (dd, 1H, J=8.2, 2.3 Hz), 7.71 (d, 1H, J=8.2 Hz), 7.24 (dd, 1H, J=6.4, 2.8 Hz), 7.25-7.09 (m, 3H), 4.92 (s, 2H), 3.27 (t, 4H, J=5.0 Hz), 2.34-2.19 (m, 10H); LRMS (ES) m/z 465.4 (M++1).

Example 248. Compound 21643: (S)—N-(3-chloro-2-fluorophenyl)-N-(4-(5-(difluoromethyl)-1,3,4-oxadiazol-2-yl)-2-fluorobenzyl)-3-(dimethylamino)pyrrolidine-1-carboxamide

[Step 1] Methyl 4-(((3-chloro-2-fluorophenyl)amino)methyl)-3-fluorobenzoate

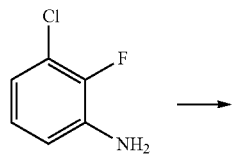

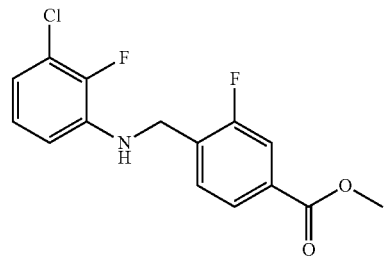

A solution of 2-chloro-3-fluoroaniline (1.000 g, 6.870 mmol), methyl 4-(bromomethyl)-3-fluorobenzoate (6.110 g, 24.732 mmol) and potassium carbonate (1.867 g, 7.557 mmol) in acetonitrile (10 mL) was stirred at the room temperature for 12 hr, and concentrated under the reduced pressure to remove the solvent. The residue was chromatographed (SiO$_2$, 40 g cartridge; ethyl acetate/hexane=0% to 10%) to give methyl 4-(((3-chloro-2-fluorophenyl)amino)methyl)-3-fluorobenzoate as pale yellow oil (0.950 g, 44.4%).

[Step 2] Methyl 4-(((3-chloro-2-fluorophenyl)((4-nitrophenoxy)carbonyl)amino)methyl)-3-fluorobenzoate

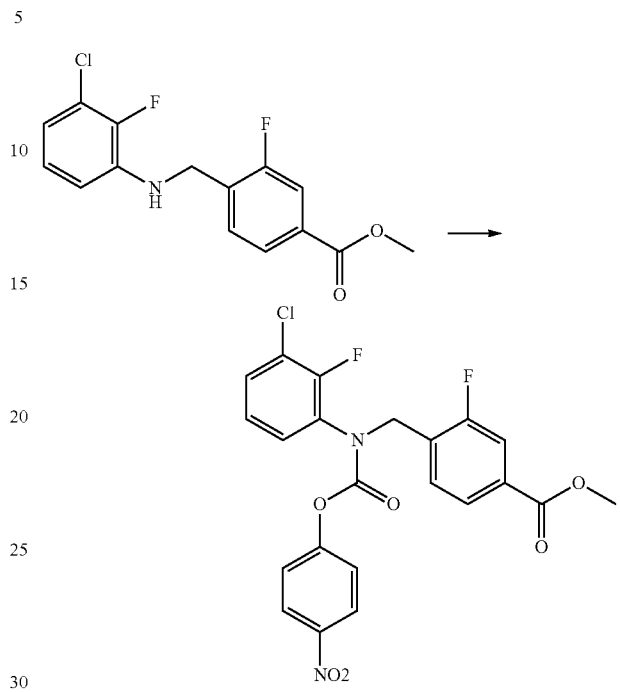

A solution of methyl 4-(((3-chloro-2-fluorophenyl)amino)methyl)-3-fluorobenzoate (1.000 g, 3.208 mmol), 4-nitrophenyl carbonochloridate (0.970 g, 4.812 mmol) and potassium carbonate (0.887 g, 6.416 mmol) in dichloromethane (10 mL) was stirred at the room temperature for 15 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 10%) to give methyl 4-(((3-chloro-2-fluorophenyl)((4-nitrophenoxy)carbonyl)amino)methyl)-3-fluorobenzoate product as pale yellow oil (0.754 g, 49.3%).

[Step 3] Methyl (S)-4-((N-(3-chloro-2-fluorophenyl)-3-(dimethylamino)pyrrolidine-1-carboxamido)methyl)-3-fluorobenzoate

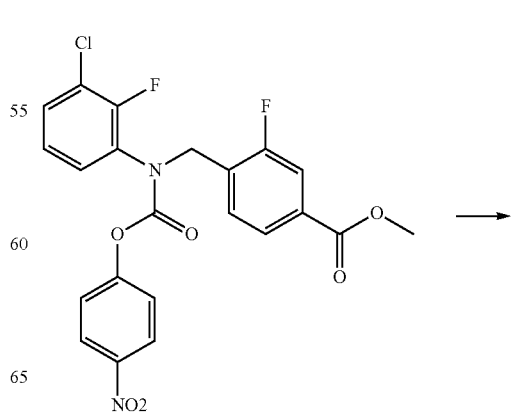

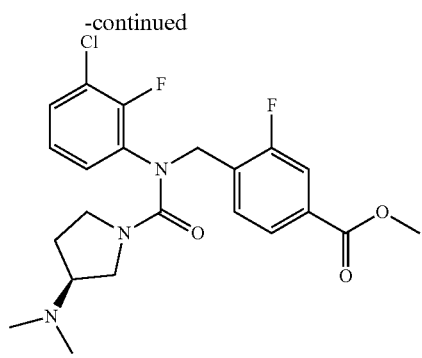

A solution of methyl 4-(((3-chloro-2-fluorophenyl)((4-nitrophenoxy)carbonyl)amino)methyl)-3-fluorobenzoate (0.300 g, 0.629 mmol), (S)—N,N-dimethylpyrrolidin-3-amine (0.216 g, 1.888 mmol) and potassium carbonate (0.435 g, 3.146 mmol) in N,N-dimethylformamide (5 mL) was stirred at 80° C. for 5 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 24 g cartridge; methanol/dichloromethane=0% to 10%) to give methyl (S)-4-((N-(3-chloro-2-fluorophenyl)-3-(dimethylamino)pyrrolidine-1-carboxamido)methyl)-3-fluorobenzoate as yellow oil (0.224 g, 78.8%).

[Step 4] (S)—N-(3-chloro-2-fluorophenyl)-3-(dimethylamino)-N-(2-fluoro-4-(hydrazinecarbonyl)benzyl)pyrrolidine-1-carboxamide

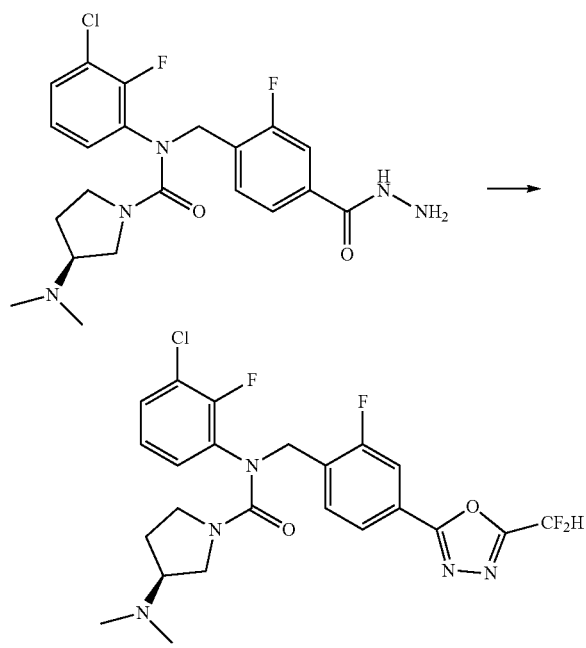

Methyl (S)-4-((N-(3-chloro-2-fluorophenyl)-3-(dimethylamino)pyrrolidine-1-carboxamido)methyl)-3-fluorobenzoate (0.202 g, 0.447 mmol) and hydrazine monohydrate (0.217 mL, 4.470 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give (S)—N-(3-chloro-2-fluorophenyl)-3-(dimethylamino)-N-(2-fluoro-4-(hydrazinecarbonyl)benzyl)pyrrolidine-1-carboxamide as yellow oil (0.193 g, 95.5%).

[Step 5] Compound 21643

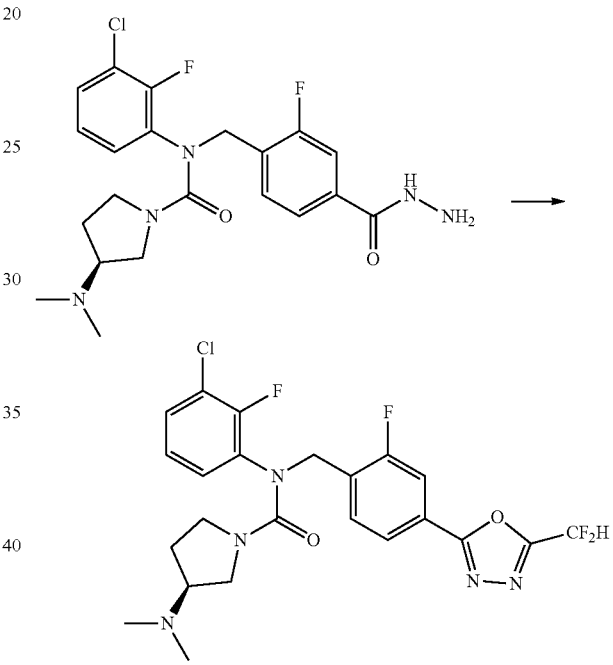

(S)—N-(3-chloro-2-fluorophenyl)-3-(dimethylamino)-N-(2-fluoro-4-(hydrazinecarbonyl)benzyl)pyrrolidine-1-carboxamide (0.096 g, 0.212 mmol), 2,2-difluoroacetic anhydride (0.069 mL, 0.637 mmol) and triethylamine (0.148 mL, 1.062 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give (S)—N-(3-chloro-2-fluorophenyl)-N-(4-(5-(difluoromethyl)-1,3,4-oxadiazol-2-yl)-2-fluorobenzyl)-3-(dimethylamino)pyrrolidine-1-carboxamide as yellow oil (0.039 g, 35.6%).

$^1$H NMR (400 MHz, CDCl$_3$) δ 7.92-7.81 (m, 2H), 7.69 (dd, 1H, J=10.0, 1.6 Hz), 7.33-7.24 (m, 1H), 7.08-6.77 (m, 3H), 4.92 (s, 2H), 3.53-3.43 (m, 1H), 3.34-3.24 (m, 1H), 3.12-3.00 (m, 1H), 2.97-2.88 (m, 1H), 2.74-2.69 (m, 1H), 2.26 (s, 6H), 2.01 (dt, 1H, J=12.4, 6.4 Hz), 1.82-1.72 (m, 1H); LRMS (ES) m/z 512.2 (M⁺+1).

Example 249. Compound 21644: (S)—N-(3-chloro-2-fluorophenyl)-3-(dimethylamino)-N-(2-fluoro-4-(5-(trifluoromethyl)-1,3,4-oxadiazol-2-yl)benzyl) pyrrolidine-1-carboxamide

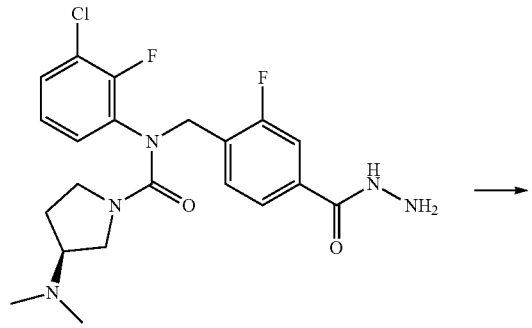

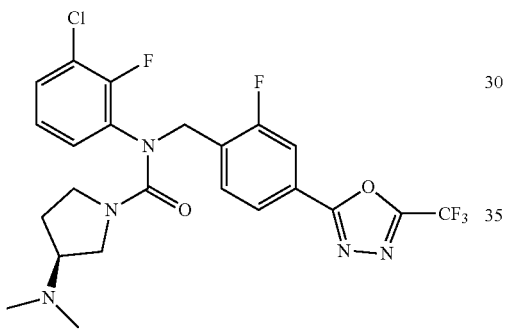

(S)—N-(3-chloro-2-fluorophenyl)-3-(dimethylamino)-N-(2-fluoro-4-(hydrazinecarbonyl)benzyl)pyrrolidine-1-carboxamide (0.096 g, 0.212 mmol), trifluoroacetic anhydride (0.090 mL, 0.617 mmol) and triethylamine (0.148 mL, 1.062 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 10%) to give (S)—N-(3-chloro-2-fluorophenyl)-3-(dimethylamino)-N-(2-fluoro-4-(5-(trifluoromethyl)-1,3,4-oxadiazol-2-yl)benzyl)pyrrolidine-1-carboxamide as yellow oil (0.025 g, 22.2%).

¹H NMR (400 MHz, CDCl₃) δ 7.92-7.82 (m, 2H), 7.74-7.66 (m, 1H), 7.30 (ddd, 1H, J=7.9, 6.6, 2.1 Hz), 7.08-6.95 (m, 2H), 4.93 (s, 2H), 3.55-3.46 (m, 1H), 3.31-3.26 (m, 1H), 3.12-2.94 (m, 2H), 2.79 (s, 2H), 2.30 (s, 6H), 2.08-2.00 (m, 2H), 1.33 (s, 1H), 1.27 (s, 1H); LRMS (ES) m/z 530.2 (M⁺+1).

Example 250. Compound 21645: (R)—N-(3-chloro-2-fluorophenyl)-3-(dimethylamino)-N-(2-fluoro-4-(5-(trifluoromethyl)-1,3,4-oxadiazol-2-yl)benzyl) pyrrolidine-1-carboxamide

[Step 1] Methyl 4-(((3-chloro-2-fluorophenyl) amino)methyl)-3-fluorobenzoate

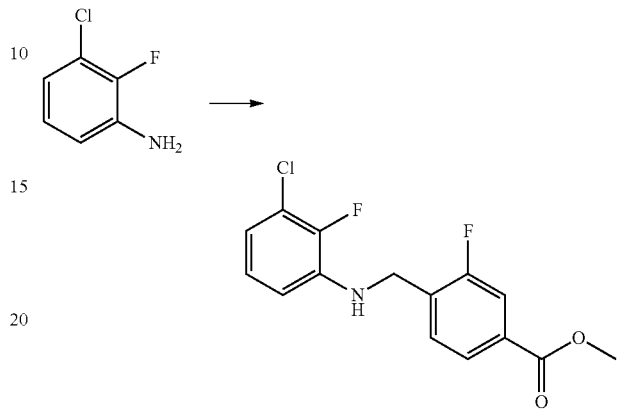

A solution of 2-chloro-3-fluoroaniline (1.000 g, 6.870 mmol), methyl 4-(bromomethyl)-3-fluorobenzoate (1.867 g, 7.557 mmol) and potassium carbonate (1.899 g, 13.74 mmol) in acetonitrile (10 mL) was stirred at the room temperature for 12 hr, filtered to remove solids, and concentrated under the reduced pressure. The residue was chromatographed (SiO₂, 40 g cartridge; ethyl acetate/hexane=0% to 10%) to give methyl 4-4-(3-chloro-2-fluorophenyl)amino)methyl)-3-fluorobenzoate as pale yellow oil (0.950 g, 44.4%).

[Step 2] Methyl 4-4-(3-chloro-2-fluorophenyl)((4-nitrophenoxy)carbonyl)amino)methyl)-3-fluorobenzoate

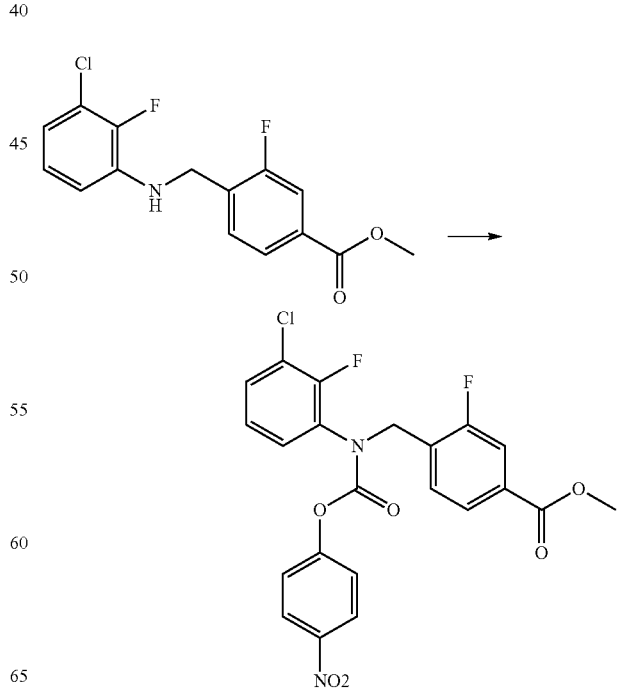

A solution of methyl 4-(((3-chloro-2-fluorophenyl)amino)methyl)-3-fluorobenzoate (1.000 g, 3.208 mmol), 4-nitrophenyl carbonochloridate (0.970 g, 4.812 mmol) and potassium carbonate (0.887 g, 6.416 mmol) in dichloromethane (10 mL) was stirred at the room temperature for 15 hr. Then, water was added to the reaction mixture, followed by extraction with dichloromethane. The organic layer was washed with aqueous saturated sodium chloride solution, dried (anhydrous MgSO₄), filtered, and concentrated in vacuo. The residue was chromatographed (SiO₂, 40 g cartridge; ethyl acetate/hexane=0% to 10%) to give methyl 4-(((3-chloro-2-fluorophenyl)((4-nitrophenoxy)carbonyl)amino)methyl)-3-fluorobenzoate as pale yellow oil (0.754 g, 49.3%).

[Step 3] Methyl (R)-4-((N-(3-chloro-2-fluorophenyl)-3-(dimethylamino)pyrrolidine-1-carboxamido)methyl)-3-fluorobenzoate

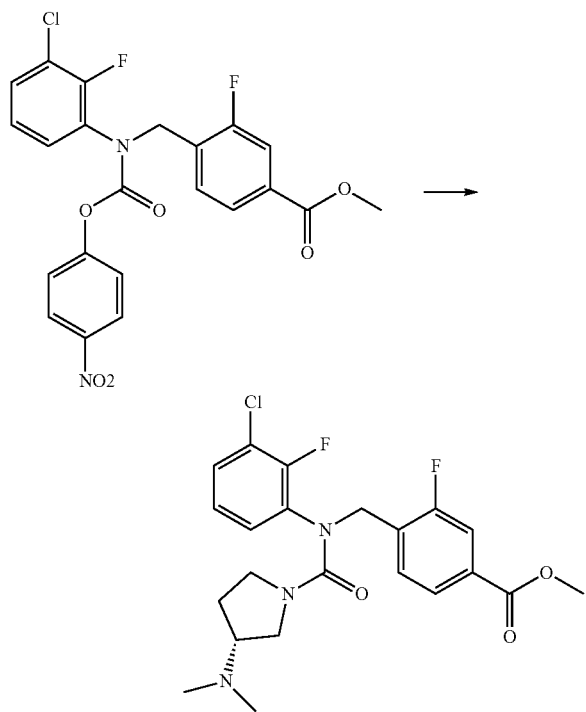

A solution of methyl 4-4-(3-chloro-2-fluorophenyl)((4-nitrophenoxy)carbonyl)amino)methyl)-3-fluorobenzoate (0.300 g, 0.629 mmol), (R)—N,N-dimethylpyrrolidin-3-amine (0.216 g, 1.888 mmol) and potassium carbonate (0.435 g, 3.146 mmol) in N,N-dimethylformamide (5 mL) was stirred at 80° C. for 5 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 24 g cartridge; methanol/dichloromethane=0% to 10%) to give methyl (R)-4-((N-(3-chloro-2-fluorophenyl)-3-(dimethylamino)pyrrolidine-1-carboxamido)methyl)-3-fluorobenzoate as yellow oil (0.201 g, 70.7%).

[Step 4] (R)—N-(3-chloro-2-fluorophenyl)-3-(dimethylamino)-N-(2-fluoro-4-(hydrazinecarbonyl)benzyl)pyrrolidine-1-carboxamide

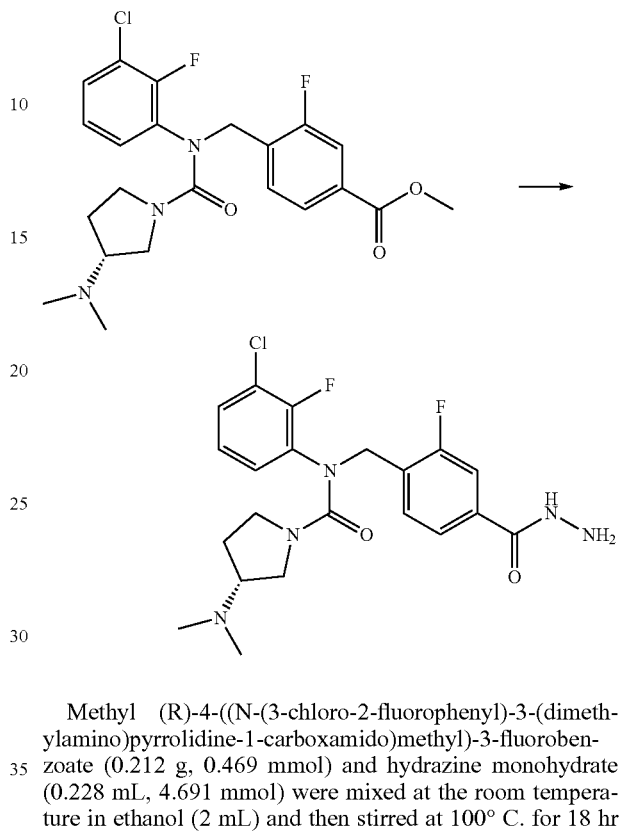

Methyl (R)-4-((N-(3-chloro-2-fluorophenyl)-3-(dimethylamino)pyrrolidine-1-carboxamido)methyl)-3-fluorobenzoate (0.212 g, 0.469 mmol) and hydrazine monohydrate (0.228 mL, 4.691 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 10%) to give (R)—N-(3-chloro-2-fluorophenyl)-3-(dimethylamino)-N-(2-fluoro-4-(hydrazinecarbonyl)benzyl)pyrrolidine-1-carboxamide as yellow oil (0.201 g, 94.8%).

[Step 5] Compound 21645

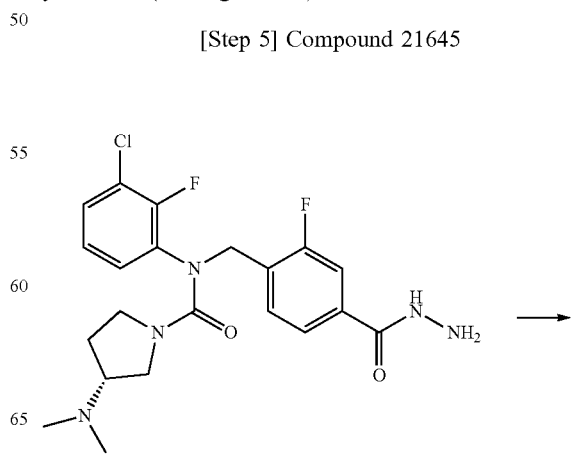

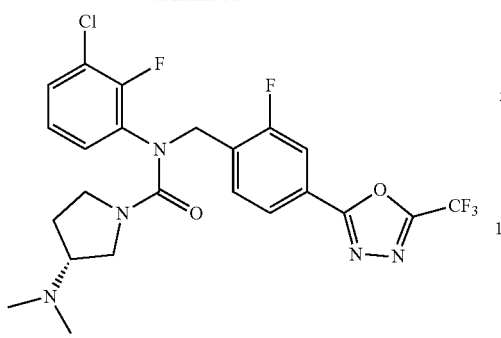

(R)—N-(3-chloro-2-fluorophenyl)-3-(dimethylamino)-N-(2-fluoro-4-(hydrazinecarbonyl)benzyl)pyrrolidine-1-carboxamide (0.101 g, 0.222 mmol), trifluoroacetic anhydride (0.094 mL, 0.667 mmol) and triethylamine (0.155 mL, 1.112 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give (R)—N-(3-chloro-2-fluorophenyl)-3-(dimethylamino)-N-(2-fluoro-4-(5-(trifluoromethyl)-1,3,4-oxadiazol-2-yl)benzyl)pyrrolidine-1-carboxamide as yellow oil (0.088 g, 74.6%).

$^1$H NMR (400 MHz, CDCl$_3$) δ 7.92-7.82 (m, 2H), 7.74-7.66 (m, 1H), 7.29 (ddd, 1H, J=7.9, 6.6, 2.1 Hz), 7.08-6.94 (m, 2H), 4.93 (s, 2H), 3.53-3.44 (m, 1H), 3.35-3.25 (m, 1H), 3.12-3.00 (m, 1H), 2.95 (s, 1H), 2.76 (s, 1H), 2.29 (s, 6H), 2.08-1.98 (m, 1H), 1.83-1.73 (m, 1H); LRMS (ES) m/z 530.2 (M$^+$+1).

Example 251. Compound 21646: N-(3-chloro-2-fluorophenyl)-N-(4-(5-(difluoromethyl)-1,3,4-oxadiazol-2-yl)-2-fluorobenzyl)-4-ethylpiperazine-1-carboxamide

[Step 1] N-(3-chloro-2-fluorophenyl)-4-ethyl-N-(2-fluoro-4-(hydrazinecarbonyl)benzyl)piperazine-1-carboxamide

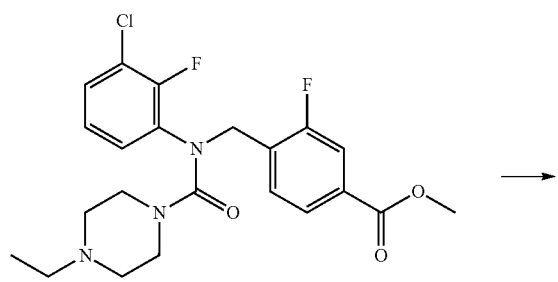

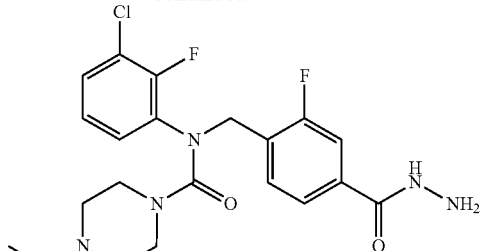

Methyl 4-((N-(3-chloro-2-fluorophenyl)-4-ethylpiperazine-1-carboxamido)methyl)-3-fluorobenzoate (0.079 g, 0.175 mmol) and hydrazine monohydrate (0.085 mL, 1.748 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(3-chloro-2-fluorophenyl)-4-ethyl-N-(2-fluoro-4-(hydrazinecarbonyl)benzyl)piperazine-1-carboxamide as yellow oil (0.076 g, 96.2%).

[Step 2] Compound 21646

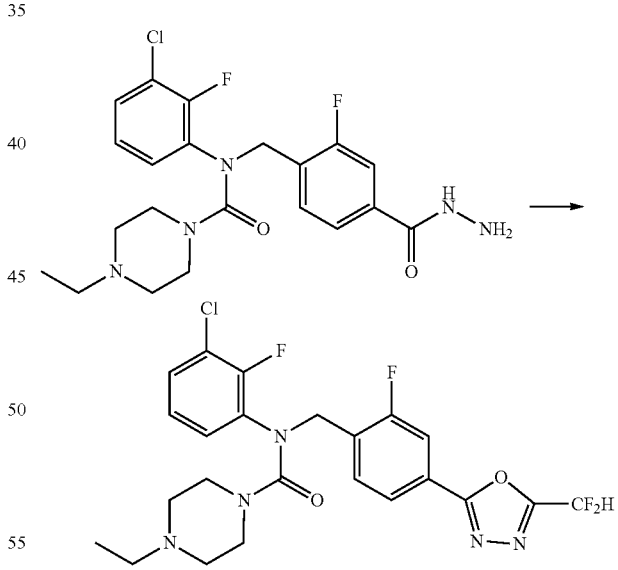

N-(3-chloro-2-fluorophenyl)-4-ethyl-N-(2-fluoro-4-(hydrazinecarbonyl)benzyl)piperazine-1-carboxamide (0.076 g, 0.168 mmol), 2,2-difluoroacetic anhydride (0.055 mL, 0.505 mmol) and triethylamine (0.117 mL, 0.841 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(3-chloro-2-fluorophenyl)-N-(4-(5-(difluoromethyl)-1,3,4-oxadiazol-2-yl)-2-fluorobenzyl)-4-ethylpiperazine-1-carboxamide as yellow oil (0.044 g, 50.5%).

$^1$H NMR (400 MHz, CDCl$_3$) δ 7.89 (dd, 1H, J=8.1, 1.7 Hz), 7.79 (t, 1H, J=7.6 Hz), 7.72 (dd, 1H, J=10.0, 1.7 Hz), 7.33-7.24 (m, 1H), 7.10-6.78 (m, 3H), 4.91 (s, 2H), 3.37 (s, 4H), 2.60-2.35 (m; 6H), 1.13 (t, 3H, J=7.2 Hz); LRMS (ES) m/z 512.4 (M$^+$+1).

Example 252. Compound 21650: N-(2-chloro-4-fluorophenyl)-N-(4-(5-(difluoromethyl)-1,3,4-oxadiazol-2-yl)-2-fluorobenzyl)-4-ethylpiperazine-1-carboxamide

[Step 1] Methyl 4-(((2-chloro-4-fluorophenyl)amino)methyl)-3-fluorobenzoate

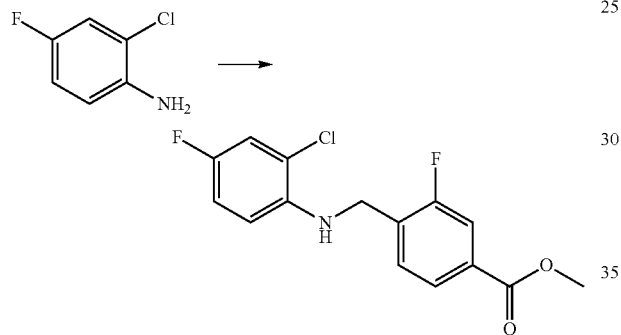

A solution of 2-chloro-4-fluoroaniline (1.000 g, 6.870 mmol), methyl 4-(bromomethyl)-3-fluorobenzoate (1.867 g, 7.557 mmol) and potassium carbonate (1.899 g, 13.740 mmol) in acetonitrile (10 mL) was stirred at the room temperature for 15 hr, filtered to remove solids, and concentrated under the reduced pressure. The residue was chromatographed (SiO$_2$, 40 g cartridge; ethyl acetate/hexane=0% to 10%) to give methyl 4-(((2-chloro-4-fluorophenyl)amino)methyl)-3-fluorobenzoate as green solid (0.974 g, 45.5%).

[Step 2] Methyl 4-4-(2-chloro-4-fluorophenyl)((4-nitrophenoxy)carbonyl)amino)methyl)-3-fluorobenzoate

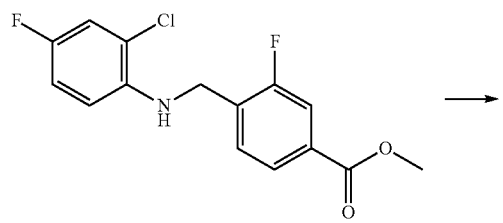

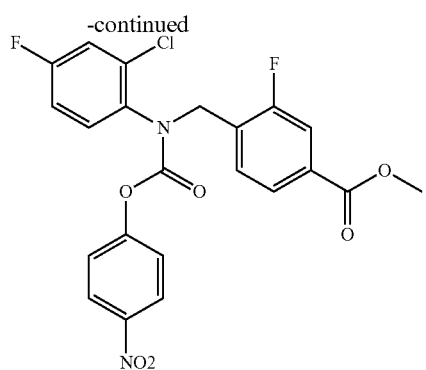

A solution of methyl 4-(((2-chloro-4-fluorophenyl)amino)methyl)-3-fluorobenzoate (0.500 g, 1.604 mmol), 4-nitrophenyl carbonochloridate (0.485 g, 2.406 mmol) and potassium carbonate (0.443 g, 3.208 mmol) in dichloromethane (5 mL) was stirred at the room temperature for 15 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 10%) to methyl 4-(((2-chloro-4-fluorophenyl)((4-nitrophenoxy)carbonyl)amino)methyl)-3-fluorobenzoate as pale yellow oil (0.441 g, 57.7%).

[Step 3] Methyl 4-((N-(2-chloro-4-fluorophenyl)-4-ethylpiperazine-1-carboxamido)methyl)-3-fluorobenzoate

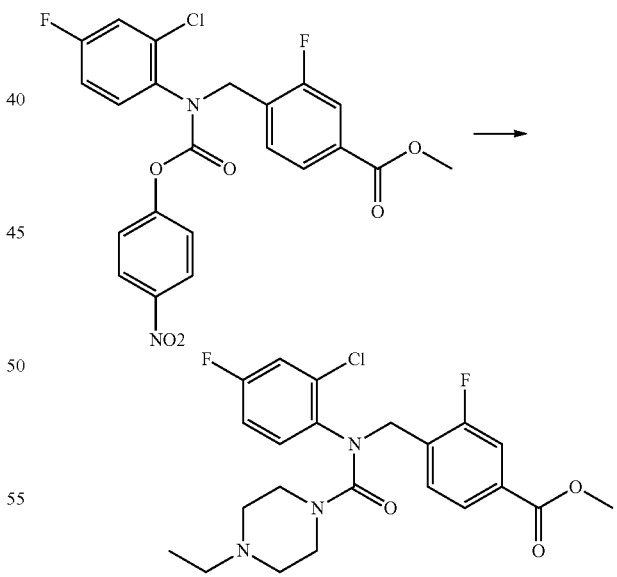

A solution of methyl 4-(((2-chloro-4-fluorophenyl)((4-nitrophenoxy)carbonyl)amino)methyl)-3-fluorobenzoate (0.300 g, 0.629 mmol), 1-ethylpiperazine (0.216 g, 1.888 mmol) and potassium carbonate (0.435 g, 3.146 mmol) in N,N-dimethylformide (5 mL) was stirred at 80° C. for 7 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 12 g cartridge; methanol/dichloromethane=0% to 10%) to give methyl 4-((N-(2-chloro-4-fluorophenyl)-4-ethylpiperazine-1-carboxamido)methyl)-3-fluorobenzoate as yellow oil (0.194 g, 68.2%).

[Step 4] N-(2-chloro-4-fluorophenyl)-4-ethyl-N-(2-fluoro-4-(hydrazinecarbonyl)benzyl)piperazine-1-carboxamide

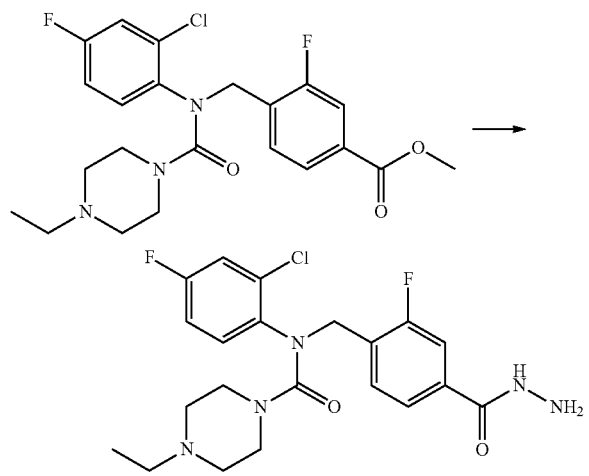

A mixture of methyl 4-((N-(2-chloro-4-fluorophenyl)-4-ethylpiperazine-1-carboxamido)methyl)-3-fluorobenzoate (0.094 g, 0.208 mmol) and hydrazine monohydrate (0.202 mL, 4.160 mmol) in ethanol (1 mL) was heated at reflux for 16 hr, and cooled down to the ambient temperature, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The crude N-(2-Chloro-4-fluorophenyl)-4-ethyl-N-(2-fluoro-4-(hydrazinecarbonyl)benzyl)piperazine-1-carboxamide was used without further purification (0.074 g, 78.7%, light yellow solid).

[Step 5] Compound 21650

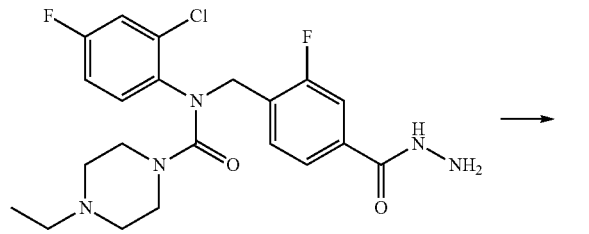

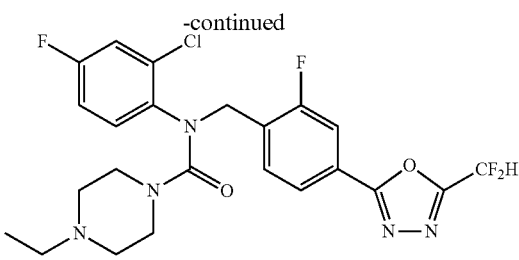

A solution of N-(2-chloro-4-fluorophenyl)-4-ethyl-N-(2-fluoro-4-(hydrazinecarbonyl)benzyl)piperazine-1-carboxamide (0.074 g, 0.164 mmol) and N,N-diisopropylethylamine (0.057 mL, 0.328 mmol) in dichloromethane (1 mL) was mixed at 0° C. with 2,2-difluoroacetic anhydride (0.036 mL, 0.328 mmol), and stirred at the room temperature for 16 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 3%) to give N-(2-chloro-4-fluorophenyl)-N-(4-(5-(difluoromethyl)-1,3,4-oxadiazol-2-yl)-2-fluorobenzyl)-4-ethylpiperazine-1-carboxamide as colorless oil (0.053 g, 62.9%).

¹H NMR (400 MHz, CDCl₃) δ 7.88-7.82 (m, 2H), 7.68-7.65 (m, 1H), 7.20 (dd, 1H, J=7.9, 2.8 Hz), 7.03-6.77 (m, 3H), 4.83 (s, 2H), 3.32-3.33 (m, 4H), 2.49-2.39 (m, 6H), 1.12-1.13 (m, 3H); LRMS (ES) m/z 512.5 (M⁺+1).

Example 253. Compound 21651: (S)—N-(2-chloro-4-fluorophenyl)-N-(4-(5-(difluoromethyl)-1,3,4-oxadiazol-2-yl)-2-fluorobenzyl)-3-(dimethylamino)pyrrolidine-1-carboxamide

[Step 1] Methyl (S)-4-((N-(2-chloro-4-fluorophenyl)-3-(dimethylamino)pyrrolidine-1-carboxamido)methyl)-3-fluorobenzoate

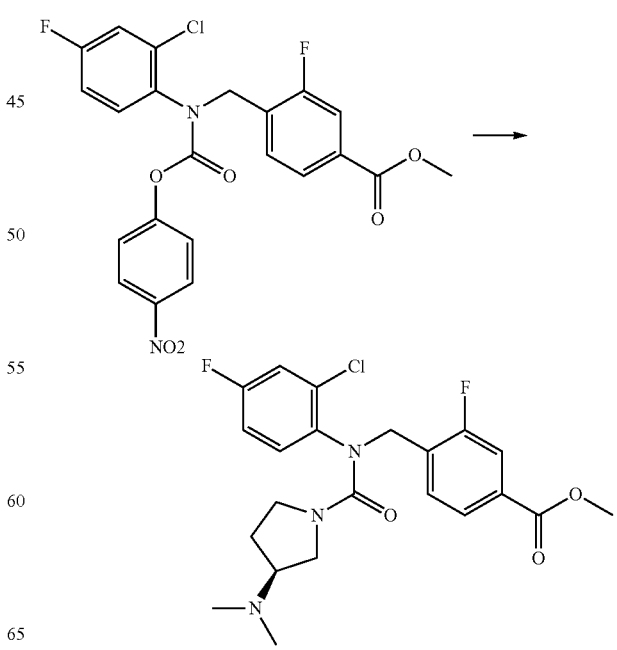

A solution of methyl 4-(((2-chloro-4-fluorophenyl)((4-nitrophenoxy)carbonyl)amino)methyl)-3-fluorobenzoate (0.300 g, 0.629 mmol), (S)—N,N-dimethylpyrrolidin-3-amine (0.216 g, 1.888 mmol) and potassium carbonate (0.435 g, 3.146 mmol) in N,N-dimethylformide (5 mL) was stirred at 80° C. for 7 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; methanol/dichloromethane=0% to 10%) to give methyl (S)-4-((N-(2-chloro-4-fluorophenyl)-3-(dimethylamino)pyrrolidine-1-carboxamido)methyl)-3-fluorobenzoate as yellow oil (0.201 g, 70.7%).

[Step 2] (S)—N-(2-chloro-4-fluorophenyl)-3-(dimethylamino)-N-(2-fluoro-4-(hydrazinecarbonyl)benzyl)pyrrolidine-1-carboxamide

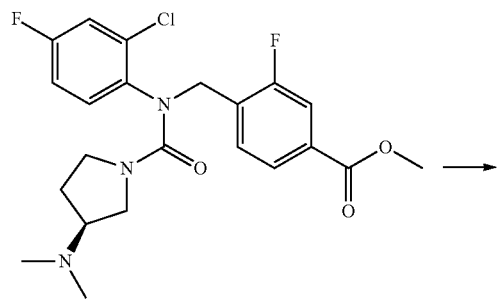

A mixture of methyl (S)-4-((N-(2-chloro-4-fluorophenyl)-3-(dimethylamino)pyrrolidine-1-carboxamido)methyl)-3-fluorobenzoate (0.082 g, 0.181 mmol) and hydrazine monohydrate (0.176 mL, 3.629 mmol) in ethanol (3 mL) was heated at reflux for 16 hr, and cooled down to the ambient temperature, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The crude (S)—N-(2-chloro-4-fluorophenyl)-3-(dimethylamino)-N-(2-fluoro-4-(hydrazinecarbonyl)benzyl)pyrrolidine-1-carboxamide was used without further purification (0.072 g, 87.8%, yellow oil).

[Step 3] Compound 21651

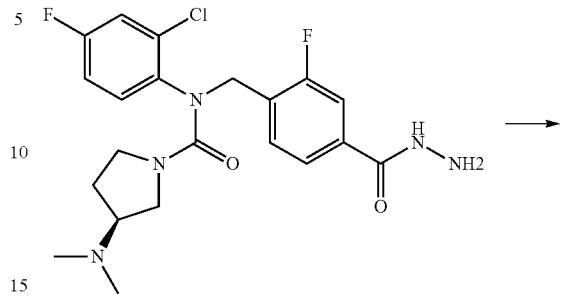

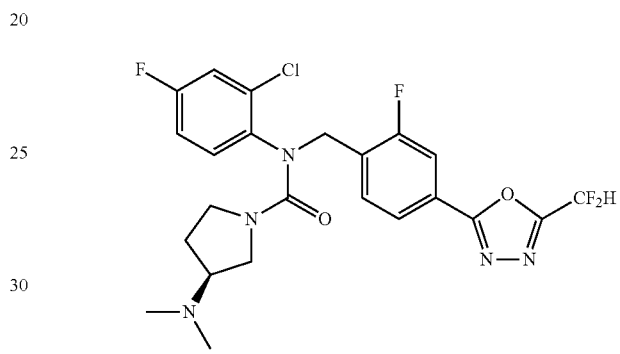

A solution of (S)—N-(2-chloro-4-fluorophenyl)-3-(dimethylamino)-N-(2-fluoro-4-(hydrazinecarbonyl)benzyl)pyrrolidine-1-carboxamide (0.072 g, 0.159 mmol) and N,N-diisopropylethylamine (0.056 mL, 0.319 mmol) in dichloromethane (1 mL) was mixed at the room temperature with 2,2-difluoroacetic anhydride (0.035 mL, 0.319 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give (S)—N-(2-chloro-4-fluorophenyl)-N-(4-(5-(difluoromethyl)-1,3,4-oxadiazol-2-yl)-2-fluorobenzyl)-3-(dimethylamino)pyrrolidine-1-carboxamide as light yellow solid (0.038 g, 46.7%).

$^1$H NMR (400 MHz, CDCl$_3$) δ 7.92-7.88 (m, 1H), 7.86 (dd 1H, J=8.0, 1.6 Hz). 7.65 (dd, 1H, J=9.9, 1.5 Hz), 7.18 (dd, 1H, J=8.0, 2.8 Hz), 7.03-6.77 (m, 3H), 4.87 (s, 2H), 3.49-3.45 (m, 1H), 3.27-3.23 (m, 1H), 3.03-2.96 (m, 1H), 2.92-2.92 (m, 1H), 2.78-2.75 (m, 1H), 2.29 (s, 6H), 2.04-2.00 (m, 1H), 1.98-1.99 (m, 1H); LRMS (ES) m/z 512.5 (M$^+$+1).

Example 254. Compound 21652: (R)—N-(2-chloro-4-fluorophenyl)-N-(4-(5-(difluoromethyl)-1,3,4-oxadiazol-2-yl)-2-fluorobenzyl)-3-(dimethylamino)pyrrolidine-1-carboxamide

[Step 1] Methyl (R)-4-((N-(2-chloro-4-fluorophenyl)-3-(dimethylamino)pyrrolidine-1-carboxamido)methyl)-3-fluorobenzoate

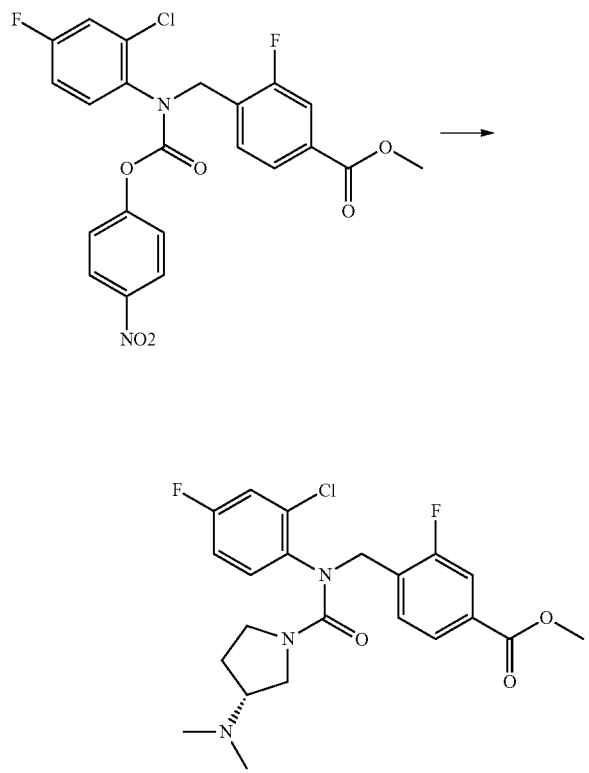

A solution of methyl 4-(((2-chloro-4-fluorophenyl)((4-nitrophenoxy)carbonyl)amino)methyl)-3-fluorobenzoate (0.300 g, 0.629 mmol), (R)—N,N-dimethylpyrrolidin-3-amine (0.216 g, 1.888 mmol) and potassium carbonate (0.435 g, 3.146 mmol) in N,N-dimethylformide (5 mL) was stirred at 80° C. for 7 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 12 g cartridge; methanol/dichloromethane=0% to 100%) to give methyl (R)-4-((N-(2-chloro-4-fluorophenyl)-3-(dimethylamino)pyrrolidine-1-carboxamido)methyl)-3-fluorobenzoate as yellow oil (0.167 g, 58.7%).

[Step 2] (R)—N-(2-chloro-4-fluorophenyl)-3-(dimethylamino)-N-(2-fluoro-4-(hydrazinecarbonyl)benzyl)pyrrolidine-1-carboxamide

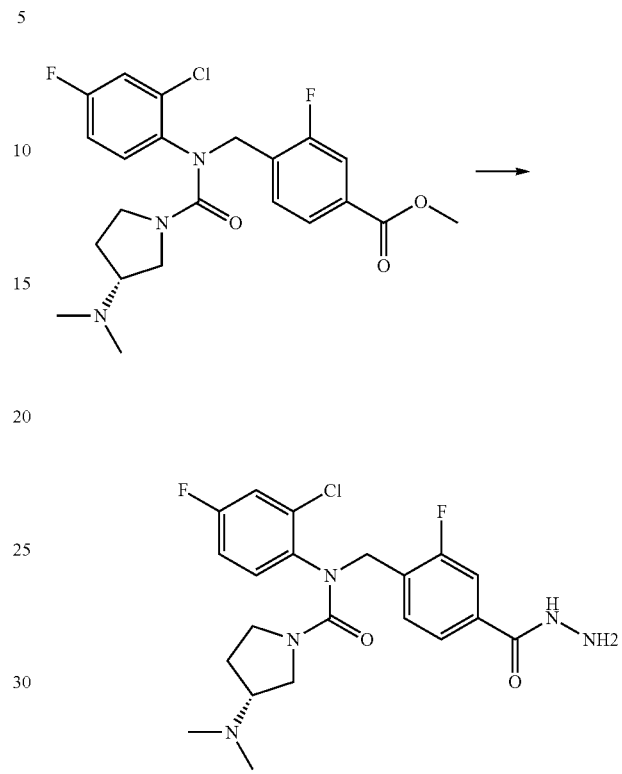

A mixture of methyl (R)-4-((N-(2-chloro-4-fluorophenyl)-3-(dimethylamino)pyrrolidine-1-carboxamido)methyl)-3-fluorobenzoate (0.089 g, 0.197 mmol) and hydrazine monohydrate (0.191 mL, 3.939 mmol) in ethanol (3 mL) was heated at reflux for 16 hr, cooled down to the ambient temperature, and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The crude (R)—N-(2-chloro-4-fluorophenyl)-3-(dimethylamino)-N-(2-fluoro-4-(hydrazinecarbonyl)benzyl)pyrrolidine-1-carboxamide was used without further purification (0.082 g, 92.1%, yellow oil).

[Step 3] Compound 21652

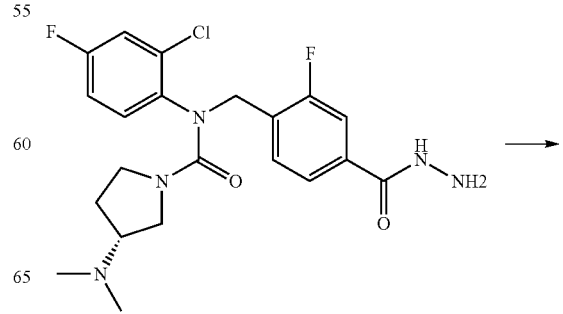

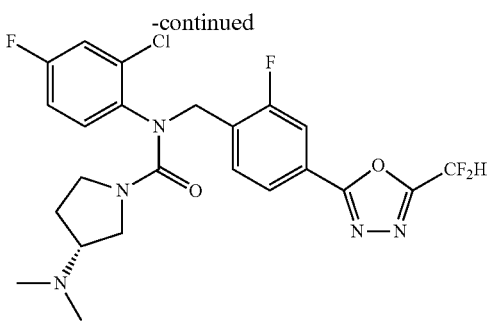

A solution of (R)—N-(2-chloro-4-fluorophenyl)-3-(dimethylamino)-N-(2-fluoro-4-(hydrazinecarbonyl)benzyl)pyrrolidine-1-carboxamide (0.082 g, 0.181 mmol), and N,N-diisopropylethylamine (0.063 mL, 0.363 mmol) in dichloromethane (1 mL) was mixed at the room temperature with 2,2-difluoroacetic anhydride (0.039 mL, 0.363 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give (R)—N-(2-chloro-4-fluorophenyl)-N-(4-(5-(difluoromethyl)-1,3,4-oxadiazol-2-yl)-2-fluorobenzyl)-3-(dimethylamino)pyrrolidine-1-carboxamide as light yellow solid (0.041 g, 43.6%).

$^1$H NMR (400 MHz, CDCl$_3$) δ 7.91-7.88 (m, 1H), 7.86 (dd, 1H, J=8.0, 1.5 Hz), 7.65 (dd, 1H, J=9.9, 1.5 Hz), 7.19 (dd, 1H, J=8.0, 2.8 Hz), 7.03-6.77 (m, 3H), 4.87 (s, 2H), 3.52-3.48 (m, 1H), 3.26-3.21 (m, 1H), 3.03-2.98 (m, 2H), 2.87-2.83 (m, 1H), 2.35 (s, 6H), 2.04-2.02 (m, 1H), 1.89-1.90 (m, 1H); LRMS (ES) m/z 512.5 (M$^+$+1).

Example 255. Compound 21653: N-(4-(5-(difluoromethyl)-1,3,4-oxadiazol-2-yl)-2-fluorobenzyl)-N-(5-fluoropyridin-2-yl)thiomorpholine-4-carboxamide 1,1-dioxide

[Step 1] Methyl 3-fluoro-4-(((5-fluoropyridin-2-yl)amino)methyl)benzoate

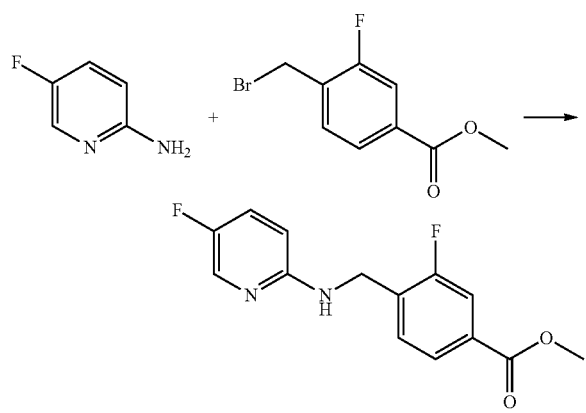

A solution of 5-fluoropyridin-2-amine (0.448 g, 4.000 mmol), methyl 4-(bromomethyl)-3-fluorobenzoate (0.988 g, 4.000 mmol) and N,N-diisopropylethylamine (1.393 mL, 8.000 mmol) in acetonitrile (16 mL) was stirred at the room temperature for 18 hr, and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 50%) to give methyl 3-fluoro-4-(((5-fluoropyridin-2-yl)amino)methyl)benzoate as colorless oil (0.147 g, 13.2%).

[Step 2] Methyl 3-fluoro-4-((N-(5-fluoropyridin-2-yl)-1,1-dioxidothiomorpholine-4-carboxamido)methyl)benzoate

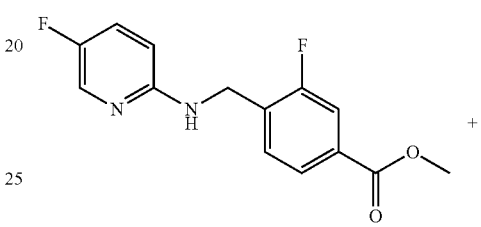

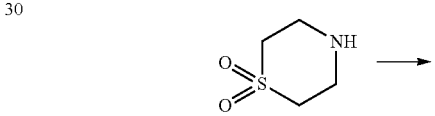

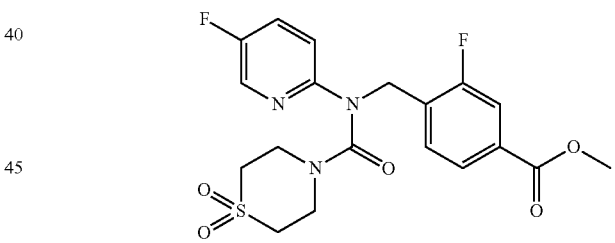

A solution of methyl 3-fluoro-4-(((5-fluoropyridin-2-yl)amino)methyl)benzoate (0.147 g, 0.528 mmol), N,N-diisopropylethylamine (0.551 mL, 3.165 mmol) and triphosgene (0.078 g, 0.264 mmol) in dichloromethane (2 mL) was stirred at the room temperature for 30 min, and mixed with thiomorpholine 1,1-dioxide (0.071 g, 0.528 mmol). The reaction mixture was stirred at the same temperature for additional 18 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 50%) to give methyl 3-fluoro-4-((N-(5-fluoropyridin-2-yl)-1,1-dioxidothiomorpholine-4-carboxamido)methyl)benzoate as pale yellow oil (0.180 g, 77.5%).

827

[Step 3] N-(2-fluoro-4-(hydrazinecarbonyl)benzyl)-N-(5-fluoropyridin-2-yl)thiomorpholine-4-carboxamide 1,1-dioxide

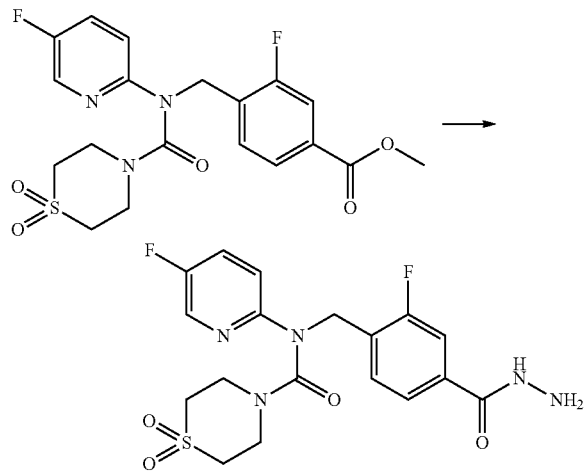

Methyl 3-fluoro-4-((N-(5-fluoropyridin-2-yl)-1,1-dioxidothiomorpholine-4-carboxamido)methyl)benzoate (0.180 g, 0.409 mmol) and hydrazine monohydrate (0.397 mL, 8.174 mmol) were mixed at the room temperature in ethanol (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 10%) to give N-(2-fluoro-4-(hydrazinecarbonyl)benzyl)-N-(5-fluoropyridin-2-yl)thiomorpholine-4-carboxamide 1,1-dioxide as colorless oil (0.139 g, 77.3%).

[Step 4] N-(4-(2-(2,2-difluoroacetyl)hydrazine-1-carbonyl)-2-fluorobenzyl)-N-(5-fluoropyridin-2-yl)thiomorpholine-4-carboxamide 1,1-dioxide

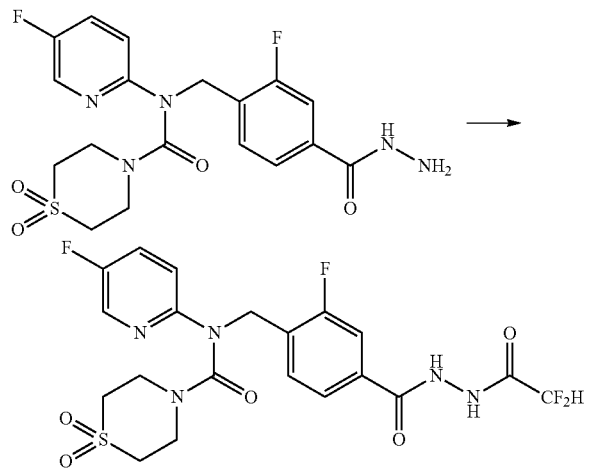

828

A solution of N-(2-fluoro-4-(hydrazinecarbonyl)benzyl)-N-(5-fluoropyridin-2-yl)thiomorpholine-4-carboxamide 1,1-dioxide (0.139 g, 0.316 mmol) and triethylamine (0.088 mL, 0.632 mmol) in dichloromethane (4 mL) was stirred at the room temperature for 10 min, and mixed with 2,2-difluoroacetic anhydride (0.035 mL, 0.284 mmol). The reaction mixture was stirred at the same temperature for additional 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 10%) to give N-(4-(2-(2,2-difluoroacetyl)hydrazine-1-carbonyl)-2-fluorobenzyl)-N-(5-fluoropyridin-2-yl)thiomorpholine-4-carboxamide 1,1-dioxide as white solid (0.078 g, 47.7%).

[Step 5] Compound 21653

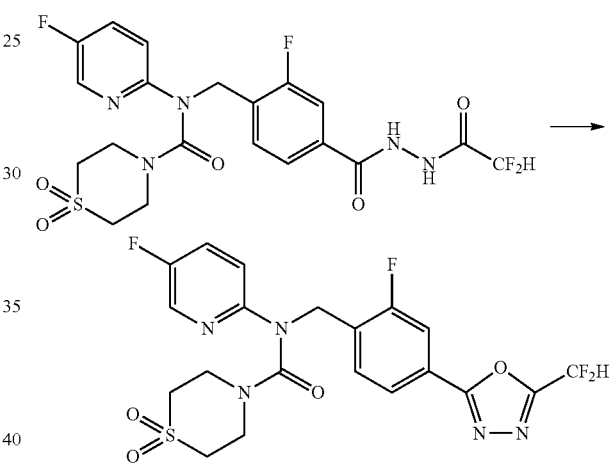

A solution of N-(4-(2-(2,2-difluoroacetyl)hydrazine-1-carbonyl)-2-fluorobenzyl)-N-(5-fluoropyridin-2-yl)thiomorpholine-4-carboxamide 1,1-dioxide (0.039 g, 0.075 mmol) and N,N-diisopropylethylamine (0.066 mL, 0.377 mmol) in tetrahydrofuran (1 mL) stirred at the room temperature for 10 min, and mixed with methanesulfonyl chloride (0.007 mL, 0.090 mmol). The reaction mixture was stirred at 80° C. for additional 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 50%) to give N-(4-(5-(difluoromethyl)-1,3,4-oxadiazol-2-yl)-2-fluorobenzyl)-N-(5-fluoropyridin-2-yl)thiomorpholine-4-carboxamide 1,1-dioxide as pale brown solid (0.018 g, 48.9%).
$^1$H NMR (400 MHz, CDCl$_3$) δ 8.28 (d, 1H, J=2.2 Hz), 7.87 (d, 1H, J=7.8 Hz), 7.79 (dd, 1H, J=10.1, 1.2 Hz), 7.68 (t, 1H, J=7.6 Hz), 7.45-7.44 (m, 1H), 7.08 (d, 1H, J=8.4 Hz), 6.93 (t, 1H, J=51.7 Hz), 5.12 (s, 2H), 3.78 (s, 4H), 2.96 (s, 4H); LRMS (ES) m/z 500.5 (M$^+$+1).

829

Example 256. Compound 21654: N-(4-(5-(difluoromethyl)-1,3,4-oxadiazol-2-yl)-2-fluorobenzyl)-4-methyl-N-(1-methyl-1H-indazol-6-yl)piperazine-1-carboxamide

[Step 1] Methyl 3-fluoro-4-(((1-methyl-1H-indazol-6-yl)amino)methyl)benzoate

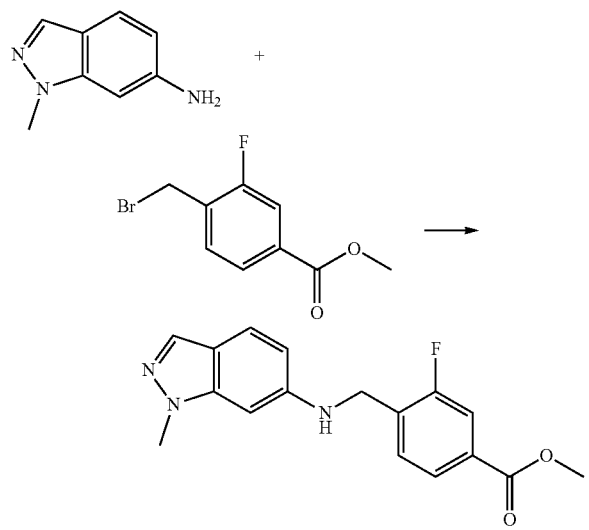

A solution of 1-methyl-1H-indazol-6-amine (0.294 g, 2.000 mmol), methyl 4-(bromomethyl)-3-fluorobenzoate (0.494 g, 2.000 mmol) and N,N-diisopropylethylamine (0.697 mL, 4.000 mmol) in acetonitrile (8 mL) was stirred at the room temperature for 18 hr and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 50%) to give methyl 3-fluoro-4-4-(1-methyl-1H-indazol-6-yl)amino)methyl)benzoate as green foam solid (0.364 g, 58.0%).

[Step 2] Methyl 3-fluoro-4-((4-methyl-N-(1-methyl-1H-indazol-6-yl)piperazine-1-carboxamido)methyl) benzoate

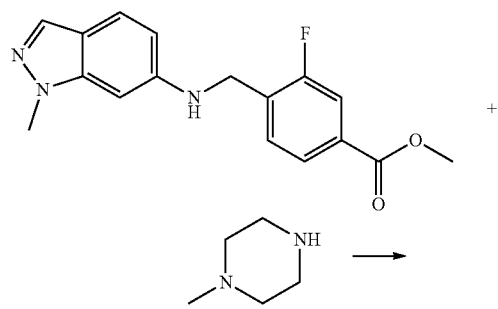

830

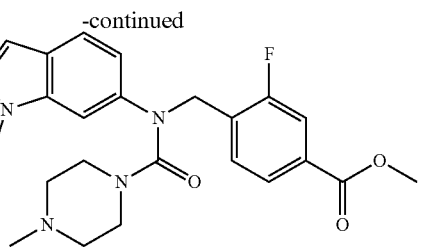

A solution of methyl 3-fluoro-4-(((1-methyl-1H-indazol-6-yl)amino)methyl)benzoate (0.364 g, 1.160 mmol), N,N-diisopropylethylamine (1.213 mL, 6.963 mmol) and triphosgene (0.172 g, 0.580 mmol) in dichloromethane (5 mL) was stirred at the room temperature for 30 min, and mixed with 1-methylpiperazine (0.129 mL, 1.160 mmol). The reaction mixture was stirred at the same temperature for additional 18 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give methyl 3-fluoro-4-((4-methyl-N-(1-methyl-1H-indazol-6-yl)piperazine-1-carboxamido)methyl) benzoate as green oil (0.384 g, 75.2%).

[Step 3] N-(2-Fluoro-4-(hydrazinecarbonyl)benzyl)-4-methyl-N-(1-methyl-1H-indazol-6-yl)piperazine-1-carboxamide

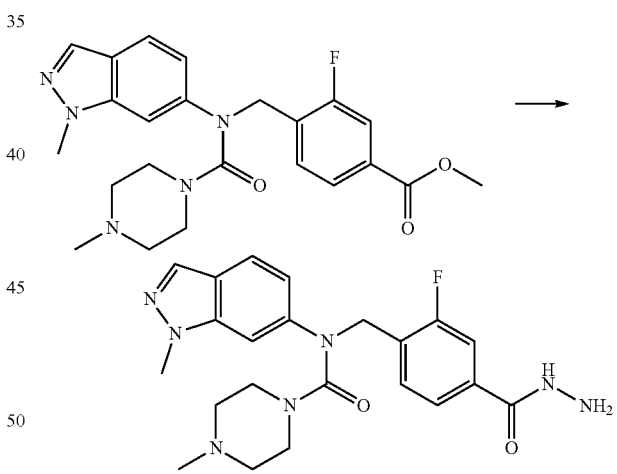

Methyl 3-fluoro-4-((4-methyl-N-(1-methyl-1H-indazol-6-yl)piperazine-1-carboxamido)methyl) benzoate (0.384 g, 0.873 mmol) and hydrazine monohydrate (0.849 mL, 17.461 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 10%) to give N-(2-fluoro-4-(hydrazinecarbonyl)

benzyl)-4-methyl-N-(1-methyl-1H-indazol-6-yl)piperazine-1-carboxamide as colorless oil (0.262 g, 68.2%).

[Step 4] N-(4-(2-(2,2-Difluoroacetyl)hydrazine-1-carbonyl)-2-fluorobenzyl)-4-methyl-N-(1-methy 1-1H-indazol-6-yl)piperazine-1-carboxamide

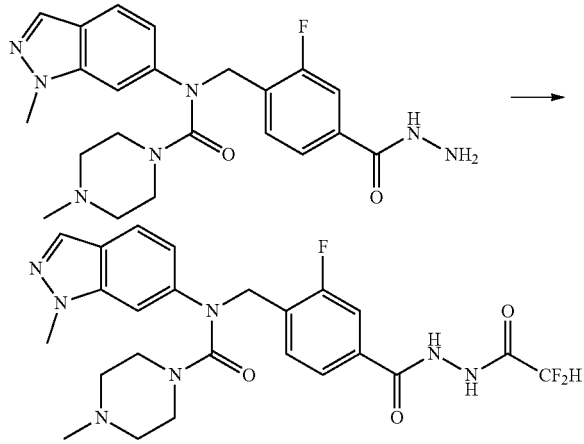

A solution of N-(2-fluoro-4-(hydrazinecarbonyl)benzyl)-4-methyl-N-(1-methyl-1H-indazol-6-yl)piperazine-1-carboxamide (0.262 g, 0.595 mmol) and triethylamine (0.166 mL, 1.191 mmol) in dichloromethane (4 mL) was stirred at the room temperature for 10 min, and mixed with 2,2-difluoroacetic anhydride (0.067 mL, 0.536 mmol). The reaction mixture was stirred at the same temperature for additional 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 10%) to give N-(4-(2-(2,2-difluoroacetyl)hydrazine-1-carbonyl)-2-fluorobenzyl)-4-methyl-N-(1-methy 1-1H-indazol-6-yl)piperazine-1-carboxamide as white solid (0.199 g, 64.7%).

[Step 5] Compound 21654

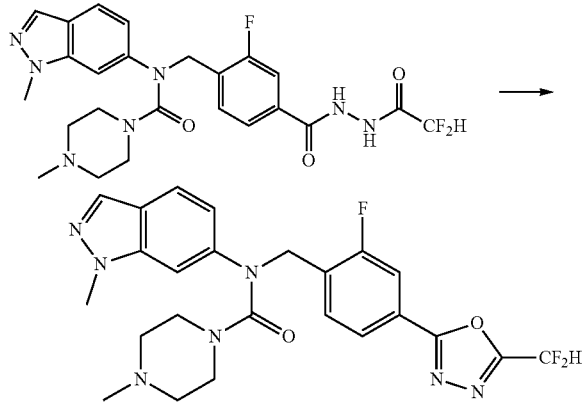

A mixture of N-(4-(2-(2,2-difluoroacetyl)hydrazine-1-carbonyl)-2-fluorobenzyl)-4-methyl-N-(1-methy 1-1H-indazol-6-yl)piperazine-1-carboxamide (0.100 g, 0.193 mmol) and 1-methoxy-N-triethylammoniosulfonyl-methanimidate (Burgess reagent, 0.069 g, 0.290 mmol) in tetrahydrofuran (1 mL) was heated at 150° C. for 30 min under the microwaves and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)-2-fluorobenzyl)-4-methyl-N-(1-methyl-1H-indazol-6-yl)piperazine-1-carboxamide as white solid (0.022 g, 23.1%).

$^1$H NMR (400 MHz, CDCl$_3$) δ 7.93 (d, 1H, J=1.0 Hz), 7.88 (dd, 1H, J=8.0, 1.6 Hz), 7.76-7.73 (m, 2H), 7.65 (dd, 1H, J=8.6, 0.5 Hz), 7.07 (t, 1H, J=0.8 Hz), 6.95 (dd, 1H, J=8.6, 1.8 Hz), 6.92 (t, 1H, J=51.7 Hz), 5.06 (s, 2H), 4.02 (s, 3H), 3.34 (t, 4H, J=4.9 Hz), 2.27-2.24 (m, 7H); LRMS (ES) m/z 500.6 (M$^+$+1).

Example 257. Compound 21655: N-(4-(5-(difluoromethyl)-1,3,4-oxadiazol-2-yl)-2-fluorobenzyl)-N-(2,3-difluorophenyl)-4-ethylpiperazine-1-carboxamide

[Step 1] Methyl 4-(((2,3-difluorophenyl)amino)methyl)-3-fluorobenzoate

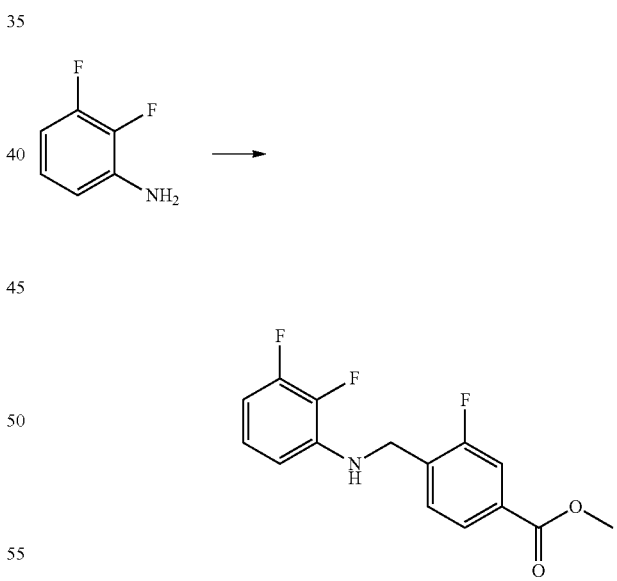

A solution of 2,3-difluoroaniline (1.000 g, 7.745 mmol), methyl 4-(bromomethyl)-3-fluorobenzoate (2.105 g, 8.520 mmol) and potassium carbonate (2.141 g, 15.491 mmol) in acetonitrile (10 mL) was stirred at the room temperature for 15 hr, filtered to remove solids, and concentrated under the reduced pressure to remove the solvents. The residue was chromatographed (SiO$_2$, 40 g cartridge; ethyl acetate/hexane=0% to 10%) to give methyl 4-(((2,3-difluorophenyl)amino)methyl)-3-fluorobenzoate as pale brown oil (0.904 g, 39.5%).

833

[Step 2] Methyl 4-4-(2,3-difluorophenyl)((4-nitrophenoxy)carbonyl)amino)methyl)-3-fluorobenzoate

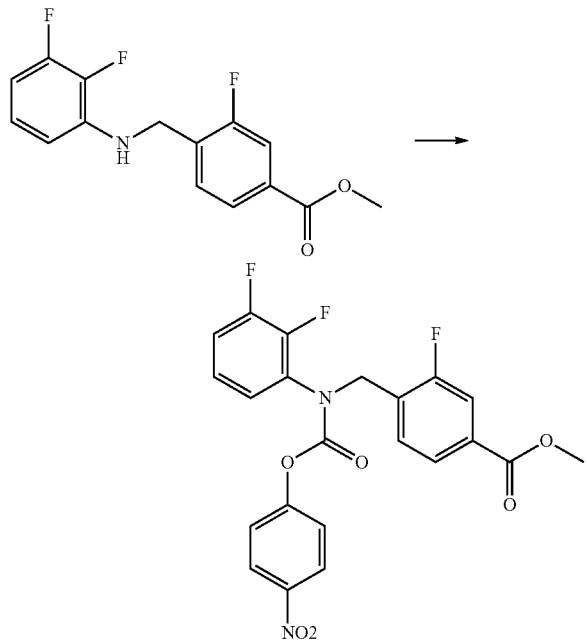

A solution of methyl 4-4-(2,3-difluorophenyl)amino)methyl)-3-fluorobenzoate (0.500 g, 1.693 mmol), 4-nitrophenyl carbonochloridate (0.512 g, 2.540 mmol) and potassium carbonate (0.468 g, 3.387 mmol) in dichloromethane (5 mL) was stirred at the room temperature for 15 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 10%) to give methyl 4-4-(2,3-difluorophenyl)((4-nitrophenoxy)carbonyl)amino)methyl)-3-fluorobenzoate as pale yellow oil (0.425 g, 54.5%).

[Step 3] Methyl 4-((N-(2,3-difluorophenyl)-4-ethyl-piperazine-1-carboxamido)methyl)-3-fluorobenzoate

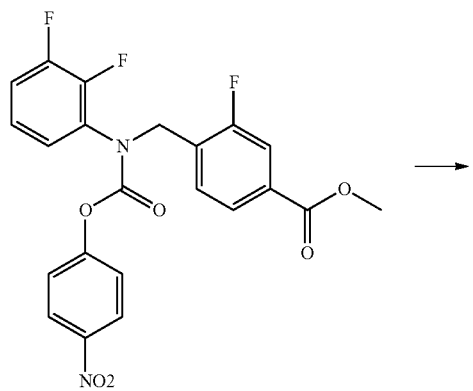

834

-continued

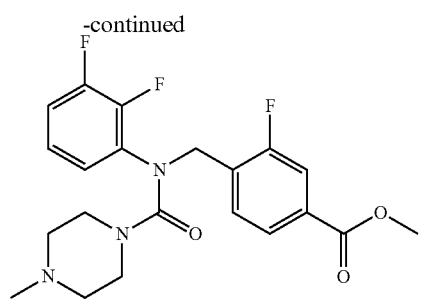

A solution of methyl 4-(((2,3-difluorophenyl)((4-nitrophenoxy)carbonyl)amino)methyl)-3-fluorobenzoate (0.300 g, 0.652 mmol), 1-ethylpiperazine (0.223 g, 1.955 mmol) and potassium carbonate (0.450 g, 3.258 mmol) in N,N-dimethylformide (5 mL) was stirred at 80° C. for 5 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 24 g cartridge; methanol/dichloromethane=0% to 10%) to give methyl 4-((N-(2,3-difluorophenyl)-4-ethylpiperazine-1-carboxamido)methyl)-3-fluorobenzoate as pale yellow oil (0.165 g, 58.1%)

[Step 4] N-(2,3-difluorophenyl)-4-ethyl-N-(2-fluoro-4-(hydrazinecarbonyl)benzyl)piperazine-1-carboxamide

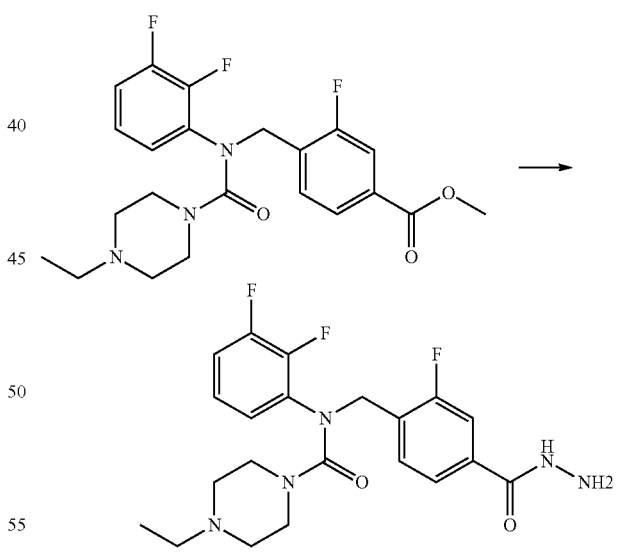

A mixture of methyl 4-((N-(2,3-difluorophenyl)-4-ethyl-piperazine-1-carboxamido)methyl)-3-fluorobenzoate (0.180 g, 0.413 mmol) and hydrazine monohydrate (0.402 mL, 8.267 mmol) in ethanol (3 mL) was heated at reflux for 16 hr, and cooled down to the ambient temperature and concentrated under the reduced pressure to remove the solvents. Then, water was added to the reaction mixture, followed by extraction with dichloromethane. The bi-phasic mixture was passed through a plastic frit to remove the solid residues and aqueous layer, and the organic layer collected was concentrated in vacuo. The crude N-(2,3-difluorophenyl)-4-ethyl-N-(2-fluoro-4-(hydrazinecarbonyl)benzyl)piperazine-1-carboxamide was used without further purification (0.178 g, 98.9%, light yellow solid).

[Step 5] Compound 21655

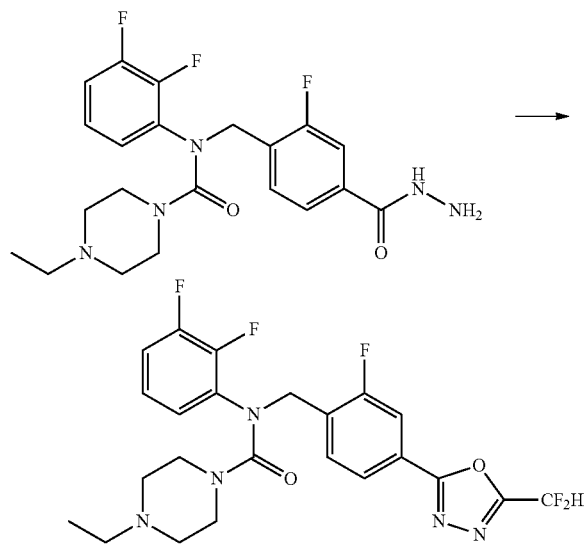

A solution of N-(2,3-difluorophenyl)-4-ethyl-N-(2-fluoro-4-(hydrazinecarbonyl)benzyl)piperazine-1-carboxamide (0.089 g, 0.204 mmol) and N,N-diisopropylethylamine (0.071 mL, 0.409 mmol) in dichloromethane (1 mL) was mixed at 0° C. with 2,2-difluoroacetic anhydride (0.044 mL, 0.409 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove the solid residues and aqueous layer, and organic layer collected was concentrated in vacuo. The residue was chromatographed (SiO$_2$, 4 g cartridge; methanol/dichloromethane=0% to 3%) to give N-(4-(5-(difluoromethyl)-1,3,4-oxadiazol-2-yl)-2-fluorobenzyl)-N-(2,3-difluorophenyl)-4-ethylpiperazine-1-carboxamide as white solid (0.041 g, 40.5%).

$^1$H NMR (400 MHz, CDCl$_3$) δ 7.86 (dd, 1H, J=8.1, 1.7 Hz), 7.80-7.76 (m, 1H), 7.69 (dd, 1H, J=10.0, 1.6 Hz), 7.04-6.77 (m, 4H), 4.90 (s, 2H), 3.33-3.34 (m, 4H), 2.45-2.37 (m, 6H), 1.10 (t, 3H, J=7.1 Hz); LRMS (ES) m/z 496.6 (M$^+$+1).

Example 258. Compound 21656: N-(3-bromo-4-fluorophenyl)-N-(4-(5-(difluoromethyl)-1,3,4-oxadiazol-2-yl)-2-fluorobenzyl)-4-ethylpiperazine-1-carboxamide

[Step 1] Methyl 4-(((3-bromo-4-fluorophenyl)amino)methyl)-3-fluorobenzoate

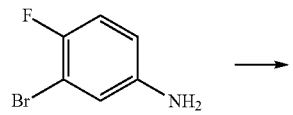

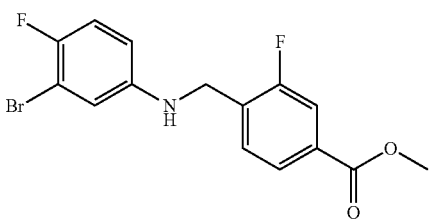

A solution of 3-bromo-4-fluoroaniline (1.000 g, 5.263 mmol), methyl 4-(bromomethyl)-3-fluorobenzoate (1.430 g, 5.789 mmol) and potassium carbonate (1.455 g, 10.525 mmol) in acetonitrile (10 mL) was stirred at the room temperature for 15 hr, filtered to remove solids, and concentrated under the reduced pressure to remove the solvents. The residue was chromatographed (SiO$_2$, 40 g cartridge; ethyl acetate/hexane=0% to 10%) to give methyl 4-4-(3-bromo-4-fluorophenyl)amino)methyl)-3-fluorobenzoate as palw brown oil (1.104 g, 58.9%).

[Step 2] Methyl 4-(((3-bromo-4-fluorophenyl)((4-nitrophenoxy)carbonyl)amino)methyl)-3-fluorobenzoate

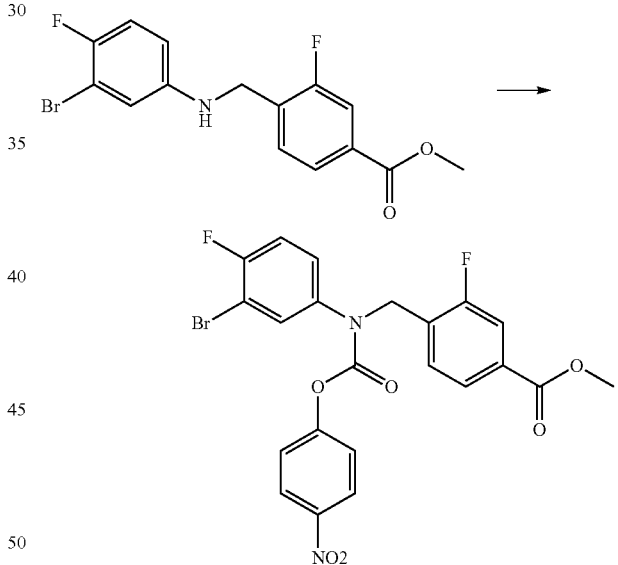

A solution of methyl 4-(((3-bromo-4-fluorophenyl)amino)methyl)-3-fluorobenzoate (0.500 g, 1.404 mmol), 4-nitrophenyl carbonochloridate (0.424 g, 2.106 mmol) and potassium carbonate (0.388 g, 2.808 mmol) in dichloromethane (5 mL) was stirred at the room temperature for 15 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 10%) to give methyl 4-(((3-bromo-4-fluorophenyl)((4-nitrophenoxy)carbonyl)amino)methyl)-3-fluorobenzoate as pale yellow oil (0.420 g, 57.4%).

[Step 3] Methyl 4-((N-(3-bromo-4-fluorophenyl)-4-ethylpiperazine-1-carboxamido)methyl)-3-fluorobenzoate

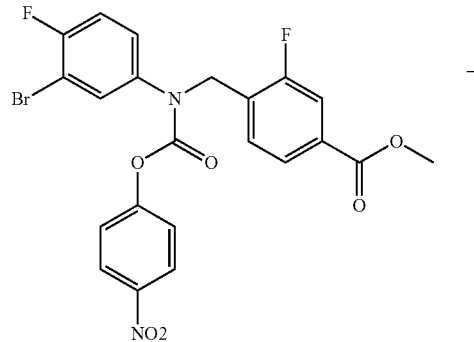

A solution of methyl 4-(((3-bromo-4-fluorophenyl)((4-nitrophenoxy)carbonyl)amino)methyl)-3-fluorobenzoate (0.300 g, 0.576 mmol), 1-ethylpiperazine (0.197 g, 1.727 mmol) and potassium carbonate (0.398 g, 2.878 mmol) in N,N-dimethylformide (5 mL) was stirred at 80° C. for 5 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 24 g cartridge; methanol/dichloromethane=0% to 10%) to give methyl 4-((N-(3-bromo-4-fluorophenyl)-4-ethylpiperazine-1-carboxamido)methyl)-3-fluorobenzoate as pale yellow oil (0.210 g, 70.0%).

[Step 4] N-(3-bromo-4-fluorophenyl)-4-ethyl-N-(2-fluoro-4-(hydrazinecarbonyl)benzyl)piperazine-1-carboxamide

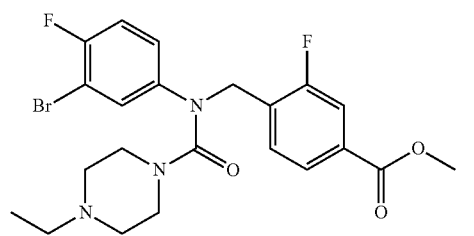

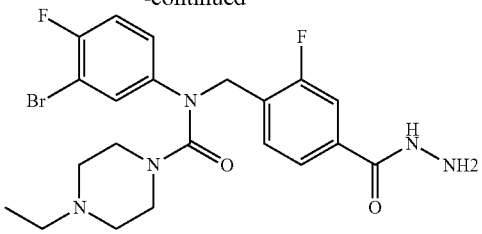

A mixture of methyl 4-((N-(3-bromo-4-fluorophenyl)-4-ethylpiperazine-1-carboxamido)methyl)-3-fluorobenzoate (0.130 g, 0.262 mmol) and hydrazine monohydrate (0.255 mL, 5.238 mmol) in ethanol (2 mL) was heated at reflux for 16 hr, cooled down to the ambient temperature, and concentrated under the reduced pressure to remove the solvents. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The crude N-(3-bromo-4-fluorophenyl)-4-ethyl-N-(2-fluoro-4-(hydrazinecarbonyl)benzyl)piperazine-1-carboxamide was used without further purification (0.129 g, 99.2%, white solid).

[Step 5] Compound 21656

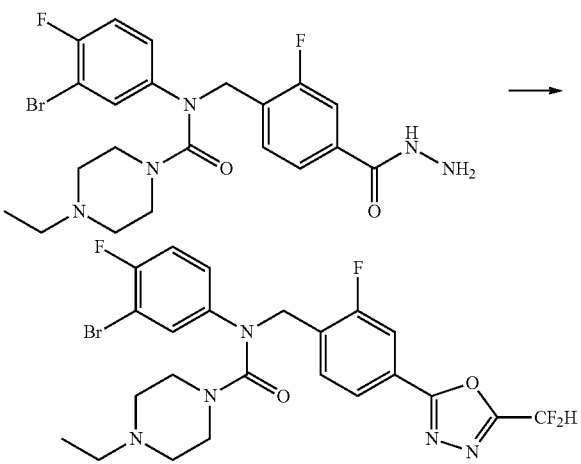

A solution of N-(3-bromo-4-fluorophenyl)-4-ethyl-N-(2-fluoro-4-(hydrazinecarbonyl)benzyl)piperazine-1-carboxamide (0.064 g, 0.129 mmol) and N,N-diisopropylethylamine (0.045 mL, 0.258 mmol) in dichloromethane (2 mL) was mixed at 0° C. with 2,2-difluoroacetic anhydride (0.028 mL, 0.258 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(3-bromo-4-fluorophenyl)-N-(4-(5-difluoromethyl)-1,3,4-oxadiazol-2-yl)-2-fluorobenzyl)-4-ethylpiperazine-1-carboxamide as white solid (0.035 g, 48.8%).

$^1$H NMR (400 MHz, CDCl$_3$) δ 7.87 (dd, 1H, J=8.0, 1.7 Hz), 7.76 (dd, 1H, J=10.1, 1.6 Hz), 7.69-7.65 (m, 1H), 7.31 (dd, 1H, J=5.8, 2.6 Hz), 7.09-6.78 (m, 3H), 4.90 (s, 2H), 3.39-3.40 (m, 4H), 2.52-2.44 (m, 6H), 1.25-1.14 (m, 3H); LRMS (ES) m/z 556.46 (M$^+$+1).

Example 259. Compound 21657: N-(3-chloro-4-methylphenyl)-N-(4-(5-(difluoromethyl)-1,3,4-oxadiazol-2-yl)-2-fluorobenzyl)-4-ethylpiperazine-1-carboxamide

[Step 1] Methyl 4-(((3-chloro-4-methylphenyl)amino)methyl)-3-fluorobenzoate

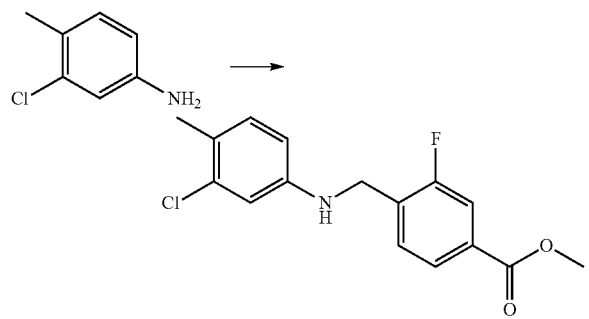

A solution of 3-chloro-4-methylaniline (1.000 g, 7.062 mmol), methyl 4-(bromomethyl)-3-fluorobenzoate (1.919 g, 7.768 mmol) and potassium carbonate (1.952 g, 14.124 mmol) in acetonitrile (10 mL) was stirred at the room temperature for 15 hr, filtered to remove solids, and concentrated under the reduced pressure to remove the solvents. The residue was chromatographed (SiO$_2$, 40 g cartridge; ethyl acetate/hexane=0% to 10%) to give methyl 4-(((3-chloro-4-methylphenyl)amino)methyl)-3-fluorobenzoate as pale yellow oil (1.041 g, 47.9%).

[Step 2] Methyl 4-(((3-chloro-4-methylphenyl)((4-nitrophenoxy)carbonyl)amino)methyl)-3-fluorobenzoate

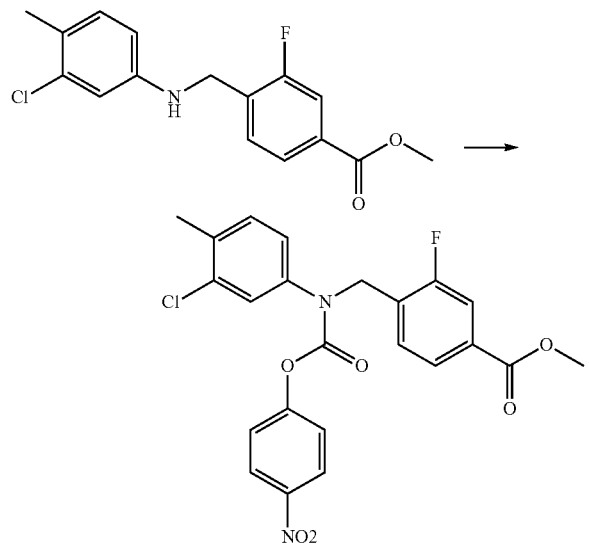

A solution of methyl 4-(((3-chloro-4-methylphenyl)amino)methyl)-3-fluorobenzoate (0.500 g, 1.625 mmol), 4-nitrophenyl carbonochloridate (0.491 g, 2.437 mmol) and potassium carbonate (0.449 g, 3.249 mmol) in dichloromethane (5 mL) was stirred at the room temperature for 15 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 10%) to give methyl 4-(((3-chloro-4-methylphenyl)((4-nitrophenoxy)carbonyl)amino)methyl)-3-fluorobenz oate as pale yellow oil (0.337 g, 43.9%).

[Step 3] Methyl 4-((N-(3-chloro-4-methylphenyl)-4-ethylpiperazine-1-carboxamido)methyl)-3-fluorobenzoate

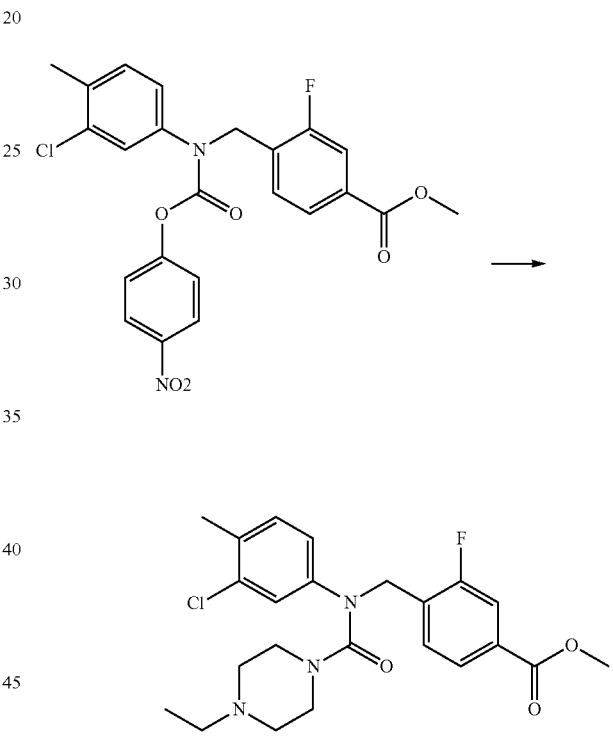

A solution of methyl 4-(((3-chloro-4-methylphenyl)((4-nitrophenoxy)carbonyl)amino)methyl)-3-fluorobenz oate (0.300 g, 0.634 mmol), 1-ethylpiperazine (0.217 g, 1.903 mmol) and potassium carbonate (0.438 g, 3.172 mmol) in N,N-dimethylformide (5 mL) was stirred at 80° C. for 5 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 24 g cartridge; methanol/dichloromethane=0% to 10%) to give methyl 4-((N-(3-chloro-4-methylphenyl)-4-ethylpiperazine-1-carboxamido)methyl)-3-fluorobenzoate as pale yellow oil (0.201 g, 70.7%).

[Step 4] N-(3-chloro-4-methylphenyl)-4-ethyl-N-(2-fluoro-4-(hydrazinecarbonyl)benzyl)piperazine-1-carboxamide

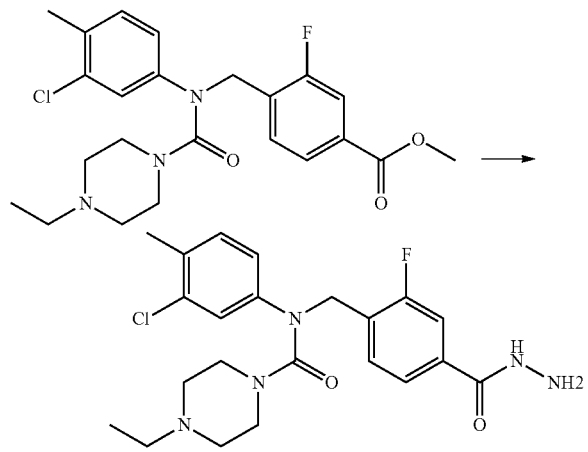

A mixture of methyl 4-((N-(3-chloro-4-methylphenyl)-4-ethylpiperazine-1-carboxamido)methyl)-3-fluorobenzoate (0.280 g, 0.625 mmol) and hydrazine monohydrate (0.608 mL, 12.502 mmol) in ethanol (3 mL) was heated at reflux for 16 hr, and cooled down to the ambient temperature, concentrated under the reduced pressure. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The crude N-(3-chloro-4-methylphenyl)-4-ethyl-N-(2-fluoro-4-(hydrazinecarbonyl)benzyl)piperazine-1-carboxamide was used without further purification (0.280 g, 100.0%, light yellow solid).

[Step 5] Compound 21657

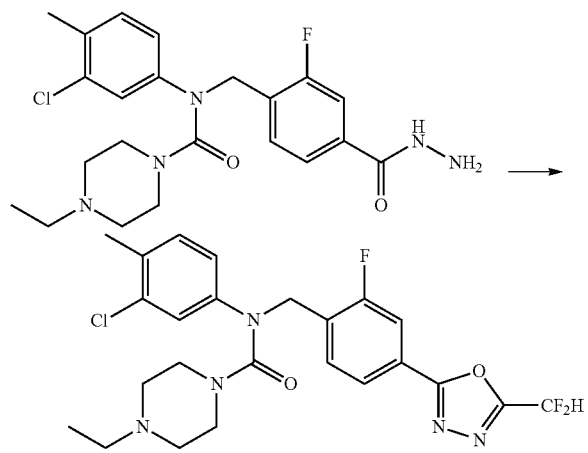

A solution of N-(3-chloro-4-methylphenyl)-4-ethyl-N-(2-fluoro-4-(hydrazinecarbonyl)benzyl)piperazine-1-carboxamide (0.140 g, 0.313 mmol) and N,N-diisopropylethylamine (0.109 mL, 0.625 mmol) in dichloromethane (2 mL) was mixed at 0° C. with 2,2-difluoroacetic anhydride (0.068 mL, 0.625 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(3-chloro-4-methylphenyl)-N-(4-(5-(difluoromethyl)-1,3,4-oxadiazol-2-yl)-2-fluorobenzyl)-4-ethylpiperazine-1-carboxamide as white solid (0.065 g, 41.2%).

$^1$H NMR (400 MHz, CDCl$_3$) δ 7.74 (dd, 1H, J=10.0, 1.6 Hz), 7.85 (dd, 1H, J=8.0, 1.6 Hz), 7.67-7.63 (m, 1H), 7.15-7.13 (m, 1H), 7.10-7.10 (m, 1H), 7.03-6.73 (m, 3H), 4.92 (s, 2H), 3.38-3.39 (m, 4H), 2.48-2.41 (m, 6H), 2.31 (s, 3H), 1.12 (t, 3H, J=6.8 Hz); LRMS (ES) m/z 508.6 (M$^+$+1).

Example 260. Compound 21658: N-(3-bromo-4-fluorophenyl)-4-ethyl-N-(2-fluoro-4-(5-(trifluoromethyl)-1,3,4-oxadiazol-2-yl)benzyl)piperazine-1-carboxamide

[Step 1] Methyl 4-(((3-bromo-4-fluorophenyl)amino)methyl)-3-fluorobenzoate

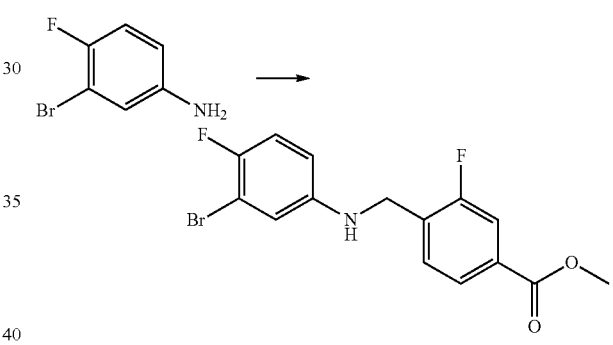

A solution of 3-bromo-4-fluoroaniline (1.000 g, 5.263 mmol), methyl 4-(bromomethyl)-3-fluorobenzoate (1.430 g, 5.789 mmol) and potassium carbonate (1.455 g, 10.525 mmol) in acetonitrile (10 mL) was stirred at the room temperature for 15 hr, filtered to remove solids, and concentrated under the reduced pressure. The residue was chromatographed (SiO$_2$, 40 g cartridge; ethyl acetate/hexane=0% to 10%) to give methyl 4-(((3-bromo-4-fluorophenyl)amino)methyl)-3-fluorobenzoate as pale brown oil (1.104 g, 58.9%).

[Step 2] Methyl 4-(((3-bromo-4-fluorophenyl)((4-nitrophenoxy)carbonyl)amino)methyl)-3-fluorobenzoate

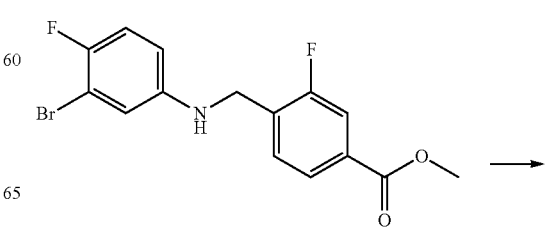

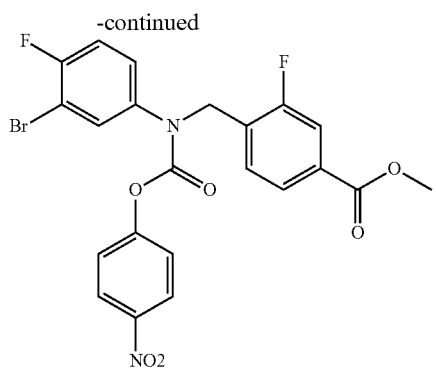

A solution of methyl 4-(((3-bromo-4-fluorophenyl)amino)methyl)-3-fluorobenzoate (0.500 g, 1.404 mmol), 4-nitrophenyl carbonochloridate (0.424 g, 2.106 mmol) and potassium carbonate (0.388 g, 2.808 mmol) in dichloromethane (5 mL) was stirred at the room temperature for 15 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 10%) to give methyl 4-(((3-bromo-4-fluorophenyl)((4-nitrophenoxy)carbonyl)amino)methyl)-3-fluorobenzoate as pale yellow oil (0.420 g, 57.4%).

[Step 3] Methyl 4-((N-(3-bromo-4-fluorophenyl)-4-ethylpiperazine-1-carboxamido)methyl)-3-fluorobenzoate

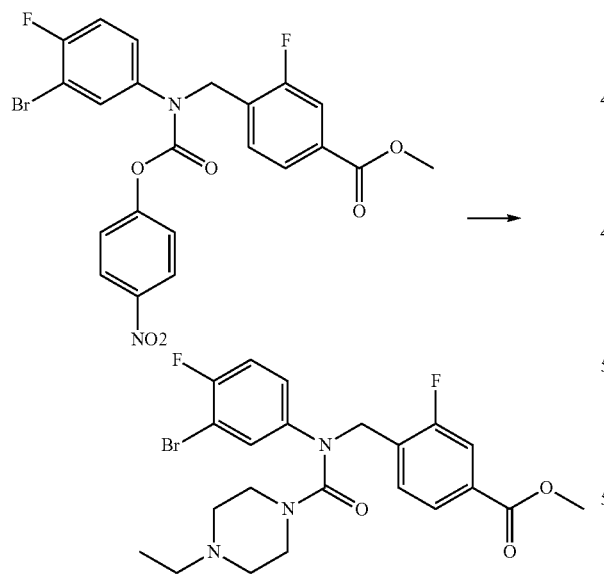

A solution of methyl 4-(((3-bromo-4-fluorophenyl)((4-nitrophenoxy)carbonyl)amino)methyl)-3-fluorobenzoate (0.300 g, 0.576 mmol), 1-ethylpiperazine (0.197 g, 1.727 mmol) and potassium carbonate (0.398 g, 2.878 mmol) in N,N-dimethylformide (5 mL) was stirred at 80° C. for 5 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 24 g cartridge; methanol/dichloromethane=0% to 10%) to give methyl 4-((N-(3-bromo-4-fluorophenyl)-4-ethylpiperazine-1-carboxamido)methyl)-3-fluorobenzoate as pale yellow oil (0.210 g, 70.0%).

[Step 4] N-(3-bromo-4-fluorophenyl)-4-ethyl-N-(2-fluoro-4-(hydrazinecarbonyl)benzyl)piperazine-1-carboxamide

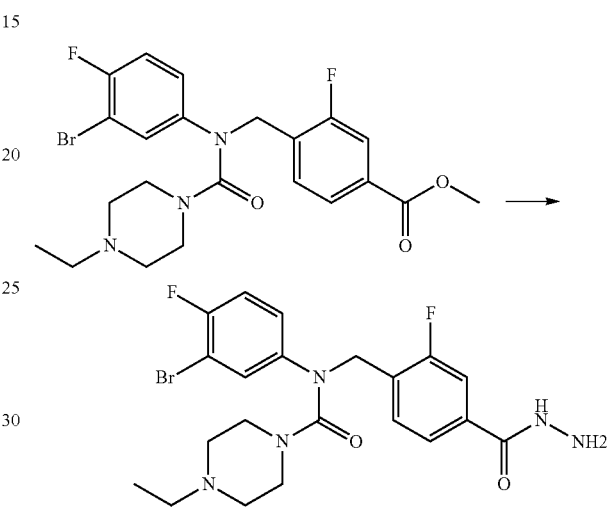

A mixture of methyl 4-((N-(3-bromo-4-fluorophenyl)-4-ethylpiperazine-1-carboxamido)methyl)-3-fluorobenzoate (0.130 g, 0.262 mmol) and hydrazine monohydrate, (0.255 mL, 5.238 mmol) in ethanol (2 mL) was heated at reflux for 16 hr, and cooled down to the ambient temperature, concentrated under the reduced pressure. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The crude N-(3-bromo-4-fluorophenyl)-4-ethyl-N-(2-fluoro-4-(hydrazinecarbonyl)benzyl)piperazine-1-carboxamide was used without further purification (0.129 g, 99.2%, white solid).

[Step 5] Compound 21658

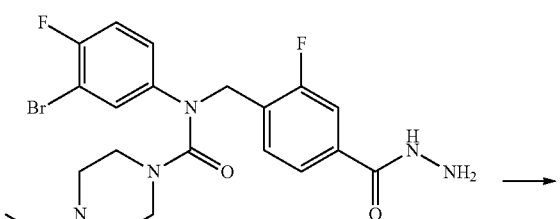

845

-continued

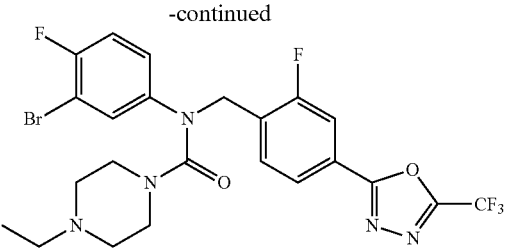

A solution of N-(3-bromo-4-fluorophenyl)-4-ethyl-N-(2-fluoro-4-(hydrazinecarbonyl)benzyl)piperazine-1-carboxamide (0.064 g, 0.129 mmol) and N,N-diisopropylethylamine (0.045 mL, 0.258 mmol) in dichloromethane (1 mL) was mixed at 0° C. with trifluoroacetic anhydride (0.036 mL, 0.258 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(3-bromo-4-fluorophenyl)-4-ethyl-N-(2-fluoro-4-(5-(trifluoromethyl)-1,3,4-oxadiazol-2-yl)benzyl)piperazine-1-carboxamide as colorless oil (0.039 g, 52.7%).

$^1$H NMR (400 MHz, CDCl$_3$) δ 7.87 (dd, 1H, J=8.0, 1.7 Hz), 7.75 (dd, 1H, J=10.0, 1.6 Hz), 7.71-7.67 (m, 1H), 7.31 (dd, 1H, J=5.8, 2.6 Hz), 7.09-6.99 (m, 2H), 4.90 (s, 2H), 3.39-3.40 (m, 4H), 2.51-2.43 (m, 6H), 1.13-1.14 (m, 3H); LRMS (ES) m/z 574.57 (M$^+$+1).

Example 261. Compound 21659: N-(2,3-difluorophenyl)-4-ethyl-N-(2-fluoro-4-(5-(trifluoromethyl)-1,3,4-oxadiazol-2-yl)benzyl)piperazine-1-carboxamide

[Step 1] Methyl 4-4-(2,3-difluorophenyl)amino) methyl)-3-fluorobenzoate

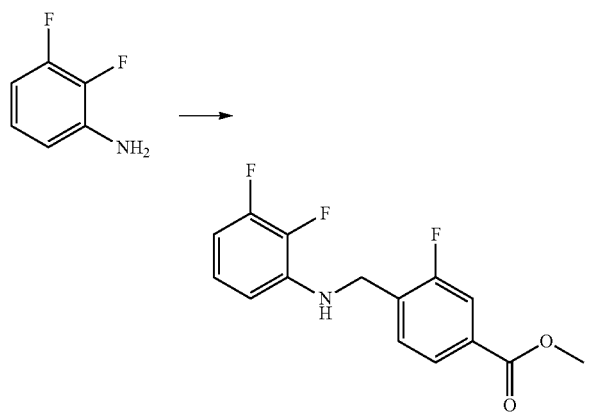

A solution of 2,3-difluoroaniline (1.000 g, 7.745 mmol), methyl 4-(bromomethyl)-3-fluorobenzoate (2.105 g, 8.520 mmol) and potassium carbonate (2.141 g, 15.491 mmol) in acetonitrile (10 mL) was stirred at the room temperature for 15 hr, filtered to remove solids, and concentrated under the reduced pressure. The residue was chromatographed (SiO$_2$, 40 g cartridge; ethyl acetate/hexane=0% to 10%) to give methyl 4-(((2,3-difluorophenyl)amino)methyl)-3-fluorobenzoate as pale brown oil (0.904 g, 39.5%).

[Step 2] Methyl 4-4-(2,3-difluorophenyl)((4-nitrophenoxy)carbonyl)amino)methyl)-3-fluorobenzoate

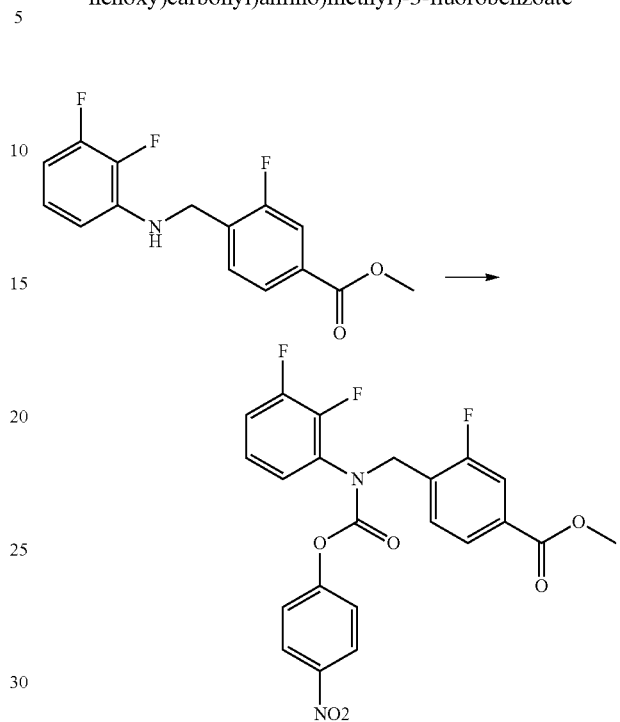

A solution of methyl 4-(((2,3-difluorophenyl)amino) methyl)-3-fluorobenzoate (0.500 g, 1.693 mmol), 4-nitrophenyl carbonochloridate (0.512 g, 2.540 mmol) and potassium carbonate (0.468 g, 3.387 mmol) in dichloromethane (5 mL) was stirred at the room temperature for 15 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 10%) to give methyl 4-(((2,3-difluorophenyl)((4-nitrophenoxy)carbonyl)amino) methyl-3-fluorobenzoate as pale yellow oil (0.425 g, 54.5%).

[Step 3] Methyl 4-((N-(2,3-difluorophenyl)-4-ethylpiperazine-1-carboxamido)methyl)-3-fluorobenzoate

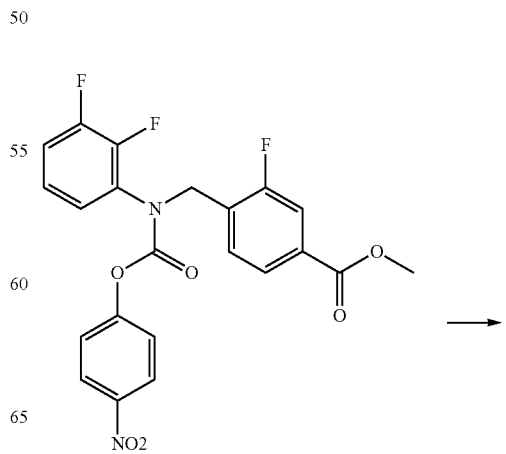

-continued

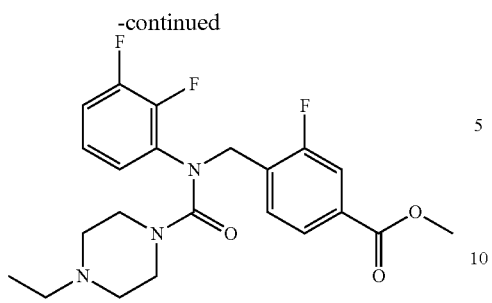

A solution of methyl 4-4-(2,3-difluorophenyl)((4-nitrophenoxy)carbonyl)amino)methyl)-3-fluorobenzoate (0.300 g, 0.652 mmol), 1-ethylpiperazine (0.223 g, 1.955 mmol) and potassium carbonate (0.450 g, 3.258 mmol) in N,N-dimethylformide (5 mL) was stirred at 80° C. for 5 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 24 g cartridge; methanol/dichloromethane=0% to 10%) to give methyl 4-((N-(2,3-difluorophenyl)-4-ethylpiperazine-1-carboxamido)methyl)-3-fluorobenzoate as pale yellow oil (0.165 g, 58.1%).

[Step 4] N-(2,3-difluorophenyl)-4-ethyl-N-(2-fluoro-4-(hydrazinecarbonyl)benzyl)piperazine-1-carboxamide

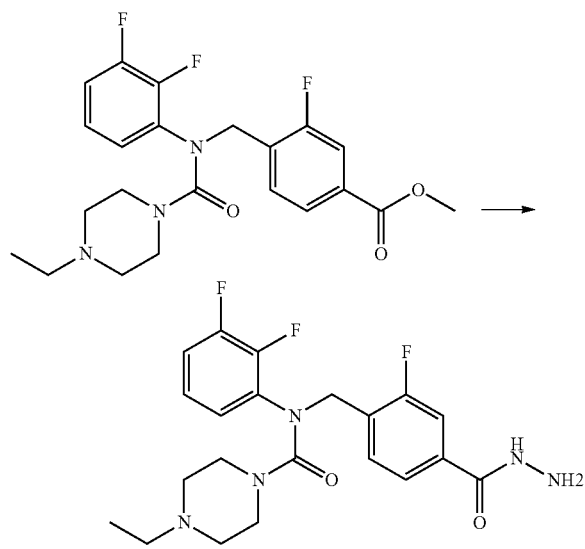

A mixture of methyl 4-((N-(2,3-difluorophenyl)-4-ethylpiperazine-1-carboxamido)methyl)-3-fluorobenzoate (0.180 g, 0.413 mmol) and hydrazine monohydrate (0.402 mL, 8.267 mmol) in ethanol (3 mL) was heated at reflux for 16 hr, cooled down to the ambient temperature, and concentrated under the reduced pressure to remove the solvents. Then, water was added to the reaction mixture, followed by extraction with dichloromethane. The bi-phasic mixture was passed through a plastic frit to remove the solid residues and aqueous layer, and the organic layer collected was concentrated in vacuo. The crude N-(2,3-difluorophenyl)-4-ethyl-N-(2-fluoro-4-(hydrazinecarbonyl)benzyl)piperazine-1-carboxamide was used without further purification (0.178 g, 98.9%, light yellow solid).

[Step 5] N-(2,3-difluorophenyl)-4-ethyl-N-(2-fluoro-4-(2-(2,2,2-trifluoroacetyl)hydrazine-1-carbonyl)benzyl)piperazine-1-carboxamide

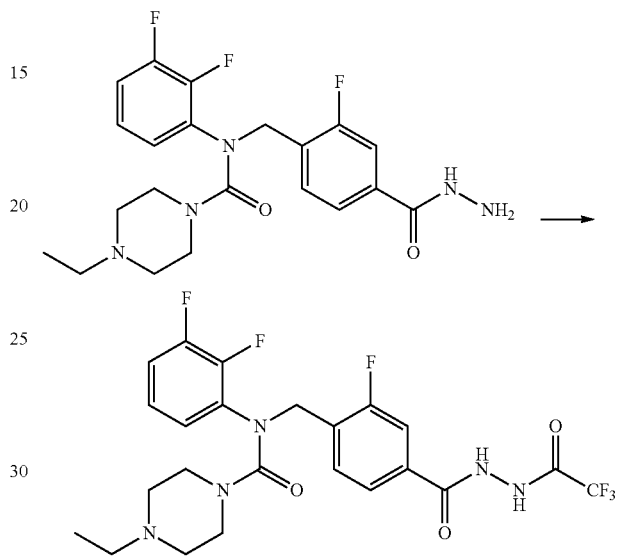

A solution of N-(2,3-difluorophenyl)-4-ethyl-N-(2-fluoro-4-(hydrazinecarbonyl)benzyl)piperazine-1-carboxamide (0.089 g, 0.204 mmol) and N,N-diisopropylethylamine (0.071 mL, 0.409 mmol) in dichloromethane (1 mL) was mixed at 0° C. with trifluoroacetic anhydride (0.058 mL, 0.409 mmol), and stirred at the room temperature for 16 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(2,3-difluorophenyl)-4-ethyl-N-(2-fluoro-4-(2-(2,2,2-trifluoroacetyl)hydrazine-1-carbonyl)benzyl)piperazine-1-carboxamide as light yellow solid (0.106 g, 97.6%).

[Step 6] Compound 21659

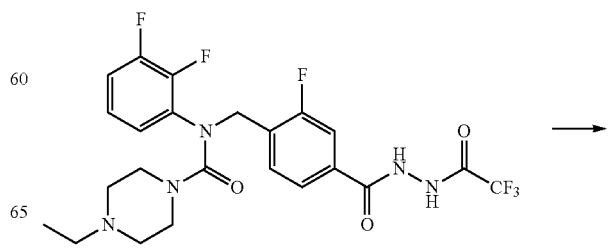

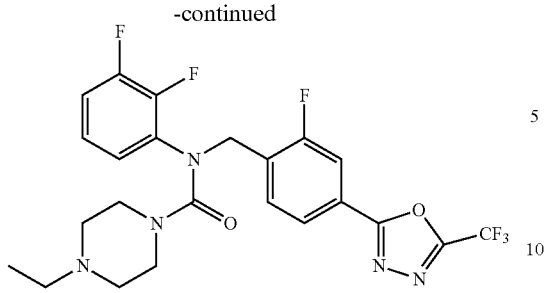

A solution of N-(2,3-difluorophenyl)-4-ethyl-N-(2-fluoro-4-(2-(2,2,2-trifluoroacetyl)hydrazine-1-carbonyl)benzyl)piperazine-1-carboxamide (0.106 g, 0.199 mmol) and 1-methoxy-N-triethylammoniosulfonyl-methanimidate (Burgess reagent, 0.071 g, 0.299 mmol) in tetrahydrofuran (1 mL) was stirred at 150° C. for 16 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(2,3-difluorophenyl)-4-ethyl-N-(2-fluoro-4-(5-(trifluoromethyl)-1,3,4-oxadiazol-2-yl)benzyl)piperazine-1-carboxamide as colorless oil (0.047 g, 45.9%).

$^1$H NMR (400 MHz, CDCl$_3$) δ 7.86 (dd, 1H, J=8.1, 1.6 Hz), 7.82-7.78 (m, 1H), 7.69 (dd, 1H, J=9.9, 1.5 Hz), 7.05-7.01 (m, 2H), 6.88-6.84 (m, 1H), 4.90 (s, 2H), 3.34-3.35 (m, 4H), 2.46-2.39 (m, 6H), 1.10 (t, 3H, J=7.0 Hz); LRMS (ES) m/z 514.4 (M$^+$+1).

Example 262. Compound 21660: N-(3-chloro-4-methylphenyl)-4-ethyl-N-(2-fluoro-4-(5-(trifluoromethyl)-1,3,4-oxadiazol-2-yl)benzyl)piperazine-1-carboxamide

[Step 1] Methyl 4-(((3-chloro-4-methylphenyl)amino)methyl)-3-fluorobenzoate

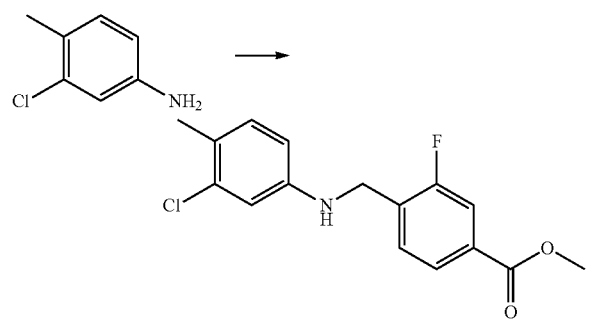

A solution of 3-chloro-4-methylaniline (1.000 g, 7.062 mmol), methyl 4-(bromomethyl)-3-fluorobenzoate (1.919 g, 7.768 mmol) and potassium carbonate (1.952 g, 14.124 mmol) in acetonitrile (10 mL) was stirred at the room temperature for 15 hr, filtered to remove solids, and concentrated under the reduced pressure. The residue was chromatographed (SiO$_2$, 40 g cartridge; ethyl acetate/hexane=0% to 10%) to give methyl 4-(((3-chloro-4-methylphenyl)amino)methyl)-3-fluorobenzoate as pale yellow oil (1.041 g, 47.9%).

[Step 2] Methyl 4-(((3-chloro-4-methylphenyl)((4-nitrophenoxy)carbonyl)amino)methyl)-3-fluorobenzoate

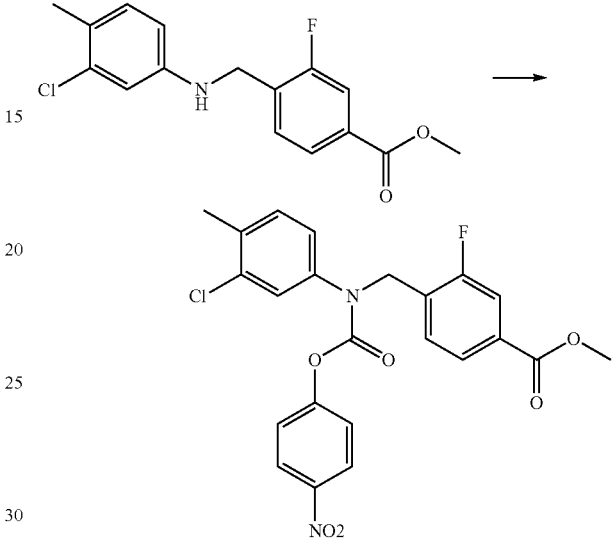

A solution of methyl 4-(((3-chloro-4-methylphenyl)amino)methyl)-3-fluorobenzoate (0.500 g, 1.625 mmol), 4-nitrophenyl carbonochloridate (0.491 g, 2.437 mmol) and potassium carbonate (0.449 g, 3.249 mmol) in dichloromethane (5 mL) was stirred at the room temperature for 15 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 10%) to give methyl 4-4-(3-chloro-4-methylphenyl)((4-nitrophenoxy)carbonyl)amino)methyl)-3-fluorobenz oate as pale yellow oil (0.337 g, 43.9%).

[Step 3] Methyl 4-((N-(3-chloro-4-methylphenyl)-4-ethylpiperazine-1-carboxamido)methyl)-3-fluorobenzoate

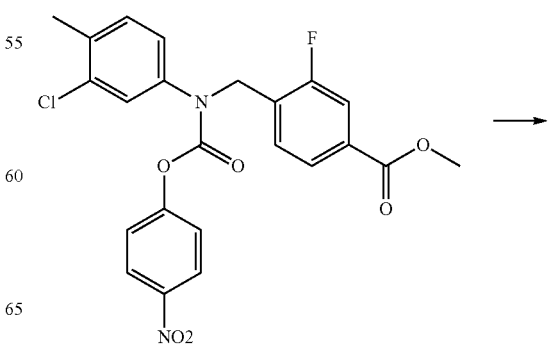

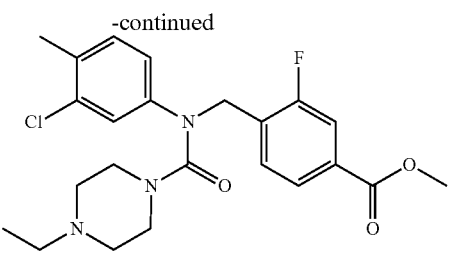

A solution of methyl 4-(((3-chloro-4-methylphenyl)((4-nitrophenoxy)carbonyl)amino)methyl)-3-fluorobenzoate (0.300 g, 0.634 mmol), 1-ethylpiperazine (0.217 g, 1.903 mmol) and potassium carbonate (0.438 g, 3.172 mmol) in N,N-dimethylformide (5 mL) was stirred at 80° C. for 5 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 24 g cartridge; methanol/dichloromethane=0% to 10%) to give methyl 4-((N-(3-chloro-4-methylphenyl)-4-ethylpiperazine-1-carboxamido)methyl)-3-fluorobenzoate as pale yellow oil (0.201 g, 70.7%).

[Step 4] N-(3-chloro-4-methylphenyl)-4-ethyl-N-(2-fluoro-4-(hydrazinecarbonyl)benzyl)piperazine-1-carboxamide

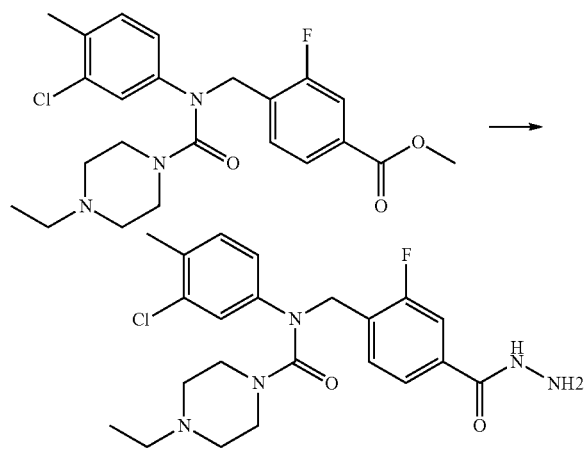

A mixture of methyl 4-((N-(3-chloro-4-methylphenyl)-4-ethylpiperazine-1-carboxamido)methyl)-3-fluorobenzoate (0.280 g, 0.625 mmol) and hydrazine monohydrate (0.608 mL, 12.502 mmol) in ethanol (3 mL) was heated at reflux for 16 hr, cooled down to the ambient temperature, and concentrated under the reduced pressure to remove the solvents. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The crude N-(3-chloro-4-methylphenyl)-4-ethyl-N-(2-fluoro-4-(hydrazinecarbonyl)benzyl)piperazine-1-carboxamide was used without further purification (0.280 g, 100.0%, light yellow solid).

[Step 5] N-(3-chloro-4-methylphenyl)-4-ethyl-N-(2-fluoro-4-(2-(2,2,2-trifluoroacetyl)hydrazine-1-carbonyl)benzyl)piperazine-1-carboxamide

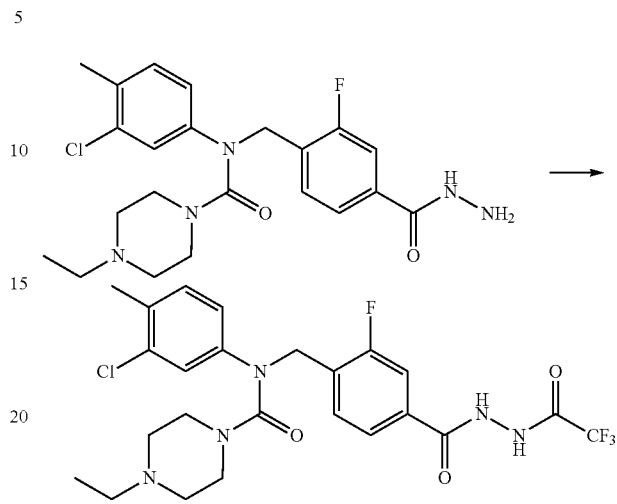

A solution of N-(3-chloro-4-methylphenyl)-4-ethyl-N-(2-fluoro-4-(hydrazinecarbonyl)benzyl)piperazine-1-carboxamide (0.140 g, 0.313 mmol) and N,N-diisopropylethylamine (0.109 mL, 0.625 mmol) in dichloromethane (2 mL) was mixed at 0° C. with trifluoroacetic anhydride (0.088 mL, 0.625 mmol), and stirred at the room temperature for 16 hr. The precipitates were collected by filtration, washed by dichloromethane, and dried to give N-(3-chloro-4-methylphenyl)-4-ethyl-N-(2-fluoro-4-(2-(2,2,2-trifluoroacetyl)hydrazine-1-carbonyl)benzyl)piperazine-1-carboxamide as white solid (0.123 g, 72.3%).

[Step 6] Compound 21660

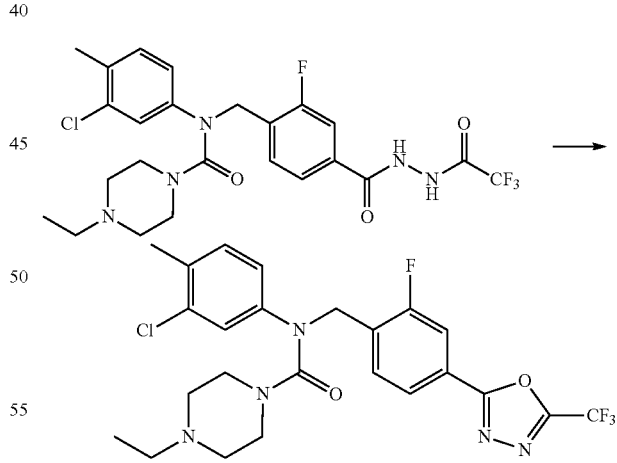

A solution of N-(3-chloro-4-methylphenyl)-4-ethyl-N-(2-fluoro-4-(2-(2,2,2-trifluoroacetyl)hydrazine-1-carbonyl)benzyl)piperazine-1-carboxamide (0.123 g, 0.226 mmol) and 1-methoxy-N-triethylammoniosulfonyl-methanimidate (Burgess reagent, 0.081 g, 0.339 mmol) in tetrahydrofuran (2 mL) was stirred at 150° C. for 16 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 3%) to give N-(3-chloro-4-methylphenyl)-4-ethyl-N-(2-fluoro-4-(5-(trifluoromethyl)-1,3,4-oxadiazol-2-yl)benzyl)piperazine-1-carboxamide as colorless oil (0.038 g, 32.0%).

$^1$H NMR (400 MHz, CDCl$_3$) δ 7.85 (dd, 1H, J=8.0, 1.6 Hz), 7.74 (dd, 1H, J=10.0, 1.6 Hz), 7.69-7.65 (m, 1H), 7.15-7.13 (m, 1H), 7.10-7.10 (m, 1H), 6.88 (dd, 1H, J=8.2, 2.3 Hz), 4.93 (s, 2H), 3.37-3.38 (m, 4H), 2.47-2.40 (m, 6H), 2.31 (s, 3H), 1.11 (t, 3H, J=7.0 Hz); LRMS (ES) m/z 526.6 (M$^+$+1).

Example 263. Compound 21664: (R)—N-(3-chloro-4-fluorophenyl)-N-(2-fluoro-4-(5-(trifluoromethyl)-1,3,4-oxadiazol-2-yl)benzyl)-3-hydroxypyrrolidine-1-carboxamide

[Step 1] Methyl (R)-4-((N-(3-chloro-4-fluorophenyl)-3-hydroxypyrrolidine-1-carboxamido)methyl)-3-fluorobenzoate

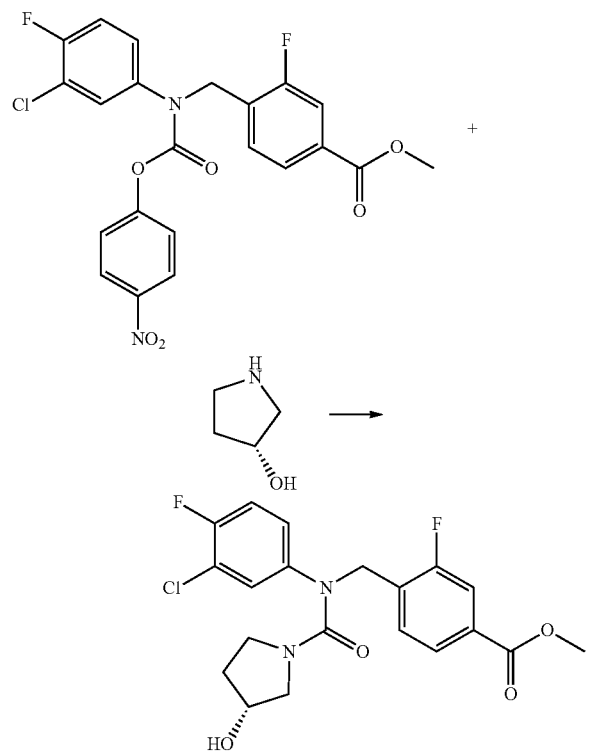

Methyl 4-(((3-chloro-4-fluorophenyl)((4-nitrophenoxy)carbonyl)amino)methyl)-3-fluorobenzoate (0.500 g, 1.049 mmol), (R)-pyrrolidin-3-ol (0.457 g, 5.243 mmol) and potassium carbonate (0.290 g, 2.097 mmol) were mixed at the room temperature in N,N-dimethylformamide (5 mL) and then stirred at 40° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give methyl (R)-4-((N-(3-chloro-4-fluorophenyl)-3-hydroxypyrrolidine-1-carboxamido)methyl)-3-fluorobenzoate as yellow oil (0.338 g, 75.8%).

[Step 2] (R)—N-(3-chloro-4-fluorophenyl)-N-(2-fluoro-4-(hydrazinecarbonyl)benzyl)-3-hydroxypyrrolidine-1-carboxamide

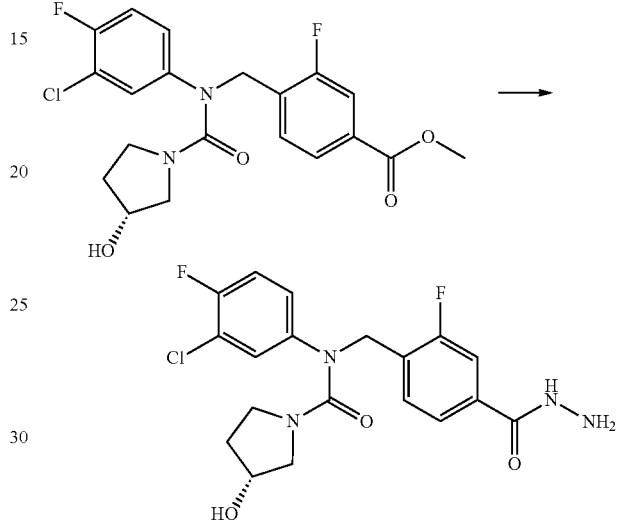

Methyl (R)-4-((N-(3-chloro-4-fluorophenyl)-3-hydroxypyrrolidine-1-carboxamido)methyl)-3-fluorobenzoate (0.338 g, 0.795 mmol) and hydrazine monohydrate (0.386 mL, 7.951 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give (R)—N-(3-chloro-4-fluorophenyl)-N-(2-fluoro-4-(hydrazinecarbonyl)benzyl)-3-hydroxypyrrolidine-1-carboxamide as white foam (0.165 g, 48.7%).

[Step 3] Compound 21664

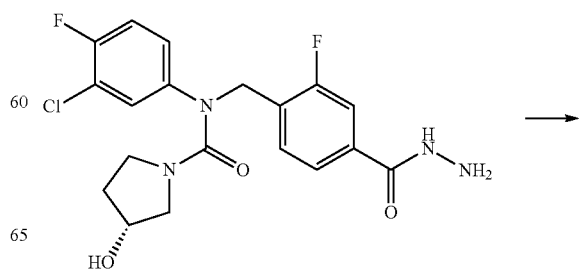

855

-continued

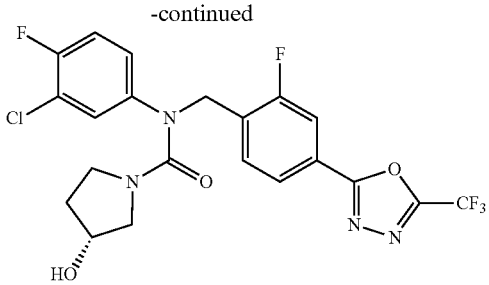

(R)—N-(3-chloro-4-fluorophenyl)-N-(2-fluoro-4-(hydrazinecarbonyl)benzyl)-3-hydroxypyrrolidine-1-carboxamide (0.082 g, 0.193 mmol), trifluoroacetic anhydride (0.082 mL, 0.580 mmol) and triethylamine (0.135 mL, 0.967 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give (R)—N-(3-chloro-4-fluorophenyl)-N-(2-fluoro-4-(5-(trifluoromethyl)-1,3,4-oxadiazol-2-yl)benzyl)-3-hydroxypyrrolidine-1-carboxamide as yellow foam (0.071 g, 73.0%).

$^1$H NMR (400 MHz, CDCl$_3$) δ 7.89 (dd, 1H, J=8.1, 1.7 Hz), 7.82-7.71 (m, 2H), 7.20 (dd, 1H, J=6.4, 2.7 Hz), 7.09 (t, 1H, J=8.6 Hz), 7.00 (ddd, 1H, J=8.9, 4.1, 2.7 Hz), 5.00 (d, 1H, J=15.5 Hz), 4.88 (d, 1H, J=15.5 Hz), 4.38 (tt, 1H, J=4.3, 2.4 Hz), 3.37-3.15 (m, 4H), 1.97-1.79 (m, 1H); LRMS (ES) m/z 503.4 (M$^+$+1).

Example 264. Compound 21665: (S)—N-(3-chloro-4-fluorophenyl)-N-(4-(5-(difluoromethyl)-1,3,4-oxadiazol-2-yl)-2-fluorobenzyl)-3-fluoropyrrolidine-1-carboxamide

[Step 1] Methyl 4-(((3-chloro-4-fluorophenyl)amino)methyl)-3-fluorobenzoate

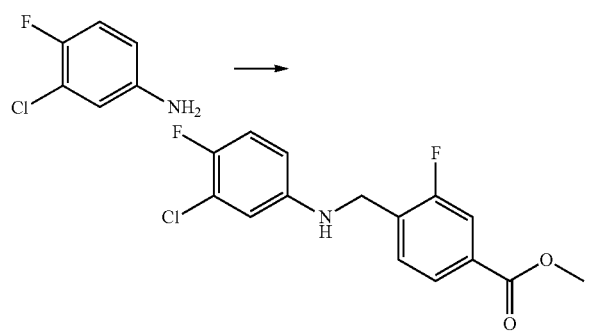

A solution of 3-chloro-4-fluoroaniline (3.000 g, 20.610 mmol), methyl 4-(bromomethyl)-3-fluorobenzoate (6.110 g, 24.732 mmol) and potassium carbonate (5.697 g, 41.220 mmol) in acetonitrile (30 mL) was stirred at the room temperature for 14 hr, filtered to remove solids, and concentrated under the reduced pressure to remove the solvents. The residue was chromatographed (SiO$_2$, 80 g cartridge; ethyl acetate/hexane=0% to 10%) to give methyl 4-(((3-chloro-4-fluorophenyl)amino)methyl-3-fluorobenzoate as yellow oil (4.030 g, 62.7%).

[Step 2] Methyl 4-(((3-chloro-4-fluorophenyl)((4-nitrophenoxy)carbonyl)amino)methyl)-3-fluorobenzoate

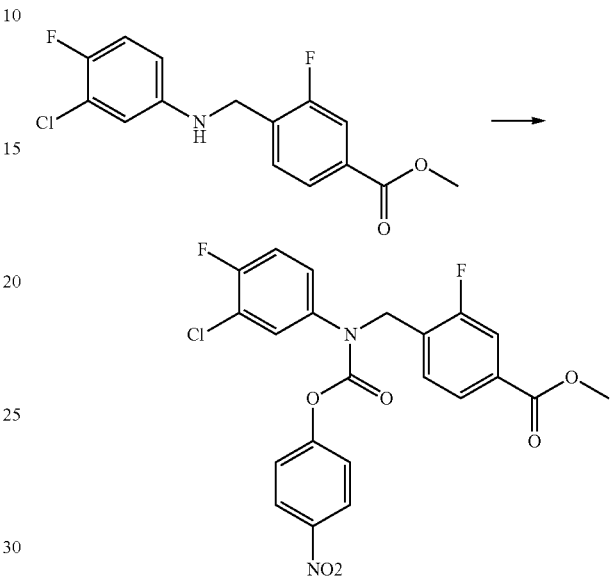

A solution of methyl 4-(((3-chloro-4-fluorophenyl)amino)methyl)-3-fluorobenzoate (2.000 g, 6.416 mmol), 4-nitrophenyl carbonochloridate (1.940 g, 9.624 mmol) and potassium carbonate (2.660 g, 19.249 mmol) in dichloromethane (20 mL) was stirred at the room temperature for 7 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 20%) to give methyl 4-(((3-chloro-4-fluorophenyl)((4-nitrophenoxy)carbonyl)amino)methyl)-3-fluorobenzoate as white solid (2.150 g, 70.3%).

[Step 3] Methyl (S)-4-((N-(3-chloro-4-fluorophenyl)-3-fluoropyrrolidine-1-carboxamido)methyl)-3-fluorobenzoate

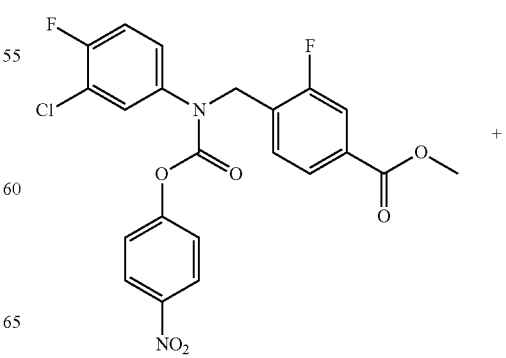

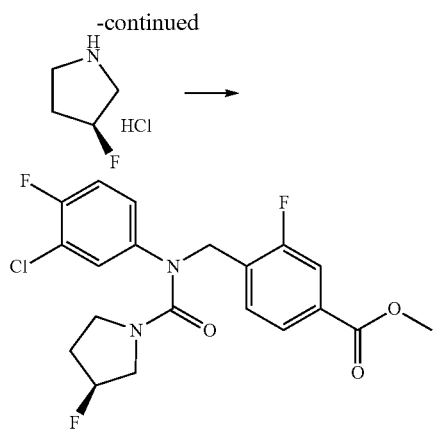

Methyl 4-(((3-chloro-4-fluorophenyl)((4-nitrophenoxy)carbonyl)amino)methyl)-3-fluorobenzoate (0.500 g, 1.049 mmol), (S)-3-fluoropyrrolidine hydrochloride (0.457 g, 5.243 mmol) and potassium carbonate (0.290 g, 2.097 mmol) were mixed at the room temperature in N,N-dimethylformamide (5 mL) and then stirred at 40° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 20%) to give methyl (S)-4-((N-(3-chloro-4-fluorophenyl)-3-fluoropyrrolidine-1-carboxamido)methyl)-3-fluorobenzoate as yellow oil (0.399 g, 89.2%).

[Step 4] (S)—N-(3-chloro-4-fluorophenyl)-3-fluoro-N-(2-fluoro-4-(hydrazinecarbonyl)benzyl)pyrrolidine-1-carboxamide

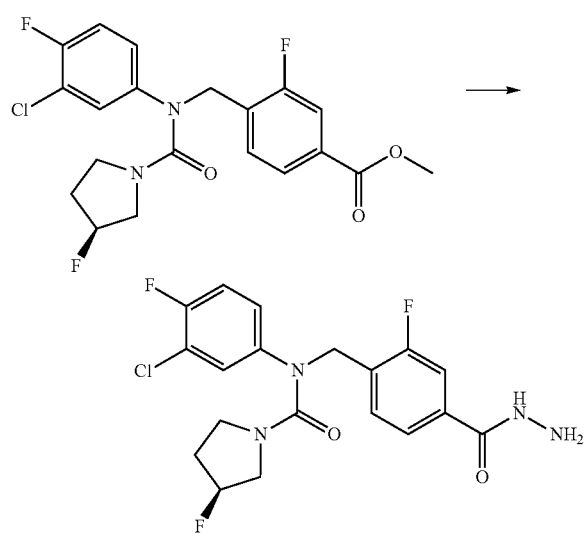

Methyl (S)-4-((N-(3-chloro-4-fluorophenyl)-3-fluoropyrrolidine-1-carboxamido)methyl)-3-fluorobenzoate (0.399 g, 0.935 mmol) and hydrazine monohydrate (0.454 mL, 9.351 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give (S)—N-(3-chloro-4-fluorophenyl)-3-fluoro-N-(2-fluoro-4-(hydrazinecarbonyl)benzyl)pyrrolidine-1-carboxamide as white foam (0.337 g, 84.4%).

[Step 5] Compound 21665

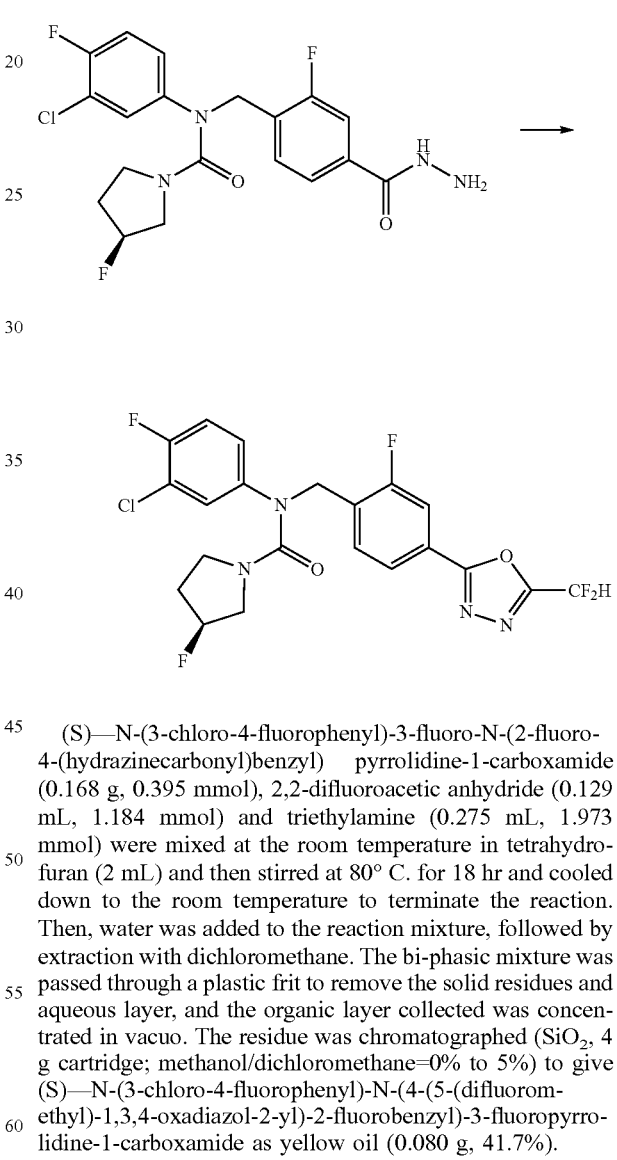

(S)—N-(3-chloro-4-fluorophenyl)-3-fluoro-N-(2-fluoro-4-(hydrazinecarbonyl)benzyl) pyrrolidine-1-carboxamide (0.168 g, 0.395 mmol), 2,2-difluoroacetic anhydride (0.129 mL, 1.184 mmol) and triethylamine (0.275 mL, 1.973 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give (S)—N-(3-chloro-4-fluorophenyl)-N-(4-(5-(difluoromethyl)-1,3,4-oxadiazol-2-yl)-2-fluorobenzyl)-3-fluoropyrrolidine-1-carboxamide as yellow oil (0.080 g, 41.7%).

$^1$H NMR (400 MHz, CDCl$_3$) δ 7.89 (dd, 1H, J=8.0, 1.6 Hz), 7.80-7.71 (m, 2H), 7.22 (dd, 1H, J=6.4, 2.6 Hz), 7.10 (t, 1H, J=8.6 Hz), 7.06-6.78 (m, 2H), 5.23-5.05 (m, 1H), 5.02 (d, 1H, J=15.4 Hz), 4.86 (d, 1H, J=15.4 Hz), 3.58-3.44 (m, 2H), 3.42-3.30 (m, 2H), 3.30-3.14 (m, 2H), 2.22- 2.08 (m, 1H), 2.01-1.76 (m, 1H); LRMS (ES) m/z 482.2 (M$^+$+1).

Example 265. Compound 21666: (S)—N-(3-chloro-4-fluorophenyl)-3-fluoro-N-(2-fluoro-4-(5-(trifluoromethyl)-1,3,4-oxadiazol-2-yl)benzyl)pyrrolidine-1-carboxamide

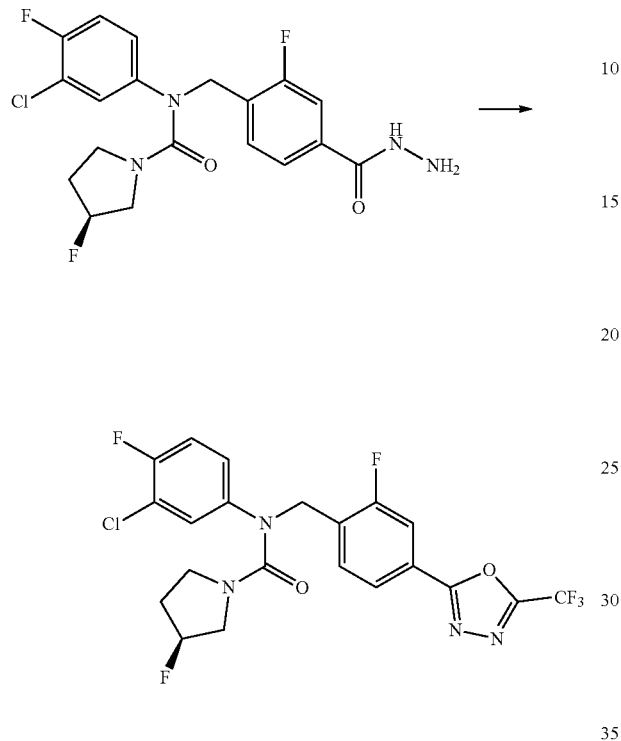

(S)—N-(3-chloro-4-fluorophenyl)-3-fluoro-N-(2-fluoro-4-(hydrazinecarbonyl)benzyl) pyrrolidine-1-carboxamide (0.168 g, 0.395 mmol), trifluoroacetic anhydride (0.167 mL, 1.184 mmol) and triethylamine (0.275 mL, 1.973 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give (S)—N-(3-chloro-4-fluorophenyl)-3-fluoro-N-(2-fluoro-4-(5-(trifluoromethyl)-1,3,4-oxadiazol-2-yl)benzyl)pyrrolidine-1-carboxamide as yellow foam (0.170 g, 85.4%).

$^1$H NMR (400 MHz, CDCl$_3$) δ 7.90 (dd, 1H, J=8.1, 1.7 Hz), 7.79 (d, 1H, J=7.5 Hz), 7.77-7.71 (m, 1H), 7.22 (dd, 1H, J=6.4, 2.7 Hz), 7.11 (t, 1H, J=8.6 Hz), 7.01 (ddd, 1H, J=8.8, 4.1, 2.7 Hz), 5.23-5.05 (m, 1H), 5.03 (d, 1H, J=15.4 Hz), 4.87 (d, 1H, J=15.4 Hz), 3.59-3.44 (m, 1H), 3.44-3.30 (m, 2H), 3.22 (qd, 1H, J=11.3, 10.8, 4.9 Hz), 2.22-2.08 (m, 1H), 2.01-1.76 (m, 1H); LRMS (ES) m/z 505.3 (M$^+$+1).

Example 266. Compound 21667: N-(3-chloro-4-fluorophenyl)-N-(4-(5-(difluoromethyl)-1,3,4-oxadiazol-2-yl)-2-fluorobenzyl)-3,3-difluoropyrrolidine-1-carboxamide

[Step 1] Methyl 4-((N-(3-chloro-4-fluorophenyl)-3,3-difluoropyrrolidine-1-carboxamido)methyl)-3-fluorobenzoate

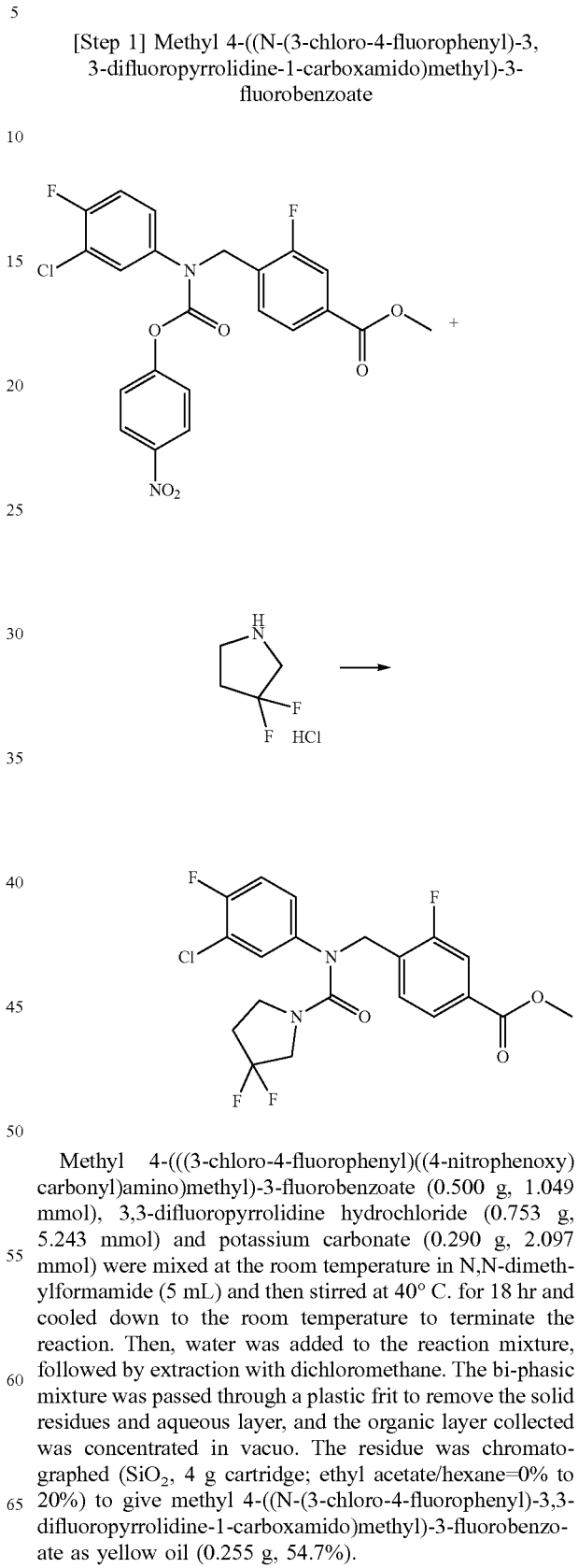

Methyl 4-(((3-chloro-4-fluorophenyl)((4-nitrophenoxy)carbonyl)amino)methyl)-3-fluorobenzoate (0.500 g, 1.049 mmol), 3,3-difluoropyrrolidine hydrochloride (0.753 g, 5.243 mmol) and potassium carbonate (0.290 g, 2.097 mmol) were mixed at the room temperature in N,N-dimethylformamide (5 mL) and then stirred at 40° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 20%) to give methyl 4-((N-(3-chloro-4-fluorophenyl)-3,3-difluoropyrrolidine-1-carboxamido)methyl)-3-fluorobenzoate as yellow oil (0.255 g, 54.7%).

861

[Step 2] N-(3-chloro-4-fluorophenyl)-3,3-difluoro-N-(2-fluoro-4-(hydrazinecarbonyl)benzyl)pyrrolidine-1-carboxamide

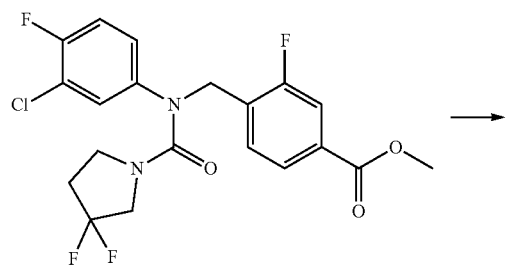

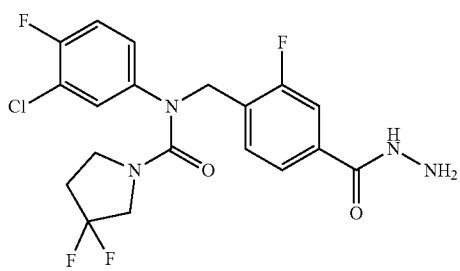

Methyl 4-((N-(3-chloro-4-fluorophenyl)-3,3-difluoropyrrolidine-1-carboxamido)methyl)-3-fluorobenzoate (0.255 g, 0.574 mmol) and hydrazine monohydrate (0.279 mL, 5.740 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(3-chloro-4-fluorophenyl)-3,3-difluoro-N-(2-fluoro-4-(hydrazinecarbonyl)benzyl)pyrrolidine-1-carboxamide as white foam (0.247 g, 96.7%).

[Step 3] Compound 21667

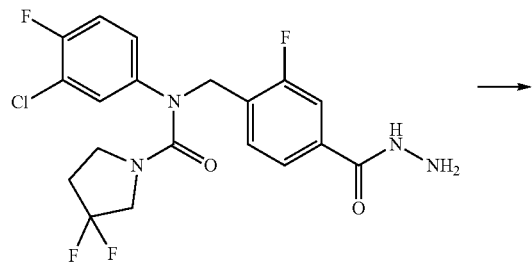

862

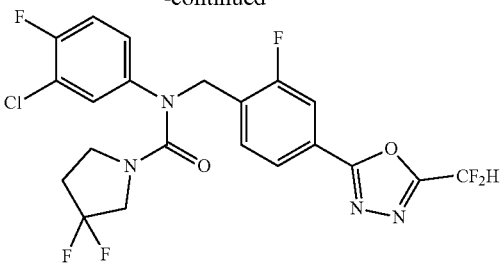

N-(3-chloro-4-fluorophenyl)-3,3-difluoro-N-(2-fluoro-4-(hydrazinecarbonyl)benzyl) pyrrolidine-1-carboxamide (0.123 g, 0.277 mmol), 2,2-difluoroacetic anhydride (0.090 mL, 0.830 mmol) and triethylamine (0.193 mL, 1.383 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-N-(4-(5-(difluoromethyl)-1,3,4-oxadiazol-2-yl)-2-fluorobenzyl)-3,3-difluoropyrrolidine-1-carboxamide as white foam (0.105 g, 75.5%).

$^1$H NMR (400 MHz, CDCl$_3$) δ 7.90 (dd, 1H, J=8.0, 1.7 Hz), 7.80-7.70 (m, 2H), 7.22 (dd, 1H, J=6.4, 2.7 Hz), 7.13 (t, 1H, J=8.6 Hz), 7.07-6.78 (m, 2H), 4.92 (s, 2H), 3.48-3.35 (m, 4H), 2.24 (tt, 2H, J=13.7, 7.4 Hz); LRMS (ES) m/z 505.3 (M$^+$+1).

Example 267. Compound 21668: N-(3-chloro-4-fluorophenyl)-3,3-difluoro-N-(2-fluoro-4-(5-(trifluoromethyl)-1,3,4-oxadiazol-2-yl)benzyl)pyrrolidine-1-carboxamide

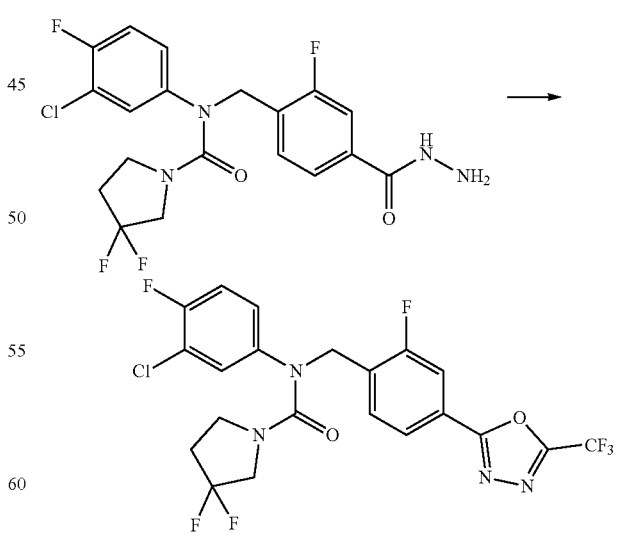

N-(3-chloro-4-fluorophenyl)-3,3-difluoro-N-(2-fluoro-4-(hydrazinecarbonyl)benzyl) pyrrolidine-1-carboxamide (0.123 g, 0.244 mmol), trifluoroacetic anhydride (0.103 mL, 0.731 mmol) and triethylamine (0.170 mL, 1.218 mmol)

were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-3,3-difluoro-N-(2-fluoro-4-(5-(trifluoromethyl)-1,3,4-oxadiazol-2-yl)benzyl)pyrrolidine-1-carboxamide as white foam (0.106 g, 83.3%).

$^1$H NMR (400 MHz, CDCl$_3$) δ 7.90 (dd, 1H, J=8.1, 1.6 Hz), 7.80-7.72 (m, 2H), 7.22 (dd, 1H, J=6.3, 2.7 Hz), 7.13 (t, 1H, J=8.6 Hz), 7.00 (ddd, 1H, J=8.8, 4.1, 2.7 Hz), 4.93 (s, 2H), 3.48-3.35 (m, 4H), 2.32-2.17 (m, 2H); LRMS (ES) m/z 523.3 (M++1).

Example 268. Compound 21669: N-(3-chloro-4-fluorophenyl)-N-(2-fluoro-4-(5-(trifluoromethyl)-1,3,4-oxadiazol-2-yl)benzyl)-4-(2-hydroxyethyl)piperazine-1-carboxamide

[Step 1] Methyl 4-((N-(3-chloro-4-fluorophenyl)-4-(2-hydroxyethyl)piperazine-1-carboxamido)methyl)-3-fluorobenzoate

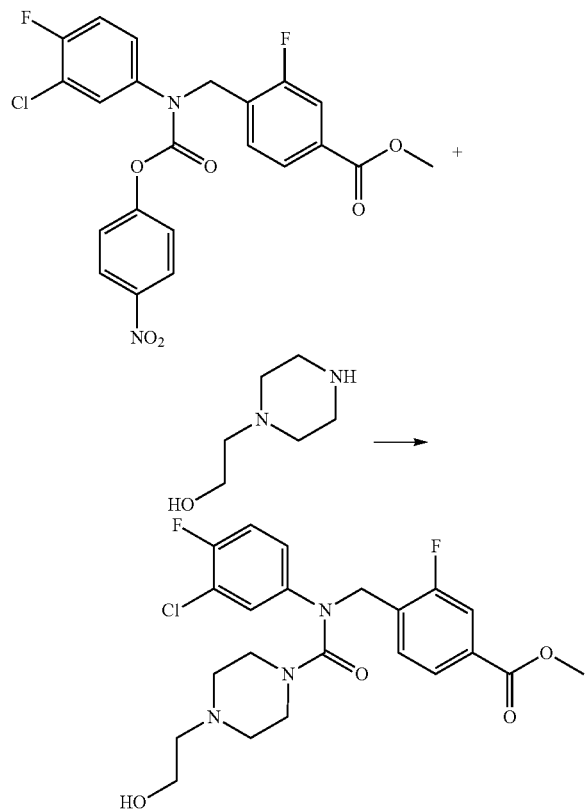

Methyl 4-(((3-chloro-4-fluorophenyl)((4-nitrophenoxy)carbonyl)amino)methyl)-3-fluorobenzoate (0.500 g, 1.049 mmol), 2-(piperazin-1-yl)ethan-1-ol (0.683 g, 5.243 mmol) and potassium carbonate (0.290 g, 2.097 mmol) were mixed at the room temperature in N,N-dimethylformamide (5 mL) and then stirred at 40° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give methyl 4-((N-(3-chloro-4-fluorophenyl)-4-(2-hydroxyethyl)piperazine-1-carboxamido)methyl)-3-fluorobenzoate as yellow oil (0.330 g, 67.3%).

[Step 2] N-(3-chloro-4-fluorophenyl)-N-(2-fluoro-4-(hydrazinecarbonyl)benzyl)-4-(2-hydroxyethyl)piperazine-1-carboxamide

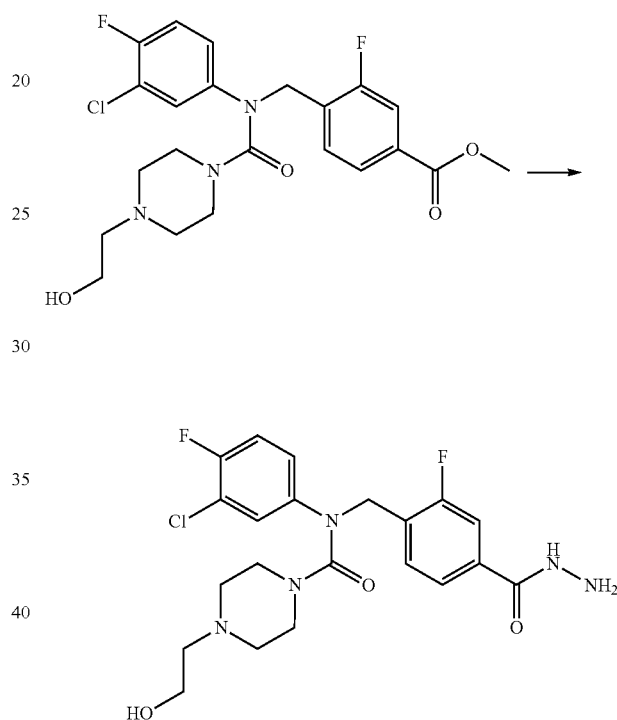

Methyl 4-((N-(3-chloro-4-fluorophenyl)-4-(2-hydroxyethyl)piperazine-1-carboxamido)methyl)-3-fluorobenzoate (0.330 g, 0.705 mmol) and hydrazine monohydrate (0.343 mL, 7.053 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(3-chloro-4-fluorophenyl)-N-(2-fluoro-4-(hydrazinecarbonyl)benzyl)-4-(2-hydroxyethyl)piperazine-1-carboxamide as yellow foam (0.137 g, 41.5%).

865

[Step 3] Compound 21669

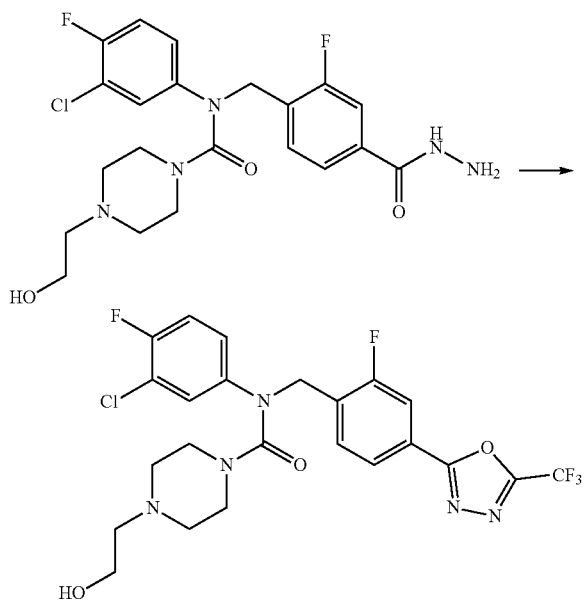

N-(3-chloro-4-fluorophenyl)-N-(2-fluoro-4-(hydrazinecarbonyl)benzyl)-4-(2-hydroxyethyl)piperazine-1-carboxamide (0.068 g, 0.138 mmol), trifluoroacetic anhydride (0.059 mL, 0.415 mmol) and triethylamine (0.096 mL, 0.691 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-N-(2-fluoro-4-(5-(trifluoromethyl)-1,3,4-oxadiazol-2-yl)benzyl)-4-(2-hydroxyethyl)piperazine-1-carboxamide as yellow oil (0.063 g, 83.6%).

$^1$H NMR (400 MHz, CDCl$_3$) δ 7.89 (dd, 1H, J=8.0, 1.7 Hz), 7.78 (dd, 1H, J=9.9, 1.7 Hz), 7.72 (t, 1H, J=7.6 Hz), 7.19 (dd, 1H, J=6.3, 2.7 Hz), 7.11 (t, 1H, J=8.6 Hz), 6.99 (ddd, 1H, J=8.9, 4.1, 2.8 Hz), 4.93 (s, 2H), 3.64 (t, 2H, J=5.3 Hz), 3.50 (s, 1H), 3.33 (t, 4H, J=5.0 Hz), 2.61-2.53 (m, 2H), 2.43 (t, 4H, J=5.0 Hz); LRMS (ES) m/z 546.5 (M$^+$+1).

Example 269. Compound 21679: N-(3-chloro-4-fluorophenyl)-N-(4-(5-(difluoromethyl)-1,3,4-oxadiazol-2-yl)-2-fluorobenzyl)-4-(2-hydroxyethyl)piperazine-1-carboxamide

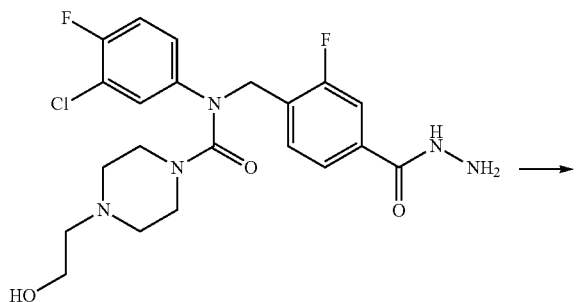

866

-continued

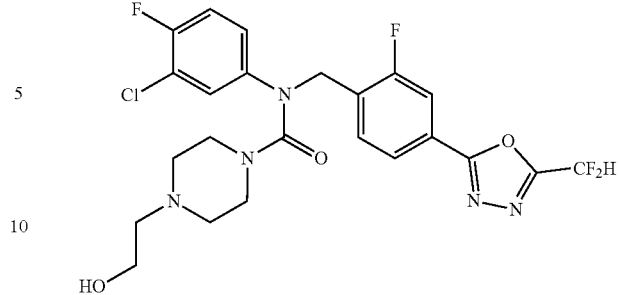

N-(3-chloro-4-fluorophenyl)-N-(2-fluoro-4-(hydrazinecarbonyl)benzyl)-4-(2-hydroxyethyl)piperazine-1-carboxamide (0.068 g, 0.138 mmol), 2,2-difluoroacetic anhydride (0.045 mL, 0.415 mmol) and triethylamine (0.096 mL, 0.691 mmol) were mixed at the room temperature in tetrahydrofuran (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit, to remove the solid residues and aqueous layer, and the organic layer collected was concentrated in vacuo. The residue was chromatographed (SiO$_2$, 4 g cartridge; methanol/dichloromethane=0% to 10%) to give N-(3-chloro-4-fluorophenyl)-N-(4-(5-(difluoromethyl)-1,3,4-oxadiazol-2-yl)-2-fluorobenzyl)-4-(2-hydroxyethyl)piperazine-1-carboxamide as yellow foam (0.020 g, 27.8%).

$^1$H NMR (400 MHz, CDCl$_3$) δ 7.90 (dd, 1H, J=8.1, 1.7 Hz), 7.78 (dd, 1H, J=10.1, 1.7 Hz), 7.69 (t, 1H, J=7.6 Hz), 7.20 (dd, 1H, J=6.3, 2.7 Hz), 7.12 (t, 1H, J=8.6 Hz), 7.03-6.78 (m, 2H), 4.92 (s, 2H), 3.75 (t, 2H, J=5.1 Hz), 3.54-3.42 (m, 4H), 2.72 (t, 2H, J=5.1 Hz), 2.62 (s, 4H); LRMS (ES) m/z 528.3 (M$^+$+1).

Example 270. Compound 21707: N-(4-(5-(Difluoromethyl)-1,3,4-oxadiazol-2-yl)-2-fluorobenzyl)-4-methyl-N-(1-methyl-1H-indazol-7-yl)piperazine-1-carboxamide

[Step 1] Methyl 3-fluoro-4-(((1-methyl-1H-indazol-7-yl)amino)methyl)benzoate

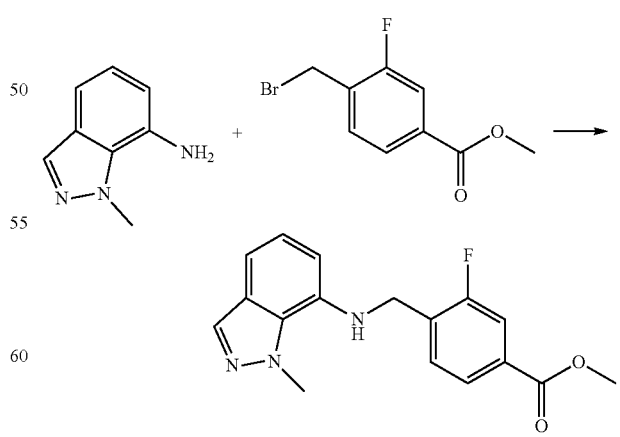

A solution of 1-methyl-1H-indazol-7-amine (1.472 g, 10.000 mmol), methyl 4-(bromomethyl)-3-fluorobenzoate (2.471 g, 10.000 mmol) and N,N-diisopropylethylamine (3.484 mL, 20.000 mmol) in acetonitrile (40 mL) was stirred at the room temperature for 18 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 40 g cartridge; ethyl acetate/hexane=0% to 30%) to give methyl 3-fluoro-4-(((1-methyl-1H-indazol-7-yl)amino)methyl)benzoate as white solid (1.768 g, 56.4%).

[Step 2] Methyl 3-fluoro-4-((4-methyl-N-(1-methyl-1H-indazol-7-yl)piperazine-1-carboxamido)methyl)benzoate

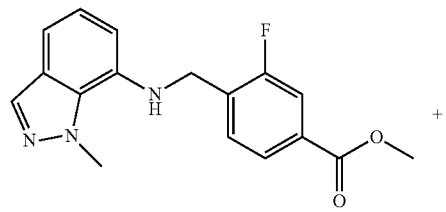

+

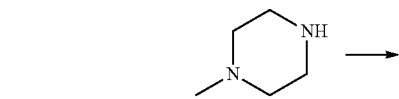

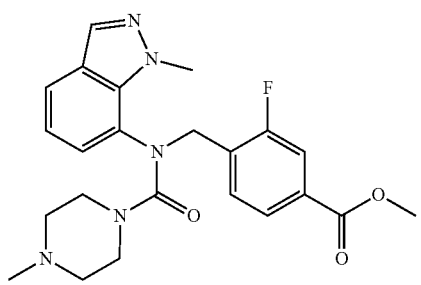

A solution of methyl 3-fluoro-4-(((1-methyl-1H-indazol-7-yl)amino)methyl)benzoate (0.384 g, 1.225 mmol), N,N-diisopropylethylamine (1.280 mL, 7.351 mmol) and triphosgene (0.182 g, 0.613 mmol) in dichloromethane (5 mL) was stirred at the room temperature for 30 min, and mixed with 1-methylpiperazine (0.136 mL, 1.225 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; methanol/dichloromethane=0% to 5%) to give methyl 3-fluoro-4-((4-methyl-N-(1-methyl-1H-indazol-7-yl)-1-carboxamido)methyl) benzoate as pale yellow oil (0.475 g, 88.2%).

[Step 3] N-(2-Fluoro-4-(hydrazinecarbonyl)benzyl)-4-methyl-N-(1-methyl-1H-indazol-7-yl)piperazine-1-carboxamide

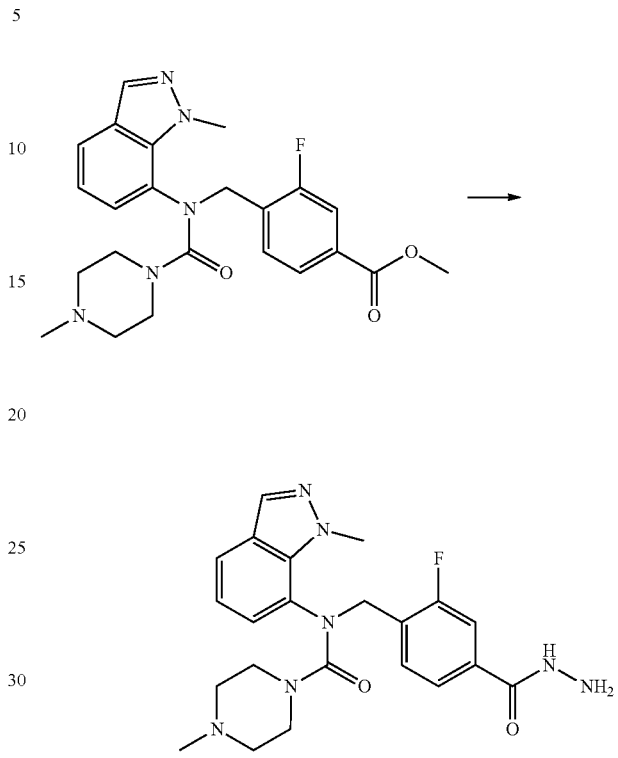

Methyl 3-fluoro-4-((4-methyl-N-(1-methyl-1H-indazol-7-yl)piperazine-1-carboxamido)methyl) benzoate (0.475 g, 1.081 mmol) and hydrazine monohydrate (1.051 mL, 21.616 mmol) were mixed at the room temperature in ethanol (5 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; methanol/dichloromethane=0% to 5%) to give N-(2-fluoro-4-(hydrazinecarbonyl)benzyl)-4-methyl-N-(1-methyl-1H-indazol-7-yl)piperazine-1-carboxamide as white solid (0.335 g, 70.5%).

[Step 4] Compound 21707

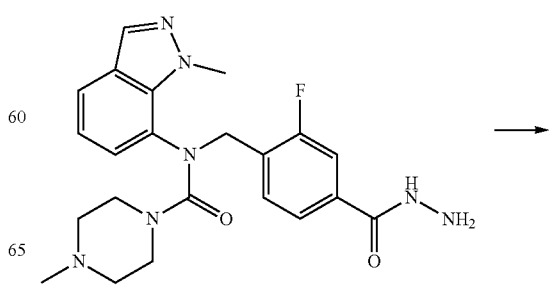

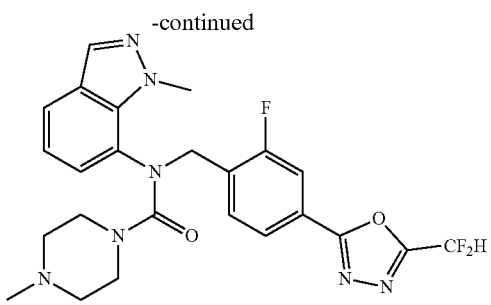

N-(2-Fluoro-4-(hydrazinecarbonyl)benzyl)-4-methyl-N-(1-methyl-1H-indazol-7-yl)piperazine-1-carboxamide (0.335 g, 0.762 mmol), triethylamine (0.531 mL, 3.808 mmol) and 2,2-difluoroacetic anhydride (0.284 mL, 2.285 mmol) were mixed at the room temperature in tetrahydrofuran (4 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)-2-fluorobenzyl)-4-methyl-N-(1-methyl-1H-indazol-7-yl)piperazine-1-carboxamide as pale brown solid (0.326 g, 85.6%).

$^1$H NMR (400 MHz, CDCl$_3$) δ 8.07 (s, 1H), 7.90 (dd, 1H, J=8.0, 1.6 Hz), 7.78 (t, 1H, J=7.6 Hz), 7.70-7.66 (m, 2H), 7.06-6.80 (m, 3H), 5.34 (d, 1H, J=16.9 Hz), 4.71 (d, 1H, J=14.7 Hz), 4.08 (s, 3H), 3.47 (brs, 4H), 2.61-2.52 (m, 7H); LRMS (ES) m/z 500.6 (M$^+$+1).

Example 271. Compound 21708: N-(4-(5-(Difluoromethyl)-1,3,4-oxadiazol-2-yl)-2-fluorobenzyl)-N-(1-methyl-1H-indazol-7-yl)thiomorpholine-4-carboxamide 1,1-dioxide

[Step 1] Methyl 3-fluoro-4-(((1-methyl-1H-indazol-7-yl)amino)methyl)benzoate

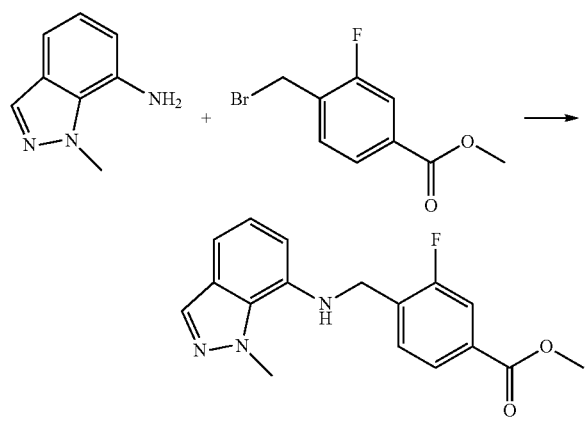

A solution of 1-methyl-1H-indazol-7-amine (1.472 g, 10.000 mmol), methyl 4-(bromomethyl)-3-fluorobenzoate (2.471 g, 10.000 mmol) and N,N-diisopropylethylamine (3.484 mL, 20.000 mmol) in acetonitrile (40 mL) was stirred at the room temperature for 18 hr, and then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 40 g cartridge; ethyl acetate/hexane=0% to 30%) to give methyl 3-fluoro-4-4-(1-methyl-1H-indazol-7-yl)amino)methyl)benzoate as white solid (1.768 g, 56.4%).

[Step 2] Methyl 3-fluoro-4-((N-(1-methyl-1H-indazol-7-yl)-1,1-dioxidothiomorpholine-4-carboxamido) methyl)benzoate

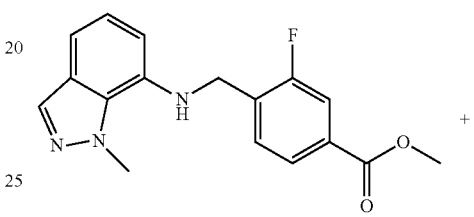

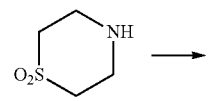

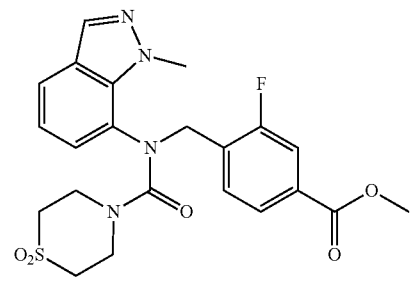

A solution of methyl 3-fluoro-4-((1-methyl-1H-indazol-7-yl)amino)methyl)benzoate (0.384 g, 1.226 mmol), N,N-diisopropylethylamine (1.281 mL, 7.353 mmol) and triphosgene (0.182 g, 0.613 mmol) in dichloromethane (5 mL) was stirred at the room temperature for 30 min, and mixed with thiomorpholine 1,1-dioxide (0.166 g, 1.226 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give methyl 3-fluoro-4-((N-(1-methyl-1H-indazol-7-yl)-1,1-dioxidothiomorpholine-4-carboxamido)methyl)benzoate as pale yellow oil (0.510 g, 87.7%).

871

[Step 3] N-(2-Fluoro-4-(hydrazinecarbonyl)benzyl)-N-(1-methyl-1H-indazol-7-yl)thiomorpholine-4-carboxamide 1,1-dioxide

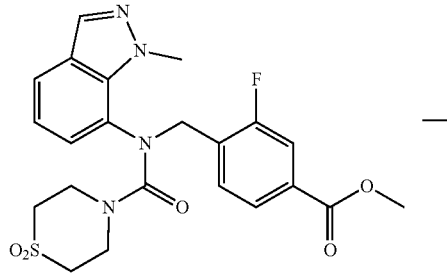

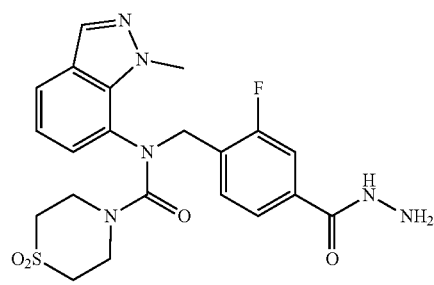

Methyl 3-fluoro-4-((N-(1-methyl-1H-indazol-7-yl)-1,1-dioxidothiomorpholine-4-carboxamido)methyl)benzoate (0.510 g, 1.075 mmol) and hydrazine monohydrate (1.045 mL, 21.496 mmol) were mixed at the room temperature in ethanol (5 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 10%) to give N-(2-fluoro-4-(hydrazinecarbonyl)benzyl)-N-(1-methyl-1H-indazol-7-yl)thiomorpholine-4-carboxamide 1,1-dioxide as white solid (0.314 g, 61.5%).

[Step 4] Compound 21708

872

-continued

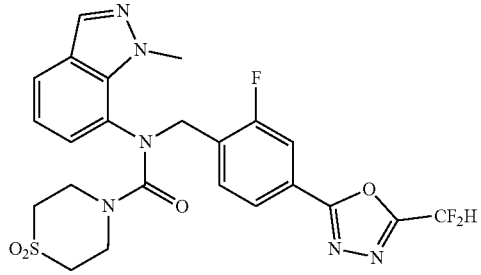

N-(2-Fluoro-4-(hydrazinecarbonyl)benzyl)-N-(1-methyl-1H-indazol-7-yl)thiomorpholine-4-carboxamide 1,1-dioxide (0.314 g, 0.661 mmol), triethylamine (0.460 mL, 3.303 mmol) and 2,2-difluoroacetic anhydride (0.246 mL, 1.982 mmol) were mixed at the room temperature in tetrahydrofuran (4 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)-2-fluorobenzyl)-N-(1-methyl-1H-indazol-7-yl)thiomorpholine-4-carboxamide 1,1-dioxide as white solid (0.298 g, 84.3%).

$^1$H NMR (400 MHz, CDCl$_3$) δ 8.09 (s, 1H), 7.91 (dd, 1H, J=8.0, 1.6 Hz), 7.78 (t, 1H, J=7.6 Hz), 7.72 (dd, 1H, J=8.0, 0.8 Hz), 7.67 (dd, 1H, J=9.9, 1.6 Hz), 7.05 (t, 1H, J=7.7 Hz), 6.93 (t, 1H, J=51.6 Hz), 6.86 (dd, 1H, J=7.4, 0.8 Hz), 5.34 (d, 1H, J=15.2 Hz), 4.68 (d, 1H, J=14.6 Hz), 4.14 (s, 3H), 3.75-3.61 (m, 4H), 2.63 (t, 4H, J=5.2 Hz); LRMS (ES) m/z 535.5 (M$^+$+1).

Example 272. Compound 21709: N-(4-(5-(difluoromethyl)-1,3,4-oxadiazol-2-yl)-2-fluorobenzyl)-4-methyl-N-(1-methyl-1H-indazol-4-yl)piperazine-1-carboxamide

[Step 1] Methyl 3-fluoro-4-(((1-methyl-1H-indazol-4-yl)amino)methyl)benzoate

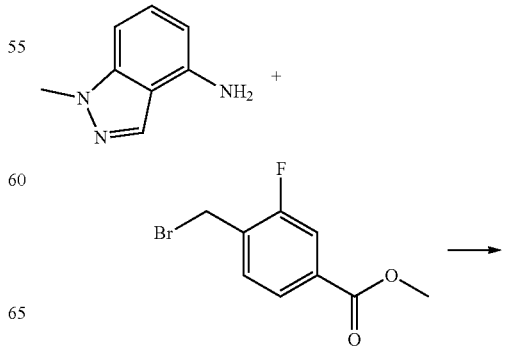

-continued

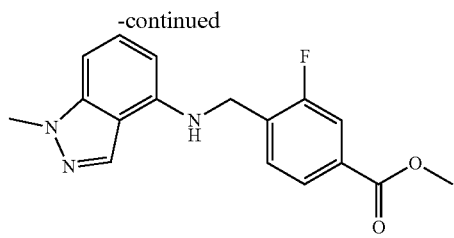

A solution of 1-methyl-1H-indazol-4-amine (0.442 g, 3.000 mmol), methyl 4-(bromomethyl)-3-fluorobenzoate (0.741 g, 3.000 mmol) and N,N-diisopropylethylamine (1.045 mL, 6.001 mmol) in acetonitrile (12 mL) was stirred at the room temperature for 18 hr, and then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 12 g cartridge; ethyl acetate/hexane=0% to 30%) to give methyl 3-fluoro-4-(((1-methyl-1H-indazol-4-yl)amino)methyl)benzoate as pale brown oil (0.768 g, 81.7%)

[Step 2] Methyl 3-fluoro-4-((4-methyl-N-(1-methyl-1H-indazol-4-yl)piperazine-1-carboxamido)methyl) benzoate

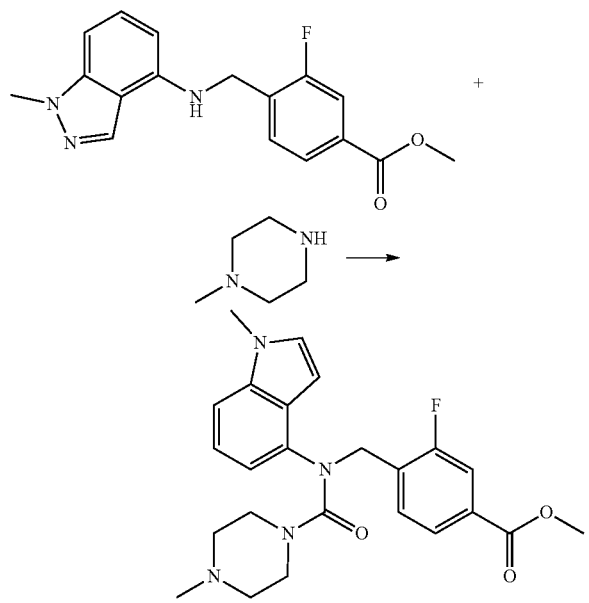

A solution of methyl 3-fluoro-4-(((1-methyl-1H-indazol-4-yl)amino)methyl)benzoate (0.384 g, 1.225 mmol), N,N-diisopropylethylamine (1.280 mL, 7.351 mmol) and triphosgene (0.182 g, 0.613 mmol) in dichloromethane (5 mL) was stirred at the room temperature for 30 min, and mixed with 1-methylpiperazine (0.136 mL, 1.225 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; methanol/dichloromethane=0% to 5%) to give methyl 3-fluoro-4-((4-methyl-N-(1-methyl-1H-indazol-4-yl)piperazine-1-carboxamido)methyl) benzoate as pale yellow oil (0.493 g, 91.6%).

[Step 3] N-(2-Fluoro-4-(hydrazinecarbonyl)benzyl)-4-methyl-N-(1-methyl-1H-indazol-4-yl)piperazine-1-carboxamide

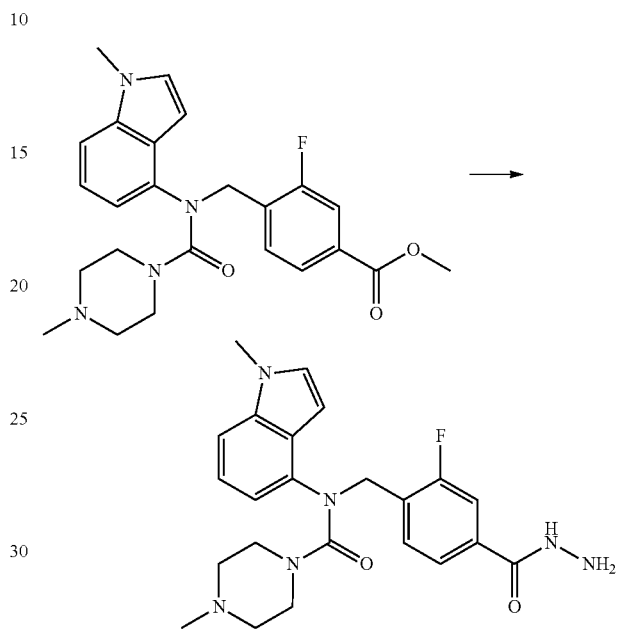

Methyl 3-fluoro-4-((4-methyl-N-(1-methyl-1H-indazol-4-yl)piperazine-1-carboxamido)methyl) benzoate (0.493 g, 1.122 mmol) and hydrazine monohydrate (1.090 mL, 22.435 mmol) were mixed at the room temperature in ethanol (5 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; methanol/dichloromethane=0% to 10%) to give N-(2-fluoro-4-(hydrazinecarbonyl)benzyl)-4-methyl-N-(1-methyl-1H-indazol-4-yl)piperazine-1-carboxamide as white solid (0.331 g, 67.2%).

[Step 4] Compound 21709

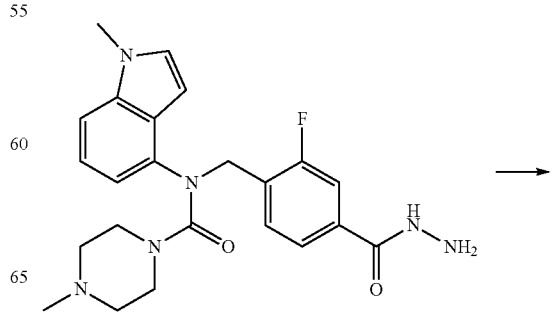

875
-continued

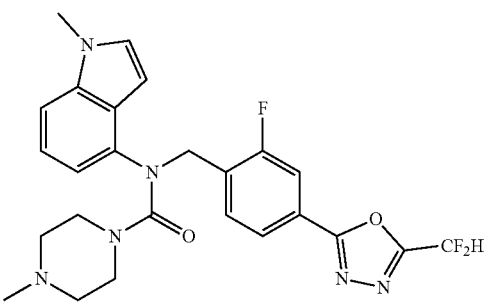

N-(2-Fluoro-4-(hydrazinecarbonyl)benzyl)-4-methyl-N-(1-methyl-1H-indazol-4-yl)piperazine-1-carboxamide (0.331 g, 0.754 mmol), triethylamine (0.525 mL, 3.769 mmol) and 2,2-difluoroacetic anhydride (0.281 mL, 2.261 mmol) were mixed at the room temperature in tetrahydrofuran (4 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; methanol/dichloromethane=0% to 5%) to give N-(4-(5-(difluoromethyl)-1,3,4-oxadiazol-2-yl)-2-fluorobenzyl)-4-methyl-N-(1-methyl-1H-indazol-4-yl)piperazine-1-carboxamide as pale brown solid (0.310 g, 82.2%)

¹H NMR (400 MHz, CDCl₃) δ 7.84 (dd, 1H, J=8.0, 1.6 Hz), 7.79 (d, 1H, J=0.8 Hz), 7.73 7.68 (m, 2H), 7.37-7.29 (m, 2H), 6.92 (t, 1H, J=51.7 Hz), 6.86 (dd, 1H, J=7.0, 0.9 Hz), 5.09 (s, 2H), 4.11 (s, 3H), 3.50 (brs, 4H), 2.81 (brs, 4H), 2.64 (s, 3H); LRMS (ES) m/z 500.6 (M⁺+1).

Example 273. Compound 21710: N-(4-(5-(difluoromethyl)-1,3,4-oxadiazol-2-yl)-2-fluorobenzyl)-N-(1-methyl-1H-indazol-4-yl)thiomorpholine-4-carboxamide 1,1-dioxide

[Step 1] Methyl 3-fluoro-4-(((1-methyl-1H-indazol-4-yl)amino)methyl)benzoate

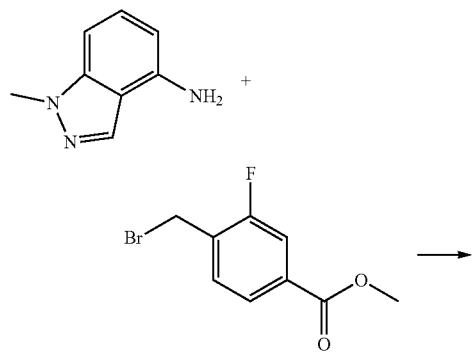 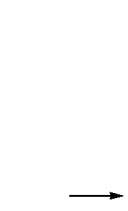

876
-continued

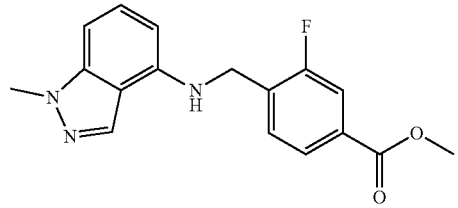

A solution of 1-methyl-1H-indazol-4-amine (0.442 g, 3.000 mmol), methyl 4-(bromomethyl)-3-fluorobenzoate (0.741 g, 3.000 mmol) and N,N-diisopropylethylamine (1.045 mL, 6.001 mmol) in acetonitrile (12 mL) was stirred at the room temperature for 18 hr. Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 12 g cartridge; ethyl acetate/hexane=0% to 30%) to give methyl 3-fluoro-4-(((1-methyl-1H-indazol-4-yl)amino)methyl)benzoate as pale brown oil (0.768 g, 81.7%).

[Step 2] Methyl 3-fluoro-4-((N-(1-methyl-1H-indazol-4-yl)-1,1-dioxidothiomorpholine-4-carboxamido) methyl)benzoate

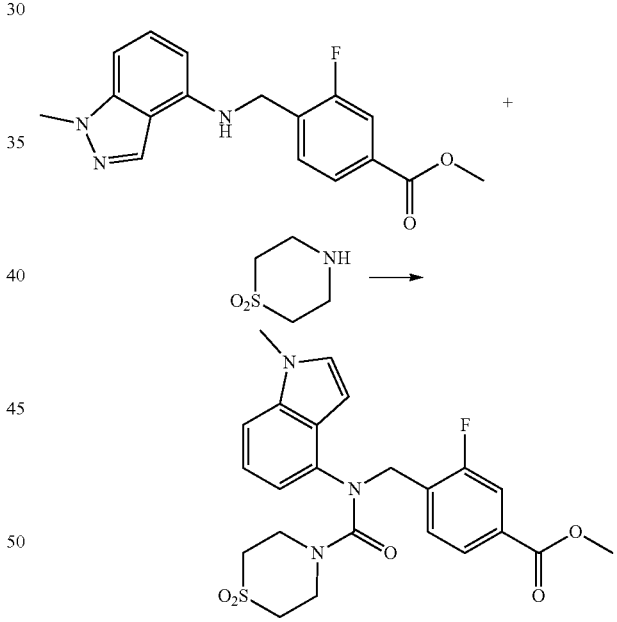

A solution of methyl 3-fluoro-4-(((1-methyl-1H-indazol-4-yl)amino)methyl)benzoate (0.384 g, 1.225 mmol), N,N-diisopropylethylamine (1.280 mL, 7.351 mmol) and triphosgene (0.182 g, 0.613 mmol) in dichloromethane (5 mL) was stirred at the room temperature for 30 min, and mixed with thiomorpholine 1,1-dioxide (0.166 g, 1.225 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; methanol/dichloromethane=0% to 5%) to give methyl 3-fluoro-4-((N-(1-methyl-1H-indazol-4-yl)-1,1-dioxidothiomorpholine-4-carboxamido)methyl)benzoate as pale yellow oil (0.531 g, 91.3%).

[Step 3] N-(2-Fluoro-4-(hydrazinecarbonyl)benzyl)-N-(1-methyl-1H-indazol-4-yl)thiomorpholine-4-carboxamide 1,1-dioxide

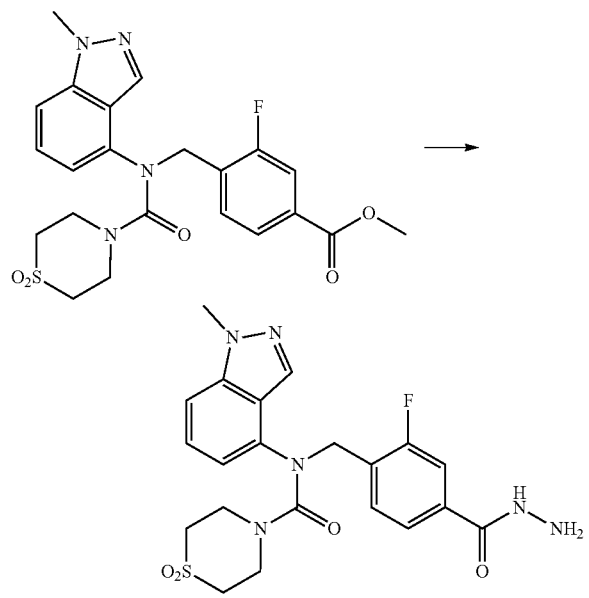

Methyl 3-fluoro-4-((N-(1-methyl-1H-indazol-4-yl)-1,1-dioxidothiomorpholine-4-carboxamido)methyl)benzoate (0.531 g, 1.119 mmol) and hydrazine monohydrate (1.088 mL, 22.381 mmol) were mixed at the room temperature in ethanol (5 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 10%) to give N-(2-fluoro-4-(hydrazinecarbonyl)benzyl)-N-(1-methyl-1H-indazol-4-yl)thiomorpholine-4-carboxamide 1,1-dioxide as white solid (0.426 g, 80.2%).

[Step 4] Compound 21710

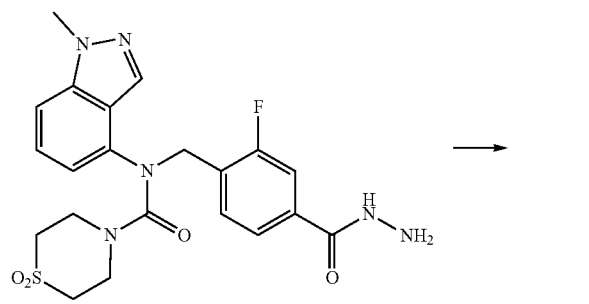

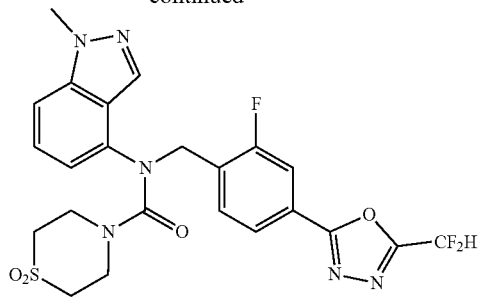

N-(2-Fluoro-4-(hydrazinecarbonyl)benzyl)-N-(1-methyl-1H-indazol-4-yl)thiomorpholine-4-carboxamide 1,1-dioxide (0.426 g, 0.898 mmol), triethylamine (0.626 mL, 4.488 mmol) and 2,2-difluoroacetic anhydride (0.335 mL, 2.693 mmol) were mixed at the room temperature in tetrahydrofuran (4 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)-2-fluorobenzyl)-N-(1-methyl-1H-indazol-4-yl)thiomorpholine-4-carboxamide 1,1-dioxide as white solid (0.396 g, 82.5%).

$^1$H NMR (400 MHz, CDCl$_3$) δ 7.86 (dd, 1H, J=8.0, 1.6 Hz), 7.82 (d, 1H, J=0.8 Hz), 7.39-7.32 (m, 2H), 6.92 (t, 1H, J=51.7 Hz), 6.90 (dd, 1H, J=6.9, 1.0 Hz), 5.07 (s, 2H), 4.12 (s, 3H), 3.72 (t, 4H, J=5.1 Hz), 2.65 (t, 4H, J=5.3 Hz); LRMS (ES) m/z 535.5 (M$^+$+1).

Example 274. Compound 21724: N-(4-(5-(Difluoromethyl)-1,3,4-oxadiazol-2-yl)-2-fluorobenzyl)-N-(1-methyl-1H-indazol-6-yl)morpholine-4-carboxamide

[Step 1] Methyl 3-fluoro-4-(((1-methyl-1H-indazol-6-yl)amino)methyl)benzoate

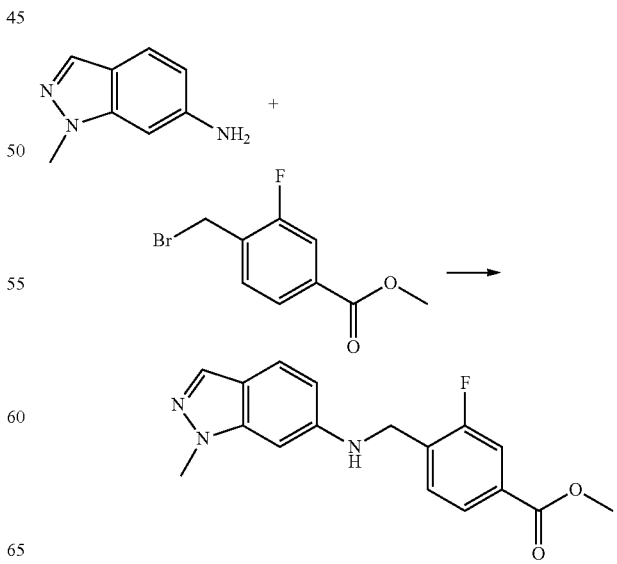

A solution of 1-methyl-1H-indazol-6-amine (2.944 g, 20.000 mmol), methyl 4-(bromomethyl)-3-fluorobenzoate (4.941 g, 20.000 mmol) and N,N-diisopropylethylamine (6.967 mL, 40.000 mmol) in acetonitrile (100 mL) was stirred at the room temperature for 18 hr, and Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 40 g cartridge; ethyl acetate/hexane=0% to 30%) to give methyl 3-fluoro-4-(((1-methyl-1H-indazol-6-yl)amino)methyl)benzoate as green solid (4.987 g, 79.6%).

[Step 2] Methyl 3-fluoro-4-((N-(1-methyl-1H-indazol-6-yl)morpholine-4-carboxamido)methyl)benzoate

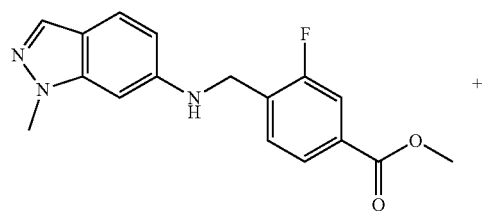

+

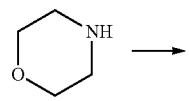

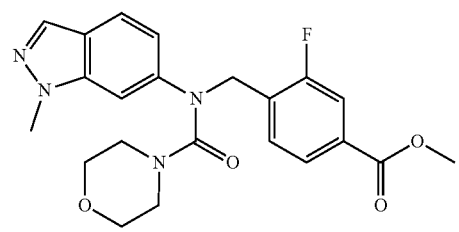

A solution of methyl 3-fluoro-4-4-(1-methyl-1H-indazol-6-yl)amino)methyl)benzoate (0.157 g, 0.500 mmol), N,N-diisopropylethylamine (0.523 mL, 3.000 mmol) and triphosgene (0.074 g, 0.250 mmol) in dichloromethane (3 mL) was stirred at the room temperature for 30 min, and mixed with morpholine (0.043 mL, 0.500 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; methanol/dichloromethane=0% to 5%) to give methyl 3-fluoro-4-((N-(1-methyl-1H-indazol-6-yl)morpholine-4-carboxamido)methyl)benzoat e as colorless oil (0.209 g, 97.9%).

[Step 3] N-(2-Fluoro-4-(hydrazinecarbonyl)benzyl)-N-(1-methyl-1H-indazol-6-yl)morpholine-4-carboxamide

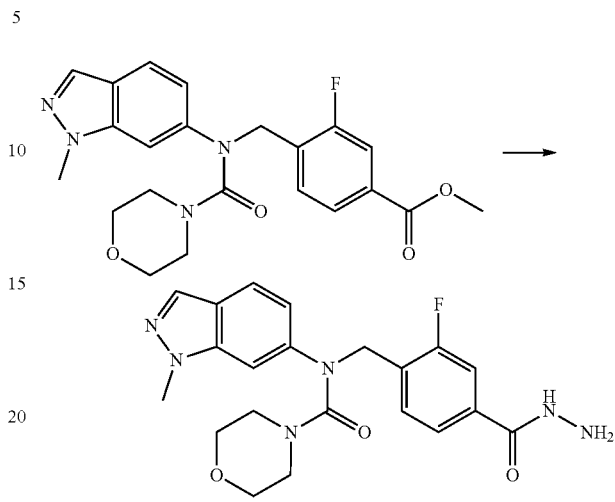

Methyl 3-fluoro-4-((N-(1-methyl-1H-indazol-6-yl)morpholine-4-carboxamido)methyl)benzoat e (0.209 g, 0.490 mmol) and hydrazine monohydrate (0.476 mL, 9,802 mmol) were mixed at the room temperature in ethanol (3 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 12 g cartridge; methanol/dichloromethane=0% to 10%) to give N-(2-fluoro-4-(hydrazinecarbonyl)benzyl)-N-(1-methyl-1H-indazol-6-yl)morpholine-4-carboxamide as pale brown oil (0.151 g, 72.4%).

[Step 4] Compound 21724

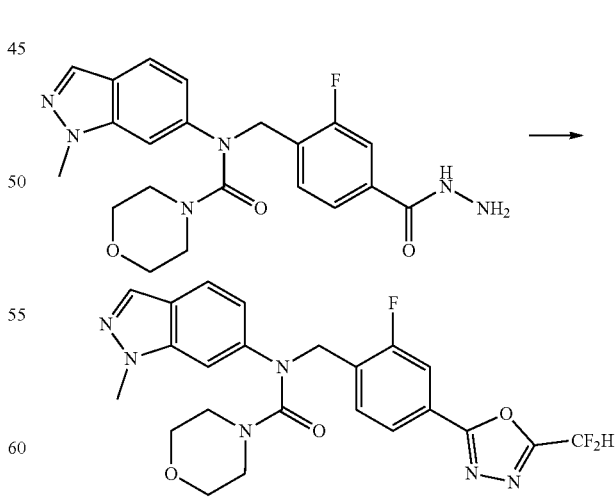

N-(2-Fluoro-4-(hydrazinecarbonyl)benzyl)-N-(1-methyl-1H-indazol-6-yl)morpholine-4-carboxamide (0.151 g, 0.354 mmol), triethylamine (0.247 mL, 1.770 mmol) and 2,2-difluoroacetic anhydride (0.132 mL, 1.062 mmol) were mixed at the room temperature in tetrahydrofuran (3 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(4-(5-(difluoromethyl)-1,3,4-oxadiazol-2-yl)-2-fluorobenzyl)-N-(1-methyl-1H-indazol-6-yl)morpholine-4-carboxamide as white solid (0.085 g, 49.3%).

$^1$H NMR (400 MHz, CDCl$_3$) δ 7.96 (d, 1H, J=1.0 Hz), 7.89 (dd, 1H, J=7.9, 1.7 Hz), 7.78-7.74 (m, 2H), 7.68 (dd, 1H, J=8.6, 0.6 Hz), 7.11 (t, 1H, J=0.9 Hz), 6.98 (dd, 1H, J=8.6, 1.8 Hz), 6.92 (t, 1H, J=51.7 Hz), 5.07 (s, 2H), 4.05 (s, 3H), 3.49 (t, 4H, J=4.8 Hz), 3.29 (t, 4H, J=4.8 Hz); LRMS (ES) m/z 487.5 (M$^+$+1).

Example 275. Compound 21735: N-(4-(5-(difluoromethyl)-1,3,4-oxadiazol-2-yl)-2-fluorobenzyl)-4-ethyl-N-(1-methyl-1H-indazol-6-yl)piperazine-1-carboxamide

[Step 1] Methyl 4-((4-ethyl-N-(1-methyl-1H-indazol-6-yl)piperazine-1-carboxamido)methyl)-3-fluorobenzoate

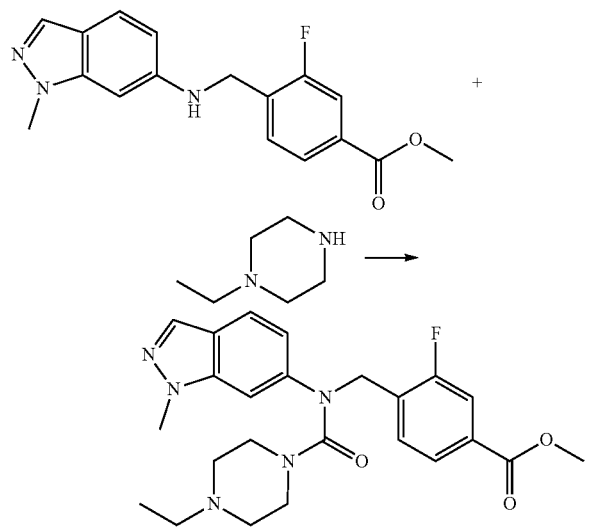

A solution of methyl 3-fluoro-4-(((1-methyl-1H-indazol-6-yl)amino)methyl)benzoate (0.157 g, 0.500 mmol), N,N-diisopropylethylamine (0.523 mL, 3.000 mmol) and triphosgene (0.074 g, 0.250 mmol) in dichloromethane (3 mL) was stirred at the room temperature for 30 min, and mixed with 1-ethylpiperazine (0.063 mL, 0.500 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=% to 5%) to give methyl 4-((4-ethyl-N-(1-methyl-1H-indazol-6-yl) piperazine-1-carboxamido)methyl)-3-fluorobenzoate as pale yellow oil (0.188 g, 82.9%).

[Step 2] 4-Ethyl-N-(2-fluoro-4-(hydrazinecarbonyl)benzyl)-N-(1-methyl-1H-indazol-6-yl)piperazine-1-carboxamide

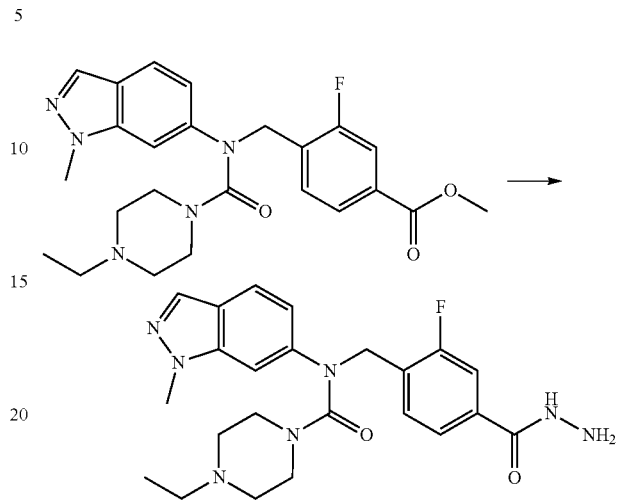

Methyl 4-((4-ethyl-N-(1-methyl-1H-indazol-6-yl)piperazine-1-carboxamido)methyl)-3-fluorobenzoate (0.188 g, 0.415 mmol) and hydrazine monohydrate (0.403 mL, 8.291 mmol) were mixed at the room temperature in ethanol (3 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 10%) to give 4-ethyl-N-(2-fluoro-4-(hydrazinecarbonyl)benzyl)-N-(1-methyl-1H-indazol-6-yl)piperazine-1-carboxamide as pale yellow oil (0.177 g, 94.0%).

[Step 3] Compound 21735

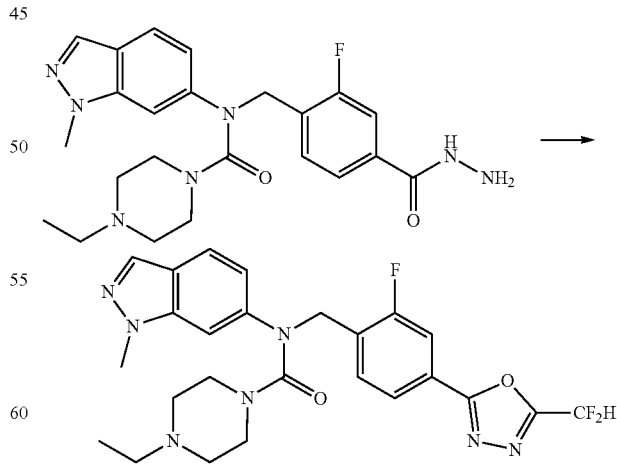

4-Ethyl-N-(2-fluoro-4-(hydrazinecarbonyl)benzyl)-N-(1-methyl-1H-indazol-6-yl)piperazine-1-carboxamide (0.177 g, 0.390 mmol), triethylamine (0.272 mL, 1.951 mmol) and 2,2-difluoroacetic anhydride (0.146 mL, 1.171 mmol) were mixed at the room temperature in tetrahydrofuran (3 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give the crude product which was re-chromatographed (SiO$_2$, 12 g cartridge; methanol/dichloromethane=0% to 5%) to give N-(4-(5-(difluoromethyl)-1,3,4-oxadiazol-2-yl)-2-fluorobenzyl)-4-ethyl-N-(1-methyl-1H-indazol-6-yl)piperazine-1-carboxamide as pale brown solid (0.010 g, 5.0%).

$^1$H NMR (400 MHz, CDCl$_3$) δ 7.94 (d, 1H, J=0.8 Hz), 7.88 (dd, 1H, J=8.0, 1.7 Hz), 7.77-7.73 (m, 2H), 7.66 (d, 1H, J=8.6 Hz), 7.07 (s, 1H), 6.95 (dd, 1H, J=8.6, 1.8 Hz), 6.92 (t, 1H, J=51.7 Hz), 5.06 (s, 2H), 4.03 (s, 3H), 3.43 (brs, 4H), 2.42 (brs, 6H), 1.12 (brs, 3H); LRMS (ES) m/z 514.7 (M$^+$+1).

Example 276. Compound 21736: (R)—N-(4-(5-(difluoromethyl)-1,3,4-oxadiazol-2-yl)-2-fluorobenzyl)-3-(dimethylamino)-N-(1-methyl-1H-indazol-6-yl)pyrrolidine-1-carboxamide

[Step 1] Methyl (R)-4-((3-(dimethylamino)-N-(1-methyl-1H-indazol-6-yl)pyrrolidine-1-carboxamido)methyl)-3-fluorobenzoate

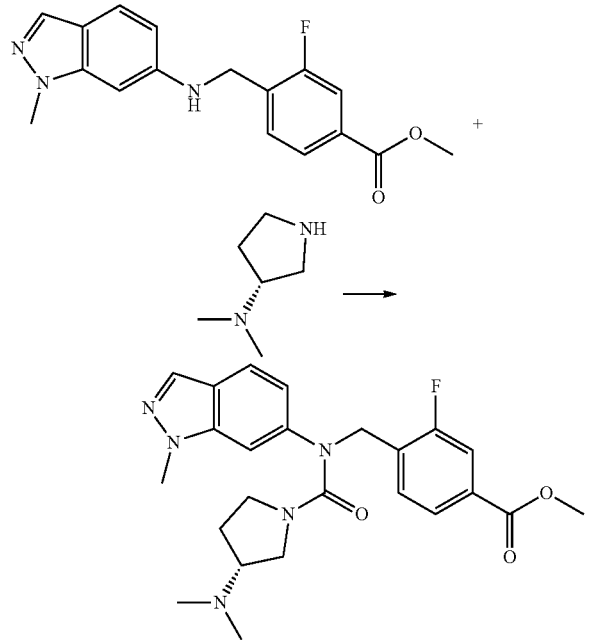

A solution of methyl 3-fluoro-4-(((1-methyl-1H-indazol-6-yl)amino)methyl)benzoate (0.157 g, 0.500 mmol), N,N-diisopropylethylamine (0.523 mL, 3.000 mmol) and triphosgene (0.074 g, 0.250 mmol) in dichloromethane (3 mL) was stirred at the room temperature for 30 min, and mixed with (R)—N,N-dimethylpyrrolidin-3-amine (0.063 mL, 0.500 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give methyl (R)-4-((3-(dimethylamino)-N-(1-methyl-1H-indazol-6-yl)pyrrolidine-1-carboxamido) methyl)-3-fluorobenzoate as colorless oil (0.213 g, 94.0%).

[Step 2] (R)-3-(Dimethylamino)-N-(2-fluoro-4-(hydrazinecarbonyl)benzyl)-N-(1-methyl-1H-indazol-6-yl)pyrrolidine-1-carboxamide

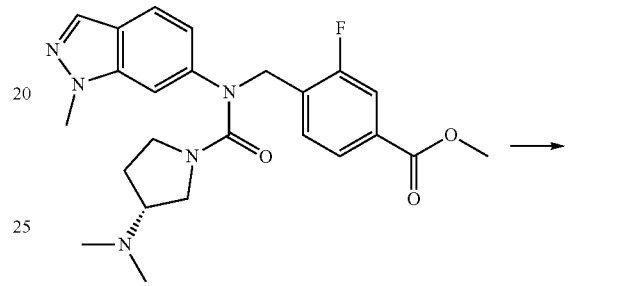

Methyl (R)-4-((3-(dimethylamino)-N-(1-methyl-1H-indazol-6-yl)pyrrolidine-1-carboxamido) methyl)-3-fluorobenzoate (0.213 g, 0.470 mmol) and hydrazine monohydrate (0.457 mL, 9.393 mmol) were mixed at the room temperature in ethanol (3 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 10%) to give (R)-3-(dimethylamino)-N-(2-fluoro-4-(hydrazinecarbonyl)benzyl)-N-(1-methyl-1H-indazol-6-yl)pyrrolidine-1-carboxamide as pale yellow oil (0.157 g, 73.7%).

885

[Step 3] Compound 21736

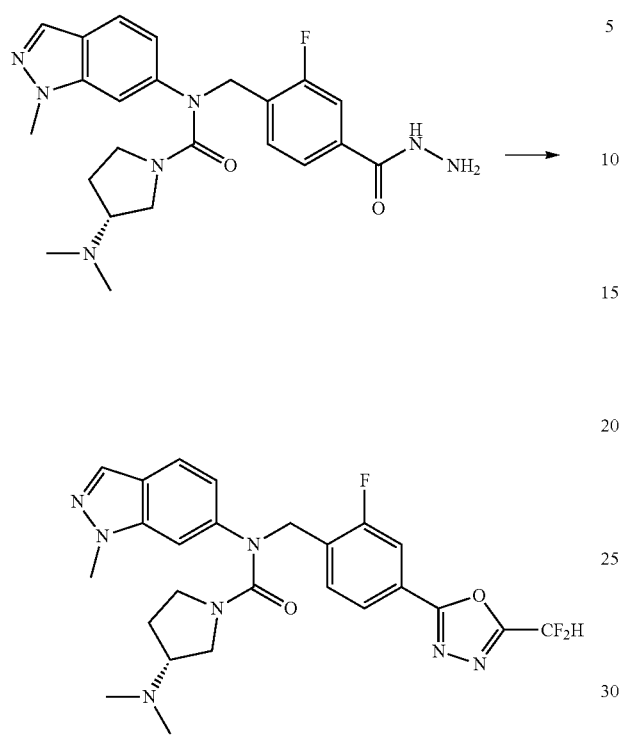

(R)-3-(Dimethylamino)-N-(2-fluoro-4-(hydrazinecarbonyl)benzyl)-N-(1-methyl-1H-indazol-6-yl)pyrrolidine-1-carboxamide (0.157 g, 0.346 mmol), triethylamine (0.241 mL, 1.731 mmol) and 2,2-difluoroacetic anhydride (0.129 mL, 1.039 mmol) were mixed at the room temperature in tetrahydrofuran (3 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give the crude product which was re-chromatographed (SiO$_2$, 12 g cartridge; methanol/dichloromethane=0% to 5%) to give (R)—N-(4-(5-(difluoromethyl)-1,3,4-oxadiazol-2-yl)-2-fluorobenzyl)-3-(dimethylamino)-N-(1-methyl-1H-indazol-6-yl)pyrrolidine-1-carboxamide as white solid (0.019 g, 10.4%).

$^1$H NMR (400 MHz, CDCl$_3$) δ 7.93 (d, 1H, J=0.9 Hz), 7.88 (dd, 1H, J=8.0, 1.6 Hz), 7.81 (t, 1H, J=7.6 Hz), 7.72 (dd, 1H, J=10.0, 1.6 Hz), 7.64 (dd, 1H, J=8.6, 0.6 Hz), 7.09 (t, 1H, J=0.8 Hz), 6.95 (dd, 1H, J=8.6, 1.8 Hz), 6.92 (t, 1H, J=51.7 Hz), 5.12-4.96 (m, 2H), 3.53-3.48 (m, 1H), 3.36-3.32 (m, 1H), 3.09-3.04 (m, 1H), 2.97 (brs, 1H), 2.66 (brs, 1H), 2.21 (s, 6H), 1.99-1.93 (m, 1H), 1.75-1.70 (m, 1H); LRMS (ES) m/z 487.5 (M$^+$+1).

886

Example 277. Compound 21759: N-(4-(5-(difluoromethyl)-1,3,4-oxadiazol-2-yl)-2-fluorobenzyl)-N-(3-fluorophenyl)-2-oxa-6-azaspiro[3.3]heptane-6-carboxamide

[Step 1] Methyl 3-fluoro-4-(((3-fluorophenyl)amino)methyl)benzoate

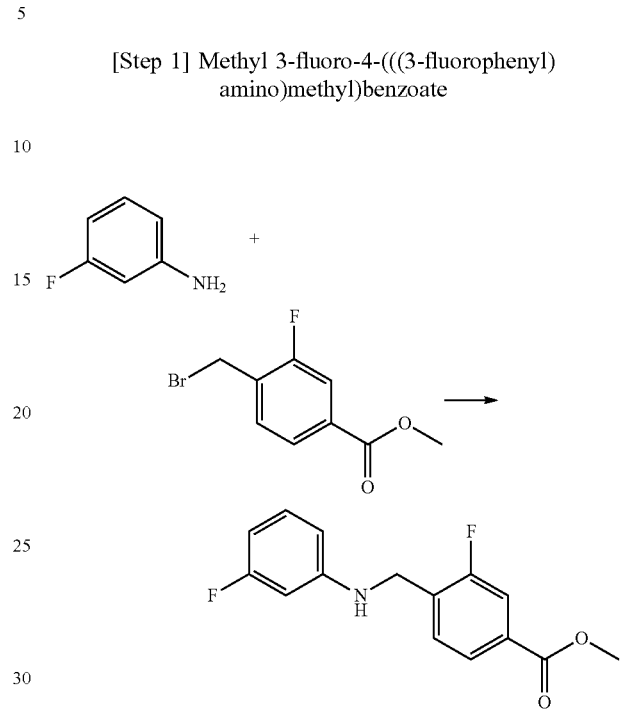

A solution of 3-fluoroaniline (0.500 g, 4.500 mmol), methyl 4-(bromomethyl)-3-fluorobenzoate (1.112 g, 4.500 mmol) and N,N-diisopropylethylamine (1.567 mL, 8.999 mmol) in acetonitrile (10 mL) was stirred at the room temperature for 18 hr, filtered through a plastic frit to remove solids, and concentrated under the reduced pressure to remove the solvents. The residue was chromatographed (SiO$_2$, 12 g cartridge; methanol/dichloromethane=0% to 5%) to give methyl 3-fluoro-4-(((3-fluorophenyl)amino)methyl)benzoate as pale brown oil (1.021 g, 81.8%).

[Step 2] Methyl 3-fluoro-4-((N-(3-fluorophenyl)-2-oxa-6-azaspiro[3.3]heptane-6-carboxamido)methyl)benzoate

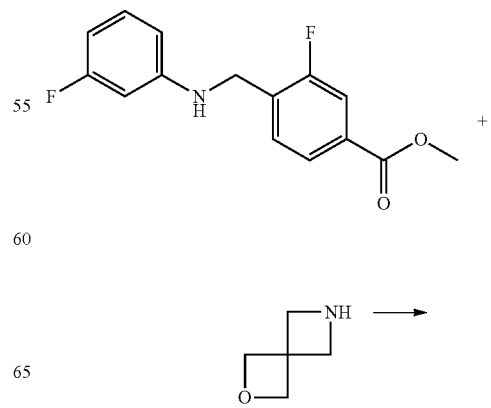

-continued

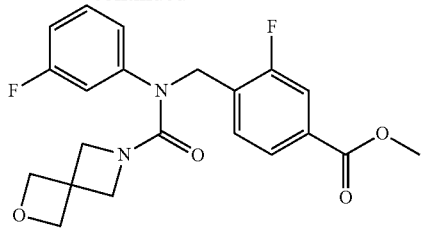

To a stirred solution of methyl 3-fluoro-4-(((3-fluorophenyl)amino)methyl)benzoate (0.550 g, 1.984 mmol) and N,N-diisopropylethylamine (2.073 mL, 11.902 mmol) in dichloromethane (5 mL) was added at 0° C. triphosgene (0.294 g, 0.992 mmol). The reaction mixture was stirred at the same temperature for 1 hr, added at the room temperature with 2-oxa-6-azaspiro[3.3]heptane (0.197 g, 1.984 mmol), and stirred for additional 4 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 3-fluoro-4-((N-(3-fluorophenyl)-2-oxa-6-azaspiro[3.3]heptane-6-carboxamido)methyl) benzoate as yellow oil (0.289 g, 36.1%).

[Step 3] N-(2-fluoro-4-(hydrazinecarbonyl)benzyl)-N-(3-fluorophenyl)-2-oxa-6-azaspiro[3.3]heptane-6-carboxamide

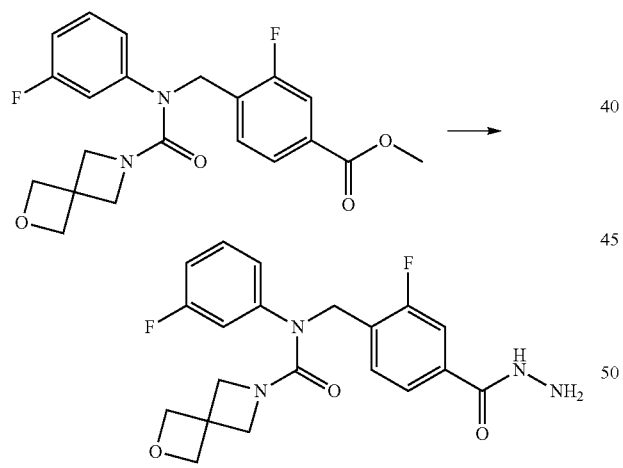

Methyl 3-fluoro-4-((N-(3-fluorophenyl)-2-oxa-6-azaspiro[3.3]heptane-6-carboxamido)methyl) benzoate (0.289 g, 0.717 mmol) and hydrazine monohydrate (0.348 mL, 7.169 mmol) were mixed at the room temperature in ethanol (2 mL) and then stirred at 100° C. for 18 hr and cooled down to the room temperature to terminate the reaction. The reaction mixture was concentrated under the reduced pressure to remove the solvents. The residue was chromatographed (SiO$_2$, 4 g cartridge; dichloromethane/methanol=0% to 10%) to give N-(2-fluoro-4-(hydrazinecarbonyl)benzyl)-N-(3-fluorophenyl)-2-oxa-6-azaspiro[3.3]heptane-6-carboxamide as yellow foam (0.228 g, 79.0%).

[Step 4] Compound 21759

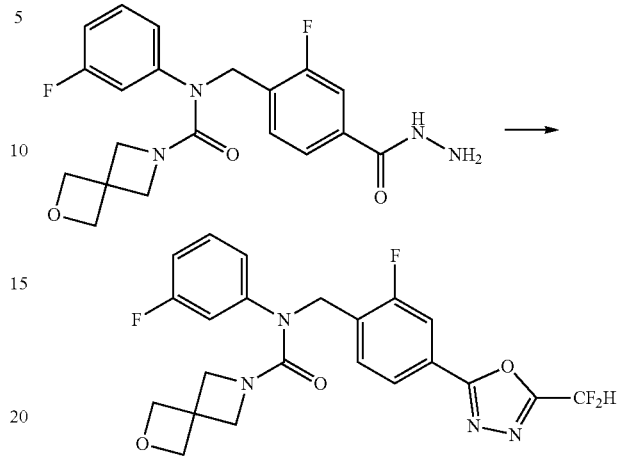

N-(2-fluoro-4-(hydrazinecarbonyl)benzyl)-N-(3-fluorophenyl)-2-oxa-6-azaspiro[3.3] heptane-6-carboxamide (0.119 g, 0.295 mmol), triethylamine (0.206 mL, 1.475 mmol) and 2,2-difluoroacetic anhydride (0.110 mL, 0.885 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=50% to 90%) to give N-(4-(5-(difluoromethyl)-1,3,4-oxadiazol-2-yl)-2-fluorobenzyl)-N-(3-fluorophenyl)-2-oxa-6-azaspiro[3.3]heptane-6-carboxamide as orange solid (0.032 g, 23.5%).

$^1$H NMR (400 MHz, CDCl$_3$) δ 7.88 (dd, 1H, J=8.1, 1.7 Hz), 7.77-7.65 (m, 2H), 7.32 (td, 1H, J=8.2, 6.4 Hz), 7.08-6.77 (m, 4H), 4.99 (s, 2H), 4.66 (s, 4H), 3.79 (s, 4H); LRMS (ES) m/z 463.4 (M$^+$+1).

Example 278. Compound 21760: N-(4-(5-(difluoromethyl)-1,3,4-oxadiazol-2-yl)-2-fluorobenzyl)-N-(m-tolyl)-2-oxa-6-azaspiro[3.3]heptane-6-carboxamide

[Step 1] Methyl 3-fluoro-4-((m-tolylamino)methyl)benzoate

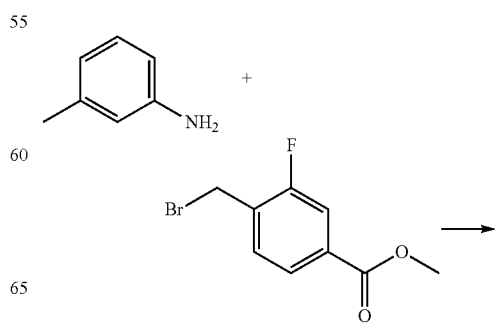

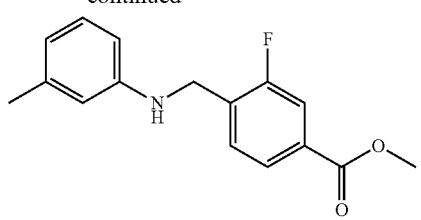

A solution of m-toluidine (0.500 g, 4.666 mmol), methyl 4-(bromomethyl)-3-fluorobenzoate (1.153 g, 4.666 mmol) and N,N-diisopropylethylamine (1.625 mL, 9.332 mmol) in acetonitrile (10 mL) was stirred at the room temperature for 18 hr, filtered through a plastic frit to remove solids, and concentrated under the reduced pressure. The residue was chromatographed (SiO$_2$, 12 g cartridge; methanol/dichloromethane=0% to 5%) to give methyl 3-fluoro-4-((m-tolylamino)methyl)benzoate as pale brown oil (0.885 g, 69.4%).

[Step 2] Methyl 3-fluoro-4-((N-(m-tolyl)-2-oxa-6-azaspiro[3.3]heptane-6-carboxamido)methyl)benzoate

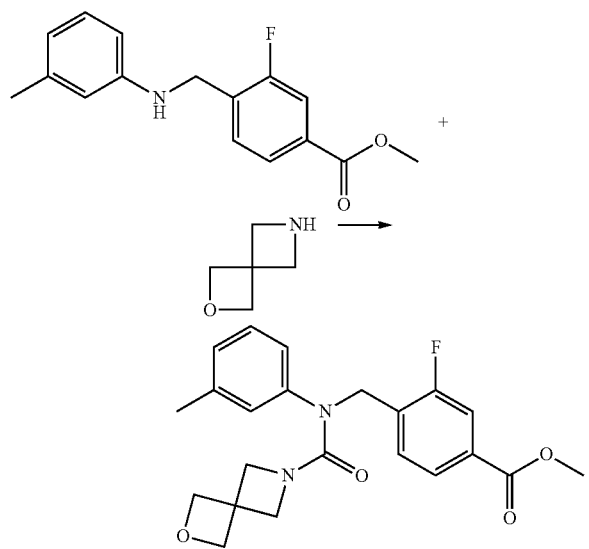

To a stirred solution of methyl 3-fluoro-4-((m-tolylamino)methyl)benzoate (0.550 g, 2.012 mmol) and N,N-diisopropylethylamine (2.103 mL, 12.074 mmol) in dichloromethane (5 mL) was added at 0° C. triphosgene (0.299 g, 1.006 mmol). The reaction mixture was stirred at the same temperature for 1 hr, added at the room temperature with 2-oxa-6-azaspiro[3.3]heptane (0.199 g, 2.012 mmol), and stirred for additional 4 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 3-fluoro-4-((N-(m-tolyl)-2-oxa-6-azaspiro[3.3]heptane-6-carboxamido)methyl)benzoat e as yellow oil (0.346 g, 43.1%).

[Step 3] N-(2-fluoro-4-(hydrazinecarbonyl)benzyl)-N-(m-tolyl)-2-oxa-6-azaspiro[3.3]heptane-6-carboxamide


Methyl 3-fluoro-4-((N-(m-tolyl)-2-oxa-6-azaspiro[3.3]heptane-6-carboxamido)methyl)benzoat e (0.346 g, 0.867 mmol) and hydrazine monohydrate (0.422 mL, 8.674 mmol) were mixed at the room temperature in ethanol (2 mL) and then stirred at 100° C. for 18 hr and cooled down to the room temperature to terminate the reaction, concentrated under the reduced pressure. The residue was chromatographed (SiO$_2$, 4 g cartridge; dichloromethane/methanol=0% to 10%) to give N-(2-fluoro-4-(hydrazinecarbonyl)benzyl)-N-(m-tolyl)-2-oxa-6-azaspiro[3.3]heptane-6-carboxamide as yellow foam (0.254 g, 73.5%).

[Step 4] Compound 21760

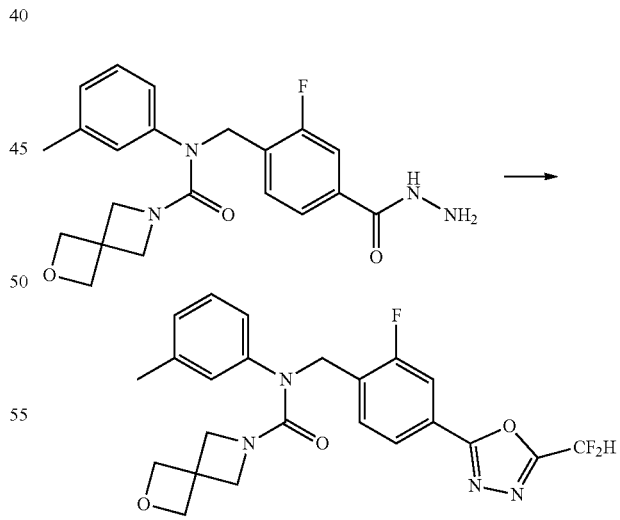

N-(2-fluoro-4-(hydrazinecarbonyl)benzyl)-N-(m-tolyl)-2-oxa-6-azaspiro[3.3]heptane-6-carboxamide (0.127 g, 0.319 mmol), triethylamine (0.222 mL, 1.595 mmol) and 2,2-difluoroacetic anhydride (0.119 mL, 0.957 mmol) were mixed at the room temperature in tetrahydrofuran (2 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=50% to 90%) to give N-(4-(5-(difluoromethyl)-1,3,4-oxadiazol-2-yl)-2-fluorobenzyl)-N-(m-tolyl)-2-oxa-6-azaspiro[3.3]heptane-6-carboxamide as orange solid (0.026 g, 17.9%).

$^1$H NMR (400 MHz, CDCl$_3$) δ 7.87 (dd, 1H, J=8.0, 1.7 Hz), 7.74-7.65 (m, 2H), 7.26-7.16 (m, 1H), 7.10-7.06 (m, 1H), 7.05-6.77 (m, 3H), 4.98 (s, 2H), 4.64 (s, 4H), 3.74 (s, 4H), 2.35 (s, 3H); LRMS (ES) m/z 459.3 (M$^+$+1).

Example 279. Compound 21765: N-(4-(5-(Difluoromethyl)-1,3,4-oxadiazol-2-yl)-2-fluorobenzyl)-2-ethyl-N-(1-methyl-1H-indazol-6-yl)-2,7-diazaspiro[3.5]nonane-7-carboxamide

[Step 1] Tert-Butyl 7-((2-fluoro-4-(methoxycarbonyl)benzyl)(1-methyl-1H-indazol-6-yl)carbamoyl)-2,7-diazaspiro[3.5]nonane-2-carboxylate

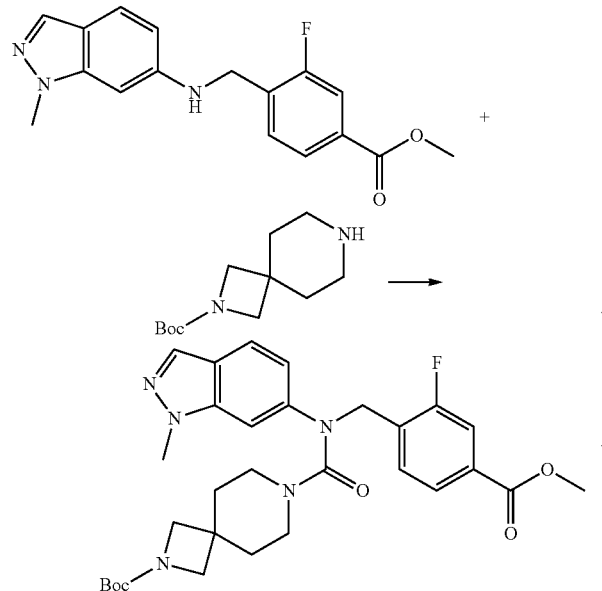

A solution of methyl 3-fluoro-4-(((1-methyl-1H-indazol-6-yl)amino)methyl)benzoate (0.940 g, 3.000 mmol), N,N-diisopropylethylamine (3.135 mL, 18.000 mmol) and triphosgene (0.445 g, 1.500 mmol) in dichloromethane (10 mL) was stirred at the room temperature for 30 min, and mixed with tert-butyl 2,7-diazaspiro[3.5]nonane-2-carboxylate (0.679 g, 3.000 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer and the organic layer collected was concentrated in vacuo. The residue was chromatographed (SiO$_2$, 24 g cartridge; methanol/dichloromethane=0% to 5%) to give tert-butyl 7-((2-fluoro-4-(methoxycarbonyl)benzyl)(1-methyl-1H-indazol-6-yl)carbamoyl)-2,7-diazaspiro[3.5]nonane-2-carboxylate as white foam solid (1.479 g, 87.2%).

[Step 2] Methyl 3-fluoro-4-((N-(1-methyl-1H-indazol-6-yl)-2,7-diazaspiro[3.5]nonane-7-carboxamido)methyl)benzoate hydrochloride

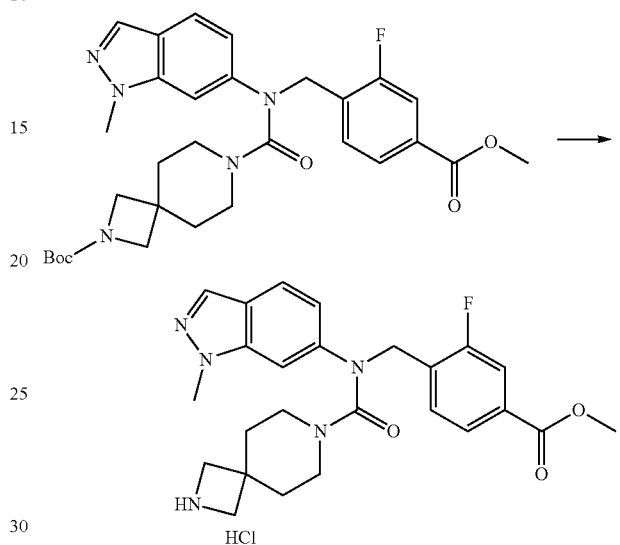

A solution of tert-butyl 7-((2-fluoro-4-(methoxycarbonyl)benzyl)(1-methyl-1H-indazol-6-yl)carbamoyl)-2,7-diazaspiro[3.5]nonane-2-carboxylate (1.479 g, 2.615 mmol) and hydrogen chloride (4.00 M solution in 1,4-dioxane, 2.615 mL, 10.459 mmol) in dichloromethane (20 mL) was stirred at the room temperature for 18 hr, and concentrated under the reduced pressure. The crude product was used without further purification (methyl 3-fluoro-4-((N-(1-methyl-1H-indazol-6-yl)-2,7-diazaspiro[3.5]nonane-7-carboxamido)methyl)benzoate hydrochloride, 1.312 g, 100.0%, white solid).

[Step 3] Methyl 4-((2-ethyl-N-(1-methyl-1H-indazol-6-yl)-2,7-diazaspiro[3.5]nonane-7-carboxamido)methyl)-3-fluorobenzoate

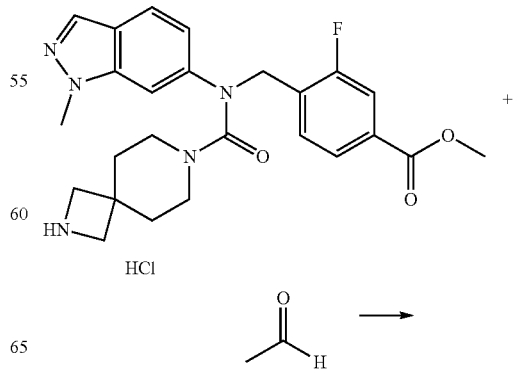

-continued

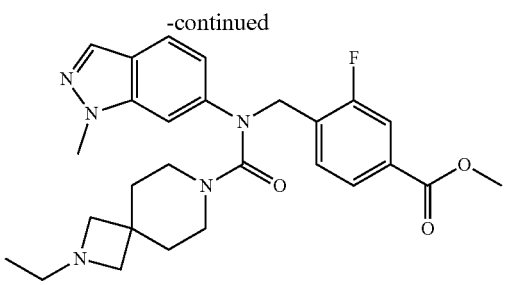

A solution of methyl 3-fluoro-4-((N-(1-methyl-1H-indazol-6-yl)-2,7-diazaspiro[3.5]nonane-7-carboxamido)methyl)benzoate hydrochloride (0.251 g, 0.500 mmol), acetaldehyde (0.042 mL, 0.750 mmol) and sodium triacetoxyborohydride (0.159 g, 0.750 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer and the organic layer collected was concentrated in vacuo. The residue was chromatographed ($SiO_2$, 12 g cartridge; methanol/dichloromethane=0% to 10%) to give methyl 4-((2-ethyl-N-(1-methyl-1H-indazol-6-yl)-2,7-diazaspiro[3.5]nonane-7-carboxamido)methyl)-3-fluorobenzoate as white solid (0.225 g, 91.3%).

[Step 4] 2-Ethyl-N-(2-fluoro-4-(hydrazinecarbonyl)benzyl)-N-(1-methyl-1H-indazol-6-yl)-2,7-diazaspiro[3.5]nonane-7-carboxamide

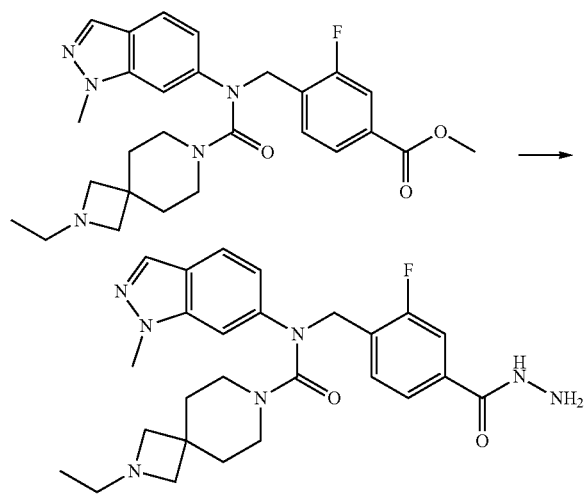

Methyl 4-((2-ethyl-N-(1-methyl-1H-indazol-6-yl)-2,7-diazaspiro[3.5]nonane-7-carboxamido) methyl)-3-fluorobenzoate (0.225 g, 0.456 mmol) and hydrazine monohydrate (0.443 mL, 9.117 mmol) were mixed at the room temperature in ethanol (2 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (2-ethyl-N-(2-fluoro-4-(hydrazinecarbonyl)benzyl)-N-(1-methyl-1H-indazol-6-yl)-2,7-diazaspiro[3.5]nonane-7-carboxamide, 0.224 g, 99.6%, pale yellow oil).

[Step 5] N-(4-(2-(2,2-Difluoroacetyl)hydrazine-1-carbonyl)-2-fluorobenzyl)-2-ethyl-N-(1-methyl-1H-indazol-6-yl)-2,7-diazaspiro[3.5]nonane-7-carboxamide

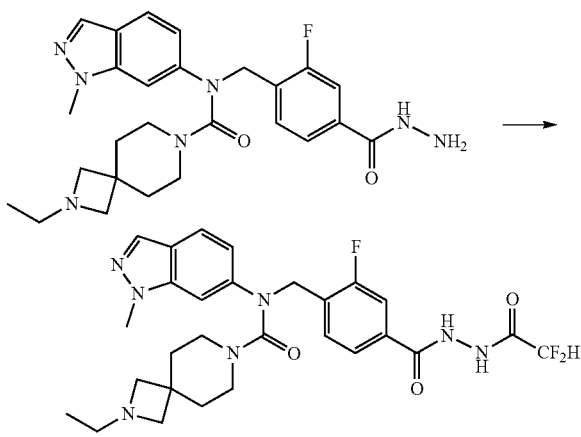

A solution of 2-ethyl-N-(2-fluoro-4-(hydrazinecarbonyl)benzyl)-N-(1-methyl-1H-indazol-6-yl)-2,7-diazaspiro[3.5]nonane-7-carboxamide (0.224 g, 0.454 mmol), triethylamine (0.127 mL, 0.908 mmol) and 2,2-difluoroacetic anhydride (0.056 mL, 0.454 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-(2-(2,2-difluoroacetyl)hydrazine-1-carbonyl)-2-fluorobenzyl)-2-ethyl-N-(1-methyl-1H-indazol-6-yl)-2,7-diazaspiro[3.5]nonane-7-carboxamide, 0.259 g, 99.8%, pale yellow solid).

[Step 6] Compound 21765

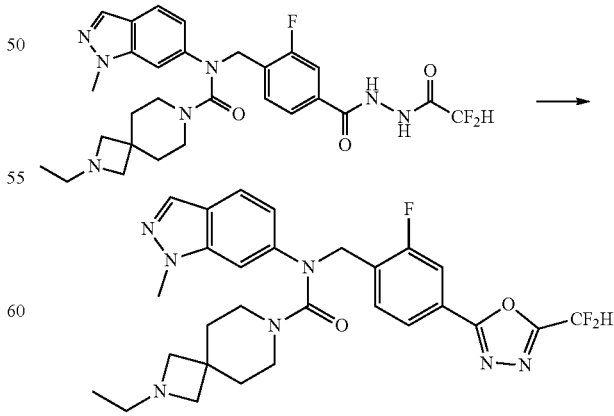

N-(4-(2-(2,2-Difluoroacetyl)hydrazine-1-carbonyl)-2-fluorobenzyl)-2-ethyl-N-(1-methyl-1H-indazol-6-yl)-2,7- diazaspiro[3.5]nonane-7-carboxamide (0.259 g, 0.453 mmol) and 1-methoxy-N-triethylammoniosulfonyl-methanimidate (Burgess reagent, 0.130 g, 0.544 mmol) were mixed at the room temperature in tetrahydrofuran (4 mL) and then stirred at 80° C. for 18 hr and cooled down to the room temperature to terminate the reaction. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)-2-fluorobenzyl)-2-ethyl-N-(1-methyl-1H-indazol-6-yl)-2,7-diazaspiro[3.5]nonane-7-carboxamide as pale yellow solid (0.017 g, 6.9%).

$^1$H NMR (400 MHz, CDCl$_3$) δ 7.93 (d, 1H, J=0.9 Hz), 7.87 (dd, 1H, J=8.0, 1.7 Hz), 7.77-7.72 (m, 2H), 7.64 (dd, 1H, J=8.6, 0.5 Hz), 7.07 (t, 1H, J=0.8 Hz), 6.93 (dd, 1H, J=8.7, 1.9 Hz), 6.92 (t, 1H, J=51.7 Hz), 5.03 (s, 2H), 4.02 (s, 3H), 3.22-3.18 (m, 4H), 3.00 (s, 4H), 2.50 (q, 2H, J=7.1 Hz), 1.58-1.54 (m, 4H), 0.95 (t, 3H, J=7.1 Hz); LRMS (ES) m/z 554.6 (M$^+$+1).

Example 280. Compound 21766: N-(3-Chloro-4-fluorophenyl)-N-((6-(5-(difluoromethyl)-1,3,4-oxadiazol-2-yl)pyridin-3-yl)methyl)morpholine-4-carboxamide

[Step 1] Methyl 5-(((3-chloro-4-fluorophenyl)amino)methyl)picolinate

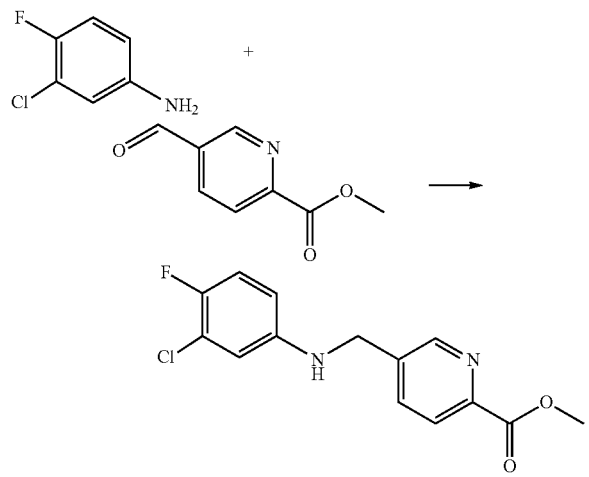

A solution of 3-chloro-4-fluoroaniline (0.437 g, 3.000 mmol), methyl 5-formylpicolinate (0.495 g, 3.000 mmol) and sodium triacetoxyborohydride (0.954 g, 4.500 mmol) in dichloromethane (15 mL) was stirred at the room temperature for 18 hr. Then, water was added to the reaction mixture, followed by extraction with dichloromethane. The organic layer was washed with aqueous saturated sodium chloride solution, dried (anhydrous MgSO$_4$), filtered, and concentrated in vacuo. The residue was chromatographed (SiO$_2$, 24 g cartridge; ethyl acetate/hexane=20% to 50%) to give methyl 5-(((3-chloro-4-fluorophenyl)amino)methyl)picolinate as brown solid (0.400 g, 45.2%).

[Step 2] Methyl 5-((N-(3-chloro-4-fluorophenyl)morpholine-4-carboxamido)methyl)picolinate

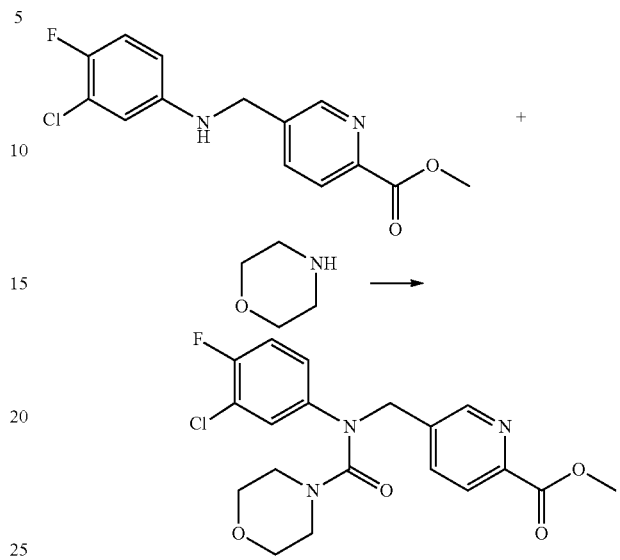

A solution of methyl 5-(((3-chloro-4-fluorophenyl)amino)methyl)picolinate (0.200 g, 0.679 mmol), N,N-diisopropylethylamine (0.355 mL, 2.036 mmol) and triphosgene (0.101 g, 0.339 mmol) in dichloromethane (5 mL) was stirred at the room temperature for 30 min, and mixed with morpholine (0.059 mL, 0.679 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=50% to 100%) to give methyl 5-((N-(3-chloro-4-fluorophenyl)morpholine-4-carboxamido)methyl)picolinate as white foam solid (0.268 g, 96.9%).

[Step 3] N-(3-Chloro-4-fluorophenyl)-N-((6-(hydrazinecarbonyl)pyridin-3-yl)methyl)morpholine-4-carboxamide

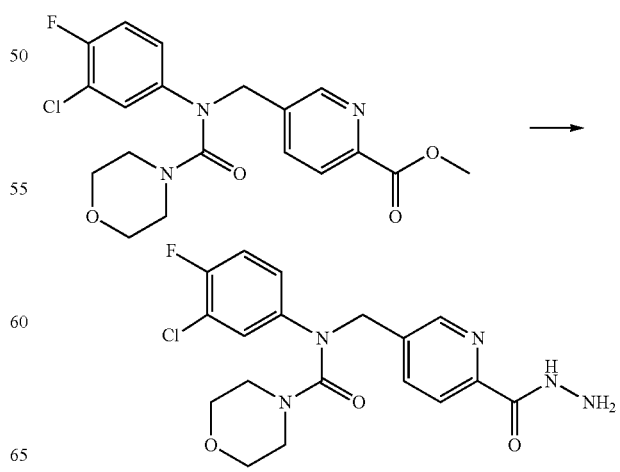

Methyl 5-((N-(3-chloro-4-fluorophenyl)morpholine-4-carboxamido)methyl)picolinate (0.268 g, 0.657 mmol) and hydrazine monohydrate (0.639 mL, 13.148 mmol) were mixed at the room temperature in 1,4-dioxane (4 mL) and then stirred at 70° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-N-((6-(hydrazinecarbonyl)pyridin-3-yl)methyl)morpholine-4-carboxamide as white solid (0.233 g, 86.8%).

[Step 4] Compound 21766

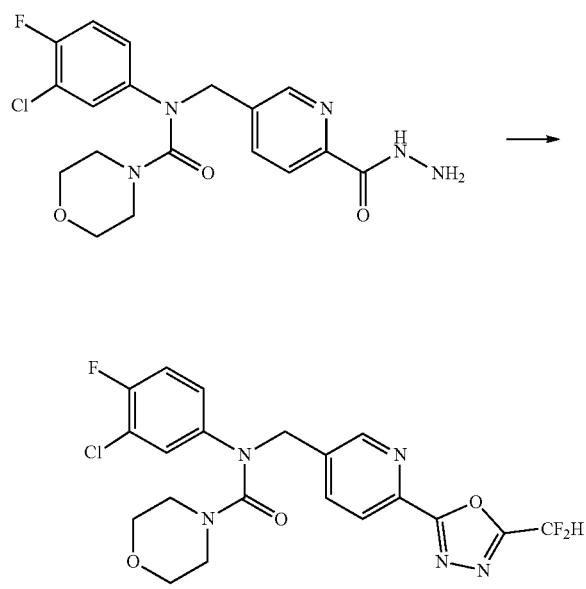

A solution of N-(3-chloro-4-fluorophenyl)-N-((6-(hydrazinecarbonyl)pyridin-3-yl)methyl)morpholine-4-carboxamide (0.180 g, 0.442 mmol), triethylamine (0.123 mL, 0.883 mmol) and 2,2-difluoroacetic anhydride (0.055 mL, 0.442 mmol) in dichloromethane (3 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(3-chloro-4-fluorophenyl)-N-((6-(5-(difluoromethyl)-1,3,4-oxadiazol-2-yl)pyridin-3-yl)methyl)morpholine-4-carboxamide as white solid (0.086 g, 41.8%).

$^1$H NMR (400 MHz, CDCl$_3$) δ 8.65 (d, 1H, J=1.5 Hz), 8.25 (dd, 1H, J=8.1, 0.6 Hz), 7.98 (dd, 1H, J=8.1, 2.2 Hz), 7.18 (dd, 1H, J=6.3, 2.7 Hz), 7.13 (t, 1H, J=8.6 Hz), 6.96-6.93 (m, 1H), 6.95 (t, 1H, J=51.7 Hz), 4.91 (s, 2H), 3.54 (t, 4H, J=4.8 Hz), 3.26 (t, 4H, J=4.8 Hz); LRMS (ES) m/z 468.4 (M$^+$+1).

Example 281. Compound 21767: N-(3-Chloro-4-fluorophenyl)-N-((6-(5-(difluoromethyl)-1,3,4-oxadiazol-2-yl)pyridin-3-yl)methyl)thiomorpholine-4-carboxamide 1,1-dioxide

[Step 1] Methyl 5-((N-(3-chloro-4-fluorophenyl)-1,1-dioxidothiomorpholine-4-carboxamido)methyl)picolinate

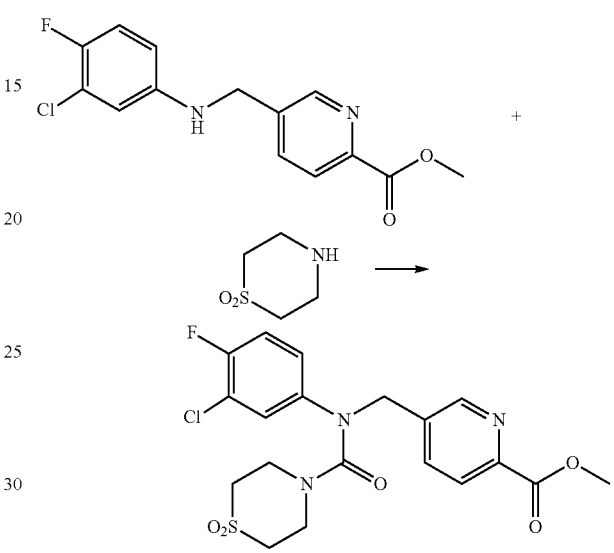

A solution of methyl 5-(((3-chloro-4-fluorophenyl)amino)methyl)picolinate (0.200 g, 0.679 mmol), N,N-diisopropylethylamine (0.355 mL, 2.036 mmol) and triphosgene (0.101 g, 0.339 mmol) in dichloromethane (5 mL) was stirred at the room temperature for 30 min, and mixed with thiomorpholine 1,1-dioxide (0.092 g, 0.679 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=50% to 100%) to give methyl 5-((N-(3-chloro-4-fluorophenyl)-1,1-dioxidothiomorpholine-4-carboxamido)methyl)picolinate as pale brown solid (0.307 g, 99.1%).

[Step 2] N-(3-Chloro-4-fluorophenyl)-N-((6-(hydrazinecarbonyl)pyridin-3-yl)methyl)thiomorpholine-4-carboxamide 1,1-dioxide

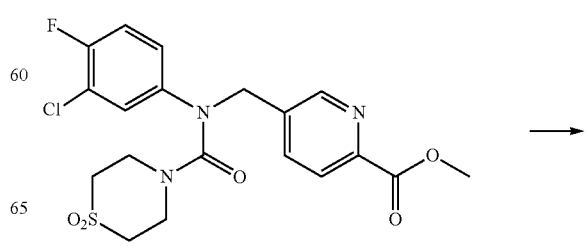

-continued

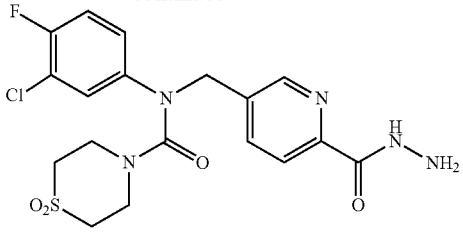

Methyl 5-((N-(3-chloro-4-fluorophenyl)-1,1-dioxidothiomorpholine-4-carboxamido)methyl)picolinate (0.307 g, 0.673 mmol) and hydrazine monohydrate (0.654 mL, 13.455 mmol) were mixed at the room temperature in 1,4-dioxane (4 mL) and then stirred at 70° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chloro-4-fluorophenyl)-N-((6-(hydrazinecarbonyl)pyridin-3-yl)methyl)thiomorpholine-4-carboxamide 1,1-dioxide as white solid (0.248 g, 80.9%).

[Step 3] Compound 21767

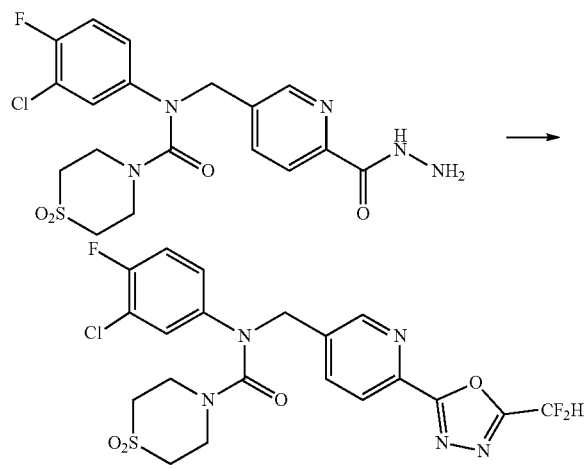

A solution of N-(3-chloro-4-fluorophenyl)-N-((6-(hydrazinecarbonyl)pyridin-3-yl)methyl)thiomorpholine-4-carboxamide 1,1-dioxide (0.194 g, 0.426 mmol), triethylamine (0.119 mL, 0.852 mmol) and 2,2-difluoroacetic anhydride (0.053 mL, 0.426 mmol) in dichloromethane (3 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(3-chloro-4-fluorophenyl)-N-((6-(5-(difluoromethyl)-1,3,4-oxadiazol-2-yl)pyridin-3-yl)methyl)thiomorpholine-4-carboxamide 1,1-dioxide as white solid (0.135 g, 61.3%).

$^1$H NMR (400 MHz, CDCl$_3$) δ 8.61 (d, 1H, J=1.6 Hz), 8.25 (dd, 1H, J=8.1, 0.6 Hz), 7.94 (dd, 1H, J=8.1, 2.2 Hz), 7.21-7.14 (m, 2H), 6.96-6.93 (m, 1H), 6.95 (t, 1H, J=51.7 Hz), 4.89 (s, 2H), 3.73 (t, 4H, J=5.3 Hz), 2.93 (t, 4H, J=5.3 Hz); LRMS (ES) m/z 516.4 (M$^+$+1).

Example 282. Compound 21797: N-(4-(5-(Difluoromethyl)-1,3,4-oxadiazol-2-yl)-2-fluorobenzyl)-N-(2,3-dihydro-1H-inden-5-yl)thiomorpholine-4-carboxamide 1,1-dioxide

[Step 1] N-(2,3-Dihydro-1H-inden-5-yl)thiomorpholine-4-carboxamide 1,1-dioxide

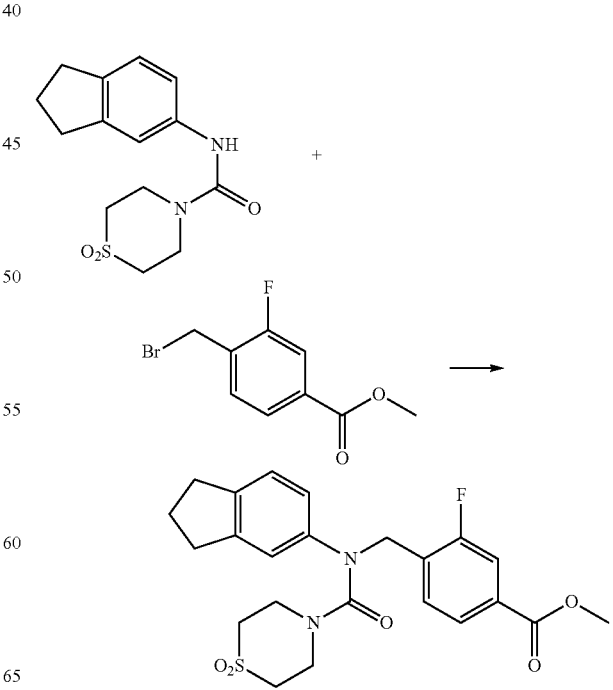

A solution of 5-isocyanato-2,3-dihydro-1H-indene (1.000 g, 6.282 mmol) and thiomorpholine 1,1-dioxide (0.858 g, 6.345 mmol) in diethylether (100 mL) was stirred at the room temperature for 16 hr. The precipitates were collected by filtration, washed by diethylether, and dried to give N-(2,3-dihydro-1H-inden-5-yl)thiomorpholine-4-carboxamide 1,1-dioxide as white solid (1.470 g, 79.5%).

[Step 2] Methyl 4-((N-(2,3-dihydro-1H-inden-5-yl)-1,1-dioxidothiomorpholine-4-carboxamido)methyl)-3-fluorobenzoate A solution of N-(2,3-dihydro-1H-inden-5-yl)thiomorpholine-4-carboxamide 1,1-dioxide (0.294 g, 1.000 mmol) and sodium hydride (60.00%, 0.044 g, 1.100 mmol) in tetrahydrofuran (5 mL) was stirred at the room temperature for 30 min, and mixed with methyl 4-(bromomethyl)-3-fluorobenzoate (0.259 g, 1.050 mmol). The reaction mixture was stirred at the same temperature for additional 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 30%) to give methyl 4-((N-(2,3-dihydro-1H-inden-5-yl)-1,1-dioxidothiomorpholine-4-carboxamido)methyl)-3-fluorobenzoate as white solid (0.392 g, 85.1%).

[Step 3] N-(2,3-Dihydro-1H-inden-5-yl)-N-(2-fluoro-4-(hydrazinecarbonyl)benzyl)thiomorpholine-4-carboxamide 1,1-dioxide

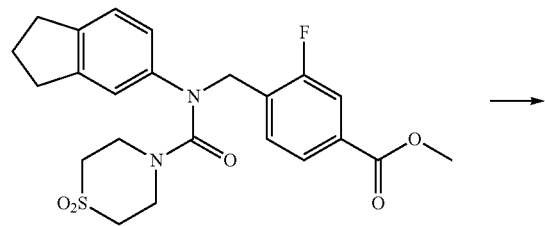

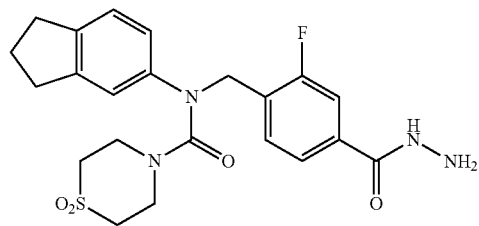

Methyl 4-((N-(2,3-dihydro-1H-inden-5-yl)-1,1-dioxidothiomorpholine-4-carboxamido)methyl)-3-fluorobenzoate (0.392 g, 0.851 mmol) and hydrazine monohydrate (0.827 mL, 17.024 mmol) were mixed at the room temperature in ethanol (5 mL) and then stirred at 80° C. for 18 hr and cooled down to the room temperature to terminate the reaction.

Then; water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(2,3-dihydro-1H-inden-5-yl)-N-(2-fluoro-4-(hydrazinecarbonyl)benzyl)thiomorpholine-4-carboxamide 1,1-dioxide, 0.391 g, 99.7%, white solid).

[Step 4] N-(4-(2-(2,2-Difluoroacetyl)hydrazine-1-carbonyl)-2-fluorobenzyl)-N-(2,3-dihydro-1H-inden-5-yl)thiomorpholine-4-carboxamide 1,1-dioxide

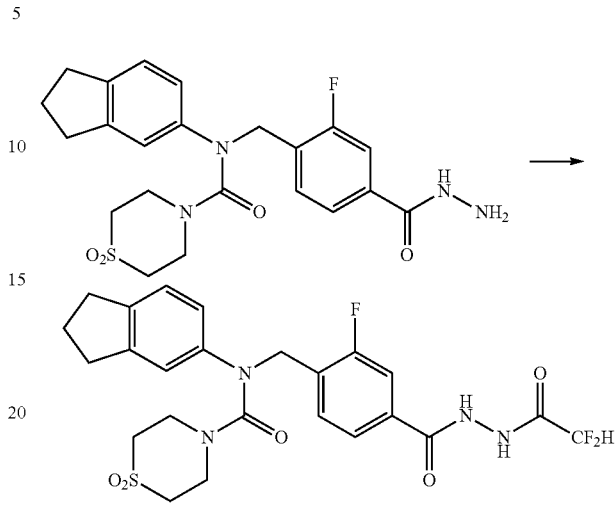

A solution of N-(2,3-dihydro-1H-inden-5-yl)-N-(2-fluoro-4-(hydrazinecarbonyl)benzyl)thiomorpholine-4-carboxamide 1,1-dioxide (0.391 g, 0.849 mmol), triethylamine (0.237 mL, 1.698 mmol) and 2,2-difluoroacetic anhydride (0.106 mL, 0.849 mmol) in dichloromethane (5 mL) was stirred at the room temperature for 18 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(4-(2-(2,2-difluoroacetyl)hydrazine-1-carbonyl)-2-fluorobenzyl)-N-(2,3-dihydro-1H-inden-5-yl)thiomorpholine-4-carboxamide 1,1-dioxide as white solid (0.226 g, 49.4%).

[Step 5] Compound 21797

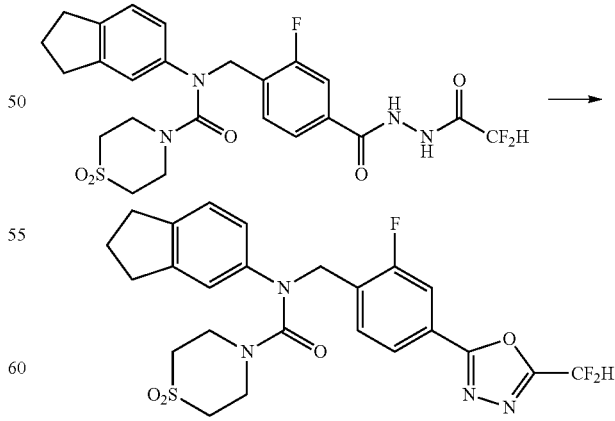

N-(4-(2-(2,2-Difluoroacetyl)hydrazine-1-carbonyl)-2-fluorobenzyl)-N-(2,3-dihydro-1H-inden-5-yl)thiomorpholine-4-carboxamide 1,1-dioxide (0.226 g, 0.419 mmol) and 1-methoxy-N-triethylammoniosulfonyl-methanimidate (Burgess reagent, 0.120 g, 0.503 mmol) were mixed at the room temperature in tetrahydrofuran (4 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=30% to 100%) to give N-(4-(5-(difluoromethyl)-1,3,4-oxadiazol-2-yl)-2-fluorobenzyl)-N-(2,3-dihydro-1H-inden-5-yl)thiomorpholine-4-carboxamide 1,1-dioxide as white solid (0.068 g, 31.2%).

$^1$H NMR (400 MHz, CDCl$_3$) δ 7.88 (dd, 1H, J=8.0, 1.5 Hz), 7.77 (dd, 1H, J=10.1, 1.5 Hz), 7.67 (t, 1H, J=7.6 Hz), 7.19 (d, 1H, J=7.9 Hz), 7.01 (d, 1H, J=1.6 Hz), 6.93 (t, 1H, J=51.6 Hz), 6.87 (dd, 1H, J=7.9, 2.0 Hz), 4.91 (s, 2H), 3.74 (t, 4H, J=5.0 Hz), 2.90 (t, 4H, J=7.4 Hz), 2.80 (t, 4H, J=5.1 Hz), 2.13 (t, 2H, J=3.8 Hz); LRMS (ES) m/z 521.4 (M$^+$+1).

Example 283. Compound 21798: N-(4-(5-(Difluoromethyl)-1,3,4-oxadiazol-2-yl)-2-fluorobenzyl)-N-(2,2-dimethyl-2,3-dihydrobenzofuran-7-yl)thiomorpholine-4-carboxamide 1,1-dioxide

[Step 1] N-(2,2-Dimethyl-2,3-dihydrobenzofuran-7-yl)thiomorpholine-4-carboxamide 1,1-dioxide

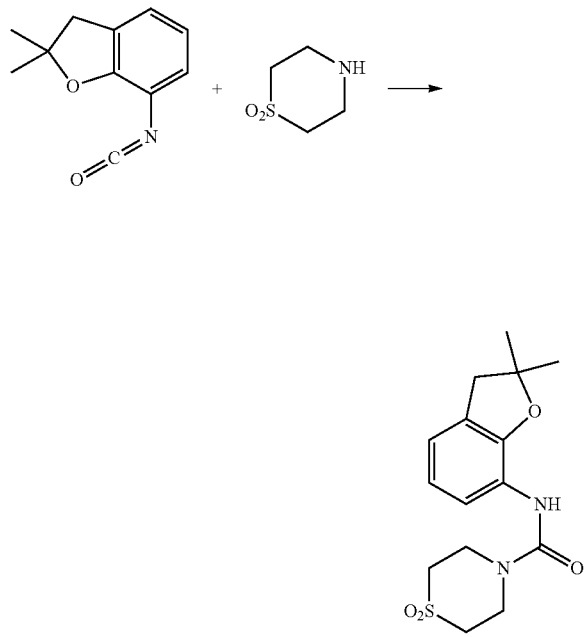

A solution of 7-isocyanato-2,2-dimethyl-2,3-dihydrobenzofuran (1.000 g, 5.285 mmol) and thiomorpholine 1,1-dioxide (0.722 g, 5.338 mmol) in diethylether (100 mL) was stirred at the room temperature for 16 hr. The precipitates were collected by filtration, washed by diethylether, and dried to give N-(2,2-dimethyl-2,3-dihydrobenzofuran-7-yl)thiomorpholine-4-carboxamide 1,1-dioxide as white solid (1.650 g, 96.2%).

[Step 2] Methyl 4-((N-(2,2-dimethyl-2,3-dihydrobenzofuran-7-yl)-1,1-dioxidothiomorpholine-4-carboxamido)methyl)-3-fluorobenzoate

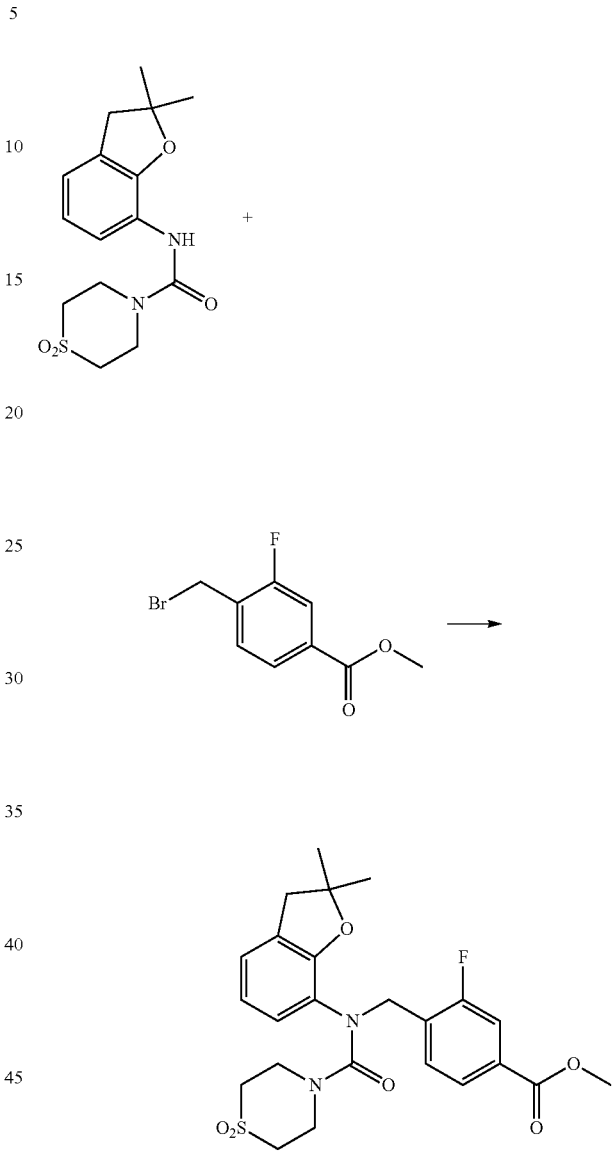

A solution of N-(2,2-dimethyl-2,3-dihydrobenzofuran-7-yl)thiomorpholine-4-carboxamide 1,1-dioxide (0.324 g, 1.000 mmol) and sodium hydride (60.00%, 0.044 g, 1.100 mmol) in tetrahydrofuran (5 mL) was stirred at the room temperature for 30 min, and mixed with methyl 4-(bromomethyl)-3-fluorobenzoate (0.259 g, 1.050 mmol). The reaction mixture was stirred at the same temperature for additional 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 30%) to give methyl 4-((N-(2,2-dimethyl-2,3-dihydrobenzofuran-7-yl)-1,1-dioxidothiomorpholine-4-carboxamido)methyl)-3-fluorobenzoate as colorless oil (0.459 g, 93.6%).

905

[Step 3] N-(2,2-Dimethyl-2,3-dihydrobenzofuran-7-yl)-N-(2-fluoro-4-(hydrazinecarbonyl)benzyl) thiomorpholine-4-carboxamide 1,1-dioxide

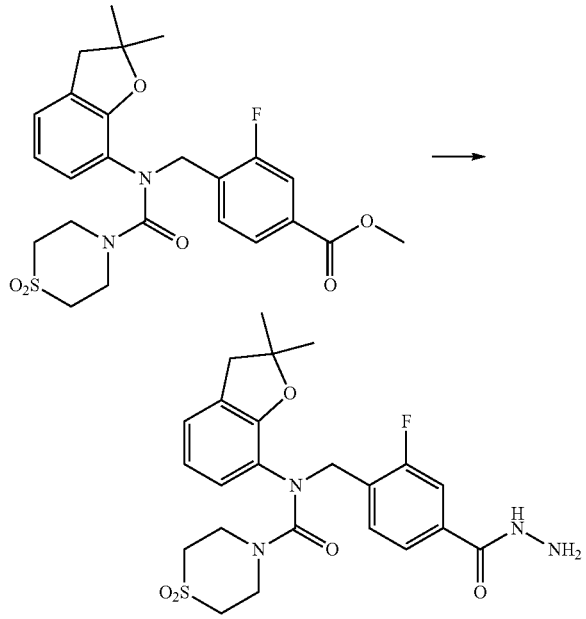

Methyl 4-((N-(2,2-dimethyl-2,3-dihydrobenzofuran-7-yl)-1,1-dioxidothiomorpholine-4-carboxamido)methyl)-3-fluorobenzoate (0.459 g, 0.936 mmol) and hydrazine monohydrate (0.910 mL, 18.714 mmol) were mixed at the room temperature in ethanol (5 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(2,2-dimethyl-2,3-dihydrobenzofuran-7-yl)-N-(2-fluoro-4-(hydrazinecarbonyl)benzyl)thiomorpholine-4-carboxamide 1,1-dioxide, 0.458 g, 99.8%, white solid).

[Step 4] N-(4-(2-(2,2-Difluoroacetyl)hydrazine-1-carbonyl)-2-fluorobenzyl)-N-(2,2-dimethyl-2,3-dihydrobenzofuran-7-yl)thiomorpholine-4-carboxamide 1,1-dioxide

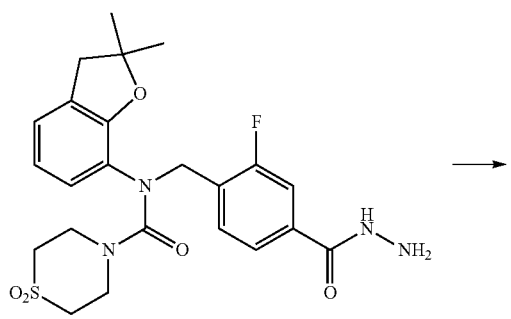

906

-continued

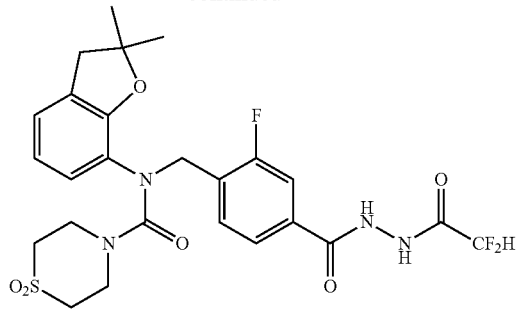

A solution of N-(2,2-dimethyl-2,3-dihydrobenzofuran-7-yl)-N-(2-fluoro-4-(hydrazinecarbonyl)benzyl)thiomorpholine-4-carboxamide 1,1-dioxide (0.458 g, 0.934 mmol), triethylamine (0.260 mL, 1.867 mmol) and 2,2-difluoroacetic anhydride (0.116 mL, 0.934 mmol) in dichloromethane (5 mL) was stirred at the room temperature for 18 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(4-(2-(2,2-difluoroacetyl)hydrazine-1-carbonyl)-2-fluorobenzyl)-N-(2,2-dimethyl-2,3-dihydrobenzofuran-7-yl)thiomorpholine-4-carboxamide 1,1-dioxide as white solid (0.248 g, 46.6%).

[Step 5] Compound 21798

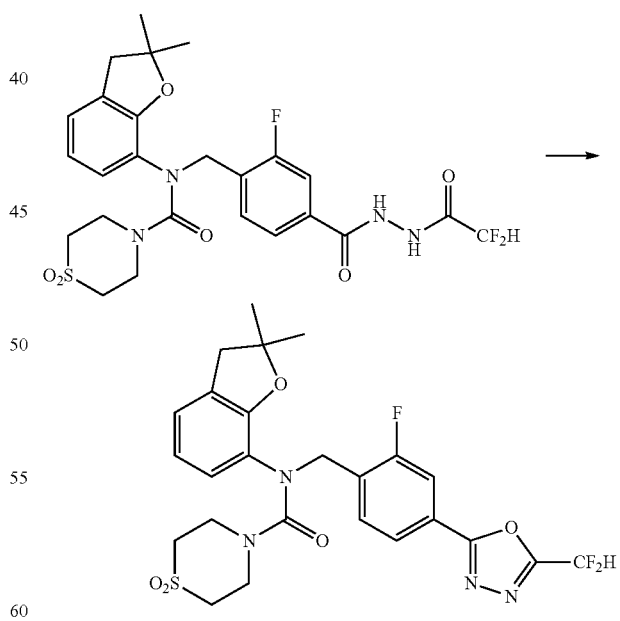

N-(4-(2-(2,2-Difluoroacetyl)hydrazine-1-carbonyl)-2-fluorobenzyl)-N-(2,2-dimethyl-2,3-dihydrobenzofuran-7-yl)thiomorpholine-4-carboxamide 1,1-dioxide (0.248 g, 0.435 mmol) and 1-methoxy-N-triethylammoniosulfonylmethanimidate (Burgess reagent, 0.124 g, 0.522 mmol) were mixed at the room temperature in tetrahydrofuran (4 mL)

and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=30% to 100%) to give N-(4-(5-(difluoromethyl)-1,3,4-oxadiazol-2-yl)-2-fluorobenzyl)-N-(2,2-dimethyl-2,3-dihydrobenzofuran-7-yl)thiomorpholine-4-carboxamide 1,1-dioxide as white solid (0.102 g, 42.5%).

$^1$H NMR (400 MHz, CDCl$_3$) δ 7.87-7.83 (m, 2H), 7.69-7.67 (m, 1H), 7.05-6.77 (m, 4H), 4.91 (s, 2H), 3.74 (t, 4H, J=5.1 Hz), 3.05 (s, 2H), 2.78 (t, 4H, J=5.1 Hz), 1.47 (s, 6H); LRMS (ES) m/z 551.4 (M$^+$+1).

Example 284. Compound 21799: N-(4-(5-(Difluoromethyl)-1,3,4-oxadiazol-2-yl)-2-fluorobenzyl)-N-(1-methyl-1H-indol-5-yl)thiomorpholine-4-carboxamide 1,1-dioxide

[Step 1] N-(1-Methyl-1H-indol-5-yl)thiomorpholine-4-carboxamide 1,1-dioxide

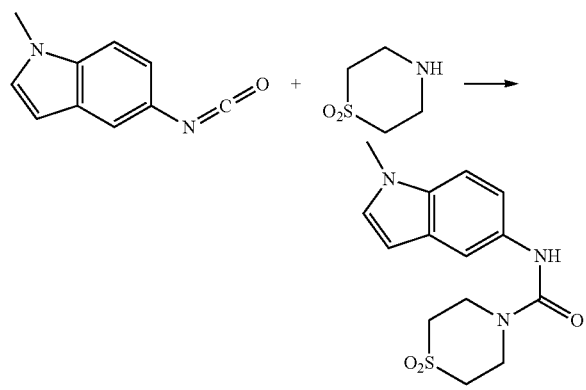

A solution of 5-isocyanato-1-methyl-1H-indole (1.000 g, 5.808 mmol) and thiomorpholine 1,1-dioxide (0.793 g, 5.866 mmol) in diethylether (100 mL) was stirred at the room temperature for 16 hr. The precipitates were collected by filtration, washed by diethylether, and dried to give N-(1-methyl-1H-indol-5-yl)thiomorpholine-4-carboxamide 1,1-dioxide as white solid (1.780 g, 99.7%).

[Step 2] Methyl 3-fluoro-4-((N-(1-methyl-1H-indol-5-yl)-1,1-dioxidothiomorpholine-4-carboxamido)methyl)benzoate

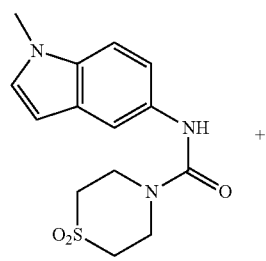

+

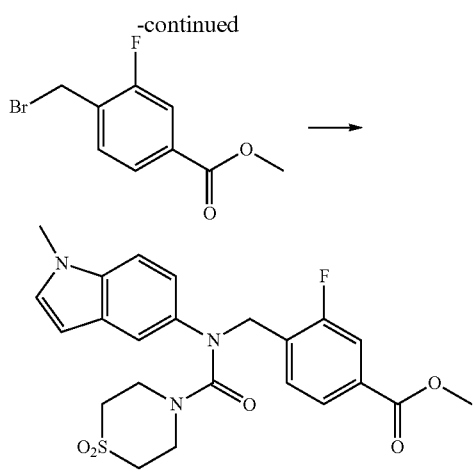

A solution of N-(1-methyl-1H-indol-5-yl)thiomorpholine-4-carboxamide 1,1-dioxide (0.307 g, 1.000 mmol) and sodium hydride (60.00%, 0.044 g, 1.100 mmol) in tetrahydrofuran (5 mL) was stirred at the room temperature for 30 min, and mixed with methyl 4-(bromomethyl)-3-fluorobenzoate (0.259 g, 1.050 mmol). The reaction mixture was stirred at the same temperature for additional 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 30%) to give methyl 3-fluoro-4-((N-(1-methyl-1H-indol-5-yl)-1,1-dioxidothiomorpholine-4-carboxamido)methyl)benzoate as white solid (0.406 g, 85.7%).

[Step 3] N-(2-Fluoro-4-(hydrazinecarbonyl)benzyl)-N-(1-methyl-1H-indol-5-yl)thiomorpholine-4-carboxamide 1,1-dioxide

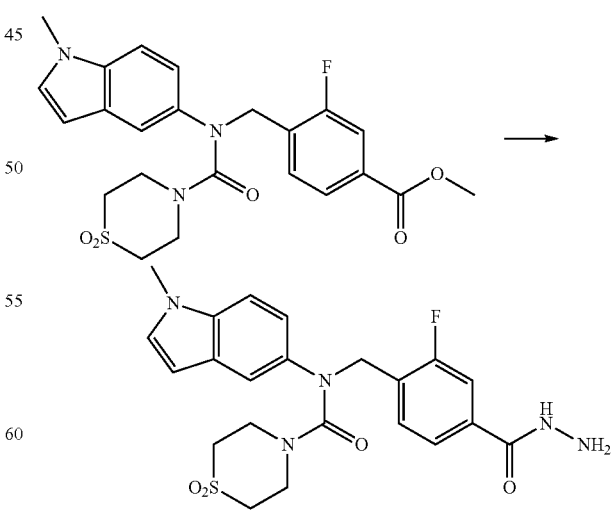

Methyl 3-fluoro-4-((N-(1-methyl-1H-indol-5-yl)-1,1-dioxidothiomorpholine-4-carboxamido)methyl)benzoate (0.406 g, 0.857 mmol) and hydrazine monohydrate (0.833 mL, 17.148 mmol) were mixed at the room temperature in ethanol (5 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(2-fluoro-4-(hydrazinecarbonyl)benzyl)-N-(1-methyl-1H-indol-5-yl)thiomorpholine-4-carboxamide 1,1-dioxide, 0.243 g, 59.8%, white solid).

[Step 4] N-(4-(2-(2,2-Difluoroacetyl)hydrazine-1-carbonyl)-2-fluorobenzyl)-N-(1-methyl-1H-indol-5-yl)thiomorpholine-4-carboxamide 1,1-dioxide

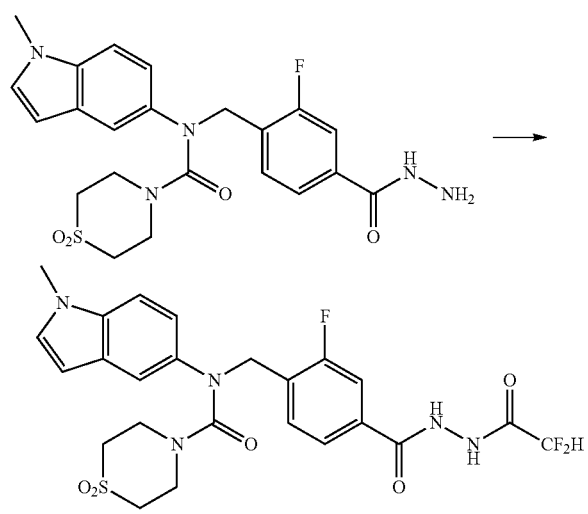

A solution of N-(2-fluoro-4-(hydrazinecarbonyl)benzyl)-N-(1-methyl-1H-indol-5-yl)thiomorpholine-4-carboxamide 1,1-dioxide (0.243 g, 0.513 mmol), triethylamine (0.143 mL, 1.026 mmol) and 2,2-difluoroacetic anhydride (0.064 mL, 0.513 mmol) in dichloromethane (5 mL) was stirred at the room temperature for 18 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(4-(2-(2,2-difluoroacetyl)hydrazine-1-carbonyl)-2-fluorobenzyl)-N-(1-methyl-1H-indo 1-5-yl)thiomorpholine-4-carboxamide 1,1-dioxide as pale yellow solid (0.206 g, 72.7%).

[Step 5] Compound 21799

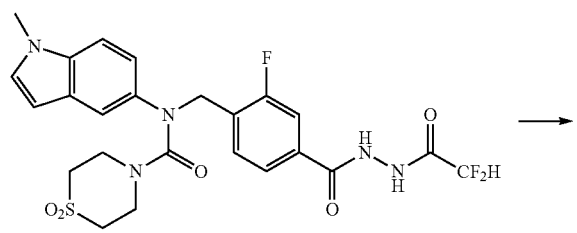

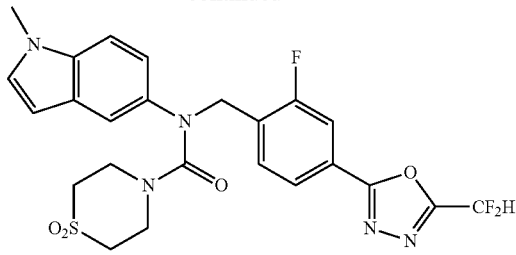

N-(4-(2-(2,2-Difluoroacetyl)hydrazine-1-carbonyl)-2-fluorobenzyl)-N-(1-methyl-1H-indol-5-yl)thiomorpholine-4-carboxamide 1,1-dioxide (0.206 g, 0.373 mmol) and 1-methoxy-N-triethylammoniosulfonyl-methanimidate (Burgess reagent, 0.107 g, 0.448 mmol) were mixed at the room temperature in tetrahydrofuran (4 mL) and then stirred at 80° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=30% to 100%) to give N-(4-(5-(difluoromethyl)-1,3,4-oxadiazol-2-yl)-2-fluorobenzyl)-N-(1-methyl-1H-indol-5-yl)thiomorpholine-4-carboxamide 1,1-dioxide as pale yellow solid (0.009 g, 4.3%).
$^1$H NMR (400 MHz, CDCl$_3$) δ 7.87 (dd, 1H, J=8.0, 1.6 Hz), 7.75-7.68 (m, 2H), 7.37 (d, 1H, J=1.9 Hz), 7.30-1H), 7.13 (d, 1H, J=3.1 Hz), 6.96 (dd, 1H, J=8.7, 2.1 Hz), 6.93 (t, 1H, J=51.7 Hz), 6.45 (dd, 1H, J=3.1, 0.8 Hz), 4.97 (s, 2H), 3.82 (s, 3H), 3.76 (t, 4H, J=4.9 Hz), 2.70 (t, 4H, J=5.2 Hz); LRMS (ES) m/z 521.4 (M$^+$+1).

Example 285. Compound 21806: N-(4-(5-(difluoromethyl)-1,3,4-oxadiazol-2-yl)-2-fluorobenzyl)-N-(4-fluorophenyl)thiomorpholine-4-carboxamide 1,1-dioxide

[Step 1]
N-(4-fluorophenyl)thiomorpholine-4-carboxamide 1,1-dioxide

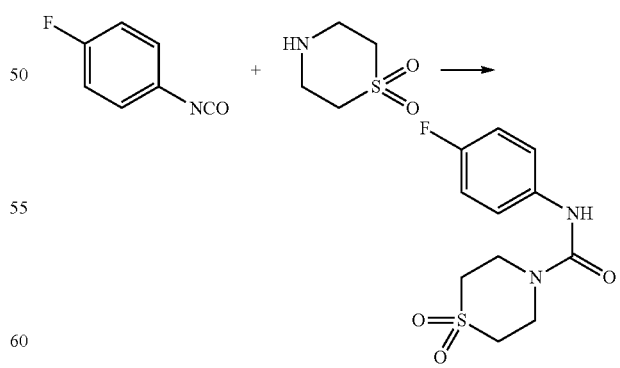

A solution of 1-fluoro-4-isocyanatobenzene (0.500 g, 3.647 mmol) in diethylether (10 mL) was mixed at 0° C. with thiomorpholine 1,1-dioxide (0.493 g, 3.647 mmol), and stirred at the same temperature for 1 hr. The reaction mixture was stirred at the room temperature for additional 4 hr. The

911 precipitates were collected by filtration, washed by diethylether, and dried to give N-(4-fluorophenyl)thiomorpholine-4-carboxamide 1,1-dioxide as white solid (0.920 g, 92.7%).

[Step 2] Methyl 3-fluoro-4-((N-(4-fluorophenyl)-1,1-dioxidothiomorpholine-4-carboxamido)methyl)benzoate

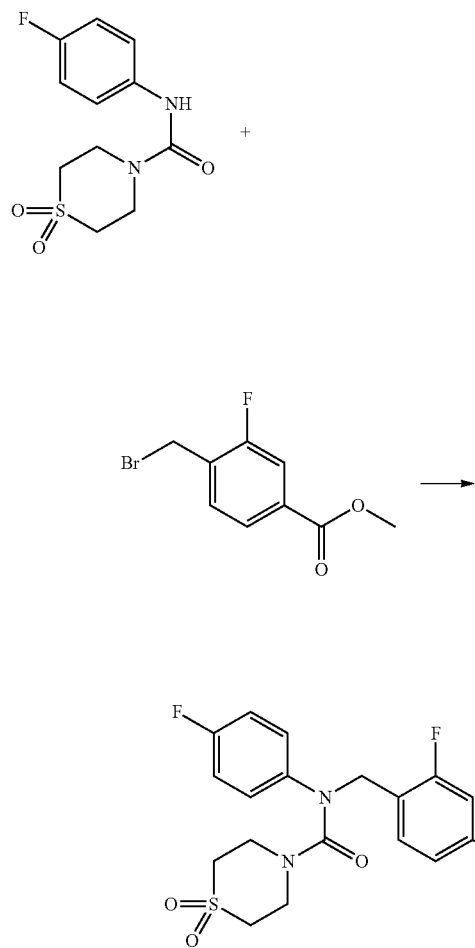

A solution of N-(4-fluorophenyl)thiomorpholine-4-carboxamide 1,1-dioxide (0.300 g, 1.102 mmol) and sodium hydride (60.00%, 0.048 g, 1.212 mmol) in N,N-dimethylformamide (5 mL) was stirred at 0° C. for 2 hr, and mixed with methyl 4-(bromomethyl)-3-fluorobenzoate (0.299 g, 1.212 mmol). The reaction mixture was stirred at the room temperature for additional 17 hr, quenched at the room temperature by the addition of water (2 mL, 10 min stirring). Then, water was added to the reaction mixture, followed by extraction with dichloromethane. The bi-phasic mixture was passed through a plastic frit to remove the solid residues and aqueous layer, and the organic layer collected was concentrated in vacuo. The crude product was crystallized at the room temperature using dichloromethane (3 mL). The resulting precipitates were filtered, washed by dichloromethane, and dried to give methyl 3-fluoro-4-((N-(4-fluorophenyl)-1,1-dioxidothiomorpholine-4-carboxamido)methyl)benzoate as white solid (0.212 g, 43.9%).

912

[Step 3] N-(2-fluoro-4-(hydrazinecarbonyl)benzyl)-N-(4-fluorophenyl)thiomorpholine-4-carboxamide 1,1-dioxide

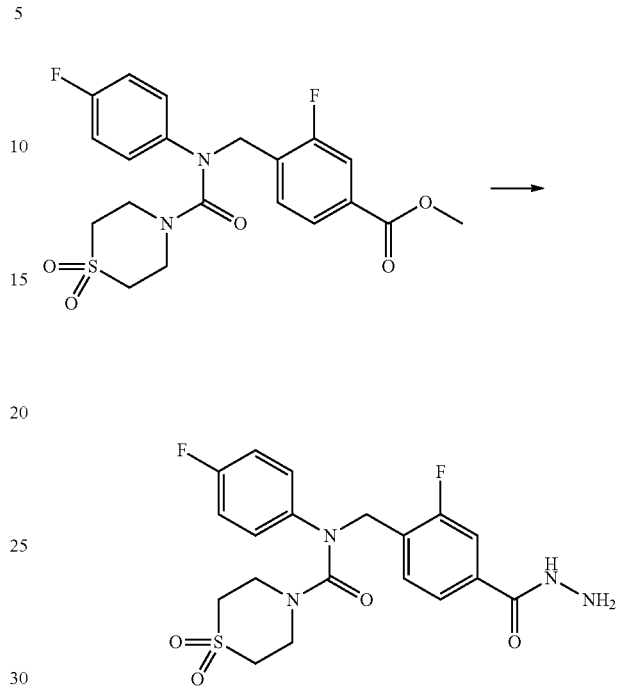

Methyl 3-fluoro-4-((N-(4-fluorophenyl)-1,1-dioxidothiomorpholine-4-carboxamido)methyl)benzoate (0.212 g, 0.484 mmol) and hydrazine monohydrate (0.470 mL, 9.670 mmol) in ethanol (4 mL) was mixed at the room temperature and then heated at 120° C. under the microwaves for 1 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was diluted with diethylether (5 mL) and ethyl acetate (1 mL) and stirred at the ambient temperature. The resulting precipitates were collected by filtration, washed by hexane, and dried to give N-(2-fluoro-4-(hydrazinecarbonyl)benzyl)-N-(4-fluorophenyl)thiomorpholine-4-carboxamide 1,1-dioxide as white solid (0.179 g, 84.4%).

[Step 4] Compound 21806

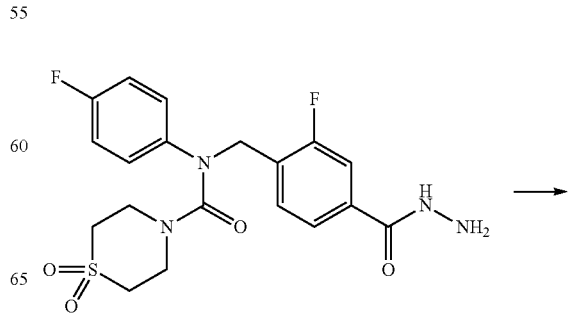

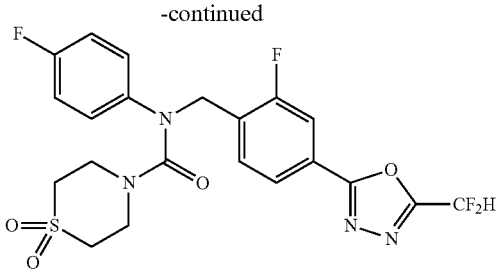

A solution of N-(2-fluoro-4-(hydrazinecarbonyl)benzyl)-N-(4-fluorophenyl)thiomorpholine-4-carboxamide 1,1-dioxide (0.100 g, 0.228 mmol) and triethylamine (0.095 mL, 0.684 mmol) in dichloromethane (4 mL) was mixed at the room temperature with 2,2-difluoroacetic anhydride (0.028 mL, 0.228 mmol), and stirred at the same temperature for 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=20% to 50%) to give N-(4-(5-(difluoromethyl)-1,3,4-oxadiazol-2-yl)-2-fluorobenzyl)-N-(4-fluorophenyl)thiomorpholine-4-carboxamide 1,1-dioxide as white solid (0.053 g, 46.6%).

$^1$H NMR (400 MHz, CDCl$_3$) δ 7.90 (dd, 1H, J=8.0, 1.6 Hz), 7.77 (dd, 1H, J=10.1, 1.6 Hz), 7.69 (t, 1H, J=7.6 Hz), 7.14-6.81 (m, 5H), 4.90 (s, 2H), 3.74-3.71 (m, 4H), 2.85-2.82 (m, 4H); LRMS (ES) m/z 499.3 (M$^+$+1).

Example 286. Compound 21807: N-(4-(5-(difluoromethyl)-1,3,4-oxadiazol-2-yl)-2-fluorobenzyl)-N-(3-fluorophenyl)thiomorpholine-4-carboxamide 1,1-dioxide

[Step 1]
N-(3-fluorophenyl)thiomorpholine-4-carboxamide 1,1-dioxide

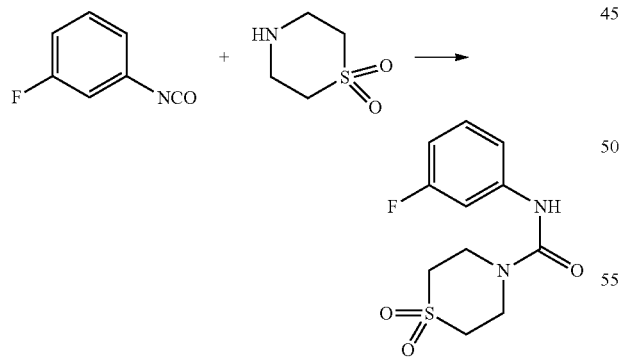

A solution of 1-fluoro-3-isocyanatobenzene (0.500 g, 3.647 mmol) in diethylether (10 mL) was mixed at 0° C. with thiomorpholine 1,1-dioxide (0.493 g, 3.647 mmol), and stirred at the same temperature for 1 hr. The reaction mixture was stirred at the room temperature for additional 4 hr. The precipitates were collected by filtration, washed by diethylether, and dried to give N-(3-fluorophenyl)thiomorpholine-4-carboxamide 1,1-dioxide as white solid (0.870 g, 87.6%).

[Step 2] Methyl 3-fluoro-4-((N-(3-fluorophenyl)-1,1-dioxidothiomorpholine-4-carboxamido)methyl)benzoate

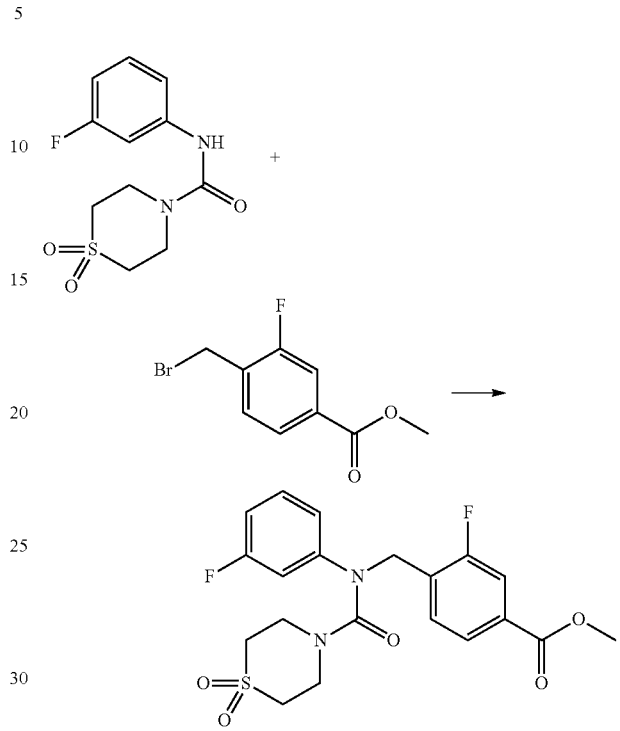

A solution of N-(3-fluorophenyl)thiomorpholine-4-carboxamide 1,1-dioxide (0.300 g, 1.102 mmol) and sodium hydride (60.00%, 0.048 g, 1.212 mmol) in N,N-dimethylformamide (5 mL) was stirred at 0° C. for 2 hr, and mixed with methyl 4-(bromomethyl)-3-fluorobenzoate (0.299 g, 1.212 mmol). The reaction mixture was stirred at the room temperature for additional 17 hr, quenched at the room temperature by the addition of water (2 mL, 10 min stirring). Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 40%) to give methyl 3-fluoro-4-((N-(3-fluorophenyl)-1,1-dioxidothiomorpholine-4-carboxamido)methyl)benzoate as white solid (0.300 g, 62.1%).

[Step 3] N-(2-fluoro-4-(hydrazinecarbonyl)benzyl)-N-(3-fluorophenyl)thiomorpholine-4-carboxamide 1,1-dioxide

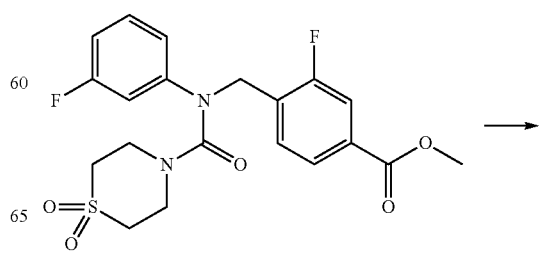

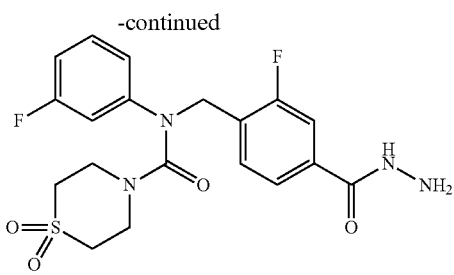

Methyl 3-fluoro-4-((N-(3-fluorophenyl)-1,1-dioxidothiomorpholine-4-carboxamido)methyl)benzoate (0.300 g, 0.684 mmol) and hydrazine monohydrate (0.665 mL, 13.685 mmol) in ethanol (4 mL) was mixed at the room temperature and then heated at 120° C. under the microwaves for 1 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was diluted with diethylether (5 mL) and ethyl acetate (1 mL) and stirred at the ambient temperature. The resulting precipitates were collected by filtration, washed by hexane, and dried to give N-(2-fluoro-4-(hydrazinecarbonyl)benzyl)-N-(3-fluorophenyl)thiomorpholine-4-carboxamide 1,1-dioxide as white solid (0.270 g, 90.0%).

[Step 4] Compound 21807

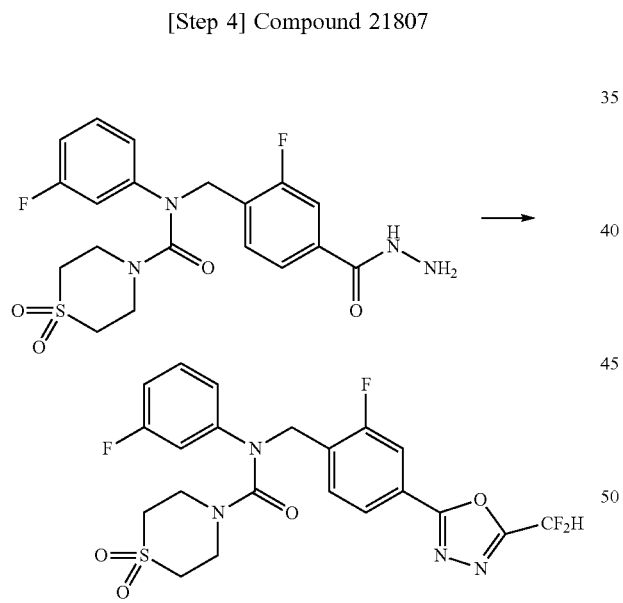

A solution of N-(2-fluoro-4-(hydrazinecarbonyl)benzyl)-N-(3-fluorophenyl)thiomorpholine-4-carboxamide 1,1-dioxide (0.100 g, 0.228 mmol) and triethylamine (0.095 mL, 0.684 mmol) in dichloromethane (4 mL) was mixed at the room temperature with 2,2-difluoroacetic anhydride (0.028 mL, 0.228 mmol), and stirred at the same temperature for 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=20% to 50%) to give N-(4-(5-(difluoromethyl)-1,3,4-oxadiazol-2-yl)-2-fluorobenzyl)-N-(3-fluorophenyl)thiomorpholine-4-carboxamide 1,1-dioxide as white solid (0.034 g, 29.9%).

$^1$H NMR (400 MHz, CDCl$_3$) δ 7.90 (dd, 1H, J=8.0, 1.6 Hz), 7.79 (dd, 1H, J=10.1, 1.6 Hz), 7.68 (t, 1H, J=7.6 Hz), 7.38-7.33 (m, 1H), 7.07-6.81 (m, 4H), 4.95 (s, 2H), 3.75 (t, 4H, J=5.2 Hz), 2.87 (t, 4H, J=5.2 Hz); LRMS (ES) m/z 499.0 (M$^+$+1).

Example 287. Compound 21808: N-(4-(5-(difluoromethyl)-1,3,4-oxadiazol-2-yl)-2-fluorobenzyl)-N-(2-fluorophenyl)thiomorpholine-4-carboxamide 1,1-dioxide

[Step 1] Methyl 3-fluoro-4-((N-(2-fluorophenyl)-1,1-dioxidothiomorpholine-4-carboxamido)methyl)benzoate A solution of N-(2-fluorophenyl)thiomorpholine-4-carboxamide 1,1-dioxide (0.300 g, 1.102 mmol) and sodium hydride (60.00%, 0.048 g, 1.212 mmol) in N,N-dimethylformamide (5 mL) was stirred at 0° C. for 2 hr, and mixed with methyl 4-(bromomethyl)-3-fluorobenzoate (0.299 g, 1.212 mmol). The reaction mixture was stirred at the room temperature for additional 17 hr, quenched at the room temperature by the addition of water (2 mL, 10 min stirring). Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 40%) to give methyl 3-fluoro-4-((N-(2-fluorophenyl)-1,1-dioxidothiomorpholine-4-carboxamido)methyl)benzoate as white solid (0.320 g, 66.2%).

917

[Step 2] N-(2-fluoro-4-(hydrazinecarbonyl)benzyl)-N-(2-fluorophenyl)thiomorpholine-4-carboxamide 1,1-dioxide

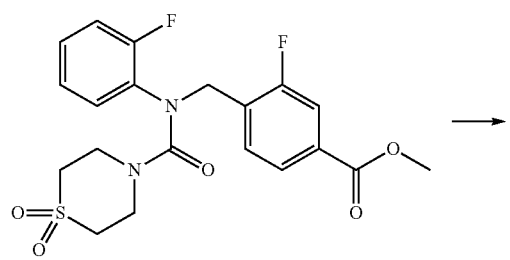

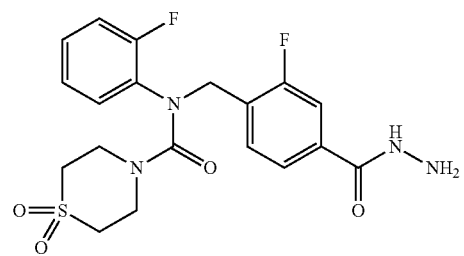

Methyl 3-fluoro-4-((N-(2-fluorophenyl)-1,1-dioxidothiomorpholine-4-carboxamido)methyl)benzoate (0.320 g, 0.730 mmol) and hydrazine monohydrate (0.709 mL, 14.597 mmol) in ethanol (4 mL) was mixed at the room temperature and then heated at 120° C. under the microwaves for 1 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was diluted with diethylether (5 mL) and ethyl acetate (1 mL) and stirred at the ambient temperature. The resulting precipitates were collected by filtration, washed by hexane, and dried to give N-(2-fluoro-4-(hydrazinecarbonyl)benzyl)-N-(2-fluorophenyl)thiomorpholine-4-carboxamide 1,1-dioxide as white solid (0.258 g, 80.6%).

[Step 3] Compound 21808

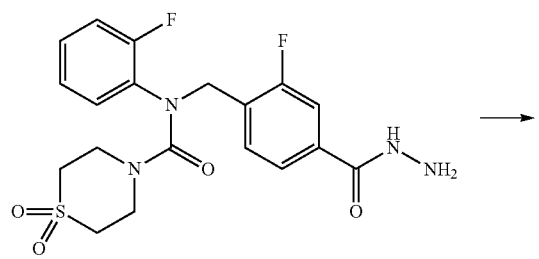

918

-continued

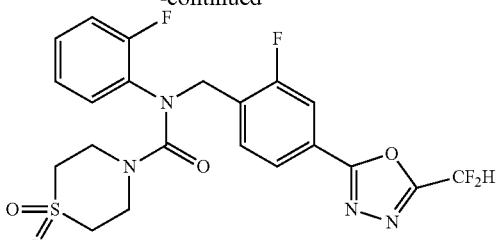

A solution of N-(2-fluoro-4-(hydrazinecarbonyl)benzyl)-N-(2-fluorophenyl)thiomorpholine-4-carboxamide 1,1-dioxide (0.100 g, 0.228 mmol) and triethylamine (0.095 mL, 0.684 mmol) in dichloromethane (4 mL) was mixed at the room temperature with 2,2-difluoroacetic anhydride (0.028 mL, 0.228 mmol), and stirred at the same temperature for 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=20% to 50%) to give N-(4-(5-(difluoromethyl)-1,3,4-oxadiazol-2-yl)-2-fluorobenzyl)-N-(2-fluorophenyl)thiomorpholine-4-carboxamide 1,1-dioxide as white solid (0.010 g, 8.8%).

$^1$H NMR (400 MHz, CDCl$_3$) δ 7.88 (dd, 1H, J=8.0, 1.5 Hz), 7.78 (t, 1H, J=7.6 Hz), 7.72 (dd, 1H, J=9.9, 1.5 Hz), 7.32-7.27 (m, 1H), 7.19-7.13 (m, 3H), 6.93 (t, 1H, J=51.6 Hz), 4.90 (s, 2H), 3.72 (t, 4H, J=5.0 Hz), 2.76 (t, 4H, J=5.2 Hz); LRMS (ES) m/z 499.0 (M$^+$+1).

Example 288. Compound 21809: N-(4-chlorophenyl)-N-(4-(5-(difluoromethyl)-1,3,4-oxadiazol-2-yl)-2-fluorobenzyl)thiomorpholine-4-carboxamide 1,1-dioxide

[Step 1]
N-(4-chlorophenyl)thiomorpholine-4-carboxamide 1,1-dioxide

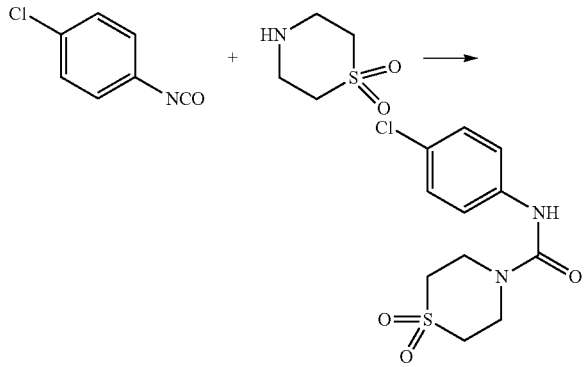

A solution of 1-chloro-4-isocyanatobenzene (0.500 g, 3.256 mmol) in diethylether (15 mL) was mixed at 0° C. with thiomorpholine 1,1-dioxide (0.440 g, 3.256 mmol), and stirred at the same temperature for 1 hr. The reaction mixture was stirred at the room temperature for additional 4 hr. The precipitates were collected by filtration, washed by diethylether, and dried to give N-(4-chlorophenyl)thiomorpholine-4-carboxamide 1,1-dioxide as white solid (0.826 g, 87.9%).

[Step 2] Methyl 4-((N-(4-chlorophenyl)-1,1-dioxidothiomorpholine-4-carboxamido)methyl)-3-fluorobenzoate

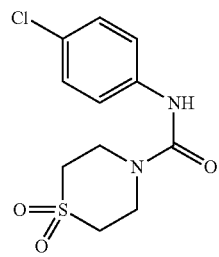

+

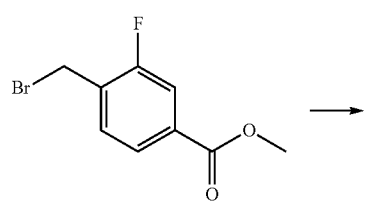

→

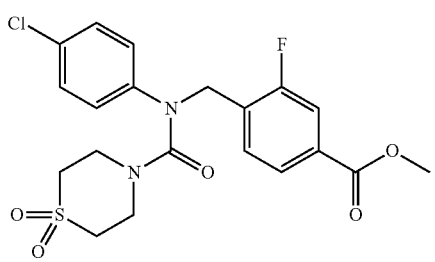

A solution of N-(4-chlorophenyl)thiomorpholine-4-carboxamide 1,1-dioxide (0.300 g, 1.039 mmol) and sodium hydride (60.00%, 0.046 g, 1.143 mmol) in N,N-dimethylformamide (5 mL) was stirred at 0° C. for 2 hr, and mixed with methyl 4-(bromomethyl)-3-fluorobenzoate (0.282 g, 1.143 mmol). The reaction mixture was stirred at the room temperature for additional 17 hr, quenched at the room temperature by the addition of water (2 mL, 10 min stirring). Then, water was added to the reaction mixture, followed by extraction with dichloromethane. The bi-phasic mixture was passed through a plastic frit to remove the solid residues and aqueous layer, and the organic layer collected was concentrated in vacuo. The crude product was crystallized at the room temperature using dichloromethane (3 mL). The resulting precipitates were filtered, washed by dichloromethane, and dried to give methyl 4-((N-(4-chlorophenyl)-1,1-dioxidothiomorpholine-4-carboxamido)methyl)-3-fluorobenzoate as white solid (0.217 g, 45.9%).

[Step 3] N-(4-chlorophenyl)-N-(2-fluoro-4-(hydrazinecarbonyl)benzyl)thiomorpholine-4-carboxamide 1,1-dioxide

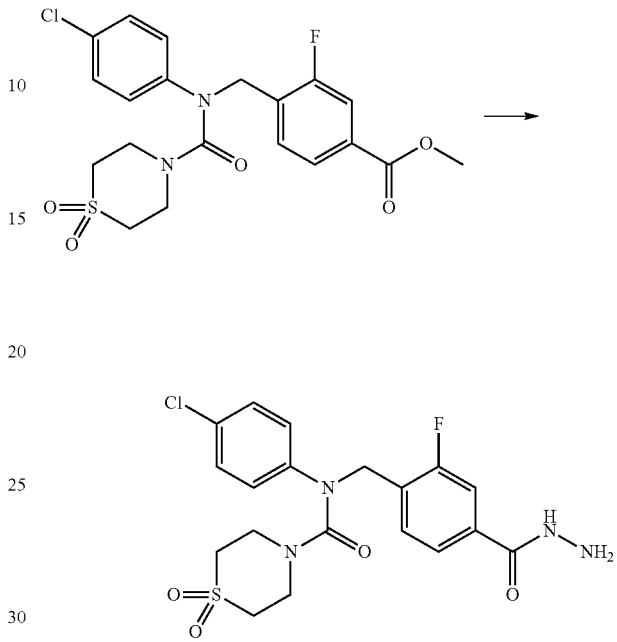

Methyl 4-((N-(4-chlorophenyl)-1,1-dioxidothiomorpholine-4-carboxamido)methyl)-3-fluorobenzoate (0.217 g, 0.477 mmol) and hydrazine monohydrate (0.464 mL, 9.541 mmol) in ethanol (4 mL) was mixed at the room temperature and then heated at 120° C. under the microwaves for 1 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-chlorophenyl)-N-(2-fluoro-4-(hydrazinecarbonyl)benzyl)thiomorpholine-4-carboxamide 1,1-dioxide as white solid (0.187 g, 86.2%).

[Step 4] Compound 21809

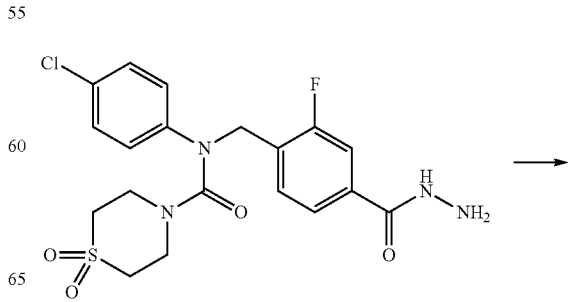

921

-continued

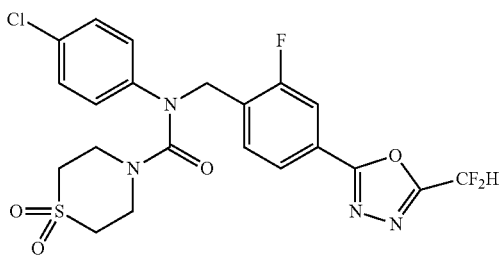

A solution of N-(4-chlorophenyl)-N-(2-fluoro-4-(hydrazinecarbonyl)benzyl)thiomorpholine-4-carboxamide 1,1-dioxide (0.100 g, 0.220 mmol) and triethylamine (0.092 mL, 0.659 mmol) in dichloromethane (4 mL) was mixed at the room temperature with 2,2-difluoroacetic anhydride (0.027 mL, 0.220 mmol), and stirred at the same temperature for 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=20% to 50%) to give N-(4-chlorophenyl)-N-(4-(5-(difluoromethyl)-1,3,4-oxadiazol-2-yl)-2-fluorobenzyl)thiomorpholine-4-carboxamide 1,1-dioxide as white solid (0.026 g, 23.0%).

$^1$H NMR (400 MHz, CDCl$_3$) δ 7.90 (dd, 1H, J=8.0, 1.6 Hz), 7.78 (dd, 1H, J=10.1, 1.6 Hz), 7.68 (t, 1H, J=7.6 Hz), 7.35 (d, 2H, J=8.8 Hz), 7.10-6.81 (m, 3H), 4.93 (s, 2H), 4.15-4.13 (m, 4H), 2.86 (t, 4H, J=5.3 Hz); LRMS (ES) m/z 515.1 (M$^+$+1).

Example 289. Compound 21810: N-(3-chlorophenyl)-N-(4-(5-(difluoromethyl)-1,3,4-oxadiazol-2-yl)-2-fluorobenzyl)thiomorpholine-4-carboxamide 1,1-dioxide

[Step 1] Methyl 4-((N-(3-chlorophenyl)-1,1-dioxidothiomorpholine-4-carboxamido)methyl)-3-fluorobenzoate

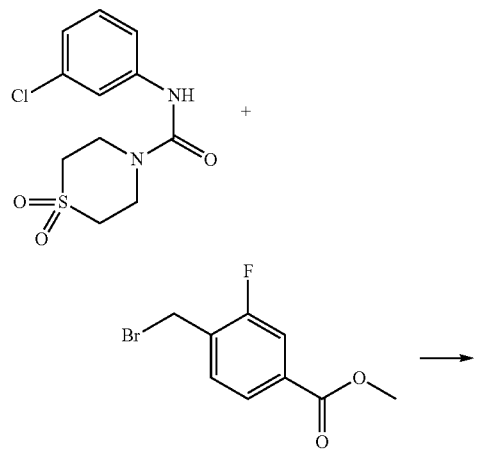

922

-continued

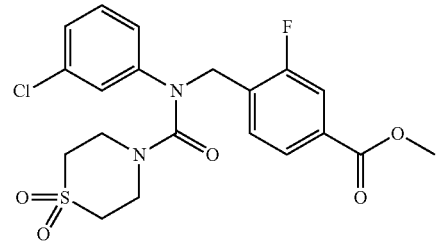

A solution of N-(3-chlorophenyl)thiomorpholine-4-carboxamide 1,1-dioxide (0.300 g, 1.039 mmol) and sodium hydride (60.00%, 0.046 g, 1.143 mmol) in N,N-dimethylformamide (5 mL) was stirred at 0° C. for 2 hr, and mixed with methyl 4-(bromomethyl)-3-fluorobenzoate (0.282 g, 1.143 mmol). The reaction mixture was stirred at the room temperature for additional 17 hr, quenched at the room temperature by the addition of water (2 mL, 10 min stirring). Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=0% to 40%) to give methyl 4-((N-(3-chlorophenyl)-1,1-dioxidothiomorpholine-4-carboxamido)methyl)-3-fluorobenzoate as white solid (0.440 g, 93.1%).

[Step 2] N-(3-chlorophenyl)-N-(2-fluoro-4-(hydrazinecarbonyl)benzyl)thiomorpholine-4-carboxamide 1,1-dioxide

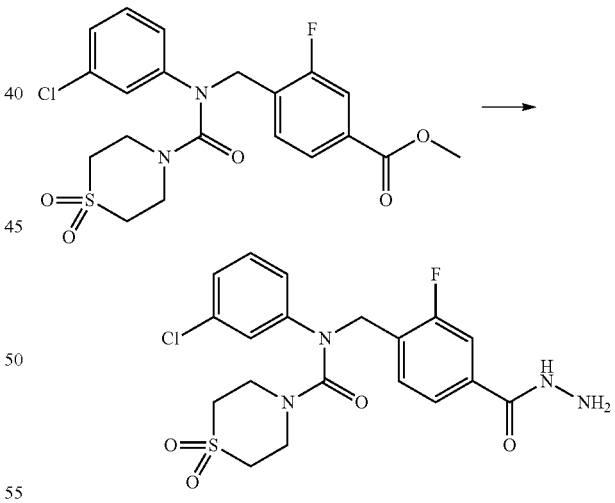

Methyl 4-((N-(3-chlorophenyl)-1,1-dioxidothiomorpholine-4-carboxamido)methyl)-3-fluorobenzoate (0.200 g, 0.440 mmol) and hydrazine monohydrate (0.427 mL, 8.793 mmol) in ethanol (4 mL) was mixed at the room temperature and then heated at 120° C. under the microwaves for 1 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was diluted with diethylether (5 mL) and ethyl acetate (1 mL) and stirred at the ambient temperature. The resulting precipitates were collected by filtration, washed by hexane, and dried to give N-(3-chlorophenyl)-N-(2-fluoro-4-(hydrazinecarbonyl)benzyl)thiomorpholine-4-carboxamide 1,1-dioxide as white solid (0.185 g, 92.5%).

[Step 3] Compound 21810

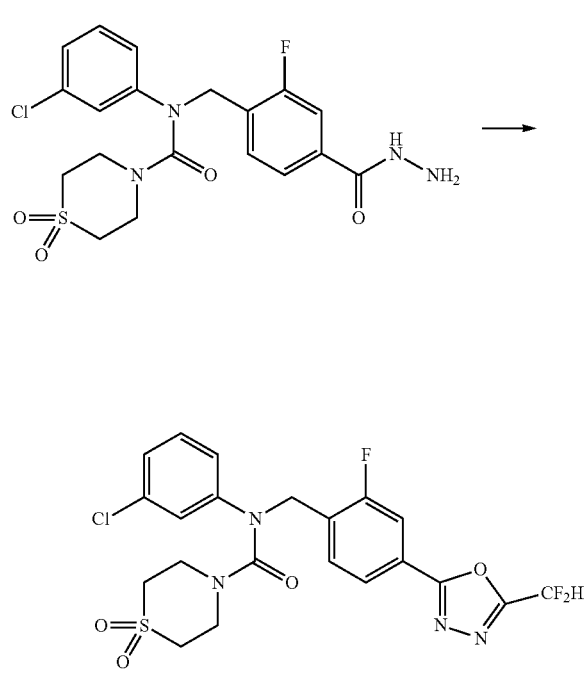

A solution of N-(3-chlorophenyl)-N-(2-fluoro-4-(hydrazinecarbonyl)benzyl)thiomorpholine-4-carboxamide 1,1-dioxide (0.100 g, 0.220 mmol) and triethylamine (0.092 mL, 0.659 mmol) in dichloromethane (4 mL) was mixed at the room temperature with 2,2-difluoroacetic anhydride (0.027 mL, 0.220 mmol), and stirred at the same temperature for 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; ethyl acetate/hexane=20% to 50%) to give N-(3-chlorophenyl)-N-(4-(5-(difluoromethyl)-1,3,4-oxadiazol-2-yl)-2-fluorobenzyl)thiomorpholine-4-carboxamide 1,1-dioxide as white solid (0.032 g, 28.3%).

$^1$H NMR (400 MHz, CDCl$_3$) δ 7.90 (dd, 1H, J=8.0, 1.4 Hz), 7.79 (dd, 1H, J=9.5, 2.0 Hz), 7.67 (t, 1H, J=7.6 Hz), 7.32 (t, 1H, J=8.0 Hz), 7.23 (d, 1H, J=8.9 Hz), 7.18 (t, 1H, J=1.9 Hz), 7.07-6.81 (m, 2H), 4.94 (s, 2H), 3.74 (t, 4H, J=4.9 Hz), 2.87 (t, 4H, J=4.7 Hz); LRMS (ES) m/z 515.1 (M$^+$+1).

Example 290. Compound 21811: N-(4-(5-(Difluoromethyl)-1,3,4-oxadiazol-2-yl)-2-fluorobenzyl)-N-(1-ethyl-1H-indazol-6-yl)thiomorpholine-4-carboxamide 1,1-dioxide

[Step 1] Methyl 4-(((1-ethyl-1H-indazol-6-yl)amino)methyl)-3-fluorobenzoate

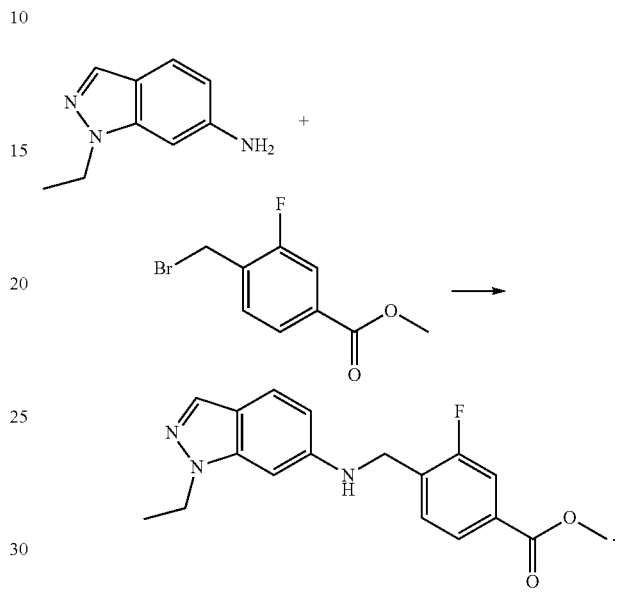

A solution of 1-ethyl-1H-indazol-6-amine (0.322 g, 2.000 mmol), methyl 4-(bromomethyl)-3-fluorobenzoate (0.494 g, 2.000 mmol) and N,N-diisopropylethylamine (0.697 mL, 4.000 mmol) in acetonitrile (8 mL) was stirred at the room temperature for 18 hr, and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 30%) to give methyl 4-((1-ethyl-1H-indazol-6-yl)amino)methyl)-3-fluorobenzoate as green oil (0.573 g, 87.5%).

[Step 2] Methyl 4-((N-(1-ethyl-1H-indazol-6-yl)-1,1-dioxidothiomorpholine-4-carboxamido)methyl)-3-fluorobenzoate

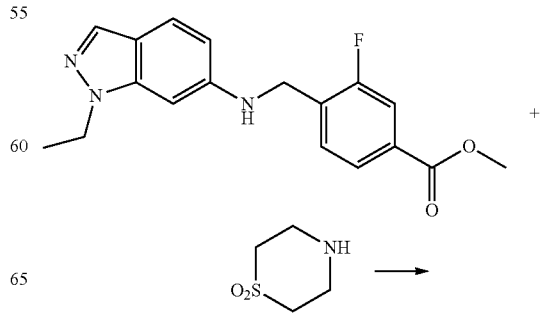

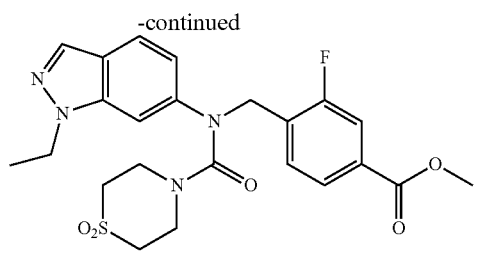

A solution of methyl 4-(((1-ethyl-1H-indazol-6-yl)amino)methyl)-3-fluorobenzoate (0.573 g, 1.750 mmol), N,N-diisopropylethylamine (0.915 mL, 5.251 mmol) and triphosgene (0.260 g, 0.875 mmol) in dichloromethane (10 mL) was stirred at the room temperature for 30 min, and mixed with thiomorpholine 1,1-dioxide (0.237 g, 1.750 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 24 g cartridge; methanol/dichloromethane=0% to 5%) to give methyl 4-((N-(1-ethyl-1H-indazol-6-yl)-1,1-dioxidothiomorpholine-4-carboxamido)methyl)-3-fluorobenzoate as pale yellow solid (0.760 g, 88.9%).

[Step 3] N-(1-Ethyl-1H-indazol-6-yl)-N-(2-fluoro-4-(hydrazinecarbonyl)benzyl)thiomorpholine-4-carboxamide 1,1-dioxide

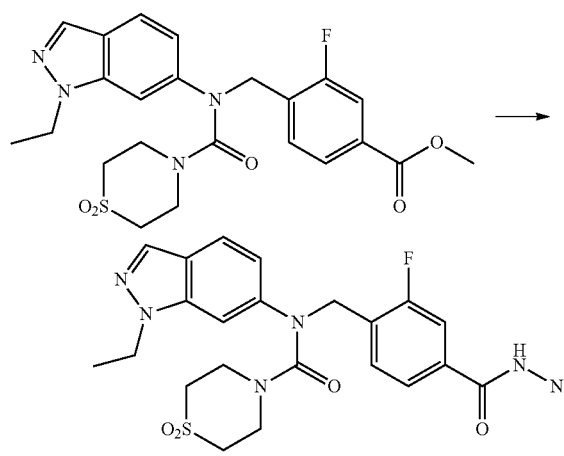

Methyl 4-((N-(1-ethyl-1H-indazol-6-yl)-1,1-dioxidothiomorpholine-4-carboxamido)methyl)-3-fluorobenzoate (0.760 g, 1.556 mmol) and hydrazine monohydrate (1.512 mL, 31.114 mmol) were mixed at the room temperature in ethanol (8 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(1-ethyl-1H-indazol-6-yl)-N-(2-fluoro-4-(hydrazinecarbonyl)benzyl)thiomorpholine-4-carboxamide 1,1-dioxide as white solid (0.747 g, 98.3%).

[Step 4] N-(4-(2-(2,2-Difluoroacetyl)hydrazine-1-carbonyl)-2-fluorobenzyl)-N-(1-ethyl-11-1-indazol-6-yl)thiomorpholine-4-carboxamide 1,1-dioxide

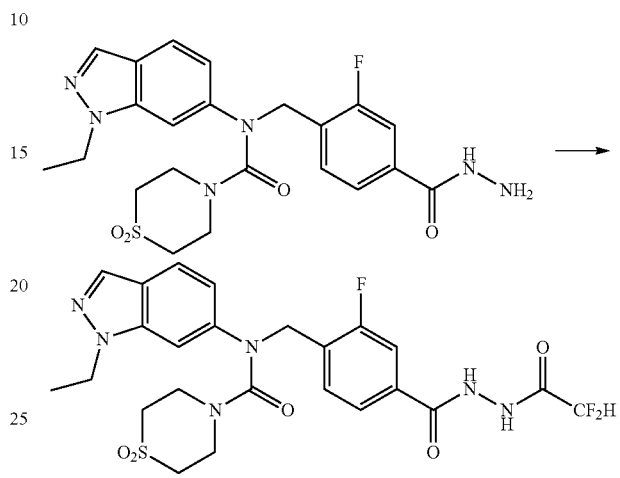

A solution of N-(1-ethyl-1H-indazol-6-yl)-N-(2-fluoro-4-(hydrazinecarbonyl)benzyl)thiomorpholine-4-carboxamide 1,1-dioxide (0.747 g, 1.529 mmol), triethylamine (0.426 mL, 3.059 mmol) and 2,2-difluoroacetic anhydride (0.190 mL, 1.529 mmol) in dichloromethane (8 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 24 g cartridge; methanol/dichloromethane=0% to 5%) to give N-(4-(2-(2,2-difluoroacetyl)hydrazine-1-carbonyl)-2-fluorobenzyl)-N-(1-ethyl-1H-indazol-6-yl)thiomorpholine-4-carboxamide 1,1-dioxide as white solid (0.518 g, 59.8%).

[Step 5] Compound 21811

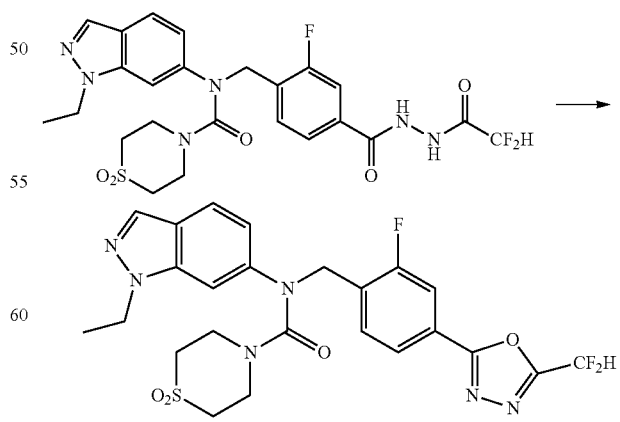

N-(4-(2-(2,2-Difluoroacetyl)hydrazine-1-carbonyl)-2-fluorobenzyl)-N-(1-ethyl-1H-indazol-6-yl)thiomorpholine- 4-carboxamide 1,1-dioxide (0.200 g, 0.353 mmol) and 1-methoxy-N-triethylammoniosulfonyl-methanimidate (Burgess reagent, 0.126 g, 0.530 mmol) were mixed at the room temperature in tetrahydrofuran (3 mL) and then stirred at 70° C. for 18 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; ethyl acetate/hexane=0% to 50%) to give (4-(5-(difluoromethyl)-1,3,4-oxadiazol-2-yl)-2-fluorobenzyl)-N-(1-ethyl-1H-indazol-6-yl)thiomorpholine-4-carboxamide 1,1-dioxide as white solid (0.101 g, 52.0%).

$^1$H NMR (400 MHz. CDCl$_3$) δ 8.00 (d, 1H, J=0.9 Hz), 7.89 (dd, 1H, J=8.0, 1.7 Hz), 7.80-7.68 (m, 3H), 7.19-7.13 (m, 1H), 7.07-6.77 (m, 2H), 5.03 (s, 2H), 4.40 (q, 2H, J=7.2 Hz), 3.79-3.72 (m, 4H), 2.86-2.78 (m, 4H), 1.50 (t, 3H, J=7.2 Hz); LRMS (ES) m/z 549.3 (M$^+$+1).

Example 291. Compound 21812: N-(4-(5-(Difluoromethyl)-1,3,4-oxadiazol-2-yl)-2-fluorobenzyl)-N-(1-isopropyl-1H-indazol-6-yl)thiomorpholine-4-carboxamide 1,1-dioxide

[Step 1] Methyl 3-fluoro-4-(((1-isopropyl-1H-indazol-6-yl)amino)methyl)benzoate

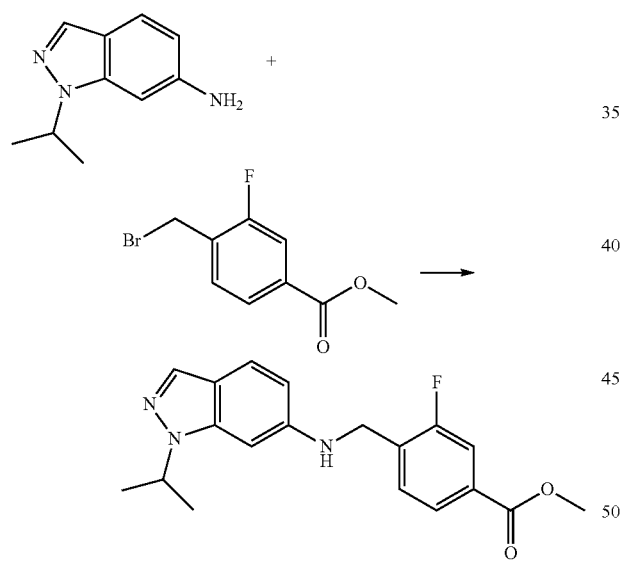

A solution of 1-isopropyl-1H-indazol-6-amine (0.351 g, 2.000 mmol), methyl 4-(bromomethyl)-3-fluorobenzoate (0.494 g, 2.000 mmol) and N,N-diisopropylethylamine (0.697 mL, 4.000 mmol) in acetonitrile (8 mL) was stirred at the room temperature for 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 30%) to give methyl 3-fluoro-4-(((1-isopropyl-1H-indazol-6-yl)amino)methyl)benzoate as green oil (0.592 g, 86.8%).

[Step 2] Methyl 3-fluoro-4-((N-(1-isopropyl-1H-indazol-6-yl)-1,1-dioxidothiomorpholine-4-carboxamido)methyl)benzoate

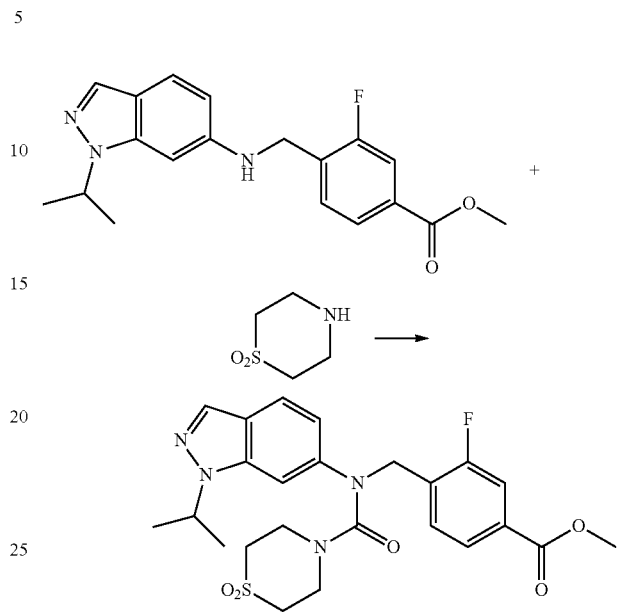

A solution of methyl 3-fluoro-4-(((1-isopropyl-1H-indazol-6-yl)amino)methyl)benzoate (0.592 g, 1.734 mmol), N,N-diisopropylethylamine (0.906 mL, 5.202 mmol) and triphosgene (0.257 g, 0.867 mmol) in dichloromethane (10 mL) was stirred at the room temperature for 30 min, and mixed with thiomorpholine 1,1-dioxide (0.234 g, 1.734 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 24 g cartridge; methanol/dichloromethane=0% to 5%) to give methyl 3-fluoro-4-((N-(1-isopropyl-1H-indazol-6-yl)-1,1-dioxidothiomorpholine-4-carboxamido)methyl)benzoate as pale yellow solid (0.755 g, 86.6%).

[Step 3] N-(2-Fluoro-4-(hydrazinecarbonyl)benzyl)-N-(1-isopropyl-1H-indazol-6-yl)thiomorpholine-4-carboxamide 1,1-dioxide

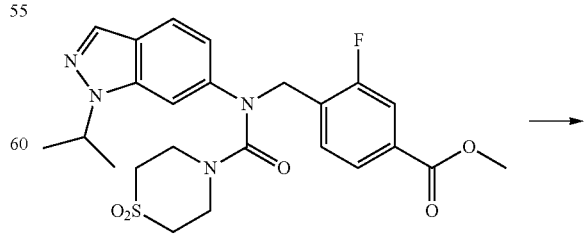

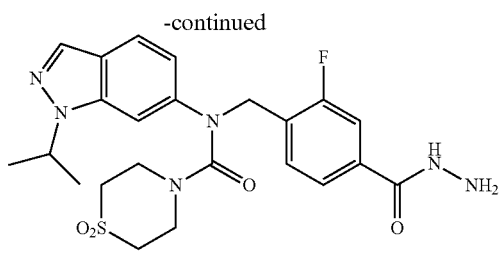

Methyl 3-fluoro-4-((N-(1-isopropyl-1H-indazol-6-yl)-1,1-dioxidothiomorpholine-4-carboxamido)methyl)benzoate (0.755 g, 1.502 mmol) and hydrazine monohydrate (1.460 mL, 30.046 mmol) were mixed at the room temperature in ethanol (8 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(2-fluoro-4-(hydrazinecarbonyl)benzyl)-N-(1-isopropyl-1H-indazol-6-yl)thiomorpholine-4-carboxamide 1,1-dioxide as white solid (0.721 g, 95.5%).

[Step 4] N-(4-(2-(2,2-Difluoroacetyl)hydrazine-1-carbonyl)-2-fluorobenzyl)-N-(1-isopropyl-1H-indazol-6-yl)thiomorpholine-4-carboxamide 1,1-dioxide

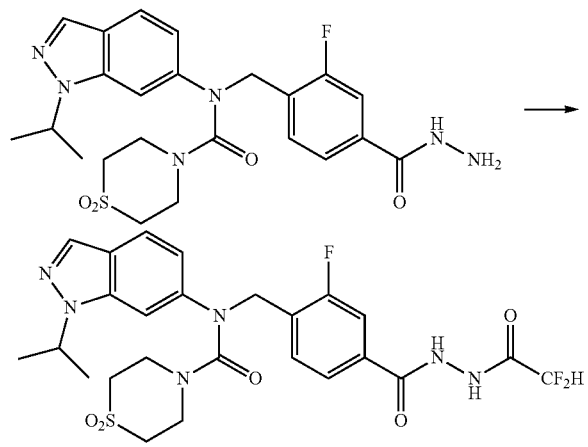

A solution of N-(2-fluoro-4-(hydrazinecarbonyl)benzyl)-N-(1-isopropyl-1H-indazol-6-yl)thiomorpholine-4-carboxamide 1,1-dioxide (0.721 g, 1.435 mmol), triethylamine (0.400 mL, 2.870 mmol) and 2,2-difluoroacetic anhydride (0.178 mL, 1.435 mmol) in dichloromethane (8 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 24 g cartridge; methanol/dichloromethane=0% to 5%) to give N-(4-(2-(2,2-difluoroacetyl)hydrazine-1-carbonyl)-2-fluorobenzyl)-N-(1-isopropyl-1H-indazol-6-yl)thiomorpholine-4-carboxamide 1,1-dioxide as white solid (0.525 g, 63.0%).

[Step 5] Compound 21812

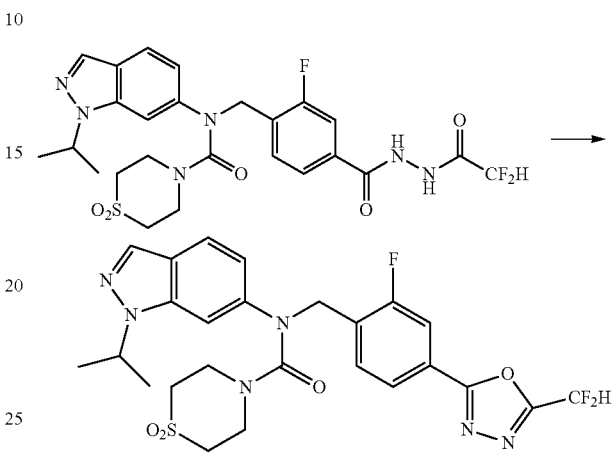

N-(4-(2-(2,2-Difluoroacetyl)hydrazine-1-carbonyl)-2-fluorobenzyl)-N-(1-isopropyl-1H-indazol-6-yl)thiomorpholine-4-carboxamide 1,1-dioxide (0.200 g, 0.344 mmol) and 1-methoxy-N-triethylammoniosulfonyl-methanimidate (Burgess reagent, 0.123 g, 0.517 mmol) were mixed at the room temperature in tetrahydrofuran (3 mL) and then stirred at 70° C. for 18 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; ethyl acetate/hexane=0% to 50%) to give N-(4-(5-(difluoromethyl)-1,3,4-oxadiazol-2-yl)-2-fluorobenzyl)-N-(1-isopropyl-1H-indazol-6-yl)thiomorpholine-4-carboxamide 1,1-dioxide as white solid (0.106 g, 54.7%).

$^1$H NMR (400 MHz, CDCl$_3$) δ 8.01 (s, 1H), 7.90 (dd, 1H, J=8.0, 1.7 Hz), 7.80-7.68 (m, 3H), 7.21-7.15 (m, 1H), 6.97-6.90 (m, 2H), 5.03 (s, 2H), 4.75 (p, 1H, J=6.6 Hz), 3.80-3.70 (m, 4H), 2.86-2.72 (m, 4H), 1.59 (d, 6H, J=6.6 Hz); LRMS (ES) m/z 563.4 (M$^+$+1).

Example 292. Compound 21813: N-(4-(5-(Difluoromethyl)-1,3,4-oxadiazol-2-yl)-2-fluorobenzyl)-N-(2-isopropylbenzo[d]thiazol-6-yl)thiomorpholine-4-carboxamide 1,1-dioxide

[Step 1] Methyl 3-fluoro-4-(((2-isopropylbenzo[d]thiazol-6-yl)amino)methyl)benzoate

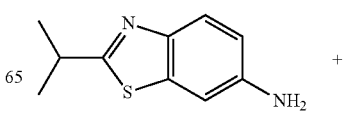

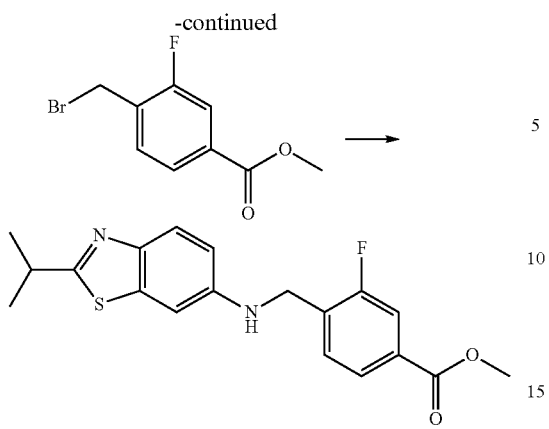

A solution of 2-isopropylbenzo[d]thiazol-6-amine (0.385 g, 2.000 mmol), methyl 4-(bromomethyl)-3-fluorobenzoate (0.494 g, 2.000 mmol) and N,N-diisopropylethylamine (0.697 mL, 4.000 mmol) in acetonitrile (8 mL) was stirred at the room temperature for 18 hr, and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; ethyl acetate/hexane=0% to 30%) to give methyl 3-fluoro-4-(((2-isopropylbenzo[d]thiazol-6-yl)amino)methyl)benzoate as orange oil (0.683 g, 95.2%).

[Step 2] Methyl 3-fluoro-4-((N-(2-isopropylbenzo[d]thiazol-6-yl)-1,1-dioxidothiomorpholine-4-carboxamido)methyl)benzoate

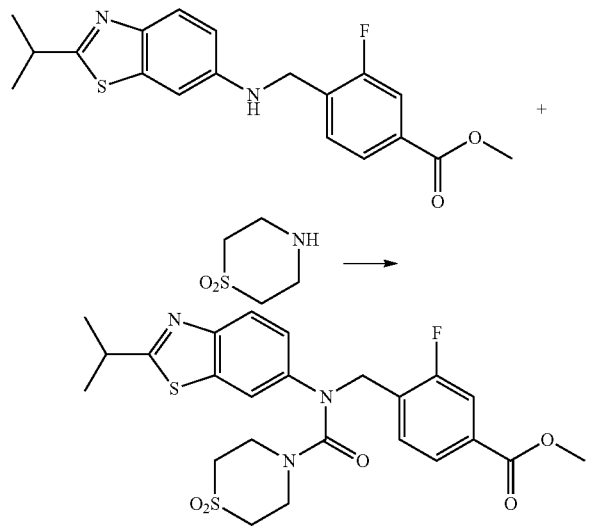

A solution of methyl 3-fluoro-4-(((2-isopropylbenzo[d]thiazol-6-yl)amino)methyl)benzoate (0.683 g, 1.906 mmol), N,N-diisopropylethylamine (0.996 mL, 5.717 mmol) and triphosgene (0.283 g, 0.953 mmol) in dichloromethane (10 mL) was stirred at the room temperature for 30 min, and mixed with thiomorpholine 1,1-dioxide (0.258 g, 1.906 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 24 g cartridge; methanol/dichloromethane=0% to 5%) to give methyl 3-fluoro-4-((N-(2-isopropylbenzo[d]thiazol-6-yl)-1,1-dioxidothiomorpholine-4-carboxamido)methyl)benzoate as orange solid (0.851 g, 85.9%).

[Step 3] N-(2-Fluoro-4-(hydrazinecarbonyl)benzyl)-N-(2-isopropylbenzo[d]thiazol-6-yl)thiomorpholine-4-carboxamide 1,1-dioxide

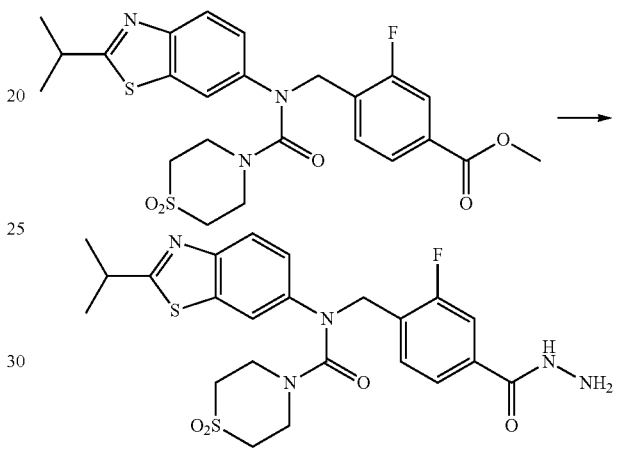

Methyl 3-fluoro-4-((N-(2-isopropylbenzo[d]thiazol-6-yl)-1,1-dioxidothiomorpholine-4-carboxamido)methyl)benzoate (0.851 g, 1.638 mmol) and hydrazine monohydrate (1.592 mL, 32.755 mmol) were mixed at the room temperature in ethanol (8 mL) and then stirred at 80° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 12 g cartridge; methanol/dichloromethane=0% to 5%) to give N-(2-fluoro-4-(hydrazinecarbonyl)benzyl)-N-(2-isopropylbenzo[d]thiazol-6-yl)thiomorpholine-4-carboxamide 1,1-dioxide as white solid (0.669 g, 78.6%).

[Step 4] N-(4-(2-(2,2-Difluoroacetyl)hydrazine-1-carbonyl)-2-fluorobenzyl)-N-(2-isopropylbenzo[d]thiazol-6-yl)thiomorpholine-4-carboxamide 1,1-dioxide

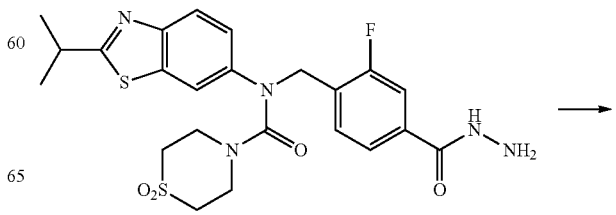

-continued

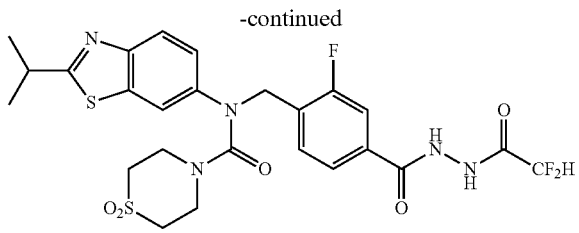

A solution of N-(2-fluoro-4-(hydrazinecarbonyl)benzyl)-N-(2-isopropylbenzo[d]thiazol-6-yl)thiomorpholine-4-carboxamide 1,1-dioxide (0.614 g, 1.181 mmol), triethylamine (0.329 mL, 2.363 mmol) and 2,2-difluoroacetic anhydride (0.147 mL, 1.181 mmol) in dichloromethane (8 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 24 g cartridge; methanol/dichloromethane=0% to 5%) to give N-(4-(2-(2,2-difluoroacetyl)hydrazine-1-carbonyl)-2-fluorobenzyl)-N-(2-isopropylbenzo[d]thiazol-6-yl)thiomorpholine-4-carboxamide 1,1-dioxide as white solid (0.423 g, 59.9%).

[Step 5] Compound 21813

N-(4-(2-(2,2-Difluoroacetyl)hydrazine-1-carbonyl)-2-fluorobenzyl)-N-(2-isopropylbenzo[d]thiazol-6-yl)thiomorpholine-4-carboxamide 1,1-dioxide (0.200 g, 0.335 mmol) and 1-methoxy-N-triethylammoniosulfonyl-methanimidate (Burgess reagent, 0.120 g, 0.502 mmol) were mixed at the room temperature in tetrahydrofuran (3 mL) and then stirred at 70° C. for 18 hr and cooled down to the room temperature to terminate the reaction. Then, water was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; ethyl acetate/hexane=0% to 50%) to give N-(4-(5-(difluoromethyl)-1,3,4-oxadiazol-2-yl)-2-fluorobenzyl)-N-(2-isopropylbenzo[d]thiazol-6-yl)thiomorpholine-4-carboxamide 1,1-dioxide as white solid (0.133 g, 68.5%)

$^1$H NMR (400 MHz, CDCl$_3$) δ 7.96 (d, 1H, J=8.7 Hz), 7.89 (dd, 1H, J=8.0, 1.7 Hz), 7.75 (dd, H, J=10.1, 1.7 Hz), 7.70 (t, 1H, J=7.6 Hz), 7.63 (d, 1H, J=2.2 Hz), 7.24 (dd, 1H, J=8.7, 2.3 Hz), 6.93 (t, 1H, J=51.6 Hz), 4.99 (s, 2H), 3.77-3.69 (m, 4H), 3.44 (p, 1H, J=6.9 Hz), 2.87-2.78 (m, 4H), 1.50 (d, 6H, J=6.9 Hz); LRMS (ES) m/z 580.3 (M$^+$+1).

Example 293. Compound 21823: N-((5-(5-(difluoromethyl)-1,3,4-oxadiazol-2-yl)pyridin-2-yl)methyl)-N-(4-(pyridin-4-yl)phenyl)thiomorpholine-4-carboxamide 1,1-dioxide

[Step 1]
N-(4-bromophenyl)thiomorpholine-4-carboxamide 1,1-dioxide

A solution of 1-bromo-4-isocyanatobenzene (1.000 g, 5.050 mmol) in diethylether (40 mL) was mixed at 0° C. with thiomorpholine 1,1-dioxide (0.683 g, 5.050 mmol), and stirred at the same temperature for 1 hr. The reaction mixture was stirred at the room temperature for additional 4 hr. The precipitates were collected by filtration, washed by diethylether, and dried to give N-(4-bromophenyl)thiomorpholine-4-carboxamide 1,1-dioxide as white solid (1.630 g, 96.9%).

[Step 2] Methyl 6-((N-(4-bromophenyl)-1,1-dioxidothiomorpholine-4-carboxamido)methyl)nicotinate -continued

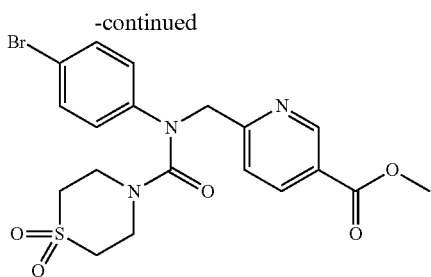

A solution of N-(4-bromophenyl)thiomorpholine-4-carboxamide 1,1-dioxide (1.300 g, 3.902 mmol) and sodium hydride (60.00%, 0.164 g, 4.097 mmol) in N,N-dimethylformamide (15 mL) was stirred at 0° C. for 30 min, and mixed with methyl 6-(bromomethyl)nicotinate (0.987 g, 4.292 mmol). The reaction mixture was stirred at the room temperature for additional 2 hr, quenched at the room temperature by the addition of saturated aqueous sodium bicarbonate solution (10 mL, 10 min stirring). Then, water was added to the reaction mixture, followed by extraction with ethyl acetate. The organic layer was washed with aqueous saturated sodium chloride solution, dried (anhydrous MgSO₄), filtered, and concentrated in vacuo. The residue was chromatographed (SiO₂, 24 g cartridge; ethyl acetate/hexane=30% to 60%) to give methyl 6-((N-(4-bromophenyl)-1,1-dioxidothiomorpholine-4-carboxamido)methyl)nicotinate as pale yellow solid (1.210 g, 64.3%).

[Step 3] Methyl 6-((1.1-dioxido-N-(4-(pyridin-4-yl)phenyl)thiomorpholine-4-carboxamido)methyl)nicotinate

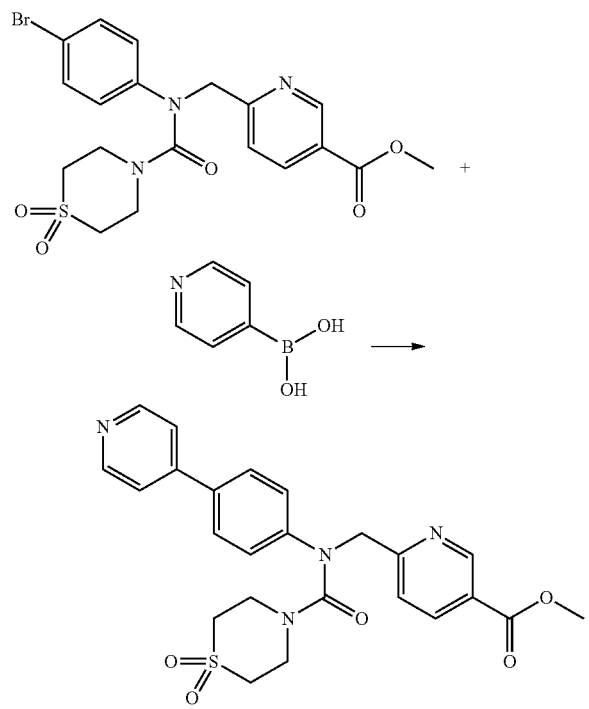

Methyl 6-((N-(4-bromophenyl)-1,1-dioxidothiomorpholine-4-carboxamido)methyl)nicotinate (0.300 g, 0.622 mmol), pyridin-4-ylboronic acid (0.092 g, 0.746 mmol), [1,1'-bis(di-tert-butylphosphino)ferrocene]palladium(II) dichloride (Pd(dtbpf)Cl₂, 0.020 g, 0.031 mmol) and cesium carbonate (0.608 g, 1.866 mmol) in 1,4-dioxane (6 mL)/water (2 mL) was mixed at the room temperature and then heated at 100° C. under the microwaves for 20 min and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried (anhydrous MgSO₄) filtered, and concentrated in vacuo. The residue was chromatographed (SiO₂, 12 g cartridge; methanol/dichloromethane=0% to 5%) to give methyl 6-((1,1-dioxido-N-(4-(pyridin-4-yl)phenyl)thiomorpholine-4-carboxamido)methyl)nicotinate as brown solid (0.166 g, 55.5%).

[Step 4] N-((5-(hydrazinecarbonyl)pyridin-2-yl)methyl)-N-(4-(pyridin-4-yl)phenyl)thiomorpholine-4-carboxamide 1,1-dioxide

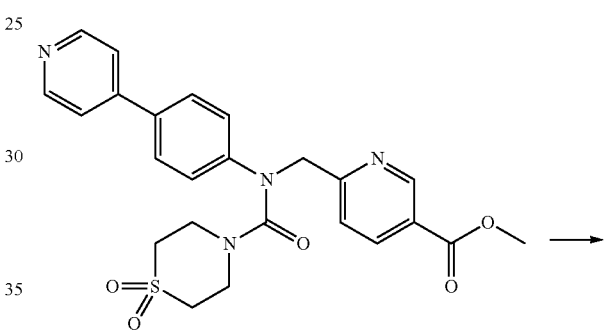

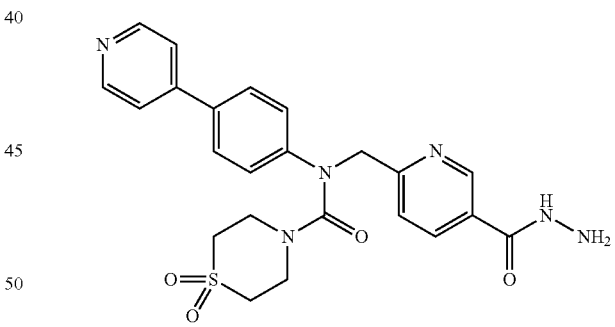

Methyl 6-((1,1-dioxido-N-(4-(pyridin-4-yl)phenyl)thiomorpholine-4-carboxamido)methyl)nicotinate (0.166 g, 0.345 mmol) and hydrazine monohydrate (0.336 mL, 6.909 mmol) were mixed at the room temperature in ethanol (5 mL) and then stirred at 100° C. for 17 hr, cooled down to the room temperature. The precipitates were collected by filtration, washed by ethanol, and dried to give N-((5-(hydrazinecarbonyl)pyridin-2-yl)methyl)-N-(4-(pyridin-4-yl)phenyl)thiomorpholine-4-carboxamide 1,1-dioxide as gray solid (0.145 g, 87.3%).

937

[Step 5] Compound 21823

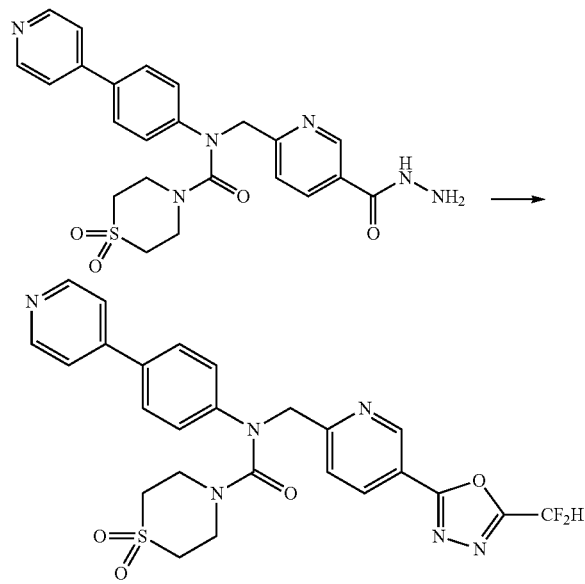

A solution of N-((5-(hydrazinecarbonyl)pyridin-2-yl)methyl)-N-(4-(pyridin-4-yl)phenyl)thiomorpholine-4-carboxamide 1,1-dioxide (0.130 g, 0.271 mmol) and triethylamine (0.113 mL, 0.812 mmol) in dichloromethane (5 mL) was mixed at the room temperature with 2,2-difluoroacetic anhydride (0.034 mL, 0.271 mmol), and stirred at the same temperature for 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-((5-(5-(difluoromethyl)-1,3,4-oxadiazol-2-yl)pyridin-2-yl)methyl)-N-(4-(pyridin-4-yl)phenyl)thiomorpholine-4-carboxamide 1,1-dioxide as white solid (0.008 g, 5.5%).

$^1$H NMR (400 MHz, MeOD) δ 9.21 (d, 1H, J=1.4 Hz), 8.62 (d, 2H, J=4.9 Hz), 8.46 (dd, 1H, J=8.2, 2.0 Hz), 7.87-7.73 (m, 4H), 7.74 (d, 1H, J=8.2 Hz), 7.45 (d, 2H, J=8.6 Hz), 7.26 (t, 1H, J=51.6 Hz), 5.22 (s, 2H), 3.78 (s, 4H), 3.10 (s, 4H); LRMS (ES) m/z 541.1 (M$^+$+1).

Example 294. Compound 21824: N-((5-(5-(difluoromethyl)-1,3,4-oxadiazol-2-yl)pyridin-2-yl)methyl)-N-(4-(pyridin-3-yl)phenyl)thiomorpholine-4-carboxamide 1,1-dioxide

[Step 1] Methyl 6-((1,1-dioxido-N-(4-(pyridin-3-yl)phenyl)thiomorpholine-4-carboxamido)methyl)nicotinate

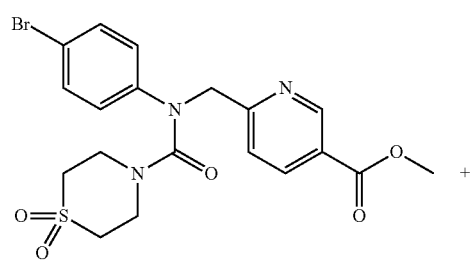

938

-continued

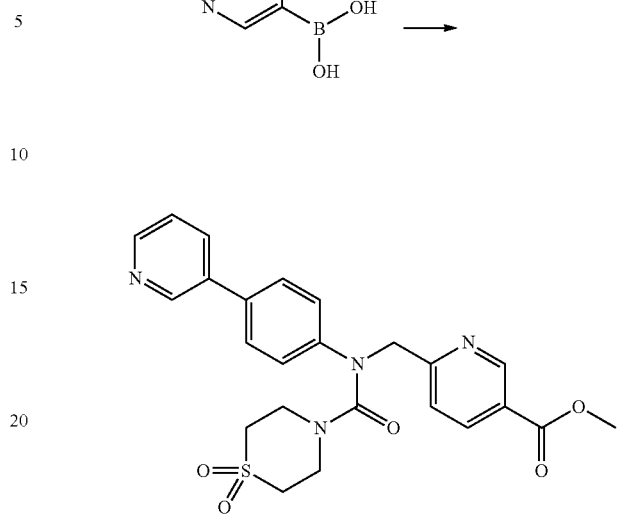

Methyl 6-((N-(4-bromophenyl)-1,1-dioxidothiomorpholine-4-carboxamido)methyl)nicotinate (0.300 g, 0.622 mmol), pyridin-3-ylboronic acid (0.092 g, 0.746 mmol), [1,1'-bis(di-tert-butylphosphino)ferrocene]palladium(II) dichloride (Pd(dtbpf)Cl2, 0.020 g, 0.031 mmol) and cesium carbonate (0.608 g, 1.866 mmol) in 1,4-dioxane (6 mL)/water (2 mL) was mixed at the room temperature and then heated at 100° C. under the microwaves for 20 min and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried (anhydrous MgSO$_4$), filtered, and concentrated in vacuo. The residue was chromatographed (SiO$_2$, 12 g cartridge; methanol/dichloromethane=0% to 5%) to give methyl 6-((1,1-dioxido-N-(4-(pyridin-3-yl)phenyl)thiomorpholine-4-carboxamido)methyl)nicotinate as brown solid (0.213 g, 71.3%).

[Step 2] N-((5-(hydrazinecarbonyl)pyridin-2-yl)methyl)-N-(4-(pyridin-3-yl)phenyl)thiomorpholine-4-carboxamide 1,1-dioxide

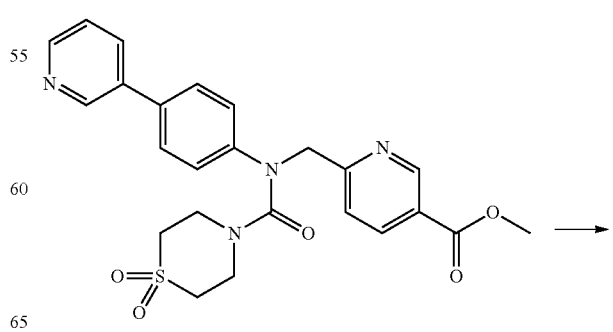

-continued

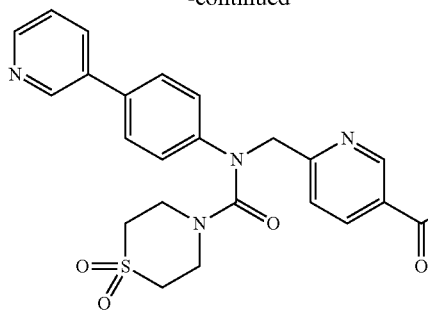

Methyl 6-((1,1-dioxido-N-(4-(pyridin-3-yl)phenyl)thiomorpholine-4-carboxamido)methyl)nicotinate (0.213 g, 0.443 mmol) and hydrazine monohydrate (0.431 mL, 8.865 mmol) in dichloromethane (5 mL) was mixed at the room temperature and then heated at 100° C. under the microwaves for 17 hr, cooled down to the room temperature. The precipitates were collected by filtration, washed by ethanol, and dried to give N-((5-(hydrazinecarbonyl)pyridin-2-yl)methyl)-N-(4-(pyridin-3-yl)phenyl)thiomorpholine-4-carboxamide 1,1-dioxide as gray solid (0.175 g, 82.2%).

[Step 3] N-((5-(2-(2,2-difluoroacetyl)hydrazine-1-carbonyl)pyridin-2-yl)methyl)-N-(4-(pyridin-3-yl)phenyl)thiomorpholine-4-carboxamide 1,1-dioxide

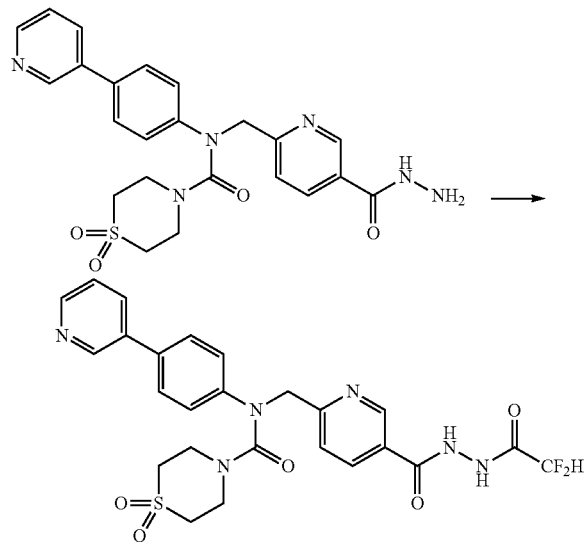

A solution of N-((5-(hydrazinecarbonyl)pyridin-2-yl)methyl)-N-(4-(pyridin-3-yl)phenyl)thiomorpholine-4-carboxamide 1,1-dioxide (0.150 g, 0.312 mmol) and triethylamine (0.131 mL, 0.936 mmol) in dichloromethane (5 mL) was mixed at the room temperature with 2,2-difluoroacetic anhydride (0.039 mL, 0.312 mmol), and stirred at the same temperature for 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-((5-(2-(2,2-difluoroacetyl)hydrazine-1-carbonyl)pyridin-2-yl)methyl)-N-(4-(pyridin-3-yl)phenyl)thiomorpholine-4-carboxamide 1,1-dioxide as pale yellow oil (0.087 g, 49.9%).

[Step 4] Compound 21824

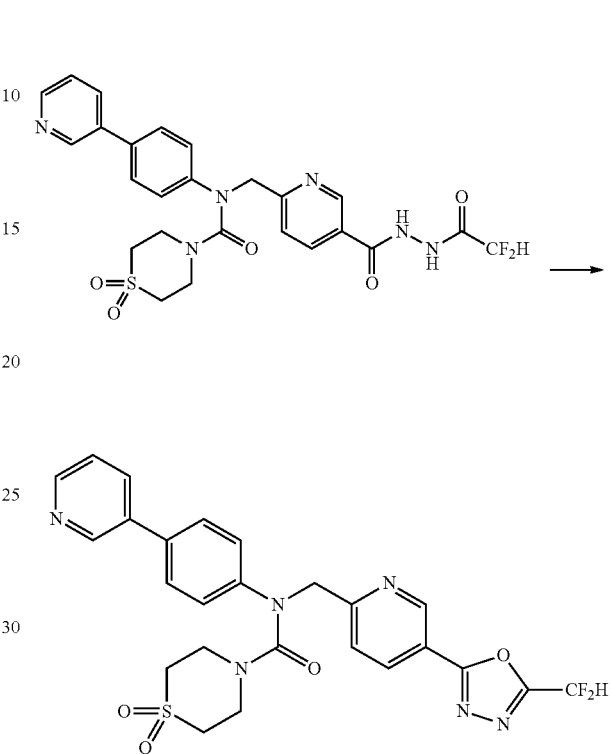

N-((5-(2-(2,2-difluoroacetyl)hydrazine-1-carbonyl)pyridin-2-yl)methyl)-N-(4-(pyridin-3-yl)phenyl)thiomorpholine-4-carboxamide 1,1-dioxide (0.087 g, 0.156 mmol) and 1-methoxy-N-triethylammoniosulfonyl-methanimidate (Burgess reagent, 0.074 g, 0.312 mmol) in tetrahydrofuran (3 mL) was mixed at the room temperature and then heated at 150° C. under the microwaves for 30 min and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-N-(4-(pyridin-3-yl)phenyl)thiomorpholine-4-carboxamide 1,1-dioxide as white solid (0.048 g, 57.0%).

$^1$H NMR (400 MHz, CDCl$_3$) δ 9.28 (d, 1H, J=1.6 Hz), 8.95 (s, 1H), 8.69 (d, 1H, J=4.2 Hz), 8.45 (dd, 1H, J=8.2, 2.2 Hz), 8.26 (d, 1H, J=8.0 Hz), 7.77-7.73 (m, 1H), 7.64-7.54 (m, 3H), 7.37 (d, 2H, J=8.5 Hz), 6.97 (t, 1H, J=51.7 Hz), 5.20 (s, 2H), 3.79 (s, 4H), 3.07 (t, 4H, J=4.9 Hz); LRMS (ES) m/z 541.3 (M$^+$+1).

Example 295. Compound 21829: N-((5-(5-(difluoromethyl)-1,3,4-oxadiazol-2-yl)pyridin-2-yl)methyl)-N-(4-fluorophenyl)thiomorpholine-4-carboxamide 1,1-dioxide

[Step 1] Methyl 6-((N-(4-fluorophenyl)-1,1-dioxidothiomorpholine-4-carboxamido)methyl)nicotinate

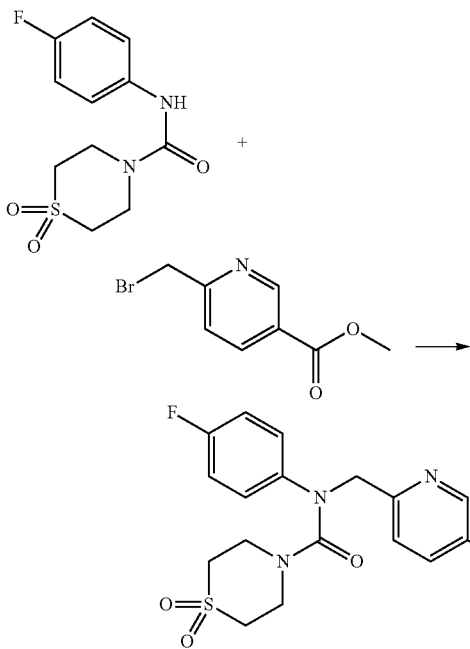

A solution of N-(4-fluorophenyl)thiomorpholine-4-carboxamide 1,1-dioxide (0.500 g, 1.836 mmol) and sodium hydride (60.00%, 0.081 g, 2.020 mmol) in N,N-dimethylformamide (10 mL) was stirred at 0° C. for 30 min, and mixed with methyl 6-(bromomethyl)nicotinate (0.465 g, 2.020 mmol). The reaction mixture was stirred at the room temperature for additional 5 hr, quenched at the room temperature by the addition of water (5 mL, 10 min stirring). Then, water was added to the reaction mixture, followed by extraction with ethyl acetate. The organic layer was washed with aqueous saturated sodium chloride solution, dried (anhydrous MgSO$_4$), filtered, and concentrated in vacuo, methyl 6-((N-(4-fluorophenyl)-1,1-dioxidothiomorpholine-4-carboxamido)methyl)nicotinate was used without further purification (0.450 g, 58.1%, brown solid).

[Step 2] N-(4-fluorophenyl)-N-((5-(hydrazinecarbonyl)pyridin-2-yl)methyl)thiomorpholine-4-carboxamide 1,1-dioxide

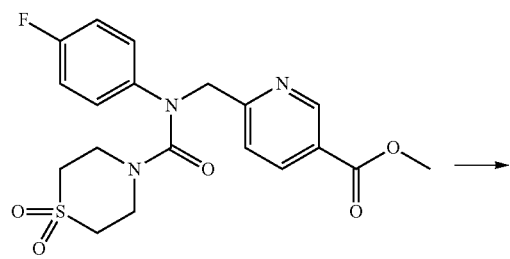

-continued

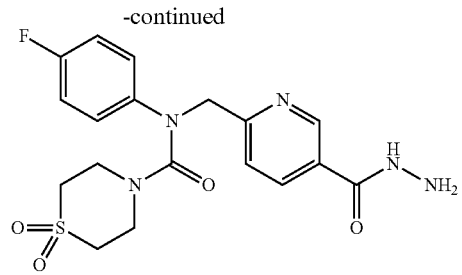

Methyl 6-((N-(4-fluorophenyl)-1,1-dioxidothiomorpholine-4-carboxamido)methyl)nicotinate (0.150 g, 0.356 mmol) and hydrazine monohydrate (0.346 mL, 7.118 mmol) were mixed at the room temperature in ethanol (5 mL) and then stirred at 100° C. for 17 hr, cooled down to the room temperature. The precipitates were collected by filtration, washed by ethanol, and dried to give N-(4-fluorophenyl)-N-((5-(hydrazinecarbonyl)pyridin-2-yl)methyl)thiomorpholine-4-carboxamide 1,1-dioxide as pale yellow solid (0.111 g, 74.0%).

[Step 3] N-((5-(2-(2,2-difluoroacetyl)hydrazine-1-carbonyl)pyridin-2-yl)methyl)-N-(4-fluorophenyl)thiomorpholine-4-carboxamide 1,1-dioxide

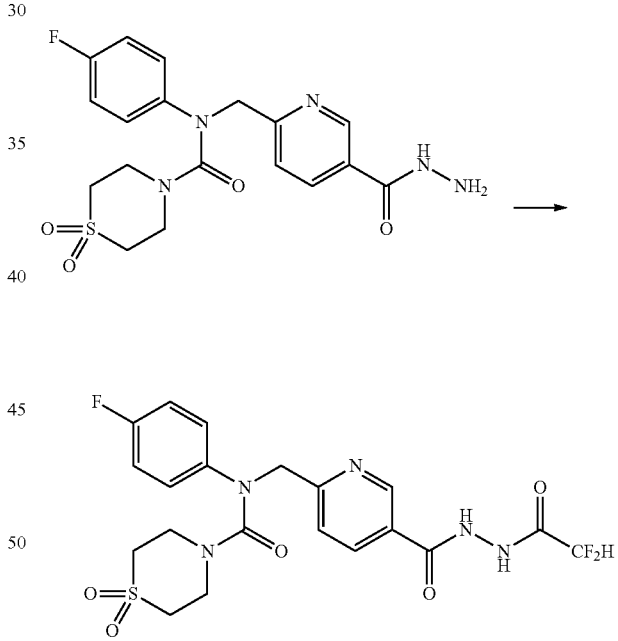

A solution of N-(4-fluorophenyl)-N-((5-(hydrazinecarbonyl)pyridin-2-yl)methyl)thiomorpholine-4-carboxamide 1,1-dioxide (0.111 g, 0.263 mmol) and triethylamine (0.110 mL, 0.790 mmol) in dichloromethane (5 mL) was mixed at the room temperature with 2,2-difluoroacetic anhydride (0.065 mL, 0.527 mmol), and stirred at the same temperature for 1 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (0.082 g, 62.3%, yellow solid).

[Step 4] Compound 21829

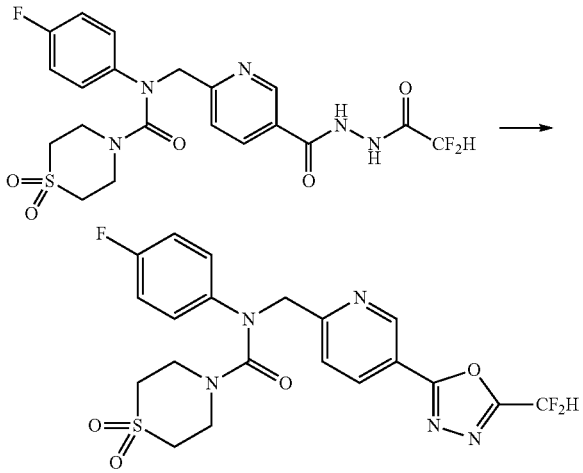

N-((5-(2-(2,2-difluoroacetyl)hydrazine-1-carbonyl)pyridin-2-yl)methyl)-N-(4-fluorophenyl)thiomorpholine-4-carboxamide 1,1-dioxide (0.082 g, 0.164 mmol) and 1-methoxy-N-triethylammoniosulfonyl-methanimidate (Burgess reagent, 0.117 g, 0.493 mmol) were mixed at the room temperature in tetrahydrofuran (5 mL) and then stirred at 70° C. for 5 hr, cooled down to the room temperature, filtered to remove solids, and concentrated under the reduced pressure. The residue was chromatographed (SiO$_2$, 4 g cartridge; methanol/dichloromethane=0% to 10%) to give N-((5-(5-(difluoromethyl)-1,3,4-oxadiazol-2-yl)pyridin-2-yl)methyl)-N-(4-fluorophenyl)thiomorpholine-4-carboxamide 1,1-dioxide as white solid (0.015 g, 19.0%).

$^1$H NMR (400 MHz, CDCl$_3$) δ 9.27 (d, 1H, J=1.6 Hz), 8.43 (dd, 1H, J=8.2, 2.2 Hz), 7.58 (d, 2H, J=8.2 Hz), 7.25-7.21 (m, 2H), 7.10-6.84 (m, 3H), 5.08 (s, 2H), 3.73 (t, 4H, J=5.1 Hz), 2.98 (t, 4H, J=5.2 Hz); LRMS (ES) m/z 482.1 (M$^+$+1).

Example 296. Compound 21830: N-((5-(5-(difluoromethyl)-1,3,4-oxadiazol-2-yl)pyridin-2-yl)methyl)-N-(3-fluorophenyl)thiomorpholine-4-carboxamide 1,1-dioxide

[Step 1] Methyl 6-((N-(3-fluorophenyl)-1,1-dioxidothiomorpholine-4-carboxamido)methyl)nicotinate

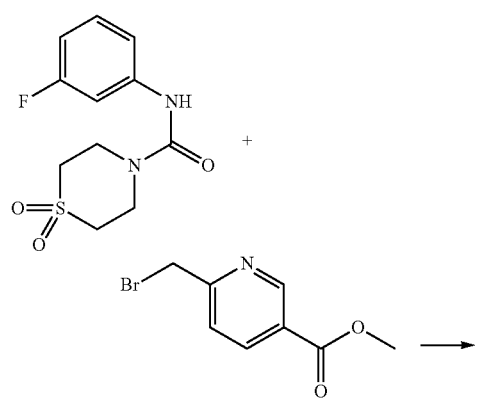

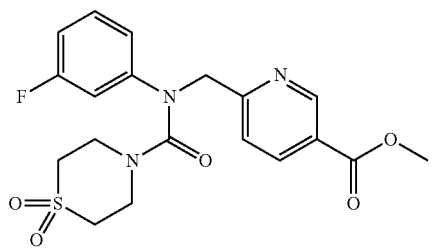

A solution of N-(3-fluorophenyl)thiomorpholine-4-carboxamide 1,1-dioxide (0.500 g, 1.836 mmol) and sodium hydride (60.00%, 0.081 g, 2.020 mmol) in N,N-dimethylformamide (10 mL) was stirred at 0° C. for 30 min, and mixed with methyl 6-(bromomethyl)nicotinate (0.465 g, 2.020 mmol). The reaction mixture was stirred at the room temperature for additional 5 hr, quenched at the room temperature by the addition of water (5 mL, 10 min stirring). Then, water was added to the reaction mixture, followed by extraction with ethyl acetate. The organic layer was washed with aqueous saturated sodium chloride solution, dried (anhydrous MgSO$_4$), filtered, and concentrated in vacuo. Methyl 6-((N-(3-fluorophenyl)-1,1-dioxidothiomorpholine-4-carboxamido)methyl)nicotinate was used without further purification (0.450 g, 58.1%, brown solid).

[Step 2] N-(3-fluorophenyl)-N-((5-(hydrazinecarbonyl)pyridin-2-yl)methyl)thiomorpholine-4-carboxamide 1,1-dioxide

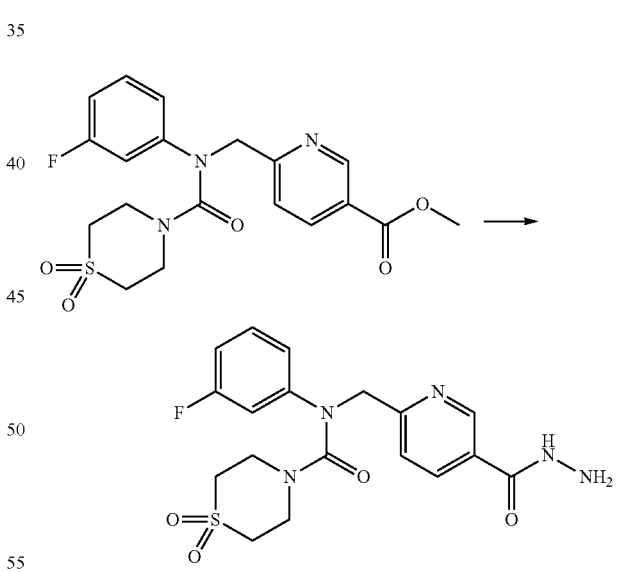

Methyl 6-((N-(3-fluorophenyl)-1,1-dioxidothiomorpholine-4-carboxamido)methyl)nicotinate (0.150 g, 0.356 mmol) and hydrazine monohydrate (0.346 mL, 7.118 mmol) were mixed at the room temperature in ethanol (5 mL) and then stirred at 100° C. for 17 hr, cooled down to the room temperature. The precipitates were collected by filtration, washed by ethanol, and dried to give N-(3-fluorophenyl)-N-((5-(hydrazinecarbonyl)pyridin-2-yl)methyl)thiomorpholine-4-carboxamide 1,1-dioxide as pale yellow solid (0.113 g, 75.3%).

945

[Step 3] N-((5-(2-(2,2-difluoroacetyl)hydrazine-1-carbonyl)pyridin-2-yl)methyl)-N-(3-fluorophenyl)thiomorpholine-4-carboxamide 1,1-dioxide

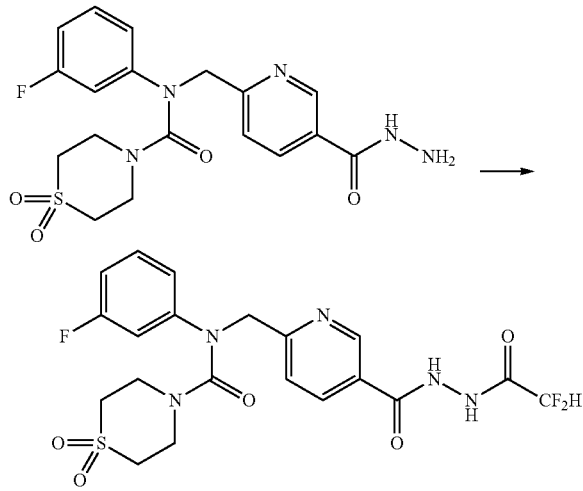

A solution of N-(3-fluorophenyl)-N-((5-(hydrazinecarbonyl)pyridin-2-yl)methyl)thiomorpholine-4-carboxamide 1,1-dioxide (0.113 g, 0.268 mmol) and triethylamine (0.112 mL, 0.804 mmol) in dichloromethane (5 mL) was mixed at the room temperature with 2,2-difluoroacetic anhydride (0.067 mL, 0.536 mmol), and stirred at the same temperature for 1 hr. Then, water was added to the reaction mixture, followed by extraction with dichloromethane. The bi-phasic mixture was passed through a plastic frit to remove the solid residues and aqueous layer, and the organic layer collected was concentrated in vacuo. N-((5-(2-(2,2-difluoroacetyl)hydrazine-1-carbonyl)pyridin-2-yl)methyl)-N-(3-fluorophenyl)thiomorpholine-4-carboxamide 1,1-dioxide was used without further purification (0.090 g, 67.2%, yellow solid).

[Step 4] Compound 21830

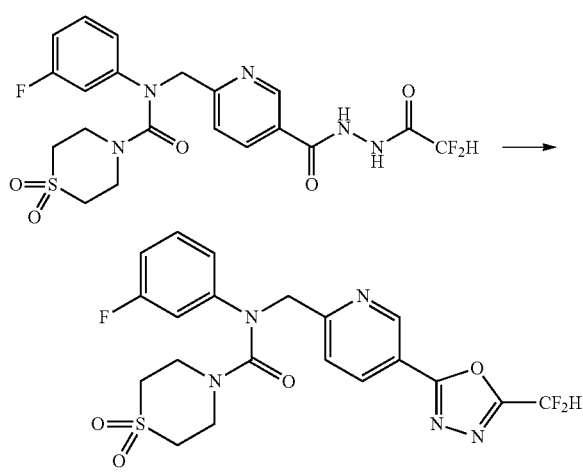

N-((5-(2-(2,2-difluoroacetyl)hydrazine-1-carbonyl)pyridin-2-yl)methyl)-N-(3-fluorophenyl)thiomorpholine-4-carboxamide 1,1-dioxide (0.090 g, 0.180 mmol) and 1-methoxy-N-triethylammoniosulfonyl-methanimidate (Burgess reagent, 0.129 g, 0.541 mmol) were mixed at the room temperature in tetrahydrofuran (5 mL) and then stirred at 70° C. for 5 hr, cooled down to the room temperature, filtered to remove solids, and concentrated under the reduced pressure. The residue was chromatographed (SiO$_2$, 4 g cartridge; methanol/dichloromethane=0% to 10%) to give N-((5-(5-(difluoromethyl)-1,3,4-oxadiazol-2-yl)pyridin-2-yl)methyl)-N-(3-fluorophenyl)thiomorpholine-4-carboxamide 1,1-dioxide as white solid (0.044 g, 50.7%).
$^1$H NMR (400 MHz, CDCl$_3$) δ 9.28 (d, 1H, J=1.6 Hz), 8.46 (dd, 1H, J=8.2, 2.2 Hz), 7.58 (d, 1H, J=8.2 Hz), 7.37-7.32 (m, 1H), 7.10-6.92 (m, 4H), 5.14 (s, 2H), 3.76 (t, 4H, J=5.1 Hz), 3.03 (t, 4H, J=5.2 Hz); LRMS (ES) m/z 482.3 (M$^+$+1).

Example 297. Compound 21831: N-(4-chlorophenyl)-N-((5-(5-(difluoromethyl)-1,3,4-oxadiazol-2-yl)pyridin-2-yl)methyl)thiomorpholine-4-carboxamide 1,1-dioxide

[Step 1] Methyl 6-((N-(4-chlorophenyl)-1,1-dioxidothiomorpholine-4-carboxamido)methyl)nicotinate

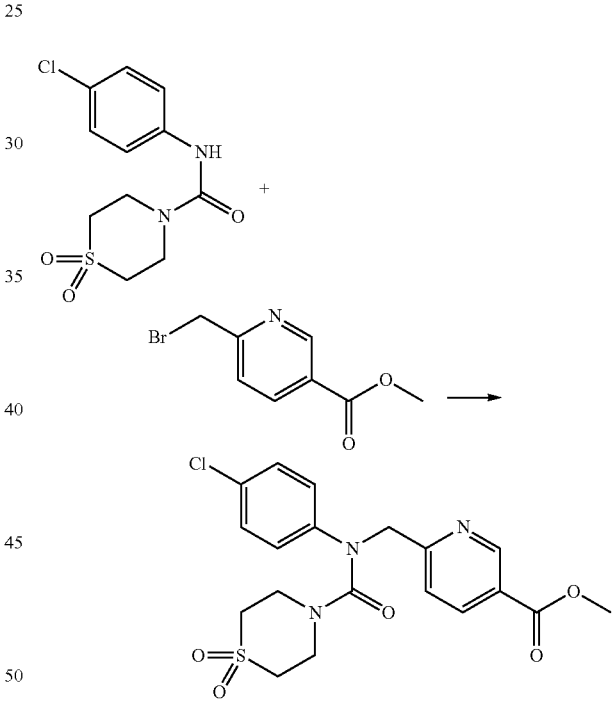

A solution of N-(4-chlorophenyl)thiomorpholine-4-carboxamide 1,1-dioxide (0.500 g, 1.732 mmol) and sodium hydride (60.00%, 0.076 g, 1.905 mmol) in N,N-dimethylformamide (10 mL) was stirred at 0° C. for 30 min, and mixed with methyl 6-(bromomethyl)nicotinate (0.438 g, 1.905 mmol). The reaction mixture was stirred at the room temperature for additional 5 hr, quenched at the room temperature by the addition of water (5 mL, 10 min stirring). Then, water was added to the reaction mixture, followed by extraction with ethyl acetate. The organic layer was washed with aqueous saturated sodium chloride solution, dried (anhydrous MgSO$_4$), filtered, and concentrated in vacuo. Methyl 6-((N-(4-chlorophenyl)-1,1-dioxidothiomorpholine-4-carboxamido)methyl)nicotinate was used without further purification (0.450 g, 59.3%, brown solid).

[Step 2] N-(4-chlorophenyl)-N-((5-(hydrazinecarbonyl)pyridin-2-yl)methyl)thiomorpholine-4-carboxamide 1,1-dioxide

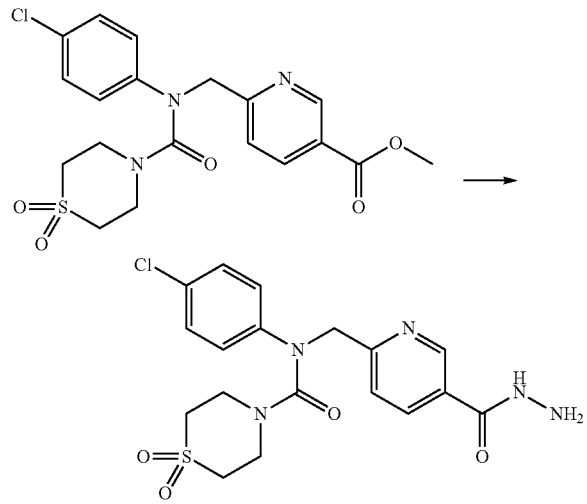

Methyl 6-((N-(4-chlorophenyl)-1,1-dioxidothiomorpholine-4-carboxamido)methyl)nicotinate (0.100 g, 0.228 mmol) and hydrazine monohydrate (0.222 mL, 4.567 mmol) were mixed at the room temperature in ethanol (5 mL) and then stirred at 100° C. for 17 hr and cooled down to the room temperature to terminate the reaction. The precipitates were collected by filtration, washed by ethanol, and dried to give N-(4-chlorophenyl)-N-((5-(hydrazinecarbonyl)pyridin-2-yl)methyl)thiomorpholine-4-carboxamide 1,1-dioxide as pale yellow solid (0.061 g, 61.0%).

[Step 3] N-(4-chlorophenyl)-N-((5-(2-(2,2-difluoroacetyl)hydrazine-1-carbonyl)pyridin-2-yl)methyl)thiomorpholine-4-carboxamide 1,1-dioxide

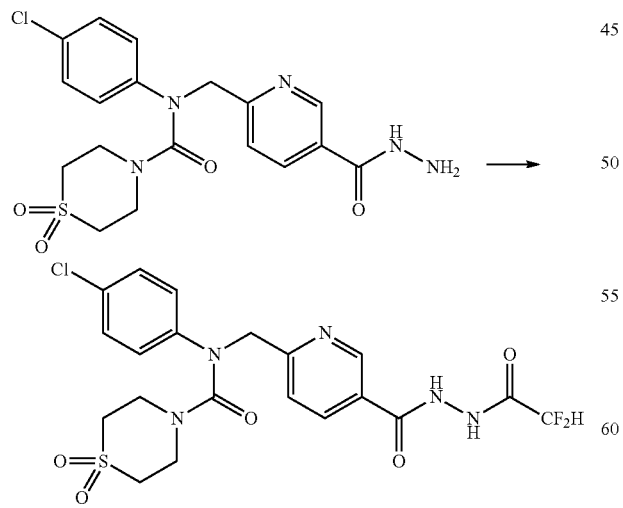

A solution of N-(4-chlorophenyl)-N-((5-(hydrazinecarbonyl)pyridin-2-yl)methyl)thiomorpholine-4-carboxamide 1,1-dioxide (0.061 g, 0.139 mmol) and triethylamine (0.058 mL, 0.418 mmol) in dichloromethane (5 mL) was mixed at the room temperature with 2,2-difluoroacetic anhydride (0.035 mL, 0.279 mmol), and stirred at the same temperature for 1 hr. Then, water was added to the reaction mixture, followed by extraction with dichloromethane. The bi-phasic mixture was passed through a plastic frit to remove the solid residues and aqueous layer, and the organic layer collected was concentrated in vacuo. N-(4-chlorophenyl)-N-((5-(2-(2,2-difluoroacetyl)hydrazine-1-carbonyl)pyridin-2-yl)methyl)thiomorpholine-4-carboxamide 1,1-dioxide was used without further purification (0.045 g, 62.6%, yellow solid).

[Step 4] Compound 21831

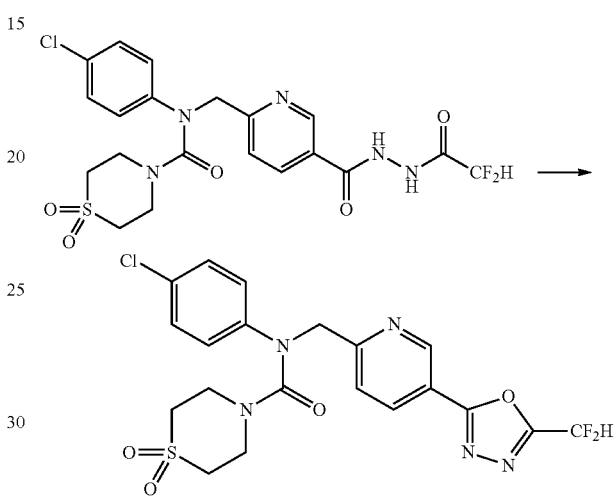

N-(4-chlorophenyl)-N-((5-(2-(2,2-difluoroacetyl)hydrazine-1-carbonyl)pyridin-2-yl) methyl)thiomorpholine-4-carboxamide 1,1-dioxide (0.045 g, 0.087 mmol) and 1-methoxy-N-triethylammoniosulfonyl-methanimidate (Burgess reagent, 0.062 g, 0.262 mmol) were mixed at the room temperature in tetrahydrofuran (5 mL) and then stirred at 70° C. for 5 hr, cooled down to the room temperature, filtered to remove solids, and concentrated under the reduced pressure to remove the solvent. The residue was chromatographed (SiO$_2$, 4 g cartridge; methanol/dichloromethane=0% to 10%) to give N-(4-chlorophenyl)-N-((5-(5-(difluoromethyl)-1,3,4-oxadiazol-2-yl)pyridin-2-yl)methyl)thiomorpholine-4-carboxamide 1,1-dioxide as white solid (0.011 g, 25.3%).
$^1$H NMR (400 MHz, CDCl$_3$) δ 9.27-9.26 (m, 1H), 8.42 (dd, 1H, J=8.2, 2.2 Hz), 7.56 (d, 1H, J=8.2 Hz), 7.34 (d, 2H, J=8.9 Hz), 7.17 (d, 2H, J=8.9 Hz), 7.09-6.83 (m, 1H), 5.10 (s, 2H), 3.73 (t, 4H, J=5.2 Hz), 3.01 (t, 4H, J=5.2 Hz); LRMS (ES) m/z 498.2 (M$^+$+1).

Example 298. Compound 21839: N-((5-(5-(difluoromethyl)-1,3,4-oxadiazol-2-yl)pyridin-2-yl)methyl)-N-(4-fluorophenyl) morpholine-4-carboxamide

[Step 1]
N-(4-fluorophenyl)morpholine-4-carboxamide

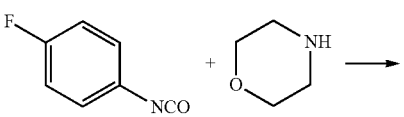

949

-continued

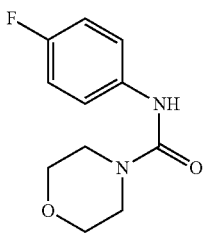

A solution of 1-fluoro-4-isocyanatobenzene (0.500 g, 3.647 mmol) in diethylether (10 mL) was mixed at 0° C. with morpholine (0.315 mL, 3.647 mmol), and stirred at the room temperature for 18 hr. The precipitates were collected by filtration, washed by diethylether, and dried to give N-(4-fluorophenyl)morpholine-4-carboxamide as white solid (0.776 g, 94.9%).

[Step 2] Methyl 6-((N-(4-fluorophenyl)morpholine-4-carboxamido)methyl)nicotinate

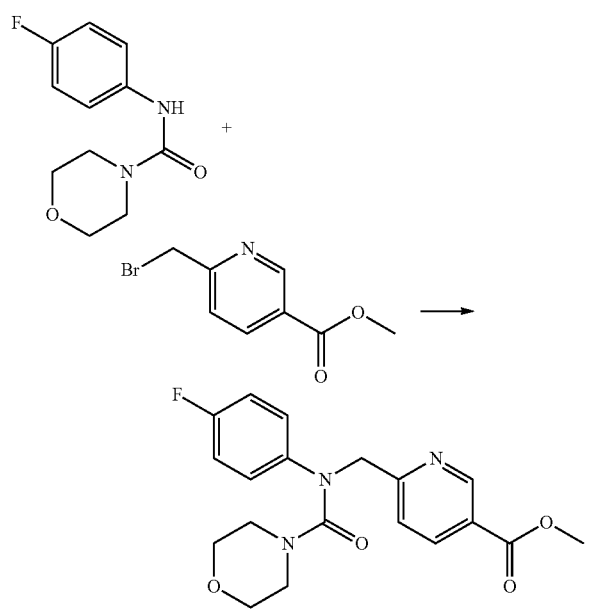

To a stirred solution of N-(4-fluorophenyl)morpholine-4-carboxamide (0.200 g, 0.892 mmol) in N,N-dimethylformamide (5 mL) was added at 0° C. sodium hydride (60.00%, 0.036 g, 0.892 mmol). The reaction mixture was stirred at the same temperature for 1 hr, added at the room temperature with methyl 6-(bromomethyl)nicotinate (0.205 g, 0.892 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 6-((N-(4-fluorophenyl)morpholine-4-carboxamido)methyl)nicotinate as yellow oil (0.274 g, 82.3%).

950

[Step 3] N-(4-fluorophenyl)-N-((5-(hydrazinecarbonyl)pyridin-2-yl)methyl)morpholine-4-carboxamide

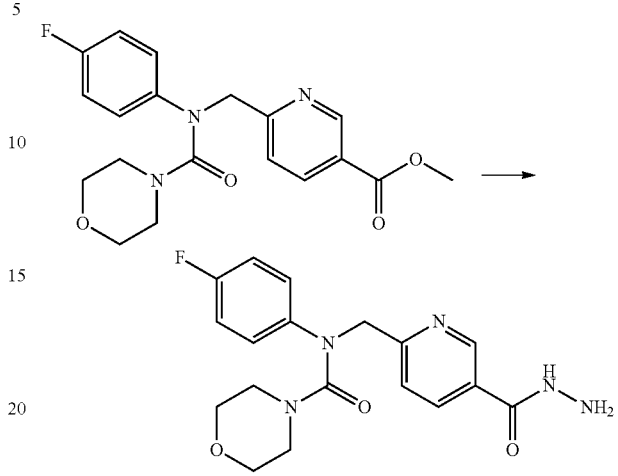

Methyl 6-((N-(4-fluorophenyl)morpholine-4-carboxamido)methyl)nicotinate (0.274 g, 0.734 mmol) and hydrazine monohydrate (0.357 mL, 7.338 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(4-fluorophenyl)-N-((5-(hydrazinecarbonyl)pyridin-2-yl)methyl)morpholine-4-carboxamide as yellow oil (0.215 g, 78.5%).

[Step 4] N-((5-(2-(2,2-difluoroacetyl)hydrazine-1-carbonyl)pyridin-2-yl)methyl)-N-(4-fluorophenyl)morpholine-4-carboxamide

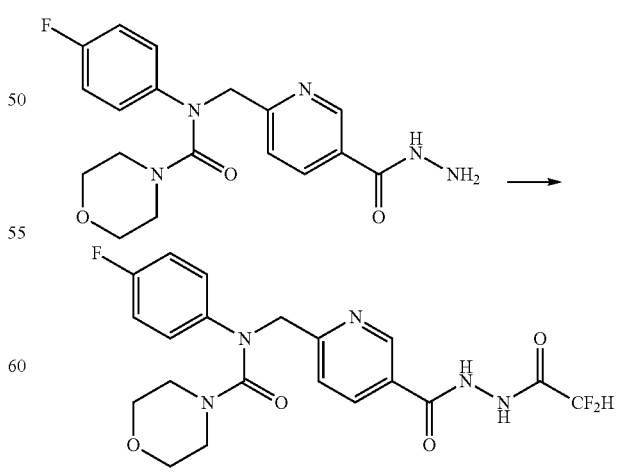

A solution of N-(4-fluorophenyl)-N-((5-(hydrazinecarbonyl)pyridin-2-yl)methyl)morpholine-4-carboxamide (0.108 g, 0.288 mmol) and triethylamine (0.080 mL, 0.576 mmol) in dichloromethane (2 mL) was mixed at the room temperature with 2,2-difluoroacetic anhydride (0.036 mL, 0.288 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification N-((5-(2-(2,2-difluoroacetyl)hydrazine-1-carbonyl)pyridin-2-yl)methyl)-N-(4-fluorophenyl)morpholine-4-carboxamide, 0.105 g, 81.0%, white foam).

[Step 5] Compound 21839

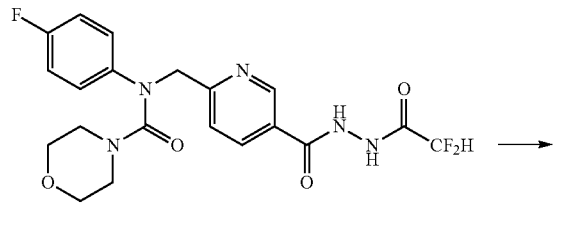

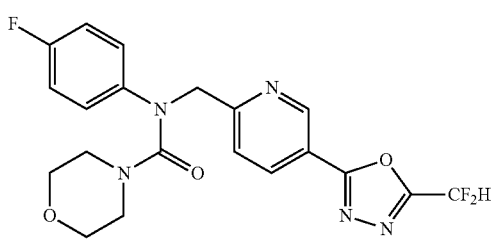

N-((5-(2-(2,2-difluoroacetyl)hydrazine-1-carbonyl)pyridin-2-yl)methyl)-N-(4-fluorophenyl)morpholine-4-carboxamide (0.105 g, 0.233 mmol) and 1-methoxy-N-triethylammoniosulfonyl-methanimidate (Burgess reagent, 0.083 g, 0.350 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-N-(4-fluorophenyl) morpholine-4-carboxamide as yellow foam (0.064 g, 63.7%).

$^1$H NMR (400 MHz, CDCl$_3$) δ 9.24 (s, 1H), 8.35 (dd, 1H, J=8.2, 2.0 Hz), 7.63 (d, 1H, J=8.2 Hz), 7.23-7.15 (m, 2H), 7.10-6.74 (m, 3H), 5.08 (s, 2H), 3.53 (t, 4H, J=4.7 Hz), 3.26 (t, 4H, J=4.7 Hz); LRMS (ES) m/z 434.0 (M$^+$+1).

Example 299. Compound 21840: N-(4-fluorophenyl)-N-((5-(5-(trifluoromethyl)-1,3,4-oxadiazol-2-yl)pyridin-2-yl)methyl) morpholine-4-carboxamide

[Step 1] N-(4-fluorophenyl)-N-((5-(2-(2,2,2-trifluoroacetyl)hydrazine-1-carbonyl)pyridin-2-yl)methyl) morpholine-4-carboxamide

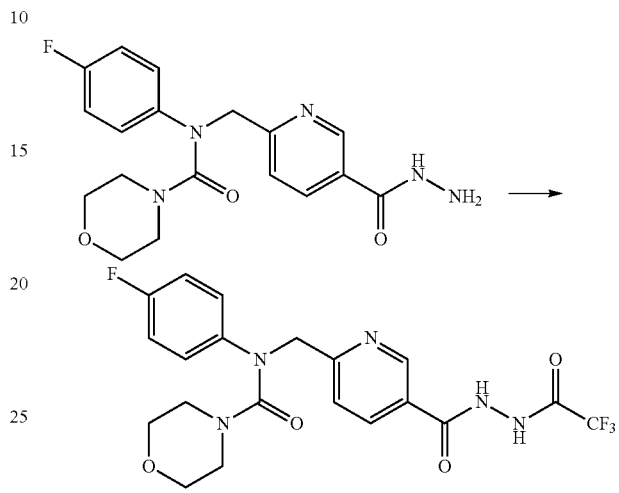

A solution of N-(4-fluorophenyl)-N-((5-(hydrazinecarbonyl)pyridin-2-yl)methyl)morpholine-4-carboxamide (0.108 g, 0.288 mmol) and triethylamine (0.080 mL, 0.576 mmol) in dichloromethane (2 mL) was mixed at the room temperature with trifluoroacetic anhydride (0.041 mL, 0.288 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-fluorophenyl)-N-((5-(2-(2,2,2-trifluoroacetyl)hydrazine-1-carbonyl)pyridin-2-yl)methyl)morpholine-4-carboxamide, 0.097 g, 72.0%, white foam).

[Step 2] Compound 21840

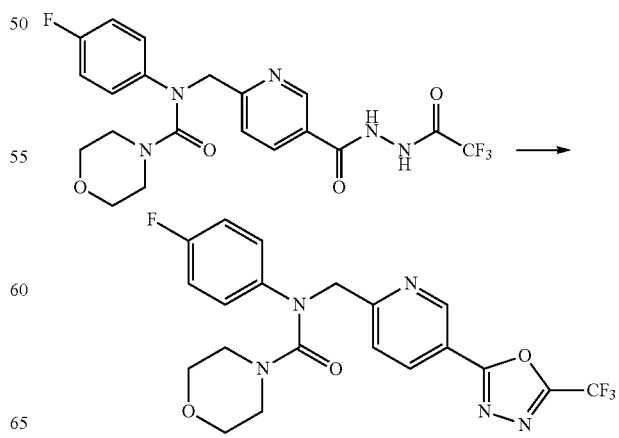

N-(4-fluorophenyl)-N-((5-(2-(2,2,2-trifluoroacetyl)hydrazine-1-carbonyl)pyridin-2-yl)methyl)morpholine-4-carboxamide (0.097 g, 0.207 mmol) and 1-methoxy-N-triethylammoniosulfonyl-methanimidate (Burgess reagent, 0.074 g, 0.311 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-fluorophenyl)-N-((5-(5-(trifluoromethyl)-1,3,4-oxadiazol-2-yl)pyridin-2-yl)methyl) morpholine-4-carboxamide as yellow foam (0.049 g, 51.8%).

$^1$H NMR (400 MHz, CDCl$_3$) δ 9.23 (s, 1H), 8.35 (dd, 1H, J=8.1, 2.1 Hz), 7.64 (d, 1H, J=8.2 Hz), 7.23-7.15 (m, 2H), 7.08-6.98 (m, 2H), 5.08 (s, 2H), 3.53 (t, 4H, J=4.7 Hz), 3.26 (t, 4H, J=4.6 Hz); LRMS (ES) m/z 452.0 (M$^+$+1).

Example 300. Compound 21841: N-(4-(5-(difluoromethyl)-1,3,4-oxadiazol-2-yl)-2-fluorobenzyl)-N-(4-fluorophenyl)morpholine-4-carboxamide

[Step 1] Methyl 3-fluoro-4-((N-(4-fluorophenyl)morpholine-4-carboxamido)methyl)benzoate

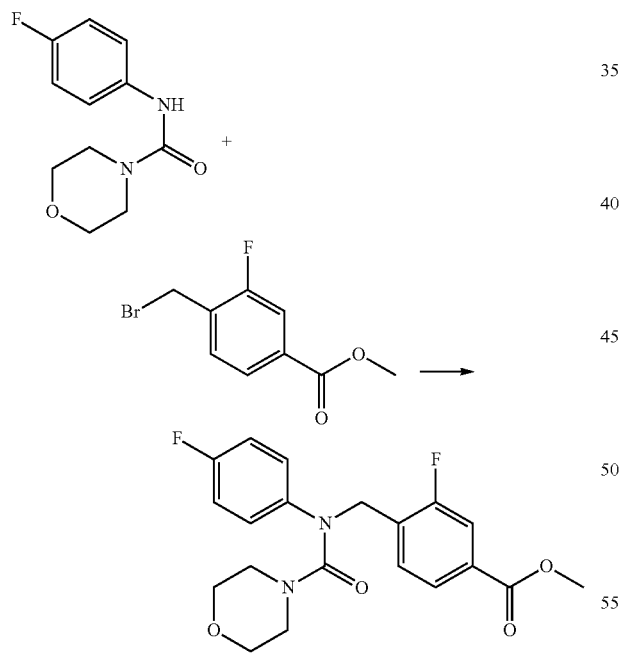

To a stirred solution of N-(4-fluorophenyl)morpholine-4-carboxamide (0.200 g, 0.892 mmol) in N,N-dimethylformamide (5 mL) was added at 0° C. sodium hydride (60.00%, 0.036 g, 0.892 mmol). The reaction mixture was stirred at the same temperature for 1 hr, treated at the room temperature with methyl 4-(bromomethyl)-3-fluorobenzoate (0.220 g, 0.892 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 3-fluoro-4-((N-(4-fluorophenyl)morpholine-4-carboxamido)methyl)benzoate as yellow oil (0.305 g, 87.6%).

[Step 2] N-(2-fluoro-4-(hydrazinecarbonyl)benzyl)-N-(4-fluorophenyl)morpholine-4-carboxamide

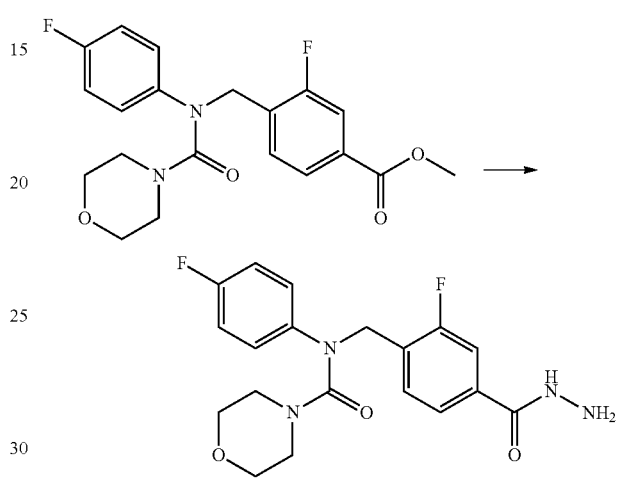

Methyl 3-fluoro-4-((N-(4-fluorophenyl)morpholine-4-carboxamido)methyl)benzoate (0.305 g, 0.781 mmol) and hydrazine monohydrate (0.380 mL, 7.813 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(2-fluoro-4-(hydrazinecarbonyl)benzyl)-N-(4-fluorophenyl)morpholine-4-carboxamide as yellow oil (0.304 g, 99.6%).

[Step 3] (N-(4-(2-(2,2-difluoroacetyl)hydrazine-1-carbonyl)-2-fluorobenzyl)-N-(4-fluorophenyl)morpholine-4-carboxamide

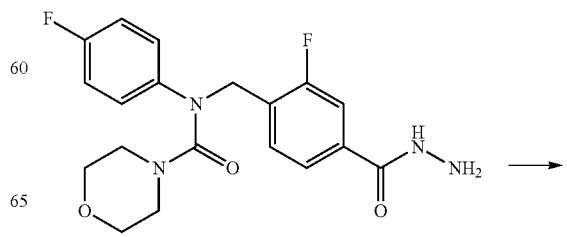

-continued

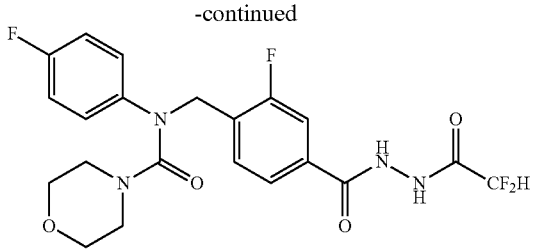

A solution of N-(2-fluoro-4-(hydrazinecarbonyl)benzyl)-N-(4-fluorophenyl)morpholine-4-carboxamide (0.152 g, 0.389 mmol) and triethylamine (0.109 mL, 0.779 mmol) in dichloromethane (2 mL) was mixed at the room temperature with 2,2-difluoroacetic anhydride (0.048 mL, 0.389 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-(2-(2,2-difluoroacetyl)hydrazine-1-carbonyl)-2-fluorobenzyl)-N-(4-fluorophenyl)morpholine-4-carboxamide, 0.125 g, 68.7%, white foam).

[Step 4] Compound 21841

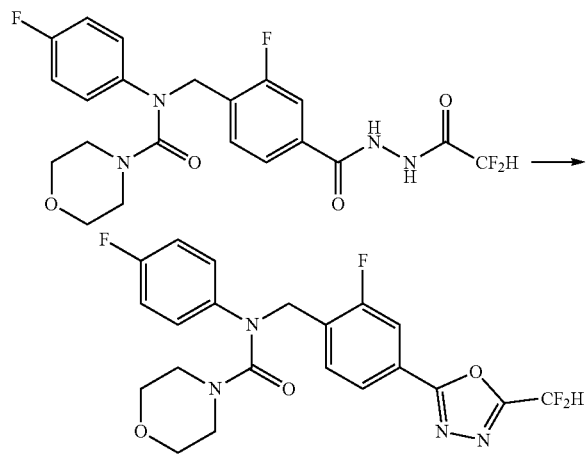

N-(4-(2-(2,2-difluoroacetyl)hydrazine-1-carbonyl)-2-fluorobenzyl)-N-(4-fluorophenyl)morpholine-4-carboxamide (0.125 g, 0.268 mmol) and 1-methoxy-N-triethylammoniosulfonyl-methanimidate (Burgess reagent, 0.096 g, 0.401 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-fluorophenyl)morpholine-4-carboxamide as white foam (0.047 g, 38.8%).

$^1$H NMR (400 MHz, CDCl$_3$) δ 7.88 (d, 1H, J=7.9 Hz), 7.79-7.68 (m, 2H), 7.14-7.07 (m, 2H), 7.04 (d, 2H, J=8.5 Hz), 6.97 (dd, 1H, J=33.7, 1.7 Hz), 4.94 (s, 2H), 3.49 (t, 4H, J=4.7 Hz), 3.25 (t, 4H, J=4.2 Hz); LRMS (ES) m/z 451.0 (M$^+$+1).

Example 301. Compound 21842: N-(2-fluoro-4-(5-(trifluoromethyl)-1,3,4-oxadiazol-2-yl)benzyl)-N-(4-fluorophenyl)morpholine-4-carboxamide

[Step 1] N-(2-fluoro-4-(2-(2,2,2-trifluoroacetyl)hydrazine-1-carbonyl)benzyl)-N-(4-fluorophenyl) morpholine-4-carboxamide

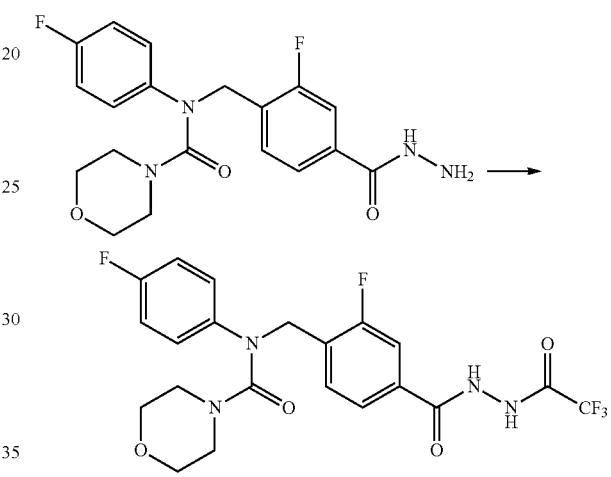

A solution of N-(2-fluoro-4-(hydrazinecarbonyl)benzyl)-N-(4-fluorophenyl)morpholine-4-carboxamide (0.152 g, 0.389 mmol) and triethylamine (0.109 mL, 0.779 mmol) in dichloromethane (2 mL) was mixed at the room temperature with trifluoroacetic anhydride (0.055 mL, 0.389 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification N-(2-fluoro-4-(2-(2,2,2-trifluoroacetyl)hydrazine-1-carbonyl)benzyl)-N-(4-fluorophenyl) morpholine-4-carboxamide, 0.134 g, 70.9%, white foam).

[Step 2] Compound 21842

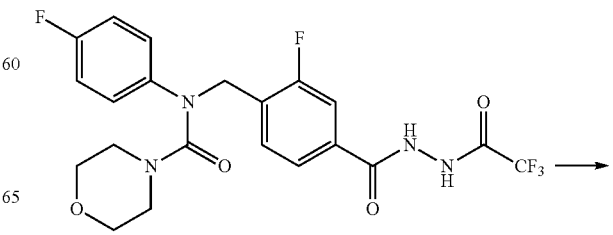

-continued

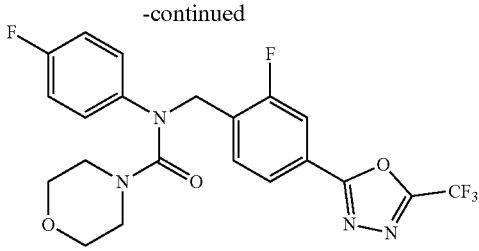

N-(2-fluoro-4-(2-(2,2,2-trifluoroacetyl)hydrazine-1-carbonyl)benzyl)-N-(4-fluorophenyl)morpholine-4-carboxamide (0.134 g, 0.276 mmol) and 1-methoxy-N-triethylammoniosulfonyl-methanimidate (Burgess reagent, 0.099 g, 0.414 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(2-fluoro-4-(5-(trifluoromethyl)-1,3,4-oxadiazol-2-yl)benzyl)-N-(4-fluorophenyl)morpholine-4-carboxamide as white foam (0.013 g, 10.0%).

$^1$H NMR (400 MHz, CDCl$_3$) δ 7.88 (d, 1H, J=8.0 Hz), 7.79-7.70 (m, 2H), 7.14-7.07 (m, 2H), 7.07-6.99 (m, 2H), 4.94 (s, 2H), 3.50 (t, 4H, J=4.7 Hz), 3.25 (t, 4H, J=4.3 Hz); LRMS (ES) m/z 469.0 (M$^+$+1).

Example 302. Compound 21843: N-((5-(5-(difluoromethyl)-1,3,4-oxadiazol-2-yl)pyridin-2-yl)methyl)-N-(3-fluorophenyl) morpholine-4-carboxamide

[Step 1]
N-(3-fluorophenyl)morpholine-4-carboxamide

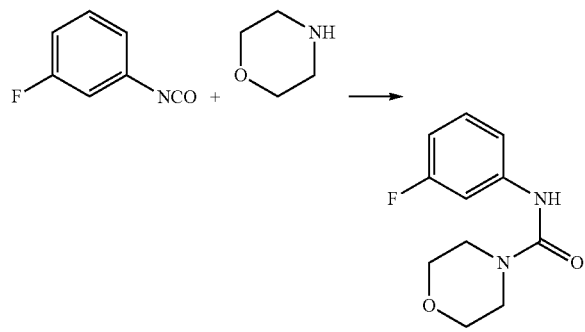

A solution of 1-fluoro-3-isocyanatobenzene (0.500 g, 3.647 mmol) in diethylether (10 mL) was mixed at 0° C. with morpholine (0.315 mL, 3.647 mmol), and stirred at the room temperature for 18 hr. The precipitates were collected by filtration, washed by diethylether, and dried to give N-(3-fluorophenyl)morpholine-4-carboxamide as white solid (0.737 g, 90.1%).

[Step 2] Methyl 6-((N-(3-fluorophenyl)morpholine-4-carboxamido)methyl)nicotinate

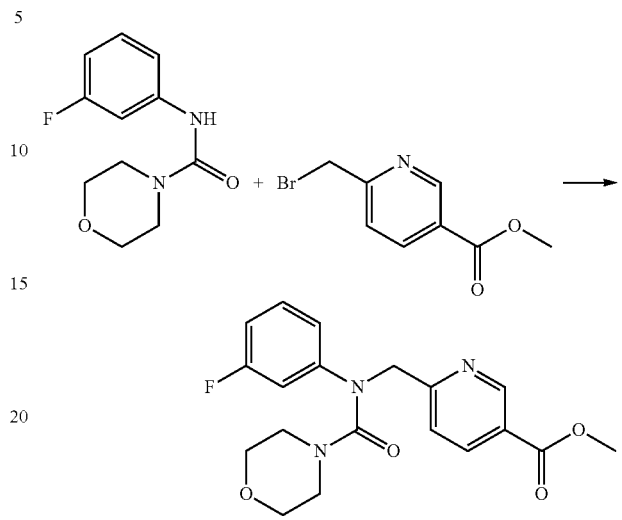

To a stirred solution of N-(3-fluorophenyl)morpholine-4-carboxamide (0.200 g, 0.892 mmol) in N,N-dimethylformamide (5 mL) was added at 0° C. sodium hydride (60.00%, 0.036 g, 0.892 mmol). The reaction mixture was stirred at the same temperature for 1 hr, added at the room temperature with methyl 6-(bromomethyl)nicotinate (0.205 g, 0.892 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 6-((N-(3-fluorophenyl)morpholine-4-carboxamido)methyl)nicotinate as yellow oil (0.265 g, 79.7%).

[Step 3], N-(3-fluorophenyl)-N-((5-(hydrazinecarbonyl)pyridin-2-yl)methyl)morpholine-4-carboxamide

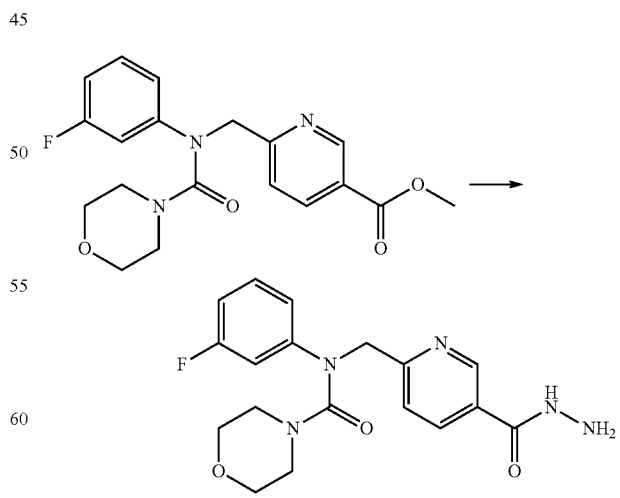

Methyl 6-((N-(3-fluorophenyl)morpholine-4-carboxamido)methyl)nicotinate (0.265 g, 0.711 mmol) and hydrazine monohydrate (0.345 mL, 7.108 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(3-fluorophenyl)-N-((5-(hydrazinecarbonyl)pyridin-2-yl)methyl)morpholine-4-carboxamide as yellow oil (0.192 g, 72.4%).

[Step 4] N-((5-(2-(2,2-difluoroacetyl)hydrazine-1-carbonyl)pyridin-2-yl)methyl)-N-(3-fluorophenyl)morpholine-4-carboxamide

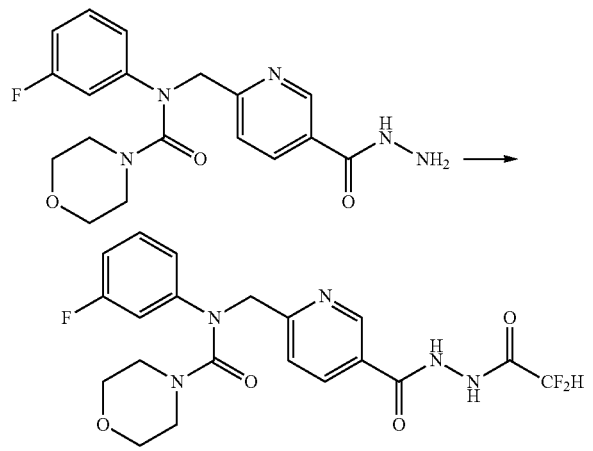

A solution of N-(3-fluorophenyl)-N-((5-(hydrazinecarbonyl)pyridin-2-yl)methyl)morpholine-4-carboxamide (0.096 g, 0.257 mmol) and triethylamine (0.072 mL, 0.514 mmol) in dichloromethane (2 mL) was mixed at the room temperature with 2,2-difluoroacetic anhydride (0.032 mL, 0.257 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification N-((5-(2-(2,2-difluoroacetyl)hydrazine-1-carbonyl)pyridin-2-yl)methyl)-N-(3-fluorophenyl)morpholine-4-carboxamide, 0.088 g, 75.4%, white foam).

[Step 5] Compound 21843

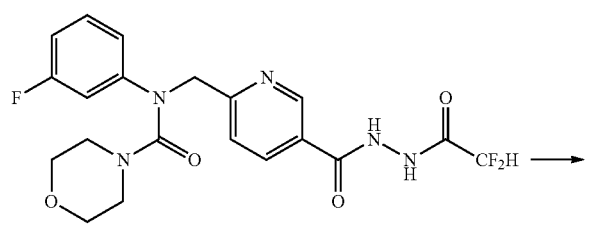

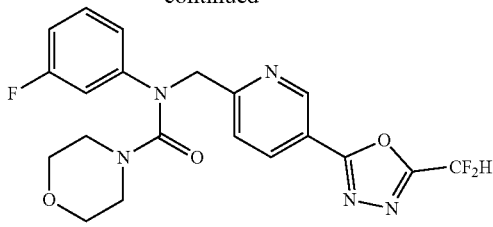

N-((5-(2-(2,2-difluoroacetyl)hydrazine-1-carbonyl)pyridin-2-yl)methyl)-N-(3-fluorophenyl)morpholine-4-carboxamide (0.088 g, 0.194 mmol) and 1-methoxy-N-triethylammoniosulfonyl-methanimidate (Burgess reagent, 0.069 g, 0.291 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-N-(3-fluorophenyl) morpholine-4-carboxamide as yellow foam (0.031 g, 37.1%).

$^1$H NMR (400 MHz, CDCl$_3$) δ 9.25 (s, 1H), 8.36 (dd, 1H, J=8.1, 2.2 Hz), 7.60 (d, 1H, J=8.2 Hz), 7.34-7.24 (m, 2H), 7.11-6.75 (m, 4H), 5.13 (s, 2H), 3.57 (t, 4H, J=4.7 Hz), 3.31 (t, 5H, J=4.7 Hz); LRMS (ES) m/z 434.4 (M$^+$+1).

Example 303. Compound 21844: N-(3-fluorophenyl)-N-((5-(5-(trifluoromethyl)-1,3,4-oxadiazol-2-yl)pyridin-2-yl)methyl) morpholine-4-carboxamide

[Step 1] N-(3-fluorophenyl)-N-((5-(2-(2,2,2-trifluoroacetyl)hydrazine-1-carbonyl)pyridin-2-yl)methyl) morpholine-4-carboxamide

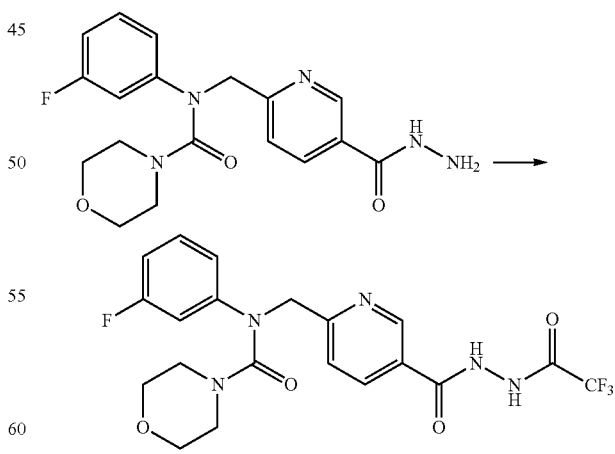

A solution of N-(3-fluorophenyl)-N-((5-(hydrazinecarbonyl)pyridin-2-yl)methyl)morpholine-4-carboxamide (0.096 g, 0.257 mmol) and triethylamine (0.072 mL, 0.514 mmol) in dichloromethane (2 mL) was mixed at the room temperature with trifluoroacetic anhydride (0.036 mL, 0.257 mmol).

The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification N-(3-fluorophenyl)-N-((5-(2-(2,2,2-trifluoroacetyl)hydrazine-1-carbonyl)pyridin-2-yl)methyl)morpholine-4-carboxamide, 0.083 g, 68.4%, white foam).

[Step 2] Compound 21844

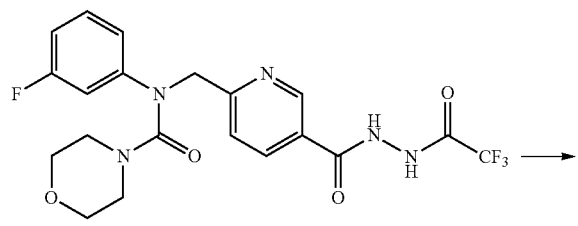

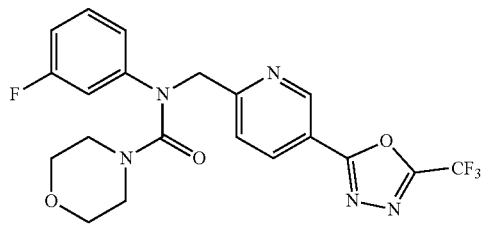

N-(3-fluorophenyl)-N-((5-(2-(2,2,2-trifluoroacetyl)hydrazine-1-carbonyl)pyridin-2-yl)methyl)morpholine-4-carboxamide (0.083 g, 0.176 mmol) and 1-methoxy-N-triethylammoniosulfonyl-methanimidate (Burgess reagent, 0.063 g, 0.264 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-fluorophenyl)-N-((5-(5-(trifluoromethyl)-1,3,4-oxadiazol-2-yl)pyridin-2-yl)methyl) morpholine-4-carboxamide as yellow foam (0.043 g, 53.9%).

$^1$H NMR (400 MHz, CDCl$_3$) δ 9.25 (s, 1H), 8.36 (dt, 1H, J=8.2, 1.9 Hz), 7.62 (d, 1H, J=8.2 Hz), 7.33-7.26 (m, 1H), 7.01-6.89 (m, 2H), 6.83 (t, 1H, J=8.3 Hz), 5.13 (s, 2H), 3.57 (t, 4H, J=4.7 Hz), 3.31 (t, 5H, J=4.7 Hz); LRMS (ES) m/z 452.0 (M$^+$+1).

Example 304. Compound 21845: N-(4-(5-(difluoromethyl)-1,3,4-oxadiazol-2-yl)-2-fluorobenzyl)-N-(3-fluorophenyl)morpholine-4-carboxamide

[Step 1] Methyl 3-fluoro-4-((N-(3-fluorophenyl)morpholine-4-carboxamido)methyl)benzoate

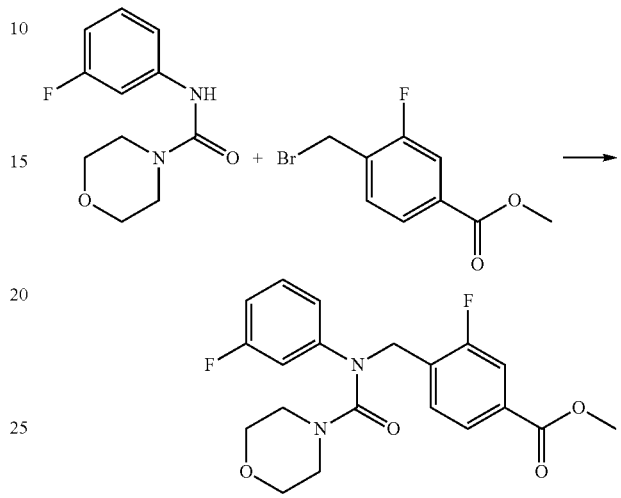

To a stirred solution of N-(3-fluorophenyl)morpholine-4-carboxamide (0.200 g, 0.892 mmol) in N,N-dimethylformamide (5 mL) was added at 0° C. sodium hydride (60.00%, 0.036 g, 0.892 mmol). The reaction mixture was stirred at the same temperature for 1 hr, added at the room temperature with methyl 4-(bromomethyl)-3-fluorobenzoate (0.220 g, 0.892 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 3-fluoro-4-((N-(3-fluorophenyl)morpholine-4-carboxamido)methyl)benzoate as yellow oil (0.328 g, 94.2%).

[Step 2] N-(2-fluoro-4-(hydrazinecarbonyl)benzyl)-N-(3-fluorophenyl)morpholine-4-carboxamide

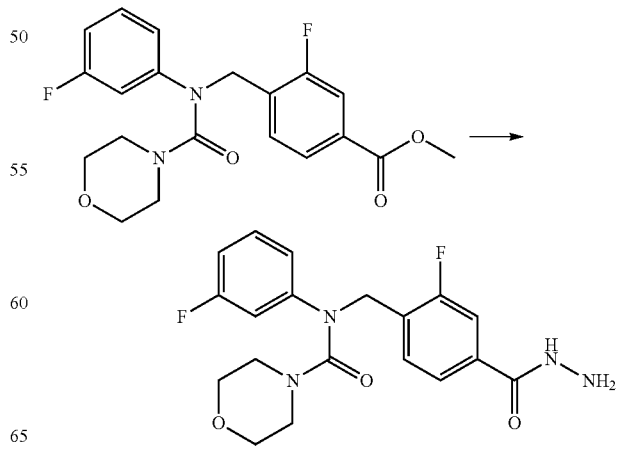

Methyl 3-fluoro-4-((N-(3-fluorophenyl)morpholine-4-carboxamido)methyl)benzoate (0.328 g, 0.840 mmol) and hydrazine monohydrate (0.408 mL, 8.402 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 10%) to give N-(2-fluoro-4-(hydrazinecarbonyl)benzyl)-N-(3-fluorophenyl)morpholine-4-carboxamide as yellow oil (0.327 g, 99.5%).

[Step 3] N-(4-(2-(2,2-difluoroacetyl)hydrazine-1-carbonyl)-2-fluorobenzyl)-N-(3-fluorophenyl)morpholine-4-carboxamide

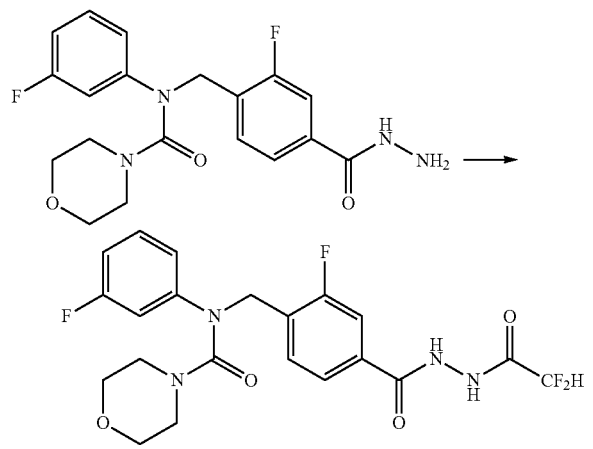

A solution of N-(2-fluoro-4-(hydrazinecarbonyl)benzyl)-N-(3-fluorophenyl)morpholine-4-carboxamide (0.164 g, 0.419 mmol) and triethylamine (0.117 mL, 0.838 mmol) in dichloromethane (2 mL) was mixed at the room temperature with 2,2-difluoroacetic anhydride (0.052 mL, 0.419 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification N-(4-(2-(2,2-difluoroacetyl)hydrazine-1-carbonyl)-2-fluorobenzyl)-N-(3-fluorophenyl)morpholine-4-carboxamide, 0.127 g, 64.7%, white foam).

[Step 4] Compound 21845

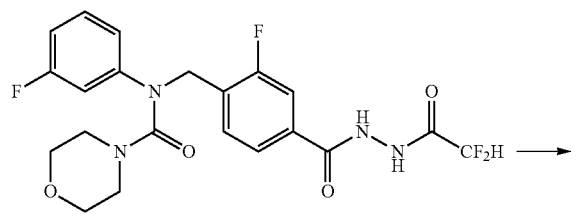

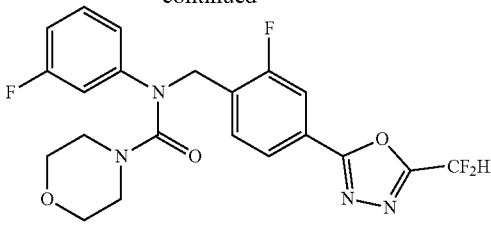

N-(4-(2-(2,2-difluoroacetyl)hydrazine-1-carbonyl)-2-fluorobenzyl)-N-(3-fluorophenyl)morpholine-4-carboxamide (0.127 g, 0.271 mmol) and 1-methoxy-N-triethylammoniosulfonyl-methanimidate (Burgess reagent, 0.097 g, 0.407 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(3-fluorophenyl)morpholine-4-carboxamide as yellow foam (0.074 g, 60.9%).

$^1$H NMR (400 MHz, CDCl$_3$) δ 7.89 (d, 1H, J=8.0 Hz), 7.78 (d, 1H, J=10.1 Hz), 7.69 (t, 1H, J=7.7 Hz), 7.35-7.26 (m, 1H), 6.95-6.77 (m, 4H), 4.99 (s, 2H), 3.53 (t, 4H, J=4.7 Hz), 3.29 (t, 4H, J=4.7 Hz); LRMS (ES) m/z 451.1 (M$^+$+1).

Example 305. Compound 21846: N-(2-fluoro-4-(5-(trifluoromethyl)-1,3,4-oxadiazol-2-yl)benzyl)-N-(3-fluorophenyl)morpholine-4-carboxamide

[Step 1] (N-(2-fluoro-4-(2-(2,2,2-trifluoroacetyl)hydrazine-1-carbonyl)benzyl)-N-(3-fluorophenyl)morpholine-4-carboxamide

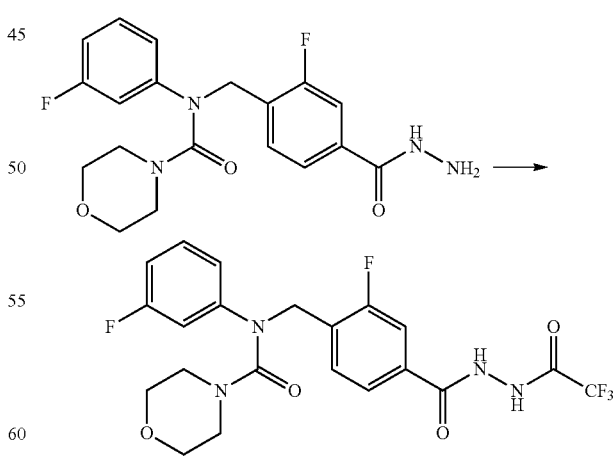

A solution of N-(2-fluoro-4-(hydrazinecarbonyl)benzyl)-N-(3-fluorophenyl)morpholine-4-carboxamide (0.164 g, 0.419 mmol) and triethylamine (0.117 mL, 0.838 mmol) in dichloromethane (2 mL) was mixed at the room temperature with trifluoroacetic anhydride (0.059 mL, 0.419 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(2-fluoro-4-(2-(2,2,2-trifluoroacetyl) hydrazine-1-carbonyl)benzyl)-N-(3-fluorophenyl)morpholine-4-carboxamide, 0.134 g, 65.8%, white foam).

[Step 2] Compound 21846

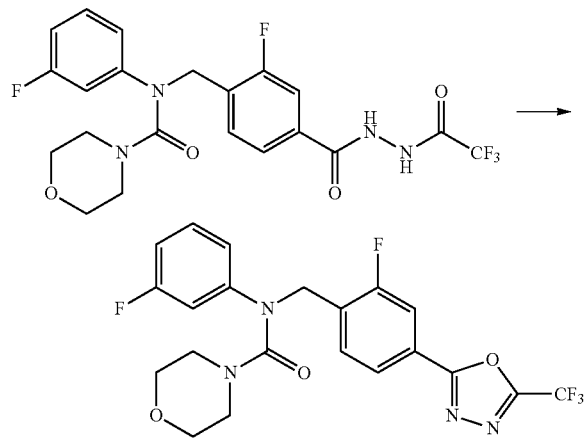

N-(2-fluoro-4-(2-(2,2,2-trifluoroacetyl)hydrazine-1-carbonyl)benzyl)-N-(3-fluorophenyl)morpholine-4-carboxamide (0.134 g, 0.275 mmol) and 1-methoxy-N-triethylammoniosulfonyl-methanimidate (Burgess reagent, 0.098 g, 0.413 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(2-fluoro-4-(5-(trifluoromethyl)-1,3,4-oxadiazol-2-yl)benzyl)-N-(3-fluorophenyl)morpholine-4-carboxamide as yellow foam (0.397 g, 307.7%).

$^1$H NMR (400 MHz, CDCl$_3$) δ 7.88 (d, 1H, J=8.0 Hz), 7.78 (d, 1H, J=10.0 Hz), 7.71 (t, 1H, J=7.6 Hz), 7.36-7.25 (m, 1H), 6.88 (dt, 3H, J=15.8, 7.5 Hz), 4.99 (s, 2H), 3.54 (t, 4H, J=4.7 Hz), 3.29 (t, 4H, J=4.7 Hz); LRMS (ES) m/z 469.0 (M$^+$+1).

Example 306. Compound 21847: N-(4-chlorophenyl)-N-((5-(5-(difluoromethyl)-1,3,4-oxadiazol-2-yl) pyridin-2-yl)methyl) morpholine-4-carboxamide

[Step 1]
N-(4-chlorophenyl)morpholine-4-carboxamide

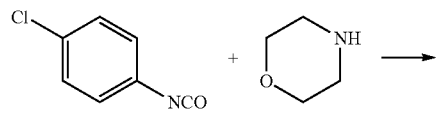

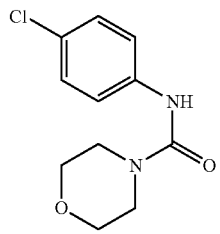

A solution of 1-chloro-4-isocyanatobenzene (0.500 g, 3.256 mmol) in diethylether (10 mL) was mixed at 0° C. with morpholine (0.282 mL, 3.256 mmol), and stirred at the room temperature for 18 hr. The precipitates were collected by filtration, washed by diethylether, and dried to give N-(4-chlorophenyl)morpholine-4-carboxamide as white solid (0.715 g, 91.2%).

[Step 2] Methyl 6-((N-(4-chlorophenyl)morpholine-4-carboxamido)methyl)nicotinate

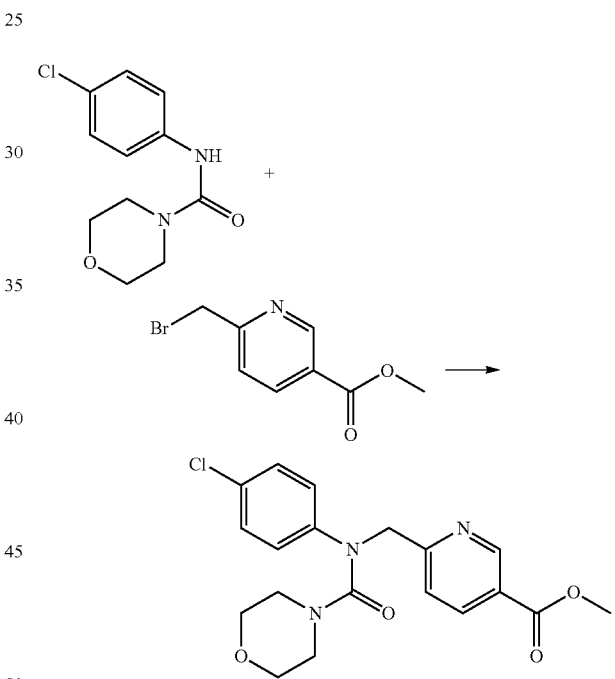

To a stirred solution of N-(4-chlorophenyl)morpholine-4-carboxamide (0.200 g, 0.831 mmol) in N,N-dimethylformamide (5 mL) was added at 0° C. sodium hydride (60.00%, 0.033 g, 0.831 mmol). The reaction mixture was stirred at the same temperature for 1 hr, added at the room temperature with methyl 6-(bromomethyl)nicotinate (0.191 g, 0.831 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 6-((N-(4-chlorophenyl)morpholine-4-carboxamido)methyl) nicotinate as yellow oil (0.220 g, 67.9%).

[Step 3] N-(4-chlorophenyl)-N-((5-(hydrazinecarbonyl)pyridin-2-yl)methyl)morpholine-4-carboxamide

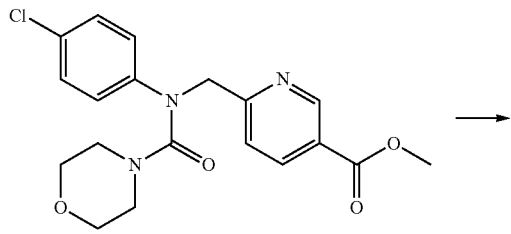

Methyl 6-((N-(4-chlorophenyl)morpholine-4-carboxamido)methyl)nicotinate (0.220 g, 0.564 mmol) and hydrazine monohydrate (0.274 mL, 5.643 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-chlorophenyl)-N-((5-(hydrazinecarbonyl)pyridin-2-yl)methyl)morpholine-4-carboxamide as yellow oil (0.215 g, 97.5%).

[Step 4] (N-(4-chlorophenyl)-N-((5-(2-(2,2-difluoroacetyl)hydrazine-1-carbonyl)pyridin-2-yl)methyl)morpholine-4-carboxamide

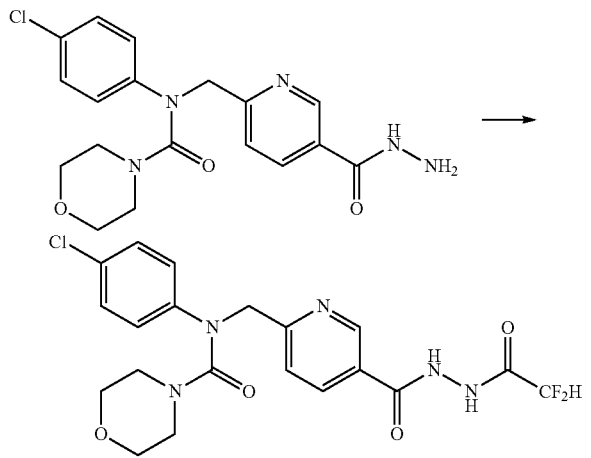

A solution of N-(4-chlorophenyl)-N-((5-(hydrazinecarbonyl)pyridin-2-yl)methyl)morpholine-4-carboxamide (0.108 g, 0.276 mmol) and triethylamine (0.077 mL, 0.552 mmol) in dichloromethane (2 mL) was mixed at the room temperature with 2,2-difluoroacetic anhydride (0.034 mL, 0.276 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-chlorophenyl)-N-((5-(2-(2,2-difluoroacetyl)hydrazine-1-carbonyl)pyridin-2-yl)methyl)morpholine-4-carboxamide, 0.092 g, 71.3%, white foam).

[Step 5] Compound 21847

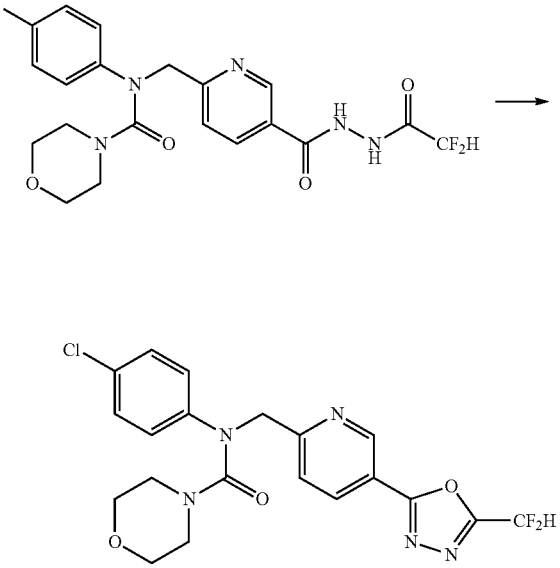

N-(4-chlorophenyl)-N-((5-(2-(2,2-difluoroacetyl)hydrazine-1-carbonyl)pyridin-2-yl) methyl)morpholine-4-carboxamide (0.092 g, 0.197 mmol) and 1-methoxy-N-triethylammoniosulfonyl-methanimidate (Burgess reagent, 0.070 g, 0.295 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-chlorophenyl)-N-((5-(5-(difluoromethyl)-1,3,4-oxadiazol-2-yl)pyridin-2-yl)methyl) morpholine-4-carboxamide as white foam (0.030 g, 33.9%).

$^1$H NMR (400 MHz, CDCl$_3$) δ 9.24 (d, 1H, J=2.3 Hz), 8.36 (dd, 1H, J=8.2, 2.0 Hz), 7.61 (d, 1H, J=8.2 Hz), 7.34-7.26 (m, 1H), 7.19-7.11 (m, 2H), 6.95 (t, 1H, J=51.7 Hz), 5.10 (s, 2H), 3.56 (t, 4H, J=4.3 Hz), 3.28 (t, 4H, J=4.9 Hz); LRMS (ES) m/z 450.2 (M$^+$+1).

Example 307. Compound 21848: N-(4-chlorophenyl)-N-((5-(5-(trifluoromethyl)-1,3,4-oxadiazol-2-yl)pyridin-2-yl)methyl) morpholine-4-carboxamide

[Step 1] (N-(4-chlorophenyl)-N-((5-(2-(2,2,2-trifluoroacetyl)hydrazine-1-carbonyl)pyridin-2-yl)methyl) morpholine-4-carboxamide

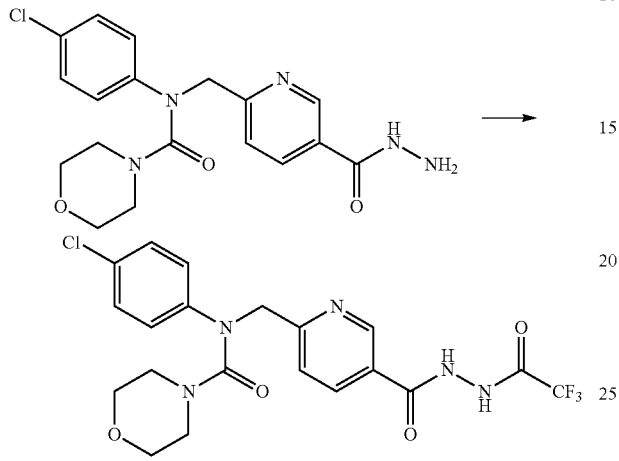

A solution of N-(4-chlorophenyl)-N-((5-(hydrazinecarbonyl)pyridin-2-yl)methyl)morpholine-4-carboxamide (0.108 g, 0.276 mmol) and triethylamine (0.077 mL, 0.552 mmol) in dichloromethane (2 mL) was mixed at the room temperature with trifluoroacetic anhydride (0.039 mL, 0.276 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-chlorophenyl)-N-((5-(2-(2,2,2-trifluoroacetyl)hydrazine-1-carbonyl)pyridin-2-yl)methyl)morpholine-4-carboxamide, 0.101 g, 75.5%, white foam).

[Step 2] Compound 21848

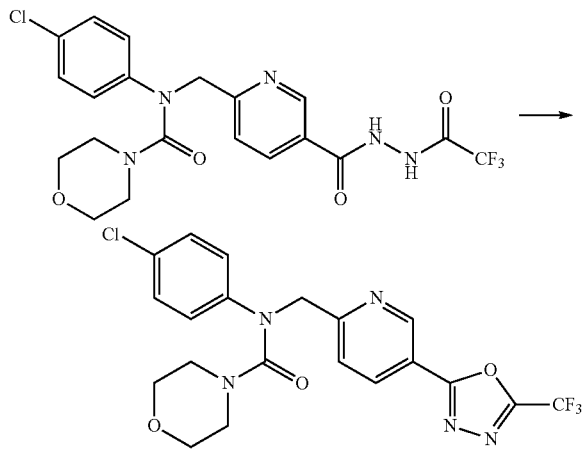

N-(4-chlorophenyl)-N-((5-(2-(2,2,2-trifluoroacetyl)hydrazine-1-carbonyl)pyridin-2-yl)methyl)morpholine-4-carboxamide (0.101 g, 0.208 mmol) and 1-methoxy-N-triethylammoniosulfonyl-methanimidate (Burgess reagent, 0.074 g, 0.312 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-chlorophenyl)-N-((5-(5-(trifluoromethyl)-1,3,4-oxadiazol-2-yl)pyridin-2-yl)methyl) morpholine-4-carboxamide as yellow foam (0.082 g, 83.8%).

$^1$H NMR (400 MHz, CDCl$_3$) δ 9.24 (s, 1H), 8.40-8.32 (m, 1H), 7.63 (d, 1H, J=8.3 Hz), 7.34-7.26 (m, 1H), 7.19-7.11 (m, 2H), 5.10 (s, 2H), 3.55 (t, 4H, J=4.7 Hz), 3.28 (t, 4H, J=4.8 Hz); LRMS (ES) m/z 468.2 (M$^+$+1).

Example 308. Compound 21849: N-(4-chlorophenyl)-N-(4-(5-(difluoromethyl)-1,3,4-oxadiazol-2-yl)-2-fluorobenzyl)morpholine-4-carboxamide

[Step 1] Methyl 4-((N-(4-chlorophenyl)morpholine-4-carboxamido)methyl)-3-fluorobenzoate

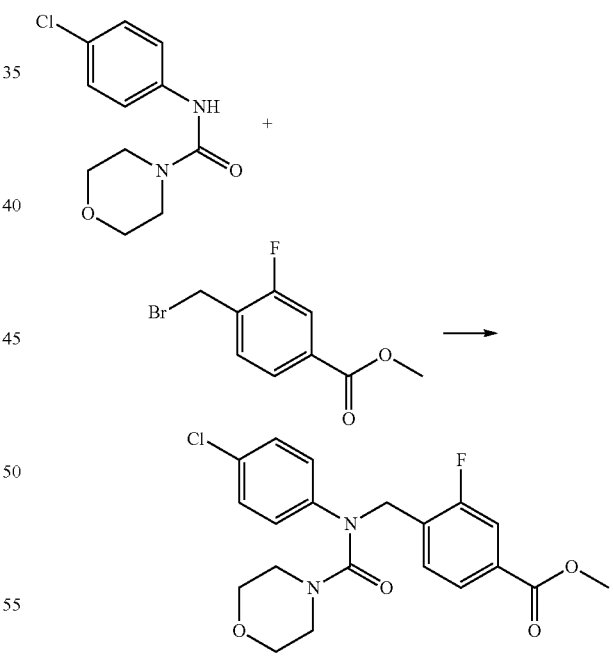

To a stirred solution of N-(4-chlorophenyl)morpholine-4-carboxamide (0.200 g, 0.831 mmol) in N,N-dimethylformamide (5 mL) was added at 0° C. sodium hydride (60.00%, 0.033 g, 0.831 mmol). The reaction mixture was stirred at the same temperature for 1 hr, added at the room temperature with methyl 4-(bromomethyl)-3-fluorobenzoate (0.205 g, 0.831 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 4-((N-(4-chlorophenyl)morpholine-4-carboxamido) methyl)-3-fluorobenzoate as yellow oil (0.261 g, 77.2%).

[Step 2] N-(4-chlorophenyl)-N-(2-fluoro-4-(hydrazinecarbonyl)benzyl)morpholine-4-carboxamide

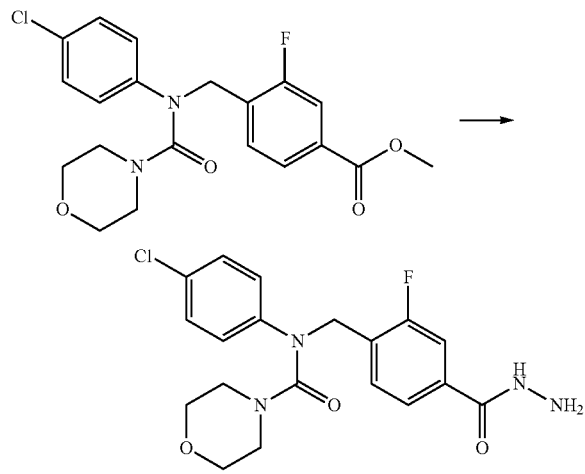

Methyl 4-((N-(4-chlorophenyl)morpholine-4-carboxamido)methyl)-3-fluorobenzoate (0.261 g, 0.642 mmol) and hydrazine monohydrate (0.312 mL, 6.415 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-chlorophenyl)-N-(2-fluoro-4-(hydrazinecarbonyl)benzyl)morpholine-4-carboxamide as yellow oil (0.258 g, 98.9%).

[Step 3] N-(4-chlorophenyl)-N-(4-(2-(2,2-difluoroacetyl)hydrazine-1-carbonyl)-2-fluorobenzyl)morpholine-4-carboxamide

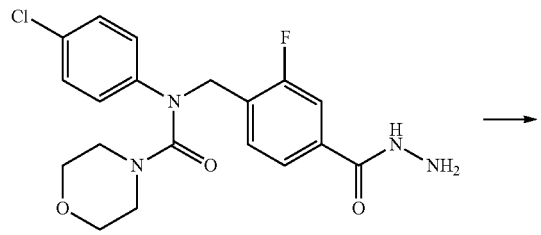

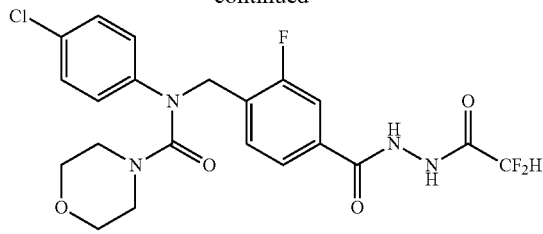

A solution of N-(4-chlorophenyl)-N-(2-fluoro-4-(hydrazinecarbonyl)benzyl)morpholine-4-carboxamide (0.149 g, 0.366 mmol) and triethylamine (0.102 mL, 0.732 mmol) in dichloromethane (2 mL) was mixed at the room temperature with 2,2-difluoroacetic anhydride (0.046 mL, 0.366 mmol). The reaction mixture was stirred at the same temperature for 18 hr. Then, water was added to the reaction mixture, followed by extraction, with dichloromethane. The bi-phasic mixture was passed through a plastic frit to remove the solid residues and aqueous layer, and the organic layer collected was concentrated in vacuo. The crude product was used without further purification (N-(4-chlorophenyl)-N-(4-(2-(2, 2-difluoroacetyl)hydrazine-1-carbonyl)-2-fluorobenzyl) morpholine-4-carboxamide, 0.126 g, 71.2%, white foam).

[Step 4] Compound 21849

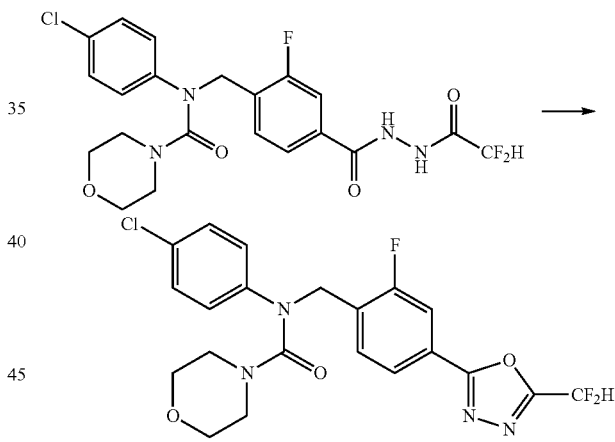

N-(4-chlorophenyl)-N-(4-(2-(2,2-difluoroacetyl)hydrazine-1-carbonyl)-2-fluorobenzyl)morpholine-4-carboxamide (0.126 g, 0.261 mmol) and 1-methoxy-N-triethylammoniosulfonyl-methanimidate (Burgess reagent, 0.093 g, 0.391 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-chlorophenyl)-N-(4-(5-(difluoromethyl)-1,3,4-oxadiazol-2-yl)-2-fluorobenzyl)morpholine-4-carboxamide as yellow foam (0.051 g, 41.8%).

¹H NMR (400 MHz, CDCl₃) δ 7.88 (d, 1H, J=8.0 Hz), 7.76 (d, 1H, J=10.1 Hz), 7.70 (t, 1H, J=7.7 Hz), 7.30 (d, 2H, J=8.5 Hz), 7.10-6.76 (m, 3H), 4.96 (s, 2H), 3.52 (t, 4H, J=4.7 Hz), 3.26 (t, 4H, J=4.7 Hz); LRMS (ES) m/z 467.0 (M⁺+1).

Example 309. Compound 21850: N-(4-chlorophenyl)-N-(2-fluoro-4-(5-(trifluoromethyl)-1,3,4-oxadiazol-2-yl)benzyl)morpholine-4-carboxamide

[Step 1] (N-(4-chlorophenyl)-N-(2-fluoro-4-(2-(2,2,2-trifluoroacetyl)hydrazine-1-carbonyl)benzyl)morpholine-4-carboxamide

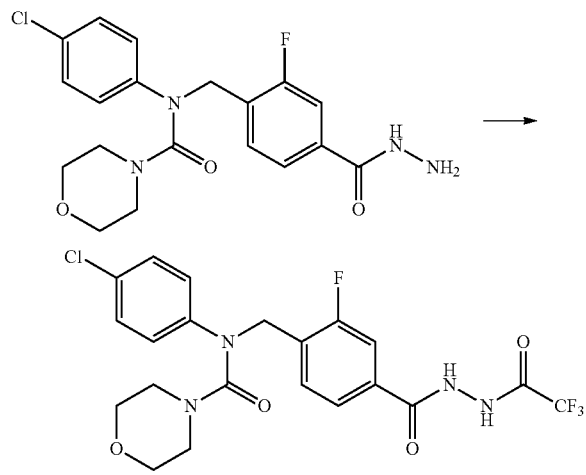

A solution of N-(4-chlorophenyl)-N-(2-fluoro-4-(hydrazinecarbonyl)benzyl)morpholine-4-carboxamide (0.149 g, 0.366 mmol) and triethylamine (0.102 mL, 0.732 mmol) in dichloromethane (2 mL) was mixed at the room temperature with trifluoroacetic anhydride (0.052 mL, 0.366 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-chlorophenyl)-N-(2-fluoro-4-(2-(2,2,2-trifluoroacetyl)hydrazine-1-carbonyl)benzyl)morpholine-4-carboxamide, 0.117 g, 63.5%, white foam).

[Step 2] Compound 21850

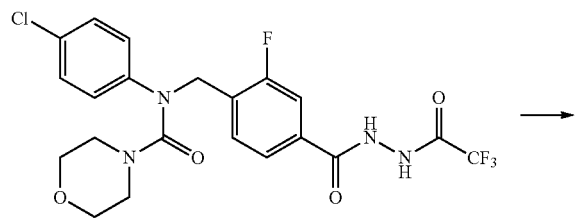

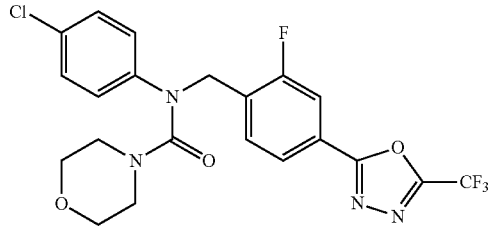

N-(4-chlorophenyl)-N-(2-fluoro-4-(2-(2,2,2-trifluoroacetyl)hydrazine-1-carbonyl)benzyl)morpholine-4-carboxamide (0.117 g, 0.233 mmol) and 1-methoxy-N-triethylammoniosulfonyl-methanimidate (Burgess reagent, 0.083 g, 0.349 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(4-chlorophenyl)-N-(2-fluoro-4-(5-(trifluoromethyl)-1,3,4-oxadiazol-2-yl)benzyl)morpholine-4-carboxamide as white foam (0.010 g, 8.8%).

¹H NMR (400 MHz, CDCl₃) δ 7.88 (d, 1H, J=8.1 Hz), 7.80-7.68 (m, 2H), 7.40-7.22 (m, 2H), 7.07 (d, 2H, J=8.3 Hz), 4.97 (s, 2H), 3.52 (t, 4H, J=4.7 Hz), 3.26 (t, 4H, J=4.6 Hz); LRMS (ES) m/z 485.0 (M⁺+1).

Example 310. Compound 21851: N-(3-chlorophenyl)-N-((5-(5-(difluoromethyl)-1,3,4-oxadiazol-2-yl)pyridin-2-yl)methyl) morpholine-4-carboxamide

[Step 1] N-(3-chlorophenyl)morpholine-4-carboxamide

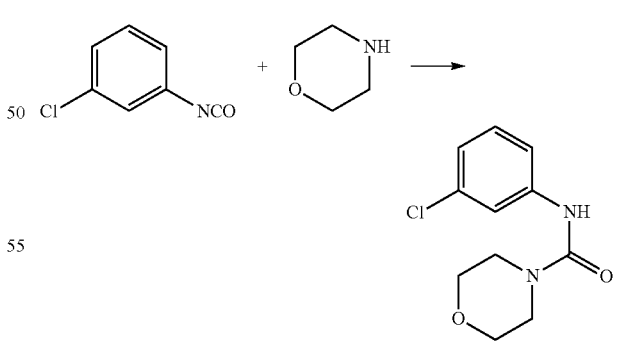

A solution of 1-chloro-3-isocyanatobenzene (0.500 g, 3.256 mmol) in diethylether (10 mL) was mixed at 0° C. with morpholine (0.282 mL, 3.256 mmol), and stirred at the room temperature for 18 hr. The precipitates were collected by filtration, washed by diethylether, and dried to give N-(3-chlorophenyl)morpholine-4-carboxamide as white solid (0.650 g, 82.9%).

[Step 2] Methyl 6-((N-(3-chlorophenyl)morpholine-4-carboxamido)methyl)nicotinate

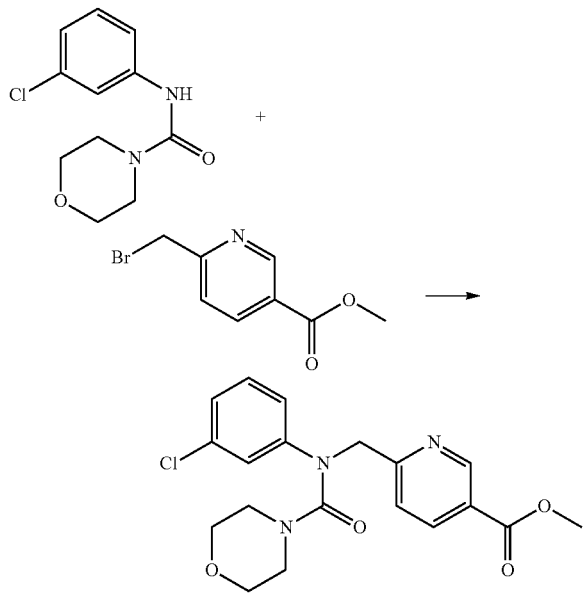

To a stirred solution of N-(3-chlorophenyl)morpholine-4-carboxamide (0.200 g, 0.831 mmol) in N,N-dimethylformamide (5 mL) was added at 0° C. sodium hydride (60.00%, 0.033 g, 0.831 mmol). The reaction mixture was stirred at the same temperature for 1 hr. added at the room temperature with methyl 6-(bromomethyl)nicotinate (0.191 g, 0.831 mmol), and stirred for additional 2 hr.

Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 6-((N-(3-chlorophenyl)morpholine-4-carboxamido)methyl)nicotinate as yellow oil (0.192 g, 59.3%).

[Step 3] N-(3-chlorophenyl)-N-((5-(hydrazinecarbonyl)pyridin-2-yl)methyl)morpholine-4-carboxamide

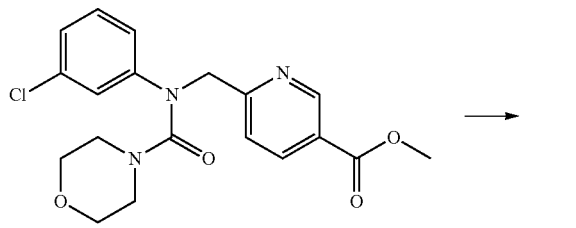

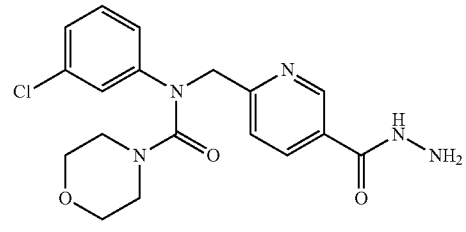

Methyl 6-((N-(3-chlorophenyl)morpholine-4-carboxamido)methyl)nicotinate (0.192 g, 0.493 mmol) and hydrazine monohydrate (0.239 mL, 4.925 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chlorophenyl)-N-((5-(hydrazinecarbonyl)pyridin-2-yl)methyl)morpholine-4-carboxamide as yellow oil (0.189 g, 98.6%).

[Step 4] (N-(3-chlorophenyl)-N-((5-(2-(2,2-difluoroacetyl)hydrazine-1-carbonyl)pyridin-2-yl)methyl)morpholine-4-carboxamide

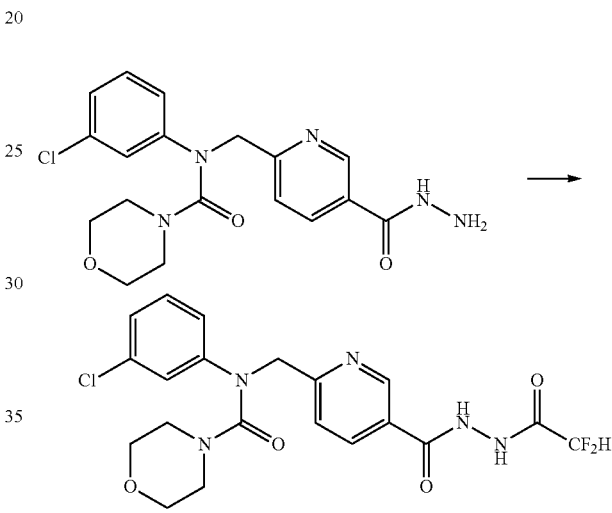

A solution of N-(3-chlorophenyl)-N-((5-(hydrazinecarbonyl)pyridin-2-yl)methyl)morpholine-4-carboxamide (0.095 g, 0.242 mmol) and triethylamine (0.068 mL, 0.485 mmol) in dichloromethane (2 mL) was mixed at the room temperature with 2,2-difluoroacetic anhydride (0.030 mL, 0.242 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(3-chlorophenyl)-N-((5-(2-(2,2-difluoroacetyl)hydrazine-1-carbonyl)pyridin-2-yl)methyl)morpholine-4-carboxamide, 0.090 g, 79.2%, white foam).

[Step 5] Compound 21851

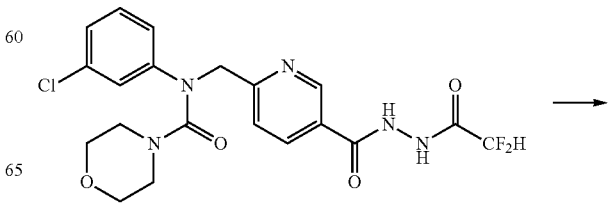

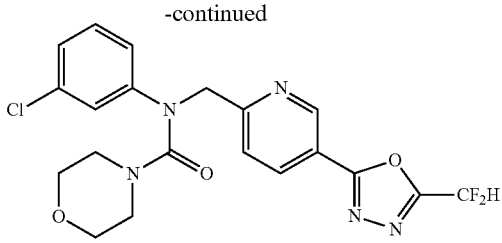

N-(3-chlorophenyl)-N-((5-(2-(2,2-difluoroacetyl)hydrazine-1-carbonyl)pyridin-2-yl) methyl)morpholine-4-carboxamide (0.090 g, 0.192 mmol) and 1-methoxy-N-triethylammoniosulfonyl-methanimidate (Burgess reagent, 0.069 g, 0.288 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chlorophenyl)-N-((5-(5-(difluoromethyl)-1,3,4-oxadiazol-2-yl)pyridin-2-yl)methyl) morpholine-4-carboxamide as yellow foam (0.029 g, 33.2%).

$^1$H NMR (400 MHz, CDCl$_3$) δ 9.26 (s, 1H), 8.36 (dd, 1H, J=8.2, 2.1 Hz), 7.60 (d, 1H, J=8.2 Hz), 7.31-7.19 (m, 2H), 7.14-6.75 (m, 3H), 5.12 (s, 2H), 3.57 (t, 4H, J=4.2 Hz), 3.30 (t, 4H, J=4.6 Hz); LRMS (ES) m/z 450.0 (M$^+$+1).

Example 311. Compound 21852: N-(3-chlorophenyl)-N-((5-(5-(trifluoromethyl)-1,3,4-oxadiazol-2-yl)pyridin-2-yl)methyl) morpholine-4-carboxamide

[Step 1] N-(3-chlorophenyl)-N-((5-(2-(2,2,2-trifluoroacetyl)hydrazine-1-carbonyl)pyridin-2-yl)methyl) morpholine-4-carboxamide

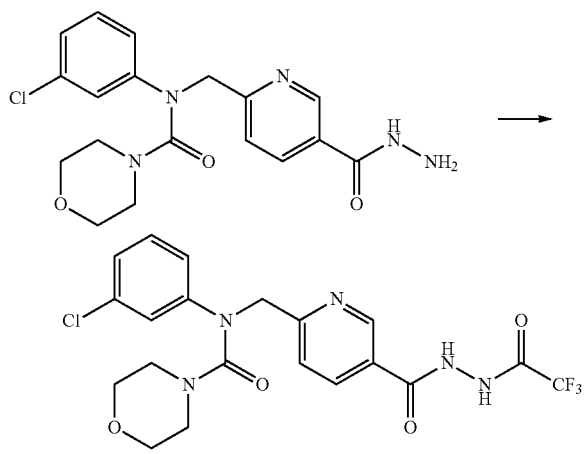

A solution of N-(3-chlorophenyl)-N-((5-(hydrazinecarbonyl)pyridin-2-yl)methyl)morpholine-4-carboxamide (0.095 g, 0.242 mmol) and triethylamine (0.068 mL, 0.485 mmol) in dichloromethane (2 mL) was mixed at the room temperature with trifluoroacetic anhydride (0.034 mL, 0.242 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification N-(3-chlorophenyl)-N-((5-(2-(2,2,2-trifluoroacetyl)hydrazine-1-carbonyl)pyridin-2-yl)methyl)morpholine-4-carboxamide, 0.079 g, 66.7%, white foam).

[Step 2] Compound 21852

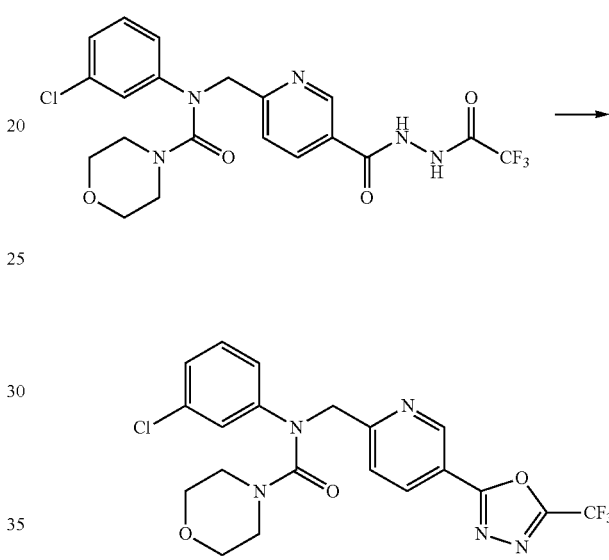

N-(3-chlorophenyl)-N-((5-(2-(2,2,2-trifluoroacetyl)hydrazine-1-carbonyl)pyridin-2-yl)methyl)morpholine-4-carboxamide (0.079 g, 0.162 mmol) and 1-methoxy-N-triethylammoniosulfonyl-methanimidate (Burgess reagent, 0.058 g, 0.242 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chlorophenyl)-N-((5-(5-(trifluoromethyl)-1,3,4-oxadiazol-2-yl)pyridin-2-yl)methyl) morpholine-4-carboxamide as yellow foam (0.019 g, 24.6%).

$^1$H NMR (400 MHz, CDCl$_3$) δ 9.26 (s, 1H), 8.37 (d, 1H, J=8.0 Hz), 7.61 (d, 1H, J=8.2 Hz), 7.31-7.16 (m, 2H), 7.10 (t, 2H, J=6.8 Hz), 5.12 (s, 2H), 3.57 (t, 4H, J=4.7 Hz), 3.30 (t, 4H, J=4.7 Hz); LRMS (ES) m/z 468.2 (M$^+$+1).

Example 312. Compound 21853: N-(3-chlorophenyl)-N-(4-(5-(difluoromethyl)-1,3,4-oxadiazol-2-yl)-2-fluorobenzyl)morpholine-4-carboxamide

[Step 1] Methyl 4-((N-(3-chlorophenyl)morpholine-4-carboxamido)methyl)-3-fluorobenzoate

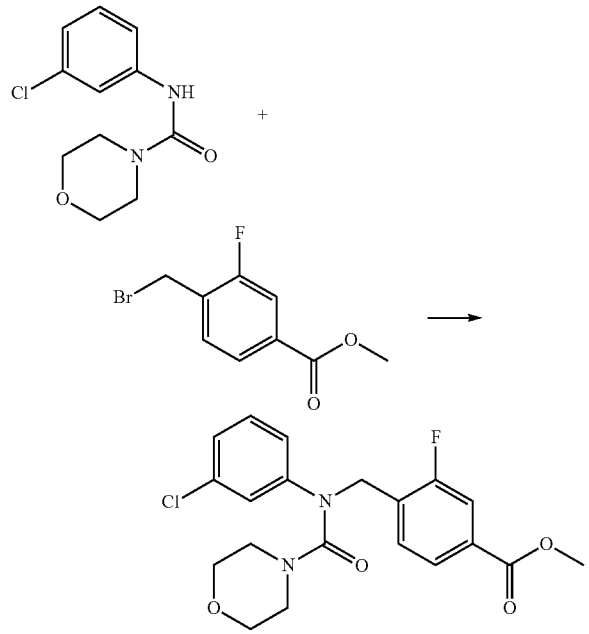

To a stirred solution of N-(3-chlorophenyl)morpholine-4-carboxamide (0.200 g, 0.831 mmol) in N,N-dimethylformamide (5 mL) was added at 0° C. sodium hydride (60.00%, 0.033 g, 0.831 mmol). The reaction mixture was stirred at the same temperature for 1 hr, treated at the room temperature with methyl 4-(bromomethyl)-3-fluorobenzoate (0.205 g, 0.831 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 4-((N-(3-chlorophenyl)morpholine-4-carboxamido)methyl)-3-fluorobenzoate as yellow oil (0.278 g, 82.2%).

[Step 2] N-(3-chlorophenyl)-N-(2-fluoro-4-(hydrazinecarbonyl)benzyl)morpholine-4-carboxamide

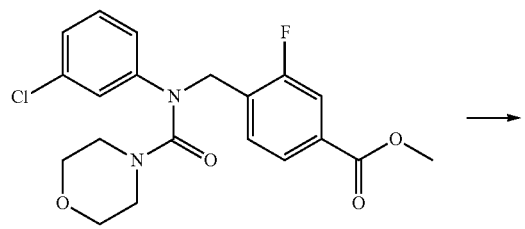

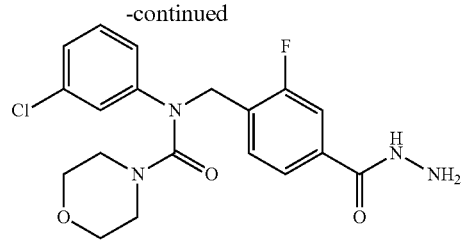

Methyl 4-((N-(3-chlorophenyl)morpholine-4-carboxamido)methyl)-3-fluorobenzoate (0.278 g, 0.683 mmol) and hydrazine monohydrate (0.332 mL, 6.833 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chlorophenyl)-N-(2-fluoro-4-(hydrazinecarbonyl)benzyl)morpholine-4-carboxamide as yellow oil (0.272 g, 97.8%).

[Step 3] (N-(3-chlorophenyl)-N-(4-(2-(2,2-difluoroacetyl)hydrazine-1-carbonyl)-2-fluorobenzyl) morpholine-4-carboxamide

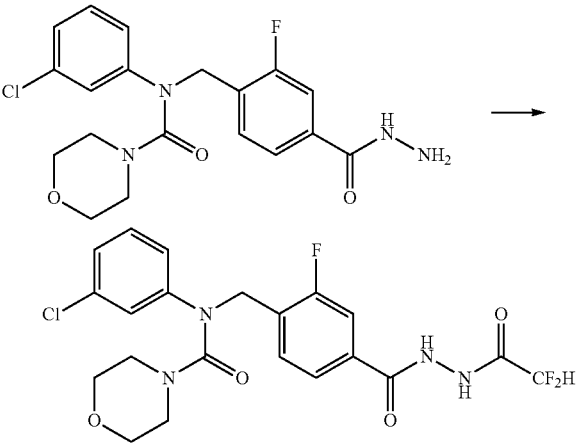

A solution of N-(3-chlorophenyl)-N-(2-fluoro-4-(hydrazinecarbonyl)benzyl)morpholine-4-carboxamide (0.136 g, 0.334 mmol) and triethylamine (0.093 mL, 0.669 mmol) in dichloromethane (2 mL) was mixed at the room temperature with 2,2-difluoroacetic anhydride (0.042 mL, 0.334 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(3-chlorophenyl)-N-(4-(2-(2,2-difluoroacetyl)hydrazine-1-carbonyl)-2-fluorobenzyl) morpholine-4-carboxamide, 0.124 g, 76.5%, white foam).

[Step 4] Compound 21853

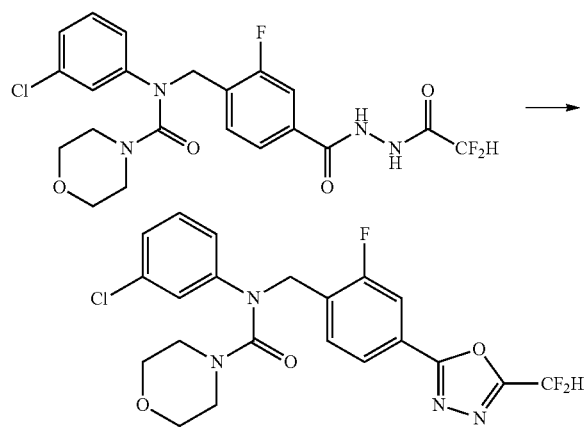

N-(3-chlorophenyl)-N-(4-(2-(2,2-difluoroacetyl)hydrazine-1-carbonyl)-2-fluorobenzyl)morpholine-4-carboxamide (0.124 g, 0.256 mmol) and 1-methoxy-N-triethylammoniosulfonyl-methanimidate (Burgess reagent, 0.091 g, 0.384 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chlorophenyl)-N-(4-(5-(difluoromethyl)-1,3,4-oxadiazol-2-yl)-2-fluorobenzyl)morpholine-4-carboxamide as white foam (0.022 g, 18.5%).

$^1$H NMR (400 MHz, CDCl$_3$) δ 7.89 (d, 1H, J=8.1 Hz), 7.78 (d, 1H, J=10.1 Hz), 7.69 (t, 1H, J=7.7 Hz), 7.31-7.21 (m, 1H), 7.19-7.10 (m, 2H), 7.08-6.76 (m, 2H), 4.98 (s, 2H), 3.53 (t, 4H, J=4.8 Hz), 3.28 (t, 4H, J=4.7 Hz); LRMS (ES) m/z 467.3 (M$^+$+1).

Example 313. Compound 21854: N-(3-chlorophenyl)-N-(2-fluoro-4-(5-(trifluoromethyl)-1,3,4-oxadiazol-2-yl)benzyl)morpholine-4-carboxamide

[Step 1] N-(3-chlorophenyl)-N-(2-fluoro-4-(2-(2,2,2-trifluoroacetyl)hydrazine-1-carbonyl)benzyl) morpholine-4-carboxamide

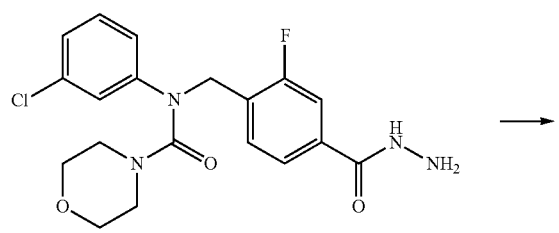

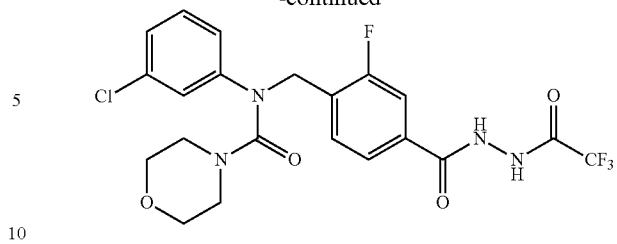

A solution of N-(3-chlorophenyl)-N-(2-fluoro-4-(hydrazinecarbonyl)benzyl)morpholine-4-carboxamide (0.136 g, 0.334 mmol) and triethylamine (0.093 mL, 0.669 mmol) in dichloromethane (2 mL) was mixed at the room temperature with trifluoroacetic anhydride (0.047 mL, 0.334 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(3-chlorophenyl)-N-(2-fluoro-4-(2-(2,2,2-trifluoroacetyl)hydrazine-1-carbonyl)benzyl)morpholine-4-carboxamide, 0.131 g, 77.9%, white foam).

[Step 2] Compound 21854

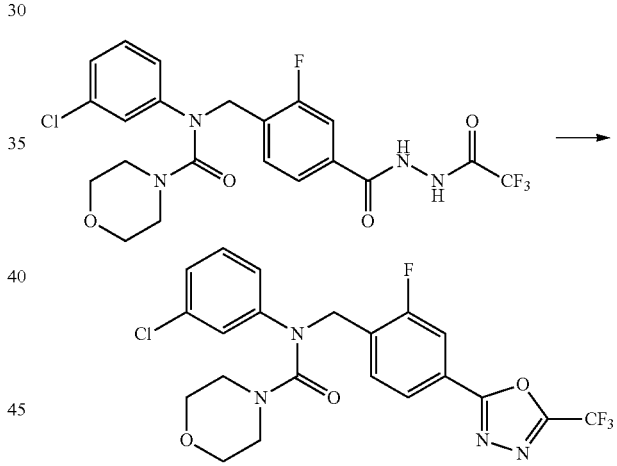

N-(3-chlorophenyl)-N-(2-fluoro-4-(2-(2,2,2-trifluoroacetyl)hydrazine-1-carbonyl)benzyl)morpholine-4-carboxamide (0.131 g, 0.261 mmol) and 1-methoxy-N-triethylammoniosulfonyl-methanimidate (Burgess reagent, 0.093 g, 0.391 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(3-chlorophenyl)-N-(2-fluoro-4-(5-(trifluoromethyl)-1,3,4-oxadiazol-2-yl)benzyl)morpholine-4-carboxamide as yellow foam (0.027 g, 21.5%).

¹H NMR (400 MHz, CDCl₃) δ 7.89 (d, 1H, J=8.1 Hz), 7.78 (d, 1H, J=10.0 Hz), 7.71 (t, 1H, J=7.6 Hz), 7.32-7.21 (m, 1H), 7.19-7.10 (m, 2H), 7.02 (d, 1H, J=8.2 Hz), 4.98 (s, 2H), 3.53 (t, 4H, J=4.7 Hz), 3.28 (t, 4H, J=4.7 Hz); LRMS (ES) m/z 485.2 (M⁺+1).

Example 314. Compound 21855: N-((5-(5-(difluoromethyl)-1,3,4-oxadiazol-2-yl)pyridin-2-yl)methyl)-N-(2-fluoro-4-methylphenyl)morpholine-4-carboxamide

[Step 1] N-(2-fluoro-4-methylphenyl)morpholine-4-carboxamide

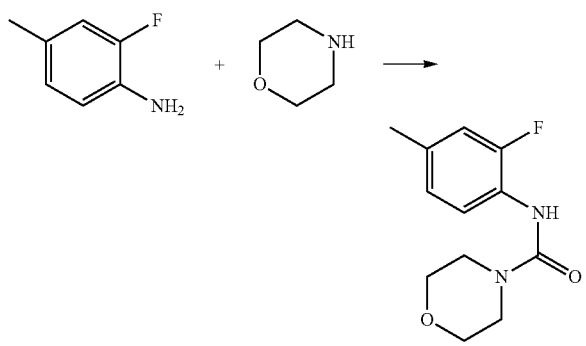

To a stirred solution of 2-fluoro-4-methylaniline (0.500 g, 3.995 mmol) and N,N-diisopropylethylamine (4.175 mL, 23.971 mmol) in dichloromethane (5 mL) was added at 0° C. triphosgene (0.593 g, 1.998 mmol). The reaction mixture was stirred at the same temperature for 0.1 min, treated at the room temperature with morpholine (0.346 mL, 3.995 mmol), and stirred for additional 2 hr. Then, water was added to the reaction mixture, followed by extraction with dichloromethane. The organic layer was washed with aqueous saturated sodium chloride solution, dried (anhydrous MgSO₄), filtered, and concentrated in vacuo. The residue was diluted with diethylether (20 mL) and stirred at the ambient temperature. The resulting precipitates were collected by filtration, washed by diethylether, and dried to give N-(2-fluoro-4-methylphenyl)morpholine-4-carboxamide as brown solid (0.349 g, 36.7%).

[Step 2] Methyl 6-((N-(2-fluoro-4-methylphenyl)morpholine-4-carboxamido)methyl)nicotinate

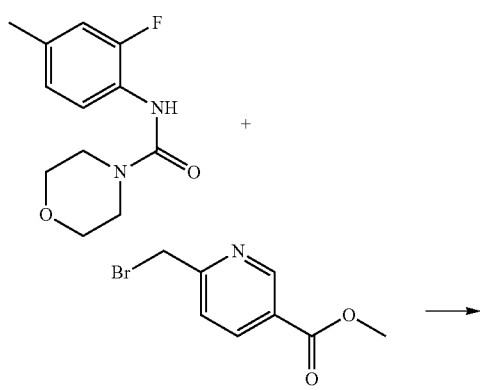

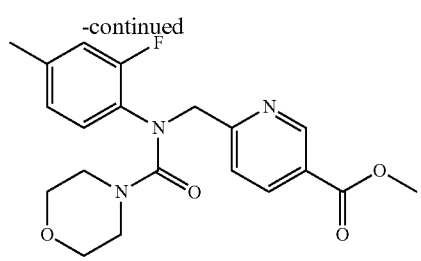

To a stirred solution of N-(2-fluoro-4-methylphenyl)morpholine-4-carboxamide (0.125 g, 0.525 mmol) in N,N-dimethylformamide (5 mL) was added at 0° C. sodium hydride (60.00%, 0.021 g, 0.525 mmol). The reaction mixture was stirred at the same temperature for 1 hr, added at the room temperature with methyl 6-(bromomethyl)nicotinate (0.121 g, 0.525 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give methyl 6-((N-(2-fluoro-4-methylphenyl)morpholine-4-carboxamido)methyl)nicotinate as yellow oil (0.105 g, 51.7%).

[Step 3] N-(2-fluoro-4-methylphenyl)-N-((5-(hydrazinecarbonyl)pyridin-2-yl)methyl)morpholine-4-carboxamide

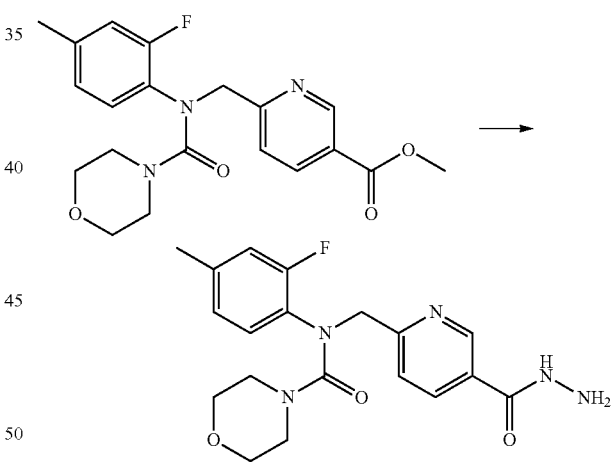

Methyl 6-((N-(2-fluoro-4-methylphenyl)morpholine-4-carboxamido)methyl)nicotinate (0.105 g, 0.271 mmol) and hydrazine monohydrate (0.132 mL, 2.710 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(2-fluoro-4-methylphenyl)-N-((5-

(hydrazinecarbonyl)pyridin-2-yl)methyl)morpholine-4-carboxamide as yellow oil (0.087 g, 82.5%).

[Step 4] (N-((5-(2-(2,2-difluoroacetyl)hydrazine-1-carbonyl)pyridin-2-yl)methyl)-N-(2-fluoro-4-methylphenyl)morpholine-4-carboxamide

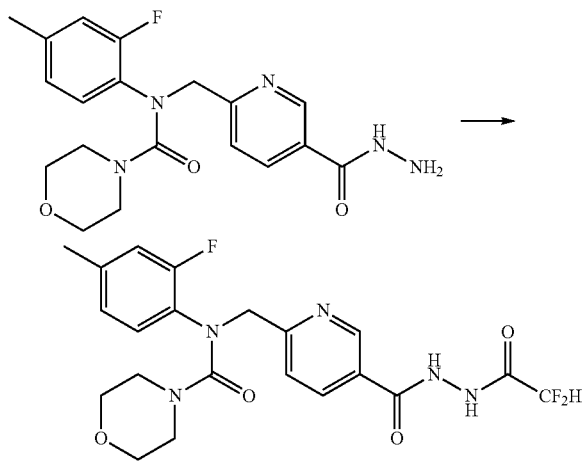

A solution of N-(2-fluoro-4-methylphenyl)-N-((5-(hydrazinecarbonyl)pyridin-2-yl)methyl)morpholine-4-carboxamide (0.087 g, 0.225 mmol) and triethylamine (0.063 mL, 0.449 mmol) in dichloromethane (2 mL) was mixed at the room temperature with 2,2-difluoroacetic anhydride (0.028 mL, 0.225 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-((5-(2-(2,2-difluoroacetyl)hydrazine-1-carbonyl)pyridin-2-yl)methyl)-N-(2-fluoro-4-methylphenyl)morpholine-4-carboxamide, 0.075 g, 71.8%, white foam).

[Step 5] Compound 21855

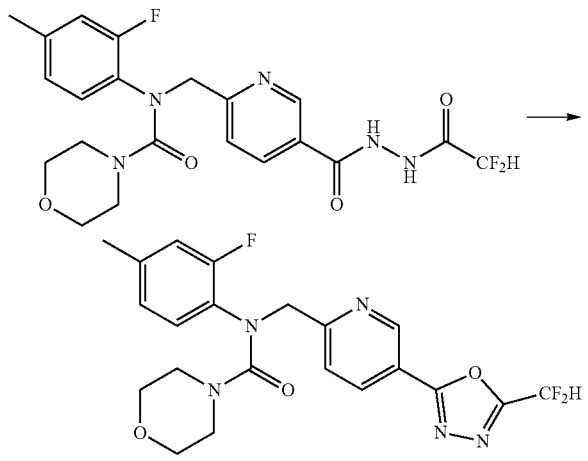

N-((5-(2-(2,2-difluoroacetyl)hydrazine-1-carbonyl)pyridin-2-yl)methyl)-N-(2-fluoro-4-methylphenyl)morpholine-4-carboxamide (0.075 g, 0.161 mmol) and 1-methoxy-N-triethylammoniosulfonyl-methanimidate (Burgess reagent, 0.058 g, 0.242 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-((5-(5-(difluoromethyl)-1,3,4-oxadiazol-2-yl)pyridin-2-yl)methyl)-N-(2-fluoro-4-methylphenyl)morpholine-4-carboxamide as white foam (0.024 g, 32.9%).

$^1$H NMR (400 MHz, CDCl$_3$) δ 9.19 (d, 1H, J=2.4 Hz), 8.34 (dd, 1H, J=8.2, 2.4 Hz), 7.74 (d, 1H, J=8.2 Hz), 7.16-7.05 (m, 1H), 6.97-6.89 (m, 3H), 5.01 (s, 2H), 3.51 (t, 4H, J=4.7 Hz), 3.26 (t, 4H, J=4.3 Hz), 2.33 (s, 3H); LRMS (ES) m/z 448.0 (M$^+$+1).

Example 115. Compound 21856: N-(4-(5-(difluoromethyl)-1,3,4-oxadiazol-2-yl)-2-fluorobenzyl)-N-(2-fluoro-4-methylphenyl)morpholine-4-carboxamide

[Step 1] Methyl 3-fluoro-4-((N-(2-fluoro-4-methylphenyl)morpholine-4-carboxamido)methyl)benzoate

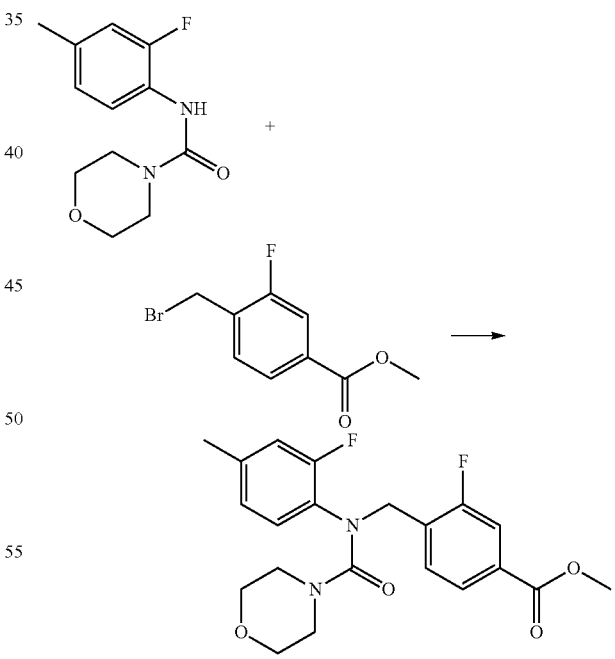

To a stirred solution of N-(2-fluoro-4-methylphenyl)morpholine-4-carboxamide (0.125 g, 0.525 mmol) in N,N-dimethylformamide (5 mL) was added at 0° C. sodium hydride (60.00%, 0.021 g, 0.525 mmol). The reaction mixture was stirred at the same temperature for 1 hr, added at the room temperature with methyl 4-(bromomethyl)-3-fluorobenzoate (0.130 g, 0.525 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give methyl 3-fluoro-4-((N-(2-fluoro-4-methylphenyl)morpholine-4-carboxamido)methyl)benzoate as yellow oil (0.123 g, 58.0%).

[Step 2] N-(2-fluoro-4-(hydrazinecarbonyl)benzyl)-N-(2-fluoro-4-methylphenyl)morpholine-4-carboxamide

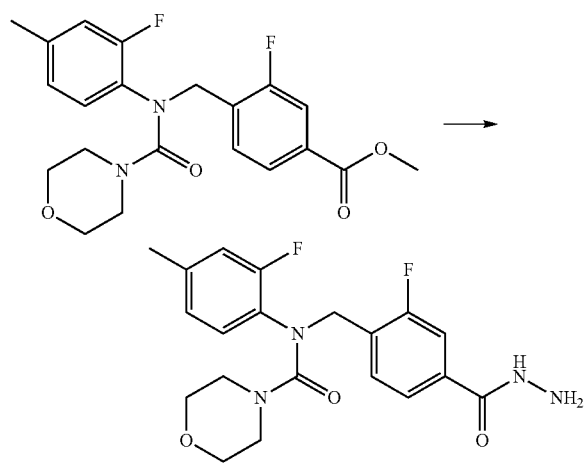

Methyl 3-fluoro-4-((N-(2-fluoro-4-methylphenyl)morpholine-4-carboxamido)methyl)benzoate (0.123 g, 0.304 mmol) and hydrazine monohydrate (0.148 mL, 3.041 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(2-fluoro-4-(hydrazinecarbonyl)benzyl)-N-(2-fluoro-4-methylphenyl)morpholine-4-carboxamide as yellow oil (0.117 g, 95.0%).

[Step 3] (N-(4-(2-(2,2-difluoroacetyl)hydrazine-1-carbonyl)-2-fluorobenzyl)-N-(2-fluoro-4-methylphenyl)morpholine-4-carboxamide

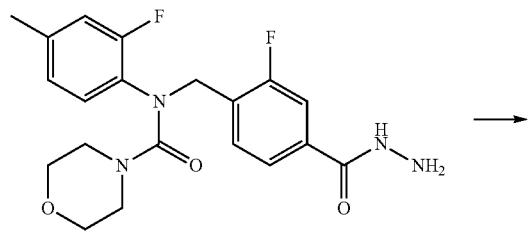

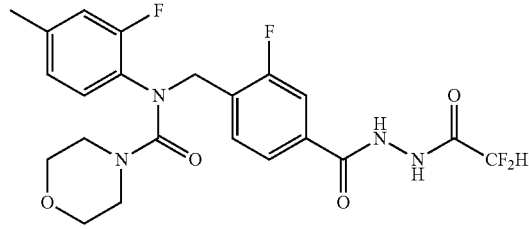

A solution of N-(2-fluoro-4-(hydrazinecarbonyl)benzyl)-N-(2-fluoro-4-methylphenyl)morpholine-4-carboxamide (0.117 g, 0.289 mmol) and triethylamine (0.081 mL, 0.579 mmol) in dichloromethane (2 mL) was mixed at the room temperature with 2,2-difluoroacetic anhydride (0.036 mL, 0.289 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-(2-(2,2-difluoroacetyl)hydrazine-1-carbonyl)-2-fluorobenzyl)-N-(2-fluoro-4-methylphenyl)morpholine-4-carboxamide, 0.092 g, 65.9%, white foam).

[Step 4] Compound 21856

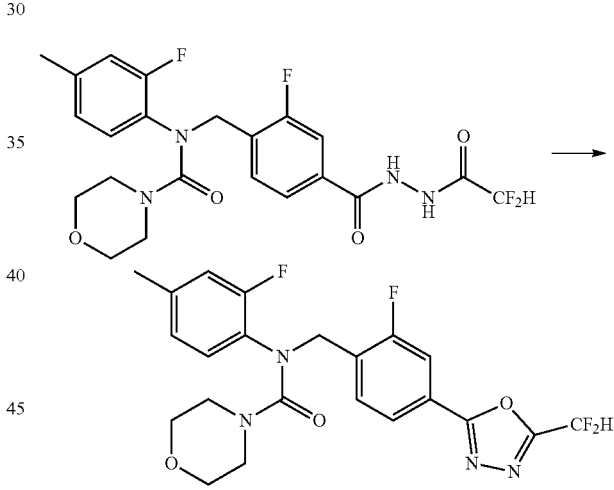

N-(4-(2-(2,2-difluoroacetyl)hydrazine-1-carbonyl)-2-fluorobenzyl)-N-(2-fluoro-4-methylphenyl)morpholine-4-carboxamide (0.092 g, 0.191 mmol) and 1-methoxy-N-triethylammoniosulfonyl-methanimidate (Burgess reagent, 0.068 g, 0.286 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(4-(5-(difluoromethyl)-1,3,4-oxadiazol-2-yl)-2-fluorobenzyl)-N-(2-fluoro-4-methylphenyl)morpholine-4-carboxamide as yellow foam (0.027 g, 30.4%).

¹H NMR (400 MHz, CDCl₃) δ 7.91-7.77 (m, 2H), 7.70 (d, 1H, J=10.0 Hz), 7.14-6.70 (m, 4H), 4.89 (s, 2H), 3.47 (t, 4H, J=4.7 Hz), 3.23 (t, 4H, J=4.7 Hz), 2.34 (s, 3H); LRMS (ES) m/z 465.0 (M⁺+1).

Example 316. Compound 21857: N-(2,4-difluorophenyl)-N-((5-(5-(trifluoromethyl)-1,3,4-oxadiazol-2-yl)pyridin-2-yl)methyl)morpholine-4-carboxamide

[Step 1] N-(2,4-difluorophenyl)morpholine-4-carboxamide

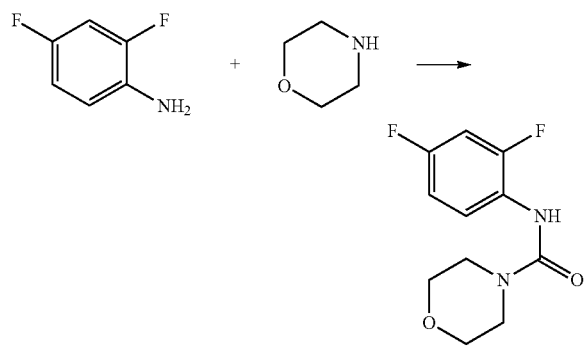

To a stirred solution of 2,4-difluoroaniline (0.500 g, 3.873 mmol) and N,N-diisopropylethylamine (4.047 mL, 23.236 mmol) in dichloromethane (5 mL) was added at 0° C. triphosgene (0.575 g, 1.936 mmol). The reaction mixture was stirred at the same temperature for 0.05 min, treated at the room temperature with morpholine (0.335 mL, 3.873 mmol), and stirred for additional 2 hr. Then, water was added to the reaction mixture, followed by extraction with dichloromethane. The organic layer was washed with aqueous saturated sodium chloride solution, dried (anhydrous MgSO₄), filtered, and concentrated in vacuo. The residue was diluted with diethylether (20 mL) and stirred at the ambient temperature. The resulting precipitates were collected by filtration, washed by diethylether, and dried to give N-(2,4-difluorophenyl)morpholine-4-carboxamide as brown solid (0.575 g, 61.3%).

[Step 2] Methyl 6-((N-(2,4-difluorophenyl)morpholine-4-carboxamido)methyl)nicotinate

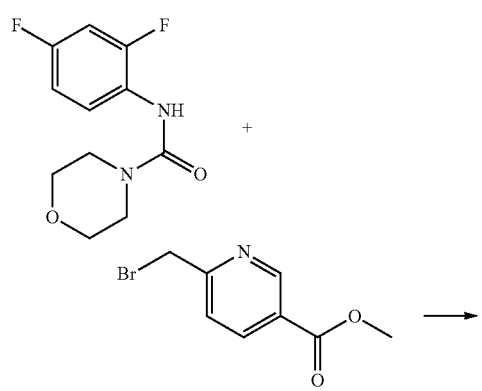

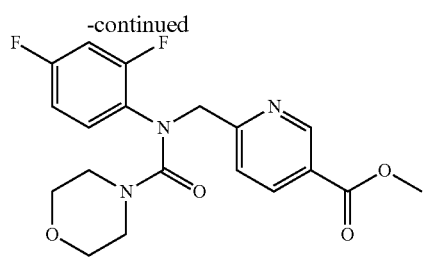

To a stirred solution of N-(2,4-difluorophenyl)morpholine-4-carboxamide (0.150 g, 0.619 mmol) in N,N-dimethylformamide (5 mL) was added at 0° C. sodium hydride (60.00%, 0.025 g, 0.619 mmol). The reaction mixture was stirred at the same temperature for 1 hr, treated at the room temperature with methyl 6-(bromomethyl)nicotinate (0.142 g, 0.619 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give methyl 6-((N-(2,4-difluorophenyl)morpholine-4-carboxamido)methyl)nicotinate as yellow oil (0.145 g, 59.8%).

[Step 3] N-(2,4-difluorophenyl)-N-((5-(hydrazinecarbonyl)pyridin-2-yl)methyl)morpholine-4-carboxamide

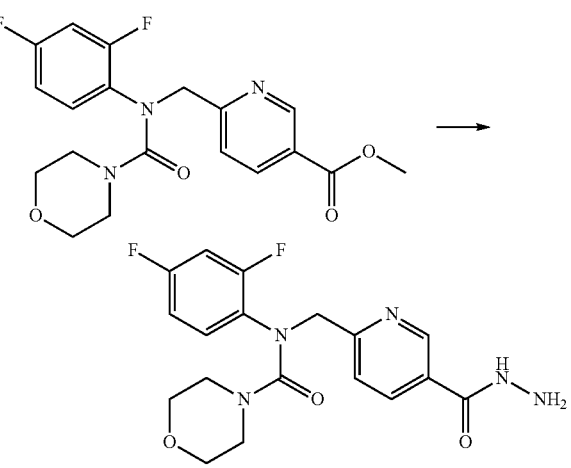

Methyl 6-((N-(2,4-difluorophenyl)morpholine-4-carboxamido)methyl)nicotinate (0.145 g, 0.370 mmol) and hydrazine monohydrate (0.180 mL, 3.705 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO₂, 4 g cartridge; methanol/dichloromethane=0% to 5%) to give N-(2,4-difluorophenyl)-N-((5-(hydrazinecarbonyl)pyridin-2-yl)methyl)morpholine-4-carboxamide as yellow oil (0.143 g, 98.3%).

[Step 4] N-(2,4-difluorophenyl)-N-((5-(2-(2,2,2-trifluoroacetyl)hydrazine-1-carbonyl)pyridin-2-yl)methyl)morpholine-4-carboxamide

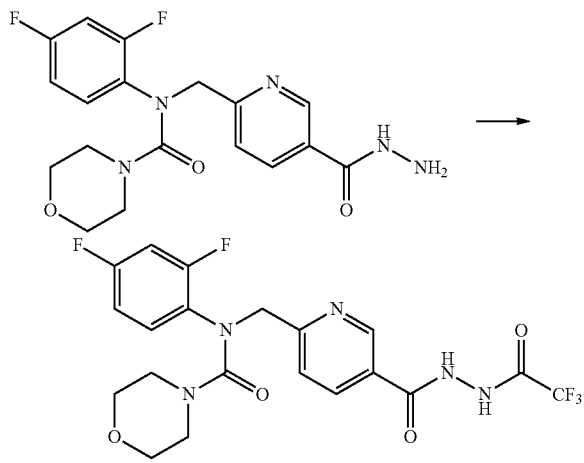

A solution of N-(2,4-difluorophenyl)-N-((5-(hydrazinecarbonyl)pyridin-2-yl)methyl)morpholine-4-carboxamide (0.072 g, 0.183 mmol) and triethylamine (0.051 mL, 0.365 mmol) in dichloromethane (2 mL) was mixed at the room temperature with trifluoroacetic anhydride (0.026 mL, 0.183 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(2,4-difluorophenyl)-N-((5-(2-(2,2,2-trifluoroacetyl)hydrazine-1-carbonyl)pyridin-2-yl)methyl)morpholine-4-carboxamide, 0.062 g, 69.6%, white foam).

[Step 5] Compound 21857

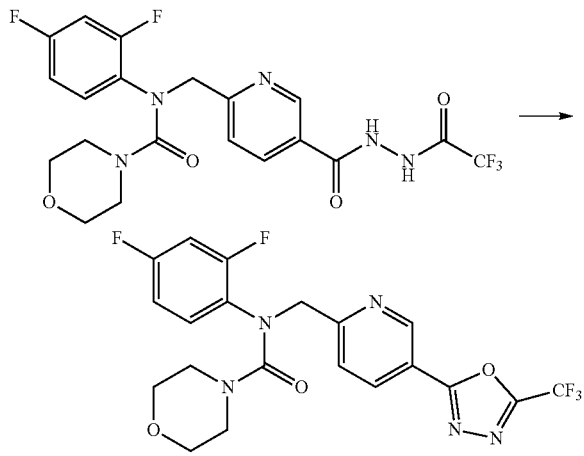

N-(2,4-difluorophenyl)-N-((5-(2-(2,2,2-trifluoroacetyl)hydrazine-1-carbonyl)pyridin-2-yl)methyl)morpholine-4-carboxamide (0.062 g, 0.127 mmol) and 1-methoxy-N-triethylammoniosulfonyl-methanimidate (Burgess reagent, 0.045 g, 0.191 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(2,4-difluorophenyl)-N-((5-(5-(trifluoromethyl)-1,3,4-oxadiazol-2-yl)pyridin-2-yl)methyl)morpholine-4-carboxamide as yellow foam (0.018 g, 29.8%).

$^1$H NMR (400 MHz, CDCl$_3$) δ 9.19 (s, 1H), 8.36 (dd, 1H, J=8.2, 2.0 Hz), 7.74 (d, 1H, J=8.2 Hz), 7.32-7.21 (m, 1H), 6.94-6.85 (m, 2H), 4.99 (s, 2H), 3.51 (t, 4H, J=4.7 Hz), 3.24 (t, 4H, J=5.0 Hz); LRMS (ES) m/z 470.0 (M$^+$+1).

Example 317. Compound 21858: N-(4-(5-(difluoromethyl)-1,3,4-oxadiazol-2-yl)-2-fluorobenzyl)-N-(2,4-difluorophenyl)morpholine-4-carboxamide

[Step 1] Methyl 4-((N-(2,4-difluorophenyl)morpholine-4-carboxamido)methyl)-3-fluorobenzoate

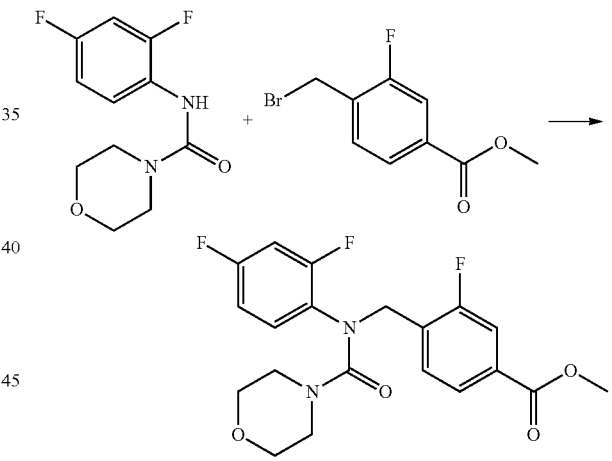

To a stirred solution of N-(2,4-difluorophenyl)morpholine-4-carboxamide (0.150 g, 0.619 mmol) in N,N-dimethylformamide (5 mL) was added at 0° C. sodium hydride (60.00%, 0.025 g, 0.619 mmol). The reaction mixture was stirred at the same temperature for 1 hr, added at the room temperature with methyl 4-(bromomethyl)-3-fluorobenzoate (0.153 g, 0.619 mmol), and stirred for additional 2 hr. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give methyl 4-((N-(2,4-difluorophenyl)morpholine-4-carboxamido)methyl)-3-fluorobenzoate as yellow oil (0.191 g, 75.5%).

[Step 2] N-(2,4-difluorophenyl)-N-(2-fluoro-4-(hydrazinecarbonyl)benzyl)morpholine-4-carboxamide

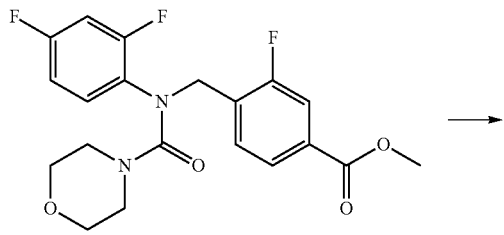

Methyl 4-((N-(2,4-difluorophenyl)morpholine-4-carboxamido)methyl)-3-fluorobenzoate (0.191 g, 0.468 mmol) and hydrazine monohydrate (0.227 mL, 4.677 mmol) were mixed at the room temperature in ethanol (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(2,4-difluorophenyl)-N-(2-fluoro-4-(hydrazinecarbonyl)benzyl)morpholine-4-carboxamide as yellow oil (0.186 g, 97.4%).

[Step 3] N-(4-(2-(2,2-difluoroacetyl)hydrazine-1-carbonyl)-2-fluorobenzyl)-N-(2,4-difluorophenyl)morpholine-4-carboxamide

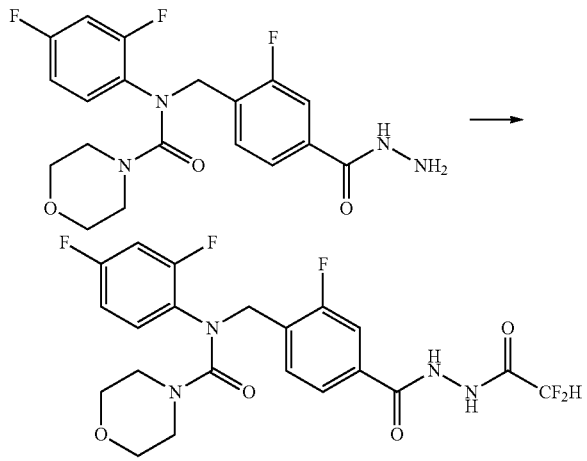

A solution of N-(2,4-difluorophenyl)-N-(2-fluoro-4-(hydrazinecarbonyl)benzyl)morpholine-4-carboxamide (0.093 g, 0.228 mmol) and triethylamine (0.063 mL, 0.455 mmol) in dichloromethane (2 mL) was mixed at the room temperature with 2,2-difluoroacetic anhydride (0.028 mL, 0.228 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification N-(4-(2-(2,2-difluoroacetyl)hydrazine-1-carbonyl)-2-fluorobenzyl)-N-(2,4-difluorophenyl)morpholine-4-carboxamide, 0.085 g, 76.7%, white foam).

[Step 4] Compound 21858

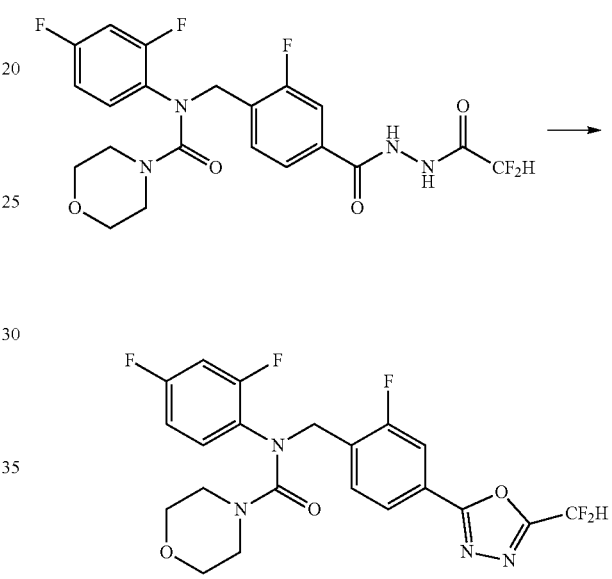

N-(4-(2-(2,2-difluoroacetyl)hydrazine-1-carbonyl)-2-fluorobenzyl)-N-(2,4-difluorophenyl)morpholine-4-carboxamide (0.085 g, 0.175 mmol), and 1-methoxy-N-triethylammoniosulfonyl-methanimidate (Burgess reagent, 0.062 g, 0.262 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(2,4-difluorophenyl)morpholine-4-carboxamide as yellow foam (0.050 g, 61.6%).
$^1$H NMR (400 MHz, CDCl$_3$) δ 7.89 (d, 1H, J=8.1 Hz), 7.85-7.77 (m, 1H), 7.71 (d, 1H, J=10.0 Hz), 7.14-7.03 (m, 1H), 6.95-6.77 (m, 3H), 4.87 (s, 2H), 3.48 (t, 4H, J=4.7 Hz), 3.22 (t, 4H, J=4.7 Hz); LRMS (ES) m/z 469.0 (M$^+$+1).

Example 318. Compound 21859: N-(2,4-difluorophenyl)-N-(2-fluoro-4-(5-(trifluoromethyl)-1,3,4-oxadiazol-2-yl)benzyl)morpholine-4-carboxamide

[Step 1] (N-(2,4-difluorophenyl)-N-(2-fluoro-4-(2-(2,2,2-trifluoroacetyl)hydrazine-1-carbonyl) benzyl)morpholine-4-carboxamide

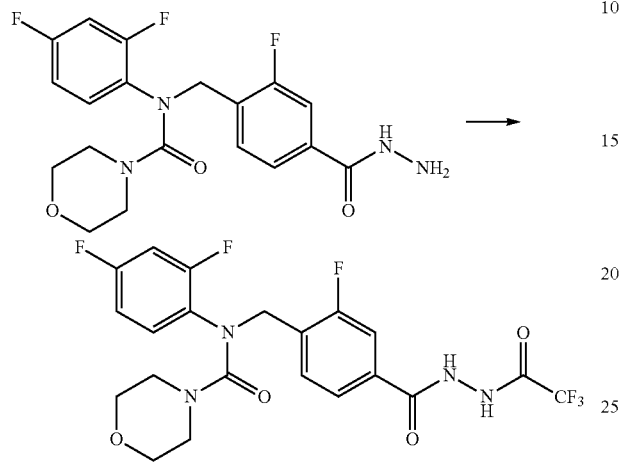

A solution of N-(2,4-difluorophenyl)-N-(2-fluoro-4-(hydrazinecarbonyl)benzyl)morpholine-4-carboxamide (0.093 g, 0.228 mmol) and triethylamine (0.063 mL, 0.455 mmol) in dichloromethane (2 mL) was mixed at the room temperature with trifluoroacetic anhydride (0.032 mL, 0.228 mmol). The reaction mixture was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification N-(2,4-difluorophenyl)-N-(2-fluoro-4-(2-(2,2,2-trifluoroacetyl)hydrazine-1-carbonyl) benzyl)morpholine-4-carboxamide, 0.088 g, 76.6%, white foam).

[Step 2] Compound 21859

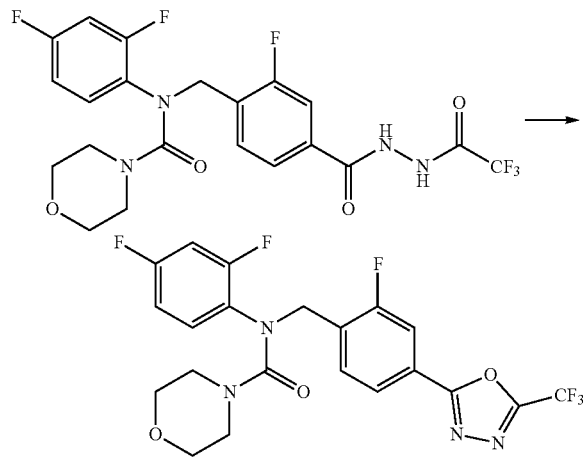

N-(2,4-difluorophenyl)-N-(2-fluoro-4-(2-(2,2,2-trifluoroacetyl)hydrazine-1-carbonyl) benzyl)morpholine-4-carboxamide (0.088 g, 0.174 mmol) and 1-methoxy-N-triethylammoniosulfonyl-methanimidate (Burgess reagent, 0.062 g, 0.262 mmol) were mixed at the room temperature in tetrahydrofuran (2 mL) and then stirred at 100° C. for 18 hr and cooled down to the room temperature to terminate the reaction. The reaction mixture was concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The residue was chromatographed (SiO$_2$, 4 g cartridge; methanol/dichloromethane=0% to 5%) to give N-(2,4-difluorophenyl)-N-(2-fluoro-4-(5-(trifluoromethyl)-1,3,4-oxadiazol-2-yl)benzyl)morpholine-4-carboxamide as yellow foam (0.022 g, 26.0%).

$^1$H NMR (400 MHz, CDCl$_3$) δ 7.92-7.80 (m, 2H), 7.71 (d, 1H, J=9.9 Hz), 7.09 (td, 1H, J=8.6, 5.6 Hz), 6.95-6.82 (m, 2H), 4.88 (s, 2H), 3.49 (t, 4H, J=4.7 Hz), 3.22 (t, 4H, J=4.7 Hz); LRMS (ES) m/z 487.0 (M$^+$+1).

Example 319. Compound 21860: N-(3-Chlorophenyl)-4-ethyl-N-(4-(5-(trifluoromethyl)-1,3,4-oxadiazol-2-yl)benzyl)piperazine-1-carboxamide

[Step 1] N-(3-Chlorophenyl)-4-ethylpiperazine-1-carboxamide

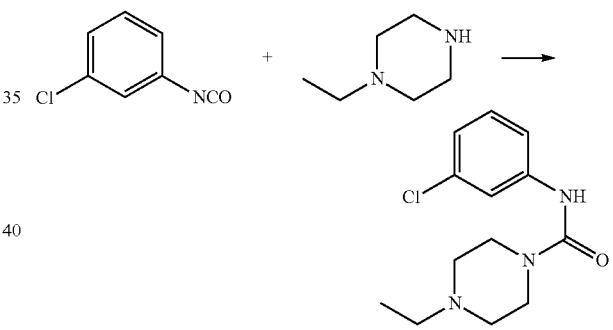

A solution of 1-chloro-3-isocyanatobenzene (0.488 mL, 4.000 mmol) and 1-ethylpiperazine (0.457 g, 4.000 mmol) in diethylether (8 mL) was stirred at the room temperature for 5 hr, and concentrated under the reduced pressure. The crude product was used without further purification (N-(3-chlorophenyl)-4-ethylpiperazine-1-carboxamide, 1.070 g, 99.9%, white solid).

[Step 2] Methyl 4-((N-(3-chlorophenyl)-4-ethylpiperazine-1-carboxamido)methyl)benzoate

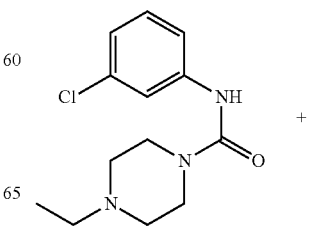

997

-continued

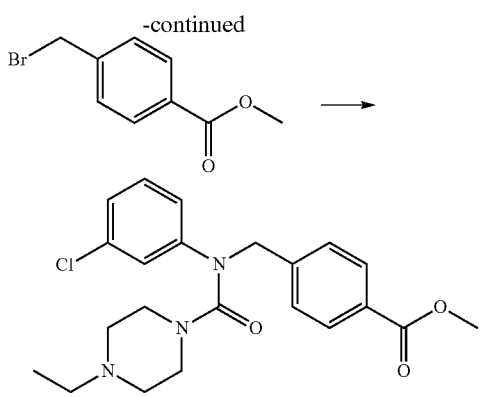

A solution of N-(3-chlorophenyl)-4-ethylpiperazine-1-carboxamide (0.356 g, 1.330 mmol) and sodium hydride (60.00%, 0.058 g, 1.463 mmol) in tetrahydrofuran (6 mL) was stirred at the room temperature for 30 min, and mixed with methyl 4-(bromomethyl)benzoate (0.335 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (methyl 4-((N-(3-chlorophenyl)-4-ethylpiperazine-1-carboxamido)methyl)benzoate, 0.552 g, 99.8%, pale yellow oil).

[Step 3] N-(3-Chlorophenyl)-4-ethyl-N-(4-(hydrazinecarbonyl)benzyl)piperazine-1-carboxamide

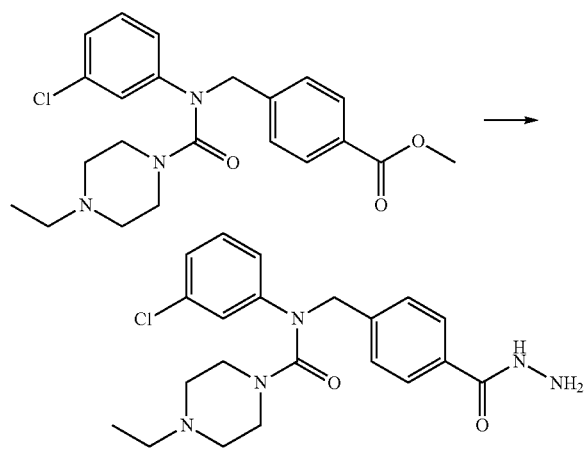

Methyl 4-((N-(3-chlorophenyl)-4-ethylpiperazine-1-carboxamido)methyl)benzoate (0.552 g, 1.327 mmol) and hydrazine monohydrate (1.290 mL, 26.544 mmol) were mixed at the room temperature in ethanol (6 mL) and then stirred at 70° C. for 18 hr and cooled down to the room temperature to terminate the reaction, concentrated under the reduced pressure. The residue was chromatographed (SiO$_2$, 24 g cartridge; methanol/dichloromethane=0% to 10%) to give N-(3-chlorophenyl)-4-ethyl-N-(4-(hydrazinecarbonyl)benzyl)piperazine-1-carboxamide as colorless oil (0.451 g, 81.8%).

998

[Step 4] N-(3-Chlorophenyl)-4-ethyl-N-(4-(2-(2,2,2-trifluoroacetyl)hydrazine-1-carbonyl)benzyl)piperazine-1-carboxamide

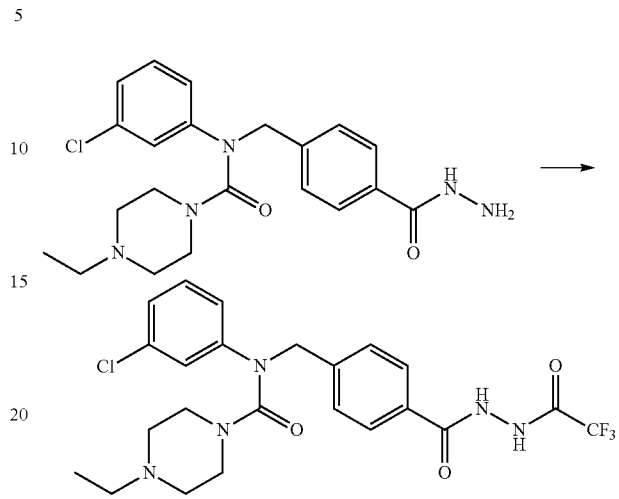

A solution of N-(3-chlorophenyl)-4-ethyl-N-(4-(hydrazinecarbonyl)benzyl)piperazine-1-carboxamide (0.226 g, 0.543 mmol), triethylamine (0.083 mL, 0.597 mmol) and trifluoroacetic anhydride (0.077 mL, 0.543 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(3-chlorophenyl)-4-ethyl-N-(4-(2-(2,2,2-trifluoroacetyl)hydrazine-1-carbonyl)benzyl)piperazine-1-carboxamide, 0.270 g, 97.2%, pale yellow oil).

[Step 5] Compound 21860

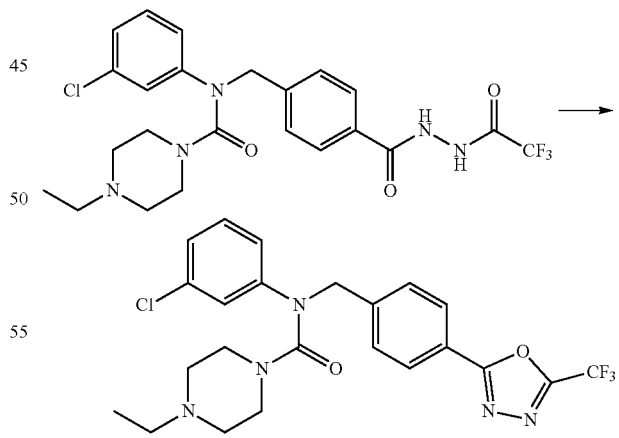

N-(3-Chlorophenyl)-4-ethyl-N-(4-(2-(2,2,2-trifluoroacetyl)hydrazine-1-carbonyl)benzyl)piperazine-1-carboxamide (0.270 g, 0.527 mmol) and 1-methoxy-N-triethylammoniosulfonyl-methanimidate (Burgess reagent, 0.189 g, 0.791 mmol) were mixed at the room temperature in tetrahydrofuran (4 mL) and then stirred at 70° C. for 18 hr and cooled down to the room temperature to terminate the reaction, concentrated under the reduced pressure. The residue was chromatographed (SiO$_2$, 4 g cartridge; methanol/dichloromethane=0% to 5%) to give N-(3-chlorophenyl)-4-ethyl-N-(4-(5-(trifluoromethyl)-1,3,4-oxadiazol-2-yl)benzyl)piperazine-1-carboxamide as pale yellow oil (0.049 g, 18.6%).

$^1$H NMR (400 MHz, CDCl$_3$) δ 8.08-8.03 (m, 2H), 7.50-7.46 (m, 2H), 7.26 (t, 1H, J=8.1 Hz), 7.15-7.12 (m, 1H), 7.10 (t, 1H, J=2.1 Hz), 6.95 (ddd, 1H, J=8.2, 2.2, 0.9 Hz), 4.94 (s, 2H), 3.54 (s, 4H), 2.69 (s, 6H), 1.36-1.20 (m, 3H); LRMS (ES) m/z 494.3 (M$^+$+1).

Example 320. Compound 21861: N-(3-Chlorophenyl)-4-ethyl-N-(2-fluoro-4-(5-(trifluoromethyl)-1,3,4-oxadiazol-2-yl)benzyl)piperazine-1-carboxamide

[Step 1] Methyl 4-((N-(3-chlorophenyl)-4-ethylpiperazine-1-carboxamido)methyl)-3-fluorobenzoate

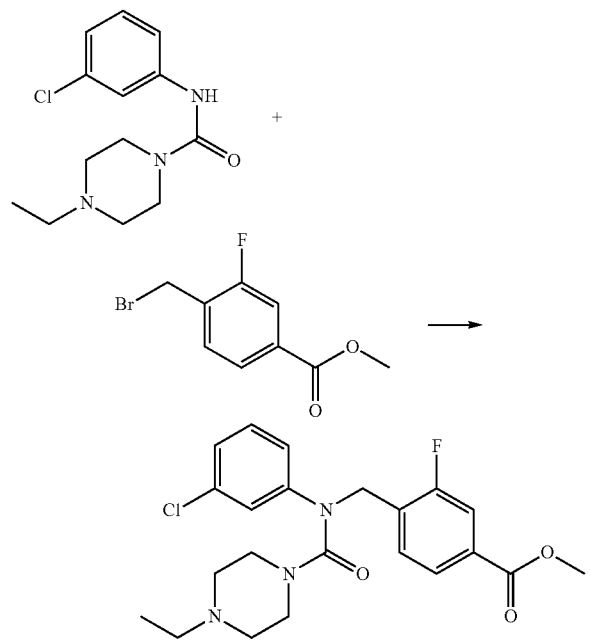

A solution of N-(3-chlorophenyl)-4-ethylpiperazine-1-carboxamide (0.356 g, 1.330 mmol) and sodium hydride (60.00%, 0.058 g, 1.463 mmol) in tetrahydrofuran (6 mL) was stirred at the room temperature for 30 min, and mixed with methyl 4-(bromomethyl)-3-fluorobenzoate (0.361 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (methyl 4-((N-(3-chlorophenyl)-4-ethylpiperazine-1-carboxamido)methyl)-3-fluorobenzoate, 0.570 g, 98.8%, pale yellow oil).

[Step 2] N-(3-Chlorophenyl)-4-ethyl-N-(2-fluoro-4-(hydrazinecarbonyl)benzyl)piperazine-1-carboxamide

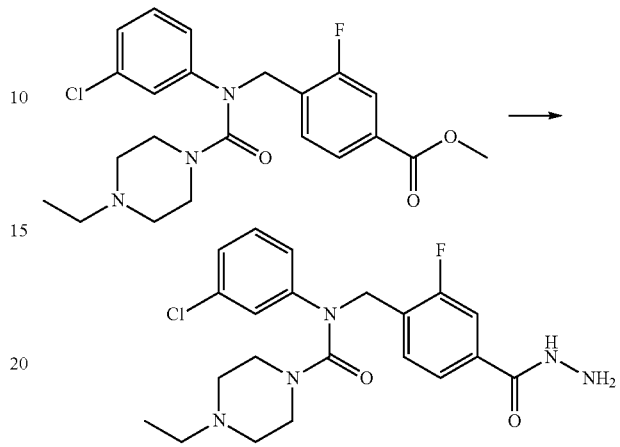

Methyl 4-((N-(3-chlorophenyl)-4-ethylpiperazine-1-carboxamido)methyl)-3-fluorobenzoate (0.570 g, 1.314 mmol) and hydrazine monohydrate (1.277 mL, 26.273 mmol) were mixed at the room temperature in ethanol (6 mL) and then stirred at 70° C. for 18 hr and cooled down to the room temperature to terminate the reaction, concentrated under the reduced pressure. The residue was chromatographed (SiO$_2$, 24 g cartridge; methanol/dichloromethane=0% to 10%) to give N-(3-chlorophenyl)-4-ethyl-N-(2-fluoro-4-(hydrazinecarbonyl)benzyl)piperazine-1-carboxamide as colorless oil (0.404 g, 70.9%).

[Step 3] N-(3-Chlorophenyl)-4-ethyl-N-(2-fluoro-4-(2-(2,2,2-trifluoroacetyl)hydrazine-1-carbonyl)benzyl)piperazine-1-carboxamide

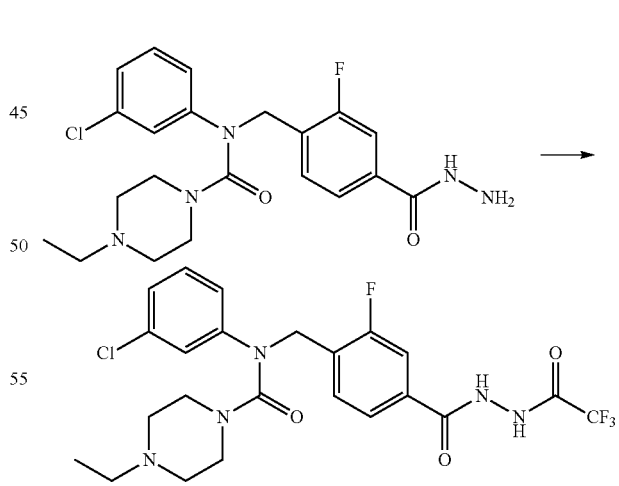

A solution of N-(3-chlorophenyl)-4-ethyl-N-(2-fluoro-4-(hydrazinecarbonyl)benzyl)piperazine-1-carboxamide (0.202 g, 0.466 mmol), triethylamine (0.071 mL, 0.512 mmol) and trifluoroacetic anhydride (0.066 mL, 0.466 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(3-chlorophenyl)-4-ethyl-N-(2-fluoro-4-(2-(2,2,2-trifluoroacetyl)hydrazine-1-carbonyl)benzyl)piperazine-1-carboxamide, 0.240 g, 97.3%, pale yellow oil).

[Step 4] Compound 21861

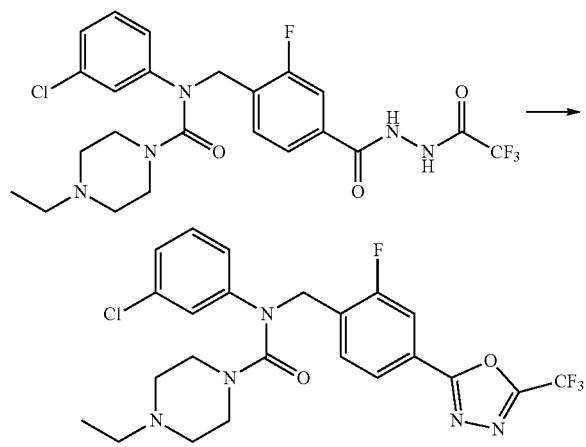

N-(3-Chlorophenyl)-4-ethyl-N-(2-fluoro-4-(2-(2,2,2-trifluoroacetyl)hydrazine-1-carbonyl)benzyl)piperazine-1-carboxamide (0.240 g, 0.453 mmol) and 1-methoxy-N-triethylammoniosulfonyl-methanimidate (Burgess reagent, 0.162 g, 0.679 mmol) were mixed at the room temperature in tetrahydrofuran (4 mL) and then stirred at 70° C. for 18 hr and cooled down to the room temperature to terminate the reaction, concentrated under the reduced pressure. The residue was chromatographed (SiO$_2$, 4 g cartridge; methanol/dichloromethane=0% to 5%) to give N-(3-chlorophenyl)-4-ethyl-N-(2-fluoro-4-(5-(trifluoromethyl)-1,3,4-oxadiazol-2-yl)benzyl)piperazine-1-carboxamide as pale yellow oil (0.076 g, 33.0%).

$^1$H NMR (400 MHz, CDCl$_3$) δ 7.89 (dd, 1H, J=8.0, 1.7 Hz), 7.78 (dd, 1H, J=10.0, 1.7 Hz), 7.69 (t, 1H, J=7.6 Hz), 7.28 (t, 1H, J=8.1 Hz), 7.20-7.12 (m, 2H), 7.00 (ddd, 1H, J=8.1, 2.2, 1.0 Hz), 4.97 (s, 2H), 3.53 (s, 4H), 2.91-2.33 (m, 6H), 1.35-1.16 (m, 3H); LRMS (ES) m/z 512.3 (M$^+$+1).

Example 321. Compound 21862: N-(4-Chlorophenyl)-4-ethyl-N-(4-(5-(trifluoromethyl)-1,3,4-oxadiazol-2-yl)benzyl)piperazine-1-carboxamide

[Step 1]
N-(4-Chlorophenyl)-4-ethylpiperazine-1-carboxamide

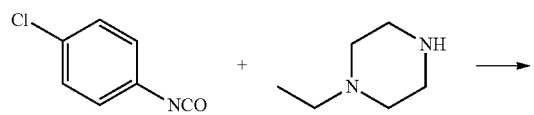

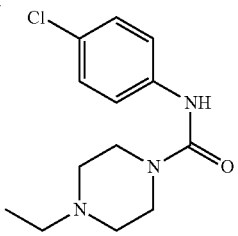

A solution of 1-chloro-4-isocyanatobenzene (0.614 g, 4.000 mmol) and 1-ethylpiperazine (0.457 g, 4.000 mmol) in diethylether (8 mL) was stirred at the room temperature for 5 hr, and concentrated under the reduced pressure. The crude product was used without further purification (N-(4-chlorophenyl)-4-ethylpiperazine-1-carboxamide, 1.070 g, 99.9%, white solid).

[Step 2] Methyl 4-((N-(4-chlorophenyl)-4-ethylpiperazine-1-carboxamido)methyl)benzoate

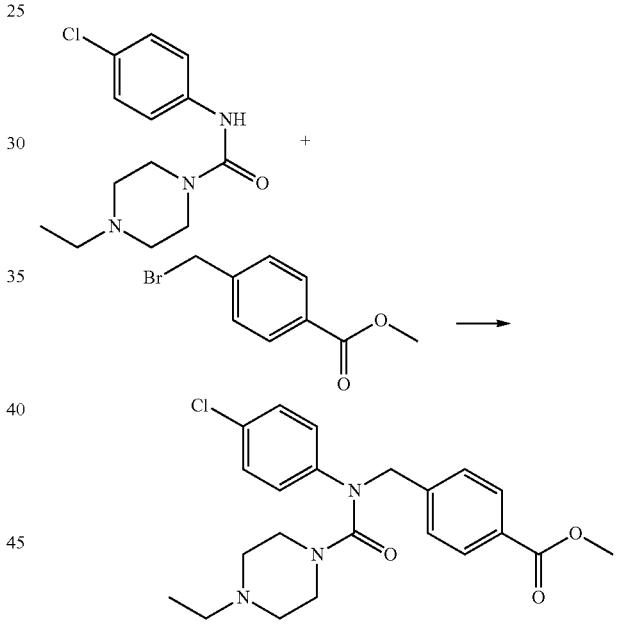

A solution of N-(4-chlorophenyl)-4-ethylpiperazine-1-carboxamide (0.356 g, 1.330 mmol) and sodium hydride (60.00%, 0.058 g, 1.463 mmol) in tetrahydrofuran (6 mL) was stirred at the room temperature for 30 min, and mixed with methyl 4-(bromomethyl)benzoate (0.335 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (methyl 4-((N-(4-chlorophenyl)-4-ethylpiperazine-1-carboxamido)methyl)benzoate, 0.552 g, 99.8%, pale yellow oil).

1003

[Step 3] N-(4-Chlorophenyl)-4-ethyl-N-(4-(hydrazinecarbonyl)benzyl)piperazine-1-carboxamide

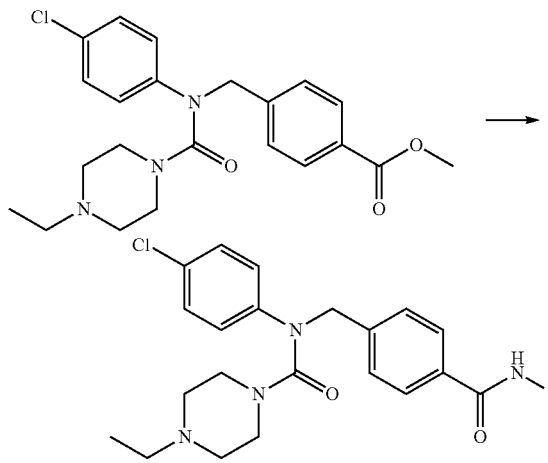

Methyl 4-((N-(4-chlorophenyl)-4-ethylpiperazine-1-carboxamido)methyl)benzoate (0.552 g, 1.327 mmol) and hydrazine monohydrate (1.290 mL, 26.544 mmol) were mixed at the room temperature in ethanol (6 mL) and then stirred at 70° C. for 18 hr and cooled down to the room temperature to terminate the reaction, concentrated under the reduced pressure. The residue was chromatographed (SiO₂, 24 g cartridge; methanol/dichloromethane=0% to 10%) to give N-(4-chlorophenyl)-4-ethyl-N-(4-(hydrazinecarbonyl)benzyl)piperazine-1-carboxamide as pale yellow oil (0.448 g, 81.1%).

[Step 4] N-(4-Chlorophenyl)-4-ethyl-N-(4-(2-(2,2,2-trifluoroacetyl)hydrazine-1-carbonyl)benzyl)piperazine-1-carboxamide

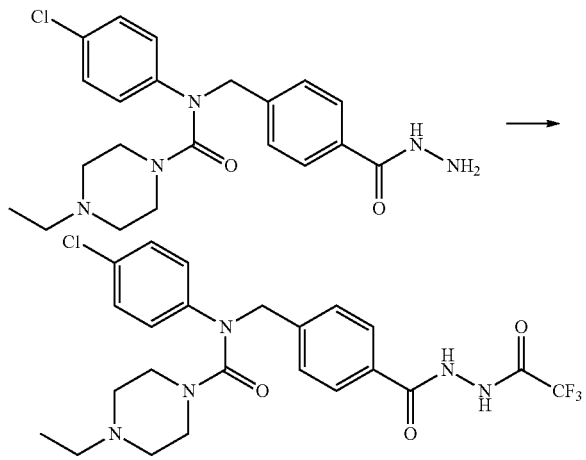

A solution of N-(4-chlorophenyl)-4-ethyl-N-(4-(hydrazinecarbonyl)benzyl)piperazine-1-carboxamide (0.224 g, 0.538 mmol), triethylamine (0.082 mL, 0.592 mmol) and trifluoroacetic anhydride (0.076 mL, 0.538 mmol) in dichloromethane (4 mL) was stirred at the room temperature for 18 hr. Then, water was added to the reaction mixture, followed by extraction with dichloromethane. The bi-phasic mixture

1004 was passed through a plastic frit to remove the solid residues and aqueous layer, and the organic layer collected was concentrated in vacuo. The crude product was used without further purification (N-(4-chlorophenyl)-4-ethyl-N-(4-(2-(2,2,2-trifluoroacetyl)hydrazine-1-carbonyl)benzyl)piperazine-1-carboxamide, 0.270 g, 98.0%, pale yellow oil).

[Step 5] Compound 21862

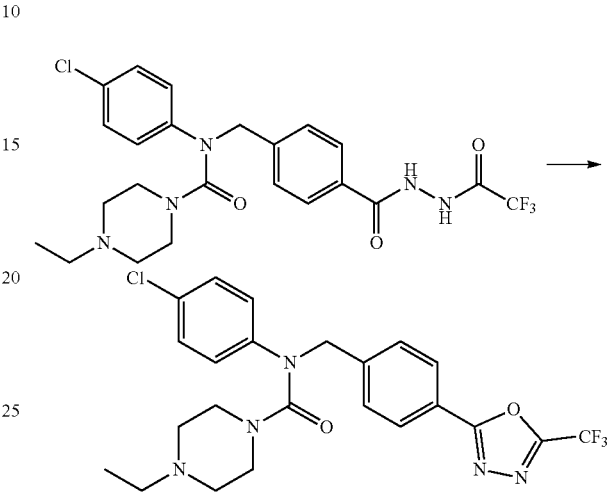

N-(4-Chlorophenyl)-4-ethyl-N-(4-(2-(2,2,2-trifluoroacetyl)hydrazine-1-carbonyl)benzyl)piperazine-1-carboxamide (0.270 g, 0.527 mmol) and 1-methoxy-N-triethylammoniosulfonyl-methanimidate (Burgess reagent, 0.189 g, 0.791 mmol) were mixed at the room temperature in tetrahydrofuran (4 mL) and then stirred at 70° C. for 18 hr and cooled down to the room temperature to terminate the reaction, concentrated under the reduced pressure. The residue was chromatographed (SiO₂, 4 g cartridge; methanol/dichloromethane=0% to 5%) to give N-(4-chlorophenyl)-4-ethyl-N-(4-(5-(trifluoromethyl)-1,3,4-oxadiazol-2-yl)benzyl)piperazine-1-carboxamide as pale yellow oil (0.029 g, 11.0%).

$^1$H NMR (400 MHz, CDCl₃) δ 8.06-8.01 (m, 2H), 7.49-7.45 (m, 2H), 7.32-7.26 (m, 2H), 7.02-6.96 (m, 2H), 4.92 (s, 2H), 3.48 (5, 4H), 2.65 (d, 6H, J=46.2 Hz), 1.22 (t, 3H, J=7.2 Hz); LRMS (ES) m/z 494.1 (M⁺+1).

Example 322. Compound 21863: N-(4-Chlorophenyl)-4-ethyl-N-(2-fluoro-4-(5-(trifluoromethyl)-1,3,4-oxadiazol-2-yl)benzyl)piperazine-1-carboxamide

[Step 1] Methyl 4-((N-(4-chlorophenyl)-4-ethylpiperazine-1-carboxamido)methyl)-3-fluorobenzoate

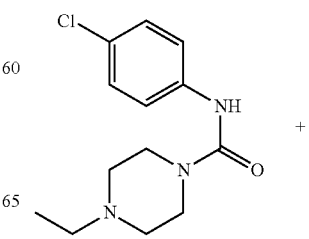 +

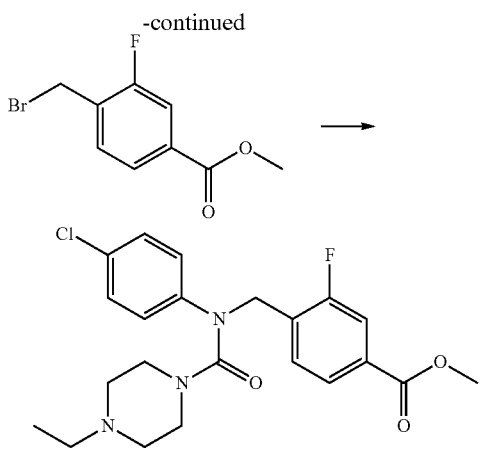

A solution of N-(4-chlorophenyl)-4-ethylpiperazine-1-carboxamide (0.356 g, 1.330 mmol) and sodium hydride (60.00%, 0.058 g, 1.463 mmol) in tetrahydrofuran (6 mL) was stirred at the room temperature for 30 min, and mixed with methyl 4-(bromomethyl)-3-fluorobenzoate (0.361 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (methyl 4-((N-(4-chlorophenyl)-4-ethylpiperazine-1-carboxamido)methyl)-3-fluorobenzoate, 0.570 g, 98.8%, pale yellow oil).

[Step 2] N-(4-Chlorophenyl)-4-ethyl-N-(2-fluoro-4-(hydrazinecarbonyl)benzyl)piperazine-1-carboxamide

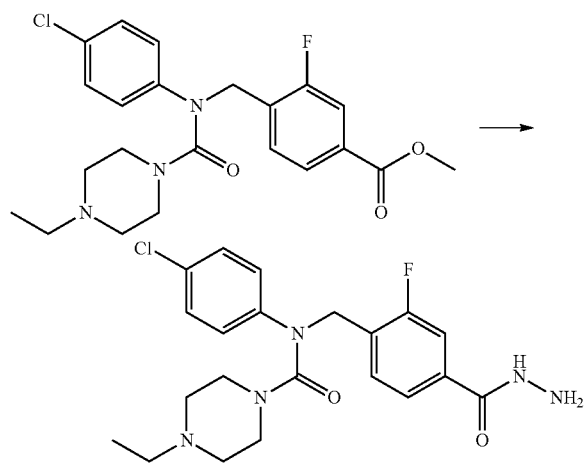

Methyl 4-((N-(4-chlorophenyl)-4-ethylpiperazine-1-carboxamido)methyl)-3-fluorobenzoate (0.570 g, 1.314 mmol) and hydrazine monohydrate (1.277 mL, 26.273 mmol) were mixed at the room temperature in ethanol (6 mL) and then stirred at 70° C. for 18 hr and cooled down to the room temperature to terminate the reaction, concentrated under the reduced pressure. The residue was chromatographed (SiO₂, 24 g cartridge; methanol/dichloromethane=0% to 10%) to give N-(4-chlorophenyl)-4-ethyl-N-(2-fluoro-4-(hydrazinecarbonyl)benzyl)piperazine-1-carboxamide as colorless oil (0.414 g, 72.7%).

[Step 3] N-(4-Chlorophenyl)-4-ethyl-N-(2-fluoro-4-(2-(2,2,2-trifluoroacetyl)hydrazine-1-carbonyl)benzyl)piperazine-1-carboxamide

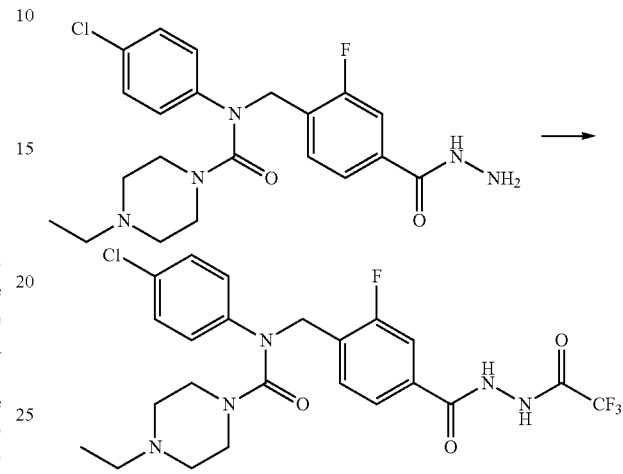

A solution of N-(4-chlorophenyl)-4-ethyl-N-(2-fluoro-4-(hydrazinecarbonyl)benzyl)piperazine-1-carboxamide (0.207 g, 0.477 mmol), triethylamine (0.073 mL, 0.525 mmol) and trifluoroacetic anhydride (0.067 mL, 0.477 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-chlorophenyl)-4-ethyl-N-(2-fluoro-4-(2-(2,2,2-trifluoroacetyl)hydrazine-1-carbonyl)benzyl)piperazine-1-carboxamide, 0.250 g, 98.8%, pale yellow oil).

[Step 4] Compound 21863

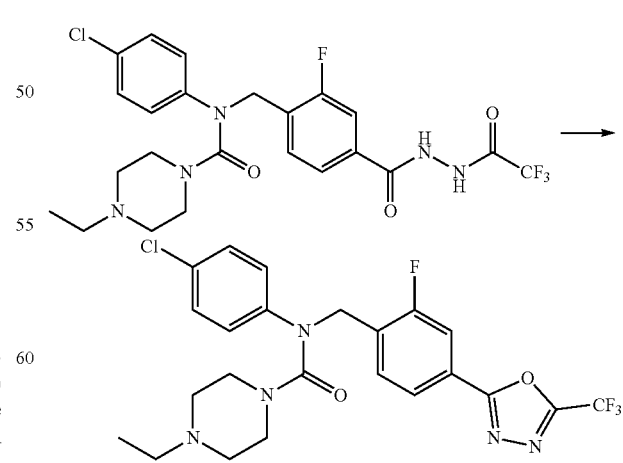

N-(4-Chlorophenyl)-4-ethyl-N-(2-fluoro-4-(2-(2,2,2-trifluoroacetyl)hydrazine-1-carbonyl)benzyl)piperazine-1-carboxamide (0.250 g, 0.472 mmol) and 1-methoxy-N-triethylammoniosulfonyl-methanimidate (Burgess reagent, 0.169 g, 0.708 mmol) were mixed at the room temperature in tetrahydrofuran (4 mL) and then stirred at 70° C. for 18 hr and cooled down to the room temperature to terminate the reaction, concentrated under the reduced pressure. The residue was chromatographed (SiO$_2$, 4 g cartridge; methanol/dichloromethane=0% to 5%) to give N-(4-chlorophenyl)-4-ethyl-N-(2-fluoro-4-(5-(trifluoromethyl)-1,3,4-oxadiazol-2-yl)benzyl)piperazine-1-carboxamide as pale yellow oil (0.032 g, 13.2%).

$^1$H NMR (400 MHz, CDCl$_3$) δ 7.87 (dd, 1H, J=8.0, 1.7 Hz), 7.76 (dd, 1H, J=9.9, 1.7 Hz), 7.70 (t, 1H, J=7.6 Hz), 7.32-7.28 (m, 2H), 7.06-7.02 (m, 2H), 4.96 (s, 2H), 3.45 (s, 4H), 2.72-2.34 (m, 6H), 1.19 (brs, 3H); LRMS (ES) m/z 512.0 (M$^+$+1).

Example 323. Compound 21864: N-(4-Chlorophenyl)-4-ethyl-N-((5-(5-(trifluoromethyl)-1,3,4-oxadiazol-2-yl)pyridin-2-yl) methyl)piperazine-1-carboxamide

[Step 1] Methyl 6-((N-(4-chlorophenyl)-4-ethylpiperazine-1-carboxamido)methyl)nicotinate

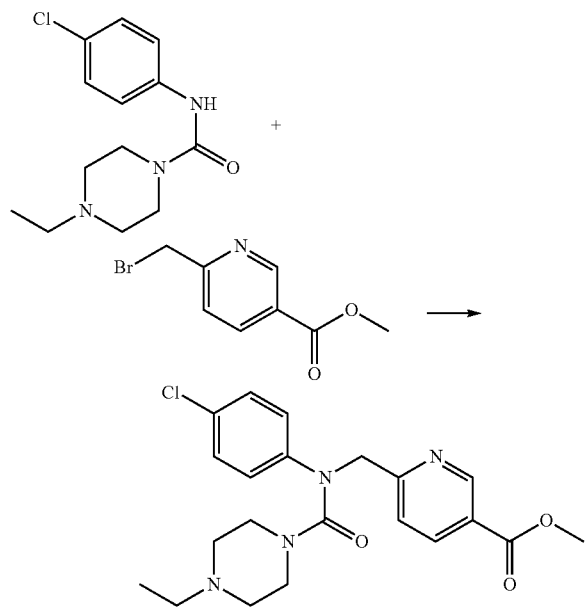

A solution of N-(4-chlorophenyl)-4-ethylpiperazine-1-carboxamide (0.356 g, 1.330 mmol) and sodium hydride (60.00%, 0.058 g, 1.463 mmol) in tetrahydrofuran (6 mL) was stirred at the room temperature for 30 min, and mixed with methyl 6-(bromomethyl)nicotinate (0.336 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (methyl 6-((N-(4-chlorophenyl)-4-ethylpiperazine-1-carboxamido) methyl)nicotinate, 0.550 g, 99.2%, brown oil).

[Step 2] N-(4-Chlorophenyl)-4-ethyl-N-((5-(hydrazinecarbonyl)pyridin-2-yl)methyl)piperazine-1-carboxamide

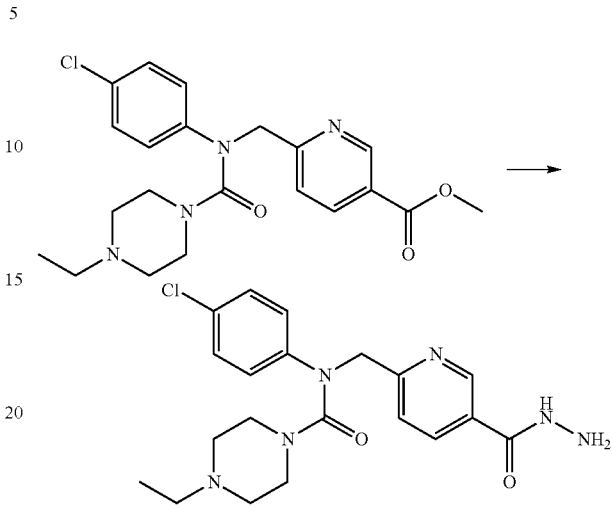

Methyl 6-((N-(4-chlorophenyl)-4-ethylpiperazine-1-carboxamido)methyl)nicotinate (0.550 g, 1.319 mmol) and hydrazine monohydrate (1.282 mL, 26.385 mmol) were mixed at the room temperature in ethanol (6 mL) and then stirred at 70° C. for 18 hr and cooled down to the room temperature to terminate the reaction, concentrated under the reduced pressure. The residue was chromatographed (SiO$_2$, 24 g cartridge; methanol/dichloromethane=0% to 10%) to give N-(4-chlorophenyl)-4-ethyl-N-((5-(hydrazinecarbonyl)pyridin-2-yl)methyl)piperazine-1-carboxamide as pale yellow oil (0.307 g, 55.8%).

[Step 3] N-(4-Chlorophenyl)-4-ethyl-N-((5-(2-(2,2,2-trifluoroacetyl)hydrazine-1-carbonyl)pyridin-2-yl) methyl)piperazine-1-carboxamide

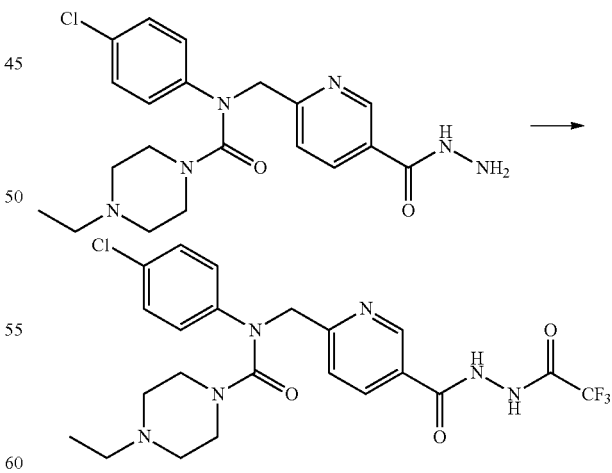

A solution of N-(4-chlorophenyl)-4-ethyl-N-((5-(hydrazinecarbonyl)pyridin-2-yl)methyl)piperazine-1-carboxamide (0.153 g, 0.367 mmol), triethylamine (0.056 mL, 0.404 mmol) and trifluoroacetic anhydride (0.052 mL, 0.367 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The crude product was used without further purification (N-(4-chlorophenyl)-4-ethyl-N-((5-(2-(2,2,2-trifluoroacetyl)hydrazine-1-carbonyl)pyridin-2-yl)methyl)piperazine-1-carboxamide, 0.180 g, 95.6%, pale yellow oil).

[Step 4] Compound 21864

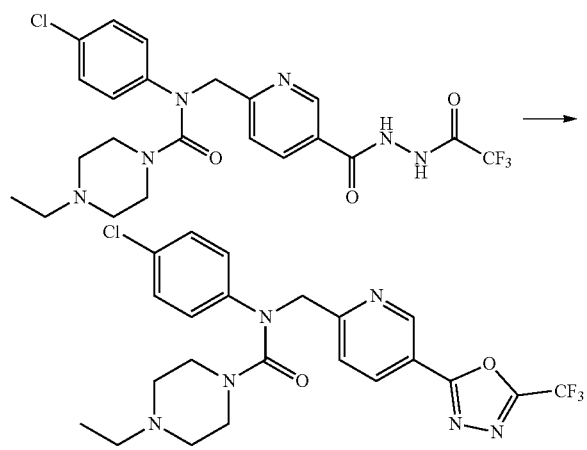

N-(4-Chlorophenyl)-4-ethyl-N-((5-(2-(2,2,2-trifluoroacetyl)hydrazine-1-carbonyl)pyridin-2-yl)methyl)piperazine-1-carboxamide (0.180 g, 0.351 mmol) and 1-methoxy-N-triethylammoniosulfonyl-methanimidate (Burgess reagent, 0.125 g, 0.526 mmol) were mixed at the room temperature in tetrahydrofuran (4 mL) and then stirred at 70° C. for 18 hr and cooled down to the room temperature to terminate the reaction, concentrated under the reduced pressure. The residue was chromatographed (SiO$_2$, 4 g cartridge; methanol/dichloromethane=0% to 5%) to give N-(4-chlorophenyl)-4-ethyl-N-((5-(5-(trifluoromethyl)-1,3,4-oxadiazol-2-yl)pyridin-2-yl) methyl)piperazine-1-carboxamide as pale yellow oil (0.060 g, 34.6%).

$^1$H NMR (400 MHz, CDCl$_3$) δ 9.24 (dd, 1H, J=2.2, 0.9 Hz), 8.36 (dd, 1H, J=8.2, 2.2 Hz), 7.60 (dd, 1H, J=8.2, 0.8 Hz), 7.32-7.26 (m, 2H), 7.15-7.08 (m, 2H), 5.10 (s, 2H), 3.51 (s, 4H), 2.68 (brs, 6H), 1.26-1.20 (m, 3H); LRMS (ES) m/z 495.0 (M$^+$+1).

Example 324. Compound 21865: 4-Ethyl-N-(3-fluorophenyl)-N-(4-(5-(trifluoromethyl)-1,3,4-oxadiazol-2-yl)benzyl)piperazine-1-carboxamide

[Step 1]
4-Ethyl-N-(3-fluorophenyl)piperazine-1-carboxamide

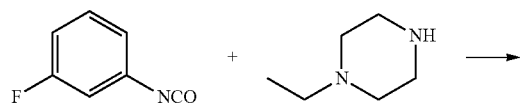

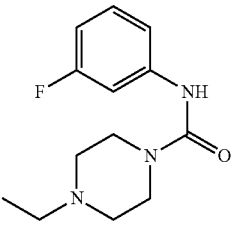

A solution of 1-fluoro-3-isocyanatobenzene (0.453 mL, 4.000 mmol) and 1-ethylpiperazine (0.457 g, 4.000 mmol) in diethylether (8 mL) prepared at the room temperature was stirred at the same temperature for 5 hr, and concentrated under the reduced pressure to remove the solvent. The title compound was used without further purification (4-ethyl-N-(3-fluorophenyl)piperazine-1-carboxamide, 1.000 g, 99.5%, white solid)

[Step 2] Methyl 4-((4-ethyl-N-(3-fluorophenyl)piperazine-1-carboxamido)methyl)benzoate

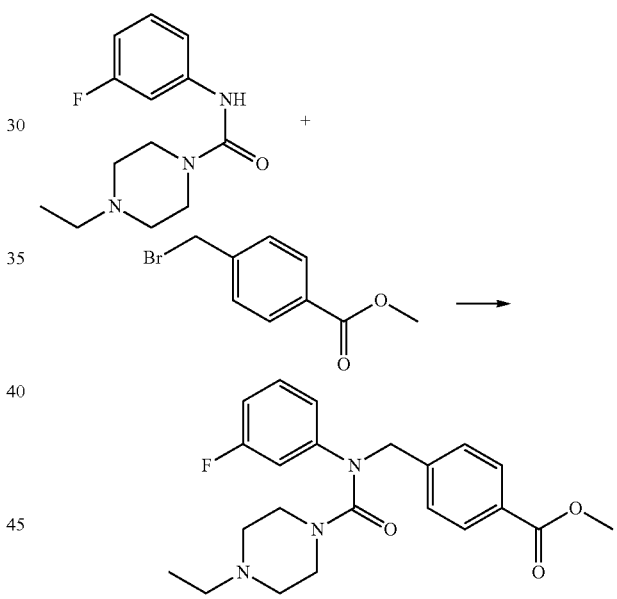

A solution of 4-ethyl-N-(3-fluorophenyl)piperazine-1-carboxamide (0.334 g, 1.330 mmol) and sodium hydride (60.00%, 0.059 g, 1.463 mmol) in tetrahydrofuran (6 mL) was stirred at the room temperature for 30 min, and mixed with methyl 4-(bromomethyl)benzoate (0.335 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((4-ethyl-N-(3-fluorophenyl)piperazine-1-carboxamido)methyl)benzoate, 0.530 g, 99.8%, pale yellow oil).

[Step 3] 4-Ethyl-N-(3-fluorophenyl)-N-(4-(hydrazinecarbonyl)benzyl)piperazine-1-carboxamide

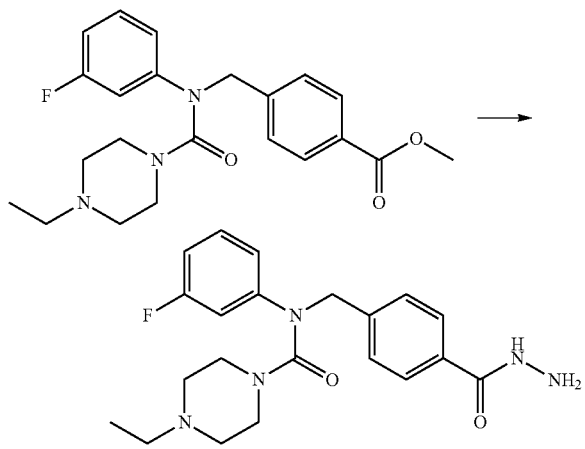

Methyl 4-((4-ethyl-N-(3-fluorophenyl)piperazine-1-carboxamido)methyl)benzoate (0.530 g, 1.327 mmol) and hydrazine monohydrate (1.290 mL, 26.535 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-(3-fluorophenyl)-N-(4-(hydrazinecarbonyl)benzyl)piperazine-1-carboxamide as pale yellow oil (0.347 g, 65.4%).

[Step 4] 4-Ethyl-N-(3-fluorophenyl)-N-(4-(2-(2,2,2-trifluoroacetyl)hydrazine-1-carbonyl)benzyl)piperazine-1-carboxamide

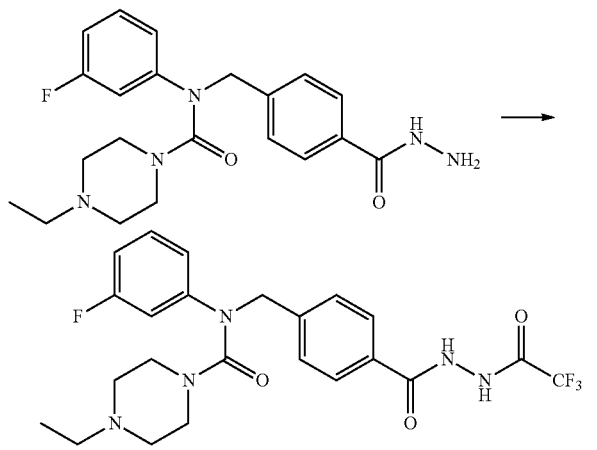

A solution of 4-ethyl-N-(3-fluorophenyl)-N-(4-(hydrazinecarbonyl)benzyl)piperazine-1-carboxamide (0.173 g, 0.433 mmol), triethylamine (0.066 mL, 0.476 mmol) and trifluoroacetic anhydride (0.061 mL, 0.433 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(3-fluorophenyl)-N-(4-(2-(2,2,2-trifluoroacetyl)hydrazine-1-carbonyl)benzyl)piperazine-1-carboxamide, 0.210 g, 97.9%, pale yellow oil).

[Step 5] Compound 21865

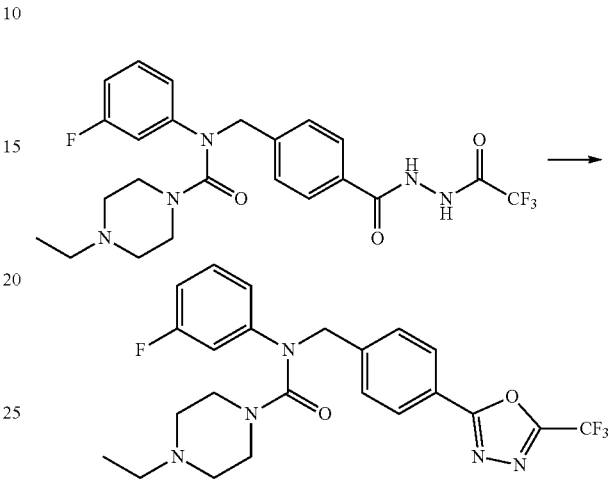

4-Ethyl-N-(3-fluorophenyl)-N-(4-(2-(2,2,2-trifluoroacetyl)hydrazine-1-carbonyl)benzyl)piperazine-1-carboxamide (0.210 g, 0.424 mmol) and 1-methoxy-N-triethylammoniosulfonyl-methanimidate (Burgess reagent, 0.151 g, 0.636 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(3-fluorophenyl)-N-(4-(5-(trifluoromethyl)-1,3,4-oxadiazol-2-yl)benzyl)piperazine-1-carboxamide as white solid (0.079 g, 39.2%).

$^1$H NMR (400 MHz, CDCl$_3$) δ 8.07-8.03 (m, 2H), 7.51-7.46 (m, 2H), 7.31-7.25 (m, 1H), 6.87-6.81 (m, 2H), 6.79 (dt, 1H, J=10.1, 2.3 Hz), 4.96 (s, 2H), 3.47 (s, 4H), 2.52 (brs, 6H), 1.23-1.14 (m, 3H); LRMS (ES) m/z 478.1 (M$^+$+1).

Example 325. Compound 21866: 4-Ethyl-N-(2-fluoro-4-(5-(trifluoromethyl)-1,3,4-oxadiazol-2-yl)benzyl)-N-(3-fluorophenyl)piperazine-1-carboxamide

[Step 1] Methyl 4-((4-ethyl-N-(3-fluorophenyl)piperazine-1-carboxamido)methyl)-3-fluorobenzoate

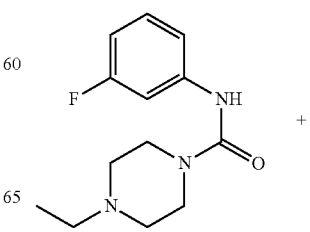 +

-continued

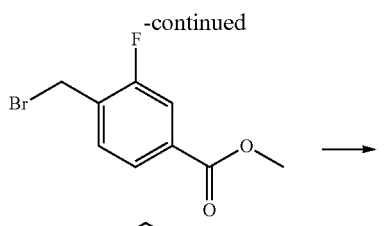

A solution of 4-ethyl-N-(3-fluorophenyl)piperazine-1-carboxamide (0.334 g, 1.330 mmol) and sodium hydride (60.00%, 0.059 g, 1.463 mmol) in tetrahydrofuran (6 mL) was stirred at the room temperature for 30 min, and mixed with methyl 4-(bromomethyl)-3-fluorobenzoate (0.361 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, to remove the solid residues and aqueous layer, and the organic layer collected was concentrated in vacuo. The title compound was used without further purification (methyl 4-((4-ethyl-N-(3-fluorophenyl)piperazine-1-carboxamido)methyl)-3-fluorobenzoate, 0.550 g, 99.1%, pale yellow oil).

[Step 2] 4-Ethyl-N-(2-fluoro-4-(hydrazinecarbonyl) benzyl)-N-(3-fluorophenyl)piperazine-1-carboxamide

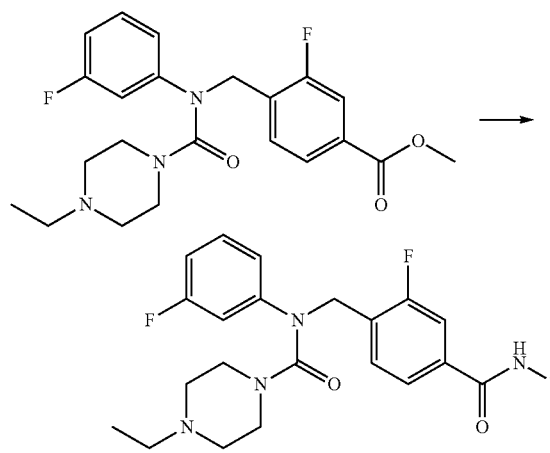

Methyl 4-((4-ethyl-N-(3-fluorophenyl)piperazine-1-carboxamido)methyl)-3-fluorobenzoate (0.530 g, 1.270 mmol) and hydrazine monohydrate (0.068 mL, 1.397 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-(2-fluoro-4-(hydrazinecarbonyl)benzyl)-N-(3-fluorophenyl)piperazine-1-carboxamide as pale yellow oil (0.356 g, 67.2%).

[Step 3] 4-Ethyl-N-(2-fluoro-4-(2-(2,2,2-trifluoroacetyl)hydrazine-1-carbonyl)benzyl)-N-(3-fluorophenyl)piperazine-1-carboxamide

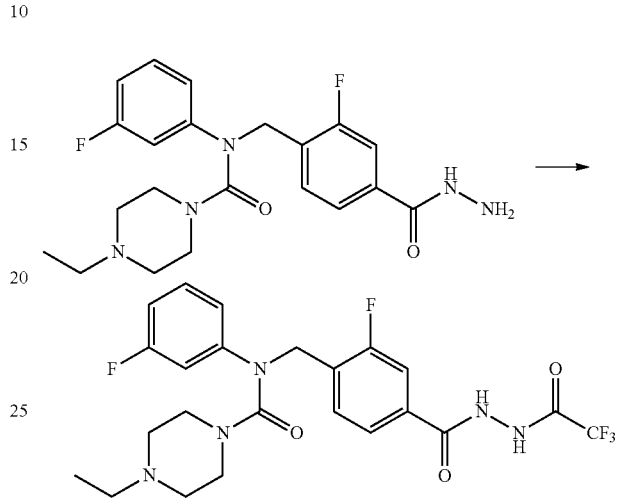

A solution of 4-ethyl-N-(2-fluoro-4-(hydrazinecarbonyl)benzyl)-N-(3-fluorophenyl)piperazine-1-carboxamide (0.178 g, 0.426 mmol), triethylamine (0.065 mL, 0.469 mmol) and trifluoroacetic anhydride (0.060 mL, 0.426 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(2-fluoro-4-(2-(2,2,2-trifluoroacetyl)hydrazine-1-carbonyl)benzyl)-N-(3-fluorophenyl)piperazine-1-carboxamide, 0.210 g, 95.9%, pale yellow oil).

[Step 4] Compound 21866

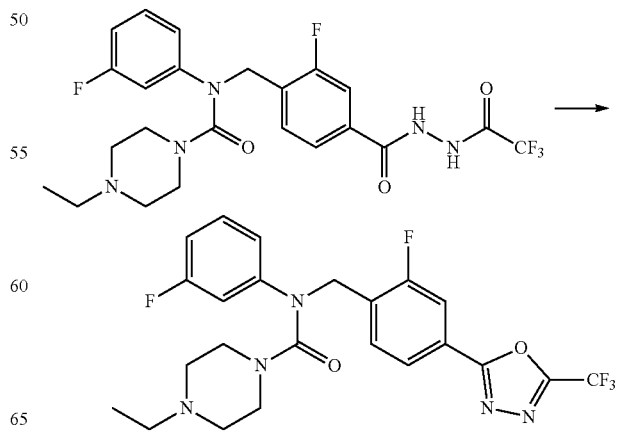

4-Ethyl-N-(2-fluoro-4-(2-(2,2,2-trifluoroacetyl)hydrazine-1-carbonyl)benzyl)-N-(3-fluorophenyl)piperazine-1-carboxamide (0.210 g, 0.409 mmol) and 1-methoxy-N-triethylammoniosulfonyl-methanimidate (Burgess reagent, 0.146 g, 0.613 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(2-fluoro-4-(5-(trifluoromethyl)-1,3,4-oxadiazol-2-yl)benzyl)-N-(3-fluorophenyl)piperazine-1-carboxamide as white solid (0.044 g, 21.9%).

$^1$H NMR (400 MHz, CDCl$_3$) δ 7.88 (dd, 1H, J=8.0, 1.7 Hz), 7.77 (dd, 1H, J=10.0, 1.7 Hz), 7.72-7.67 (m, 1H), 7.34-7.26 (m, 1H), 6.89 (ddd, 1H, J=8.1, 2.1, 1.0 Hz), 6.88-6.80 (m, 2H), 4.99 (s, 2H), 3.42 (s, 4H), 2.65-2.29 (m, 6H), 1.14 (s, 3H); LRMS (ES) m/z 496.1 (M$^+$+1).

Example 326. Compound 21867: 4-Ethyl-N-(3-fluorophenyl)-N-((5-(5-(trifluoromethyl)-1,3,4-oxadiazol-2-yl)pyridin-2-yl)methyl)piperazine-1-carboxamide

[Step 1] Methyl 6-((4-ethyl-N-(3-fluorophenyl)piperazine-1-carboxamido)methyl)nicotinate

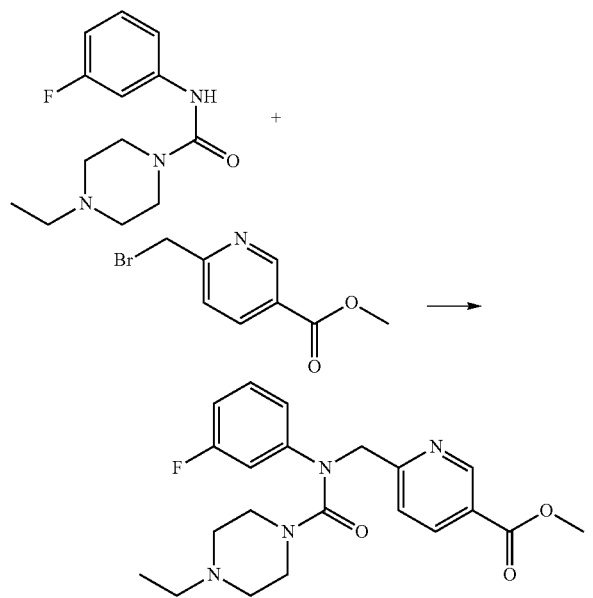

A solution of 4-ethyl-N-(3-fluorophenyl)piperazine-1-carboxamide (0.334 g, 1.330 mmol) and sodium hydride (60.00%, 0.059 g, 1.463 mmol) in tetrahydrofuran (6 mL) was stirred at the room temperature for 30 min, and mixed with methyl 6-(bromomethyl)nicotinate (0.337 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((4-ethyl-N-(3-fluorophenyl)piperazine-1-carboxamido)methyl)nicotinate, 0.530 g, 99.5%, brown oil).

[Step 2] 4-Ethyl-N-(3-fluorophenyl)-N-((5-(hydrazinecarbonyl)pyridin-2-yl)methyl)piperazine-1-carboxamide

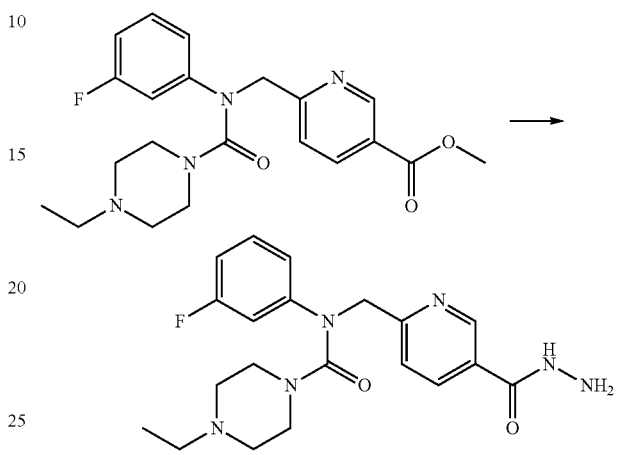

Methyl 6-((4-ethyl-N-(3-fluorophenyl)piperazine-1-carboxamido)methyl)nicotinate (0.530 g, 1.324 mmol) and hydrazine monohydrate (1.287 mL, 26.470 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-(3-fluorophenyl)-N-((5-(hydrazinecarbonyl)pyridin-2-yl)methyl)piperazine-1-carboxamide as pale yellow oil (0.310 g, 58.5%).

[Step 3] 4-Ethyl-N-(3-fluorophenyl)-N-((5-(2-(2,2,2-trifluoroacetyl)hydrazine-1-carbonyl)pyridin-2-yl)methyl)piperazine-1-carboxamide

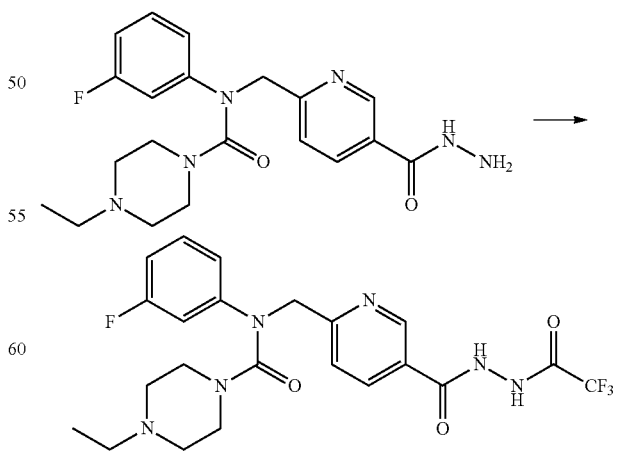

A solution of 4-ethyl-N-(3-fluorophenyl)-N-((5-(hydrazinecarbonyl)pyridin-2-yl)methyl)piperazine-1-carboxamide (0.155 g, 0.387 mmol), triethylamine (0.059 mL, 0.426 mmol) and trifluoroacetic anhydride (0.055 mL, 0.387 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(3-fluorophenyl)-N-((5-(2-(2,2,2-trifluoroacetyl)hydrazine-1-carbonyl)pyridin-2-yl)methyl)piperazine-1-carboxamide, 0.190 g, 98.9%, pale yellow oil).

[Step 4] Compound 21867

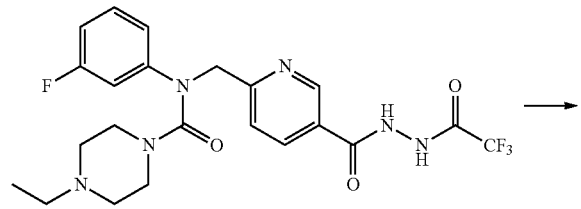

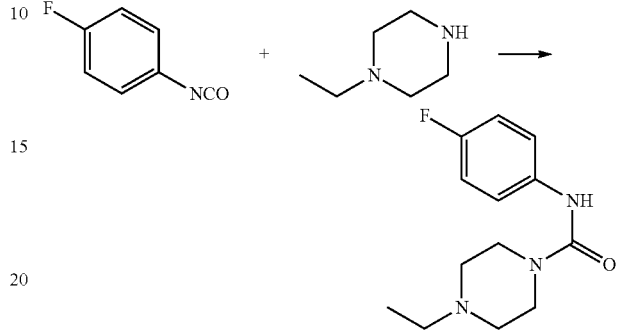

4-Ethyl-N-(3-fluorophenyl)-N-((5-(2-(2,2,2-trifluoroacetyl)hydrazine-1-carbonyl)pyridin-2-yl)methyl)piperazine-1-carboxamide (0.190 g, 0.383 mmol) and 1-methoxy-N-triethylammoniosulfonyl-methanimidate (Burgess reagent, 0.137 g, 0.574 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(3-fluorophenyl)-N-((5-(5-(trifluoromethyl)-1,3,4-oxadiazol-2-yl)pyridin-2-yl)methyl)piperazine-1-carboxamide as white solid (0.067 g, 36.7%).

$^1$H NMR (400 MHz, CDCl$_3$) δ 9.25 (dd, 1H, J=2.3, 0.9 Hz), 8.36 (dd, 1H, J=8.2, 2.2 Hz), 7.60 (dd, 1H, J=8.2, 0.9 Hz), 7.31-7.25 (m, 1H), 6.94 (ddd, 1H, J=8.1, 2.1, 0.9 Hz), 6.90 (dt, 1H, J=10.3, 2.3 Hz), 6.85-6.79 (m, 1H), 5.13 (s, 2H), 3.46 (s, 4H), 2.55 (s, 6H), 1.23-1.11 (m, 3H); LRMS (ES) m/z 479.1 (M$^+$+1).

Example 327. Compound 21868: 4-Ethyl-N-(4-fluorophenyl)-N-(4-(5-(trifluoromethyl)-1,3,4-oxadiazol-2-yl)benzyl)piperazine-1-carboxamide

[Step 1]
4-Ethyl-N-(4-fluorophenyl)piperazine-1-carboxamide

A solution of 1-fluoro-4-isocyanatobenzene (0.450 mL, 4.000 mmol) and 1-ethylpiperazine (0.457 g, 4.000 mmol) in diethylether (8 mL) was stirred at the room temperature for 5 hr. The reaction mixture was concentrated under the reduced pressure to remove the solvent The title compound was used without further purification (4-ethyl-N-(4-fluorophenyl)piperazine-1-carboxamide, 1.000 g, 99.5%, white solid).

[Step 2] Methyl 4-((4-ethyl-N-(4-fluorophenyl)piperazine-1-carboxamido)methyl)benzoate

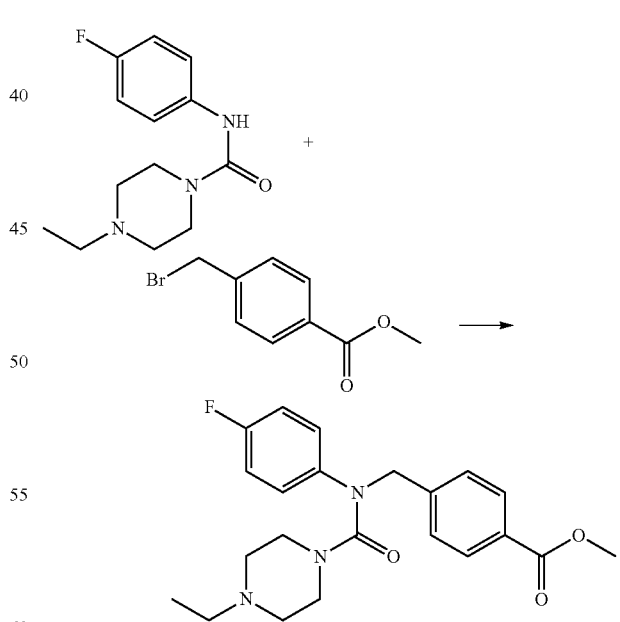

A solution of 4-ethyl-N-(4-fluorophenyl)piperazine-1-carboxamide (0.334 g, 1.330 mmol) and sodium hydride (60.00%, 0.059 g, 1.463 mmol) in tetrahydrofuran (6 mL) was stirred at the room temperature for 30 min, and mixed with methyl 4-(bromomethyl)benzoate (0.335 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((4-ethyl-N-(4-fluorophenyl)piperazine-1-carboxamido)methyl)benzoate, 0.530 g, 99.8%, pale yellow oil).

[Step 3] 4-Ethyl-N-(4-fluorophenyl)-N-(4-(hydrazinecarbonyl)benzyl)piperazine-1-carboxamide

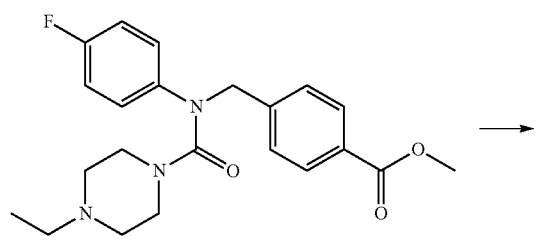

Methyl 4-((4-ethyl-N-(4-fluorophenyl)piperazine-1-carboxamido)methyl)benzoate (0.530 g, 1.327 mmol) and hydrazine monohydrate (1.290 mL, 26.535 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-(4-fluorophenyl)-N-(4-(hydrazinecarbonyl)benzyl)piperazine-1-carboxamide as colorless oil (0.375 g, 70.7%).

[Step 4] 4-Ethyl-N-(4-fluorophenyl)-N-(4-(2-(2,2,2-trifluoroacetyl)hydrazine-1-carbonyl)benzyl)piperazine-1-carboxamide

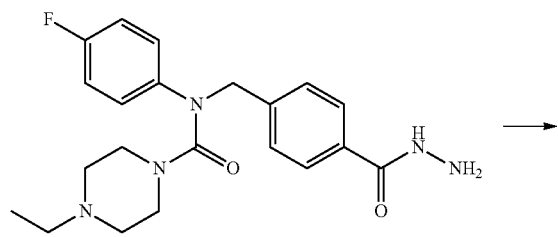

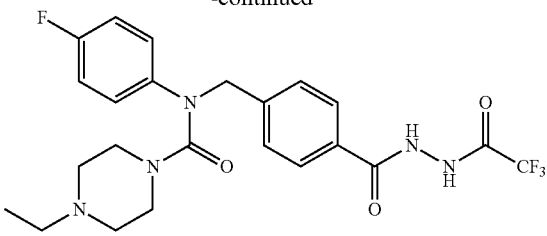

A solution of 4-ethyl-N-(4-fluorophenyl)-N-(4-(hydrazinecarbonyl)benzyl)piperazine-1-carboxamide (0.187 g, 0.468 mmol), triethylamine (0.072 mL, 0.515 mmol) and trifluoroacetic anhydride (0.066 mL, 0.468 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(4-fluorophenyl)-N-(4-(2-(2,2,2-trifluoroacetyl)hydrazine-1-carbonyl)benzyl)piperazine-1-carboxamide, 0.230 g, 99.2%, pale yellow oil).

[Step 5] Compound 21868

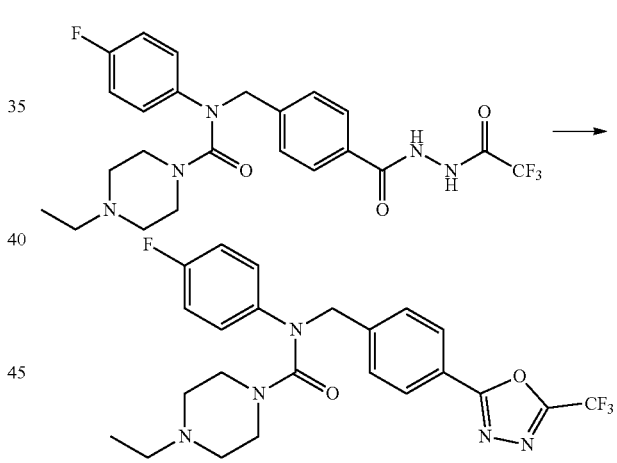

4-Ethyl-N-(4-fluorophenyl)-N-(4-(2-(2,2,2-trifluoroacetyl)hydrazine-1-carbonyl)benzyl)piperazine-1-carboxamide (0.230 g, 0.464 mmol) and 1-methoxy-N-triethylammoniosulfonyl-methanimidate (Burgess reagent, 0.166 g, 0.696 mmol) were mixed at the room temperature in tetrahydrofuran (4 mL) and then stirred at 70° C. for 18 hr, and cooled down to the room temperature to terminate the reaction. The reaction mixture was concentrated under the reduced pressure to remove the solvent The concentrate was purified and concentrated by column chromatography (SiO$_2$, 4 g cartridge; methanol/dichloromethane=0% to 5%) to give 4-ethyl-N-(4-fluorophenyl)-N-(4-(5-(trifluoromethyl)-1,3,4-oxadiazol-2-yl)benzyl)piperazine-1-carboxamide as pale yellow oil (0.050 g, 22.3%).

$^1$H NMR (400 MHz, CDCl$_3$) δ 8.06-8.01 (m, 2H), 7.48-7.44 (m, 2H), 7.06-6.99 (m, 4H), 4.90 (s, 2H), 3.49 (s, 4H), 2.66 (brs, 6H), 1.23 (brs, 3H).

Example 328. Compound 21869: 4-Ethyl-N-(2-fluoro-4-(5-(trifluoromethyl)-1,3,4-oxadiazol-2-yl)benzyl)-N-(4-fluorophenyl)piperazine-1-carboxamide

[Step 1] Methyl 4-((4-ethyl-N-(4-fluorophenyl)piperazine-1-carboxamido)methyl)-3-fluorobenzoate

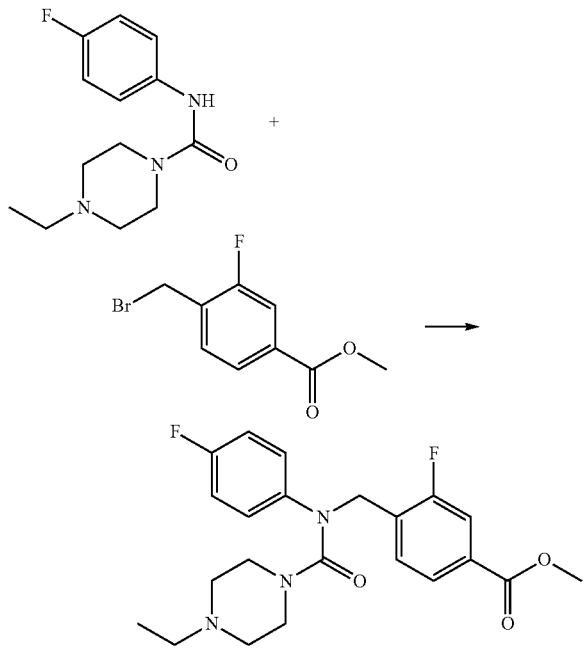

A solution of 4-ethyl-N-(4-fluorophenyl)piperazine-1-carboxamide (0.334 g, 1.330 mmol) and sodium hydride (60.00%, 0.059 g, 1.463 mmol) in tetrahydrofuran (6 mL) was stirred at the room temperature for 30 min, and mixed with methyl 4-(bromomethyl)-3-fluorobenzoate (0.361 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((4-ethyl-N-(4-fluorophenyl)piperazine-1-carboxamido)methyl)-3-fluorobenzoate, 0.550 g, 99.1%, pale yellow oil).

[Step 2] 4-Ethyl-N-(2-fluoro-4-(hydrazinecarbonyl)benzyl)-N-(4-fluorophenyl)piperazine-1-carboxamide

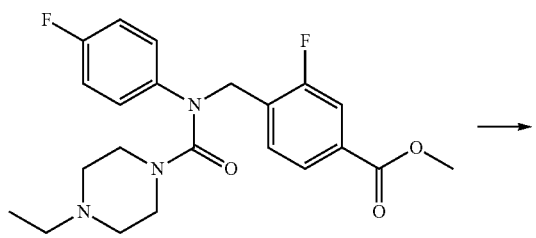

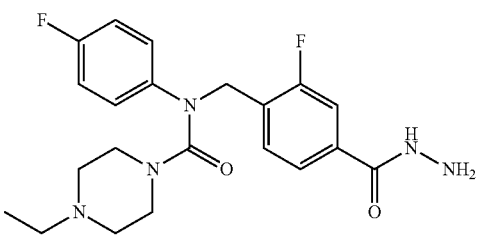

Methyl 4-((4-ethyl-N-(4-fluorophenyl)piperazine-1-carboxamido)methyl)-3-fluorobenzoate (0.550 g, 1.317 mmol) and hydrazine monohydrate (1.281 mL, 26.350 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-(2-fluoro-4-(hydrazinecarbonyl)benzyl)-N-(4-fluorophenyl)piperazine-1-carboxamide as colorless oil (0.423 g, 76.8%).

[Step 3] 4-Ethyl-N-(2-fluoro-4-(2-(2,2,2-trifluoroacetyl)hydrazine-1-carbonyl)benzyl)-N-(4-fluorophenyl)piperazine-1-carboxamide

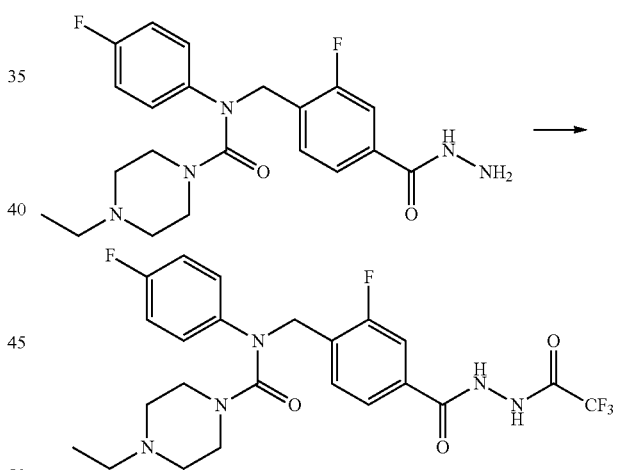

A solution of 4-ethyl-N-(2-fluoro-4-(hydrazinecarbonyl)benzyl)-N-(4-fluorophenyl)piperazine-1-carboxamide (0.211 g, 0.505 mmol), triethylamine (0.077 mL, 0.556 mmol) and trifluoroacetic anhydride (0.071 mL, 0.505 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(2-fluoro-4-(2-(2,2,2-trifluoroacetyl)hydrazine-1-carbonyl)benzyl)-N-(4-fluorophenyl)piperazine-1-carboxamide, 0.250 g, 96.3%, pale yellow solid).

[Step 4] Compound 21869

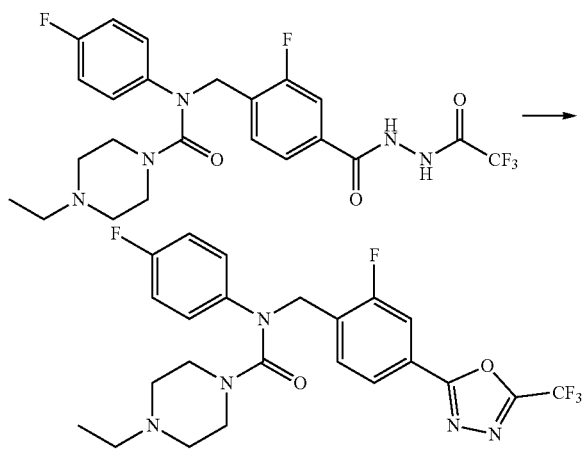

4-Ethyl-N-(2-fluoro-4-(2-(2,2,2-trifluoroacetyl)hydrazine-1-carbonyl)benzyl)-N-(4-fluorophenyl)piperazine-1-carboxamide (0.250 g, 0.487 mmol) and 1-methoxy-N-triethylammoniosulfonyl-methanimidate (Burgess reagent, 0.174 g, 0.730 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(2-fluoro-4-(5-(trifluoromethyl)-1,3,4-oxadiazol-2-yl)benzyl)-N-(4-fluorophenyl)piperazine-1-carboxamide as pale yellow oil (0.063 g, 26.3%).

$^1$H NMR (400 MHz, CDCl$_3$) δ 7.87 (dd, 1H, J=8.0, 1.7 Hz), 7.77-7.70 (m, 2H), 7.10-7.04 (m, 2H), 7.06-6.99 (m, 2H), 4.93 (s, 2H), 3.38 (s, 4H), 2.64-2.23 (m, 6H), 1.13 (t, 3H, J=7.2 Hz).

Example 329. Compound 21870: 4-Ethyl-N-(4-fluorophenyl)-N-((5-(5-(trifluoromethyl)-1,3,4-oxadiazol-2-yl)pyridin-2-yl)methyl)piperazine-1-carboxamide

[Step 1] Methyl 6-((4-ethyl-N-(4-fluorophenyl)piperazine-1-carboxamido)methyl)nicotinate

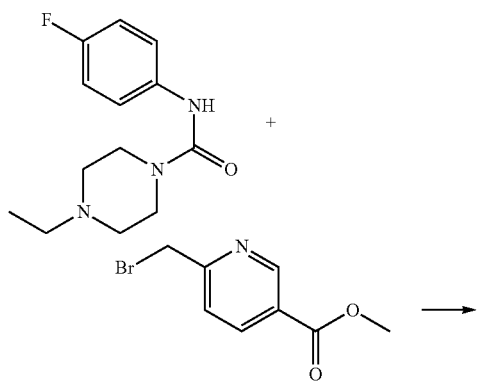

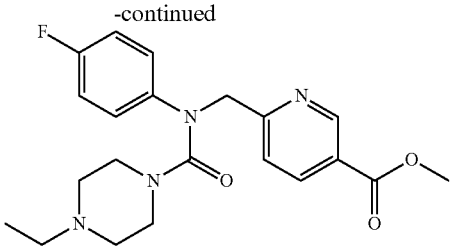

A solution of 4-ethyl-N-(4-fluorophenyl)piperazine-1-carboxamide (0.334 g, 1.330 mmol) and sodium hydride (60.00%, 0.059 g, 1.463 mmol) in tetrahydrofuran (6 mL) was stirred at the room temperature for 30 min, and mixed with methyl 6-(bromomethyl)nicotinate (0.337 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((4-ethyl-N-(4-fluorophenyl)piperazine-1-carboxamido)methyl)nicotinate, 0.530 g, 99.5%, brown oil).

[Step 2] 4-Ethyl-N-(4-fluorophenyl)-N-((5-(hydrazinecarbonyl)pyridin-2-yl)methyl)piperazine-1-carboxamide

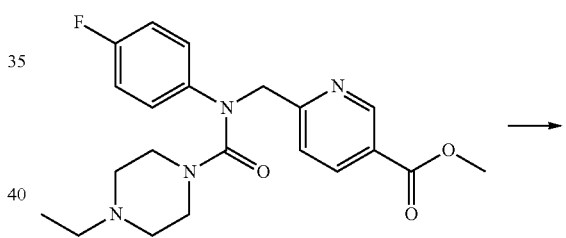

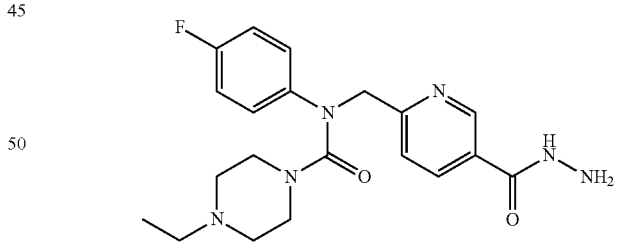

Methyl 6-((4-ethyl-N-(4-fluorophenyl)piperazine-1-carboxamido)methyl)nicotinate (0.530 g, 1.324 mmol) and hydrazine monohydrate (1.287 mL, 26.470 mmol) were mixed at the room temperature in ethanol (6 mL) and then stirred at 70° C. for 18 hr, cooled down to the room temperature to terminate the reaction and concentrated under the reduced pressure to remove the solvent. The concentrate was purified and concentrated by column chromatography (SiO$_2$, 24 g cartridge; methanol/dichloromethane=0% to 10%) to give 4-ethyl-N-(4-fluorophenyl)-N-((5-(hydrazinecarbonyl)pyridin-2-yl)methyl)piperazine-1-carboxamide as pale yellow oil (0.353 g, 66.5%).

[Step 3] 4-Ethyl-N-(4-fluorophenyl)-N-((5-(2-(2,2,2-trifluoroacetyl)hydrazine-1-carbonyl)pyridin-2-yl)methyl)piperazine-1-carboxamide

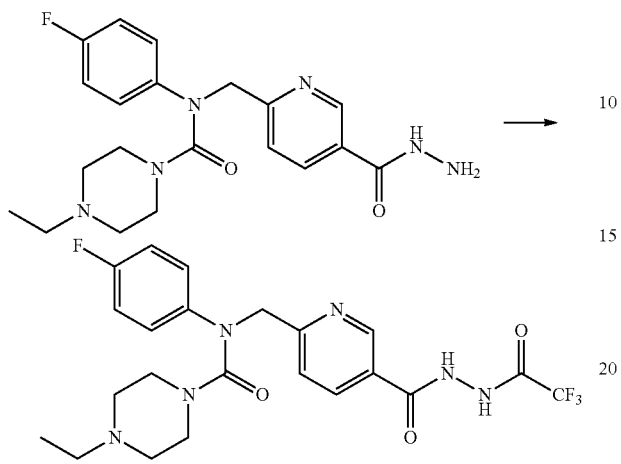

A solution of 4-ethyl-N-(4-fluorophenyl)-N-((5-(hydrazinecarbonyl)pyridin-2-yl)methyl)piperazine-1-carboxamide (0.176 g, 0.439 mmol), triethylamine (0.067 mL, 0.483 mmol) and trifluoroacetic anhydride (0.062 mL, 0.439 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(4-fluorophenyl)-N-((5-(2-(2,2,2-trifluoroacetyl)hydrazine-1-carbonyl)pyridin-2-yl)methyl)piperazine-1-carboxamide, 0.210 g, 96.2%, pale yellow oil).

[Step 4] Compound 21870

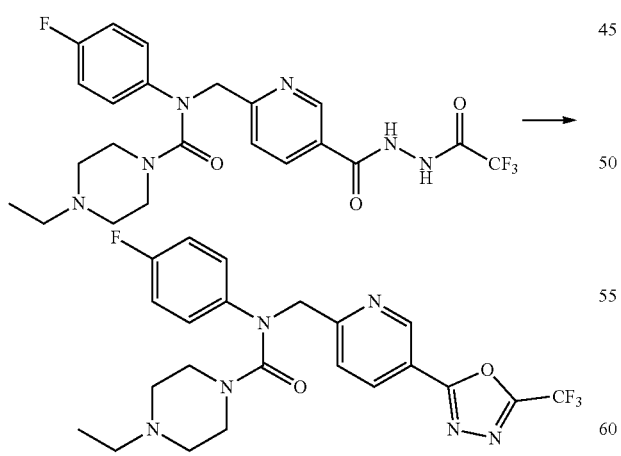

4-Ethyl-N-(4-fluorophenyl)-N-((5-(2-(2,2,2-trifluoroacetyl)hydrazine-1-carbonyl)pyridin-2-yl)methyl)piperazine-1-carboxamide (0.210 g, 0.423 mmol) and 1-methoxy-N-triethylammoniosulfonyl-methanimidate (Burgess reagent, 0.151 g, 0.634 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(4-fluorophenyl)-N-((5-(5-(trifluoromethyl)-1,3,4-oxadiazol-2-yl)pyridin-2-yl)methyl)piperazine-1-carboxamide as pale yellow oil (0.050 g, 24.6%).

$^1$H NMR (400 MHz, CDCl$_3$) δ 9.24 (dd, 1H, J=2.3, 0.8 Hz), 8.37 (dd, 1H, J=8.2, 2.2 Hz), 7.60 (d, 1H, J=8.2 Hz), 7.20-7.13 (m, 2H), 7.07-7.01 (m, 2H), 5.08 (s, 2H), 3.55 (s, 4H), 2.97-2.43 (m, 6H), 1.42-1.20 (m, 3H).

Example 330. Compound 21871: 4-Ethyl-N-(3-methoxyphenyl)-N-(4-(5-(trifluoromethyl)-1,3,4-oxadiazol-2-yl)benzyl)piperazine-1-carboxamide

[Step 1] 4-Ethyl-N-(3-methoxyphenyl)piperazine-1-carboxamide

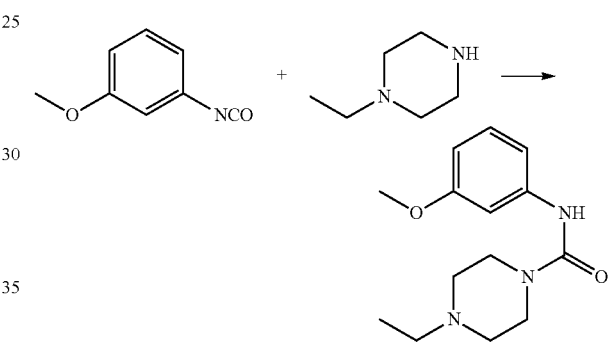

A solution of 1-isocyanato-3-methoxybenzene (0.516 mL, 4.000 mmol) and 1-ethylpiperazine (0.457 g, 4.000 mmol) in diethylether (8 mL) prepared at the room temperature was stirred at the same temperature for 5 hr. The reaction mixture was concentrated under the reduced pressure to remove the solvent. The title compound was used without further purification (4-ethyl-N-(3-methoxyphenyl)piperazine-1-carboxamide, 1.050 g, 99.7%, whitesolid).

[Step 2] Methyl 4-((4-ethyl-N-(3-methoxyphenyl)piperazine-1-carboxamido)methyl)benzoate

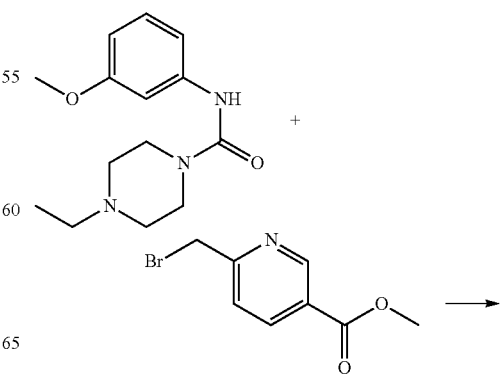

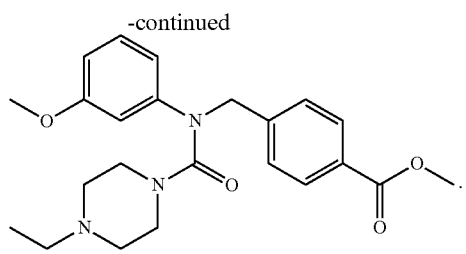

A solution of 4-ethyl-N-(3-methoxyphenyl)piperazine-1-carboxamide (0.350 g, 1.330 mmol) and sodium hydride (60.00%, 0.059 g, 1.463 mmol) in tetrahydrofuran (6 mL) was stirred at the room temperature for 30 min, and mixed with methyl 4-(bromomethyl)benzoate (0.335 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((4-ethyl-N-(3-methoxyphenyl)piperazine-1-carboxamido)methyl)benzoate, 0.546 g, 99.8%, pale yellow oil).

[Step 3] 4-Ethyl-N-(4-(hydrazinecarbonyl)benzyl)-N-(3-methoxyphenyl)piperazine-1-carboxamide

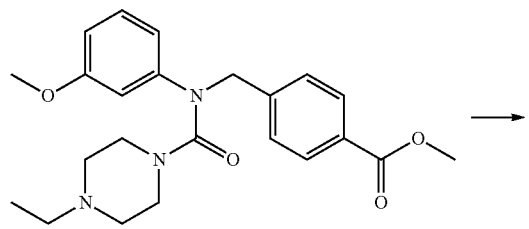

Methyl 4-((4-ethyl-N-(3-methoxyphenyl)piperazine-1-carboxamido)methyl)benzoate (0.546 g, 1.327 mmol) and hydrazine monohydrate (1.290 mL, 26.537 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO₂, 24 g cartridge; methanol/dichloromethane=0% to 10%) to give 4-ethyl-N-(4-(hydrazinecarbonyl)benzyl)-N-(3-methoxyphenyl)piperazine-1-carboxamide as colorless oil (0.479 g, 87.8%).

[Step 4] 4-Ethyl-N-(3-methoxyphenyl)-N-(4-(2-(2,2,2-trifluoroacetyl)hydrazine-1-carbonyl)benzyl)piperazine-1-carboxamide

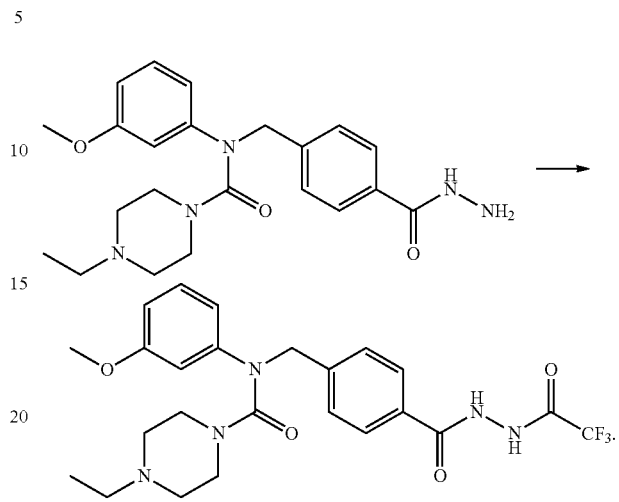

A solution of 4-ethyl-N-(4-(hydrazinecarbonyl)benzyl)-N-(3-methoxyphenyl)piperazine-1-carboxamide (0.239 g, 0.581 mmol), triethylamine (0.089 mL, 0.639 mmol) and trifluoroacetic anhydride (0.082 mL, 0.581 mmol) in dichloromethane (4 mL) prepared at the room temperature was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(3-methoxyphenyl)-N-(4-(2-(2,2,2-trifluoroacetyl)hydrazine-1-carbonyl)benzyl)piperazine-1-carboxamide, 0.290 g, 98.4%, pale yellow oil).

[Step 5] Compound 21871

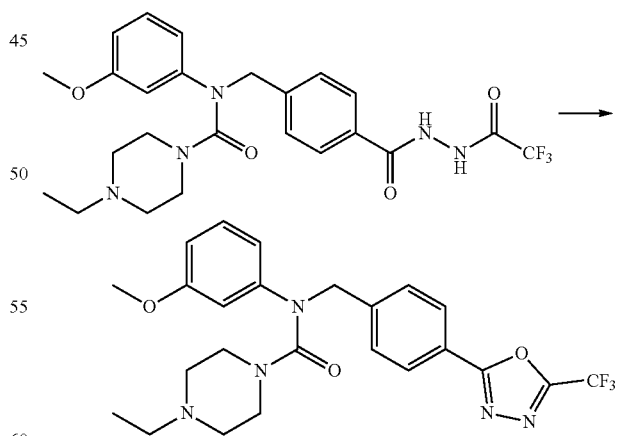

4-Ethyl-N-(3-methoxyphenyl)-N-(4-(2-(2,2,2-trifluoroacetyl)hydrazine-1-carbonyl)benzyl)piperazine-1-carboxamide (0.290 g, 0.571 mmol) and 1-methoxy-N-triethylammoniosulfonyl-methanimidate (Burgess reagent, 0.204 g, 0.857 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(3-methoxyphenyl)-N-(4-(5-(trifluoromethyl)-1,3,4-oxadiazol-2-yl)benzyl)piperazine-1-carboxamide as pale yellow oil (0.036 g, 12.9%).

$^1$H NMR (400 MHz, CDCl$_3$) δ 8.07-8.00 (m, 2H), 7.51-7.47 (m, 2H), 7.23 (t, 1H, J=8.2 Hz), 6.70 (ddd, 1H, J=8.3, 2.4, 0.8 Hz), 6.65 (ddd, 1H, J=8.0, 2.2, 0.9 Hz), 6.61 (t, 1H, J=2.3 Hz), 4.93 (s, 2H), 3.78 (s, 3H), 3.53 (s, 4H), 2.86-2.53 (m, 6H), 1.26-1.23 (m, 3H); LRMS (ES) m/z 490.1 (M$^+$+1).

Example 331. Compound 21872: 4-Ethyl-N-(2-fluoro-4-(5-(trifluoromethyl)-1,3,4-oxadiazol-2-yl)benzyl)-N-(3-methoxy phenyl)piperazine-1-carboxamide

[Step 1] Methyl 4-((4-ethyl-N-(3-methoxyphenyl)piperazine-1-carboxamido)methyl)-3-fluorobenzoate

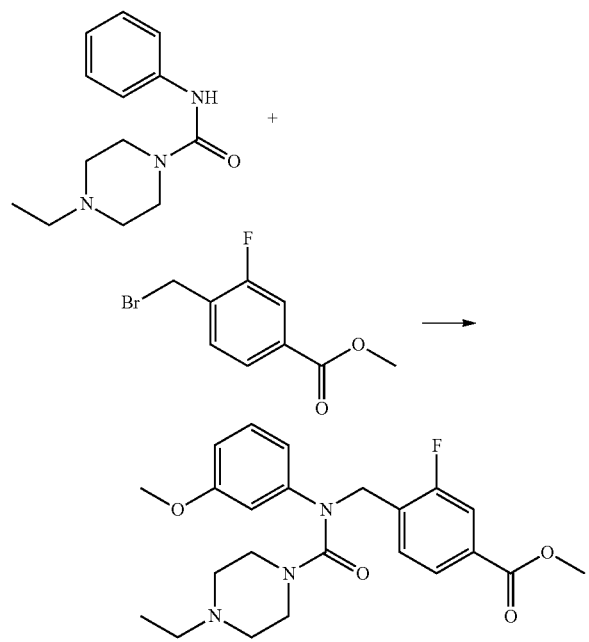

A solution of 4-ethyl-N-(3-methoxyphenyl)piperazine-1-carboxamide (0.350 g, 1.330 mmol) and sodium hydride (60.00%, 0.059 g, 1.463 mmol) in tetrahydrofuran (6 mL) was stirred at the room temperature for 30 min, and mixed with methyl 4-(bromomethyl)-3-fluorobenzoate (0.361 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((4-ethyl-N-(3-methoxyphenyl)piperazine-1-carboxamido)methyl)-3-fluorobenzoate, 0.570 g, 99.8%, pale yellow oil).

[Step 2] 4-Ethyl-N-(2-fluoro-4-(hydrazinecarbonyl)benzyl)-N-(3-methoxyphenyl)piperazine-1-carboxamide

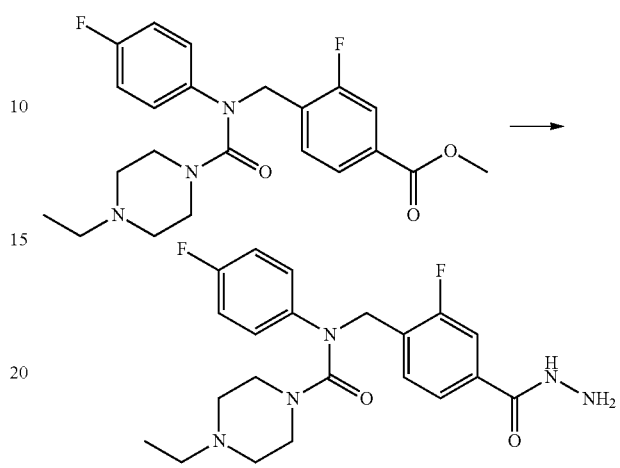

Methyl 4-((4-ethyl-N-(3-methoxyphenyl)piperazine-1-carboxamido)methyl)-3-fluorobenzoate (0.570 g, 1.327 mmol) and hydrazine monohydrate (1.290 mL, 26.543 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-(2-fluoro-4-(hydrazinecarbonyl)benzyl)-N-(3-methoxyphenyl)piperazine-1-carboxamide as colorless oil (0.513 g, 90.0%).

[Step 3] 4-Ethyl-N-(2-fluoro-4-(2-(2,2,2-trifluoroacetyl)hydrazine-1-carbonyl)benzyl)-N-(3-methoxyphenyl)piperazine-1-carboxamide

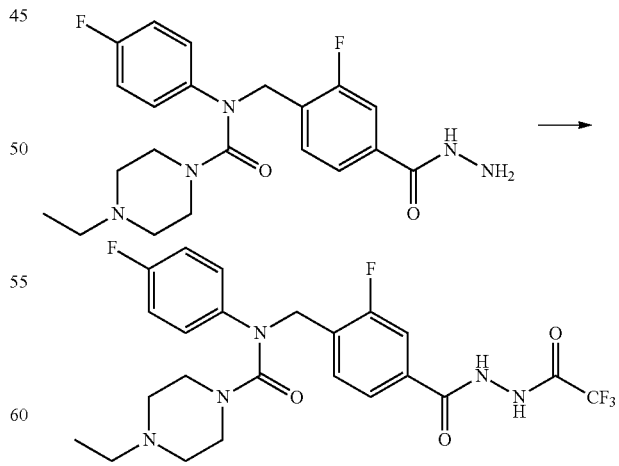

A solution of 4-ethyl-N-(2-fluoro-4-(hydrazinecarbonyl)benzyl)-N-(3-methoxyphenyl)piperazine-1-carboxamide (0.256 g, 0.596 mmol), triethylamine (0.091 mL, 0.656 mmol) and trifluoroacetic anhydride (0.084 mL, 0.596 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(2-fluoro-4-(2-(2,2,2-trifluoroacetyl)hydrazine-1-carbonyl)benzyl)-N-(3-methoxyphenyl)piperazine-1-carboxamide, 0.310 g, 99.0%, pale yellow oil).

[Step 4] Compound 21872

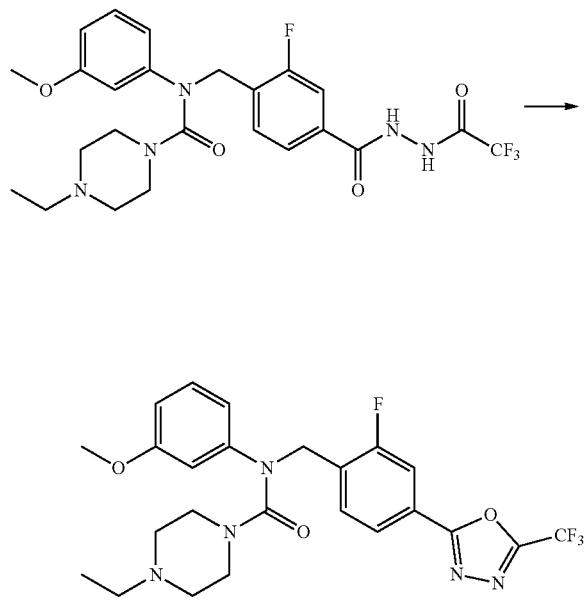 [SMILES: CCN1CCN(C(=O)N(Cc2ccc(C(=O)NNC(=O)C(F)(F)F)cc2)c2cccc(OC)c2)CC1 ; CCN1CCN(C(=O)N(Cc2ccc(-c3nnc(C(F)(F)F)o3)cc2)c2cccc(OC)c2)CC1]

4-Ethyl-N-(2-fluoro-4-(2-(2,2,2-trifluoroacetyl)hydrazine-1-carbonyl)benzyl)-N-(3-methoxyphenyl)piperazine-1-carboxamide (0.310 g, 0.590 mmol) and 1-methoxy-N-triethylammoniosulfonyl-methanimidate (Burgess reagent, 0.211 g, 0.885 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(2-fluoro-4-(5-(trifluoromethyl)-1,3,4-oxadiazol-2-yl)benzyl)-N-(3-methoxy phenyl)piperazine-1-carboxamide as pale yellow oil (0.033 g, 11.1%).

$^1$H NMR (400 MHz, CDCl$_3$) δ 7.87 (dd, 1H, J=8.0, 1.7 Hz), 7.76 (dd, 1H, J=9.9, 1.7 Hz), 7.69 (t, 1H, J=7.6 Hz), 7.23 (t, 1H, J=8.1 Hz), 6.73-6.65 (m, 2H), 6.66 (t, 1H, J=2.3 Hz), 4.98 (s, 2H), 3.79 (s, 3H), 3.49 (s, 4H), 2.75-2.36 (m, 6H), 1.20 (brs, 3H); LRMS (ES) m/z 508.1 (M$^+$+1).

Example 332. Compound 21873: 4-Ethyl-N-(3-methoxyphenyl)-N-((5-(5-(trifluoromethyl)-1,3,4-oxadiazol-2-yl)pyridin-2-yl)methyl)piperazine-1-carboxamide

[Step 1] Methyl 6-((4-ethyl-N-(3-methoxyphenyl)piperazine-1-carboxamido)methyl)nicotinate

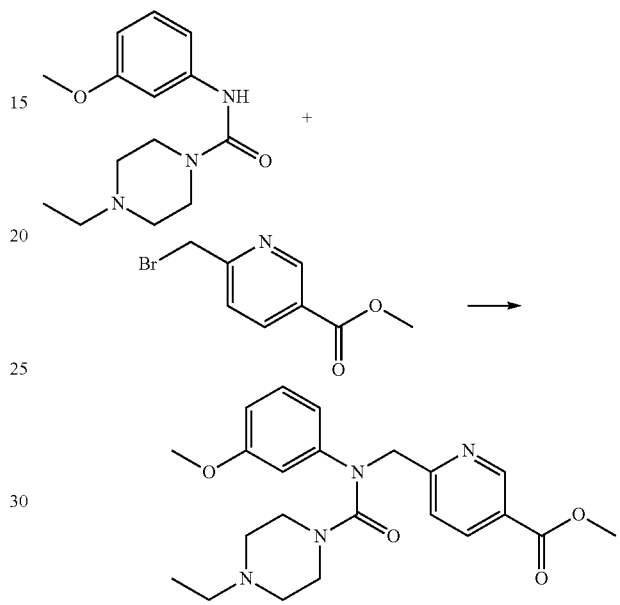

A solution of 4-ethyl-N-(3-methoxyphenyl)piperazine-1-carboxamide (0.350 g, 1.330 mmol) and sodium hydride (60.00%, 0.059 g, 1.463 mmol) in tetrahydrofuran (6 mL) was stirred at the room temperature for 30 min, and mixed with methyl 6-(bromomethyl)nicotinate (0.337 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((4-ethyl-N-(3-methoxyphenyl)piperazine-1-carboxamido)methyl)nicotinate, 0.548 g, 99.9%, brown oil).

[Step 2] 4-Ethyl-N-((5-(hydrazinecarbonyl)pyridin-2-yl)methyl)-N-(3-methoxyphenyl)piperazine-1-carboxamide

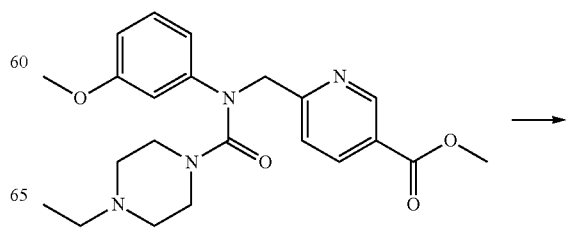

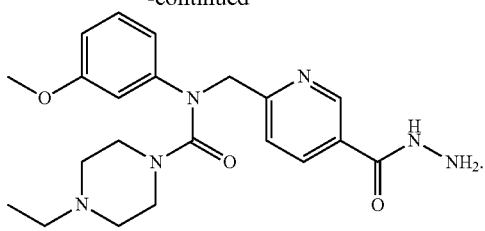

Methyl 6-((4-ethyl-N-(3-methoxyphenyl)piperazine-1-carboxamido)methyl)nicotinate (0.548 g, 1.329 mmol) and hydrazine monohydrate (1.291 mL, 26.570 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-((5-(hydrazinecarbonyl)pyridin-2-yl)methyl)-N-(3-methoxyphenyl)piperazine-1-carboxamide as pale yellow oil (0.346 g, 63.1%).

[Step 3] 4-Ethyl-N-(3-methoxyphenyl)-N-((5-(2-(2,2,2-trifluoroacetyl)hydrazine-1-carbonyl)pyridin-2-yl)methyl)piperazine-1-carboxamide

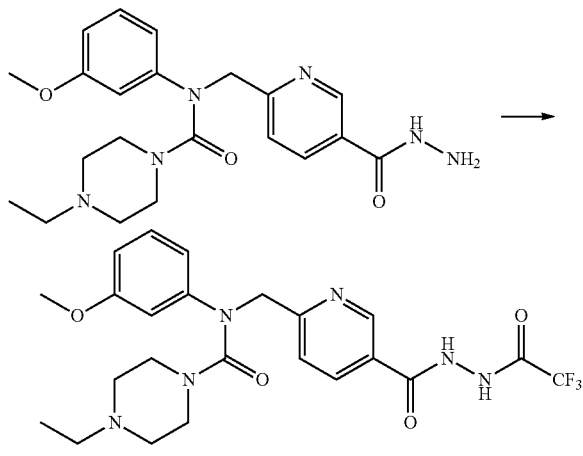

A solution of 4-ethyl-N-((5-(hydrazinecarbonyl)pyridin-2-yl)methyl)-N-(3-methoxyphenyl)piperazine-1-carboxamide (0.172 g, 0.417 mmol), triethylamine (0.064 mL, 0.459 mmol) and trifluoroacetic anhydride (0.059 mL, 0.417 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(3-methoxyphenyl)-N-((5-(2-(2,2,2-trifluoroacetyl)hydrazine-1-carbonyl)pyridin-2-yl)methyl)piperazine-1-carboxamide, 0.210 g, 99.0%, pale yellow oil).

[Step 4] Compound 21873

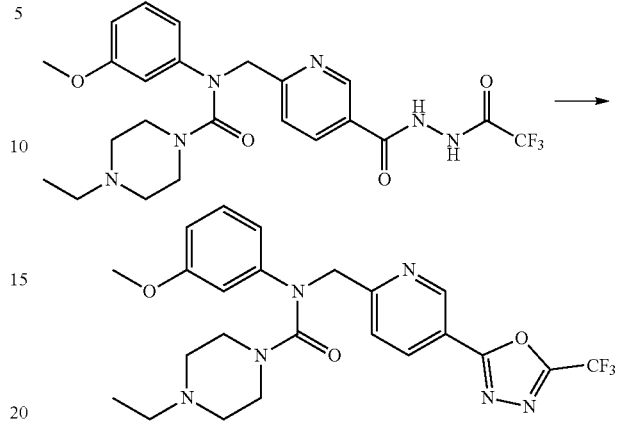

4-Ethyl-N-(3-methoxyphenyl)-N-((5-(2-(2,2,2-trifluoroacetyl)hydrazine-1-carbonyl) pyridin-2-yl)methyl)piperazine-1-carboxamide (0.210 g, 0.413 mmol) and 1-methoxy-N-triethylammoniosulfonyl-methanimidate (Burgess reagent, 0.148 g, 0.619 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(3-methoxyphenyl)-N-((5-(5-(trifluoromethyl)-1,3,4-oxadiazol-2-yl)pyridin-2-yl)methyl)piperazine-1-carboxamide as pale yellow oil (0.053 g, 26.2%).
$^1$H NMR (400 MHz, CDCl$_3$) δ 9.24 (dd, 1H, J=2.3, 0.8 Hz), 8.34 (dd, 1H, J=8.3, 2.2 Hz), 7.61 (dd, 1H, J=8.2, 0.9 Hz), 7.22 (t, 1H, J=8.1 Hz), 6.75 (ddd, 1H, J=8.0, 2.1, 0.8 Hz), 6.71 (t, 1H, J=2.3 Hz), 6.68-6.65 (m, 1H), 5.13 (s, 2H), 3.79 (s, 3H), 3.47 (s, 4H), 2.55 (brs, 6H), 1.18 (s, 3H); LRMS (ES) m/z 491.1 (M$^+$+1).

Example 333. Compound 21874: 4-Ethyl-N-(4-methoxyphenyl)-N-(4-(5-(trifluoromethyl)-1,3,4-oxadiazol-2-yl)benzyl)piperazine-1-carboxamide

[Step 1] 4-Ethyl-N-(4-methoxyphenyl)piperazine-1-carboxamide

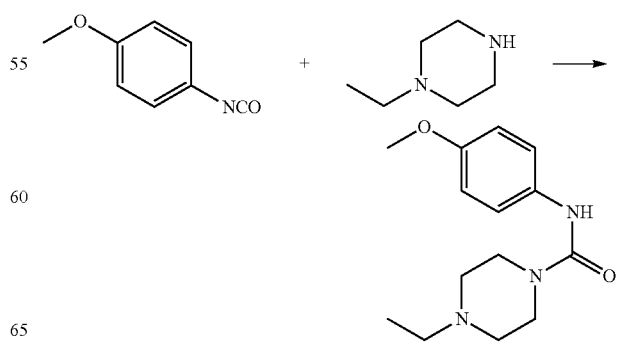

A solution of 1-isocyanato-4-methoxybenzene (0.514 mL, 4.000 mmol) and 1-ethylpiperazine (0.457 g, 4.000 mmol) in diethylether (8 mL) prepared at the room temperature was stirred at the same temperature for 5 hr. The reaction mixture was concentrated under the reduced pressure to remove the solvent The title compound was used without further purification (4-ethyl-N-(4-methoxyphenyl)piperazine-1-carboxamide, 1.050 g, 99.7%, white solid).

[Step 2] Methyl 4-((4-ethyl-N-(4-methoxyphenyl)piperazine-1-carboxamido)methyl)benzoate

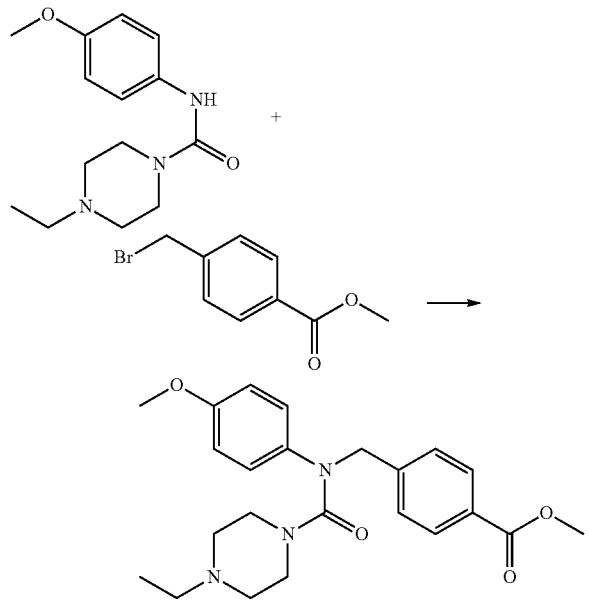

A solution of 4-ethyl-N-(4-methoxyphenyl)piperazine-1-carboxamide (0.350 g, 1.330 mmol) and sodium hydride (60.00%, 0.059 g, 1.463 mmol) in tetrahydrofuran (6 mL) was stirred at the room temperature for 30 min, and mixed with methyl 4-(bromomethyl)benzoate (0.335 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((4-ethyl-N-(4-methoxyphenyl)piperazine-1-carboxamido)methyl) benzoate, 0.546 g, 99.5%, pale yellow oil).

[Step 3] 4-Ethyl-N-(4-(hydrazinecarbonyl)benzyl)-N-(4-methoxyphenyl)piperazine-1-carboxamide

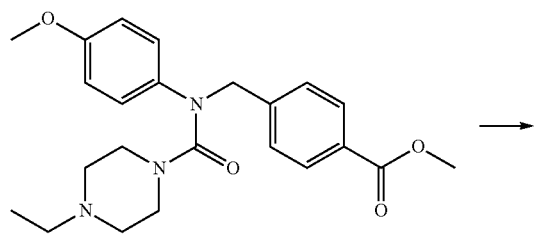

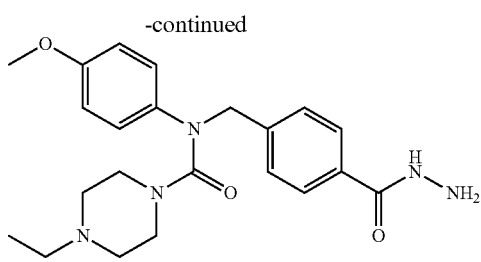

Methyl 4-((4-ethyl-N-(4-methoxyphenyl)piperazine-1-carboxamido)methyl)benzoate (0.546 g, 1.327 mmol) and hydrazine monohydrate (1.290 mL, 26.537 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography ($SiO_2$, 24 g cartridge; methanol/dichloromethane=0% to 10%) to give 4-ethyl-N-(4-(hydrazinecarbonyl)benzyl)-N-(4-methoxyphenyl)piperazine-1-carboxamide as colorless oil (0.527 g, 96.5%).

[Step 4] 4-Ethyl-N-(4-methoxyphenyl)-N-(4-(2-(2,2,2-trifluoroacetyl)hydrazine-1-carbonyl)benzyl)piperazine-1-carboxamide

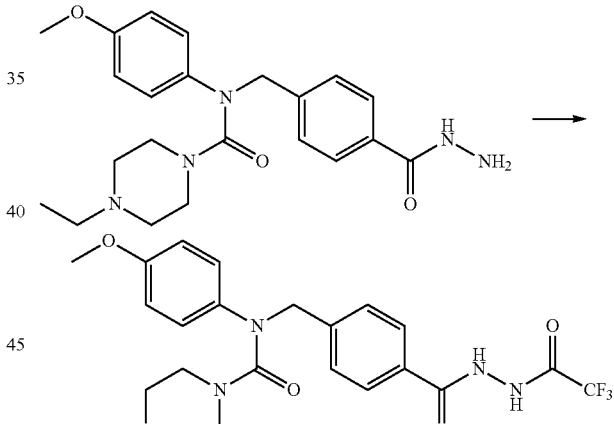

A solution of 4-ethyl-N-(4-(hydrazinecarbonyl)benzyl)-N-(4-methoxyphenyl)piperazine-1-carboxamide (0.263 g, 0.639 mmol), triethylamine (0.098 mL, 0.703 mmol) and trifluoroacetic anhydride (0.090 mL, 0.639 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(4-methoxyphenyl)-N-(4-(2-(2,2,2-trifluoroacetyl)hydrazine-1-carbonyl)benzyl)piperazine-1-carboxamide, 0.320 g, 98.7%, pale yellow oil).

1037

[Step 5] Compound 21874

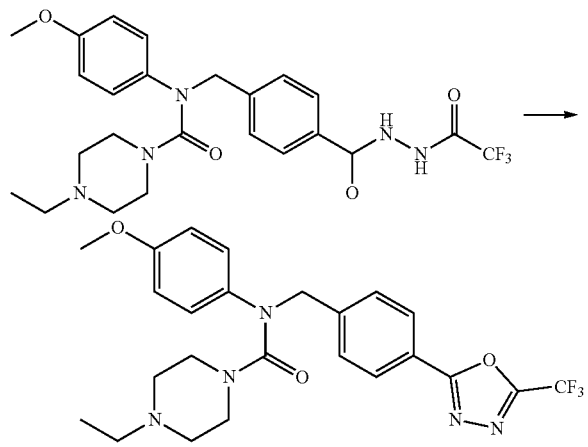

4-Ethyl-N-(4-methoxyphenyl)-N-(4-(2-(2,2,2-trifluoroacetyl)hydrazine-1-carbonyl)benzyl)piperazine-1-carboxamide (0.320 g, 0.631 mmol) and 1-methoxy-N-triethylammoniosulfonyl-methanimidate (Burgess reagent, 0.225 g, 0.946 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(4-methoxyphenyl)-N-(4-(5-(trifluoromethyl)-1,3,4-oxadiazol-2-yl)benzyl)piperazine-1-carboxamide as pale yellow oil (0.032 g, 10.2%).

$^1$H NMR (400 MHz, CDCl$_3$) δ 8.05-8.00 (m, 2H), 7.49-7.44 (m, 2H), 6.99-6.92 (m, 2H), 6.86-6.81 (m, 2H), 4.87 (s, 2H), 3.80 (s, 3H), 3.43 (s, 4H), 2.70-2.40 (m, 6H), 1.24-1.13 (m, 3H); LRMS (ES) m/z 490.4 (M$^+$+1).

Example 334. Compound 21875: 4-Ethyl-N-(2-fluoro-4-(5-(trifluoromethyl)-1,3,4-oxadiazol-2-yl)benzyl)-N-(4-methoxyphenyl)piperazine-1-carboxamide

[Step 1] Methyl 4-((4-ethyl-N-(4-methoxyphenyl)piperazine-1-carboxamido)methyl)-3-fluorobenzoate

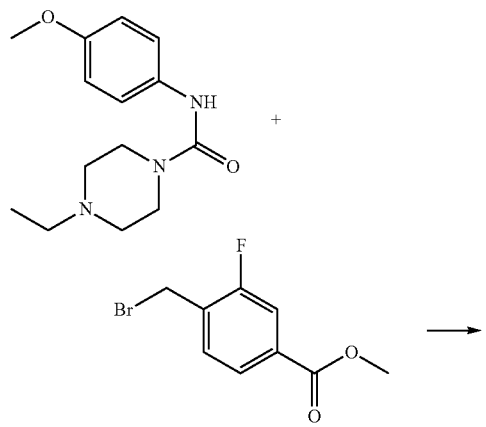

1038

-continued

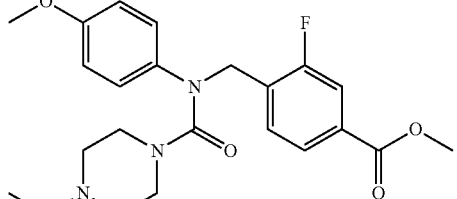

A solution of 4-ethyl-N-(4-methoxyphenyl)piperazine-1-carboxamide (0.350 g, 1.330 mmol) and sodium hydride (60.00%, 0.059 g, 1.463 mmol) in tetrahydrofuran (6 mL) was stirred at the room temperature for 30 min, and mixed with methyl 4-(bromomethyl)-3-fluorobenzoate (0.361 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((4-ethyl-N-(4-methoxyphenyl)piperazine-1-carboxamido)methyl)-3-fluorobenzoate, 0.570 g, 99.8%, pale yellow oil).

[Step 2] 4-Ethyl-N-(2-fluoro-4-(hydrazinecarbonyl)benzyl)-N-(4-methoxyphenyl)piperazine-1-carboxamide

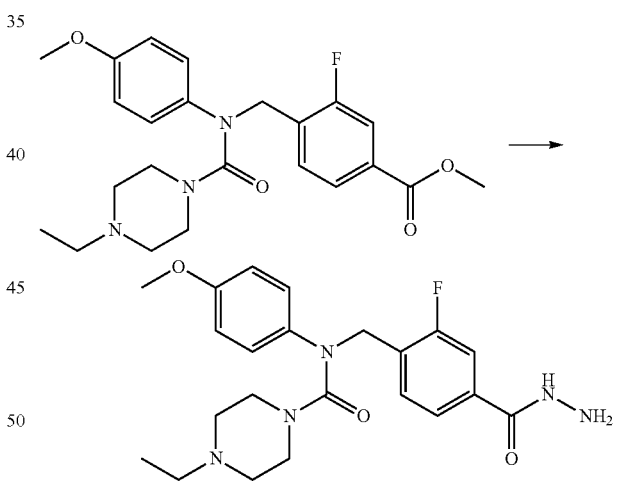

Methyl 4-((4-ethyl-N-(4-methoxyphenyl)piperazine-1-carboxamido)methyl)-3-fluorobenzoate (0.570 g, 1.327 mmol) and hydrazine monohydrate (1.290 mL, 26.543 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-(2-fluoro-4-(hydrazinecarbonyl)benzyl)-N-(4-methoxyphenyl)piperazine-1-carboxamide as colorless oil (0.456 g, 80.0%).

[Step 3] 4-Ethyl-N-(2-fluoro-4-(2-(2,2,2-trifluoro-acetyl)hydrazine-1-carbonyl)benzyl)-N-(4-methoxyphenyl)piperazine-1-carboxamide

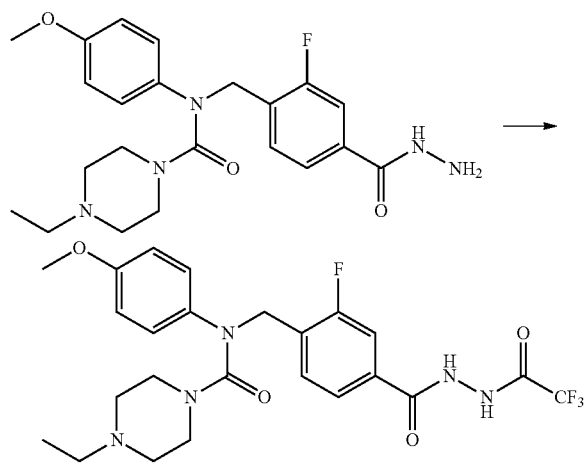

A solution of 4-ethyl-N-(2-fluoro-4-(hydrazinecarbonyl)benzyl)-N-(4-methoxyphenyl)piperazine-1-carboxamide (0.227 g, 0.529 mmol), triethylamine (0.081 mL, 0.581 mmol) and trifluoroacetic anhydride (0.075 mL, 0.529 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(2-fluoro-4-(2-(2,2,2-trifluoroacetyl)hydrazine-1-carbonyl)benzyl)-N-(4-methoxyphenyl)piperazine-1-carboxamide, 0.270 g, 97.2%, pale yellow oil).

[Step 4] Compound 21875

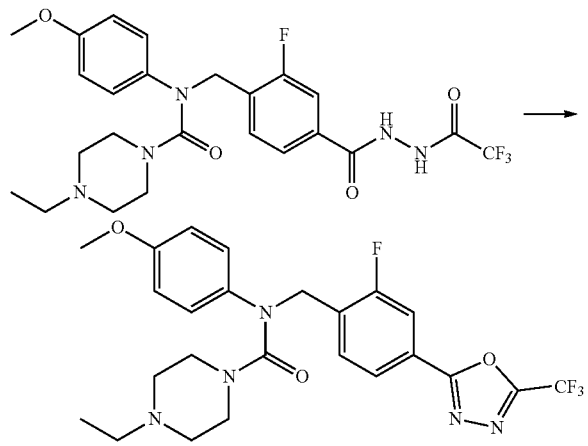

4-Ethyl-N-(2-fluoro-4-(2-(2,2,2-trifluoroacetyl)hydrazine-1-carbonyl)benzyl)-N-(4-methoxyphenyl)piperazine-1-carboxamide (0.270 g, 0.514 mmol) and 1-methoxy-N-triethylammoniosulfonyl-methanimidate (Burgess reagent, 0.184 g, 0.771 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(2-fluoro-4-(5-(trifluoromethyl)-1,3,4-oxadiazol-2-yl)benzyl)-N-(4-methoxyphenyl)piperazine-1-carboxamide as pale yellow oil (0.045 g, 17.2%).

$^1$H NMR (400 MHz, CDCl$_3$) δ 7.87 (dd, 1H, J=8.0, 1.7 Hz), 7.76-7.69 (m, 2H), 7.04-6.98 (m, 2H), 6.87-6.81 (m, 2H), 4.92 (s, 2H), 3.80 (s, 3H), 3.41 (s, 4H), 2.65-2.27 (m, 6H), 1.16 (s, 3H); LRMS (ES) m/z 508.0 (M$^+$+1).

Example 335. Compound 21876: 4-Ethyl-N-(4-methoxyphenyl)-N-((5-(5-(trifluoromethyl)-1,3,4-oxadiazol-2-yl)pyridin-2-yl)methyl)piperazine-1-carboxamide

[Step 1] Methyl 6-((4-ethyl-N-(4-methoxyphenyl)piperazine-1-carboxamido)methyl)nicotinate

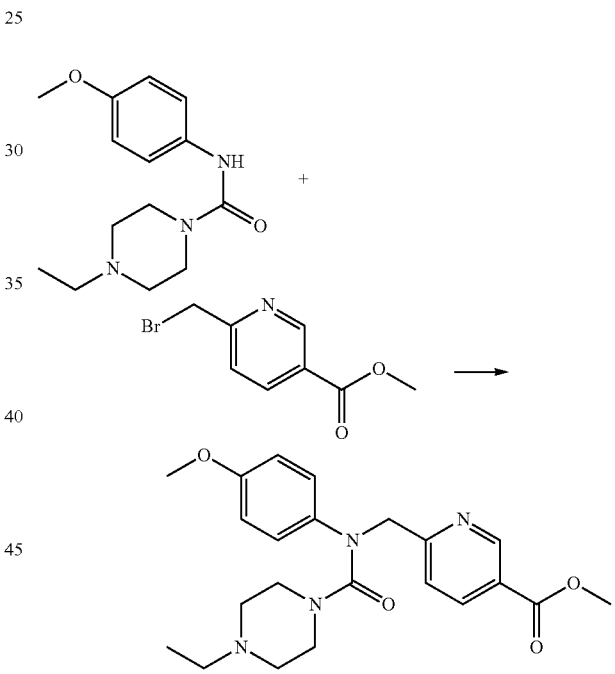

A solution of 4-ethyl-N-(4-methoxyphenyl)piperazine-1-carboxamide (0.350 g, 1.330 mmol) and sodium hydride (60.00%, 0.059 g, 1.463 mmol) in tetrahydrofuran (6 mL) was stirred at the room temperature for 30 min, and mixed with methyl 6-(bromomethyl)nicotinate (0.337 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((4-ethyl-N-(4-methoxyphenyl)piperazine-1-carboxamido)methyl)nicotinate, 0.548 g, 99.9%, brown oil).

[Step 2] 4-Ethyl-N-((5-(hydrazinecarbonyl)pyridin-2-yl)methyl)-N-(4-methoxyphenyl)piperazine-1-carboxamide

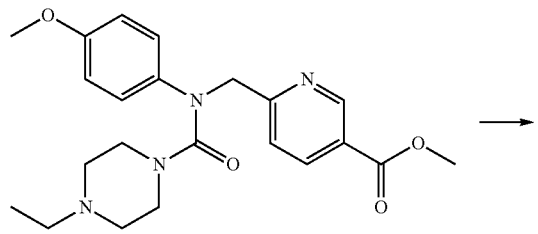

Methyl 6-((4-ethyl-N-(4-methoxyphenyl)piperazine-1-carboxamido)methyl)nicotinate (0.548 g, 1.329 mmol) and hydrazine monohydrate (1.291 mL, 26.570 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give 4-ethyl-N-((5-(hydrazinecarbonyl)pyridin-2-yl)methyl)-N-(4-methoxyphenyl)piperazine-1-carboxamide as pale yellow oil (0.424 g, 77.4%).

[Step 3] 4-Ethyl-N-(4-methoxyphenyl)-N-((5-(2-(2,2,2-trifluoroacetyl)hydrazine-1-carbonyl)pyridin-2-yl)methyl)piperazine-1-carboxamide

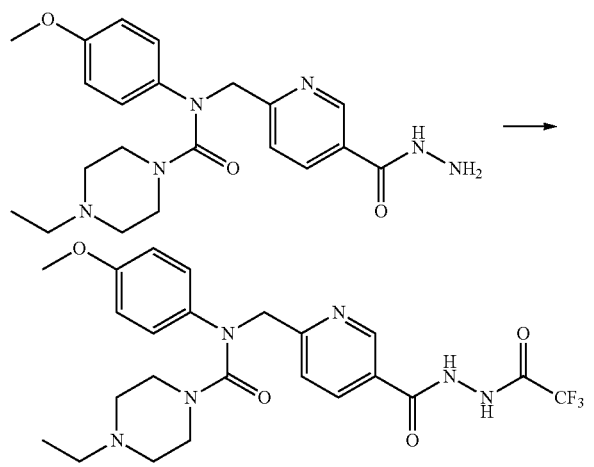

A solution of 4-ethyl-N-((5-(hydrazinecarbonyl)pyridin-2-yl)methyl)-N-(4-methoxyphenyl)piperazine-1-carboxamide (0.211 g, 0.512 mmol), triethylamine (0.078 mL, 0.563 mmol) and trifluoroacetic anhydride (0.072 mL, 0.512 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (4-ethyl-N-(4-methoxyphenyl)-N-((5-(2-(2,2,2-trifluoroacetyl)hydrazine-1-carbonyl)pyridin-2-yl)methyl)piperazine-1-carboxamide, 0.250 g, 96.1%, pale yellow oil).

[Step 4] Compound 21876

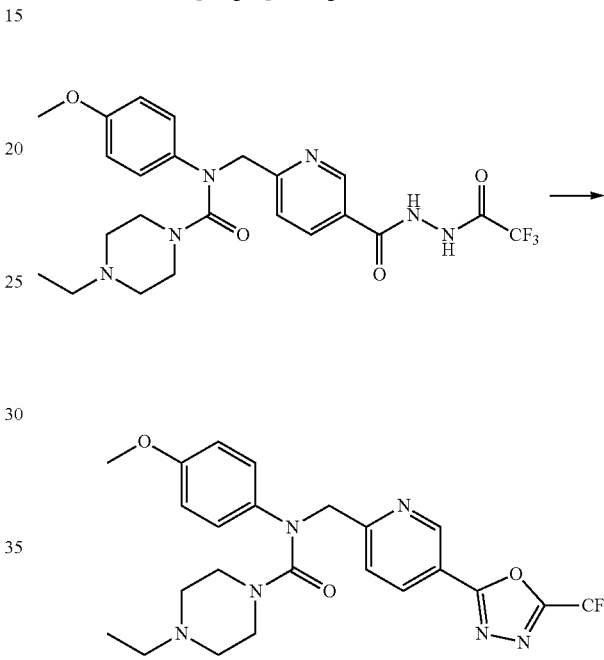

4-Ethyl-N-(4-methoxyphenyl)-N-((5-(2-(2,2,2-trifluoroacetyl)hydrazine-1-carbonyl) pyridin-2-yl)methyl)piperazine-1-carboxamide (0.250 g, 0.492 mmol) and 1-methoxy-N-triethylammoniosulfonyl-methanimidate (Burgess reagent, 0.176 g, 0.737 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give 4-ethyl-N-(4-methoxyphenyl)-N-((5-(5-(trifluoromethyl)-1,3,4-oxadiazol-2-yl)pyridin-2-yl)methyl)piperazine-1-carboxamide as pale yellow oil (0.028 g, 11.6%).

$^1$H NMR (400 MHz, CDCl$_3$) δ 9.23 (dd, 1H, J=2.3, 0.8 Hz), 8.35 (dd, 1H, J=8.2, 2.2 Hz), 7.65-7.60 (m, 1H), 7.13-7.06 (m, 2H), 6.87-6.82 (m, 2H), 5.07 (s, 2H), 3.80 (s, 3H), 3.48 (s, 4H), 2.66 (brs, 6H), 1.22 (brs, 3H); LRMS (ES) m/z 491.3 (M$^+$+1).

Example 336. Compound 21877: N-(3-Chlorophenyl)-N-(4-(5-(difluoromethyl)-1,3,4-oxadiazol-2-yl)benzyl)-4-ethylpiperazine-1-carboxamide

[Step 1] N-(3-Chlorophenyl)-N-(4-(2-(2,2-difluoroacetyl)hydrazine-1-carbonyl)benzyl)-4-ethylpiperazine-1-carboxamide

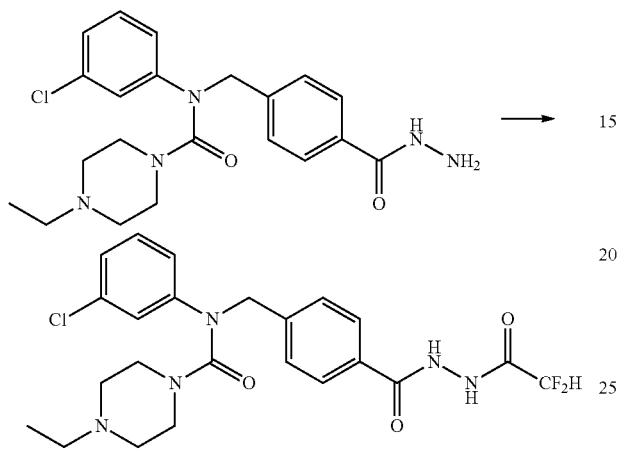

A solution of N-(3-chlorophenyl)-4-ethyl-N-(4-(hydrazinecarbonyl)benzyl)piperazine-1-carboxamide (0.226 g, 0.543 mmol), triethylamine (0.083 mL, 0.597 mmol) and 2,2-difluoroacetic anhydride (0.067 mL, 0.543 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(3-chlorophenyl)-N-(4-(2-(2,2-difluoroacetyl)hydrazine-1-carbonyl)benzyl)-4-ethylpiperazine-1-carboxamide, 0.260 g, 97.0%, pale yellow oil).

[Step 2] Compound 21877

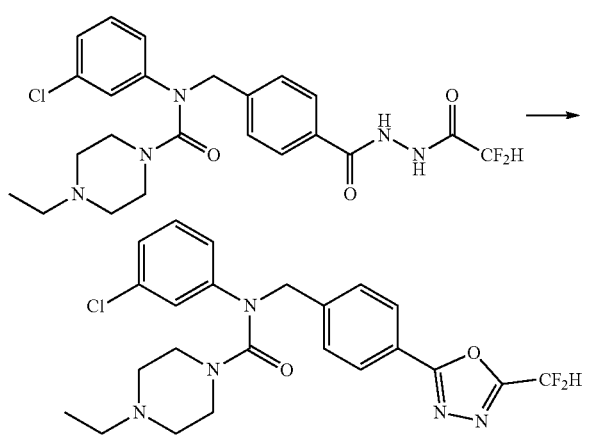

N-(3-Chlorophenyl)-N-(4-(2-(2,2-difluoroacetyl)hydrazine-1-carbonyl)benzyl)-4-ethylpiperazine-1-carboxamide (0.260 g, 0.526 mmol) and 1-methoxy-N-triethylammoniosulfonyl-methanimidate (Burgess reagent, 0.188 g, 0.790 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(3-chlorophenyl)-N-(4-(5-(difluoromethyl)-1,3,4-oxadiazol-2-yl)benzyl)-4-ethylpiperazine-1-carboxamide as white solid (0.080 g, 31.8%).

$^1$H NMR (400 MHz, CDCl$_3$) δ 8.08-8.03 (m, 2H), 7.50-7.46 (m, 2H), 7.24 (t, 1H, J=8.0 Hz), 7.14-7.07 (m, 2H), 7.01-6.84 (m, 2H), 4.94 (s, 2H), 3.45 (s, 4H), 2.71-2.29 (m, 6H), 1.17 (s, 3H); LRMS (ES) m/z 476.3 (M$^+$+1).

Example 337. Compound 21878: N-(3-Chlorophenyl)-N-(4-(5-(difluoromethyl)-1,3,4-oxadiazol-2-yl)-2-fluorobenzyl)-4-ethylpiperazine-1-carboxamide

[Step 1] N-(3-Chlorophenyl)-N-(4-(2-(2,2-difluoroacetyl)hydrazine-1-carbonyl)-2-fluorobenzyl)-4-ethylpiperazine-1-carboxamide

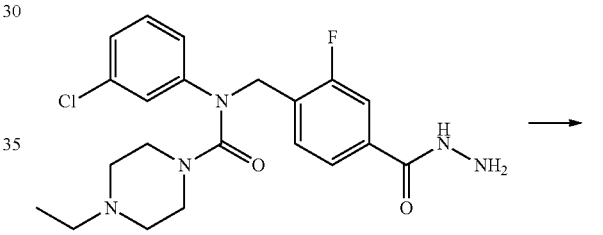

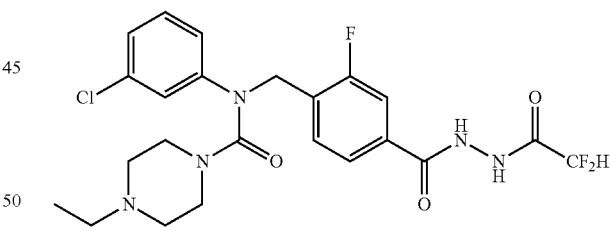

A solution of N-(3-chlorophenyl)-4-ethyl-N-(2-fluoro-4-(hydrazinecarbonyl)benzyl)piperazine-1-carboxamide (0.202 g, 0.466 mmol), triethylamine (0.071 mL, 0.512 mmol) and 2,2-difluoroacetic anhydride (0.058 mL, 0.466 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(3-chlorophenyl)-N-(4-(2-(2,2-difluoroacetyl)hydrazine-1-carbonyl)-2-fluorobenzyl)-4-ethylpiperazine-1-carboxamide, 0.230 g, 96.5%, pale yellow oil).

[Step 2] Compound 21878

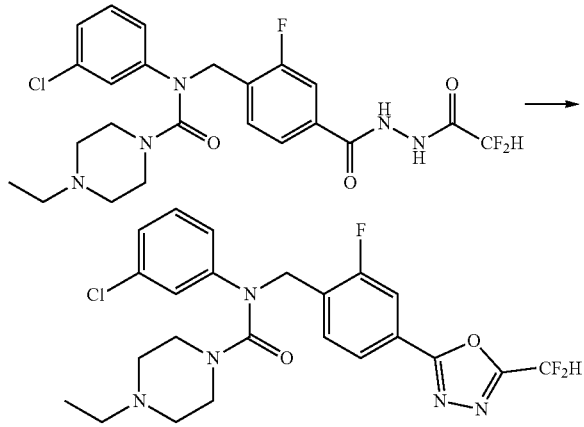

N-(3-Chlorophenyl)-N-(4-(2-(2,2-difluoroacetyl)hydrazine-1-carbonyl)-2-fluorobenzyl)-4-ethylpiperazine-1-carboxamide (0.230 g, 0.449 mmol) and 1-methoxy-N-triethylammoniosulfonyl-methanimidate (Burgess reagent, 0.161 g, 0.674 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(3-chlorophenyl)-N-(4-(5-(difluoromethyl)-1,3,4-oxadiazol-2-yl)-2-fluorobenzyl)-4-ethylpiperazine-1-carboxamide as pale yellow oil (0.077 g, 34.6%).

$^1$H NMR (400 MHz, CDCl$_3$) δ 7.88 (dd, 1H, J=8.0, 1.7 Hz), 7.78 (dd, 1H, J=10.0, 1.7 Hz), 7.68 (t, 1H, J=7.6 Hz), 7.27-7.23 (m, 1H), 7.16-6.82 (m, 4H), 4.97 (s, 2H), 3.41 (s, 4H), 2.51-2.41 (m, 6H), 1.21-1.04 (m, 3H); LRMS (ES) m/z 494.3 (M$^+$+1).

Example 338. Compound 21879: N-(3-Chlorophenyl)-N-((5-(5-(difluoromethyl)-1,3,4-oxadiazol-2-yl)pyridin-2-yl)methyl)-4-ethylpiperazine-1-carboxamide

[Step 1] Methyl 6-((N-(3-chlorophenyl)-4-ethylpiperazine-1-carboxamido)methyl)nicotinate

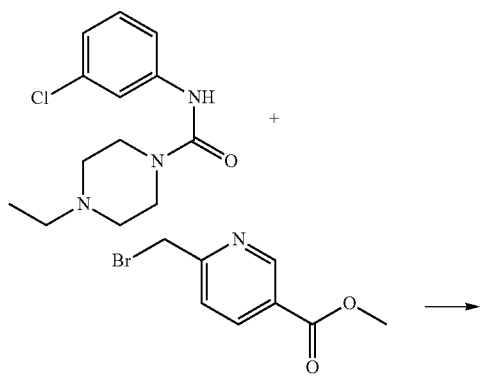

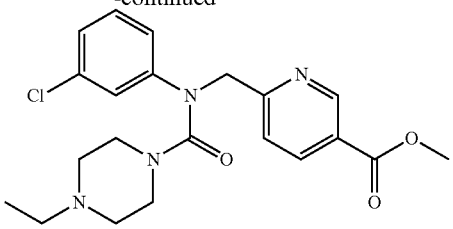

A solution of N-(3-chlorophenyl)-4-ethylpiperazine-1-carboxamide (0.356 g, 1.330 mmol) and sodium hydride (60.00%, 0.058 g, 1.463 mmol) in tetrahydrofuran (6 mL) was stirred at the room temperature for 30 min, and mixed with methyl 6-(bromomethyl)nicotinate (0.336 g, 1.463 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((N-(3-chlorophenyl)-4-ethylpiperazine-1-carboxamido)methyl)nicotinate, 0.550 g, 99.2%, brown oil).

[Step 2] N-(3-Chlorophenyl)-4-ethyl-N-((5-(hydrazinecarbonyl)pyridin-2-yl)methyl)piperazine-1-carboxamide

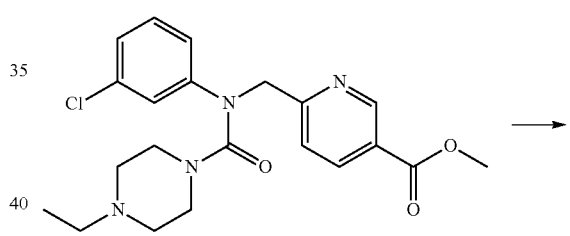

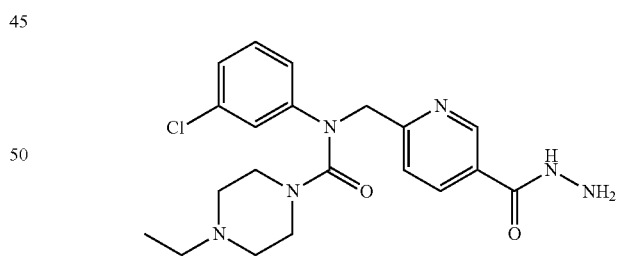

Methyl 6-((N-(3-chlorophenyl)-4-ethylpiperazine-1-carboxamido)methyl)nicotinate (0.550 g, 1.319 mmol) and hydrazine monohydrate (1.282 mL, 26.385 mmol) were mixed at the room temperature in ethanol (6 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 24 g cartridge; methanol/dichloromethane=0% to 10%) to give N-(3-chlorophenyl)-4-ethyl-N-((5-(hydrazinecarbonyl)pyridin-2-yl)methyl)piperazine-1-carboxamide as pale yellow oil (0.220 g, 40.1%).

1047

[Step 3] N-(3-Chlorophenyl)-N-((5-(2-(2,2-difluoro-acetyl)hydrazine-1-carbonyl)pyridin-2-yl)methyl)-4-ethylpiperazine-1-carboxamide

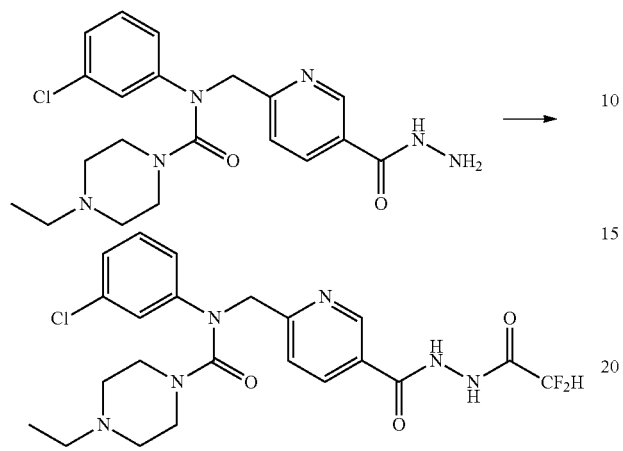

A solution of N-(3-chlorophenyl)-4-ethyl-N-((5-(hydra-zinecarbonyl)pyridin-2-yl)methyl)piperazine-1-carboxam-ide (0.110 g, 0.264 mmol), triethylamine (0.040 mL, 0.290 mmol) and 2,2-difluoroacetic anhydride (0.033 mL, 0.264 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(3-chlorophenyl)-N-((5-(2-(2,2-difluoroacetyl)hydrazine-1-carbonyl)pyridin-2-yl)methyl)-4-ethylpiperazine-1-carboxamide, 0.130 g, 99.6%, pale yellow oil).

[Step 4] Compound 21879

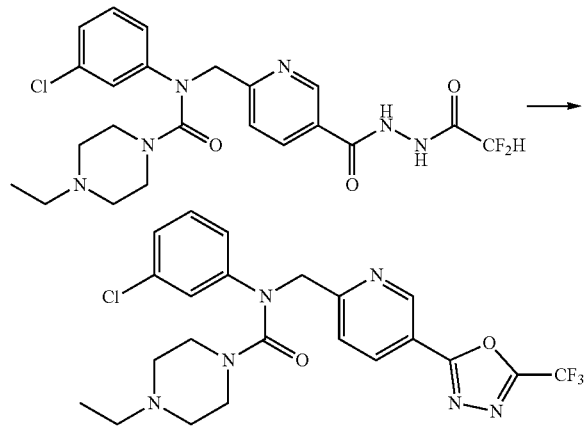

N-(3-Chlorophenyl)-N-((5-(2-(2,2-difluoroacetyl)hydra-zine-1-carbonyl)pyridin-2-yl) methyl)-4-ethylpiperazine-1-carboxamide (0.130 g, 0.263 mmol) and 1-methoxy-N-triethylammoniosulfonyl-methanimidate (Burgess reagent, 0.094 g, 0.394 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(3-chlorophenyl)-N-((5-(5-(difluoromethyl)-1,3,4-oxadi-azol-2-yl)pyridin-2-yl)methyl)-4-ethylpiperazine-1-carbox-amide as pale yellow oil (0.046 g, 36.8%).

$^1$H NMR (400 MHz, CDCl$_3$) δ 9.26 (dd, 1H, J=2.3, 0.8 Hz), 8.38 (dd, 1H, J=8.2, 2.2 Hz), 7.57 (d, 1H, J=8.2 Hz), 7.31-7.25 (m, 1H), 7.18 (t, 1H, J=2.1 Hz), 7.15-7.12 (m, 1H), 7.07 (ddd, 1H, J=8.1, 2.2, 0.9 Hz), 6.96 (t, 1H, J=51.6 Hz), 5.12 (s, 2H), 3.93-3.29 (m, 4H), 3.10-2.25 (m, 6H), 1.29-1.26 (m, 3H); LRMS (ES) m/z 477.1 (M$^+$+1).

Example 339. Compound 21880: N-(4-Chlorophe-nyl)-N-(4-(5-(difluoromethyl)-1,3,4-oxadiazol-2-yl)benzyl)-4-ethylpiperazine-1-carboxamide

[Step 1] N-(4-Chlorophenyl)-N-(4-(2-(2,2-difluoro-acetyl)hydrazine-1-carbonyl)benzyl)-4-ethylpipera-zine-1-carboxamide

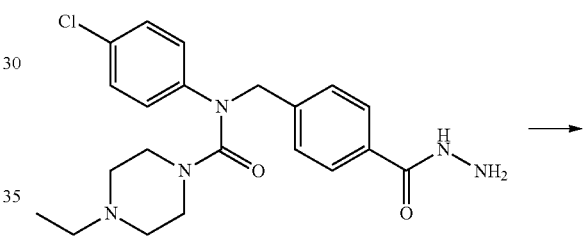

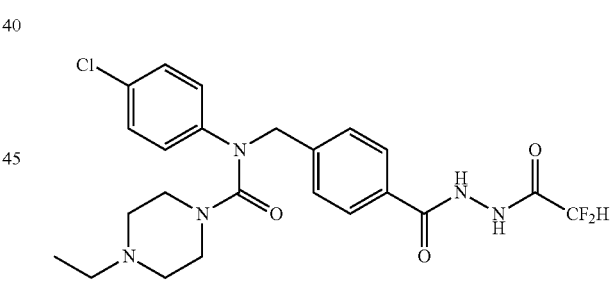

A solution of N-(4-chlorophenyl)-4-ethyl-N-(4-(hydra-zinecarbonyl)benzyl)piperazine-1-carboxamide (0.224 g, 0.538 mmol), triethylamine (0.082 mL, 0.592 mmol) and 2,2-difluoroacetic anhydride (0.067 mL, 0.538 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-chlorophenyl)-N-(4-(2-(2,2-difluoroacetyl)hydrazine-1-carbonyl)benzyl)-4-ethylpip-erazine-1-carboxamide, 0.260 g, 97.8%, pale yellow oil).

[Step 2] Compound 21880

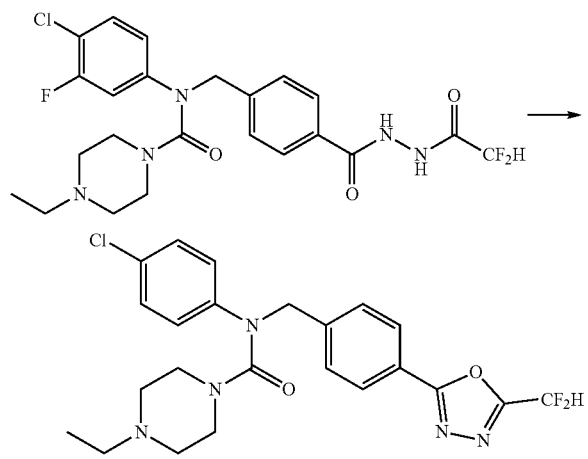

N-(4-Chlorophenyl)-N-(4-(2-(2,2-difluoroacetyl)hydrazine-1-carbonyl)benzyl)-4-ethylpiperazine-1-carboxamide (0.260 g, 0.526 mmol) and 1-methoxy-N-triethylammoniosulfonyl-methanimidate (Burgess reagent, 0.188 g, 0.790 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO₂, 4 g cartridge; methanol/dichloromethane=0% to 5%) to give N-(4-chlorophenyl)-N-(4-(5-(difluoromethyl)-1,3,4-oxadiazol-2-yl)benzyl)-4-ethylpiperazine-1-carboxamide as pale yellow oil (0.067 g, 26.8%).

¹H NMR (400 MHz, CDCl₃) δ 8.07-8.02 (m, 2H), 7.46 (d, 2H, J=8.2 Hz), 7.32-7.27 (m, 2H), 7.05-6.80 (m, 3H), 4.92 (s, 2H), 3.58-3.31 (m, 4H), 2.80-2.30 (m, 6H), 1.29-1.22 (m, 3H); LRMS (ES) m/z 476.1 (M⁺+1).

Example 340. Compound 21881: N-(4-Chlorophenyl)-N-(4-(5-(difluoromethyl)-1,3,4-oxadiazol-2-yl)-2-fluorobenzyl)-4-ethylpiperazine-1-carboxamide

[Step 1] N-(4-Chlorophenyl)-N-(4-(2-(2,2-difluoroacetyl)hydrazine-1-carbonyl)-2-fluorobenzyl)-4-ethylpiperazine-1-carboxamide

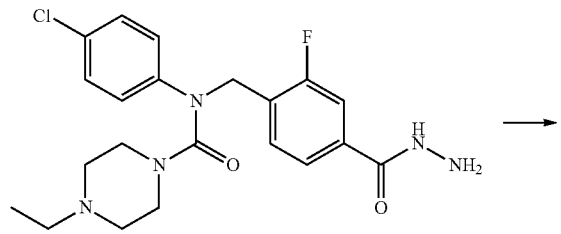

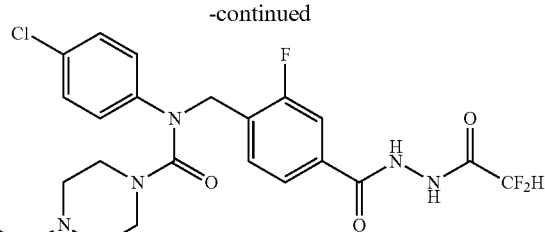

A solution of N-(4-chlorophenyl)-4-ethyl-N-(2-fluoro-4-(hydrazinecarbonyl)benzyl)piperazine-1-carboxamide (0.207 g, 0.477 mmol), triethylamine (0.073 mL, 0.525 mmol) and 2,2-difluoroacetic anhydride (0.059 mL, 0.477 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-chlorophenyl)-N-(4-(2-(2,2-difluoroacetyl)hydrazine-1-carbonyl)-2-fluorobenzyl)-4-ethylpiperazine-1-carboxamide, 0.240 g, 98.2%, pale yellow oil).

[Step 2] Compound 21881

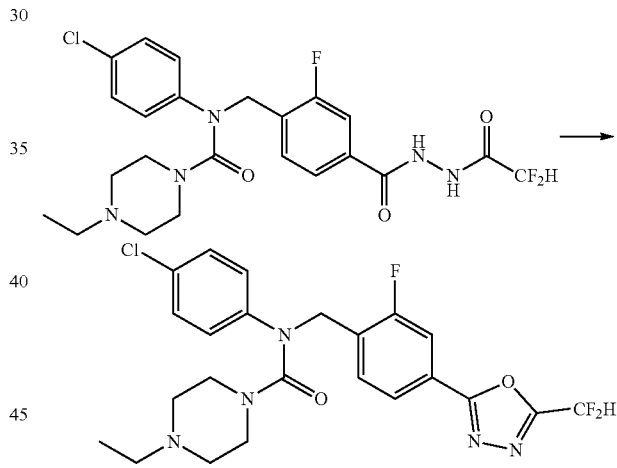

N-(4-Chlorophenyl)-N-(4-(2-(2,2-difluoroacetyl)hydrazine-1-carbonyl)-2-fluorobenzyl)-4-ethylpiperazine-1-carboxamide (0.240 g, 0.469 mmol) and 1-methoxy-N-triethylammoniosulfonyl-methanimidate (Burgess reagent, 0.168 g, 0.703 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO₂, 4 g cartridge; methanol/dichloromethane=0% to 5%) to give N-(4-chlorophenyl)-N-(4-(5-(difluoromethyl)-1,3,4-oxadiazol-2-yl)-2-fluorobenzyl)-4-ethylpiperazine-1-carboxamide as pale yellow oil (0.054 g, 23.4%).

¹H NMR (400 MHz, CDCl₃) δ 7.87 (dd, 1H, J=8.0, 1.7 Hz), 7.76 (dd, 1H, J=10.0, 1.7 Hz), 7.69 (t, 1H, J=7.6 Hz), 7.32-7.27 (m, 2H), 7.07-7.00 (m, 2H), 7.01-6.83 (m, 1H), 4.95 (s, 2H), 3.42 (s, 4H), 2.69-2.28 (m, 6H), 1.16 (s, 3H); LRMS (ES) m/z 494.1 (M⁺+1).

Example 341. Compound 21882: N-(4-Chlorophenyl)-N-((5-(5-(difluoromethyl)-1,3,4-oxadiazol-2-yl)pyridin-2-yl)methyl)-4-ethylpiperazine-1-carboxamide

[Step 1] N-(4-Chlorophenyl)-N-((5-(2-(2,2-difluoroacetyl)hydrazine-1-carbonyl)pyridin-2-yl)methyl)-4-ethylpiperazine-1-carboxamide

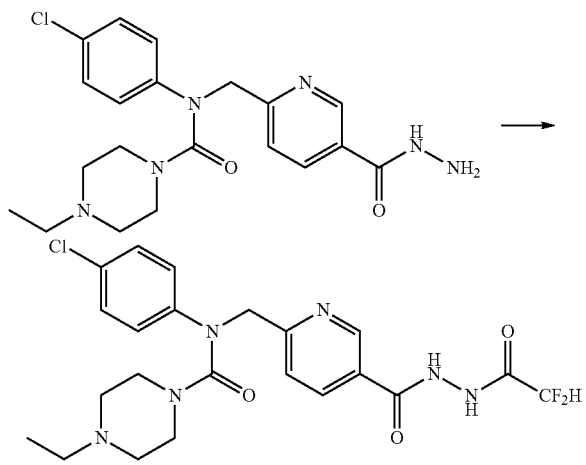

A solution of N-(4-chlorophenyl)-4-ethyl-N-((5-(hydrazinecarbonyl)pyridin-2-yl)methyl)piperazine-1-carboxamide (0.153 g, 0.367 mmol), triethylamine (0.056 mL, 0.404 mmol) and 2,2-difluoroacetic anhydride (0.046 mL, 0.367 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-chlorophenyl)-N-((5-(2-(2,2-difluoroacetyl)hydrazine-1-carbonyl)pyridin-2-yl)methyl)-4-ethylpiperazine-1-carboxamide, 0.180 g, 99.1%, pale yellow oil).

[Step 2] Compound 21882

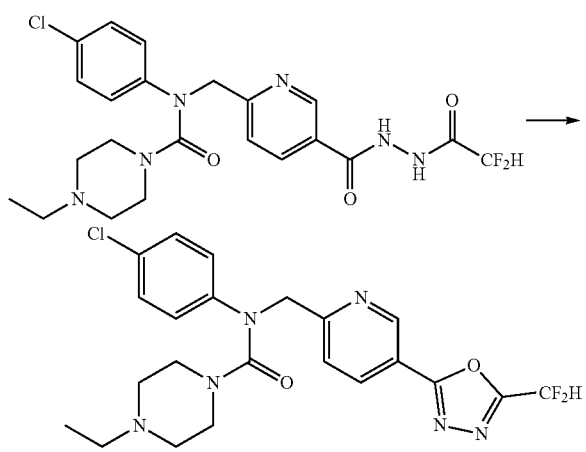

N-(4-Chlorophenyl)-N-((5-(2-(2,2-difluoroacetyl)hydrazine-1-carbonyl)pyridin-2-yl) methyl)-4-ethylpiperazine-1-carboxamide (0.180 g, 0.364 mmol) and 1-methoxy-N-triethylammoniosulfonyl-methanimidate (Burgess reagent, 0.130 g, 0.546 mmol) were mixed at the room temperature in tetrahydrofuran (4 mL) and then stirred at 70° C. for 18 hr. and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-chlorophenyl)-N-((5-(5-(difluoromethyl)-1,3,4-oxadiazol-2-yl)pyridin-2-yl)methyl)-4-ethylpiperazine-1-carboxamide as pale yellow oil (0.035 g, 19.9%).

$^1$H NMR (400 MHz, CDCl$_3$) δ 9.25 (dd, 1H, J=2.2, 0.8 Hz), 8.37 (dd, 1H, J=8.2, 2.2 Hz), 7.59-7.55 (m, 1H), 7.34-7.27 (m, 2H), 7.15-7.09 (m, 2H), 7.05-6.85 (m, 1H), 5.10 (s, 2H), 3.79-3.45 (m, 4H), 2.84 (brs, 6H), 1.30-1.22 (m, 3H); LRMS (ES) m/z 477.3 (M$^+$+1).

Example 342. Compound 21883: N-(4-(5-(Difluoromethyl)-1,3,4-oxadiazol-2-yl)benzyl)-4-ethyl-N-(3-fluorophenyl)piperazine-1-carboxamide

[Step 1] N-(4-(2-(2,2-Difluoroacetyl)hydrazine-1-carbonyl)benzyl)-4-ethyl-N-(3-fluorophenyl)piperazine-1-carboxamide

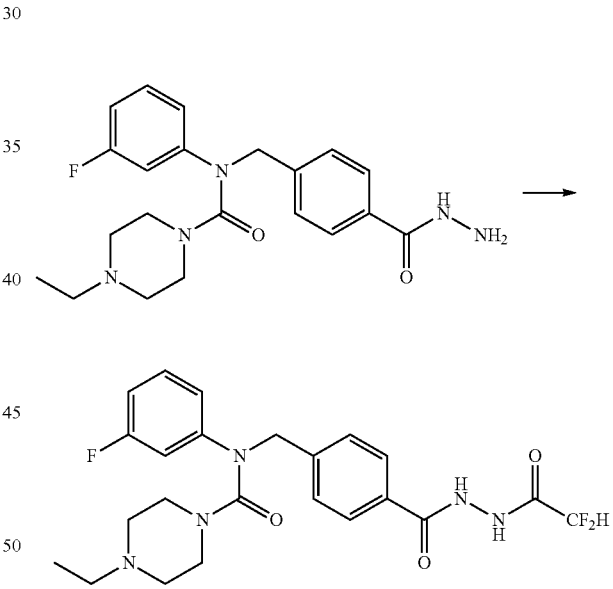

A solution of 4-ethyl-N-(3-fluorophenyl)-N-(4-(hydrazinecarbonyl)benzyl)piperazine-1-carboxamide (0.173 g, 0.433 mmol), triethylamine (0.066 mL, 0.476 mmol) and 2,2-difluoroacetic anhydride (0.054 mL, 0.433 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(2-(2,2-difluoroacetyl)hydrazine-1-carbonyl)benzyl)-4-ethyl-N-(3-fluorophenyl)piperazine-1-carboxamide, 0.200 g, 96.7%, pale yellow oil).

[Step 2] Compound 21883

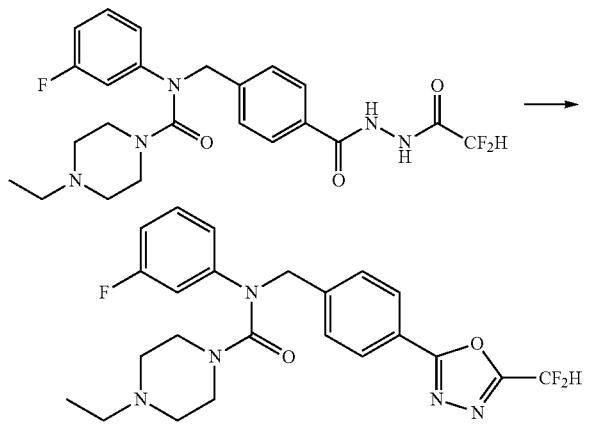

N-(4-(2-(2,2-Difluoroacetyl)hydrazine-1-carbonyl)benzyl)-4-ethyl-N-(3-fluorophenyl)piperazine-1-carboxamide (0.200 g, 0.419 mmol) and 1-methoxy-N-triethylammoniosulfonyl-methanimidate (Burgess reagent, 0.150 g, 0.628 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)benzyl)-4-ethyl-N-(3-fluorophenyl)piperazine-1-carboxamide as pale yellow oil (0.057 g, 29.6%).

$^1$H NMR (400 MHz, CDCl$_3$) δ 8.07-8.02 (m, 2H), 7.50-7.46 (m, 2H), 7.31-7.24 (m, 1H), 7.04-6.75 (m, 4H), 4.95 (s, 2H), 3.48-3.45 (m, 4H), 2.73-2.28 (m, 6H), 1.18 (s, 3H); LRMS (ES) m/z 460.4 (M$^+$+1).

Example 343. Compound 21884: N-(4-(5-(Difluoromethyl)-1,3,4-oxadiazol-2-yl)-2-fluorobenzyl)-4-ethyl-N-(3-fluorophenyl)piperazine-1-carboxamide

[Step 1] N-(4-(2-(2,2-Difluoroacetyl)hydrazine-1-carbonyl)-2-fluorobenzyl)-4-ethyl-N-(3-fluorophenyl)piperazine-1-carboxamide

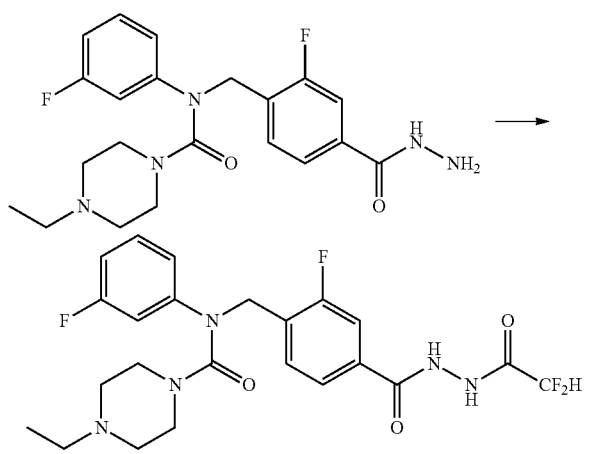

A solution of 4-ethyl-N-(2-fluoro-4-(hydrazinecarbonyl)benzyl)-N-(3-fluorophenyl)piperazine-1-carboxamide (0.178 g, 0.426 mmol), triethylamine (0.065 mL, 0.469 mmol) and 2,2-difluoroacetic anhydride (0.053 mL, 0.426 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(2-(2,2-difluoroacetyl)hydrazine-1-carbonyl)-2-fluorobenzyl)-4-ethyl-N-(3-fluorophenyl)piperazine-1-carboxamide, 0.210 g, 99.4%, pale yellow oil).

[Step 2] Compound 21884

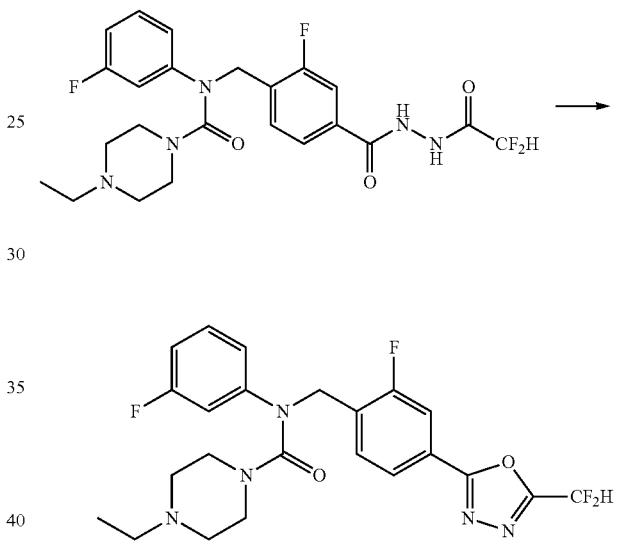

N-(4-(2-(2,2-Difluoroacetyl)hydrazine-1-carbonyl)-2-fluorobenzyl)-4-ethyl-N-(3-fluorophenyl)piperazine-1-carboxamide (0.210 g, 0.424 mmol) and 1-methoxy-N-triethylammoniosulfonyl-methanimidate (Burgess reagent, 0.151 g, 0.636 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-4-ethyl-N-(3-fluorophenyl)piperazine-1-carboxamide as pale yellow oil (0.054 g, 26.8%).

$^1$H NMR (400 MHz, CDCl$_3$) δ 7.88 (dd, 1H, J=8.0, 1.7 Hz), 7.77 (dd, 1H, J=10.1, 1.7 Hz), 7.70-7.65 (m, 1H), 7.32-7.26 (m, 1H), 7.02-6.80 (m, 4H), 4.98 (s, 2H), 3.44 (s, 4H), 2.71-2.32 (m, 6H), 1.19-1.14 (m, 3H); LRMS (ES) m/z 478.1 (M$^+$+1).

Example 344. Compound 21885: N-((5-(5-(Difluoromethyl)-1,3,4-oxadiazol-2-yl)pyridin-2-yl)methyl)-4-ethyl-N-(3-fluorophenyl)piperazine-1-carboxamide

[Step 1] N-((5-(2-(2,2-Difluoroacetyl)hydrazine-1-carbonyl)pyridin-2-yl)methyl)-4-ethyl-N-(3-fluorophenyl)piperazine-1-carboxamide

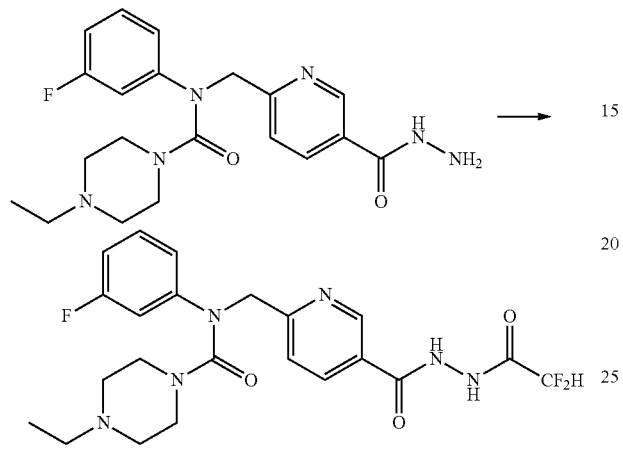

A solution of 4-ethyl-N-(3-fluorophenyl)-N-((5-(hydrazinecarbonyl)pyridin-2-yl)methyl)piperazine-1-carboxamide (0.155 g, 0.387 mmol), triethylamine (0.059 mL, 0.426 mmol) and 2,2-difluoroacetic anhydride (0.048 mL, 0.387 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-((5-(2-(2,2-difluoroacetyl)hydrazine-1-carbonyl)pyridin-2-yl)methyl)-4-ethyl-N-(3-fluorophenyl)piperazine-1-carboxamide, 0.180 g, 97.2%, pale yellow oil).

[Step 2] Compound 21885

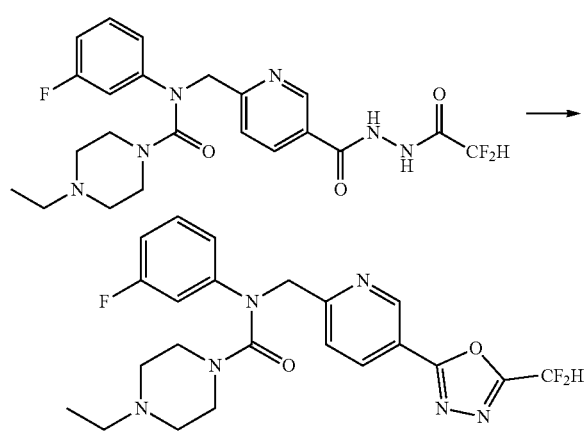

N-((5-(2-(2,2-Difluoroacetyl)hydrazine-1-carbonyl)pyridin-2-yl)methyl)-4-ethyl-N-(3-fluorophenyl)piperazine-1-carboxamide (0.180 g, 0.376 mmol) and 1-methoxy-N-triethylammoniosulfonyl-methanimidate (Burgess reagent, 0.134 g, 0.564 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-((5-(5-(difluoromethyl)-1,3,4-oxadiazol-2-yl)pyridin-2-yl)methyl)-4-ethyl-N-(3-fluorophenyl)piperazine-1-carboxamide as pale yellow oil (0.036 g, 21.0%).

$^1$H NMR (400 MHz, CDCl$_3$) δ 9.25 (dd, 1H, J=2.2, 0.8 Hz), 8.36 (dd, 1H, J=8.2, 2.3 Hz); 7.59 (dd, 1H, J=8.2, 0.8 Hz), 7.28 (td, 1H, J=8.2, 6.4 Hz), 7.06-6.86 (m, 3H), 6.83 (td, 1H, J=8.2, 2.6 Hz), 5.13 (s, 2H), 3.51 (s, 4H), 2.78-2.41 (m, 6H), 1.24-1.10 (m, 3H); LRMS (ES) m/z 461.1 (M$^+$+1).

Example 345. Compound 21886: N-(4-(5-(Difluoromethyl)-1,3,4-oxadiazol-2-yl)benzyl)-4-ethyl-N-(4-fluorophenyl)piperazine-1-carboxamide

[Step 1] N-(4-(2-(2,2-Difluoroacetyl)hydrazine-1-carbonyl)benzyl)-4-ethyl-N-(4-fluorophenyl)piperazine-1-carboxamide

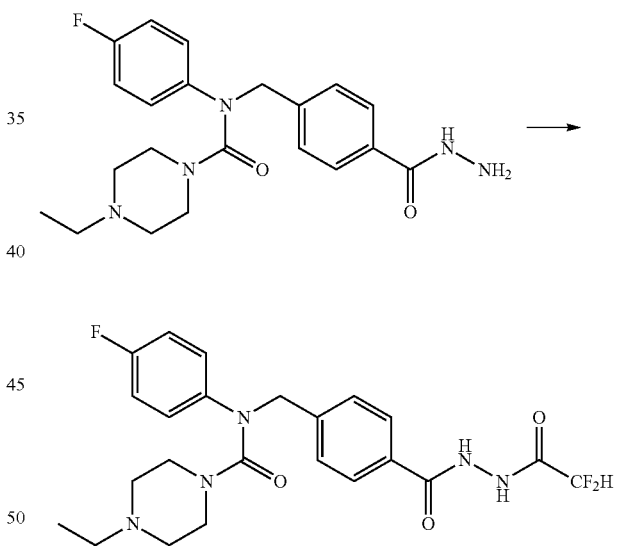

A solution of 4-ethyl-N-(4-fluorophenyl)-N-(4-(hydrazinecarbonyl)benzyl)piperazine-1-carboxamide (0.187 g, 0.468 mmol), triethylamine (0.072 mL, 0.515 mmol) and 2,2-difluoroacetic anhydride (0.058 mL, 0.468 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(2-(2,2-difluoroacetyl)hydrazine-1-carbonyl)benzyl)-4-ethyl-N-(4-fluorophenyl)piperazine-1-carboxamide, 0.220 g, 98.4%, pale yellow oil).

[Step 2] Compound 21886

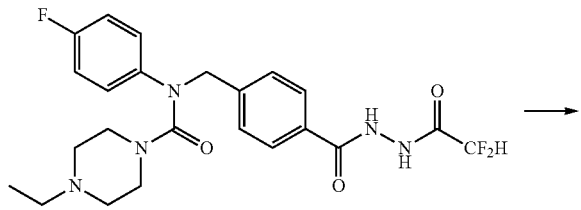

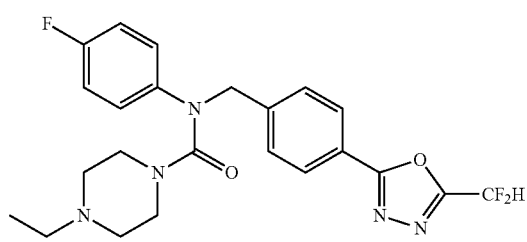

N-(4-(2-(2,2-Difluoroacetyl)hydrazine-1-carbonyl)benzyl)-4-ethyl-N-(4-fluorophenyl)piperazine-1-carboxamide (0.220 g, 0.461 mmol) and 1-methoxy-N-triethylammoniosulfonyl-methanimidate (Burgess reagent, 0.165 g, 0.691 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)benzyl)-4-ethyl-N-(4-fluorophenyl)piperazine-1-carboxamide as pale yellow oil (0.045 g, 21.2%).

$^1$H NMR (400 MHz, CDCl$_3$) δ 8.06-8.02 (m, 2H), 7.45 (d, 2H, J=8.2 Hz), 7.05-7.00 (m, 4H), 7.00-6.81 (m, 1H), 4.90 (s, 2H), 3.49 (s, 4H), 2.65 (s, 6H), 1.26-1.20 (m, 3H); LRMS (ES) m/z 460.1 (M$^+$+1).

Example 346. Compound 21887: N-(4-(5-(Difluoromethyl)-1,3,4-oxadiazol-2-yl)-2-fluorobenzyl)-4-ethyl-N-(4-fluorophenyl)piperazine-1-carboxamide

[Step 1] N-(4-(2-(2,2-Difluoroacetyl)hydrazine-1-carbonyl)-2-fluorobenzyl)-4-ethyl-N-(4-fluorophenyl)piperazine-1-carboxamide

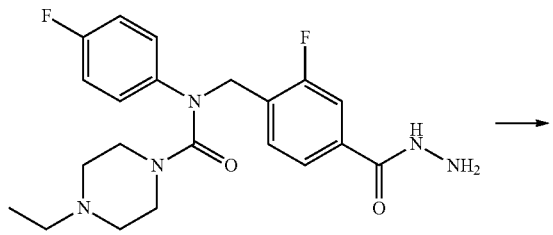

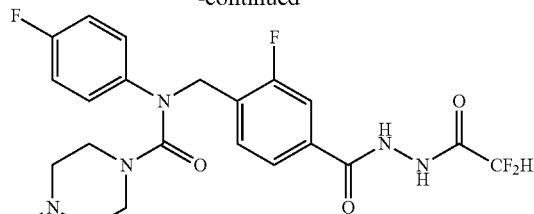

A solution of 4-ethyl-N-(2-fluoro-4-(hydrazinecarbonyl)benzyl)-N-(4-fluorophenyl)piperazine-1-carboxamide (0.211 g, 0.505 mmol), triethylamine (0.077 mL, 0.556 mmol) and 2,2-difluoroacetic anhydride (0.063 mL, 0.505 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(2-(2,2-difluoroacetyl)hydrazine-1-carbonyl)-2-fluorobenzyl)-4-ethyl-N-(4-fluorophenyl)piperazine-1-carboxamide, 0.250 g, 99.8%, pale yellow oil).

[Step 2] Compound 21887

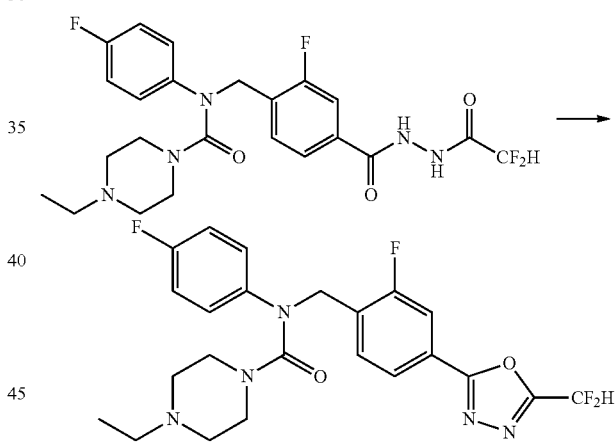

N-(4-(2-(2,2-Difluoroacetyl)hydrazine-1-carbonyl)-2-fluorobenzyl)-4-ethyl-N-(4-fluorophenyl)piperazine-1-carboxamide (0.250 g, 0.505 mmol) and 1-methoxy-N-triethylammoniosulfonyl-methanimidate (Burgess reagent, 0.180 g, 0.757 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-4-ethyl-N-(4-fluorophenyl)piperazine-1-carboxamide as pale yellow oil (0.055 g, 22.9%).

$^1$H NMR (400 MHz, CDCl$_3$) δ 7.88 (dd, 1H, J=8.0, 1.7 Hz), 7.75 (dd, 1H, J=10.0, 1.7 Hz), 7.71 (t, 1H, J=7.6 Hz), 7.13-7.01 (m, 4H), 7.00-6.81 (m, 1H), 4.93 (s, 2H), 3.40-3.36 (m, 4H), 2.62-2.23 (m, 6H), 1.12 (s, 3H); LRMS (ES) m/z 478.1 (M$^+$+1).

1059

Example 347. Compound 21888: N-((5-(5-(Difluoromethyl)-1,3,4-oxadiazol-2-yl)pyridin-2-yl)methyl)-4-ethyl-N-(4-fluorophenyl)piperazine-1-carboxamide

[Step 1] N-((5-(2-(2,2-Difluoroacetyl)hydrazine-1-carbonyl)pyridin-2-yl)methyl)-4-ethyl-N-(4-fluorophenyl)piperazine-1-carboxamide

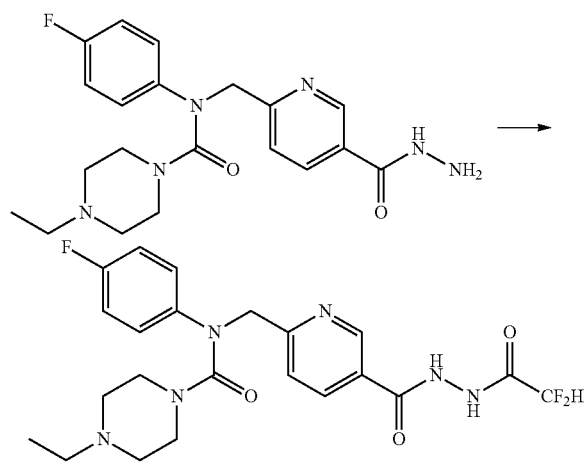

A solution of 4-ethyl-N-(4-fluorophenyl)-N-((5-(hydrazinecarbonyl)pyridin-2-yl)methyl)piperazine-1-carboxamide (0.176 g, 0.439 mmol), triethylamine (0.067 mL, 0.483 mmol) and 2,2-difluoroacetic anhydride (0.055 mL, 0.439 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-((5-(2-(2,2-difluoroacetyl)hydrazine-1-carbonyl)pyridin-2-yl)methyl)-4-ethyl-N-(4-fluorophenyl)piperazine-1-carboxamide, 0.210 g, 99.9%, pale yellow oil).

[Step 2] Compound 21888

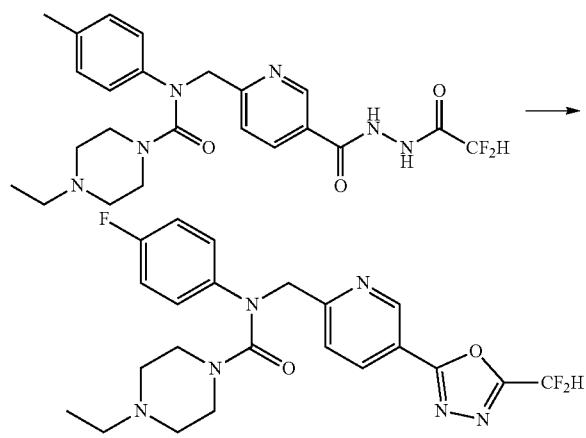

1060

N-((5-(2-(2,2-Difluoroacetyl)hydrazine-1-carbonyl)pyridin-2-yl)methyl)-4-ethyl-N-(4-fluorophenyl)piperazine-1-carboxamide (0.210 g, 0.439 mmol) and 1-methoxy-N-triethylammoniosulfonyl-methanimidate (Burgess reagent, 0.157 g, 0.658 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-((5-(5-(difluoromethyl)-1,3,4-oxadiazol-2-yl)pyridin-2-yl)methyl)-4-ethyl-N-(4-fluorophenyl)piperazine-1-carboxamide as pale yellow oil (0.042 g, 20.8%).

$^1$H NMR (400 MHz, CDCl$_3$) δ 9.24 (dd, 1H, J=2.3, 0.8 Hz), 8.36 (dd, 1H, J=8.2, 2.2 Hz), 7.61 (d, 1H, J=8.2 Hz), 7.19-7.13 (m, 2H), 7.05-6.87 (m, 3H), 5.08 (s, 2H), 3.47 (s, 4H), 2.60 (brs, 6H), 1.24-1.11 (m, 3H); LRMS (ES) m/z 461.1 (M$^+$+1).

Example 348. Compound 21889: N-(4-(5-(Difluoromethyl)-1,3,4-oxadiazol-2-yl)benzyl)-4-ethyl-N-(3-methoxyphenyl)piperazine-1-carboxamide

[Step 1] N-(4-(2-(2,2-Difluoroacetyl)hydrazine-1-carbonyl)benzyl)-4-ethyl-N-(3-methoxyphenyl)piperazine-1-carboxamide

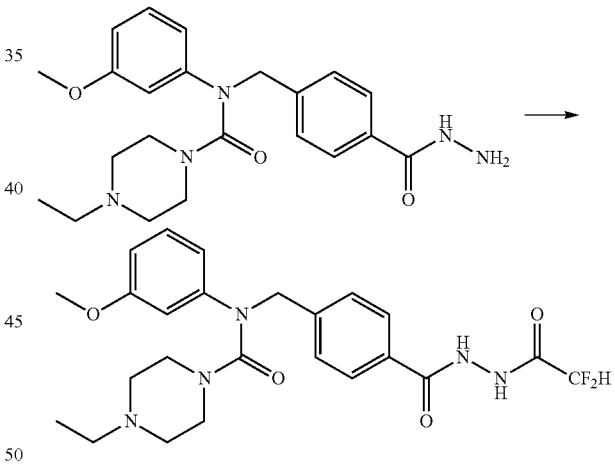

A solution of 4-ethyl-N-(4-(hydrazinecarbonyl)benzyl)-N-(3-methoxyphenyl)piperazine-1-carboxamide (0.239 g, 0.581 mmol), triethylamine (0.089 mL, 0.639 mmol) and 2,2-difluoroacetic anhydride (0.072 mL, 0.581 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(2-(2,2-difluoroacetyl)hydrazine-1-carbonyl)benzyl)-4-ethyl-N-(3-methoxyphenyl)piperazine-1-carboxamide, 0.280 g, 98.5%, pale yellow oil).

[Step 2] Compound 21889

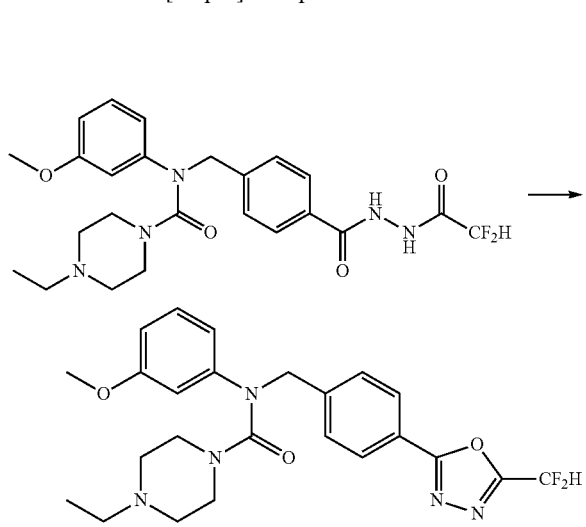

N-(4-(2-(2,2-Difluoroacetyl)hydrazine-1-carbonyl)benzyl)-4-ethyl-N-(3-methoxyphenyl)piperazine-1-carboxamide (0.280 g, 0.572 mmol) and 1-methoxy-N-triethylammoniosulfonyl-methanimidate (Burgess reagent, 0.204 g, 0.858 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)benzyl)-4-ethyl-N-(3-methoxyphenyl)piperazine-1-carboxamide as white solid (0.104 g, 38.5%).

$^1$H NMR (400 MHz, CDCl$_3$) δ 8.08-8.01 (m, 2H), 7.55-7.47 (m, 2H), 7.22 (t, 1H, J=8.1 Hz), 7.01-6.82 (m, 1H), 6.69-6.67 (m, 1H), 6.66-6.64 (m, 1H), 6.60 (t, 1H, J=2.3 Hz), 4.94 (s, 2H), 3.77 (s, 3H), 3.45 (s, 4H), 2.52 (brs, 6H), 1.17 (s, 3H).

Example 349. Compound 21890: N-(4-(5-(Difluoromethyl)-1,3,4-oxadiazol-2-yl)-2-fluorobenzyl)-4-ethyl-N-(3-methoxyphenyl)piperazine-1-carboxamide

[Step 1] N-(4-(2-(2,2-Difluoroacetyl)hydrazine-1-carbonyl)-2-fluorobenzyl)-4-ethyl-N-(3-methoxyphenyl)piperazine-1-carboxamide

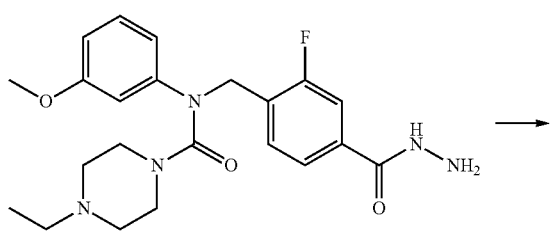

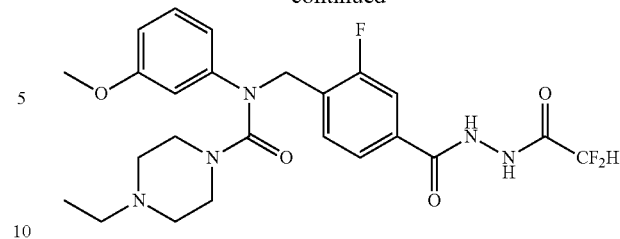

A solution of 4-ethyl-N-(2-fluoro-4-(hydrazinecarbonyl)benzyl)-N-(3-methoxyphenyl)piperazine-1-carboxamide (0.256 g, 0.596 mmol), triethylamine (0.091 mL, 0.656 mmol) and 2,2-difluoroacetic anhydride (0.074 mL, 0.596 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(2-(2,2-difluoroacetyl)hydrazine-1-carbonyl)-2-fluorobenzyl)-4-ethyl-N-(3-methoxyphenyl)piperazine-1-carboxamide, 0.300 g, 99.2%, pale yellow oil).

[Step 2] Compound 21890

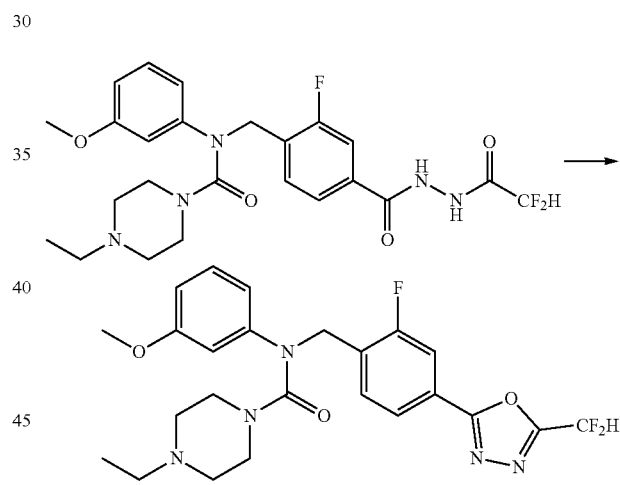

N-(4-(2-(2,2-Difluoroacetyl)hydrazine-1-carbonyl)-2-fluorobenzyl)-4-ethyl-N-(3-methoxyphenyl)piperazine-1-carboxamide (0.300 g, 0.591 mmol) and 1-methoxy-N-triethylammoniosulfonyl-methanimidate (Burgess reagent, 0.211 g, 0.887 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-4-ethyl-N-(3-methoxyphenyl)piperazine-1-carboxamide as pale yellow oil (0.111 g, 38.5%).

$^1$H NMR (400 MHz, CDCl$_3$) δ 7.85 (dd, 1H, J=8.0, 1.7 Hz), 7.75 (dd, 1H, J=10.0, 1.7 Hz), 7.70-7.65 (m, 1H), 7.20 (t, 1H, J=8.1 Hz), 7.00-6.83 (m, 1H), 6.69-6.67 (m, 1H), 6.67-6.65 (m, 1H), 6.64 (t, 1H, J=2.2 Hz), 4.98 (s, 2H), 3.77

(s, 3H), 3.35 (t, 4H, J=4.9 Hz), 2.41 (q, 2H, J=7.2 Hz), 2.34 (d, 4H, J=5.3 Hz), 1.07 (t, 3H, J=7.2 Hz); LRMS (ES) m/z 490.1 (M⁺+1).

Example 350. Compound 21891: N-((5-(5-(Difluoromethyl)-1,3,4-oxadiazol-2-yl)pyridin-2-yl)methyl)-4-ethyl-N-(3-methoxyphenyl)piperazine-1-carboxamide

[Step 1] N-((5-(2-(2,2-Difluoroacetyl)hydrazine-1-carbonyl)pyridin-2-yl)methyl)-4-ethyl-N-(3-methoxyphenyl)piperazine-1-carboxamide

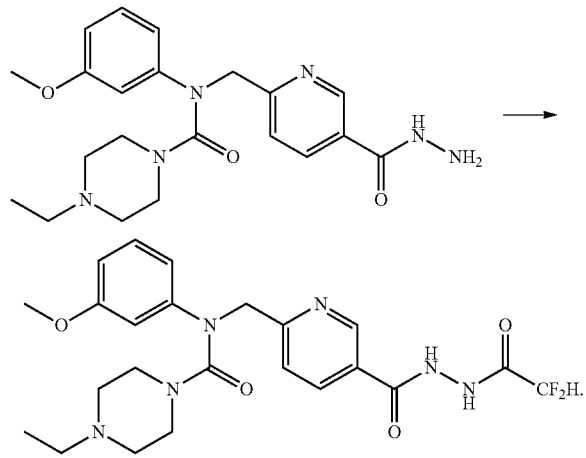

A solution of 4-ethyl-N-((5-(hydrazinecarbonyl)pyridin-2-yl)methyl)-N-(3-methoxyphenyl)piperazine-1-carboxamide (0.172 g, 0.417 mmol), triethylamine (0.064 mL, 0.459 mmol) and 2,2-difluoroacetic anhydride (0.052 mL, 0.417 mmol) in dichloromethane (4 mL) was stirred at the room temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-((5-(2-(2,2-difluoroacetyl)hydrazine-1-carbonyl)pyridin-2-yl)methyl)-4-ethyl-N-(3-methoxyphenyl)piperazine-1-carboxamide, 0.200 g, 97.8%, pale yellow oil).

[Step 2] Compound 21891

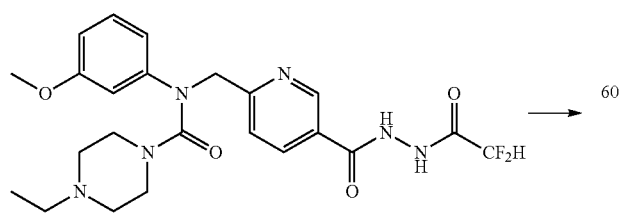

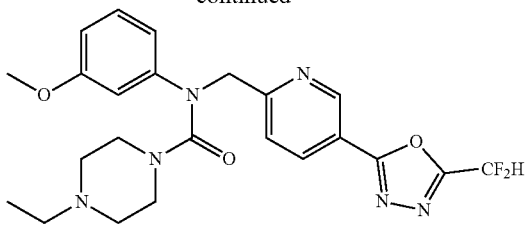

N-((5-(2-(2,2-Difluoroacetyl)hydrazine-1-carbonyl)pyridin-2-yl)methyl)-4-ethyl-N-(3-methoxyphenyl)piperazine-1-carboxamide (0.200 g, 0.408 mmol) and 1-methoxy-N-triethylammoniosulfonyl-methanimidate (Burgess reagent, 0.146 g, 0.612 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO₂, 4 g cartridge; methanol/dichloromethane=0% to 5%) to give N-((5-(5-(difluoromethyl)-1,3,4-oxadiazol-2-yl)pyridin-2-yl)methyl)-4-ethyl-N-(3-methoxyphenyl)piperazine-1-carboxamide as pale yellow oil (0.072 g, 37.4%).

¹H NMR (400 MHz, CDCl₃) δ 9.23 (dd, 1H, J=2.2, 0.9 Hz), 8.33 (dd, 1H, J=8.2, 2.2 Hz), 7.60 (dd, 1H, J=8.2, 0.8 Hz), 7.21 (t, 1H, J=8.1 Hz), 7.03-6.86 (m, 1H), 6.75-6.73 (m, 1H), 6.71 (t, 1H, J=2.3 Hz), 6.66-6.63 (m, 1H), 5.12 (s, 2H), 3.78 (s, 3H), 3.42 (t, 4H, J=5.0 Hz), 2.55-2.36 (m, 6H), 1.13 (t, 3H, J=7.2 Hz); LRMS (ES) m/z 473.1 (M⁺+1).

Example 351. Compound 21892: N-(4-(5-(Difluoromethyl)-1,3,4-oxadiazol-2-yl)benzyl)-4-ethyl-N-(4-methoxyphenyl)piperazine-1-carboxamide

[Step 1] N-(4-(2-(2,2-Difluoroacetyl)hydrazine-1-carbonyl)benzyl)-4-ethyl-N-(4-methoxyphenyl)piperazine-1-carboxamide

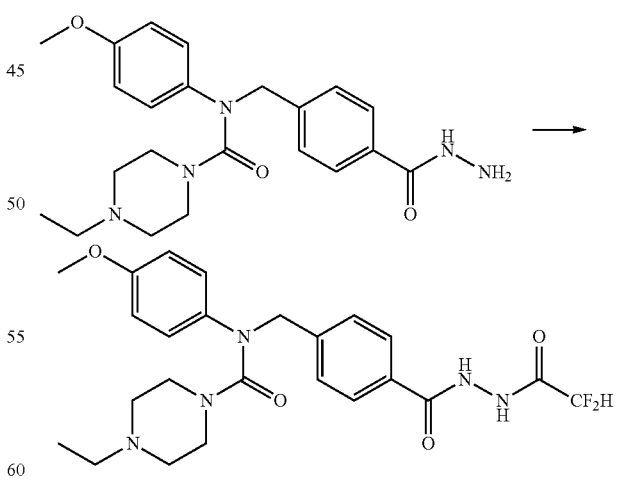

A solution of 4-ethyl-N-(4-(hydrazinecarbonyl)benzyl)-N-(4-methoxyphenyl)piperazine-1-carboxamide (0.263 g, 0.639 mmol), triethylamine (0.098 mL, 0.703 mmol) and 2,2-difluoroacetic anhydride (0.079 mL, 0.639 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(2-(2,2-difluoroacetyl)hydrazine-1-carbonyl)benzyl)-4-ethyl-N-(4-methoxyphenyl)piperazine-1-carboxamide, 0.310 g, 99.1%, pale yellow oil).

[Step 2] Compound 21892

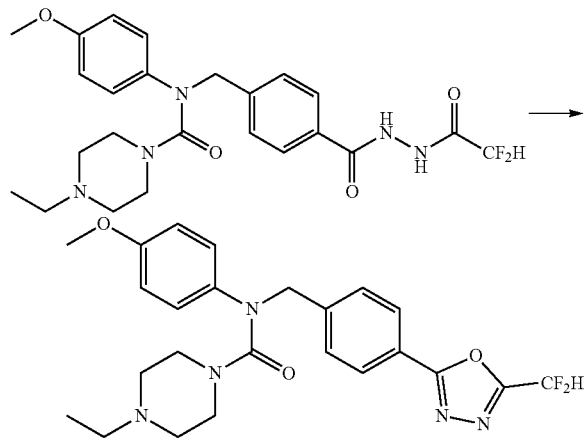

N-(4-(2-(2,2-Difluoroacetyl)hydrazine-1-carbonyl)benzyl)-4-ethyl-N-(4-methoxyphenyl)piperazine-1-carboxamide (0.310 g, 0.633 mmol) and 1-methoxy-N-triethylammoniosulfonyl-methanimidate (Burgess reagent, 0.226 g, 0.950 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)benzyl)-4-ethyl-N-(4-methoxyphenyl)piperazine-1-carboxamide as pale yellow oil (0.096 g, 32.3%).

$^1$H NMR (400 MHz, CDCl$_3$) δ 8.04-7.99 (m, 2H), 7.48-7.44 (m, 2H), 7.03-6.79 (m, 5H), 4.87 (s, 2H), 3.79 (s, 3H), 3.36-3.30 (m, 4H), 2.44 (q, 2H, J=8.2 Hz), 2.35 (s, 4H), 1.09 (t, 3H, J=7.2 Hz); LRMS (ES) m/z 472.1 (M$^+$+1).

Example 352. Compound 21893: N-(4-(5-(Difluoromethyl)-1,3,4-oxadiazol-2-yl)-2-fluorobenzyl)-4-ethyl-N-(4-methoxyphenyl)piperazine-1-carboxamide

[Step 1] N-(4-(2-(2,2-Difluoroacetyl)hydrazine-1-carbonyl)-2-fluorobenzyl)-4-ethyl-N-(4-methoxyphenyl)piperazine-1-carboxamide

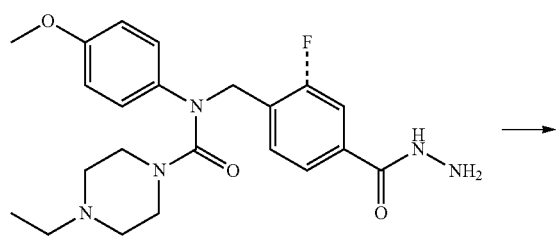

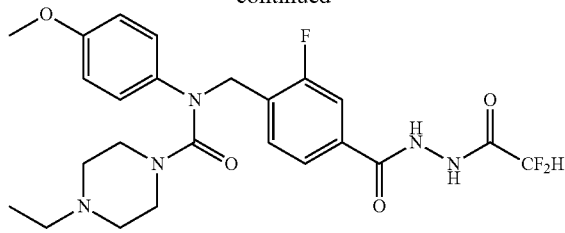

A solution of 4-ethyl-N-(2-fluoro-4-(hydrazinecarbonyl)benzyl)-N-(4-methoxyphenyl)piperazine-1-carboxamide (0.227 g, 0.529 mmol), triethylamine (0.081 mL, 0.581 mmol) and 2,2-difluoroacetic anhydride (0.066 mL, 0.529 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-(4-(2-(2,2-difluoroacetyl)hydrazine-1-carbonyl)-2-fluorobenzyl)-4-ethyl-N-(4-methoxyphenyl)piperazine-1-carboxamide, 0.260 g, 96.9%, pale yellow oil).

[Step 2] Compound 21893

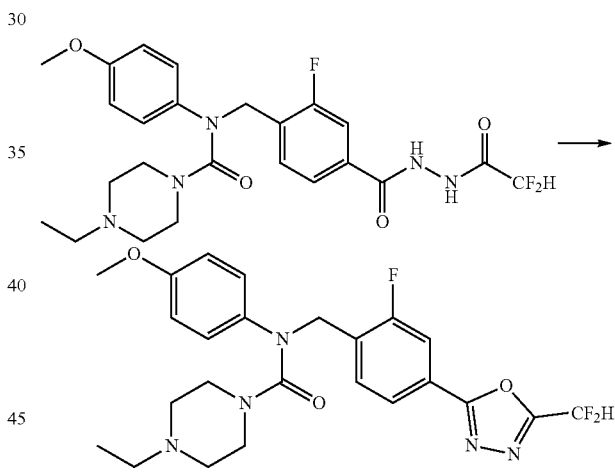

N-(4-(2-(2,2-Difluoroacetyl)hydrazine-1-carbonyl)-2-fluorobenzyl)-4-ethyl-N-(4-methoxyphenyl)piperazine-1-carboxamide (0.260 g, 0.512 mmol) and 1-methoxy-N-triethylammoniosulfonyl-methanimidate (Burgess reagent, 0.183 g, 0.768 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-4-ethyl-N-(4-methoxyphenyl)piperazine-1-carboxamide as pale yellow oil (0.096 g, 38.4%).

$^1$H NMR (400 MHz, CDCl$_3$) δ 7.86 (dd, 1H, J=8.0, 1.7 Hz), 7.75-7.68 (m, 2H), 7.03-7.00 (m, 2H), 7.00-6.84 (m, 1H), 6.84-6.81 (m, 2H), 4.91 (s, 2H), 3.79 (s, 3H), 3.34 (s, 4H), 2.43 (s, 2H), 2.33 (s, 4H), 1.08 (t, 3H, J=7.1 Hz); LRMS (ES) m/z 490.1 (M$^+$+1).

Example 353. Compound 21894: N-((5-(5-(Difluoromethyl)-1,3,4-oxadiazol-2-yl)pyridin-2-yl)methyl)-4-ethyl-N-(4-methoxyphenyl)piperazine-1-carboxamide

[Step 1] N-((5-(2-(2,2-Difluoroacetyl)hydrazine-1-carbonyl)pyridin-2-yl)methyl)-4-ethyl-N-(4-methoxyphenyl)piperazine-1-carboxamide

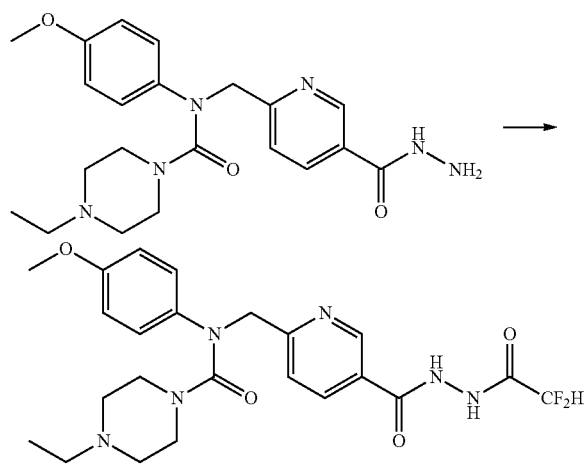

A solution of 4-ethyl-N-((5-(hydrazinecarbonyl)pyridin-2-yl)methyl)-N-(4-methoxyphenyl)piperazine-1-carboxamide (0.211 g, 0.512 mmol), triethylamine (0.078 mL, 0.563 mmol) and 2,2-difluoroacetic anhydride (0.064 mL, 0.512 mmol) in dichloromethane (4 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-((5-(2-(2,2-difluoroacetyl)hydrazine-1-carbonyl)pyridin-2-yl)methyl)-4-ethyl-N-(4-methoxyphenyl)piperazine-1-carboxamide, 0.250 g, 99.6%, pale yellow oil).

[Step 2] Compound 21894

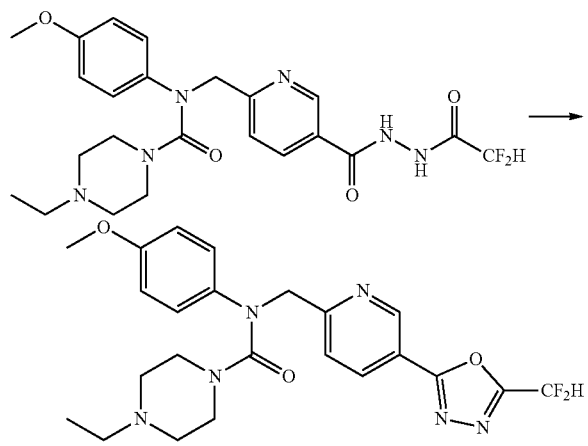

N-((5-(2-(2,2-Difluoroacetyl)hydrazine-1-carbonyl)pyridin-2-yl)methyl)-4-ethyl-N-(4-methoxyphenyl)piperazine-1-carboxamide (0.250 g, 0.510 mmol) and 1-methoxy-N-triethylammoniosulfonyl-methanimidate (Burgess reagent, 0.182 g, 0.765 mmol) were mixed at the room temperature in tetrahydrofuran (4 mL) and then stirred at 70° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 5%) to give N-((5-(5-(difluoromethyl)-1,3,4-oxadiazol-2-yl)pyridin-2-yl)methyl)-4-ethyl-N-(4-methoxyphenyl)piperazine-1-carboxamide as pale yellow oil (0.037 g, 15.4%).

$^1$H NMR (400 MHz, CDCl$_3$) δ 9.24 (dd, 1H, J=2.3, 0.8 Hz), 8.36 (dd, 1H, J=8.2, 2.2 Hz), 7.59-7.55 (m, 1H), 7.13-7.07 (m, 2H), 7.04-6.88 (m, 1H), 6.87-6.84 (m, 2H), 5.07 (s, 2H), 3.81 (s, 3H), 3.68-3.51 (m, 4H), 2.97 (s, 2H), 2.72 (brs, 4H), 1.49-1.34 (m, 3H); LRMS (ES) m/z 473.1 (M$^+$+1).

Example 354. Compound 21895: N-(4-(5-(difluoromethyl)-1,3,4-oxadiazol-2-yl)-2-fluorobenzyl)-N-(4-((4-neopentylpiperazin-1-yl)methyl)phenyl)thiomorpholine-4-carboxamide 1,1-dioxide

[Step 1] N-(4-(chloromethyl)phenyl)thiomorpholine-4-carboxamide 1,1-dioxide

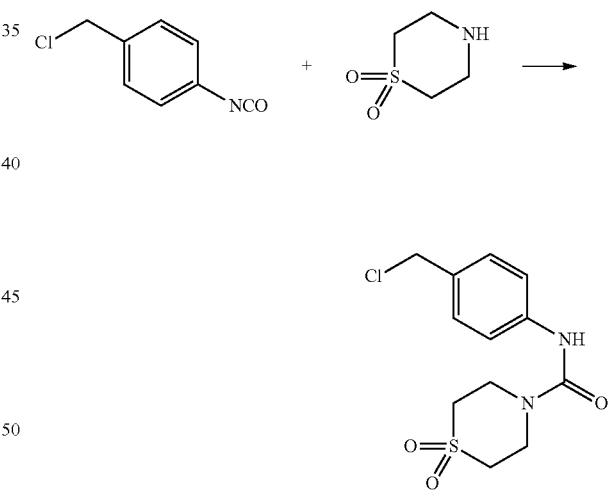

A solution of 1-(chloromethyl)-4-isocyanatobenzene (2.000 g, 11.934 mmol) and thiomorpholine 1,1-dioxide (1.613 g, 11.934 mmol) in diethylether (30 mL) prepared at the room temperature was stirred at the same temperature for 18 hr. The precipitates were collected by filtration, washed by diethylether, and dried to give N-(4-(chloromethyl)phenyl)thiomorpholine-4-carboxamide 1,1-dioxide as orange solid (3.210 g, 88.8%).

1069

[Step 2] Tert-butyl 4-(4-(1,1-dioxidothiomorpho-line-4-carboxamido)benzyl)piperazine-1-carboxylate

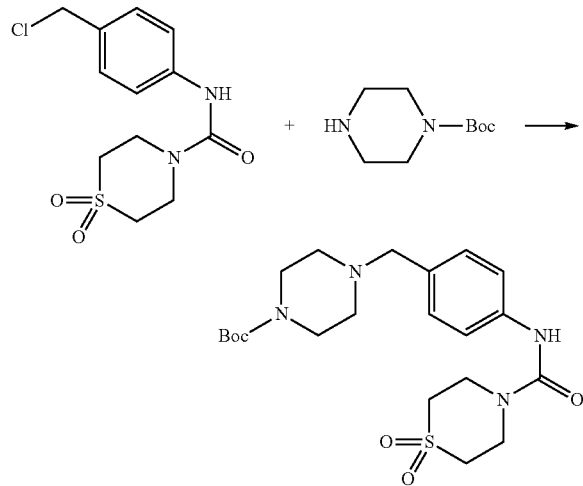

A solution of N-(4-(chloromethyl)phenyl)thiomorpholine-4-carboxamide 1,1-dioxide (1.500 g, 4.954 mmol), tert-butyl piperazine-1-carboxylate (2.768 g, 14.863 mmol) and potassium carbonate (2.054 g, 14.863 mmol) in acetonitrile (50 mL) prepared at the room temperature was stirred at the same temperature for 18 hr, concentrated under the reduced pressure to remove the solvent. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with diethylether (15 mL) and stirred. The resulting precipitates were collected by filtration, washed by diethylether, and dried to give tert-butyl 4-(4-(1,1-dioxidothiomorpholine-4-carboxamido)benzyl)piperazine-1-carboxylate as white solid (1.990 g, 88.8%).

[Step 3] Tert-butyl 4-(4-(N-(2-fluoro-4-(methoxycarbonyl)benzyl)-1,1-dioxidothiomorpholine-4-carboxamido)benzyl)piperazine-1-carboxylate

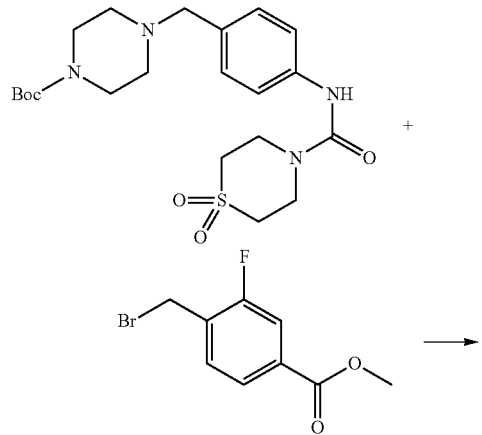

1070

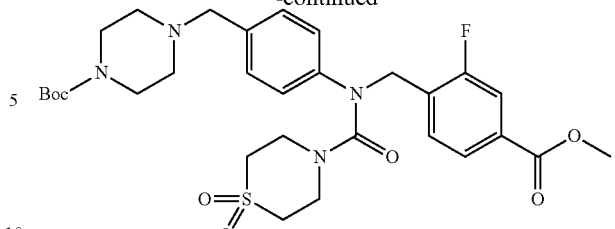

A solution of tert-butyl 4-(4-(1,1-dioxidothiomorpholine-4-carboxamido)benzyl)piperazine-1-carboxylate (1.990 g, 4.397 mmol) and sodium hydride (60.00%, 0.193 g, 4.837 mmol) in N,N-dimethylformamide (20 mL) was stirred at 0° C. for 30 min, and mixed with methyl 4-(bromomethyl)-3-fluorobenzoate (1.195 g, 4.837 mmol). The reaction mixture was stirred at the room temperature for additional 17 hr, quenched at the room temperature by the addition of water (50 mL, 10 min stirring). Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 24 g cartridge; methanol/dichloromethane=0% to 5%) to give tert-butyl 4-(4-(N-(2-fluoro-4-(methoxycarbonyl)benzyl)-1,1-dioxidothiomorpholine-4-carboxamido)benzyl)piperazine-1-carboxylate as yellow solid (2.700 g, 99.2%).

[Step 4] Methyl 4-((1,1-dioxido-N-(4-(piperazin-1-ylmethyl)phenyl)thiomorpholine-4-carboxamido)methyl)-3-fluorobenzoate hydrochloride

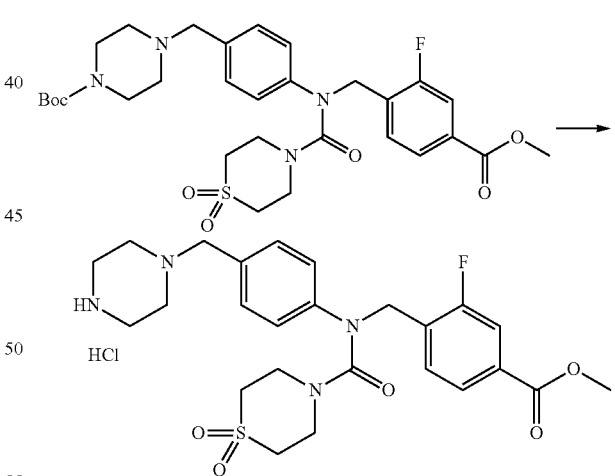

A solution of tert-butyl 4-(4-(N-(2-fluoro-4-(methoxycarbonyl)benzyl)-1,1-dioxidothiomorpholine-4-carboxamido)benzyl)piperazine-1-carboxylate (1.990 g, 3.216 mmol) and hydrochloric acid (4.00 M solution, 1.608 mL, 6.433 mmol) in dichloromethane (100 mL) prepared at the room temperature was stirred at the same temperature for 18 hr. The reaction mixture was concentrated under the reduced pressure to remove the solvent The residue was diluted with ethyl acetate (100 mL) and stirred. The resulting precipitates were collected by filtration, washed by ethyl acetate, and dried to give methyl 4-((1,1-dioxido-N-(4-(piperazin-1-ylmethyl)phenyl)thiomorpholine-4-carboxamido)methyl)-3-fluorobenzoate hydrochloride as white solid (1.780 g, 99.7%).

[Step 5] Methyl 3-fluoro-4-((N-(4-((4-neopentylpiperazin-1-yl)methyl)phenyl)-1,1-dioxidothiomorpholine-4-carboxamido)methyl)benzoate

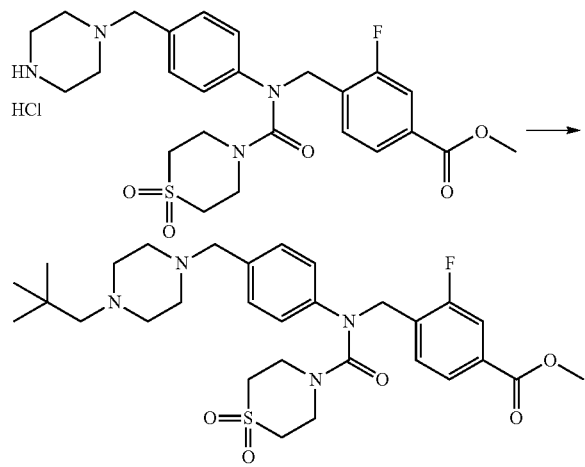

Pivalaldehyde (0.070 g, 0.811 mmol) was added to a solution of methyl 4-((1,1-dioxido-N-(4-(piperazin-1-ylmethyl)phenyl)thiomorpholine-4-carboxamido)methyl)-3-fluorobenzoate hydrochloride (0.300 g, 0.540 mmol) and N,N-diisopropylethylamine (0.094 mL, 0.540 mmol) in dichloromethane (5 mL) at the room temperature, and the mixture was stirred for 10 min at the same temperature. The reaction mixture was treated at the same temperature with sodium triacetoxyborohydride (0.229 g, 1.081 mmol) and stirred for additional 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give methyl 3-fluoro-4-((N-(4-((4-neopentylpiperazin-1-yl)methyl)phenyl)-1,1-dioxidothiomorpholine-4-carboxamido)methyl)benzoate as white solid (0.148 g, 46.5%).

[Step 6] N-(2-fluoro-4-(hydrazinecarbonyl)benzyl)-N-(4-((4-neopentylpiperazin-1-yl)methyl)phenyl) thiomorpholine-4-carboxamide

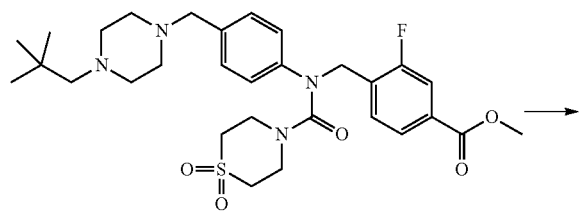

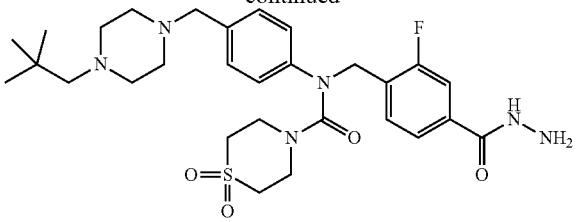

Methyl 3-fluoro-4-((N-(4-((4-neopentylpiperazin-1-yl)methyl)phenyl)-1,1-dioxidothiomorpholine-4-carboxamido)methyl)benzoate (0.148 g, 0.251 mmol) and hydrazine monohydrate (0.244 mL, 5.028 mmol) were mixed at the room temperature in ethanol (5 mL) and then stirred at 100° C. for 5 hr, cooled down to the room temperature to terminate the reaction. The precipitates were collected by filtration, washed by ethanol, and dried to give N-(2-fluoro-4-(hydrazinecarbonyl)benzyl)-N-(4-((4-neopentylpiperazin-1-yl)methyl)phenyl)thiomorpholine-4-carboxamide as white solid (0.098 g, 66.2%).

[Step 7] N-(4-(2-(2,2-difluoroacetyl)hydrazine-1-carbonyl)-2-fluorobenzyl)-N-(4-((4-neopentylpiperazin-1-yl)methyl)phenyl)thiomorpholine-4-carboxamide 1,1-dioxide

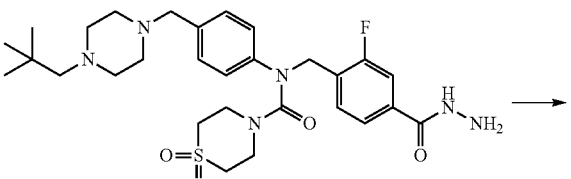

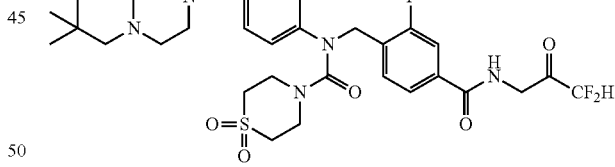

A solution of N-(2-fluoro-4-(hydrazinecarbonyl)benzyl)-N-(4-((4-neopentylpiperazin-1-yl)methyl)phen yl)thiomorpholine-4-carboxamide 1,1-dioxide (0.050 g, 0.085 mmol) and triethylamine (0.036 mL, 0.255 mmol) in tetrahydrofuran (5 mL) was mixed at the room temperature with 2,2-difluoroacetic anhydride (0.021 mL, 0.170 mmol), stirred at the same temperature for 17 hr. The reaction mixture was concentrated under the reduced pressure to remove the solvent The concentrate was purified and concentrated by column chromatography (SiO$_2$, 4 g cartridge; methanol/dichloromethane=0% to 10%) to give N-(4-(2-(2,2-difluoroacetyl)hydrazine-1-carbonyl)-2-fluorobenzyl)-N-(4-((4-neopentylpiperazin-1-yl)methyl)phenyl)thiomorpholine-4-carboxamide 1,1-dioxide as white solid (0.055 g, 97.1%).

[Step 8] Compound 21895

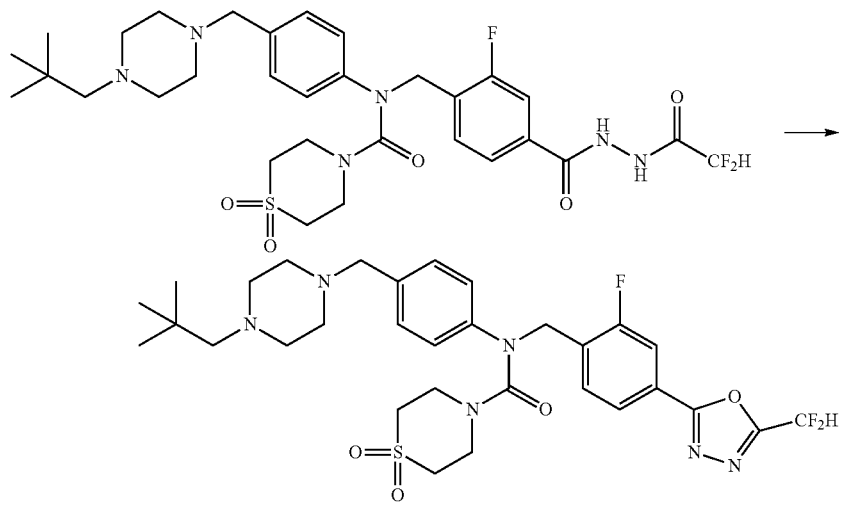

N-(4-(2-(2,2-difluoroacetyl)hydrazine-1-carbonyl)-2-fluorobenzyl)-N-(4-((4-neopentylpiperazin-1-yl)methyl)phenyl)thiomorpholine-4-carboxamide 1,1-dioxide (0.055 g, 0.082 mmol) and 1-methoxy-N-triethylammoniosulfonyl-methanimidate (Burgess reagent, 0.059 g, 0.247 mmol) in tetrahydrofuran (4 mL) was mixed at the room temperature and then heated at 150° C. under the microwaves for 30 min, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 10%) to give N-(4-(5-(difluoromethyl)-1,3,4-oxadiazol-2-yl)-2-fluorobenzyl)-N-(4-((4-neopentylpiperazin-1-yl)methyl)phenyl)thiomorpholine-4-carboxamide 1,1-dioxide as yellow solid (0.009 g, 16.8%).

$^1$H NMR (400 MHz, CDCl$_3$) δ 7.89 (dd, 1H, J=8.0, 1.5 Hz), 7.76 (dd, 1H, J=10.0, 1.4 Hz), 7.68 (t, 1H, J=7.6 Hz), 7.35-7.33 (m, 2H), 7.15-6.80 (m, 3H), 4.93 (s, 2H), 3.73 (t, 4H, J=4.9 Hz), 3.49 (brs, 2H), 2.79 (s, 4H), 2.59-2.44 (m, 8H), 2.08 (brs, 2H), 0.88 (s, 9H); LRMS (ES) m/z 649.3 (M$^+$+1).

Example 355. Compound 21896: N-(4-(5-(difluoromethyl)-1,3,4-oxadiazol-2-yl)-2-fluorobenzyl)-N-(4-((4-(oxetan-3-yl)piperazin-1-yl)methyl)phenyl)thiomorpholine-4-carboxamide 1,1-dioxide

[Step 1] Methyl 3-fluoro-4-((N-(4-((4-(oxetan-3-yl)piperazin-1-yl)methyl)phenyl)-1,1-dioxidothiomorpholine-4-carboxamido)methyl)benzoate

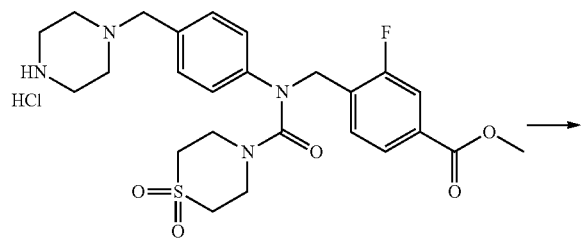

-continued

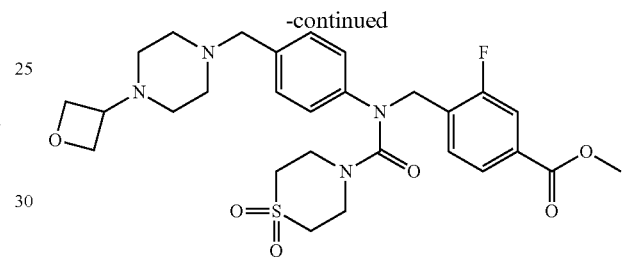

Oxetan-3-one (0.058 g, 0.811 mmol) was added to a solution of methyl 4-((1,1-dioxido-N-(4-(piperazin-1-ylmethyl)phenyl)thiomorpholine-4-carboxamido)methyl)-3-fluorobenzoate hydrochloride (0.300 g, 0.540 mmol) and N,N-diisopropylethylamine (0.094 mL, 0.540 mmol) in dichloromethane (5 mL) at the room temperature, and the mixture was stirred for 10 min at the same temperature. The mixture was treated at the same temperature with sodium triacetoxyborohydride (0.229 g, 1.081 mmol), stirred for additional 17 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give methyl 3-fluoro-4-((N-(4-((4-(oxetan-3-yl)piperazin-1-yl)methyl)phenyl)-1,1-dioxidothiomorpholine-4-carboxamido)methyl)benzoate as colorless oil (0.226 g, 72.8%).

1075

[Step 2] N-(2-fluoro-4-(hydrazinecarbonyl)benzyl)-N-(4-((4-(oxetan-3-yl)piperazin-1-yl)methyl)phenyl)thiomorpholine-4-carboxamide 1,1-dioxide

1076

[Step 3] N-(4-(2-(2,2-difluoroacetyl)hydrazine-1-carbonyl)-2-fluorobenzyl)-N-(4-((4-(oxetan-3-yl)piperazin-1-yl)methyl)phenyl)thiomorpholine-4-carboxamide 1,1-dioxide

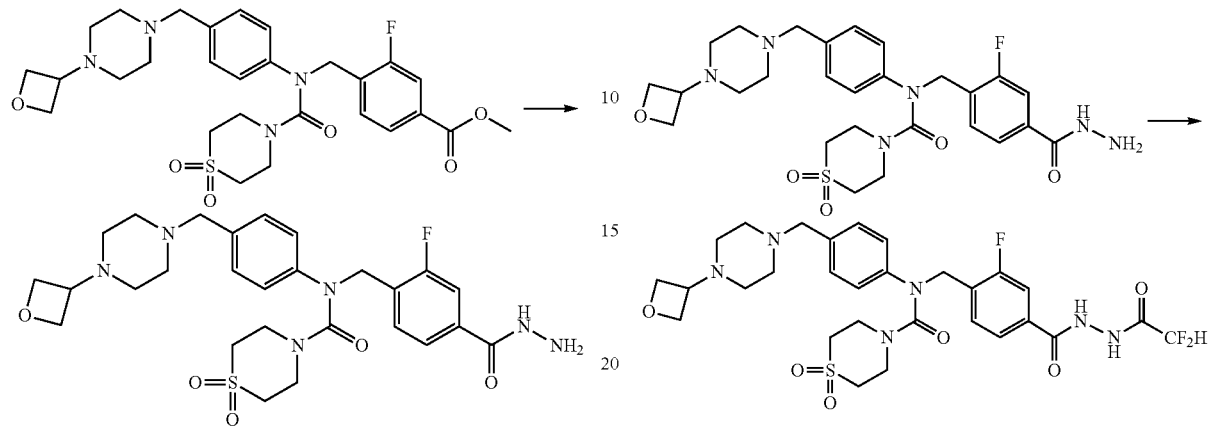

Methyl 3-fluoro-4-((N-(4-((4-(oxetan-3-yl)piperazin-1-yl)methyl)phenyl)-1,1-dioxidothiomorpholine-4-carboxamido)methyl)benzoate (0.226 g, 0.393 mmol) and hydrazine monohydrate (0.382 mL, 7.865 mmol) were mixed at the room temperature in ethanol (5 mL) and then stirred at 100° C. for 5 hr, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. N-(2-fluoro-4-(hydrazinecarbonyl)benzyl)-N-(4-((4-(oxetan-3-yl)piperazin-1-yl)methyl)phenyl)thiomorpholine-4-carboxamide 1,1-dioxide was used without further purification (0.222 g, 98.2%, pale yellow solid).

A solution of N-(2-fluoro-4-(hydrazinecarbonyl)benzyl)-N-(4-((4-(oxetan-3-yl)piperazin-1-yl)methyl)phenyl)thiomorpholine-4-carboxamide 1,1-dioxide (0.100 g, 0.174 mmol) and triethylamine (0.073 mL, 0.522 mmol) in tetrahydrofuran (5 mL) was mixed at the room temperature with 2,2-difluoroacetic anhydride (0.043 mL, 0.348 mmol), stirred at the same temperature for 17 hr. The reaction mixture was concentrated under the reduced pressure to remove the solvent The concentrate was purified and concentrated by column chromatography (SiO$_2$, 4 g cartridge; methanol/dichloromethane=0% to 10%) to give N-(4-(2-(2,2-difluoroacetyl)hydrazine-1-carbonyl)-2-fluorobenzyl)-N-(4-((4-(oxetan-3-yl)piperazin-1-yl)methyl)phenyl)thiomorpholine-4-carboxamide 1,1-dioxide as pale yellow solid (0.105 g, 92.4%)

[Step 4] Compound 21896

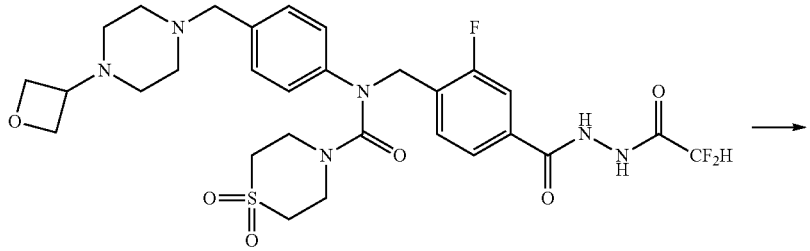

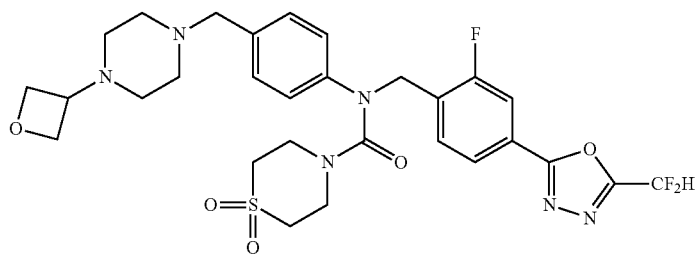

N-(4-(2-(2,2-difluoroacetyl)hydrazine-1-carbonyl)-2-fluorobenzyl)-N-(4-((4-(oxetan-3-yl)piperazin-1-yl)methyl)phenyl)thiomorpholine-4-carboxamide 1,1-dioxide (0.105 g, 0.161 mmol) and 1-methoxy-N-triethylammoniosulfonyl-methanimidate (Burgess reagent, 0.115 g, 0.483 mmol) in tetrahydrofuran (4 mL) was mixed at the room temperature and then heated at 150° C. under the microwaves for 30 min, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound which was purified and concentrated by re-column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-((4-(oxetan-3-yl)piperazin-1-yl)methyl)phenyl)thiomorpholine-4-carboxamide 1,1-dioxide as white solid (0.009 g, 8.8%).

$^1$H NMR (400 MHz, MeOD) δ 7.89 (dd, 1H, J=8.0, 1.6 Hz), 7.81-7.74 (m, 2H), 7.38 (d, 2H, J=8.4 Hz), 7.26-7.10 (m, 3H), 5.00 (s, 2H), 4.69 (t, 2H, J=6.7 Hz), 4.59 (t, 2H, J=6.3 Hz), 3.71-3.70 (m, 4H), 3.54-3.49 (m, 3H), 2.86 (t, 4H, J=5.2 Hz), 2.52-2.39 (m, 8H); LRMS (ES) m/z 635.5 (M$^+$+1).

Example 356. Compound 21897: N-(2-fluoro-4-(5-(trifluoromethyl)-1,3,4-oxadiazol-2-yl)benzyl)-N-(4-((4-neopentylpiperazin-1-yl)methyl)phenyl)thiomorpholine-4-carboxamide 1,1-dioxide

[Step 1] N-(2-fluoro-4-(2-(2,2,2-trifluoroacetyl)hydrazine-1-carbonyl)benzyl)-N-(4-((4-neopentylpiperazin-1-yl)methyl)phenyl)thiomorpholine-4-carboxamide 1,1-dioxide

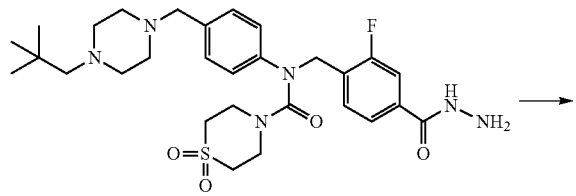

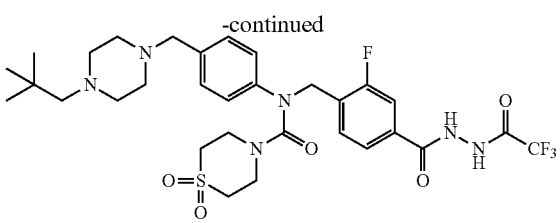

A solution of N-(2-fluoro-4-(hydrazinecarbonyl)benzyl)-N-(4-((4-neopentylpiperazin-1-yl)methyl)phenyl)thiomorpholine-4-carboxamide 1,1-dioxide (0.050 g, 0.085 mmol) and triethylamine (0.036 mL, 0.255 mmol) in tetrahydrofuran (5 mL) was mixed at the room temperature with trifluoroacetic anhydride (0.024 mL, 0.170 mmol), stirred at the same temperature for 17 hr. The reaction mixture was concentrated under the reduced pressure to remove the solvent The concentrate was purified and concentrated by column chromatography (SiO$_2$, 4 g cartridge; methanol/dichloromethane=0% to 10%) to give N-(2-fluoro-4-(2-(2,2,2-trifluoroacetyl)hydrazine-1-carbonyl)benzyl)-N-(4-((4-neopentylpiperazin-1-yl)methyl)phenyl)thiomorpholine-4-carboxamide 1,1-dioxide as white solid (0.055 g, 94.6%).

[Step 2] Compound 21897

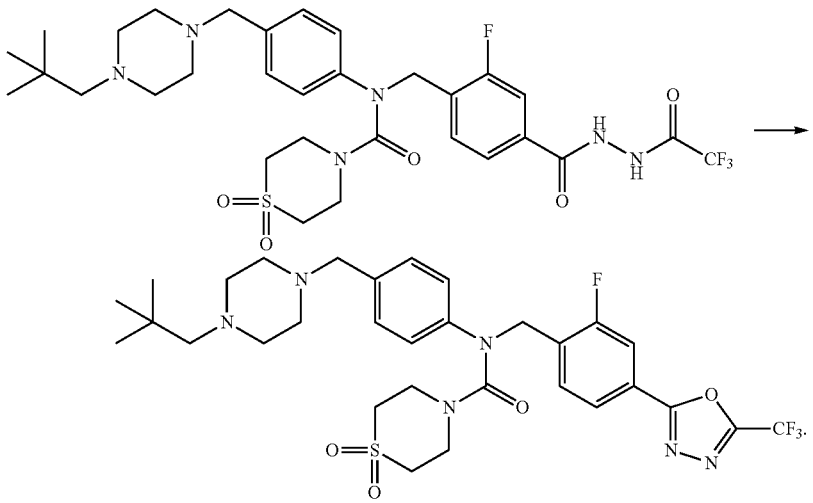

N-(2-fluoro-4-(2-(2,2,2-trifluoroacetyl)hydrazine-1-carbonyl)benzyl)-N-(4-((4-neopentylpiperazin-1-yl)methyl)phenyl)thiomorpholine-4-carboxamide 1,1-dioxide (0.055 g, 0.080 mmol) and 1-methoxy-N-triethylammoniosulfonyl-methanimidate (Burgess reagent, 0.057 g, 0.241 mmol) in tetrahydrofuran (4 mL) was mixed at the room temperature and then heated at 150° C. under the microwaves for 30 min, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 10%) to give N-(2-fluoro-4-(5-(trifluoromethyl)-1,3,4-oxadiazol-2-yl)benzyl)-N-(4-((4-neopentylpiperazin-1-yl)methyl)phenyl)thiomorpholine-4-carboxamide 1,1-dioxide as pale yellow solid (0.015 g, 28.0%).

$^1$H NMR (400 MHz, CDCl$_3$) δ 7.88 (dd, 1H, J=8.0, 1.6 Hz), 7.75 (dd, 1H, J=10.0, 1.6 Hz), 7.69 (t, 1H, J=7.6 Hz), 7.35 (brs, 2H), 7.08 (d, 2H, J=8.2 Hz), 4.93 (s, 2H), 3.73 (t, 4H, J=5.0 Hz), 3.49 (brs, 2H), 2.78 (t, 4H, J=4.9 Hz), 2.57-2.44 (m, 8H), 2.08 (brs, 2H), 0.88 (s, 9H); LRMS (ES) m/z 667.3 (M$^+$+1).

Example 357. Compound 21898: N-(2-fluoro-4-(5-(trifluoromethyl)-1,3,4-oxadiazol-2-yl)benzyl)-N-(4-((4-(oxetan-3-yl)piperazin-1-yl)methyl)phenyl)thiomorpholine-4-carboxamide 1,1-dioxide

[Step 1] N-(2-fluoro-4-(2-(2,2,2-trifluoroacetyl)hydrazine-1-carbonyl)benzyl)-N-(4-((4-(oxetan-3-yl)piperazin-1-yl)methyl)phenyl)thiomorpholine-4-carboxamide 1,1-dioxide

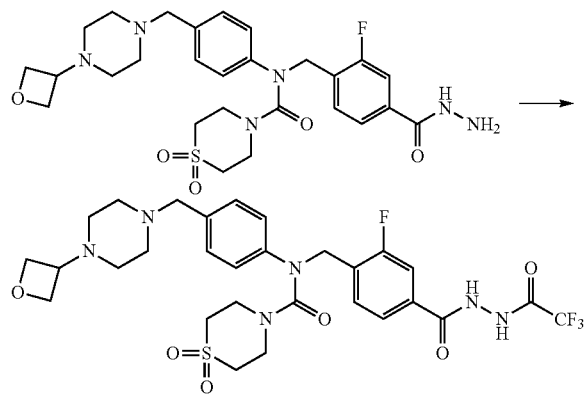

A solution of N-(2-fluoro-4-(hydrazinecarbonyl)benzyl)-N-(4-((4-(oxetan-3-yl)piperazin-1-yl)methyl)phenyl)thiomorpholine-4-carboxamide 1,1-dioxide (0.100 g, 0.174 mmol) and triethylamine (0.073 mL, 0.522 mmol) in tetrahydrofuran (5 mL) was mixed at the room temperature with trifluoroacetic anhydride (0.049 mL, 0.348 mmol), stirred at the same temperature for 17 hr. The reaction mixture was concentrated under the reduced pressure to remove the solvent The concentrate was purified and concentrated by column chromatography (SiO$_2$, 4 g cartridge; methanol/dichloromethane=0% to 10%) to give N-(2-fluoro-4-(2-(2,2,2-trifluoroacetyl)hydrazine-1-carbonyl)benzyl)-N-(4-((4-(oxetan-3-yl)piperazin-1-yl)methyl)phenyl)thiomorpholine-4-carboxamide 1,1-dioxide as pale yellow solid (0.105 g, 90.0%).

[Step 2] Compound 21898

N-(2-fluoro-4-(2-(2,2,2-trifluoroacetyl)hydrazine-1-carbonyl)benzyl)-N-(4-((4-(oxetan-3-yl)piperazin-1-yl)methyl)phenyl)thiomorpholine-4-carboxamide 1,1-dioxide (0.100 g, 0.149 mmol) and 1-methoxy-N-triethylammoniosulfonyl-methanimidate (Burgess reagent, 0.107 g, 0.447 mmol) in tetrahydrofuran (4 mL) was mixed at the room temperature and then heated at 150° C. under the microwaves for 30 min, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound which was purified and concentrated by re-column chromatography (SiO$_2$, 4 g cartridge; methanol/dichloromethane=0% to 5%) to give N-(2-fluoro-4-(5-(trifluoromethyl)-1,3,4-oxadiazol-2-yl)benzyl)-N-(4-((4-(oxetan-3-yl)piperazin-1-yl)methyl)phenyl)thiomorpholine-4-carboxamide 1,1-dioxide as white solid (0.004 g, 4.1%).

$^1$H NMR (400 MHz, CDCl$_3$) δ 7.89 (dd, 1H, J=8.0, 1.4 Hz), 7.77 (d, 1H, J=9.4 Hz), 7.70 (t, 1H, J=7.6 Hz), 7.36-7.32 (m, 2H), 7.13-7.11 (m, 2H), 4.94 (s, 2H), 4.71-4.57 (m, 4H), 3.72-3.53 (m, 7H), 2.80-2.35 (m, 12H); LRMS (ES) m/z 653.3 (M$^+$+1).

Example 358. Compound 21899: N-(4-(5-(difluoromethyl)-1,3,4-oxadiazol-2-yl)-2-fluorobenzyl)-N-(4-((4-ethylpiperazin-1-yl)methyl)phenyl)thiomorpholine-4-carboxamide 1,1-dioxide

[Step 1] N-(4-((4-ethylpiperazin-1-yl)methyl)phenyl)thiomorpholine-4-carboxamide 1,1-dioxide

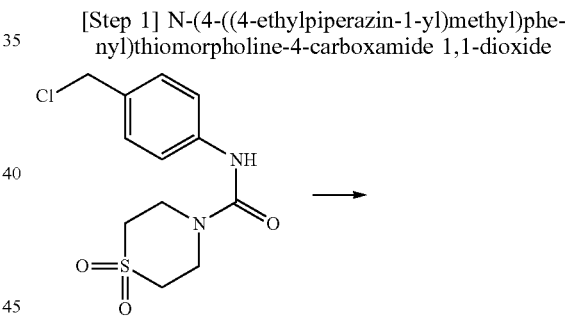

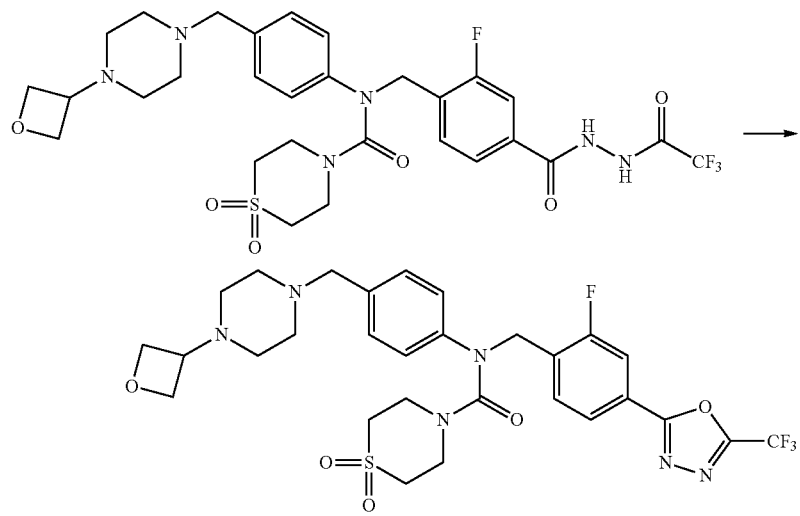

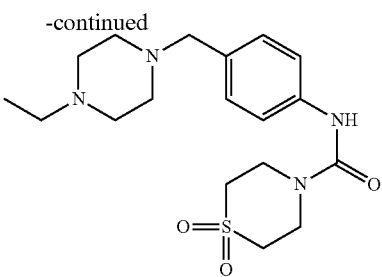

A solution of N-(4-(chloromethyl)phenyl)thiomorpholine-4-carboxamide 1,1-dioxide (0.500 g, 1.651 mmol), 1-ethylpiperazine (0.420 mL, 3.303 mmol) and potassium carbonate (0.685 g, 4.954 mmol) in acetonitrile (10 mL) prepared at the room temperature was stirred at the same temperature for 5 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was diluted with ethyl acetate (2 mL) and diethylether (20 mL) and stirred. The resulting precipitates were collected by filtration, washed by diethylether, and dried to give N-(4-((4-ethylpiperazin-1-yl)methyl)phenyl)thiomorpholine-4-carboxamide 1,1-dioxide as white solid (0.360 g, 57.3%).

[Step 2] Methyl 4-((N-(4-((4-ethylpiperazin-1-yl)methyl)phenyl)-1,1-dioxidothiomorpholine-4-carboxamido)methyl)-3-fluorobenzoate

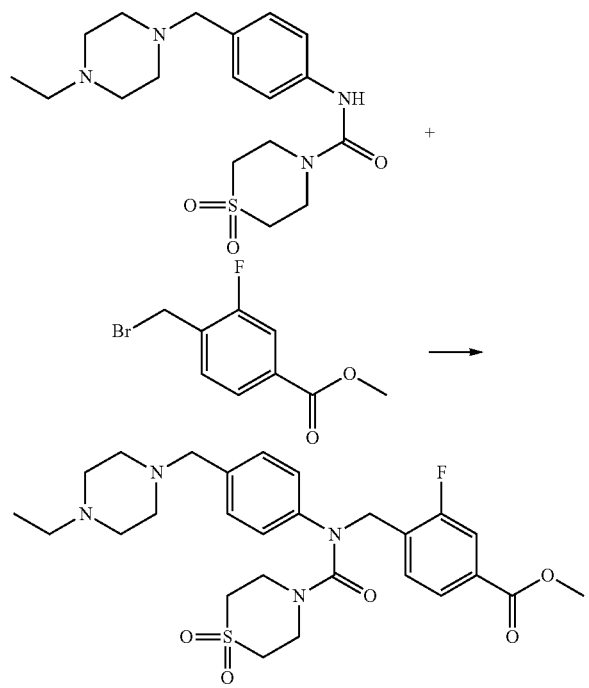

A solution of N-(4-((4-ethylpiperazin-1-yl)methyl)phenyl)thiomorpholine-4-carboxamide 1,1-dioxide (0.360 g, 0.946 mmol) and sodium hydride (60.00%, 0.042 g, 1.041 mmol) in N,N-dimethylformamide (10 mL) was stirred at 0° C. for 10 min, and mixed with methyl 4-(bromomethyl)-3-fluorobenzoate (0.257 g, 1.041 mmol). The reaction mixture was stirred at the room temperature for additional 2 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 12 g cartridge; methanol/dichloromethane=0% to 5%) to give methyl 4-((N-(4-((4-ethylpiperazin-1-yl)methyl)phenyl)-1,1-dioxidothiomorpholine-4-carboxamido)methyl)-3-fluorobenzoate as pale yellow solid (0.397 g, 76.8%).

[Step 3] N-(4-((4-ethylpiperazin-1-yl)methyl)phenyl)-N-(2-fluoro-4-(hydrazinecarbonyl)benzyl)thiomorpholine-4-carboxamide 1,1-dioxide

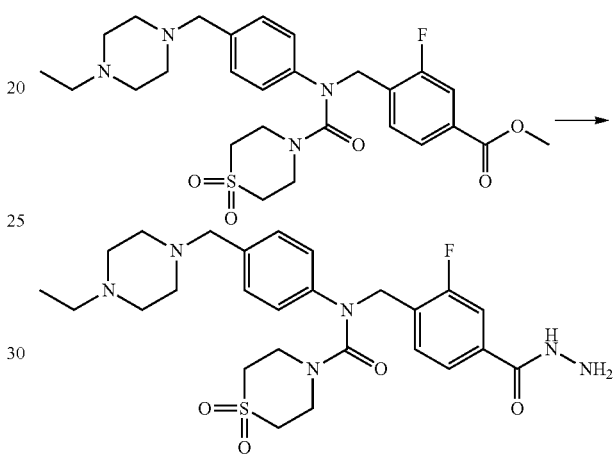

Methyl 4-((N-(4-((4-ethylpiperazin-1-yl)methyl)phenyl)-1,1-dioxidothiomorpholine-4-carboxamido)methyl)-3-fluorobenzoate (0.397 g, 0.726 mmol) and hydrazine monohydrate (0.706 mL, 14.525 mmol) were mixed at the room temperature in ethanol (4 mL) and then stirred at 100° C. for 3 hr, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography ($SiO_2$, 4 g cartridge; methanol/dichloromethane=0% to 10%) to give N-(4-((4-ethylpiperazin-1-yl)methyl)phenyl)-N-(2-fluoro-4-(hydrazinecarbonyl)benzyl)thiomorpholine-4-carboxamide 1,1-dioxide as white solid (0.297 g, 74.8%).

[Step 4] N-(4-(2-(2,2-difluoroacetyl)hydrazine-1-carbonyl)-2-fluorobenzyl)-N-(4-((4-ethylpiperazin-1-yl)methyl)phenyl)thiomorpholine-4-carboxamide 1,1-dioxide

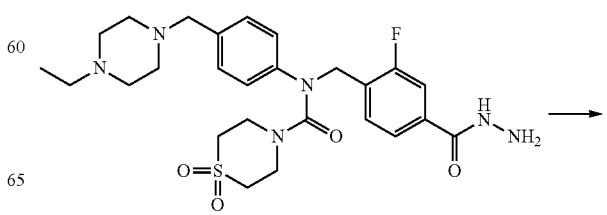

-continued

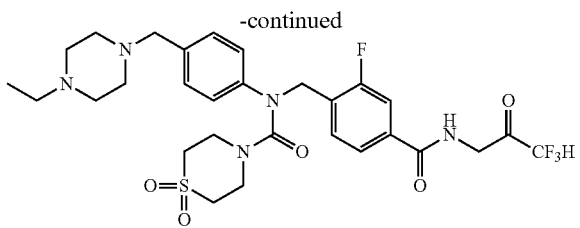

A solution of N-(4-(((4-ethylpiperazin-1-yl)methyl)phenyl)-N-(2-fluoro-4-(hydrazinecarbonyl)benzyl)thiomorpholine-4-carboxamide 1,1-dioxide (0.150 g, 0.274 mmol) and triethylamine (0.076 mL, 0.549 mmol) in dichloromethane (5 mL) was mixed at the room temperature with 2,2-difluoroacetic anhydride (0.038 mL, 0.302 mmol), stirred at the same temperature for 1 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-(2-(2,2-difluoroacetyl)hydrazine-1-carbonyl)-2-fluorobenzyl)-N-(4-((4-ethylpiperazin-1-yl)methyl)phenyl)thiomorpholine-4-carboxamide 1,1-dioxide as white solid (0.167 g, 97.4%).

[Step 5] Compound 21899

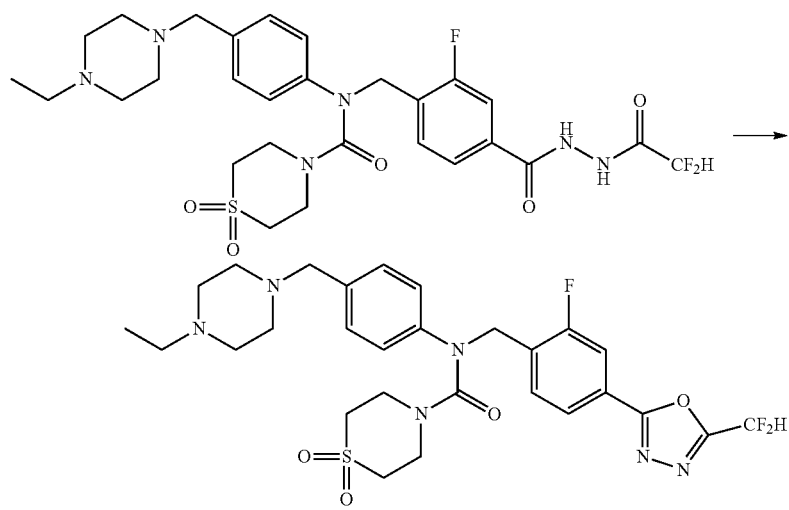

N-(4-(2-(2,2-difluoroacetyl)hydrazine-1-carbonyl)-2-fluorobenzyl)-N-(4-((4-ethylpiperazin-1-yl)methyl)phenyl)thiomorpholine-4-carboxamide 1,1-dioxide (0.167 g, 0.267 mmol) and 1-methoxy-N-triethylammoniosulfonyl-methanimidate (Burgess reagent, 0.191 g, 0.802 mmol) in tetrahydrofuran (4 mL) was mixed at the room temperature and then heated at 150° C. under the microwaves for 30 min, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 10%) to give N-(4-(5-(difluoromethyl)-1,3,4-oxadiazol-2-yl)-2-fluorobenzyl)-N-(4-((4-ethylpiperazin-1-yl)methyl)phenyl)thiomorpholine-4-carboxamide 1,1-dioxide as orange solid (0.064 g, 39.5%).

$^1$H NMR (400 MHz, CDCl$_3$) δ 7.89 (dd, 1H, J=8.0, 1.6 Hz), 7.76 (dd, 1H, J=10.1, 1.6 Hz), 7.68 (t, 1H, J=7.7 Hz), 7.33 (d, 2H, J=8.4 Hz), 7.10-6.80 (m, 3H), 4.92 (s, 2H), 3.73 (t, 4H, J=5.0 Hz), 2.80-2.64 (m, 14H), 1.24-1.23 (m, 3H); LRMS (ES) m/z 607.1 (M$^+$+1).

Example 359. Compound 21900: N-(4-((4-benzylpiperazin-1-yl)methyl)phenyl)-N-(4-(5-(difluoromethyl)-1,3,4-oxadiazol-2-yl)-2-fluorobenzyl)thiomorpholine-4-carboxamide 1,1-dioxide

[Step 1] N-(4-((4-benzylpiperazin-1-yl)methyl)phenyl)thiomorpholine-4-carboxamide 1,1-dioxide

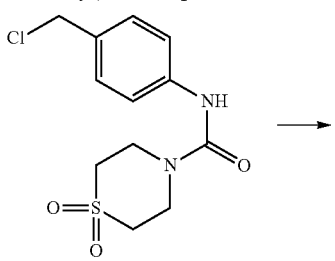

-continued

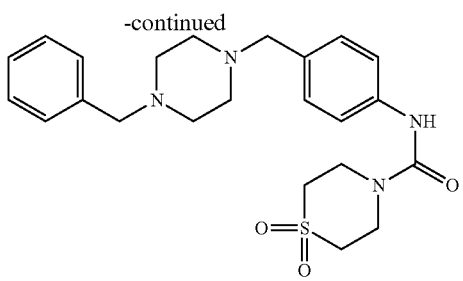

A solution of N-(4-(chloromethyl)phenyl)thiomorpholine-4-carboxamide 1,1-dioxide (0.500 g, 1.651 mmol), 1-benzylpiperazine (0.582 g, 3.303 mmol) and potassium carbonate (0.685 g, 4.954 mmol) in acetonitrile (10 mL) was stirred at the room temperature for 5 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with diethylether (20 mL) and stirred. The resulting precipitates were collected by filtration, washed by diethylether, and dried to give N-(4-((4-benzylpiperazin-1-yl) methyl)phenyl)thiomorpholine-4-carboxamide 1,1-dioxide as white solid (0.618 g, 84.6%).

[Step 2] Methyl 4-((N-(4-((4-benzylpiperazin-1-yl) methyl)phenyl)-1,1-dioxidothiomorpholine-4-carboxamido)methyl)-3-fluorobenzoate

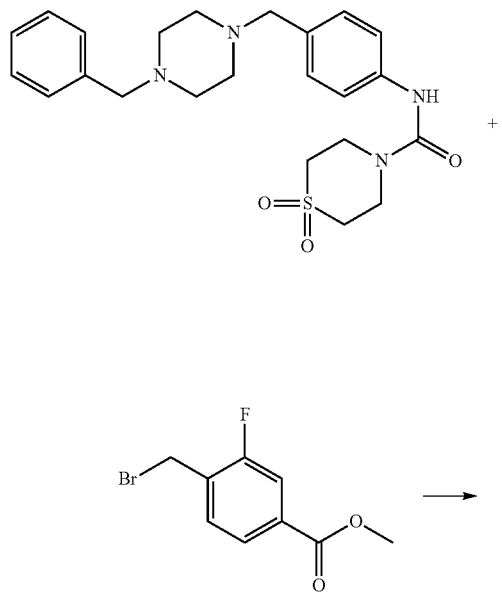

A solution of N-(4-((4-benzylpiperazin-1-yl)methyl)phenyl)thiomorpholine-4-carboxamide 1,1-dioxide (0.618 g, 1.396 mmol) and sodium hydride (60.00%, 0.061 g, 1.536 mmol) in N,N-dimethylformamide (10 mL) was stirred at 0° C. for 10 min, and mixed with methyl 4-(bromomethyl)-3-fluorobenzoate (0.379 g, 1.536 mmol). The reaction mixture was stirred at the room temperature for additional 2 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 5%) to give methyl 4-((N-(4-((4-benzylpiperazin-1-yl)methyl)phenyl)-1,1-dioxidothiomorpholine-4-carboxamido)methyl)-3-fluorobenzoate as white solid (0.761 g, 89.5%).

[Step 3] N-(4-((4-benzylpiperazin-1-yl)methyl)phenyl)-N-(2-fluoro-4-(hydrazinecarbonyl)benzyl) thiomorpholine-4-carboxamide 1,1-dioxide

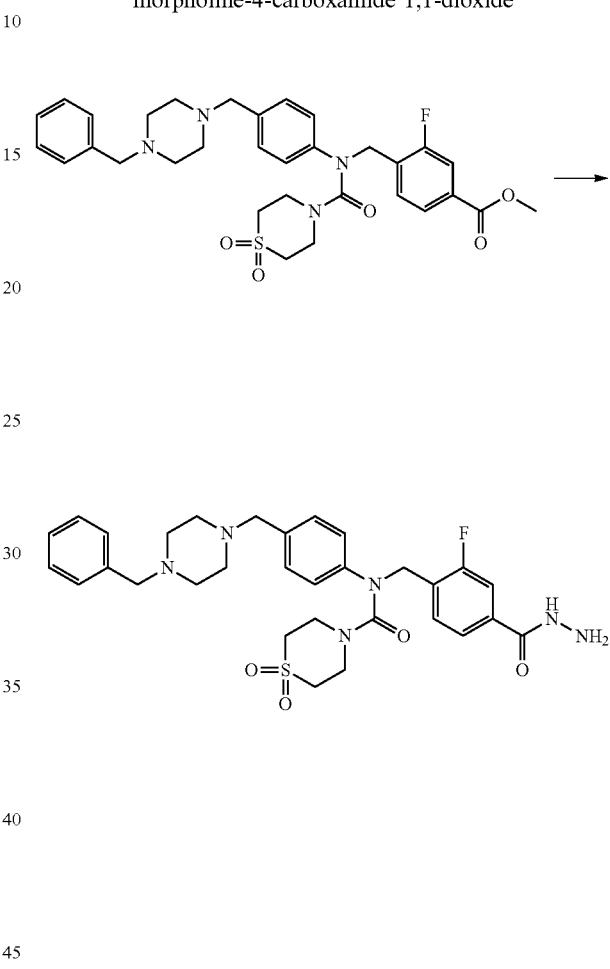

methyl 4-((N-(4-((4-benzylpiperazin-1-yl)methyl)phenyl)-1,1-dioxidothiomorpholine-4-carboxamido)methyl)-3-fluorobenzoate (0.400 g, 0.657 mmol) and hydrazine monohydrate (0.639 mL, 13.142 mmol) were mixed at the room temperature in ethanol (4 mL) and then stirred at 100° C. for 3 hr, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 10%) to give N-(4-((4-benzylpiperazin-1-yl)methyl)phenyl)-N-(2-fluoro-4-(hydrazinecarbonyl)benzyl) thiomorpholine-4-carboxamide 1,1-dioxide as white solid (0.300 g, 75.0%).

[Step 4] N-(4-((4-benzylpiperazin-1-yl)methyl)phenyl)-N-(4-(2-(2,2-difluoroacetyl)hydrazine-1-carbonyl)-2-fluorobenzyl)thiomorpholine-4-carboxamide 1,1-dioxide

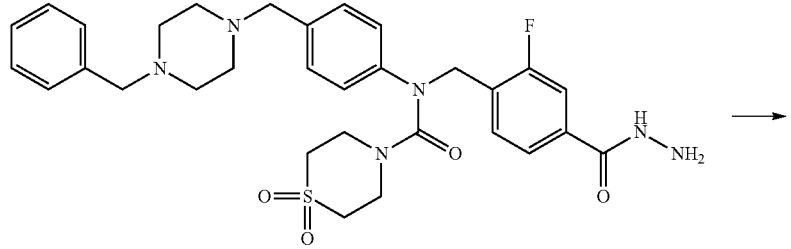

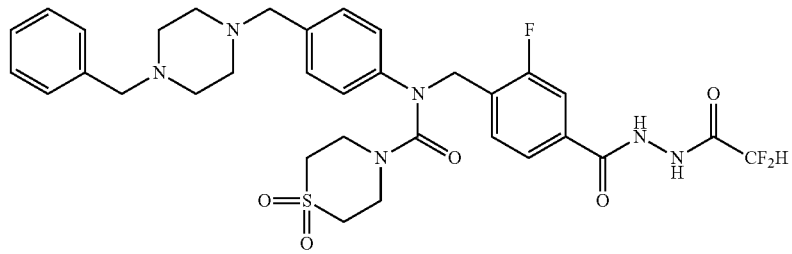

A solution of N-(4-((4-benzylpiperazin-1-yl)methyl)phenyl)-N-(2-fluoro-4-(hydrazinecarbonyl)benzyl) thiomorpholine-4-carboxamide 1,1-dioxide (0.150 g, 0.246 mmol) and triethylamine (0.069 mL, 0.493 mmol) in dichloromethane (5 mL) was mixed at the room temperature with 2,2-difluoroacetic anhydride (0.034 mL, 0.271 mmol), stirred at the same temperature for 1 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-((4-benzylpiperazin-1-yl)methyl)phenyl)-N-(4-(2-(2,2-difluoroacetyl)hydrazine-1-carbonyl)-2-fluorobenzyl)thiomorpholine-4-carboxamide 1,1-dioxide as white solid (0.172 g, 101.6%).

[Step 5] Compound 21900

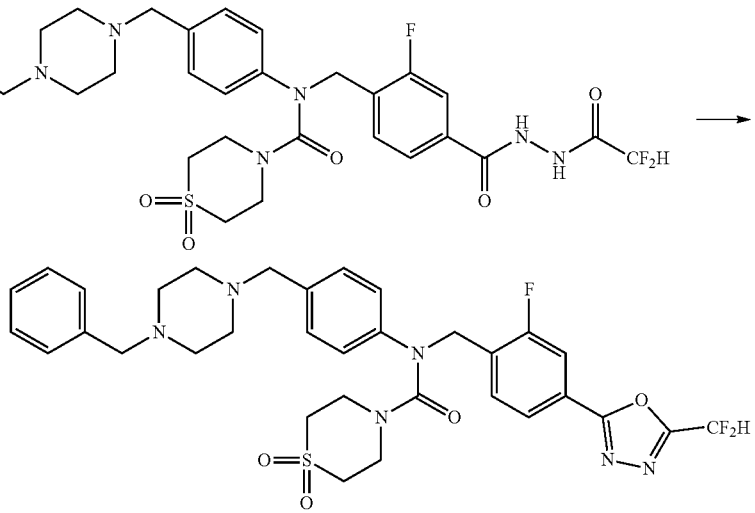

N-(4-((4-benzylpiperazin-1-yl)methyl)phenyl)-N-(4-(2-(2,2-difluoroacetyl)hydrazine-1-carbonyl)-2-fluorobenzyl)thiomorpholine-4-carboxamide 1,1-dioxide (0.172 g, 0.250 mmol) and 1-methoxy-N-triethylammoniosulfonyl-methanimidate (Burgess reagent, 0.179 g, 0.751 mmol) in tetrahydrofuran (4 mL) was mixed at the room temperature and then heated at 150° C. under the microwaves for 30 min, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 10%) to give the title compound which was purified and concentrated by re-column chromatography (SiO$_2$, 4 g cartridge; ethyl acetate/hexane=50% to 80%) to give (4-((4-benzylpiperazin-1-yl)methyl)phenyl)-N-(4-(5-(difluoromethyl)-1,3,4-oxadiazol-2-yl)-2-fluorobenzyl)thiomorpholine-4-carboxamide 1,1-dioxide as pale yellow solid (0.070 g, 41.8%).

$^1$H NMR (400 MHz; CDCl$_3$) δ 7.88 (dd, 1H, J=8.0, 1.6 Hz), 7.76 (dd, 1H, J=10.1, 1.6 Hz), 7.67 (t, 1H, J=7.7 Hz), 7.34-7.33 (m, 7H), 7.08-6.80 (m, 3H), 4.92 (s, 2H), 3.72 (t, 4H, J=4.9 Hz), 3.56-3.50 (m, 4H), 2.79 (t, 4H, J=5.0 Hz), 2.52-2.49 (m, 8H); LRMS (ES) m/z 669.2 (M$^+$+1).

Example 360. Compound 21901: N-(4-(5-(difluoromethyl)-1,3,4-oxadiazol-2-yl)-2-fluorobenzyl)-N-(4-((4-(2-fluoro-2-methylpropyl)piperazin-1-yl)methyl)phenyl)thiomorpholine-4-carboxamide 1,1-dioxide

[Step 1] Ethyl 3-fluoro-4-((N-(4-((4-(2-hydroxy-2-methylpropyl)piperazin-1-yl)methyl)phenyl)-1,1-dioxidothiomorpholine-4-carboxamido)methyl)benzoate

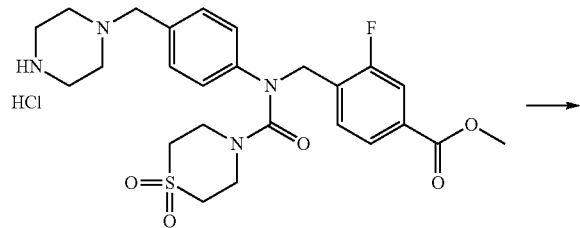

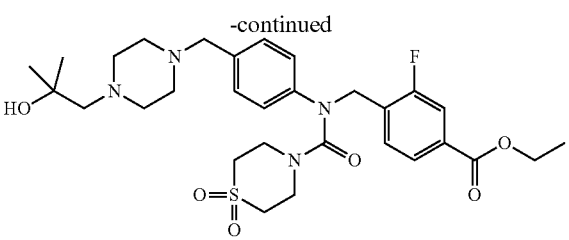

Methyl 4-((1,1-dioxido-N-(4-(piperazin-1-ylmethyl)phenyl)thiomorpholine-4-carboxamido)methyl)-3-fluorobenzoate hydrochloride (0.250 g, 0.450 mmol), 2,2-dimethyloxirane (0.325 g, 4.504 mmol) and potassium carbonate (1.245 g, 9.008 mmol) in ethanol (5 mL) was mixed at the room temperature and then heated at 110° C. under the microwaves for 20 min, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give ethyl 3-fluoro-4-((N-(4-((4-(2-hydroxy-2-methylpropyl)piperazin-1-yl)methyl)phenyl)-1,1-dioxidothiomorpholine-4-carboxamido)methyl)benzoate as pale orange solid (0.247 g, 90.7%).

[Step 2] Ethyl 3-fluoro-4-((N-(4-((4-(2-fluoro-2-methylpropyl)piperazin-1-yl)methyl)phenyl)-1,1-dioxidothiomorpholine-4-carboxamido)methyl)benzoate

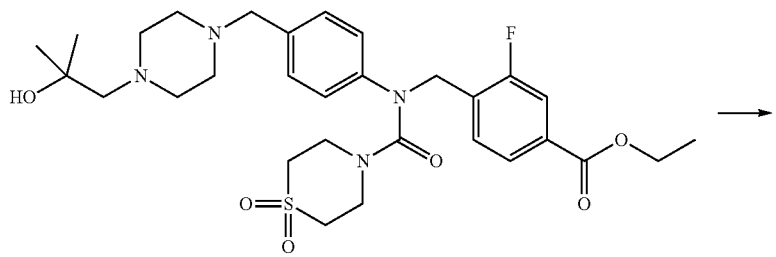

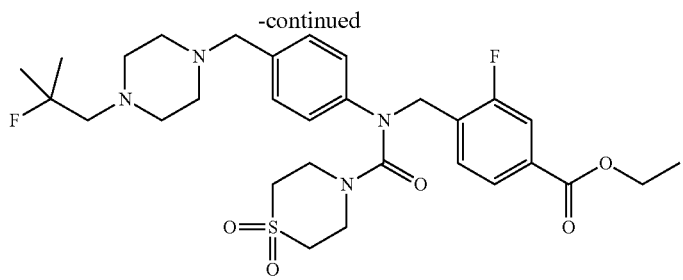

A solution of ethyl 3-fluoro-4-((N-(4-((4-(2-hydroxy-2-methylpropyl)piperazin-1-yl)methyl)phenyl)-1,1-dioxidothiomorpholine-4-carboxamido)methyl)benzoate (0.247 g, 0.408 mmol) in dichloromethane (5 mL) was mixed at 0° C. with diethylaminosulfur trifluoride (DAST, 0.059 mL, 0.449 mmol), stirred at the same temperature for 1 hr. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. Ethyl 3-fluoro-4-((N-(4-((4-(2-fluoro-2-methylpropyl)piperazin-1-yl)methyl)phenyl)-1,1-dioxidothiomorpholine-4-carboxamido)methyl)benzoate was used without further purification (0.167 g, 67.4%, pale yellow solid).

[Step 3] N-(4-((4-(2-fluoro-2-methylpropyl)piperazin-1-yl)methyl)phenyl)-N-(2-fluoro-4-(hydrazinecarbonyl)benzyl)thiomorpholine-4-carboxamide 1,1-dioxide

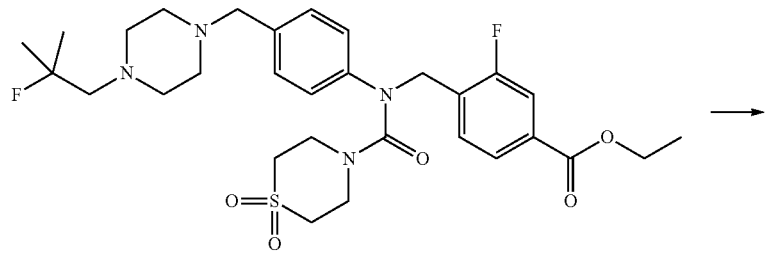

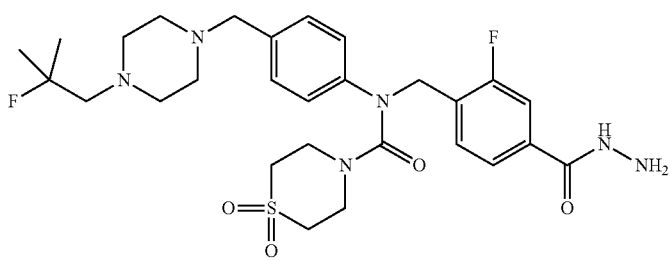

Ethyl 3-fluoro-4-((N-(4-((4-(2-fluoro-2-methylpropyl)piperazin-1-yl)methyl)phenyl)-1,1-dioxidothiomorpholine-4-carboxamido)methyl)benzoate (0.167 g, 0.278 mmol) and hydrazine monohydrate (0.270 mL, 5.561 mmol) were mixed at the room temperature in ethanol (5 mL) and then stirred at 100° C. for 3 hr, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. N-(4-((4-(2-fluoro-2-methylpropyl)piperazin-1-yl)methyl)phenyl)-N-(2-fluoro-4-(hydrazinecarbonyl)benzyl)thiomorpholine-4-carboxamide 1,1-dioxide was used without further purification (0.155 g, 82.1%, white solid).

[Step 4] Compound 21901

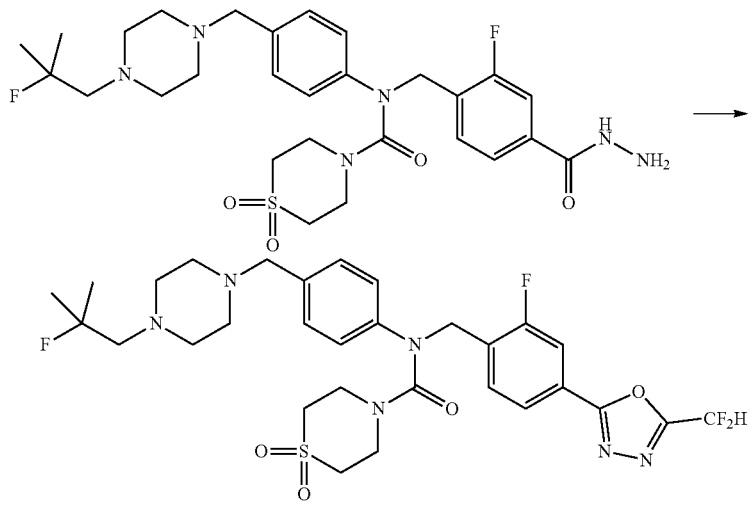

A solution of N-(4-((4-(2-fluoro-2-methylpropyl)piperazin-1-yl)methyl)phenyl)-N-(2-fluoro-4-(hydrazinecarbonyl)benzyl)thiomorpholine-4-carboxamide 1,1-dioxide (0.140 g, 0.236 mmol) and triethylamine (0.066 mL, 0.472 mmol) in dichloromethane (5 mL) was mixed at the room temperature with 2,2-difluoroacetic anhydride (0.032 mL, 0.260 mmol), stirred at the same temperature for 1 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=50% to 80%) to give N-(4-(5-(difluoromethyl)-1,3,4-oxadiazol-2-yl)-2-fluorobenzyl)-N-(4-((4-(2-fluoro-2-methylpropyl)piperazin-1-yl)methyl)phenyl)thiomorpholine-4-carboxamide 1,1-dioxide as yellow solid (0.021 g, 13.6%).

$^1$H NMR (400 MHz, CDCl$_3$) δ 7.88 (d, 1H, J=7.5 Hz), 7.76 (d, 1H, J=10.8 Hz), 7.67 (t, 1H, J=7.6 Hz), 7.35 (d, 2H, J=7.5 Hz), 7.09-6.80 (m, 3H), 4.93 (s, 2H), 3.73 (s, 4H), 3.52 (brs, 2H), 2.79 (s, 4H), 2.62-2.43 (m, 10H), 1.37 (d, 6H, J=21.4 Hz); LRMS (ES) m/z 653.1 (M$^+$+1).

Example 361. Compound 21902: N-(4-(5-(difluoromethyl)-1,3,4-oxadiazol-2-yl)-2-fluorobenzyl)-N-(4-((4-(2,2,2-trifluoroethyl)piperazin-1-yl)methyl)phenyl)thiomorpholine-4-carboxamide 1,1-dioxide

[Step 1] Methyl 4-((1,1-dioxido-N-(4-((4-(2,2,2-trifluoroethyl)piperazin-1-yl)methyl)phenyl)thiomorpholine-4-carboxamido)methyl)-3-fluorobenzoate

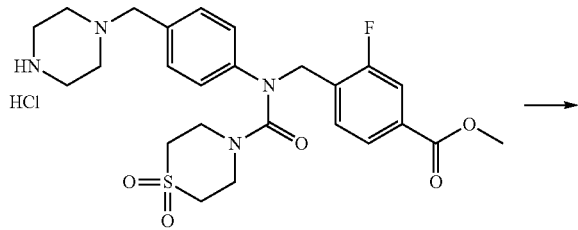

-continued

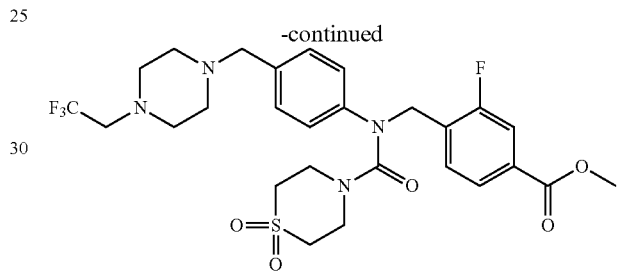

A solution of methyl 4-((1,1-dioxido-N-(4-(piperazin-1-ylmethyl)phenyl)thiomorpholine-4-carboxamido)methyl)-3-fluorobenzoate hydrochloride (0.300 g, 0.540 mmol), 2,2,2-trifluoroethyl trifluoromethanesulfonate (0.138 g, 0.595 mmol) and cesium carbonate (0.264 g, 0.811 mmol) in acetonitrile (5 mL) prepared at the room temperature was stirred at the same temperature for 17 hr, concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give methyl 4-((1,1-dioxido-N-(4-((4-(2,2,2-trifluoroethyl)piperazin-1-yl)methyl)phenyl)thiomorpholine-4-carboxamido)methyl)-3-fluorobenzoate as white solid (0.213 g, 65.6%).

1095

[Step 2] N-(2-fluoro-4-(hydrazinecarbonyl)benzyl)-N-(4-((4-(2,2,2-trifluoroethyl)piperazin-1-yl)methyl)phenyl)thiomorpholine-4-carboxamide 1,1-dioxide

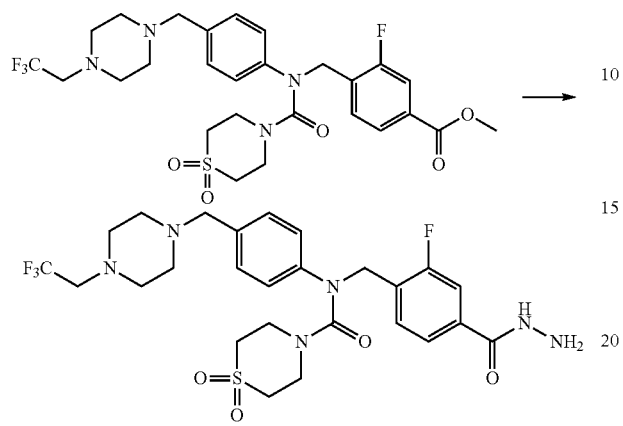

Methyl 4-((1,1-dioxido-N-(4-((4-((2,2,2-trifluoroethyl)piperazin-1-yl)methyl)phenyl)thiomorpholine-4-carboxamido)methyl)-3-fluorobenzoate (0.213 g, 0.355 mmol) and hydrazine monohydrate (0.345 mL, 7.093 mmol) were mixed at the room temperature in ethanol (5 mL) and then stirred at 100° C. for 3 hr, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. N-(2-fluoro-4-(hydrazinecarbonyl)benzyl)-N-(4-((4-(2,2,2-trifluoroethyl)piperazin-1-yl) methyl)phenyl)thiomorpholine-4-carboxamide 1,1-dioxide was used without further purification (0.208 g, 97.7%, white solid).

1096

[Step 3] N-(4-(2-(2,2-difluoroacetyl)hydrazine-1-carbonyl)-2-fluorobenzyl)-N-(4-((4-(2,2,2-trifluoroethyl)piperazin-1-yl)methyl)phenyl)thiomorpholine-4-carboxamide 1,1-dioxide

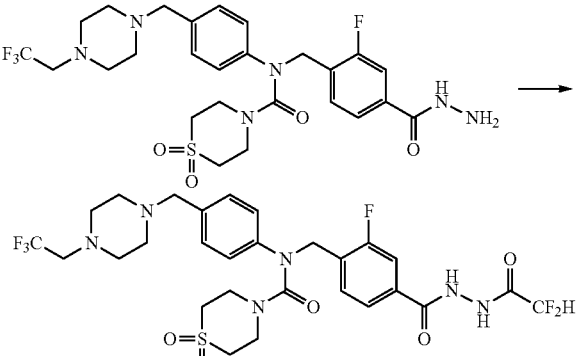

A solution of N-(2-fluoro-4-(hydrazinecarbonyl)benzyl)-N-(4-((4-(2,2,2-trifluoroethyl)piperazin-1-yl) methyl)phenyl)thiomorpholine-4-carboxamide 1,1-dioxide (0.100 g, 0.166 mmol) and triethylamine (0.046 mL, 0.333 mmol) in dichloromethane (4 mL) was mixed at the room temperature with 2,2-difluoroacetic anhydride (0.023 mL, 0.183 mmol), stirred at the same temperature for 1 hr. Then, water was added to the reaction mixture, followed by extraction with dichloromethane. The bi-phasic mixture was passed through a plastic frit to remove the solid residues and aqueous layer, and the organic layer collected was concentrated in vacuo. N-(4-(2-(2,2-difluoroacetyl)hydrazine-1-carbonyl)-2-fluorobenzyl)-N-(4-((4-(2,2,2-trifluoroethyl)piperazin-1-yl) methyl)phenyl)thiomorpholine-4-carboxamide 1,1-dioxide was used without further purification (0.122 g, 108.0%, white solid).

[Step 4] Compound 21902

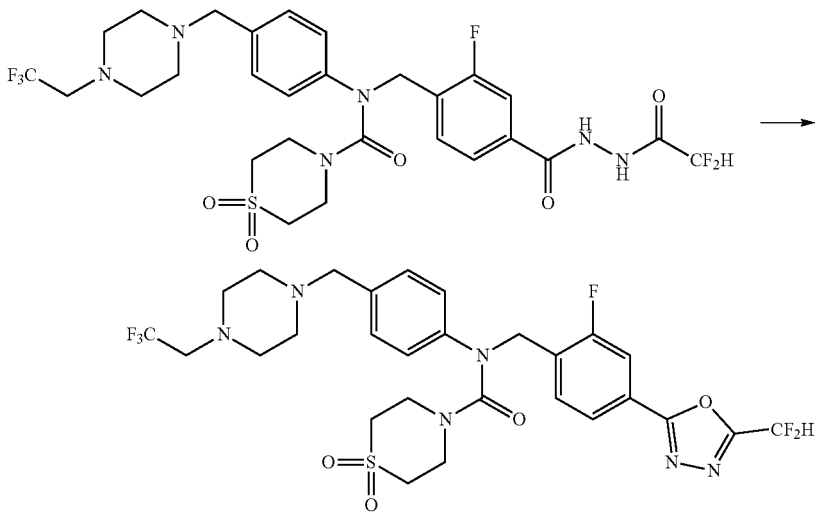

N-(4-(2-(2,2-difluoroacetyl)hydrazine-1-carbonyl)-2-fluorobenzyl)-N-(4-((4-(2,2,2-trifluoroethyl)piperazin-1-yl)methyl)phenyl)thiomorpholine-4-carboxamide 1,1-dioxide (0.122 g, 0.180 mmol) and 1-methoxy-N-triethylammonio-sulfonyl-methanimidate (Burgess reagent, 0.129 g, 0.539 mmol) in tetrahydrofuran (4 mL) was mixed at the room temperature and then heated at 150° C. under the microwaves for 30 min, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=50% to 100%) to give N-(4-(5-(difluoromethyl)-1,3,4-oxadiazol-2-yl)-2-fluorobenzyl)-N-(4-((4-(2,2,2-trifluoroethyl)piperazin-1-yl)methyl)phenyl)thiomorpholine-4-carboxamide 1,1-dioxide as orange solid (0.050 g, 42.1%).

$^1$H NMR (400 MHz, CDCl$_3$) δ 7.88 (dd, 1H, J=8.0, 1.4 Hz), 7.75 (dd, 1H, J=10.1, 1.3 Hz), 7.67 (t, 1H, J=7.6 Hz), 7.38-7.31 (m, 2H), 7.10-6.80 (m, 3H), 4.92 (s, 2H), 3.72 (s, 4H), 3.53-3.51 (m, 2H), 2.99 (q, 2H, J=9.6 Hz), 2.80-2.73 (m, 8H), 2.50 (brs, 4H); LRMS (ES) m/z 661.1 (M$^+$+1).

Example 362. Compound 21905: N-((5-(5-(Difluoromethyl)-1,3,4-oxadiazol-2-yl)pyridin-2-yl)methyl)-4-(oxetan-3-yl)-N-phenylpiperazine-1-carboxamide

[Step 1] Tert-Butyl 4-(oxetan-3-yl)piperazine-1-carboxylate

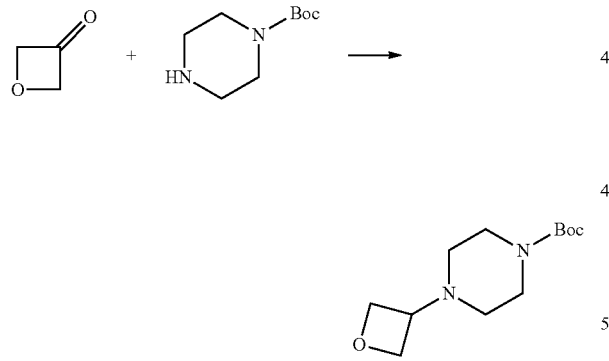

A solution of oxetan-3-one (1.172 mL, 20.000 mmol) and tert-butyl piperazine-1-carboxylate (4.470 g, 24.000 mmol) in 1,2-dichloroethane (80 mL) was stirred at the room temperature for 10 min, and mixed with sodium triacetoxyborohydride (6.782 g, 32.000 mmol). The reaction mixture was stirred at the same temperature for additional 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; methanol/dichloromethane=0% to 5%) to give tert-butyl 4-(oxetan-3-yl)piperazine-1-carboxylate as white solid (4.840 g, 99.9%).

[Step 2] 1-(Oxetan-3-yl)piperazine 2,2,2-trifluoroacetate

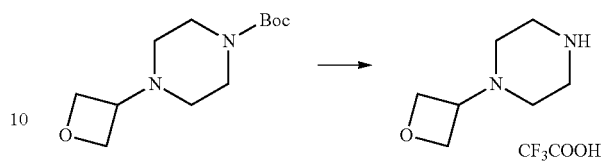

A solution of tert-butyl 4-(oxetan-3-yl)piperazine-1-carboxylate (4.840 g, 19.974 mmol) and trifluoroacetic acid (15.295 mL, 199.736 mmol) in dichloromethane (100 mL) prepared at the room temperature was stirred at the same temperature for 5 hr. The reaction mixture was concentrated under the reduced pressure to remove the solvent The title compound was used without further purification (1-(oxetan-3-yl)piperazine 2,2,2-trifluoroacetate, 5.110 g, 99.8%, pale yellow solid).

[Step 3] 4-(Oxetan-3-yl)-N-phenylpiperazine-1-carboxamide

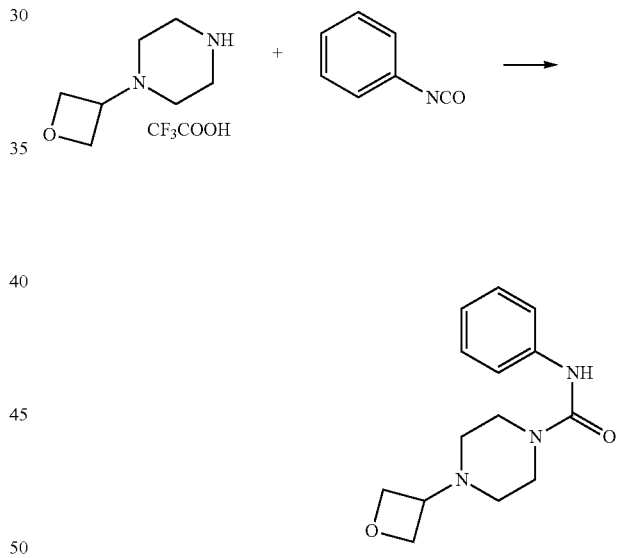

A solution of 1-(oxetan-3-yl)piperazine 2,2,2-trifluoroacetate (0.256 g, 1.000 mmol) and triethylamine (0.418 mL, 3.000 mmol) in diethylether (5 mL) was stirred at the room temperature for 30 min, and mixed with isocyanatobenzene (0.217 mL, 2.000 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give 4-(oxetan-3-yl)-N-phenylpiperazine-1-carboxamide as pale yellow solid (0.155 g, 59.3%).

1099

[Step 4] Methyl 6-((4-(oxetan-3-yl)-N-phenylpiperazine-1-carboxamido)methyl)nicotinate

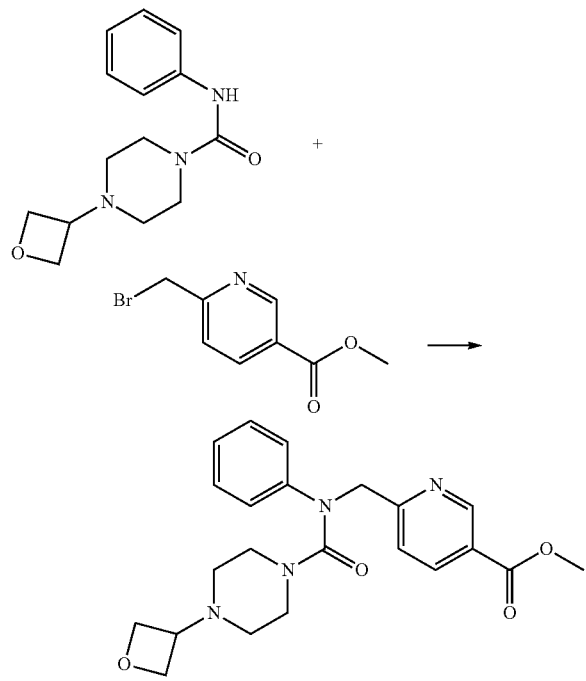

A solution of 4-(oxetan-3-yl)-N-phenylpiperazine-1-carboxamide (0.155 g, 0.593 mmol) and sodium hydride (60.00%, 0.028 g, 0.712 mmol) in tetrahydrofuran (3 mL) was stirred at the room temperature for 30 min, and mixed with methyl 6-(bromomethyl)nicotinate (0.136 g, 0.593 mmol). The reaction mixture was stirred at the same temperature for additional 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 5%) to give methyl 6-((4-(oxetan-3-yl)-N-phenylpiperazine-1-carboxamido)methyl)nicotinate as pale yellow oil (0.055 g, 22.5%).

[Step 5] N-((5-(hydrazinecarbonyl)pyridin-2-yl)methyl)-4-(oxetan-3-yl)-N-phenylpiperazine-1-carboxamide

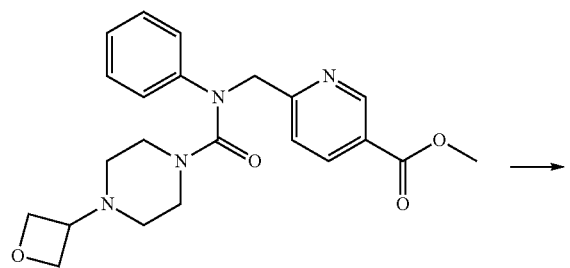

1100

-continued

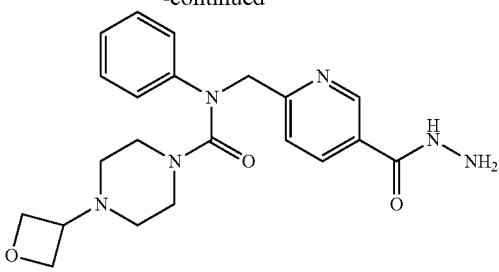

Methyl 6-((4-(oxetan-3-yl)-N-phenylpiperazine-1-carboxamido)methyl)nicotinate (0.055 g, 0.133 mmol) and hydrazine monohydrate (0.130 mL, 2.665 mmol) were mixed at the room temperature in ethanol (2 mL) and then stirred at 75° C. for 18 hr, cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (N-((5-(hydrazinecarbonyl)pyridin-2-yl)methyl)-4-(oxetan-3-yl)-N-phenylpiperazine-1-carboxamide, 0.054 g, 98.7%, white solid).

[Step 6] Compound 21905

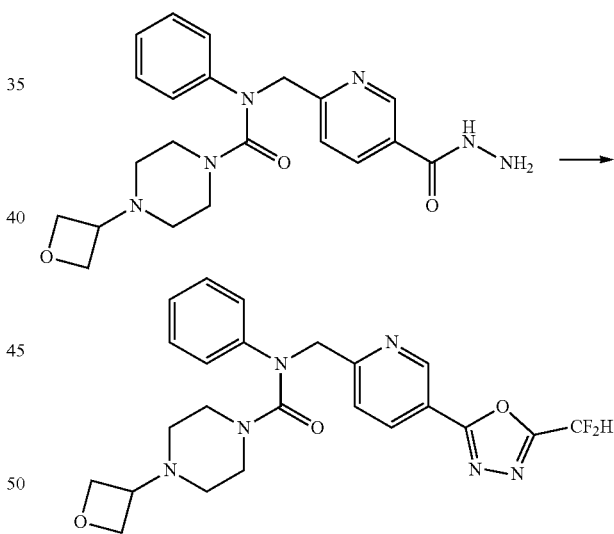

N-((5-(hydrazinecarbonyl)pyridin-2-yl)methyl)-4-(oxetan-3-yl)-N-phenylpiperazine-1-carboxamide (0.054 g, 0.132 mmol), triethylamine (0.055 mL, 0.395 mmol) and 2,2-difluoroacetic anhydride (0.049 mL, 0.395 mmol) were mixed at the room temperature in dichloromethane (2 mL) and then stirred at 40° C. for 18 hr, cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-((5-(5-(difluoromethyl)-1, 3,4-oxadiazol-2-yl)pyridin-2-yl)methyl)-4-(oxetan-3-yl)-N-phenylpiperazine-1-carboxamide as white solid (0.041 g, 65.6%).

¹H NMR (400 MHz, CDCl₃) δ 9.23 (dd, 1H, J=2.3, 0.9 Hz), 8.34 (dd, 1H, J=8.2, 2.3 Hz), 7.62 (d, 1H, J=8.2 Hz), 7.37-7.27 (m, 2H), 7.19-7.15 (m, 2H), 7.12 (t, 1H, J=7.5 Hz), 6.95 (t, 1H, J=51.7 Hz), 5.13 (s, 2H), 4.69-4.61 (m, 4H), 3.40 (brs, 5H), 2.25 (brs, 4H); LRMS (ES) m/z 471.4 (M⁺+1).

Example 363. Compound 21910: N-((3s,5s,7s)-adamantan-1-yl)-N-(4-(5-(difluoromethyl)-1,3,4-oxadiazol-2-yl)-2-fluorobenzyl)morpholine-4-carboxamide

[Step 1] Methyl 4-((((3s,5s,7s)-adamantan-1-yl)amino)methyl)-3-fluorobenzoate

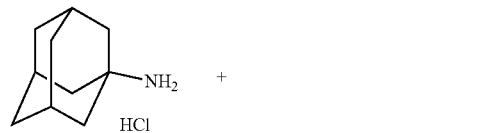

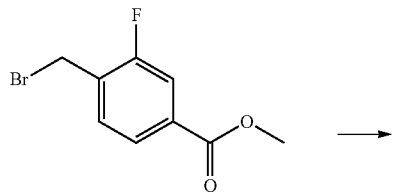

A solution of (3s,5s,7s)-adamantan-1-amine-hydrochloride (2.000 g, 10.689 mmol), methyl 4-(bromomethyl)-3-fluorobenzoate (2.905 g, 11.758 mmol) and N,N-diisopropylethylamine (5.585 mL, 32.067 mmol) in acetonitrile (30 mL) was stirred at the room temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give methyl 4-((((3s,5s,7s)-adamantan-1-yl)amino)methyl)-3-fluorobenzoate as white solid (1.385 g, 40.8%).

[Step 2] Methyl 4-((N-((3s,5s,7s)-adamantan-1-yl)morpholine-4-carboxamido)methyl)-3-fluorobenzoate

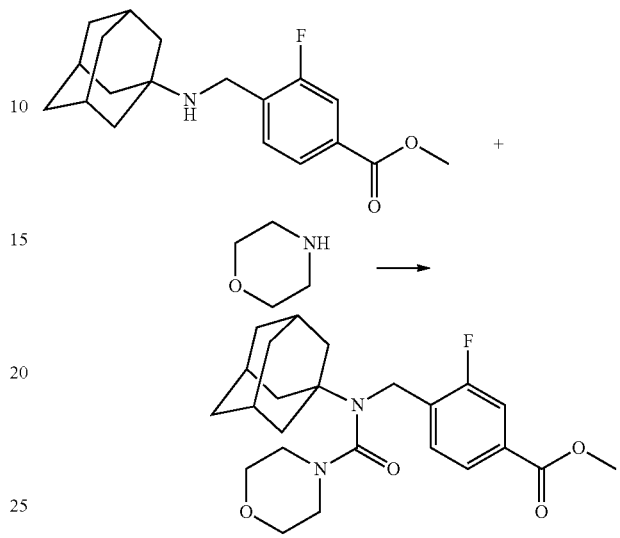

A solution of methyl 4-((((3s,5s,7s)-adamantan-1-yl)amino)methyl)-3-fluorobenzoate (0.500 g, 1.575 mmol), morpholine (0.143 mL, 1.654 mmol), triphosgene (0.234 g, 0.788 mmol) and N,N-diisopropylethylamine (1.646 mL, 9.452 mmol) in dichloromethane (5 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give methyl 4-((N-((3s,5s,7s)-adamantan-1-yl)morpholine-4-carboxamido)methyl)-3-fluorobenzoate as yellow solid (0.659 g, 97.1%).

[Step 3] N-((3s,5s,7s)-adamantan-1-yl)-N-(2-fluoro-4-(hydrazinecarbonyl)benzyl)morpholine-4-carboxamide

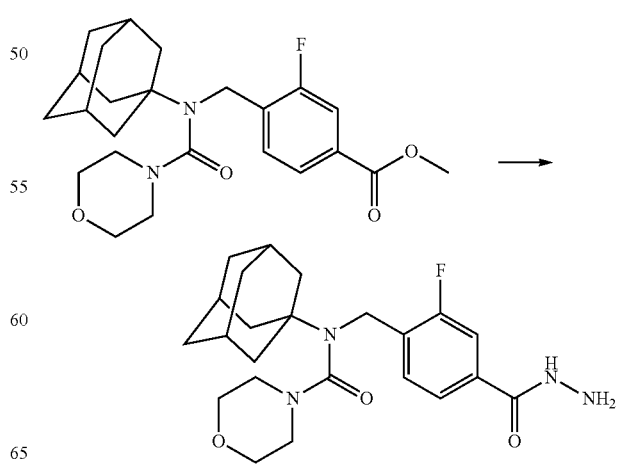

Methyl 4-((N-((3s,5s,7s)-adamantan-1-yl)morpholine-4-carboxamido)methyl)-3-fluorobenzoate (0.659 g, 1.530 mmol) and hydrazine monohydrate (0.744 mL, 15.300 mmol) were mixed at the room temperature in ethanol (2 mL) and then stirred at 100° C. for 18 hr, cooled down to the room temperature to terminate the reaction and concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 10%) to give N-((3s,5s,7s)-adamantan-1-yl)-N-(2-fluoro-4-(hydrazinecarbonyl)benzyl)morpholine-4-carboxamide as white foam (0.587 g, 89.1%).

[Step 4] N-((3s,5s,7s)-adamantan-1-yl)-N-(4-(2-(2,2-difluoroacetyl)hydrazine-1-carbonyl)-2-fluorobenzyl)morpholine-4-carboxamide

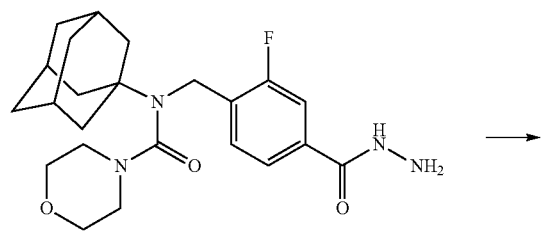

A solution of N-((3s,5s,7s)-adamantan-1-yl)-N-(2-fluoro-4-(hydrazinecarbonyl)benzyl)morpholine-4-carboxamide (0.268 g, 0.623 mmol) and triethylamine (0.174 mL, 1.246 mmol) in dichloromethane (5 mL) was mixed at 0° C. with 2,2-difluoroacetic anhydride (0.077 mL, 0.623 mmol), stirred at the same temperature for 2 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N-((3s,5s,7s)-adamantan-1-yl)-N-(4-(2-(2,2-difluoroacetyl)hydrazine-1-carbonyl)-2-fluorobenzyl)morpholine-4-carboxamide as colorless oil (0.275 g, 86.8%).

[Step 5] Compound 21910

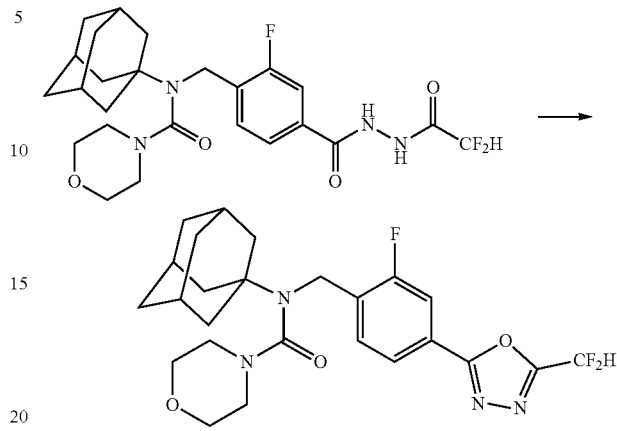

N-((3s,5s,7s)-adamantan-1-yl)-N-(4-(2-(2,2-difluoroacetyl)hydrazine-1-carbonyl)-2-fluorobenzyl)morpholine-4-carboxamide (0.268 g, 0.528 mmol) and 1-methoxy-N-triethylammoniosulfonyl-methanimidate (Burgess reagent, 0.189 g, 0.791 mmol) were mixed at the room temperature in tetrahydrofuran (2 mL) and then stirred at 100° C. for 16 hr, cooled down to the room temperature to terminate the reaction concentrated under the reduced pressure to remove the solvent. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 30%) to give N-((3s,5s,7s)-adamantan-1-yl)-N-(4-(5-(difluoromethyl)-1,3,4-oxadiazol-2-yl)-2-fluorobenzyl)morpholine-4-carboxamide as white foam (0.038 g, 14.6%).

$^1$H NMR (400 MHz, CDCl$_3$) δ 7.88-7.77 (m, 2H), 7.50 (t, 1H, J=7.6 Hz), 6.94 (t, 1H, J=51.7 Hz), 4.19 (s, 2H), 3.41 (q, 4H, J=10.2, 7.6 Hz), 3.23 (s, 4H), 2.14 (s, 3H), 1.96-1.91 (m, 6H), 1.78-1.55 (m, 6H); LRMS (ES) m/z 491.0 (M$^+$+1).

Example 364. Compound 21914: N-(4-((3,3-difluoroazetidin-1-yl)methyl)phenyl)-N-(4-(5-(difluoromethyl)-1,3,4-oxadiazol-2-yl)-2-fluorobenzyl)thiomorpholine-4-carboxamide 1,1-dioxide

[Step 1] N-(4-((3,3-difluoroazetidin-1-yl)methyl)phenyl)thiomorpholine-4-carboxamide 1,1-dioxide

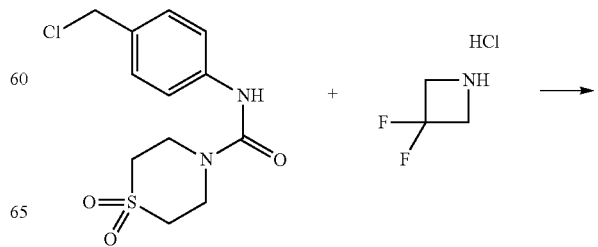

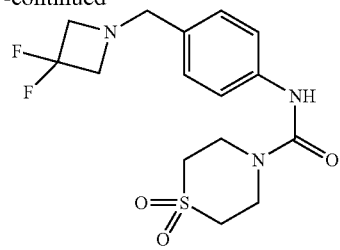

A solution of N-(4-(chloromethyl)phenyl)thiomorpholine-4-carboxamide 1,1-dioxide (0.500 g, 1.651 mmol), 3,3-difluoroazetidine hydrochloride (0.428 g, 3.303 mmol) and potassium carbonate (0.685 g, 4.954 mmol) in acetonitrile (30 mL) was stirred at the room temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate (10 mL) and stirred at the ambient temperature. The resulting precipitates were collected by filtration, washed by ethyl acetate, and dried to give N-(4-((3,3-difluoroazetidin-1-yl)methyl)phenyl)thiomorpholine-4-carboxamide 1,1-dioxide as white solid (0.338 g, 56.9%).

[Step 2] Compound 21914

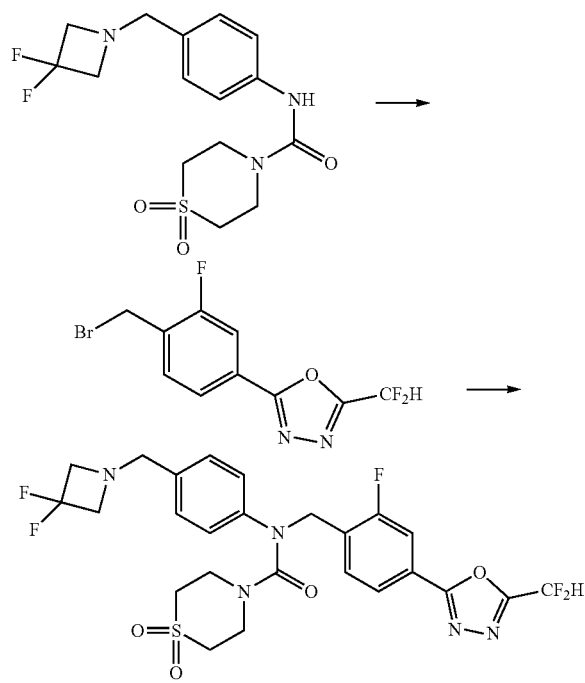

A solution of N-(4-((3,3-difluoroazetidin-1-yl)methyl)phenyl)thiomorpholine-4-carboxamide 1,1-dioxide (0.030 g, 0.083 mmol) and sodium hydride (60.00%, 0.004 g, 0.092 mmol) in N,N-dimethylformamide (2 mL) was stirred at 0° C. for 10 min, and mixed with 2-(4-(bromomethyl)-3-fluorophenyl)-5-(difluoromethyl)-1,3,4-oxadiazole (0.028 g, 0.092 mmol). The reaction mixture was stirred at the room temperature for additional 17 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 4 g cartridge; ethyl acetate/hexane=10% to 60%) to give N-(4-((3,3-difluoroazetidin-1-yl)methyl)phenyl)-N-(4-(5-(difluoromethyl)-1,3,4-oxadiazol-2-yl)-2-fluorobenzyl)thiomorpholine-4-carboxamide 1,1-dioxide as white solid (0.007 g, 14.3%).

$^1$H NMR (400 MHz, CDCl$_3$) δ 7.89 (dd, 1H, J=8.0, 1.6 Hz), 7.76 (dd, 1H, J=10.1, 1.6 Hz), 7.68 (t, 1H, J=7.6 Hz), 7.32 (d, 2H, J=8.4 Hz), 7.12-6.80 (m, 3H), 5.32 (s, 2H), 3.95-3.71 (m, 6H), 3.61 (t, 4H, J=12.0 Hz), 2.79 (t, 4H, J=5.2 Hz); LRMS (ES) m/z 586.2 (M$^+$+1).

Example 365. Compound 21915: N-(4-(5-(difluoromethyl)-1,3,4-oxadiazol-2-yl)-2-fluorobenzyl)-N-(4-((3,3-difluoropyrrolidin-1-yl)methyl)phenyl)thiomorpholine-4-carboxamide 1,1-dioxide

[Step 1] N-(4-((3,3-difluoropyrrolidin-1-yl)methyl)phenyl)thiomorpholine-4-carboxamide 1,1-dioxide

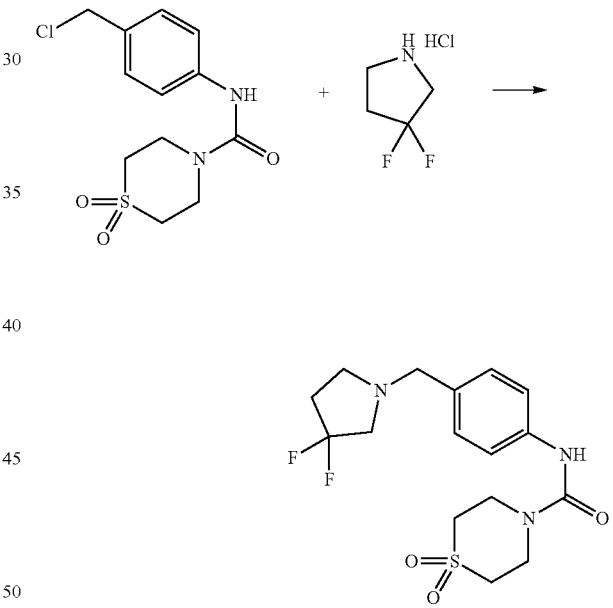

A solution of N-(4-(chloromethyl)phenyl)thiomorpholine-4-carboxamide 1,1-dioxide (0.500 g, 1.651 mmol), 3,3-difluoropyrrolidine hydrochloride (0.474 g, 3.303 mmol) and potassium carbonate (0.685 g, 4.954 mmol) in acetonitrile (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate (10 mL) and stirred. The resulting precipitates were collected by filtration, washed by ethyl acetate, and dried to give N-(4-((3,3-difluoropyrrolidin-1-yl)methyl)phenyl)thiomorpholine-4-carboxamide 1,1-dioxide as pale yellow solid (0.545 g, 88.4%).

1107

[Step 2] Compound 21915

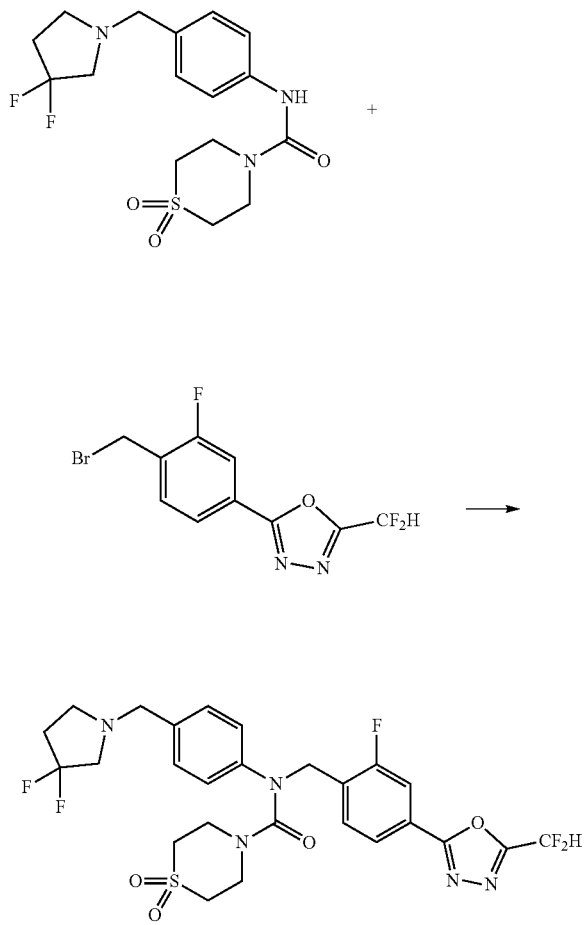

A solution of N-(4-((3,3-difluoropyrrolidin-1-yl)methyl)phenyl)thiomorpholine-4-carboxamide 1,1-dioxide (0.050 g, 0.134 mmol) and sodium hydride (60.00%, 0.006 g, 0.147 mmol) in N,N-dimethylformamide (2 mL) was stirred at 0° C. for 10 min, and mixed with 2-(4-(bromomethyl)-3-fluorophenyl)-5-(difluoromethyl)-1,3,4-oxadiazole (0.045 g, 0.147 mmol). The reaction mixture was stirred at the same temperature for additional 1 hr and concentrated under the reduced pressure to remove the solvent. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 4 g cartridge; ethyl acetate/hexane=10% to 50%) to give N-(4-(5-(difluoromethyl)-1,3,4-oxadiazol-2-yl)-2-fluorobenzyl)-N-(4-((3,3-difluoropyrrolidin-1-yl)methyl)phenyl)thiomorpholine-4-carboxamide 1,1-dioxide as white solid (0.065 g, 81.0%).

$^1$H NMR (400 MHz, CDCl$_3$) δ 7.89 (dd, 1H, J=8.0, 1.6 Hz), 7.77 (dd, 1H, J=10.1, 1.6 Hz), 7.69 (t, 1H, J=7.7 Hz), 7.36-7.33 (m, 2H), 7.12-6.80 (m, 3H), 5.32 (s, 2H), 3.73 (t, 4H, J=5.1 Hz), 3.64 (brs, 2H), 2.91-2.89 (m, 2H), 2.81 (t, 4H, J=5.0 Hz), 2.76 (brs, 2H); LRMS (ES) m/z 600.3 (M$^+$+1).

1108

Example 366. Compound 21916: N-(4-(5-(difluoromethyl)-1,3,4-oxadiazol-2-yl)-2-fluorobenzyl)-N-(4-((4,4-difluoropiperidin-1-yl)methyl)phenyl)thiomorpholine-4-carboxamide 1,1-dioxide

[Step 1] N-(4-((4,4-difluoropiperidin-1-yl)methyl)phenyl)thiomorpholine-4-carboxamide 1,1-dioxide

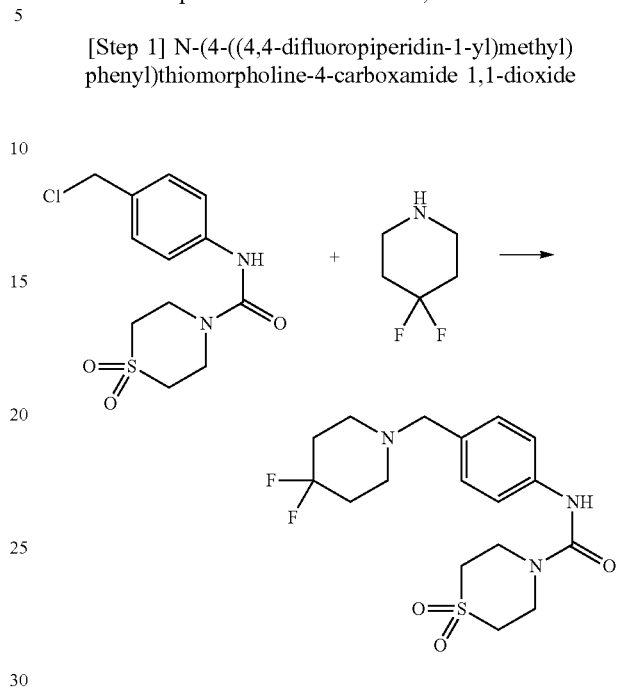

A solution of N-(4-(chloromethyl)phenyl)thiomorpholine-4-carboxamide 1,1-dioxide (0.500 g, 1.651 mmol), 4,4-difluoropiperidine (0.400 g, 3.303 mmol) and potassium carbonate (0.685 g, 4.954 mmol) in acetonitrile (30 mL) was stirred at the room temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate (10 mL) and stirred. The resulting precipitates were collected by filtration, washed by ethyl acetate, and dried to give N-(4-((4,4-difluoropiperidin-1-yl)methyl)phenyl)thiomorpholine-4-carboxamide 1,1-dioxide as pale yellow solid (0.446 g, 69.7%).

[Step 2] Compound 21916

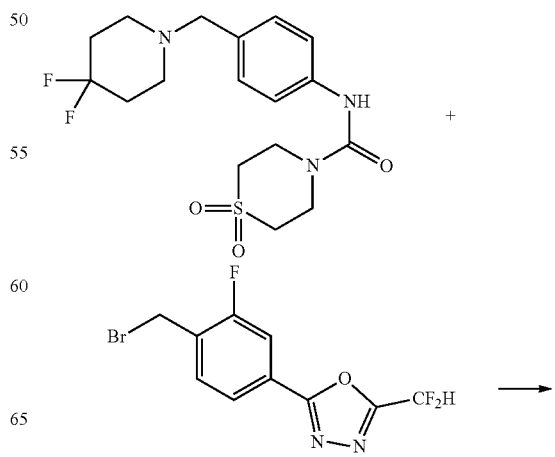

1109
-continued

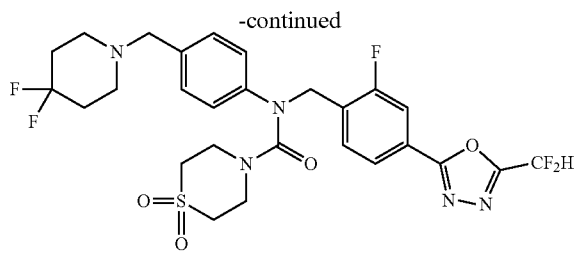

A solution of N-(4-((4,4-difluoropiperidin-1-yl)methyl)phenyl)thiomorpholine-4-carboxamide 1,1-dioxide (0.030 g, 0.077 mmol) and sodium hydride (60.00%, 0.003 g, 0.085 mmol) in N,N-dimethylformamide (2 mL) was stirred at 0° C. for 10 min, and mixed with 2-(4-(bromomethyl)-3-fluorophenyl)-5-(difluoromethyl)-1,3,4-oxadiazole (0.026 g, 0.085 mmol). The reaction mixture was stirred at the room temperature for additional 17 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 12 g cartridge; ethyl acetate/hexane=10% to 60%) to give N-(4-(5-(difluoromethyl)-1,3,4-oxadiazol-2-yl)-2-fluorobenzyl)-N-(4-((4,4-difluoropiperidin-1-yl)methyl)phenyl)thiomorpholine-4-carboxamide 1,1-dioxide as white solid (0.038 g, 80.0%).

$^1$H NMR (400 MHz, $CDCl_3$) δ 7.89 (dd, 1H, J=8.0, 1.6 Hz), 7.76 (dd, 1H, J=10.1, 1.6 Hz), 7.69 (t, 1H, J=7.6 Hz), 7.34 (d, 2H, J=8.2 Hz), 7.11-6.81 (m, 3H), 5.32 (s, 2H), 3.73 (t, 4H, J=5.0 Hz), 3.54 (s, 2H), 2.79 (t, 4H, J=4.8 Hz), 2.54 (s, 4H), 2.07-1.98 (m, 4H); LRMS (ES) m/z 614.3 (M$^+$+1).

Example 367. Compound 21917: (R)—N-(4-(5-(difluoromethyl)-1,3,4-oxadiazol-2-yl)-2-fluorobenzyl)-N-(4-((3-(dimethylamino)pyrrolidin-1-yl)methyl)phenyl)thiomorpholine-4-carboxamide 1,1-dioxide

[Step 1] (R)—N-(4-((3-(dimethylamino)pyrrolidin-1-yl)methyl)phenyl)thiomorpholine-4-carboxamide 1,1-dioxide

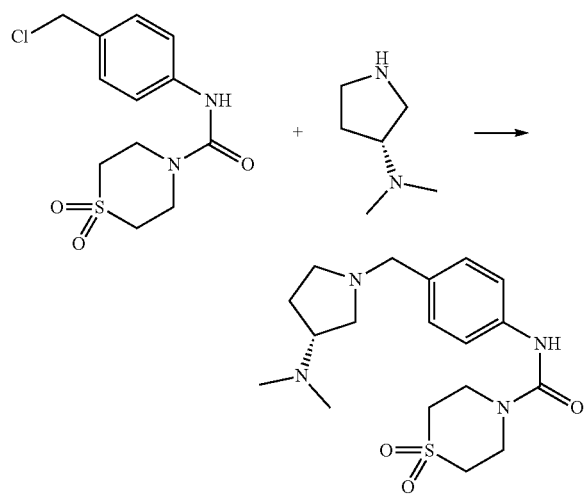

1110

A solution of N-(4-(chloromethyl)phenyl)thiomorpholine-4-carboxamide 1,1-dioxide (0.500 g, 1.651 mmol), (R)—N,N-dimethylpyrrolidin-3-amine (0.377 g, 3.303 mmol) and potassium carbonate (0.685 g, 4.954 mmol) in acetonitrile (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was diluted with ethyl acetate (10 mL) and stirred. The resulting precipitates were collected by filtration, washed by ethyl acetate, and dried to give (R)—N-(4-((3-(dimethylamino)pyrrolidin-1-yl)methyl)phenyl)thiomorpholine-4-carboxamide 1,1-dioxide as pale yellow solid (0.384 g, 61.1%).

[Step 2] Compound 21917

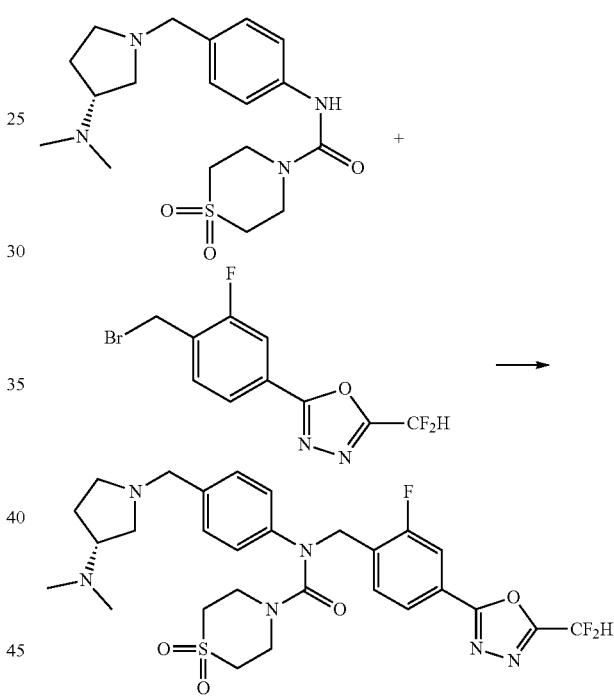

A solution of (R)—N-(4-((3-(dimethylamino)pyrrolidin-1-yl)methyl)phenyl)thiomorpholine-4-carboxamide 1,1-dioxide (0.030 g, 0.079 mmol) and sodium hydride (60.00%, 0.003 g, 0.087 mmol) in N,N-dimethylformamide (2 mL) was stirred at 0° C. for 10 min, and mixed with 2-(4-(bromomethyl)-3-fluorophenyl)-5-(difluoromethyl)-1,3,4-oxadiazole (0.027 g, 0.087 mmol). The reaction mixture was stirred at the room temperature for additional 17 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 4 g cartridge; methanol/dichloromethane=0% to 10%) to give (R)—N-(4-(5-(difluoromethyl)-1,3,4-oxadiazol-2-yl)-2-fluorobenzyl)-N-(4-((3-(dimethylamino)pyrrolidin-1-yl)methyl)phenyl)thiomorpholine-4-carboxamide 1,1-dioxide as yellow solid (0.013 g, 27.2%).

¹H NMR (400 MHz, CDCl₃) δ 7.88 (dd, 1H, J=8.0, 1.6 Hz), 7.75 (dd, 1H, J=10.1, 1.6 Hz), 7.68 (t, 1H, J=7.6 Hz), 7.33 (d, 2H, J=8.4 Hz), 7.09-6.80 (m, 3H), 5.32 (s, 2H), 3.73 (t, 4H, J=5.0 Hz), 3.59 (q, 2H, J=16.7 Hz), 2.97-2.96 (m, 1H), 2.78 (t, 5H, J=5.1 Hz), 2.66-2.58 (m, 2H), 2.49-2.48 (m, 1H), 2.32 (s, 6H), 2.07-2.03 (m, 1H), 1.85-1.82 (m, 1H); LRMS (ES) m/z 607.1 (M⁺+1).

Example 368. Compound 21918: N-(4-(5-(difluoromethyl)-1,3,4-oxadiazol-2-yl)-2-fluorobenzyl)-N-(4-(morpholinomethyl)phenyl)thiomorpholine-4-carboxamide 1,1-dioxide

[Step 1] N-(4-(morpholinomethyl)phenyl)thiomorpholine-4-carboxamide 1,1-dioxid

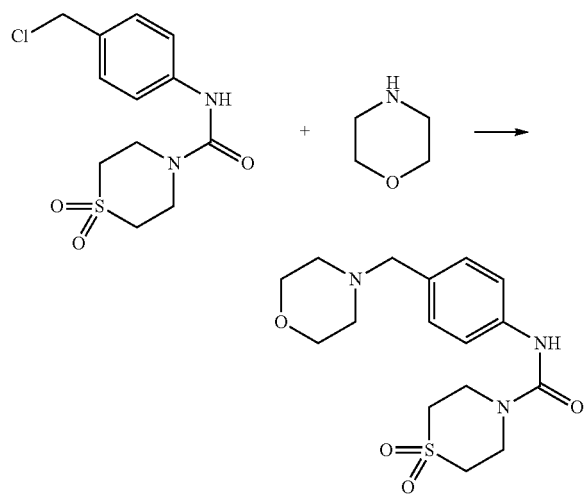

A solution of N-(4-(chloromethyl)phenyl)thiomorpholine-4-carboxamide 1,1-dioxide (0.500 g, 1.651 mmol), morpholine (0.286 mL, 3.303 mmol) and potassium carbonate (0.685 g, 4.954 mmol) in acetonitrile (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with ethyl acetate (10 mL) and stirred. The resulting precipitates were collected by filtration, washed by ethyl acetate, and dried to give N-(4-(morpholinomethyl)phenyl)thiomorpholine-4-carboxamide 1,1-dioxid as pale yellow solid (0.450 g, 77.1%).

[Step 2] Compound 21918

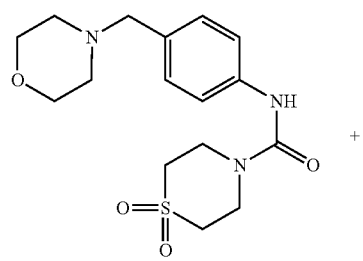

-continued

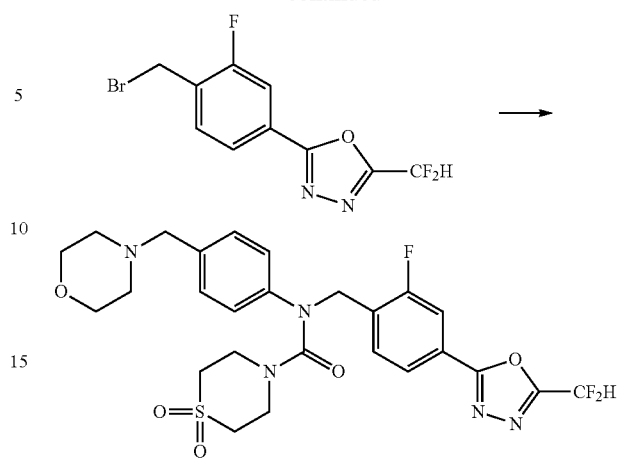

A solution of N-(4-(morpholinomethyl)phenyl)thiomorpholine-4-carboxamide 1,1-dioxide (0.030 g, 0.085 mmol) and sodium hydride (60.00%, 0.004 g, 0.093 mmol) in N,N-dimethylformamide (2 mL) was stirred at 0° C. for 10 min, and mixed with 2-(4-(bromomethyl)-3-fluorophenyl)-5-(difluoromethyl)-1,3,4-oxadiazole (0.029 g, 0.093 mmol). The reaction mixture was stirred at the room temperature for additional 17 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 4 g cartridge; methanol/dichloromethane=0% to 5%) to give N-(4-(5-(difluoromethyl)-1,3,4-oxadiazol-2-yl)-2-fluorobenzyl)-N-(4-(morpholinomethyl)phenyl)thiomorpholine-4-carboxamide 1,1-dioxide as white solid (0.022 g, 44.7%).

¹H NMR (400 MHz, CDCl₃) δ 7.89 (dd, 1H, J=8.0, 1.5 Hz), 7.78-7.75 (m, 1H), 7.68 (t, 1H, J=7.7 Hz), 7.36-7.34 (m, 2H), 7.08-6.81 (m, 3H), 5.32 (s, 2H), 3.73-3.69 (m, 8H), 3.49 (s, 2H), 2.85-2.80 (m, 4H), 2.44 (s, 4H); LRMS (ES) m/z 580.2 (M⁺+1).

Example 369. Compound 21919: N-(4-(5-(difluoromethyl)-1,3,4-oxadiazol-2-yl)-2-fluorobenzyl)-N-(4-(piperidin-1-ylmethyl)phenyl)thiomorpholine-4-carboxamide 1,1-dioxide

[Step 1] N-(4-(piperidin-1-ylmethyl)phenyl)thiomorpholine-4-carboxamide 1,1-dioxide

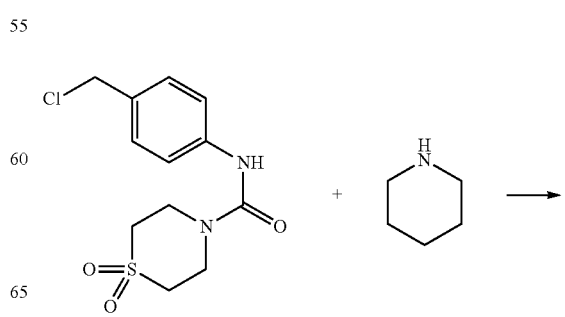

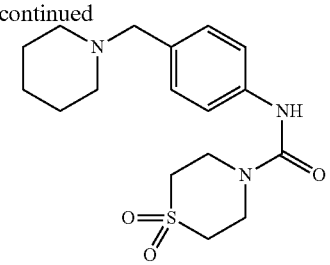

A solution of N-(4-(chloromethyl)phenyl)thiomorpholine-4-carboxamide 1,1-dioxide (0.500 g, 1.651 mmol), piperdine (0.326 mL, 3.303 mmol) and potassium carbonate (0.685 g, 4.954 mmol) in acetonitrile (30 mL) prepared at the room temperature was stirred at the same temperature for 17 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was diluted with ethyl acetate (10 mL) and stirred. The resulting precipitates were collected by filtration, washed by ethyl acetate, and dried to give N-(4-(piperidin-1-ylmethyl)phenyl)thiomorpholine-4-carboxamide 1,1-dioxide as pale yellow solid (0.371 g, 63.9%).

[Step 2] Compound 21919

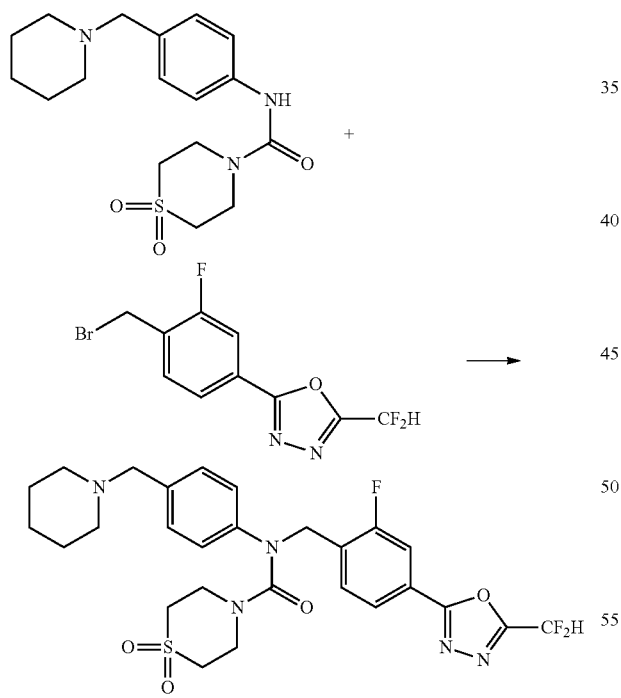

A solution of N-(4-(piperidin-1-ylmethyl)phenyl)thiomorpholine-4-carboxamide 1,1-dioxide (0.030 g, 0.085 mmol) and sodium hydride (60.00%, 0.004 g, 0.094 mmol) in N,N-dimethylformamide (2 mL) was stirred at 0° C. for 10 min, and mixed with 2-(4-(bromomethyl)-3-fluorophenyl)-5-(difluoromethyl)-1,3,4-oxadiazole (0.029 g, 0.094 mmol). The reaction mixture was stirred at the room temperature for additional 17 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 4 g cartridge; methanol/dichloromethane=0% to 5%) to give N-(4-(5-(difluoromethyl)-1,3,4-oxadiazol-2-yl)-2-fluorobenzyl)-N-(4-(piperidin-1-ylmethyl)phenyl)thiomorpholine-4-carboxamide 1,1-dioxide as white solid (0.018 g, 36.5%).

$^1$H NMR (400 MHz, DMSO-$d_6$) δ 7.86 (dd, 1H, J=8.0, 1.6 Hz), 7.78-7.42 (m, 3H), 7.27 (d, 2H, J=8.5 Hz), 7.23 (d, 2H, J=8.7 Hz), 4.91 (s, 2H), 3.56-3.55 (m, 4H), 3.37 (s, 2H), 2.88-2.87 (m, 4H), 2.27 (brs, 4H), 1.48-1.45 (m, 4H), 1.37-1.36 (m, 2H); LRMS (ES) m/z 578.3 (M⁺+1)

Example 370. Compound 21924: N-(4-((1-benzylpiperidin-4-yl)oxy)phenyl)-N-(4-(5-(difluoromethyl)-1,3,4-oxadiazol-2-yl)-2-fluorobenzyl)thiomorpholine-4-carboxamide 1,1-dioxide

[Step 1] Tert-butyl 4-(4-nitrophenoxy)piperidine-1-carboxylate

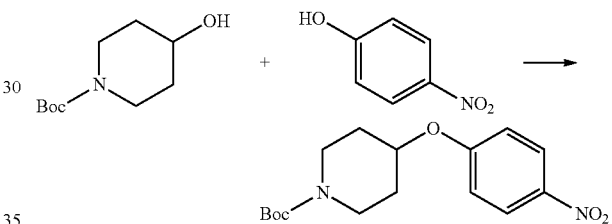

A solution of 4-nitrophenol (1.000 g, 7.189 mmol), tert-butyl 4-hydroxypiperidine-1-carboxylate (1.736 g, 8.626 mmol) and triphenylphosphinetriphenylphosphine (2.263 g, 8.626 mmol) in tetrahydrofuran (30 mL) was mixed at the room temperature with diisopropyl azodicarboxylate (DIAD, 1.698 mL, 8.626 mmol). The reaction mixture was stirred at the same temperature for 18 hr, and concentrated under the reduced pressure. The concentrate was purified and concentrated by column chromatography (SiO₂, 24 g cartridge; ethyl acetate/hexane=0% to 10%) to give tert-butyl 4-(4-nitrophenoxy)piperidine-1-carboxylate as pale yellow solid (1.560 g, 67.3%).

[Step 2] Tert-butyl 4-(4-aminophenoxy)piperidine-1-carboxylate

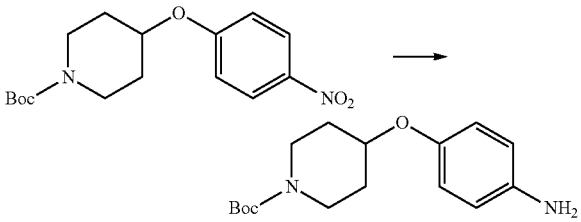

A solution of tert-butyl 4-(4-nitrophenoxy)piperidine-1-carboxylate (1.560 g, 4.839 mmol) in ethanol (100 mL) was slowly added dropwise at the room temperature with 10%-

Pd/C (200 mg), stirred at the same temperature under the hydrogen atmosphere (H₂ balloon) for 18 hr, filtered through a celite pad to remove solids, and concentrated under the reduced pressure. The concentrate was purified and concentrated by column chromatography (SiO₂, 24 g cartridge; ethyl acetate/hexane=0% to 50%) to give tert-butyl 4-(4-aminophenoxy)piperidine-1-carboxylase as brown oil (1.420 g, 100.4%)

[Step 3] Tert-butyl 4-(4-((2-fluoro-4-(methoxycarbonyl)benzyl)amino)phenoxy)piperidine-1-carboxylate

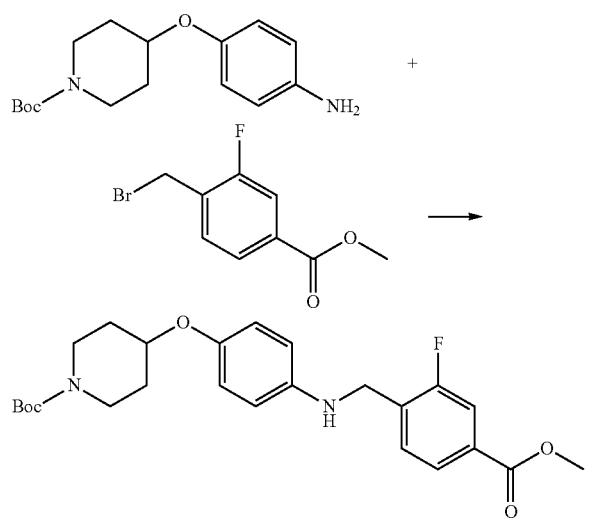

A solution of tert-butyl 4-(4-aminophenoxy)piperidine-1-carboxylate (1.420 g, 4.857 mmol) and sodium hydride (60.00%, 0.204 g, 5.100 mmol) in N,N-dimethylformamide (20 mL) was stirred at 0° C. for 30 min, and mixed with methyl 4-(bromomethyl)-3-fluorobenzoate (1.260 g, 5.100 mmol). The reaction mixture was stirred at the room temperature for additional 17 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 24 g cartridge; ethyl acetate/hexane=0% to 40%) to give tert-butyl 4-(4-((2-fluoro-4-(methoxycarbonyl)benzyl)amino)phenoxy)piperidine-1-carboxylate as yellow oil (1.810 g, 81.3%).

[Step 4] Tert-butyl 4-(4-(N-(2-fluoro-4-(methoxycarbonyl)benzyl)-1,1-dioxidothiomorpholine-4-carboxamido)phenoxy)piperidine-1-carboxylate

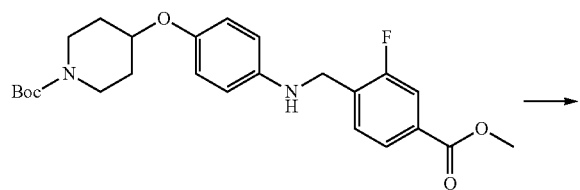

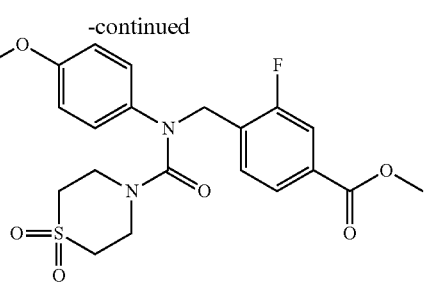

A solution of tert-butyl 4-(4-((2-fluoro-4-(methoxycarbonyl)benzyl)amino)phenoxy)piperidine-1-carboxylate (1.810 g, 3.947 mmol), triphosgene (0.586 g, 1.974 mmol) and N,N-diisopropylethylamine (3.438 mL, 19.737 mmol) in dichloromethane (20 mL) was mixed at 0° C. with thiomorpholine 1,1-dioxide (0.587 g, 4.342 mmol) and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 24 g cartridge; ethyl acetate/hexane=10% to 50%) to give tert-butyl 4-(4-(N-(2-fluoro-4-(methoxycarbonyl)benzyl)-1,1-dioxidothiomorpholine-4-carboxamido)phenoxy)piperidine-1-carboxylate as pale yellow solid (0.935 g, 38.2%).

[Step 5] Methyl 4-((1,1-dioxido-N-(4-(piperidin-4-yloxy)phenyl)thiomorpholine-4-carboxamido)methyl)-3-fluorobenzoate hydrochloride

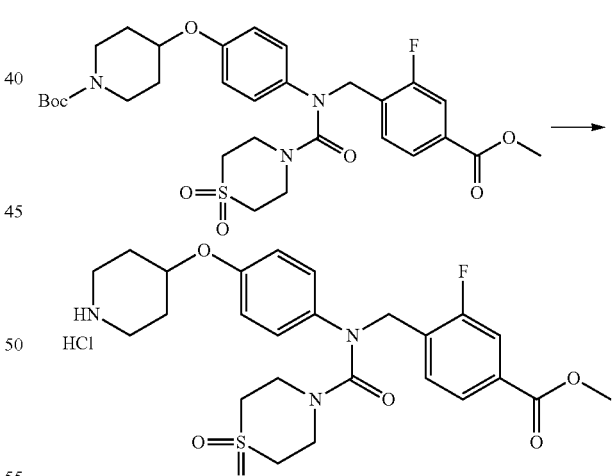

A solution of tert-butyl 4-(4-(N-(2-fluoro-4-(methoxycarbonyl)benzyl)-1,1-dioxidothiomorpholine-4-carboxamido)phenoxy)piperidine-1-carboxylate (0.935 g, 1.509 mmol) in dichloromethane (10 mL) was mixed at the room temperature with hydrochloric acid (4.00 M solution, 1.132 mL, 4.526 mmol), stirred at the same temperature for 17 hr, and concentrated under the reduced pressure. The residue was diluted with ethyl acetate (20 mL) and stirred. The resulting precipitates were collected by filtration, washed by ethyl acetate, and dried to give methyl 4-((1,1-dioxido-N-(4-

(piperidin-4-yloxy)phenyl)thiomorpholine-4-carboxamido)methyl)-3-fluorobenzoate hydrochloride as white solid (0.662 g, 78.9%).

[Step 6] Methyl 4-((N-(4-((1-benzylpiperidin-4-yl)oxy)phenyl)-1,1-dioxidothiomorpholine-4-carboxamido)methyl)-3-fluorobenzoate

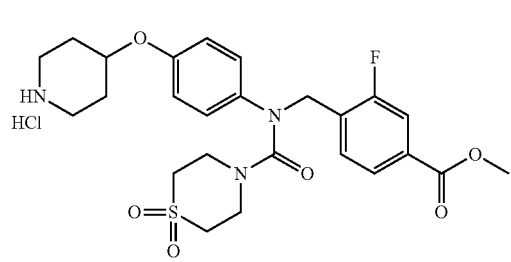

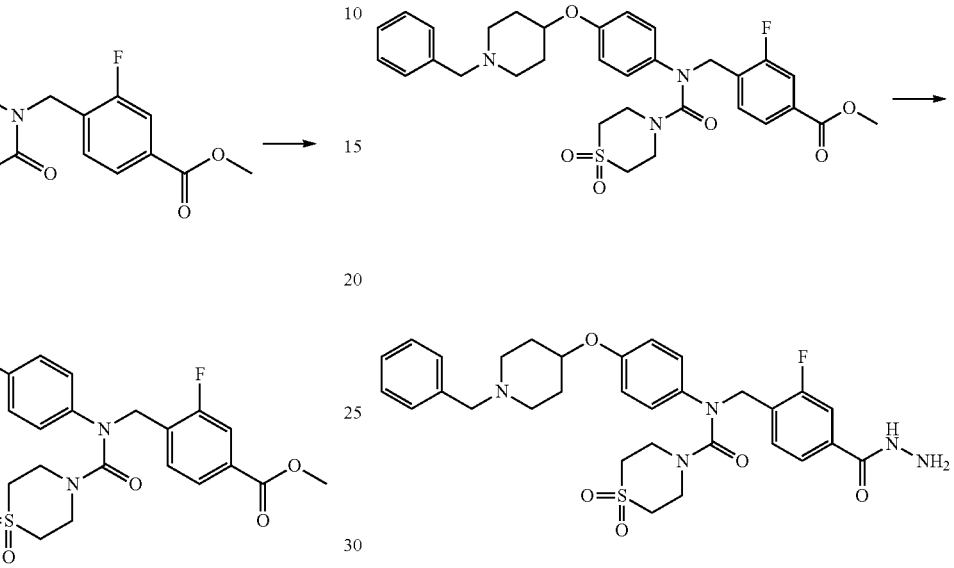

To a stirred solution of methyl 4-((1,1-dioxido-N-(4-(piperidin-4-yloxy)phenyl)thiomorpholine-4-carboxamido)methyl)-3-fluorobenzoate hydrochloride (0.300 g, 0.540 mmol) and N,N-diisopropylethylamine (0.094 mL, 0.540 mmol) in dichloromethane (5 mL) was added at the room temperature benzaldehyde (0.082 mL, 0.809 mmol). The reaction mixture was stirred at the same temperature for 10 min, treated at the same temperature with sodium triacetoxyborohydride (0.229 g, 1.079 mmol), stirred for additional 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; methanol/dichloromethane=0% to 5%) to give methyl 4-((N-(4-((1-benzylpiperidin-4-yl)oxy)phenyl)-1,1-dioxidothiomorpholine-4-carboxamido)methyl)-3-fluorobenzoate as white solid (0.329 g, 100.0%).

[Step 7] N-(4-((1-benzylpiperidin-4-yl)oxy)phenyl)-N-(2-fluoro-4-(hydrazinecarbonyl)benzyl)thiomorpholine-4-carboxamide 1,1-dioxide Methyl 4-((N-(4-((1-benzylpiperidin-4-yl)oxy)phenyl)-1,1-dioxidothiomorpholine-4-carboxamido)methyl)-3-fluorobenzoate (0.329 g, 0.540 mmol) and hydrazine monohydrate (0.525 mL, 10.792 mmol) were mixed at the room temperature in ethanol (4 mL) and then stirred at 100° C. for 17 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. N-(4-((1-benzylpiperidin-4-yl)oxy)phenyl)-N-(2-fluoro-4-(hydrazinecarbonyl)benzyl)thiomorpholine-4-carboxamide 1,1-dioxide was used without further purification (0.246 g, 74.8%, white solid).

[Step 8] Compound 21924

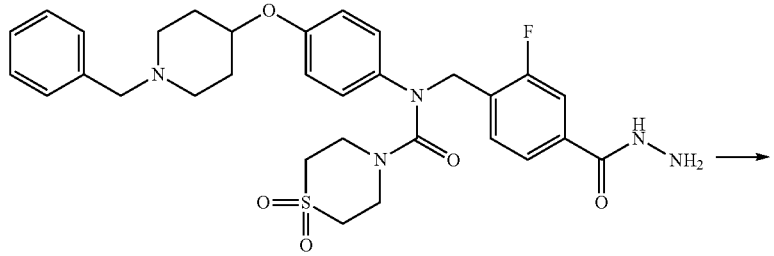

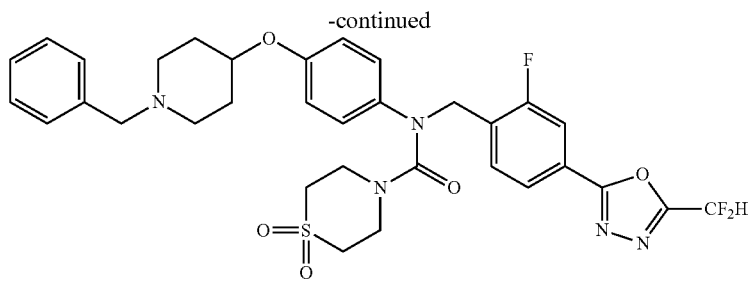

A solution of N-(4-((1-benzylpiperidin-4-yl)oxy)phenyl)-N-(2-fluoro-4-(hydrazinecarbonyl)benzyl)thiomorpholine-4-carboxamide 1,1-dioxide (0.200 g, 0.328 mmol) and triethylamine (0.137 mL, 0.984 mmol) in dichloromethane (5 mL) was mixed at the room temperature with 2,2-difluoroacetic anhydride (0.061 mL, 0.492 mmol). The reaction mixture was stirred at the same temperature for 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-((1-benzylpiperidin-4-yl)oxy)phenyl)-N-(4-(5-(difluoromethyl)-1,3,4-oxadiazol-2-yl)-2-fluorobenzyl)thiomorpholine-4-carboxamide 1,1-dioxide as white solid (0.117 g, 53.3%).

$^1$H NMR (400 MHz, CDCl$_3$) δ 7.88 (dd, 1H, J=8.0, 1.6 Hz), 7.76 (dd, 1H, J=10.0, 1.6 Hz), 7.67 (t, 1H, J=7.6 Hz), 7.37-7.30 (m, 5H), 7.06-6.80 (m, 5H), 4.87 (s, 2H), 4.33 (brs, 1H), 3.73 (t, 4H, J=4.9 Hz), 3.61 (brs, 2H), 2.79 (t, 6H, J=5.0 Hz), 2.40 (brs, 2H), 2.12-2.07 (m, 2H), 1.90-1.87 (m, 2H); LRMS (ES) m/z 670.0 (M$^+$+1).

Example 371. Compound 21925: N-(4-4-(2R,6S)-4-benzyl-2,6-dimethylpiperazin-1-yl)methyl)phenyl)-N-(4-(5-(difluoromethyl)-1,3,4-oxadiazol-2-yl)-2-fluorobenzyl)thiomorpholine-4-carboxamide 1,1-dioxide

[Step 1] Tert-butyl (2S,6R)-4-(4-(1,1-dioxidothiomorpholine-4-carboxamido)benzyl)-2,6-dimethyl-piperazine-1-carboxylate

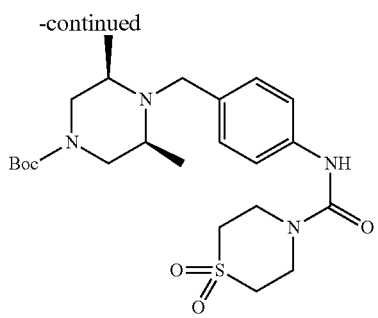

A solution of N-(4-(chloromethyl)phenyl)thiomorpholine-4-carboxamide 1,1-dioxide (1.000 g, 3.303 mmol), tert-butyl (3S,5R)-3,5-dimethylpiperazine-1-carboxylate (1.416 g, 6.606 mmol) and potassium carbonate (1.369 g, 9.909 mmol) in acetonitrile (50 mL) prepared at the room temperature was stirred at the same temperature for 18 hr and concentrated under the reduced pressure. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with diethylether (15 mL) and stirred. The resulting precipitates were collected by filtration, washed by diethylether, and dried to give tert-butyl (2S,6R)-4-(4-(1,1-dioxidothiomorpholine-4-carboxamido)benzyl)-2,6-dimethylpiperazine-1-carboxylate as pale yellow solid (1.580 g, 99.5%).

[Step 2] Tert-butyl (3R,5S)-4-(4-(N-(2-fluoro-4-(methoxycarbonyl)benzyl)-1,1-dioxidothiomorpholine-4-carboxamido)benzyl)-3,5-dimethylpiperazine-1-carboxylate

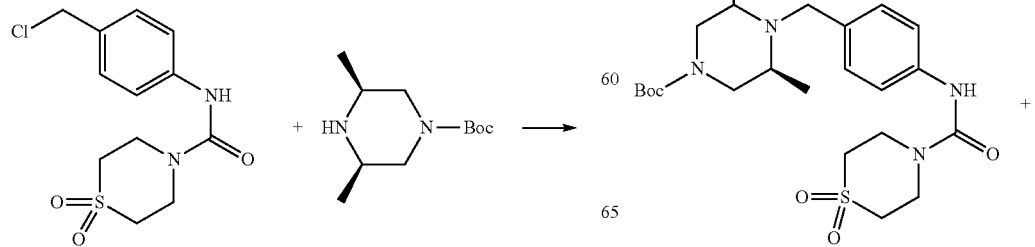

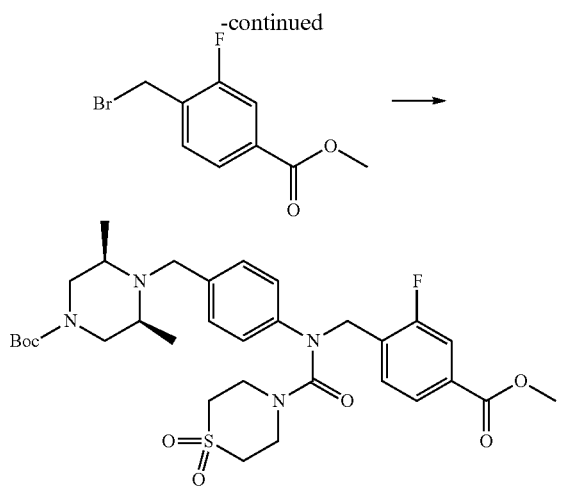

A solution of tert-butyl (2S,6R)-4-(4-(1,1-dioxidothiomorpholine-4-carboxamido)benzyl)-2,6-dimethylpiperazine-1-carboxylate (2.000 g, 4.161 mmol) and sodium hydride (60.00%, 0.183 g, 4.577 mmol) in N,N-dimethylformamide (100 mL) was stirred at 0° C. for 30 min, and mixed with methyl 4-(bromomethyl)-3-fluorobenzoate (1.131 g, 4.577 mmol). The reaction mixture was stirred at the room temperature for additional 3 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 40 g cartridge; methanol/dichloromethane=0% to 10%) to give tert-butyl (3R,5S)-4-(4-(N-(2-fluoro-4-(methoxycarbonyl)benzyl)-1,1-dioxidothiomorpholine-4-carboxamido)benzyl)-3,5-dimethylpiperazine-1-carboxylate as yellow solid (1.980 g, 73.6%).

[Step 3] Methyl 4-((N-(4-(((2R,6S)-2,6-dimethylpiperazin-1-yl)methyl)phenyl)-1,1-dioxidothiomorpholine-4-carboxamido)methyl)-3-fluorobenzoate hydrochloride

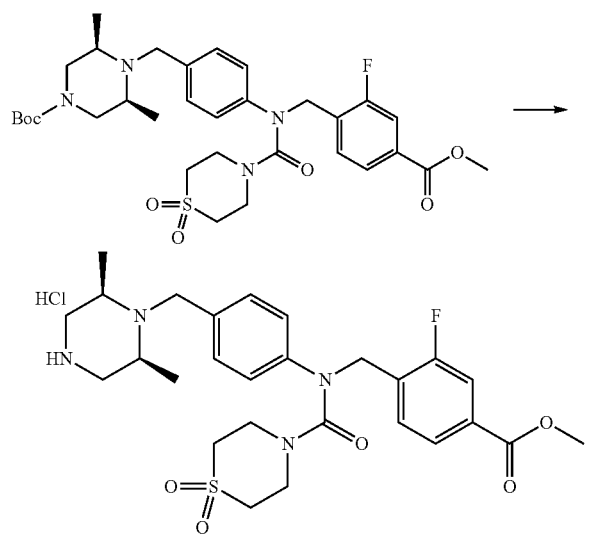

A solution of tert-butyl (3R,5S)-4-(4-(N-(2-fluoro-4-(methoxycarbonyl)benzyl)-1,1-dioxidothiomorpholine-4-carboxamido)benzyl)-3,5-dimethylpiperazine-1-carboxylate (1.980 g, 3.061 mmol) and hydrochloric acid (4.00 M solution, 2.296 mL, 9.184 mmol) in dichloromethane (100 mL) prepared at the room temperature was stirred at the same temperature for 18 hr, and concentrated under the reduced pressure. The residue was diluted with ethyl acetate (100 mL) and stirred. The resulting precipitates were collected by filtration, washed by ethyl acetate, and dried to give methyl 4-((N-(4-(((2R,6S)-2,6-dimethylpiperazin-1-yl)methyl)phenyl)-1,1-dioxidothiomorpholine-4-carboxamido)methyl)-3-fluorobenzoate hydrochloride as white solid (1.730 g, 96.9%).

[Step 4] Methyl 4-((N-(4-(((2R,6S)-4-benzyl-2,6-dimethylpiperazin-1-yl)methyl)phenyl)-1,1-dioxidothiomorpholine-4-carboxamido)methyl)-3-fluorobenzoate

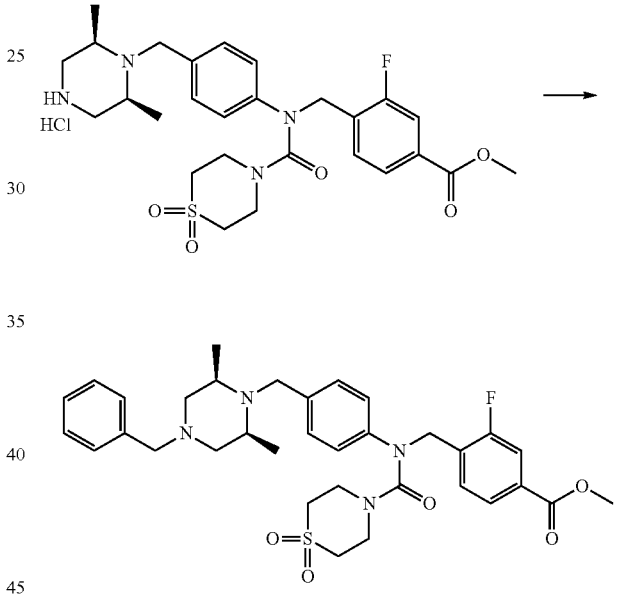

Benzaldehyde (0.078 mL, 0.772 mmol) was added to a solution of methyl 4-((N-(4-(((2R,6S)-2,6-dimethylpiperazin-1-yl)methyl)phenyl)-1,1-dioxidothiomorpholine-4-carboxamido)methyl)-3-fluorobenzoate hydrochloride (0.300 g, 0.514 mmol) and N,N-diisopropylethylamine (0.090 mL, 0.514 mmol) in dichloromethane (5 mL) at the room temperature and the mixture was stirred for 10 min at the same temperature. The reaction mixture was treated at the same temperature with sodium triacetoxyborohydride (0.218 g, 1.029 mmol) and stirred for additional 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give methyl 4-((N-(4-4-(2R,6S)-4-benzyl-2,6-dimethylpiperazin-1-yl)methyl)phenyl)-1,1-dioxidothiomorpholine-4-carboxamido)methyl)-3-fluorobenzoate as pale yellow solid (0.279 g, 85.2%).

1123

[Step 5] N-(4-(((2R,6S)-4-benzyl-2,6-dimethylpiperazin-1-yl)methyl)phenyl)-N-(2-fluoro-4-(hydrazinecarbonyl)benzyl)thiomorpholine-4-carboxamide 1,1-dioxide

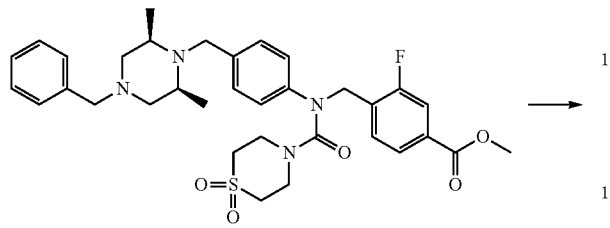

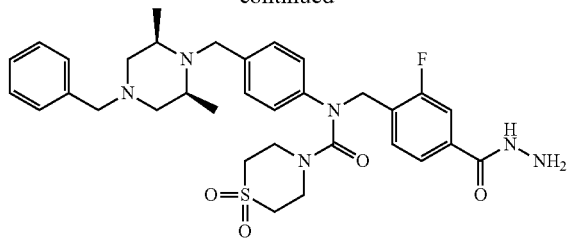

Methyl 4-((N-(4-(((2R,6S)-4-benzyl-2,6-dimethylpiperazin-1-yl)methyl)phenyl)-1,1-dioxidothiomorpholine-4-carboxamido)methyl)-3-fluorobenzoate (0.279 g, 0.438 mmol) and hydrazine monohydrate (0.426 mL, 8.763 mmol) were mixed at the room temperature in ethanol (4 mL) and then stirred at 100° C. for 17 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. N-(4-(((2R,6S)-4-benzyl-2,6-dimethylpiperazin-1-yl)methyl)phenyl)-N-(2-fluoro-4-(hydrazinecarbonyl)benzyl)thiomorpholine-4-carboxamide 1,1-dioxide was used without further purification (0.249 g, 89.2%, white solid).

[Step 6] N-(4-(((2R,6S)-4-benzyl-2,6-dimethylpiperazin-1-yl)methyl)phenyl)-N-(4-(2-(2,2-difluoroacetyl)hydrazine-1-carbonyl)-2-fluorobenzyl)thiomorpholine-4-carboxamide 1,1-dioxide

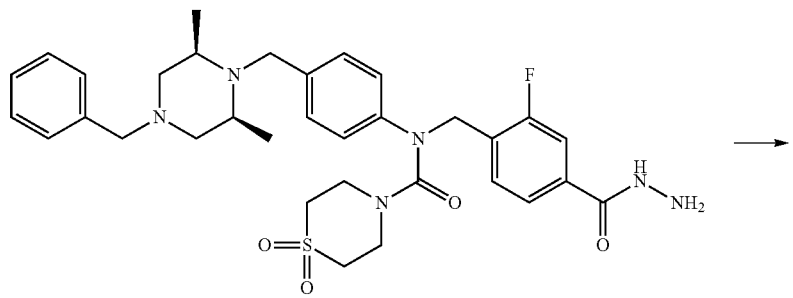

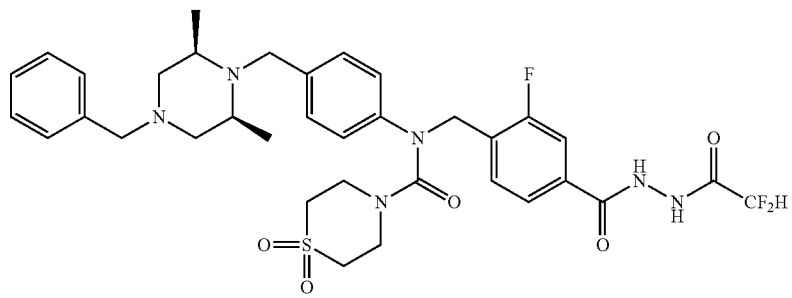

A solution of N-(4-(((2R,6S)-4-benzyl-2,6-dimethylpiperazin-1-yl)methyl)phenyl)-N-(2-fluoro-4-(hydrazinecarbonyl)benzyl)thiomorpholine-4-carboxamide 1,1-dioxide (0.200 g, 0.314 mmol) and triethylamine (0.131 mL, 0.942 mmol) in dichloromethane (5 mL) was mixed at the room temperature with 2,2-difluoroacetic anhydride (0.059 mL, 0.471 mmol). The reaction mixture was stirred at the same temperature for 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; methanol/dichloromethane=0% to 10%) to give N-(4-(((2R,6S)-4-benzyl-2,6-dimethylpiperazin-1-yl)methyl)phenyl)-N-(4-(2-(2,2-difluoroacetyl)hydrazine-1-carbonyl)-2-fluorobenzyl)thiomorpholine-4-carboxamide 1,1-dioxide as white solid (0.117 g, 52.1%).

[Step 7] Compound 21925

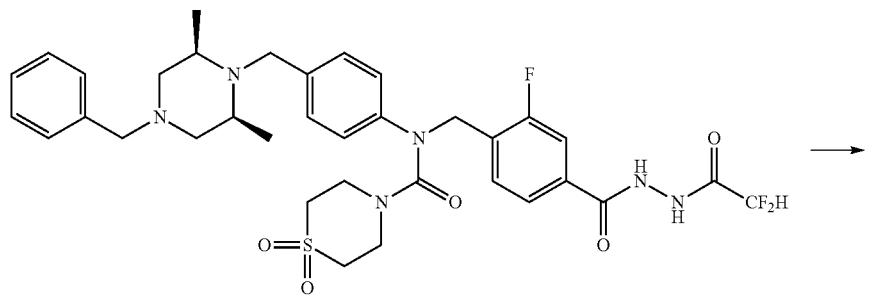

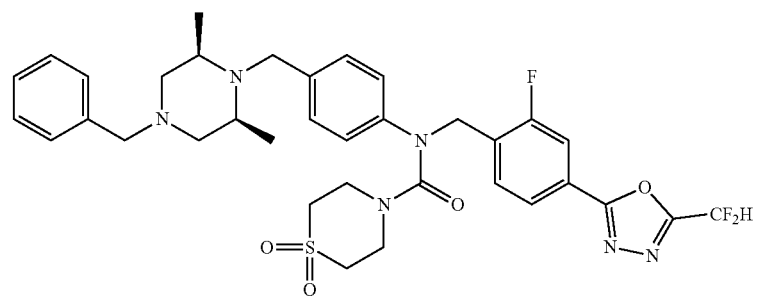

N-(4-(((2R,6S)-4-benzyl-2,6-dimethylpiperazin-1-yl)methyl)phenyl)-N-(4-(2-(2,2-difluoroacetyl)hydrazine-1-carbonyl)-2-fluorobenzyl)thiomorpholine-4-carboxamide 1,1-dioxide (0.100 g, 0.140 mmol) and 1-methoxy-N-triethylammoniosulfonyl-methanimidate (Burgess reagent, 0.100 g, 0.420 mmol) in tetrahydrofuran (4 mL) was mixed at the room temperature and then heated at 150° C. under the microwaves for 30 min, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 50%) to give N-(4-4-(2R,6S)-4-benzyl-2,6-dimethylpiperazin-1-yl)methyl)phenyl)-N-(4-(5-(difluoromethyl)-1,3,4-oxadiazol-2-yl)-2-fluorobenzyl)thiomorpholine-4-carboxamide 1,1-dioxide as pale yellow solid (0.069 g, 70.8%).

$^1$H NMR (400 MHz, DMSO-d$_6$) δ 7.85 (dd, 1H, J=8.0, 1.6 Hz), 7.77-7.71 (m, 2H), 7.55 (t, 1H, J=51.3 Hz), 7.35-7.20 (m, 9H), 4.89 (s, 2H), 3.67 (s, 2H), 3.56 (s, 4H), 3.39 (s, 2H), 2.84 (s, 4H), 2.64-2.62 (m, 2H), 2.53-2.51 (m, 2H), 1.80-1.77 (m, 2H), 0.85 (d, 6H, J=6.1 Hz); LRMS (ES) m/z 697.4 (M$^+$+1).

Example 372. Compound 21926: N-(4-4-(3S,5R)-4-benzyl-3,5-dimethylpiperazin-1-yl)methyl)phenyl)-N-(4-(5-(difluoromethyl)-1,3,4-oxadiazol-2-yl)-2-fluorobenzyl)thiomorpholine-4-carboxamide 1,1-dioxide

[Step 1] Benzyl (3S,5R)-3,5-dimethylpiperazine-1-carboxylate

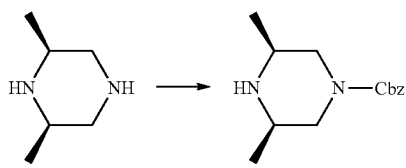

A solution of (2S,6R)-2,6-dimethylpiperazine (10.000 g, 87.573 mmol) and triethylamine (18.309 mL, 131.360 mmol) in dichloromethane (300 mL) was mixed at 0° C. with benzyl chloroformate (13.752 mL, 96.331 mmol) and stirred at the same temperature for 2 hr. Then, saturated aqueous potassium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. Benzyl (3S,5R)-3,5-dimethylpiperazine-1-carboxylate was used without further purification (11.000 g, 50.6%, pale yellow oil).

1127

[Step 2] 4-Benzyl 1-(tert-butyl) (2R,6S)-2,6-dimethylpiperazine-1,4-dicarboxylate

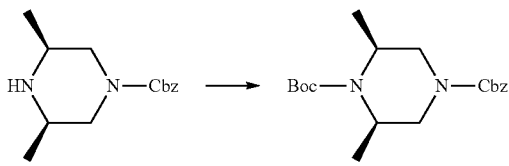 [SMILES: C[C@@H]1CN(C(=O)OCc2ccccc2)C[C@H](C)N1 ; C[C@@H]1CN(C(=O)OCc2ccccc2)C[C@H](C)N1C(=O)OC(C)(C)C]

A solution of benzyl (3S,5R)-3,5-dimethylpiperazine-1-carboxylate (11.000 g, 44.296 mmol), di-tert-butyl dicarbonate (10.634 g, 48.725 mmol) and triethylamine (9.261 mL, 66.444 mmol) in dichloromethane (300 mL) prepared at the room temperature was stirred at the same temperature for 18 hr. Then, water was added to the reaction mixture, followed by extraction with dichloromethane. The organic layer was washed with aqueous saturated sodium chloride solution, dried with anhydrous $MgSO_4$, filtered, and concentrated in vacuo. The concentrate was purified and concentrated by column chromatography ($SiO_2$, 12 g cartridge; ethyl acetate/hexane=0% to 20%) to give 4-benzyl 1-(tert-butyl) (2R,6S)-2,6-dimethylpiperazine-1,4-dicarboxylate as pale yellow oil (6.350 g, 41.2%).

[Step 3] Tert-butyl (2R,6S)-2,6-dimethylpiperazine-1-carboxylate

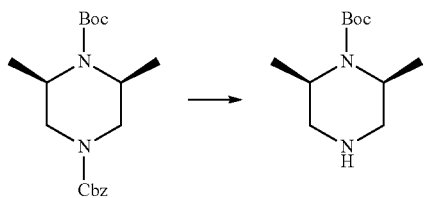

A stirred solution of 4-benzyl 1-(tert-butyl) (2R,6S)-2,6-dimethylpiperazine-1,4-dicarboxylate (6.350 g, 18.224 mmol) in ethanol (150 mL) was slowly added dropwise at the room temperature with 10%-Pd/C (1 g). The reaction mixture was stirred at the same temperature under the hydrogen atmosphere ($H_2$ balloon) for additional 17 hr, filtered through a celite pad to remove solids, and concentrated under the reduced pressure. Tert-butyl (2R,6S)-2,6-dimethylpiperazine-1-carboxylate was used without further purification (3.820 g, 97.8%, yellow oil).

[Step 4] Tert-butyl (2S,6R)-4-(4-(1,1-dioxidothiomorpholine-4-carboxamido)benzyl)-2,6-dimethylpiperazine-1-carboxylate

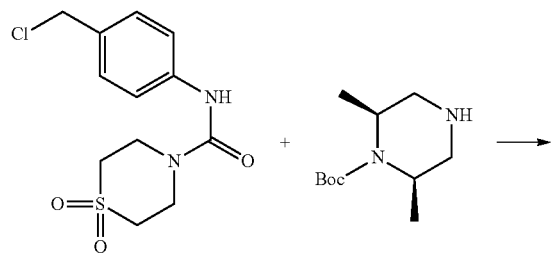

1128

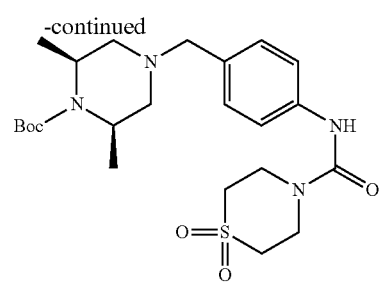

N-(4-(chloromethyl)phenyl)thiomorpholine-4-carboxamide 1,1-dioxide (1.000 g, 3.303 mmol), tert-butyl (2S,6R)-2,6-dimethylpiperazine-1-carboxylate (1.062 g, 4.954 mmol) and potassium carbonate (1.369 g, 9.909 mmol) were mixed at the room temperature in acetonitrile (20 mL) and then stirred at the same temperature for 17 hr, concentrated under the reduced pressure. Then, water was added to the reaction mixture, followed by extraction with ethyl acetate. The organic layer was washed with aqueous saturated sodium chloride solution, dried with anhydrous $MgSO_4$, filtered, and concentrated in vacuo. The concentrate was purified and concentrated by column chromatography ($SiO_2$, 24 g cartridge; ethyl acetate/hexane=10% to 60%) to give tert-butyl (2S,6R)-4-(4-(1,1-dioxidothiomorpholine-4-carboxamido)benzyl)-2,6-dimethylpiperazine-1-carboxylate as white solid (1.950 g, 99.6%).

[Step 5] Tert-butyl (2S,6R)-4-(4-(N-(2-fluoro-4-(methoxycarbonyl)benzyl)-1,1-dioxidothiomorpholine-4-carboxamido)benzyl)-2,6-dimethylpiperazine-1-carboxylate

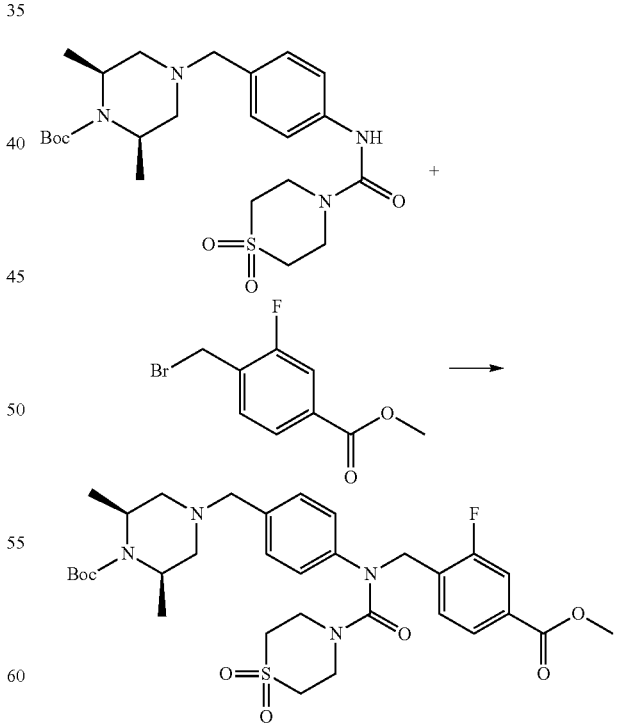

A solution of tert-butyl (2S,6R)-4-(4-(1,1-dioxidothiomorpholine-4-carboxamido)benzyl)-2,6-dimethylpiperazine-1-carboxylate (1.450 g, 3.017 mmol) and sodium hydride (60.00%, 0.133 g, 3.319 mmol) in N,N-dimethylformamide (30 mL) was stirred at 0° C. for 10 min, and mixed with methyl 4-(bromomethyl)-3-fluorobenzoate (0.820 g, 3.319 mmol). The reaction mixture was stirred at the same temperature for additional 1 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=10% to 60%) to give tert-butyl (2S,6R)-4-(4-(N-(2-fluoro-4-(methoxycarbonyl)benzyl)-1,1-dioxidothiomorpholine-4-carboxamido)benzyl)-2,6-dimethylpiperazine-1-carboxylate as yellow solid (1.950 g, 99.9%).

[Step 6] Methyl 4-((N-(4-4-(3S,5R)-3,5-dimethyl-piperazin-1-yl)methyl)phenyl)-1,1-dioxidothiomorpholine-4-carboxamido)methyl)-3-fluorobenzoate hydrochloride

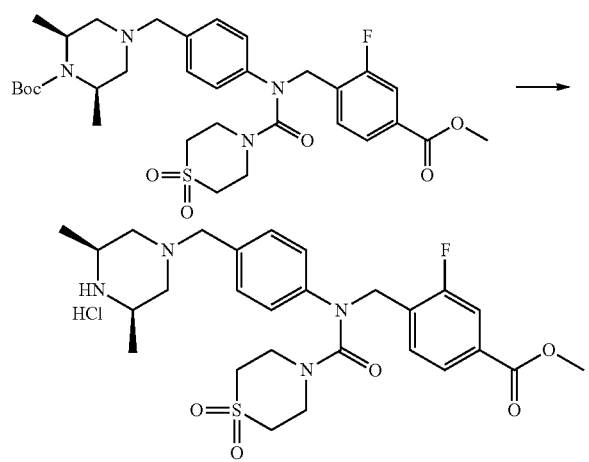

A solution of tert-butyl (2S,6R)-4-(4-(N-(2-fluoro-4-(methoxycarbonyl)benzyl)-1,1-dioxidothiomorpholine-4-carboxamido)benzyl)-2,6-dimethylpiperazine-1-carboxylate (1.950 g, 3.015 mmol) and hydrochloric acid (4.00 M solution, 3.769 mL, 15.075 mmol) in dichloromethane (30 mL) was stirred at the room temperature for 17 hr and then for additional 17 hr at the same temperature, and concentrated under the reduced pressure. The residue was diluted with ethyl acetate (20 mL) and stirred. The resulting precipitates were collected by filtration, washed by ethyl acetate, and dried to give methyl 4-((N-(4-(((3S,5R)-3,5-dimethylpiperazin-1-yl)methyl)phenyl)-1,1-dioxidothiomorpholine-4-carboxamido)methyl)-3-fluorobenzoate hydrochloride as pale yellow solid (1.650 g, 93.9%).

[Step 7] Methyl 4-((N-(4-(((3S,5R)-4-benzyl-3,5-dimethylpiperazin-1-yl)methyl)phenyl)-1,1-dioxido-thiomorpholine-4-carboxamido)methyl)-3-fluorobenzoate

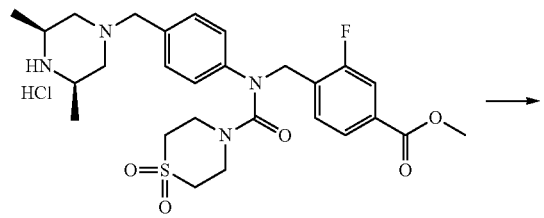

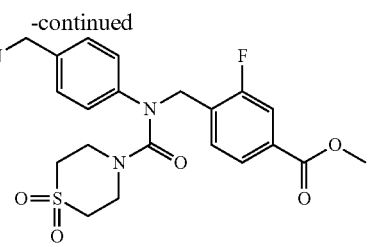

A solution of methyl 4-((N-(4-(((3S,5R)-3,5-dimethylpiperazin-1-yl)methyl)phenyl)-1,1-dioxidothiomorpholine-4-carboxamido)methyl)-3-fluorobenzoate hydrochloride (0.300 g, 0.514 mmol), (bromomethyl)benzene (0.067 mL, 0.566 mmol) and potassium carbonate (0.213 g, 1.543 mmol) in acetonitrile (5 mL) was stirred at the room temperature for 17 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=30% to 100%) to give methyl 4-((N-(4-(((3S,5R)-4-benzyl-3,5-dimethylpiperazin-1-yl)methyl)phenyl)-1,1-dioxidothiomorpholine-4-carboxamido)methyl)-3-fluorobenzoate as pale yellow solid (0.120 g, 36.6%).

[Step 8] N-(4-(((3S,5R)-4-benzyl-3,5-dimethylpiperazin-1-yl)methyl)phenyl)-N-(2-fluoro-4-(hydrazinecarbonyl)benzyl)thiomorpholine-4-carboxamide 1,1-dioxide

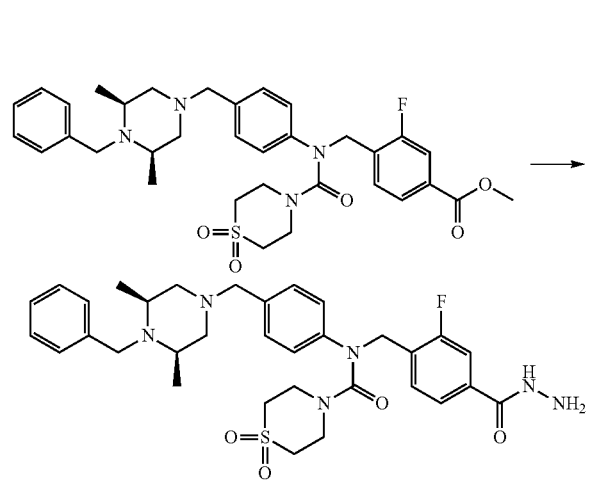

Methyl 4-((N-(4-(((3S,5R)-4-benzyl-3,5-dimethylpiperazin-1-yl)methyl)phenyl)-1,1-dioxidothiomorpholine-4-carboxamido)methyl)-3-fluorobenzoate (0.120 g, 0.188 mmol) and hydrazine monohydrate (0.183 mL, 3.769 mmol) were mixed at the room temperature in ethanol (4 mL) and then stirred at 100° C. for 17 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. N-(4-(((3S,5R)-4-benzyl-3,5-dimethylpiperazin-1-yl)methyl)phenyl)-N-(2-fluoro-4-(hydrazinecarbonyl)benzyl)thiomorpholine-4-carboxamide 1,1-dioxide was used without further purification (0.122 g, 101.7%, pale yellow solid).

[Step 9] Compound 21926

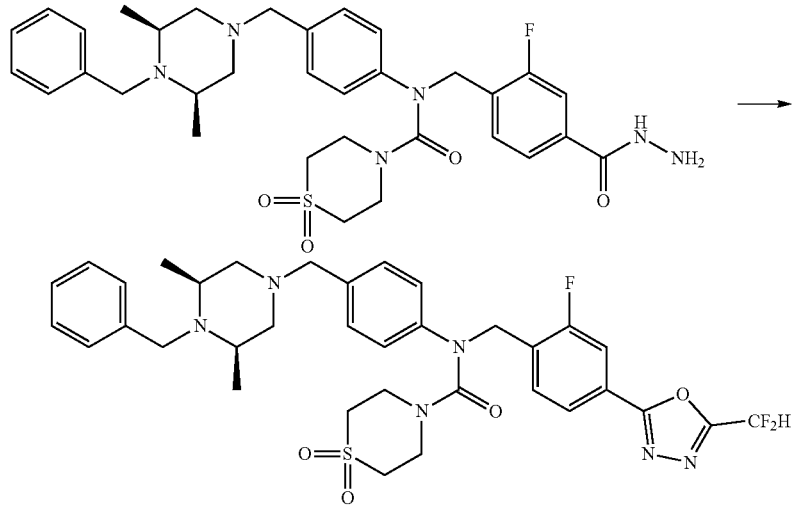

2,2-Difluoroacetic anhydride (0.032 mL, 0.259 mmol) was added to a solution of N-(4-4-(3S,5R)-4-benzyl-3,5-dimethylpiperazin-1-yl)methyl)phenyl)-N-(2-fluoro-4-(hydrazinecarbonyl)benzyl)thiomorpholine-4-carboxamide 1,1-dioxide (0.110 g, 0.173 mmol) and triethylamine (0.072 mL, 0.518 mmol) in dichloromethane (5 mL) was mixed at the room temperature, the reaction mixture was heated at reflux for 17 hr and cooled down to the room temperature to terminate the reaction. Then; water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-4-(3S,5R)-4-benzyl-3,5-dimethylpiperazin-1-yl) methyl)phenyl)-N-(4-(5-(difluoromethyl)-1,3,4-oxadiazol-2-yl)-2-fluorobenzyl)thiomorpholine-4-carboxamide 1,1-dioxide as yellow solid (0.038 g, 31.6%).

$^1$H NMR (400 MHz, CDCl$_3$) δ 7.88 (dd, 1H, J=8.0, 1.6 Hz), 7.76 (dd, 1H, J=10.0, 1.6 Hz), 7.67 (t, 1H, J=7.6 Hz), 7.37-7.30 (m, 5H), 7.06-6.80 (m, 5H), 4.87 (s, 2H), 4.33 (brs, 1H), 3.73 (t, 4H, J=4.9 Hz), 3.61 (brs, 2H), 2.79 (t, 6H, J=5.0 Hz), 2.40 (brs, 2H), 2.12-2.07 (m, 2H), 1.90-1.87 (m, 2H); LRMS (ES) m/z 670.0 (M$^+$+1).

Example 373. Compound 21929: N-(3-chloro-4-fluorophenyl)-N-(4-(5-(difluoromethyl)-1,3,4-oxadiazol-2-yl)-2-fluorobenzyl)morpholine-4-carboxamide

[Step 1] Methyl 4-(((3-chloro-4-fluorophenyl)amino)methyl)-3-fluorobenzoate

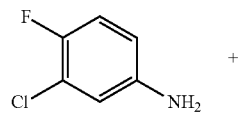

-continued

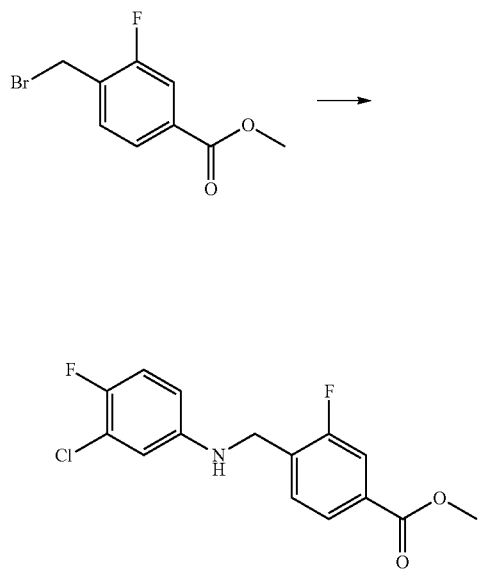

A solution of 3-chloro-4-fluoroaniline (0.500 g, 3.435 mmol), methyl 4-(bromomethyl)-3-fluorobenzoate (0.934 g, 3.779 mmol) and N,N-diisopropylethylamine (1.197 mL, 6.870 mmol) in acetonitrile (5 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=0% to 30%) to give methyl 4-(((3-chloro-4-fluorophenyl)amino)methyl)-3-fluorobenzoate as orange solid (0.943 g, 88.1%).

[Step 2] Methyl 4-((N-(3-chloro-4-fluorophenyl)morpholine-4-carboxamido)methyl)-3-fluorobenzoate

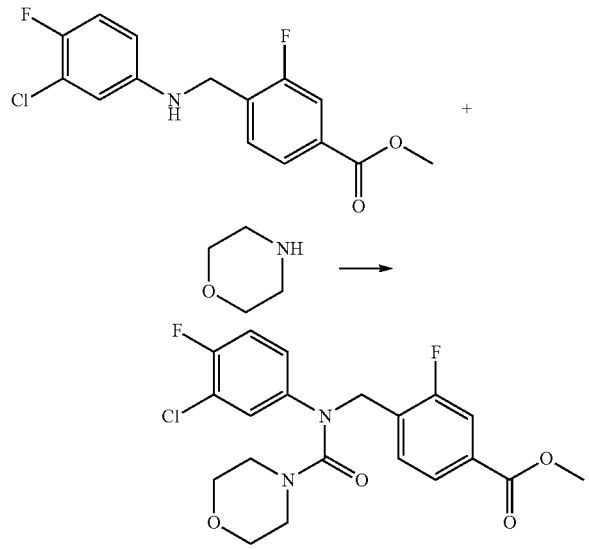

Triphosgene (0.449 g, 1.513 mmol) was added to a solution of methyl 4-(((3-chloro-4-fluorophenyl)amino)methyl)-3-fluorobenzoate (0.943 g, 3.025 mmol) and N,N-diisopropylethylamine (3.162 mL, 18.151 mmol) in dichloromethane (10 mL) at 0° C., and the reaction mixture was stirred at the same temperature for 1 hr. The reaction mixture was treated at the room temperature with morpholine (0.275 mL, 3.177 mmol) and stirred for additional 4 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; ethyl acetate/hexane=10% to 30%) to give methyl 4-((N-(3-chloro-4-fluorophenyl)morpholine-4-carboxamido)methyl)-3-fluorobenzoate as colorless oil (0.802 g, 62.4%).

[Step 3] N-(3-chloro-4-fluorophenyl)-N-(2-fluoro-4-(hydrazinecarbonyl)benzyl)morpholine-4-carboxamide

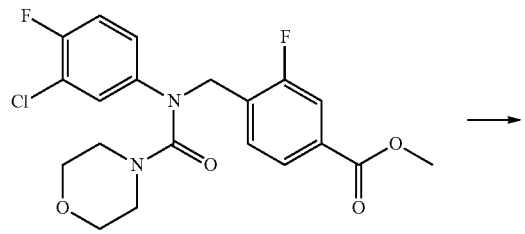

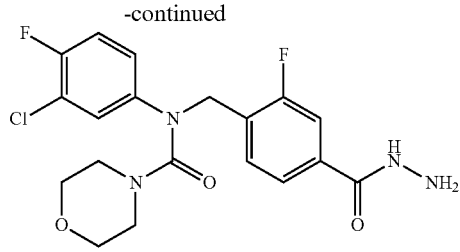

Methyl 4-((N-(3-chloro-4-fluorophenyl)morpholine-4-carboxamido)methyl)-3-fluorobenzoate (0.802 g, 1.887 mmol) and hydrazine monohydrate (0.917 mL, 18.869 mmol) were mixed at the room temperature in ethanol (2 mL) and then stirred at 100° C. for 18 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 10%) to give N-(3-chloro-4-fluorophenyl)-N-(2-fluoro-4-(hydrazinecarbonyl)benzyl)morpholine-4-carboxamide as white foam (0.687 g, 85.7%).

[Step 4] N-(3-chloro-4-fluorophenyl)-N-(4-(2-(2,2-difluoroacetyl)hydrazine-1-carbonyl)-2-fluorobenzyl)morpholine-4-carboxamide

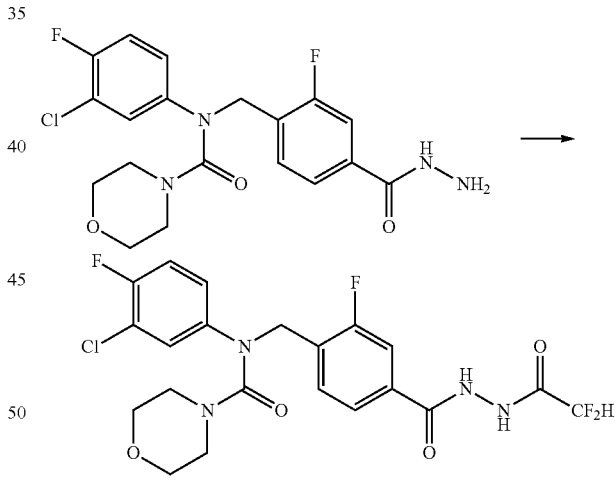

A solution of N-(3-chloro-4-fluorophenyl)-N-(2-fluoro-4-(hydrazinecarbonyl)benzyl)morpholine-4-carboxamide (0.321 g, 0.756 mmol) and triethylamine (0.211 mL, 1.511 mmol) in dichloromethane (5 mL) was mixed at 0° C. with 2,2-difluoroacetic anhydride (0.094 mL, 0.756 mmol), stirred at the same temperature for 2 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10% to give N-(3-chloro-4-fluorophenyl)-N-(4-

(2-(2,2-difluoroacetyl)hydrazine-1-carbonyl)-2-fluorobenzyl)morpholine-4-carboxamide as colorless oil (0.287 g, 75.5%).

[Step 5] Compound 21929

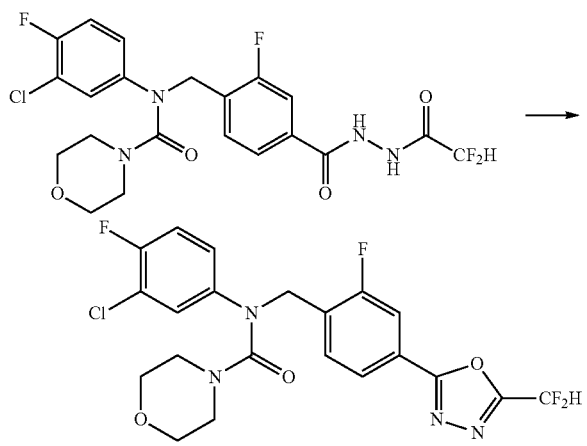

N-(3-chloro-4-fluorophenyl)-N-(4-(2-(2,2-difluoroacetyl)hydrazine-1-carbonyl)-2-fluorobenzyl)morpholine-4-carboxamide (0.034 g, 0.068 mmol) and 1-methoxy-N-triethylammoniosulfonyl-methanimidate (Burgess reagent, 0.024 g, 0.101 mmol) were mixed at the room temperature in tetrahydrofuran (2 mL) and then stirred at 100° C. for 16 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 30%) to give N-(3-chloro-4-fluorophenyl)-N-(4-(5-(difluoromethyl)-1,3,4-oxadiazol-2-yl)-2-fluorobenzyl)morpholine-4-carboxamide as white foam (0.006 g, 18.3%).

$^1$H NMR (400 MHz, CDCl$_3$) δ 7.90 (d, 1H, J=8.0 Hz), 7.78 (d, 1H, J=10.0 Hz), 7.71 (t, 1H, J=7.6 Hz), 7.21 (dd, 1H, J=6.4, 2.6 Hz), 7.12 (t, 1H, J=8.6 Hz), 7.08-6.78 (m, 2H), 4.93 (s, 2H), 3.53 (t, 4H, J=4.7 Hz), 3.27 (t, 4H, J=4.7 Hz); LRMS (ES) m/z 485.0 (M$^+$+1)

Example 374. Compound 21930: N-(3-chloro-4-fluorophenyl)-N-(2-fluoro-4-(5-(trifluoromethyl)-1,3,4-oxadiazol-2-yl)benzyl)morpholine-4-carboxamide

[Step 1] N-(3-chloro-4-fluorophenyl)-N-(2-fluoro-4-(2-(2,2,2-trifluoroacetyl)hydrazine-1-carbonyl)benzyl)morpholine-4-carboxamide

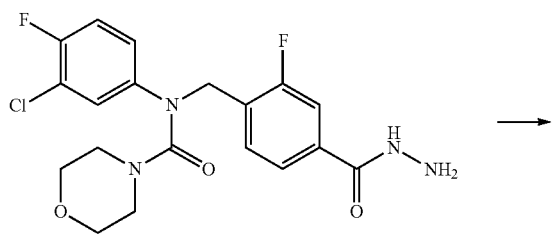

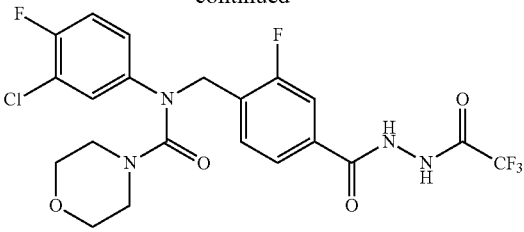

A solution of N-(3-chloro-4-fluorophenyl)-N-(2-fluoro-4-(hydrazinecarbonyl)benzyl)morpholine-4-carboxamide (0.321 g, 0.756 mmol) and triethylamine (0.211 mL, 1.511 mmol) in dichloromethane (5 mL) was mixed at 0° C. with trifluoroacetic anhydride (0.107 mL, 0.756 mmol), stirred at the same temperature for 2 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N-(3-chloro-4-fluorophenyl)-N-(2-fluoro-4-(2-(2,2,2-trifluoroacetyl)hydrazine-1-carbonyl)benzyl)morpholine-4-carboxamide as colorless oil (0.286 g, 72.7%).

[Step 2] Compound 21930

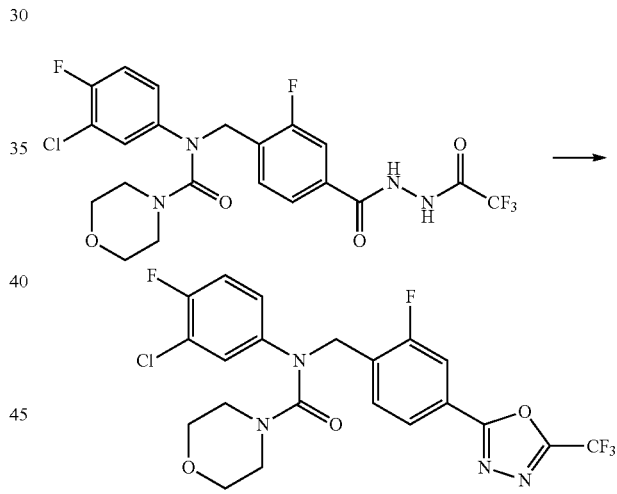

N-(3-chloro-4-fluorophenyl)-N-(2-fluoro-4-(2-(2,2,2-trifluoroacetyl)hydrazine-1-carbonyl)benzyl)morpholine-4-carboxamide (0.321 g, 0.616 mmol) and 1-methoxy-N-triethylammoniosulfonyl-methanimidate (Burgess reagent, 0.220 g, 0.924 mmol) were mixed at the room temperature in tetrahydrofuran (2 mL) and then stirred at 100° C. for 16 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 30%) to give N-(3-chloro-4-fluorophenyl)-N-(2-fluoro-4-(5-(trifluoromethyl)-1,3,4-oxadiazol-2-yl)benzyl)morpholine-4-carboxamide as white foam (0.121 g, 38.9%).

1137

$^1$H NMR (400 MHz, CDCl$_3$) δ 7.90 (d, 1H, J=8.0 Hz), 7.82-7.69 (m, 2H), 7.22 (dd, 1H, J=6.4, 2.3 Hz), 7.12 (t, 1H, J=8.4 Hz), 7.01 (ddd, 1H, J=8.6, 4.2, 2.1 Hz), 4.93 (s, 2H), 3.53 (t, 4H, J=4.7 Hz), 3.26 (t, 4H, J=4.7 Hz); LRMS (ES) m/z 503.1 (M$^+$+1).

Example 375. Compound 21931: N-((3s,5s,7s)-adamantan-1-yl)-N-(2-fluoro-4-(5-(trifluoromethyl)-1,3,4-oxadiazol-2-yl)benzyl)morpholine-4-carboxamide

[Step 1] N-((3s,5s,7s)-adamantan-1-yl)-N-(2-fluoro-4-(2-(2,2,2-trifluoroacetyl)hydrazine-1-carbonyl)benzyl)morpholine-4-carboxamide

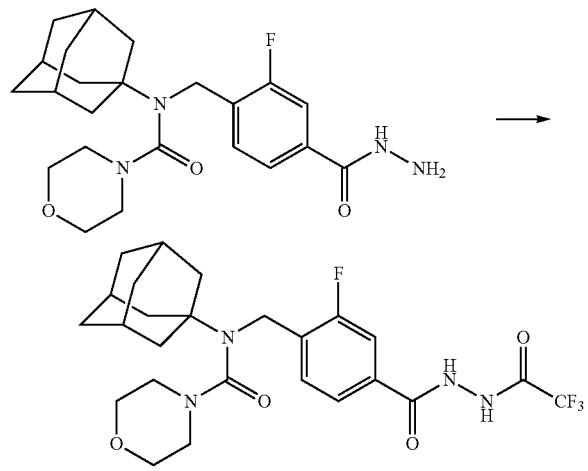

A solution of N-((3s,5s,7s)-adamantan-1-yl)-N-(2-fluoro-4-(hydrazinecarbonyl)benzyl)morpholine-4-carboxamide (0.268 g, 0.623 mmol) and triethylamine (0.174 mL, 1.246 mmol) in dichloromethane (5 mL) was mixed at 0° C. with trifluoroacetic anhydride (0.088 mL, 0.623 mmol), stirred at the same temperature for 2 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 12 g cartridge; methanol/dichloromethane=0% to 10%) to give N-((3s,5s,7s)-adamantan-1-yl)-N-(2-fluoro-4-(2-(2,2,2-trifluoroacetyl)hydrazine-1-carbonyl)benzyl)morpholine-4-carboxamide as colorless oil (0.258 g, 78.6%).

[Step 2] Compound 21931

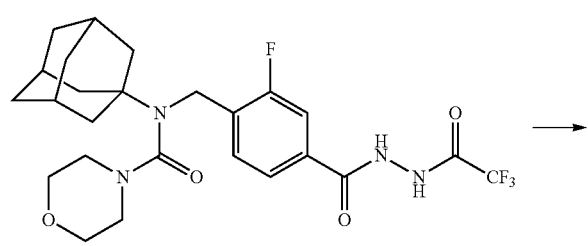

1138

-continued

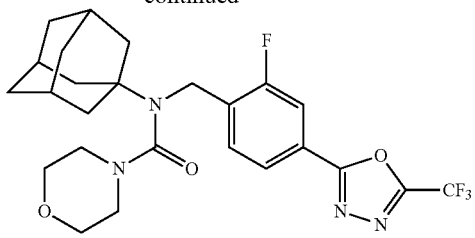

N-((3s,5s,7s)-adamantan-1-yl)-N-(2-fluoro-4-(2-(2,2,2-trifluoroacetyl)hydrazine-1-carbonyl)benzyl)morpholine-4-carboxamide (0.268 g, 0.510 mmol) and 1-methoxy-N-triethylammoniosulfonyl-methanimidate (Burgess reagent, 0.182 g, 0.764 mmol) were mixed at the room temperature in tetrahydrofuran (2 mL) and then stirred at 100° C. for 16 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 30%) to give N-((3s,5s,7s)-adamantan-1-yl)-N-(2-fluoro-4-(5-(trifluoromethyl)-1,3,4-oxadiazol-2-yl)benzyl)morpholine-4-carboxamide as white foam (0.124 g, 47.9%).

$^1$H NMR (400 MHz, CDCl$_3$) δ 7.83 (dd, 2H, J=13.6, 8.9 Hz), 7.51 (t, 1H, J=7.6 Hz), 4.20 (s, 2H), 3.42 (s, 4H), 3:24 (s, 4H), 2.14 (s, 3H), 1.94 (s, 6H), 1.75-1.62 (m, 6H); LRMS (ES) m/z 509.4 (M$^+$+1).

Example 376. Compound 21932: N-(((3r,5r,7r)-adamantan-1-yl)methyl)-N-(4-(5-(difluoromethyl)-1,3,4-oxadiazol-2-yl)-2-fluorobenzyl)morpholine-4-carboxamide

[Step 1] Methyl 4-(((((3r,5r,7r)-adamantan-1-yl)methyl)amino)methyl)-3-fluorobenzoate

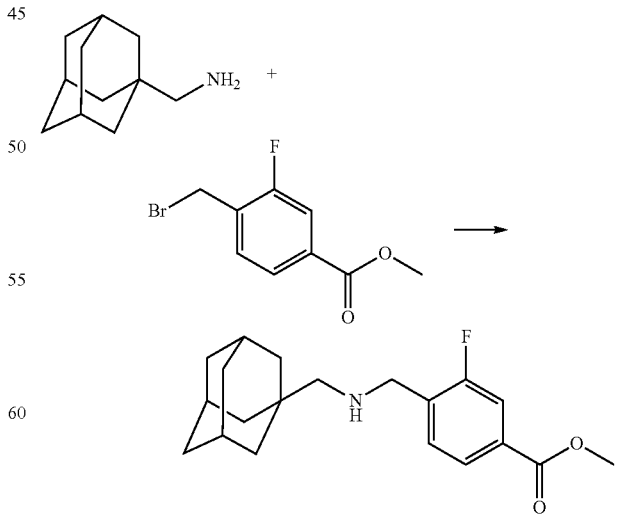

A solution of ((3r,5r,7r)-adamantan-1-yl)methanamine (1.500 g, 9.076 mmol), methyl 4-(bromomethyl)-3-fluorobenzoate (2.466 g, 9.983 mmol) and N,N-diisopropylethylamine (3.162 mL, 18.151 mmol) in acetonitrile (30 mL) prepared at the room temperature was stirred at the same temperature for 18 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=0% to 30%) to give methyl 4-(((((3r,5r,7r)-adamantan-1-yl)methyl)amino)methyl)-3-fluorobenzoate as yellow solid (2.474 g, 82.3%).

[Step 2] Methyl 4-((N-(((3r,5r,7r)-adamantan-1-yl)methyl)morpholine-4-carboxamido)methyl)-3-fluoro benzoate

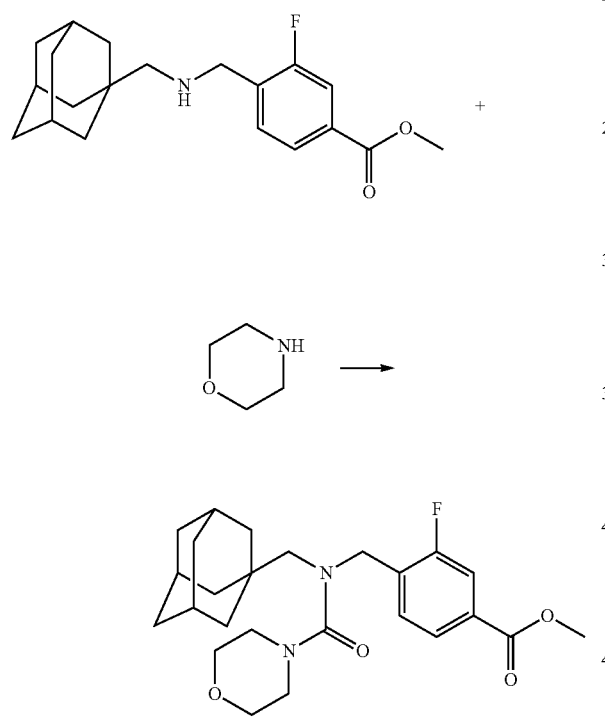

Triphosgene (0.224 g, 0.754 mmol) was added to a solution of methyl 4-(((((3r,5r,7r)-adamantan-1-yl)methyl)amino)methyl)-3-fluorobenzoate (0.500 g, 1.509 mmol) and N,N-diisopropylethylamine (1.577 mL, 9.052 mmol) in dichloromethane (10 mL) at 0° C., and the reaction mixture was stirred at the same temperature for 1 hr. The reaction mixture was treated with morpholine (0.137 mL, 1.584 mmol) and stirred for additional 4 hr at the room temperature. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=10% to 30%) to give methyl 4-((N-(((3r,5r,7r)-adamantan-1-yl)methyl)morpholine-4-carboxamido)methyl)-3-fluoro benzoate as yellow solid (0.559 g, 83.3%).

[Step 3] N-(((3r,5r,7r)-adamantan-1-yl)methyl)-N-(2-fluoro-4-(hydrazinecarbonyl)benzyl)morpholine-4-carboxamide

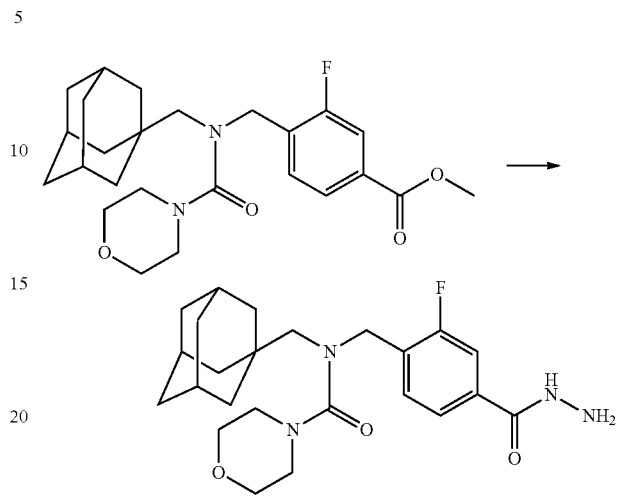

Methyl 4-((N-(((3r,5r,7r)-adamantan-1-yl)methyl)morpholine-4-carboxamido)methyl)-3-fluoro benzoate (0.559 g, 1.257 mmol) and hydrazine monohydrate (0.611 mL, 12.566 mmol) were mixed at the room temperature in ethanol (2 mL) and then stirred at 100° C. for 18 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 12 g cartridge; methanol/dichloromethane=0% to 10%) to give N-(((3r,5r,7r)-adamantan-1-yl)methyl)-N-(2-fluoro-4-(hydrazinecarbonyl)benzyl)morpholine-4-carboxamide as white solid (0.475 g, 85.1%).

[Step 4] N-((3r,5r,7r)-adamantan-1-yl)methyl)-N-(4-(2-(2,2-difluoroacetyl)hydrazine-1-carbonyl)-2-fluorobenzyl)morpholine-4-carboxamide

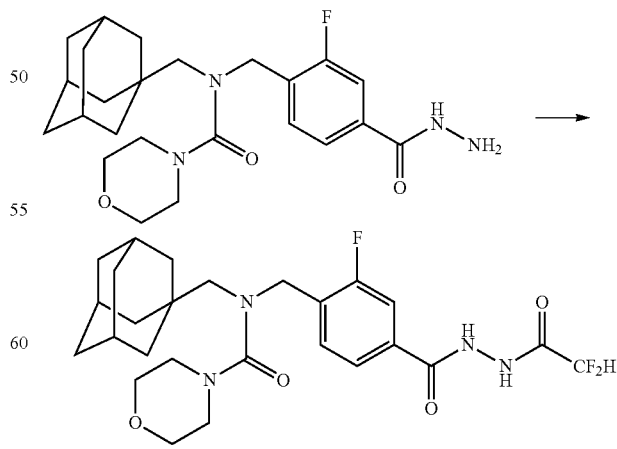

A solution of N-(((3r,5r,7r)-adamantan-1-yl)methyl)-N-(2-fluoro-4-(hydrazinecarbonyl)benzyl)morpholine-4-carboxamide (0.313 g, 0.703 mmol) and triethylamine (0.196 mL, 1.406 mmol) in dichloromethane (5 mL) was mixed at 0° C. with 2,2-difluoroacetic anhydride (0.087 mL, 0.703 mmol) and stirred at the same temperature for 2 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give N-(((3r,5r,7r)-adamantan-1-yl)methyl)-N-(4-(2-(2,2-difluoroacetyl)hydrazine-1-carbonyl)-2-fluorobenzyl)morpholine-4-carboxamide as colorless oil (0.274 g, 74.6%).

[Step 5] Compound 21932

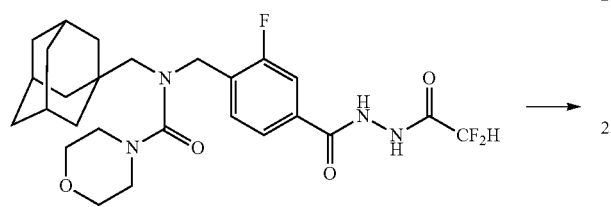

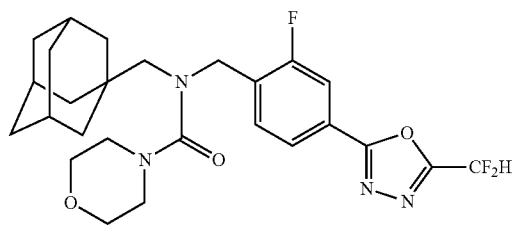

N-(((3r,5r,7r)-adamantan-1-yl)methyl)-N-(4-(2-(2,2-difluoroacetyl)hydrazine-1-carbonyl)-2-fluorobenzyl)morpholine-4-carboxamide (0.313 g, 0.598 mmol) and 1-methoxy-N-triethylammoniosulfonyl-methanimidate (Burgess reagent, 0.214 g, 0.897 mmol) were mixed at the room temperature in tetrahydrofuran (2 mL) and then stirred at 100° C. for 16 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; ethyl acetate/hexane=10% to 30%) to give N-(((3r,5r,7r)-adamantan-1-yl)methyl)-N-(4-(5-(difluoromethyl)-1,3,4-oxadiazol-2-yl)-2-fluorobenzyl)morpholine-4-carboxamide as white foam (0.096 g, 31.8%).

$^1$H NMR (400 MHz, CDCl$_3$) δ 7.89 (d, 1H, J=8.0 Hz), 7.83 (d, 1H, J=10.0 Hz), 7.41 (t, 1H, J=7.6 Hz), 6.94 (t, 1H, J=51.7 Hz), 4.58 (s, 2H), 3.72 (t, 4H, J=4.6 Hz), 3.33 (t, 4H, J=4.6 Hz), 2.96 (s, 2H), 2.00 (s, 3H), 1.74 (d, 3H, J=12.5 Hz), 1.64 (d, 3H, J=12.7 Hz), 1.53 (d, 6H, J=2.7 Hz); LRMS (ES) m/z 505.0 (M⁺+1).

Example 377. Compound 21933: N-(((3r,5r,7r)-adamantan-1-yl)methyl)-N-(2-fluoro-4-(5-(trifluoromethyl)-1,3,4-oxadiazol-2-yl)benzyl)morpholine-4-carboxamide

[Step 1] N-(((3r,5r,7r)-adamantan-1-yl)methyl)-N-(2-fluoro-4-(2-(2,2,2-trifluoroacetyl)hydrazine-1-carbonyl)benzyl)morpholine-4-carboxamide

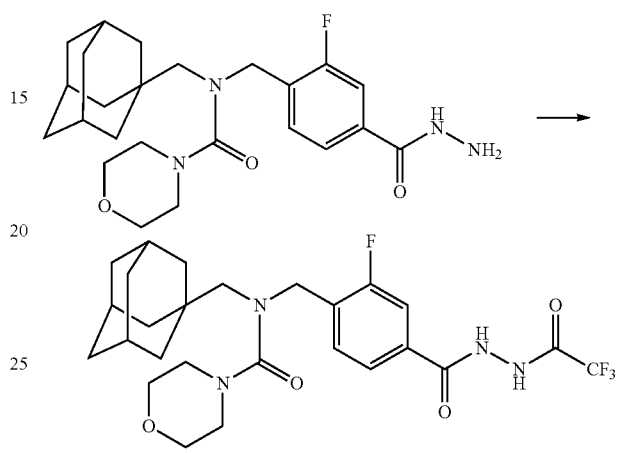

A solution of N-(((3r,5r,7r)-adamantan-1-yl)methyl)-N-(2-fluoro-4-(hydrazinecarbonyl)benzyl)morpholine-4-carboxamide (0.313 g, 0.703 mmol) and triethylamine (0.196 mL, 1.406 mmol) in dichloromethane (5 mL) was mixed at 0° C. with trifluoroacetic anhydride (0.099 mL, 0.703 mmol) and stirred at the same temperature for 2 hr. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; methanol/dichloromethane=0% to 10%) to give N-(((3r,5r,7r)-adamantan-1-yl)methyl)-N-(2-fluoro-4-(2-(2,2,2-trifluoroacetyl)hydrazine-1-carbonyl)benzyl)morpholine-4-carboxamide as colorless oil (0.251 g, 65.9%).

[Step 2] Compound 21933

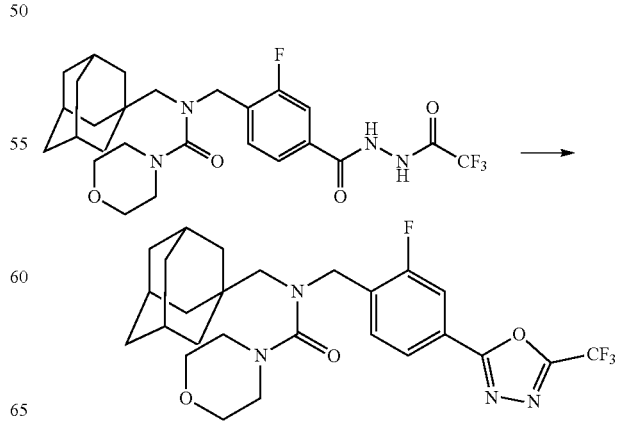

N-(((3r,5r,7r)-adamantan-1-yl)methyl)-N-(2-fluoro-4-(2-(2,2,2-trifluoroacetyl)hydrazine-1-carbonyl)benzyl)morpholine-4-carboxamide (0.313 g, 0.578 mmol) and 1-methoxy-N-triethylammoniosulfonyl-methanimidate (Burgess reagent, 0.207 g, 0.867 mmol) were mixed at the room temperature in tetrahydrofuran (2 mL) and then stirred at 100° C. for 16 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 30%) to give N-(((3r,5r,7r)-adamantan-1-yl)methyl)-N-(2-fluoro-4-(5-(trifluoromethyl)-1,3,4-oxadiazol-2-yl)benzyl)morpholine-4-carboxamide as white foam (0.105 g, 34.7%).

$^1$H NMR (400 MHz, CDCl$_3$) δ 7.89 (d, 1H, J=8.1 Hz), 7.83 (d, 1H, J=9.9 Hz), 7.43 (t, 1H, J=7.6 Hz), 4.59 (s, 2H), 3.72 (t, 4H, J=4.6 Hz), 3.33 (t, 4H, J=4.5 Hz), 2.97 (s, 2H), 2.01 (s, 3H), 1.74 (d, 3H, J=12.5 Hz), 1.64 (d, 3H, J=12.3 Hz), 1.54 (s, 6H); LRMS (ES) m/z 522.5 (M$^+$+1).

Example 378. Compound 21934: N-(4-(5-(difluoromethyl)-1,3,4-oxadiazol-2-yl)-2-fluorobenzyl)-N-(4-(((2R,6S)-4-ethyl-2,6-dimethylpiperazin-1-yl)methyl)phenyl)thiomorpholine-4-carboxamide 1,1-dioxide

[Step 1] Methyl 4-((N-(4-(((2R,6S)-4-ethyl-2,6-dimethylpiperazin-1-yl)methyl)phenyl)-1,1-dioxidothiomorpholine-4-carboxamido)methyl)-3-fluorobenzoate

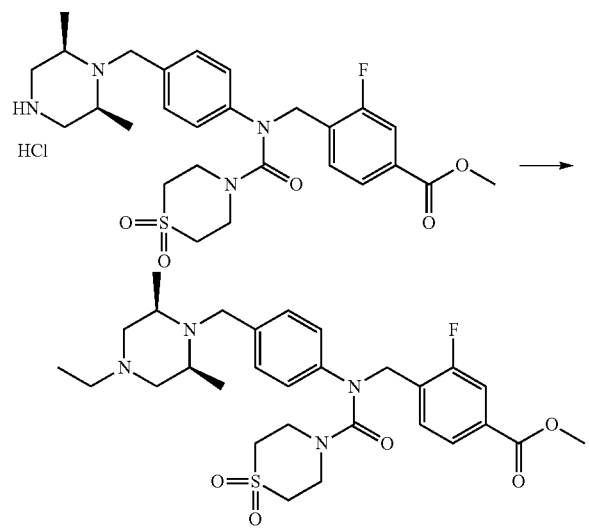

Acetaldehyde (0.034 g, 0.772 mmol) was added to a solution of methyl 4-((N-(4-(((2R,6S)-2,6-dimethylpiperazin-1-yl)methyl)phenyl)-1,1-dioxidothiomorpholine-4-carboxamido)methyl)-3-fluorobenzoate hydrochloride (0.300 g, 0.514 mmol) and N,N-diisopropylethylamine (0.090 mL, 0.514 mmol) in dichloromethane (5 mL) at the room temperature and the reaction mixture was stirred at the same temperature for 10 min. The reaction mixture was treated at the same temperature with sodium triacetoxyborohydride (0.218 g, 1.029 mmol) and stirred for additional 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give methyl 4-((N-(4-(((2R,6S)-4-ethyl-2,6-dimethylpiperazin-1-yl)methyl)phenyl)-1,1-dioxidothiomorpholine-4-carboxamido)methyl)-3-fluorobenzoate as white solid (0.094 g, 31.8%).

[Step 2] N-(4-(((2R,6S)-4-ethyl-2,6-dimethylpiperazin-1-yl)methyl)phenyl)-N-(2-fluoro-4-(hydrazinecarbonyl)benzyl)thiomorpholine-4-carboxamide 1,1-dioxide

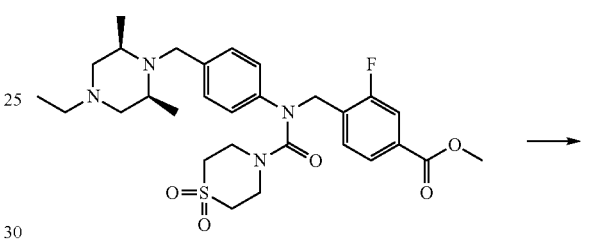

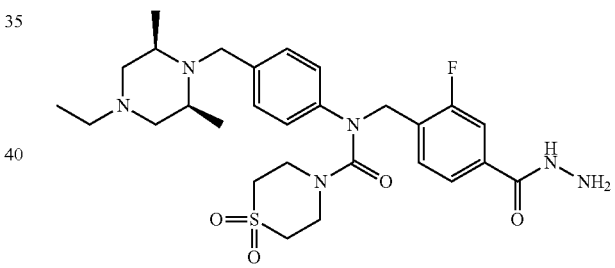

Methyl 4-((N-(4-(((2R,6S)-4-ethyl-2,6-di methylpiperazin-1-yl)methyl)phenyl)-1,1-dioxidothiomorpholine-4-carboxamido)methyl)-3-fluorobenzoate (0.094 g, 0.164 mmol) and hydrazine monohydrate (0.159 mL, 3.271 mmol) were mixed at the room temperature in ethanol (4 mL) and then stirred at 100° C. for 17 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. N-(4-(((2R,6S)-4-ethyl-2,6-dimethylpiperazin-1-yl)methyl)phenyl)-N-(2-fluoro-4-(hydrazinecarbonyl)benzyl)thiomorpholine-4-carboxamide 1,1-dioxide was used without further purification (0.090 g, 95.7%, white solid).

1145

[Step 3] Compound 21934

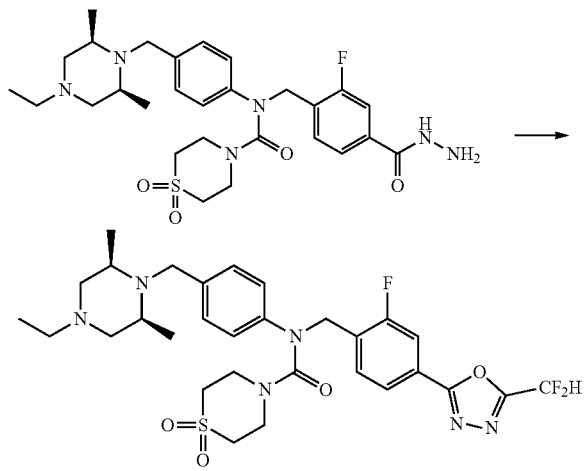

A solution of N-(4-(((2R,6S)-4-ethyl-2,6-dimethylpiperazin-1-yl)methyl)phenyl)-N-(2-fluoro-4-(hydrazinecarbonyl)benzyl)thiomorpholine-4-carboxamide 1,1-dioxide (0.085 g, 0.148 mmol) and triethylamine (0.062 mL, 0.444 mmol) in dichloromethane (5 mL) was mixed at the room temperature with 2,2-difluoroacetic anhydride (0.028 mL, 0.222 mmol). The reaction mixture was heated at reflux for 17 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-(((2R,6S)-4-ethyl-2,6-dimethylpiperazin-1-yl)methyl)phenyl)thiomorpholine-4-carboxamide 1,1-dioxide as white solid (0.047 g, 50.1%).

$^1$H NMR (400 MHz, CDCl$_3$) δ 7.88 (dd, 1H, J=8.0, 1.6 Hz), 7.75 (dd, 1H, J=10.1, 1.6 Hz), 7.68 (t, 1H, J=7.6 Hz), 7.36 (d, 2H, J=8.4 Hz), 7.07-6.80 (m, 3H), 4.92 (s, 2H), 3.80 (s, 2H), 3.73-3.72 (m, 4H), 3.12 (d, 2H, J=11.4 Hz), 3.01-3.00 (m, 2H), 2.78-2.72 (m, 6H), 2.18 (t, 2H, J=10.9 Hz), 1.32-1.26 (m, 3H), 1.03 (d, 6H, J=6.2 Hz); LRMS (ES) m/z 635.3 (M$^+$+1).

Example 379. Compound 21935: N-(4-(5-(difluoromethyl)-1,3,4-oxadiazol-2-yl)-2-fluorobenzyl)-N-(4-(((3S,5R)-4-ethyl-3,5-dimethylpiperazin-1-yl)methyl)phenyl)thiomorpholine-4-carboxamide 1,1-dioxide

[Step 1] Methyl 4-((N-(4-(((3S,5R)-4-ethyl-3,5-dimethylpiperazin-1-yl)methyl)phenyl)-1,1-dioxidothiomorpholine-4-carboxamido)methyl)-3-fluorobenzoate

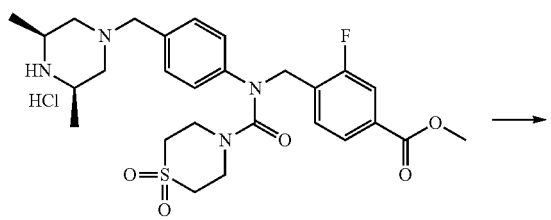

1146

-continued

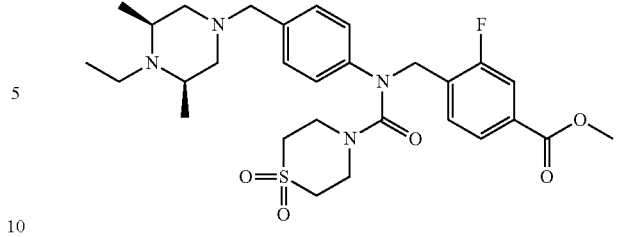

A solution of methyl 4-((N-(4-(((3S,5R)-3,5-dimethylpiperazin-1-yl)methyl)phenyl)-1,1-dioxidothiomorpholine-4-carboxamido)methyl)-3-fluorobenzoate hydrochloride (0.300 g, 0.514 mmol) and N,N-diisopropylethylamine (0.090 mL, 0.514 mmol) in dichloromethane (5 mL) was added at the room temperature acetaldehyde (0.034 g, 0.772 mmol). The reaction mixture was stirred at the same temperature for 10 min, treated at the same temperature with sodium triacetoxyborohydride (0.218 g, 1.029 mmol) and stirred for additional 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give methyl 4-((N-(4-(((3S,5R)-4-ethyl-3,5-dimethylpiperazin-1-yl)methyl)phenyl)-1,1-dioxidothiomorpholine-4-carboxamido)methyl)-3-fluorobenzoate as white solid (0.159 g, 53.8%).

[Step 2] N-(4-(((3S,5R)-4-ethyl-3,5-dimethylpiperazin-1-yl)methyl)phenyl)-N-(2-fluoro-4-(hydrazinecarbonyl)benzyl)thiomorpholine-4-carboxamide 1,1-dioxide

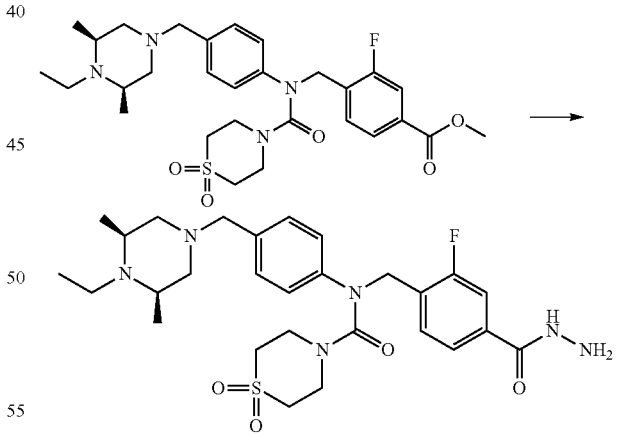

Methyl 4-((N-(4-(((3S,5R)-4-ethyl-3,5-dimethylpiperazin-1-yl)methyl)phenyl)-1,1-dioxidothiomorpholine-4-carboxamido)methyl)-3-fluorobenzoate (0.159 g, 0.277 mmol) and hydrazine monohydrate (0.269 mL, 5.533 mmol) were mixed at the room temperature in ethanol (4 mL) and then stirred at 100° C. for 17 hr, cooled down to the room temperature to terminate the reaction and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. N-(4-(((3S,5R)-4-ethyl-3,5-dimethylpiperazin-1-yl)methyl)phenyl)-N-(2-fluoro-4-(hydrazinecarbonyl)benzyl)thiomorpholine-4-carboxamide 1,1-dioxide was used without further purification (0.155 g, 97.5%, white solid).

[Step 3] Compound 21935

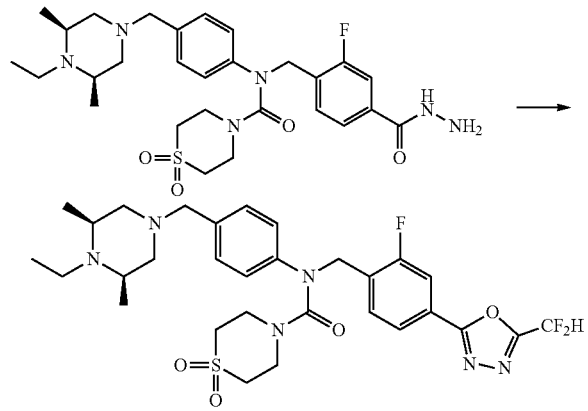

A solution of N-(4-(((3S,5R)-4-ethyl-3,5-dimethylpiperazin-1-yl)methyl)phenyl)-N-(2-fluoro-4-(hydrazinecarbonyl)benzyl)thiomorpholine-4-carboxamide 1,1-dioxide (0.150 g, 0.261 mmol) and triethylamine (0.109 mL, 0.783 mmol) in dichloromethane (5 mL) was mixed at the room temperature with 2,2-difluoroacetic anhydride (0.049 mL, 0.391 mmol). The reaction mixture was heated at reflux for 17 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-(((3S,5R)-4-ethyl-3,5-dimethylpiperazin-1-yl)methyl)phenyl)thiomorpholine-4-carboxamide 1,1-dioxide as white solid (0.032 g, 19.3%).

$^1$H NMR (400 MHz, DMSO-d$_6$) δ 7.86 (dd, 1H, J=8.0, 1.6 Hz), 7.77-7.72 (m, 7.28-7.22 (m, 4H), 4.91 (s, 2H), 3.57 (s, 4H), 3.32 (s, 2H), 2.85 (s, 4H), 2.75-2.74 (m, 2H), 2.56-2.54 (m, 4H), 1.67 (t, 2H, J=10.5 Hz), 0.90 (d, 6H, J=6.0 Hz); LRMS (ES) m/z 635.4 (M$^+$+1).

Example 380. Compound 21936: N-(4-(5-(Difluoromethyl)-1,3,4-oxadiazol-2-yl)benzyl)-N-(3-fluorophenyl)-4-(oxetan-3-yl)piperazine-1-carboxamide

[Step 1] Tert-Butyl 4-((3-fluorophenyl)carbamoyl)piperazine-1-carboxylate

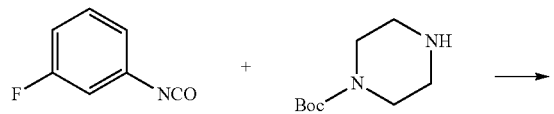

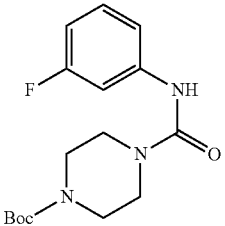

A solution of 1-fluoro-3-isocyanatobenzene (0.453 mL, 4.000 mmol) and tert-butyl piperazine-1-carboxylate (0.745 g, 4.000 mmol) in diethylether (10 mL) was stirred at the room temperature for 3 hr, and concentrated under the reduced pressure. The title compound was used without further purification (tert-butyl 4-((3-fluorophenyl)carbamoyl)piperazine-1-carboxylate, 1.292 g, 99.9%, white solid).

[Step 2] Tert-Butyl 4-((3-fluorophenyl)(4-(methoxycarbonyl)benzyl)carbamoyl)piperazine-1-carboxylate

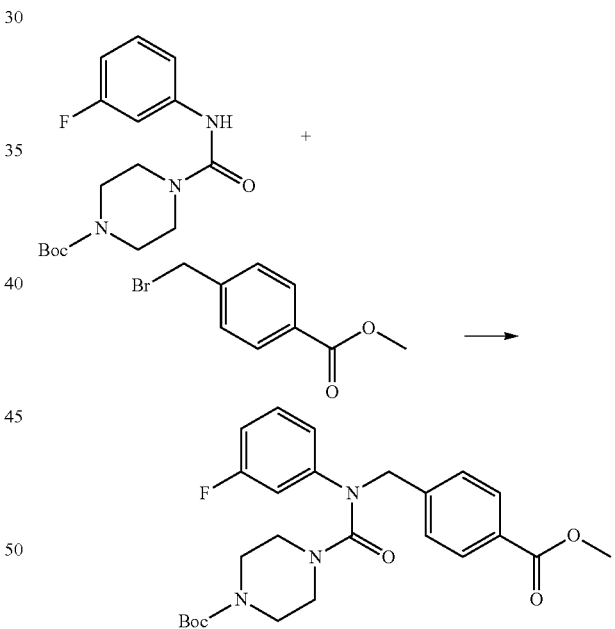

A solution of tert-butyl 4-((3-fluorophenyl)carbamoyl)piperazine-1-carboxylate (0.541 g, 1.674 mmol) and sodium hydride (60.00%, 0.100 g, 2.510 mmol) in tetrahydrofuran (6 mL) was stirred at the room temperature for 30 min. and mixed with methyl 4-(bromomethyl)benzoate (0.422 g, 1.841 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((3-fluorophenyl)(4-(methoxycarbonyl)benzyl)carbamoyl)piperazine-1-carboxylate as white solid (0.317 g, 40.2%).

1149

[Step 3] Methyl 4-((N-(3-fluorophenyl)piperazine-1-carboxamido)methyl)benzoate hydrochloride

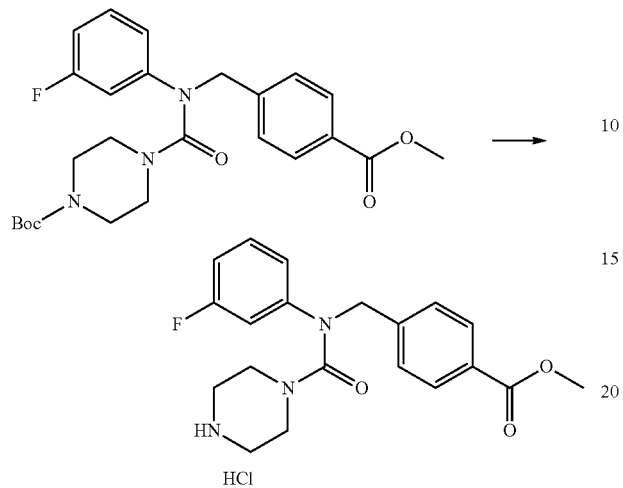

A solution of tert-butyl 4-((3-fluorophenyl)(4-(methoxycarbonyl)benzyl)carbamoyl)piperazine-1-carboxylate (0.317 g, 0.672 mmol) and hydrogen chloride (4.00 M solution in 1,4-dioxane, 0.672 mL, 2.689 mmol) in dichloromethane (5 mL) was stirred at the room temperature for 18 hr, and concentrated under the reduced pressure. The title compound was used without further purification (methyl 4-((N-(3-fluorophenyl)piperazine-1-carboxamido)methyl)benzoate hydrochloride, 0.274 g, 99.9%, pale yellow solid).

[Step 4] Methyl 4-((N-(3-fluorophenyl)-4-(oxetan-3-yl)piperazine-1-carboxamido)methyl)benzoate

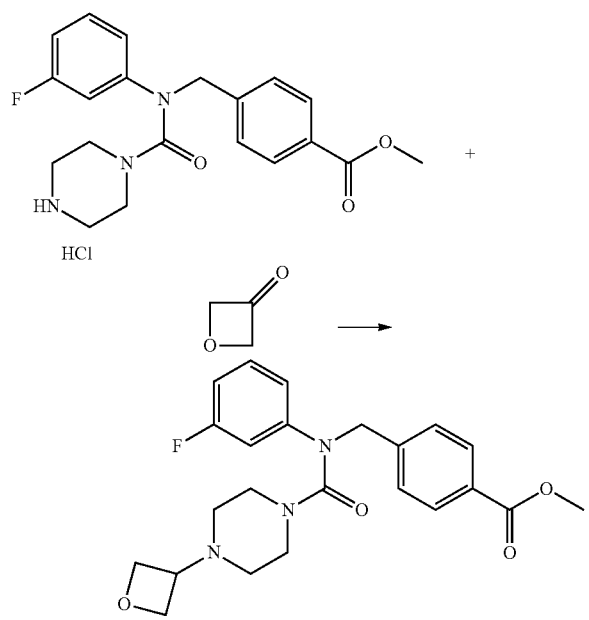

A solution of methyl 4-((N-(3-fluorophenyl)piperazine-1-carboxamido)methyl)benzoate hydrochloride (0.274 g, 0.672 mmol), oxetan-3-one (0.059 mL, 1.008 mmol) and

1150 sodium triacetoxyborohydride (0.214 g, 1.008 mmol) in dichloromethane (5 mL) was stirred at the room temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give methyl 4-((N-(3-fluorophenyl)-4-(oxetan-3-yl)piperazine-1-carboxamido)methyl)benzoate as pale yellow oil (0.256 g, 89.0%).

[Step 5] N-(3-Fluorophenyl)-N-(4-(hydrazinecarbonyl)benzyl)-4-(oxetan-3-yl)piperazine-1-carboxamide

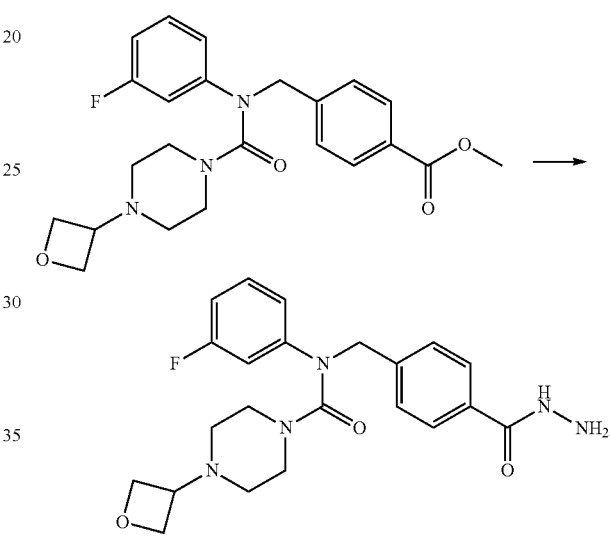

Methyl 4-((N-(3-fluorophenyl)-4-(oxetan-3-yl)piperazine-1-carboxamido)methyl)benzoate (0.256 g, 0.599 mmol) and hydrazine monohydrate (0.582 mL, 11.977 mmol) were mixed at the room temperature in ethanol (5 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(3-fluorophenyl)-N-(4-(hydrazinecarbonyl)benzyl)-4-(oxetan-3-yl)piperazine-1-carboxamide as white solid (0.115 g, 45.0%).

[Step 6] Compound 21936

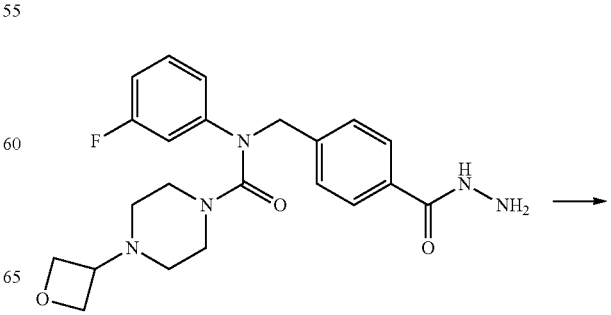

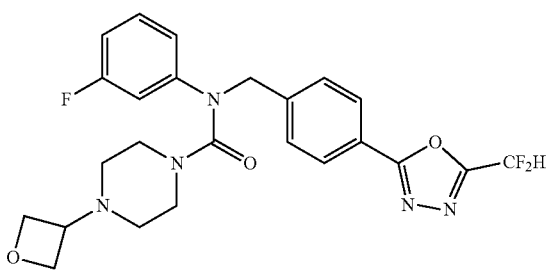

N-(3-Fluorophenyl)-N-(4-(hydrazinecarbonyl)benzyl)-4-(oxetan-3-yl)piperazine-1-carboxamide (0.115 g, 0.269 mmol), triethylamine (0.113 mL, 0.808 mmol) and 2,2-difluoroacetic anhydride (0.100 mL, 0.808 mmol) were mixed at the room temperature in dichloromethane (4 mL) and then stirred at 40° C. for 18 hr, cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)benzyl)-N-(3-fluorophenyl)-4-(oxetan-3-yl)piperazine-1-carboxamide as white solid (0.090 g, 68.9%).

$^1$H NMR (400 MHz, CDCl$_3$) δ 8.05 (d, 2H, J=8.4 Hz), 7.48 (d, 2H, J=8.4 Hz), 7.33-7.22 (m, 1H), 7.10-6.74 (m, 4H), 4.95 (s, 2H), 4.68-4.50 (m, 4H), 3.49 (s, 1H), 3.39 (s, 4H), 2.24 (s, 4H); LRMS (ES) m/z 488.2 (M$^+$+1).

Example 381. Compound 21937: N-(4-(5-(Difluoromethyl)-1,3,4-oxadiazol-2-yl)-2-fluorobenzyl)-N-(3-fluorophenyl)-4-(oxetan-3-yl)piperazine-1-carboxamide

[Step 1] Tert-Butyl 4-((2-fluoro-4-(methoxycarbonyl)benzyl)(3-fluorophenyl)carbamoyl)piperazine-1-carboxylate

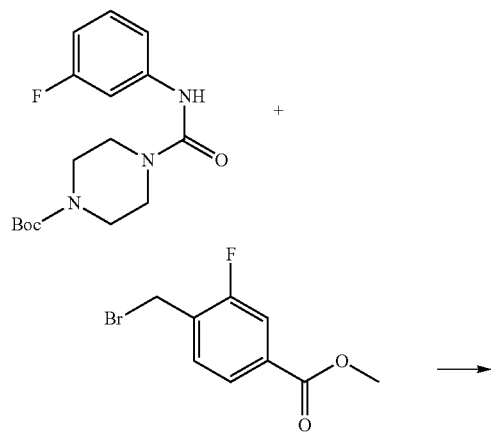

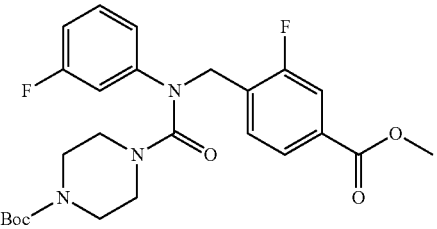

A solution of tert-butyl 4-((3-fluorophenyl)carbamoyl)piperazine-1-carboxylate (0.431 g, 1.333 mmol) and sodium hydride (60.00%, 0.080 g, 1.999 mmol) in tetrahydrofuran (6 mL) was stirred at the room temperature for 30 min, and mixed with methyl 4-(bromomethyl)-3-fluorobenzoate (0.362 g, 1.466 mmol). The reaction mixture was stirred at the same temperature for additional 18 hi, and concentrated under the reduced pressure. The concentrate was purified and concentrated by column chromatography (SiO$_2$, 12 g cartridge; ethyl acetate/hexane=0% to 50%) to give tert-butyl 4-((2-fluoro-4-(methoxycarbonyl)benzyl)(3-fluorophenyl)carbamoyl)piperazine-1-carboxylate as colorless oil (0.292 g, 44.7%).

[Step 2] Methyl 3-fluoro-4-((N-(3-fluorophenyl)piperazine-1-carboxamido)methyl)benzoate hydrochloride

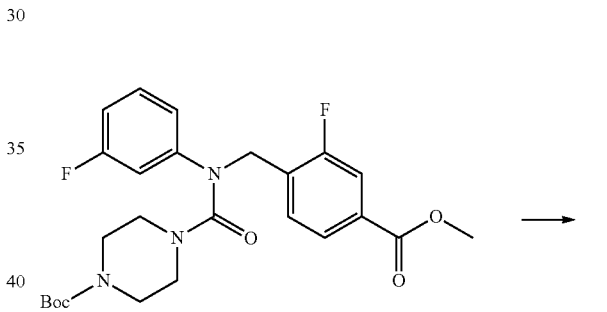


A solution of tert-butyl 4-((2-fluoro-4-(methoxycarbonyl)benzyl)(3-fluorophenyl)carbamoyl)piperazine-1-carboxylate (0.292 g, 0.595 mmol) and hydrogen chloride (4.00 M solution in 1,4-dioxane, 0.595 mL, 2.382 mmol) in dichloromethane (4 mL) was stirred at the room temperature for 18 hr, and concentrated under the reduced pressure. The title compound was used without further purification (methyl 3-fluoro-4-((N-(3-fluorophenyl)piperazine-1-carboxamido)methyl)benzoate hydrochloride, 0.253 g 99.8%, pale yellow solid).

[Step 3] Methyl 3-fluoro-4-((N-(3-fluorophenyl)-4-(oxetan-3-yl)piperazine-1-carboxamido)methyl)benzoate

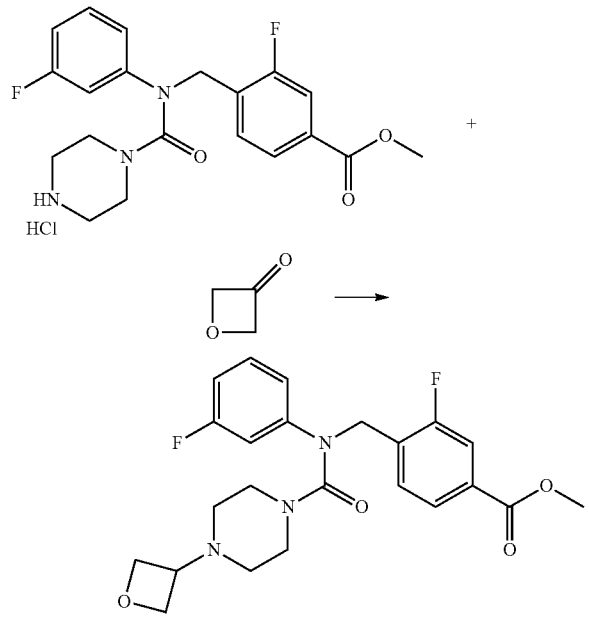

A solution of methyl 3-fluoro-4-((N-(3-fluorophenyl)piperazine-1-carboxamido)methyl)benzoate hydrochloride (0.253 g, 0.594 mmol), oxetan-3-one (0.052 mL, 0.891 mmol) and sodium triacetoxyborohydride (0.189 g, 0.891 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 3-fluoro-4-((N-(3-fluorophenyl)-4-(oxetan-3-yl)piperazine-1-carboxamido)methyl)benzoate, 0.264 g, 99.8%, pale yellow oil).

[Step 4] N-(2-Fluoro-4-(hydrazinecarbonyl)benzyl)-N-(3-fluorophenyl)-4-(oxetan-3-yl)piperazine-1-carboxamide

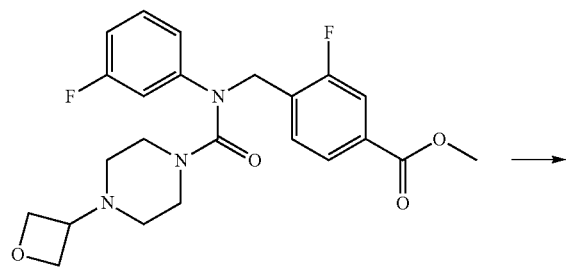

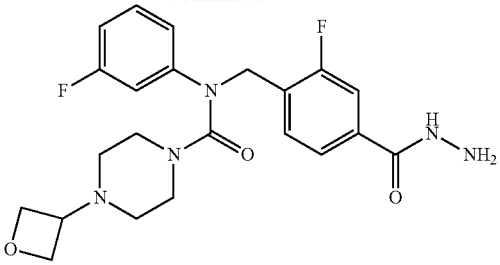

Methyl 3-fluoro-4-((N-(3-fluorophenyl)-4-(oxetan-3-yl)piperazine-1-carboxamido)methyl)benzoate (0.264 g, 0.593 mmol) and hydrazine monohydrate (0.576 mL, 11.853 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(2-fluoro-4-(hydrazinecarbonyl)benzyl)-N-(3-fluorophenyl)-4-(oxetan-3-yl)piperazine-1-carboxamide as white solid (0.187 g, 70.9%).

[Step 5] Compound 21937

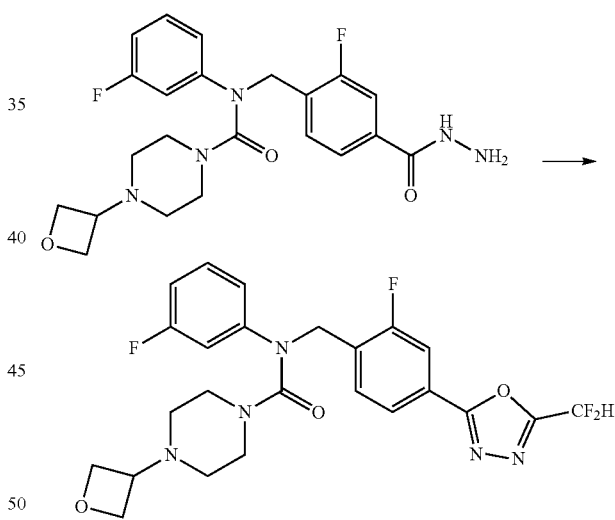

N-(2-Fluoro-4-(hydrazinecarbonyl)benzyl)-N-(3-fluorophenyl)-4-(oxetan-3-yl)piperazine-1-carboxamide (0.187 g, 0.420 mmol), triethylamine (0.176 mL, 1.259 mmol) and 2,2-difluoroacetic anhydride (0.157 mL, 1.259 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)-2-fluorobenzyl)-N-(3-fluorophenyl)-4-(oxetan-3-yl)piperazine-1-carboxamide as white solid (0.040 g, 18.7%).

$^1$H NMR (400 MHz, CDCl$_3$) δ 7.88 (dd, 1H, J=8.0, 1.7 Hz), 7.78 (dd, 1H, J=10.1. 1.7 Hz), 7.68 (t, 1H, J=7.6 Hz), 7.34-7.24 (m, 1H), 7.07-6.78 (m, 4H), 4.98 (s, 2H), 4.72-4.47 (m, 4H), 3.50 (s, 1H), 3.39 (s, 4H), 2.24 (s, 4H); LRMS (ES) m/z 506.3 (M++1).

Example 382. Compound 21938: N-((5-(5-(Difluoromethyl)-1,3,4-oxadiazol-2-yl)pyridin-2-yl)methyl)-N-(3-fluorophenyl)-4-(oxetan-3-yl)piperazine-1-carboxamide

[Step 1] Tert-Butyl 4-((3-fluorophenyl)((5-(methoxycarbonyl)pyridin-2-yl)methyl)carbamoyl)piperazine-1-carboxylate

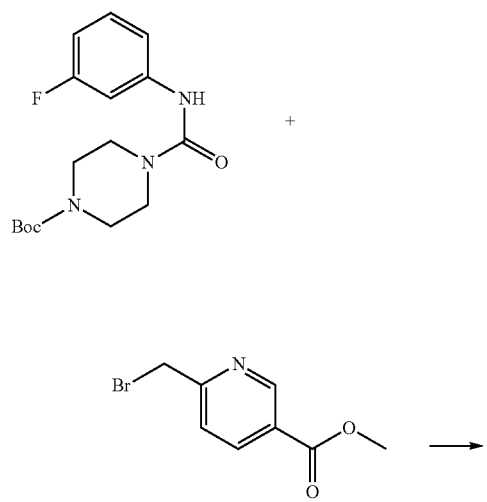

A solution of tert-butyl 4-((3-fluorophenyl)carbamoyl)piperazine-1-carboxylate (0.431 g, 1.333 mmol) and sodium hydride (60.00%, 0.080 g, 1.999 mmol) in tetrahydrofuran (6 mL) was stirred at the room temperature for 30 min, and mixed with methyl 6-(bromomethyl)nicotinate (0.337 g, 1.466 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((3-fluorophenyl)((5-(methoxycarbonyl)pyridin-2-yl)methyl)carbamoyl)piperazine-1-carboxylate as yellow solid (0.229 g, 36.4%).

[Step 2] Methyl 6-((N-(3-fluorophenyl)piperazine-1-carboxamido)methyl)nicotinate hydrochloride

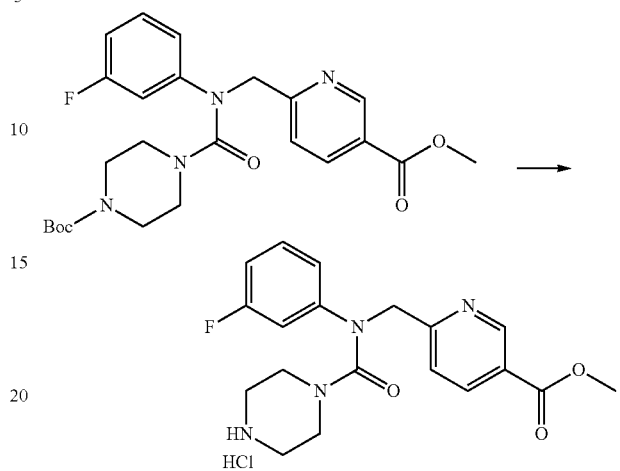

A solution of tert-butyl 4-((3-fluorophenyl)((5-(methoxycarbonyl)pyridin-2-yl)methyl)carbamoyl)piperazine-1-carboxylate (0.229 g, 0.485 mmol) and hydrogen chloride (4.00 M solution in 1,4-dioxane, 0.485 mL, 1.939 mmol) in dichloromethane (4 mL) prepared at the room temperature was stirred at the same temperature for 18 hr, and concentrated under the reduced pressure. The title compound was used without further purification (methyl 6-((N-(3-fluorophenyl)piperazine-1-carboxamido)methyl)nicotinate hydrochloride, 0.198 g, 99.9%, pale yellow solid).

[Step 3] Methyl 6-((N-(3-fluorophenyl)-4-(oxetan-3-yl)piperazine-1-carboxamido)methyl)nicotinate

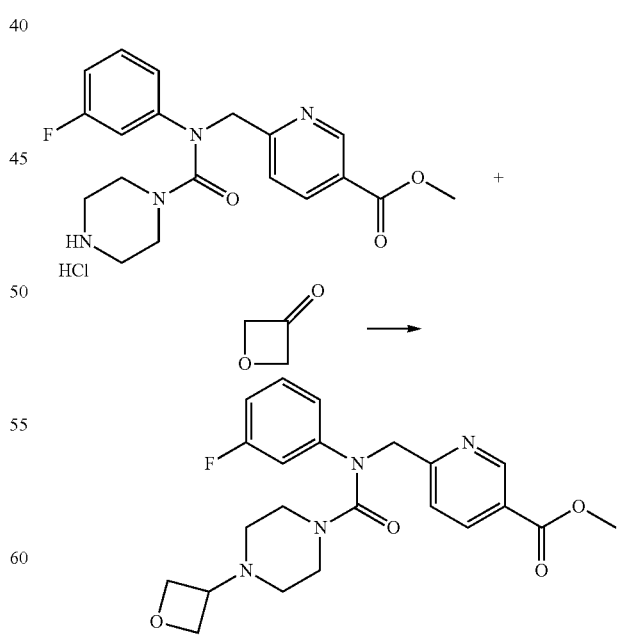

A solution of methyl 6-((N-(3-fluorophenyl)piperazine-1-carboxamido)methyl)nicotinate hydrochloride (0.198 g, 0.484 mmol), oxetan-3-one (0.03 mL, 0.726 mmol) and sodium triacetoxyborohydride (0.154 g, 0.726 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((N-(3-fluorophenyl)-4-(oxetan-3-yl)piperazine-1-carboxamido)methyl)nicotinate, 0.207 g, 99.8%, pale yellow oil).

[Step 4] N-(3-Fluorophenyl)-N-((5-(hydrazinecarbonyl)pyridin-2-yl)methyl)-4-(oxetan-3-yl)piperazine-1-carboxamide

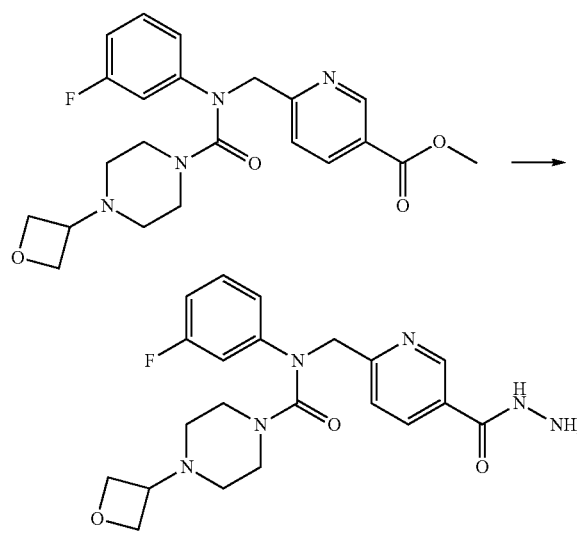

Methyl 6-((N-(3-fluorophenyl)-4-(oxetan-3-yl)piperazine-1-carboxamido)methyl)nicotinate (0.207 g, 0.483 mmol) and hydrazine monohydrate (0.470 mL, 9.663 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(3-fluorophenyl)-N-((5-(hydrazinecarbonyl)pyridin-2-yl)methyl-4-(oxetan-3-yl)piperazine-1-carboxamide as pale yellow solid (0.098 g, 47.4%).

[Step 5] Compound 21938

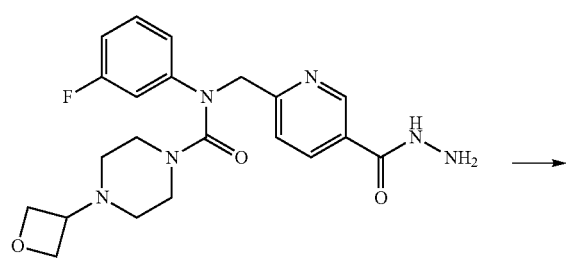

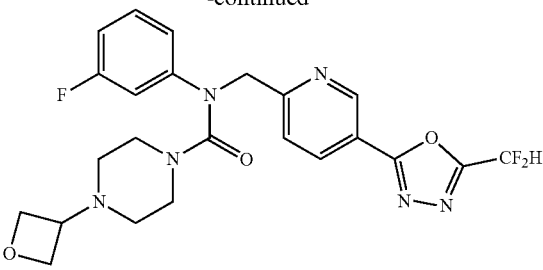

N-(3-Fluorophenyl)-N-((5-(hydrazinecarbonyl)pyridin-2-yl)methyl)-4-(oxetan-3-yl)piperazine-1-carboxamide (0.098 g, 0.229 mmol), triethylamine (0.096 mL, 0.686 mmol) and 2,2-difluoroacetic anhydride (0.085 mL, 0.686 mmol) were mixed at the room temperature in dichloromethane (4 mL) and then stirred at 40° C. for 18 hr, cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-((5-(5-(difluoromethyl)-1,3,4-oxadiazol-2-yl)pyridin-2-yl)methyl)-N-(3-fluorophenyl)-4-(oxetan-3-yl)piperazine-1-carboxamide as white solid (0.033 g, 29.8%).

$^1$H NMR (400 MHz, CDCl$_3$) δ 9.25 (dd, 1H, J=2.3, 0.8 Hz), 8.36 (dd, 1H, J=8.2, 2.2 Hz), 7.59 (d, 1H, J=8.1 Hz), 7.34-7.23 (m, 1H), 7.14-6.74 (m, 4H), 5.12 (s, 2H), 4.76-4.50 (m, 4H), 3.44 (brs, 5H), 2.30 (s, 4H); LRMS (ES) m/z 489.3 (M$^+$+1).

Example 383. Compound 21939: N-(4-(5-(Difluoromethyl)-1,3,4-oxadiazol-2-yl)benzyl)-N-(4-fluorophenyl)-4-(oxetan-3-yl)piperazine-1-carboxamide

[Step 1] Tert-Butyl 4-((4-fluorophenyl)carbamoyl)piperazine-1-carboxylate

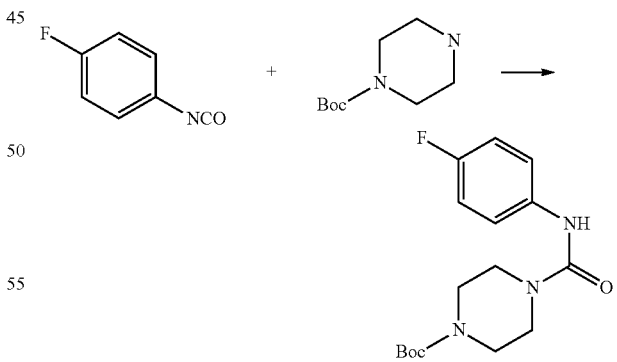

A solution of 1-fluoro-4-isocyanatobenzene (0:450 mL, 4.000 mmol) and tert-butyl piperazine-1-carboxylate (0.745 g, 4.000 mmol) in diethylether (10 mL) prepared at the room temperature was stirred at the same temperature for 3 hr, and concentrated under the reduced pressure. The title compound was used without further purification (tert-butyl 4-((4-fluorophenyl)carbamoyl)piperazine-1-carboxylate, 1.292 g, 99.9%, white solid).

1159

[Step 2] Tert-Butyl 4-((4-fluorophenyl)(4-(methoxy-carbonyl)benzyl)carbamoyl)piperazine-1-carboxylate

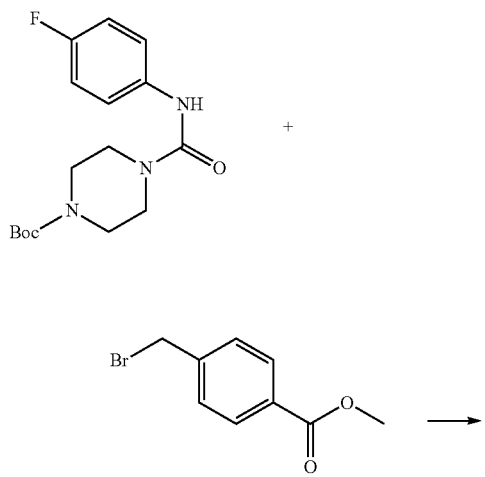

A solution of tert-butyl 4-((4-fluorophenyl)carbamoyl)piperazine-1-carboxylate (0.373 g, 1.152 mmol) and sodium hydride (60.00%, 0.069 g, 1.728 mmol) in tetrahydrofuran (6 mL) was stirred at the room temperature for 30 min, and mixed with methyl 4-(bromomethyl)benzoate (0.290 g, 1.267 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((4-fluorophenyl)(4-(methoxycarbonyl)benzyl)carbamoyl)piperazine-1-carboxylate as white solid (0.360 g, 66.2%).

[Step 3] Methyl 4-((N-(4-fluorophenyl)piperazine-1-carboxamido)methyl)benzoate hydrochloride

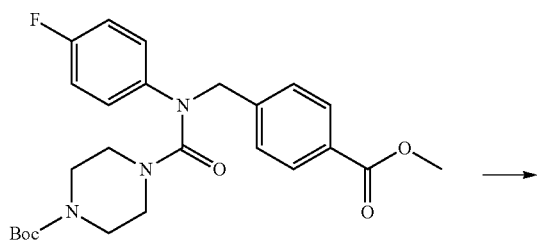

1160

-continued

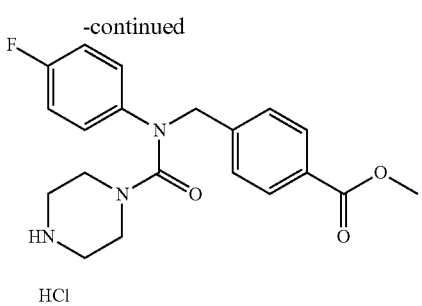

A solution of tert-butyl 4-((4-fluorophenyl)(4-(methoxy-carbonyl)benzyl)carbamoyl)piperazine-1-carboxylate (0.360 g, 0.763 mmol) and hydrogen chloride (4.00 M solution in 1,4-dioxane, 0.763 mL, 3.054 mmol) in dichloromethane (5 mL) prepared at the room temperature was stirred at the same temperature for 18 hr, and concentrated under the reduced pressure. The title compound was used without further purification (methyl 4-((N-(4-fluorophenyl)piperazine-1-carboxamido)methyl)benzoate hydrochloride, 0.311 g, 99.9%, pale yellow solid).

[Step 4] Methyl 4-((N-(4-fluorophenyl)-4-(oxetan-3-yl)piperazine-1-carboxamido)methyl)benzoate

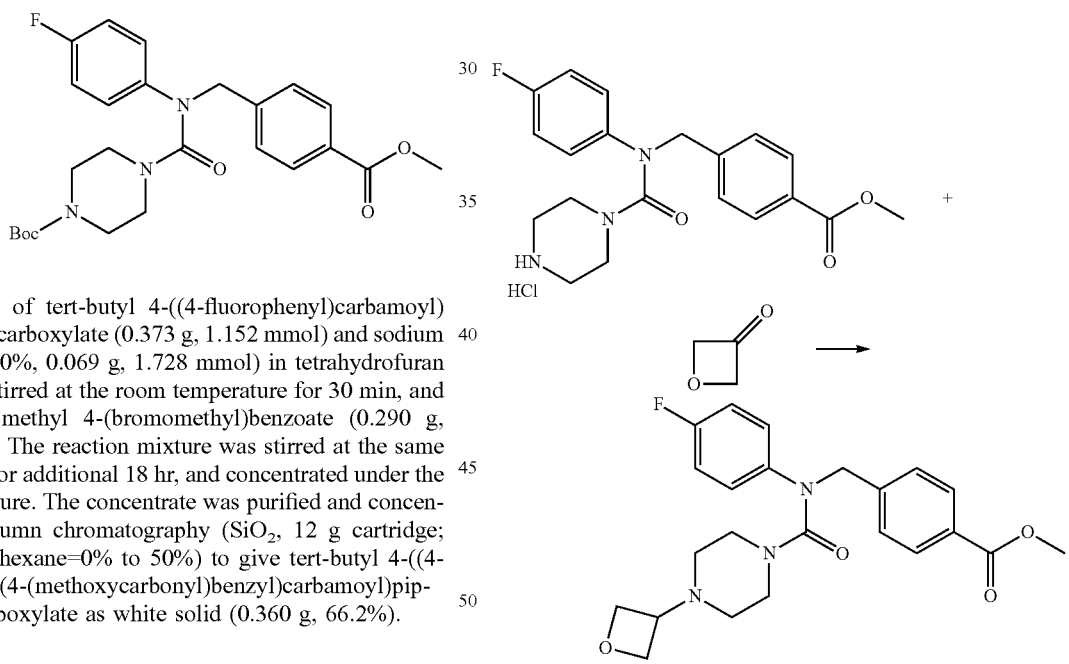

A solution of methyl 4-((N-(4-fluorophenyl)piperazine-1-carboxamido)methyl)benzoate hydrochloride (0.311 g, 0.762 mmol), oxetan-3-one (0.067 mL, 1.144 mmol) and sodium triacetoxyborohydride (0.242 g, 1.144 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to

1161 give methyl 4-((N-(4-fluorophenyl)-4-(oxetan-3-yl)piperazine-1-carboxamido)methyl)benzoate as pale yellow oil (0.252 g, 77.2%).

[Step 5] N-(4-Fluorophenyl)-N-(4-(hydrazinecarbonyl)benzyl)-4-(oxetan-3-yl)piperazine-1-carboxamide

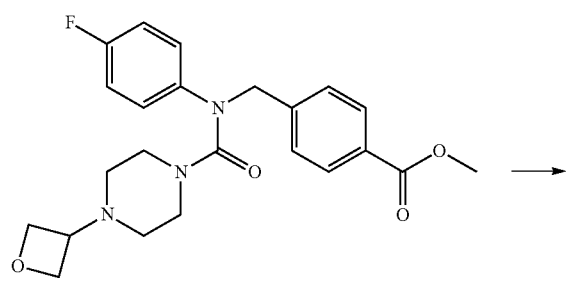

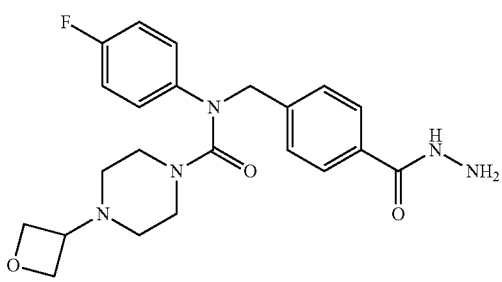

Methyl 4-((N-(4-fluorophenyl)-4-(oxetan-3-yl)piperazine-1-carboxamido)methyl)benzoate (0.252 g, 0.590 mmol) and hydrazine monohydrate (0.573 mL, 11.790 mmol) were mixed at the room temperature in ethanol (5 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(4-fluorophenyl)-N-(4-(hydrazinecarbonyl)benzyl)-4-(oxetan-3-yl)piperazine-1-carboxamide as white solid (0.159 g, 63.1%).

[Step 6] Compound 21939

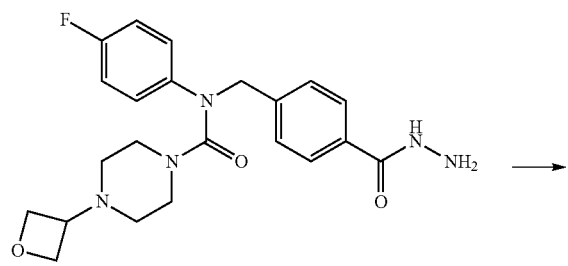

1162

-continued

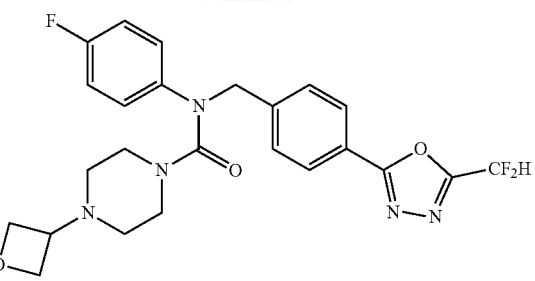

N-(4-Fluorophenyl)-N-(4-(hydrazinecarbonyl)benzyl)-4-(oxetan-3-yl)piperazine-1-carboxamide (0.159 g, 0.372 mmol), triethylamine (0.156 mL, 1.116 mmol) and 2,2-difluoroacetic anhydride (0.139 mL, 1.116 mmol) were mixed at the room temperature in dichloromethane (4 mL) and then stirred at 40° C. for 18 hr, cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)benzyl)-N-(4-fluorophenyl)-4-(oxetan-3-yl)piperazine-1-carboxamide as white solid (0.084 g, 46.4%).

$^1$H NMR (400 MHz, CDCl$_3$) δ 8.10-8.00 (m, 2H), 7.50-7.43 (m, 2H), 7.08-6.78 (m, 5H), 4.90 (s, 2H), 4.68-4.60 (m, 4H), 3.49 (s, 1H), 3.36 (s, 4H), 2.22 (s, 4H); LRMS (ES) m/z 488.3 (M$^+$+1).

Example 384. Compound 21940: N-(4-(5-(Difluoromethyl)-1,3,4-oxadiazol-2-yl)-2-fluorobenzyl)-N-(4-fluorophenyl)-4-(oxetan-3-yl)piperazine-1-carboxamide

[Step 1] Tert-Butyl 4-((2-fluoro-4-(methoxycarbonyl)benzyl)(4-fluorophenyl)carbamoyl)piperazine-1-carboxylate

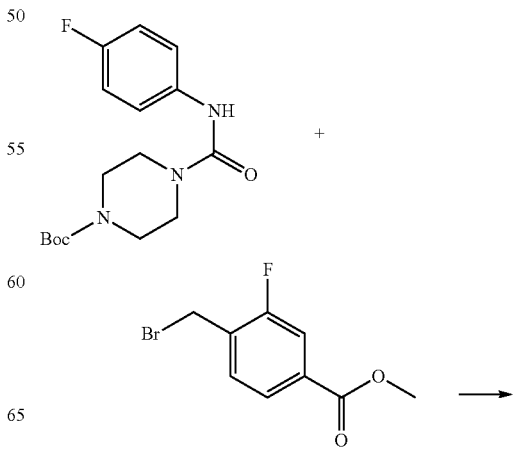

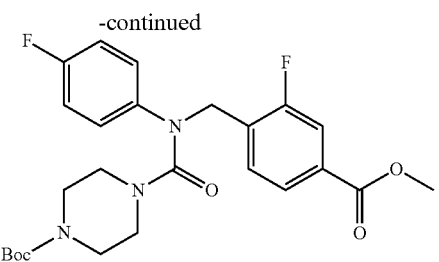

A solution of tert-butyl 4-((4-fluorophenyl)carbamoyl)piperazine-1-carboxylate (0.431 g, 1.333 mmol) and sodium hydride (60.00%, 0.080 g, 1.999 mmol) in tetrahydrofuran (6 mL) was stirred at the room temperature for 30 min, and mixed with methyl 4-(bromomethyl)-3-fluorobenzoate (0.362 g, 1.466 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((2-fluoro-4-(methoxycarbonyl)benzyl)(4-fluorophenyl)carbamoyl)piperazine-1-carboxylate as colorless oil (0.337 g, 51.7%).

[Step 2] Methyl 3-fluoro-4-((N-(4-fluorophenyl)piperazine-1-carboxamido)methyl)benzoate hydrochloride

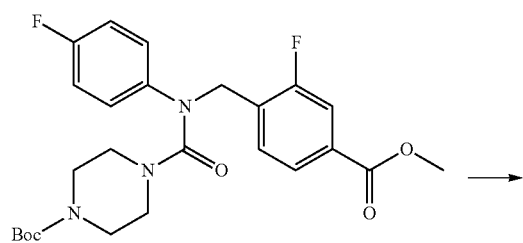

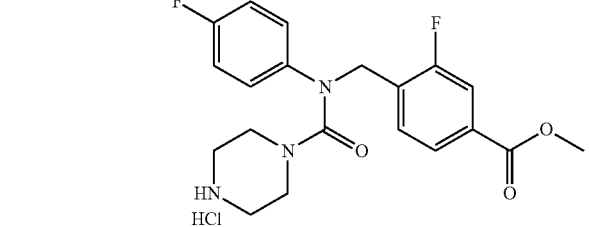

A solution of tert-butyl 4-((2-fluoro-4-(methoxycarbonyl)benzyl)(4-fluorophenyl)carbamoyl)piperazine-1-carboxylate (0.337 g, 0.689 mmol) and hydrogen chloride (4.00 M solution in 1,4-dioxane, 0.689 mL, 2.756 mmol) in dichloromethane (4 mL) prepared at the room temperature was stirred at the same temperature for 18 hr, and concentrated under the reduced pressure. The title compound was used without further purification (methyl 3-fluoro-4-((N-(4-fluorophenyl)piperazine-1-carboxamido)methyl)benzoate hydrochloride, 0.293 g, 99.9%, pale yellow solid).

[Step 3] Methyl 3-fluoro-4-((N-(4-fluorophenyl)-4-(oxetan-3-yl)piperazine-1-carboxamido)methyl)benzoate

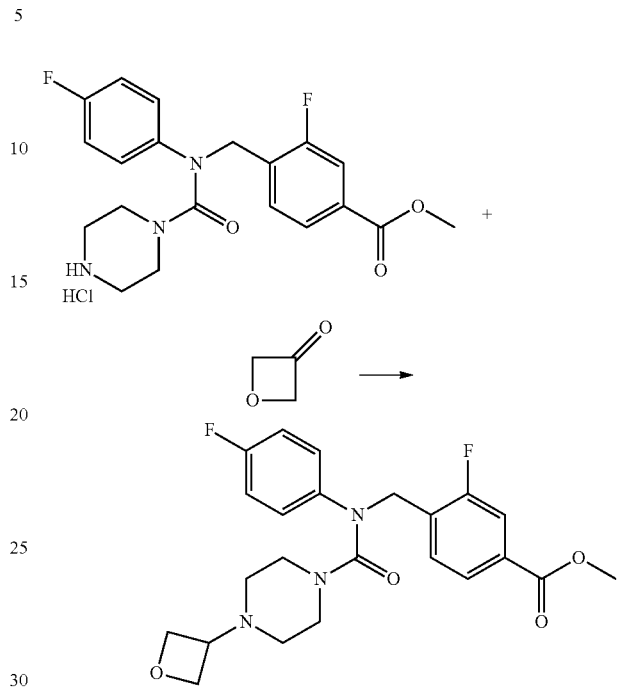

A solution of methyl 3-fluoro-4-((N-(4-fluorophenyl)piperazine-1-carboxamido)methyl)benzoate hydrochloride (0.293 g, 0.688 mmol), oxetan-3-one (0.060 mL, 1.032 mmol) and sodium triacetoxyborohydride (0.219 g, 1.032 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 3-fluoro-4-((N-(4-fluorophenyl)-4-(oxetan-3-yl)piperazine-1-carboxamido)methyl benzoate, 0.306 g, 99.8%, pale yellow oil).

[Step 4] N-(2-Fluoro-4-(hydrazinecarbonyl)benzyl)-N-(4-fluorophenyl)-4-(oxetan-3-yl)piperazine-1-carboxamide

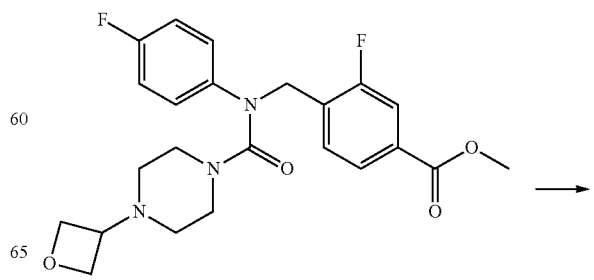

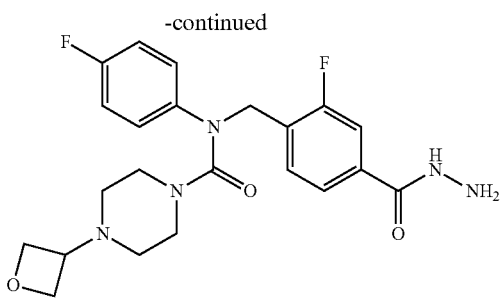

Methyl 3-fluoro-4-((N-(4-fluorophenyl)-4-(oxetan-3-yl)piperazine-1-carboxamido)methyl)benzoate (0.306 g, 0.687 mmol) and hydrazine monohydrate (0.668 mL, 13.738 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO₂, 4 g cartridge; methanol/dichloromethane=0% to 10%) to give N-(2-fluoro-4-(hydrazinecarbonyl)benzyl)-N-(4-fluorophenyl)-4-(oxetan-3-yl)piperazine-1-carboxamide as white solid (0.292 g, 95.4%).

[Step 5] Compound 21940

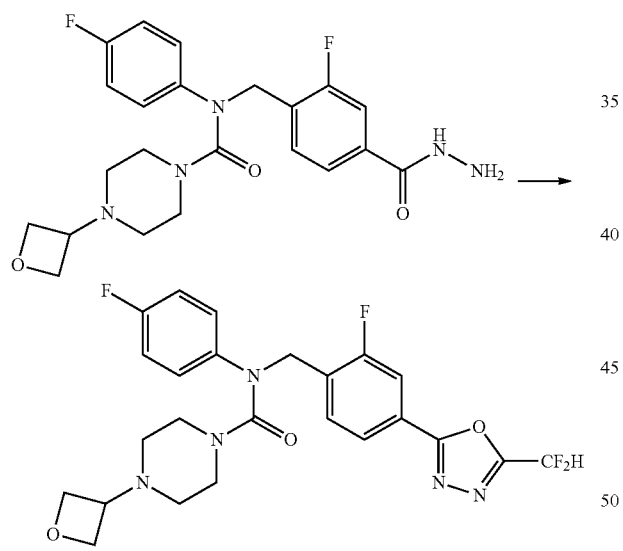

N-(2-Fluoro-4-(hydrazinecarbonyl)benzyl)-N-(4-fluorophenyl)-4-(oxetan-3-yl)piperazine-1-carboxamide (0.292 g, 0.655 mmol), triethylamine (0.274 mL, 1.966 mmol) and 2,2-difluoroacetic anhydride (0.244 mL, 1.966 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 12 g cartridge; methanol/dichloromethane=0% to 5%) to give N-(4-(5-(difluoromethyl)-1,3,4-oxadiazol-2-yl)-2-fluorobenzyl)-N-(4-fluorophenyl)-4-(oxetan-3-yl)piperazine-1-carboxamide as white solid (0.110 g, 33.2%).

¹H NMR (400 MHz, CDCl₃) δ 7.79 (d, 1H, J=8.0 Hz), 7.70-7.58 (m, 2H), 7.05-6.66 (m, 5H), 4.84 (s, 2H), 4.59-4.48 (m, 4H), 3.38 (s, 1H), 3.25 (s, 4H), 2.11 (s, 4H); LRMS (ES) m/z 506.2 (M⁺+1).

Example 385. Compound 21941: N-((5-(5-(Difluoromethyl)-1,3,4-oxadiazol-2-yl)pyridin-2-yl)methyl)-N-(4-fluorophenyl)-4-(oxetan-3-yl)piperazine-1-carboxamide

[Step 1] Tert-Butyl 4-((4-fluorophenyl)((5-(methoxycarbonyl)pyridin-2-yl)methyl)carbamoyl)piperazine-1-carboxylate

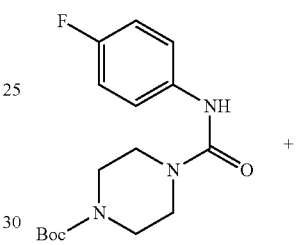

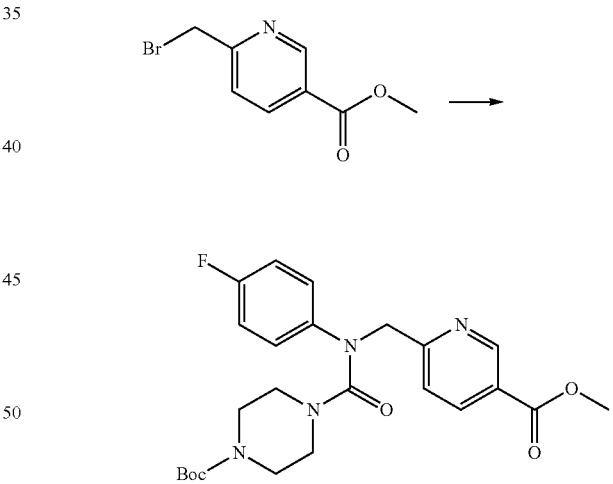

A solution of tert-butyl 4-((4-fluorophenyl)carbamoyl)piperazine-1-carboxylate (0.431 g, 1.333 mmol) and sodium hydride (60.00%, 0.080 g, 1.999 mmol) in tetrahydrofuran (6 mL) was stirred at the room temperature for 30 min, and mixed with methyl 6-(bromomethyl)nicotinate (0.337 g, 1.466 mmol). The reaction mixture was stirred at the same temperature for additional 18 hr, and concentrated under the reduced pressure. The concentrate was purified and concentrated by column chromatography (SiO₂, 12 g cartridge; ethyl acetate/hexane=0% to 50%) to give tert-butyl 4-((4-fluorophenyl)((5-(methoxycarbonyl)pyridin-2-yl)methyl)carbamoyl)piperazine-1-carboxylate as pale yellow oil (0.338 g, 53.6%).

1167

[Step 2] Methyl 6-((N-(4-fluorophenyl)piperazine-1-carboxamido)methyl)nicotinate hydrochloride

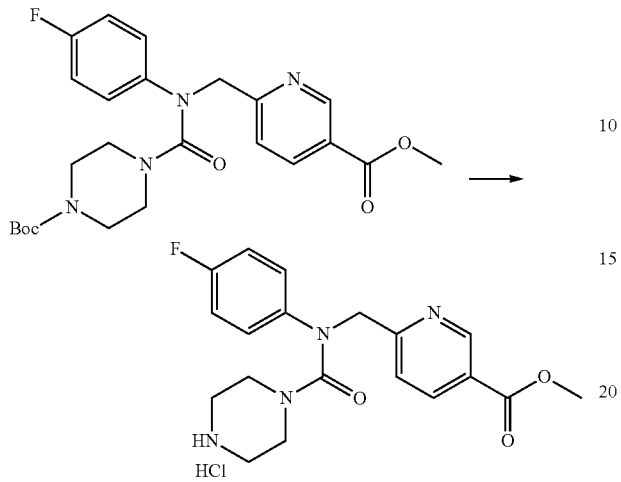

A solution of tert-butyl 4-(((4-fluorophenyl)((5-(methoxycarbonyl)pyridin-2-yl)methyl)carbamoyl)piperazine-1-carboxylate (0.338 g, 0.715 mmol) and hydrogen chloride (4.00 M solution in 1,4-dioxane, 0.715 mL, 2.859 mmol) in dichloromethane (4 mL) prepared at the room temperature was stirred at the same temperature for 18 hr, and concentrated under the reduced pressure. The title compound was used without further purification (methyl 6-((N-(4-fluorophenyl)piperazine-1-carboxamido)methyl)nicotinate hydrochloride, 0.292 g, 99.9%, pale yellow solid).

[Step 3] Methyl 6-((N-(4-fluorophenyl)-4-(oxetan-3-yl)piperazine-1-carboxamido)methyl)nicotinate

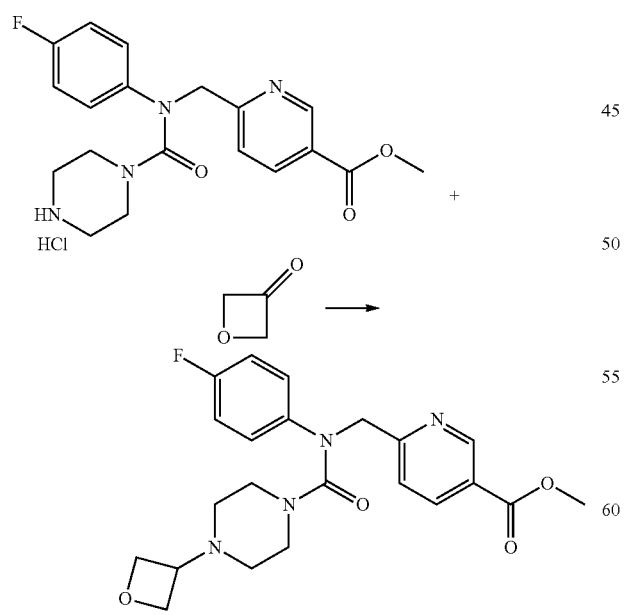

A solution of methyl 6-((N-(4-fluorophenyl)piperazine-1-carboxamido)methyl)nicotinate hydrochloride (0.292 g, 0.714 mmol), oxetan-3-one (0.063 mL, 1.071 mmol) and sodium triacetoxyborohydride (0.227 g, 1.071 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((N-(4-fluorophenyl)-4-(oxetan-3-yl)piperazine-1-carboxamido)methyl)nicotinate, 0.305 g, 99.7%, pale yellow oil).

[Step 4] N-(4-Fluorophenyl)-N-((5-(hydrazinecarbonyl)pyridin-2-yl)methyl)-4-(oxetan-3-yl)piperazine-1-carboxamide

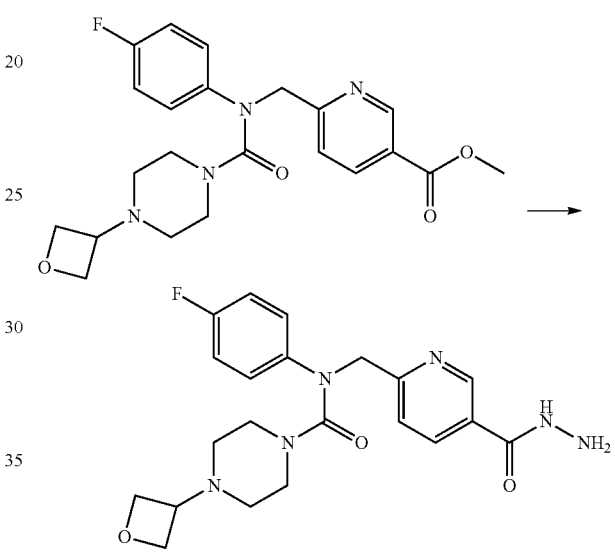

Methyl 6-((N-(4-fluorophenyl)-4-(oxetan-3-yl)piperazine-1-carboxamido)methyl)nicotinate (0.305 g, 0.712 mmol) and hydrazine monohydrate (0.692 mL, 14.237 mmol) were mixed at the room temperature in ethanol (4 mL) and then stirred at 80° C. for 18 hr, cooled down to the room temperature to terminate the reaction and concentrated under the reduced pressure. The concentrate was purified and concentrated by column chromatography (SiO$_2$, 4 g cartridge; methanol/dichloromethane=0% to 10%) to give N-(4-fluorophenyl)-N-((5-(hydrazinecarbonyl)pyridin-2-yl)methyl)-4-(oxetan-3-yl)piperazine-1-carboxamide as pale yellow solid (0.133 g, 43.6%).

[Step 5] Compound 21941

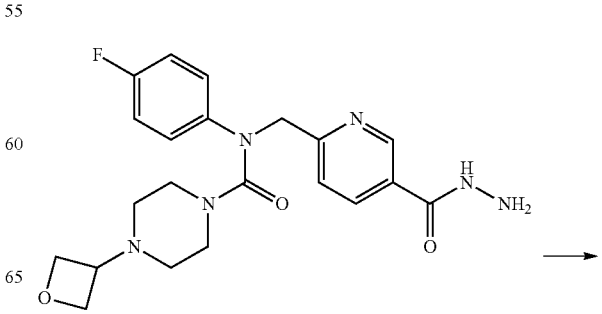

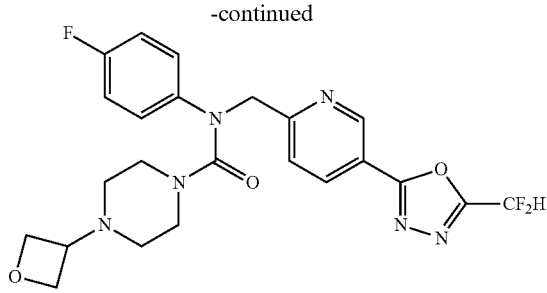

N-(4-Fluorophenyl)-N-((5-(hydrazinecarbonyl)pyridin-2-yl)methyl)-4-(oxetan-3-yl)piperazine-1-carboxamide (0.133 g, 0.310 mmol), triethylamine (0.130 mL, 0.931 mmol) and 2,2-difluoroacetic anhydride (0.116 mL, 0.931 mmol) were mixed at the room temperature in dichloromethane (4 mL) and then stirred at 40° C. for 18 hr, cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-((5-(5-(difluoromethyl)-1,3,4-oxadiazol-2-yl)pyridin-2-yl)methyl)-N-(4-fluorophenyl)-4-(oxetan-3-yl)piperazine-1-carboxamide as white solid (0.057 g, 37.3%).

$^1$H NMR (400 MHz, CDCl$_3$) δ 9.23 (s, 1H), 8.35 (dd, 1H, J=8.2, 2.0 Hz), 7.61 (d, 1H, J=8.2 Hz), 7.21-7.12 (m, 2H), 7.10-6.76 (m, 3H), 5.07 (s, 2H), 4.70-4.62 (m, 4H), 3.56 (s, 1H), 3.42 (s, 4H), 2.32 (s, 4H); LRMS (ES) m/z 489.3 (M$^+$+1).

Example 386. Compound 21942: N-(3-Chlorophenyl)-N-(4-(5-(difluoromethyl)-1,3,4-oxadiazol-2-yl)benzyl)-4-(oxetan-3-yl)piperazine-1-carboxamide

[Step 1] Tert-Butyl 4-((3-chlorophenyl)carbamoyl)piperazine-1-carboxylate

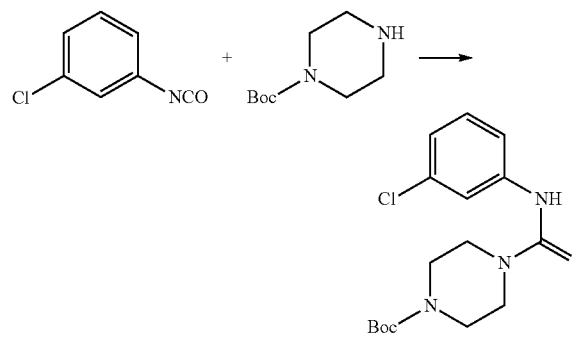

A solution of 1-chloro-3-isocyanatobenzene (0.488 mL, 4.000 mmol) and tert-butyl piperazine-1-carboxylate (0.745 g, 4.000 mmol) in diethylether (10 mL) prepared at the room temperature was stirred at the same temperature for 3 hr, and concentrated under the reduced pressure. The title compound was used without further purification (tert-butyl 4-((3-chlorophenyl)carbamoyl)piperazine-1-carboxylate, 1.358 g, 99.9%, white solid).

[Step 2] Tert-Butyl 4-((3-chlorophenyl)(4-(methoxycarbonyl)benzyl)carbamoyl)piperazine-1-carboxylate

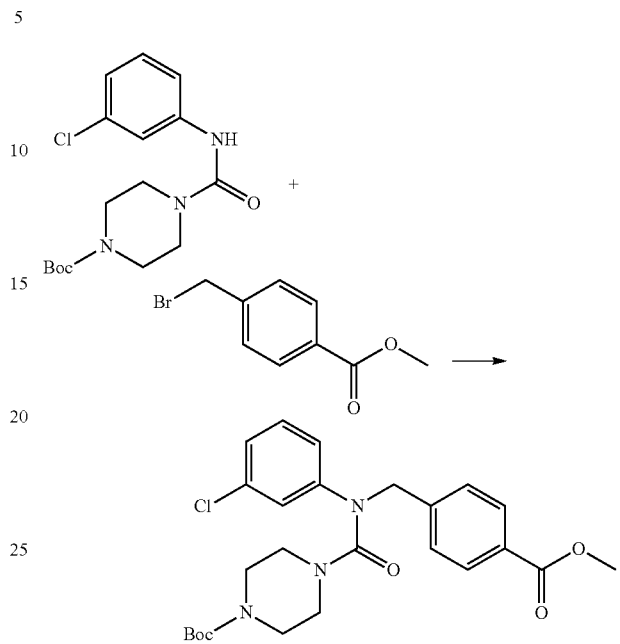

A solution of tert-butyl 4-((3-chlorophenyl)carbamoyl)piperazine-1-carboxylate (0.462 g, 1.360 mmol) and sodium hydride (60.00%, 0.082 g, 2.040 mmol) in tetrahydrofuran (6 mL) was stirred at the room temperature for 30 min, and mixed with methyl 4-(bromomethyl)benzoate (0.343 g, 1.496 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((3-chlorophenyl)(4-(methoxycarbonyl)benzyl)carbamoyl)piperazine-1-carboxylate as white solid (0.325 g, 49.0%).

[Step 3] Methyl 4-((N-(3-chlorophenyl)piperazine-1-carboxamido)methyl)benzoate hydrochloride

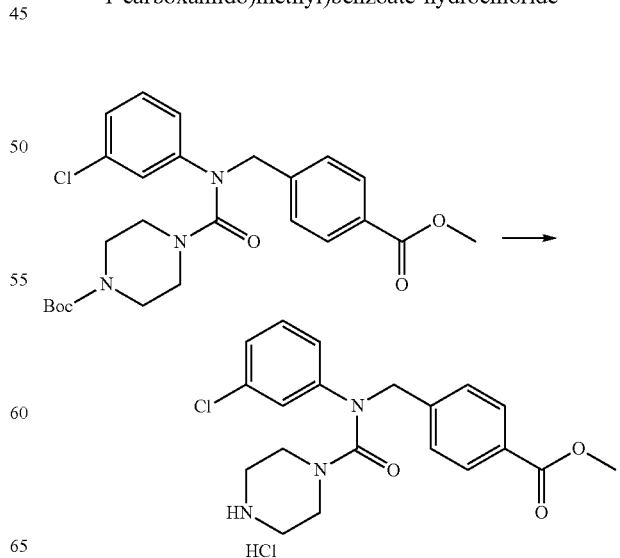

A solution of tert-butyl 4-((3-chlorophenyl)(4-(methoxycarbonyl)benzyl)carbamoyl)piperazine-1-carboxylate (0.325 g, 0.666 mmol) and hydrogen chloride (4.00 M solution in 1,4-dioxane, 0.666 mL, 2.664 mmol) in dichloromethane (5 mL) was stirred at the room temperature for 18 hr, and concentrated under the reduced pressure. The title compound was used without further purification (methyl 4-((N-(3-chlorophenyl)piperazine-1-carboxamido)methyl)benzoate hydrochloride, 0.282 g, 99.8%, pale yellow solid).

[Step 4] Methyl 4-((N-(3-chlorophenyl)-4-(oxetan-3-yl)piperazine-1-carboxamido)methyl)benzoate

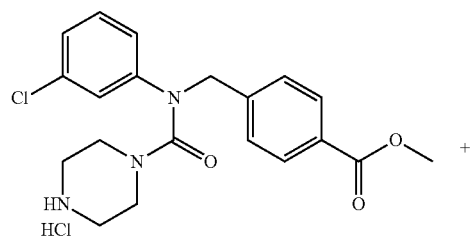

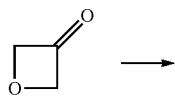

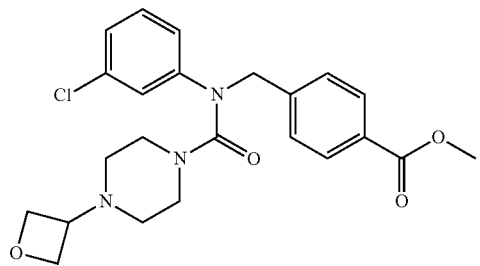

A solution of methyl 4-((N-(3-chlorophenyl)piperazine-1-carboxamido)methyl)benzoate hydrochloride (0.282 g, 0.665 mmol), oxetan-3-one (0.058 mL, 0.997 mmol) and sodium triacetoxyborohydride (0.211 g, 0.997 mmol) in dichloromethane (5 mL) was stirred at the room temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give methyl 4-((N-(3-chlorophenyl)-4-(oxetan-3-yl)piperazine-1-carboxamido)methyl)benzoate as colorless oil (0.293 g, 99.4%).

[Step 5] N-(3-Chlorophenyl)-N-(4-(hydrazinecarbonyl)benzyl)-4-(oxetan-3-yl)piperazine-1-carboxamide

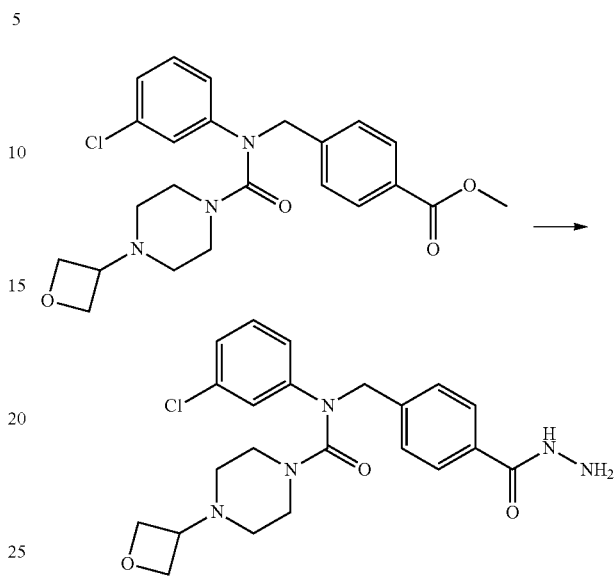

Methyl 4-((N-(3-chlorophenyl)-4-(oxetan-3-yl)piperazine-1-carboxamido)methyl)benzoate (0.293 g, 0.660 mmol) and hydrazine monohydrate (0.642 mL, 13.200 mmol) were mixed at the room temperature in ethanol (5 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(3-chlorophenyl)-N-(4-(hydrazinecarbonyl)benzyl)-4-(oxetan-3-yl)piperazine-1-carboxamide as white solid (0.158 g, 53.8%).

[Step 6] Compound 21942

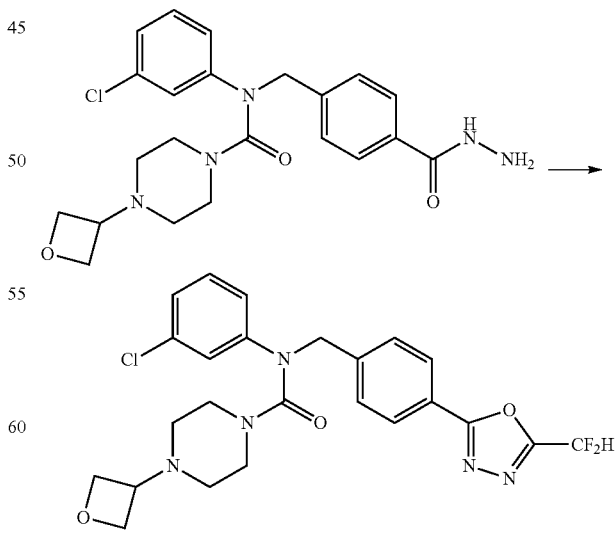

N-(3-Chlorophenyl)-N-(4-(hydrazinecarbonyl)benzyl)-4-(oxetan-3-yl)piperazine-1-carboxamide (0.158 g, 0.355 mmol), triethylamine (0.149 mL, 1.066 mmol) and 2,2-difluoroacetic anhydride (0.132 mL, 1.066 mmol) were mixed at the room temperature in dichloromethane (4 mL) and then stirred at 40° C. for 18 hr, cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(3-chlorophenyl)-N-(4-(5-(difluoromethyl)-1,3,4-oxadiazol-2-yl)benzyl)-4-(oxetan-3-yl)piperazine-1-carboxamide as white solid (0.060 g, 33.7%).

$^1$H NMR (400 MHz, CDCl$_3$) δ 8.05 (d, 2H, J=7.9 Hz), 7.48 (d, 2H, J=7.9 Hz), 7.24 (t, 1H, J=8.0 Hz), 7.14-6.74 (m, 4H), 4.94 (s, 2H), 4.69-4.55 (m, 4H), 3.49 (s, 1H), 3.37 (s, 4H), 2.23 (s, 4H); LRMS (ES) m/z 504.2 (M$^+$+1).

Example 387. Compound 21943: N-(3-Chlorophenyl)-N-(4-(5-(difluoromethyl)-1,3,4-oxadiazol-2-yl)-2-fluorobenzyl)-4-(oxetan-3-yl)piperazine-1-carboxamide

[Step 1] Tert-Butyl 4-((3-chlorophenyl)(2-fluoro-4-(methoxycarbonyl)benzyl)carbamoyl)piperazine-1-carboxylate

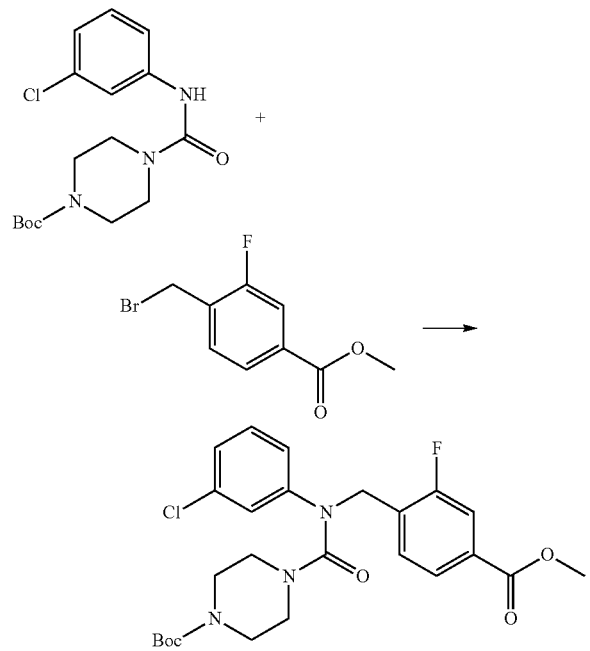

A solution of tert-butyl 4-((3-chlorophenyl)carbamoyl)piperazine-1-carboxylate (0.453 g, 1.333 mmol) and sodium hydride (60.00%, 0.080 g, 1.999 mmol) in tetrahydrofuran (6 mL) was stirred at the room temperature for 30 min, and mixed with methyl 4-(bromomethyl)-3-fluorobenzoate (0.362 g, 1.466 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((3-chlorophenyl)(2-fluoro-4-(methoxycarbonyl)benzyl)carbamoyl)piperazine-1-carboxylate as colorless oil (0.391 g, 58.0%).

[Step 2] Methyl 4-((N-(3-chlorophenyl)piperazine-1-carboxamido)methyl)-3-fluorobenzoate hydrochloride

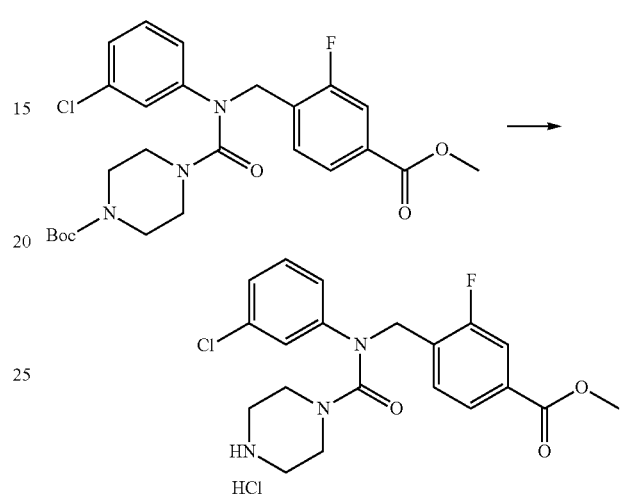

A solution of tert-butyl 4-((3-chlorophenyl)(2-fluoro-4-(methoxycarbonyl)benzyl)carbamoyl)piperazine-1-carboxylate (0.391 g, 0.773 mmol) and hydrogen chloride (4.00 M solution in 1,4-dioxane, 0.773 mL, 3.093 mmol) in dichloromethane (4 mL) was stirred at the room temperature for 18 hr, and concentrated under the reduced pressure. The title compound was used without further purification (methyl 4-((N-(3-chlorophenyl)piperazine-1-carboxamido)methyl)-3-fluorobenzoate hydrochloride, 0.341 g, 99.7%, pale yellow solid).

[Step 3] Methyl 4-((N-(3-chlorophenyl)-4-(oxetan-3-yl)piperazine-1-carboxamido)methyl)-3-fluorobenzoate

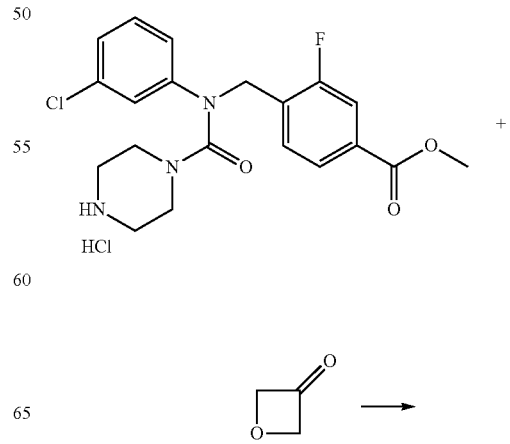

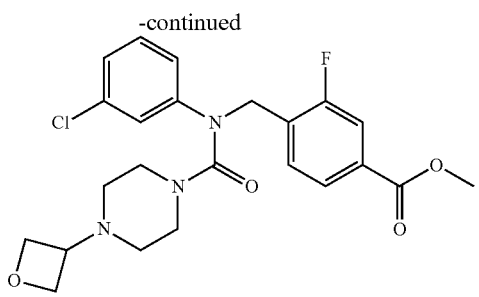

A solution of methyl 4-((N-(3-chlorophenyl)piperazine-1-carboxamido)methyl)-3-fluorobenzoate hydrochloride (0.341 g, 0.771 mmol), oxetan-3-one (0.068 mL, 1.156 mmol) and sodium triacetoxyborohydride (0.245 g, 1.156 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((N-(3-chlorophenyl)-4-(oxetan-3-yl)piperazine-1-carboxamido)methyl)-3-fluorobenzoate, 0.355 g, 99.7%, pale yellow oil).

[Step 4] N-(3-Chlorophenyl)-N-(2-fluoro-4-(hydrazinecarbonyl)benzyl)-4-(oxetan-3-yl)piperazine-1-carboxamide

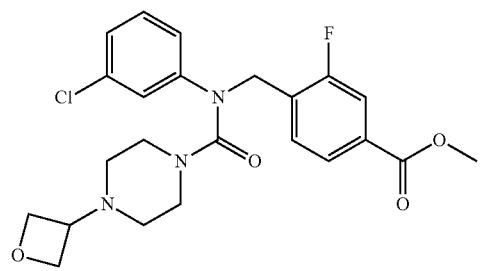

Methyl 4-((N-(3-chlorophenyl)-4-(oxetan-3-yl)piperazine-1-carboxamido)methyl)-3-fluorobenzoate (0.355 g, 0.769 mmol) and hydrazine monohydrate (0.747 mL, 15.371 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(3-chlorophenyl)-N-(2-fluoro-4-(hydrazinecarbonyl)benzyl)-4-(oxetan-3-yl)piperazine-1-carboxamide as white solid (0.307 g, 86.4%).

[Step 5] Compound 21943

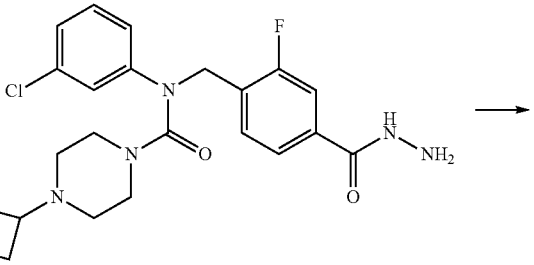

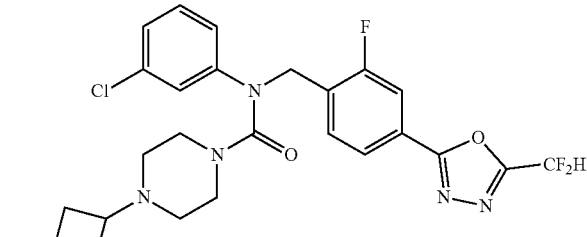

N-(3-Chlorophenyl)-N-(2-fluoro-4-(hydrazinecarbonyl)benzyl)-4-(oxetan-3-yl)piperazine-1-carboxamide (0.307 g, 0.664 mmol), triethylamine (0.278 mL, 1.991 mmol) and 2,2-difluoroacetic anhydride (0.248 mL, 1.991 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(3-chlorophenyl)-N-(4-(5-(difluoromethyl)-1,3,4-oxadiazol-2-yl)-2-fluorobenzyl)-4-(oxetan-3-yl)piperazine-1-carboxamide as white solid (0.085 g, 24.6%).

$^1$H NMR (400 MHz, CDCl$_3$) δ 7.79 (d, 1H, J=8.0 Hz), 7.69 (d, 1H, J=10.1 Hz), 7.59 (t, 1H, J=7.6 Hz), 7.17 (t, 1H, J=7.9 Hz), 7.07-7.00 (m, 2H), 6.98-6.68 (m, 2H), 4.88 (s, 2H), 4.59-4.45 (m, 4H), 3.43-3.32 (m, 1H), 3.27 (s, 4H), 2.12 (s, 4H); LRMS (ES) m/z 522.2 (M$^+$+1).

1177

Example 388. Compound 21944: N-(3-Chlorophenyl)-N-((5-(5-(difluoromethyl)-1,3,4-oxadiazol-2-yl)pyridin-2-yl)methyl)-4-(oxetan-3-yl)piperazine-1-carboxamide

[Step 1] Tert-Butyl 4-((3-chlorophenyl)((5-(methoxycarbonyl)pyridin-2-yl)methyl)carbamoyl)piperazine-1-carboxylate

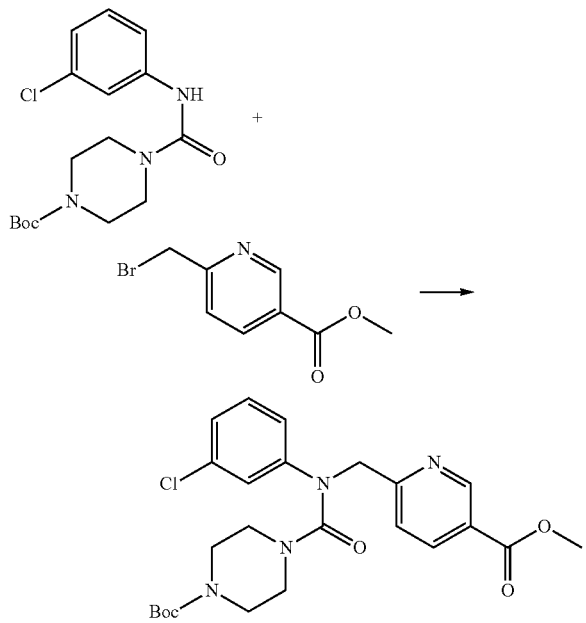

A solution of tert-butyl 4-((3-chlorophenyl)carbamoyl)piperazine-1-carboxylate (0.453 g, 1.333 mmol) and sodium hydride (60.00%, 0.080 g, 1.999 mmol) in tetrahydrofuran (6 mL) was stirred at the room temperature for 30 min, and mixed with methyl 6-(bromomethyl)nicotinate (0.337 g, 1.466 mmol). The reaction mixture was stirred at the same temperature for additional 18 hr, and concentrated under the reduced pressure. The concentrate was purified and concentrated by column chromatography-(SiO$_2$, 12 g cartridge; ethyl acetate/hexane=0% to 50-%) to give tert-butyl 4-((3-chlorophenyl)((5-(methoxycarbonyl)pyridin-2-yl)methyl)carbamoyl)piperazine-1-carboxylate as pale yellow oil (0.353 g, 54.2%).

[Step 2] Methyl 6-((N-(3-chlorophenyl)piperazine-1-carboxamido)methyl)nicotinate hydrochloride

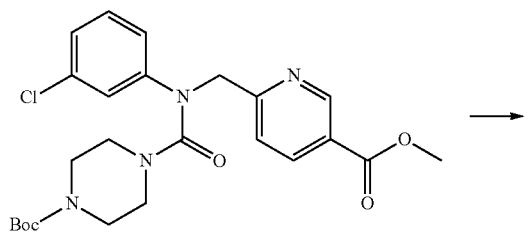

1178

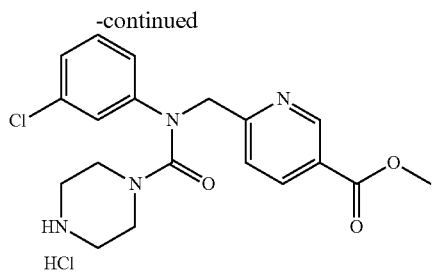

A solution of tert-butyl 4-((3-chlorophenyl)((5-(methoxycarbonyl)pyridin-2-yl)methyl)carbamoyl)piperazine-1-carboxylate (0.353 g, 0.723 mmol) and hydrogen chloride (4.00 M solution in 1,4-dioxane, 0.723 mL, 2.891 mmol) in dichloromethane (4 mL) was stirred at the room temperature for 18 hr, and concentrated under the reduced pressure. The title compound was used without further purification (methyl 6-((N-(3-chlorophenyl)piperazine-1-carboxamido)methyl)nicotinate hydrochloride, 0.307 g, 99.9%, pale yellow solid).

[Step 3] Methyl 6-((N-(3-chlorophenyl)-4-(oxetan-3-yl)piperazine-1-carboxamido)methyl)nicotinate

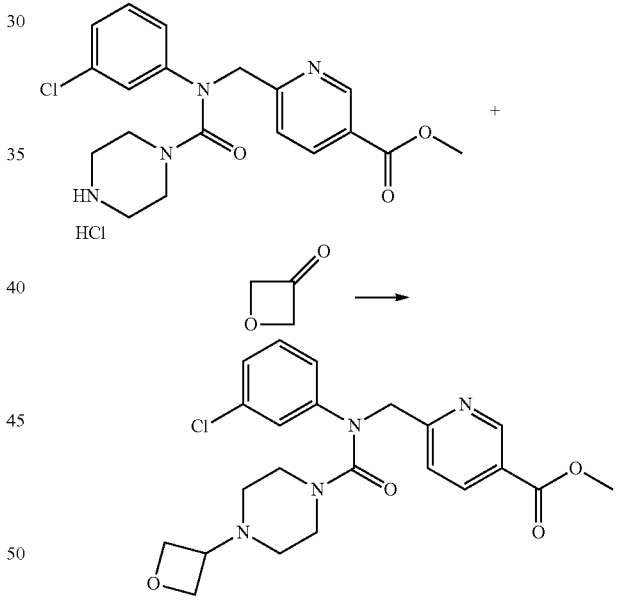

A solution of methyl 6-((N-(3-chlorophenyl)piperazine-1-carboxamido)methyl)nicotinate hydrochloride (0.307 g, 0.722 mmol), oxetan-3-one (0.063 mL, 1.083 mmol) and sodium triacetoxyborohydride (0.229 g, 1.083 mmol) in dichloromethane (5 mL) to terminate the reaction was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((N-(3-chlorophenyl)-4-(oxetan-3-yl)piperazine-1-carboxamido)methyl)nicotinate, 0.320 g, 99.6%, pale yellow oil).

[Step 4] N-(3-Chlorophenyl)-N-((5-(hydrazinecarbonyl)pyridin-2-yl)methyl)-4-(oxetan-3-yl)piperazine-1-carboxamide

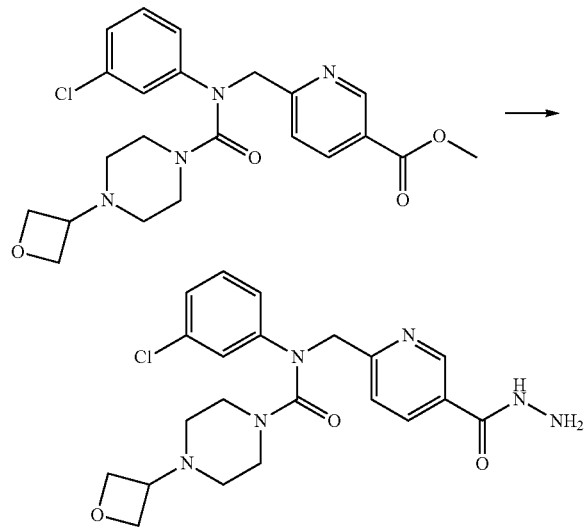

Methyl 6-((N-(3-chlorophenyl)-4-(oxetan-3-yl)piperazine-1-carboxamido)methyl)nicotinate (0.320 g, 0.719 mmol) and hydrazine monohydrate (0.699 mL, 14.385 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(3-chlorophenyl)-N-((5-(hydrazinecarbonyl)pyridin-2-yl)methyl)-4-(oxetan-3-yl)piperazine-1-carboxamide as orange solid (0.098 g, 30.7%).

[Step 5] Compound 21944

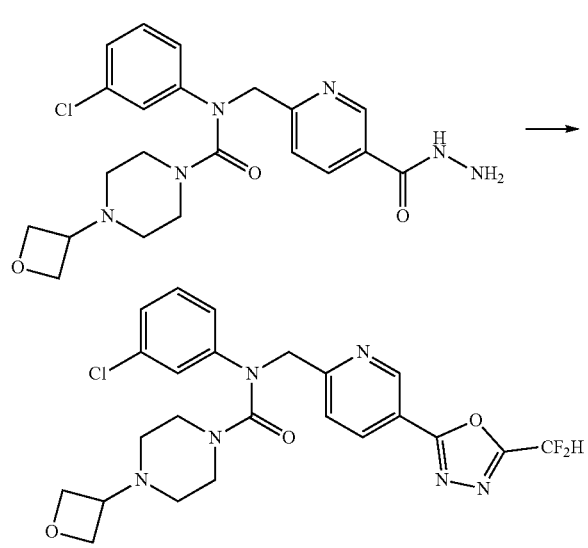

N-(3-Chlorophenyl)-N-((5-(hydrazinecarbonyl)pyridin-2-yl)methyl)-4-(oxetan-3-yl)piperazine-1-carboxamide (0.098 g, 0.221 mmol), triethylamine (0.092 mL, 0.662 mmol) and 2,2-difluoroacetic anhydride (0.082 mL, 0.662 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(3-chlorophenyl)-N-((5-(5-(difluoromethyl)-1,3,4-oxadiazol-2-yl)pyridin-2-yl)methyl)-4-(oxetan-3-yl)piperazine-1-carboxamide as pale yellow solid (0.021 g, 18.5%).

$^1$H NMR (400 MHz, CDCl$_3$) δ 9.24 (dd, 1H, J=2.2, 0.8 Hz), 8.35 (dd, 1H, J=8.2, 2.2 Hz), 7.58 (dd, 1H, J=8.2, 0.9 Hz), 7.25 (t, 1H, J=8.1 Hz), 7.18 (t, 1H, J=2.1 Hz), 7.11-6.80 (m, 3H), 5.10 (s, 2H), 4.69-4.56 (m, 4H), 3.49 (s, 1H), 3.38 (s, 4H), 2.25 (s, 4H); LRMS (ES) m/z 505.3 (M$^+$+1).

Example 389. Compound 21945: N-(4-Chlorophenyl)-N-(4-(5-(difluoromethyl)-1,3,4-oxadiazol-2-yl)benzyl)-4-(oxetan-3-yl)piperazine-1-carboxamide

[Step 1] Tert-Butyl 4-((4-chlorophenyl)carbamoyl)piperazine-1-carboxylate

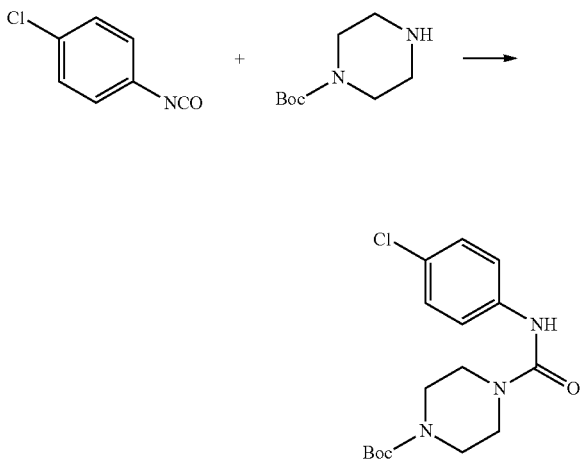

A solution of 1-chloro-4-isocyanatobenzene (0.614 g, 4.000 mmol) and tert-butyl piperazine-1-carboxylate (0.745 g, 4.000 mmol) in diethylether (10 mL) prepared at the room temperature was stirred at the same temperature for 3 hr, and concentrated under the reduced pressure. The title compound was used without further purification (tert-butyl 4-((4-chlorophenyl)carbamoyl)piperazine-1-carboxylate, 1.358 g, 99.9%, white solid).

1181

[Step 2] Tert-Butyl 4-((4-chlorophenyl)(4-(methoxycarbonyl)benzyl)carbamoyl)piperazine-1-carboxylate

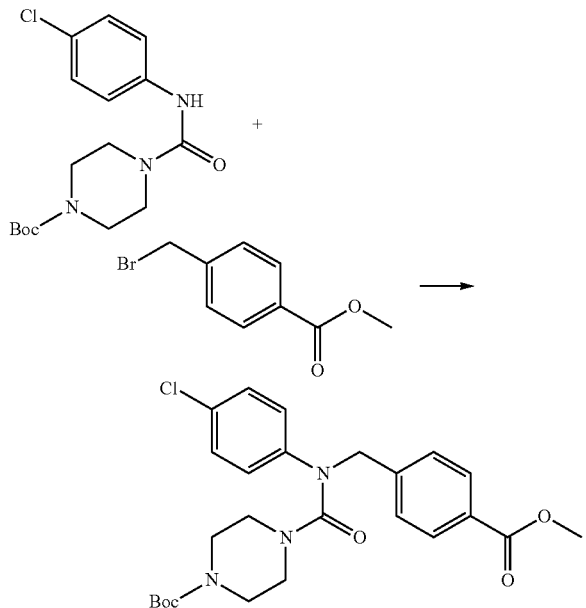

A solution of tert-butyl 4-((4-chlorophenyl)carbamoyl)piperazine-1-carboxylate (0.356 g, 1.046 mmol) and sodium hydride (60.00%, 0.063 g, 1.569 mmol) in tetrahydrofuran (6 mL) was stirred at the room temperature for 30 min, and mixed with methyl 4-(bromomethyl)benzoate (0.264 g, 1.151 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((4-chlorophenyl)(4-(methoxycarbonyl)benzyl)carbamoyl)piperazine-1-carboxylate as white solid (0.279 g, 54.7%).

[Step 3] Methyl 4-((N-(4-chlorophenyl)piperazine-1-carboxamido)methyl)benzoate hydrochloride

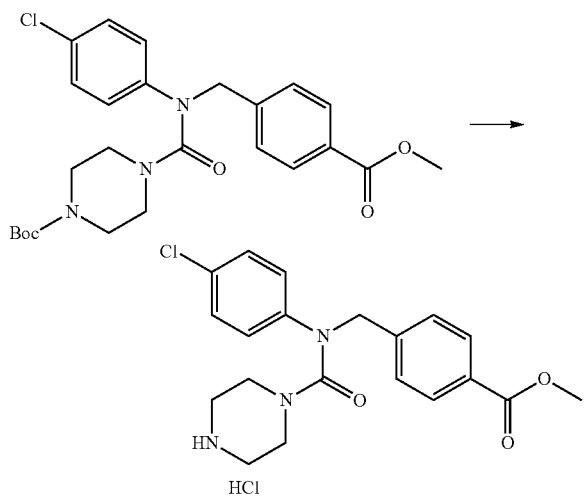

1182

A solution of tert-butyl 4-((4-chlorophenyl)(4-(methoxycarbonyl)benzyl)carbamoyl)piperazine-1-carboxylate (0.279 g, 0.572 mmol) and hydrogen chloride (4.00 M solution in 1,4-dioxane, 0.572 mL, 2.287 mmol) in dichloromethane (5 mL) prepared at the room temperature was stirred at the same temperature for 18 hr, and concentrated under the reduced pressure. The title compound was used without further purification (methyl 4-((N-(4-chlorophenyl)piperazine-1-carboxamido)methyl)benzoate hydrochloride, 0.242 g, 99.8%, pale yellow solid).

[Step 4] Methyl 4-((N-(4-chlorophenyl)-4-(oxetan-3-yl)piperazine-1-carboxamido)methyl)benzoate

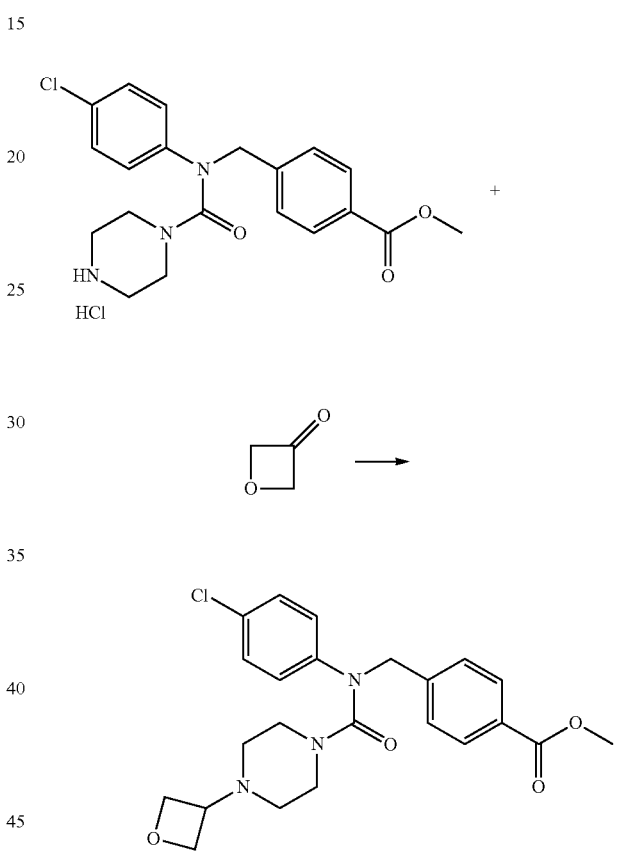

A solution of methyl 4-((N-(4-chlorophenyl)piperazine-1-carboxamido)methyl)benzoate hydrochloride (0.242 g, 0.570 mmol), oxetan-3-one (0.050 mL, 0.855 mmol) and sodium triacetoxyborohydride (0.181 g, 0.855 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give methyl 4-((N-(4-chlorophenyl)-4-(oxetan-3-yl)piperazine-1-carboxamido)methyl)benzoate as colorless oil (0.207 g, 81.9%).

1183

[Step 5] N-(4-Chlorophenyl)-N-(4-(hydrazinecarbonyl)benzyl)-4-(oxetan-3-yl)piperazine-1-carboxamide

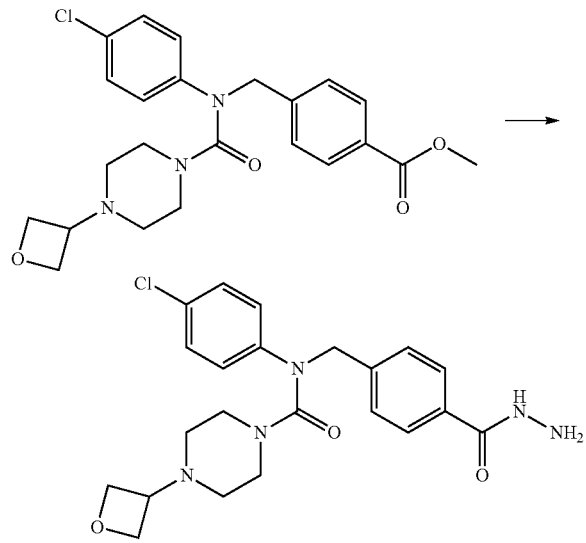

Methyl 4-((N-(4-chlorophenyl)-4-(oxetan-3-yl)piperazine-1-carboxamido)methyl)benzoate (0.207 g, 0.466 mmol) and hydrazine monohydrate (0.453 mL, 9.326 mmol) were mixed at the room temperature in ethanol (5 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(4-chlorophenyl)-N-(4-(hydrazinecarbonyl)benzyl)-4-(oxetan-3-yl)piperazine-1-carboxamide as white solid (0.090 g, 43.2%).

[Step 6] Compound 21945

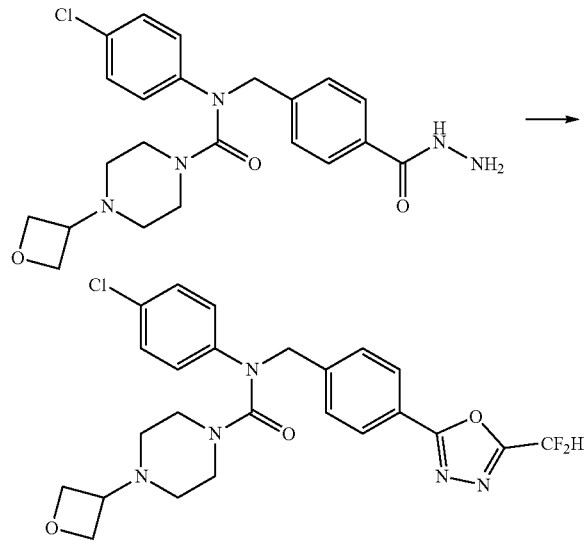

1184

N-(4-Chlorophenyl)-N-(4-(hydrazinecarbonyl)benzyl)-4-(oxetan-3-yl)piperazine-1-carboxamide (0.090 g, 0.202 mmol), triethylamine (0.084 mL, 0.605 mmol) and 2,2-difluoroacetic anhydride (0.075 mL, 0.605 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-chlorophenyl)-N-(4-(5-(difluoromethyl)-1,3,4-oxadiazol-2-yl)benzyl)-4-(oxetan-3-yl)piperazine-1-carboxamide as white solid (0.039 g, 38.6%).

$^1$H NMR (400 MHz, CDCl$_3$) δ 7.96 (d, 2H, J=7.9 Hz), 7.37 (d, 2H, J=7.9 Hz), 7.19 (t, 2H, J=4.3 Hz), 7.04-6.58 (m, 3H), 4.83 (s, 2H), 4.61-4.53 (m, 4H), 3.44 (s, 1H), 3.31 (s, 4H), 2.18 (s, 4H); LRMS (ES) m/z 504.3 (M$^+$+1).

Example 390. Compound 21946: N-(4-Chlorophenyl)-N-(4-(5-(difluoromethyl)-1,3,4-oxadiazol-2-yl)-2-fluorobenzyl)-4-(oxetan-3-yl)piperazine-1-carboxamide

[Step 1] Tert-Butyl 4-((4-chlorophenyl)(2-fluoro-4-(methoxycarbonyl)benzyl)carbamoyl)piperazine-1-carboxylate

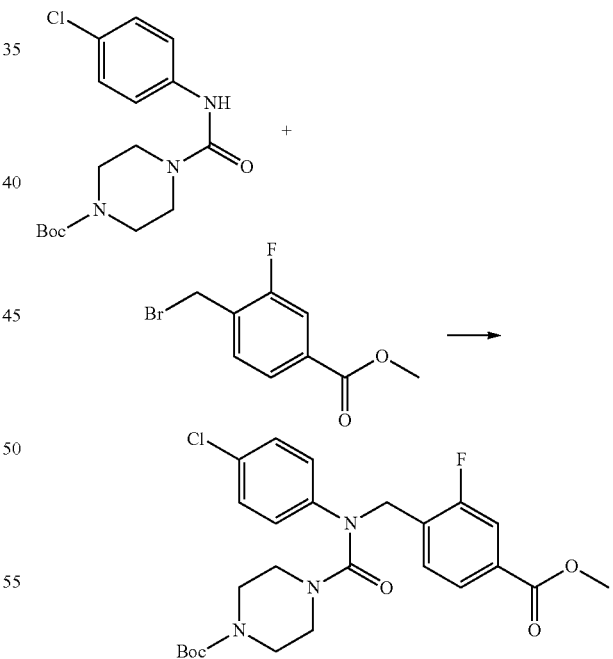

A solution of tert-butyl 4-((4-chlorophenyl)carbamoyl)piperazine-1-carboxylate (0.453 g, 1.333 mmol) and sodium hydride (60.00%, 0.080 g, 1.999 mmol) in tetrahydrofuran (6 mL) was stirred at the room temperature for 30 min, and mixed with methyl 4-(bromomethyl)-3-fluorobenzoate (0.362 g, 1.466 mmol). The reaction mixture was stirred at the same temperature for additional 18 hr, and concentrated under the reduced pressure. The concentrate was purified and concentrated by column chromatography (SiO₂, 12 g cartridge; ethyl acetate/hexane=0% to 50%) to give tert-butyl 4-((4-chlorophenyl)(2-fluoro-4-(methoxycarbonyl)benzyl)carbamoyl)piperazine-1-carboxylate as colorless oil (0.347 g, 51.4%).

[Step 2] Methyl 4-((N-(4-chlorophenyl)piperazine-1-carboxamido)methyl)-3-fluorobenzoate hydrochloride

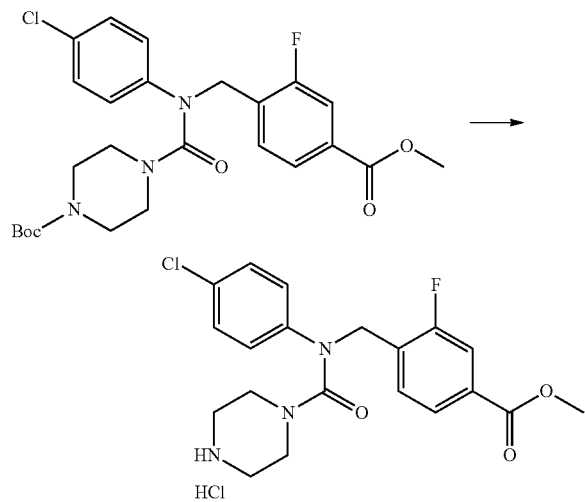

A solution of tert-butyl 4-((4-chlorophenyl)(2-fluoro-4-(methoxycarbonyl)benzyl)carbamoyl)piperazine-1-carboxylate (0.347 g, 0.685 mmol) and hydrogen chloride (4.00 M solution in 1,4-dioxane, 0.685 mL, 2.739 mmol) in dichloromethane (4 mL) prepared at the room temperature was stirred at the same temperature for 18 hr, and concentrated under the reduced pressure. The title compound was used without further purification (methyl 4-((N-(4-chlorophenyl)piperazine-1-carboxamido)methyl)-3-fluorobenzoate hydrochloride, 0.302 g, 99.7%, pale yellow solid).

[Step 3] Methyl 4-((N-(4-chlorophenyl)-4-(oxetan-3-yl)piperazine-1-carboxamido)methyl)-3-fluorobenzoate

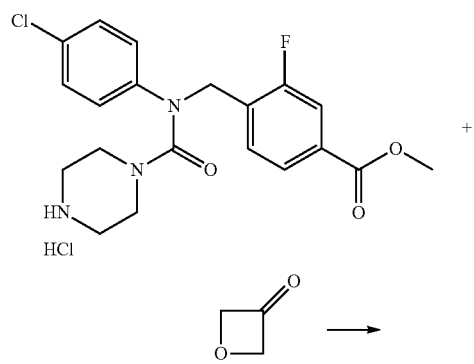

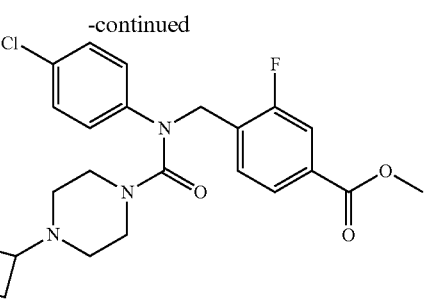

A solution of methyl 4-((N-(4-chlorophenyl)piperazine-1-carboxamido)methyl)-3-fluorobenzoate hydrochloride (0.302 g, 0.683 mmol), oxetan-3-one (0.060 mL, 1.024 mmol) and sodium triacetoxyborohydride (0.217 g, 1.024 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 4-((N-(4-chlorophenyl)-4-(oxetan-3-yl)piperazine-1-carboxamido)methyl)-3-fluorobenzoate, 0.315 g, 99.9%, pale yellow oil).

[Step 4] N-(4-Chlorophenyl)-N-(2-fluoro-4-(hydrazinecarbonyl)benzyl)-4-(oxetan-3-yl)piperazine-1-carboxamide

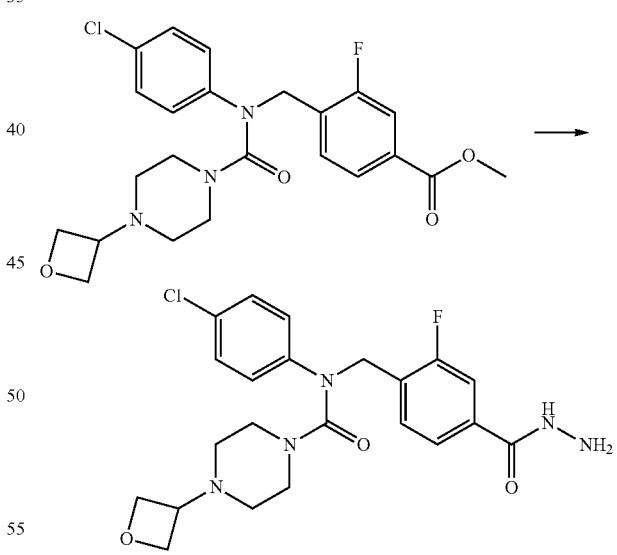

Methyl 4-((N-(4-chlorophenyl)-4-(oxetan-3-yl)piperazine-1-carboxamido)methyl)-3-fluorobenzoate (0.315 g, 0.682 mmol) and hydrazine monohydrate (0.663 mL, 13.639 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO₂, 4 g cartridge; methanol/dichloromethane=0% to 10%) to give N-(4-chlorophenyl)-N-(2-fluoro-4-(hydrazinecarbonyl)benzyl)-4-(oxetan-3-yl)piperazine-1-carboxamide as white solid (0.283 g, 89.7%).

[Step 5] Compound 21946

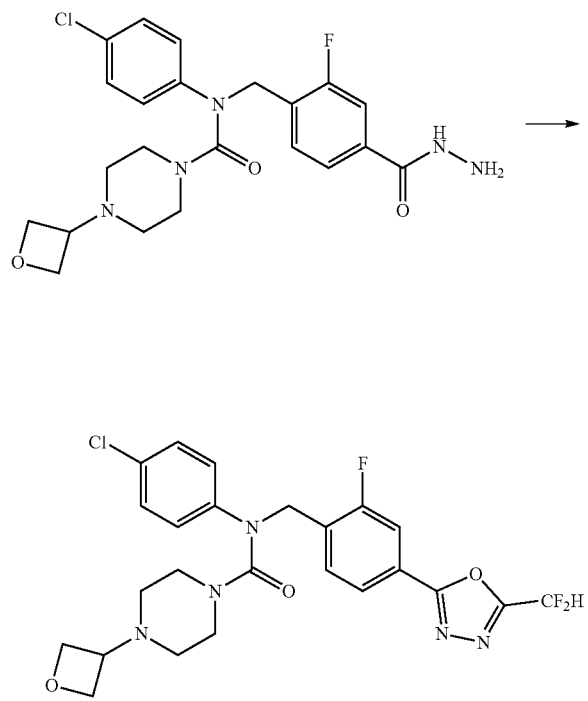 [SMILES: COc1ccc(N(Cc2ccc(C(=O)NN)cc2)C(=O)N2CCN(C3COC3)CC2)cc1 ; COc1ccc(N(Cc2ccc(-c3nnc(C(F)F)o3)cc2)C(=O)N2CCN(C3COC3)CC2)cc1]

N-(4-Chlorophenyl)-N-(2-fluoro-4-(hydrazinecarbonyl)benzyl)-4-(oxetan-3-yl)piperazine-1-carboxamide (0.283 g, 0.612 mmol), triethylamine (0.256 mL, 1.835 mmol) and 2,2-difluoroacetic anhydride (0.228 mL, 1.835 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-chlorophenyl)-N-(4-(5-(difluoromethyl)-1,3,4-oxadiazol-2-yl)-2-fluorobenzyl)-4-(oxetan-3-yl)piperazine-1-carboxamide as white solid (0.099 g, 31.0%).

$^1$H NMR (400 MHz, CDCl$_3$) δ 7.78 (d, 1H, J=8.0 Hz), 7.67 (d, 1H, J=10.0 Hz), 7.60 (t, 1H, J=7.6 Hz), 7.19 (s, 1H), 7.01-6.66 (m, 3H), 4.86 (s, 2H), 4.59-4.49 (m, 4H), 3.40 (s, 1H), 3.27 (s, 4H), 2.13 (s, 4H); LRMS (ES) m/z 522.2 (M$^+$+1).

Example 391. Compound 21947: N-(4-Chlorophenyl)-N-((5-(5-(difluoromethyl)-1,3,4-oxadiazol-2-yl)pyridin-2-yl)methyl)-4-(oxetan-3-yl)piperazine-1-carboxamide

[Step 1.] Tert-Butyl 4-((4-chlorophenyl)((5-(methoxycarbonyl)pyridin-2-yl)methyl)carbamoyl)piperazine-1-carboxylate

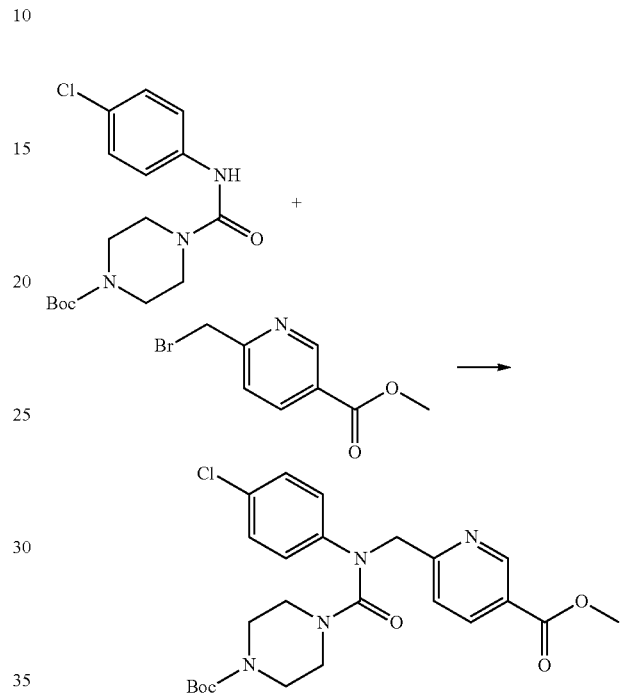

A solution of tert-butyl 4-((4-chlorophenyl)carbamoyl)piperazine-1-carboxylate (0.453 g, 1.333 mmol) and sodium hydride (60.00%, 0.080 g, 1.999 mmol) in tetrahydrofuran (6 mL) was stirred at the room temperature for 30 min, and mixed with methyl 6-(bromomethyl)nicotinate (0.337 g, 1.466 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((4-chlorophenyl)((5-(methoxycarbonyl)pyridin-2-yl)methyl)carbamoyl)piperazine-1-carboxylate as pale yellow oil (0.287 g, 44.0%).

[Step 2] Methyl 6-((N-(4-chlorophenyl)piperazine-1-carboxamido)methyl)nicotinate hydrochloride

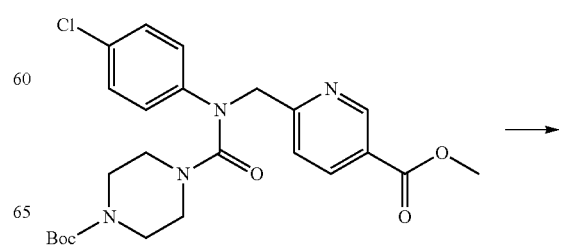

-continued

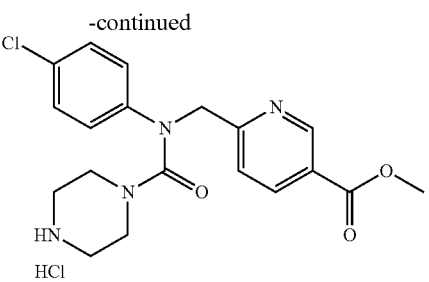

A solution of tert-butyl 4-((4-chlorophenyl)((5-(methoxycarbonyl)pyridin-2-yl)methyl)carbamoyl)piperazine-1-carboxylate (0.287 g, 0.586 mmol) and hydrogen chloride (4.00 M solution in 1,4-dioxane, 0.586 mL, 2.345 mmol) in dichloromethane (4 mL) prepared at the room temperature was stirred at the same temperature for 18 hr, and concentrated under the reduced pressure. The title compound was used without further purification (methyl 6-((N-(4-chlorophenyl)piperazine-1-carboxamido)methyl)nicotinate hydrochloride, 0.249 g, 99.9%, pale yellow solid).

[Step 3] Methyl 6-((N-(4-chlorophenyl)-4-(oxetan-3-yl)piperazine-1-carboxamido)methyl)nicotinate

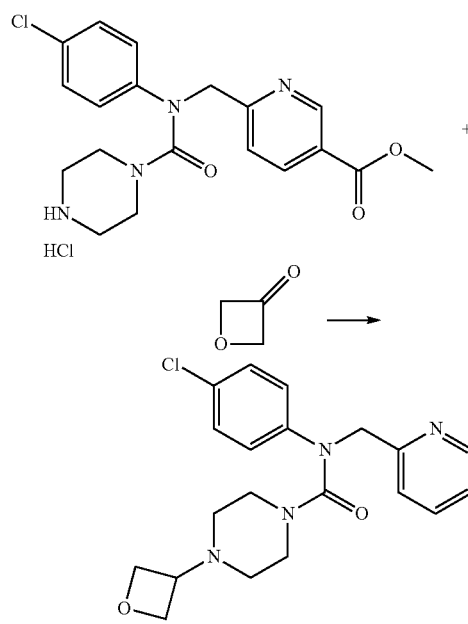

A solution of methyl 6-((N-(4-chlorophenyl)piperazine-1-carboxamido)methyl)nicotinate hydrochloride (0.249 g, 0.585 mmol), oxetan-3-one (0.051 mL, 0.878 mmol) and sodium triacetoxyborohydride (0.186 g, 0.878 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((N-(4-chlorophenyl)-4-(oxetan-3-yl)piperazine-1-carboxamido) methyl)nicotinate, 0.260 g, 99.8 To, pale yellow oil).

[Step 4] N-(4-Chlorophenyl)-N-((5-(hydrazinecarbonyl)pyridin-2-yl)methyl)-4-(oxetan-3-yl)piperazine-1-carboxamide

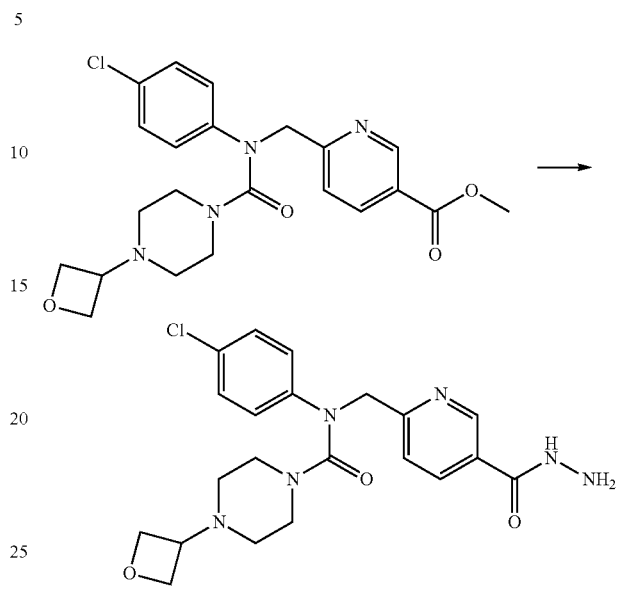

Methyl 6-((N-(4-chlorophenyl)-4-(oxetan-3-yl)piperazine-1-carboxamido)methyl)nicotinate (0.260 g, 0.584 mmol) and hydrazine monohydrate (0.568 mL, 11.687 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO₂, 4 g cartridge; methanol/dichloromethane=0% to 10%) to give N-(4-chlorophenyl)-N-((5-(hydrazinecarbonyl)pyridin-2-yl)methyl)-4-(oxetan-3-yl)piperazine-1-carboxamide as orange solid (0.121 g, 46.3%).

[Step 5] Compound 21947

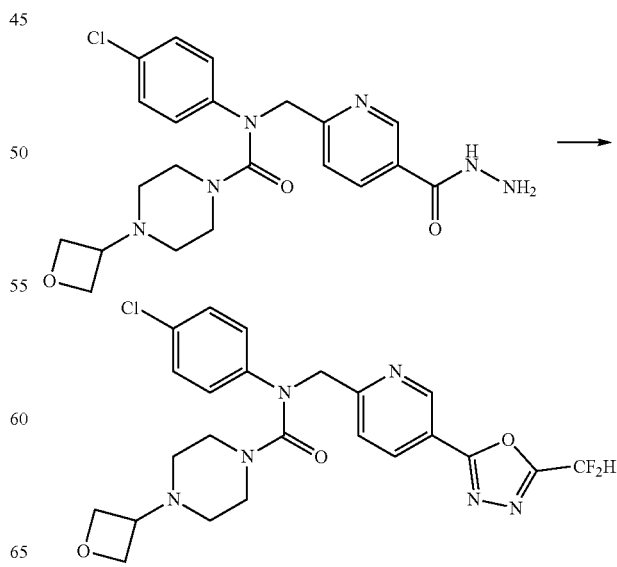

N-(4-Chlorophenyl)-N-((5-(hydrazinecarbonyl)pyridin-2-yl)methyl)-4-(oxetan-3-yl)piperazine-1-carboxamide (0.121 g, 0.271 mmol), triethylamine (0.113 mL, 0.813 mmol) and 2,2-difluoroacetic anhydride (0.101 mL, 0.813 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-chlorophenyl)-N-((5-(5-(difluoromethyl)-1,3,4-oxadiazol-2-yl)pyridin-2-yl)methyl)-4-(oxetan-3-yl)piperazine-1-carboxamide as pale yellow solid (0.030 g, 21.6%).

$^1$H NMR (400 MHz, CDCl$_3$) δ 9.15 (d, 1H, J=2.1 Hz), 8.27 (dd, 1H, J=8.1, 2.3 Hz), 7.50 (d, 1H, J=8.2 Hz), 7.20 (d, 2H, J=7.0 Hz), 7.03 (d, 2H, J=8.3 Hz), 6.87 (t, 1H, J=51.6 Hz), 5.01 (s, 2H), 4.62-4.54 (m, 4H), 3.34 (brs, 5H), 2.23 (s, 4H); LRMS (ES) m/z 505.3 (M$^+$+1).

Example 392. Compound 21948: N-(4-(5-(Difluoromethyl)-1,3,4-oxadiazol-2-yl)benzyl)-N-(3-methoxyphenyl)-4-(oxetan-3-yl)piperazine-1-carboxamide

[Step 1] Tert-Butyl 4-((3-methoxyphenyl)carbamoyl)piperazine-1-carboxylate

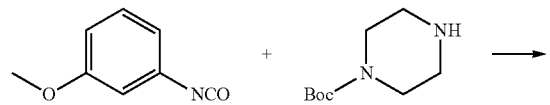

A solution of 1-isocyanato-3-methoxybenzene (0.514 mL, 4.000 mmol) and tert-butyl piperazine-1-carboxylate (0.745 g, 4.000 mmol) in diethylether (10 mL) prepared at the room temperature was stirred at the same temperature for 3 hr, and concentrated under the reduced pressure. The title compound was used without further purification (tert-butyl 4-((3-methoxyphenyl)carbamoyl)piperazine-1-carboxylate, 1.340 g, 99.9%, white solid).

[Step 2] Tert-Butyl 4-((4-(methoxycarbonyl)benzyl)(3-methoxyphenyl)carbamoyl)piperazine-1-carboxylate

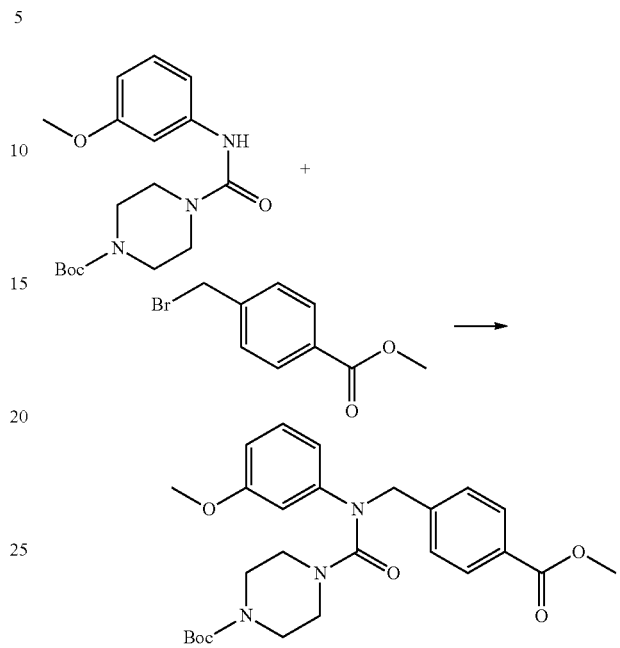

A solution of tert-butyl 4-((3-methoxyphenyl)carbamoyl)piperazine-1-carboxylate (0.527 g, 1.572 mmol) and sodium hydride (60.00%, 0.094 g, 2.358 mmol) in tetrahydrofuran (6 mL) was stirred at the room temperature for 30 min, and mixed with methyl 4-(bromomethyl)benzoate (0.396 g, 1.729 mmol). The reaction mixture was stirred at the same temperature for additional 18 hr, and concentrated under the reduced pressure. The concentrate was purified and concentrated by column chromatography (SiO$_1$, 12 g cartridge; ethyl acetate/hexane=0% to 50%) to give tert-butyl 4-((4-(methoxycarbonyl)benzyl)(3-methoxyphenyl)carbamoyl)piperazine-1-carboxylat e as white solid (0.582 g, 76.6%).

[Step 3] Methyl 4-((N-(3-methoxyphenyl)piperazine-1-carboxamido)methyl)benzoate hydrochloride

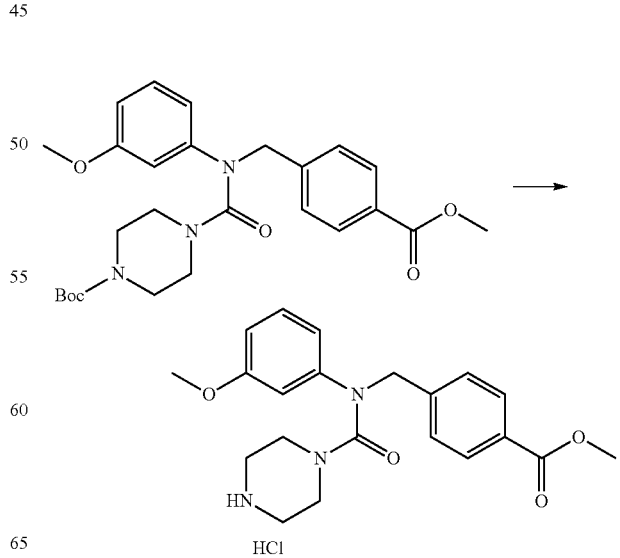

A solution of tert-butyl 4-((4-(methoxycarbonyl)benzyl)(3-methoxyphenyl)carbamoyl)piperazine-1-carboxylate (0.582 g, 1.204 mmol) and hydrogen chloride (4.00 M solution in 1,4-dioxane, 1.204 mL, 4.814 mmol) in dichloromethane (5 mL) was stirred at the room temperature for 18 hr, and concentrated under the reduced pressure. The title compound was used without further purification (methyl 4-((N-(3-methoxyphenyl)piperazine-1-carboxamido)methyl)benzoate hydrochloride, 0.505 g, 99.9%, pale yellow solid).

[Step 4] Methyl 4-((N-(3-methoxyphenyl)-4-(oxetan-3-yl)piperazine-1-carboxamido)methyl)benzoate

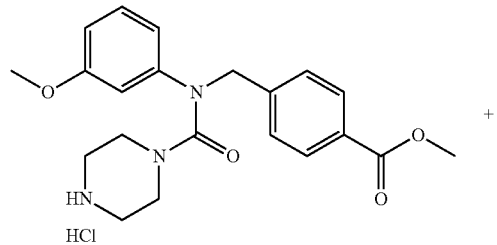

+

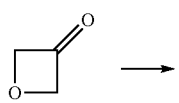

→

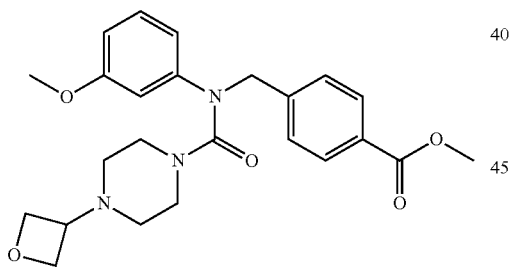

A solution of methyl 4-((N-(3-methoxyphenyl)piperazine-1-carboxamido)methyl)benzoate hydrochloride (0.505 g, 1.203 mmol), oxetan-3-one (0.106 mL, 1.804 mmol) and sodium triacetoxyborohydride (0.382 g, 1.804 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give methyl 4-((N-(3-methoxyphenyl)-4-(oxetan-3-yl)piperazine-1-carboxamido)methyl)benzoate as colorless oil (0.443 g, 83.8%).

[Step 5] N-(4-(hydrazinecarbonyl)benzyl)-N-(3-methoxyphenyl)-4-(oxetan-3-yl)piperazine-1-carboxamide

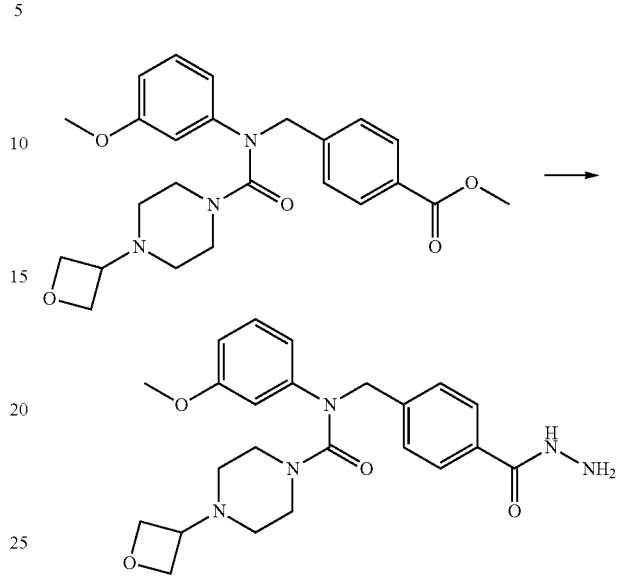

Methyl 4-((N-(3-methoxyphenyl)-4-(oxetan-3-yl)piperazine-1-carboxamido)methyl)benzoate (0.443 g, 1.008 mmol) and hydrazine monohydrate (0.980 mL, 20.159 mmol) were mixed at the room temperature in ethanol (5 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(4-(hydrazinecarbonyl)benzyl)-N-(3-methoxyphenyl)-4-(oxetan-3-yl)piperazine-1-carboxamide as white solid (0.308 g, 69.5%).

[Step 6] Compound 21948

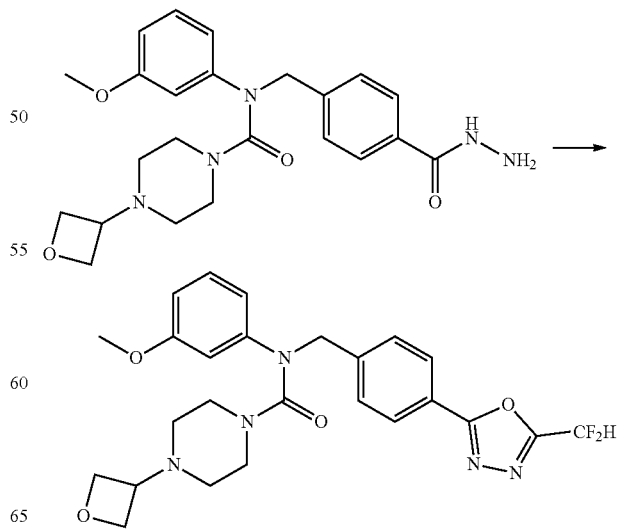

N-(4-(hydrazinecarbonyl)benzyl)-N-(3-methoxyphenyl)-4-(oxetan-3-yl)piperazine-1-carboxamide (0.308 g, 0.700 mmol), triethylamine (0.293 mL, 2.100 mmol) and 2,2-difluoroacetic anhydride (0.261 mL, 2.100 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)benzyl)-N-(3-methoxyphenyl)-4-(oxetan-3-yl)piperazine-1-carboxamide as white solid (0.058 g, 16.6%).

$^1$H NMR (400 MHz, CDCl$_3$) δ 7.99-7.91 (m, 2H), 7.40 (d, 2H, J=8.0 Hz), 7.12 (t, 1H, J=8.2 Hz), 7.00-6.67 (m, 1H), 6.57 (t, 2H, J=7.6 Hz), 6.52-6.48 (m, 1H), 4.85 (s, 2H), 4.59-4.48 (m, 4H), 3.68 (d, 3H, J=1.6 Hz), 3.38 (s, 1H), 3.29 (s, 4H), 2.13 (s, 4H); LRMS (ES) m/z 500.3 (M$^+$+1).

Example 393. Compound 21949: N-(4-(5-(Difluoromethyl)-1,3,4-oxadiazol-2-yl)-2-fluorobenzyl)-N-(3-methoxyphenyl)-4-(oxetan-3-yl)piperazine-1-carboxamide

[Step 1] Tert-Butyl 4-((2-fluoro-4-(methoxycarbonyl)benzyl)(3-methoxyphenyl)carbamoyl)piperazine-1-carboxylate

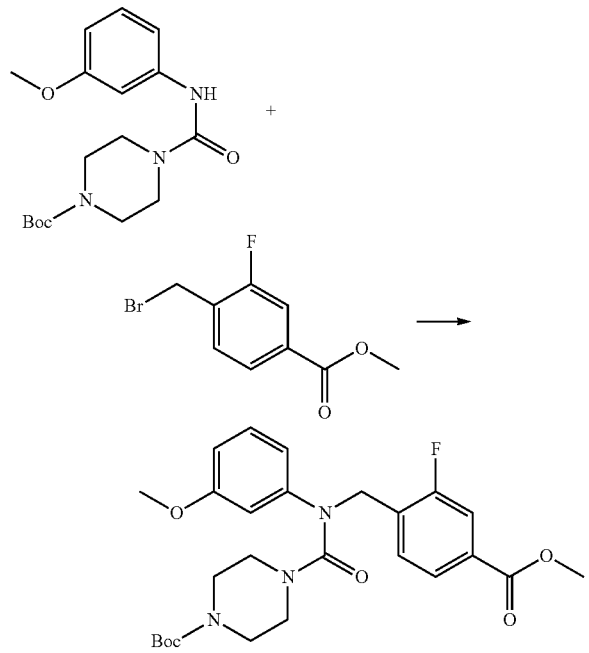

solution of tert-butyl 4-((3-methoxyphenyl)carbamoyl)piperazine-1-carboxylate (0.447 g, 1.333 mmol) and sodium hydride (60.00%, 0.080 g, 1.999 mmol) in tetrahydrofuran (6 mL) was stirred at the room temperature for 30 min, and mixed with methyl 4-(bromomethyl)-3-fluorobenzoate (0.362 g, 1.466 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((2-fluoro-4-(methoxycarbonyl)benzyl)(3-methoxyphenyl)carbamoyl)piperazine-1-carboxylate as colorless oil (0.397 g, 59.5%).

[Step 2] Methyl 3-fluoro-4-((N-(3-methoxyphenyl)piperazine-1-carboxamido)methyl)benzoate hydrochloride

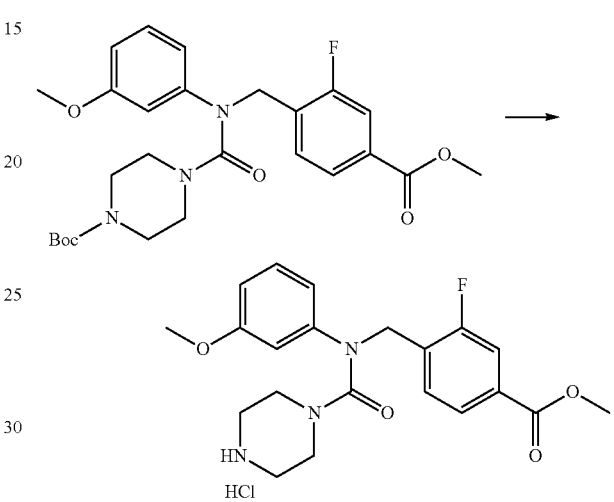

A solution of tert-butyl 4-((2-fluoro-4-(methoxycarbonyl)benzyl)(3-methoxyphenyl)carbamoyl)piperazine-1-carboxylate (0.397 g, 0.792 mmol) and hydrogen chloride (4.00 M solution in 1,4-dioxane, 0.792 mL, 3.169 mmol) in dichloromethane (4 mL) prepared at the room temperature was stirred at the same temperature for 18 hr, and concentrated under the reduced pressure. The title compound was used without further purification (methyl 3-fluoro-4-((N-(3-methoxyphenyl)piperazine-1-carboxamido)methyl)benzoate hydrochloride, 0.346 g, 99.7%, pale yellow solid).

[Step 3] Methyl 3-fluoro-4-((N-(3-methoxyphenyl)-4-(oxetan-3-yl)piperazine-1-carboxamido)methyl)benzoate

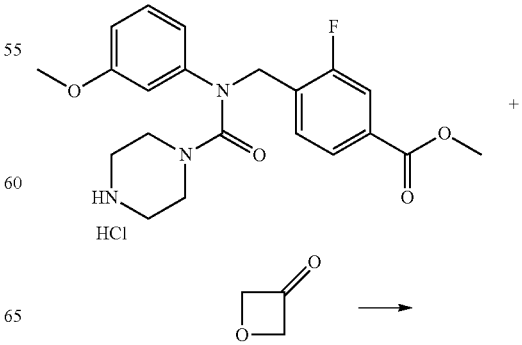

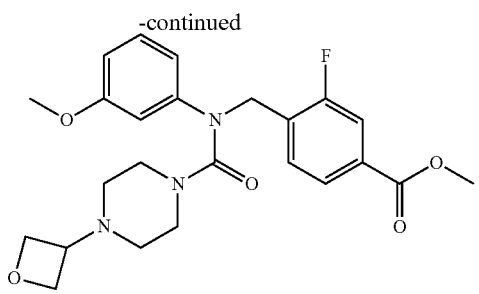

A solution of methyl 3-fluoro-4-((N-(3-methoxyphenyl)piperazine-1-carboxamido)methyl)benzoate hydrochloride (0.346 g, 0.790 mmol), oxetan-3-one (0.069 mL, 1.185 mmol) and sodium triacetoxyborohydride (0.251 g, 1.185 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 3-fluoro-4-((N-(3-methoxyphenyl)-4-(oxetan-3-yl)piperazine-1-carboxamido)methyl)benzoate, 0.361 g, 99.9%, pale yellow oil).

[Step 4] N-(2-Fluoro-4-(hydrazinecarbonyl)benzyl)-N-(3-methoxyphenyl)-4-(oxetan-3-yl)piperazine-1-carboxamide

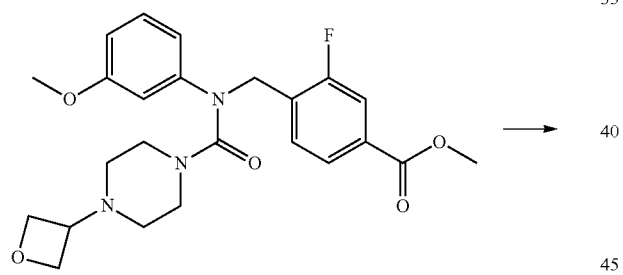

Methyl 3-fluoro-4-((N-(3-methoxyphenyl)-4-(oxetan-3-yl)piperazine-1-carboxamido)methyl)benzoate (0.361 g, 0.789 mmol) and hydrazine monohydrate (0.767 mL, 15.781 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(2-fluoro-4-(hydrazinecarbonyl)benzyl)-N-(3-methoxyphenyl)-4-(oxetan-3-yl)piperazine-1-carboxamide as white solid (0.354 g, 98.1%).

[Step 5] Compound 21949

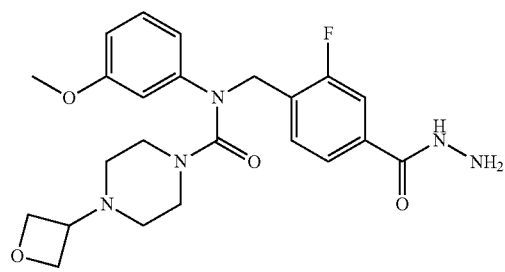

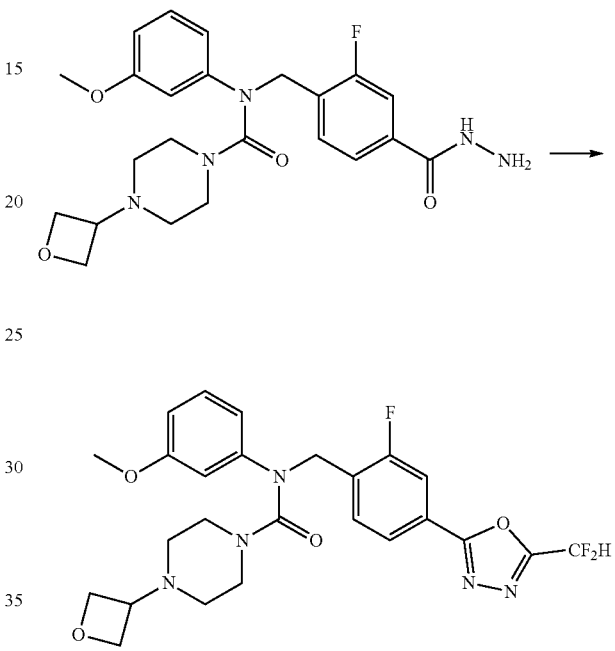

N-(2-fluoro-4-(hydrazinecarbonyl)benzyl)-N-(3-methoxyphenyl)-4-(oxetan-3-yl)piperazine-1-carboxamide (0.393 g, 0.859 mmol), triethylamine (0.359 mL, 2.576 mmol) and 2,2-difluoroacetic anhydride (0.320 mL, 2.576 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)-2-fluorobenzyl)-N-(3-methoxyphenyl)-4-(oxetan-3-yl)piperazine-1-carboxamide as pale yellow solid (0.106 g, 23.9%).

$^1$H NMR (400 MHz, CDCl$_3$) δ 7.77 (d, 1H, J=8.0 Hz), 7.67 (d, 1H, J=10.1 Hz), 7.59 (t, 1H, J=7.7 Hz), 7.17-7.05 (m, 1H), 7.01-6.68 (m, 1H), 6.63-6.54 (m, 3H), 4.89 (s, 2H), 4.58-4.44 (m, 4H), 3.69 (d, 3H, J=1.7 Hz), 3.41-3.31 (m, 1H), 3.32-3.13 (m, 4H), 2.26-1.95 (m, 4H); LRMS (ES) m/z 518.3 (M$^+$+1).

Example 394. Compound 21950: N-((5-(5-(Difluoromethyl)-1,3,4-oxadiazol-2-yl)pyridin-2-yl)methyl)-N-(3-methoxyphenyl)-4-(oxetan-3-yl)piperazine-1-carboxamide

[Step 1] Tert-Butyl 4-(((5-(methoxycarbonyl)pyridin-2-yl)methyl)(3-methoxyphenyl)carbamoyl)piperazine-1-carboxylate

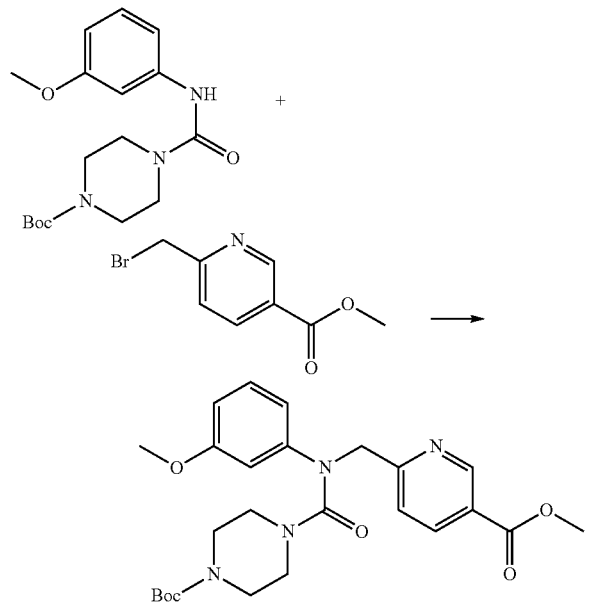

A solution of tert-butyl 4-((3-methoxyphenyl)carbamoyl)piperazine-1-carboxylate (0.447 g, 1.333 mmol) and sodium hydride (60.00%, 0.080 g, 1.999 mmol) in tetrahydrofuran (6 mL) was stirred at the room temperature for 30 min, and mixed with methyl 6-(bromomethyl)nicotinate (0.337 g, 1.466 mmol). The reaction mixture was stirred at the same temperature for additional 18 hr, and concentrated under the reduced pressure. The concentrate was purified and concentrated by column chromatography (SiO₂, 12 g cartridge; ethyl acetate/hexane=0% to 50%) to give tert-butyl 4-(((5-(methoxycarbonyl)pyridin-2-yl)methyl)(3-methoxyphenyl)carbamoyl)piperazine-1-carboxylate as pale yellow oil (0.315 g, 48.8%).

[Step 2] Methyl 6-((N-(3-methoxyphenyl)piperazine-1-carboxamido)methyl)nicotinate hydrochloride

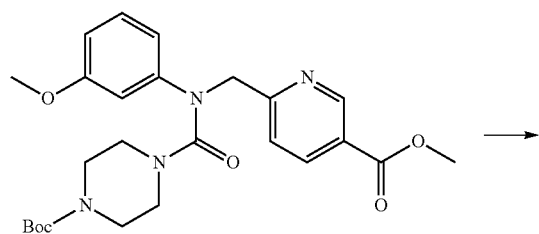

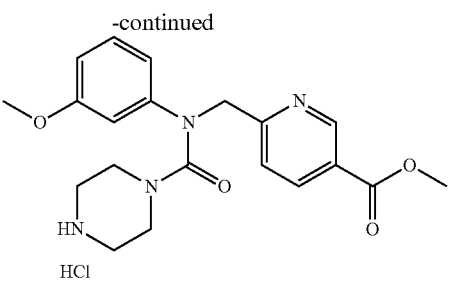

A solution of tert-butyl 4-(((5-(methoxycarbonyl)pyridin-2-yl)methyl)(3-methoxyphenyl)carbamoyl)piperazine-1-carboxylate (0.315 g, 0.650 mmol) and hydrogen chloride (4.00 M solution in 1,4-dioxane, 0.650 mL, 2.600 mmol) in dichloromethane (4 mL) prepared at the room temperature was stirred at the same temperature for 18 hr, and concentrated under the reduced pressure. The title compound was used without further purification (methyl 6-((N-(3-methoxyphenyl)piperazine-1-carboxamido)methyl)nicotinate hydrochloride, 0.273 g, 99.8%, pale yellow solid).

[Step 3] Methyl 6-((N-(3-methoxyphenyl)-4-(oxetan-3-yl)piperazine-1-carboxamido)methyl)nicotinate

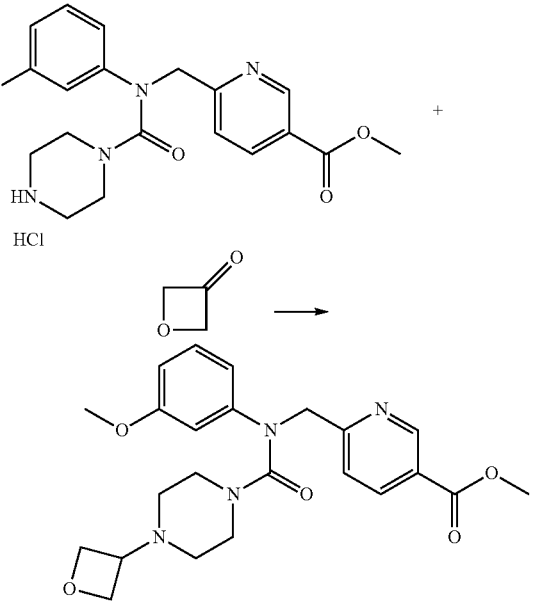

A solution of methyl 6-((N-(3-methoxyphenyl)piperazine-1-carboxamido)methyl)nicotinate hydrochloride (0.273 g, 0.649 mmol), oxetan-3-one (0.057 mL, 0.973 mmol) and sodium triacetoxyborohydride (0.206 g, 0.973 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer; and the organic layer collected was concentrated in vacuo. The title compound was used without further purification (methyl 6-((N-(3-methoxyphenyl)-4-(oxetan-3-yl)piperazine-1-carboxamido)methyl)nicotinate, 0.285 g, 99.7%, pale yellow oil).

[Step 4] N-((5-(hydrazinecarbonyl)pyridin-2-yl)methyl)-N-(3-methoxyphenyl)-4-(oxetan-3-yl)piperazine-1-carboxamide

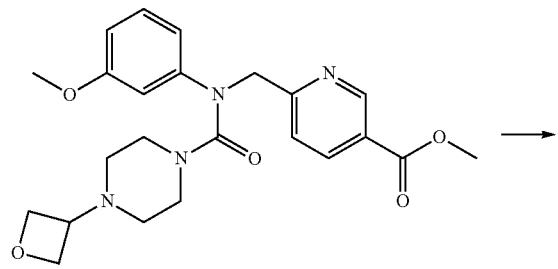

Methyl 6-((N-(3-methoxyphenyl)-4-(oxetan-3-yl)piperazine-1-carboxamido)methyl)nicotinate (0.285 g, 0.647 mmol) and hydrazine monohydrate (0.629 mL, 12.940 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-((5-(hydrazinecarbonyl)pyridin-2-yl)methyl)-N-(3-methoxyphenyl)-4-(oxetan-3-yl)piperazine-1-carboxamide as orange solid (0.183 g, 64.1%).

[Step 5] Compound 21950

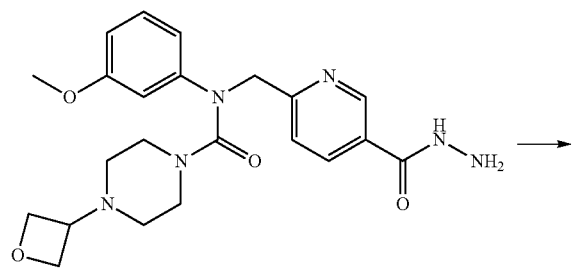

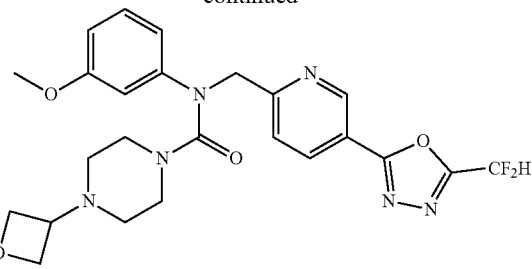

N-((5-(hydrazinecarbonyl)pyridin-2-yl)methyl)-N-(3-methoxyphenyl)-4-(oxetan-3-yl)piperazine-1-carboxamide (0.183 g, 0.415 mmol), triethylamine (0.174 mL, 1.245 mmol) and 2,2-difluoroacetic anhydride (0.155 mL, 1.245 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-((5-(5-(difluoromethyl)-1,3,4-oxadiazol-2-yl)pyridin-2-yl)methyl)-N-(3-methoxyphenyl)-4-(oxetan-3-yl)piperazine-1-carboxamide as pale yellow solid (0.072 g, 34.8%).
$^1$H NMR (400 MHz, CDCl$_3$) δ 9.15 (s, 1H), 8.25 (dd, 1H, J=8.2, 2.0 Hz), 7.51 (d, 1H, J=8.2 Hz), 7.22-7.09 (m, 1H), 7.03-6.70 (m, 1H), 6.69-6.53 (m, 3H), 5.03 (5, 2H), 4.61-4.52 (m, 4H), 3.70 (d, 3H, J=1.5 Hz), 3.42 (s, 1H), 3.33 (s, 4H), 2.18 (s, 4H); LRMS (ES) m/z 501.2 (M$^+$+1).

Example 395. Compound 21951: N-(4-(5-(Difluoromethyl)-1,3,4-oxadiazol-2-yl)benzyl)-N-(4-methoxyphenyl)-4-(oxetan-3-yl)piperazine-1-carboxamide

[Step 1] Tert-Butyl 4-((4-methoxyphenyl)carbamoyl)piperazine-1-carboxylate

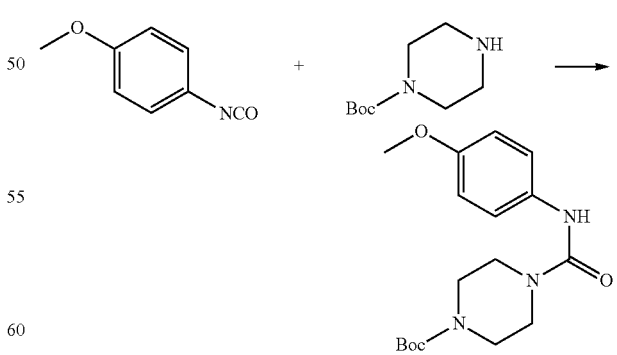

A solution of 1-isocyanato-4-methoxybenzene (0.514 mL, 4.000 mmol) and tert-butyl piperazine-1-carboxylate (0.745 g, 4.000 mmol) in diethylether (10 mL) prepared at the room temperature was stirred at the same temperature for 3 hr, and concentrated under the reduced pressure. The title compound was used without further purification (tert-butyl 4-((4-methoxyphenyl)carbamoyl)piperazine-1-carboxylate, 1.340 g, 99.9%, white solid).

[Step 2] Tert-Butyl 4-((4-(methoxycarbonyl)benzyl)(4-methoxyphenyl)carbamoyl)piperazine-1-carboxylate

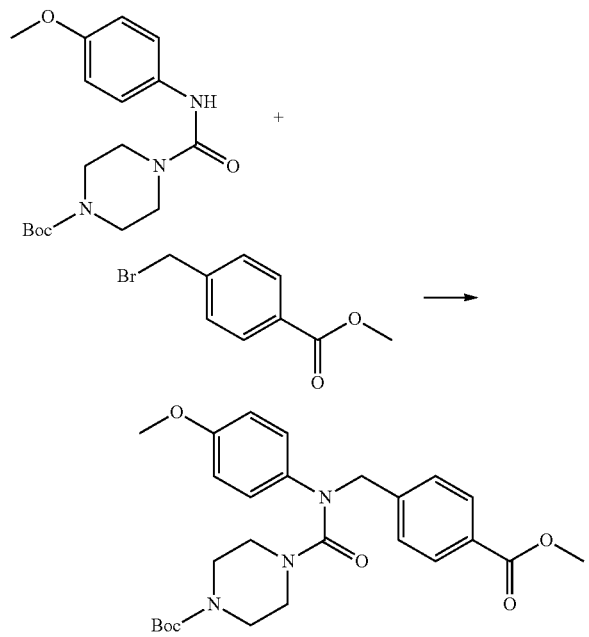

A solution of tert-butyl 4-((4-methoxyphenyl)carbamoyl)piperazine-1-carboxylate (0.420 g, 1.253 mmol) and sodium hydride (60.00%, 0.075 g, 1.879 mmol) in tetrahydrofuran (6 mL) was stirred at the room temperature for 30 min, and mixed with methyl 4-(bromomethyl)benzoate (0.316 g, 1.378 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tentbutyl 4-((4-(methoxycarbonyl)benzyl)(4-methoxyphenyl)carbamoyl)piperazine-1-carboxylat e as white solid (0.440 g, 72.7%).

[Step 3] Methyl 4-((N-(4-methoxyphenyl)piperazine-1-carboxamido)methyl)benzoate hydrochloride

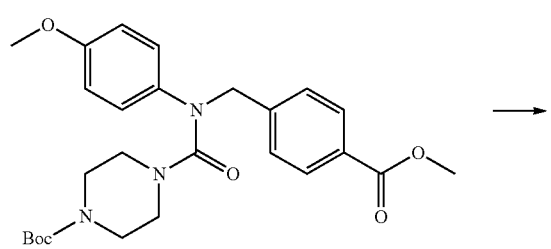

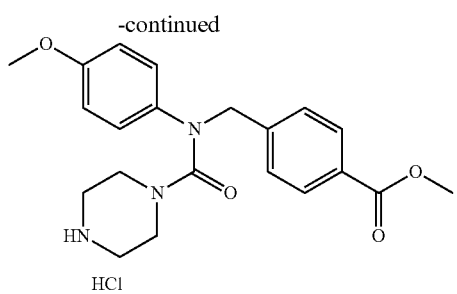

A solution of tert-butyl 4-((4-(methoxycarbonyl)benzyl)(4-methoxyphenyl)carbamoyl)piperazine-1-carboxylat e (0.440 g, 0.910 mmol) and hydrogen chloride (4.00 M solution in 1,4-dioxane, 0.910 mL, 3.640 mmol) in dichloromethane (5 mL) prepared at the room temperature was stirred at the same temperature for 18 hr, and concentrated under the reduced pressure. The title compound was used without further purification (methyl 4-((N-(4-methoxyphenyl)piperazine-1-carboxamido)methyl)benzoate hydrochloride, 0.381 g, 99.7%, pale yellow solid).

[Step 4] Methyl 4-((N-(4-methoxyphenyl)-4-(oxetan-3-yl)piperazine-1-carboxamido)methyl)benzoate

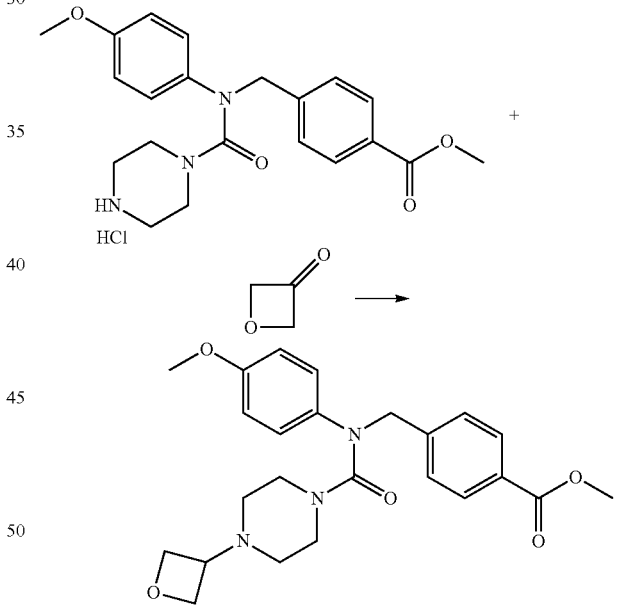

A solution of methyl 4-((N-(4-methoxyphenyl)piperazine-1-carboxamido)methyl)benzoate hydrochloride (0.381 g, 0.907 mmol), oxetan-3-one (0.080 mL, 1.361 mmol) and sodium triacetoxyborohydride (0.288 g, 1.361 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to

1205 give methyl 4-((N-(4-methoxyphenyl)-4-(oxetan-3-yl)piperazine-1-carboxamido)methyl)benzoate as colorless oil (0.380 g, 95.4%).

[Step 5] N-(4-(hydrazinecarbonyl)benzyl)-N-(4-methoxyphenyl)-4-(oxetan-3-yl)piperazine-1-carboxamide

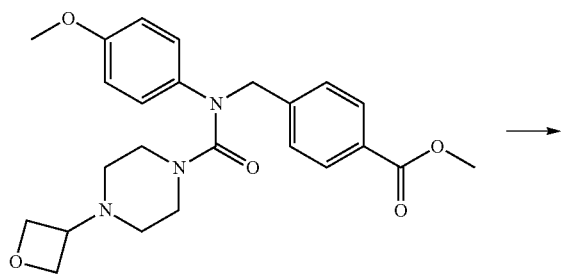

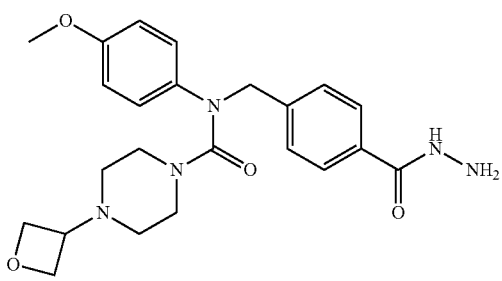

Methyl 4-((N-(4-methoxyphenyl)-4-(oxetan-3-yl)piperazine-1-carboxamido)methyl)benzoate (0.380 g, 0.865 mmol) and hydrazine monohydrate (0.840 mL, 17.292 mmol) were mixed at the room temperature in ethanol (5 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(4-(hydrazinecarbonyl)benzyl)-N-(4-methoxyphenyl)-4-(oxetan-3-yl)piperazine-1-carboxamide as white solid (0.147 g, 38.8%).

[Step 6] Compound 21951

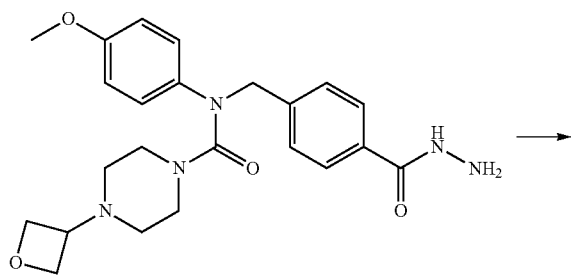

1206

-continued

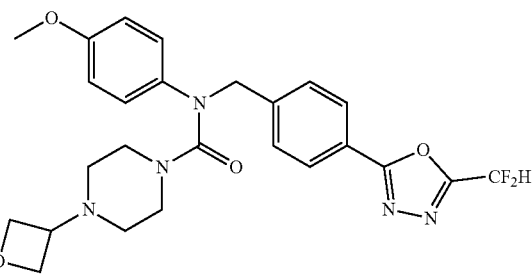

N-(4-(hydrazinecarbonyl)benzyl)-N-(4-methoxyphenyl)-4-(oxetan-3-yl)piperazine-1-carboxamide (0.147 g, 0.335 mmol), triethylamine (0.140 mL, 1.006 mmol) and 2,2-difluoroacetic anhydride (0.125 mL, 1.006 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)benzyl)-N-(4-methoxyphenyl)-4-(oxetan-3-yl)piperazine-1-carboxamide as white solid (0.088 g, 52.8%).

$^1$H NMR (400 MHz, CDCl$_3$) δ 7.97-7.90 (m, 2H), 7.37 (d, 2H, J=7.9 Hz), 7.00-6.67 (m, 5H), 4.78 (s, 2H), 4.58-4.47 (m, 4H), 3.71 (d, 3H, J=1.5 Hz), 3.37 (s, 1H), 3.25 (s, 4H), 2.13-2.06 (m, 4H); LRMS (ES) m/z 500.5 (M$^+$+1).

Example 396. Compound 21952: N-(4-(5-(Difluoromethyl)-1,3,4-oxadiazol-2-yl)-2-fluorobenzyl)-N-(4-methoxyphenyl)-4-(oxetan-3-yl)piperazine-1-carboxamide

[Step 1] Tert-Butyl 4-((2-fluoro-4-(methoxycarbonyl)benzyl)(4-methoxyphenyl)carbamoyl)piperazine-1-carboxylate

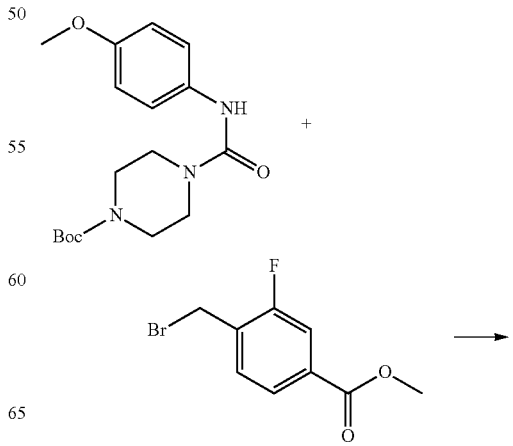

1207

-continued

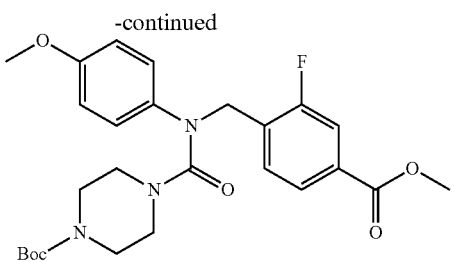

A solution of tert-butyl 4-((4-methoxyphenyl)carbamoyl)piperazine-1-carboxylate (0.447 g, 1.333 mmol) and sodium hydride (60.00%, 0.080 g, 1.999 mmol) in tetrahydrofuran (6 mL) was stirred at the room temperature for 30 min, and mixed with methyl 4-(bromomethyl)-3-fluorobenzoate (0.362 g, 1.466 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((2-fluoro-4-(methoxycarbonyl)benzyl)(4-methoxyphenyl)carbamoyl)piperazine-1-carboxylate as pale yellow oil (0.333 g, 49.9%).

[Step 2] Methyl 3-fluoro-4-((N-(4-methoxyphenyl)piperazine-1-carboxamido)methyl)benzoate hydrochloride

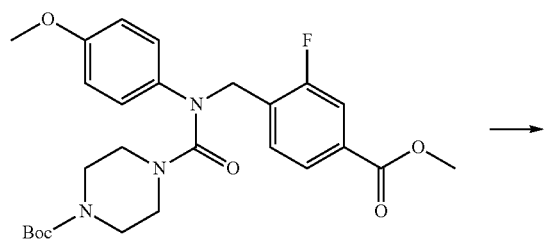

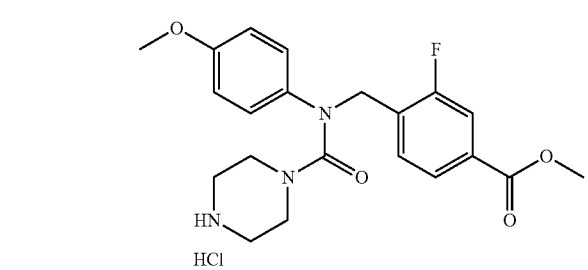

A solution of tert-butyl 4-((2-fluoro-4-(methoxycarbonyl)benzyl)(4-methoxyphenyl)carbamoyl)piperazine-1-carboxylate (0.333 g, 0.665 mmol) and hydrogen chloride (4.00 M solution in 1,4-dioxane, 0.665 mL, 2.658 mmol) in dichloromethane (4 mL) was stirred at the room temperature for 18 hr, and concentrated under the reduced pressure. The title compound was used without further purification (methyl 3-fluoro-4-((N-(4-methoxyphenyl)piperazine-1-carboxamido)methyl)benzoate hydrochloride, 0.290 g, 99.7%, pale yellow solid).

1208

[Step 3] Methyl 3-fluoro-4-((N-(4-methoxyphenyl)-4-(oxetan-3-yl)piperazine-1-carboxamido)methyl)benzoate

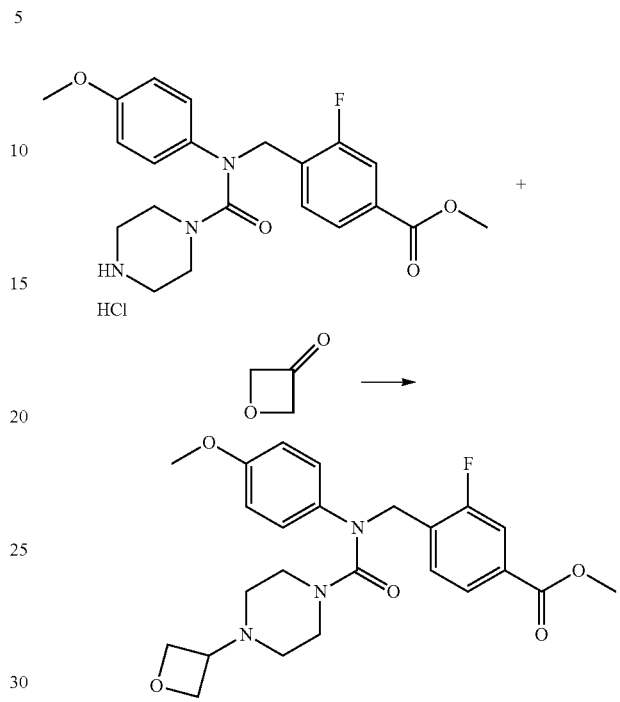

A solution of methyl 3-fluoro-4-((N-(4-methoxyphenyl)piperazine-1-carboxamido)methyl)benzoate hydrochloride (0.290 g, 0.662 mmol), oxetan-3-one (0.058 mL, 0.993 mmol) and sodium triacetoxyborohydride (0.211 g, 0.993 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 3-fluoro-4-((N-(4-methoxyphenyl)-4-(oxetan-3-yl)piperazine-1-carboxamido)methyl)benzoate, 0.302 g, 99.7%, pale yellow oil).

[Step 4] N-(2-Fluoro-4-(hydrazinecarbonyl)benzyl)-N-(4-methoxyphenyl)-4-(oxetan-3-yl)piperazine-1-carboxamide

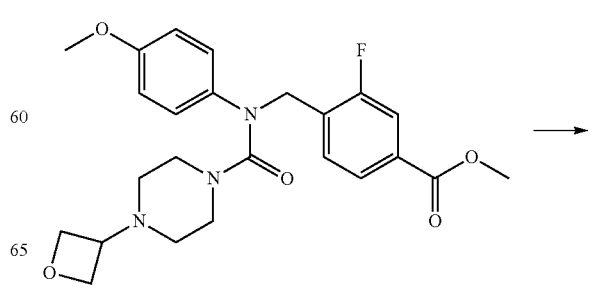

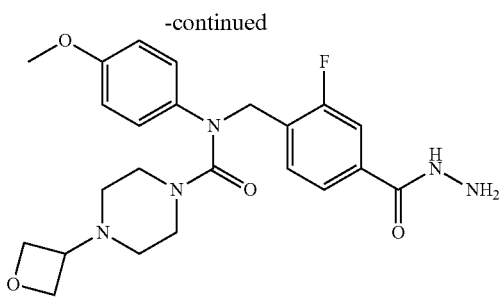

Methyl 3-fluoro-4-((N-(4-methoxyphenyl)-4-(oxetan-3-yl)piperazine-1-carboxamido)methyl)benzoate (0.302 g, 0.660 mmol) and hydrazine monohydrate (0.642 mL, 13.202 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(2-fluoro-4-(hydrazinecarbonyl)benzyl)-N-(4-methoxyphenyl)-4-(oxetan-3-yl)piperazine-1-carboxamide as white solid (0.109 g, 36.2%).

[Step 5] Compound 21952

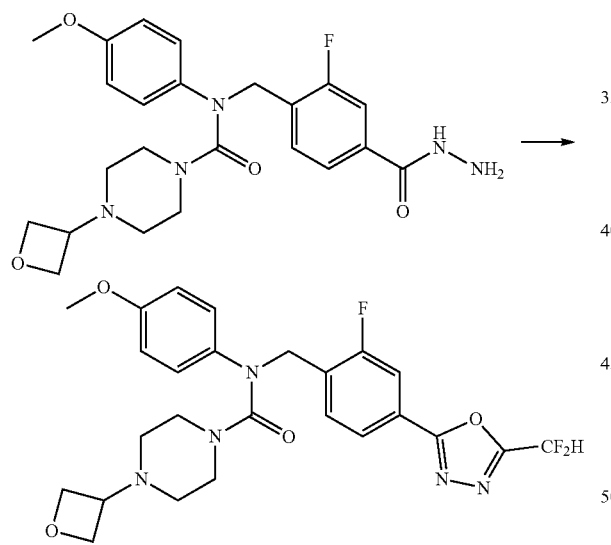

N-(2-Fluoro-4-(hydrazinecarbonyl)benzyl)-N-(4-methoxyphenyl)-4-(oxetan-3-yl)piperazine-1-carboxamide (0.109 g, 0.239 mmol), triethylamine (0.100 mL, 0.717 mmol) and 2,2-difluoroacetic anhydride (0.089 mL, 0.717 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)-2-fluorobenzyl)-N-(4-methoxyphenyl)-4-(oxetan-3-yl)piperazine-1-carboxamide as white solid (0.071 g, 57.5%).

$^1$H NMR (400 MHz, CDCl$_3$) δ 7.78 (d, 1H, J=8.0 Hz), 7.68-7.57 (m, 2H), 7.01-6.66 (m, 5H), 4.82 (s, 2H), 4.58-4.48 (m, 4H), 3.71 (d, 3H, J=1.5 Hz), 3.38 (s, 3H), 3.25 (s, 4H), 2.10 (s, 4H); LRMS (ES) m/z 518.4 (M$^+$+1).

Example 397. Compound 21953: N-((5-(5-(Difluoromethyl)-1,3,4-oxadiazol-2-yl)pyridin-2-yl)methyl)-N-(4-methoxyphenyl)-4-(oxetan-3-yl)piperazine-1-carboxamide

[Step 1] Tert-Butyl 4-(((5-(methoxycarbonyl)pyridin-2-yl)methyl)(4-methoxyphenyl)carbamoyl)piperazine-1-carboxylate

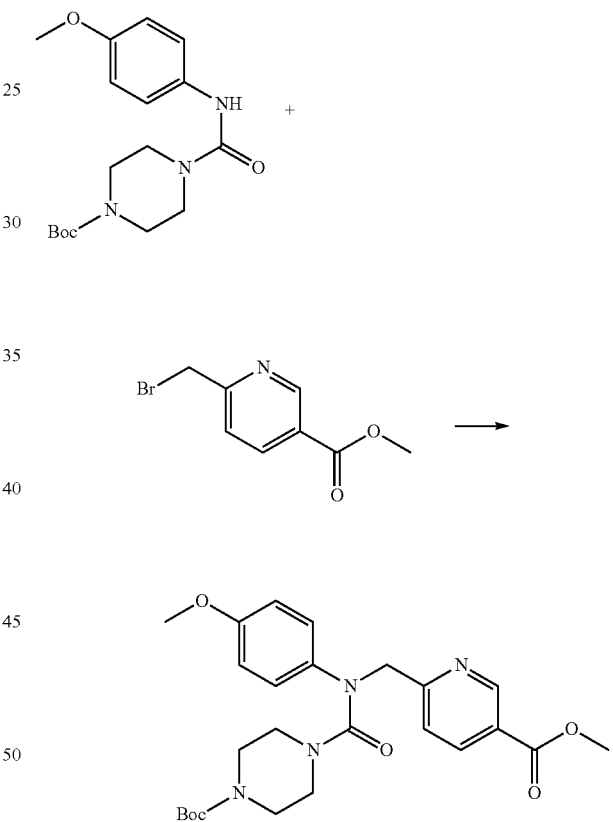

A solution of tert-butyl 4-((4-methoxyphenyl)carbamoyl)piperazine-1-carboxylate (0.447 g, 1.333 mmol) and sodium hydride (60.00%, 0.080 g, 1.999 mmol) in tetrahydrofuran (6 mL) was stirred at the room temperature for 30 min, and mixed with methyl 6-(bromomethyl)nicotinate (0.337 g, 1.466 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-(((5-(methoxycarbonyl)pyridin-2-yl)methyl)(4-methoxyphenyl)carbamoyl)piperazine-1-carboxylate as pale brown oil (0.320 g, 49.5%).

[Step 2] Methyl 6-((N-(4-methoxyphenyl)piperazine-1-carboxamido)methyl)nicotinate hydrochloride

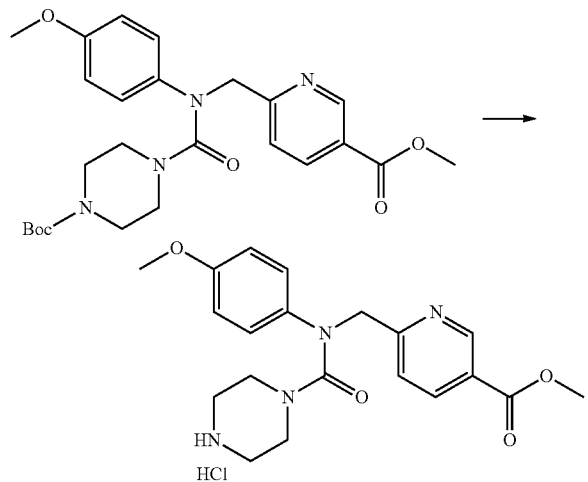

A solution of tert-butyl 4-(((5-(methoxycarbonyl)pyridin-2-yl)methyl)(4-methoxyphenyl)carbamoyl)piperazine-1-carboxylate (0.320 g, 0.660 mmol) and hydrogen chloride (4.00 M solution in 1,4-dioxane, 0.660 mL, 2.641 mmol) in dichloromethane (4 mL) prepared at the room temperature was stirred at the same temperature for 18 hr, and concentrated under the reduced pressure. The title compound was used without further purification (methyl 6-((N-(4-methoxyphenyl)piperazine-1-carboxamido)methyl)nicotinate hydrochloride, 0.277 g, 99.7%, pale yellow solid).

[Step 3] Methyl 6-((N-(4-methoxyphenyl)-4-(oxetan-3-yl)piperazine-1-carboxamido)methyl)nicotinate

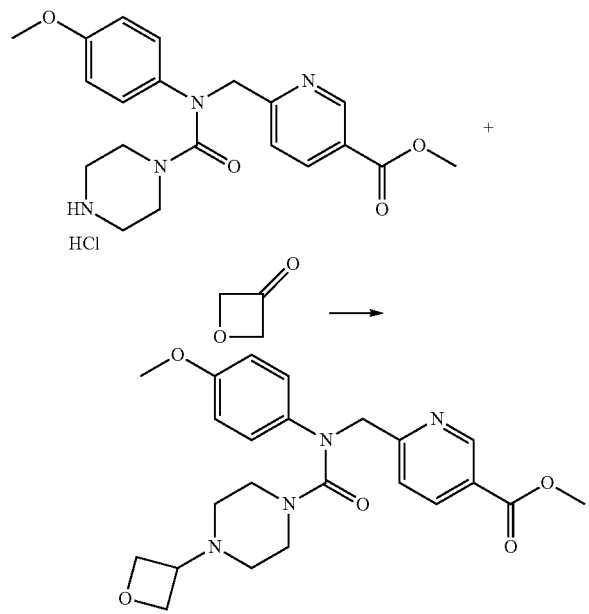

A solution of methyl 6-((N-(4-methoxyphenyl)piperazine-1-carboxamido)methyl)nicotinate hydrochloride (0.277 g, 0.658 mmol), oxetan-3-one (0.058 mL, 0.987 mmol) and sodium triacetoxyborohydride (0.209 g, 0.987 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 6-((N-(4-methoxyphenyl)-4-(oxetan-3-yl)piperazine-1-carboxamido)methyl)nicotinate, 0.289 g, 99.7%, pale yellow oil).

[Step 4] N-((5-(hydrazinecarbonyl)pyridin-2-yl)methyl)-N-(4-methoxyphenyl)-4-(oxetan-3-yl)piperazine-1-carboxamide

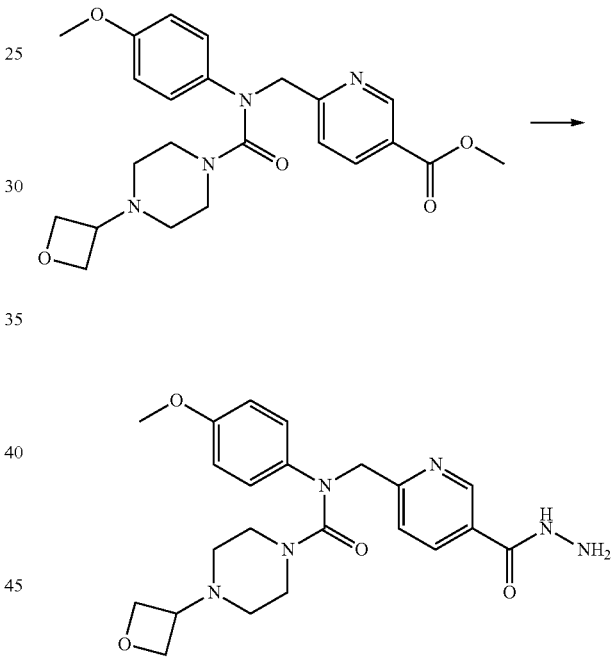

Methyl 6-((N-(4-methoxyphenyl)-4-(oxetan-3-yl)piperazine-1-carboxamido)methyl)nicotinate (0.289 g, 0.656 mmol) and hydrazine monohydrate (0.638 mL, 13.121 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-((5-(hydrazinecarbonyl)pyridin-2-yl)methyl)-N-(4-methoxyphenyl)-4-(oxetan-3-yl)piperazine-1-carboxamide as orange solid (0.174 g, 60.3%).

1213

[Step 5] Compound 21953

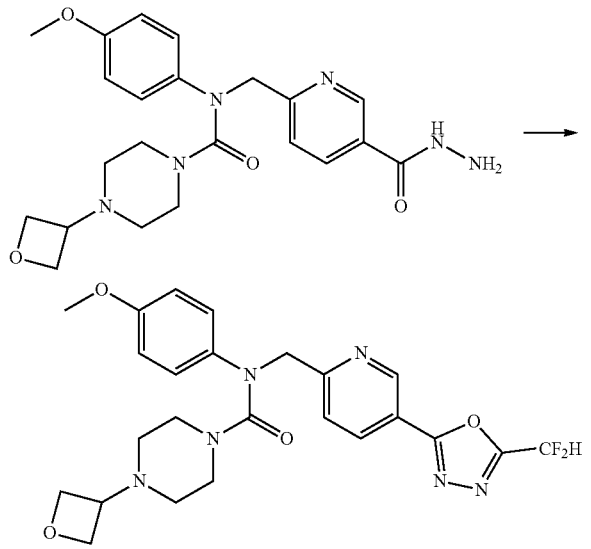

N-((5-(hydrazinecarbonyl)pyridin-2-yl)methyl)-N-(4-methoxyphenyl)-4-(oxetan-3-yl)piperazine-1-carboxamide (0.174 g, 0.396 mmol), triethylamine (0.165 mL, 1.187 mmol) and 2,2-difluoroacetic anhydride (0.148 mL, 1.187 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-((5-(5-(difluoromethyl)-1,3,4-oxadiazol-2-yl)pyridin-2-yl)methyl)-N-(4-methoxyphenyl)-4-(oxetan-3-yl)piperazine-1-carboxamide as pale yellow solid (0.062 g, 31.4%).

$^1$H NMR (400 MHz, CDCl$_3$) δ 9.21 (d, 1H, J=2.4 Hz), 8.33 (dd, 1H, J=8.2, 2.1 Hz), 7.63 (d, 1H, J=8.2 Hz), 7.16-6.73 (m, 5H), 5.06 (s, 2H), 4.68-4.60 (m, 4H), 3.79 (d, 3H, J=1.7 Hz), 3.49 (s, 1H), 3.37 (s, 4H), 2.24 (s, 4H); LRMS (ES) m/z 501.3 (M$^+$+1).

Example 398. Compound 21954: N-(4-(5-(Difluoromethyl)-1,3,4-oxadiazol-2-yl)benzyl)-4-(oxetan-3-yl)-N-phenylpiperazine-1-carboxamide

[Step 1] Tert-Butyl 4-(phenylcarbamoyl)piperazine-1-carboxylate

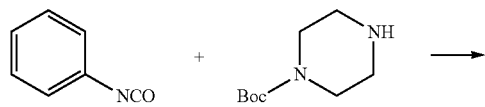

1214

-continued

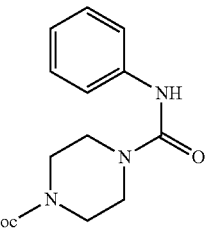

A solution of isocyanatobenzene (0.435 mL, 4.000 mmol) and tert-butyl piperazine-1-carboxylate (0.745 g, 4.000 mmol) in diethylether (10 mL) prepared at the room temperature was stirred at the same temperature for 3 hr, and concentrated under the reduced pressure. The title compound was used without further purification (tert-butyl 4-(phenylcarbamoyl)piperazine-1-carboxylate, 1.220 g, 99.9%, white solid).

[Step 2] Tert-Butyl 4-((4-(methoxycarbonyl)benzyl)(phenyl)carbamoyl)piperazine-1-carboxylate

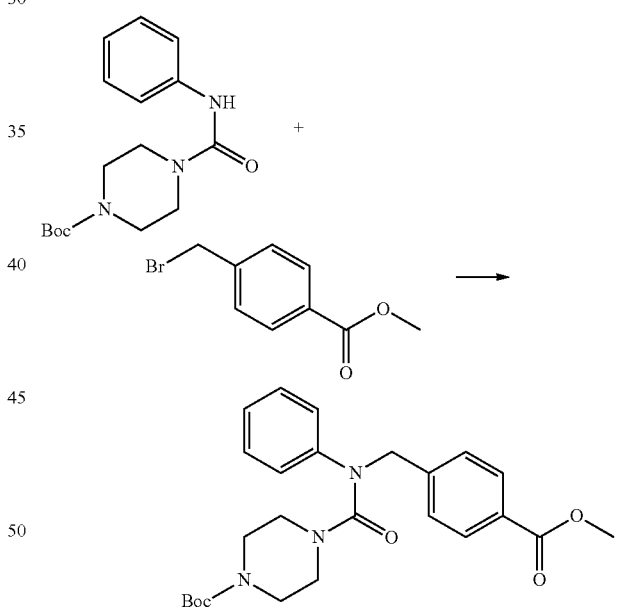

A solution of tert-butyl 4-(phenylcarbamoyl)piperazine-1-carboxylate (0.577 g, 1.889 mmol) and sodium hydride (60.00%, 0.113 g, 2.834 mmol) in tetrahydrofuran (6 mL) was stirred at the room temperature for 30 min, and mixed with methyl 4-(bromomethyl)benzoate (0.476 g, 2.078 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((4-(methoxycarbonyl)benzyl)(phenyl)carbamoyl)piperazine-1-carboxylate as white solid (0.671 g, 78.3%).

1215

[Step 3] Methyl 4-((N-phenylpiperazine-1-carboxamido)methyl)benzoate hydrochloride

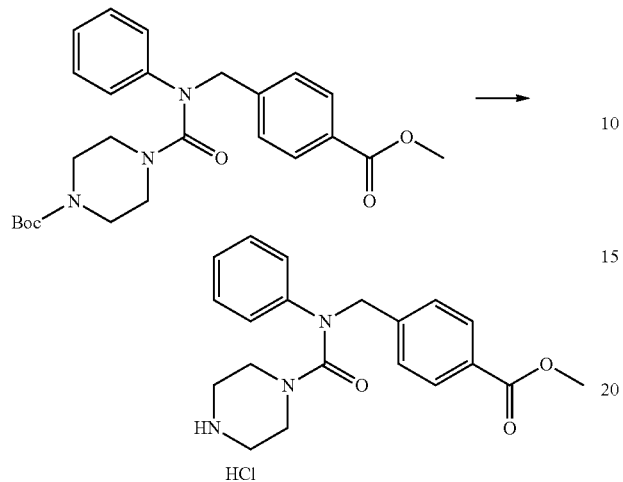

A solution of tert-butyl 4-((4-(methoxycarbonyl)benzyl)(phenyl)carbamoyl)piperazine-1-carboxylate (0.671 g, 1.479 mmol) and hydrogen chloride (4.00 M solution in 1,4-dioxane, 1.479 mL, 5.918 mmol) in dichloromethane (5 mL) prepared at the room temperature was stirred at the same temperature for 18 hr, and concentrated under the reduced pressure. The title compound was used without further purification (methyl 4-((N-phenylpiperazine-1-carboxamido)methyl)benzoate hydrochloride, 0.576 g, 99.9%, pale yellow solid).

[Step 4] Methyl 4-((4-(oxetan-3-yl)-N-phenylpiperazine-1-carboxamido)methyl)benzoate

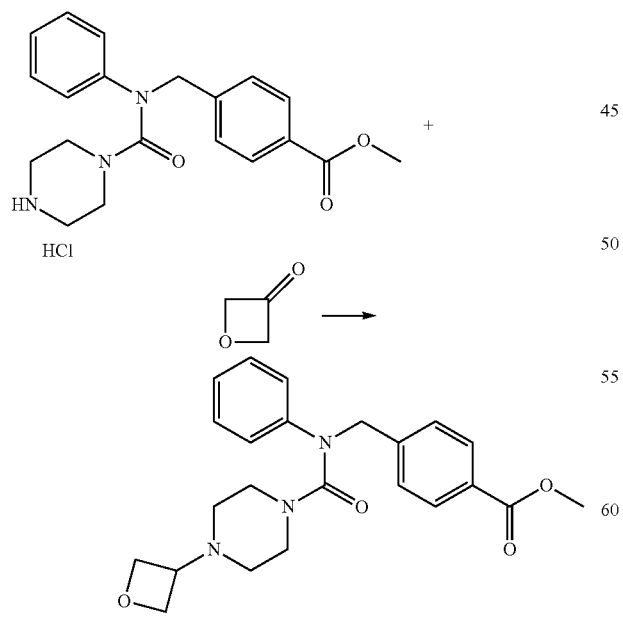

A solution of methyl 4-((N-phenylpiperazine-1-carboxamido)methyl)benzoate hydrochloride (0.576 g, 1.477 mmol), oxetan-3-one (0.130 mL, 2.216 mmol) and sodium triacetoxyborohydride (0.470 g, 2.216 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give methyl 4-((4-(oxetan-3-yl)-N-phenylpiperazine-1-carboxamido)methyl)benzoate as pale yellow oil (0.535 g, 88.4%).

[Step 5] N-(4-(hydrazinecarbonyl)benzyl)-4-(oxetan-3-yl)-N-phenylpiperazine-1-carboxamide

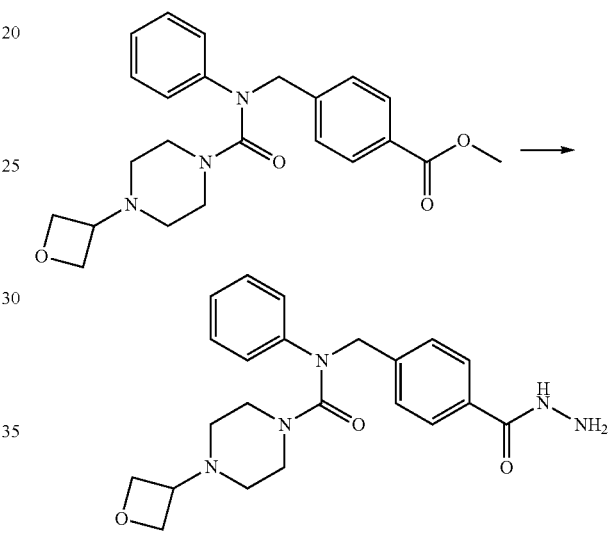

Methyl 4-((4-(oxetan-3-yl)-N-phenylpiperazine-1-carboxamido)methyl)benzoate (0.535 g, 1.307 mmol) and hydrazine monohydrate (1.270 mL, 26.130 mmol) were mixed at the room temperature in ethanol (5 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(4-(hydrazinecarbonyl)benzyl)-4-(oxetan-3-yl)-N-phenylpiperazine-1-carboxamide as white solid (0.344 g, 64.2%).

[Step 6] Compound 21954

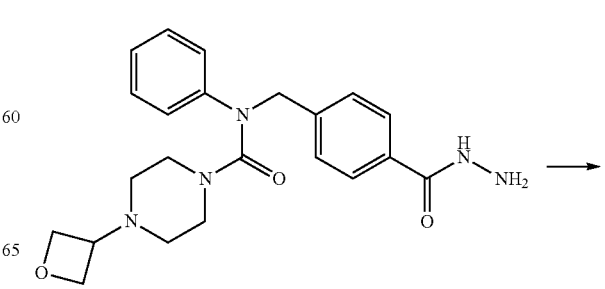

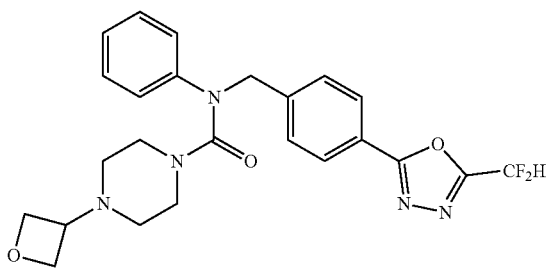

N-(4-(hydrazinecarbonyl)benzyl)-4-(oxetan-3-yl)-N-phenylpiperazine-1-carboxamide (0.344 g, 0.839 mmol), triethylamine (0.351 mL, 2.518 mmol) and 2,2-difluoroacetic anhydride (0.313 mL, 2.518 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)benzyl)-4-(oxetan-3-yl)-N-phenylpiperazine-1-carboxamide as white solid (0.110 g, 27.9%).

$^1$H NMR (400 MHz, CDCl$_3$) δ 7.95 (d, 2H, J=7.9 Hz), 7.39 (d, 2H, J=7.9 Hz), 7.25-7.17 (m, 2H), 7.05 (t, 1H, J=7.5 Hz), 6.99-6.67 (m, 3H), 4.86 (s, 2H), 4.58-4.48 (m, 4H), 3.38 (s, 1H), 3.27 (s, 4H), 2.11 (s, 4H); LRMS (ES) m/z 470.3 (M$^+$+1).

Example 399. Compound 21955: N-(4-(5-(Difluoromethyl)-1,3,4-oxadiazol-2-yl)-2-fluorobenzyl)-4-(oxetan-3-yl)-N-phenylpiperazine-1-carboxamide

[Step 1] Tert-Butyl 4-((2-fluoro-4-(methoxycarbonyl)benzyl)(phenyl)carbamoyl)piperazine-1-carboxylat

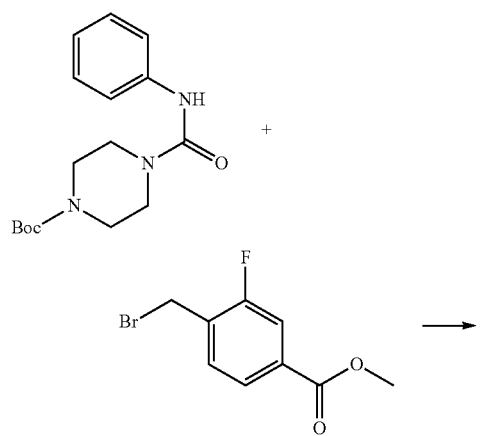

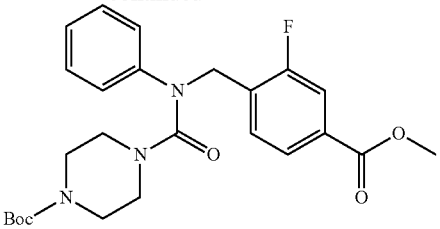

A solution of tert-butyl 4-(phenylcarbamoyl)piperazine-1-carboxylate (0.610 g, 1.998 mmol) and sodium hydride (60.00%, 0.120 g, 2.996 mmol) in tetrahydrofuran (6 mL) was stirred at the room temperature for 30 min, and mixed with methyl 4-(bromomethyl)-3-fluorobenzoate (0.543 g, 2.197 mmol). The reaction mixture was stirred at the same temperature for additional 18 hr, and concentrated under the reduced pressure. The concentrate was purified and concentrated by column chromatography (SiO$_2$, 12 g cartridge; ethyl acetate/hexane=0% to 50%) to give tert-butyl 4-((2-fluoro-4-(methoxycarbonyl)benzyl)(phenyl)carbamoyl)piperazine-1-carboxylate as colorless oil (0.699 g, 74.2%).

[Step 2] Methyl 3-fluoro-4-((N-phenylpiperazine-1-carboxamido)methyl)benzoate hydrochloride

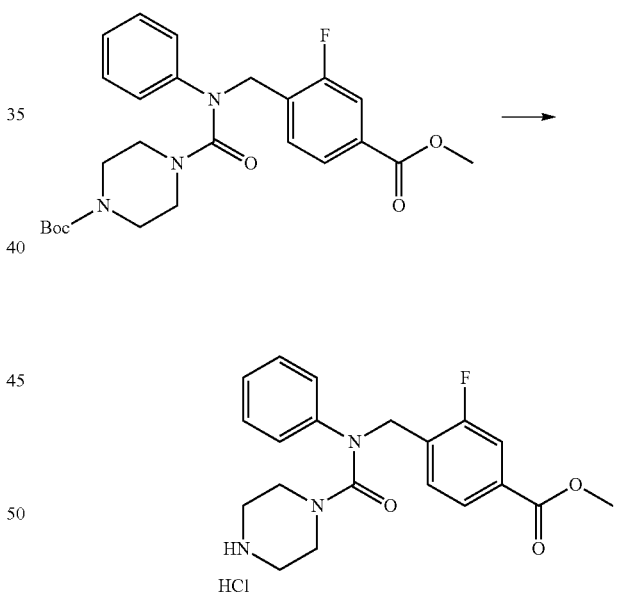

A solution of tert-butyl 4-((2-fluoro-4-(methoxycarbonyl)benzyl)(phenyl)carbamoyl)piperazine-1-carboxylate (0.699 g, 1.482 mmol) and hydrogen chloride (4.00 M solution in 1,4-dioxane, 1.482 mL, 5.929 mmol) in dichloromethane (4 mL) was stirred at the room temperature for 18 hr, and concentrated under the reduced pressure. The title compound was used without further purification (methyl 3-fluoro-4-((N-phenylpiperazine-1-carboxamido)methyl)benzoate hydrochloride, 0.604 g, 99.9%, pale yellow solid).

1219

[Step 3] Methyl 3-fluoro-4-((4-(oxetan-3-yl)-N-phenylpiperazine-1-carboxamido)methyl)benzoate

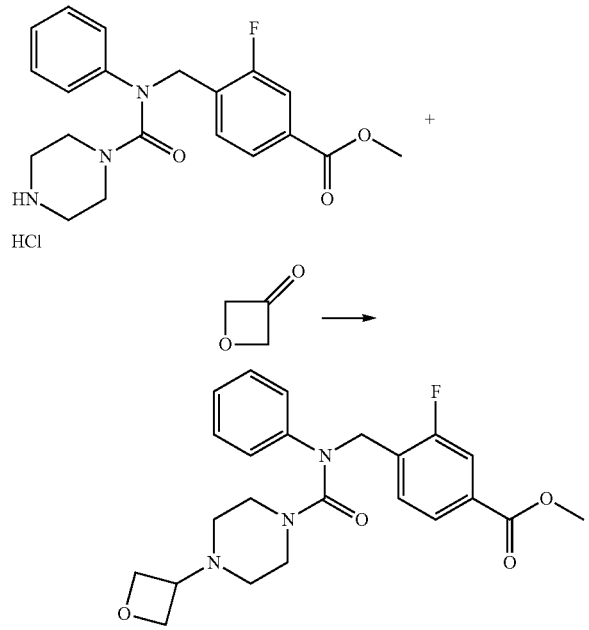

A solution of methyl 3-fluoro-4-((N-phenylpiperazine-1-carboxamido)methyl)benzoate hydrochloride (0.604 g, 1.481 mmol), oxetan-3-one (0.130 mL, 2.221 mmol) and sodium triacetoxyborohydride (0.471 g, 2.221 mmol) in dichloromethane (5 mL) prepared at the room temperature was stirred at the same temperature for 18 hr. Then, saturated aqueous sodium chloride solution was added to the reaction mixture, followed by extraction with dichloromethane. The bi-phasic mixture was passed through a plastic frit to remove the solid residues and aqueous layer, and the organic layer collected was concentrated in vacuo. The title compound was used without further purification (methyl 3-fluoro-4-((4-(oxetan-3-yl)-N-phenylpiperazine-1-carboxamido)methyl)benzoate, 0.632 g, 99.8%, pale yellow oil).

[Step 4] N-(2-Fluoro-4-(hydrazinecarbonyl)benzyl)-4-(oxetan-3-yl)-N-phenylpiperazine-1-carboxamide

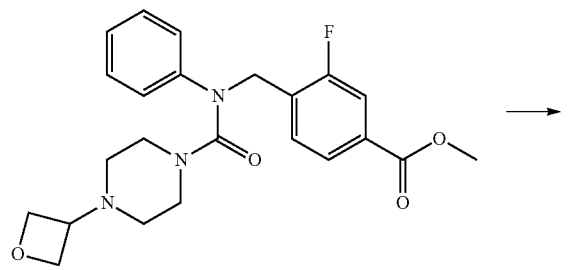

1220

-continued

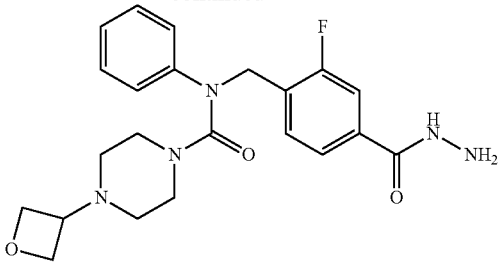

Methyl 3-fluoro-4-((4-(oxetan-3-yl)-N-phenylpiperazine-1-carboxamido)methyl)benzoate (0.632 g, 1.478 mmol) and hydrazine monohydrate (1.437 mL, 29.569 mmol) were mixed at the room temperature in ethanol (4 mL) and then stirred at 80° C. for 18 hr and cooled down to the room temperature to terminate the reaction. The reaction mixture was concentrated under the reduced pressure to remove the solvent. The concentrate was purified and concentrated by column chromatography (SiO$_2$, 4 g cartridge; methanol/dichloromethane=0% to 10%) to give N-(2-fluoro-4-(hydrazinecarbonyl)benzyl)-4-(oxetan-3-yl)-N-phenylpiperazine-1-carboxamide as white solid (0.623 g, 98.5%).

[Step 5] Compound 21955

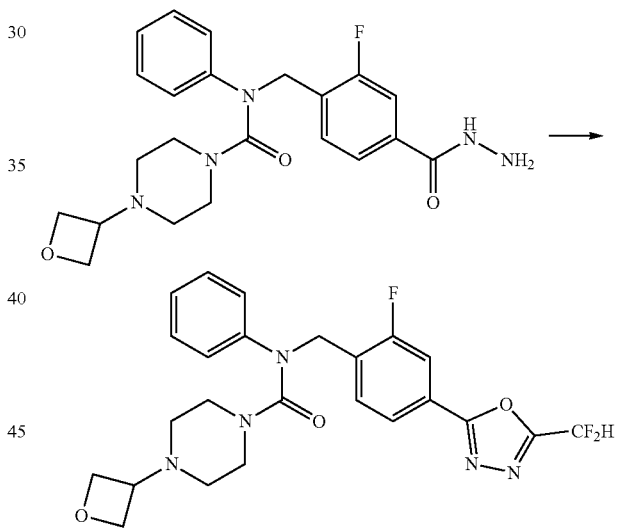

N-(2-Fluoro-4-(hydrazinecarbonyl)benzyl)-4-(oxetan-3-yl)-N-phenylpiperazine-1-carboxamide (0.623 g, 1.457 mmol), triethylamine (0.609 mL, 4.371 mmol) and 2,2-difluoroacetic anhydride (0.543 mL, 4.371 mmol) were mixed at the room temperature in dichloromethane (4 mL) and then stirred at 40° C. for 18 hr and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 5%) to give N-(4-(5-(difluoromethyl)-1,3,4-oxadiazol-2-yl)-2-fluorobenzyl)-4-(oxetan-3-yl)-N-phenylpiperazine-1-carboxamide as pale yellow solid (0.195 g, 27.5%).

¹H NMR (400 MHz, CDCl₃) δ 7.78 (d, 1H, J=8.0 Hz), 7.66 (d, 1H, J=10.0 Hz), 7.61 (t, 1H, J=7.6 Hz), 7.28-7.17 (m, 2H), 7.12-6.98 (m, 3H), 6.84 (t, 1H, J=51.7 Hz), 4.90 (s, 2H), 4.59-4.50 (m, 4H), 3.40 (s, 1H), 3.28 (s, 4H), 2.12 (s, 4H); LRMS (ES) m/z 488.3 (M⁺+1).

Example 400. Compound 21956: 1-(4-(5-(Difluoromethyl)-1,3,4-oxadiazol-2-yl)-2-fluorobenzyl)-1-phenyl-3-(2-(pyrrolidin-1-yl)ethyl)urea

[Step 1] 3-Fluoro-4-methylbenzohydrazide

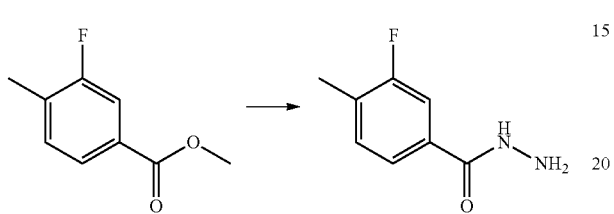

Methyl 3-fluoro-4-methylbenzoate (10.000 g, 59.464 mmol) and hydrazine monohydrate (28.900 mL, 594.636 mmol) were mixed at the room temperature in ethanol (150 mL) and then stirred at 100° C. for 18 hr, cooled down to the room temperature to terminate the reaction concentrated under the reduced pressure. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 80 g cartridge; methanol/dichloromethane=0% to 10%) to give 3-fluoro-4-methylbenzohydrazide as white solid (9.600 g, 96.0%).

[Step 2] (2-(Difluoromethyl)-5-(3-fluoro-4-methylphenyl)-1,3,4-oxadiazole

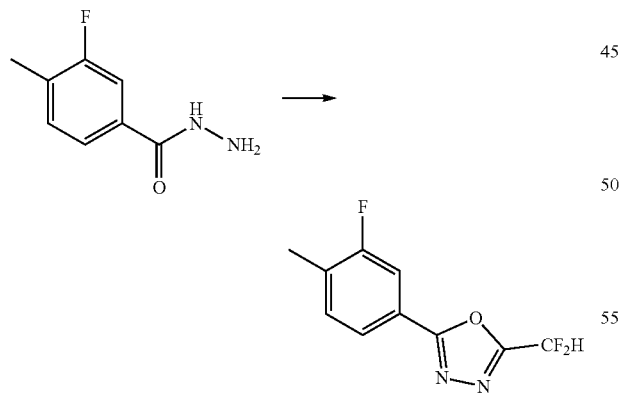

3-fluoro-4-methylbenzohydrazide (9.600 g, 52.689 mmol), imidazole (10.761 g, 158.068 mmol) and 2,2-difluoroacetic anhydride (19.651 mL, 158.068 mmol) were mixed at the room temperature in dichloromethane (200 mL) and then stirred at 50° C. for 18 hr and cooled down to the room temperature to terminate the reaction. Then, saturated aqueous ammonium chloride solution was added to the reaction mixture, followed by extraction with dichloromethane. The organic layer was washed with aqueous saturated sodium bicarbonate solution, dried with anhydrous MgSO₄, filtered, and concentrated in vacuo. The title compound was used without further purification (2-(difluoromethyl)-5-(3-fluoro-4-methylphenyl)-1,3,4-oxadiazole, 11.900 g, 99.0%, white solid).

[Step 3] 2-(4-(Bromomethyl)-3-fluorophenyl)-5-(difluoromethyl)-1,3,4-oxadiazole

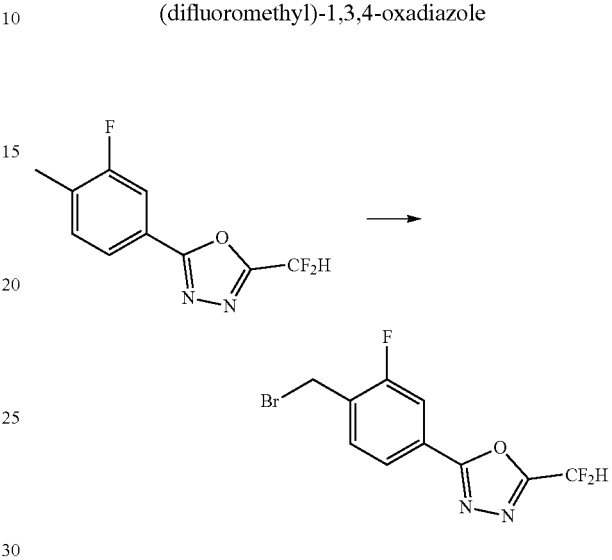

A solution of 2-(difluoromethyl)-5-(3-fluoro-4-methylphenyl)-1,3,4-oxadiazole (11.900 g, 52.154 mmol), 1-bromopyrrolidine-2,5-dione (NBS, 9.747 g, 54.762 mmol) and Azobisisobutyronitrile (AIBN, 0.428 g, 2.608 mmol) in dichloromethane (200 mL) prepared at the room temperature was heated at reflux for 18 hr and cooled down to the room temperature to terminate the reaction. Then, water was added to the reaction mixture, followed by extraction with dichloromethane. The organic layer was washed with aqueous saturated sodium chloride solution, dried with anhydrous MgSO₄, filtered, and concentrated in vacuo. The concentrate was purified and concentrated by column chromatography (SiO₂, 120 g cartridge; ethyl acetate/hexane=0% to 10%) to give 2-(4-(bromomethyl)-3-fluorophenyl)-5-(difluoromethyl)-1,3,4-oxadiazole as white solid (11.946 g, 74.6%).

[Step 4] N-(4-(5-(difluoromethyl)-1,3,4-oxadiazol-2-yl)-2-fluorobenzyl)aniline

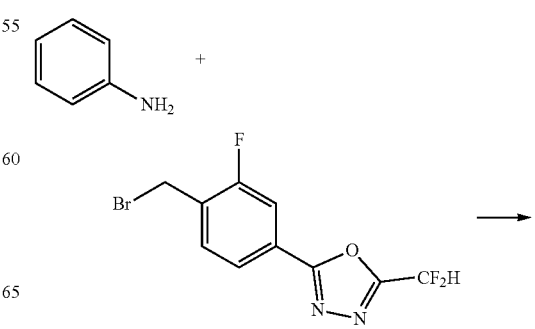

-continued

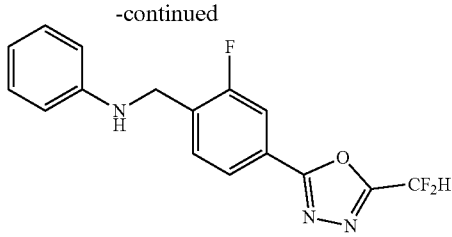

A solution of 2-(4-(bromomethyl)-3-fluorophenyl)-5-(difluoromethyl)-1,3,4-oxadiazole (6.000 g, 19.540 mmol), aniline (1.784 mL, 19.540 mmol) and N,N-diisopropylethylamine (6.807 mL, 39.079 mmol) in acetonitrile (50 mL) prepared at the room temperature was stirred at the same temperature for 18 hr, filtered to remove solids, and concentrated under the reduced pressure. The concentrate was purified and concentrated by column chromatography ($SiO_2$, 24 g cartridge; ethyl acetate/hexane=0% to 10%) to give N-(4-(5-(difluoromethyl)-1,3,4-oxadiazol-2-yl)-2-fluorobenzyl)aniline as white foam (4.939 g, 79.2%).

[Step 5] 3-(2-Chloroethyl)-1-(4-(5-(difluoromethyl)-1,3,4-oxadiazol-2-yl)-2-fluorobenzyl)-1-phenylurea

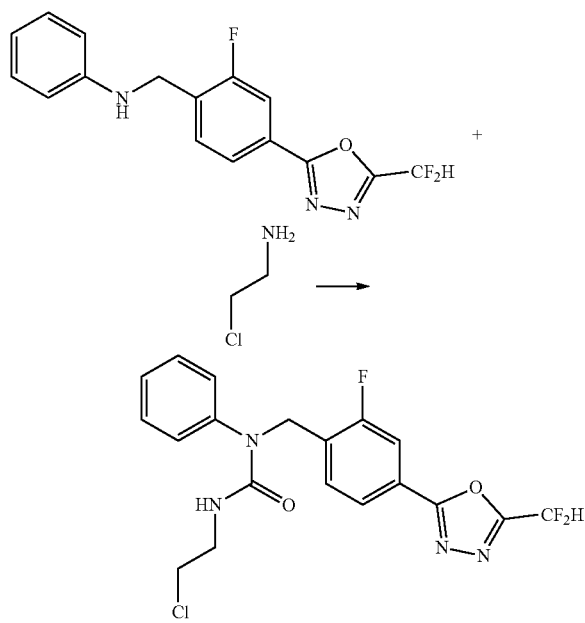

Triphosgene (0.251 g, 0.846 mmol) was added to a solution of N-(4-(5-(difluoromethyl)-1,3,4-oxadiazol-2-yl)-2-fluorobenzyl)aniline (0.540 g, 1.691 mmol) and N,N-diisopropylethylamine (1.767 mL, 10.148 mmol) in dichloromethane (5 mL) at 0° C., and the reaction mixture was stirred at the same temperature for 1 hr. The reaction mixture was treated at the room temperature with 2-chloroethan-1-amine hydrochloride (0.196 g, 1.691 mmol), and stirred for additional 18 hr. Then, water was added to the reaction mixture, followed by extraction with dichloromethane. The organic layer was washed with aqueous saturated sodium chloride solution, dried with anhydrous $MgSO_4$, filtered, and concentrated in vacuo. The concentrate was purified and concentrated by column chromatography ($SiO_2$, 24 g cartridge; ethyl acetate/hexane=0% to 10%) to give 3-(2-chloroethyl)-1-(4-(5-(difluoromethyl)-1,3,4-oxadiazol-2-yl)-2-fluorobenzyl)-1-phenylurea as yellow oil (0.712 g, 99.1%).

[Step 6] Compound 21956

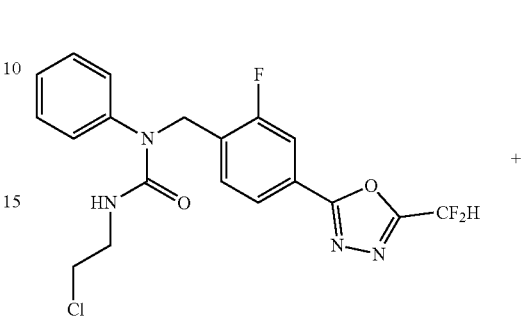

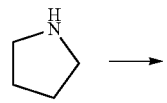

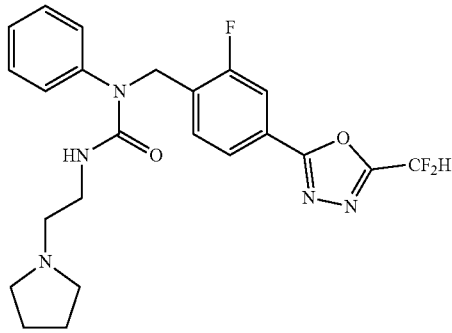

3-(2-chloroethyl)-1-(4-(5-(difluoromethyl)-1,3,4-oxadiazol-2-yl)-2-fluorobenzyl)-1-phenylurea (0.030 g, 0.071 mmol), pyrrolidine (0.005 g, 0.074 mmol) and triethylamine (0.020 mL, 0.141 mmol) were mixed at the room temperature in acetonitrile (2 mL) and then stirred at 80° C. for 18 hr, cooled down to the room temperature to terminate the reaction concentrated under the reduced pressure. Then, water was added to the reaction mixture, followed by extraction with dichloromethane. The bi-phasic was passed through a plastic frit to remove the solid residues and aqueous layer, and the organic layer collected was concentrated in vacuo. The concentrate was purified and concentrated by column chromatography ($SiO_2$, 4 g cartridge; methanol/dichloromethane=0% to 10%) to give 1-(4-(5-(difluoromethyl)-1,3,4-oxadiazol-2-yl)-2-fluorobenzyl)-1-phenyl-3-(2-(pyrrolidin-1-yl)ethyl)urea as colorless oil (0.018 g, 55.8%).

$^1$H NMR (400 MHz, $CDCl_3$) δ 7.89 (dd, 1H, J=8.0, 1.7 Hz), 7.74 (dd, 1H, J=9.9, 1.6 Hz), 7.65 (t, 1H, J=7.6 Hz), 7.46-7.30 (m, 3H), 7.23-7.15 (m, 2H), 6.93 (t, 1H, J=51.7 Hz), 5.25 (s, 1H), 5.04 (s, 2H), 3.62 (s, 2H), 3.44-2.49 (m, 6H), 2.04 (s, 4H); LRMS (ES) m/z 460.0 (M$^+$+1).

Example 401. Compound 21957: 1-(4-(5-(Difluoromethyl)-1,3,4-oxadiazol-2-yl)-2-fluorobenzyl)-1-phenyl-3-(2-(piperidin-1-yl)ethyl)urea Example 402. Compound 21958: 1-(4-(5-(Difluoromethyl)-1,3,4-oxadiazol-2-yl)-2-fluorobenzyl)-3-(2-(4-methylpiperazin-1-yl)ethyl)-1-phenylurea

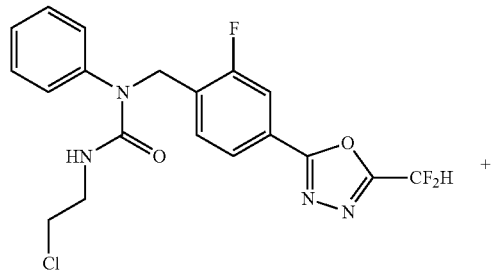

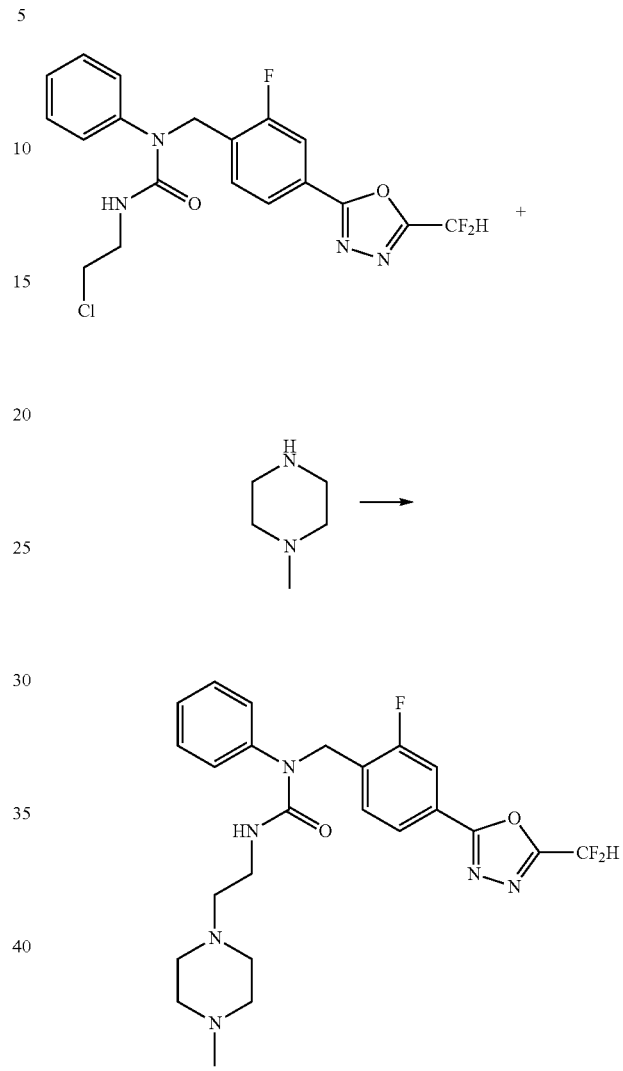

3-(2-chloroethyl)-1-(4-(5-(difluoromethyl)-1,3,4-oxadiazol-2-yl)-2-fluorobenzyl)-1-phenylurea (0.050 g, 0.118 mmol), piperdine (0.013 mL, 0.129 mmol) and triethylamine (0.033 mL, 0.235 mmol) were mixed at the room temperature in acetonitrile (2 mL) and then stirred at 80° C. for 18 hr, cooled down to the room temperature to terminate the reaction concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 10%) to give 1-(4-(5-(difluoromethyl)-1,3,4-oxadiazol-2-yl)-2-fluorobenzyl)-1-phenyl-3-(2-(piperidin-1-yl)ethyl)urea as colorless oil (0.031 g, 55.1%).

$^1$H NMR (400 MHz, CDCl$_3$) δ 7.80 (dd, 1H, J=8.0, 1.5 Hz), 7.62 (dd, 2H, J=8.8, 6.6 Hz), 7.31 (t, 2H, J=7.5 Hz), 7.23 (t, 1H, J=7.3 Hz), 7.10 (d, 2H, J=7.6 Hz), 6.84 (t, 1H, J=51.7 Hz), 5.14 (s, 1H), 4.97 (s, 2H), 3.24-3.16 (m, 2H), 2.27 (s, 2H), 2.18 (s, 4H), 1.22 (s, 6H); LRMS (ES) m/z 474.1 (M$^+$+1).

3-(2-chloroethyl)-1-(4-(5-(difluoromethyl)-1,3,4-oxadiazol-2-yl)-2-fluorobenzyl)-1-phenylurea (0.050 g, 0.118 mmol), 1-methylpiperazine (0.014 mL, 0.129 mmol) and triethylamine (0.033 mL, 0.235 mmol) were mixed at the room temperature in acetonitrile (2 mL) and then stirred at 80° C. for 18 hr, cooled down to the room temperature to terminate the reaction concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 12 g cartridge; methanol/dichloromethane=0% to 10%) to give 1-(4-(5-(difluoromethyl)-1,3,4-oxadiazol-2-yl)-2-fluorobenzyl)-3-(2-(4-methylpiperazin-1-yl)ethyl)-1-phenylurea as colorless oil (0.029 g, 50.6%).

$^1$H NMR (400 MHz, CDCl$_3$) δ 7.89 (d, 1H, J=8.0 Hz), 7.77-7.67 (m, 2H), 7.41 (t, 2H, J=7.7 Hz), 7.37-7.30 (m, 1H), 7.22-7.15 (m, 2H), 6.93 (t, 1H, J=51.5 Hz), 5.12 (s, 1H), 5.06 (s, 2H), 3.31 (q, 2H, J=5.7 Hz), 2.77-1.69 (m, 13H); LRMS (ES) m/z 489.1 (M$^+$+1).

Example 403. Compound 21970: N-(4-(5-(difluoromethyl)-1,3,4-oxadiazol-2-yl)-2-fluorobenzyl)-N-(4-(1-methylpiperidin-4-yl)phenyl)thiomorpholine-4-carboxamide 1,1-dioxide

[Step 1] N-(4-bromophenyl)-N-(4-(5-(difluoromethyl)-1,3,4-oxadiazol-2-yl)-2-fluorobenzyl)thiomorpholine-4-carboxamide 1,1-dioxide

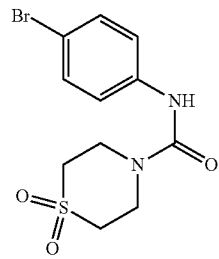

+

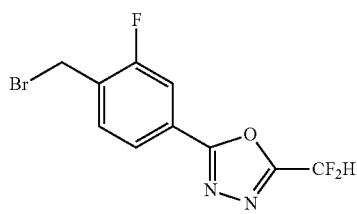

→

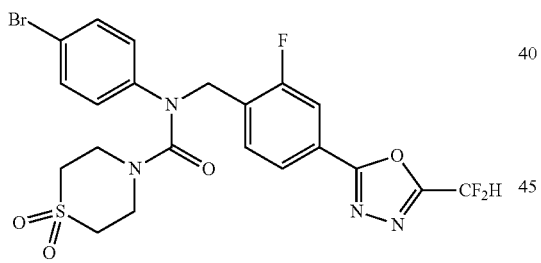

A solution of N-(4-bromophenyl)thiomorpholine-4-carboxamide 1,1-dioxide (0.250 g, 0.750 mmol), 2-(4-(bromomethyl)-3-fluorophenyl)-5-(difluoromethyl)-1,3,4-oxadiazole (0.242 g, 0.788 mmol) and sodium hydride (60.00%, 0.032 g, 0.788 mmol) in N,N-dimethylformamide (5 mL) prepared at the room temperature was stirred at the same temperature for 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 50%) to give N-(4-bromophenyl)-N-(4-(5-(difluoromethyl)-1,3,4-oxadiazol-2-yl)-2-fluorobenzyl)thiomorpholine-4-carboxamide 1,1-dioxide as white solid (0.208 g, 49.6%).

[Step 2] N-(4-(5-(difluoromethyl)-1,3,4-oxadiazol-2-yl)-2-fluorobenzyl)-N-(4-(1-methyl-1,2,3,6-tetrahydropyridin-4-yl)phenyl)thiomorpholine-4-carboxamide 1,1-dioxide

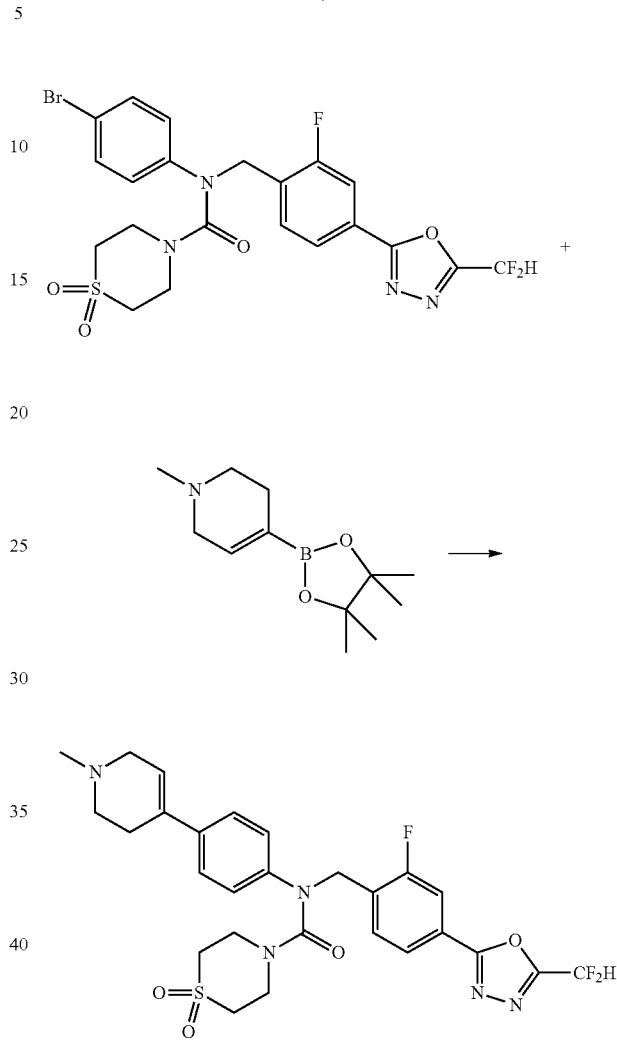

N-(4-bromophenyl)-N-(4-(5-(difluoromethyl)-1,3,4-oxadiazol-2-yl)-2-fluorobenzyl)thiomorpholine-4-carboxamide 1,1-dioxide (0.200 g, 0.358 mmol), 1-methyl-4-(4,4,5,5-tetramethyl-1,3,2-dioxaborolan-2-yl)-1,2,3,6-tetrahydropyridine (0.096 g, 0.429 mmol), [1,1'-bis(di-tert-butylphosphino)ferrocene]palladium(II) dichloride (Pd(dtbpf)Cl2, 0.012 g, 0.018 mmol) and cesium carbonate (0.349 g, 1.073 mmol) in 1,4-dioxane (3 mL)/water (1 mL) was mixed at the room temperature and then heated at 100° C. under the microwaves for 20 min and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-(1-methyl-1,2,3,6-tetrahydropyridin-4-yl)phenyl)thiomorpholine-4-carboxamide 1,1-dioxide as orange solid (0.159 g, 77.3%).

[Step 3] Compound 21970

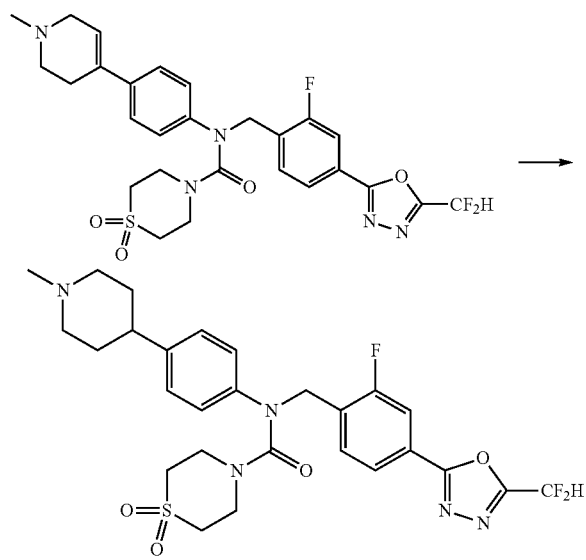

A solution of N-(4-(5-(difluoromethyl)-1,3,4-oxadiazol-2-yl)-2-fluorobenzyl)-N-(4-(1-methyl-1,2,3,6-tetrahydropyridin-4-yl)phenyl)thiomorpholine-4-carboxamide 1,1-dioxide (0.150 g, 0.261 mmol) in methanol (5 mL)/tetrahydrofuran (1 mL) was slowly added dropwise with 10%-Pd/C (20 mg) and stirred at the room temperature for 6 hr. The reaction mixture was stirred at 40° C. under the hydrogen atmosphere (H$_2$ balloon) for additional 17 hr, cooled down to the room temperature to terminate the reaction filtered through a celite pad to remove solids, and concentrated under the reduced pressure. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-(1-methylpiperidin-4-yl)phenyl)thiomorpholine-4-carboxamide 1,1-dioxide as white solid (0.040 g, 26.6%).

$^1$H NMR (400 MHz, CDCl$_3$) δ 7.89 (dd, 1H, J=8.0, 1.5 Hz), 7.77 (dd, 1H, J=10.1, 1.5 Hz), 7.67 (t, 1H, J=7.6 Hz), 7.28-7.27 (m, 2H), 7.10-6.80 (m, 3H), 4.92 (s, 2H), 3.72-3.70 (m, 4H), 3.47 (brs, 2H), 2.81-2.69 (m, 10H), 2.41 (brs, 2H), 1.98 (d, 2H, J=13.4 Hz); LRMS (ES) m/z 578.1 (M$^+$+1).

Example 404. Compound 21971: N-(4-(5-(difluoromethyl)-1,3,4-oxadiazol-2-yl)-2-fluorobenzyl)-N-(4-(2-(4-ethylpiperazin-1-yl)ethoxy)phenyl)thiomorpholine-4-carboxamide 1,1-dioxide

[Step 1] 1-(2-Bromoethoxy)-4-nitrobenzene

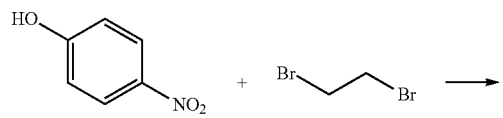

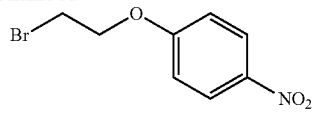

A solution of 4-nitrophenol (2.000 g, 14.377 mmol), 1,2-dibromoethane (2.478 mL, 28.754 mmol) and potassium carbonate (5.961 g, 43.131 mmol) in acetonitrile (30 mL) was heated at reflux for 17 hr, cooled down to the room temperature to terminate the reaction concentrated under the reduced pressure. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=0% to 10%) to give 1-(2-bromoethoxy)-4-nitrobenzene as pale yellow solid (1.130 g, 32.1%).

[Step 2] 1-Ethyl-4-(2-(4-nitrophenoxy)ethyl)piperazine

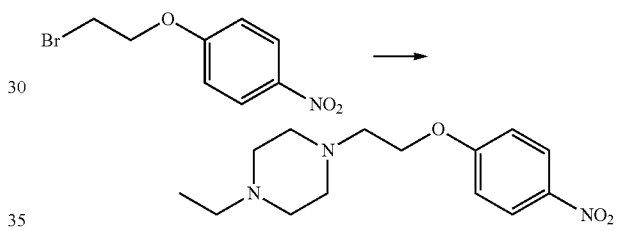

A solution of 1-(2-bromoethoxy)-4-nitrobenzene (0.500 g, 2.032 mmol), ethylpiperazine (0.284 mL, 2.235 mmol) and potassium carbonate (0.421 g, 3.048 mmol) in acetonitrile (20 mL) was heated at reflux for 17 hr, cooled down to the room temperature to terminate the reaction concentrated under the reduced pressure. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-Ethyl-4-(2-(4-nitrophenoxy)ethyl)piperazine was used without further purification (0.570 g, 100.4%, yellow oil).

[Step 3] 4-(2-(4-Ethylpiperazin-1-yl)ethoxy)aniline

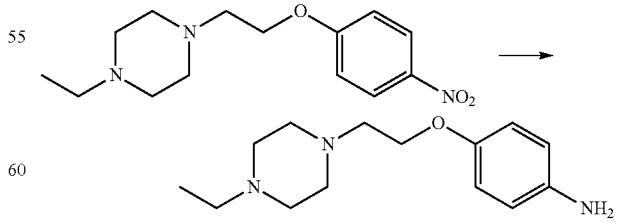

A solution of 1-ethyl-4-(2-(4-nitrophenoxy)ethyl)piperazine (0.570 g, 2.041 mmol) in methanol (10 mL) was slowly added dropwise at the room temperature with 10%-Pd/C (80 mg), stirred at the same temperature under the hydrogen

[Step 4] N-(4-(5-(Difluoromethyl)-1,3,4-oxadiazol-2-yl)-2-fluorobenzyl)-4-(2-(4-ethylpiperazin-1-yl)ethoxy)aniline

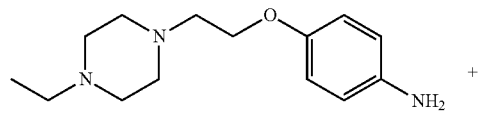

+

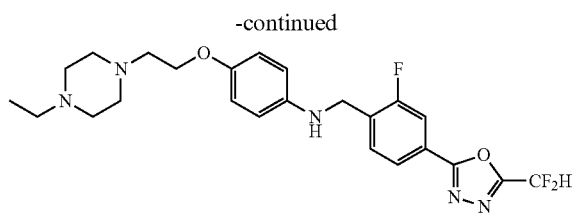

→

-continued

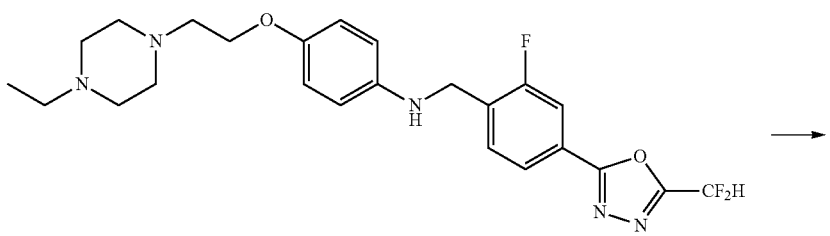

4-(2-(4-ethylpiperazin-1-yl)ethoxy)aniline (0.250 g, 1.003 mmol), 2-(4-(bromomethyl)-3-fluorophenyl)-5-(difluoromethyl)-1,3,4-oxadiazole (0.308 g, 1.003 mmol) and N,N-diisopropylethylamine (0.524 mL, 3.008 mmol) were mixed at the room temperature in tetrahydrofuran (5 mL) and then stirred at the same temperature for 17 hr, and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-4-(2-(4-ethylpiperazin-1-yl)ethoxy)aniline as yellow oil (0.161 g, 33.8%).

[Step 5] (4-(5-(Difluoromethyl)-1,3,4-oxadiazol-2-yl)-2-fluorobenzyl)(4-(2-(4-ethylpiperazin-1-yl)ethoxy)phenyl)carbamic chloride

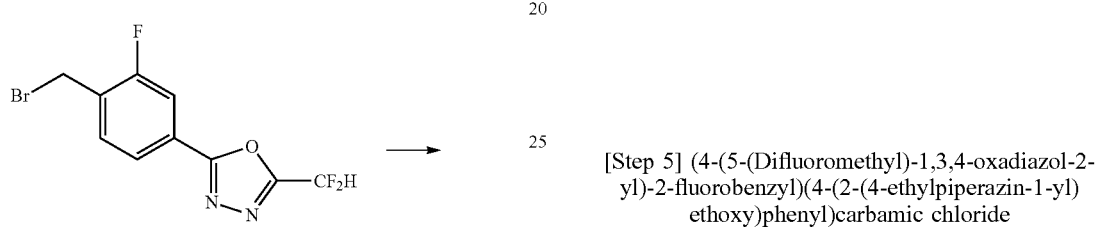

→

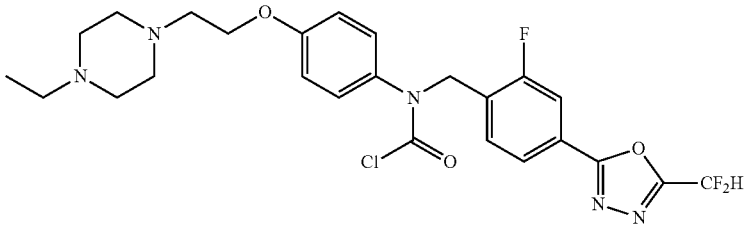

A solution of N-(4-(5-(difluoromethyl)-1,3,4-oxadiazol-2-yl)-2-fluorobenzyl)-4-(2-(4-ethylpiperazin-1-yl)ethoxy)aniline (0.160 g, 0.336 mmol) in dichloromethane (5 mL) was stirred at 0° C. for 10 min, and mixed with triphosgene (0.050 g, 0.168 mmol) and N,N-diisopropylethylamine (0.176 mL, 1.009 mmol). The reaction mixture was stirred at the same temperature for additional 1 hr, and concentrated under the reduced pressure. (4-(5-(difluoromethyl)-1,3,4-oxadiazol-2-yl)-2-fluorobenzyl)(4-(2-(4-ethylpiperazin-1-yl)ethoxy)phenyl)carbamic chloride was used without further purification (0.180 g, 99.4%, yellow solid).

[Step 6] Compound 21971

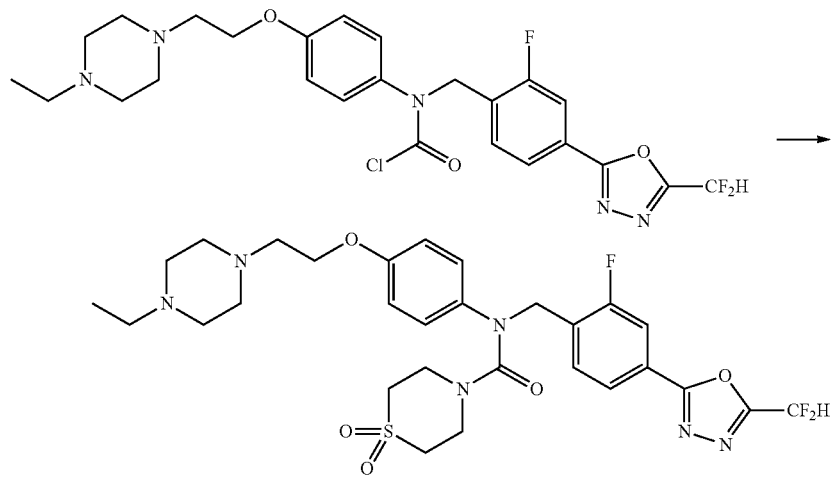

A solution of thiomorpholine (0.090 g, 0.669 mmol) and sodium hydride (60.00%, 0.027 g, 0.669 mmol) in N,N-dimethylformamide (3 mL) was stirred at 0° C. for 10 min, and mixed with (4-(5-(difluoromethyl)-1,3,4-oxadiazol-2-yl)-2-fluorobenzyl)(4-(2-(4-ethylpiperazin-1-yl)ethoxy)phenyl)carbamic chloride (0.180 g, 0.335 mmol). The reaction mixture was stirred at the room temperature for additional 1 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-(2-(4-ethylpiperazin-1-yl)ethoxy)phenyl)thiomorpholine-4-carboxamide 1,1-dioxide as yellow solid (0.061 g, 28.6%).

$^1$H NMR (400 MHz, DMSO-d$_6$) δ 7.86 (dd, 1H, J=8.0, 1.6 Hz), 7.78-7.73 (m, 2H), 7.55 (t, 1H, J=51.3 Hz), 7.21 (d, 2, J=8.9 Hz), 6.92 (d, 2H, J=9.0 Hz), 4.87 (s, 2H), 4.04-4.03 (m, 2H), 3.55 (s, 4H), 2.89 (s, 4H), 2.70-2.50 (m, 12H), 1.06 (brs, 3H), 1.06 (brs, 3H); LRMS (ES) m/z 637.3 (M$^+$+1).

Example 405. Compound 21972: N-(4-(5-(difluoromethyl)-1,3,4-oxadiazol-2-yl)-2-fluorobenzyl)-N-(4-(3-(4-ethylpiperazin-1-yl)propoxy)phenyl)thiomorpholine-4-carboxamide 1,1-dioxide

[Step 1] 1-(3-Bromopropoxy)-4-nitrobenzene

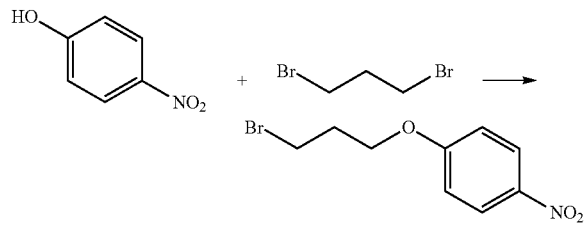

A solution of 4-nitrophenol (2.000 g, 14.377 mmol), 1,3-dibromopropane (2.919 mL, 28.754 mmol) and potassium carbonate (5.961 g, 43.131 mmol) in acetonitrile (30 mL) was heated at reflux for 17 hr, cooled down to the room temperature to terminate the reaction and concentrated under the reduced pressure. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=0% to 10%) to give 1-(3-bromopropoxy)-4-nitrobenzene as pale yellow solid (2.990 g, 80.0%).

[Step 2] 1-Ethyl-4-(3-(4-nitrophenoxy)propyl)piperazine

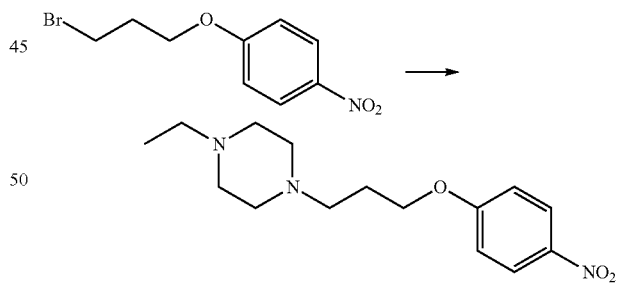

A solution of 1-(3-bromopropoxy)-4-nitrobenzene (0.500 g, 1.922 mmol), ethylpiperazine (0.269 mL, 2.115 mmol) and potassium carbonate (0.399 g, 2.884 mmol) in acetonitrile (20 mL) was heated at reflux for 17 hr, cooled down to the room temperature to terminate the reaction concentrated under the reduced pressure. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-Ethyl-4-(3-(4-nitrophenoxy)propyl)piperazine was used without further purification (0.562 g, 99.6%, yellow oil).

[Step 3] 4-(3-(4-Ethylpiperazin-1-yl)propoxy)aniline

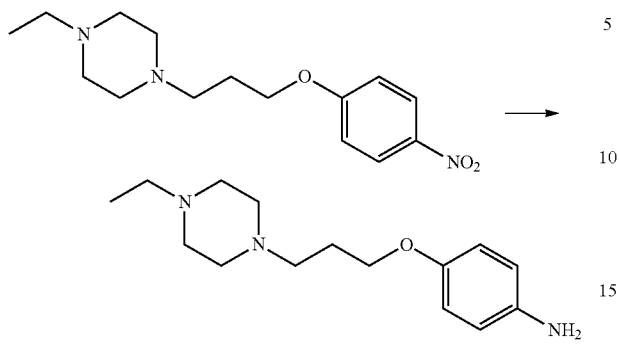

A solution of 1-ethyl-4-(3-(4-nitrophenoxy)propyl)piperazine (0.562 g, 1.916 mmol) in methanol (20 mL) was slowly added dropwise at the room temperature with 10%-Pd/C (80 mg), stirred at the same temperature under the hydrogen atmosphere ($H_2$ balloon) for 3 hr, filtered through a celite pad to remove solids, and concentrated under the reduced pressure. 4-(3-(4-ethylpiperazin-1-yl)propoxy)aniline was used without further purification (0.537 g, 106.4%, red oil).

[Step 4] N-(4-(5-(difluoromethyl)-1,3,4-oxadiazol-2-yl)-2-fluorobenzyl)-4-(3-(4-ethylpiperazin-1-yl)propoxy)aniline

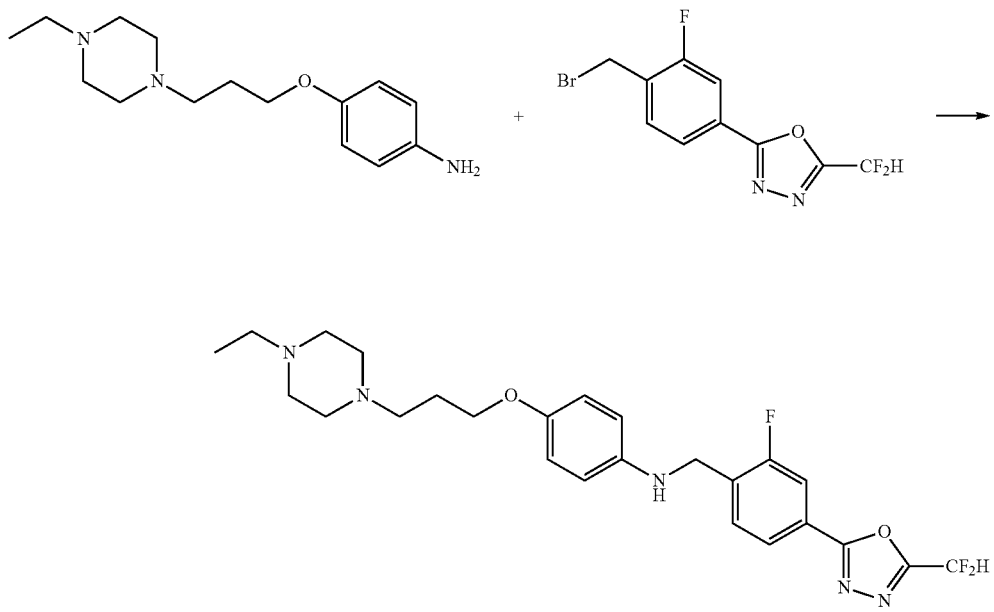

4-(3-(4-ethylpiperazin-1-yl)propoxy)aniline (0.300 g, 1.139 mmol), 2-(4-(bromomethyl)-3-fluorophenyl)-5-(difluoromethyl)-1,3,4-oxadiazole (0.385 g, 1.253 mmol) and N,N-diisopropylethylamine (0.208 mL, 1.196 mmol) were mixed at the room temperature in tetrahydrofuran (5 mL) and then stirred at the same temperature for 17 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography ($SiO_2$, 4 g cartridge; methanol/dichloromethane=0% to 5%) to give N-(4-(5-(difluoromethyl)-1,3,4-oxadiazol-2-yl)-2-fluorobenzyl)-4-(3-(4-ethylpiperazin-1-yl)propoxy)aniline as yellow oil (0.417 g, 74.8%).

[Step 5] (4-(5-(Difluoromethyl)-1,3,4-oxadiazol-2-yl)-2-fluorobenzyl)(4-(3-(4-ethylpiperazin-1-yl)propoxy)phenyl)carbamic chloride

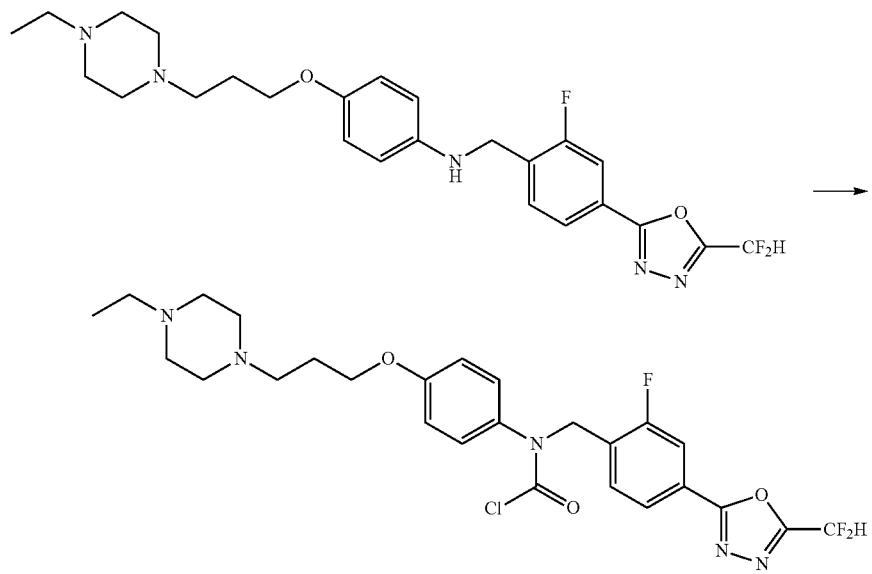

A solution of N-(4-(5-(difluoromethyl)-1,3,4-oxadiazol-2-yl)-2-fluorobenzyl)-4-(3-(4-ethylpiperazin-1-yl)propoxy)aniline (0.182 g, 0.372 mmol) in dichloromethane (5 mL) was mixed at 0° C. with triphosgene (0.055 g, 0.186 mmol) and N,N-diisopropylethylamine (0.194 mL, 1.115 mmol), and stirred at the same temperature for 10 min. The reaction mixture was stirred at the same temperature for additional 1 hr, and concentrated under the reduced pressure. (4-(5-(difluoromethyl)-1,3,4-oxadiazol-2-yl)-2-fluorobenzyl)(4-(3-(4-ethylpiperazin-1-yl)propoxy)phenyl)carbamic chloride was used without further purification (0.200 g, 97.5%, yellow oil).

[Step 6] Compound 21972

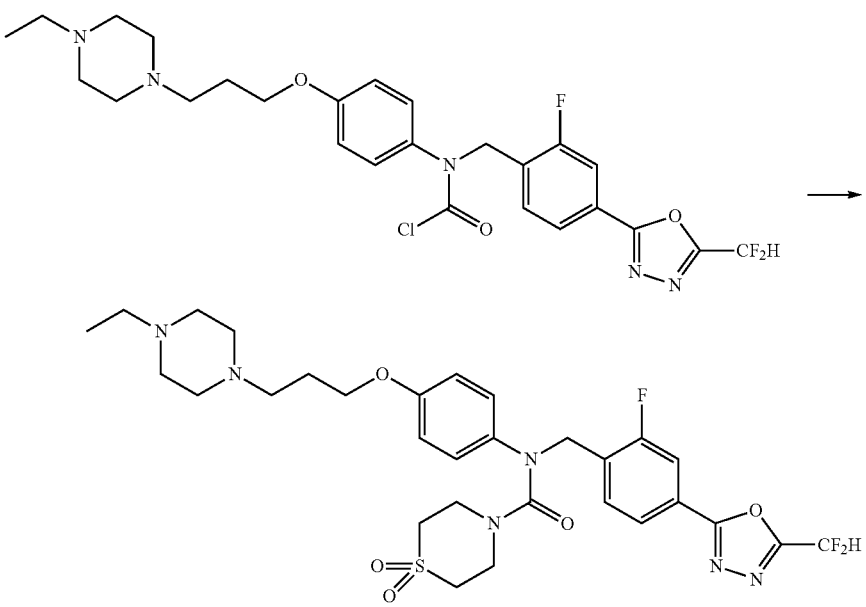

A solution of thiomorpholine (0.098 g, 0.725 mmol) and sodium hydride (60.00%, 0.029 g, 0.725 mmol) in N,N-dimethylformamide (3 mL) was stirred at 0° C. for 10 min, and mixed with (4-(5-(difluoromethyl)-1,3,4-oxadiazol-2-yl)-2-fluorobenzyl)(4-(3-(4-ethylpiperazin-1-yl)propoxy)phenyl)carbamic chloride (0.200 g, 0.362 mmol). The reaction mixture was stirred at the room temperature for additional 1 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-(3-(4-ethylpiperazin-1-yl)propoxy)phenyl)thiomorpholine-4-carboxamide 1,1-dioxide as yellow solid (0.041 g, 17.4%).

$^1$H NMR (400 MHz, DMSO-d$_6$) δ 7.86 (dd, 1H, J=8.0, 1.6 Hz), 7.78-7.73 (m, 2H), 7.55 (t, 1H, J=51.3 Hz), 7.19 (d, 2H, J=8.9 Hz), 6.90 (d, 2H, J=9.0 Hz), 4.86 (s, 2H), 3.95 (t, 2H, J=6.3 Hz), 3.55 (s, 4H), 2.90-2.89 (m, 4H), 2.46-2.28 (m, 12H), 1.84-1.81 (m, 2H), 0.97 (t, 3H, J=7.2 Hz); LRMS (ES) m/z 651.4 (M$^+$+1).

Example 406. Compound 21973: N-(4-(5-(difluoromethyl)-1,3,4-oxadiazol-2-yl)-2-fluorobenzyl)-N-(4-(4-(4-ethylpiperazin-1-yl)butoxy)phenyl)thiomorpholine-4-carboxamide 1,1-dioxide

[Step 1] 1-(4-Bromobutoxy)-4-nitrobenzene

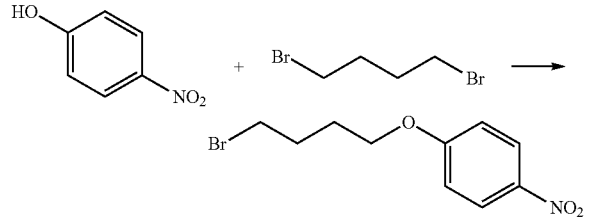

A solution of 4-nitrophenol (2.000 g, 14.377 mmol), 1,4-dibromobutane (6.209 g, 28.754 mmol) and potassium carbonate (5.961 g, 43.131 mmol) in acetonitrile (30 mL) prepared at the room temperature was heated at reflux for 17 hr, cooled down to the room temperature to terminate the reaction concentrated under the reduced pressure. Then, water was added to the reaction mixture, followed by extraction with ethyl acetate. The organic layer was washed with aqueous saturated sodium chloride solution, dried with anhydrous MgSO$_4$, filtered, and concentrated in vacuo. The concentrate was purified and concentrated by column chromatography (SiO$_2$, 24 g cartridge; ethyl acetate/hexane=0% to 10%) to give 1-(bromobutoxy)-4-nitrobenzene as pale yellow oil (2.700 g, 68.5%).

[Step 2] 1-Ethyl-4-(4-(4-nitrophenoxy)butyl)piperazine

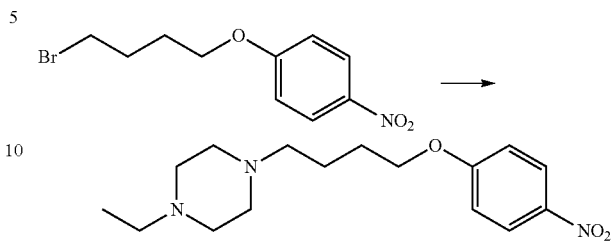

A solution of 1-(4-bromobutoxy)-4-nitrobenzene (0.500 g, 1.824 mmol), ethylpiperazine (0.255 mL, 2.006 mmol) and potassium carbonate (0.378 g, 2.736 mmol) in acetonitrile (20 mL) prepared at the room temperature was heated at reflux for 17 hr, cooled down to the room temperature to terminate the reaction concentrated under the reduced pressure. Then, water was added to the reaction mixture, followed by extraction with ethyl acetate. The organic layer was washed with aqueous saturated sodium chloride solution, dried with anhydrous MgSO$_4$, filtered, and concentrated in vacuo. 1-Ethyl-4-(4-(4-nitrophenoxy)butyl)piperazine was used without further purification (0.558 g, 99.5%, yellow oil).

[Step 3] 4-(4-(4-Ethylpiperazin-1-yl)butoxy)aniline

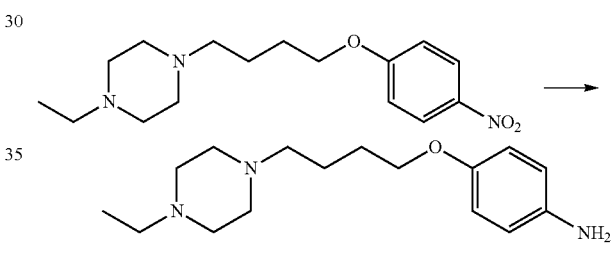

A solution of 1-ethyl-4-(4-(4-nitrophenoxy)butyl)piperazine (0.558 g, 1.815 mmol) in methanol (20 mL) was slowly added dropwise at the room temperature with 10%-Pd/C (80 mg), stirred at the same temperature under the hydrogen atmosphere (H$_2$ balloon) for 4 hr, filtered through a celite pad to remove solids, and concentrated under the reduced pressure. 4-(4-(4-ethylpiperazin-1-yl)butoxy)aniline was used without further purification (0.501 g, 99.5%, red oil).

[Step 4] N-(4-(5-(difluoromethyl)-1,3,4-oxadiazol-2-yl)-2-fluorobenzyl)-4-(4-(4-ethylpiperazin-1-yl)butoxy)aniline

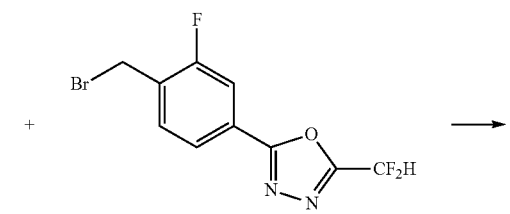

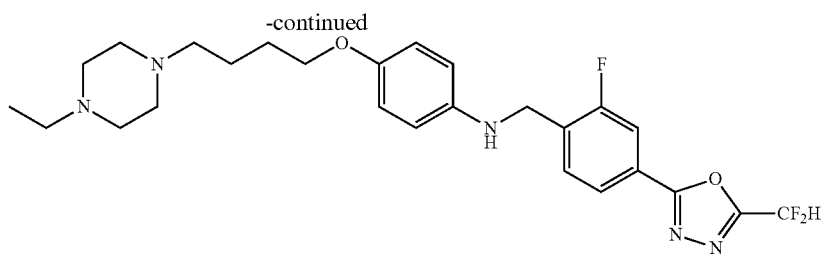

4-(4-(4-ethylpiperazin-1-yl)butoxy)aniline (0.250 g, 0.901 mmol), 2-(4-(bromomethyl)-3-fluorophenyl)-5-(difluoromethyl)-1,3,4-oxadiazole (0.277 g, 0.901 mmol) and N,N-diisopropylethylamine (0.471 mL, 2.704 mmol) were mixed at the room temperature in tetrahydrofuran (5 mL) and then stirred at the same temperature for 17 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo.

The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-4-(4-(4-ethylpiperazin-1-yl)butoxy)aniline as yellow oil (0.149 g, 32.8%).

[Step 5] (4-(5-(Difluoromethyl)-1,3,4-oxadiazol-2-yl)-2-fluorobenzyl)(4-(4-(4-ethylpiperazin-1-yl)butoxy)phenyl)carbamic chloride

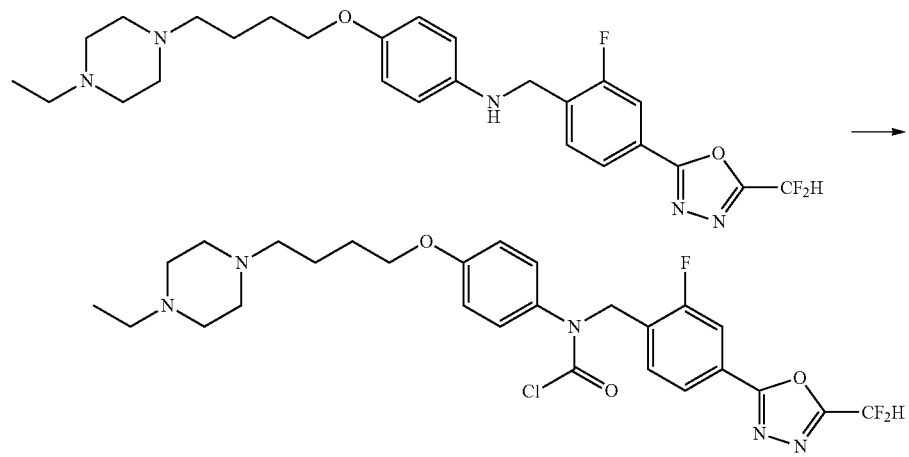

A solution of N-(4-(5-(difluoromethyl)-1,3,4-oxadiazol-2-yl)-2-fluorobenzyl)-4-(4-(4-ethylpiperazin-1-yl)butoxy)aniline (0.149 g, 0.296 mmol) in dichloromethane (5 mL) was stirred at 0° C. for 10 min, and mixed with triphosgene (0.004 g, 0.015 mmol) and N,N-diisopropylethylamine (0.155 mL, 0.888 mmol). The reaction mixture was stirred at the same temperature for additional 1 hr, and concentrated under the reduced pressure. (4-(5-(difluoromethyl)-1,3,4-oxadiazol-2-yl)-2-fluorobenzyl)(4-(4-(4-ethylpiperazin-1-yl)butoxy)phenyl)carbamic chloride was used without further purification (0.160 g, 95.5%, yellow oil).

[Step 6] Compound 21973

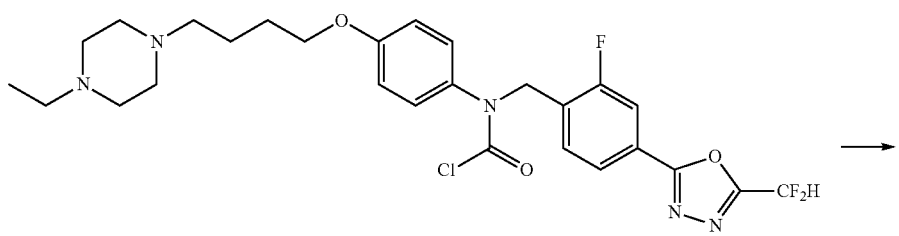

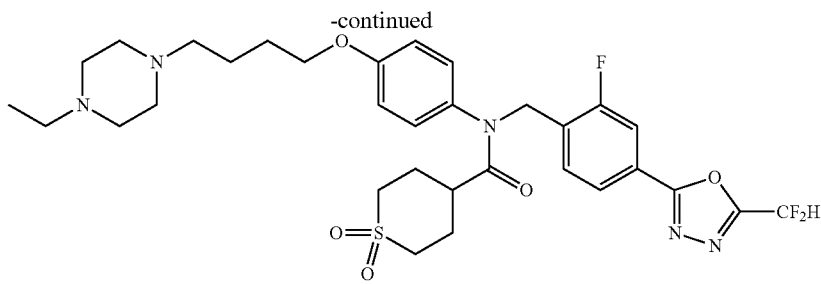

A solution of sodium hydride (60.00%, 0.023 g, 0.565 mmol) and Thiomorpholine (0.076 g, 0.565 mmol) in N,N-dimethylformamide (3 mL) was stirred at 0° C. for 10 min, and mixed with (4-(5-(difluoromethyl)-1,3,4-oxadiazol-2-yl)-2-fluorobenzyl)(4-(4-(4-ethylpiperazin-1-yl)butoxy)phenyl)carbamic chloride (0.160 g, 0.283 mmol). The reaction mixture was stirred at the room temperature for additional 1 hr, and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)-N-(4-(4-(4-ethylpiperazin-1-yl)butoxy)phenyl)thiomorpholine-4-carboxamide 1,1-dioxide as yellow oil (0.104 g, 55.3%).

$^1$H NMR (400 MHz, DMSO-d$_6$) δ 7.86 (dd, 1H, J=8.0, 1.7 Hz), 7.78-7.73 (m, 2H), 7.55 (t, 1H, J=51.3 Hz), 7.20 (d, 2H, J=9.0 Hz), 6.90 (d, 2H, J=9:0 Hz), 4.86 (s, 2H), 3.94 (t, 2H, J=6.4 Hz), 3.55 (s, 4H), 2.89 (s, 4H), 2.34-2.29 (m, 12H), 1.70-1.66 (m, 2H), 1.55-1.51 (m, 2H), 0.97 (t, 3H, J=7.1 Hz); LRMS (ES) m/z 665.2 (M$^+$+1).

Example 407. Compound 21979: N-(4-(5-(difluoromethyl)-1,3,4-oxadiazol-2-yl)-2-fluorobenzyl)-N-(5-methyl-1,3,4-thiadiazol-2-yl)thiomorpholine-4-carboxamide 1,1-dioxide

[Step 1] N-(4-(5-(difluoromethyl)-1,3,4-oxadiazol-2-yl)-2-fluorobenzyl)-5-methyl-1,3,4-thiadiazol-2-amine

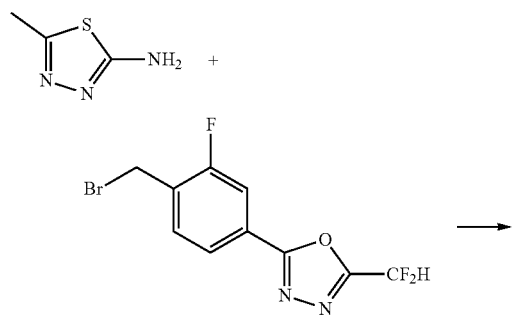

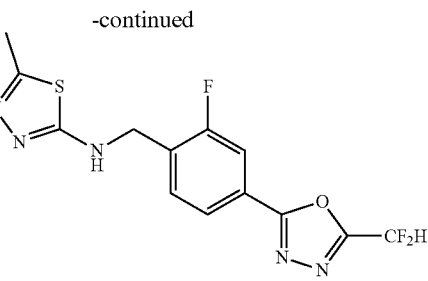

A solution of 5-methyl-1,3,4-thiadiazol-2-amine (0.200 g, 1.737 mmol), 2-(4-(bromomethyl)-3-fluorophenyl)-5-(difluoromethyl)-1,3,4-oxadiazole (0.533 g, 1.737 mmol) and N,N-diisopropylethylamine (0.908 mL, 5.211 mmol) in N,N-dimethylformamide (5 mL) prepared at the room temperature was stirred at the same temperature for 17 hr, and concentrated under the reduced pressure. The residue was diluted with water (4 mL) and dichloromethane (4 mL) and stirred. The resulting precipitates were collected by filtration, washed by dichloromethane, and dried to give N-(4-(5-(difluoromethyl)-3,4-oxadiazol-2-yl)-2-fluorobenzyl)-5-methyl-1,3,4-thiadiazol-2-amine as pale yellow solid (0.095 g, 16.0%).

[Step 2] Compound 21979

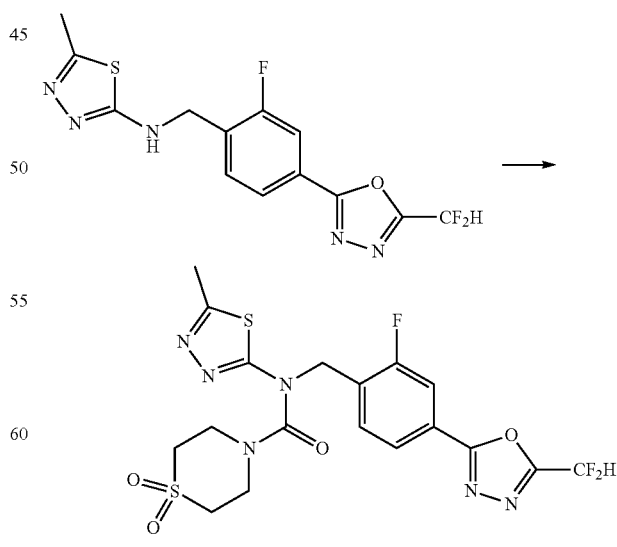

A solution of N-(4-(5-(difluoromethyl)-1,3,4-oxadiazol-2-yl)-2-fluorobenzyl)-5-methyl-1,3,4-thiadiazol-2-amine (0.080 g, 0.234 mmol), triphosgene (60.00%, 0.122 g, 0.246 mmol) and N,N-diisopropylethylamine (0.122 mL, 0.703 mmol) in dichloromethane (5 mL) was stirred at 0° C. for 10 min, and mixed with thiomorpholine (0.035 g, 0.258 mmol). The reaction mixture was stirred at the room temperature for additional 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 50%) to give N-(4-(5-(difluoromethyl)-1,3,4-oxadiazol-2-yl)-2-fluorobenzyl)-N-(5-methyl-1,3,4-thiadiazol-2-yl)thiomorpholine-4-carboxamide 1,1-dioxide as white solid (0.003 g, 2.5%).

$^1$H NMR (400 MHz, DMSO-d$_6$) δ 7.92 (d, 2H, J=8.9 Hz), 7.69-7.44 (m, 2H), 5.53 (s, 2H), 4.14 (s, 2H), 3.91 (s, 2H), 3.11-3.10 (m, 4H), 2.47 (s, 3H); LRMS (ES) m/z 503.2 (M$^+$+1).

Example 408. Compound 21980: N-(4-(5-(difluoromethyl)-1,3,4-oxadiazol-2-yl)-2-fluorobenzyl)-N-(5-methyl-1,3,4-thiadiazol-2-yl)morpholine-4-carboxamide

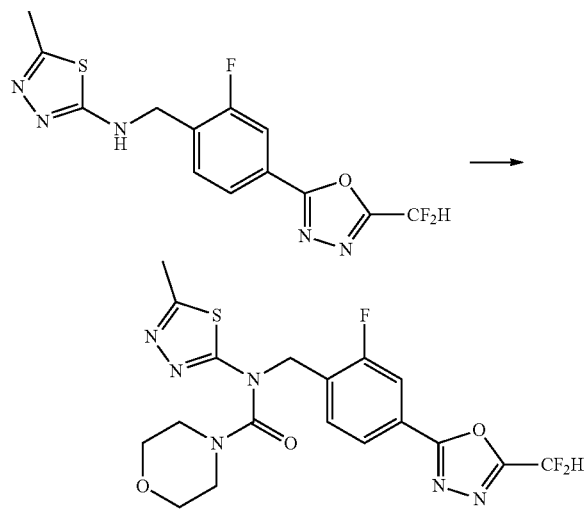

A solution of N-(4-(5-(difluoromethyl)-1,3,4-oxadiazol-2-yl)-2-fluorobenzyl)-5-methyl-1,3,4-thiadiazol-2-amine (0.030 g, 0.088 mmol), triethylamine (0.018 mL, 0.132 mmol) and N,N-dimethylpyridin-4-amine (DMAP, 0.001 g, 0.009 mmol) in dichloromethane (5 mL) was mixed at the room temperature with morpholine-4-carbonyl chloride (0.020 g, 0.132 mmol), stirred at the same temperature for 17 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 60%) to give N-(4-(5-(difluoromethyl)-1,3,4-oxadiazol-2-yl)-2-fluorobenzyl)-N-(5-methyl-1,3,4-thiadiazol-2-yl)morpholine-4-carboxamide as white solid (0.017 g, 42.6%).

$^1$H NMR (400 MHz, CDCl$_3$) δ 7.90-7.85 (m, 2H), 7.42 (t, 1H, J=7.7 Hz), 6.94 (t, 1H, J=51.6 Hz), 5.52 (s, 2H), 3.72-3.69 (m, 8H); LRMS (ES) m/z 463.0 (M$^+$+1).

Example 409. Compound 21981: N-(4-(5-(difluoromethyl)-1,3,4-oxadiazol-2-yl)-2-fluorobenzyl)-N-(1,3,4-thiadiazol-2-yl) morpholine-4-carboxamide

[Step 1] N-(4-(5-(difluoromethyl)-1,3,4-oxadiazol-2-yl)-2-fluorobenzyl)-1,3,4-thiadiazol-2-amine

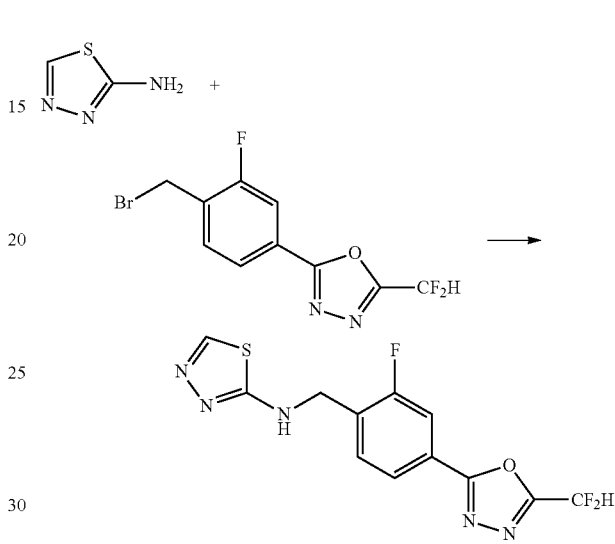

A solution of 1,3,4-thiadiazol-2-amine (0.200 g, 1.978 mmol), 2-(4-(bromomethyl)-3-fluorophenyl)-5-(difluoromethyl)-1,3,4-oxadiazole (0.607 g, 1.978 mmol) and N,N-diisopropylethylamine (1.033 mL, 5.933 mmol) in N,N-dimethylformamide (5 mL) prepared at the room temperature was stirred at the same temperature for 18 hr and concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=50% to 100%) to give N-(4-(5-(difluoromethyl)-1,3,4-oxadiazol-2-yl)-2-fluorobenzyl)-1,3,4-thiadiazol-2-amine as yellow oil (0.100 g, 15.4%).

[Step 2] Compound 21981

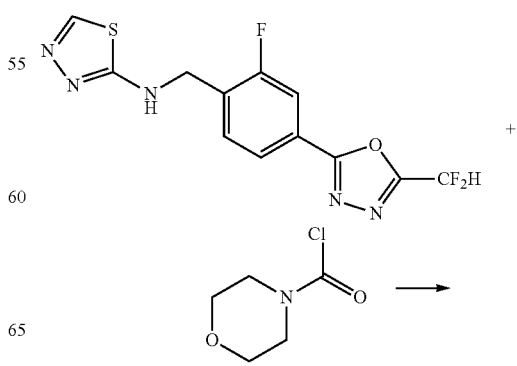

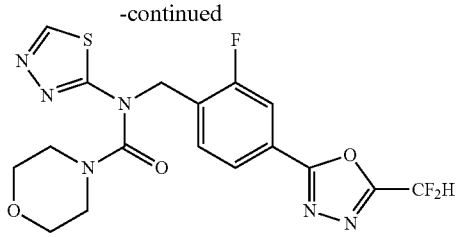

A solution of N-(4-(5-(difluoromethyl)-1,3,4-oxadiazol-2-yl)-2-fluorobenzyl)-1,3,4-thiadiazol-2-amine (0.100 g, 0.306 mmol), morpholine-4-carbonyl chloride (0.070 mL, 0.611 mmol), N,N-diisopropylethylamine (0.160 mL, 0.917 mmol) and N,N-dimethylpyridin-4-amine (DMAP, 0.004 g, 0.031 mmol) in dichloromethane (5 mL) prepared at the room temperature was stirred at the same temperature for 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=10% to 50%) to give N-(4-(5-(difluoromethyl)-1,3,4-oxadiazol-2-yl)-2-fluorobenzyl)-N-(1,3,4-thiadiazol-2-yl) morpholine-4-carboxamide as white solid (0.015 g, 11.1%).

$^1$H NMR (400 MHz, CDCl$_3$) δ 8.24 (s, 1H), 7.91-7.87 (m, 2H), 7.45-7.41 (m, 1H), 6.94 (t, 1H, J=51.6 Hz), 5.58 (s, 2H), 3.73-3.70 (m, 8H); LRMS (ES) m/z 441.2 (M++1).

Example 410. Compound 21982: 1-(4-(5-(Difluoromethyl)-1,3,4-oxadiazol-2-yl)-2-fluorobenzyl)-3-(2-morpholinoethyl)-1-phenylurea

[Step 1] 3-(2-Bromoethyl)-1-(4-(5-(difluoromethyl)-1,3,4-oxadiazol-2-yl)-2-fluorobenzyl)-1-phenylurea

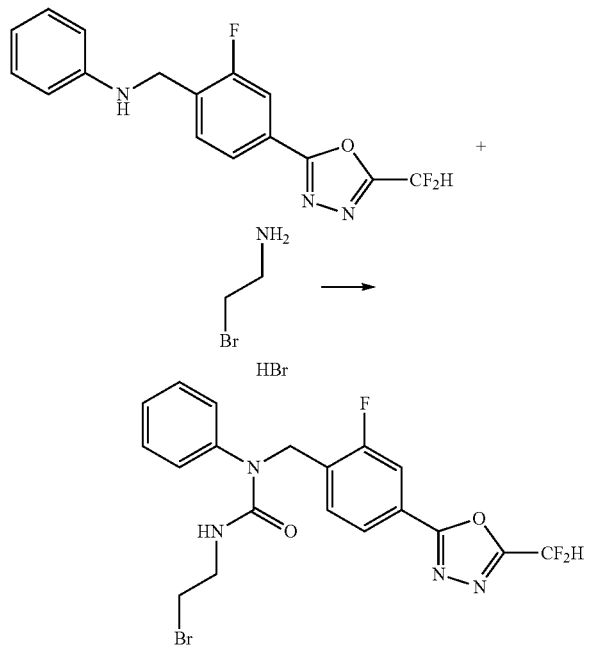

Triphosgene (2.295 g, 7.734 mmol) was added to a solution of N-(4-(5-(difluoromethyl)-1,3,4-oxadiazol-2-yl)-2-fluorobenzyl)aniline (4.939 g, 15.469 mmol) and N,N-diisopropylethylamine (16.166 mL, 92.812 mmol) in dichloromethane (50 mL) at 0° C., and the reaction mixture was stirred at the same temperature for 1 hr. The reaction mixture was treated at the room temperature with 2-bromoethan-1-amine hydrobromide (4.754 g, 23.203 mmol) and stirred for additional 4 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The concentrate was purified and concentrated by column chromatography (SiO$_2$, 80 g cartridge; ethyl acetate/hexane=0% to 10%) to give 3-(2-bromoethyl)-1-(4-(5-(difluoromethyl)-1,3,4-oxadiazol-2-yl)-2-fluorobenzyl)-1-phenylurea as colorless oil (2.764 g, 38.1%).

[Step 2] Compound 21982

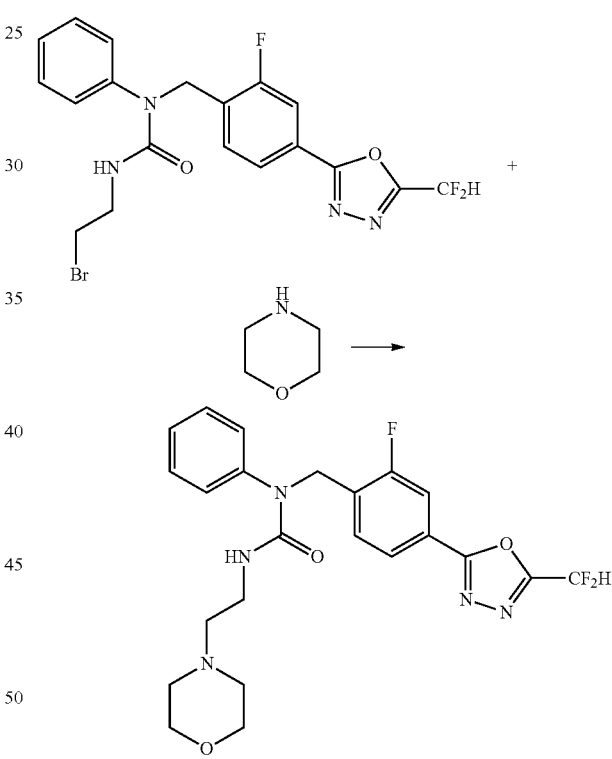

3-(2-bromoethyl)-1-(4-(5-(difluoromethyl)-1,3,4-oxadiazol-2-yl)-2-fluorobenzyl)-1-phenylurea (0.050 g, 0.107 mmol) and morpholine (0.010 mL, 0117 mmol) were mixed at the room temperature in acetonitrile (5 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 10%) to give 1-(4-(5-(difluoromethyl)-1, 3,4-oxadiazol-2-yl)-2-fluorobenzyl)-3-(2-morpholino-ethyl)-1-phenylurea as yellow oil (0.023 g, 45.8%).

$^1$H NMR (400 MHz, CDCl$_3$) δ 7.89 (dd, 1H, J=8.0, 1.7 Hz), 7.77-7.66 (m, 2H), 7.46-7.36 (m, 2H), 7.39-7.30 (m, 1H), 7.23-7.14 (m, 2H), 6.93 (t, 1H, J=51.7 Hz), 5.11 (t, 1H, J=4.8 Hz), 5.05 (s, 2H), 3.49 (s, 4H), 3.32 (td, 2H, J=6.0, 4.7 Hz), 2.41 (t, 2H, J=6.1 Hz), 2.34 (t, 4H, J=4.6 Hz); LRMS (ES) m/z 476.3 (M$^+$+1).

Example 411. Compound 21983: 3-(2-(3,3-Difluoroazetidin-1-yl)ethyl)-1-(4-(5-(difluoromethyl)-1,3,4-oxadiazol-2-yl)-2-fluorobenzyl)-1-phenylurea

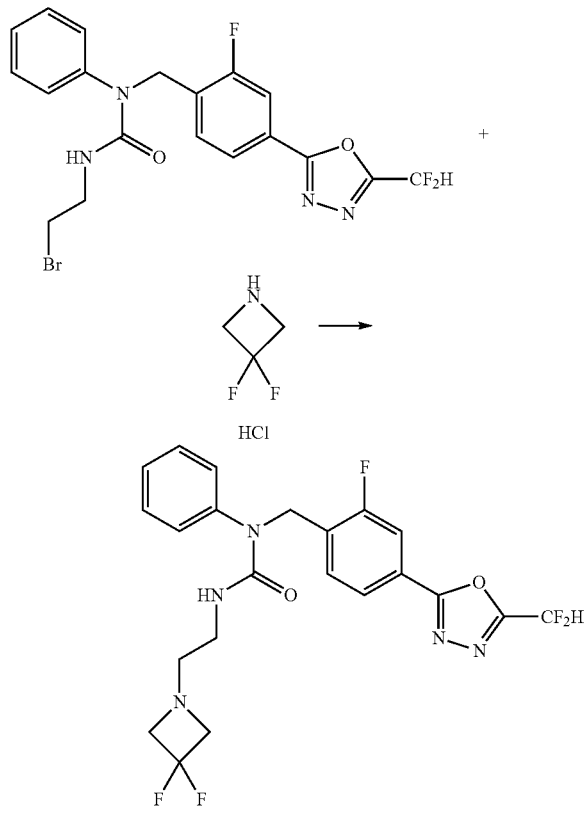

3-(2-bromoethyl)-1-(4-(5-(difluoromethyl)-1,3,4-oxadiazol-2-yl)-2-fluorobenzyl)-1-phenylurea (0.050 g, 0.107 mmol) and 3,3-difluoroazetidine hydrochloride (0.015 g, 0.117 mmol) were mixed at the room temperature in dichloromethane (1 mL) and then stirred at 50° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(3,3-difluoroazetidin-1-yl)ethyl)-1-(4-(5-(difluoromethyl)-1,3,4-oxadiazol-2-yl)-2-fluorobenzyl)-1-phenylurea as colorless oil (0.005 g, 9.7%).

$^1$H NMR (700 MHz, CDCl$_3$) δ 7.90 (dd, 1H, J=8.0, 1.7 Hz), 7.73 (dd, 1H, J=9.8, 1.7 Hz), 7.71-7.66 (m, 1H), 7.41 (dd, 2H, J=8.2, 7.0 Hz), 7.37-7.32 (m, 1H), 7.20-7.15 (m, 2H), 6.93 (t, 1H, J=51.7 Hz), 5.05 (s, 2H), 3.54 (t, 4H, J=12.0 Hz), 3.26 (q, 2H, J=5.9 Hz), 2.65 (tt, 2H, J=6.0, 1.2 Hz); LRMS (ES) m/z 482.3 (M$^+$+1).

Example 412. Compound 21984: 1-(4-(5-(Difluoromethyl)-1,3,4-oxadiazol-2-yl)-2-fluorobenzyl)-3-(2-(4-(2-morpholino-2-oxoethyl)piperazin-1-yl)ethyl)-1-phenylurea

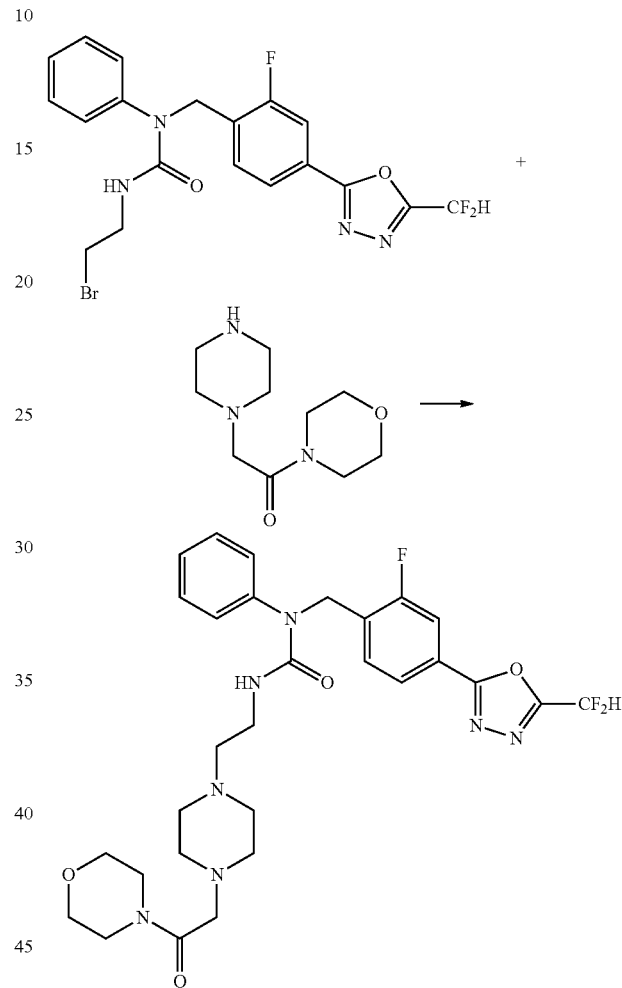

3-(2-bromoethyl)-1-(4-(5-(difluoromethyl)-1,3,4-oxadiazol-2-yl)-2-fluorobenzyl)-1-phenylurea (0.050 g, 0.197 mmol) and 1-morpholino-2-(piperazin-1-yl)ethan-1-one (0.025 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-(2-morpholino-2-oxoethyl)piperazin-1-yl)ethyl)-1-phenylurea as yellow solid (0.013 g, 20.3%).

$^1$H NMR (700 MHz, CDCl$_3$) δ 7.89 (dd, 1H, J=8.0, 1.7 Hz), 7.73 (dd, 1H, J=9.8, 1.7 Hz), 7.70 (t, 1H, J=7.6 Hz), 7.44-7.38 (m, 2H), 7.37-7.32 (m, 2H), 7.20-7.15 (m, 2H), 7.03-6.82 (m, 2H), 5.10 (t, 1H, J=4.7 Hz), 5.05 (s, 2H), 3.71-3.65 (m, 4H), 3.65-3.59 (m, 4H), 3.30 (q, 2H, J=5.6 Hz), 3.11 (s, 2H), 2.65-2.05 (m, 10H); LRMS (ES) m/z 602.0 ($M^+$+1).

Example 413. Compound 21985: 1-(4-(5-(Difluoromethyl)-1,3,4-oxadiazol-2-yl)-2-fluorobenzyl)-3-(2-(1,1-dioxidothiomorpholino)ethyl)-1-phenylurea

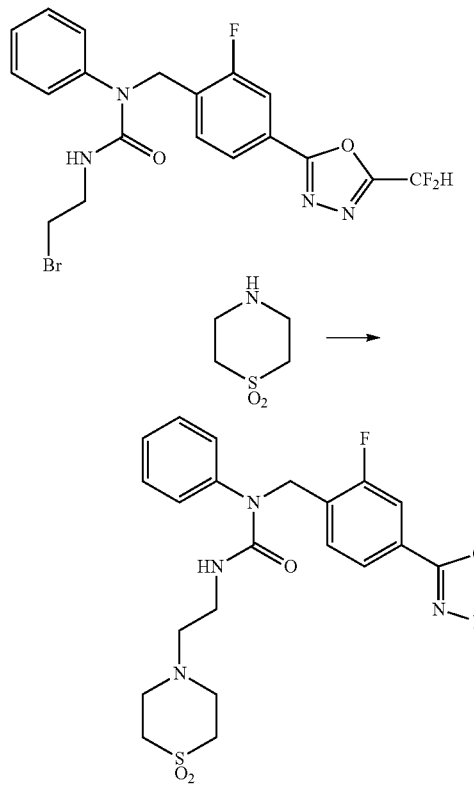

Example 414. Compound 21986: 3-(2-(1,4-Oxazepan-4-yl)ethyl)-1-(4-(5-(difluoromethyl)-1,3,4-oxadiazol-2-yl)-2-fluorobenzyl)-1-phenylurea

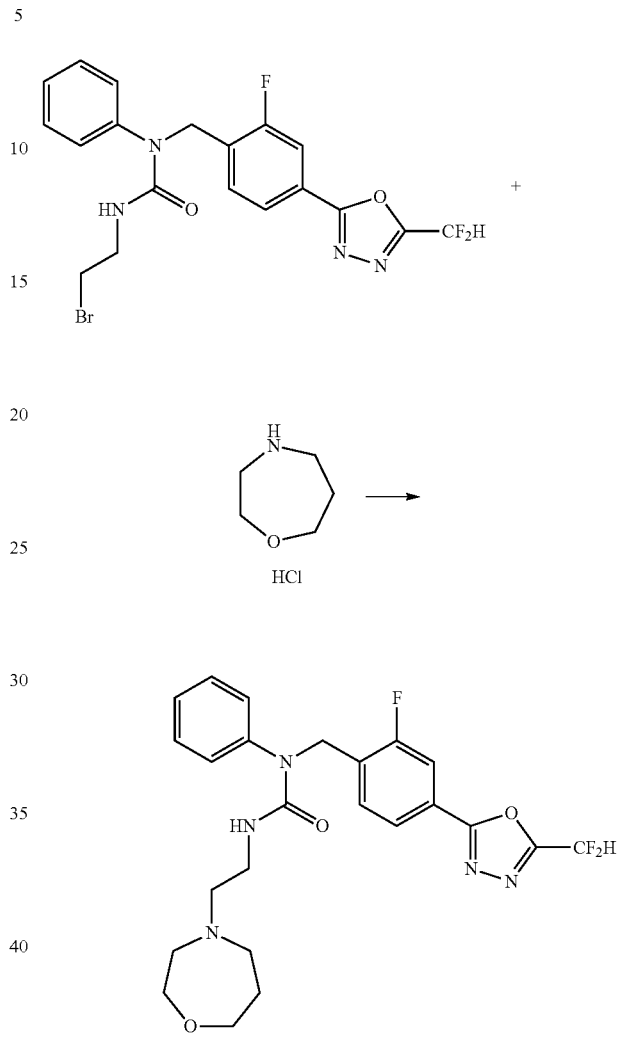

3-(2-bromoethyl)-1-(4-(5-(difluoromethyl)-1,3,4-oxadiazol-2-yl)-2-fluorobenzyl)-1-phenylurea (0.050 g, 0.107 mmol) and thiomorpholine 1,1-dioxide (0.016 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography ($SiO_2$ plate, 20×20×1 mm; methanol/dichloromethane=10%) to give 1-(4-(5-(difluoromethyl)-1,3,4-oxadiazol-2-yl)-2-fluorobenzyl)-3-(2-(1,1-dioxidothiomorpholino)ethyl)-1-phenylurea as white solid (0.009 g, 16.1%).

$^1$H NMR (700 MHz, $CDCl_3$) δ 7.90 (dd, 1H, J=8.0, 1.6 Hz), 7.74 (dd, 1H, J=9.8, 1.7 Hz), 7.70-7.65 (m, 1H), 7.47-7.41 (m, 2H), 7.44-7.37 (m, 1H), 7.21-7.16 (m, 2H), 6.93 (t, 1H, J=51.7 Hz), 5.05 (s, 2H), 4.81 (t, 1H, J=5.1 Hz), 3.33 (td, 2H, J=6.1, 5.1 Hz), 2.93 (dd, 4H, J=7.1, 3.6 Hz), 2.85 (dd, 4H, J=6.5, 3.4 Hz), 2.59 (t, 2H, J=6.1 Hz); LRMS (ES) m/z 524.1 ($M^+$+1).

3-(2-bromoethyl)-1-(4-(5-(difluoromethyl)-1,3,4-oxadiazol-2-yl)-2-fluorobenzyl)-1-phenylurea (0.050 g, 0.107 mmol) and 1,4-oxazepane hydrochloride (0.016 g, 0.117 mmol) were mixed at the room temperature in dichloromethane (1 mL) and then stirred at 50° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography ($SiO_2$ plate, 20×20×1 mm; methanol/dichloromethane=10%) to give 3-(2-(1,4-oxazepan-4-yl)ethyl)-1-(4-(5-(difluoromethyl)-1,3,4-oxadiazol-2-yl)-2-fluorobenzyl)-1-phenylurea as white oil (0.004 g, 7.7%).

$^1$H NMR (700 MHz, $CDCl_3$) δ 7.89 (dd, 1H, J=8.0, 1.7 Hz), 7.75-7.69 (m, 2H), 7.44-7.38 (m, 2H), 7.37-7.32 (m, 1H), 7.23-7.17 (m, 2H), 6.93 (t, 1H, J=51.7 Hz), 5.17 (t, 1H, J=4.9 Hz), 5.06 (s, 2H), 3.59 (t, 2H, J=6.0 Hz), 3.47 (t, 2H, J=4.5 Hz), 3.29 (q, 2H, J=5.6 Hz), 2.56 (dt, 6H, J=19.0, 6.5 Hz), 1.74-1.57 (m, 2H); LRMS (ES) m/z 490.0 ($M^+$+1).

Example 415. Compound 21987: (R)-1-(4-(5-(difluoromethyl)-1,3,4-oxadiazol-2-yl)-2-fluorobenzyl)-1-phenyl-3-(2-(2-(trifluoromethyl)pyrrolidin-1-yl)ethyl)urea

Example 416. Compound 21988: (S)-1-(4-(5-(difluoromethyl)-1,3,4-oxadiazol-2-yl)-2-fluorobenzyl)-1-phenyl-3-(2-(2-(trifluoromethyl)pyrrolidin-1-yl)ethyl)urea

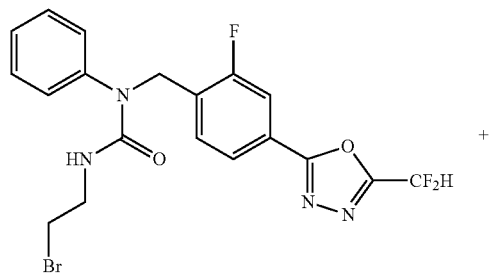

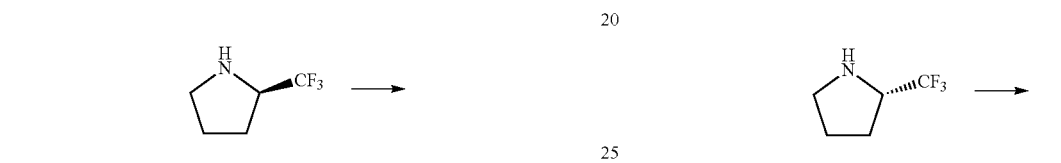

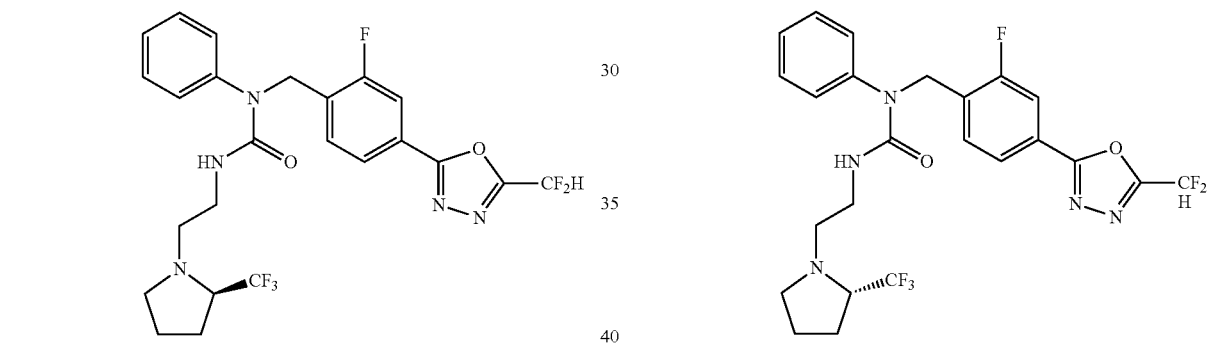

3-(2-bromoethyl)-1-(4-(5-(difluoromethyl)-1,3,4-oxadiazol-2-yl)-2-fluorobenzyl)-1-phenylurea (0.050 g, 0.107 mmol) and (R)-2-(trifluoromethyl)pyrrolidine (0.016 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give (R)-1-(4-(5-(difluoromethyl)-1,3,4-oxadiazol-2-yl)-2-fluorobenzyl)-1-phenyl-3-(2-(2-(trifluoromethyl)pyrrolidin-1-yl)ethyl)urea as yellow oil (0.015 g, 26.7%).

$^1$H NMR (700 MHz, CDCl$_3$) δ 7.89 (dd, 1H, J=8.0, 1.7 Hz), 7.74-7.68 (m, 2H), 7.41-7.34 (m, 2H), 7.35-7.28 (m, 1H), 7.21-7.15 (m, 2H), 7.04-6.82 (m, 1H), 5.10-4.99 (m, 2H), 4.94 (dd, 1H, J=6.6, 3.6 Hz), 3.46 (dddd, 1H, J=13.6, 6.6, 4.9, 3.5 Hz), 3.21 (ddt, 1H, J=14.0, 10.5, 4.0 Hz), 3.10-3.01 (m, 2H), 2.93 (ddd, 1H, J=12.2, 10.6, 4.9 Hz), 2.68 (dt, 1H, J=12.2, 3.9 Hz), 2.31 (ddd, 1H, J=10.5, 8.8, 5.8 Hz), 1.97-1.84 (m, 2H), 1.81-1.72 (m, 1H), 1.74-1.68 (m, 1H); LRMS (ES) m/z 528.1 (M$^+$+1).

3-(2-bromoethyl)-1-(4-(5-(difluoromethyl)-1,3,4-oxadiazol-2-yl)-2-fluorobenzyl)-1-phenylurea (0.050 g, 0.107 mmol) and (S)-2-(trifluoromethyl)pyrrolidine (0.016 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give (S)-1-(4-(5-(difluoromethyl)-1,3,4-oxadiazol-2-yl)-2-fluorobenzyl)-1-phenyl-3-(2-(2-(trifluoromethyl)pyrrolidin-1-yl)ethyl)urea as yellow oil (0.021 g, 37.4%).

$^1$H NMR (700 MHz, CDCl$_3$) δ 7.89 (dd, 1H, J=8.0, 1.7 Hz), 7.74-7.68 (m, 2H), 7.41-7.33 (m, 2H), 7.34-7.28 (m; 1H), 7.21-7.15 (m, 2H), 7.03-6.82 (m, 1H), 5.10-4.98 (m, 2H), 4.94 (dd, 1H, J=6.6, 3.6 Hz), 3.46 (dddd, 1H, J=13.6, 6.5, 4.9, 3.5 Hz), 3.21 (ddt, 1H, J=14.0, 10.5, 4.0 Hz), 3.09-3.00 (m, 2H), 2.93 (ddd, 1H, J=12.2, 10.6, 4.9 Hz), 2.68 (dt, 1H, J=12.2, 3.9 Hz), 2.34-2.27 (m, 1H), 1.96-1.90 (m, 1H), 1.90-1.84 (m, 1H), 1.81-1.75 (m, 1H), 1.75-1.69 (m, 1H); LRMS (ES) m/z 528.0 (M$^+$+1).

Example 417. Compound 21989: 1-(4-(5-(Difluoromethyl)-1,3,4-oxadiazol-2-yl)-2-fluorobenzyl)-3-(2-(4-methylpiperidin-1-yl)ethyl)-1-phenylurea

Example 418. Compound 21990: 1-(4-(5-(Difluoromethyl)-1,3,4-oxadiazol-2-yl)-2-fluorobenzyl)-3-(2-(4-fluoropiperidin-1-yl)ethyl)-1-phenylurea

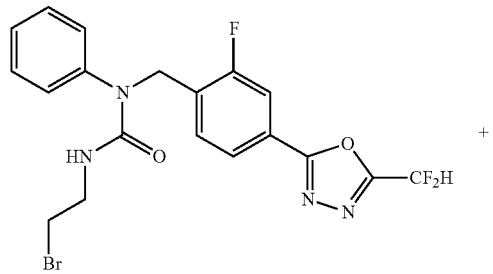

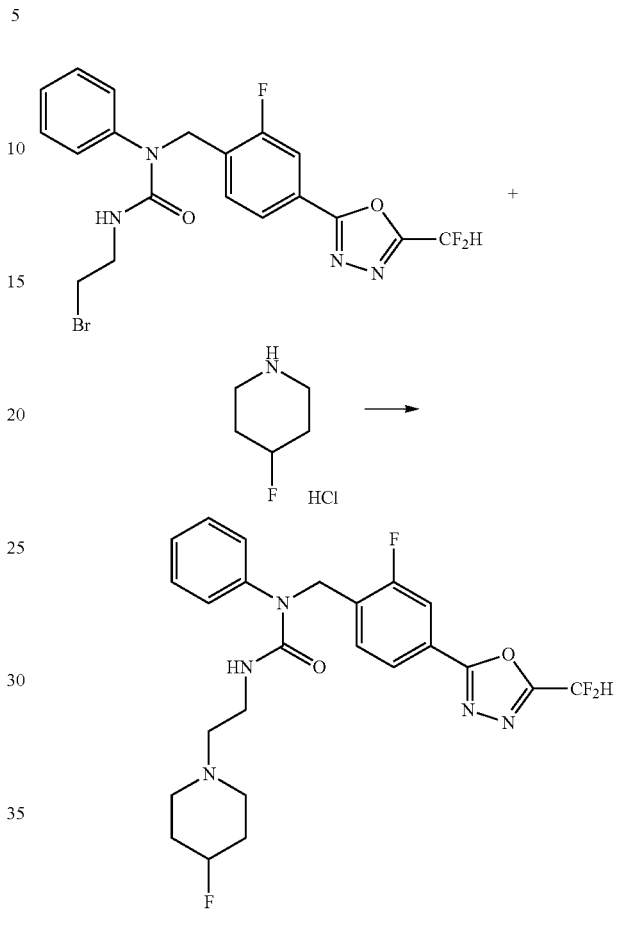

3-(2-bromoethyl)-1-(4-(5-(difluoromethyl)-1,3,4-oxadiazol-2-yl)-2-fluorobenzyl)-1-phenylurea (0.050 g, 0.107 mmol) and 4-methylpiperidine (0.012 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-methylpiperidin-1-yl)ethyl)-1-phenylurea as yellow oil (0.023 g, 44.3%).

$^1$H NMR (700 MHz, CDCl$_3$) δ 7.89 (dd, 1H, J=8.0, 1.7 Hz), 7.75-7.69 (m, 2H), 7.43-7.37 (m, 2H), 7.35-7.30 (m, 1H), 7.21-7.16 (m, 2H), 6.93 (t, 1H, J=51.7 Hz), 5.25 (s, 1H), 5.06 (s, 2H), 3.30 (s, 2H), 2.66 (s, 2H), 2.39 (s, 2H), 1.91 (s, 2H), 1.69 (d, 1H, J=41.4 Hz), 1.51 (d, 2H, J=12.5 Hz), 0.87 (d, 5H, J=6.6 Hz); LRMS (ES) m/z 488.0 (M$^+$+1).

3-(2-bromoethyl)-1-(4-(5-(difluoromethyl)-1,3,4-oxadiazol-2-yl)-2-fluorobenzyl)-1-phenylurea (0.050 g, 0.107 mmol) and 4-fluoropiperidine hydrochloride (0.016 g, 0.117 mmol) were mixed at the room temperature in dichloromethane (1 mL) and then stirred at 50° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-fluoropiperidin-1-yl)ethyl)-1-phenylurea as colorless oil (0.006 g, 11.5%).

$^1$H NMR (700 MHz, CDCl$_3$) δ 7.89 (dd, 1H, J=8.0, 1.7 Hz), 7.75-7.69 (m, 2H), 7.43-7.37 (m, 2H), 7.36-7.31 (m, 1H), 7.21-7.16 (m, 2H), 6.93 (t, 1H, J=51.8 Hz), 5.13 (s, 1H), 5.06 (s, 2H), 4.58 (d, 1H, J=48.7 Hz), 3.30 (q, 2H, J=5.6 Hz), 2.50 (s, 2H), 2.41 (t, 2H, J=6.1 Hz), 2.27-2.21 (m, 2H), 1.80-1.53 (m, 5H); LRMS (ES) m/z 492.0 (M$^+$+1).

Example 419. Compound 21991: 1-(4-(5-(Difluoromethyl)-1,3,4-oxadiazol-2-yl)-2-fluorobenzyl)-3-(2-(4-oxopiperidin-1-yl)ethyl)-1-phenylurea

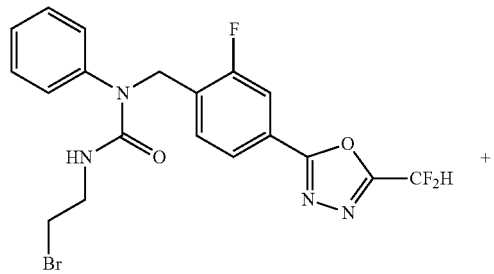

+

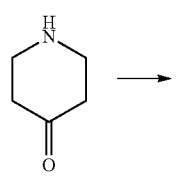

→

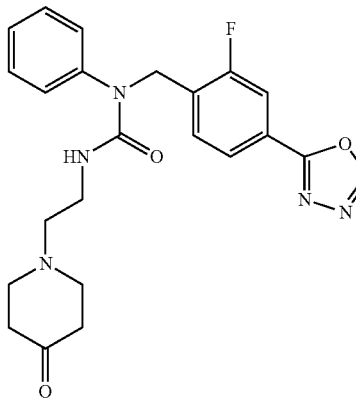

3-(2-bromoethyl)-1-(4-(5-(difluoromethyl)-1,3,4-oxadiazol-2-yl)-2-fluorobenzyl)-1-phenylurea (0.050 g, 0.107 mmol) and piperidin-4-one (0.012 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-oxopiperidin-1-yl)ethyl)-1-phenylurea as colorless oil (0.008 g, 15.4%).

$^1$H NMR (700 MHz, CDCl$_3$) δ 7.89 (dd, 1H, J=8.0, 1.7 Hz), 7.75-7.68 (m, 2H), 7.43-7.37 (m, 2H), 7.36-7.30 (m, 1H), 7.23-7.18 (m, 2H), 6.93 (t, 1H, J=51.7 Hz), 5.10 (t, 1H, J=4.9 Hz), 5.06 (s, 2H), 3.36 (td, 2H, J=6.1, 4.9 Hz), 2.66 (t, 4H, J=6.0 Hz), 2.55 (t, 2H, J=6.1 Hz), 2.23 (t, 4H, J=6.1 Hz); LRMS (ES) m/z 488.3 (M$^+$+1).

Example 420. Compound 21992: 1-(4-(5-(Difluoromethyl)-1,3,4-oxadiazol-2-yl)-2-fluorobenzyl)-3-(2-((3S,5R)-3,5-dimethylpiperazin-1-yl)ethyl)-1-phenylurea

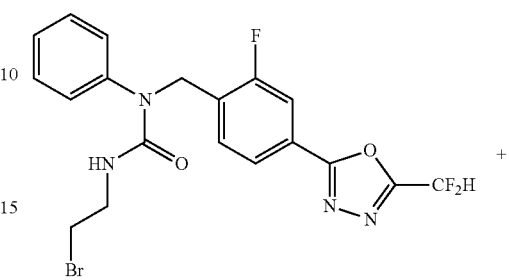

+

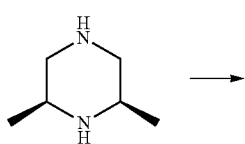

→

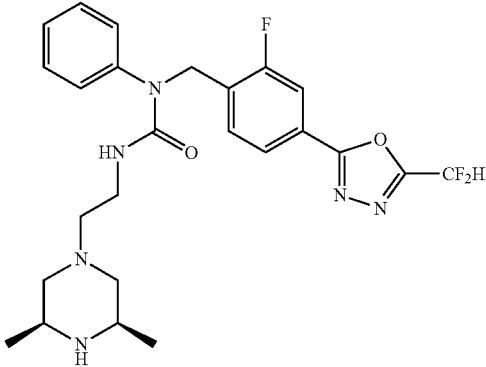

3-(2-bromoethyl)-1-(4-(5-(difluoromethyl)-1,3,4-oxadiazol-2-yl)-2-fluorobenzyl)-1-phenylurea (0.050 g, 0.107 mmol) and (2S,6R)-2,6-dimethylpiperazine (0.013 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-((3S,5R)-3,5-dimethylpiperazin-1-yl)ethyl)-1-phenylurea as yellow oil (0.021 g, 39.2%).

$^1$H NMR (700 MHz, CDCl$_3$) δ 7.89 (dd, 1H, J=8.0, 1.7 Hz), 7.75-7.68 (m, 2H), 7.42-7.36 (m, 2H), 7.35-7.30 (m, 1H), 7.20-7.15 (m, 2H), 7.02-6.83 (m, 1H), 5.08 (s, 1H), 5.05 (s, 2H), 3.32 (td, 2H, J=6.1, 4.8 Hz), 2.59 (d, 4H, J=10.2 Hz), 2.40 (t, 2H, J=6.1 Hz), 1.65 (s, 4H); LRMS (ES) m/z 503.1 (M$^+$+1).

Example 421. Compound 21993: 1-(4-(5-(Difluoromethyl)-1,3,4-oxadiazol-2-yl)-2-fluorobenzyl)-3-(2-(4-methylpiperazin-1-yl)ethyl)-1-phenylurea

Example 422. Compound 21994: 1-(4-(5-(Difluoromethyl)-1,3,4-oxadiazol-2-yl)-2-fluorobenzyl)-3-(2-(4-ethylpiperazin-1-yl)ethyl)-1-phenylurea

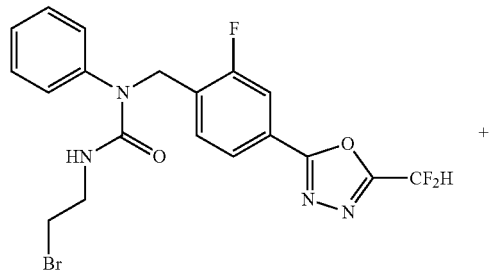

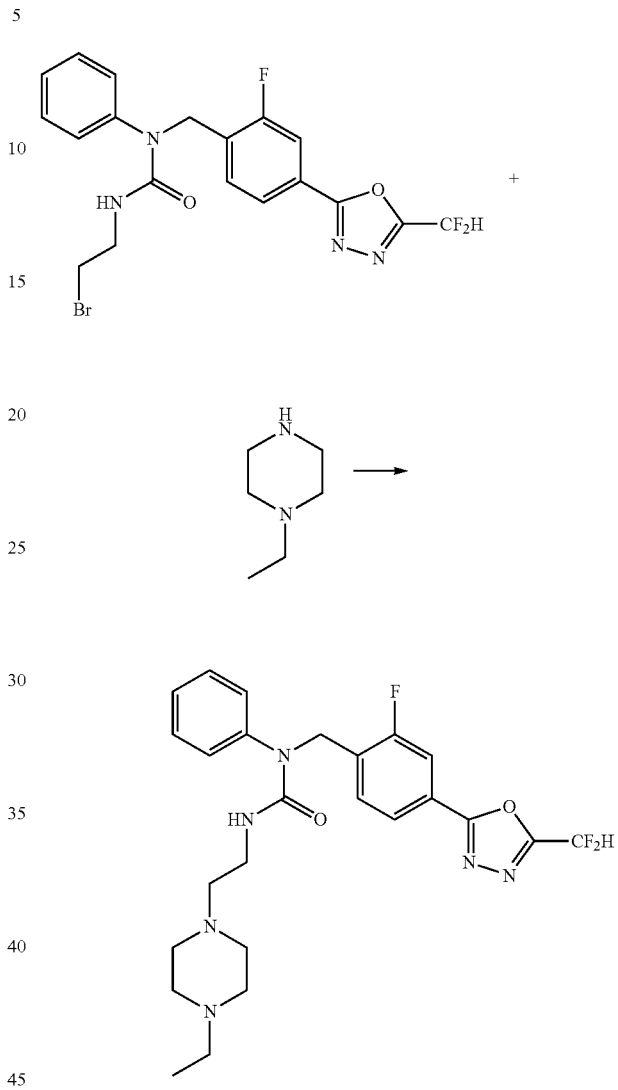

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-methylpiperazine (0.013 mL, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-methylpiperazin-1-yl)ethyl)-1-phenylurea as yellow oil (0.018 g, 34.6%).

$^1$H NMR (700 MHz, CDCl$_3$) δ 7.89 (dd, 1H, J=8.0, 1.7 Hz), 7.75-7.69 (m, 2H), 7.44-7.38 (m, 2H), 7.34 (ddt, 1H, J=8.0, 6.8, 1.2 Hz), 7.21-7.15 (m, 2H), 7.03-6.83 (m, 1H), 5.12 (t, 1H, J=4.8 Hz), 5.06 (s, 2H), 3.31 (td, 2H, J=6.1, 4.8 Hz), 2.42 (t, 7H, J=6.1 Hz), 2.24 (s, 3H), 1.92-1.49 (m, 3H); LRMS (ES) m/z 489.0 (M$^+$+1).

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-ethylpiperazine (0.013 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-ethylpiperazin-1-yl)ethyl)-1-phenylurea as yellow oil (0.019 g, 35.5%).

$^1$H NMR (700 MHz, CDCl$_3$) δ 7.89 (dd, 1H, J=8.0, 1.6 Hz), 7.75-7.69 (m, 2H), 7.40 (dd, 2H, J=8.3, 7.2 Hz), 7.36-7.30 (m, 1H), 7.21-7.16 (m, 2H), 6.93 (t, 1H, J=51.7 Hz), 5.12 (t, 1H, J=4.7 Hz), 5.05 (s, 2H), 3.31 (td, 2H, J=6.1, 4.8 Hz), 2.41 (dt, 12H, J=26.4, 5.0 Hz), 1.09 (t, 3H, J=7.2 Hz); LRMS (ES) m/z 503.0 (M$^+$+1).

Example 423. Compound 21995: 3-(2-(4-Acetylpiperazin-1-yl)ethyl)-1-(4-(5-(difluoromethyl)-1,3,4-oxadiazol-2-yl)-2-fluorobenzyl)-1-phenylurea

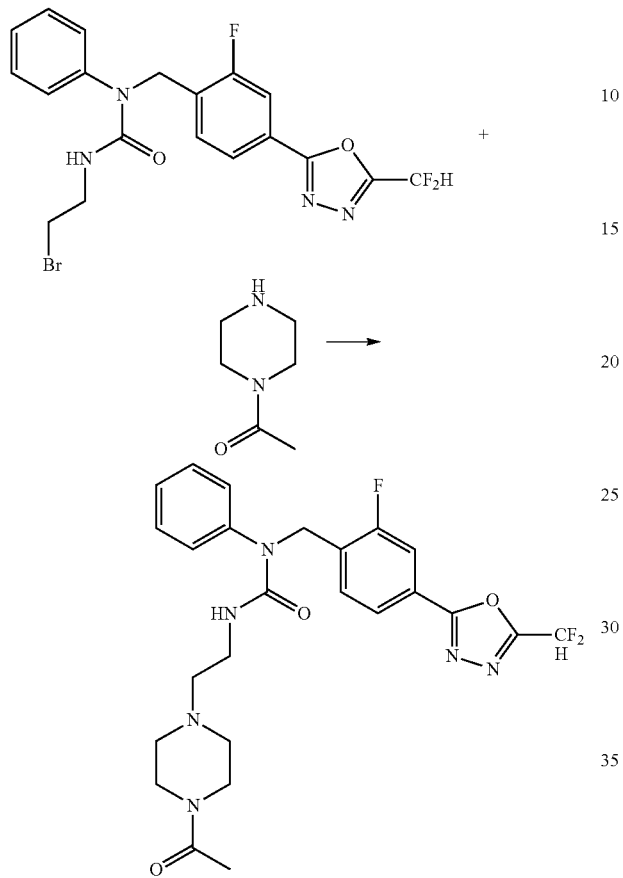

Example 424. Compound 21996: 1-(4-(5-(Difluoromethyl)-1,3,4-oxadiazol-2-yl)-2-fluorobenzyl)-3-(2-(4-(2-hydroxyethyl)piperazin-1-yl)ethyl)-1-phenylurea

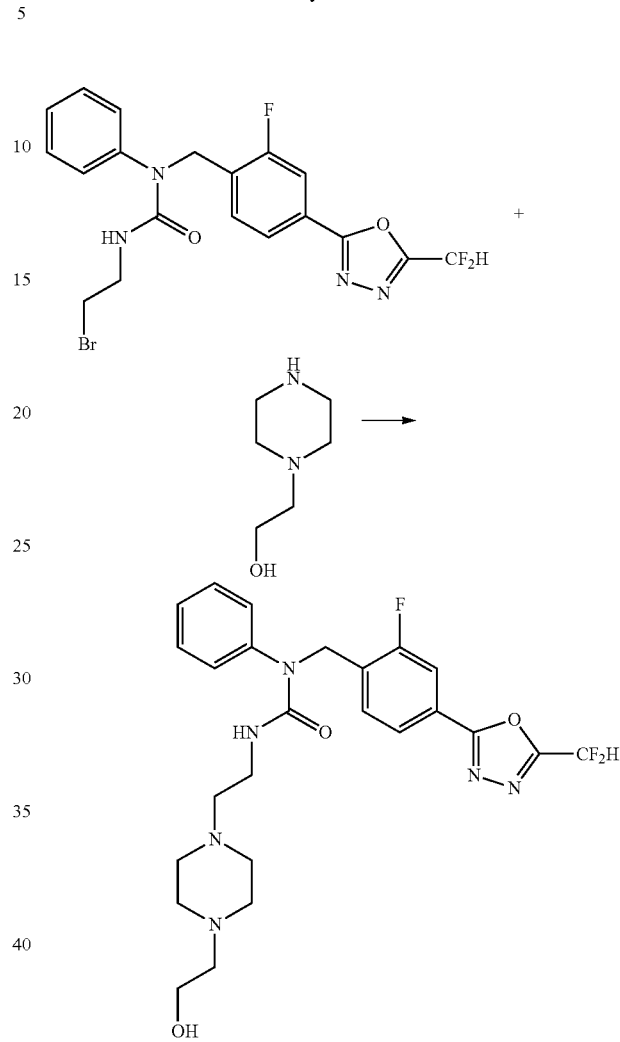

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-(piperazin-1-yl)ethan-1-one (0.015 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(4-acetylpiperazin-1-yl)ethyl)-1-(4-(5-(difluoromethyl)-1,3,4-oxadiazol-2-yl)-2-fluorobenzyl)-1-phenylurea as yellow oil (0.015 g, 27.3%).

$^1$H NMR (700 MHz, CDCl$_3$) δ 7.89 (dd, 1H, J=8.0, 1.7 Hz), 7.75-7.68 (m, 2H), 7.43-7.37 (m, 2H), 7.36-7.31 (m, 1H), 7.21-7.16 (m, 2H), 7.03-6.83 (m, 1H), 5.05 (s, 2H), 5.04-5.01 (m, 1H), 3.42-3.38 (m, 1H), 3.33 (q, 2H, J=5.7 Hz), 3.24 (t, 2H, J=5.0 Hz), 2.44 (t, 2H, J=6.0 Hz), 2.33 (dt, 4H, J=30.2, 5.1 Hz), 2.07 (s, 3H); LRMS (ES) m/z 517.3 (M$^+$+1).

3-(2-bromoethyl)-1-(4-(5-(difluoromethyl)-1,3,4-oxadiazol-2-yl)-2-fluorobenzyl)-1-phenylurea (0.050 g, 0.107 mmol) and 2-(piperazin-1-yl)ethan-1-ol (0.015 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-(2-hydroxyethyl)piperazin-1-yl)ethyl)-1-phenylurea as white solid (0.010 g, 18.1%).

$^1$H NMR (700 MHz, CDCl$_3$) δ 7.89 (dd, J=8.0, 1.7 Hz), 7.75-7.68 (m, 2H), 7.43-7.37 (m, 2H), 7.33 (ddt, 1H, J=8.0, 6.8, 1.2 Hz), 7.21-7.15 (m, 2H), 6.93 (t, 1H, J=51.7 Hz), 5.10 (t, 1H, J=4.8 Hz), 5.05 (s, 2H), 3.63-3.59 (m, 2H), 3.32 (td, 2H, J=6.1, 4.8 Hz), 2.82-1.92 (m, 14H), LRMS (ES) m/z 519.0 (M$^+$+1).

Example 425. Compound 21997: 1-(4-(5-(Difluoromethyl)-1,3,4-oxadiazol-2-yl)-2-fluorobenzyl)-3-(2-(4-(2-methoxyethyl)piperazin-1-yl)ethyl)-1-phenylurea

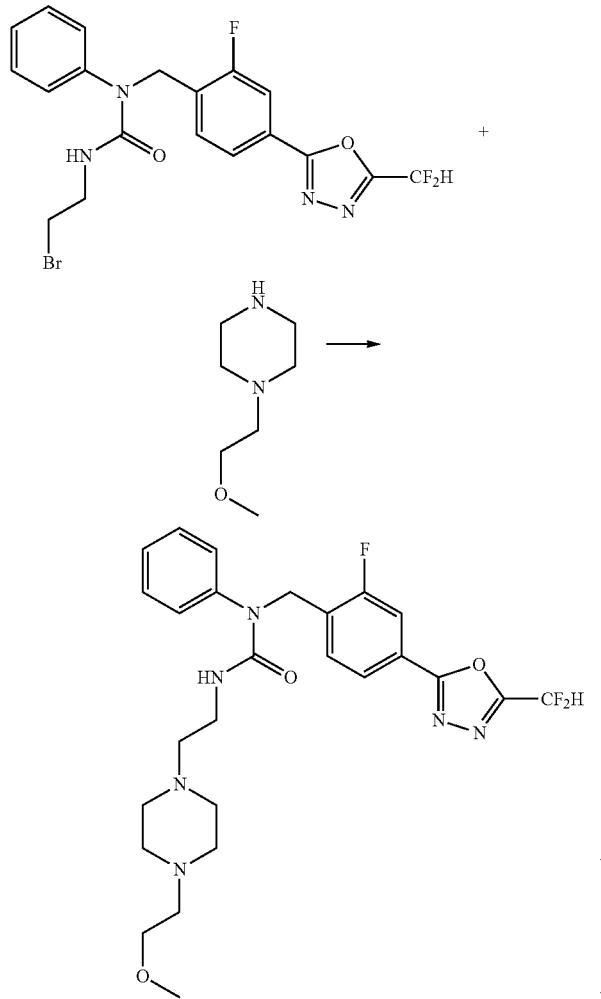

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-(2-methoxyethyl)piperazine (0.017 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂ plate, 20×20×1 mm; methanol/dichloromethane=10%) to give 1-(4-(5-(difluoromethyl)-1,3,4-oxadiazol-2-yl)-2-fluorobenzyl)-3-(2-(4-(2-methoxyeth yl)piperazin-1-yl)ethyl)-1-phenylurea as yellow oil (0.020 g, 35.2%).

$^1$H NMR (700 MHz, CDCl$_3$) δ 7.89 (dd, 1H, J=8.0, 1.7 Hz), 7.75-7.69 (m, 2H), 7.43-7.37 (m, 2H), 7.35-7.30 (m, 1H), 7.21-7.16 (m, 2H), 6.93 (s, 1H), 5.13 (s, 1H), 5.05 (s, 2H), 3.50 (t, 2H, J=5.6 Hz), 3.36 (s, 3H), 3.31 (q, 2H, J=5.7 Hz), 2.47 (dt, 12H, J=74.2, 5.9 Hz); LRMS (ES) m/z 533.0 (M$^+$+1).

Example 426. Compound 21998: 1-(4-(5-(Difluoromethyl)-1,3,4-oxadiazol-2-yl)-2-fluorobenzyl)-3-(2-(4-(3-hydroxypropyl)piperazin-1-yl)ethyl)-1-phenylurea

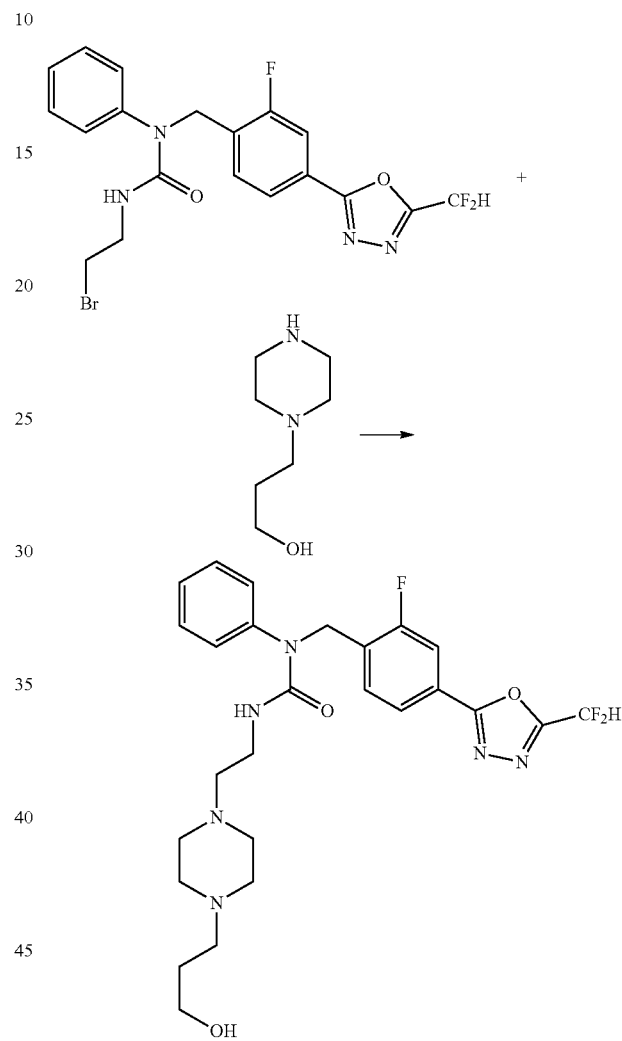

3-(2-bromoethyl)-1-(4-(5-(difluoromethyl)-1,3,4-oxadiazol-2-yl)-2-fluorobenzyl)-1-phenylurea (0.050 g, 0.107 mmol) and 3-(piperazin-1-yl)propan-1-ol (0.017 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂ plate, 20×20×1 mm; methanol/dichloromethane=10%) to give 1-(4-(5-(difluoromethyl)-1,3,4-oxadiazol-2-yl)-2-fluorobenzyl)-3-(2-(4-(3-hydroxypropyl)piperazin-1-yl)ethyl)-1-phenylurea as yellow oil (0.011 g, 19.4%).

$^1$H NMR (700 MHz, CDCl$_3$) δ 7.89 (dd, 1H, J=8.0, 1.7 Hz), 7.75-7.68 (m, 2H), 7.43-7.37 (m, 2H), 7.35-7.30 (m,

1H), 7.20-7.16 (m, 2H), 7.02-6.83 (m, 1H), 5.07 (t, 1H, J=4.8 Hz), 5.05 (s, 2H), 3.82-3.77 (m, 2H), 3.30 (td, 2H, J=6.1, 4.8 Hz), 2.48 (dt, 12H, J=107.7, 5.9 Hz), 1.71 (dtd, 2H, J=6.7, 5.4, 5.0, 3.3 Hz); LRMS (ES) m/z 533.1 (M$^+$+1).

Example 427. Compound 21999: 3-(2-(4-Acetyl-1,4-diazepan-1-yl)ethyl)-1-(4-(5-(difluoromethyl)-1,3,4-oxadiazol-2-yl)-2-fluorobenzyl)-1-phenylurea

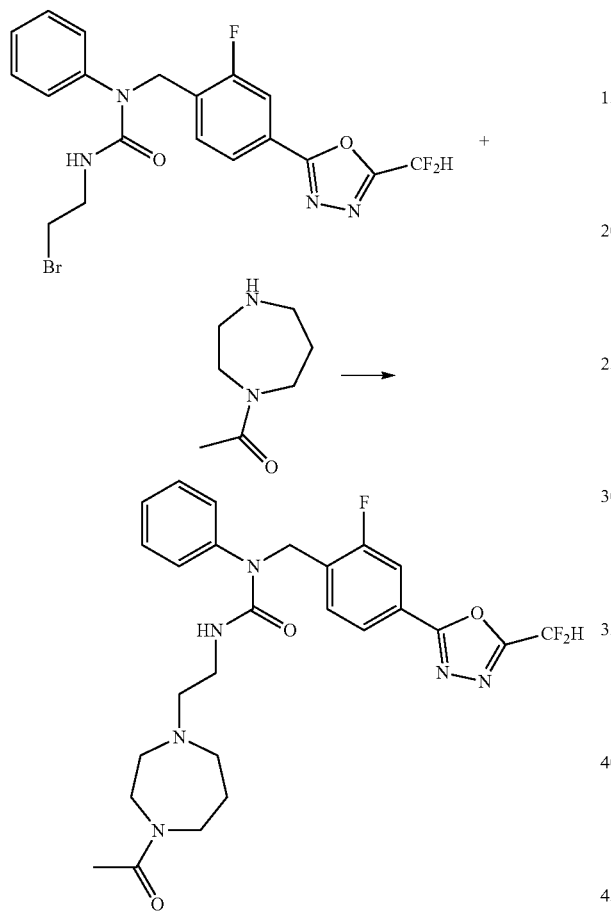

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-(1,4-diazepan-1-yl)ethan-1-one (0.017 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(4-acetyl-1,4-diazepan-1-yl)ethyl)-1-(4-(5-(difluoromethyl)-1,3,4-oxadiazol-2-yl)-2-fluorobenzyl)-1-phenylurea as yellow oil (0.022 g, 38.9%).

$^1$H NMR (700 MHz, CDCl$_3$) δ 7.89 (dt, 1H, J=7.9, 1.2 Hz), 7.75-7.67 (m, 2H), 7.43-7.37 (m, 2H), 7.37-7.30 (m, 1H), 7.21-7.16 (m, 2H), 7.04-6.82 (m, 1H), 5.10-5.02 (m, 1H), 5.05 (s, 2H), 3.43 (t, 1H, J=6.3 Hz), 3.41 (t, 1H, J=5.0 Hz), 3.33 (t, 1H, J=6.3 Hz), 3.32-3.26 (m, 3H), 2.61-2.57 (m, 1H), 2.57-2.47 (m, 5H), 2.08-2.04 (m, 3H), 1.71 (s, 1H), 1.62 (dt, 2H, J=12.0, 6.0 Hz); LRMS (ES) m/z 531.0 (M++1).

Example 428. Compound 22000: 3-(2-(4-Benzyl-1,4-diazepan-1-yl)ethyl)-1-(4-(5-(difluoromethyl)-1,3,4-oxadiazol-2-yl)-2-fluorobenzyl)-1-phenylurea

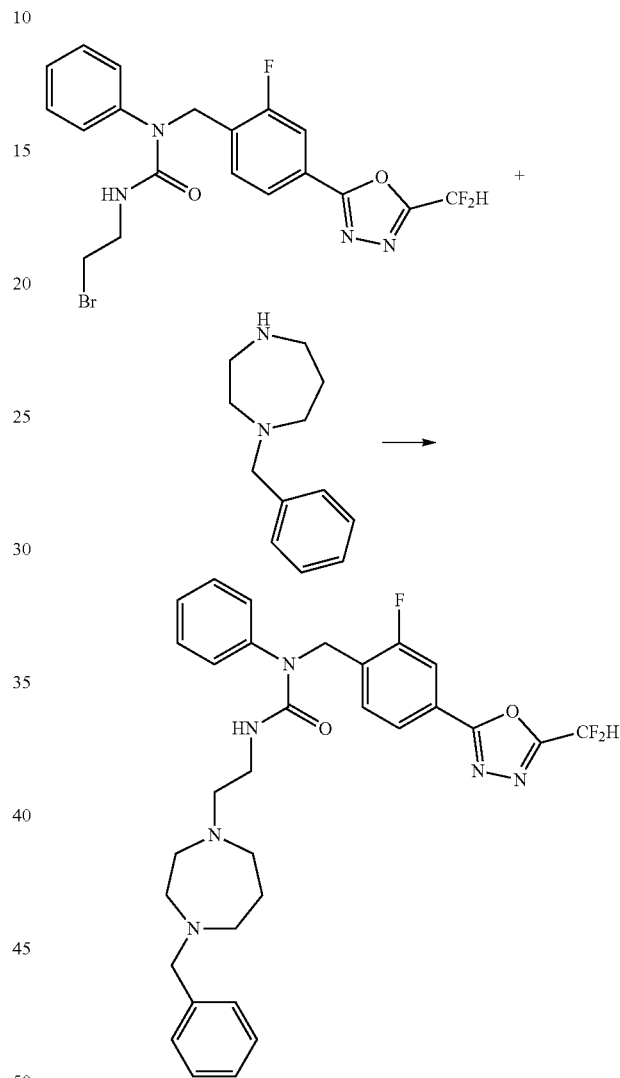

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-benzyl-1,4-diazepane (0.022 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(4-benzyl-1,4-diazepan-1-yl)ethyl)-1-(4-(5-(difluoromethyl)-1,3,4-oxadiazol-2-yl)-2-fluorobenzyl)-1-phenylurea as colorless oil (0.009 g, 14.6%).

$^1$H NMR (700 MHz, CDCl$_3$) δ 7.89 (dd, 1H, J=8.0, 1.7 Hz), 7.75-7.69 (m, 2H), 7.42-7.36 (m, 2H), 7.37-7.28 (m, 5H), 7.29-7.24 (m, 1H), 7.22-7.17 (m, 2H), 7.02-6.83 (m, 1H), 5.21 (t, 1H, J=4.7 Hz), 5.06 (s, 2H), 3.54 (s, 2H), 3.28 (q, 2H, J=5.5 Hz), 2.59 (s, 2H), 2.56-2.49 (m, 4H), 2.46 (s, 2H), 2.42 (s, 2H), 1.89-1.68 (m, 2H); LRMS (ES) m/z 579.0 (M$^+$+1).

Example 429. Compound 22001: 3-(2-(4-(Cyclopropanecarbonyl)piperazin-1-yl)ethyl)-1-(4-(5-(difluoromethyl)-1,3,4-oxadiazol-2-yl)-2-fluorobenzyl)-1-phenylurea $^1$H NMR (700 MHz, CDCl$_3$) δ 7.89 (dd, 1H, J=8.0, 1.7 Hz), 7.75-7.68 (m, 2H), 7.43-7.38 (m, 2H), 7.37-7.31 (m, 1H), 7.21-7.16 (m, 2H), 6.93 (t, 1H, J=51.7 Hz), 5.06 (s, 3H), 3.44 (d, 4H, J=34.7 Hz), 3.34 (q, 2H, J=5.7 Hz), 2.45 (t, 2H, J=6.0 Hz), 2.39 (s, 2H), 2.32 (s, 2H), 1.03-0.94 (m, 2H), 0.80-0.72 (m, 2H); LRMS (ES) m/z 543.3 (M$^+$+1).

Example 430. Compound 22002: 1-(4-(5-(Difluoromethyl)-1,3,4-oxadiazol-2-yl)-2-fluorobenzyl)-3-(2-(4-(3-(dimethylamino)propyl)piperazin-1-yl)ethyl)-1-phenylurea

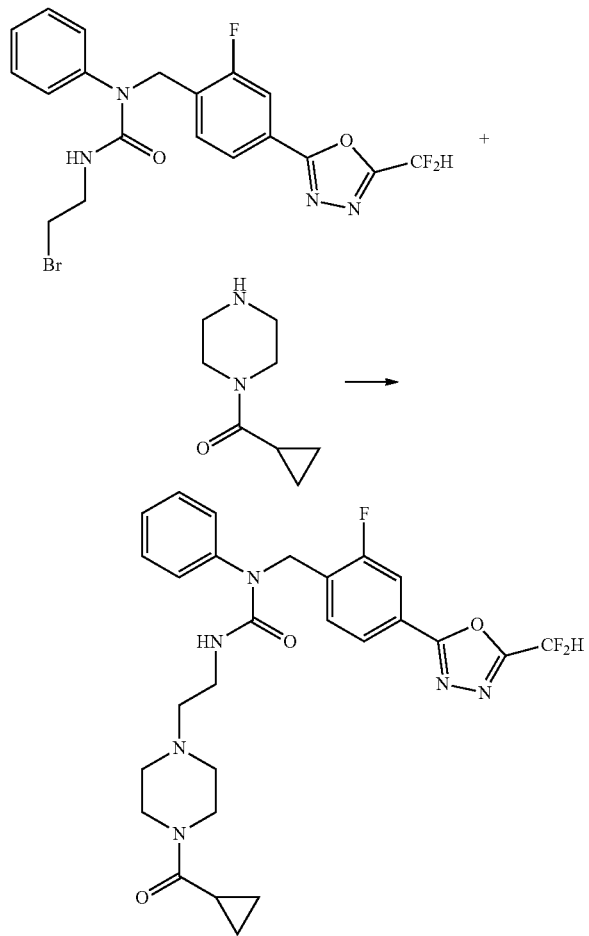

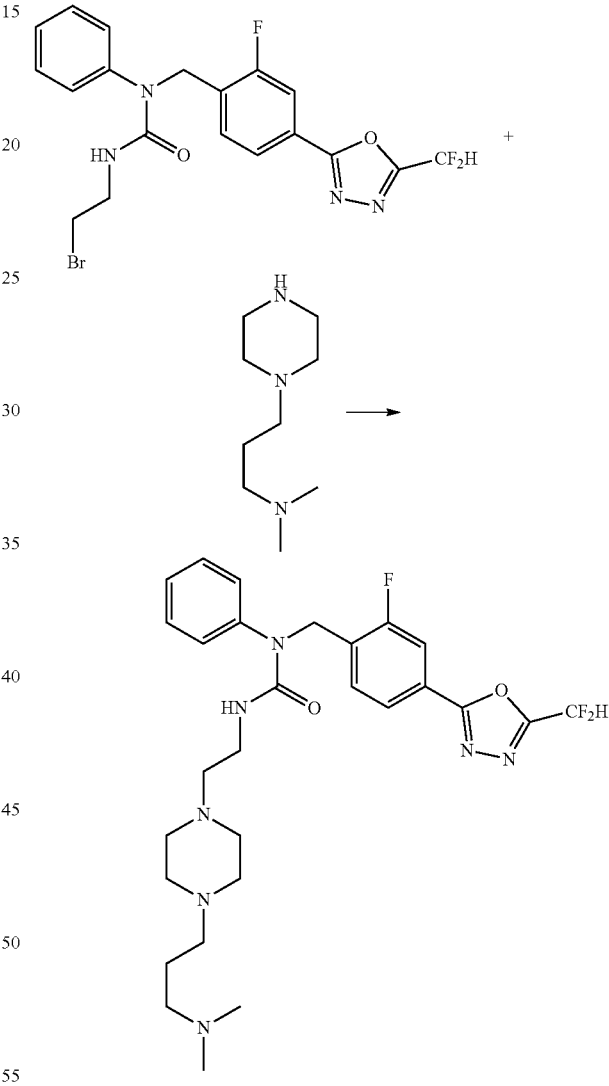

3-(2-bromoethyl)-1-(4-(5-(difluoromethyl)-1,3,4-oxadiazol-2-yl)-2-fluorobenzyl)-1-phenylurea (0.050 g, 0.107 mmol) and cyclopropyl(piperazin-1-yl)methanone (0.018 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(4-(cyclopropanecarbonyl)piperazin-1-yl)ethyl)-1-(4-(5-(difluoromethyl)-1,3,4-oxadiazol-2-yl)-2-fluorobenzyl)-1-phenylurea as white foam (0.024 g, 41.5%).

3-(2-bromoethyl)-1-(4-(5-(difluoromethyl)-1,3,4-oxadiazol-2-yl)-2-fluorobenzyl)-1-phenylurea (0.050 g, 0.107 mmol) and N,N-dimethyl-3-(piperazin-1-yl)propan-1-amine (0.020 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂ plate, 20×20×1 mm; methanol/dichloromethane=10%) to give 1-(4-(5-(difluoromethyl)-1,3,4-oxadiazol-2-yl)-2-fluorobenzyl)-3-(2-(4-(3-(dimethylamino)propyl)piperazin-1-yl)ethyl)-1-phenylurea as colorless oil (0.005 g, 8.4%).

¹H NMR (700 MHz, CDCl₃) δ 7.89 (dd, 1H, J=8.0, 1.7 Hz), 7.75-7.68 (m, 2H), 7.43-7.36 (m, 2H), 7.35-7.30 (m, 1H), 7.20-7.16 (m, 2H), 7.04-6.82 (m, 1H), 5.12 (t, 1H, J=4.7 Hz), 5.04 (d, 2H, J=12.5 Hz), 3.30 (td, 2H, J=6.1, 4.7 Hz), 2.69-2.05 (m, 20H), 1.72-1.63 (m, 2H); LRMS (ES) m/z 543.3 (M⁺+1).

Example 431. Compound 22003: 1-(4-(5-(Difluoromethyl)-1,3,4-oxadiazol-2-yl)-2-fluorobenzyl)-3-(2-(4-morpholinopiperidin-1-yl)ethyl)-1-phenylurea

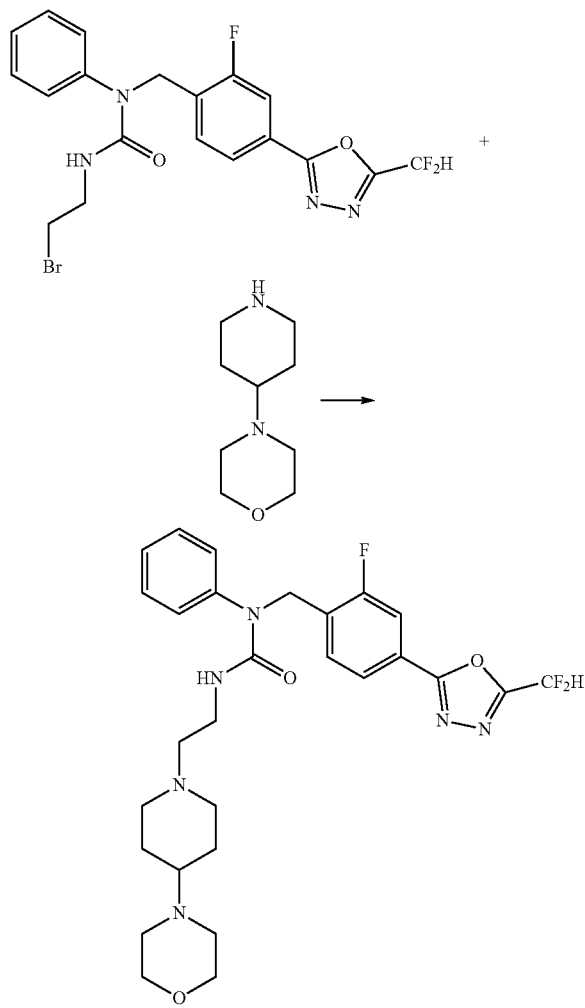

3-(2-bromoethyl)-1-(4-(5-(difluoromethyl)-1,3,4-oxadiazol-2-yl)-2-fluorobenzyl)-1-phenylurea (0.050 g, 0.107 mmol) and 4-(piperidin-4-yl)morpholine (0.020 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂ plate, 20×20×1 mm; methanol/dichloromethane=10%) to give 1-(4-(5-(difluoromethyl)-1,3,4-oxadiazol-2-yl)-2-fluorobenzyl)-3-(2-(4-morpholinopiperidin-1-yl)ethyl)-1-phenylurea as yellow oil (0.019 g, 31.9%).

¹H NMR (700 MHz, CDCl₃) δ 7.89 (dd, 1H, J=8.0, 1.7 Hz), 7.75-7.68 (m, 2H), 7.42-7.36 (m, 2H), 7.34-7.28 (m, 1H), 7.21-7.16 (m, 2H), 7.03-6.83 (m, 1H), 5.11 (t, 1H, J=4.9 Hz), 5.04 (d, 2H, J=12.4 Hz), 3.75-3.71 (m, 4H), 3.30 (q, 2H, J=5.7 Hz), 2.78 (d, 2H, J=11.2 Hz), 2.51 (t, 4H, J=4.7 Hz), 2.39 (t, 2H, J=6.1 Hz), 2.13 (td, 1H, J=12.2, 11.8, 6.1 Hz), 1.93 (t, 2H, J=11.5 Hz), 1.71 (d, 2H, J=12.3 Hz), 1.25-1.17 (m, 2H); LRMS (ES) m/z 560.3 (M⁺+1).

Example 432. Compound 22004: 3-(2-(4-Benzylpiperidin-1-yl)ethyl)-1-(4-(5-(difluoromethyl)-1,3,4-oxadiazol-2-yl)-2-fluorobenzyl)-1-phenylurea

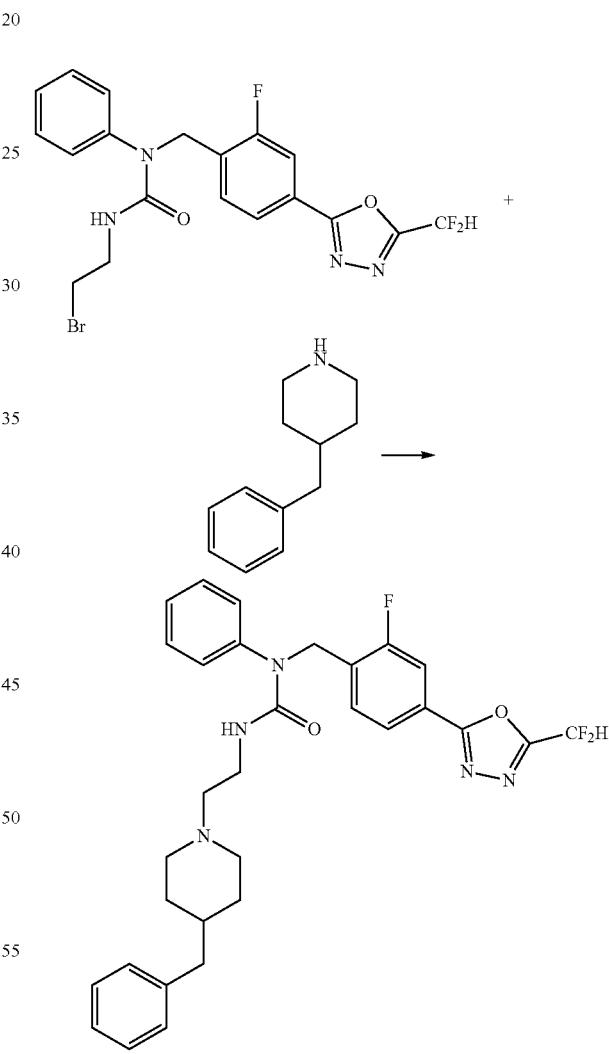

3-(2-bromoethyl)-1-(4-(5-(difluoromethyl)-1,3,4-oxadiazol-2-yl)-2-fluorobenzyl)-1-phenylurea (0.050 g, 0.107 mmol) and 4-benzylpiperidine (0.021 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(4-benzylpiperidin-1-yl)ethyl)-1-(4-(5-(difluoromethyl)-1,3,4-oxadiazol-2-yl)-2-fluorobenzyl)-1-phenylurea as colorless oil (0.018 g, 30.0%).

$^1$H NMR (700 MHz, CDCl$_3$) δ 7.89 (dd, 1H, J=8.0, 1.7 Hz), 7.75-7.69 (m, 2H), 7.42-7.36 (m, 2H), 7.36-7.30 (m, 3H), 7.25-7.20 (m, 1H), 7.21-7.16 (m, 2H), 7.15-7.11 (m, 2H), 6.89 (d, 1H, J=51.7 Hz), 5.21 (t, 1H, J=4.7 Hz), 5.06 (s, 2H), 3.28 (q, 2H, J=5.7 Hz), 2.69-2.64 (m, 2H), 2.47 (d, 2H, J=7.0 Hz), 2.36 (t, 2H, J=6.1 Hz), 1.86 (t, 2H, J=11.5 Hz), 1.79-1.57 (m, 2H), 1.52 (d, 2H, J=12.6 Hz), 0.95-0.88 (m, 1H); LRMS (ES) m/z 559.1 (M$^+$+1).

Example 433. Compound 22005: 1-(4-(5-(Difluoromethyl)-1,3,4-oxadiazol-2-yl)-2-fluorobenzyl)-3-(2-(4-(3-methyl-1,2,4-oxadiazol-5-yl)piperidin-1-yl)ethyl)-1-phenylurea

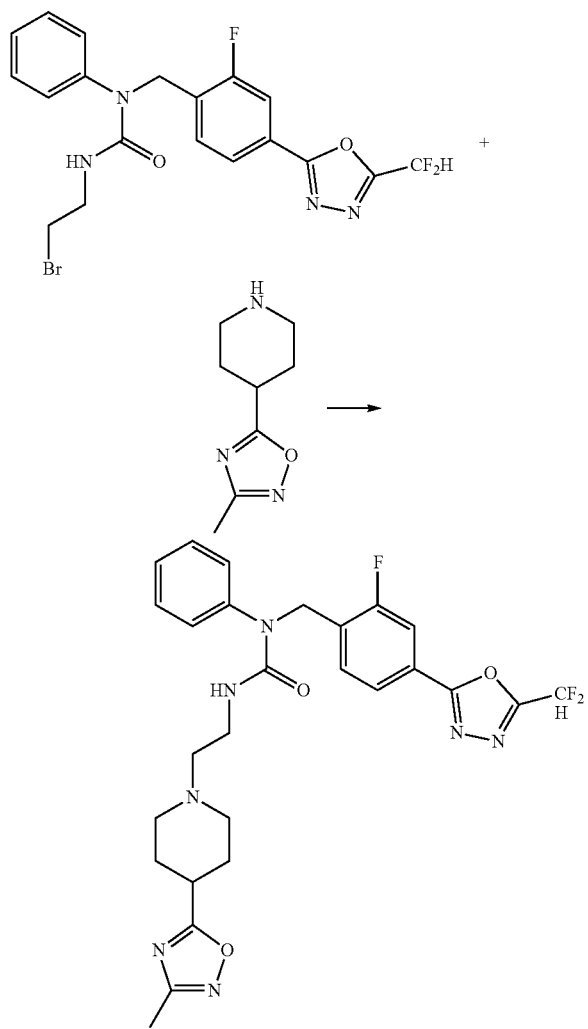

3-(2-bromoethyl)-1-(4-(5-(difluoromethyl)-1,3,4-oxadiazol-2-yl)-2-fluorobenzyl)-1-phenylurea (0.050 g, 0.107 mmol) and 3-methyl-5-(piperidin-4-yl)-1,2,4-oxadiazole (0.020 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-(3-methyl-1,2,4-oxadiazol-5-yl)piperidin-1-yl)ethyl)-1-phenylurea as colorless oil (0.003 g, 5.1%).

$^1$H NMR (700 MHz, CDCl$_3$) δ 7.89 (dd, 1H, J=8.0, 1.6 Hz), 7.75-7.68 (m, 2H), 7.43-7.37 (m, 2H), 7.34-7.28 (m, 1H), 7.21-7.16 (m, 2H), 6.93 (t, 1H, J=51.7 Hz), 5.12 (t, 1H, J=4.7 Hz), 5.05 (s, 2H), 3.31 (td, 2H, J=6.0, 4.7 Hz), 2.83 (tt, 1H, J=11.3, 3.9 Hz), 2.76 (d, 2H, J=11.7 Hz), 2.43 (t, 2H, J=6.0 Hz), 2.41 (s, 3H), 2.13-2.06 (m, 2H), 1.98-1.92 (m, 2H), 1.65-1.53 (m, 2H); LRMS (ES) m/z 564.0 (M$^+$+1).

Example 434. Compound 22006: 3-(2-(Benzyl(ethyl)amino)ethyl)-1-(4-(5-(difluoromethyl)-1,3,4-oxadiazol-2-yl)-2-fluorobenzyl)-1-phenylurea

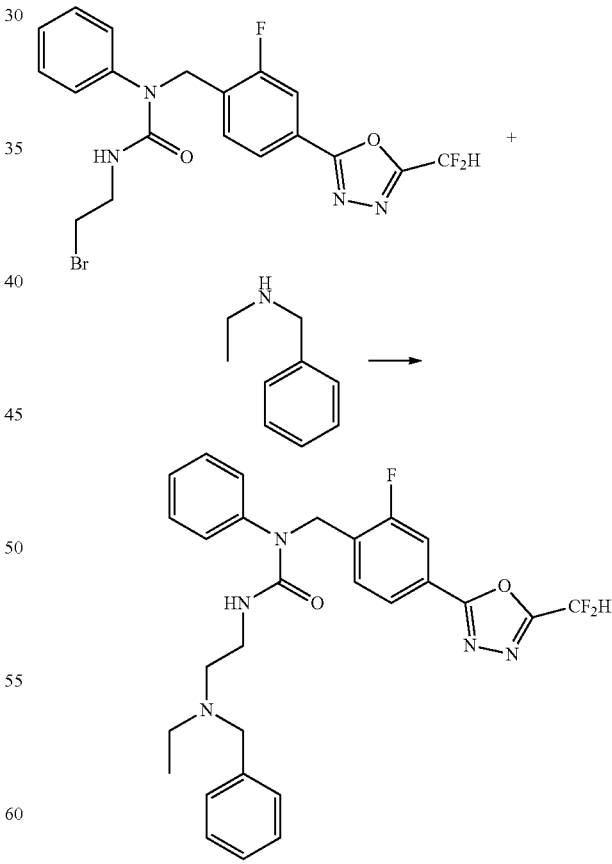

3-(2-bromoethyl)-1-(4-(5-(difluoromethyl)-1,3,4-oxadiazol-2-yl)-2-fluorobenzyl)-1-phenylurea (0.050 g, 0.107 mmol) and N-benzylethanamine (0.016 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(benzyl(ethyl)amino) ethyl)-1-(4-(5-(difluoromethyl)-1,3,4-oxadiazol-2-yl)-2-fluorobenzyl)-1-phenylurea as colorless oil (0.013 g, 23.3%).

$^1$H NMR (700 MHz, CDCl$_3$) δ 7.88 (dd, 1H, J=8.0, 1.6 Hz), 7.75-7.68 (m, 2H), 7.48-7.43 (m, 2H), 7.42-7.37 (m, 1H), 7.24-7.18 (m, 5H), 7.02-6.82 (m, 3H), 5.19 (t, 1H, J=4.6 Hz), 5.05 (s, 2H), 3.43 (s, 2H), 3.33-3.28 (m, 2H), 2.50 (dd, 2H, J=6.6, 5.1 Hz), 2.36 (q, 2H, J=7.1 Hz), 0.85 (t, 3H, J=7.1 Hz); LRMS (ES) m/z 524.1 (M$^+$+1).

Example 435. Compound 22007: 1-(4-(5-(Difluoromethyl)-1,3,4-oxadiazol-2-yl)-2-fluorobenzyl)-1-phenyl-3-(2-(4-phenylpiperazin-1-yl)ethyl)urea

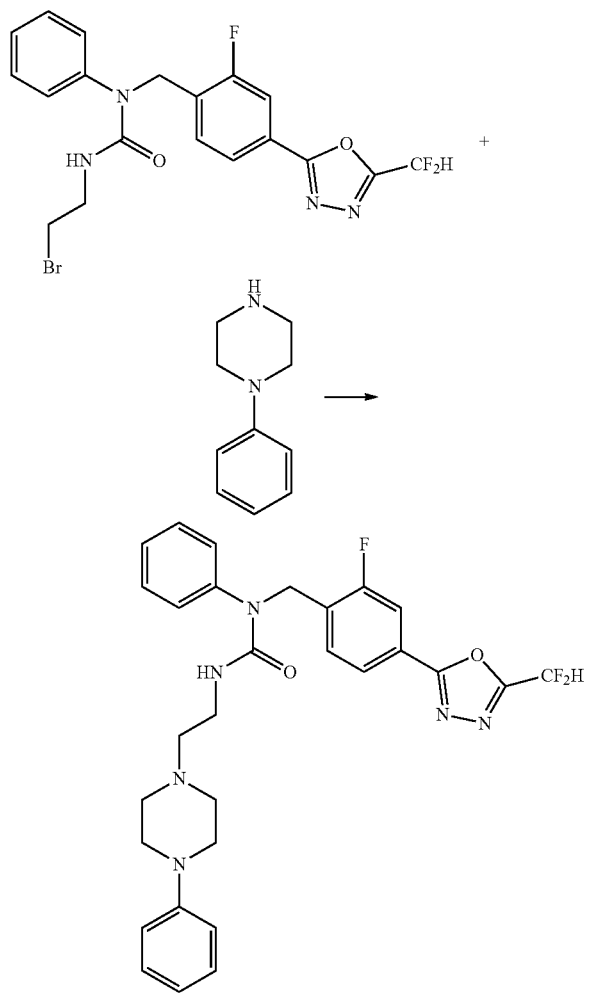

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-phenylpiperazine (0.019 g, 0.117 mmol) were mixed at the room temperature in acetonitrile (1 mL) and then stirred at 100° C. for 18 hr and cooled down to the room temperature to terminate the reaction. Then, water, was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-1-phenyl-3-(2-(4-phenylpiperazin-1-yl)ethyl)urea as white solid (0.017 g, 29.0%).

$^1$H NMR (700 MHz, CDCl$_3$) δ 7.89 (dd, 1H, J=8.0, 1.7 Hz), 7.75-7.69 (m, 2H), 7.40-7.33 (m, 2H), 7.34-7.24 (m, 2H), 7.21-7.16 (m, 2H), 6.94-6.84 (m, 5H), 5.13 (t, 1H, J=4.9 Hz), 5.06 (s, 2H), 3.36 (q, 2H, J=5.6 Hz), 2.99 (t, 4H, J=5.0 Hz), 2.50 (dt, 6H, J=23.2, 5.5 Hz); LRMS (ES) m/z 551.0 (M$^+$+1).

Example 436. Compound 22008: 1-(4-(5-(Difluoromethyl)-1,3,4-oxadiazol-2-yl)-2-fluorobenzyl)-1-phenyl-3-(2-(4-(pyridin-2-yl)piperazin-1-yl)ethyl) urea

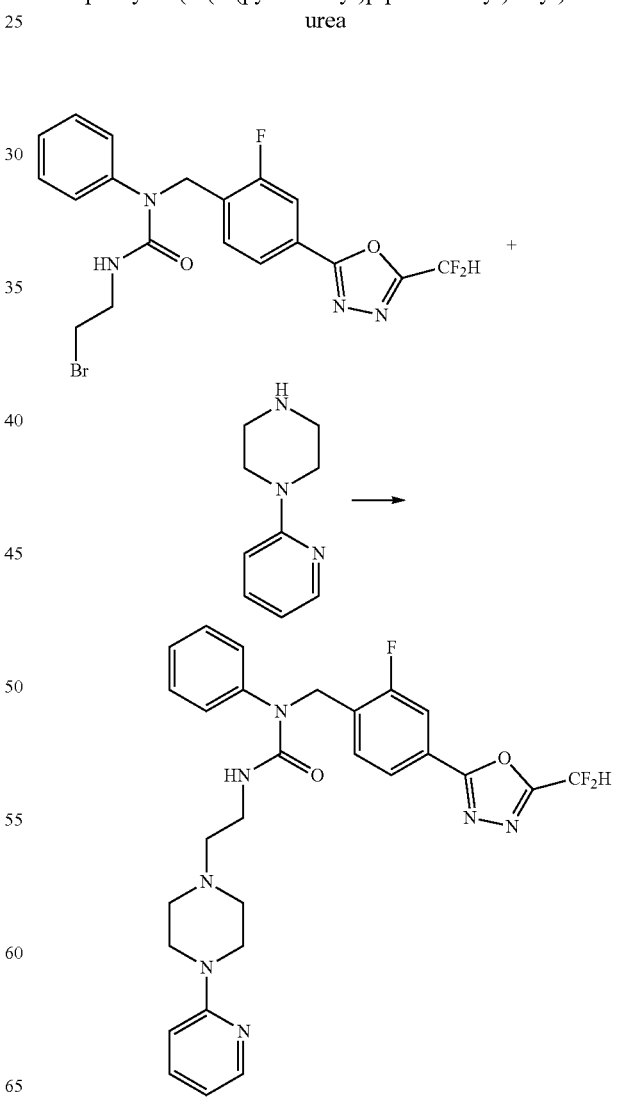

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-(pyridin-2-yl)piperazine (0.019 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-1-phenyl-3-(2-(4-(pyridin-2-yl)piperazin-1-yl)ethyl)urea as colorless oil (0.015 g, 25.5%).

$^1$H NMR (700 MHz, CDCl$_3$) δ 8.20 (ddd, 1H, J=4.9, 2.0, 0.9 Hz), 7.89 (dd, 1H, J=8.0, 1.7 Hz), 7.75-7.69 (m, 2H), 7.49 (ddd, 1H, J=8.6, 7.1, 2.0 Hz), 7.40-7.35 (m, 2H), 7.31-7.26 (m, 1H), 7.21-7.17 (m, 2H), 7.02-6.82 (m, 1H), 6.65 (ddd 7.1, 4.9, 0.8 Hz), 6.62 (dt, 1H, J=8.6, 0.9 Hz), 5.14 (t, 1H, J=4.6 Hz), 5.06 (s, 2H), 3.39-3.31 (m, 4H), 3.34 (s, 2H), 2.47 (td, 6H, J=7.0, 5.8, 3.3 Hz); LRMS (ES) m/z 552.1 (M$^+$+1).

Example 437. Compound 22009: 1-(4-(5-(Difluoromethyl)-1,3,4-oxadiazol-2-yl)-2-fluorobenzyl)-1-phenyl-3-(2-(4-(pyridin-4-yl)piperazin-1-yl)ethyl)urea

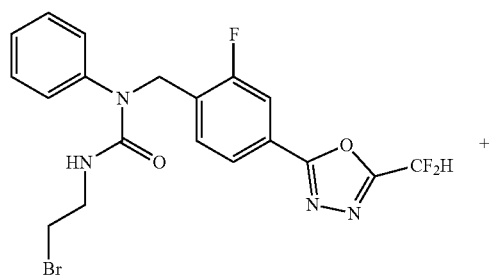

+

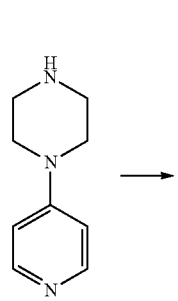

→

-continued

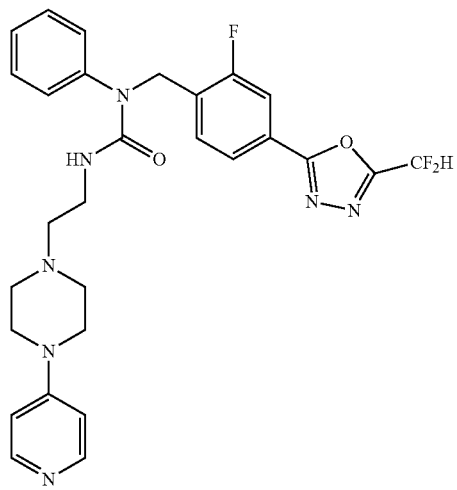

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-(pyridin-4-yl)piperazine (0.019 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-1-phenyl-3-(2-(4-(pyridin-4-yl)piperazin-1-yl)ethyl)urea as colorless oil (0.012 g, 20.4%).

$^1$H NMR (700 MHz, CDCl$_3$) δ 8.31-8.27 (m, 2H), 7.88 (dd, 1H, J=8.0, 1.7 Hz), 7.75-7.68 (m, 2H), 7.40-7.35 (m, 2H), 7.31-7.26 (m, 1H), 7.21-7.14 (m, 2H), 7.02-6.82 (m, 2H), 6.66-6.61 (m, 2H), 5.05 (d, 3H, J=8.9 Hz), 3.36 (td, 2H, J=6.1, 4.9 Hz), 3.15-3.11 (m, 4H), 2.51-2.46 (m, 6H); LRMS (ES) m/z 552.0 (M$^+$+1).

Example 438. Compound 22010: 1-(4-(5-(Difluoromethyl)-1,3,4-oxadiazol-2-yl)-2-fluorobenzyl)-3-(2-(4-(4-fluorophenyl)piperazin-1-yl)ethyl)-1-phenylurea

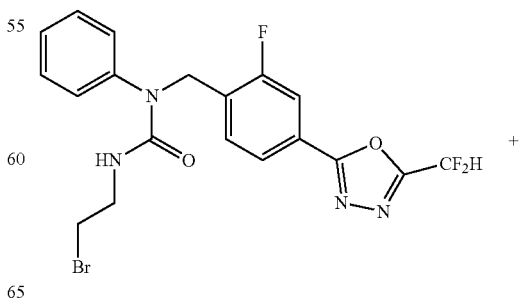

+

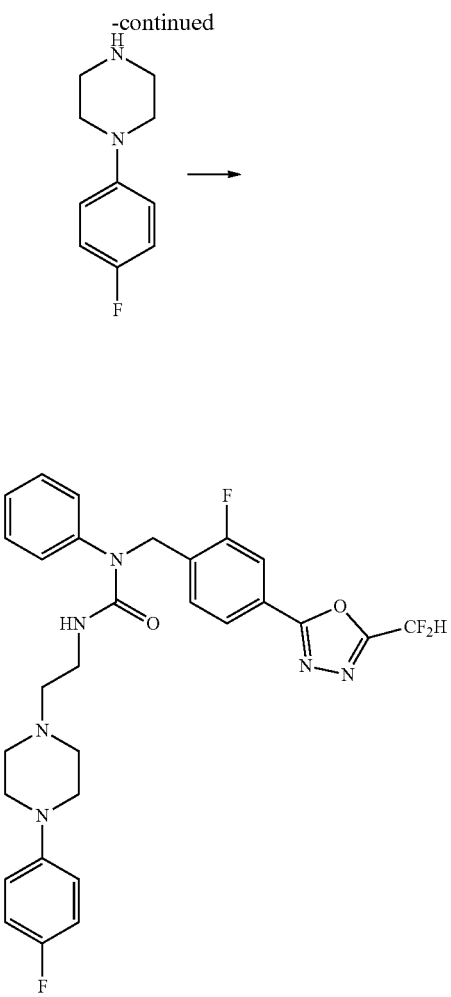

Example 439. Compound 22011: 3-(2-(4-(Benzo[d]isoxazol-3-yl)piperazin-1-yl)ethyl)-1-(4-(5-(difluoromethyl)-1,3,4-oxadiazol-2-yl)-2-fluorobenzyl)-1-phenylurea

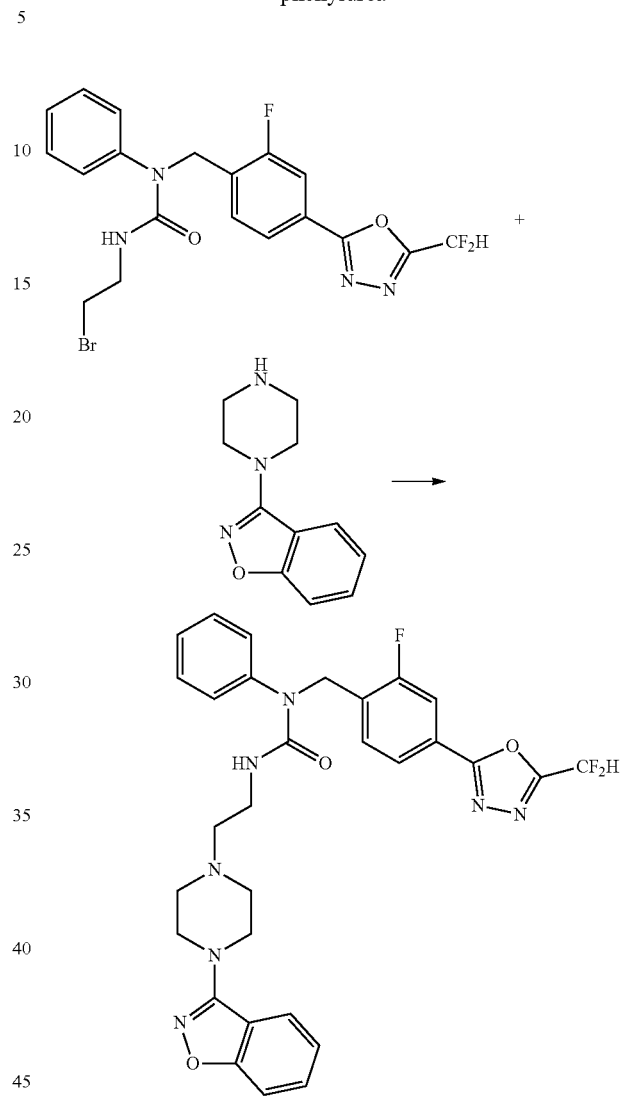

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-(4-fluorophenyl)piperazine (0.021 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography ($SiO_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-(4-fluorophenyl)piperazin-1-yl)ethyl)-1-phenylurea as colorless oil (0.012 g, 19.8%).

$^1$H NMR (700 MHz, $CDCl_3$) δ 7.89 (dd, 1H, J=8.0, 1.7 Hz), 7.75-7.69 (m, 2H), 7.40-7.34 (m, 2H), 7.31-7.26 (m, 1H), 7.21-7.16 (m, 2H), 7.02-6.91 (m, 3H), 6.87-6.81 (m, 2H), 5.11 (s, 1H), 5.06 (s, 2H), 3.36 (d, 2H, J=6.0 Hz), 2.91 (s, 4H), 2.52 (s, 4H), 2.49 (s, 2H); LRMS (ES) m/z 569.3 ($M^+$+1).

3-(2-bromoethyl)-1-(4-(5-(difluoromethyl)-1,3,4-oxadiazol-2-yl)-2-fluorobenzyl)-1-phenylurea (0.050 g, 0.107 mmol) and 3-(piperazin-1-yl)benzo[d]isoxazole (0.024 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography ($SiO_2$ plate, 20×20×1 mm; methanol/dichloromethane=10%) to give 3-(2-(4-(benzo[d]isoxazol-3-yl)piperazin-1-yl)ethyl)-1-(4-(5-(difluoromethyl)-1,3,4-oxadiazol-2-yl)-2-fluorobenzyl)-1-phenylurea as white solid (0.021 g, 33.3%).

$^1$H NMR (700 MHz, $CDCl_3$) δ 7.89 (dd, 1H, J=8.0, 1.7 Hz), 7.75-7.69 (m, 2H), 7.72-7.65 (m, 1H), 7.54-7.46 (m, 2H), 7.42-7.37 (m, 2H), 7.31 (ddt, 1H, J=8.0, 6.9, 1.2 Hz), 7.24 (ddd, 1H, J=8.0, 6.8, 1.1 Hz), 7.21-7.17 (m, 2H), 6.93

(t, 1H, J=51.8 Hz), 5.11 (t, 1H, J=4.8 Hz), 5.06 (s, 2H), 3.40-3.34 (m, 3H), 3.37-3.35 (m, 3H), 2.56 (t, 4H, J=5.0 Hz), 2.51 (t, 2H, J=6.0 Hz); LRMS (ES) m/z 592.0 (M$^+$+1).

Example 440. Compound 22012: 3-(2-(4-(3,4-Dichlorophenyl)piperazin-1-yl)ethyl)-1-(4-(5-(difluoromethyl)-1,3,4-oxadiazol-2-yl)-2-fluorobenzyl)-1-phenylurea

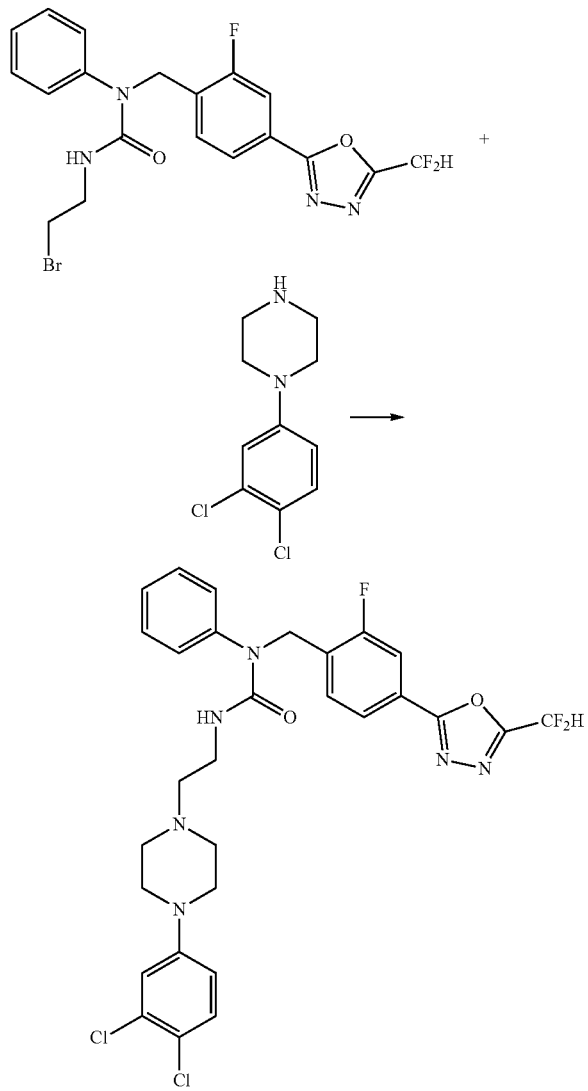

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-(3,4-dichlorophenyl)piperazine (0.027 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(4-(3,4-dichlorophenyl)piperazin-1-yl)ethyl)-1-(4-(5-(difluoromethyl)-1,3,4-oxadiazol-2-yl)-2-fluorobenzyl)-1-phenylurea as white foam (0.026 g, 39.4%).

$^1$H NMR (700 MHz, CDCl$_3$) δ 7.89 (dd, 1H, J=8.0, 1.7 Hz), 7.75-7.68 (m, 2H), 7.40-7.34 (m, 2H), 7.32-7.26 (m, 1H), 7.21-7.16 (m, 2H), 7.03-6.83 (m, 3H), 6.71 (dd, 1H, J=8.9, 2.9 Hz), 5.10-5.05 (m, 1H), 5.06 (s, 2H), 3.36 (q, 2H, J=5.7 Hz), 2.95 (t, 4H, J=5.1 Hz), 2.52-2.46 (m, 6H); LRMS (ES) m/z 621.0 (M$^+$+1).

Example 441. Compound 22013: 3-(2-(4-Benzylpiperazin-1-yl)ethyl)-1-(4-(5-(difluoromethyl)-1,3,4-oxadiazol-2-yl)-2-fluorobenzyl)-1-phenylurea

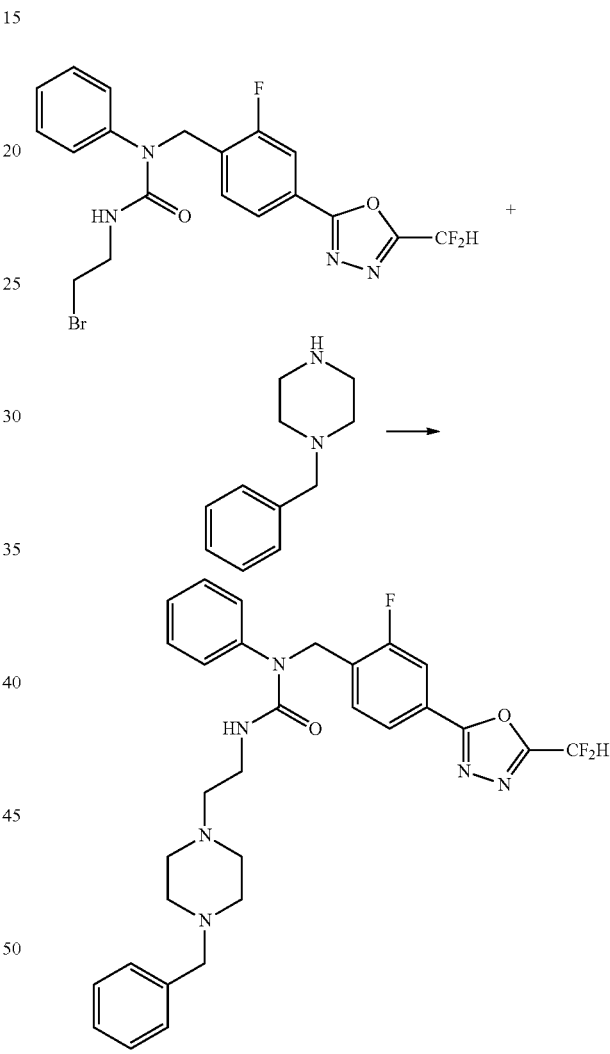

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-benzylpiperazine (0.021 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(4-benzylpiperazin-1-yl)ethyl)-1-(4-(5-(difluoromethyl)-1,3,4-oxadiazol-2-yl)-2-fluorobenzyl)-1-phenylurea as yellow oil (0.008 g, 13.3%).

$^1$H NMR (700 MHz, CDCl$_3$) δ 7.89 (dd, 1H, J=8.0, 1.7 Hz), 7.75-7.68 (m, 2H), 7.39-7.32 (m, 4H), 7.32-7.26 (m, 4H), 7.19-7.14 (m, 2H), 7.02-6.83 (m, 1H), 5.14 (t, 1H, J=4.7 Hz), 5.05 (s, 2H), 3.47 (s, 2H), 3.30 (td, 2H, J=6.1, 4.8 Hz), 2.59-2.01 (m, 10H); LRMS (ES) m/z 561.5 (M$^+$+1).

Example 442. Compound 22014: 1-(4-(5-(Difluoromethyl)-1,3,4-oxadiazol-2-yl)-2-fluorobenzyl)-3-(2-(4-phenethylpiperazin-1-yl)ethyl)-1-phenylurea

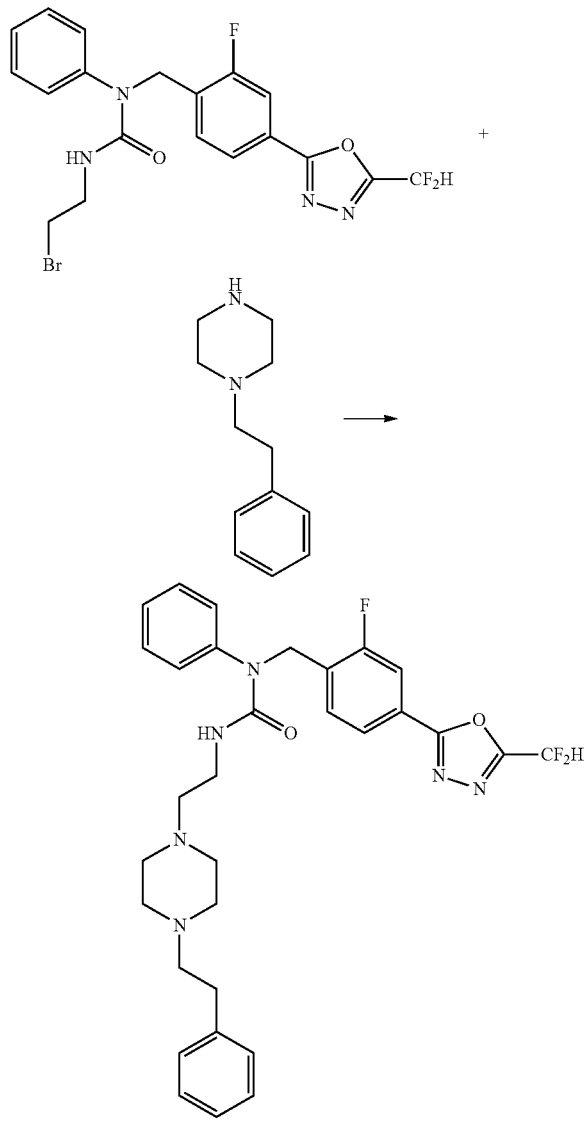

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-phenethylpiperazine (0.022 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-3-(2-(4-phenethylpiperazin-1-yl)ethyl)-1-phenylurea as colorless oil (0.010 g, 16.2%).

$^1$H NMR (700 MHz, CDCl$_3$) δ 7.89 (dd, 1H, J=8.0, 1.7 Hz), 7.72 (ddd, 2H, J=10.3, 7.2, 4.4 Hz), 7.43-7.37 (m, 2H), 7.35-7.28 (m, 3H), 7.26-7.17 (m, 5H), 7.04-6.80 (m, 1H), 5.14 (t, 1H, J=4.7 Hz), 5.06 (s, 2H), 3.32 (td, 2H, J=6.1, 4.8 Hz), 2.86-2.76 (m, 2H), 2.66-2.14 (m, 12H); LRMS (ES) m/z 579.0 (M$^+$+1).

Example 443. Compound 22015: 1-(4-(5-(Difluoromethyl)-1,3,4-oxadiazol-2-yl)-2-fluorobenzyl)-1-phenyl-3-(2-(4-(2-(pyridin-4-yl)ethyl)piperazin-1-yl)ethyl)urea

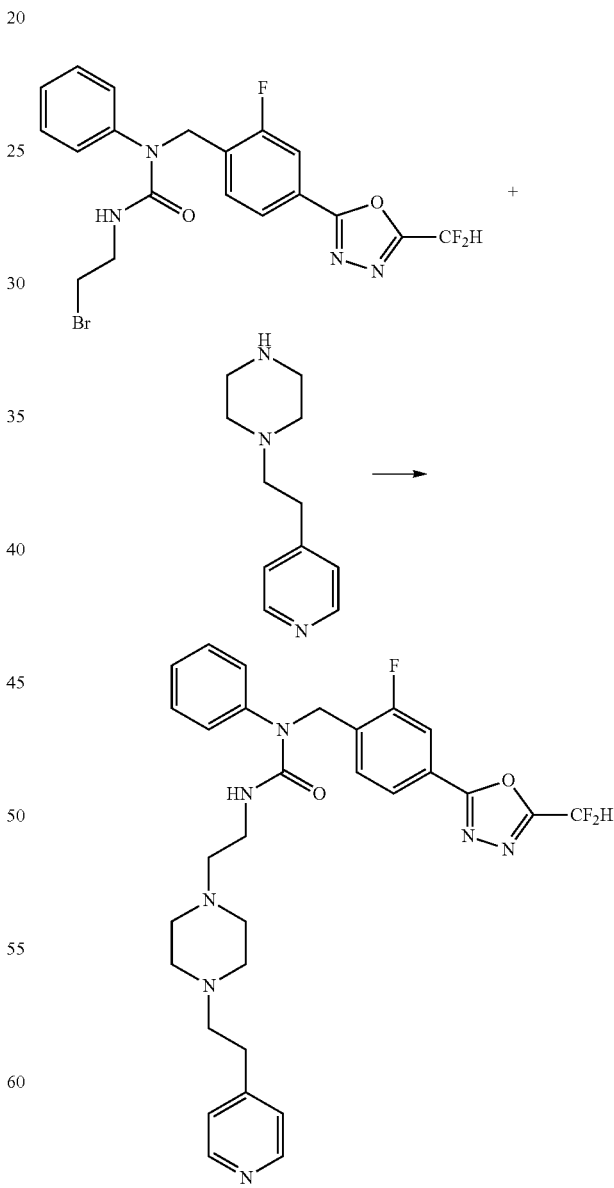

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-(2-(pyridin-4-yl)ethyl)piperazine (0.022 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 1-(4-(5-(difluoromethyl)-1,3,4-oxadiazol-2-yl)-2-fluorobenzyl)-1-phenyl-3-(2-(4-(2-(pyridin-4-yl)ethyl)piperazin-1-yl)ethyl)urea as colorless oil (0.009 g, 14.6%).

$^1$H NMR (700 MHz, CDCl$_3$) δ 8.55-8.50 (m, 2H), 7.89 (dd, 1H, J=8.0, 1.7 Hz), 7.75-7.69 (m, 2H), 7.43-7.37 (m, 2H), 7.35-7.29 (m, 1H), 7.21-7.16 (m, 2H), 7.17-7.13 (m, 2H), 7.02-6.83 (m, 1H), 5.10 (t, 1H, J=4.8 Hz), 5.06 (s, 2H), 3.32 (q, 2H, J=5.9 Hz), 2.80-2.74 (m, 2H), 2.62-2.15 (m, 12H); LRMS (ES) m/z 591.0 (M$^+$+1).

Example 444. Compound 22016: 3-(2-(4-Cinnamylpiperazin-1-yl)ethyl)-1-(4-(5-(difluoromethyl)-1,3,4-oxadiazol-2-yl)-2-fluorobenzyl)-1-phenylurea

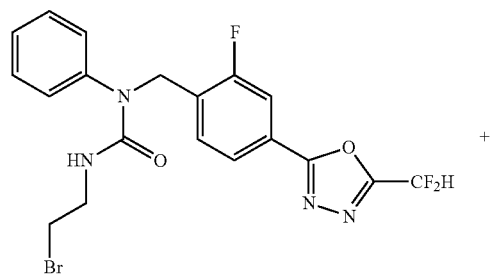

+

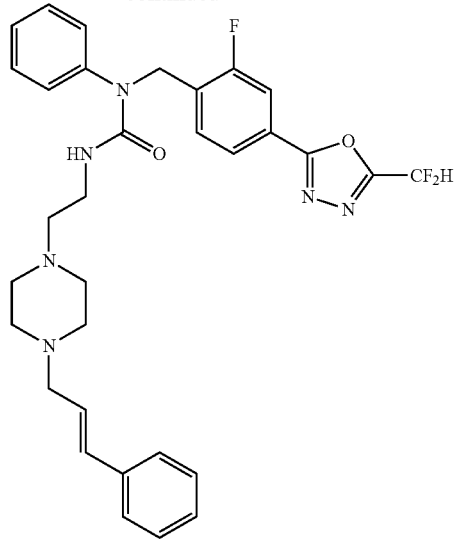

3-(2-bromoethyl)-1-(4-(5-(difluoromethyl)-1,3,4-oxadiazol-2-yl)-2-fluorobenzyl)-1-phenylurea (0.050 g, 0.107 mmol) and 1-cinnamylpiperazine (0.024 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(4-cinnamylpiperazin-1-yl)ethyl)-1-(4-(5-(difluoromethyl)-1,3,4-oxadiazol-2-yl)-2-fluorobenzyl)-1-phenylurea as colorless oil (0.017 g, 27.0%).

$^1$H NMR (700 MHz, CDCl$_3$) δ 7.89 (dd, 1H, J=8.0, 1.7 Hz), 7.75-7.69 (m, 2H), 7.43-7.37 (m, 4H), 7.37-7.28 (m, 3H), 7.29-7.22 (m, 1H), 7.21-7.16 (m, 2H), 7.02-6.82 (m, 1H), 6.56-6.50 (m, 1H), 6.26 (dt, 1H, J=15.9, 6.8 Hz), 5.13 (t, 1H, J=4.7 Hz), 5.06 (s, 2H), 3.31 (td, 2H, J=6.1, 4.7 Hz), 3.12 (dd, 2H, J=6.8, 1.4 Hz), 2.43 (t, 10H, J=6.1 Hz); LRMS (ES) m/z 586.2 (M$^+$+1).

Example 445. Compound 22017: 3-(2-(Dibenzylamino)ethyl)-1-(4-(5-(difluoromethyl)-1,3,4-oxadiazol-2-yl)-2-fluorobenzyl)-1-phenylurea

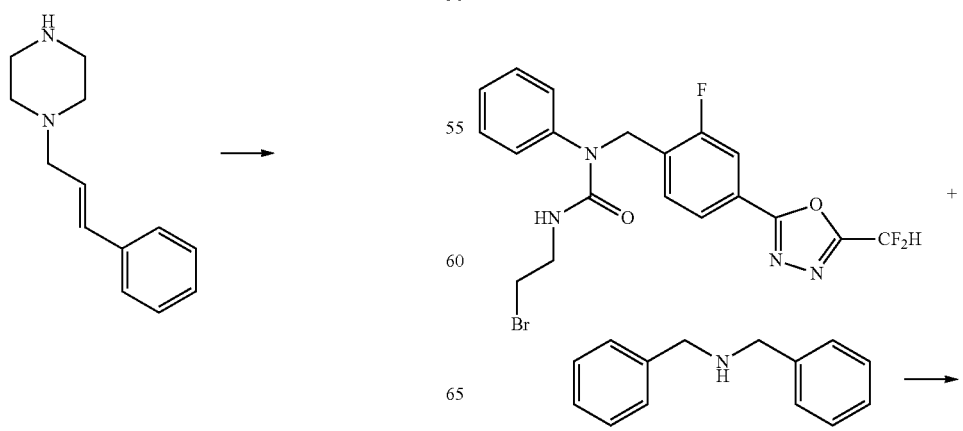

-continued

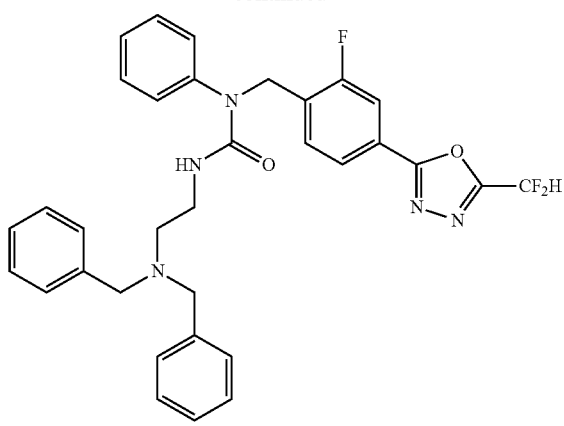

3-(2-bromoethyl)-1-(4-(5-(difluoromethyl)-1,3,4-oxadiazol-2-yl)-2-fluorobenzyl)-1-phenylurea (0.050 g, 0.107 mmol) and dibenzylamine (0.023 g, 0.117 mmol) were mixed at the room temperature in acetonitrile (1 mL) and then stirred at 100° C. for 18 hr and cooled down to the room temperature to terminate the reaction. Then, water was added to the reaction mixture, followed by extraction with dichloromethane. The bi-phasic mixture was passed through aplastic frit to remove the solid residues and aqueous layer, and the organic layer collected was concentrated in vacuo. The concentrate was purified and concentrated by column chromatography (SiO$_2$ plate, 20×20×1 mm; methanol/dichloromethane=10%) to give 3-(2-(dibenzylamino)ethyl)-1-(4-(5-(difluoromethyl)-1,3,4-oxadiazol-2-yl)-2-fluorobenzyl)-1-phenylurea as colorless oil (0.023 g, 36.9%).

$^1$H NMR (700 MHz, CDCl$_3$) δ 7.87 (dd, 1H, J=8.0, 1.7 Hz), 7.72 (dd, 1H, J=9.8, 1.7 Hz), 7.66 (t, 1H, J=7.6 Hz), 7.58-7.52 (m, 2H), 7.52-7.47 (m, 1H), 7.41-7.33 (m, 1H), 7.27-7.20 (m, 7H), 7.02-6.84 (m, 5H), 5.10 (t, 1H, J=4.6 Hz), 5.04 (s, 2H), 3.44 (s, 4H), 3.37 (dt, 2H, J=6.0, 4.6 Hz), 2.53-2.48 (m, 2H); LRMS (ES) m/z 438.0 (M$^+$+1).

Example 446. Compound 22018: N-(4-(5-(Difluoromethyl)-1,3,4-oxadiazol-2-yl)-2-fluorobenzyl)-N-(thiazol-2-yl)morpholine-4-carboxamide

[Step 1] N-(4-(5-(Difluoromethyl)-1,3,4-oxadiazol-2-yl)-2-fluorobenzyl)thiazol-2-amine

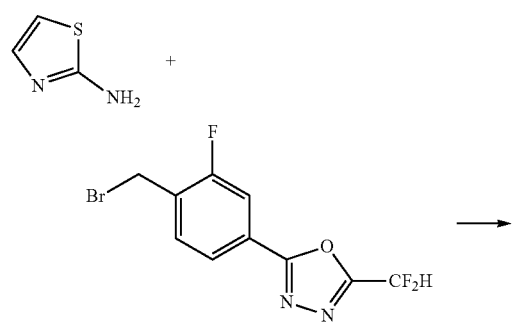

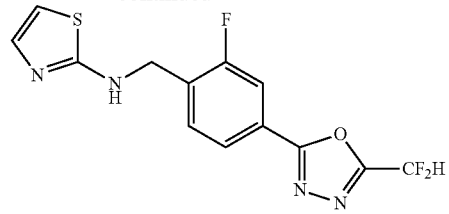

A solution of thiazol-2-amine (0.200 g, 2.000 mmol), 2-(4-(bromomethyl)-3-fluorophenyl)-5-(difluoromethyl)-1,3,4-oxadiazole (0.614 g, 2.000 mmol) and N,N-diisopropylethylamine (1.045 mL, 6.000 mmol) in N,N-dimethylformamide (8 mL) prepared at the room temperature was stirred at the same temperature for 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; methanol/dichloromethane=0% to 5%) to give N-(4-(5-(difluoromethyl)-1,3,4-oxadiazol-2-yl)-2-fluorobenzyl)thiazol-2-amine as pale yellow oil (0.207 g, 31.7%).

[Step 2] Compound 22018

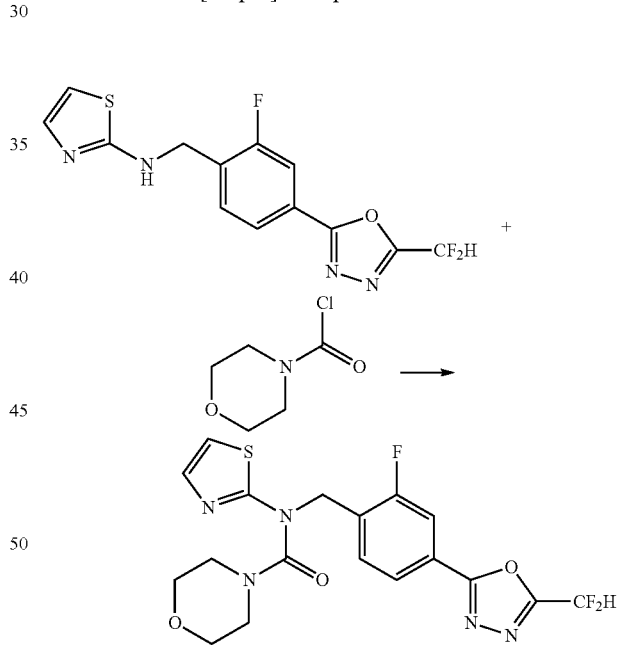

A solution of N-(4-(5-(difluoromethyl)-1,3,4-oxadiazol-2-yl)-2-fluorobenzyl)thiazol-2-amine (0.207 g, 0.635 mmol), N,N-diisopropylethylamine (0.221 mL, 1.270 mmol) and N,N-dimethylpyridin-4-amine (DMAP, 0.008 g, 0.063 mmol) in dichloromethane (3 mL) was stirred at the room temperature for 10 min, and mixed with morpholine-4-carbonyl chloride (0.145 mL, 1.270 mmol). The reaction mixture was stirred at the same temperature for additional 18 hr. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 50%) to give N-(4-(5-(difluoromethyl)-1,3,4-oxadiazol-2-yl)-2-fluorobenzyl)-N-(thiazol-2-yl)morpholine-4-carboxamide as pale yellow solid (0.140 g, 50.3%).

$^1$H NMR (400 MHz, CDCl$_3$) δ 7.91-7.83 (m, 2H), 7.43 (dd, 1H, J=8.2, 7.2 Hz), 7.07-6.77 (m, 2H), 6.53 (d, 1H, J=4.8 Hz), 5.36 (s, 2H), 3.73-3.63 (m, 4H), 3.31-3.24 (m, 4H); LRMS (ES) m/z 440.2 (M$^+$+1).

Example 447. Compound 22019: N-(4-(5-(Difluoromethyl)-1,3,4-oxadiazol-2-yl)-2-fluorobenzyl)-N-(thiophen-2-yl)morpholine-4-carboxamide

[Step 1]
N-(Thiophen-2-yl)morpholine-4-carboxamide

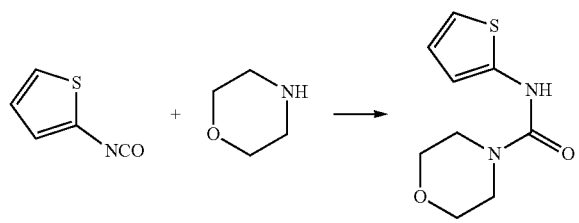

A solution of 2-isocyanatothiophene (0.250 g, 2.000 mmol) and morpholine (0.173 mL, 2.000 mmol) in diethylether (5 mL) prepared at the room temperature was stirred at the same temperature for 18 hr, and concentrated under the reduced pressure. The title compound was used without further purification (N-(thiophen-2-yl)morpholine-4-carboxamide, 0.420 g, 98.9%, pale brown solid).

[Step 2] Compound 22019

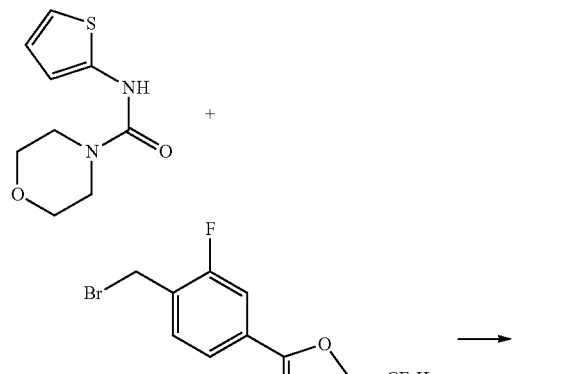

A solution of N-(thiophen-2-yl)morpholine-4-carboxamide (0.100 g, 0.471 mmol) and sodium hydride (60.00%, 0.023 g, 0.565 mmol) in N,N-dimethylformamide (2 mL) was stirred at the room temperature for 30 min, and mixed with 2-(4-(bromomethyl)-3-fluorophenyl)-5-(difluoromethyl)-1,3,4-oxadiazole (0.145 g, 0.471 mmol). The reaction mixture was stirred at the same temperature for additional 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 50%) to give N-(4-(5-(difluoromethyl)-1,3,4-oxadiazol-2-yl)-2-fluorobenzyl)-N-(thiophen-2-yl)morpholine-4-carboxamide as brown solid (0.067 g, 32.2%).

$^1$H NMR (400 MHz, CDCl$_3$) δ 7.89 (dd, 1H, J=8.0, 1.7 Hz), 7.85-7.74 (m, 1H), 7.71-7.62 (m, 1H), 7.09-6.77 (m, 3H), 6.64 (dd, 1H, J=3.7, 1.3 Hz), 4.97 (s, 2H), 3.64-3.51 (m, 4H), 3.41-3.29 (m, 4H); LRMS (ES) m/z 439.3 (M$^+$+1).

Example 448. Compound 22020: N-(4-(5-(Difluoromethyl)-1,3,4-oxadiazol-2-yl)-2-fluorobenzyl)-N-(thiophen-2-yl)thiomorpholine-4-carboxamide 1,1-dioxide

[Step 1]
N-(Thiophen-2-yl)thiomorpholine-4-carboxamide 1,1-dioxide

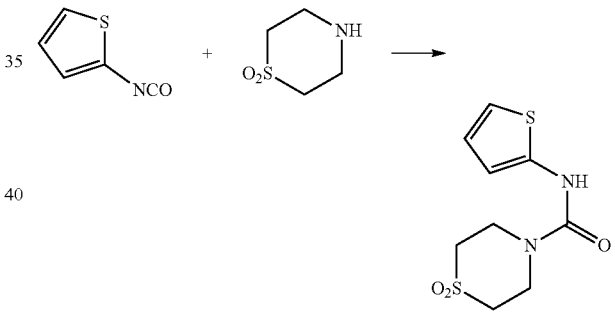

A solution of 2-isocyanatothiophene (0.250 g, 2.000 mmol) and thiomorpholine 1,1-dioxide (0.270 g, 2.000 mmol) in diethylether (5 mL) prepared at the room temperature was stirred at the same temperature for 18 hr, and concentrated under the reduced pressure. The title compound was used without further purification (N-(thiophen-2-yl)thiomorpholine-4-carboxamide 1,1-dioxide, 0.520 g, 99.9%, pale brown solid).

[Step 2] Compound 22020

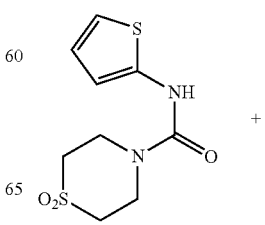

1289

-continued

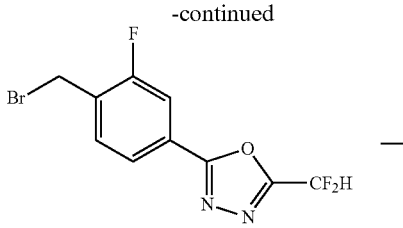

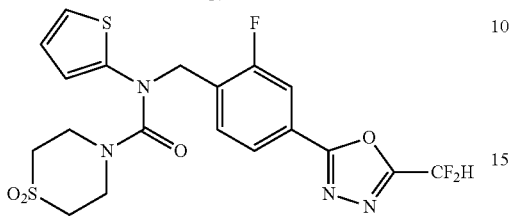

A solution of N-(thiophen-2-yl)thiomorpholine-4-carboxamide 1,1-dioxide (0.100 g, 0.384 mmol) and sodium hydride (60.00%, 0.018 g, 0.461 mmol) in N,N-dimethylformamide (2 mL) was stirred at the room temperature for 30 min, and mixed with 2-(4-(bromomethyl)-3-fluorophenyl)-5-(difluoromethyl)-1,3,4-oxadiazole (0.118 g, 0.384 mmol). The reaction mixture was stirred at the same temperature for additional 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 50%) to give N-(4-(5-(difluoromethyl)-1,3,4-oxadiazol-2-yl)-2-fluorobenzyl)-N-(thiophen-2-yl)thiomorpholine-4-carboxamide 1,1-dioxide as pale brown solid (0.050 g, 26.5%).

$^1$H NMR (400 MHz, CDCl$_3$) δ 7.90 (dd, 1H, J=8.1, 1.6 Hz), 7.81 (dd, 1H, J=10.0, 1.7 Hz), 7.63 (t, 1H, J=7.6 Hz), 7.10 (dd, 1H, J=5.6, 1.3 Hz), 7.08-6.78 (m, 2H), 6.69 (dd, 1H, J=3.7, 1.3 Hz), 4.93 (s, 2H), 3.88-3.78 (m, 4H), 2.89-2.78 (m, 4H); LRMS (ES) m/z 487.2 (M$^+$+1).

Example 449. Compound 22021: N-(4-(5-(Difluoromethyl)-1,3,4-oxadiazol-2-yl)-2-fluorobenzyl)-N-(thiophen-3-yl)thiomorpholine-4-carboxamide 1,1-dioxide

[Step 1]
N-(Thiophen-3-yl)thiomorpholine-4-carboxamide 1,1-dioxide

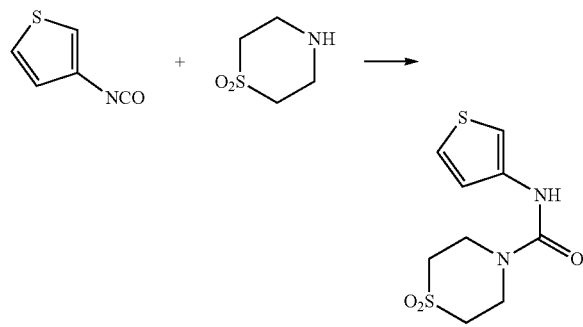

A solution of 3-isocyanatothiophene (0.250 g, 2.000 mmol) and thiomorpholine 1,1-dioxide (0.270 g, 2.000 mmol) in diethylether (5 mL) prepared at the room temperature was stirred at the same temperature for 18 hr, and concentrated under the reduced pressure. The title compound was used without further purification (N-(thiophen-3-yl)thiomorpholine-4-carboxamide 1,1-dioxide, 0.520 g, 99.9%, white solid).

[Step 2] Compound 22021

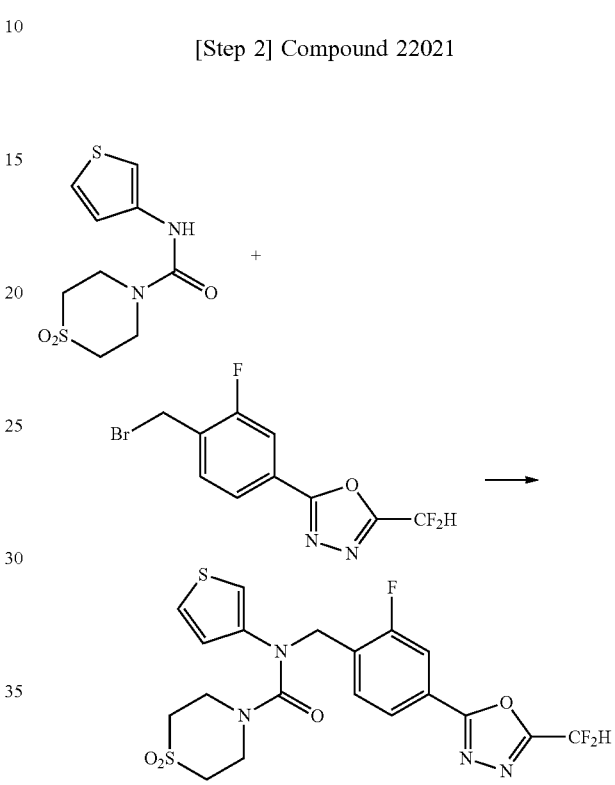

A solution of N-(thiophen-3-yl)thiomorpholine-4-carboxamide 1,1-dioxide (0.100 g, 0.384 mmol) and sodium hydride (60.00%, 0.018 g, 0.461 mmol) in N,N-dimethylformamide (2 mL) was stirred at the room temperature for 30 min, and mixed with 2-(4-(bromomethyl)-3-fluorophenyl)-5-(difluoromethyl)-1,3,4-oxadiazole (0.118 g, 0.384 mmol). The reaction mixture was stirred at the same temperature for additional 18 hr, concentrated under the reduced pressure. Then, water was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO$_2$, 4 g cartridge; ethyl acetate/hexane=0% to 50%) to give N-(4-(5-(difluoromethyl)-1,3,4-oxadiazol-2-yl)-2-fluorobenzyl)-N-(thiophen-3-yl)thiomorpholine-4-carboxamide 1,1-dioxide as pale yellow solid (0.071 g, 37.8%).

$^1$H NMR (400 MHz, CDCl$_3$) δ 7.89 (dd, 1H, J=7.9, 1.7 Hz), 7.80 (dd, 1H, J=10.1, 1.6 Hz), 7.63 (t, 1H, J=7.6 Hz), 7.38-7.31 (m, 1H), 7.08-6.78 (m, 3H), 4.92 (s, 2H), 3.80-3.73 (m, 4H), 2.89-2.83 (m, 4H); LRMS (ES) m/z 487.2 (M$^+$+1).

Example 450. Compound 22024: N-(4-(5-(difluoromethyl)-1,3,4-oxadiazol-2-yl)-2-fluorobenzyl)-N-(3-((4-ethylpiperazin-1-yl)methyl)phenyl)thiomorpholine-4-carboxamide 1,1-dioxide

[Step 1] 3-((4-(5-(Difluoromethyl)-1,3,4-oxadiazol-2-yl)-2-fluorobenzyl)amino)benzaldehyde

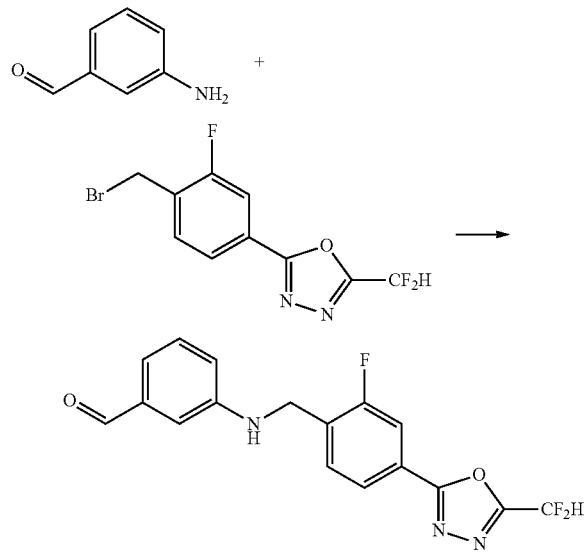

A solution of 3-aminobenzaldehyde (0.300 g, 2.476 mmol), 2-(4-(bromomethyl)-3-fluorophenyl)-5-(difluoromethyl)-1,3,4-oxadiazole (0.760 g, 2.476 mmol) and N,N-diisopropylethylamine (1.294 mL, 7.429 mmol) in N,N-dimethylformamide (7 mL) prepared at the room temperature was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=10% to 40%) to give 3-((4-(5-(difluoromethyl)-1,3,4-oxadiazol-2-yl)-2-fluorobenzyl)amino)benzaldehyde as white solid (0.280 g, 32.6%).

[Step 2] N-(4-(5-(difluoromethyl)-1,3,4-oxadiazol-2-yl)-2-fluorobenzyl)-N-(3-formylphenyl)thiomorpholine-4-carboxamide 1,1-dioxide

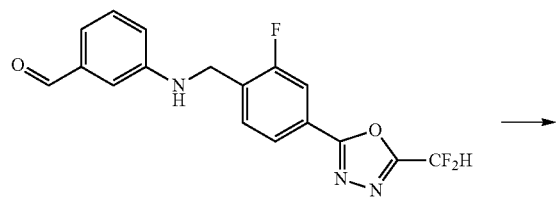

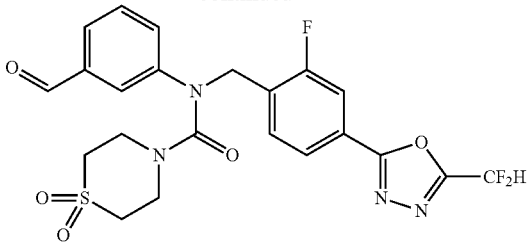

A solution of 3-((4-(5-(difluoromethyl)-1,3,4-oxadiazol-2-yl)-2-fluorobenzyl)amino)benzaldehyde (0.280 g, 0.806 mmol), triphosgene (0.120 g, 0.403 mmol) and N,N-diisopropylethylamine (0.421 mL, 2.419 mmol) in dichloromethane (10 mL) was stirred at 0° C. for 30 min, and mixed with thiomorpholine (0.131 g, 0.967 mmol). The reaction mixture was stirred at the same temperature for additional 3 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The concentrate was purified and concentrated by column chromatography (SiO₂, 12 g cartridge; ethyl acetate/hexane=10% to 60%) to give N-(4-(5-(difluoromethyl)-1,3,4-oxadiazol-2-yl)-2-fluorobenzyl)-N-(3-formylphenyl)thiomorpholine-4-carboxamide 1,1-dioxide as white solid (0.298 g, 72.7%).

[Step 3] Compound 22024

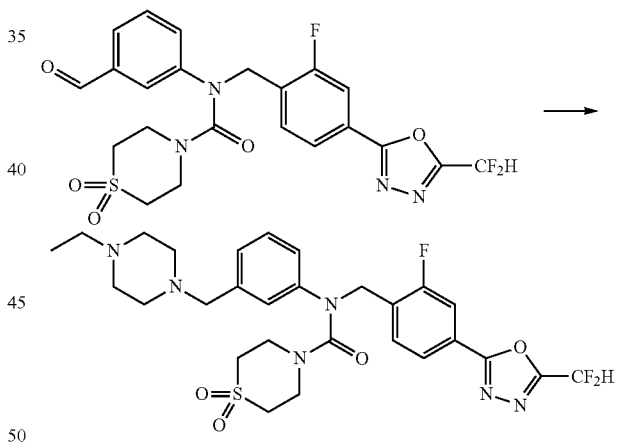

A solution of N-(4-(5-(difluoromethyl)-1,3,4-oxadiazol-2-yl)-2-fluorobenzyl)-N-(3-formylphenyl)thiomorpholine-4-carboxamide 1,1-dioxide (0.150 g, 0.295 mmol) and ethyl piperazine (0.051 g, 0.443 mmol) in dichloromethane (5 mL) was stirred at the room temperature for 10 min, and mixed with sodium triacetoxyborohydride (0.125 g, 0.590 mmol). The reaction mixture was stirred at the same temperature for additional 17 hr. Then, saturated aqueous ammonium chloride solution was added to the reaction mixture, followed by extraction with dichloromethane. The bi-phasic mixture was passed through a plastic frit to remove the solid residues and aqueous layer, and the organic layer collected was concentrated in vacuo. The concentrate was purified and concentrated by column chromatography (SiO₂, 4 g cartridge; methanol/dichloromethane=0% to 10%) to give N-(4-(5-(difluoromethyl)-1,3,4-oxadiazol-2-yl)-2-fluorobenzyl)-N-(3-((4-ethylpiperazin-1-yl)methyl)phenyl)thiomorpholine-4-carboxamide 1,1-dioxide as white solid (0.110 g, 61.5%).

$^1$H NMR (400 MHz, DMSO-d$_6$) δ 7.85 (dd, 1H, J=8.0, 1.6 Hz), 7.78-7.71 (m, 2H), 7.55 (t, 1H, J=51.3 Hz), 7.33 (t, 1H, J=7.7 Hz), 7.22-7.17 (m, 2H), 7.08 (d, 1H, J=7.3 Hz), 4.94 (s, 2H), 3.58 (s, 4H), 3.45 (s, 2H), 2.92 (s, 4H), 2.33-2.19 (m, 10H), 1.08 (brs, 3H); LRMS (ES) m/z 607.4 (M$^+$+1).

Experimental Example 1: HDAC Enzyme Activity Inhibition Assays (In Vitro)

In order to examine the HDAC6 selectivity of the compounds of formula I of the present invention by HDAC1 and HDAC6 enzymatic activity inhibition assays, an experiment was performed using a conventional substance as a control.

HDAC enzyme activity was measured using a HDAC Fluorimetric Drug Discovery Kit (BML-AK511, 516, Enzo Life Science). For the HDAC1 enzyme activity test, human recombinant HDAC1 (BML-SE456) was used as an enzyme source, and Fluor de Lys®-"SIRT1 (BNL-KI177) was used as a substrate. A 5-fold dilution of the compound was seeded into a 96-well plate, and then 0.3 μg of the enzyme and 10 μM of the substrate were added to each well of the plate and allowed to react at 30° C. for 60 minutes. Then, Fluor de Lys®-Developer II (BML-KI176) was added thereto and allowed to react for 30 minutes, after which the fluorescence value (Ex 360, Em 460) was measured using a multi-plate reader (Flexstation 3, Molecular Device). The HDAC6 enzyme was tested using human recombinant HDAC6 (382180) (Calbiochem) according to the same protocol as the HDAC1 enzyme activity test method. Based on the resulting values, each IC$_5$, value was calculated using GraphPad Prism4.0 program.

TABLE 2

Results of HDAC enzyme activity inhibition assays

| Ex. | Comp. | HDAC1 (nM) | HDAC6 (nM) | HDAC6 selectivity (fold) |
|---|---|---|---|---|
| 1 | 21249 | 10000 | 87 | 115 |
| 2 | 21285 | ND | 110 | 91 |
| 3 | 21318 | ND | 69 | 145 |
| 4 | 21319 | ND | 192 | 52 |
| 5 | 21325 | ND | 49 | 204 |
| 6 | 21327 | ND | ND | 1 |
| 7 | 21329 | ND | ND | 1 |
| 8 | 21333 | ND | ND | 1 |
| 9 | 21336 | ND | 95 | 105 |
| 10 | 21337 | ND | 28 | 357 |
| 11 | 21340 | ND | 836 | 12 |
| 12 | 21341 | ND | 1190 | 8 |
| 13 | 21342 | ND | 1990 | 5 |
| 14 | 21343 | ND | 10740 | 1 |
| 15 | 21344 | ND | 830 | 12 |
| 16 | 21345 | ND | 185 | 54 |
| 17 | 21346 | ND | 173 | 58 |
| 18 | 21347 | ND | 183 | 55 |
| 19 | 21348 | ND | 8360 | 1 |
| 20 | 21349 | ND | 430 | 23 |
| 21 | 21350 | ND | 530 | 19 |
| 22 | 21351 | ND | 261 | 38 |
| 23 | 21352 | ND | 1100 | 9 |
| 24 | 21353 | ND | 720 | 14 |
| 25 | 21354 | ND | 380 | 26 |
| 26 | 21355 | ND | 6910 | 1 |
| 27 | 21357 | ND | 472 | 21 |
| 28 | 21358 | ND | 1046 | 10 |
| 29 | 21359 | ND | 2280 | 4 |
| 30 | 21360 | ND | 35.4 | 282 |
| 31 | 21361 | ND | 67.8 | 147 |
| 32 | 21362 | ND | 55.7 | 180 |
| 33 | 21363 | ND | 84.8 | 118 |
| 34 | 21364 | ND | 92.4 | 108 |
| 35 | 21365 | ND | 145 | 69 |
| 36 | 21366 | ND | 126 | 79 |
| 37 | 21367 | ND | 234 | 43 |
| 38 | 21368 | ND | 420 | 24 |
| 39 | 21369 | ND | 56 | 179 |
| 40 | 21370 | ND | 25 | 400 |
| 41 | 21371 | ND | 1090 | 9 |
| 42 | 21372 | ND | 76 | 132 |
| 43 | 21373 | ND | 20 | 500 |
| 44 | 21374 | ND | 1010 | 10 |
| 45 | 21375 | ND | 1750 | 6 |
| 46 | 21376 | ND | 448 | 22 |
| 47 | 21377 | ND | 334 | 30 |
| 48 | 21378 | ND | 20 | 500 |
| 49 | 21379 | ND | 76 | 132 |
| 50 | 21380 | ND | 165 | 61 |
| 51 | 21381 | ND | 132 | 76 |
| 52 | 21382 | ND | 79 | 127 |
| 53 | 21383 | ND | 50 | 200 |
| 54 | 21384 | ND | 79 | 127 |
| 55 | 21385 | ND | 57 | 175 |
| 56 | 21386 | ND | 47 | 213 |
| 57 | 21387 | ND | 241 | 41 |
| 58 | 21388 | ND | 240 | 42 |
| 59 | 21389 | 6357 | 93 | 68 |
| 60 | 21390 | 5279 | 317 | 17 |
| 61 | 21391 | ND | 366 | 27 |
| 62 | 21392 | ND | 153 | 65 |
| 63 | 21393 | 8956 | 137 | 65 |
| 64 | 21394 | ND | 177 | 56 |
| 65 | 21395 | ND | 73 | 137 |
| 66 | 21396 | ND | 292 | 34 |
| 67 | 21397 | ND | 882 | 11 |
| 68 | 21398 | ND | 849 | 12 |
| 69 | 21399 | ND | 780 | 13 |
| 70 | 21400 | ND | 582 | 17 |
| 71 | 21401 | ND | 497 | 20 |
| 72 | 21402 | ND | 222 | 45 |
| 73 | 21403 | ND | 334 | 30 |
| 74 | 21404 | ND | 247 | 40 |
| 75 | 21405 | ND | 354 | 28 |
| 76 | 21406 | ND | 619 | 16 |
| 77 | 21407 | ND | 140 | 71 |
| 78 | 21408 | ND | 706 | 14 |
| 79 | 21409 | ND | 304 | 33 |
| 80 | 21410 | ND | 840 | 12 |
| 81 | 21411 | ND | 2150 | 5 |
| 82 | 21412 | ND | 470 | 21 |
| 83 | 21413 | ND | 246 | 41 |
| 84 | 21414 | ND | 126 | 79 |
| 85 | 21415 | ND | 299 | 33 |
| 86 | 21416 | ND | 1585 | 6 |
| 87 | 21417 | ND | 70 | 143 |
| 88 | 21418 | ND | 154 | 65 |
| 89 | 21419 | ND | 77 | 130 |
| 90 | 21420 | ND | 70 | 143 |
| 91 | 21421 | ND | 67 | 149 |
| 92 | 21422 | ND | 105 | 95 |
| 93 | 21423 | ND | 26.5 | 377 |
| 94 | 21424 | ND | 184 | 54 |
| 95 | 21425 | ND | 130 | 77 |
| 96 | 21426 | ND | 489 | 20 |
| 97 | 21427 | ND | 126 | 79 |
| 98 | 21428 | ND | 134 | 75 |
| 99 | 21429 | ND | 2080 | 5 |
| 100 | 21431 | ND | 256 | 39 |
| 101 | 21432 | ND | 48 | 208 |
| 102 | 21433 | ND | 58 | 172 |
| 103 | 21434 | ND | 188 | 53 |
| 104 | 21435 | 3378 | 286 | 12 |
| 105 | 21436 | 5735 | 433 | 13 |
| 106 | 21437 | 8219 | 740 | 11 |

TABLE 2-continued

Results of HDAC enzyme activity inhibition assays

| Ex. | Comp. | HDAC1 (nM) | HDAC6 (nM) | HDAC6 selectivity (fold) |
|---|---|---|---|---|
| 107 | 21438 | 2697 | 750 | 4 |
| 108 | 21439 | 6114 | 1007 | 6 |
| 109 | 21440 | ND | 267 | 37 |
| 110 | 21441 | 2530 | 139 | 18 |
| 111 | 21442 | 8730 | 114 | 77 |
| 112 | 21443 | 7440 | 366 | 20 |
| 113 | 21444 | ND | 175 | 57 |
| 114 | 21445 | ND | 303 | 33 |
| 115 | 21446 | ND | 87 | 115 |
| 116 | 21447 | ND | 51 | 196 |
| 117 | 21448 | ND | 36 | 278 |
| 118 | 21449 | ND | 1527 | 7 |
| 119 | 21450 | ND | 530 | 19 |
| 120 | 21451 | ND | 333 | 30 |
| 121 | 21452 | ND | 108 | 93 |
| 122 | 21453 | ND | 117 | 85 |
| 123 | 21454 | ND | 106 | 94 |
| 124 | 21455 | ND | 34 | 294 |
| 125 | 21456 | ND | 578 | 17 |
| 126 | 21457 | ND | 190 | 53 |
| 127 | 21458 | ND | ND | 1 |
| 128 | 21459 | ND | ND | 1 |
| 129 | 21460 | ND | ND | 1 |
| 130 | 21461 | ND | 731 | 14 |
| 131 | 21462 | ND | 1420 | 7 |
| 132 | 21463 | ND | 4530 | 2 |
| 133 | 21464 | ND | 1728 | 6 |
| 134 | 21465 | ND | 30 | 333 |
| 135 | 21466 | ND | 78 | 128 |
| 136 | 21467 | ND | 31 | 323 |
| 137 | 21468 | ND | 63 | 159 |
| 138 | 21469 | ND | 41 | 244 |
| 139 | 21470 | ND | 32 | 313 |
| 140 | 21471 | ND | 47 | 213 |
| 141 | 21472 | ND | 46 | 217 |
| 142 | 21473 | ND | 32 | 313 |
| 143 | 21474 | ND | 130 | 77 |
| 144 | 21475 | ND | 69 | 145 |
| 145 | 21476 | ND | 51 | 196 |
| 146 | 21477 | ND | 73 | 137 |
| 147 | 21478 | ND | 37 | 270 |
| 148 | 21479 | ND | 60 | 167 |
| 149 | 21480 | ND | 49 | 204 |
| 150 | 21481 | ND | 58 | 172 |
| 151 | 21482 | ND | 31 | 323 |
| 152 | 21483 | ND | 71 | 141 |
| 153 | 21484 | ND | 21 | 476 |
| 154 | 21485 | 4424 | 369 | 12 |
| 155 | 21486 | ND | 83 | 120 |
| 156 | 21487 | 1951 | 344 | 6 |
| 157 | 21488 | ND | 111 | 90 |
| 158 | 21489 | 1652 | 89 | 18 |
| 159 | 21490 | ND | 37 | 270 |
| 160 | 21491 | 4039 | 157 | 25 |
| 161 | 21492 | ND | 36 | 278 |
| 162 | 21493 | 1740 | 313 | 6 |
| 163 | 21494 | ND | 112 | 89 |
| 164 | 21495 | ND | 34 | 294 |
| 165 | 21496 | ND | 20 | 500 |
| 166 | 21497 | ND | 34 | 294 |
| 167 | 21498 | ND | 14 | 714 |
| 168 | 21499 | ND | 17 | 588 |
| 169 | 21500 | ND | 25 | 400 |
| 170 | 21501 | ND | 28 | 357 |
| 171 | 21502 | ND | 279 | 36 |
| 172 | 21511 | ND | 332 | 30 |
| 173 | 21512 | ND | 93 | 108 |
| 174 | 21513 | ND | 212 | 47 |
| 175 | 21514 | ND | 35 | 286 |
| 176 | 21515 | ND | 87 | 115 |
| 177 | 21516 | ND | 40 | 250 |
| 178 | 21517 | 2921 | 93 | 31 |
| 179 | 21518 | ND | 25 | 400 |
| 180 | 21519 | 2653 | 131 | 20 |
| 181 | 21520 | ND | 63 | 159 |
| 182 | 21521 | ND | 565 | 18 |
| 183 | 21522 | ND | 22 | 455 |
| 184 | 21527 | ND | 28 | 357 |
| 185 | 21528 | ND | 214 | 47 |
| 186 | 21529 | ND | 36 | 278 |
| 187 | 21530 | ND | 60 | 167 |
| 188 | 21531 | ND | 13 | 769 |
| 189 | 21532 | ND | 48 | 208 |
| 190 | 21533 | ND | 143 | 70 |
| 191 | 21534 | ND | 57 | 175 |
| 192 | 21535 | ND | 44 | 227 |
| 193 | 21536 | ND | 18 | 556 |
| 194 | 21537 | ND | 69 | 145 |
| 195 | 21540 | ND | 30 | 333 |
| 196 | 21541 | ND | 64 | 156 |
| 197 | 21542 | ND | 61 | 164 |
| 198 | 21543 | 4745 | 73 | 64 |
| 199 | 21544 | ND | 34 | 294 |
| 200 | 21545 | 4444 | 52 | 85 |
| 201 | 21546 | ND | 21 | 476 |
| 202 | 21552 | ND | 1520 | 7 |
| 203 | 21553 | ND | 697 | 14 |
| 204 | 21554 | ND | 155 | 65 |
| 205 | 21555 | ND | 386 | 26 |
| 206 | 21556 | ND | 281 | 36 |
| 207 | 21557 | ND | 244 | 41 |
| 208 | 21564 | ND | 113 | 88 |
| 209 | 21566 | ND | 16 | 625 |
| 210 | 21566 | ND | 19 | 526 |
| 211 | 21568 | ND | 237 | 42 |
| 212 | 21569 | ND | 170 | 59 |
| 213 | 21570 | ND | 309 | 32 |
| 214 | 21576 | ND | 409 | 24 |
| 215 | 21577 | ND | 66 | 152 |
| 216 | 21578 | ND | 43 | 233 |
| 217 | 21583 | ND | 12 | 833 |
| 218 | 21584 | ND | 27 | 370 |
| 219 | 21585 | ND | 27 | 370 |
| 220 | 21586 | ND | 21 | 476 |
| 221 | 21587 | ND | 11 | 909 |
| 222 | 21591 | ND | 15 | 668 |
| 223 | 21592 | 8283 | 100 | 100 |
| 224 | 21593 | ND | 20 | 494 |
| 225 | 21594 | ND | 87 | 115 |
| 226 | 21597 | ND | 31 | 323 |
| 227 | 21598 | ND | 42 | 238 |
| 228 | 21599 | ND | 20 | 500 |
| 229 | 21600 | ND | 25 | 400 |
| 230 | 21601 | ND | 52 | 192 |
| 231 | 21602 | ND | 19 | 526 |
| 232 | 21619 | ND | 19 | 517 |
| 233 | 21620 | ND | 26 | 383 |
| 234 | 21621 | ND | 637 | 16 |
| 235 | 21622 | ND | 44 | 226 |
| 236 | 21623 | ND | 35 | 290 |
| 237 | 21624 | ND | 29 | 347 |
| 238 | 21625 | ND | 24 | 422 |
| 239 | 21626 | ND | 16 | 645 |
| 240 | 21627 | ND | 457 | 22 |
| 241 | 21628 | ND | 271 | 37 |
| 242 | 21629 | ND | 11 | 880 |
| 243 | 21630 | ND | 18 | 549 |
| 244 | 21631 | ND | 72 | 138 |
| 245 | 21632 | ND | 41 | 245 |
| 246 | 21633 | ND | 173 | 58 |
| 247 | 21634 | ND | 120 | 83 |
| 248 | 21643 | ND | 28 | 352 |
| 249 | 21644 | ND | 135 | 74 |
| 250 | 21645 | ND | 216 | 46 |
| 251 | 21646 | ND | 32 | 317 |
| 252 | 21650 | 36055 | 77 | 468 |
| 253 | 21651 | 49162 | 61 | 806 |
| 254 | 21652 | 36518 | 46 | 787 |
| 255 | 21653 | ND | 41 | 246 |
| 256 | 21654 | 18829 | 12 | 1518 |

TABLE 2-continued

Results of HDAC enzyme activity inhibition assays

| Ex. | Comp. | HDAC1 (nM) | HDAC6 (nM) | HDAC6 selectivity (fold) |
|---|---|---|---|---|
| 257 | 21655 | ND | 15 | 690 |
| 258 | 21656 | 36460 | 33 | 1122 |
| 259 | 21657 | ND | 44 | 226 |
| 260 | 21658 | 8444 | 144 | 59 |
| 261 | 21659 | 15663 | 102 | 153 |
| 262 | 21660 | 24801 | 309 | 80 |
| 263 | 21664 | 17121 | 151 | 114 |
| 264 | 21665 | 19148 | 21 | 917 |
| 265 | 21666 | 20464 | 374 | 55 |
| 266 | 21667 | 20092 | 41 | 485 |
| 267 | 21668 | 10398 | 253 | 41 |
| 268 | 21669 | 7467 | 164 | 46 |
| 269 | 21679 | 23199 | 34 | 675 |
| 270 | 21707 | ND | 50 | 199 |
| 271 | 21708 | ND | 60 | 167 |
| 272 | 21709 | 58550 | 26 | 2255 |
| 273 | 21710 | 67685 | 26 | 2651 |
| 274 | 21724 | 20737 | 28 | 736 |
| 275 | 21735 | 19085 | 29 | 662 |
| 276 | 21736 | 17695 | 41 | 432 |
| 277 | 21759 | ND | 25 | 405 |
| 278 | 21760 | ND | 46 | 215 |
| 279 | 21765 | ND | 114 | 88 |
| 280 | 21766 | ND | 114 | 88 |
| 281 | 21767 | ND | 1142 | 9 |
| 282 | 21797 | ND | 268 | 37 |
| 283 | 21798 | ND | 1318 | 8 |
| 284 | 21799 | ND | 305 | 33 |
| 285 | 21806 | ND | 38 | 261 |
| 286 | 21807 | ND | 39 | 256 |
| 287 | 21808 | 42600 | 21 | 2023 |
| 288 | 21809 | ND | 57 | 174 |
| 289 | 21810 | 15741 | 18 | 883 |
| 290 | 21811 | ND | 70 | 144 |
| 291 | 21812 | ND | 107 | 94 |
| 292 | 21813 | ND | 330 | 30 |
| 293 | 21823 | 20828 | 56 | 370 |
| 294 | 21824 | 17685 | 31 | 563 |
| 295 | 21829 | 47047 | 31 | 1542 |
| 296 | 21830 | 40925 | 32 | 1298 |
| 297 | 21831 | 64364 | 42 | 1538 |
| 298 | 21839 | 56734 | 34 | 1689 |
| 299 | 21840 | 31903 | 188 | 170 |
| 300 | 21841 | ND | 26 | 382 |
| 301 | 21842 | 25163 | 187 | 135 |
| 302 | 21843 | ND | 22 | 461 |
| 303 | 21844 | 32253 | 80 | 404 |
| 304 | 21845 | 62336 | 32 | 1919 |
| 305 | 21846 | 21301 | 123 | 173 |
| 306 | 21847 | 70230 | 39 | 1811 |
| 307 | 21848 | 41912 | 261 | 161 |
| 308 | 21849 | ND | 106 | 95 |
| 309 | 21850 | 68552 | 436 | 157 |
| 310 | 21851 | ND | 25 | 407 |
| 311 | 21852 | 15349 | 131 | 118 |
| 312 | 21853 | 28836 | 53 | 540 |
| 313 | 21854 | 12656 | 276 | 46 |
| 314 | 21855 | ND | 40 | 248 |
| 315 | 21856 | ND | 95 | 105 |
| 316 | 21857 | 23880 | 131 | 182 |
| 317 | 21858 | 37132 | 38 | 966 |
| 318 | 21859 | 23528 | 133 | 177 |
| 319 | 21860 | 18019 | 220 | 82 |
| 320 | 21861 | 13725 | 343 | 40 |
| 321 | 21862 | 33705 | 472 | 71 |
| 322 | 21863 | 25787 | 400 | 65 |
| 323 | 21864 | 28839 | 152 | 190 |
| 324 | 21865 | 16785 | 96 | 174 |
| 325 | 21866 | 23870 | 137 | 174 |
| 326 | 21867 | 35897 | 73 | 489 |
| 327 | 21868 | 27500 | 160 | 172 |
| 328 | 21869 | 18913 | 138 | 137 |
| 329 | 21870 | 45096 | 113 | 400 |
| 330 | 21871 | 9126 | 321 | 28 |
| 331 | 21872 | 9426 | 249 | 38 |
| 332 | 21873 | 14945 | 269 | 55 |
| 333 | 21874 | 6170 | 308 | 20 |
| 334 | 21875 | 8995 | 386 | 23 |
| 335 | 21876 | 11662 | 255 | 46 |
| 336 | 21877 | 65015 | 46 | 1424 |
| 337 | 21878 | 21486 | 41 | 522 |
| 338 | 21879 | 27908 | 26 | 1064 |
| 339 | 21880 | 44427 | 95 | 467 |
| 340 | 21881 | ND | 49 | 204 |
| 341 | 21882 | ND | 40 | 251 |
| 342 | 21883 | ND | 37 | 268 |
| 343 | 21884 | ND | 33 | 303 |
| 344 | 21885 | ND | 18 | 555 |
| 345 | 21886 | ND | 46 | 218 |
| 346 | 21887 | ND | 46 | 218 |
| 347 | 21888 | ND | 26 | 388 |
| 348 | 21889 | ND | 98 | 103 |
| 349 | 21890 | ND | 54 | 185 |
| 350 | 21891 | ND | 57 | 174 |
| 351 | 21892 | 48704 | 89 | 548 |
| 352 | 21893 | 37567 | 59 | 640 |
| 353 | 21894 | 76291 | 48 | 1588 |
| 354 | 21895 | ND | 236 | 42 |
| 355 | 21896 | 28465 | 346 | 82 |
| 356 | 21897 | 68109 | 487 | 140 |
| 357 | 21898 | 40570 | 247 | 164 |
| 358 | 21899 | 75683 | 55 | 1364 |
| 359 | 21900 | ND | 190 | 53 |
| 360 | 21901 | ND | 349 | 29 |
| 361 | 21902 | ND | 398 | 25 |
| 362 | 21905 | 56088 | 39 | 1454 |
| 363 | 21910 | ND | 470 | 21 |
| 364 | 21914 | ND | 158 | 63 |
| 365 | 21915 | ND | 160 | 62 |
| 366 | 21916 | ND | 232 | 43 |
| 367 | 21917 | ND | 66 | 151 |
| 368 | 21918 | ND | 193 | 52 |
| 369 | 21919 | ND | 357 | 28 |
| 370 | 21924 | ND | 213 | 47 |
| 371 | 21925 | ND | 829 | 12 |
| 372 | 21926 | ND | 356 | 28 |
| 373 | 21929 | ND | 57 | 176 |
| 374 | 21930 | 14587 | 419 | 35 |
| 375 | 21931 | ND | 1742 | 6 |
| 376 | 21932 | ND | 684 | 15 |
| 377 | 21933 | ND | 2412 | 4 |
| 378 | 21934 | ND | 667 | 15 |
| 379 | 21935 | ND | 265 | 38 |
| 380 | 21936 | ND | 110 | 91 |
| 381 | 21937 | ND | 65 | 153 |
| 382 | 21938 | ND | 82 | 122 |
| 383 | 21939 | ND | 161 | 62 |
| 384 | 21940 | ND | 85 | 118 |
| 385 | 21941 | 45955 | 103 | 446 |
| 386 | 21942 | ND | 62 | 160 |
| 387 | 21943 | 29605 | 48 | 611 |
| 388 | 21944 | ND | 50 | 201 |
| 389 | 21945 | ND | 193 | 52 |
| 390 | 21946 | ND | 123 | 81 |
| 391 | 21947 | ND | 90 | 112 |
| 392 | 21948 | 46287 | 246 | 188 |
| 393 | 21949 | 48275 | 126 | 383 |
| 394 | 21950 | ND | 157 | 64 |
| 395 | 21951 | ND | 391 | 26 |
| 396 | 21952 | ND | 172 | 58 |
| 397 | 21953 | ND | 160 | 62 |
| 398 | 21954 | 35674 | 145 | 245 |
| 399 | 21955 | ND | 89 | 113 |
| 400 | 21956 | ND | 167 | 60 |
| 401 | 21957 | ND | 86 | 116 |
| 402 | 21958 | ND | 87 | 115 |
| 403 | 21970 | ND | 1554 | 6 |
| 404 | 21971 | ND | 169 | 59 |
| 405 | 21972 | ND | 266 | 38 |
| 406 | 21973 | ND | 256 | 39 |

TABLE 2-continued

Results of HDAC enzyme activity inhibition assays

| Ex. | Comp. | HDAC1 (nM) | HDAC6 (nM) | HDAC6 selectivity (fold) |
|---|---|---|---|---|
| 407 | 21979 | ND | 669 | 15 |
| 408 | 21980 | ND | 1031 | 10 |
| 409 | 21981 | ND | 758 | 13 |
| 410 | 21982 | ND | 104 | 96 |
| 411 | 21983 | ND | 160 | 63 |
| 412 | 21984 | ND | 93 | 107 |
| 413 | 21985 | 21449 | 45 | 480 |
| 414 | 21986 | ND | 48 | 207 |
| 415 | 21987 | ND | 213 | 47 |
| 416 | 21988 | ND | 301 | 33 |
| 417 | 21989 | ND | 124 | 80 |
| 418 | 21990 | ND | 100 | 100 |
| 419 | 21991 | ND | 83 | 120 |
| 420 | 21992 | ND | 75 | 133 |
| 421 | 21993 | ND | 86 | 117 |
| 422 | 21994 | ND | 123 | 81 |
| 423 | 21995 | ND | 90 | 111 |
| 424 | 21996 | ND | 92 | 108 |
| 425 | 21997 | ND | 91 | 109 |
| 426 | 21998 | ND | 66 | 153 |
| 427 | 21999 | ND | 117 | 85 |
| 428 | 22000 | ND | 165 | 61 |
| 429 | 22001 | ND | 87 | 116 |
| 430 | 22002 | ND | 118 | 85 |
| 431 | 22003 | ND | 101 | 99 |
| 432 | 22004 | ND | 412 | 24 |
| 433 | 22005 | ND | 126 | 79 |
| 434 | 22006 | ND | 270 | 37 |
| 435 | 22007 | ND | 249 | 40 |
| 436 | 22008 | ND | 138 | 73 |
| 437 | 22009 | ND | 103 | 97 |
| 438 | 22010 | ND | 341 | 29 |
| 439 | 22011 | ND | 320 | 31 |
| 440 | 22012 | ND | 1020 | 10 |
| 441 | 22013 | ND | 197 | 51 |
| 442 | 22014 | ND | 219 | 46 |
| 443 | 22015 | ND | 95 | 105 |
| 444 | 22016 | ND | 237 | 42 |
| 445 | 22017 | ND | 1385 | 7 |
| 446 | 22018 | ND | 2388 | 4 |
| 447 | 22019 | ND | 127 | 79 |
| 448 | 22020 | ND | 138 | 73 |
| 449 | 22021 | ND | 99 | 101 |
| 450 | 22024 | ND | 281 | 36 |

As can be seen in Table 2 above, the 1,3,4-oxadiazole derivative compounds, stereoisomers thereof or pharmaceutically acceptable salts thereof according to the present invention showed up to 2651 times higher selective HDAC6 inhibitory activities in the HDAC1 and HDAC6 activity inhibition assays.

Experimental Example 2: Analysis of the Effect of HDAC6-Specific Inhibitors on Mitochondrial Axonal Transport (In Vitro)

The effect of HDAC6-specific inhibitors on mitochondrial axonal transport was analyzed. Specifically, in order to examine whether the compounds represented by formula I according to the present invention selectively inhibit HDAC6 activity to increase the acetylation of tubulin, which is a major substrate of HDAC6, thereby improving the mitochondrial axonal transport velocity reduced by amyloid-beta treatment in neuronal axons, a comparison experiment was performed using a compound that have already been developed as a control.

Hippocampal neurons from Sprague-Dawley (SD) rat embryos at embryonic day 17-18 (E17-18) were cultured in an extracellular matrix-coated dish for imaging for 7 days, and then treated with 1 μM of an amyloid-beta peptides. After 24 hours, the neurons were treated with compounds for 3 hours on the 8th days in vitro and treated with MitoTracker Red CMXRos (Life Technologies, NY, USA) for the last 5 minutes to stain the mitochondria. Axonal transport of the stained mitochondria was imaged using a confocal microscope (Leica SP8; Leica Microsystems, UK) at 1-second intervals for 1 minute, and the transport velocity per second of each mitochondrion was determined using the IMARIS analysis software (BITPLANE, Zurich, Switzerland).

As a result, it was found that the 1,3,4-oxadiazole derivative compounds, stereoisomers thereof or pharmaceutically acceptable salts according to the present invention improved the velocity of mitochondrial axonal transport.

The invention claimed is:

1. An 1,3,4-oxadiazole derivative compound represented by the following formula I, a stereoisomer thereof or a pharmaceutically acceptable salt thereof:

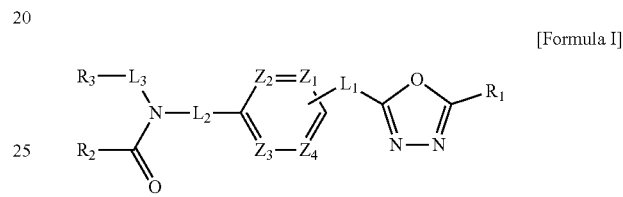

[Formula I]

wherein $L_1$ or $L_3$ are each independently a bond or —($C_1$-$C_2$ alkylene)-;
$R_1$ is —$CX_2H$ or —$CX_3$;
$L_2$ is —($C_1$-$C_2$ alkylene)-;
$R_2$ is —$NR^AR^B$, —$OR^C$,

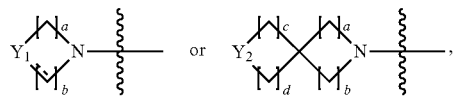

wherein at least one H of

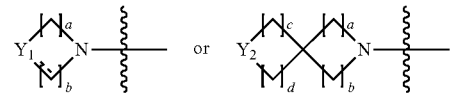

may be substituted with —X, —OH, —O($C_1$-$C_4$ alkyl), —$NR^DR^E$, —($C_1$-$C_4$ alkyl), —$CF_3$, —$CF_2H$, —CN, -aryl, -heteroaryl, —($C_1$-$C_4$ alkyl)-aryl or —($C_1$-$C_4$ alkyl)-heteroaryl, wherein at least one H of the -aryl, -heteroaryl, —($C_1$-$C_4$ alkyl)-aryl or —($C_1$-$C_4$ alkyl)-heteroaryl may be substituted with —X, —OH, —$CF_3$ or —$CF_2H$;
$R_3$ is —H, —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_3$-$C_7$ cycloalkyl), —($C_2$-$C_6$ heterocycloalkyl), -aryl, -heteroaryl, -adamantyl,

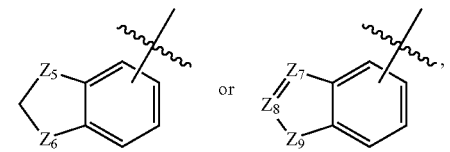

wherein at least one H of the —(C$_1$-C$_4$ alkyl) may be substituted with —X or —OH,
at least one H of the -aryl or -heteroaryl may be substituted with —X, —OH, —O(C$_1$-C$_4$ alkyl), —OCF$_3$, —O-aryl, —NR$^D$R$^E$, —(C$_1$-C$_4$ alkyl), —CF$_3$, —CF$_2$H, —C(=O)—(C$_1$-C$_4$ alkyl), —C(=O)—O(C$_1$-C$_4$ alkyl), —C(=O)—NR$^D$R$^E$, —S(=O)$_2$—(C$_1$-C$_4$ alkyl), -aryl, -heteroaryl

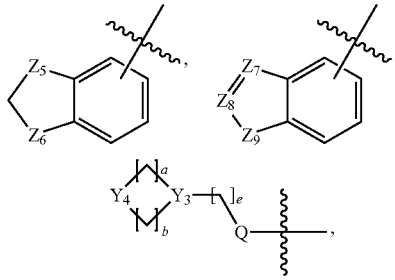

or wherein at least one H of

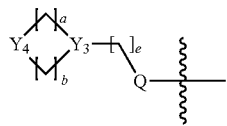

may be substituted with —X, —(C$_1$-C$_4$ alkyl), —CF$_3$ or —CF$_2$H, and
at least one H of the —(C$_3$-C$_7$ cycloalkyl), —(C$_2$-C$_6$ heterocycloalkyl), -adamantyl,

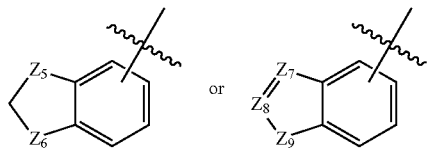

may be substituted with —X, —OH or —(C$_1$-C$_4$ alkyl);
Y$_1$, Y$_2$ and Y$_4$ are each independently —CH$_2$—, —NR$^F$—, —O—, —C(=O)— or —S(=O)$_2$—;
Y$_3$ is —CH$_2$— or —N—;
Z$_1$ to Z$_4$ are each independently N or CR$^Z$, wherein at least three of Z$_1$ to Z$_4$ may not be simultaneously N, and R$^Z$ is —H, —X or —O(C$_1$-C$_4$ alkyl);
Z$_5$ and Z$_6$ are each independently —CH$_2$— or —O—;
Z$_7$ and Z$_8$ are each independently =CH— or =N—;
Z$_9$ is —NR$^G$— or —S—;
R$^A$ and R$^B$ are each independently —H, —(C$_1$-C$_4$ alkyl), —(C$_1$-C$_4$ alkyl)-OH, —(C$_1$-C$_4$ alkyl)-NR$^D$R$^E$, -aryl, —(C$_1$-C$_4$ alkyl)-aryl, -heteroaryl, —(C$_1$-C$_4$ alkyl)-heteroaryl, —(C$_3$-C$_7$ cycloalkyl), —(C$_2$-C$_6$ heterocycloalkyl) or

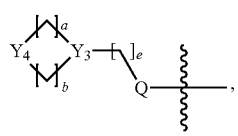

wherein at least one H of the —(C$_1$-C$_4$ alkyl), —(C$_1$-C$_4$ alkyl)-OH or —(C$_1$-C$_4$ alkyl)-NR$^D$R$^E$ may be substituted with —X,
at least one H of the -aryl, —(C$_1$-C$_4$ alkyl)-aryl, -heteroaryl, —(C$_1$-C$_4$ alkyl)-heteroaryl, —(C$_3$-C$_7$ cycloalkyl) or —(C$_2$-C$_6$ heterocycloalkyl) may be substituted with —X, —OH, —O(C$_1$-C$_4$ alkyl), —(C$_1$-C$_4$ alkyl), —CF$_3$, —CF$_2$H or —CN, and
at least one H of

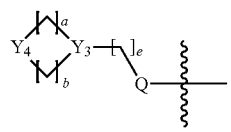

may be substituted with —X, —OH, —O(C$_1$-C$_4$ alkyl), —(C$_1$-C$_4$ alkyl), —CF$_3$, —CF$_2$H, —CN, —(C$_2$-C$_6$ heterocycloalkyl), -aryl, —(C$_1$-C$_4$ alkyl)-aryl or -heteroaryl;
R$^C$ is —(C$_1$-C$_4$ alkyl), -aryl, —(C$_1$-C$_4$ alkyl)-aryl, -heteroaryl or —(C$_1$-C$_4$ alkyl)-heteroaryl,
wherein at least one H of the —(C$_1$-C$_4$ alkyl) may be substituted with —X or —OH, and
at least one H of the -aryl, —(C$_1$-C$_4$ alkyl)-aryl, -heteroaryl or —(C$_1$-C$_4$ alkyl)-heteroaryl may be substituted with —X, —OH, —CF$_3$ or —CF$_2$H;
R$^D$ and R$^E$ are each independently —H, —(C$_1$-C$_4$ alkyl), -aryl or —(C$_1$-C$_4$ alkyl)-aryl,
wherein at least one H of the —(C$_1$-C$_4$ alkyl) may be substituted with —X or —OH, and
at least one H of the -aryl or —(C$_1$-C$_4$ alkyl)-aryl may be substituted with —X, —OH, —CF$_3$ or —CF$_2$H;
R$^F$ is —H, —(C$_1$-C$_6$ alkyl), —(C$_1$-C$_4$ alkyl)-OH, —(C$_1$-C$_4$ alkyl)-O—(C$_1$-C$_4$ alkyl), —C(=O)—(C$_1$-C$_4$ alkyl), —C(=O)—O(C$_1$-C$_4$ alkyl), —(C$_1$-C$_4$ alkyl)-C(=O)—O(C$_1$-C$_4$ alkyl), —(C$_1$-C$_4$ alkyl)-NR$^D$R$^E$, —S(=O)$_2$—(C$_1$-C$_4$ alkyl), -aryl, —(C$_1$-C$_4$ alkyl)-aryl, —(C$_2$-C$_4$ alkenyl)-aryl, -heteroaryl, —(C$_1$-C$_4$ alkyl)-heteroaryl, —C(=O)—(C$_3$-C$_7$ cycloalkyl), —(C$_2$-C$_6$ heterocycloalkyl) or —(C$_1$-C$_4$ alkyl)-C(=O)—(C$_2$-C$_6$ heterocycloalkyl),
wherein at least one H of the —(C$_1$-C$_4$ alkyl), —(C$_1$-C$_4$ alkyl)-OH, —(C$_1$-C$_4$ alkyl)-O—(C$_1$-C$_4$ alkyl), —C(=O)—(C$_1$-C$_4$ alkyl), —C(=O)—O(C$_1$-C$_4$ alkyl), —(C$_1$-C$_4$ alkyl)-C(=O)—O(C$_1$-C$_4$ alkyl), —(C$_1$-C$_4$ alkyl)-NR$^D$R$^E$ or —S(=O)$_2$—(C$_1$-C$_4$ alkyl) may be substituted with —X, and
wherein at least one H of the -aryl, —(C$_1$-C$_4$ alkyl)-aryl, —(C$_2$-C$_4$ alkenyl)-aryl, -heteroaryl, —(C$_1$-C$_4$ alkyl)-heteroaryl, —C(=O)—(C$_3$-C$_7$ cycloalkyl), —(C$_2$-C$_6$ heterocycloalkyl) or —(C$_1$-C$_4$ alkyl)-C(=O)—(C$_2$-C$_6$ heterocycloalkyl) may be substituted with —X, —OH, —CF$_3$ or —CF$_2$H;
R$^G$ is —H or —(C$_1$-C$_4$ alkyl);
Q is —O— or a bond,
==== is a single bond or a double bond, provided that when ==== is a double bond, then Y$_1$ is =CH—;
a to e are each independently an integer of 0, 1, 2, 3 or 4, provided that a and b may not be simultaneously 0, and c and d may not be simultaneously 0; and
X is F, Cl, Br or I.

2. The 1,3,4-oxadiazole derivative compound represented by formula I, stereoisomer thereof or pharmaceutically acceptable salt thereof according to claim 1, wherein $L_1$ or $L_3$ are each independently a bond or —($C_1$-$C_2$ alkylene)-;

$R_1$ is —$CX_2H$ or —$CX_3$;

$L_2$ is —($C_1$-$C_2$ alkylene)-;

$R_2$ is —$NR^AR^B$, —$OR^C$,

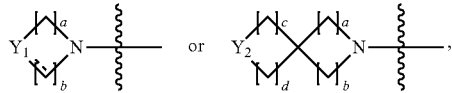

wherein at least one H of

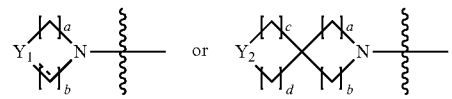

may be substituted with —X, —OH, —$NR^DR^E$, —($C_1$-$C_4$ alkyl) or -aryl, wherein at least one H of the -aryl may be substituted with —X, —OH, —$CF_3$ or —$CF_2H$;

$R_3$ is —H, —($C_1$-$C_4$ alkyl), —($C_3$-$C_7$ cycloalkyl), -aryl, -heteroaryl, -adamantyl,

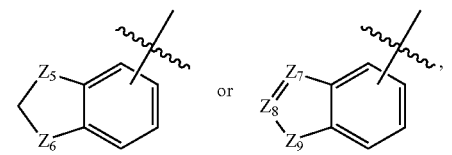

wherein at least one H of the —($C_1$-$C_4$ alkyl) may be substituted with —X or —OH, at least one H of the -aryl or -heteroaryl may be substituted with —X, —O($C_1$-$C_4$ alkyl), —$OCF_3$, —O-aryl, —($C_1$-$C_4$ alkyl), —$CF_3$, —$S(=O)_2$—($C_1$-$C_4$ alkyl), -aryl, -heteroaryl,

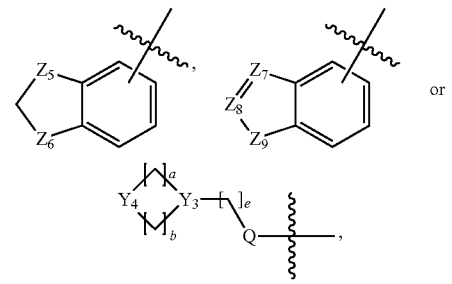

wherein at least one H of

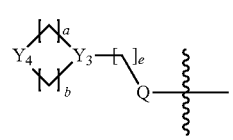

may be substituted with —X or —($C_1$-$C_4$ alkyl), and at least one H of the —($C_3$-$C_7$ cycloalkyl), -adamantyl,

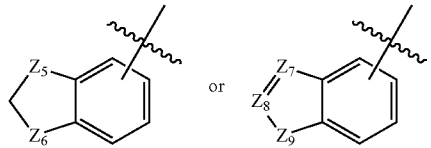

may be substituted with —X, —OH or —($C_1$-$C_4$ alkyl);

$Y_1$, $Y_2$ and $Y_4$ are each independently —$CH_2$—, —$NR^F$—, —O—, —C(=O)— or —$S(=O)_2$—;

$Y_3$ is —$CH_2$— or —N—;

$Z_1$ to $Z_4$ are each independently N or $CR^Z$, wherein at least three of $Z_1$ to $Z_4$ may not be simultaneously N, and $R^Z$ is —H, —X or —O($C_1$-$C_4$ alkyl);

$Z_5$ and $Z_6$ are each independently —$CH_2$— or —O—;

$Z_7$ and $Z_8$ are each independently =CH— or =N—;

$Z_9$ is —$NR^G$— or —S—;

$R^A$ and $R^B$ are each independently —H, —($C_1$-$C_4$ alkyl), —($C_1$-$C_4$ alkyl)-OH, —($C_1$-$C_4$ alkyl)-$NR^DR^E$, -aryl, —($C_1$-$C_4$ alkyl)-aryl, —($C_3$-$C_7$ cycloalkyl) or

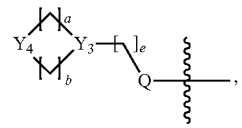

wherein at least one H of the —($C_1$-$C_4$ alkyl), —($C_1$-$C_4$ alkyl)-OH or —($C_1$-$C_4$ alkyl)-$NR^DR^E$ may be substituted with —X, at least one H of the -aryl, —($C_1$-$C_4$ alkyl)-aryl or —($C_3$-$C_7$ cycloalkyl) may be substituted with —X, —OH, —O($C_1$-$C_4$ alkyl), —($C_1$-$C_4$ alkyl), —$CF_3$, —$CF_2H$ or —CN, and at least one H of

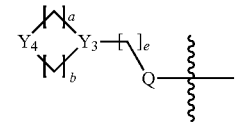

may be substituted with —X, —($C_1$-$C_4$ alkyl), —$CF_3$, —($C_2$-$C_6$ heterocycloalkyl), —($C_1$-$C_4$ alkyl)-aryl or -heteroaryl;

$R^C$ is —($C_1$-$C_4$ alkyl) or -aryl, wherein at least one H of the —($C_1$-$C_4$ alkyl) may be substituted with —X or —OH, and at least one H of the -aryl may be substituted with —X, —OH, —$CF_3$ or —$CF_2H$;

$R^D$ and $R^E$ are each independently —($C_1$-$C_4$ alkyl) or —($C_1$-$C_4$ alkyl)-aryl, wherein at least one H of the —($C_1$-$C_4$ alkyl) may be substituted with —X or —OH, and at least one H of the —($C_1$-$C_4$ alkyl)-aryl may be substituted with —X, —OH, —$CF_3$ or —$CF_2H$;

$R^F$ is —H, —($C_1$-$C_6$ alkyl), —($C_1$-$C_4$ alkyl)-OH, —($C_1$-$C_4$ alkyl)-O—($C_1$-$C_4$ alkyl), —C(=O)—($C_1$-$C_4$ alkyl), —C(=O)—O($C_1$-$C_4$ alkyl), —($C_1$-$C_4$ alkyl)-C(=O)—O($C_1$-$C_4$ alkyl), —($C_1$-$C_4$ alkyl)-$NR^DR^E$, —$S(=O)_2$—($C_1$-$C_4$ alkyl), -aryl, —($C_1$-$C_4$ alkyl)-aryl, —($C_2$-$C_4$ alkenyl)-aryl, -heteroaryl, —($C_1$-$C_4$ alkyl)-heteroaryl, —C(=O)—($C_3$-$C_7$ cycloalkyl), —($C_2$-$C_6$ heterocycloalkyl) or —($C_1$-$C_4$ alkyl)-C(=O)—($C_2$-$C_6$ heterocycloalkyl), wherein at least one H of the —(C$_1$-C$_4$ alkyl), —(C$_1$-C$_4$ alkyl)-OH, —(C$_1$-C$_4$ alkyl)-O—(C$_1$-C$_4$ alkyl), —C(=O)—(C$_1$-C$_4$ alkyl), —C(=O)—O(C$_1$-C$_4$ alkyl), —(C$_1$-C$_4$ alkyl)-C(=O)—O(C$_1$-C$_4$ alkyl), —(C$_1$-C$_4$ alkyl)-NR$^D$R$^E$ or —S(=O)$_2$—(C$_1$-C$_4$ alkyl) may be substituted with —X, and wherein at least one H of the -aryl, —(C$_1$-C$_4$ alkyl)-aryl, —(C$_2$-C$_4$ alkenyl)-aryl, -heteroaryl, —(C$_1$-C$_4$ alkyl)-heteroaryl, —C(=O)—(C$_3$-C$_7$ cycloalkyl), —(C$_2$-C$_6$ heterocycloalkyl) or —(C$_1$-C$_4$ alkyl)-C(=O)—(C$_2$-C$_6$ heterocycloalkyl) may be substituted with —X, —OH, —CF$_3$ or —CF$_2$H;

R$^G$ is —H or —(C$_1$-C$_4$ alkyl);

Q is —O— or a bond,

==== is a single bond or a double bond, provided that when ==== is a double bond, then Y$_1$ is =CH—;

a to e are each independently an integer of 0, 1, 2, 3 or 4, provided that a and b may not be simultaneously 0, and c and d may not be simultaneously 0; and X is F, Cl, Br or I.

3. The 1,3,4-oxadiazole derivative compound represented by formula I, stereoisomer thereof or pharmaceutically acceptable salt thereof according to claim 2, wherein L$_1$ or L$_3$ are each independently a bond;

L$_2$ is —(C$_1$-C$_2$ alkylene)-;

R$_1$ is —CF$_2$H or —CF$_3$;

R$_2$ is —NR$^A$R$^B$,

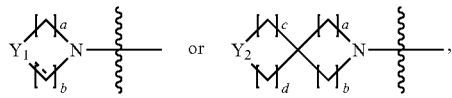

wherein at least one H of

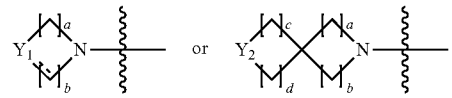

may be substituted with —X, —NR$^D$R$^E$ or —(C$_1$-C$_4$ alkyl);

R$_3$ is -aryl, -heteroaryl,

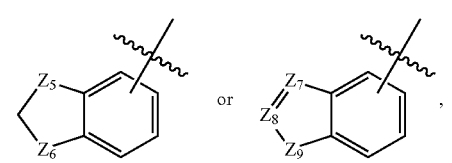

wherein at least one H of the -aryl or -heteroaryl may be substituted with —X, —O(C$_1$-C$_4$ alkyl), —OCF$_3$, —(C$_1$-C$_4$ alkyl), -heteroaryl or

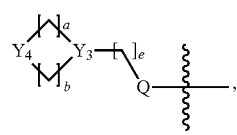

wherein at least one H of

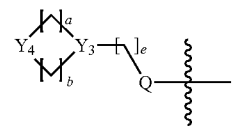

may be substituted with —X or —(C$_1$-C$_4$ alkyl), and at least one H of the

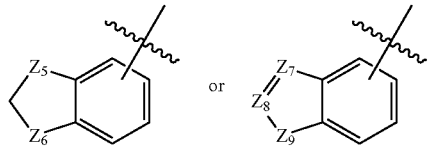

may be substituted with —X, —OH or —(C$_1$-C$_4$ alkyl);

Y$_1$ is —CH$_2$—, —NR$^F$—, —O— or —S(=O)$_2$—;

Y$_2$ is —NR$^F$—, or —O—;

Y$_3$ is —N—;

Y$_4$ is —NR$^F$—, —O— or —S(=O)$_2$—;

Z$_1$ to Z$_4$ are each independently N or CR$^Z$, wherein at least two of Z$_1$ to Z$_4$ may not be simultaneously N, and R$^Z$ is —H or —X;

Z$_5$ and Z$_6$ are each independently —CH$_2$— or —O—;

Z$_7$ and Z$_8$ are each independently =CH— or =N—;

Z$_9$ is —NR$^G$—;

R$^A$ and R$^B$ are each independently —(C$_1$-C$_4$ alkyl), —(C$_1$-C$_4$ alkyl)-OH, —(C$_1$-C$_4$ alkyl)-NR$^D$R$^E$ or

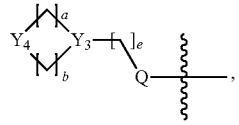

wherein at least one H of the —(C$_1$-C$_4$ alkyl), —(C$_1$-C$_4$ alkyl)-OH or —(C$_1$-C$_4$ alkyl)-NR$^D$R$^E$ may be substituted with —X, and at least one H of

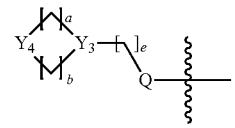

may be substituted with —X or —(C$_1$-C$_4$ alkyl);

R$^D$ and R$^E$ are each independently —(C$_1$-C$_4$ alkyl), wherein at least one H of the —(C$_1$-C$_4$ alkyl) may be substituted with —X or —OH;

R$^F$ is —H, —(C$_1$-C$_6$ alkyl), —(C$_1$-C$_4$ alkyl)-OH, —C(=O)—(C$_1$-C$_4$ alkyl), —S(=O)$_2$—(C$_1$-C$_4$ alkyl) or —(C$_2$-C$_6$ heterocycloalkyl), wherein at least one H of the —(C$_1$-C$_4$ alkyl), —(C$_1$-C$_4$ alkyl)-OH, —C(=O)—(C$_1$-C$_4$ alkyl) or —S(=O)$_2$—(C$_1$-C$_4$ alkyl) may be substituted with —X, and wherein at least one H of the —(C$_2$-C$_6$ heterocycloalkyl) may be substituted with —X, —OH, —CF$_3$ or —CF$_2$H;

R$^G$ is —H or —(C$_1$-C$_4$ alkyl);

Q is —O— or a bond,

---- is a single bond;
a to d are each independently an integer of 1 or 2;
e is an integer of 0, 1, 2, 3 or 4; and
X is F, Cl or Br.

4. The 1,3,4-oxadiazole derivative compound represented by formula I, stereoisomer thereof or pharmaceutically acceptable salt thereof according to claim 3,
wherein $L_1$ or $L_3$ are each independently a bond;
$L_2$ is —($C_1$-$C_2$ alkylene)-;
$R_1$ is —$CF_2H$;
$R_2$ is —$NR^A R^B$,

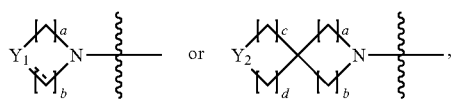

wherein at least one H of

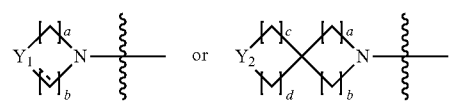

may be substituted with —X or —$NR^D R^E$;
$R_3$ is -aryl, -heteroaryl or

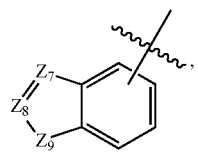

wherein at least one H of the -aryl or -heteroaryl may be substituted with —X, —($C_1$-$C_4$ alkyl) or -heteroaryl, and at least one H of the

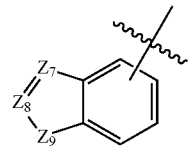

may be substituted with —X, —OH or —($C_1$-$C_4$ alkyl);
$Y_1$ is —$CH_2$—, —$NR^F$—, —O— or —$S(=O)_2$—;
$Y_2$ is —$NR^F$—, or —O—;
$Z_1$ to $Z_4$ are each independently N or $CR^Z$, wherein at least two of $Z_1$ to $Z_4$ may not be simultaneously N, and $R^Z$ is —H or —X;
$Z_7$ and $Z_8$ are each independently =CH— or =N—;
$Z_9$ is —$NR^G$—;
$R^A$ and $R^B$ are each independently —($C_1$-$C_4$ alkyl) or —($C_1$-$C_4$ alkyl)-OH,
wherein at least one H of the —($C_1$-$C_4$ alkyl) or —($C_1$-$C_4$ alkyl)-OH may be substituted with —X;
$R^D$ and $R^E$ are each independently —($C_1$-$C_4$ alkyl), wherein at least one H of the —($C_1$-$C_4$ alkyl) may be substituted with —X or —OH;
$R^F$ is —H, —($C_1$-$C_6$ alkyl), —($C_1$-$C_4$ alkyl)-OH, —C(=O)—($C_1$-$C_4$ alkyl), —S(=O)_2—($C_1$-$C_4$ alkyl) or —($C_2$-$C_6$ heterocycloalkyl),
wherein at least one H of the —($C_1$-$C_4$ alkyl), —($C_1$-$C_4$ alkyl)-OH, —C(=O)—($C_1$-$C_4$ alkyl) or —S(=O)_2—($C_1$-$C_4$ alkyl) may be substituted with —X, and
wherein at least one H of the —($C_2$-$C_6$ heterocycloalkyl) may be substituted with —X, —OH, —$CF_3$ or —$CF_2H$;
$R^G$ is —H or —($C_1$-$C_4$ alkyl);
==== is a single bond;
a to d are each independently an integer of 1 or 2; and
X is F, Cl or Br.

5. A 1,3,4-oxadiazole derivative compound, stereoisomer thereof or pharmaceutically acceptable salt thereof, wherein the compound is selected from the group consisting of compounds described in the following table:

| Ex. | Comp. | Structure |
|---|---|---|
| 1 | 21249 | 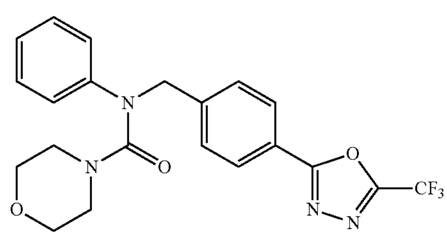 [SMILES: O=C(N1CCOCC1)N(Cc1ccc(-c2nnc(C(F)(F)F)o2)cc1)c1ccccc1] |
| 2 | 21285 | 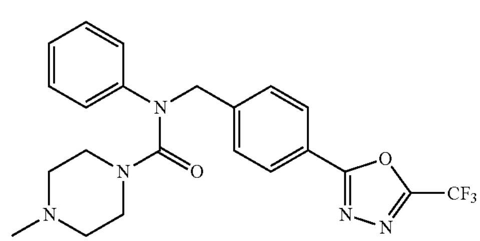 [SMILES: CN1CCN(C(=O)N(Cc2ccc(-c3nnc(C(F)(F)F)o3)cc2)c2ccccc2)CC1] |

-continued
| Ex. | Comp. | Structure |
|---|---|---|
| 3 | 21318 | 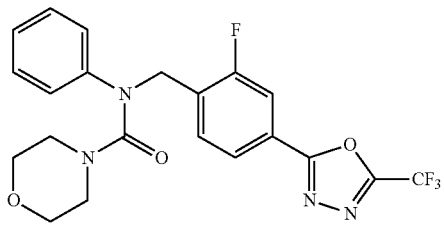 [SMILES: O=C(N1CCOCC1)N(Cc1ccc(-c2nnc(C(F)(F)F)o2)cc1F)c1ccccc1] |
| 4 | 21319 | 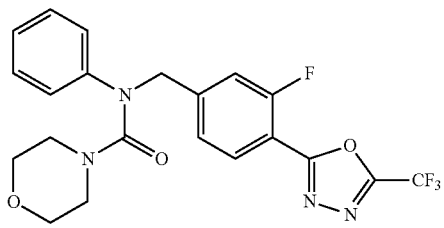 [SMILES: O=C(N1CCOCC1)N(Cc1ccc(-c2nnc(C(F)(F)F)o2)c(F)c1)c1ccccc1] |
| 5 | 21325 | 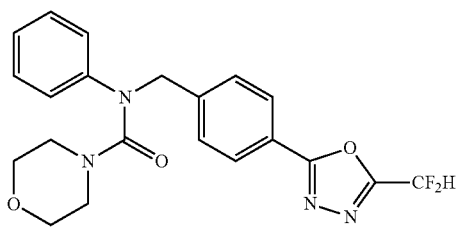 [SMILES: O=C(N1CCOCC1)N(Cc1ccc(-c2nnc(C(F)F)o2)cc1)c1ccccc1] |
| 6 | 21327 | 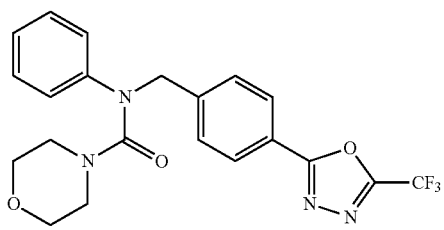 |
| 7 | 21329 | 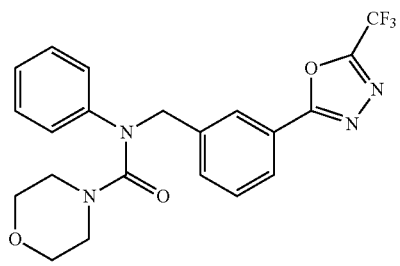 [SMILES: O=C(N1CCOCC1)N(Cc1cccc(-c2nnc(C(F)(F)F)o2)c1)c1ccccc1] |
| 8 | 21333 | 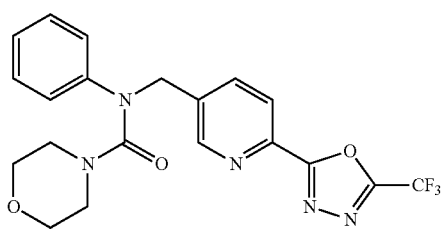 [SMILES: O=C(N1CCOCC1)N(Cc1ccc(-c2nnc(C(F)(F)F)o2)nc1)c1ccccc1] |

| Ex. | Comp. | Structure |
|---|---|---|
| 9 | 21336 | 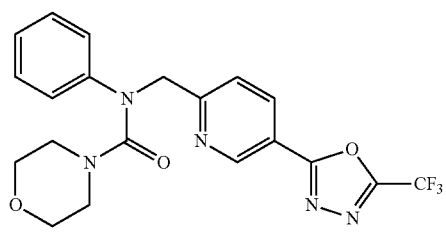 [SMILES: O=C(N1CCOCC1)N(Cc1ccc(-c2nnc(C(F)(F)F)o2)cn1)c1ccccc1] |
| 10 | 21337 | 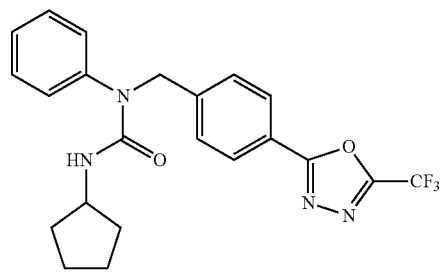 [SMILES: O=C(NC1CCCC1)N(Cc1ccc(-c2nnc(C(F)(F)F)o2)cc1)c1ccccc1] |
| 11 | 21340 | 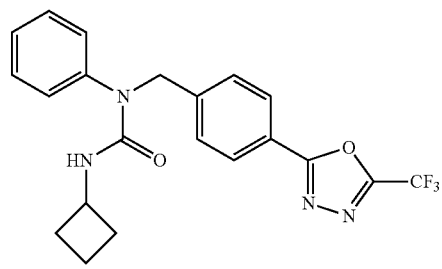 [SMILES: O=C(NC1CCC1)N(Cc1ccc(-c2nnc(C(F)(F)F)o2)cc1)c1ccccc1] |
| 12 | 21341 | 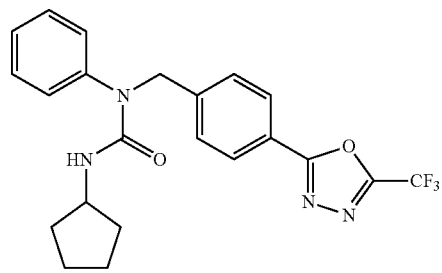 [SMILES: O=C(NC1CCCC1)N(Cc1ccc(-c2nnc(C(F)(F)F)o2)cc1)c1ccccc1] |
| 13 | 21342 | 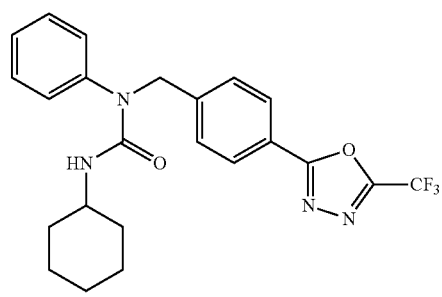 [SMILES: O=C(NC1CCCCC1)N(Cc1ccc(-c2nnc(C(F)(F)F)o2)cc1)c1ccccc1] |
| 14 | 21343 | 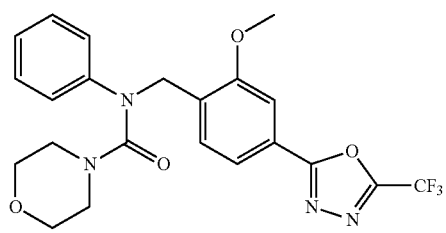 |

-continued
| Ex. | Comp. | Structure |
|---|---|---|
| 15 | 21344 | 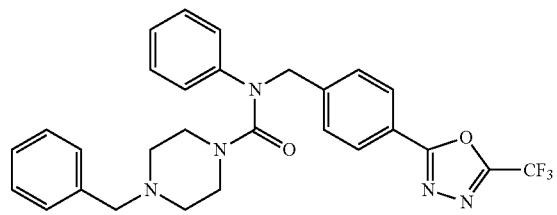 [SMILES: O=C(N1CCN(Cc2ccccc2)CC1)N(Cc1ccc(-c2nnc(C(F)(F)F)o2)cc1)c1ccccc1] |
| 16 | 21345 | 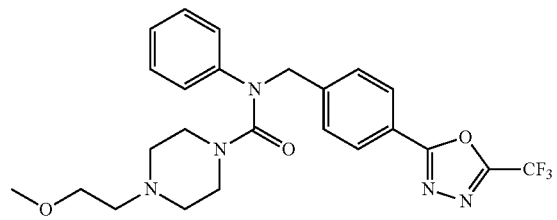 [SMILES: COCCN1CCN(C(=O)N(Cc2ccc(-c3nnc(C(F)(F)F)o3)cc2)c2ccccc2)CC1] |
| 17 | 21346 | 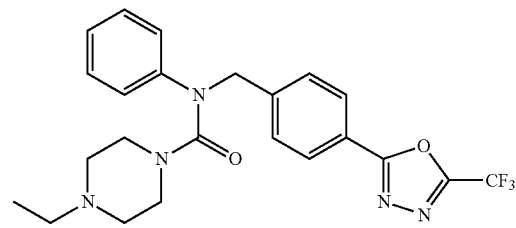 [SMILES: CCN1CCN(C(=O)N(Cc2ccc(-c3nnc(C(F)(F)F)o3)cc2)c2ccccc2)CC1] |
| 18 | 21347 | 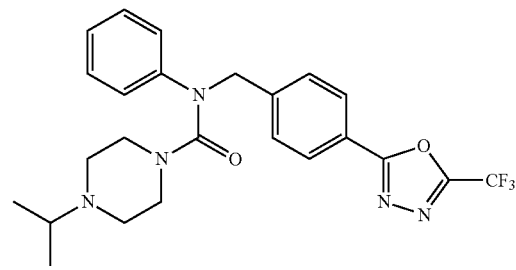 [SMILES: CC(C)N1CCN(C(=O)N(Cc2ccc(-c3nnc(C(F)(F)F)o3)cc2)c2ccccc2)CC1] |
| 19 | 21348 | 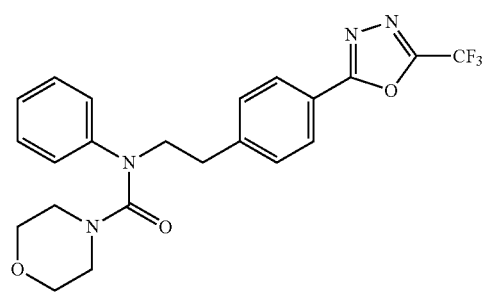 [SMILES: O=C(N1CCOCC1)N(CCc1ccc(-c2nnc(C(F)(F)F)o2)cc1)c1ccccc1] |
| 20 | 21349 | 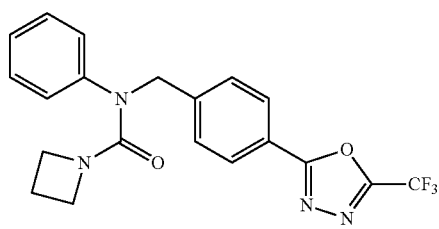 [SMILES: O=C(N1CCC1)N(Cc1ccc(-c2nnc(C(F)(F)F)o2)cc1)c1ccccc1] |

| Ex. | Comp. | Structure |
|---|---|---|
| 21 | 21350 | 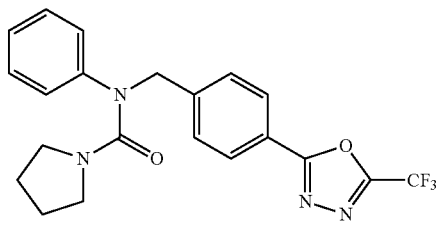 [SMILES: O=C(N1CCCC1)N(Cc1ccc(-c2nnc(C(F)(F)F)o2)cc1)c1ccccc1] |
| 22 | 21351 | 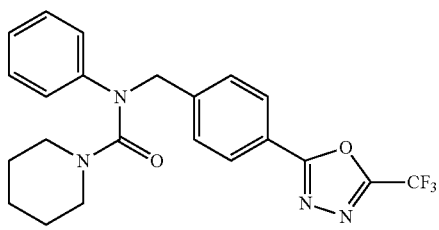 [SMILES: O=C(N1CCCCC1)N(Cc1ccc(-c2nnc(C(F)(F)F)o2)cc1)c1ccccc1] |
| 23 | 21352 | 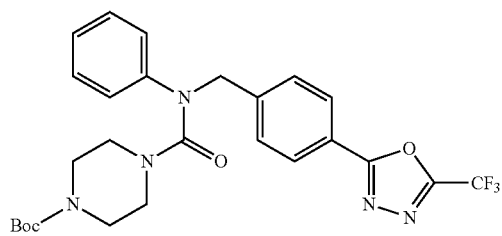 [SMILES: CC(C)(C)OC(=O)N1CCN(C(=O)N(Cc2ccc(-c3nnc(C(F)(F)F)o3)cc2)c2ccccc2)CC1] |
| 24 | 21353 | 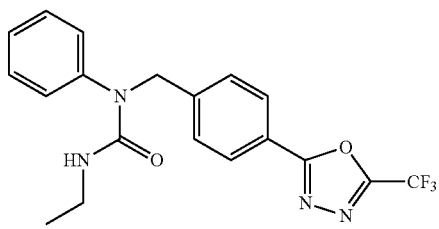 [SMILES: CCNC(=O)N(Cc1ccc(-c2nnc(C(F)(F)F)o2)cc1)c1ccccc1] |
| 25 | 21354 | 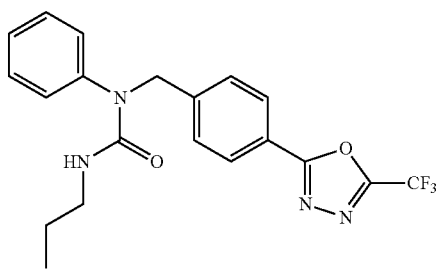 [SMILES: CCCNC(=O)N(Cc1ccc(-c2nnc(C(F)(F)F)o2)cc1)c1ccccc1] |
| 26 | 21355 | 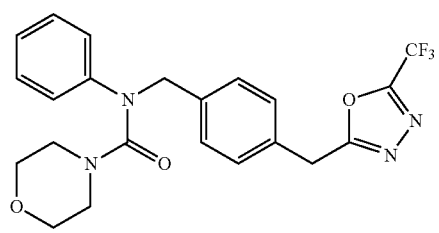 [SMILES: O=C(N1CCOCC1)N(Cc1ccc(Cc2nnc(C(F)(F)F)o2)cc1)c1ccccc1] |

| Ex. | Comp. | Structure |
|---|---|---|
| 27 | 21357 | 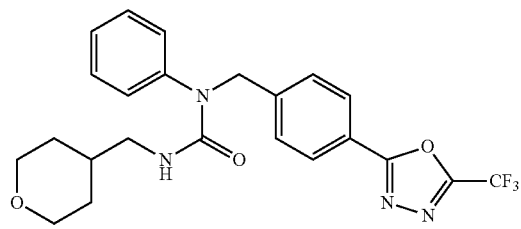 [SMILES: O=C(NCC1CCOCC1)N(Cc1ccc(-c2nnc(C(F)(F)F)o2)cc1)c1ccccc1] |
| 28 | 21358 | 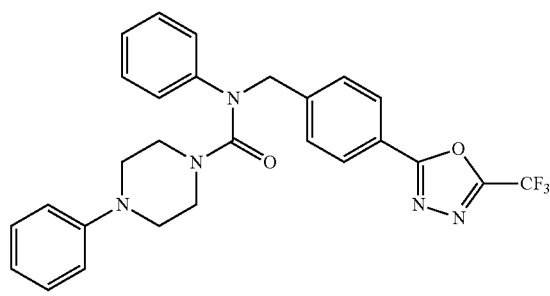 [SMILES: O=C(N1CCN(c2ccccc2)CC1)N(Cc1ccc(-c2nnc(C(F)(F)F)o2)cc1)c1ccccc1] |
| 29 | 21359 | 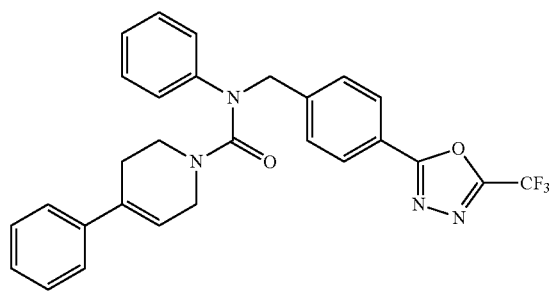 [SMILES: O=C(N1CC=C(c2ccccc2)CC1)N(Cc1ccc(-c2nnc(C(F)(F)F)o2)cc1)c1ccccc1] |
| 30 | 21360 | 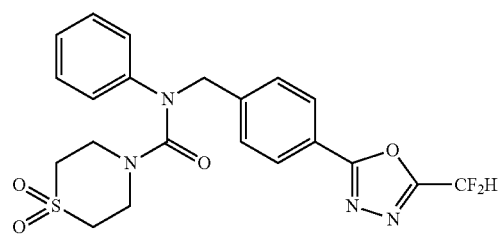 [SMILES: O=C(N1CCS(=O)(=O)CC1)N(Cc1ccc(-c2nnc(C(F)F)o2)cc1)c1ccccc1] |
| 31 | 21361 | 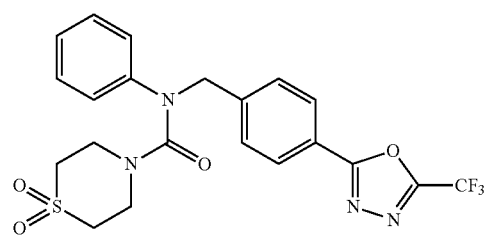 [SMILES: O=C(N1CCS(=O)(=O)CC1)N(Cc1ccc(-c2nnc(C(F)(F)F)o2)cc1)c1ccccc1] |
| 32 | 21362 | 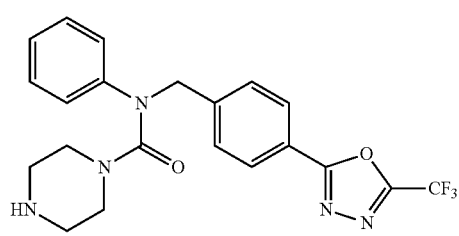 [SMILES: O=C(N1CCNCC1)N(Cc1ccc(-c2nnc(C(F)(F)F)o2)cc1)c1ccccc1] |

| Ex. | Comp. | Structure |
|---|---|---|
| 33 | 21363 | 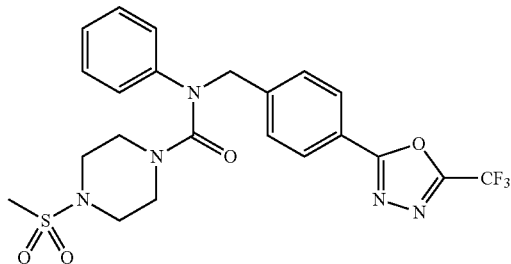 [SMILES: CS(=O)(=O)N1CCN(C(=O)N(Cc2ccc(-c3nnc(C(F)(F)F)o3)cc2)c2ccccc2)CC1] |
| 34 | 21364 | 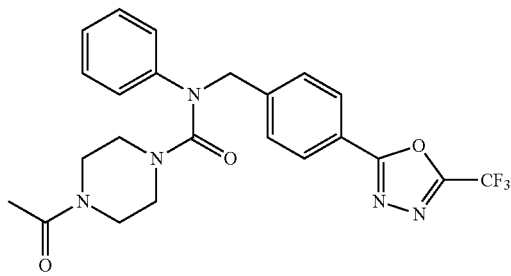 [SMILES: CC(=O)N1CCN(C(=O)N(Cc2ccc(-c3nnc(C(F)(F)F)o3)cc2)c2ccccc2)CC1] |
| 35 | 21365 | 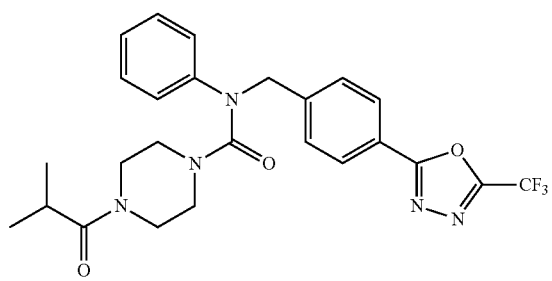 |
| 36 | 21366 | 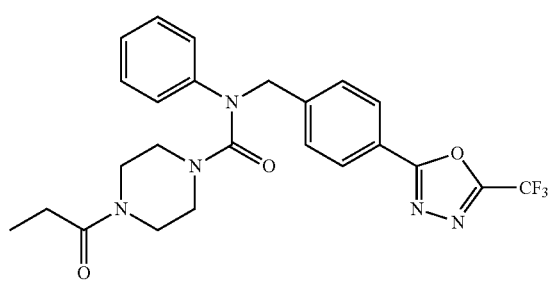 [SMILES: CCC(=O)N1CCN(C(=O)N(Cc2ccc(-c3nnc(C(F)(F)F)o3)cc2)c2ccccc2)CC1] |
| 37 | 21367 | 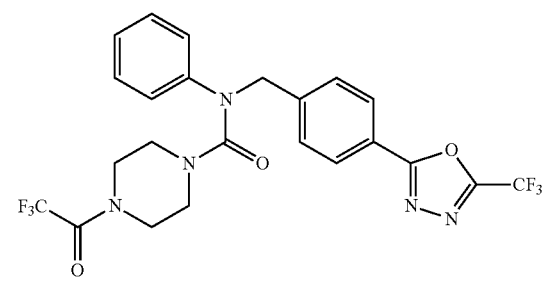 [SMILES: O=C(N1CCN(C(=O)C(F)(F)F)CC1)N(Cc1ccc(-c2nnc(C(F)(F)F)o2)cc1)c1ccccc1] |

-continued
| Ex. | Comp. | Structure |
|---|---|---|
| 38 | 21368 | 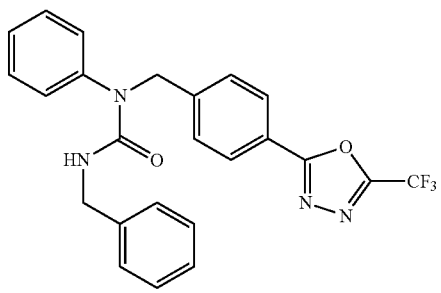 [SMILES: O=C(NCc1ccccc1)N(Cc1ccc(-c2nnc(C(F)(F)F)o2)cc1)c1ccccc1] |
| 39 | 21369 | 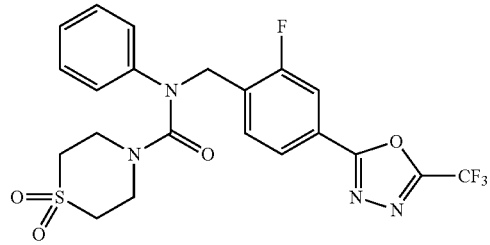 [SMILES: O=C(N1CCS(=O)(=O)CC1)N(Cc1ccc(-c2nnc(C(F)(F)F)o2)cc1F)c1ccccc1] |
| 40 | 21370 | 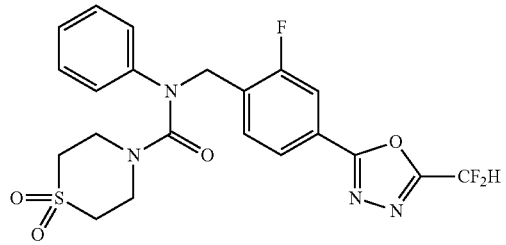 [SMILES: O=C(N1CCS(=O)(=O)CC1)N(Cc1ccc(-c2nnc(C(F)F)o2)cc1F)c1ccccc1] |
| 41 | 21371 | 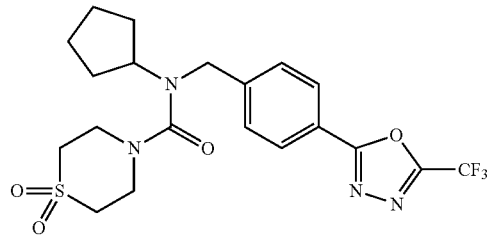 [SMILES: O=C(N1CCS(=O)(=O)CC1)N(Cc1ccc(-c2nnc(C(F)(F)F)o2)cc1)C1CCCC1] |
| 42 | 21372 | 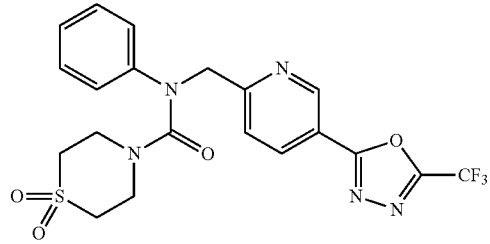 [SMILES: O=C(N1CCS(=O)(=O)CC1)N(Cc1ccc(-c2nnc(C(F)(F)F)o2)cn1)c1ccccc1] |
| 43 | 21373 | 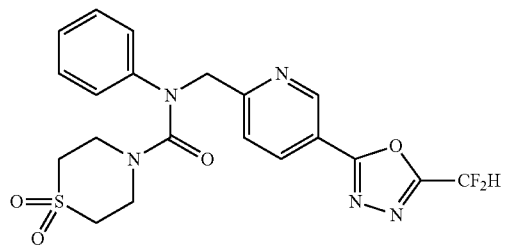 [SMILES: O=C(N1CCS(=O)(=O)CC1)N(Cc1ccc(-c2nnc(C(F)F)o2)cn1)c1ccccc1] |

-continued
| Ex. | Comp. | Structure |
|---|---|---|
| 44 | 21374 | 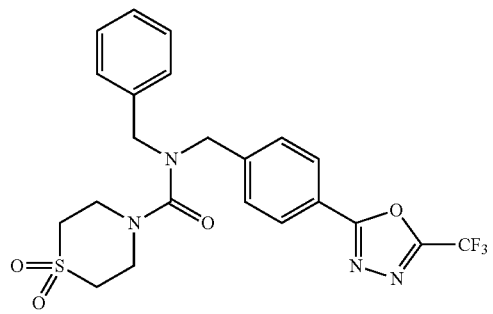 [SMILES: O=C(N1CCS(=O)(=O)CC1)N(Cc1ccccc1)Cc1ccc(-c2nnc(C(F)(F)F)o2)cc1] |
| 45 | 21375 | 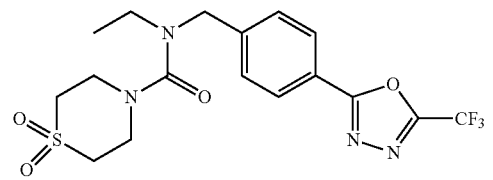 [SMILES: CCN(Cc1ccc(-c2nnc(C(F)(F)F)o2)cc1)C(=O)N1CCS(=O)(=O)CC1] |
| 46 | 21376 | 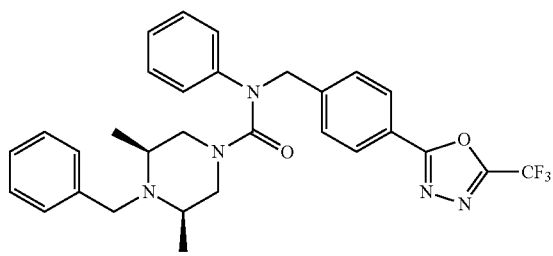 [SMILES: C[C@@H]1CN(C(=O)N(Cc2ccc(-c3nnc(C(F)(F)F)o3)cc2)c2ccccc2)C[C@H](C)N1Cc1ccccc1] |
| 47 | 21377 | 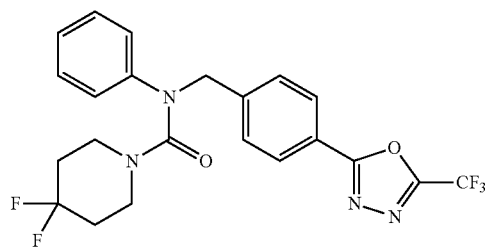 [SMILES: O=C(N1CCC(F)(F)CC1)N(Cc1ccc(-c2nnc(C(F)(F)F)o2)cc1)c1ccccc1] |
| 48 | 21378 | 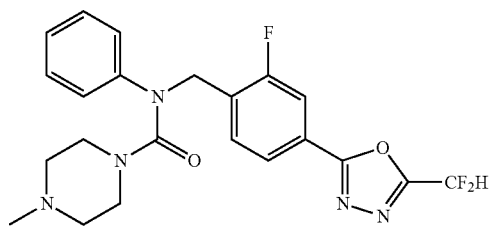 [SMILES: CN1CCN(C(=O)N(Cc2ccc(-c3nnc(C(F)F)o3)cc2F)c2ccccc2)CC1] |
| 49 | 21379 | 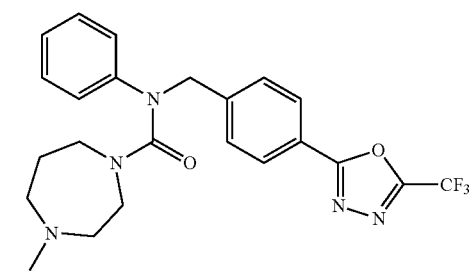 [SMILES: CN1CCCN(C(=O)N(Cc2ccc(-c3nnc(C(F)(F)F)o3)cc2)c2ccccc2)CC1] |

-continued
| Ex. | Comp. | Structure |
|---|---|---|
| 50 | 21380 | 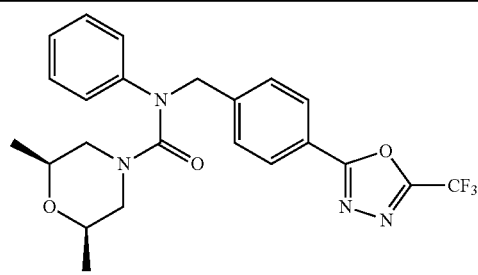 |
| 51 | 21381 | 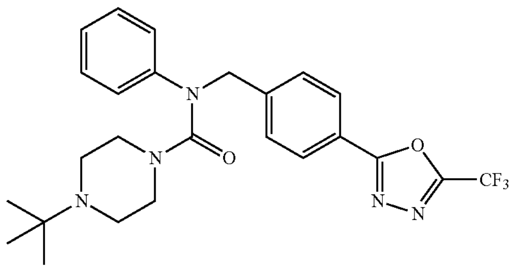 [SMILES: CC(C)(C)N1CCN(C(=O)N(Cc2ccc(-c3nnc(C(F)(F)F)o3)cc2)c2ccccc2)CC1] |
| 52 | 21382 | 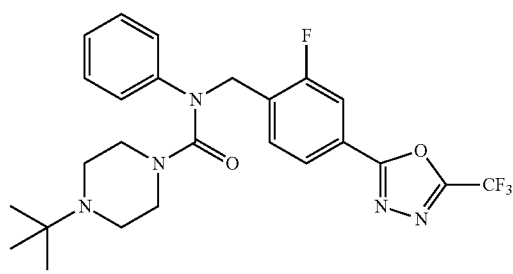 [SMILES: CC(C)(C)N1CCN(C(=O)N(Cc2ccc(-c3nnc(C(F)(F)F)o3)cc2F)c2ccccc2)CC1] |
| 53 | 21383 | 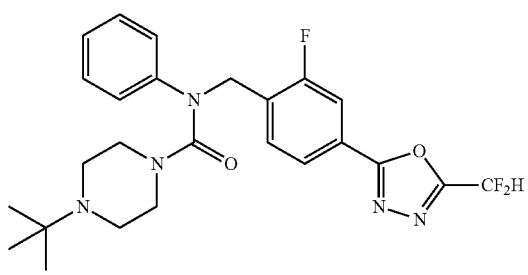 [SMILES: CC(C)(C)N1CCN(C(=O)N(Cc2ccc(-c3nnc(C(F)F)o3)cc2F)c2ccccc2)CC1] |
| 54 | 21384 | 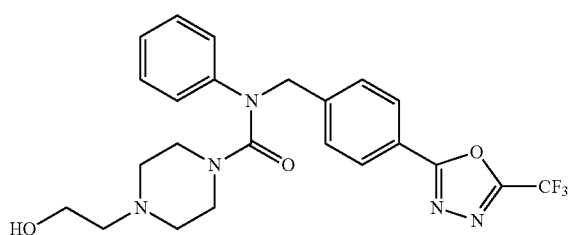 [SMILES: O=C(N1CCN(CCO)CC1)N(Cc1ccc(-c2nnc(C(F)(F)F)o2)cc1)c1ccccc1] |
| 55 | 21385 | 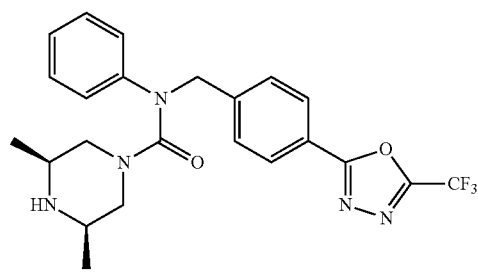 |

-continued
| Ex. | Comp. | Structure |
|---|---|---|
| 56 | 21386 | 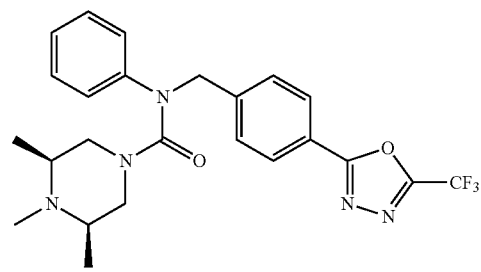 [SMILES: C[C@@H]1CN(C(=O)N(Cc2ccc(-c3nnc(C(F)(F)F)o3)cc2)c2ccccc2)C[C@H](C)N1C] |
| 57 | 21387 | 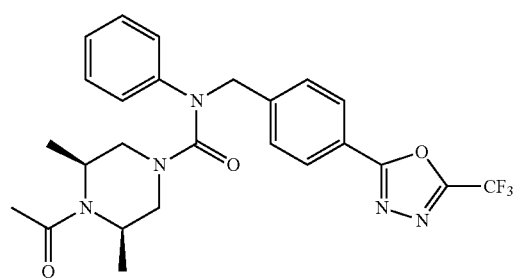 [SMILES: CC(=O)N1[C@H](C)CN(C(=O)N(Cc2ccc(-c3nnc(C(F)(F)F)o3)cc2)c2ccccc2)C[C@@H]1C] |
| 58 | 21388 | 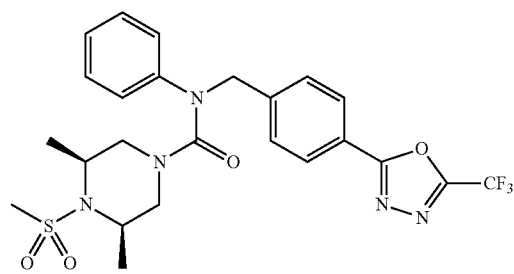 [SMILES: C[C@@H]1CN(C(=O)N(Cc2ccc(-c3nnc(C(F)(F)F)o3)cc2)c2ccccc2)C[C@H](C)N1S(C)(=O)=O] |
| 59 | 21389 | 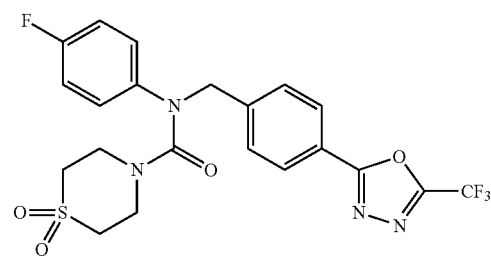 [SMILES: O=C(N1CCS(=O)(=O)CC1)N(Cc1ccc(-c2nnc(C(F)(F)F)o2)cc1)c1ccc(F)cc1] |
| 60 | 21390 | 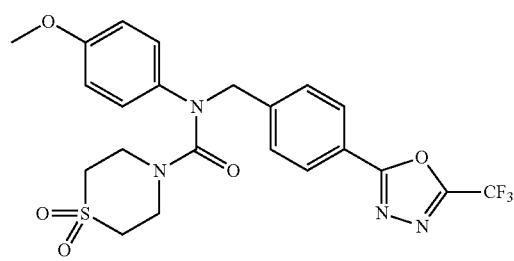 |

-continued
| Ex. | Comp. | Structure |
|---|---|---|
| 61 | 21391 | 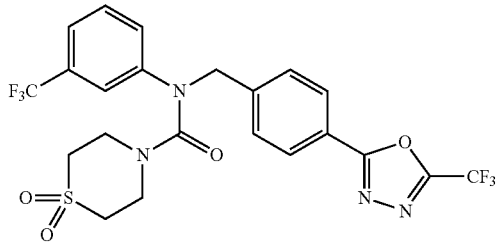 [SMILES: O=C(N1CCS(=O)(=O)CC1)N(Cc1ccc(-c2nnc(C(F)(F)F)o2)cc1)c1cccc(C(F)(F)F)c1] |
| 62 | 21392 | 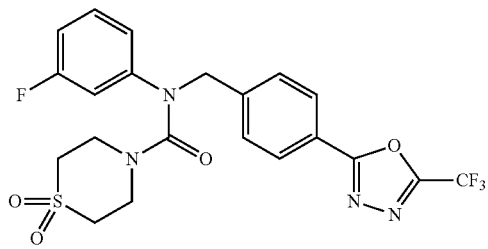 [SMILES: O=C(N1CCS(=O)(=O)CC1)N(Cc1ccc(-c2nnc(C(F)(F)F)o2)cc1)c1cccc(F)c1] |
| 63 | 21393 | 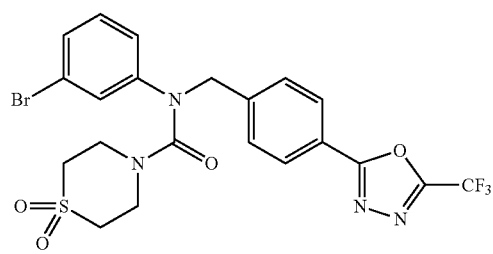 |
| 64 | 21394 | 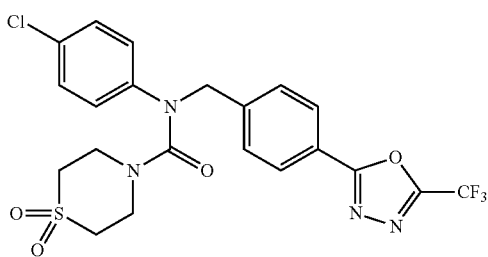 [SMILES: O=C(N1CCS(=O)(=O)CC1)N(Cc1ccc(-c2nnc(C(F)(F)F)o2)cc1)c1ccc(Cl)cc1] |
| 65 | 21395 | 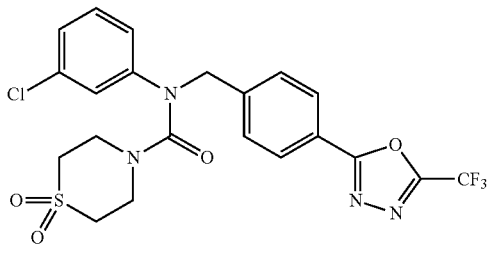 [SMILES: O=C(N1CCS(=O)(=O)CC1)N(Cc1ccc(-c2nnc(C(F)(F)F)o2)cc1)c1cccc(Cl)c1] |
| 66 | 21396 | 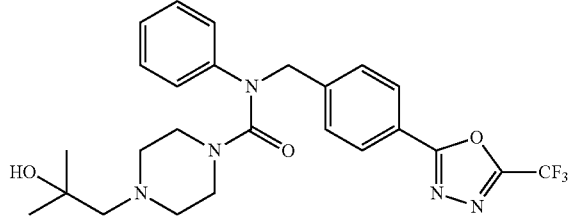 [SMILES: CC(C)(O)CN1CCN(C(=O)N(Cc2ccc(-c3nnc(C(F)(F)F)o3)cc2)c2ccccc2)CC1] |

-continued
| Ex. | Comp. | Structure |
|---|---|---|
| 67 | 21397 | 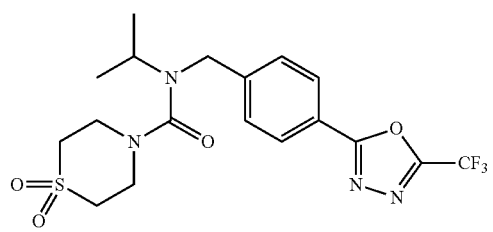 [SMILES: CC(C)N(Cc1ccc(-c2nnc(C(F)(F)F)o2)cc1)C(=O)N1CCS(=O)(=O)CC1] |
| 68 | 21398 | 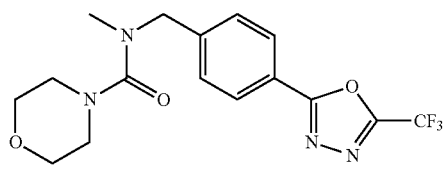 [SMILES: CN(Cc1ccc(-c2nnc(C(F)(F)F)o2)cc1)C(=O)N1CCOCC1] |
| 69 | 21399 | 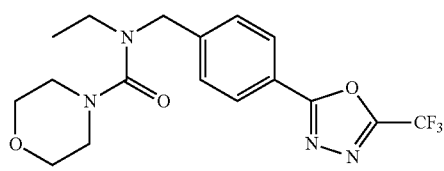 |
| 70 | 21400 | 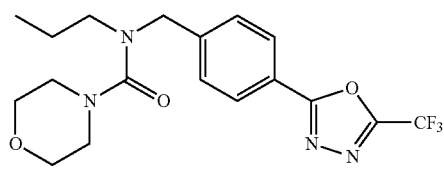 [SMILES: CCCN(Cc1ccc(-c2nnc(C(F)(F)F)o2)cc1)C(=O)N1CCOCC1] |
| 71 | 21401 | 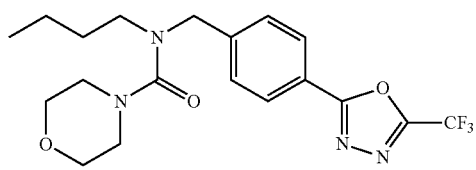 [SMILES: CCCCN(Cc1ccc(-c2nnc(C(F)(F)F)o2)cc1)C(=O)N1CCOCC1] |
| 72 | 21402 | 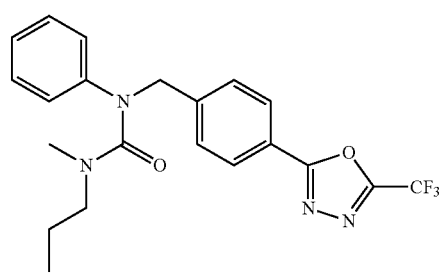 [SMILES: CCCN(C)C(=O)N(Cc1ccc(-c2nnc(C(F)(F)F)o2)cc1)c1ccccc1] |
| 73 | 21403 | 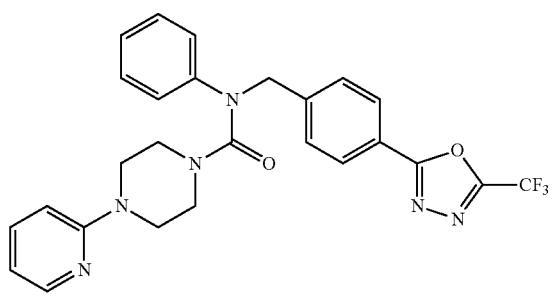 [SMILES: O=C(N1CCN(c2ccccn2)CC1)N(Cc1ccc(-c2nnc(C(F)(F)F)o2)cc1)c1ccccc1] |

| Ex. | Comp. | Structure |
|---|---|---|
| 74 | 21404 | 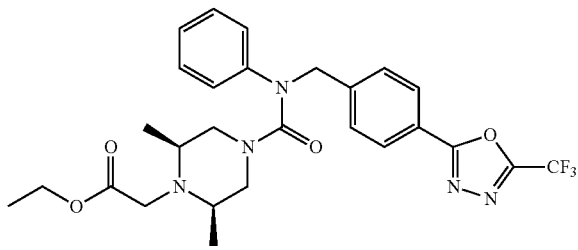 [SMILES: CCOC(=O)CN1[C@H](C)CN(C(=O)N(Cc2ccc(-c3nnc(C(F)(F)F)o3)cc2)c2ccccc2)C[C@@H]1C] |
| 75 | 21405 | 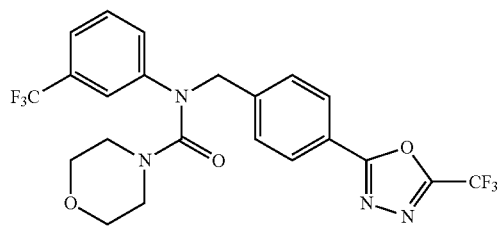 [SMILES: O=C(N1CCOCC1)N(Cc1ccc(-c2nnc(C(F)(F)F)o2)cc1)c1cccc(C(F)(F)F)c1] |
| 76 | 21406 | 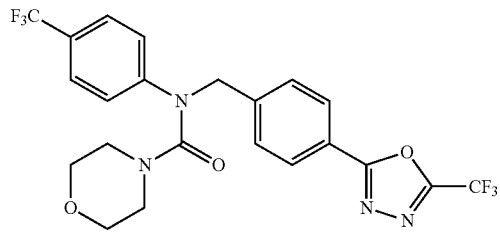 [SMILES: O=C(N1CCOCC1)N(Cc1ccc(-c2nnc(C(F)(F)F)o2)cc1)c1ccc(C(F)(F)F)cc1] |
| 77 | 21407 | 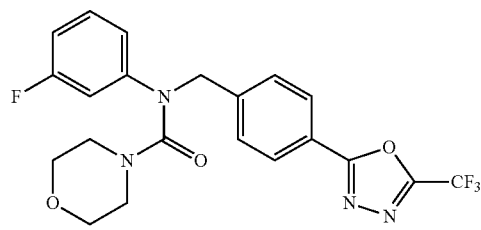 [SMILES: O=C(N1CCOCC1)N(Cc1ccc(-c2nnc(C(F)(F)F)o2)cc1)c1cccc(F)c1] |
| 78 | 21408 | 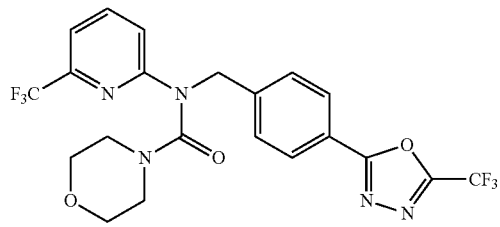 [SMILES: O=C(N1CCOCC1)N(Cc1ccc(-c2nnc(C(F)(F)F)o2)cc1)c1cccc(C(F)(F)F)n1] |
| 79 | 21409 | 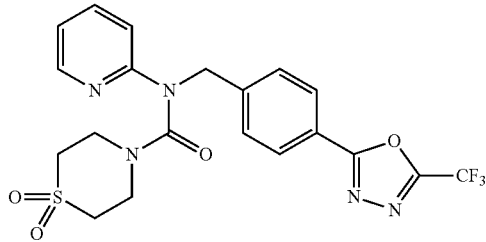 [SMILES: O=C(N1CCS(=O)(=O)CC1)N(Cc1ccc(-c2nnc(C(F)(F)F)o2)cc1)c1ccccn1] |

-continued
| Ex. | Comp. | Structure |
|---|---|---|
| 80 | 21410 | 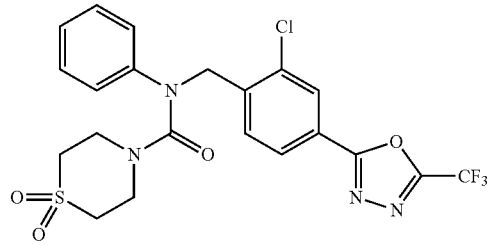 [SMILES: O=C(N1CCS(=O)(=O)CC1)N(Cc1ccc(-c2nnc(C(F)(F)F)o2)cc1Cl)c1ccccc1] |
| 81 | 21411 | 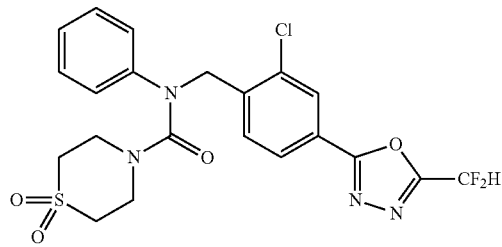 [SMILES: O=C(N1CCS(=O)(=O)CC1)N(Cc1ccc(-c2nnc(C(F)F)o2)cc1Cl)c1ccccc1] |
| 82 | 21412 | 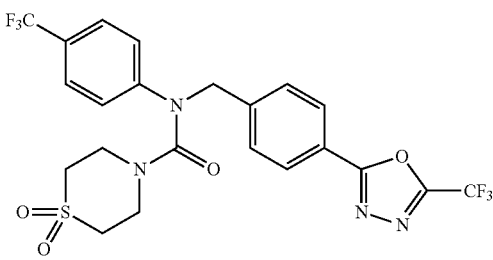 [SMILES: O=C(N1CCS(=O)(=O)CC1)N(Cc1ccc(-c2nnc(C(F)(F)F)o2)cc1)c1ccc(C(F)(F)F)cc1] |
| 83 | 21413 | 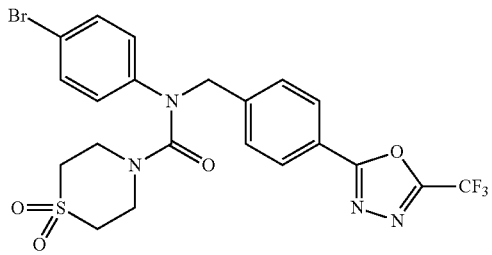 [SMILES: O=C(N1CCS(=O)(=O)CC1)N(Cc1ccc(-c2nnc(C(F)(F)F)o2)cc1)c1ccc(Br)cc1] |
| 84 | 21414 | 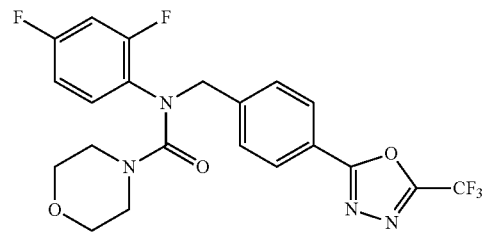 [SMILES: O=C(N1CCOCC1)N(Cc1ccc(-c2nnc(C(F)(F)F)o2)cc1)c1ccc(F)cc1F] |
| 85 | 21415 | 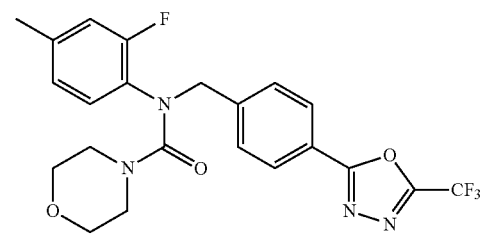 [SMILES: Cc1ccc(N(Cc2ccc(-c3nnc(C(F)(F)F)o3)cc2)C(=O)N2CCOCC2)c(F)c1] |

| Ex. | Comp. | Structure |
|---|---|---|
| 86 | 21416 | 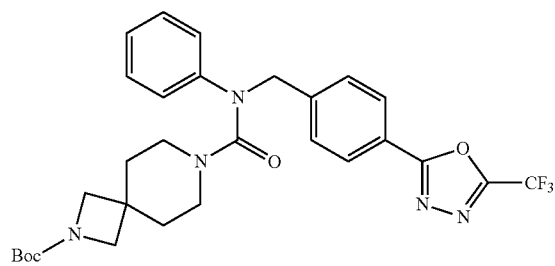 [SMILES: CC(C)(C)OC(=O)N1CC2(CCN(C(=O)N(Cc3ccc(-c4nnc(C(F)(F)F)o4)cc3)c3ccccc3)CC2)C1] |
| 87 | 21417 | 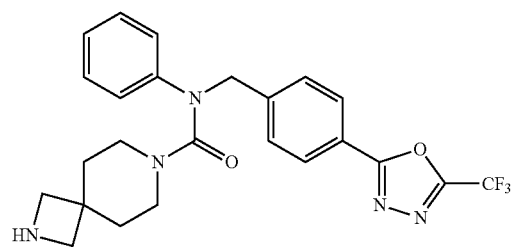 [SMILES: O=C(N1CCC2(CC1)CNC2)N(Cc1ccc(-c2nnc(C(F)(F)F)o2)cc1)c1ccccc1] |
| 88 | 21418 | 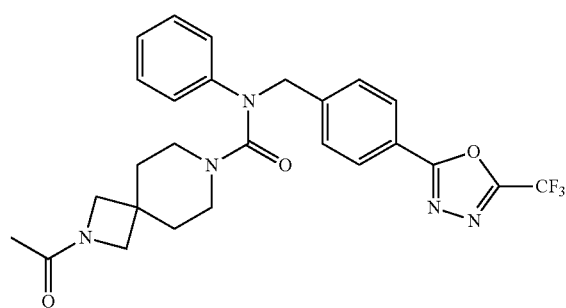 [SMILES: CC(=O)N1CC2(CCN(C(=O)N(Cc3ccc(-c4nnc(C(F)(F)F)o4)cc3)c3ccccc3)CC2)C1] |
| 89 | 21419 | 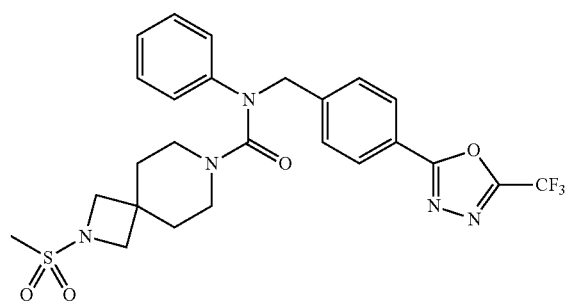 [SMILES: CS(=O)(=O)N1CC2(CCN(C(=O)N(Cc3ccc(-c4nnc(C(F)(F)F)o4)cc3)c3ccccc3)CC2)C1] |
| 90 | 21420 | 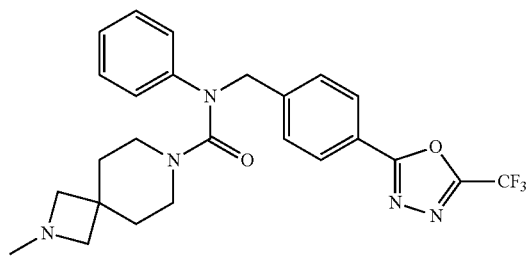 [SMILES: CN1CC2(CCN(C(=O)N(Cc3ccc(-c4nnc(C(F)(F)F)o4)cc3)c3ccccc3)CC2)C1] |

-continued
| Ex. | Comp. | Structure |
|---|---|---|
| 91 | 21421 | 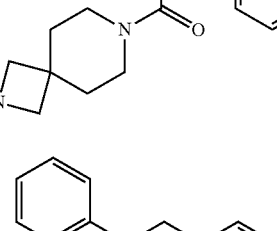 |
| 92 | 21422 | 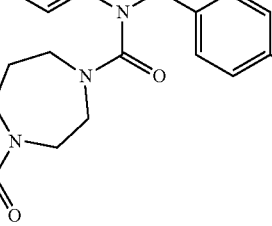 |
| 93 | 21423 | 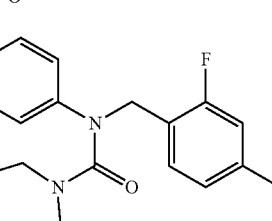 |
| 94 | 21424 | 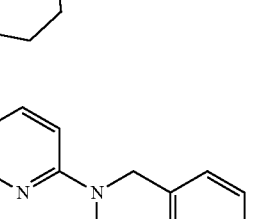 |
| 95 | 21425 | 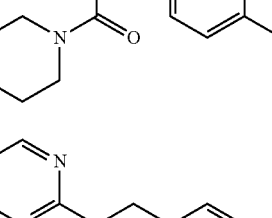 |
| 96 | 21426 | 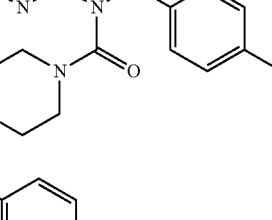 |

-continued
| Ex. | Comp. | Structure |
|---|---|---|
| 97 | 21427 | 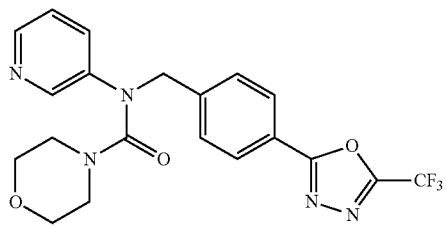 |
| 98 | 21428 | 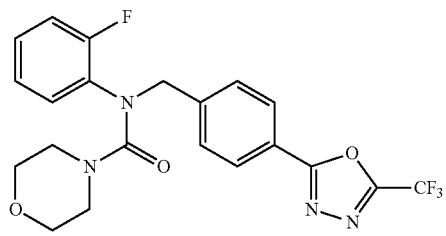 [SMILES: O=C(N1CCOCC1)N(Cc1ccc(-c2nnc(C(F)(F)F)o2)cc1)c1ccccc1F] |
| 99 | 21429 | 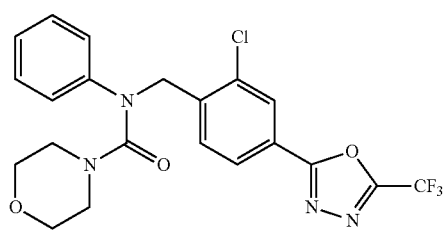 |
| 100 | 21431 | 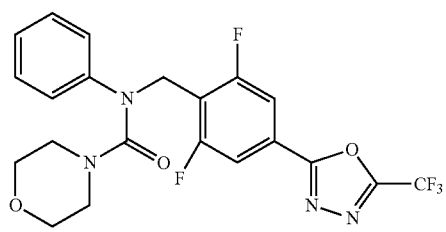 [SMILES: O=C(N1CCOCC1)N(Cc1c(F)cc(-c2nnc(C(F)(F)F)o2)cc1F)c1ccccc1] |
| 101 | 21432 | 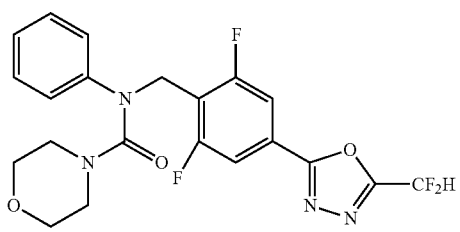 [SMILES: O=C(N1CCOCC1)N(Cc1c(F)cc(-c2nnc(C(F)F)o2)cc1F)c1ccccc1] |
| 102 | 21433 | 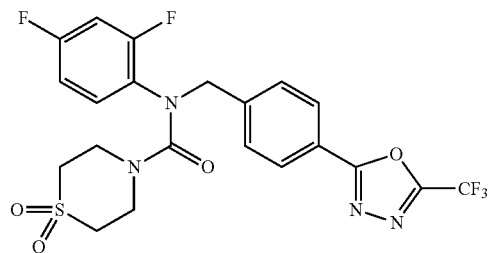 [SMILES: O=C(N1CCS(=O)(=O)CC1)N(Cc1ccc(-c2nnc(C(F)(F)F)o2)cc1)c1ccc(F)cc1F] |

-continued
| Ex. | Comp. | Structure |
|---|---|---|
| 103 | 21434 | 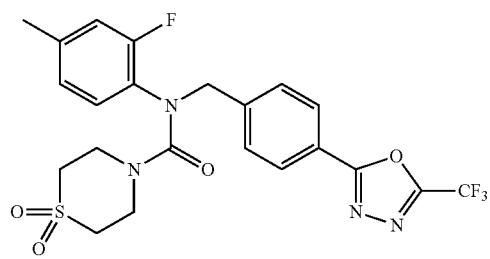 [SMILES: Cc1ccc(N(Cc2ccc(-c3nnc(C(F)(F)F)o3)cc2)C(=O)N2CCS(=O)(=O)CC2)c(F)c1] |
| 104 | 21435 | 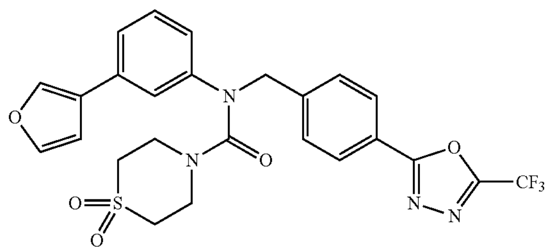 [SMILES: O=C(N1CCS(=O)(=O)CC1)N(Cc1ccc(-c2nnc(C(F)(F)F)o2)cc1)c1cccc(-c2ccoc2)c1] |
| 105 | 21436 | 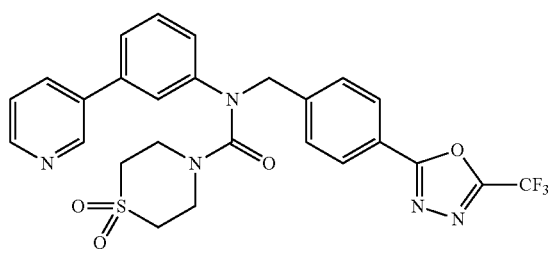 [SMILES: O=C(N1CCS(=O)(=O)CC1)N(Cc1ccc(-c2nnc(C(F)(F)F)o2)cc1)c1cccc(-c2cccnc2)c1] |
| 106 | 21437 | 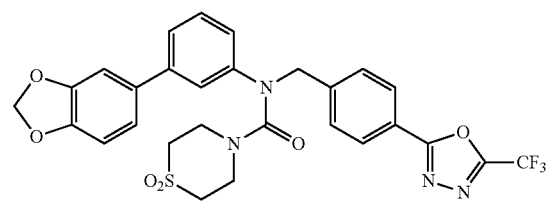 [SMILES: O=C(N1CCS(=O)(=O)CC1)N(Cc1ccc(-c2nnc(C(F)(F)F)o2)cc1)c1cccc(-c2ccc3c(c2)OCO3)c1] |
| 107 | 21438 | 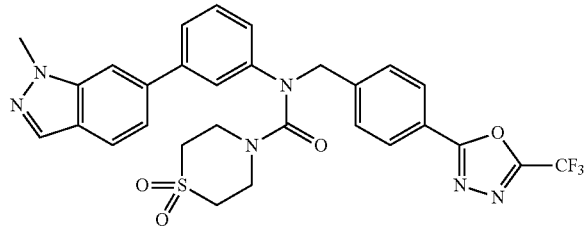 [SMILES: Cn1ncc2ccc(-c3cccc(N(Cc4ccc(-c5nnc(C(F)(F)F)o5)cc4)C(=O)N4CCS(=O)(=O)CC4)c3)cc21] |
| 108 | 21439 | 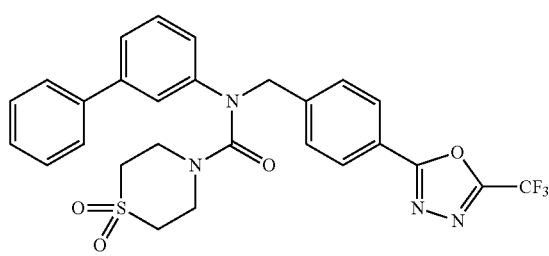 [SMILES: O=C(N1CCS(=O)(=O)CC1)N(Cc1ccc(-c2nnc(C(F)(F)F)o2)cc1)c1cccc(-c2ccccc2)c1] |

| Ex. | Comp. | Structure |
|---|---|---|
| 109 | 21440 | 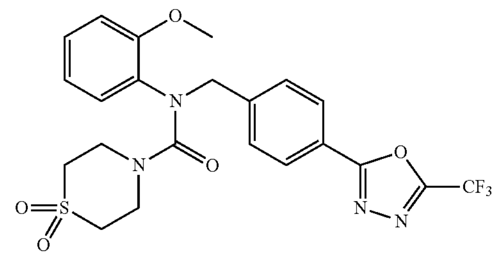 [SMILES: COc1ccccc1N(Cc1ccc(-c2nnc(C(F)(F)F)o2)cc1)C(=O)N1CCS(=O)(=O)CC1] |
| 110 | 21441 | 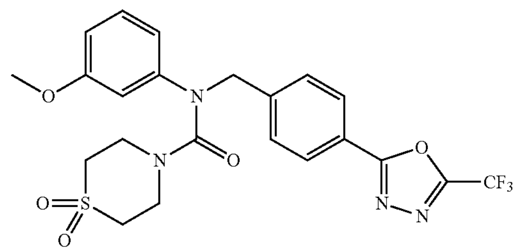 [SMILES: COc1cccc(N(Cc2ccc(-c3nnc(C(F)(F)F)o3)cc2)C(=O)N2CCS(=O)(=O)CC2)c1] |
| 111 | 21442 | 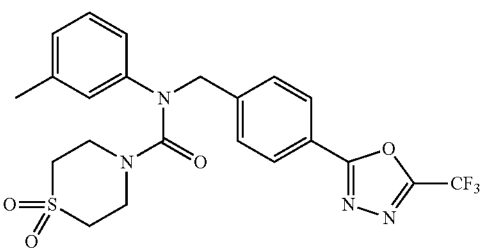 |
| 112 | 21443 | 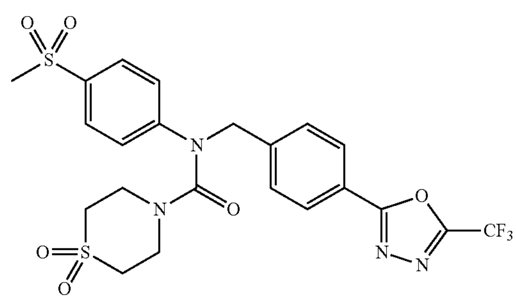 [SMILES: CS(=O)(=O)c1ccc(N(Cc2ccc(-c3nnc(C(F)(F)F)o3)cc2)C(=O)N2CCS(=O)(=O)CC2)cc1] |
| 113 | 21444 | 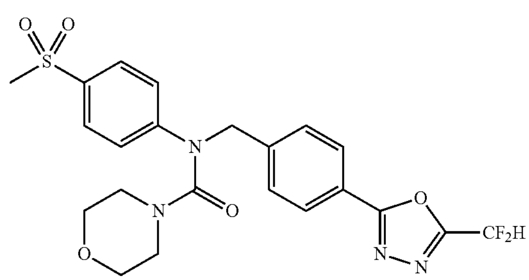 [SMILES: CS(=O)(=O)c1ccc(N(Cc2ccc(-c3nnc(C(F)F)o3)cc2)C(=O)N2CCOCC2)cc1] |
| 114 | 21445 | 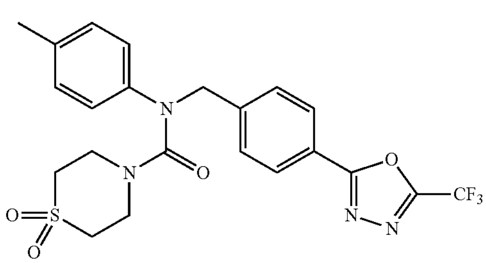 [SMILES: Cc1ccc(N(Cc2ccc(-c3nnc(C(F)(F)F)o3)cc2)C(=O)N2CCS(=O)(=O)CC2)cc1] |

| Ex. | Comp. | Structure |
|---|---|---|
| 115 | 21446 | 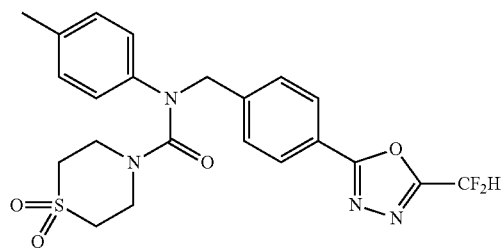 [SMILES: Cc1ccc(N(Cc2ccc(-c3nnc(C(F)F)o3)cc2)C(=O)N2CCS(=O)(=O)CC2)cc1] |
| 116 | 21447 | 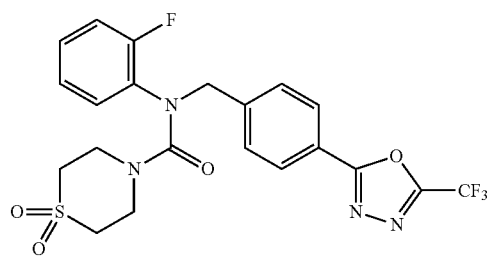 [SMILES: O=C(N1CCS(=O)(=O)CC1)N(Cc1ccc(-c2nnc(C(F)(F)F)o2)cc1)c1ccccc1F] |
| 117 | 21448 | 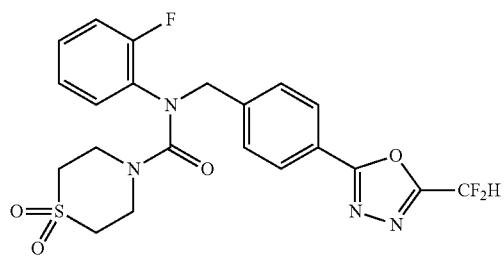 [SMILES: O=C(N1CCS(=O)(=O)CC1)N(Cc1ccc(-c2nnc(C(F)F)o2)cc1)c1ccccc1F] |
| 118 | 21449 | 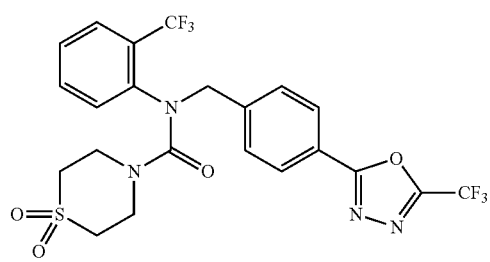 [SMILES: O=C(N1CCS(=O)(=O)CC1)N(Cc1ccc(-c2nnc(C(F)(F)F)o2)cc1)c1ccccc1C(F)(F)F] |
| 119 | 21450 | 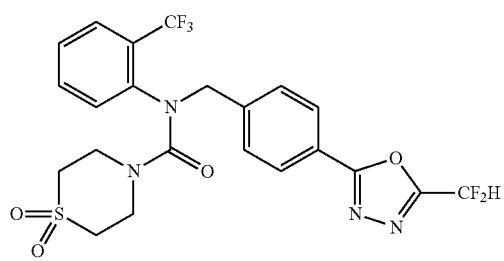 [SMILES: O=C(N1CCS(=O)(=O)CC1)N(Cc1ccc(-c2nnc(C(F)F)o2)cc1)c1ccccc1C(F)(F)F] |
| 120 | 21451 | 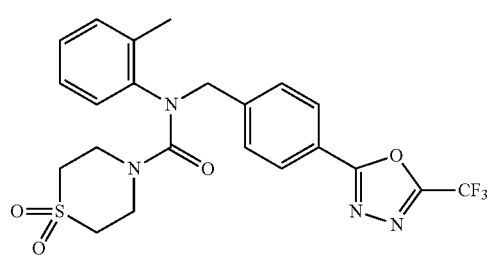 [SMILES: Cc1ccccc1N(Cc1ccc(-c2nnc(C(F)(F)F)o2)cc1)C(=O)N1CCS(=O)(=O)CC1] |

-continued
| Ex. | Comp. | Structure |
|---|---|---|
| 121 | 21452 | 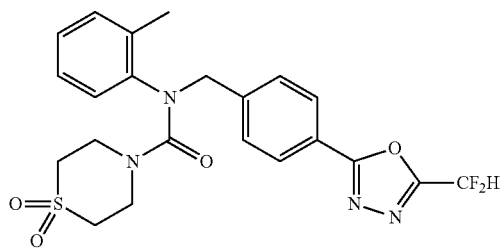 [SMILES: Cc1ccccc1N(Cc1ccc(-c2nnc(C(F)F)o2)cc1)C(=O)N1CCS(=O)(=O)CC1] |
| 122 | 21453 | 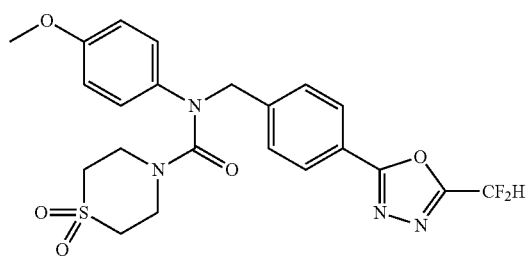 [SMILES: COc1ccc(N(Cc2ccc(-c3nnc(C(F)F)o3)cc2)C(=O)N2CCS(=O)(=O)CC2)cc1] |
| 123 | 21454 | 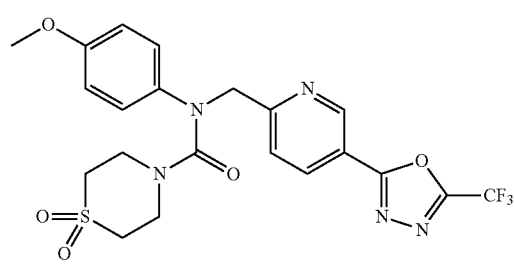 [SMILES: COc1ccc(N(Cc2ccc(-c3nnc(C(F)(F)F)o3)cn2)C(=O)N2CCS(=O)(=O)CC2)cc1] |
| 124 | 21455 | 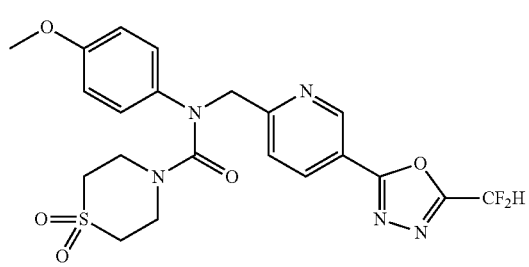 |
| 125 | 21456 | 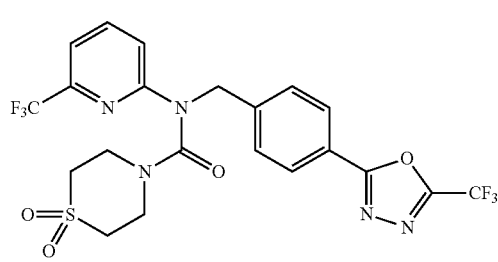 [SMILES: O=C(N1CCS(=O)(=O)CC1)N(Cc1ccc(-c2nnc(C(F)(F)F)o2)cc1)c1cccc(C(F)(F)F)n1] |
| 126 | 21457 | 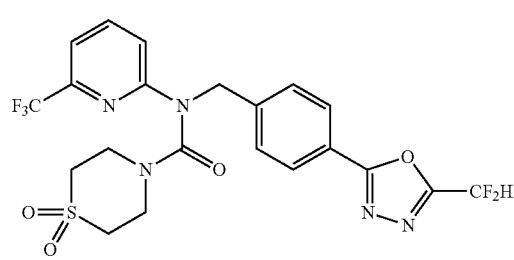 [SMILES: O=C(N1CCS(=O)(=O)CC1)N(Cc1ccc(-c2nnc(C(F)F)o2)cc1)c1cccc(C(F)(F)F)n1] |

| Ex. | Comp. | Structure |
|---|---|---|
| 127 | 21458 | 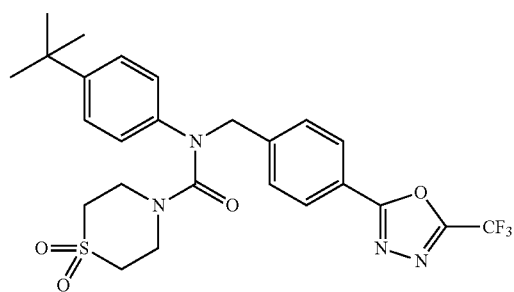 [SMILES: CC(C)(C)c1ccc(N(Cc2ccc(-c3nnc(C(F)(F)F)o3)cc2)C(=O)N2CCS(=O)(=O)CC2)cc1] |
| 128 | 21459 | 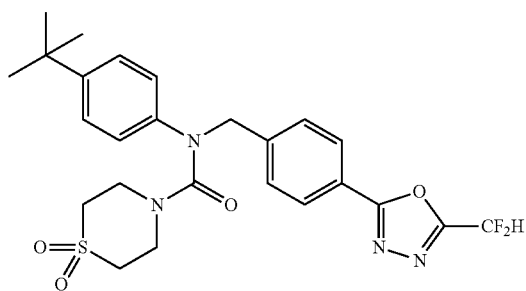 [SMILES: CC(C)(C)c1ccc(N(Cc2ccc(-c3nnc(C(F)F)o3)cc2)C(=O)N2CCS(=O)(=O)CC2)cc1] |
| 129 | 21460 | 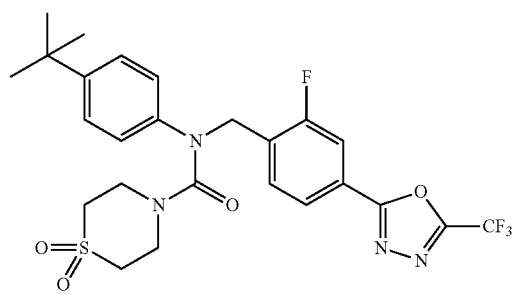 [SMILES: CC(C)(C)c1ccc(N(Cc2ccc(-c3nnc(C(F)(F)F)o3)cc2F)C(=O)N2CCS(=O)(=O)CC2)cc1] |
| 130 | 21461 | 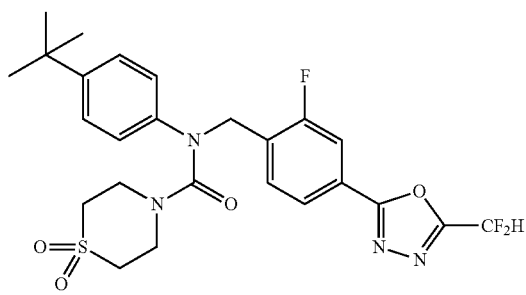 [SMILES: CC(C)(C)c1ccc(N(Cc2ccc(-c3nnc(C(F)F)o3)cc2F)C(=O)N2CCS(=O)(=O)CC2)cc1] |
| 131 | 21462 | 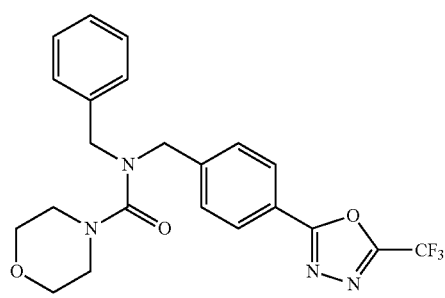 [SMILES: O=C(N1CCOCC1)N(Cc1ccccc1)Cc1ccc(-c2nnc(C(F)(F)F)o2)cc1] |

| Ex. | Comp. | Structure |
|---|---|---|
| 132 | 21463 | 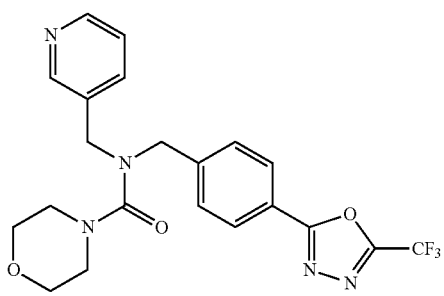 |
| 133 | 21464 | 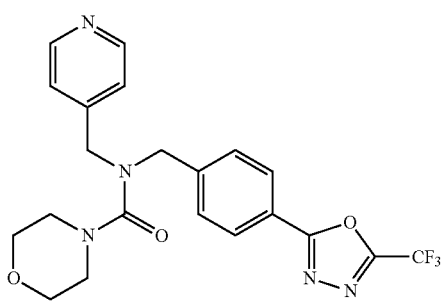 [SMILES: O=C(N1CCOCC1)N(Cc1ccncc1)Cc1ccc(-c2nnc(C(F)(F)F)o2)cc1] |
| 134 | 21465 | 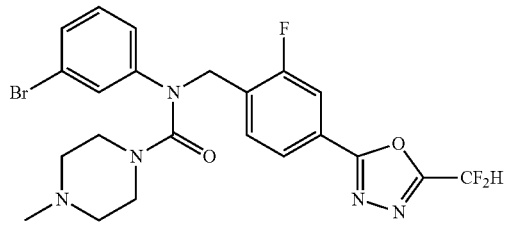 [SMILES: CN1CCN(C(=O)N(Cc2ccc(-c3nnc(C(F)F)o3)cc2F)c2cccc(Cl)c2)CC1] |
| 135 | 21466 | 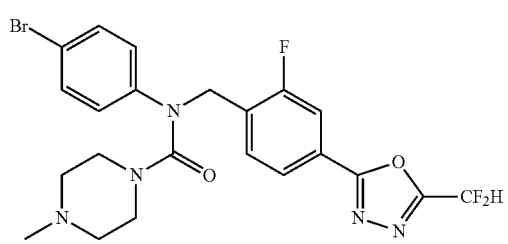 [SMILES: CN1CCN(C(=O)N(Cc2ccc(-c3nnc(C(F)F)o3)cc2F)c2ccc(Cl)cc2)CC1] |
| 136 | 21467 | 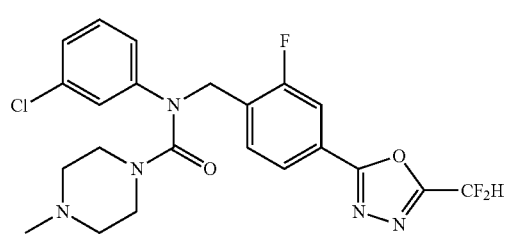 |
| 137 | 21468 | 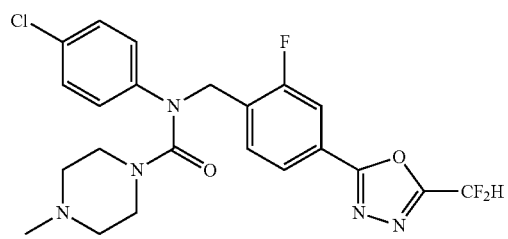 |

| Ex. | Comp. | Structure |
|---|---|---|
| 138 | 21469 | 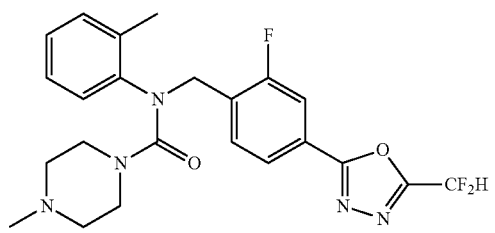 [SMILES: Cc1ccccc1N(Cc1ccc(-c2nnc(C(F)F)o2)cc1F)C(=O)N1CCN(C)CC1] |
| 139 | 21470 | 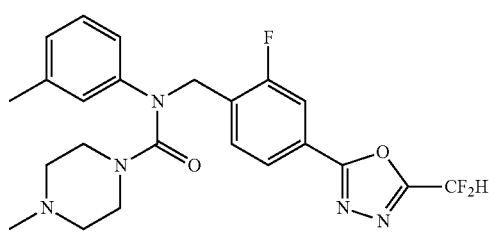 [SMILES: Cc1cccc(N(Cc2ccc(-c3nnc(C(F)F)o3)cc2F)C(=O)N2CCN(C)CC2)c1] |
| 140 | 21471 | 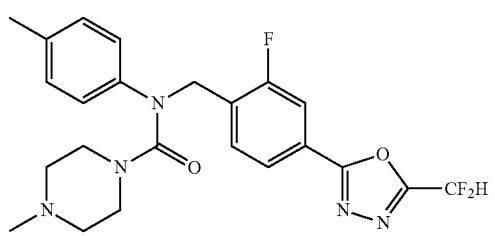 [SMILES: Cc1ccc(N(Cc2ccc(-c3nnc(C(F)F)o3)cc2F)C(=O)N2CCN(C)CC2)cc1] |
| 141 | 21472 | 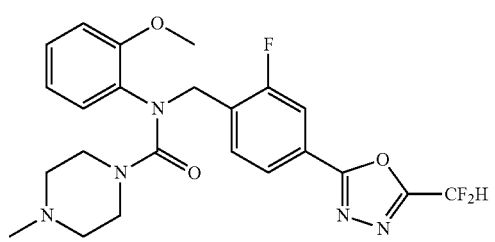 [SMILES: COc1ccccc1N(Cc1ccc(-c2nnc(C(F)F)o2)cc1F)C(=O)N1CCN(C)CC1] |
| 142 | 21473 | 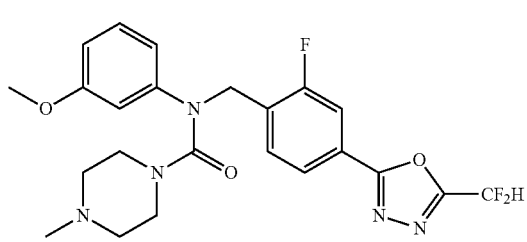 [SMILES: COc1cccc(N(Cc2ccc(-c3nnc(C(F)F)o3)cc2F)C(=O)N2CCN(C)CC2)c1] |
| 143 | 21474 | 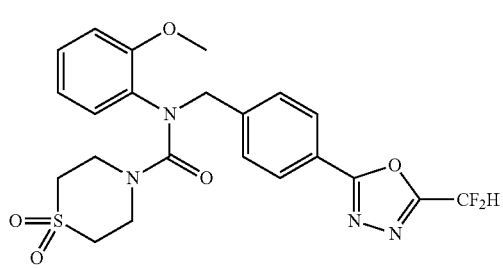 [SMILES: COc1ccccc1N(Cc1ccc(-c2nnc(C(F)F)o2)cc1)C(=O)N1CCS(=O)(=O)CC1] |

| Ex. | Comp. | Structure |
|---|---|---|
| 144 | 21475 | 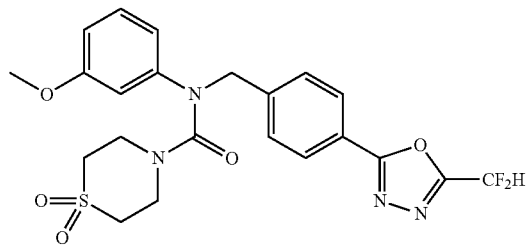 [SMILES: COc1cccc(N(Cc2ccc(-c3nnc(C(F)F)o3)cc2)C(=O)N2CCS(=O)(=O)CC2)c1] |
| 145 | 21476 | 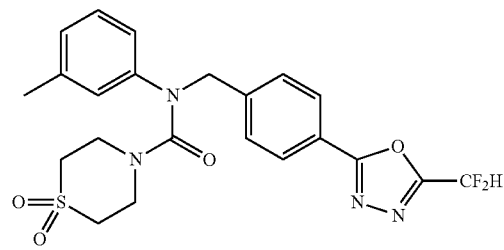 [SMILES: Cc1cccc(N(Cc2ccc(-c3nnc(C(F)F)o3)cc2)C(=O)N2CCS(=O)(=O)CC2)c1] |
| 146 | 21477 | 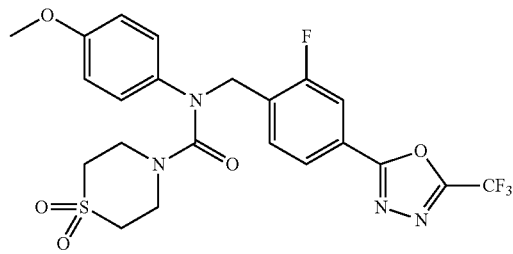 [SMILES: COc1ccc(N(Cc2ccc(-c3nnc(C(F)(F)F)o3)cc2F)C(=O)N2CCS(=O)(=O)CC2)cc1] |
| 147 | 21478 | 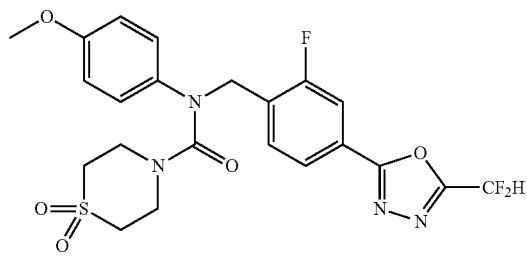 [SMILES: COc1ccc(N(Cc2ccc(-c3nnc(C(F)F)o3)cc2F)C(=O)N2CCS(=O)(=O)CC2)cc1] |
| 148 | 21479 | 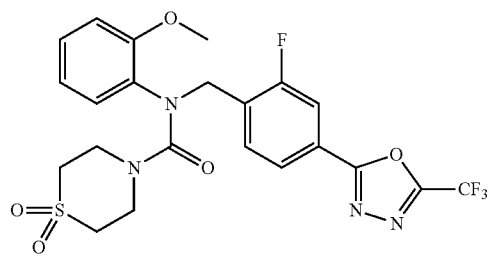 [SMILES: COc1ccccc1N(Cc1ccc(-c2nnc(C(F)(F)F)o2)cc1F)C(=O)N1CCS(=O)(=O)CC1] |
| 149 | 21480 | 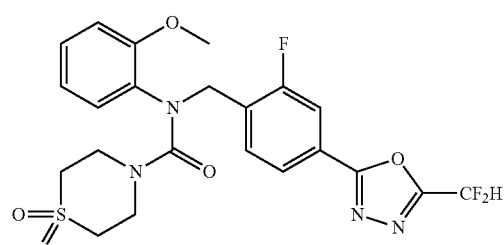 |

-continued
| Ex. | Comp. | Structure |
|---|---|---|
| 150 | 21481 | 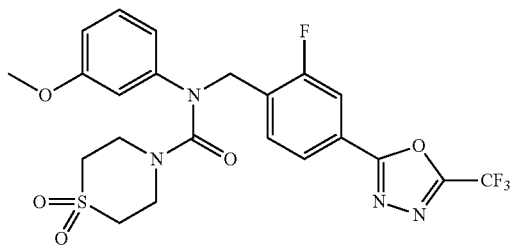 [SMILES: COc1cccc(N(Cc2ccc(-c3nnc(C(F)(F)F)o3)cc2F)C(=O)N2CCS(=O)(=O)CC2)c1] |
| 151 | 21482 | 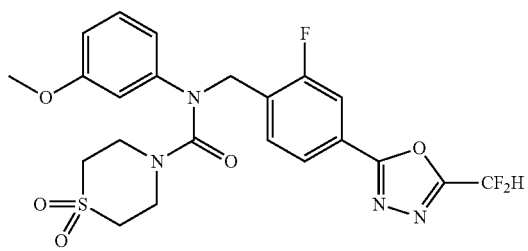 [SMILES: COc1cccc(N(Cc2ccc(-c3nnc(C(F)F)o3)cc2F)C(=O)N2CCS(=O)(=O)CC2)c1] |
| 152 | 21483 | 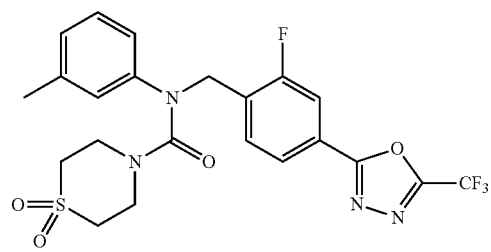 [SMILES: Cc1cccc(N(Cc2ccc(-c3nnc(C(F)(F)F)o3)cc2F)C(=O)N2CCS(=O)(=O)CC2)c1] |
| 153 | 21484 | 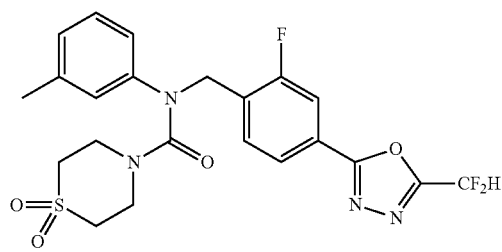 |
| 154 | 21485 | 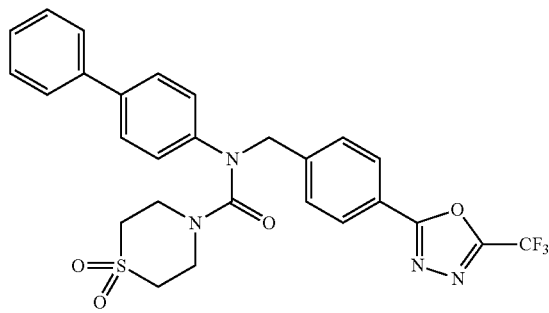 [SMILES: O=C(N1CCS(=O)(=O)CC1)N(Cc1ccc(-c2nnc(C(F)(F)F)o2)cc1)c1ccc(-c2ccccc2)cc1] |

-continued
| Ex. | Comp. | Structure |
|---|---|---|
| 155 | 21486 | 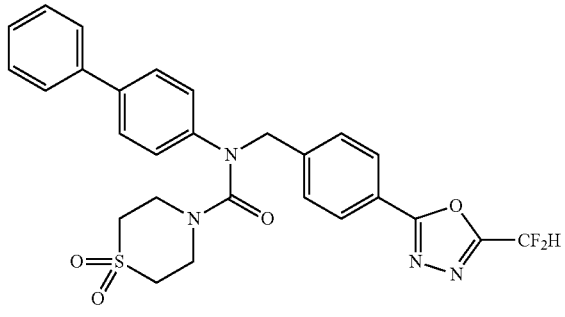 [SMILES: O=C(N1CCS(=O)(=O)CC1)N(Cc1ccc(-c2nnc(C(F)F)o2)cc1)c1ccc(-c2ccccc2)cc1] |
| 156 | 21487 | 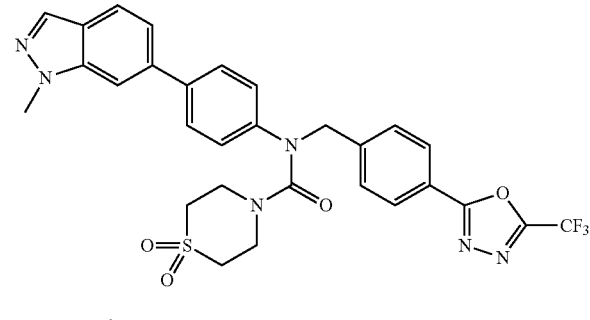 |
| 157 | 21488 | 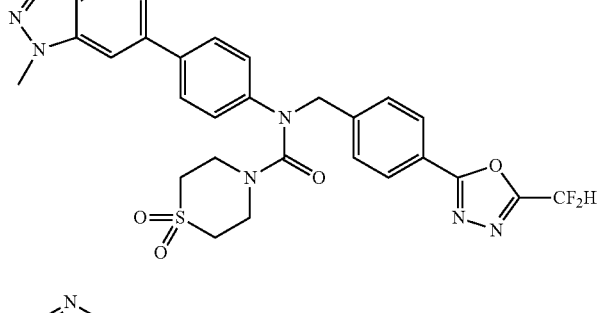 |
| 158 | 21489 | 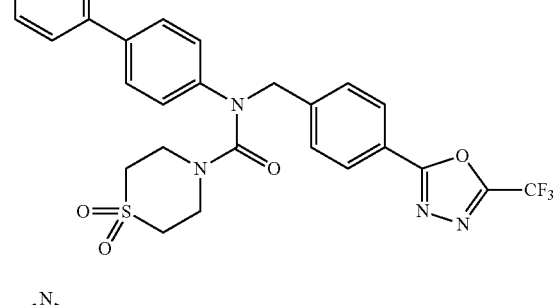 |
| 159 | 21490 | 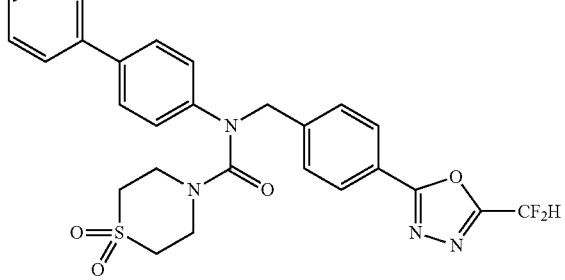 |

-continued
| Ex. | Comp. | Structure |
|---|---|---|
| 160 | 21491 | 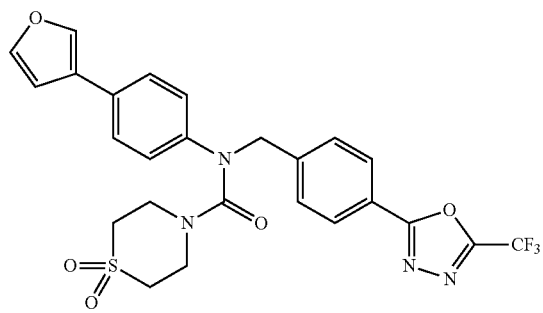 [SMILES: O=C(N1CCS(=O)(=O)CC1)N(Cc1ccc(-c2nnc(C(F)(F)F)o2)cc1)c1ccc(-c2ccoc2)cc1] |
| 161 | 21492 | 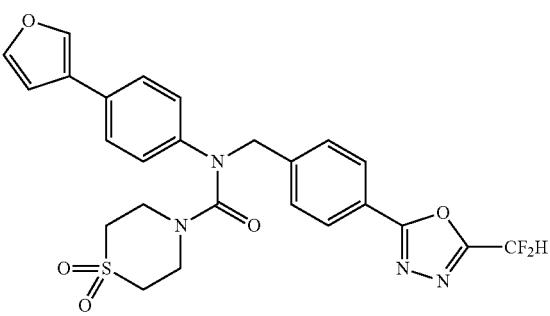 [SMILES: O=C(N1CCS(=O)(=O)CC1)N(Cc1ccc(-c2nnc(C(F)F)o2)cc1)c1ccc(-c2ccoc2)cc1] |
| 162 | 21493 | 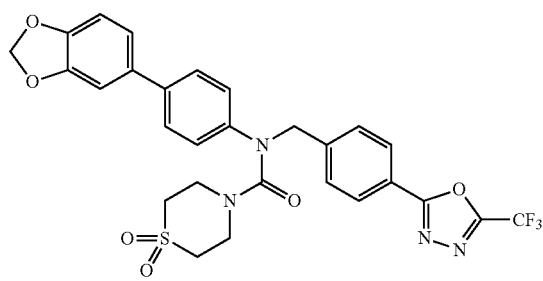 [SMILES: O=C(N1CCS(=O)(=O)CC1)N(Cc1ccc(-c2nnc(C(F)(F)F)o2)cc1)c1ccc(-c2ccc3c(c2)OCO3)cc1] |
| 163 | 21494 | 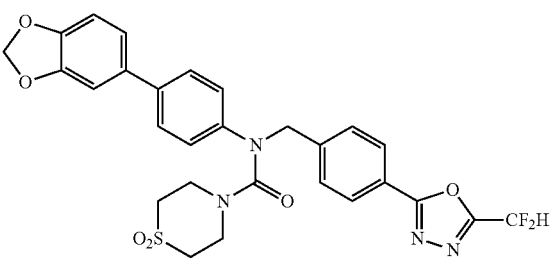 [SMILES: O=C(N1CCS(=O)(=O)CC1)N(Cc1ccc(-c2nnc(C(F)F)o2)cc1)c1ccc(-c2ccc3c(c2)OCO3)cc1] |
| 164 | 21495 | 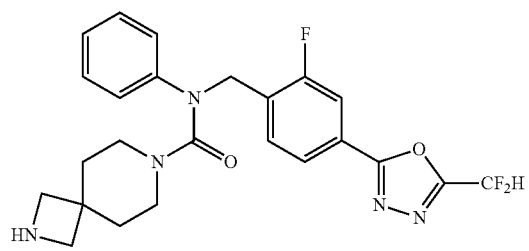 [SMILES: O=C(N1CCC2(CC1)CNC2)N(Cc1ccc(-c2nnc(C(F)F)o2)cc1F)c1ccccc1] |

| Ex. | Comp. | Structure |
|---|---|---|
| 165 | 21496 | 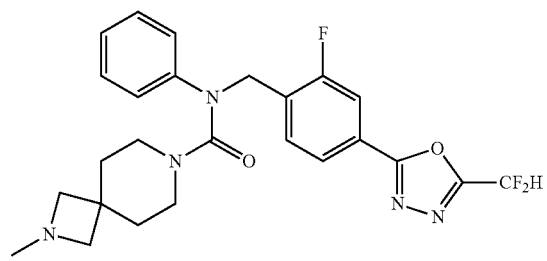 [SMILES: CN1CC2(CCN(C(=O)N(Cc3ccc(-c4nnc(C(F)F)o4)cc3F)c3ccccc3)CC2)C1] |
| 166 | 21497 | 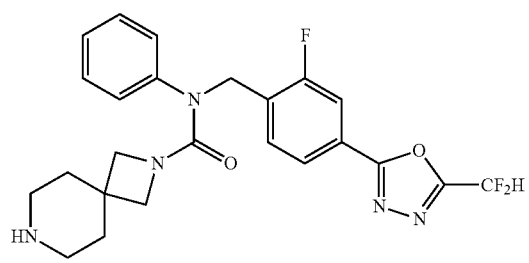 [SMILES: O=C(N1CC2(CCNCC2)C1)N(Cc1ccc(-c2nnc(C(F)F)o2)cc1F)c1ccccc1] |
| 167 | 21498 | 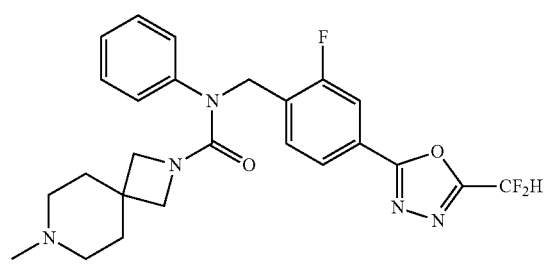 [SMILES: CN1CCC2(CC1)CN(C(=O)N(Cc1ccc(-c3nnc(C(F)F)o3)cc1F)c1ccccc1)C2] |
| 168 | 21499 | 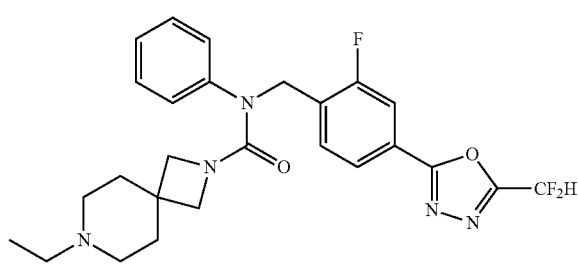 [SMILES: CCN1CCC2(CC1)CN(C(=O)N(Cc1ccc(-c3nnc(C(F)F)o3)cc1F)c1ccccc1)C2] |
| 169 | 21500 | 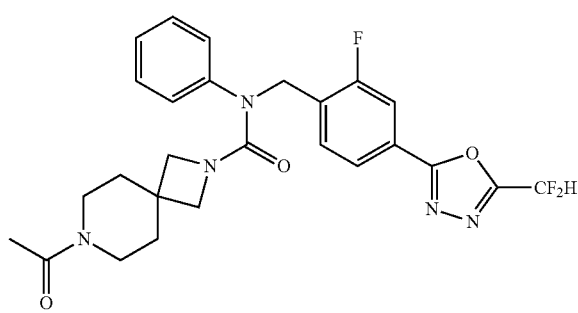 [SMILES: CC(=O)N1CCC2(CC1)CN(C(=O)N(Cc1ccc(-c3nnc(C(F)F)o3)cc1F)c1ccccc1)C2] |

| Ex. | Comp. | Structure |
|---|---|---|
| 170 | 21501 | 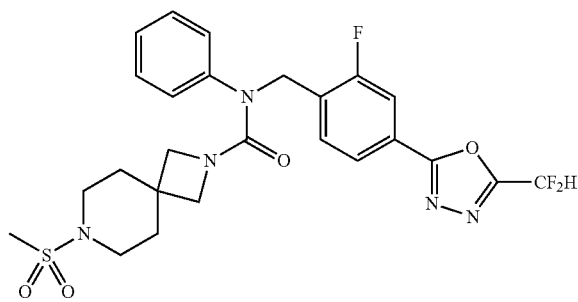 [SMILES: CS(=O)(=O)N1CCC2(CC1)CN(C(=O)N(Cc1ccc(-c3nnc(C(F)F)o3)cc1F)c1ccccc1)C2] |
| 171 | 21502 | 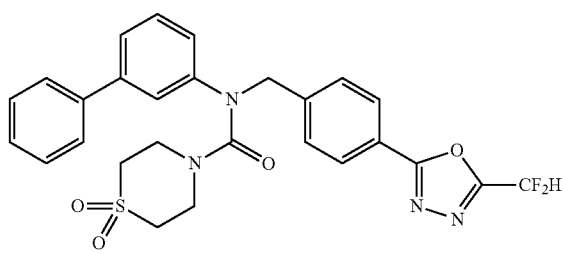 [SMILES: O=C(N1CCS(=O)(=O)CC1)N(Cc1ccc(-c2nnc(C(F)F)o2)cc1)c1cccc(-c2ccccc2)c1] |
| 172 | 21511 | 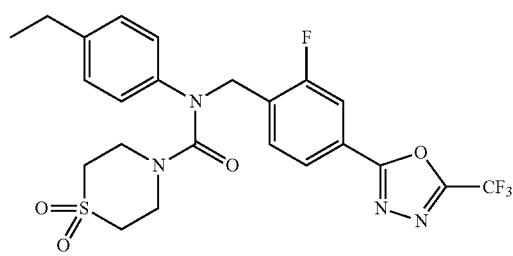 [SMILES: CCc1ccc(N(Cc2ccc(-c3nnc(C(F)(F)F)o3)cc2F)C(=O)N2CCS(=O)(=O)CC2)cc1] |
| 173 | 21512 | 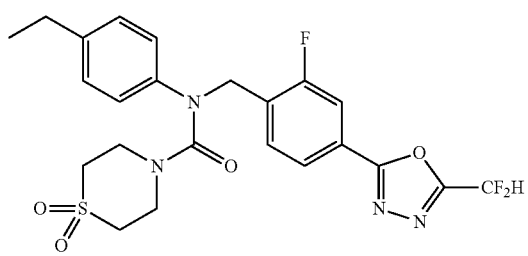 [SMILES: CCc1ccc(N(Cc2ccc(-c3nnc(C(F)F)o3)cc2F)C(=O)N2CCS(=O)(=O)CC2)cc1] |
| 174 | 21513 | 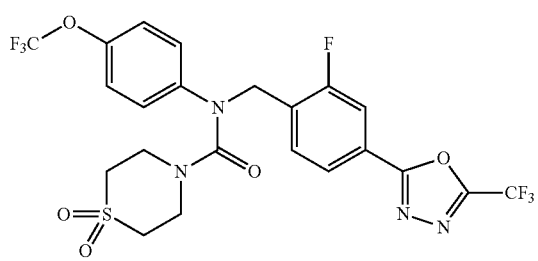 [SMILES: O=C(N1CCS(=O)(=O)CC1)N(Cc1ccc(-c2nnc(C(F)(F)F)o2)cc1F)c1ccc(OC(F)(F)F)cc1] |
| 175 | 21514 | 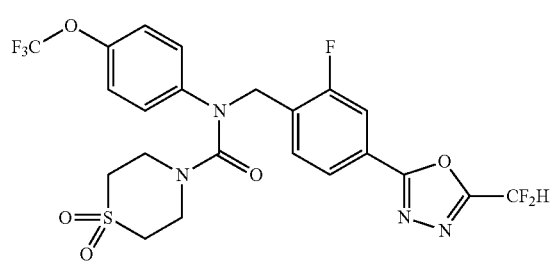 [SMILES: O=C(N1CCS(=O)(=O)CC1)N(Cc1ccc(-c2nnc(C(F)F)o2)cc1F)c1ccc(OC(F)(F)F)cc1] |

| Ex. | Comp. | Structure |
|---|---|---|
| 176 | 21515 | 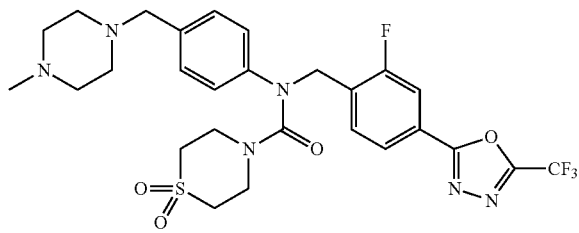 [SMILES: CN1CCN(Cc2ccc(N(Cc3ccc(-c4nnc(C(F)(F)F)o4)cc3F)C(=O)N3CCS(=O)(=O)CC3)cc2)CC1] |
| 177 | 21516 | 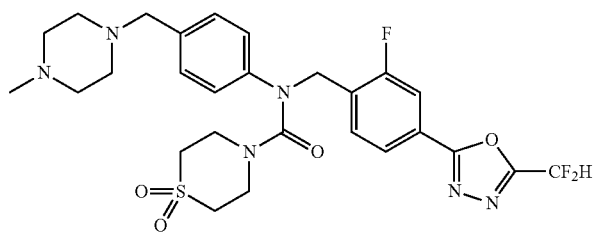 [SMILES: CN1CCN(Cc2ccc(N(Cc3ccc(-c4nnc(C(F)F)o4)cc3F)C(=O)N3CCS(=O)(=O)CC3)cc2)CC1] |
| 178 | 21517 | 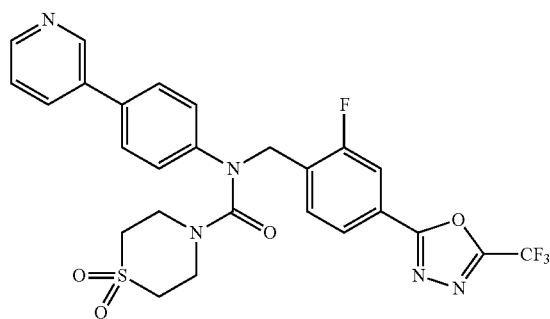 [SMILES: O=C(N1CCS(=O)(=O)CC1)N(Cc1ccc(-c2nnc(C(F)(F)F)o2)cc1F)c1ccc(-c2cccnc2)cc1] |
| 179 | 21518 | 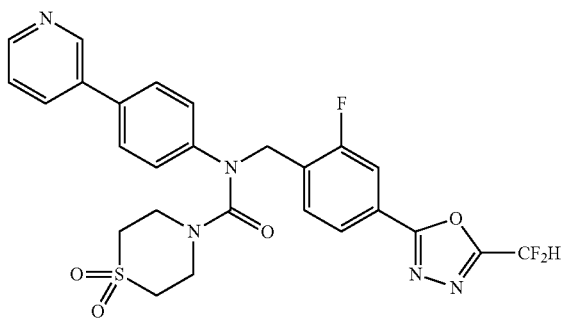 [SMILES: O=C(N1CCS(=O)(=O)CC1)N(Cc1ccc(-c2nnc(C(F)F)o2)cc1F)c1ccc(-c2cccnc2)cc1] |
| 180 | 21519 | 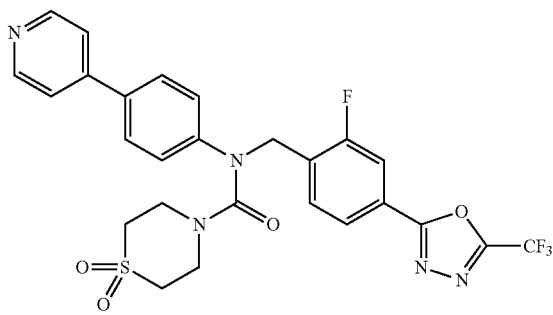 [SMILES: O=C(N1CCS(=O)(=O)CC1)N(Cc1ccc(-c2nnc(C(F)(F)F)o2)cc1F)c1ccc(-c2ccncc2)cc1] |

| Ex. | Comp. | Structure |
|---|---|---|
| 181 | 21520 | 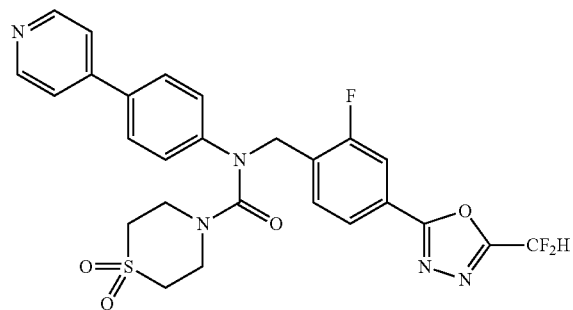 [SMILES: O=C(N1CCS(=O)(=O)CC1)N(Cc1ccc(-c2nnc(C(F)F)o2)cc1F)c1ccc(-c2ccncc2)cc1] |
| 182 | 21521 | 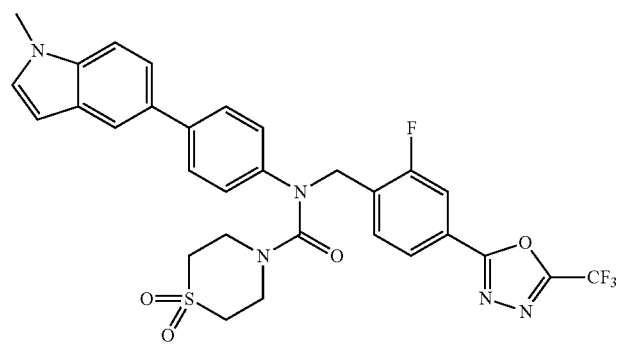 [SMILES: Cn1ccc2cc(-c3ccc(N(Cc4ccc(-c5nnc(C(F)(F)F)o5)cc4F)C(=O)N4CCS(=O)(=O)CC4)cc3)ccc21] |
| 183 | 21522 | 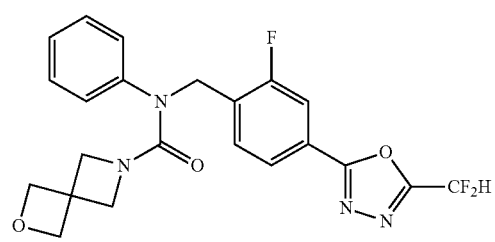 [SMILES: O=C(N1CC2(COC2)C1)N(Cc1ccc(-c2nnc(C(F)F)o2)cc1F)c1ccccc1] |
| 184 | 21527 | 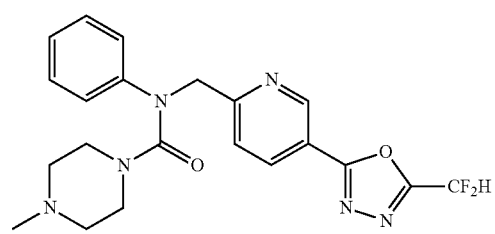 [SMILES: CN1CCN(C(=O)N(Cc2ccc(-c3nnc(C(F)F)o3)cn2)c2ccccc2)CC1] |
| 185 | 21528 | 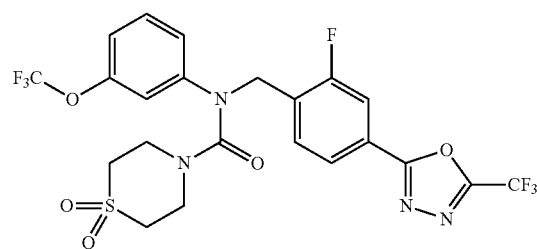 [SMILES: O=C(N1CCS(=O)(=O)CC1)N(Cc1ccc(-c2nnc(C(F)(F)F)o2)cc1F)c1cccc(OC(F)(F)F)c1] |

-continued
| Ex. | Comp. | Structure |
|---|---|---|
| 186 | 21529 | 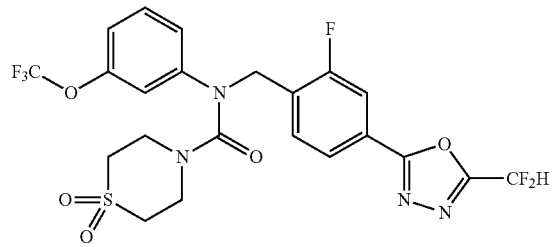 [SMILES: O=C(N1CCS(=O)(=O)CC1)N(Cc1ccc(-c2nnc(C(F)F)o2)cc1F)c1cccc(OC(F)(F)F)c1] |
| 187 | 21530 | 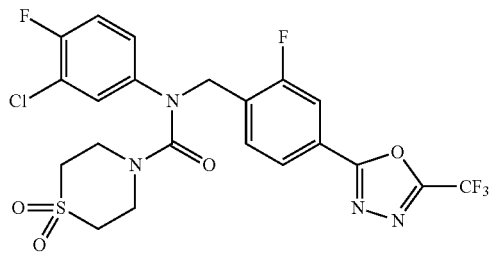 [SMILES: O=C(N1CCS(=O)(=O)CC1)N(Cc1ccc(-c2nnc(C(F)(F)F)o2)cc1F)c1ccc(F)c(Cl)c1] |
| 188 | 21531 | 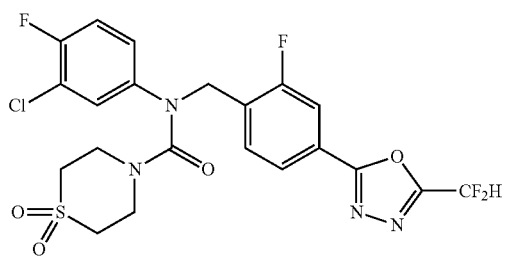 [SMILES: O=C(N1CCS(=O)(=O)CC1)N(Cc1ccc(-c2nnc(C(F)F)o2)cc1F)c1ccc(F)c(Cl)c1] |
| 189 | 21532 | 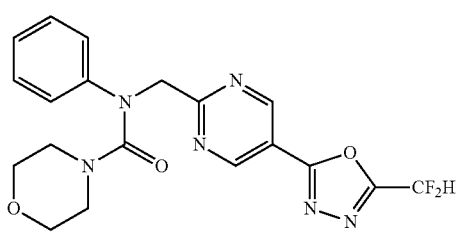 [SMILES: O=C(N1CCOCC1)N(Cc1ncc(-c2nnc(C(F)F)o2)cn1)c1ccccc1] |
| 190 | 21533 | 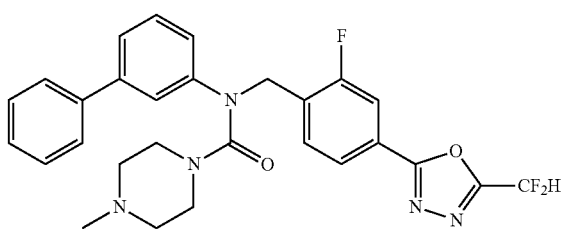 [SMILES: CN1CCN(C(=O)N(Cc2ccc(-c3nnc(C(F)F)o3)cc2F)c2cccc(-c3ccccc3)c2)CC1] |
| 191 | 21534 | 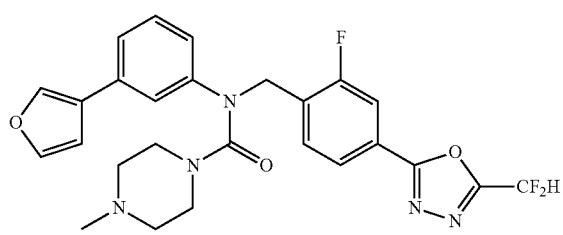 [SMILES: CN1CCN(C(=O)N(Cc2ccc(-c3nnc(C(F)F)o3)cc2F)c2cccc(-c3ccoc3)c2)CC1] |

| Ex. | Comp. | Structure |
|---|---|---|
| 192 | 21535 | 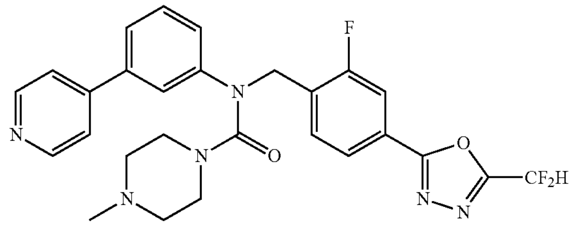 [SMILES: CN1CCN(C(=O)N(Cc2ccc(-c3nnc(C(F)F)o3)cc2F)c2cccc(-c3ccncc3)c2)CC1] |
| 193 | 21536 | 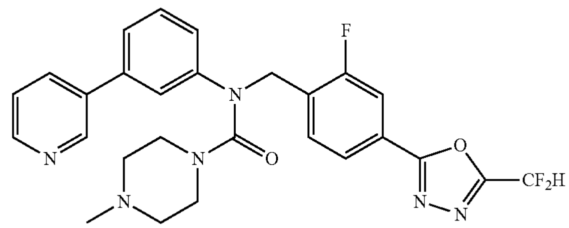 |
| 194 | 21537 | 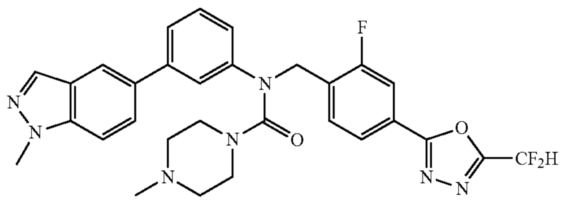 [SMILES: CN1CCN(C(=O)N(Cc2ccc(-c3nnc(C(F)F)o3)cc2F)c2cccc(-c3ccc4c(cnn4C)c3)c2)CC1] |
| 195 | 21540 | 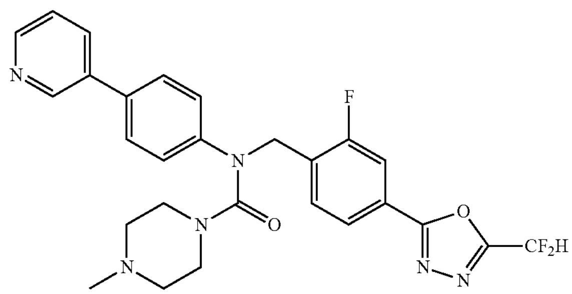 [SMILES: CN1CCN(C(=O)N(Cc2ccc(-c3nnc(C(F)F)o3)cc2F)c2ccc(-c3cccnc3)cc2)CC1] |
| 196 | 21541 | 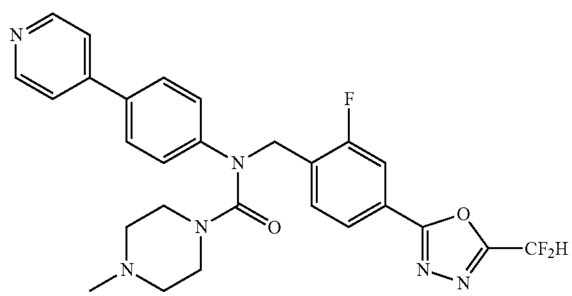 [SMILES: CN1CCN(C(=O)N(Cc2ccc(-c3nnc(C(F)F)o3)cc2F)c2ccc(-c3ccncc3)cc2)CC1] |
| 197 | 21542 | 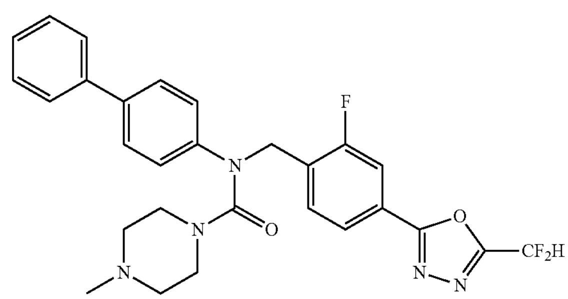 [SMILES: CN1CCN(C(=O)N(Cc2ccc(-c3nnc(C(F)F)o3)cc2F)c2ccc(-c3ccccc3)cc2)CC1] |

-continued
| Ex. | Comp. | Structure |
|---|---|---|
| 198 | 21543 | 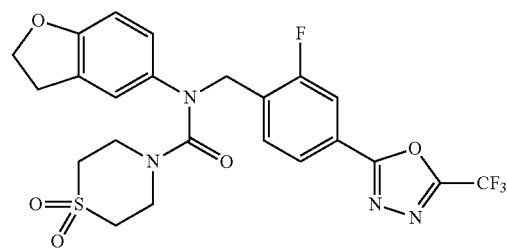 [SMILES: O=C(N1CCS(=O)(=O)CC1)N(Cc1ccc(-c2nnc(C(F)(F)F)o2)cc1F)c1ccc2c(c1)CCO2] |
| 199 | 21544 | 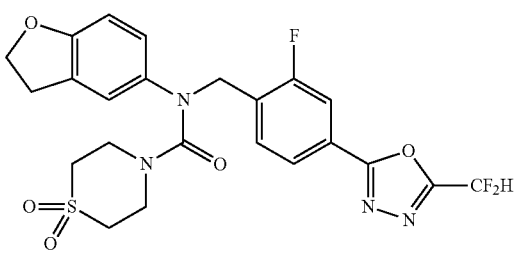 |
| 200 | 21545 | 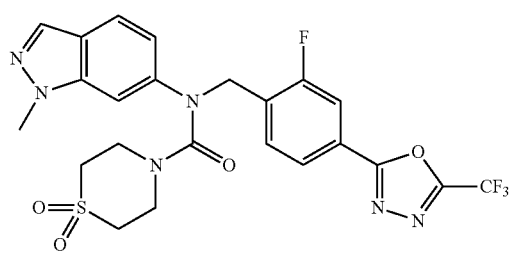 |
| 201 | 21546 | 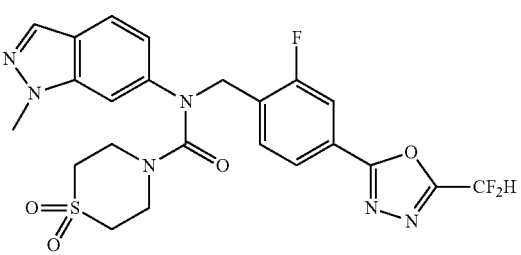 [SMILES: Cn1ncc2ccc(N(Cc3ccc(-c4nnc(C(F)F)o4)cc3F)C(=O)N3CCS(=O)(=O)CC3)cc21] |
| 202 | 21552 | 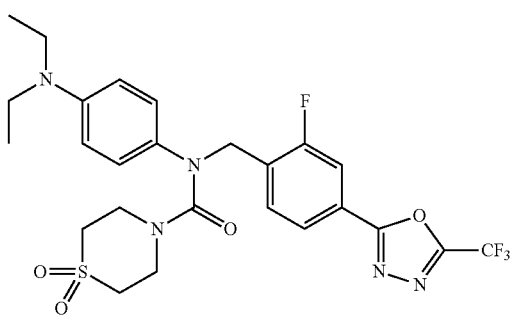 [SMILES: CCN(CC)c1ccc(N(Cc2ccc(-c3nnc(C(F)(F)F)o3)cc2F)C(=O)N2CCS(=O)(=O)CC2)cc1] |

| Ex. | Comp. | Structure |
|---|---|---|
| 203 | 21553 | 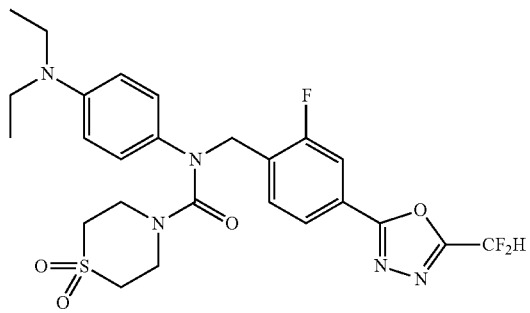 [SMILES: CCN(CC)c1ccc(N(Cc2ccc(-c3nnc(C(F)F)o3)cc2F)C(=O)N2CCS(=O)(=O)CC2)cc1] |
| 204 | 21554 | 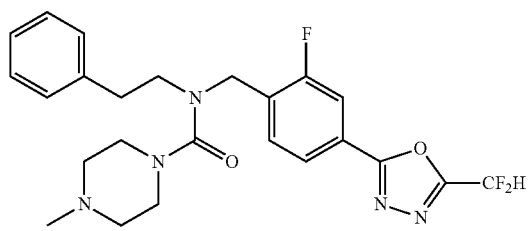 [SMILES: CN1CCN(C(=O)N(CCc2ccccc2)Cc2ccc(-c3nnc(C(F)F)o3)cc2F)CC1] |
| 205 | 21555 | 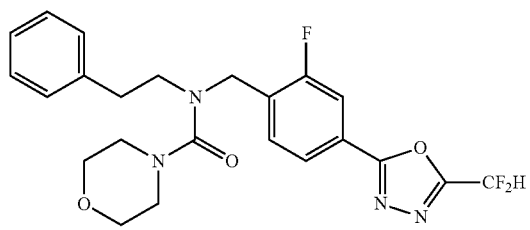 [SMILES: O=C(N1CCOCC1)N(CCc1ccccc1)Cc1ccc(-c2nnc(C(F)F)o2)cc1F] |
| 206 | 21556 | 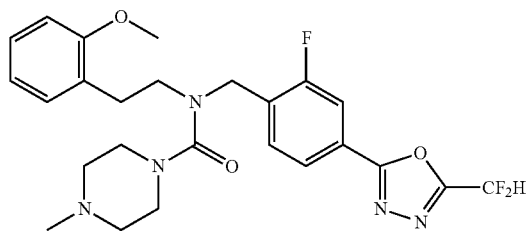 [SMILES: COc1ccccc1CCN(Cc1ccc(-c2nnc(C(F)F)o2)cc1F)C(=O)N1CCN(C)CC1] |
| 207 | 21557 | 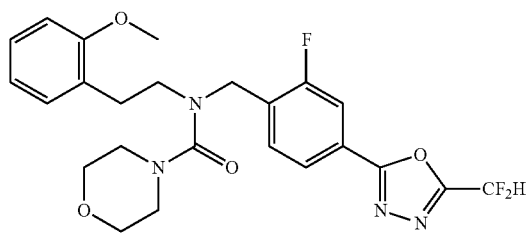 [SMILES: COc1ccccc1CCN(Cc1ccc(-c2nnc(C(F)F)o2)cc1F)C(=O)N1CCOCC1] |
| 208 | 21564 | 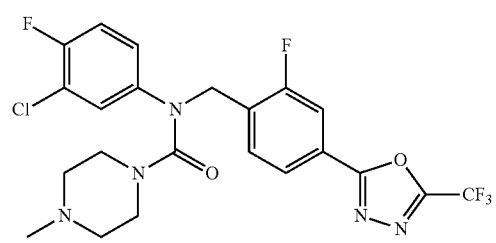 [SMILES: CN1CCN(C(=O)N(Cc2ccc(-c3nnc(C(F)(F)F)o3)cc2F)c2ccc(F)c(Cl)c2)CC1] |

-continued
| Ex. | Comp. | Structure |
|---|---|---|
| 209 | 21565 | 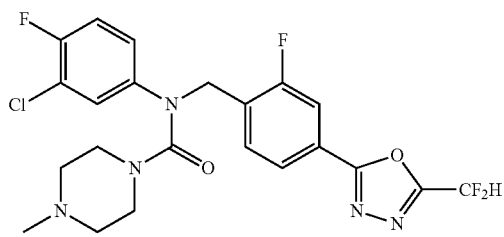 [SMILES: CN1CCN(C(=O)N(Cc2ccc(-c3nnc(C(F)F)o3)cc2F)c2ccc(F)c(Cl)c2)CC1] |
| 210 | 21566 | 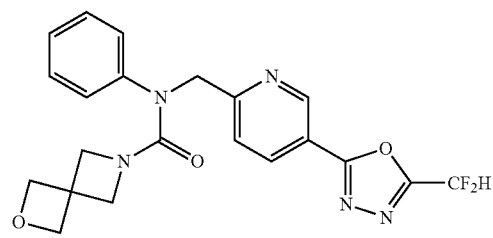 [SMILES: O=C(N1CC2(COC2)C1)N(Cc1ccc(-c2nnc(C(F)F)o2)cn1)c1ccccc1] |
| 211 | 21568 | 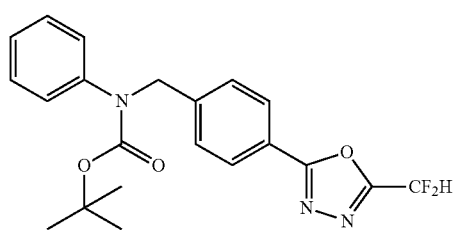 [SMILES: CC(C)(C)OC(=O)N(Cc1ccc(-c2nnc(C(F)F)o2)cc1)c1ccccc1] |
| 212 | 21569 | 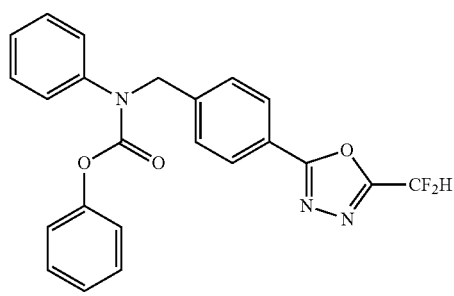 [SMILES: O=C(Oc1ccccc1)N(Cc1ccc(-c2nnc(C(F)F)o2)cc1)c1ccccc1] |
| 213 | 21570 | 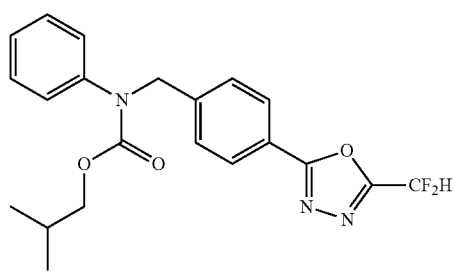 [SMILES: CC(C)COC(=O)N(Cc1ccc(-c2nnc(C(F)F)o2)cc1)c1ccccc1] |
| 214 | 21576 | 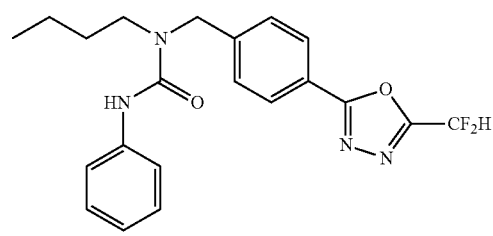 [SMILES: CCCCN(Cc1ccc(-c2nnc(C(F)F)o2)cc1)C(=O)Nc1ccccc1] |

| Ex. | Comp. | Structure |
|---|---|---|
| 215 | 21577 | 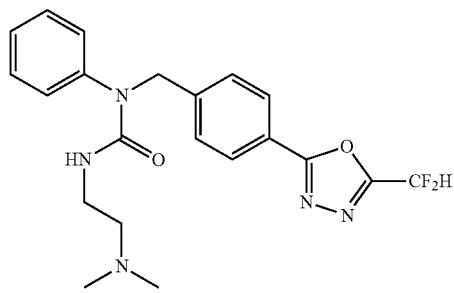 [SMILES: CN(C)CCNC(=O)N(Cc1ccc(-c2nnc(C(F)F)o2)cc1)c1ccccc1] |
| 216 | 21578 | 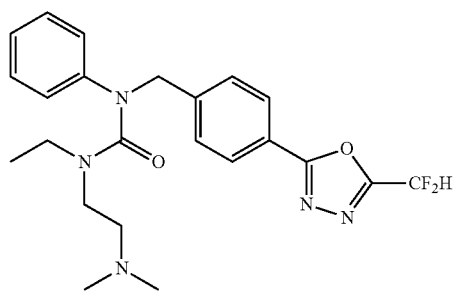 [SMILES: CCN(CCN(C)C)C(=O)N(Cc1ccc(-c2nnc(C(F)F)o2)cc1)c1ccccc1] |
| 217 | 21583 | 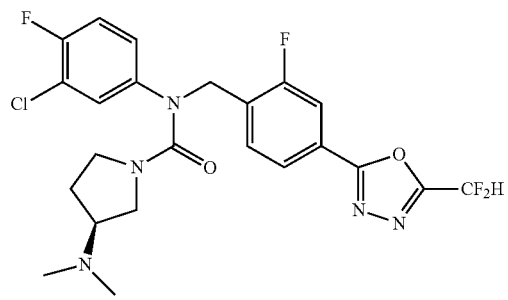 [SMILES: CN(C)[C@H]1CCN(C(=O)N(Cc2ccc(-c3nnc(C(F)F)o3)cc2F)c2ccc(F)c(Cl)c2)C1] |
| 218 | 21584 | 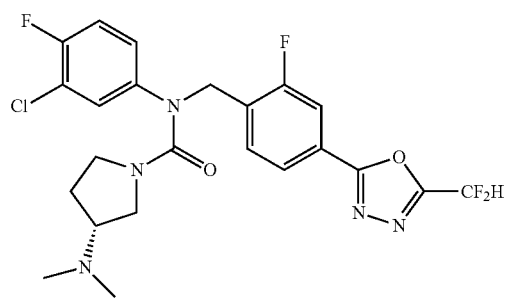 [SMILES: CN(C)[C@@H]1CCN(C(=O)N(Cc2ccc(-c3nnc(C(F)F)o3)cc2F)c2ccc(F)c(Cl)c2)C1] |
| 219 | 21585 | 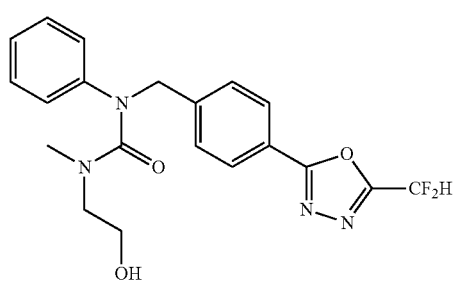 [SMILES: CN(CCO)C(=O)N(Cc1ccc(-c2nnc(C(F)F)o2)cc1)c1ccccc1] |

-continued
| Ex. | Comp. | Structure |
|---|---|---|
| 220 | 21586 | 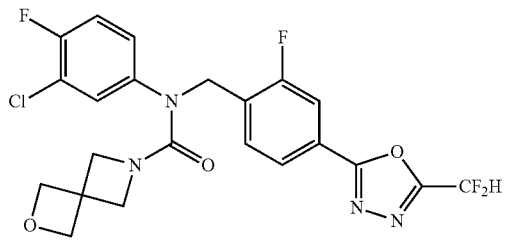 [SMILES: O=C(N1CC2(COC2)C1)N(Cc1ccc(-c2nnc(C(F)F)o2)cc1F)c1ccc(F)c(Cl)c1] |
| 221 | 21587 | 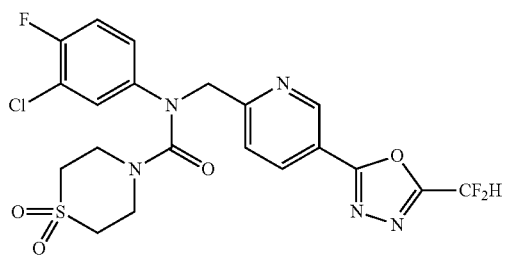 [SMILES: O=C(N1CCS(=O)(=O)CC1)N(Cc1ccc(-c2nnc(C(F)F)o2)cn1)c1ccc(F)c(Cl)c1] |
| 222 | 21591 | 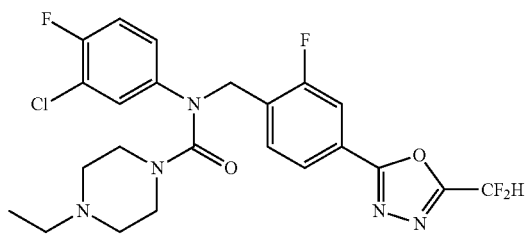 |
| 223 | 21592 | 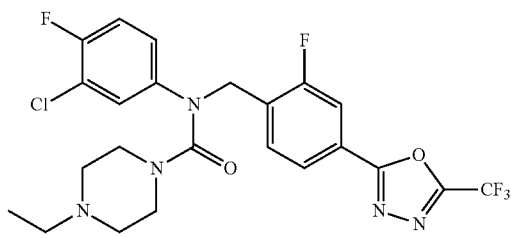 [SMILES: CCN1CCN(C(=O)N(Cc2ccc(-c3nnc(C(F)(F)F)o3)cc2F)c2ccc(F)c(Cl)c2)CC1] |
| 224 | 21593 | 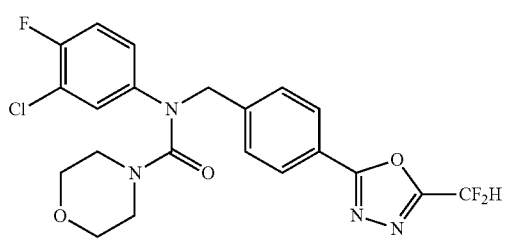 [SMILES: O=C(N1CCOCC1)N(Cc1ccc(-c2nnc(C(F)F)o2)cc1)c1ccc(F)c(Cl)c1] |
| 225 | 21594 | 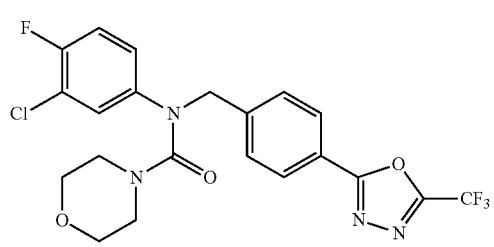 [SMILES: O=C(N1CCOCC1)N(Cc1ccc(-c2nnc(C(F)(F)F)o2)cc1)c1ccc(F)c(Cl)c1] |

| Ex. | Comp. | Structure |
|---|---|---|
| 226 | 21597 | 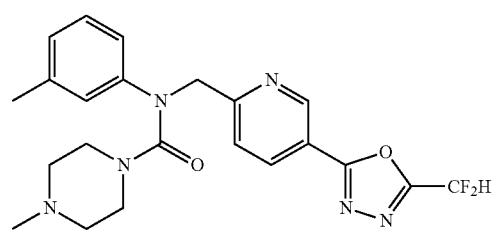 [SMILES: Cc1cccc(N(Cc2ccc(-c3nnc(C(F)F)o3)cn2)C(=O)N2CCN(C)CC2)c1] |
| 227 | 21598 | 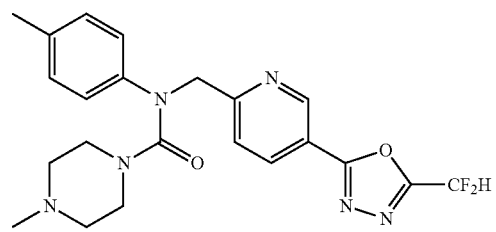 [SMILES: Cc1ccc(N(Cc2ccc(-c3nnc(C(F)F)o3)cn2)C(=O)N2CCN(C)CC2)cc1] |
| 228 | 21599 | 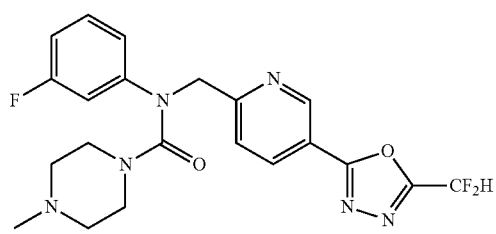 [SMILES: CN1CCN(C(=O)N(Cc2ccc(-c3nnc(C(F)F)o3)cn2)c2cccc(F)c2)CC1] |
| 229 | 21600 | 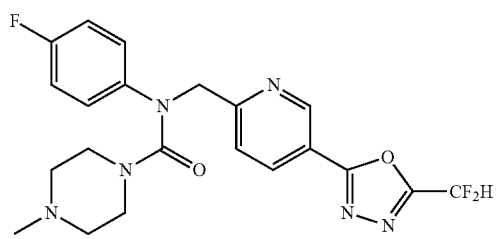 [SMILES: CN1CCN(C(=O)N(Cc2ccc(-c3nnc(C(F)F)o3)cn2)c2ccc(F)cc2)CC1] |
| 230 | 21601 | 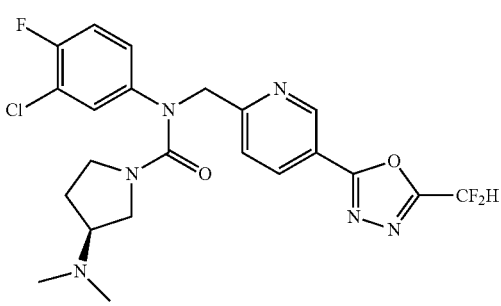 [SMILES: CN(C)[C@H]1CCN(C(=O)N(Cc2ccc(-c3nnc(C(F)F)o3)cn2)c2ccc(F)c(Cl)c2)C1] |
| 231 | 21602 | 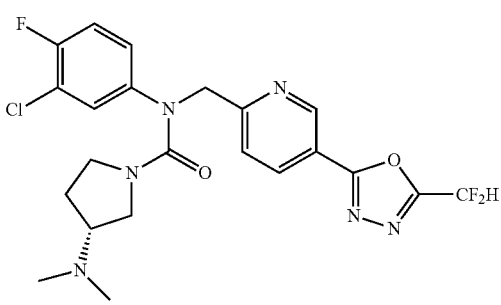 [SMILES: CN(C)[C@@H]1CCN(C(=O)N(Cc2ccc(-c3nnc(C(F)F)o3)cn2)c2ccc(F)c(Cl)c2)C1] |

| Ex. | Comp. | Structure |
|---|---|---|
| 232 | 21619 | 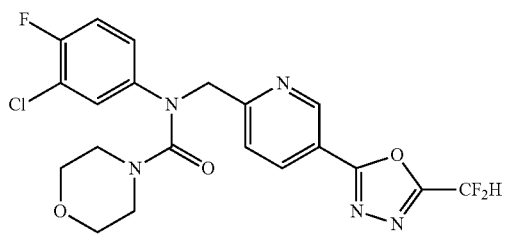 |
| 233 | 21620 | 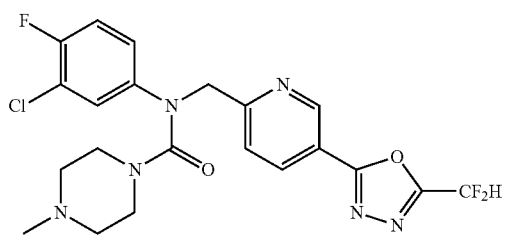 [SMILES: CN1CCN(C(=O)N(Cc2ccc(-c3nnc(C(F)F)o3)cn2)c2ccc(F)c(Cl)c2)CC1] |
| 234 | 21621 | 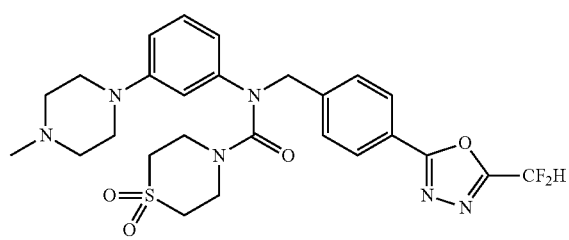 [SMILES: CN1CCN(c2cccc(N(Cc3ccc(-c4nnc(C(F)F)o4)cc3)C(=O)N3CCS(=O)(=O)CC3)c2)CC1] |
| 235 | 21622 | 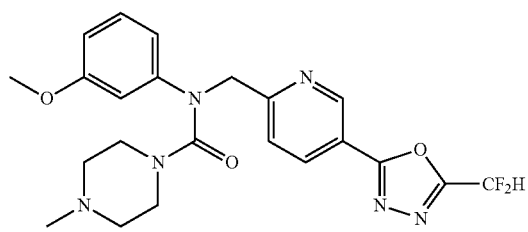 [SMILES: COc1cccc(N(Cc2ccc(-c3nnc(C(F)F)o3)cn2)C(=O)N2CCN(C)CC2)c1] |
| 236 | 21623 | 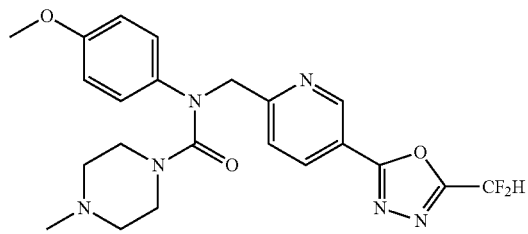 [SMILES: COc1ccc(N(Cc2ccc(-c3nnc(C(F)F)o3)cn2)C(=O)N2CCN(C)CC2)cc1] |
| 237 | 21624 | 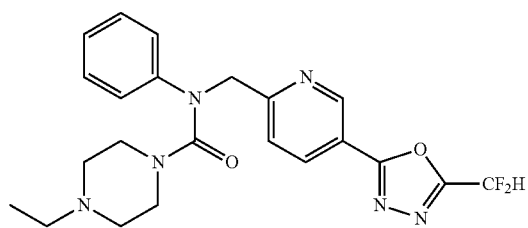 [SMILES: CCN1CCN(C(=O)N(Cc2ccc(-c3nnc(C(F)F)o3)cn2)c2ccccc2)CC1] |

-continued

| Ex. | Comp. | Structure |
|---|---|---|
| 238 | 21625 | 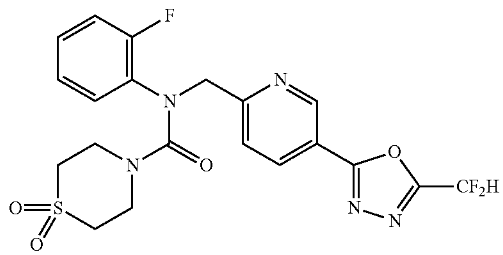 |
| 239 | 21626 | 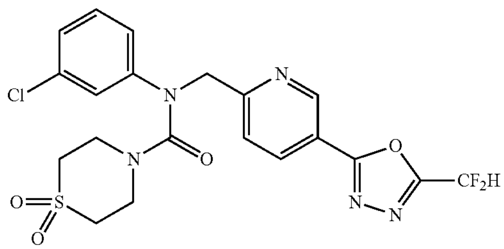 [SMILES: O=C(N1CCS(=O)(=O)CC1)N(Cc1ccc(-c2nnc(C(F)F)o2)cn1)c1cccc(Cl)c1] |
| 240 | 21627 | 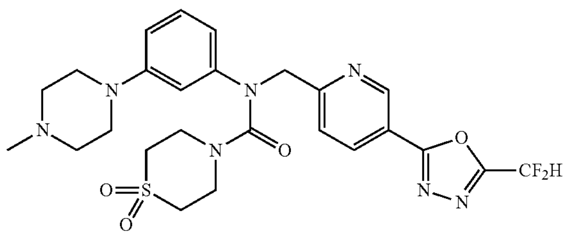 [SMILES: CN1CCN(c2cccc(N(Cc3ccc(-c4nnc(C(F)F)o4)cn3)C(=O)N3CCS(=O)(=O)CC3)c2)CC1] |
| 241 | 21628 | 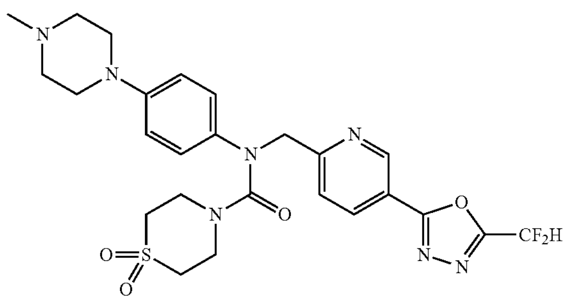 [SMILES: CN1CCN(c2ccc(N(Cc3ccc(-c4nnc(C(F)F)o4)cn3)C(=O)N3CCS(=O)(=O)CC3)cc2)CC1] |
| 242 | 21629 | 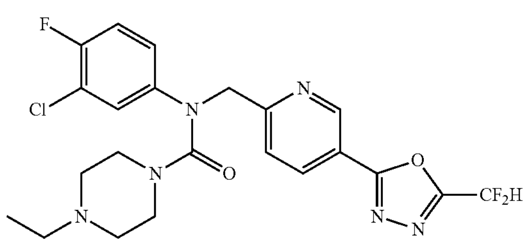 [SMILES: CCN1CCN(C(=O)N(Cc2ccc(-c3nnc(C(F)F)o3)cn2)c2ccc(F)c(Cl)c2)CC1] |
| 243 | 21630 | 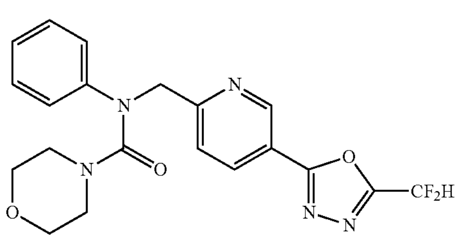 |

-continued
| Ex. | Comp. | Structure |
|---|---|---|
| 244 | 21631 | 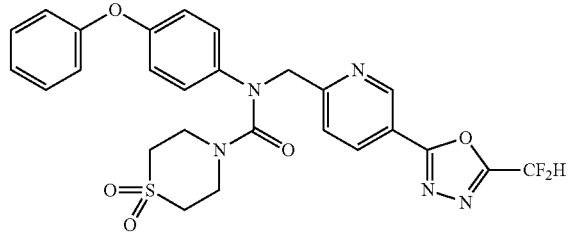 [SMILES: O=C(N1CCS(=O)(=O)CC1)N(Cc1ccc(-c2nnc(C(F)F)o2)cn1)c1ccc(Oc2ccccc2)cc1] |
| 245 | 21632 | 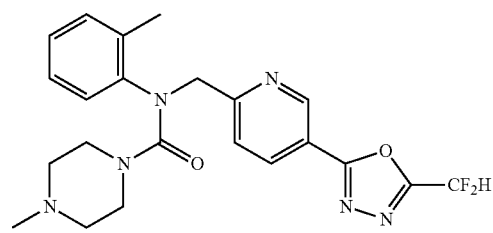 [SMILES: Cc1ccccc1N(Cc1ccc(-c2nnc(C(F)F)o2)cn1)C(=O)N1CCN(C)CC1] |
| 246 | 21633 | 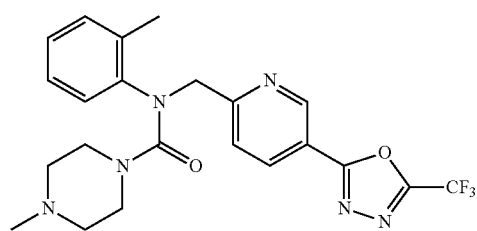 [SMILES: Cc1ccccc1N(Cc1ccc(-c2nnc(C(F)(F)F)o2)cn1)C(=O)N1CCN(C)CC1] |
| 247 | 21634 | 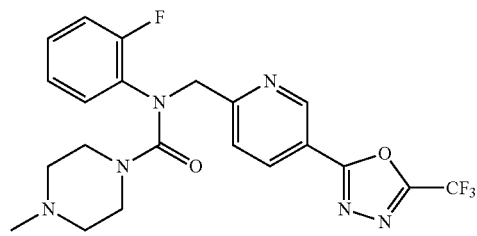 [SMILES: CN1CCN(C(=O)N(Cc2ccc(-c3nnc(C(F)(F)F)o3)cn2)c2ccccc2F)CC1] |
| 248 | 21643 | 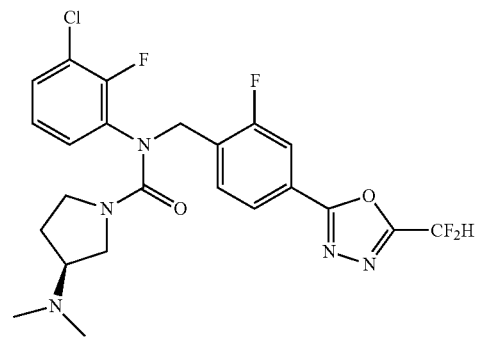 [SMILES: CN(C)[C@H]1CCN(C(=O)N(Cc2ccc(-c3nnc(C(F)F)o3)cc2F)c2cccc(Cl)c2F)C1] |

| Ex. | Comp. | Structure |
|---|---|---|
| 249 | 21644 | 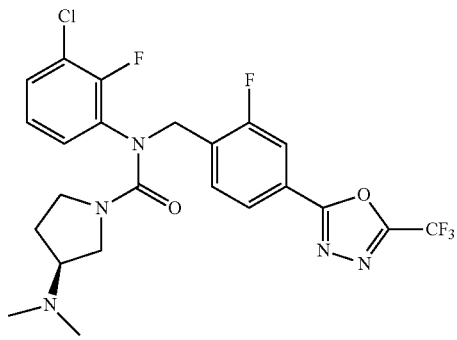 [SMILES: CN(C)[C@H]1CCN(C(=O)N(Cc2ccc(-c3nnc(C(F)(F)F)o3)cc2F)c2cccc(Cl)c2F)C1] |
| 250 | 21645 | 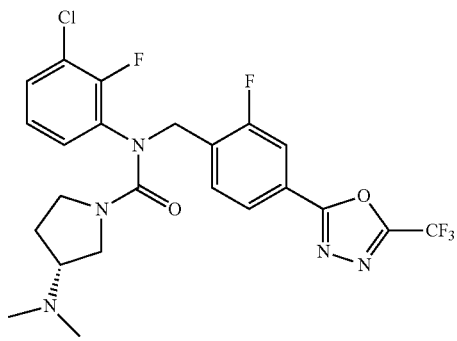 [SMILES: CN(C)[C@@H]1CCN(C(=O)N(Cc2ccc(-c3nnc(C(F)(F)F)o3)cc2F)c2cccc(Cl)c2F)C1] |
| 251 | 21646 | 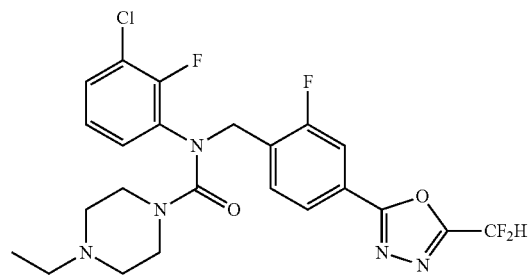 [SMILES: CCN1CCN(C(=O)N(Cc2ccc(-c3nnc(C(F)F)o3)cc2F)c2cccc(Cl)c2F)CC1] |
| 252 | 21650 | 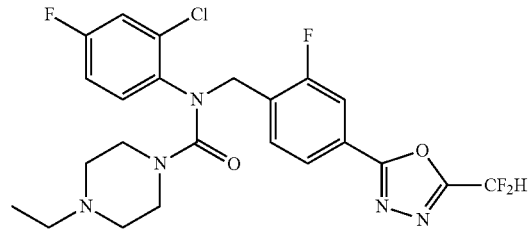 [SMILES: CCN1CCN(C(=O)N(Cc2ccc(-c3nnc(C(F)F)o3)cc2F)c2ccc(F)cc2Cl)CC1] |
| 253 | 21651 | 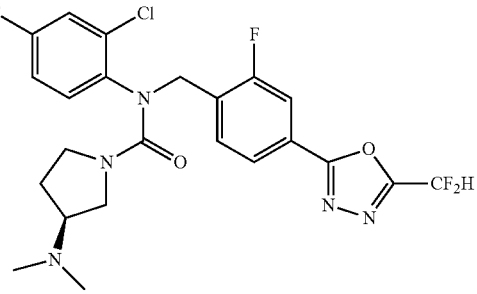 |

-continued
| Ex. | Comp. | Structure |
|---|---|---|
| 254 | 21652 | 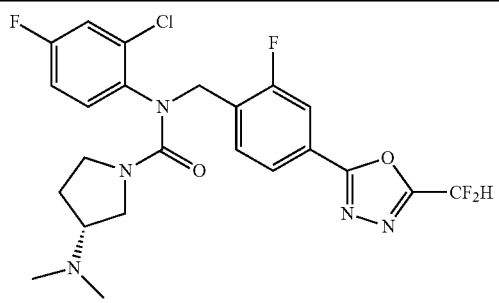 |
| 255 | 21653 | 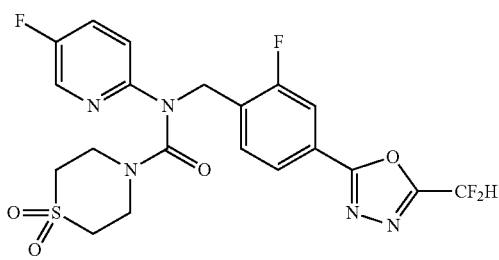 [SMILES: O=C(N1CCS(=O)(=O)CC1)N(Cc1ccc(-c2nnc(C(F)F)o2)cc1F)c1ccc(F)cn1] |
| 256 | 21654 | 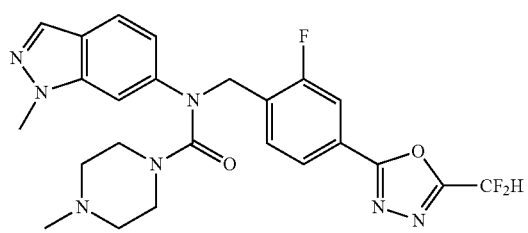 [SMILES: CN1CCN(C(=O)N(Cc2ccc(-c3nnc(C(F)F)o3)cc2F)c2ccc3cnn(C)c3c2)CC1] |
| 257 | 21655 | 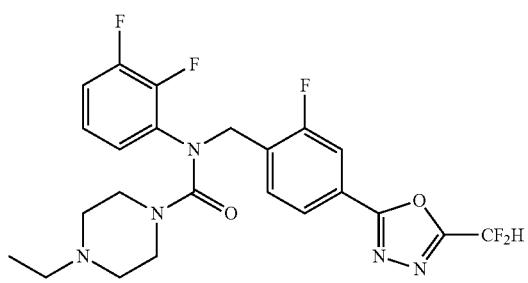 [SMILES: CCN1CCN(C(=O)N(Cc2ccc(-c3nnc(C(F)F)o3)cc2F)c2cccc(F)c2F)CC1] |
| 258 | 21656 | 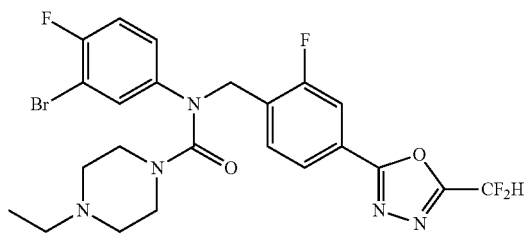 [SMILES: CCN1CCN(C(=O)N(Cc2ccc(-c3nnc(C(F)F)o3)cc2F)c2ccc(F)c(Br)c2)CC1] |
| 259 | 21657 | 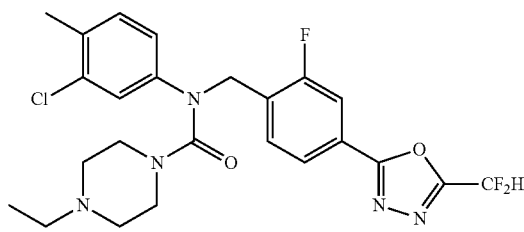 [SMILES: CCN1CCN(C(=O)N(Cc2ccc(-c3nnc(C(F)F)o3)cc2F)c2ccc(C)c(Cl)c2)CC1] |

-continued

| Ex. | Comp. | Structure |
|---|---|---|
| 260 | 21658 | 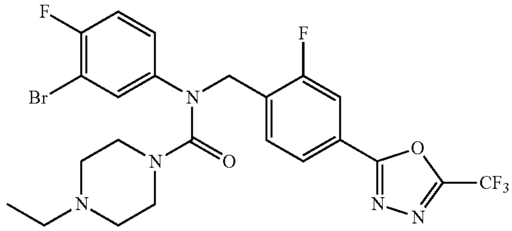 [SMILES: CCN1CCN(C(=O)N(Cc2ccc(-c3nnc(C(F)(F)F)o3)cc2F)c2ccc(F)c(Br)c2)CC1] |
| 261 | 21659 | 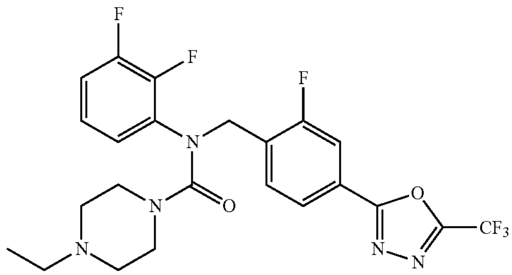 [SMILES: CCN1CCN(C(=O)N(Cc2ccc(-c3nnc(C(F)(F)F)o3)cc2F)c2cccc(F)c2F)CC1] |
| 262 | 21660 | 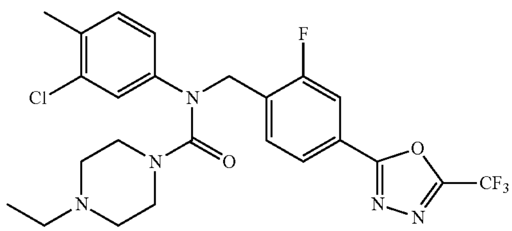 [SMILES: CCN1CCN(C(=O)N(Cc2ccc(-c3nnc(C(F)(F)F)o3)cc2F)c2ccc(C)c(Cl)c2)CC1] |
| 263 | 21664 | 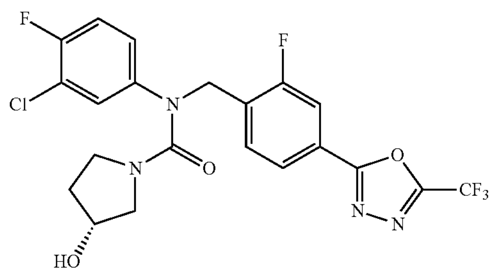 [SMILES: O=C(N1CC[C@@H](O)C1)N(Cc1ccc(-c2nnc(C(F)(F)F)o2)cc1F)c1ccc(F)c(Cl)c1] |
| 264 | 21665 | 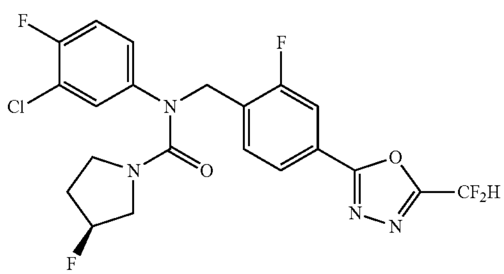 [SMILES: O=C(N1CC[C@H](F)C1)N(Cc1ccc(-c2nnc(C(F)F)o2)cc1F)c1ccc(F)c(Cl)c1] |
| 265 | 21666 | 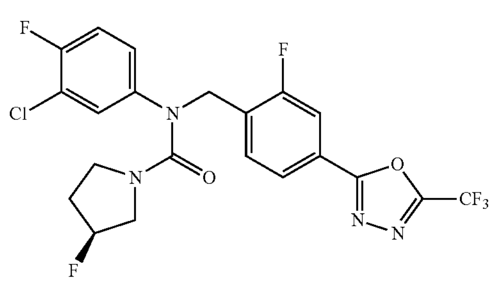 [SMILES: O=C(N1CC[C@H](F)C1)N(Cc1ccc(-c2nnc(C(F)(F)F)o2)cc1F)c1ccc(F)c(Cl)c1] |

-continued
| Ex. | Comp. | Structure |
|---|---|---|
| 266 | 21667 | 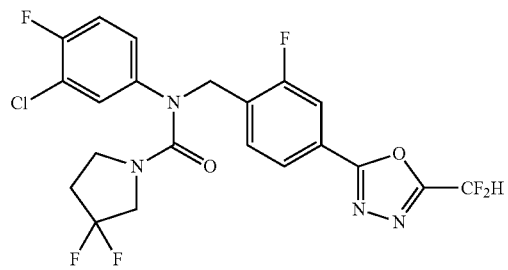 [SMILES: O=C(N1CCC(F)(F)C1)N(Cc1ccc(-c2nnc(C(F)F)o2)cc1F)c1ccc(F)c(Cl)c1] |
| 267 | 21668 | 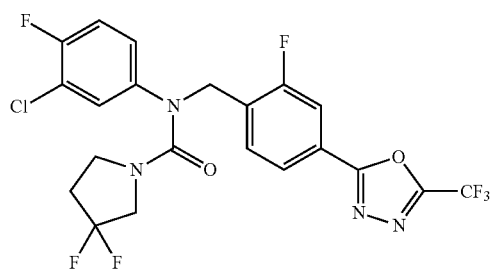 [SMILES: O=C(N1CCC(F)(F)C1)N(Cc1ccc(-c2nnc(C(F)(F)F)o2)cc1F)c1ccc(F)c(Cl)c1] |
| 268 | 21669 | 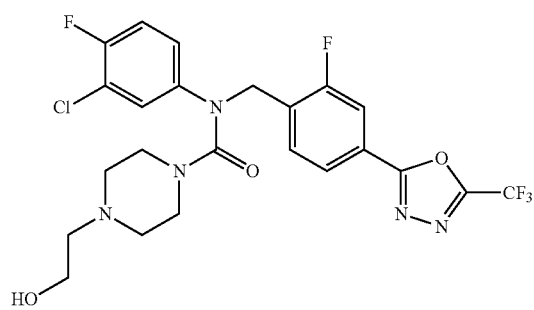 [SMILES: O=C(N1CCN(CCO)CC1)N(Cc1ccc(-c2nnc(C(F)(F)F)o2)cc1F)c1ccc(F)c(Cl)c1] |
| 269 | 21679 | 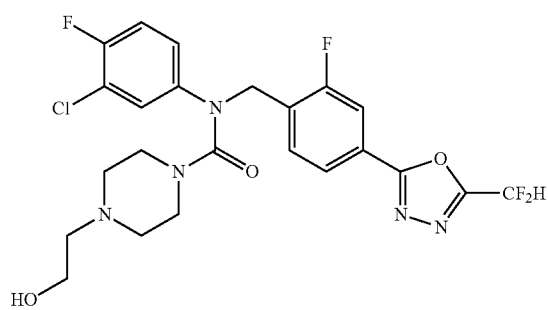 [SMILES: O=C(N1CCN(CCO)CC1)N(Cc1ccc(-c2nnc(C(F)F)o2)cc1F)c1ccc(F)c(Cl)c1] |
| 270 | 21707 | 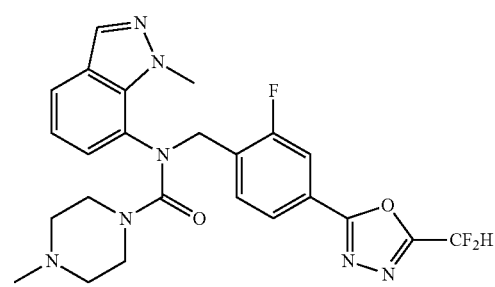 [SMILES: CN1CCN(C(=O)N(Cc2ccc(-c3nnc(C(F)F)o3)cc2F)c2cccc3cnn(C)c23)CC1] |

| Ex. | Comp. | Structure |
|---|---|---|
| 271 | 21708 | 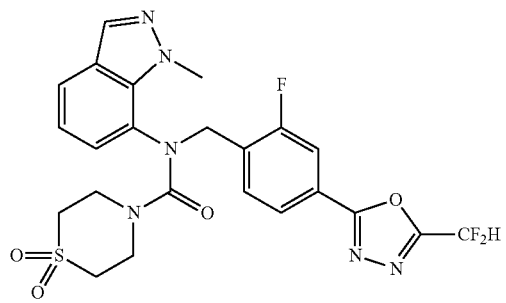 [SMILES: Cn1ncc2cccc(N(Cc3ccc(-c4nnc(C(F)F)o4)cc3F)C(=O)N3CCS(=O)(=O)CC3)c21] |
| 272 | 21709 | 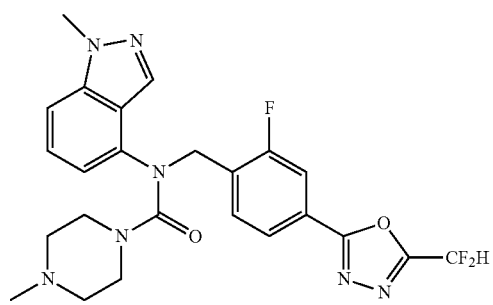 [SMILES: CN1CCN(C(=O)N(Cc2ccc(-c3nnc(C(F)F)o3)cc2F)c2cccc3c2cnn3C)CC1] |
| 273 | 21710 | 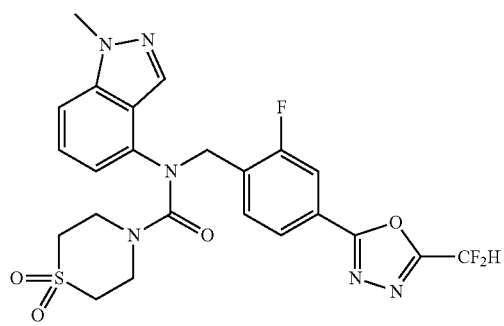 [SMILES: Cn1ncc2c(N(Cc3ccc(-c4nnc(C(F)F)o4)cc3F)C(=O)N3CCS(=O)(=O)CC3)cccc21] |
| 274 | 21724 | 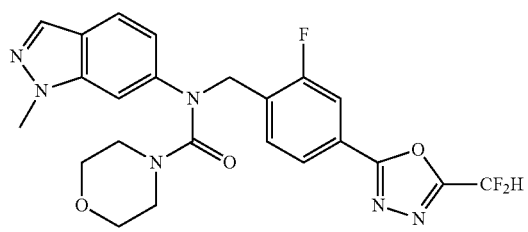 [SMILES: Cn1ncc2ccc(N(Cc3ccc(-c4nnc(C(F)F)o4)cc3F)C(=O)N3CCOCC3)cc21] |
| 275 | 21735 | 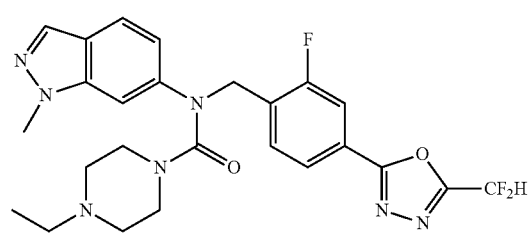 [SMILES: CCN1CCN(C(=O)N(Cc2ccc(-c3nnc(C(F)F)o3)cc2F)c2ccc3cnn(C)c3c2)CC1] |

-continued

| Ex. | Comp. | Structure |
|---|---|---|
| 276 | 21736 | 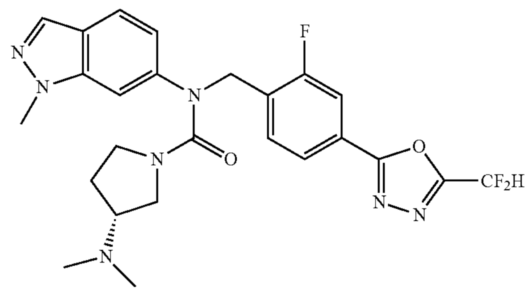 [SMILES: CN(C)[C@@H]1CCN(C(=O)N(Cc2ccc(-c3nnc(C(F)F)o3)cc2F)c2ccc3cnn(C)c3c2)C1] |
| 277 | 21759 | 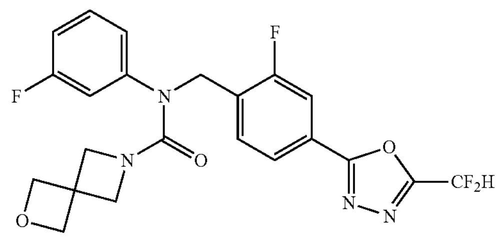 [SMILES: O=C(N1CC2(COC2)C1)N(Cc1ccc(-c2nnc(C(F)F)o2)cc1F)c1cccc(F)c1] |
| 278 | 21760 | 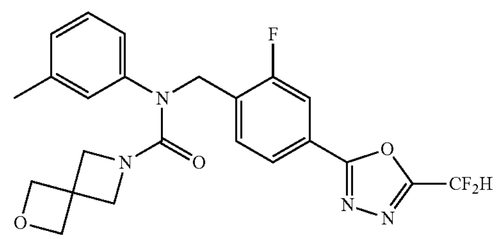 [SMILES: Cc1cccc(N(Cc2ccc(-c3nnc(C(F)F)o3)cc2F)C(=O)N2CC3(COC3)C2)c1] |
| 279 | 21765 | 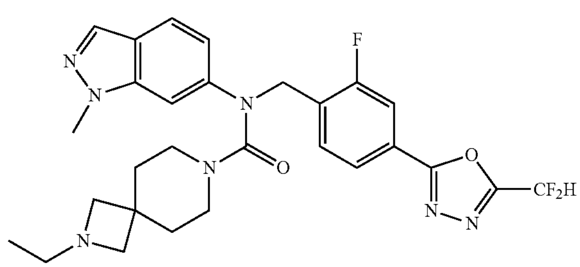 [SMILES: CCN1CC2(CCN(C(=O)N(Cc3ccc(-c4nnc(C(F)F)o4)cc3F)c3ccc4cnn(C)c4c3)CC2)C1] |
| 280 | 21766 | 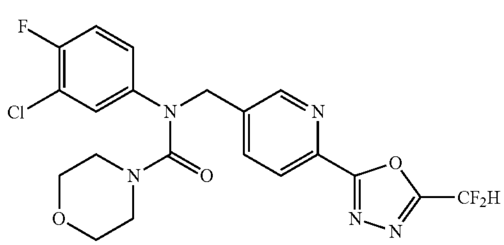 [SMILES: O=C(N1CCOCC1)N(Cc1ccc(-c2nnc(C(F)F)o2)nc1)c1ccc(F)c(Cl)c1] |
| 281 | 21767 | 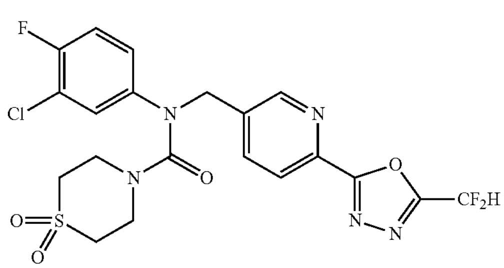 [SMILES: O=C(N1CCS(=O)(=O)CC1)N(Cc1ccc(-c2nnc(C(F)F)o2)nc1)c1ccc(F)c(Cl)c1] |

| Ex. | Comp. | Structure |
|---|---|---|
| 282 | 21797 | 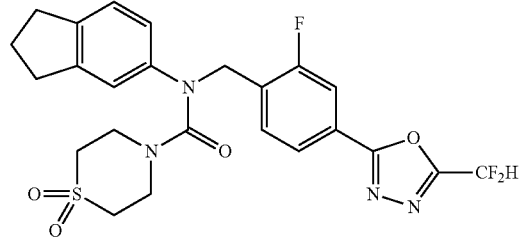 [SMILES: O=C(N1CCS(=O)(=O)CC1)N(Cc1ccc(-c2nnc(C(F)F)o2)cc1F)c1ccc2c(c1)CCC2] |
| 283 | 21798 | 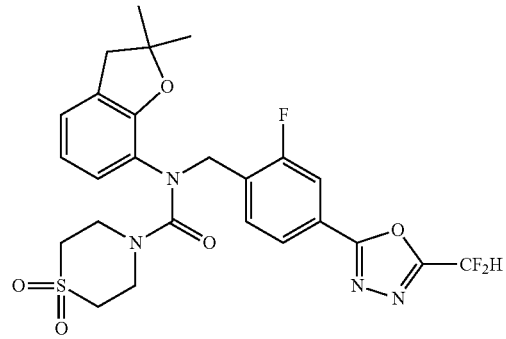 [SMILES: CC1(C)Cc2cccc(N(Cc3ccc(-c4nnc(C(F)F)o4)cc3F)C(=O)N3CCS(=O)(=O)CC3)c2O1] |
| 284 | 21799 | 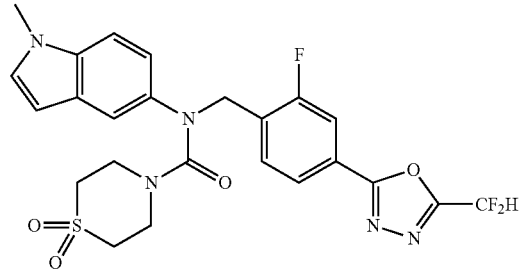 [SMILES: Cn1ccc2cc(N(Cc3ccc(-c4nnc(C(F)F)o4)cc3F)C(=O)N3CCS(=O)(=O)CC3)ccc21] |
| 285 | 21806 | 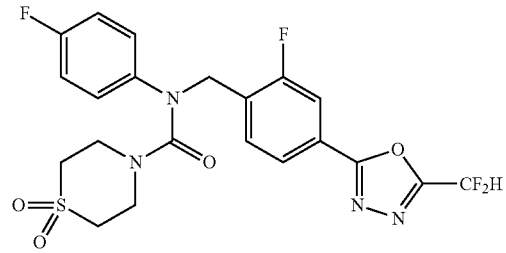 [SMILES: O=C(N1CCS(=O)(=O)CC1)N(Cc1ccc(-c2nnc(C(F)F)o2)cc1F)c1ccc(F)cc1] |
| 286 | 21807 | 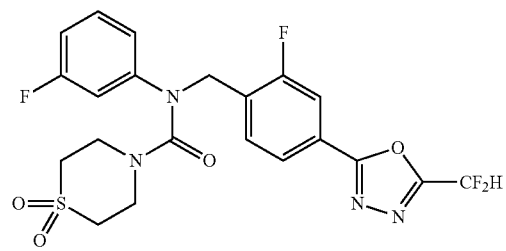 |

-continued

| Ex. | Comp. | Structure |
|---|---|---|
| 287 | 21808 | 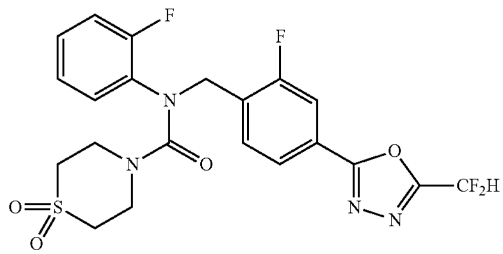 [SMILES: O=C(N1CCS(=O)(=O)CC1)N(Cc1ccc(-c2nnc(C(F)F)o2)cc1F)c1ccccc1F] |
| 288 | 21809 | 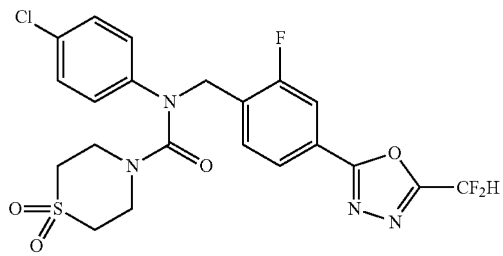 [SMILES: O=C(N1CCS(=O)(=O)CC1)N(Cc1ccc(-c2nnc(C(F)F)o2)cc1F)c1ccc(Cl)cc1] |
| 289 | 21810 | 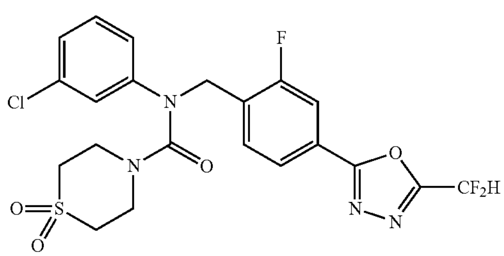 [SMILES: O=C(N1CCS(=O)(=O)CC1)N(Cc1ccc(-c2nnc(C(F)F)o2)cc1F)c1cccc(Cl)c1] |
| 290 | 21811 | 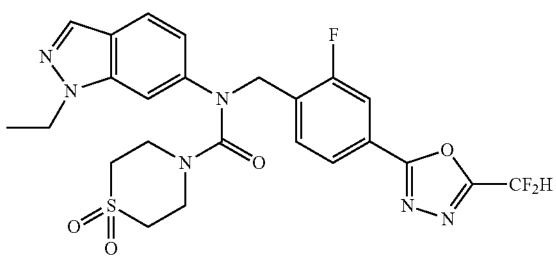 [SMILES: CCn1ncc2ccc(N(Cc3ccc(-c4nnc(C(F)F)o4)cc3F)C(=O)N3CCS(=O)(=O)CC3)cc21] |
| 291 | 21812 | 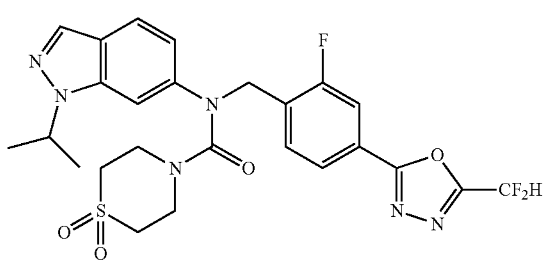 [SMILES: CC(C)n1ncc2ccc(N(Cc3ccc(-c4nnc(C(F)F)o4)cc3F)C(=O)N3CCS(=O)(=O)CC3)cc21] |
| 292 | 21813 | 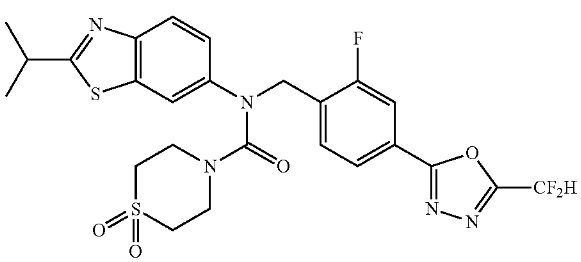 [SMILES: CC(C)c1nc2ccc(N(Cc3ccc(-c4nnc(C(F)F)o4)cc3F)C(=O)N3CCS(=O)(=O)CC3)cc2s1] |

| Ex. | Comp. | Structure |
|---|---|---|
| 293 | 21823 | 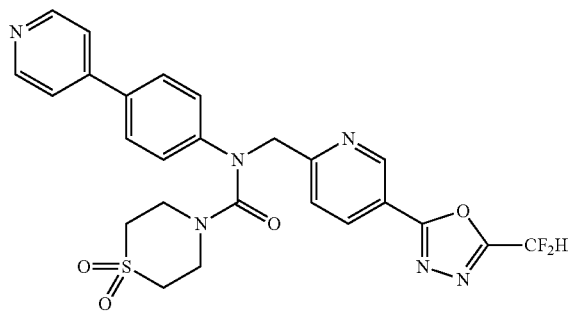 [SMILES: O=C(N1CCS(=O)(=O)CC1)N(Cc1ccc(-c2nnc(C(F)F)o2)cn1)c1ccc(-c2ccncc2)cc1] |
| 294 | 21824 | 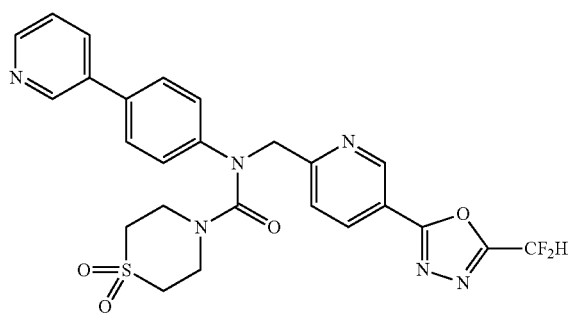 |
| 295 | 21829 | 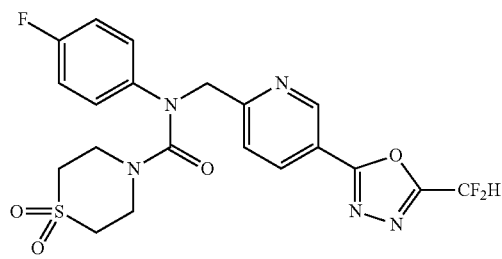 [SMILES: O=C(N1CCS(=O)(=O)CC1)N(Cc1ccc(-c2nnc(C(F)F)o2)cn1)c1ccc(F)cc1] |
| 296 | 21830 | 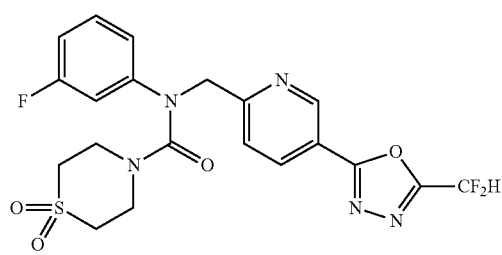 |
| 297 | 21831 | 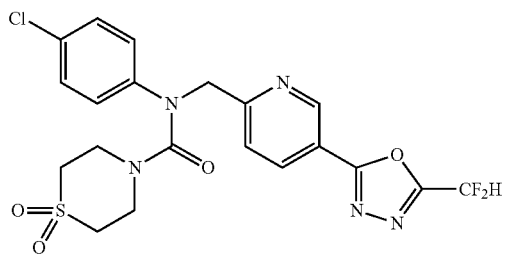 [SMILES: O=C(N1CCS(=O)(=O)CC1)N(Cc1ccc(-c2nnc(C(F)F)o2)cn1)c1ccc(Cl)cc1] |

-continued

| Ex. | Comp. | Structure |
|---|---|---|
| 298 | 21839 | 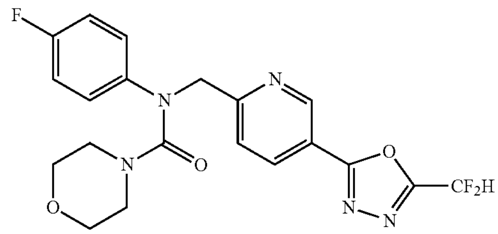 [SMILES: O=C(N1CCOCC1)N(Cc1ccc(-c2nnc(C(F)F)o2)cn1)c1ccc(F)cc1] |
| 299 | 21840 | 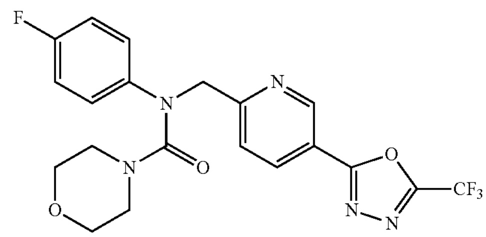 [SMILES: O=C(N1CCOCC1)N(Cc1ccc(-c2nnc(C(F)(F)F)o2)cn1)c1ccc(F)cc1] |
| 300 | 21841 | 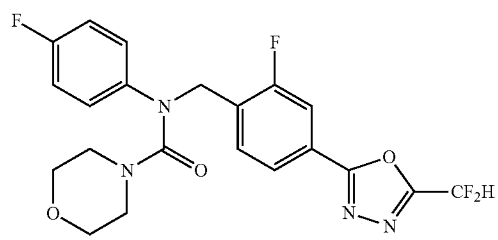 [SMILES: O=C(N1CCOCC1)N(Cc1ccc(-c2nnc(C(F)F)o2)cc1F)c1ccc(F)cc1] |
| 301 | 21842 | 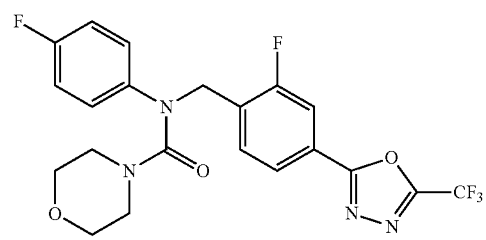 |
| 302 | 21843 | 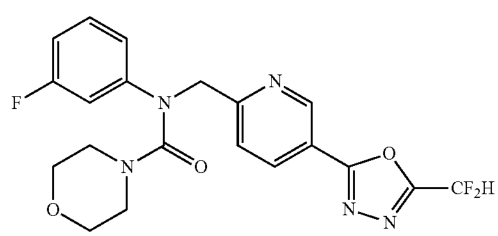 [SMILES: O=C(N1CCOCC1)N(Cc1ccc(-c2nnc(C(F)F)o2)cn1)c1cccc(F)c1] |
| 303 | 21844 | 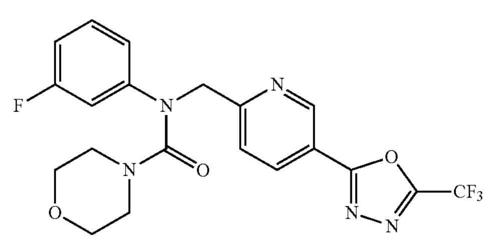 [SMILES: O=C(N1CCOCC1)N(Cc1ccc(-c2nnc(C(F)(F)F)o2)cn1)c1cccc(F)c1] |

| Ex. | Comp. | Structure |
|---|---|---|
| 304 | 21845 | 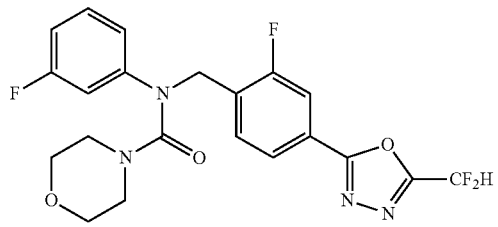 [SMILES: O=C(N1CCOCC1)N(Cc1ccc(-c2nnc(C(F)F)o2)cc1F)c1cccc(F)c1] |
| 305 | 21846 | 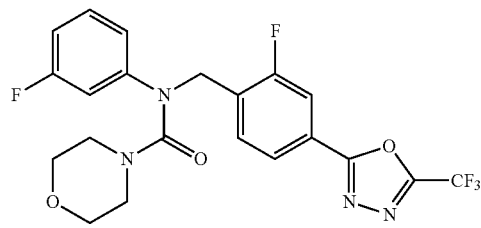 [SMILES: O=C(N1CCOCC1)N(Cc1ccc(-c2nnc(C(F)(F)F)o2)cc1F)c1cccc(F)c1] |
| 306 | 21847 | 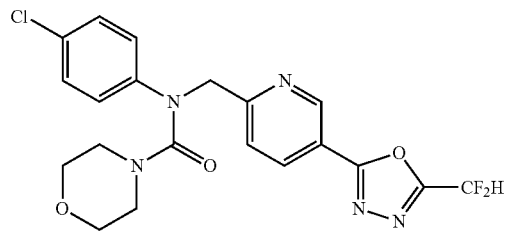 [SMILES: O=C(N1CCOCC1)N(Cc1ccc(-c2nnc(C(F)F)o2)cn1)c1ccc(Cl)cc1] |
| 307 | 21848 | 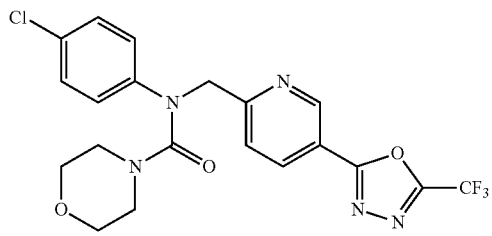 [SMILES: O=C(N1CCOCC1)N(Cc1ccc(-c2nnc(C(F)(F)F)o2)cn1)c1ccc(Cl)cc1] |
| 308 | 21849 | 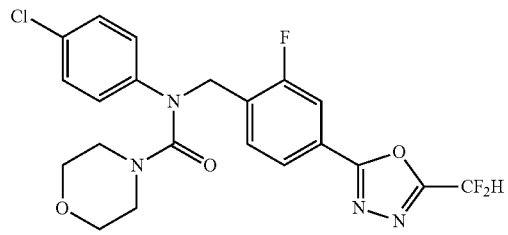 [SMILES: O=C(N1CCOCC1)N(Cc1ccc(-c2nnc(C(F)F)o2)cc1F)c1ccc(Cl)cc1] |
| 309 | 21850 | 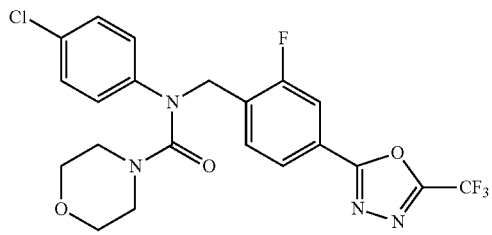 [SMILES: O=C(N1CCOCC1)N(Cc1ccc(-c2nnc(C(F)(F)F)o2)cc1F)c1ccc(Cl)cc1] |

-continued
| Ex. | Comp. | Structure |
|---|---|---|
| 310 | 21851 | 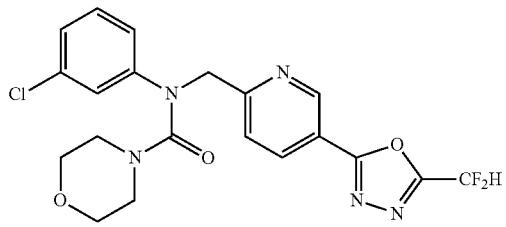 [SMILES: O=C(N1CCOCC1)N(Cc1ccc(-c2nnc(C(F)F)o2)cn1)c1cccc(Cl)c1] |
| 311 | 21852 | 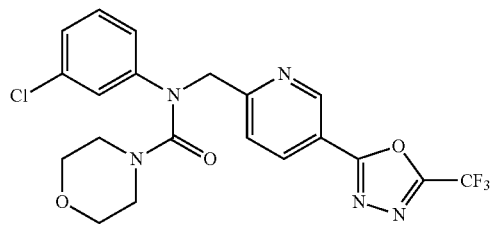 [SMILES: O=C(N1CCOCC1)N(Cc1ccc(-c2nnc(C(F)(F)F)o2)cn1)c1cccc(Cl)c1] |
| 312 | 21853 | 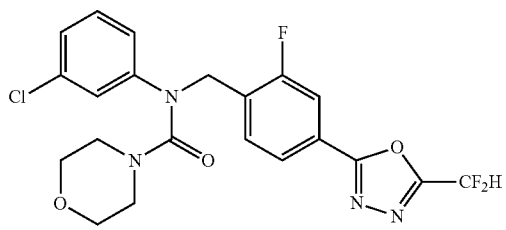 [SMILES: O=C(N1CCOCC1)N(Cc1ccc(-c2nnc(C(F)F)o2)cc1F)c1cccc(Cl)c1] |
| 313 | 21854 | 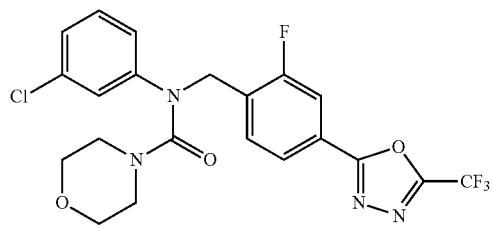 [SMILES: O=C(N1CCOCC1)N(Cc1ccc(-c2nnc(C(F)(F)F)o2)cc1F)c1cccc(Cl)c1] |
| 314 | 21855 | 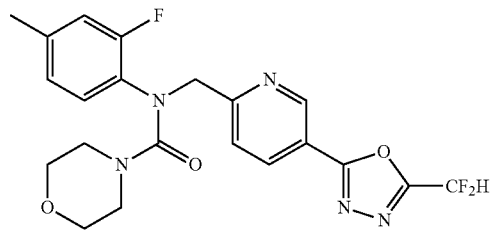 [SMILES: Cc1ccc(N(Cc2ccc(-c3nnc(C(F)F)o3)cn2)C(=O)N2CCOCC2)c(F)c1] |
| 315 | 21856 | 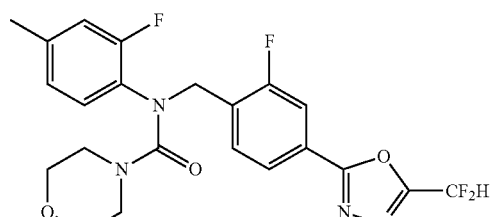 |

-continued
| Ex. | Comp. | Structure |
|---|---|---|
| 316 | 21857 | 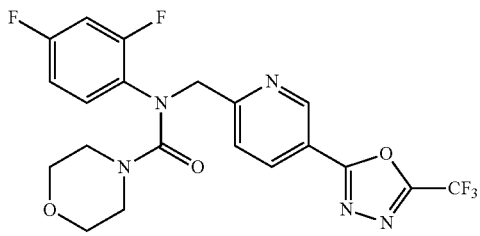 [SMILES: O=C(N1CCOCC1)N(Cc1ccc(-c2nnc(C(F)(F)F)o2)cn1)c1ccc(F)cc1F] |
| 317 | 21858 | 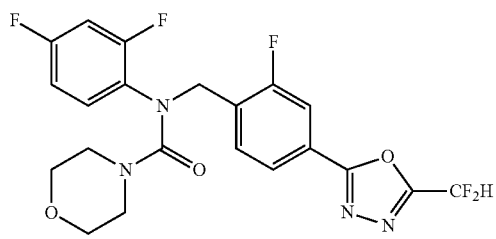 [SMILES: O=C(N1CCOCC1)N(Cc1ccc(-c2nnc(C(F)F)o2)cc1F)c1ccc(F)cc1F] |
| 318 | 21859 | 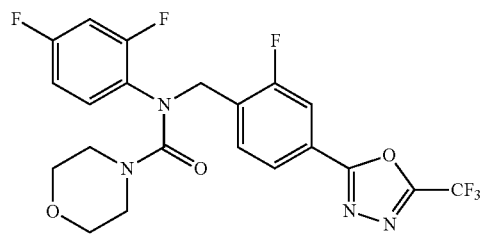 |
| 319 | 21860 | 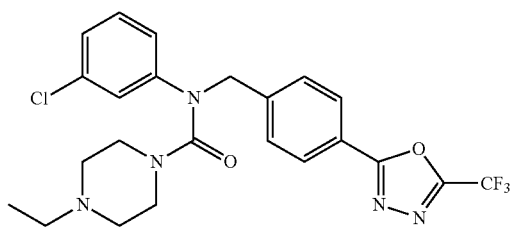 |
| 320 | 21861 | 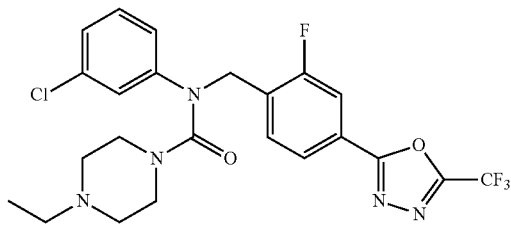 [SMILES: CCN1CCN(C(=O)N(Cc2ccc(-c3nnc(C(F)(F)F)o3)cc2F)c2cccc(Cl)c2)CC1] |
| 321 | 21862 | 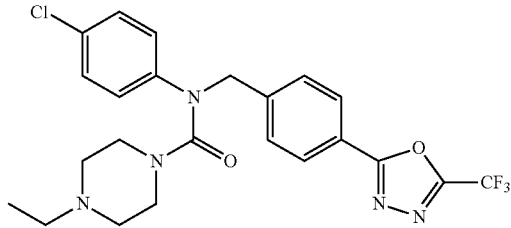 |

| Ex. | Comp. | Structure |
|---|---|---|
| 322 | 21863 | 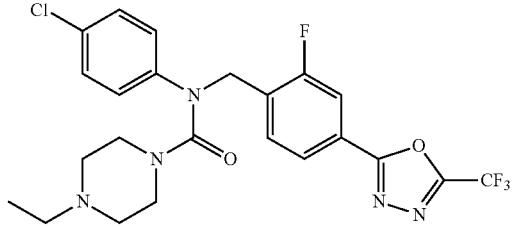 |
| 323 | 21864 | 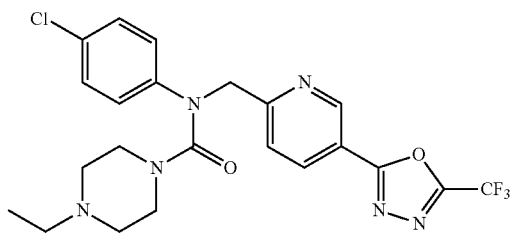 |
| 324 | 21865 | 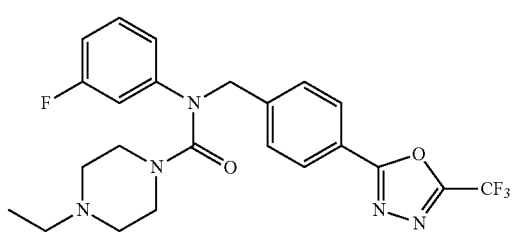 [SMILES: CCN1CCN(C(=O)N(Cc2ccc(-c3nnc(C(F)(F)F)o3)cc2)c2cccc(F)c2)CC1] |
| 325 | 21866 | 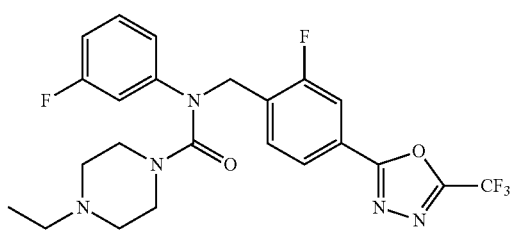 |
| 326 | 21867 | 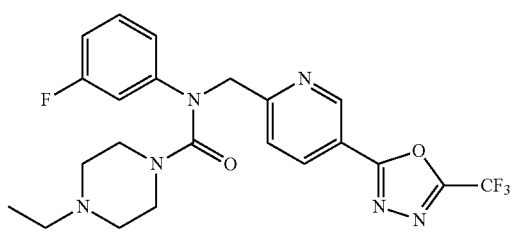 [SMILES: CCN1CCN(C(=O)N(Cc2ccc(-c3nnc(C(F)(F)F)o3)cn2)c2cccc(F)c2)CC1] |
| 327 | 21868 | 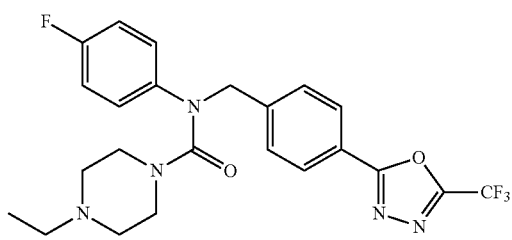 |

-continued
| Ex. | Comp. | Structure |
|---|---|---|
| 328 | 21869 | 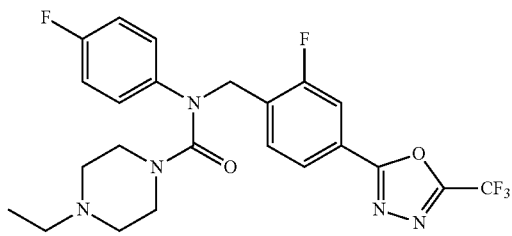 |
| 329 | 21870 | 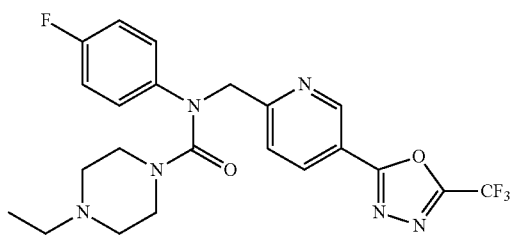 |
| 330 | 21871 | 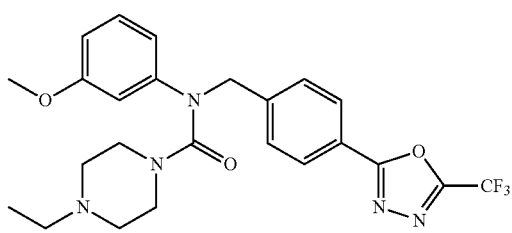 [SMILES: CCN1CCN(C(=O)N(Cc2ccc(-c3nnc(C(F)(F)F)o3)cc2)c2cccc(OC)c2)CC1] |
| 331 | 21872 | 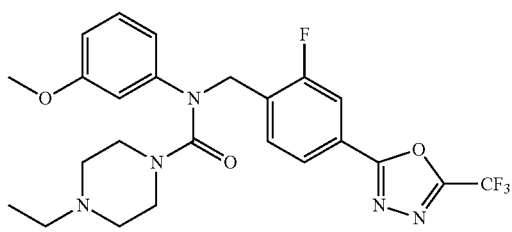 [SMILES: CCN1CCN(C(=O)N(Cc2ccc(-c3nnc(C(F)(F)F)o3)cc2F)c2cccc(OC)c2)CC1] |
| 332 | 21873 | 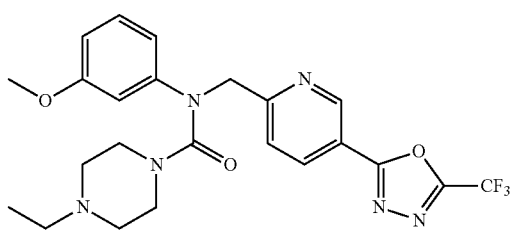 [SMILES: CCN1CCN(C(=O)N(Cc2ccc(-c3nnc(C(F)(F)F)o3)cn2)c2cccc(OC)c2)CC1] |
| 333 | 21874 | 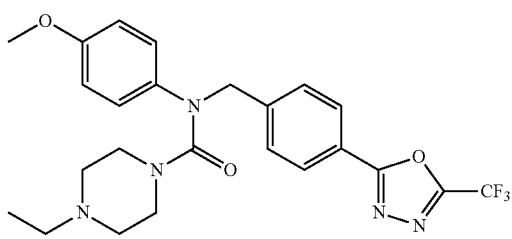 [SMILES: CCN1CCN(C(=O)N(Cc2ccc(-c3nnc(C(F)(F)F)o3)cc2)c2ccc(OC)cc2)CC1] |

-continued
| Ex. | Comp. | Structure |
|---|---|---|
| 334 | 21875 | 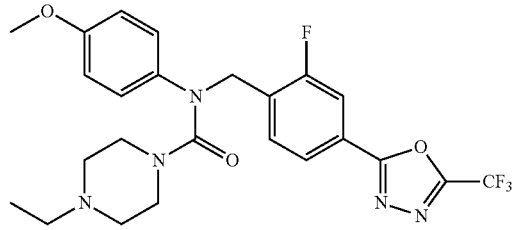 |
| 335 | 21876 | 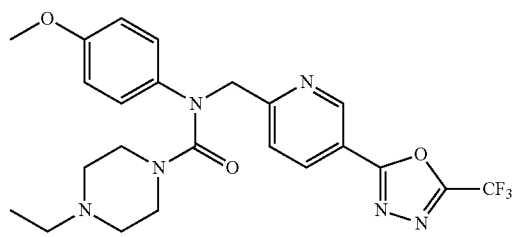 [SMILES: CCN1CCN(C(=O)N(Cc2ccc(-c3nnc(C(F)(F)F)o3)cn2)c2ccc(OC)cc2)CC1] |
| 336 | 21877 | 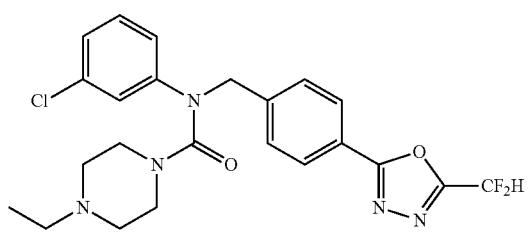 [SMILES: CCN1CCN(C(=O)N(Cc2ccc(-c3nnc(C(F)F)o3)cc2)c2cccc(Cl)c2)CC1] |
| 337 | 21878 | 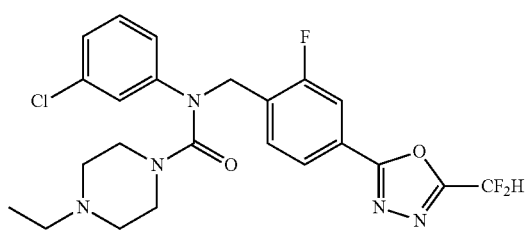 [SMILES: CCN1CCN(C(=O)N(Cc2ccc(-c3nnc(C(F)F)o3)cc2F)c2cccc(Cl)c2)CC1] |
| 338 | 21879 | 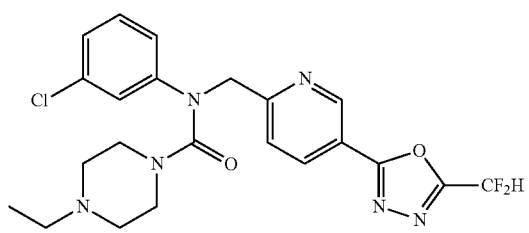 [SMILES: CCN1CCN(C(=O)N(Cc2ccc(-c3nnc(C(F)F)o3)cn2)c2cccc(Cl)c2)CC1] |
| 339 | 21880 | 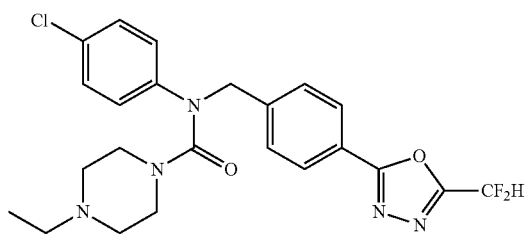 |

-continued
| Ex. | Comp. | Structure |
|---|---|---|
| 340 | 21881 | 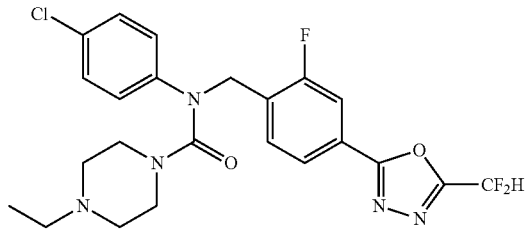 [SMILES: CCN1CCN(C(=O)N(Cc2ccc(-c3nnc(C(F)F)o3)cc2F)c2ccc(Cl)cc2)CC1] |
| 341 | 21882 | 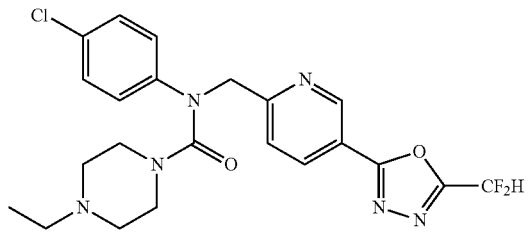 |
| 342 | 21883 | 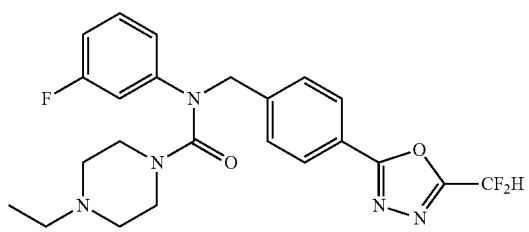 [SMILES: CCN1CCN(C(=O)N(Cc2ccc(-c3nnc(C(F)F)o3)cc2)c2cccc(F)c2)CC1] |
| 343 | 21884 | 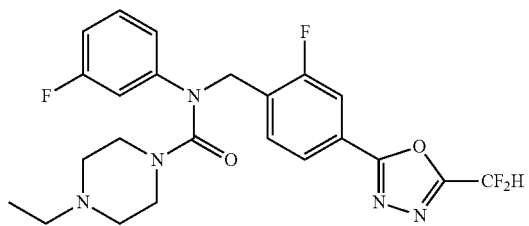 [SMILES: CCN1CCN(C(=O)N(Cc2ccc(-c3nnc(C(F)F)o3)cc2F)c2cccc(F)c2)CC1] |
| 344 | 21885 | 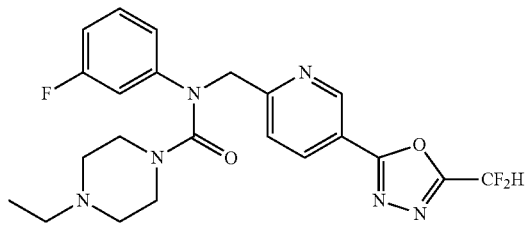 [SMILES: CCN1CCN(C(=O)N(Cc2ccc(-c3nnc(C(F)F)o3)cn2)c2cccc(F)c2)CC1] |
| 345 | 21886 | 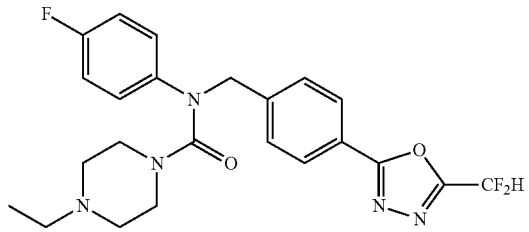 [SMILES: CCN1CCN(C(=O)N(Cc2ccc(-c3nnc(C(F)F)o3)cc2)c2ccc(F)cc2)CC1] |

| Ex. | Comp. | Structure |
|---|---|---|
| 346 | 21887 | 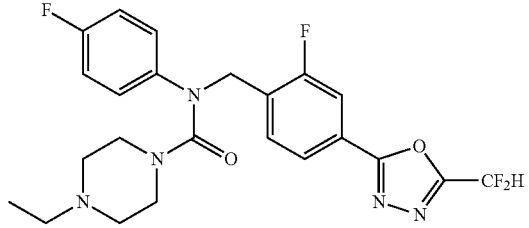 [SMILES: CCN1CCN(C(=O)N(Cc2ccc(-c3nnc(C(F)F)o3)cc2F)c2ccc(F)cc2)CC1] |
| 347 | 21888 | 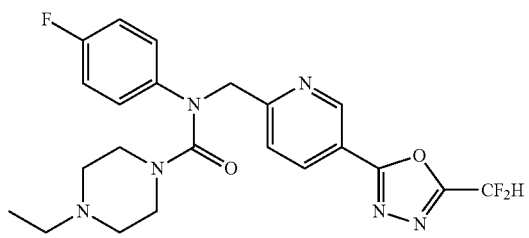 [SMILES: CCN1CCN(C(=O)N(Cc2ccc(-c3nnc(C(F)F)o3)cn2)c2ccc(F)cc2)CC1] |
| 348 | 21889 | 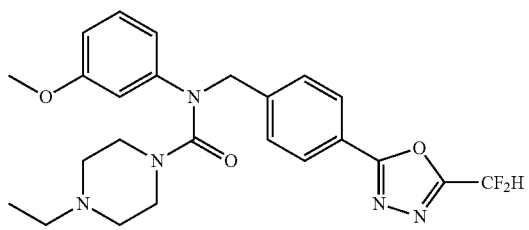 [SMILES: CCN1CCN(C(=O)N(Cc2ccc(-c3nnc(C(F)F)o3)cc2)c2cccc(OC)c2)CC1] |
| 349 | 21890 | 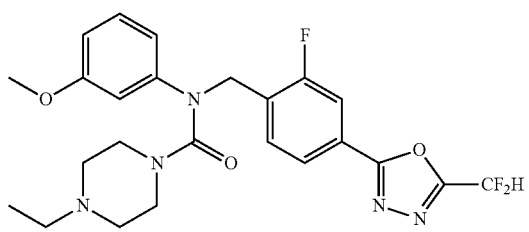 [SMILES: CCN1CCN(C(=O)N(Cc2ccc(-c3nnc(C(F)F)o3)cc2F)c2cccc(OC)c2)CC1] |
| 350 | 21891 | 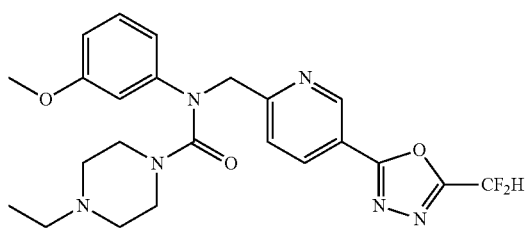 [SMILES: CCN1CCN(C(=O)N(Cc2ccc(-c3nnc(C(F)F)o3)cn2)c2cccc(OC)c2)CC1] |
| 351 | 21892 | 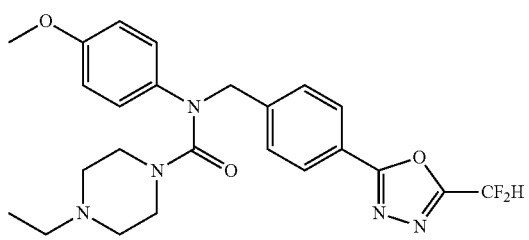 |

| Ex. | Comp. | Structure |
|---|---|---|
| 352 | 21893 | 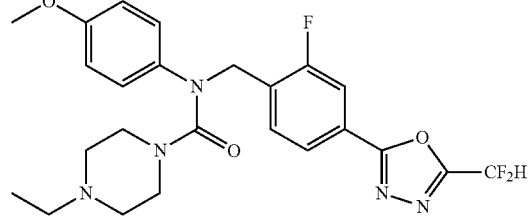 |
| 353 | 21894 | 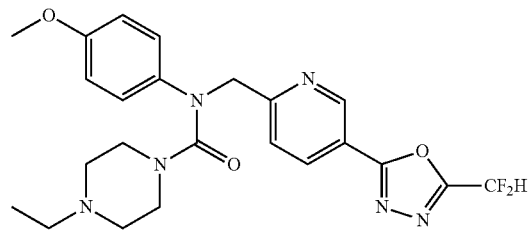 [SMILES: CCN1CCN(C(=O)N(Cc2ccc(-c3nnc(C(F)F)o3)cn2)c2ccc(OC)cc2)CC1] |
| 354 | 21895 | 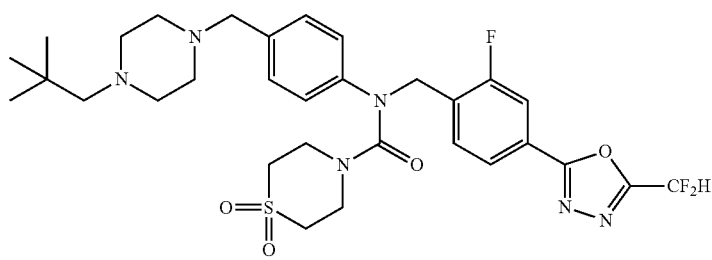 [SMILES: CC(C)(C)CN1CCN(Cc2ccc(N(Cc3ccc(-c4nnc(C(F)F)o4)cc3F)C(=O)N3CCS(=O)(=O)CC3)cc2)CC1] |
| 355 | 21896 | 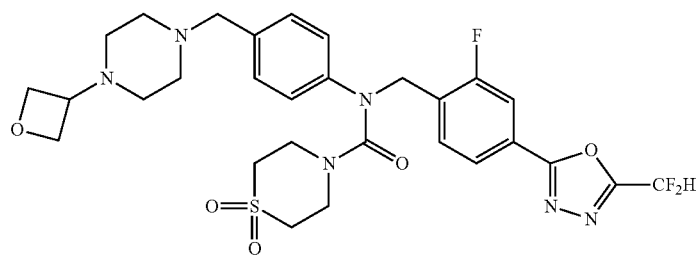 [SMILES: O=C(N1CCS(=O)(=O)CC1)N(Cc1ccc(-c2nnc(C(F)F)o2)cc1F)c1ccc(CN2CCN(C3COC3)CC2)cc1] |
| 356 | 21897 | 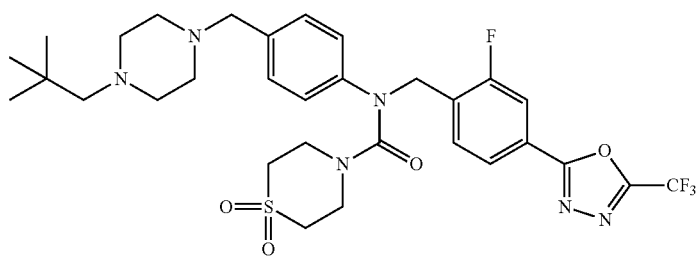 [SMILES: CC(C)(C)CN1CCN(Cc2ccc(N(Cc3ccc(-c4nnc(C(F)(F)F)o4)cc3F)C(=O)N3CCS(=O)(=O)CC3)cc2)CC1] |
| 357 | 21898 | 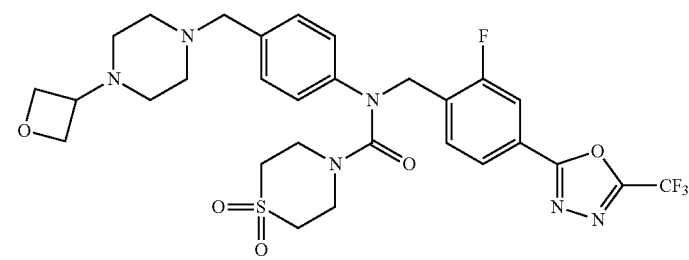 [SMILES: O=C(N1CCS(=O)(=O)CC1)N(Cc1ccc(-c2nnc(C(F)(F)F)o2)cc1F)c1ccc(CN2CCN(C3COC3)CC2)cc1] |

-continued

| Ex. | Comp. | Structure |
|---|---|---|
| 358 | 21899 | 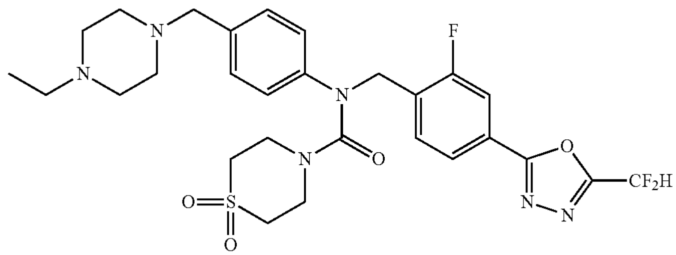 [SMILES: CCN1CCN(Cc2ccc(N(Cc3ccc(-c4nnc(C(F)F)o4)cc3F)C(=O)N3CCS(=O)(=O)CC3)cc2)CC1] |
| 359 | 21900 | 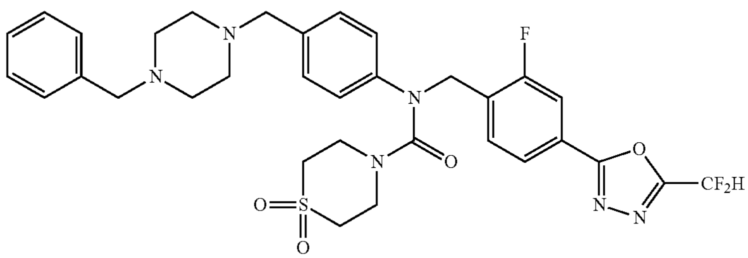 [SMILES: O=C(N1CCS(=O)(=O)CC1)N(Cc1ccc(-c2nnc(C(F)F)o2)cc1F)c1ccc(CN2CCN(Cc3ccccc3)CC2)cc1] |
| 360 | 21901 | 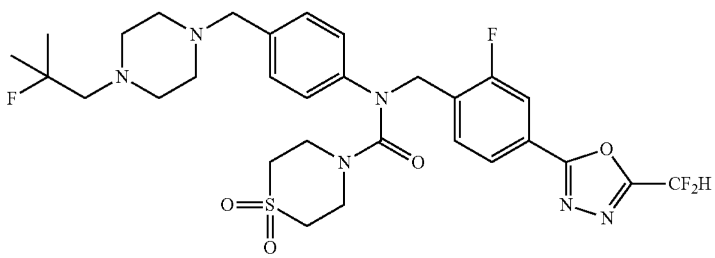 [SMILES: CC(C)(F)CN1CCN(Cc2ccc(N(Cc3ccc(-c4nnc(C(F)F)o4)cc3F)C(=O)N3CCS(=O)(=O)CC3)cc2)CC1] |
| 361 | 21902 | 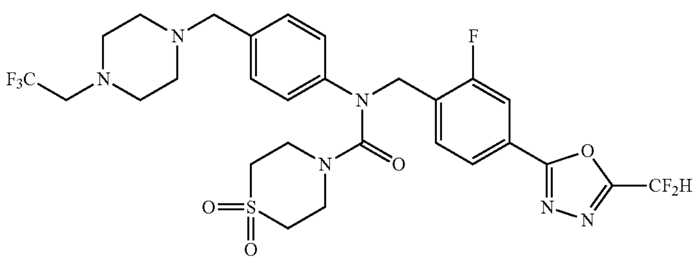 [SMILES: O=C(N1CCS(=O)(=O)CC1)N(Cc1ccc(-c2nnc(C(F)F)o2)cc1F)c1ccc(CN2CCN(CC(F)(F)F)CC2)cc1] |
| 362 | 21905 | 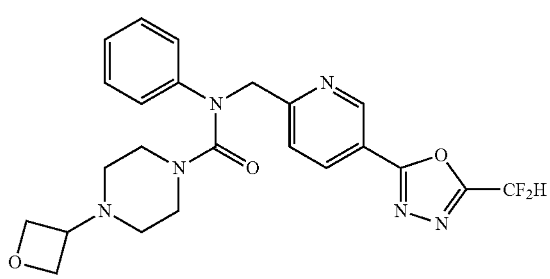 [SMILES: O=C(N1CCN(C2COC2)CC1)N(Cc1ccc(-c2nnc(C(F)F)o2)cn1)c1ccccc1] |
| 363 | 21910 | 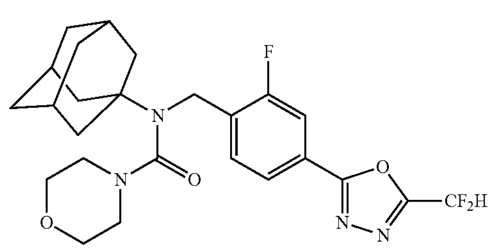 [SMILES: O=C(N1CCOCC1)N(Cc1ccc(-c2nnc(C(F)F)o2)cc1F)C12CC3CC(CC(C3)C1)C2] |

| Ex. | Comp. | Structure |
|---|---|---|
| 364 | 21914 | 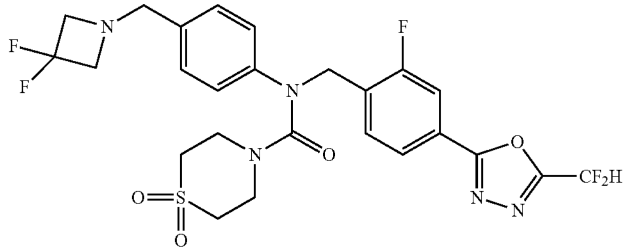 [SMILES: O=C(N1CCS(=O)(=O)CC1)N(Cc1ccc(-c2nnc(C(F)F)o2)cc1F)c1ccc(CN2CC(F)(F)C2)cc1] |
| 365 | 21915 | 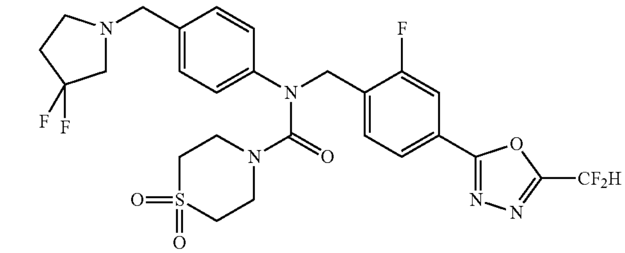 [SMILES: O=C(N1CCS(=O)(=O)CC1)N(Cc1ccc(-c2nnc(C(F)F)o2)cc1F)c1ccc(CN2CCC(F)(F)C2)cc1] |
| 366 | 21916 | 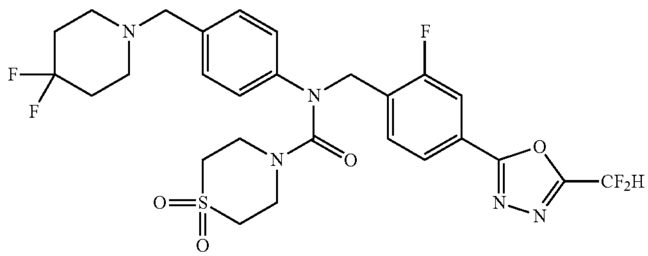 [SMILES: O=C(N1CCS(=O)(=O)CC1)N(Cc1ccc(-c2nnc(C(F)F)o2)cc1F)c1ccc(CN2CCC(F)(F)CC2)cc1] |
| 367 | 21917 | 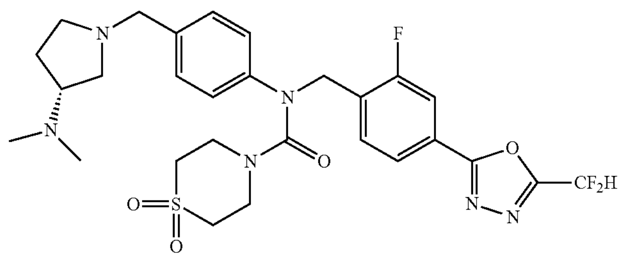 [SMILES: CN(C)[C@@H]1CCN(Cc2ccc(N(Cc3ccc(-c4nnc(C(F)F)o4)cc3F)C(=O)N3CCS(=O)(=O)CC3)cc2)C1] |
| 368 | 21918 | 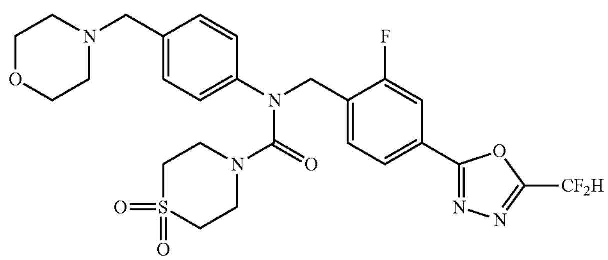 [SMILES: O=C(N1CCS(=O)(=O)CC1)N(Cc1ccc(-c2nnc(C(F)F)o2)cc1F)c1ccc(CN2CCOCC2)cc1] |
| 369 | 21919 | 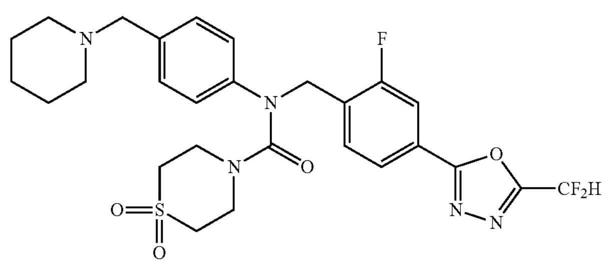 [SMILES: O=C(N1CCS(=O)(=O)CC1)N(Cc1ccc(-c2nnc(C(F)F)o2)cc1F)c1ccc(CN2CCCCC2)cc1] |

| Ex. | Comp. | Structure |
|---|---|---|
| 370 | 21924 | 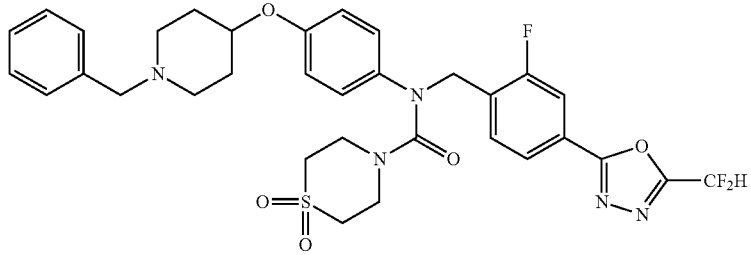 [SMILES: O=C(N1CCS(=O)(=O)CC1)N(Cc1ccc(-c2nnc(C(F)F)o2)cc1F)c1ccc(OC2CCN(Cc3ccccc3)CC2)cc1] |
| 371 | 21925 | 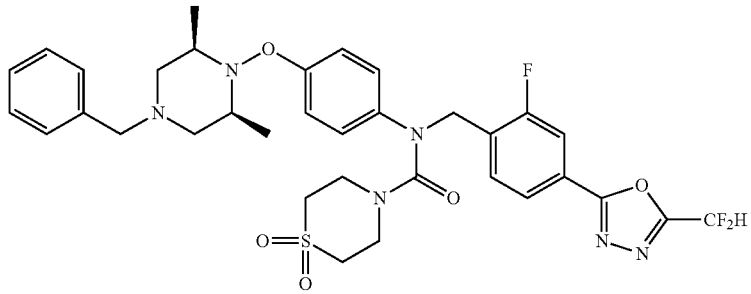 |
| 372 | 21926 | 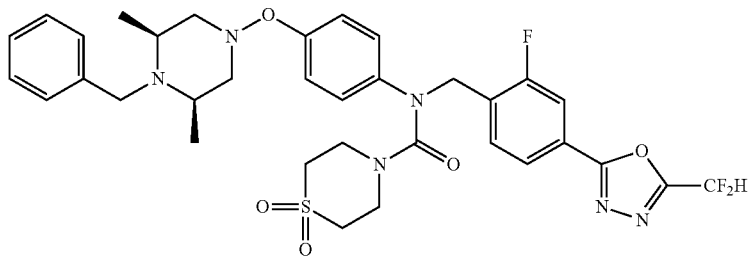 [SMILES: C[C@@H]1CN(Oc2ccc(N(Cc3ccc(-c4nnc(C(F)F)o4)cc3F)C(=O)N3CCS(=O)(=O)CC3)cc2)C[C@H](C)N1Cc1ccccc1] |
| 373 | 21929 | 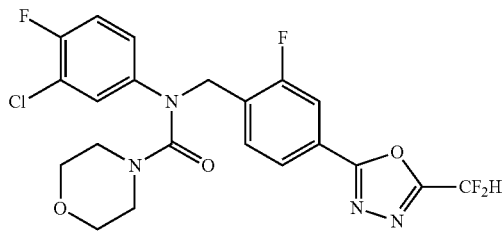 [SMILES: O=C(N1CCOCC1)N(Cc1ccc(-c2nnc(C(F)F)o2)cc1F)c1ccc(F)c(Cl)c1] |
| 374 | 21930 | 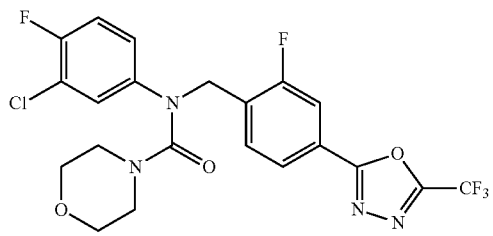 [SMILES: O=C(N1CCOCC1)N(Cc1ccc(-c2nnc(C(F)(F)F)o2)cc1F)c1ccc(F)c(Cl)c1] |
| 375 | 21931 | 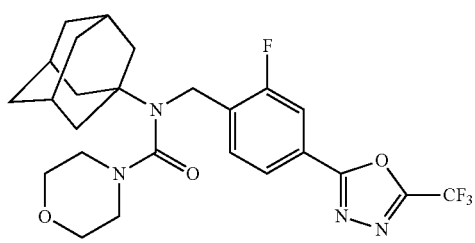 [SMILES: O=C(N1CCOCC1)N(Cc1ccc(-c2nnc(C(F)(F)F)o2)cc1F)C12CC3CC(CC(C3)C1)C2] |

-continued
| Ex. | Comp. | Structure |
|---|---|---|
| 376 | 21932 | 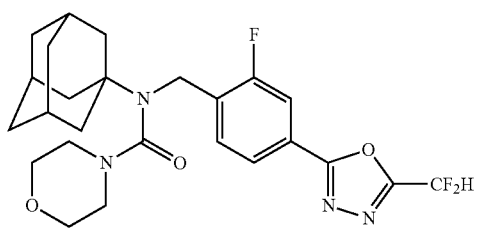 [SMILES: O=C(N1CCOCC1)N(Cc1ccc(-c2nnc(C(F)F)o2)cc1F)C12CC3CC(CC(C3)C1)C2] |
| 377 | 21933 | 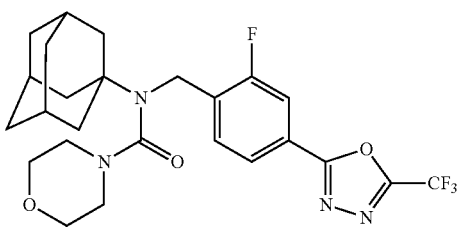 [SMILES: O=C(N1CCOCC1)N(Cc1ccc(-c2nnc(C(F)(F)F)o2)cc1F)C12CC3CC(CC(C3)C1)C2] |
| 378 | 21934 | 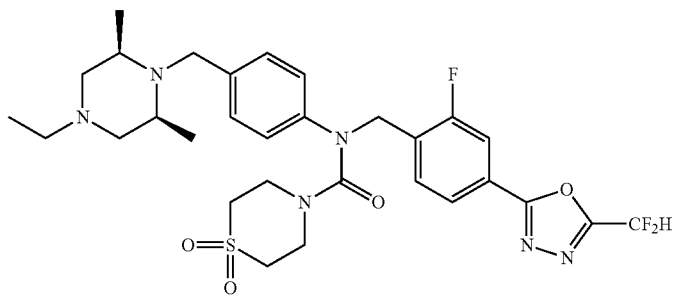 [SMILES: CCN1C[C@@H](C)N(Cc2ccc(N(Cc3ccc(-c4nnc(C(F)F)o4)cc3F)C(=O)N3CCS(=O)(=O)CC3)cc2)[C@@H](C)C1] |
| 379 | 21935 | 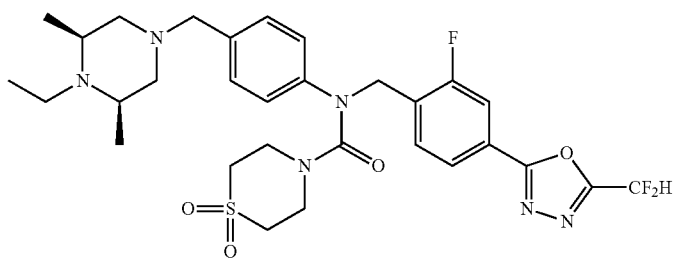 [SMILES: CCN1[C@H](C)CN(Cc2ccc(N(Cc3ccc(-c4nnc(C(F)F)o4)cc3F)C(=O)N3CCS(=O)(=O)CC3)cc2)C[C@@H]1C] |
| 380 | 21936 | 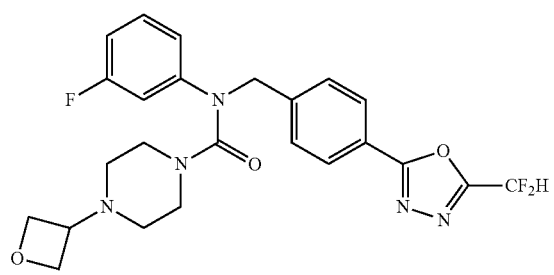 [SMILES: O=C(N1CCN(C2COC2)CC1)N(Cc1ccc(-c2nnc(C(F)F)o2)cc1)c1cccc(F)c1] |
| 381 | 21937 | 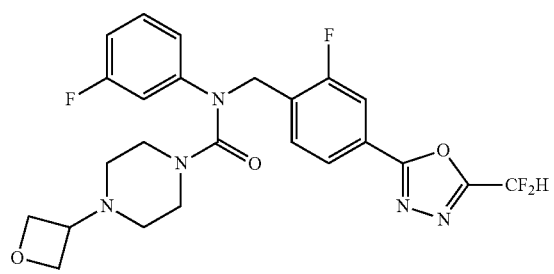 |

| Ex. | Comp. | Structure |
|---|---|---|
| 382 | 21938 | 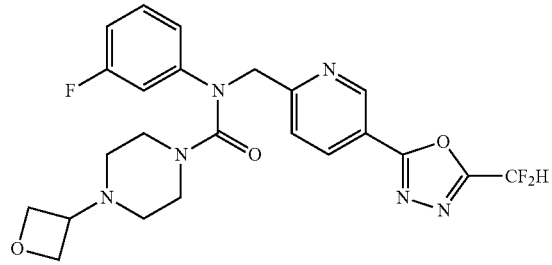 [SMILES: O=C(N1CCN(C2COC2)CC1)N(Cc1ccc(-c2nnc(C(F)F)o2)cn1)c1cccc(F)c1] |
| 383 | 21939 | 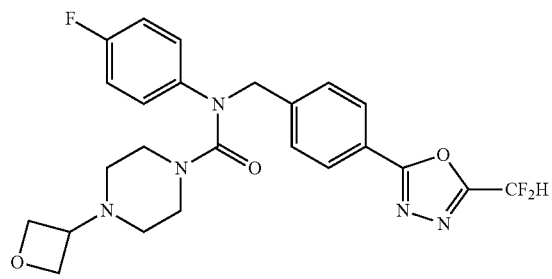 [SMILES: O=C(N1CCN(C2COC2)CC1)N(Cc1ccc(-c2nnc(C(F)F)o2)cc1)c1ccc(F)cc1] |
| 384 | 21940 | 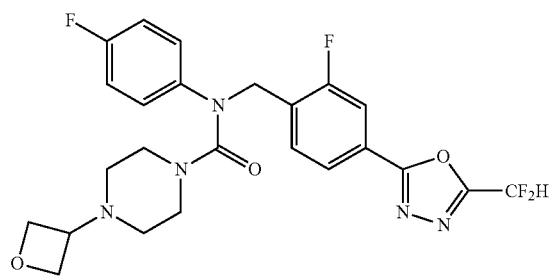 |
| 385 | 21941 | 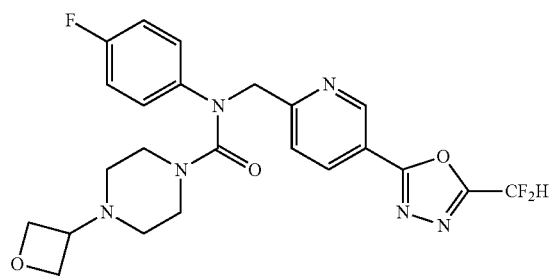 |
| 386 | 21942 | 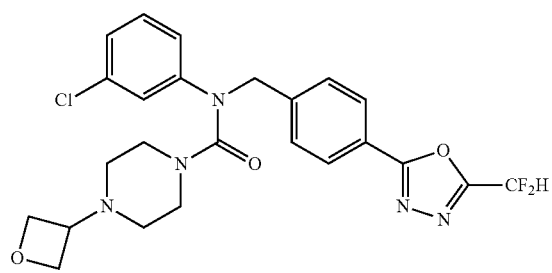 |

-continued
| Ex. | Comp. | Structure |
|---|---|---|
| 387 | 21943 | 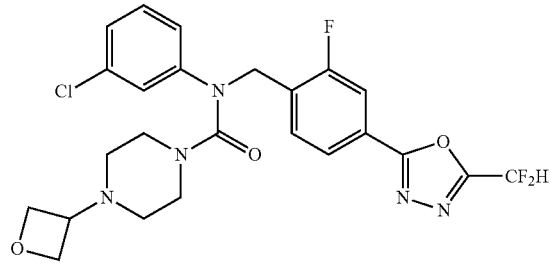 [SMILES: O=C(N1CCN(C2COC2)CC1)N(Cc1ccc(-c2nnc(C(F)F)o2)cc1F)c1cccc(Cl)c1] |
| 388 | 21944 | 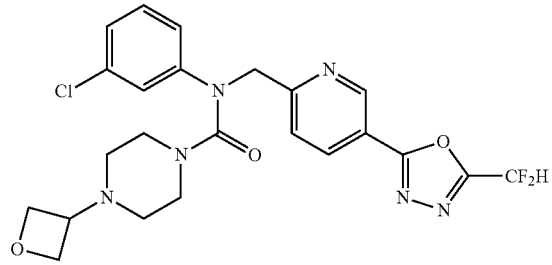 |
| 389 | 21945 | 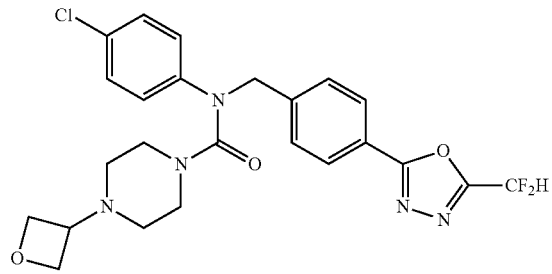 [SMILES: O=C(N1CCN(C2COC2)CC1)N(Cc1ccc(-c2nnc(C(F)F)o2)cc1)c1ccc(Cl)cc1] |
| 390 | 21946 | 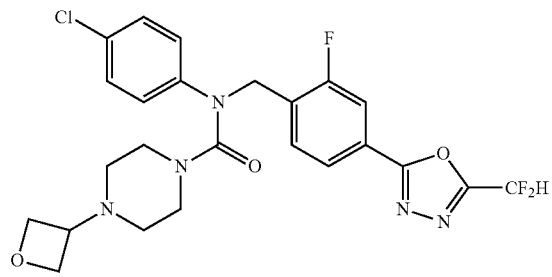 |
| 391 | 21947 | 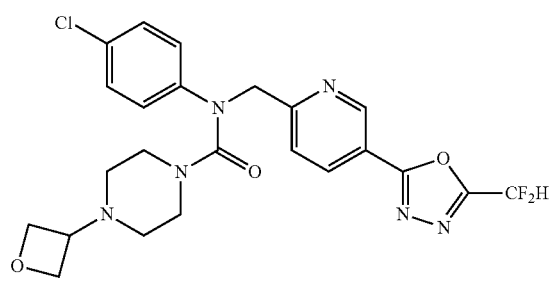 |

| Ex. | Comp. | Structure |
|---|---|---|
| 392 | 21948 | 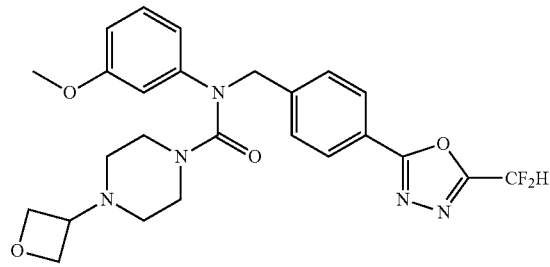 [SMILES: COc1cccc(N(Cc2ccc(-c3nnc(C(F)F)o3)cc2)C(=O)N2CCN(C3COC3)CC2)c1] |
| 393 | 21949 | 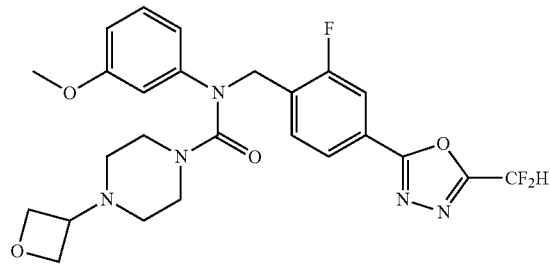 [SMILES: COc1cccc(N(Cc2ccc(-c3nnc(C(F)F)o3)cc2F)C(=O)N2CCN(C3COC3)CC2)c1] |
| 394 | 21950 | 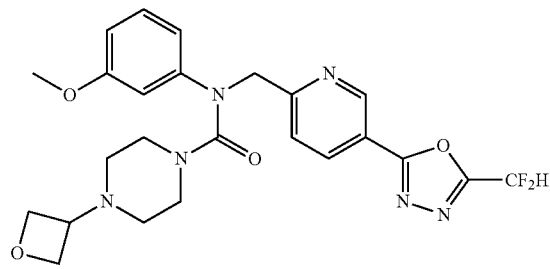 [SMILES: COc1cccc(N(Cc2ccc(-c3nnc(C(F)F)o3)cn2)C(=O)N2CCN(C3COC3)CC2)c1] |
| 395 | 21951 | 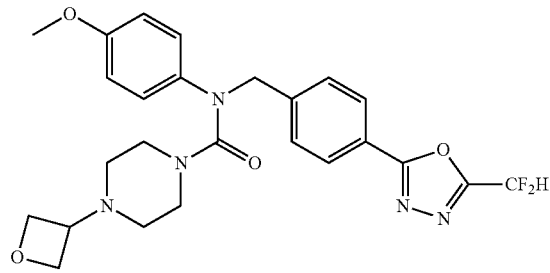 [SMILES: COc1ccc(N(Cc2ccc(-c3nnc(C(F)F)o3)cc2)C(=O)N2CCN(C3COC3)CC2)cc1] |
| 396 | 21952 | 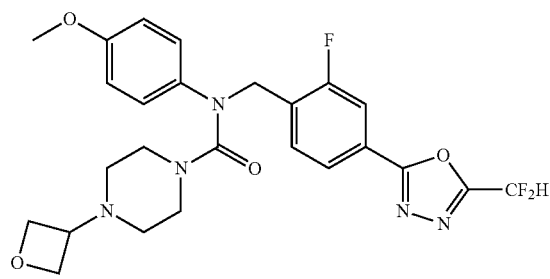 [SMILES: COc1ccc(N(Cc2ccc(-c3nnc(C(F)F)o3)cc2F)C(=O)N2CCN(C3COC3)CC2)cc1] |

| Ex. | Comp. | Structure |
|---|---|---|
| 397 | 21953 | 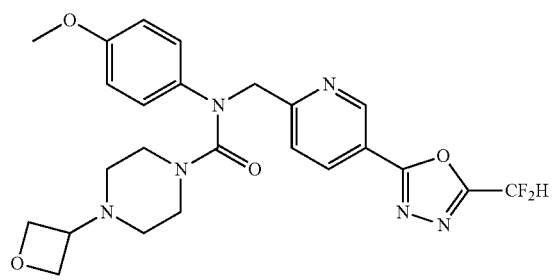 [SMILES: COc1ccc(N(Cc2ccc(-c3nnc(C(F)F)o3)cn2)C(=O)N2CCN(C3COC3)CC2)cc1] |
| 398 | 21954 | 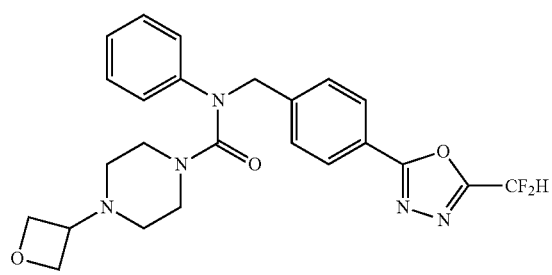 [SMILES: O=C(N1CCN(C2COC2)CC1)N(Cc1ccc(-c2nnc(C(F)F)o2)cc1)c1ccccc1] |
| 399 | 21955 | 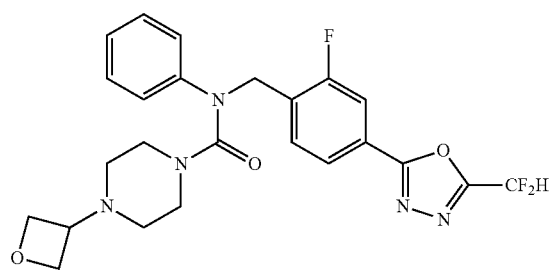 [SMILES: O=C(N1CCN(C2COC2)CC1)N(Cc1ccc(-c2nnc(C(F)F)o2)cc1F)c1ccccc1] |
| 400 | 21956 | 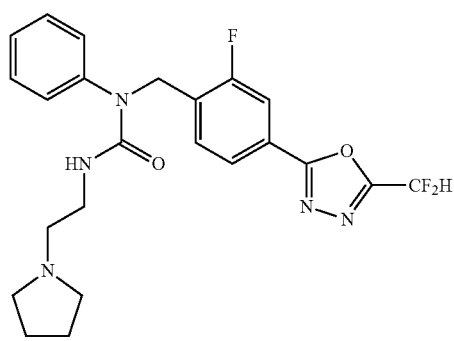 [SMILES: O=C(NCCN1CCCC1)N(Cc1ccc(-c2nnc(C(F)F)o2)cc1F)c1ccccc1] |
| 401 | 21957 | 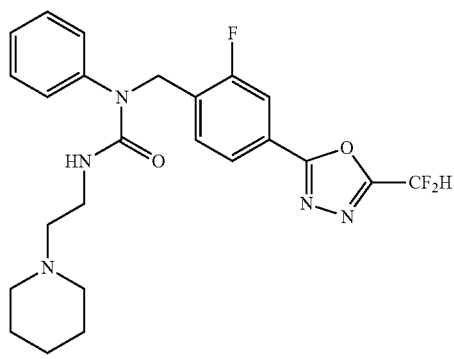 [SMILES: O=C(NCCN1CCCCC1)N(Cc1ccc(-c2nnc(C(F)F)o2)cc1F)c1ccccc1] |

-continued

| Ex. | Comp. | Structure |
|---|---|---|
| 402 | 21958 | 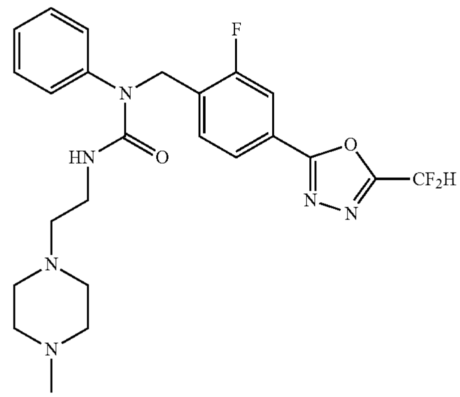 [SMILES: CN1CCN(CCNC(=O)N(Cc2ccc(-c3nnc(C(F)F)o3)cc2F)c2ccccc2)CC1] |
| 403 | 21970 | 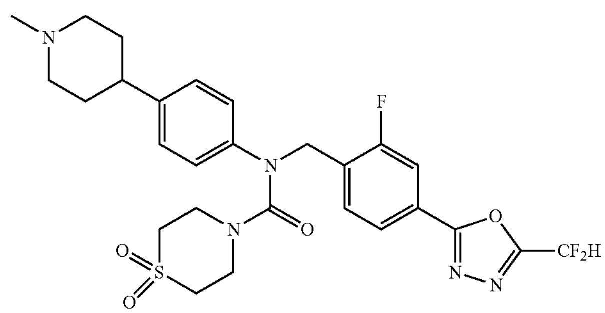 [SMILES: CN1CCC(c2ccc(N(Cc3ccc(-c4nnc(C(F)F)o4)cc3F)C(=O)N3CCS(=O)(=O)CC3)cc2)CC1] |
| 404 | 21971 | 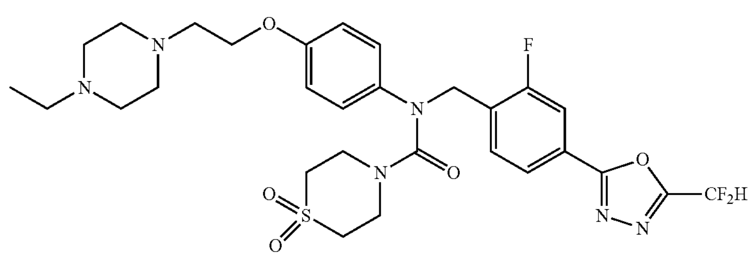 [SMILES: CCN1CCN(CCOc2ccc(N(Cc3ccc(-c4nnc(C(F)F)o4)cc3F)C(=O)N3CCS(=O)(=O)CC3)cc2)CC1] |
| 405 | 21972 | 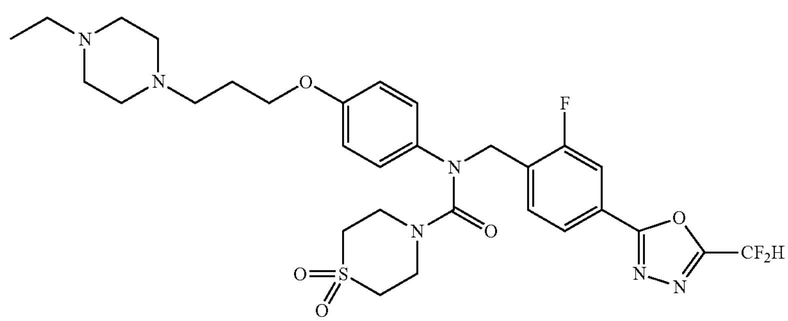 [SMILES: CCN1CCN(CCCOc2ccc(N(Cc3ccc(-c4nnc(C(F)F)o4)cc3F)C(=O)N3CCS(=O)(=O)CC3)cc2)CC1] |
| 406 | 21973 | 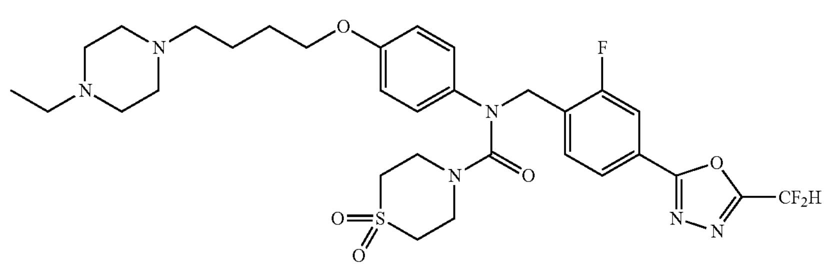 [SMILES: CCN1CCN(CCCCOc2ccc(N(Cc3ccc(-c4nnc(C(F)F)o4)cc3F)C(=O)N3CCS(=O)(=O)CC3)cc2)CC1] |

| Ex. | Comp. | Structure |
|---|---|---|
| 407 | 21979 | 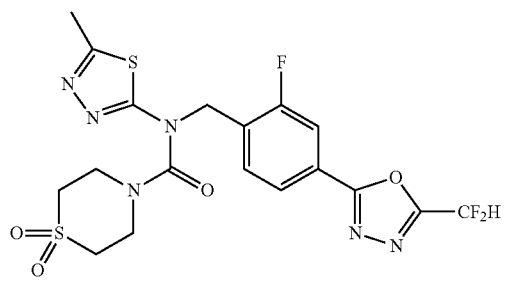 [SMILES: Cc1nnc(N(Cc2ccc(-c3nnc(C(F)F)o3)cc2F)C(=O)N2CCS(=O)(=O)CC2)s1] |
| 408 | 21980 | 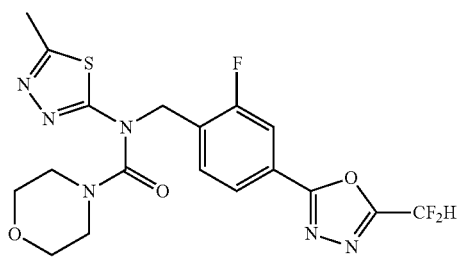 [SMILES: Cc1nnc(N(Cc2ccc(-c3nnc(C(F)F)o3)cc2F)C(=O)N2CCOCC2)s1] |
| 409 | 21981 | 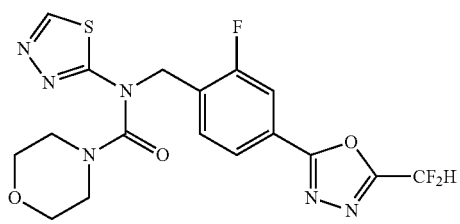 |
| 410 | 21982 | 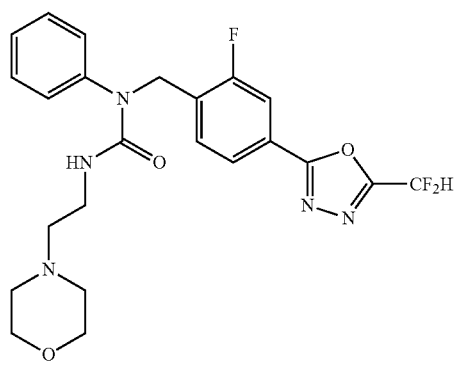 [SMILES: O=C(NCCN1CCOCC1)N(Cc1ccc(-c2nnc(C(F)F)o2)cc1F)c1ccccc1] |
| 411 | 21983 | 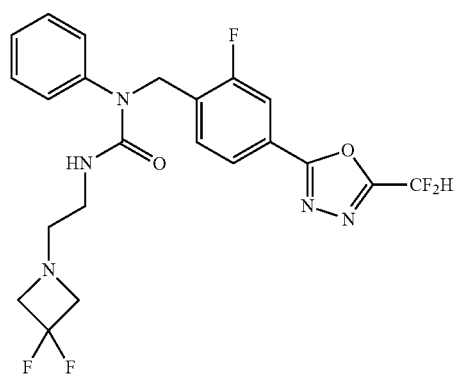 [SMILES: O=C(NCCN1CC(F)(F)C1)N(Cc1ccc(-c2nnc(C(F)F)o2)cc1F)c1ccccc1] |

| Ex. | Comp. | Structure |
|---|---|---|
| 412 | 21984 | Ph-N(CH₂-[2-F,4-(5-CF₂H-1,3,4-oxadiazol-2-yl)phenyl])-C(O)NH-CH₂CH₂-N(piperazine)-CH₂-C(O)-N(morpholine) |
| 413 | 21985 | Ph-N(CH₂-[2-F,4-(5-CF₂H-1,3,4-oxadiazol-2-yl)phenyl])-C(O)NH-CH₂CH₂-N(thiomorpholine-1,1-dioxide) |
| 414 | 21986 | Ph-N(CH₂-[2-F,4-(5-CF₂H-1,3,4-oxadiazol-2-yl)phenyl])-C(O)NH-CH₂CH₂-N(1,4-oxazepane) |
| 415 | 21987 | Ph-N(CH₂-[2-F,4-(5-CF₂H-1,3,4-oxadiazol-2-yl)phenyl])-C(O)NH-CH₂CH₂-N[(2S)-2-(CF₃)pyrrolidin-1-yl] |

| Ex. | Comp. | Structure |
|---|---|---|
| 416 | 21988 | 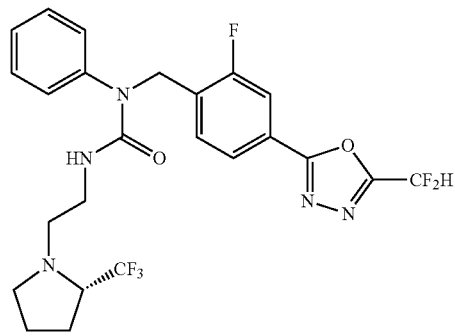 [SMILES: O=C(NCCN1CCC[C@H]1C(F)(F)F)N(Cc1ccc(-c2nnc(C(F)F)o2)cc1F)c1ccccc1] |
| 417 | 21989 | 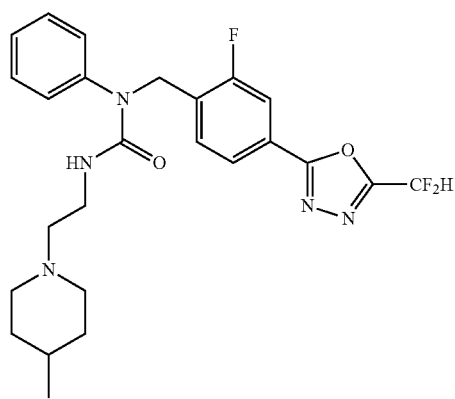 |
| 418 | 21990 | 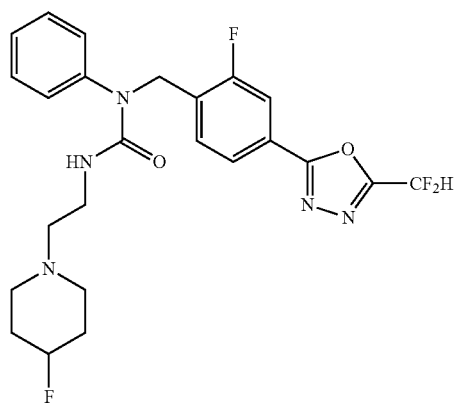 [SMILES: O=C(NCCN1CCC(F)CC1)N(Cc1ccc(-c2nnc(C(F)F)o2)cc1F)c1ccccc1] |
| 419 | 21991 | 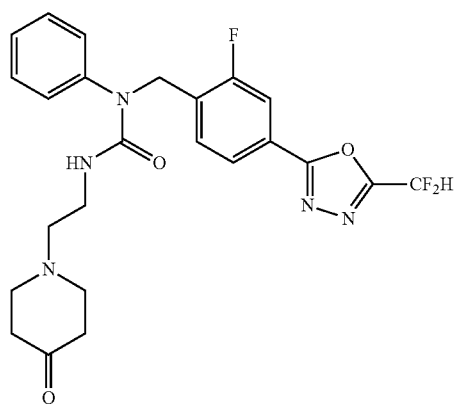 [SMILES: O=C1CCN(CCNC(=O)N(Cc2ccc(-c3nnc(C(F)F)o3)cc2F)c2ccccc2)CC1] |

| Ex. | Comp. | Structure |
|---|---|---|
| 420 | 21992 | *(structure shown)* |
| 421 | 21993 | *(structure shown)* |
| 422 | 21994 | *(structure shown)* |
| 423 | 21995 | *(structure shown)* |

| Ex. | Comp. | Structure |
|---|---|---|
| 424 | 21996 | 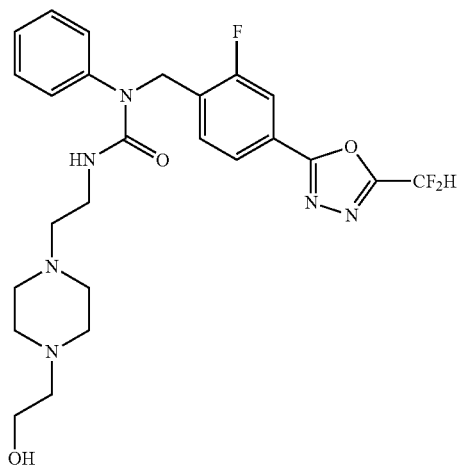 [SMILES: O=C(NCCN1CCN(CCO)CC1)N(Cc1ccc(-c2nnc(C(F)F)o2)cc1F)c1ccccc1] |
| 425 | 21997 | 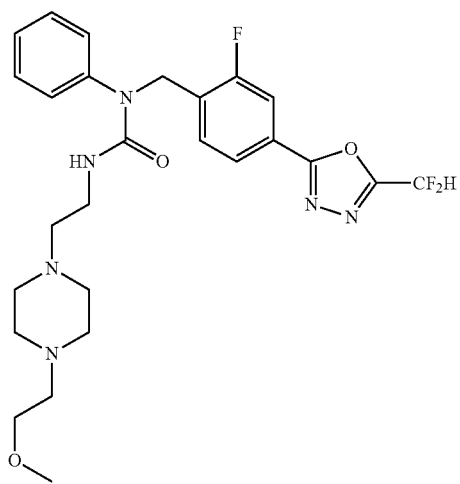 [SMILES: COCCN1CCN(CCNC(=O)N(Cc2ccc(-c3nnc(C(F)F)o3)cc2F)c2ccccc2)CC1] |
| 426 | 21998 | 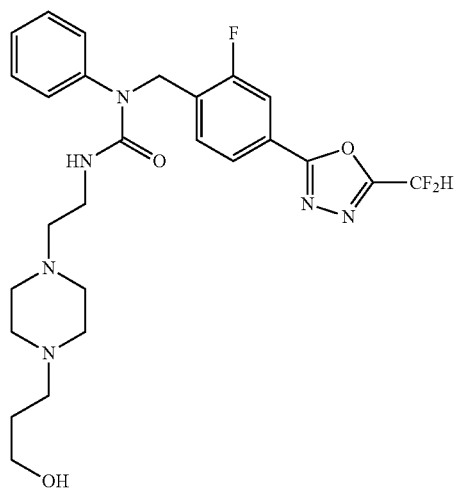 [SMILES: O=C(NCCN1CCN(CCCO)CC1)N(Cc1ccc(-c2nnc(C(F)F)o2)cc1F)c1ccccc1] |

| Ex. | Comp. | Structure |
|---|---|---|
| 427 | 21999 | 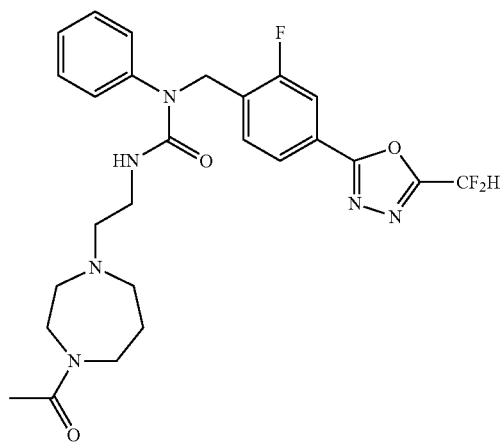 [SMILES: CC(=O)N1CCCN(CCNC(=O)N(Cc2ccc(-c3nnc(C(F)F)o3)cc2F)c2ccccc2)CC1] |
| 428 | 22000 | 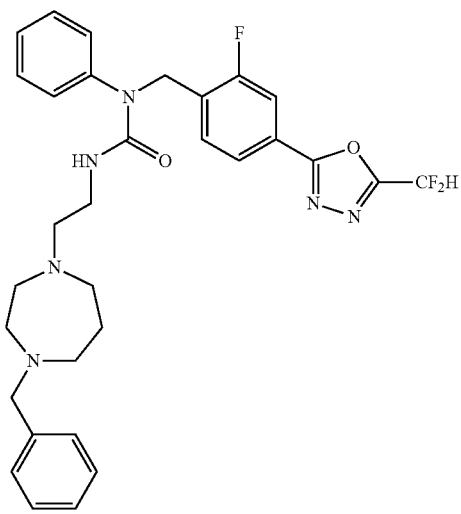 [SMILES: O=C(NCCN1CCCN(Cc2ccccc2)CC1)N(Cc1ccc(-c2nnc(C(F)F)o2)cc1F)c1ccccc1] |
| 429 | 22001 | 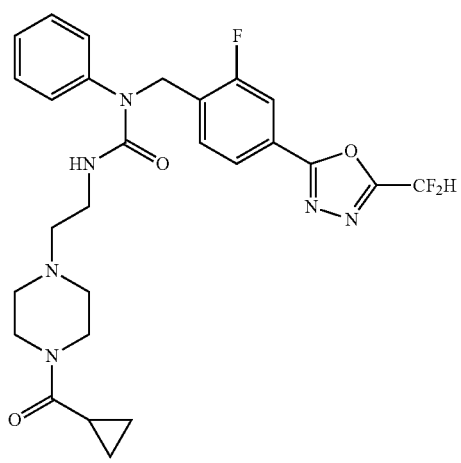 [SMILES: O=C(C1CC1)N1CCN(CCNC(=O)N(Cc2ccc(-c3nnc(C(F)F)o3)cc2F)c2ccccc2)CC1] |

| Ex. | Comp. | Structure |
|---|---|---|
| 430 | 22002 | 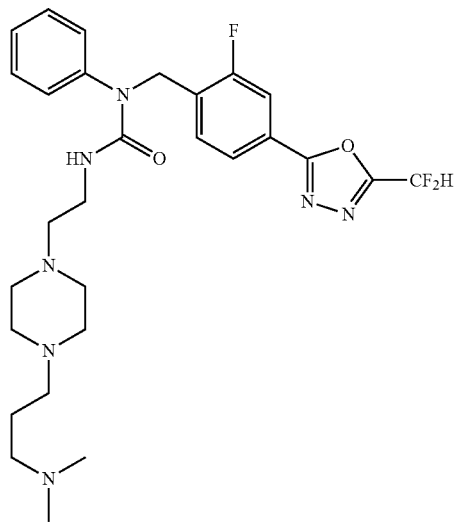 [SMILES: CN(C)CCCN1CCN(CCNC(=O)N(Cc2ccc(-c3nnc(C(F)F)o3)cc2F)c2ccccc2)CC1] |
| 431 | 22003 | 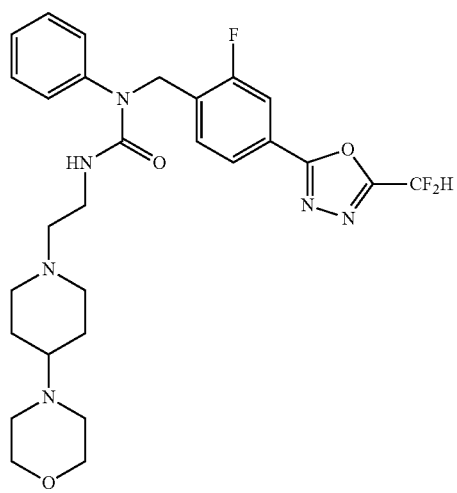 [SMILES: O=C(NCCN1CCC(N2CCOCC2)CC1)N(Cc1ccc(-c2nnc(C(F)F)o2)cc1F)c1ccccc1] |
| 432 | 22004 | 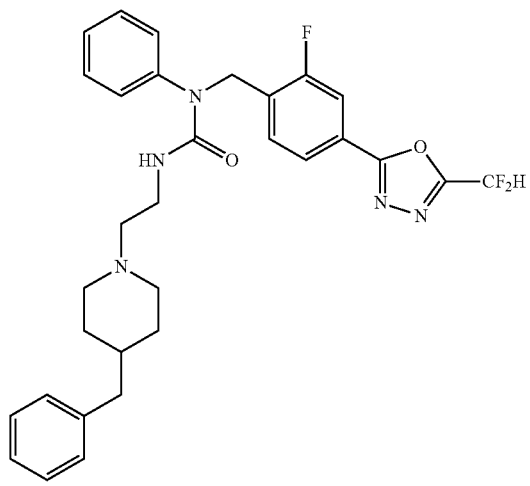 |

| Ex. | Comp. | Structure |
|---|---|---|
| 433 | 22005 | 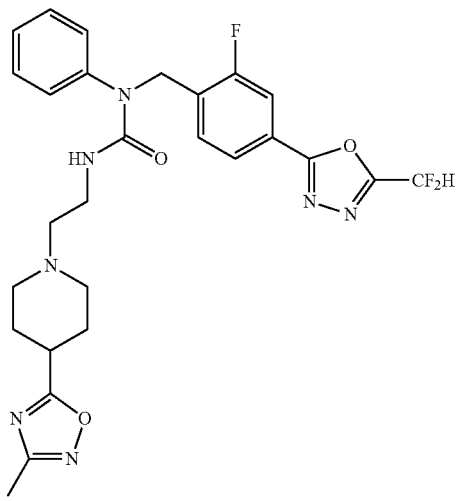 [SMILES: Cc1noc(C2CCN(CCNC(=O)N(Cc3ccc(-c4nnc(C(F)F)o4)cc3F)c3ccccc3)CC2)n1] |
| 434 | 22006 | 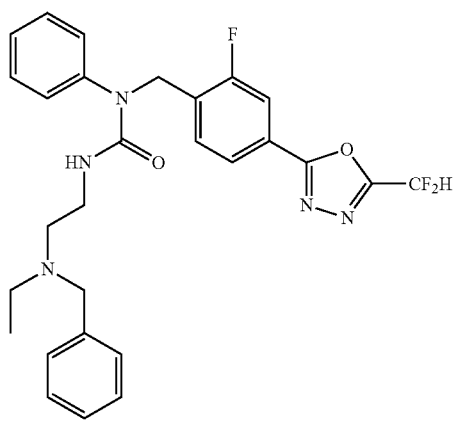 [SMILES: CCN(CCNC(=O)N(Cc1ccc(-c2nnc(C(F)F)o2)cc1F)c1ccccc1)Cc1ccccc1] |
| 435 | 22007 | 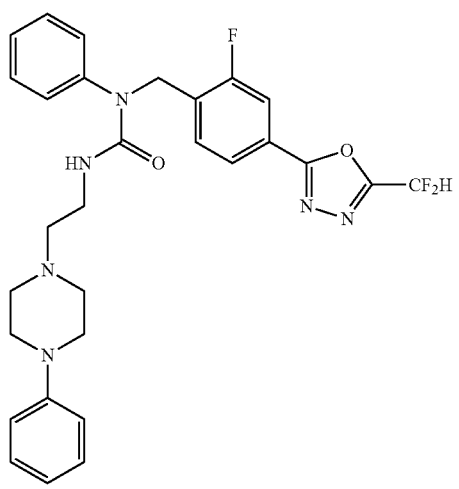 [SMILES: O=C(NCCN1CCN(c2ccccc2)CC1)N(Cc1ccc(-c2nnc(C(F)F)o2)cc1F)c1ccccc1] |

| Ex. | Comp. | Structure |
|---|---|---|
| 436 | 22008 | 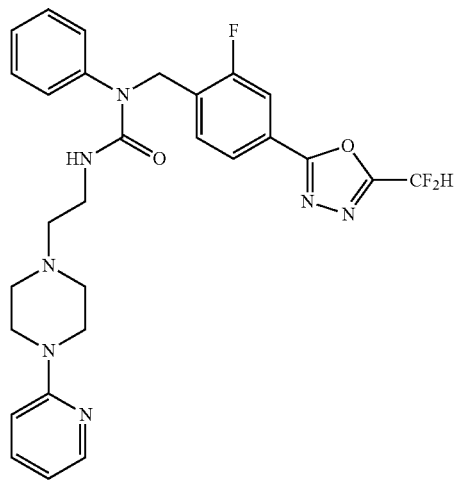 [SMILES: O=C(NCCN1CCN(c2ccccn2)CC1)N(Cc1ccc(-c2nnc(C(F)F)o2)cc1F)c1ccccc1] |
| 437 | 22009 | 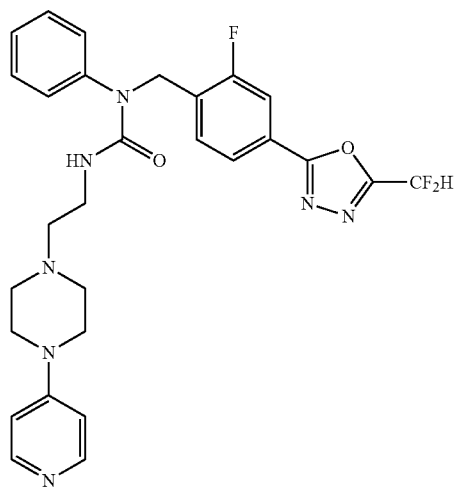 [SMILES: O=C(NCCN1CCN(c2ccncc2)CC1)N(Cc1ccc(-c2nnc(C(F)F)o2)cc1F)c1ccccc1] |
| 438 | 22010 | 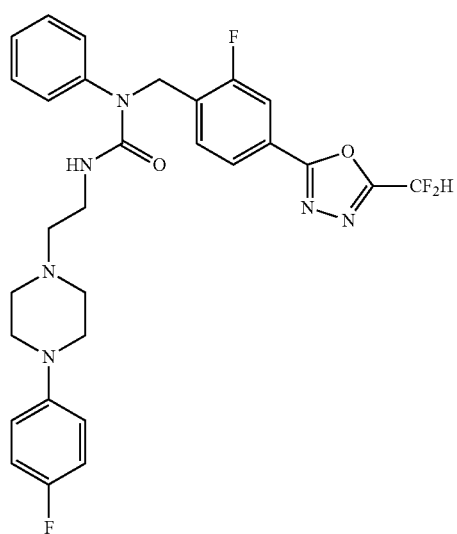 [SMILES: O=C(NCCN1CCN(c2ccc(F)cc2)CC1)N(Cc1ccc(-c2nnc(C(F)F)o2)cc1F)c1ccccc1] |

-continued
| Ex. | Comp. | Structure |
|---|---|---|
| 439 | 22011 | 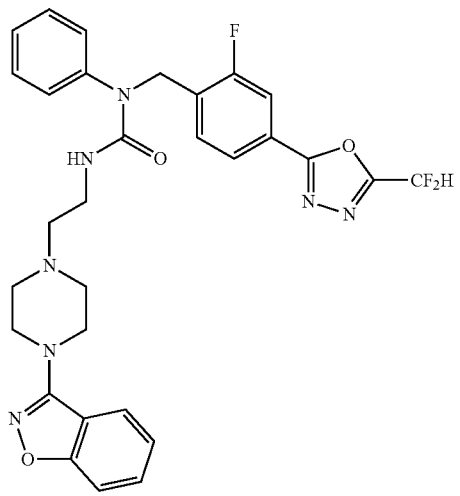 [SMILES: O=C(NCCN1CCN(c2noc3ccccc23)CC1)N(Cc1ccc(-c2nnc(C(F)F)o2)cc1F)c1ccccc1] |
| 440 | 22012 | 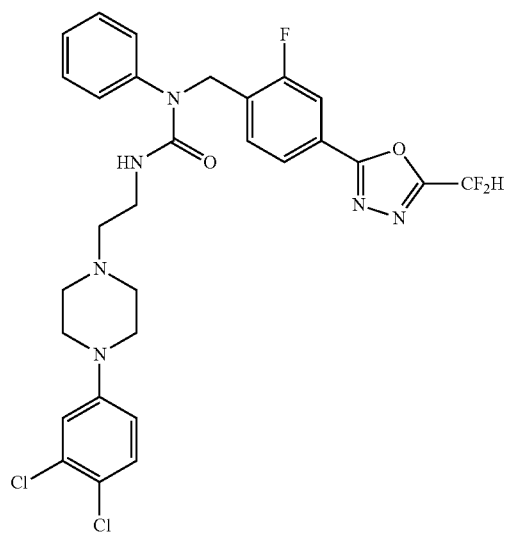 [SMILES: O=C(NCCN1CCN(c2ccc(Cl)c(Cl)c2)CC1)N(Cc1ccc(-c2nnc(C(F)F)o2)cc1F)c1ccccc1] |
| 441 | 22013 | 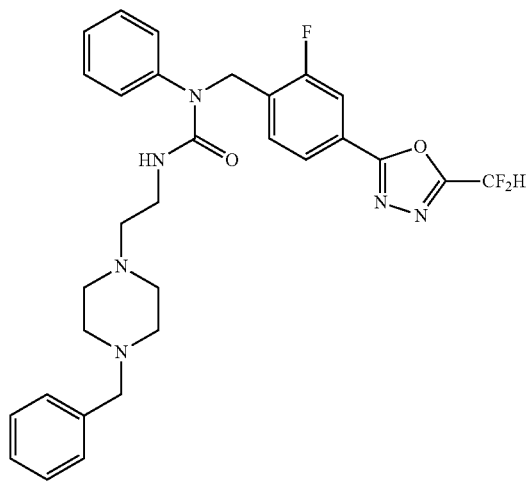 |

| Ex. | Comp. | Structure |
|---|---|---|
| 442 | 22014 | 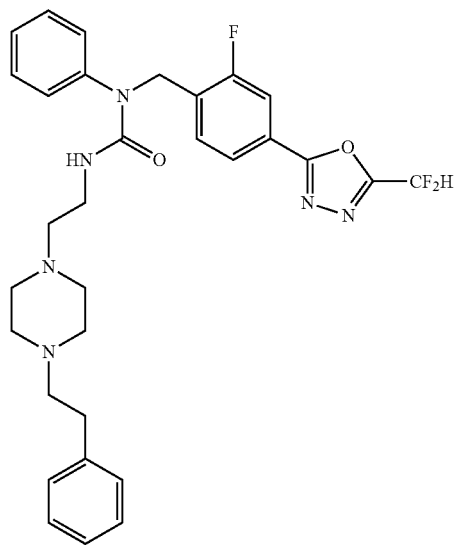 [SMILES: O=C(NCCN1CCN(CCc2ccccc2)CC1)N(Cc1ccc(-c2nnc(C(F)F)o2)cc1F)c1ccccc1] |
| 443 | 22015 | 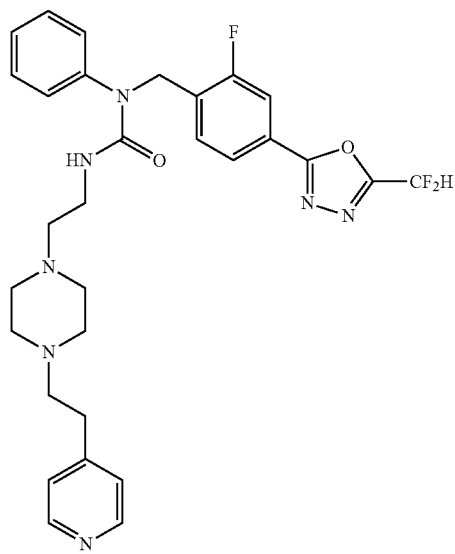 [SMILES: O=C(NCCN1CCN(CCc2ccncc2)CC1)N(Cc1ccc(-c2nnc(C(F)F)o2)cc1F)c1ccccc1] |

| Ex. | Comp. | Structure |
|---|---|---|
| 444 | 22016 | 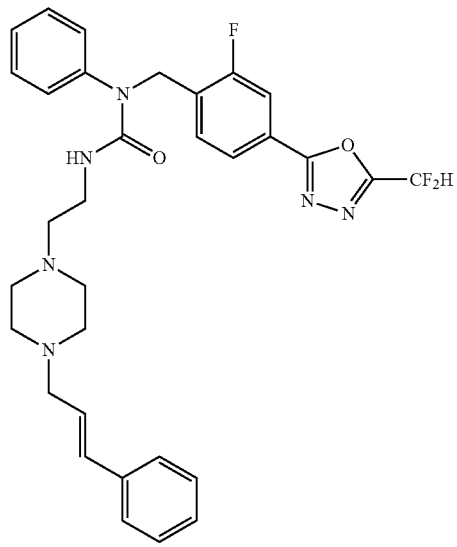 [SMILES: O=C(NCCN1CCN(C/C=C/c2ccccc2)CC1)N(Cc1ccc(-c2nnc(C(F)F)o2)cc1F)c1ccccc1] |
| 445 | 22017 | 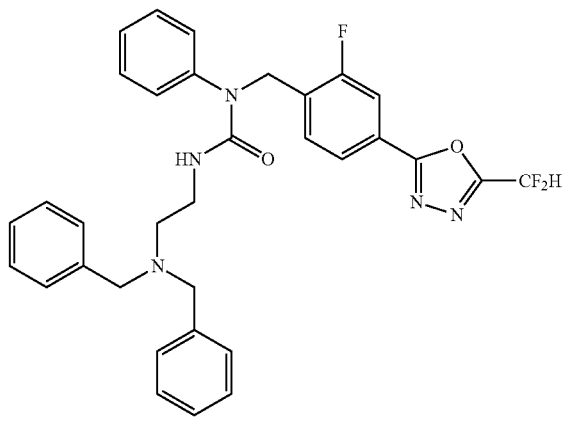 [SMILES: O=C(NCCN(Cc1ccccc1)Cc1ccccc1)N(Cc1ccc(-c2nnc(C(F)F)o2)cc1F)c1ccccc1] |
| 446 | 22018 | 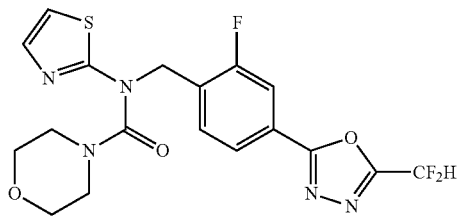 [SMILES: O=C(N1CCOCC1)N(Cc1ccc(-c2nnc(C(F)F)o2)cc1F)c1nccs1] |
| 447 | 22019 | 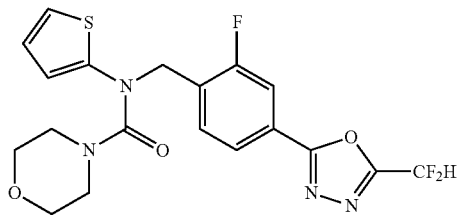 [SMILES: O=C(N1CCOCC1)N(Cc1ccc(-c2nnc(C(F)F)o2)cc1F)c1cccs1] |

-continued
| Ex. | Comp. | Structure |
|---|---|---|
| 448 | 22020 | 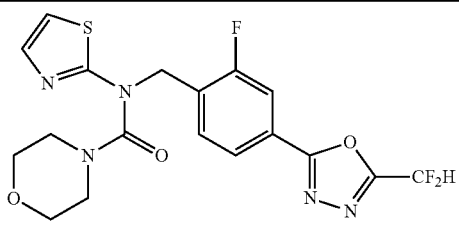 |
| 449 | 22021 | 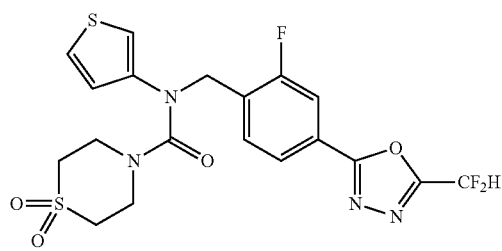 [SMILES: O=C(N1CCS(=O)(=O)CC1)N(Cc1ccc(-c2nnc(C(F)F)o2)cc1F)c1ccsc1] |
| 450 | 22024 | 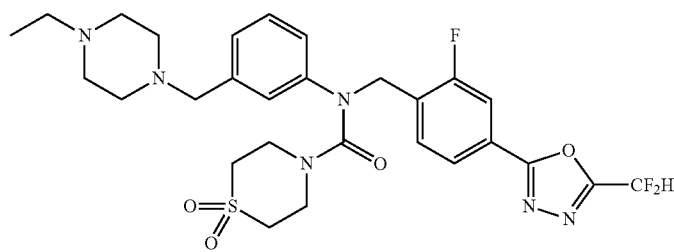 [SMILES: CCN1CCN(Cc2cccc(N(Cc3ccc(-c4nnc(C(F)F)o4)cc3F)C(=O)N3CCS(=O)(=O)CC3)c2)CC1] |
6. The 1,3,4-oxadiazole derivative compound represented by formula I, stereoisomer thereof or pharmaceutically acceptable salt thereof according to claim 1, wherein the compound represented by formula I is selected from the group consisting of compounds described in the following table:
| Ex. | Comp. | Structure |
|---|---|---|
| 5 | 21325 | 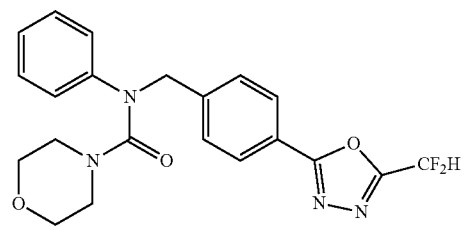 [SMILES: O=C(N1CCOCC1)N(Cc1ccc(-c2nnc(C(F)F)o2)cc1)c1ccccc1] |
| 10 | 21337 | 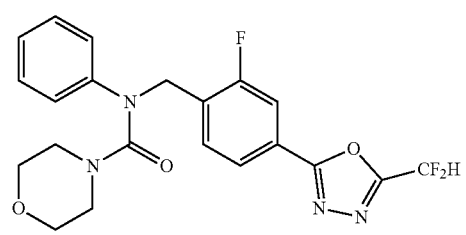 [SMILES: O=C(N1CCOCC1)N(Cc1ccc(-c2nnc(C(F)F)o2)cc1F)c1ccccc1] |

| Ex. | Comp. | Structure |
|---|---|---|
| 30 | 21360 | 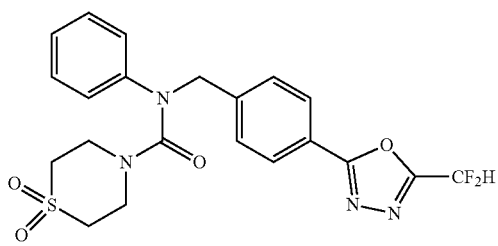 [SMILES: O=C(N1CCS(=O)(=O)CC1)N(Cc1ccc(-c2nnc(C(F)F)o2)cc1)c1ccccc1] |
| 40 | 21370 | 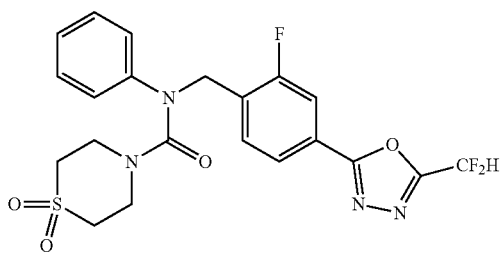 [SMILES: O=C(N1CCS(=O)(=O)CC1)N(Cc1ccc(-c2nnc(C(F)F)o2)cc1F)c1ccccc1] |
| 43 | 21373 | 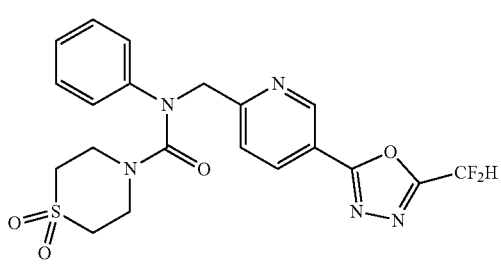 [SMILES: O=C(N1CCS(=O)(=O)CC1)N(Cc1ccc(-c2nnc(C(F)F)o2)cn1)c1ccccc1] |
| 48 | 21378 | 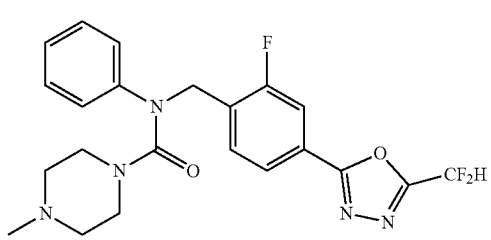 [SMILES: CN1CCN(C(=O)N(Cc2ccc(-c3nnc(C(F)F)o3)cc2F)c2ccccc2)CC1] |
| 53 | 21383 | 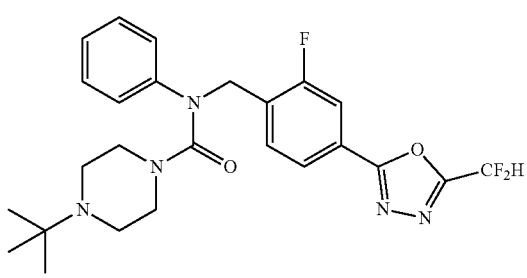 [SMILES: CC(C)(C)N1CCN(C(=O)N(Cc2ccc(-c3nnc(C(F)F)o3)cc2F)c2ccccc2)CC1] |
| 56 | 21386 | 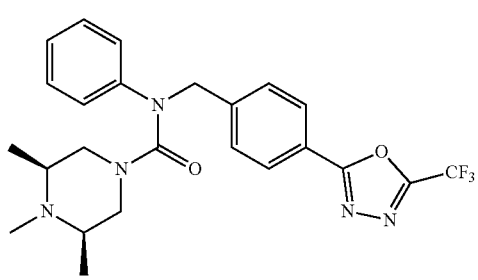 [SMILES: C[C@@H]1CN(C(=O)N(Cc2ccc(-c3nnc(C(F)(F)F)o3)cc2)c2ccccc2)C[C@H](C)N1C] |

| Ex. | Comp. | Structure |
|---|---|---|
| 93 | 21423 | 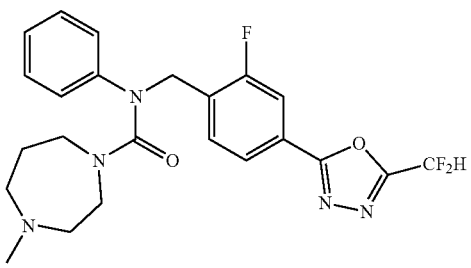 [SMILES: CN1CCCN(C(=O)N(Cc2ccc(-c3nnc(C(F)F)o3)cc2F)c2ccccc2)CC1] |
| 101 | 21432 | 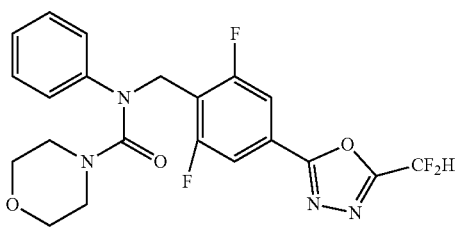 [SMILES: O=C(N1CCOCC1)N(Cc1c(F)cc(-c2nnc(C(F)F)o2)cc1F)c1ccccc1] |
| 117 | 21448 | 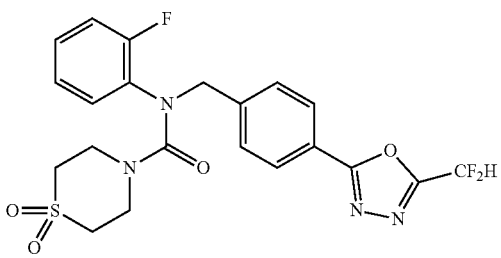 [SMILES: O=C(N1CCS(=O)(=O)CC1)N(Cc1ccc(-c2nnc(C(F)F)o2)cc1)c1ccccc1F] |
| 124 | 21455 | 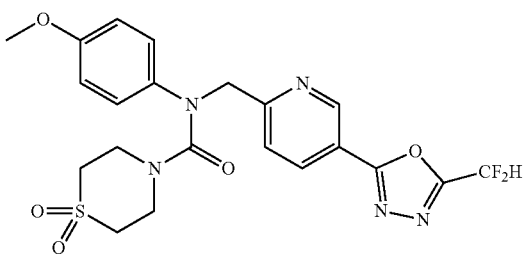 [SMILES: COc1ccc(N(Cc2ccc(-c3nnc(C(F)F)o3)cn2)C(=O)N2CCS(=O)(=O)CC2)cc1] |
| 134 | 21465 | 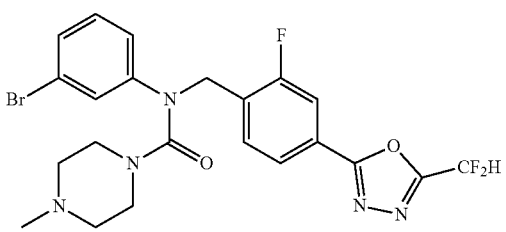 |
| 136 | 21467 | 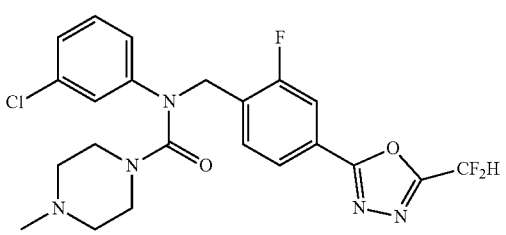 [SMILES: CN1CCN(C(=O)N(Cc2ccc(-c3nnc(C(F)F)o3)cc2F)c2cccc(Cl)c2)CC1] |

-continued
| Ex. | Comp. | Structure |
|---|---|---|
| 138 | 21469 | 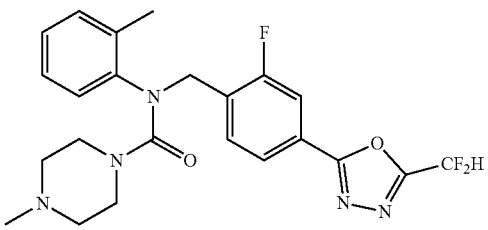 [SMILES: Cc1ccccc1N(Cc1ccc(-c2nnc(C(F)F)o2)cc1F)C(=O)N1CCN(C)CC1] |
| 139 | 21470 | 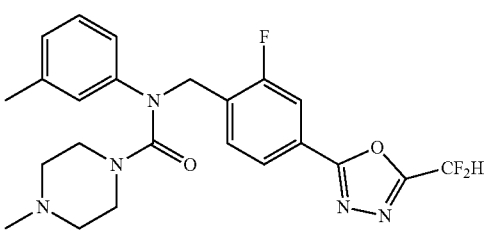 [SMILES: Cc1cccc(N(Cc2ccc(-c3nnc(C(F)F)o3)cc2F)C(=O)N2CCN(C)CC2)c1] |
| 140 | 21471 | 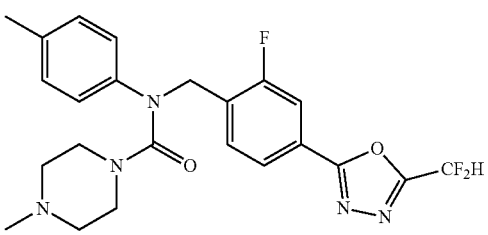 [SMILES: Cc1ccc(N(Cc2ccc(-c3nnc(C(F)F)o3)cc2F)C(=O)N2CCN(C)CC2)cc1] |
| 141 | 21472 | 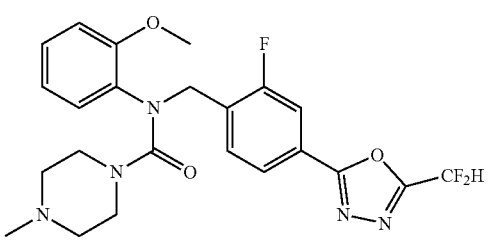 [SMILES: COc1ccccc1N(Cc1ccc(-c2nnc(C(F)F)o2)cc1F)C(=O)N1CCN(C)CC1] |
| 142 | 21473 | 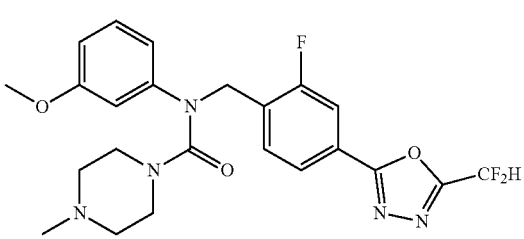 [SMILES: COc1cccc(N(Cc2ccc(-c3nnc(C(F)F)o3)cc2F)C(=O)N2CCN(C)CC2)c1] |
| 147 | 21478 | 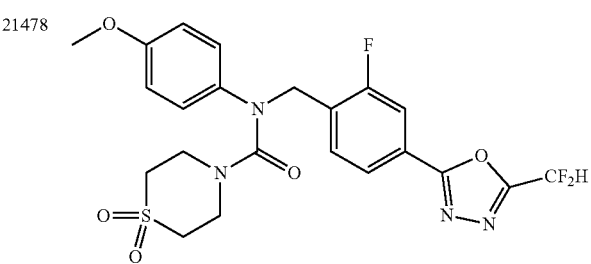 |

| Ex. | Comp. | Structure |
|---|---|---|
| 149 | 21480 | 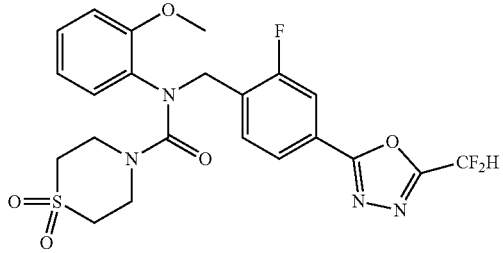 [SMILES: COc1ccccc1N(Cc1ccc(-c2nnc(C(F)F)o2)cc1F)C(=O)N1CCS(=O)(=O)CC1] |
| 151 | 21482 | 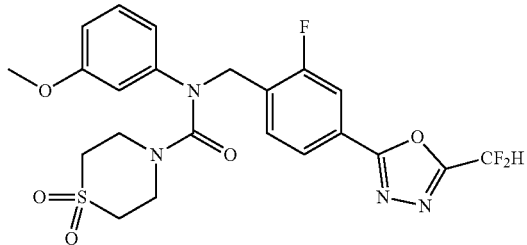 [SMILES: COc1cccc(N(Cc2ccc(-c3nnc(C(F)F)o3)cc2F)C(=O)N2CCS(=O)(=O)CC2)c1] |
| 153 | 21484 | 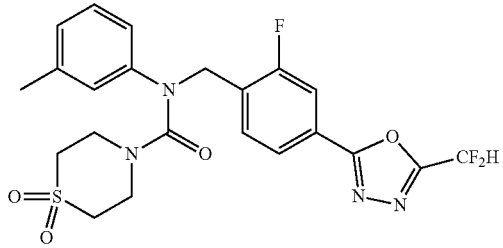 [SMILES: Cc1cccc(N(Cc2ccc(-c3nnc(C(F)F)o3)cc2F)C(=O)N2CCS(=O)(=O)CC2)c1] |
| 159 | 21490 | 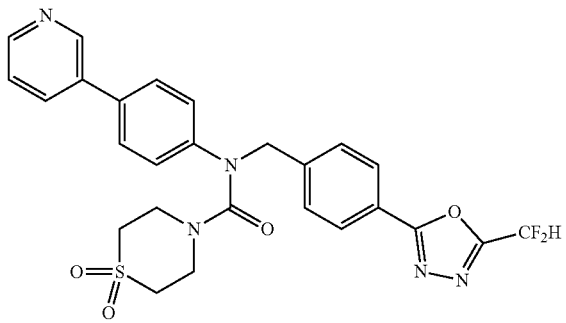 [SMILES: O=C(N1CCS(=O)(=O)CC1)N(Cc1ccc(-c2nnc(C(F)F)o2)cc1)c1ccc(-c2cccnc2)cc1] |
| 161 | 21492 | 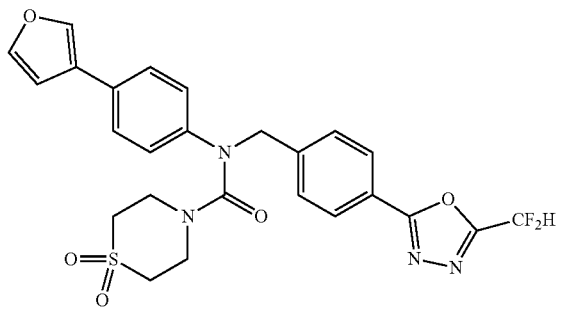 [SMILES: O=C(N1CCS(=O)(=O)CC1)N(Cc1ccc(-c2nnc(C(F)F)o2)cc1)c1ccc(-c2ccoc2)cc1] |

-continued
| Ex. | Comp. | Structure |
|---|---|---|
| 164 | 21495 | 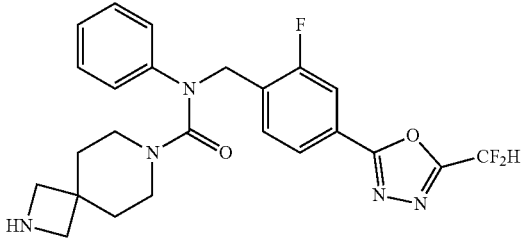 [SMILES: O=C(N1CCC2(CC1)CNC2)N(Cc1ccc(-c2nnc(C(F)F)o2)cc1F)c1ccccc1] |
| 165 | 21496 | 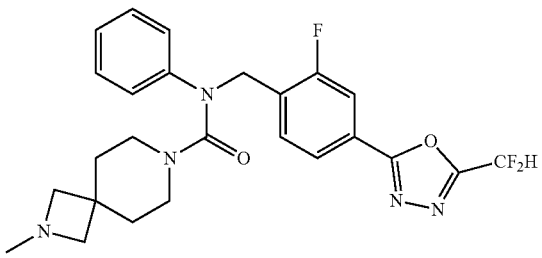 [SMILES: CN1CC2(CCN(C(=O)N(Cc3ccc(-c4nnc(C(F)F)o4)cc3F)c3ccccc3)CC2)C1] |
| 166 | 21497 | 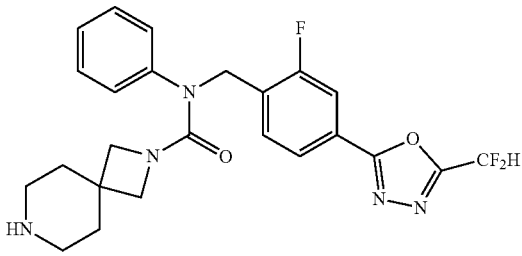 [SMILES: O=C(N1CC2(CCNCC2)C1)N(Cc1ccc(-c2nnc(C(F)F)o2)cc1F)c1ccccc1] |
| 167 | 21498 | 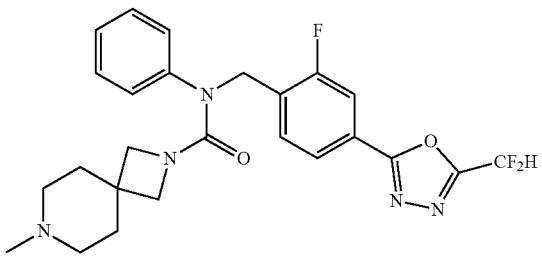 [SMILES: CN1CCC2(CC1)CN(C(=O)N(Cc1ccc(-c3nnc(C(F)F)o3)cc1F)c1ccccc1)C2] |
| 168 | 21499 | 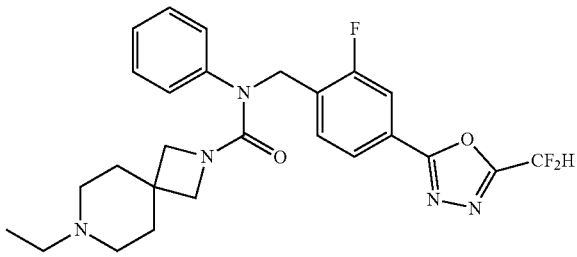 [SMILES: CCN1CCC2(CC1)CN(C(=O)N(Cc1ccc(-c3nnc(C(F)F)o3)cc1F)c1ccccc1)C2] |

-continued
| Ex. | Comp. | Structure |
|---|---|---|
| 169 | 21500 | 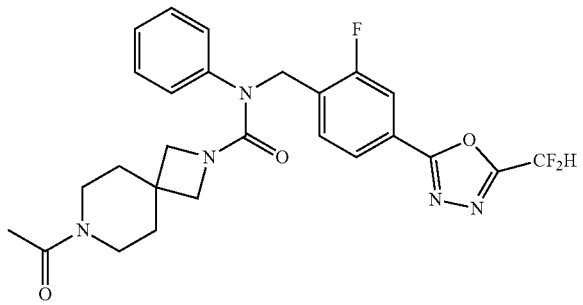 [SMILES: CC(=O)N1CCC2(CC1)CN(C(=O)N(Cc1ccc(-c3nnc(C(F)F)o3)cc1F)c1ccccc1)C2] |
| 170 | 21501 | 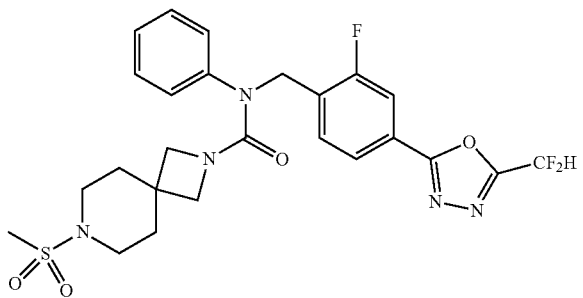 [SMILES: CS(=O)(=O)N1CCC2(CC1)CN(C(=O)N(Cc1ccc(-c3nnc(C(F)F)o3)cc1F)c1ccccc1)C2] |
| 175 | 21514 | 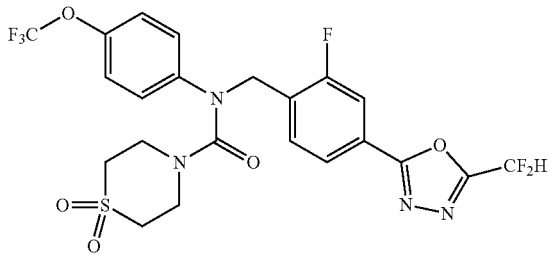 [SMILES: O=C(N1CCS(=O)(=O)CC1)N(Cc1ccc(-c2nnc(C(F)F)o2)cc1F)c1ccc(OC(F)(F)F)cc1] |
| 177 | 21516 | 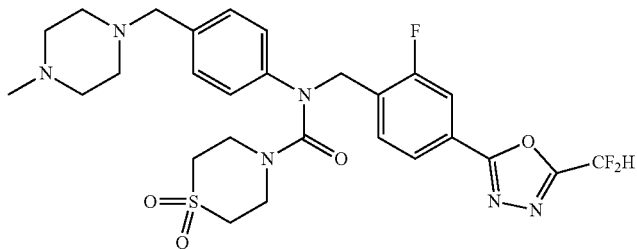 [SMILES: CN1CCN(Cc2ccc(N(Cc3ccc(-c4nnc(C(F)F)o4)cc3F)C(=O)N3CCS(=O)(=O)CC3)cc2)CC1] |
| 179 | 21518 | 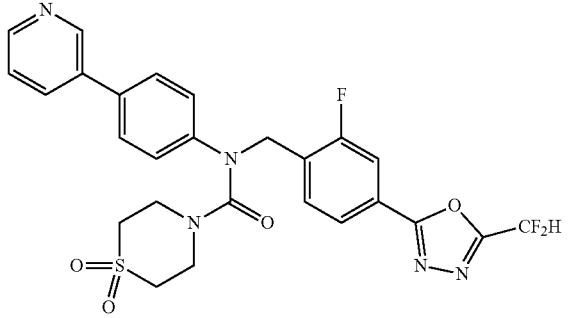 [SMILES: O=C(N1CCS(=O)(=O)CC1)N(Cc1ccc(-c2nnc(C(F)F)o2)cc1F)c1ccc(-c2cccnc2)cc1] |

-continued
| Ex. | Comp. | Structure |
|---|---|---|
| 183 | 21522 | 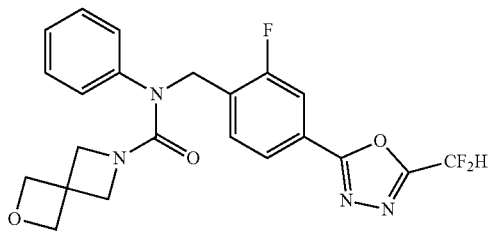 [SMILES: O=C(N1CC2(COC2)C1)N(Cc1ccc(-c2nnc(C(F)F)o2)cc1F)c1ccccc1] |
| 184 | 21527 | 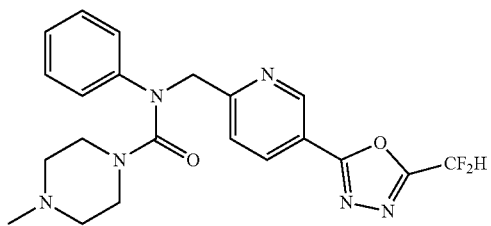 [SMILES: CN1CCN(C(=O)N(Cc2ccc(-c3nnc(C(F)F)o3)cn2)c2ccccc2)CC1] |
| 186 | 21529 | 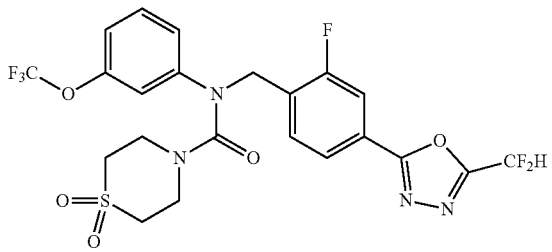 [SMILES: O=C(N1CCS(=O)(=O)CC1)N(Cc1ccc(-c2nnc(C(F)F)o2)cc1F)c1cccc(OC(F)(F)F)c1] |
| 188 | 21531 | 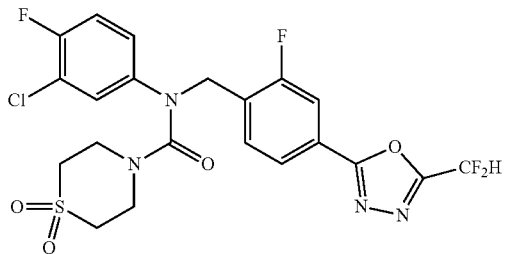 [SMILES: O=C(N1CCS(=O)(=O)CC1)N(Cc1ccc(-c2nnc(C(F)F)o2)cc1F)c1ccc(F)c(Cl)c1] |
| 189 | 21532 | 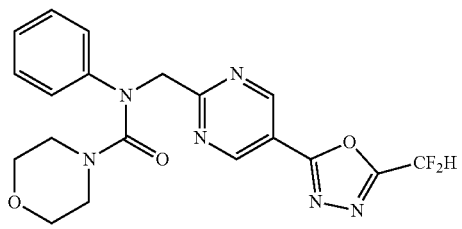 |
| 192 | 21535 | 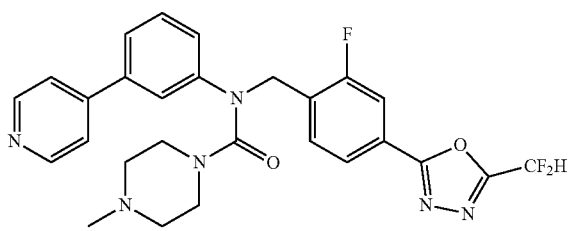 [SMILES: CN1CCN(C(=O)N(Cc2ccc(-c3nnc(C(F)F)o3)cc2F)c2cccc(-c3ccncc3)c2)CC1] |

-continued

| Ex. | Comp. | Structure |
|---|---|---|
| 193 | 21536 | 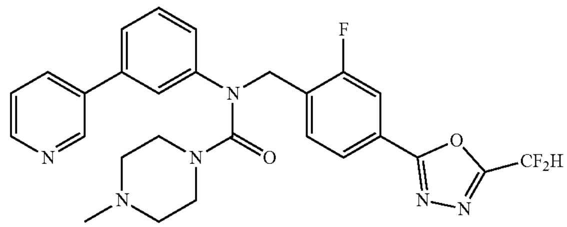 [SMILES: CN1CCN(C(=O)N(Cc2ccc(-c3nnc(C(F)F)o3)cc2F)c2cccc(-c3cccnc3)c2)CC1] |
| 195 | 21540 | 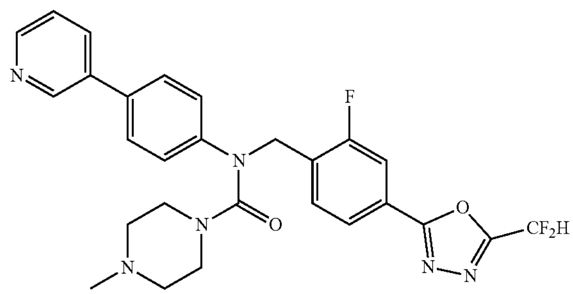 [SMILES: CN1CCN(C(=O)N(Cc2ccc(-c3nnc(C(F)F)o3)cc2F)c2ccc(-c3cccnc3)cc2)CC1] |
| 199 | 21544 | 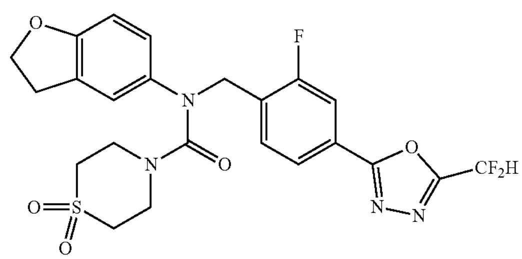 [SMILES: O=C(N1CCS(=O)(=O)CC1)N(Cc1ccc(-c2nnc(C(F)F)o2)cc1F)c1ccc2c(c1)CCO2] |
| 201 | 21546 | 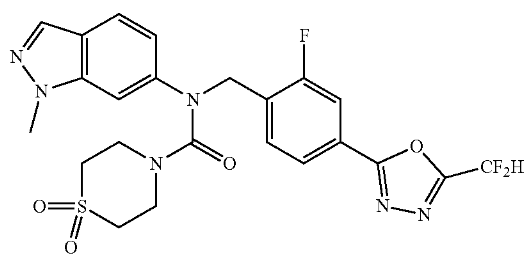 [SMILES: Cn1ncc2ccc(N(Cc3ccc(-c4nnc(C(F)F)o4)cc3F)C(=O)N3CCS(=O)(=O)CC3)cc21] |
| 209 | 21565 | 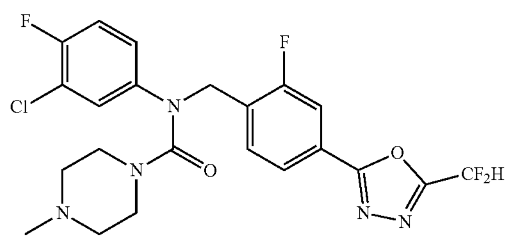 [SMILES: CN1CCN(C(=O)N(Cc2ccc(-c3nnc(C(F)F)o3)cc2F)c2ccc(F)c(Cl)c2)CC1] |
| 210 | 21566 | 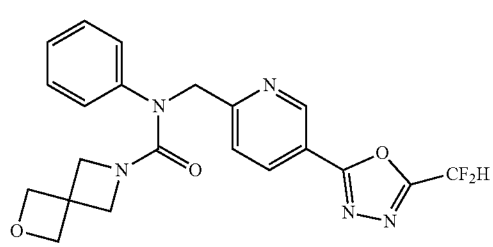 [SMILES: O=C(N1CC2(COC2)C1)N(Cc1ccc(-c2nnc(C(F)F)o2)cn1)c1ccccc1] |

| Ex. | Comp. | Structure |
|---|---|---|
| 216 | 21578 | 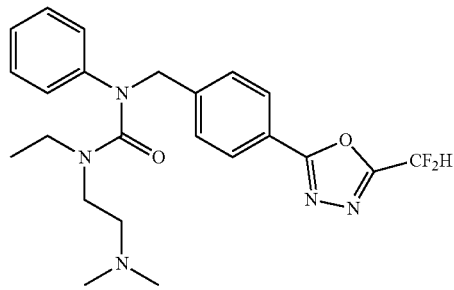 [SMILES: CCN(CCN(C)C)C(=O)N(Cc1ccc(-c2nnc(C(F)F)o2)cc1)c1ccccc1] |
| 217 | 21583 | 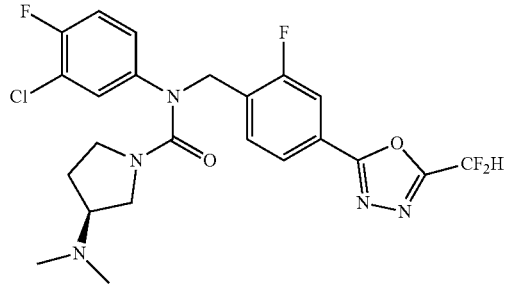 [SMILES: CN(C)[C@H]1CCN(C(=O)N(Cc2ccc(-c3nnc(C(F)F)o3)cc2F)c2ccc(F)c(Cl)c2)C1] |
| 218 | 21584 | 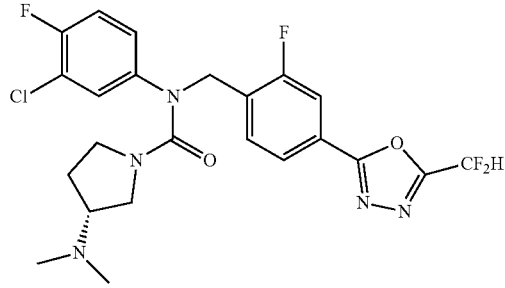 [SMILES: CN(C)[C@@H]1CCN(C(=O)N(Cc2ccc(-c3nnc(C(F)F)o3)cc2F)c2ccc(F)c(Cl)c2)C1] |
| 219 | 21585 | 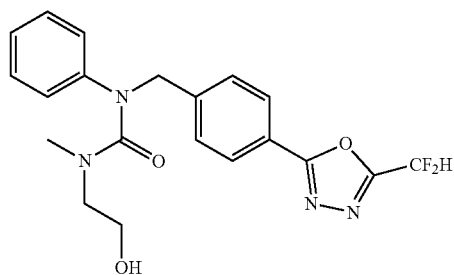 [SMILES: CN(CCO)C(=O)N(Cc1ccc(-c2nnc(C(F)F)o2)cc1)c1ccccc1] |
| 220 | 21586 | 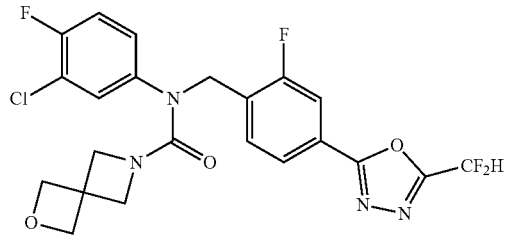 [SMILES: O=C(N1CC2(COC2)C1)N(Cc1ccc(-c2nnc(C(F)F)o2)cc1F)c1ccc(F)c(Cl)c1] |

-continued
| Ex. | Comp. | Structure |
|---|---|---|
| 221 | 21587 | 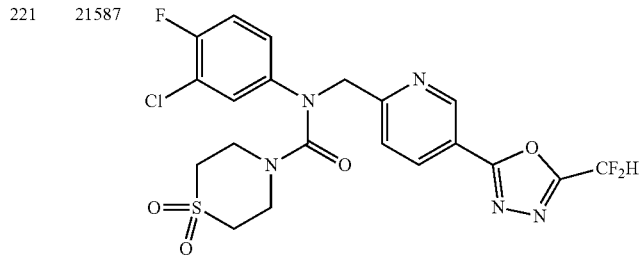 |
| 222 | 21591 | 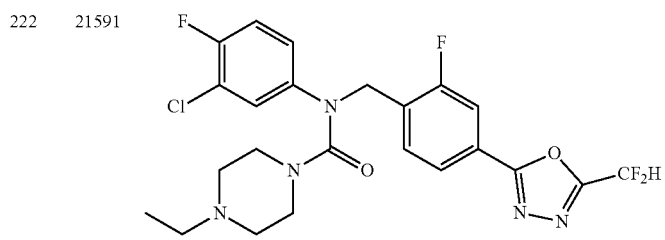 |
| 224 | 21593 | 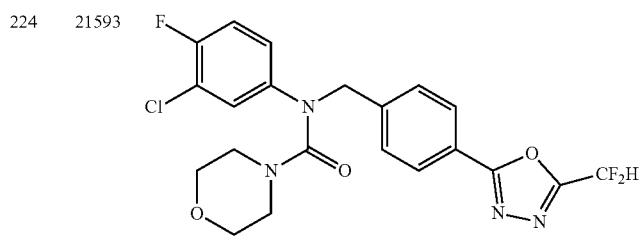 |
| 226 | 21597 | 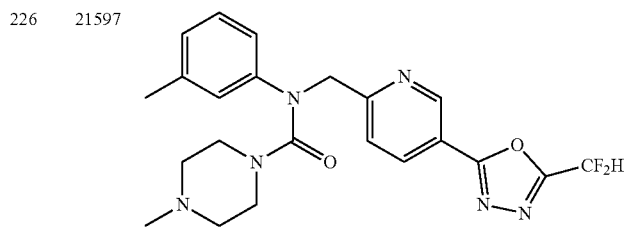 |
| 227 | 21598 | 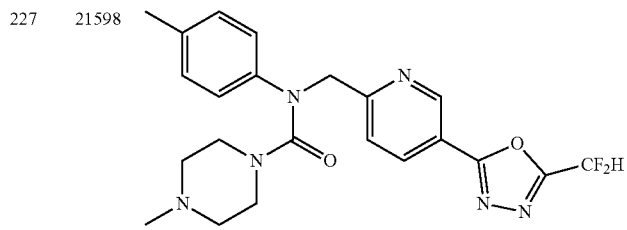 |
| 228 | 21599 | 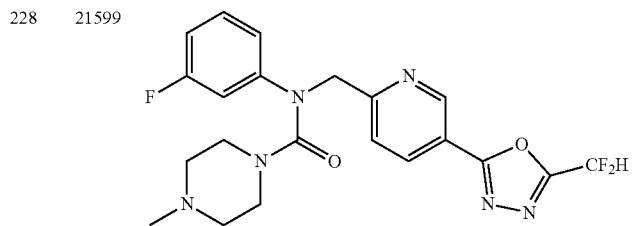 |

-continued

| Ex. | Comp. | Structure |
|---|---|---|
| 229 | 21600 | 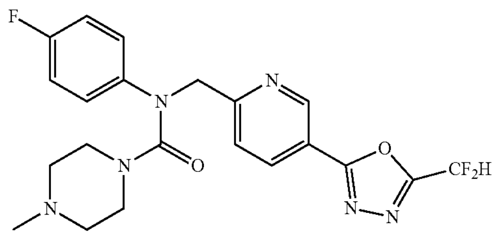 [SMILES: CN1CCN(C(=O)N(Cc2ccc(-c3nnc(C(F)F)o3)cn2)c2ccc(F)cc2)CC1] |
| 231 | 21602 | 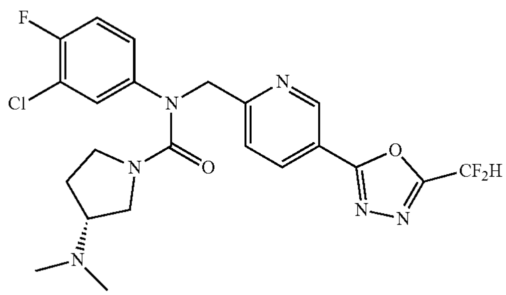 [SMILES: CN(C)[C@@H]1CCN(C(=O)N(Cc2ccc(-c3nnc(C(F)F)o3)cn2)c2ccc(F)c(Cl)c2)C1] |
| 232 | 21619 | 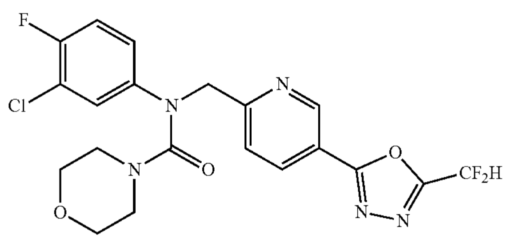 [SMILES: O=C(N1CCOCC1)N(Cc1ccc(-c2nnc(C(F)F)o2)cn1)c1ccc(F)c(Cl)c1] |
| 233 | 21620 | 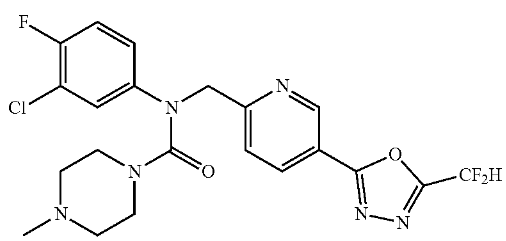 [SMILES: CN1CCN(C(=O)N(Cc2ccc(-c3nnc(C(F)F)o3)cn2)c2ccc(F)c(Cl)c2)CC1] |
| 235 | 21622 | 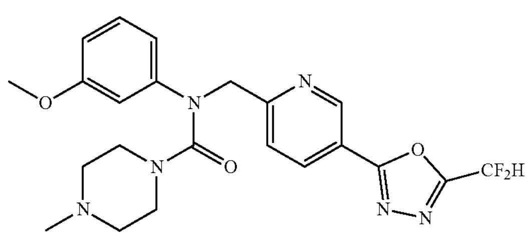 [SMILES: COc1cccc(N(Cc2ccc(-c3nnc(C(F)F)o3)cn2)C(=O)N2CCN(C)CC2)c1] |
| 236 | 21623 | 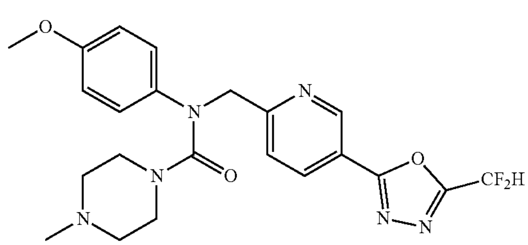 [SMILES: COc1ccc(N(Cc2ccc(-c3nnc(C(F)F)o3)cn2)C(=O)N2CCN(C)CC2)cc1] |

| Ex. | Comp. | Structure |
|---|---|---|
| 237 | 21624 | 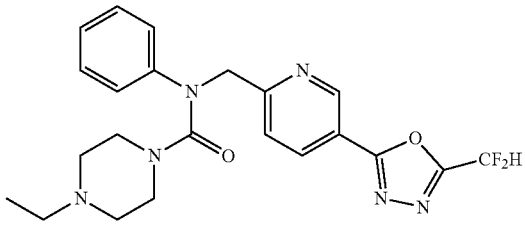 [SMILES: CCN1CCN(C(=O)N(Cc2ccc(-c3nnc(C(F)F)o3)cn2)c2ccccc2)CC1] |
| 238 | 21625 | 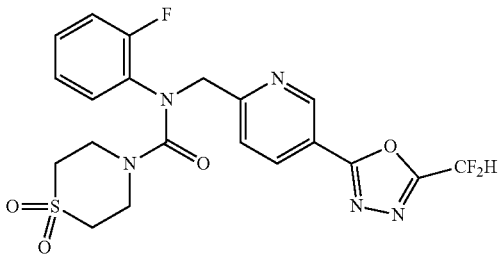 [SMILES: O=C(N1CCS(=O)(=O)CC1)N(Cc1ccc(-c2nnc(C(F)F)o2)cn1)c1ccccc1F] |
| 239 | 21626 | 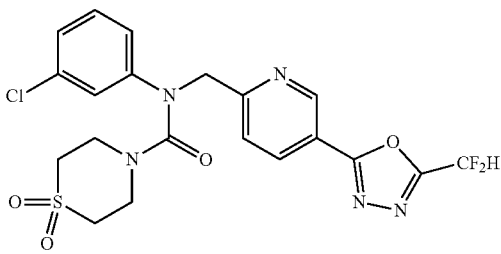 [SMILES: O=C(N1CCS(=O)(=O)CC1)N(Cc1ccc(-c2nnc(C(F)F)o2)cn1)c1cccc(Cl)c1] |
| 242 | 21629 | 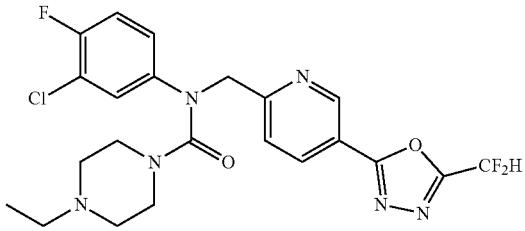 [SMILES: CCN1CCN(C(=O)N(Cc2ccc(-c3nnc(C(F)F)o3)cn2)c2ccc(F)c(Cl)c2)CC1] |
| 243 | 21630 | 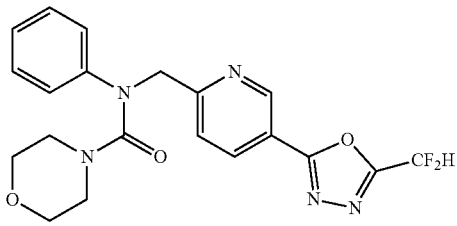 [SMILES: O=C(N1CCOCC1)N(Cc1ccc(-c2nnc(C(F)F)o2)cn1)c1ccccc1] |
| 245 | 21632 | 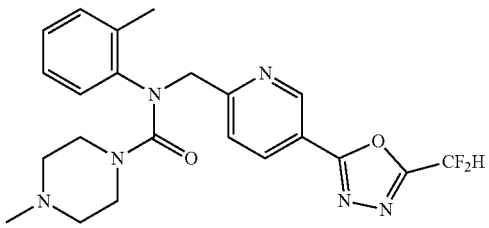 [SMILES: Cc1ccccc1N(Cc1ccc(-c2nnc(C(F)F)o2)cn1)C(=O)N1CCN(C)CC1] |

| Ex. | Comp. | Structure |
|---|---|---|
| 248 | 21643 | 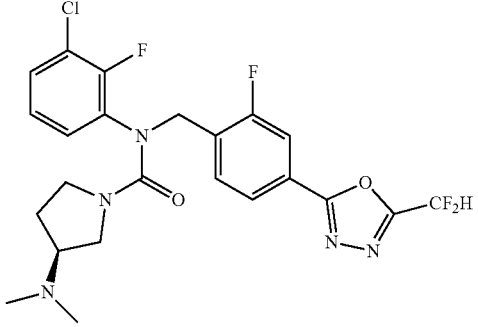 [SMILES: CN(C)[C@H]1CCN(C(=O)N(Cc2ccc(-c3nnc(C(F)F)o3)cc2F)c2cccc(Cl)c2F)C1] |
| 251 | 21646 | 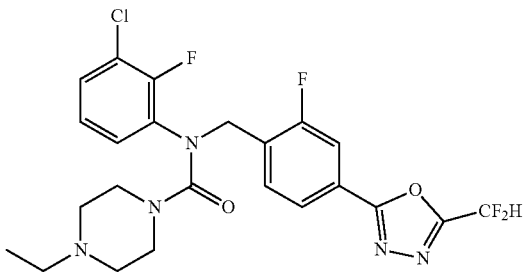 [SMILES: CCN1CCN(C(=O)N(Cc2ccc(-c3nnc(C(F)F)o3)cc2F)c2cccc(Cl)c2F)CC1] |
| 254 | 21652 | 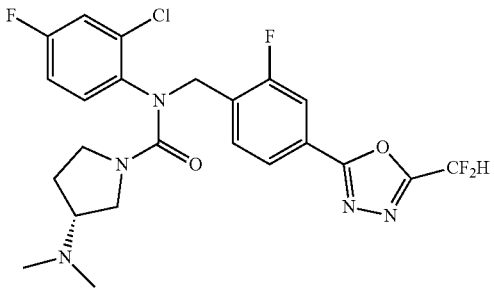 [SMILES: CN(C)[C@@H]1CCN(C(=O)N(Cc2ccc(-c3nnc(C(F)F)o3)cc2F)c2ccc(F)cc2Cl)C1] |
| 255 | 21653 | 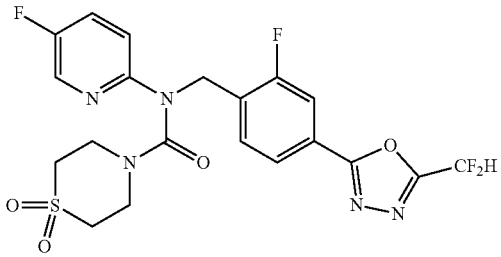 |
| 256 | 21654 | 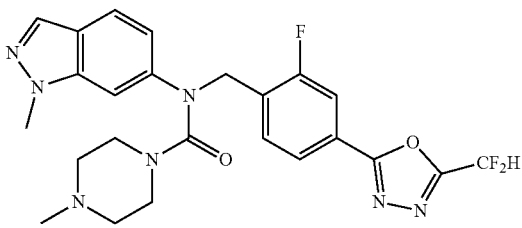 [SMILES: CN1CCN(C(=O)N(Cc2ccc(-c3nnc(C(F)F)o3)cc2F)c2ccc3cnn(C)c3c2)CC1] |

-continued

| Ex. | Comp. | Structure |
|---|---|---|
| 257 | 21655 | 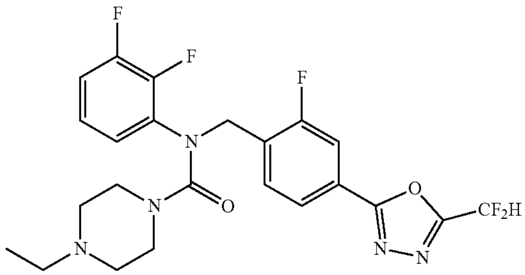 [SMILES: CCN1CCN(C(=O)N(Cc2ccc(-c3nnc(C(F)F)o3)cc2F)c2cccc(F)c2F)CC1] |
| 258 | 21656 | 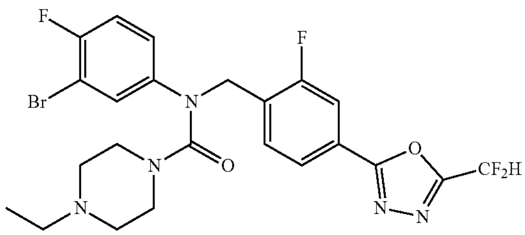 |
| 259 | 21657 | 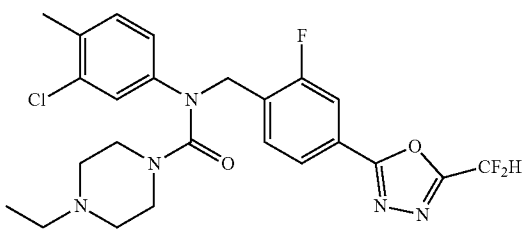 [SMILES: CCN1CCN(C(=O)N(Cc2ccc(-c3nnc(C(F)F)o3)cc2F)c2ccc(C)c(Cl)c2)CC1] |
| 264 | 21665 | 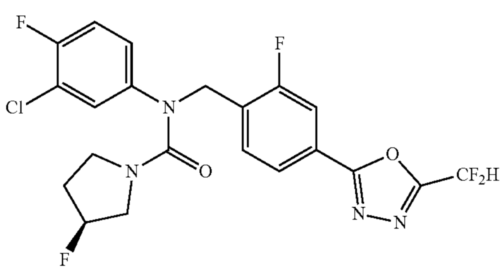 [SMILES: O=C(N1CC[C@H](F)C1)N(Cc1ccc(-c2nnc(C(F)F)o2)cc1F)c1ccc(F)c(Cl)c1] |
| 266 | 21667 | 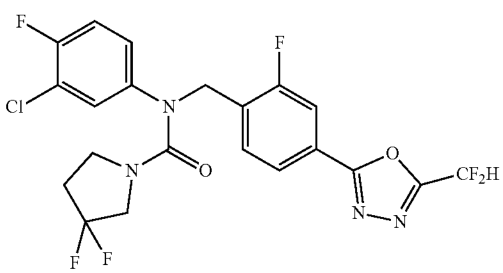 [SMILES: O=C(N1CCC(F)(F)C1)N(Cc1ccc(-c2nnc(C(F)F)o2)cc1F)c1ccc(F)c(Cl)c1] |
| 269 | 21679 | 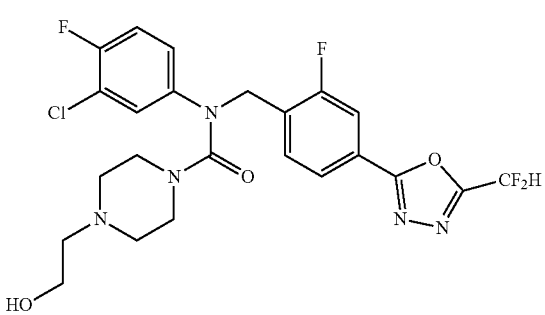 [SMILES: O=C(N1CCN(CCO)CC1)N(Cc1ccc(-c2nnc(C(F)F)o2)cc1F)c1ccc(F)c(Cl)c1] |

-continued
| Ex. | Comp. | Structure |
|---|---|---|
| 270 | 21707 | 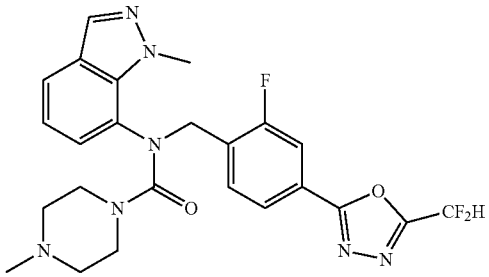 [SMILES: CN1CCN(C(=O)N(Cc2ccc(-c3nnc(C(F)F)o3)cc2F)c2cccc3cnn(C)c23)CC1] |
| 272 | 21709 | 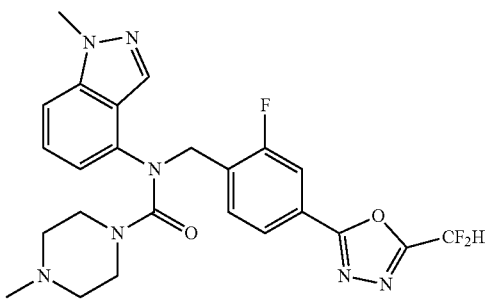 [SMILES: CN1CCN(C(=O)N(Cc2ccc(-c3nnc(C(F)F)o3)cc2F)c2cccc3c2cnn3C)CC1] |
| 273 | 21710 | 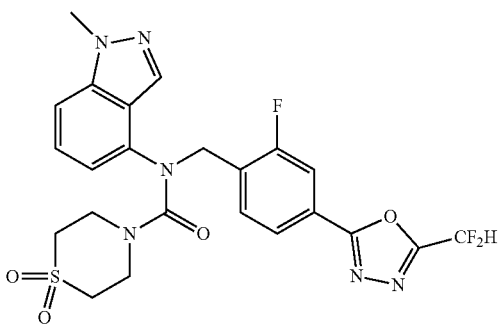 [SMILES: Cn1ncc2c(N(Cc3ccc(-c4nnc(C(F)F)o4)cc3F)C(=O)N3CCS(=O)(=O)CC3)cccc21] |
| 274 | 21724 | 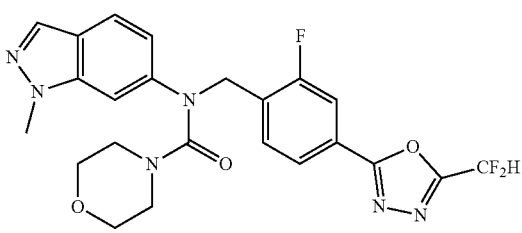 [SMILES: Cn1ncc2ccc(N(Cc3ccc(-c4nnc(C(F)F)o4)cc3F)C(=O)N3CCOCC3)cc21] |
| 275 | 21735 | 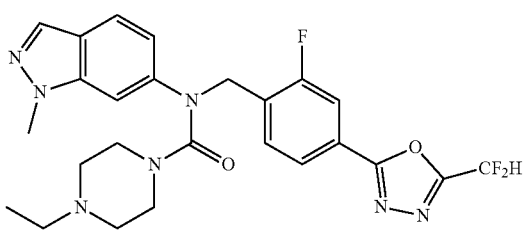 [SMILES: CCN1CCN(C(=O)N(Cc2ccc(-c3nnc(C(F)F)o3)cc2F)c2ccc3cnn(C)c3c2)CC1] |

-continued

| Ex. | Comp. | Structure |
|---|---|---|
| 276 | 21736 | 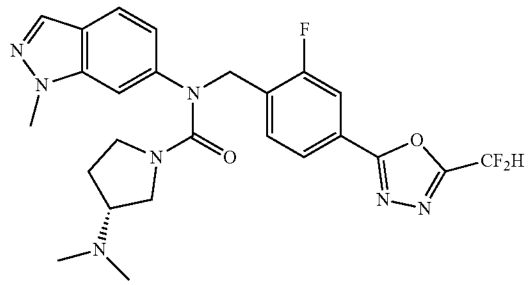 [SMILES: CN(C)[C@@H]1CCN(C(=O)N(Cc2ccc(-c3nnc(C(F)F)o3)cc2F)c2ccc3cnn(C)c3c2)C1] |
| 277 | 21759 | 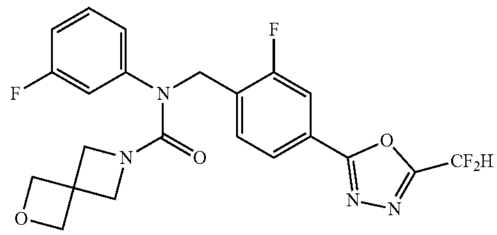 [SMILES: O=C(N1CC2(COC2)C1)N(Cc1ccc(-c2nnc(C(F)F)o2)cc1F)c1cccc(F)c1] |
| 278 | 21760 | 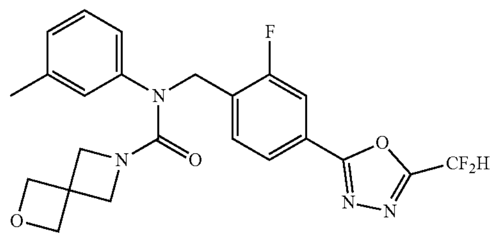 [SMILES: Cc1cccc(N(Cc2ccc(-c3nnc(C(F)F)o3)cc2F)C(=O)N2CC3(COC3)C2)c1] |
| 285 | 21806 | 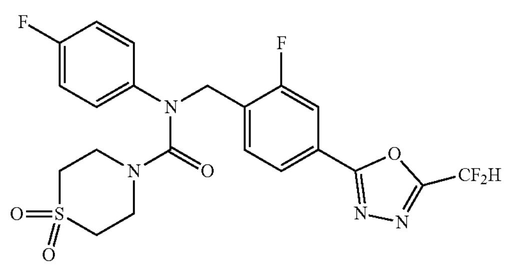 |
| 286 | 21807 | 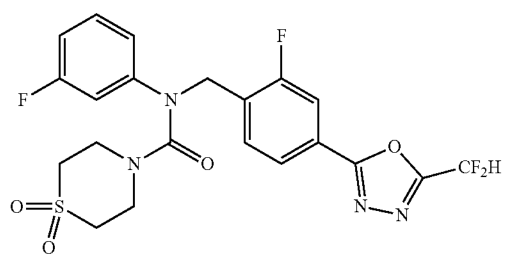 |
| 287 | 21808 | 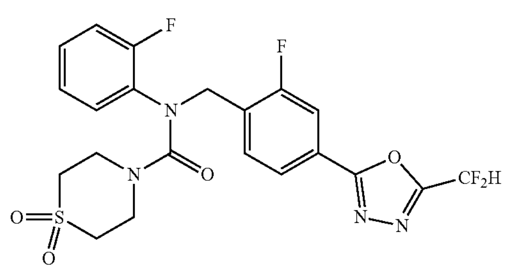 [SMILES: O=C(N1CCS(=O)(=O)CC1)N(Cc1ccc(-c2nnc(C(F)F)o2)cc1F)c1ccccc1F] |

-continued

| Ex. | Comp. | Structure |
|---|---|---|
| 289 | 21810 | 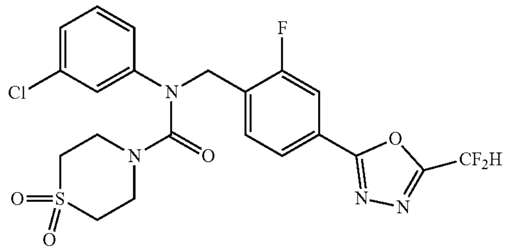 [SMILES: O=C(N1CCS(=O)(=O)CC1)N(Cc1ccc(-c2nnc(C(F)F)o2)cc1F)c1cccc(Cl)c1] |
| 294 | 21824 | 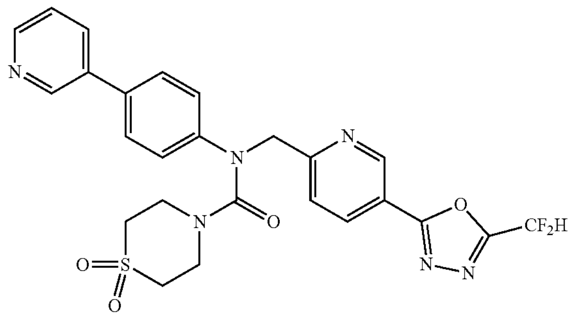 [SMILES: O=C(N1CCS(=O)(=O)CC1)N(Cc1ccc(-c2nnc(C(F)F)o2)cn1)c1ccc(-c2cccnc2)cc1] |
| 295 | 21829 | 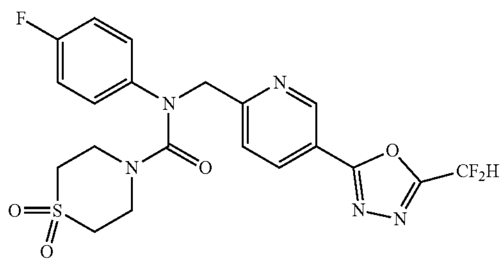 [SMILES: O=C(N1CCS(=O)(=O)CC1)N(Cc1ccc(-c2nnc(C(F)F)o2)cn1)c1ccc(F)cc1] |
| 296 | 21830 | 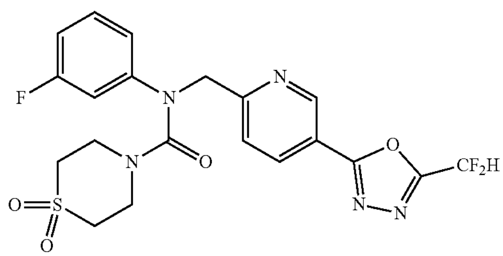 [SMILES: O=C(N1CCS(=O)(=O)CC1)N(Cc1ccc(-c2nnc(C(F)F)o2)cn1)c1cccc(F)c1] |
| 297 | 21831 | 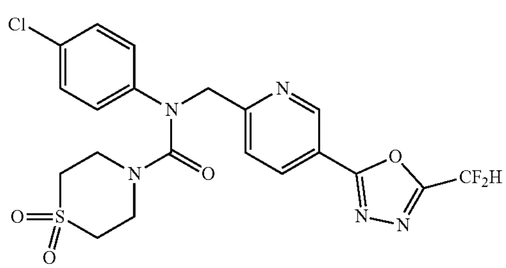 [SMILES: O=C(N1CCS(=O)(=O)CC1)N(Cc1ccc(-c2nnc(C(F)F)o2)cn1)c1ccc(Cl)cc1] |
| 298 | 21839 | 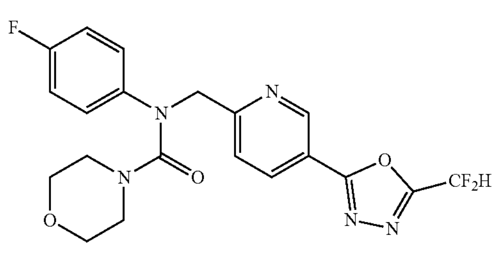 [SMILES: O=C(N1CCOCC1)N(Cc1ccc(-c2nnc(C(F)F)o2)cn1)c1ccc(F)cc1] |

-continued

| Ex. | Comp. | Structure |
|---|---|---|
| 300 | 21841 | 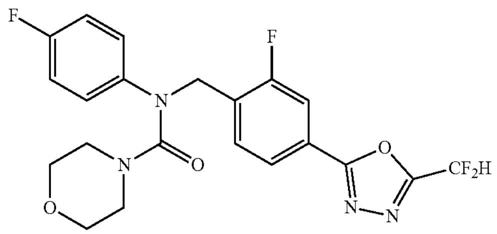 [SMILES: O=C(N1CCOCC1)N(Cc1ccc(-c2nnc(C(F)F)o2)cc1F)c1ccc(F)cc1] |
| 302 | 21843 | 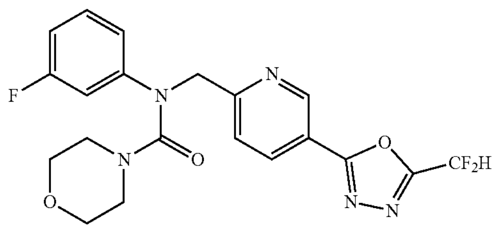 [SMILES: O=C(N1CCOCC1)N(Cc1ccc(-c2nnc(C(F)F)o2)cn1)c1cccc(F)c1] |
| 304 | 21845 | 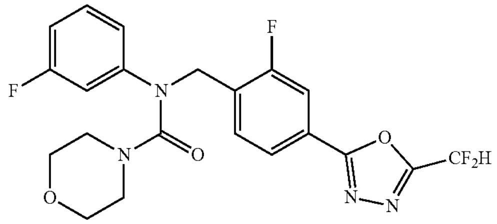 [SMILES: O=C(N1CCOCC1)N(Cc1ccc(-c2nnc(C(F)F)o2)cc1F)c1cccc(F)c1] |
| 306 | 21847 | 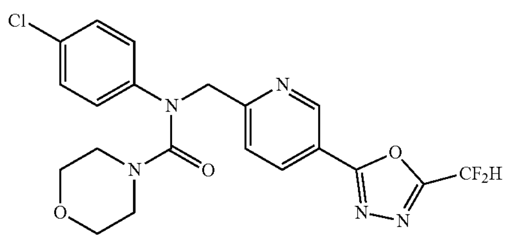 [SMILES: O=C(N1CCOCC1)N(Cc1ccc(-c2nnc(C(F)F)o2)cn1)c1ccc(Cl)cc1] |
| 310 | 21851 | 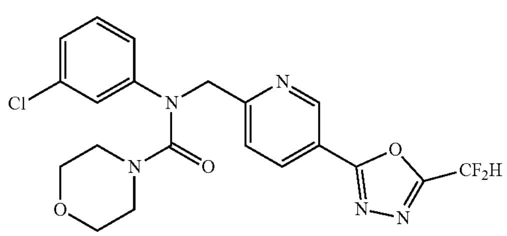 [SMILES: O=C(N1CCOCC1)N(Cc1ccc(-c2nnc(C(F)F)o2)cn1)c1cccc(Cl)c1] |
| 314 | 21855 | 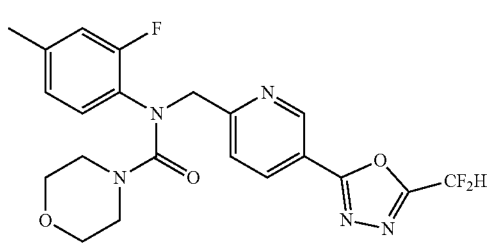 [SMILES: Cc1ccc(N(Cc2ccc(-c3nnc(C(F)F)o3)cn2)C(=O)N2CCOCC2)c(F)c1] |

| Ex. | Comp. | Structure |
|---|---|---|
| 317 | 21858 | 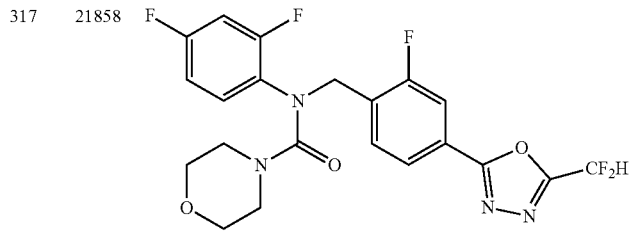 |
| 336 | 21877 | 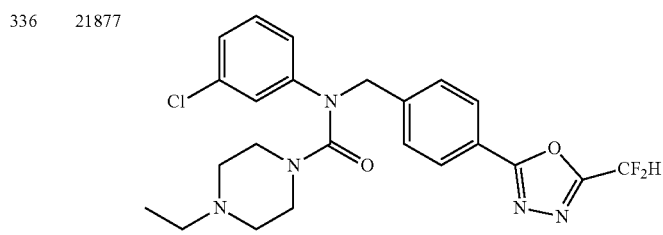 |
| 337 | 21878 | 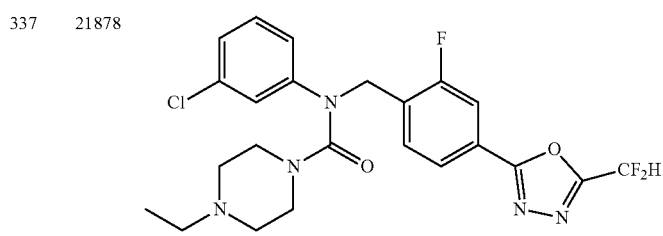 |
| 338 | 21879 | 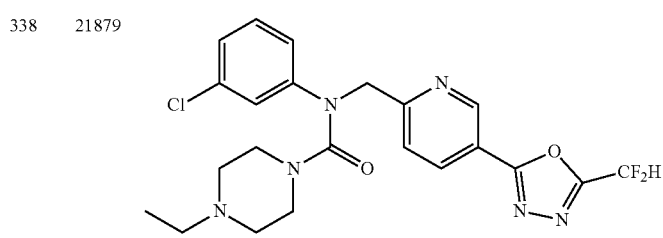 |
| 340 | 21881 | 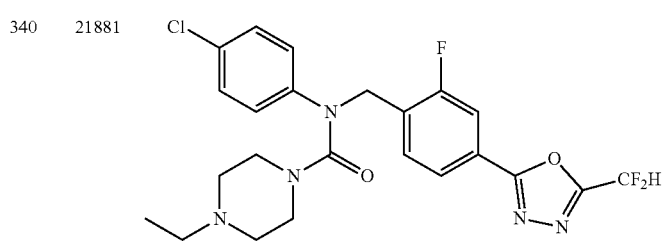 |
| 341 | 21882 | 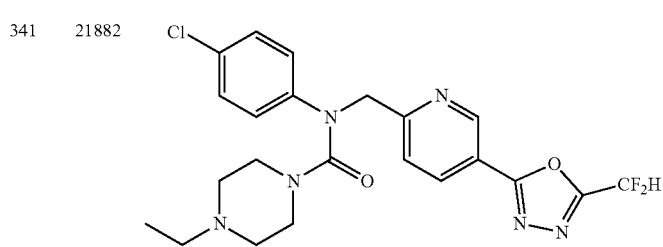 |

-continued
| Ex. | Comp. | Structure |
|---|---|---|
| 342 | 21883 | 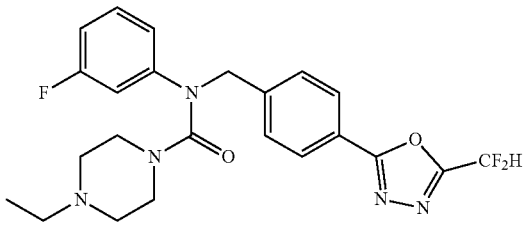 [SMILES: CCN1CCN(C(=O)N(Cc2ccc(-c3nnc(C(F)F)o3)cc2)c2cccc(F)c2)CC1] |
| 343 | 21884 | 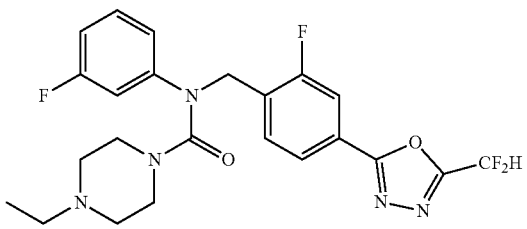 |
| 344 | 21885 | 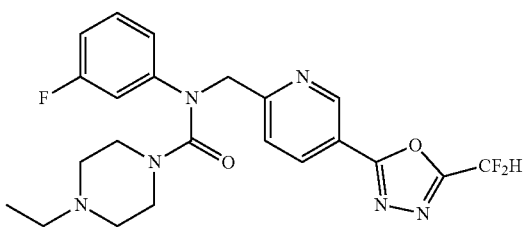 [SMILES: CCN1CCN(C(=O)N(Cc2ccc(-c3nnc(C(F)F)o3)cn2)c2cccc(F)c2)CC1] |
| 345 | 21886 | 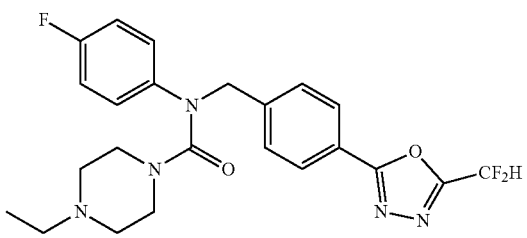 [SMILES: CCN1CCN(C(=O)N(Cc2ccc(-c3nnc(C(F)F)o3)cc2)c2ccc(F)cc2)CC1] |
| 346 | 21887 | 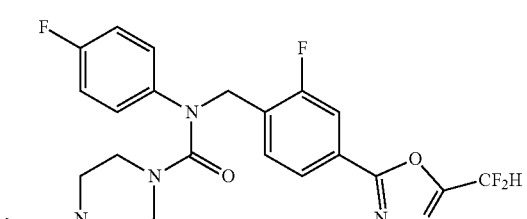 |
| 347 | 21888 | 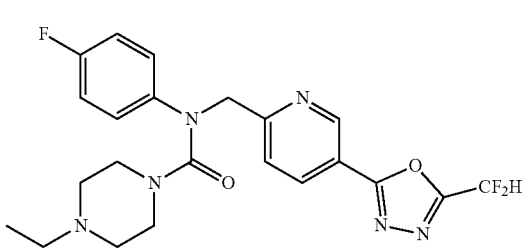 [SMILES: CCN1CCN(C(=O)N(Cc2ccc(-c3nnc(C(F)F)o3)cn2)c2ccc(F)cc2)CC1] |

-continued

| Ex. | Comp. | Structure |
|---|---|---|
| 353 | 21894 | 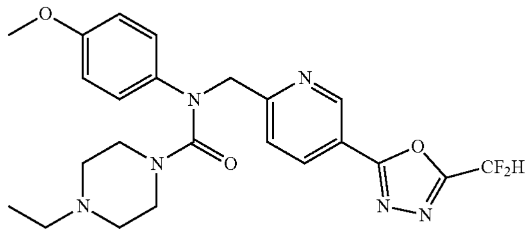 [SMILES: CCN1CCN(C(=O)N(Cc2ccc(-c3nnc(C(F)F)o3)cn2)c2ccc(OC)cc2)CC1] |
| 362 | 21905 | 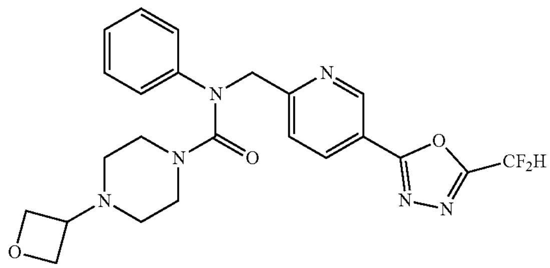 [SMILES: O=C(N1CCN(C2COC2)CC1)N(Cc1ccc(-c2nnc(C(F)F)o2)cn1)c1ccccc1] |
| 387 | 21943 | 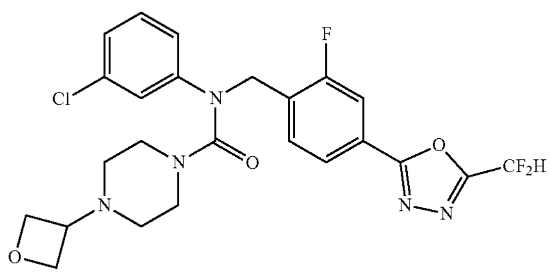 [SMILES: O=C(N1CCN(C2COC2)CC1)N(Cc1ccc(-c2nnc(C(F)F)o2)cc1F)c1cccc(Cl)c1] |
| 388 | 21944 | 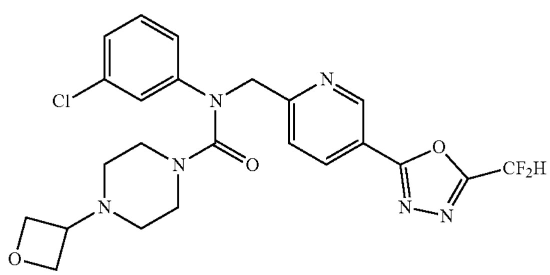 [SMILES: O=C(N1CCN(C2COC2)CC1)N(Cc1ccc(-c2nnc(C(F)F)o2)cn1)c1cccc(Cl)c1] |
| 413 | 21985 | 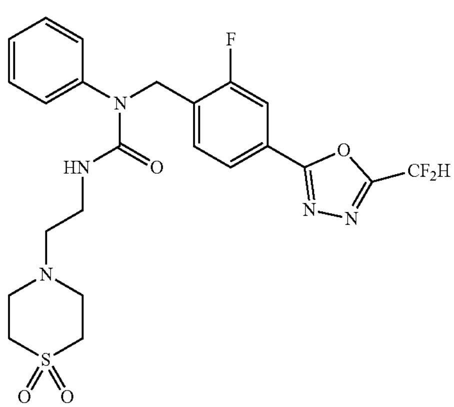 [SMILES: O=C(NCCN1CCS(=O)(=O)CC1)N(Cc1ccc(-c2nnc(C(F)F)o2)cc1F)c1ccccc1] |

| Ex. | Comp. | Structure |
|---|---|---|
| 414 | 21986 | 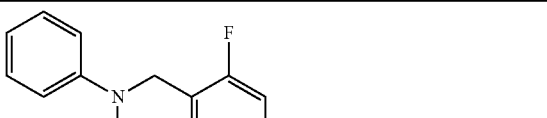 |
7. The 1,3,4-oxadiazole derivative compound represented by formula I, stereoisomer thereof or pharmaceutically acceptable salt thereof according to claim 6, wherein the compound represented by formula I is selected from the group consisting of compounds described in the following table:
| Ex. | Comp. | Structure |
|---|---|---|
| 10 | 21337 | 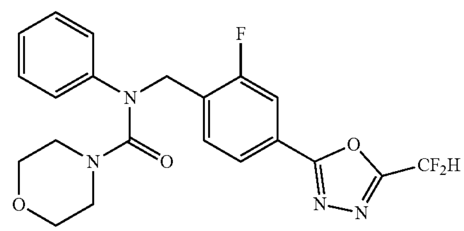 [SMILES: O=C(N1CCOCC1)N(Cc1ccc(-c2nnc(C(F)F)o2)cc1F)c1ccccc1] |
| 40 | 21370 | 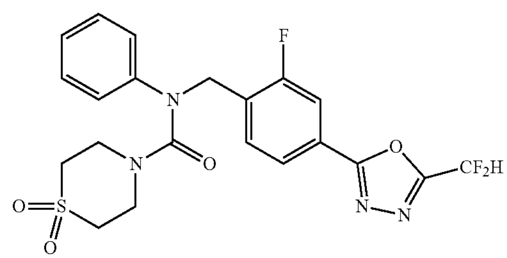 [SMILES: O=C(N1CCS(=O)(=O)CC1)N(Cc1ccc(-c2nnc(C(F)F)o2)cc1F)c1ccccc1] |
| 43 | 21373 | 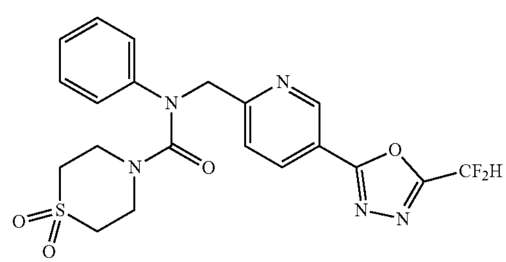 [SMILES: O=C(N1CCS(=O)(=O)CC1)N(Cc1ccc(-c2nnc(C(F)F)o2)cn1)c1ccccc1] |
| 48 | 21378 | 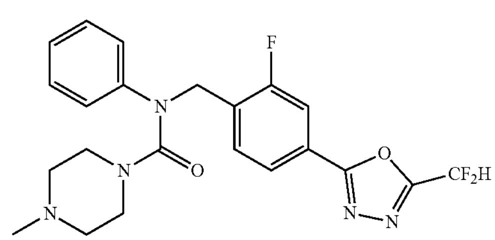 [SMILES: CN1CCN(C(=O)N(Cc2ccc(-c3nnc(C(F)F)o3)cc2F)c2ccccc2)CC1] |

-continued
| Ex. | Comp. | Structure |
|---|---|---|
| 93 | 21423 | 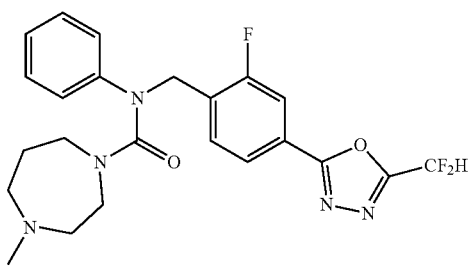 [SMILES: CN1CCCN(C(=O)N(Cc2ccc(-c3nnc(C(F)F)o3)cc2F)c2ccccc2)CC1] |
| 134 | 21465 | 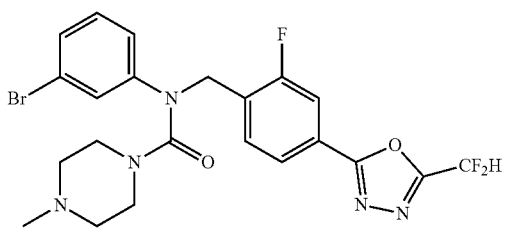 |
| 153 | 21484 | 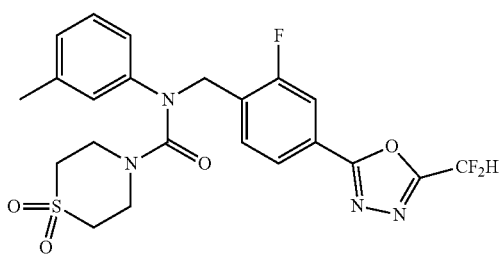 [SMILES: Cc1cccc(N(Cc2ccc(-c3nnc(C(F)F)o3)cc2F)C(=O)N2CCS(=O)(=O)CC2)c1] |
| 165 | 21496 | 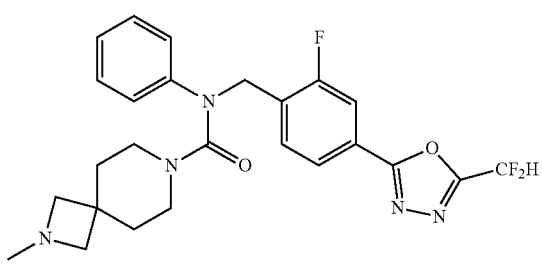 |
| 167 | 21498 | 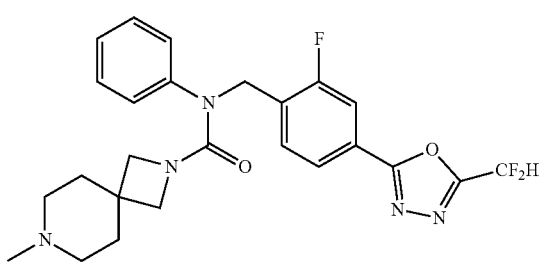 [SMILES: CN1CCC2(CC1)CN(C(=O)N(Cc1ccc(-c3nnc(C(F)F)o3)cc1F)c1ccccc1)C2] |
| 168 | 21499 | 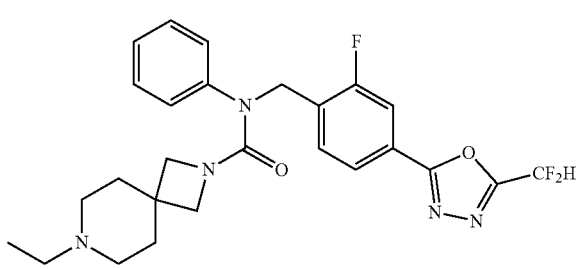 [SMILES: CCN1CCC2(CC1)CN(C(=O)N(Cc1ccc(-c3nnc(C(F)F)o3)cc1F)c1ccccc1)C2] |

-continued
| Ex. | Comp. | Structure |
|---|---|---|
| 169 | 21500 | 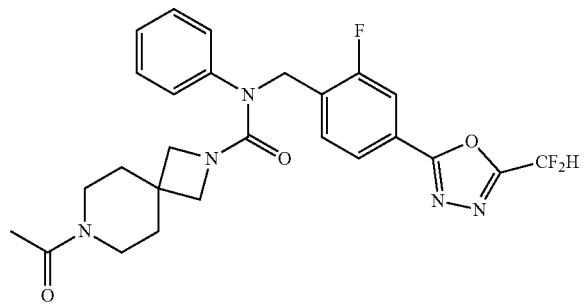 [SMILES: CC(=O)N1CCC2(CC1)CN(C(=O)N(Cc1ccc(-c3nnc(C(F)F)o3)cc1F)c1ccccc1)C2] |
| 170 | 21501 | 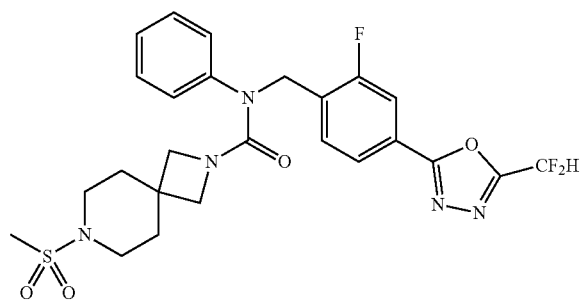 [SMILES: CS(=O)(=O)N1CCC2(CC1)CN(C(=O)N(Cc1ccc(-c3nnc(C(F)F)o3)cc1F)c1ccccc1)C2] |
| 179 | 21518 | 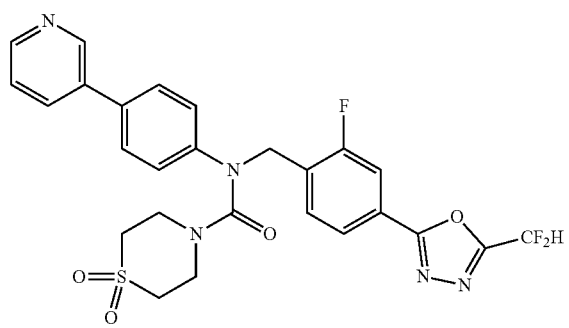 [SMILES: O=C(N1CCS(=O)(=O)CC1)N(Cc1ccc(-c2nnc(C(F)F)o2)cc1F)c1ccc(-c2cccnc2)cc1] |
| 183 | 21522 | 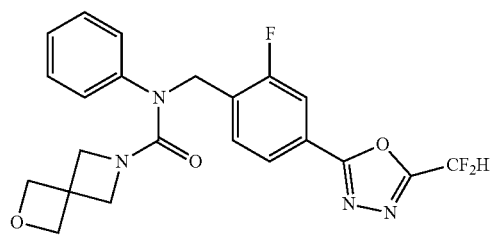 [SMILES: O=C(N1CC2(COC2)C1)N(Cc1ccc(-c2nnc(C(F)F)o2)cc1F)c1ccccc1] |
| 184 | 21527 | 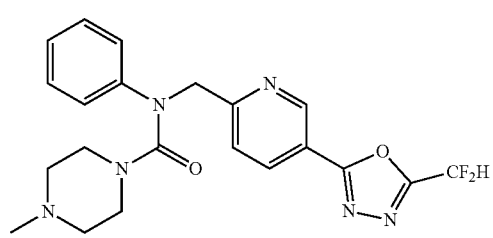 [SMILES: CN1CCN(C(=O)N(Cc2ccc(-c3nnc(C(F)F)o3)cn2)c2ccccc2)CC1] |

| Ex. | Comp. | Structure |
|---|---|---|
| 186 | 21531 | 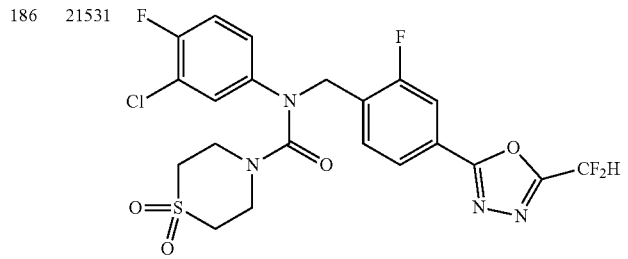 |
| 193 | 21536 | 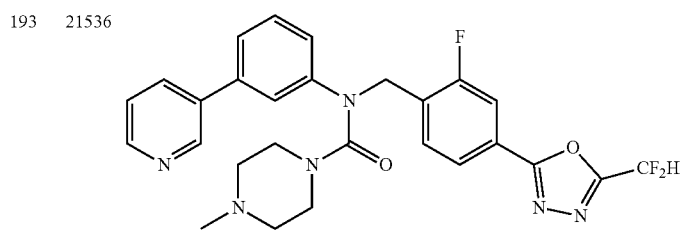 |
| 195 | 21540 | 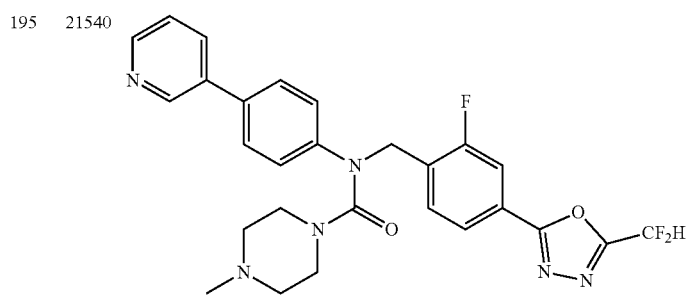 |
| 201 | 21546 | 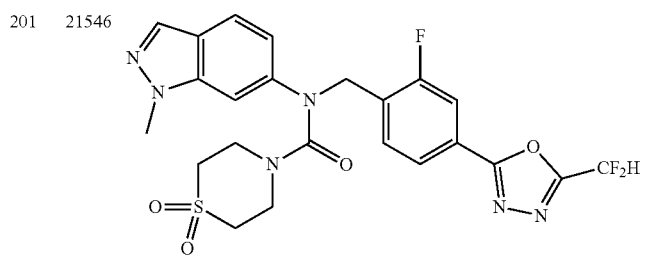 |
| 209 | 21565 | 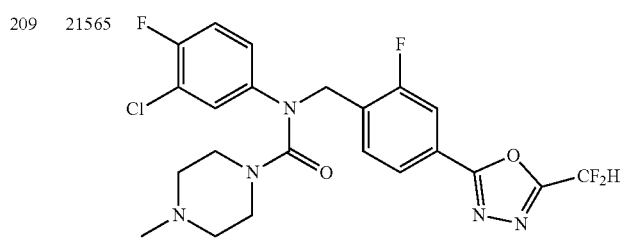 |
| 210 | 21566 | 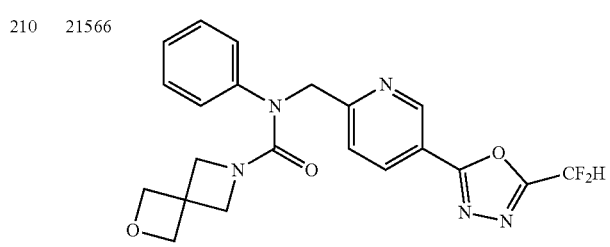 |

-continued
| Ex. | Comp. | Structure |
|---|---|---|
| 217 | 21583 | 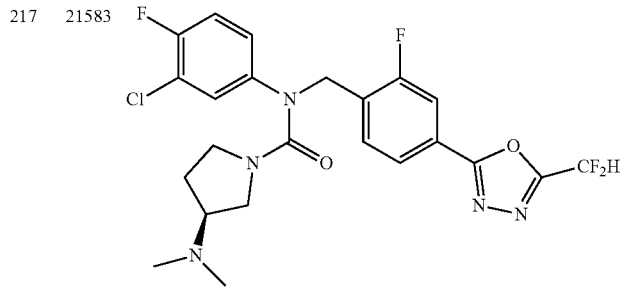 |
| 218 | 21584 | 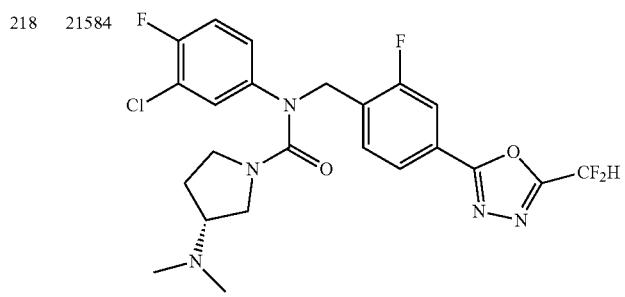 |
| 219 | 21585 | 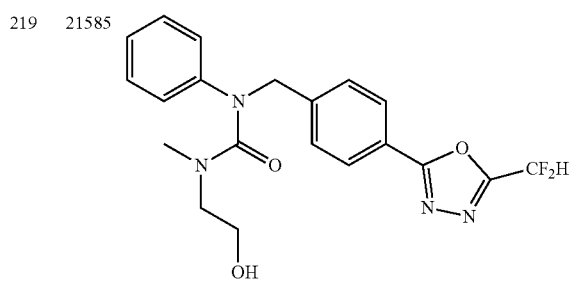 |
| 220 | 21586 | 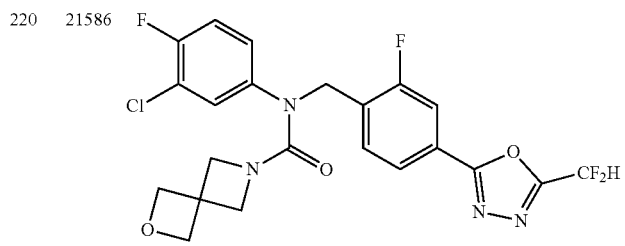 |
| 221 | 21587 | 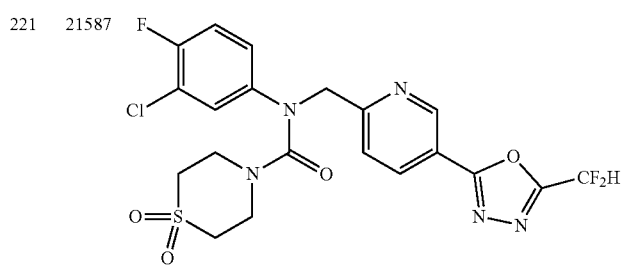 |

| Ex. | Comp. | Structure |
|---|---|---|
| 222 | 21591 | 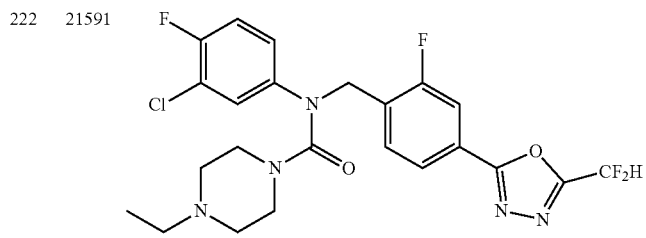 |
| 224 | 21593 | 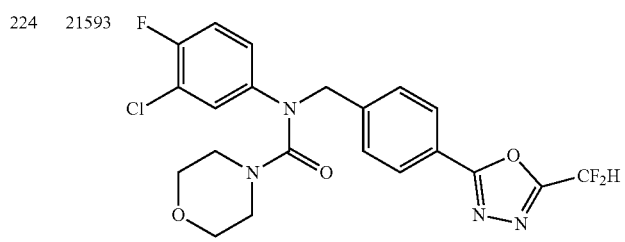 |
| 228 | 21599 | 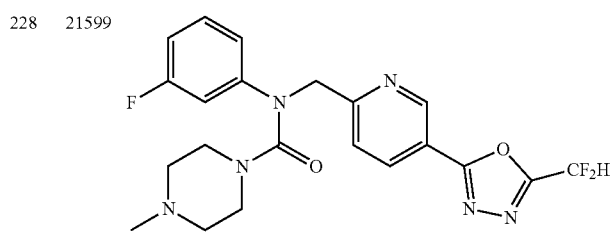 |
| 229 | 21600 | 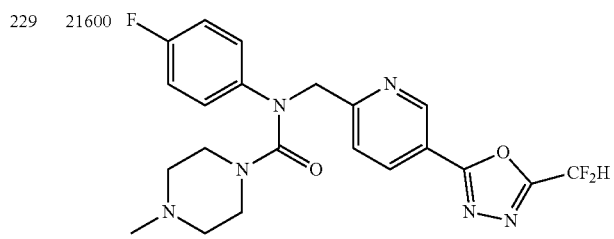 |
| 231 | 21602 | 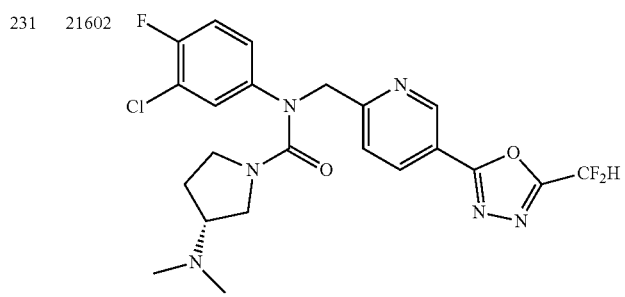 |
| 232 | 21619 | 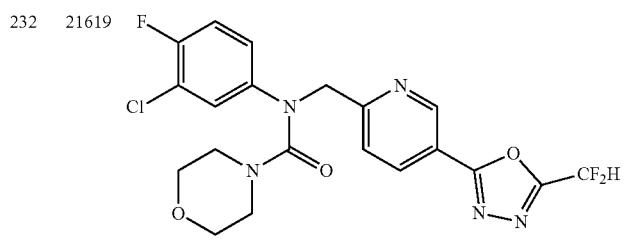 |

-continued

| Ex. | Comp. | Structure |
|---|---|---|
| 233 | 21620 | 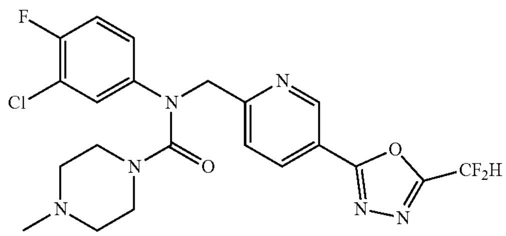 [SMILES: CN1CCN(C(=O)N(Cc2ccc(-c3nnc(C(F)F)o3)cn2)c2ccc(F)c(Cl)c2)CC1] |
| 237 | 21624 | 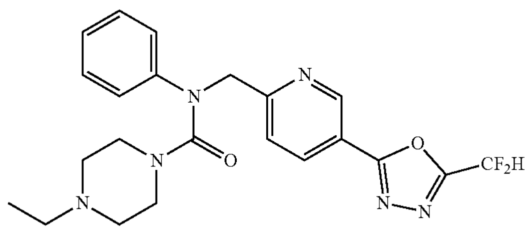 [SMILES: CCN1CCN(C(=O)N(Cc2ccc(-c3nnc(C(F)F)o3)cn2)c2ccccc2)CC1] |
| 238 | 21625 | 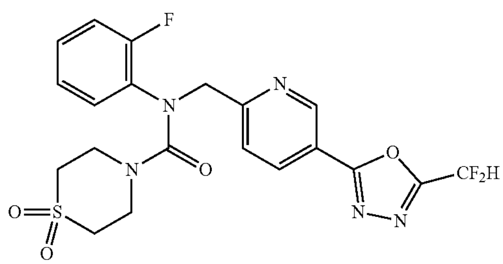 [SMILES: O=C(N1CCS(=O)(=O)CC1)N(Cc1ccc(-c2nnc(C(F)F)o2)cn1)c1ccccc1F] |
| 239 | 21626 | 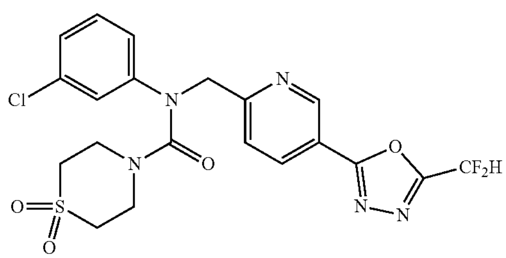 [SMILES: O=C(N1CCS(=O)(=O)CC1)N(Cc1ccc(-c2nnc(C(F)F)o2)cn1)c1cccc(Cl)c1] |
| 242 | 21629 | 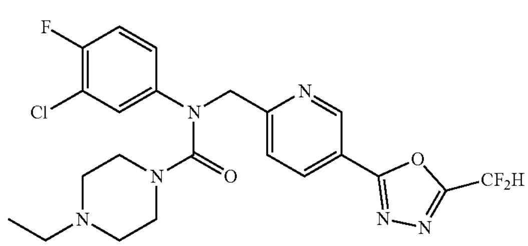 [SMILES: CCN1CCN(C(=O)N(Cc2ccc(-c3nnc(C(F)F)o3)cn2)c2ccc(F)c(Cl)c2)CC1] |
| 243 | 21630 | 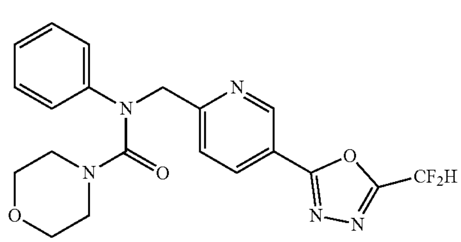 [SMILES: O=C(N1CCOCC1)N(Cc1ccc(-c2nnc(C(F)F)o2)cn1)c1ccccc1] |

-continued
| Ex. | Comp. | Structure |
|---|---|---|
| 248 | 21643 | 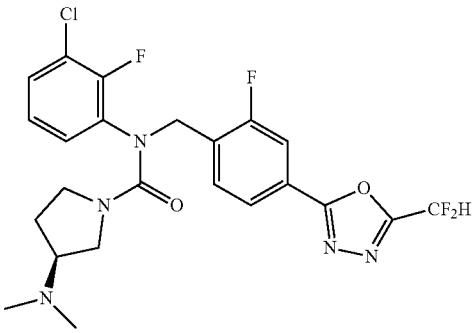 [SMILES: CN(C)[C@H]1CCN(C(=O)N(Cc2ccc(-c3nnc(C(F)F)o3)cc2F)c2cccc(Cl)c2F)C1] |
| 256 | 21654 | 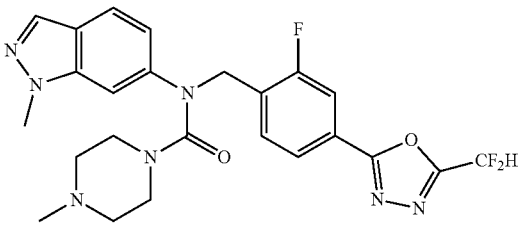 [SMILES: CN1CCN(C(=O)N(Cc2ccc(-c3nnc(C(F)F)o3)cc2F)c2ccc3cnn(C)c3c2)CC1] |
| 257 | 21655 | 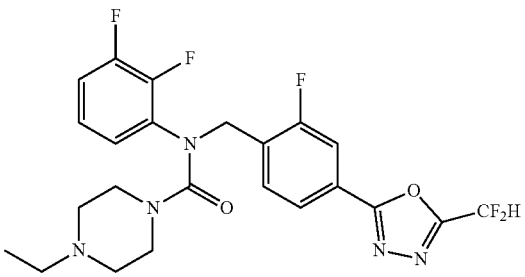 [SMILES: CCN1CCN(C(=O)N(Cc2ccc(-c3nnc(C(F)F)o3)cc2F)c2cccc(F)c2F)CC1] |
| 264 | 21665 | 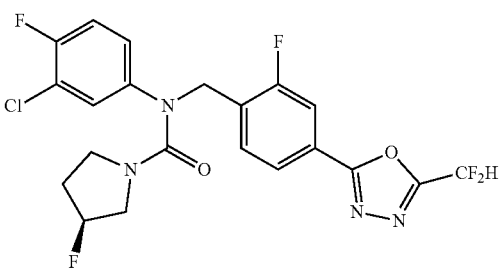 [SMILES: O=C(N1CC[C@H](F)C1)N(Cc1ccc(-c2nnc(C(F)F)o2)cc1F)c1ccc(F)c(Cl)c1] |
| 272 | 21709 | 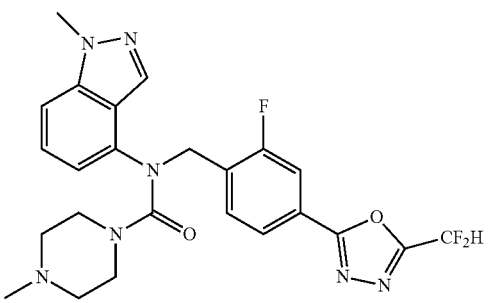 [SMILES: CN1CCN(C(=O)N(Cc2ccc(-c3nnc(C(F)F)o3)cc2F)c2cccc3c2cnn3C)CC1] |

| Ex. | Comp. | Structure |
|---|---|---|
| 273 | 21710 | 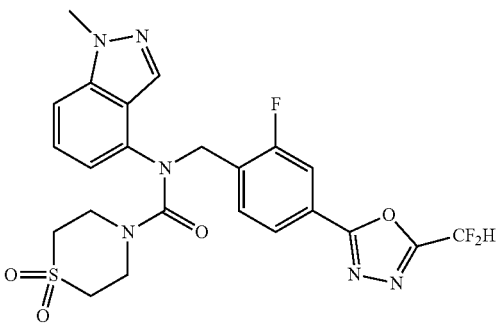 [SMILES: Cn1ncc2c(N(Cc3ccc(-c4nnc(C(F)F)o4)cc3F)C(=O)N3CCS(=O)(=O)CC3)cccc21] |
| 274 | 21724 | 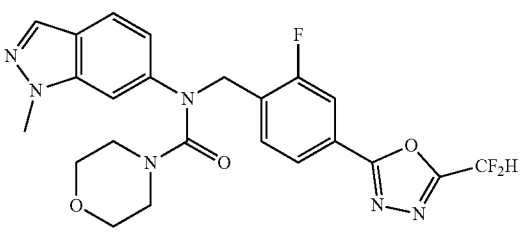 [SMILES: Cn1ncc2ccc(N(Cc3ccc(-c4nnc(C(F)F)o4)cc3F)C(=O)N3CCOCC3)cc21] |
| 275 | 21735 | 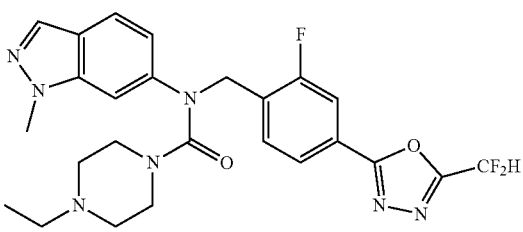 [SMILES: CCN1CCN(C(=O)N(Cc2ccc(-c3nnc(C(F)F)o3)cc2F)c2ccc3cnn(C)c3c2)CC1] |
| 277 | 21759 | 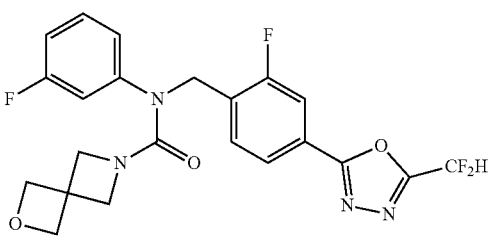 |
| 287 | 21808 | 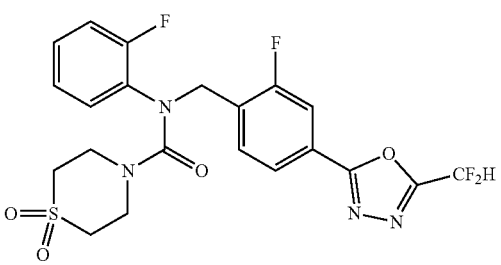 [SMILES: O=C(N1CCS(=O)(=O)CC1)N(Cc1ccc(-c2nnc(C(F)F)o2)cc1F)c1ccccc1F] |
| 289 | 21810 | 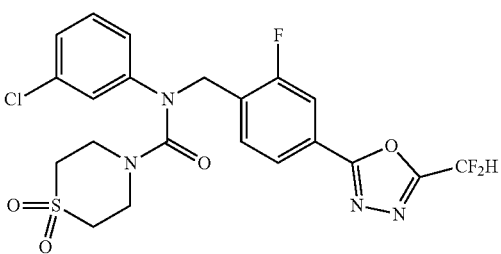 [SMILES: O=C(N1CCS(=O)(=O)CC1)N(Cc1ccc(-c2nnc(C(F)F)o2)cc1F)c1cccc(Cl)c1] |

-continued
| Ex. | Comp. | Structure |
|---|---|---|
| 300 | 21841 | 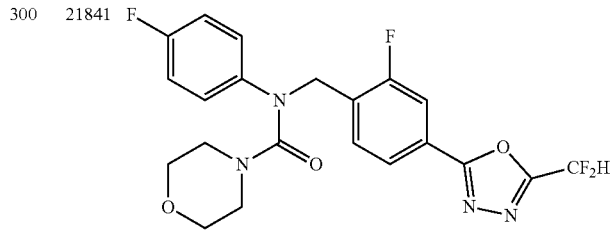 |
| 302 | 21843 | 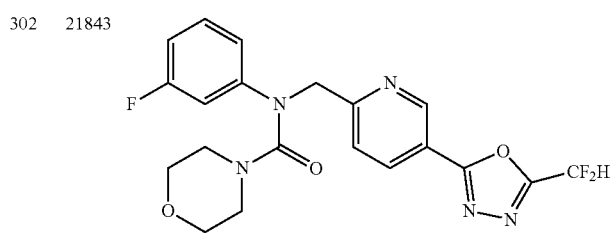 |
| 310 | 21851 | 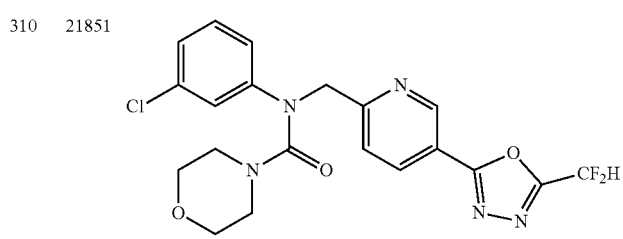 |
| 338 | 21879 | 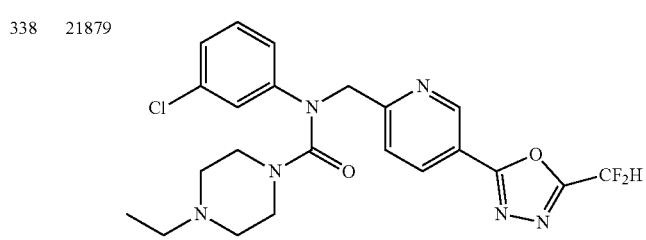 |
| 344 | 21885 | 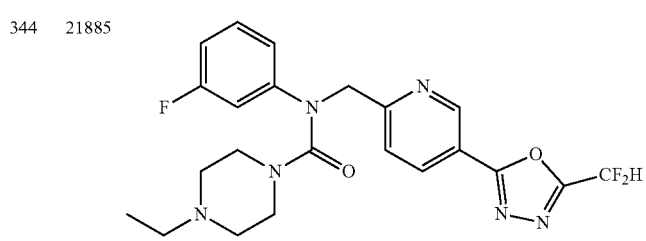 |
| 347 | 21888 | 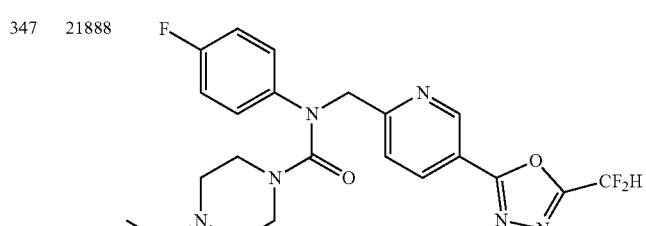 |

8. A pharmaceutical composition comprising, as an active ingredient, the compound represented by formula I, stereoisomer thereof or pharmaceutically acceptable salt thereof according to claim 1.

9. A pharmaceutical composition comprising, as an active ingredient, the compound represented by formula I, stereoisomer thereof or pharmaceutically acceptable salt thereof according to claim 5.

10. A pharmaceutical composition comprising, as an active ingredient, the compound represented by formula I, stereoisomer thereof or pharmaceutically acceptable salt thereof according to claim 1; and a pharmaceutically acceptable carrier.

11. A pharmaceutical composition comprising, as an active ingredient, the compound represented by formula I, stereoisomer thereof or pharmaceutically acceptable salt thereof according to claim 2; and a pharmaceutically acceptable carrier.

12. A pharmaceutical composition comprising, as an active ingredient, the compound represented by formula I, stereoisomer thereof or pharmaceutically acceptable salt thereof according to claim 3; and a pharmaceutically acceptable carrier.

13. A pharmaceutical composition comprising, as an active ingredient, the compound represented by formula I, stereoisomer thereof or pharmaceutically acceptable salt thereof according to claim 4; and a pharmaceutically acceptable carrier.

14. A pharmaceutical composition comprising, as an active ingredient, the compound represented by formula I, stereoisomer thereof or pharmaceutically acceptable salt thereof according to claim 5; and a pharmaceutically acceptable carrier.

15. A pharmaceutical composition comprising, as an active ingredient, the compound represented by formula I, stereoisomer thereof or pharmaceutically acceptable salt thereof according to claim 6; and a pharmaceutically acceptable carrier.

16. A pharmaceutical composition comprising, as an active ingredient, the compound represented by formula I, stereoisomer thereof or pharmaceutically acceptable salt thereof according to claim 7; and a pharmaceutically acceptable carrier.

* * * * *

UNITED STATES PATENT AND TRADEMARK OFFICE
CERTIFICATE OF CORRECTION

Page 1 of 3

PATENT NO. : 10,717,716 B2
APPLICATION NO. : 15/750067
DATED : July 21, 2020
INVENTOR(S) : Jaekwang Lee et al.

It is certified that error appears in the above-identified patent and that said Letters Patent is hereby corrected as shown below:

On the Title Page

Column 2, Item (57) in the Abstract, Line 2:
Delete "in-hibitory" and insert -- inhibitory --, therefor.

Column 2, Item (57) in the Abstract, Line 3:
Delete "salts thereof" and insert -- salts thereof, --, therefor.

Column 2, Item (57) in the Abstract, Line 8:
Delete "compounds" and insert -- compounds, --, therefor.

Column 2, Item (57) in the Abstract, Line 14:
Delete "be-havioral" and insert -- behavioral --, therefor.

In the Claims

Column 1301, Line 8:
In Claim 1, Delete "-heteroaryl" and insert -- -heteroaryl, --, therefor.

Column 1306, Line 23:
In Claim 3, Delete "—$NR^F$—," and insert -- —$NR^F$— --, therefor.

Column 1308, Line 13:
In Claim 4, Delete "—$NR^F$—," and insert -- —$NR^F$— --, therefor.

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,717,716 B2

Column 1345-1346, Line 4:

In Claim 5, Delete " 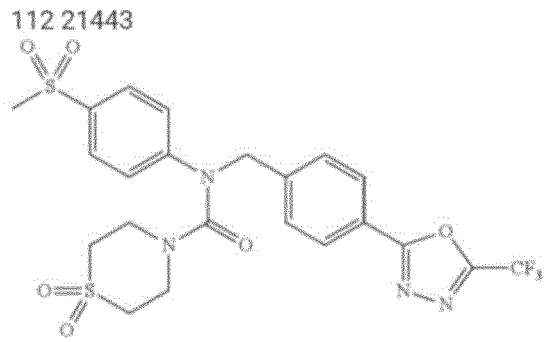 " and insert -- 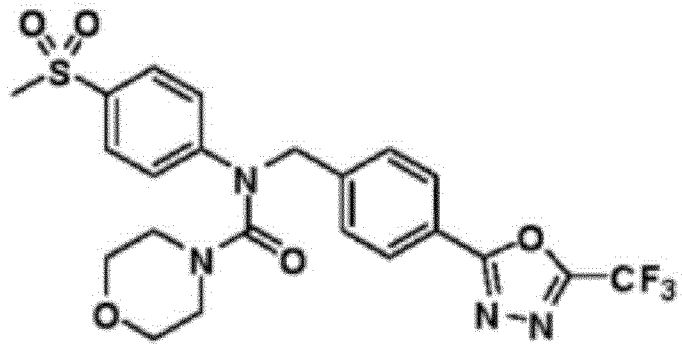 --, therefor.

Column 1437-1438, Line 2:

In Claim 5, Delete " 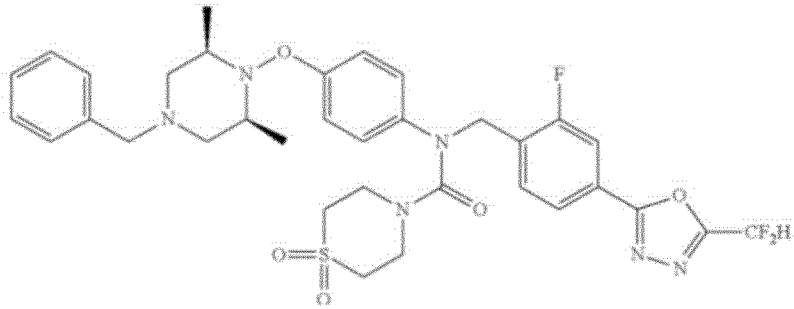 " and

CERTIFICATE OF CORRECTION (continued)
U.S. Pat. No. 10,717,716 B2 insert -- 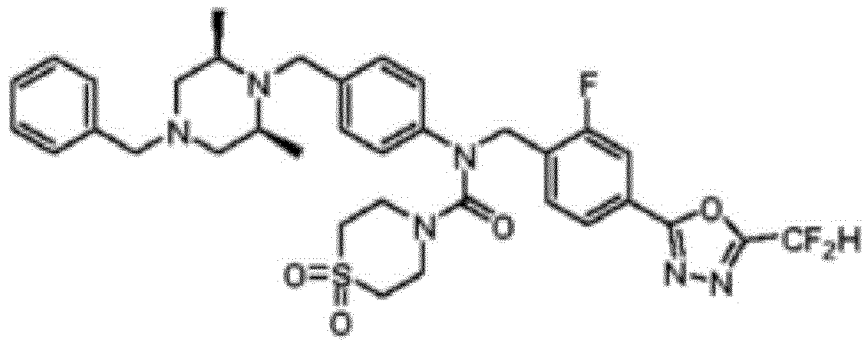 --, thereof.

Column 1437-1438, Line 3:

In Claim 5, Delete " 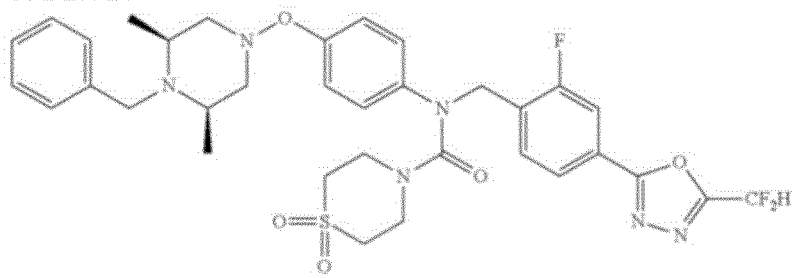 " and insert -- 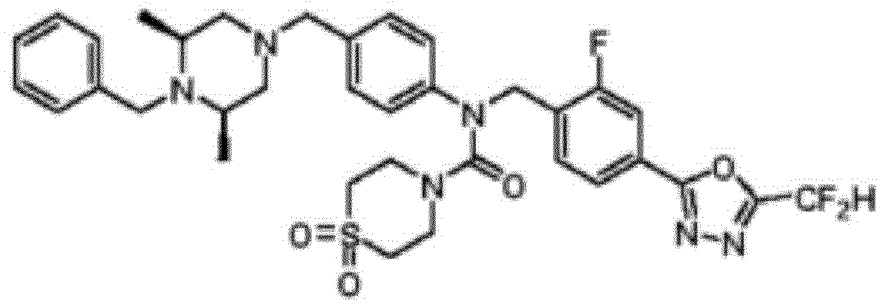 --, thereof.

Column 1525-1526, Line 3:
In Claim 7, Delete "186" and insert -- 188 --, therefor.